US012324353B2

(12) United States Patent
Kim et al.

(10) Patent No.: US 12,324,353 B2
(45) Date of Patent: Jun. 3, 2025

(54) ORGANIC LIGHT EMITTING DEVICE

(71) Applicant: LG CHEM, LTD., Seoul (KR)

(72) Inventors: Minjun Kim, Daejeon (KR); Dong Hoon Lee, Daejeon (KR); Sang Duk Suh, Daejeon (KR); Donghee Kim, Daejeon (KR); Seoyeon Kim, Daejeon (KR); Da Jung Lee, Daejeon (KR); Seung Won Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1072 days.

(21) Appl. No.: 17/286,792

(22) PCT Filed: Mar. 13, 2020

(86) PCT No.: PCT/KR2020/003555
§ 371 (c)(1),
(2) Date: Apr. 19, 2021

(87) PCT Pub. No.: WO2020/189984
PCT Pub. Date: Sep. 24, 2020

(65) Prior Publication Data
US 2023/0049674 A1 Feb. 16, 2023

(30) Foreign Application Priority Data

Mar. 15, 2019 (KR) ........................ 10-2019-0030167
Mar. 12, 2020 (KR) ........................ 10-2020-0031032

(51) Int. Cl.
*H10K 85/60* (2023.01)
*C07D 209/86* (2006.01)
(Continued)

(52) U.S. Cl.
CPC ....... *H10K 85/6574* (2023.02); *C07D 209/86* (2013.01); *C07D 405/14* (2013.01);
(Continued)

(58) Field of Classification Search
None
See application file for complete search history.

(56) References Cited

U.S. PATENT DOCUMENTS

2004/0251816 A1 12/2004 Leo et al.
2015/0236262 A1 8/2015 Cho et al.
(Continued)

FOREIGN PATENT DOCUMENTS

CN 107973786 A 5/2018
CN 108698994 A 10/2018
(Continued)

*Primary Examiner* — Jeffrey D Washville
(74) *Attorney, Agent, or Firm* — Bryan Cave Leighton Paisner LLP

(57) ABSTRACT

An organic light emitting device comprising a first electrode, a second electrode provided to face the first electrode, and a light emitting layer provided between the first electrode and the second electrode and including a first compound represented by Chemical Formula 1 and a second compound represented by Chemical Formula 2, the organic light emitting device which exhibits low driving voltage, high emission efficiency, and long lifespan characteristics.

[Chemical Formula 1]

(Continued)

-continued

[Chemical Formula 2]

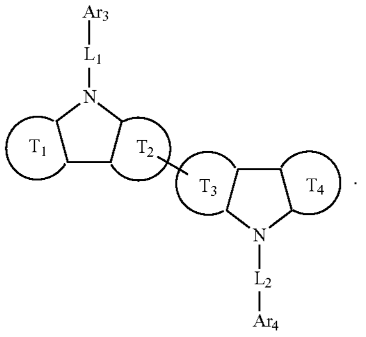

12 Claims, 1 Drawing Sheet

(51) Int. Cl.
*C07D 405/14* (2006.01)
*C07D 409/14* (2006.01)
*C09K 11/06* (2006.01)
*H10K 50/11* (2023.01)
*H10K 101/00* (2023.01)

(52) U.S. Cl.
CPC ............ *C07D 409/14* (2013.01); *C09K 11/06* (2013.01); *H10K 85/615* (2023.02); *H10K 85/624* (2023.02); *H10K 85/626* (2023.02); *H10K 85/654* (2023.02); *H10K 85/6572* (2023.02); *H10K 85/6576* (2023.02); *C09K 2211/1018* (2013.01); *H10K 50/11* (2023.02); *H10K 2101/90* (2023.02)

(56) References Cited

U.S. PATENT DOCUMENTS

| | | | |
|---|---|---|---|
| 2016/0013427 | A1 | 1/2016 | Kim et al. |
| 2016/0164002 | A1 | 6/2016 | Parham et al. |
| 2016/0181548 | A1 | 6/2016 | Parham et al. |
| 2017/0054087 | A1 * | 2/2017 | Zeng .................... C09K 11/025 |
| 2018/0037546 | A1 | 2/2018 | Sugino et al. |
| 2019/0393430 | A1 | 12/2019 | Park et al. |
| 2022/0259187 | A1 * | 8/2022 | Lee .................... H10K 85/6576 |

FOREIGN PATENT DOCUMENTS

| | | | |
|---|---|---|---|
| CN | 109385266 | A | 2/2019 |
| KR | 10-2000-0051826 | A | 8/2000 |
| KR | 10-2012-0081539 | A | 7/2012 |
| KR | 10-2014-0046541 | A | 4/2014 |
| KR | 10-2014-0132244 | A | 11/2014 |
| KR | 10-2015-0134248 | A | 12/2015 |
| KR | 10-2016-0039657 | A | 4/2016 |
| KR | 10-2017-0102000 | A | 9/2017 |
| KR | 10-2018-0041607 | A | 4/2018 |
| KR | 10-2018-0045798 | A | 5/2018 |
| KR | 10-2018-0061077 | A | 6/2018 |
| KR | 10-2018-0071621 | A | 6/2018 |
| KR | 10-2019-0007789 | A | 1/2019 |
| KR | 10-2019-0024772 | A | 3/2019 |
| WO | 2003-012890 | A2 | 2/2003 |
| WO | 2014-054912 | A1 | 4/2014 |
| WO | 2019-045405 | A1 | 3/2019 |

* cited by examiner

【FIG. 1】
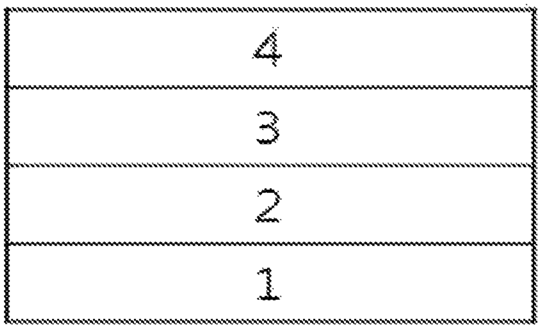
【FIG. 2】
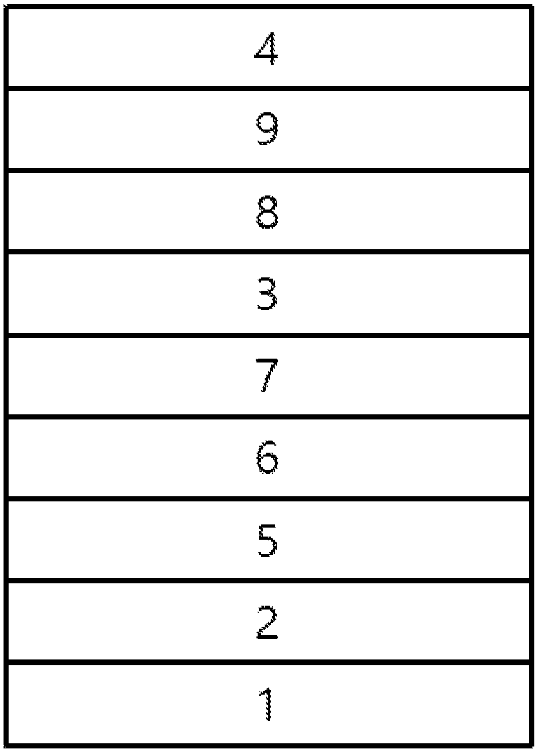

ORGANIC LIGHT EMITTING DEVICE

CROSS-REFERENCE TO RELATED APPLICATION(S)

This application is a National Stage Application of International Application No. PCT/KR2020/003555 filed on Mar. 13, 2020, which claims priority to and benefit of Korean Patent Application No. 10-2019-0030167 filed on Mar. 15, 2019 and Korean Patent Application No. 10-2020-0031032 filed on Mar. 12, 2020, the disclosures of which are incorporated herein by reference in their entirety.

FIELD OF DISCLOSURE

The present disclosure relates to an organic light emitting device having low driving voltage, high emission efficiency and excellent lifespan.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

RELATED ARTS

Korean Unexamined Patent Publication No. 10-2000-0051826

SUMMARY

It is an object of the present invention to provide an organic light emitting device having low driving voltage, high emission efficiency and excellent lifespan.

In one aspect of the present disclosure, organic light emitting device is provided therein.

An organic light emitting device according to the present disclosure comprises a first electrode;

a second electrode that is provided to face the first electrode; and a light emitting layer that is provided between the first electrode and the second electrode, wherein the light emitting layer includes a first compound represented by the following Chemical Formula 1 and a second compound represented by the following Chemical Formula 2:

[Chemical Formula 1]

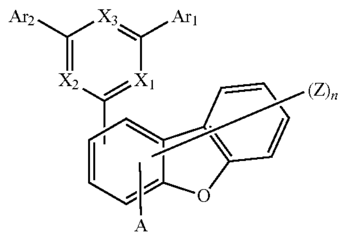

in the Chemical Formula 1, $X_1$ to $X_3$ are each independently N or CH, and at least two of $X_1$ to $X_3$ are N, $Ar_1$ and $Ar_2$ are each independently deuterium; a substituted or unsubstituted $C_{6-60}$ aryl; or a substituted or unsubstituted $C_{2-60}$ heteroaryl containing any one or more heteroatoms selected from the group consisting of N, O and S, each Z is independently hydrogen or deuterium, or two adjacent groups of Zs may combine with each other to form a $C_{6-60}$ aromatic ring unsubstituted or substituted with deuterium; or to form a $C_{2-60}$ heteroaromatic ring unsubstituted or substituted with deuterium and containing any one or more heteroatoms selected from the group consisting of N, O and S, n is an integer from 0 to 6, and A is a substituent represented by the following Chemical Formula 1-1,

[Chemical Formula 1-1]

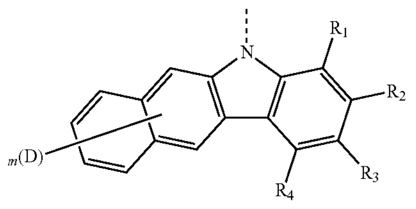

in the Chemical Formula 1-1, $R_1$ to $R_4$ are each independently hydrogen or deuterium, or two adjacent groups of $R_1$ to $R_4$ may combine with each other to form a $C_{6-60}$ aromatic ring unsubstituted or substituted with deuterium; or to form a $C_{2-60}$ heteroaromatic ring unsubstituted or substituted with deuterium and containing any one or more heteroatoms selected from the group consisting of N, O and S, D is deuterium, and m is an integer from 0 to 6,

[Chemical Formula 2]

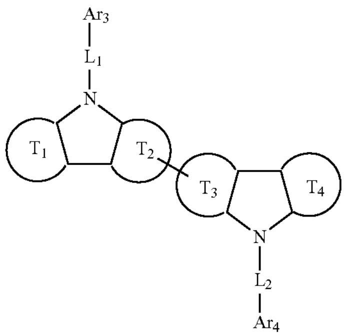

in the Chemical Formula 2, $T_1$ to $T_4$ are each independently a substituted or unsubstituted $C_{6-60}$ aromatic ring fused to an adjacent pentagonal ring; or a substituted or unsubstituted $C_{2-60}$ heteroaromatic ring containing any one or more heteroatoms selected from the group consisting of N, O and S fused to an adjacent pentagonal ring, $L_1$ and $L_2$ are each independently a single bond; a substituted or unsubstituted $C_{6-60}$ arylene; or a substituted or unsubstituted $C_{2-60}$ heteroarylene containing any one or more heteroatoms selected from the group consisting of N, O and S, and $Ar_3$ and $Ar_3$ are each independently a substituted or unsubstituted $C_{6-60}$ aryl; or a substituted or unsubstituted $C_{2-60}$ heteroaryl containing any one or more heteroatoms selected from the group consisting of N, O and S.

Advantageous Effects

The above-described organic light emitting device can exhibit low driving voltage, high emission efficiency, and long lifespan characteristics by simultaneously including a first compound and a second compound as a host material in the light emitting layer.

BRIEF DESCRIPTION OF DRAWINGS

FIG. 1 depicts an example of an organic light emitting device comprising a substrate 1, an anode 2, a light emitting layer 3, and a cathode 4.

FIG. 2 depicts an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4.

DETAILED DESCRIPTION

Hereinafter, embodiments of the present disclosure will be described in more detail to facilitate understanding of the present disclosure.

As used herein, the notation

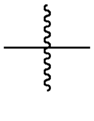 or means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may be interpreted as a substituent in which two phenyl groups are connected.

In the present specification, the carbon number of a carbonyl group is not particularly limited, but is preferably 1 to 40. Specifically, the carbonyl group may be a compound having the following structural Formulae, but is not limited thereto.

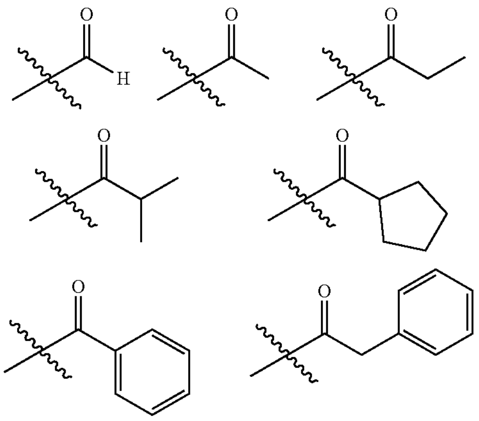

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural Formulae, but is not limited thereto.

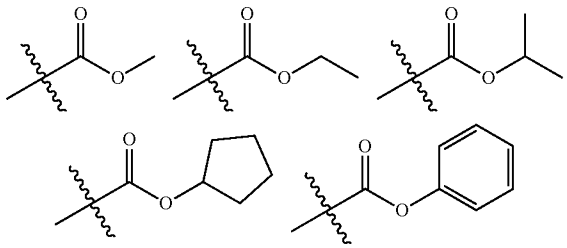

-continued

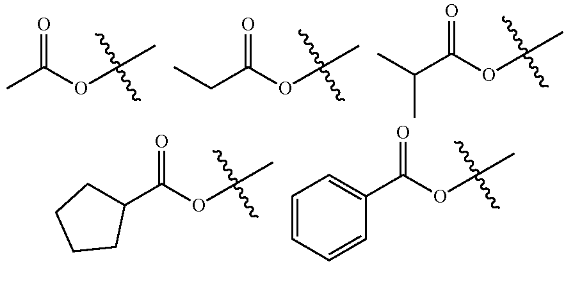

In the present specification, the carbon number of an imide group is not particularly limited, but is preferably 1 to 25. Specifically, the imide group may be a compound having the following structural Formulae, but is not limited thereto.

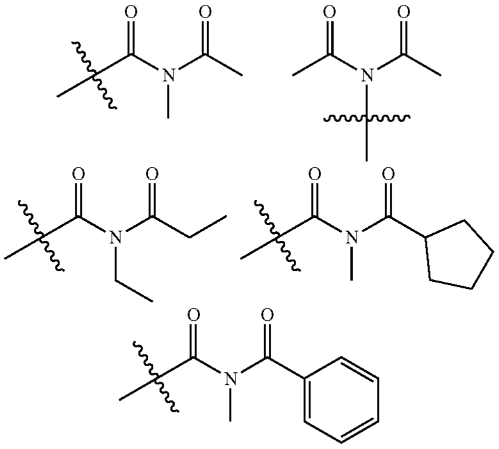

in the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment; the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trim ethylcyclohexyl, 4-tert-butylcyclohexyl, cycloheptyl, cyclooctyl, and the like, but are not limited thereto.

In the present specification, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be bonded to each other to form a spiro structure. In the case where the fluorenyl group is substituted,

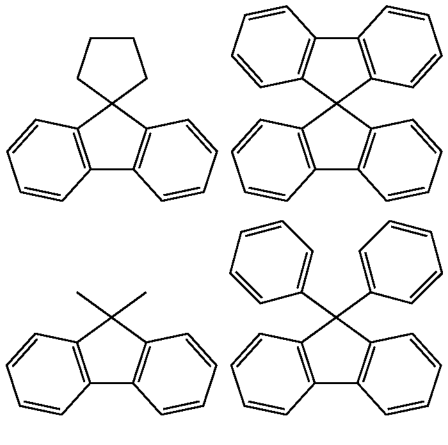

-continued

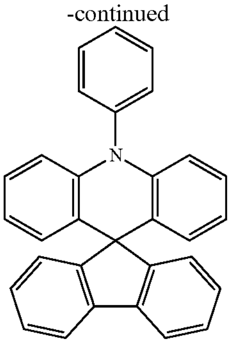

and the like can be formed. However, the structure is not limited thereto.

In the present specification, a heteroaryl is a heteroaryl group containing one or more of O, N, Si and S as a heteroatom, and the carbon number thereof is not particularly limited, but is preferably 2 to 60. Examples of the heteroaryl include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the term “aromatic ring” is understood to include only a condensed monocyclic or condensed polycyclic ring in which the entire molecule has aromaticity while containing only carbon as a ring-forming atom, but also a condensed polycyclic ring formed by connecting a plurality of condensed monocyclic rings such as a fluorene ring to adjacent substituents. At this time, the carbon number of the aromatic ring is 6 to 60, or 6 to 30, or 6 to 20, but is not limited thereto. In addition, the aromatic ring may be a benzene ring, a naphthalene ring, an anthracene ring, a phenanthrene ring, a pyrene ring, a fluorene ring, but is not limited thereto.

As used herein, the term “heteroaromatic ring (heterocyclic ring)” means a hetero-condensed monocyclic or hetero-condensed polycyclic ring in which the entire molecule has aromaticity, while including at least one heteroatom of O, N, and S other than carbon as a ring-forming atom. The carbon number of the hetero ring is 2 to 60, or 2 to 30, or 2 to 20, but is not limited thereto. In addition, the hetero ring may be a benzofuran ring, a benzothiophene ring, a dibenzofuran ring, a dibenzothiophene ring, or the like, but is not limited thereto.

In the present specification, the aryl group in the aralkyl group, the aralkenyl group, the alkylaryl group and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heteroaryl group can be applied, except that the heteroaryl group is not a monovalent group but formed by combining two substituent groups.

Hereinafter, the present disclosure will be described in detail for each configuration.

First Electrode and Second Electrode

The organic light emitting diode according to one embodiment includes on a substrate a first electrode and a second electrode that is provided to face the first electrode, wherein when the first electrode is an anode, the second electrode is a cathode, and when the first electrode is a cathode, the second electrode is an anode.

Specifically, the organic light emitting device may be a normal type organic light emitting device in which an anode, a light emitting layer, and a cathode are sequentially stacked on a substrate. Alternatively, the organic light emitting device may be an inverted type organic light emitting device in which a cathode, a light emitting layer and an anode are sequentially stacked on a substrate.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Light Emitting Layer

The organic light emitting device according to one embodiment includes a light emitting layer which is provided between the first electrode and the second electrode and which is a layer that emits light in the visible light region by combining holes and electrons transported from the hole transport layer and the electron transport layer, wherein the light emitting layer includes a first compound represented by the Chemical Formula 1 and a second compound represented by the Chemical Formula 2.

At this time, both the first compound and the second compound are used as host materials in the light emitting layer. Specifically, the first compound is an N-type host material, and the second compound is a P-type host material. When the light-emitting layer of the organic light emitting device includes the N-type host material and the P-type host material at the same time, it may exhibit improved effects in terms of efficiency and lifespan as compared with the case of using a single material host.

In particular, the first compound has a structure in which both an N-containing 6-membered heterocyclic group and an A substituent (benzocarbazolyl-based substituent) are bonded to one benzene ring of the dibenzofuran-based core. The first compound having such a structure has high stability to electrons and holes, and can stably maintain the balance of electrons and holes, as compared with a compound having a structure in which an N-containing 6-membered heterocyclic group and an A substituent (benzocarbazolyl-based substituent) are respectively bonded to another benzene ring of the dibenzofuran-based core, and a compound in which a substituted/unsubstituted carbazolyl substituent is combined instead of the A substituent (benzocarbazolyl-based substituent). Therefore, the organic light emitting device employing the first compound exhibits the characteristics of low driving voltage, high efficiency and long lifespan as compared with an organic light emitting device employing (i) a compound having a structure in which an N-containing 6-membered heterocyclic group and an A substituent (benzocarbazolyl-based substituent) are respectively bonded to another benzene ring of the dibenzofuran-based core, and (ii) a compound in which a substituted/unsubstituted carbazolyl substituent is combined instead of the A substituent (benzocarbazolyl-based substituent).

Preferably, the first compound is represented by any one of the following Chemical Formulae 1A to 1D depending on the binding position of the N-containing 6-membered-heterocyclic group in the dibenzofuran-based core:

[Chemical Formula 1A]

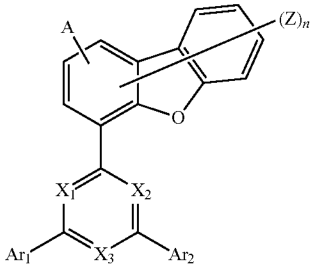

[Chemical Formula 1B]

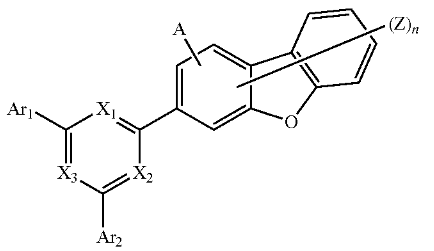

[Chemical Formula 1C]

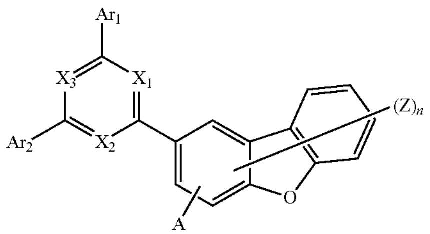

-continued

[Chemical Formula 1D]

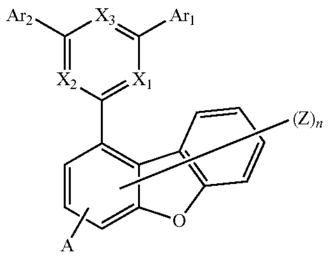

in the Chemical Formulae 1A to 1D, the descriptions of each substituent are the same as defined in the Chemical Formula 1.

Preferably, $X_1$ to $X_3$ are N.

Preferably, Z are each independently hydrogen or deuterium, or two adjacent groups of Zs may combine with each other to form a $C_{6-20}$ aromatic ring, for example, a benzene ring unsubstituted or substituted with deuterium.

At this time, n, which means the number of Z, is 0, 1, 2, 3, 4, 5, or 6.

More specifically; the first compound may be represented by any one of the following Chemical Formulae 1A-1 to 1D-1:

1A-1

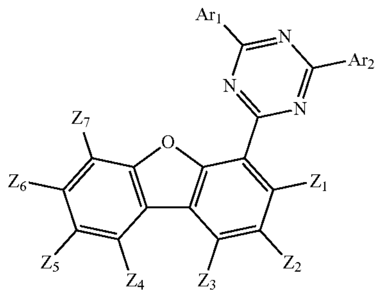

1B-1

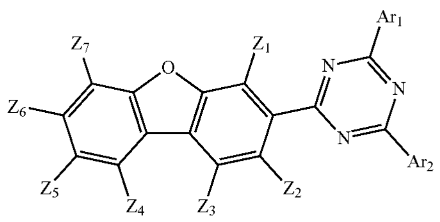

1C-1

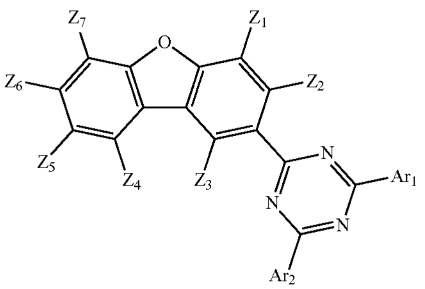

-continued 1D-1

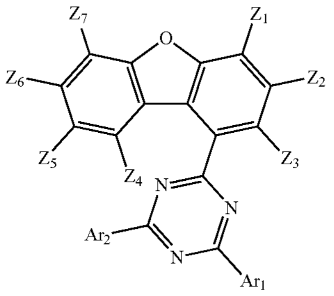

in the Chemical Formulae 1A-1 to 1D-1, one of $Z_1$ to $Z_3$ is a substituent A represented by the Chemical Formula 1-1, and the rest are each independently hydrogen or deuterium, or two adjacent groups of $Z_1$ to $Z_3$ may combine with each other to form a benzene ring unsubstituted or substituted with deuterium, $Z_4$ to $Z_7$ are each independently hydrogen or deuterium, or two adjacent groups of $Z_4$ to $Z_7$ may combine with each other to form a benzene ring unsubstituted or substituted with deuterium, and $Ar_1$ and $Ar_2$ are the same as defined in the Chemical Formula 1.

Specifically, in the Chemical Formula 1A-1, $Z_1$ is A, and $Z_2$ and $Z_3$ are each independently hydrogen or deuterium, or both $Z_2$ and $Z_3$ are bonded to each other to form a benzene ring unsubstituted or substituted with deuterium; or $Z_2$ is A, and $Z_1$ and $Z_3$ are each independently hydrogen or deuterium; or $Z_3$ is A, and $Z_1$ and $Z_2$ are each independently hydrogen or deuterium, or both $Z_1$ and $Z_2$ may combine with each other to form a benzene ring unsubstituted or substituted with deuterium.

In addition, in the Chemical Formula 1B-1, $Z_1$ is A, and $Z_2$ and $Z_3$ are each independently hydrogen or deuterium, or both $Z_2$ and $Z_3$ combine with each other to form a benzene ring unsubstituted or substituted with deuterium; or $Z_2$ is A, and $Z_1$ and $Z_3$ are each independently hydrogen or deuterium; or $Z_3$ is A, and $Z_1$ and $Z_2$ are each independently hydrogen or deuterium.

In addition, in the Chemical Formula 1C-1, $Z_1$ is A, and $Z_2$ and $Z_3$ are each independently hydrogen or deuterium; or $Z_2$ is A, and $Z_1$ and $Z_3$ are each independently hydrogen or deuterium; or $Z_3$ is A, and $Z_1$ and $Z_2$ are each independently hydrogen or deuterium, or both $Z_1$ and $Z_2$ may combine with each other to form a benzene ring unsubstituted or substituted with deuterium.

Specifically, in the Chemical Formula 1D-1, $Z_1$ is A, and $Z_2$ and $Z_3$ are each independently hydrogen or deuterium, or both $Z_2$ and $Z_3$ may combine with each other to form a benzene ring unsubstituted or substituted with deuterium;

$Z_2$ is A, and $Z_1$ and $Z_3$ are each independently hydrogen or deuterium; or $Z_3$ is A, and $Z_1$ and $Z_2$ are each independently hydrogen or deuterium, or both $Z_1$ and $Z_2$ may combine with each other to form a benzene ring unsubstituted or substituted with deuterium.

Alternatively, the first compound may be represented by any one of the following Chemical Formulae 3-1 to 3-7:

3-1

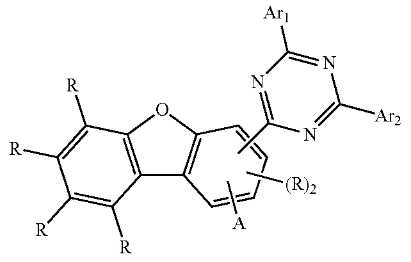

3-2

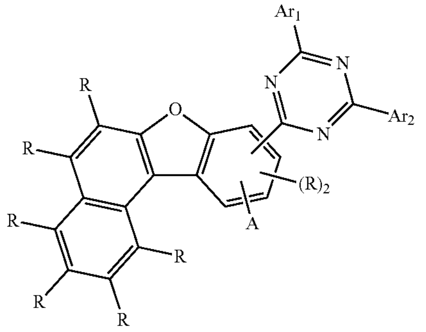

3-3

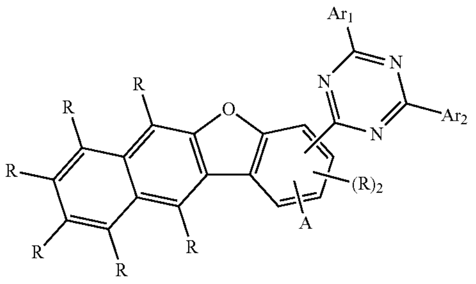

3-4

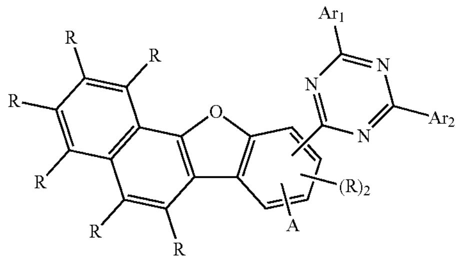

3-5

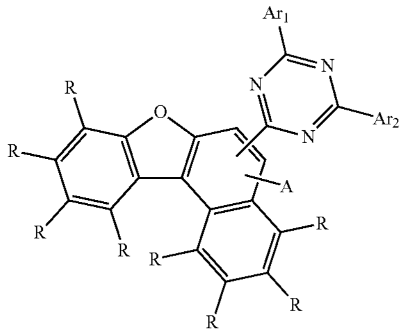

-continued 3-6

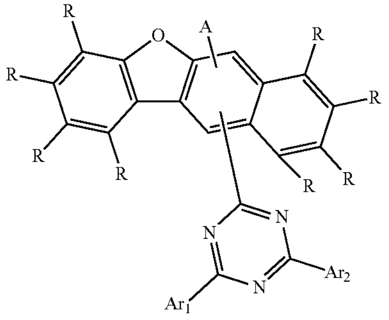

3-7

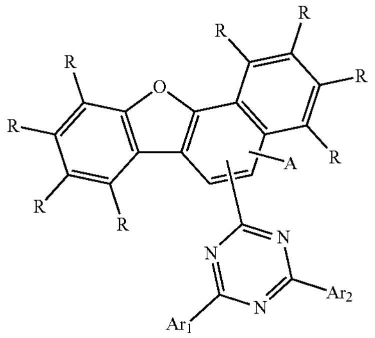

in the Chemical Formulae 3-1 to 3-7, each R is independently hydrogen or deuterium, and A, $Ar_1$ and $Ar_2$ are the same as defined in the Chemical Formula 1.

Preferably, $Ar_1$ and $Ar_2$ are each independently a $C_{6-20}$ aryl unsubstituted or substituted with deuterium or $C_{6-20}$ aryl.

More preferably, $Ar_1$ and $Ar_2$ are each independently phenyl, biphenylyl, terphenylyl, naphthyl, phenanthrenyl, dibenzothiophenyl, dibenzofuranyl, or carbazolyl, where $Ar_1$ and $Ar_2$ may be unsubstituted or substituted with 1 to 5 substituents each independently selected from the group consisting of deuterium and $C_{6-20}$ aryl.

Most preferably, $Ar_1$ and $Ar_2$ are each independently any one selected from the group consisting of the following:

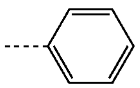
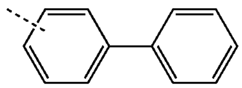
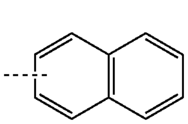
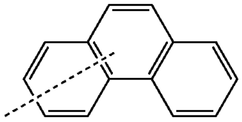
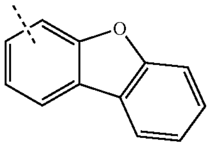
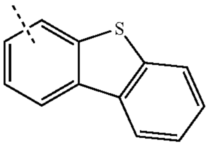

-continued

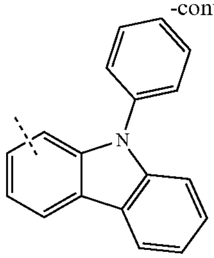
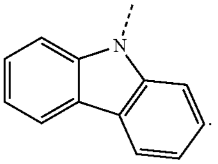

In this case, $Ar_1$ and $Ar_2$ may be the same as or different from each other.

Further, in A which is a substituent represented by the Chemical Formula 1-1, $R_1$ to $R_4$ are each independently hydrogen or deuterium, or two adjacent groups of $R_1$ to $R_4$ may combine with each other to form a benzene ring unsubstituted or substituted with deuterium.

At this time, m, which is the number of deuterium (D), is 0, 1, 2, 3, 4, 5, orb.

For example, A is any one of the substituents represented by the following Chemical Formulae a1 to a4:

a1

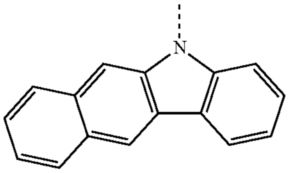

a2

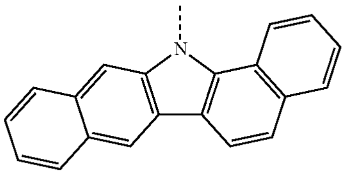

a3

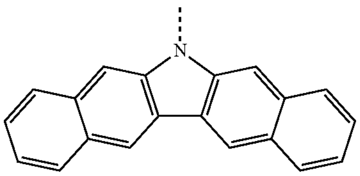

a4

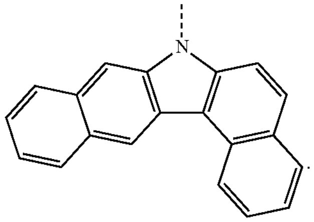

Specific examples of the first compound are as follows:
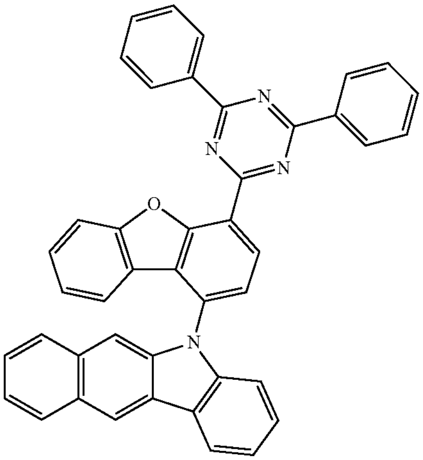
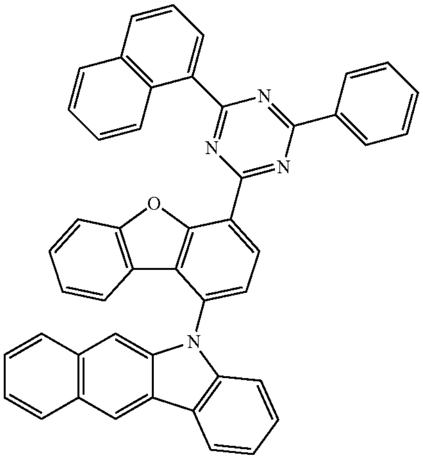
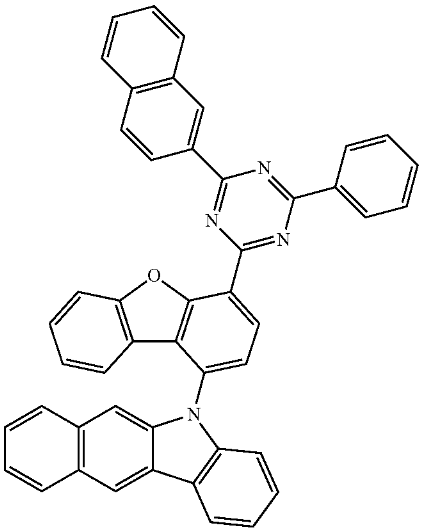
-continued
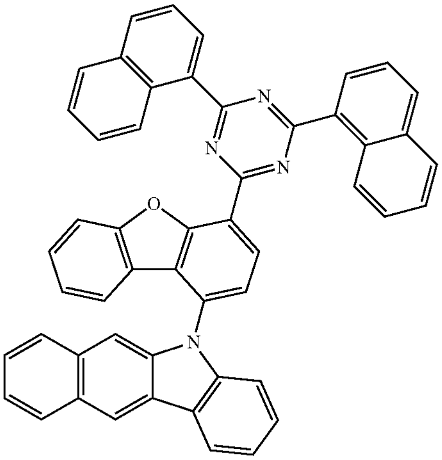
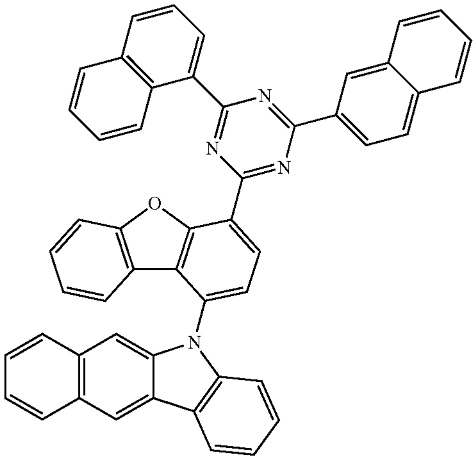
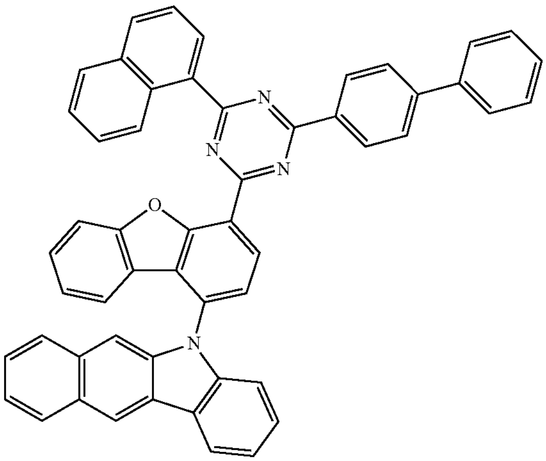

-continued
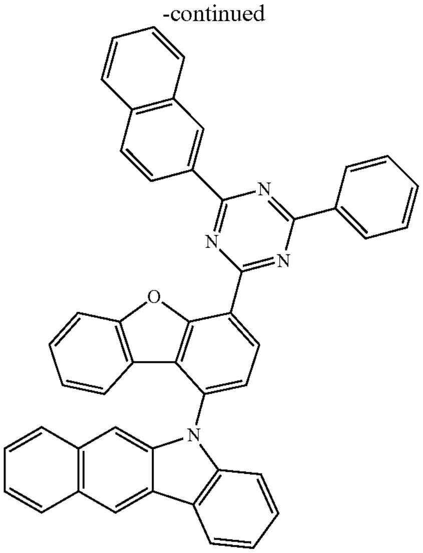
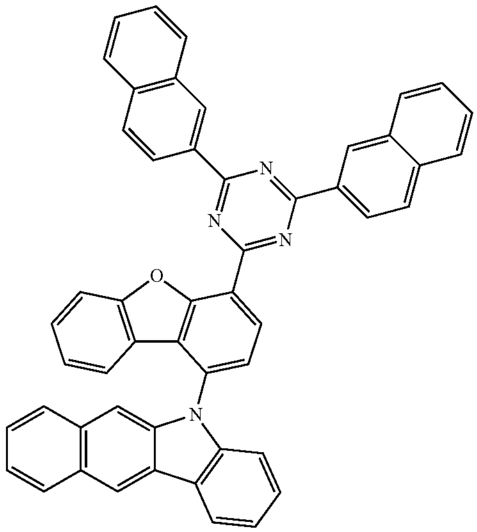
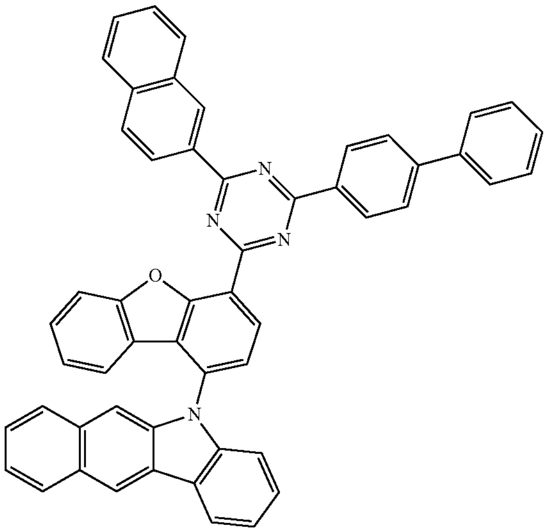
-continued
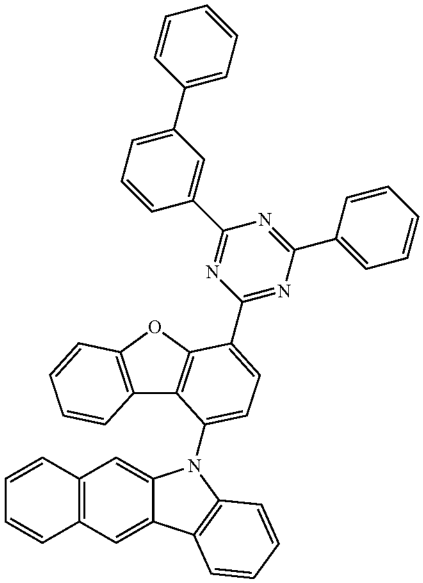
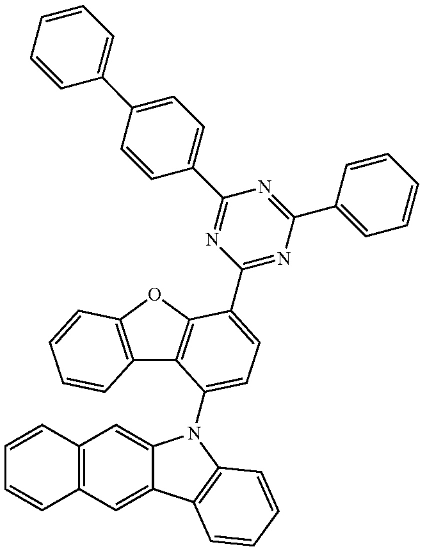
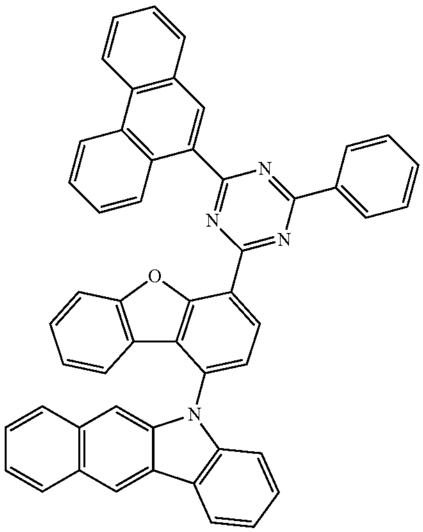

-continued
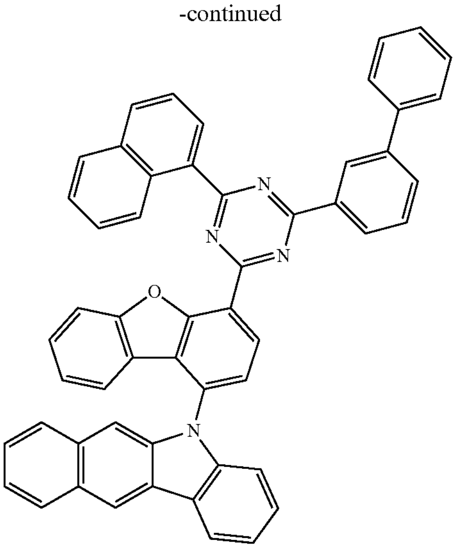
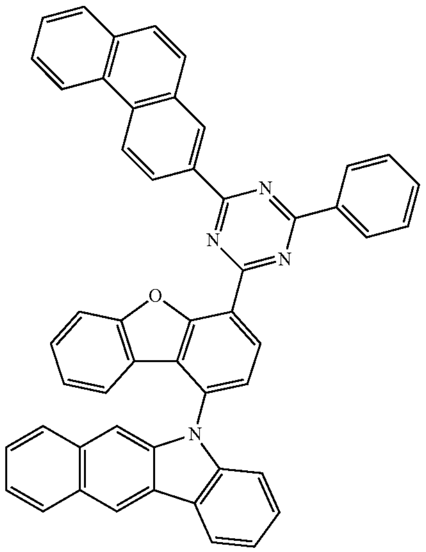
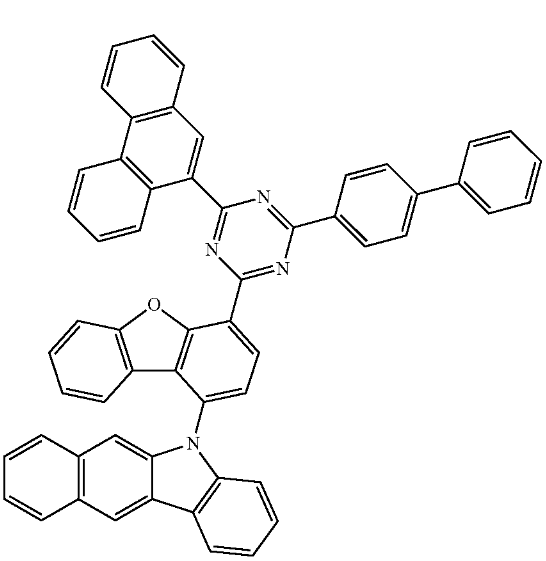
-continued
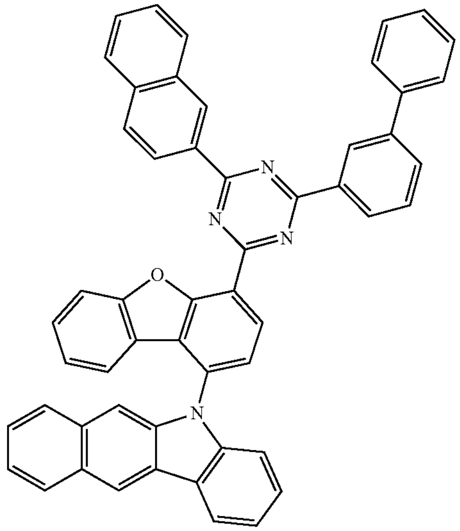
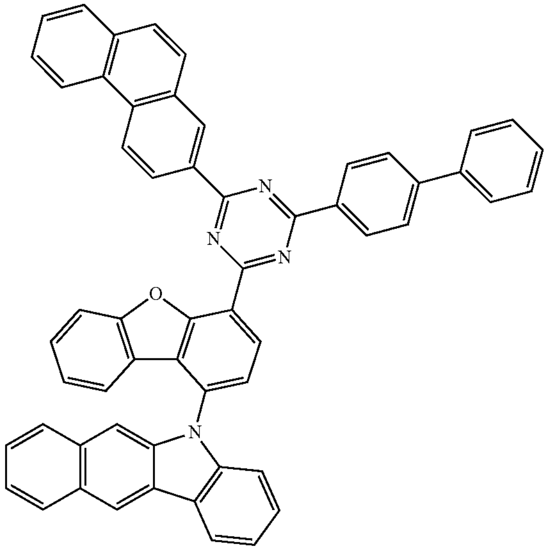
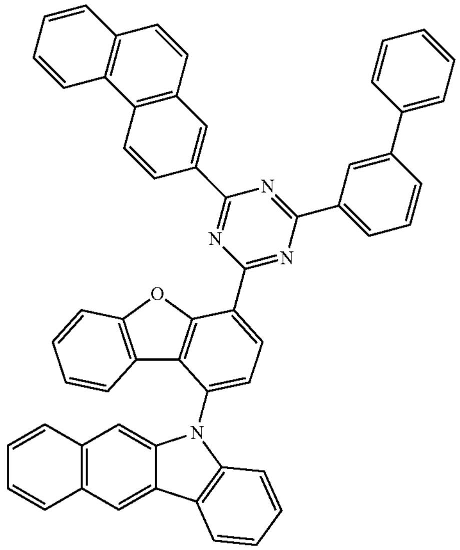

-continued
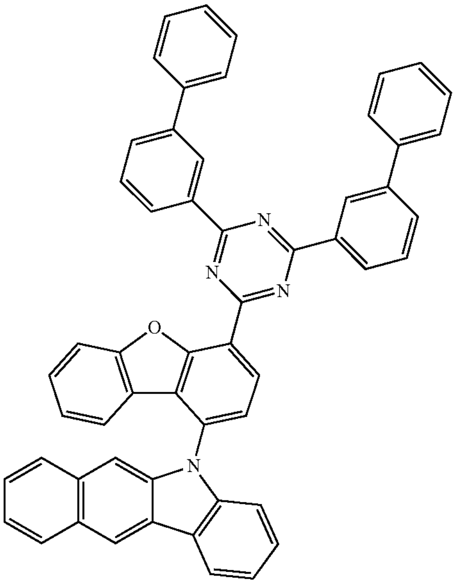
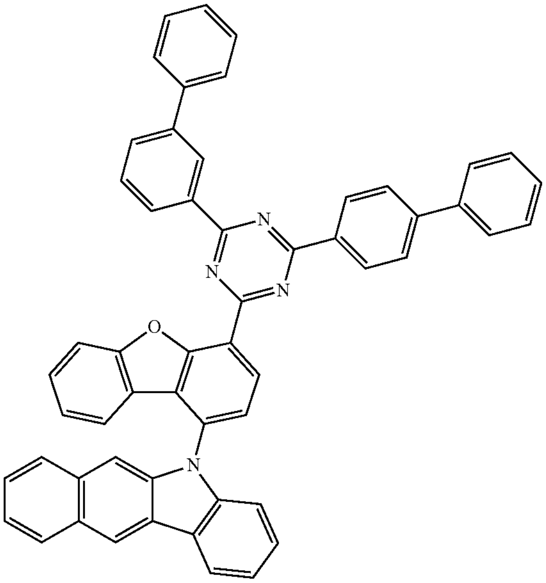
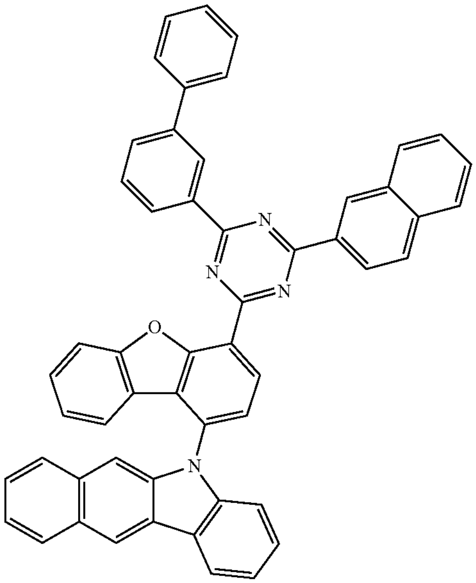
-continued
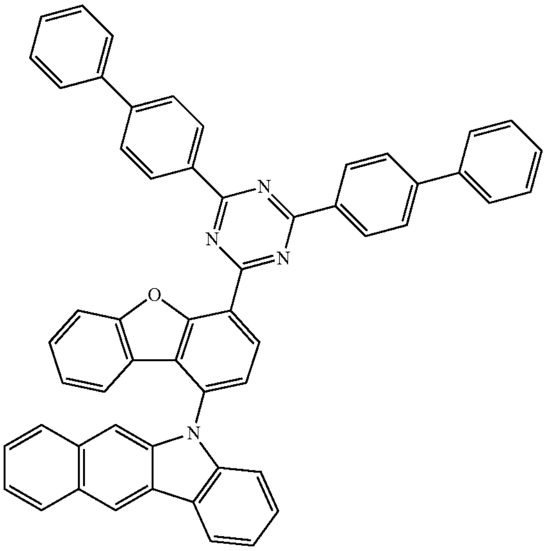
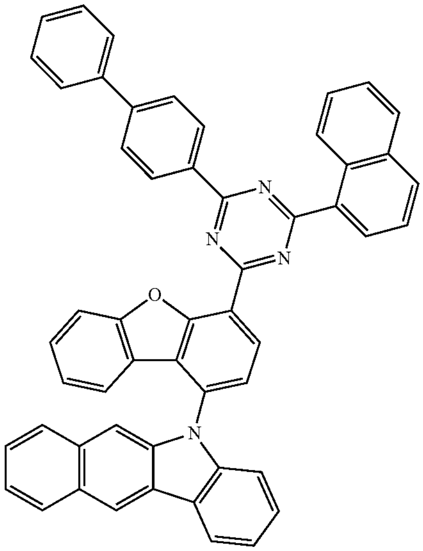

-continued
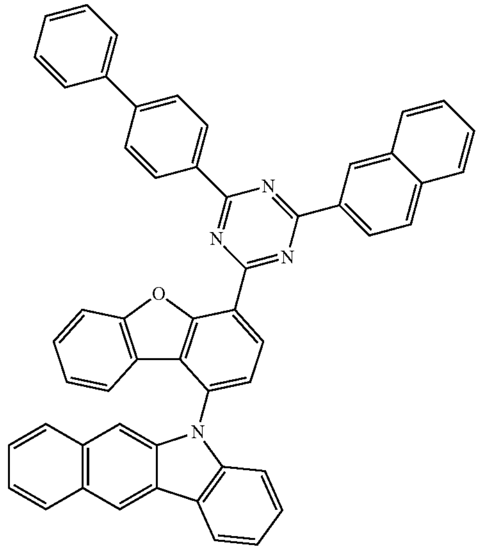
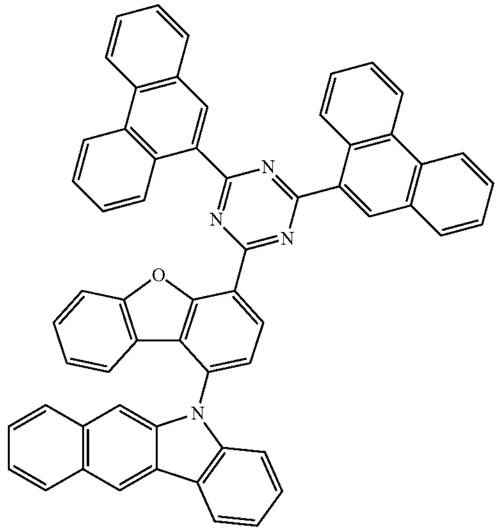
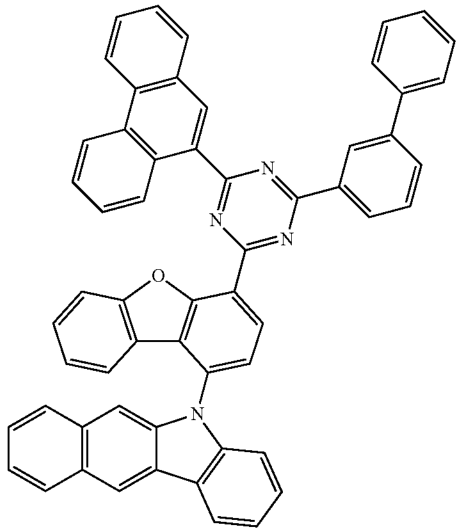
-continued
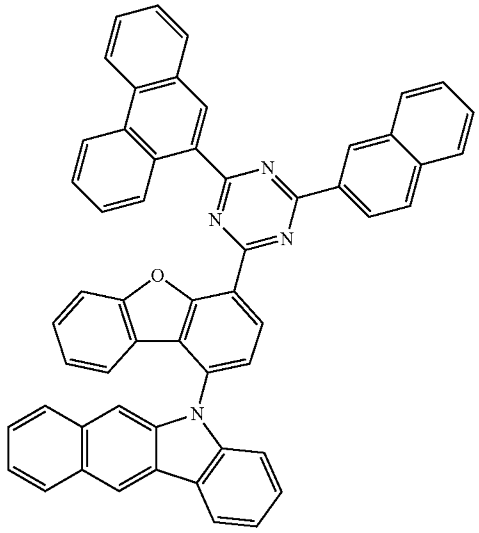
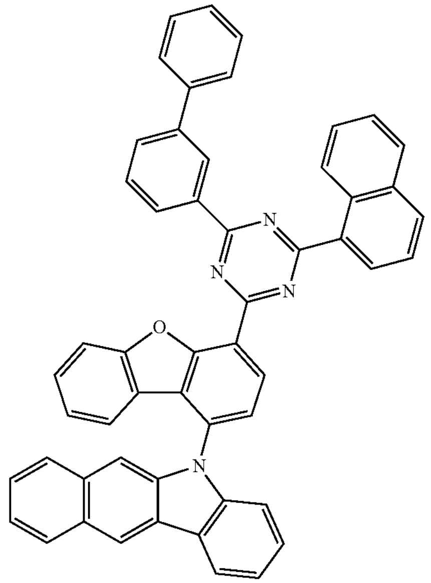
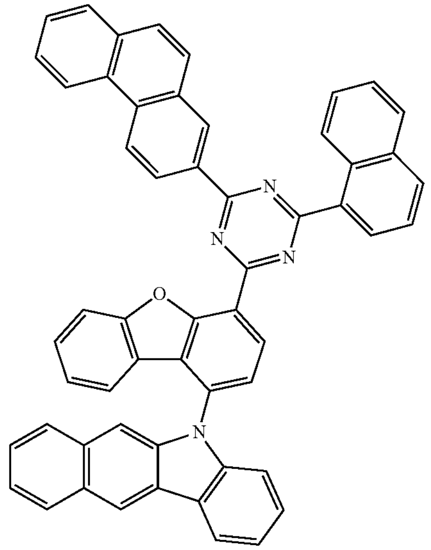

-continued
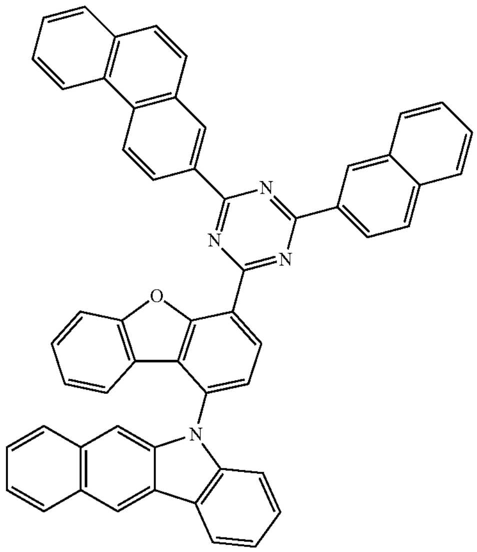
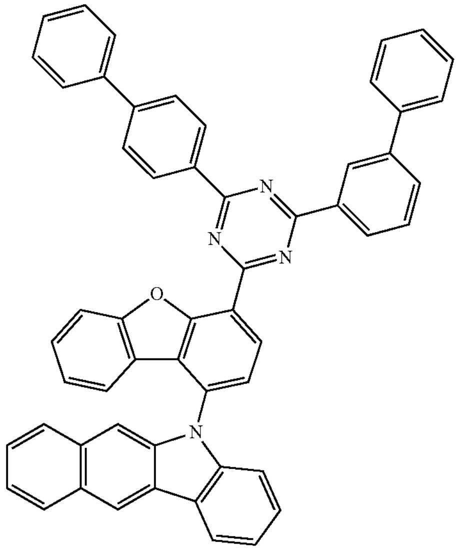
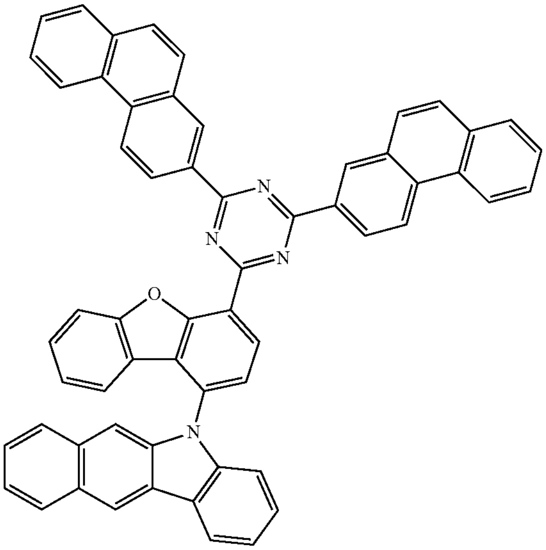
-continued
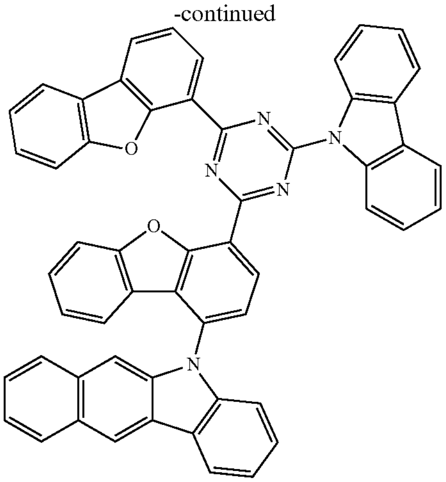
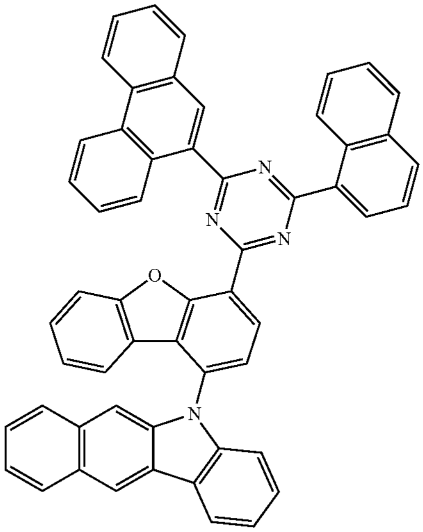
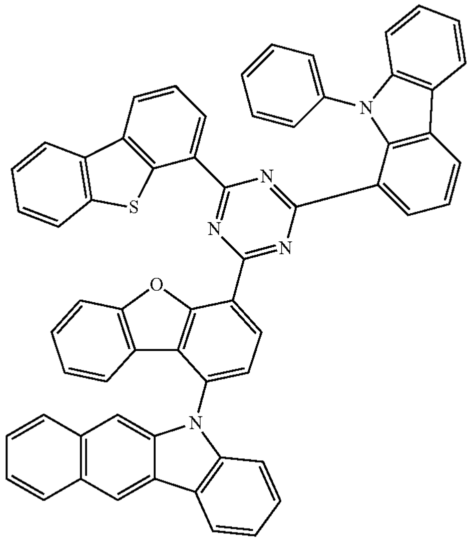

-continued
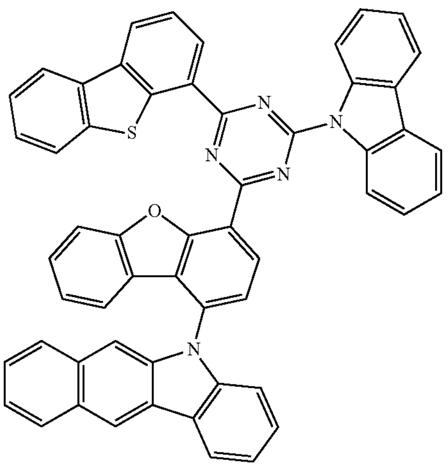
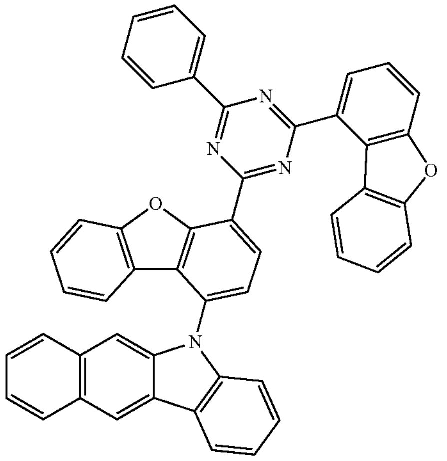
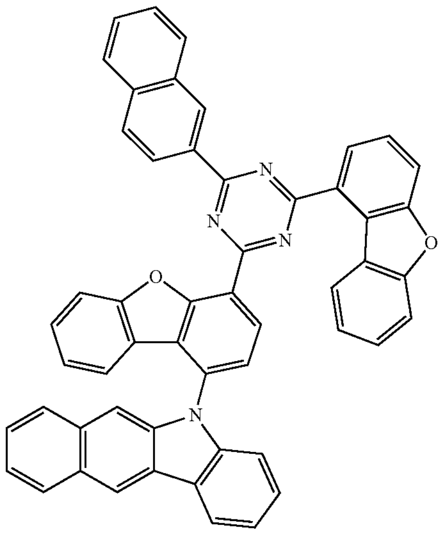
-continued
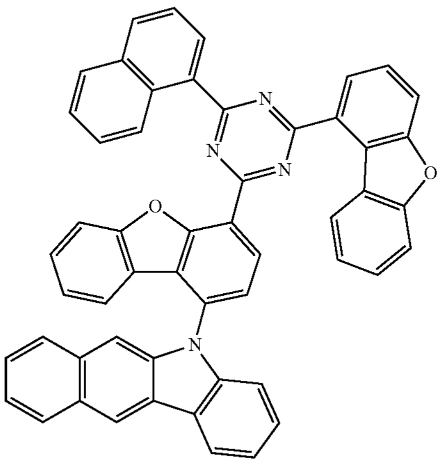
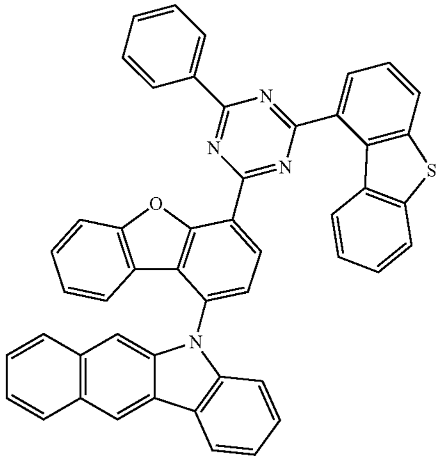
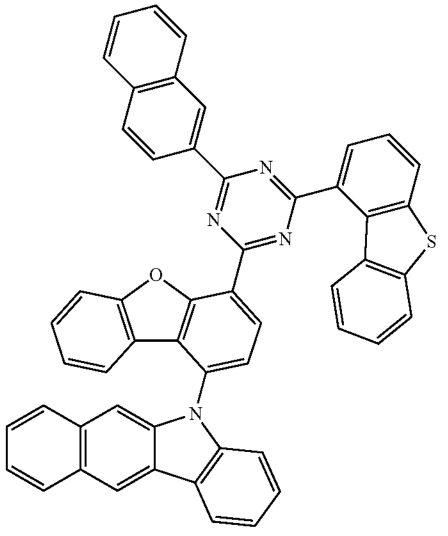

-continued
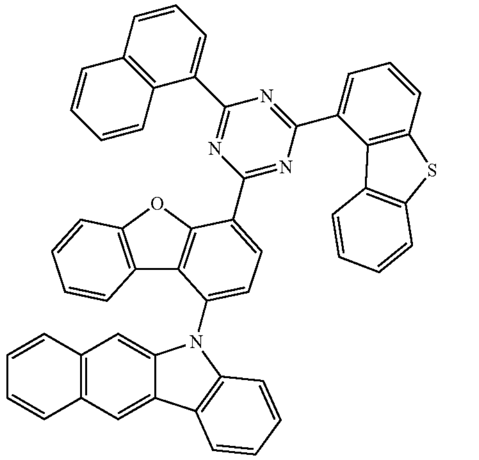
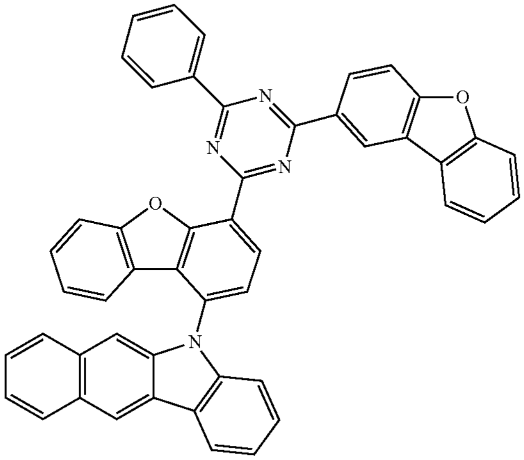
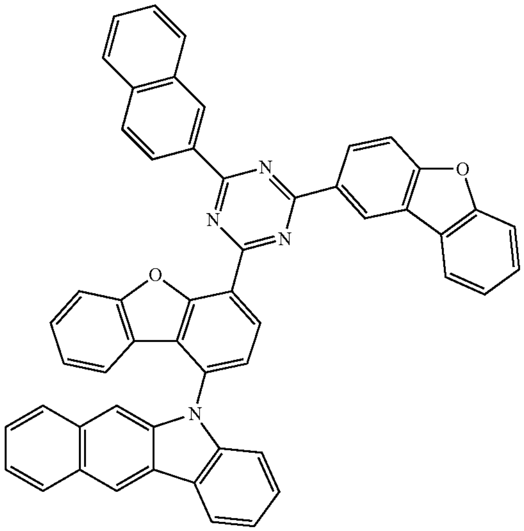
-continued
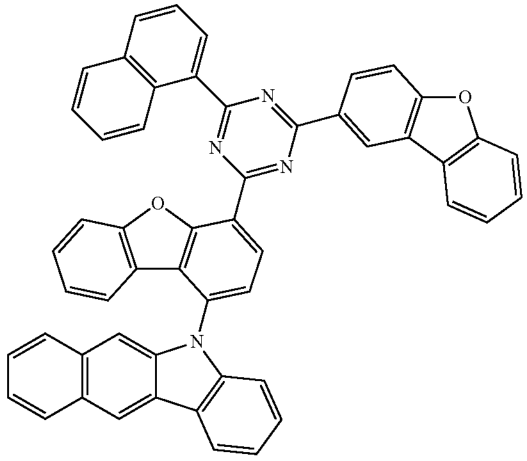
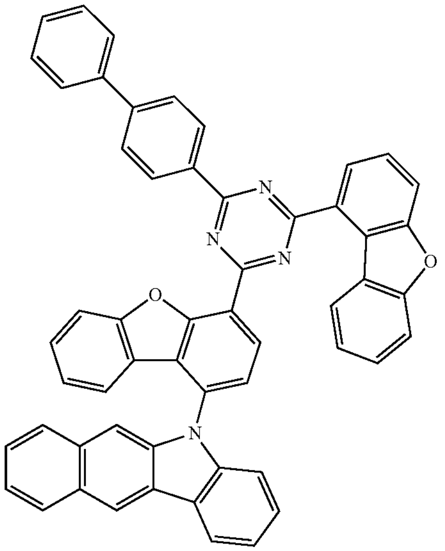
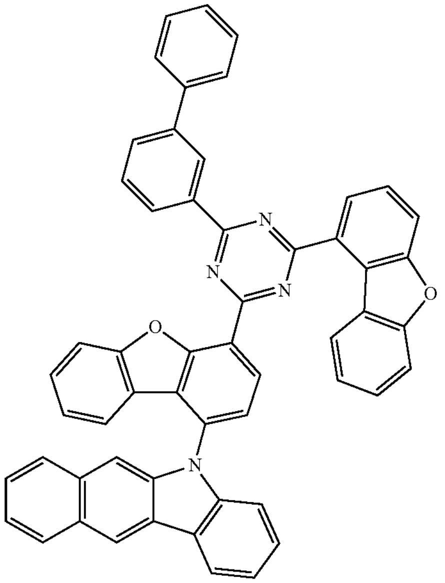

-continued
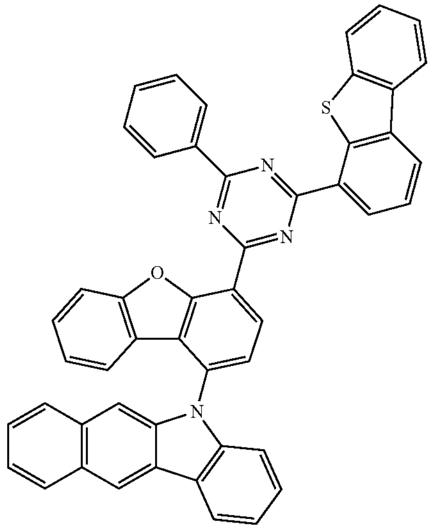
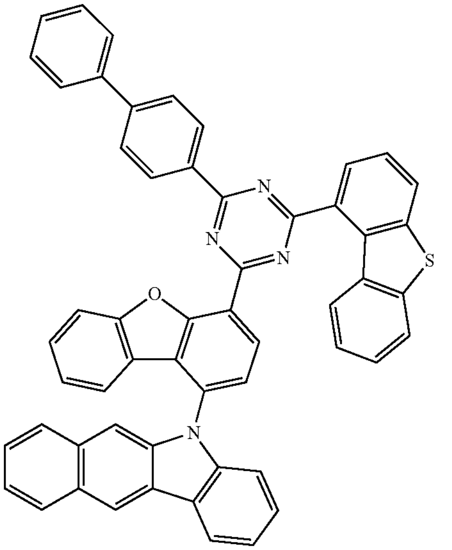
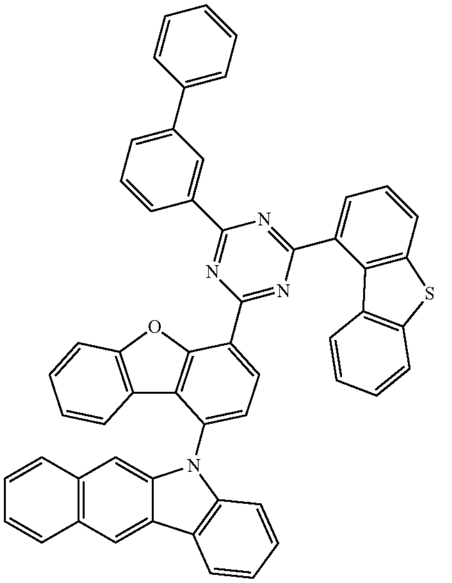
-continued
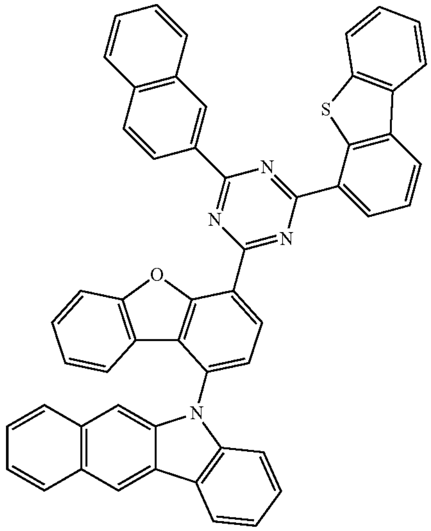
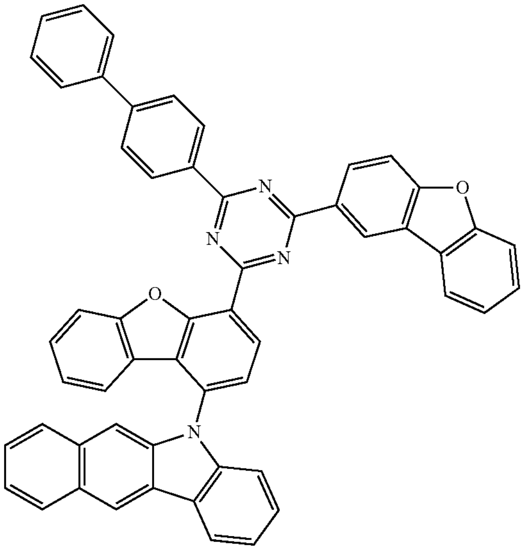
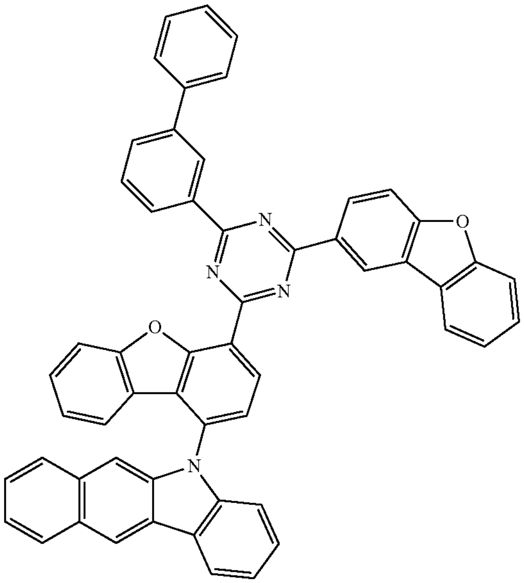

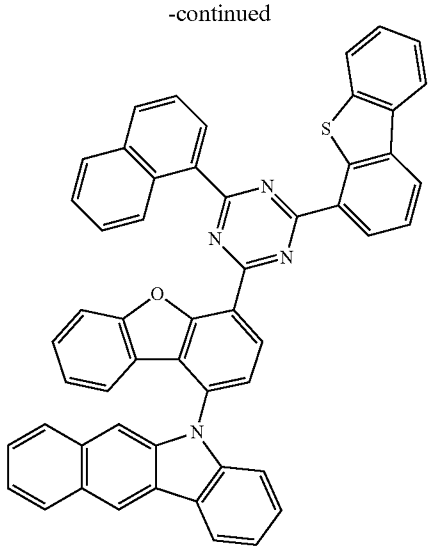
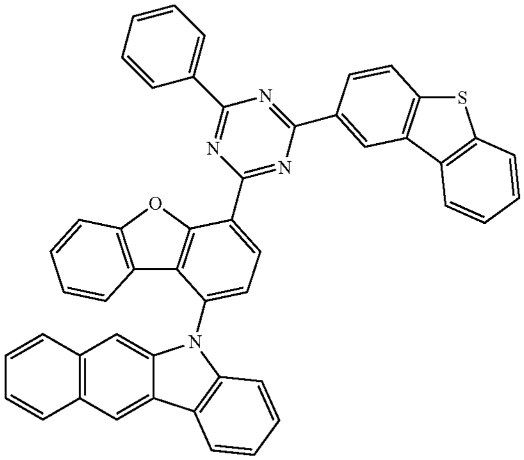
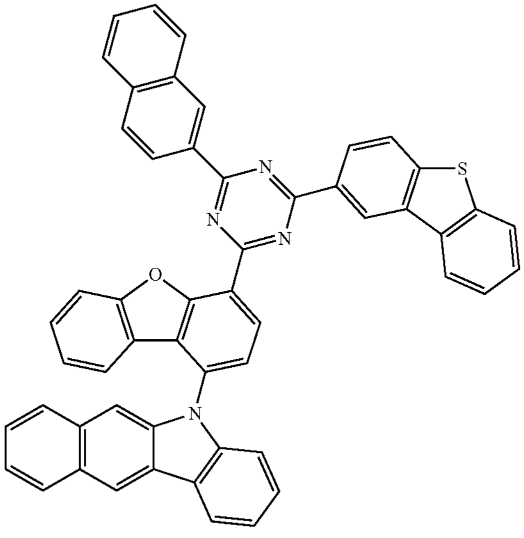
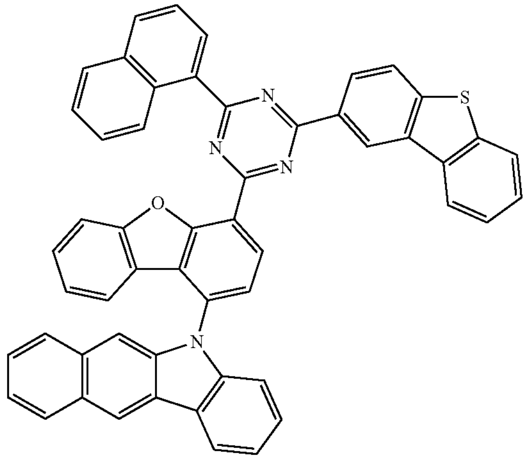
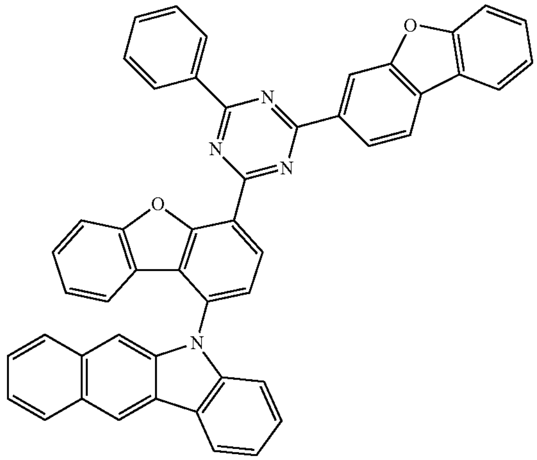
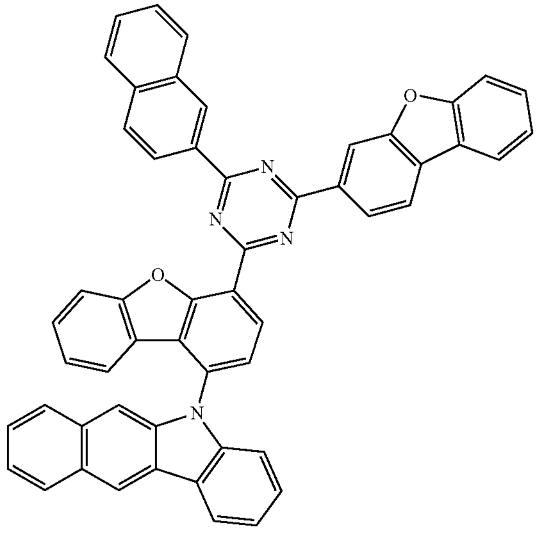

-continued
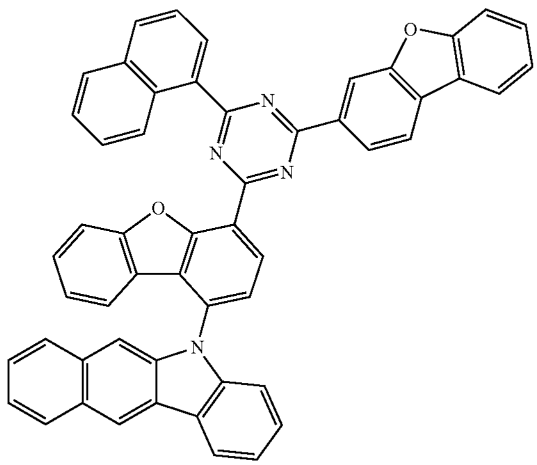
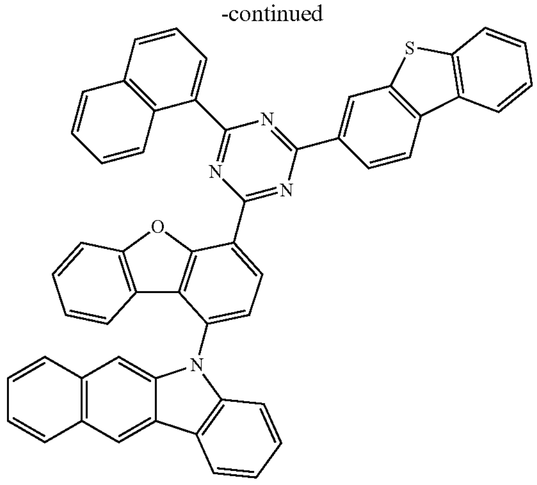
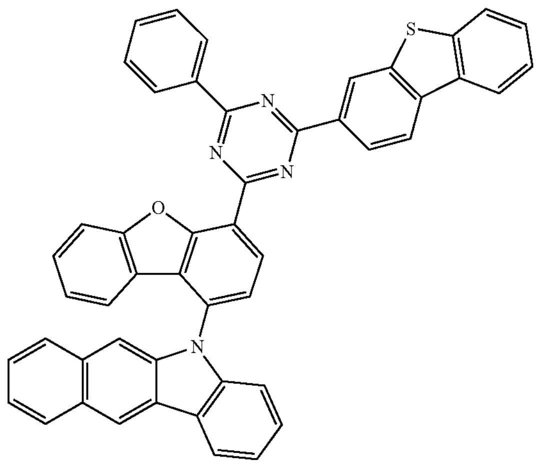
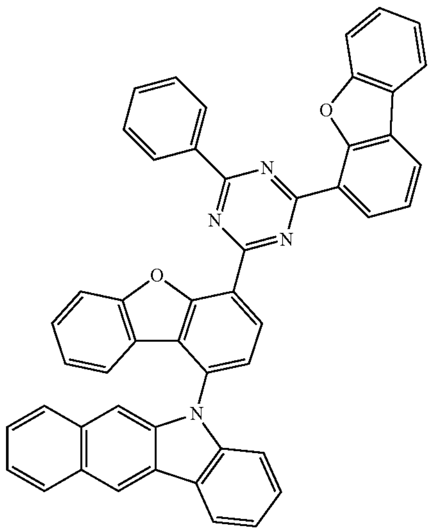
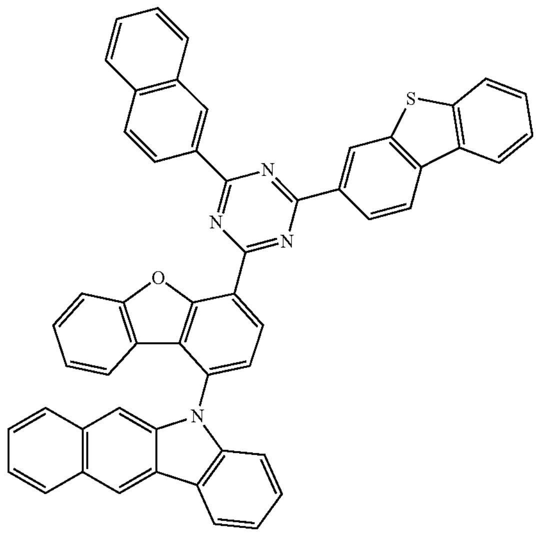
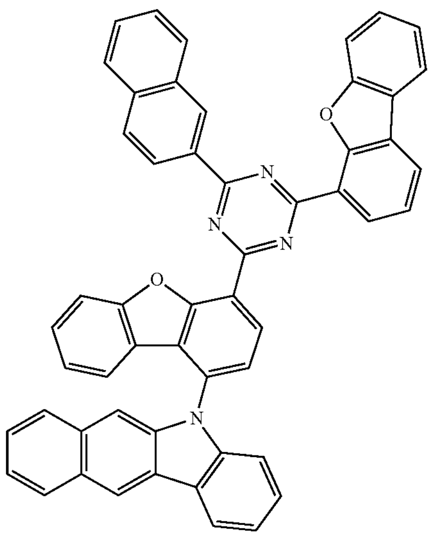
-continued -continued
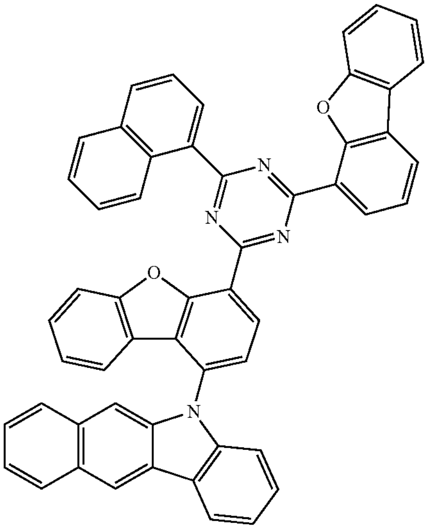
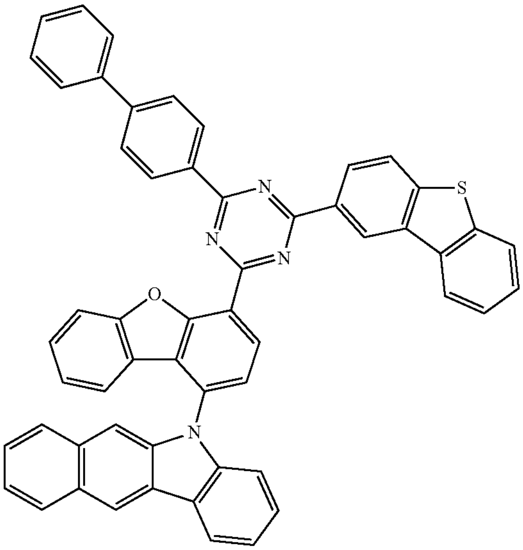
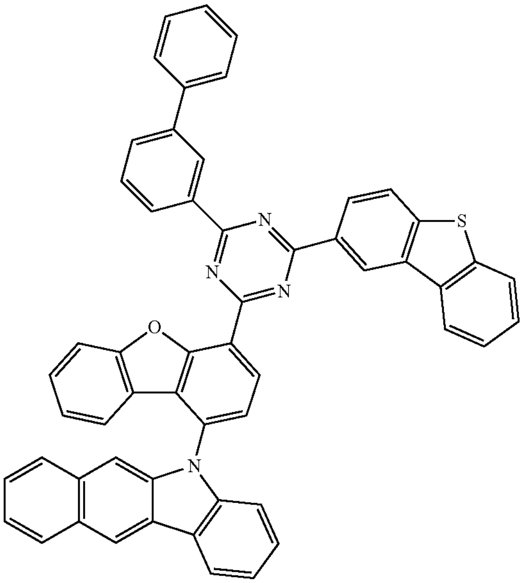
-continued
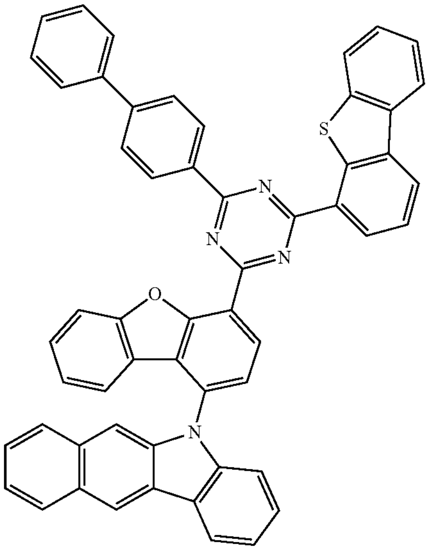
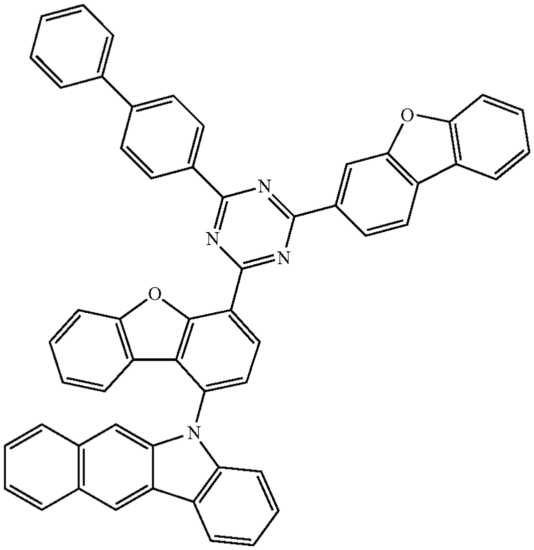
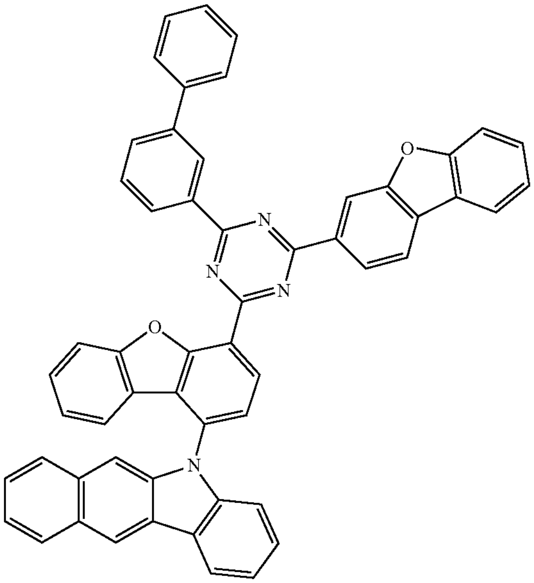

-continued
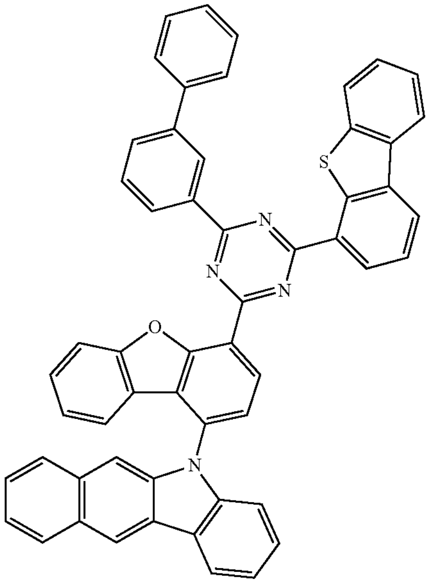
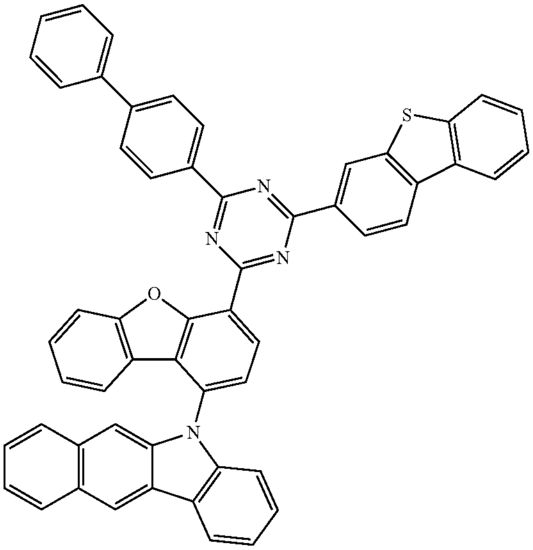
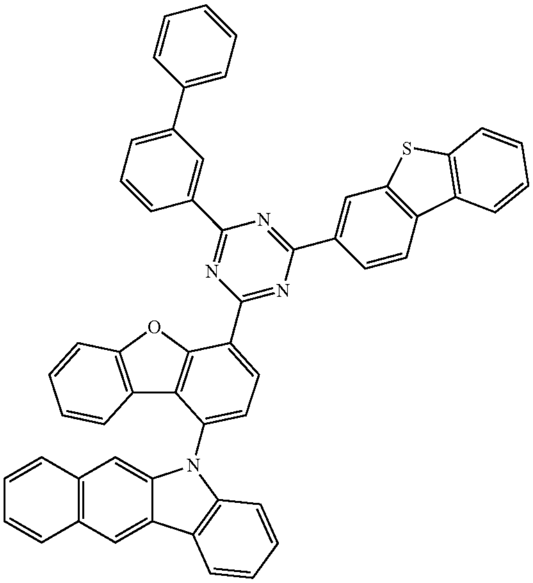
-continued
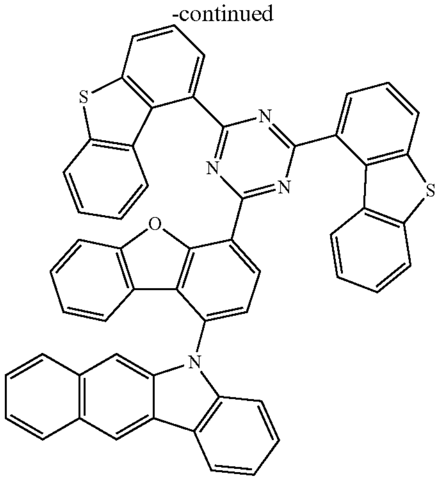
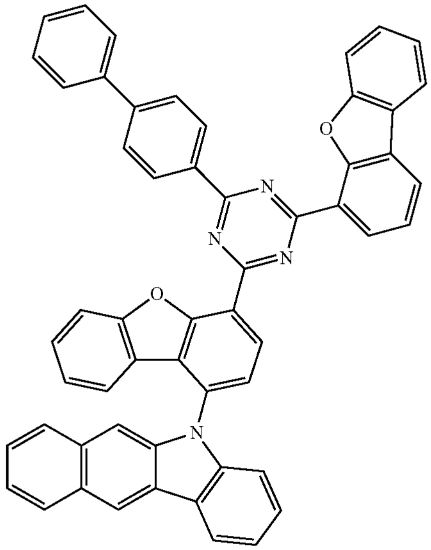
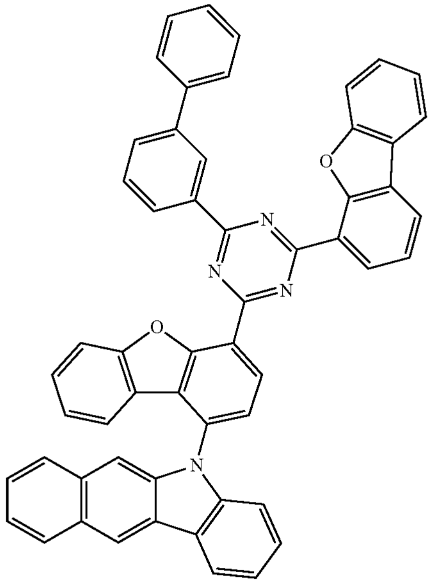

-continued
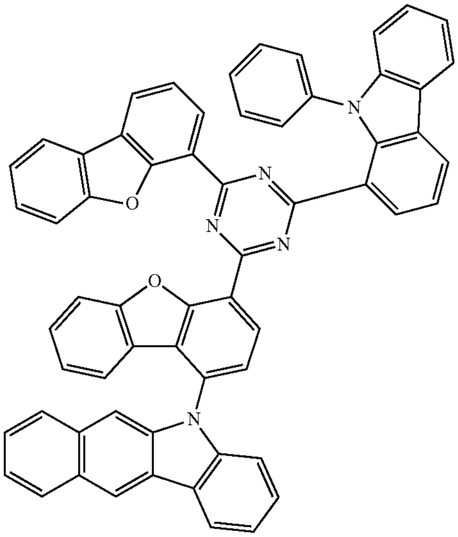
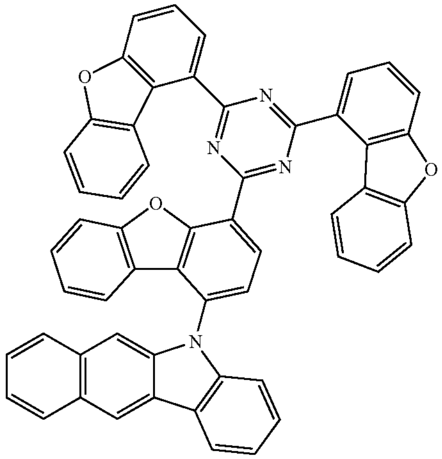
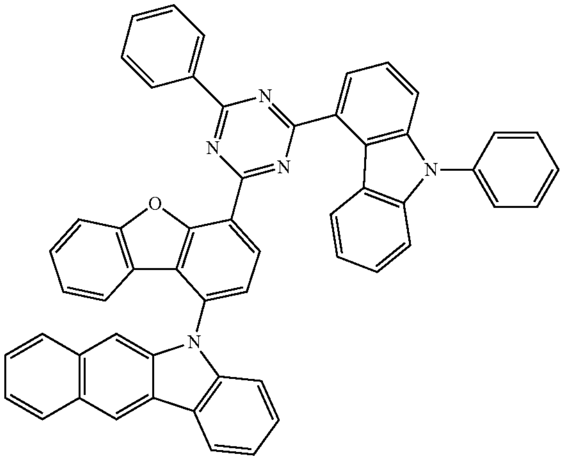
-continued
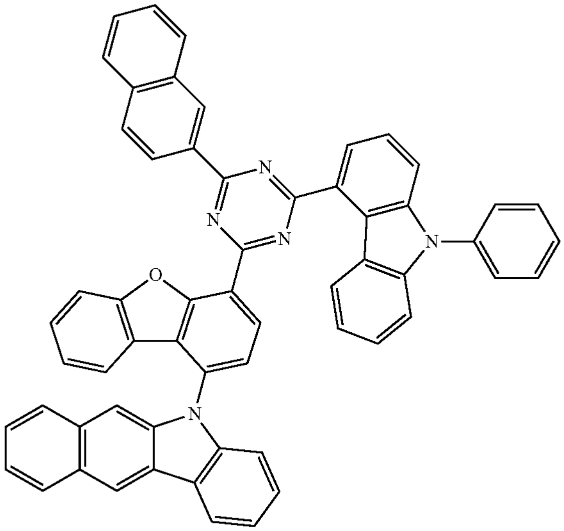
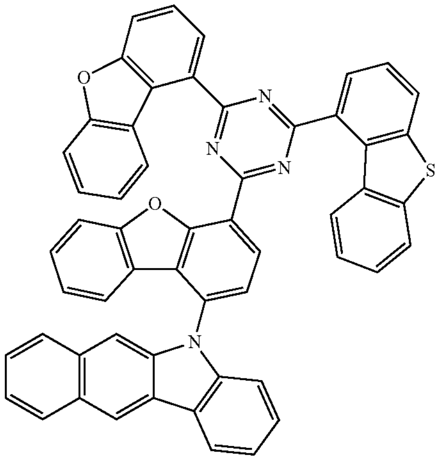
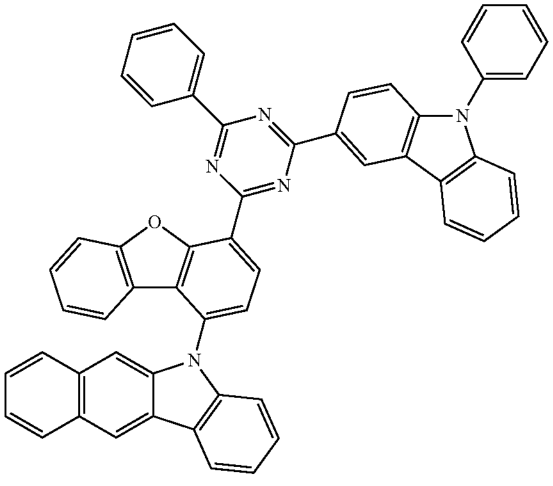

-continued
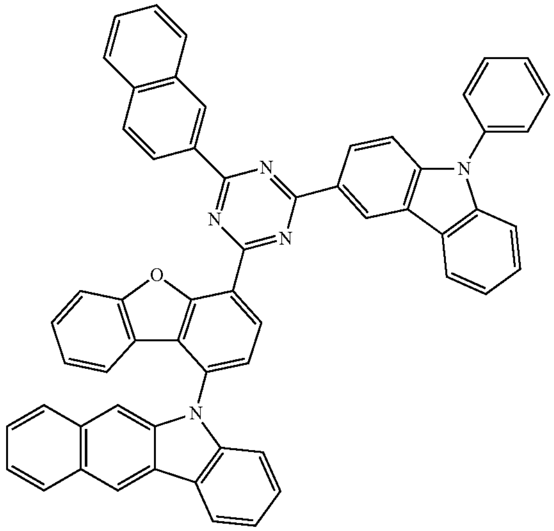
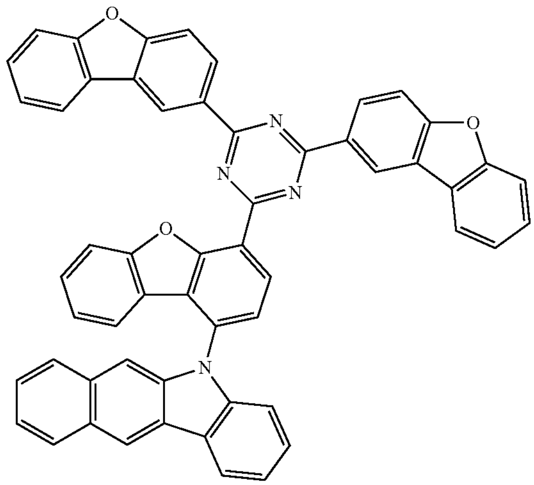
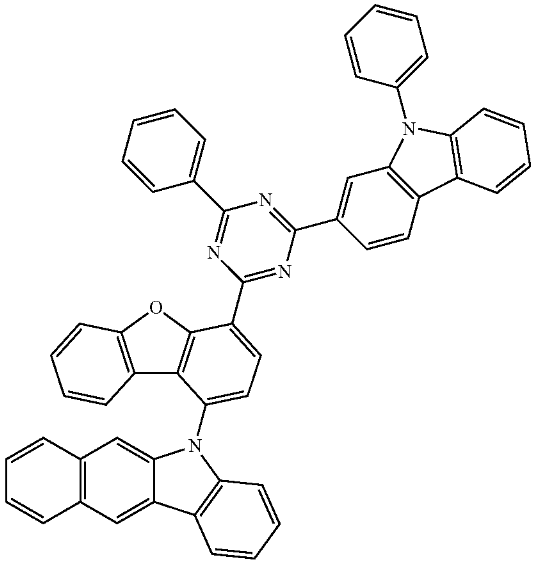
-continued
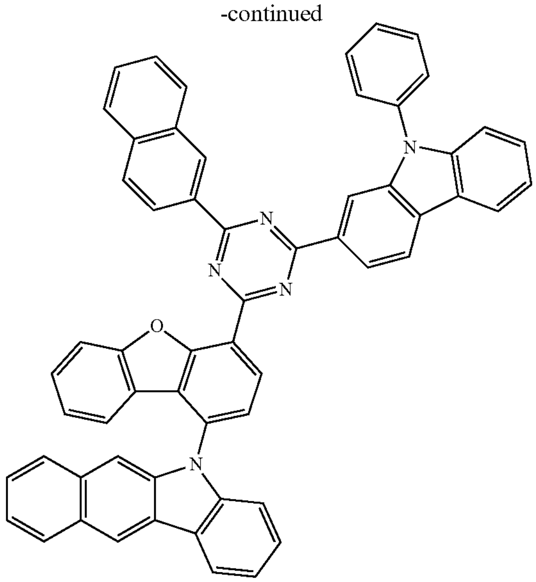
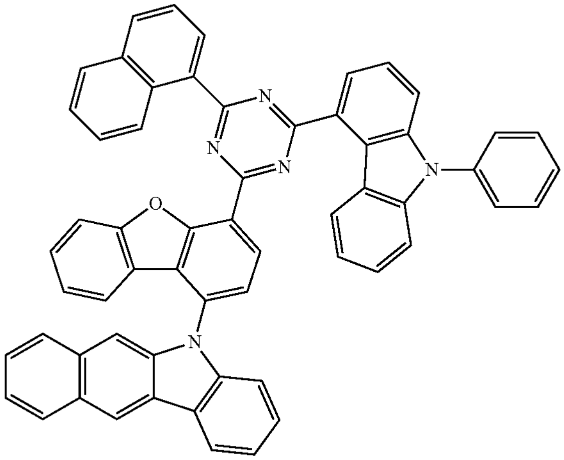
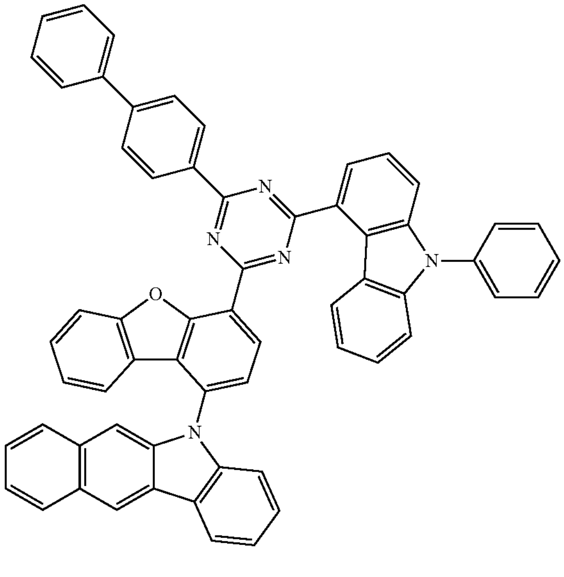

-continued
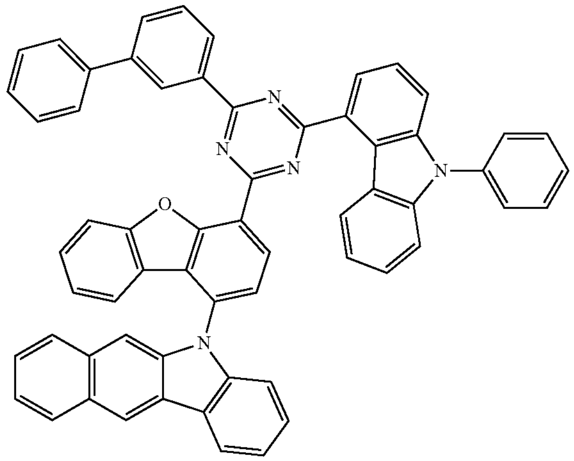
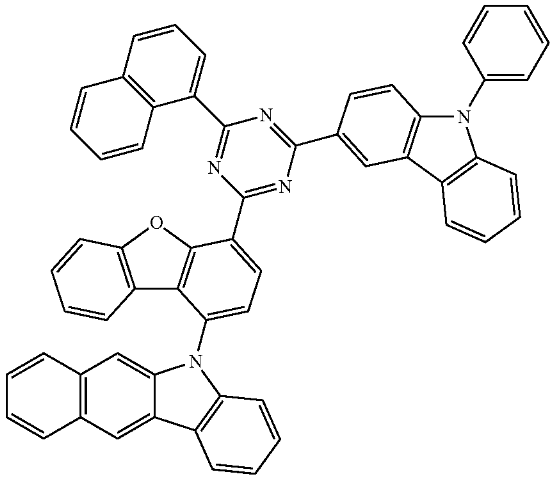
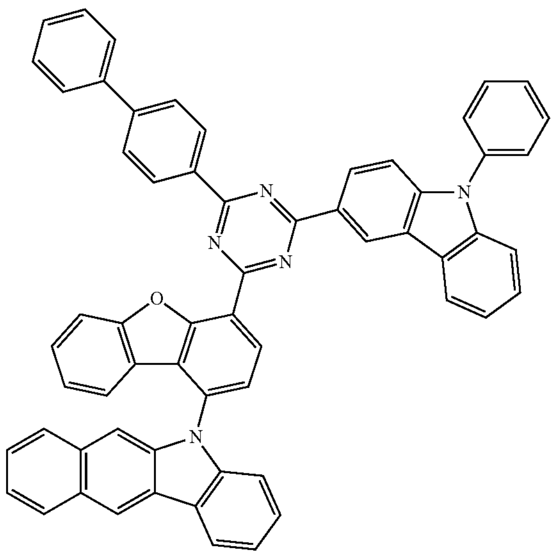
-continued
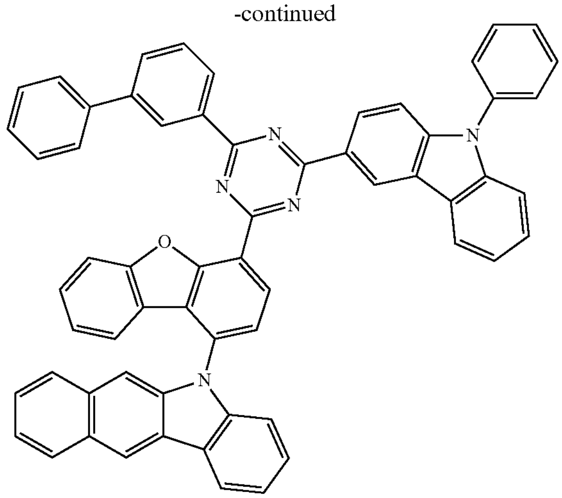
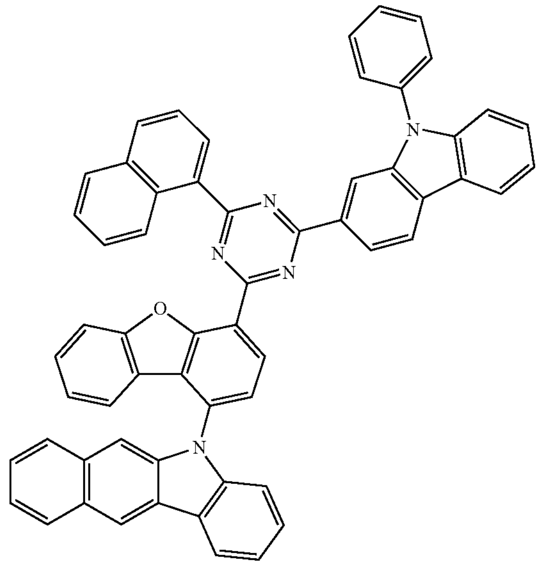
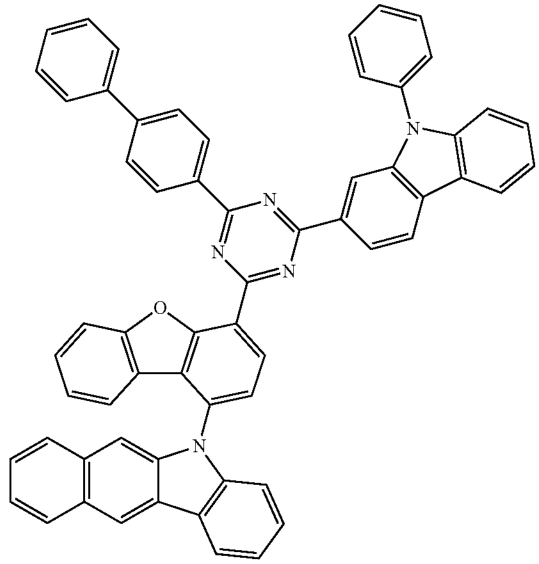

-continued
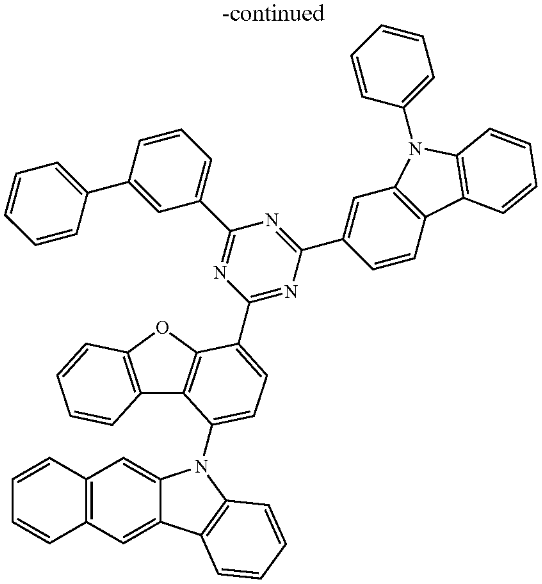
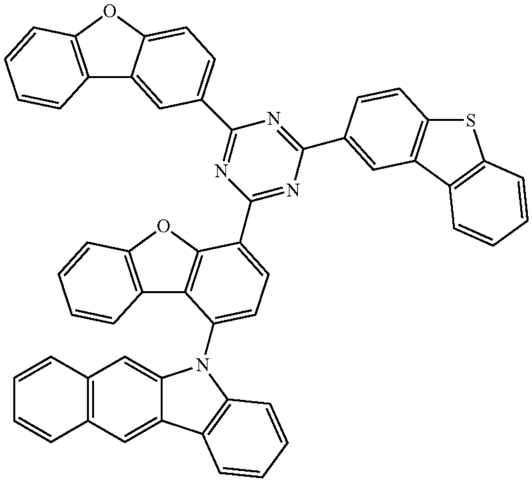
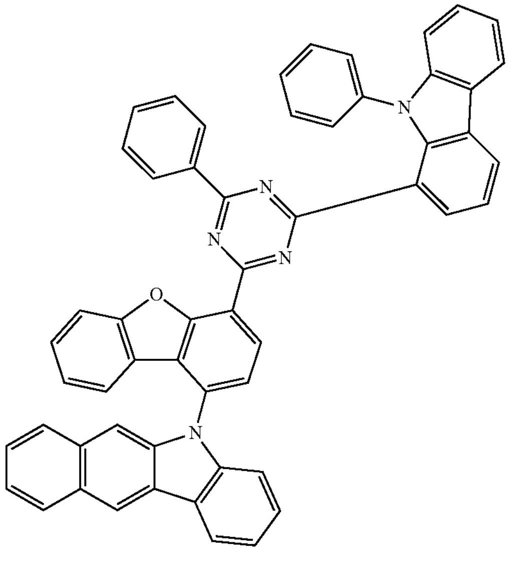
-continued
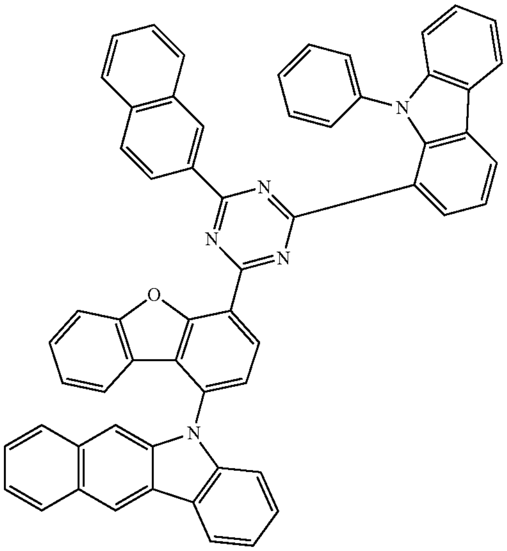
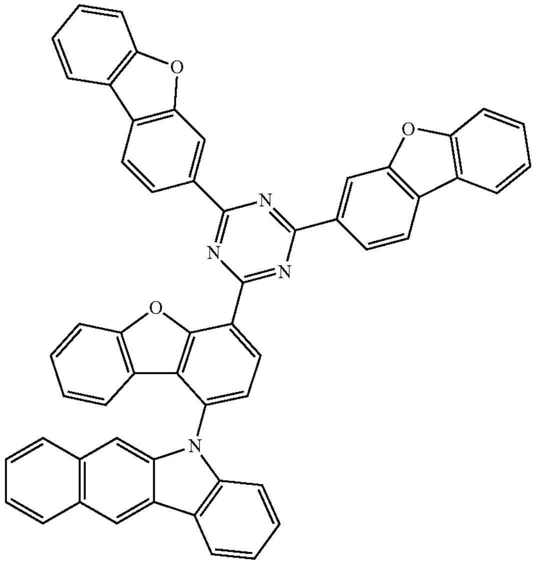
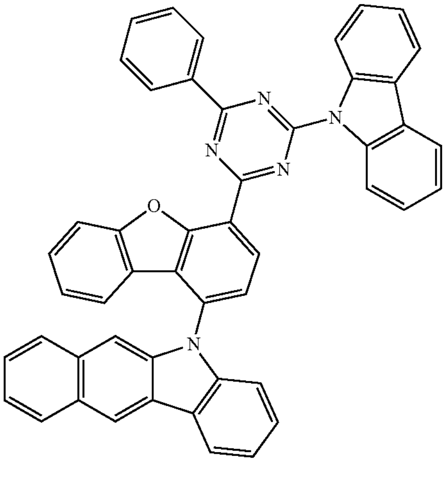

-continued
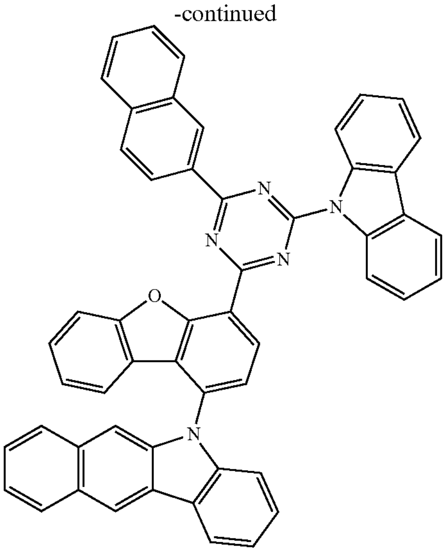
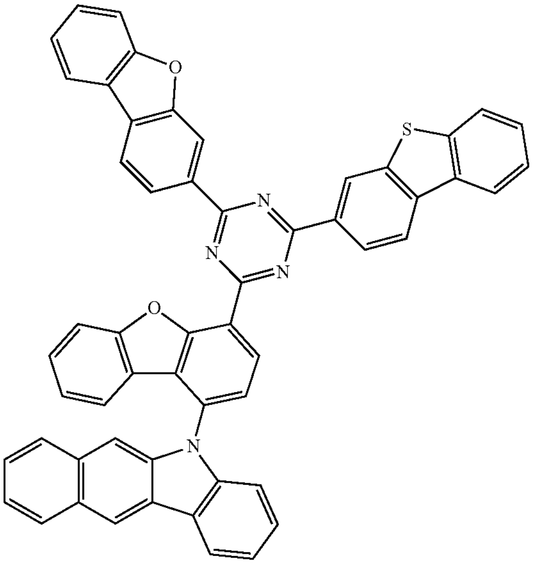
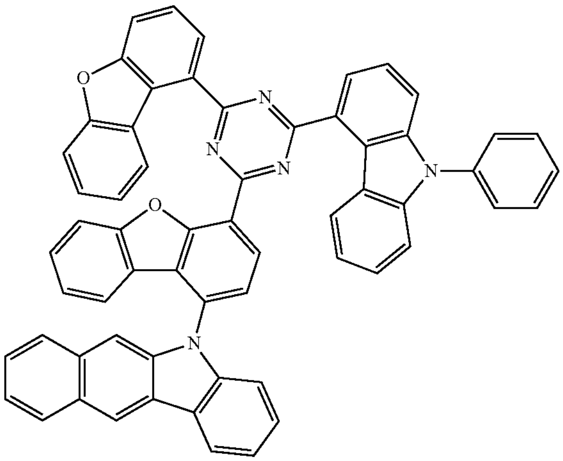
-continued
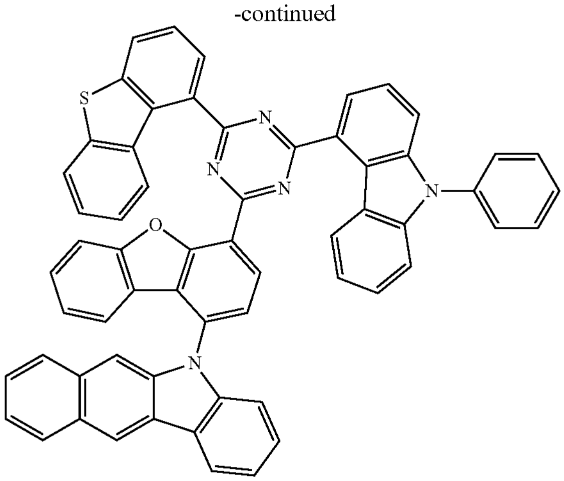
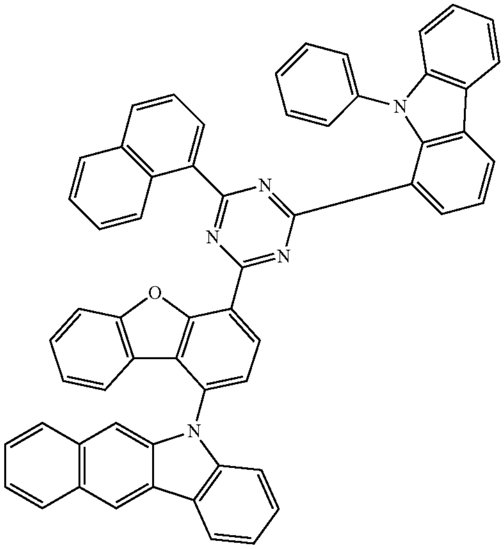
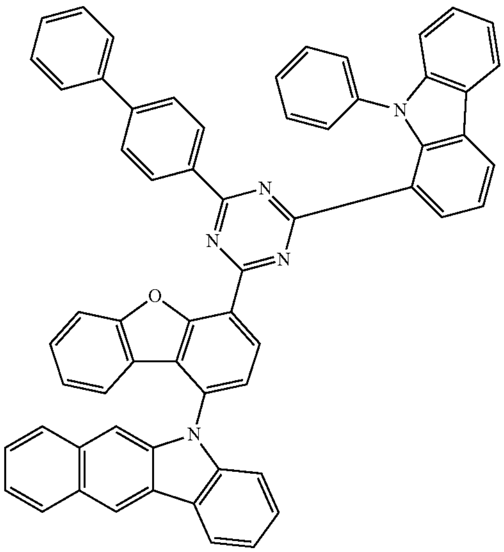

-continued
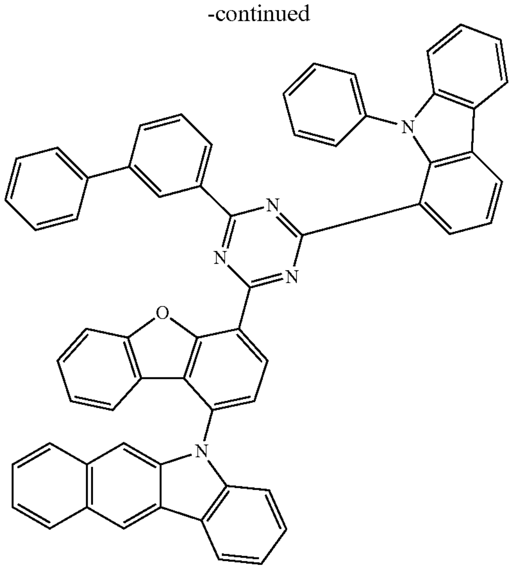
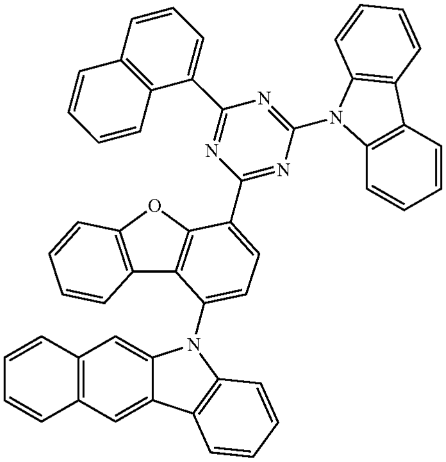
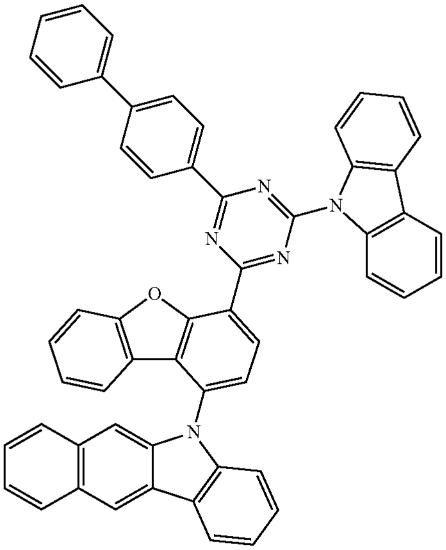
-continued
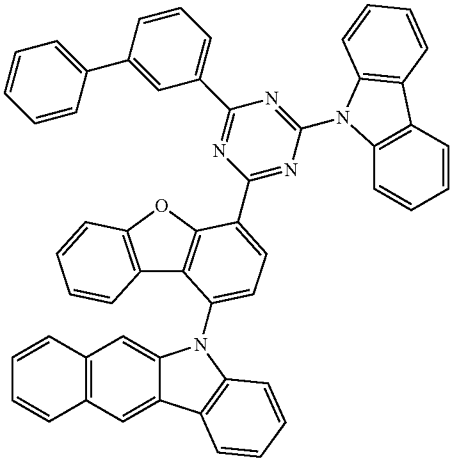
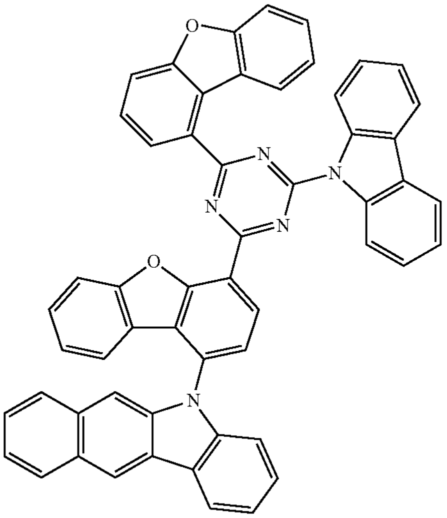
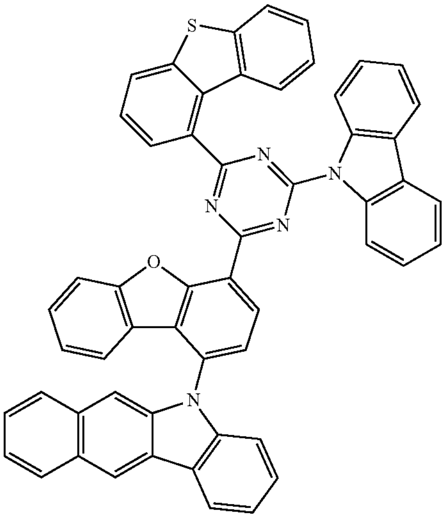

-continued
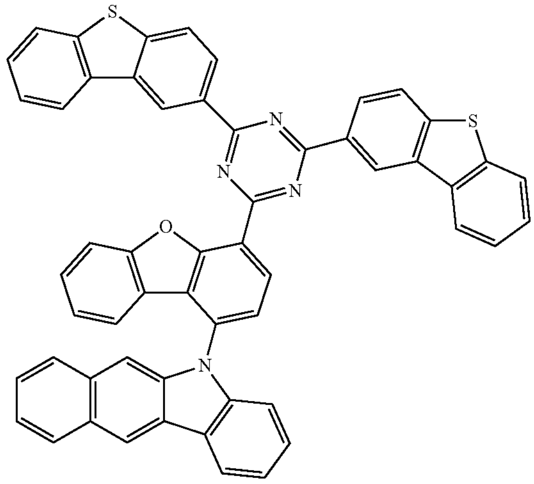
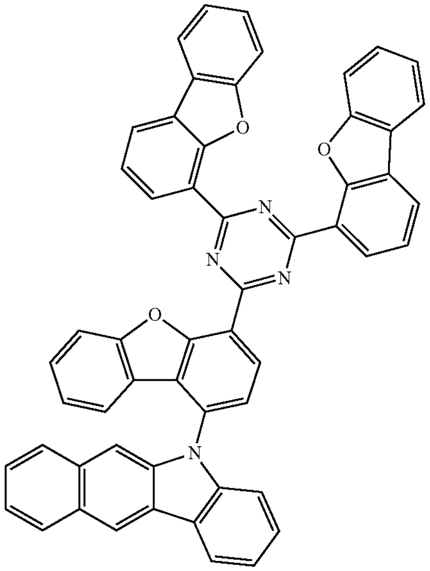
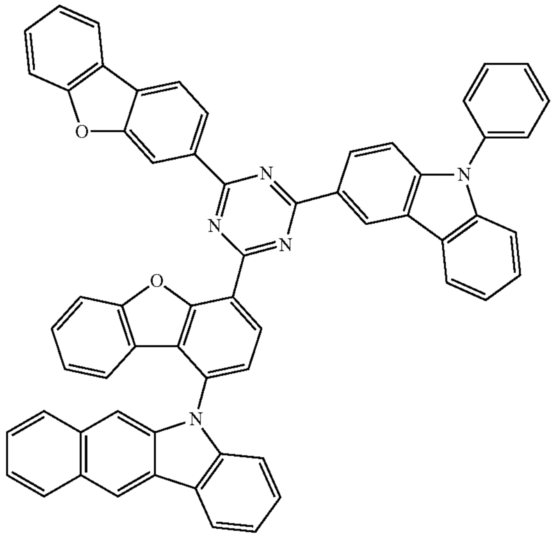
-continued
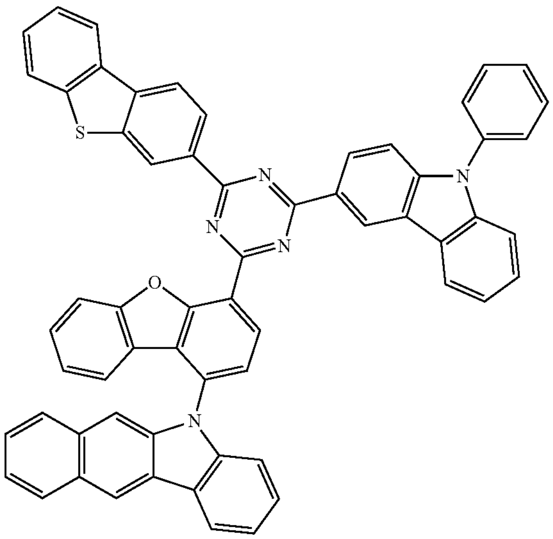
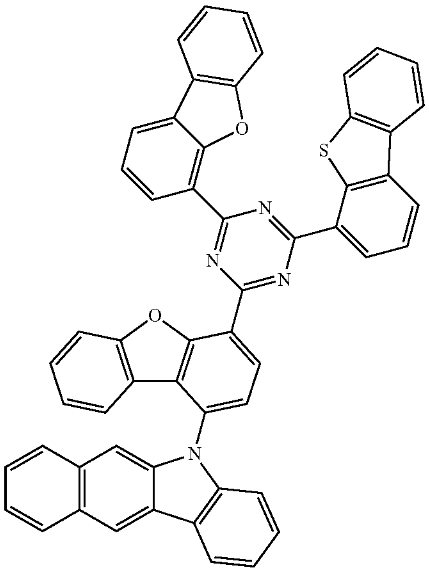
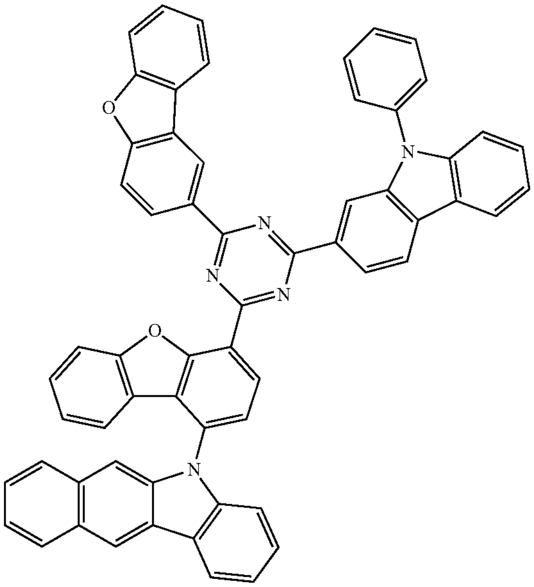

-continued
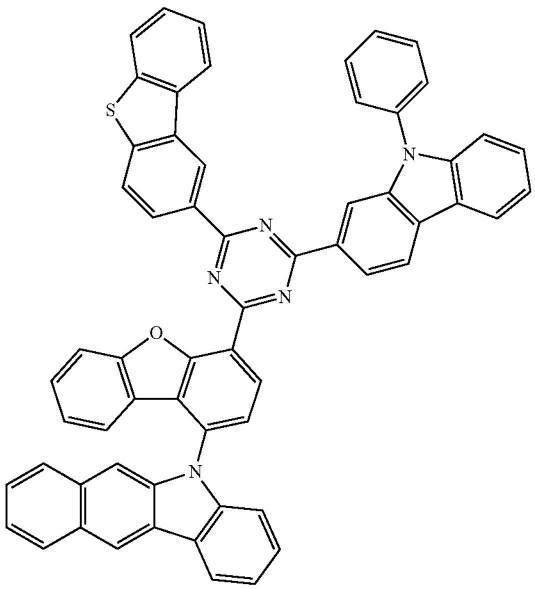
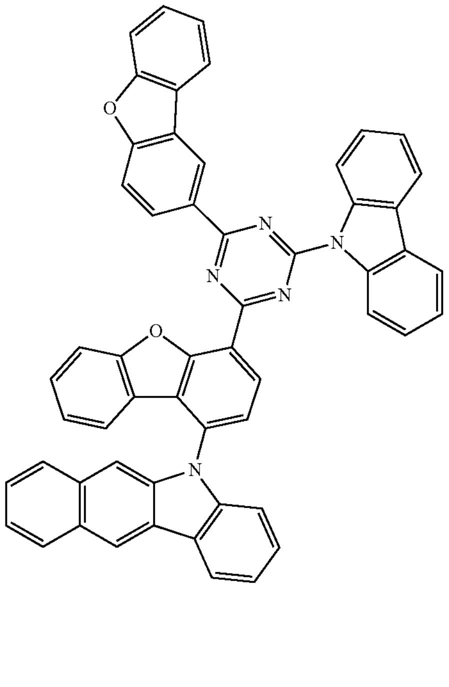
-continued
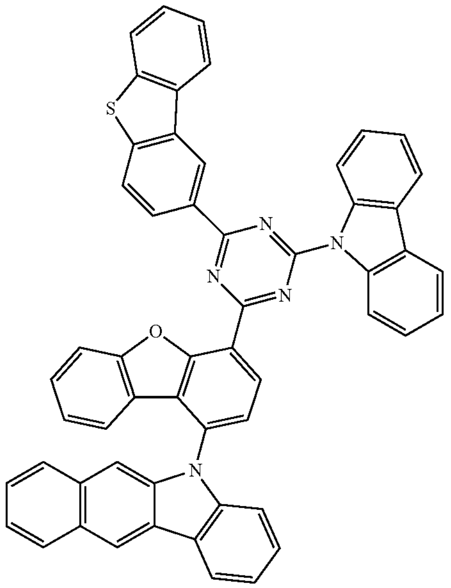
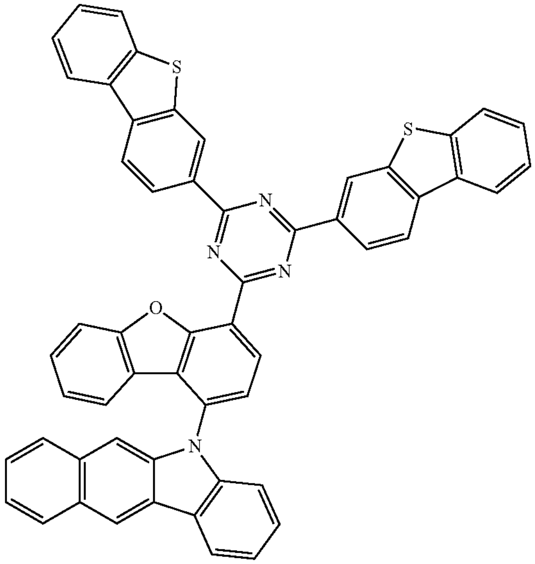
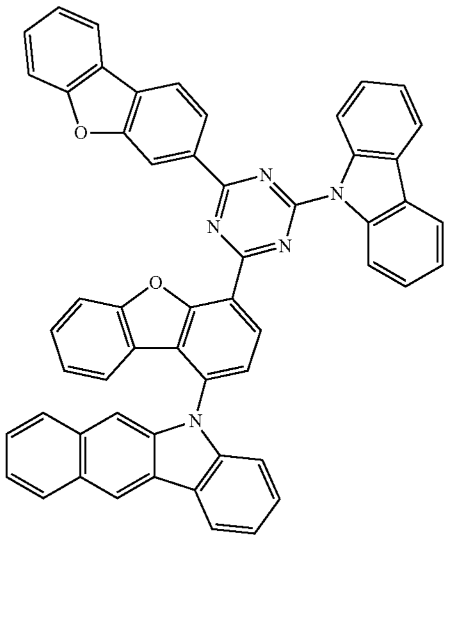

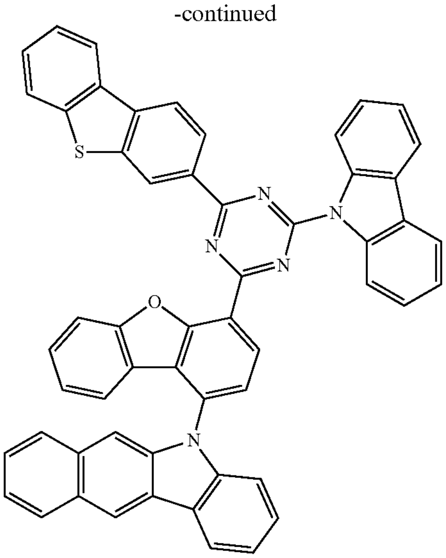
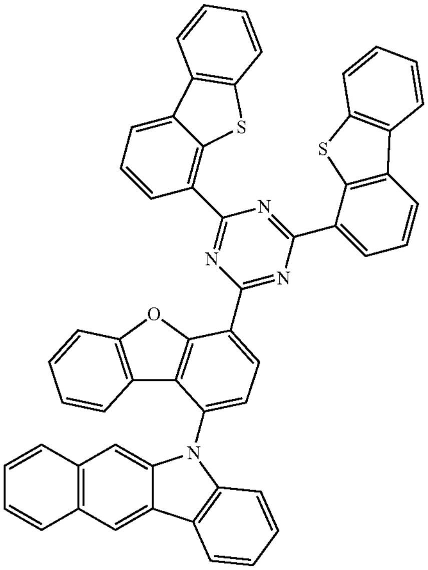
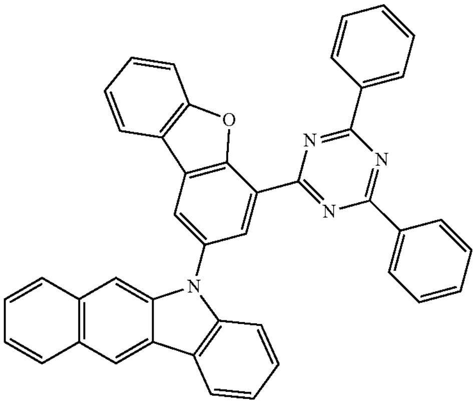
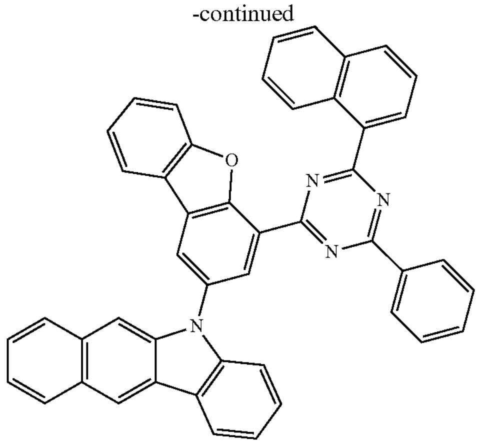
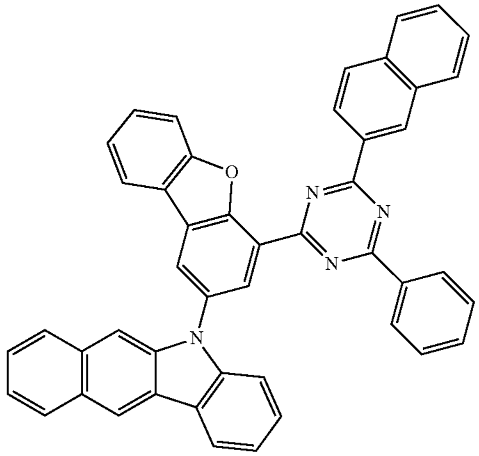
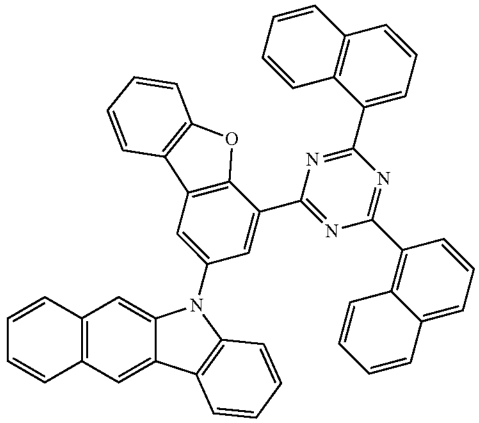
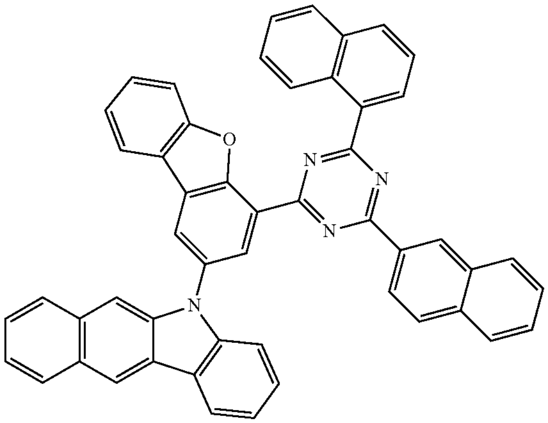

-continued
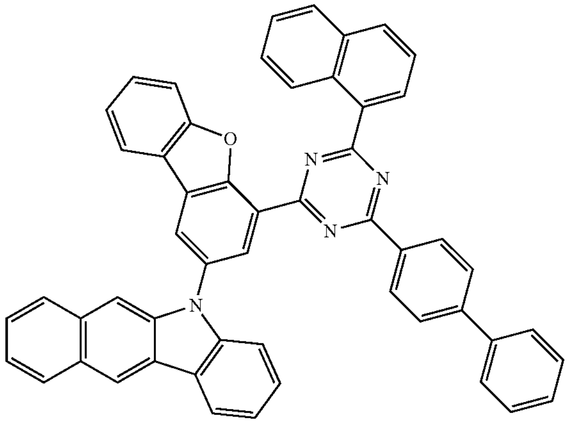
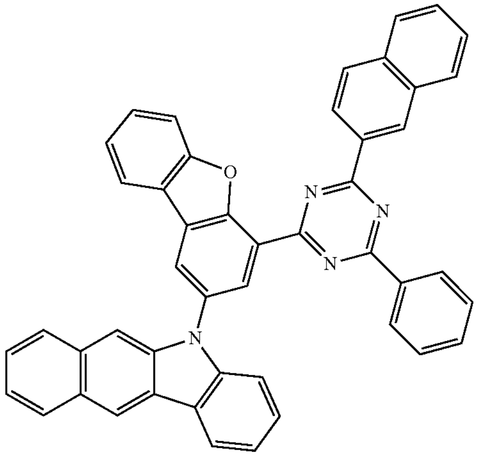
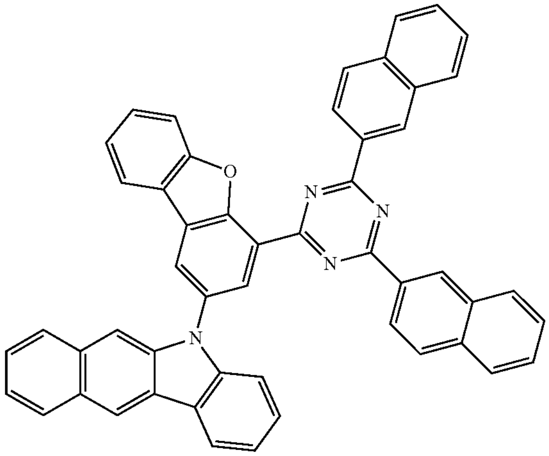
-continued
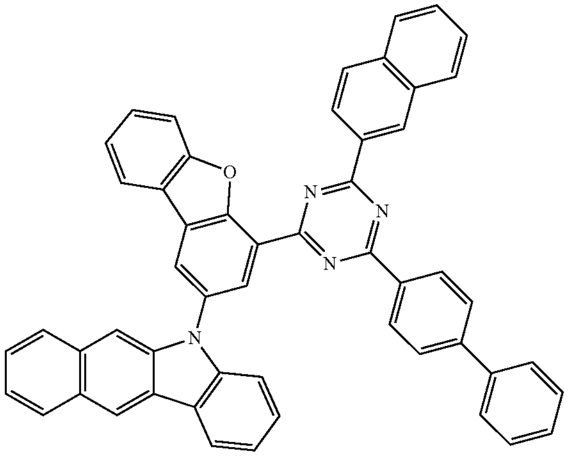
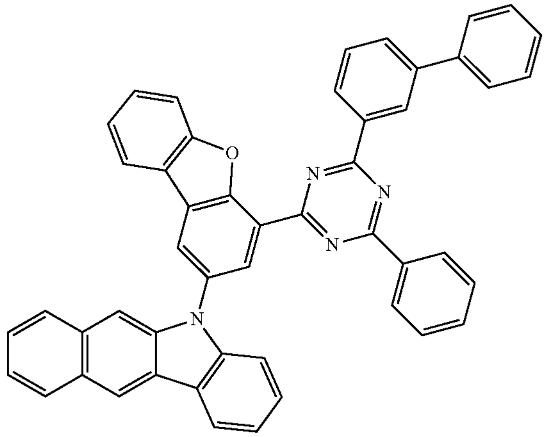
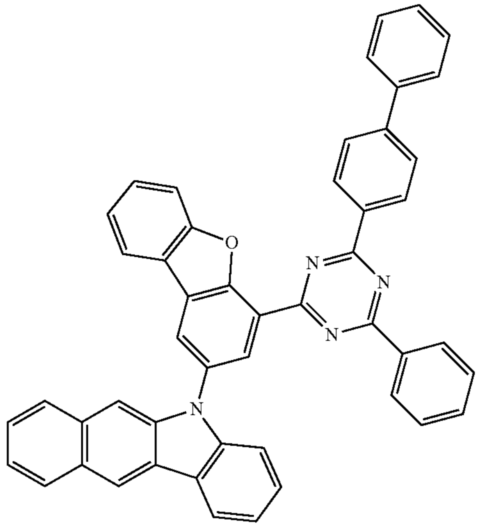

-continued
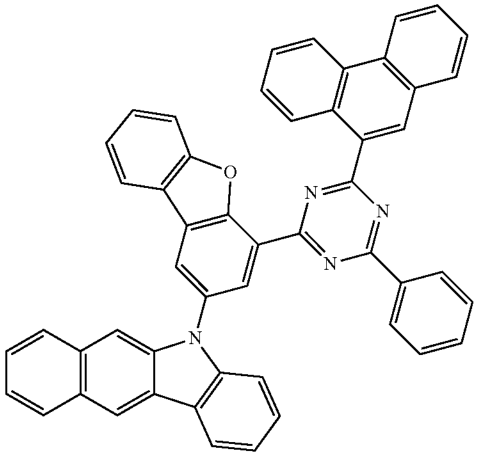
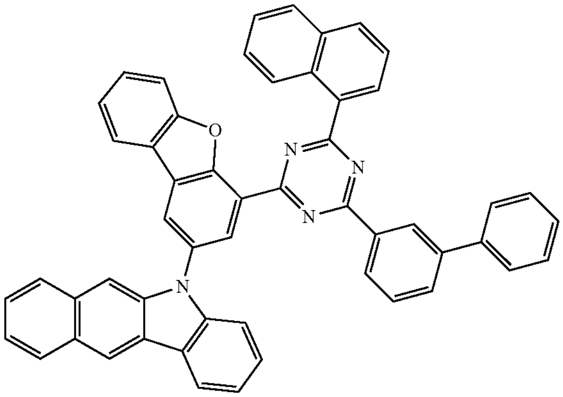
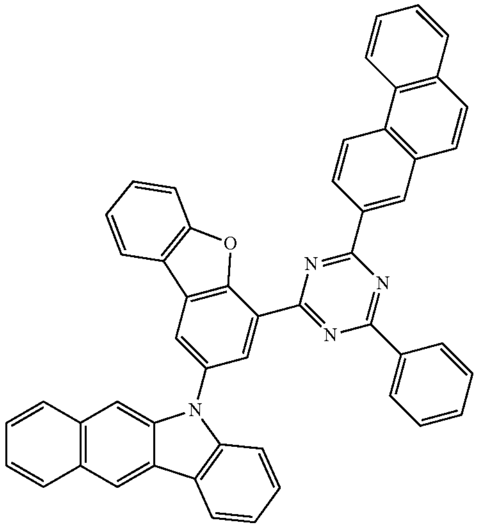
-continued
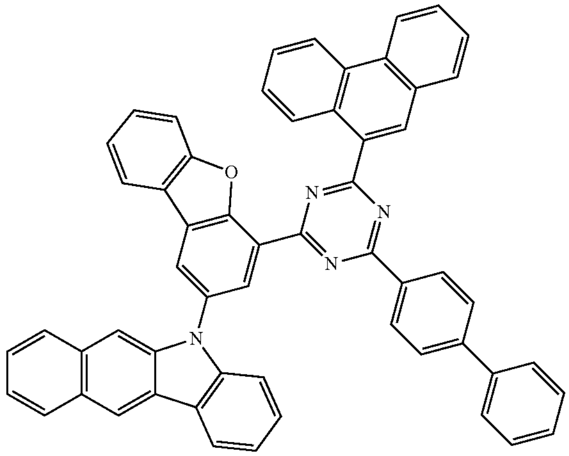
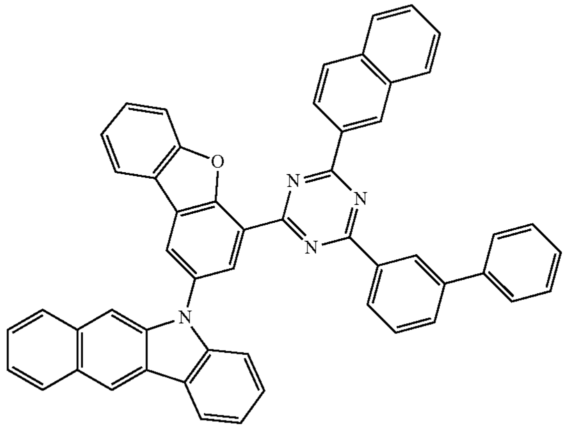
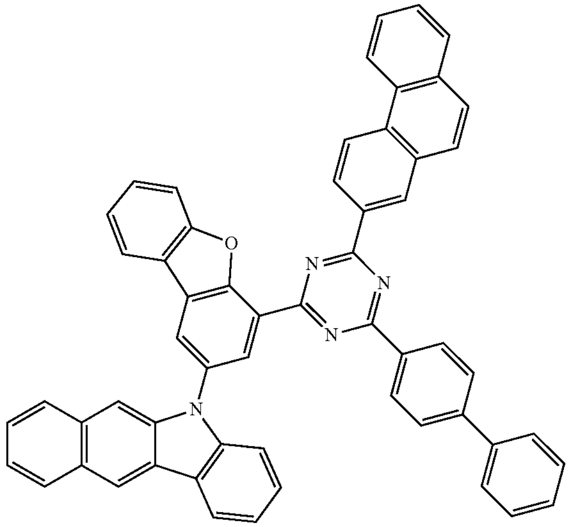

-continued
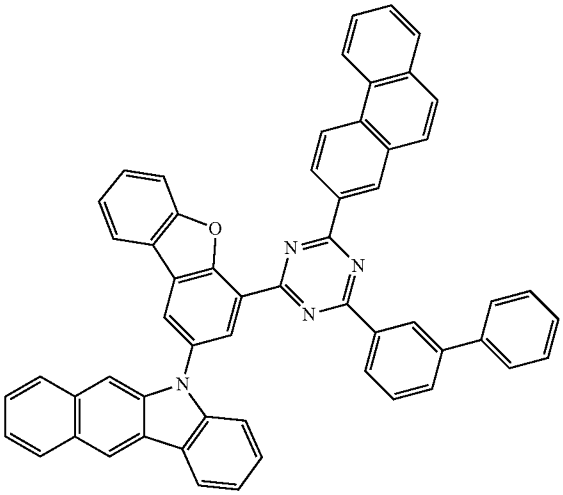
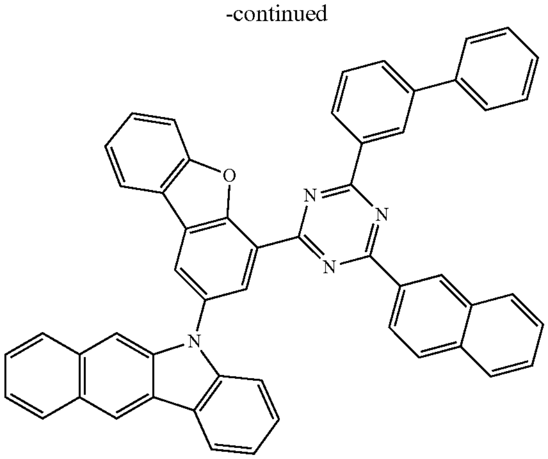
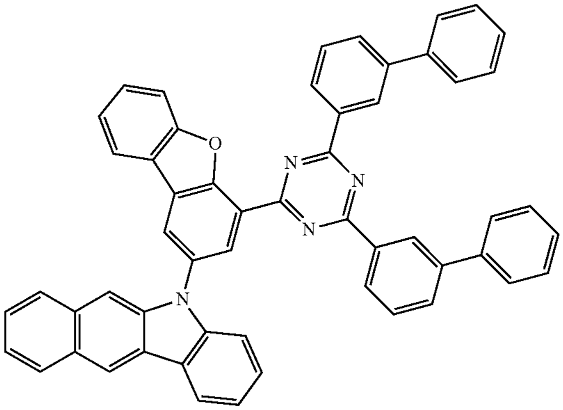
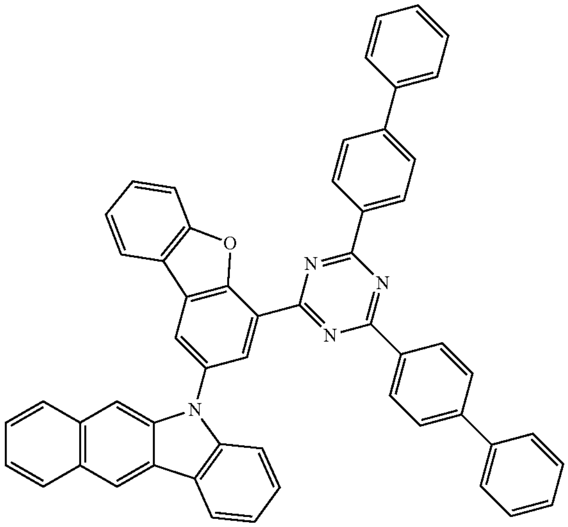
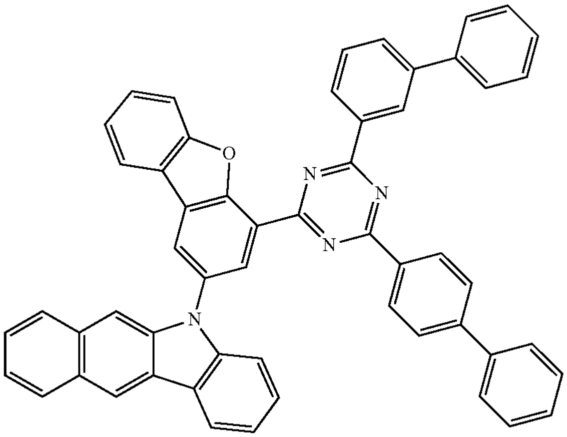
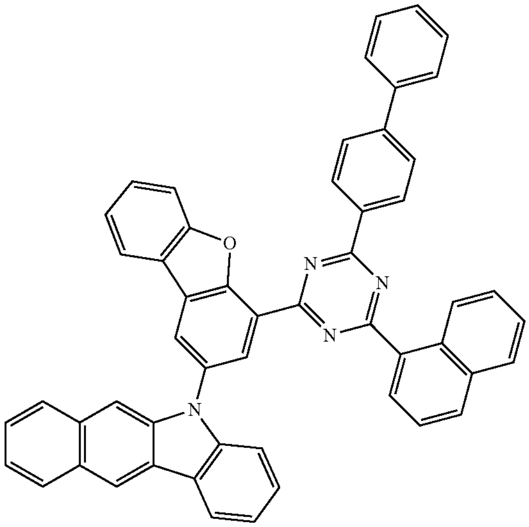
-continued -continued
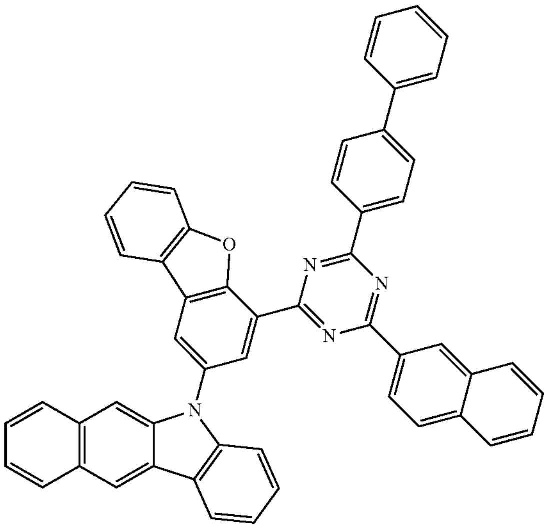
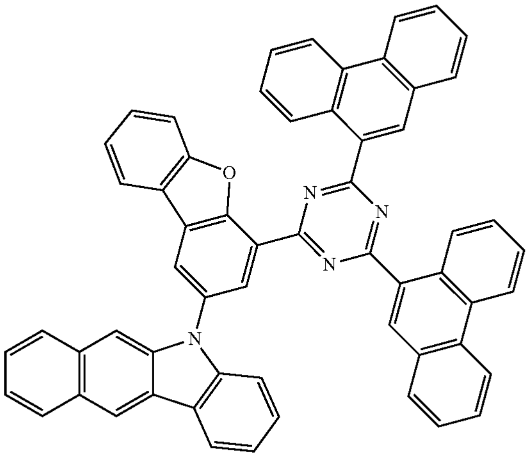
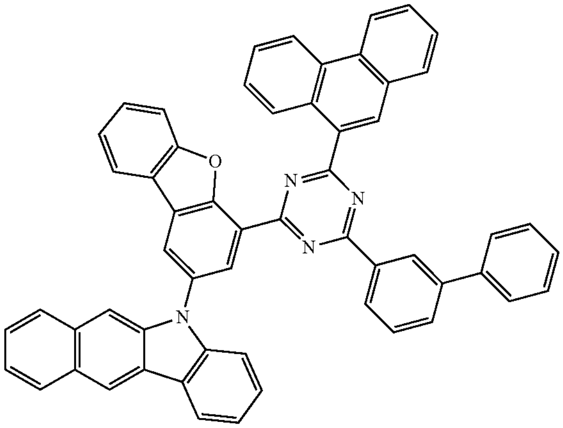
-continued
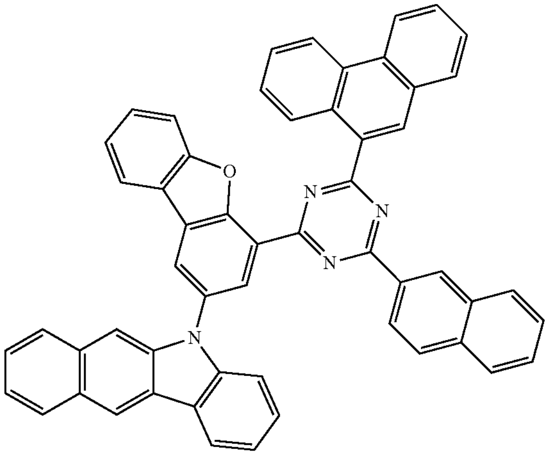
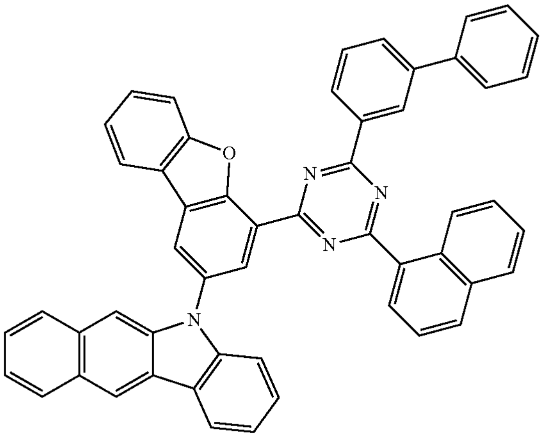
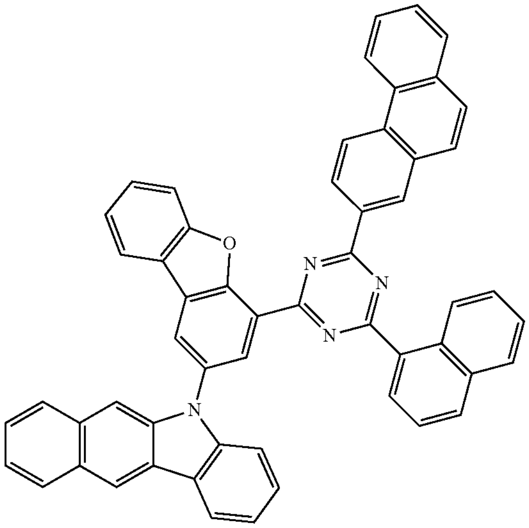

-continued
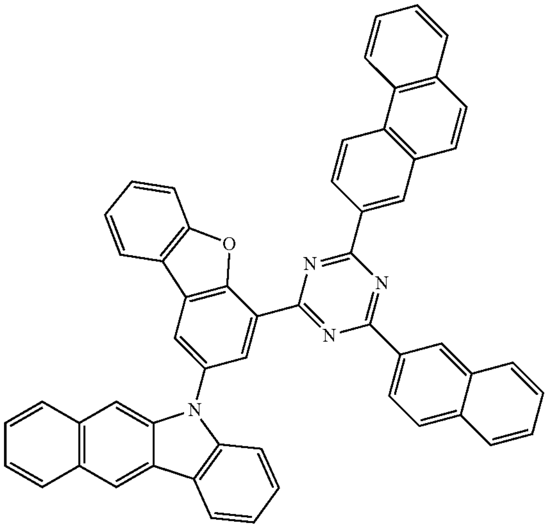
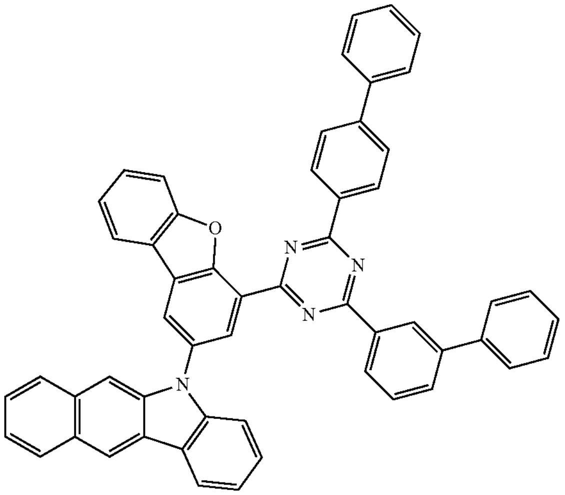
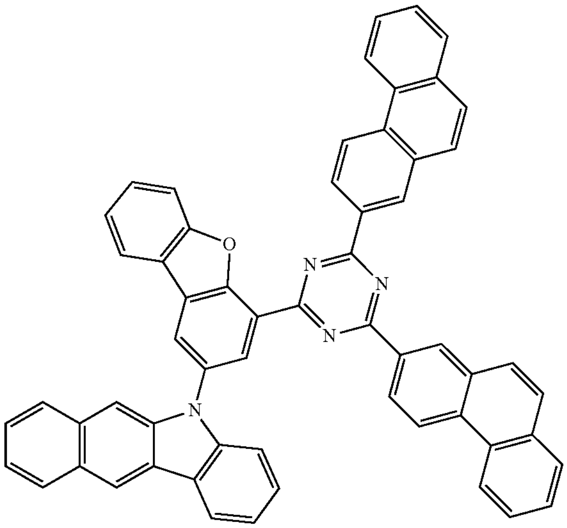
-continued
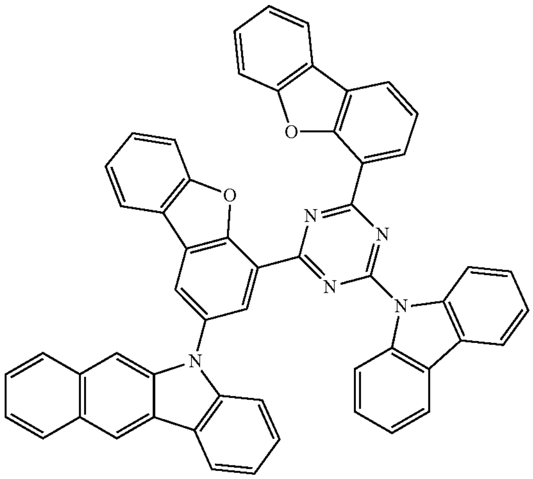
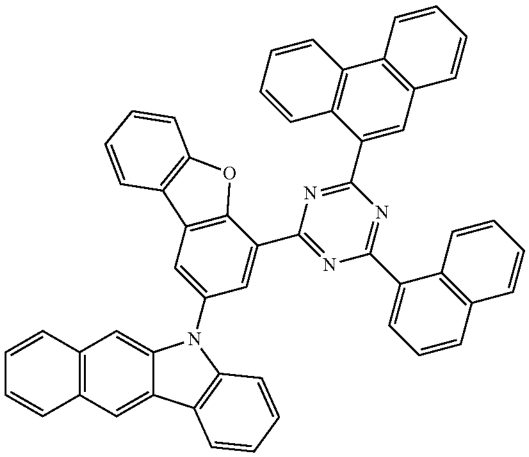
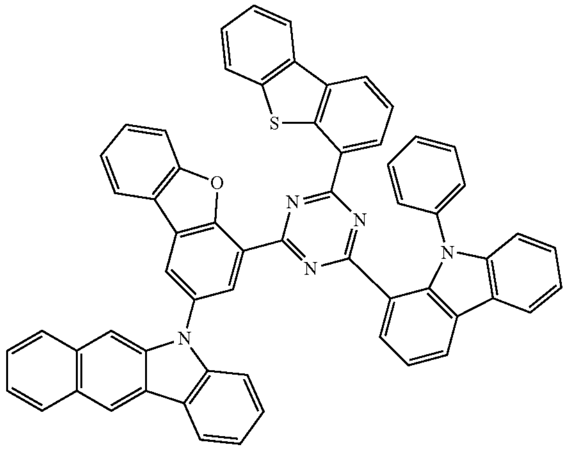

-continued
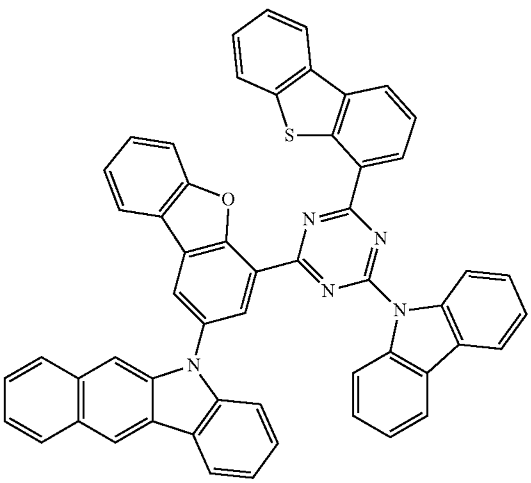
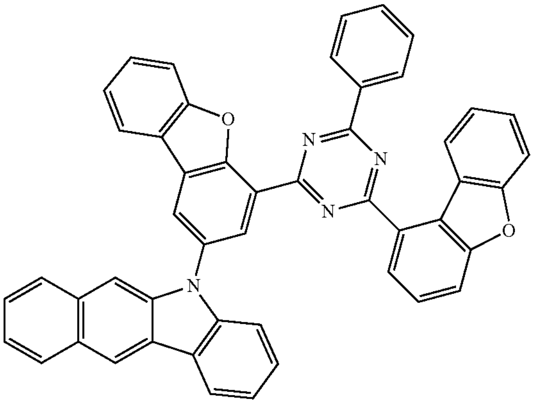
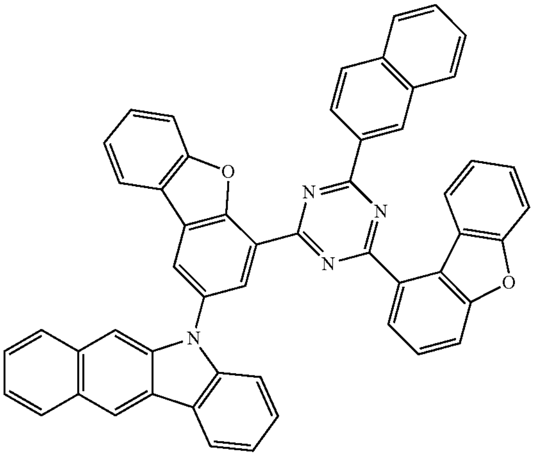
-continued
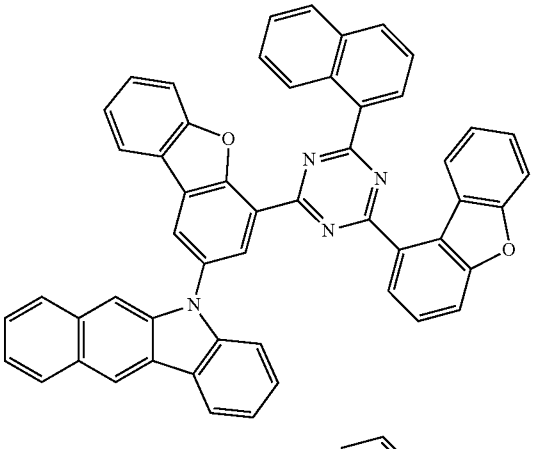
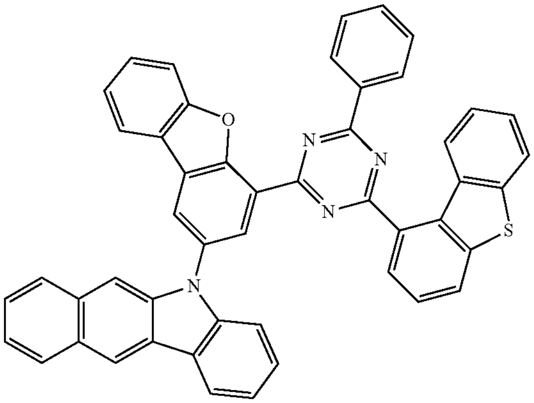
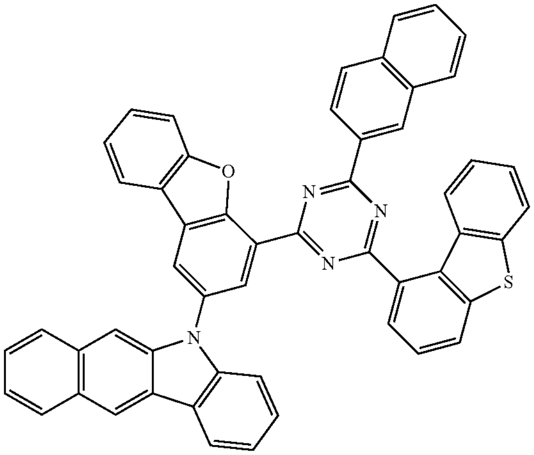
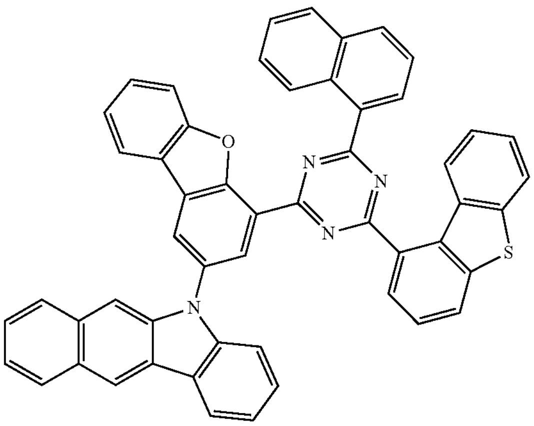

-continued
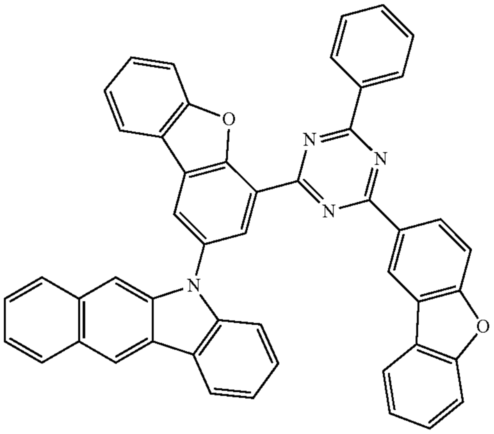
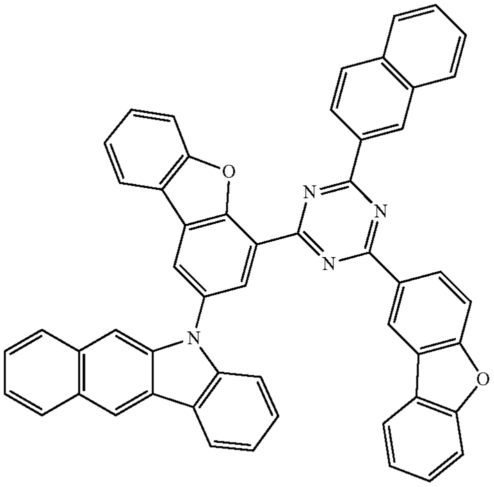
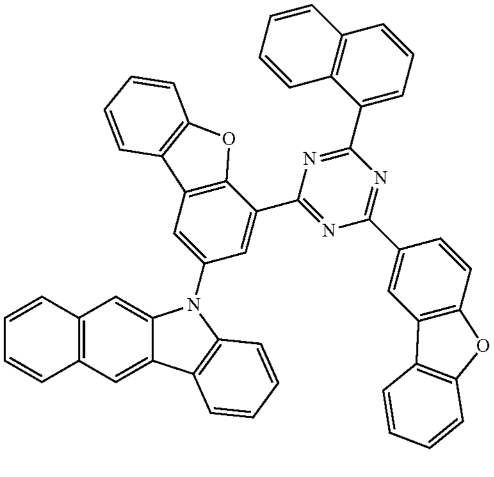
-continued
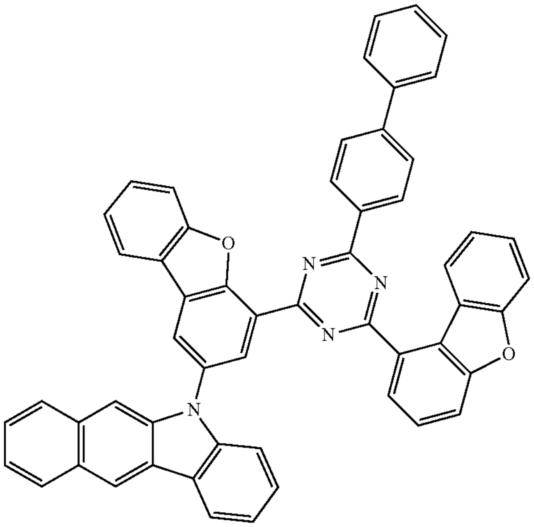
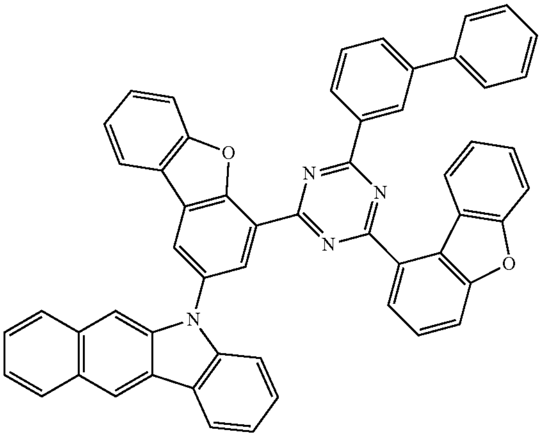
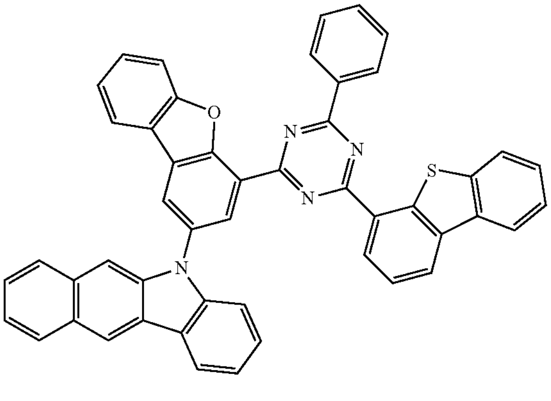

-continued
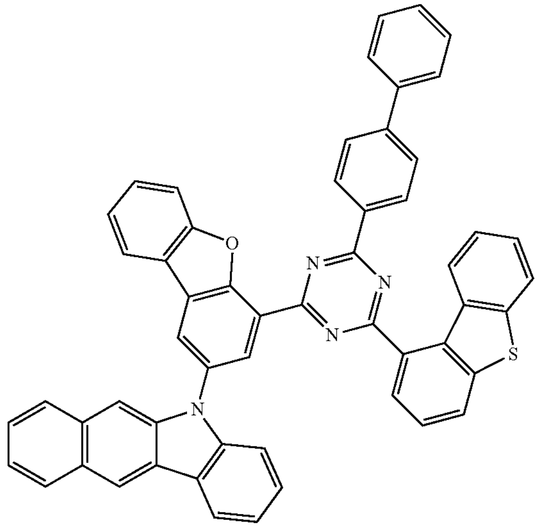
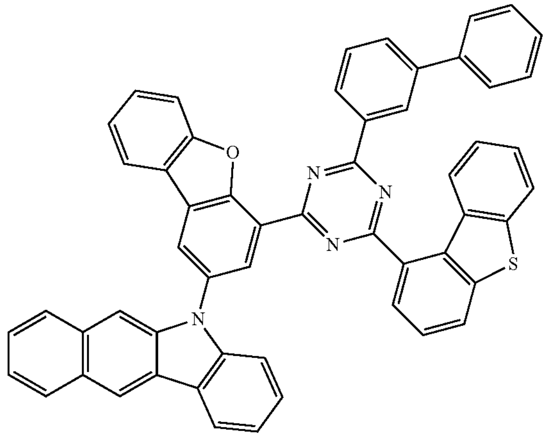
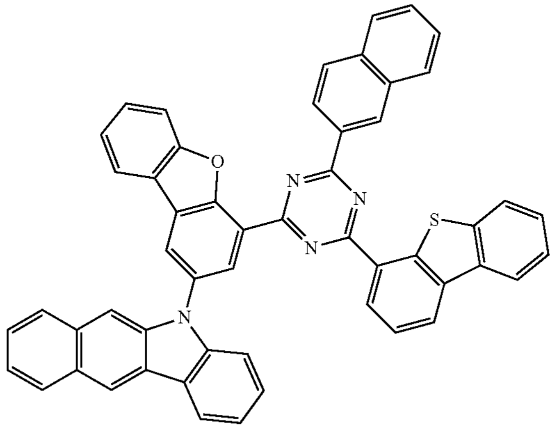
-continued
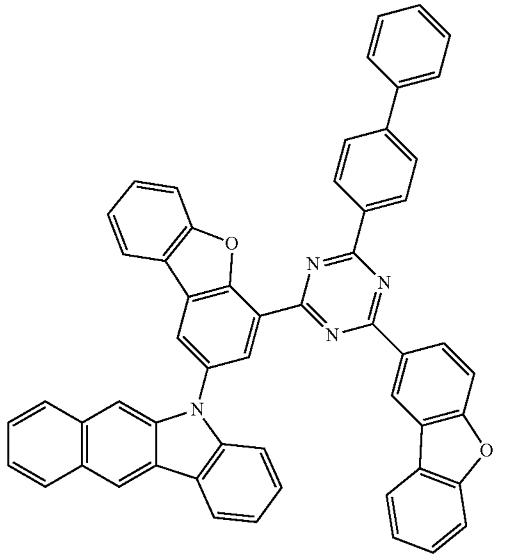
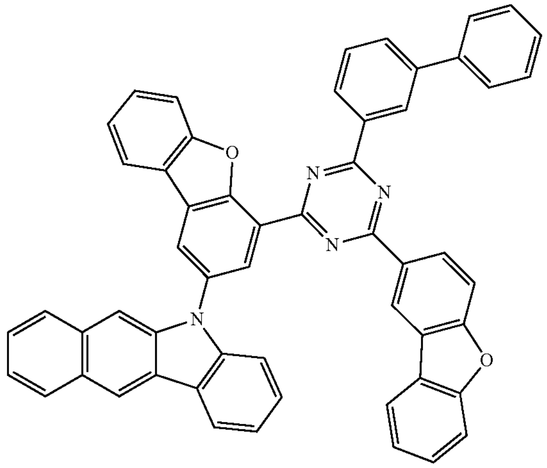
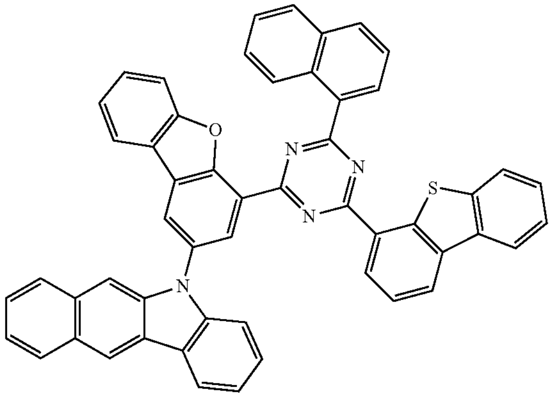

-continued
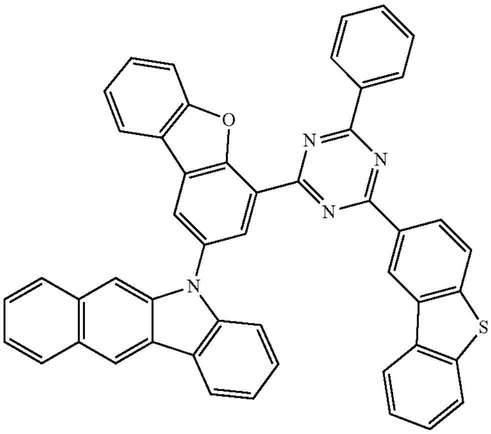
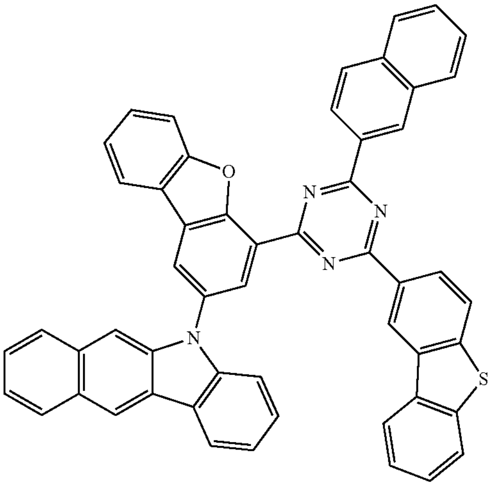
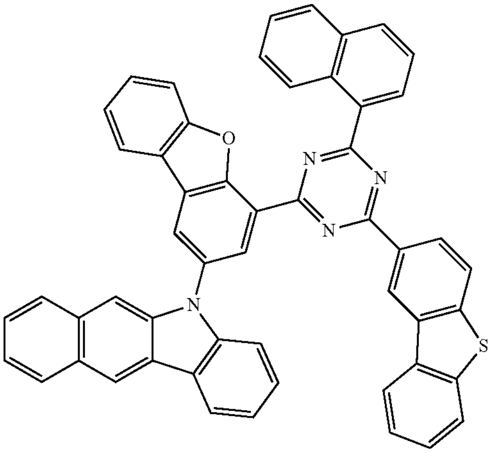
-continued
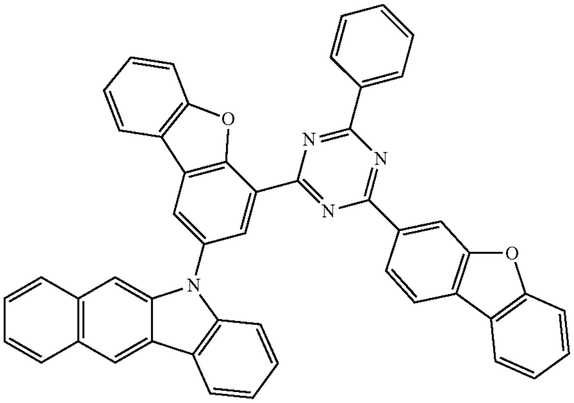
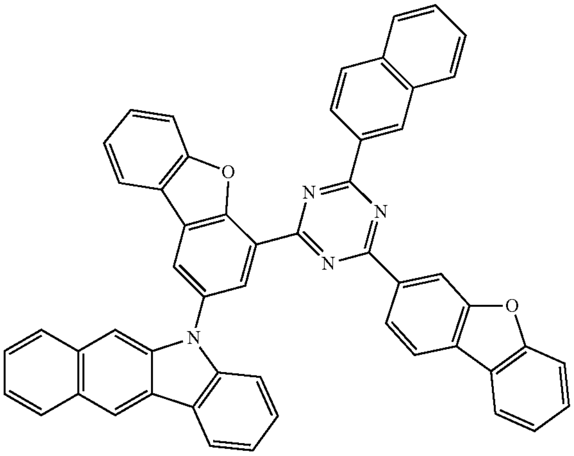
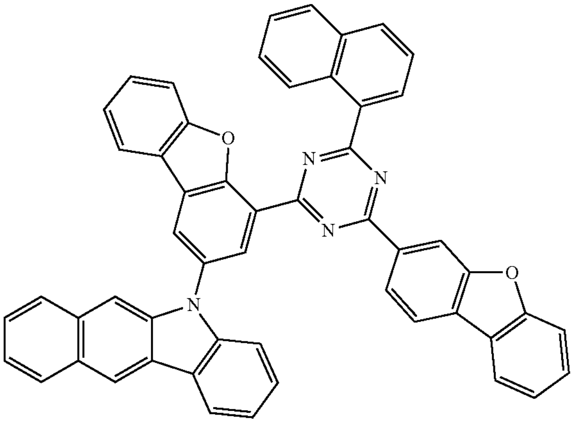
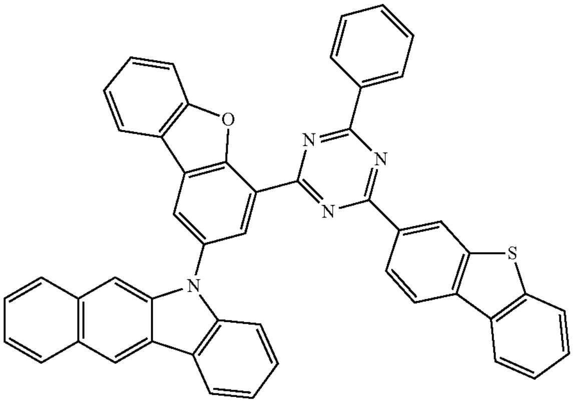

-continued
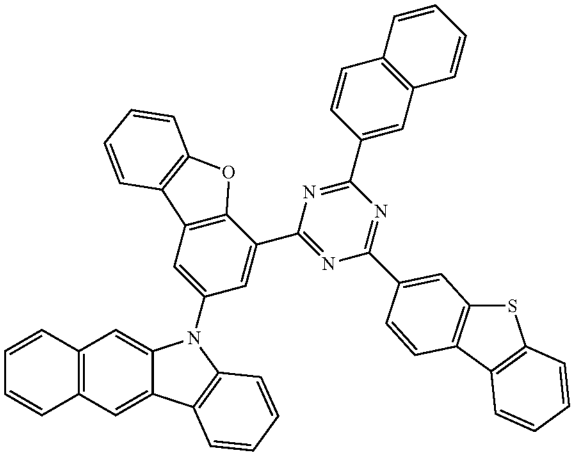
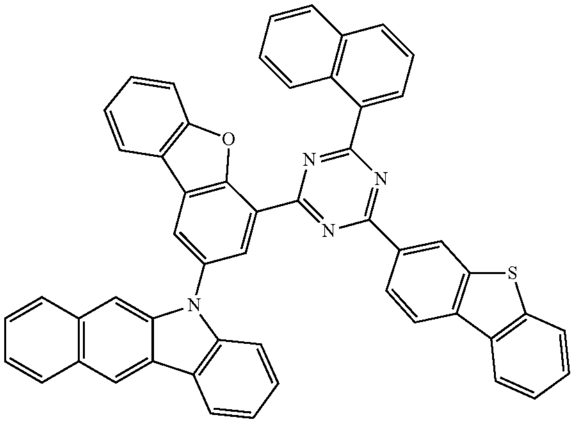
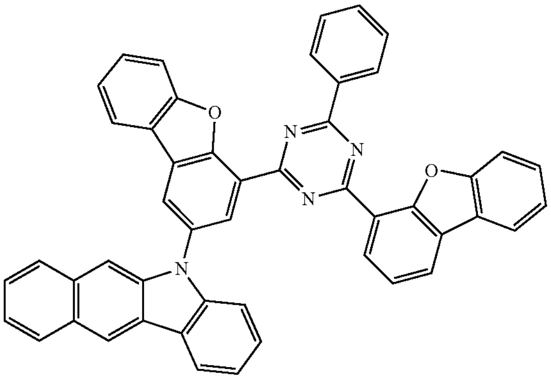
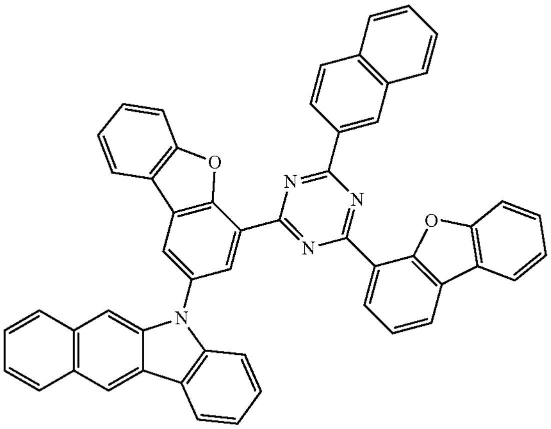
-continued
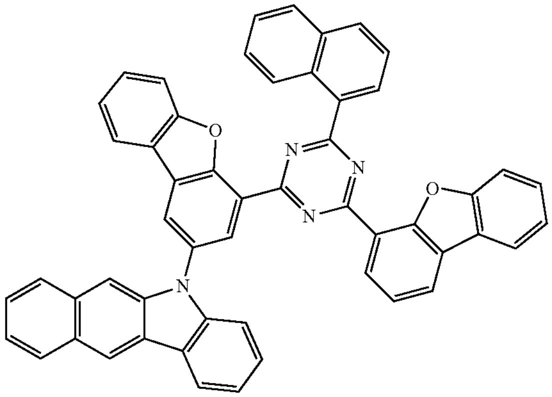
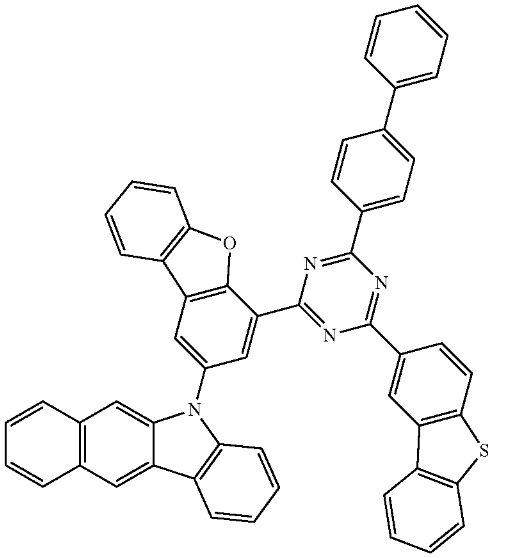
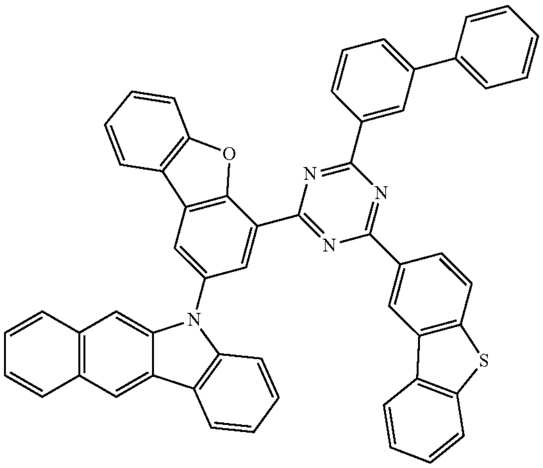

-continued
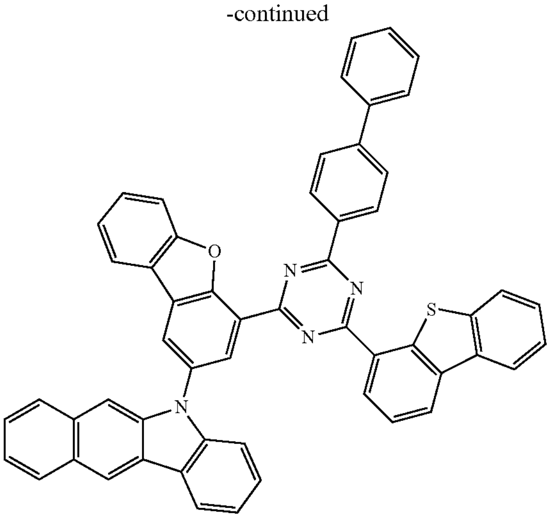
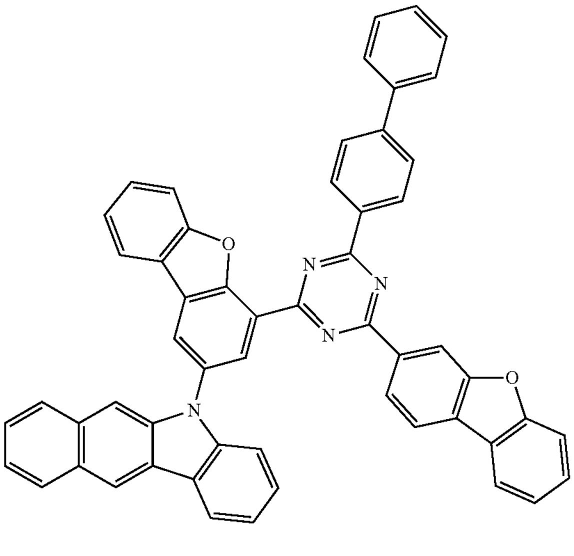
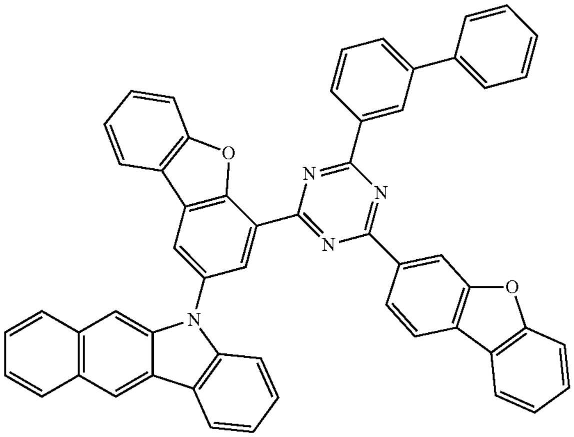
-continued
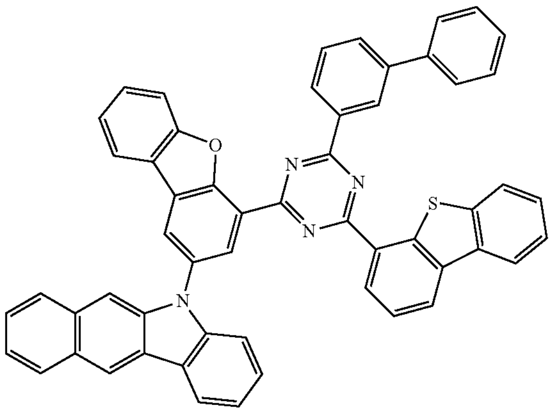
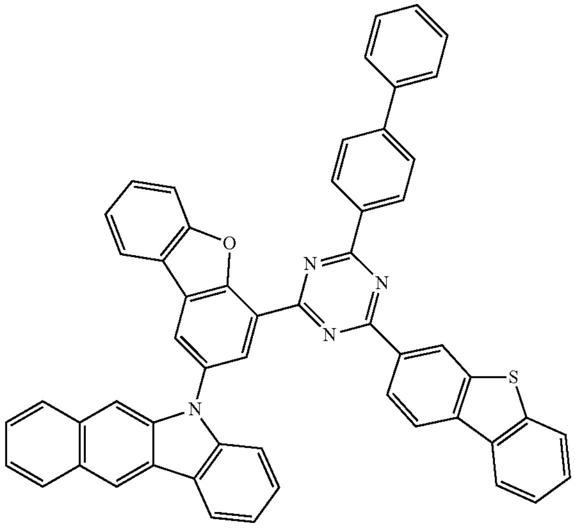
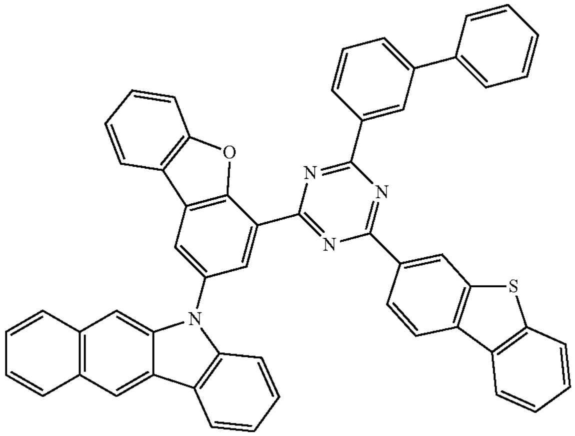

-continued
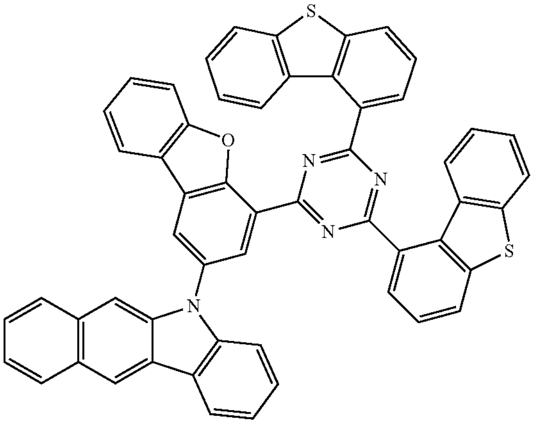
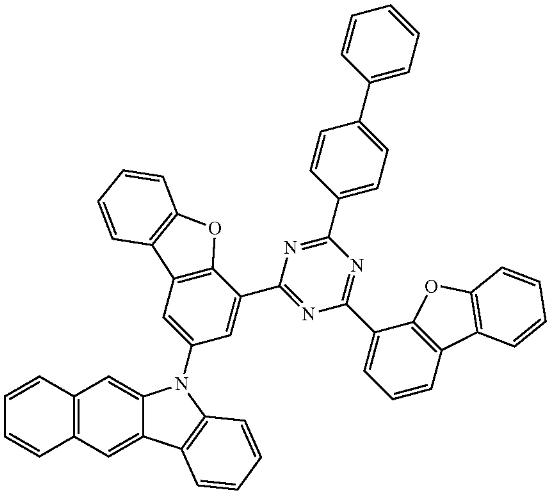
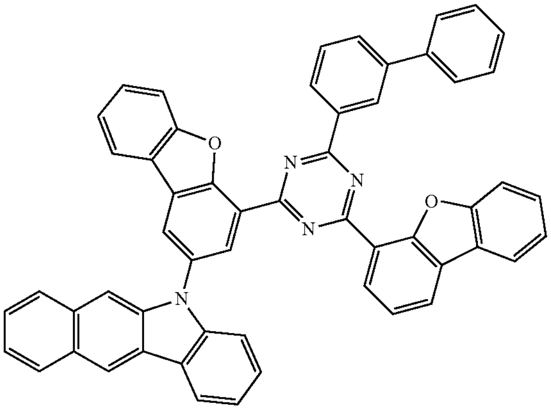
-continued
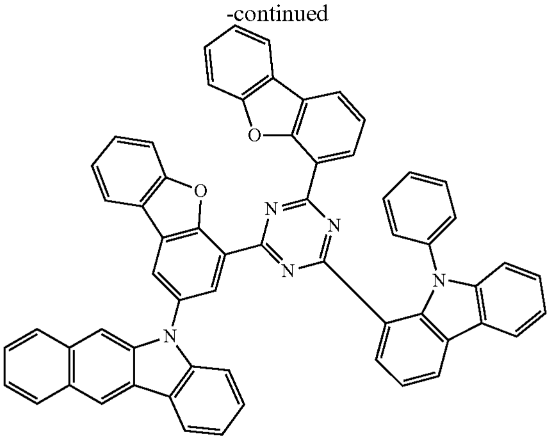
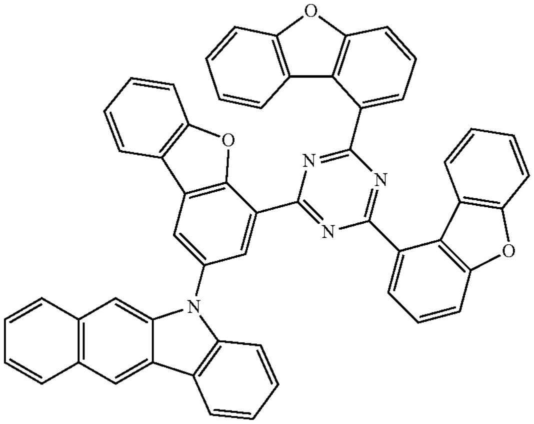
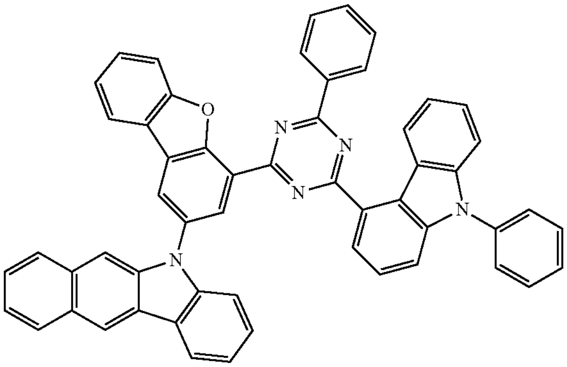
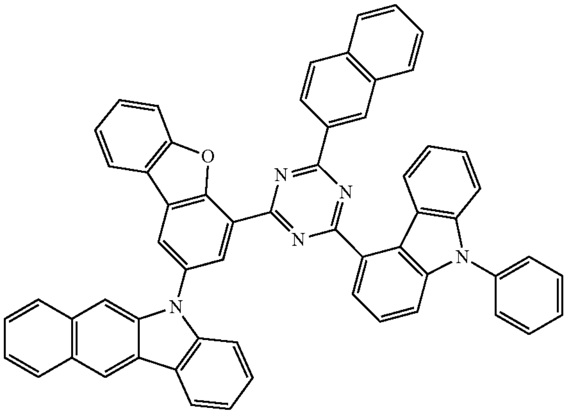

-continued
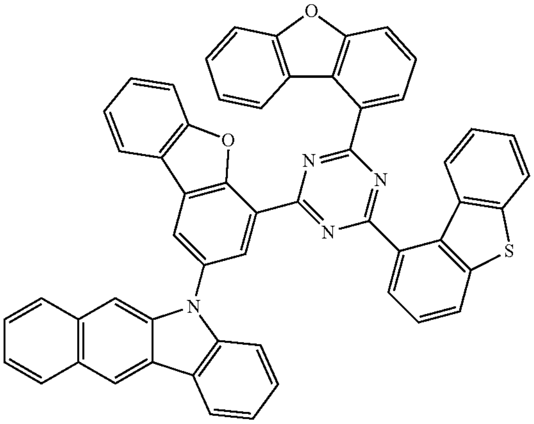
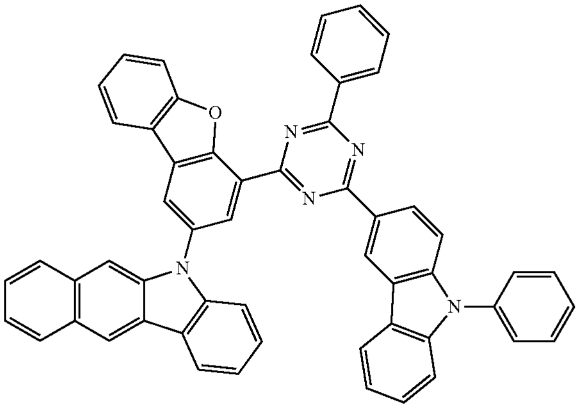
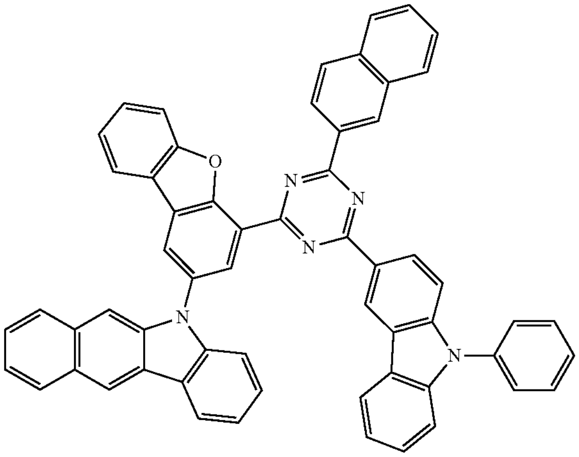
-continued
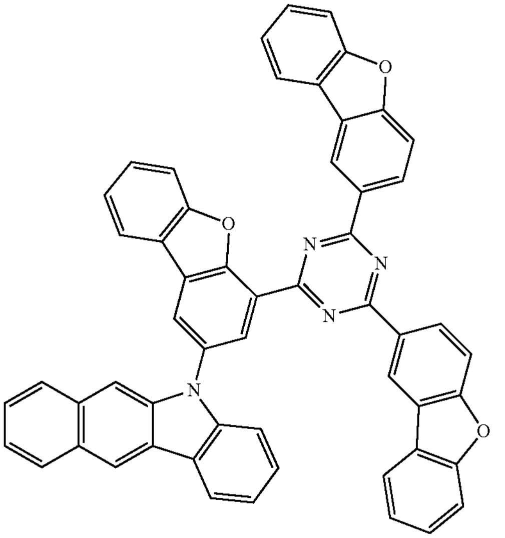
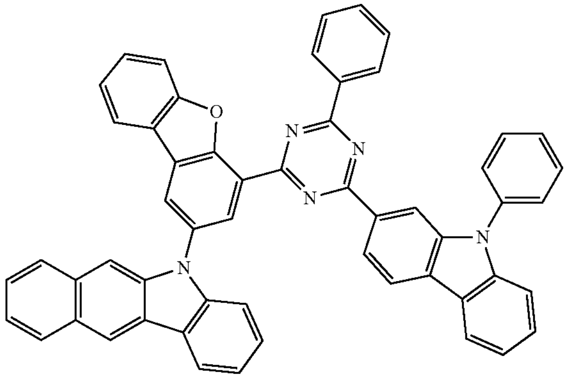
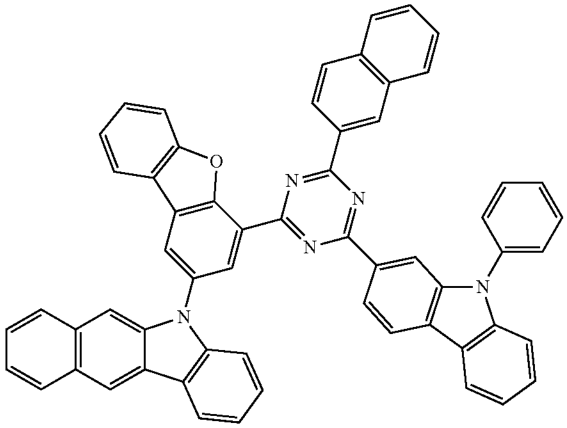
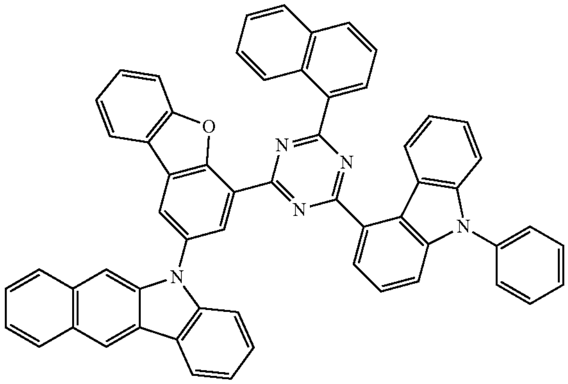

-continued
-continued
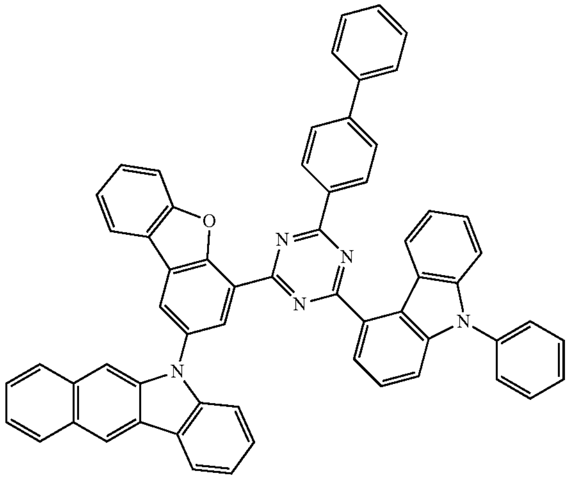
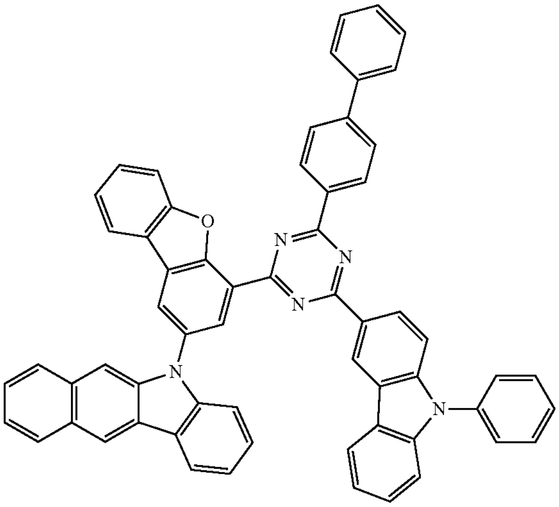
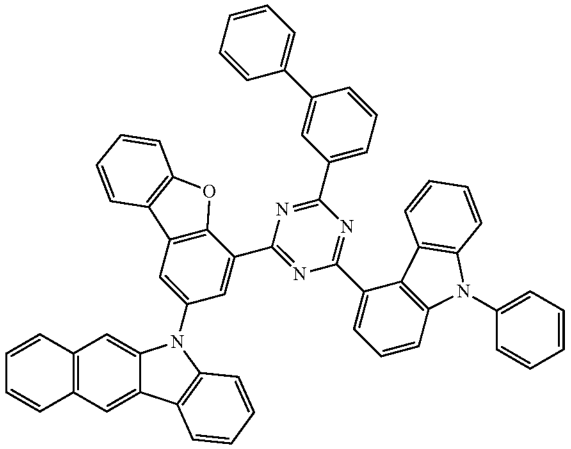
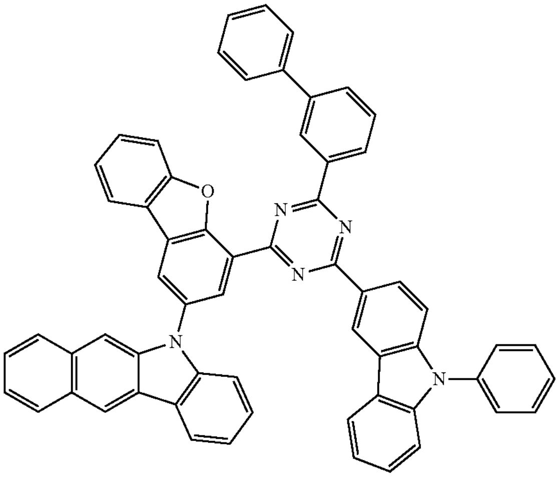
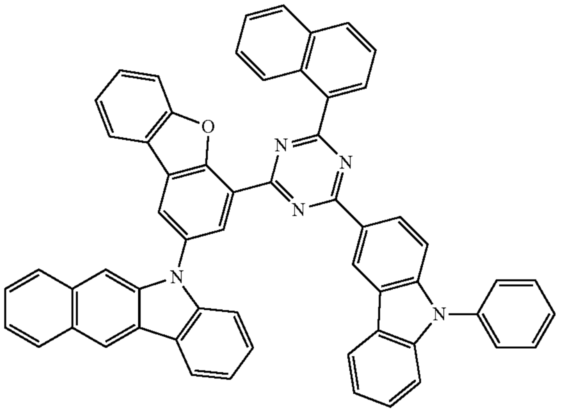
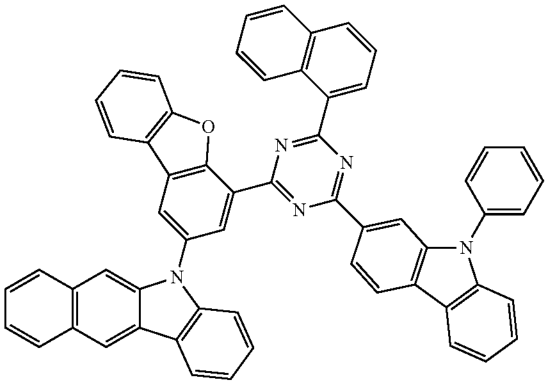

-continued
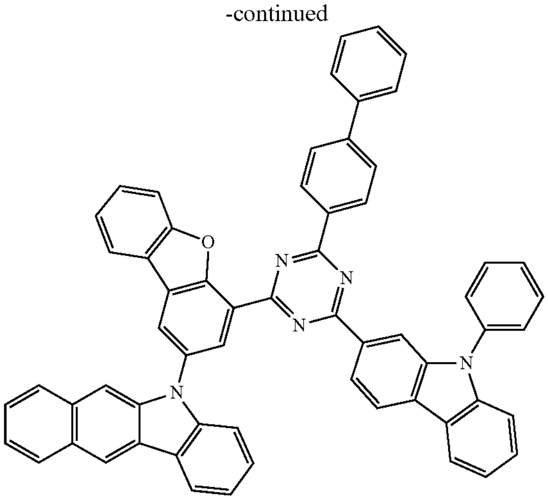
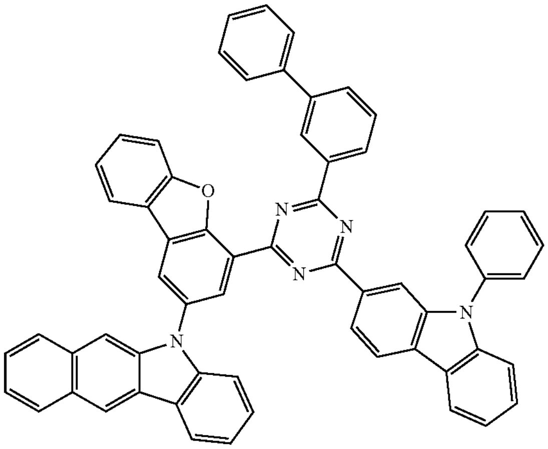
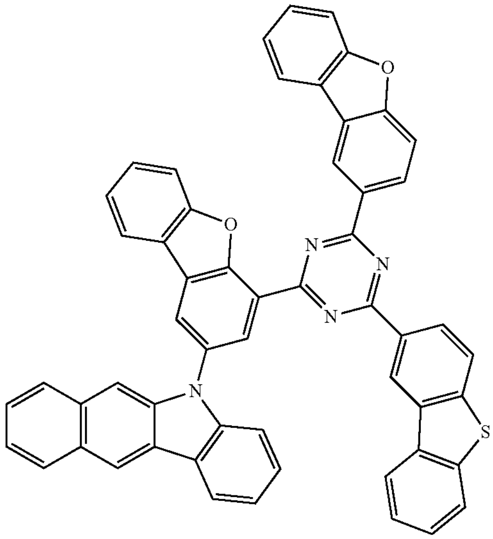
-continued
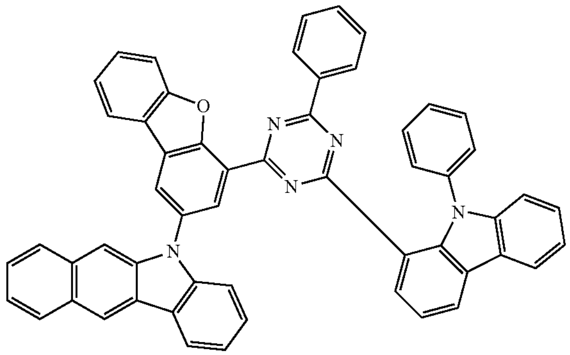
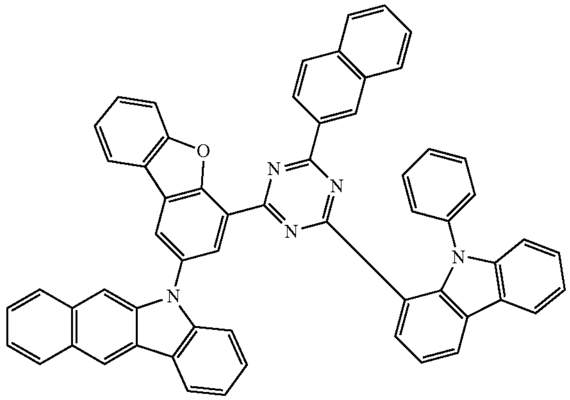
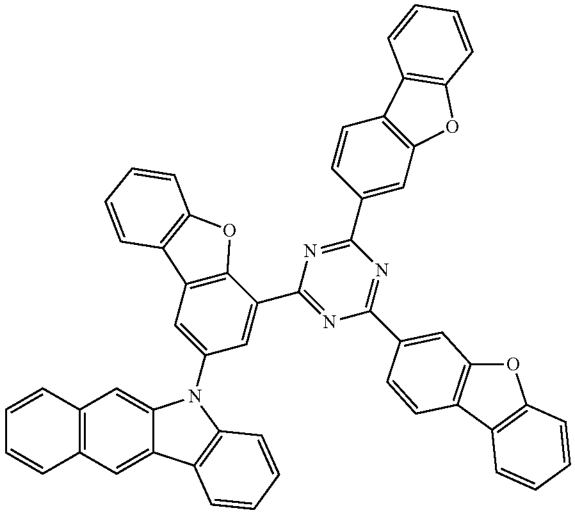
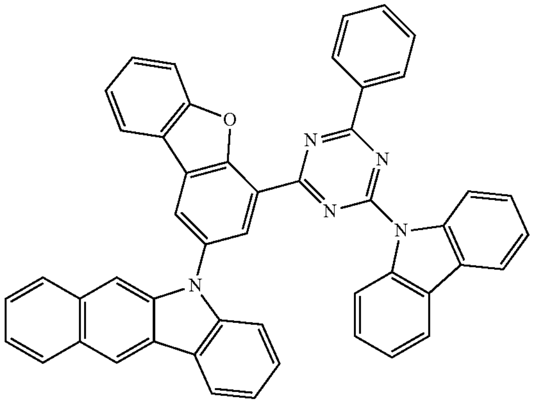

-continued
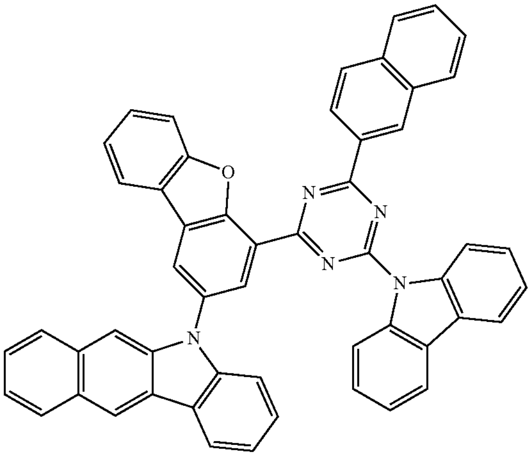
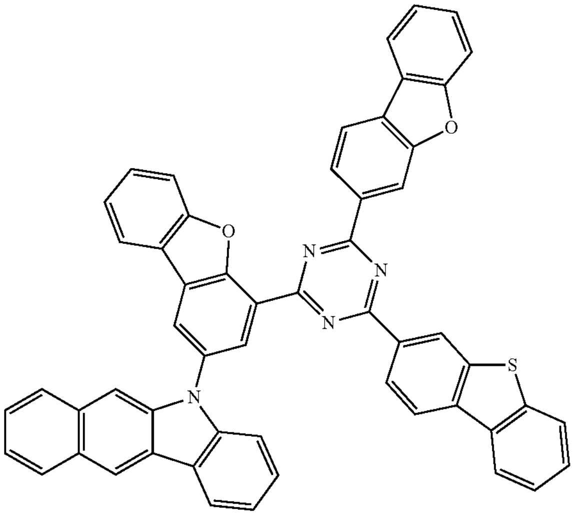
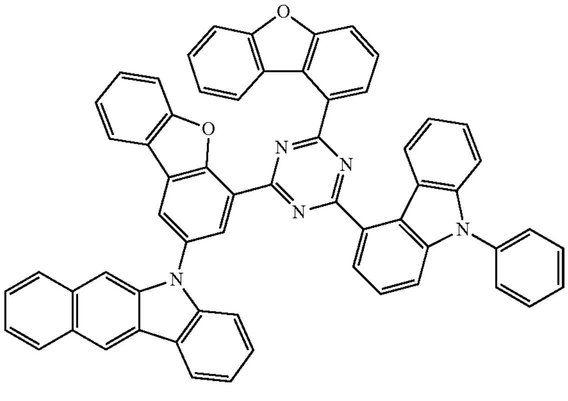
-continued
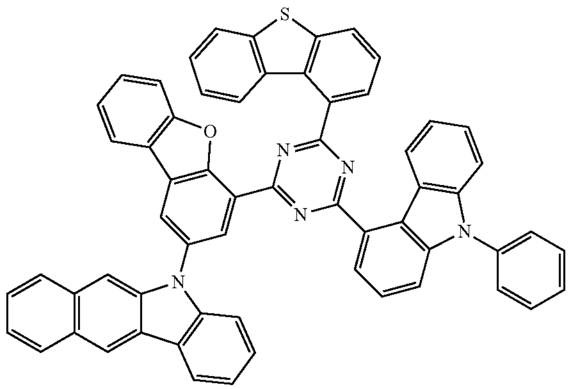
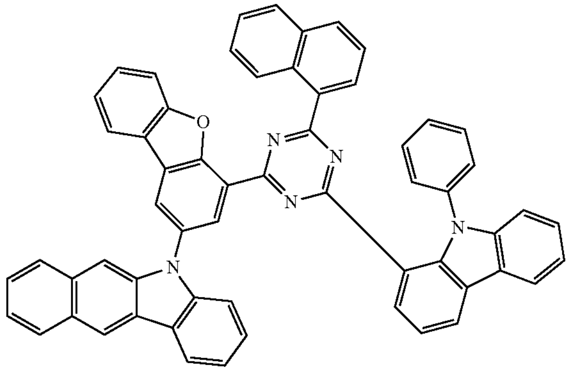
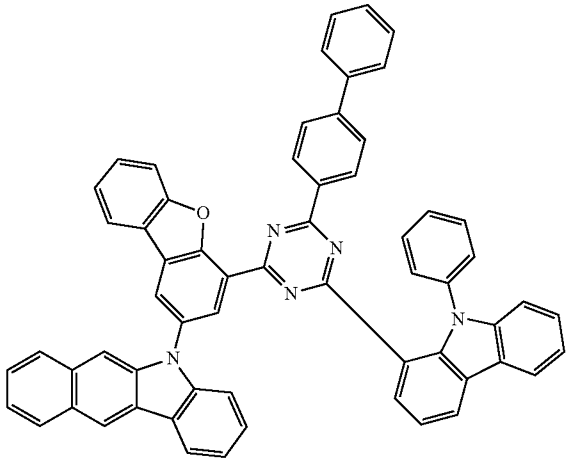
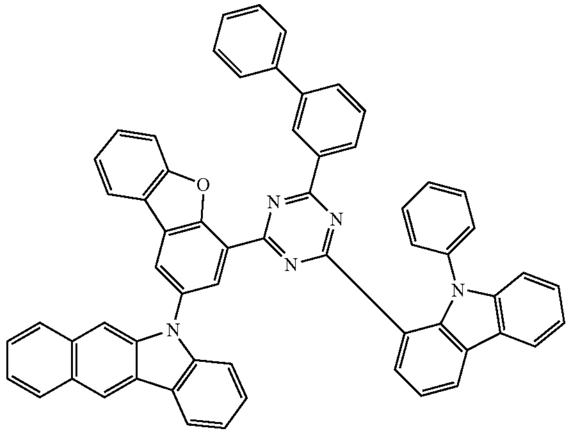

-continued
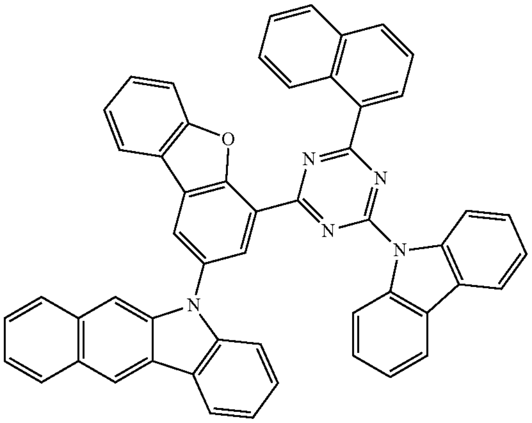
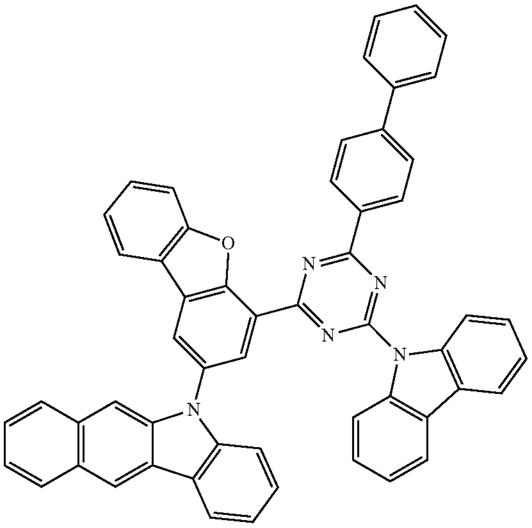
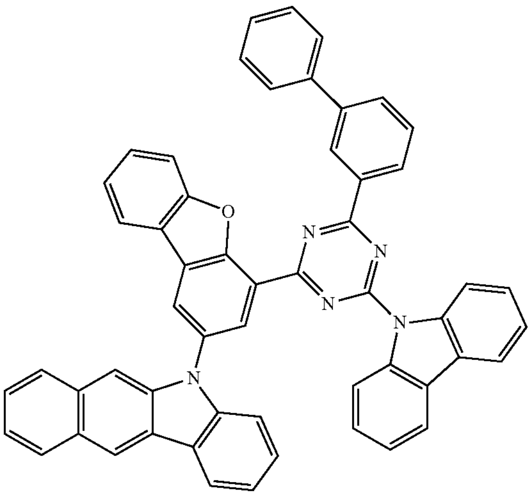
-continued
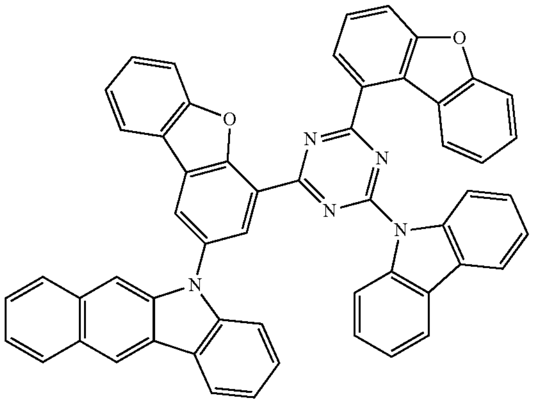
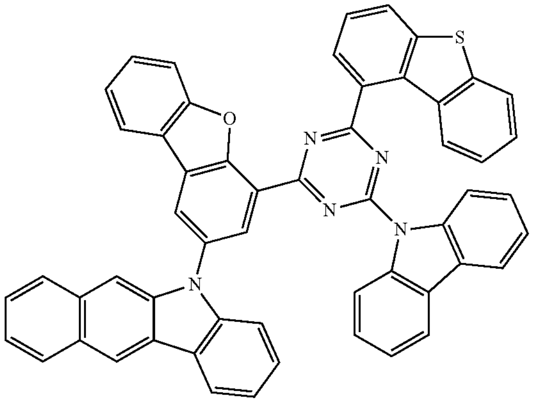
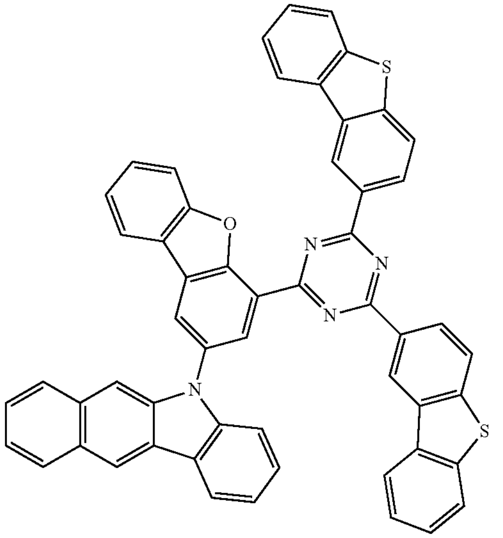
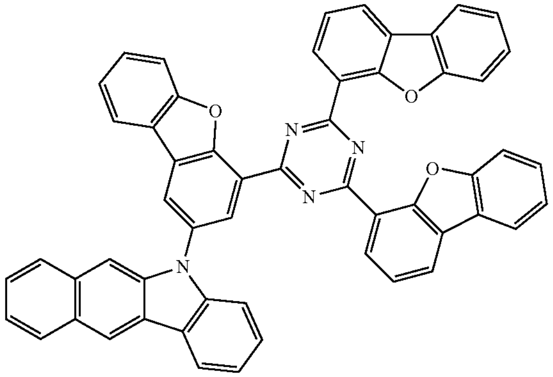

-continued
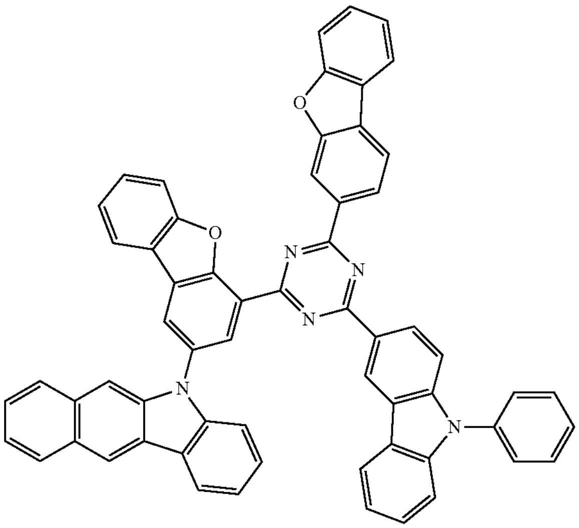
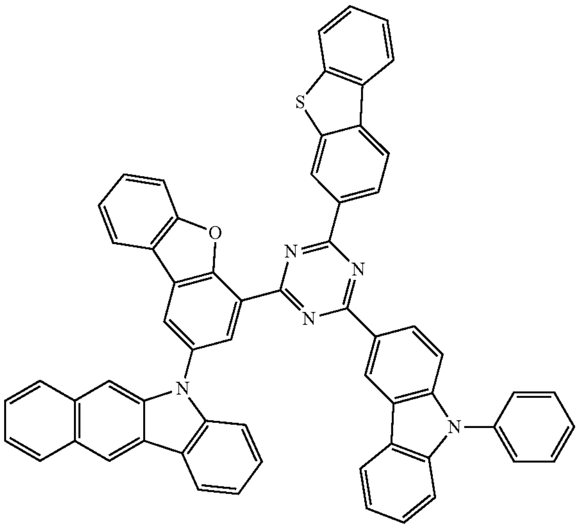
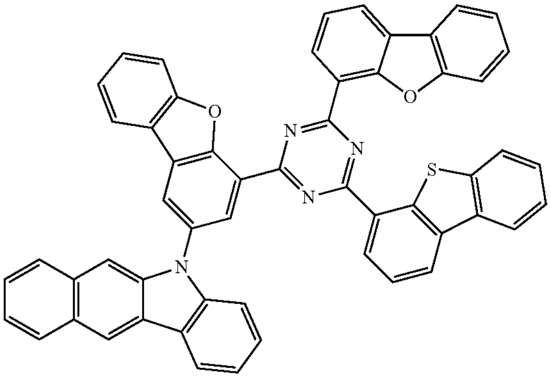
-continued
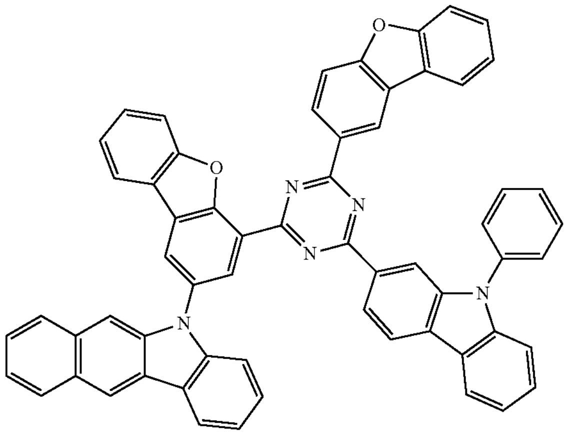
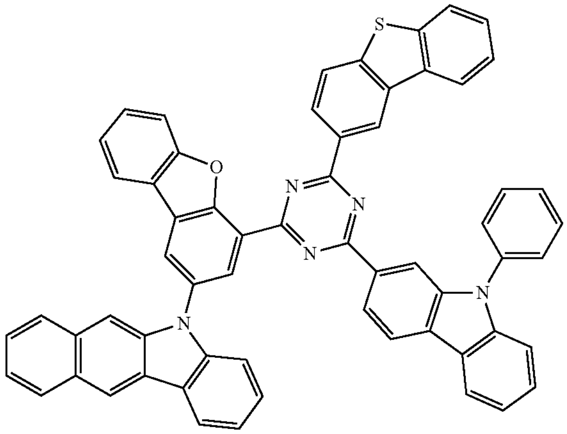
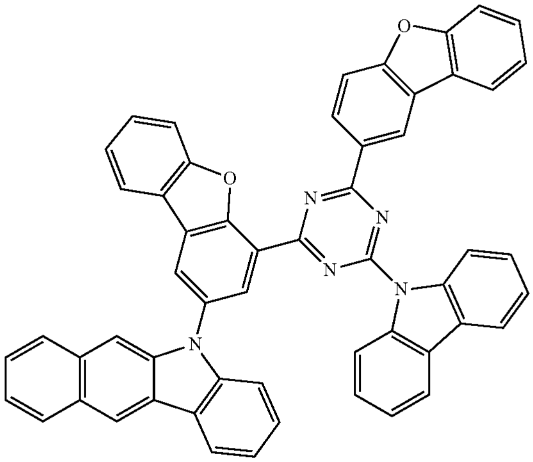

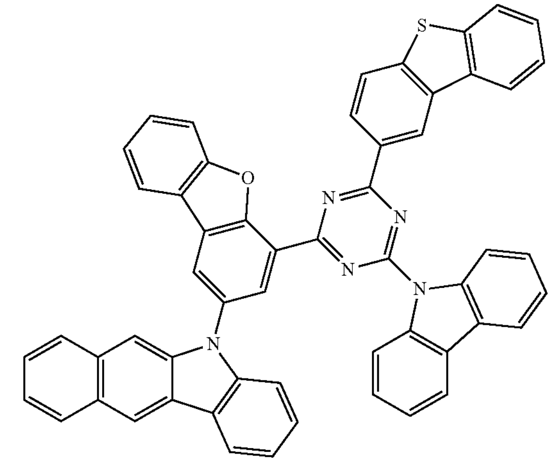
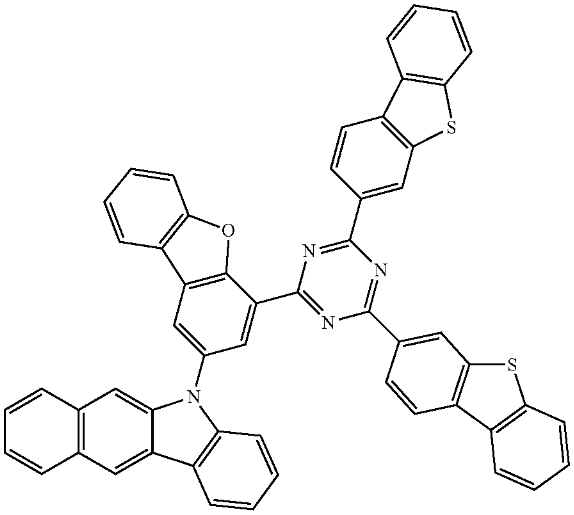
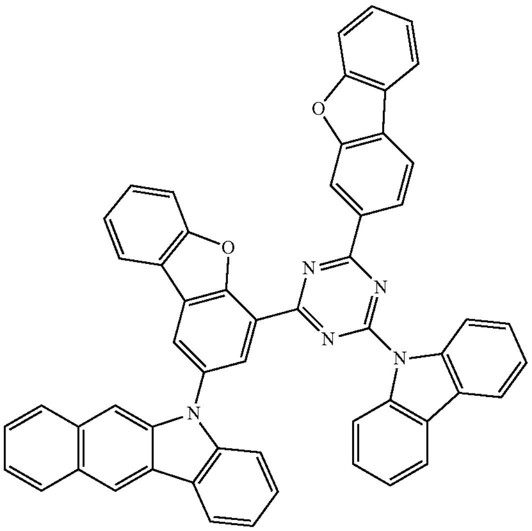
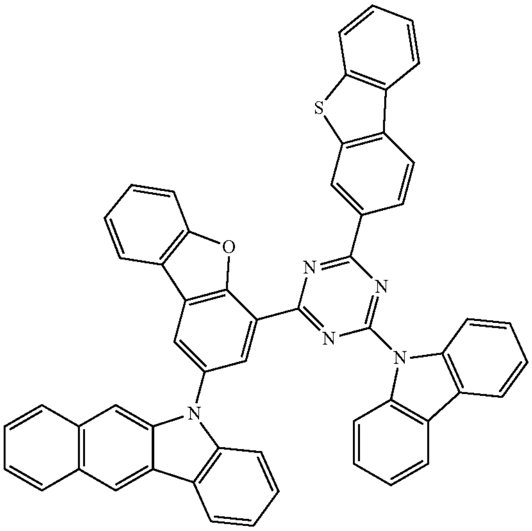
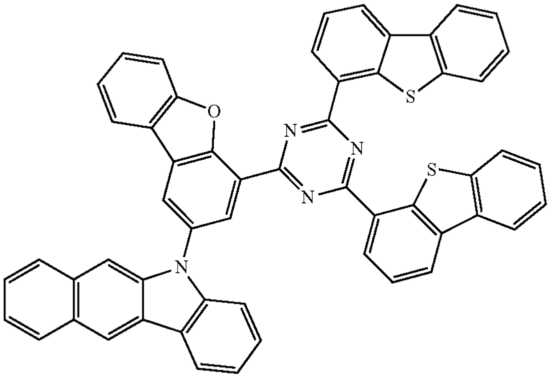
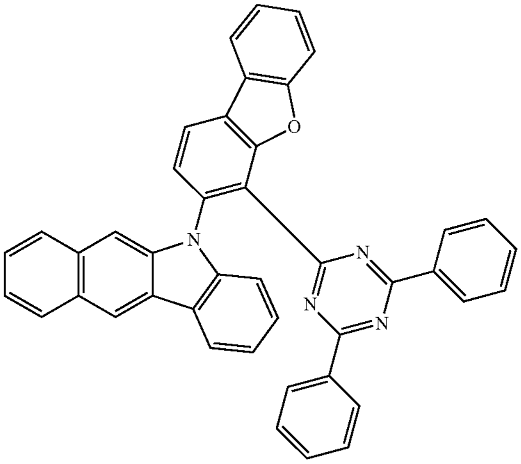

-continued
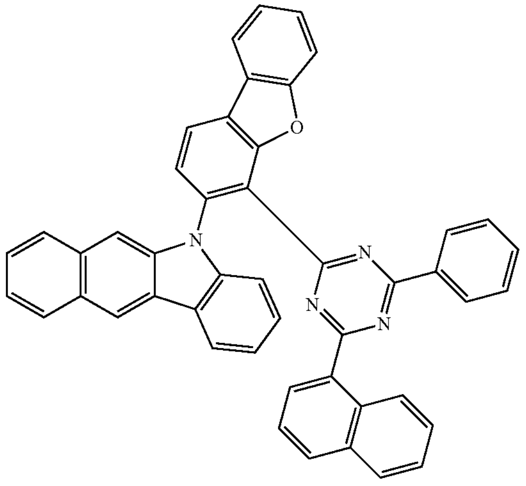
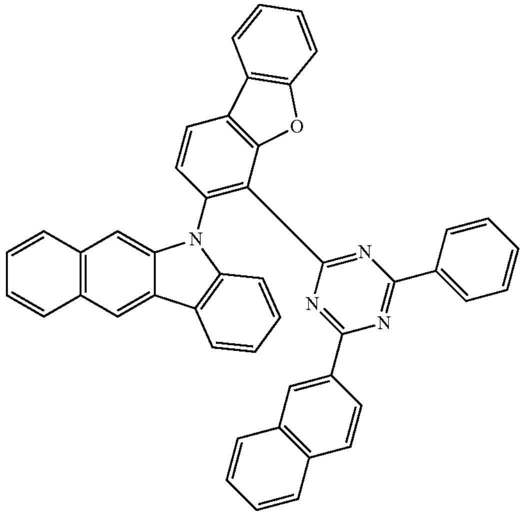
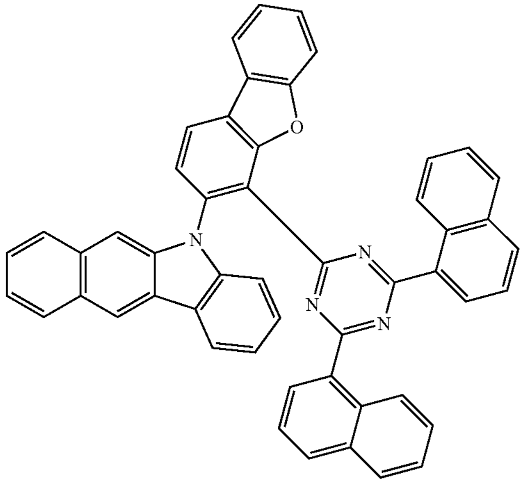
-continued
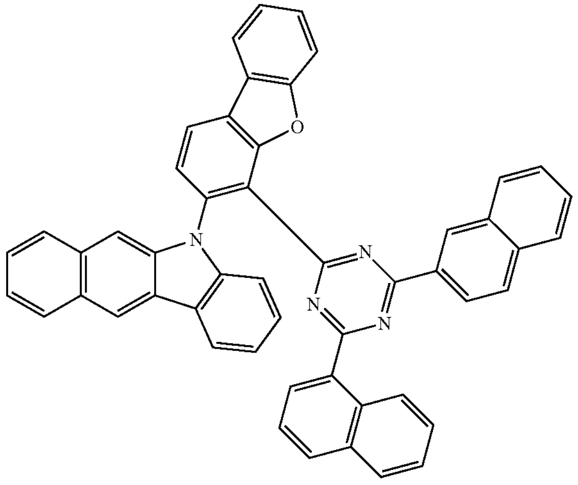
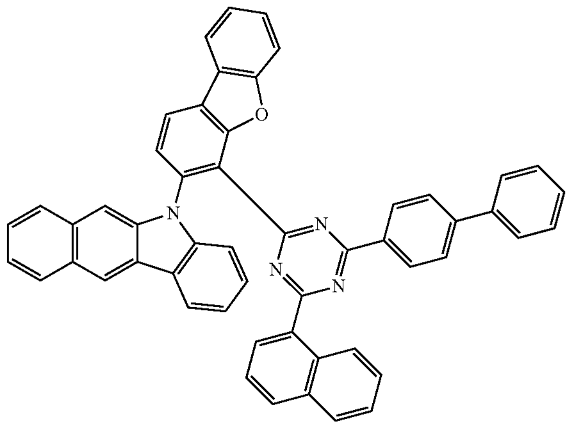
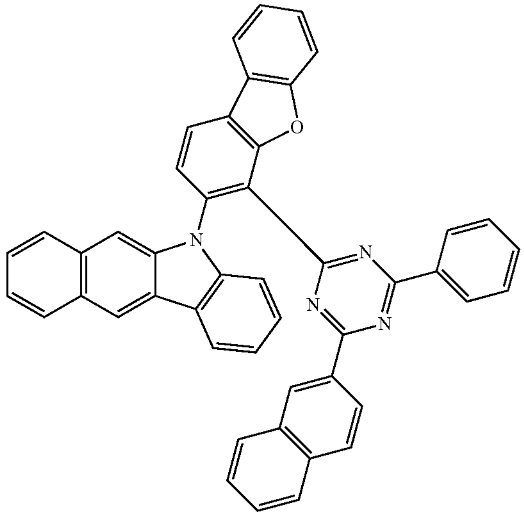

-continued
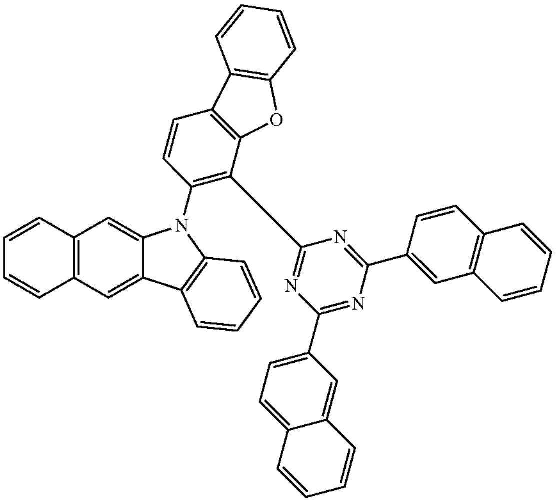
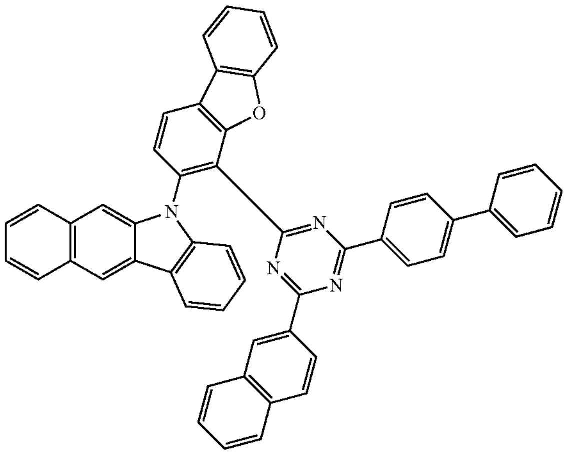
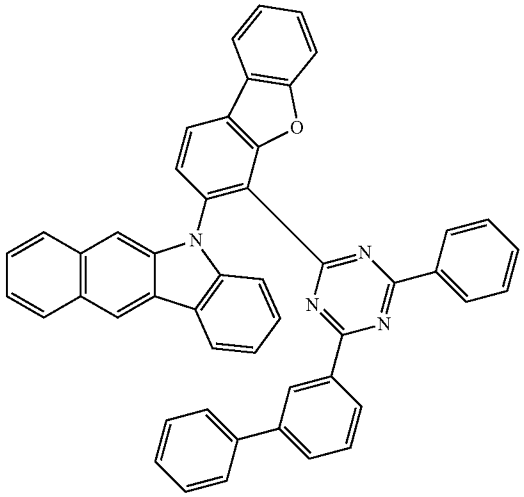
-continued
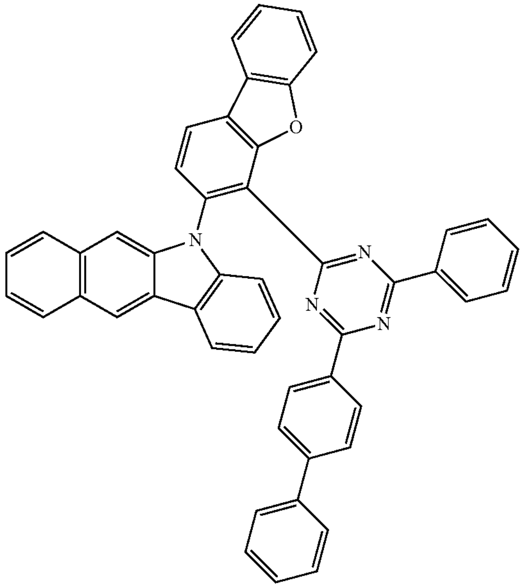
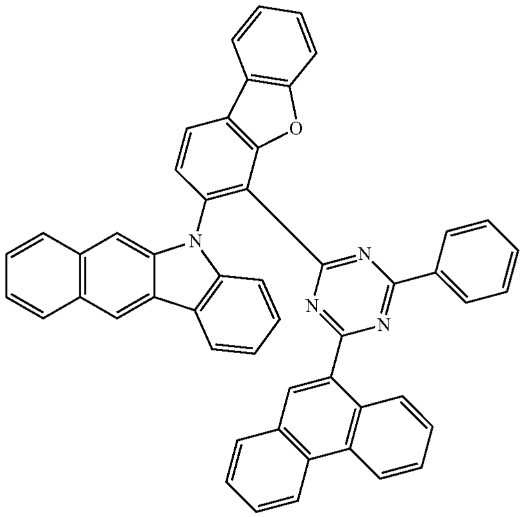
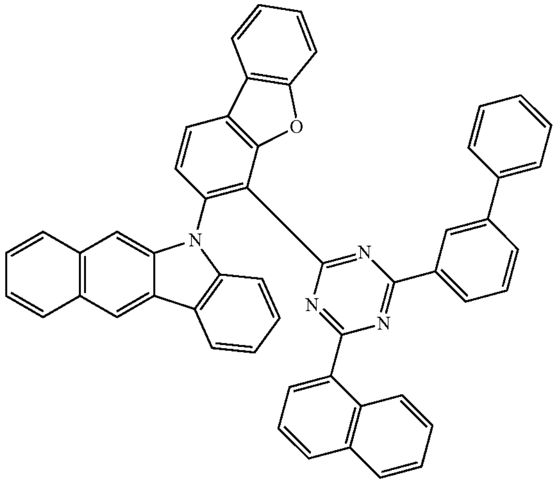

-continued
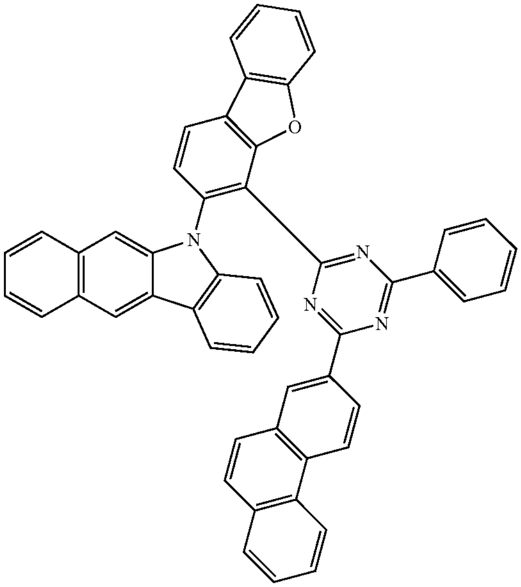
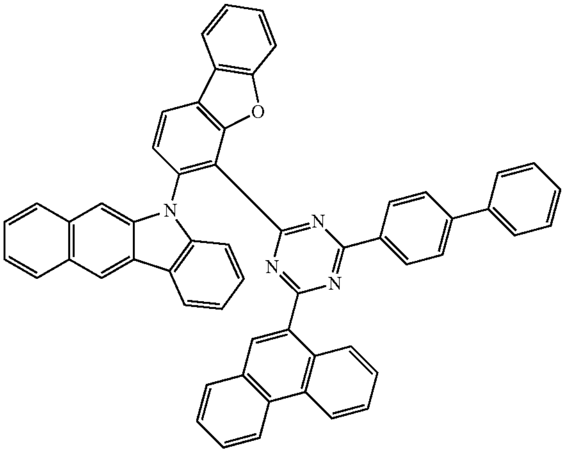
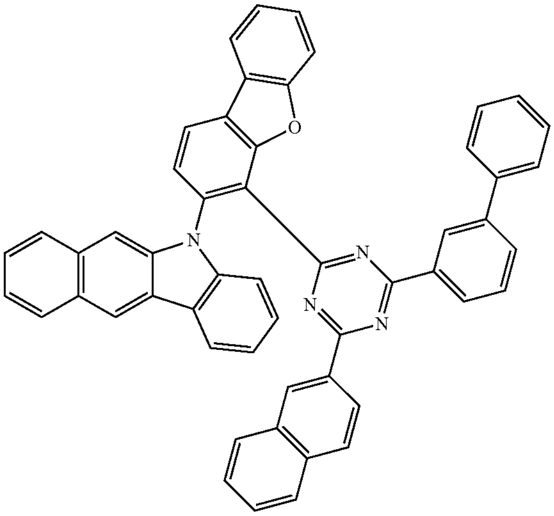
-continued
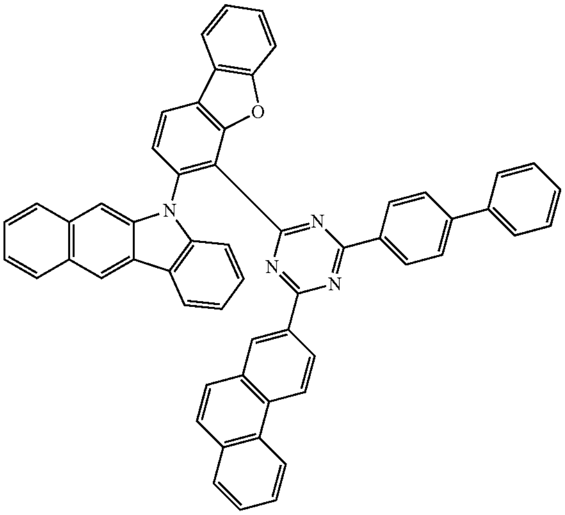
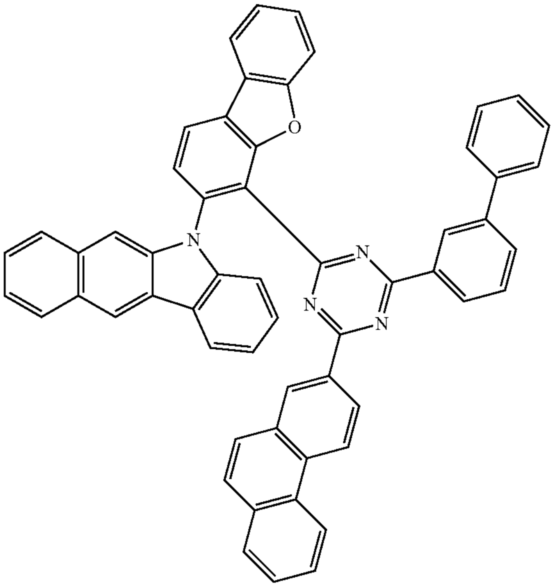
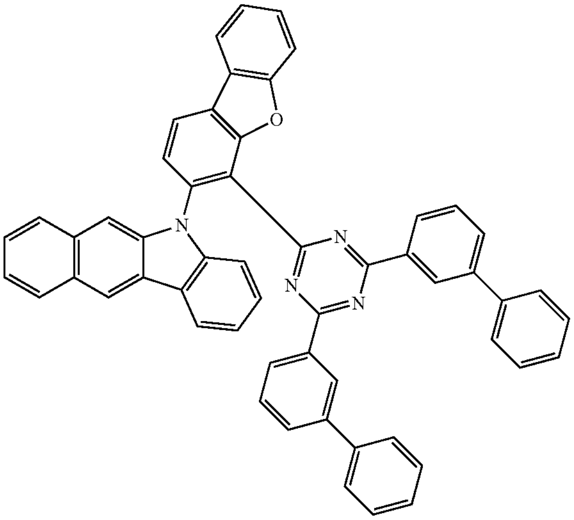

-continued
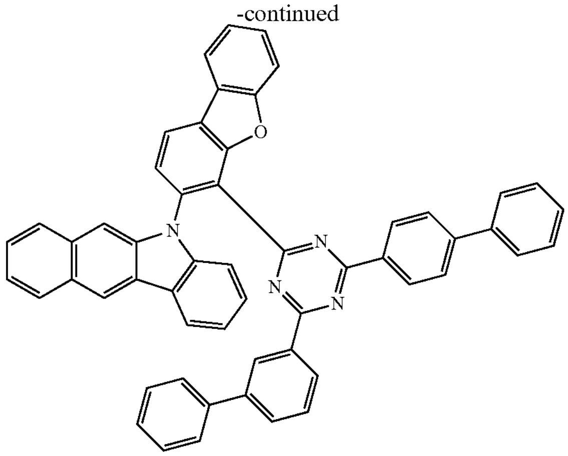
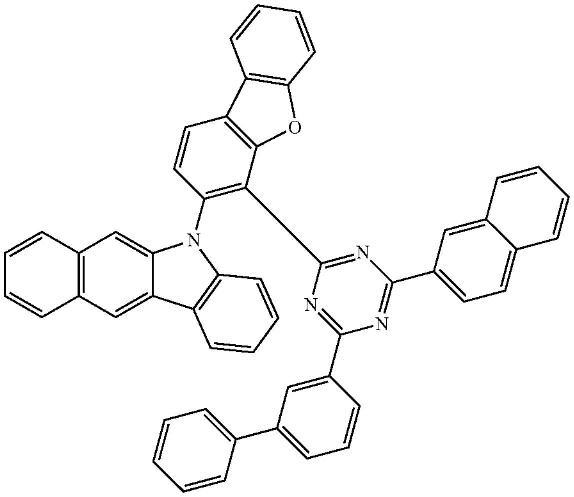
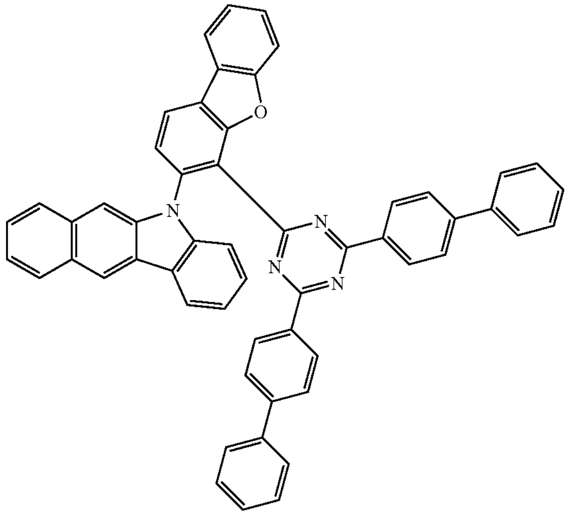
-continued
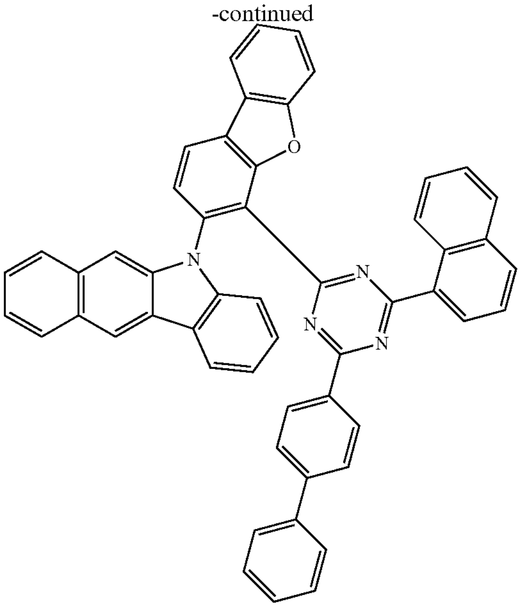
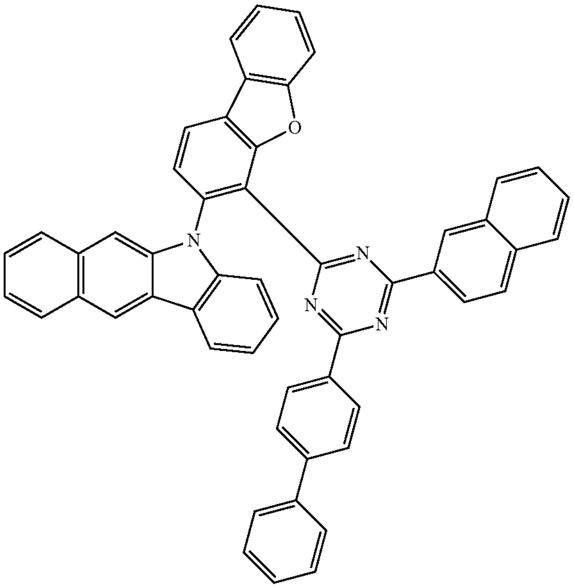
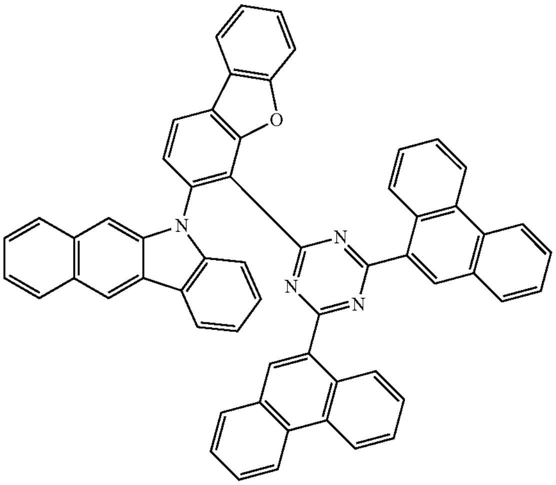

-continued
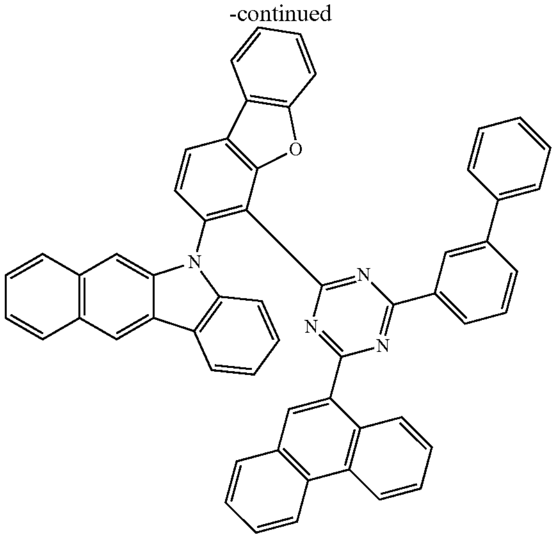
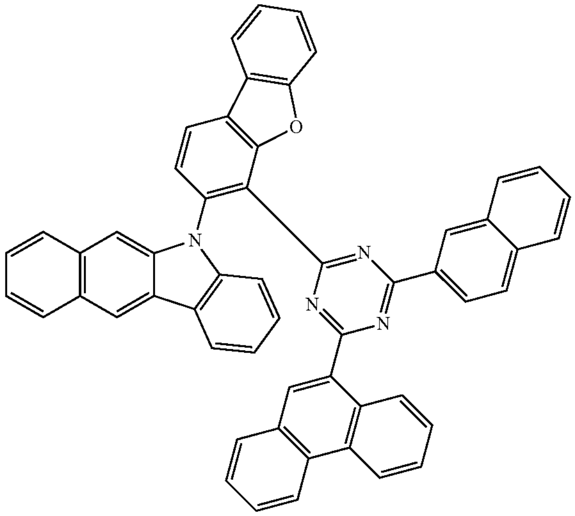
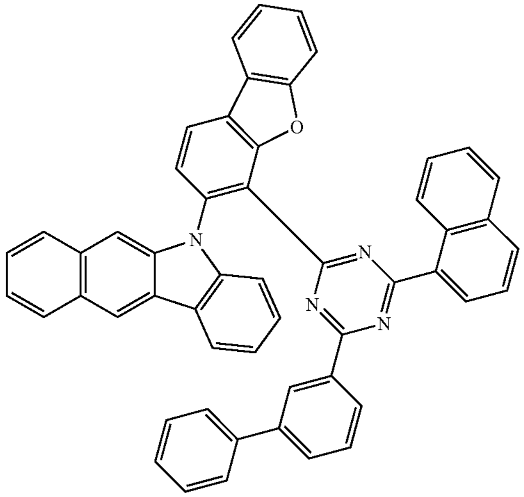
-continued
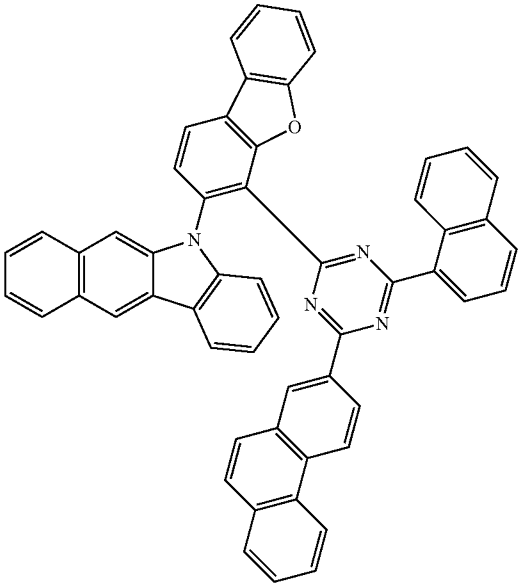
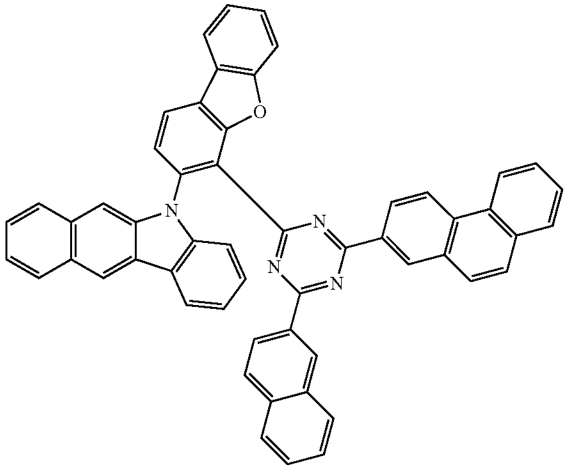
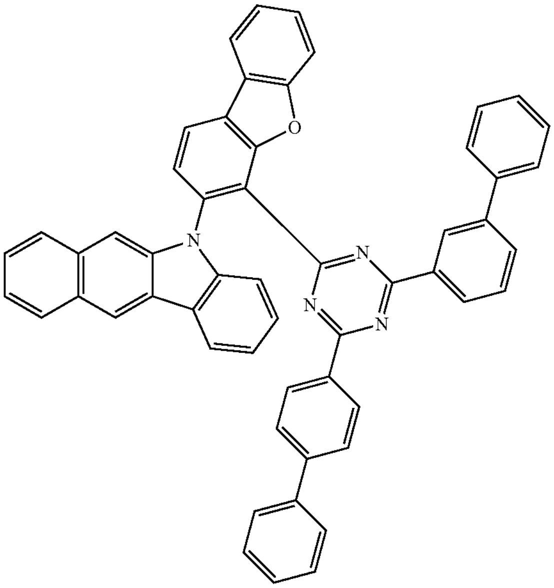

-continued
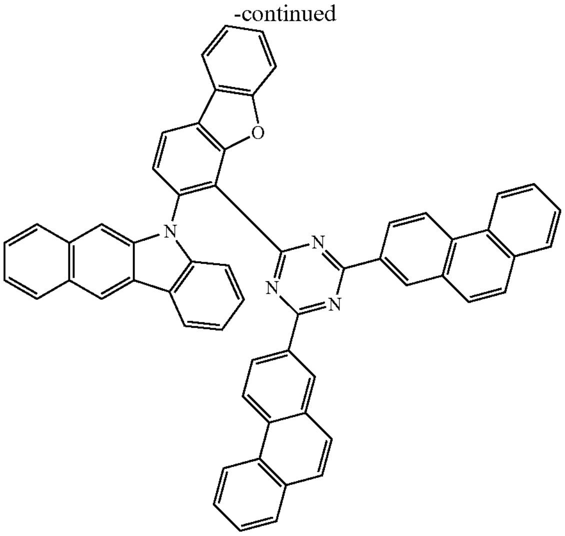
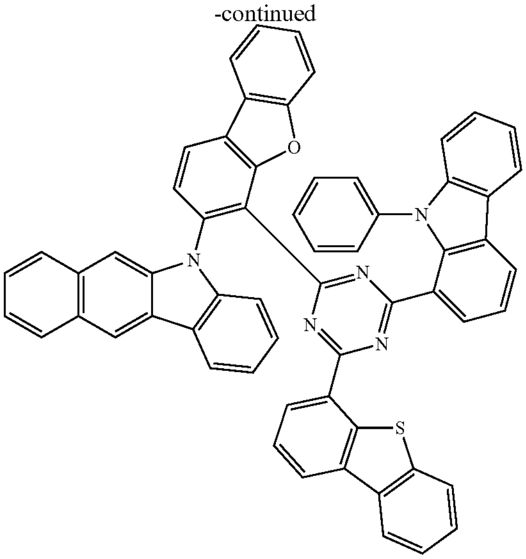
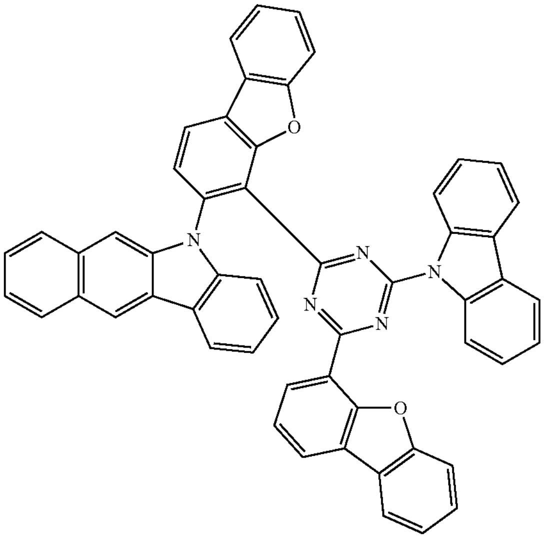
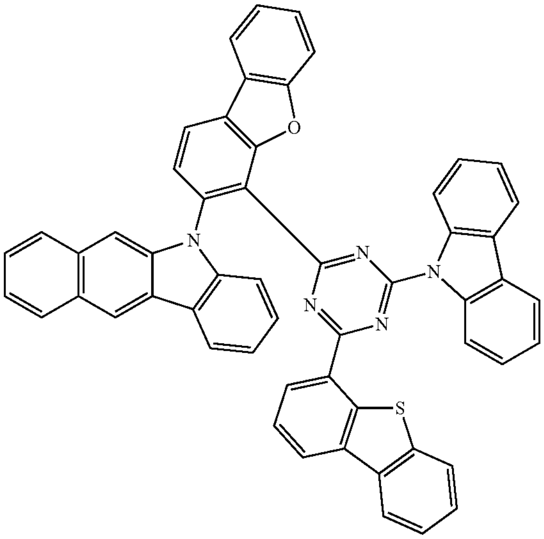
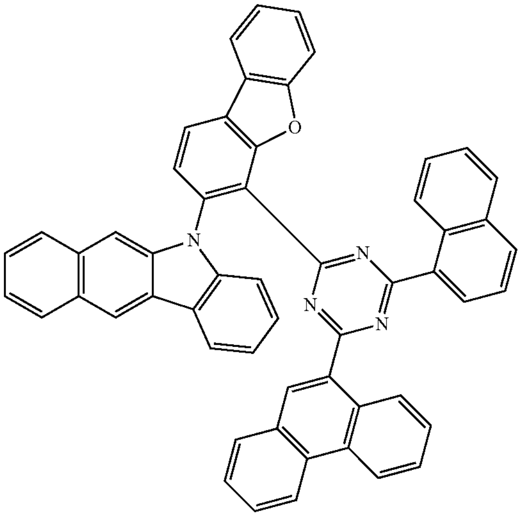
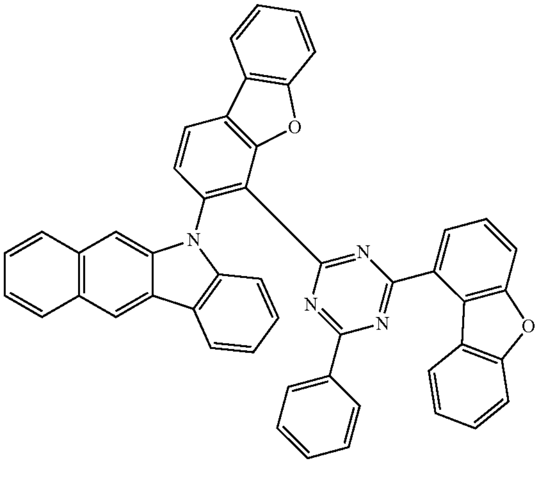
-continued -continued
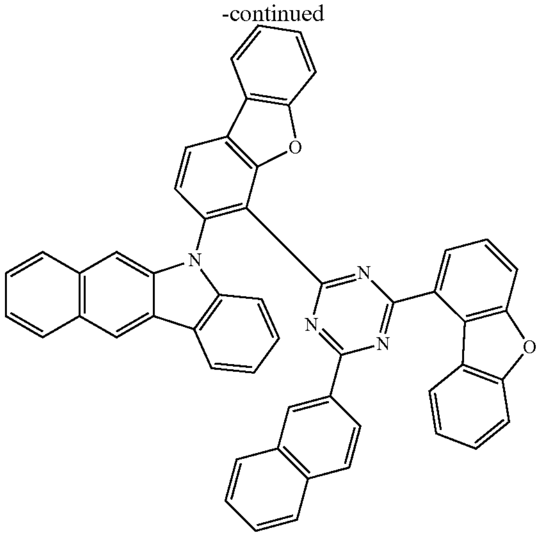
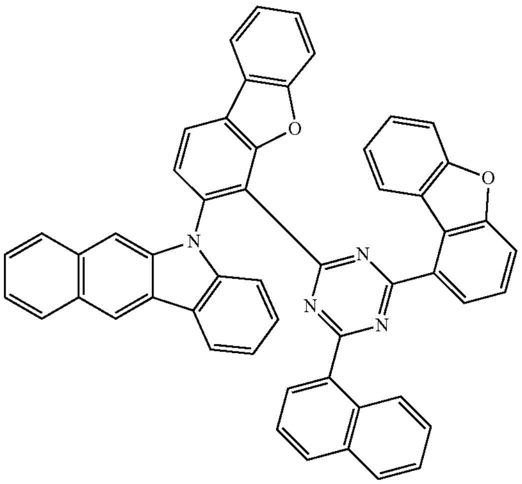
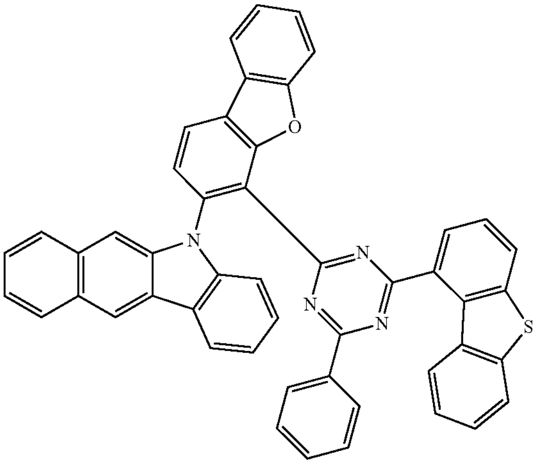
-continued
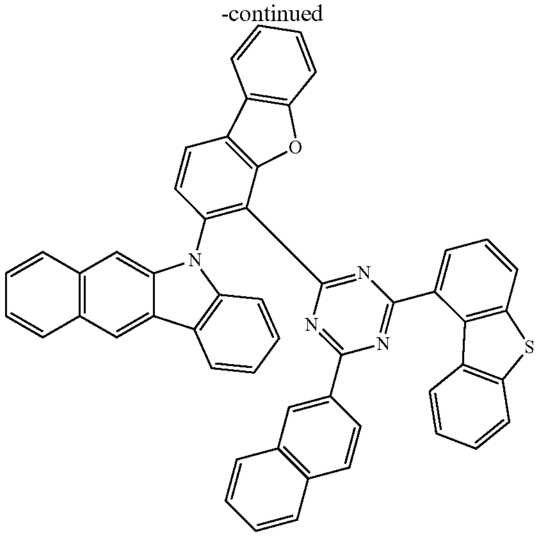
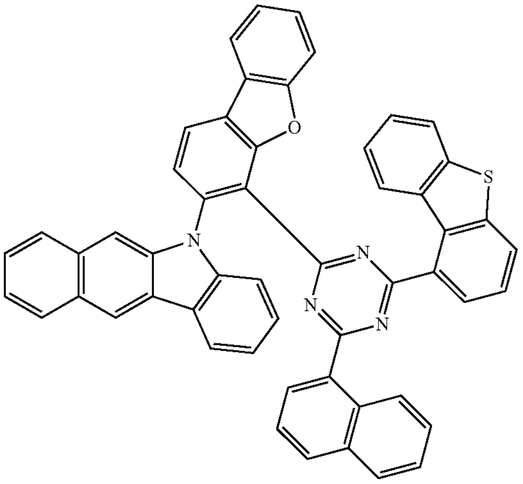
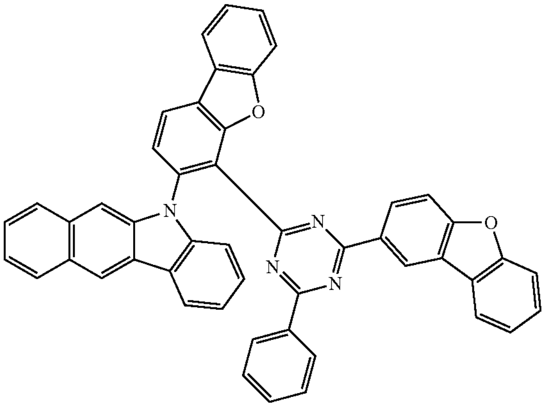

-continued
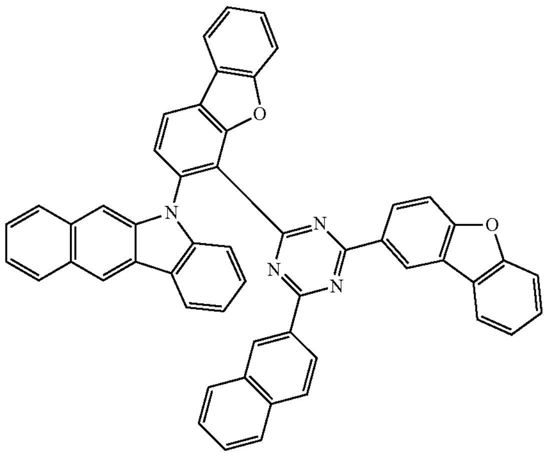
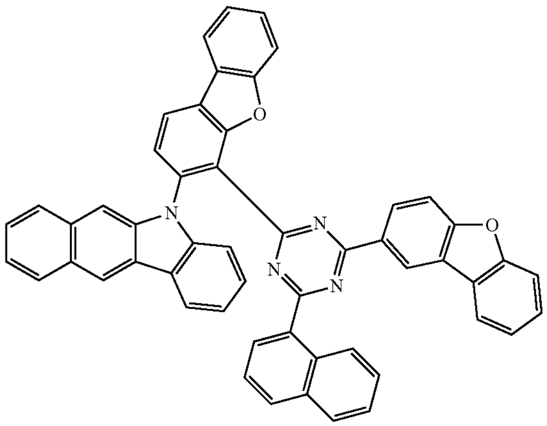
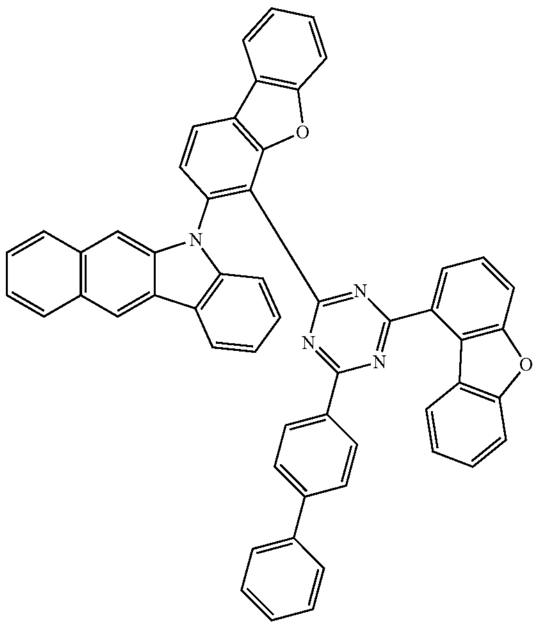
-continued
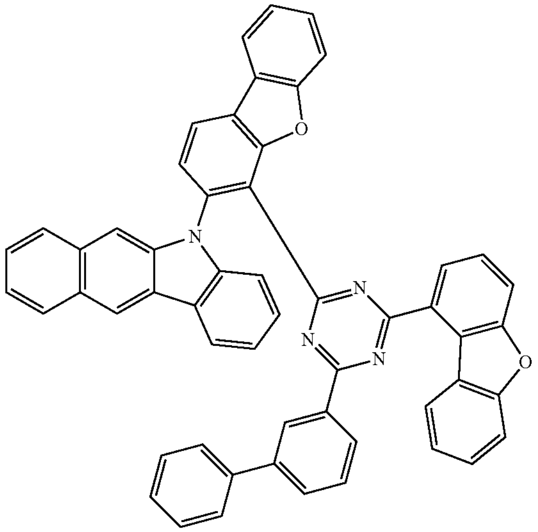
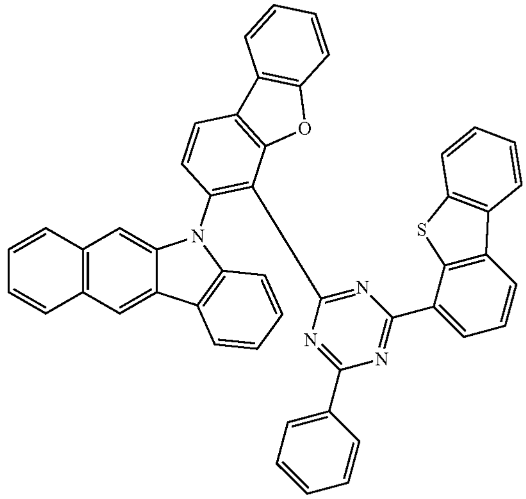
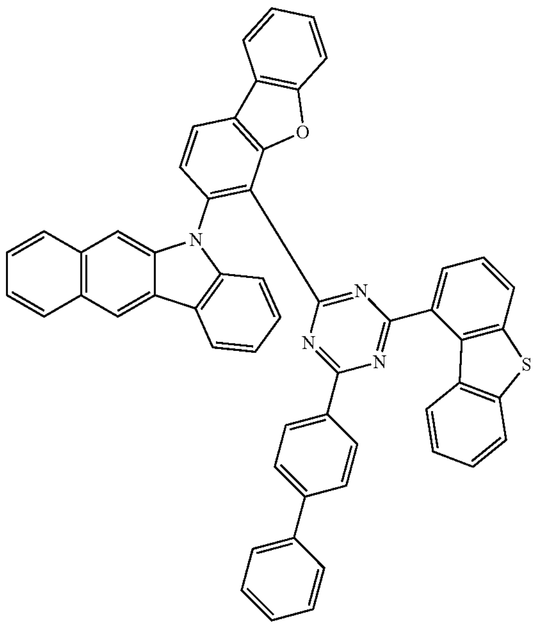

-continued
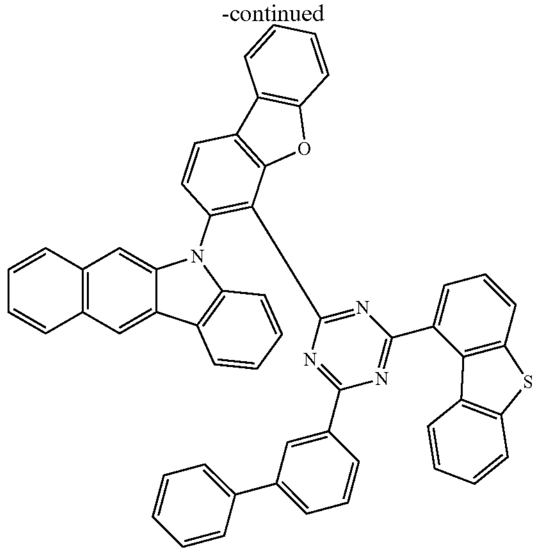
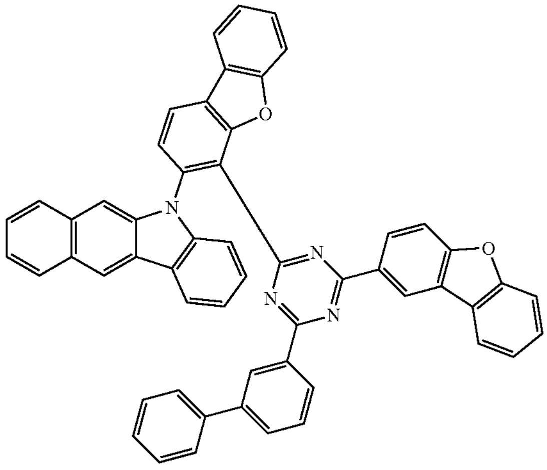
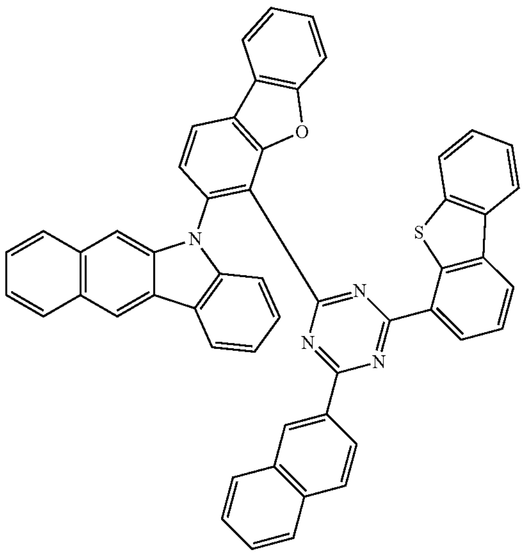
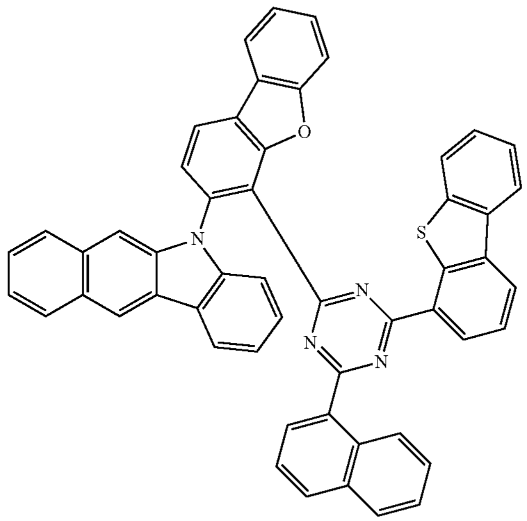
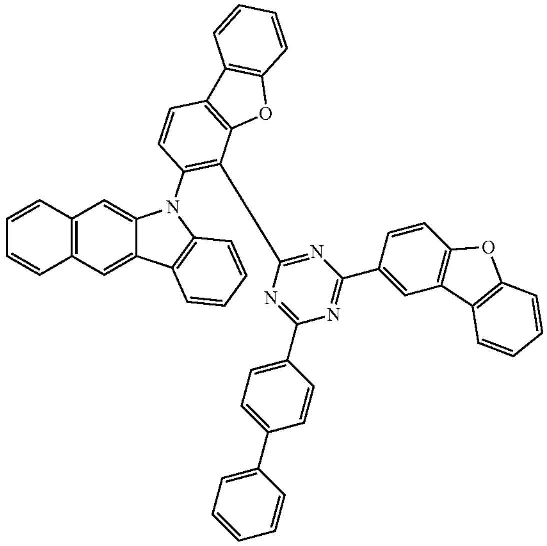
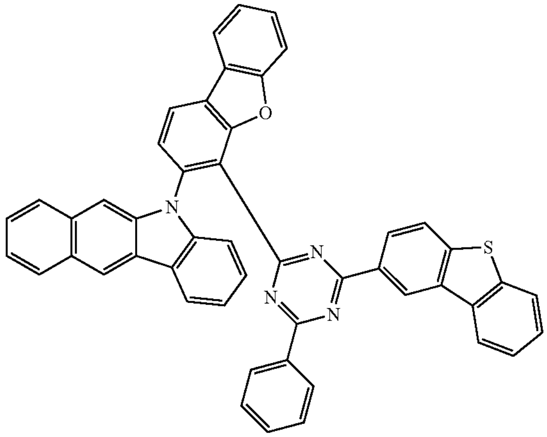
-continued -continued
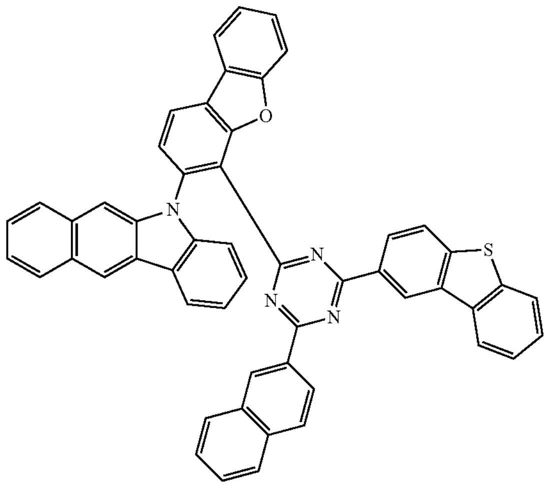
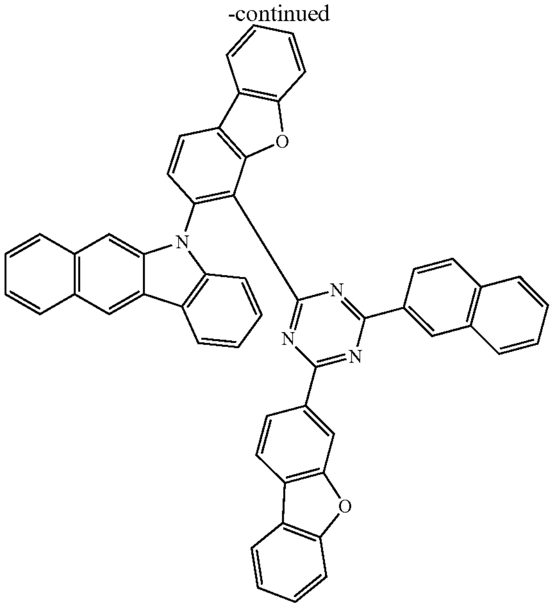
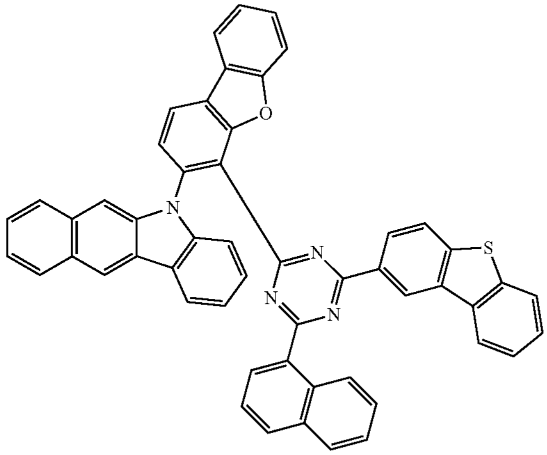
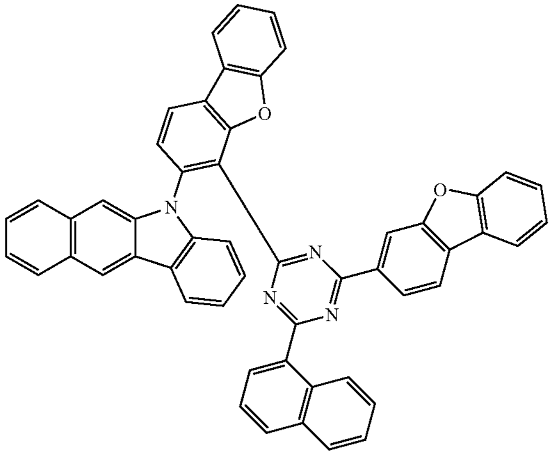
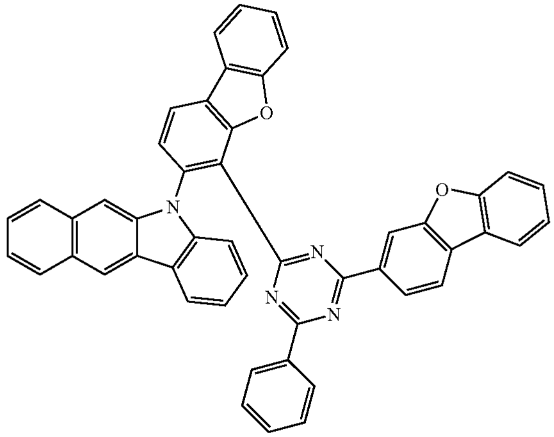
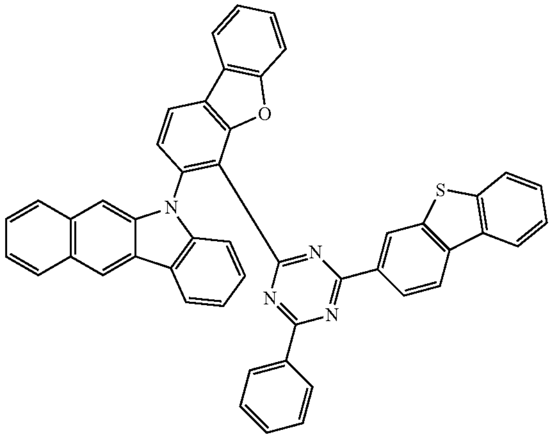
-continued -continued
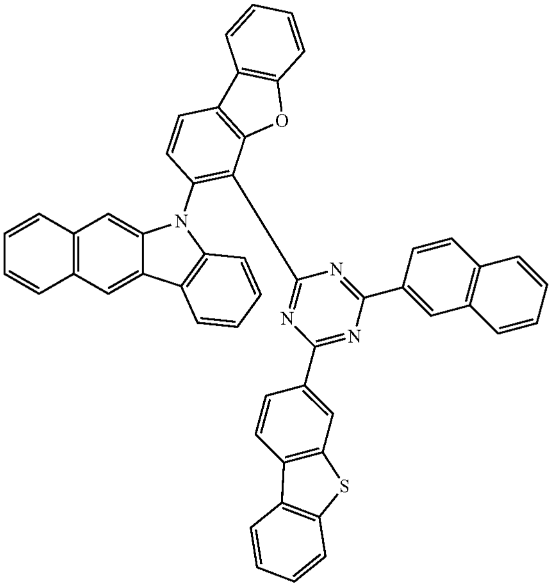
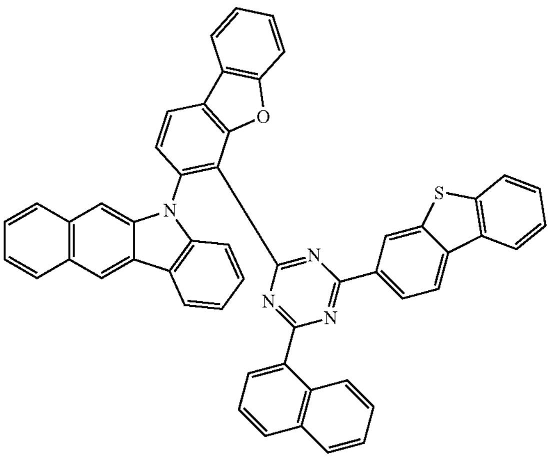
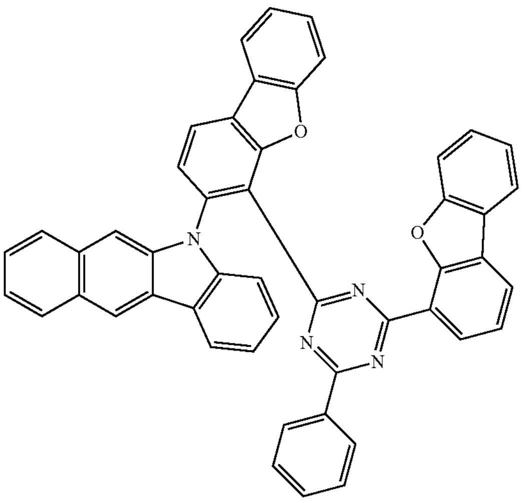
-continued
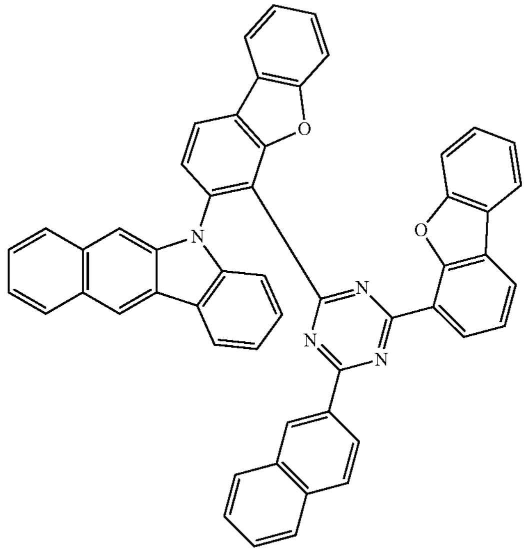
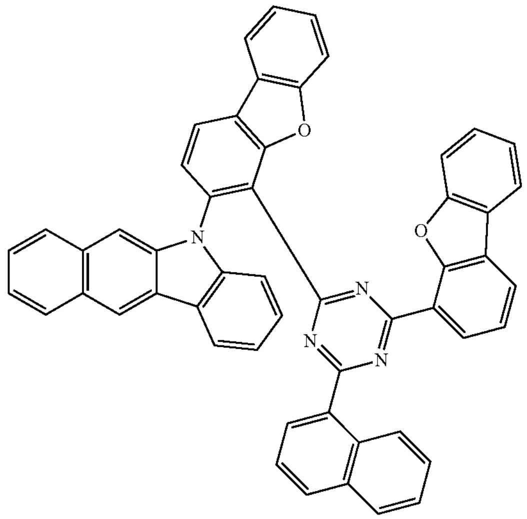
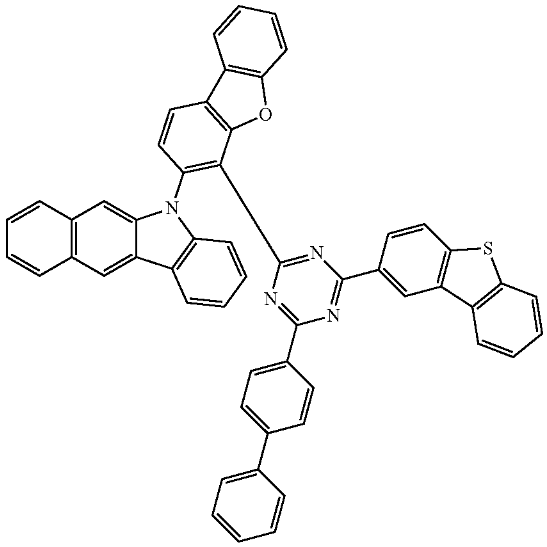

-continued
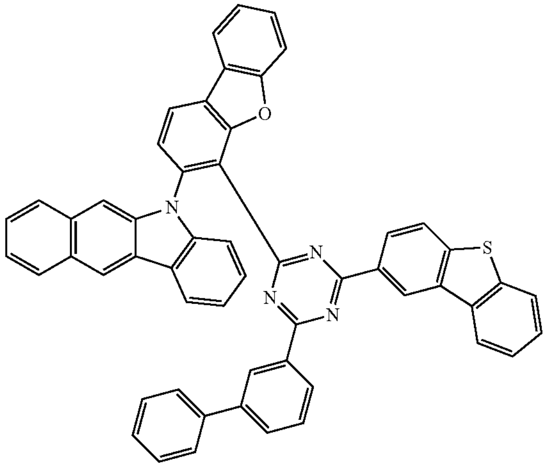
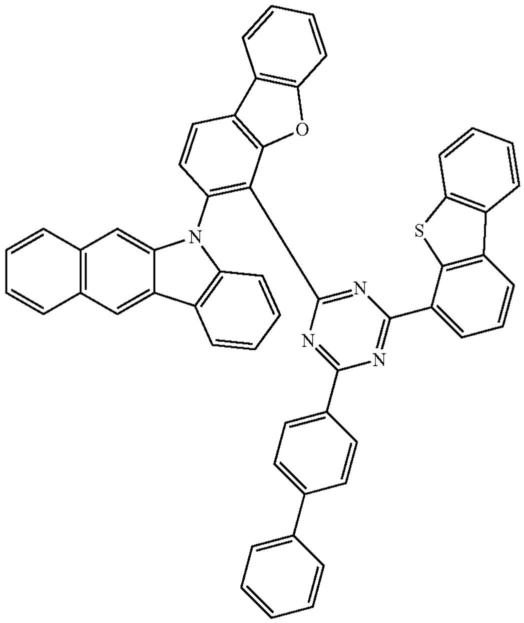
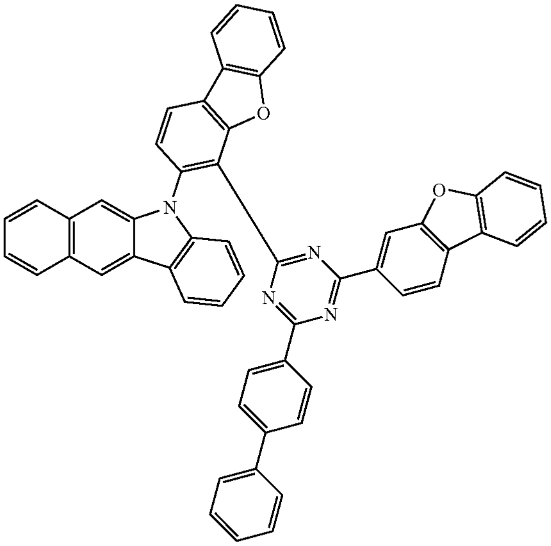
-continued
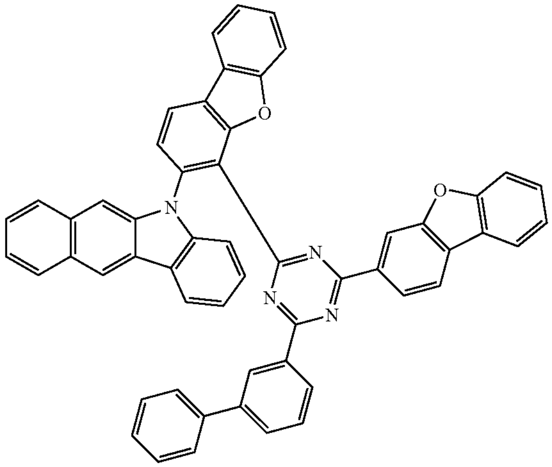
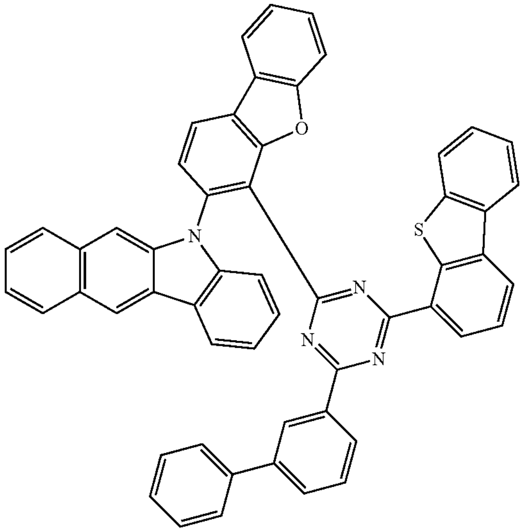
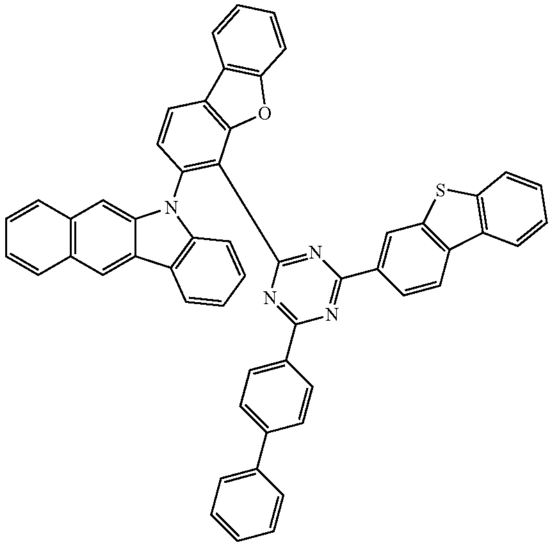

-continued
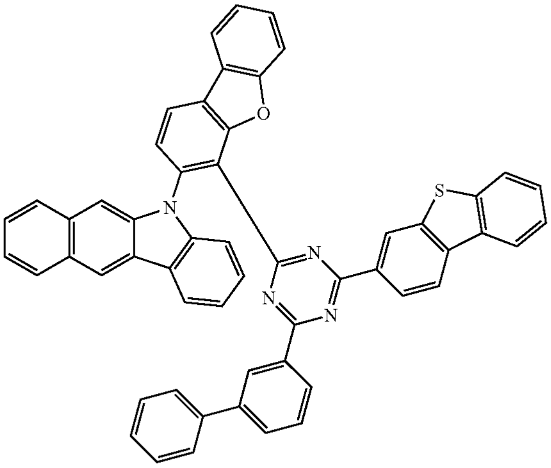
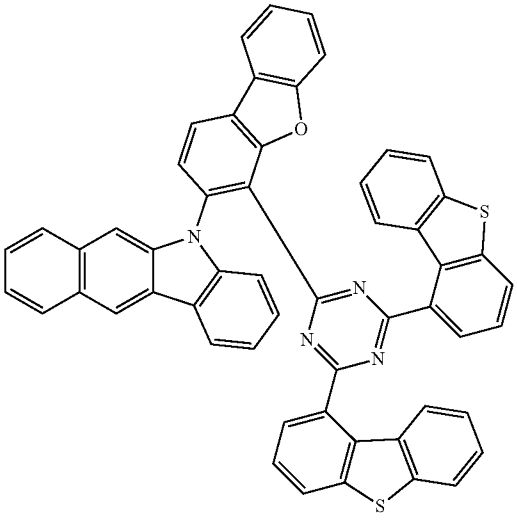
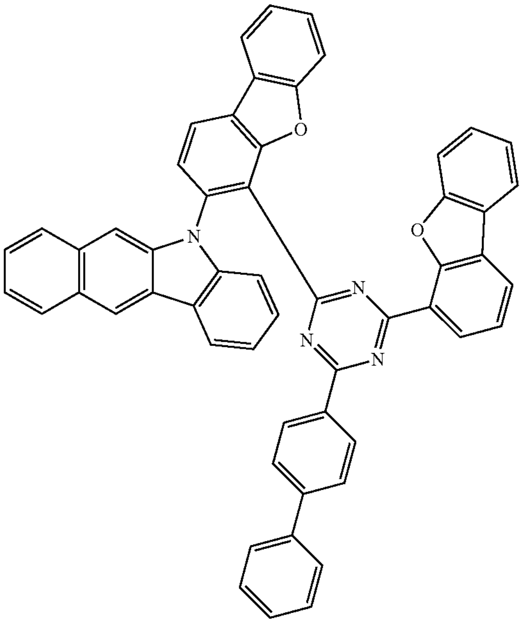
-continued
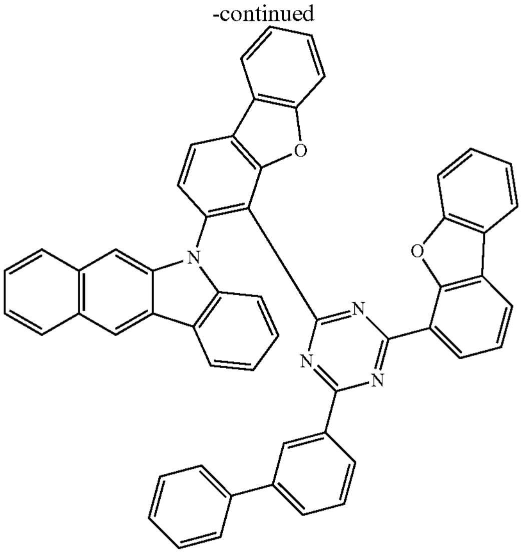
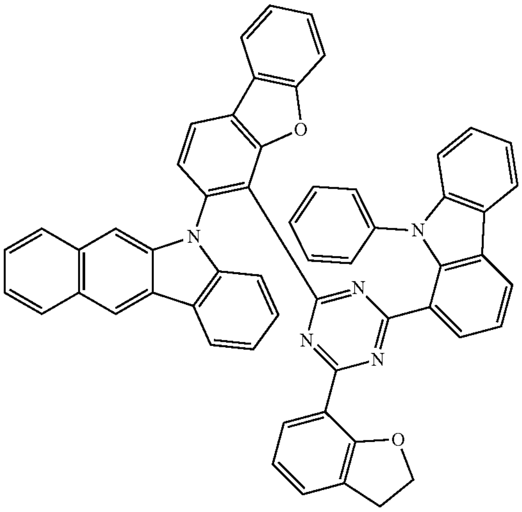
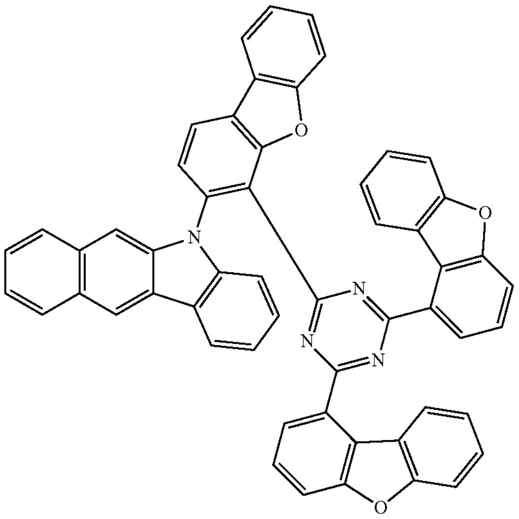

-continued
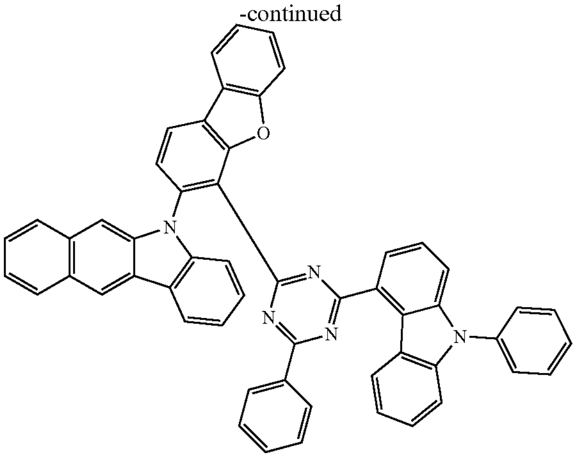
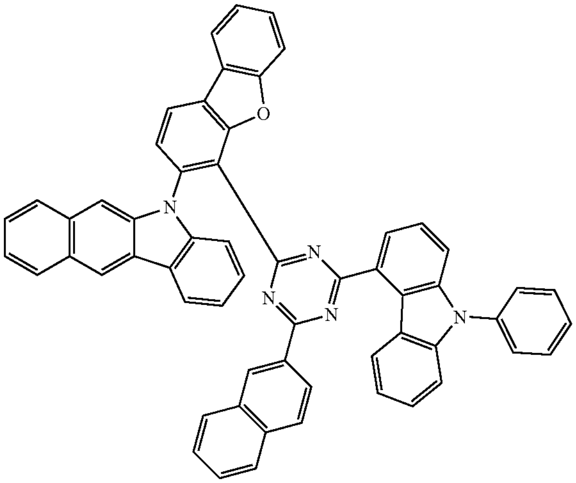
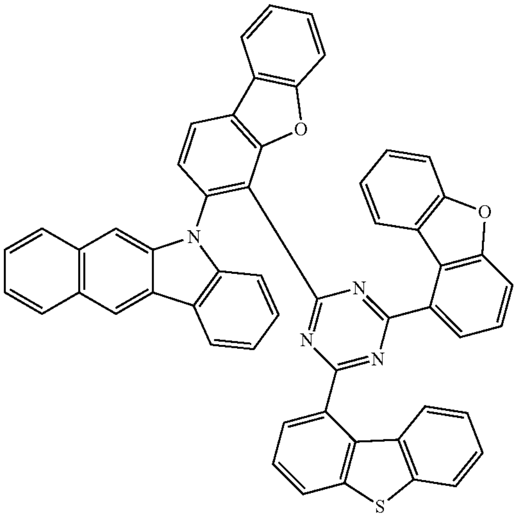
-continued
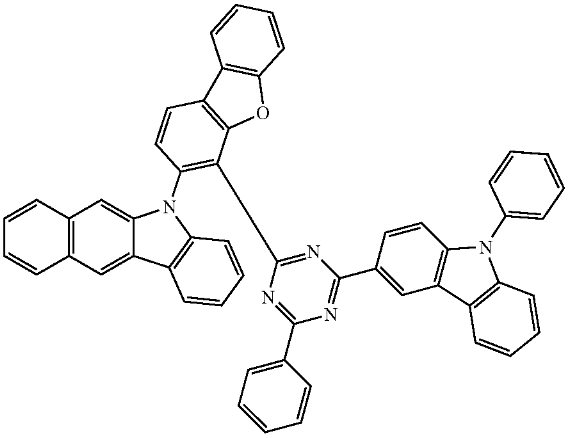
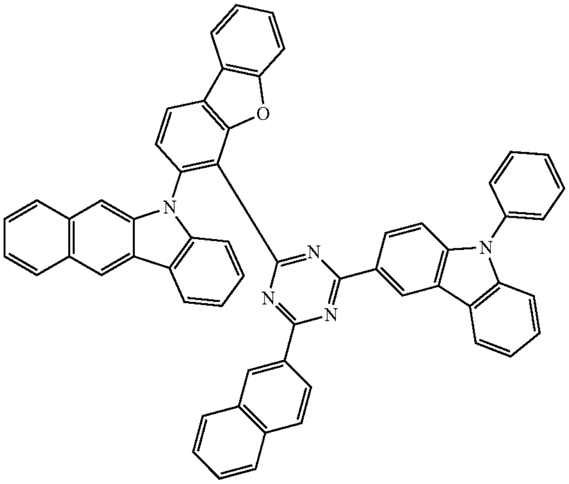
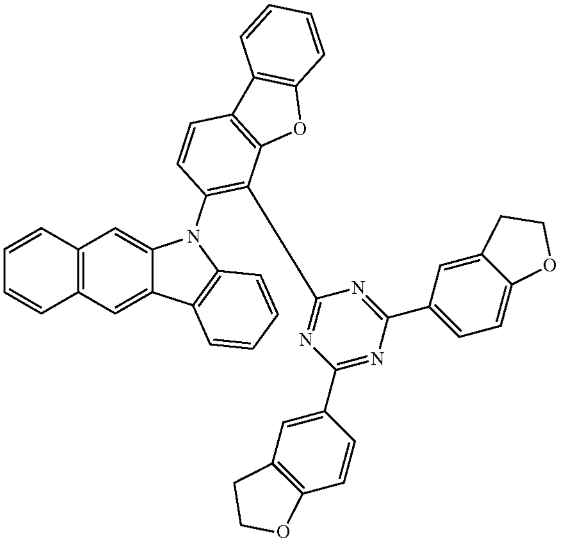

-continued
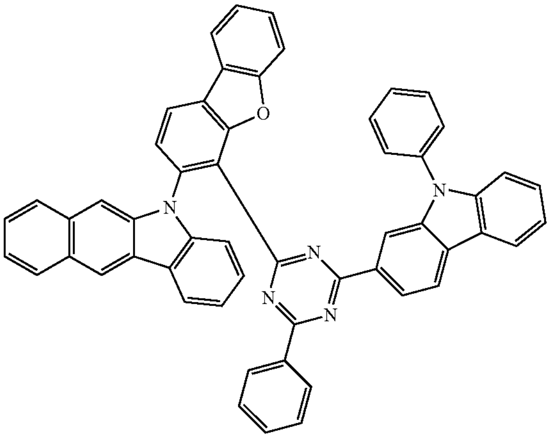
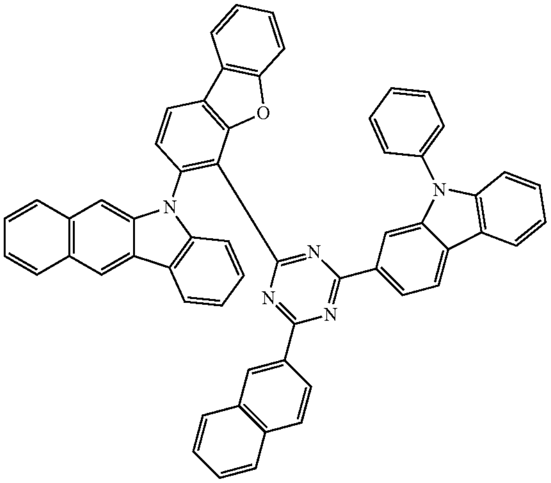
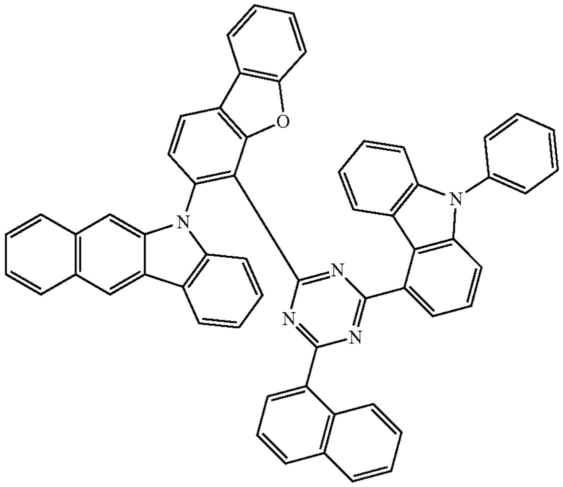
-continued
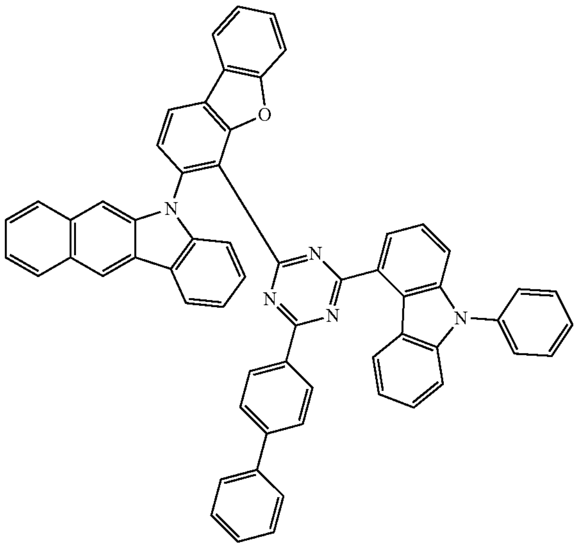
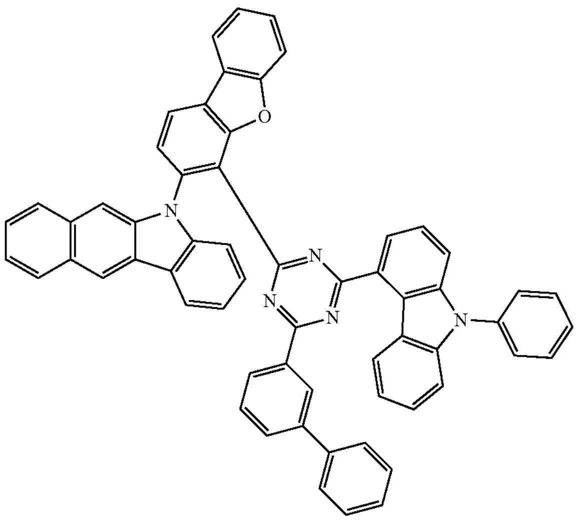
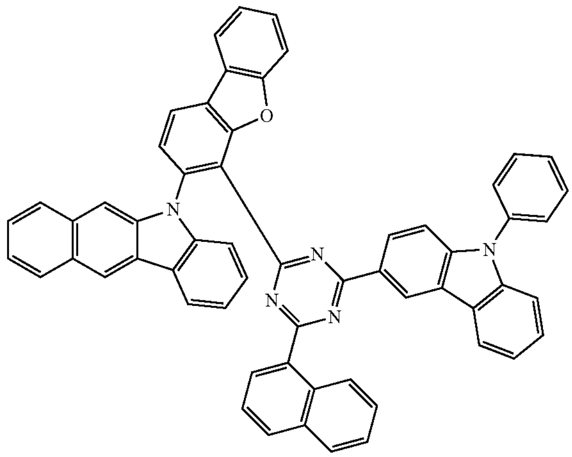

-continued
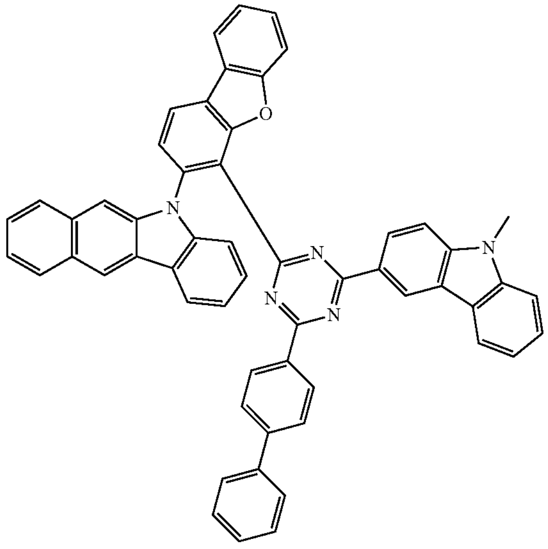
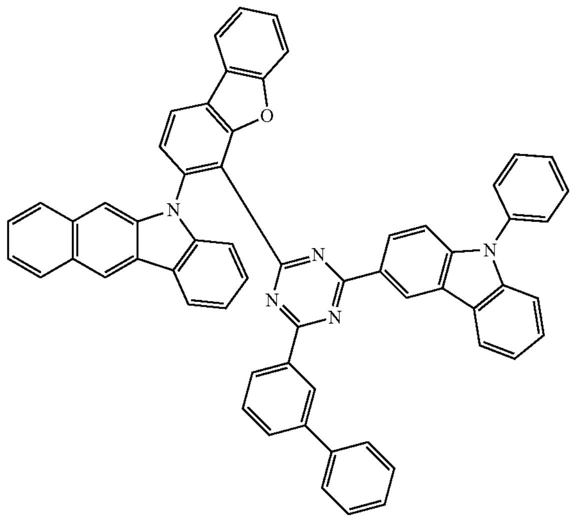
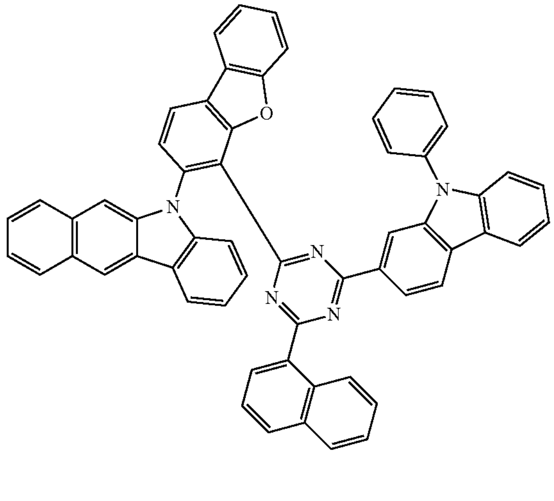
-continued
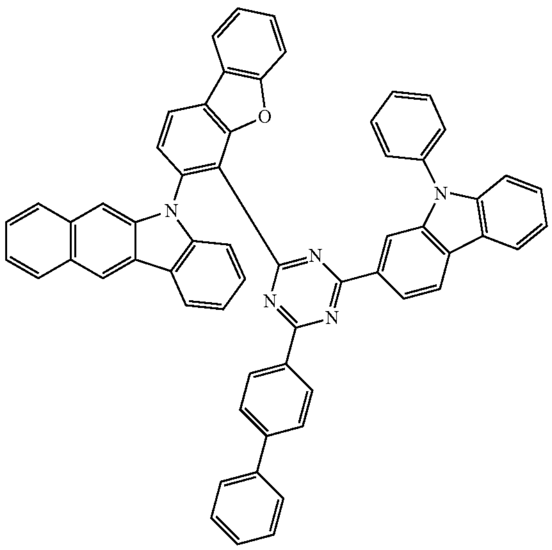
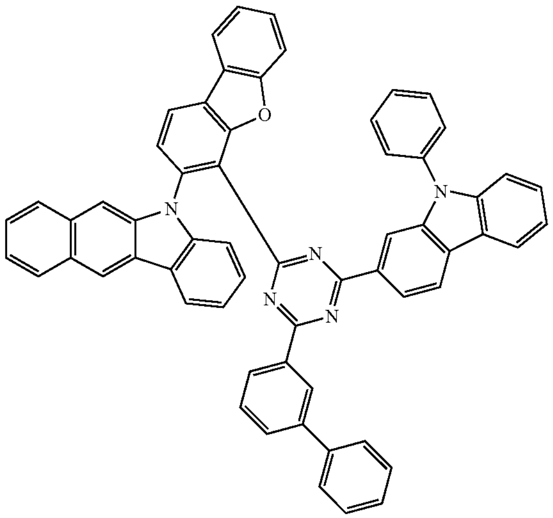
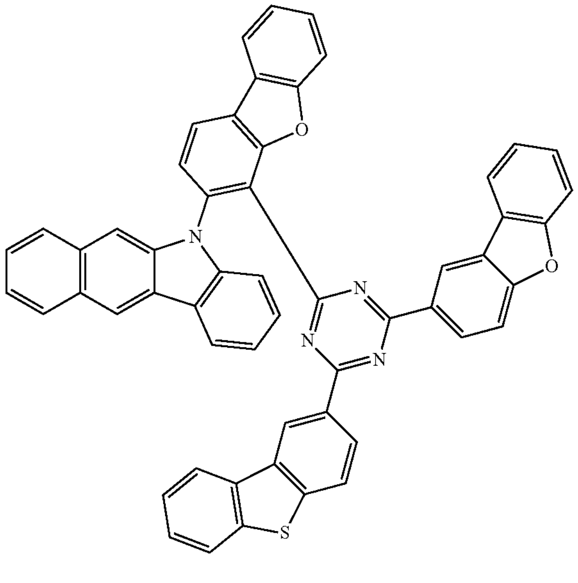

-continued
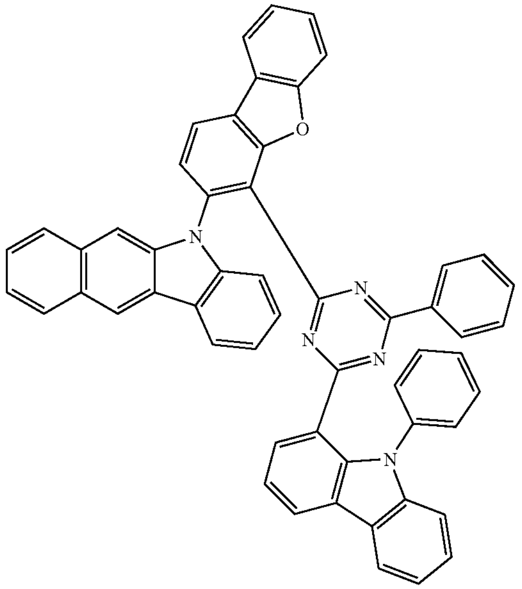
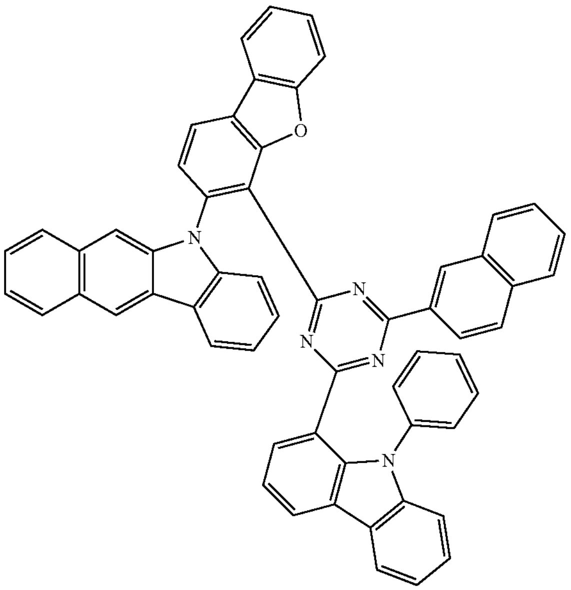
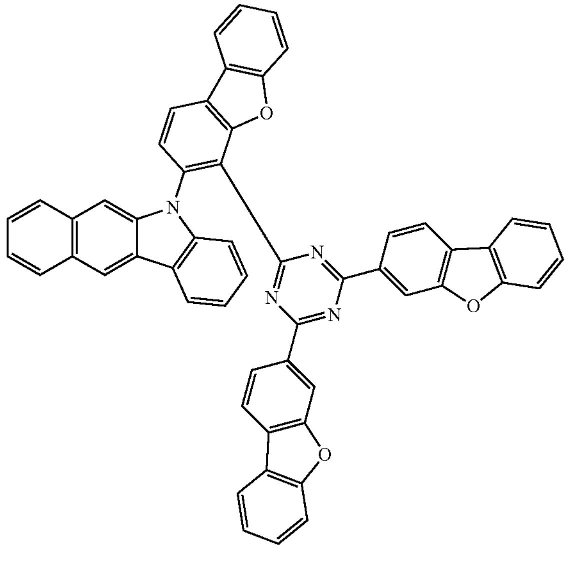
-continued
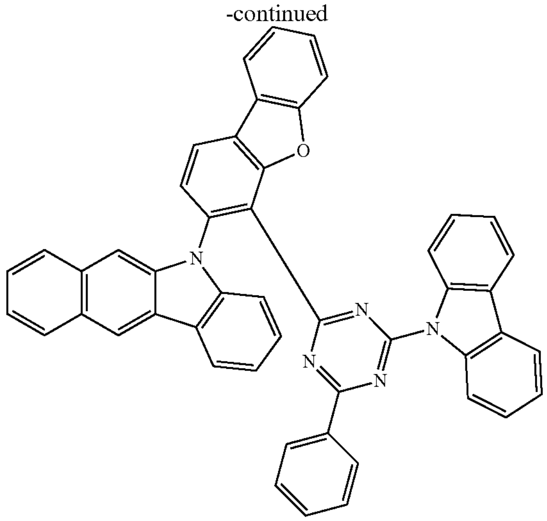
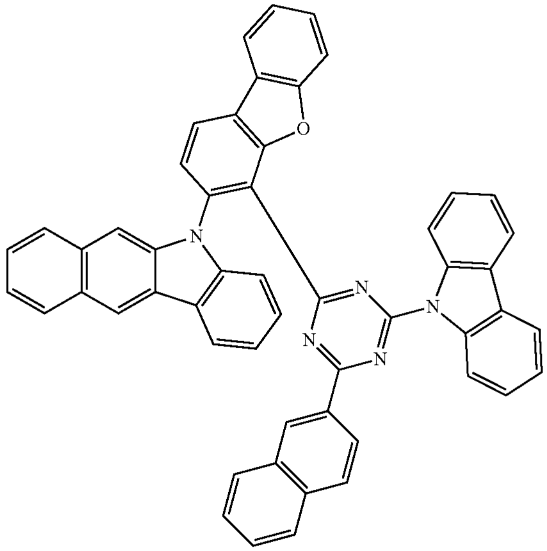
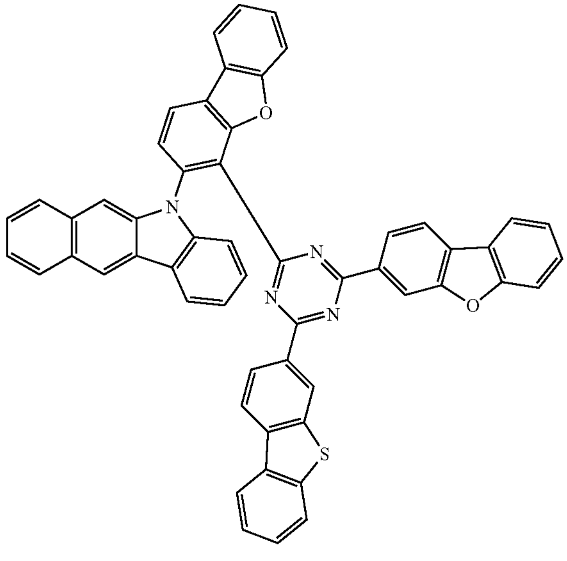

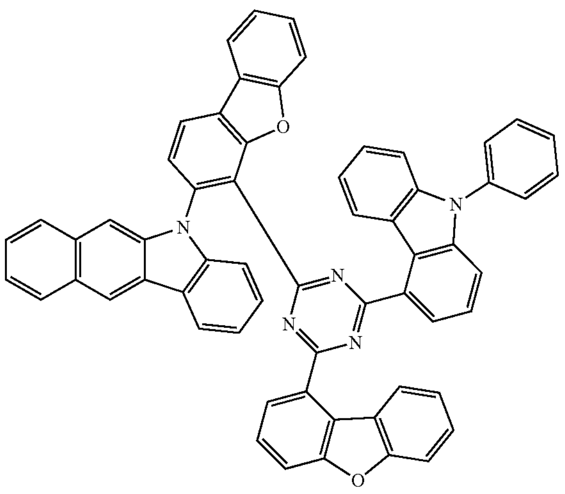
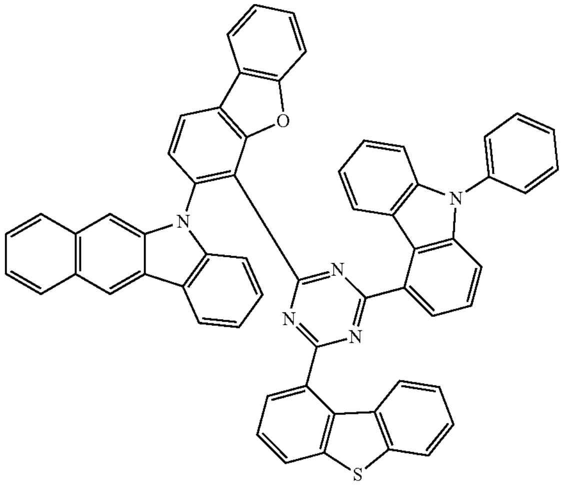
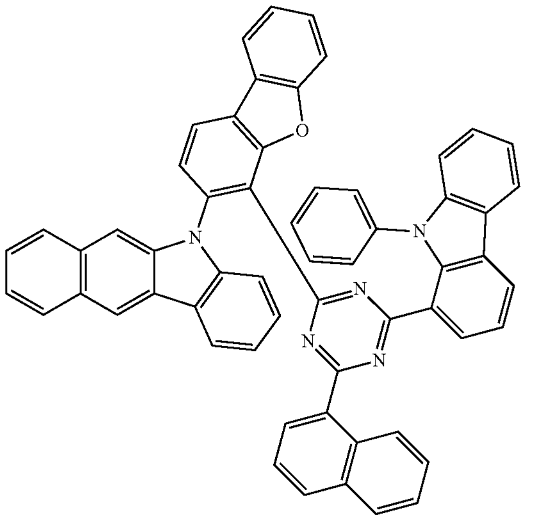
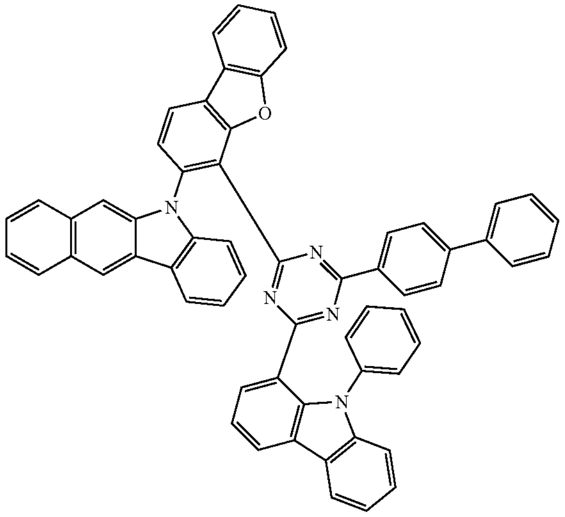
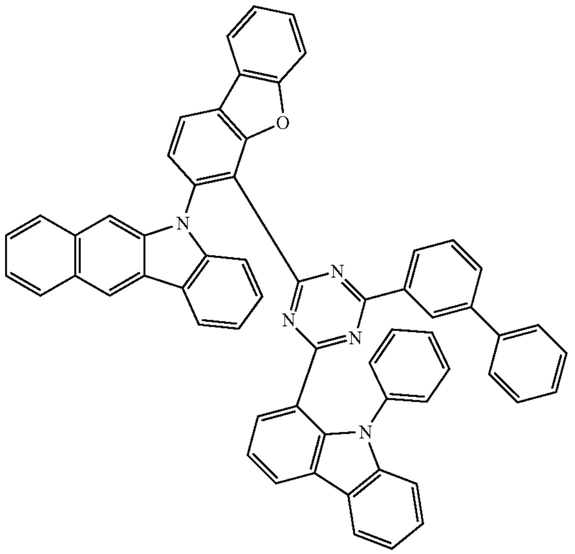
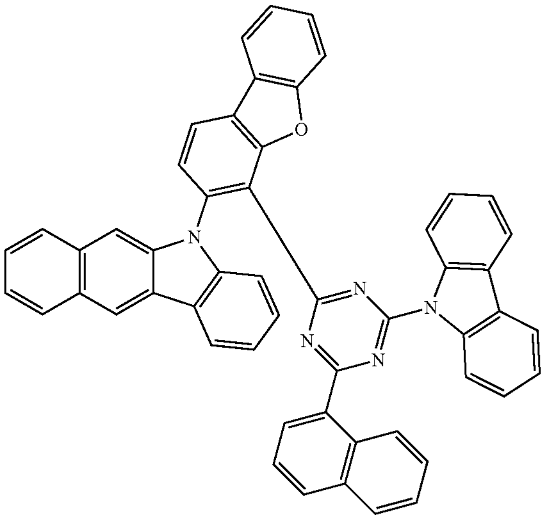

-continued
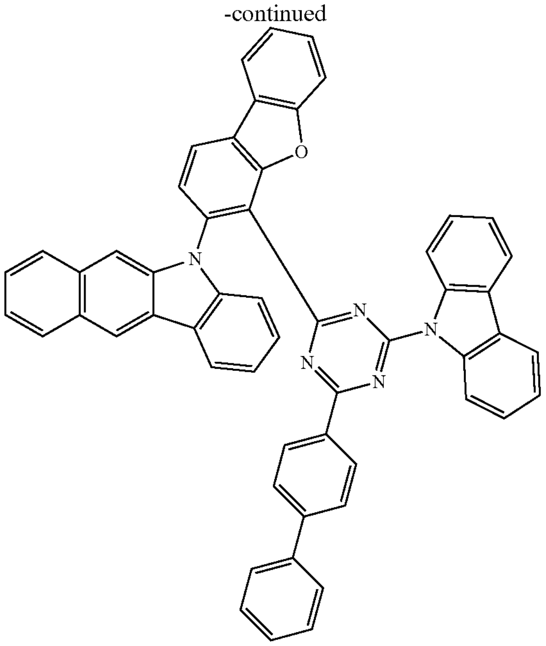
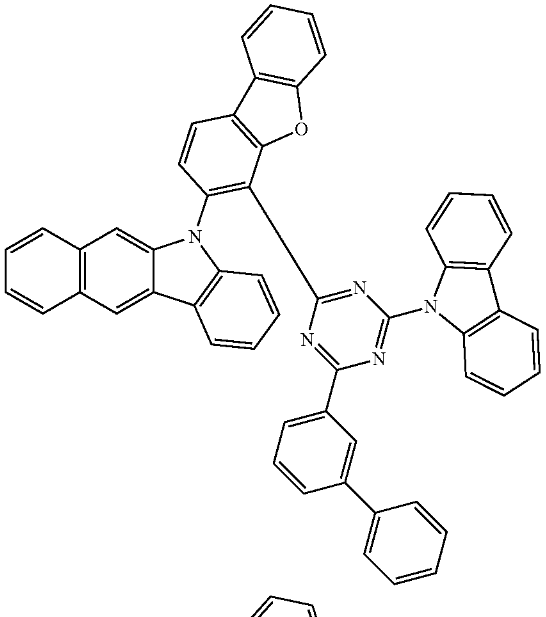
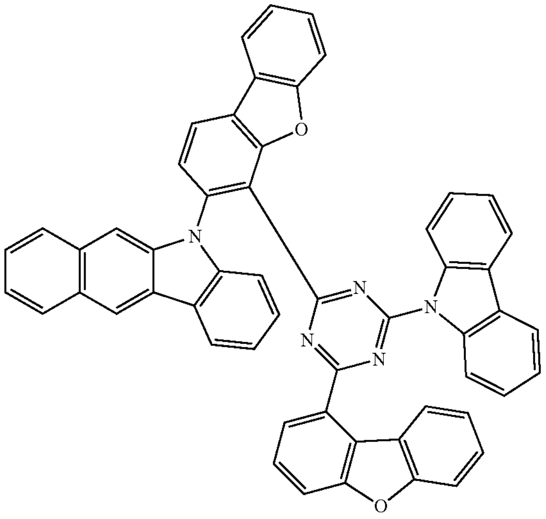
-continued
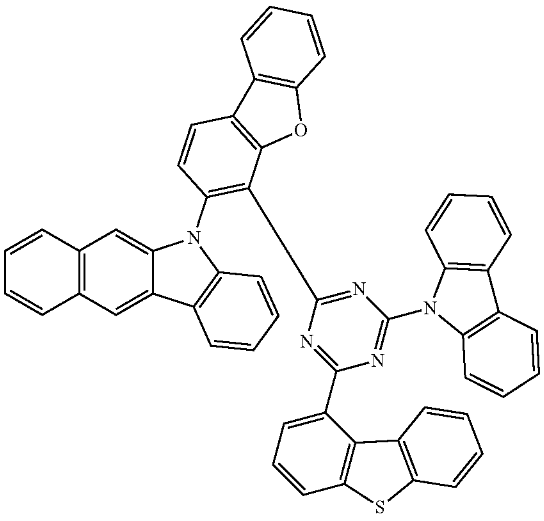
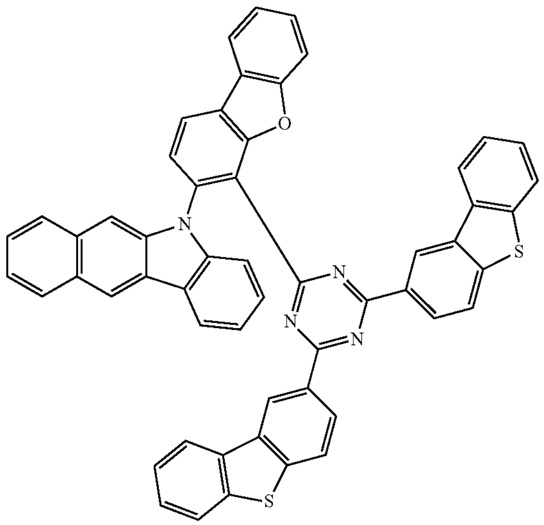
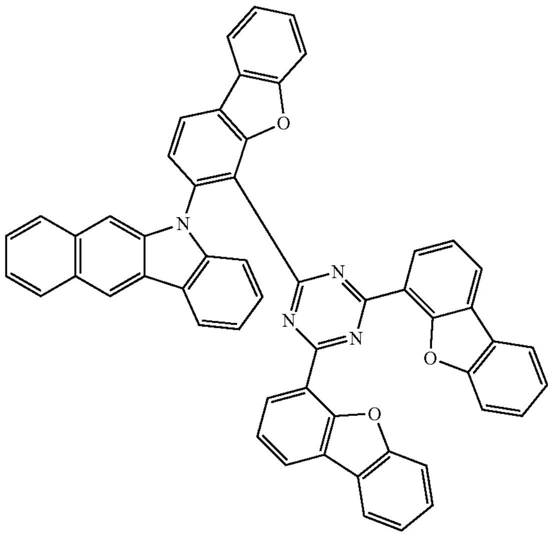

-continued
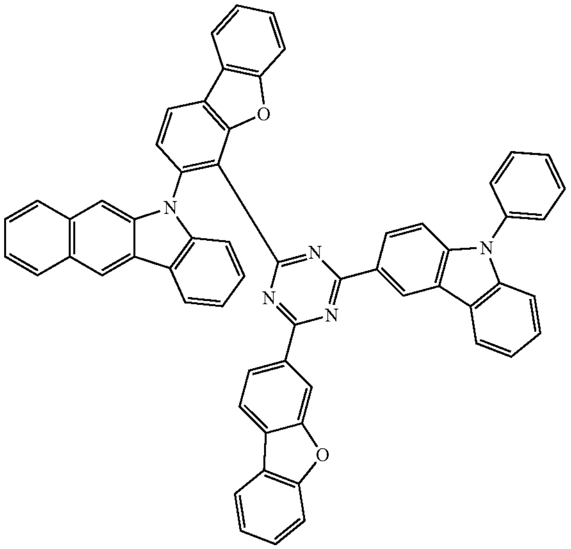
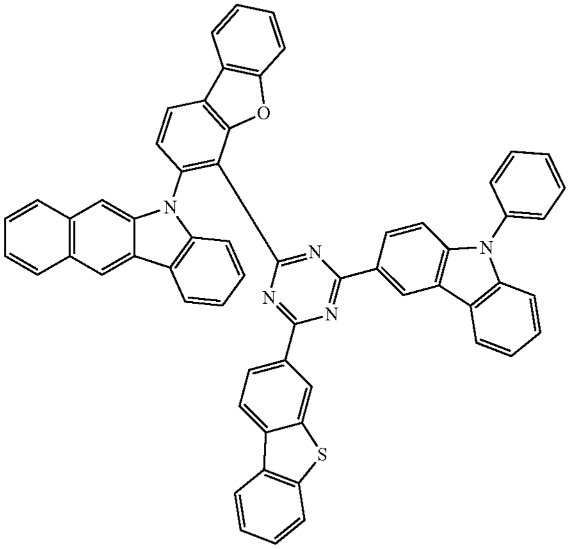
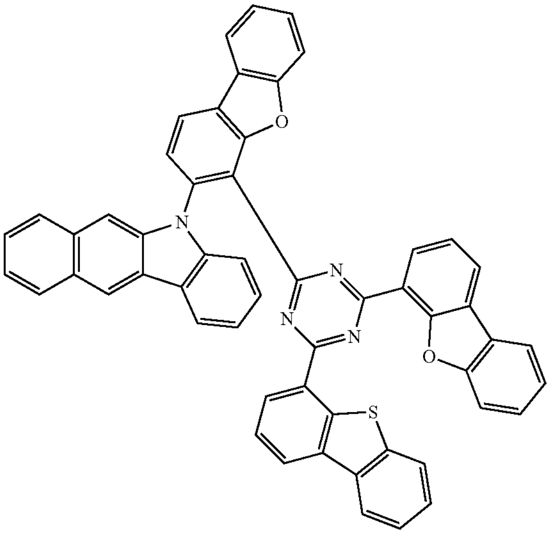
-continued
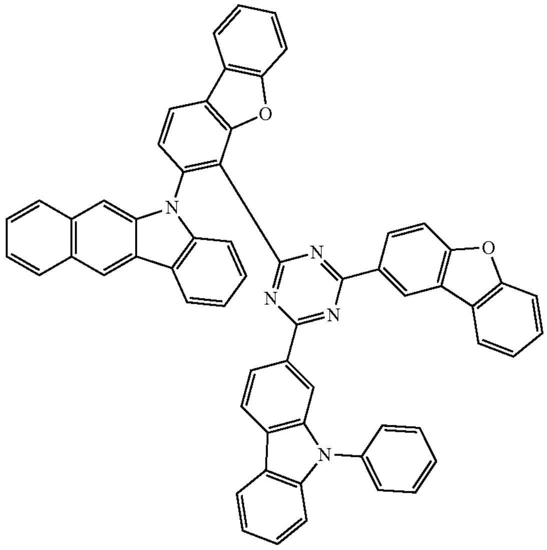
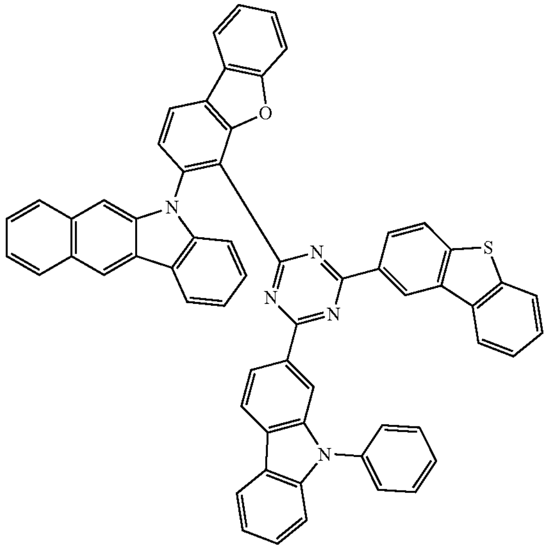
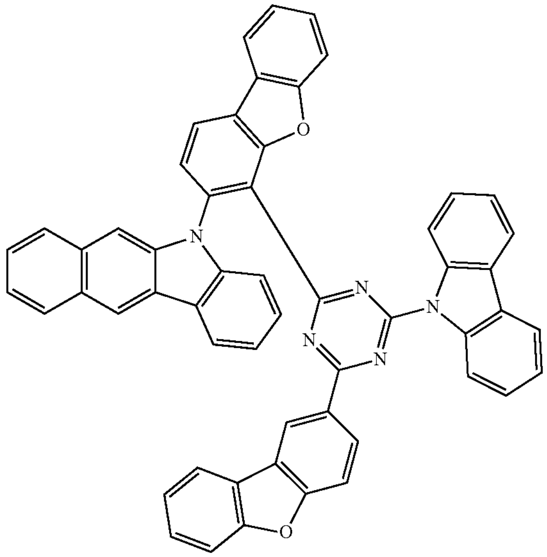

-continued
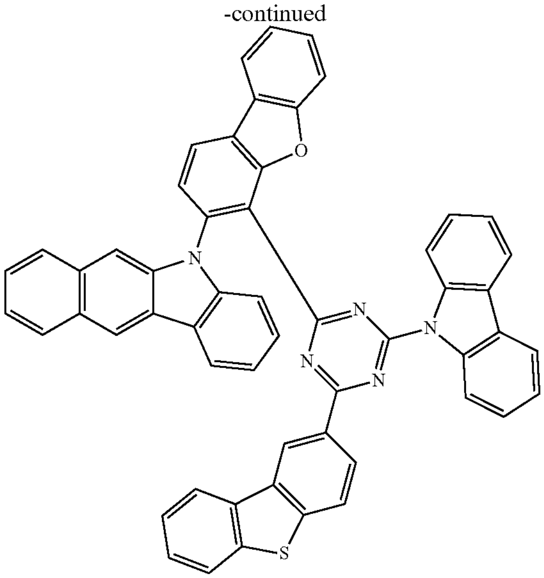
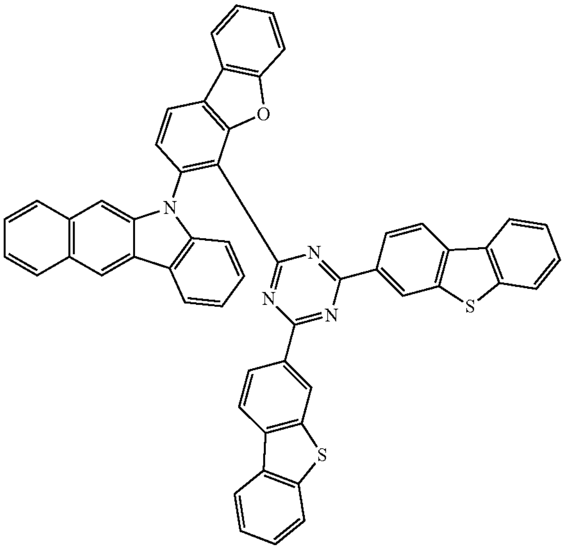
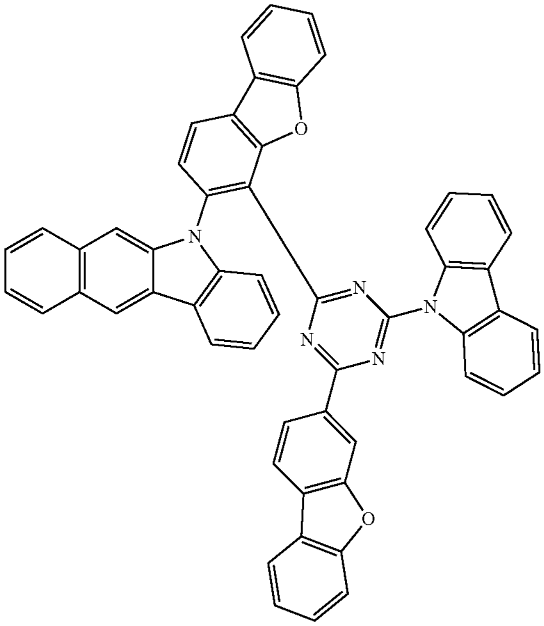
-continued
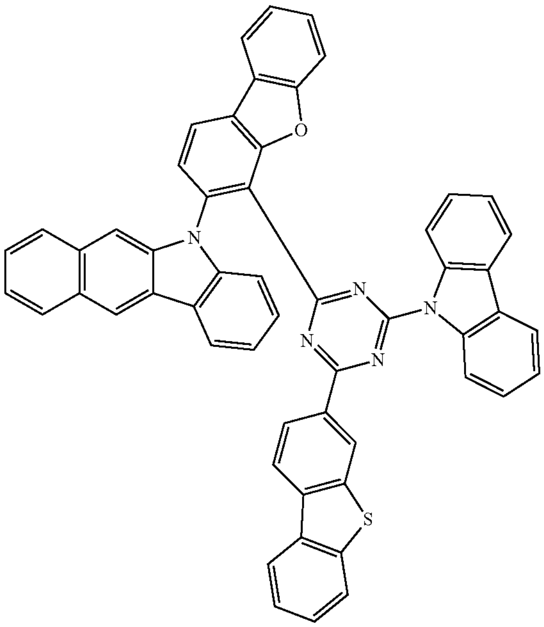
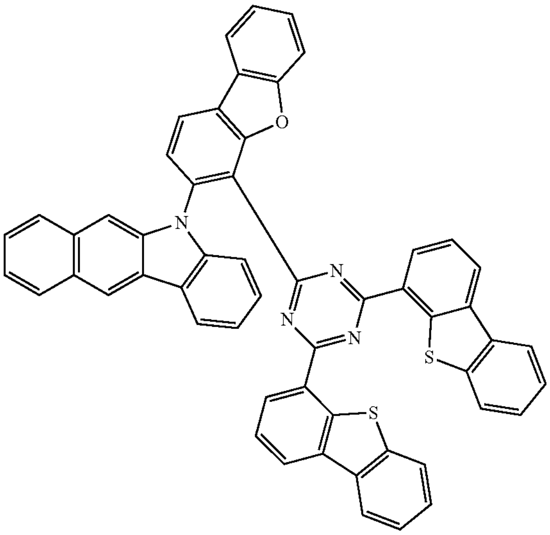
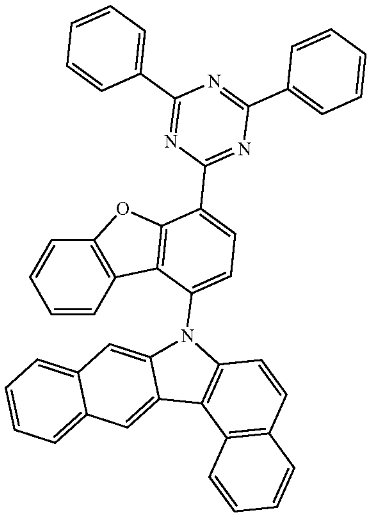

-continued
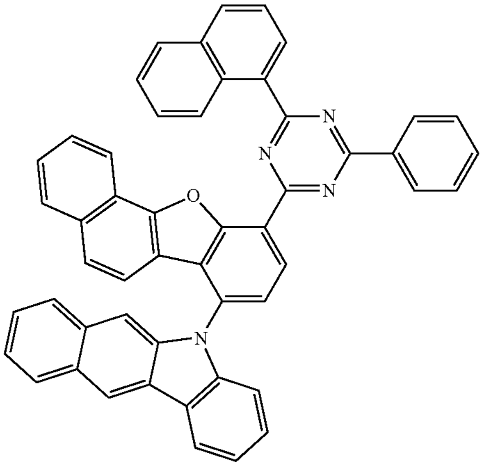
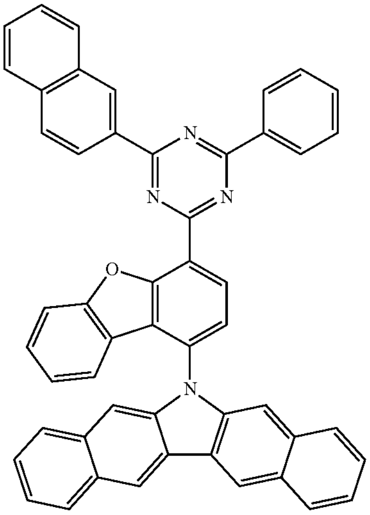
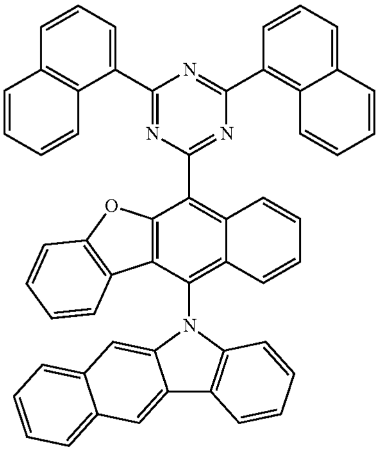
-continued
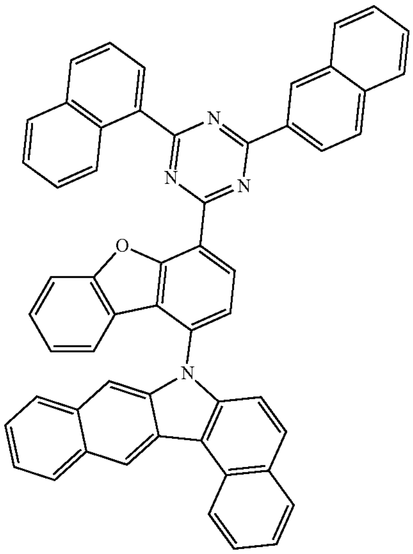
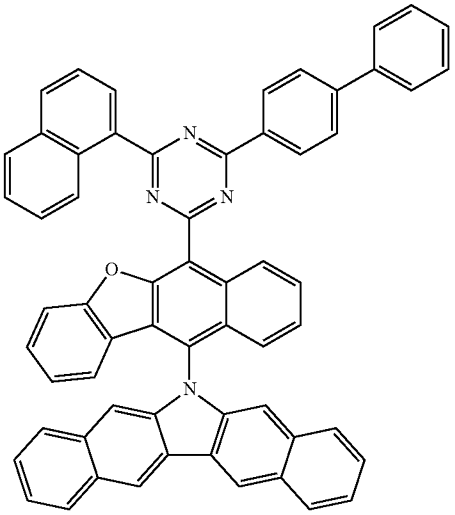
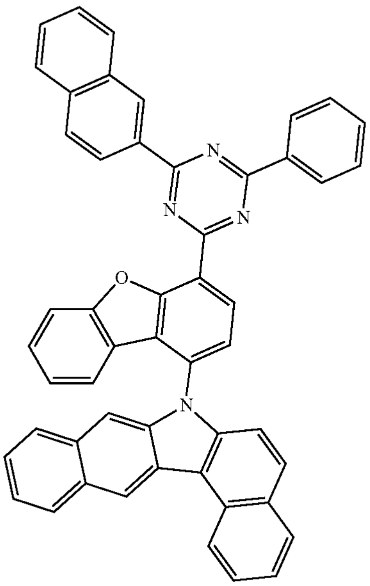

-continued
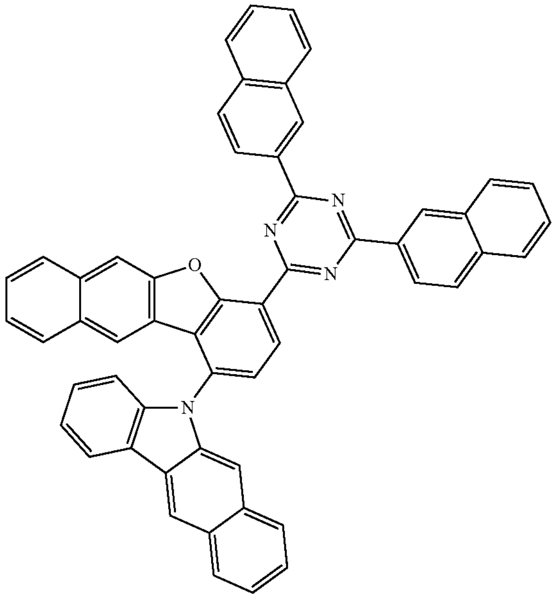
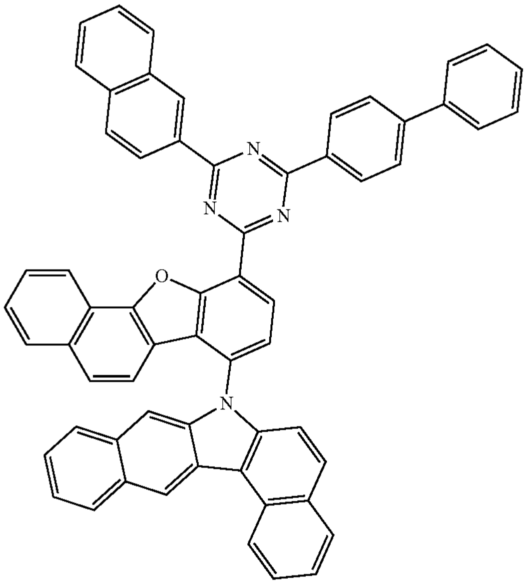
-continued
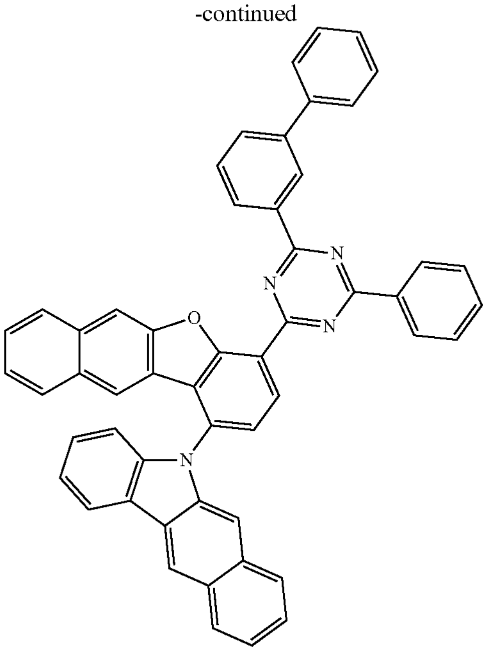
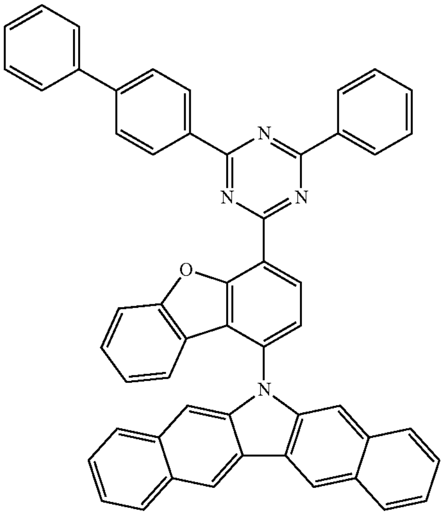
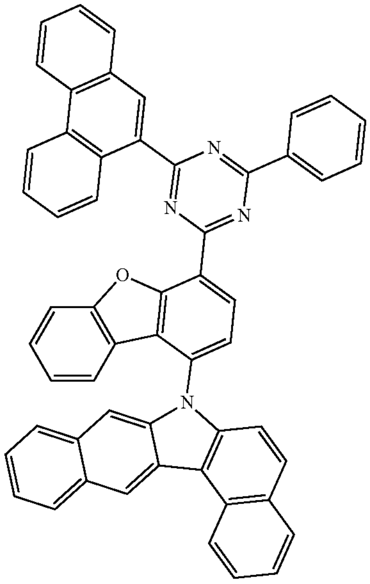

-continued
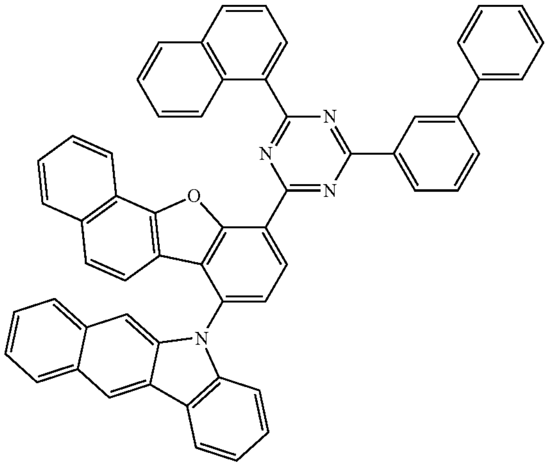
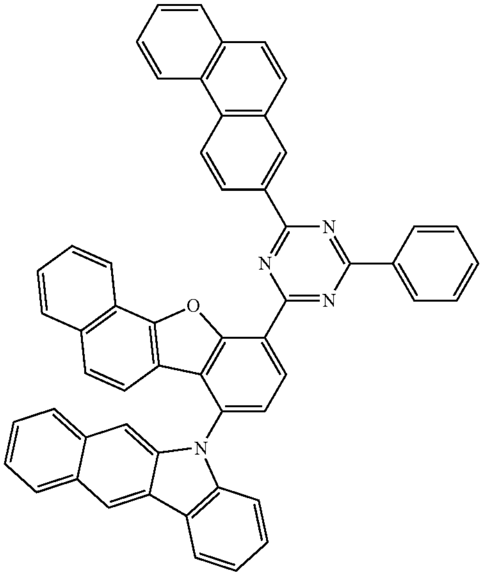
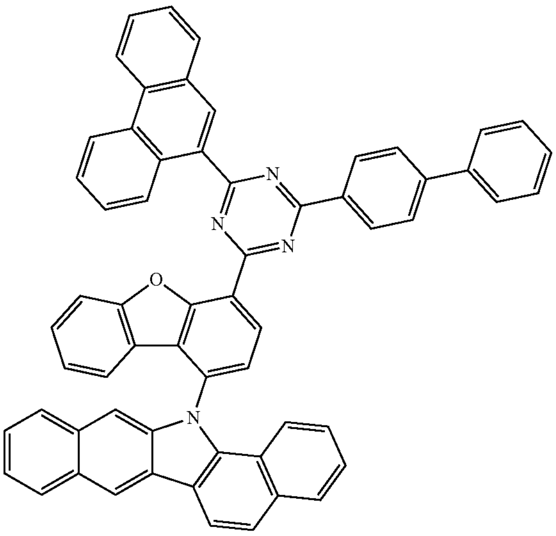
-continued
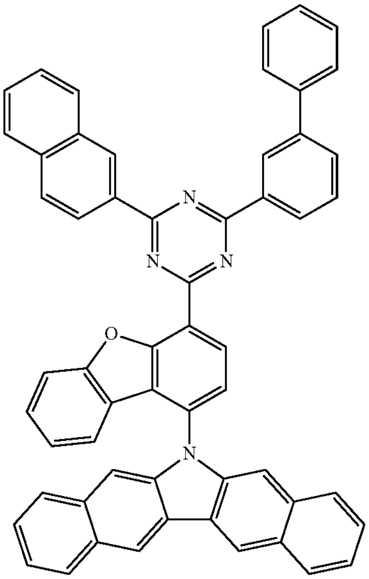
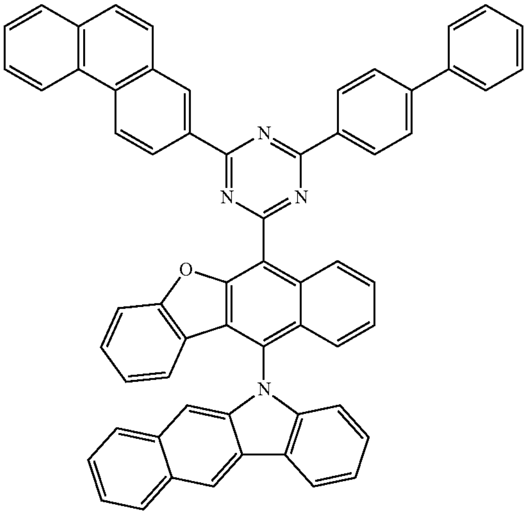
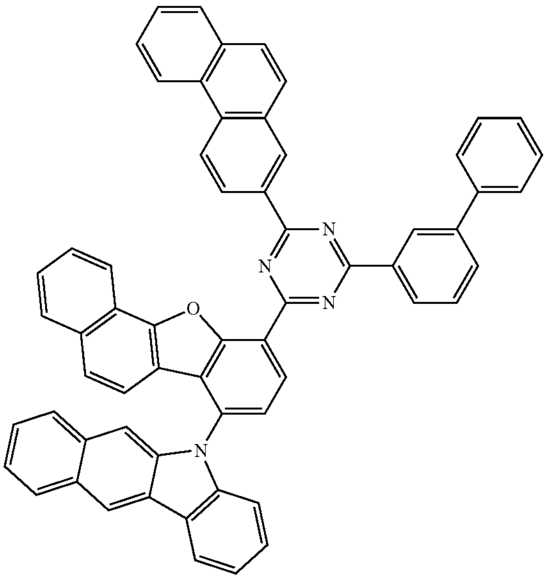

-continued
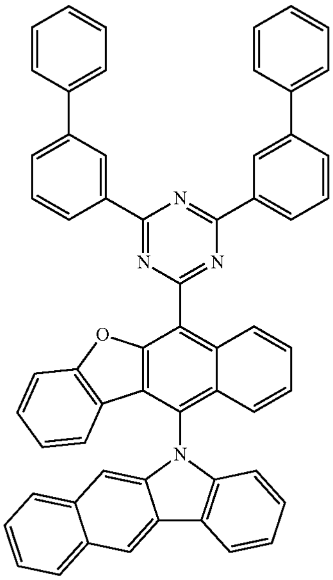
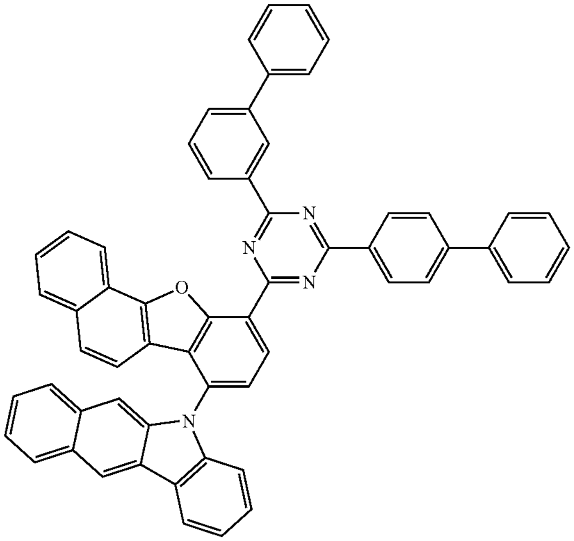
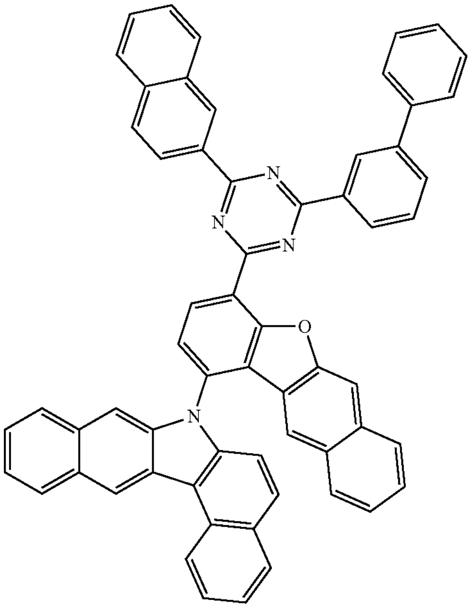
-continued
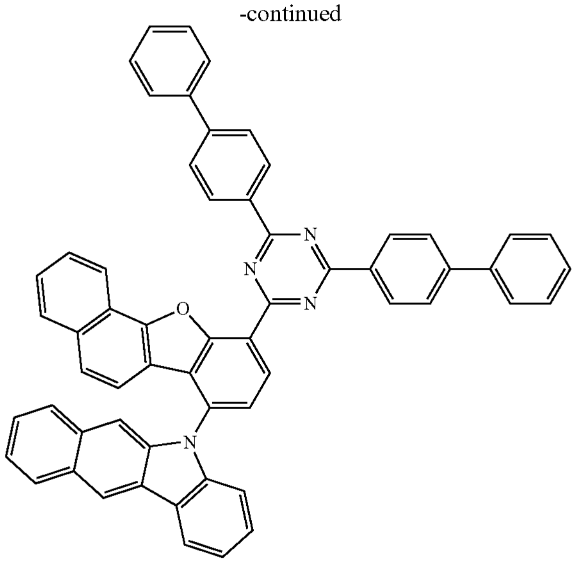
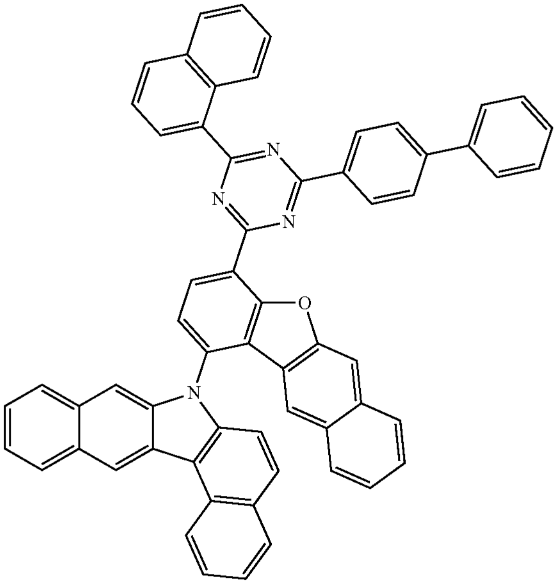
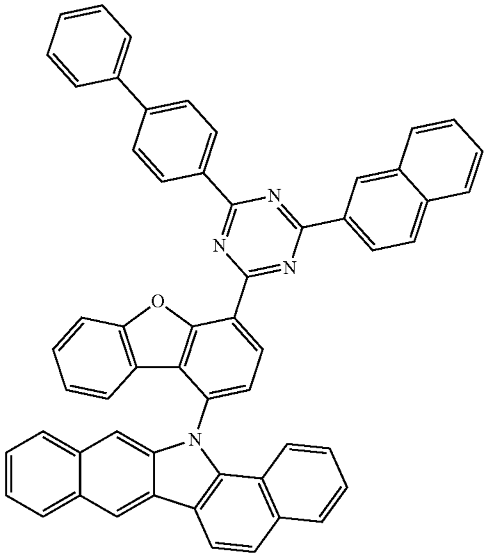

-continued
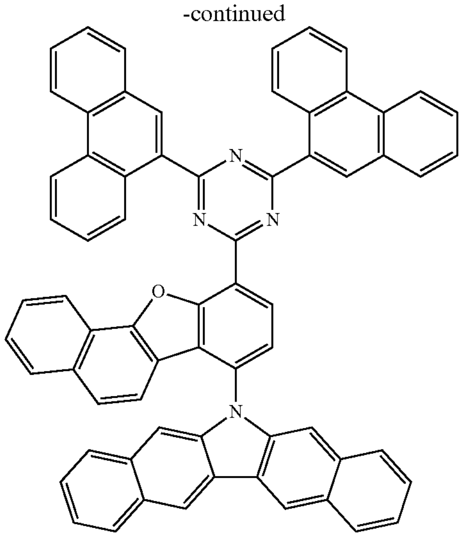
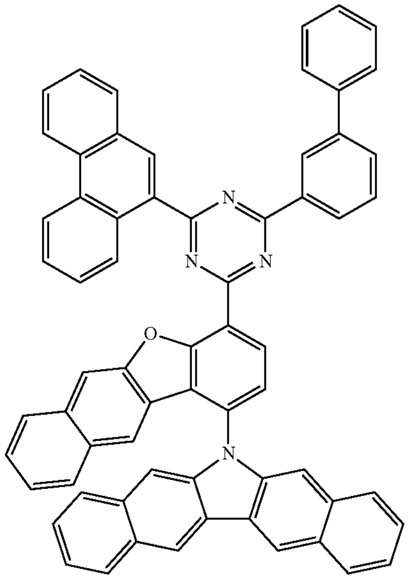
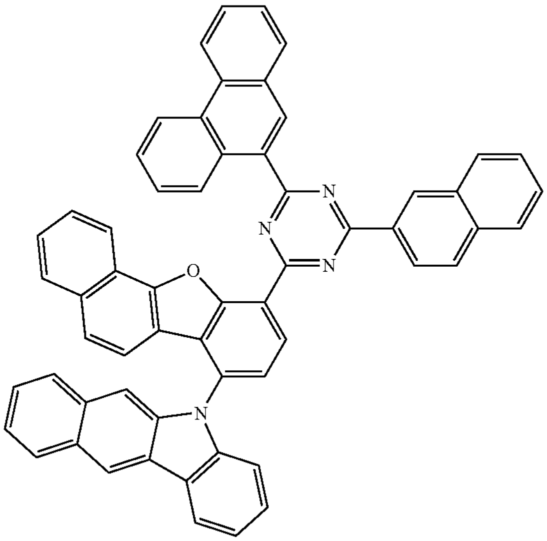
-continued
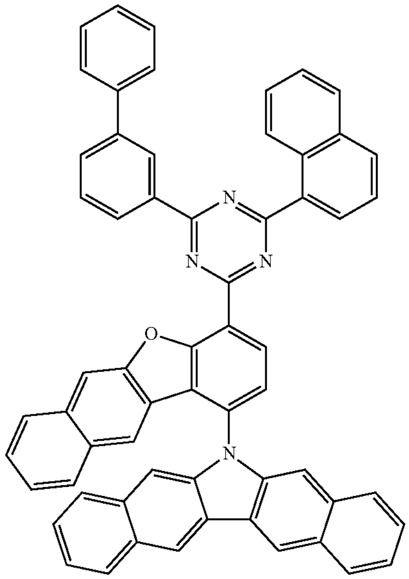
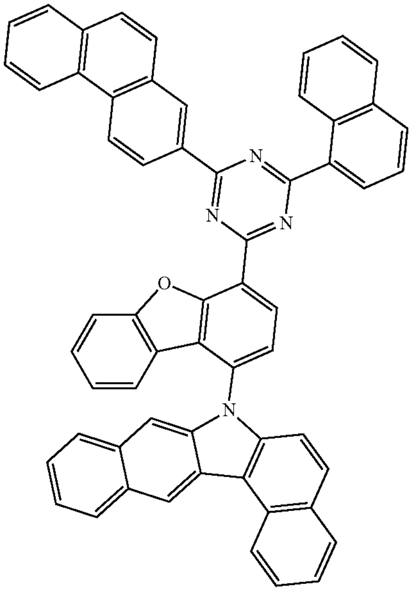
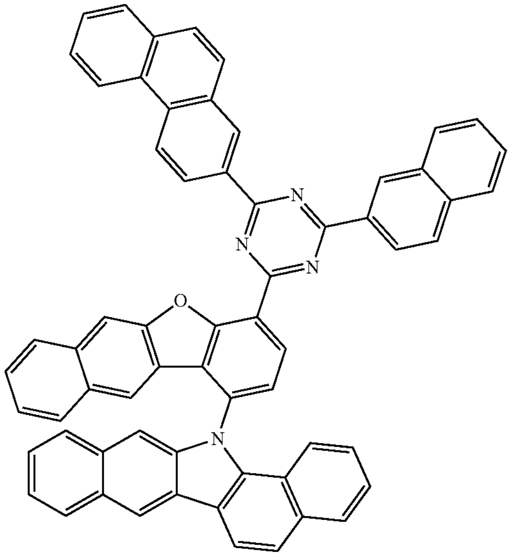

-continued
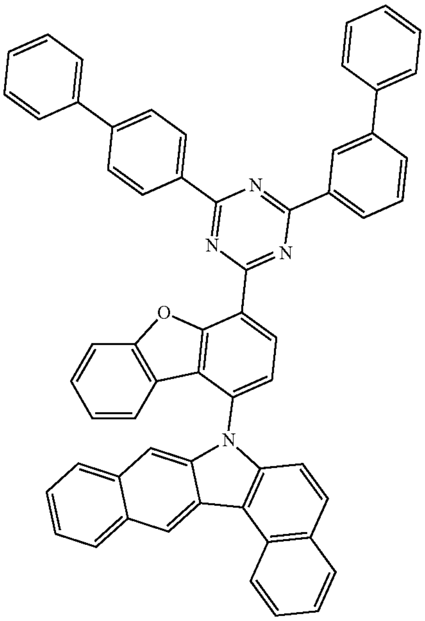
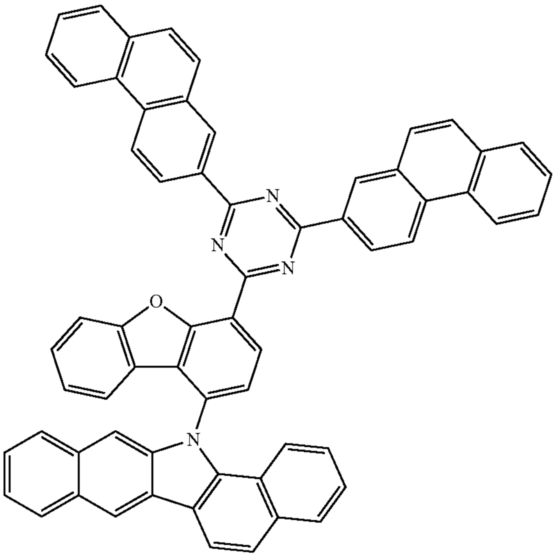
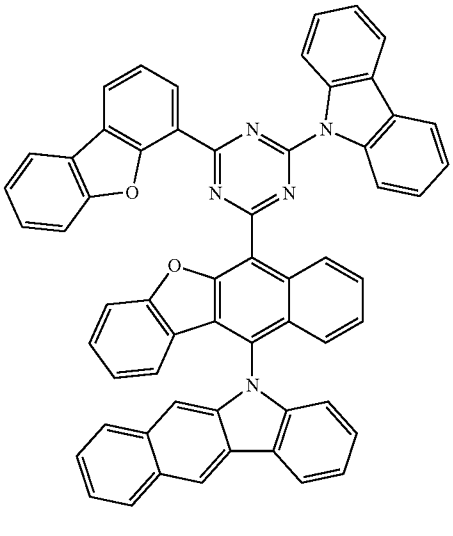
-continued
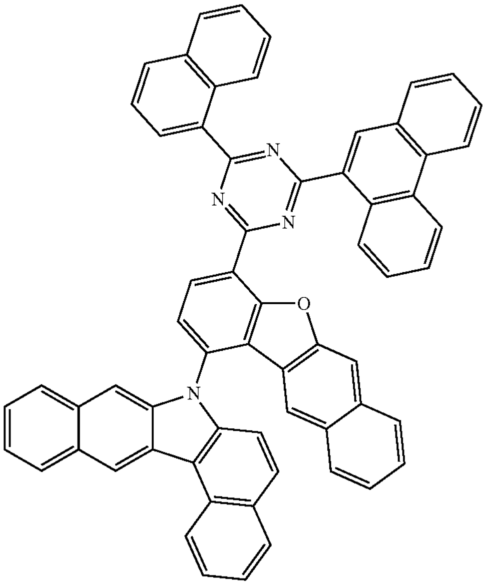
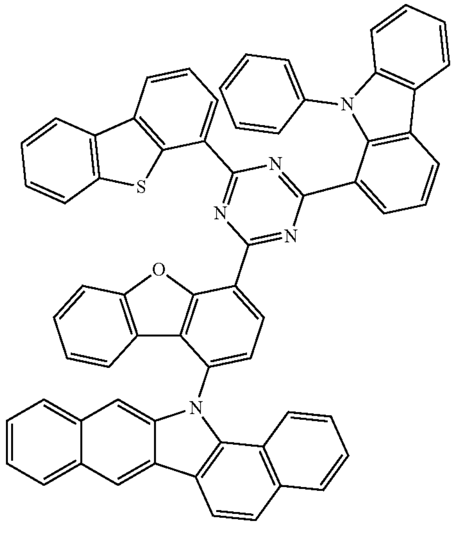
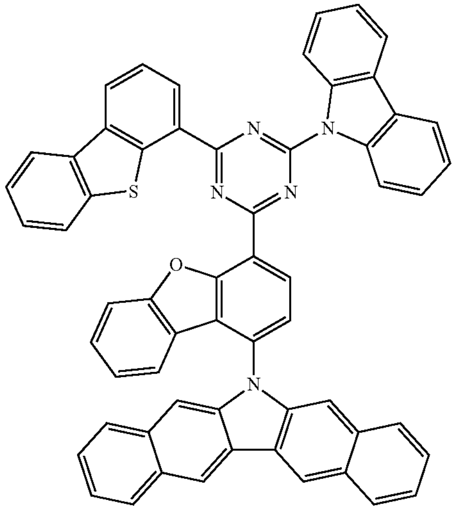

-continued
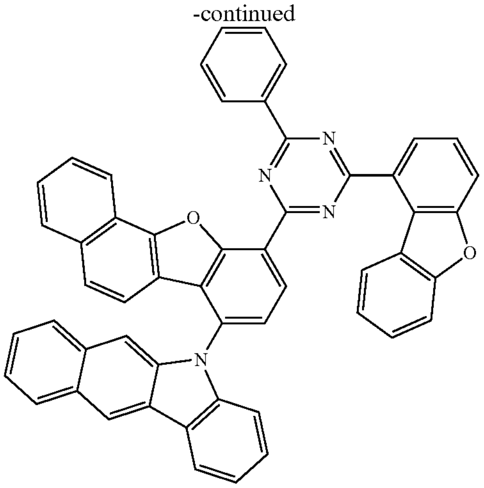
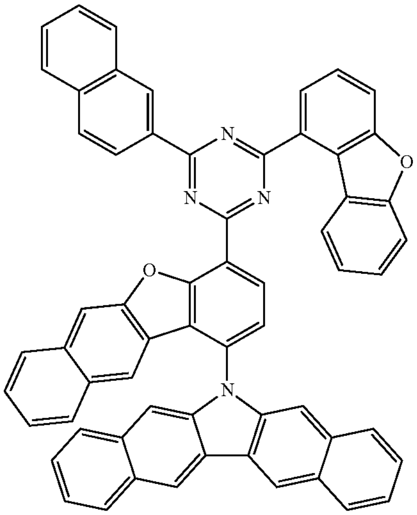
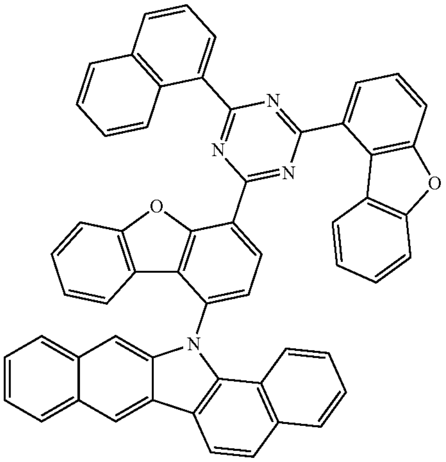
-continued
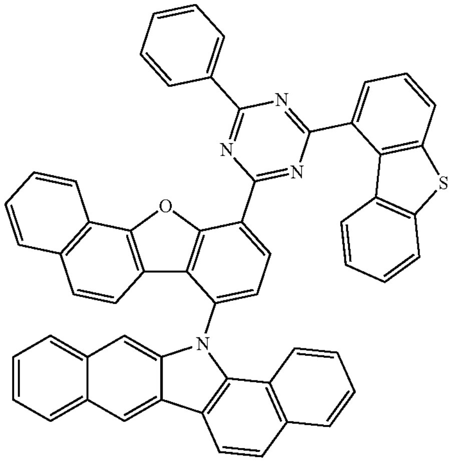
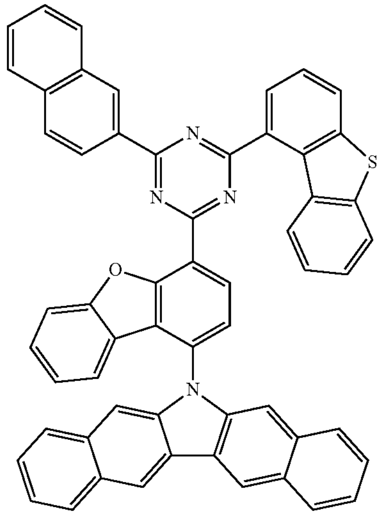
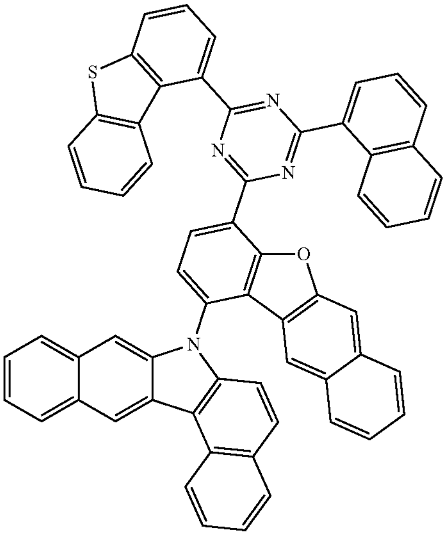

-continued
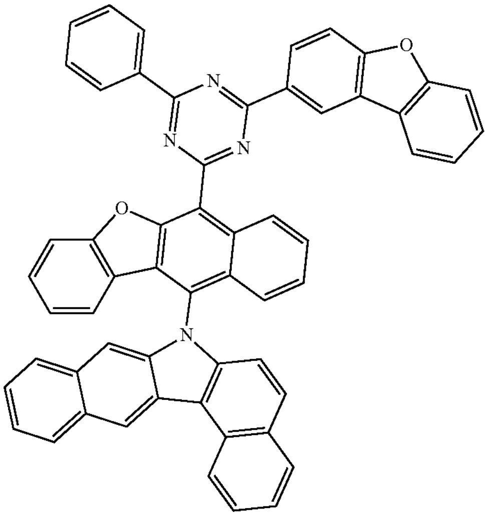
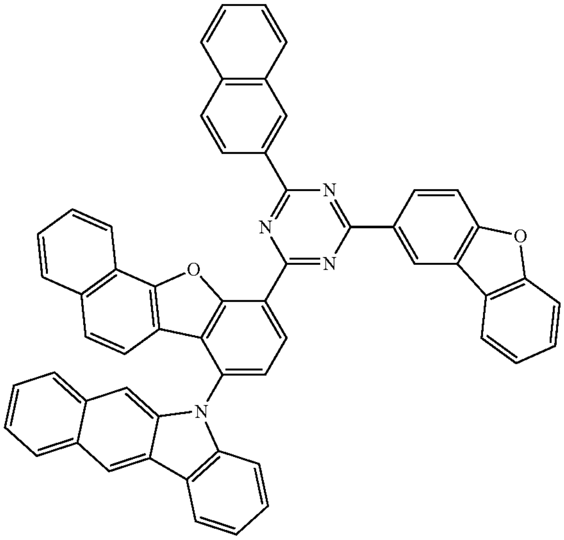
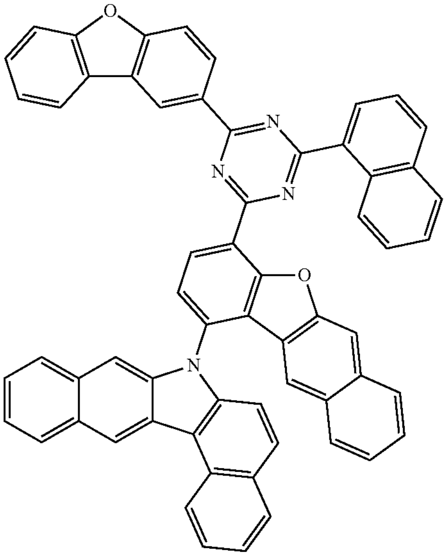
-continued
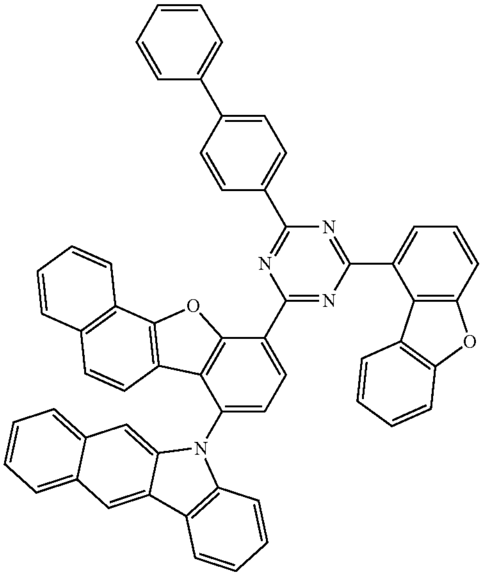
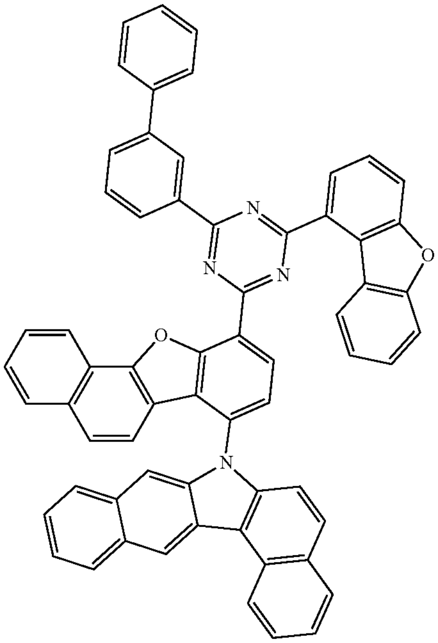

-continued
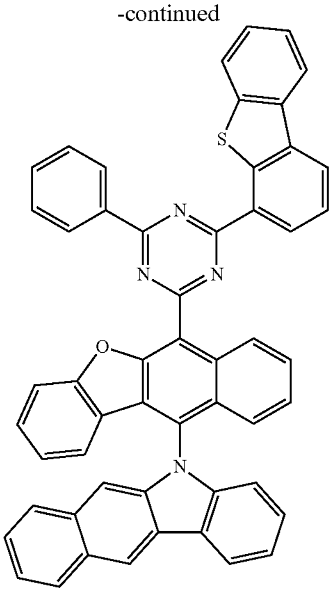
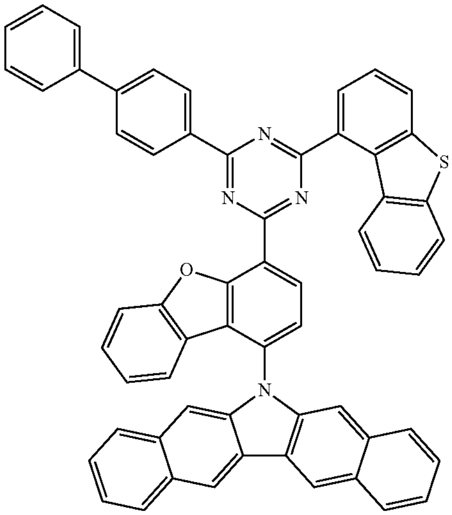
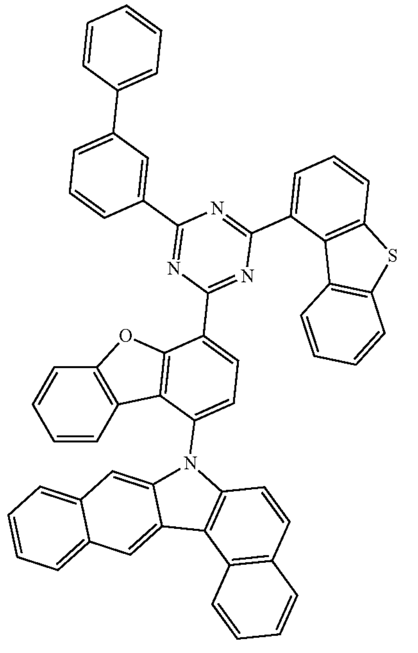
-continued
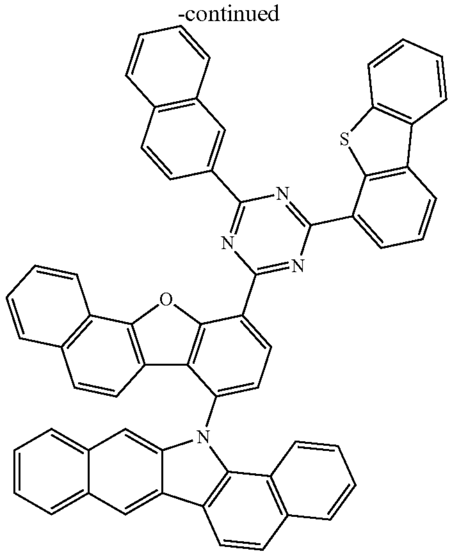
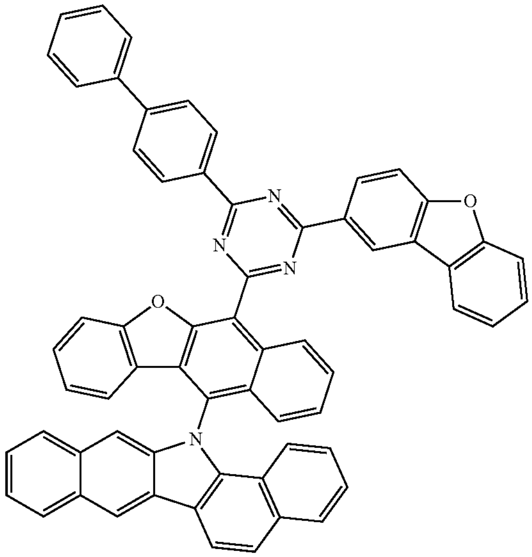
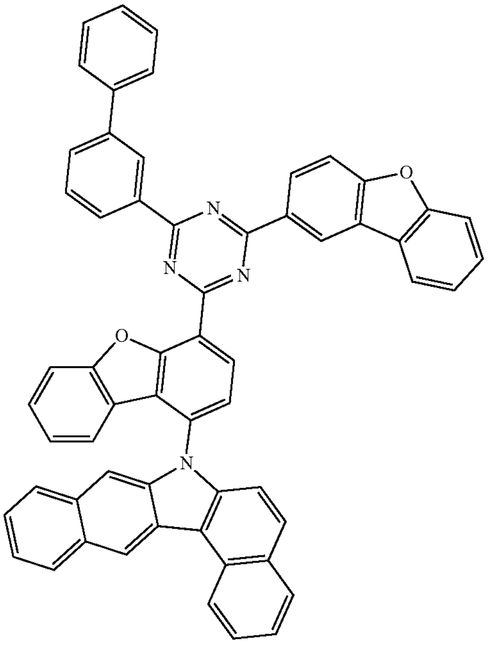

-continued
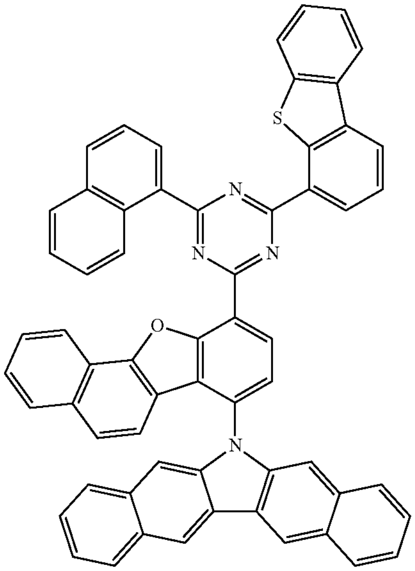
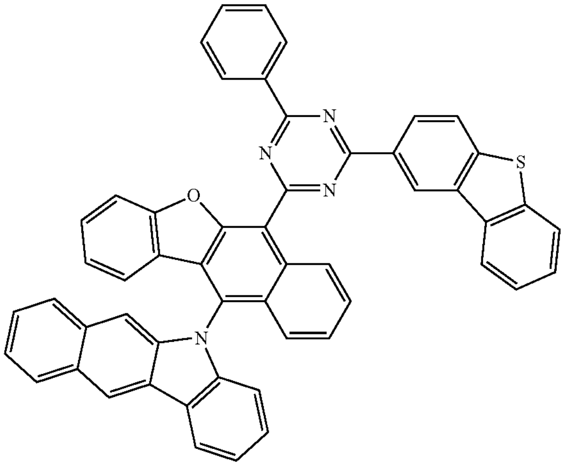
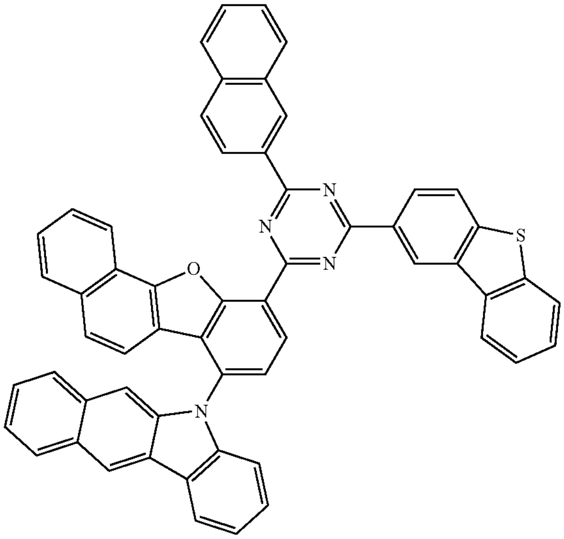
-continued
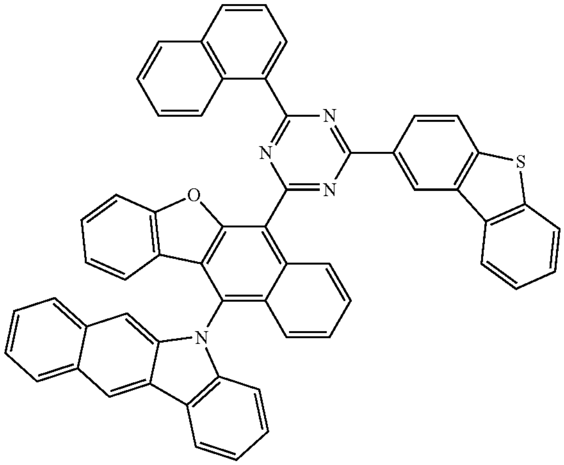
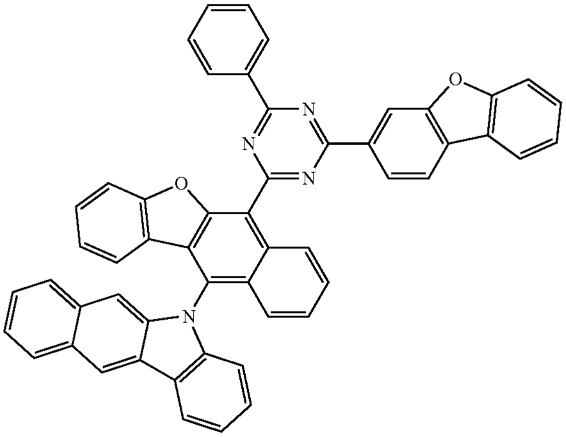
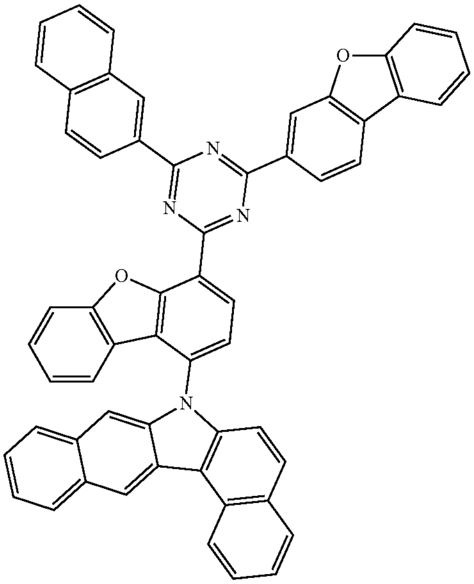

-continued
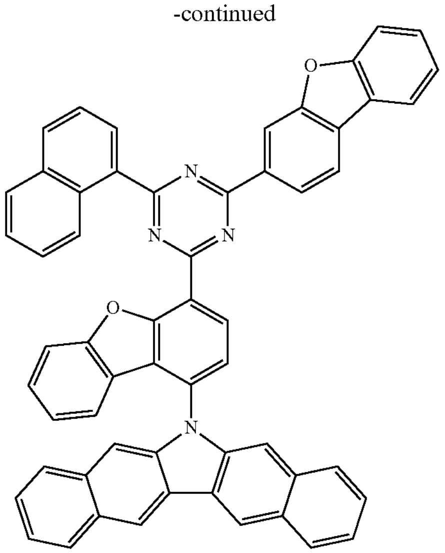
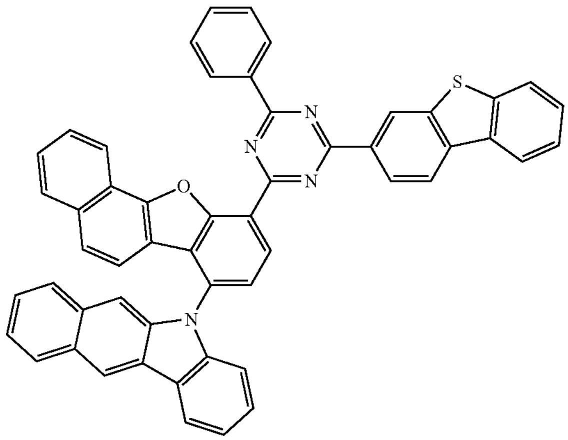
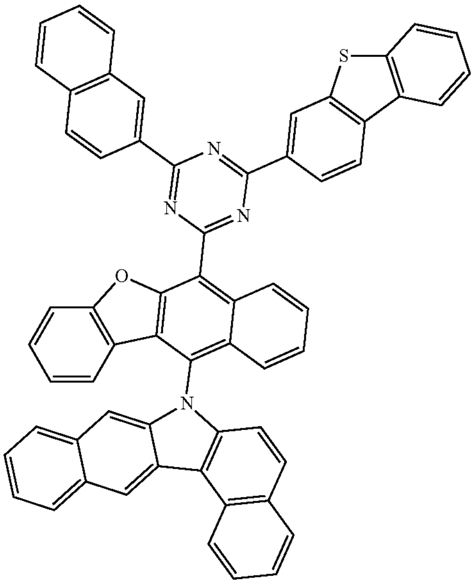
-continued
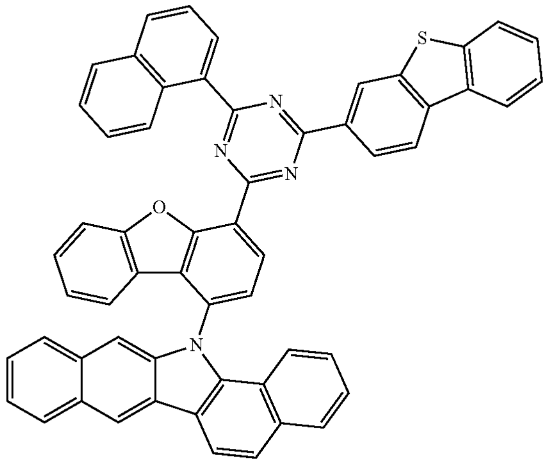
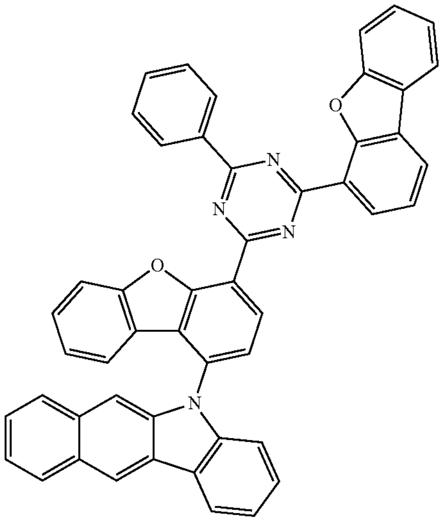
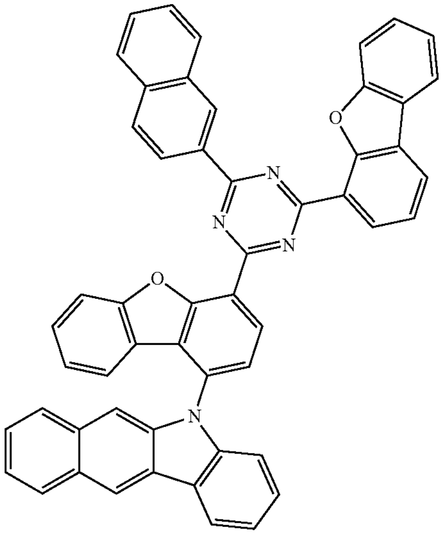

-continued
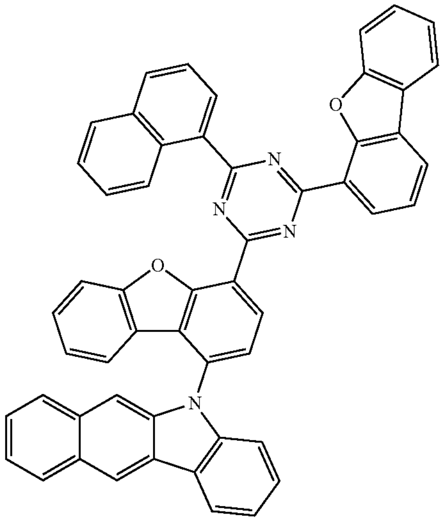
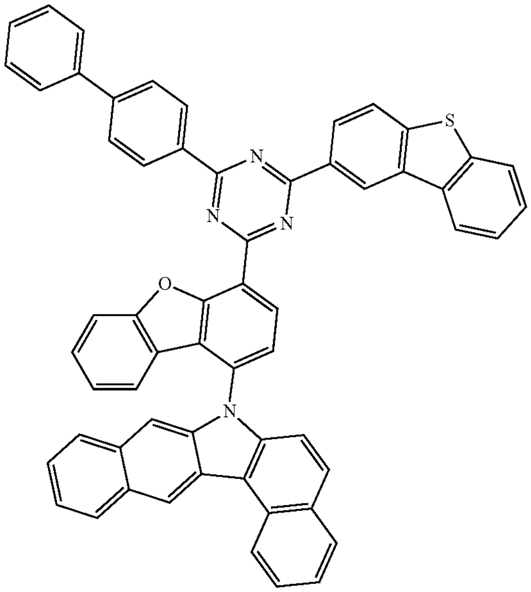
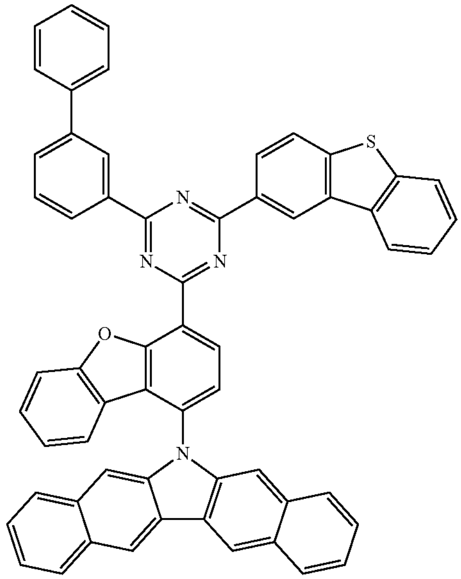
-continued
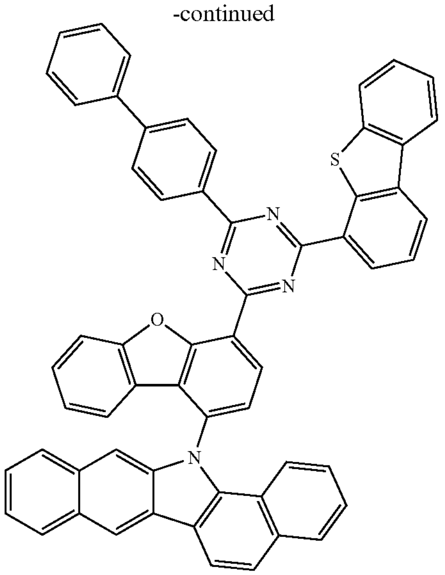
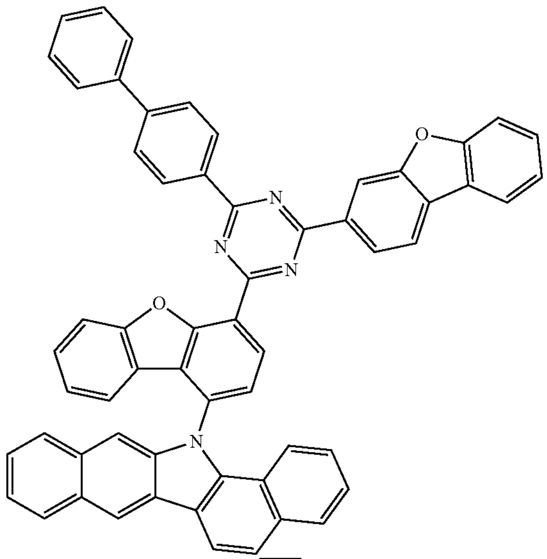
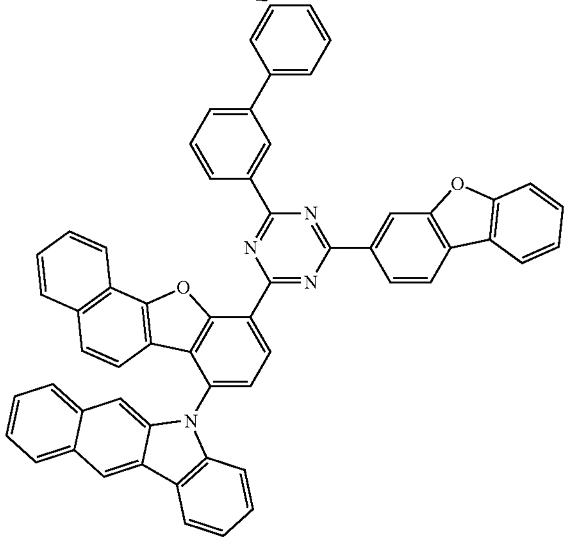

-continued
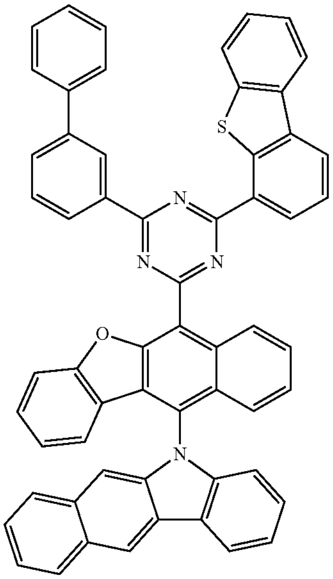
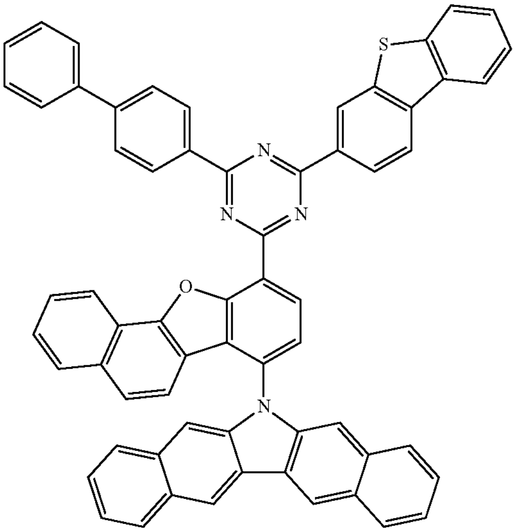
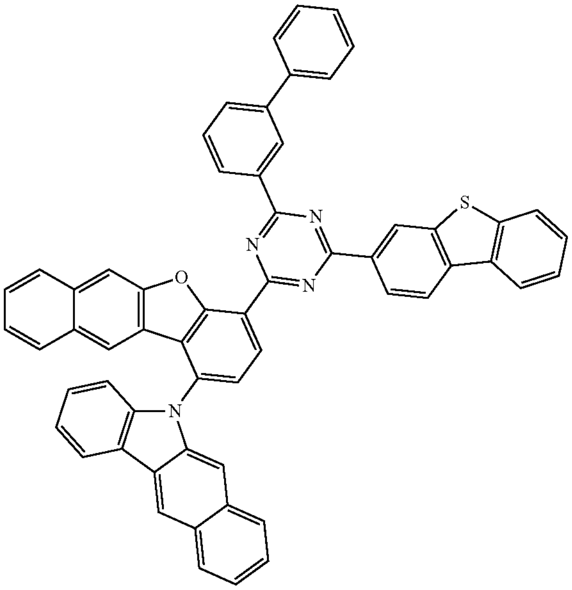
-continued
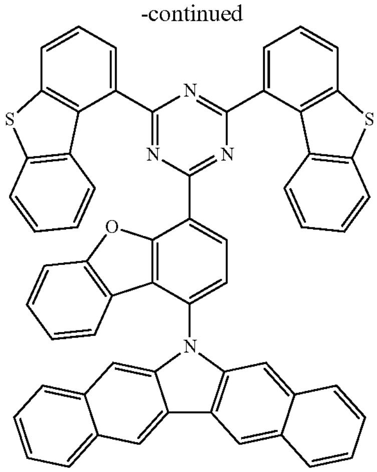
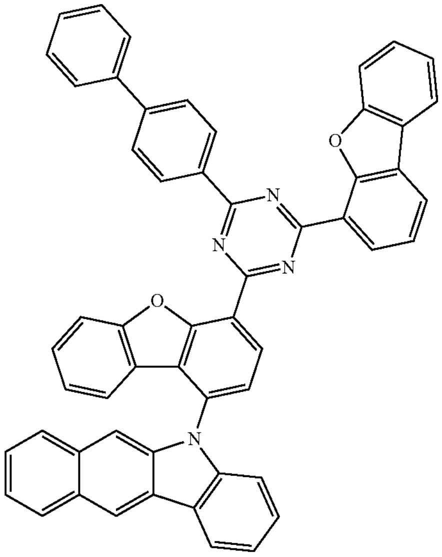
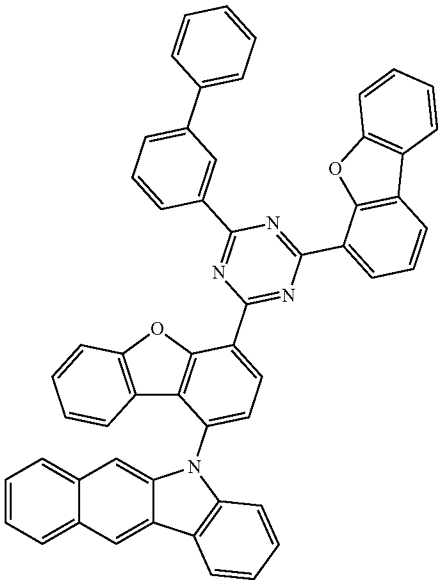

-continued
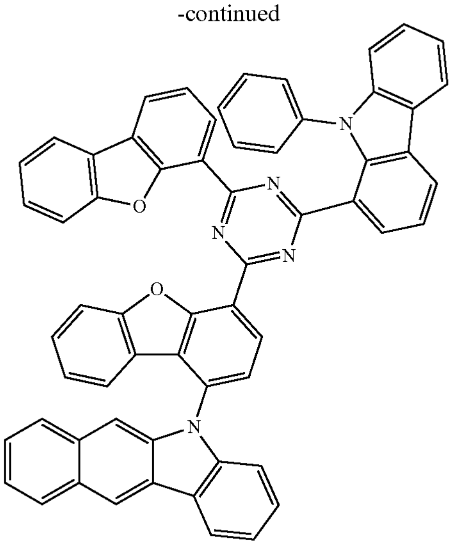
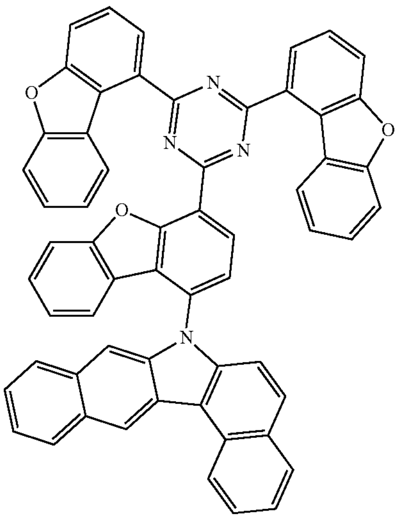
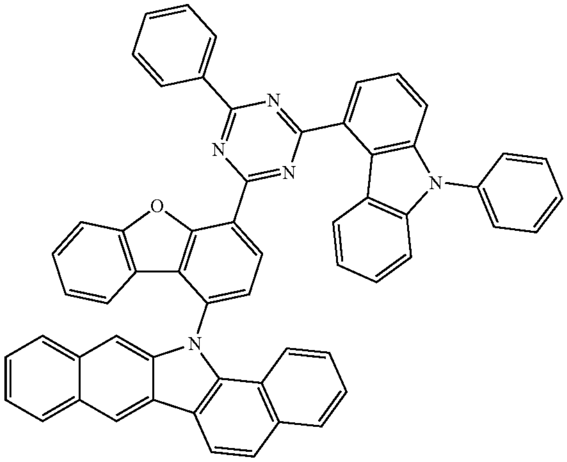
-continued
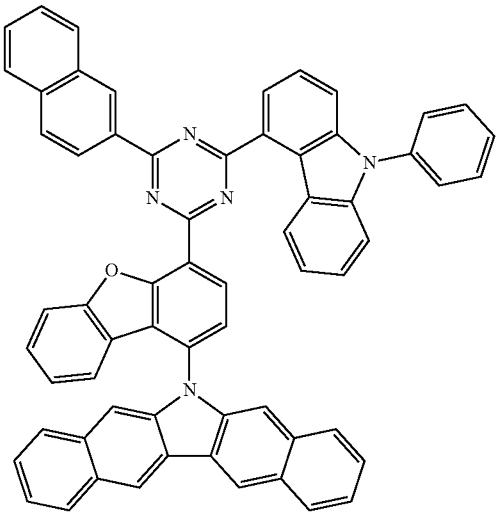
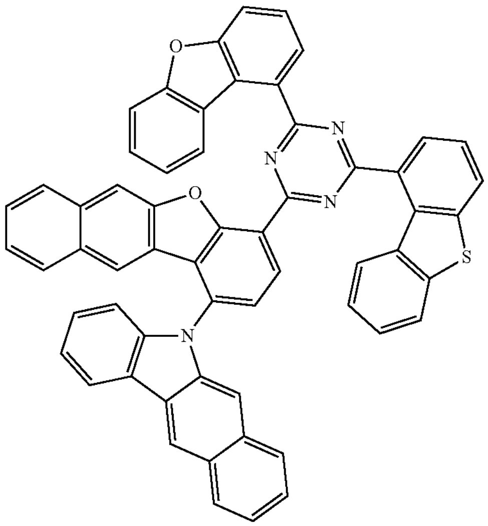
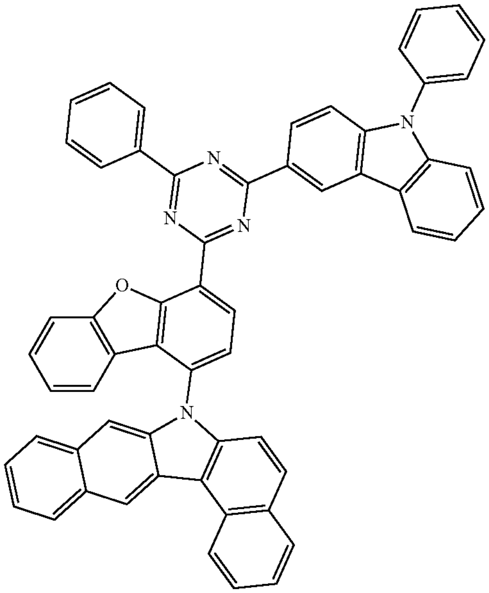

-continued
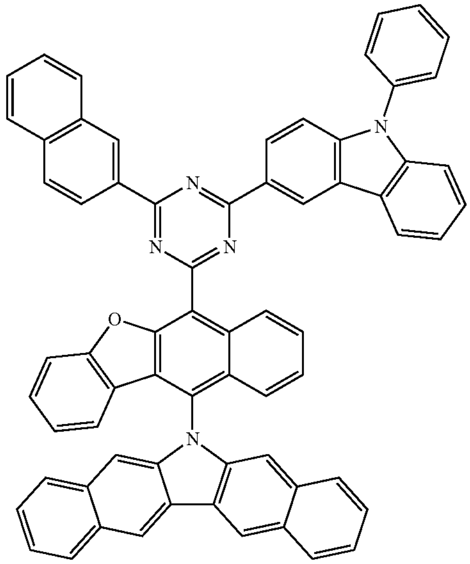
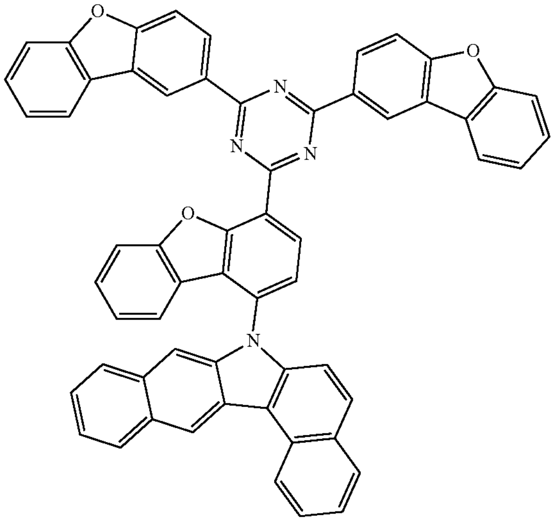
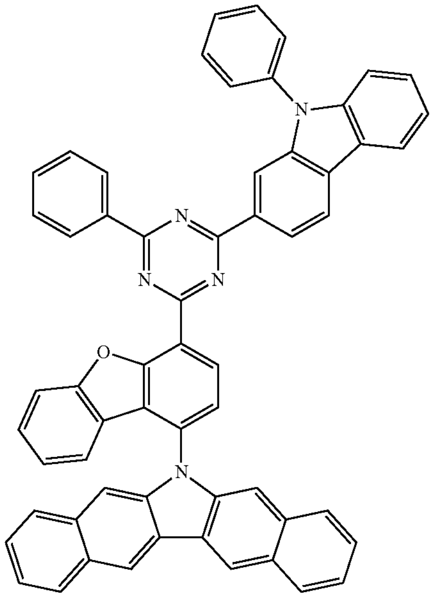
-continued
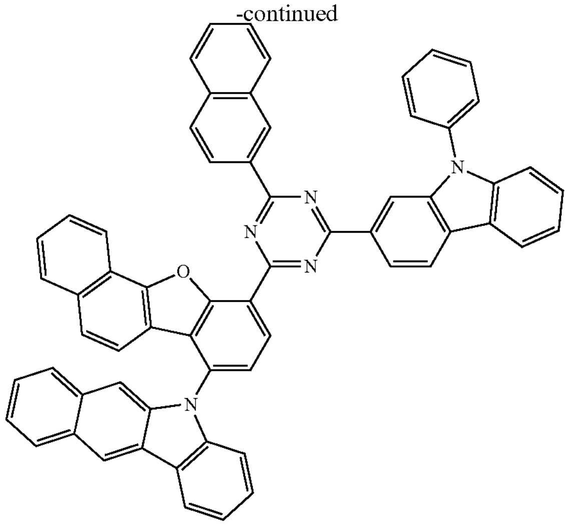
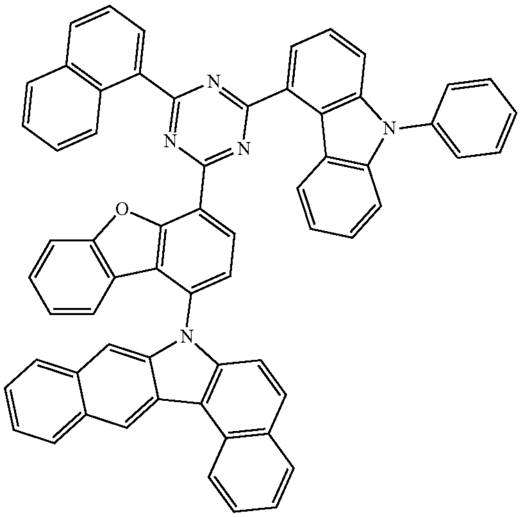
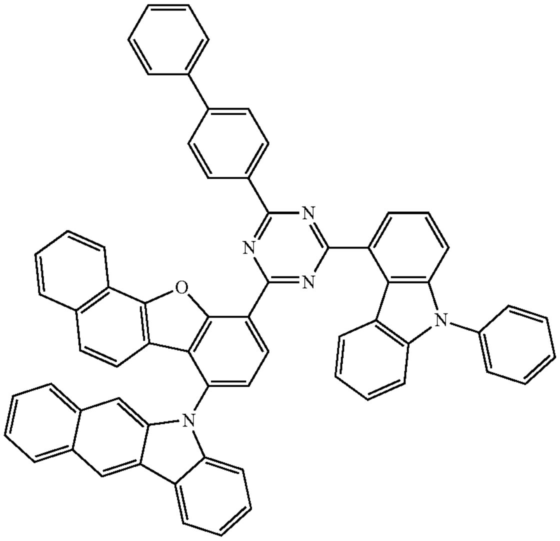

-continued
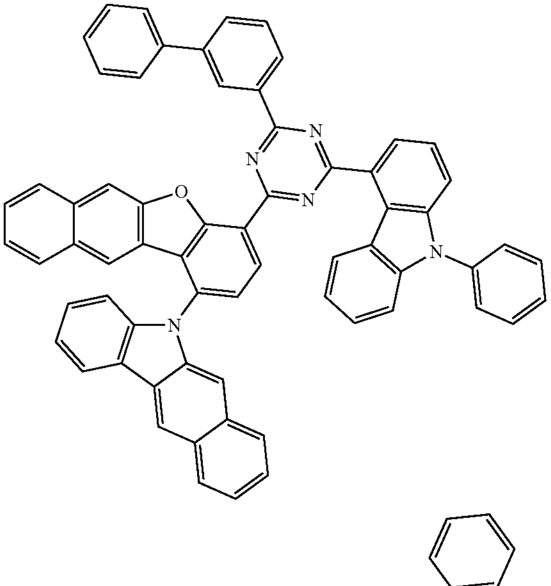
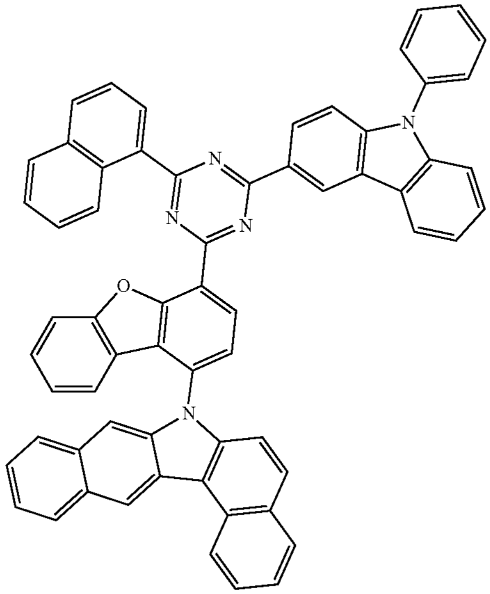
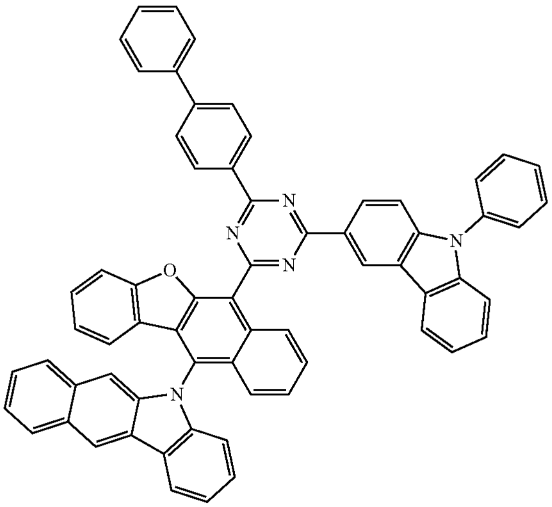
-continued
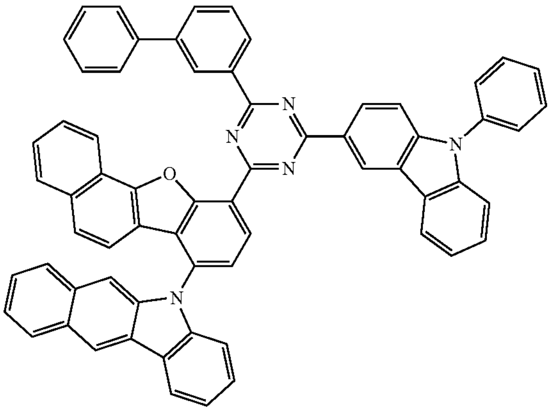
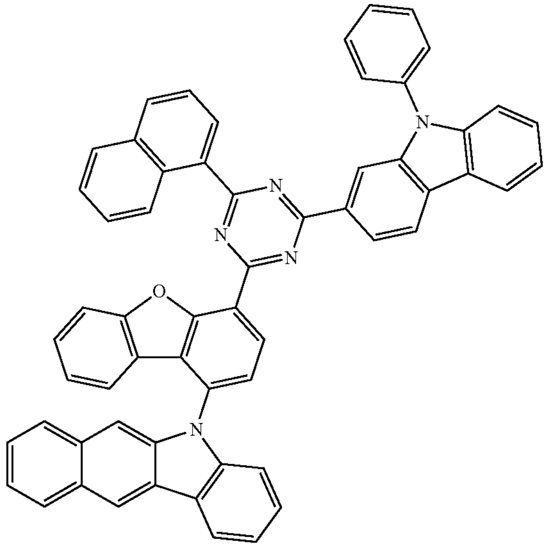
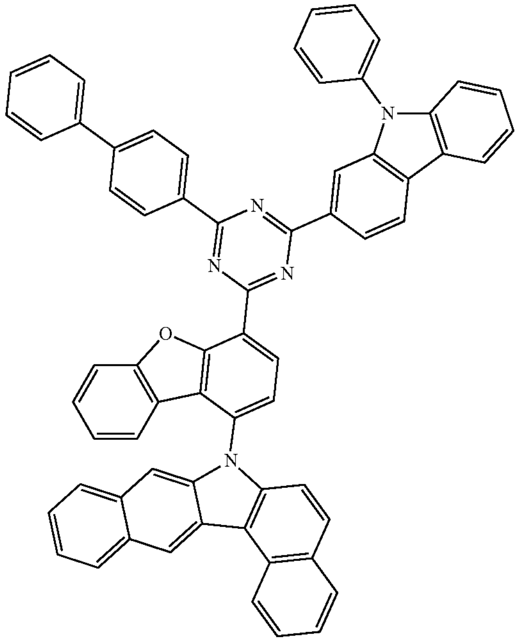

-continued
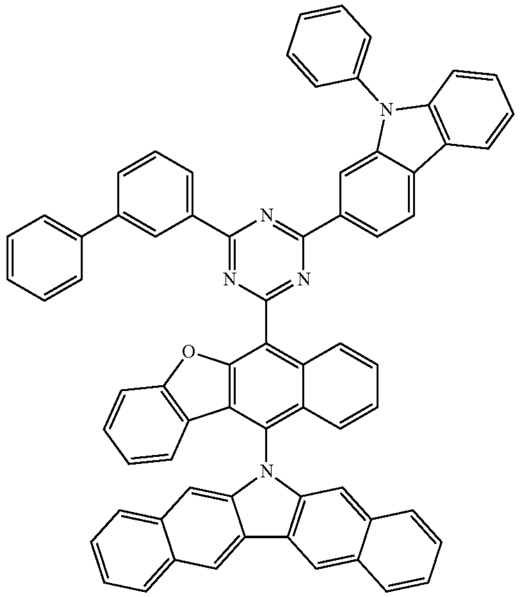
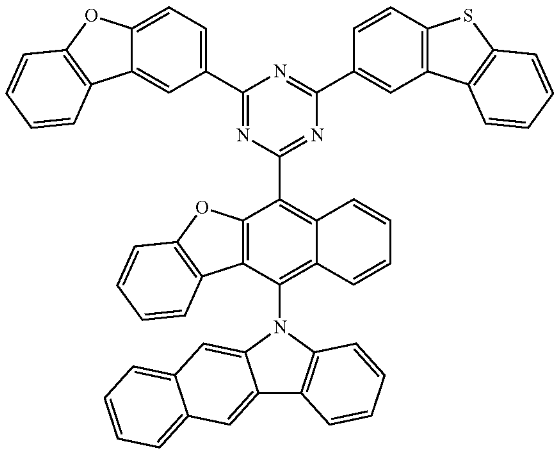
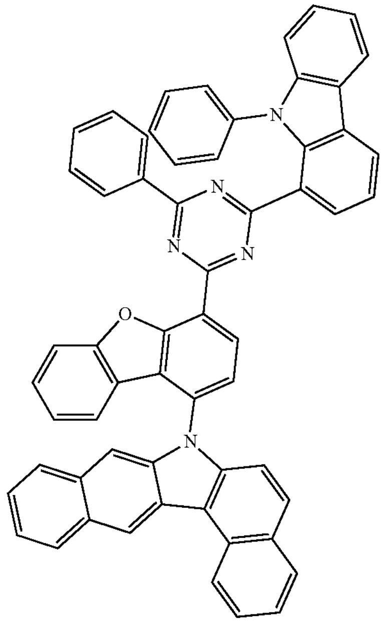
-continued
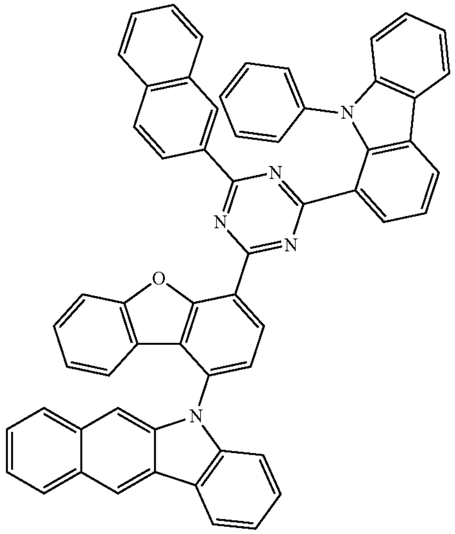
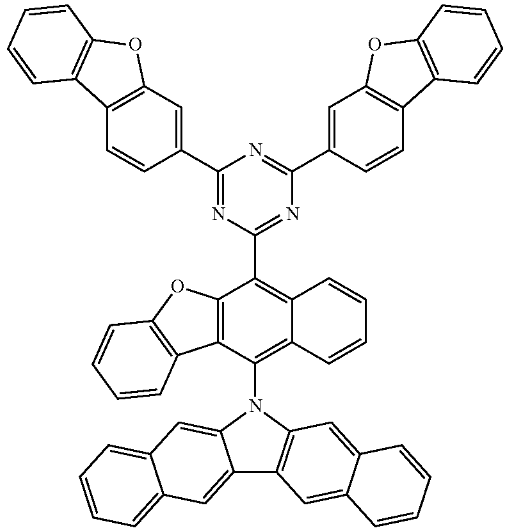
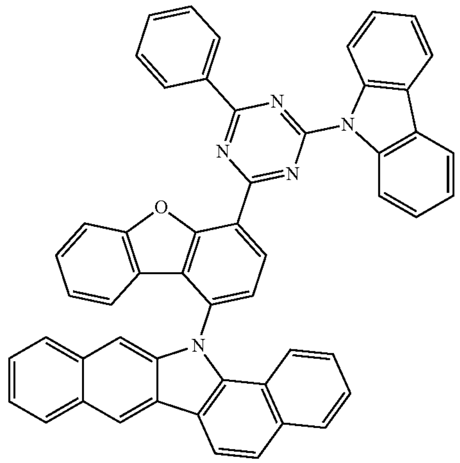

-continued
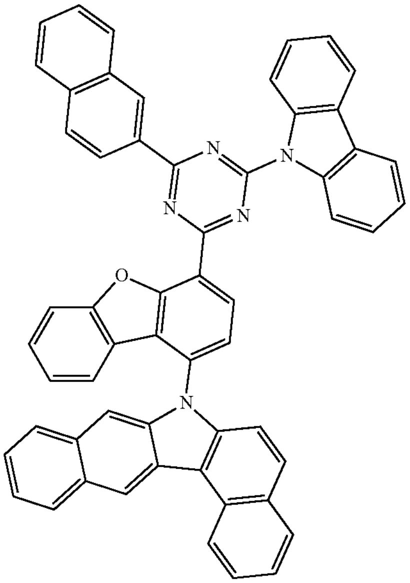
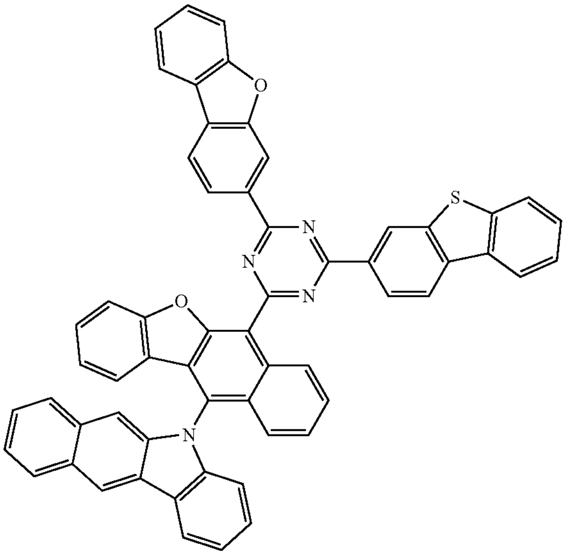
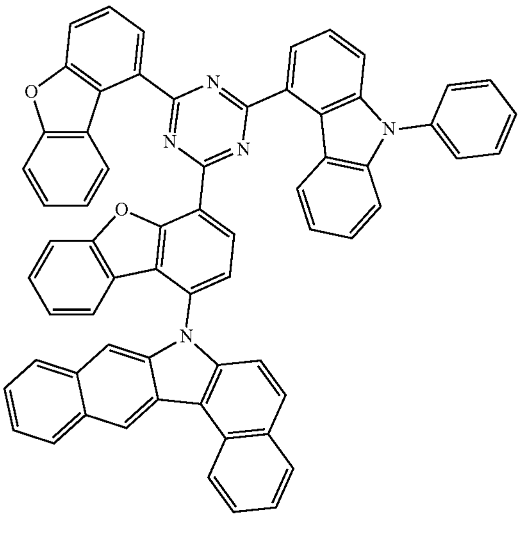
-continued
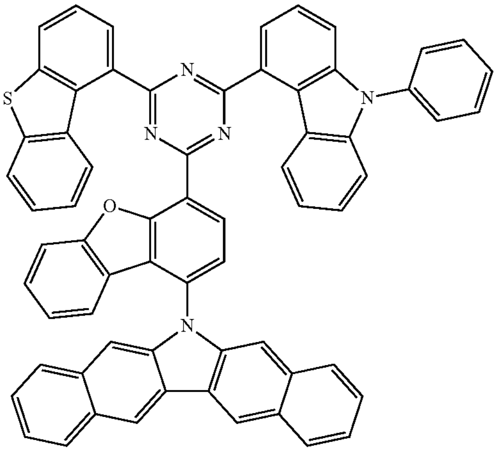
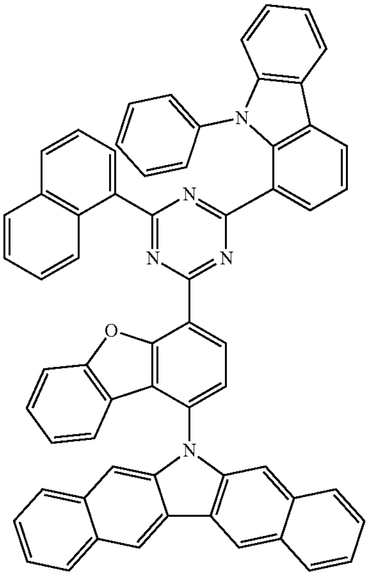
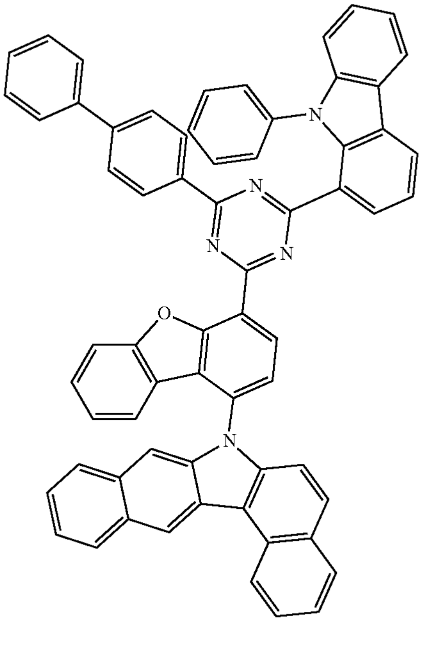

-continued
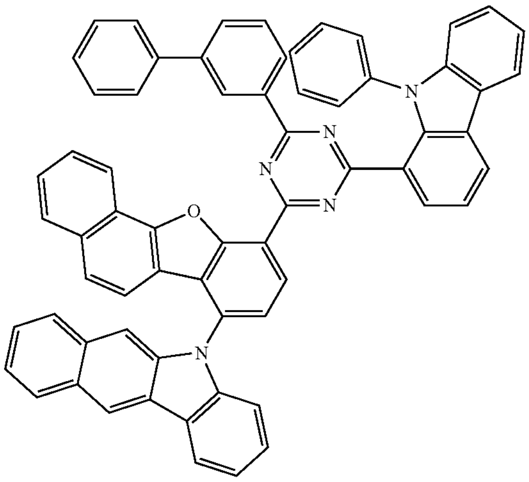
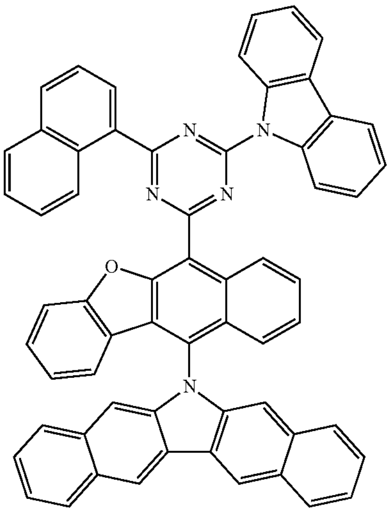
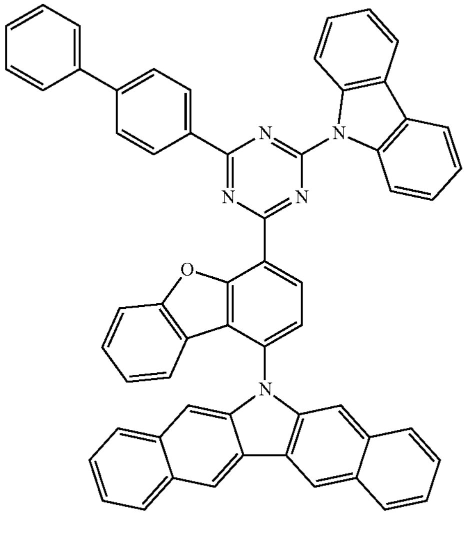
-continued
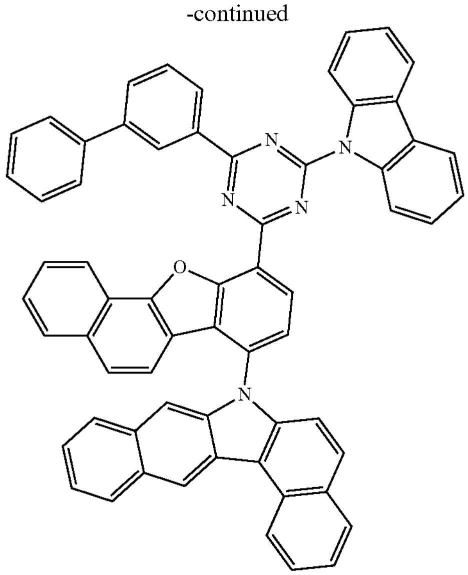
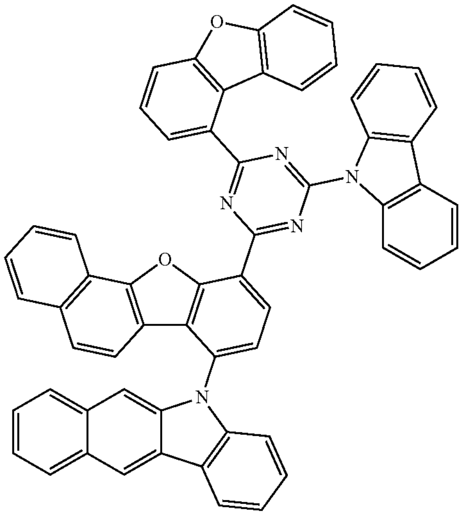
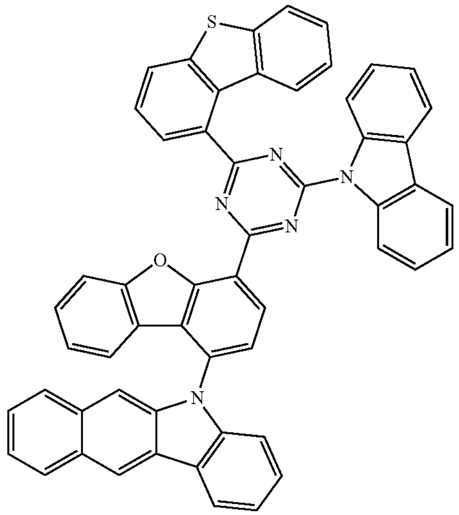

-continued
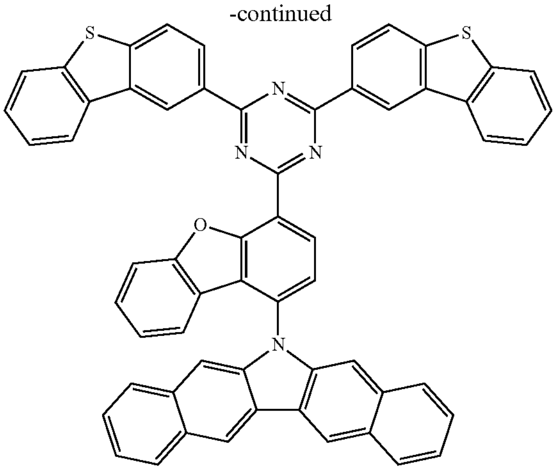
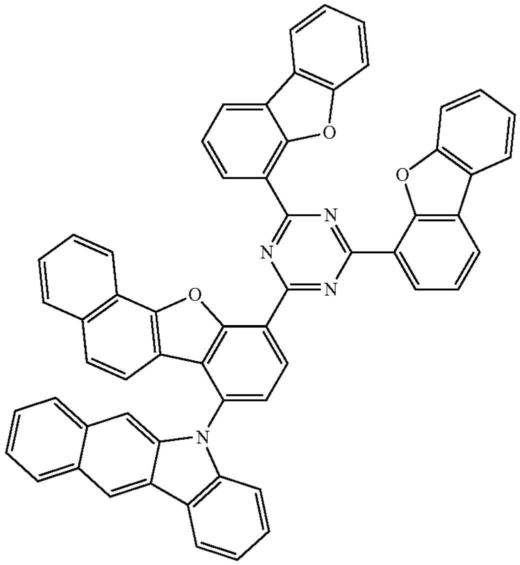
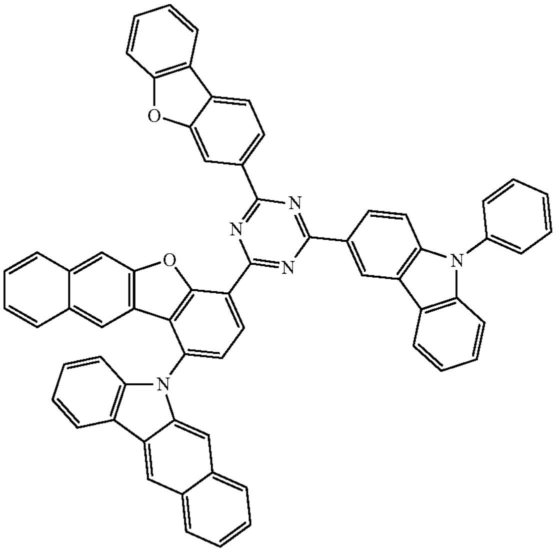
-continued
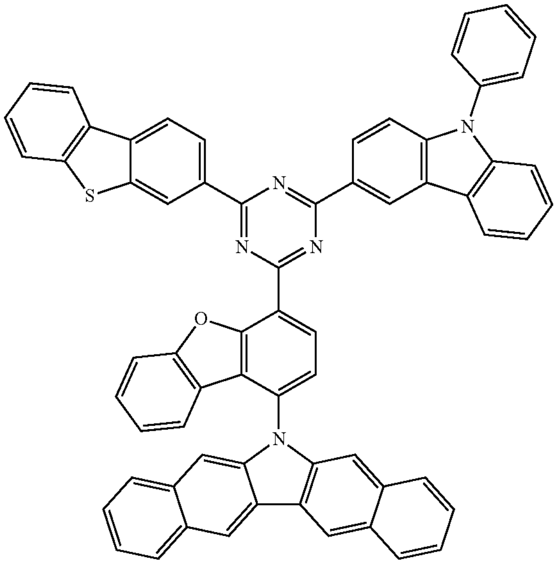
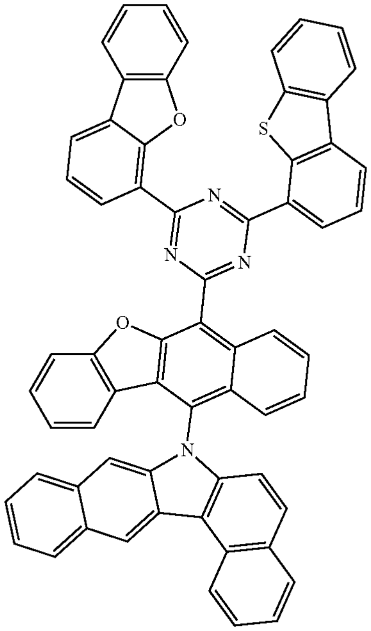

-continued
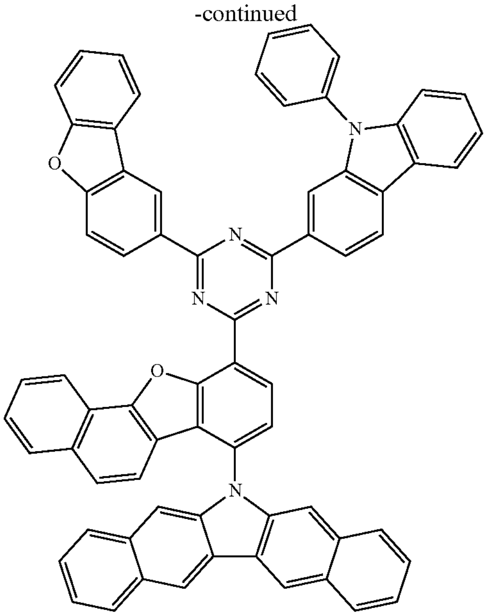
-continued
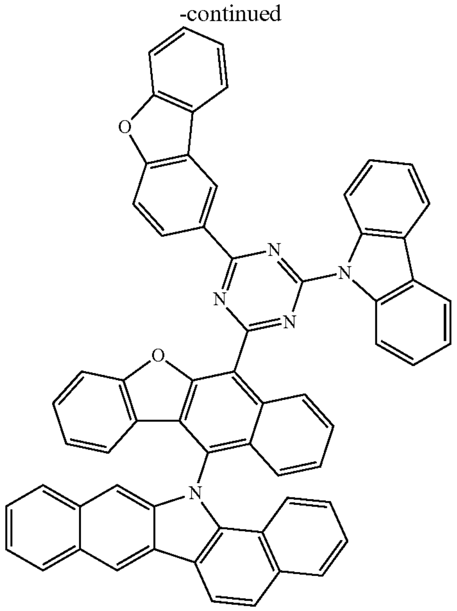
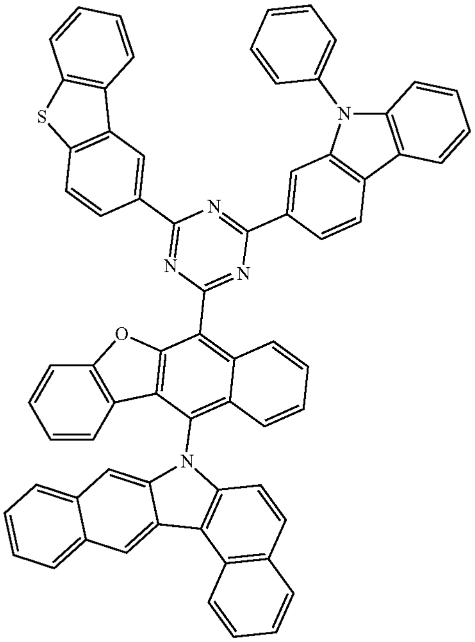
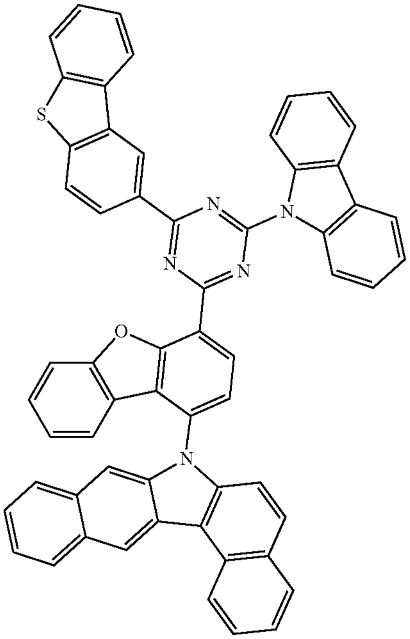

-continued
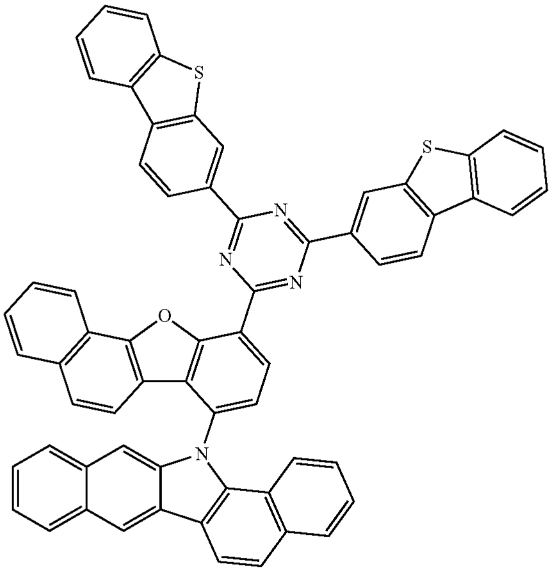
-continued
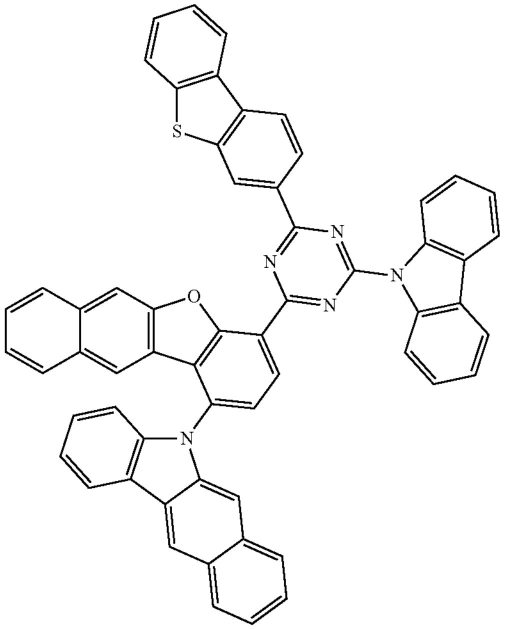
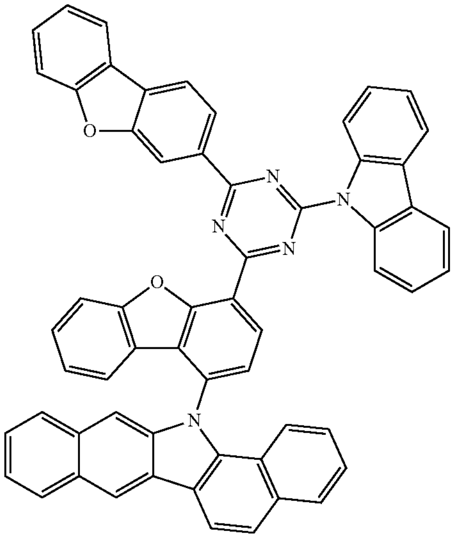
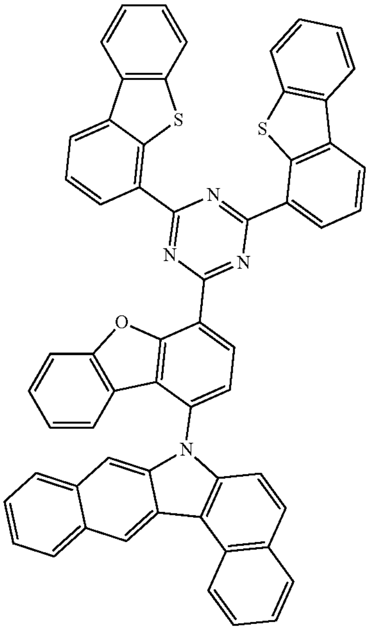

-continued
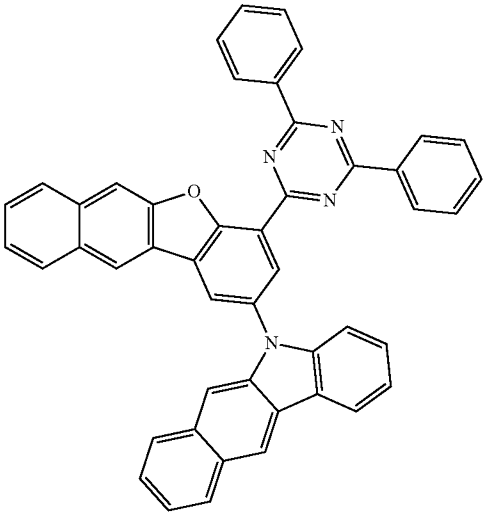
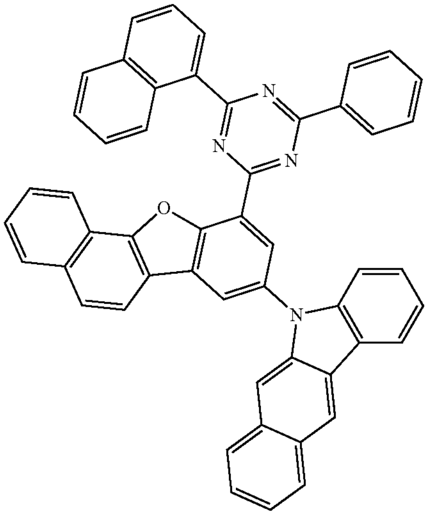
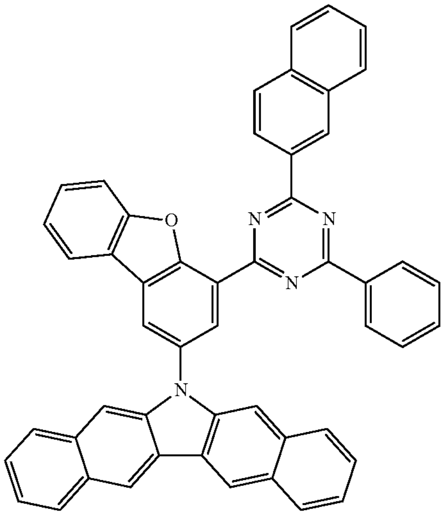
-continued
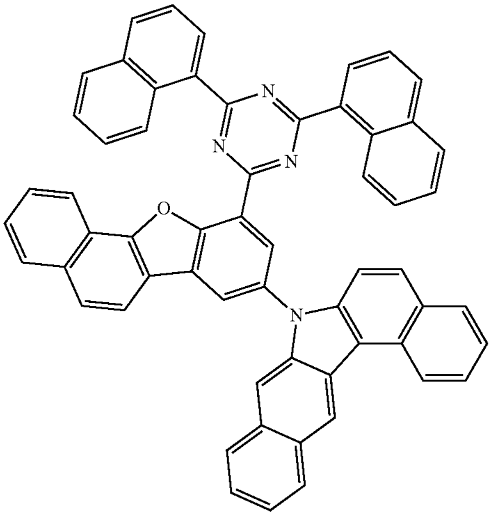
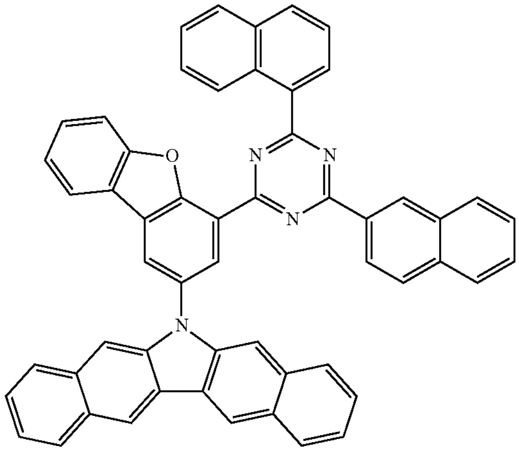
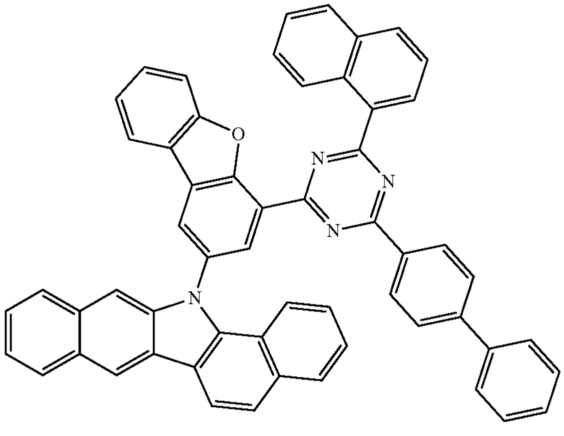

-continued
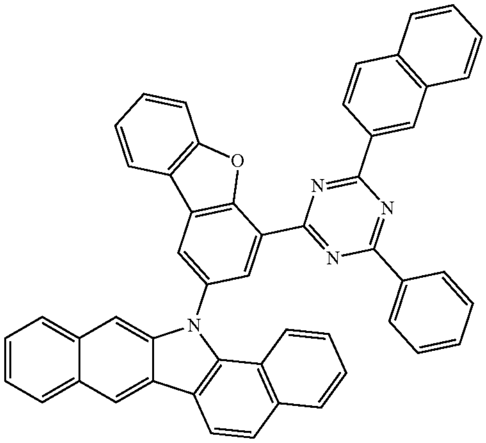
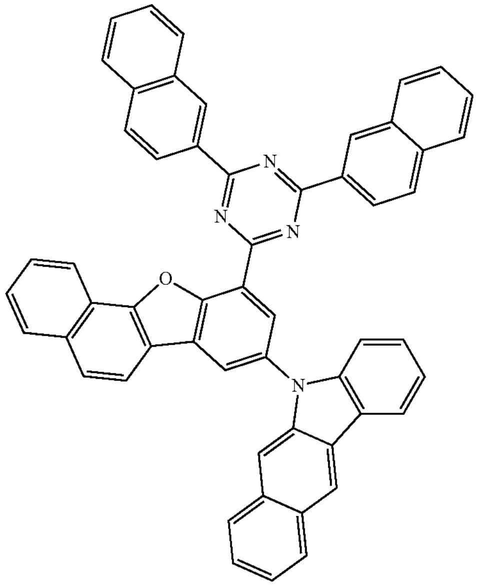
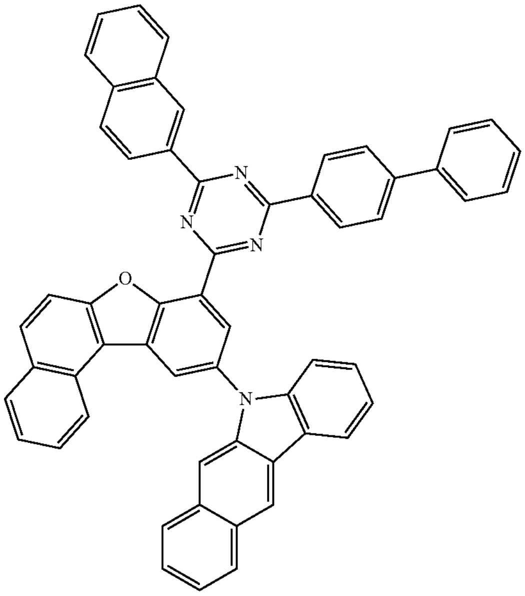
-continued
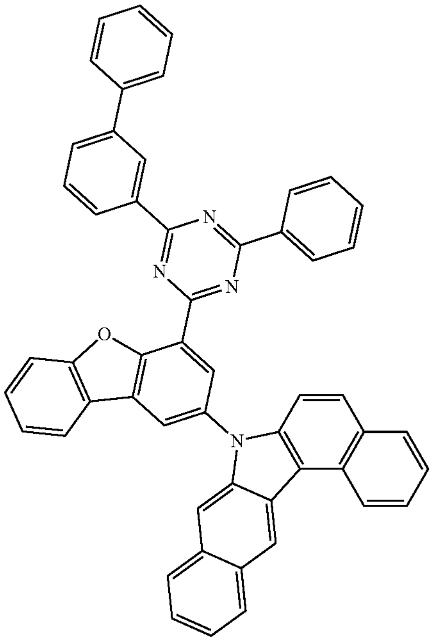
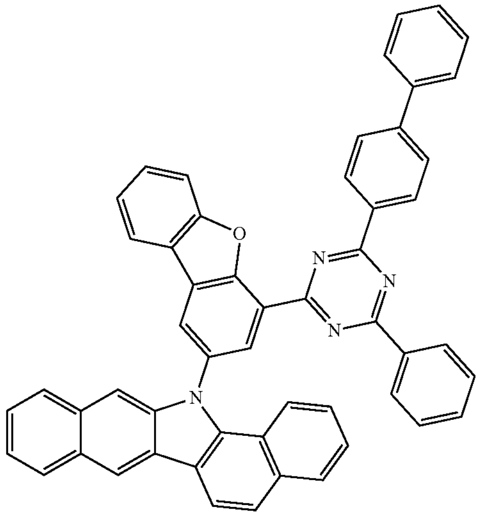

-continued
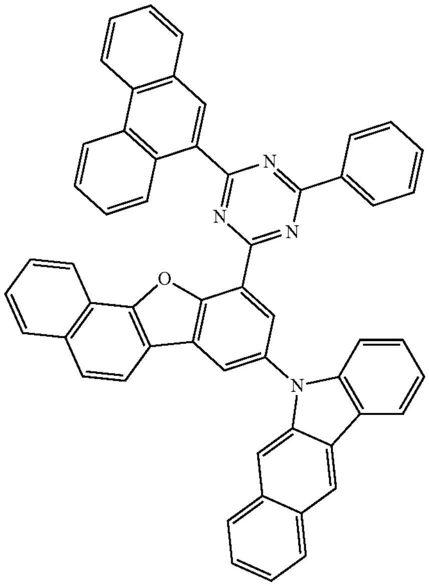
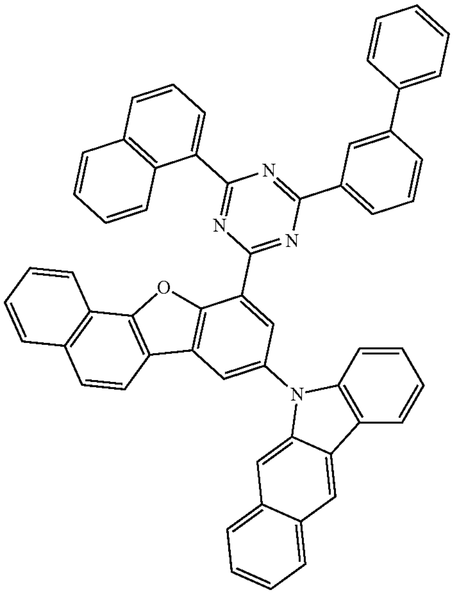
-continued
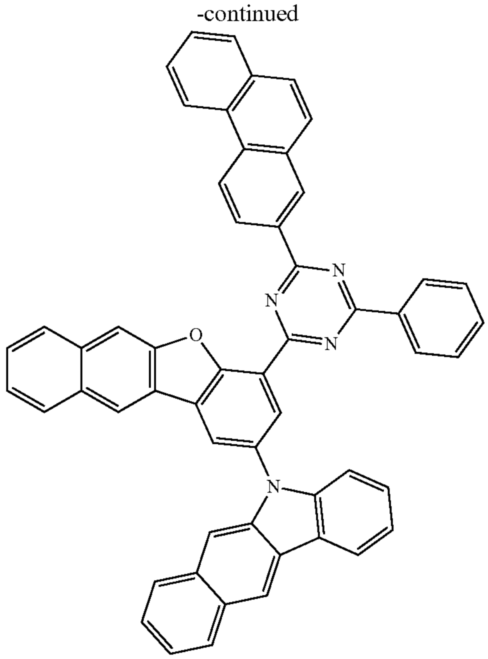
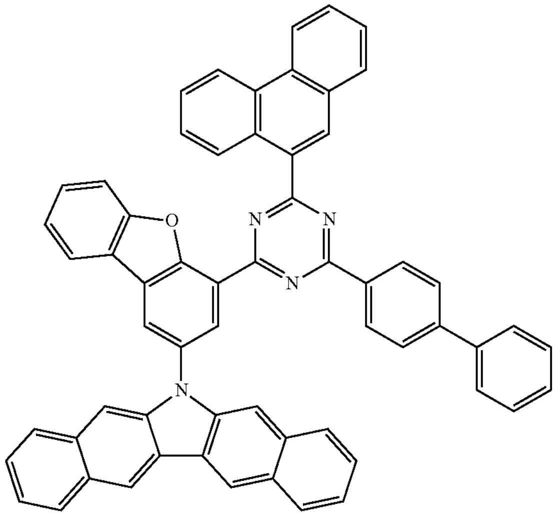
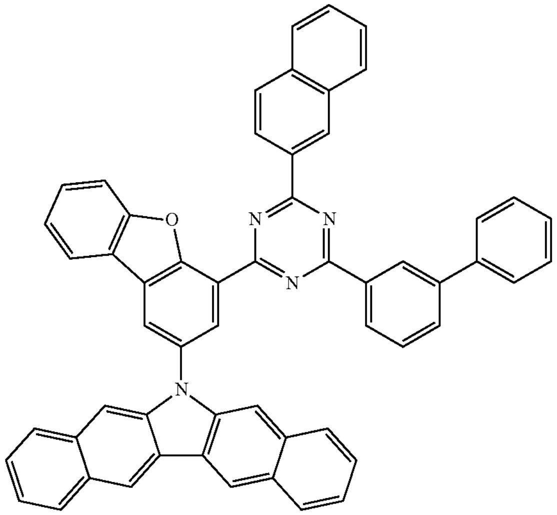

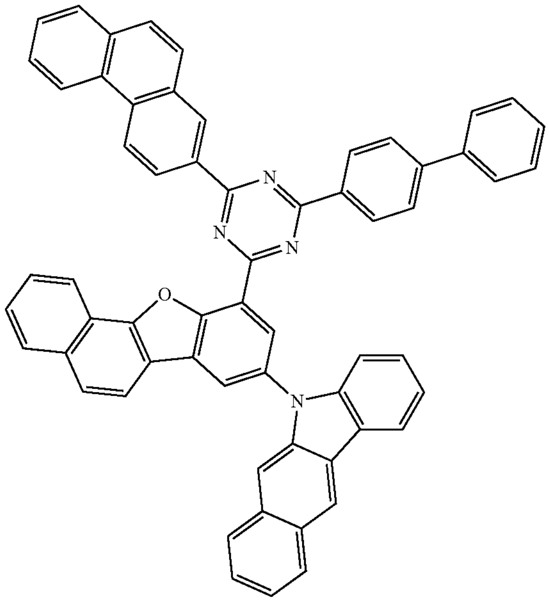
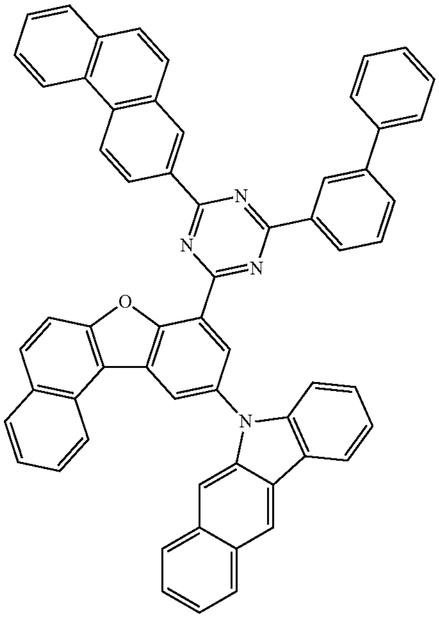
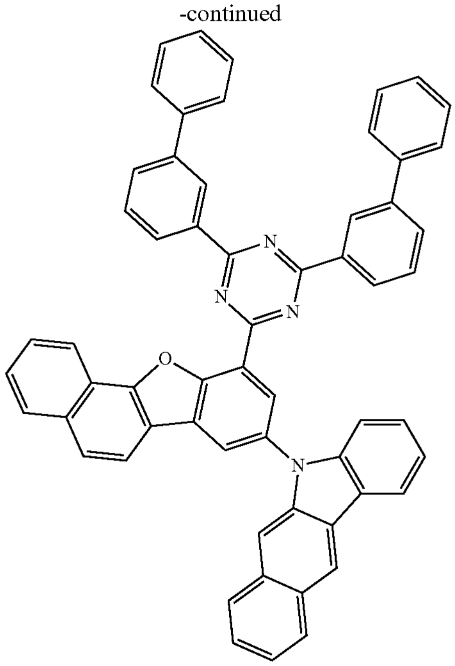
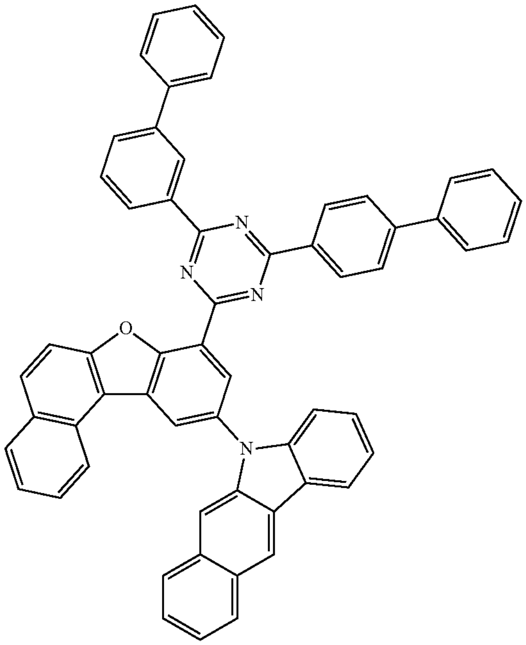

-continued
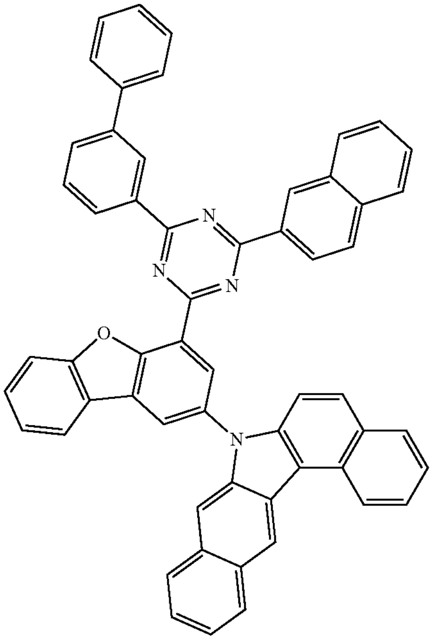
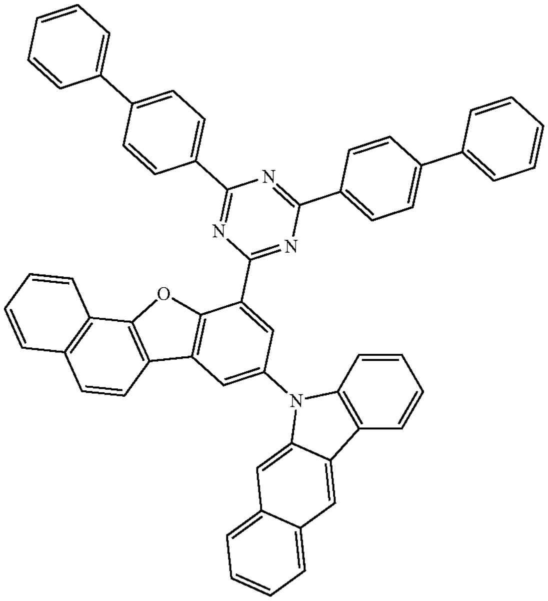
-continued
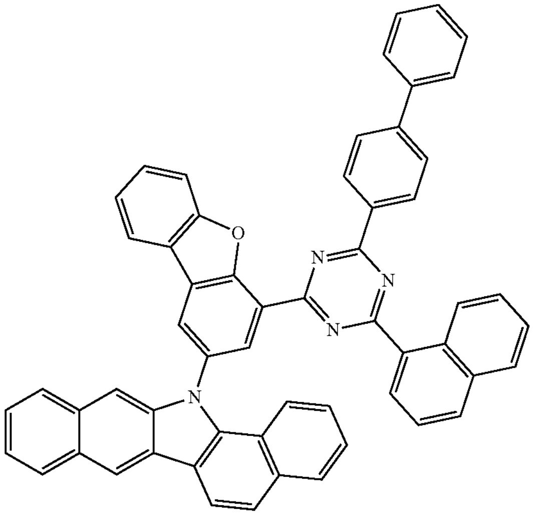
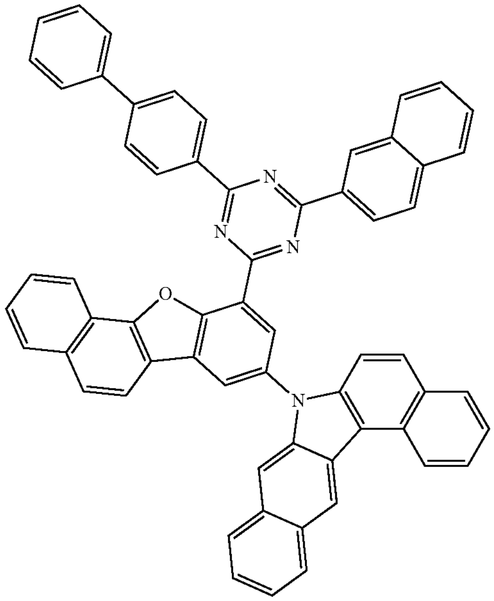
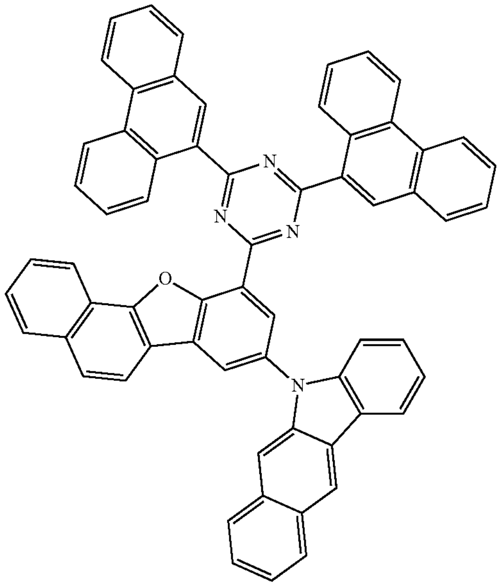

-continued
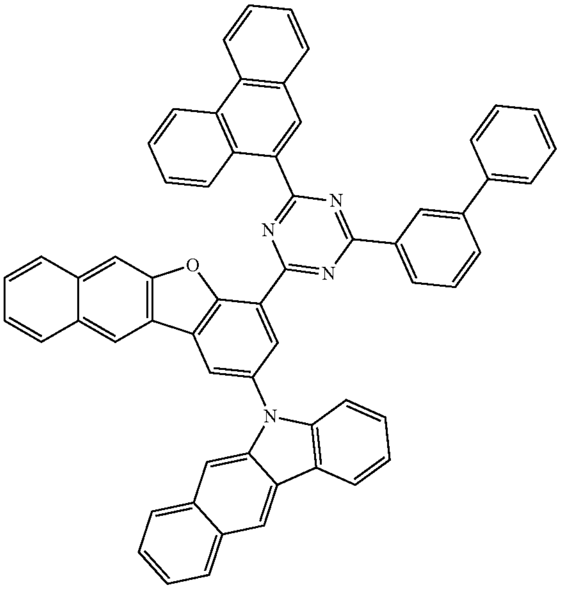
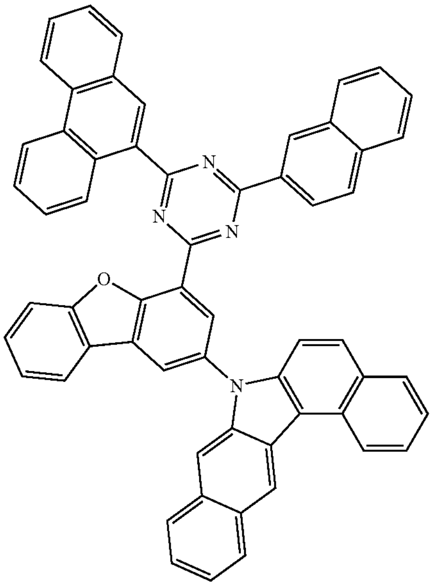
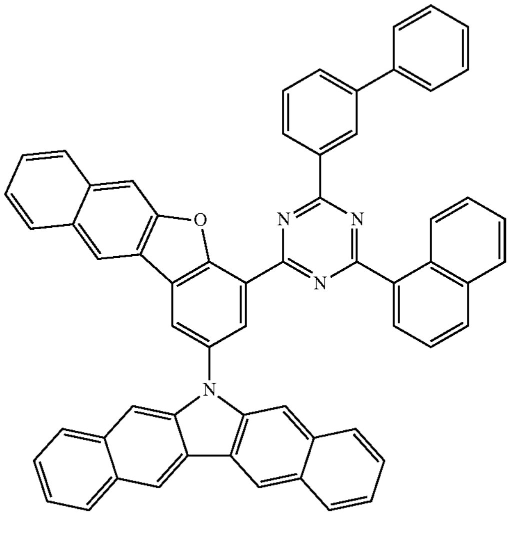
-continued
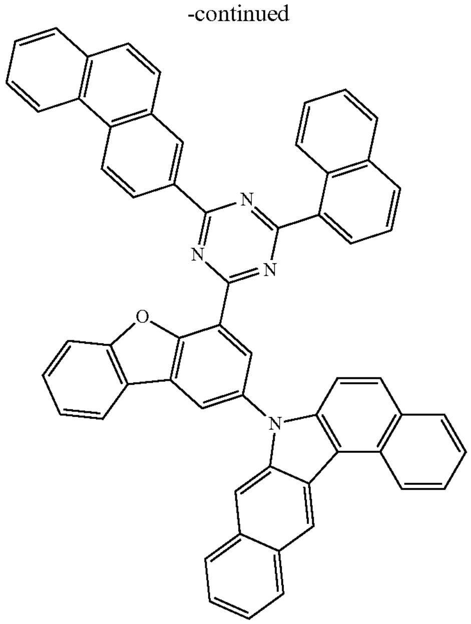
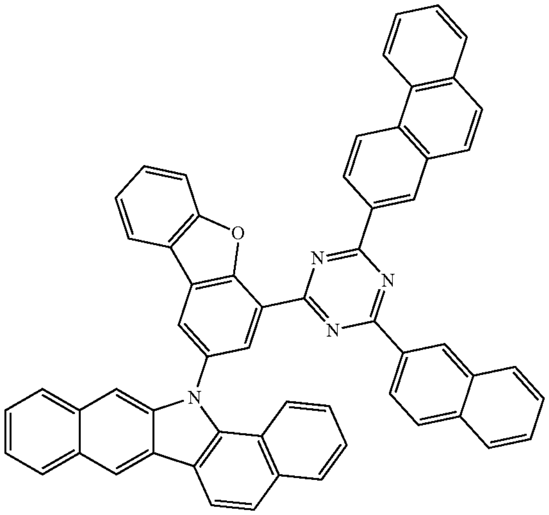
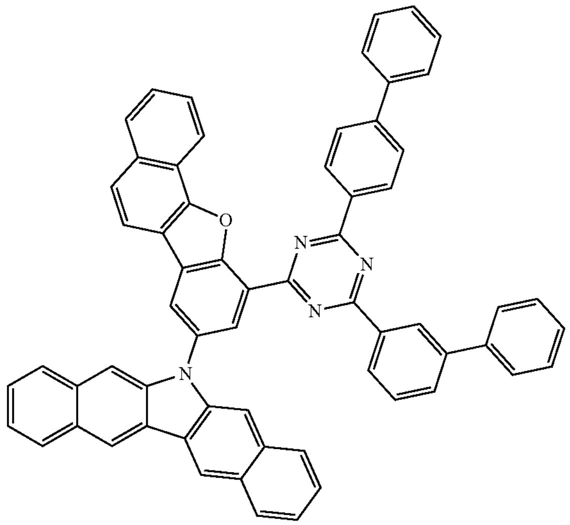

-continued
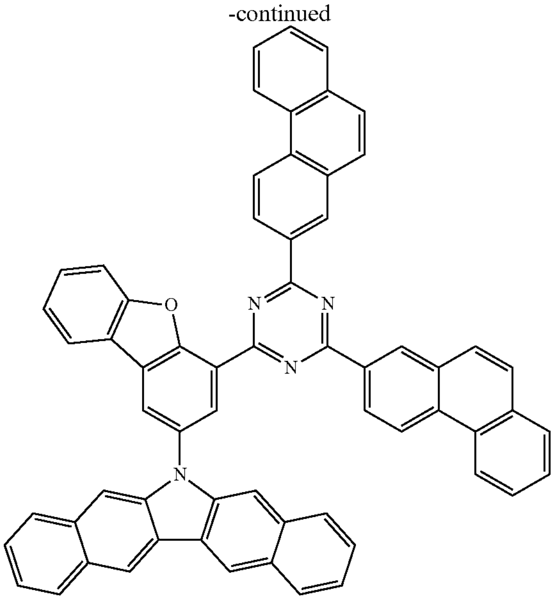
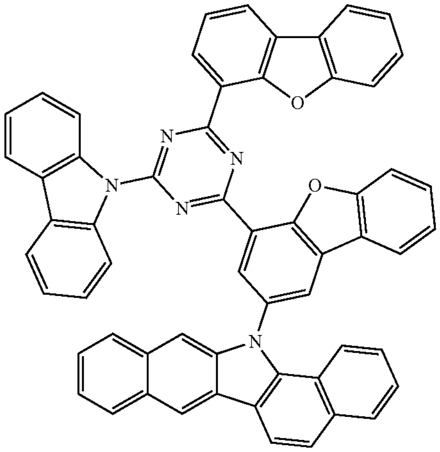
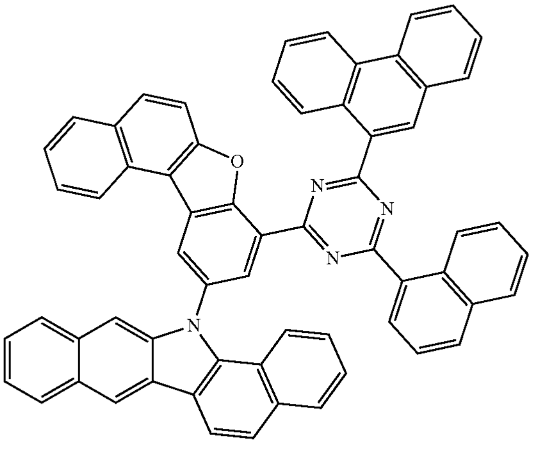
-continued
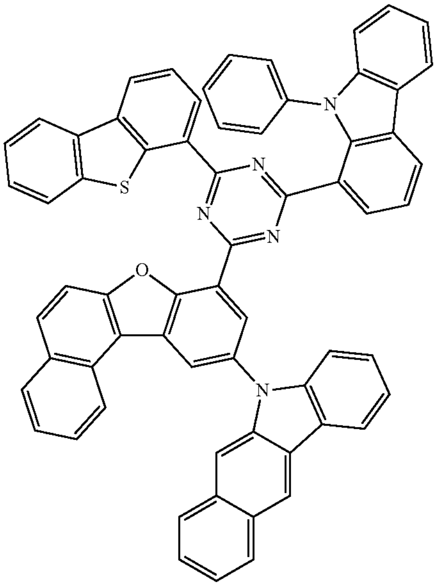
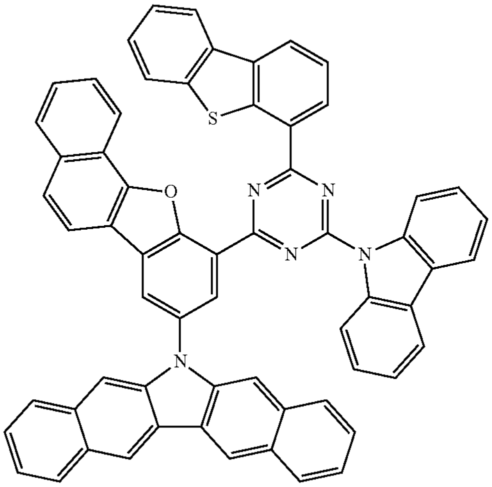
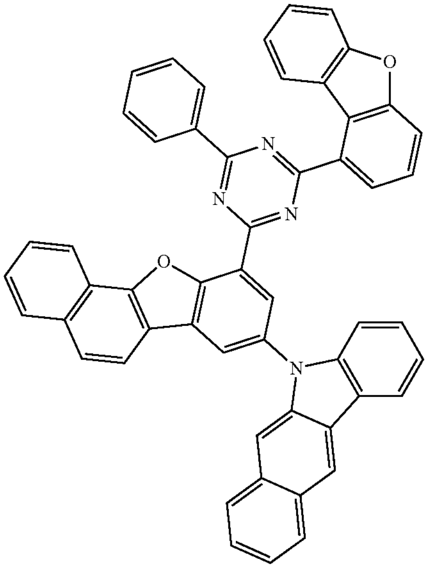

-continued
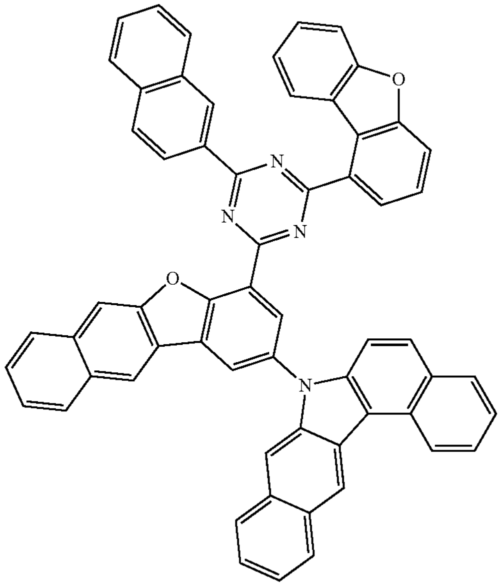
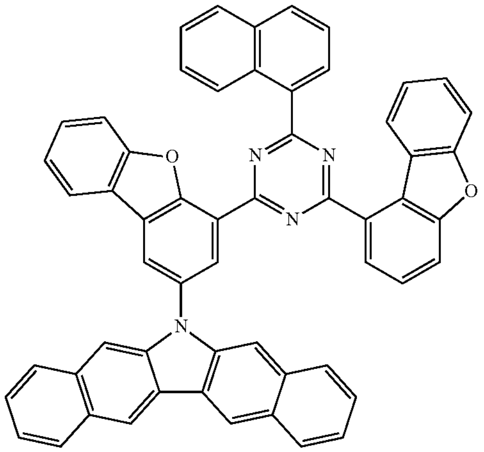
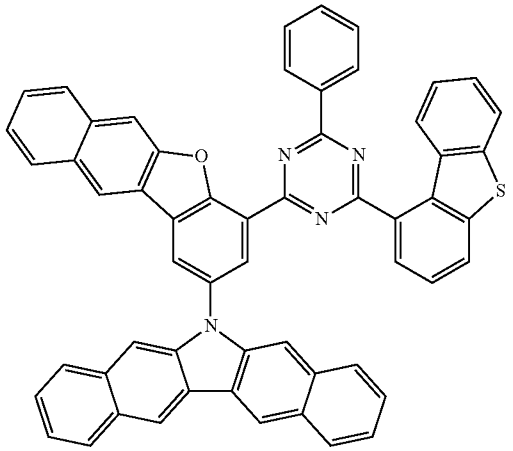
-continued
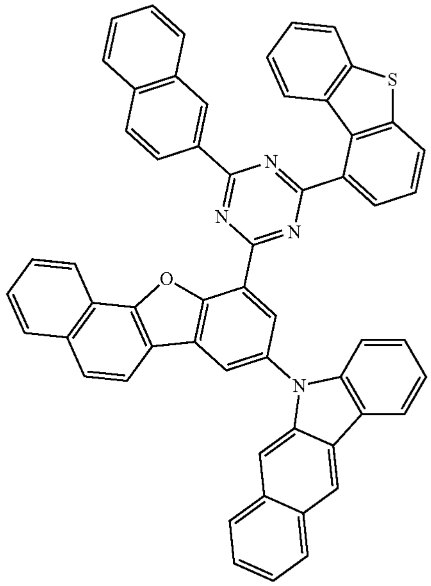
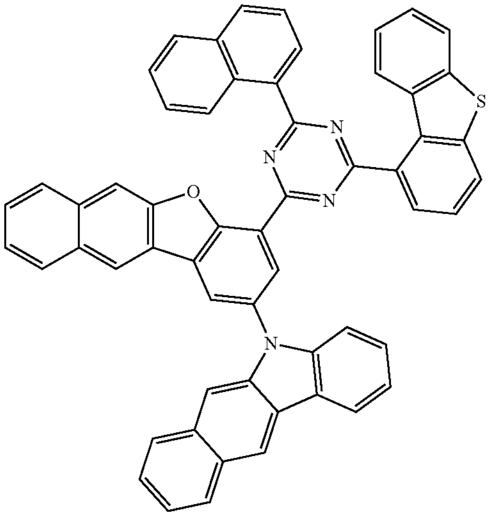
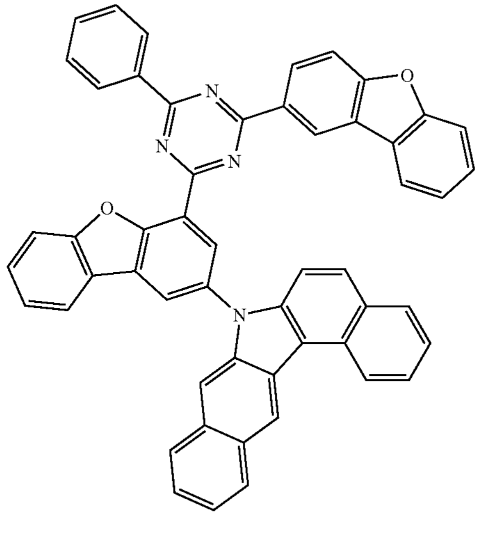

-continued
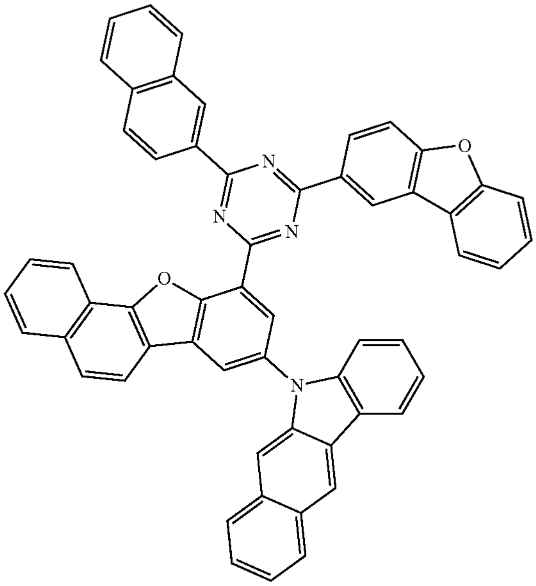
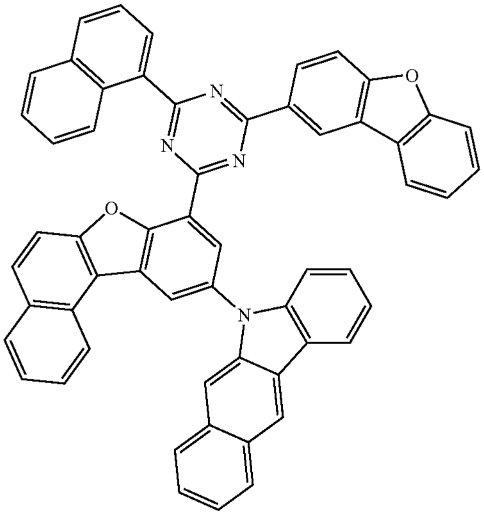
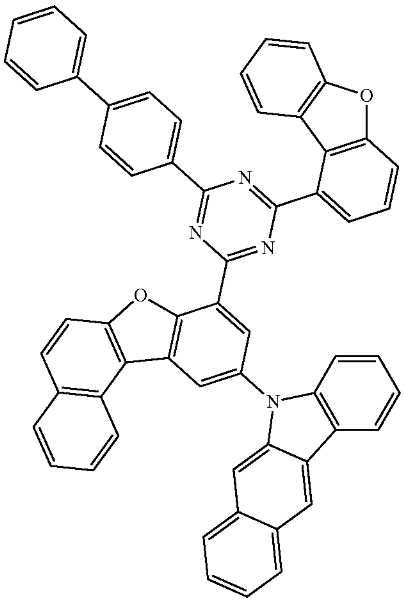
-continued
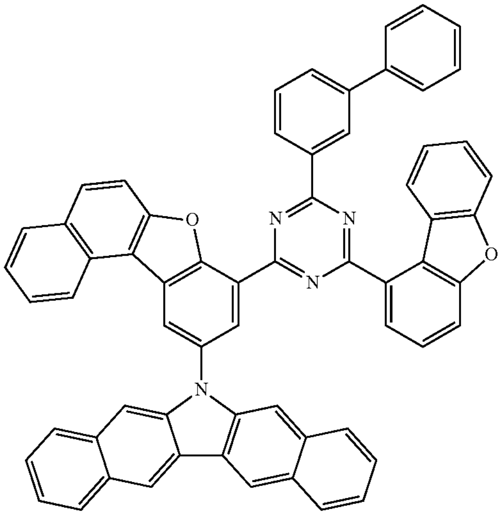
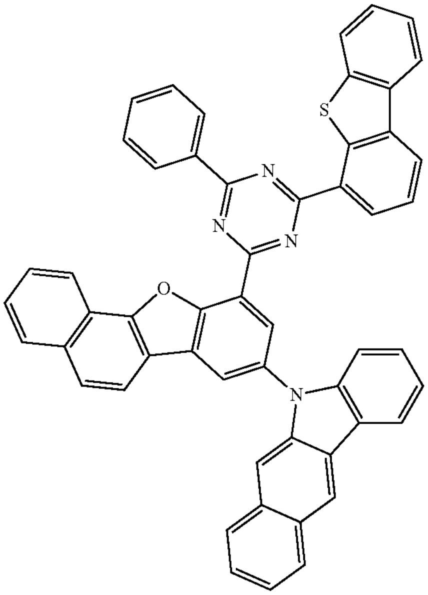
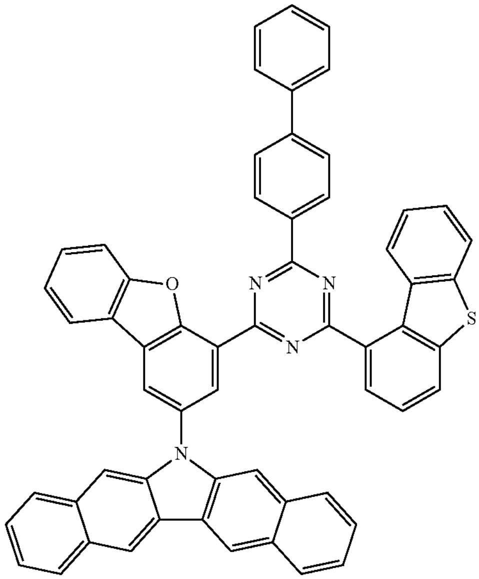

-continued
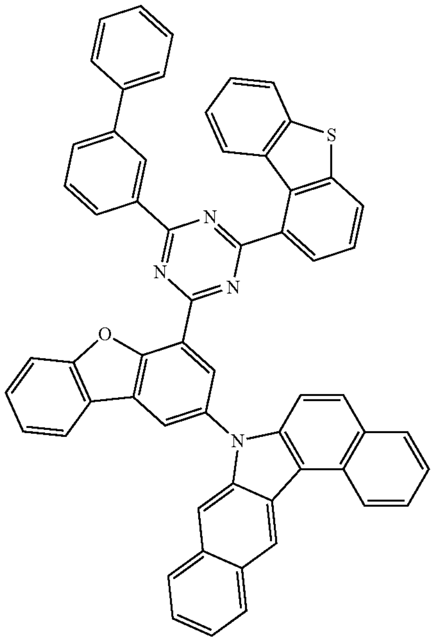
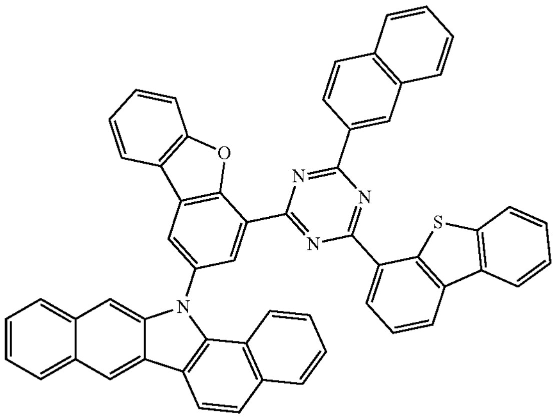
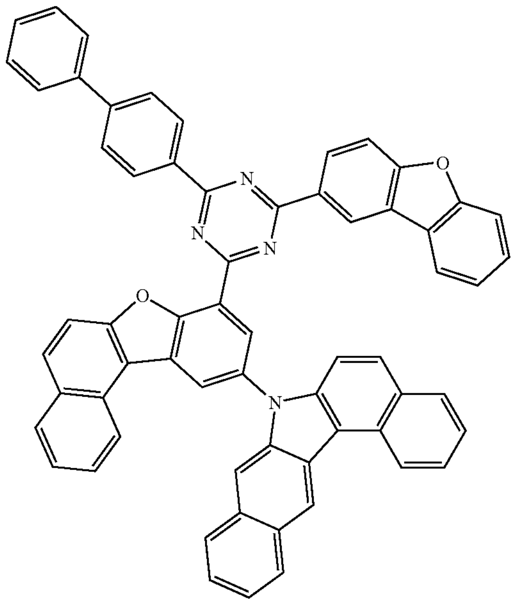
-continued
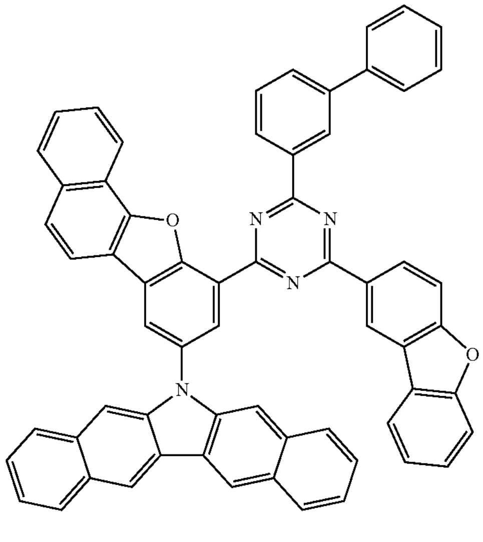
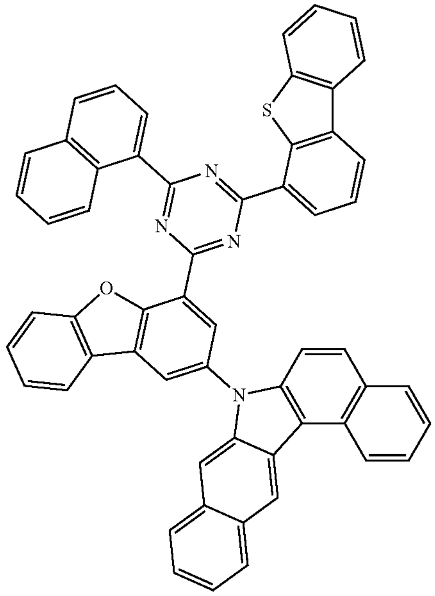
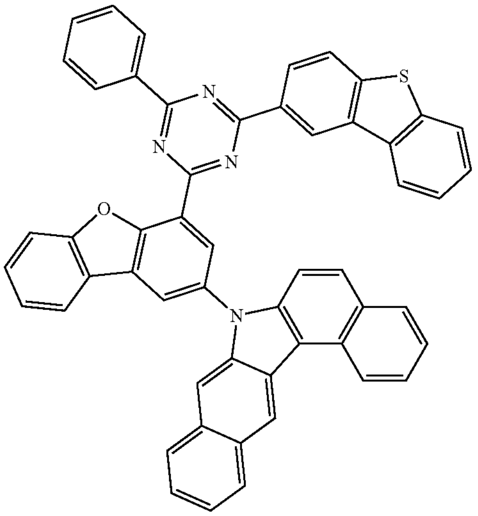

-continued
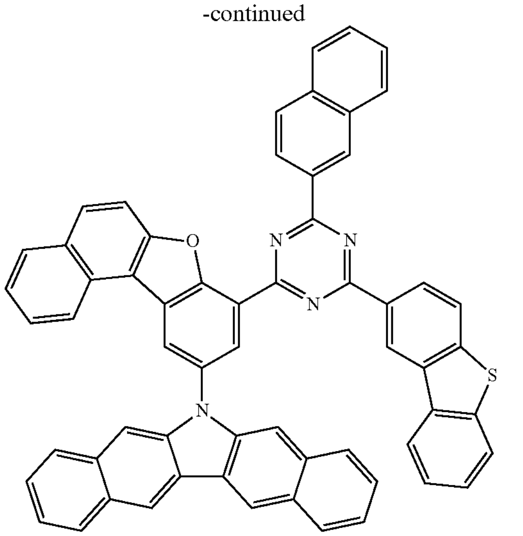
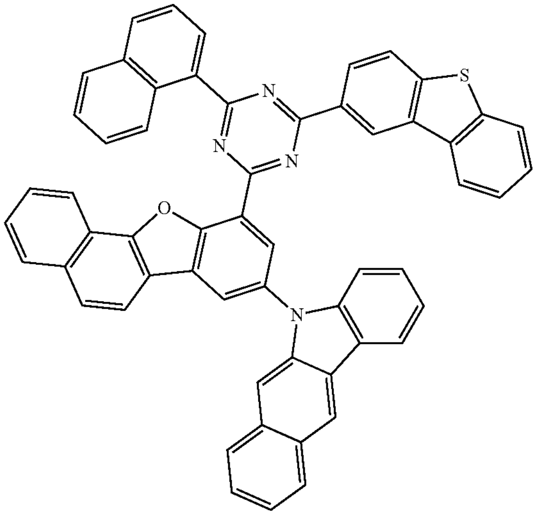
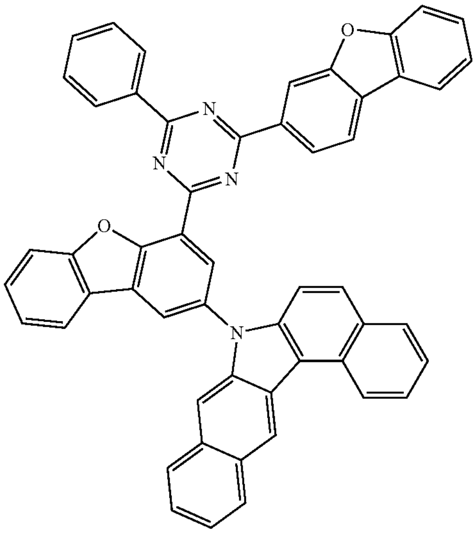
-continued
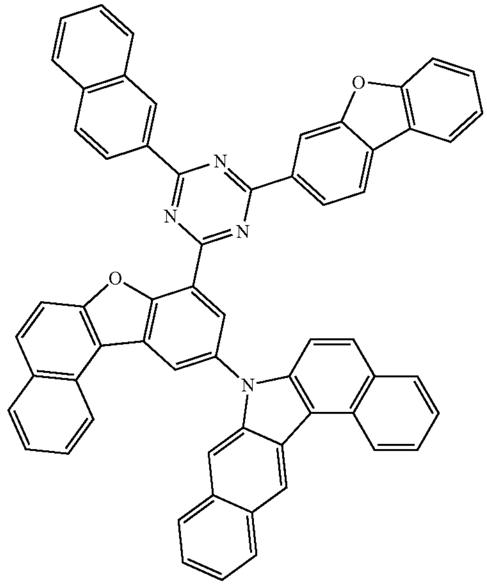
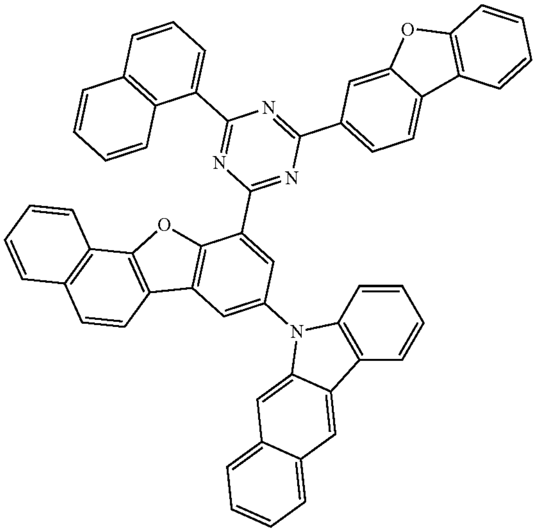
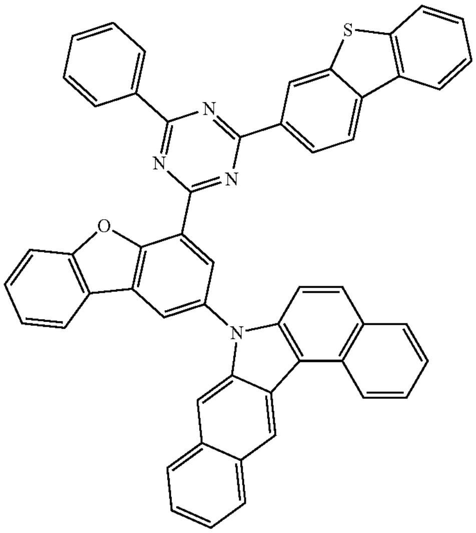

-continued
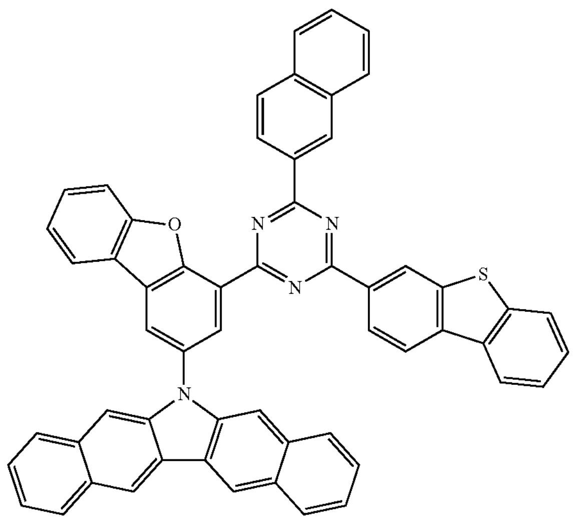
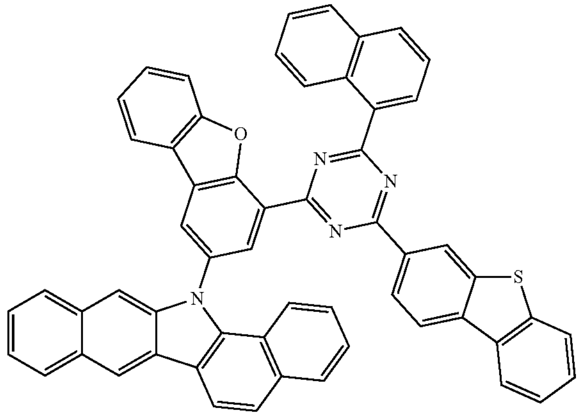
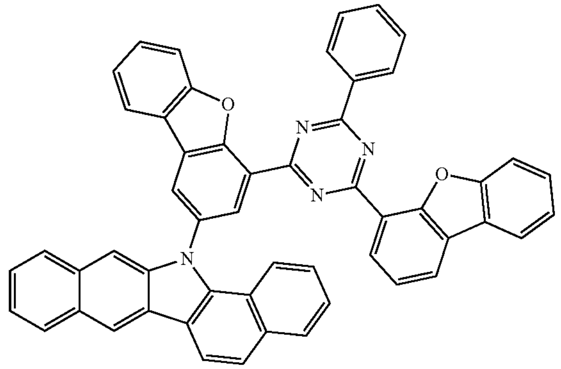
-continued
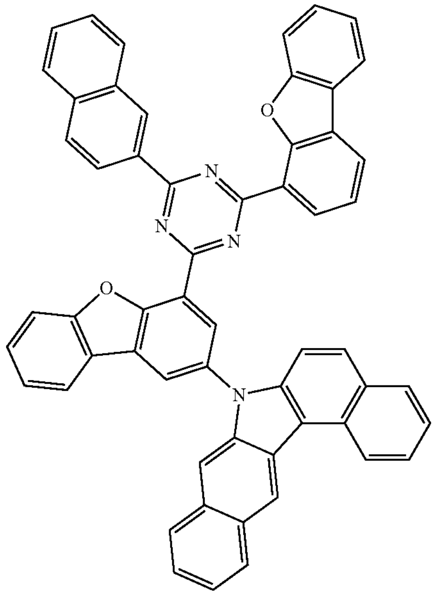
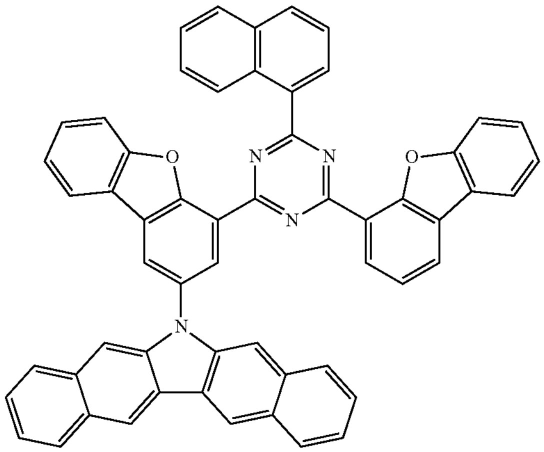
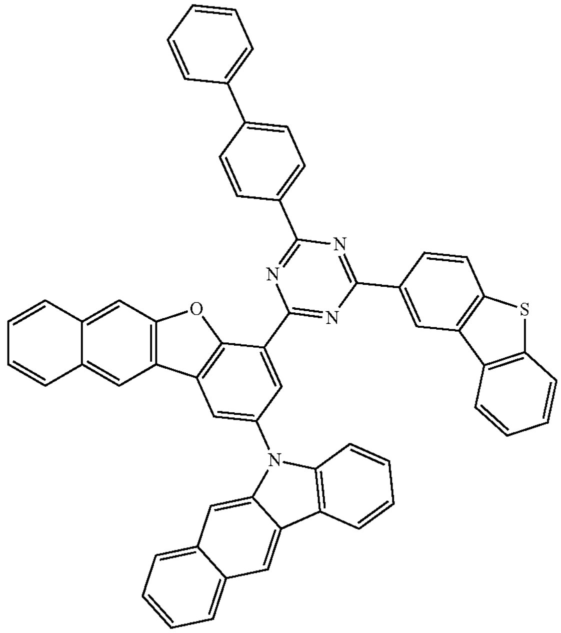

-continued
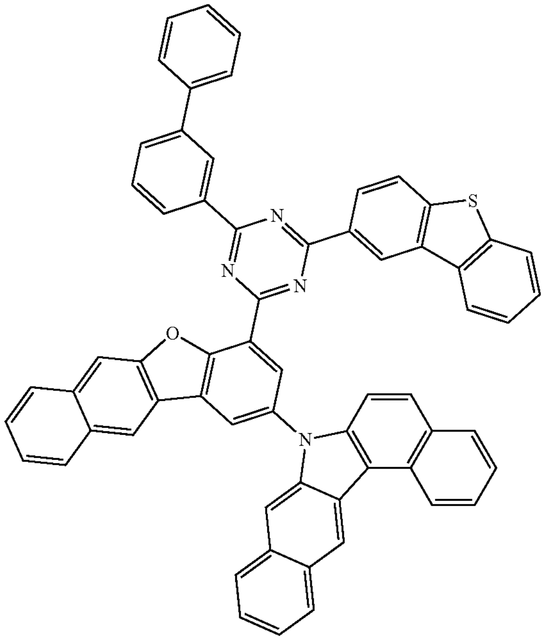
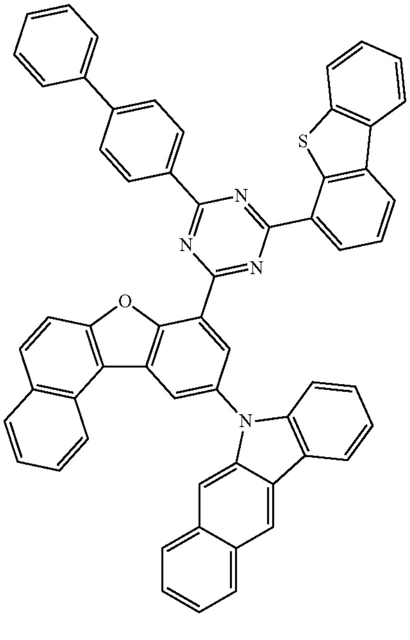
-continued
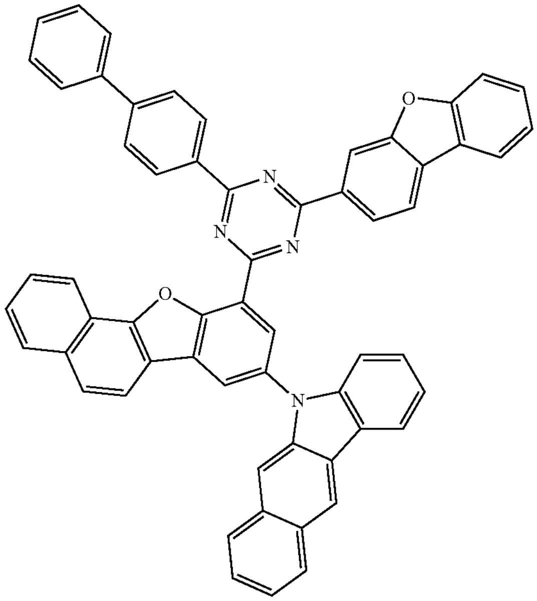
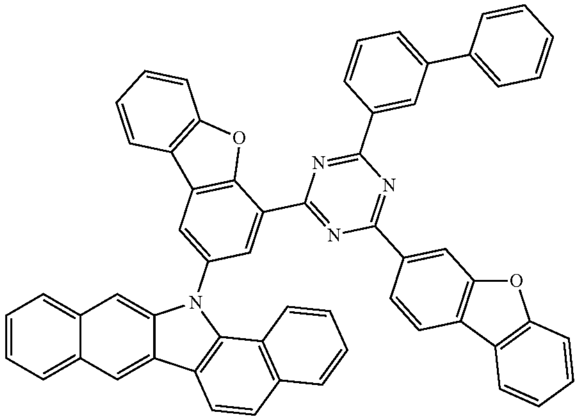
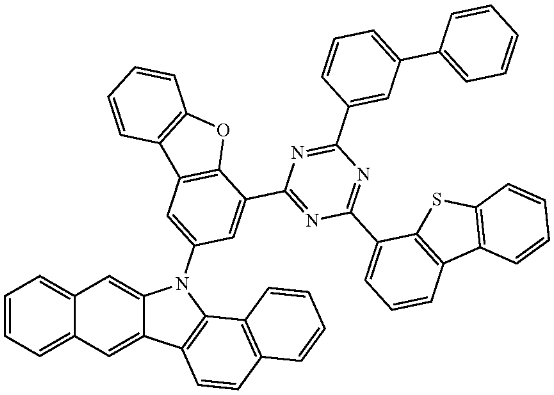

-continued
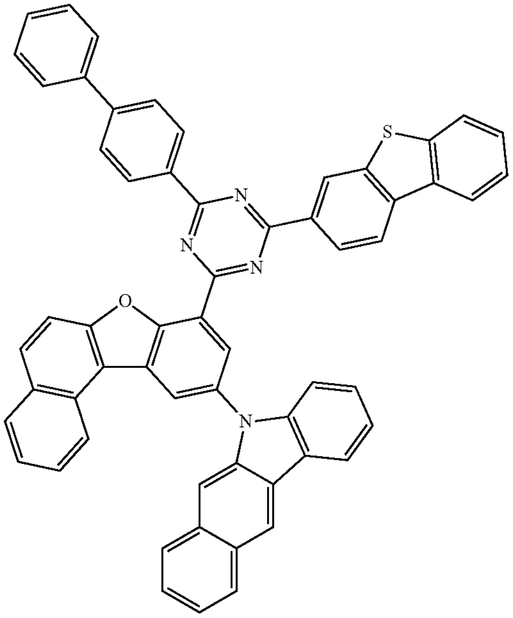
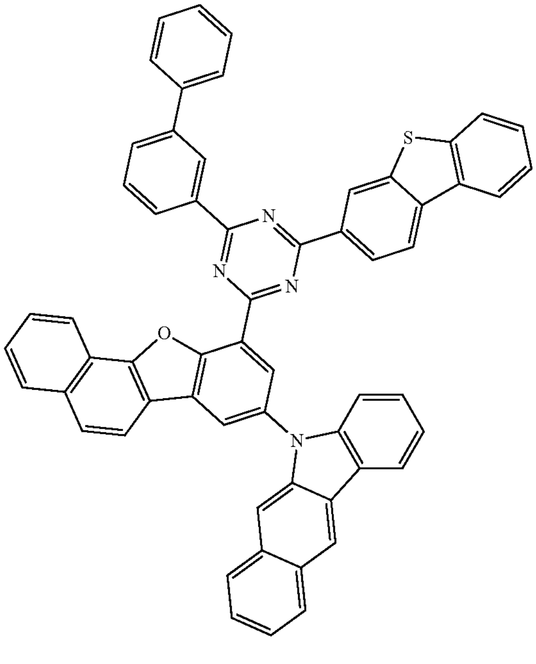
-continued
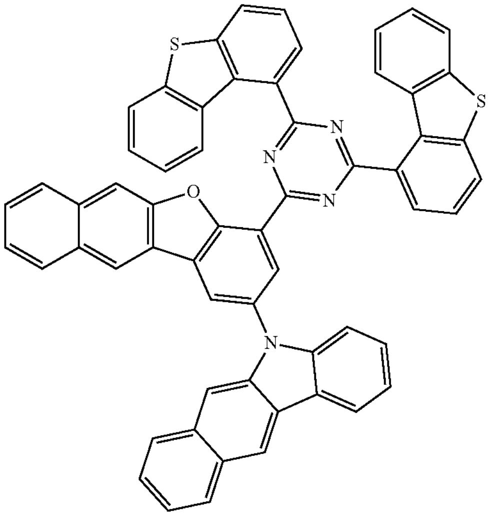
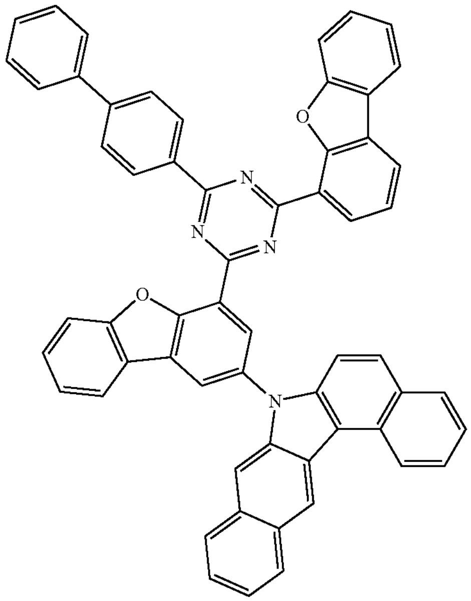
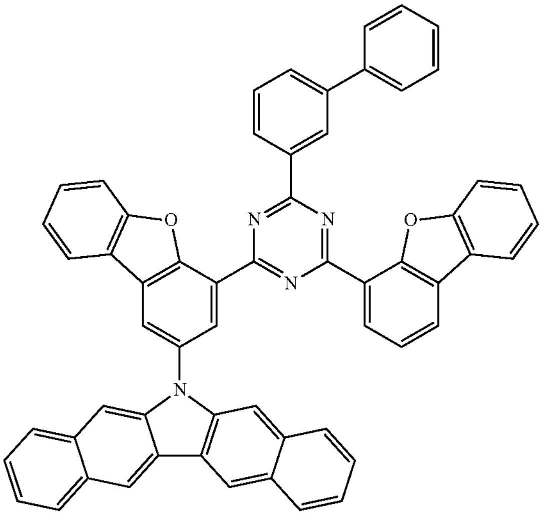

-continued
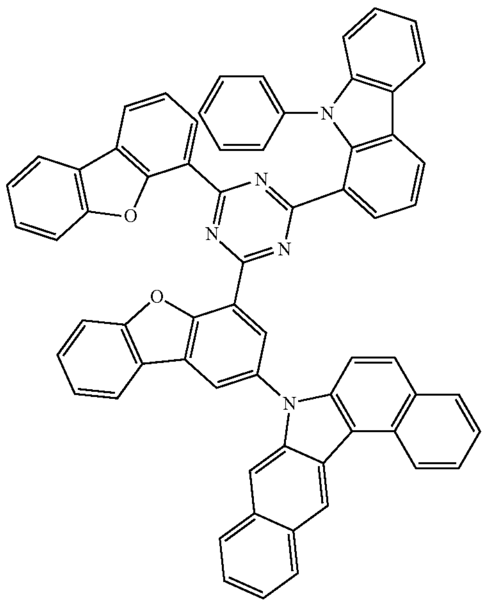
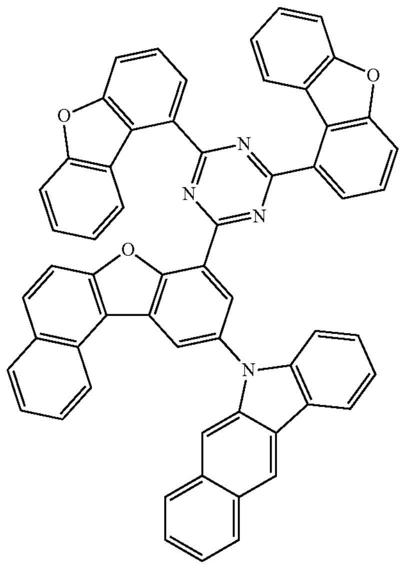
-continued
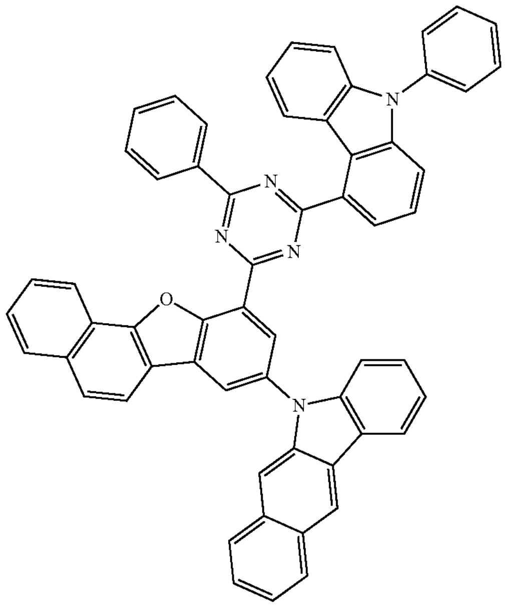
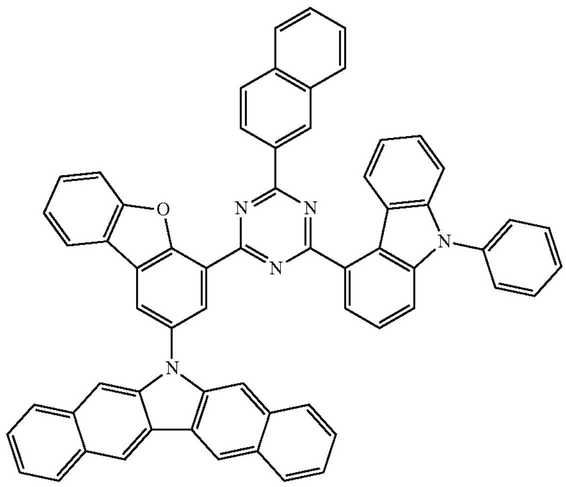
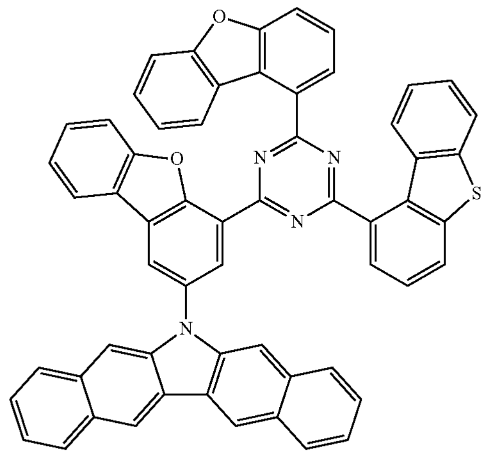

-continued
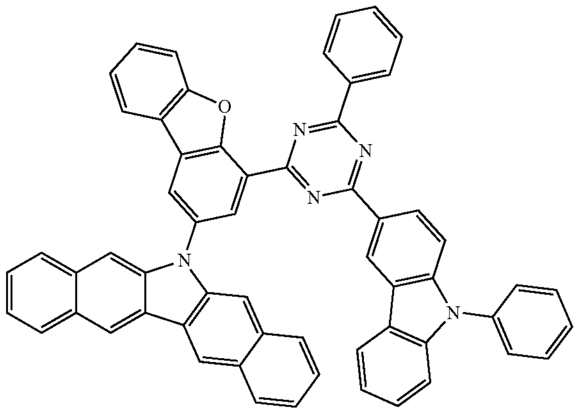
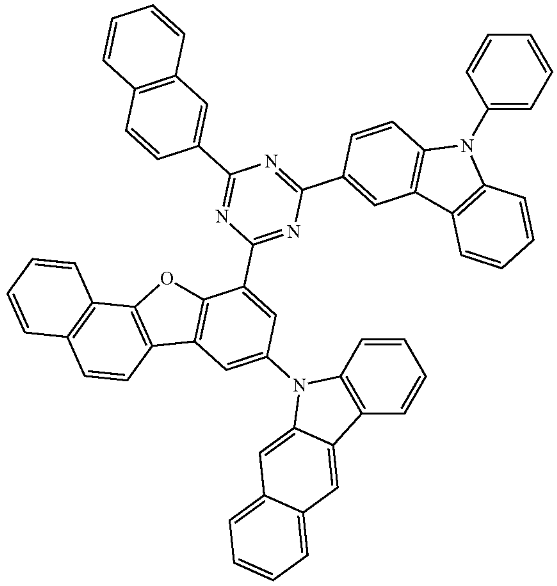
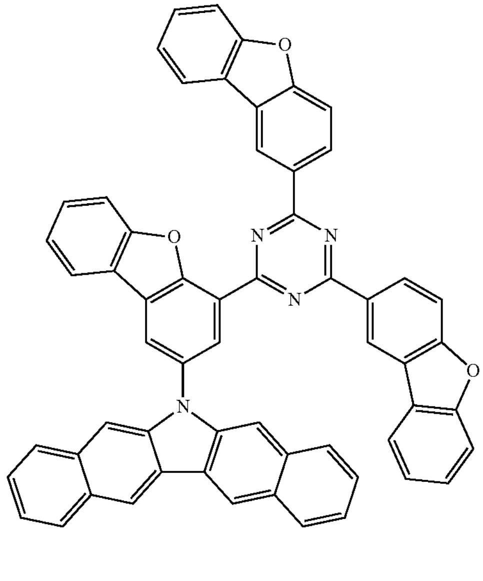
-continued
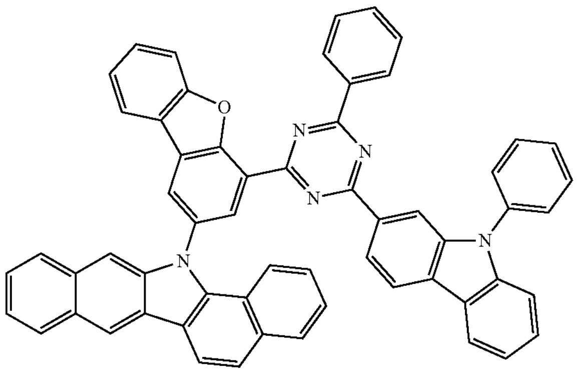
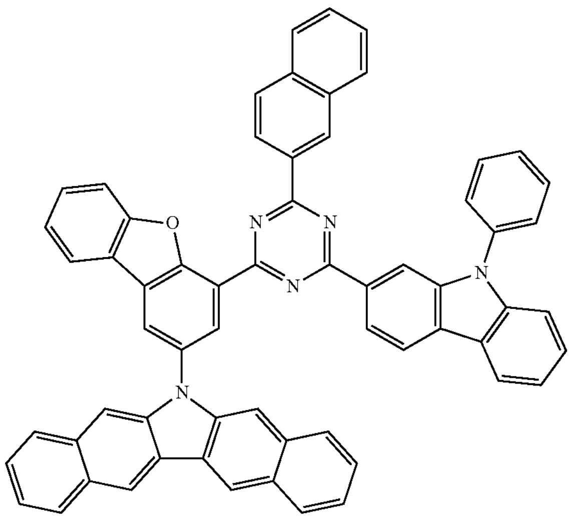
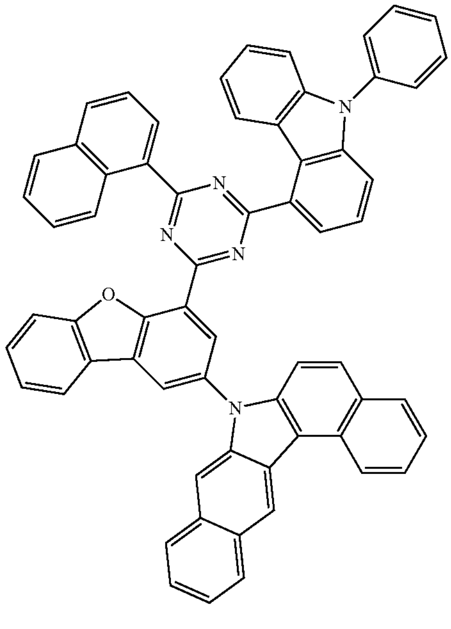

-continued
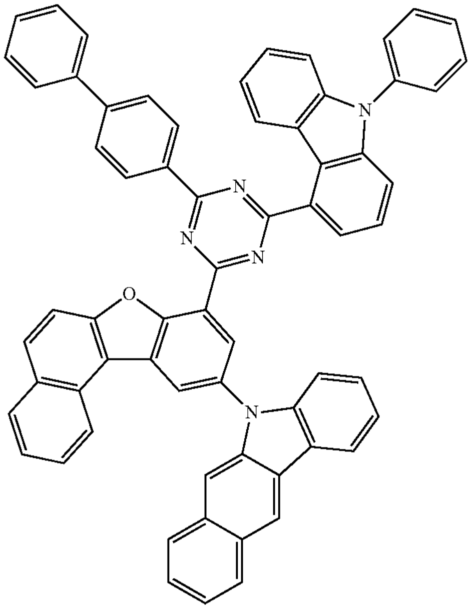
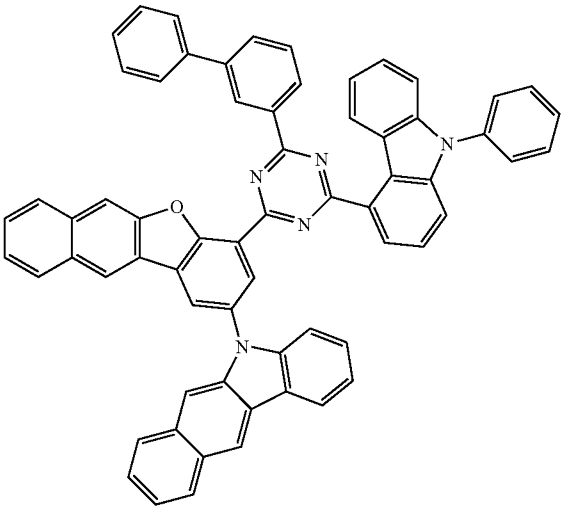
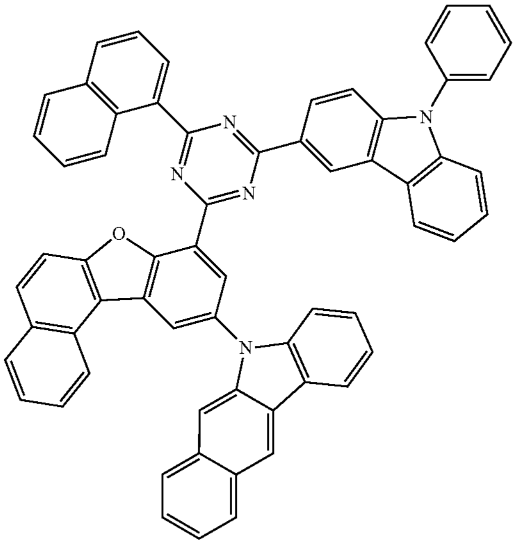
-continued
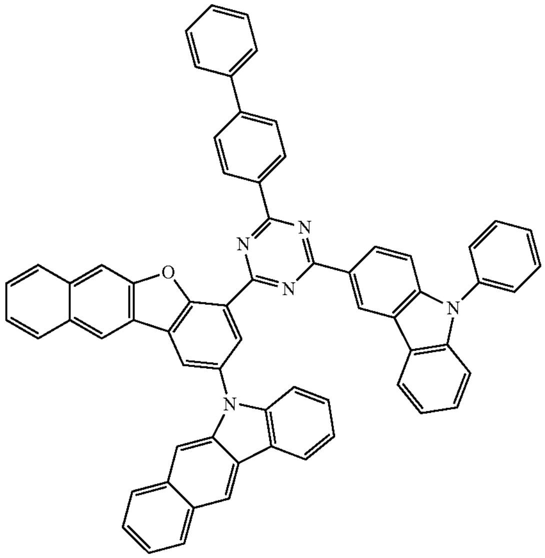
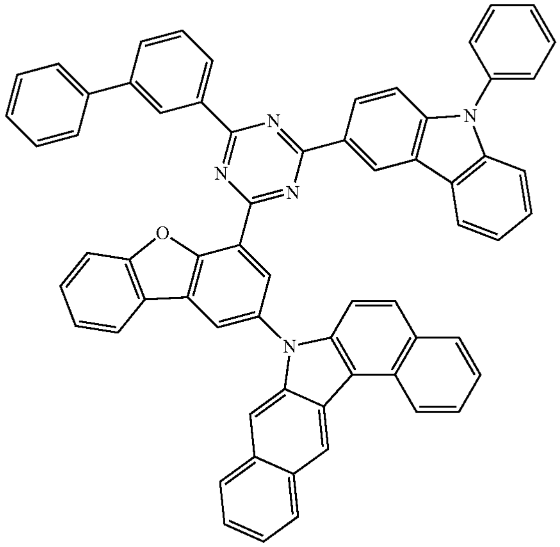
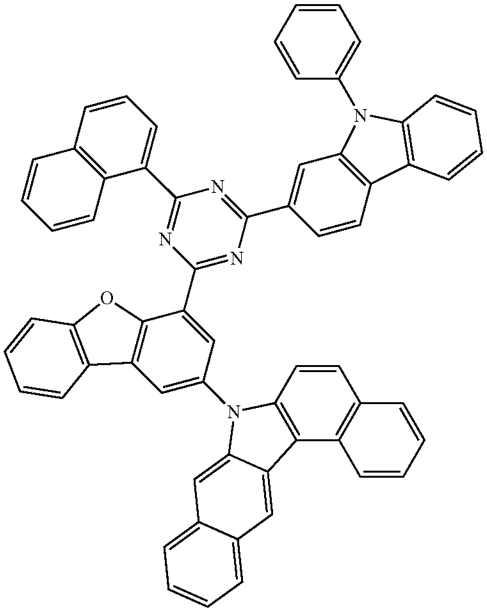

-continued
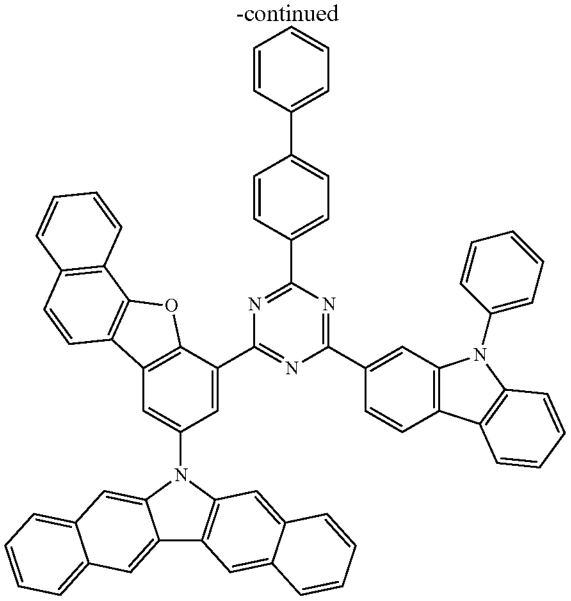
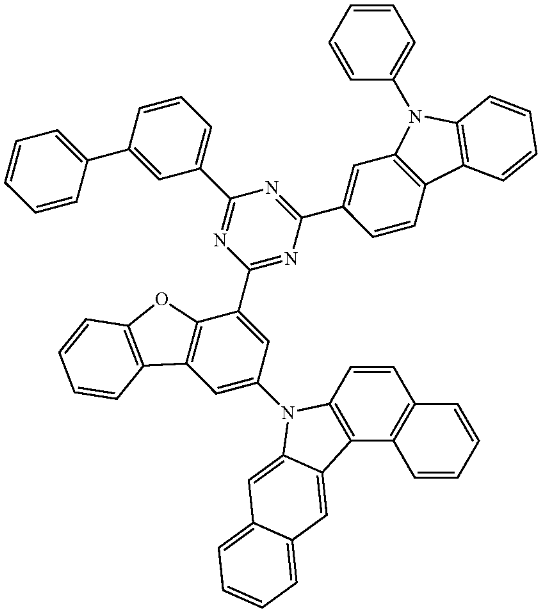
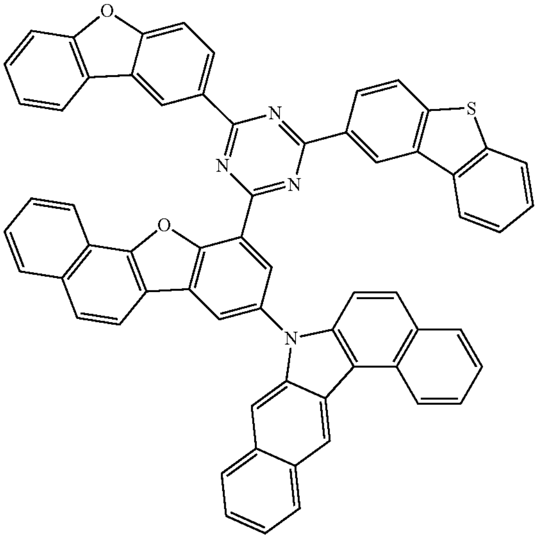
-continued
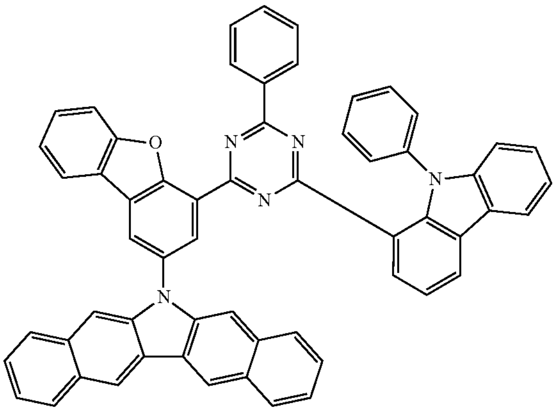
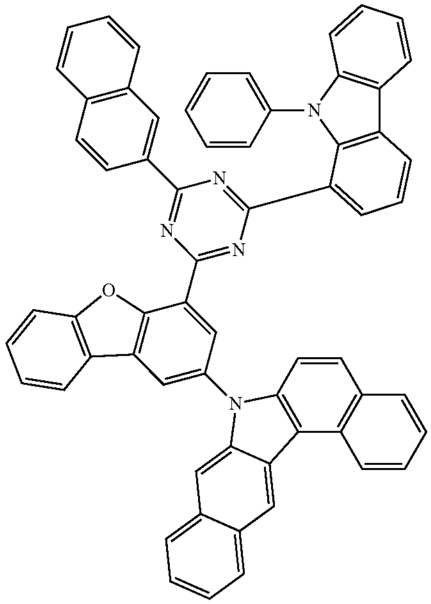
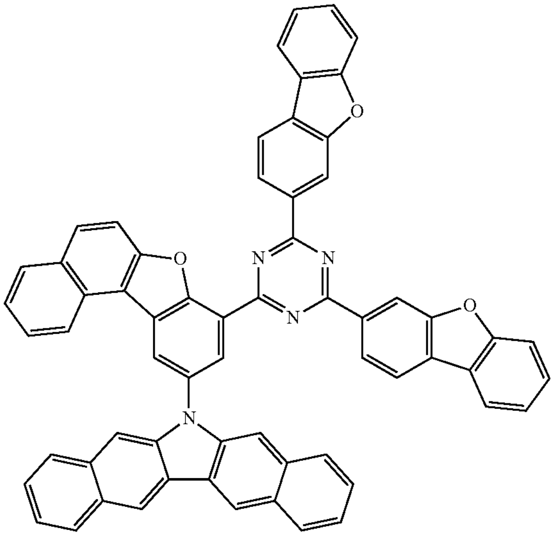

-continued
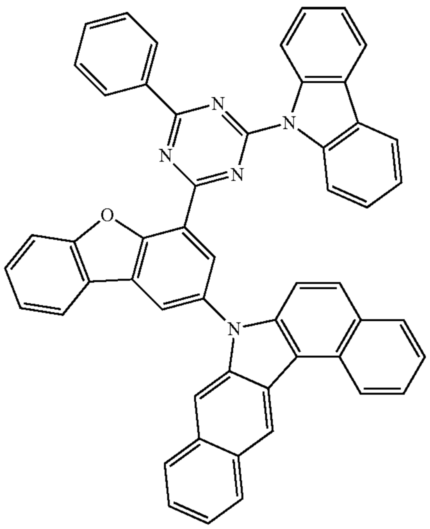
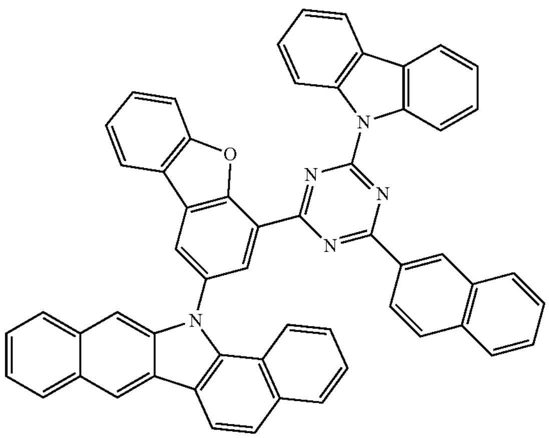
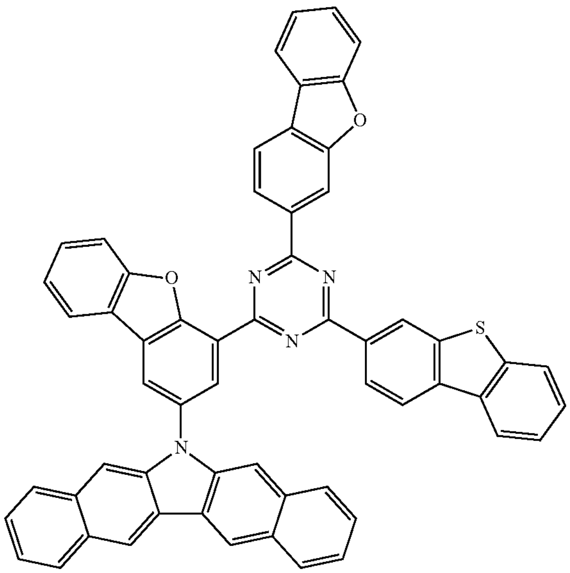
-continued
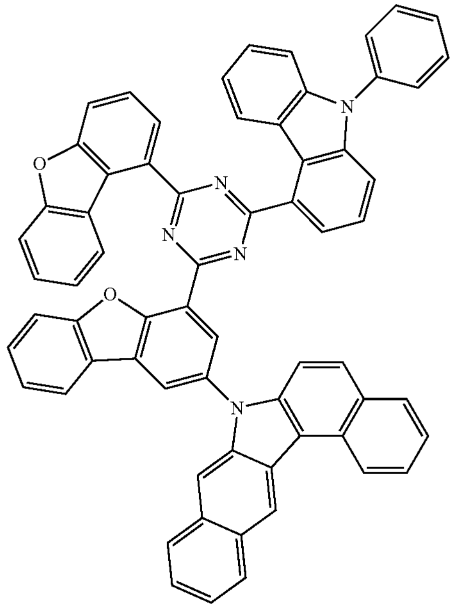
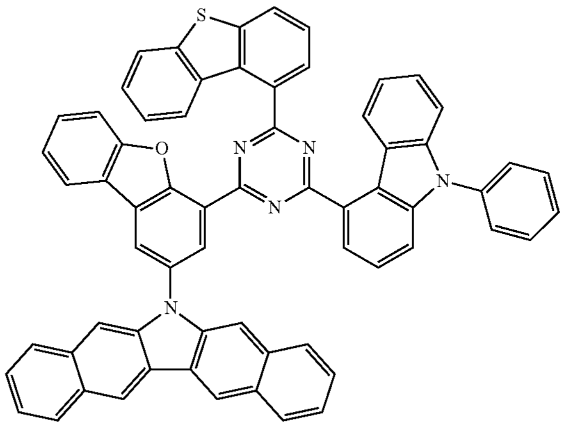
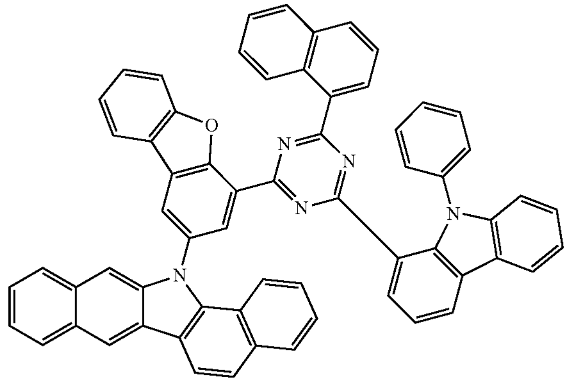

-continued
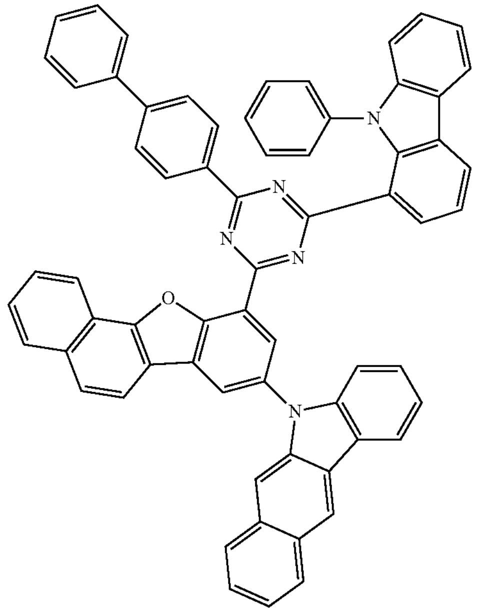
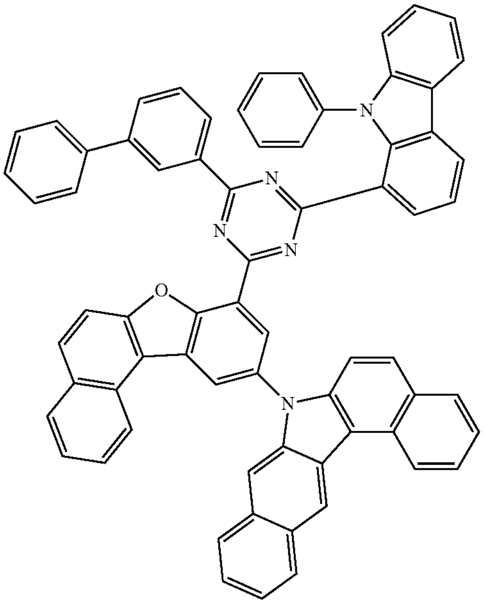
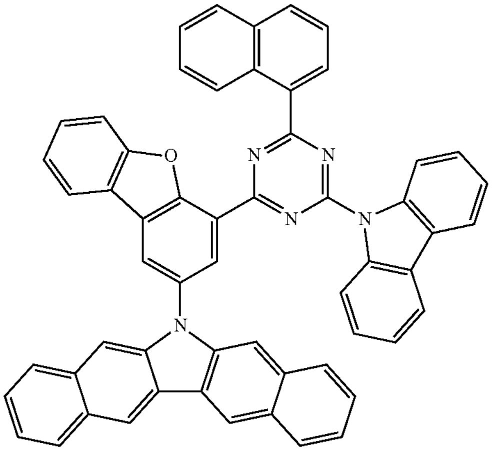
-continued
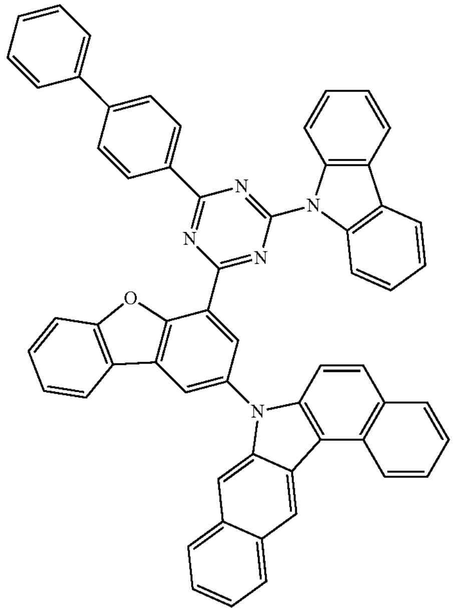
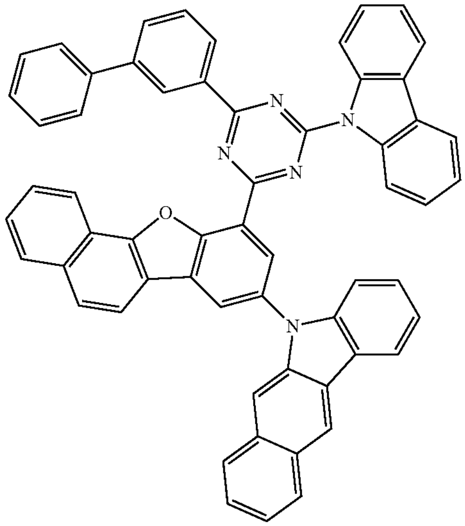
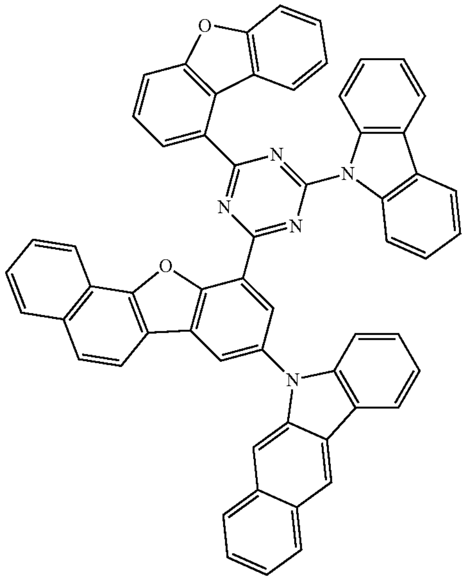

-continued
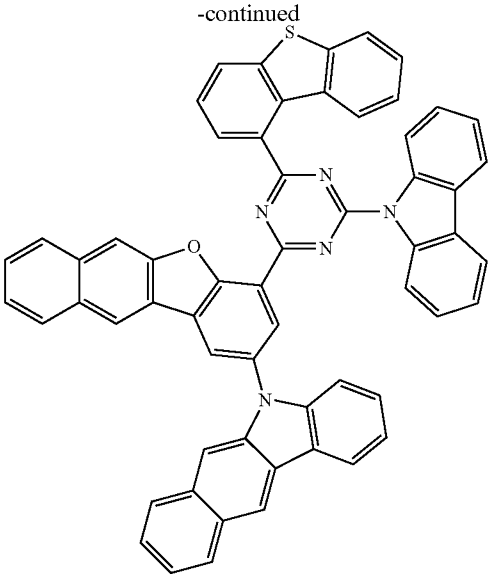
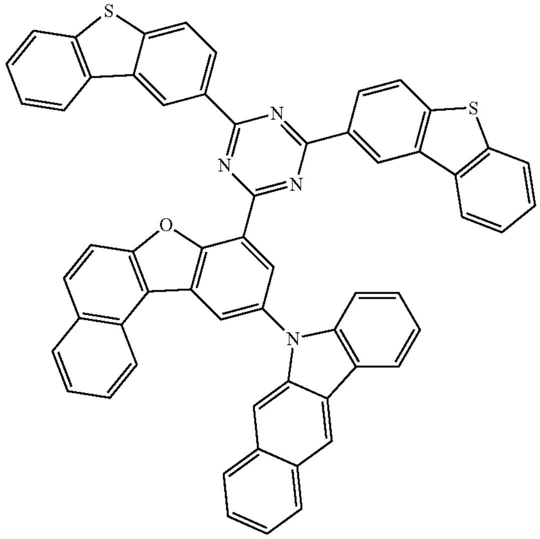
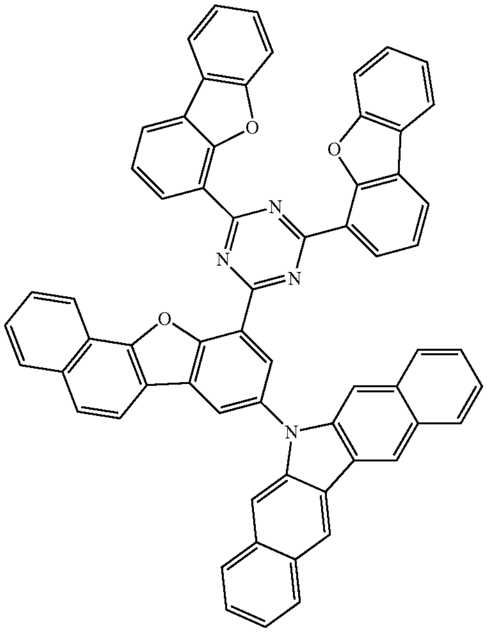
-continued
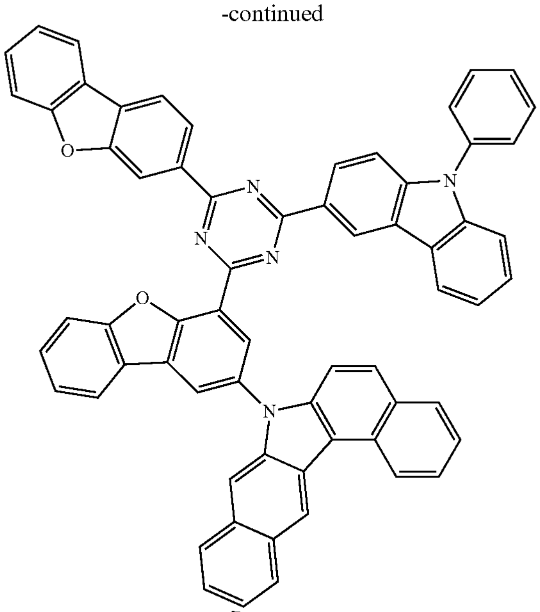
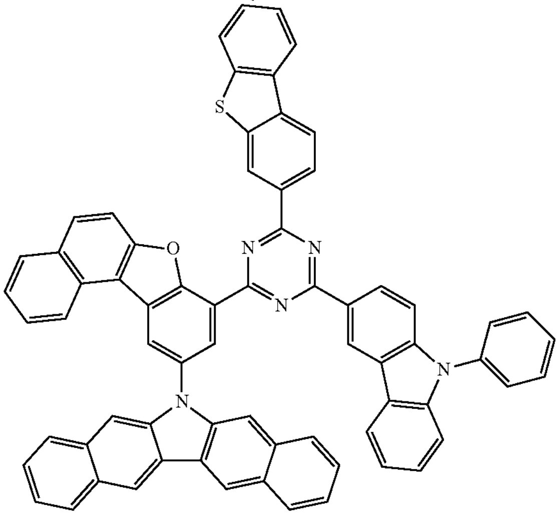
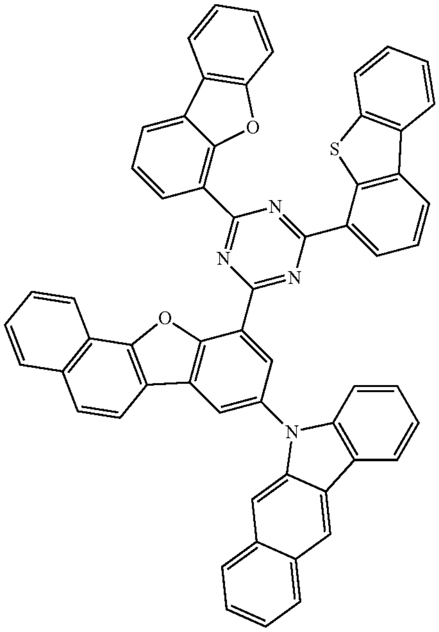

-continued
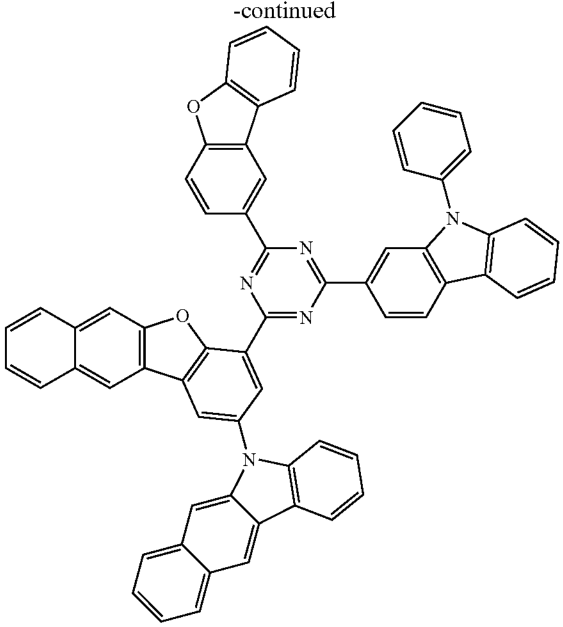
-continued
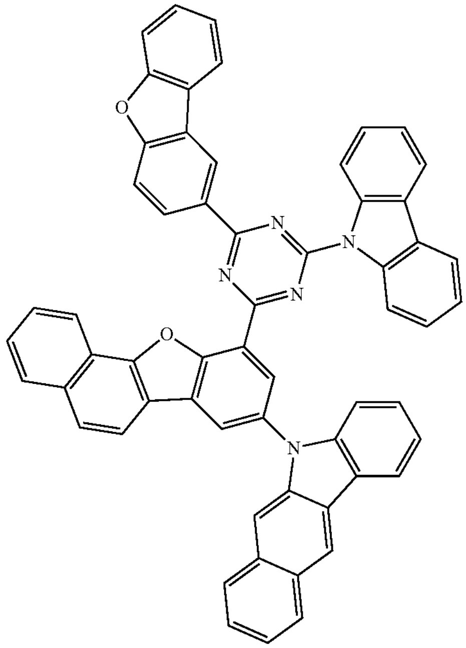
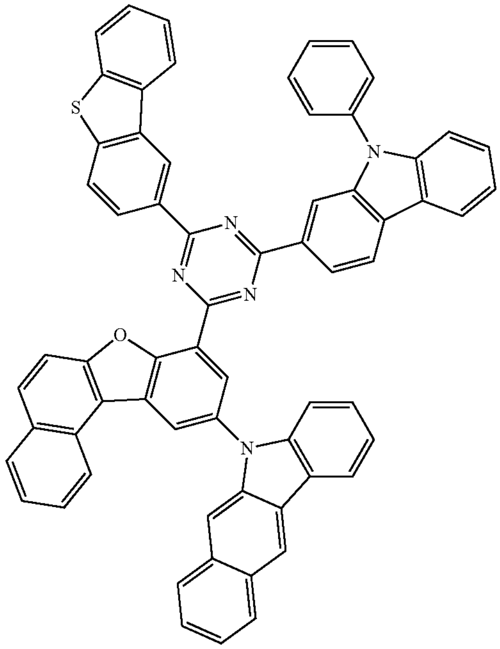 [SMILES: c1ccc(-n2c3ccccc3c3ccc(-c4nc(-c5ccc6sc7ccccc7c6c5)nc(-c5cc(-n6c7ccccc7c7cc8ccccc8cc76)cc6c5oc5ccc7ccccc7c56)n4)cc32)cc1]
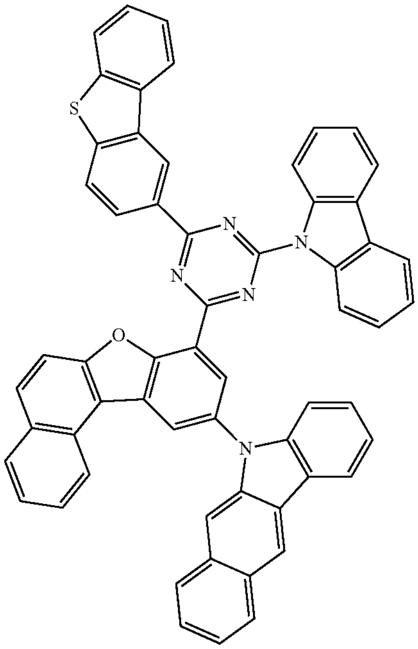

-continued
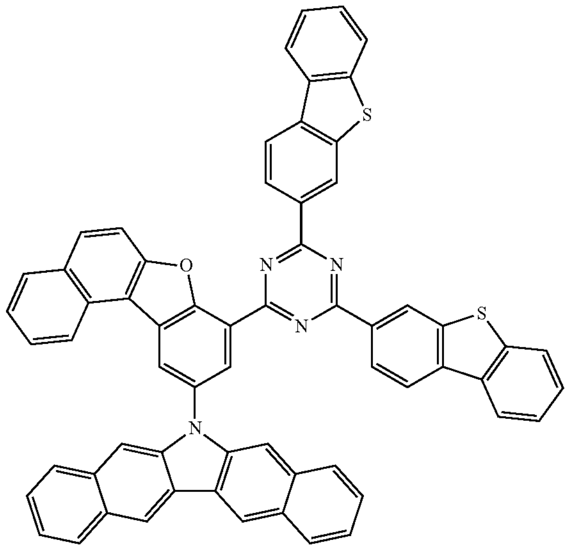
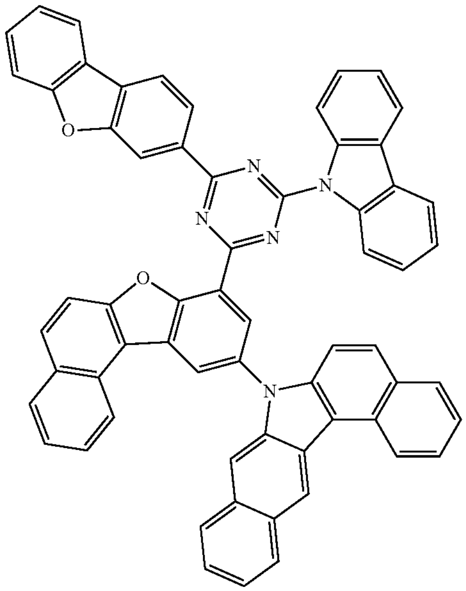
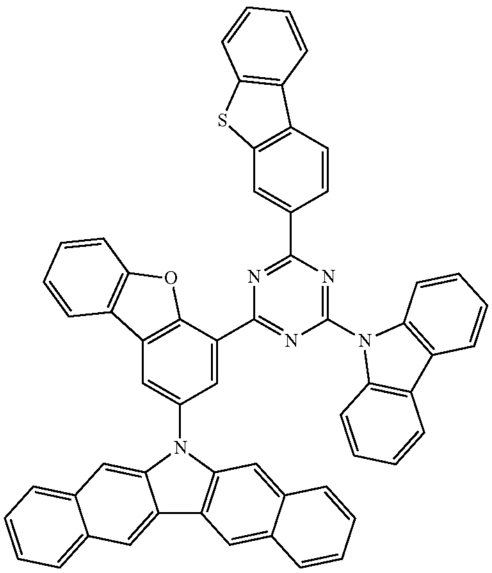
-continued
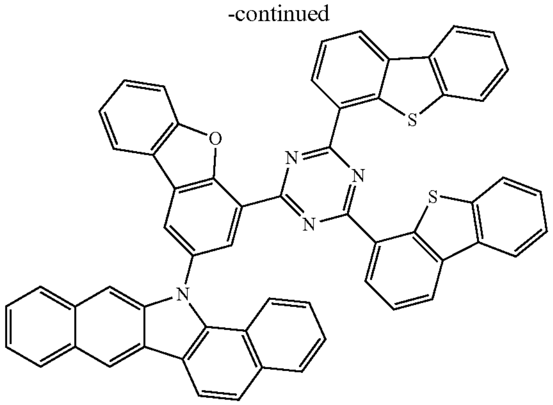
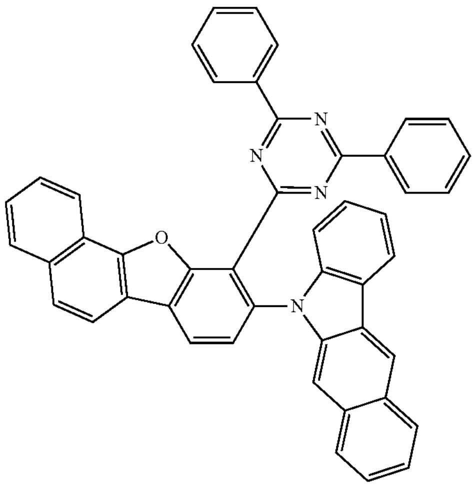
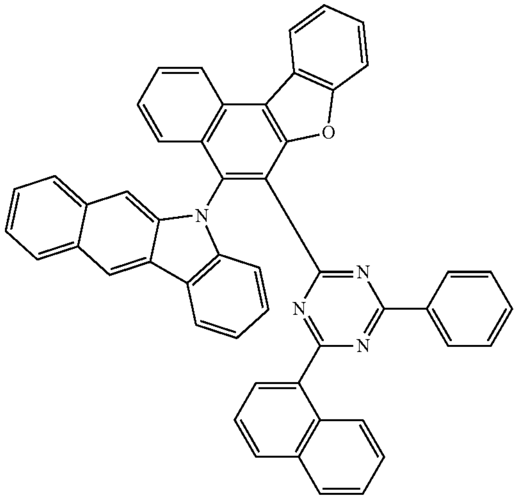

-continued
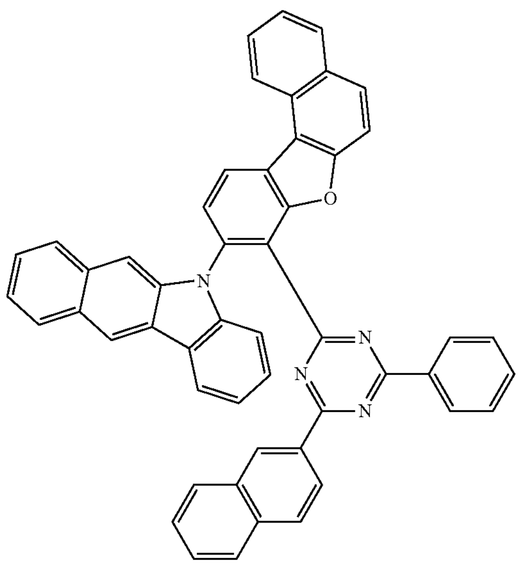
-continued
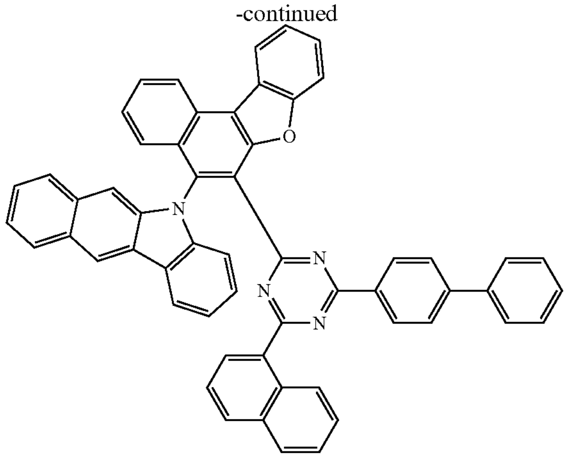
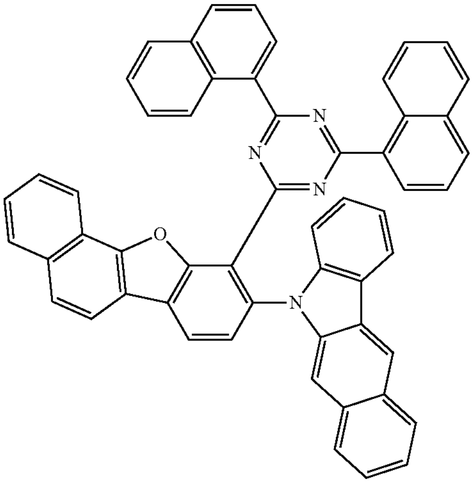
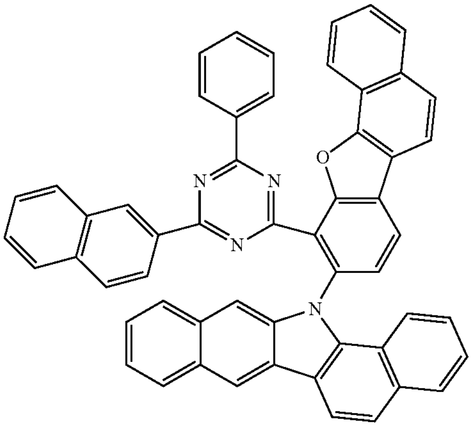
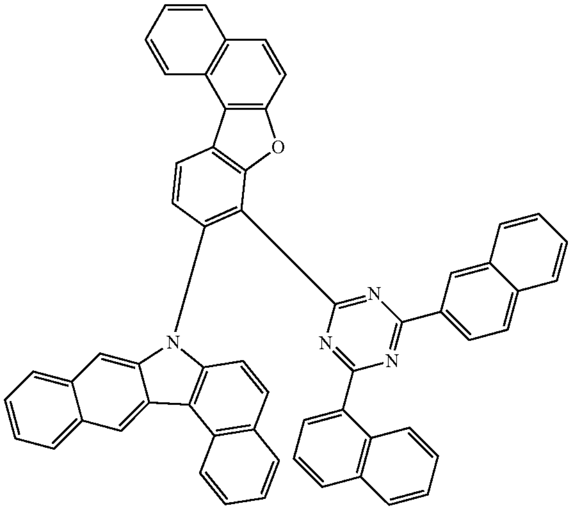
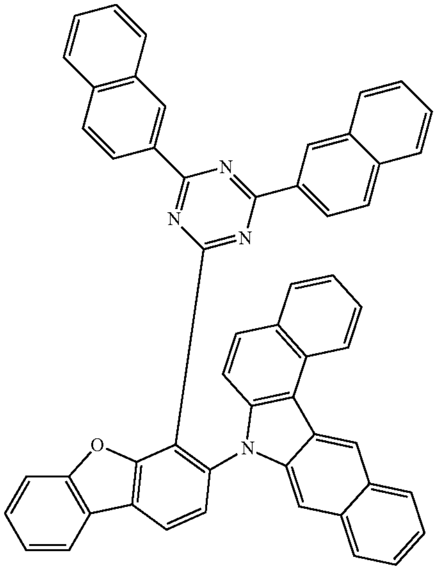

-continued
-continued
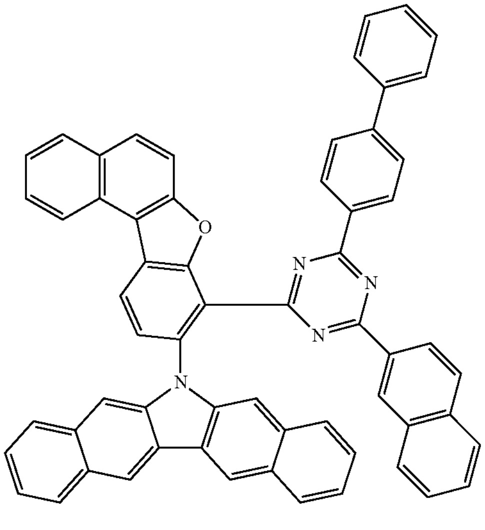
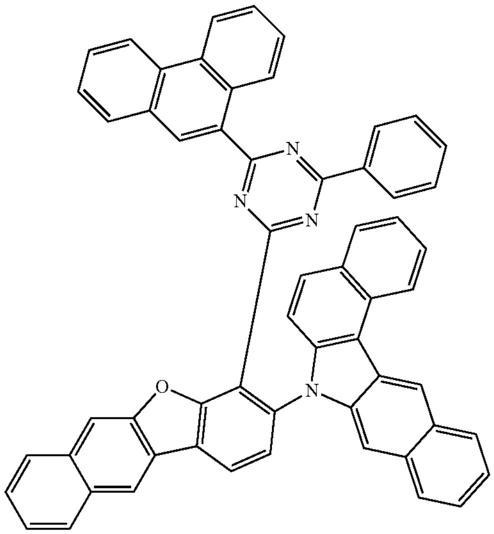
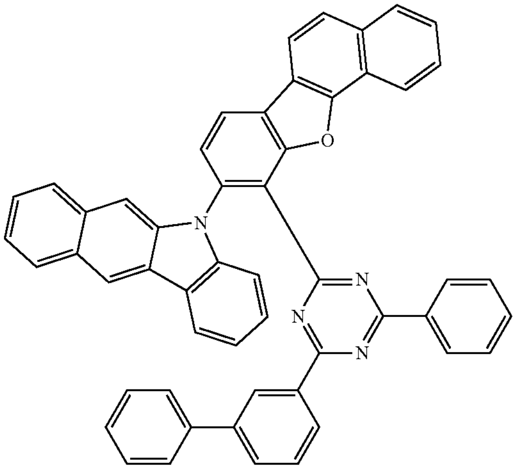
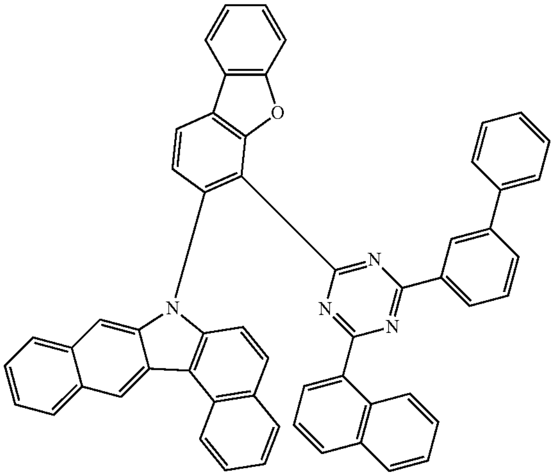
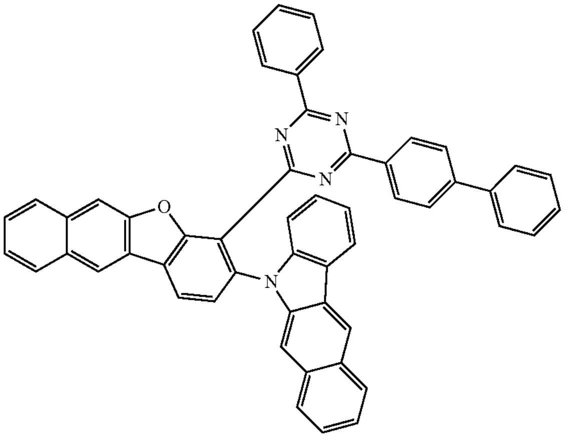
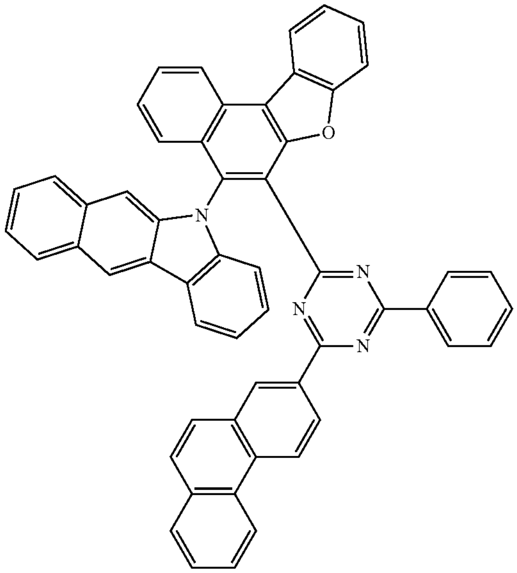

-continued
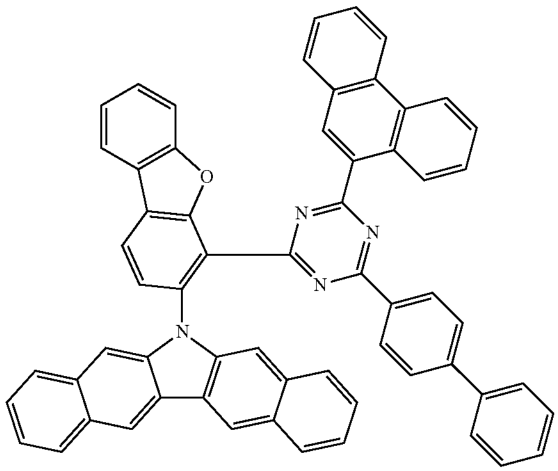
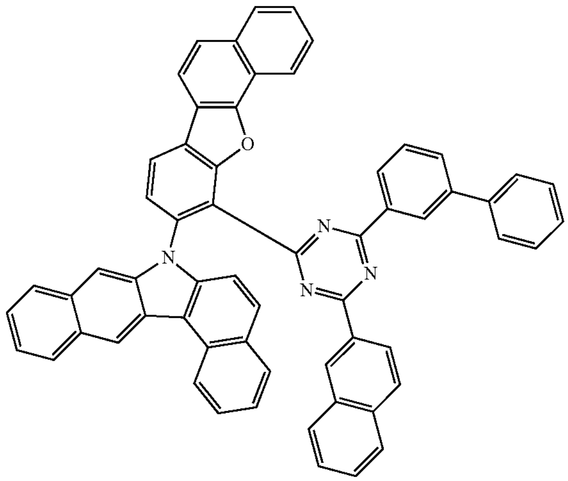
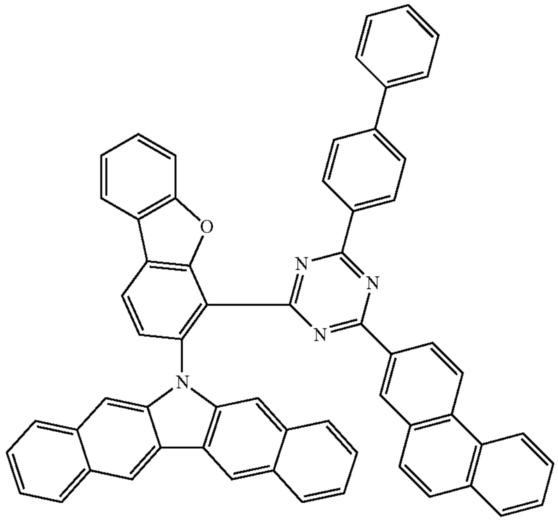
-continued
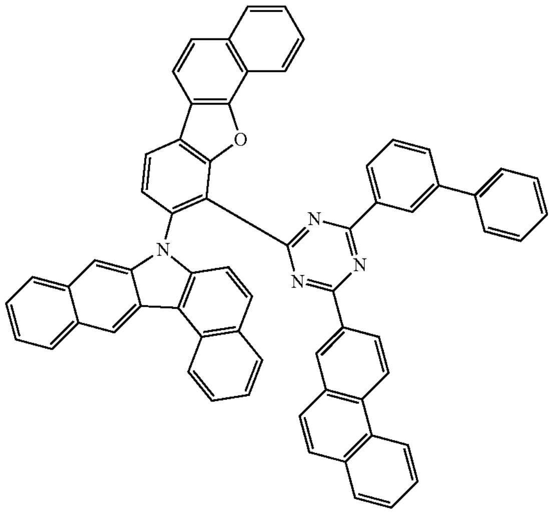
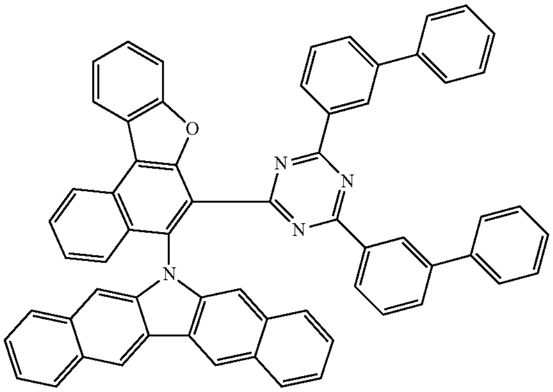
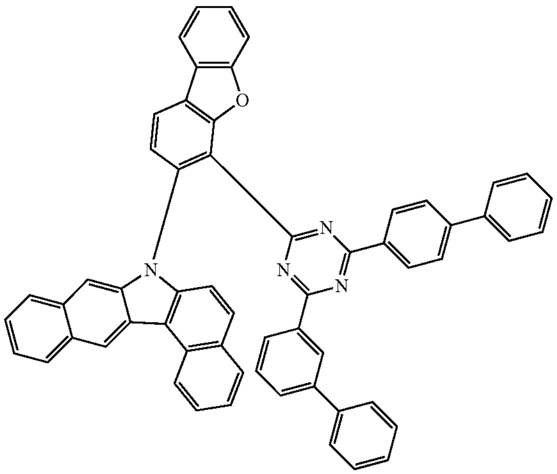

-continued
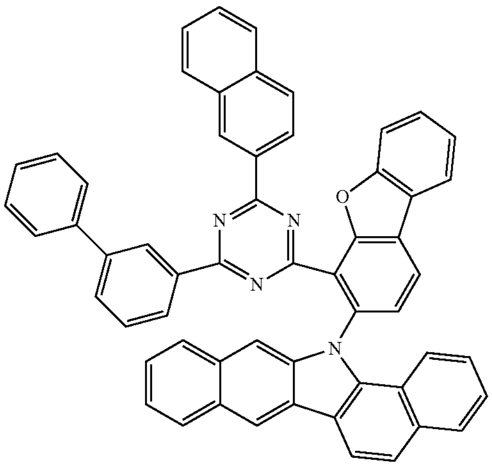
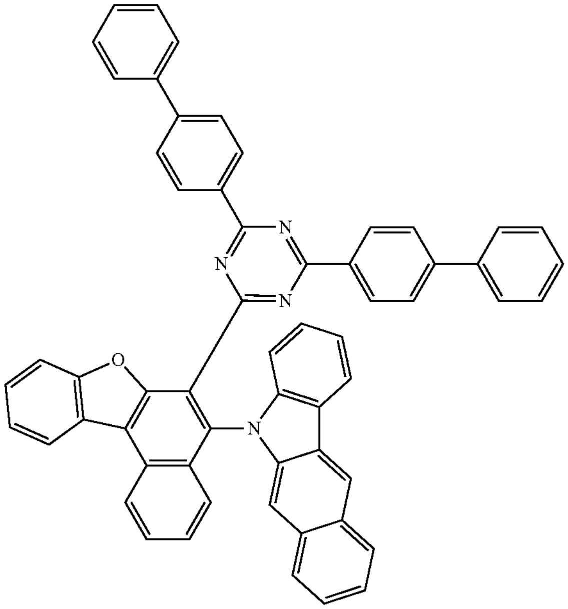
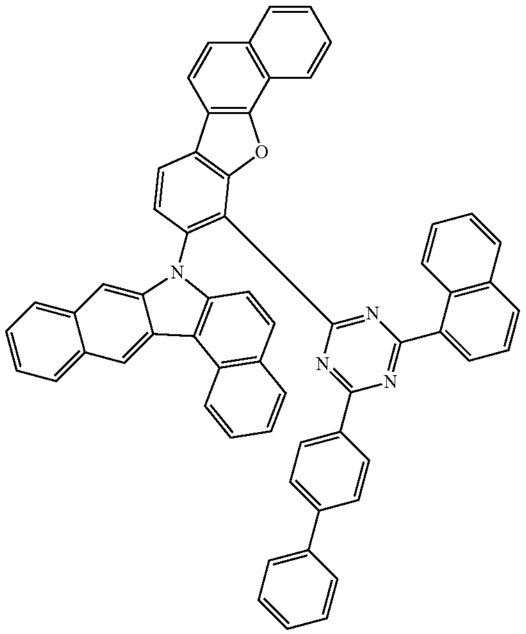
-continued
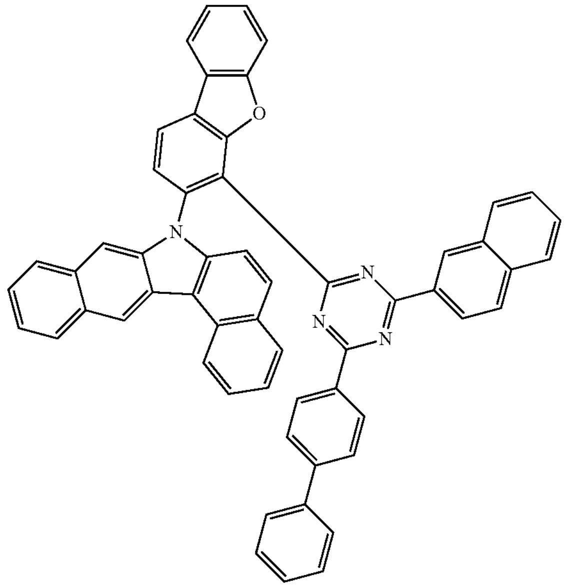 [SMILES: c1ccc(-c2ccc(-c3nc(-c4ccc5ccccc5c4)nc(-c4c(-n5c6cc7ccccc7cc6c6c7ccccc7ccc65)ccc5c4oc4ccccc45)n3)cc2)cc1]
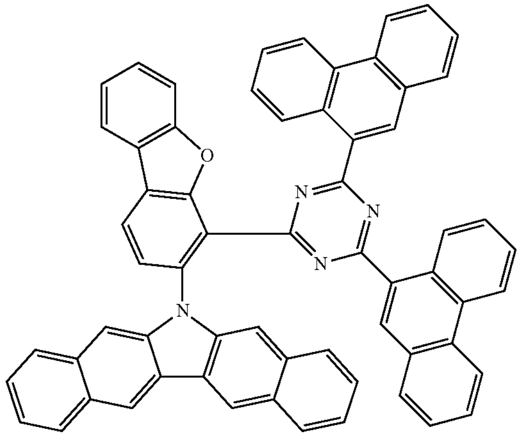
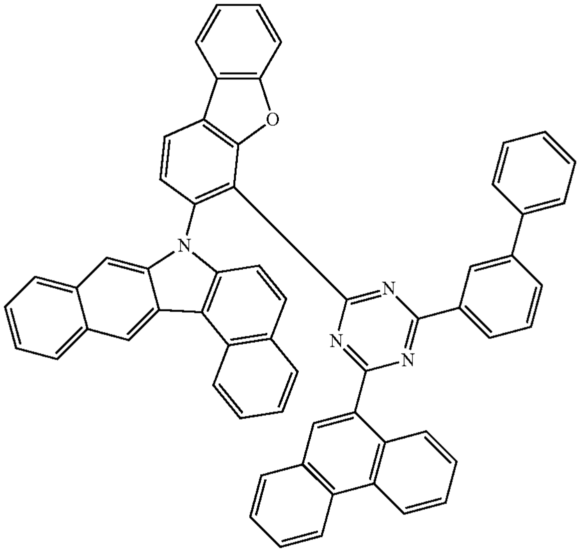

-continued
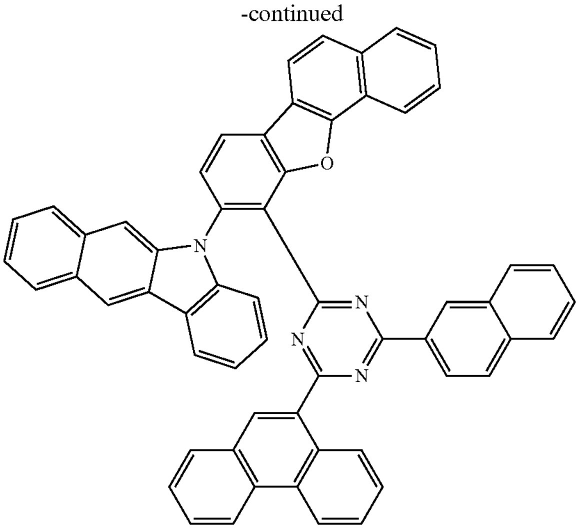
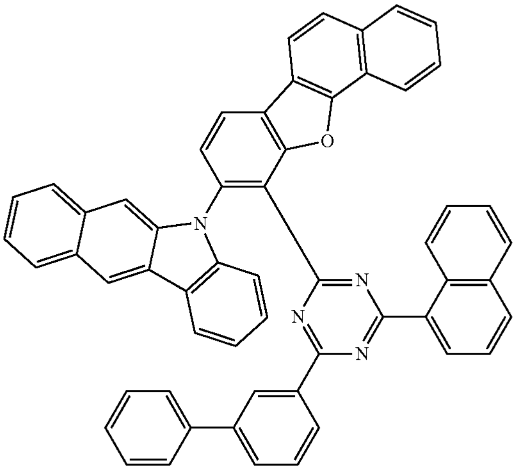
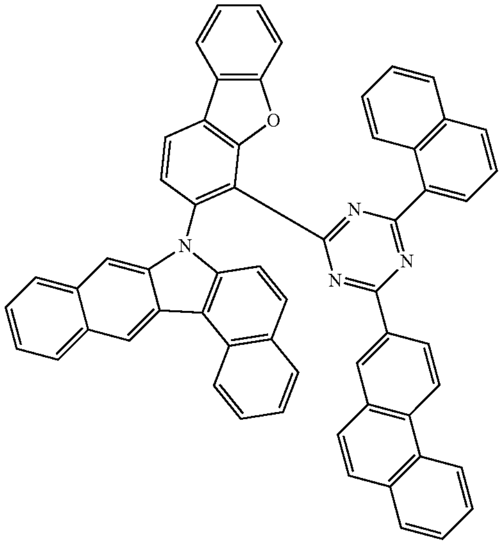
-continued
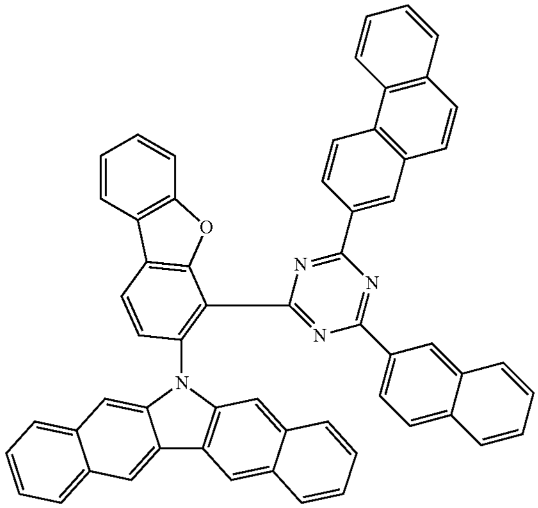
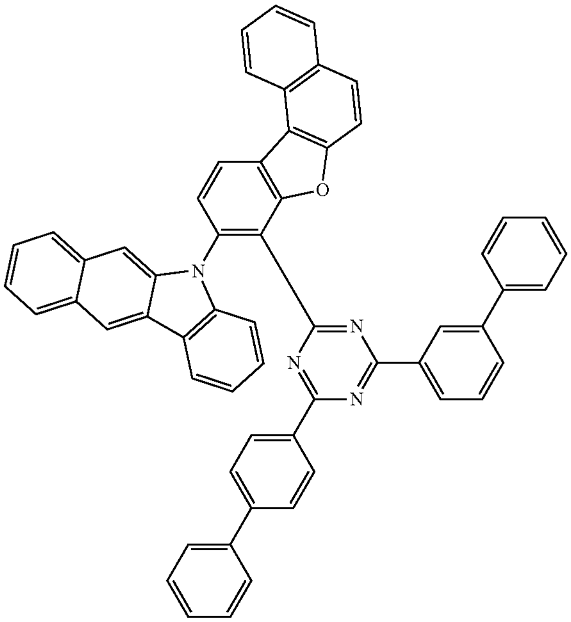
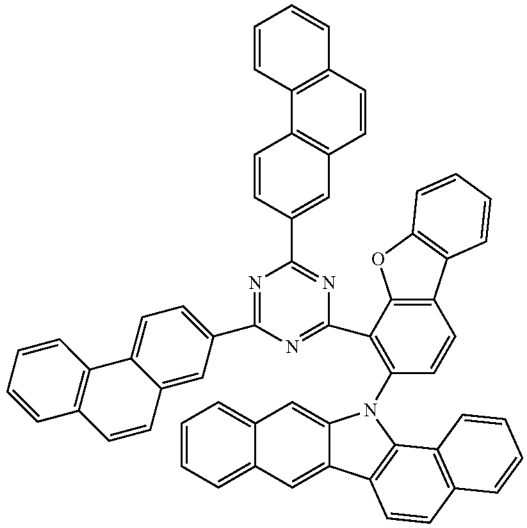

-continued
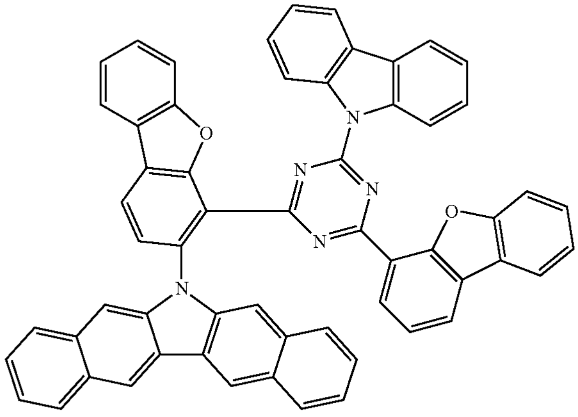
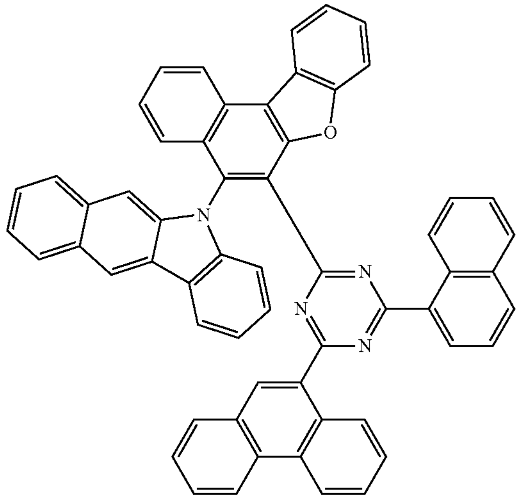
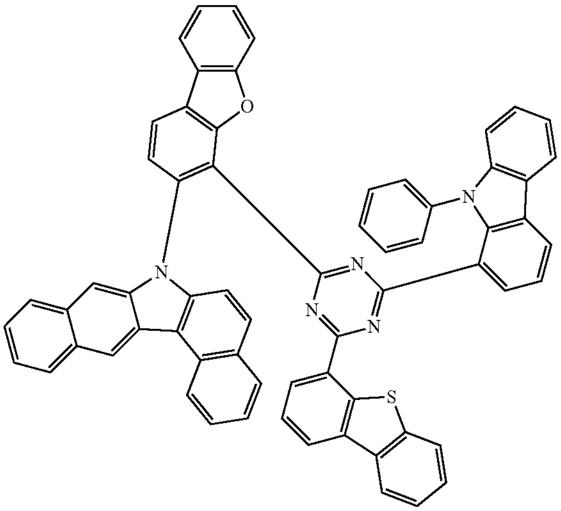
-continued
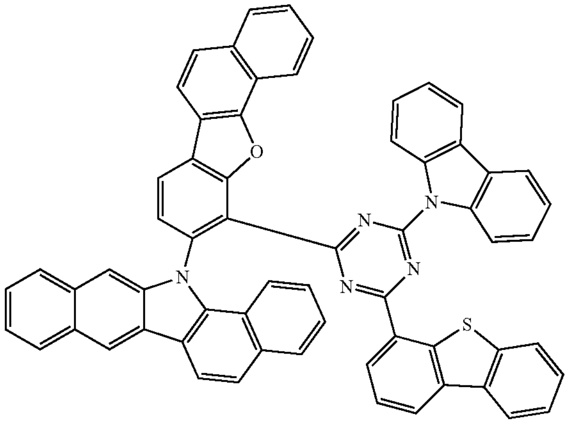
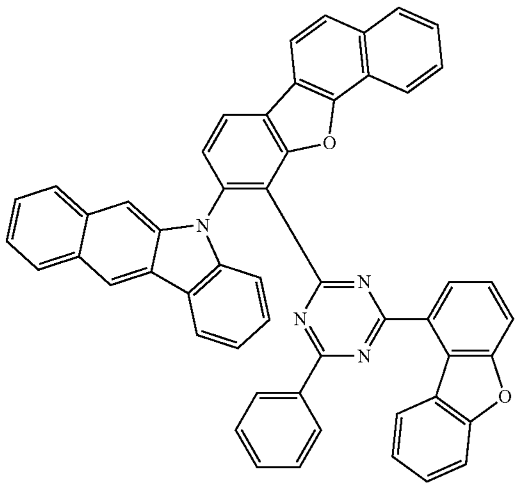
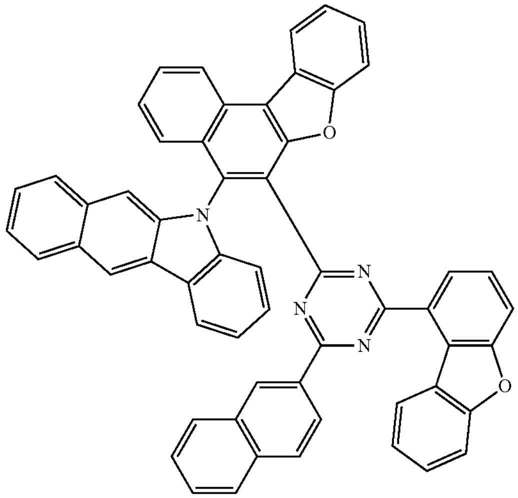

-continued
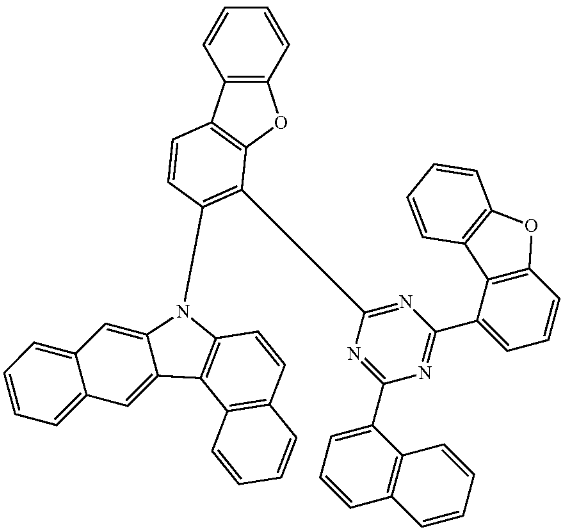
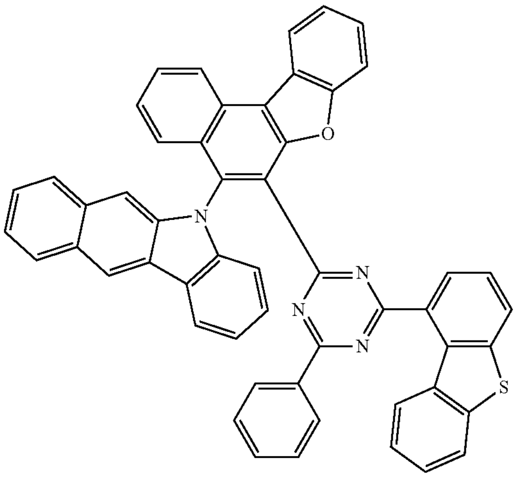
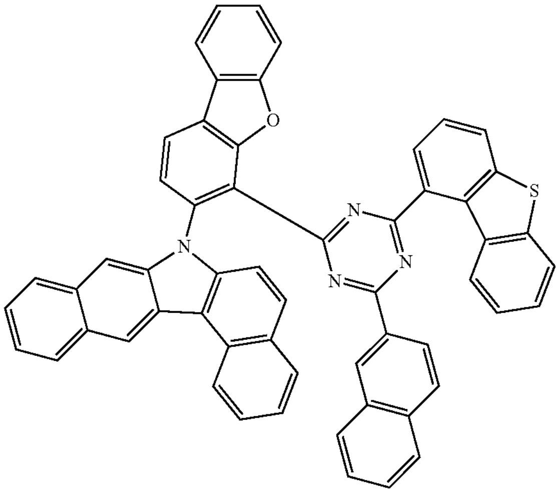
-continued
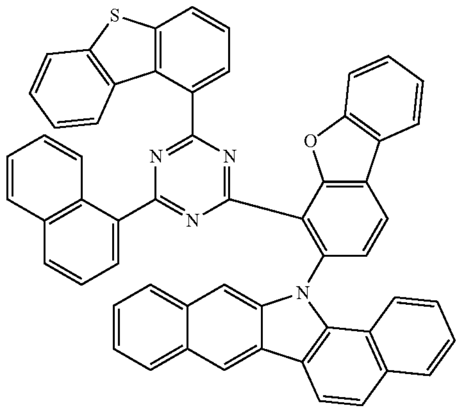
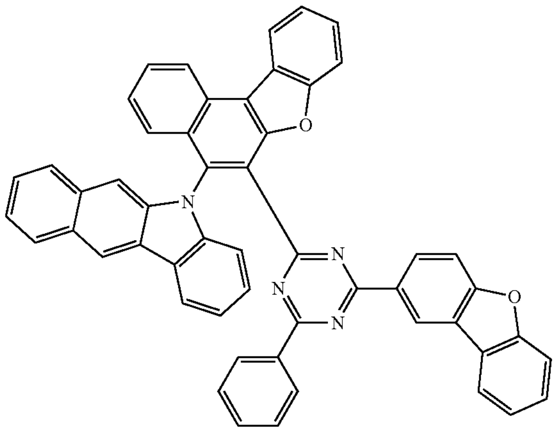
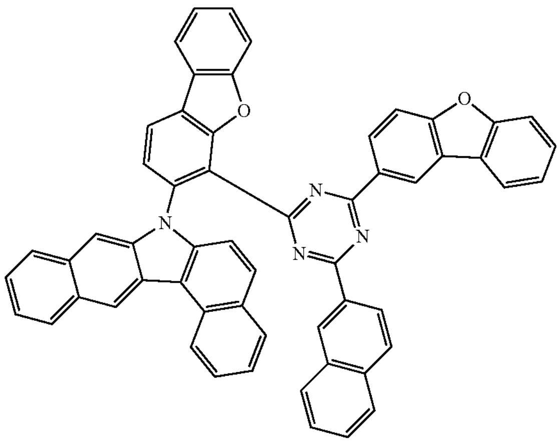

-continued
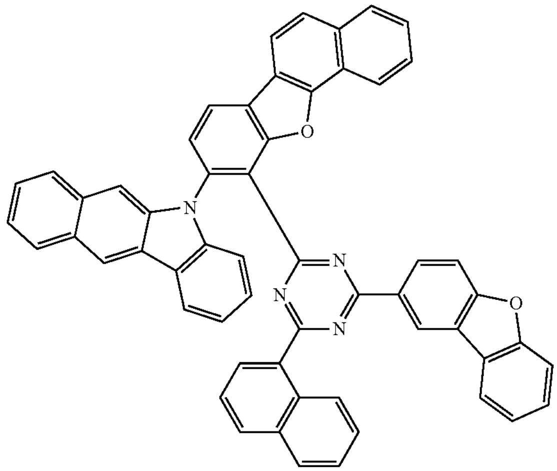
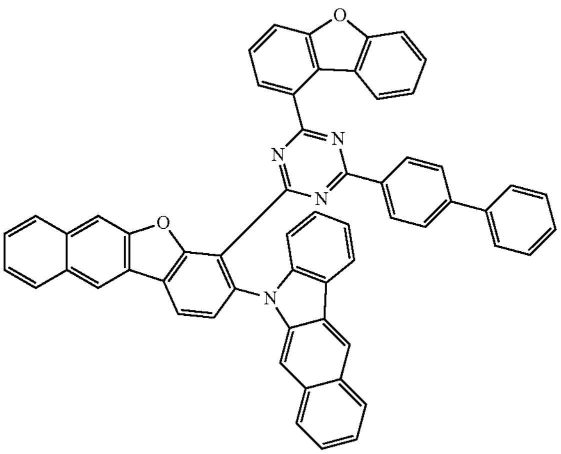
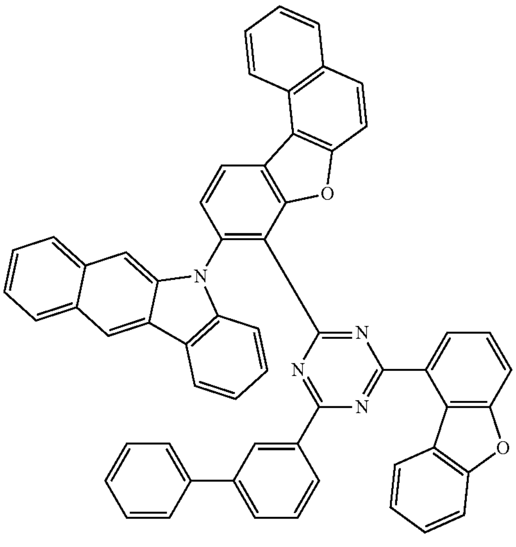
-continued
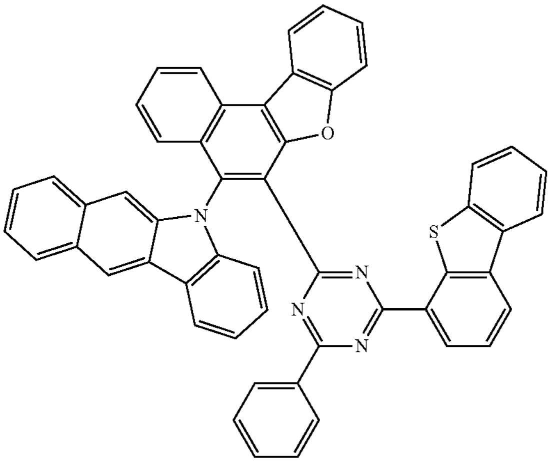
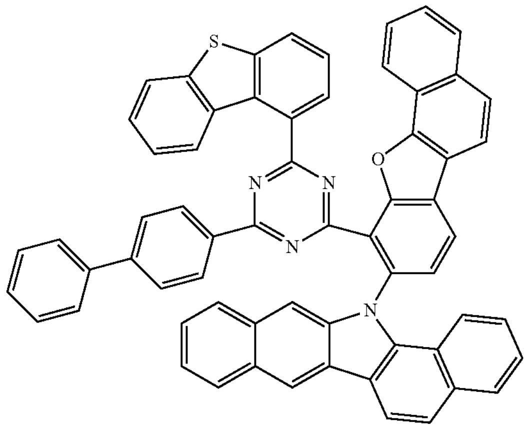
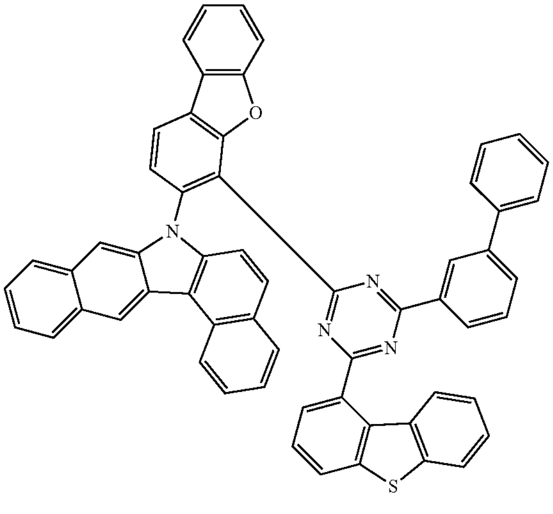

-continued
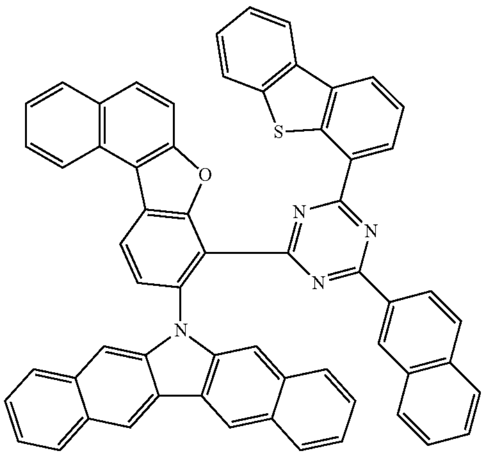
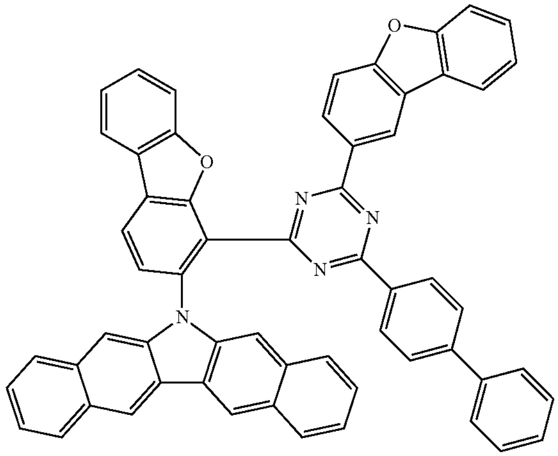
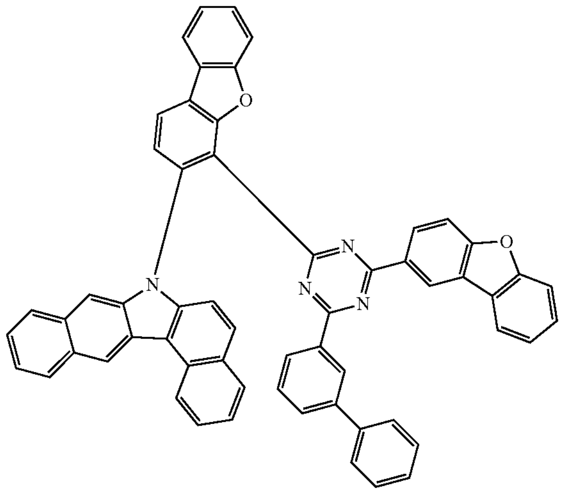
-continued
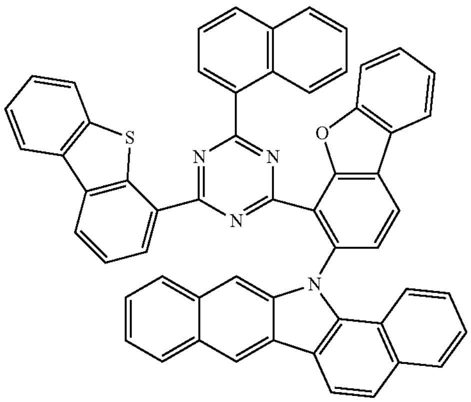
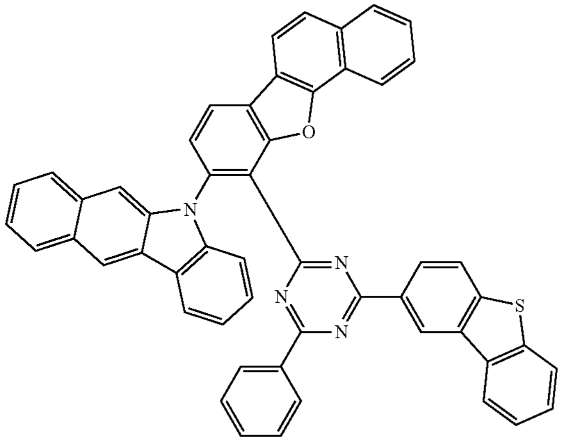
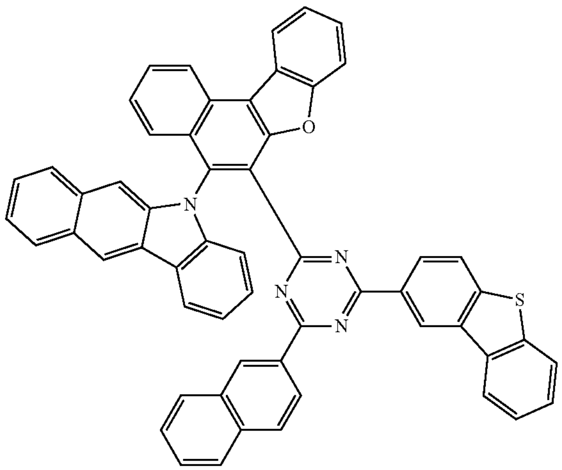

-continued
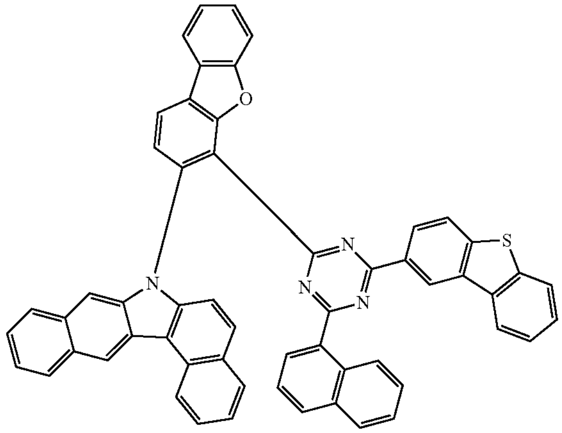
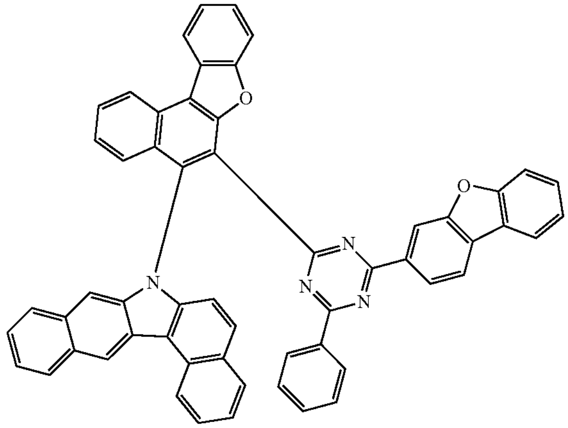
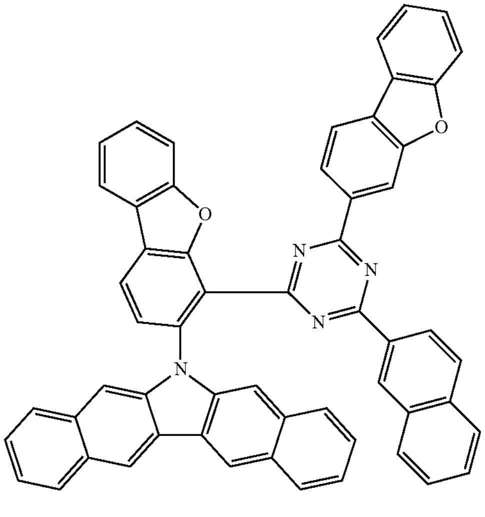
-continued
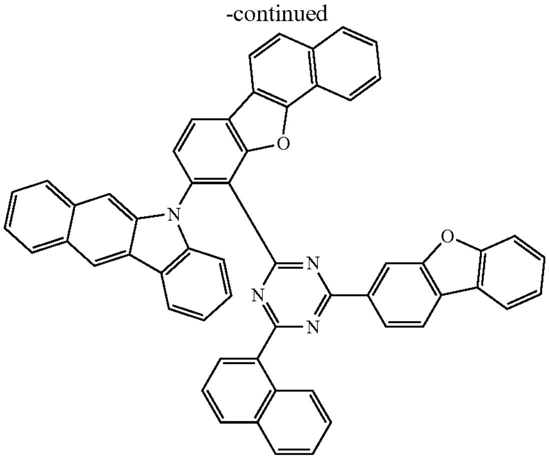
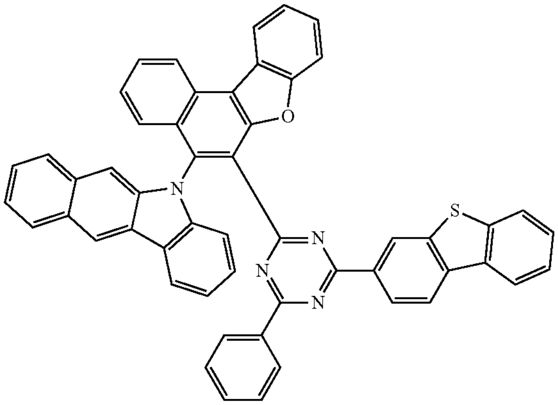
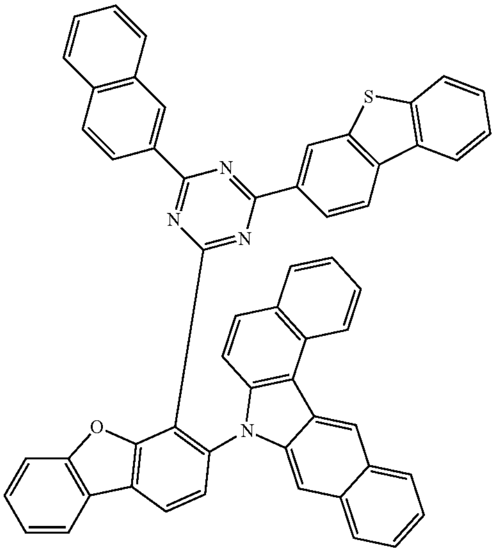

-continued
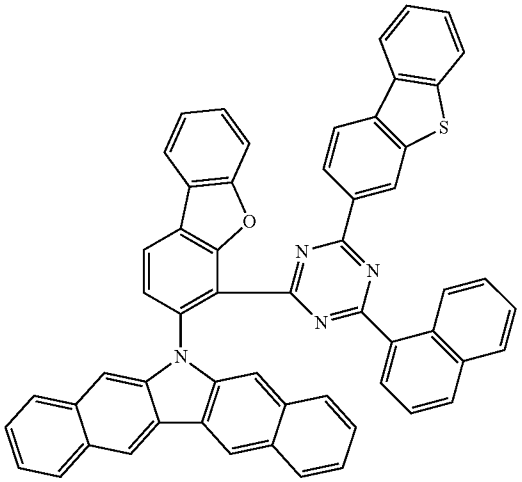
-continued
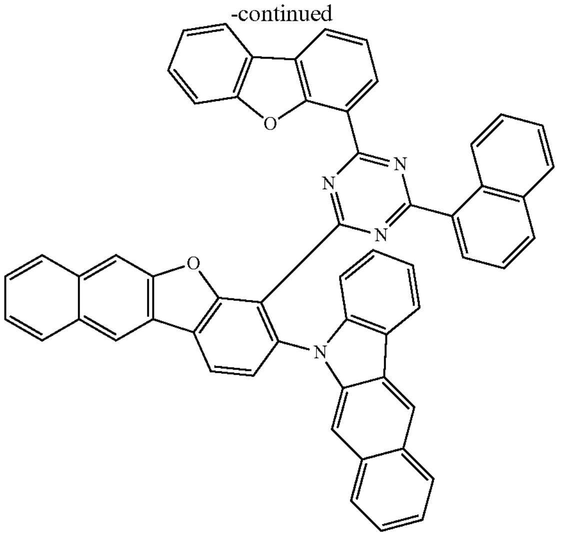
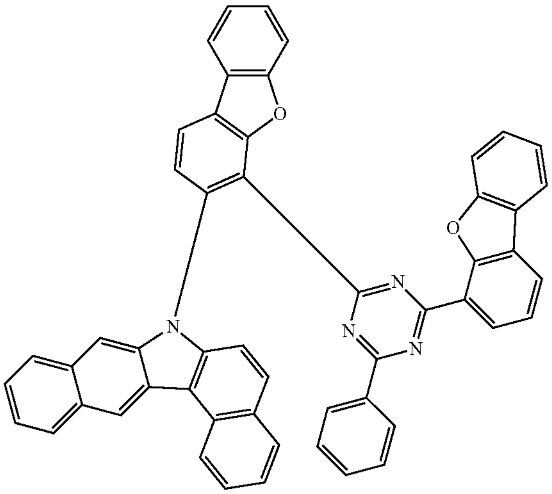
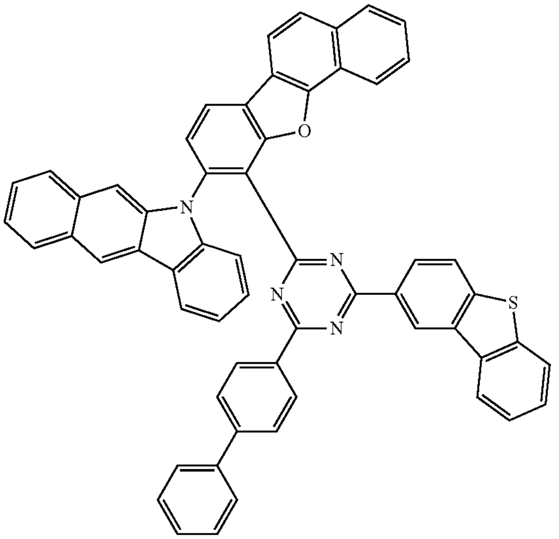
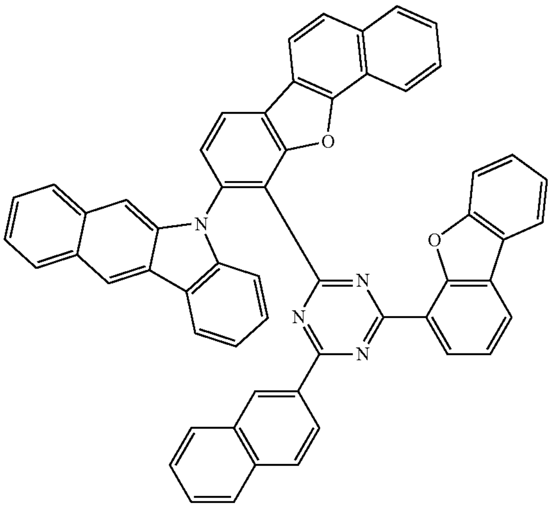
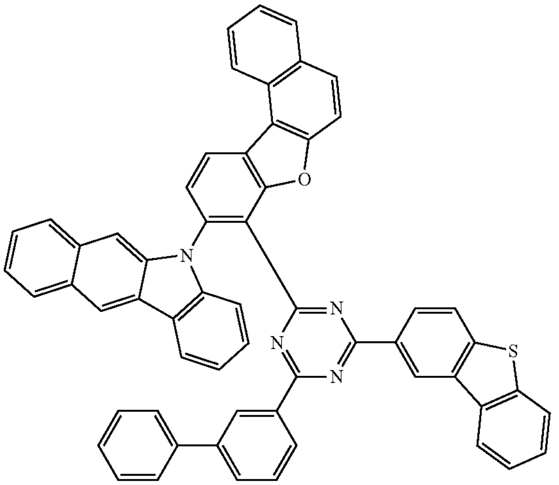

-continued
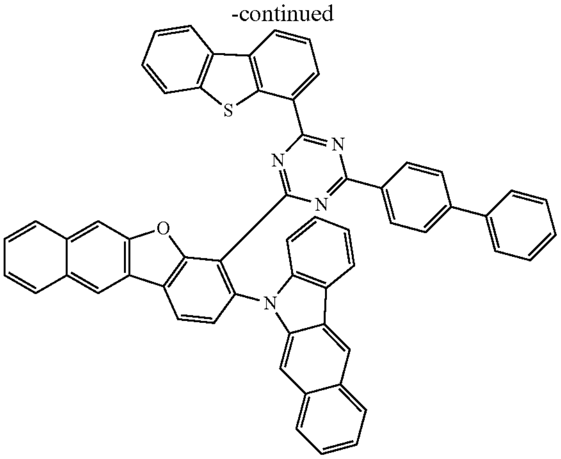
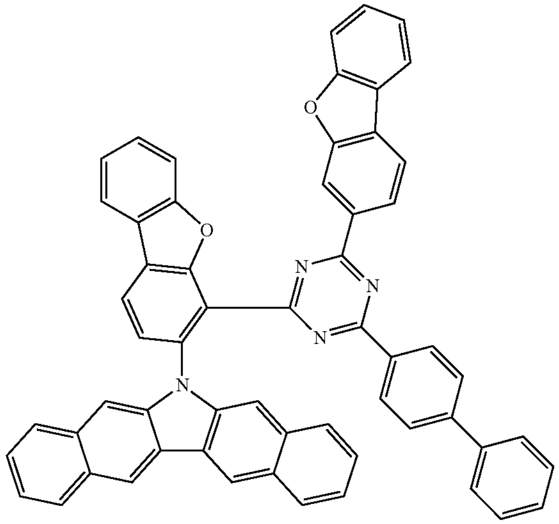
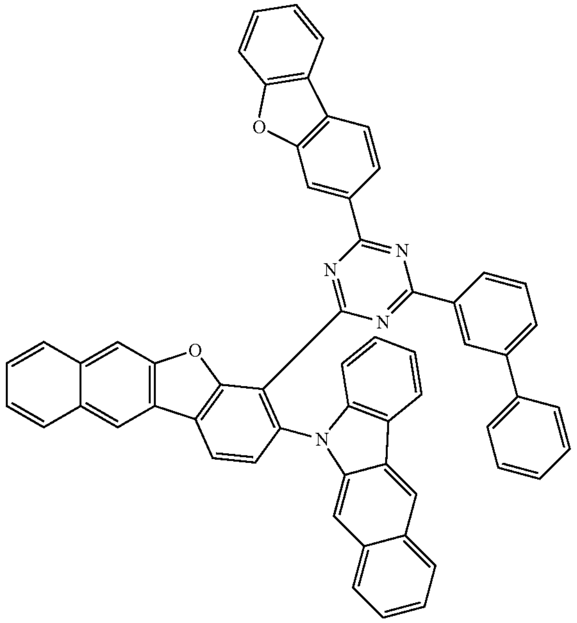
-continued
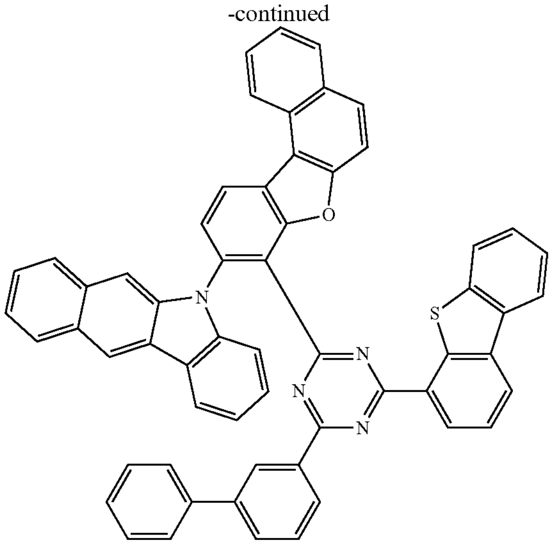
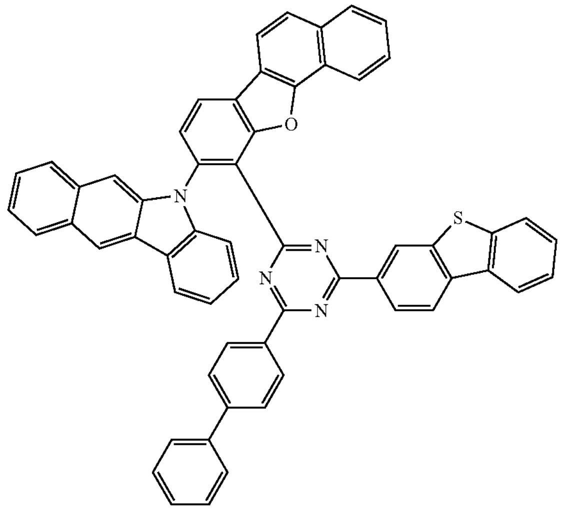
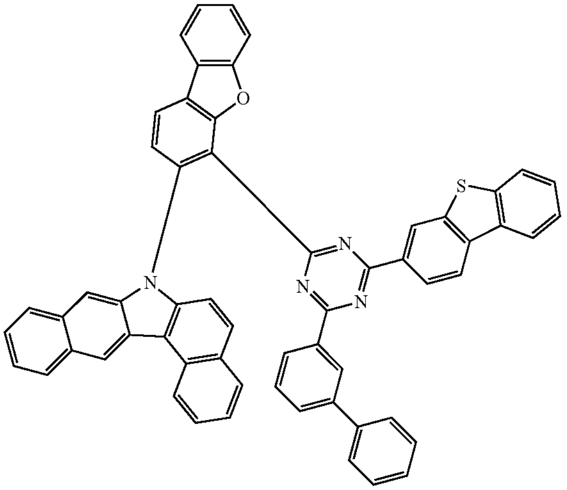

-continued
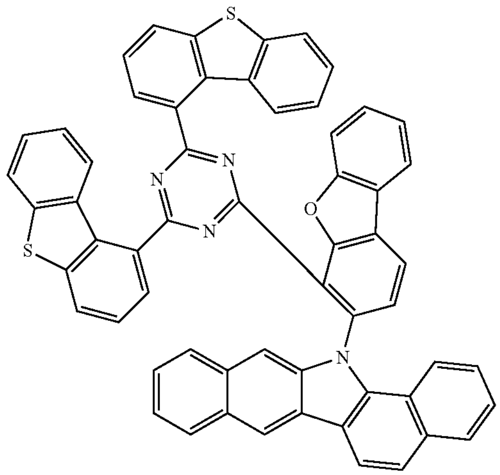
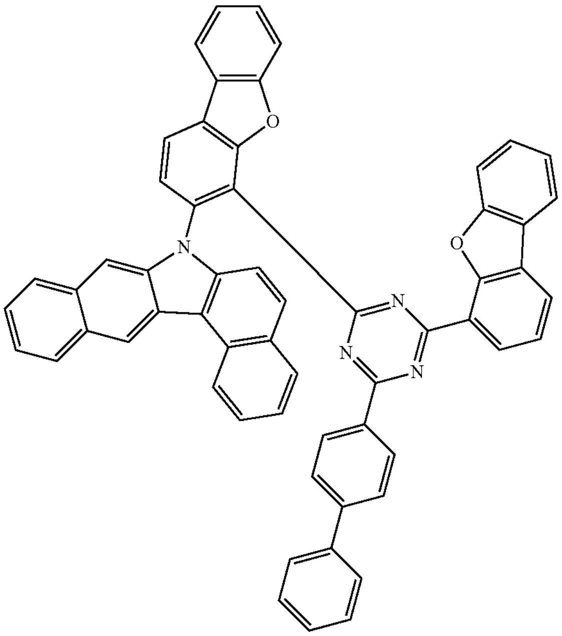
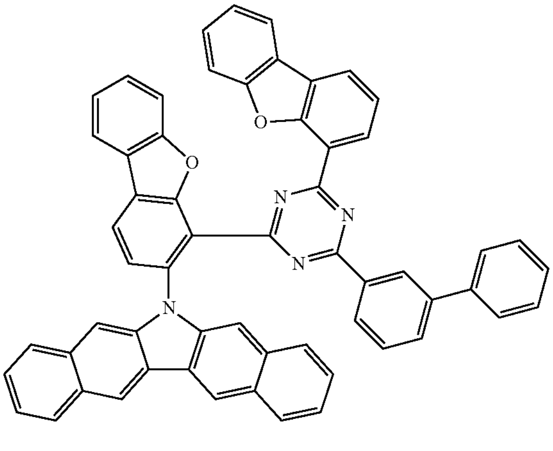
-continued
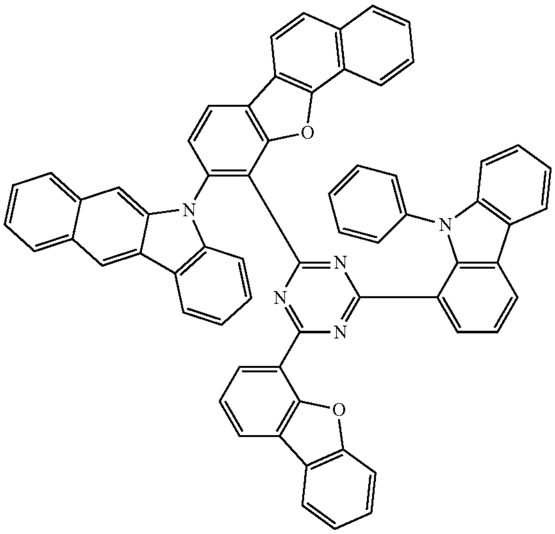
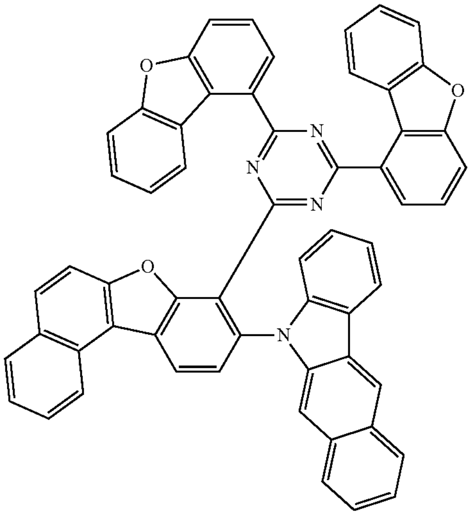
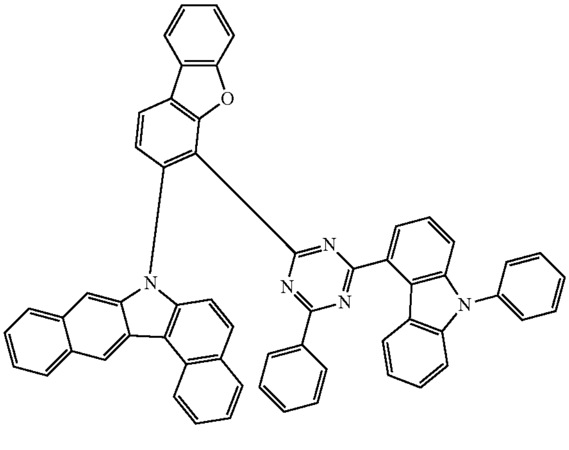

-continued
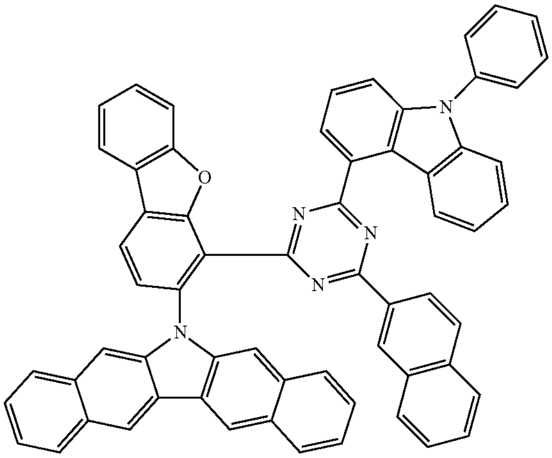
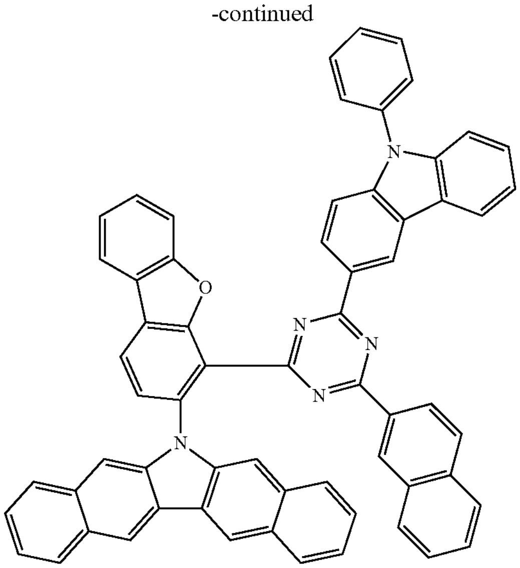
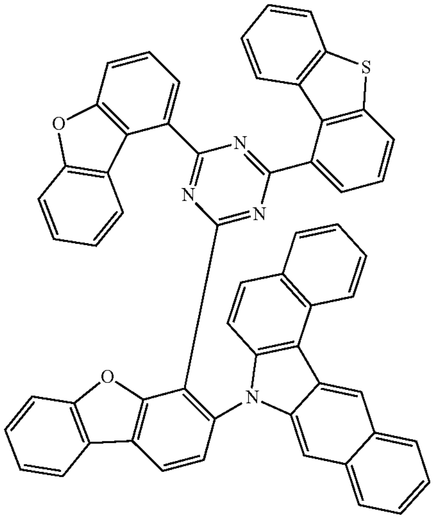
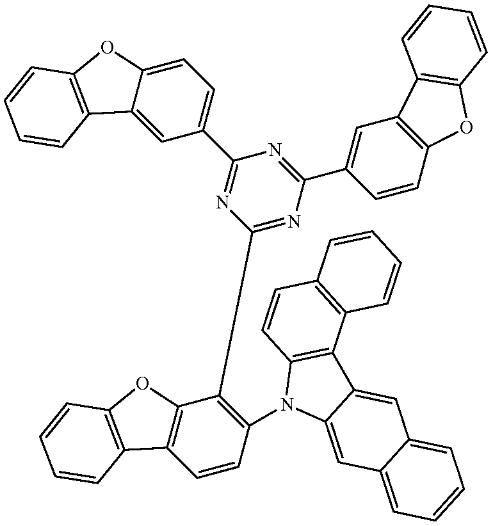
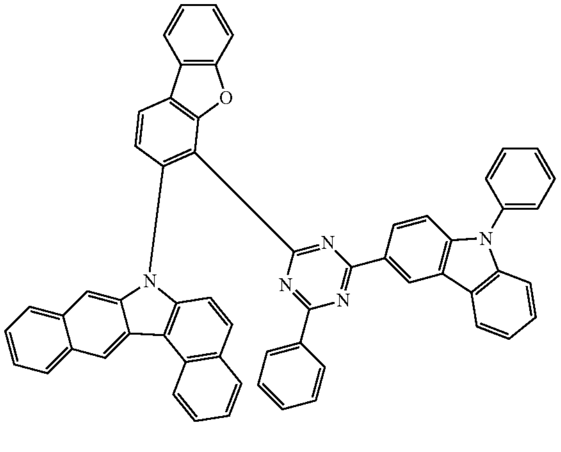
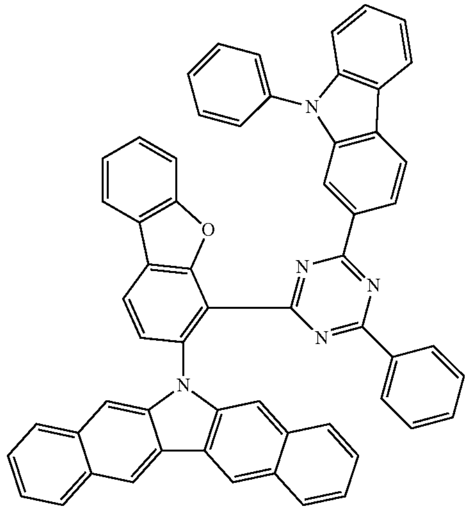
-continued -continued
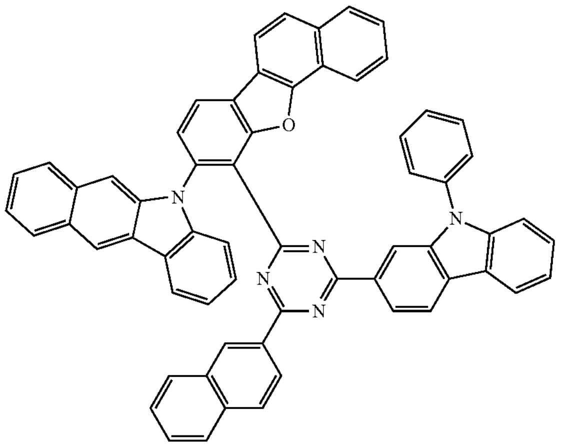
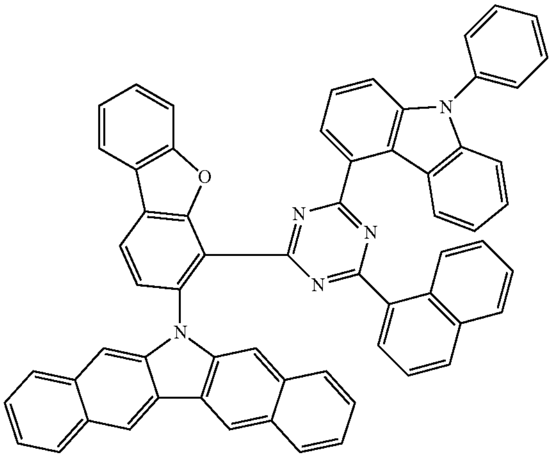
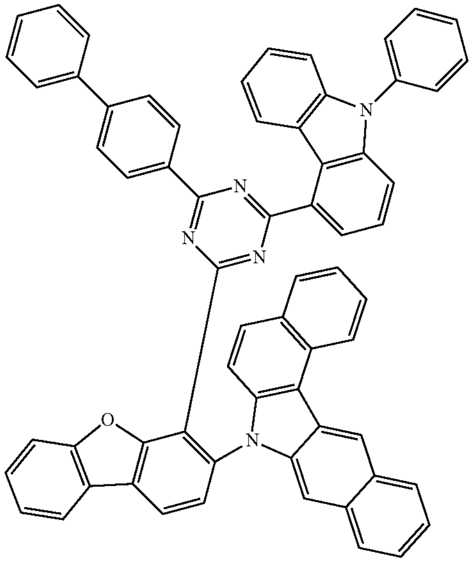
-continued
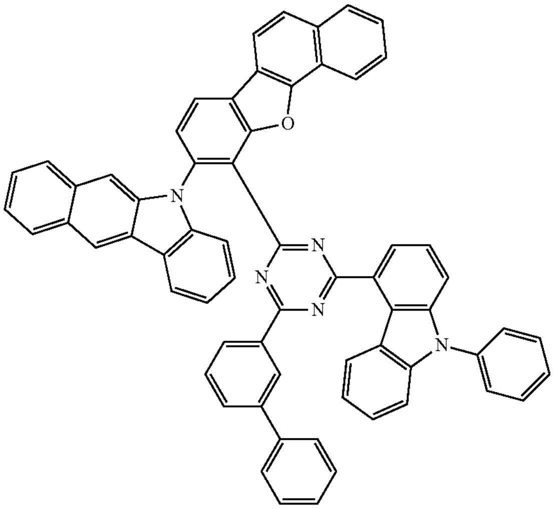
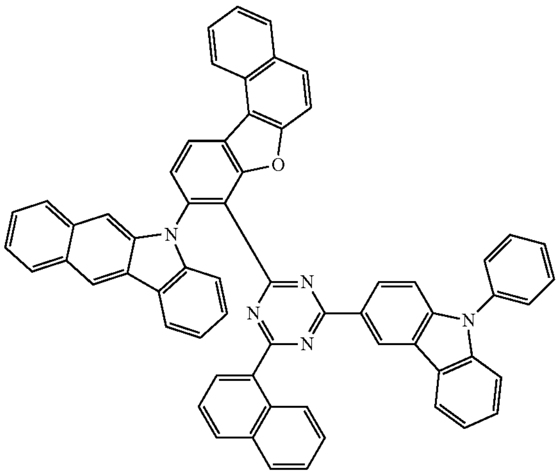
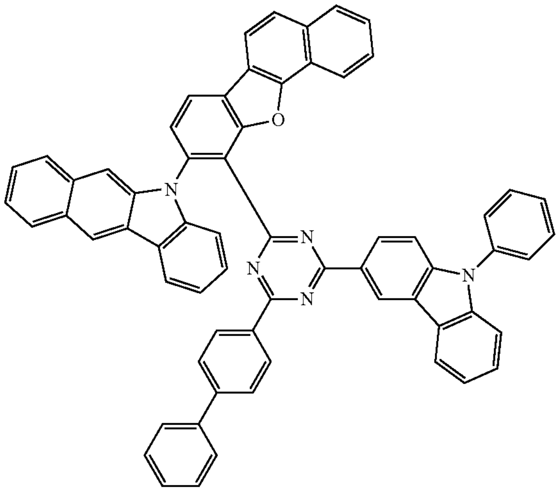

-continued
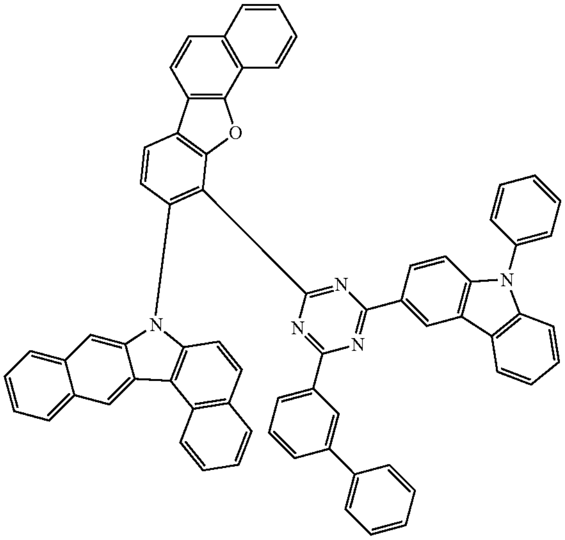
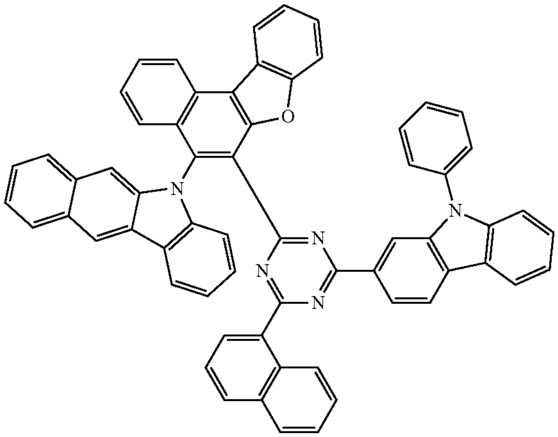
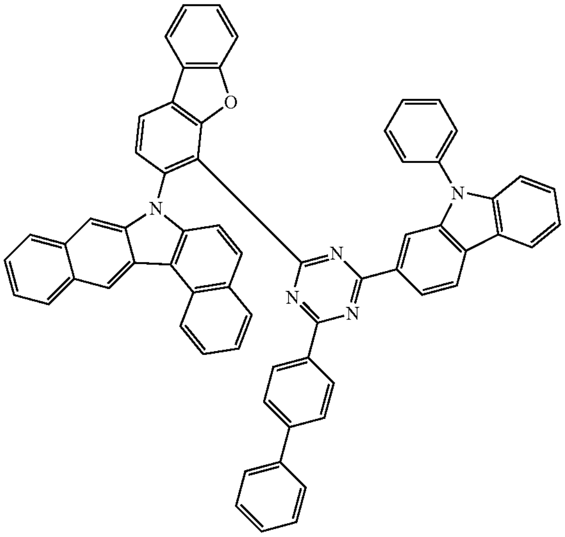
-continued
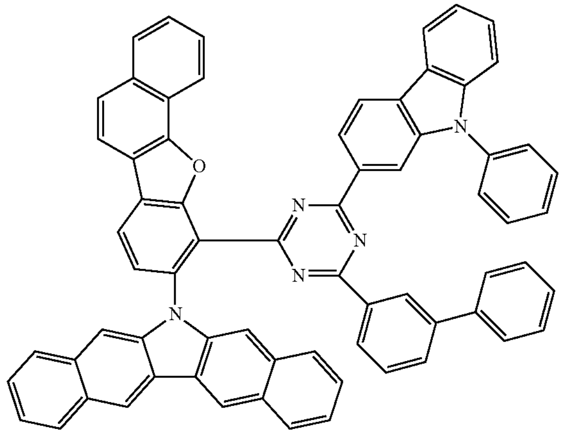
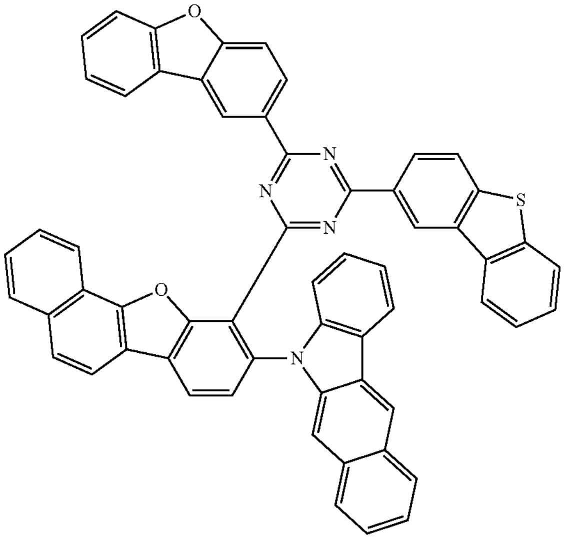
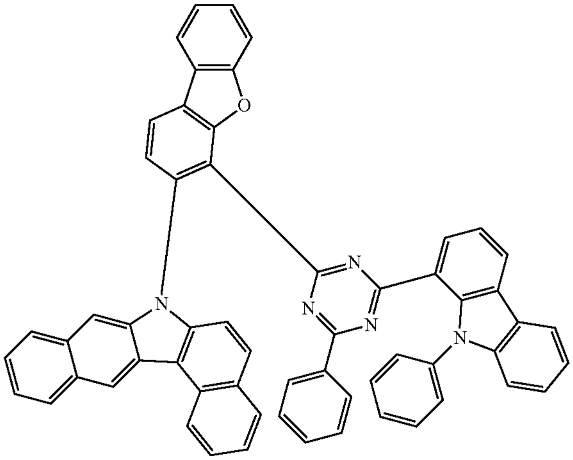

-continued
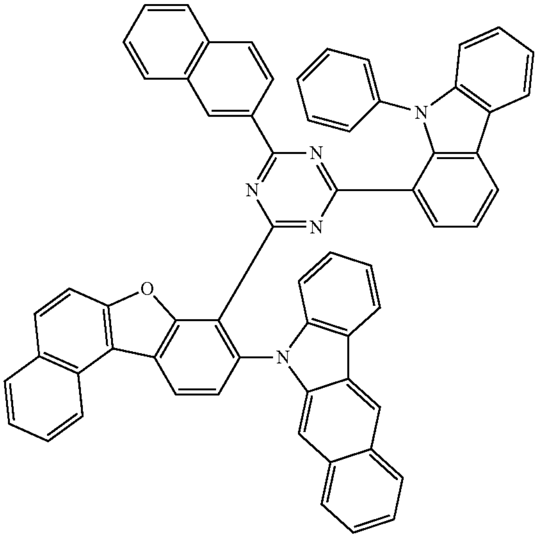
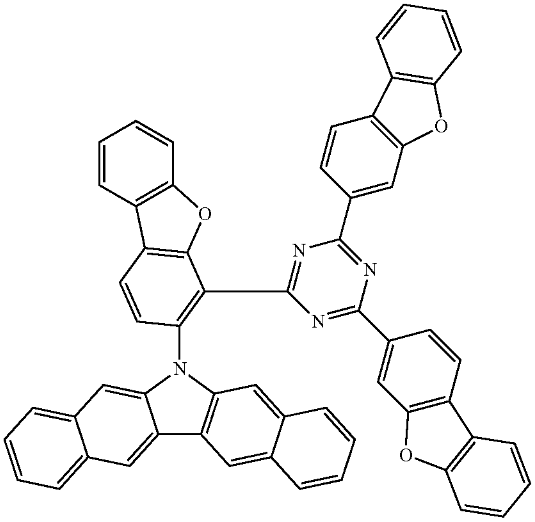
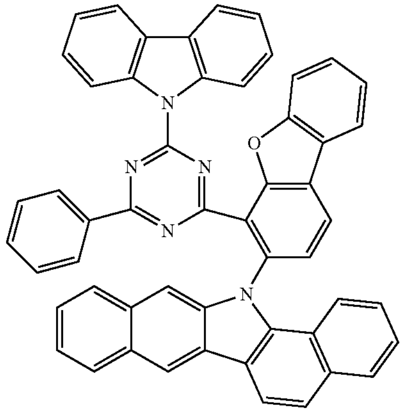
-continued
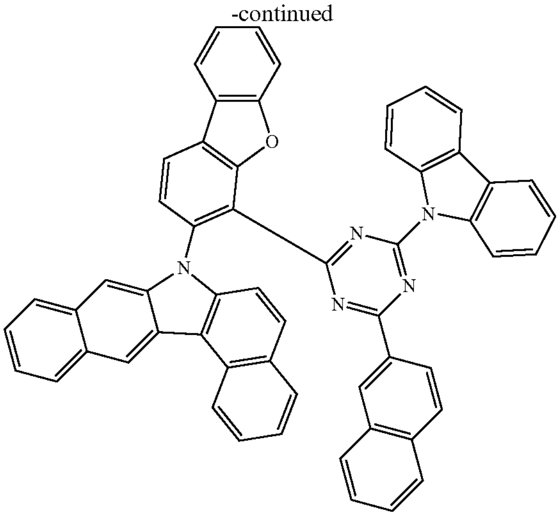
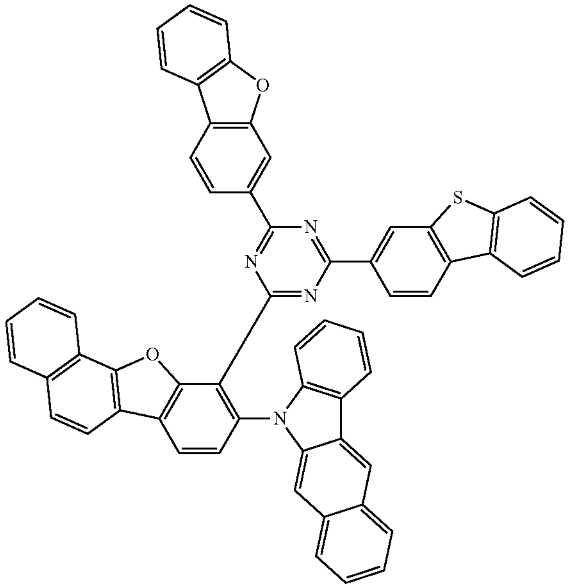
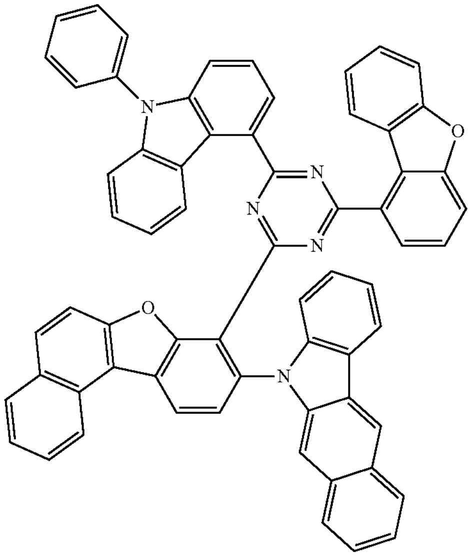

-continued
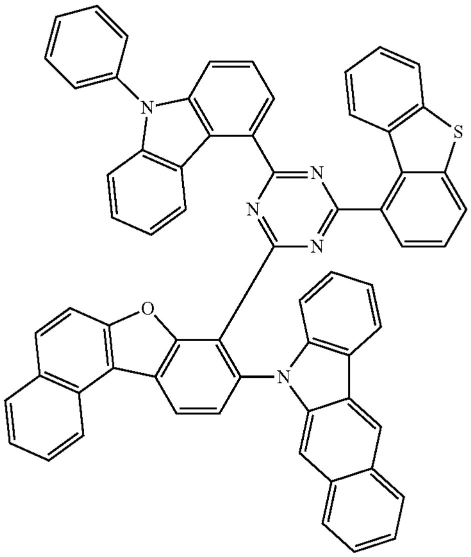
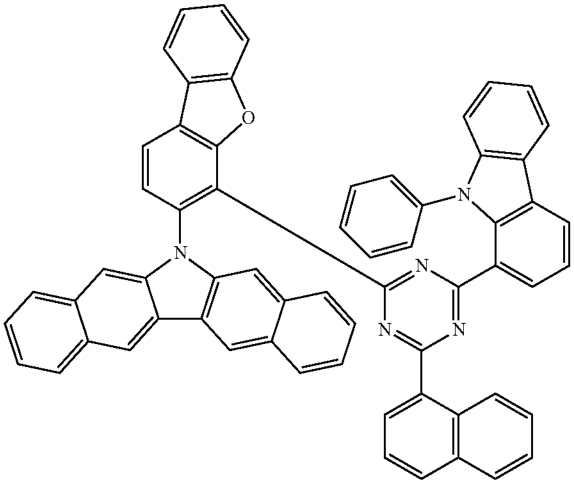
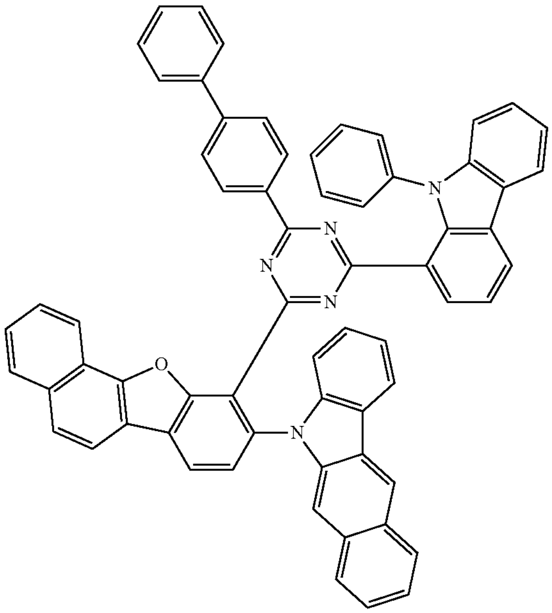
-continued
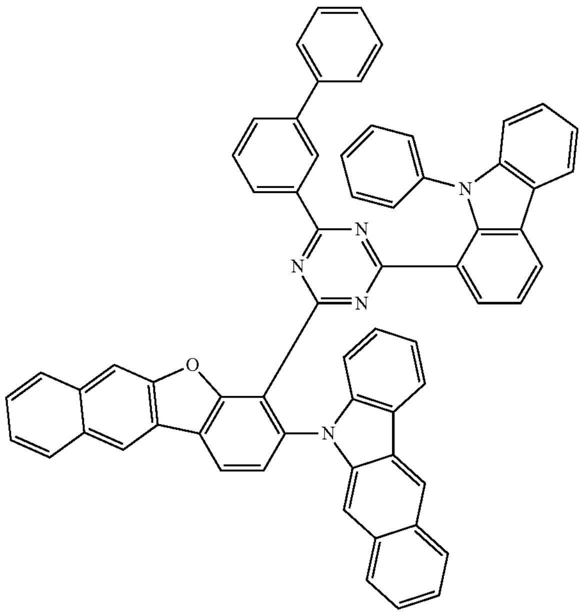
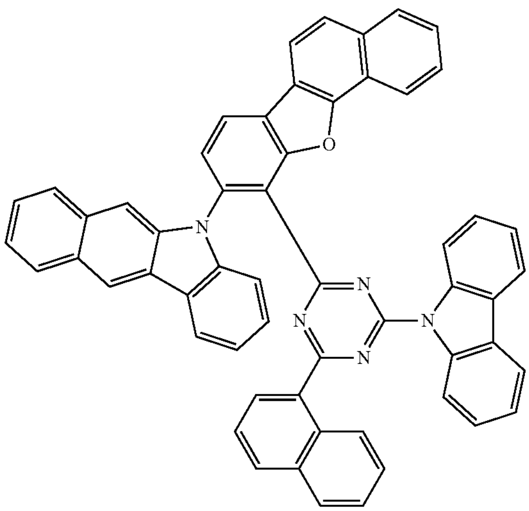

-continued
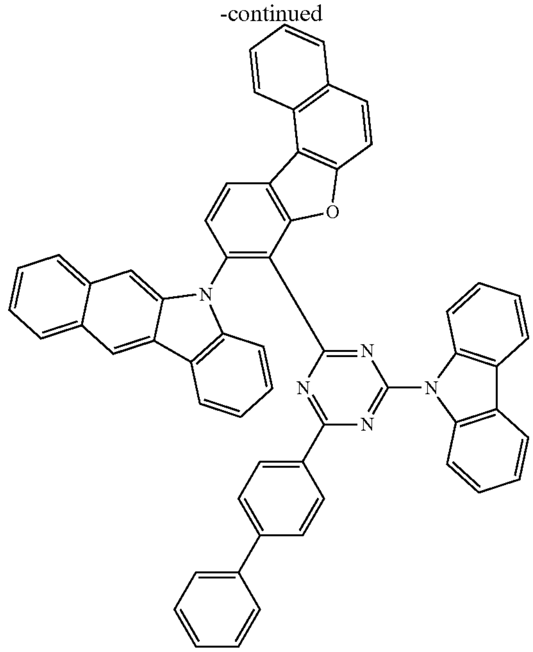
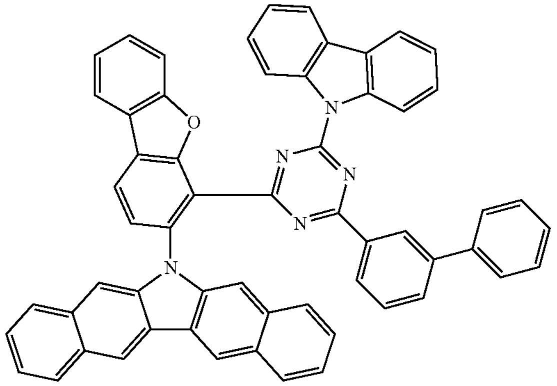
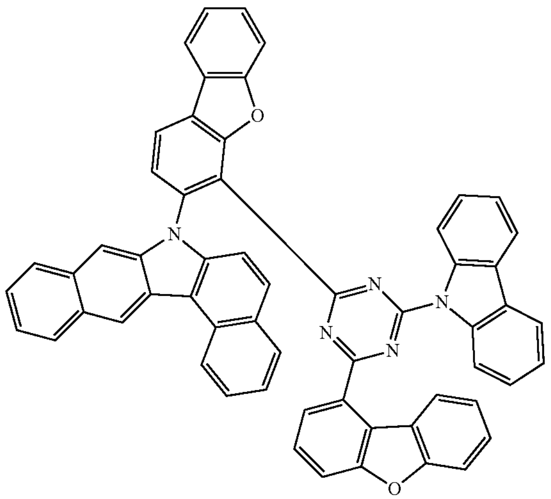
-continued
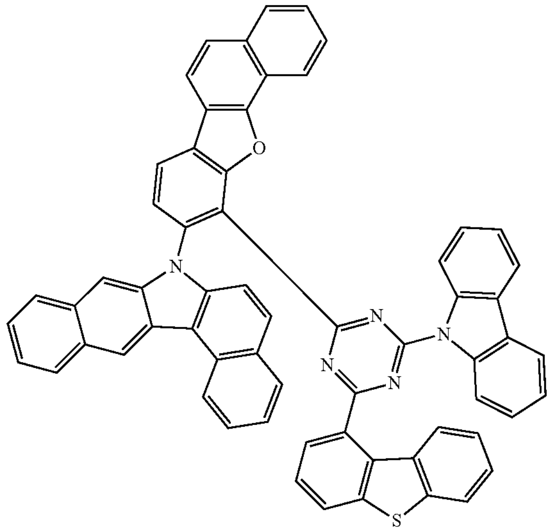
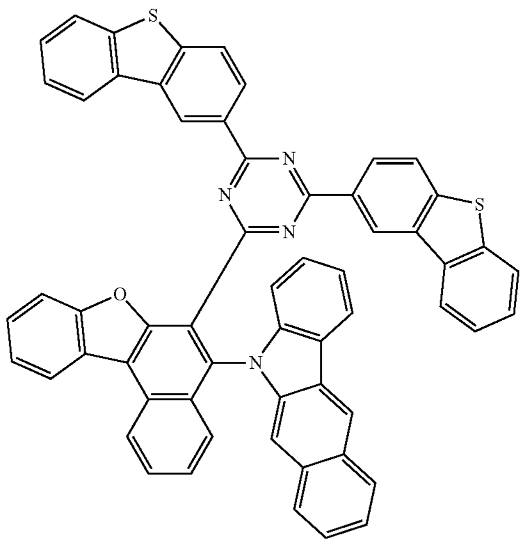
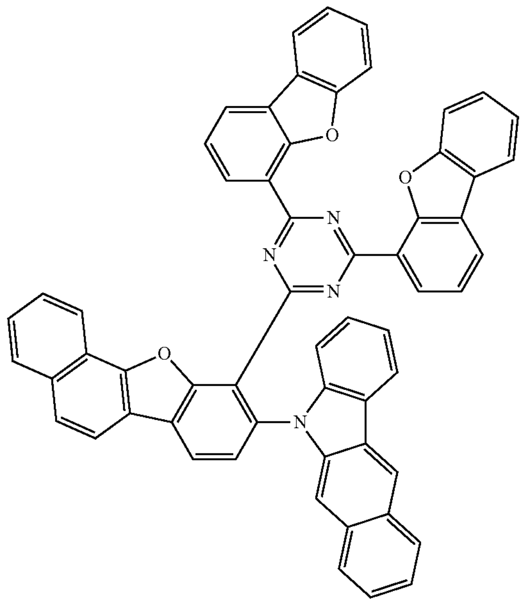

-continued
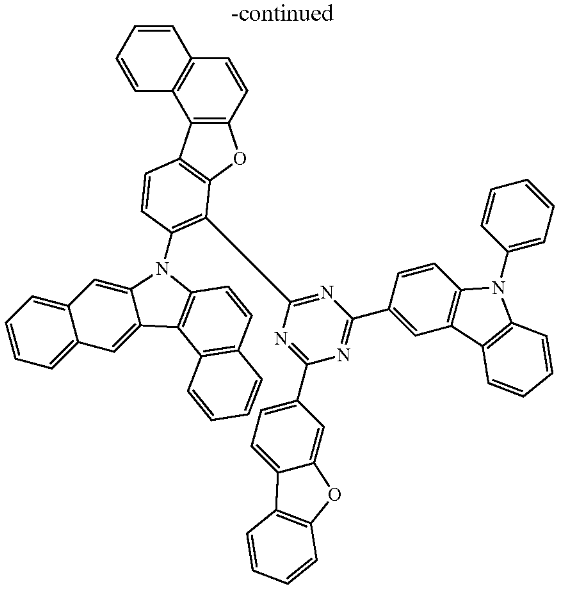
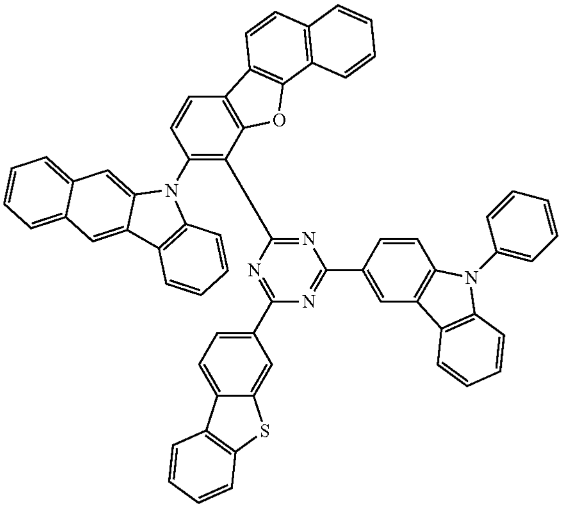
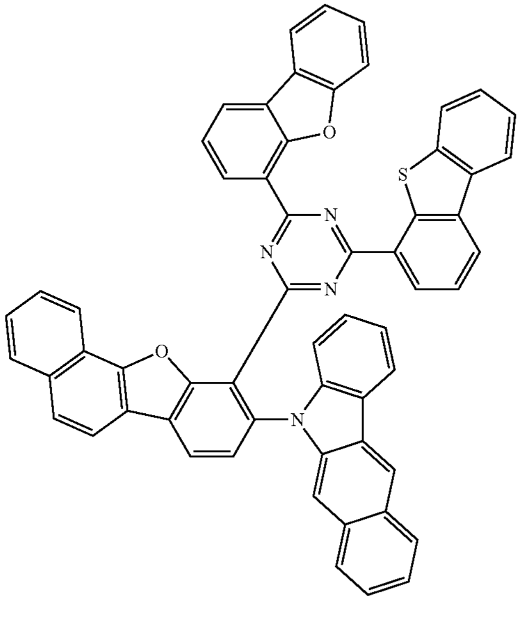
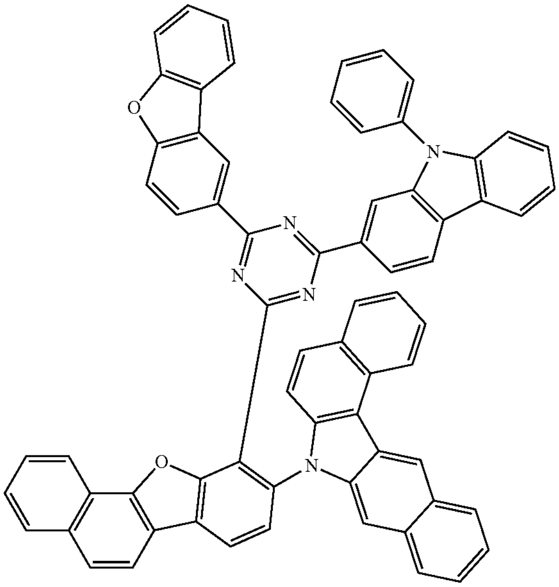
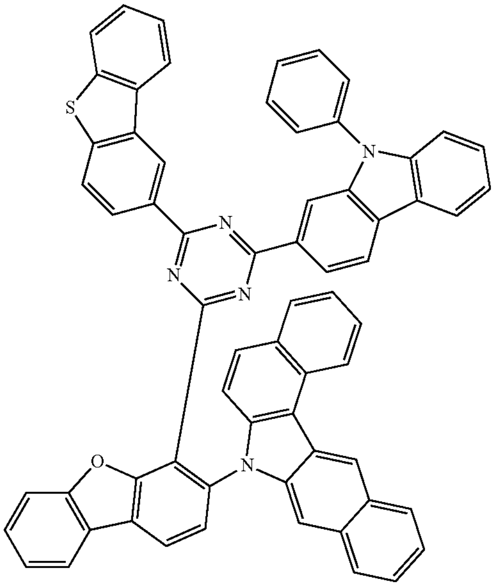
-continued
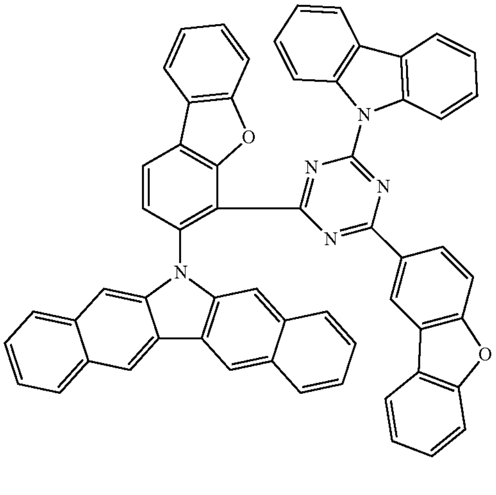

-continued
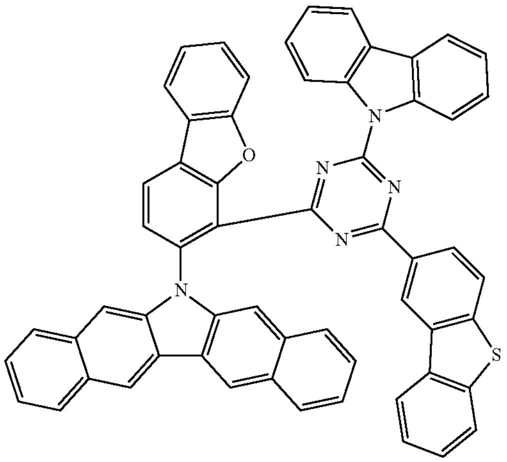
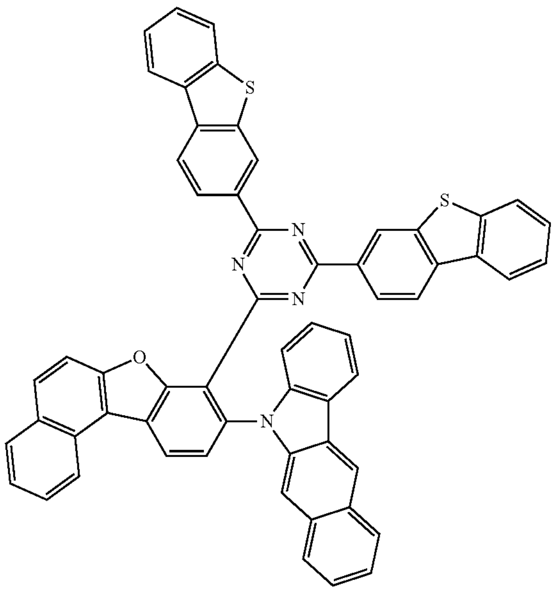
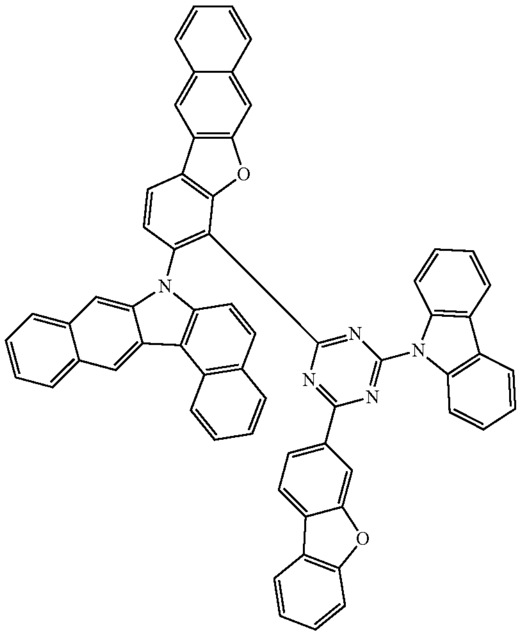
-continued
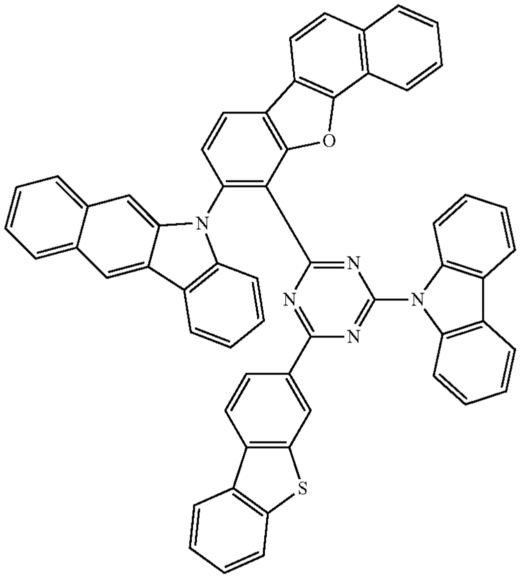
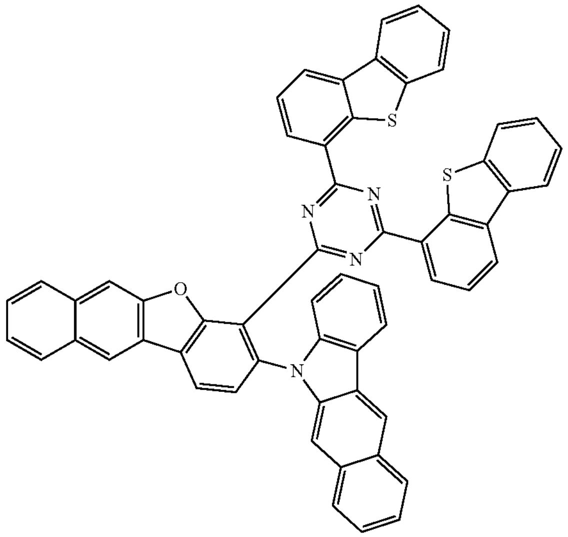
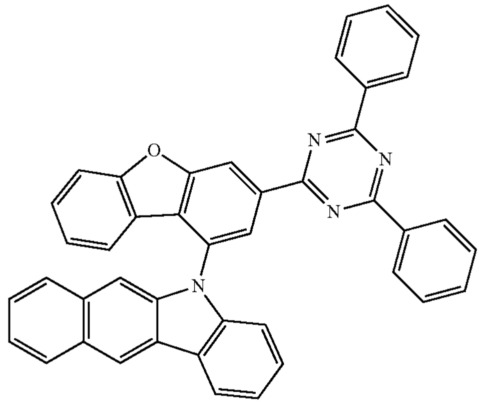

-continued
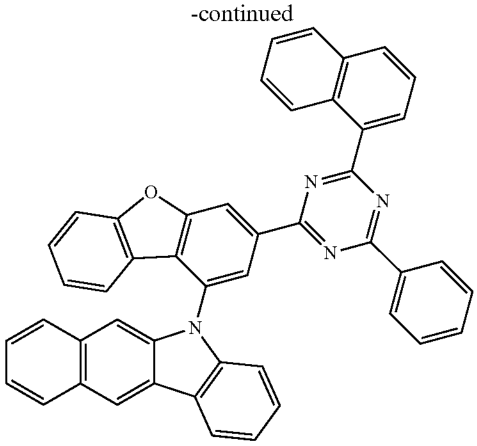
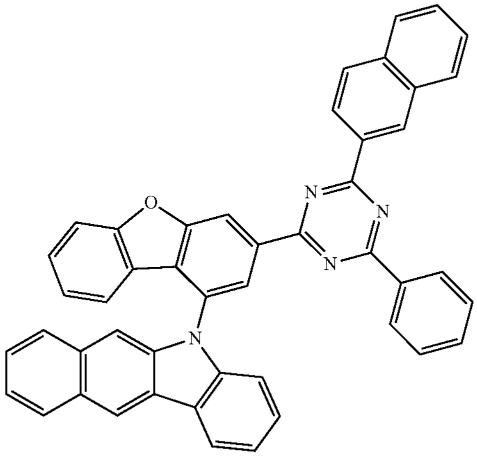
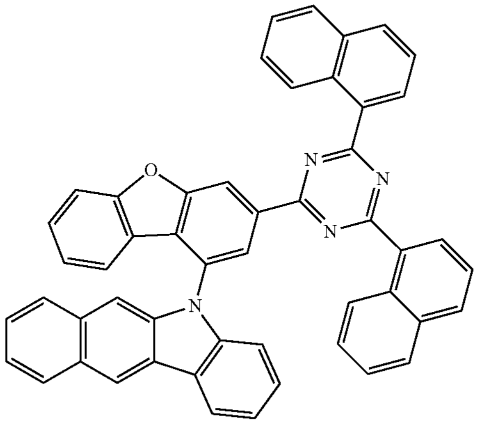
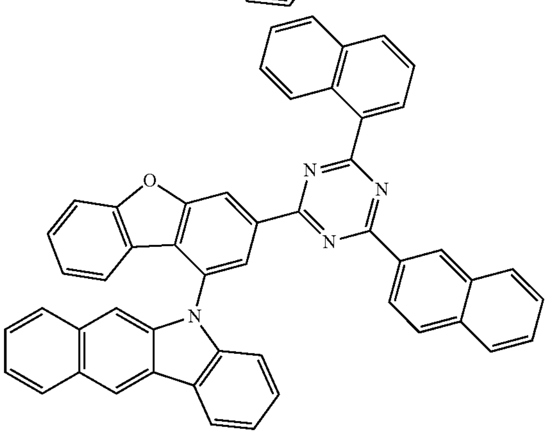
-continued
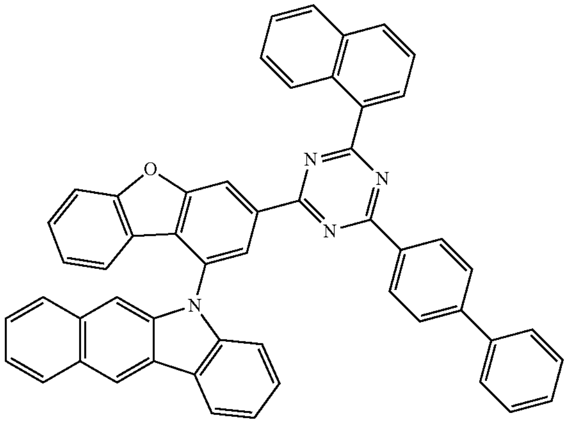
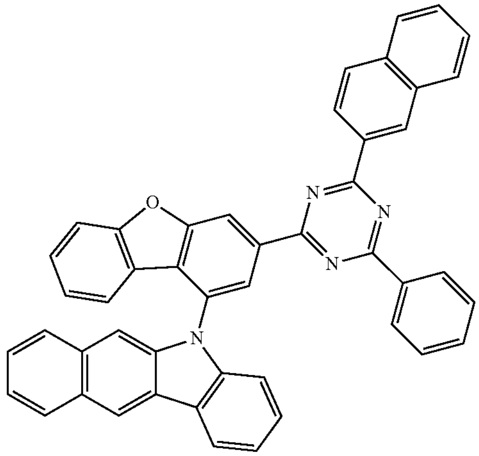
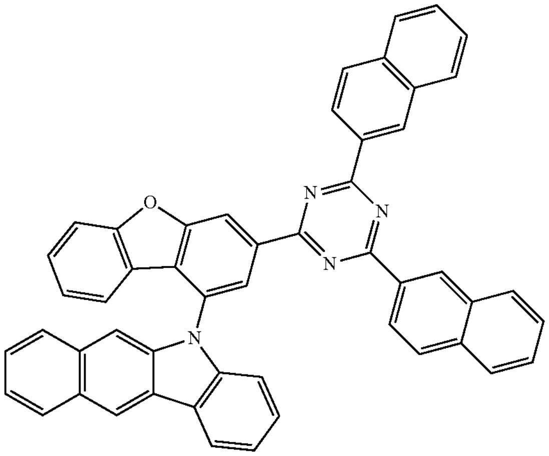

-continued
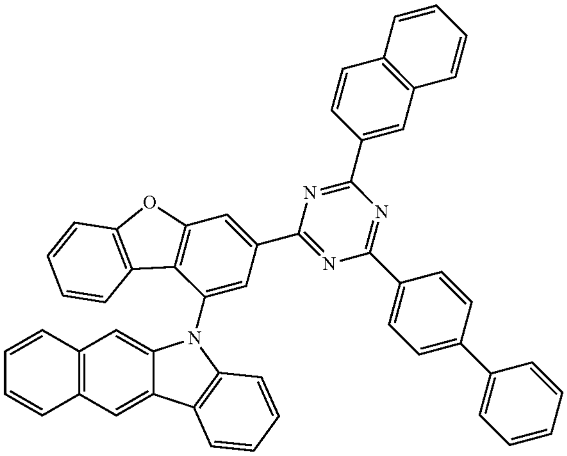
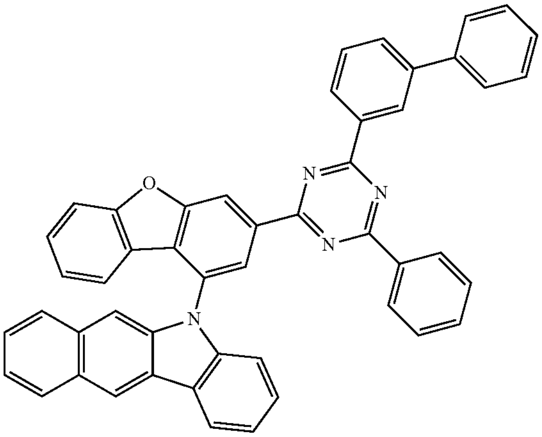
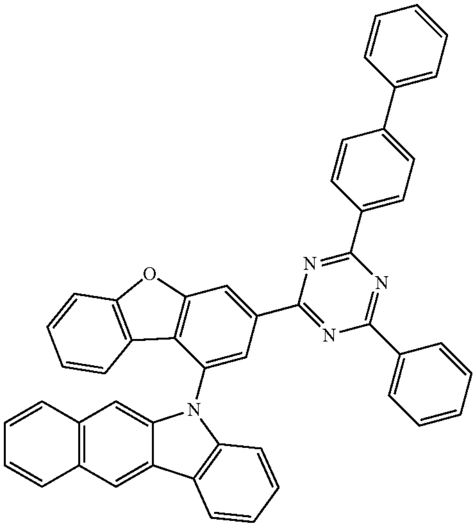
-continued
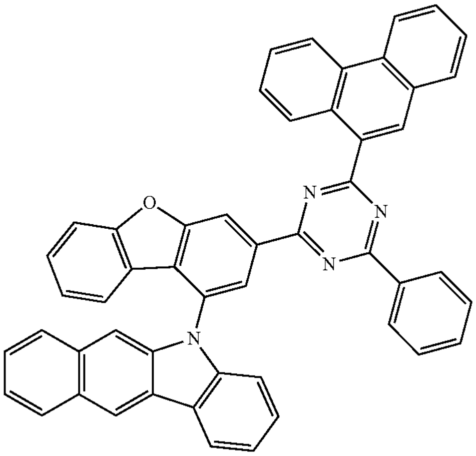
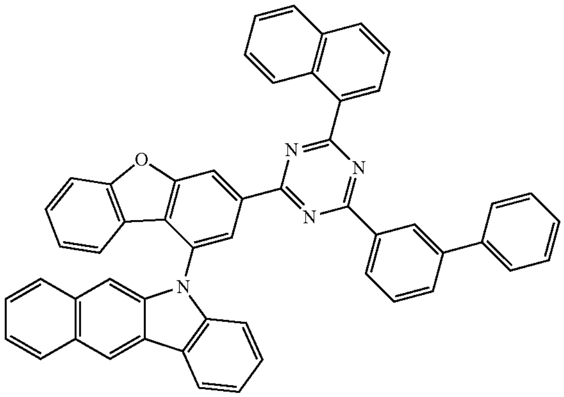
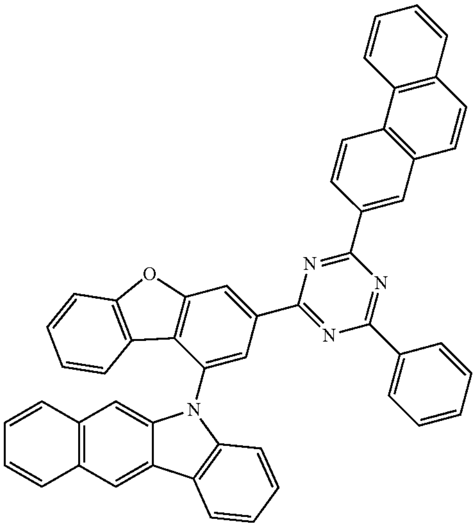

-continued
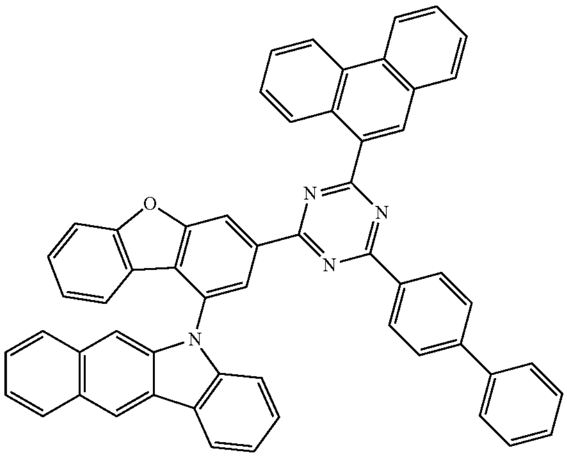
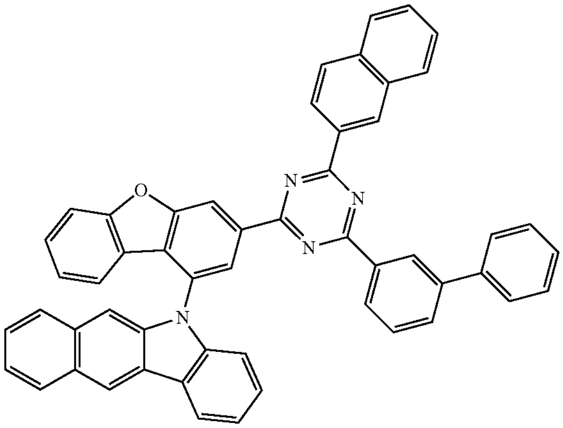
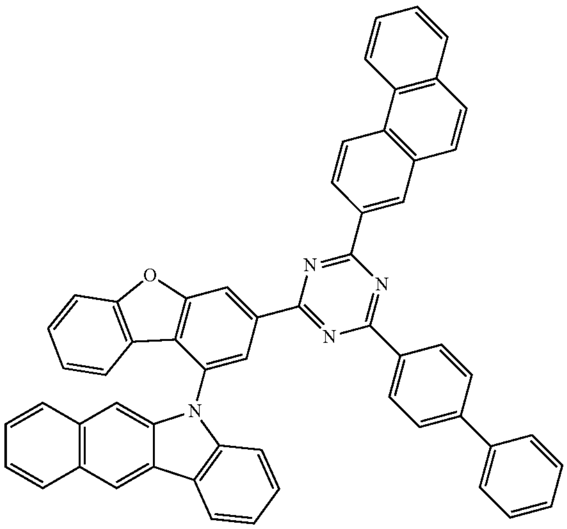
-continued
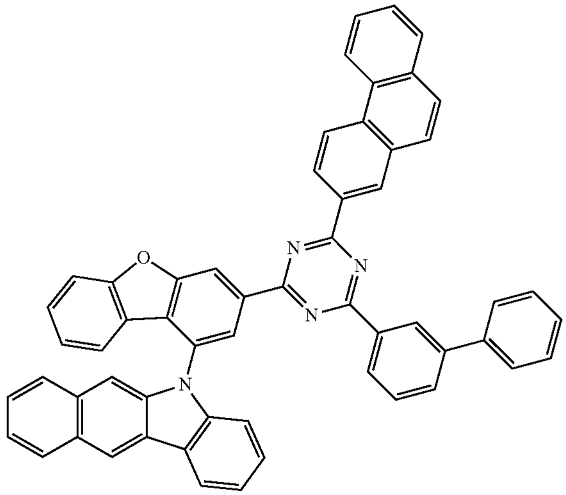
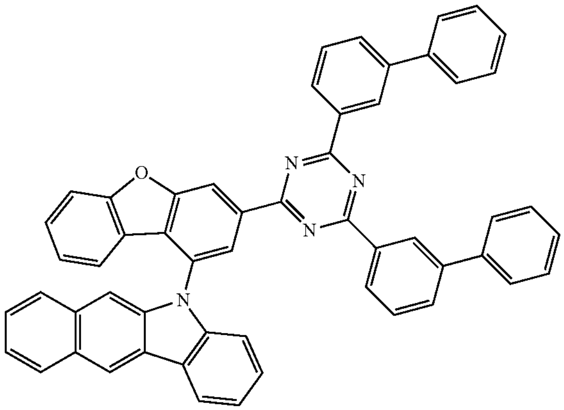
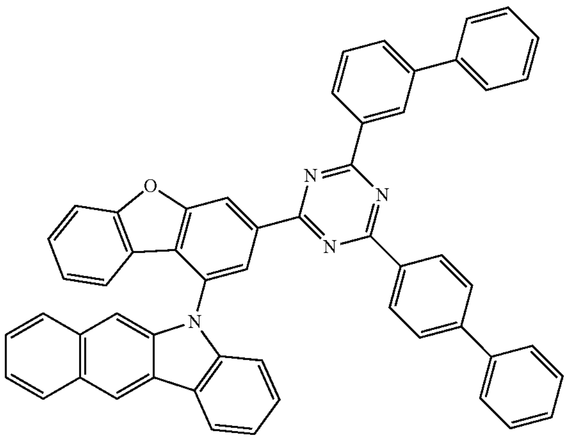

-continued
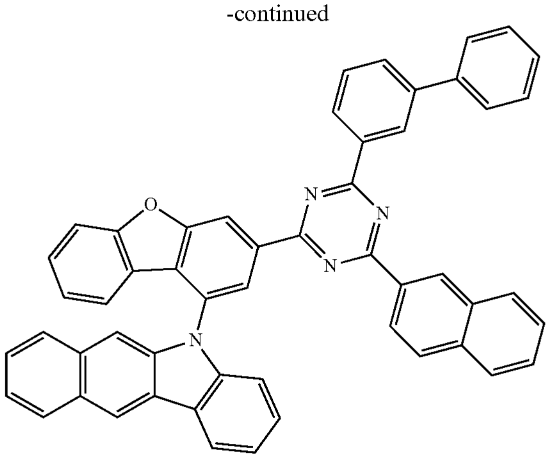
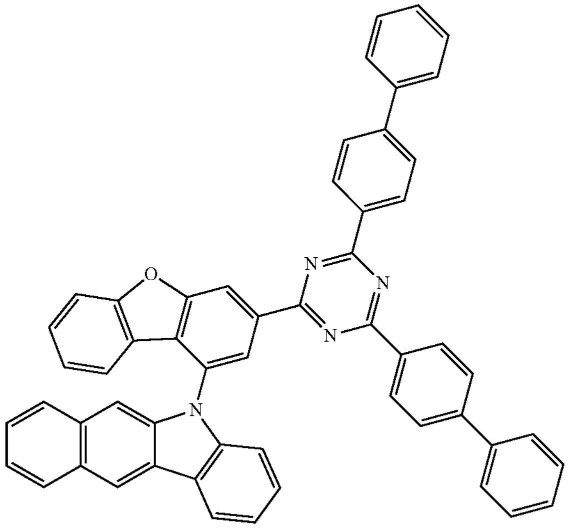
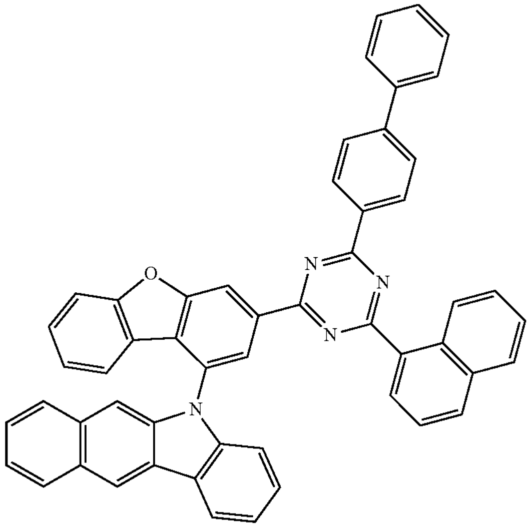
-continued
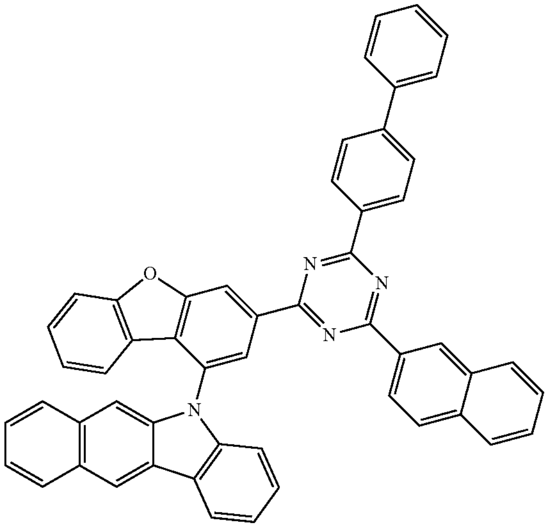
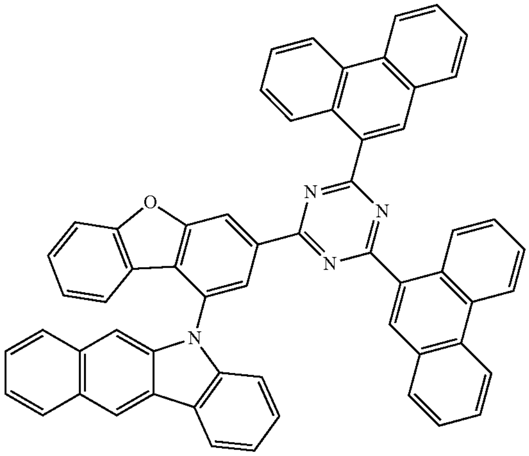
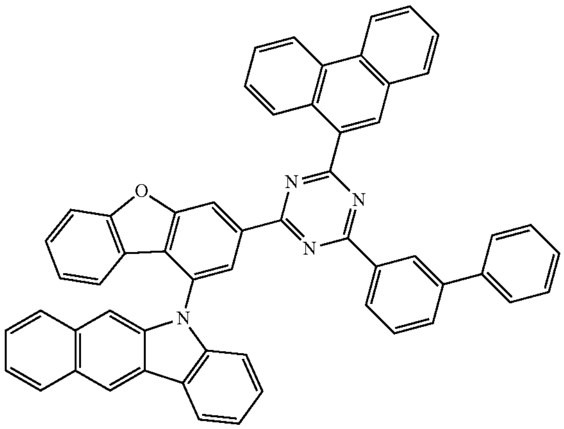

-continued
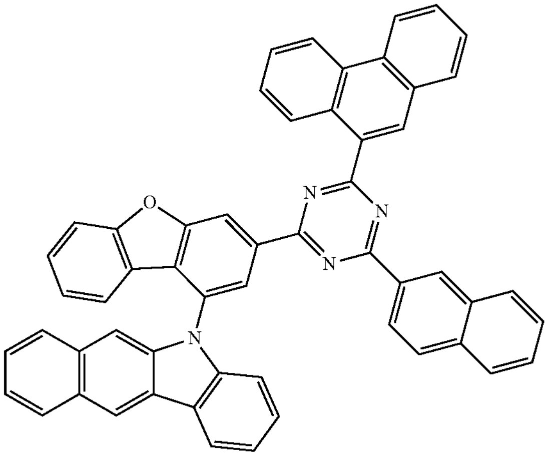
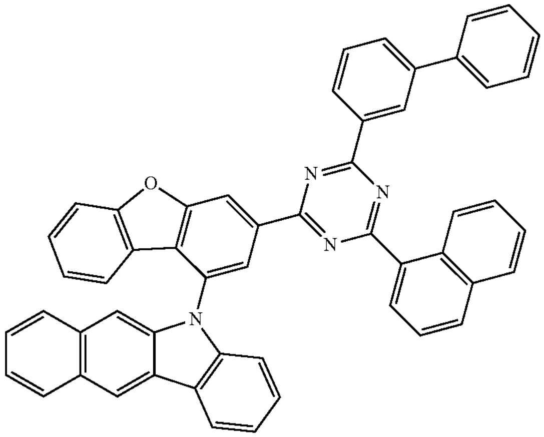
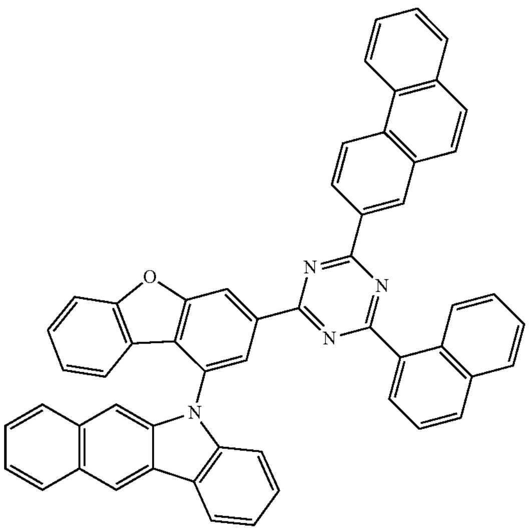
-continued
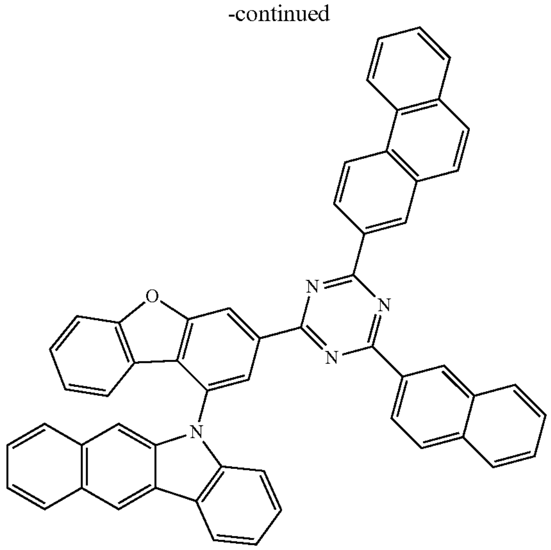
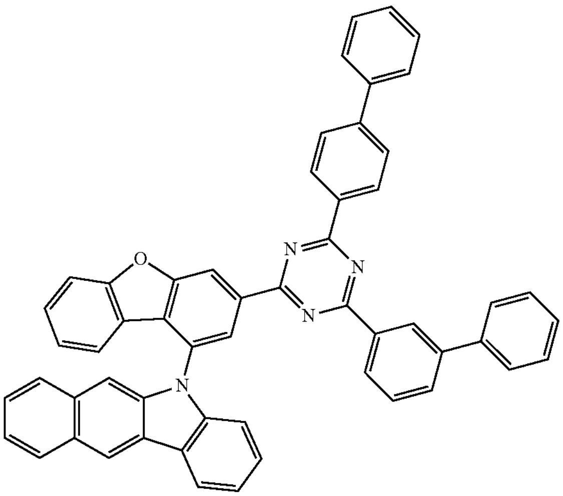
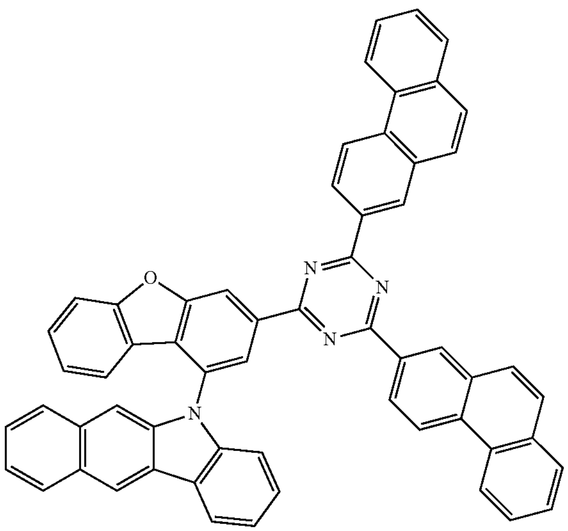

-continued
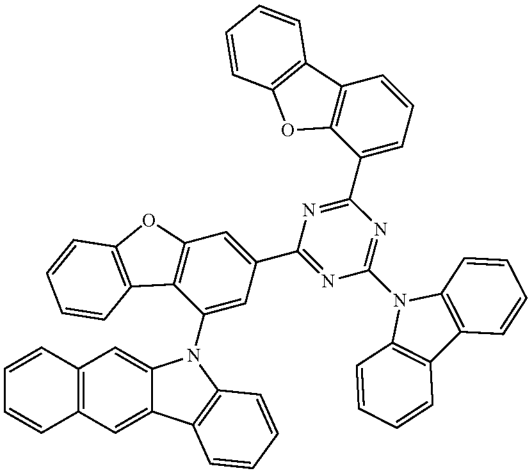
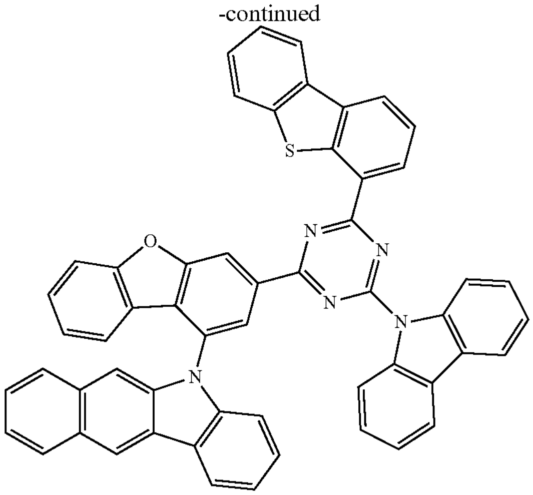
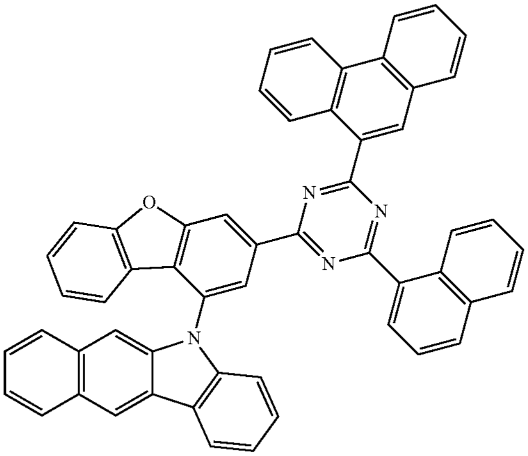
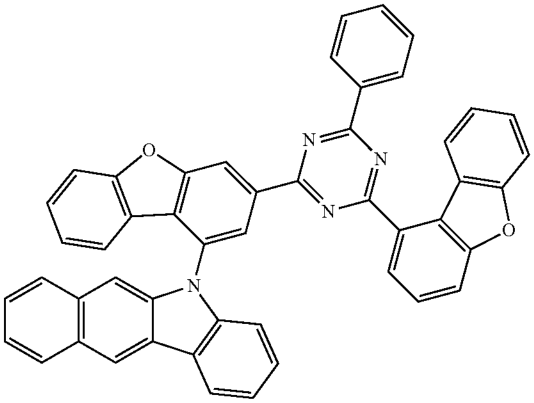
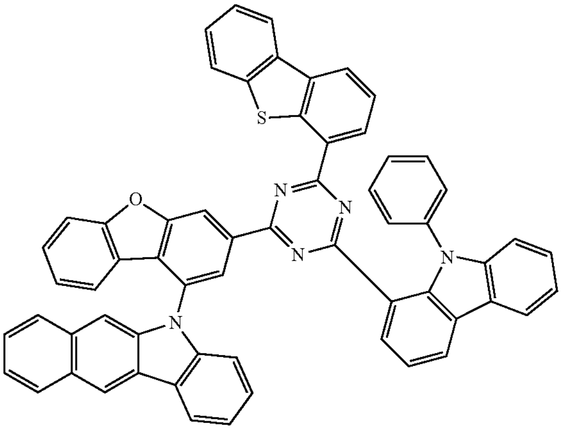
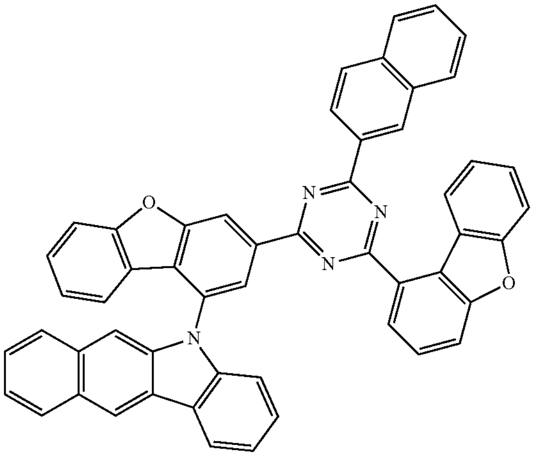
-continued -continued
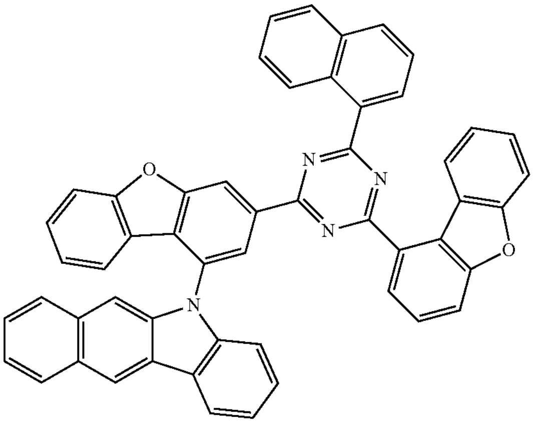
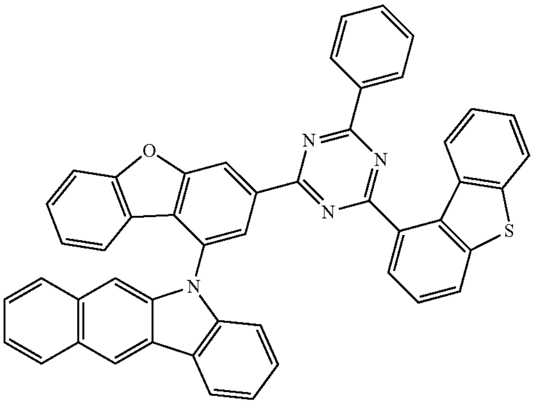
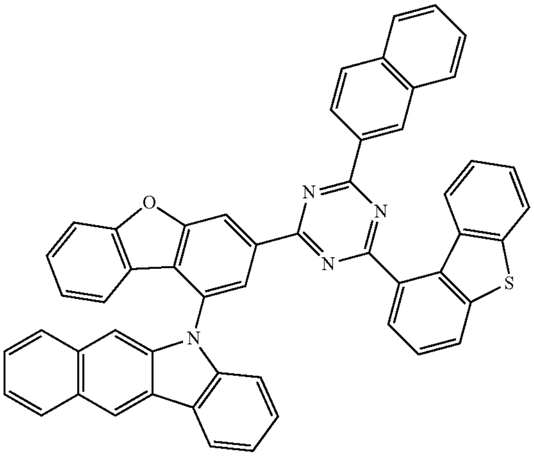
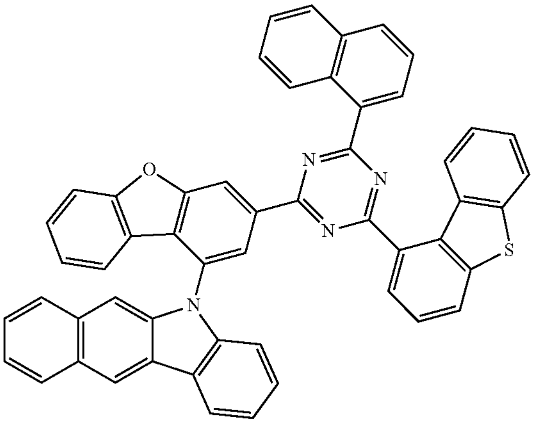
-continued
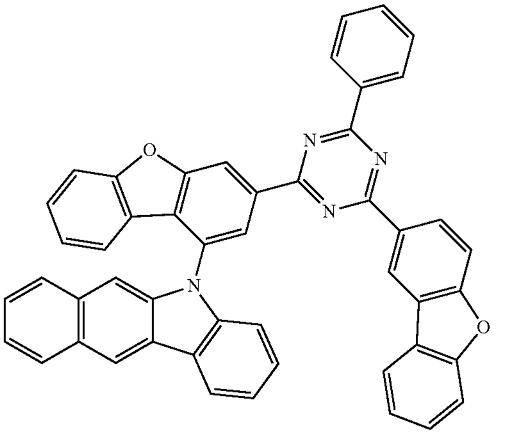
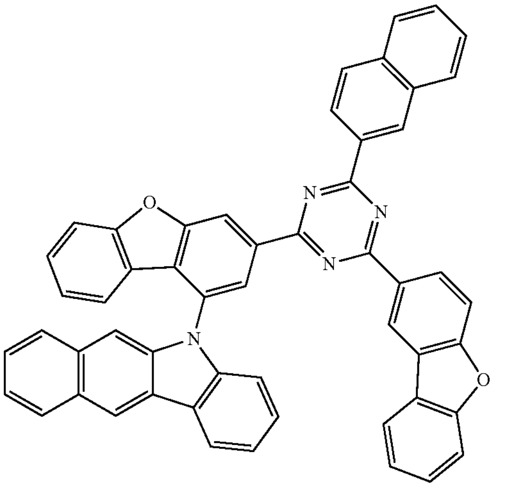
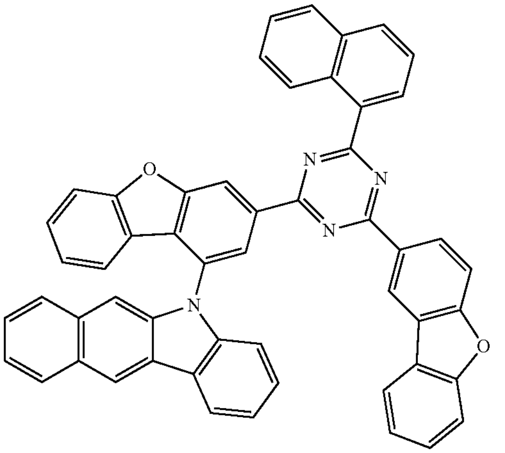

-continued
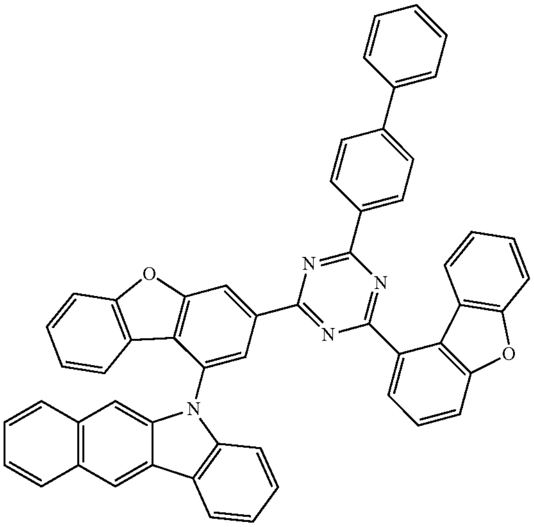
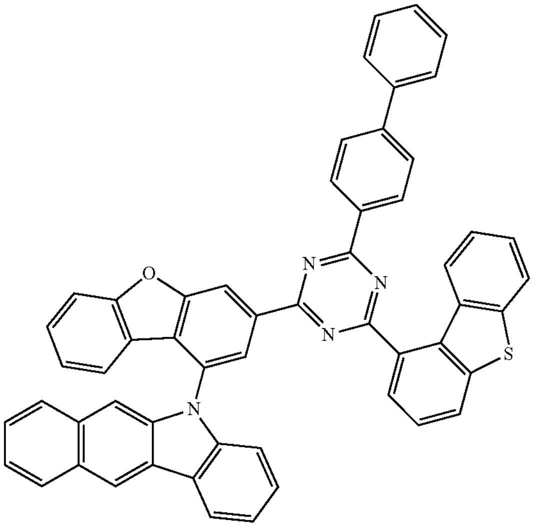
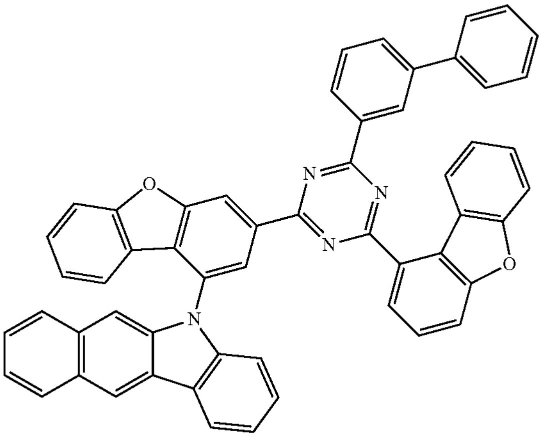
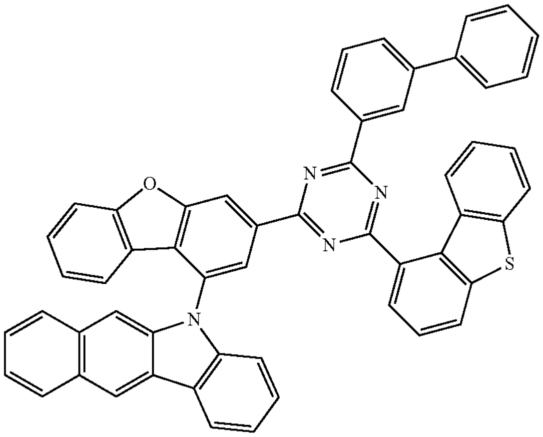
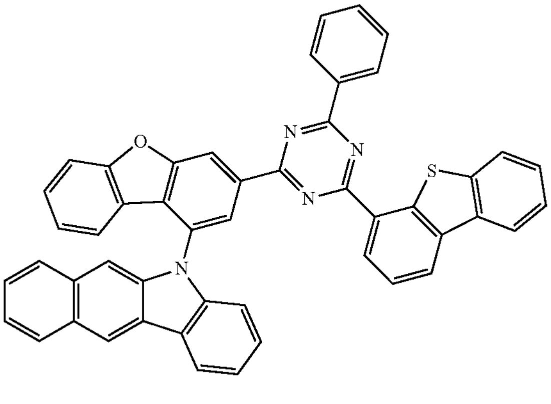
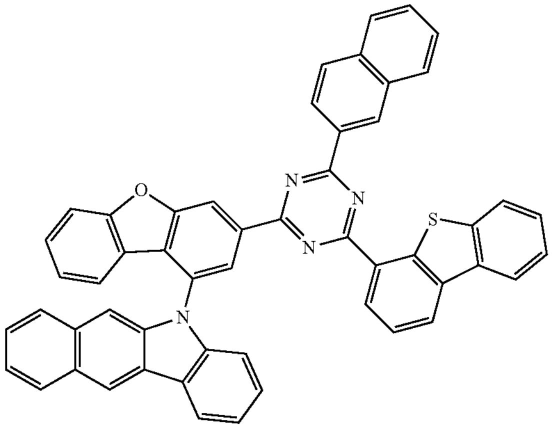
-continued

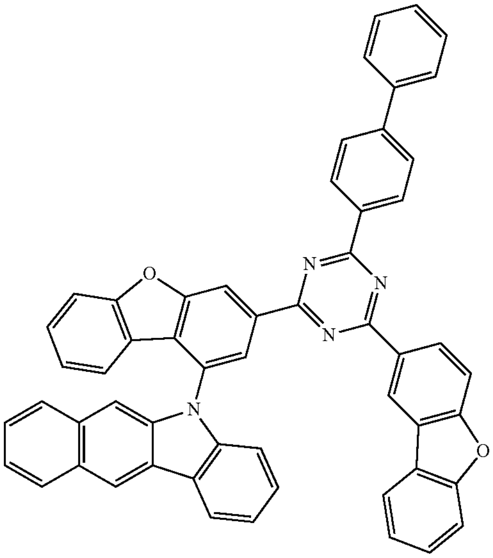
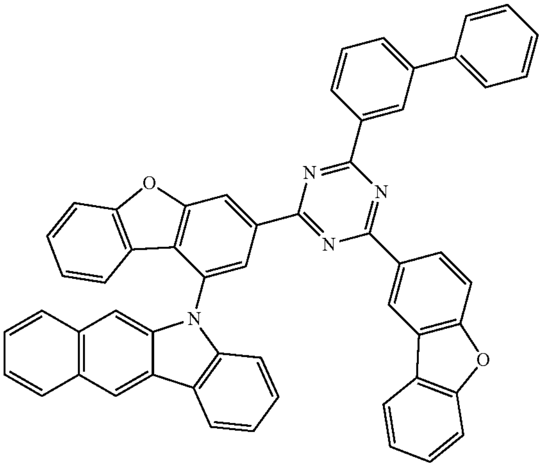
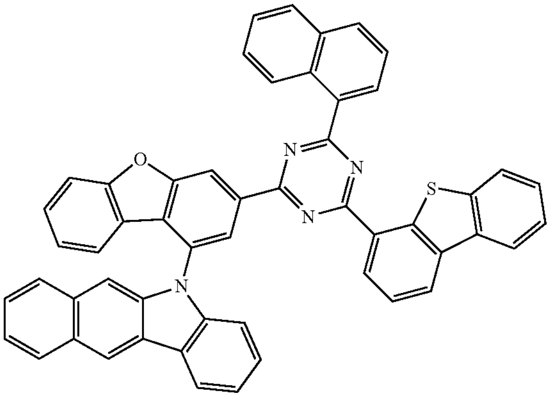
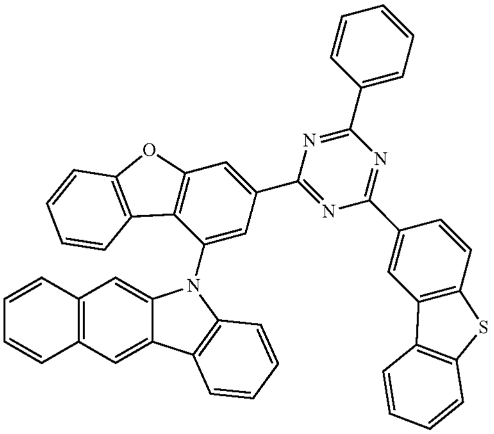
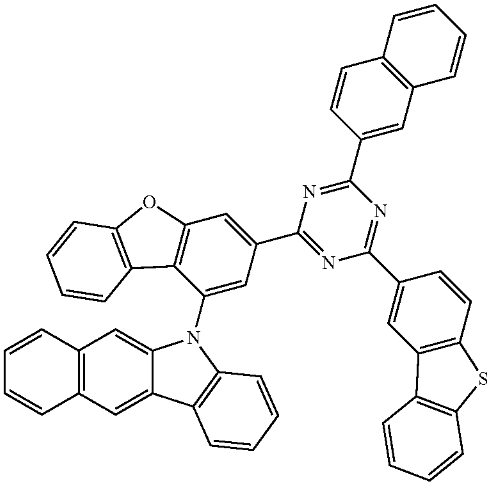
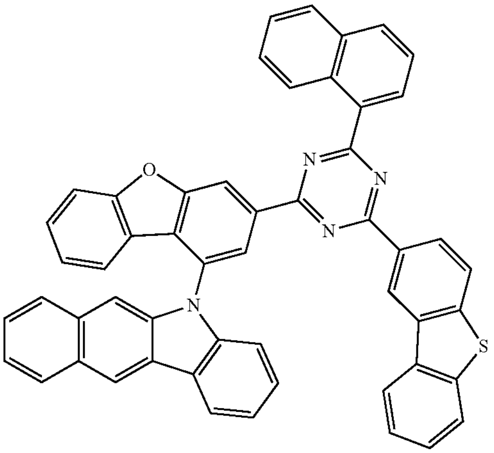

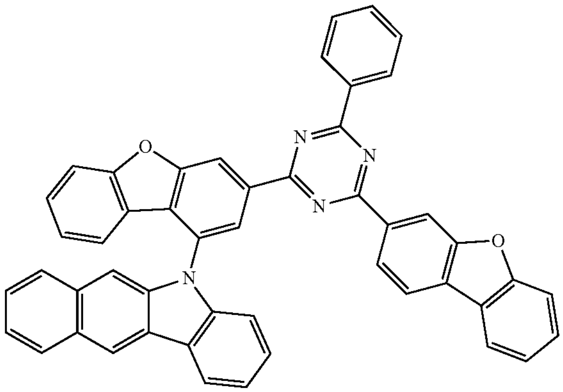
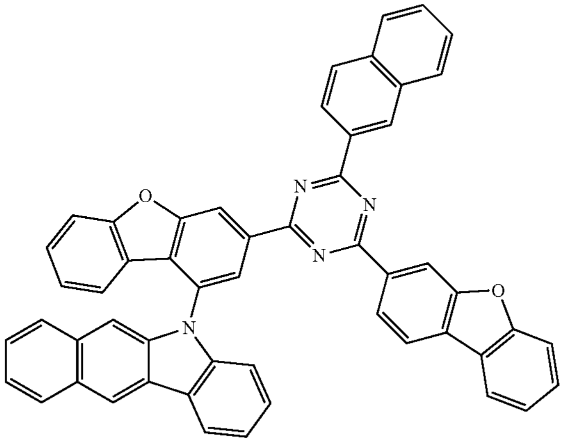
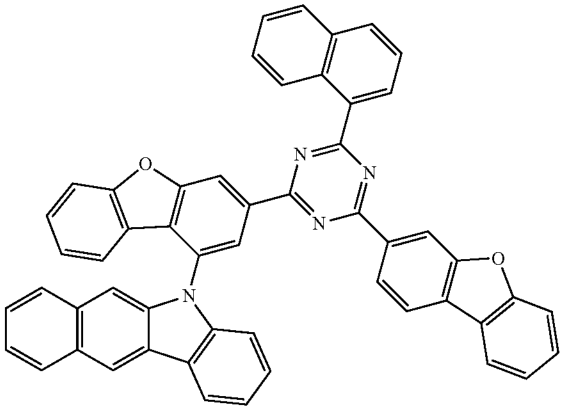
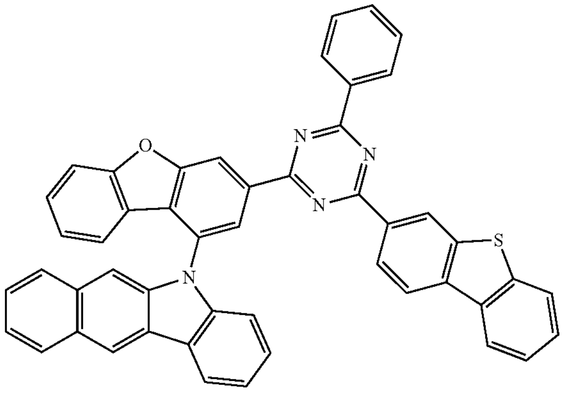
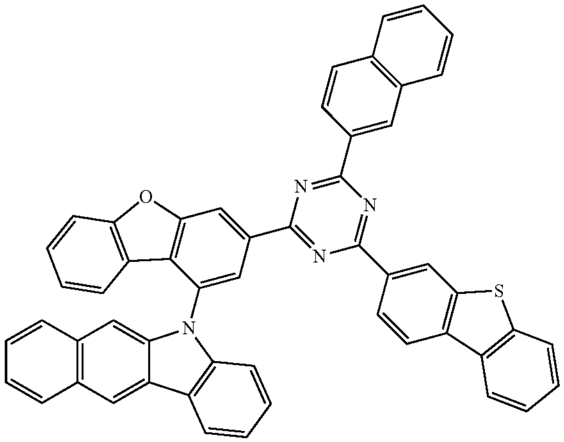
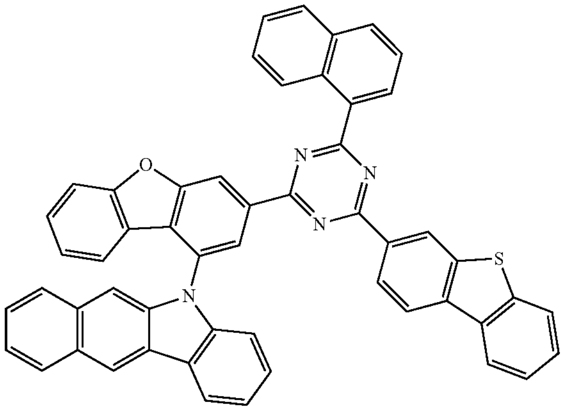
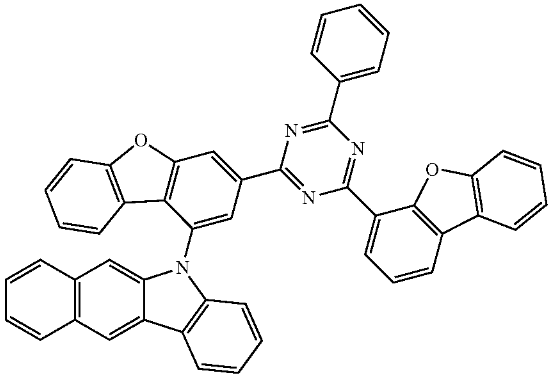
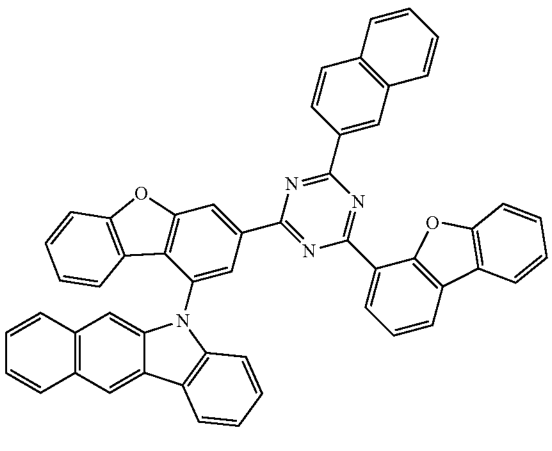

-continued
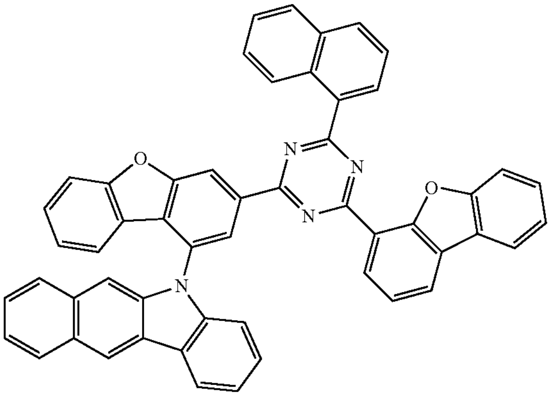
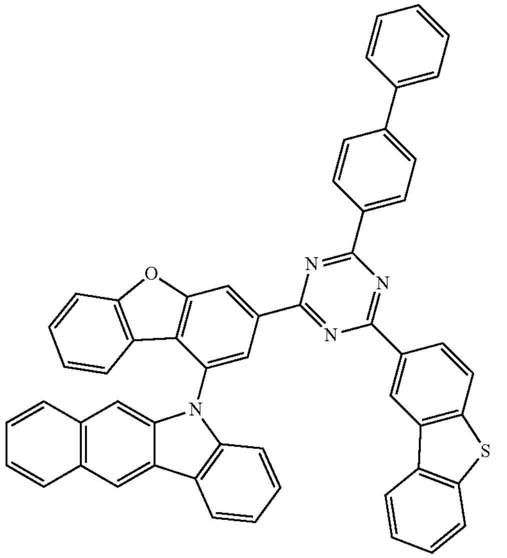
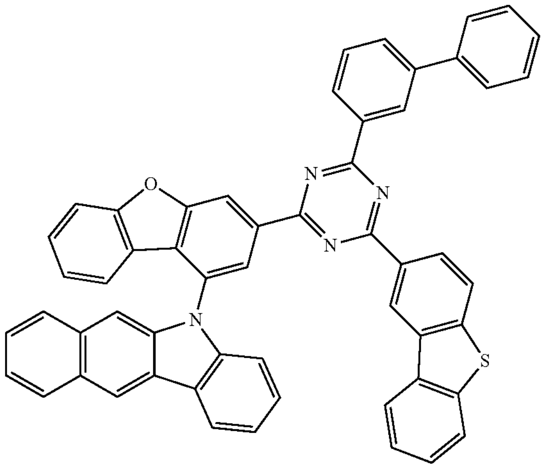
-continued
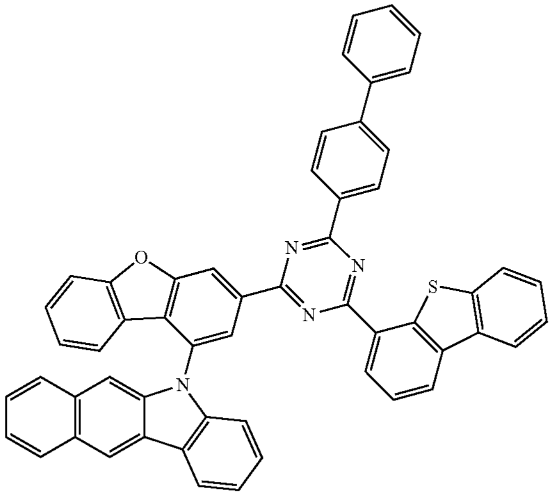
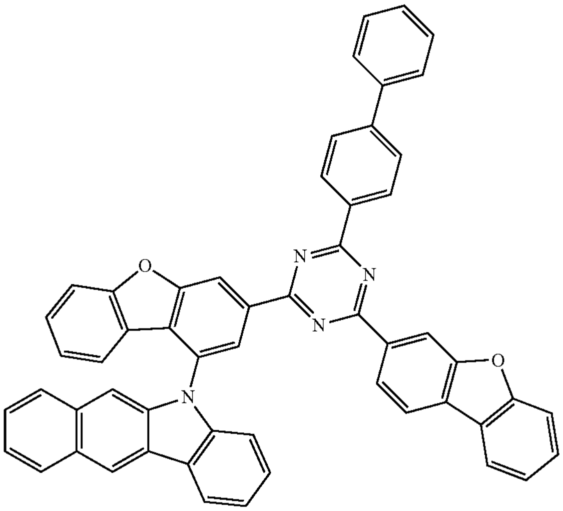
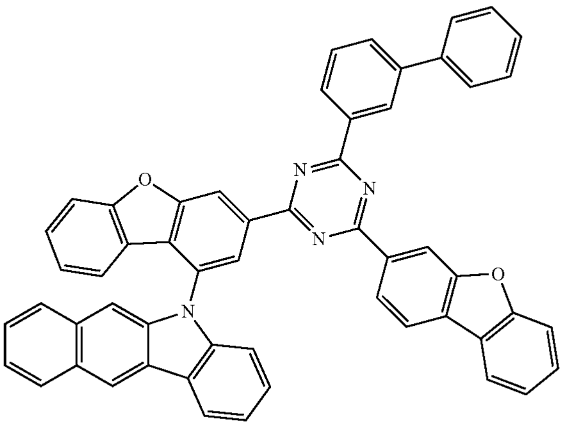

-continued
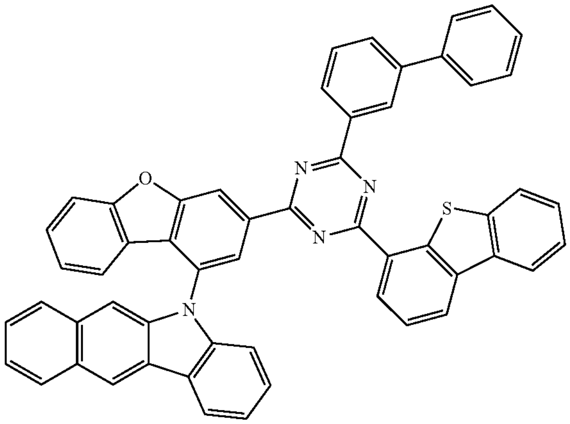
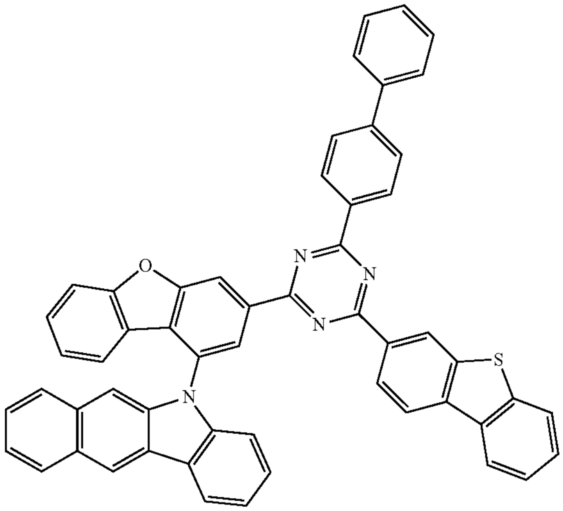
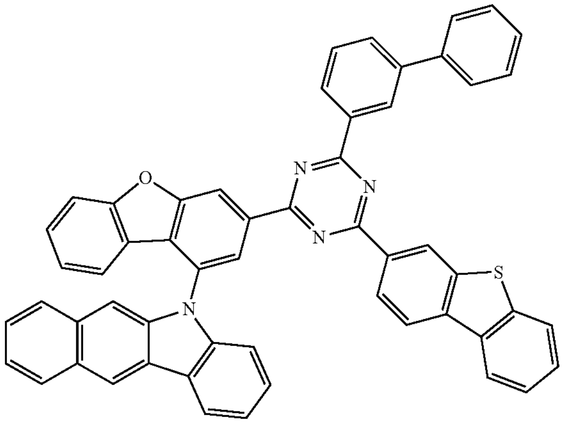
-continued
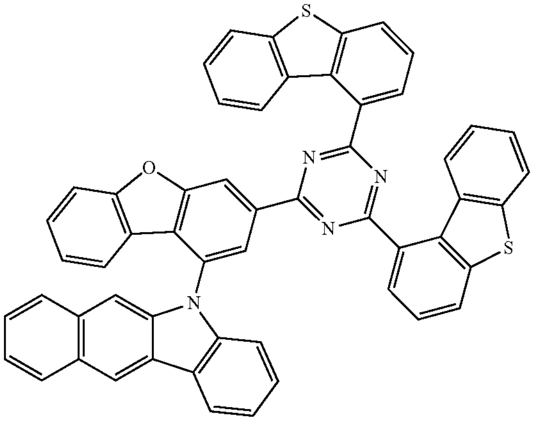
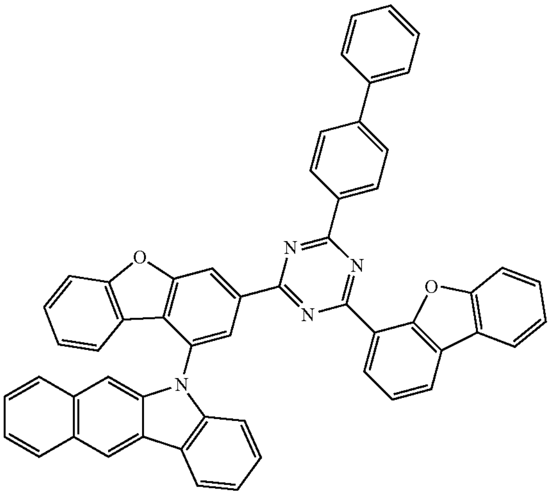
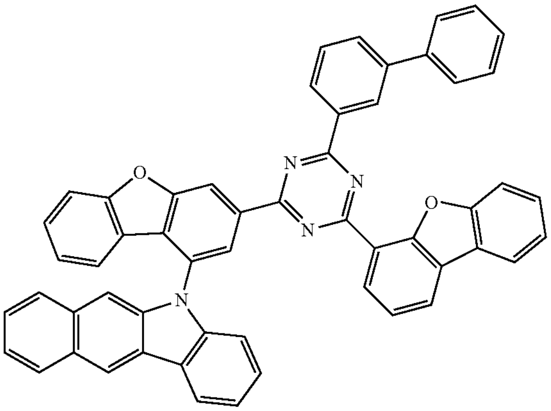

-continued
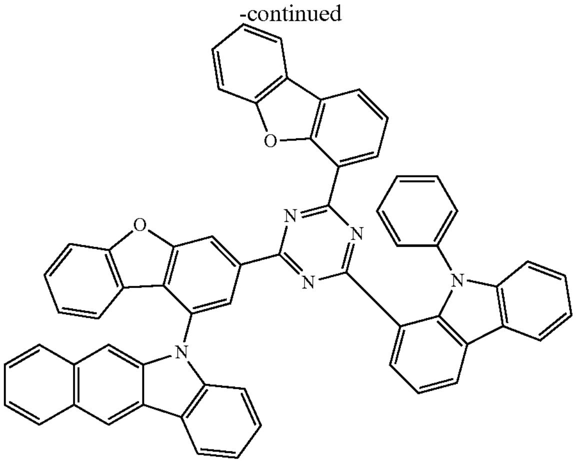
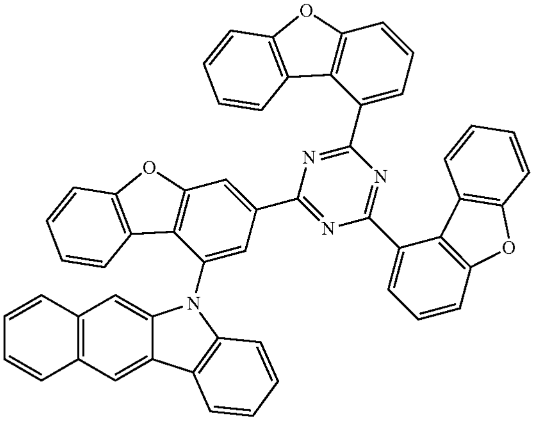
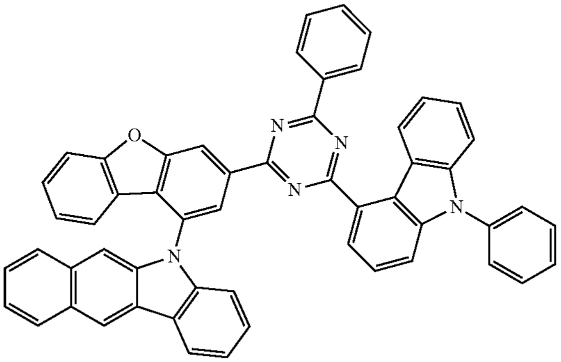
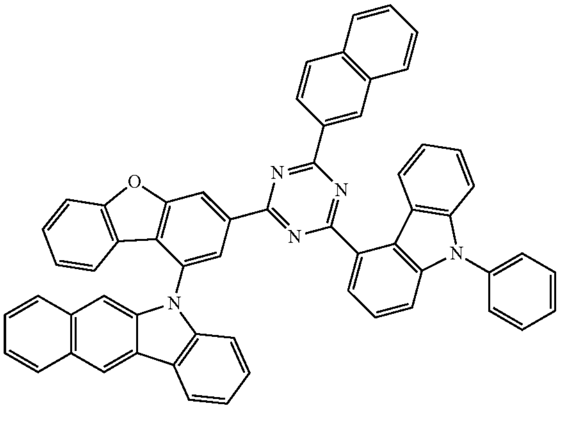
-continued
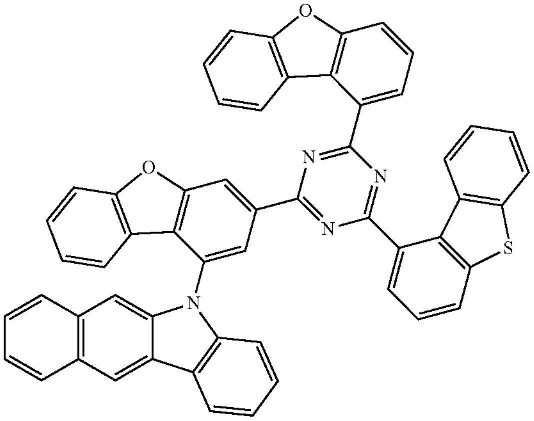
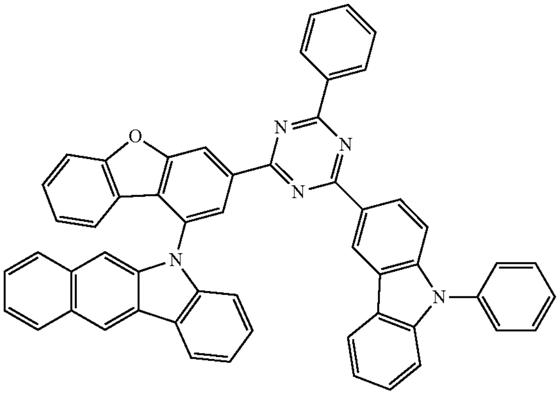
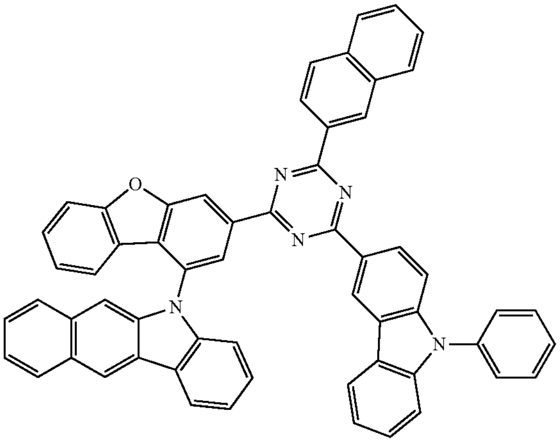

-continued
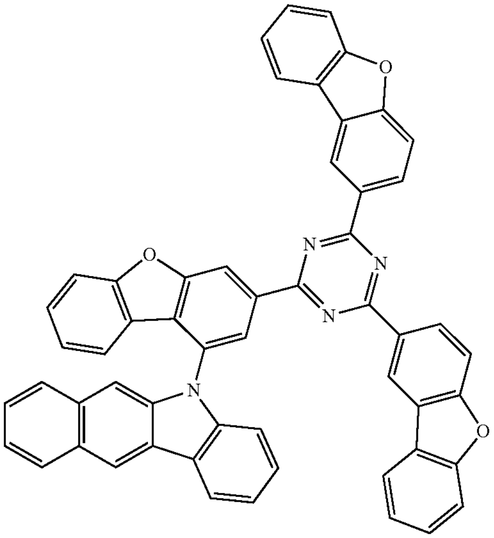
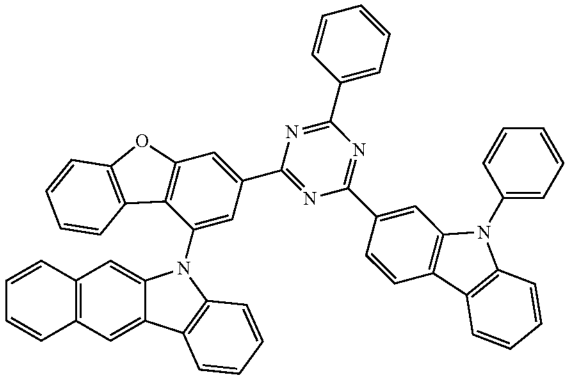
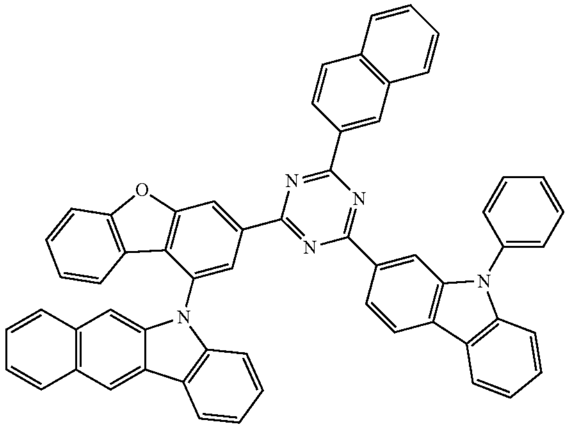
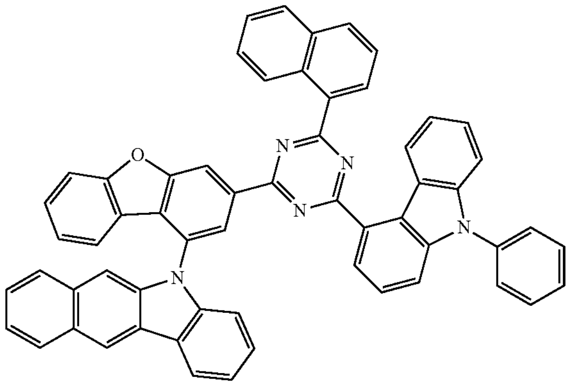
-continued
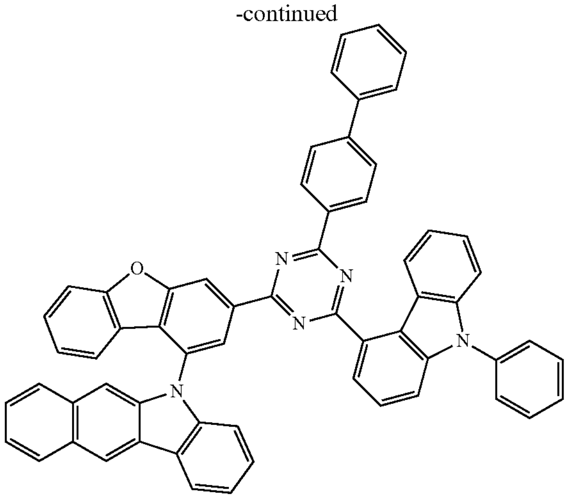
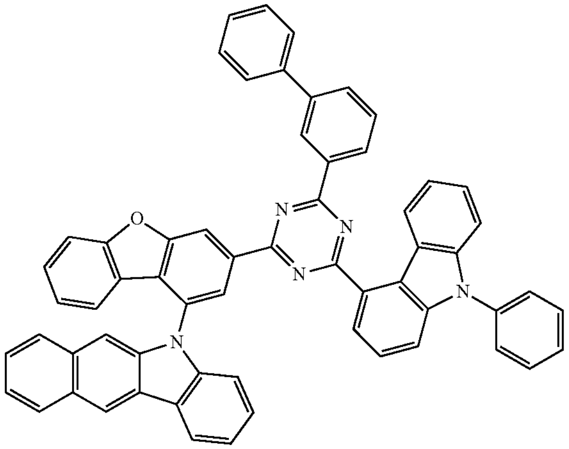
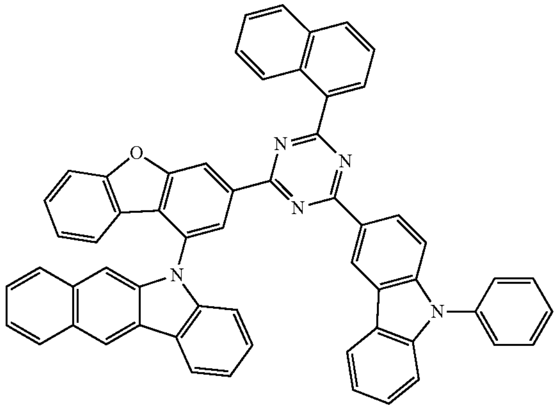

-continued
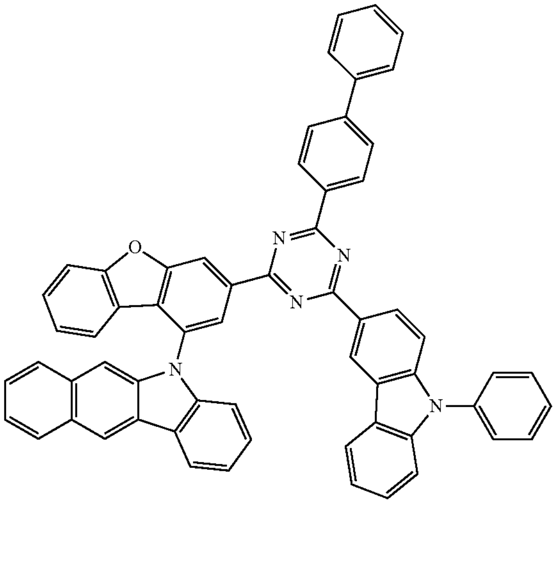
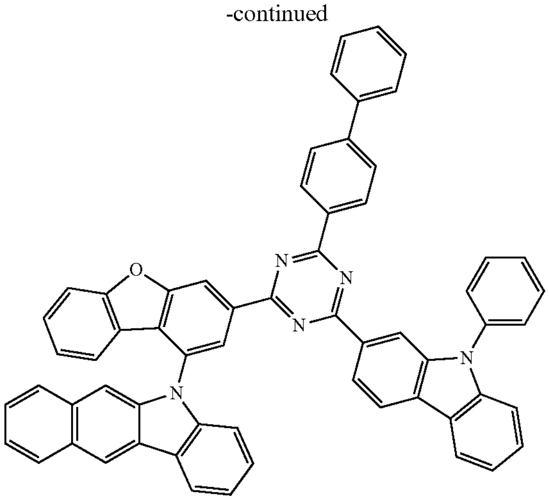
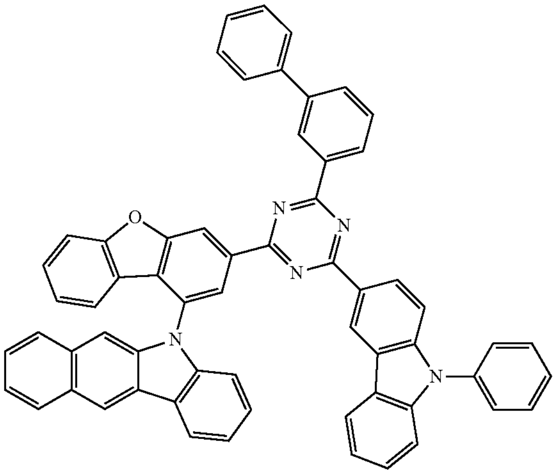
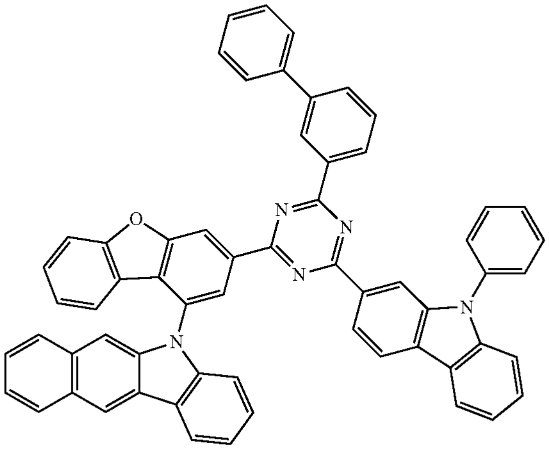
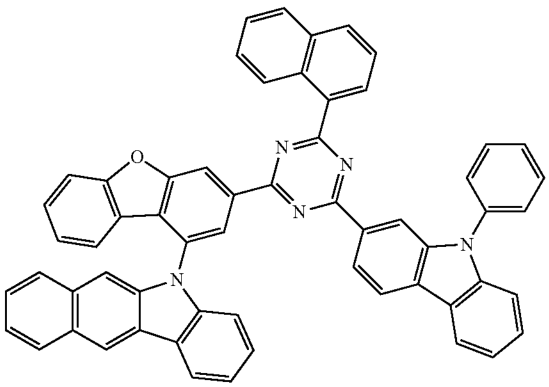
-continued
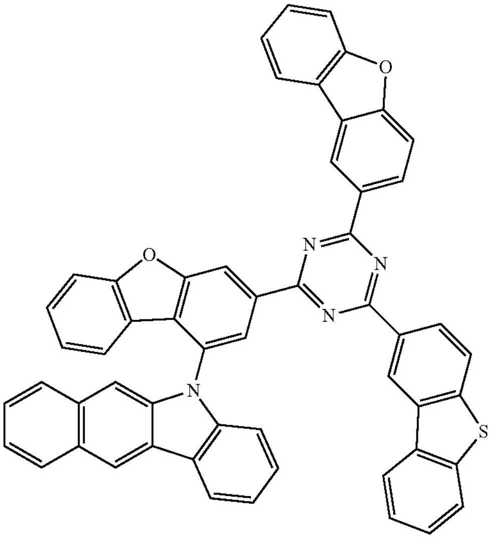

-continued
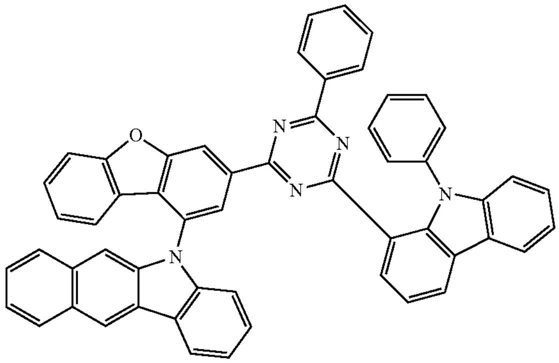
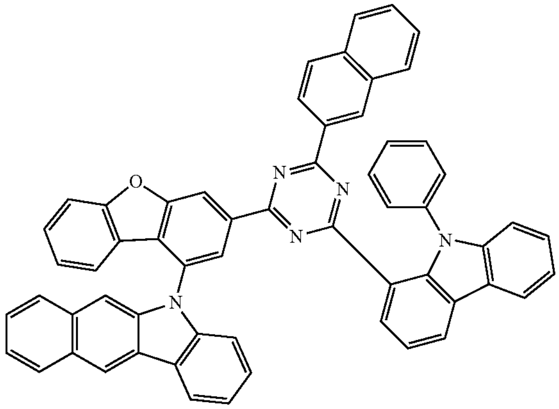
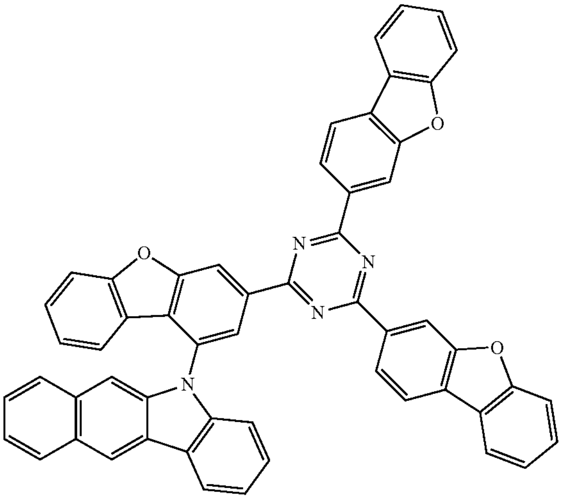
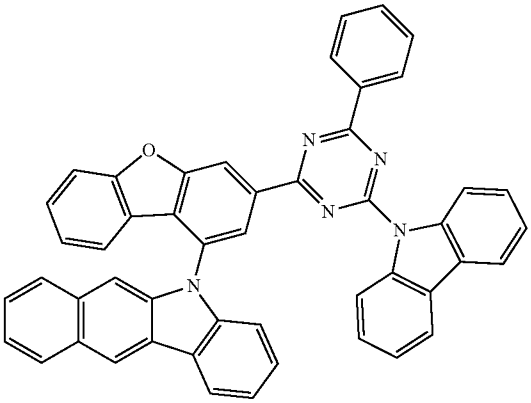
-continued
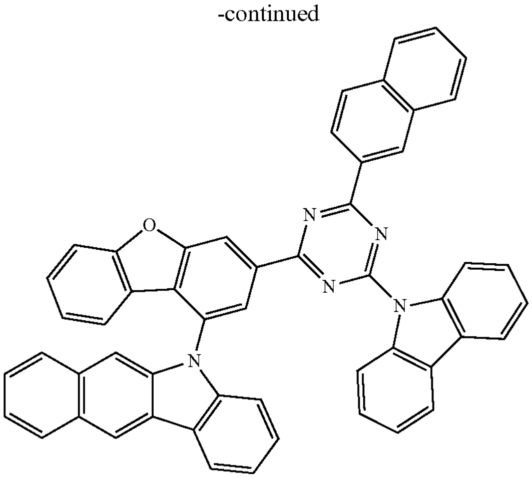
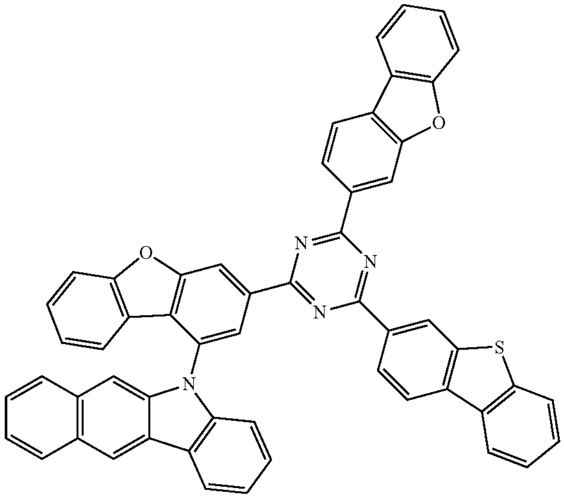
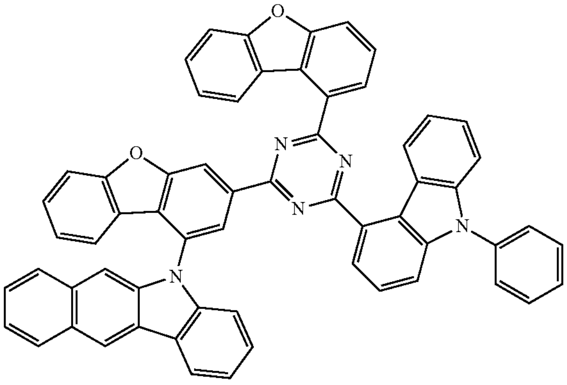
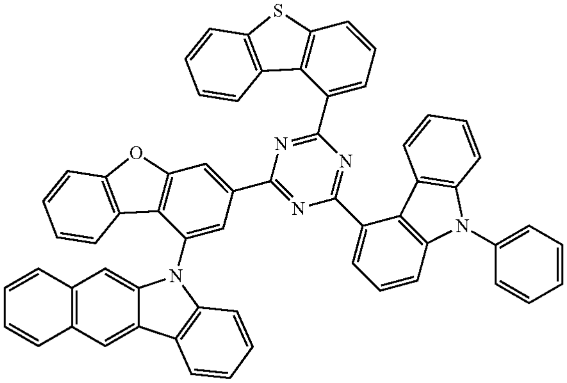

-continued
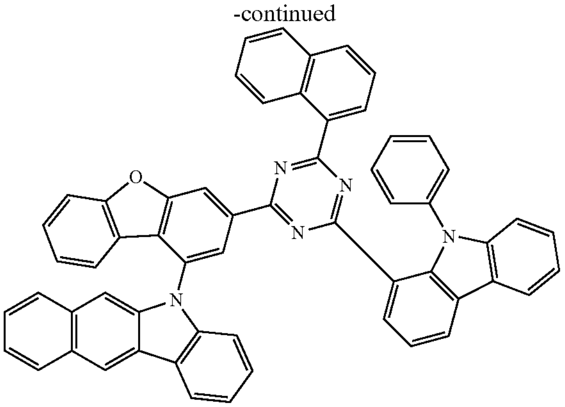
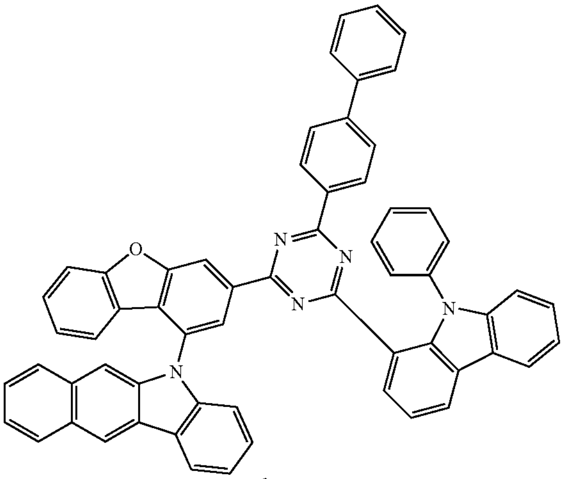
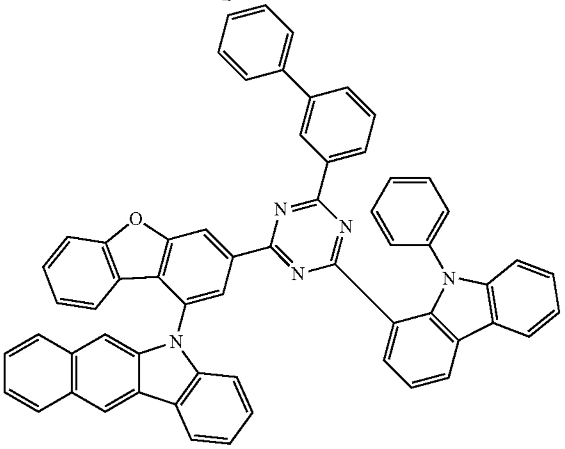
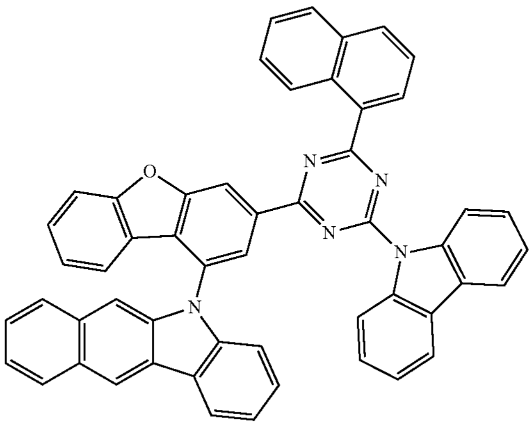
-continued
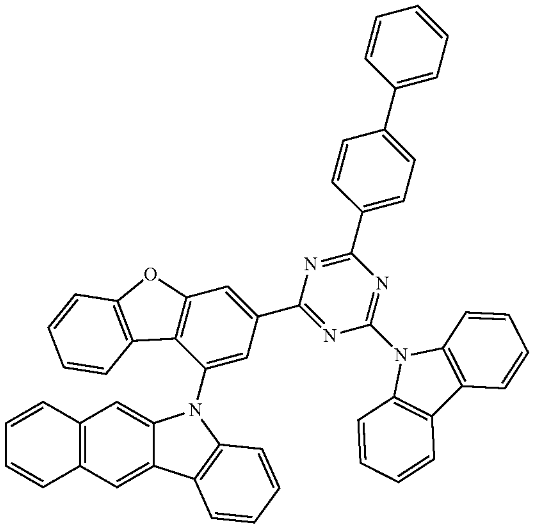
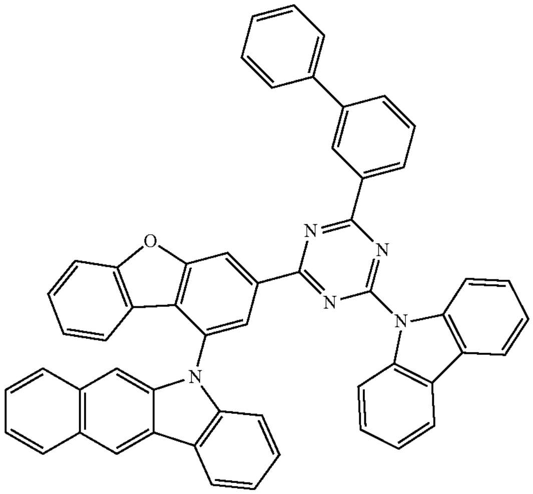
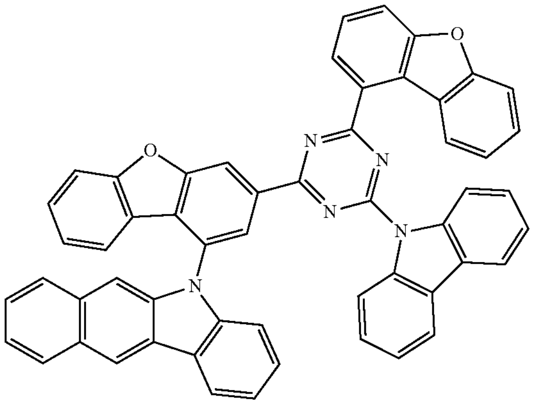

-continued
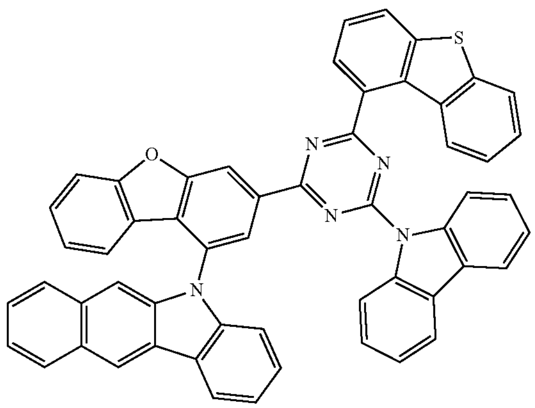
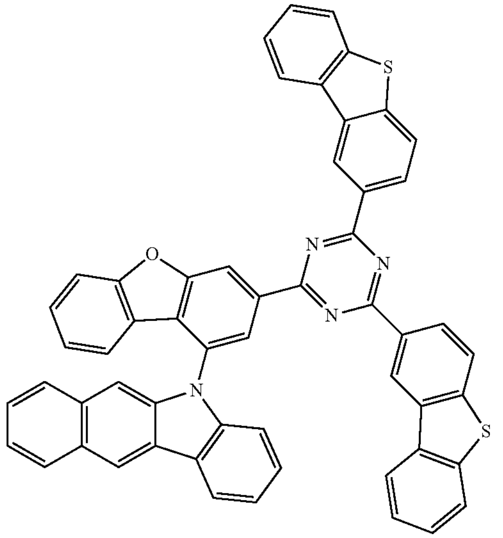
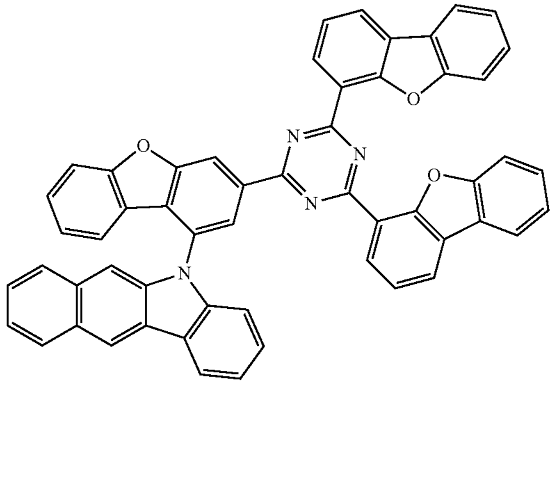
-continued
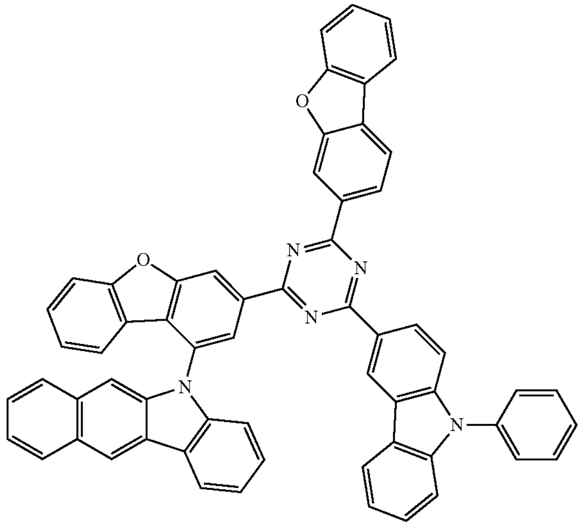
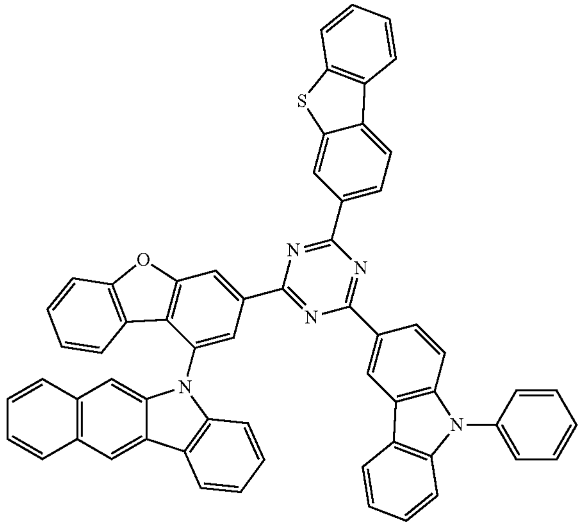
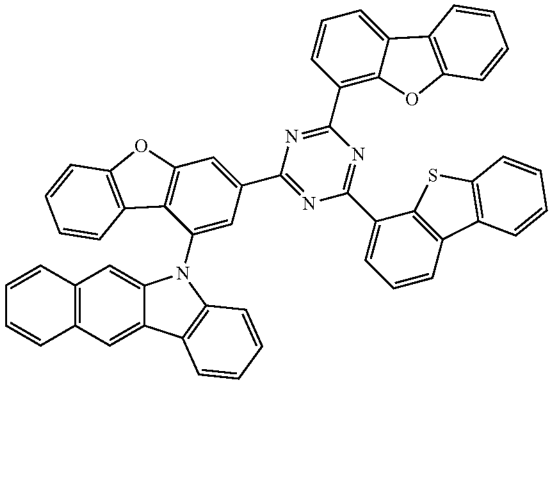

-continued
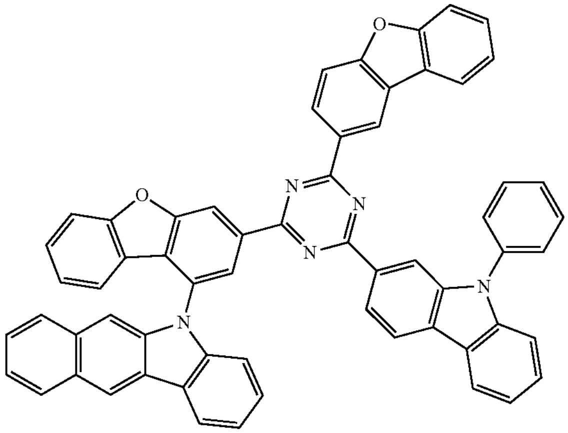
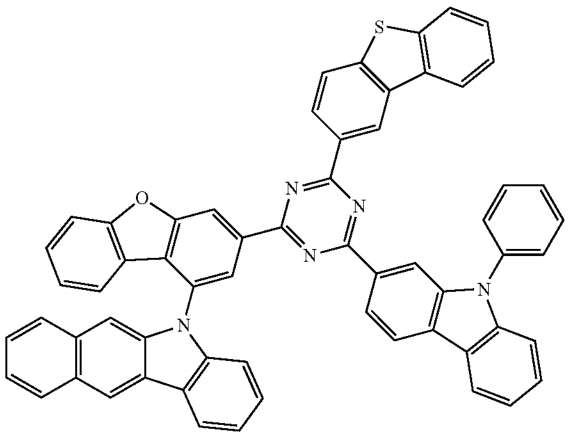
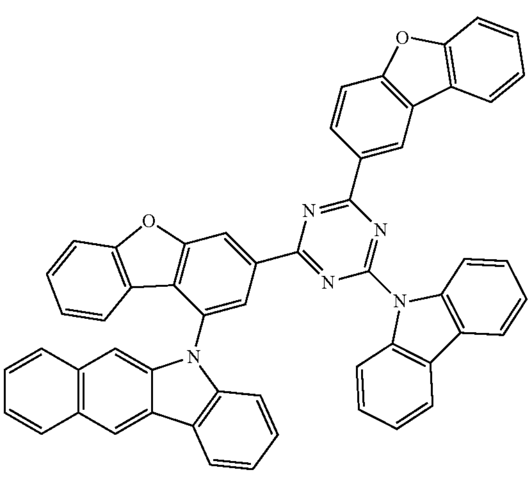
-continued
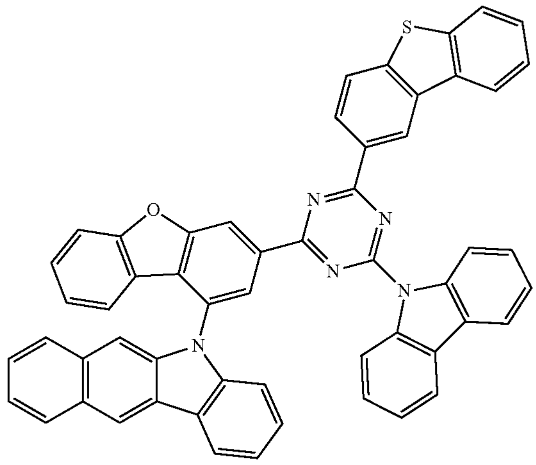
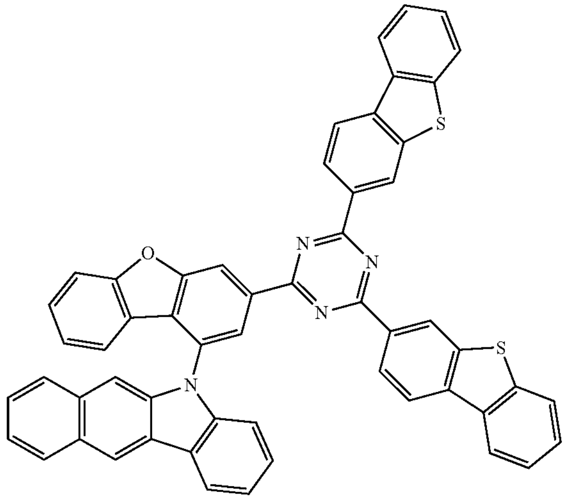
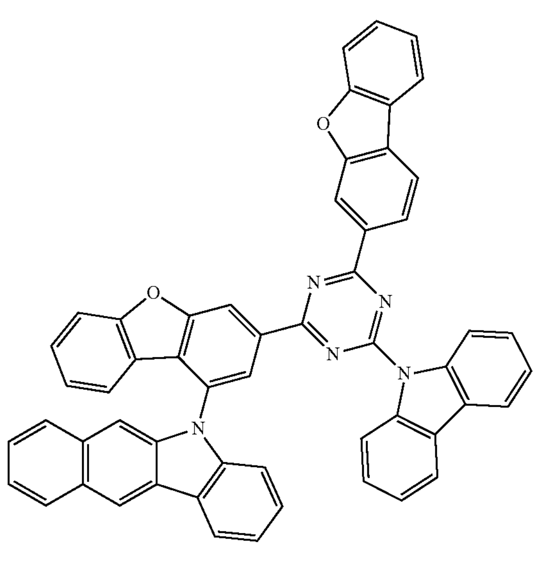

-continued
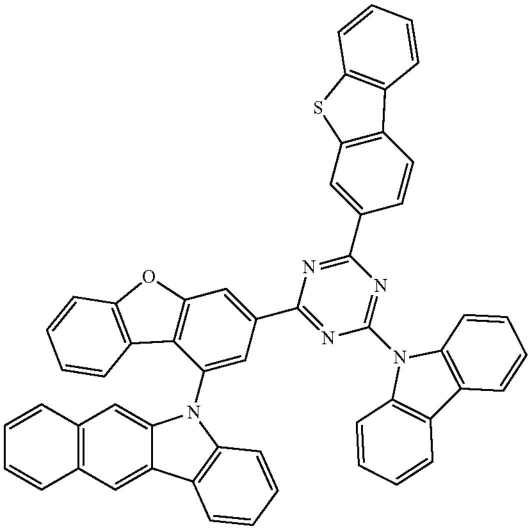
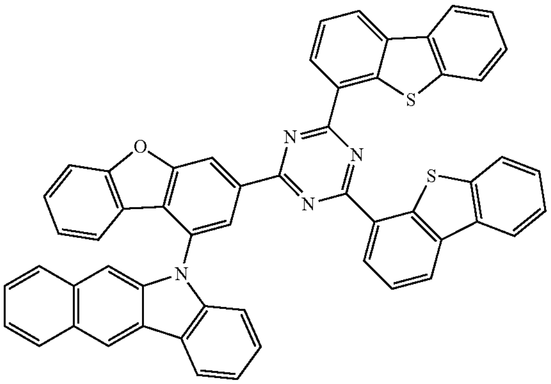
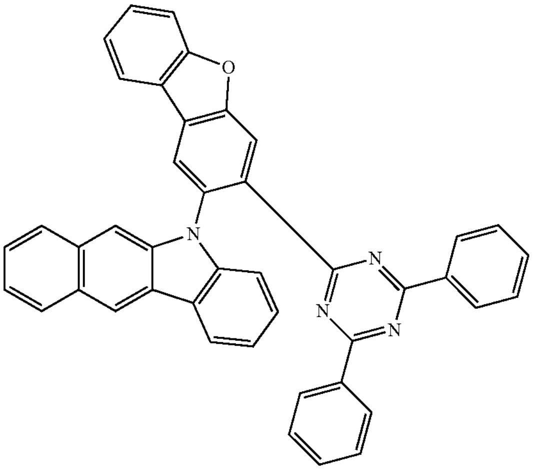
-continued
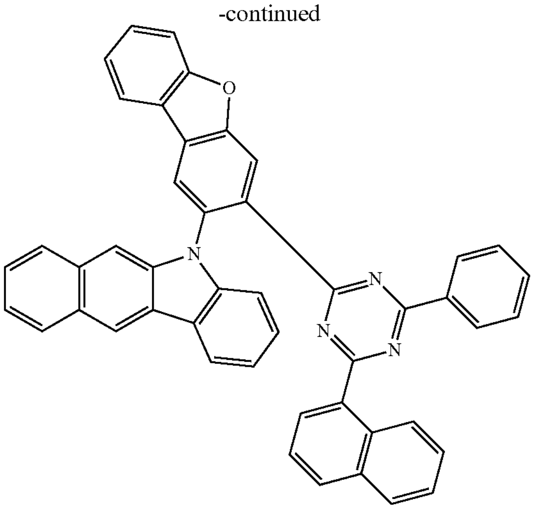
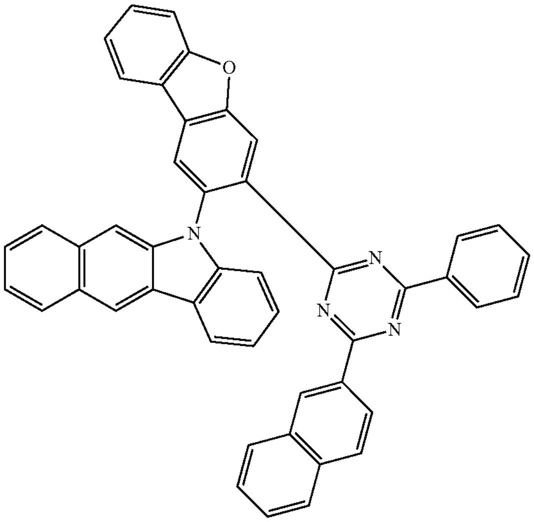
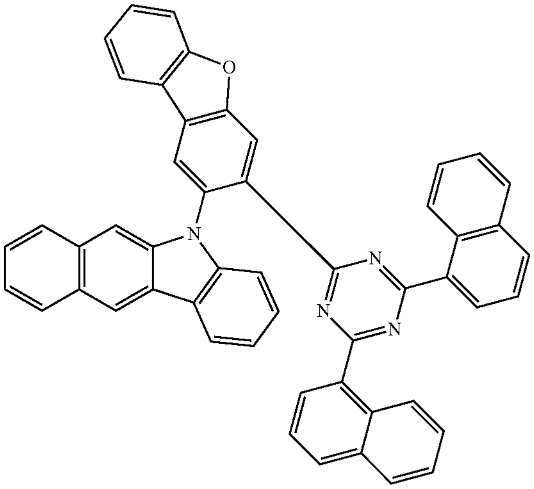

-continued
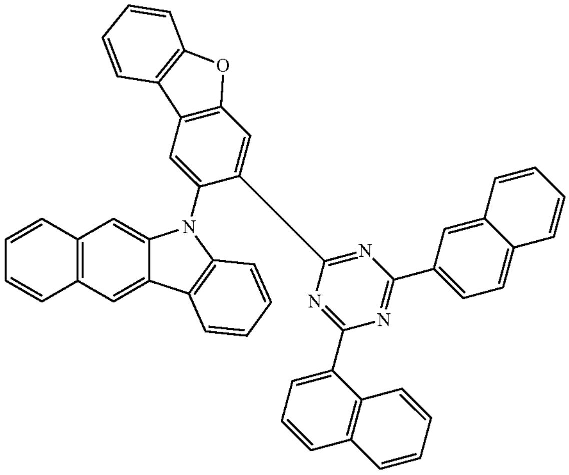
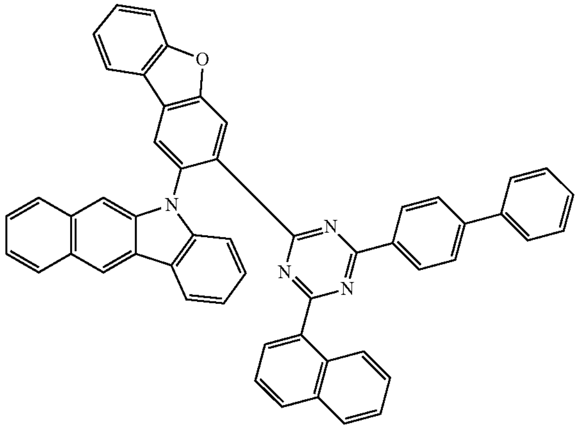
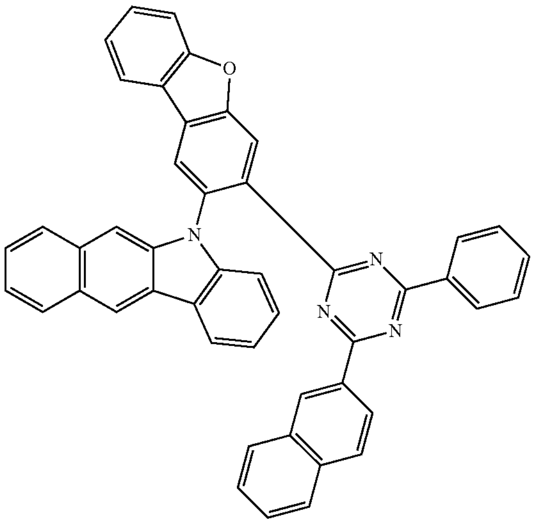
-continued
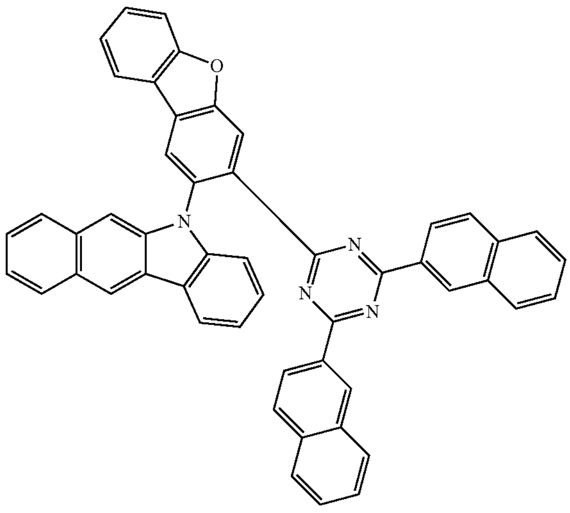
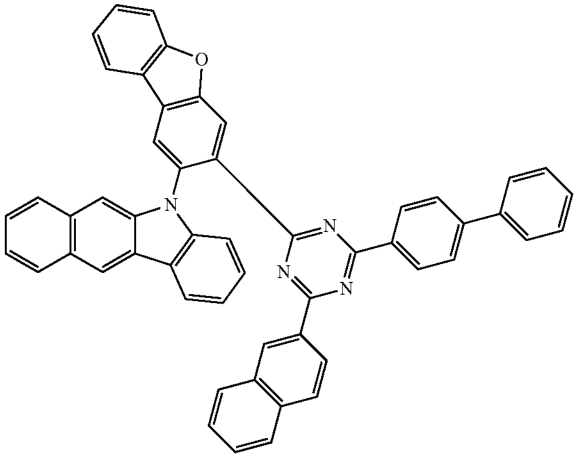
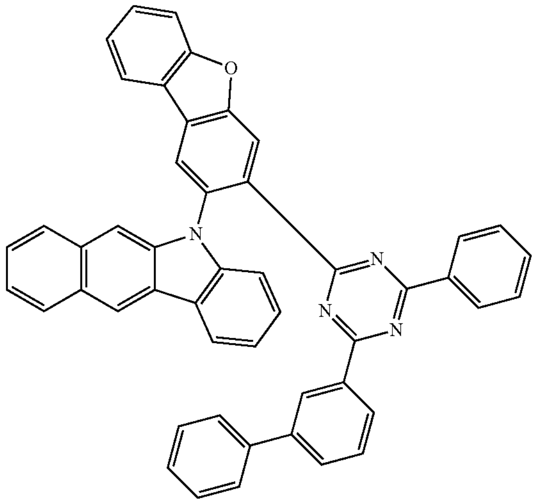

-continued
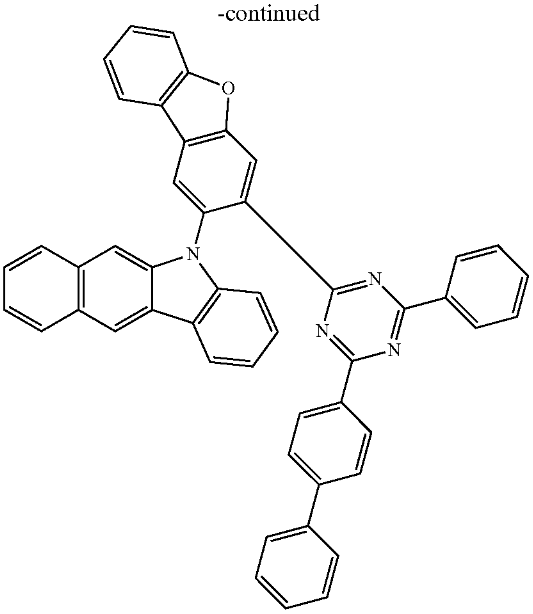
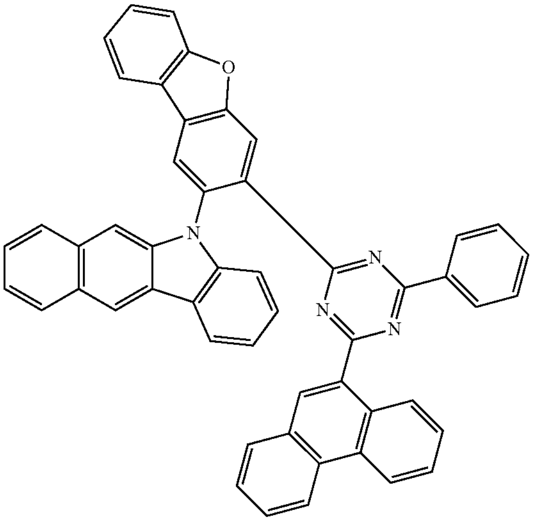
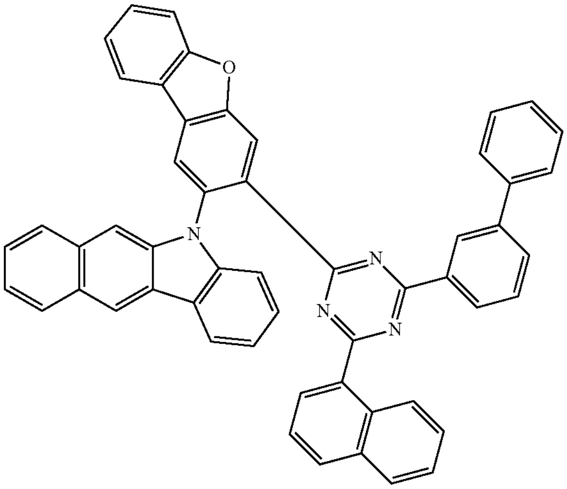
-continued
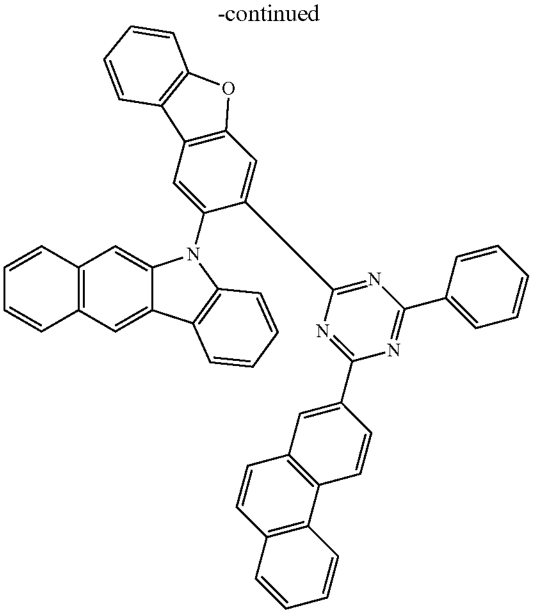
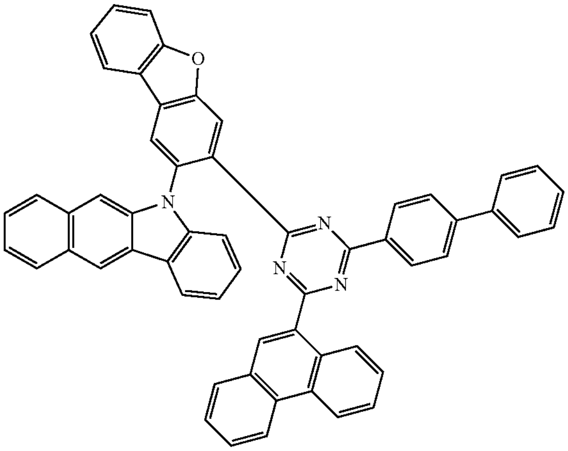
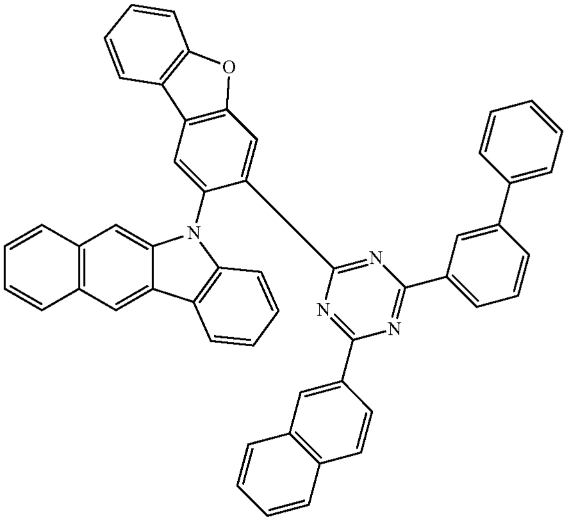

-continued
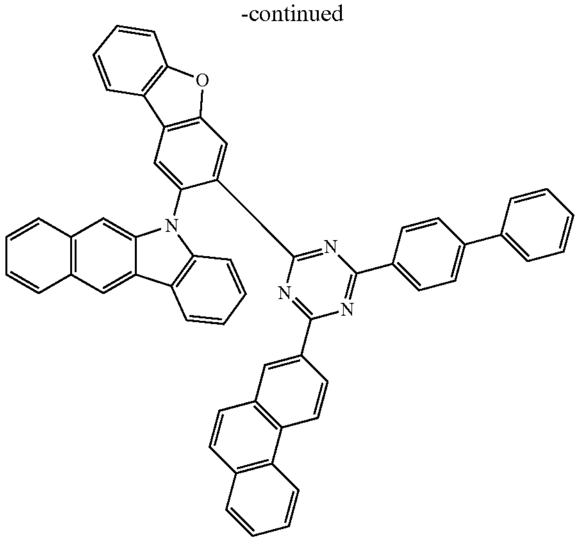
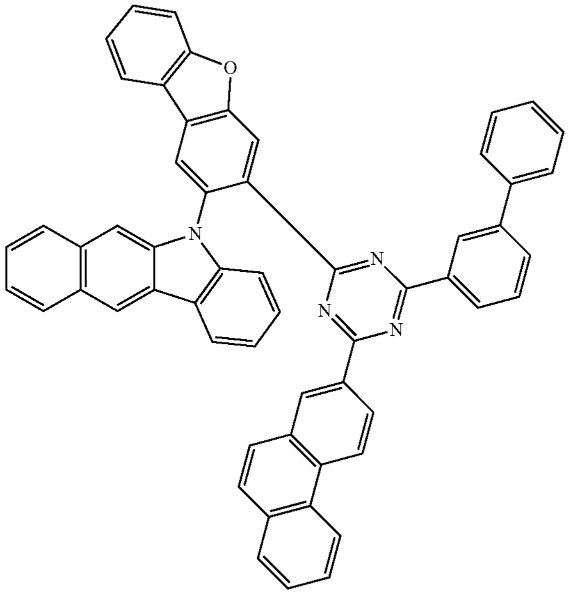
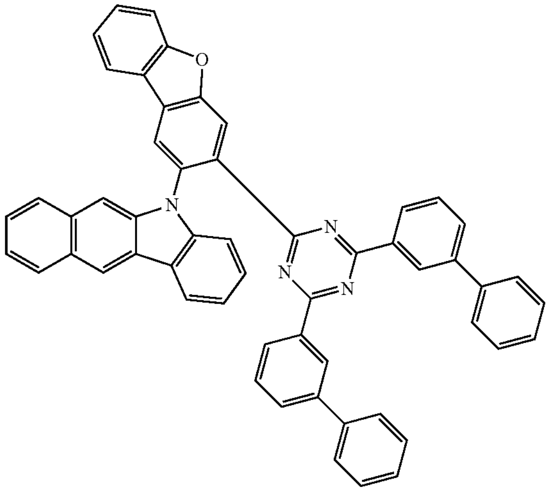
-continued
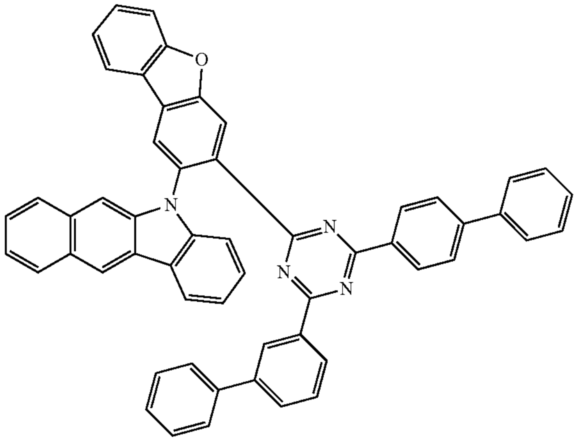
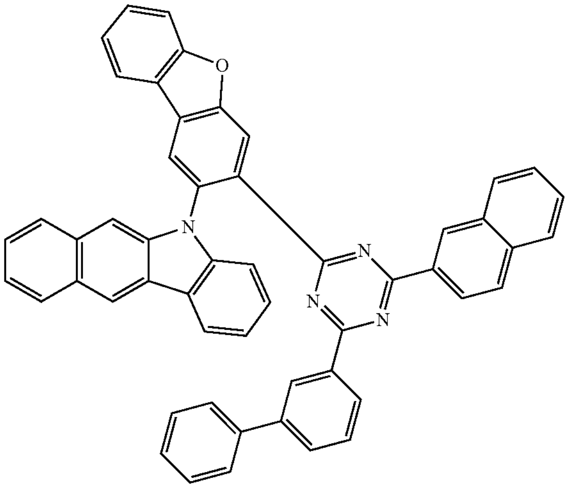
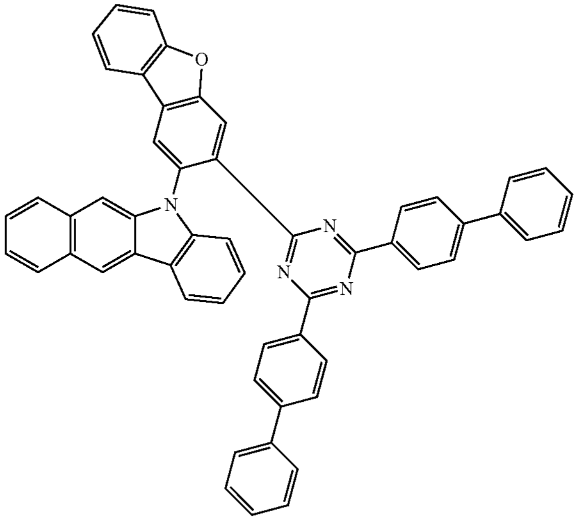

-continued
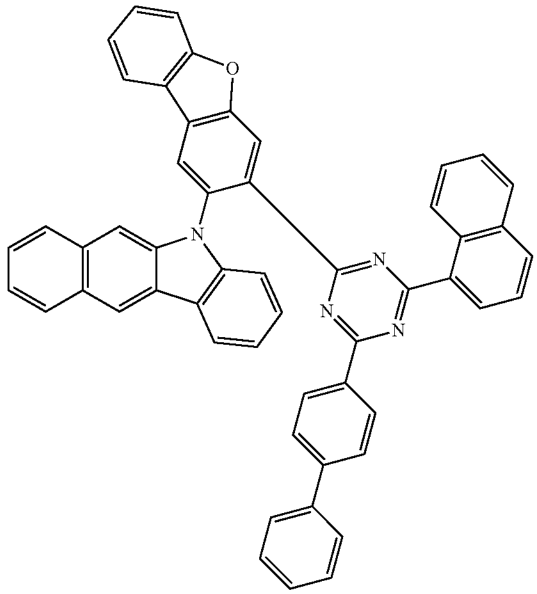
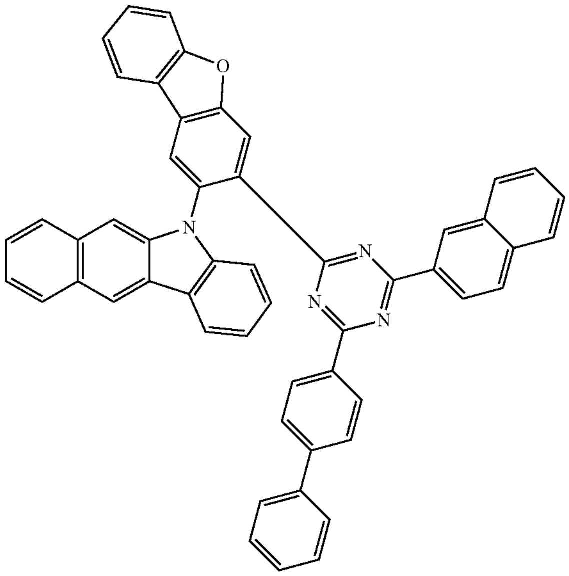
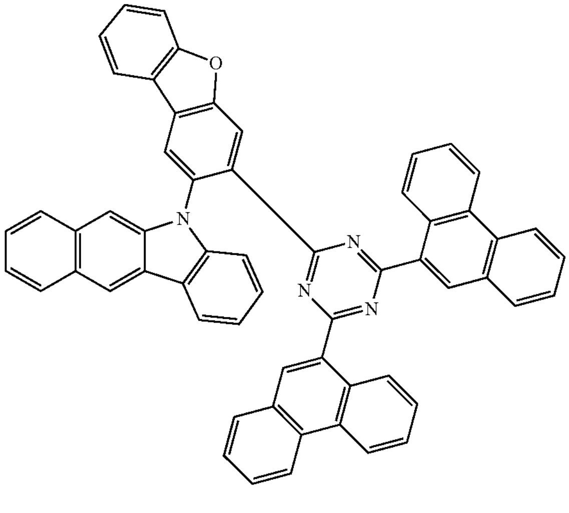
-continued
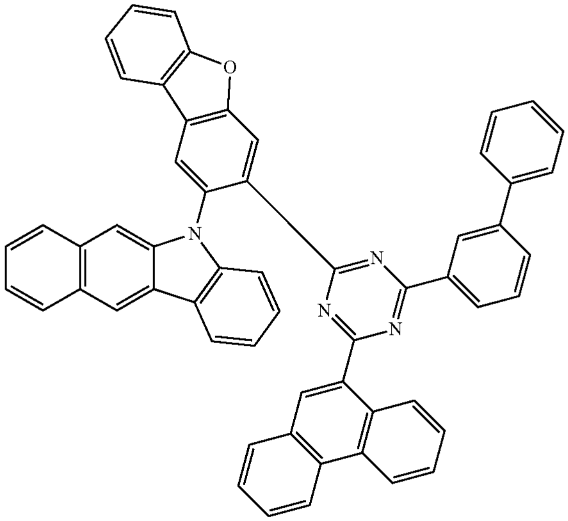
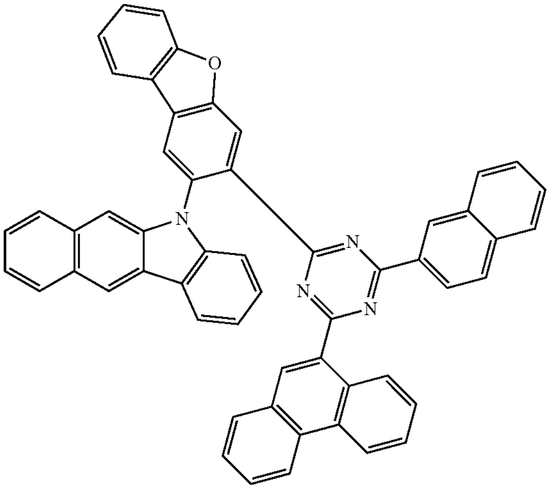
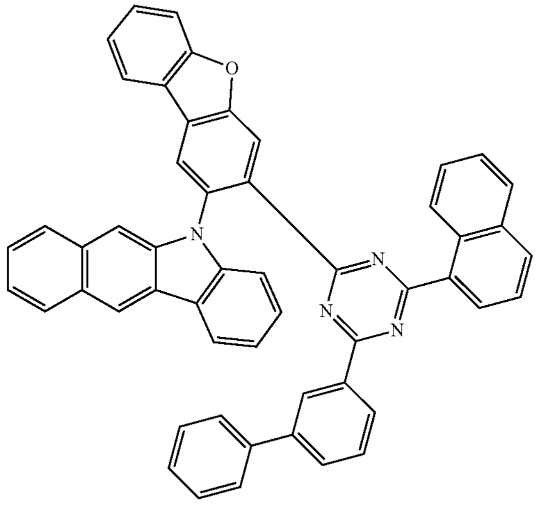

-continued
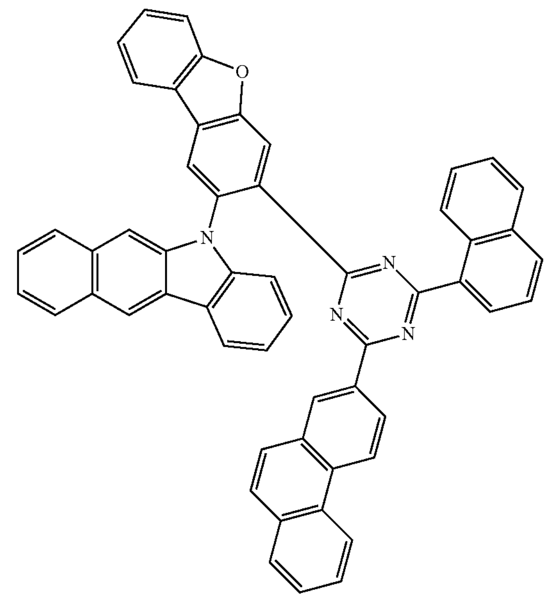
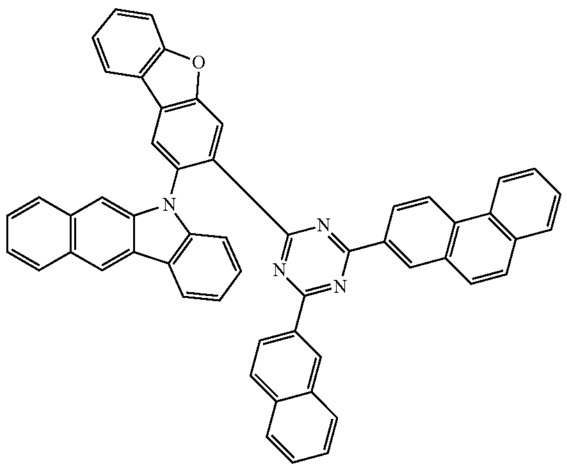
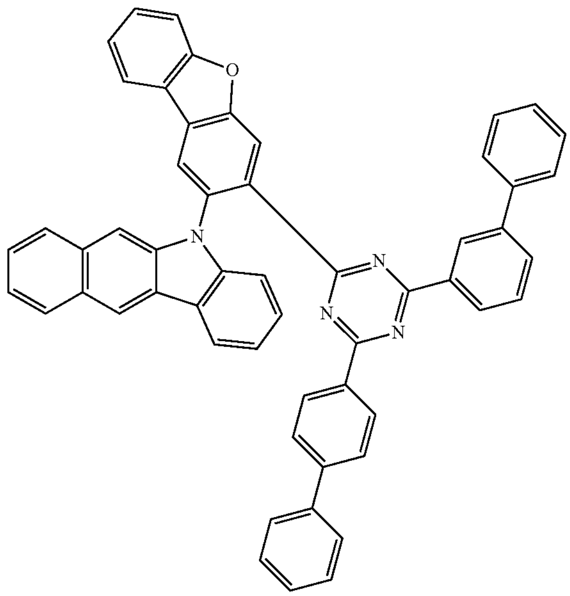
-continued
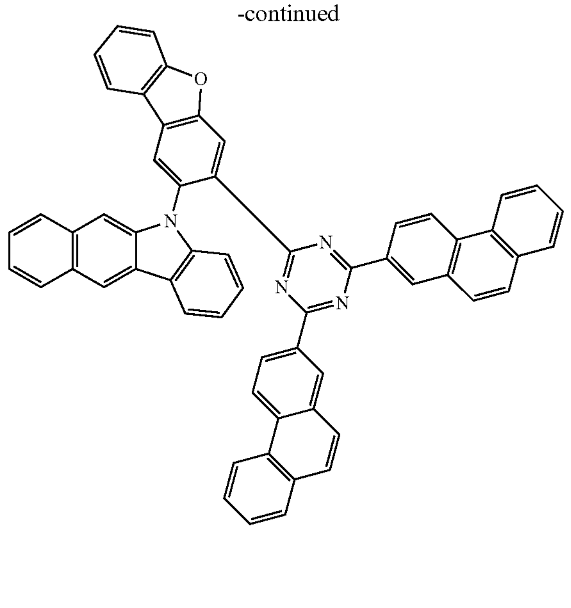
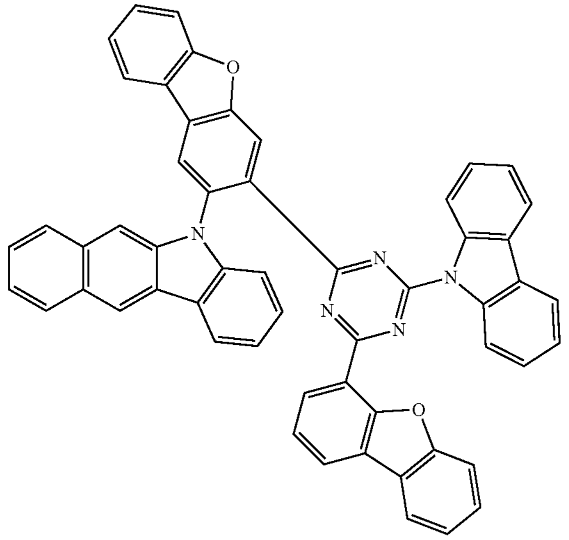
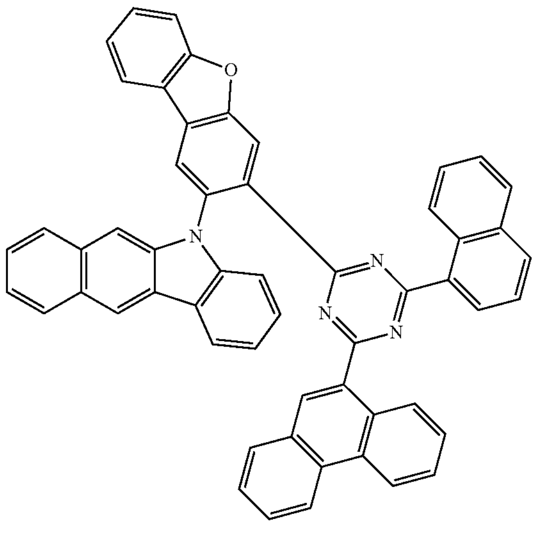

-continued
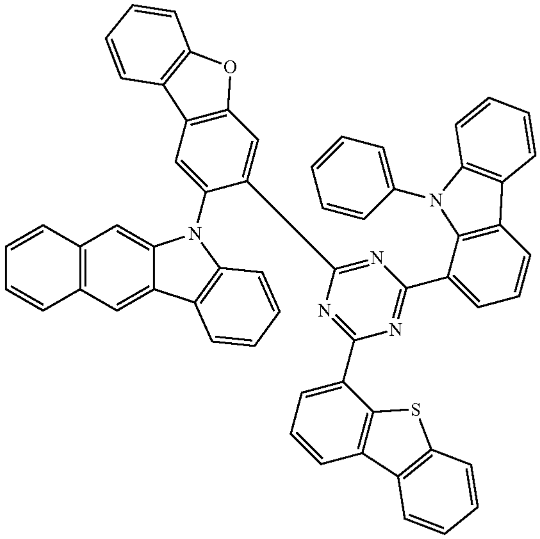
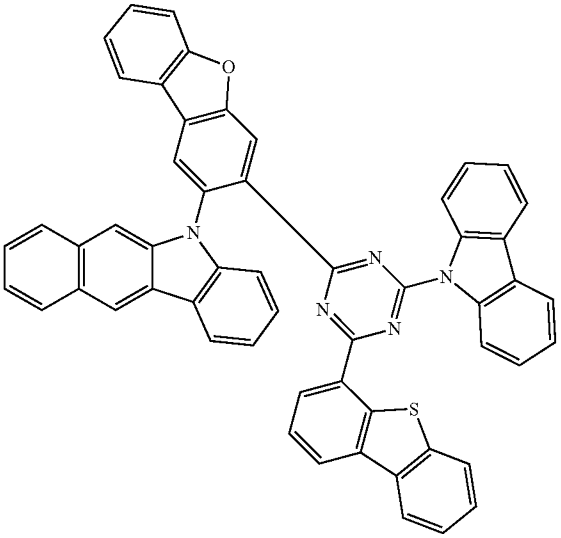
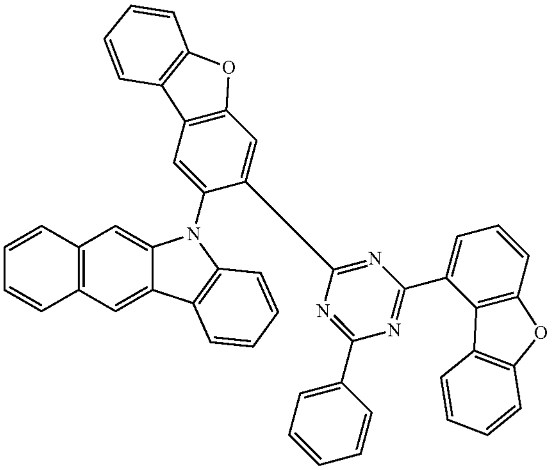
-continued
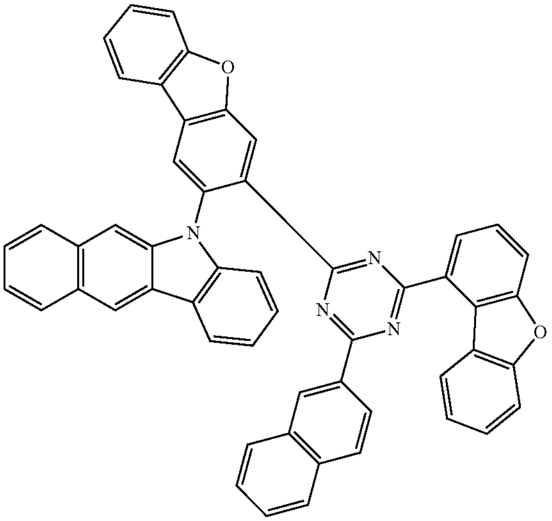
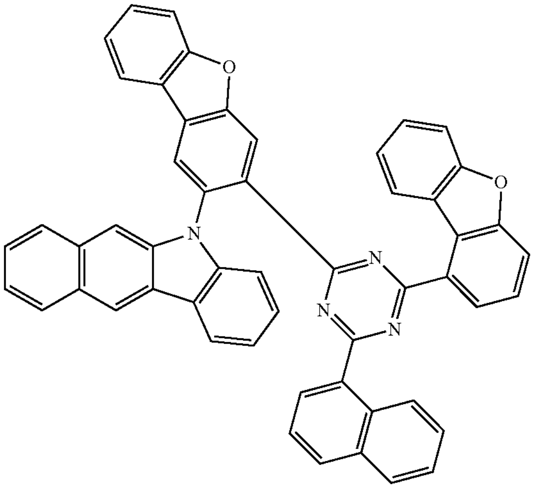
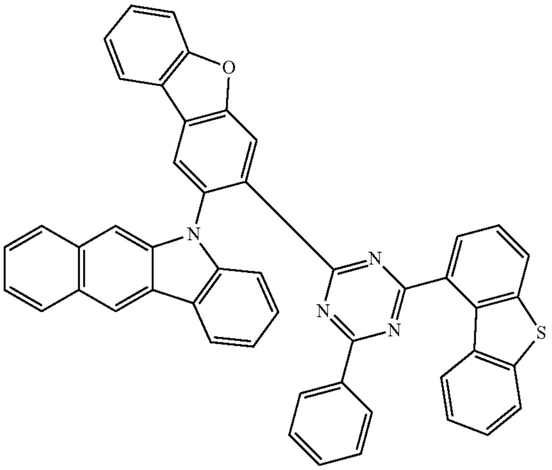

-continued
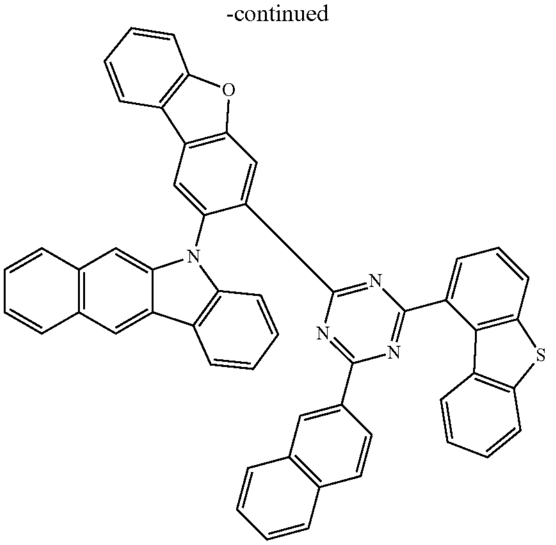
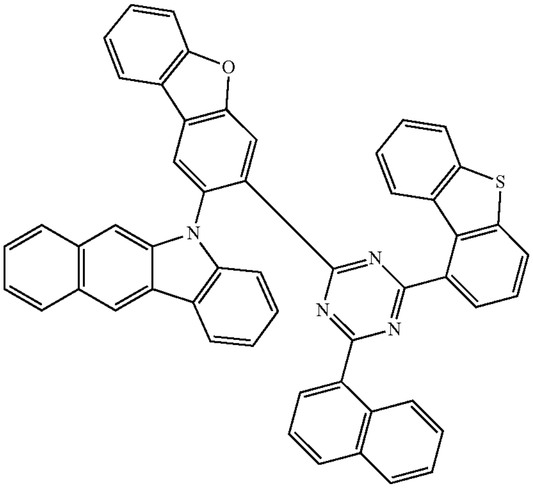
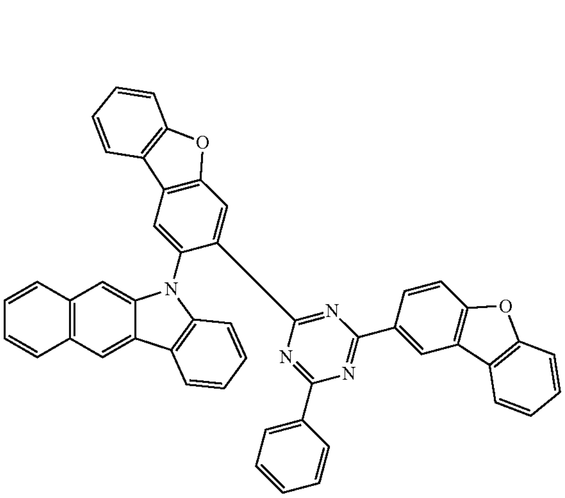
-continued
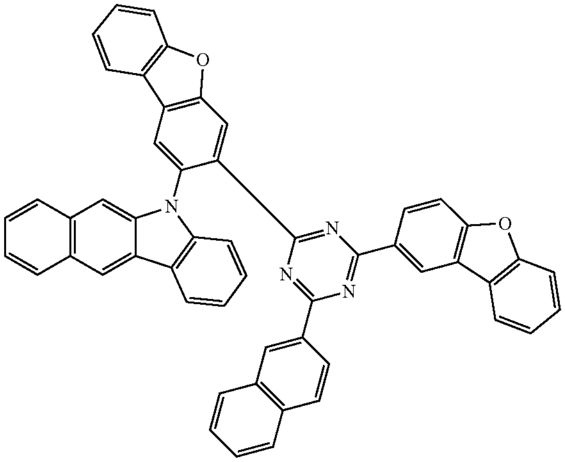
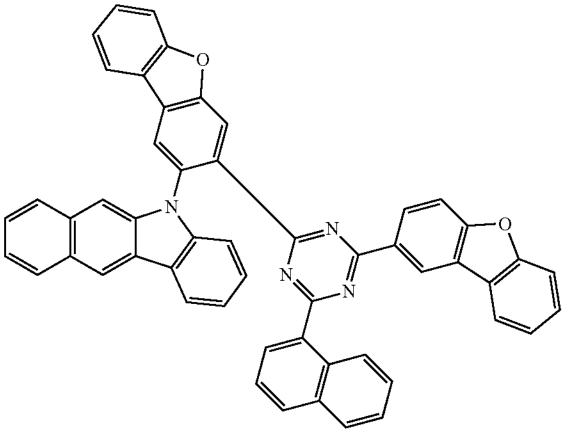
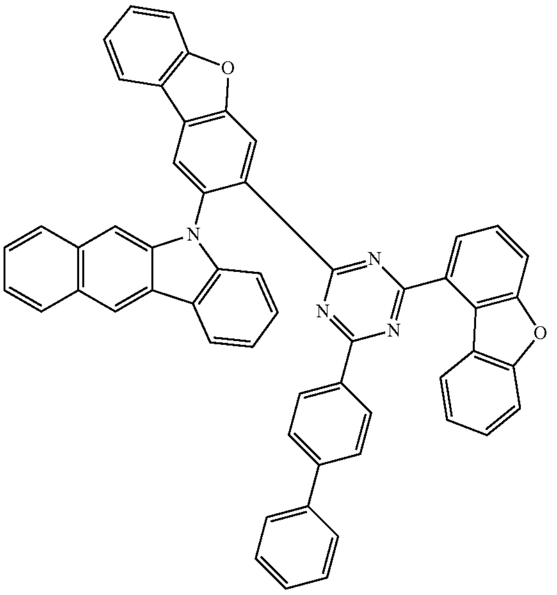

-continued
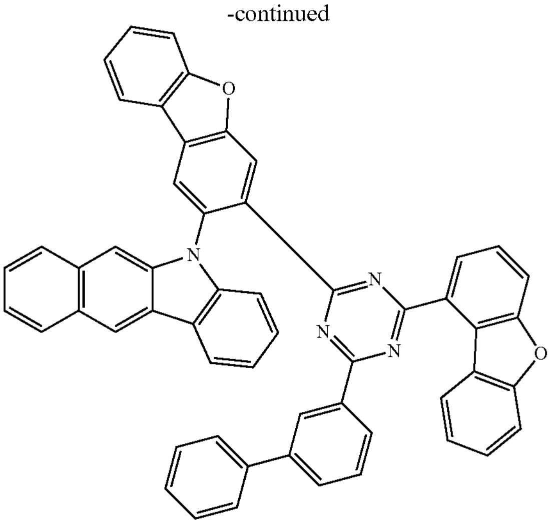
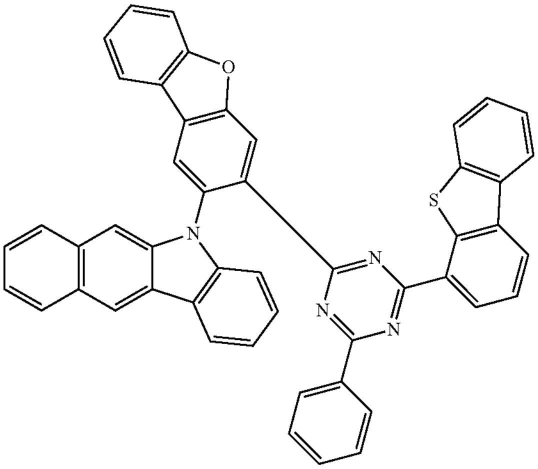
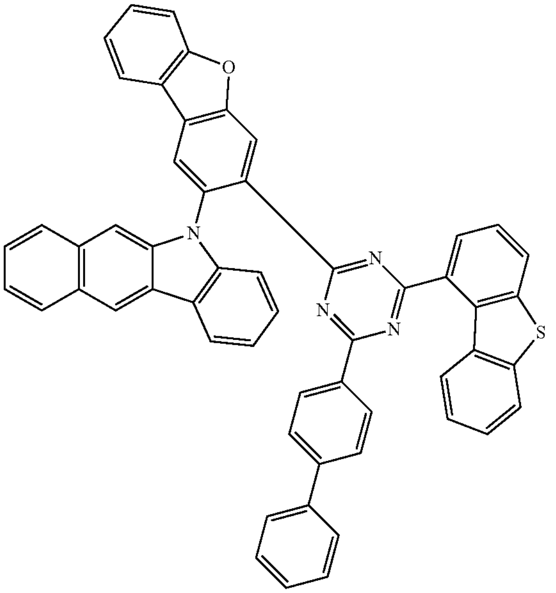
-continued
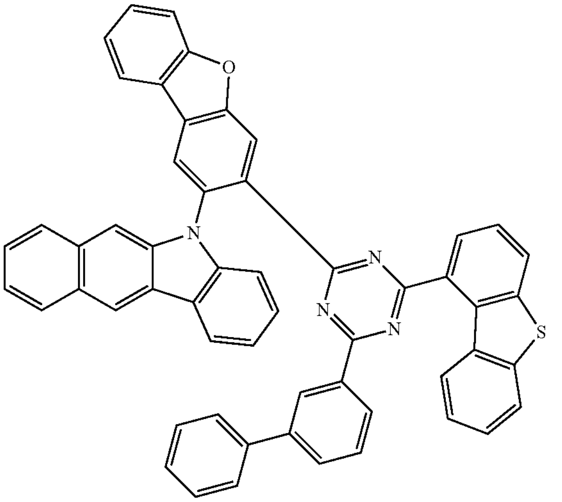
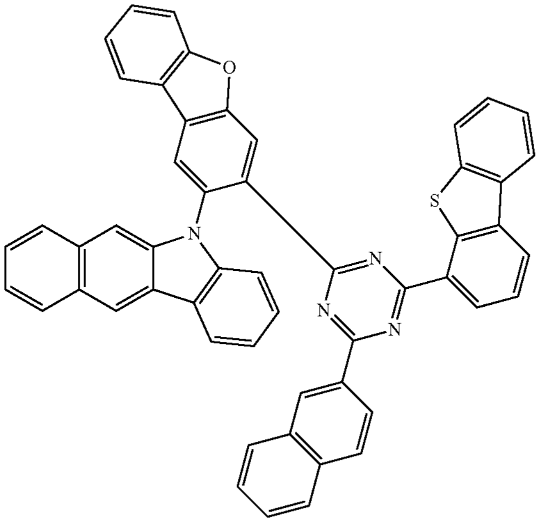
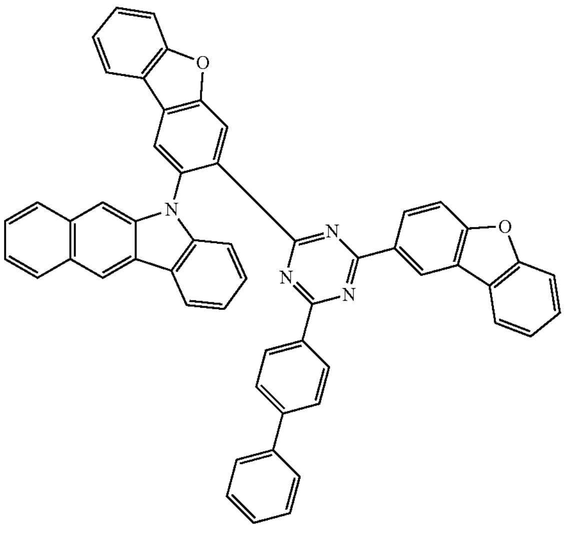

-continued
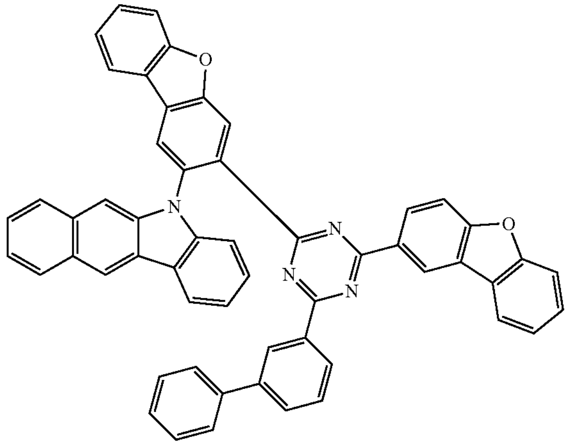
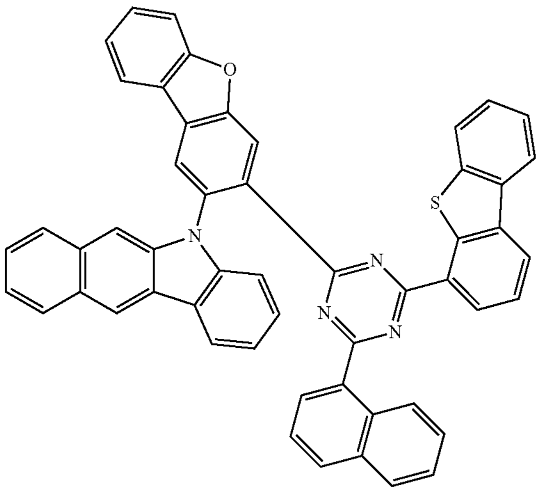
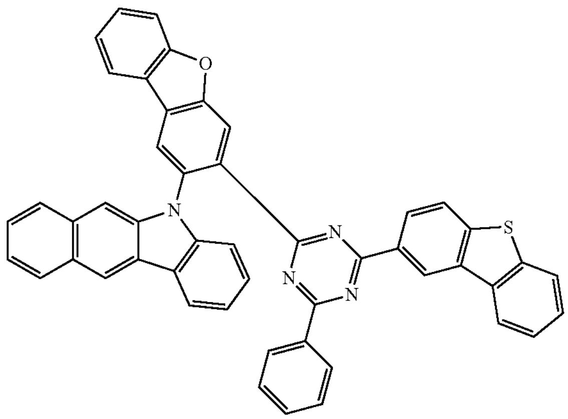
-continued
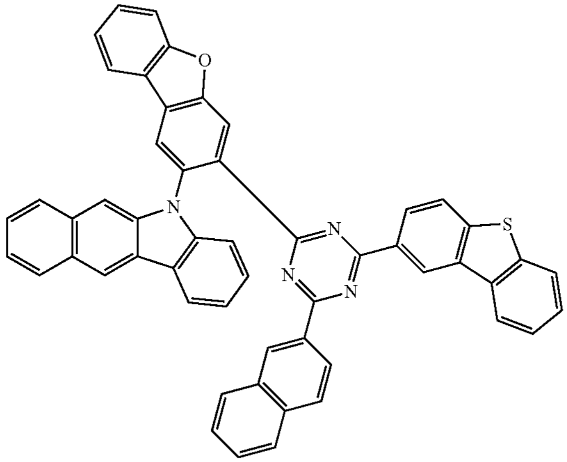
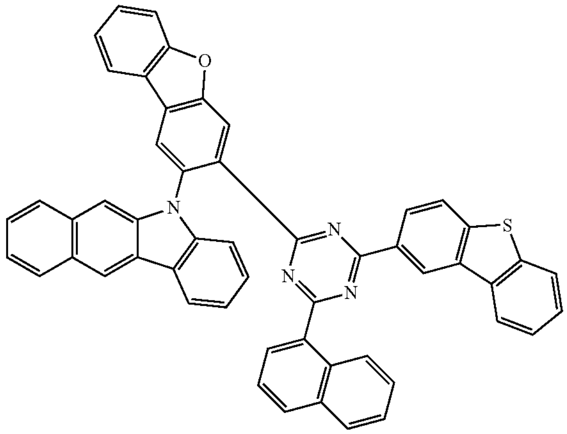
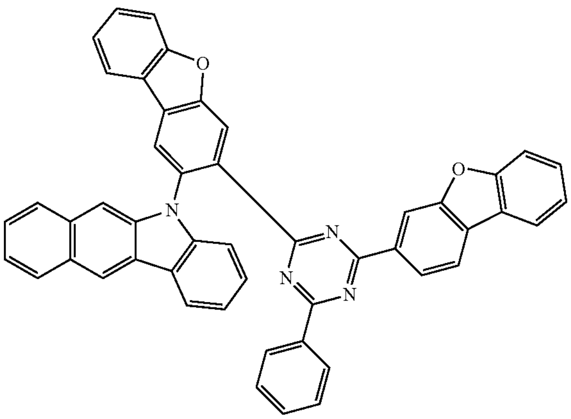

-continued
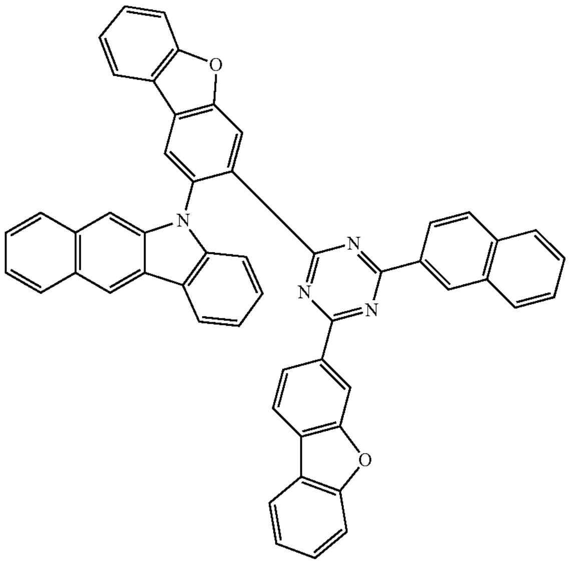
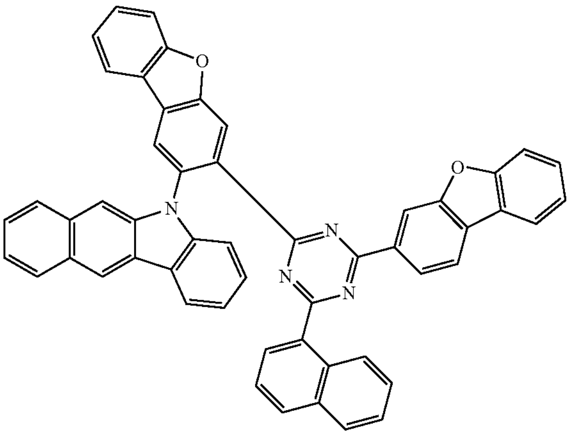
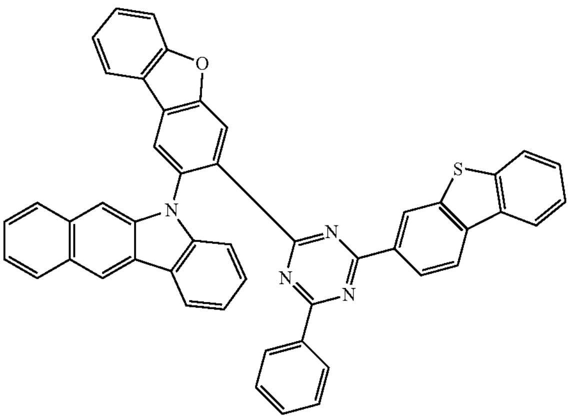
-continued
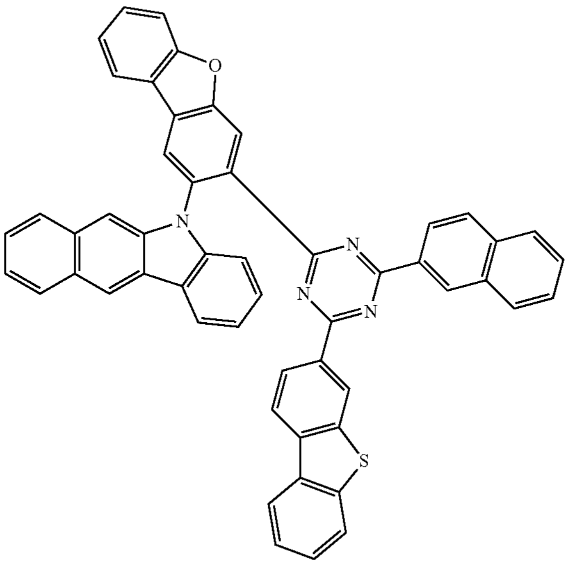
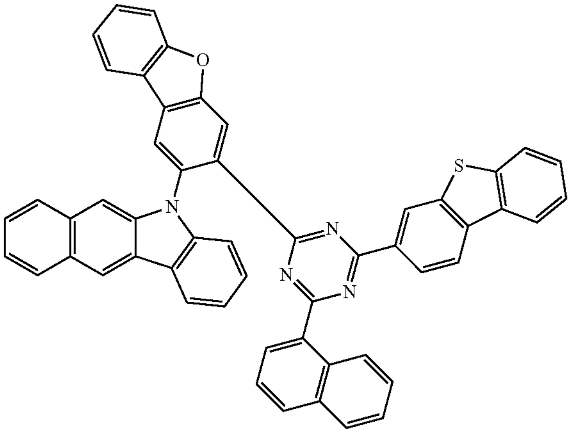
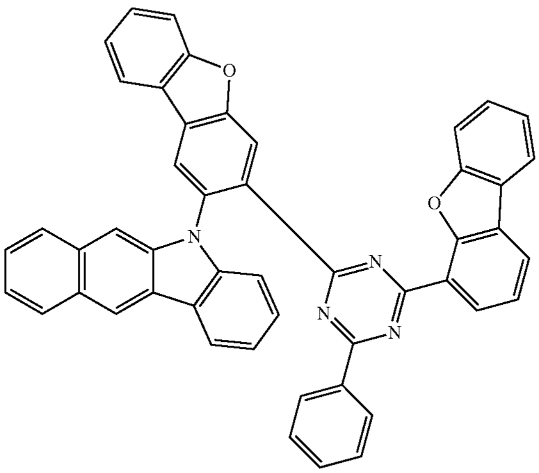

-continued
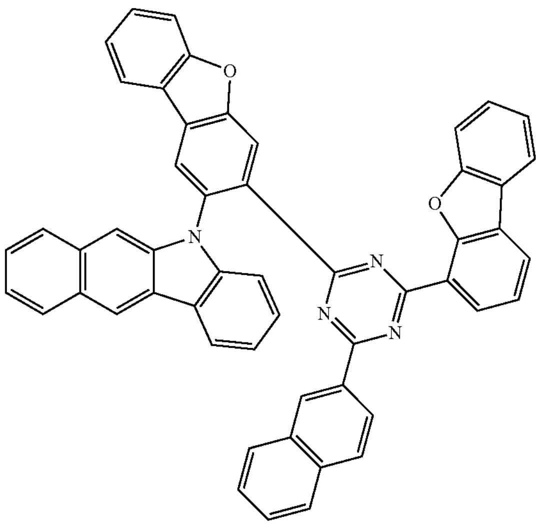
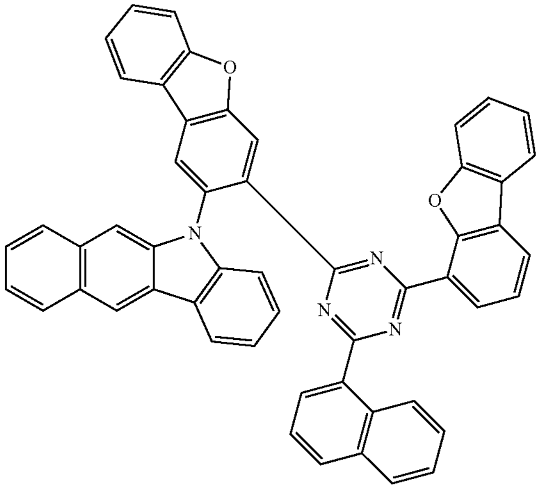
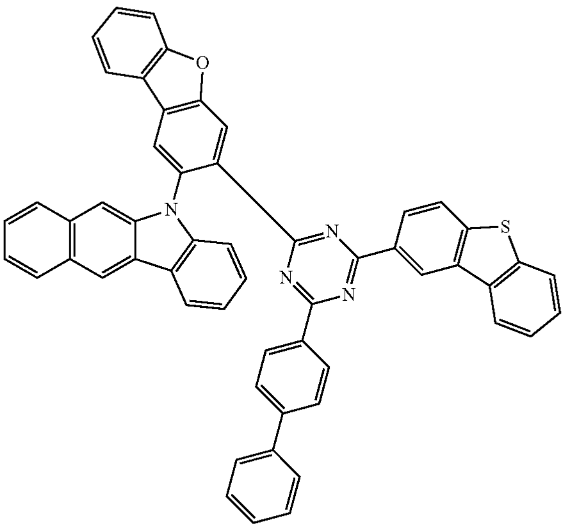
-continued
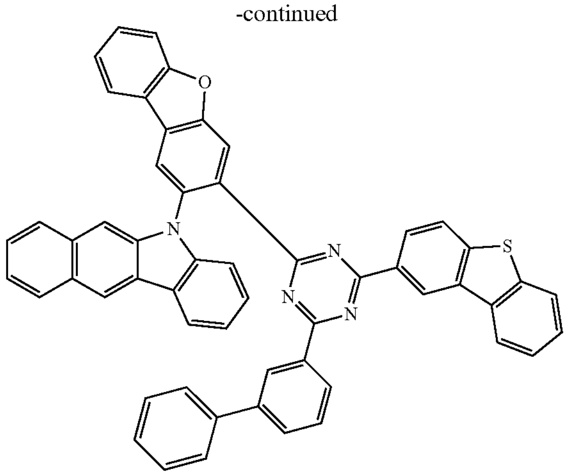
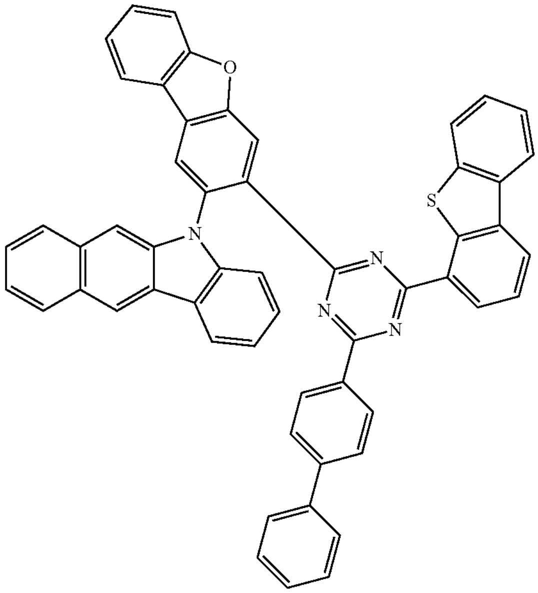
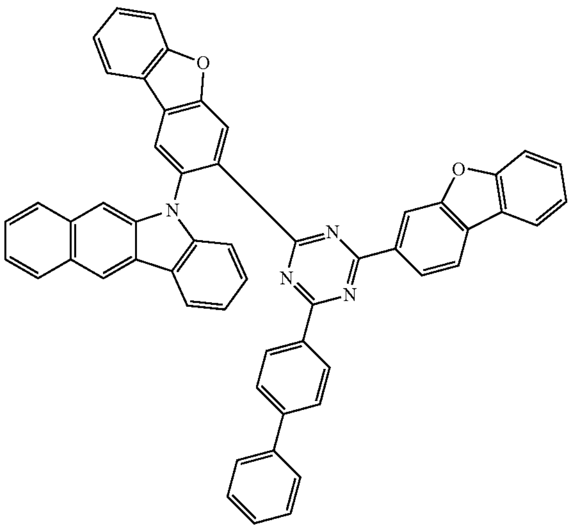

-continued
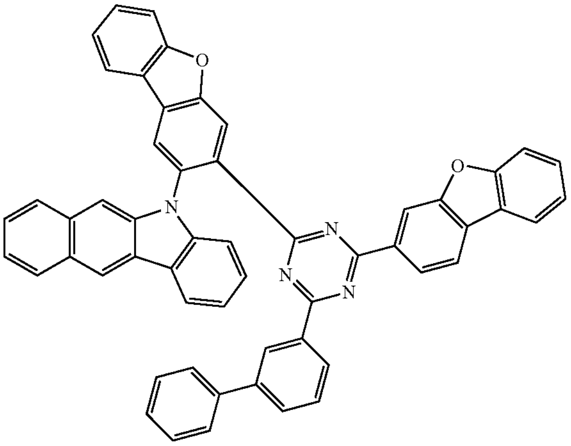
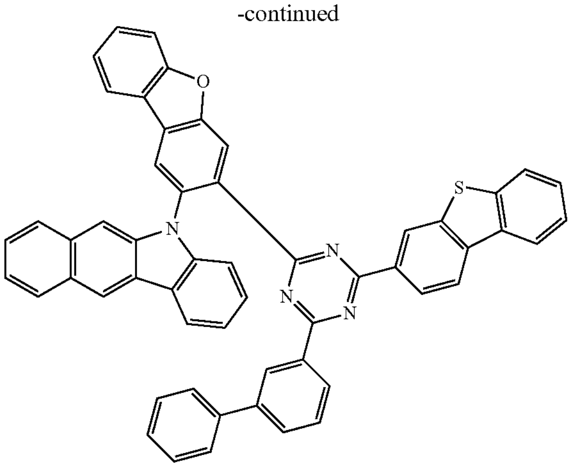
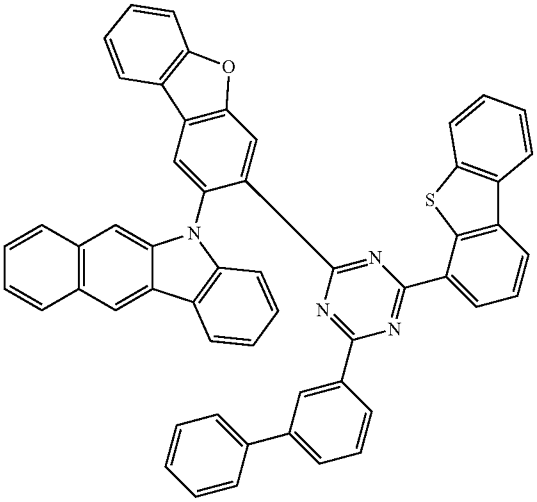
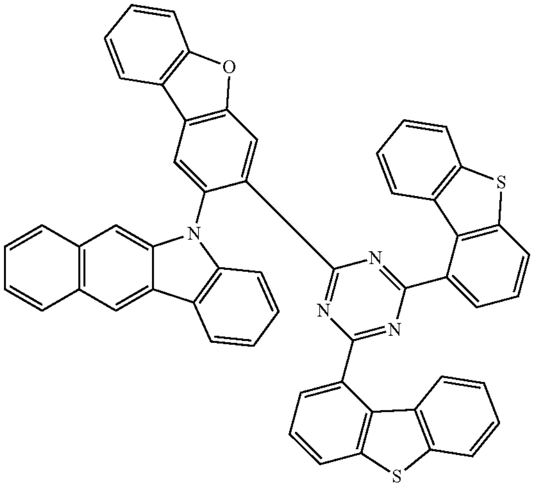
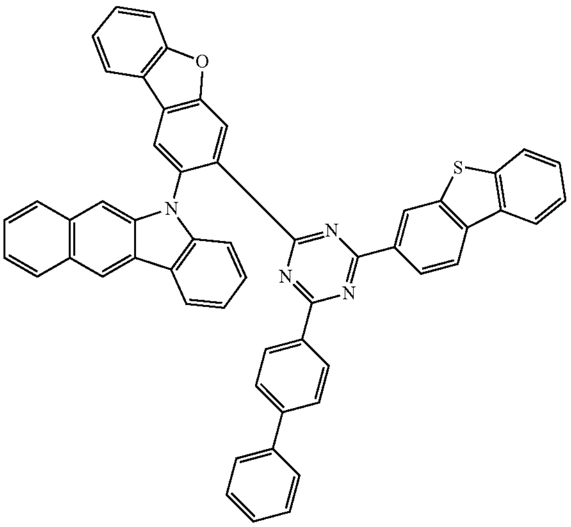
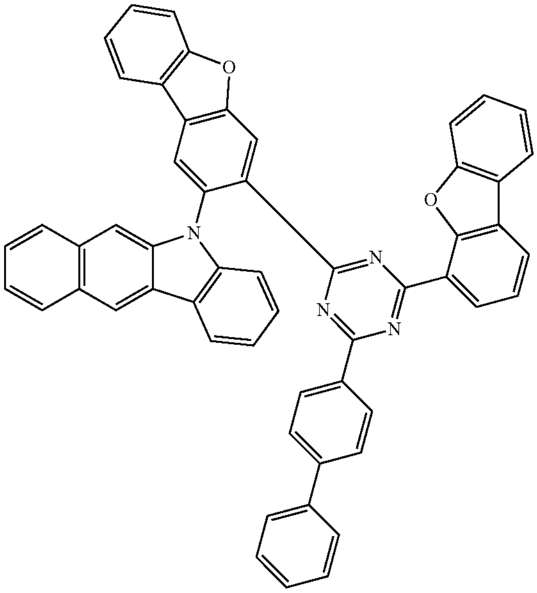
-continued

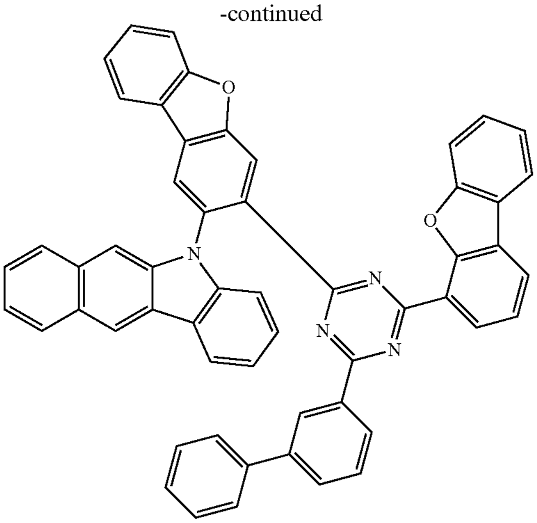
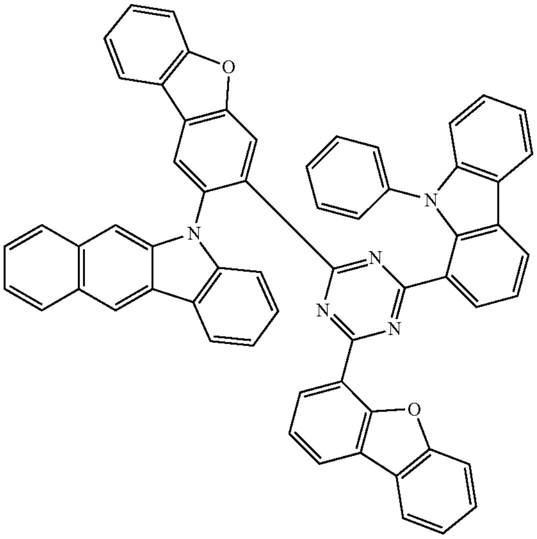
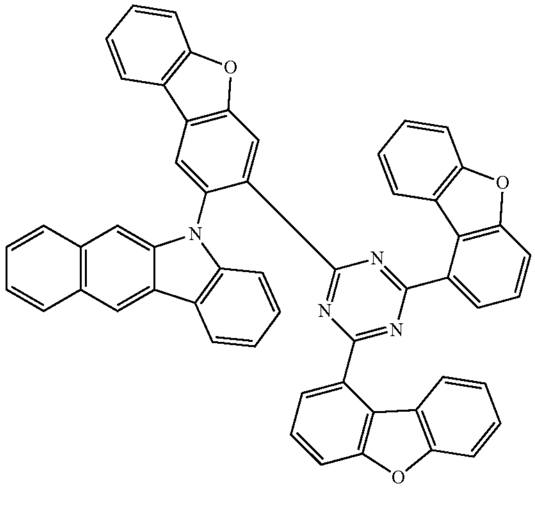
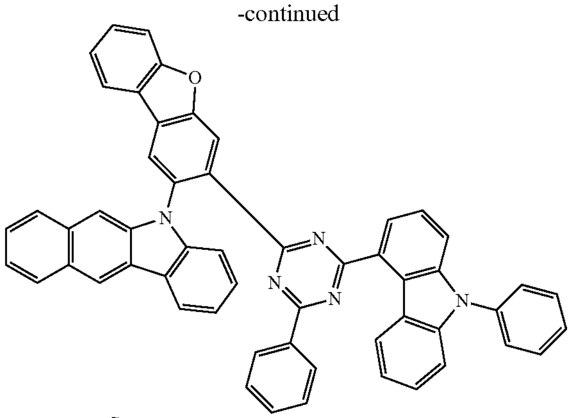
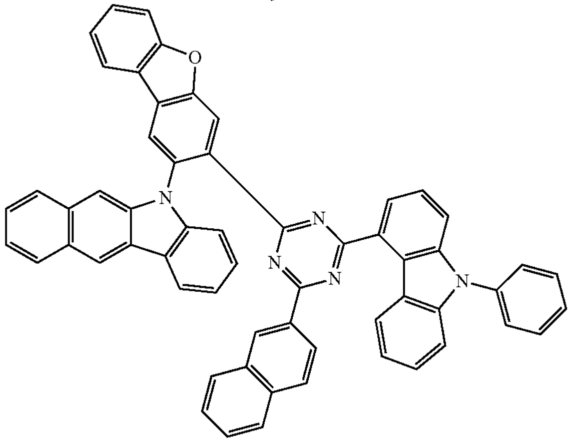
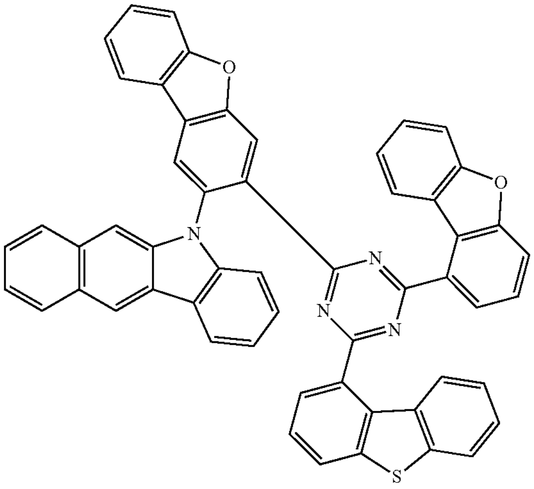
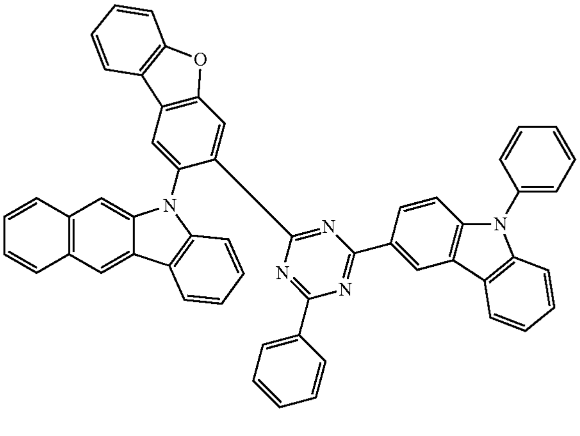

-continued
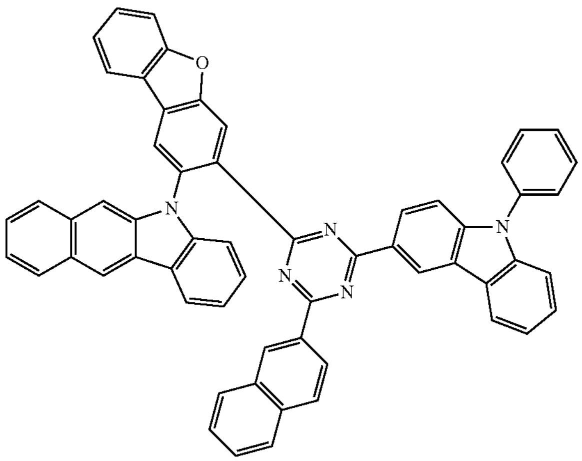
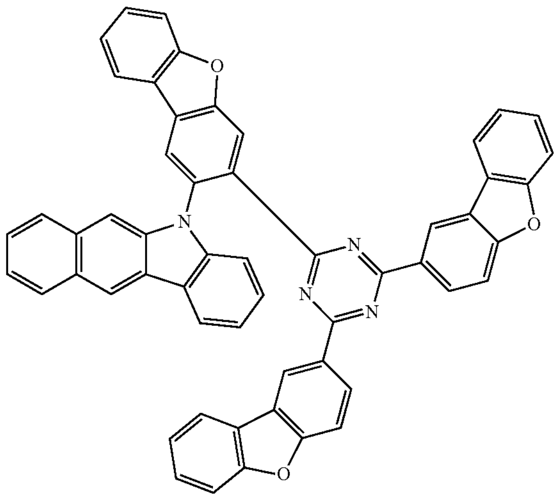
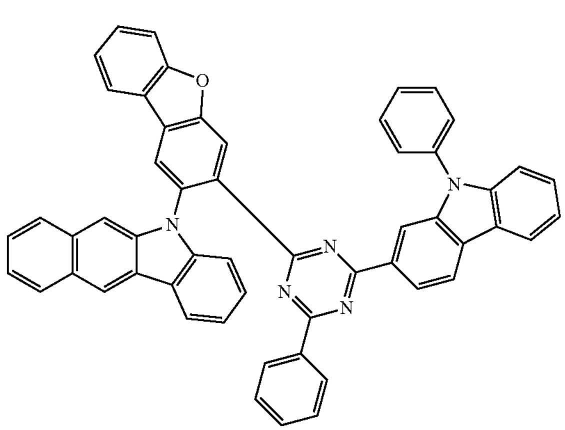
-continued
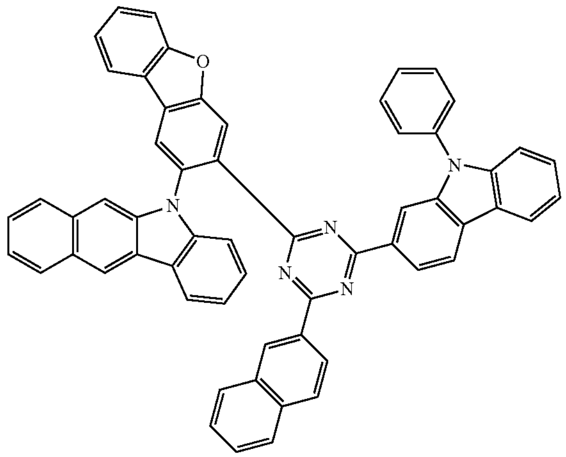
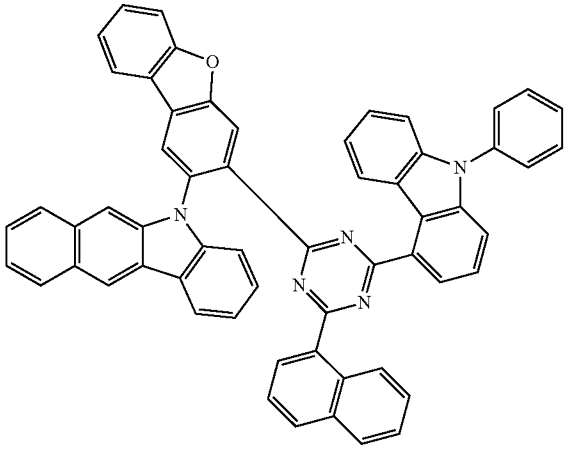
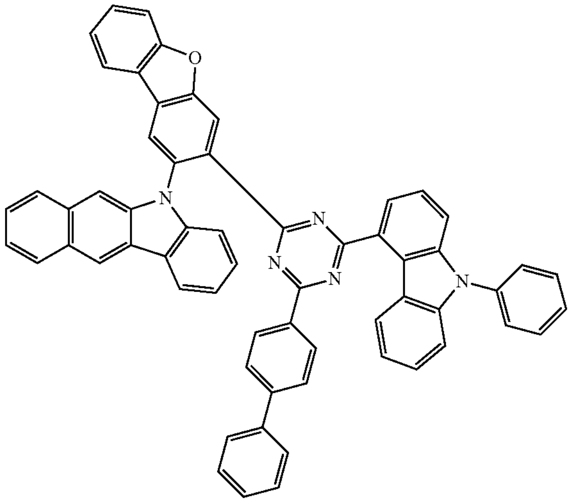

-continued
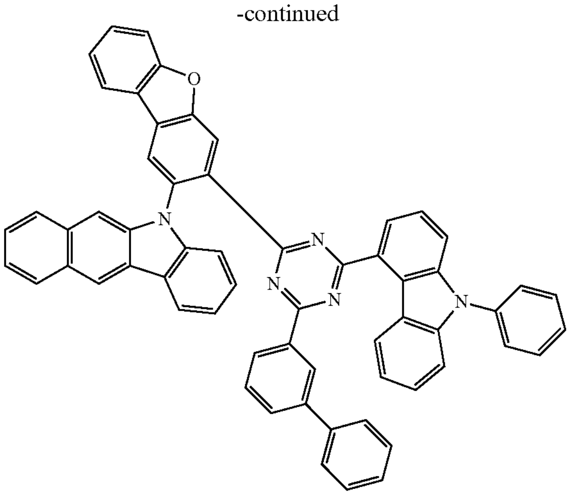
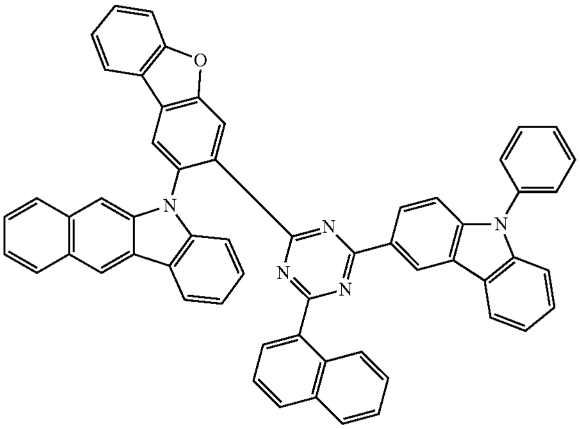
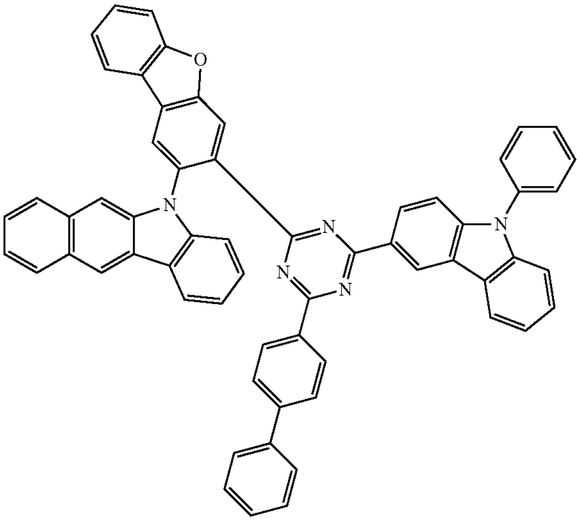
-continued
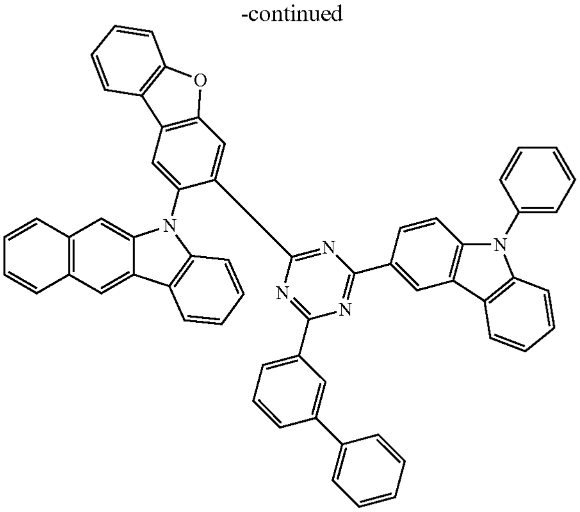
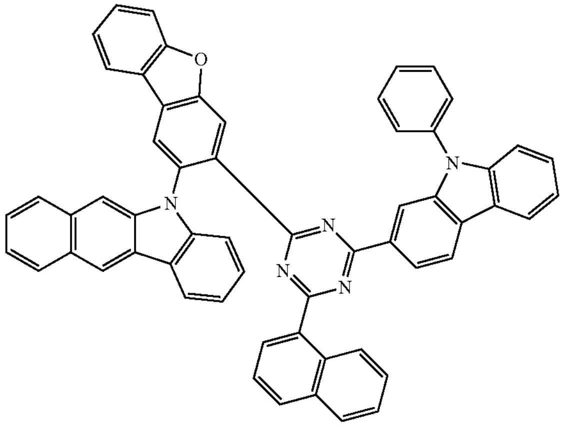
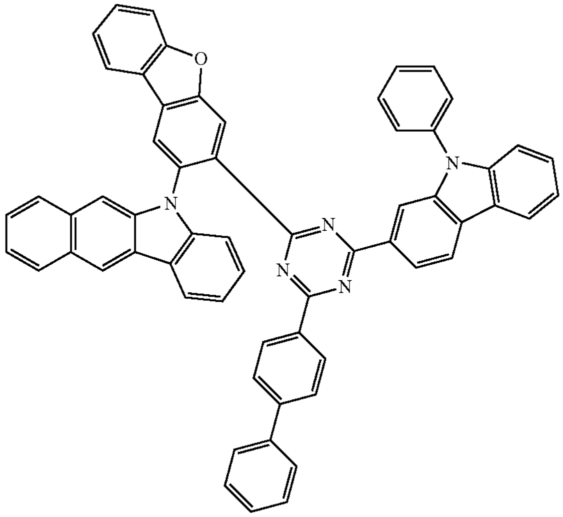

-continued
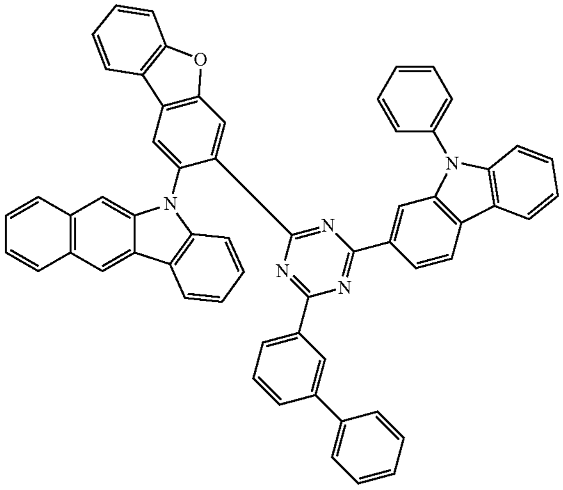
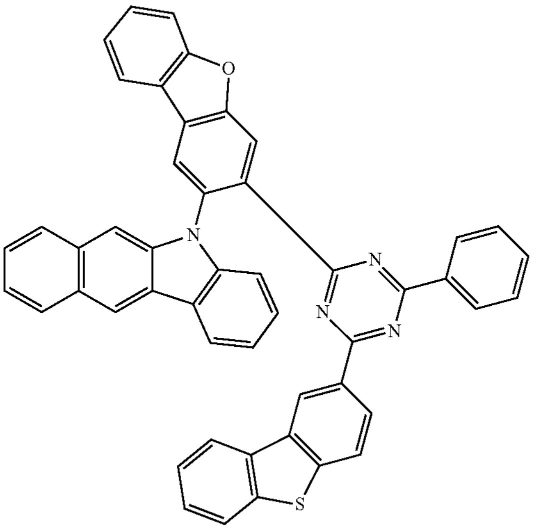
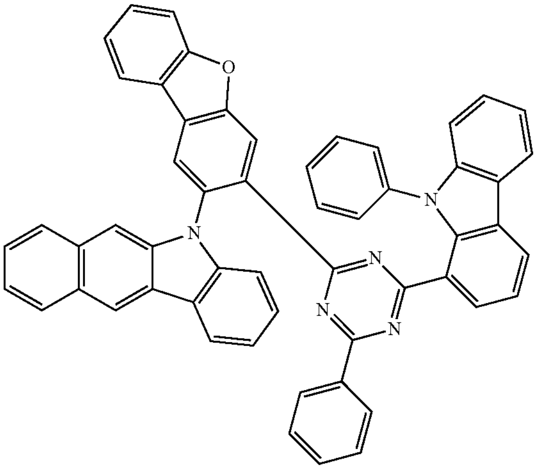
-continued
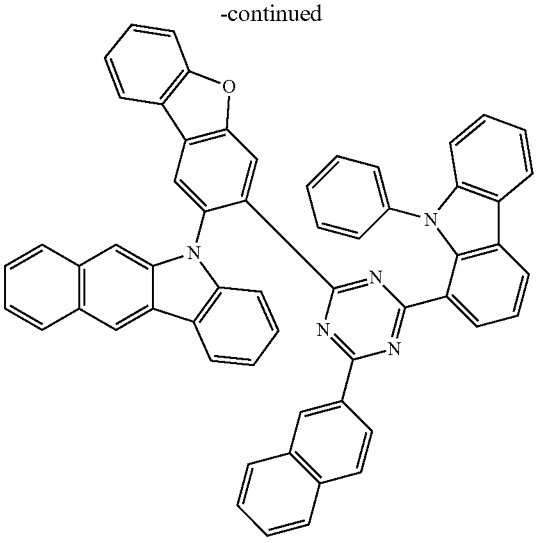
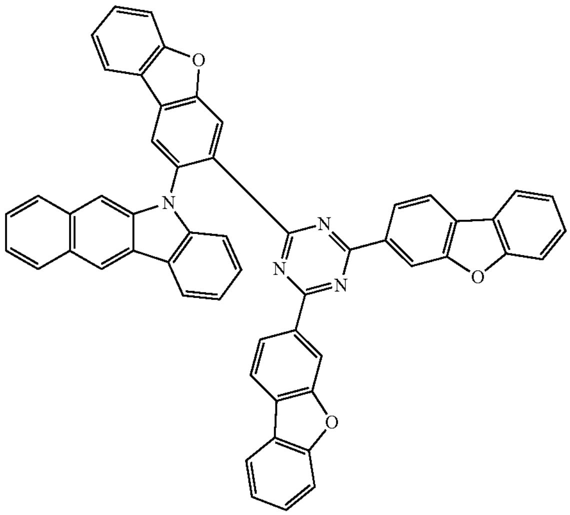
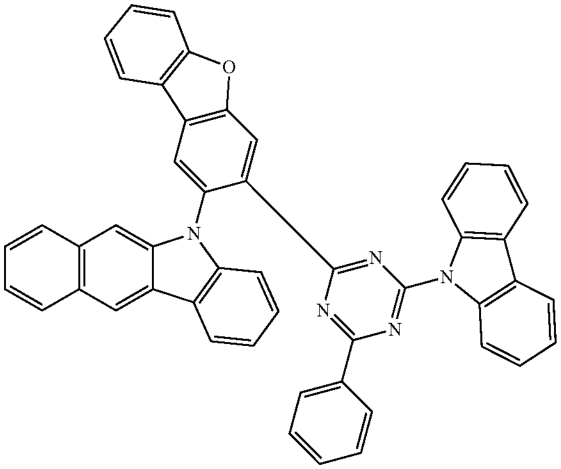

-continued
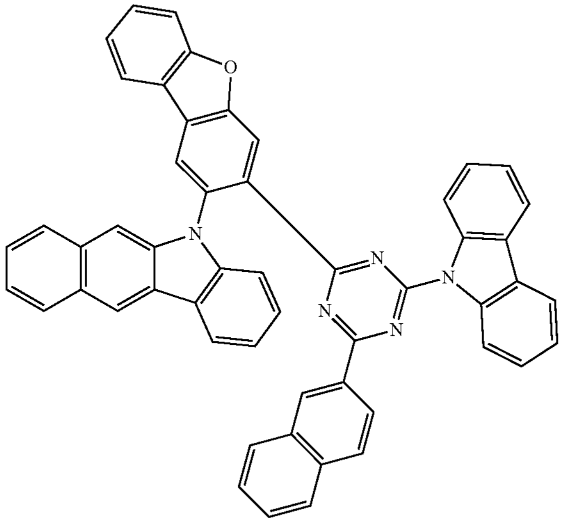
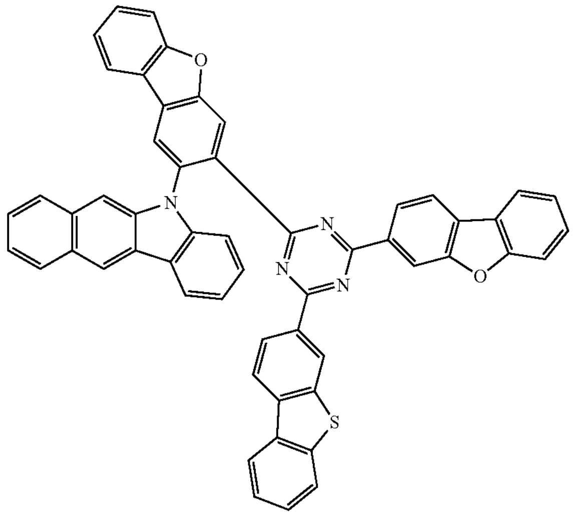
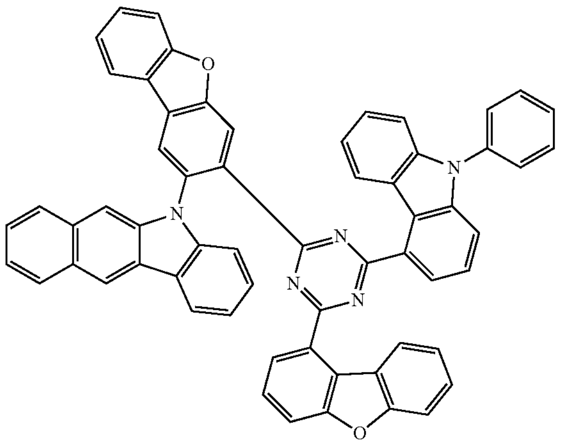
-continued
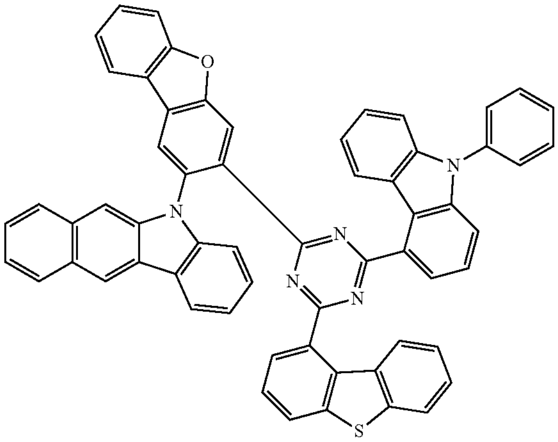
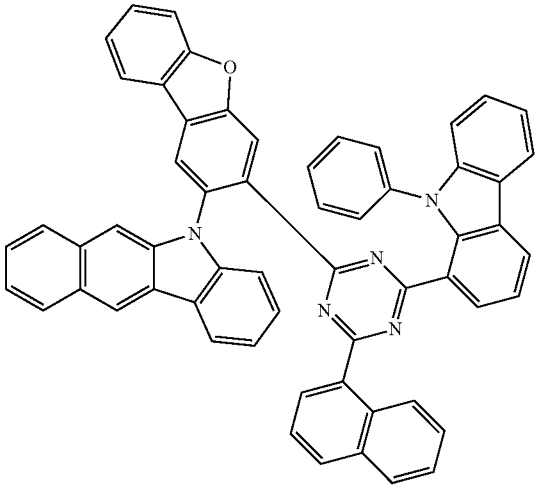
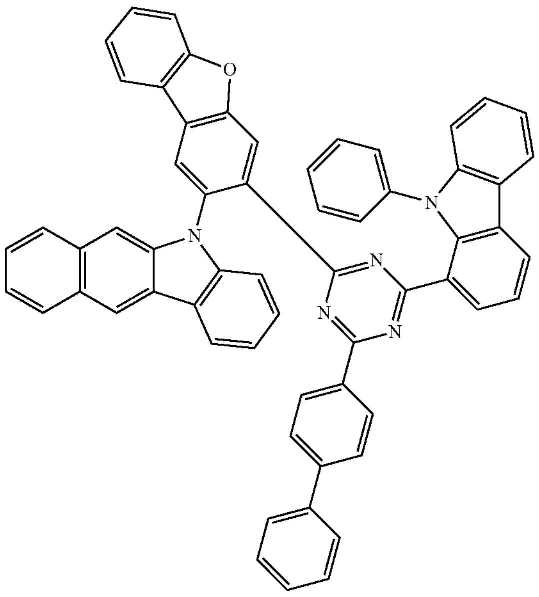

-continued
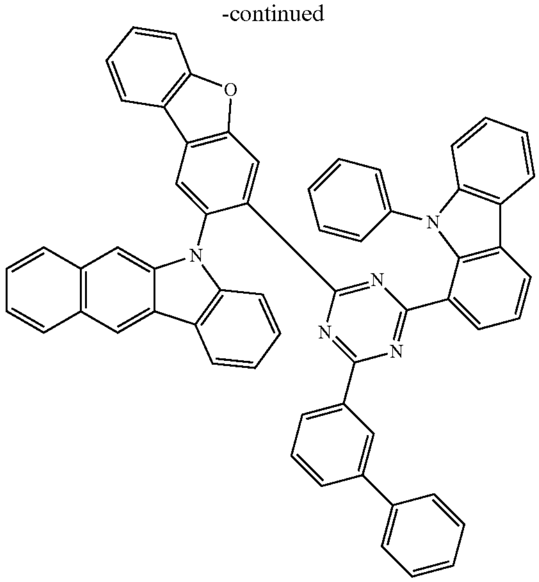
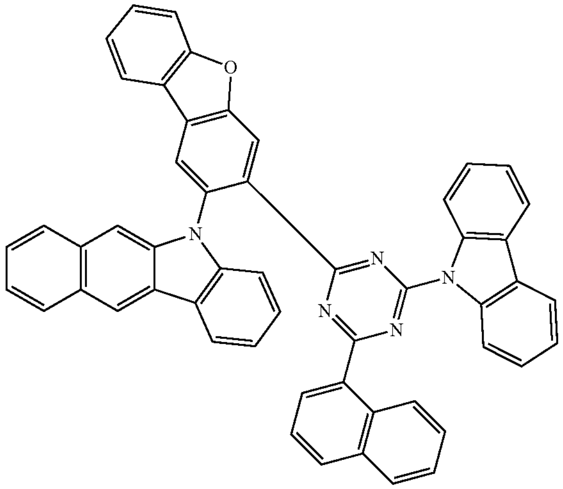
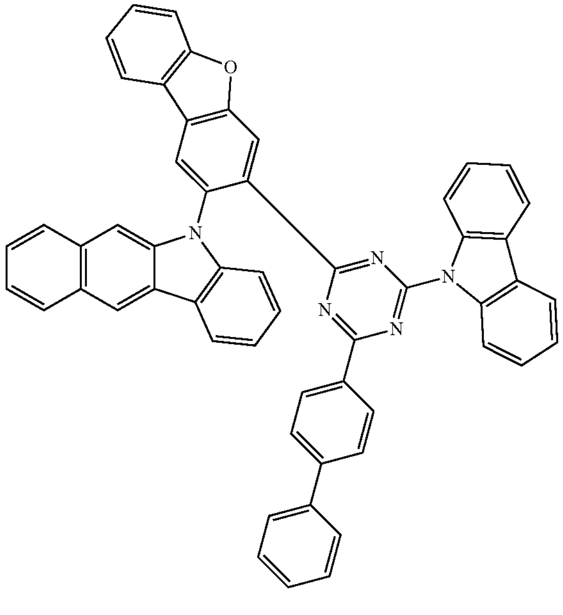
-continued
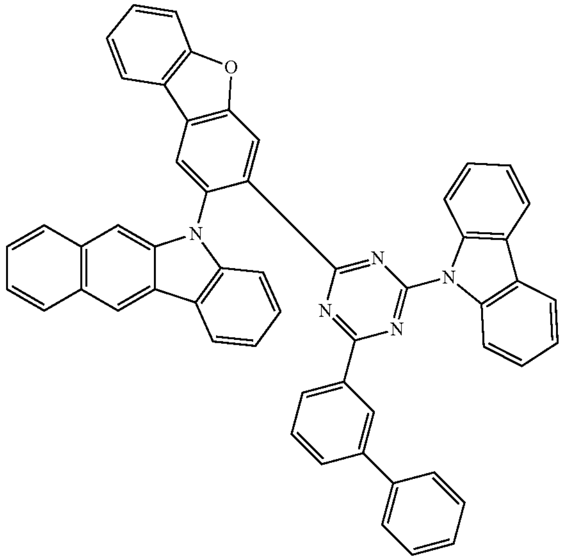
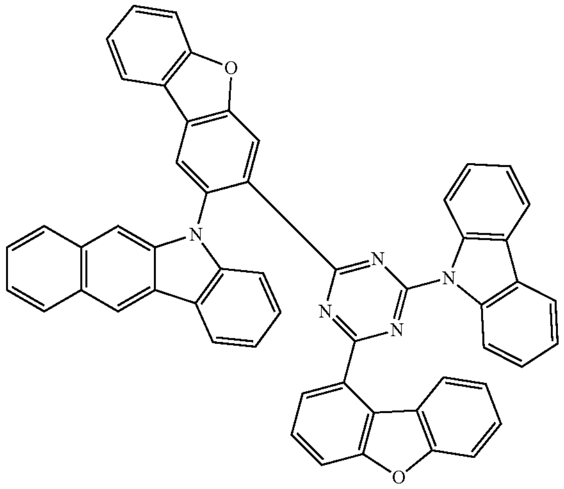
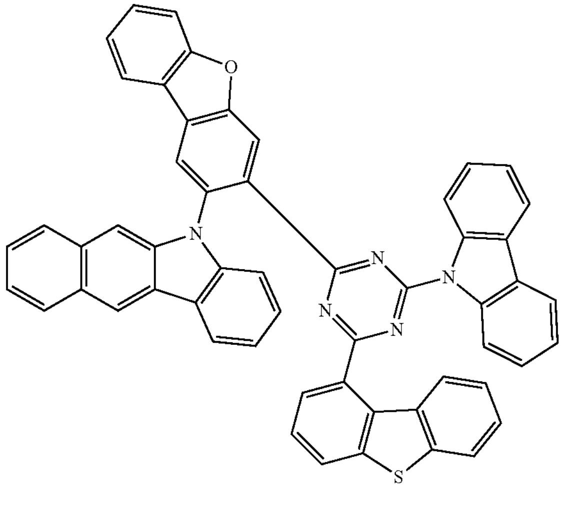

-continued
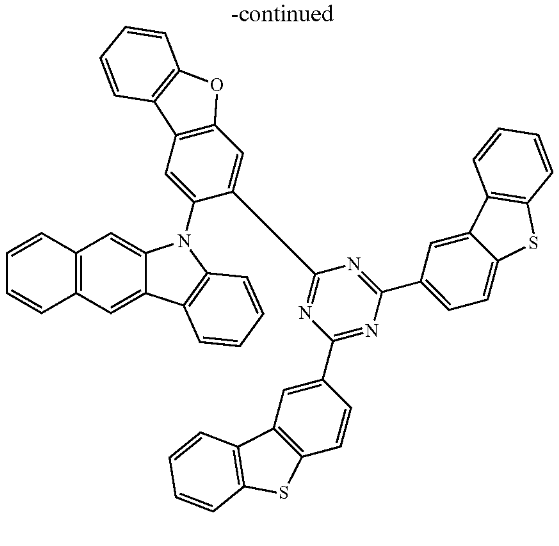
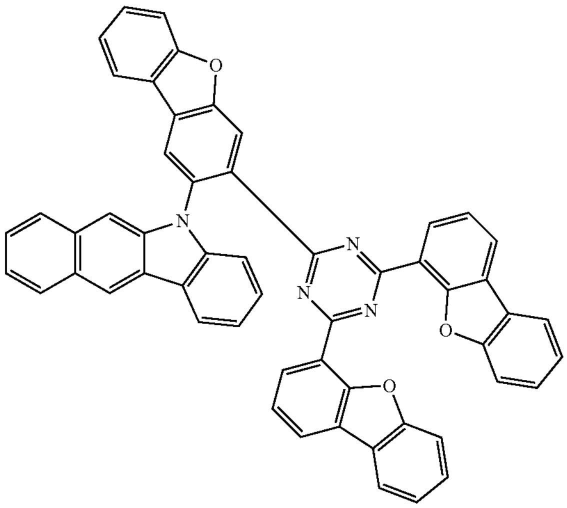
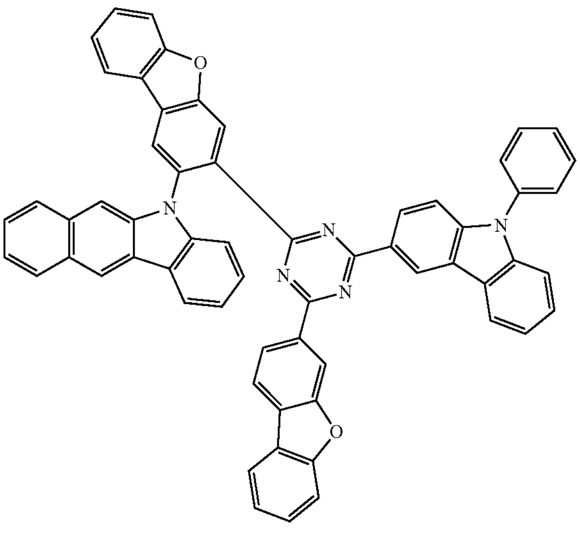
-continued
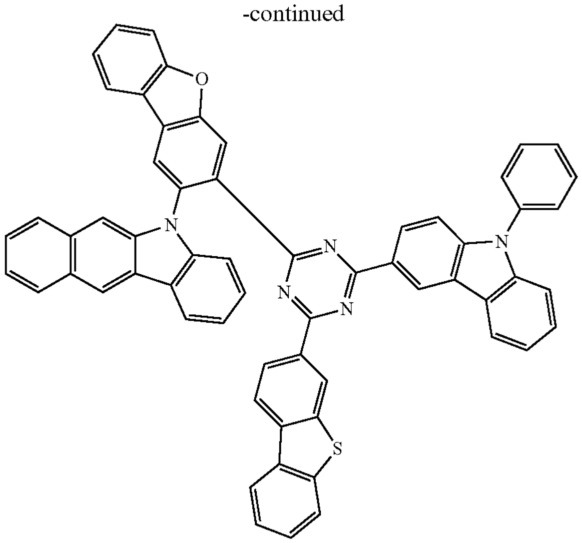
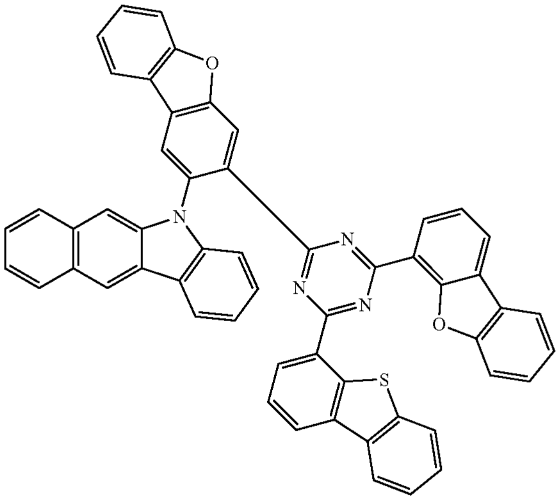
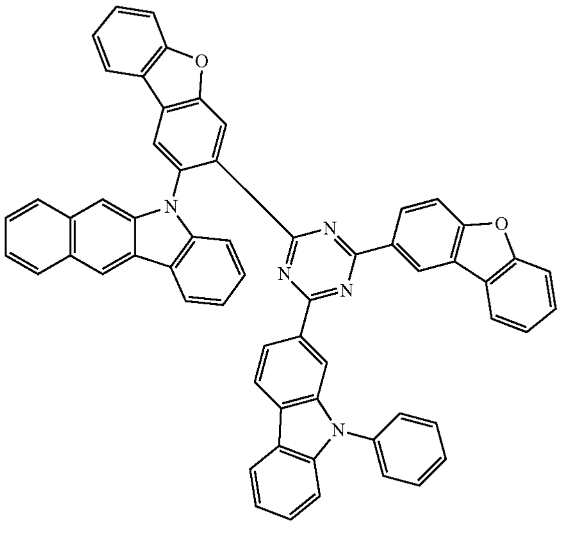

-continued
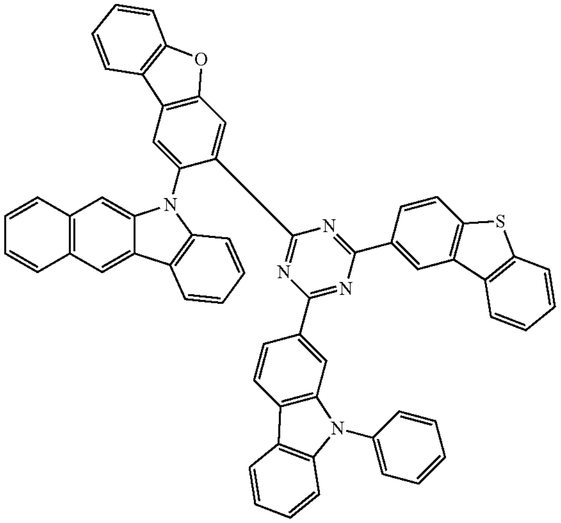
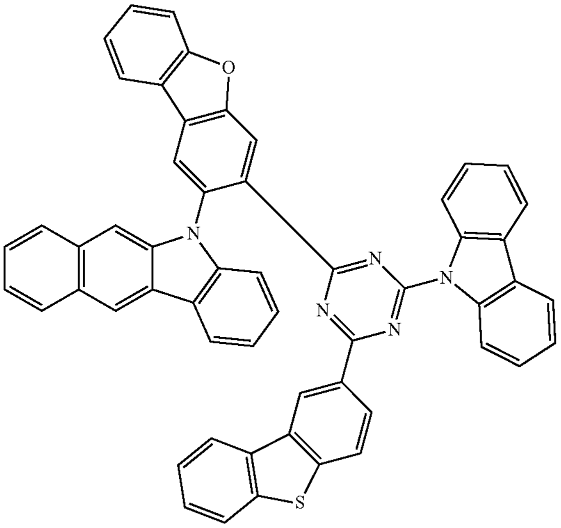
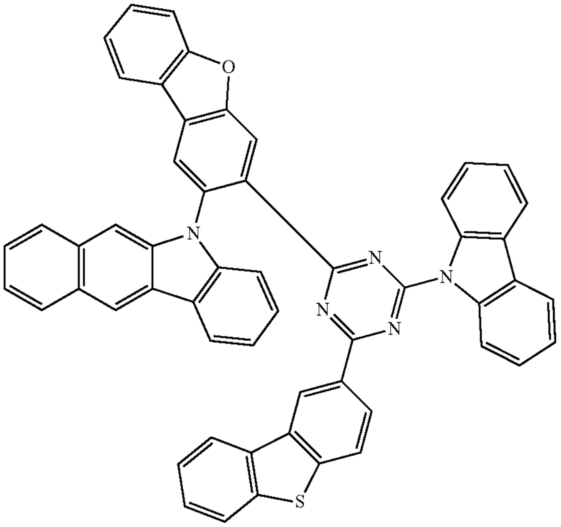
-continued
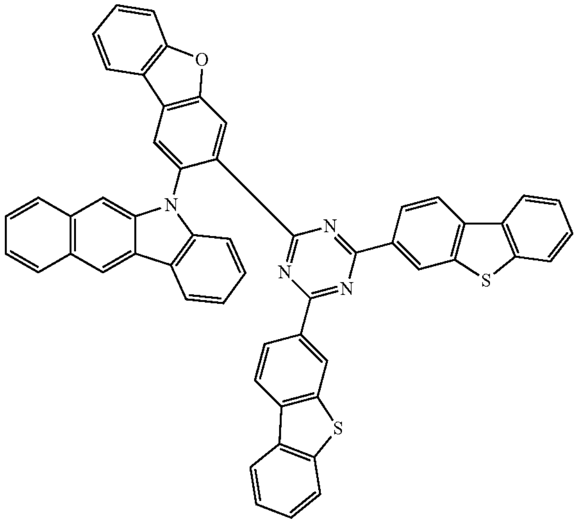
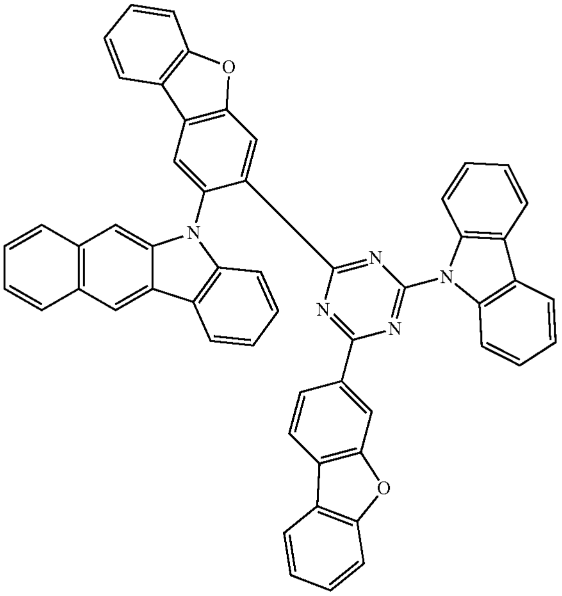
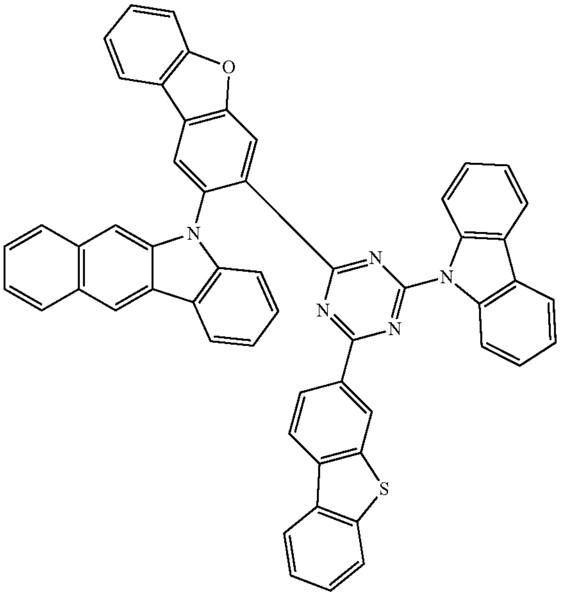

-continued
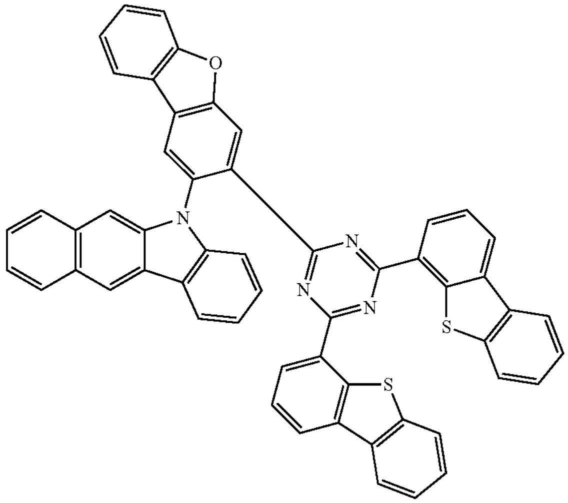
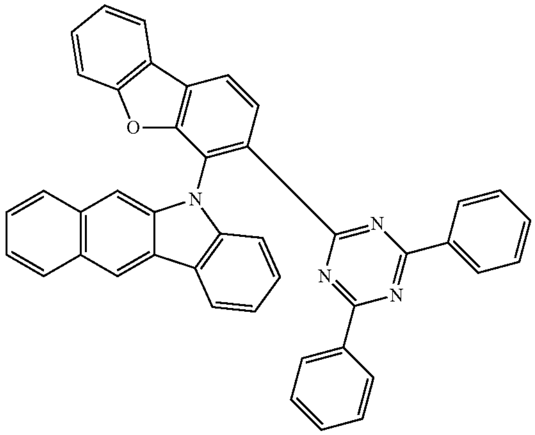
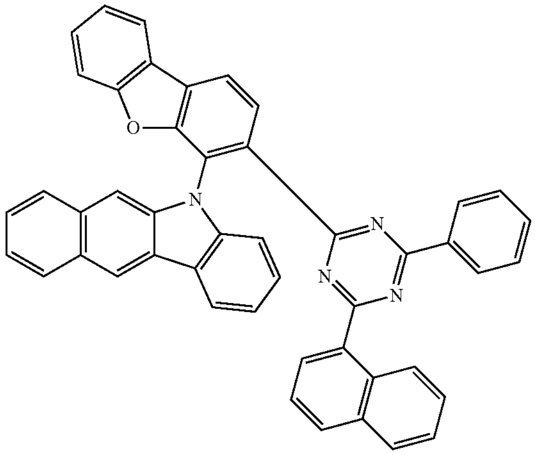
-continued
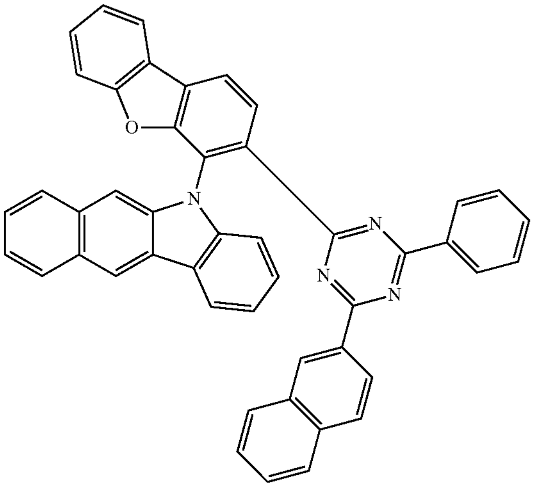
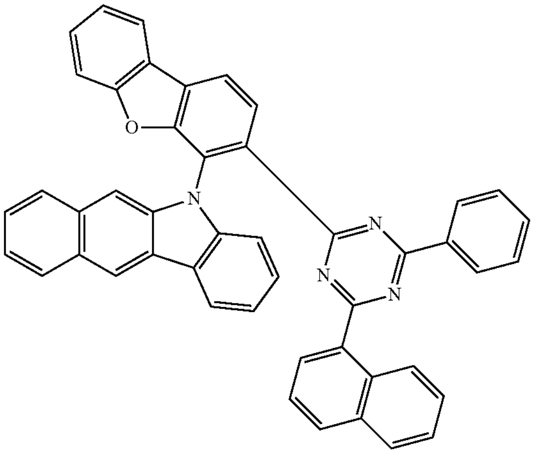
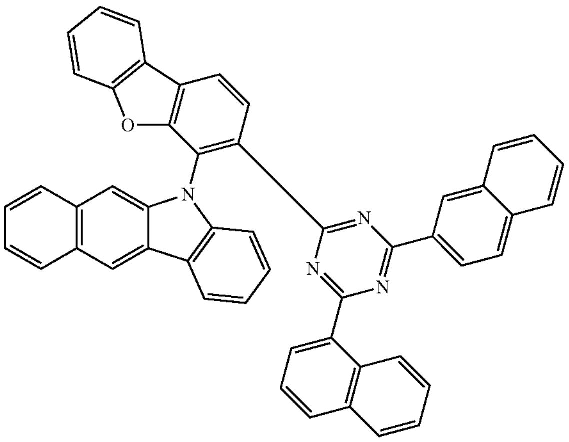

-continued
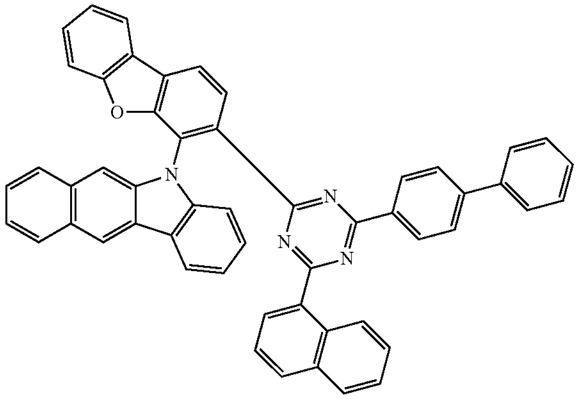
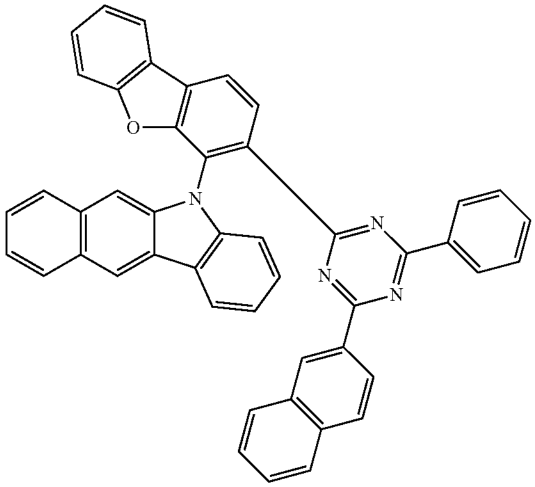
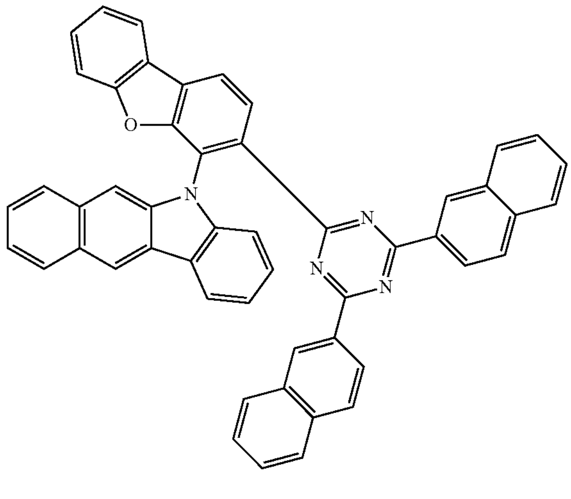
-continued
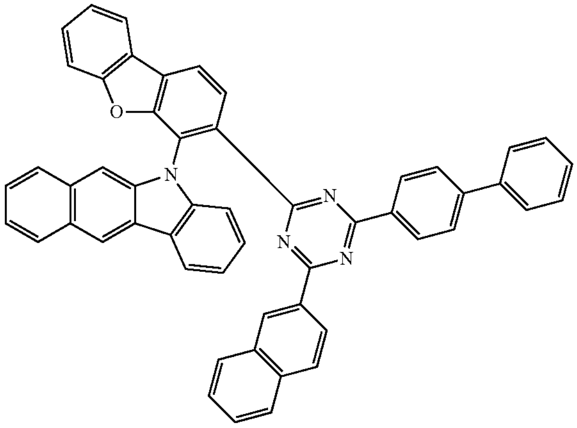
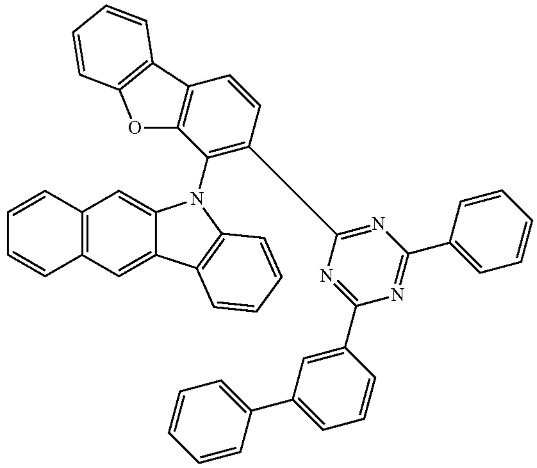
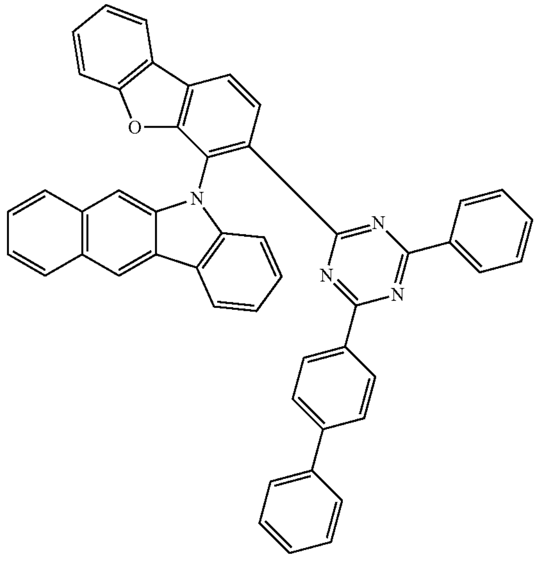

-continued
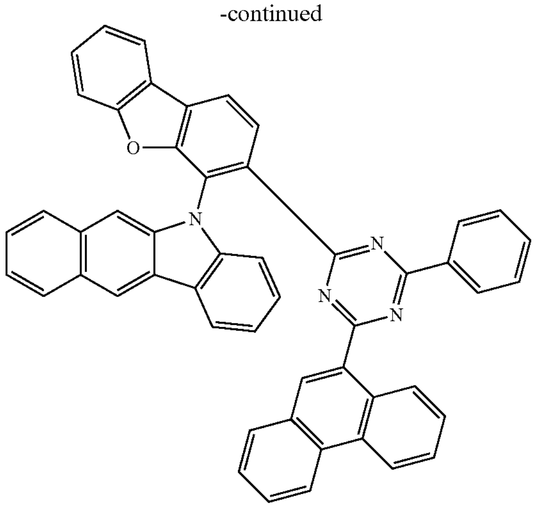
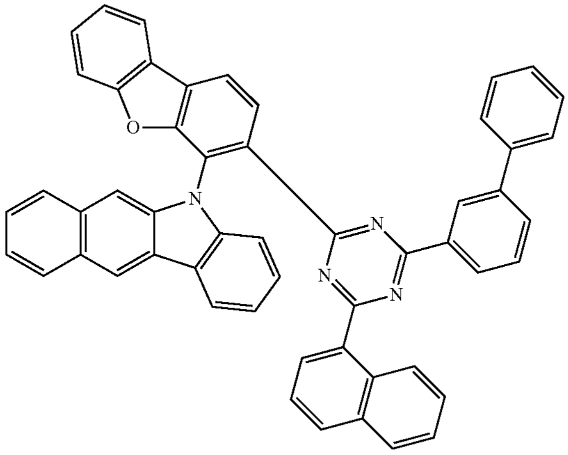
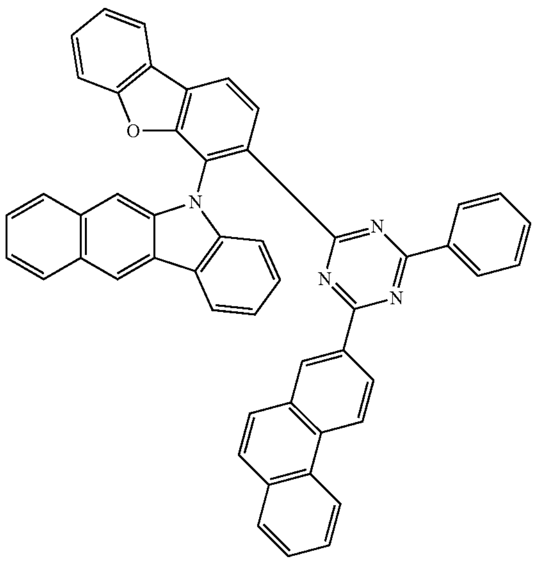
-continued
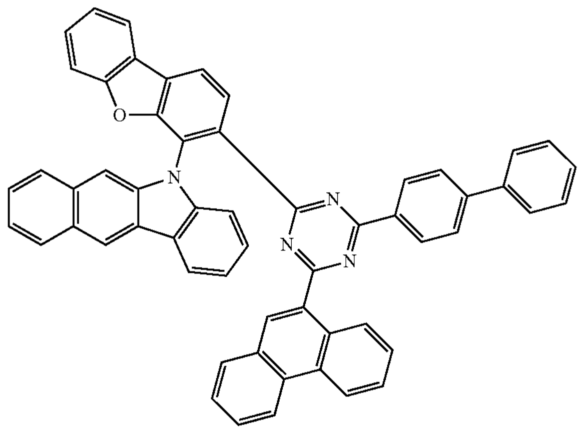
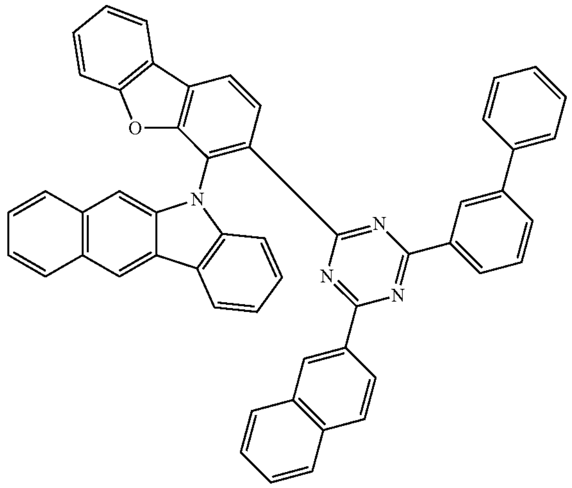
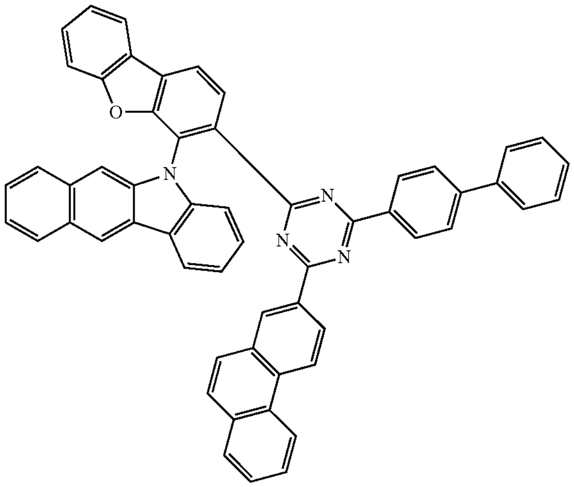

-continued
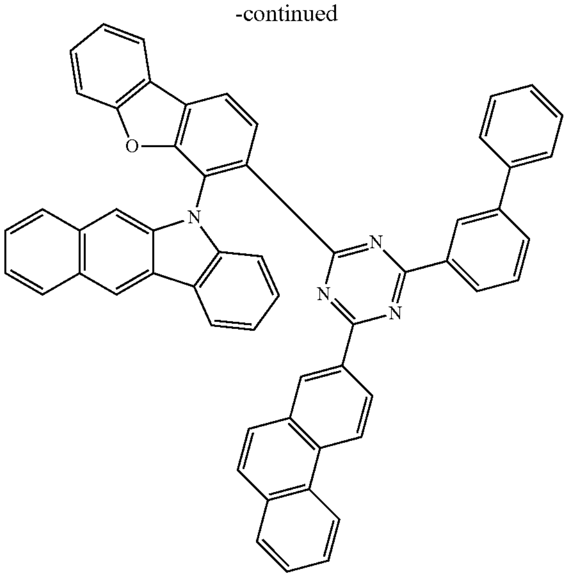
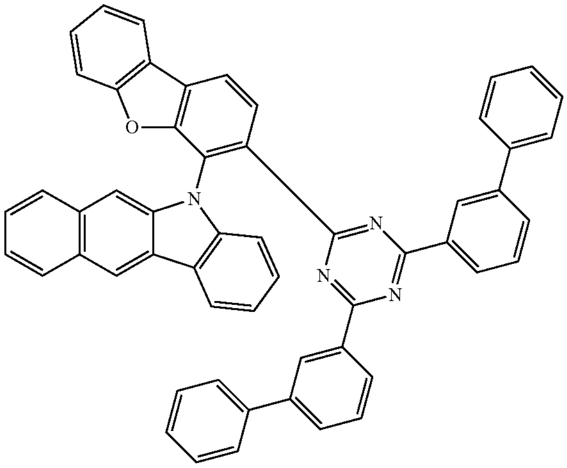
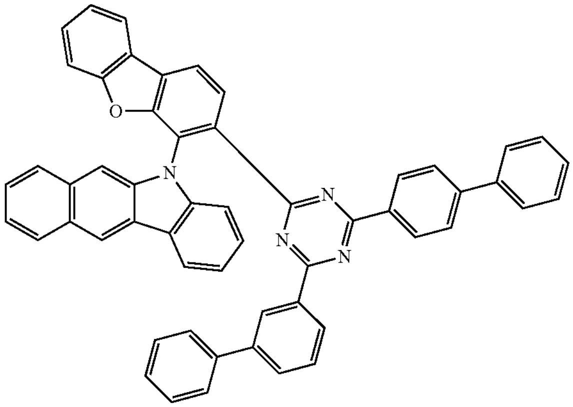
-continued
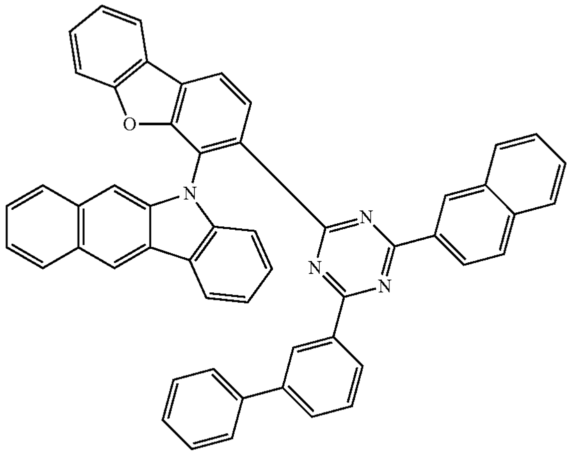
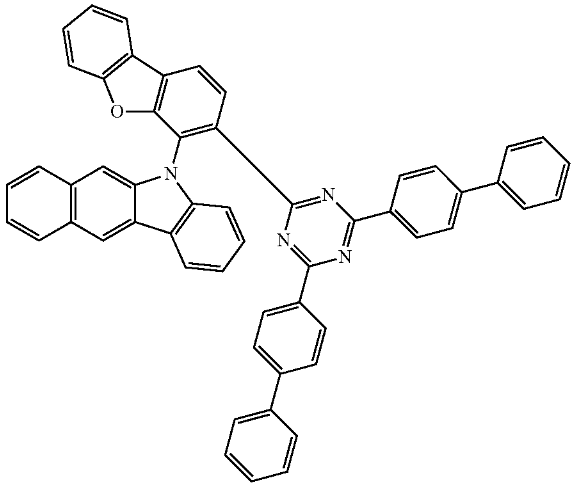
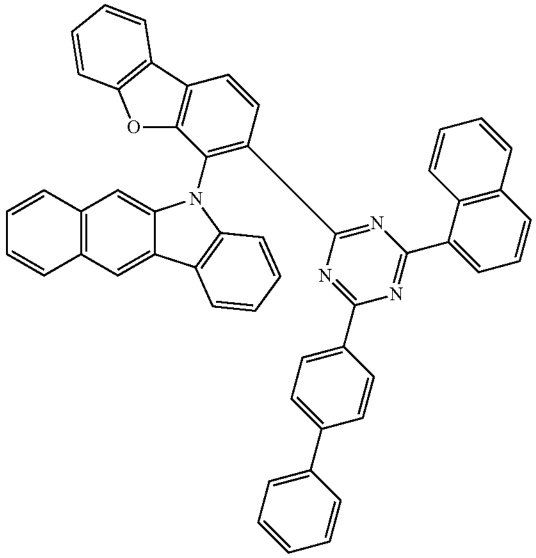

-continued
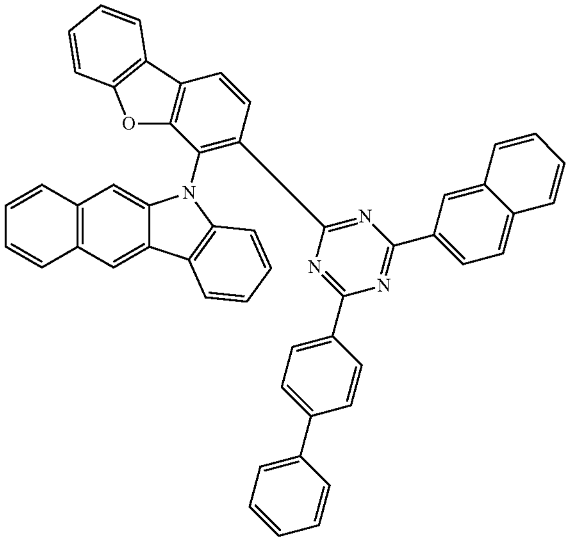
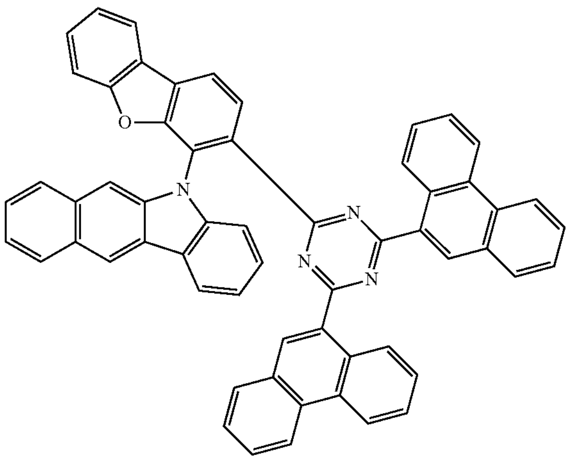
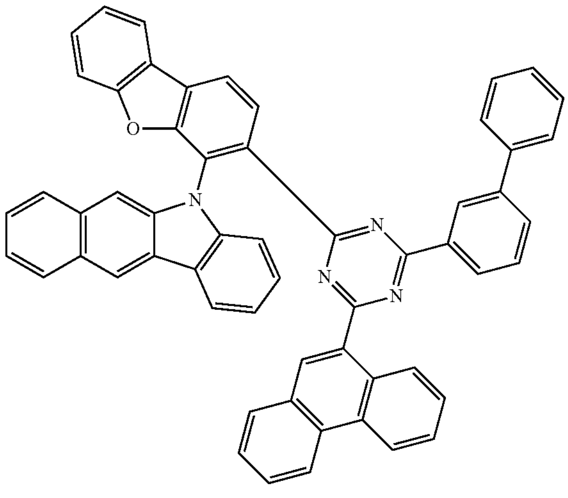
-continued
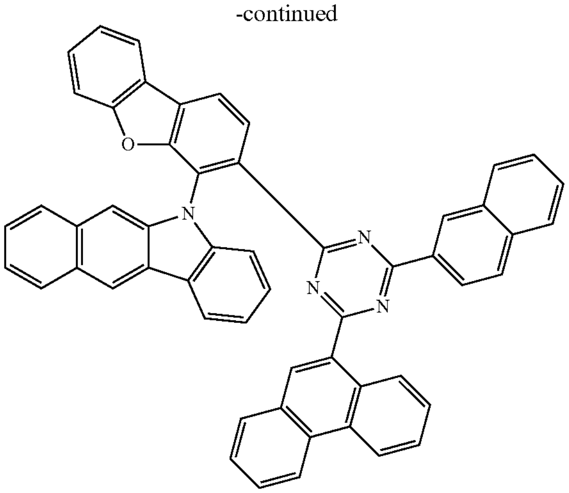
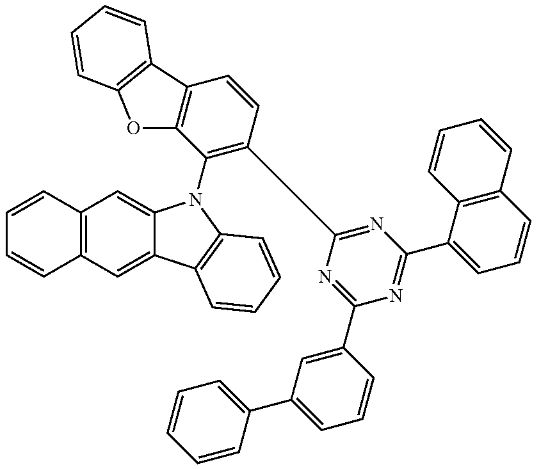
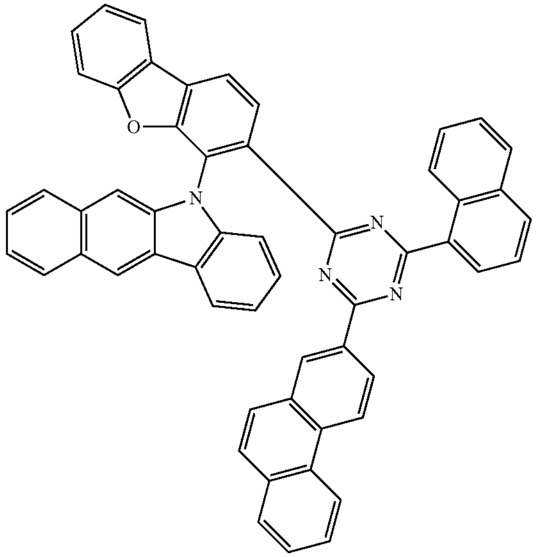

-continued
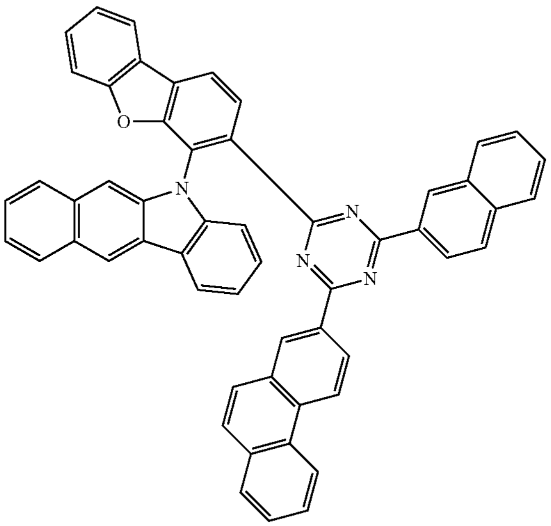
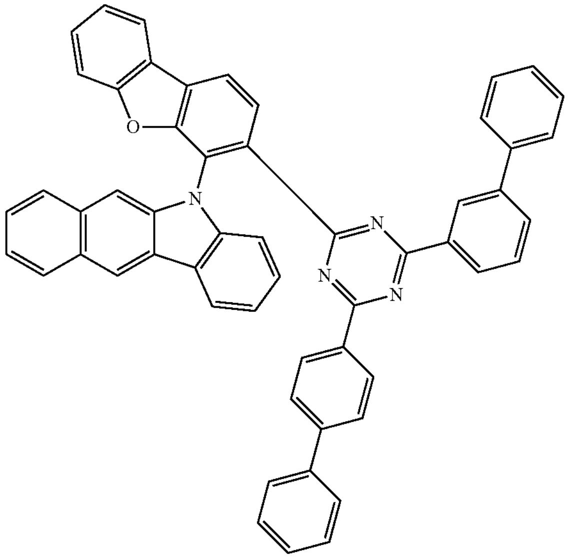
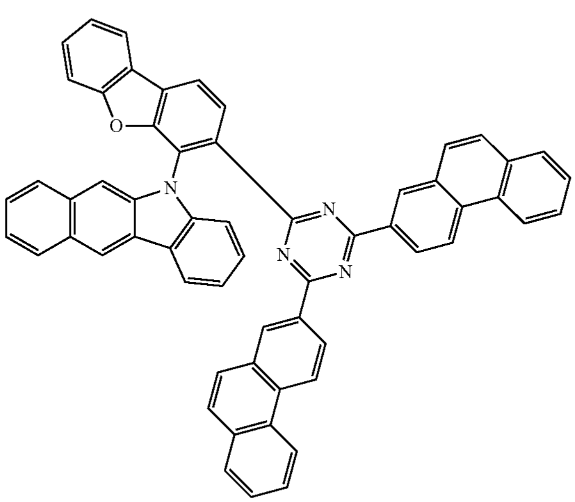
-continued
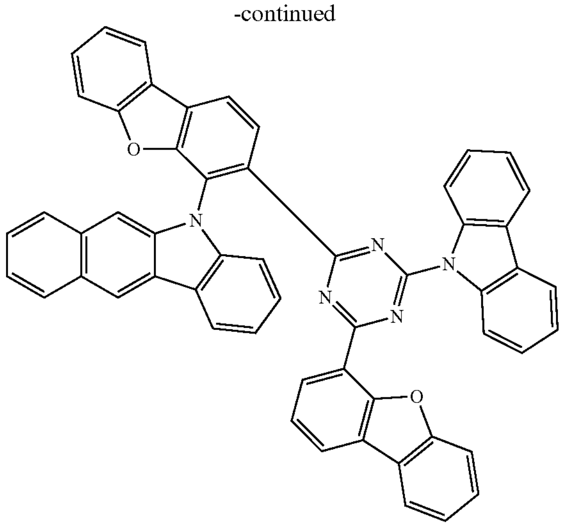
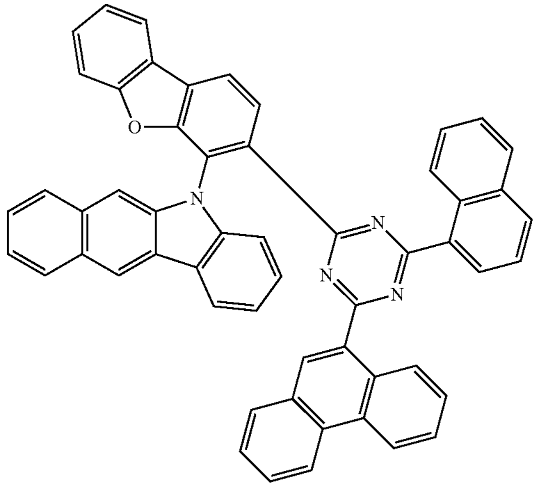
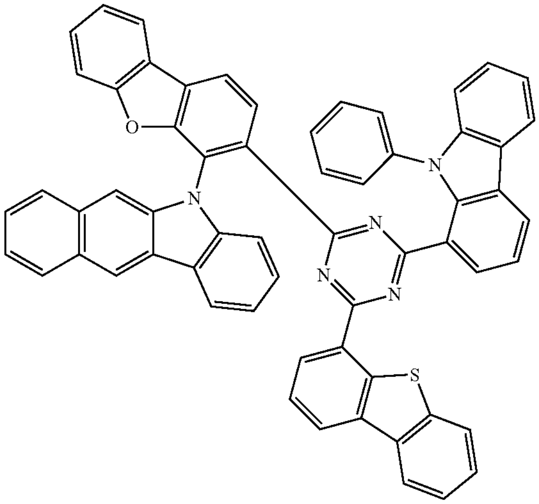

-continued
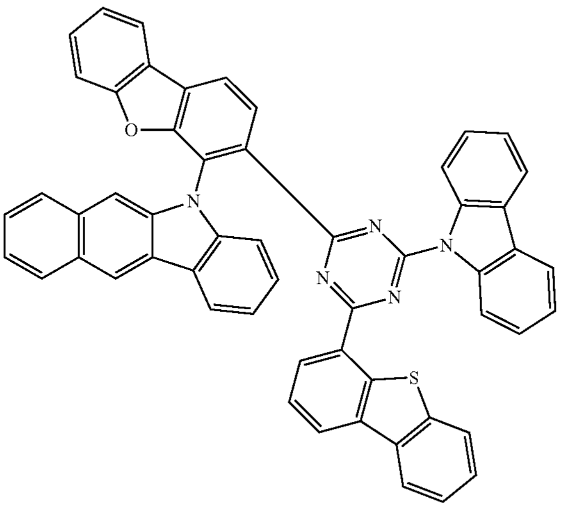
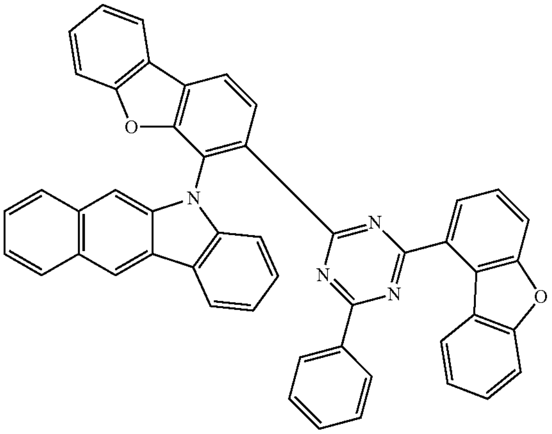
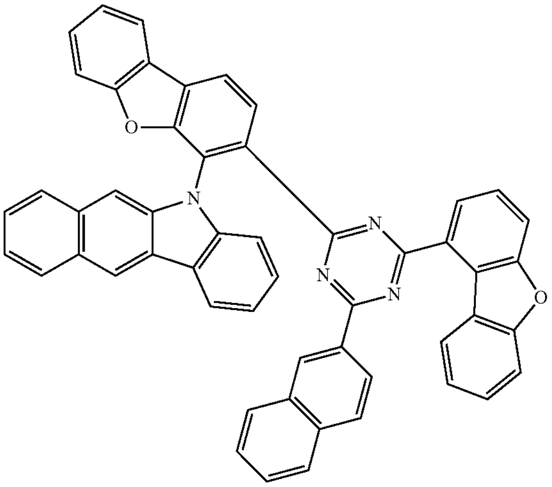
-continued
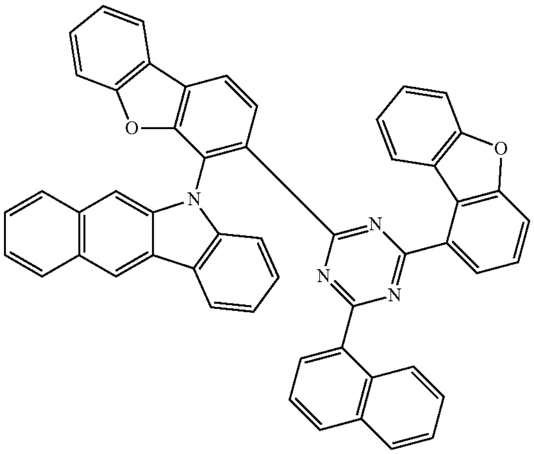
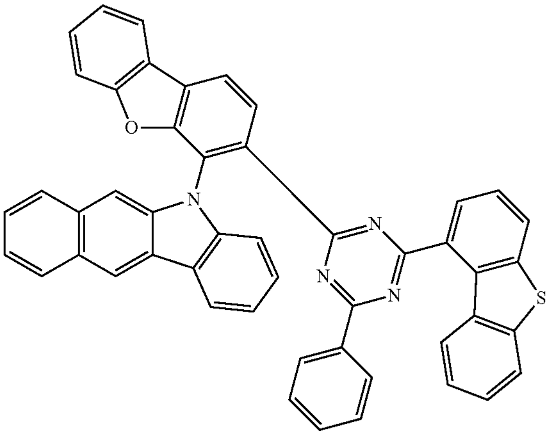
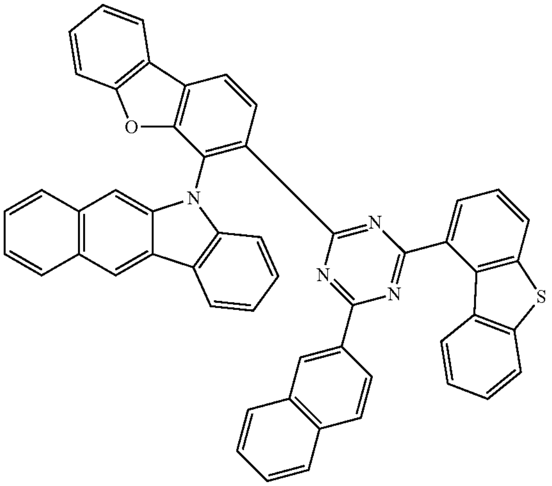

-continued
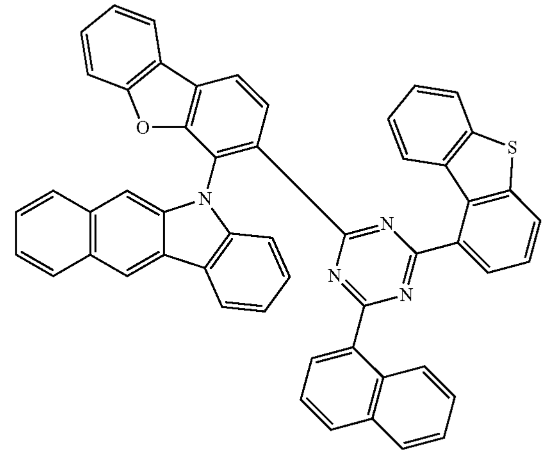
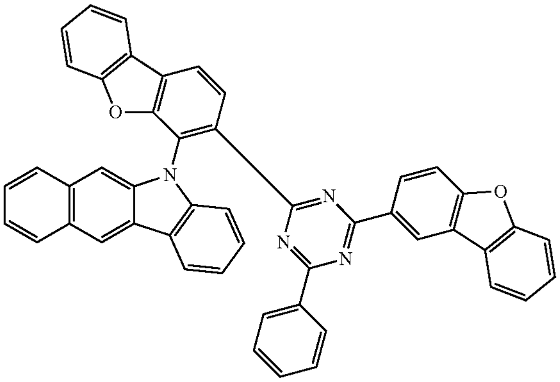
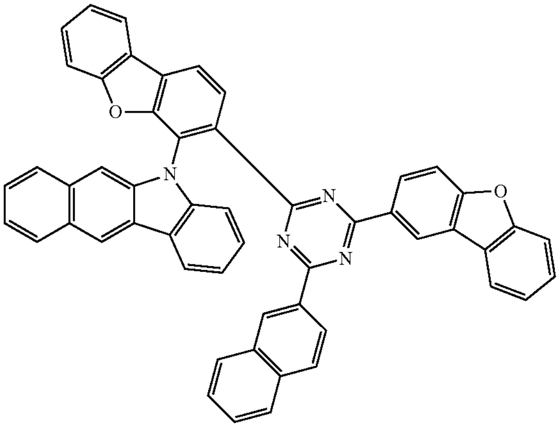
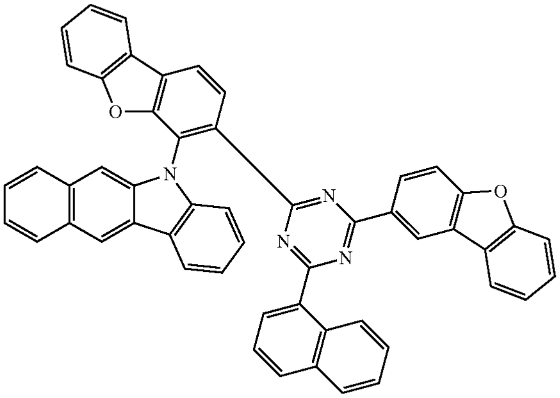
-continued
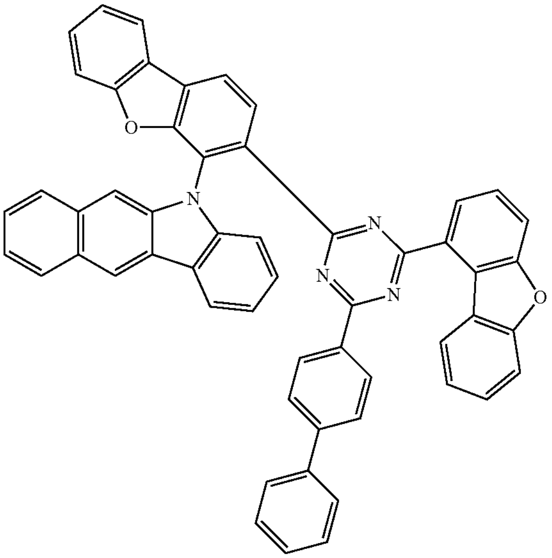
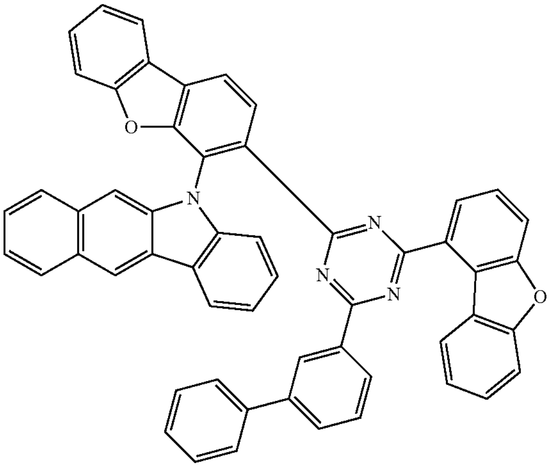
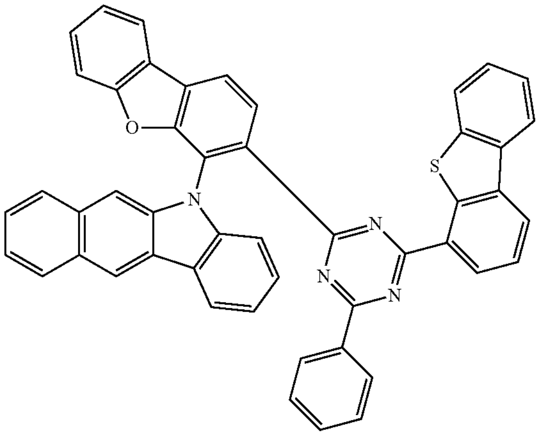

-continued
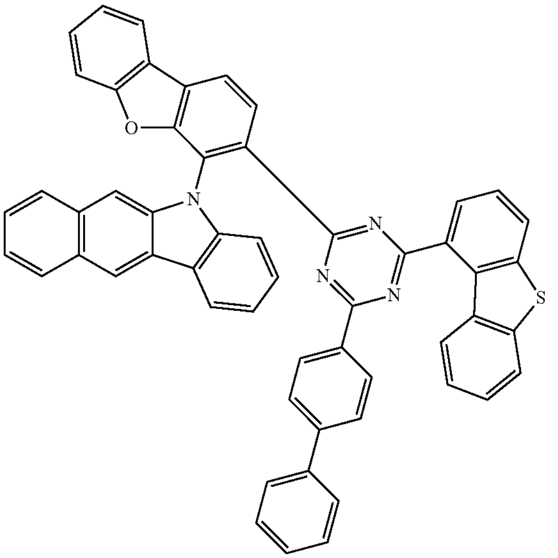
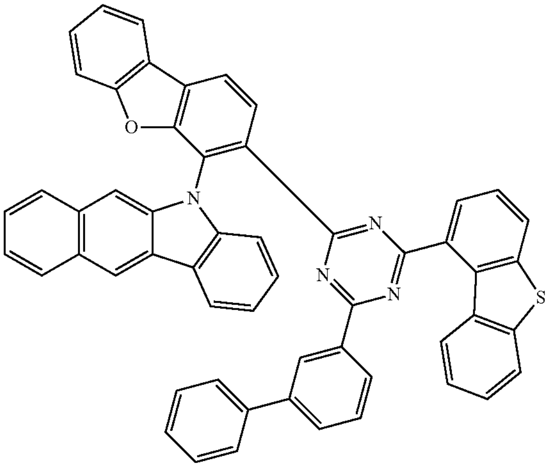
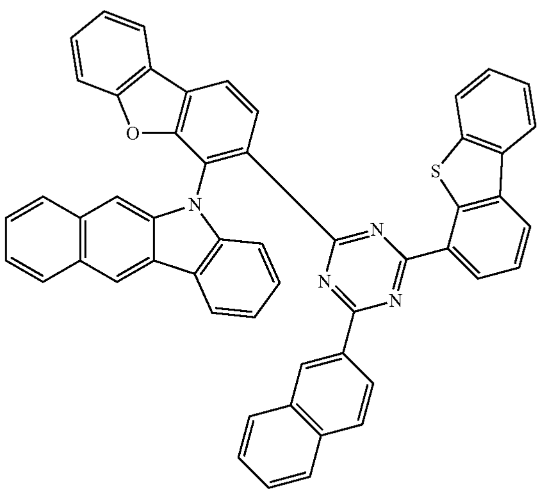
-continued
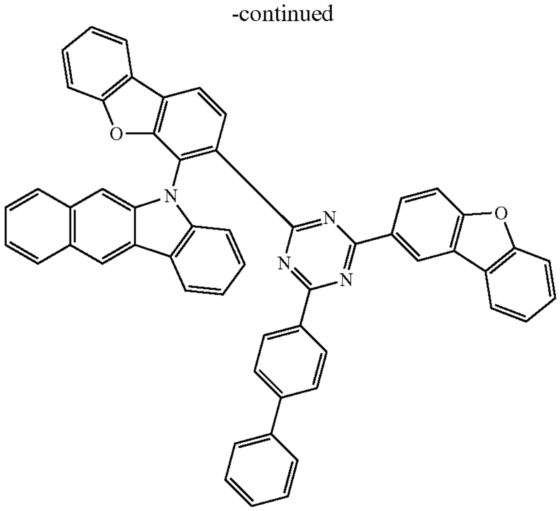
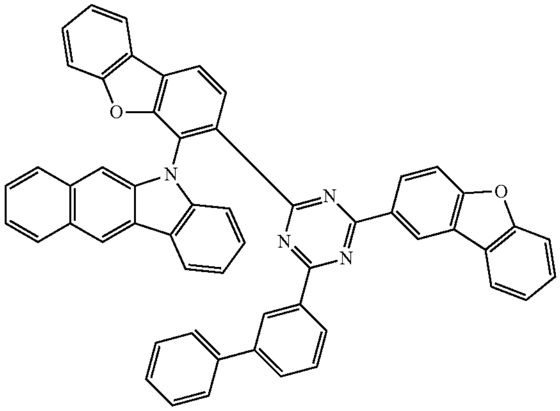
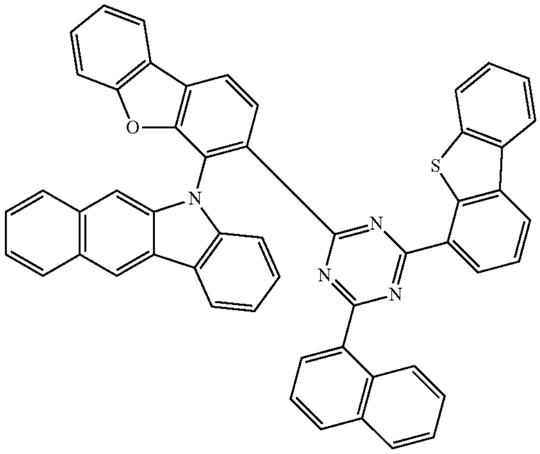
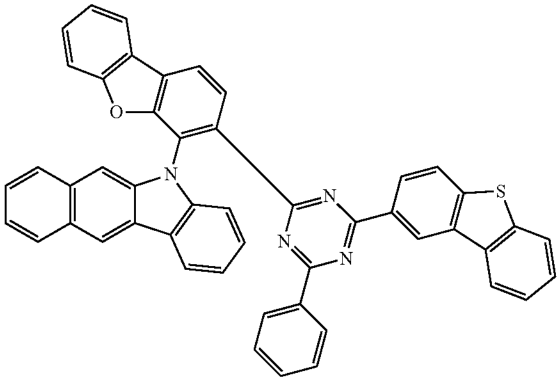

-continued
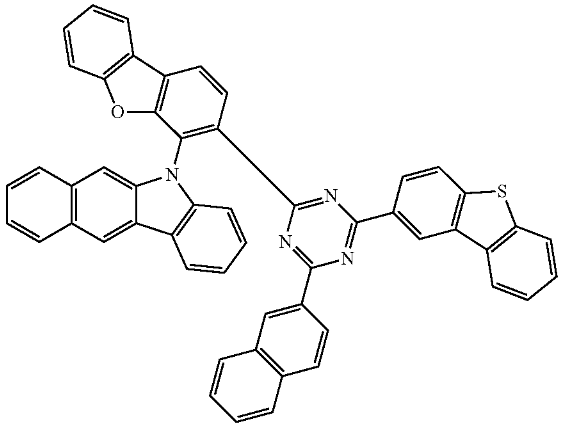
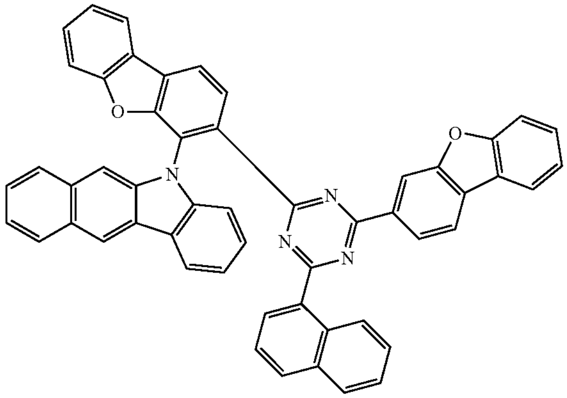
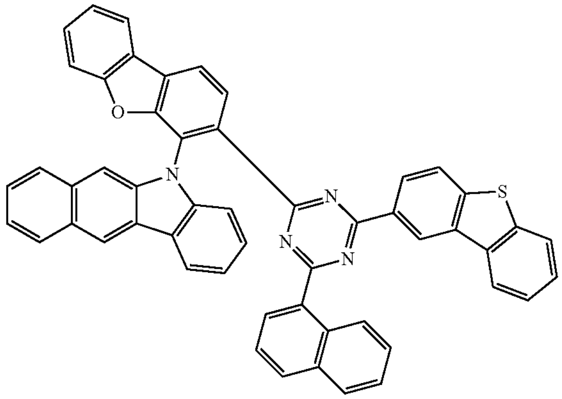
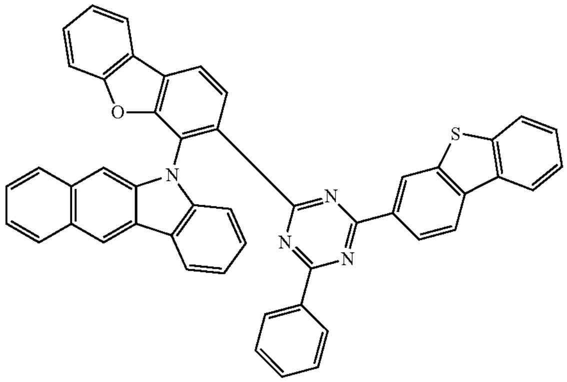
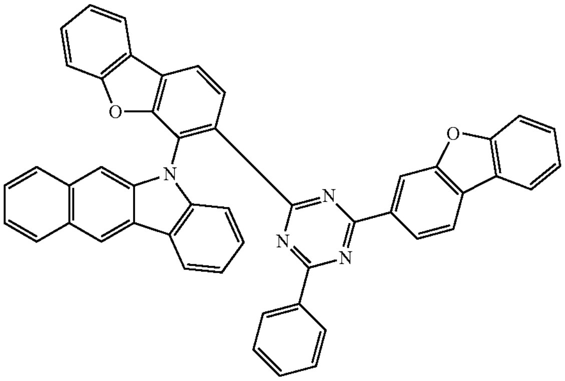
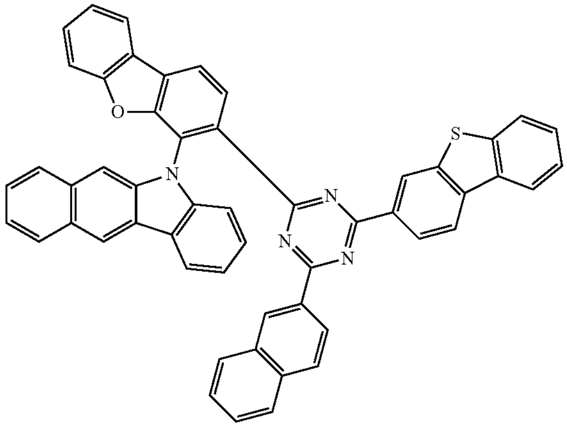
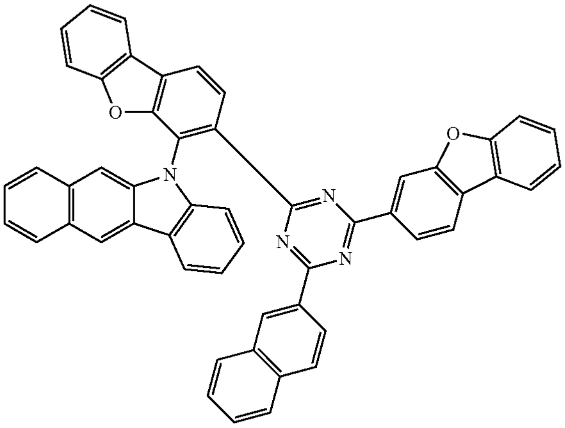
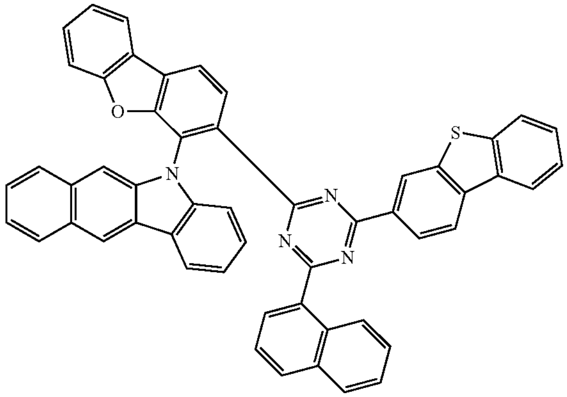

-continued
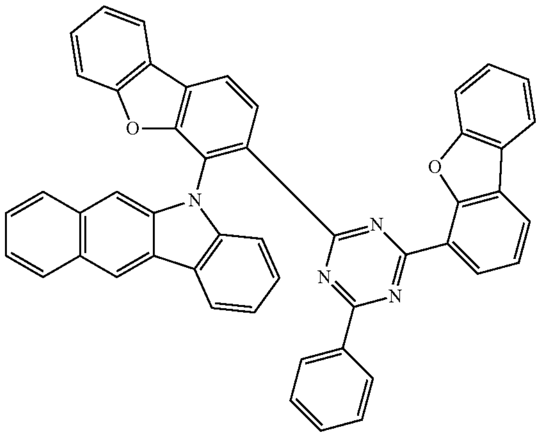
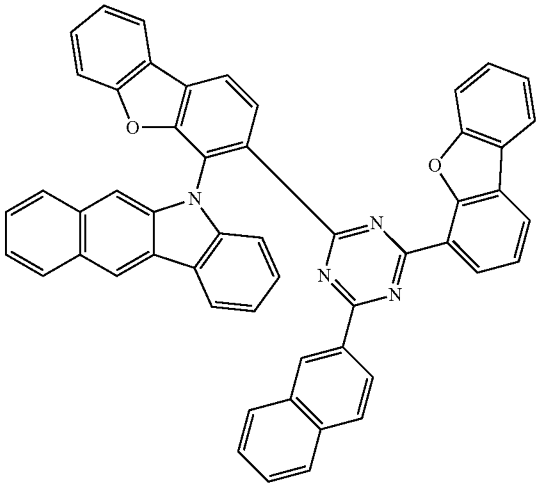
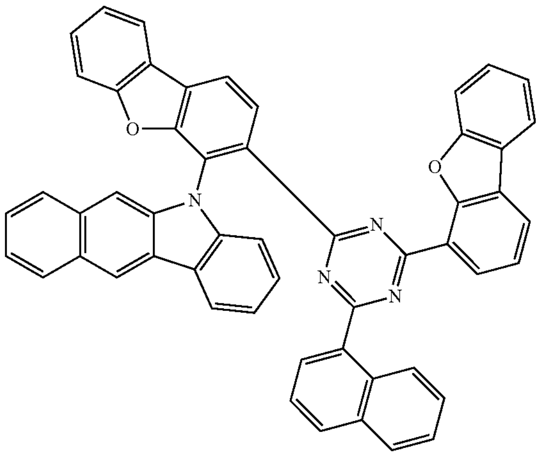
-continued
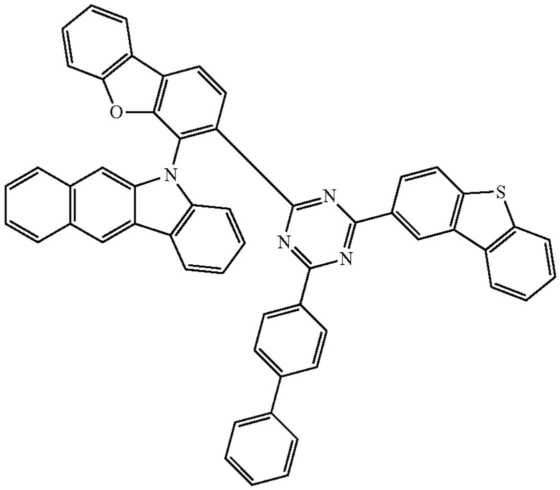
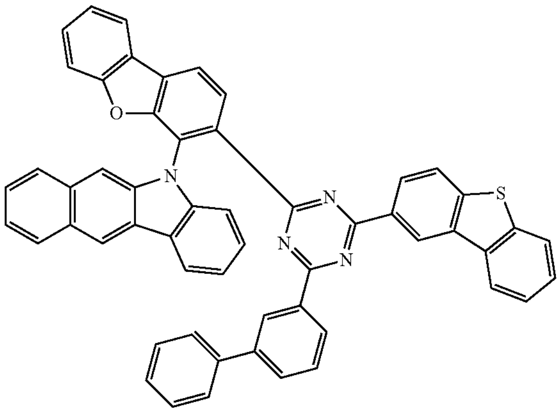
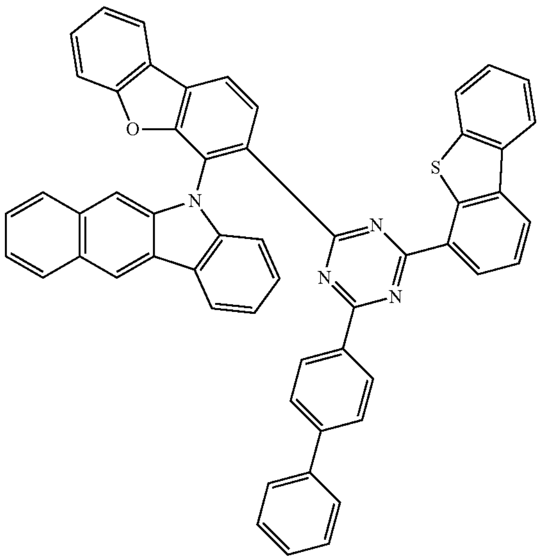

-continued
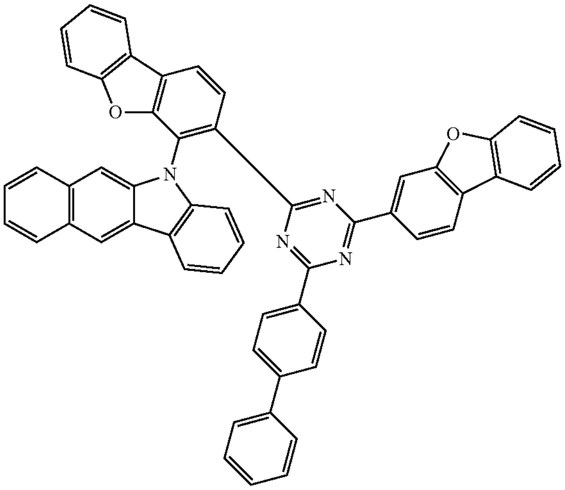
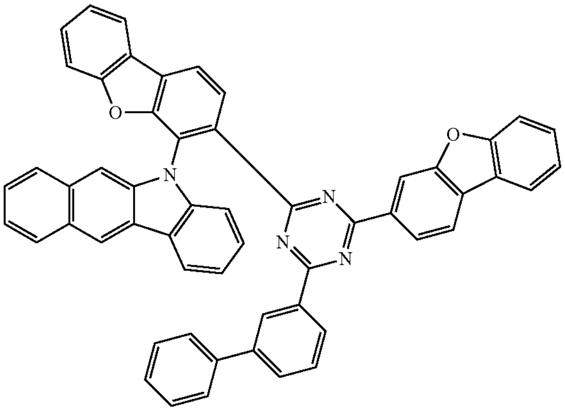
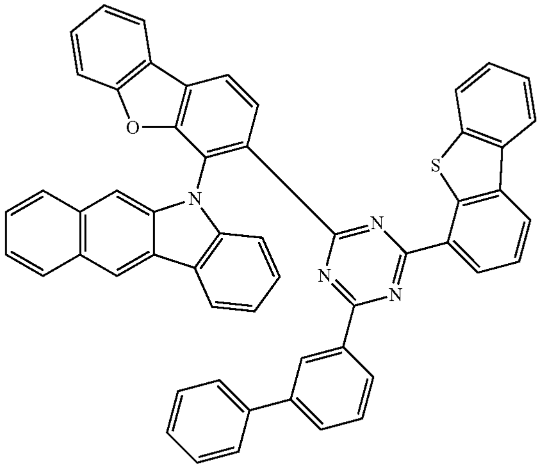
-continued
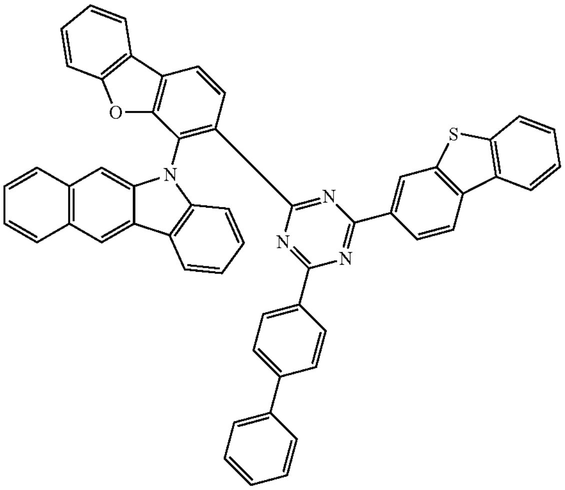
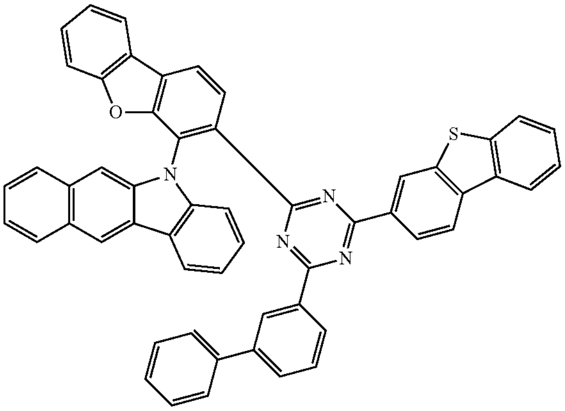
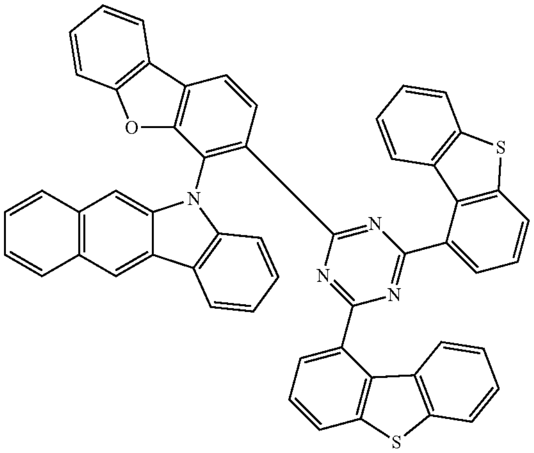

-continued
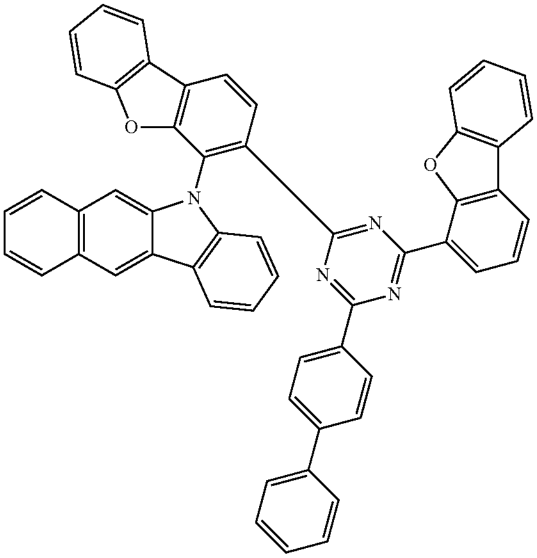
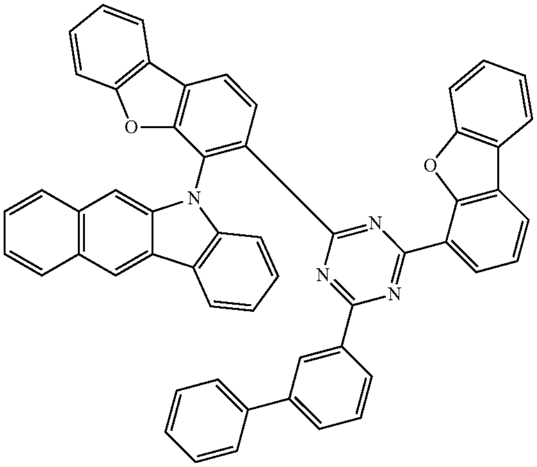
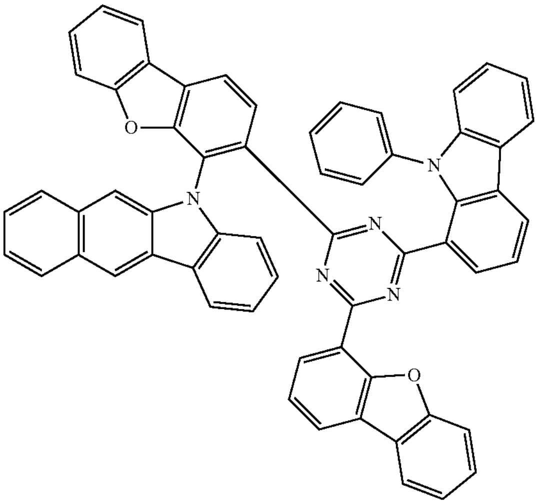
-continued
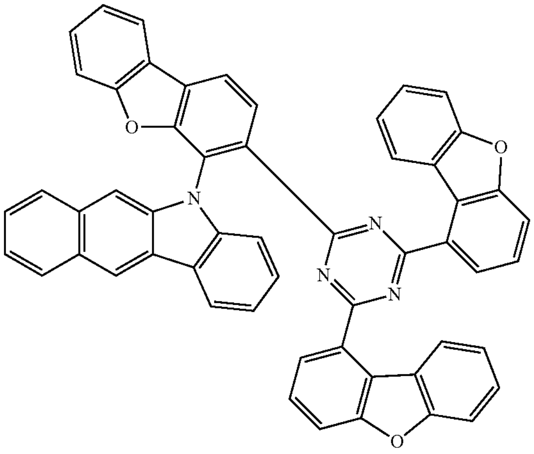
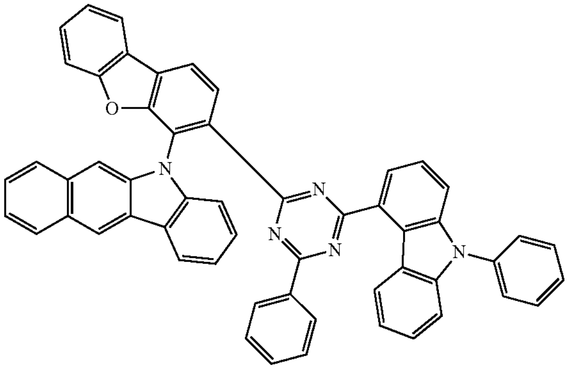
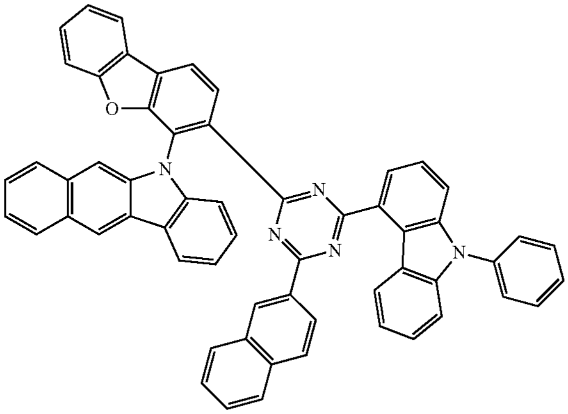
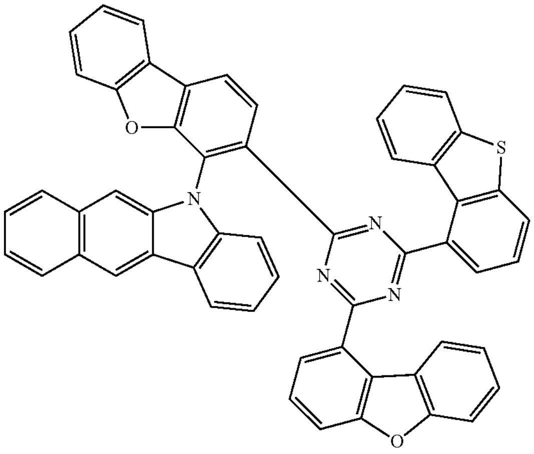

-continued
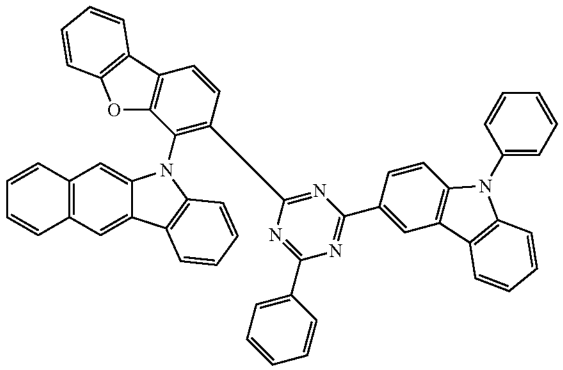
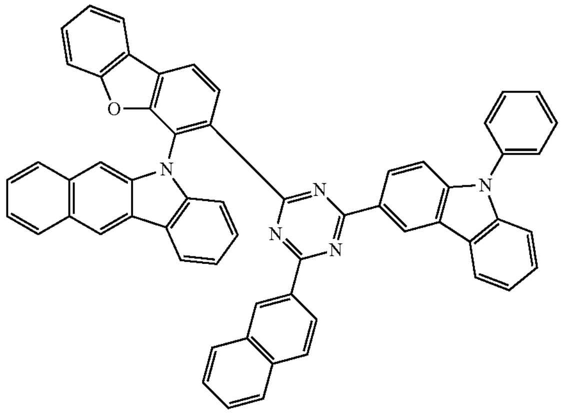
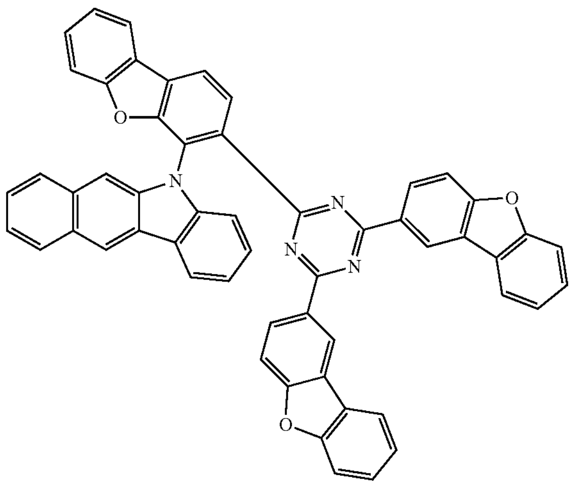
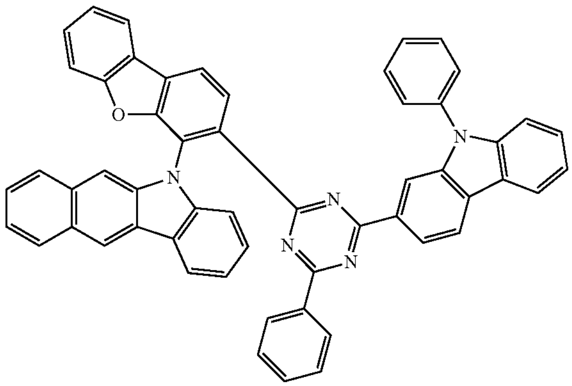
-continued
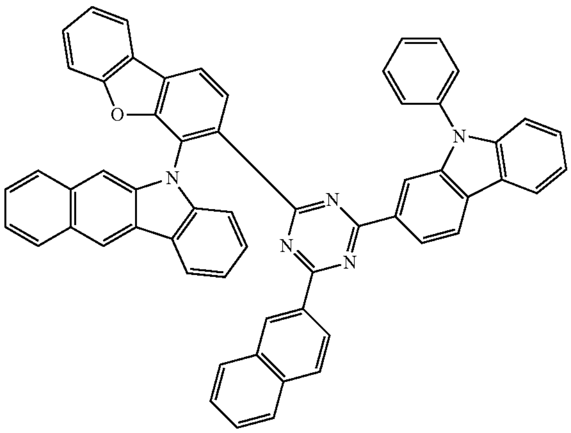
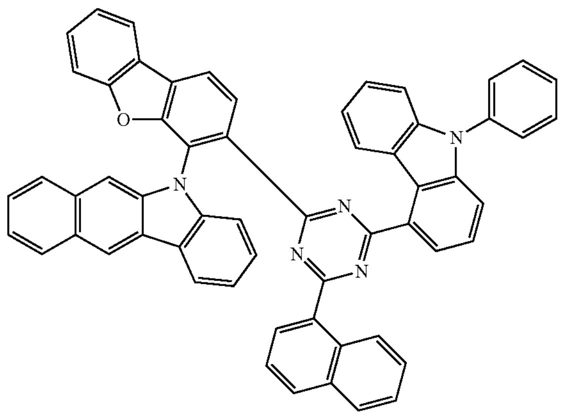
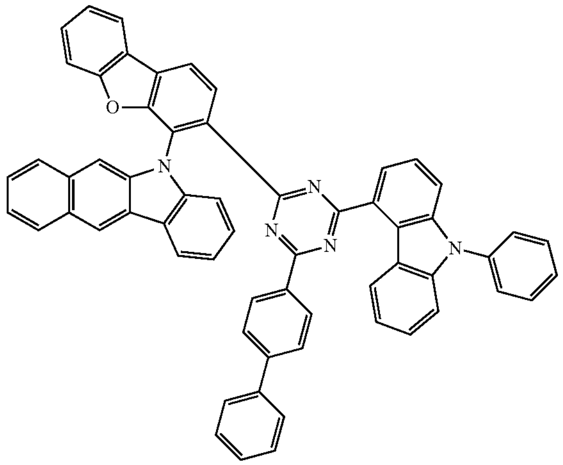

-continued
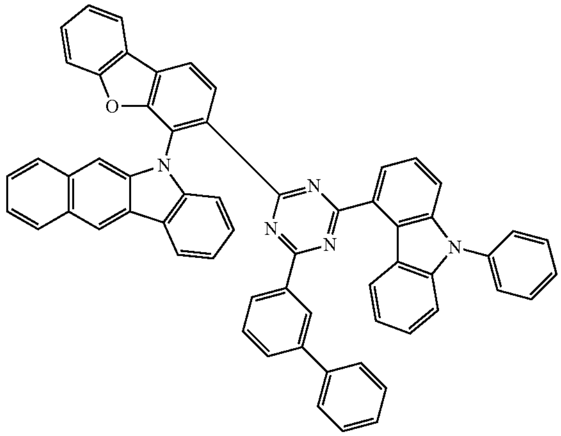
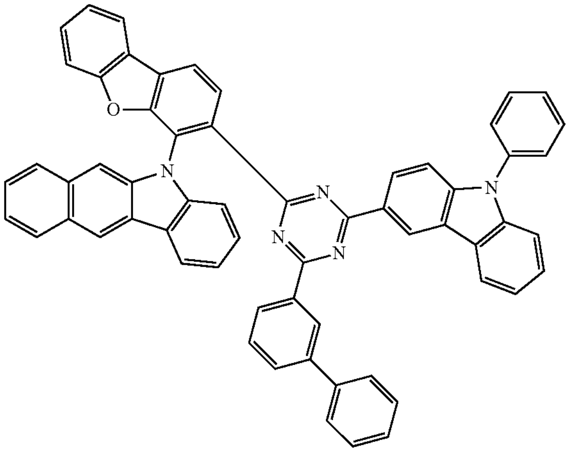
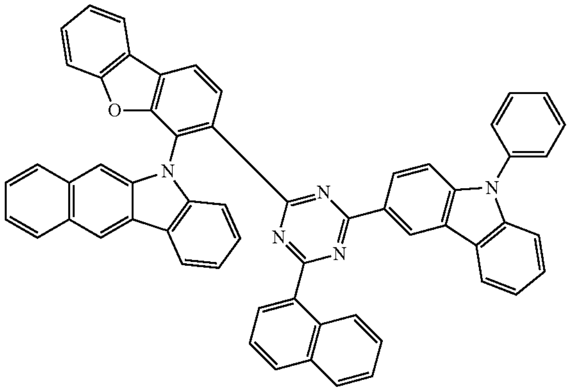
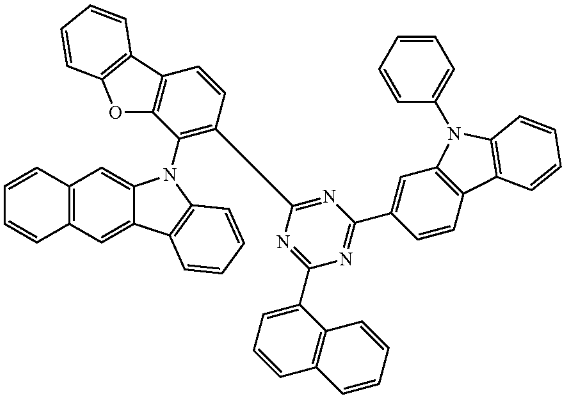
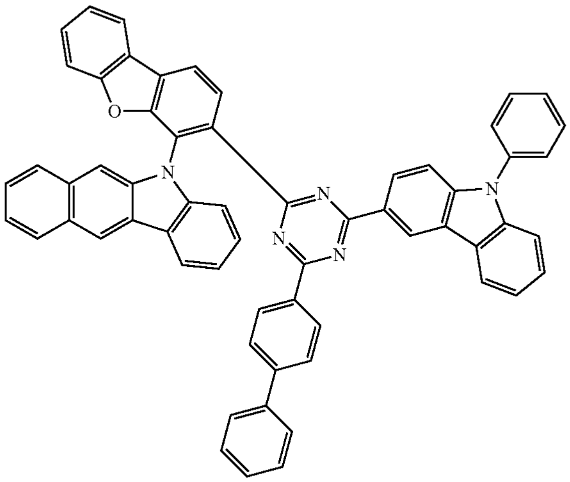
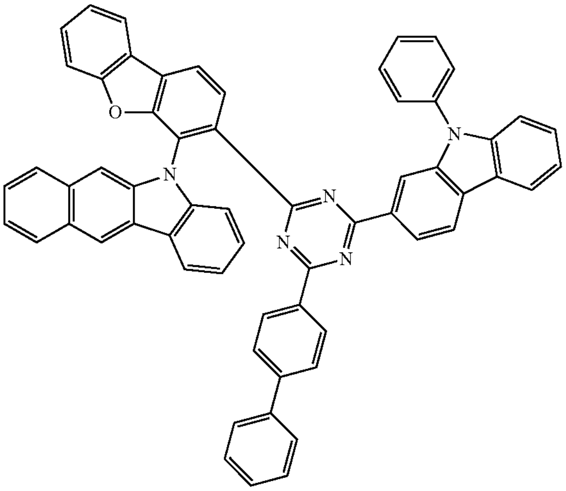
-continued -continued
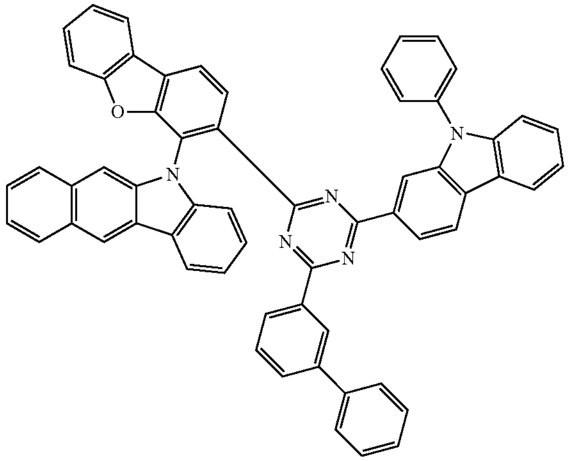
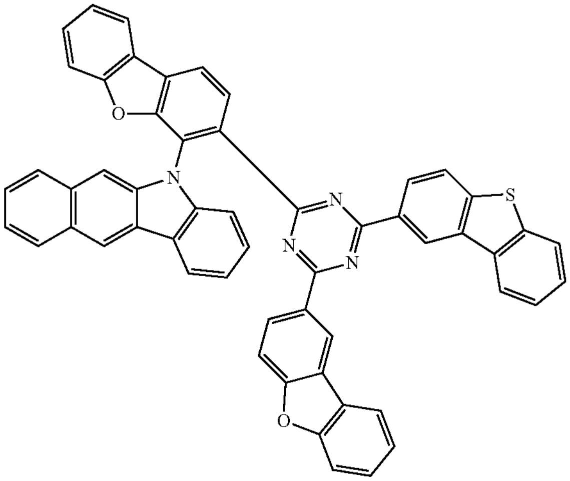
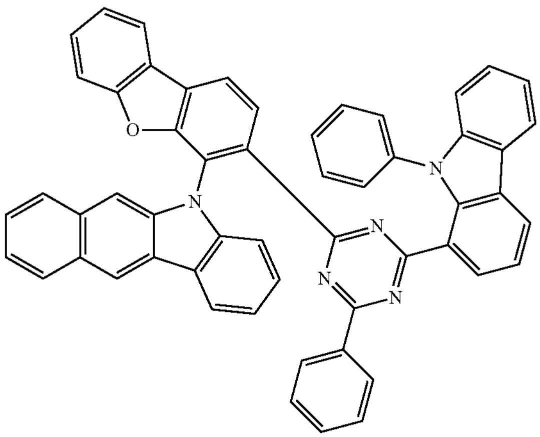
-continued
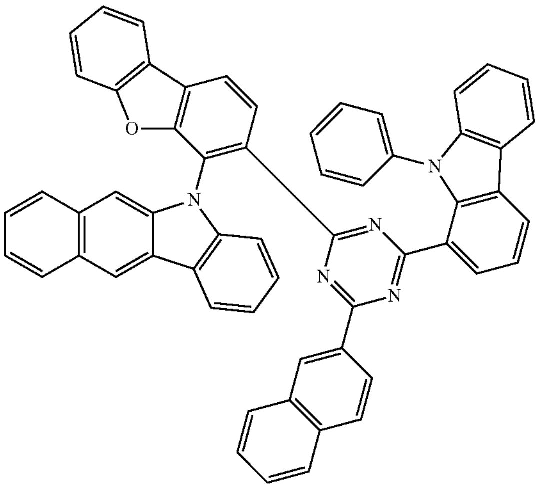
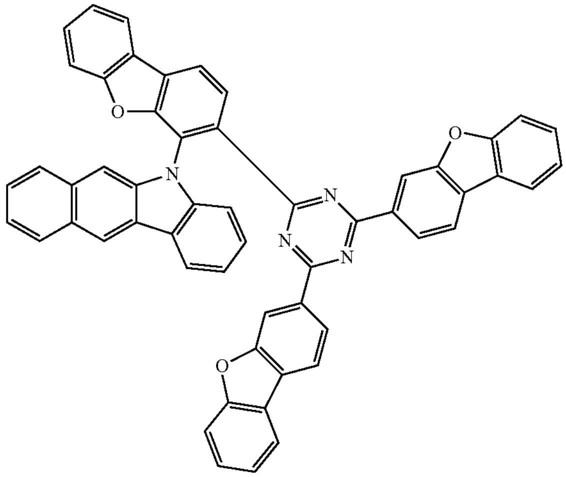
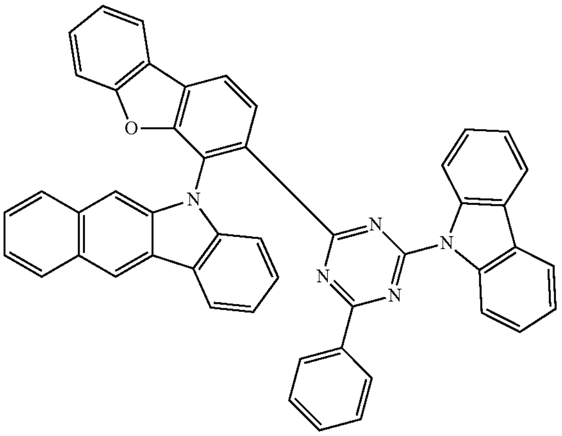

-continued
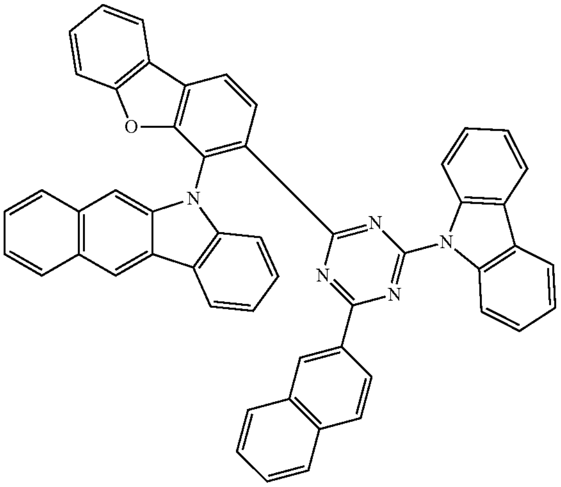
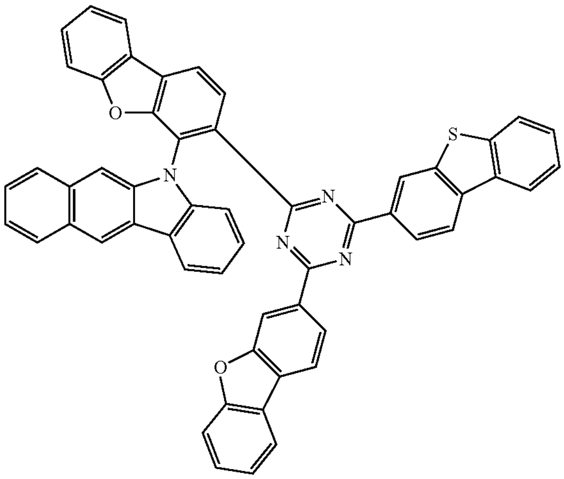
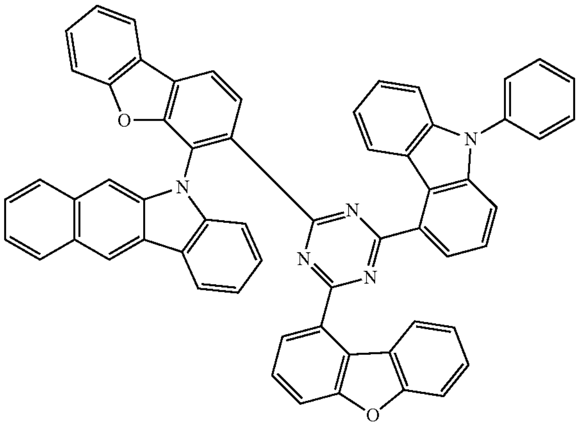
-continued
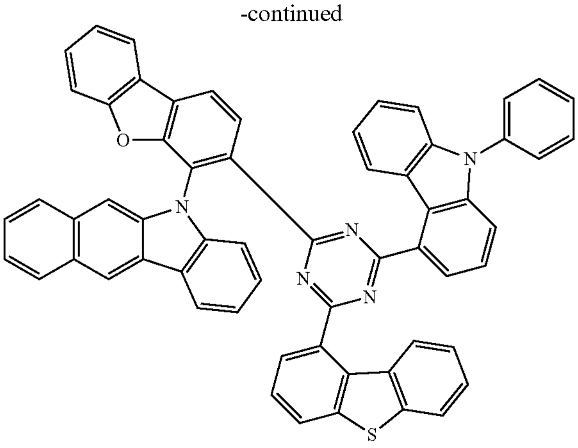
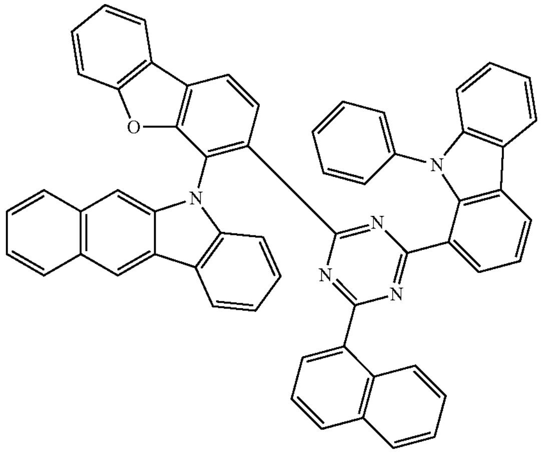
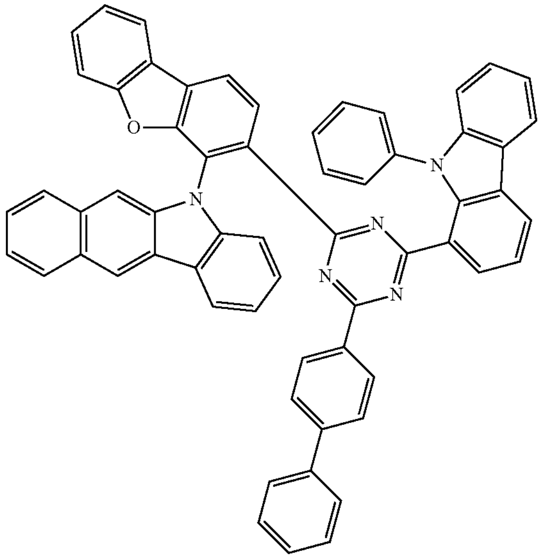

-continued
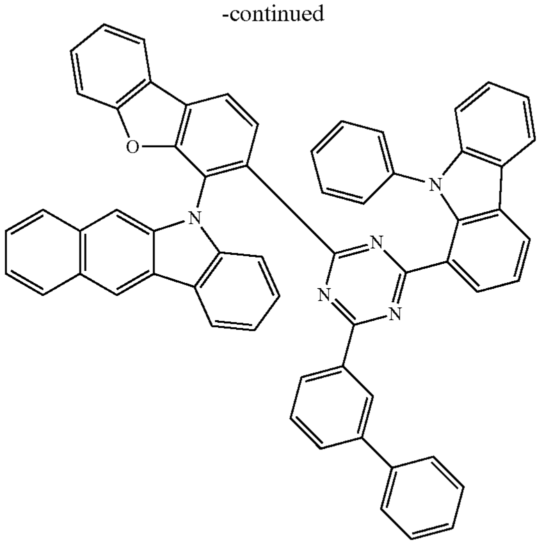
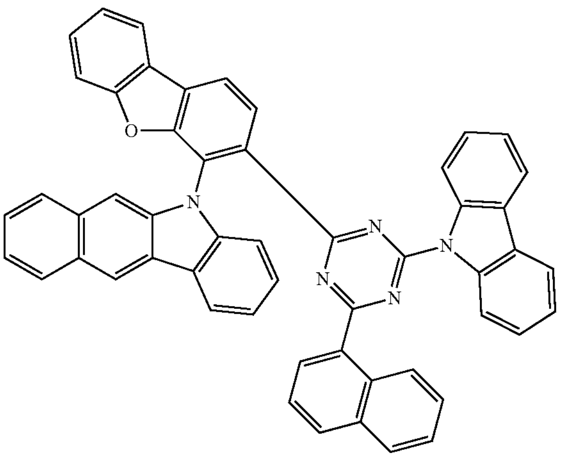
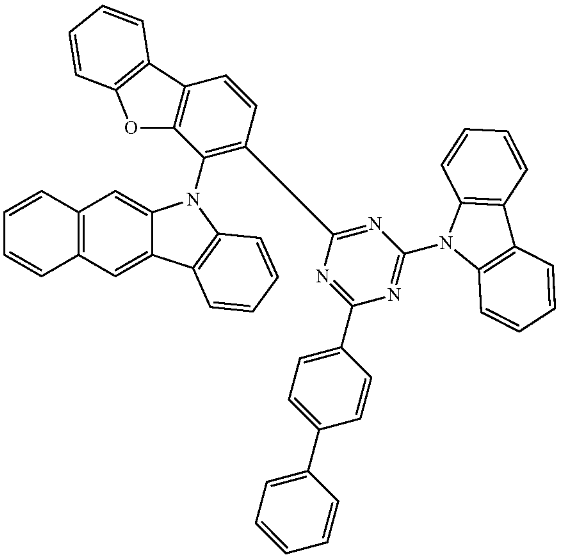
-continued
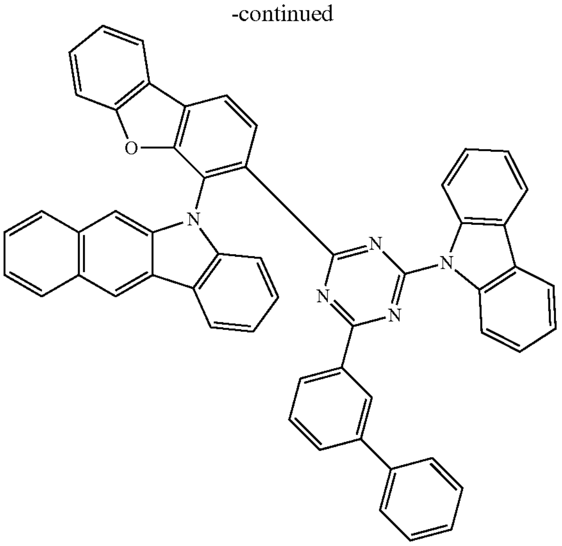
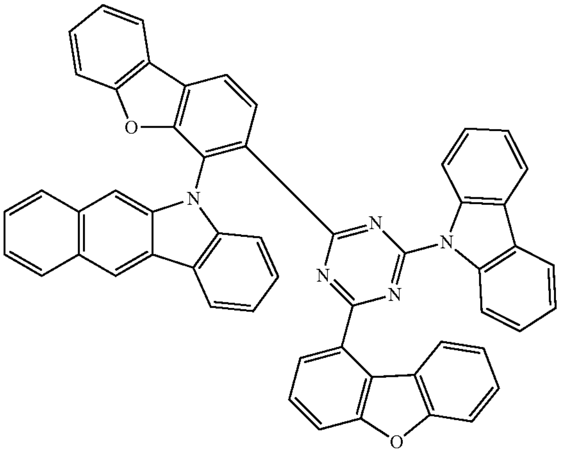
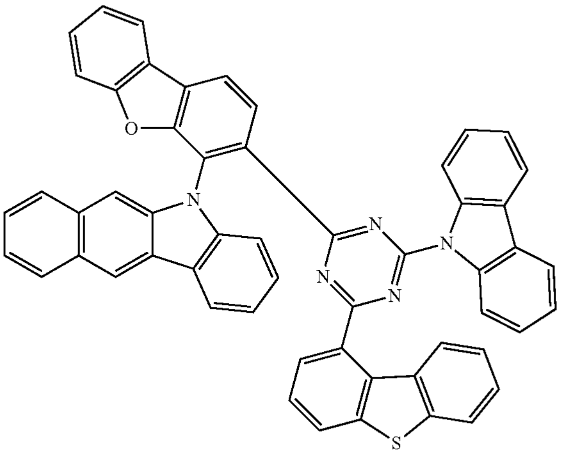

-continued
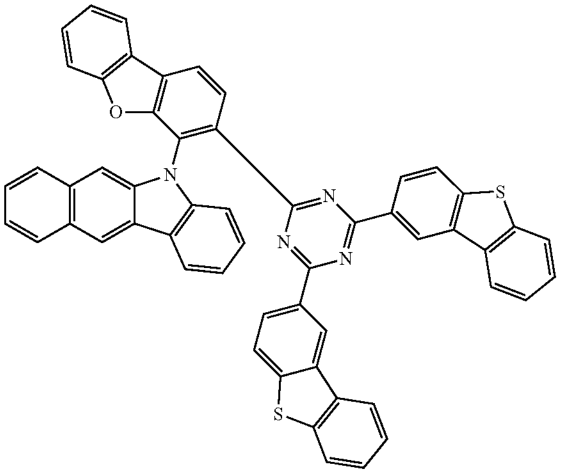
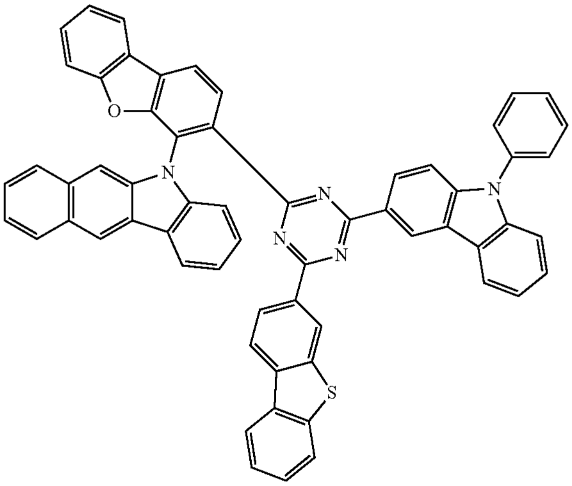
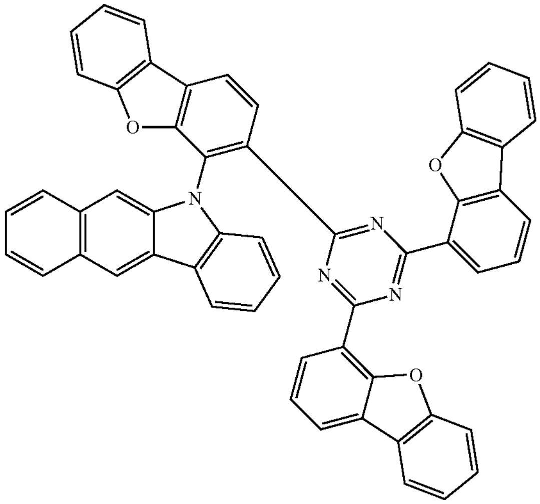
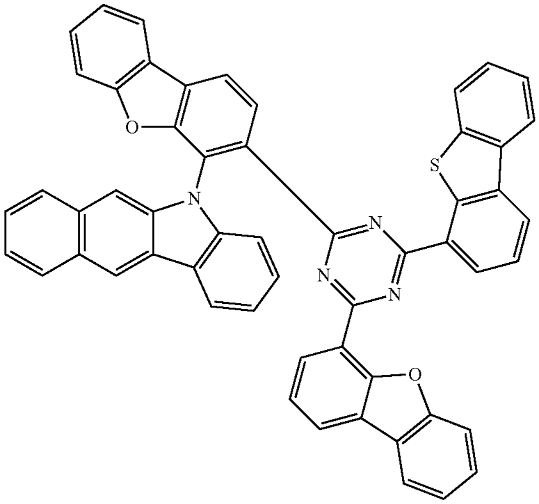
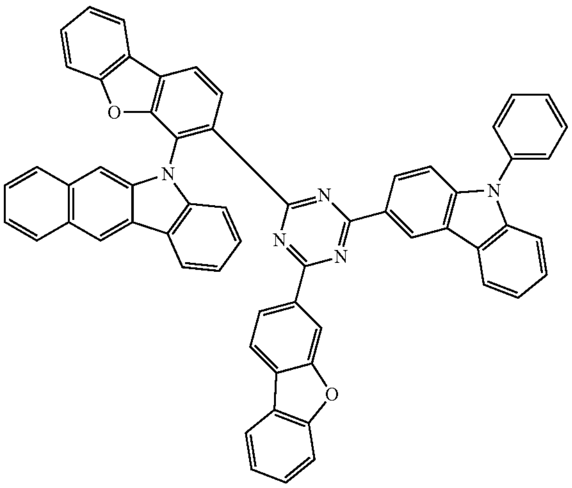
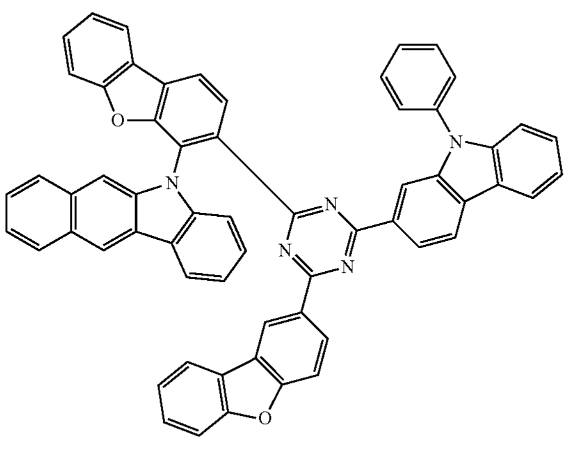
-continued -continued
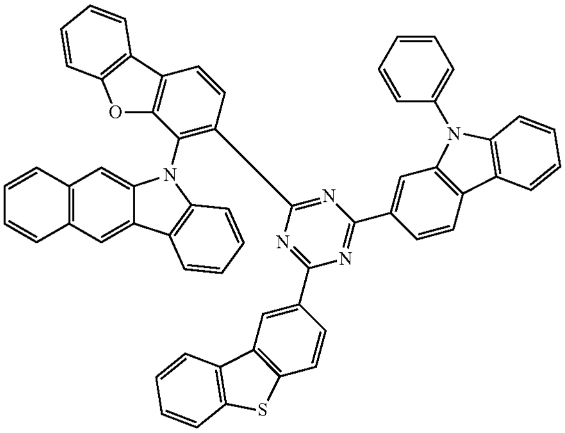
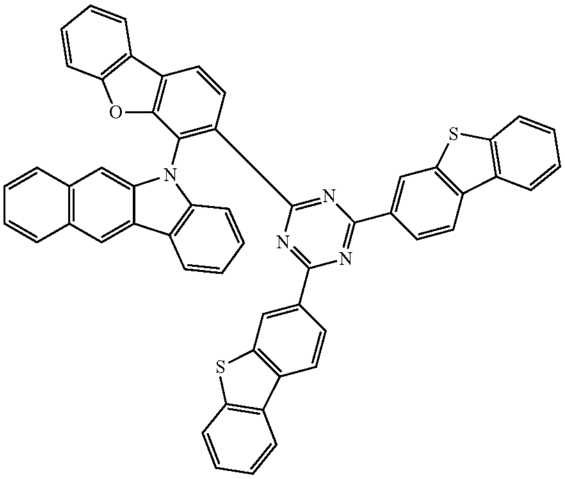
-continued
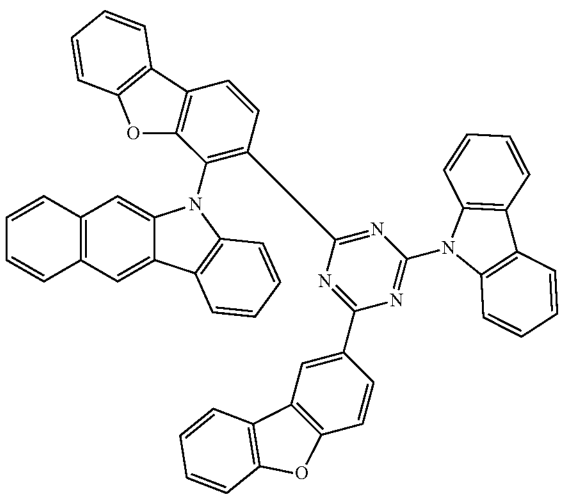
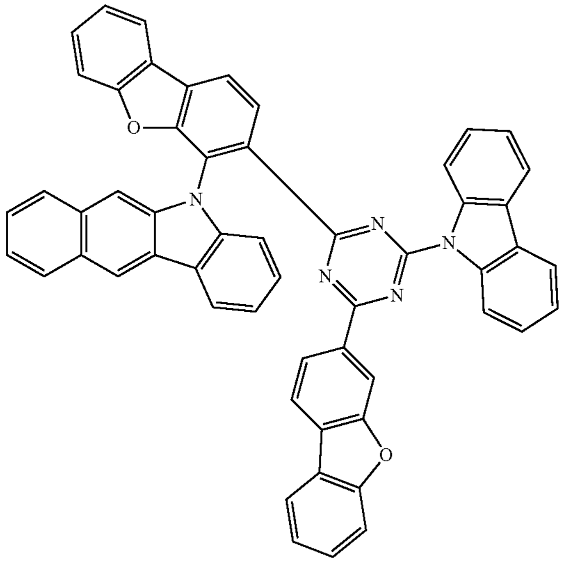
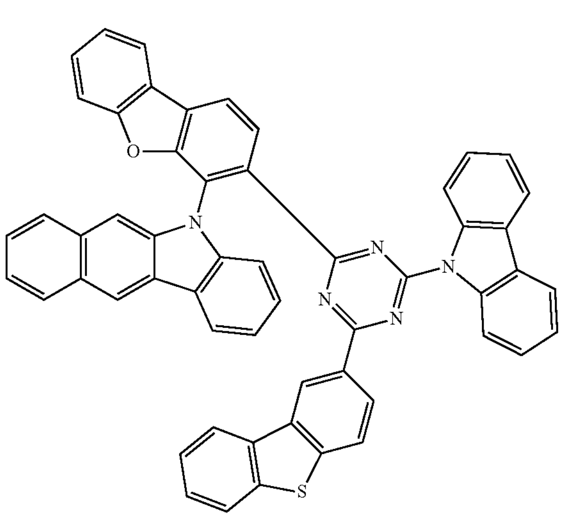
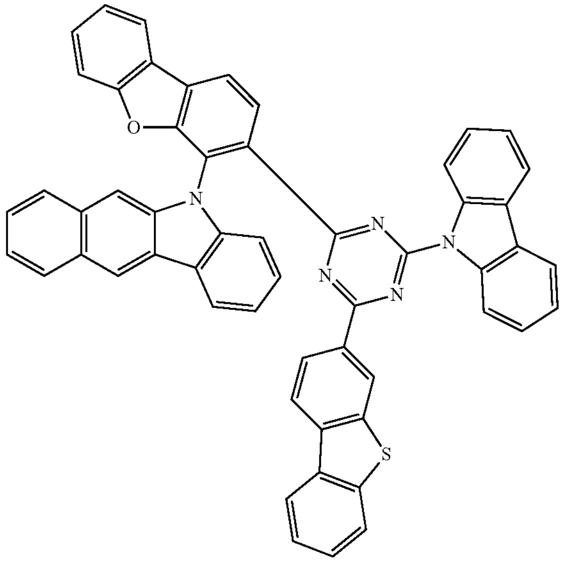

-continued
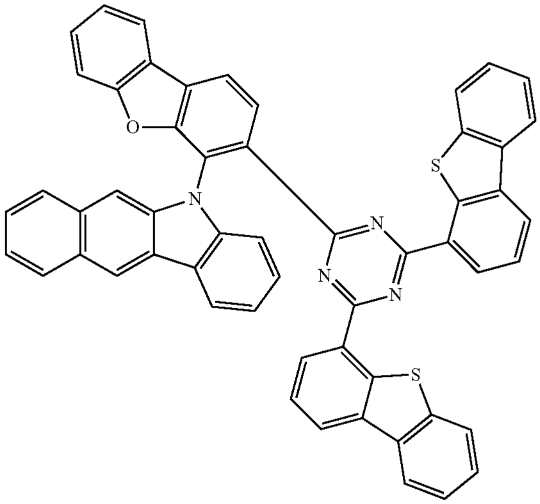
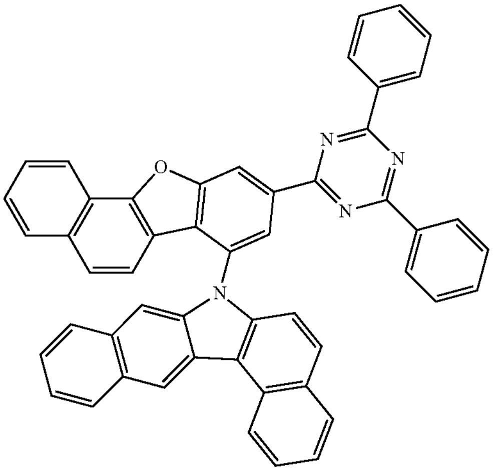
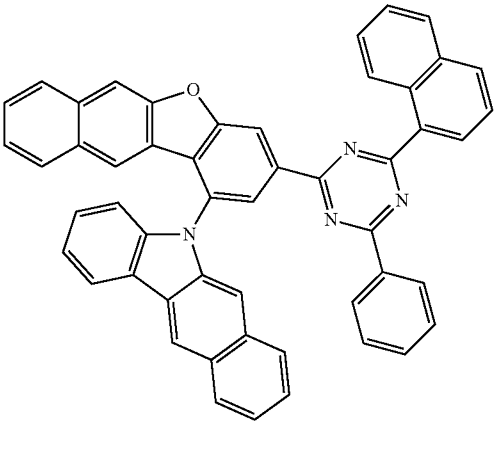
-continued
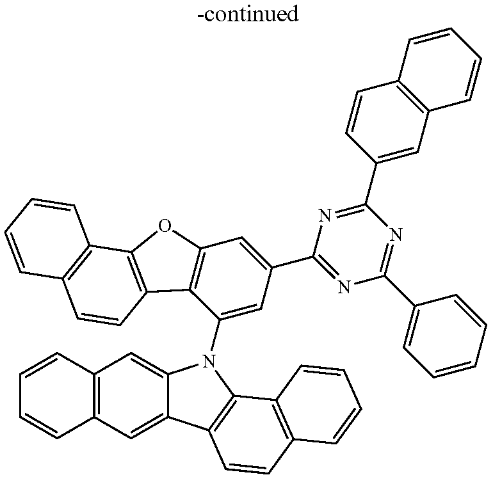
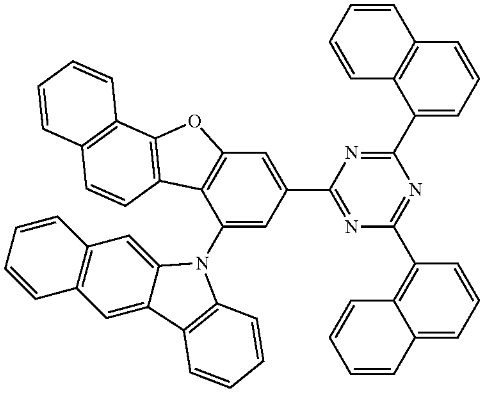
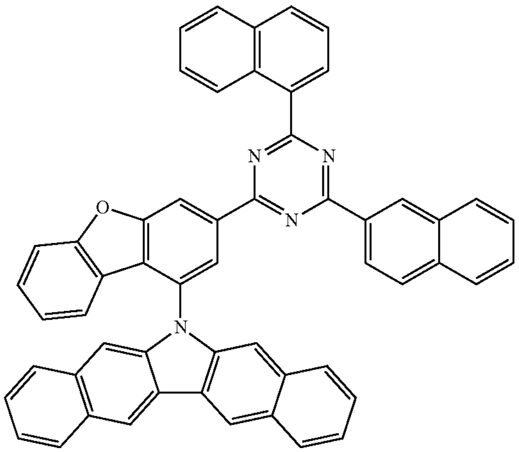
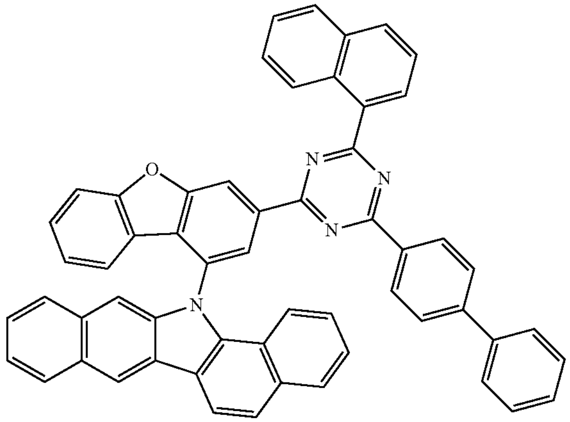

-continued
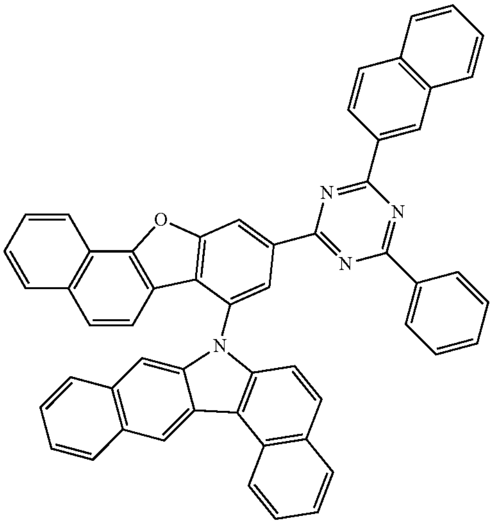
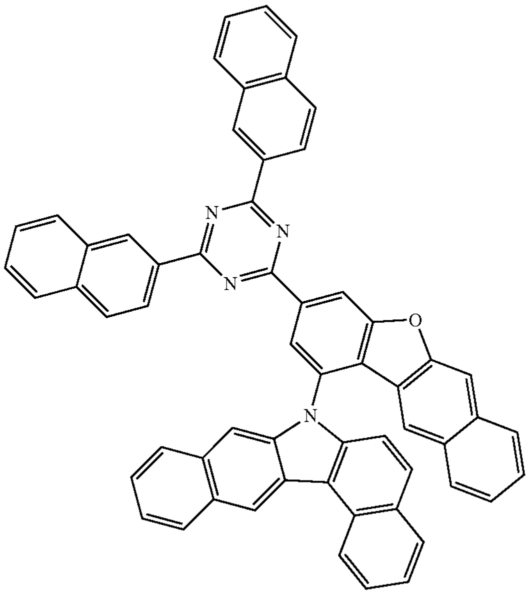
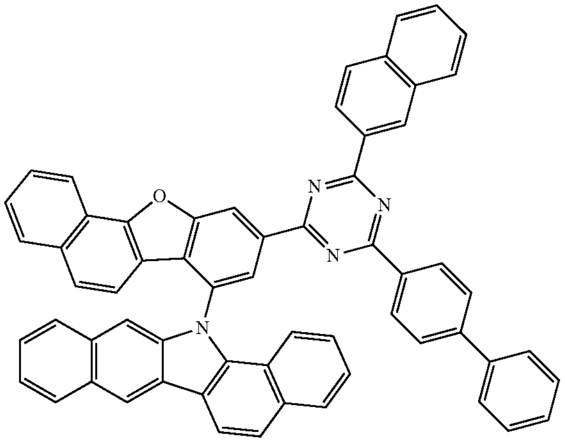
-continued
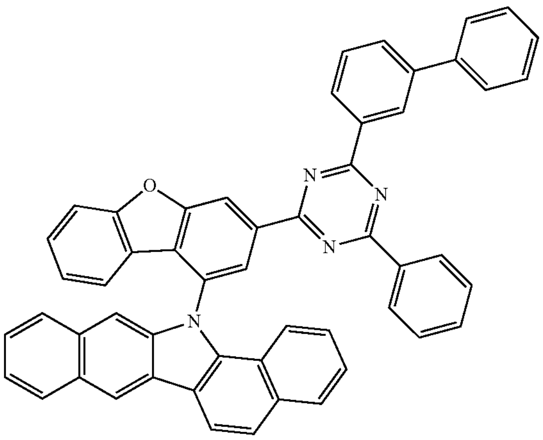
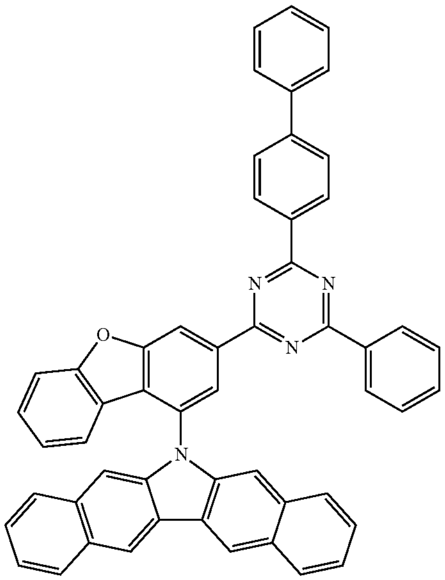
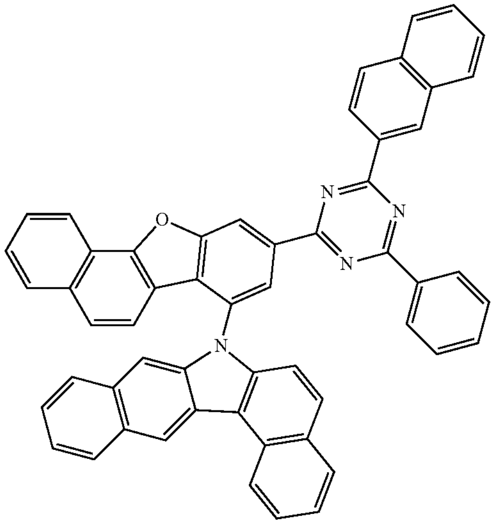

-continued
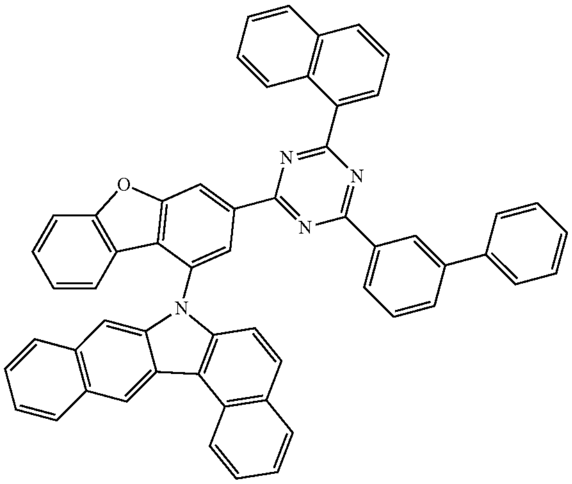
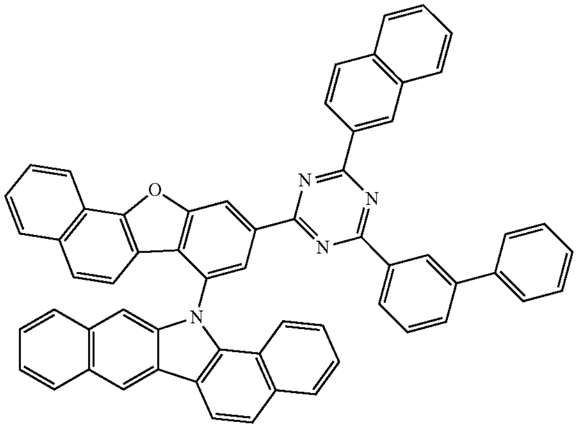
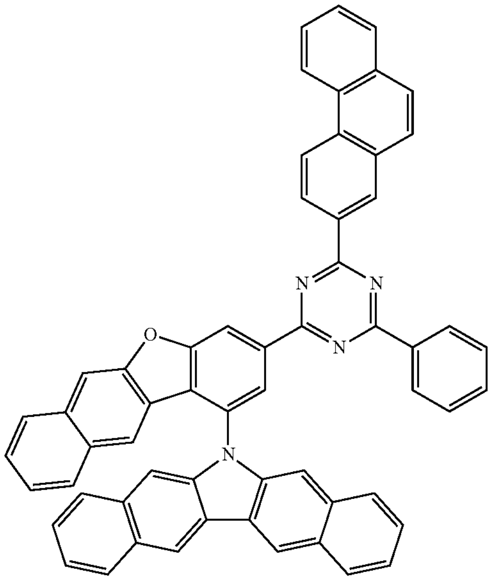
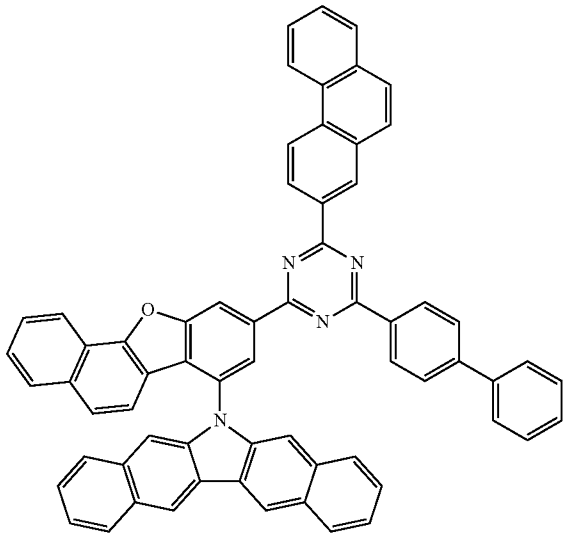
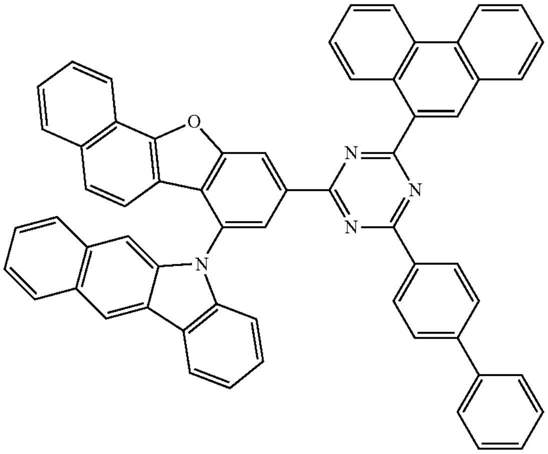
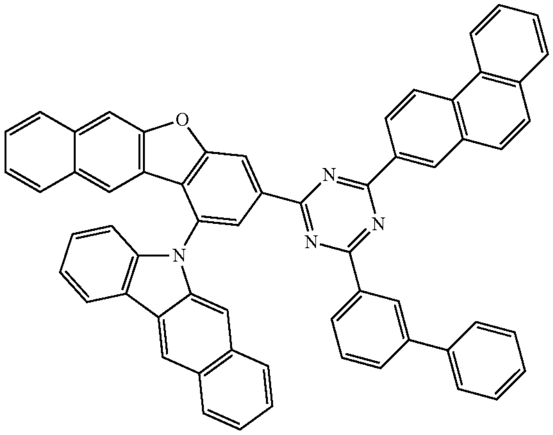
-continued -continued
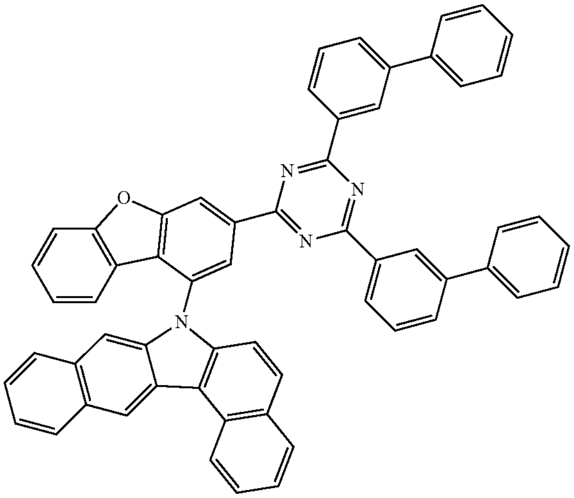
-continued
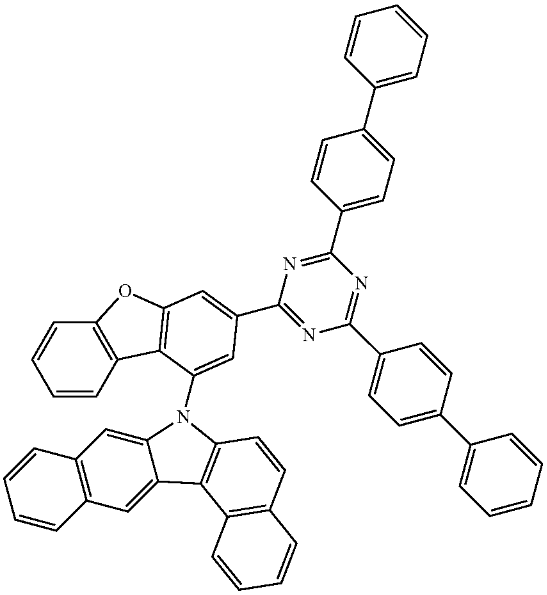
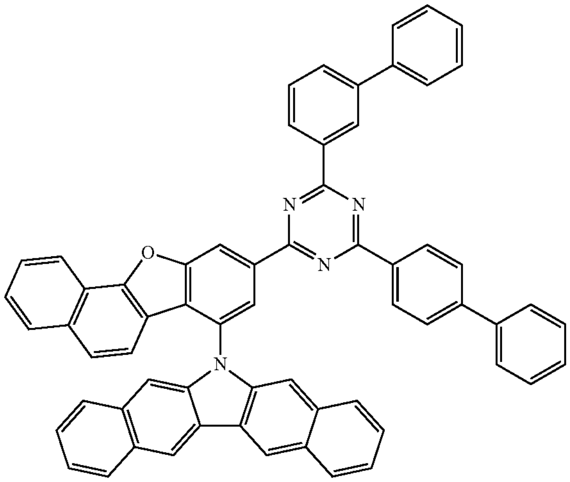
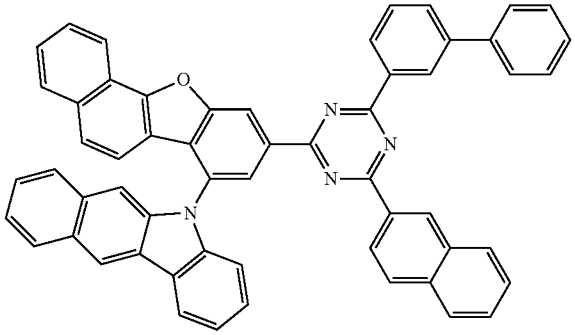
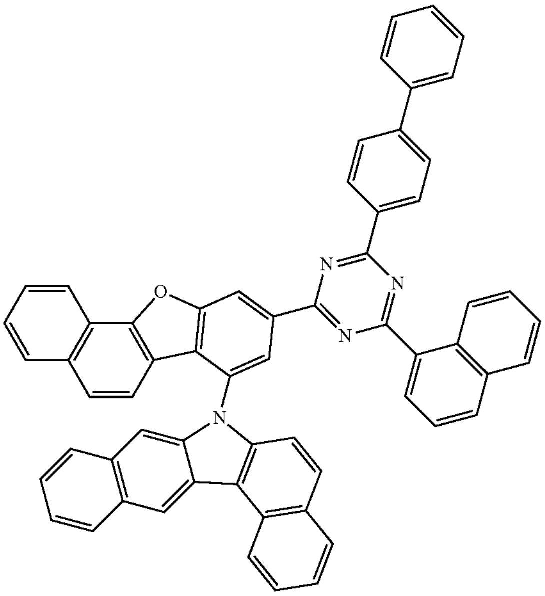

-continued
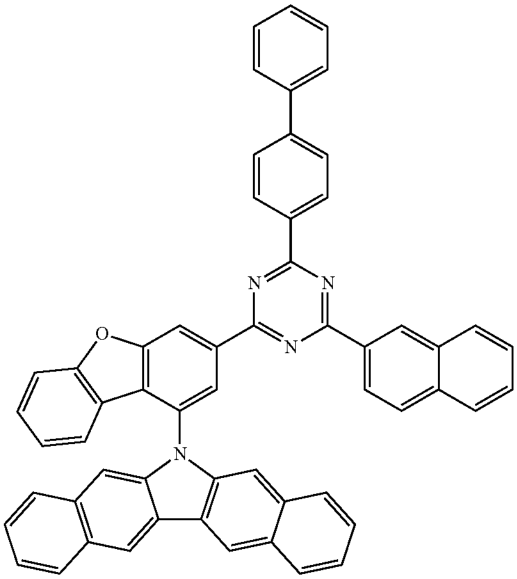
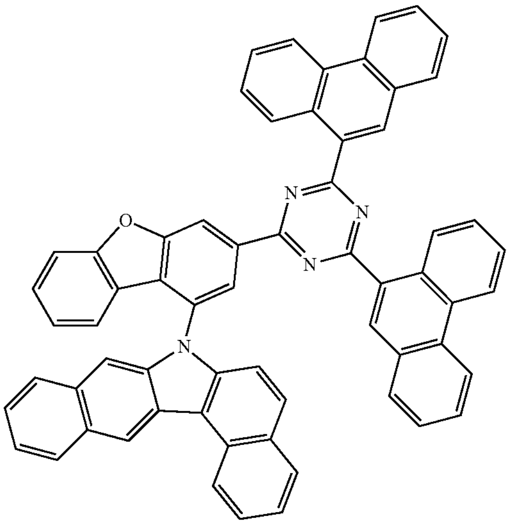
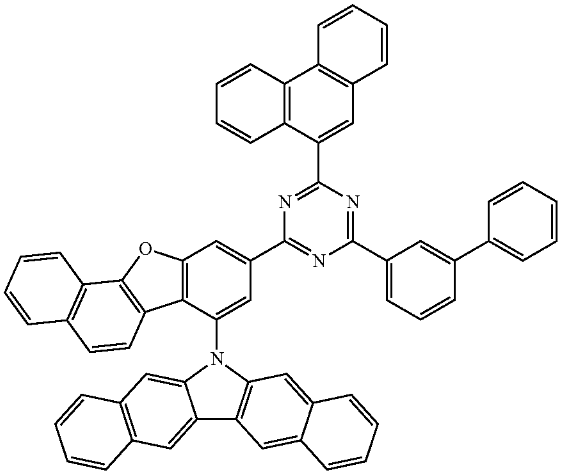
-continued
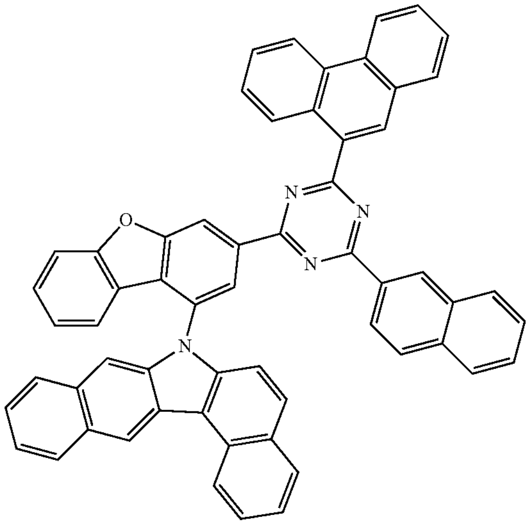
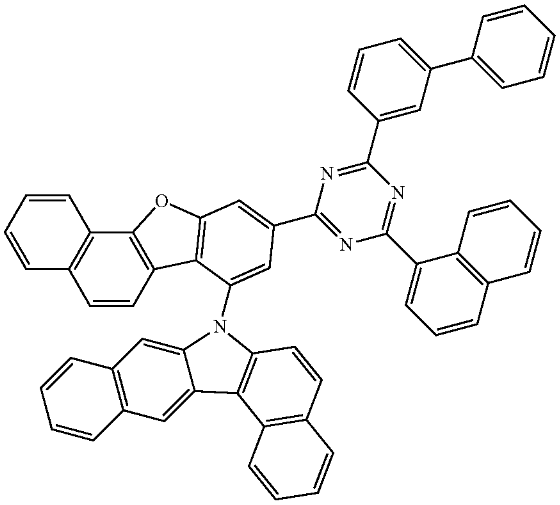
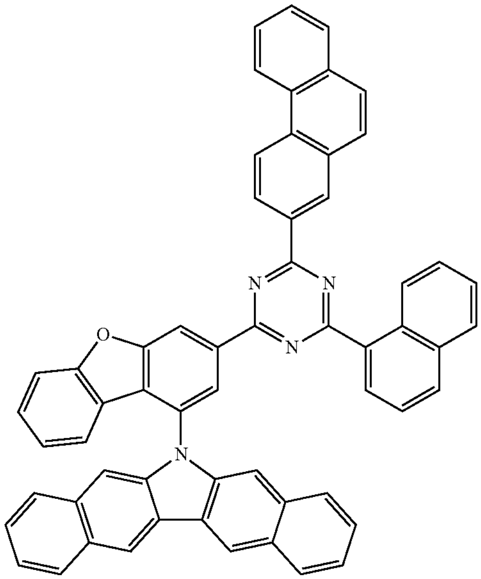

-continued
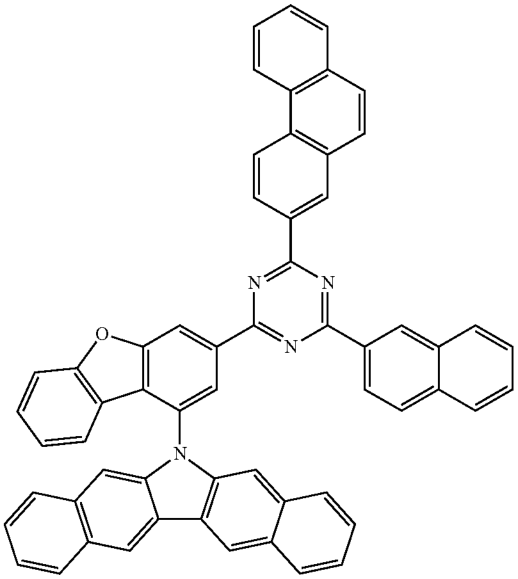
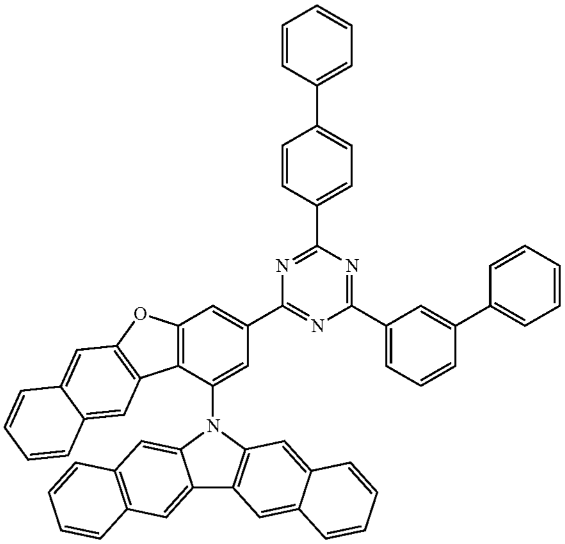
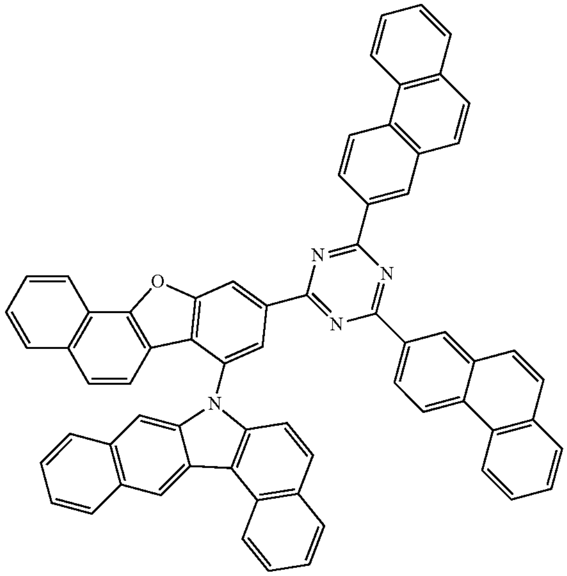
-continued
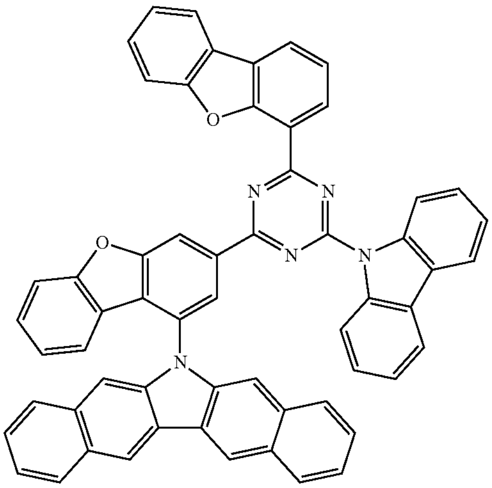
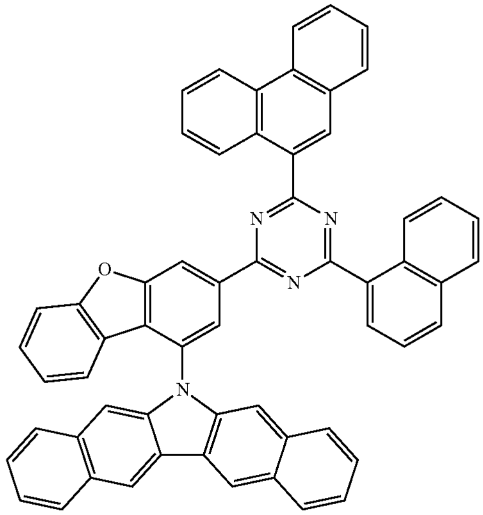
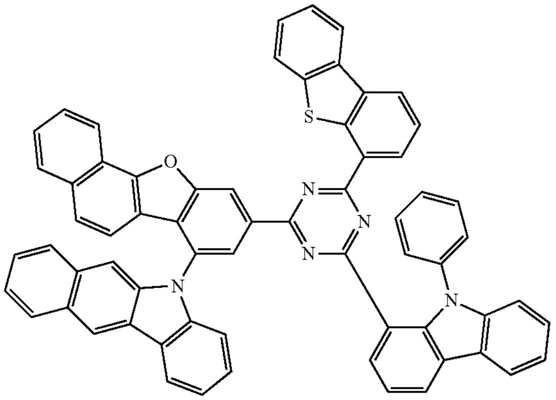

-continued
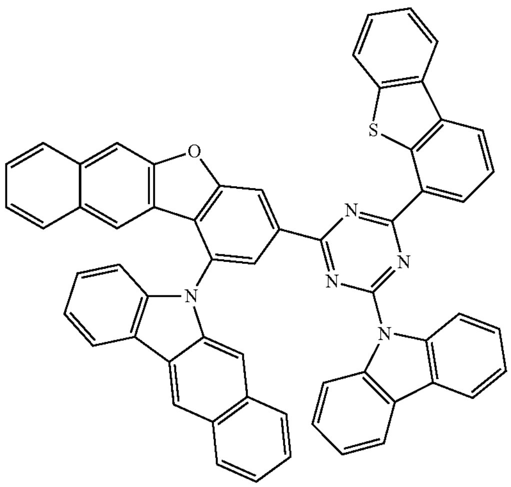
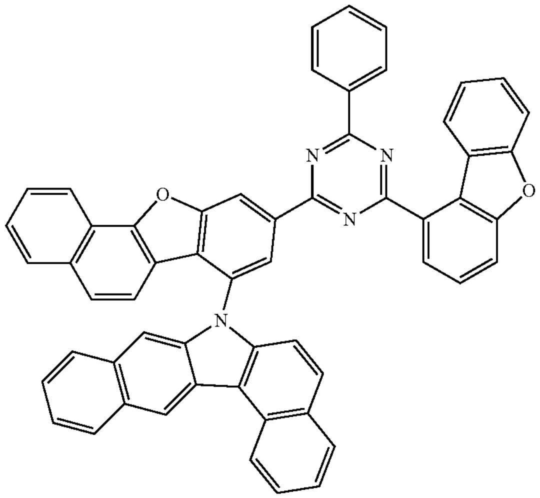
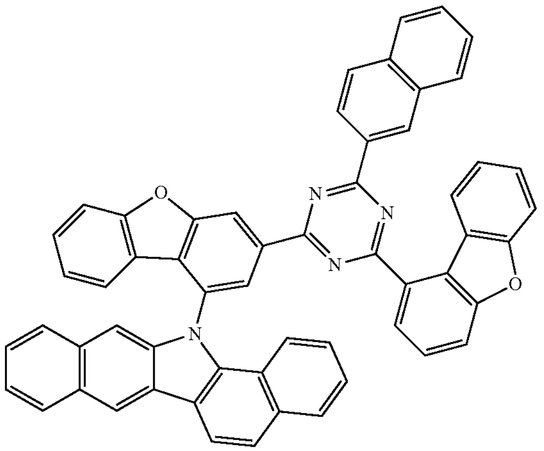
-continued
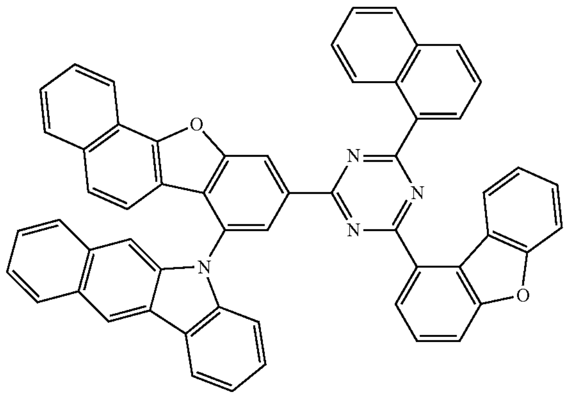
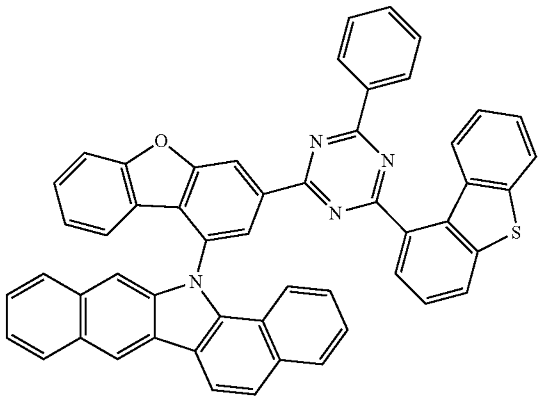
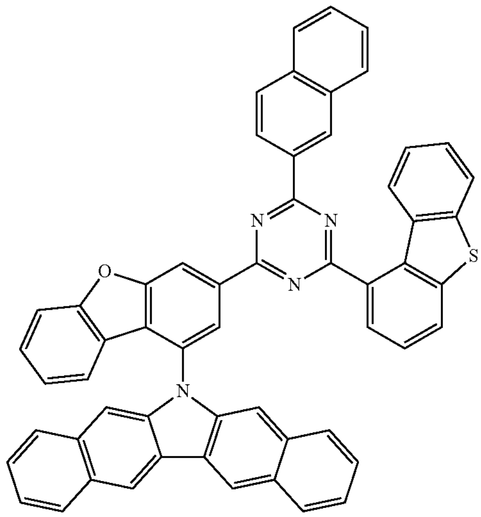

-continued
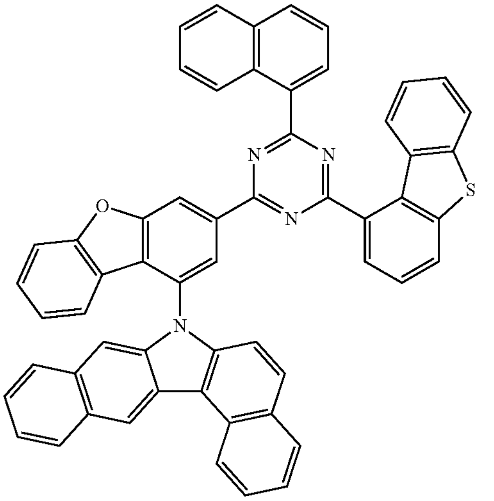
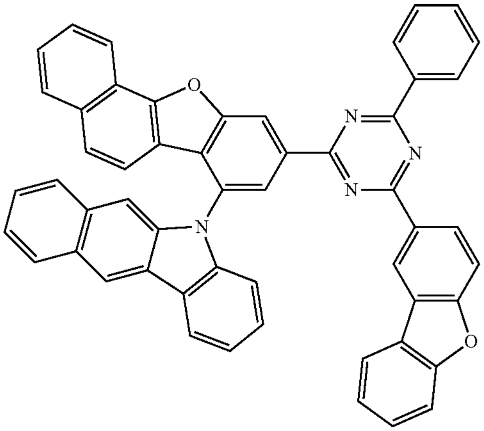
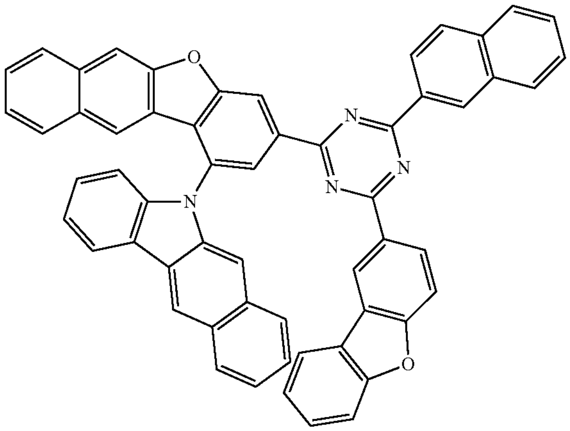
-continued
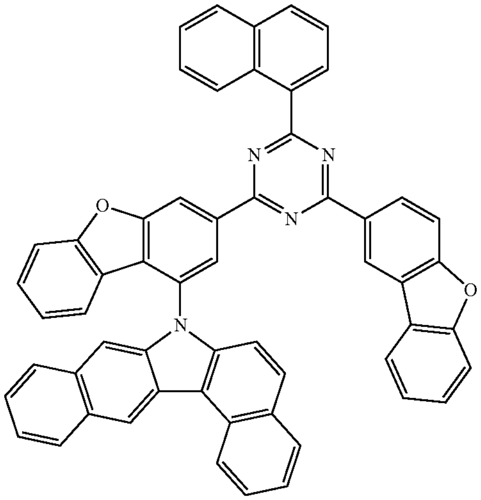
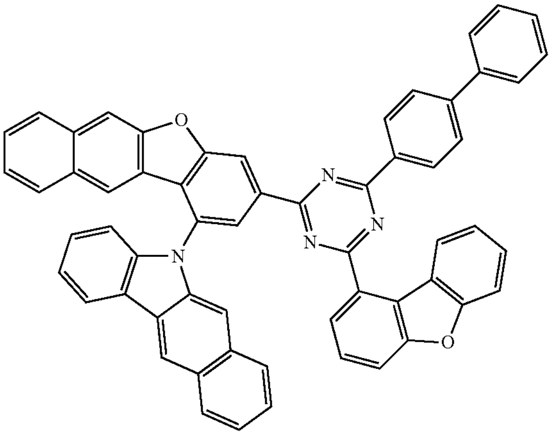
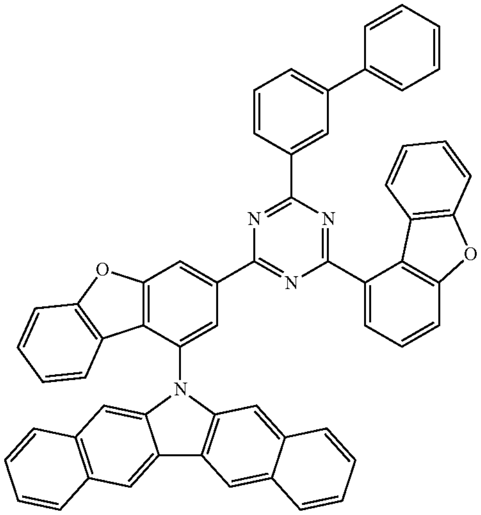

-continued
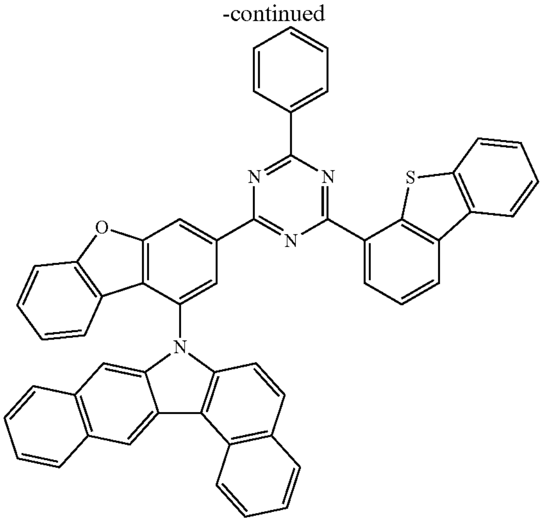
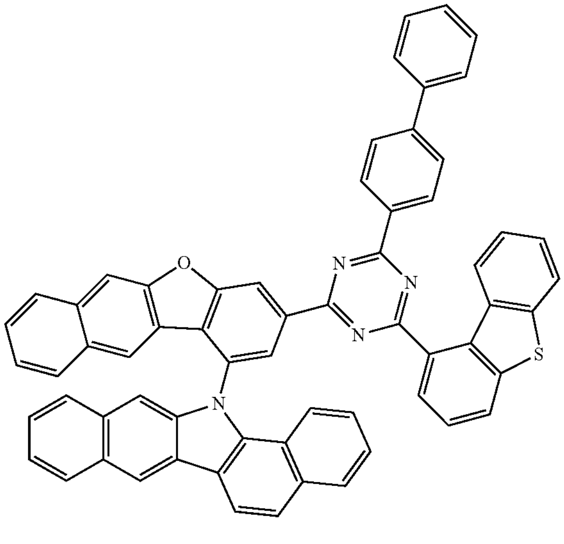
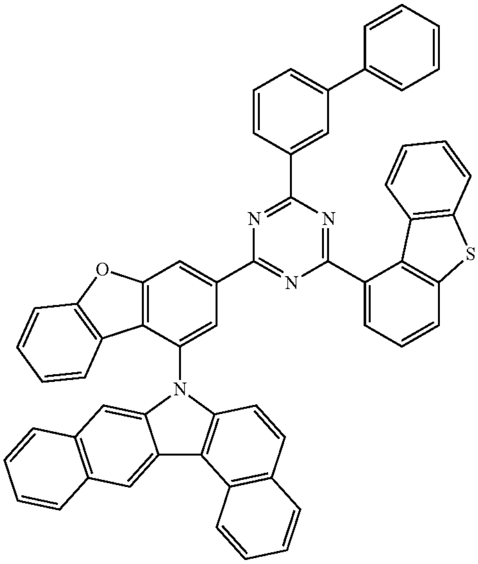
-continued
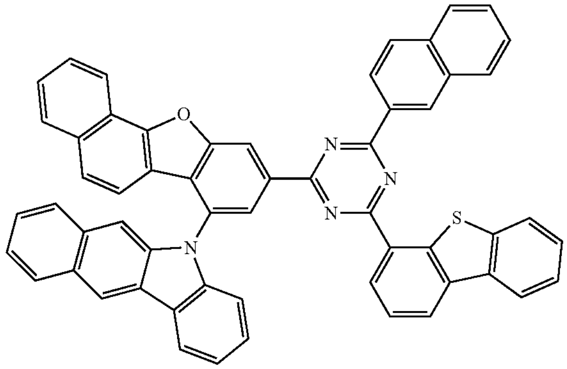
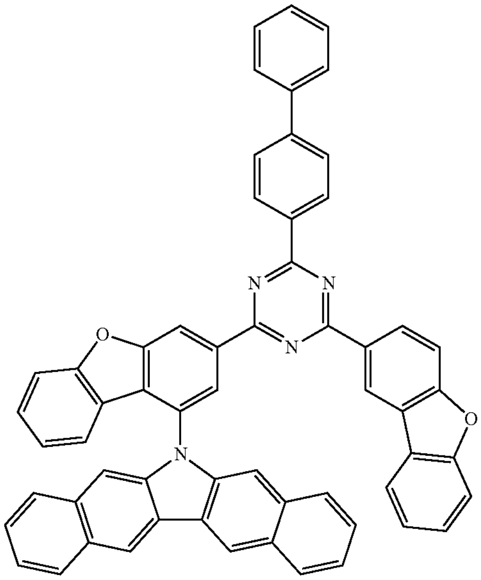
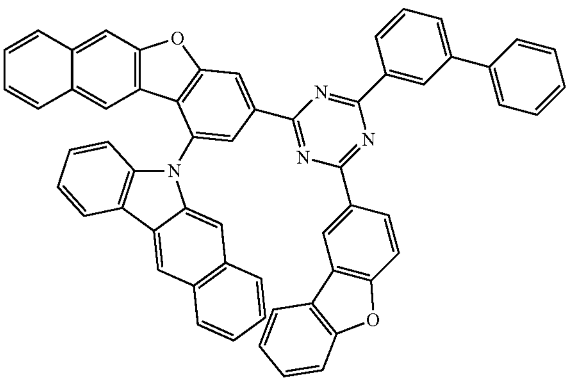

-continued
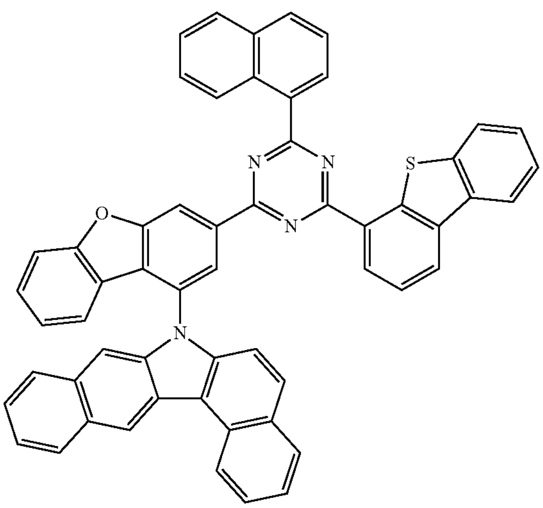
-continued
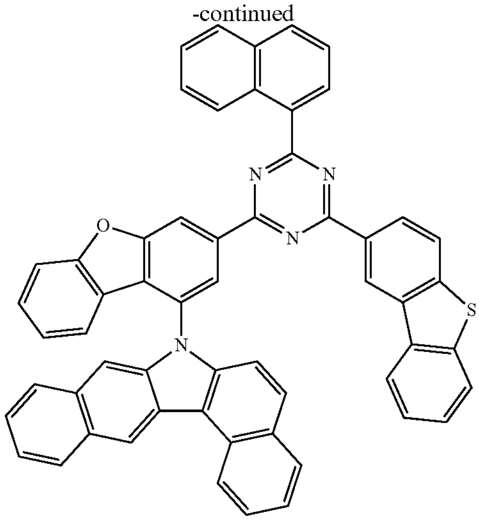
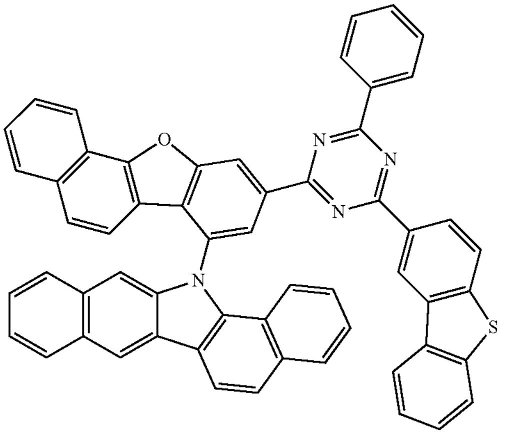
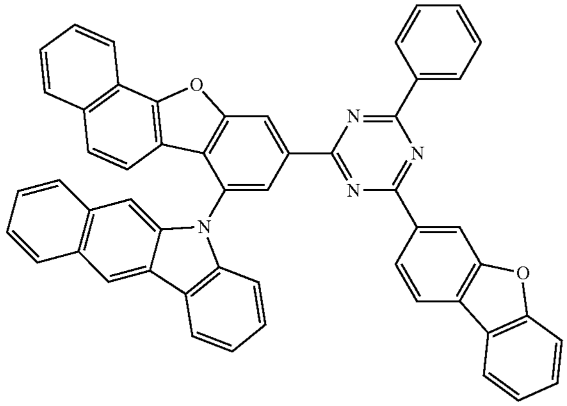
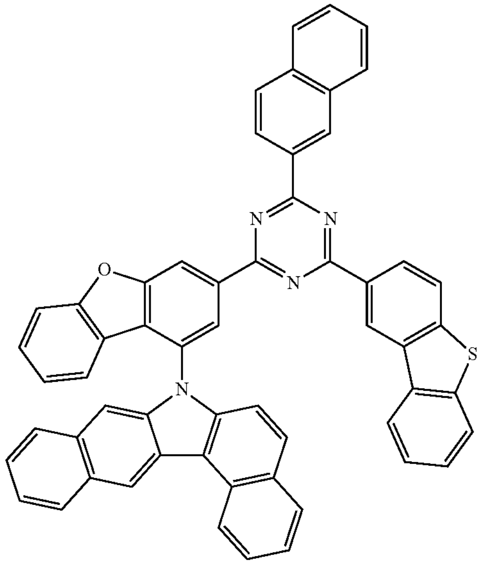
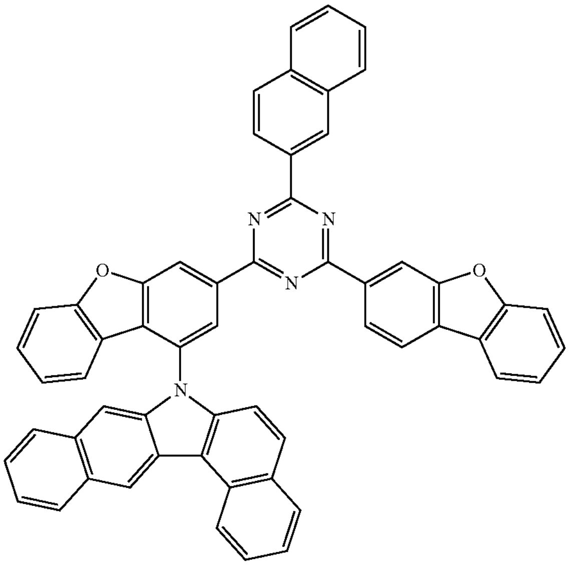

-continued
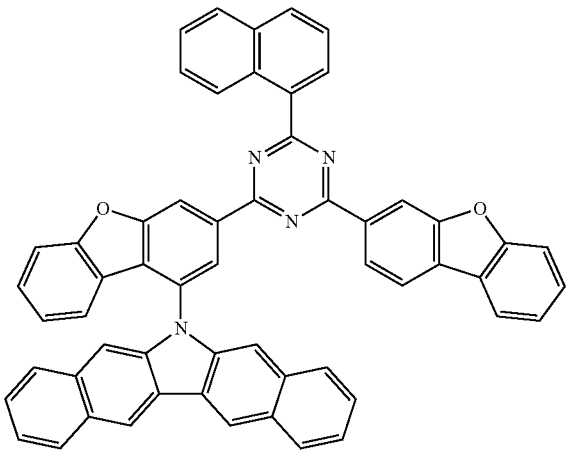
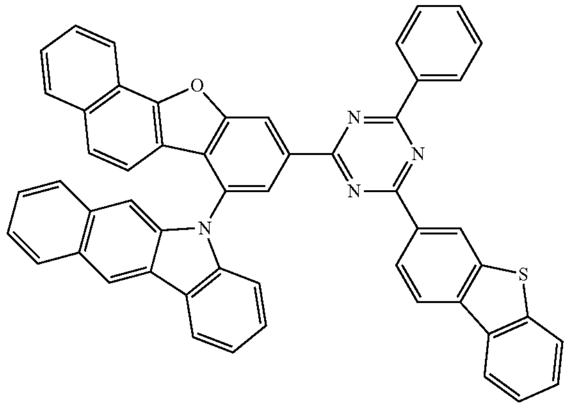
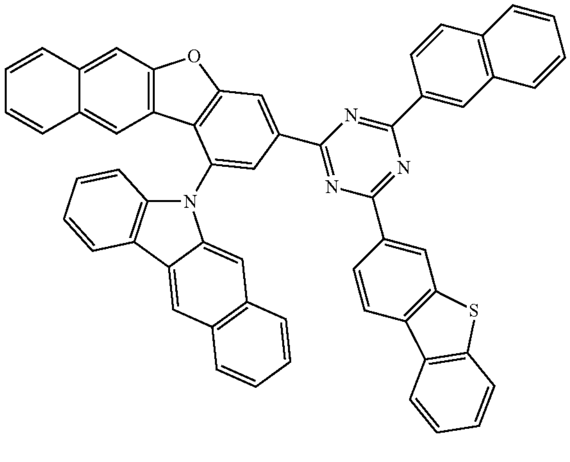
-continued
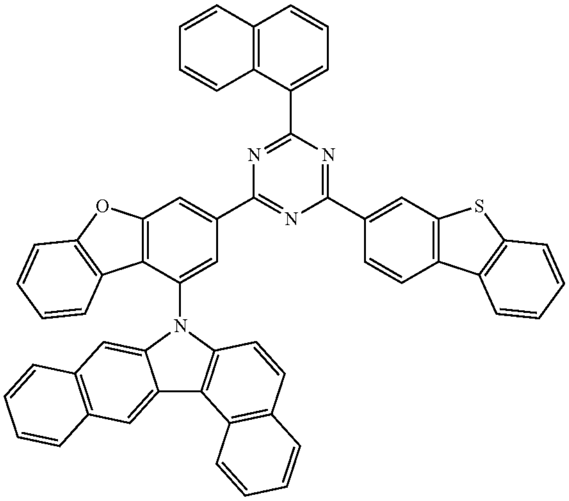
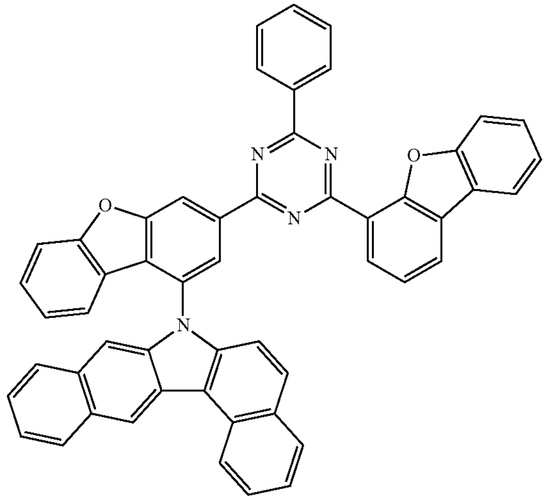
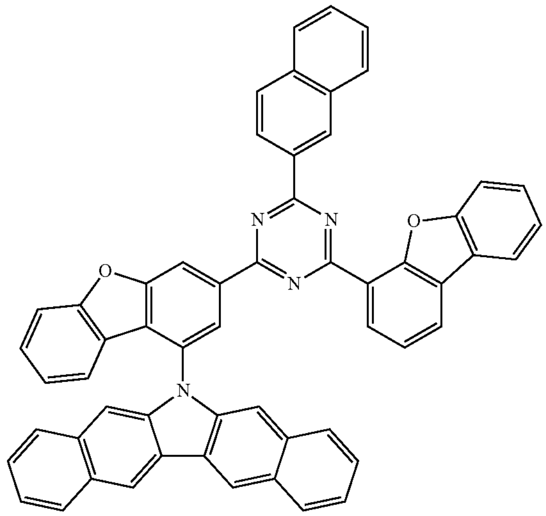

-continued
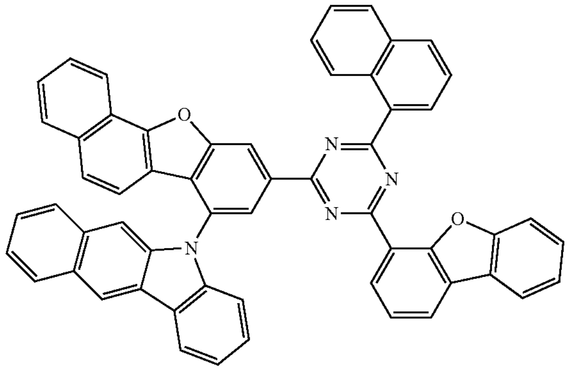
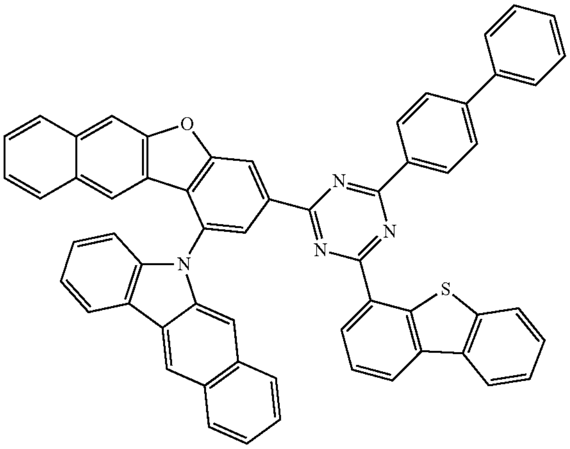
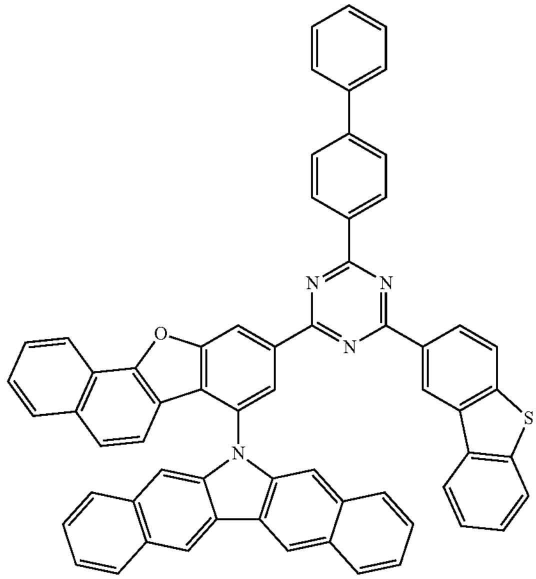
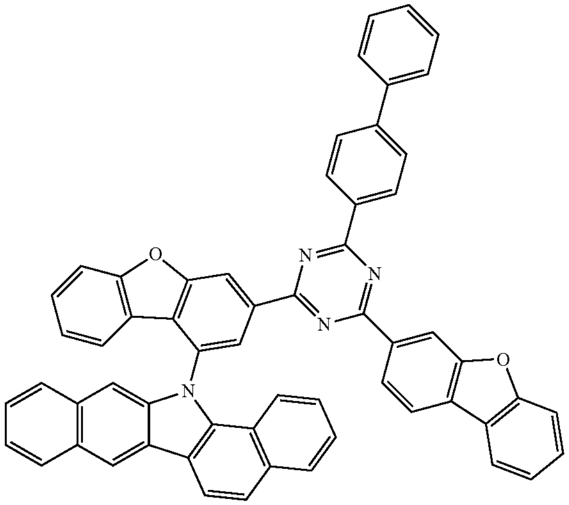
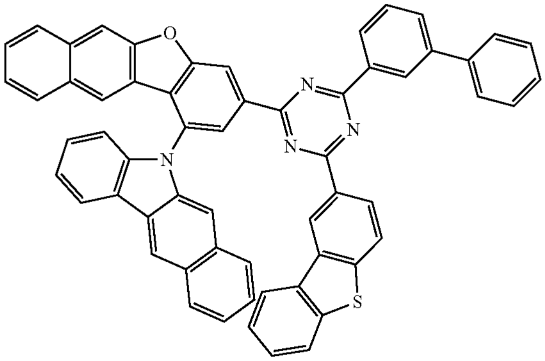
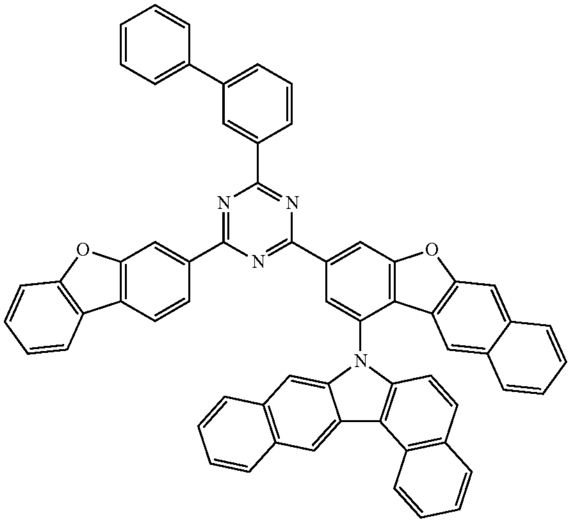
-continued -continued
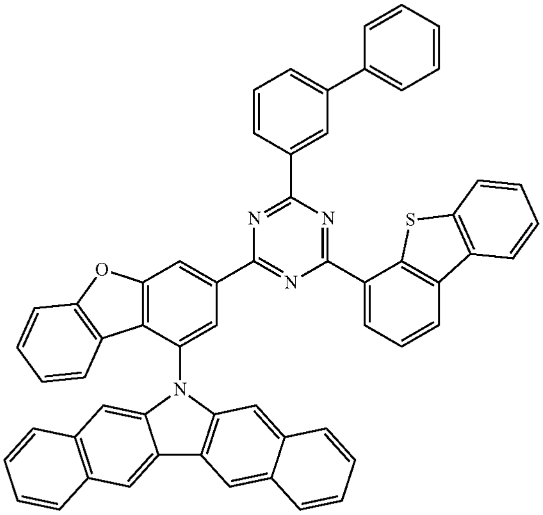
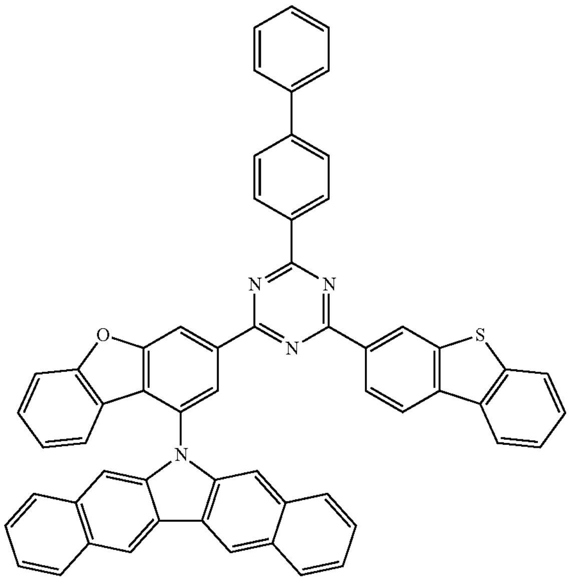
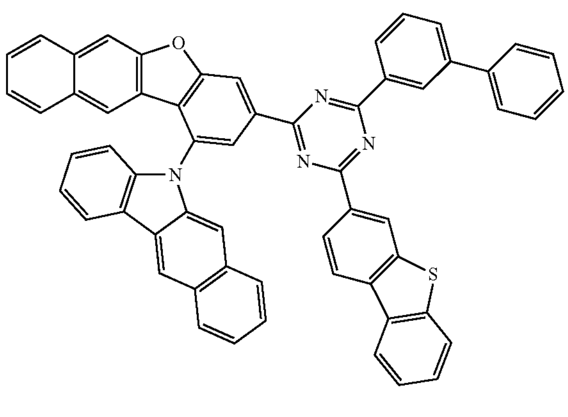
-continued
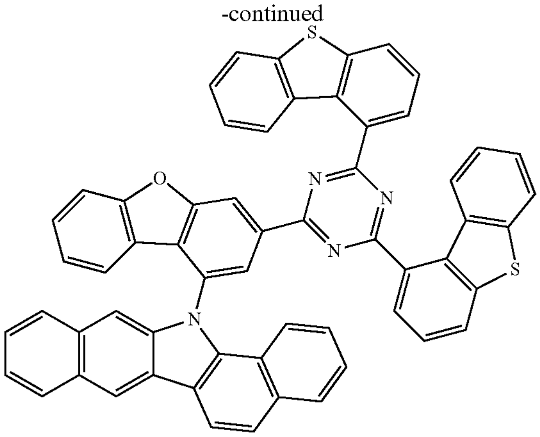
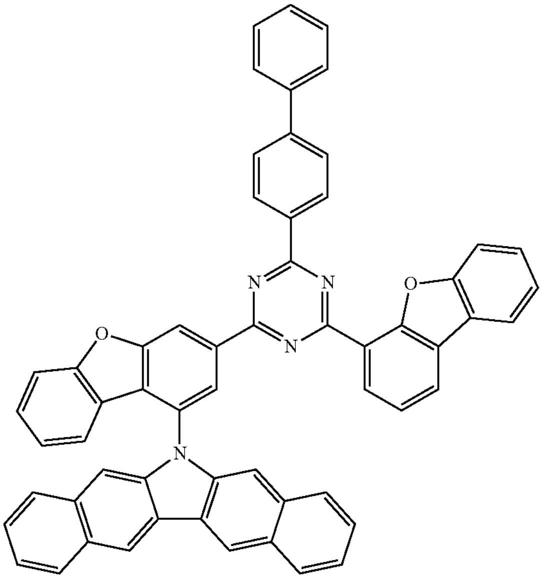
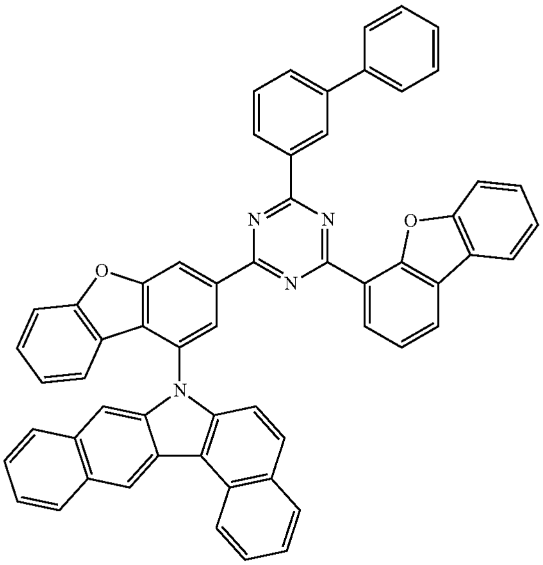

-continued
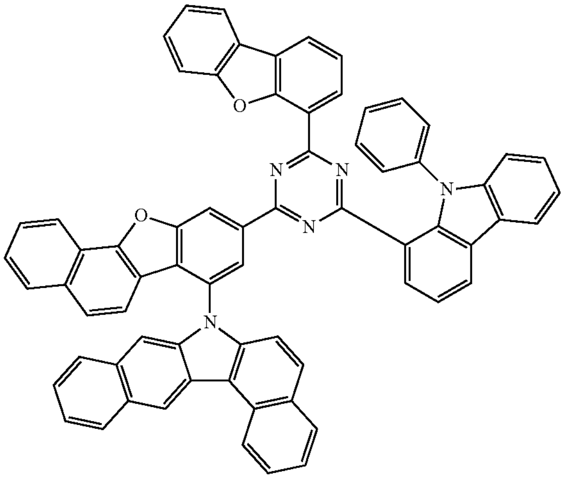
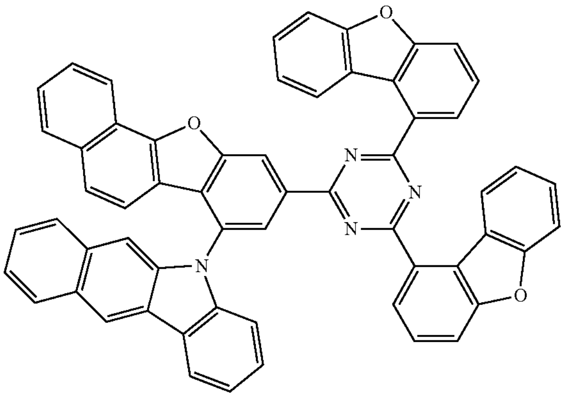
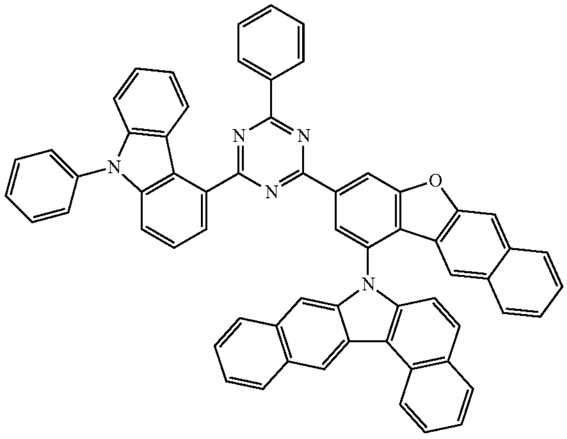
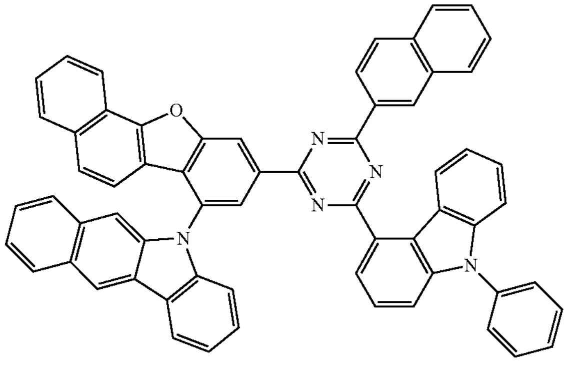
-continued
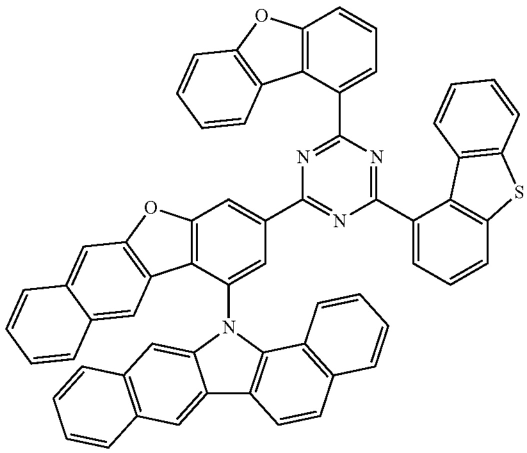
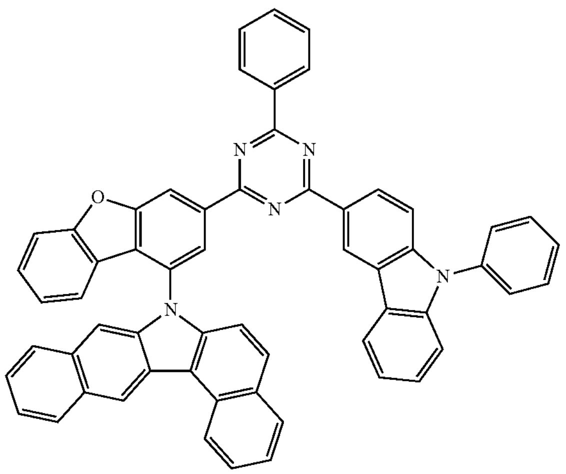
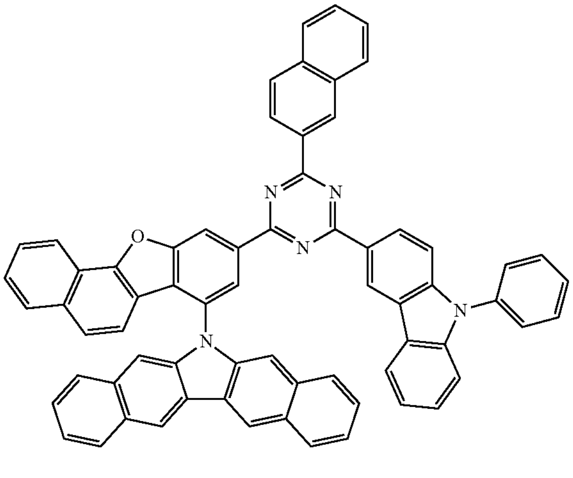

-continued
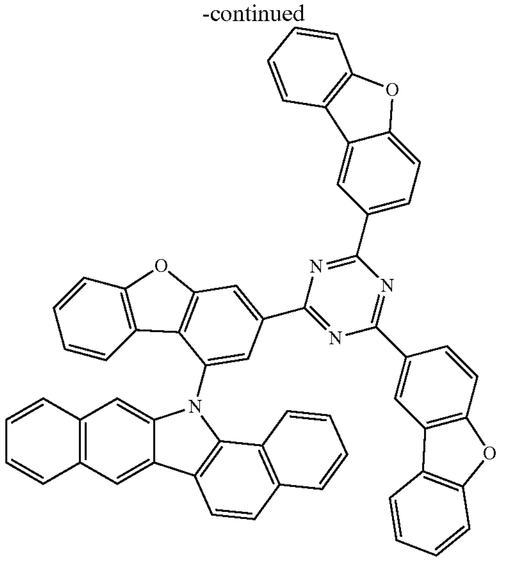
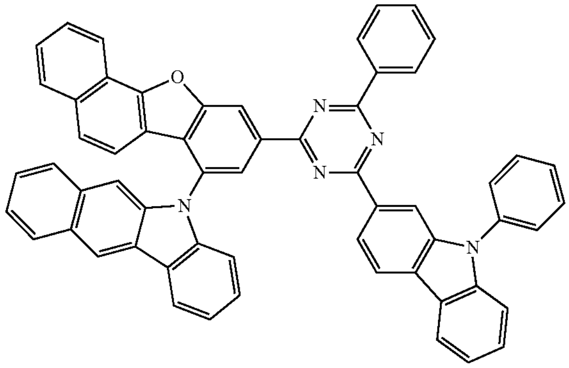
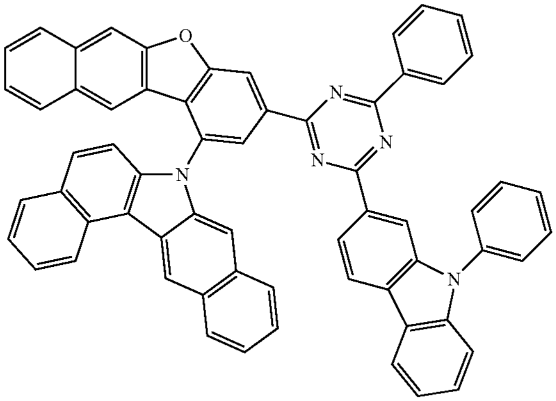
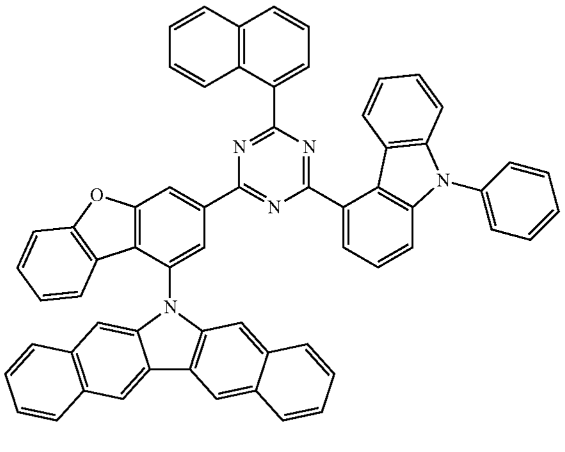
-continued
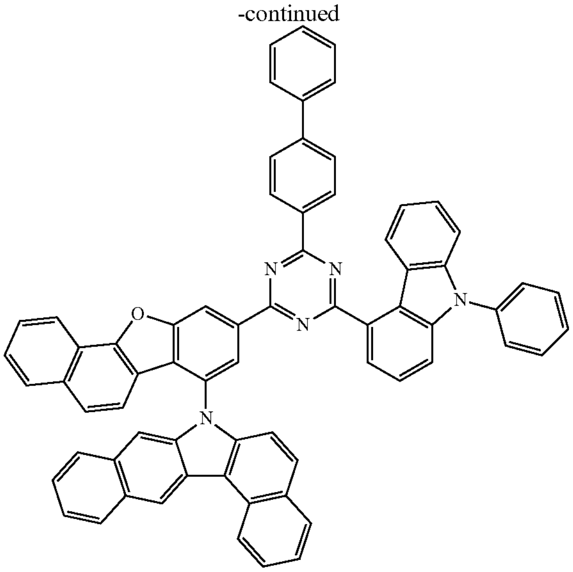
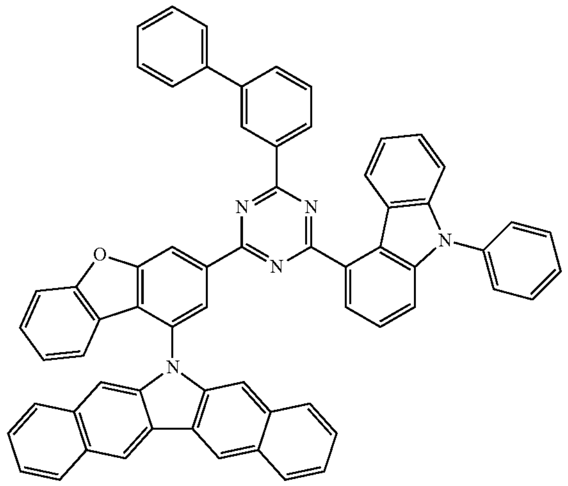
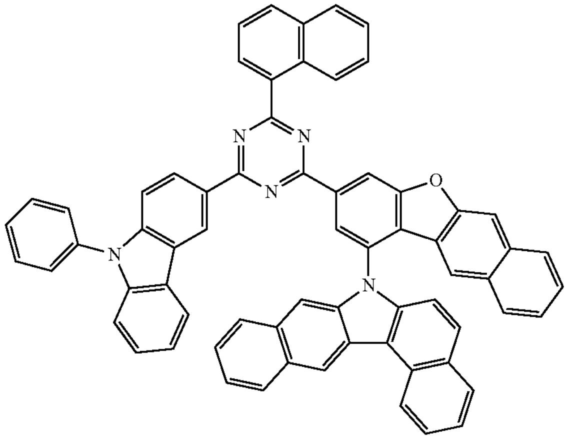

-continued
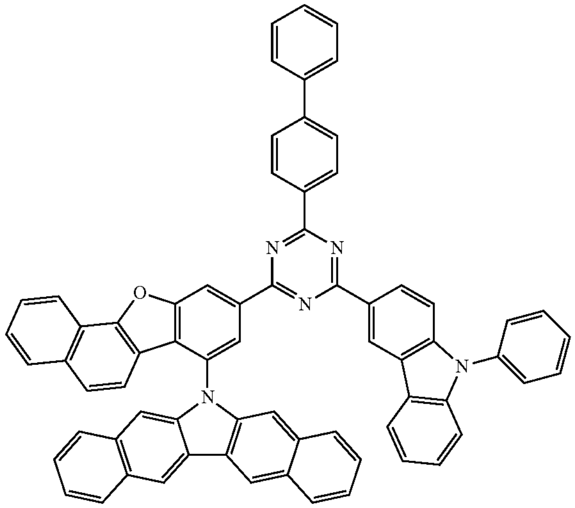
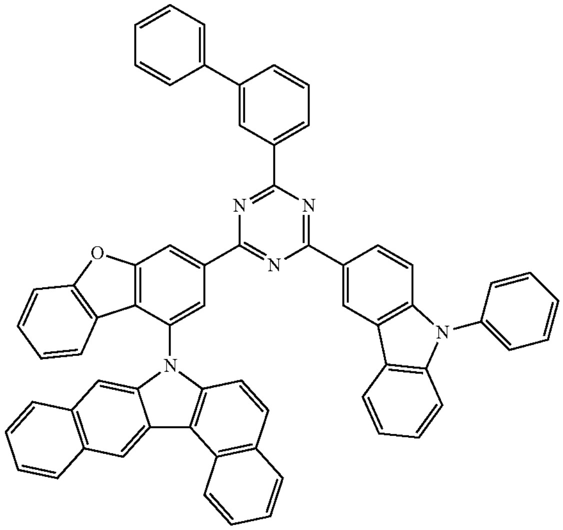
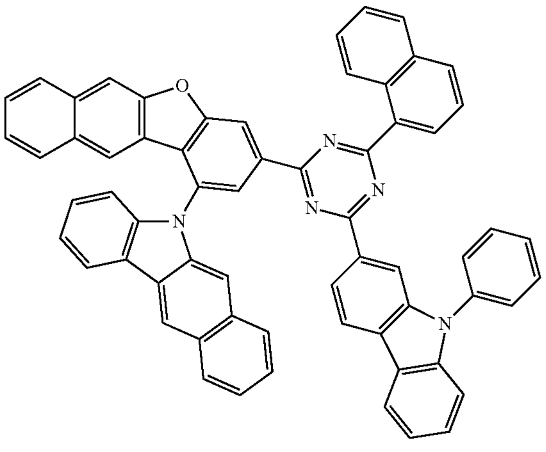
-continued
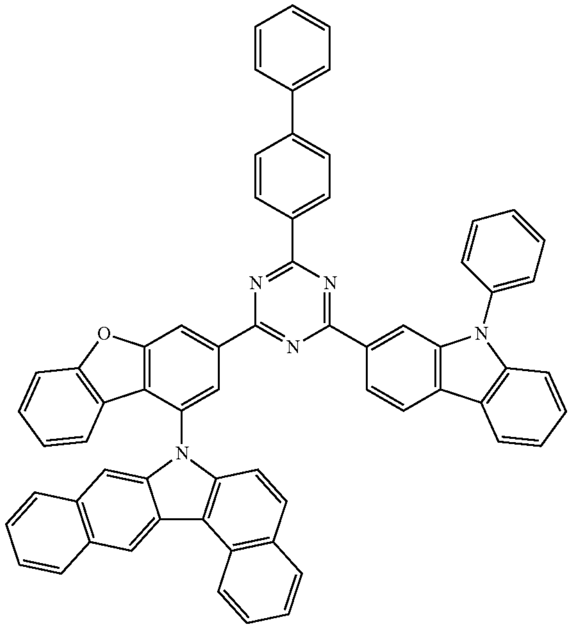
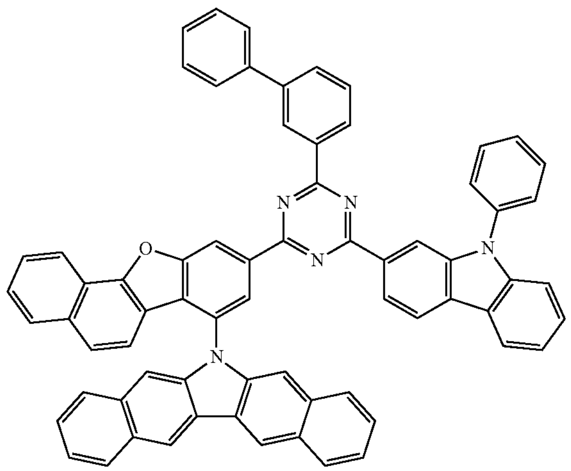
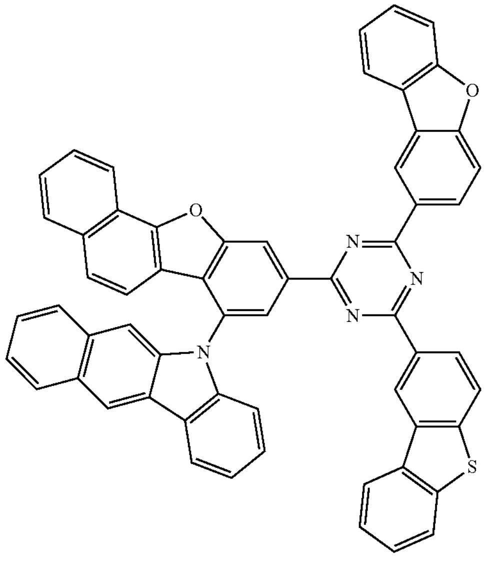

-continued
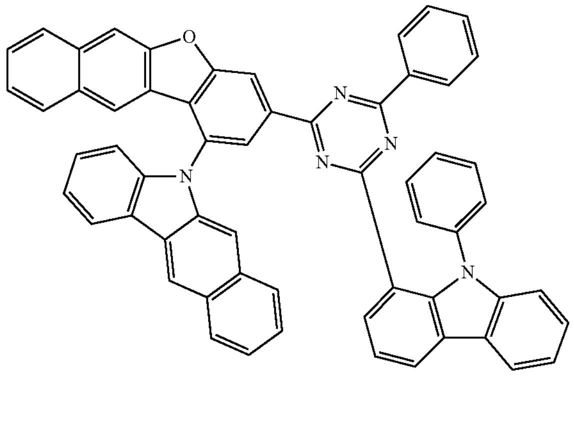
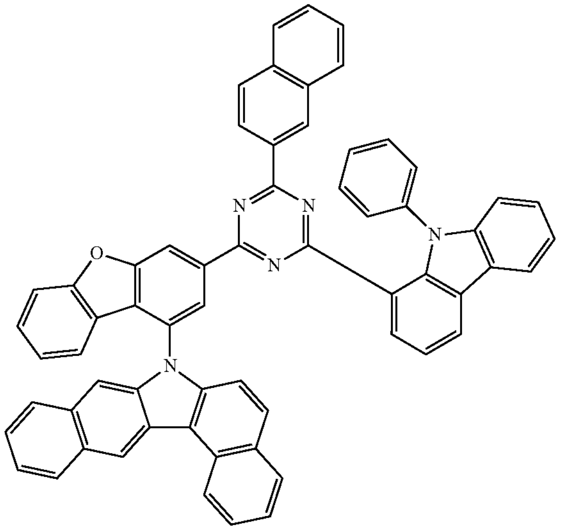
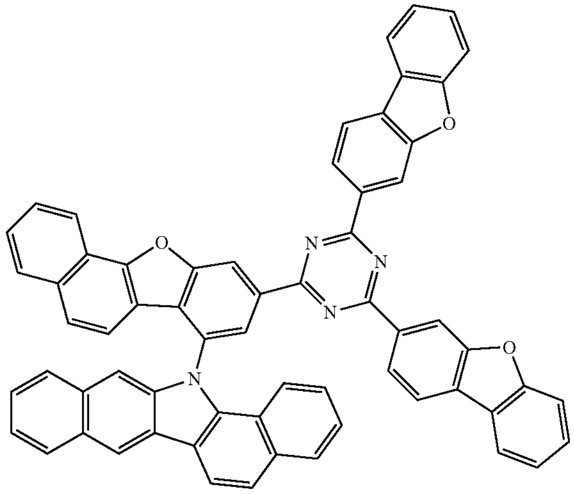
-continued
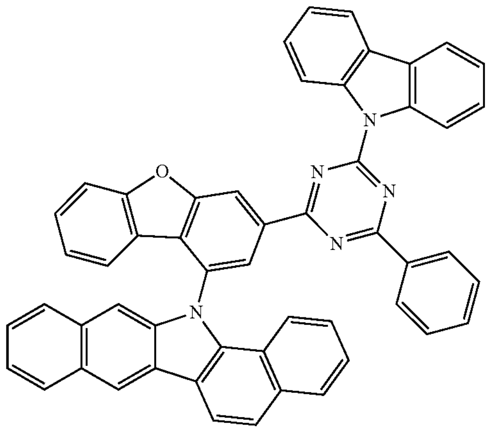
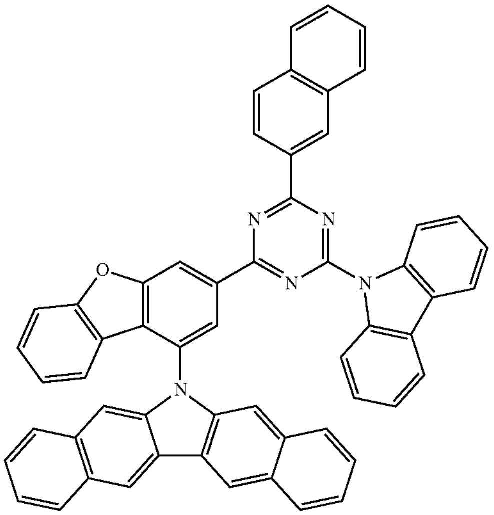
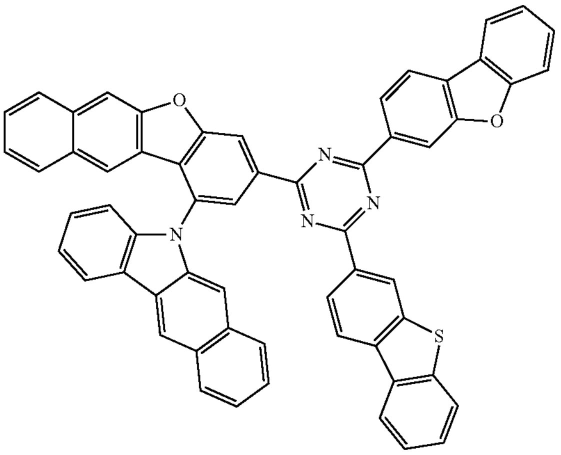

-continued
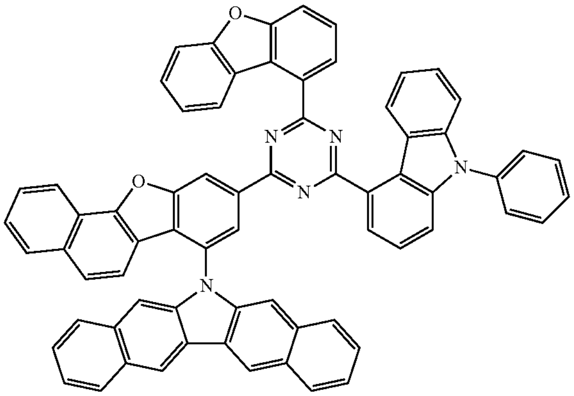
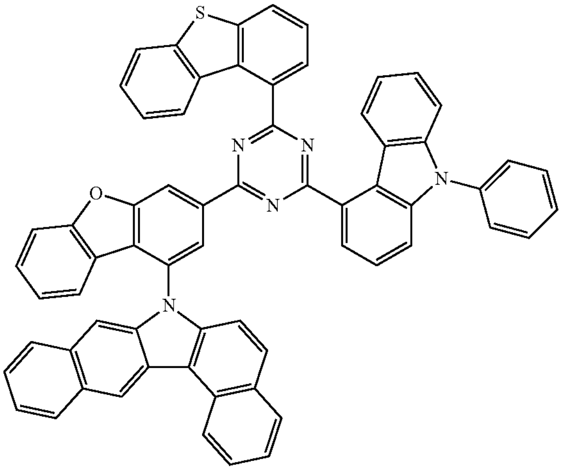
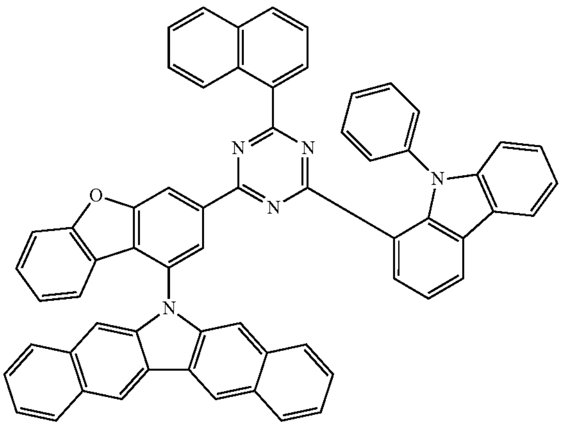
-continued
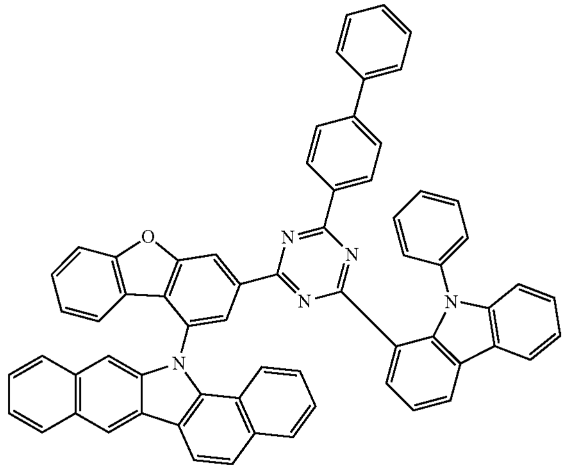
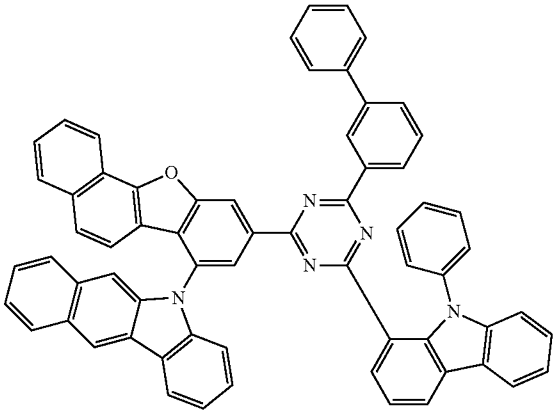
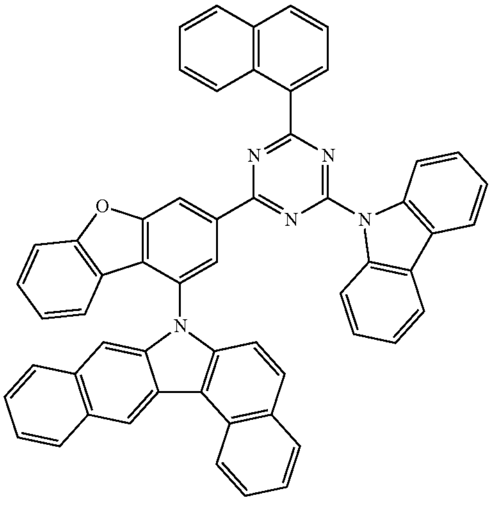

-continued
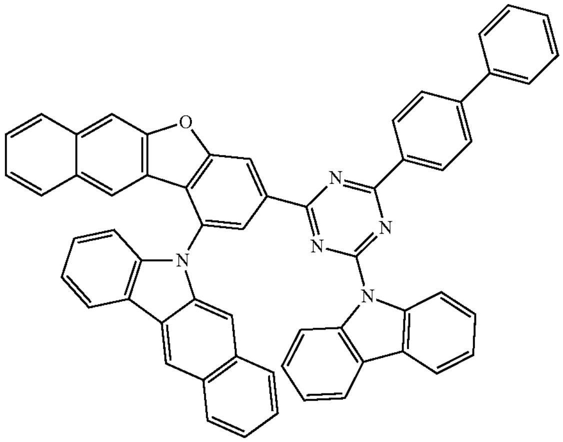
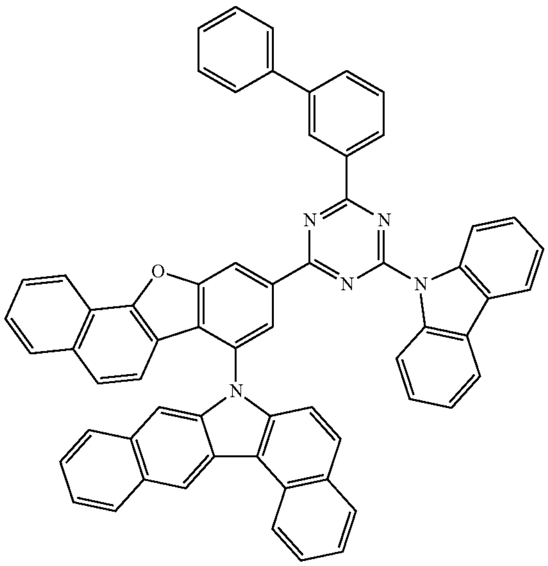
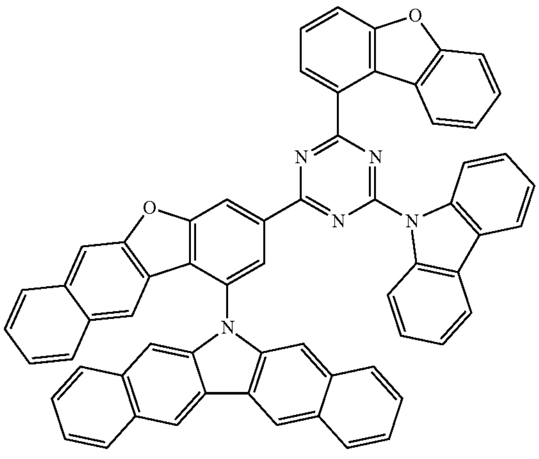
-continued
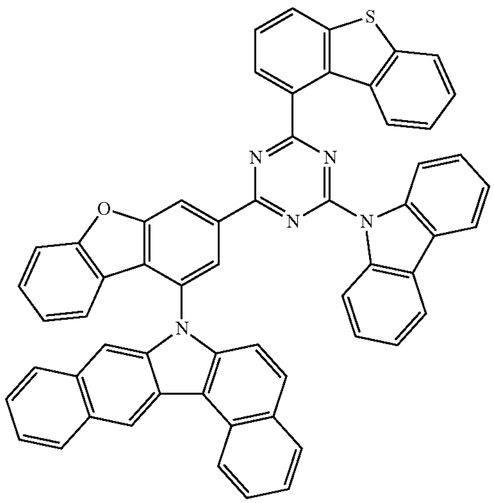
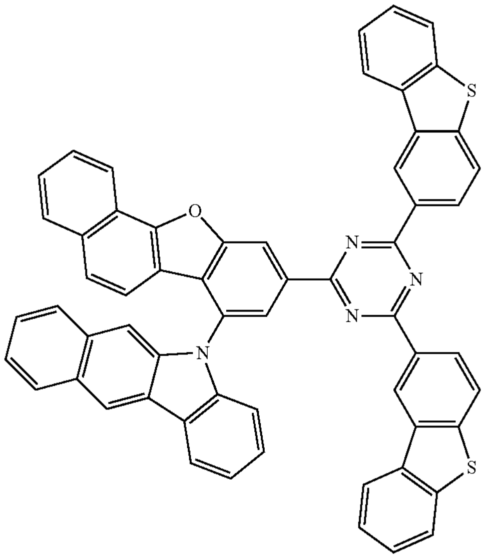
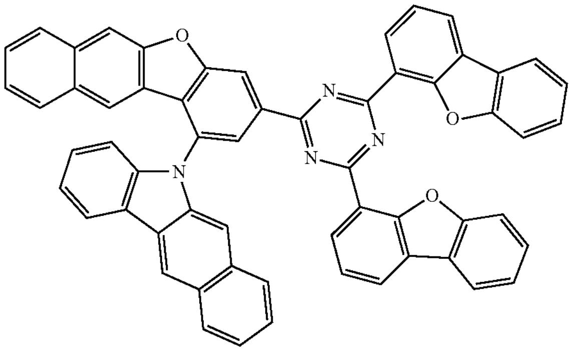

-continued
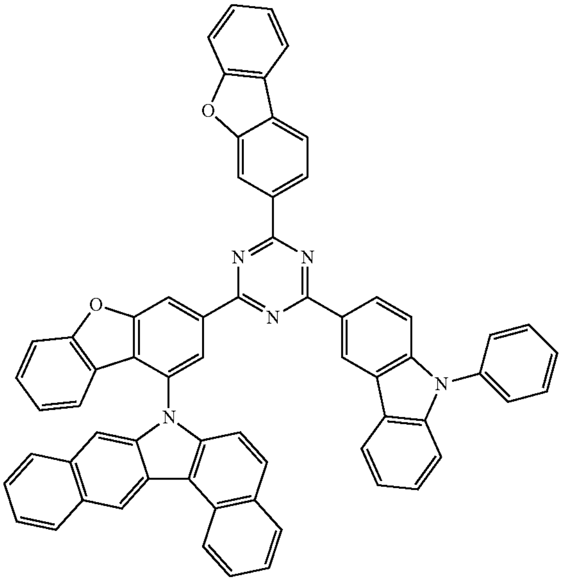
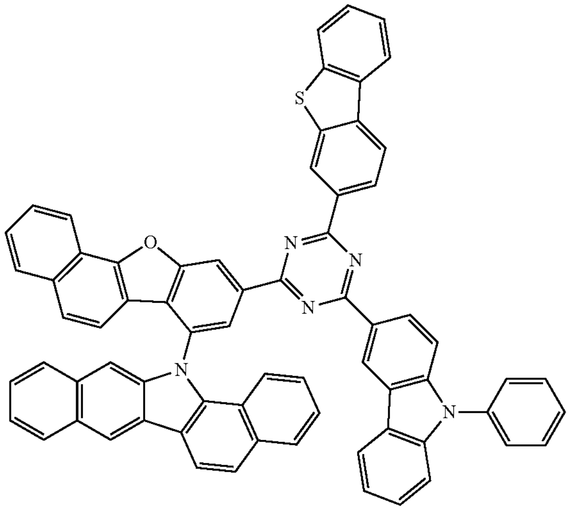
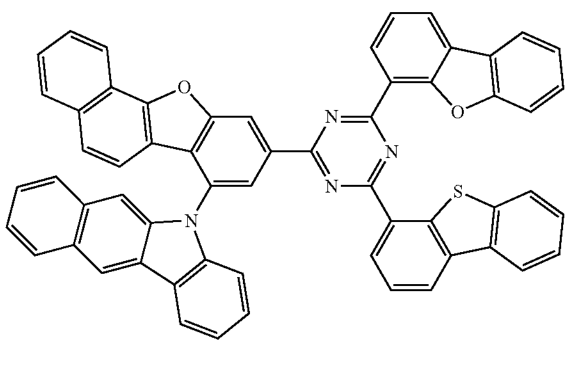
-continued
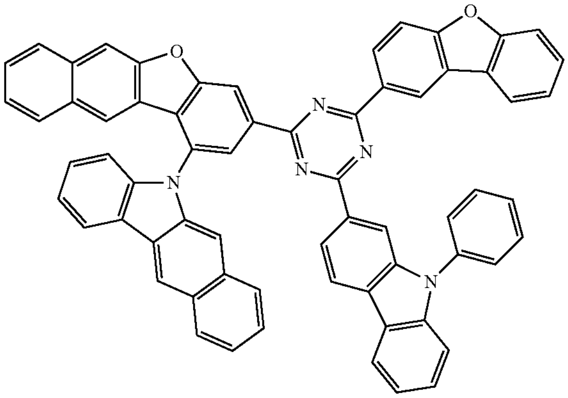
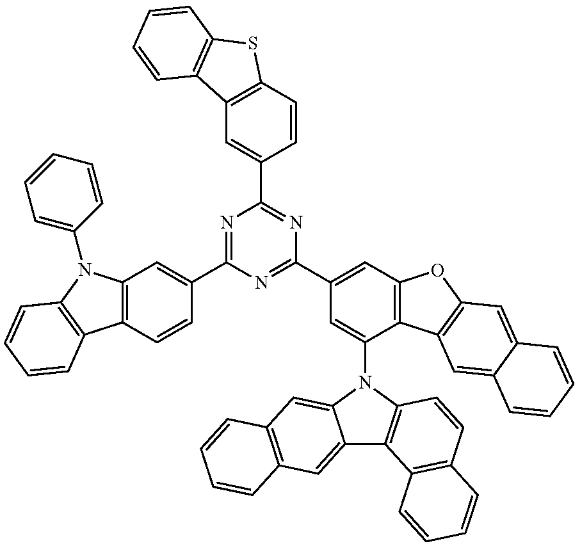
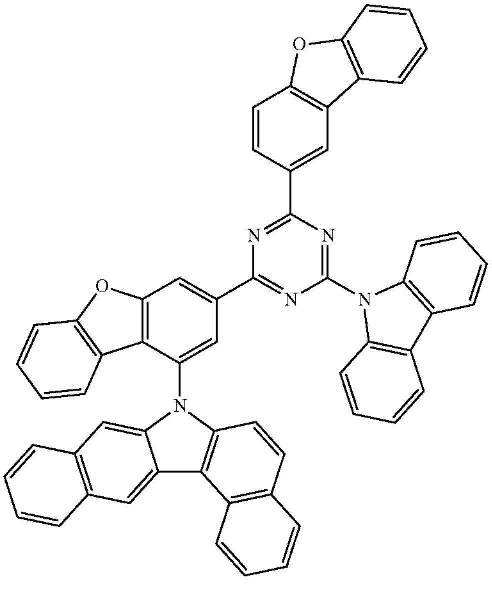

-continued
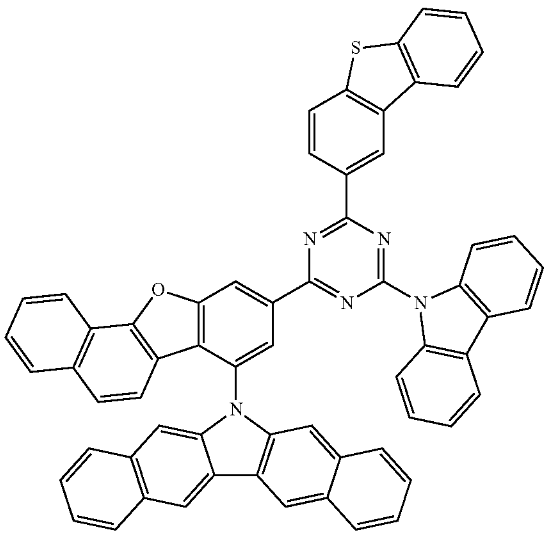
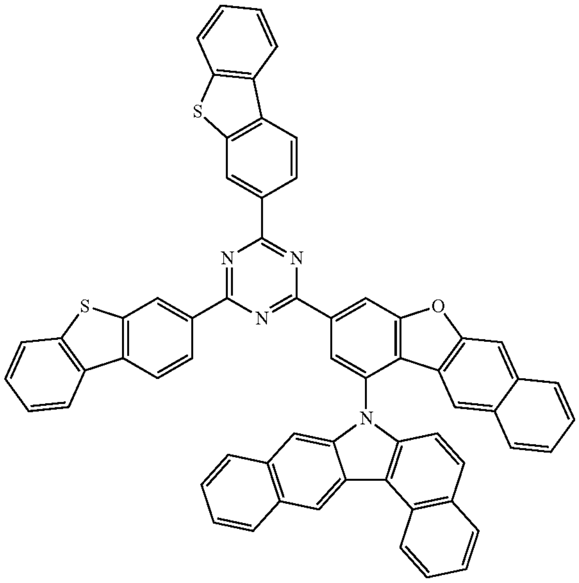
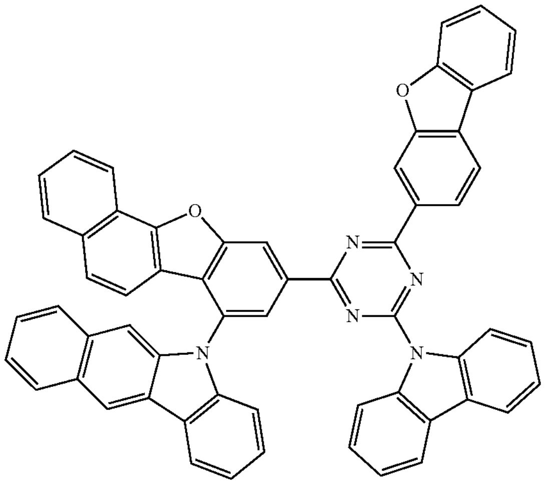
-continued
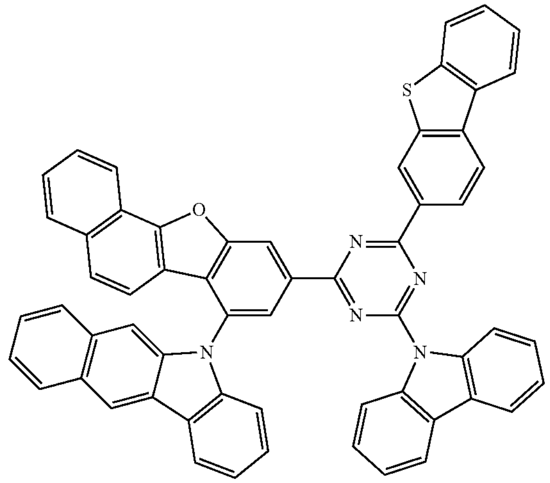
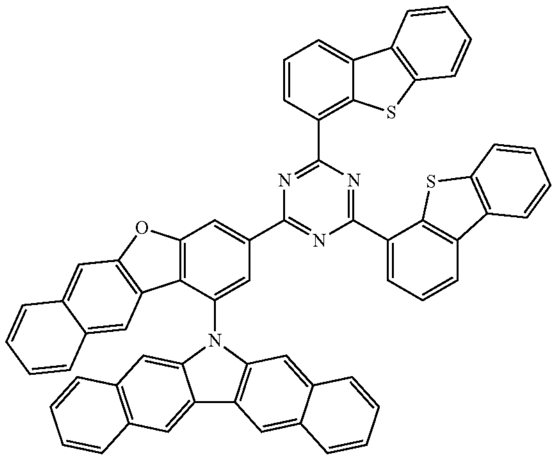
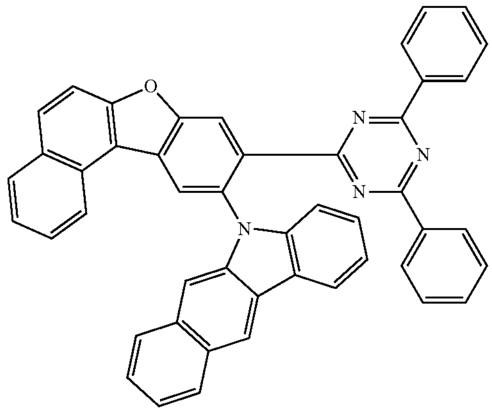
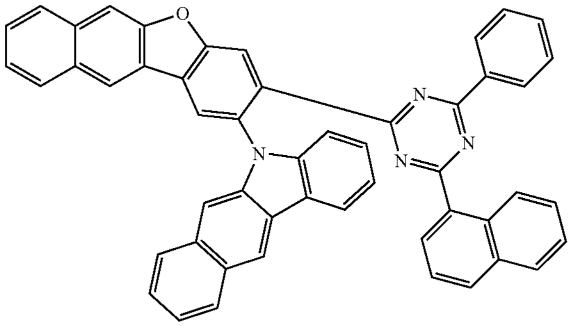

-continued
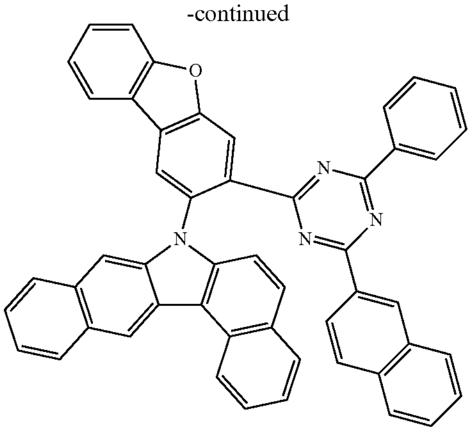
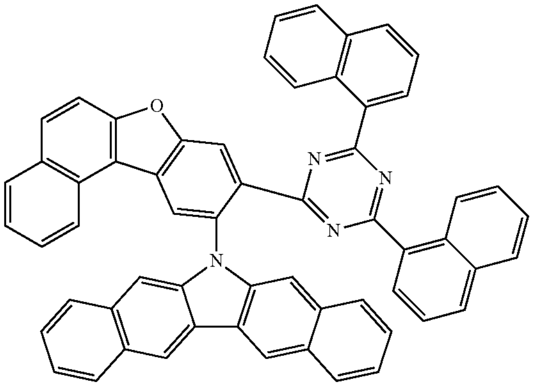
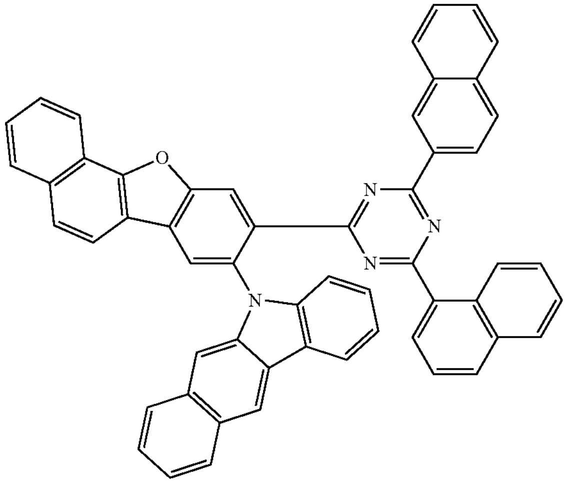
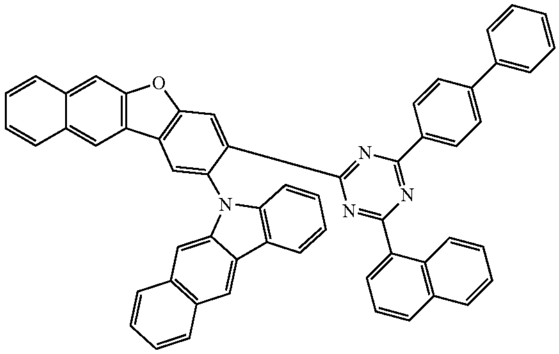
-continued
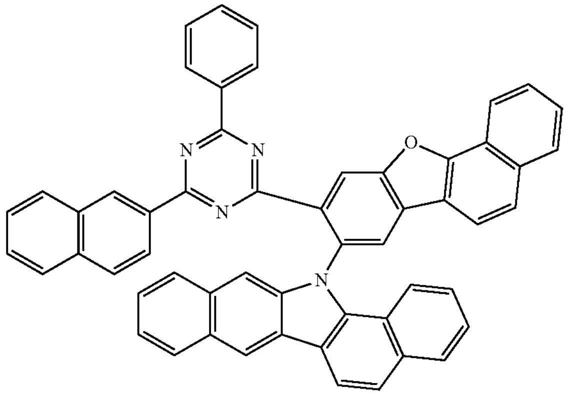
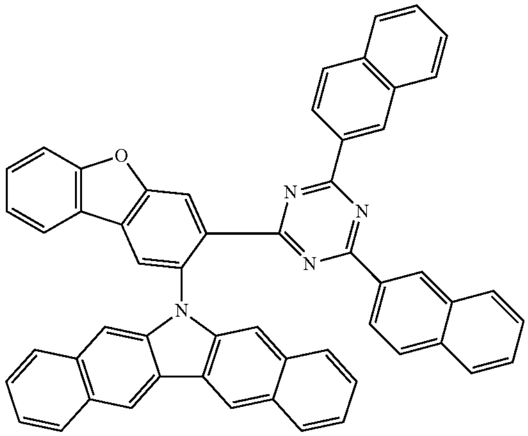
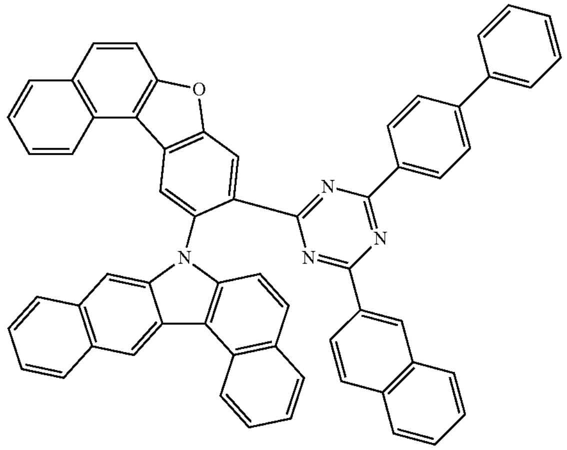
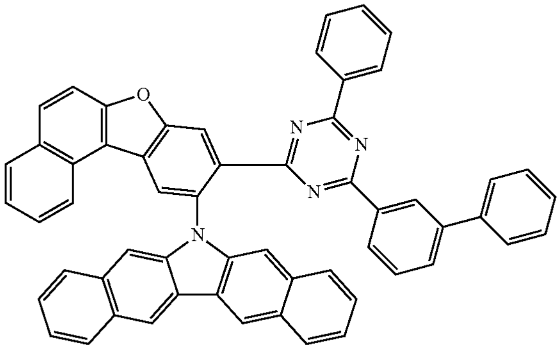

-continued
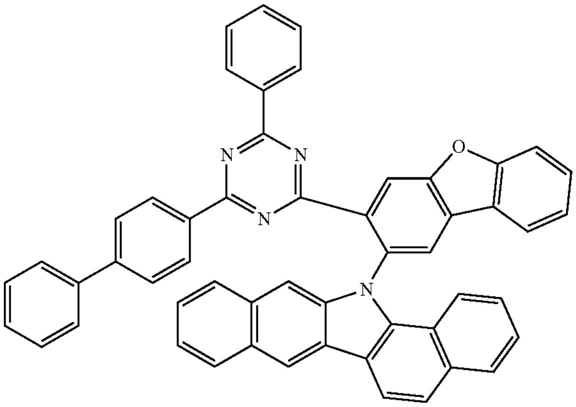
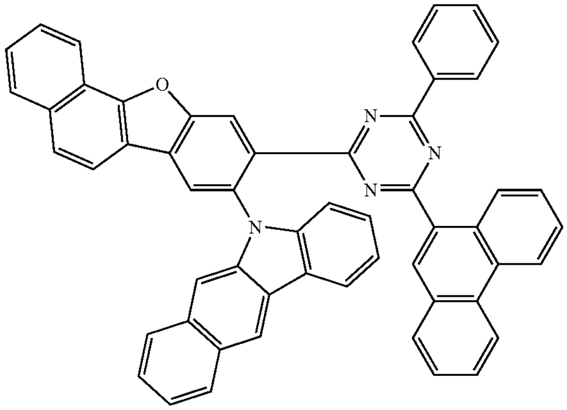
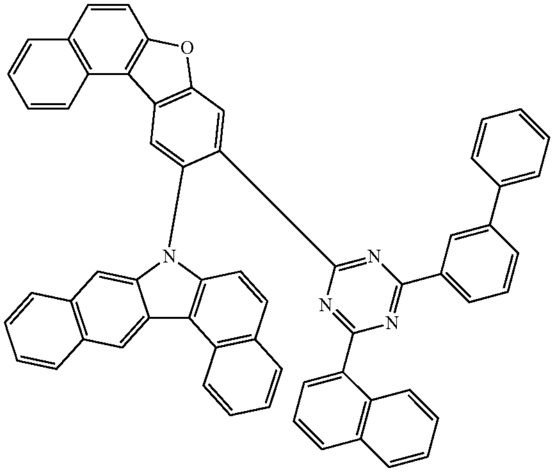
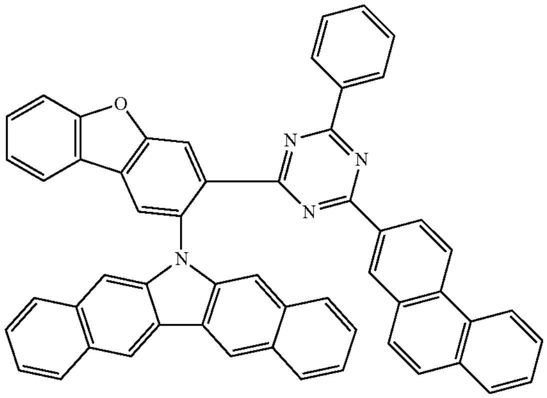
-continued
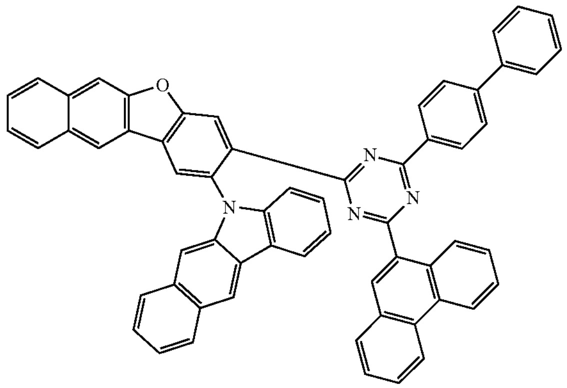
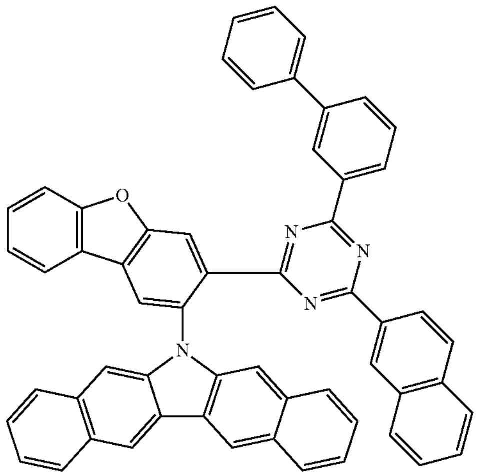
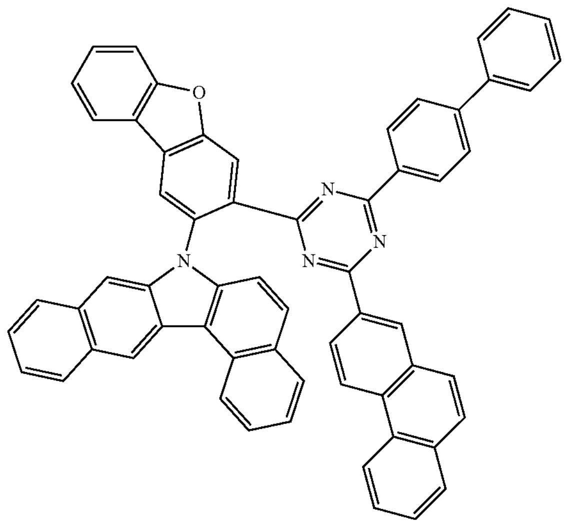

-continued
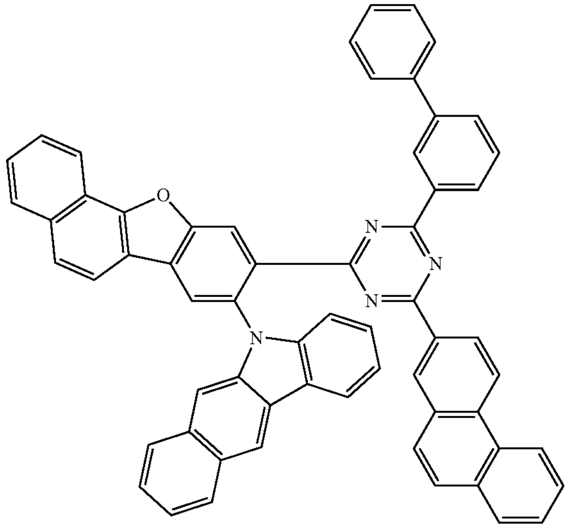
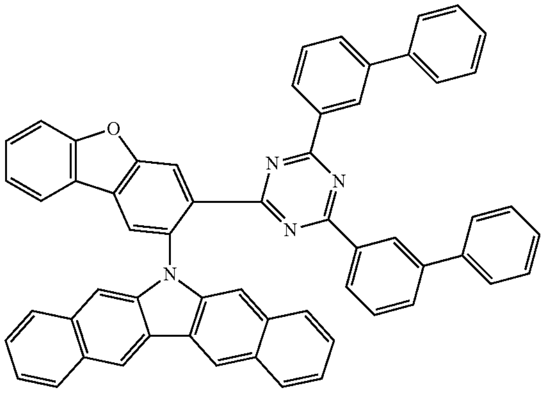
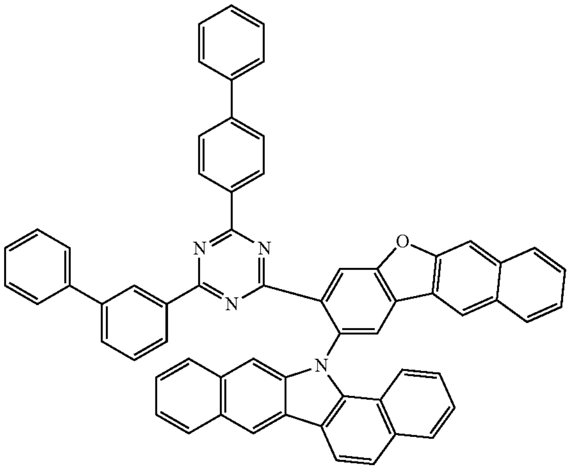
-continued
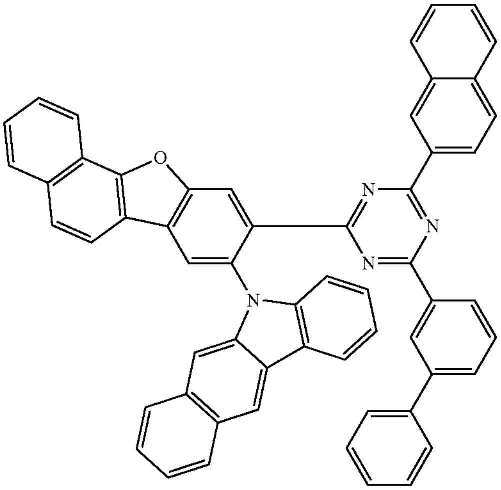
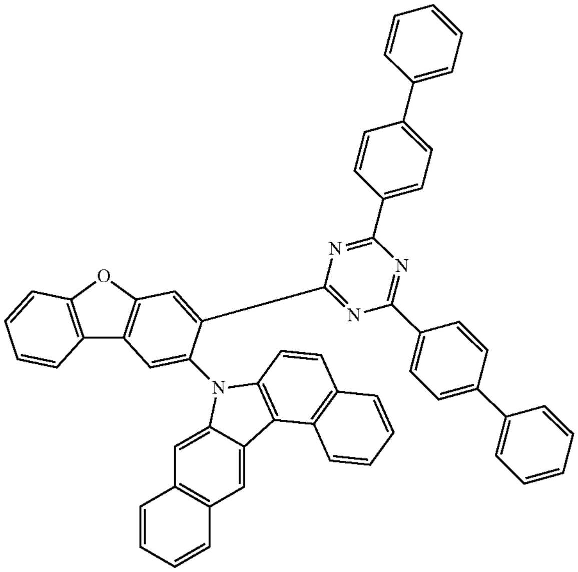
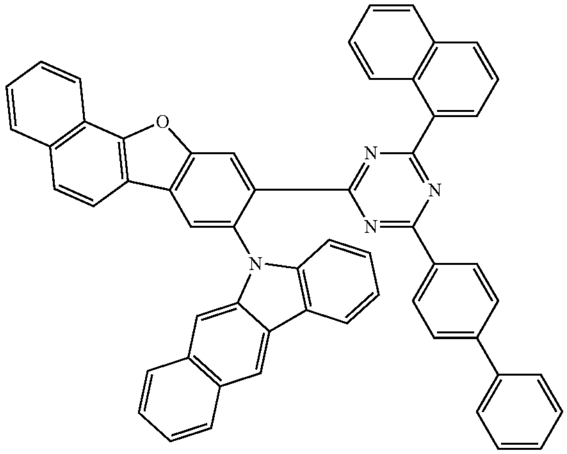

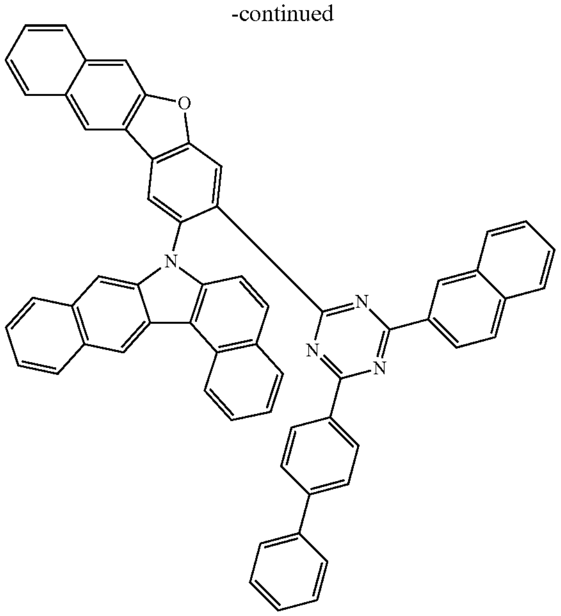
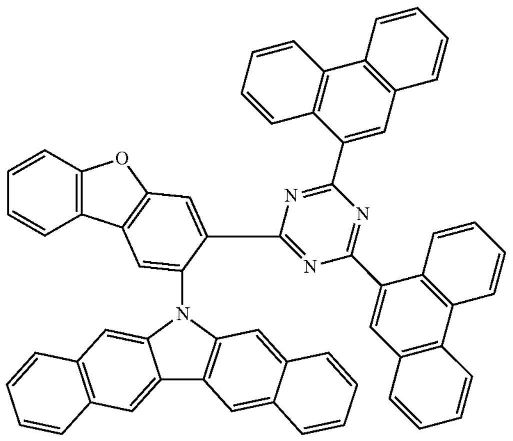
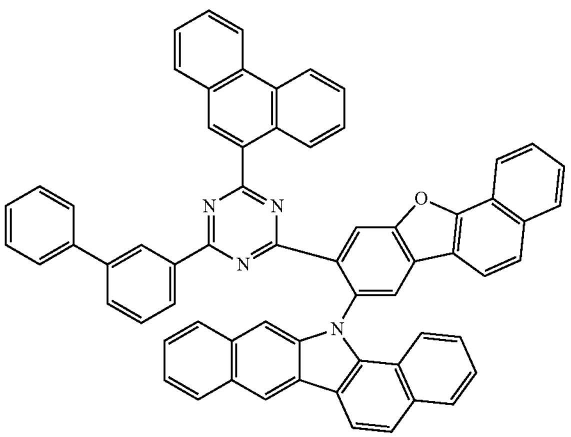
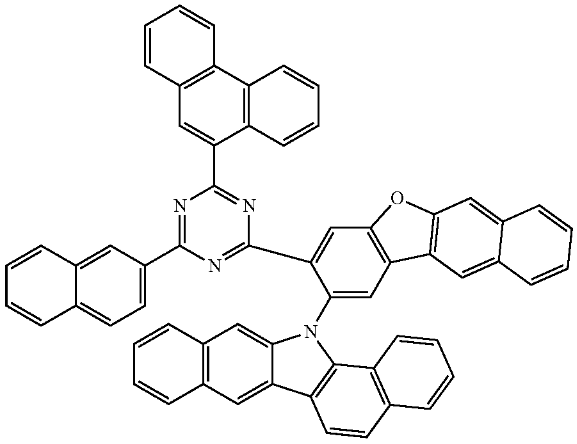
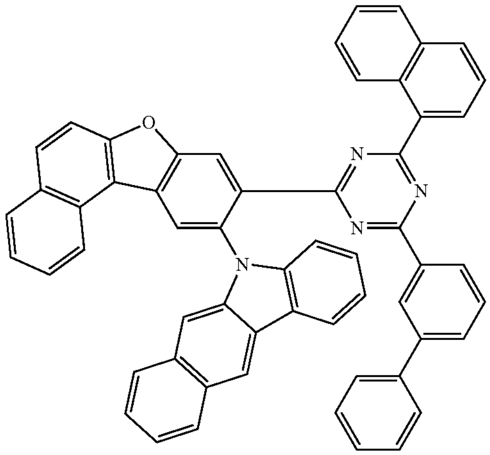
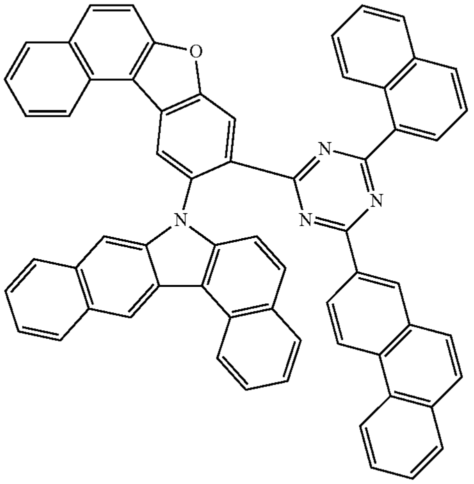

-continued
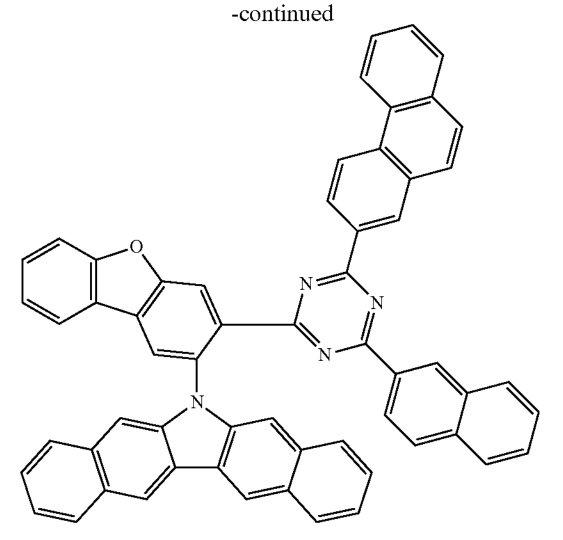
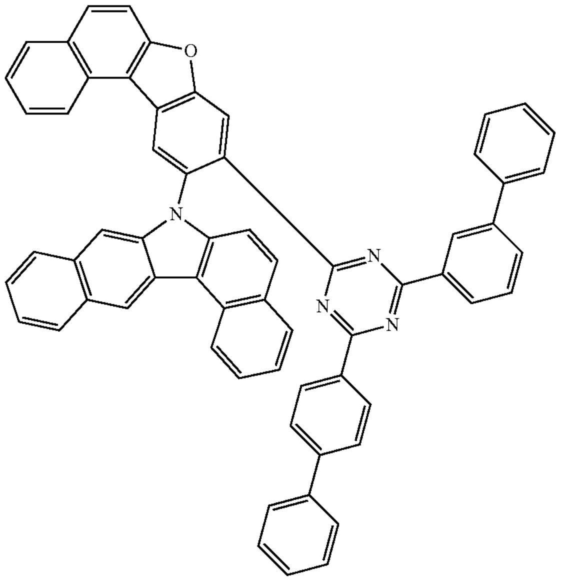
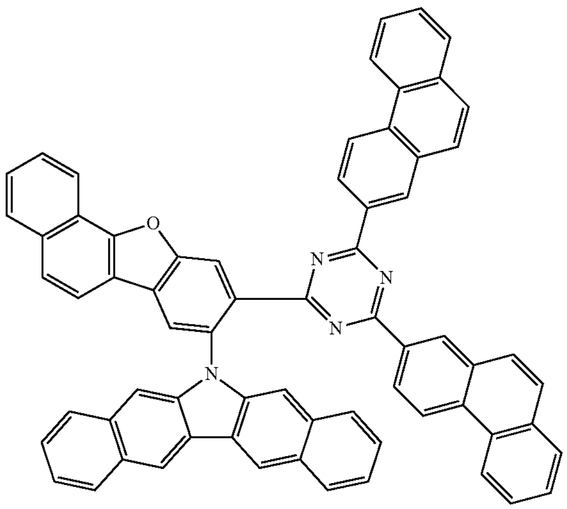
-continued
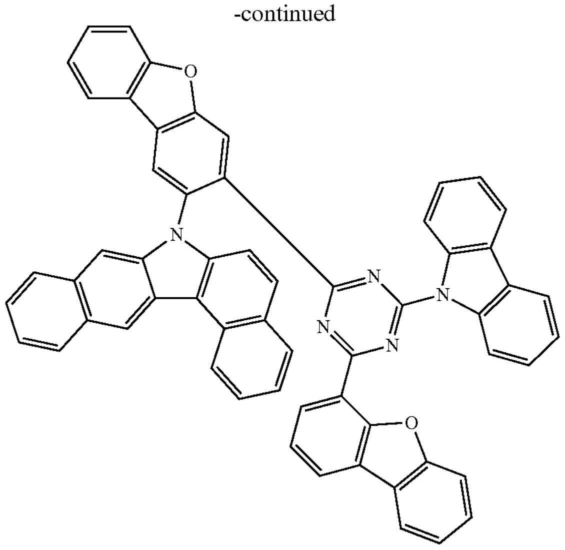
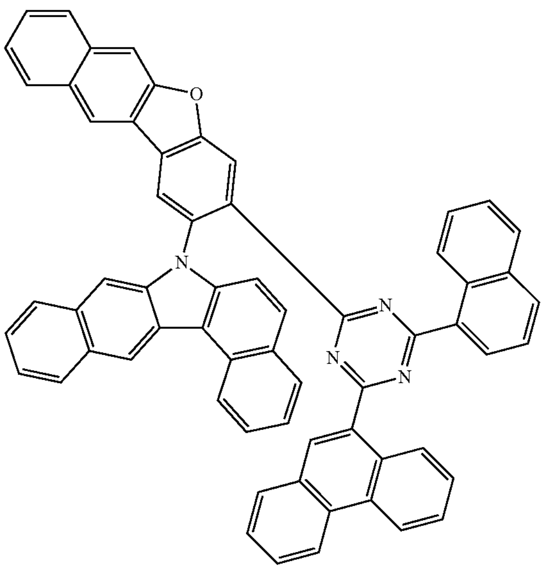
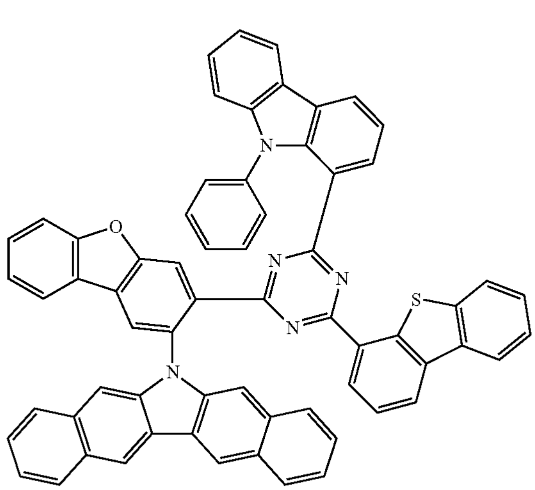

-continued
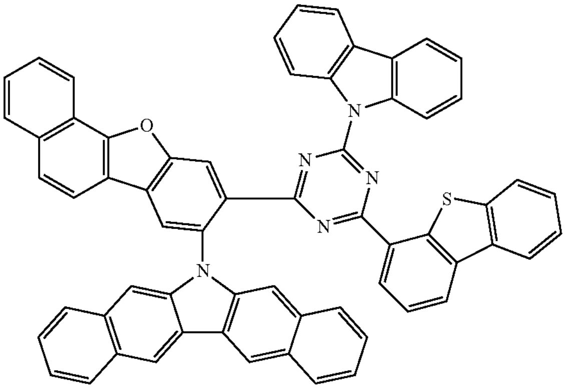
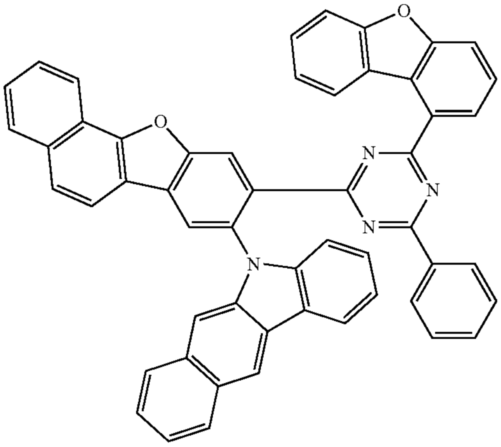
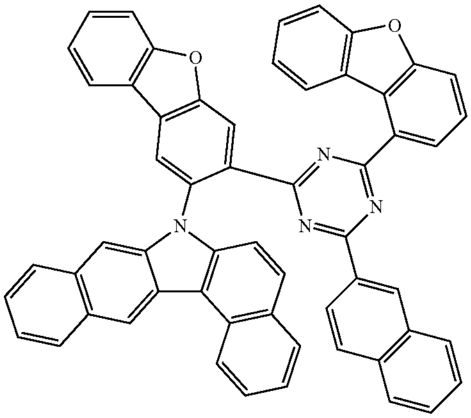
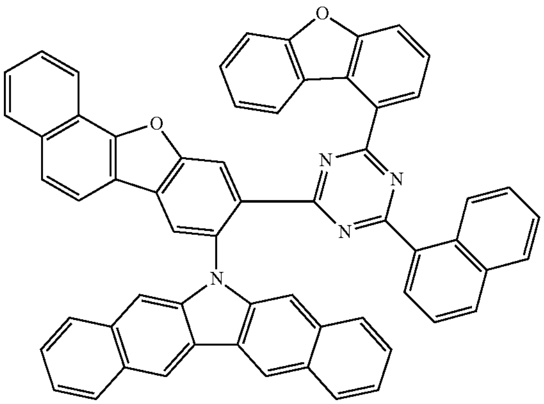
-continued
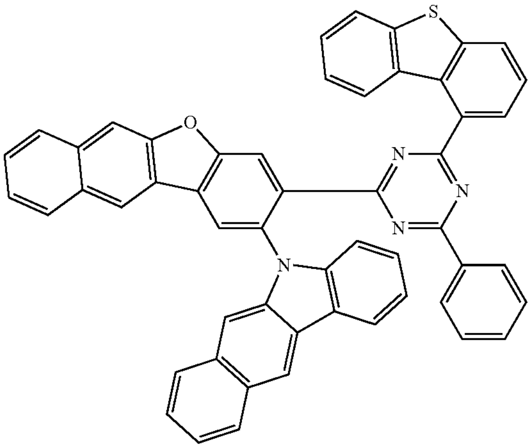
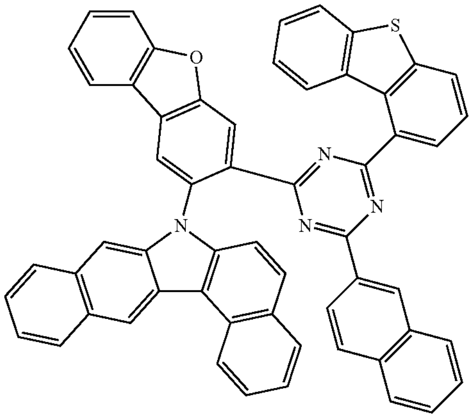
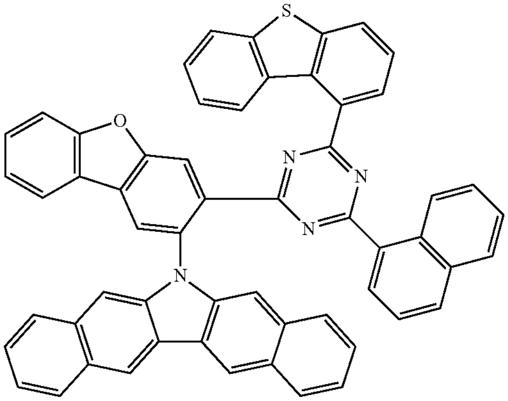
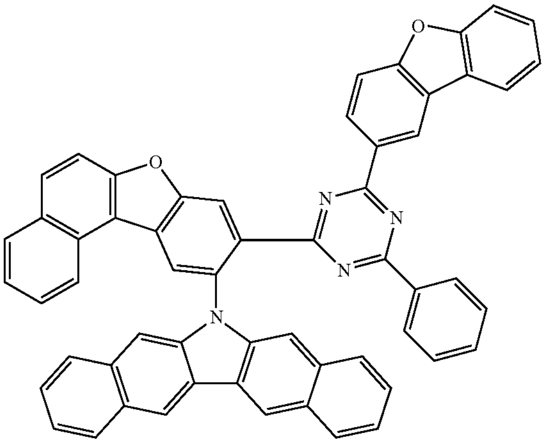

-continued
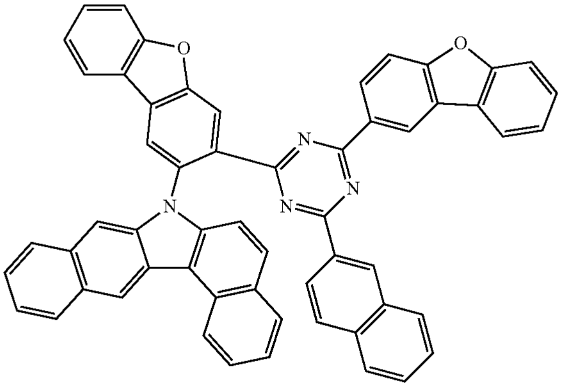
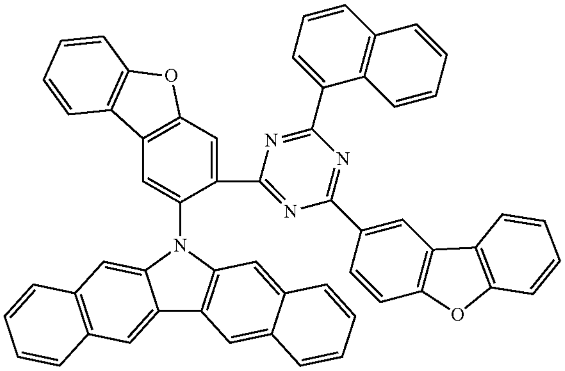
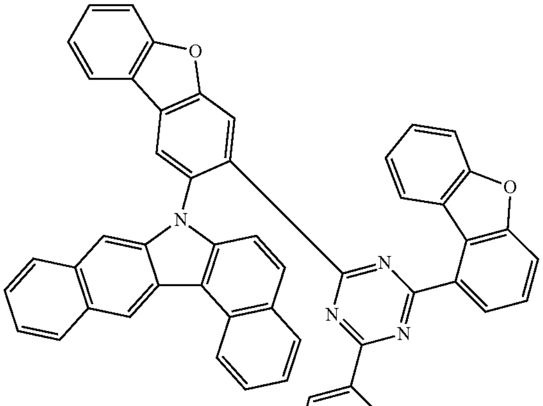
-continued
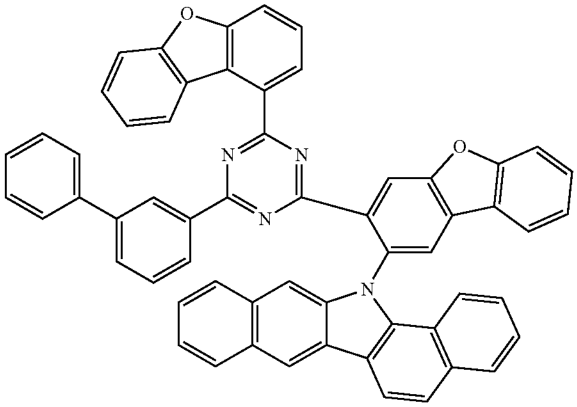
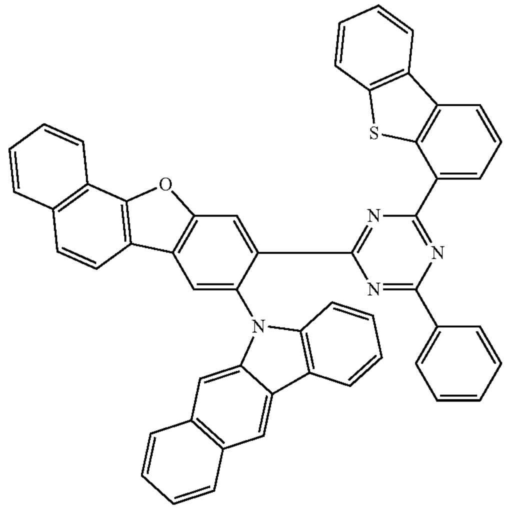
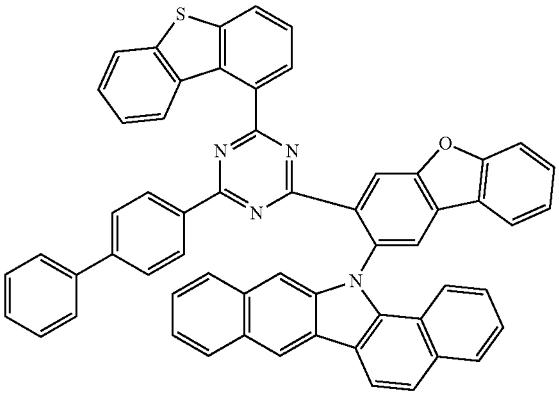

-continued
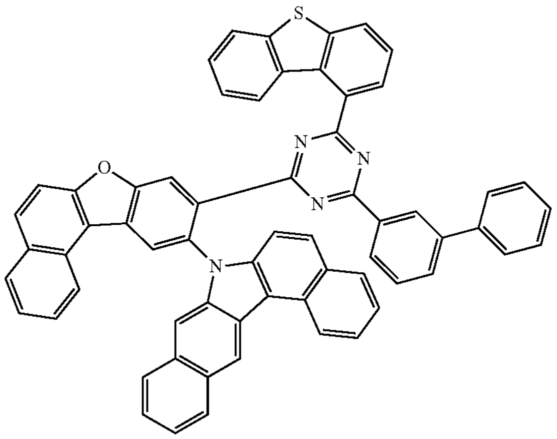
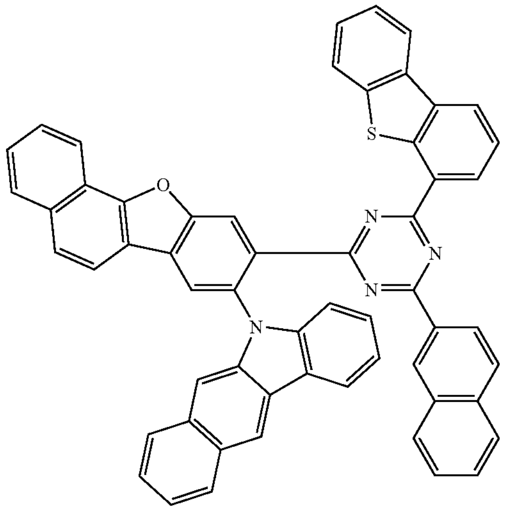
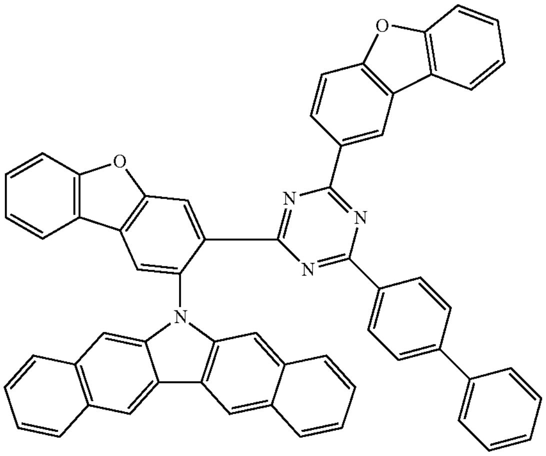
-continued
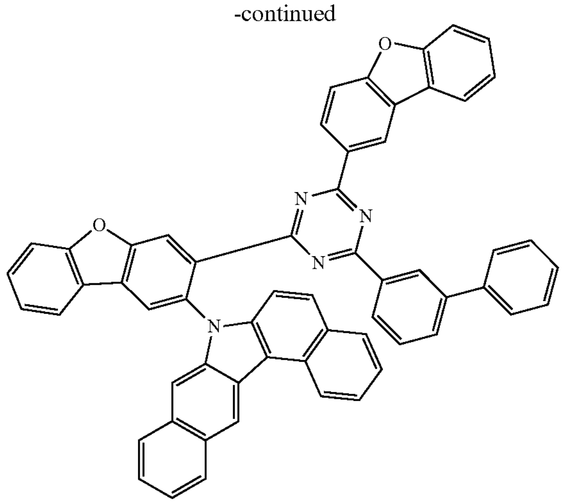
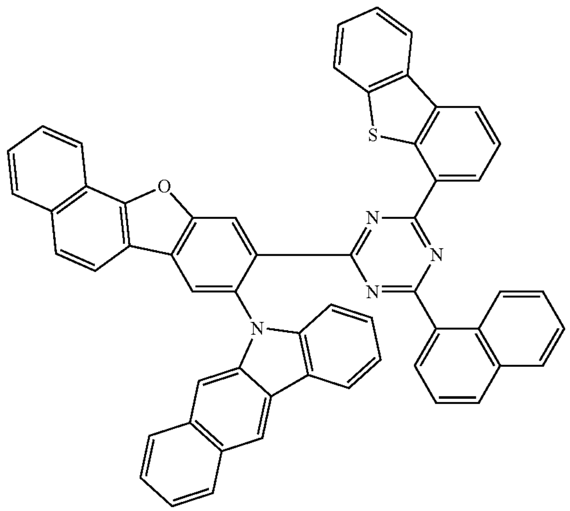
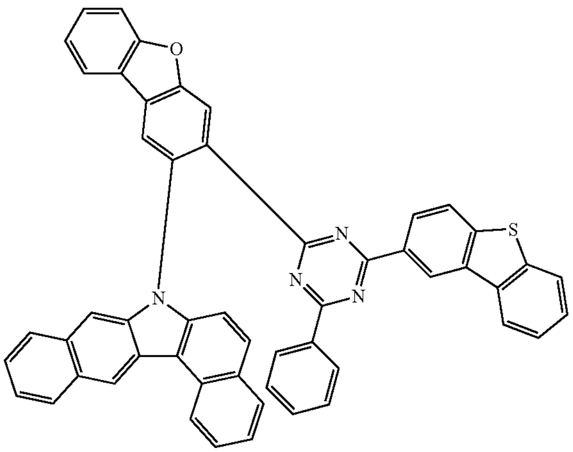

-continued
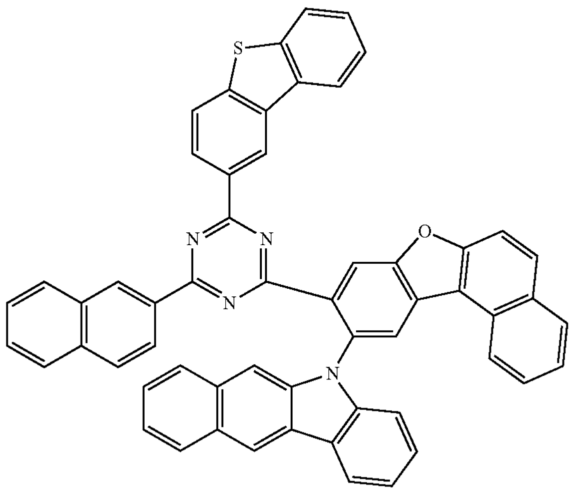
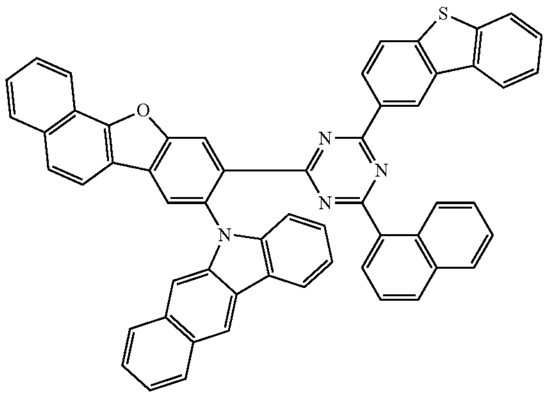
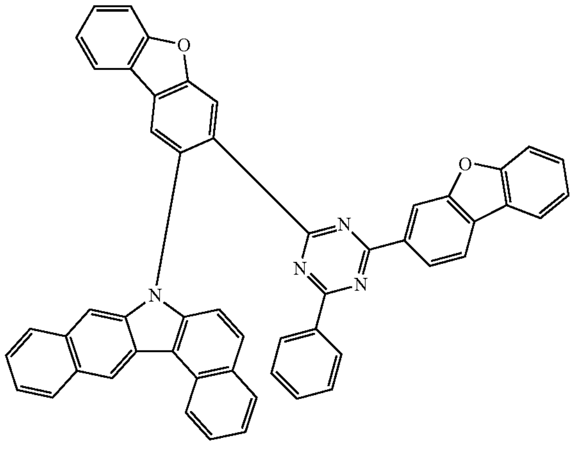
-continued
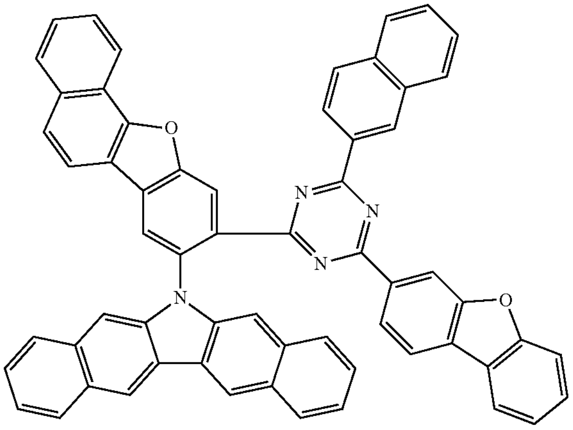
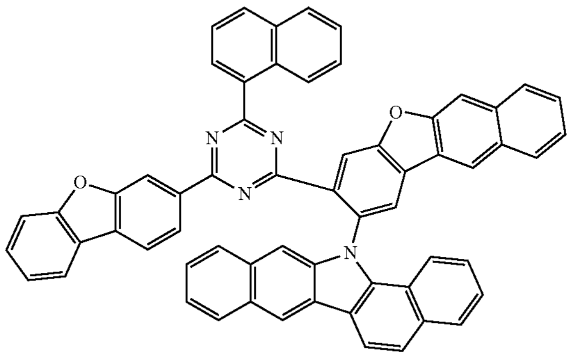
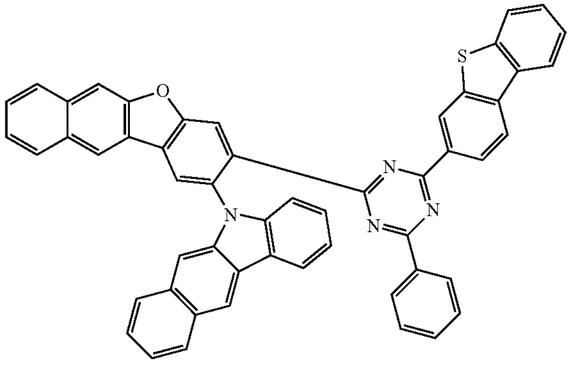
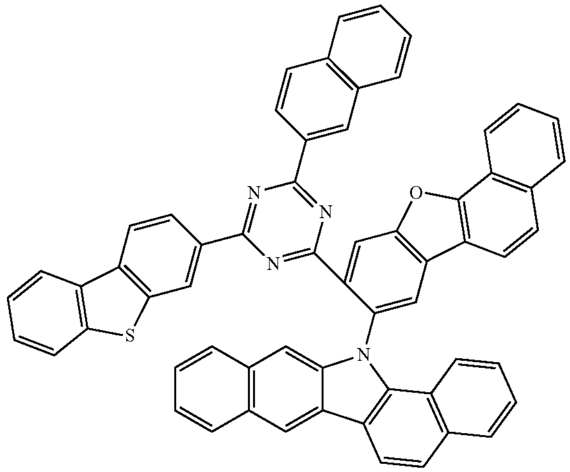

-continued
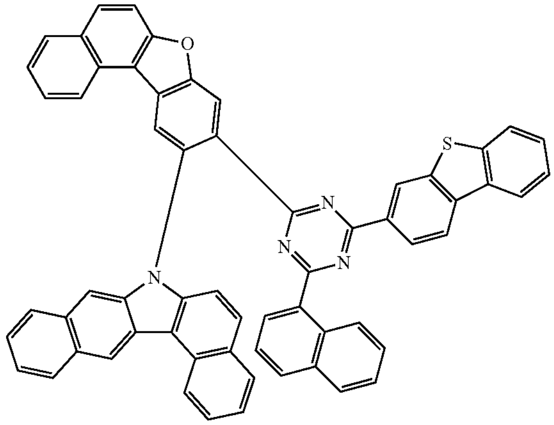
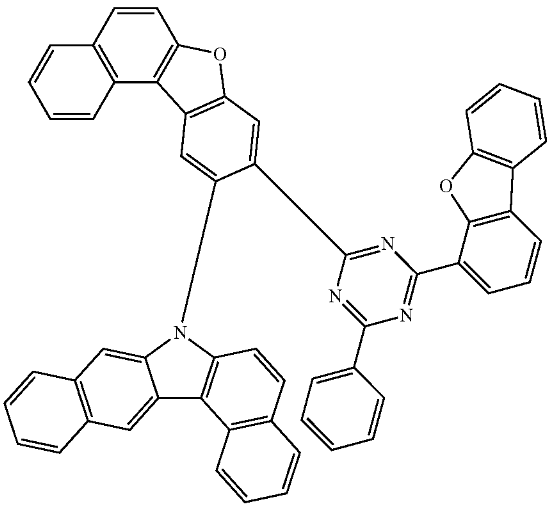
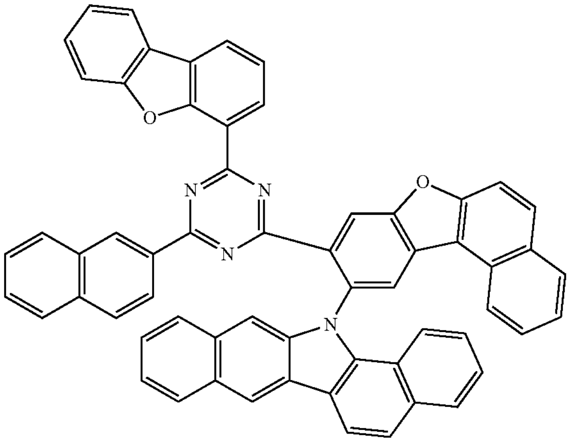
-continued
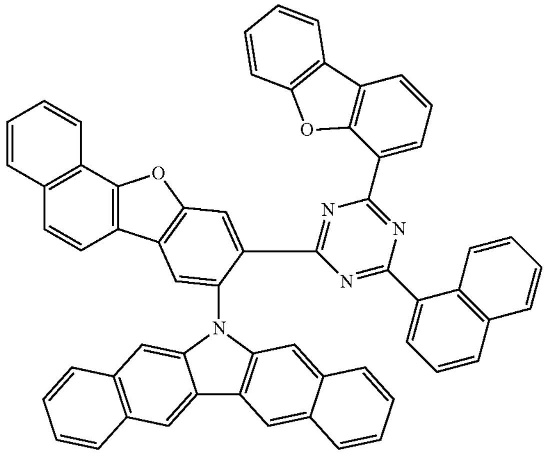
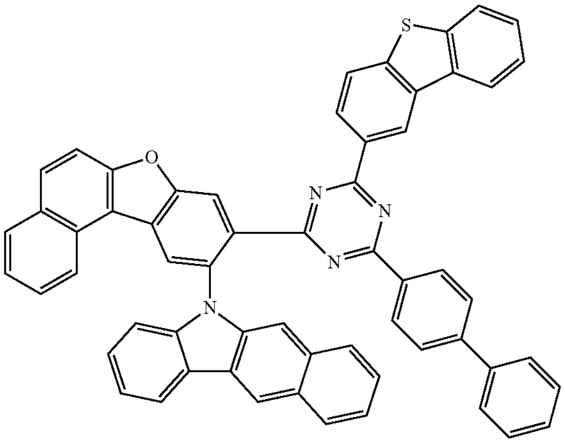
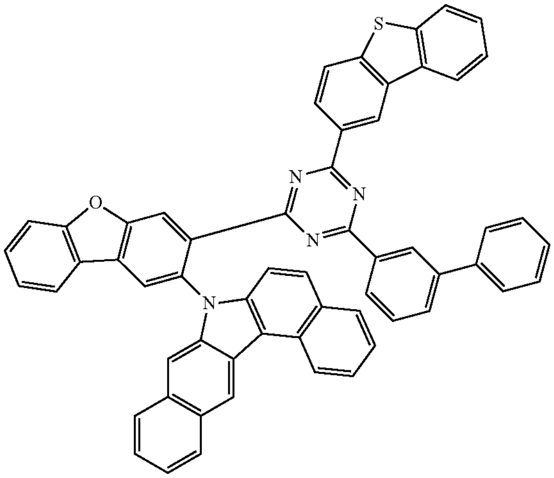

-continued
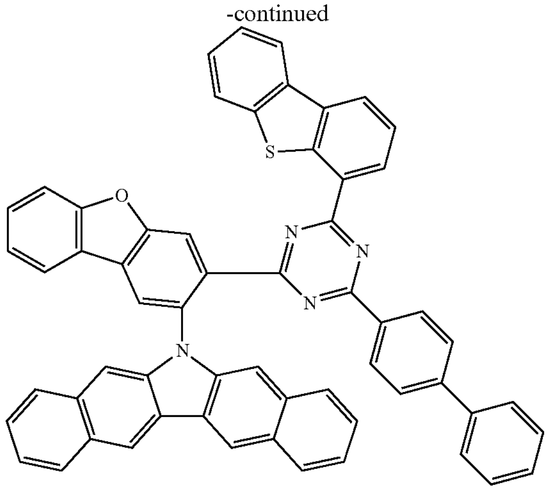
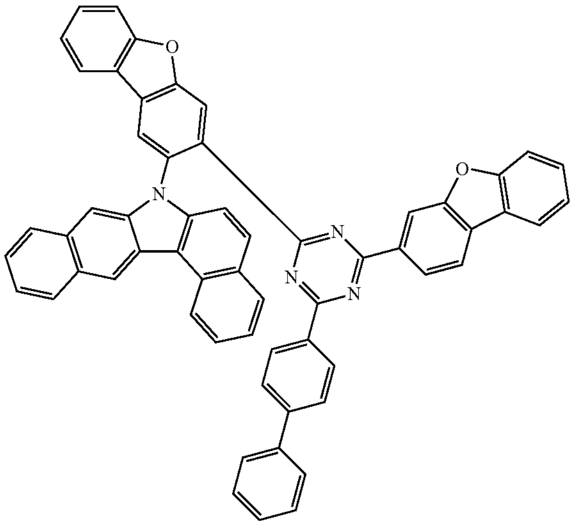
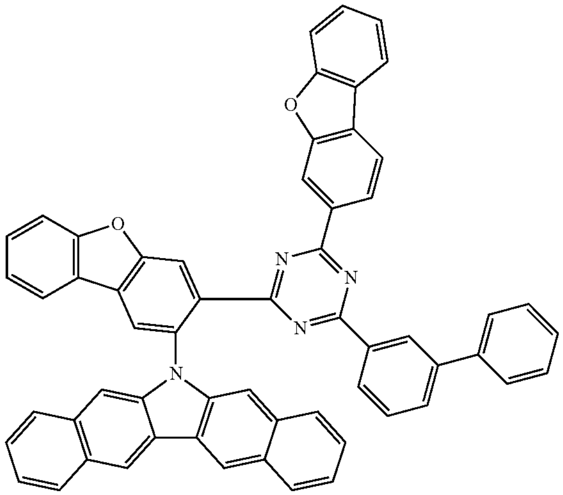
-continued
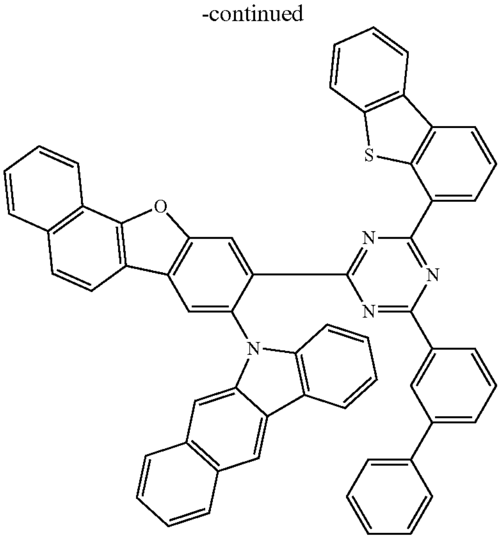
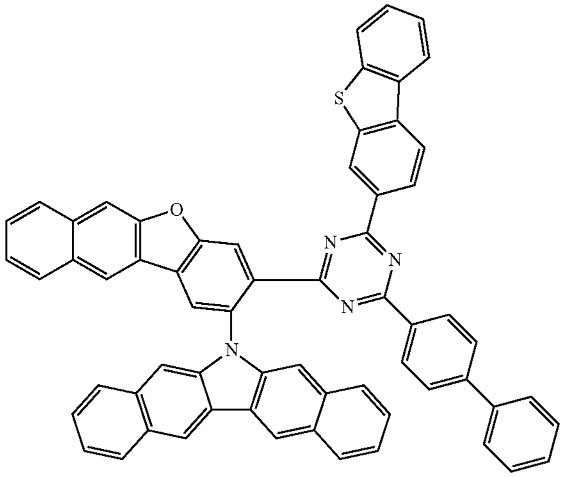
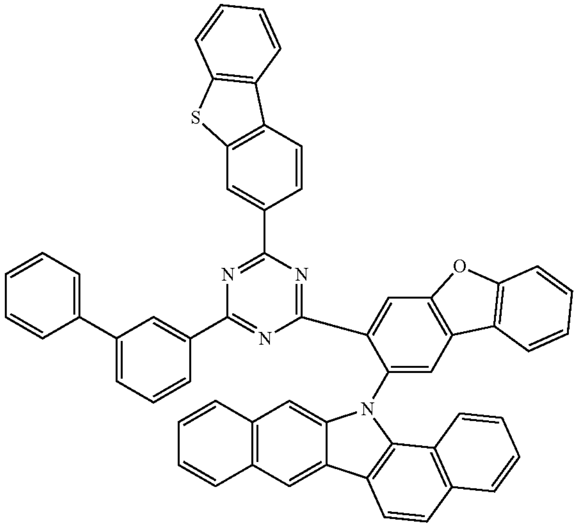

-continued
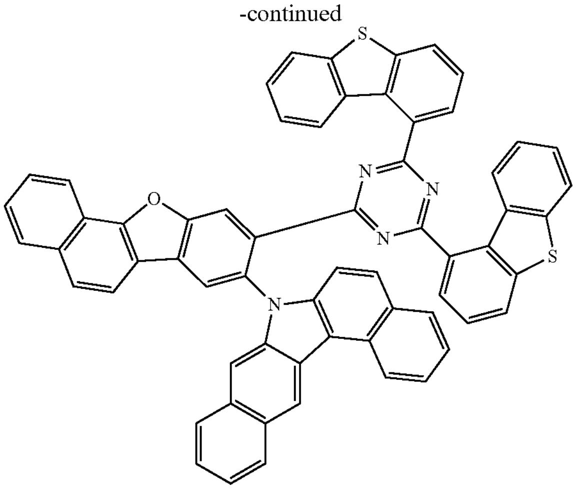
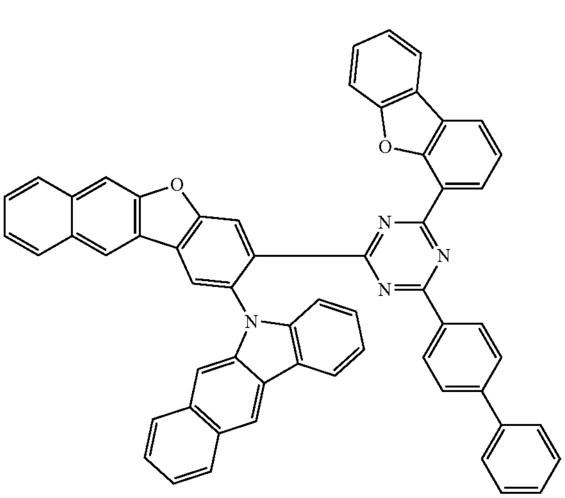
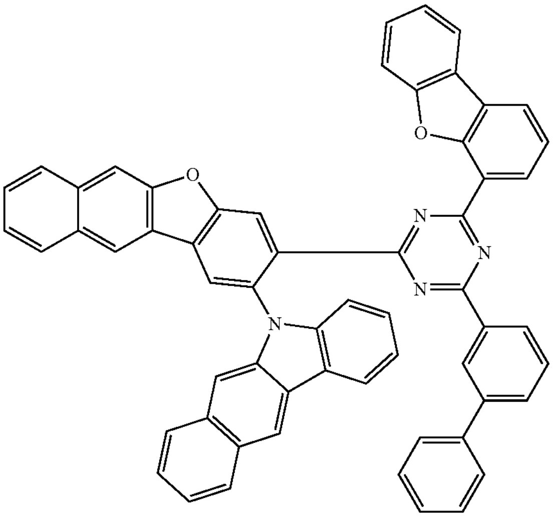
-continued
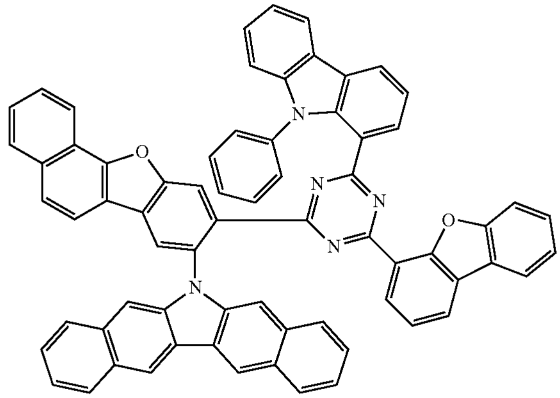
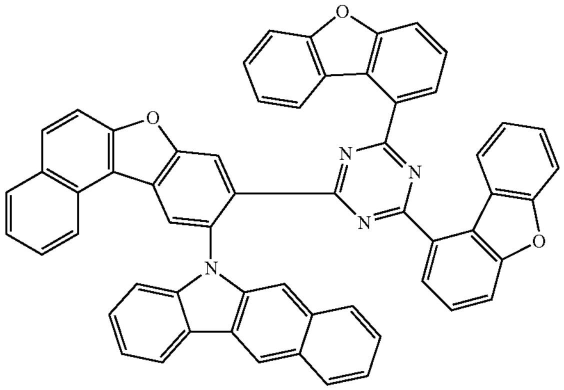
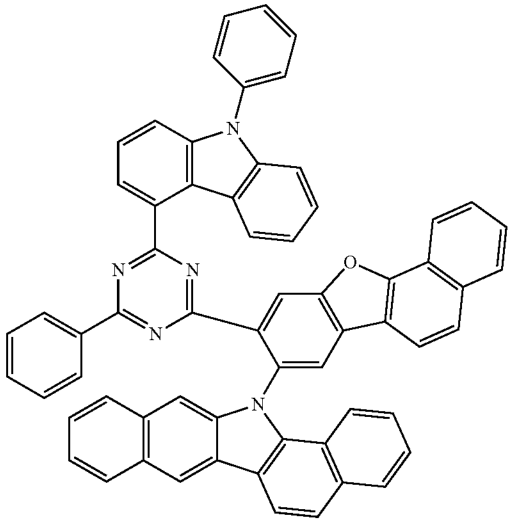

-continued
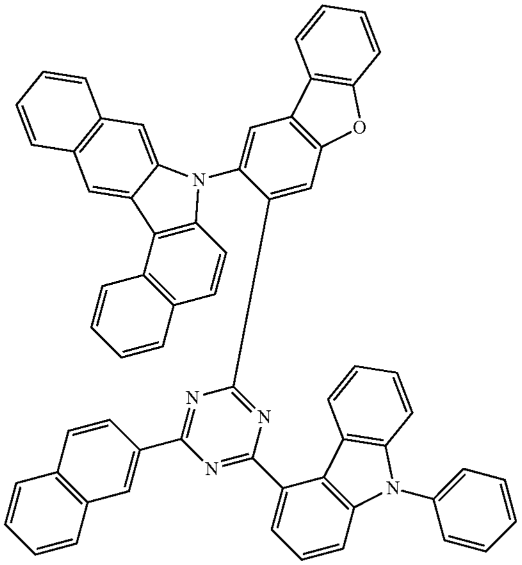
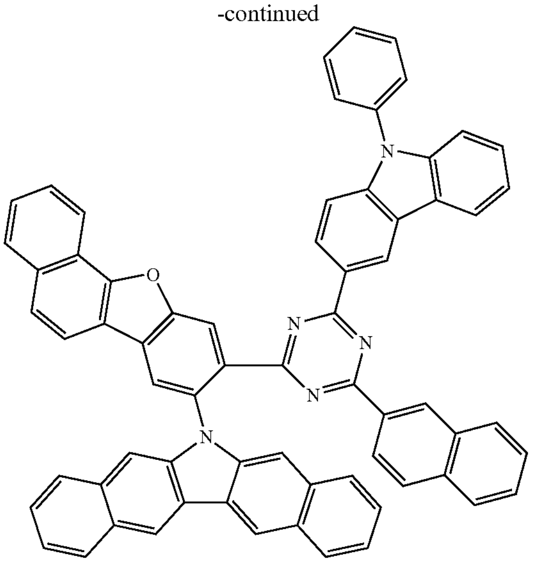
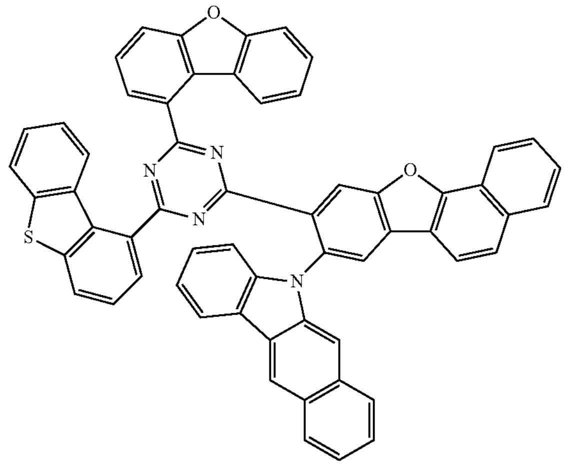
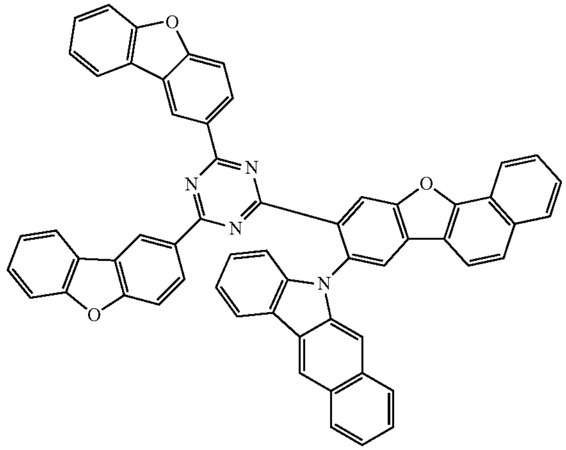
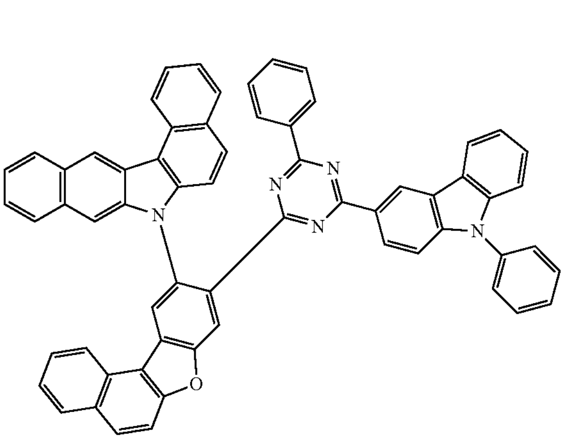
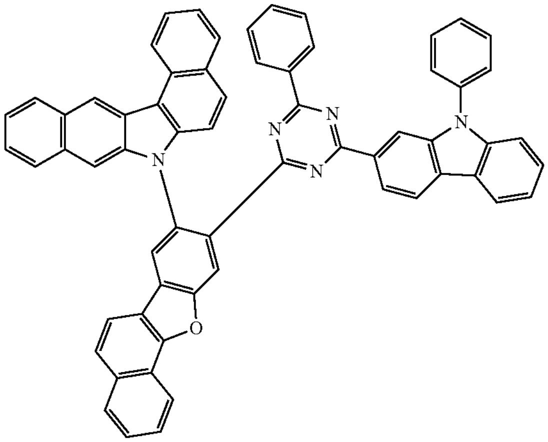
-continued -continued
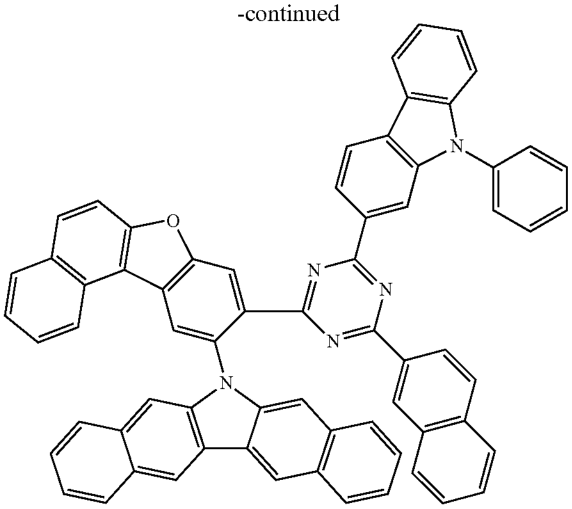
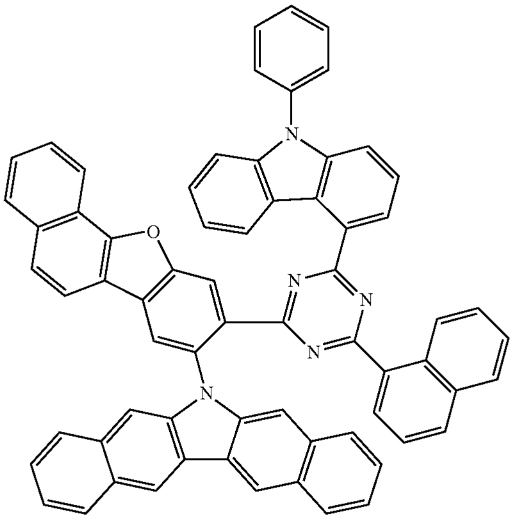
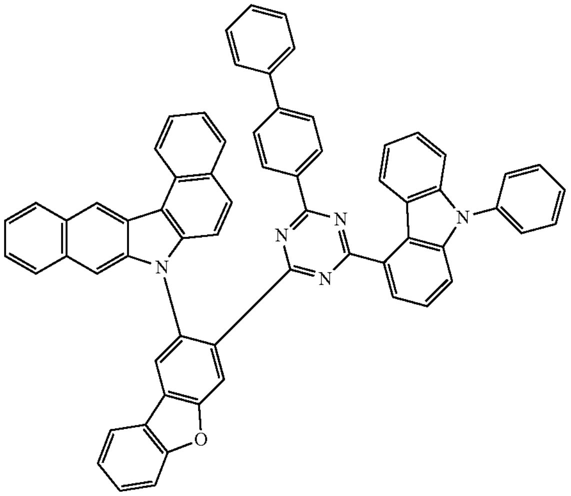
-continued
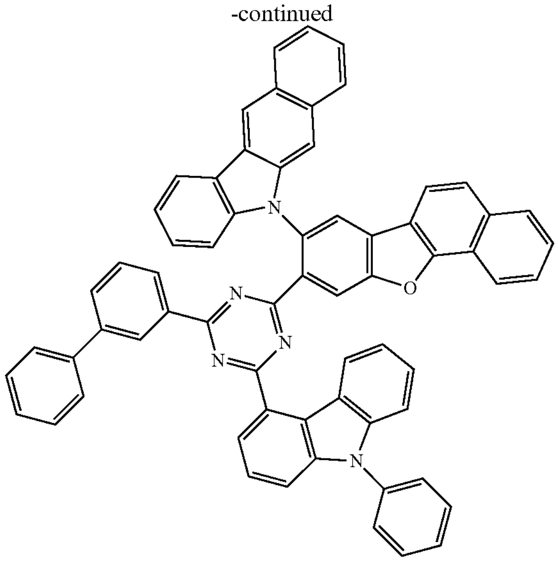
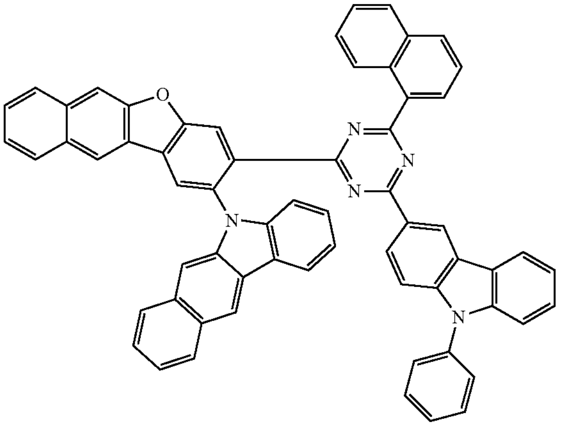
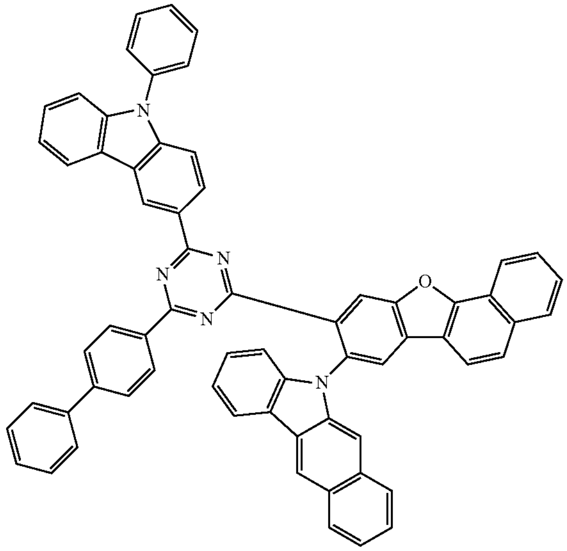

-continued
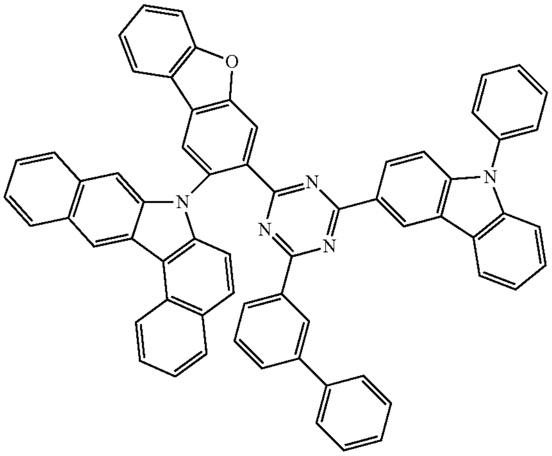
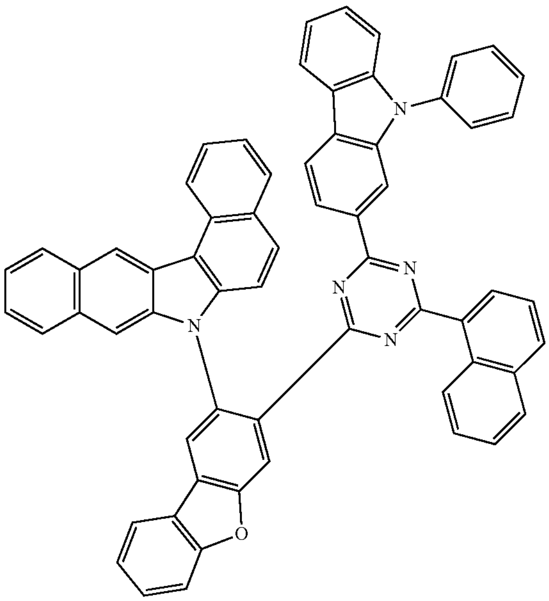
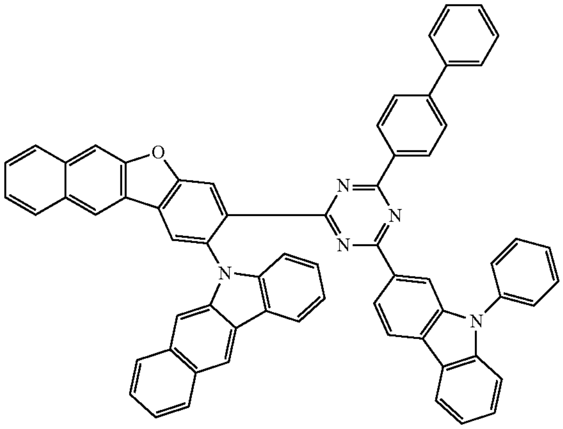
-continued
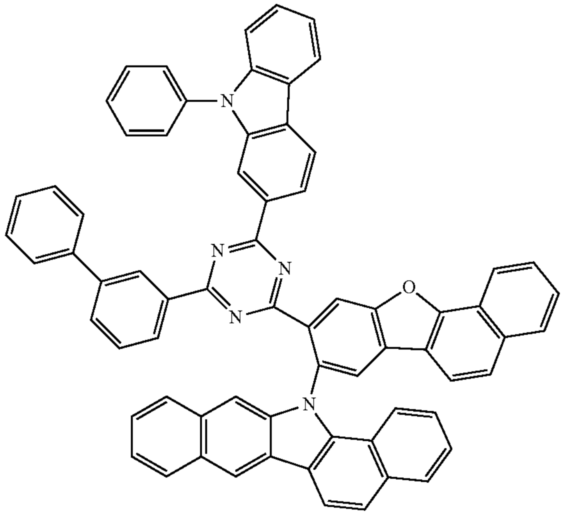
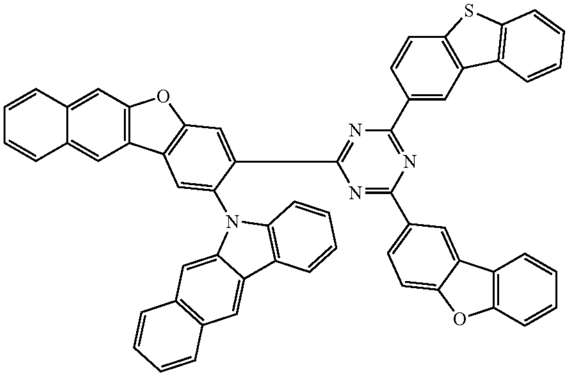
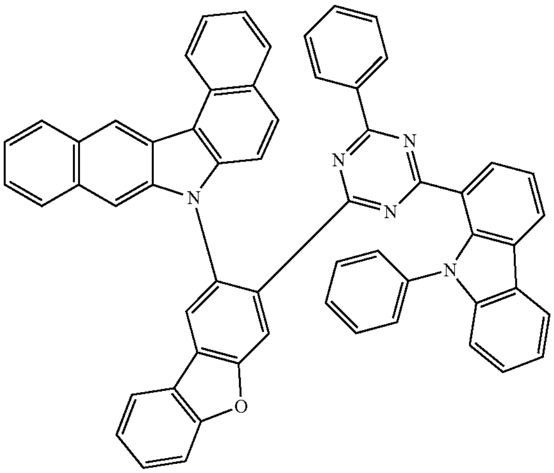

-continued
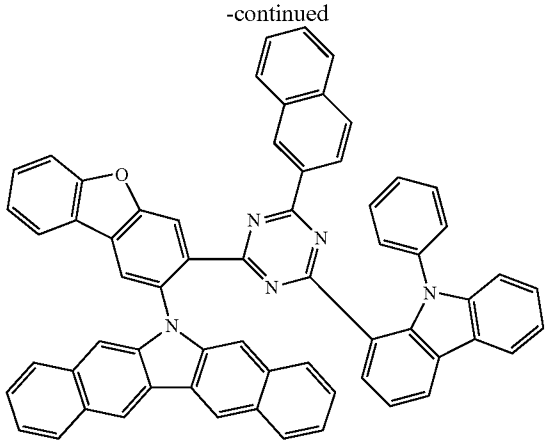
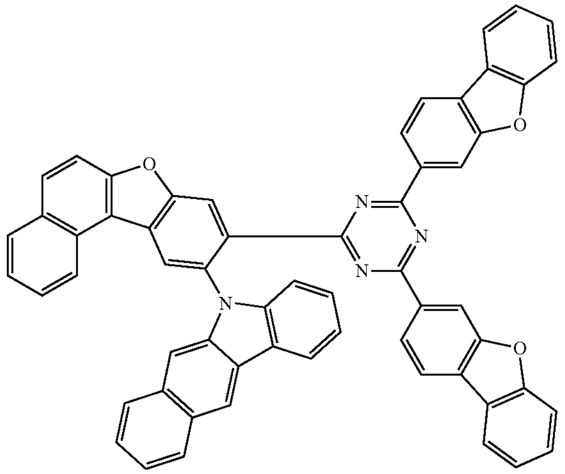
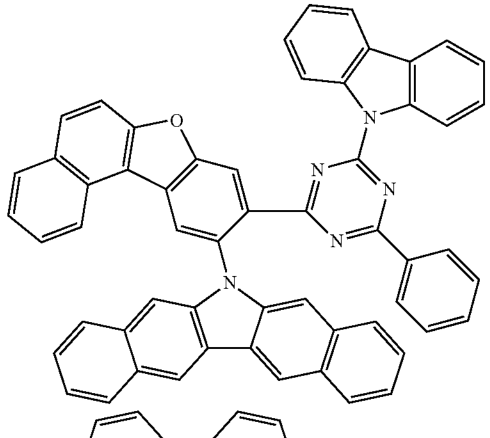
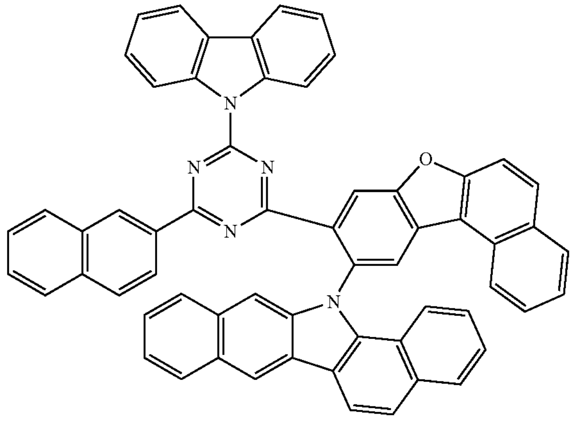
-continued
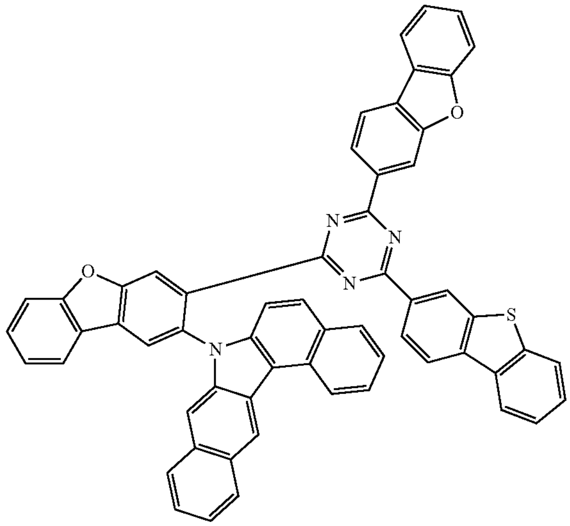
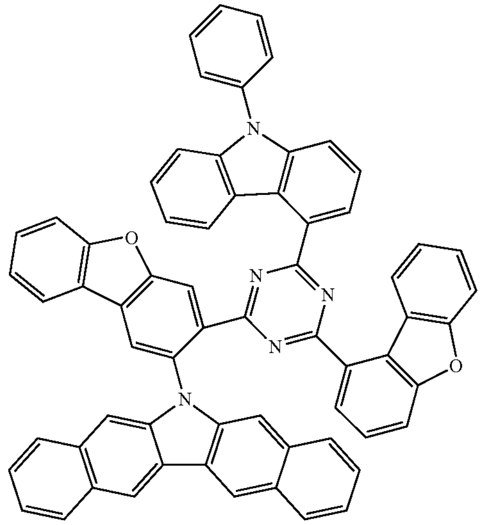
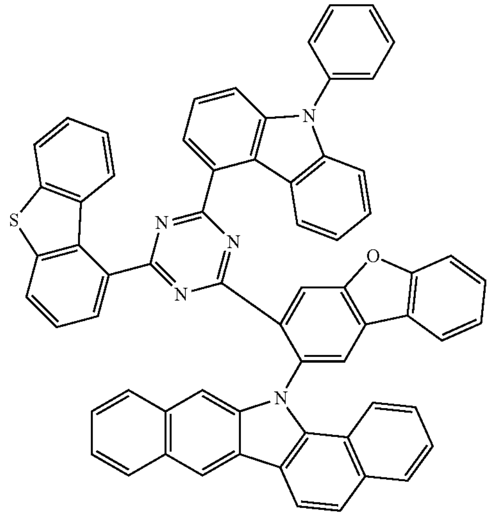

-continued
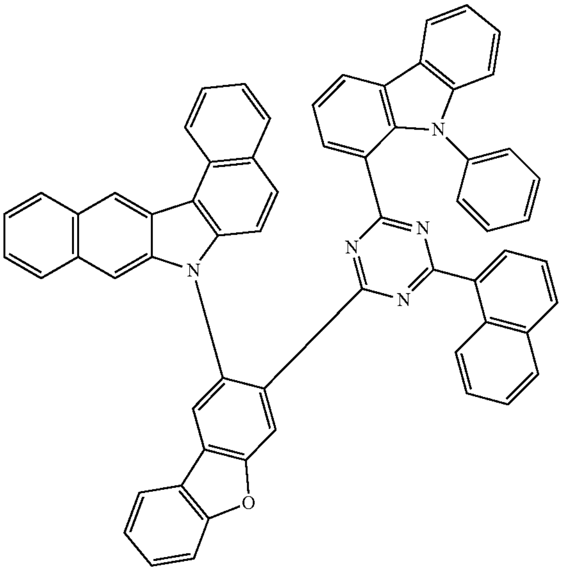
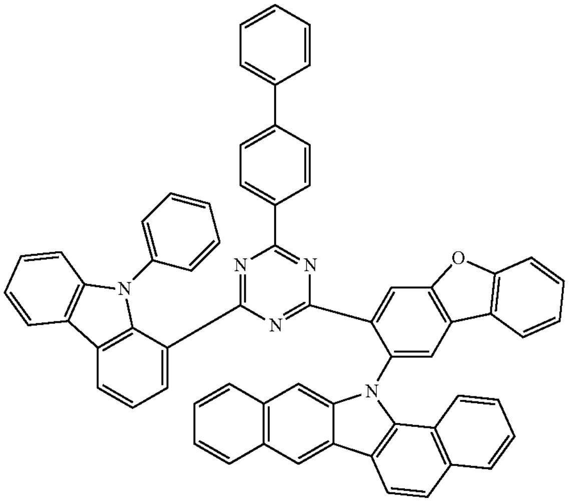
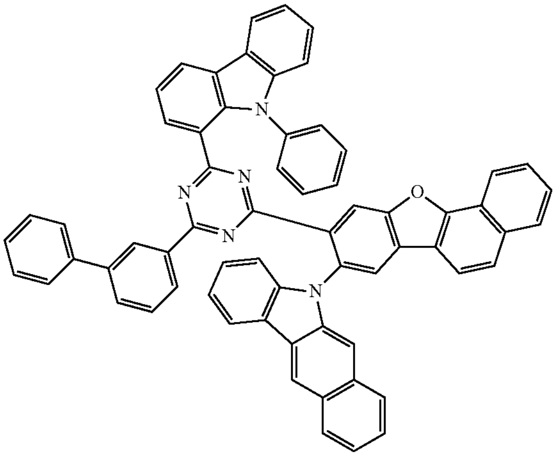
-continued
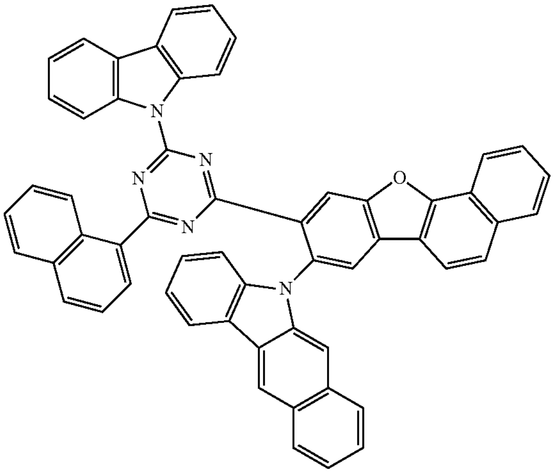
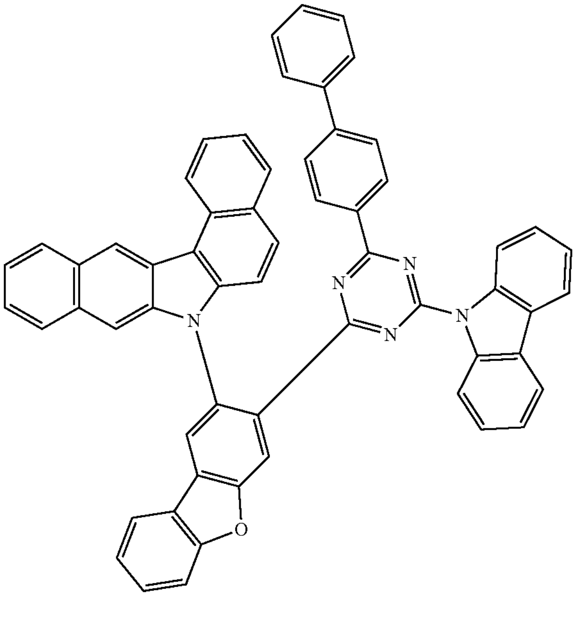
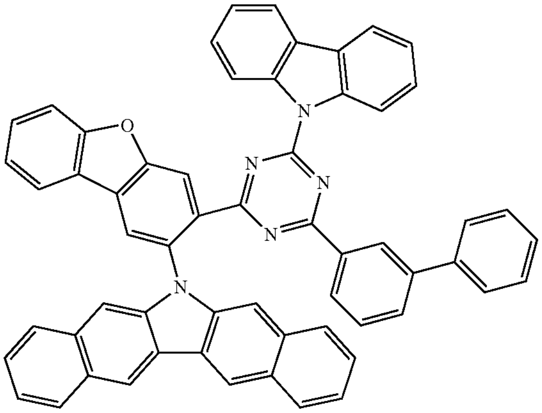

-continued
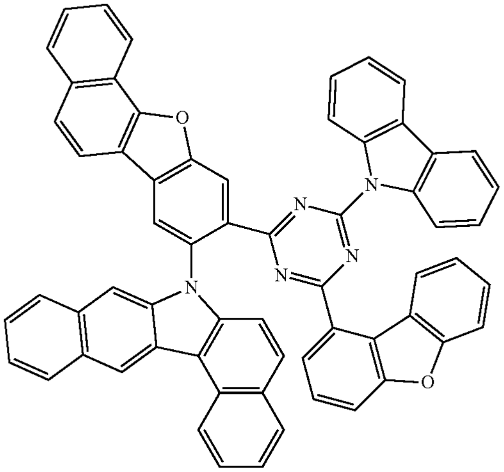
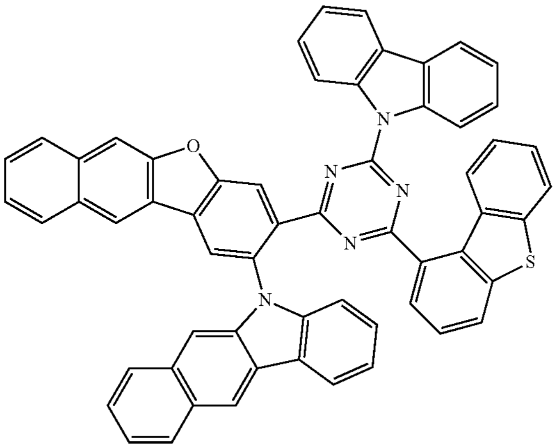
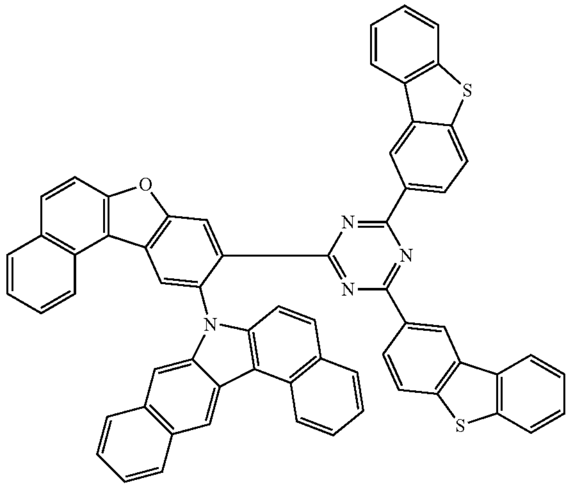
-continued
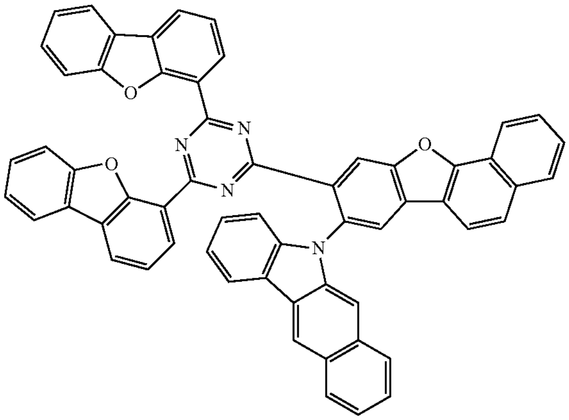
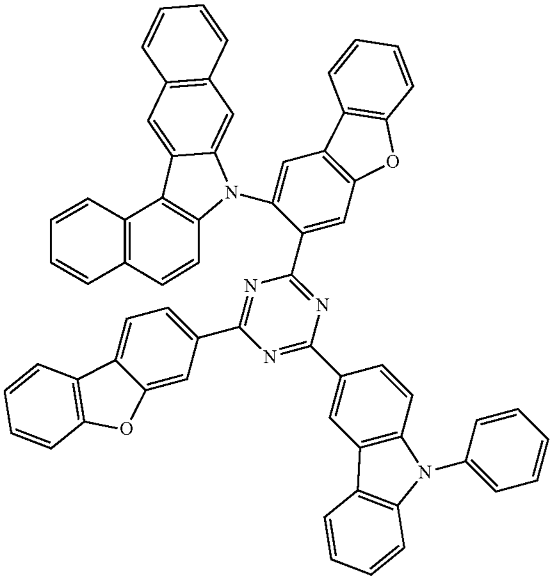
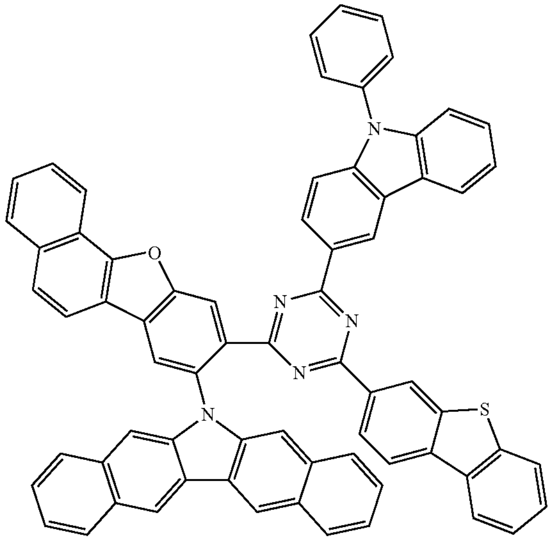

-continued
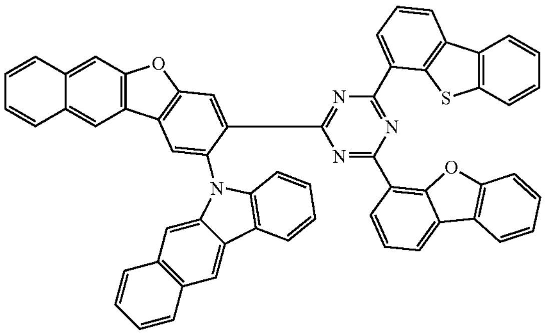
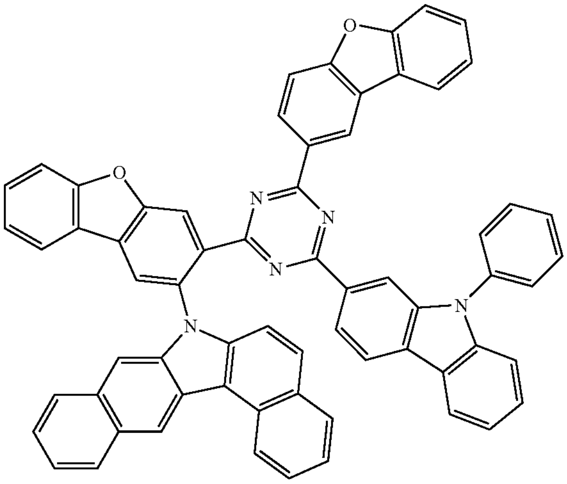
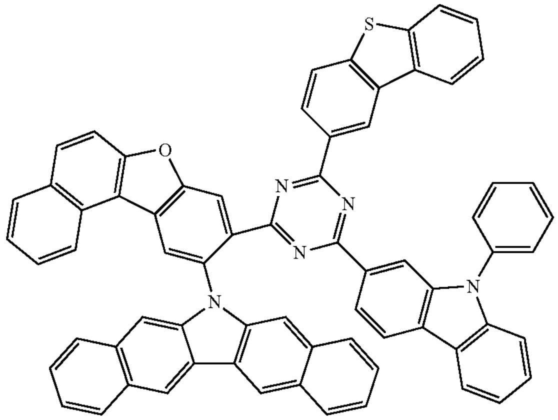
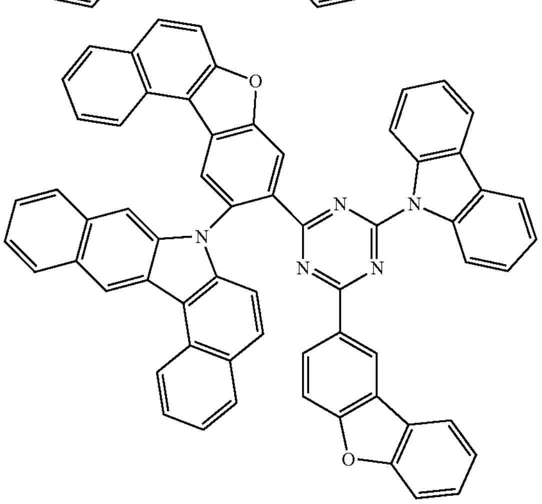
-continued
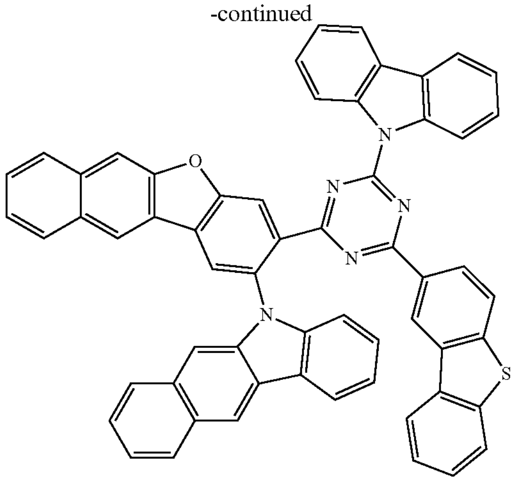
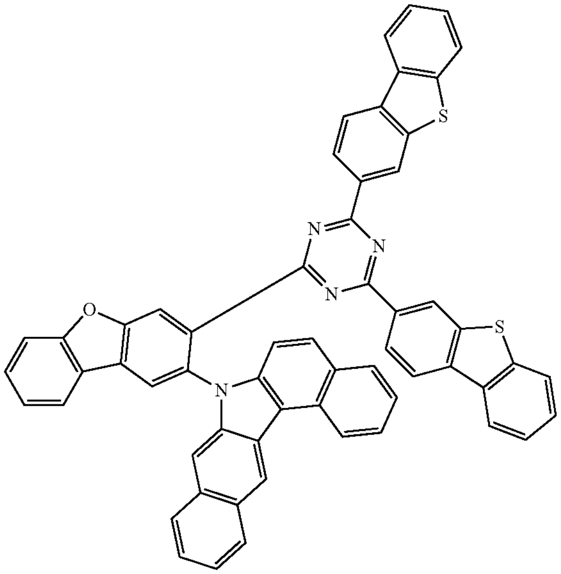
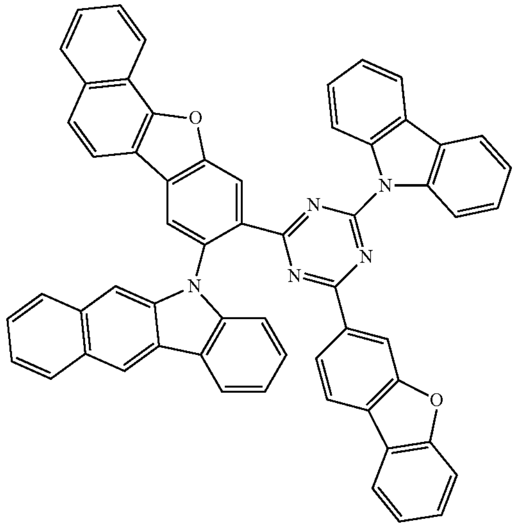

-continued
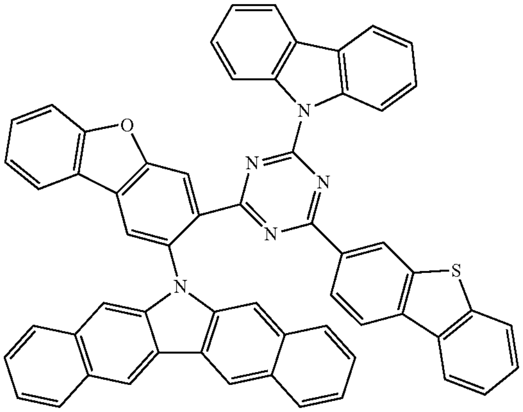
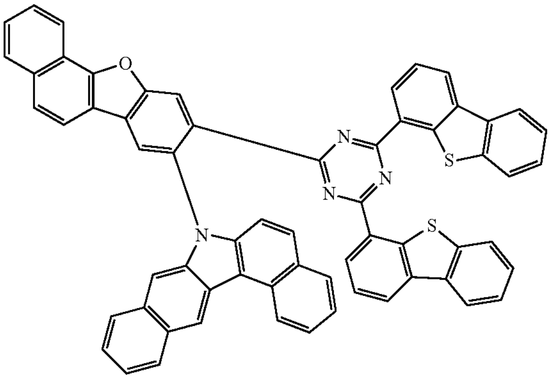
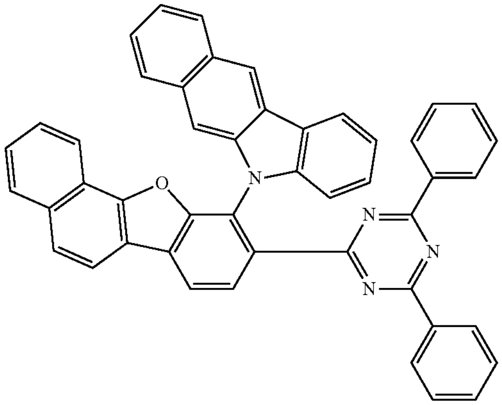
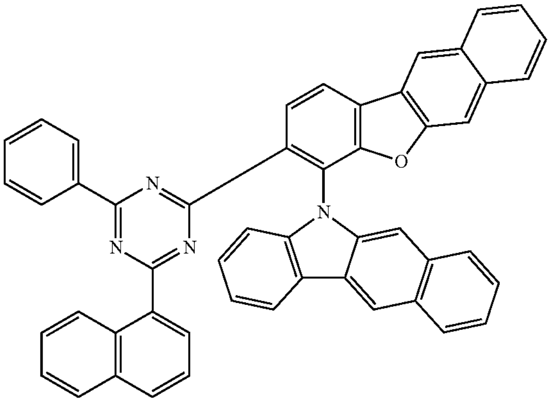
-continued
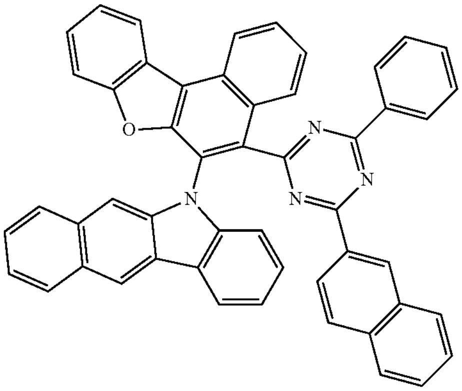
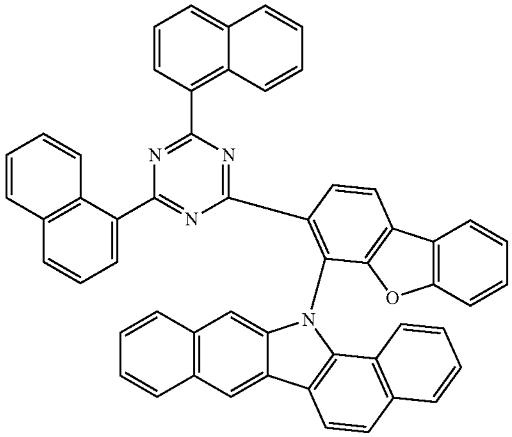
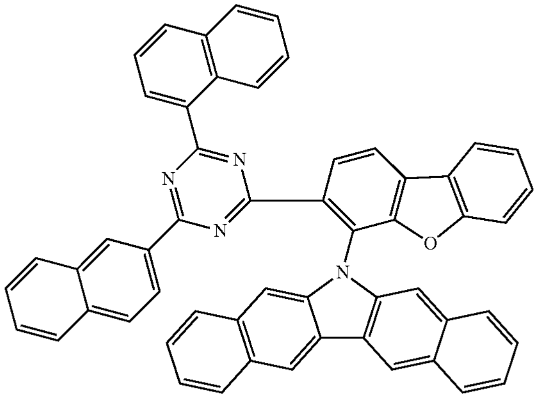
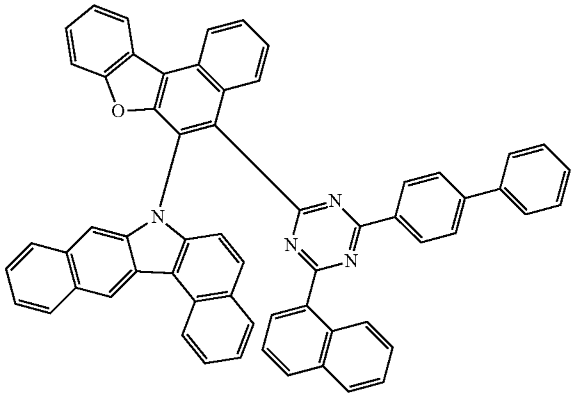

-continued
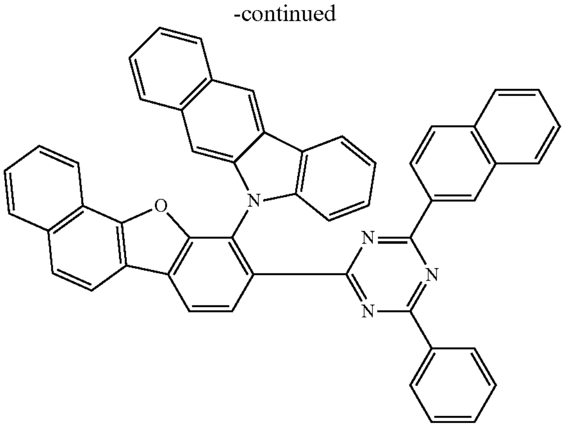
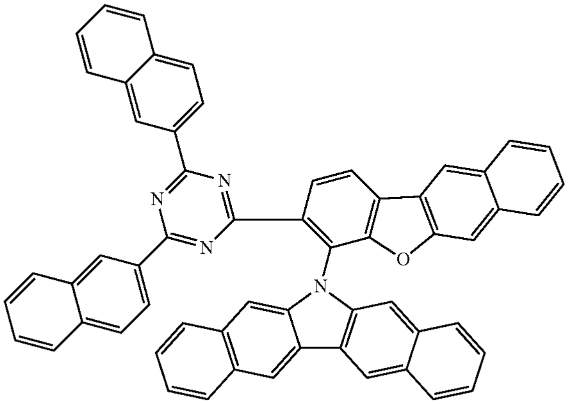
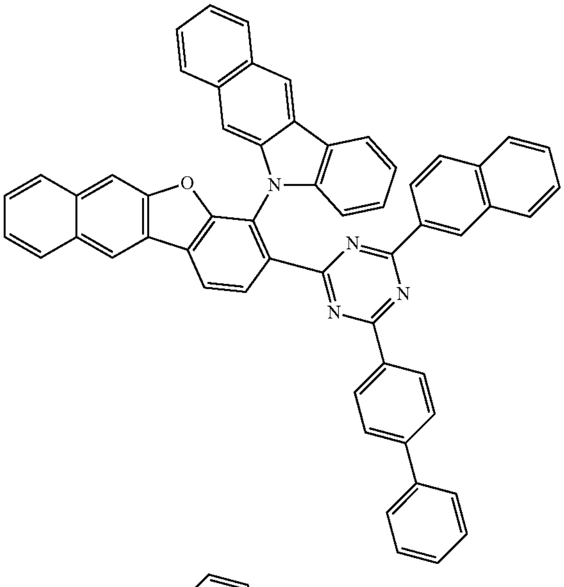
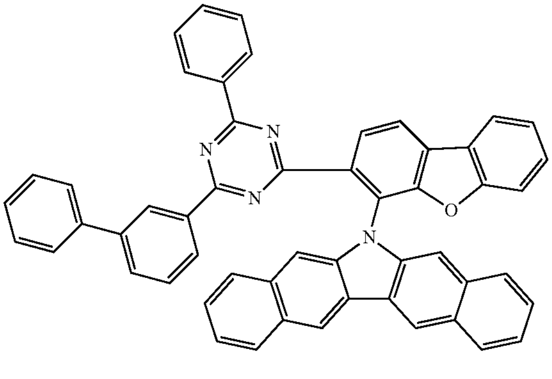
-continued
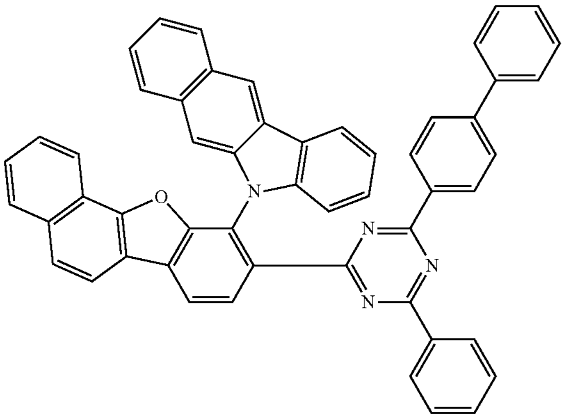
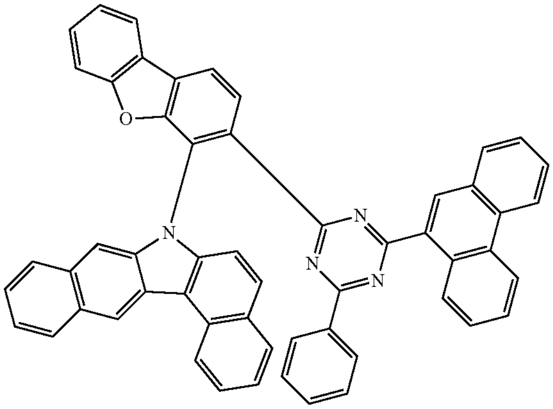
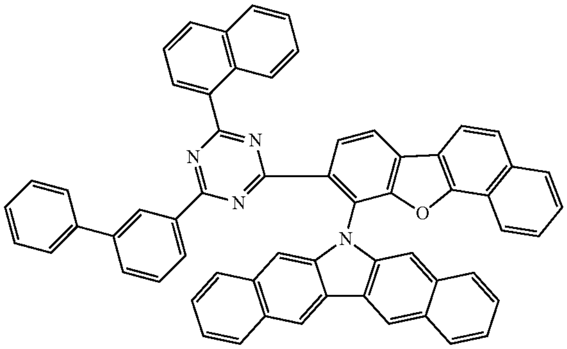
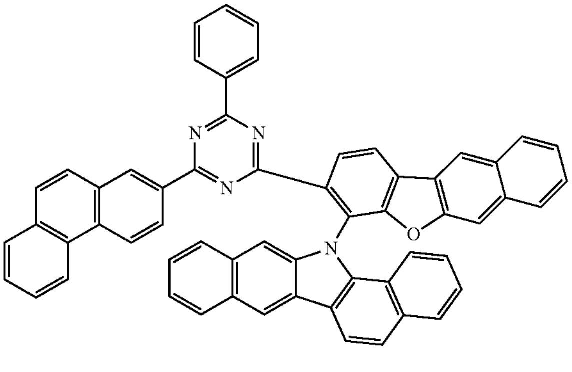

-continued
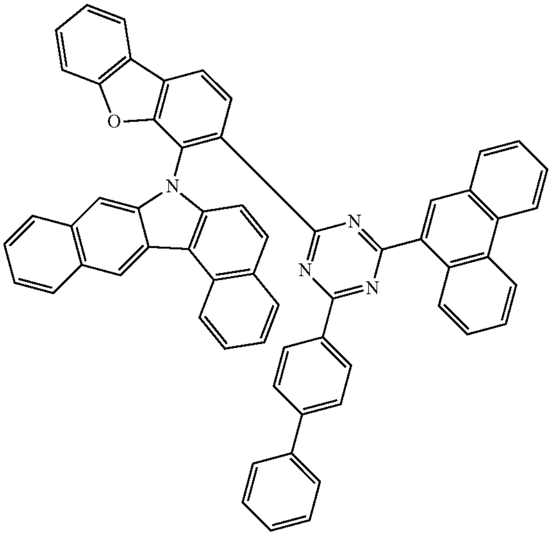
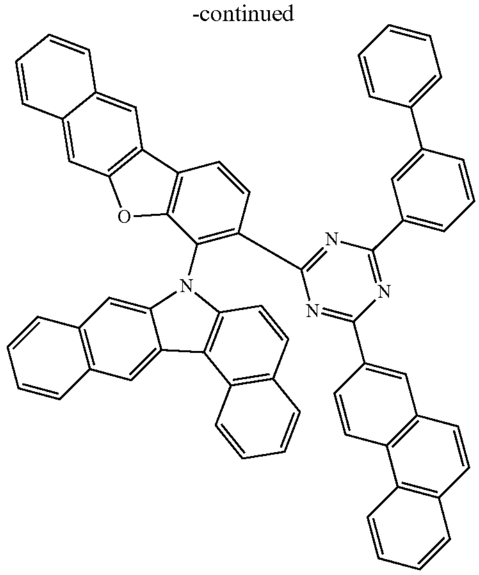
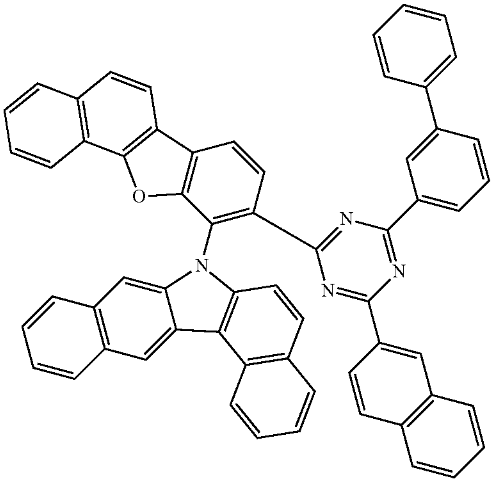
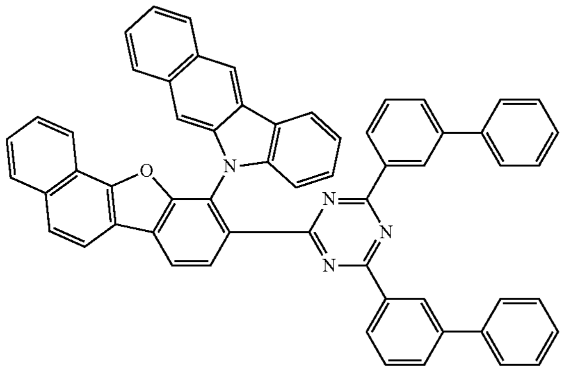
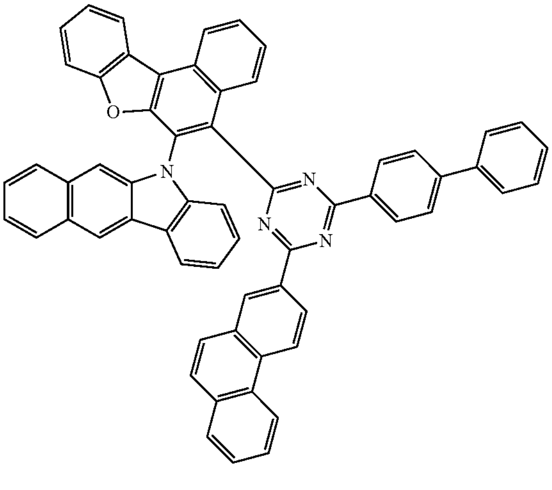
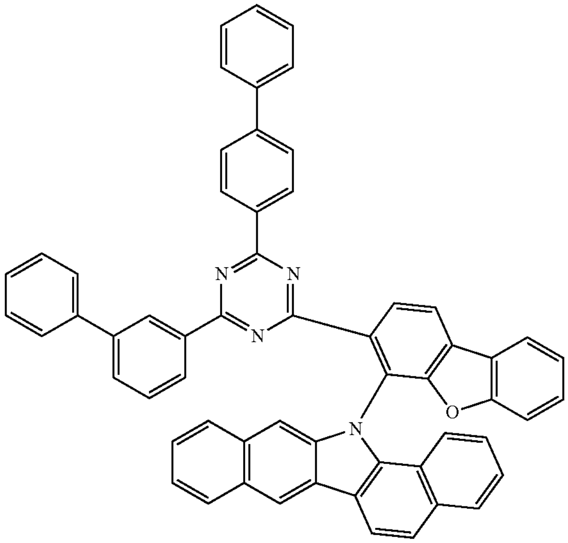
-continued -continued
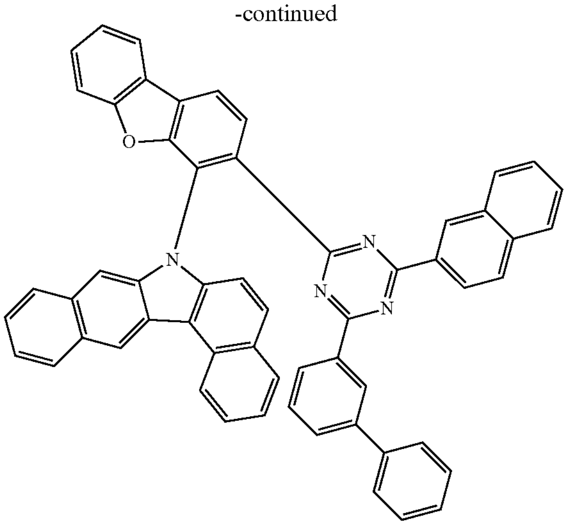
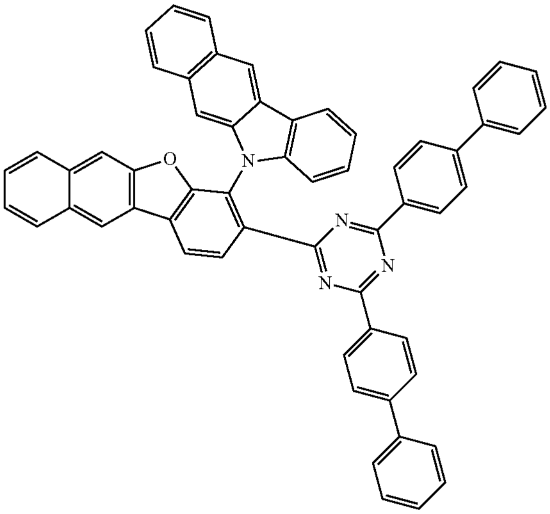
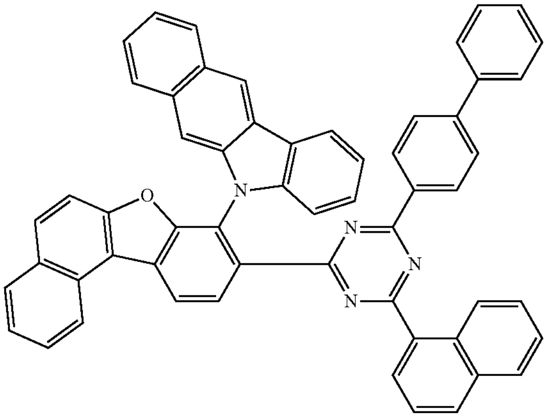
-continued
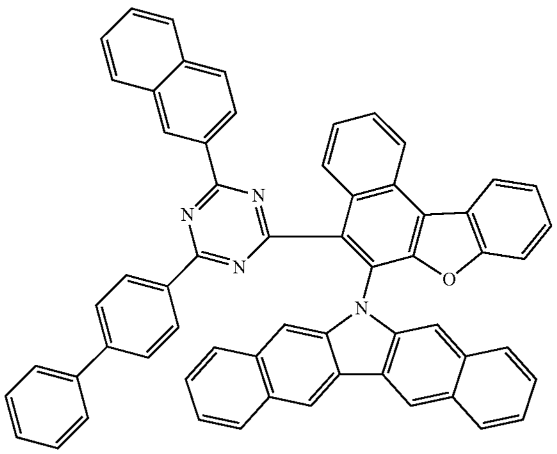
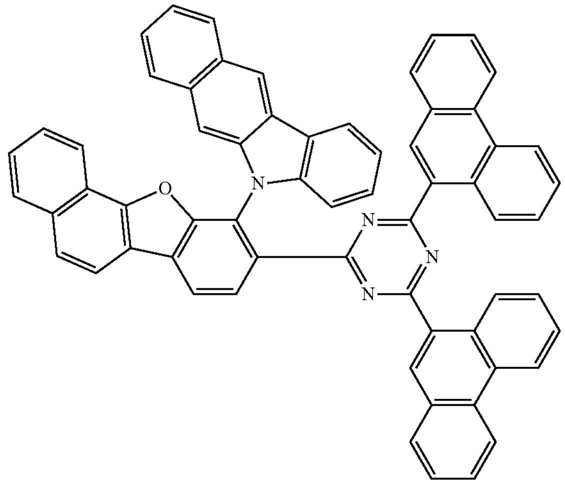
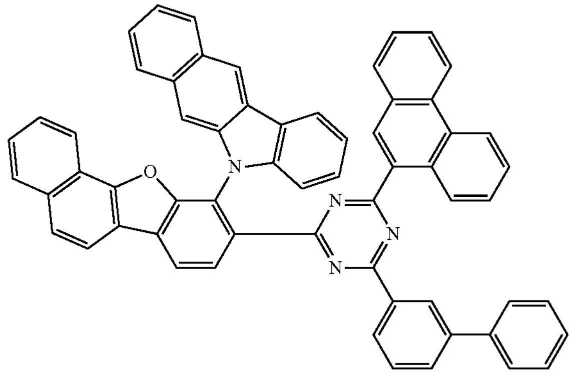

-continued
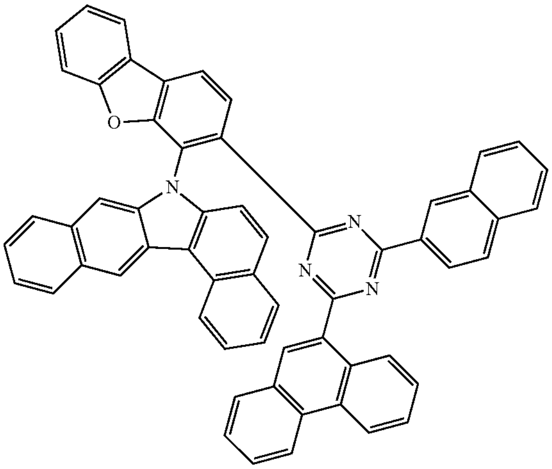
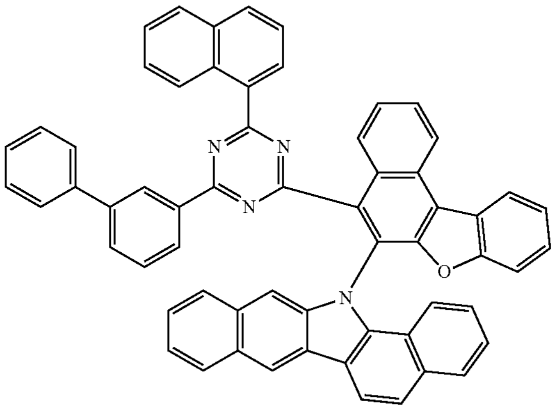
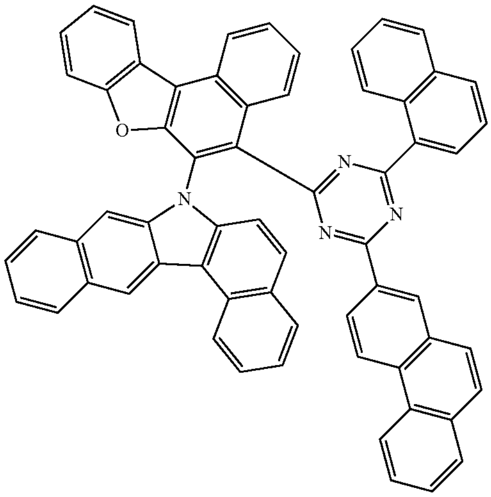
-continued
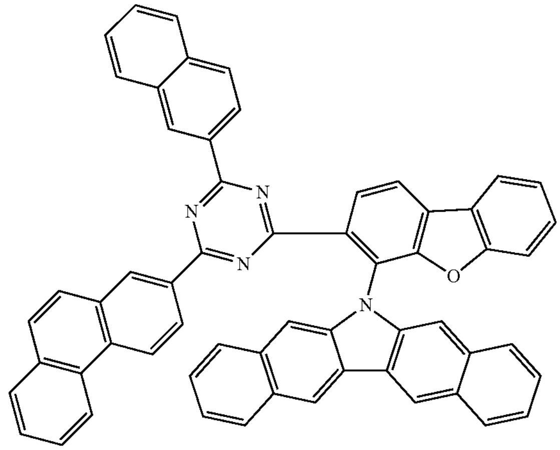
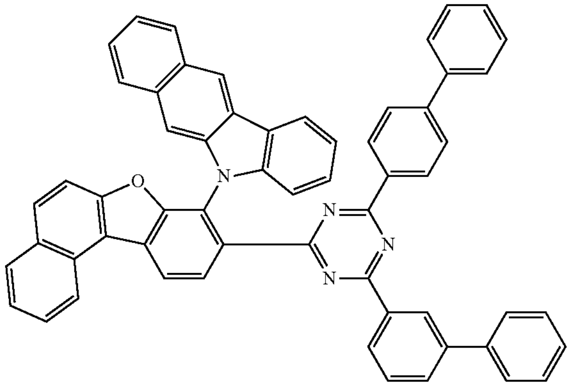
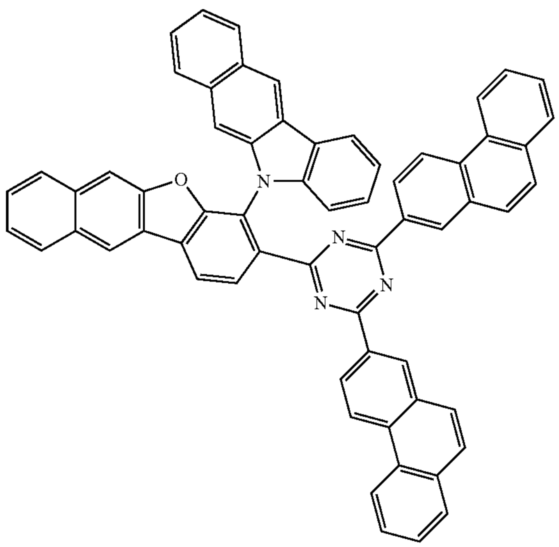

-continued
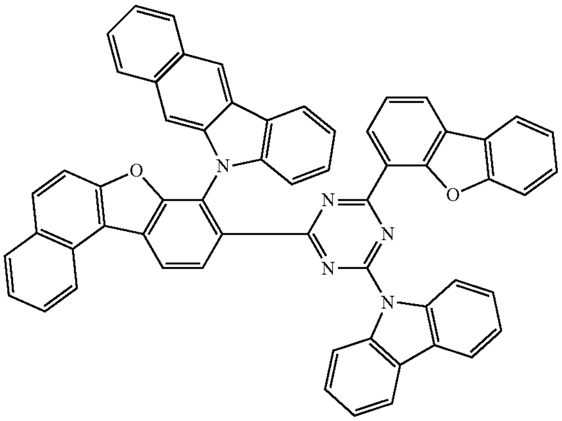
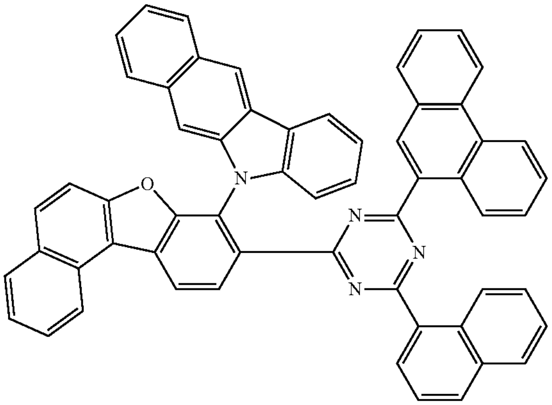
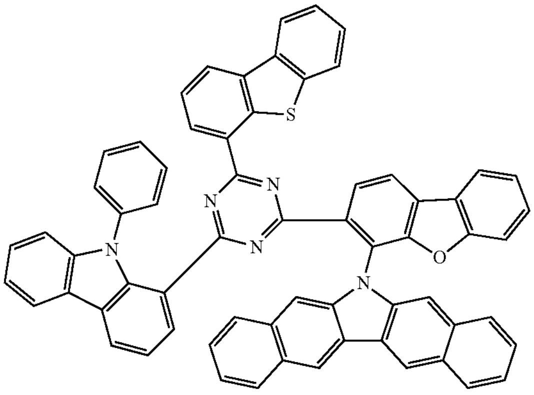
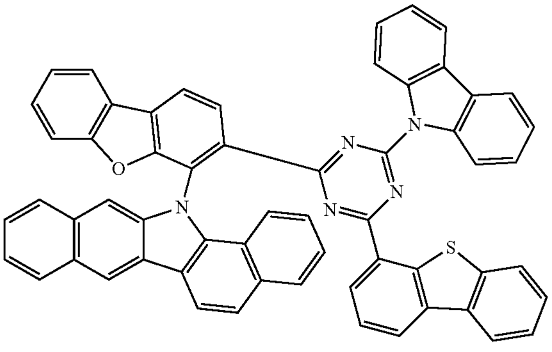
-continued
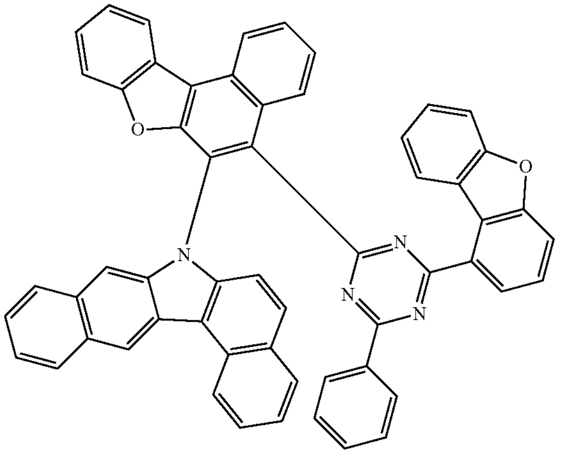
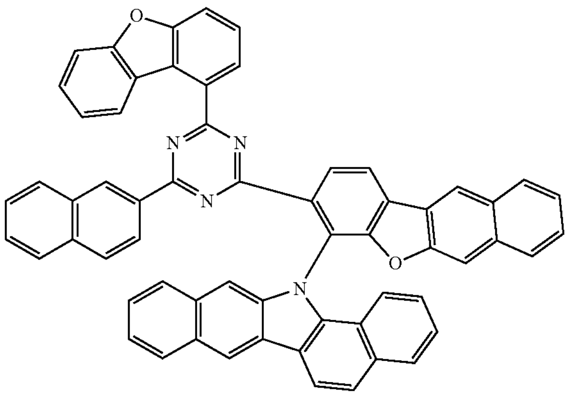
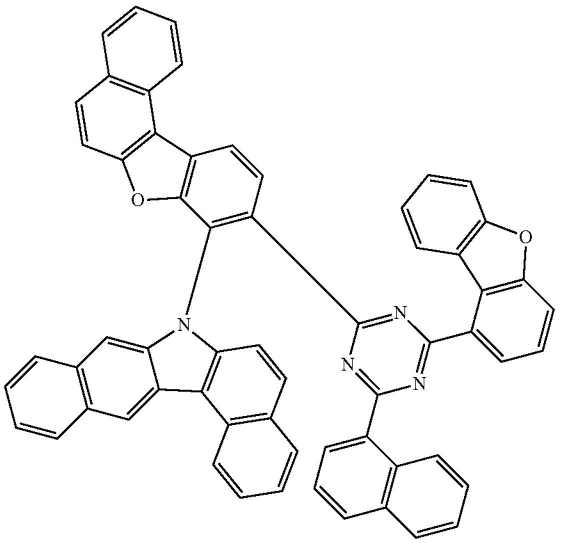

-continued
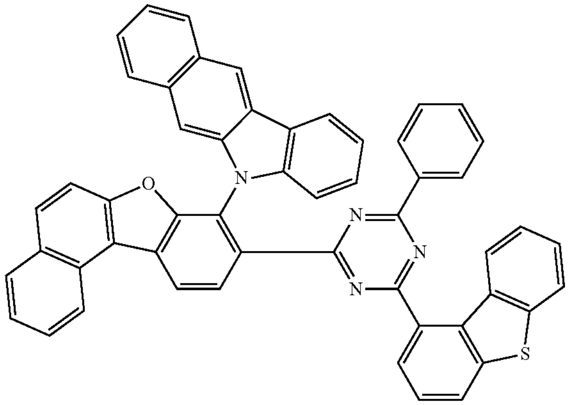
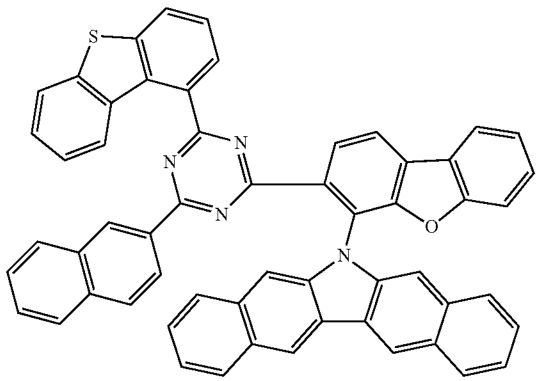
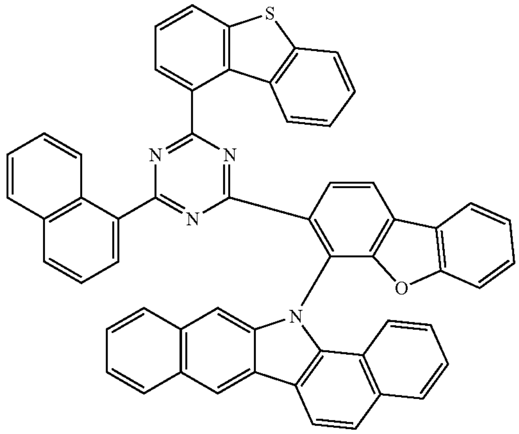
-continued
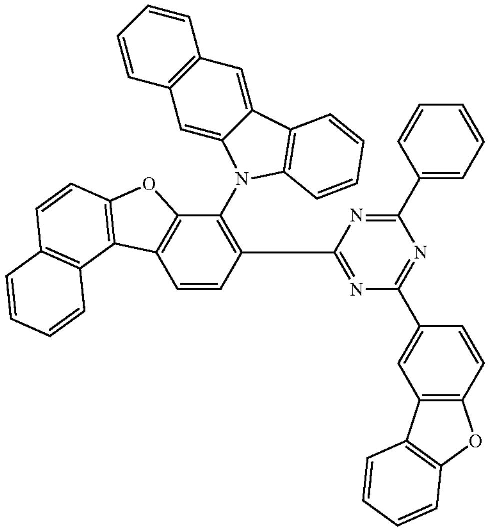
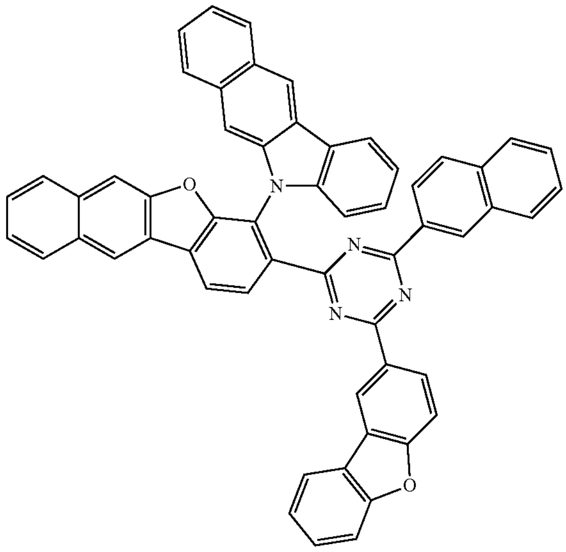
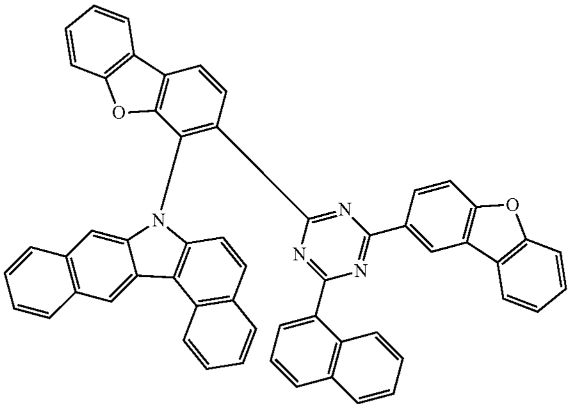

-continued
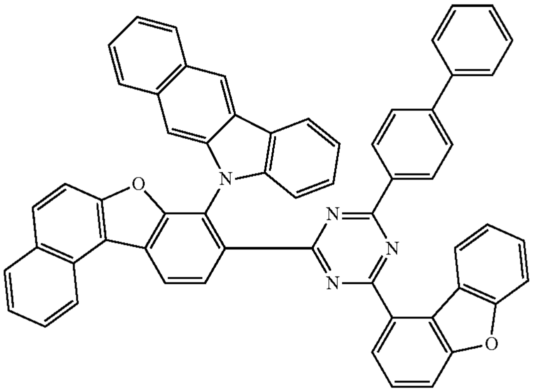
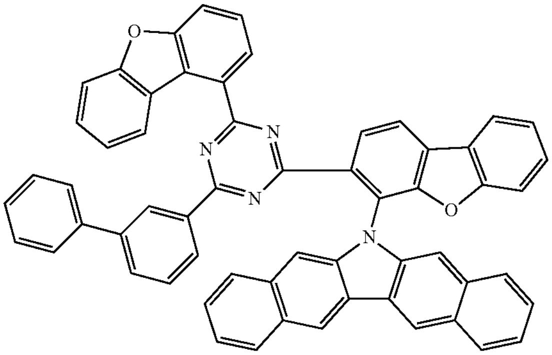
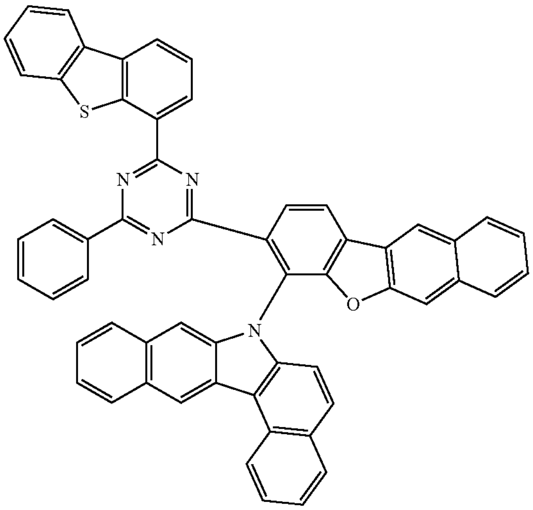
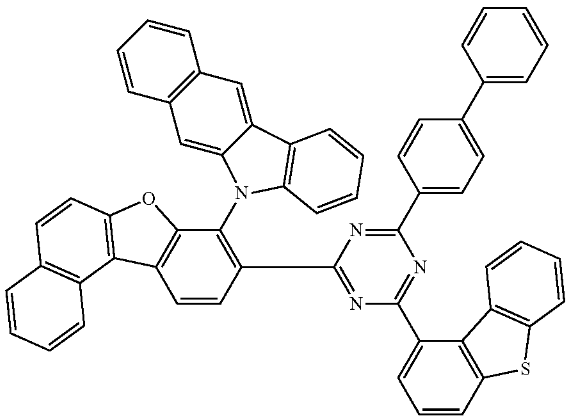
-continued
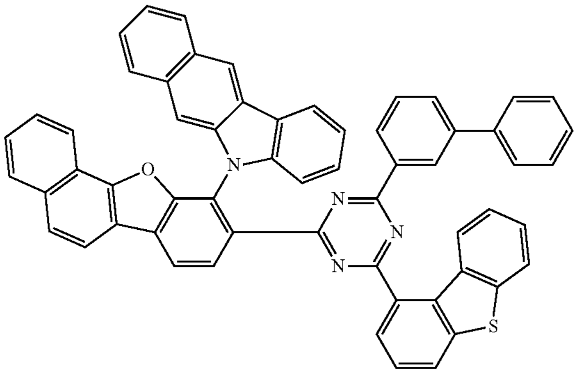
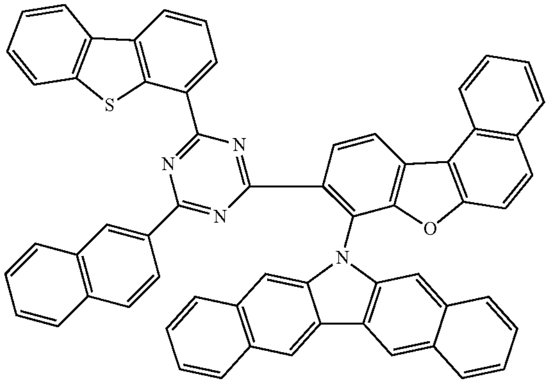
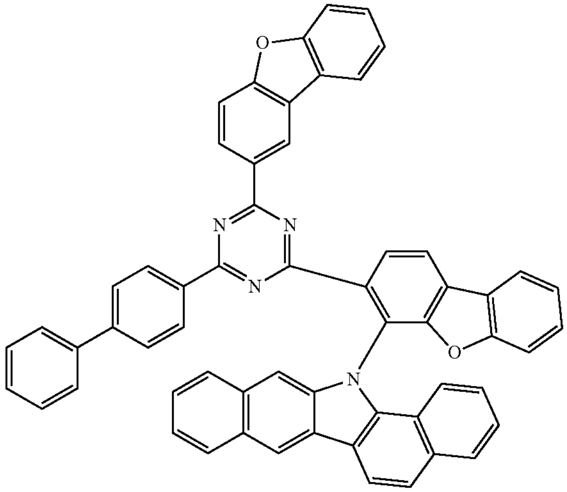
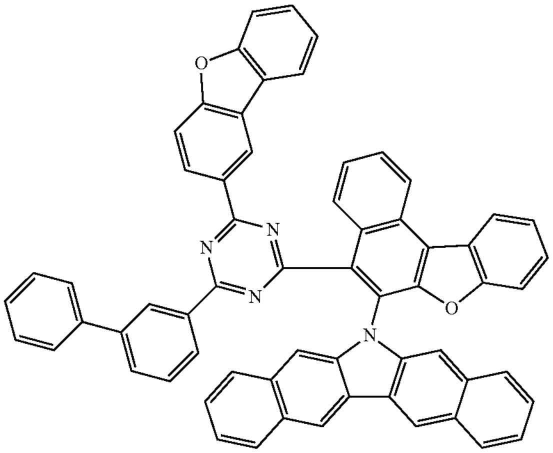

-continued
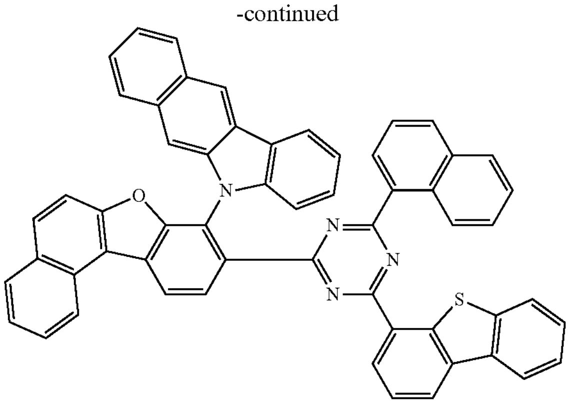
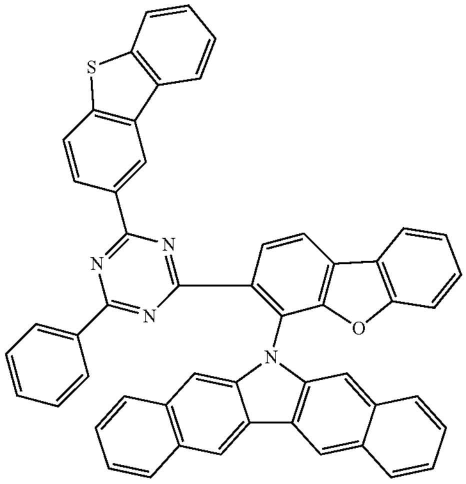
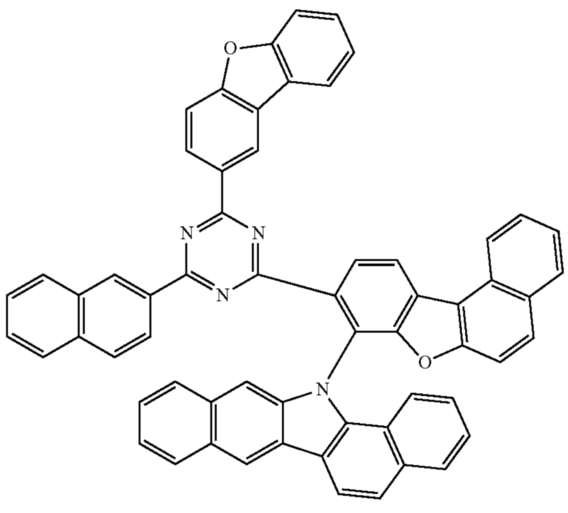
-continued
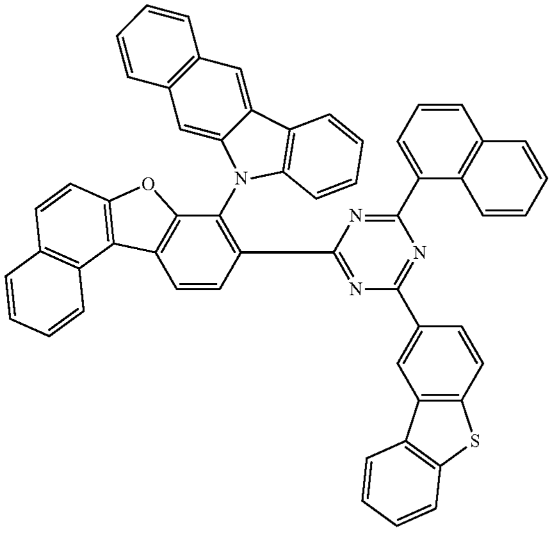
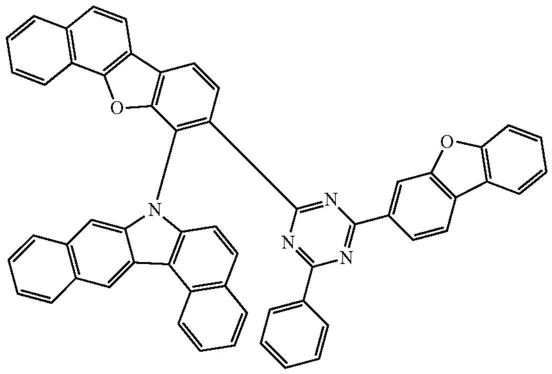
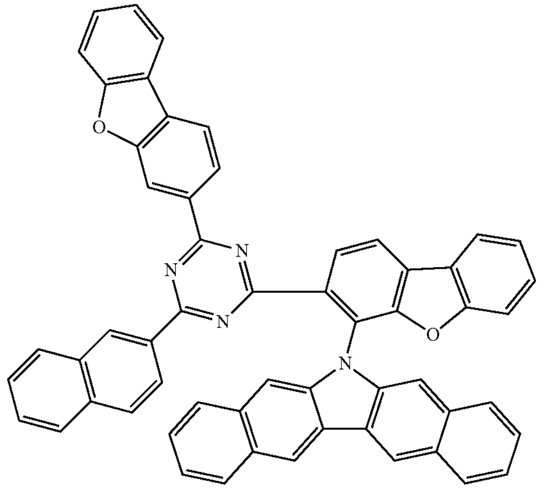

-continued
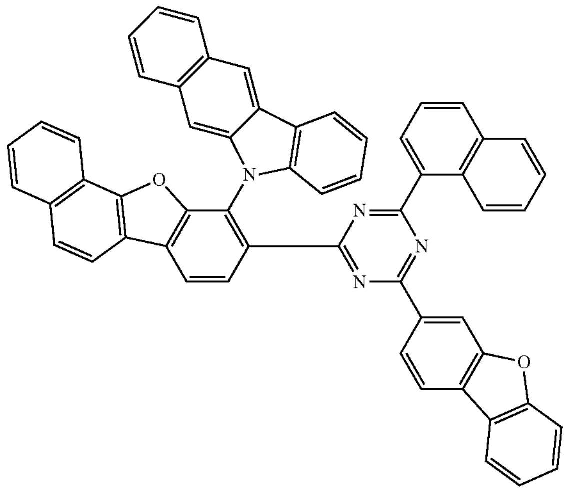
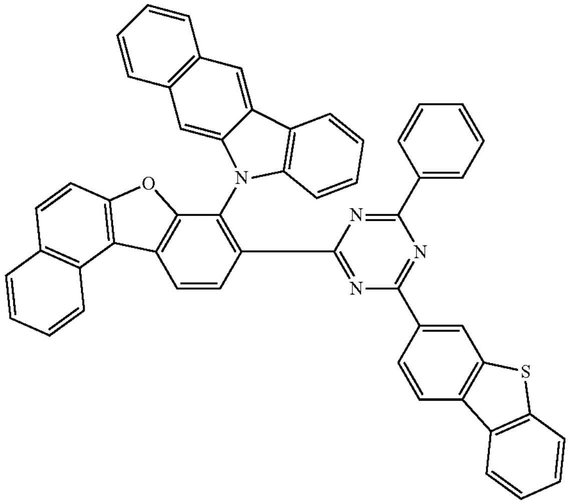
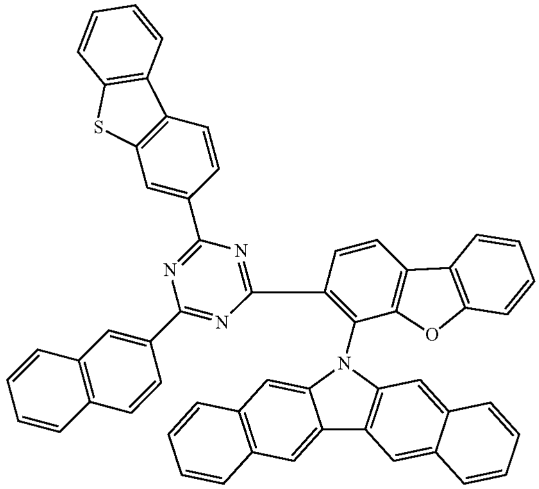
-continued
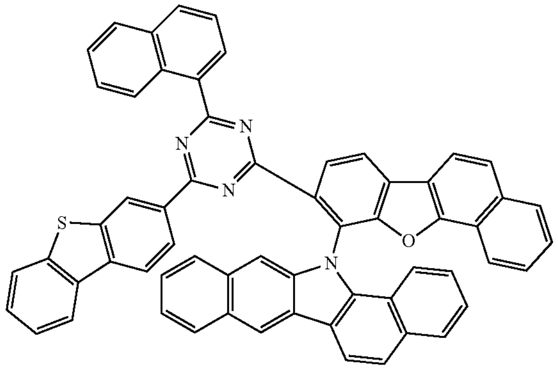
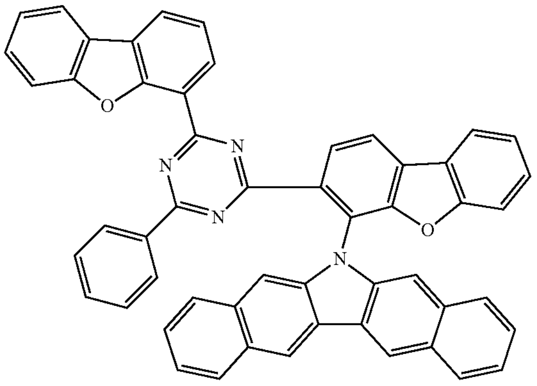
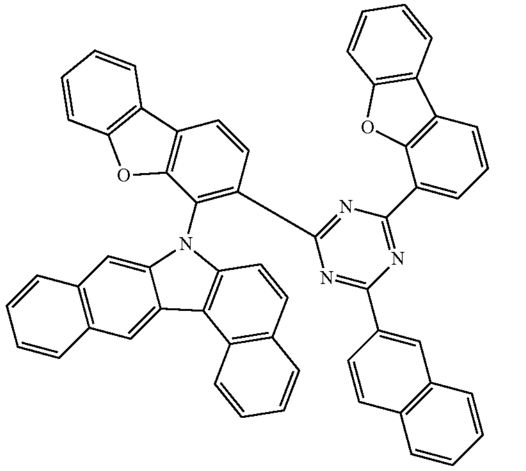
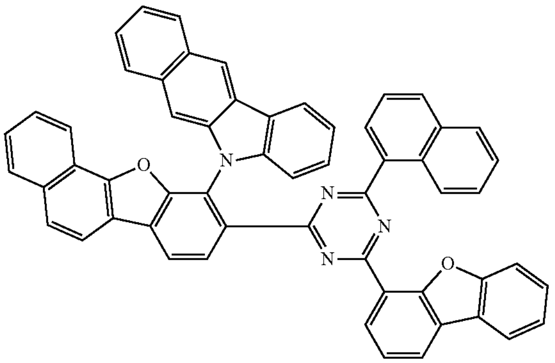

-continued
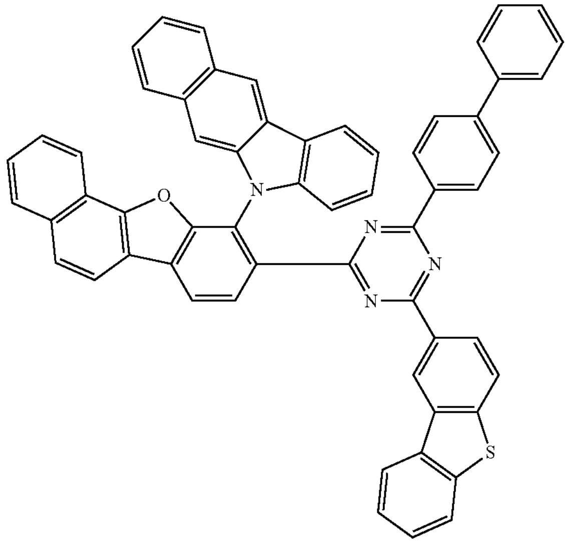
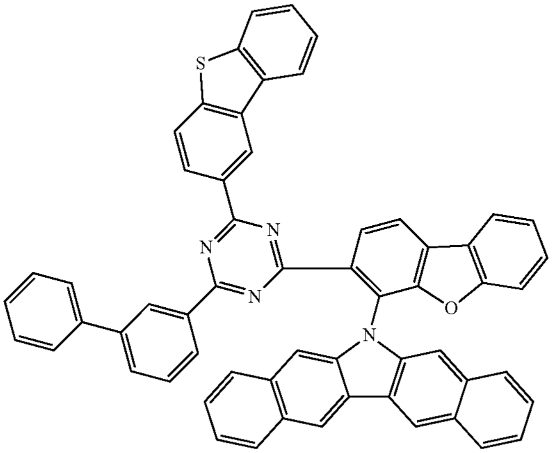
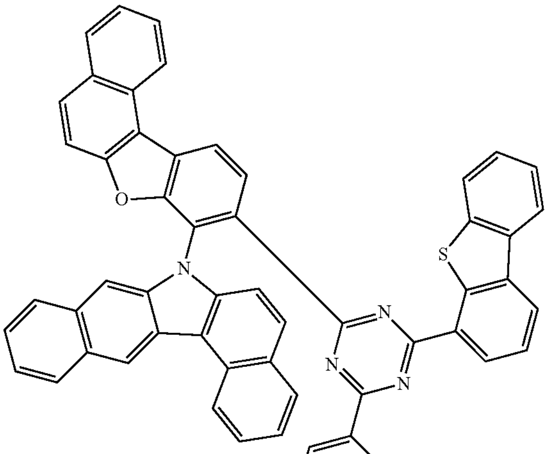
-continued
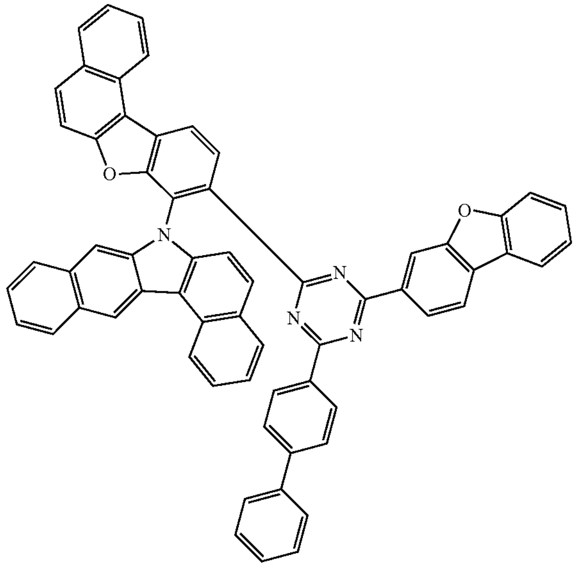
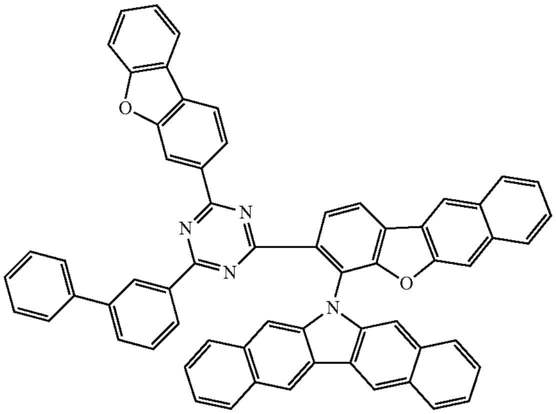
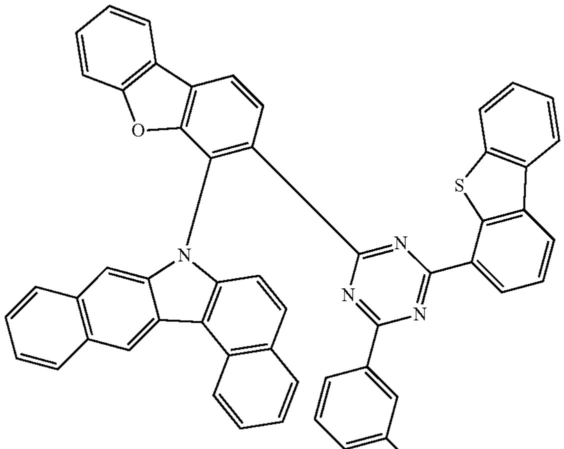

-continued
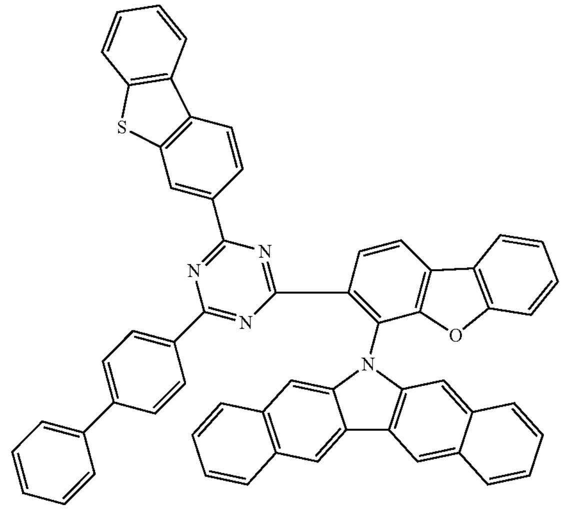
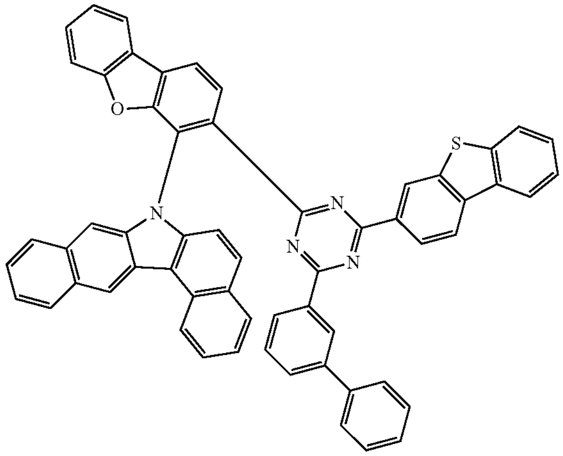
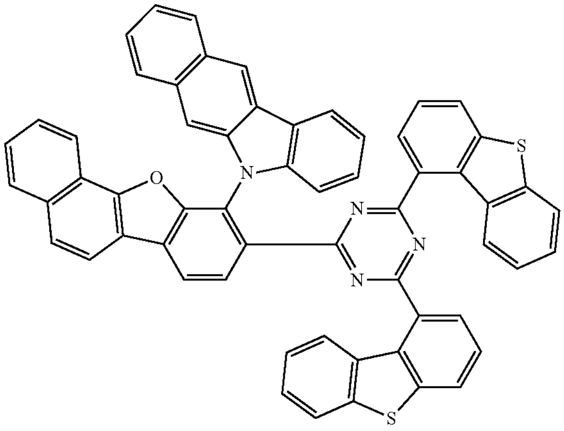
-continued
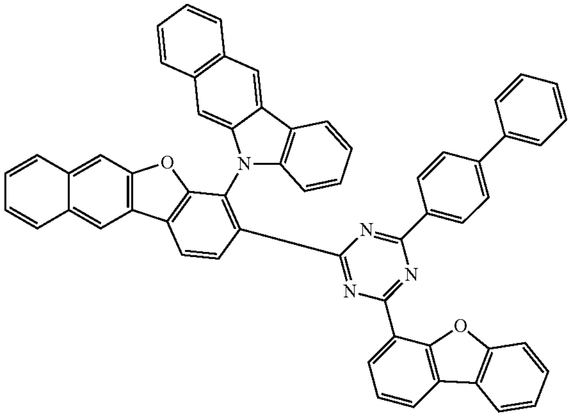
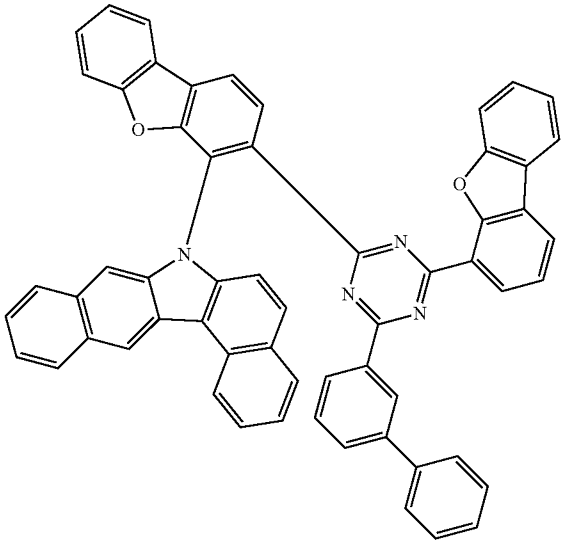
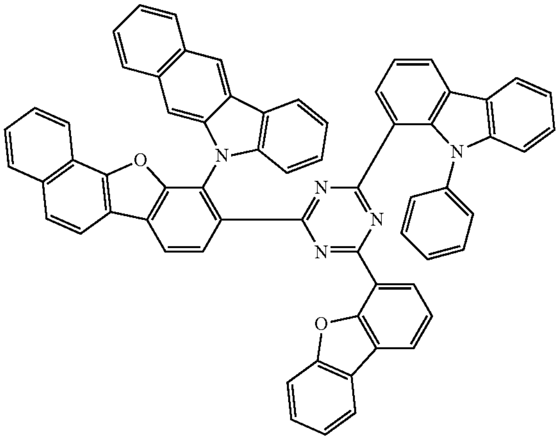

-continued
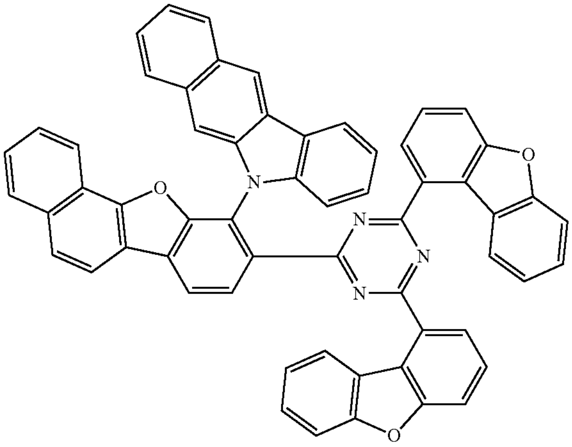
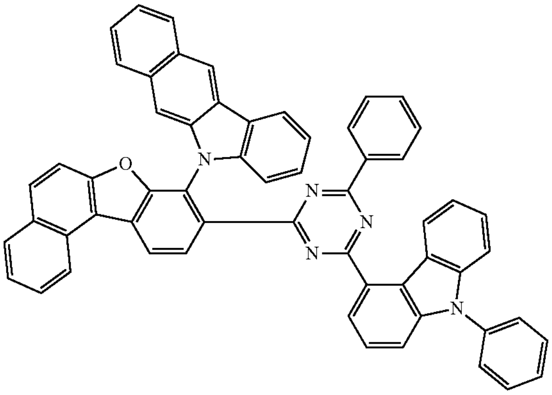
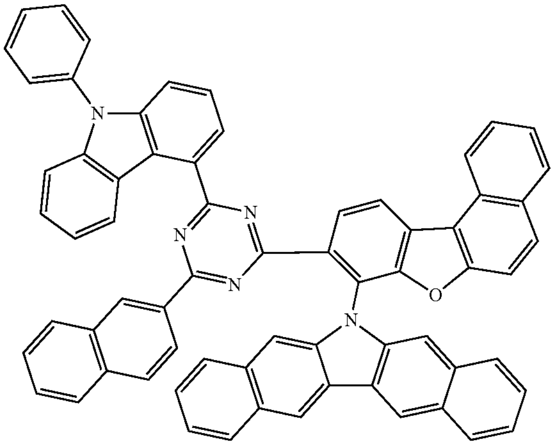
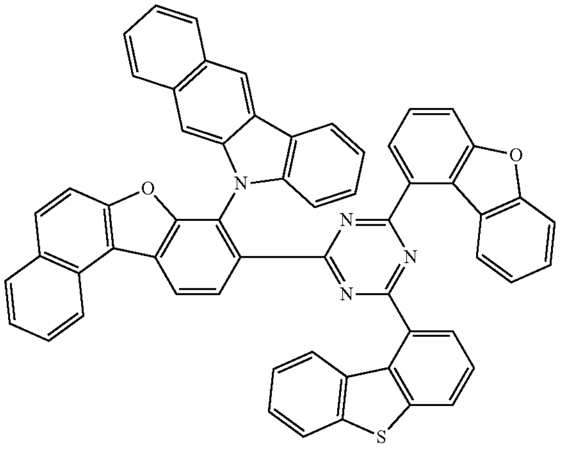
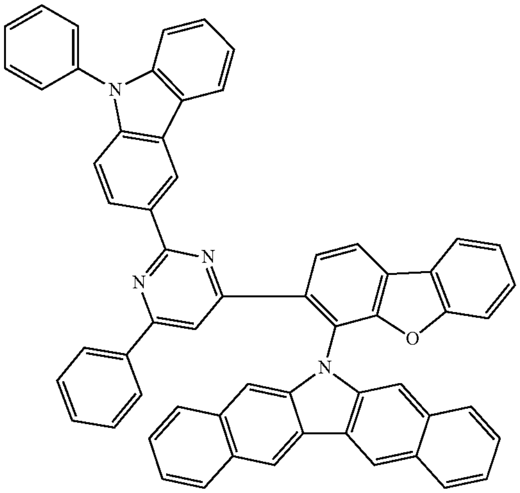
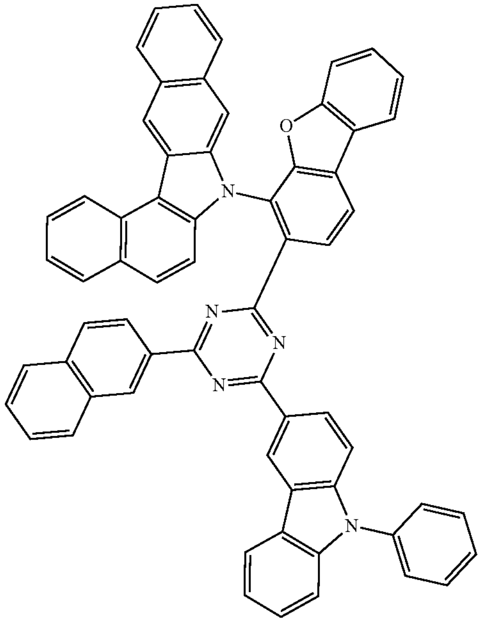
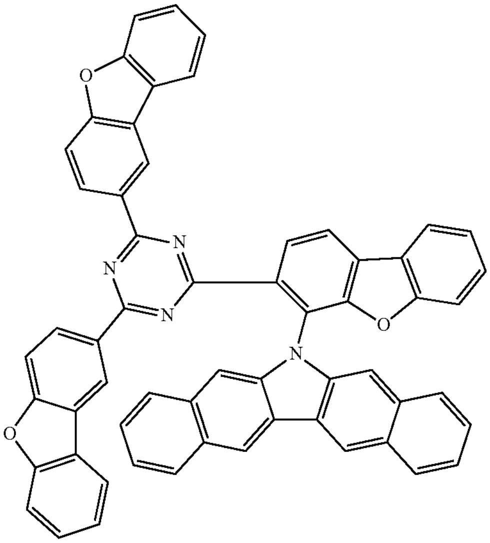

-continued
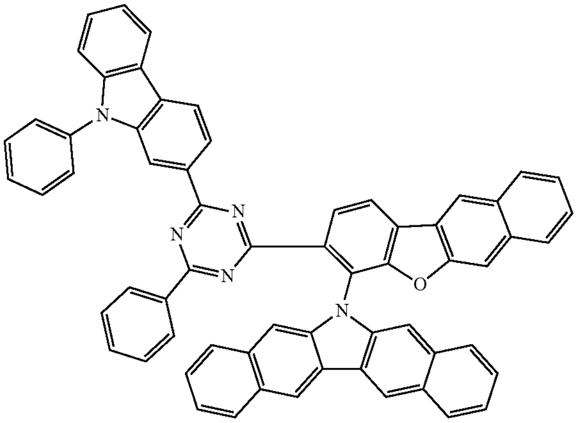
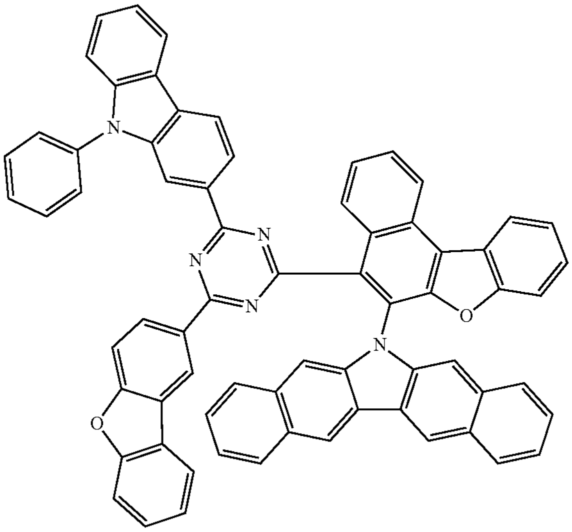
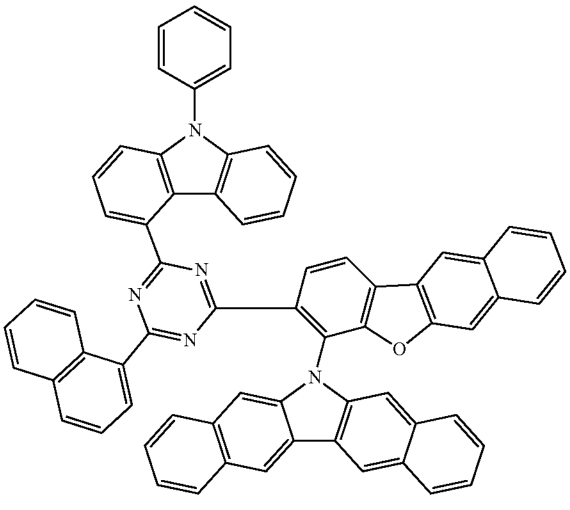
-continued
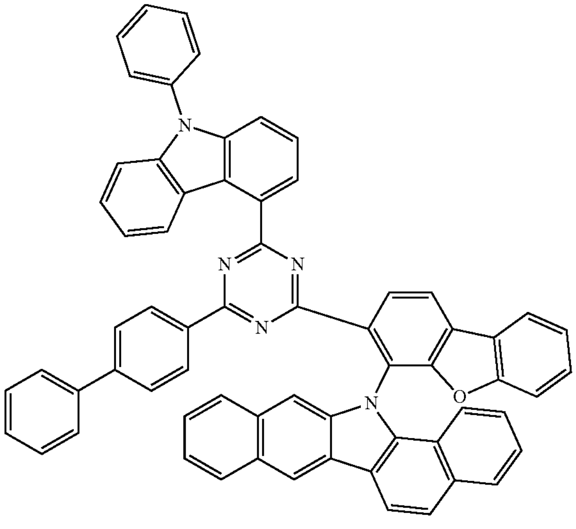
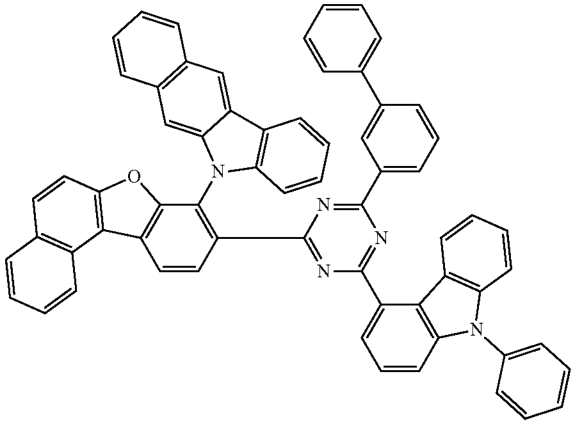
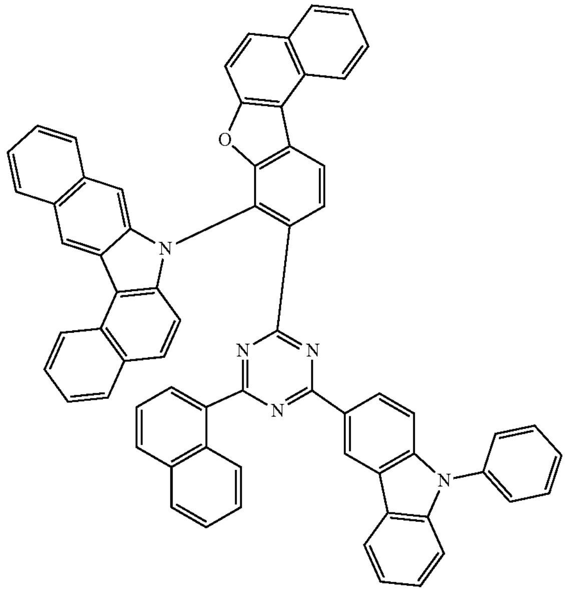

-continued
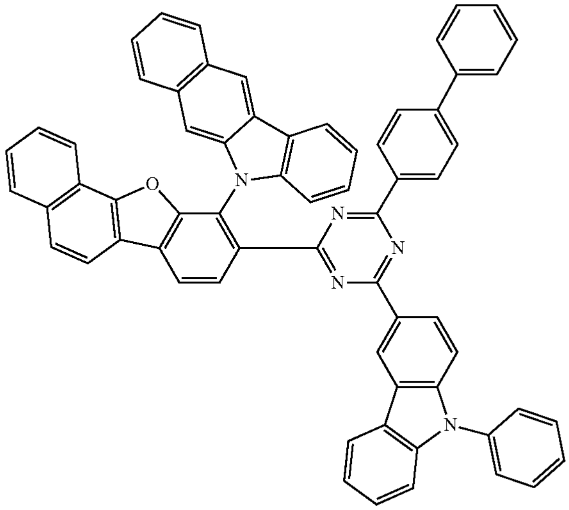
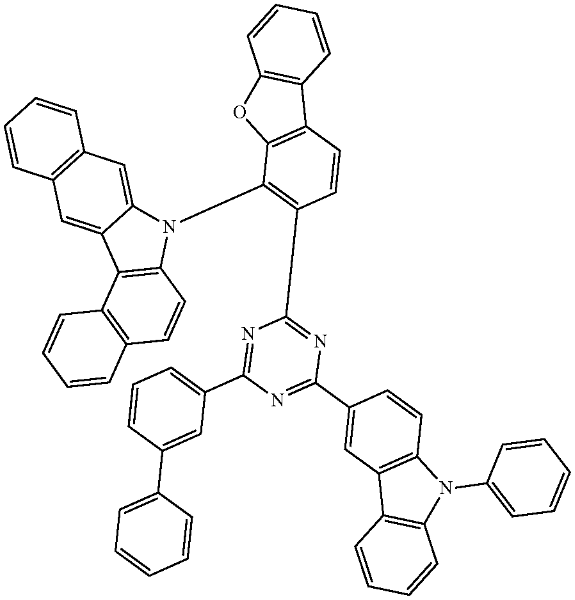
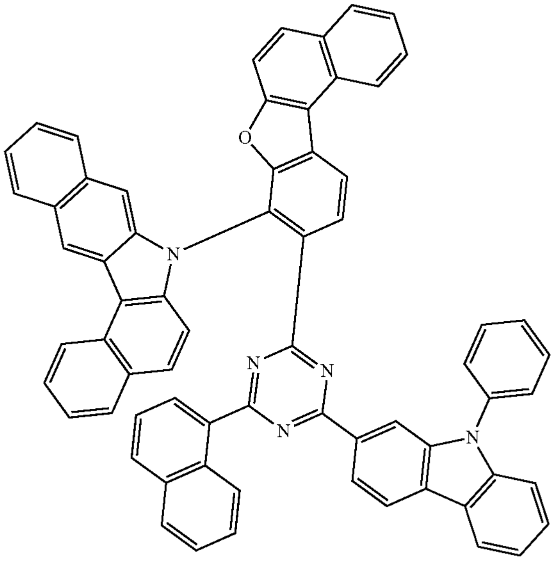
-continued
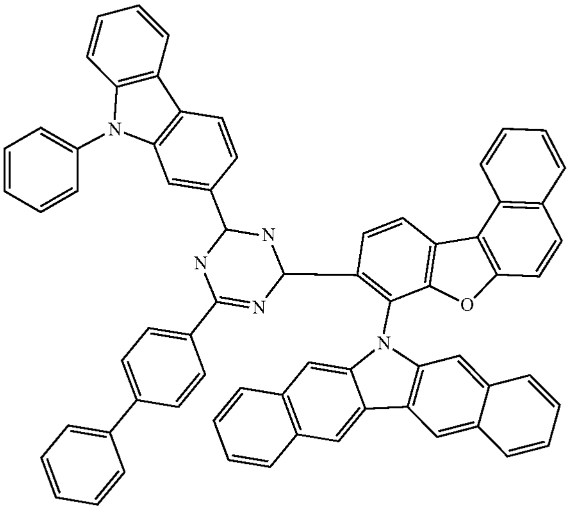
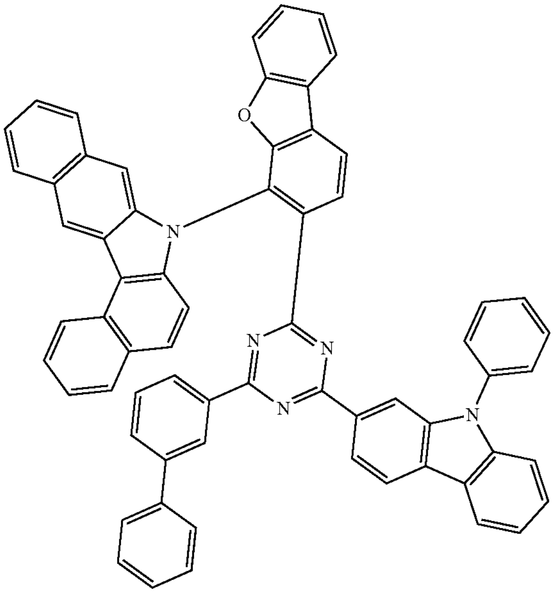
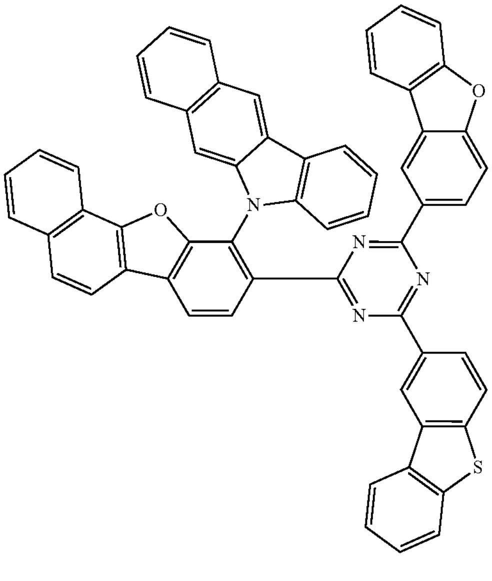

-continued
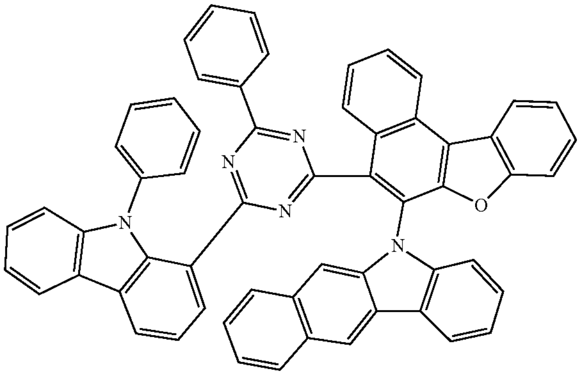
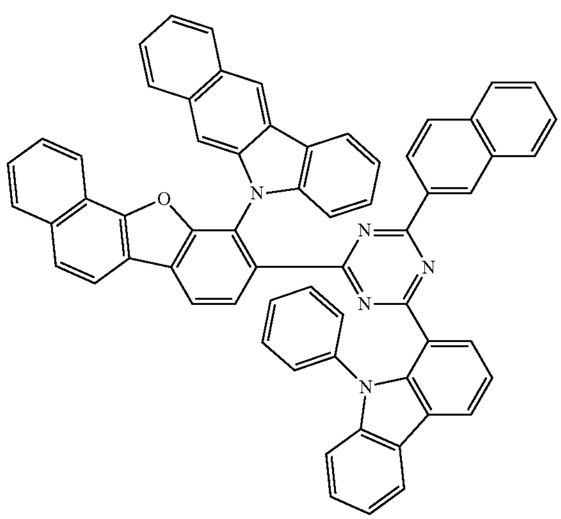
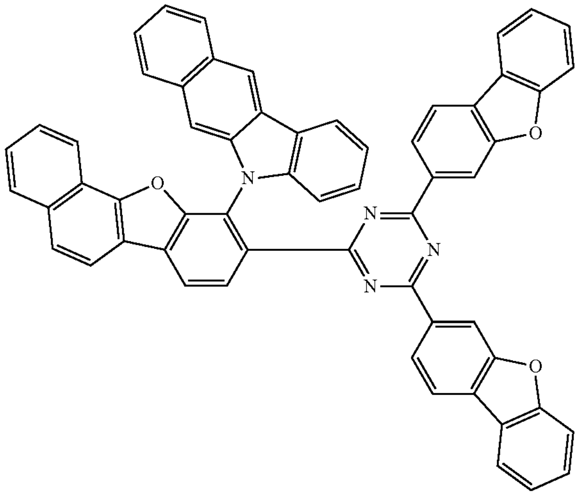
-continued
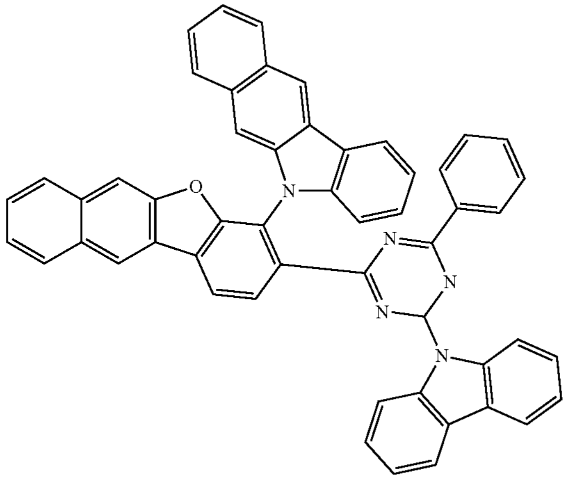
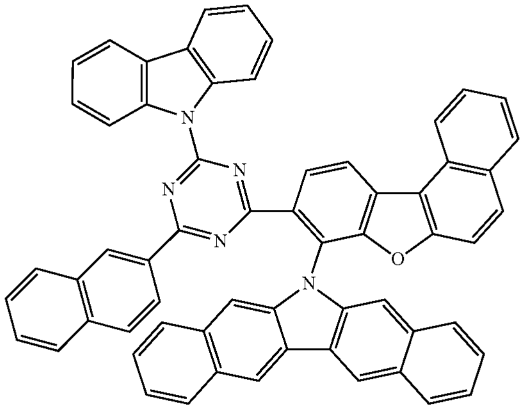
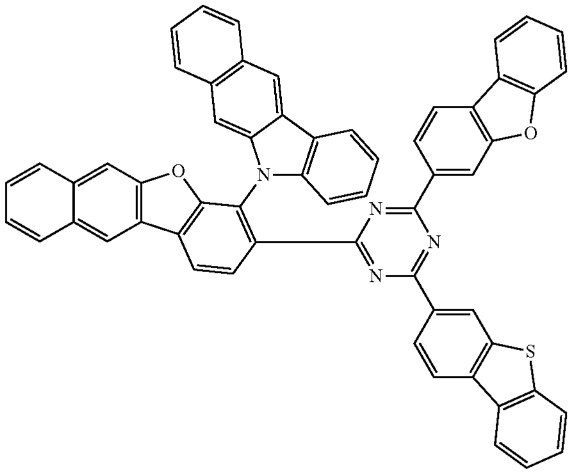

-continued
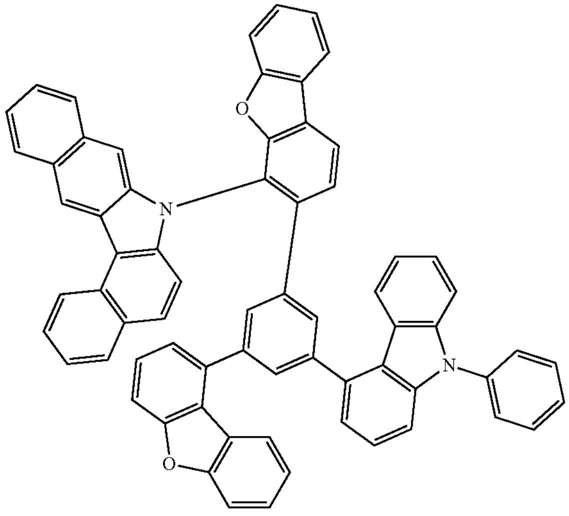
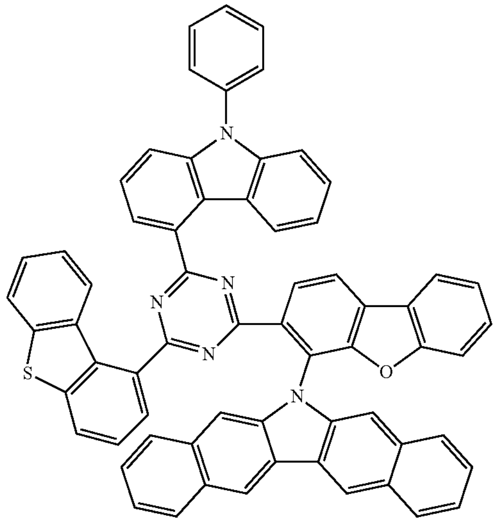
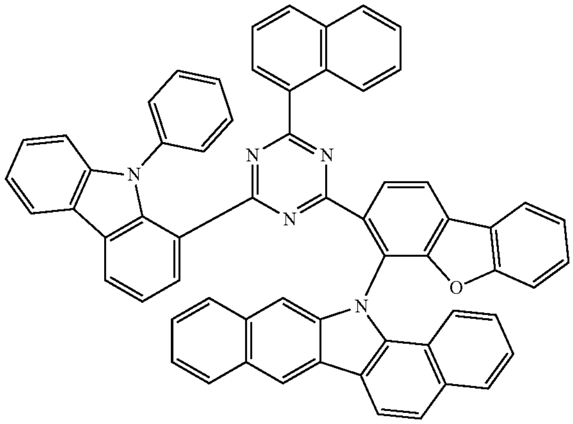
-continued
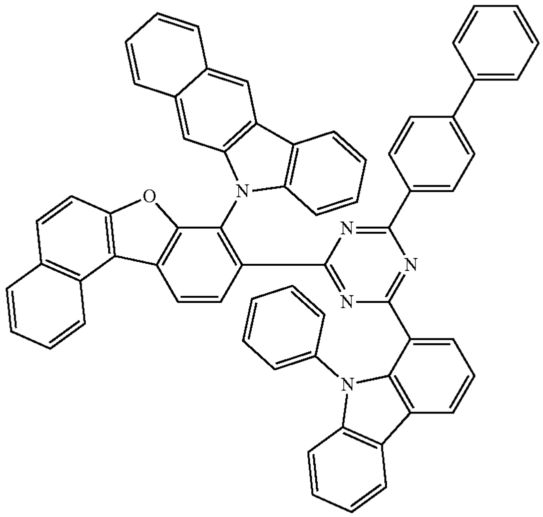
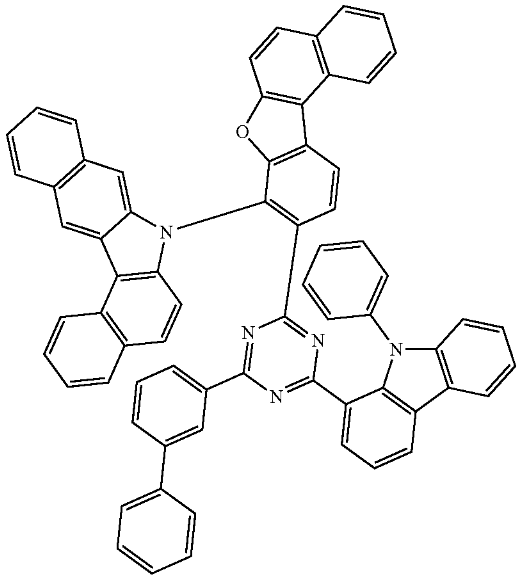
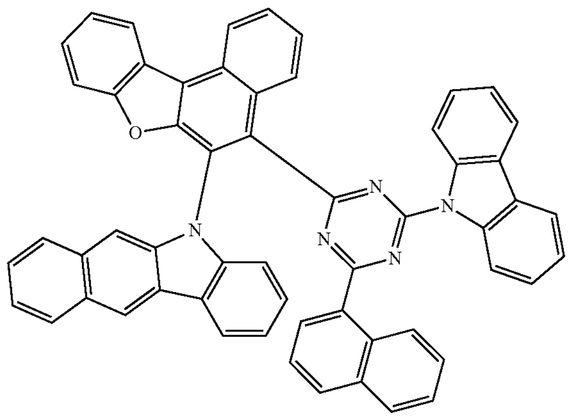

-continued
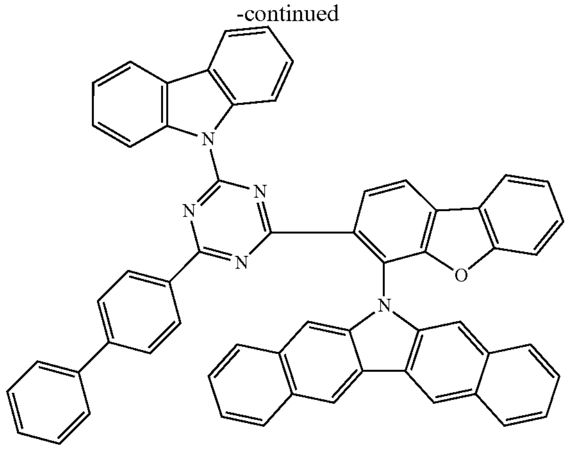
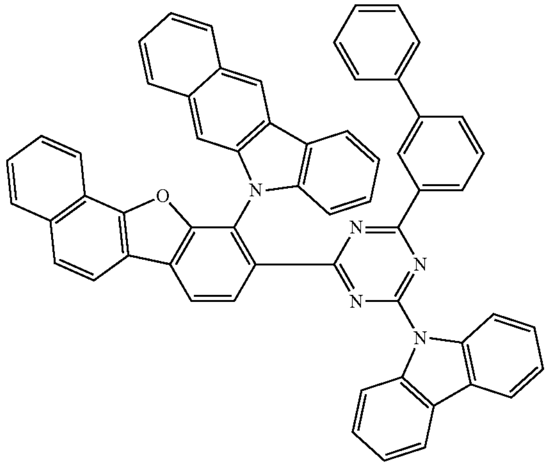
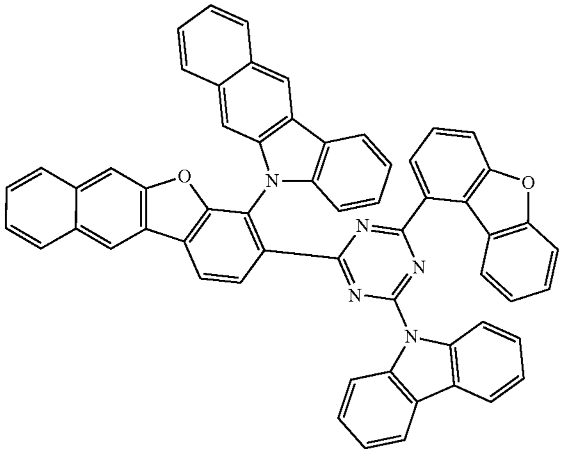
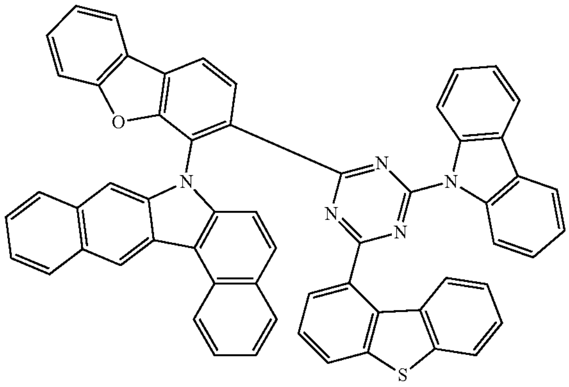
-continued
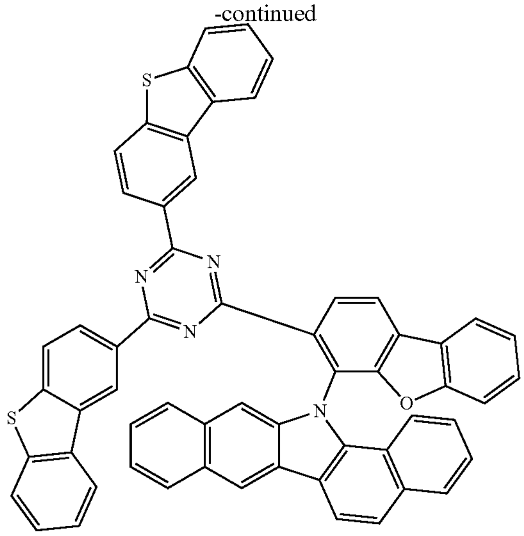
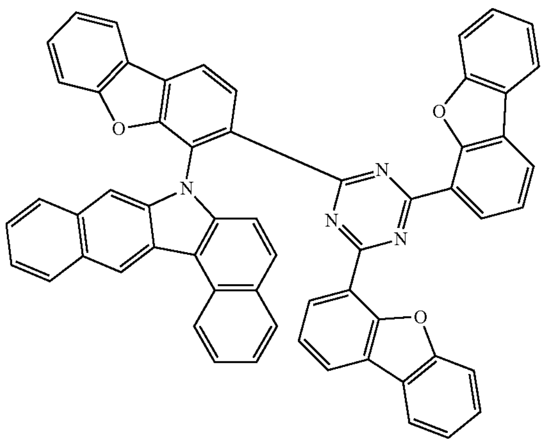
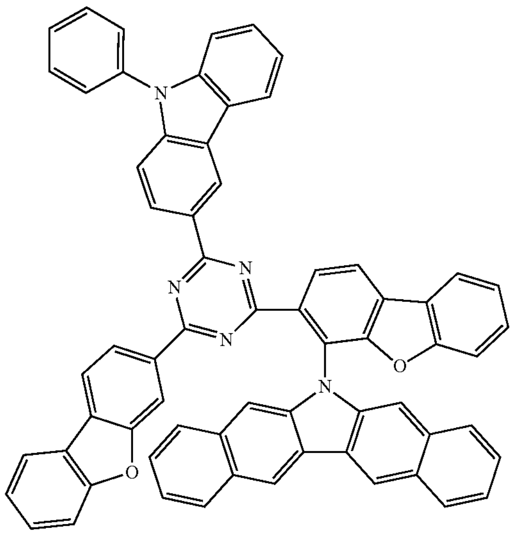

-continued
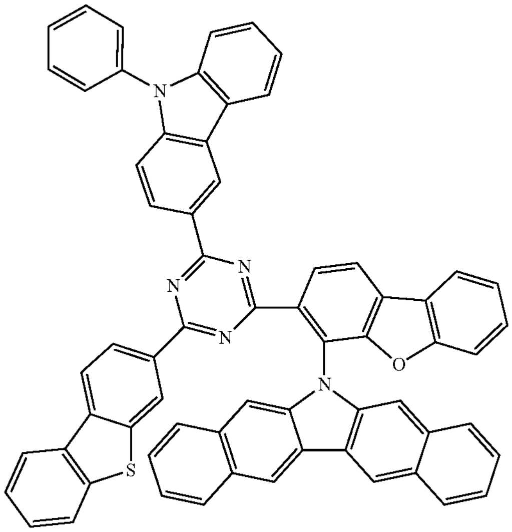
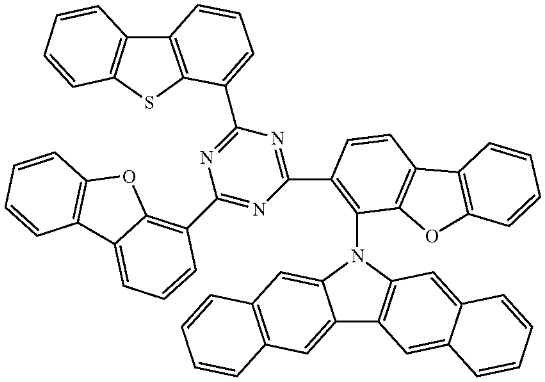
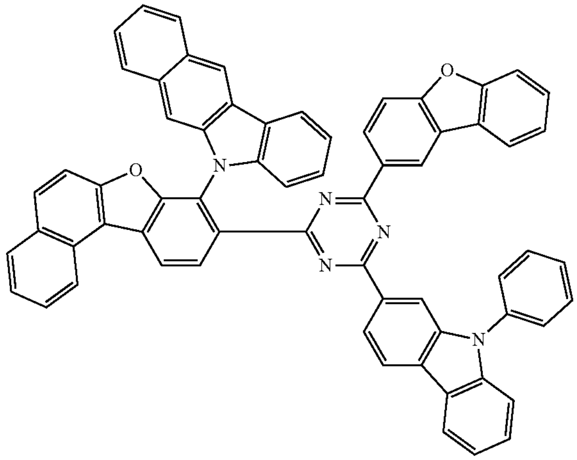
-continued
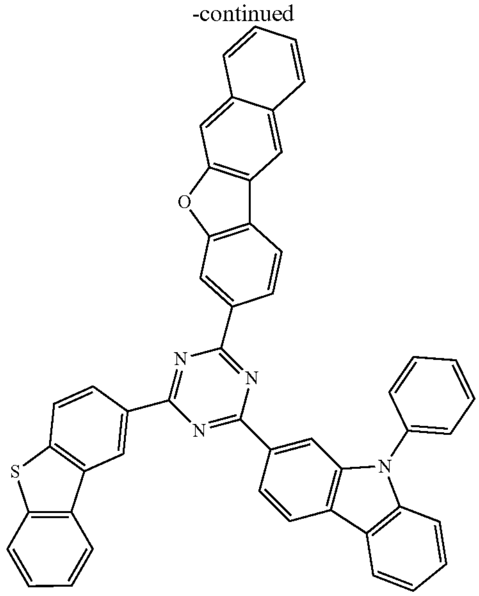
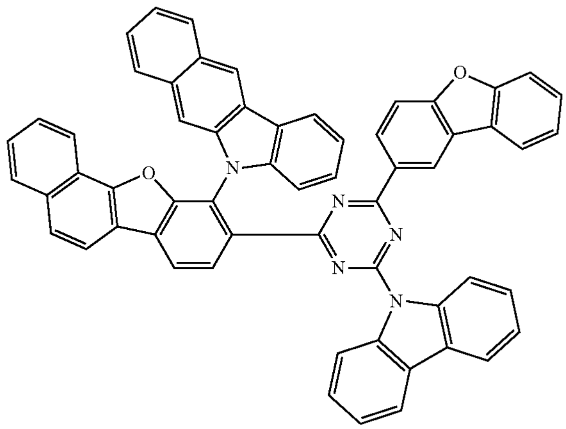
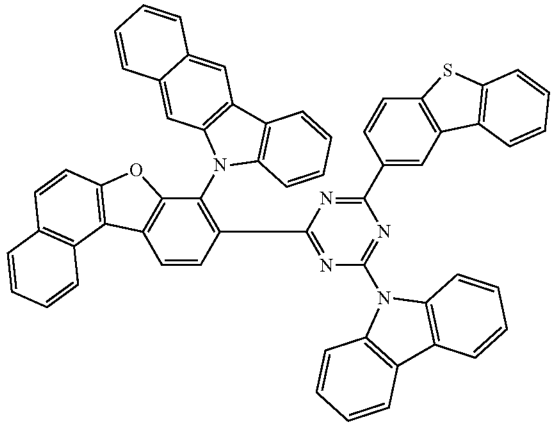

-continued
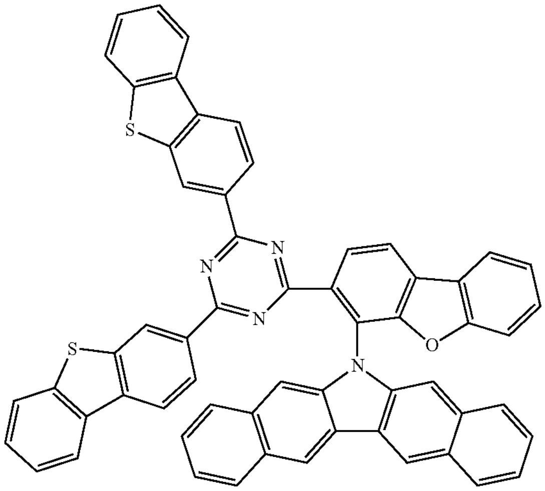
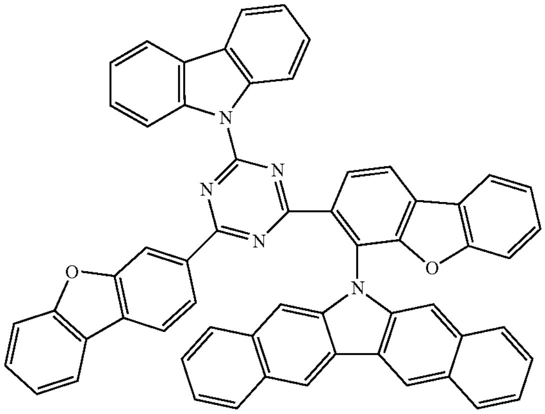
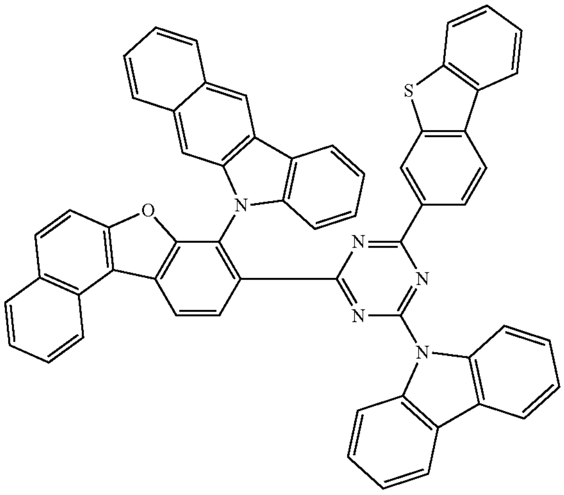
-continued
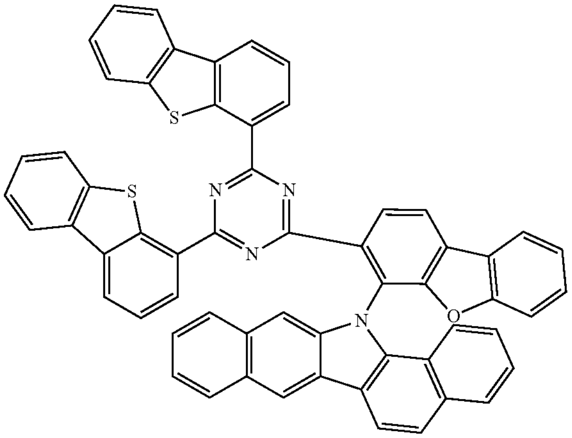
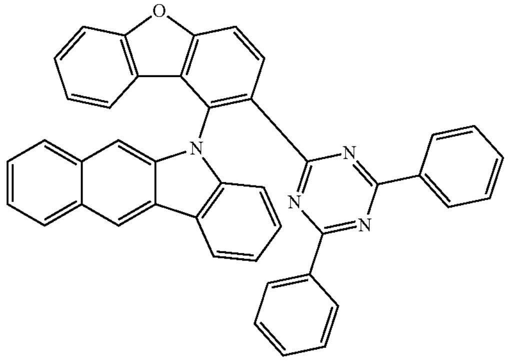
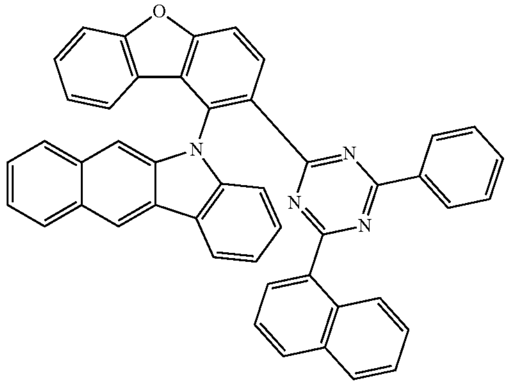
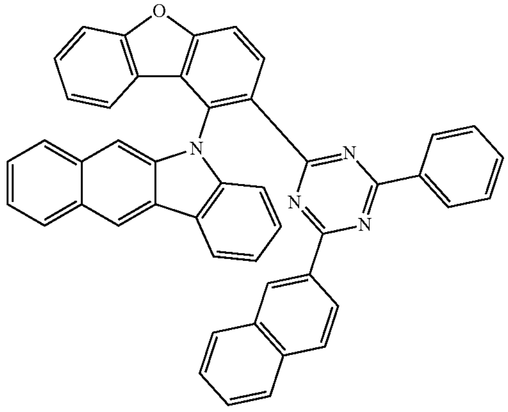

-continued
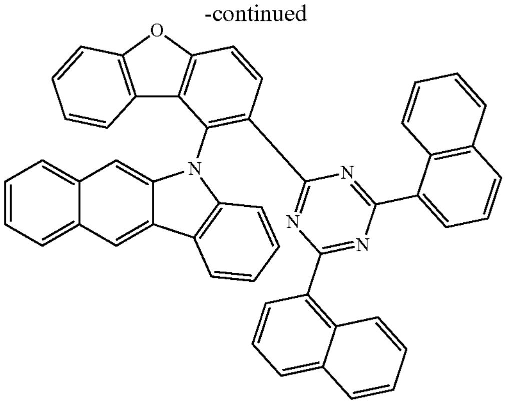
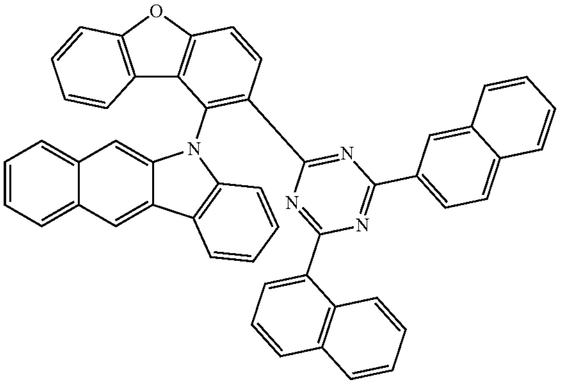
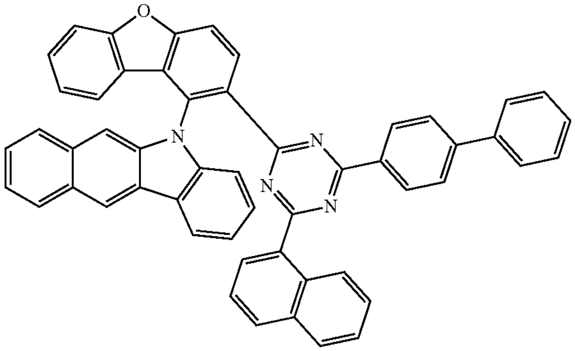
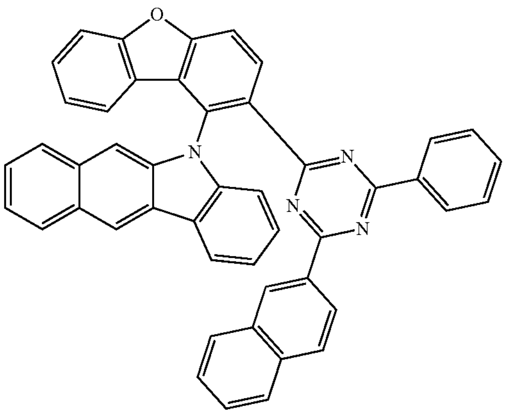
-continued
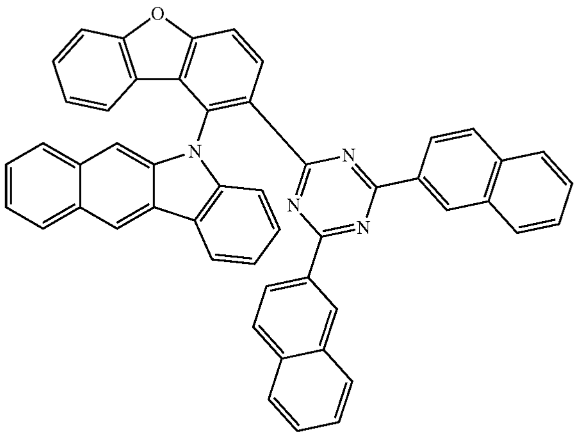
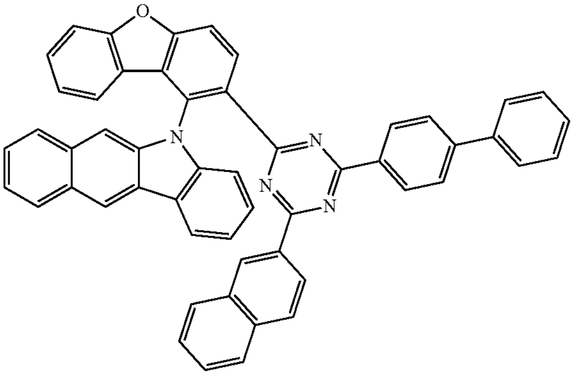
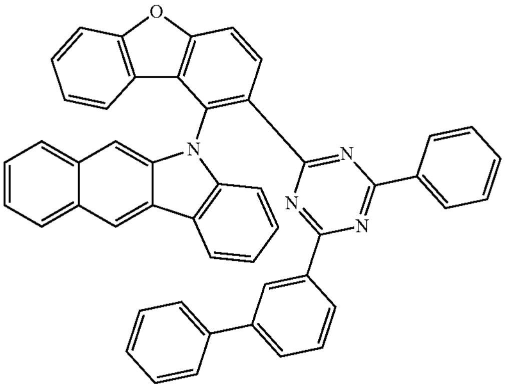
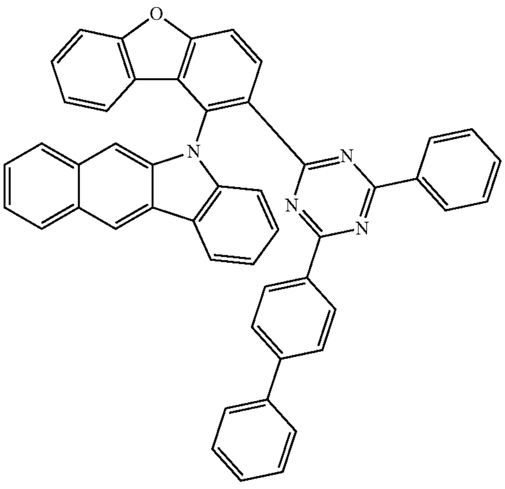

-continued
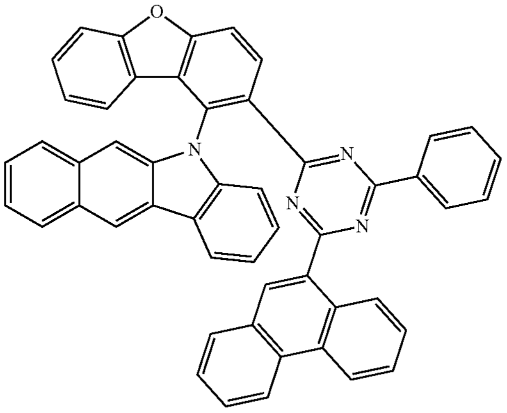
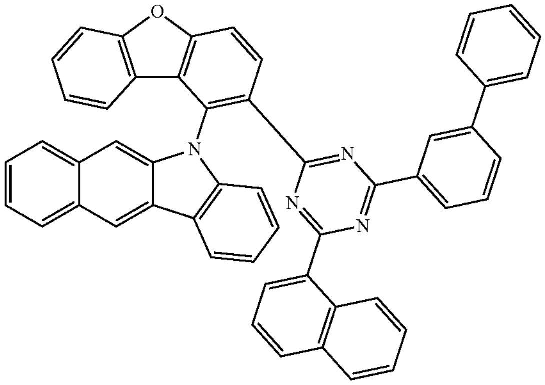
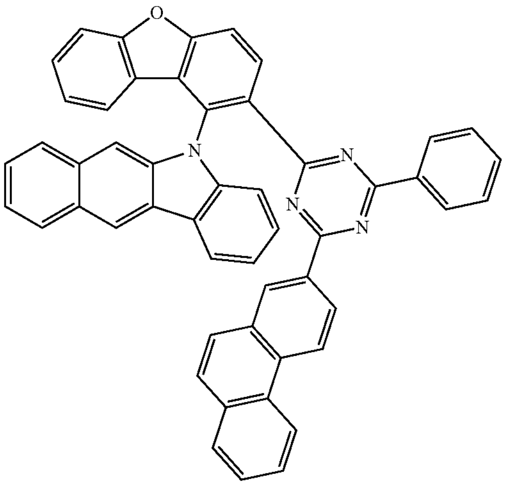
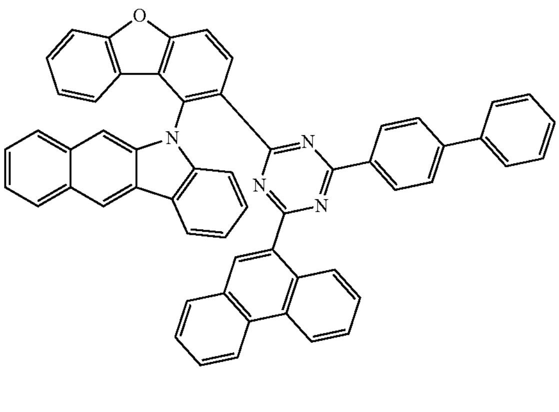
-continued
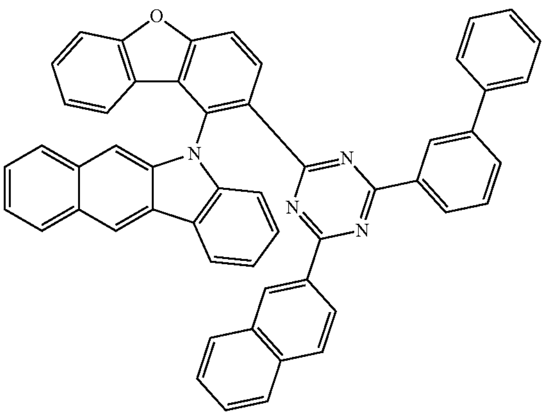
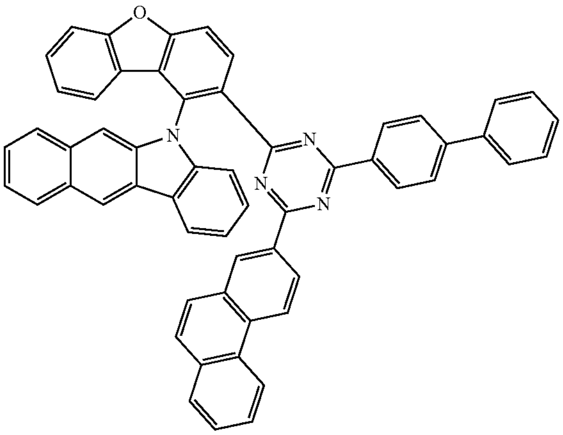
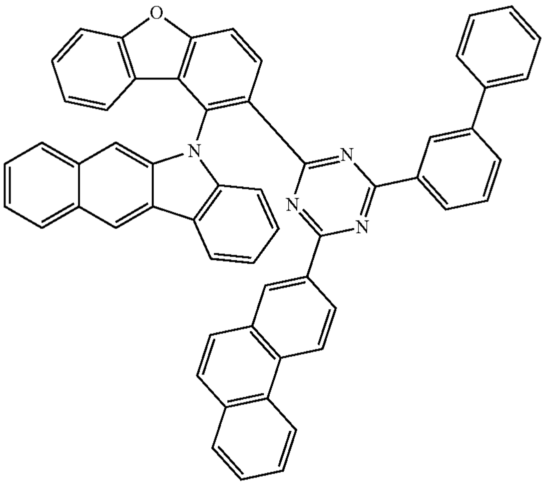

-continued
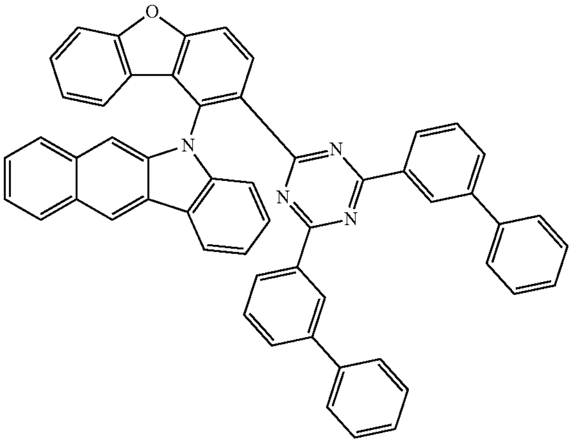
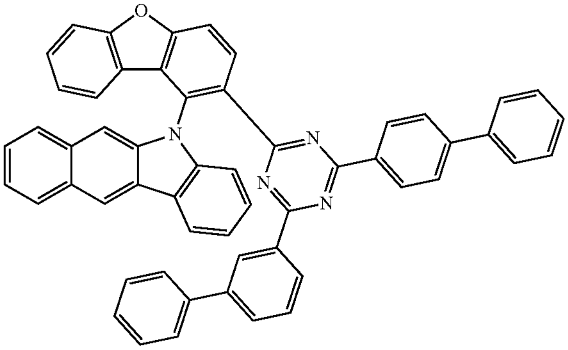
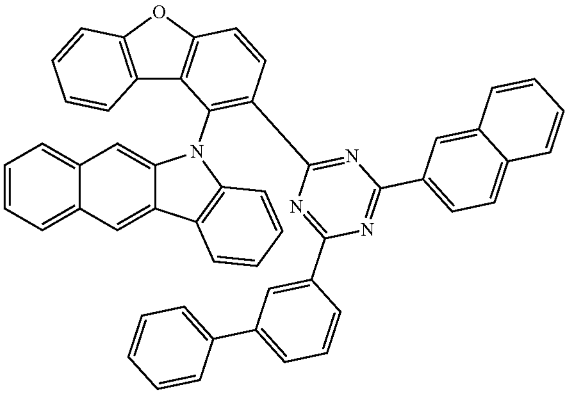
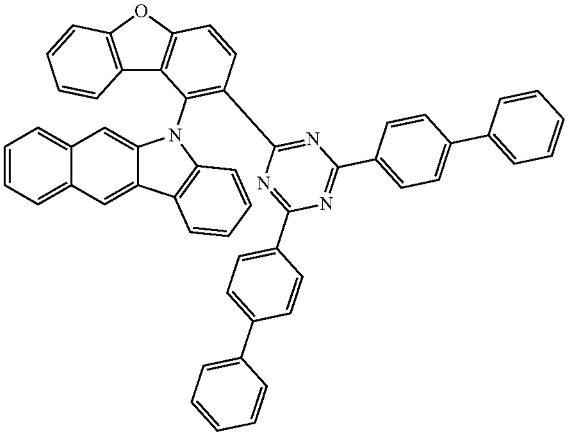
-continued
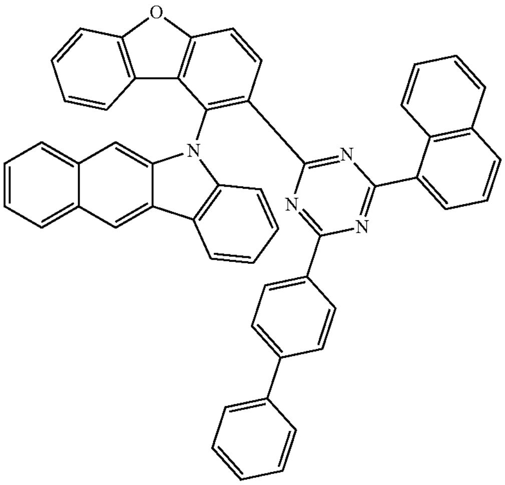
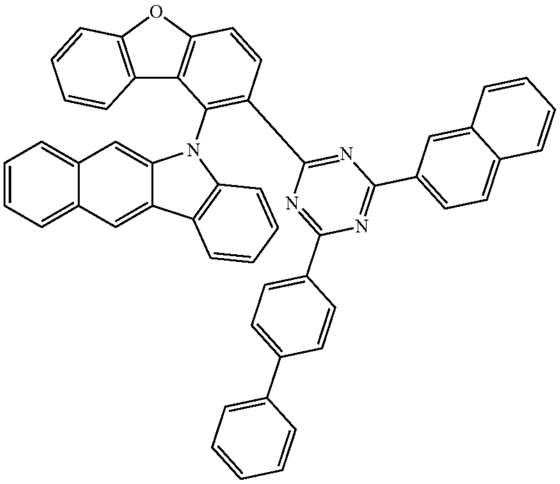
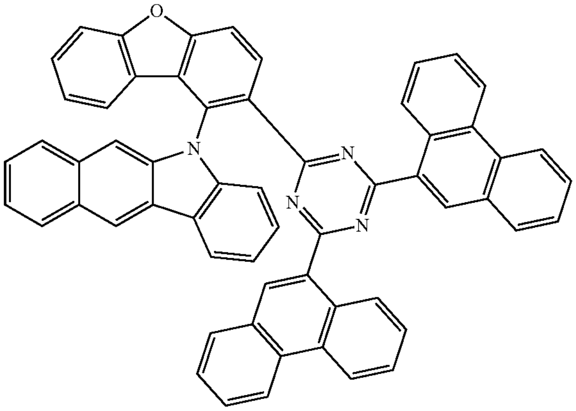

-continued
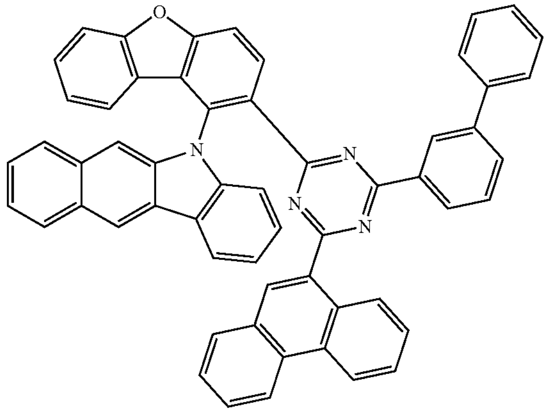
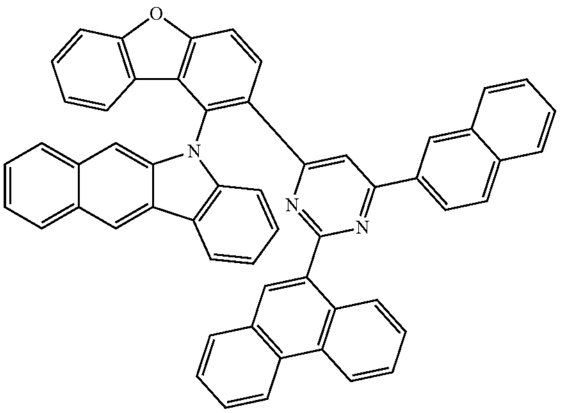 [SMILES: c1ccc2cc(-c3cc(-c4ccc5oc6ccccc6c5c4-n4c5ccccc5c5cc6ccccc6cc54)nc(-c4cc5ccccc5c5ccccc45)n3)ccc2c1]
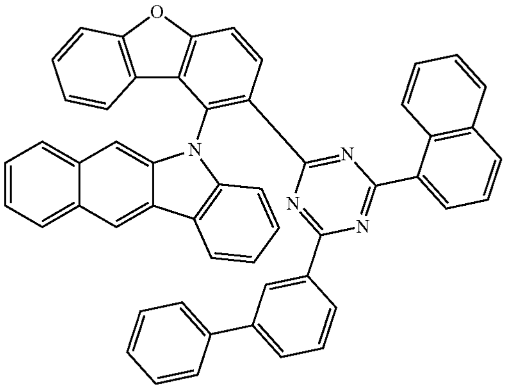
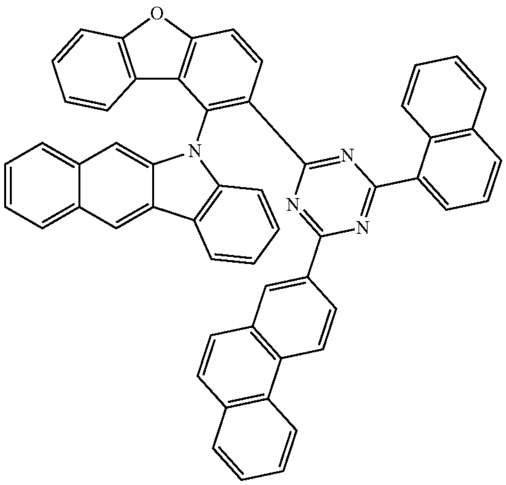
-continued
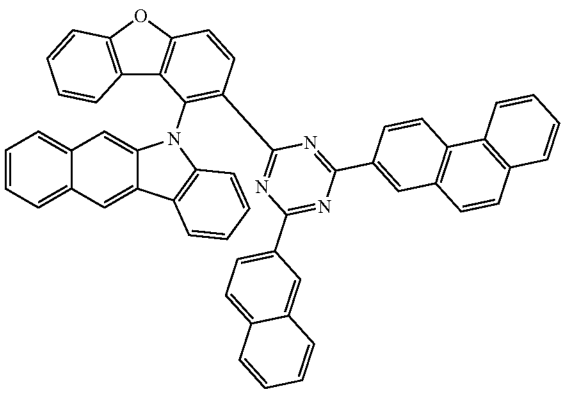
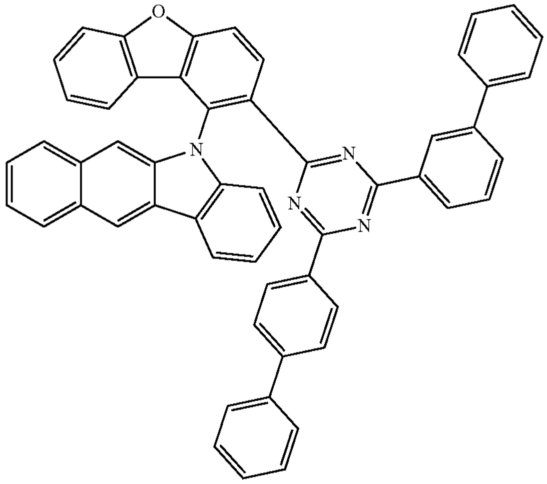
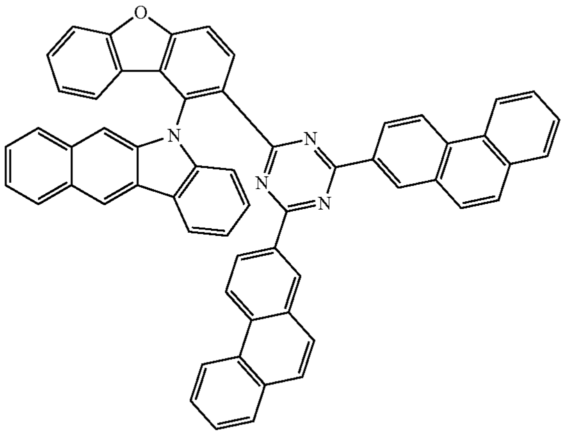

-continued
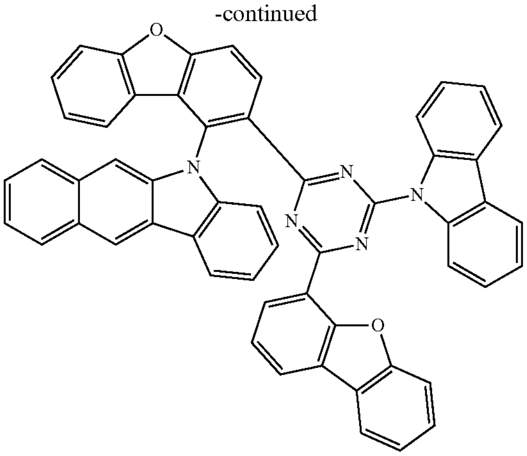
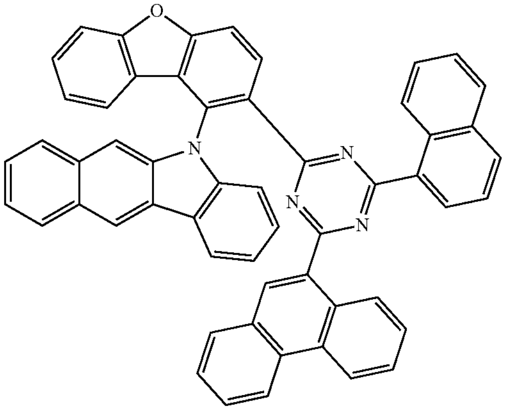
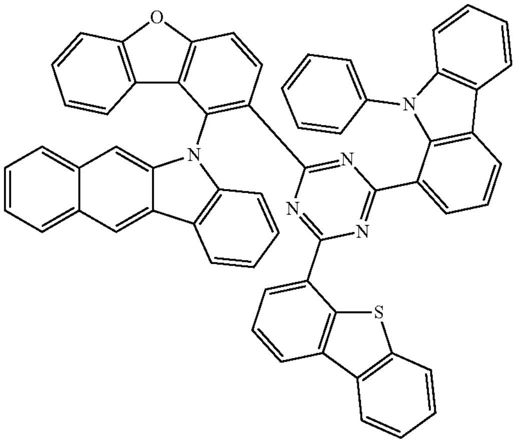
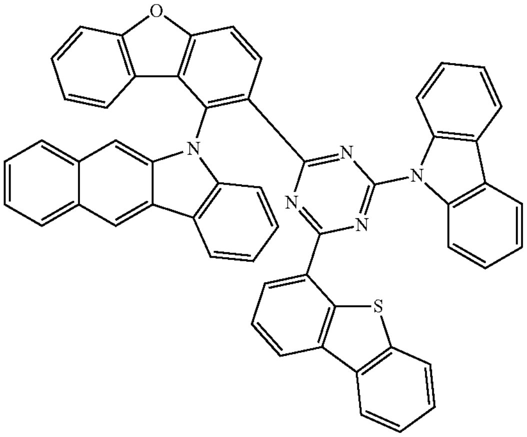
-continued
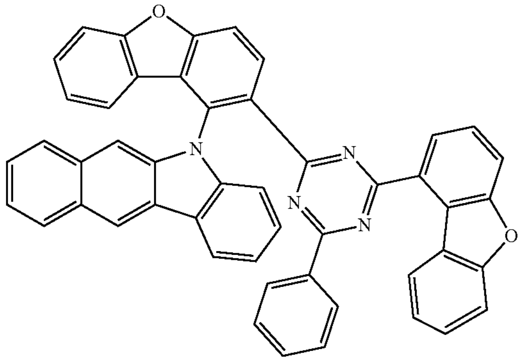
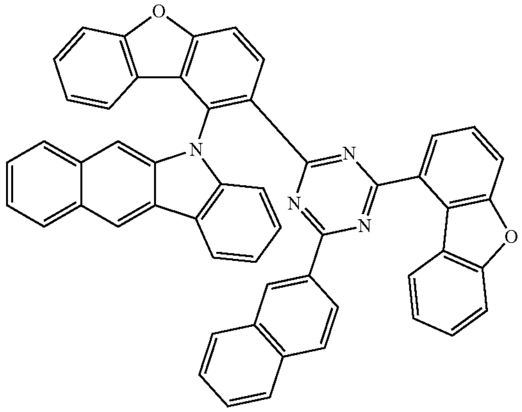
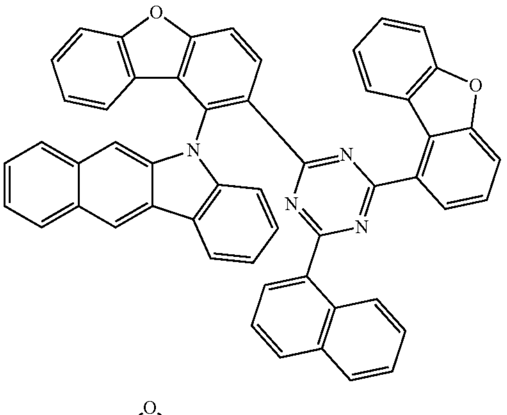
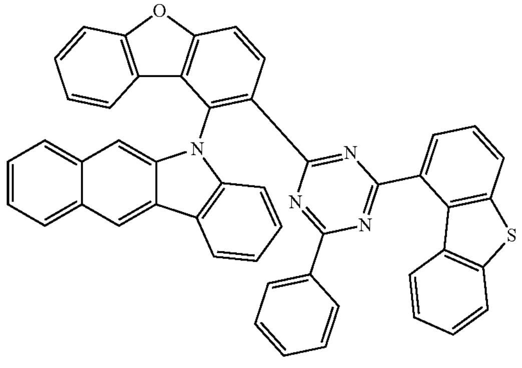

-continued
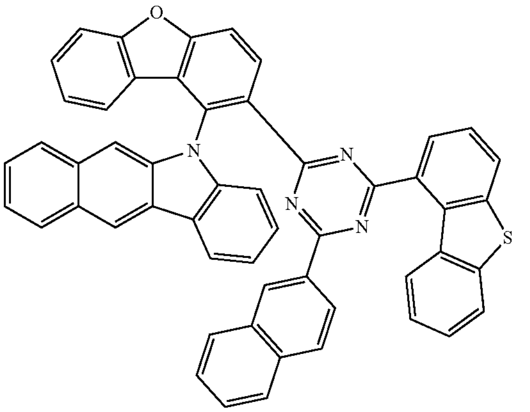
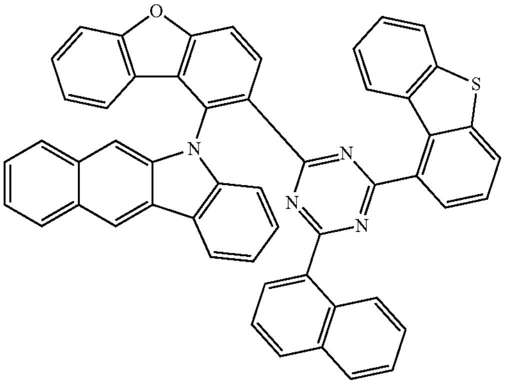
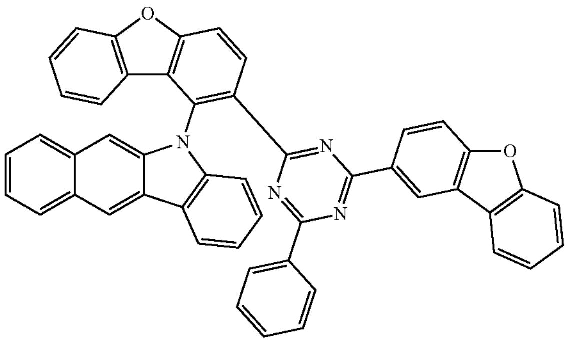
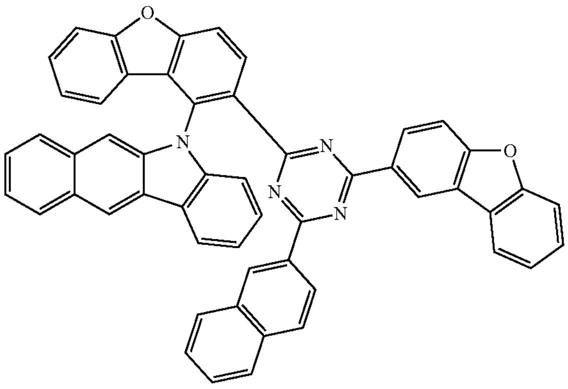
-continued
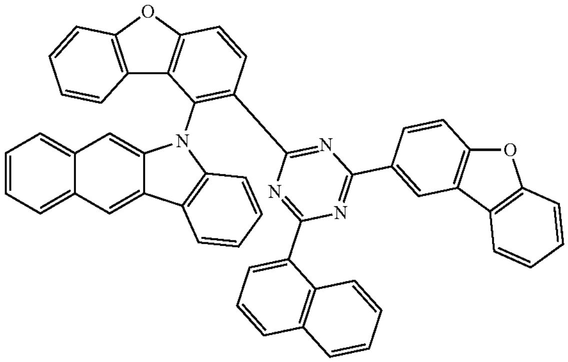
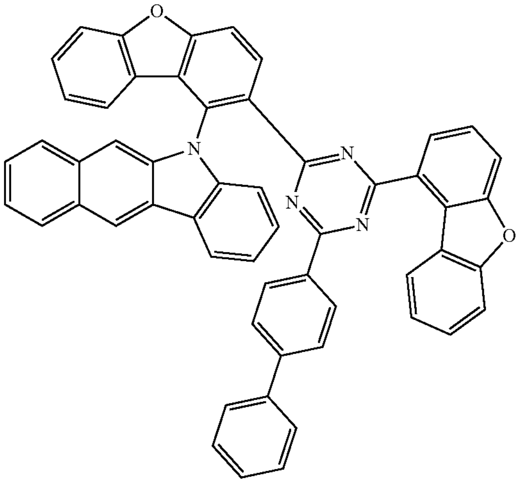
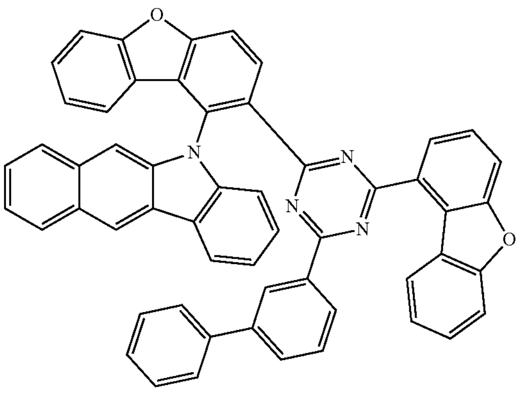
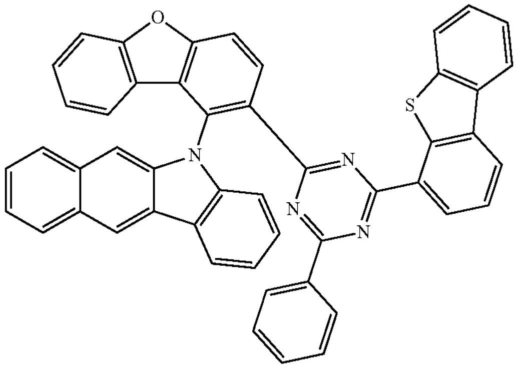

-continued
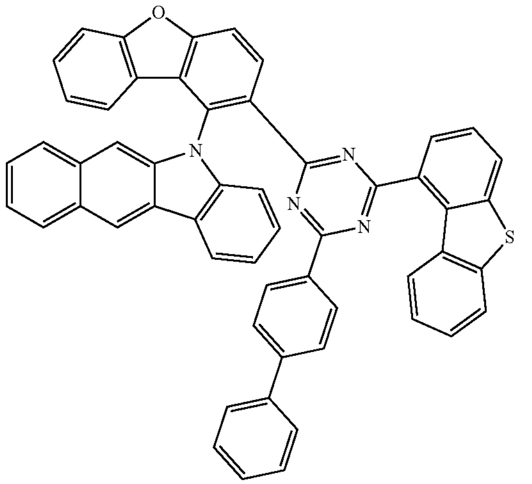
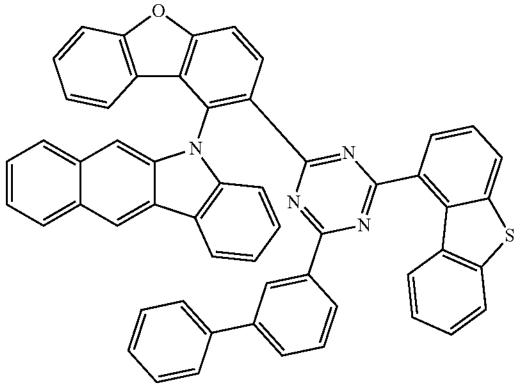
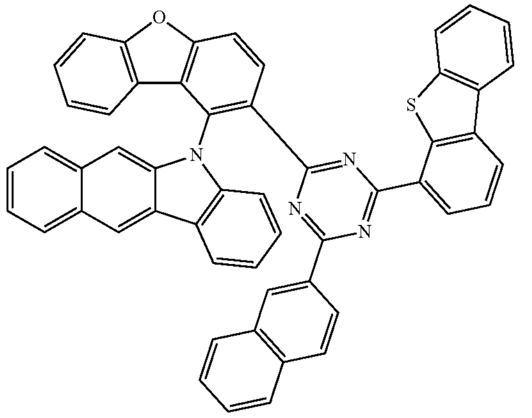
-continued
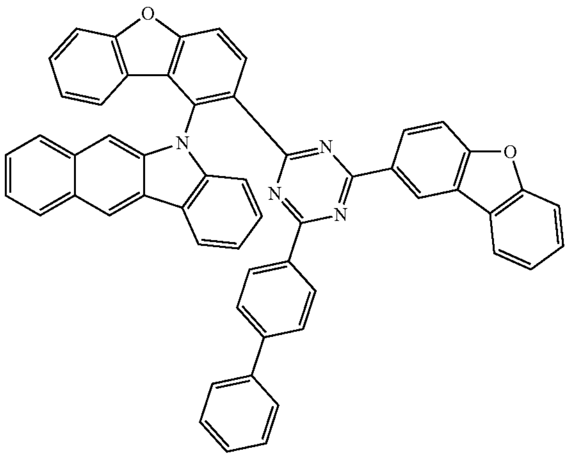
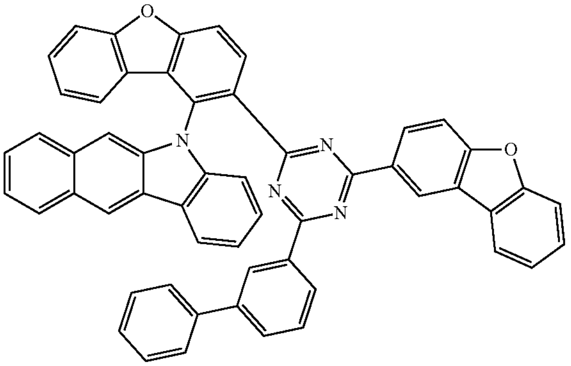
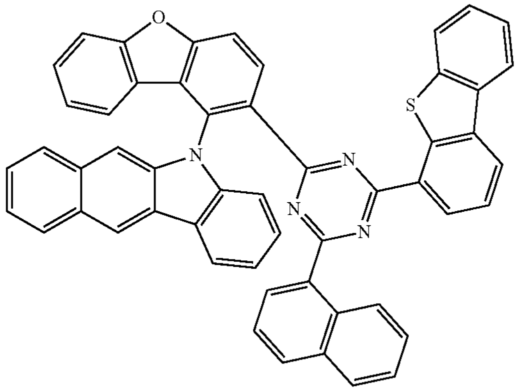
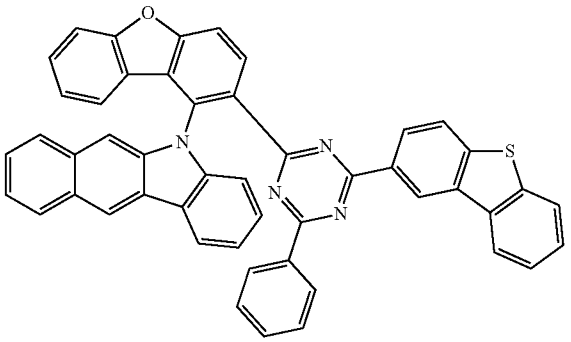

-continued
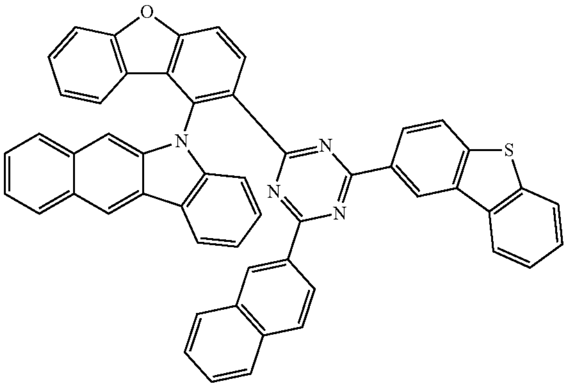
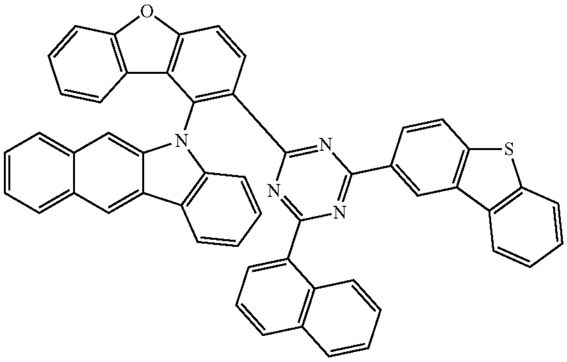
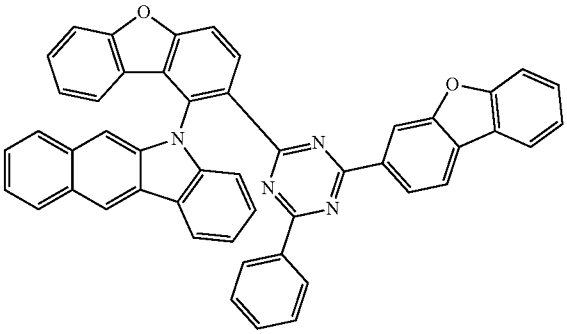
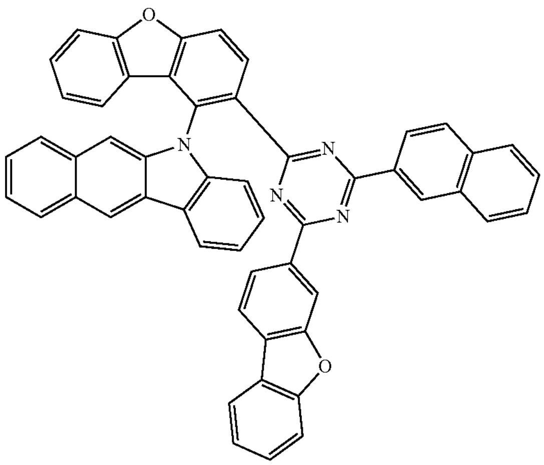
-continued
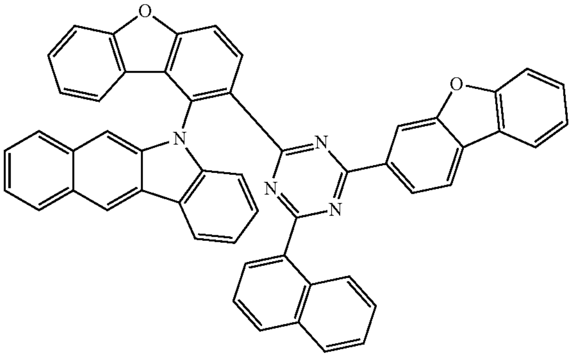
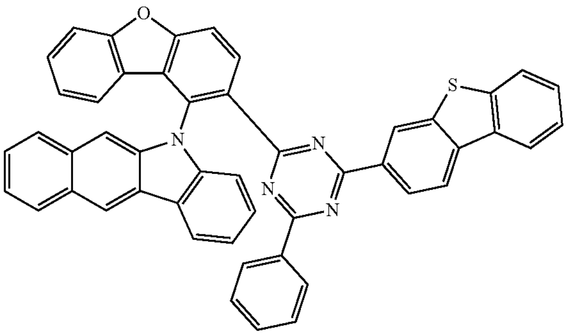
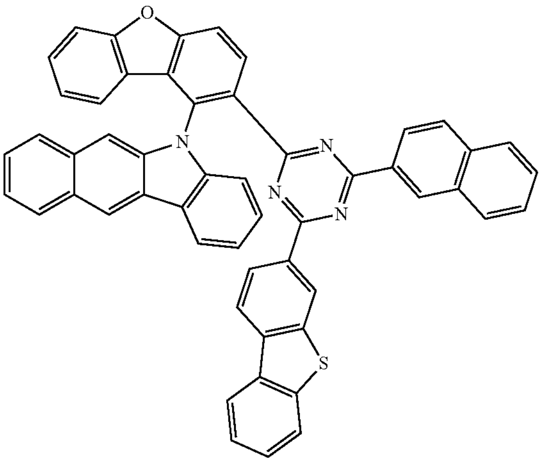
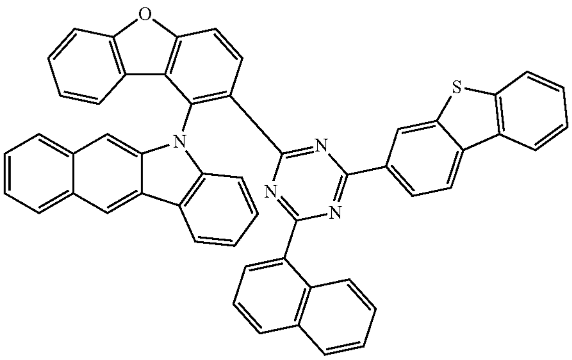

-continued
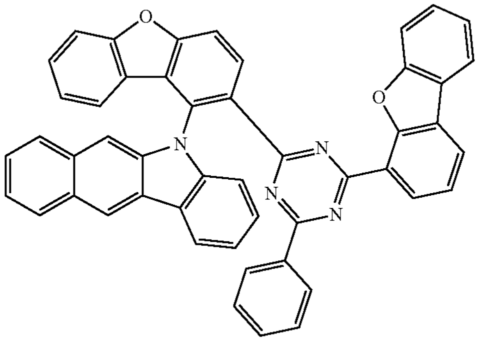
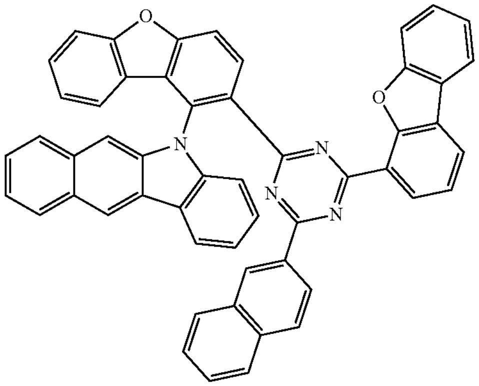
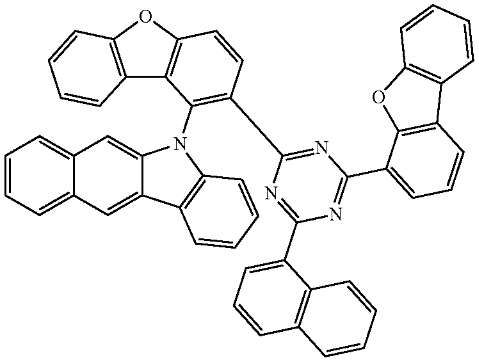
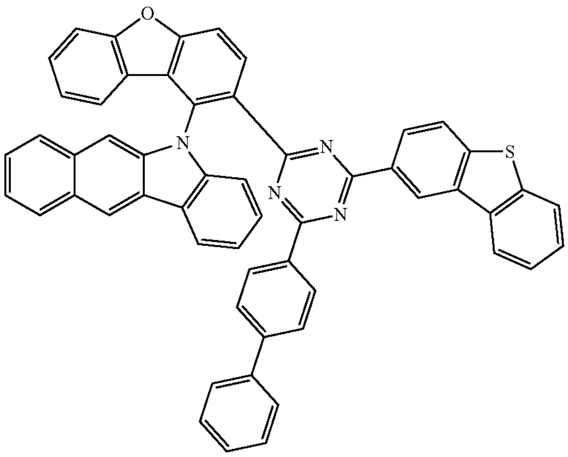
-continued
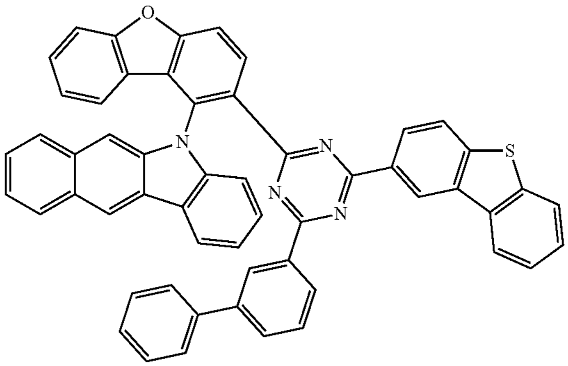
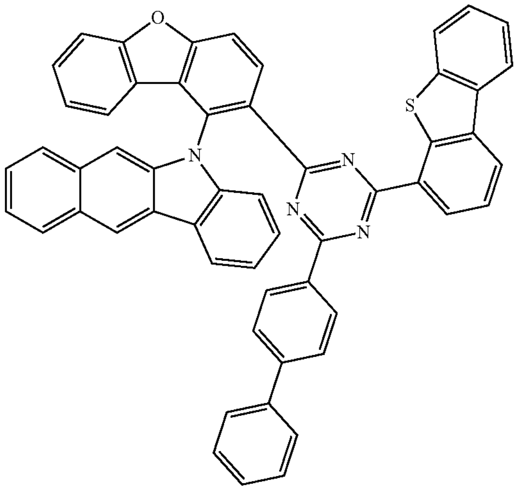
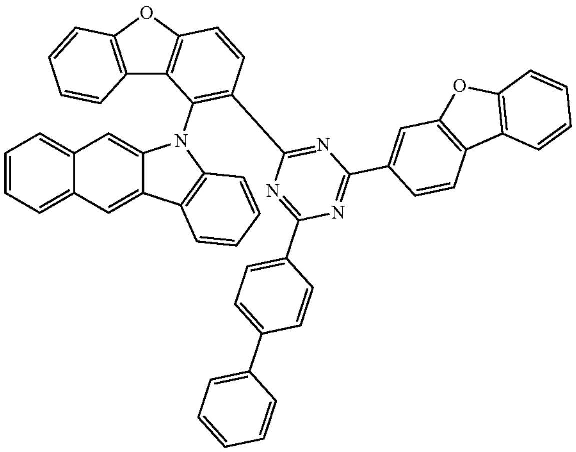
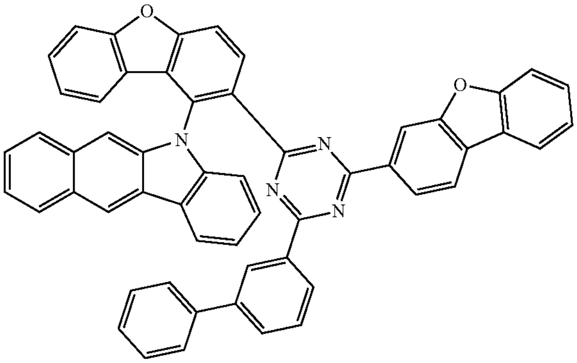

-continued
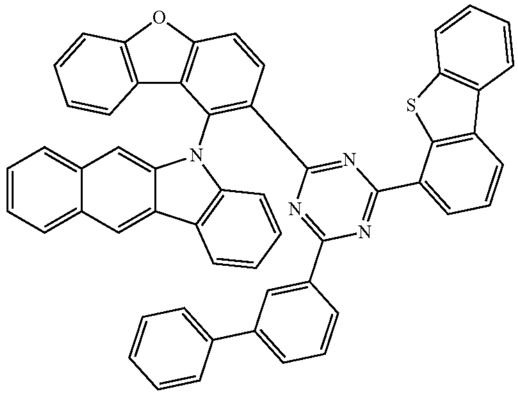
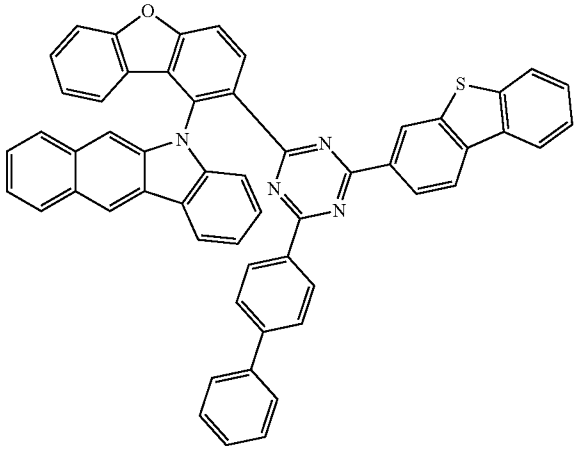
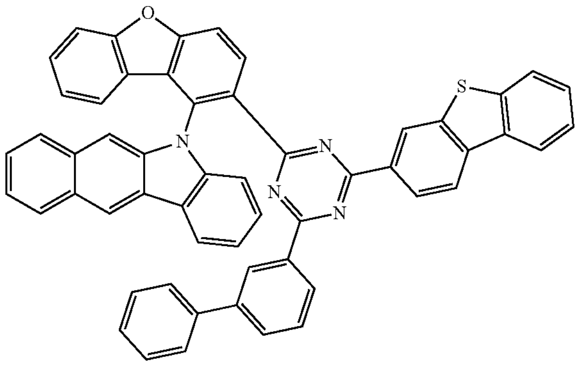
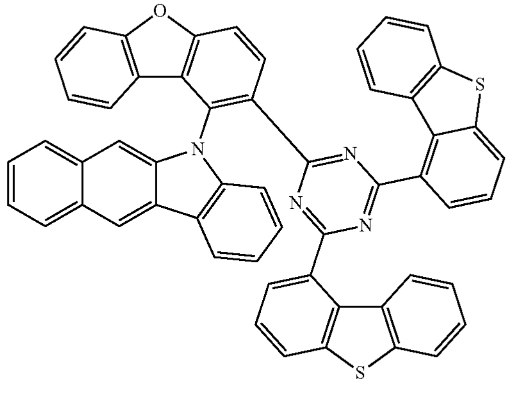
-continued
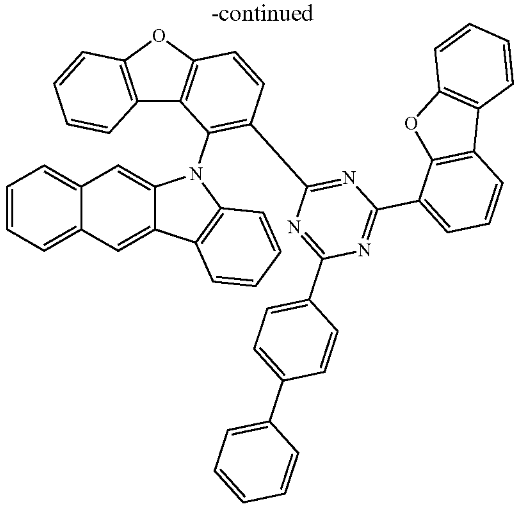
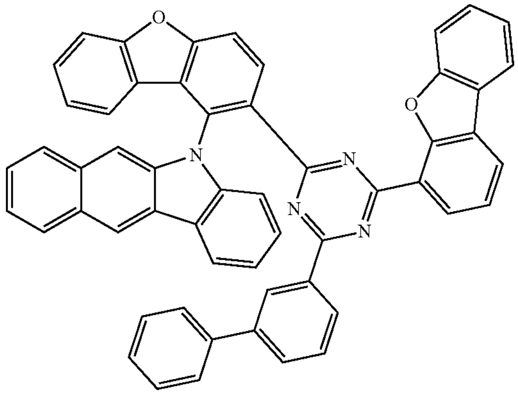
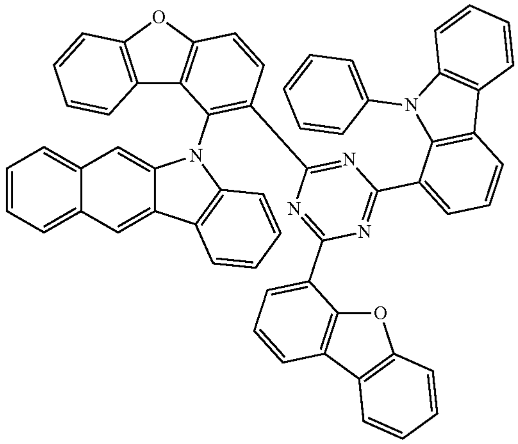
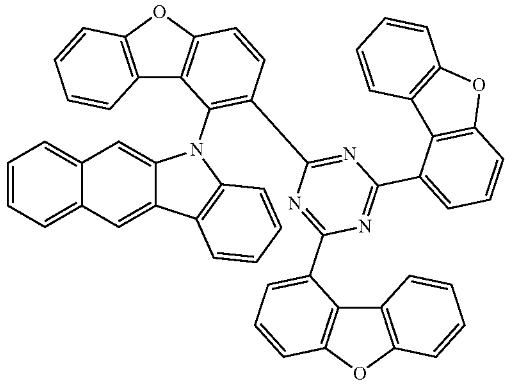

-continued
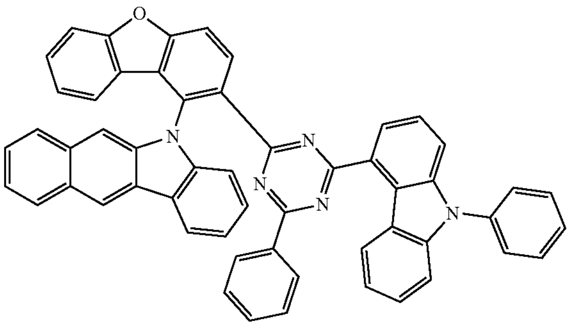
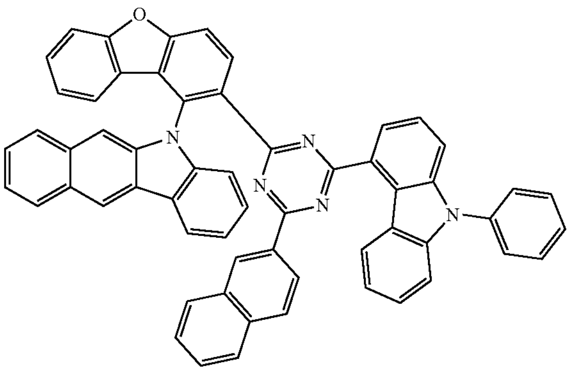
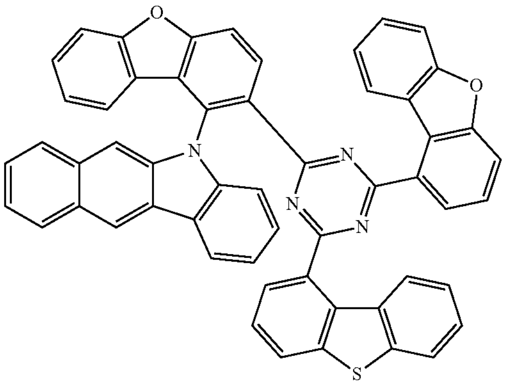
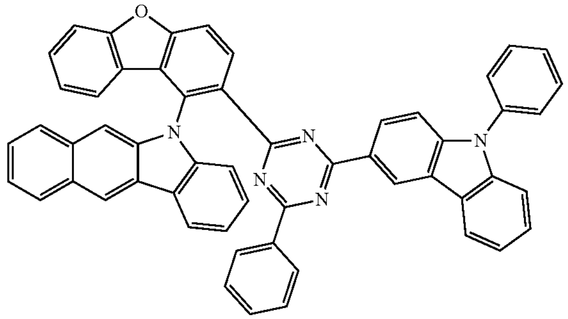
-continued
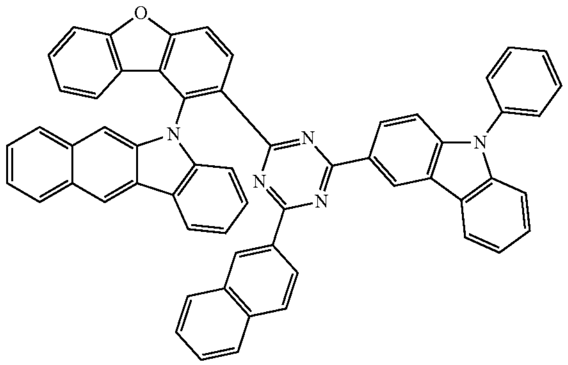
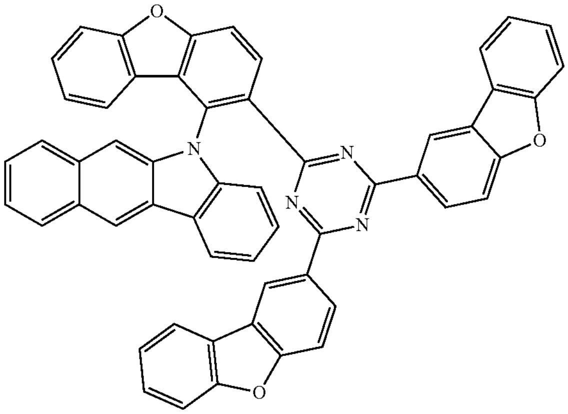
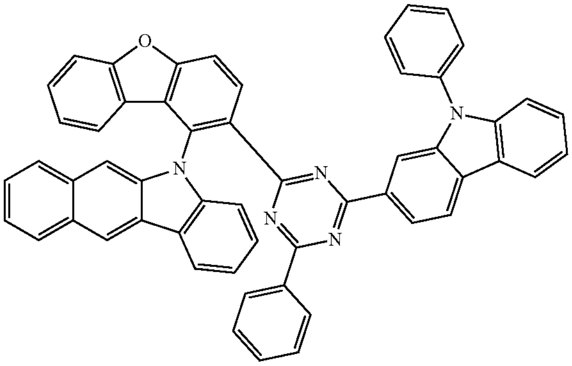
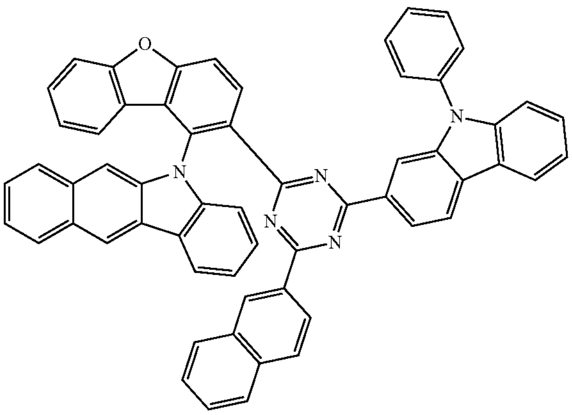

-continued
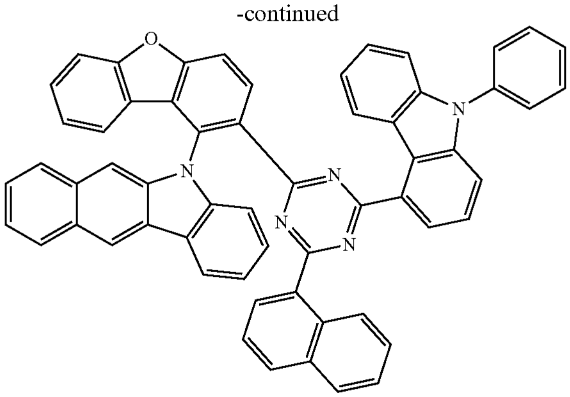
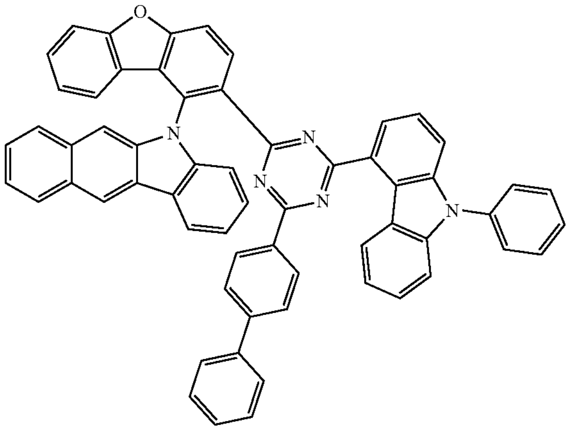
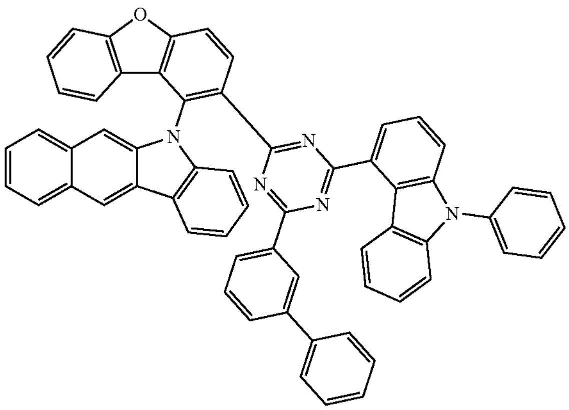
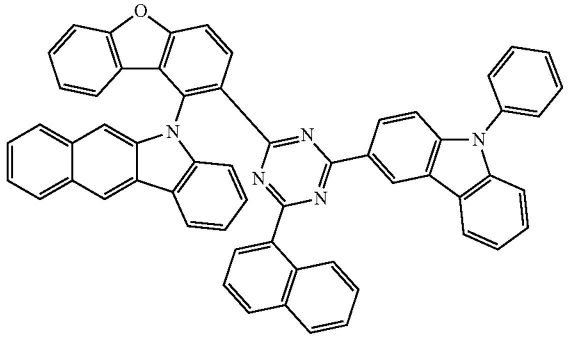
-continued
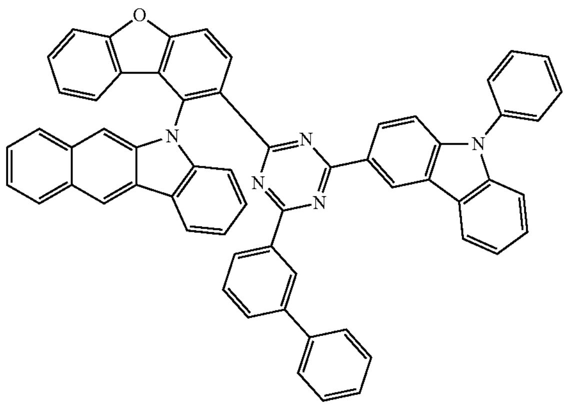
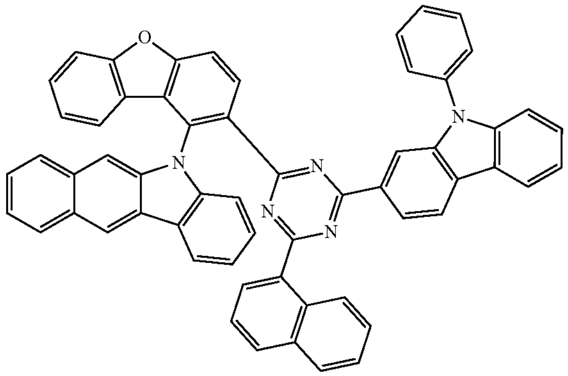
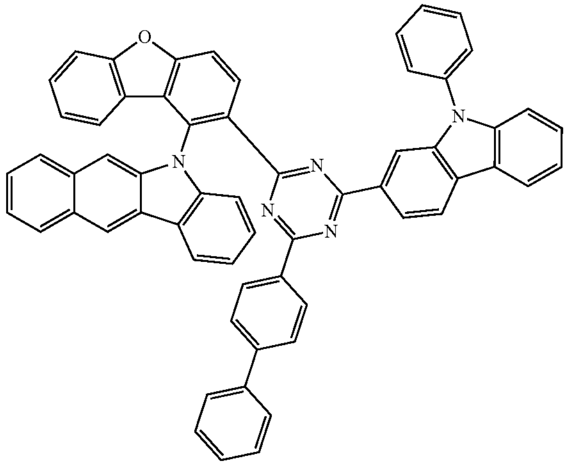
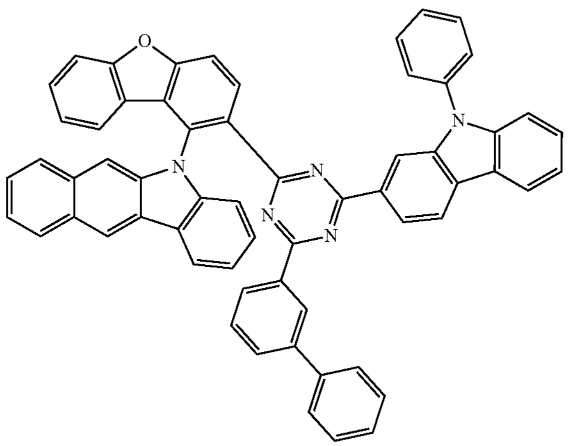

-continued
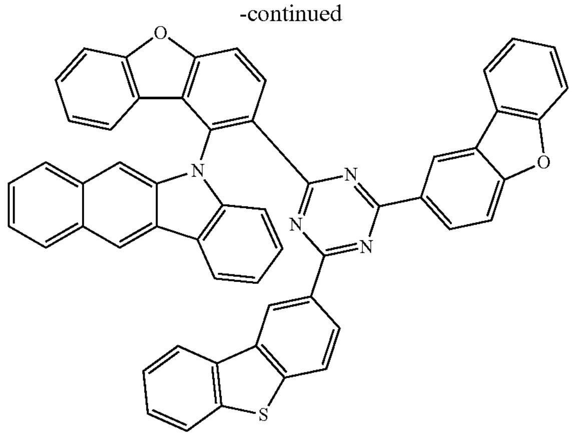
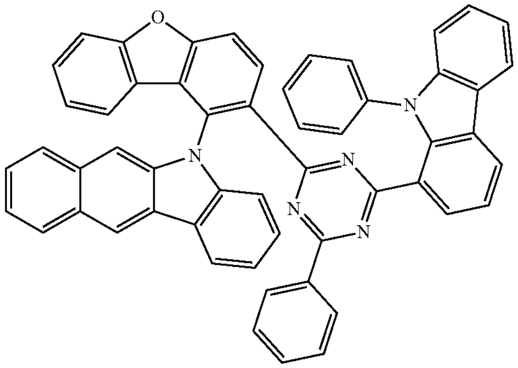
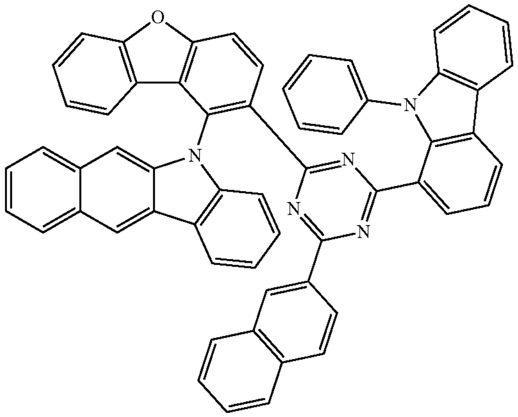
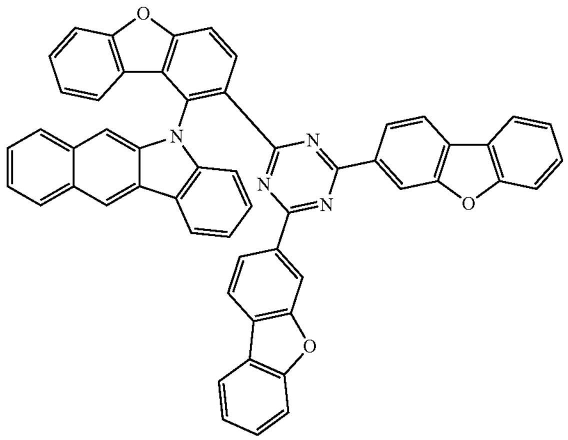
-continued
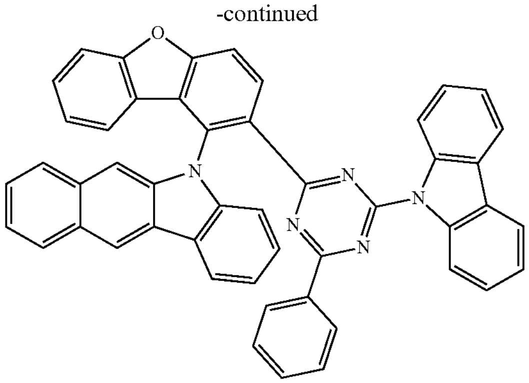
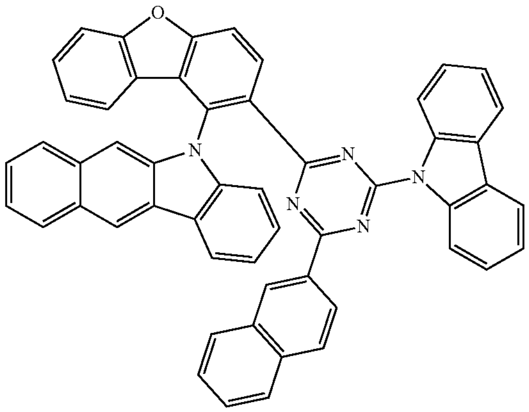
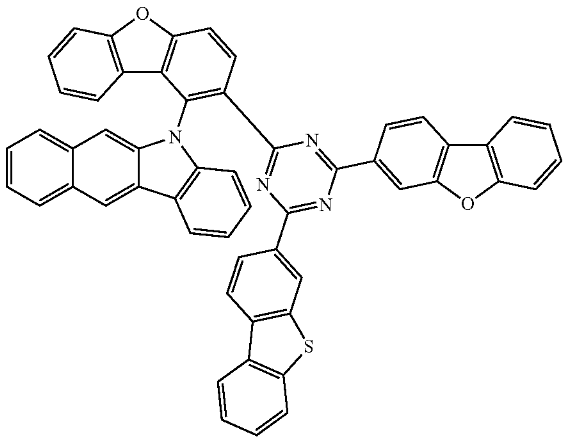
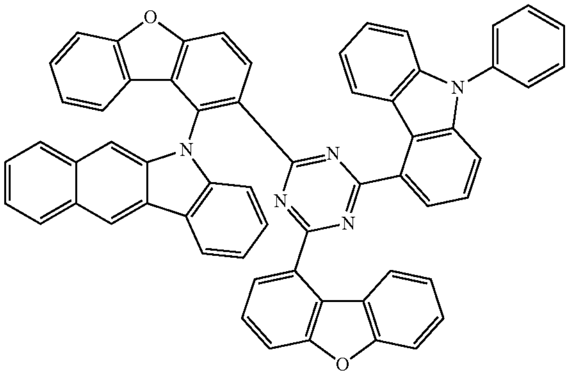

-continued
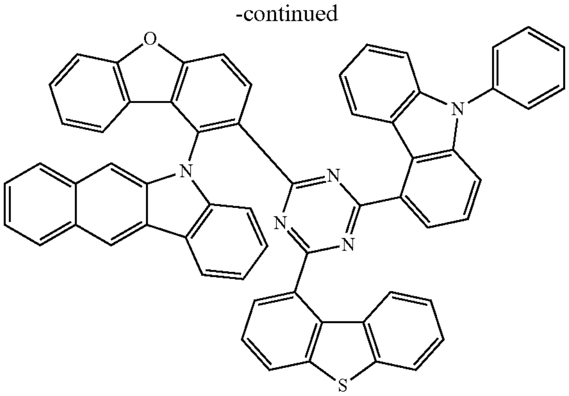
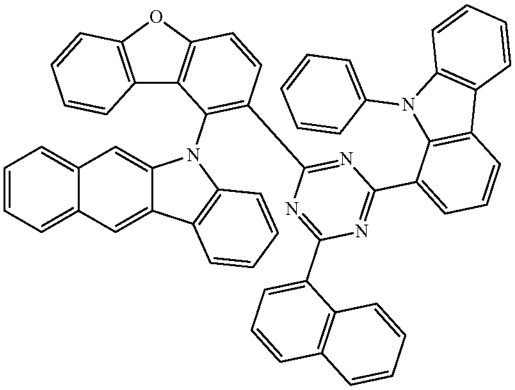
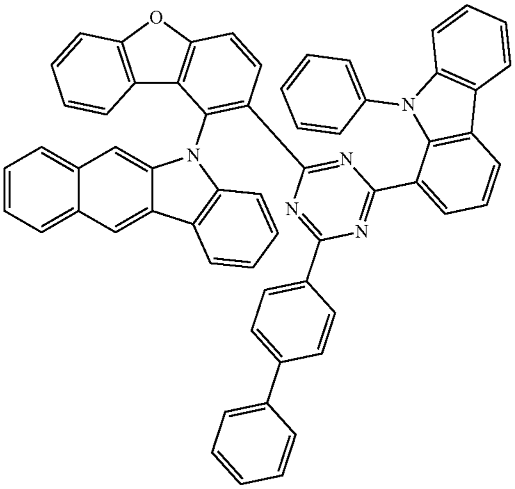
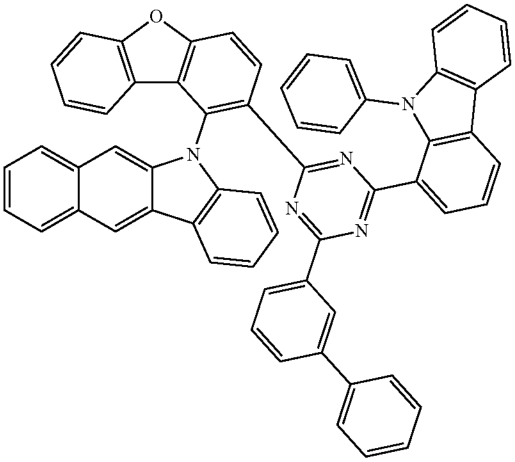
-continued
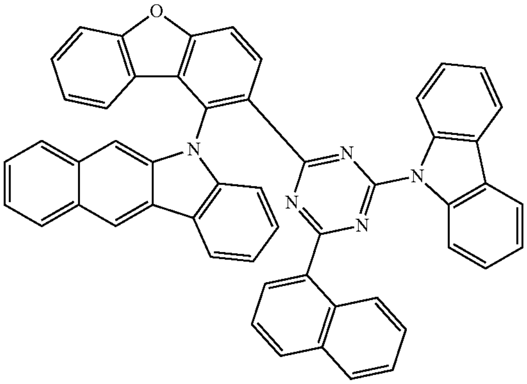
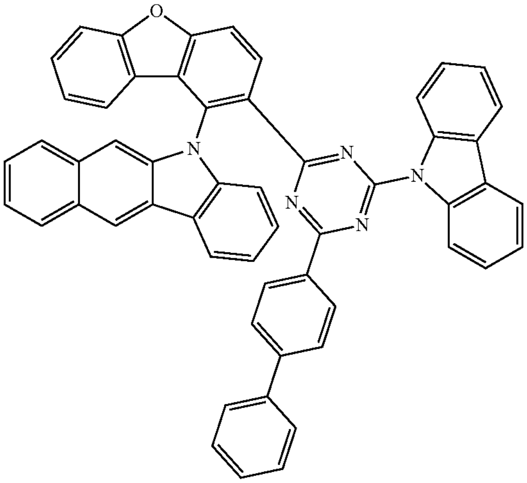
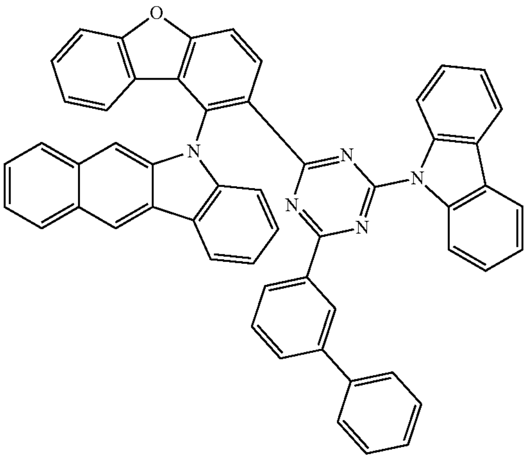
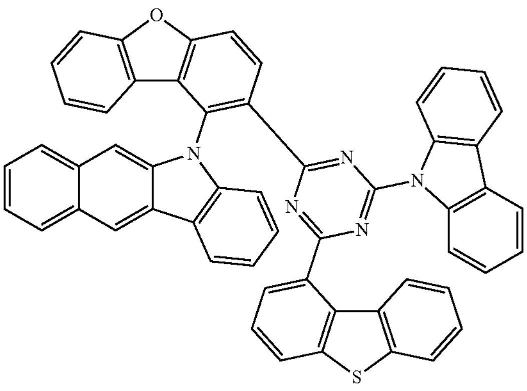

-continued
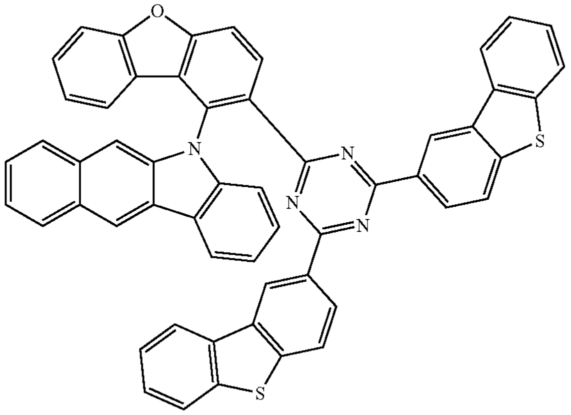
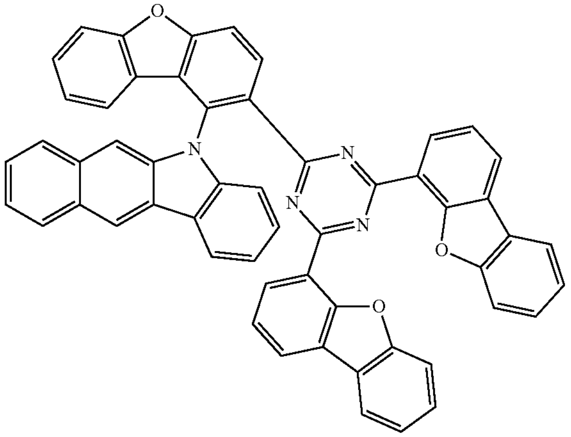
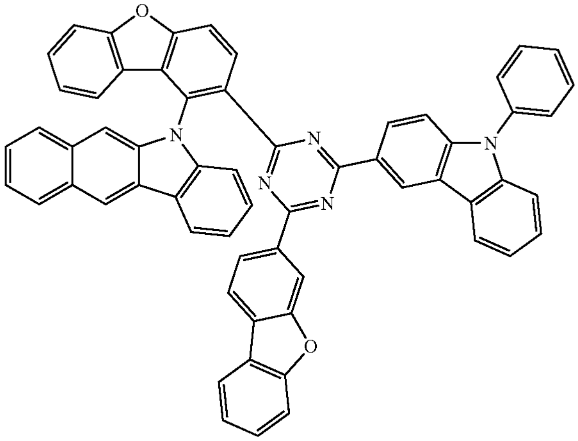
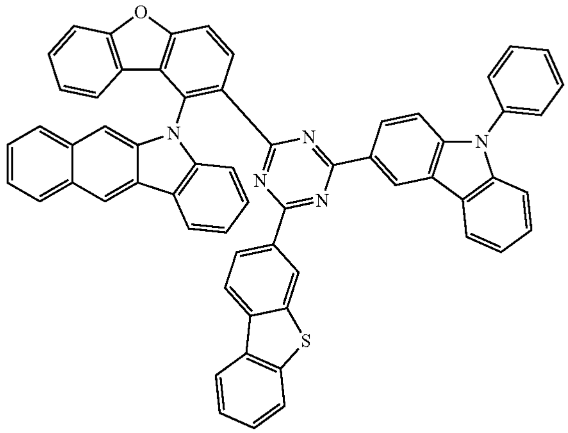
-continued
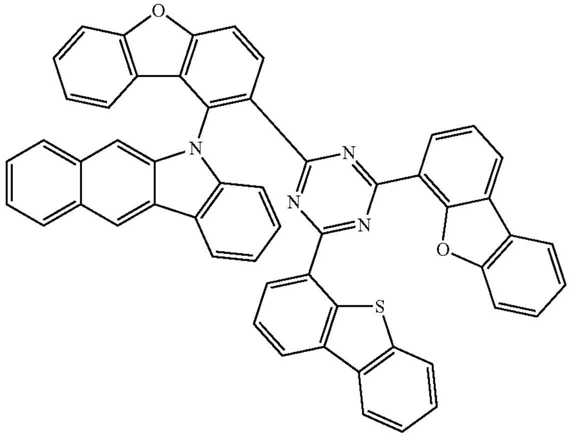
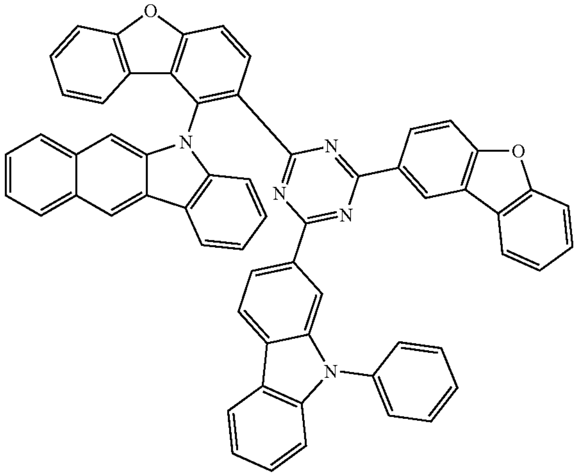
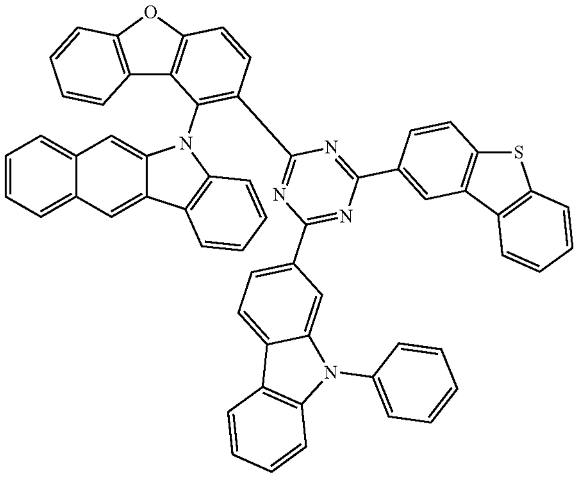

-continued
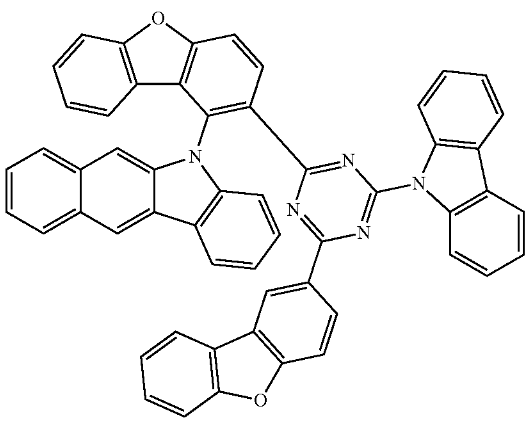
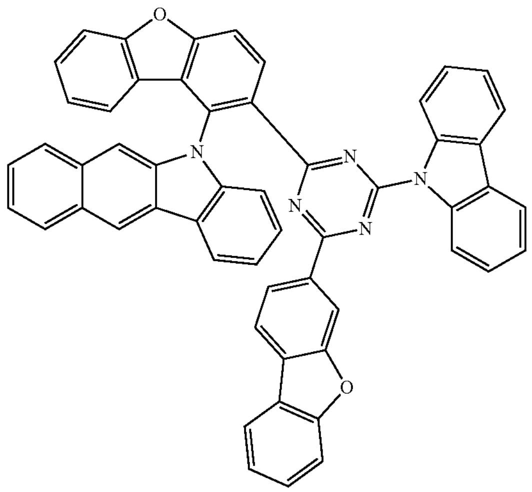
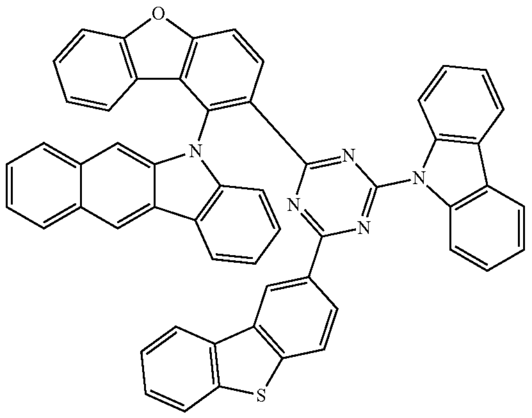
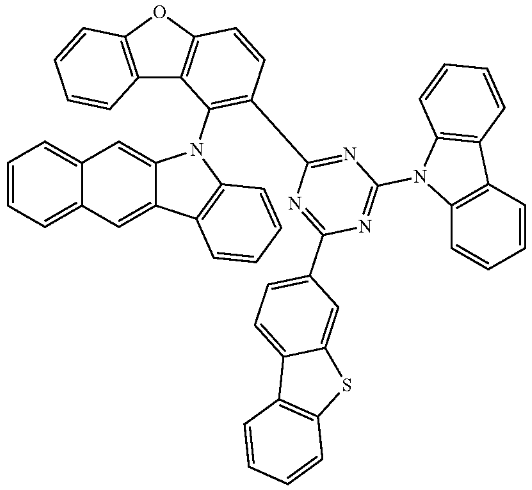
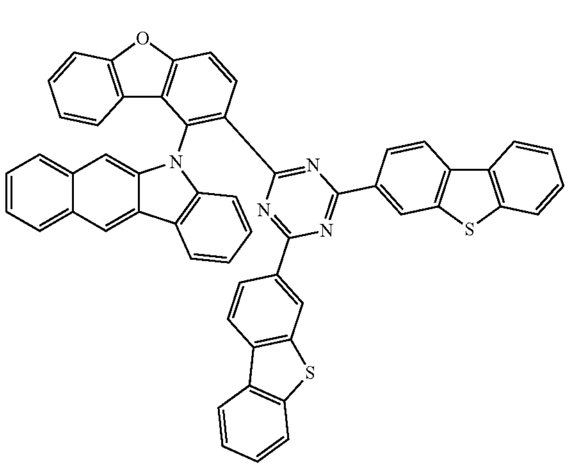
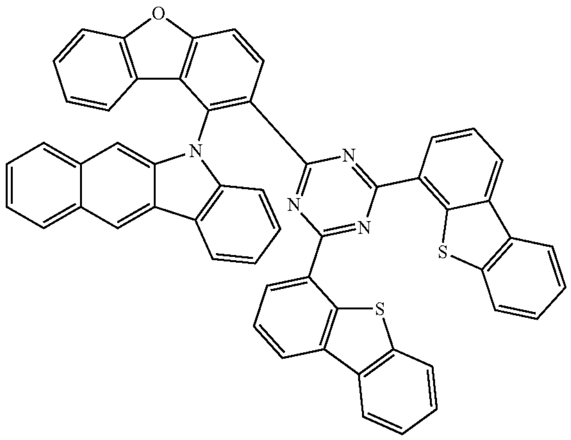
-continued -continued
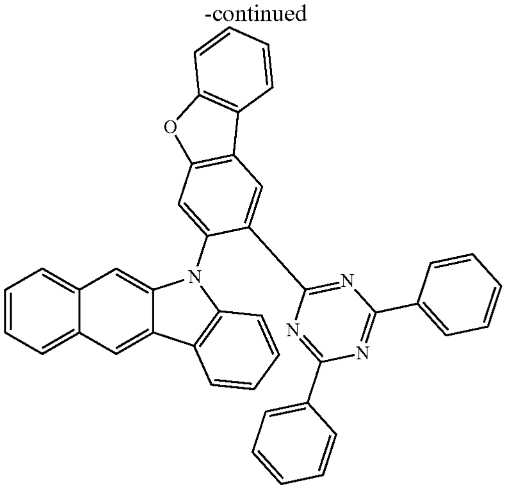
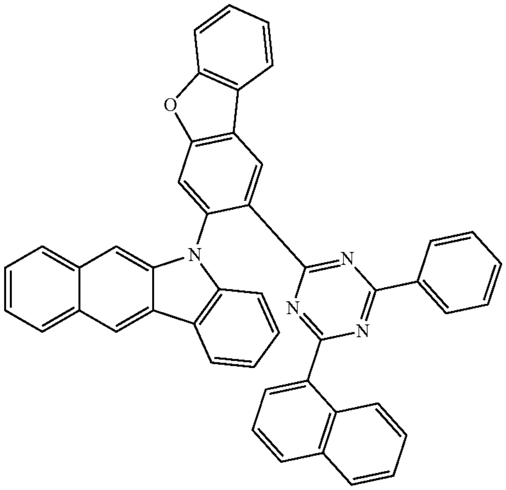
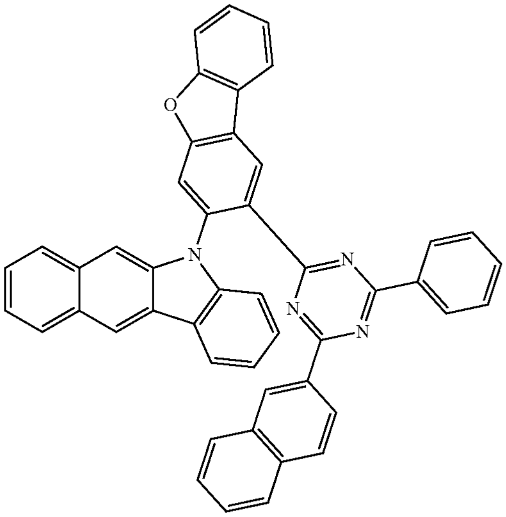
-continued
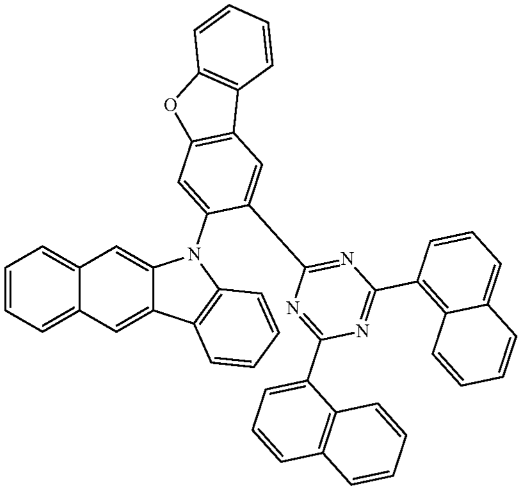
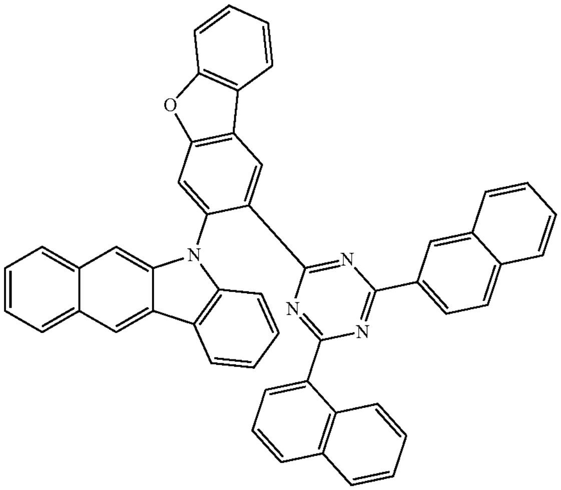
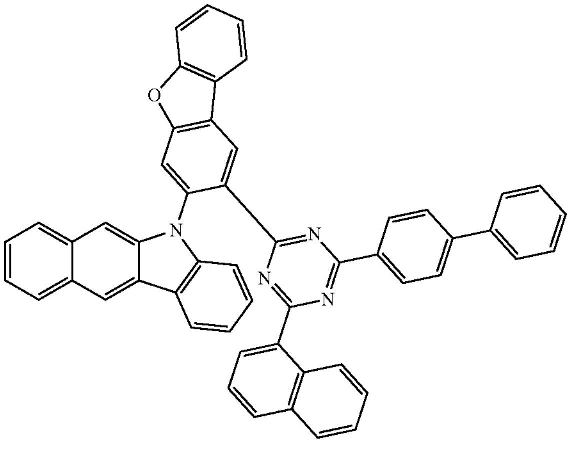

-continued
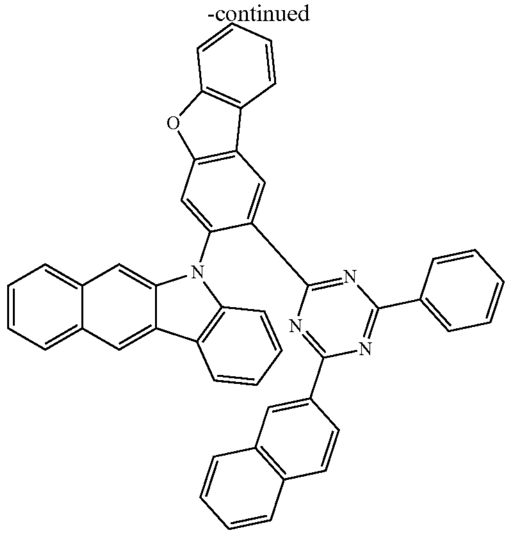
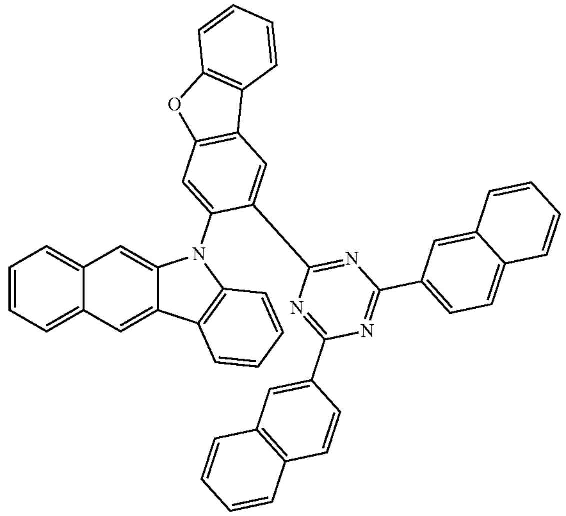
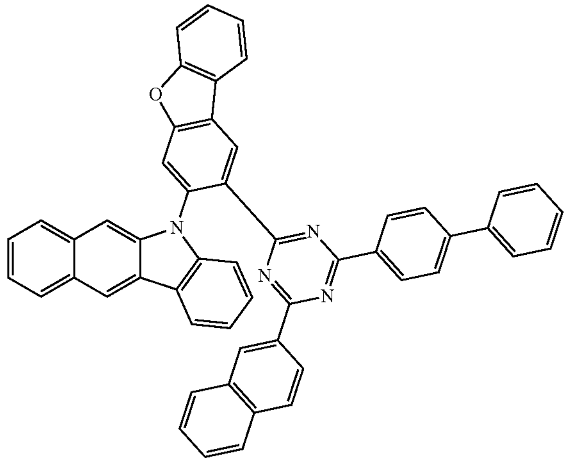
-continued
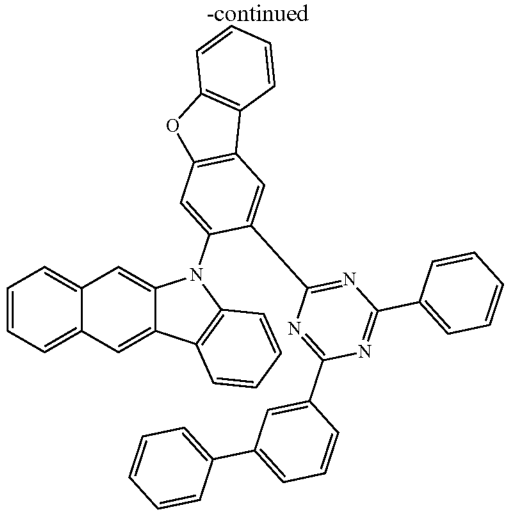
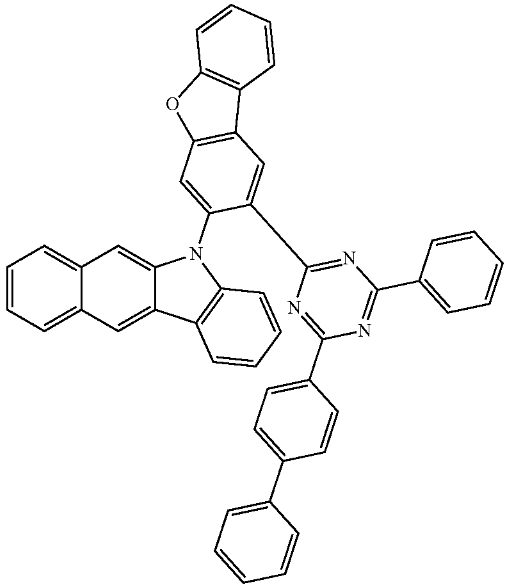
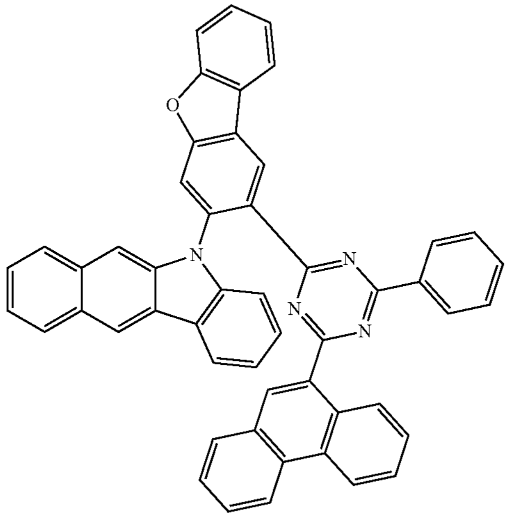

-continued
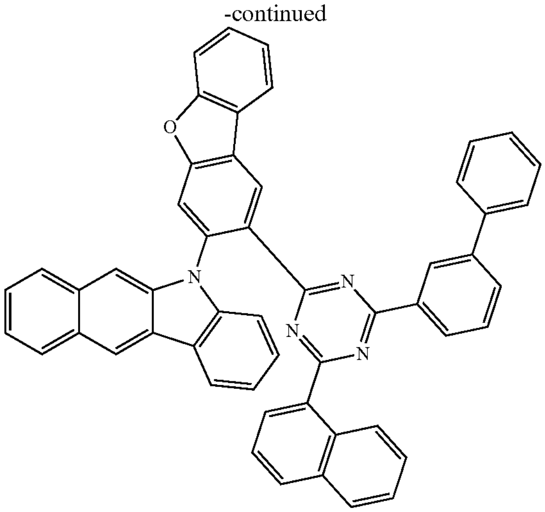
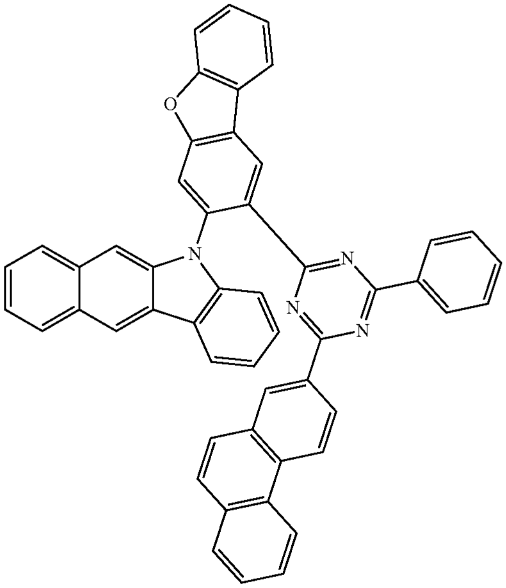
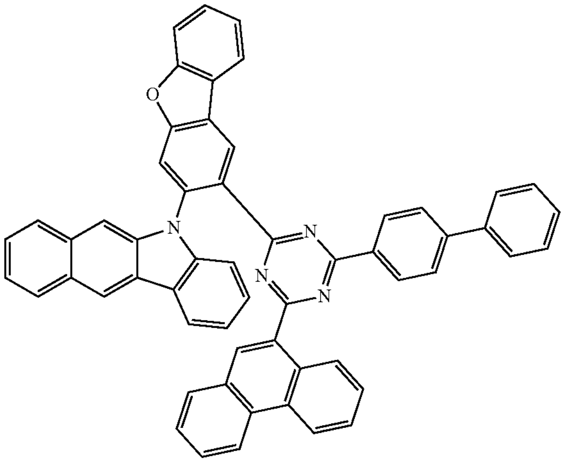
-continued
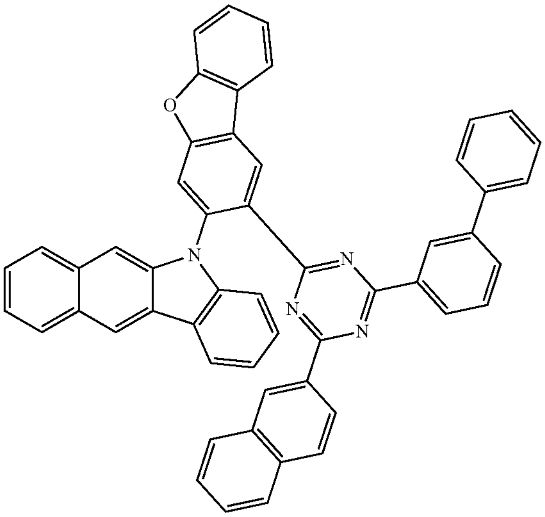
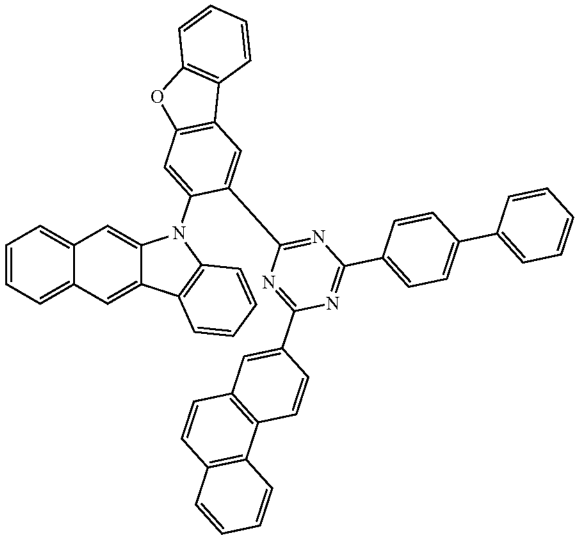
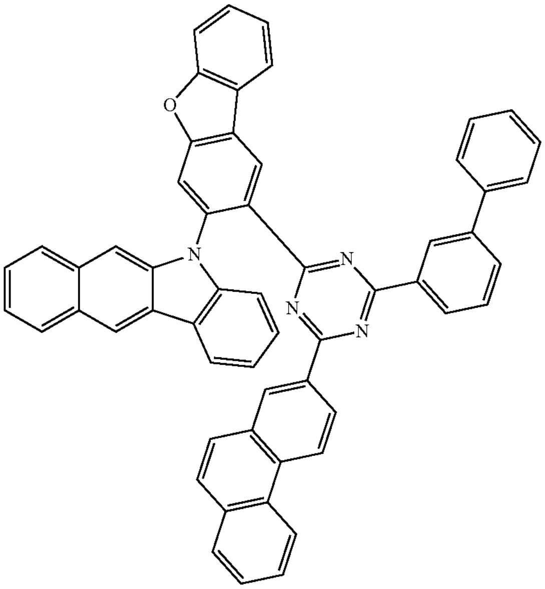

-continued
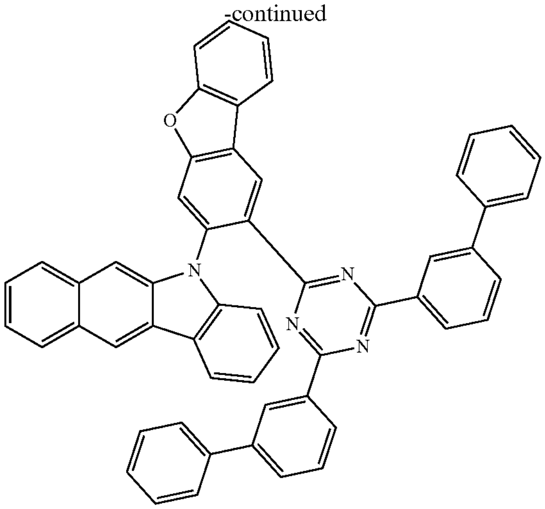
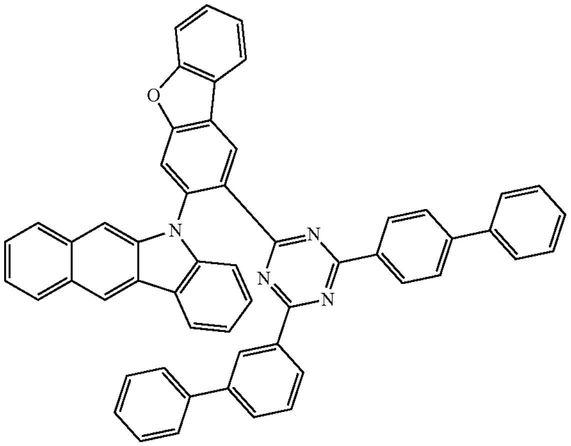
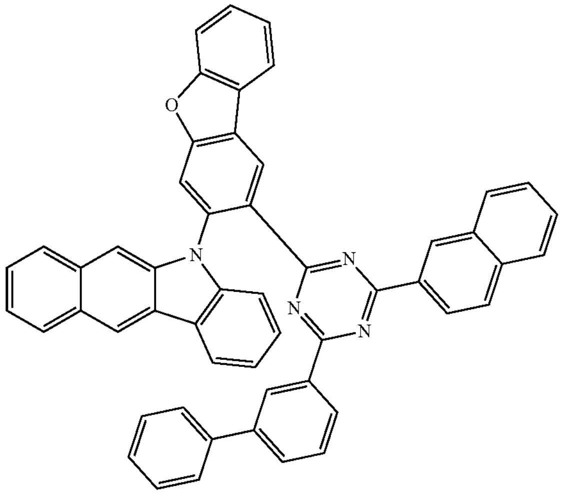
-continued
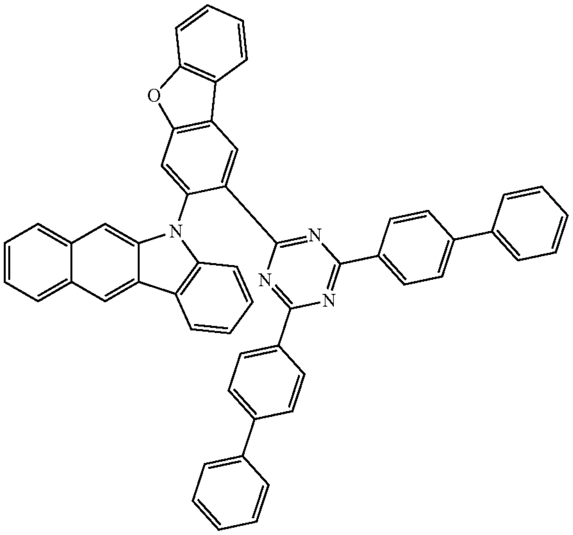
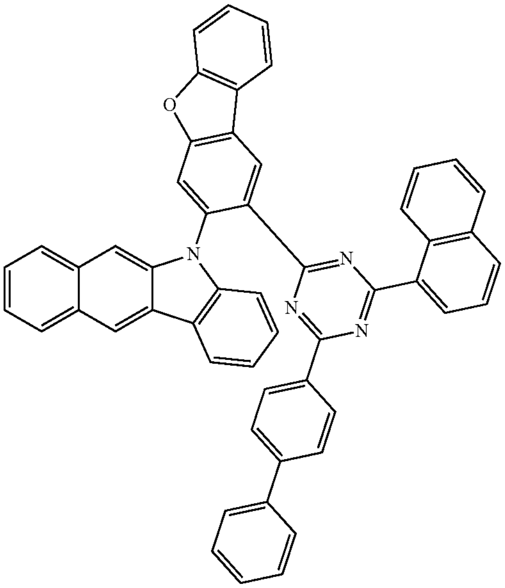
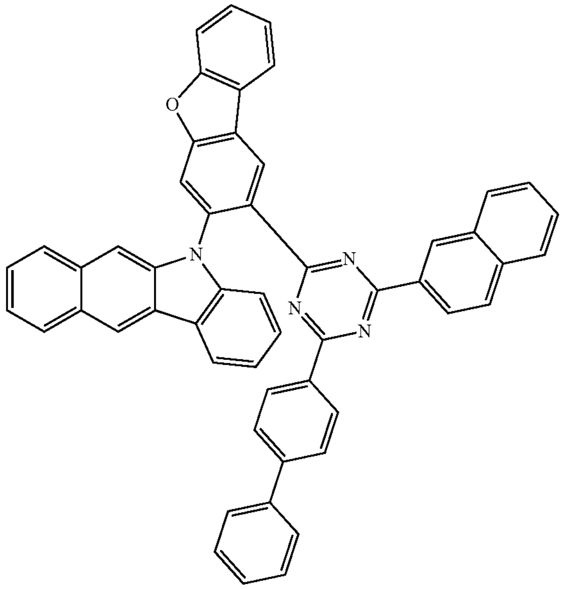

-continued
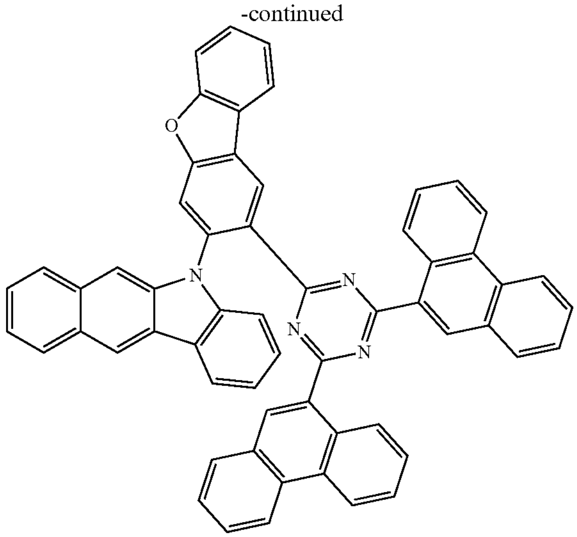
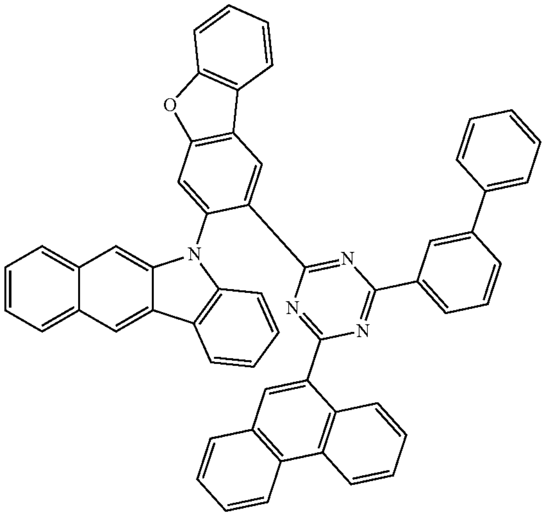
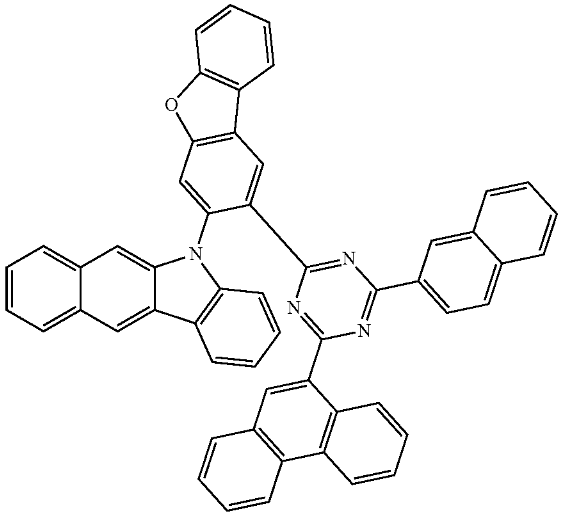
-continued
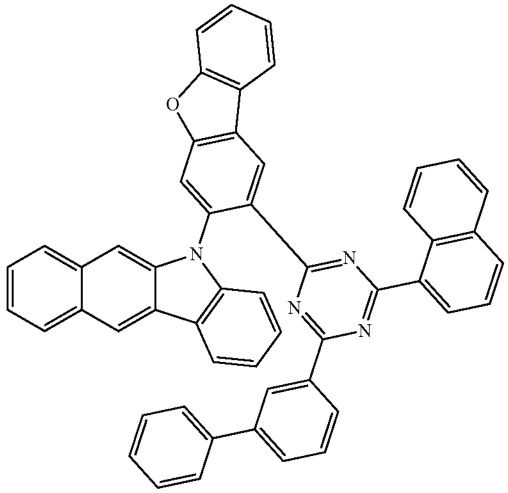
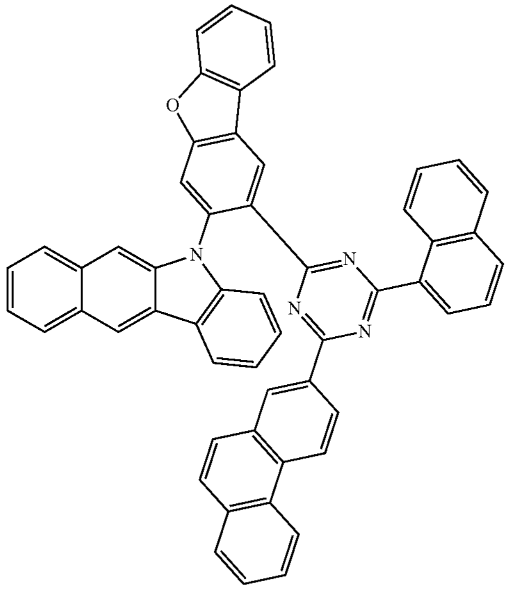
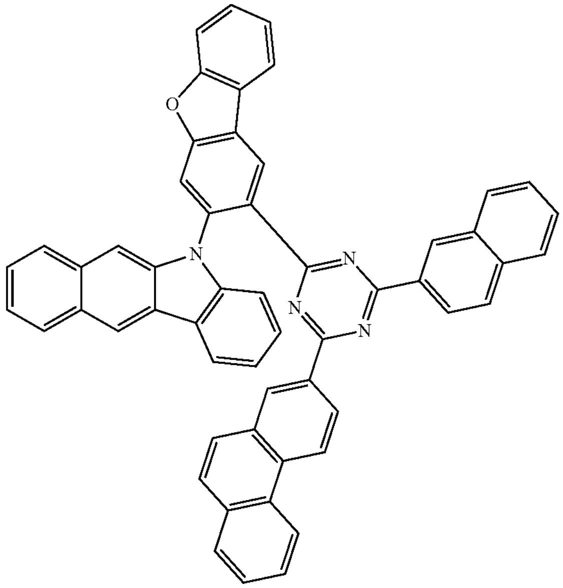

-continued
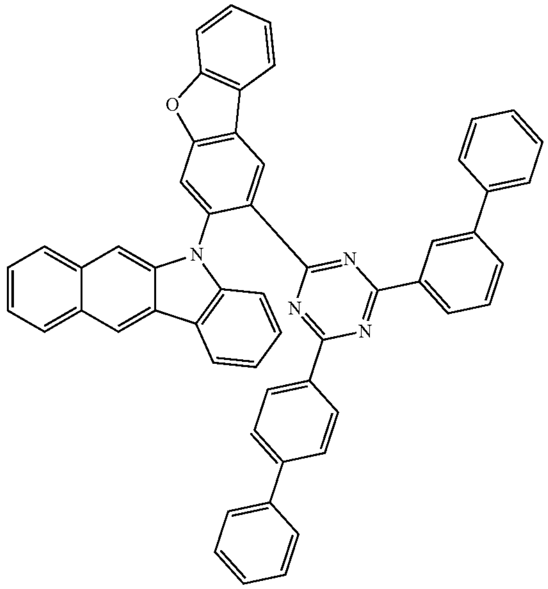
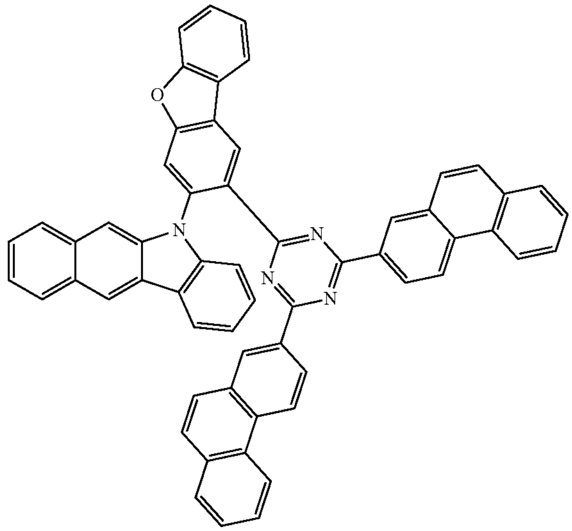
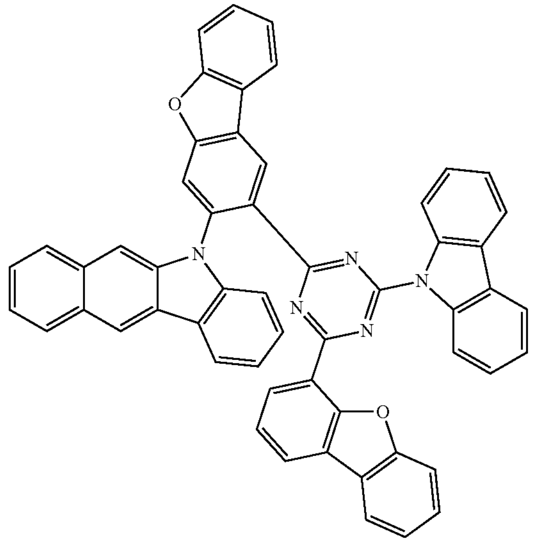
-continued
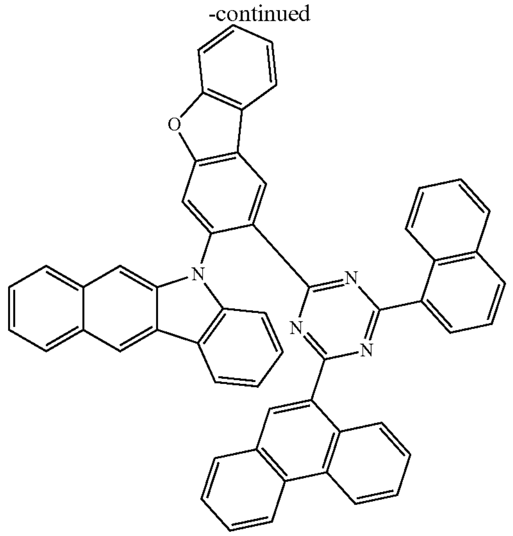
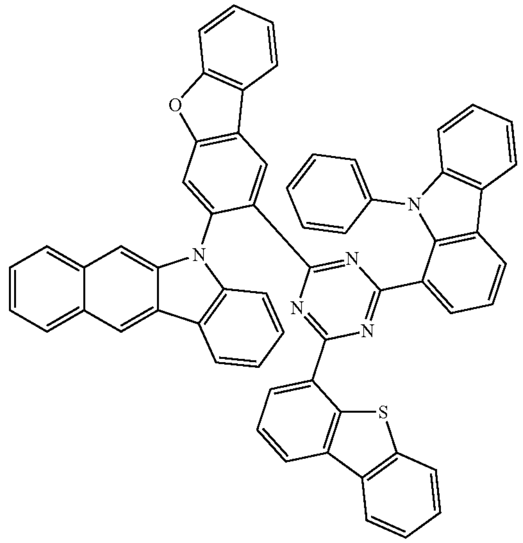
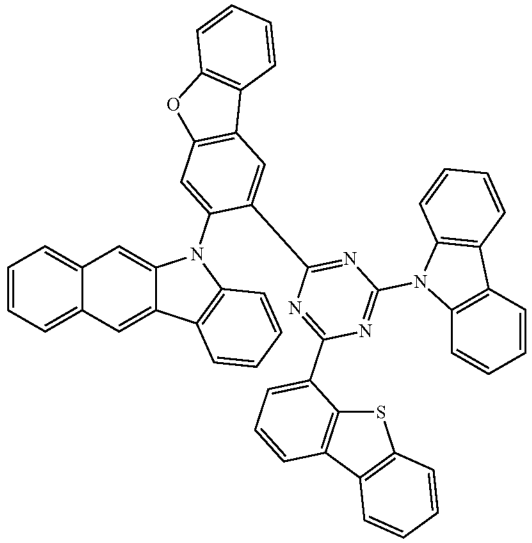

-continued
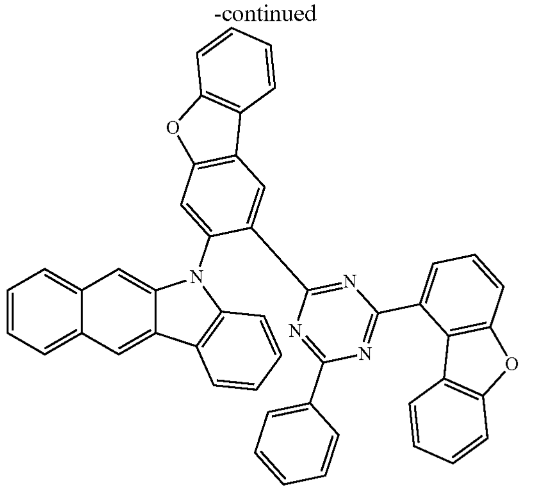
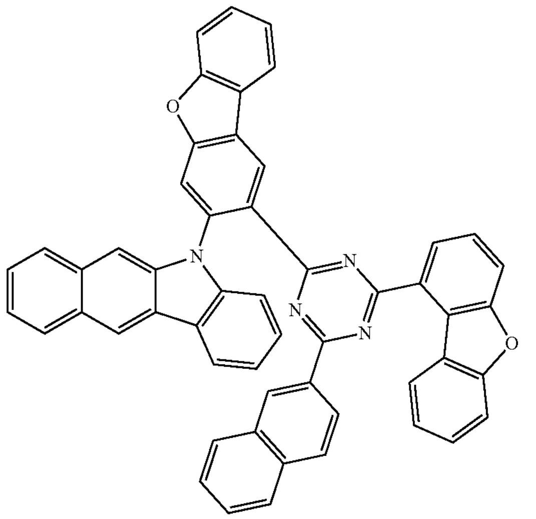
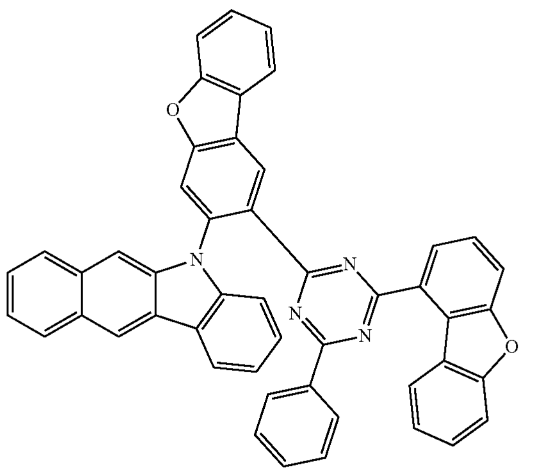
-continued
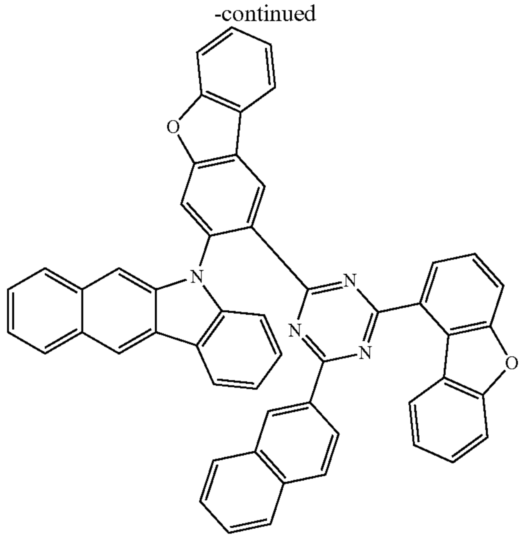
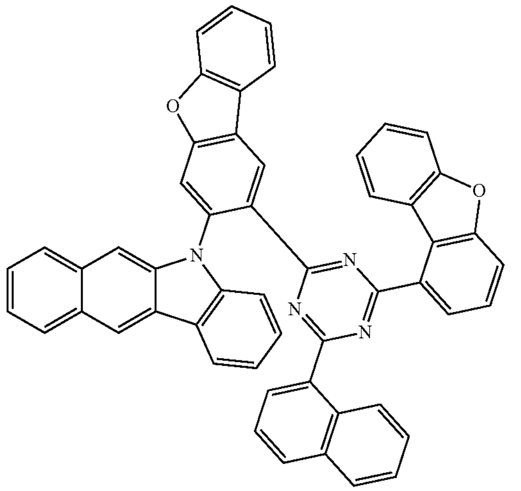
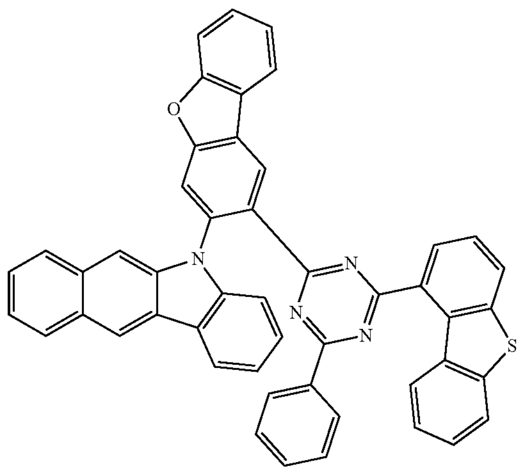

-continued
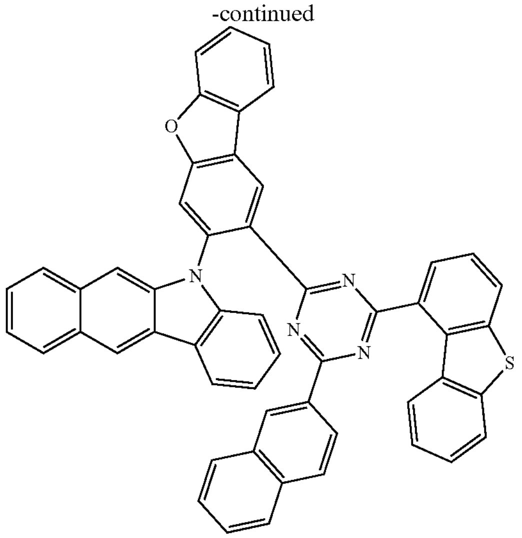
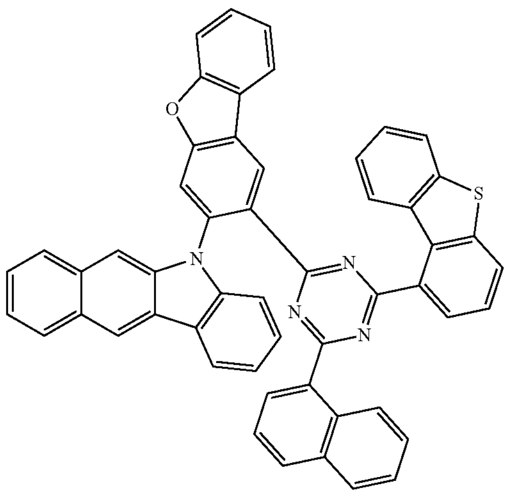
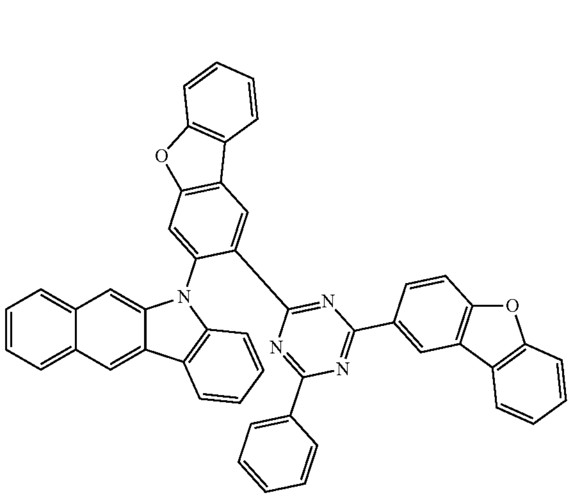
-continued
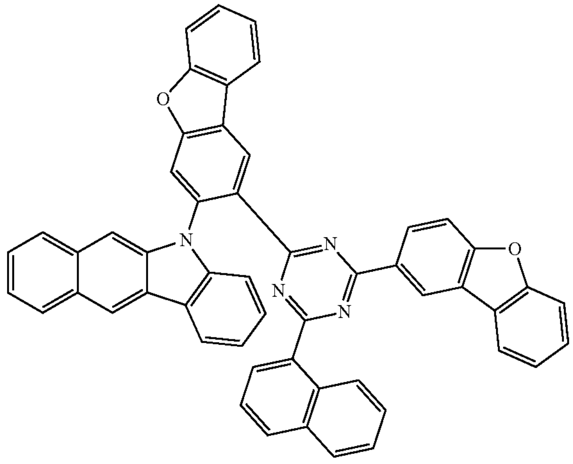
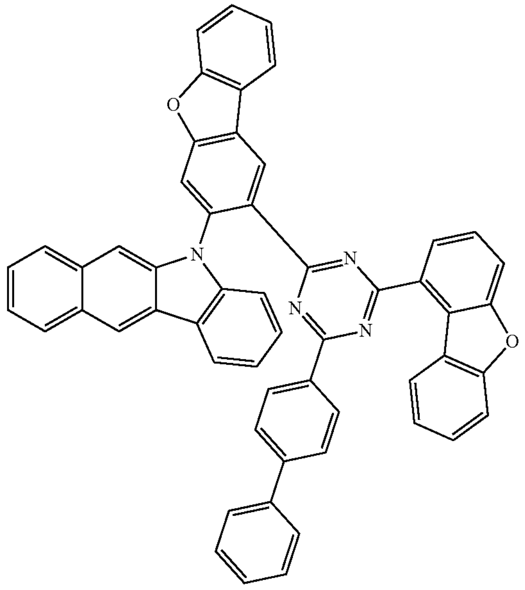
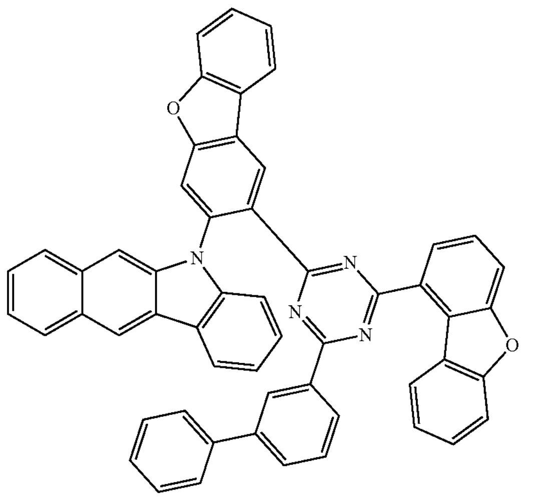

-continued
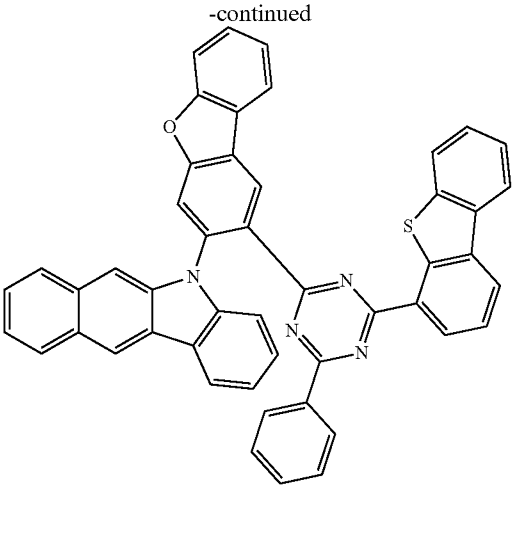
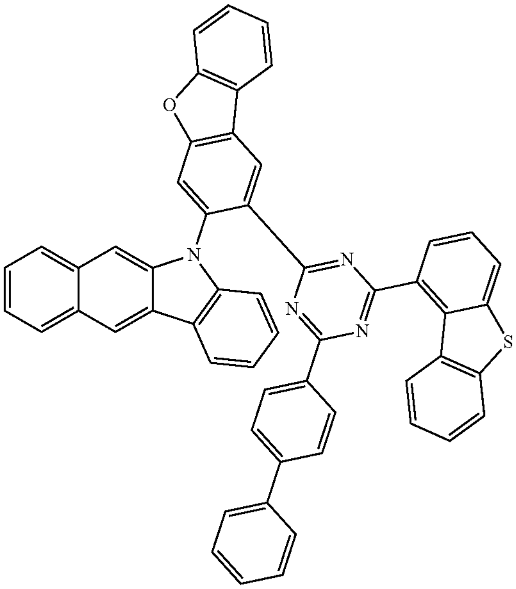
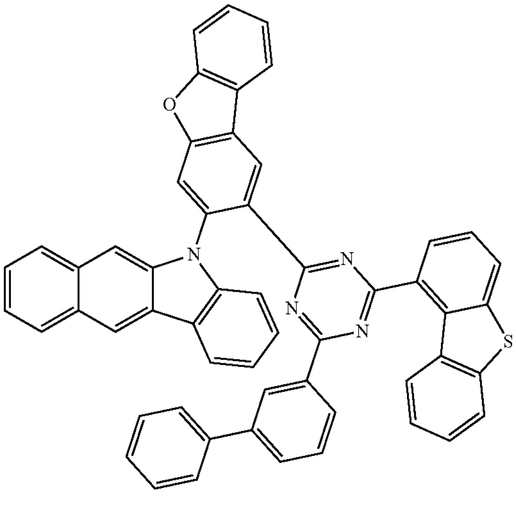
-continued
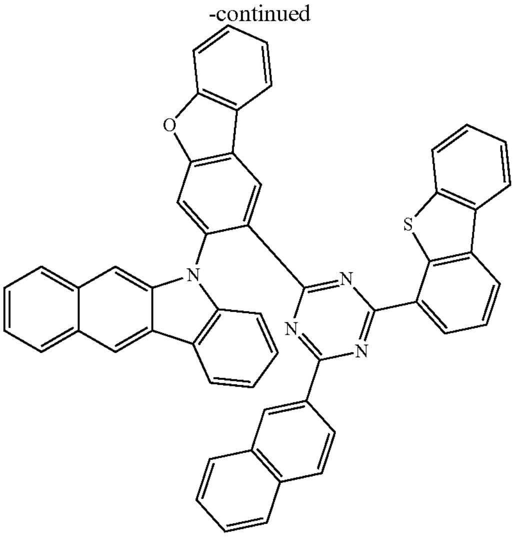
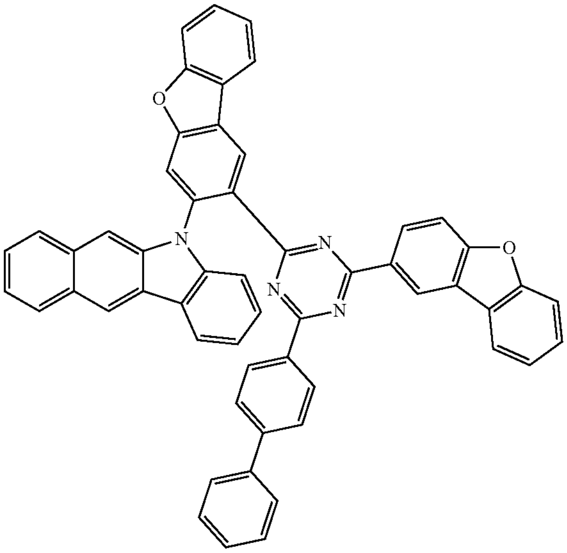
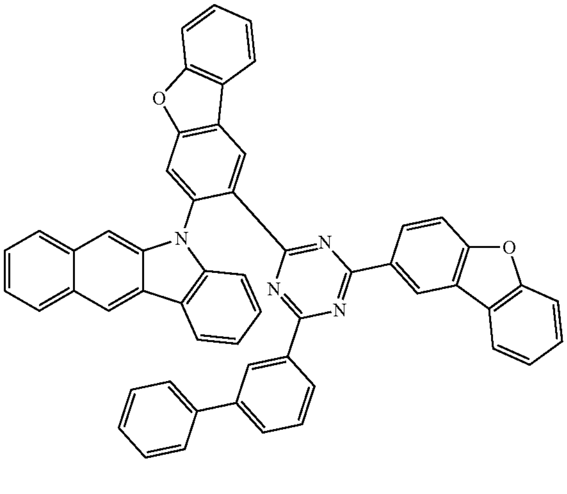

-continued
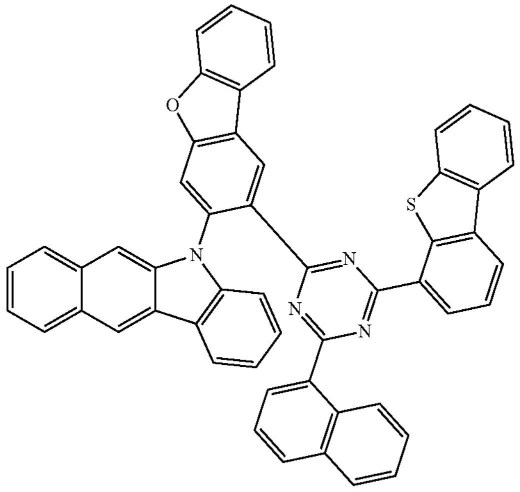
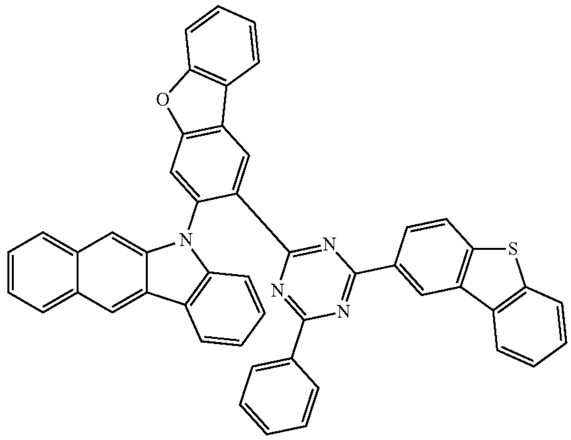
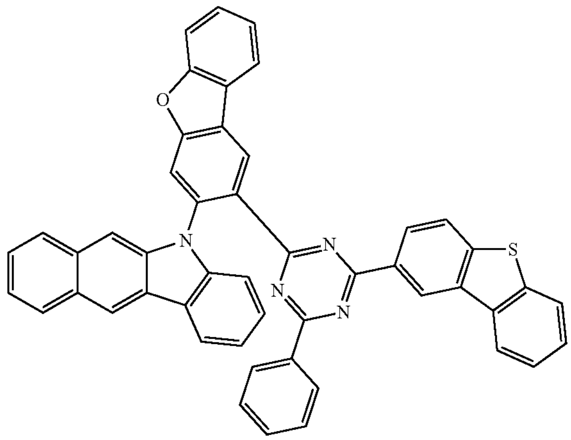
-continued
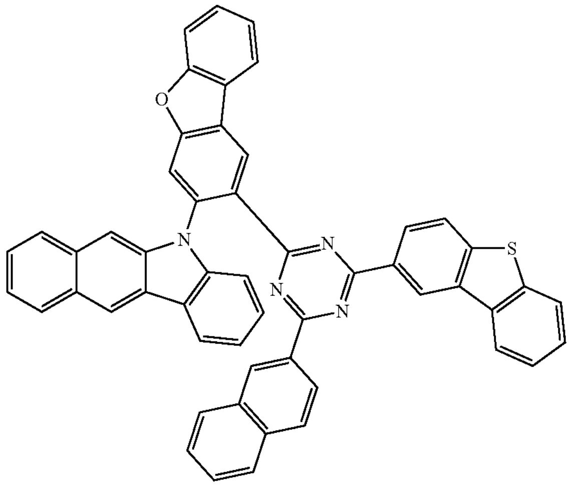
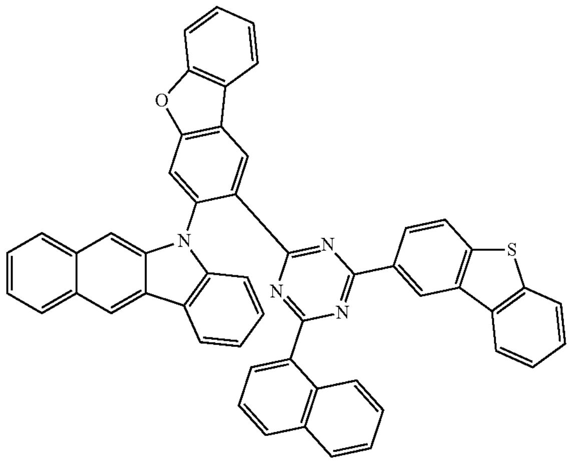
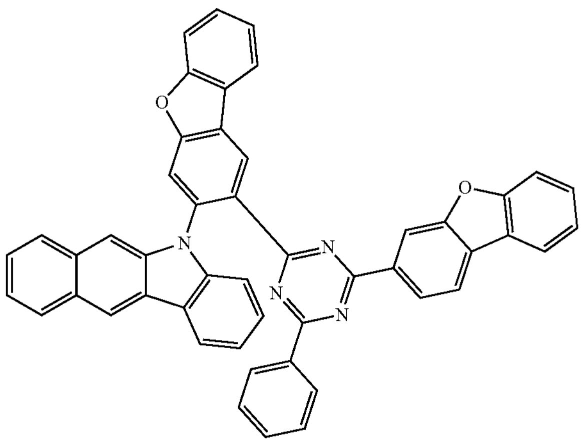

-continued
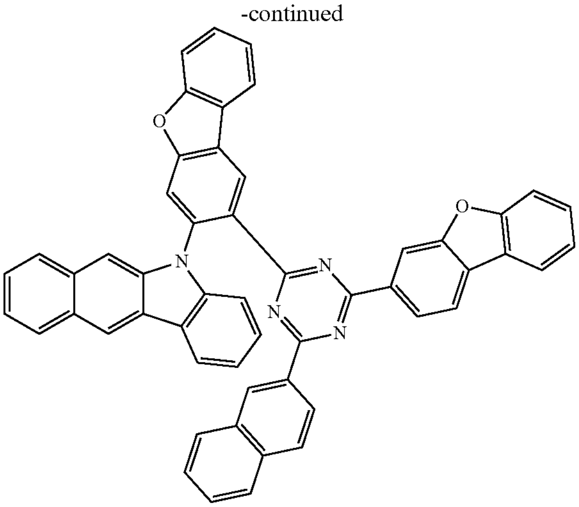
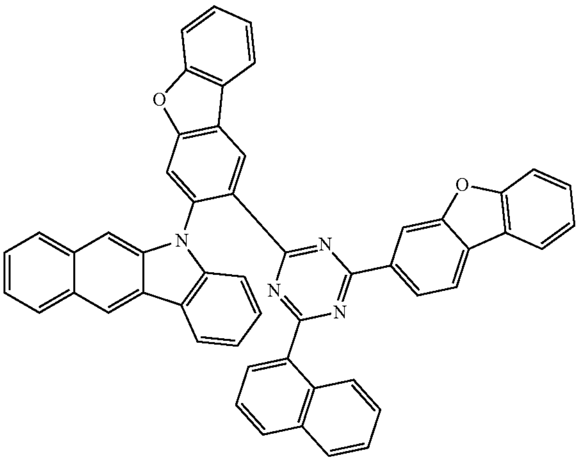
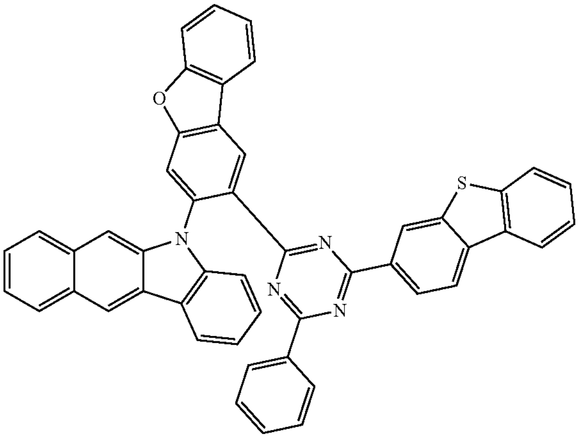
-continued
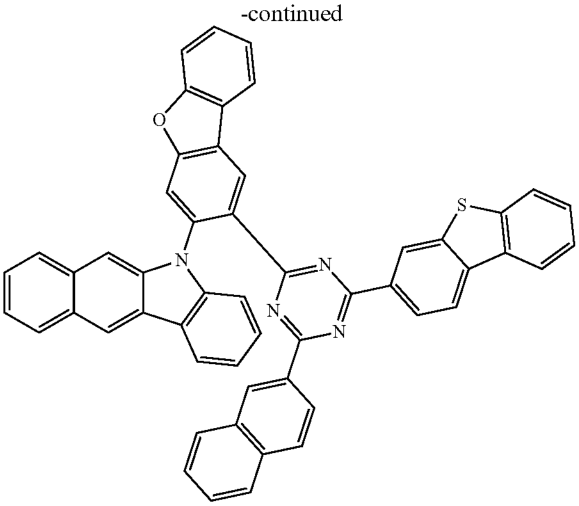
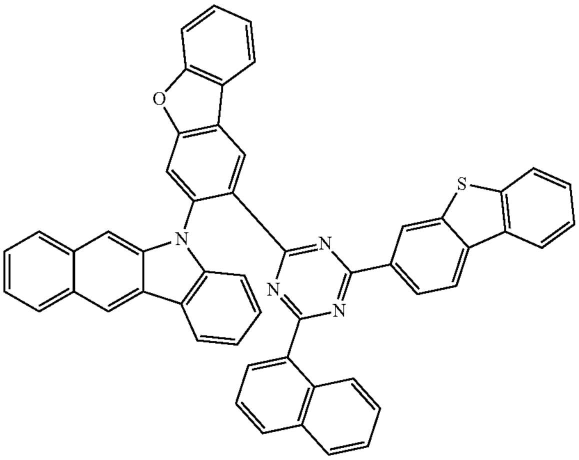
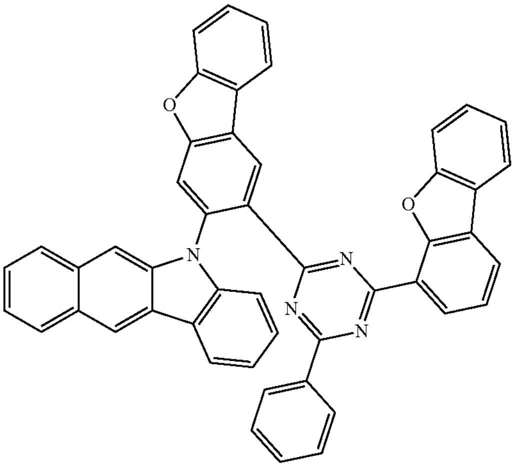

-continued
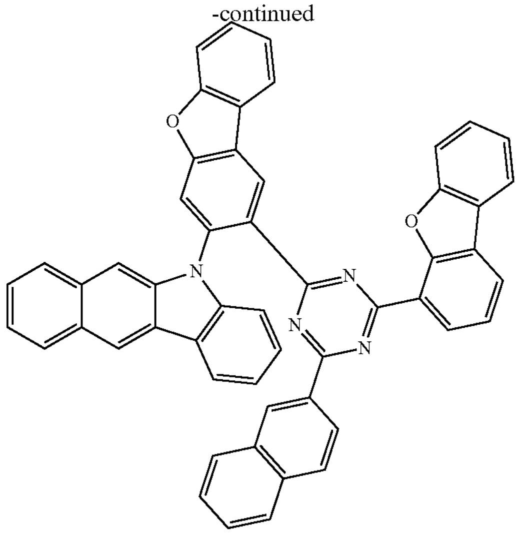
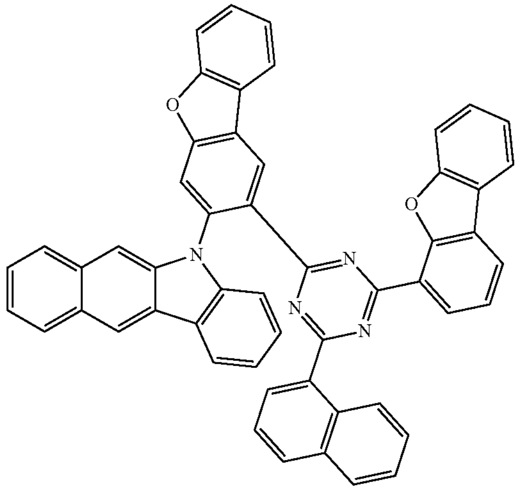
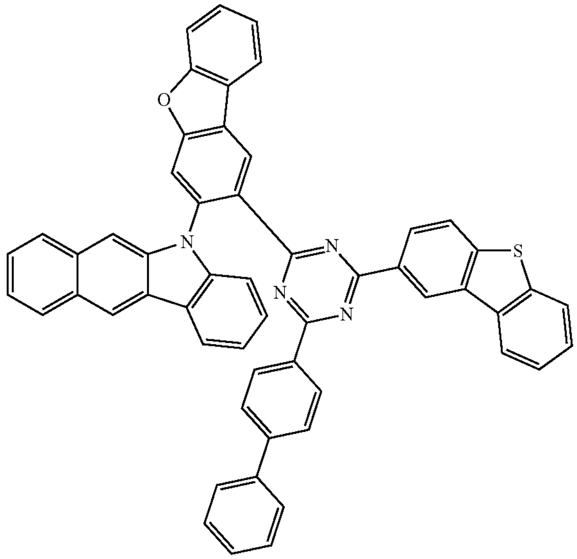
-continued
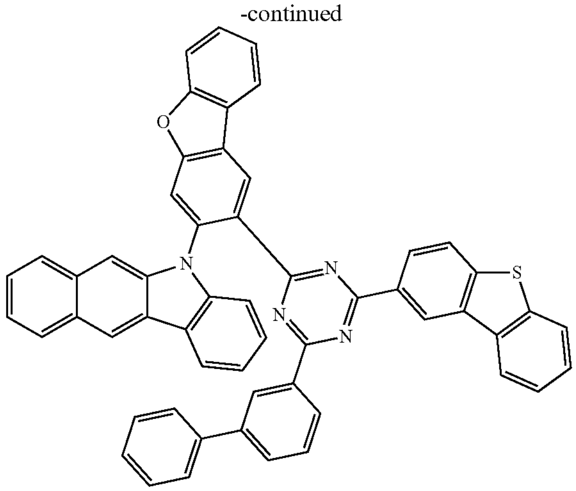
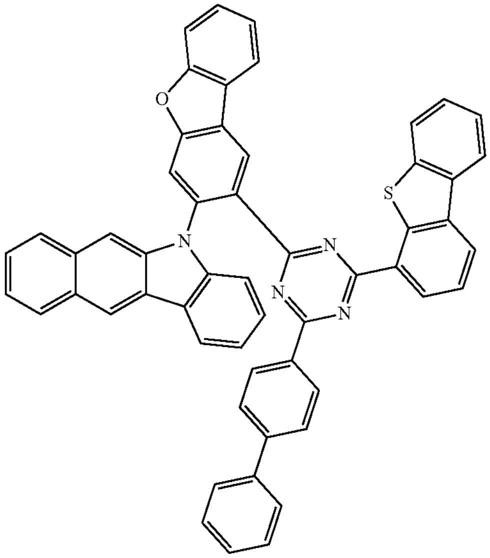
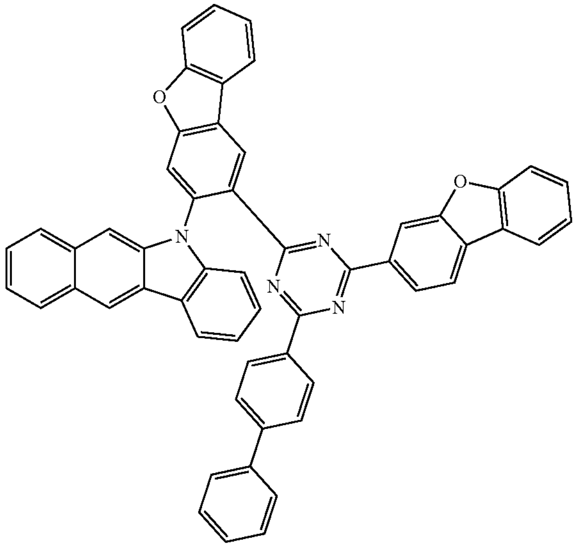

-continued
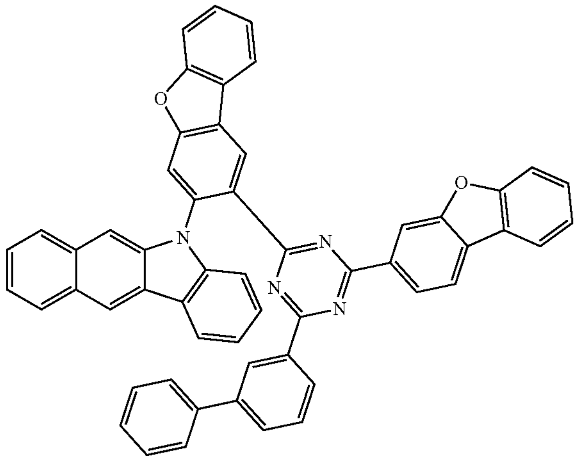
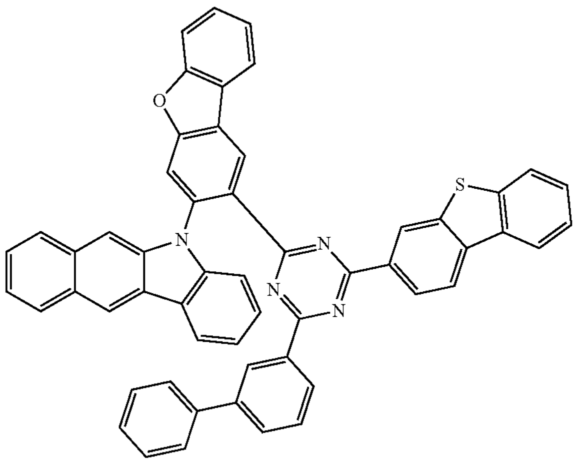
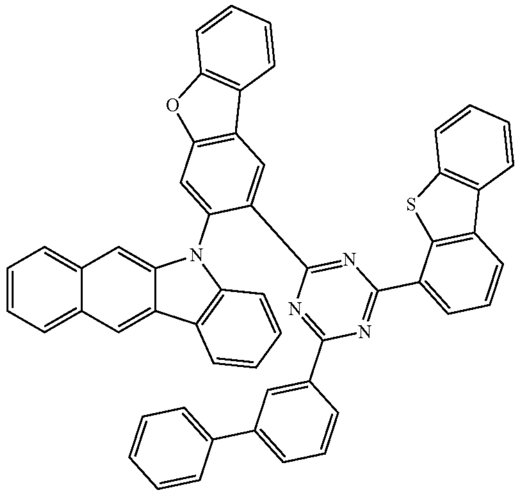
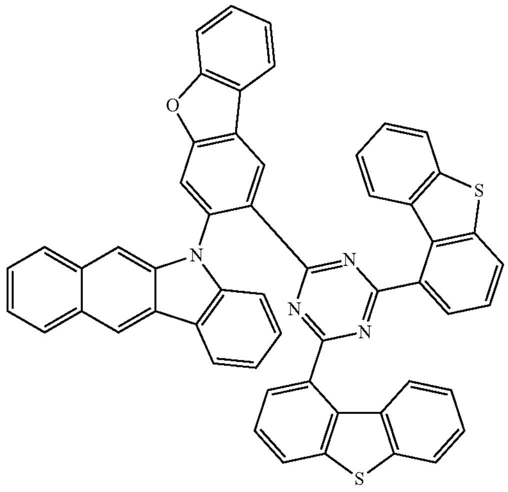
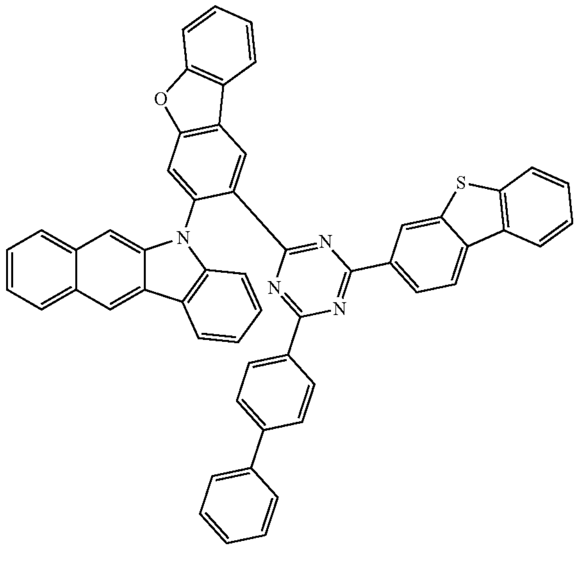
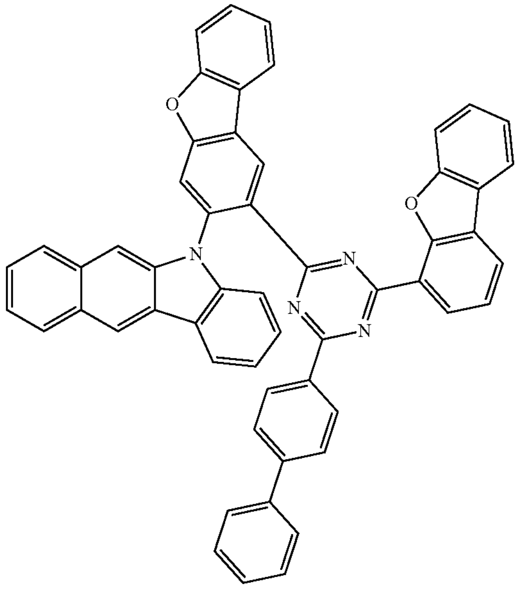

-continued
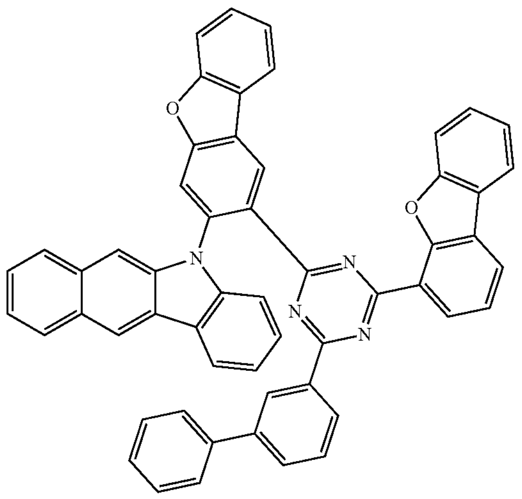
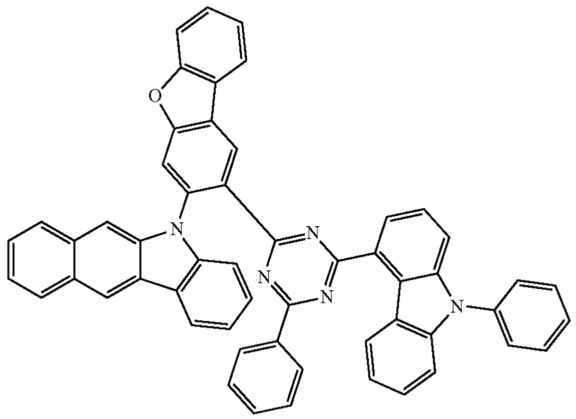
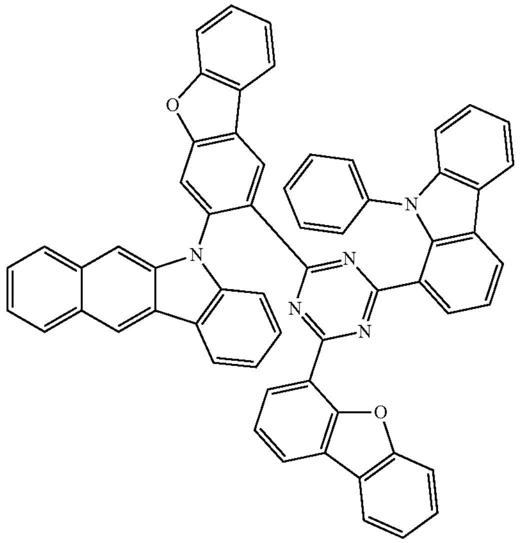
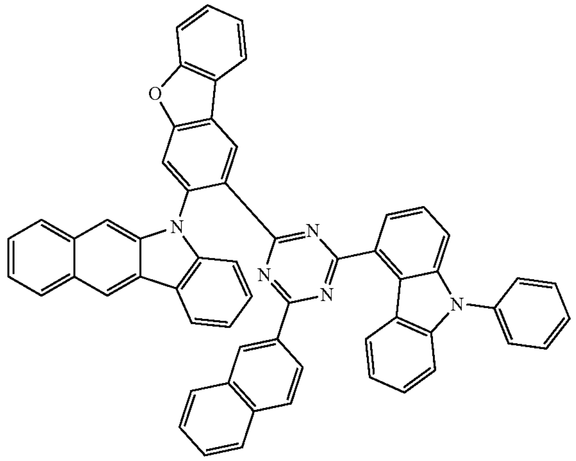
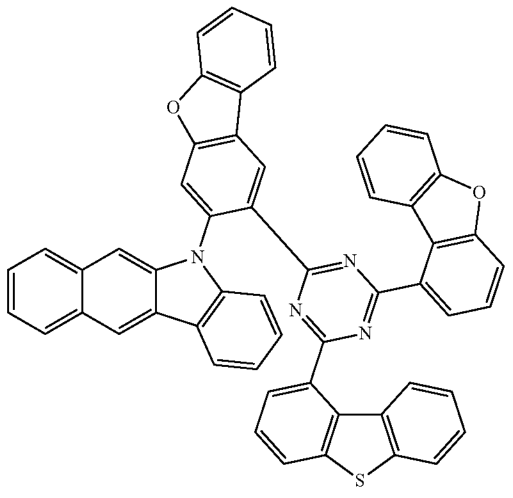
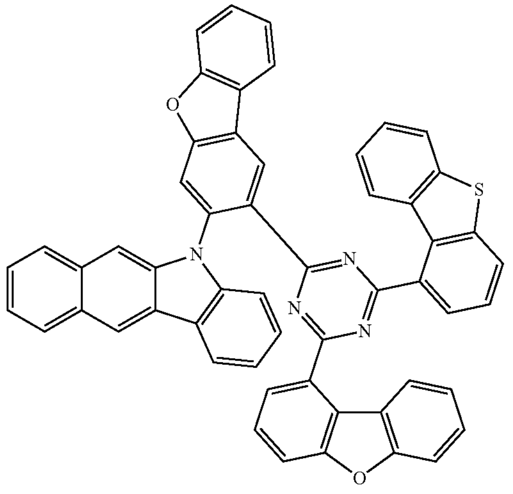
-continued -continued
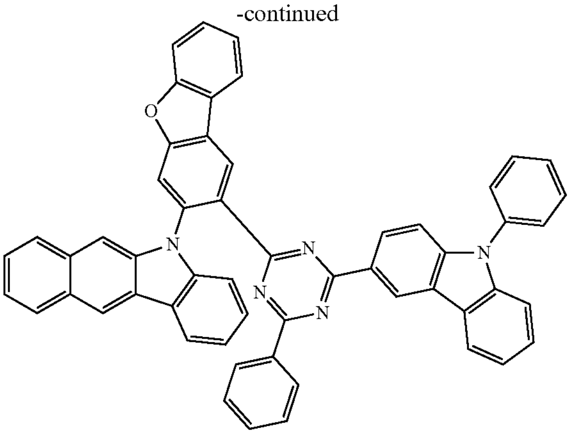
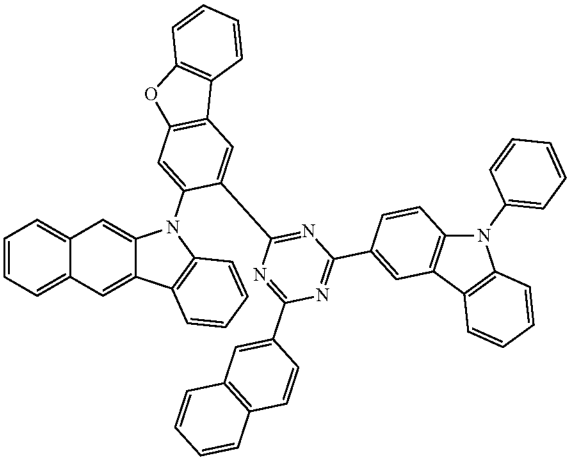
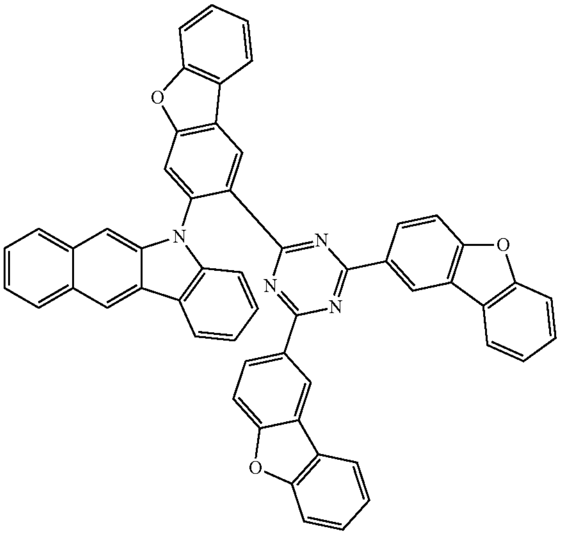
-continued
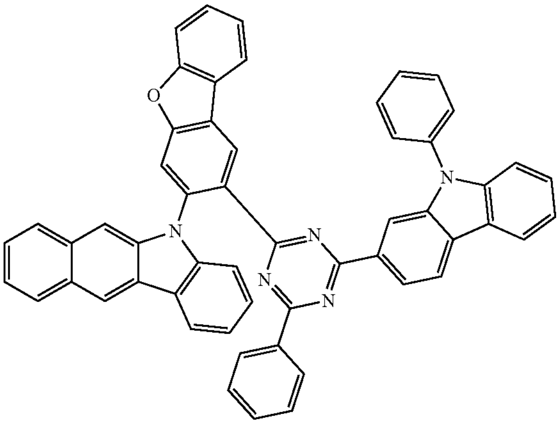
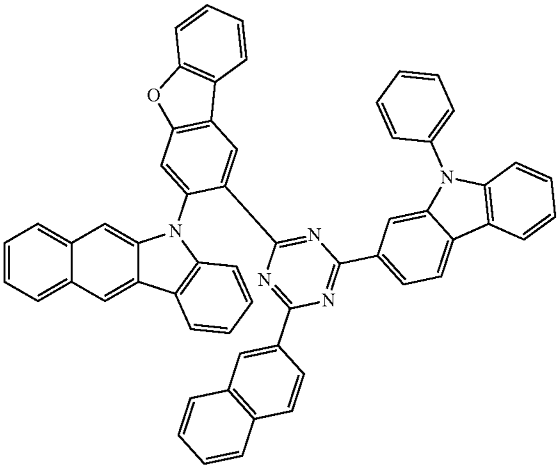
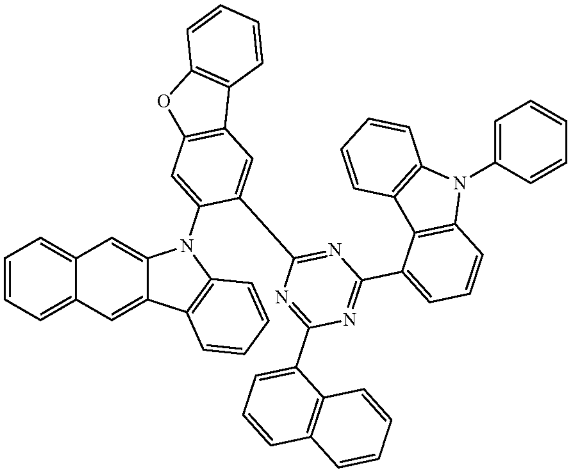

-continued
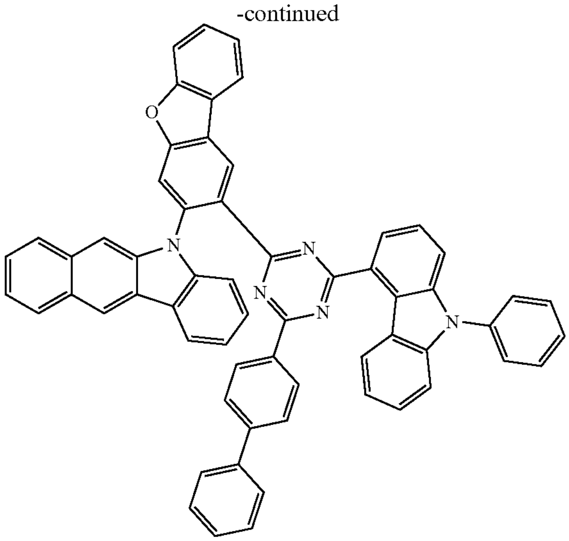
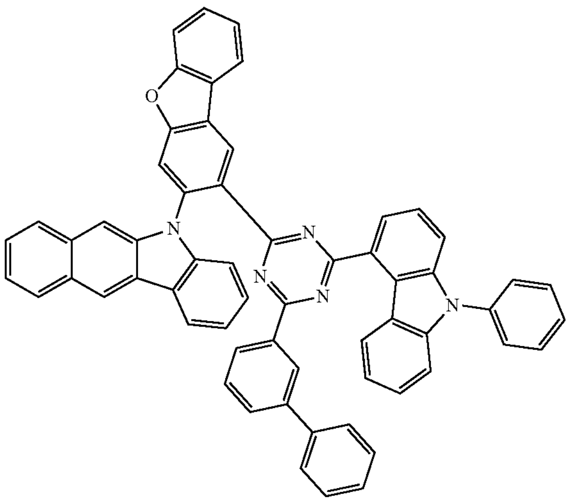
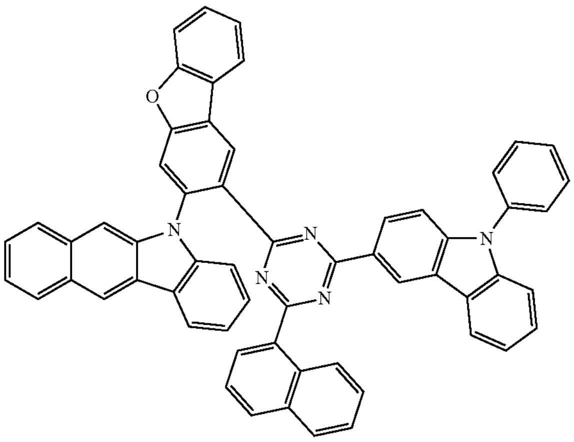
-continued
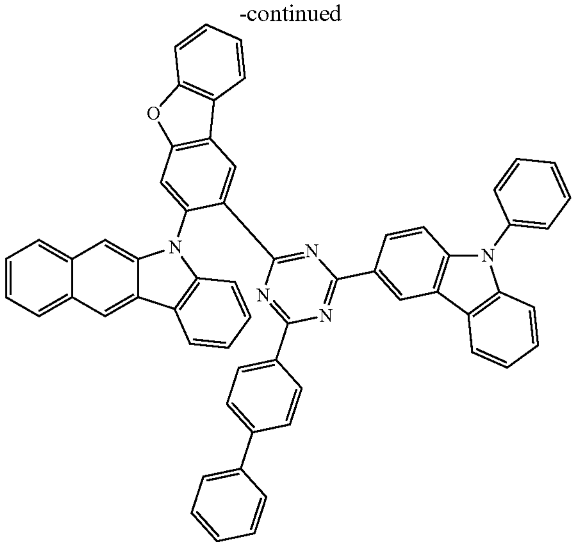
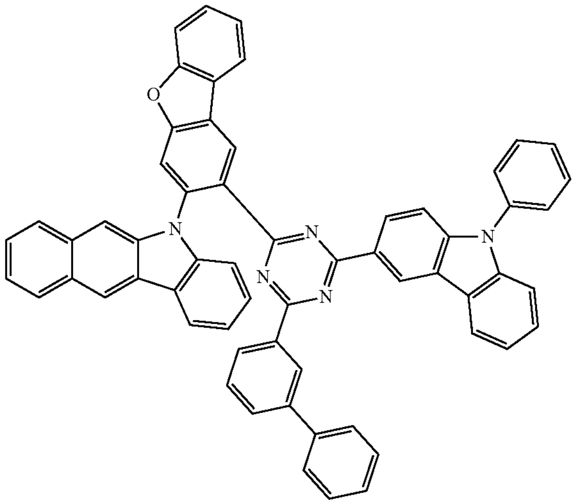
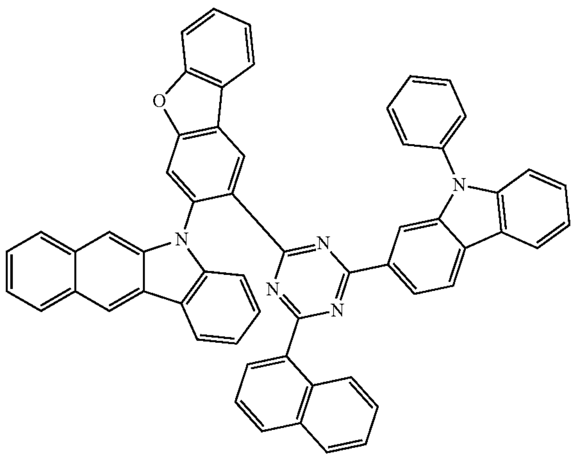

-continued
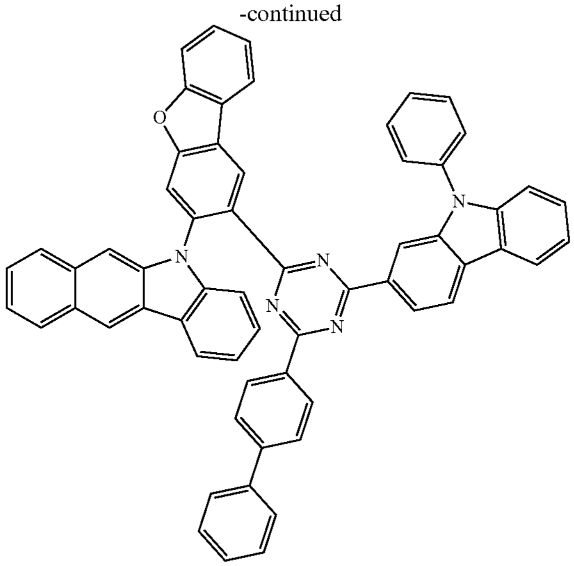
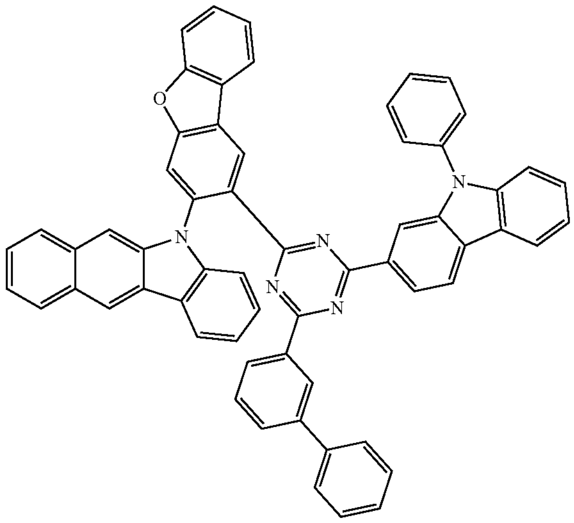
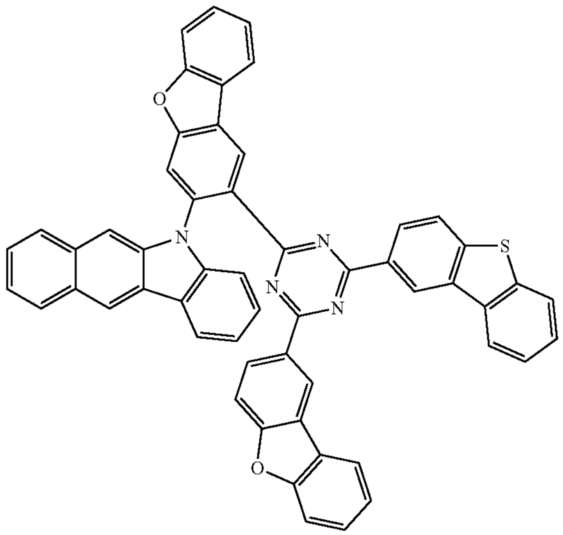
-continued
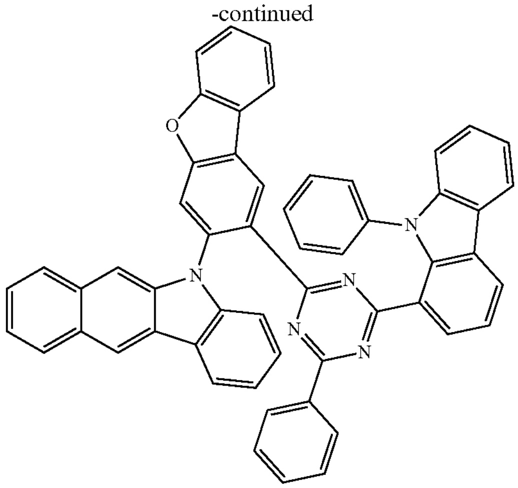
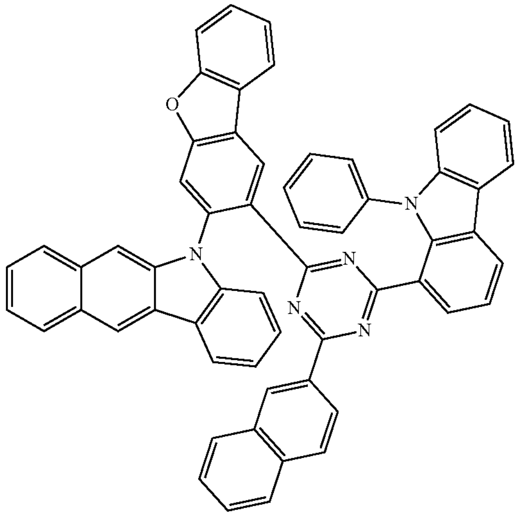
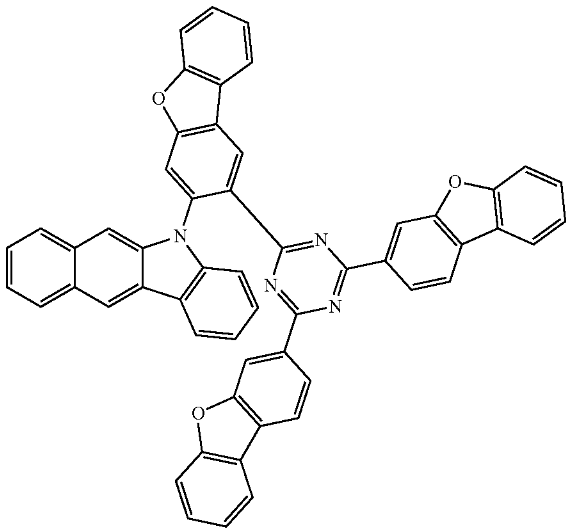

-continued
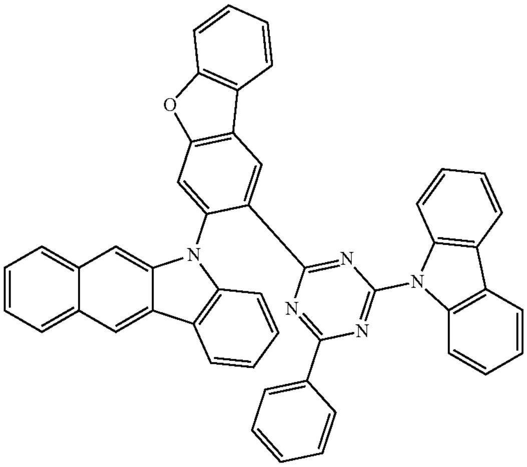
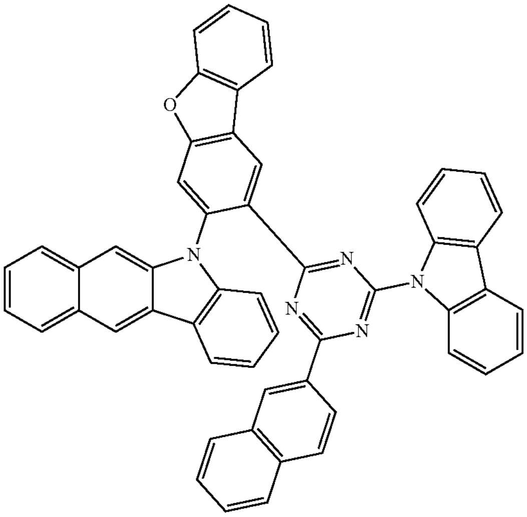
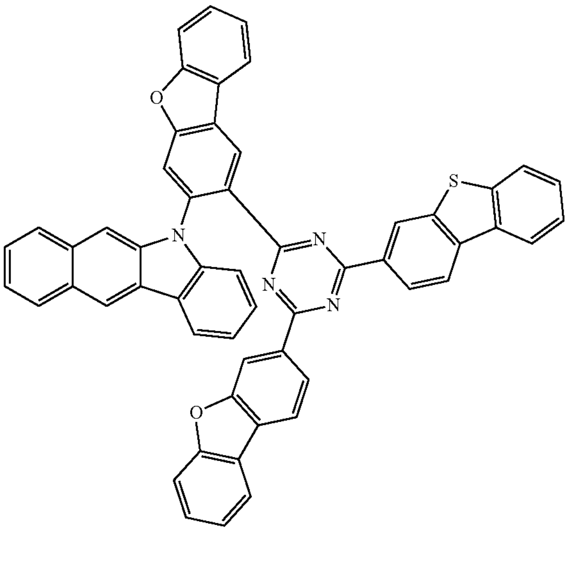
-continued
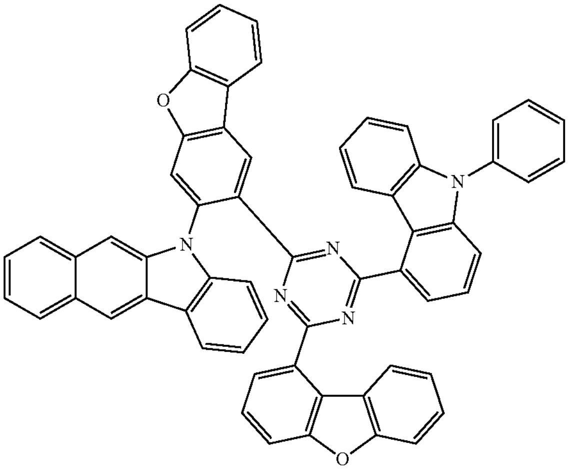
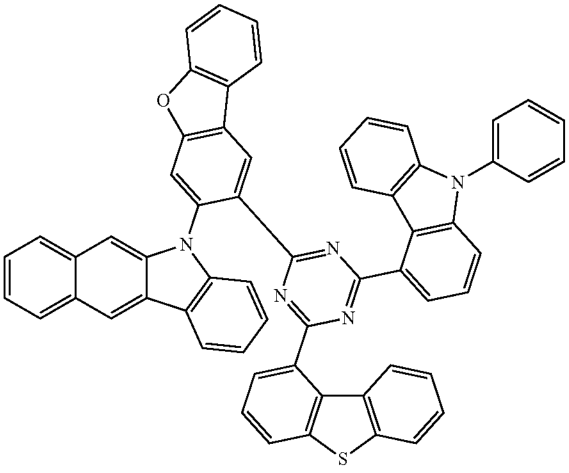
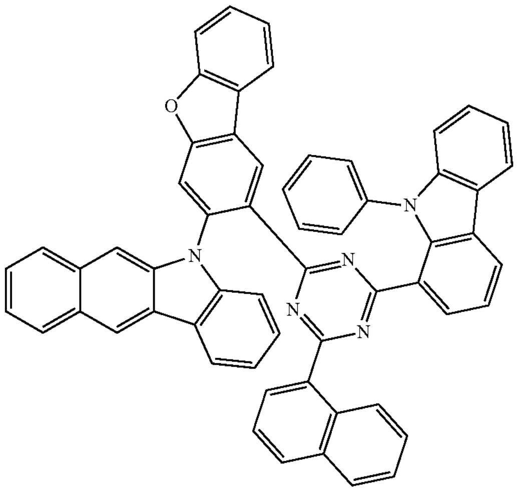

-continued
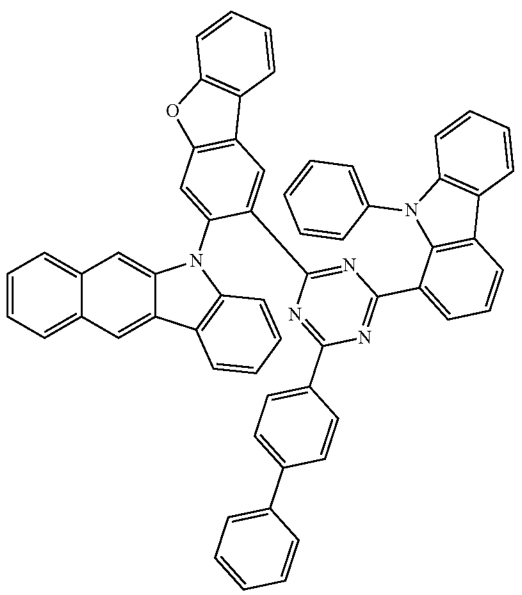
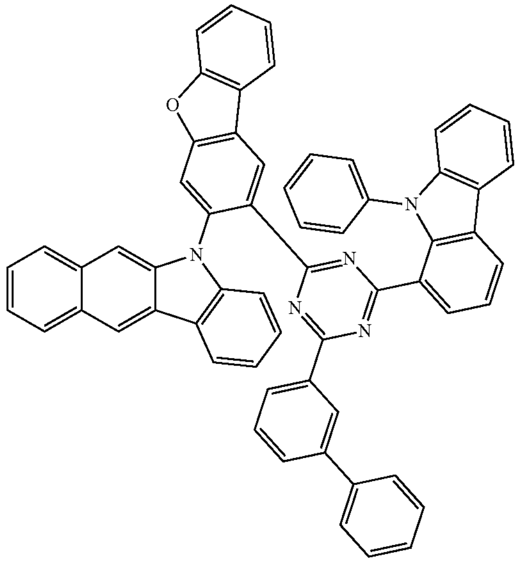
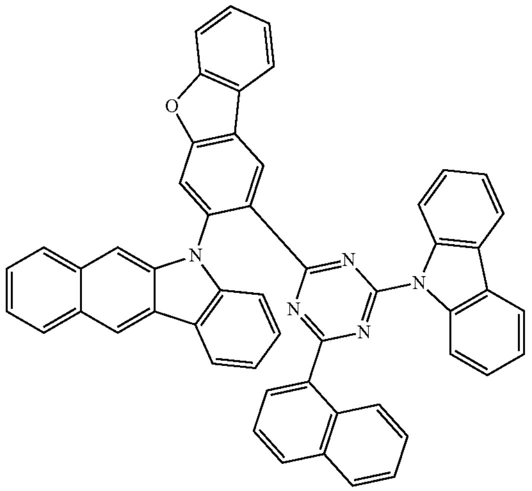
-continued
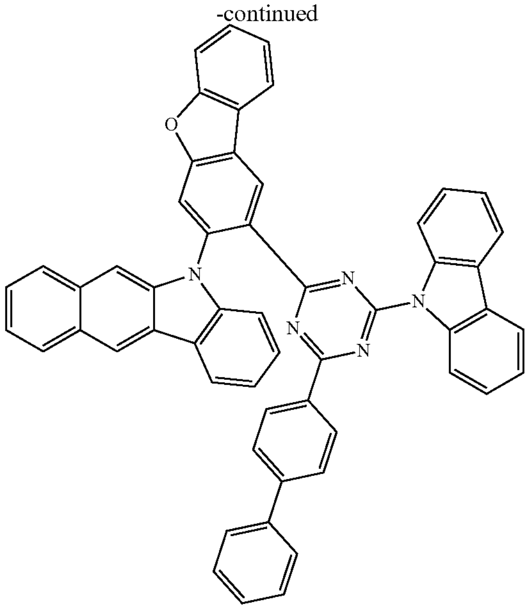
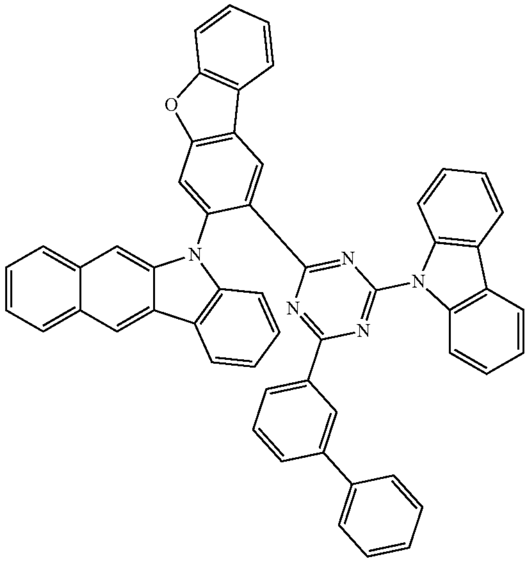
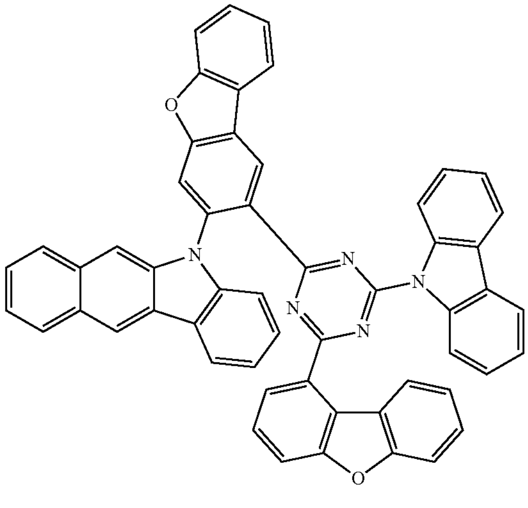

-continued
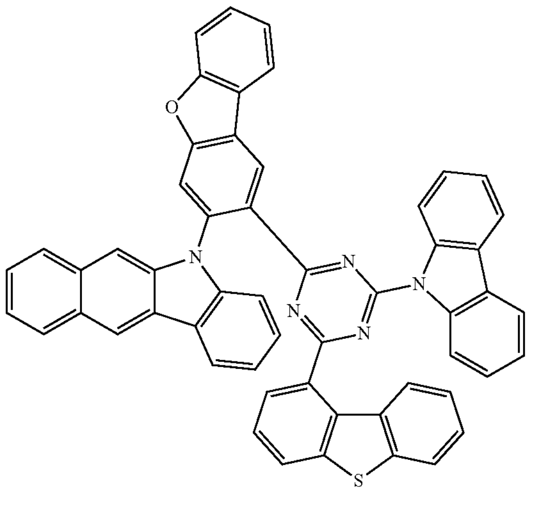
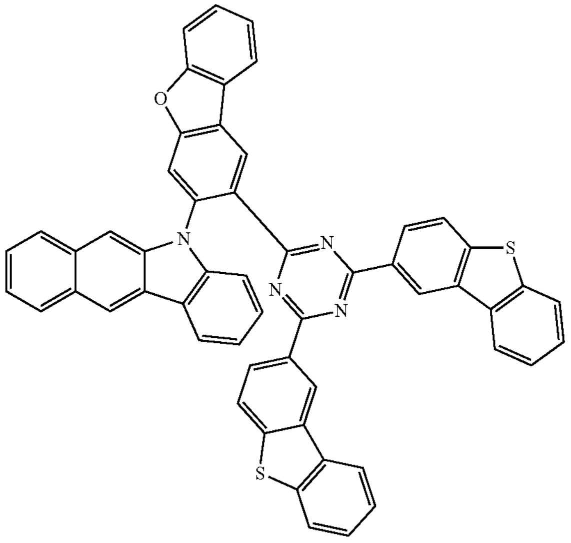
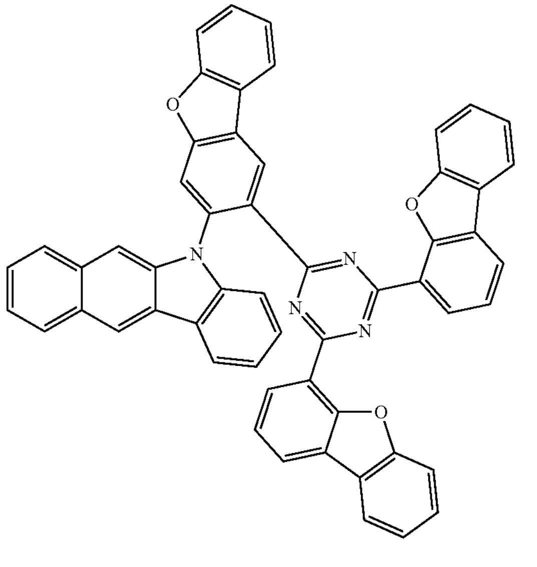
-continued
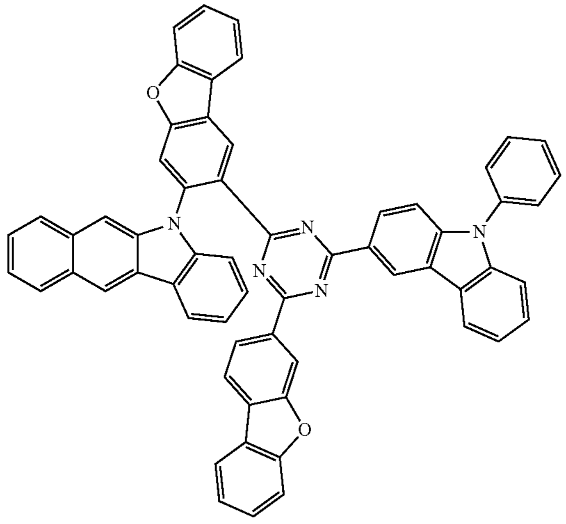
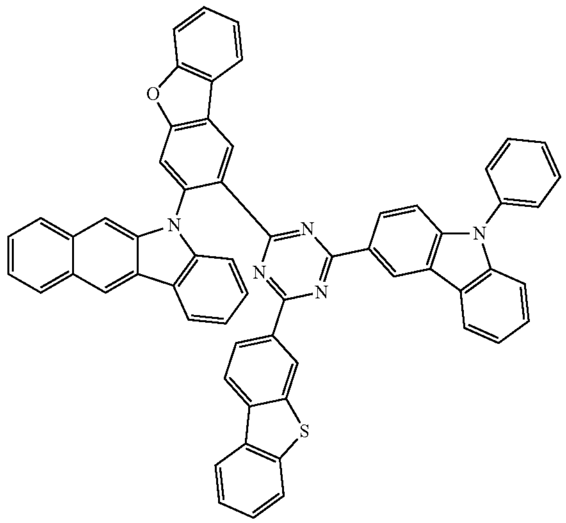
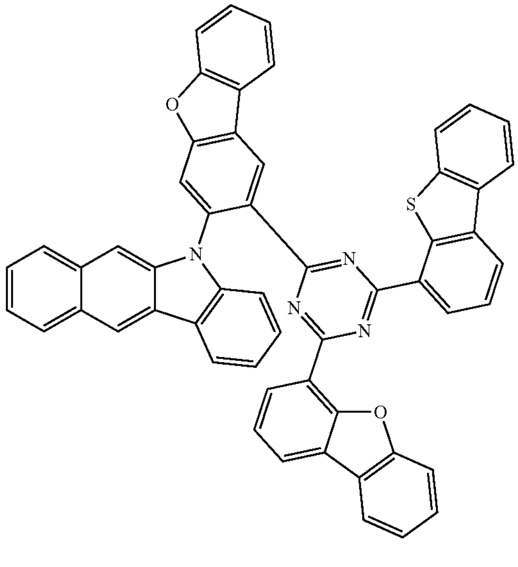

-continued
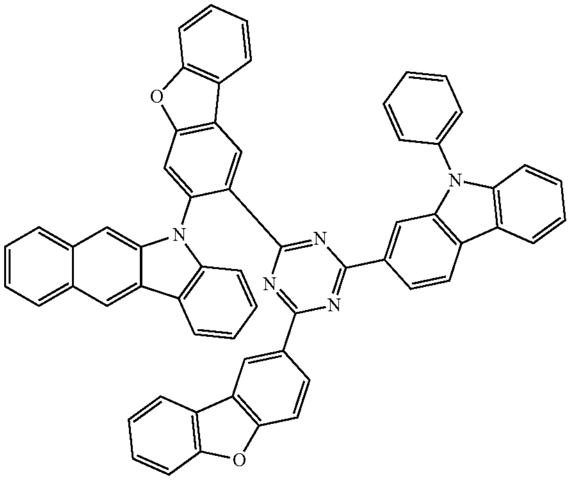
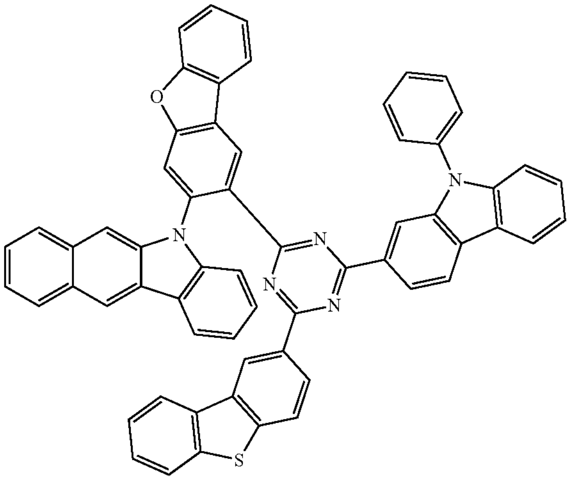
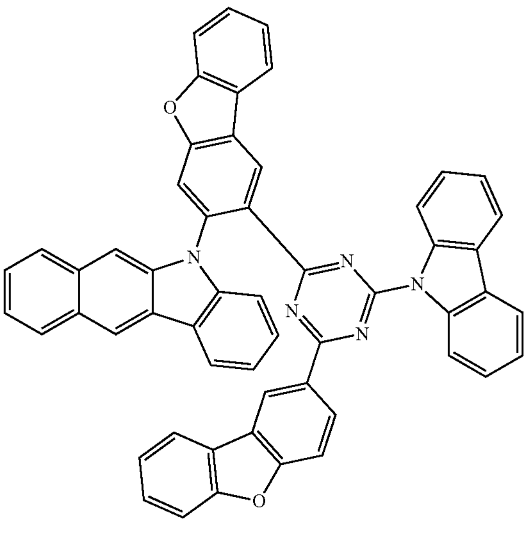
-continued
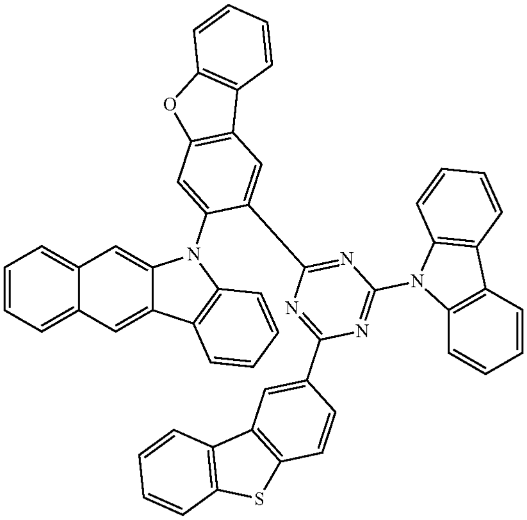
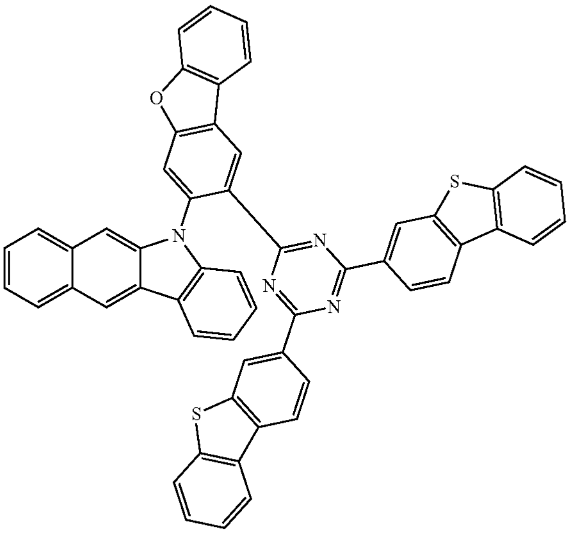
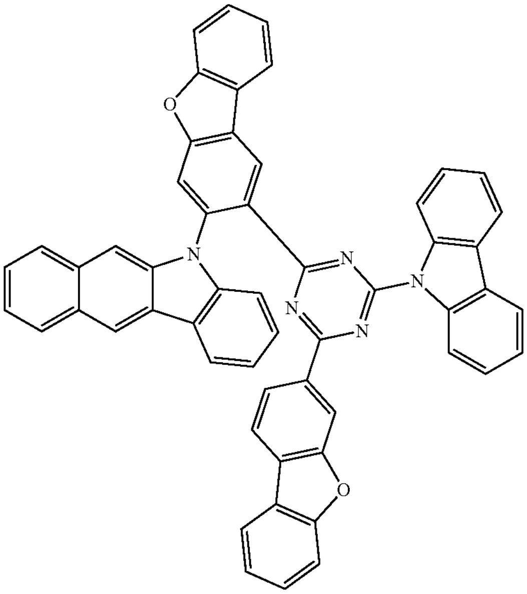

-continued
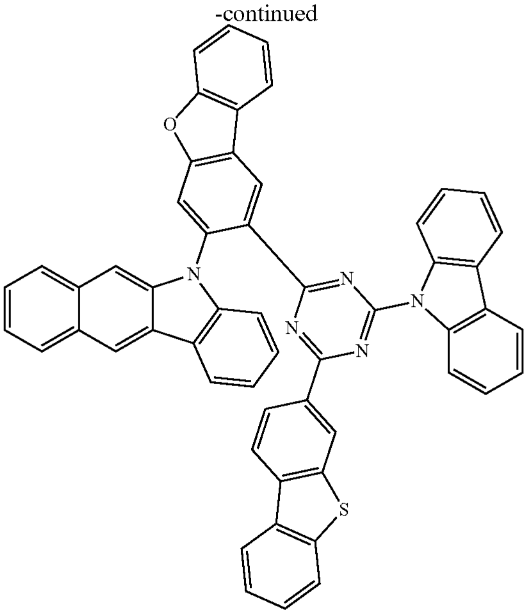
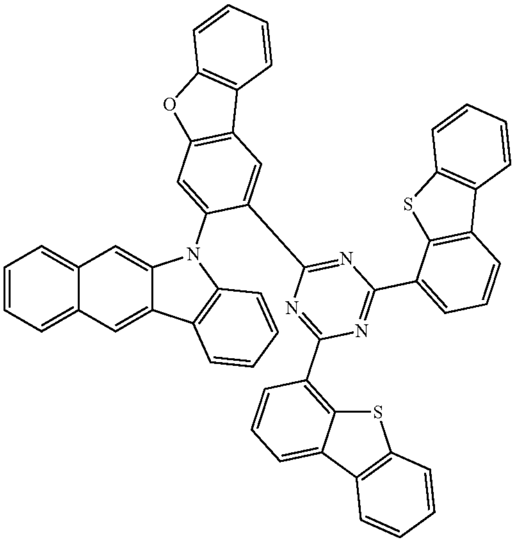
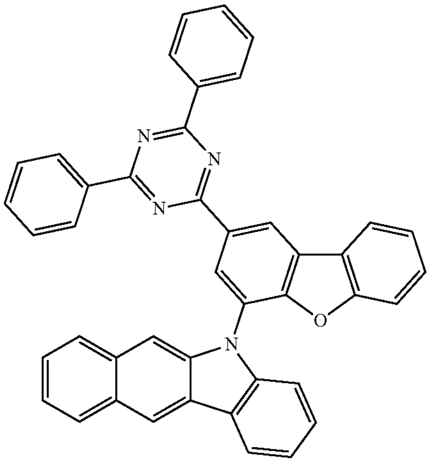
-continued
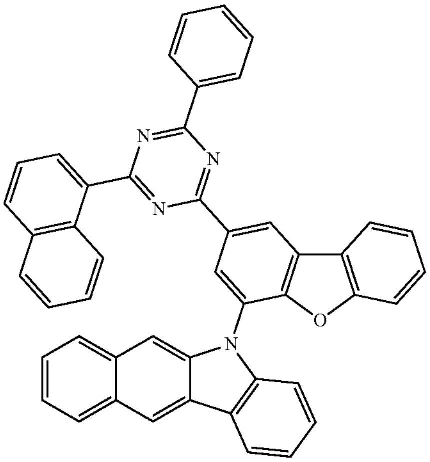
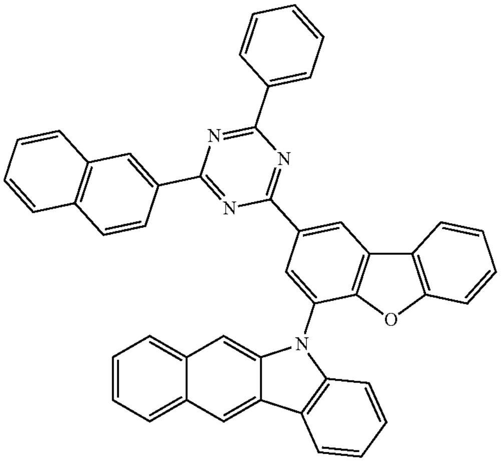
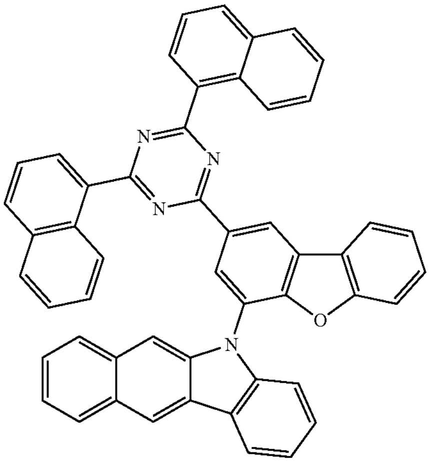

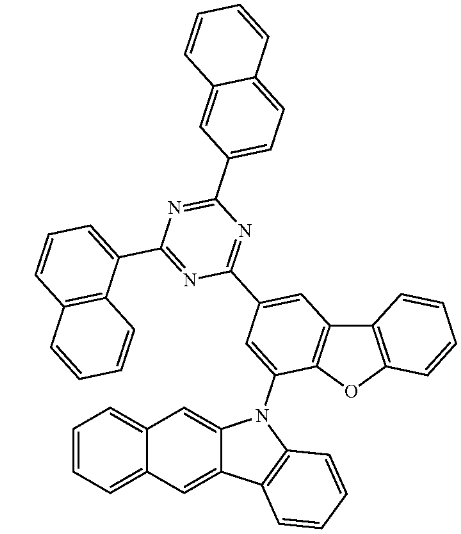
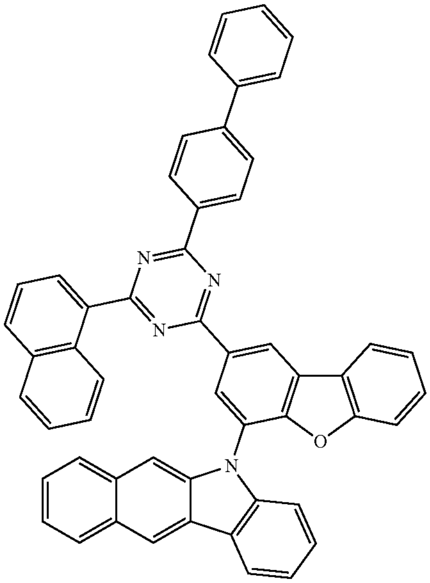
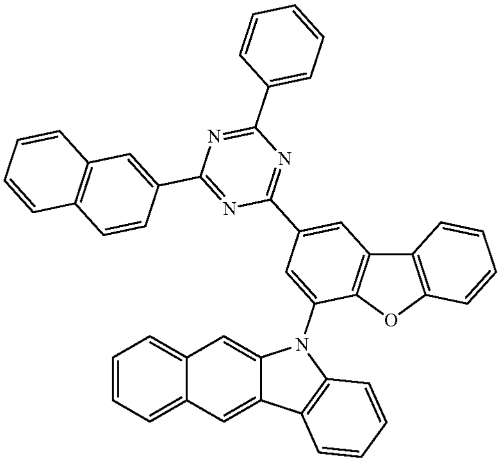
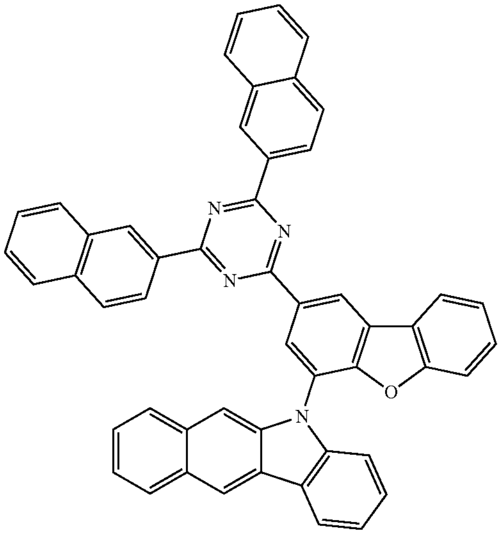
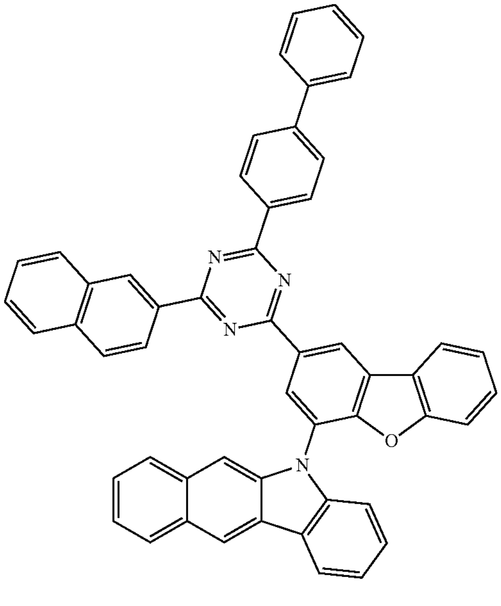
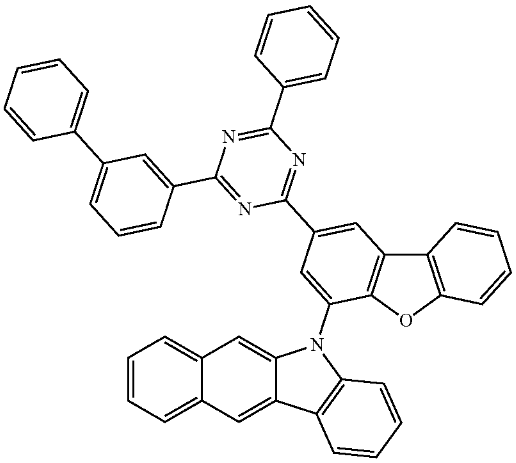

-continued
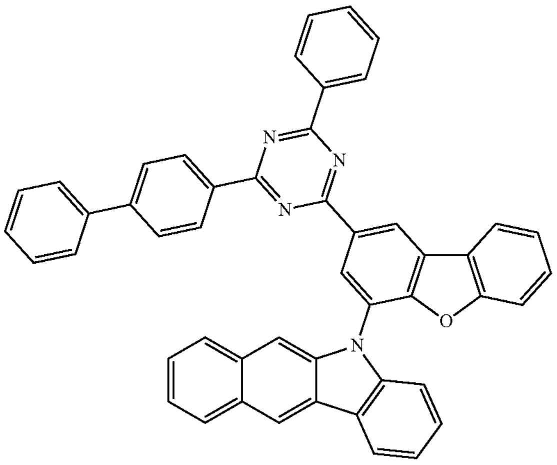
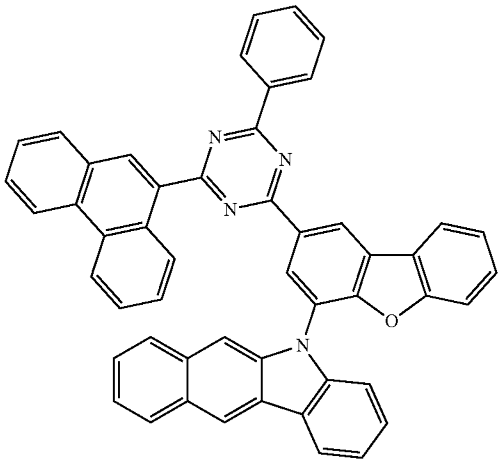
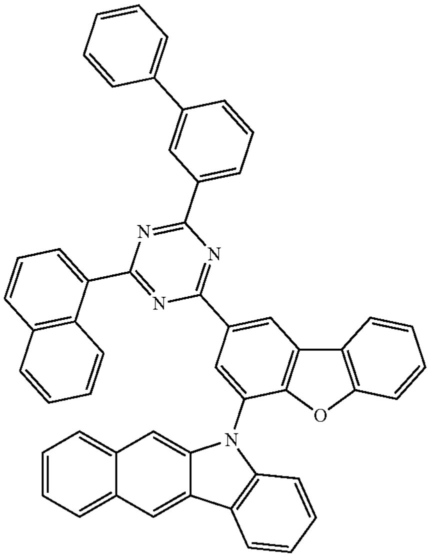
-continued
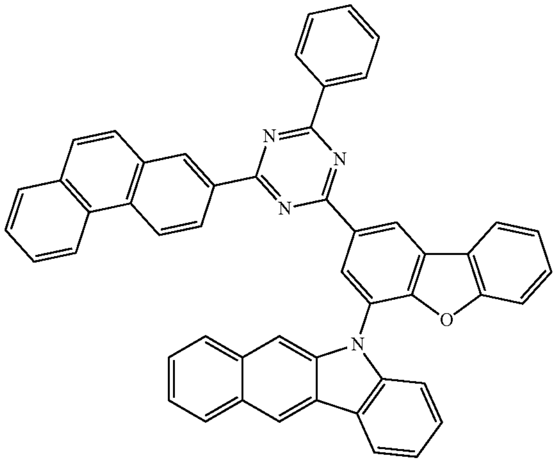
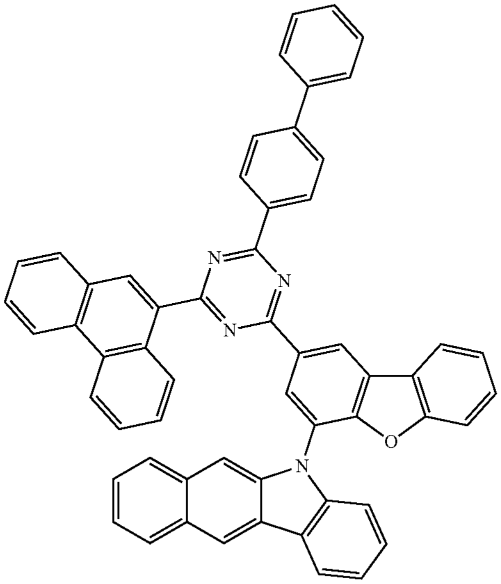
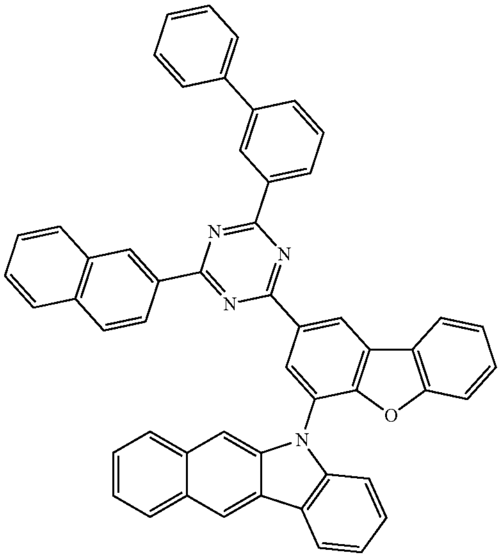

-continued
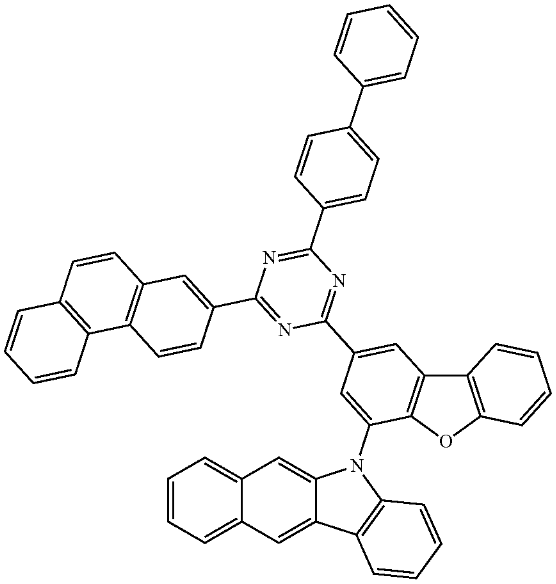
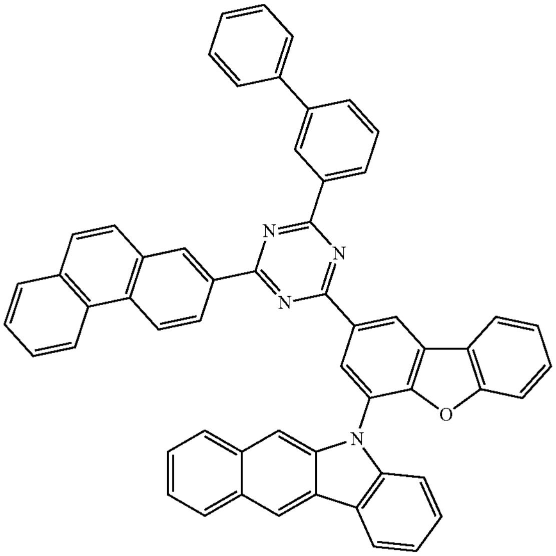
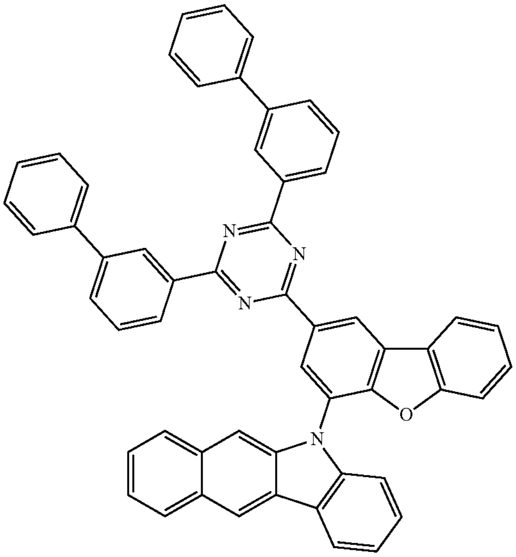
-continued
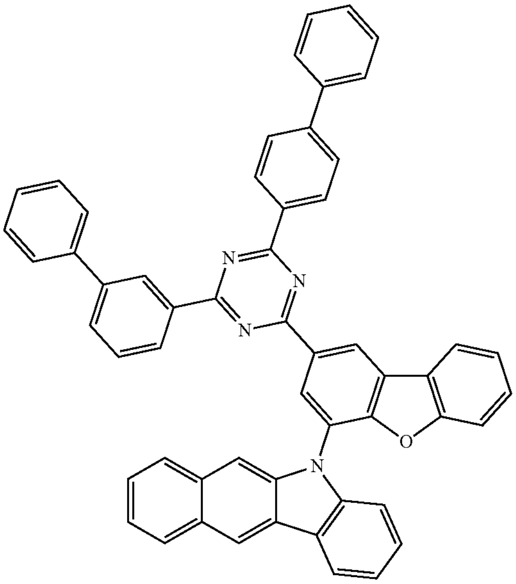
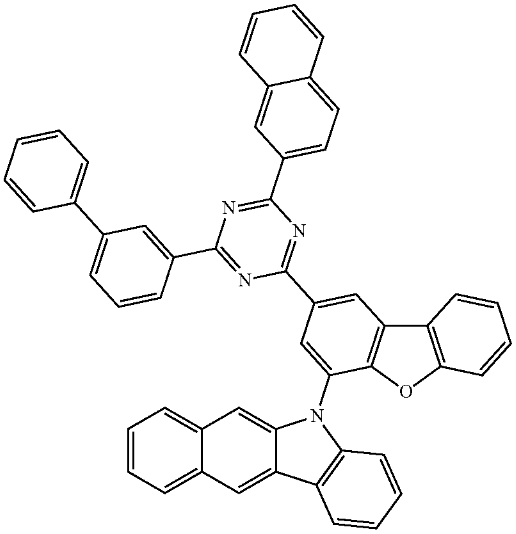
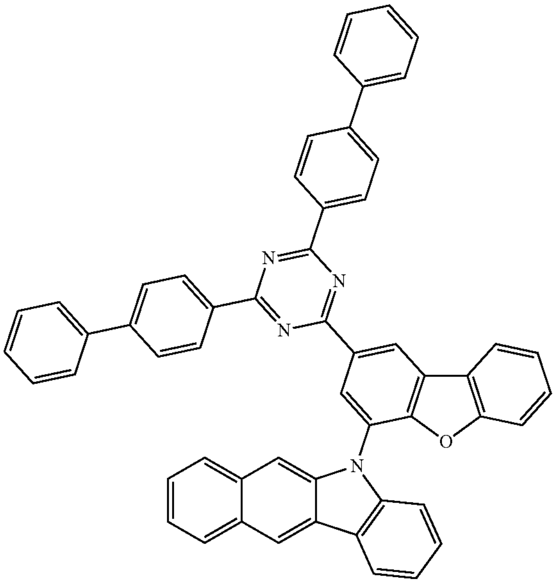

-continued
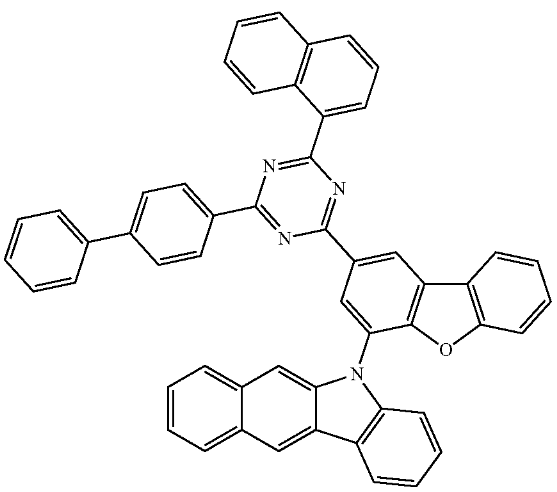
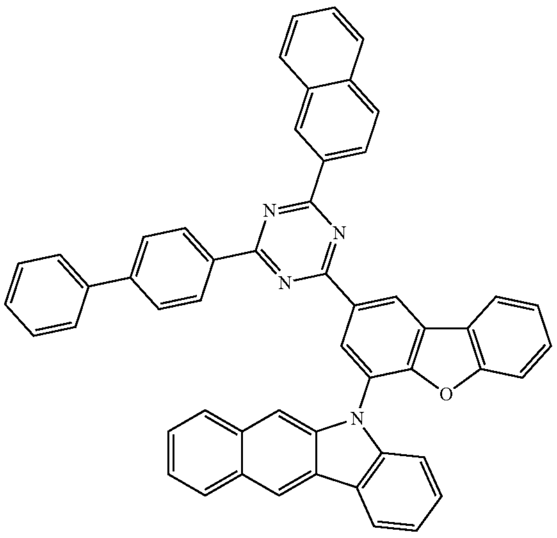
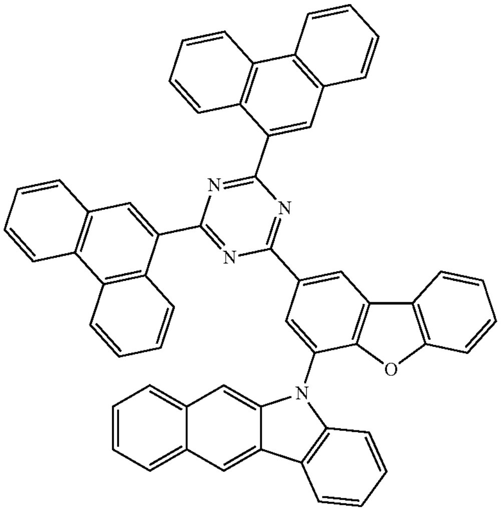
-continued
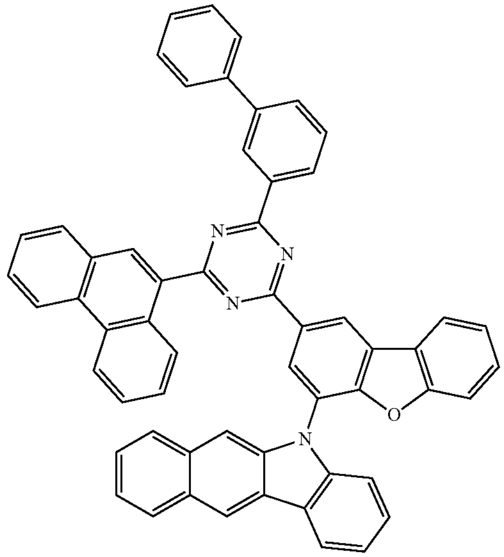
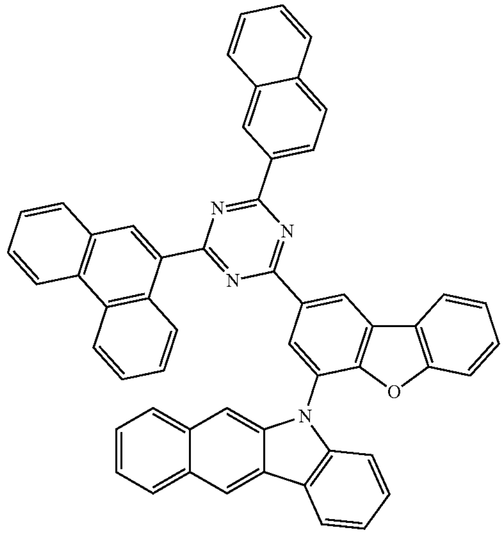
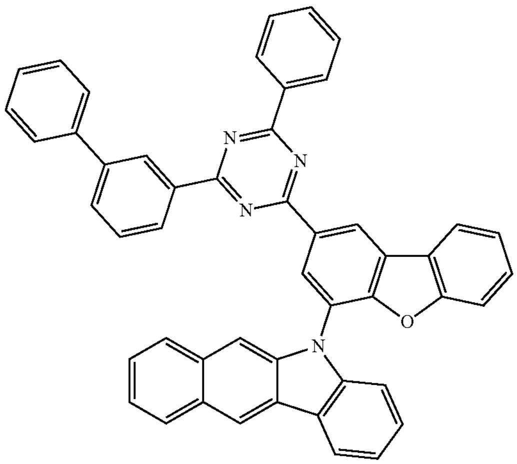

-continued
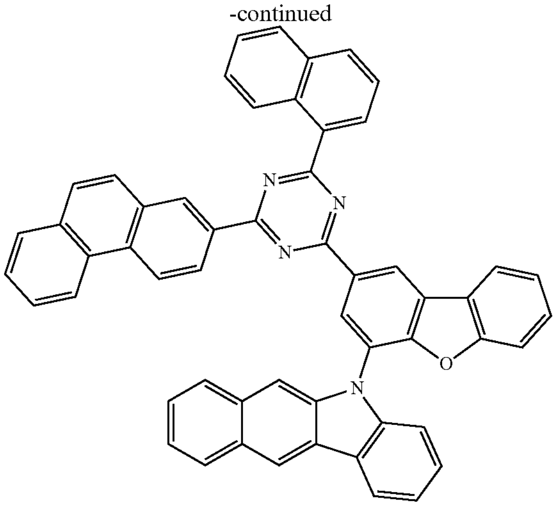
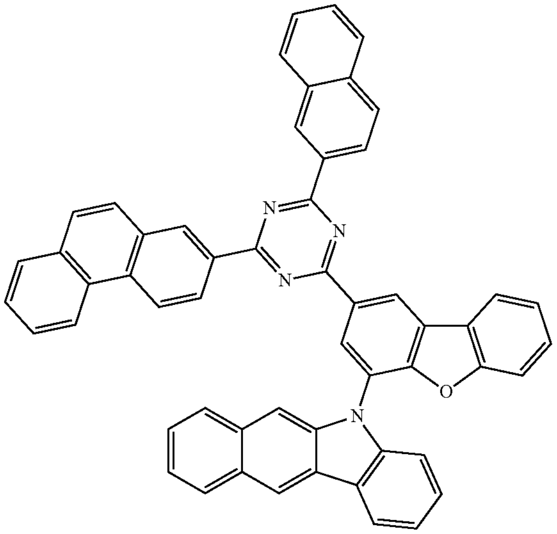
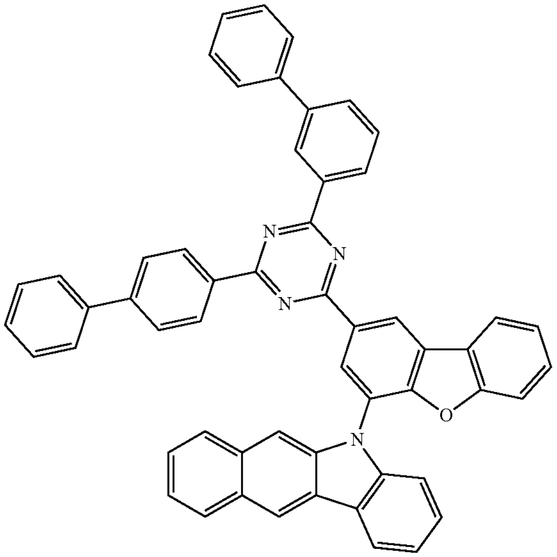
-continued
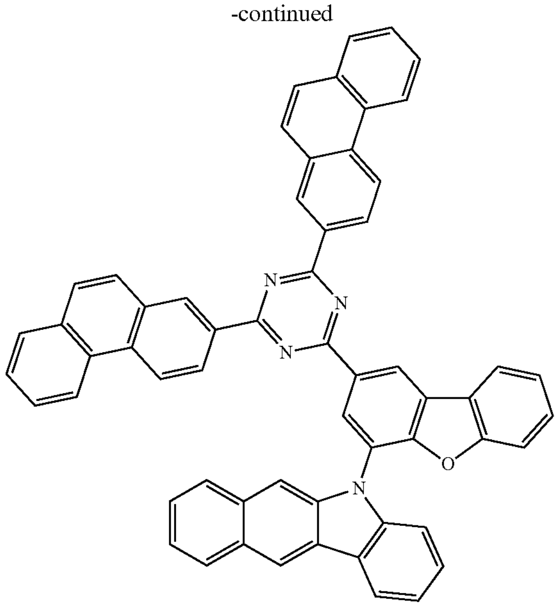
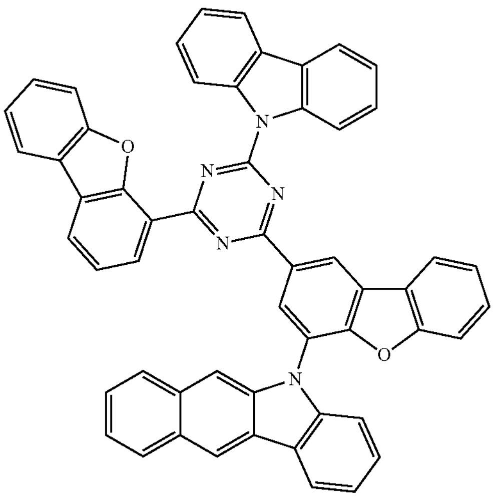
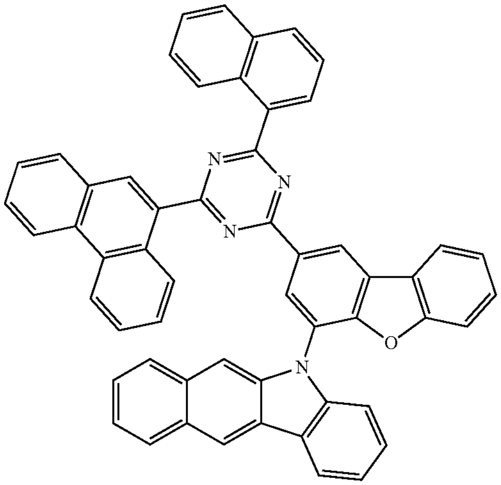

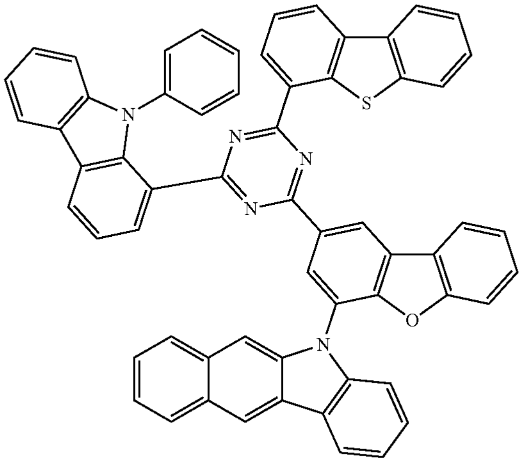
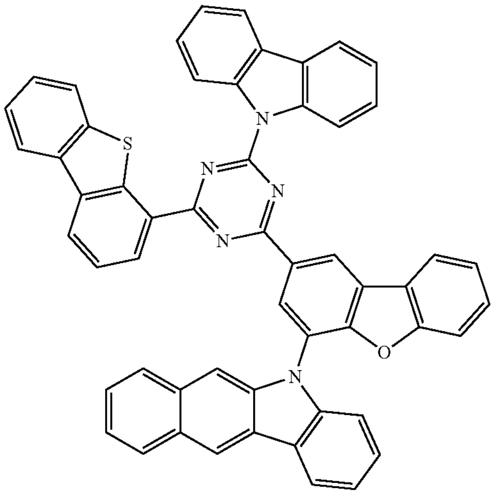
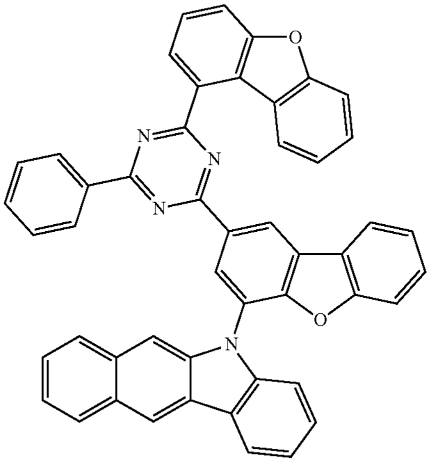
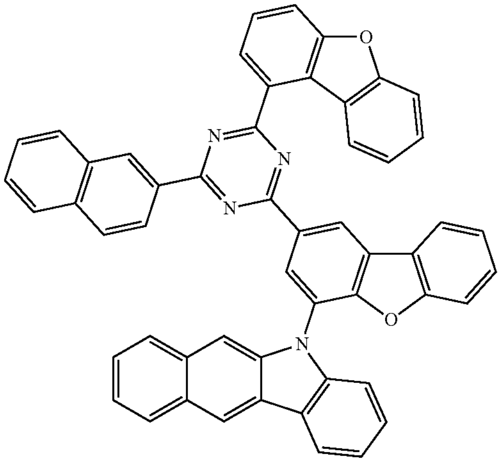
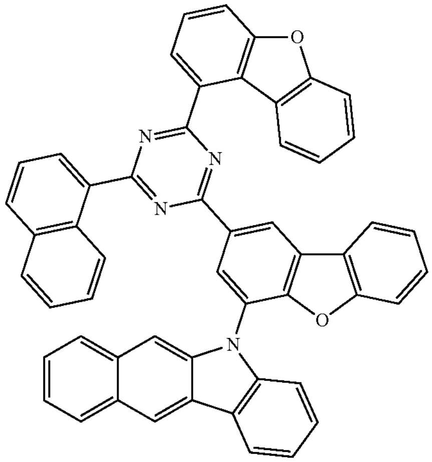
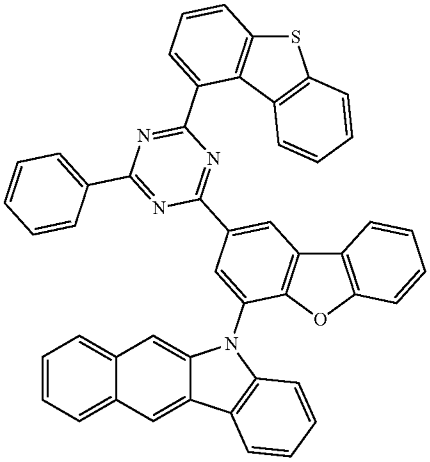

-continued
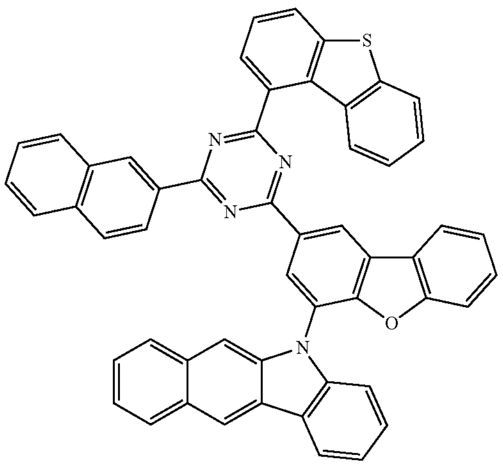
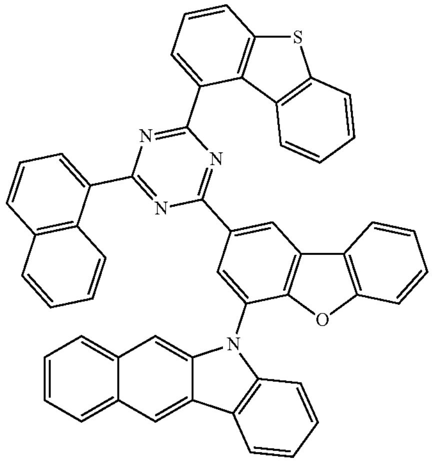
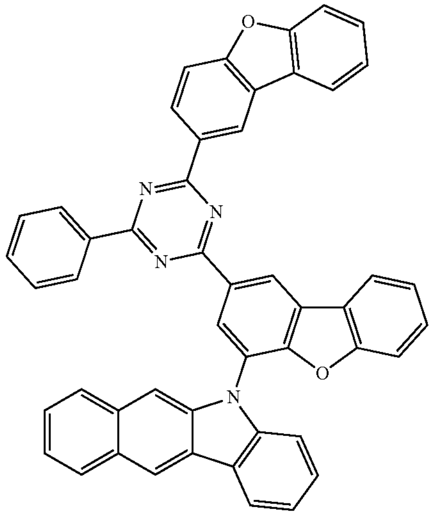
-continued
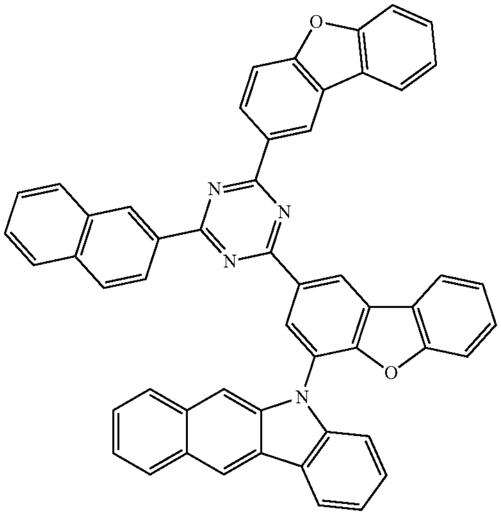
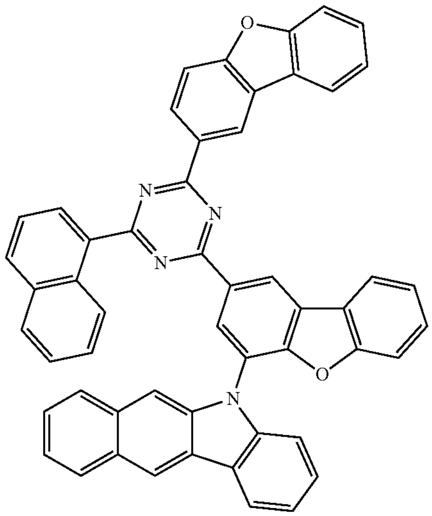
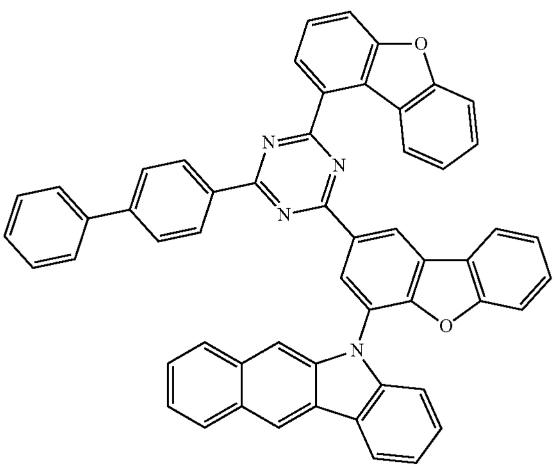

-continued
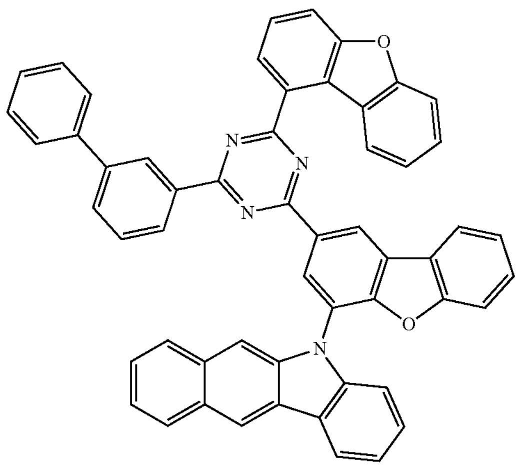
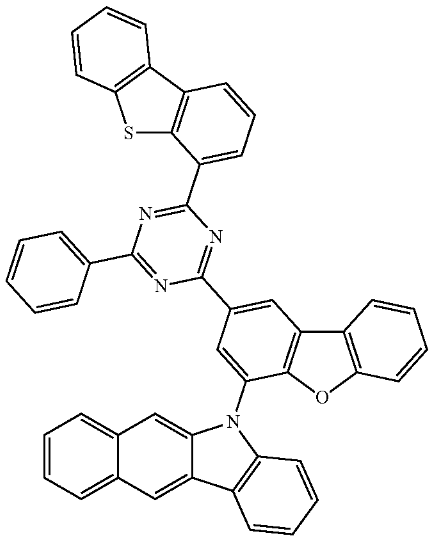
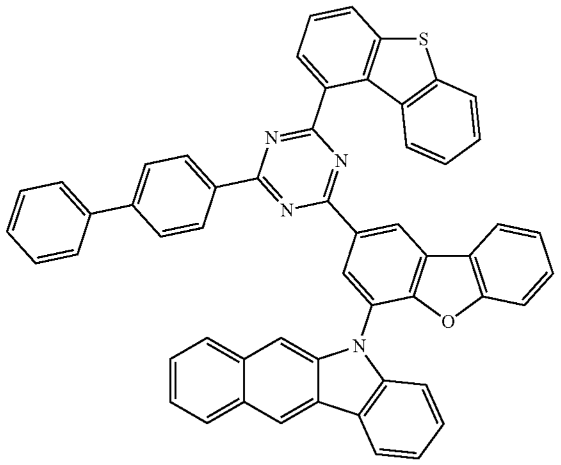
-continued
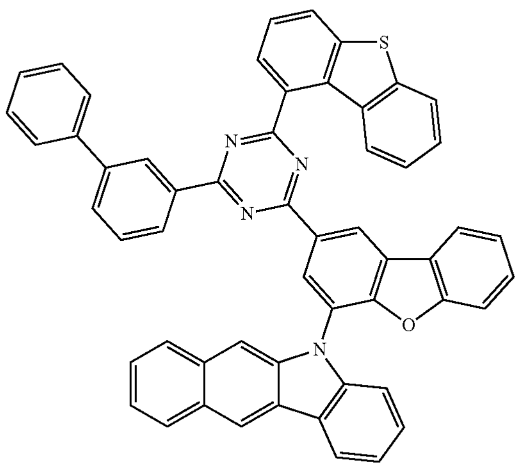
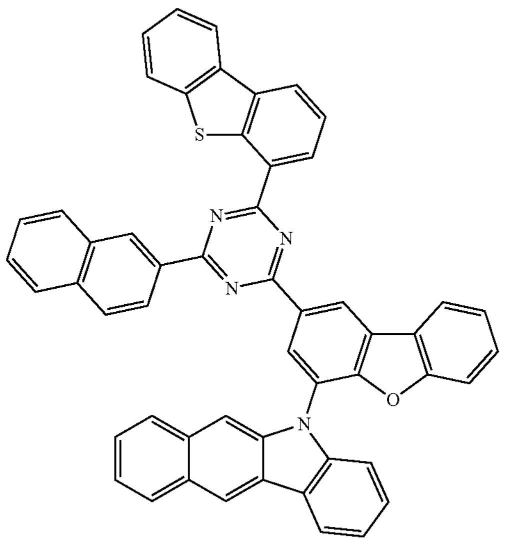
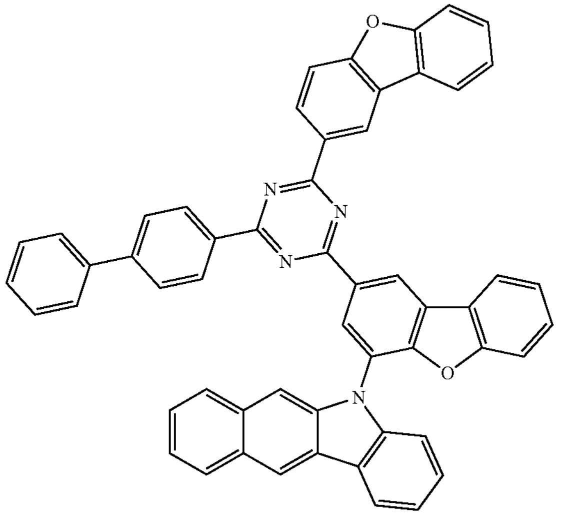

-continued
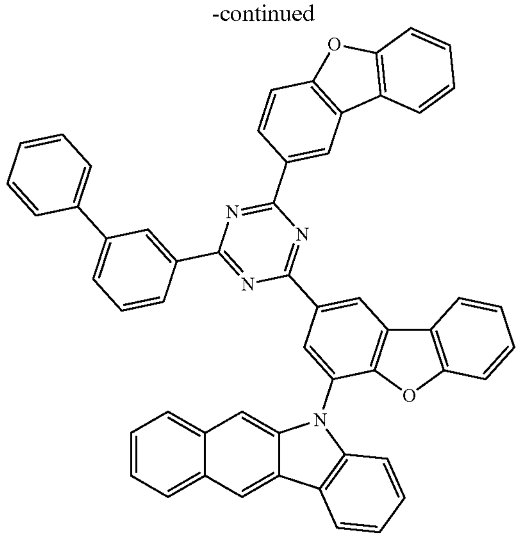
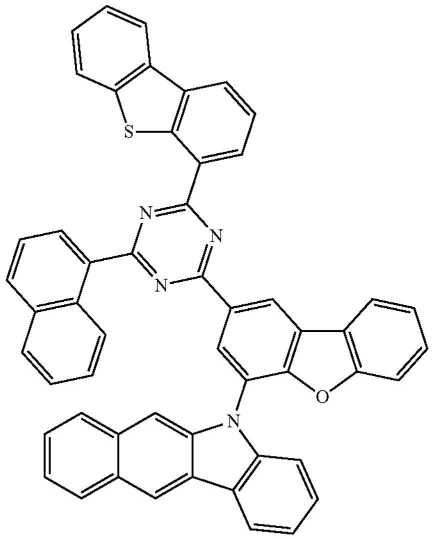
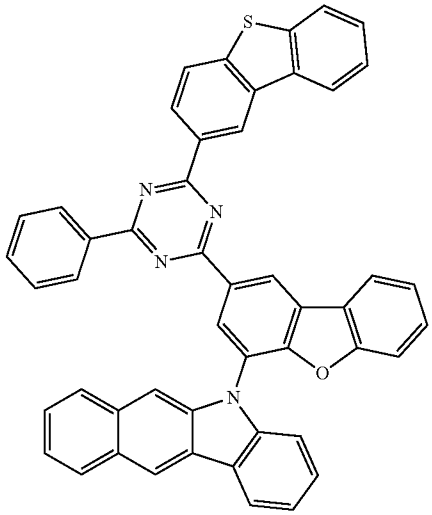
-continued
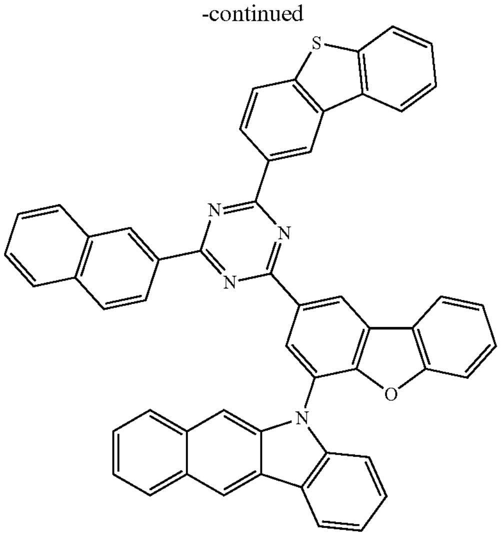
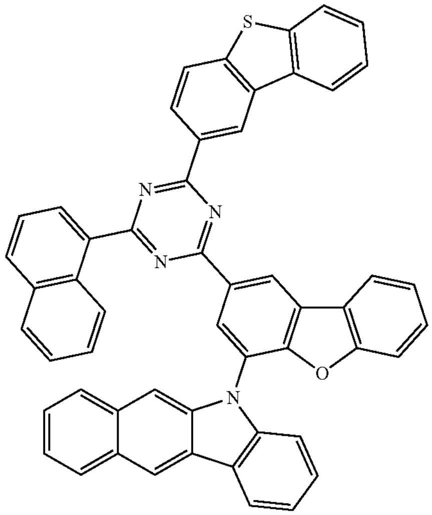
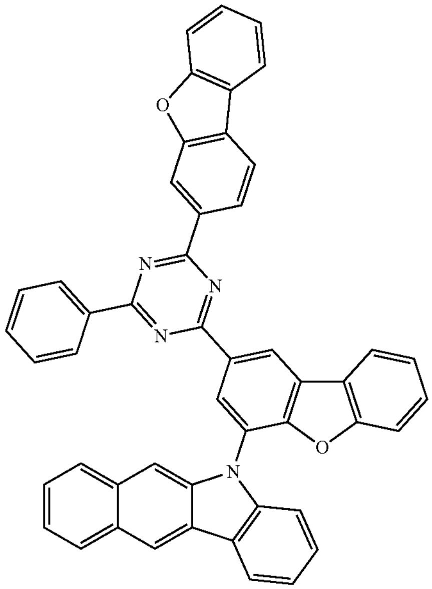

-continued
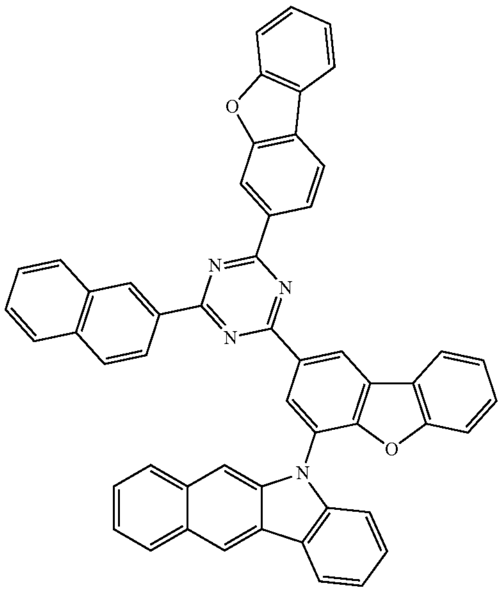
-continued
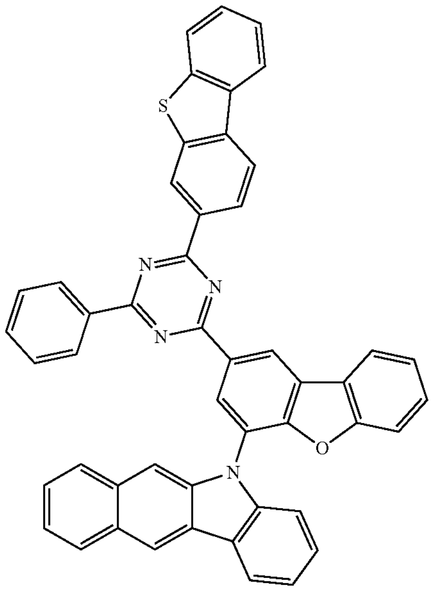
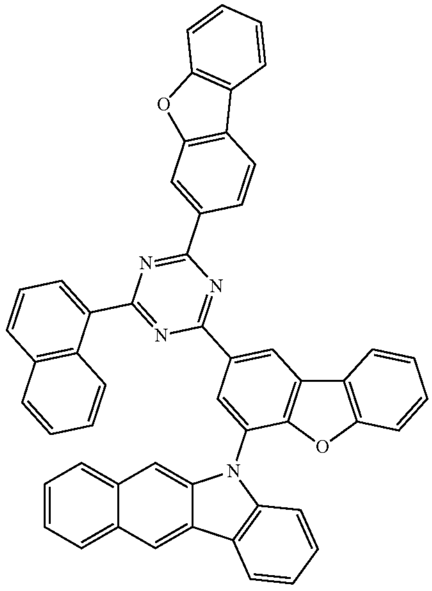
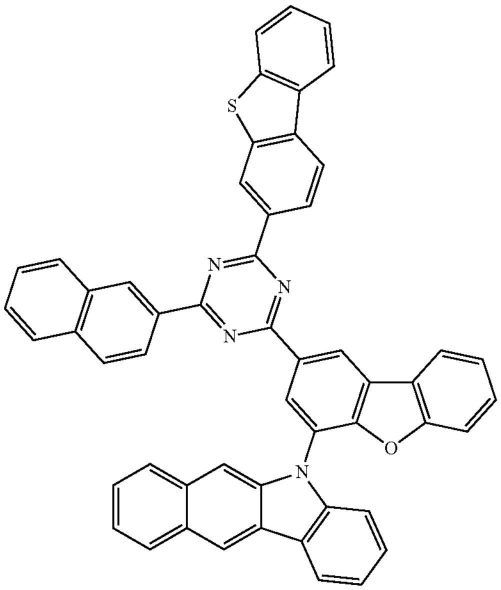

-continued
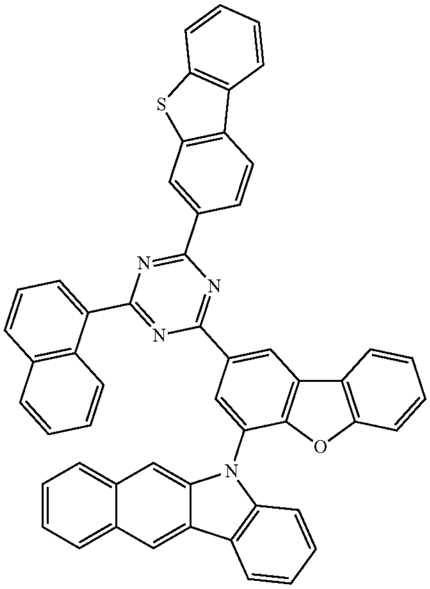
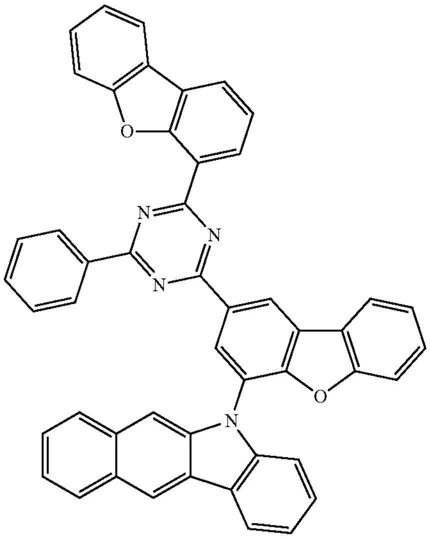
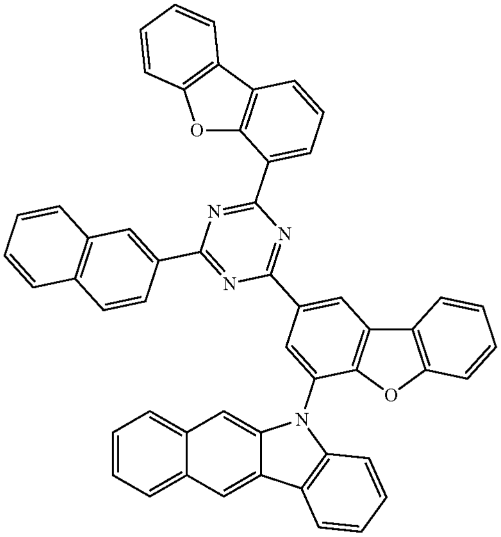
-continued
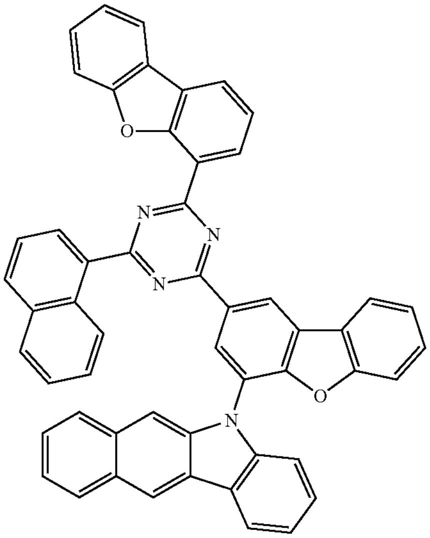
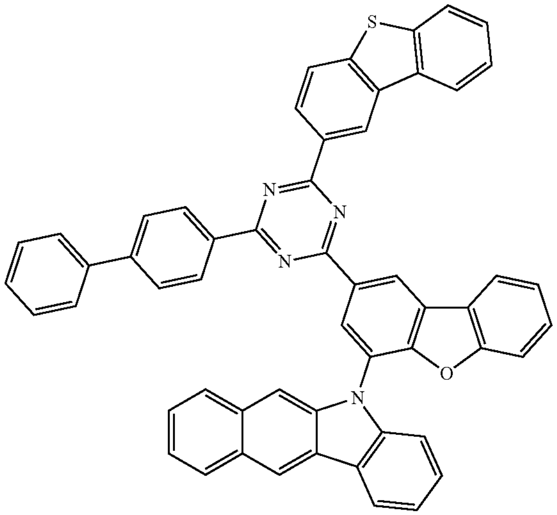
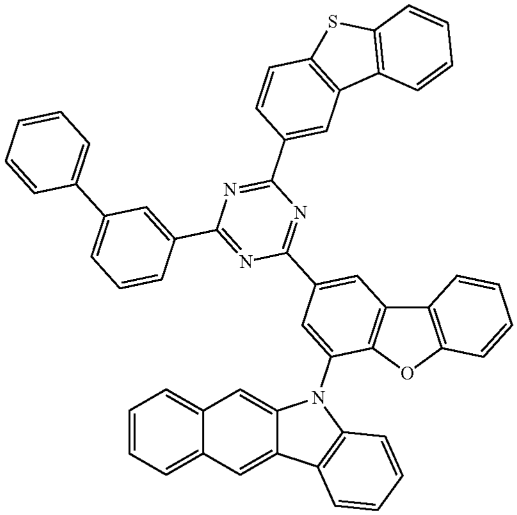

-continued
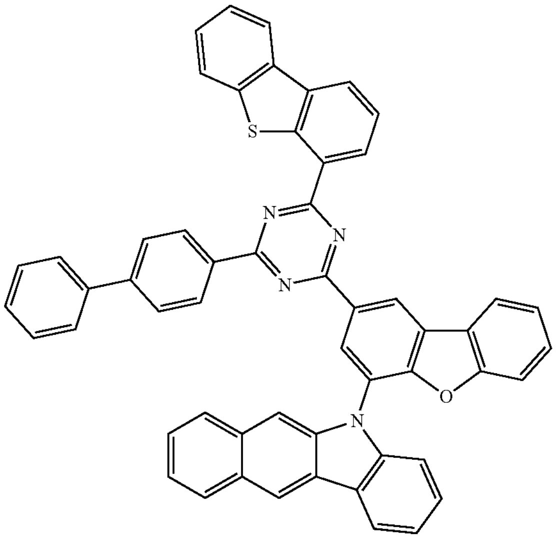
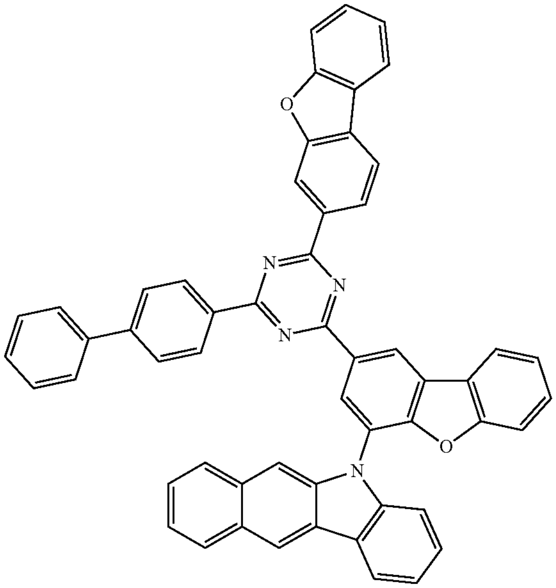
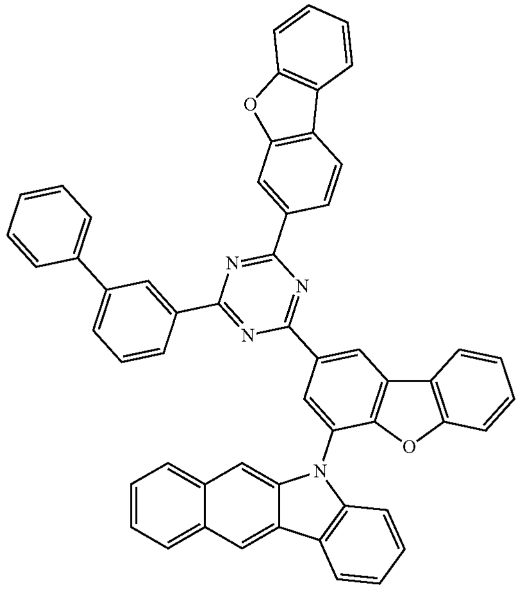
-continued
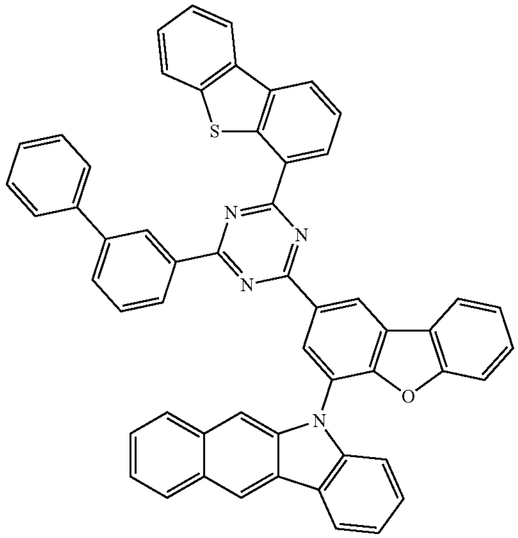
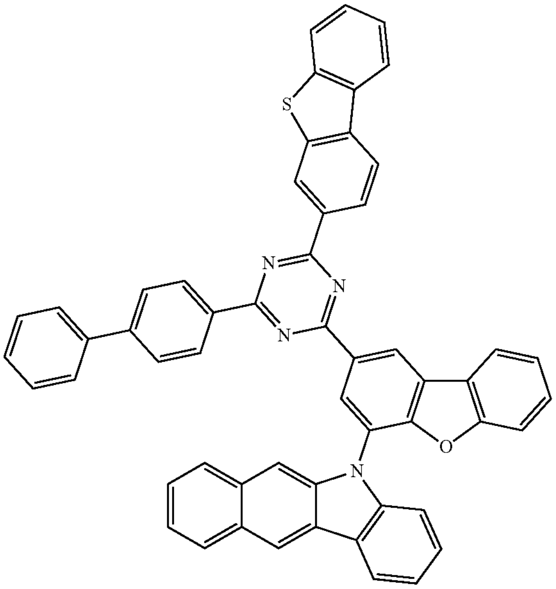
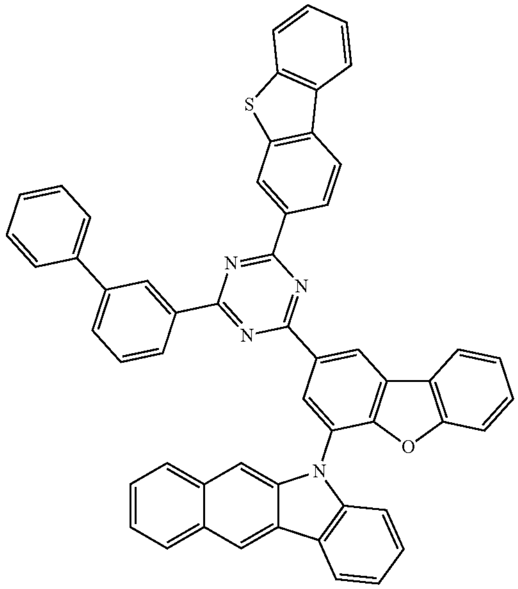

-continued
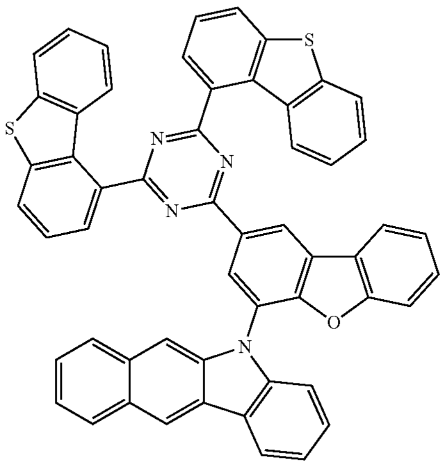
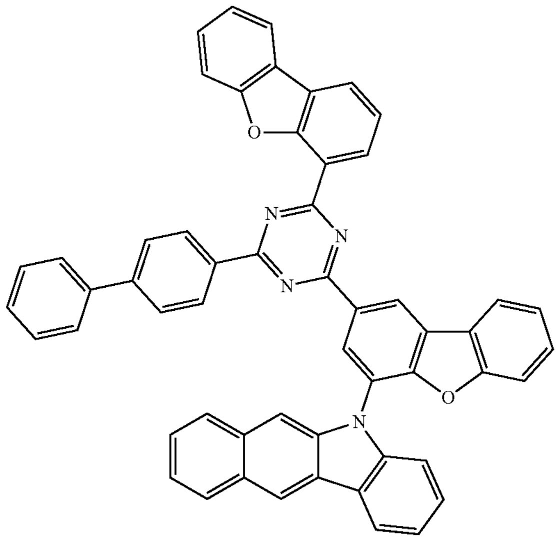
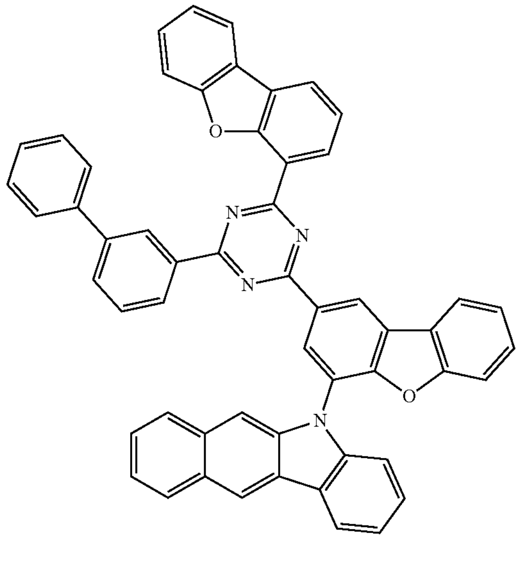
-continued
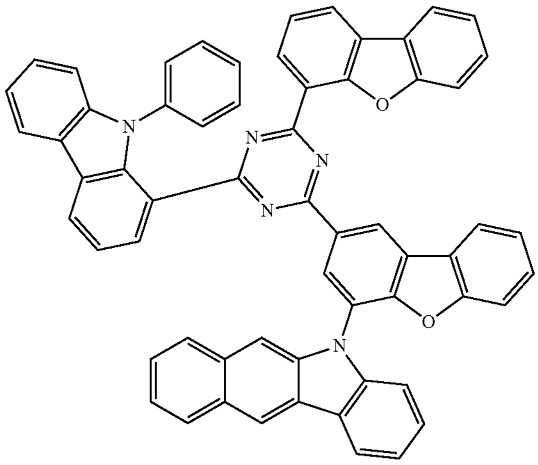
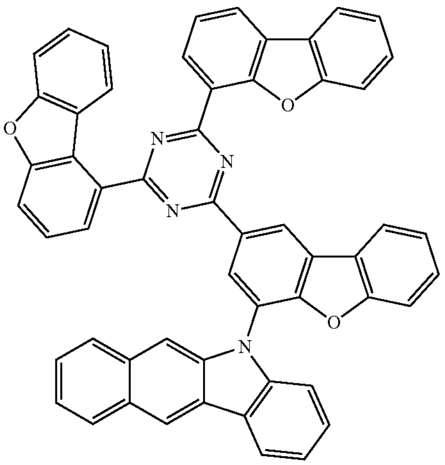
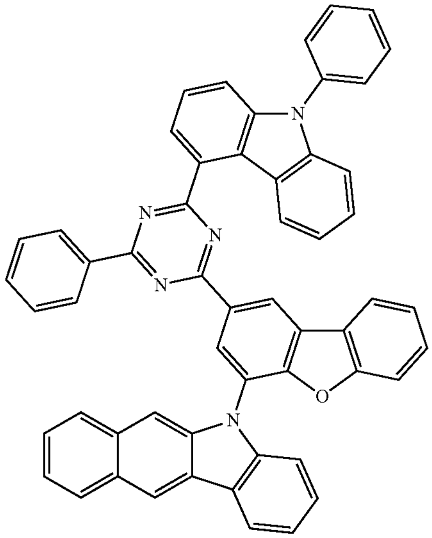

-continued
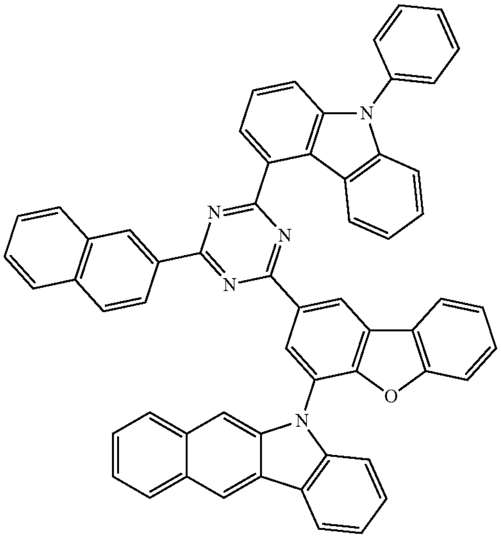
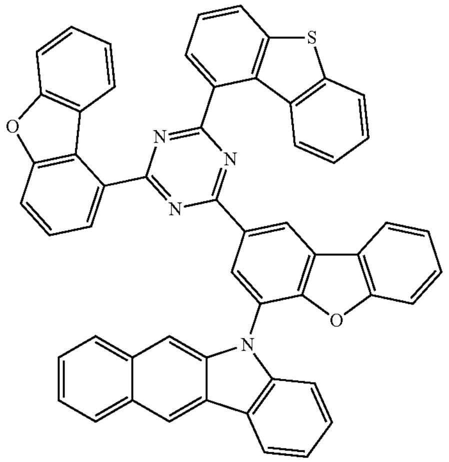
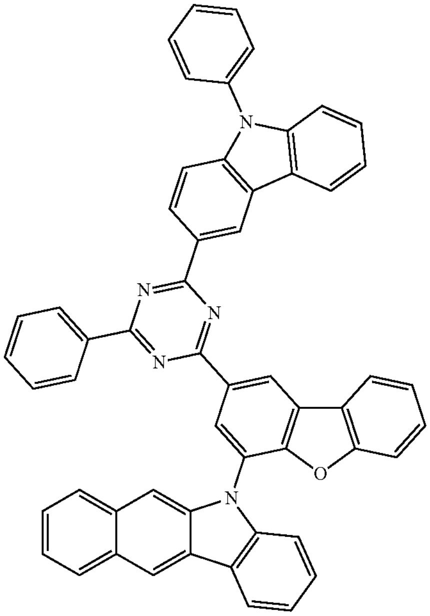
-continued
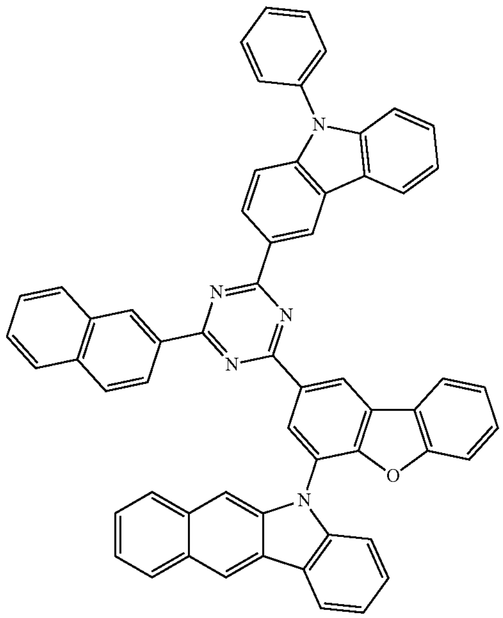
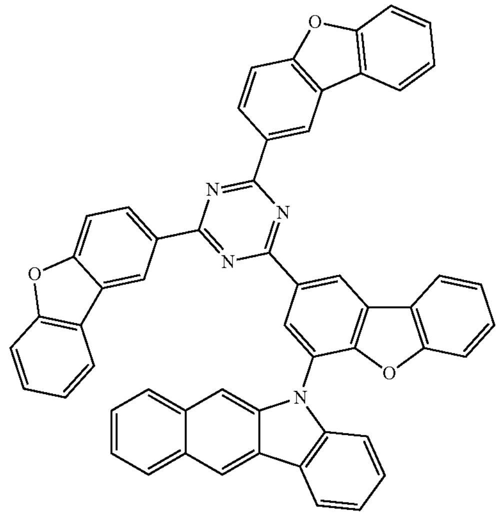
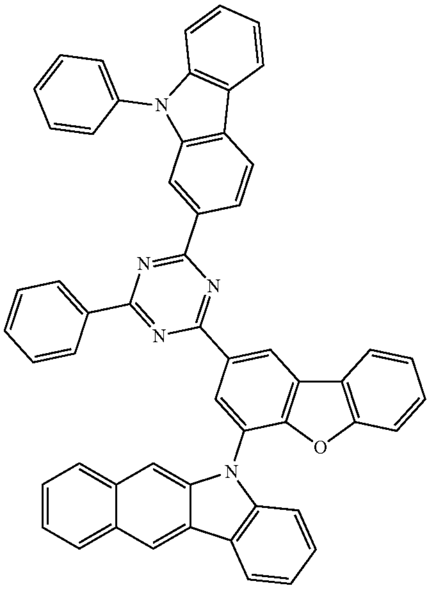

-continued
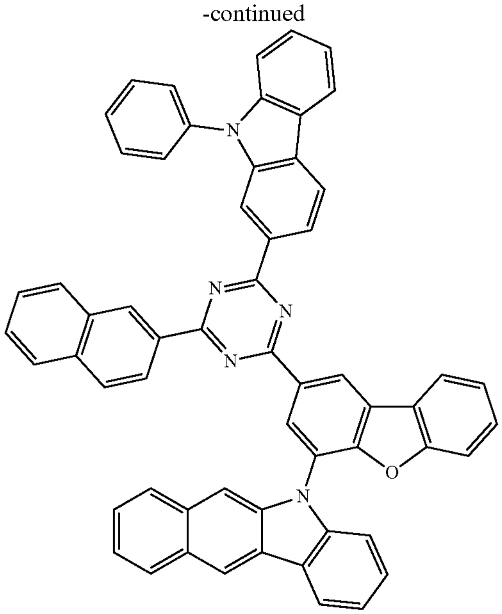
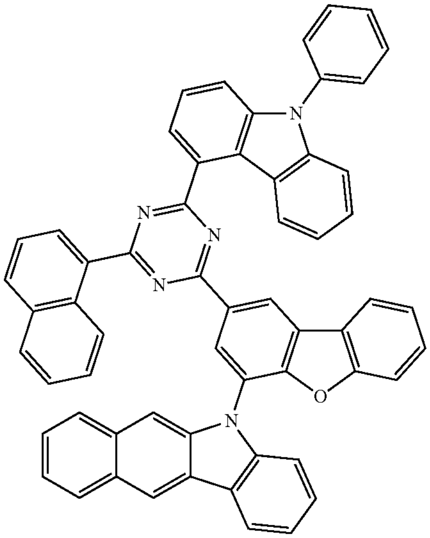
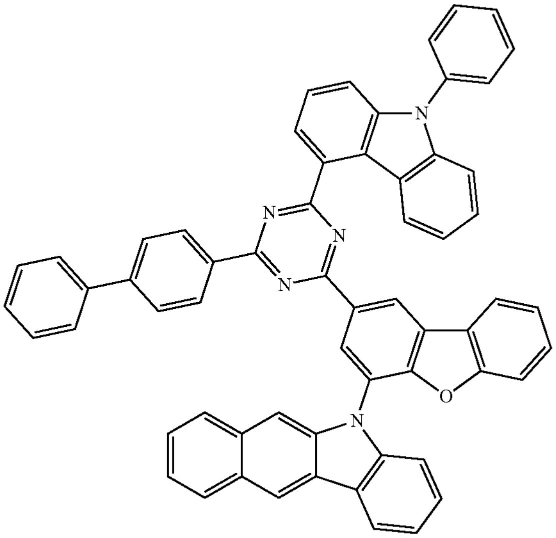
-continued
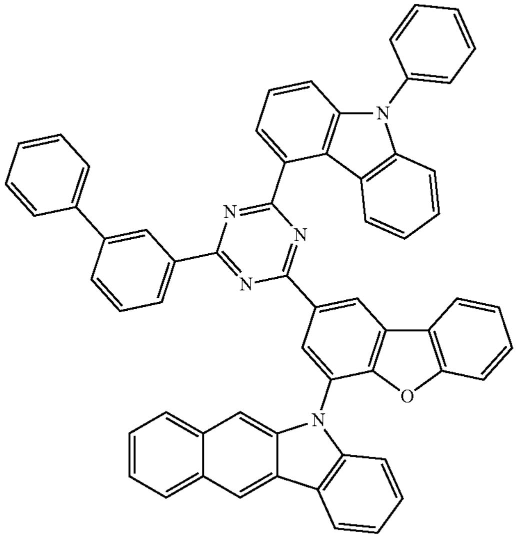
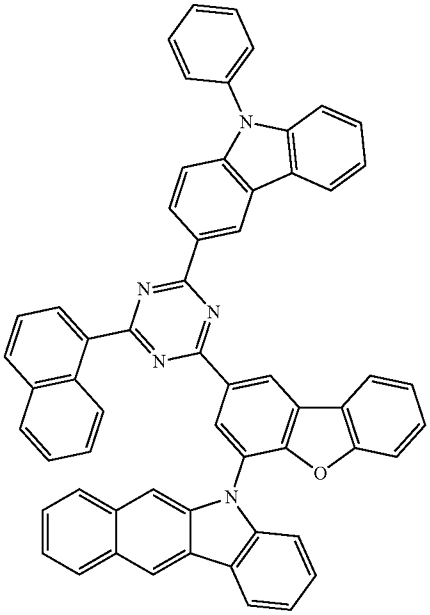

-continued
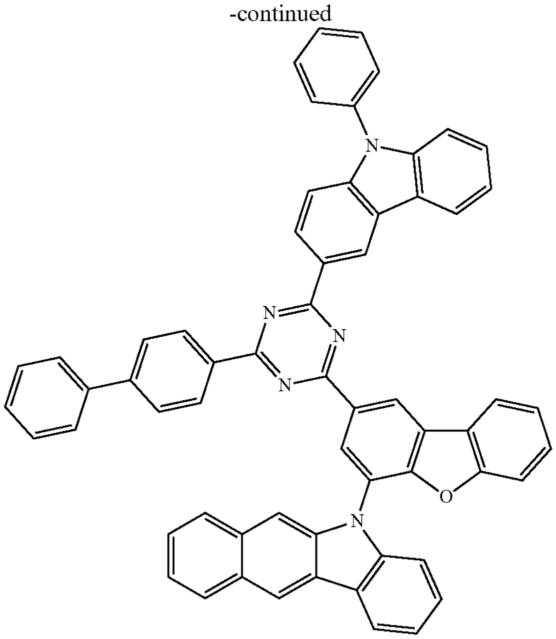
-continued
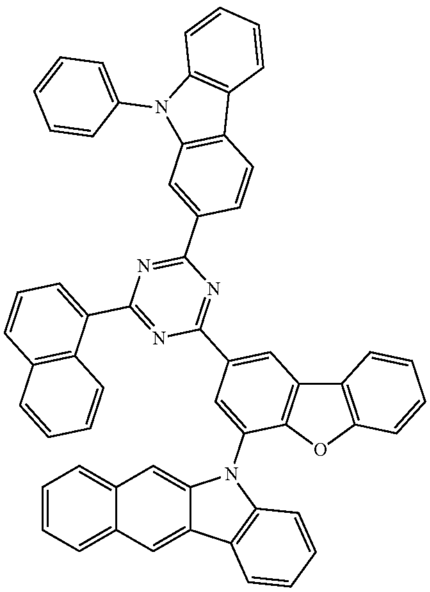
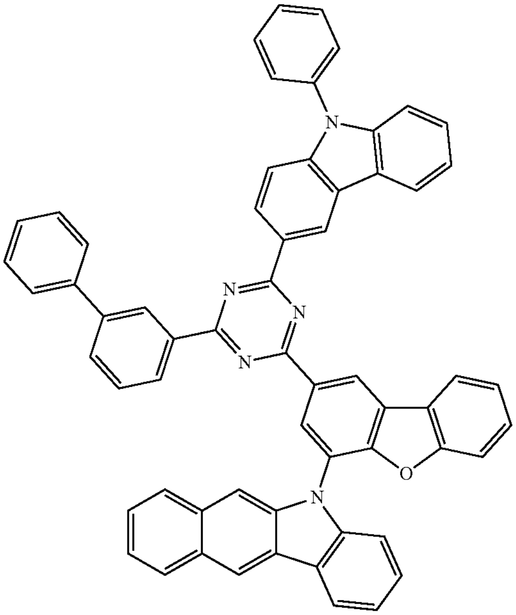
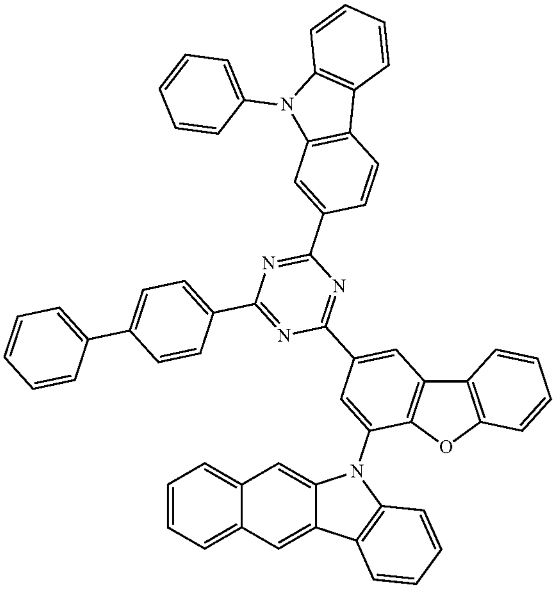

-continued
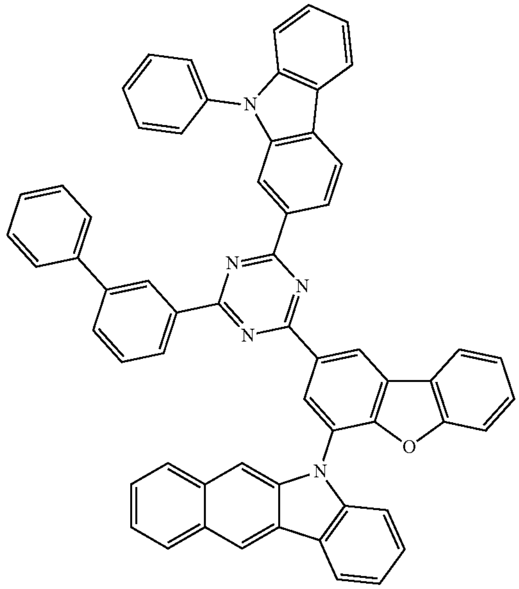
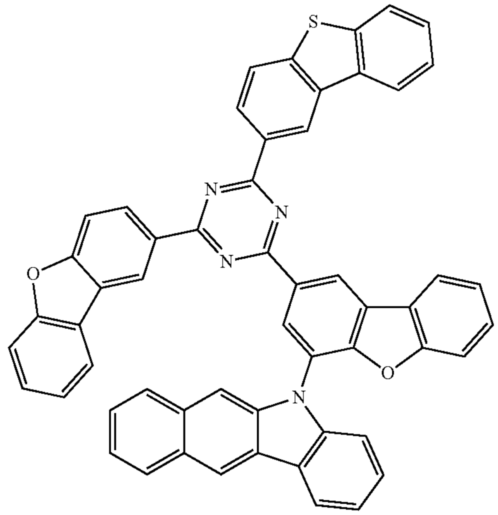
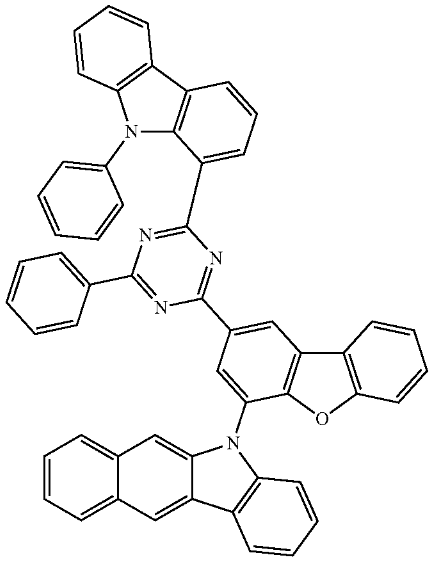
-continued
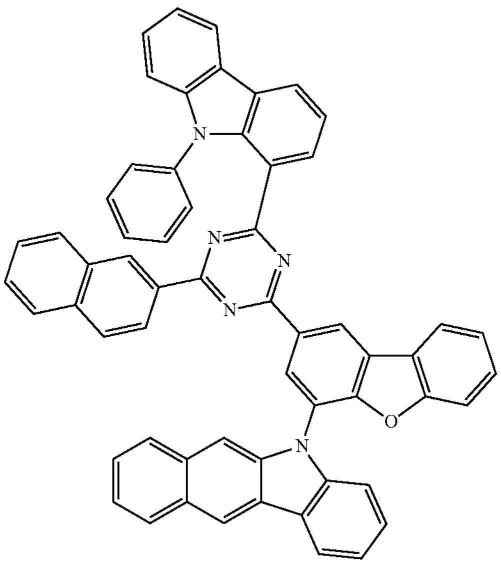
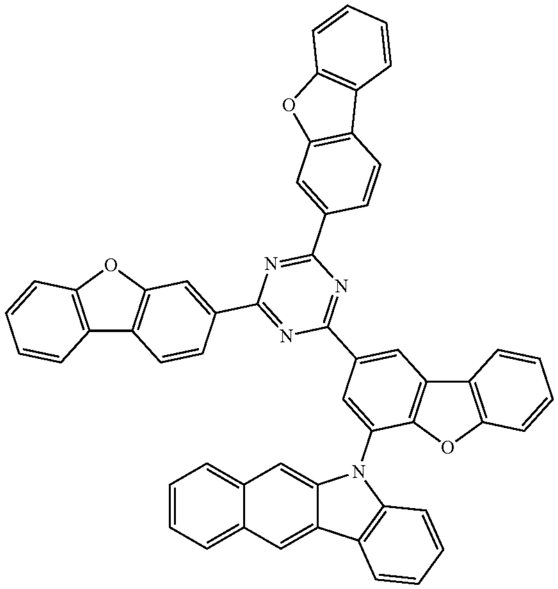
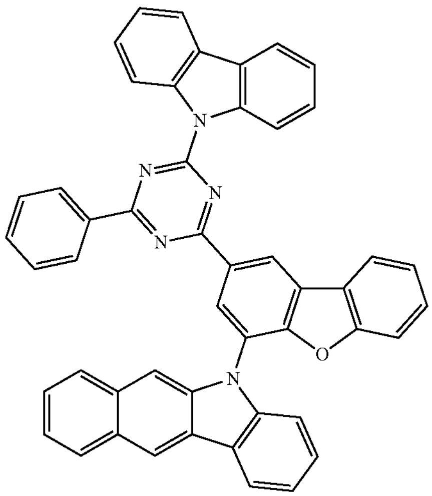

-continued
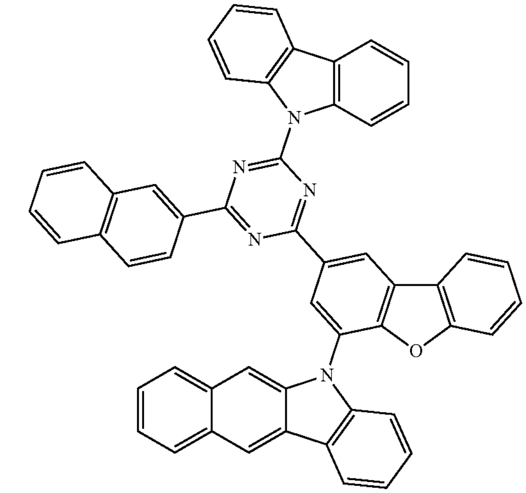
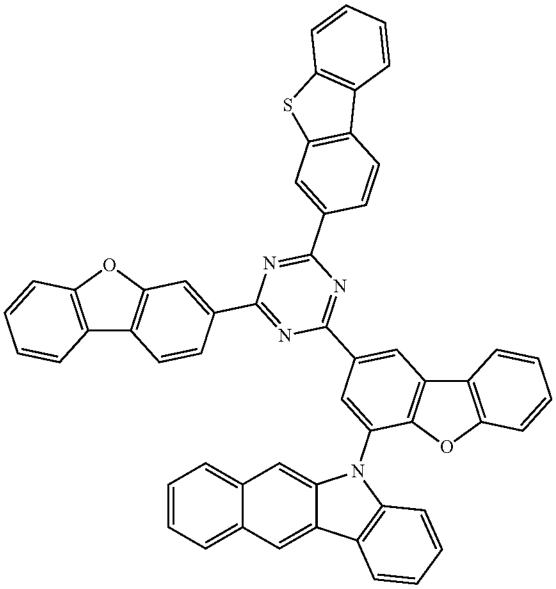
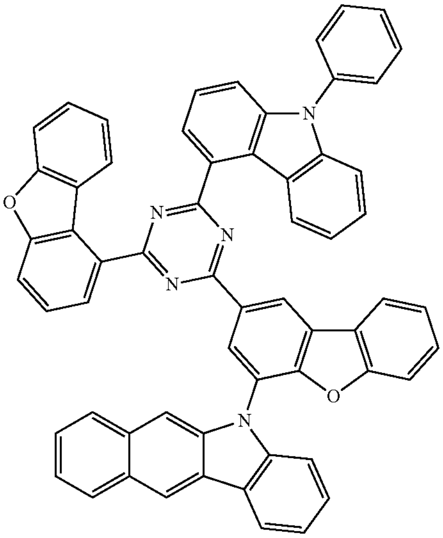
-continued
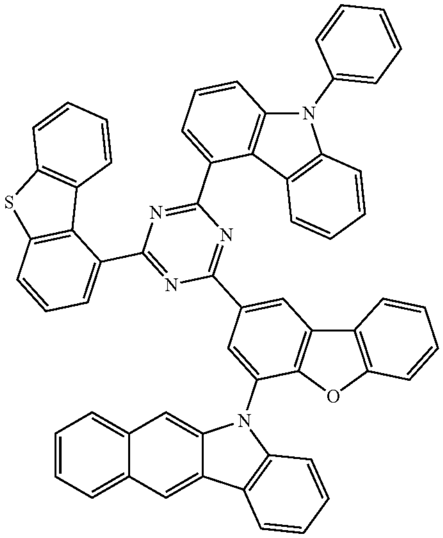
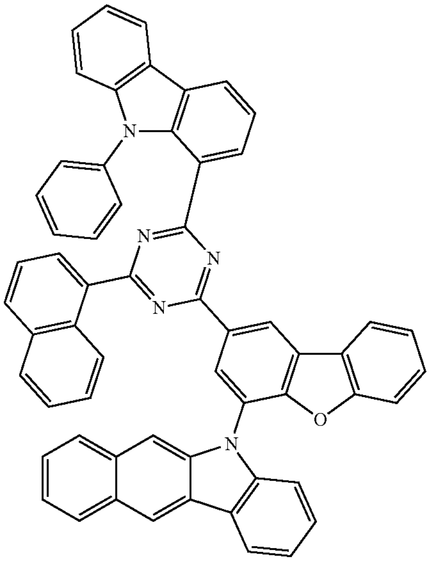
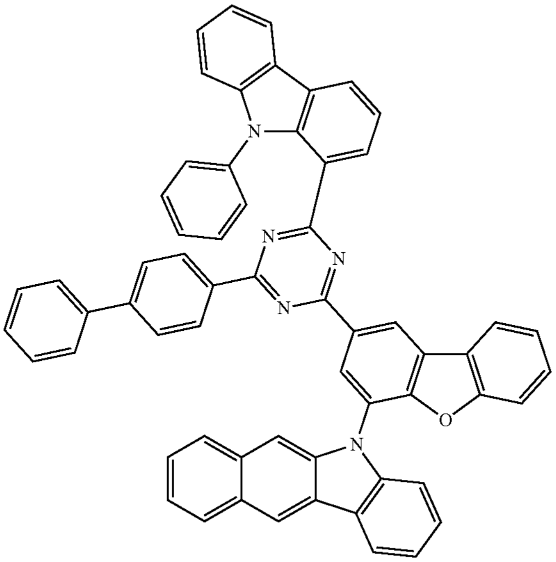

-continued
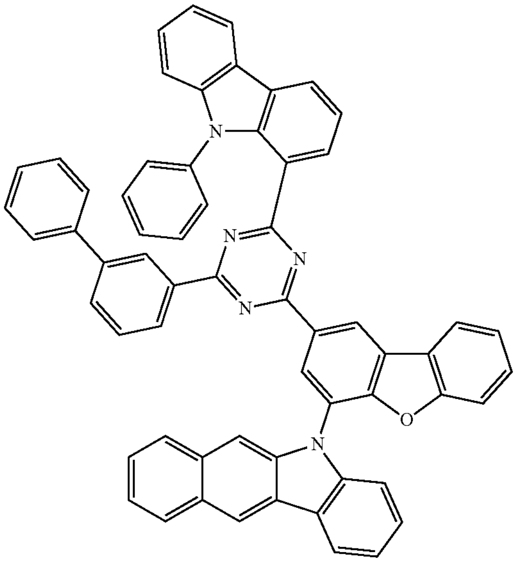
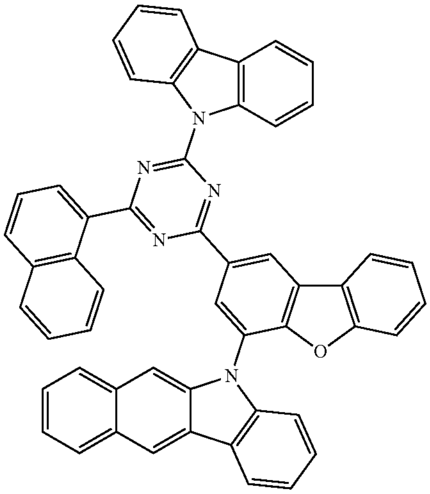
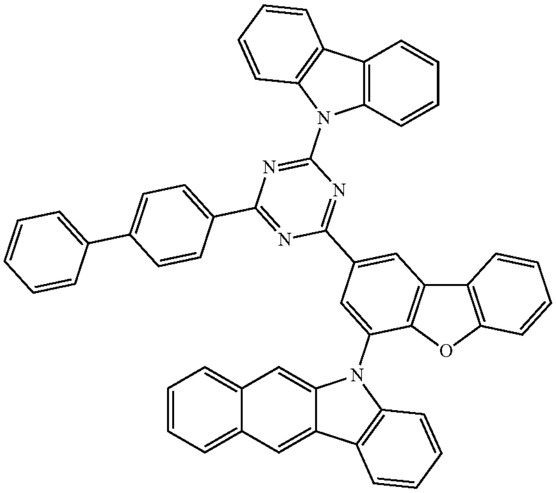
-continued
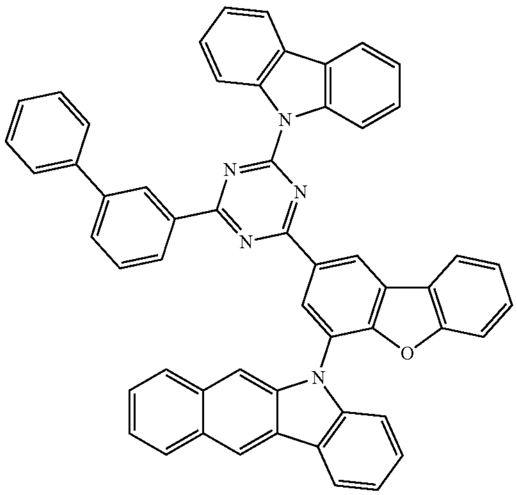
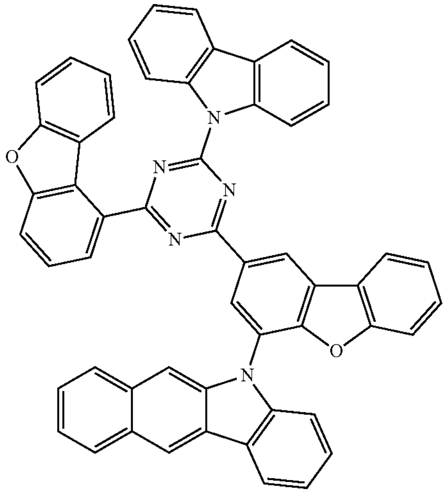
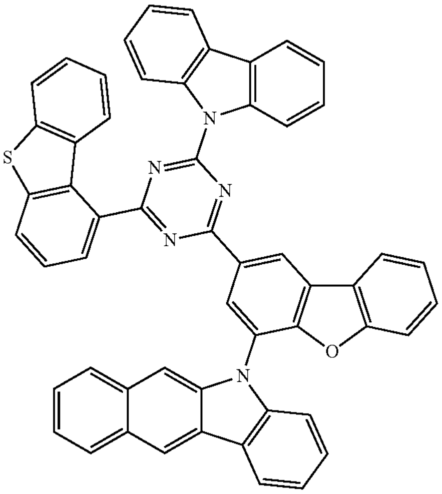

-continued
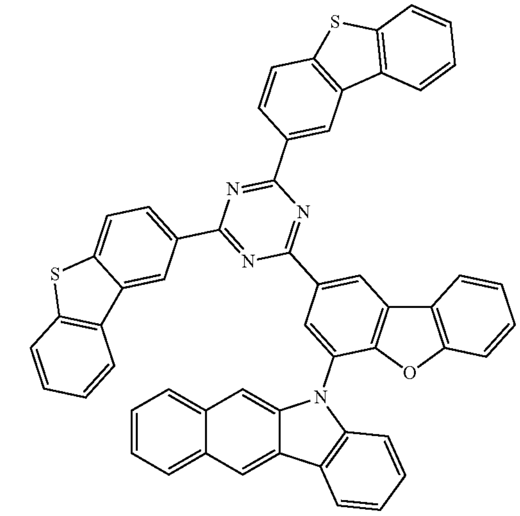
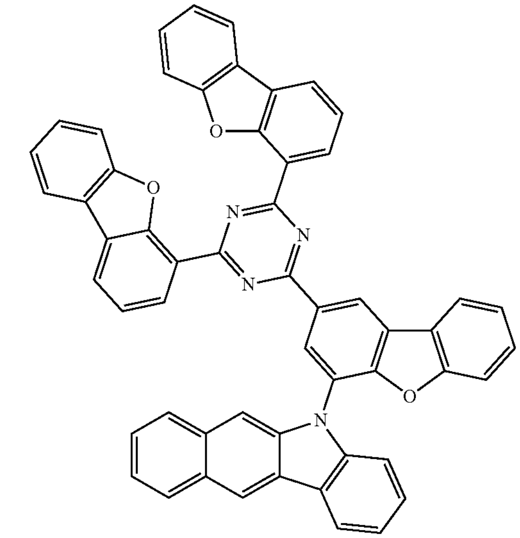
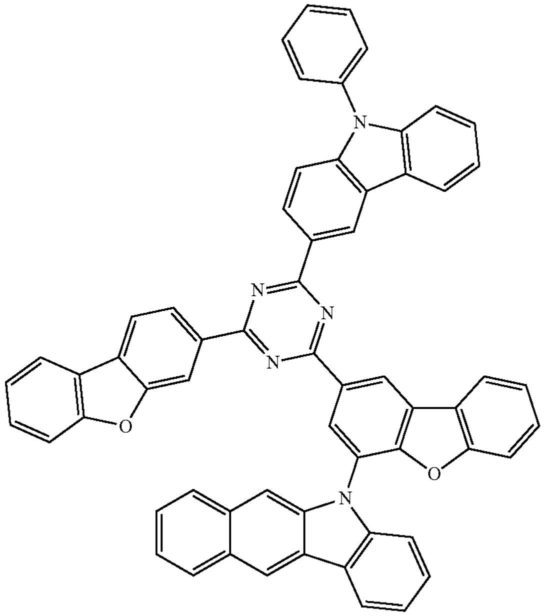
-continued
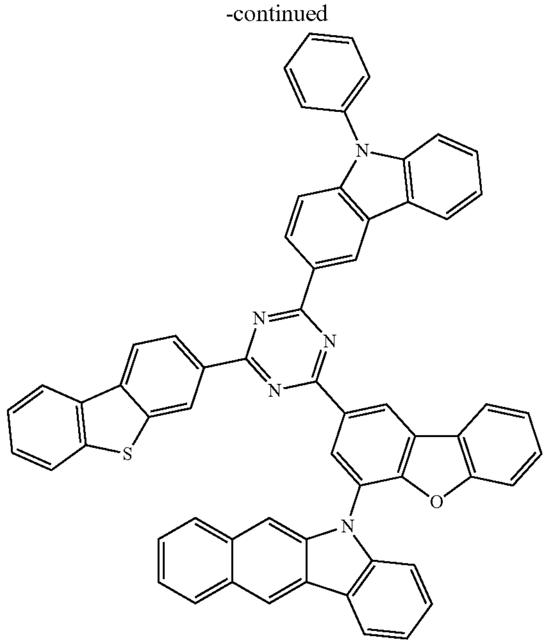
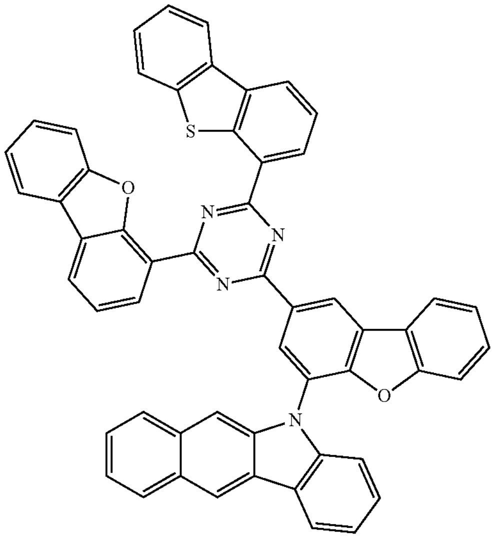

-continued
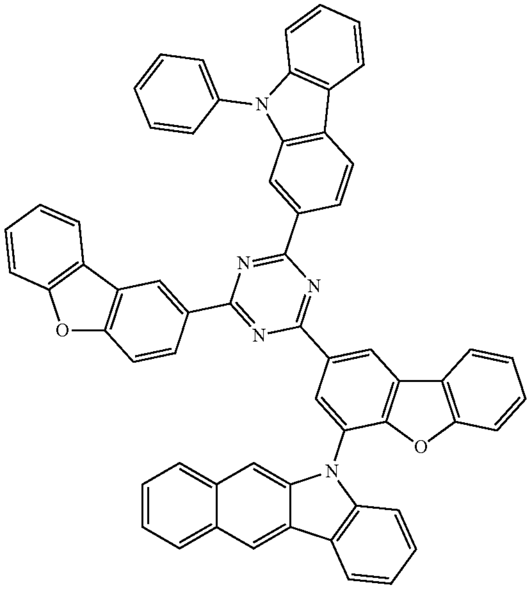
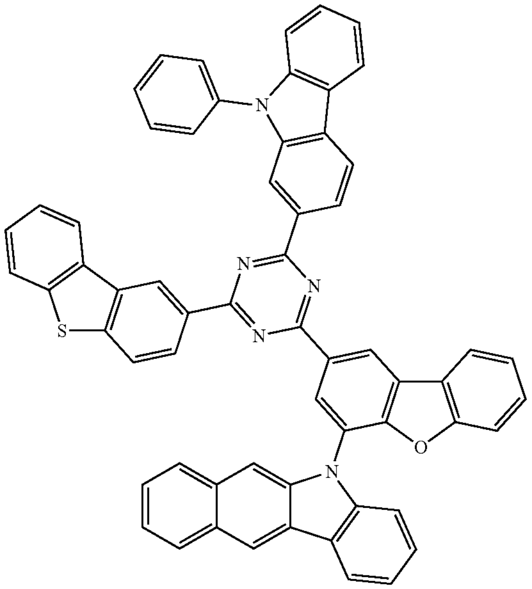
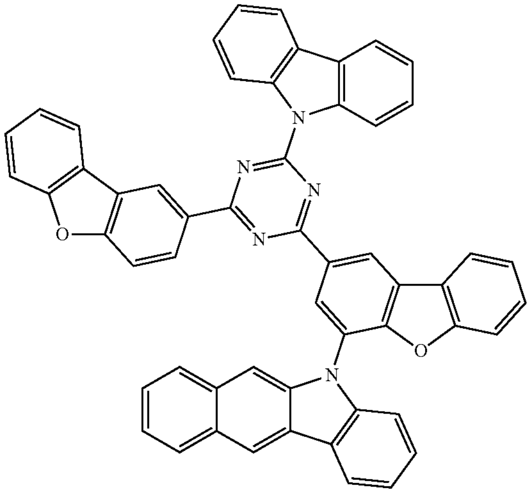
-continued
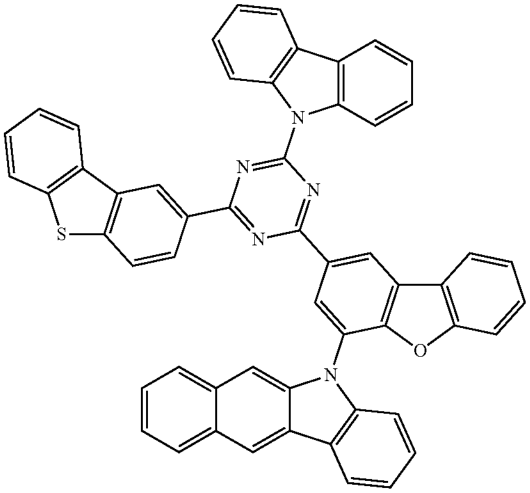
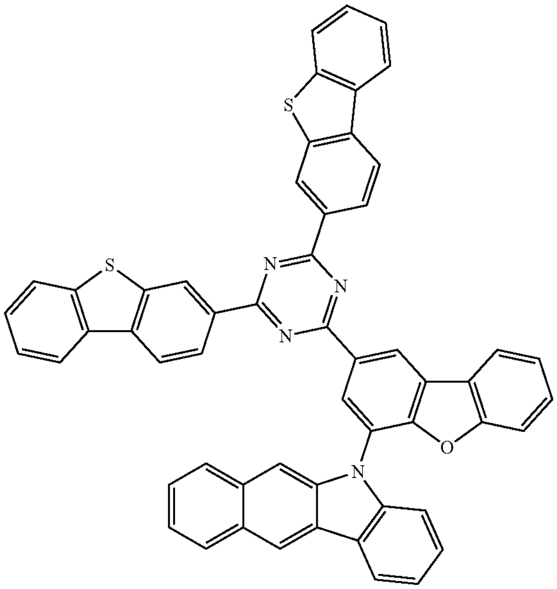
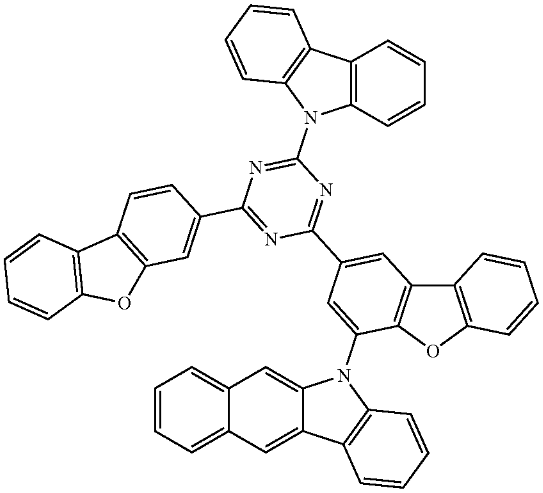

-continued
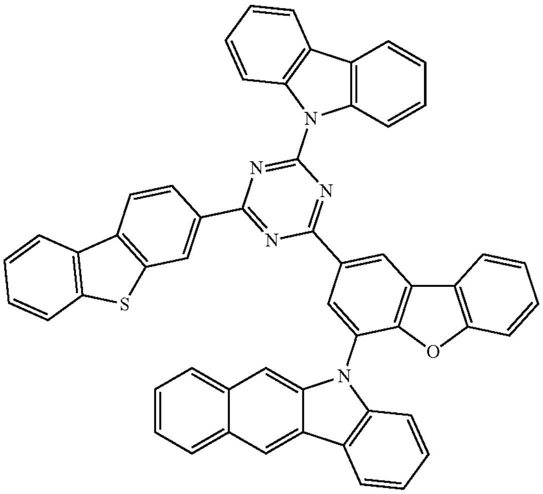
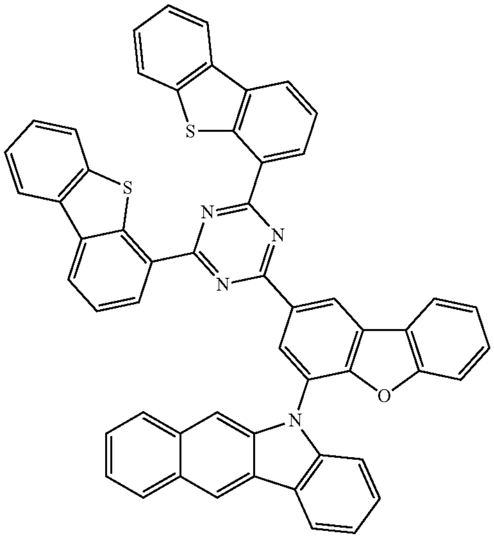
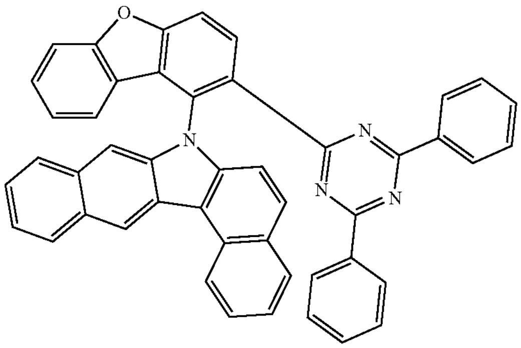
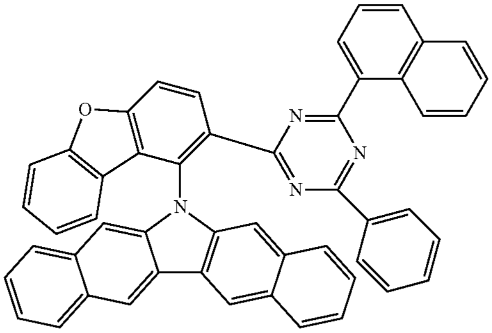
-continued
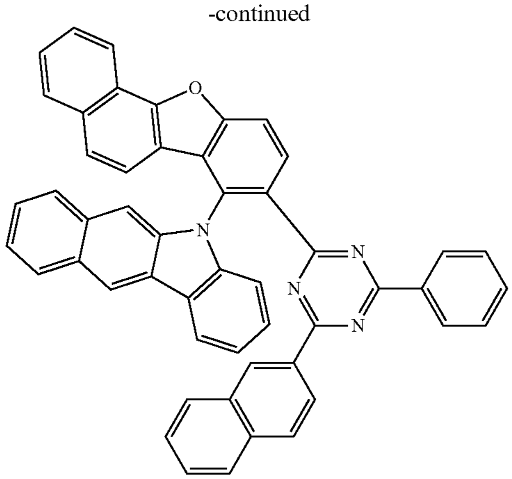
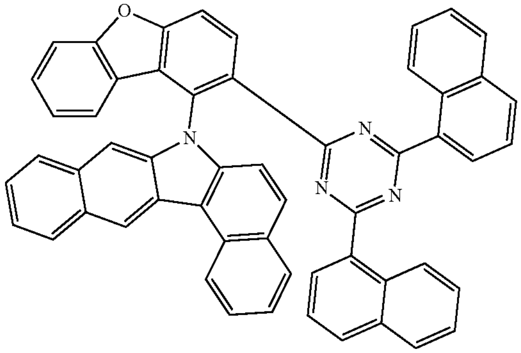
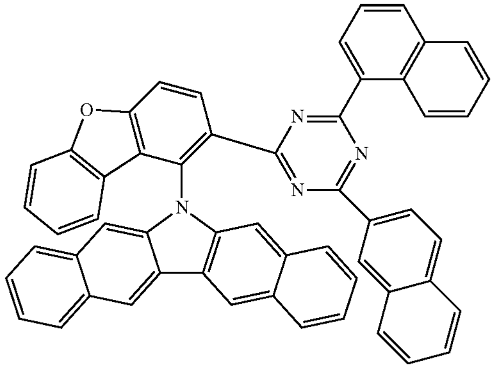
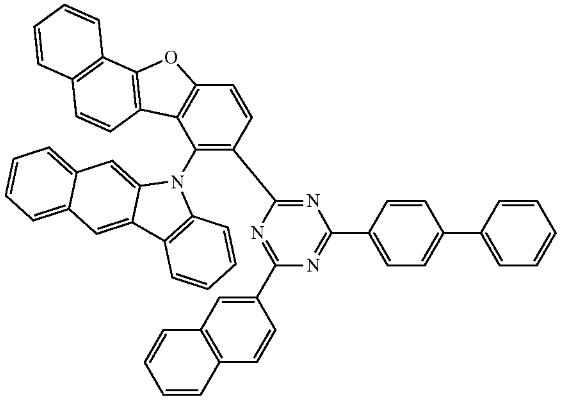

-continued
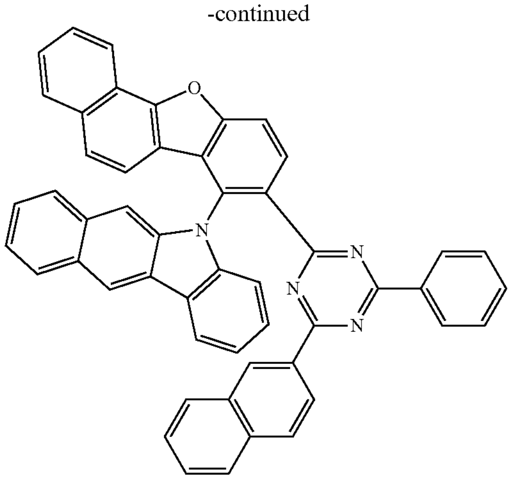
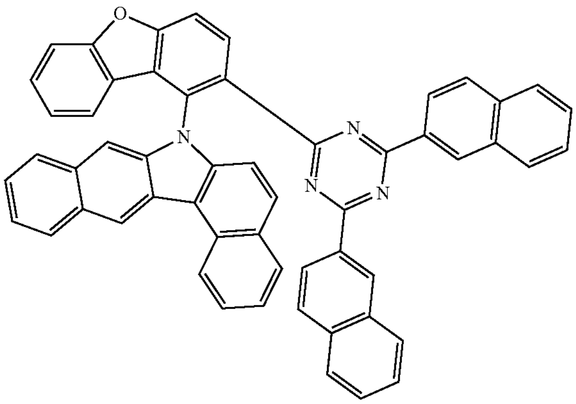
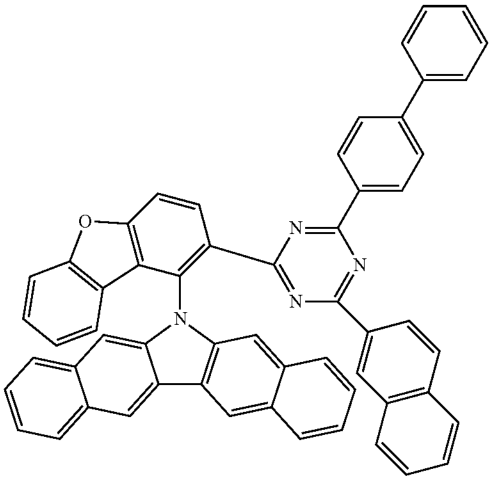
-continued
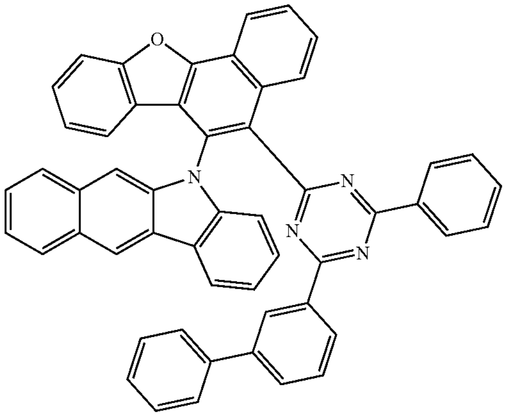
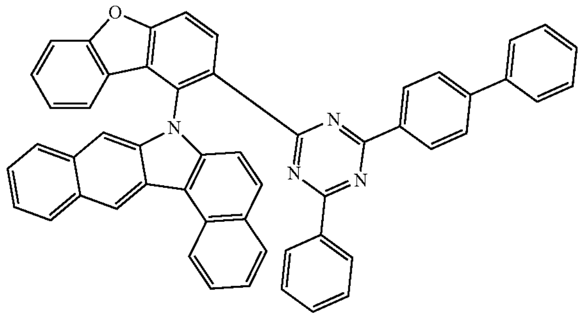
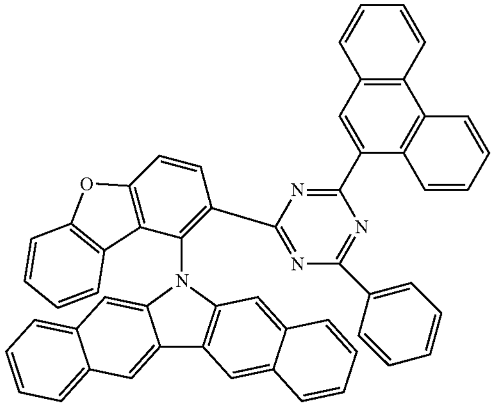
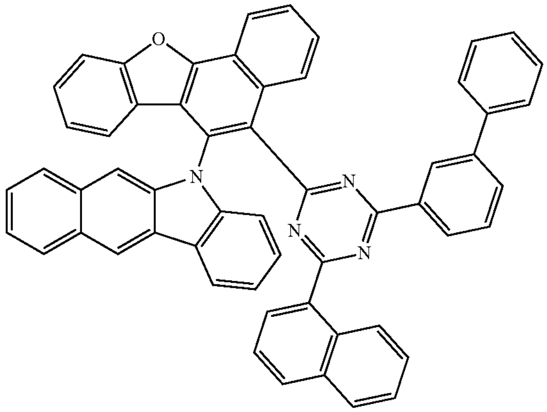

-continued
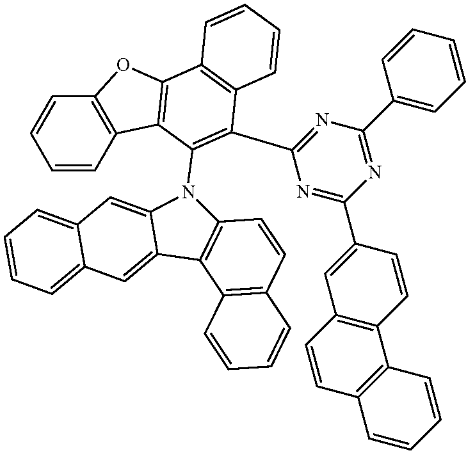
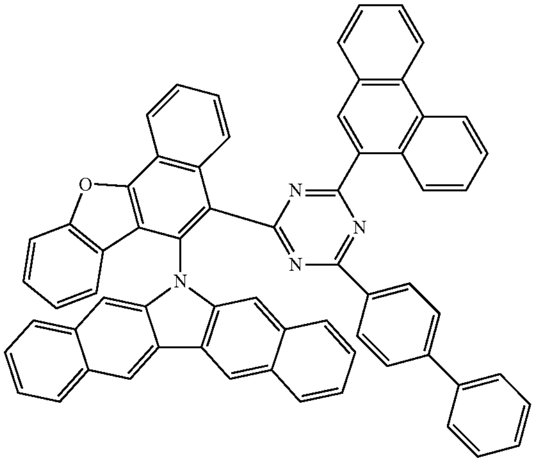
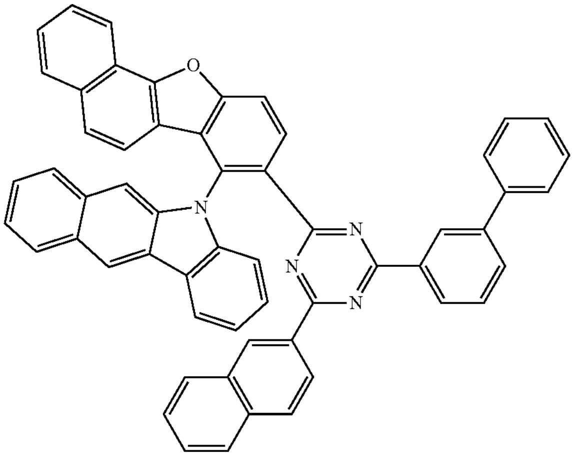
-continued
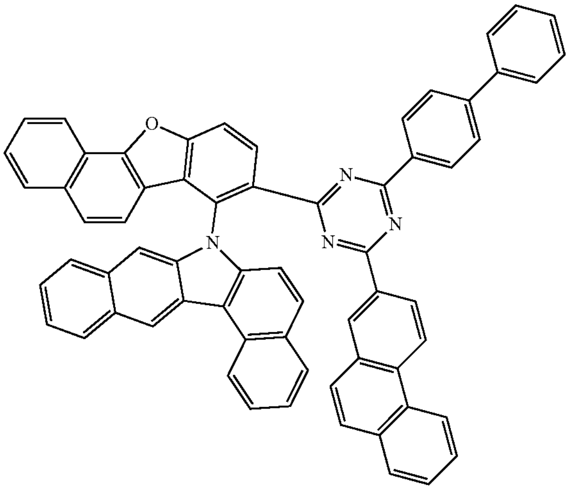
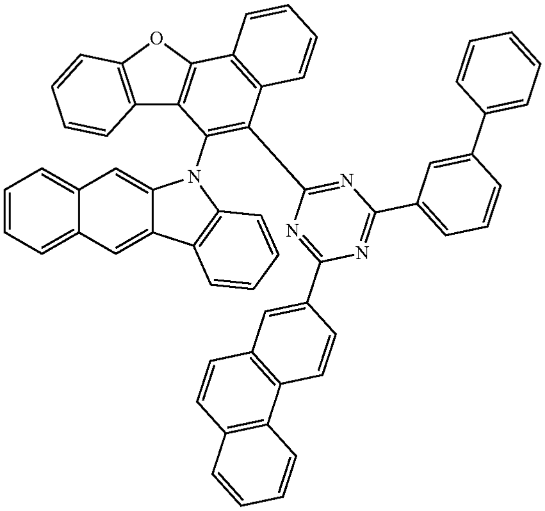
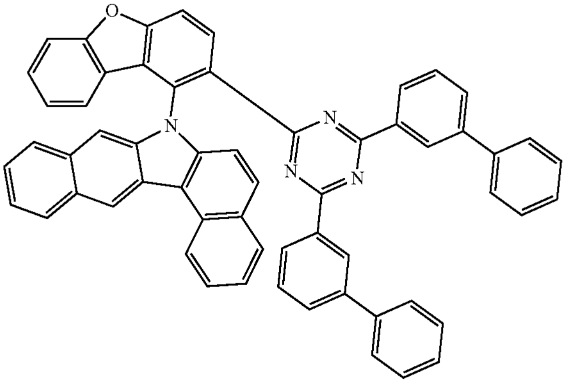

-continued
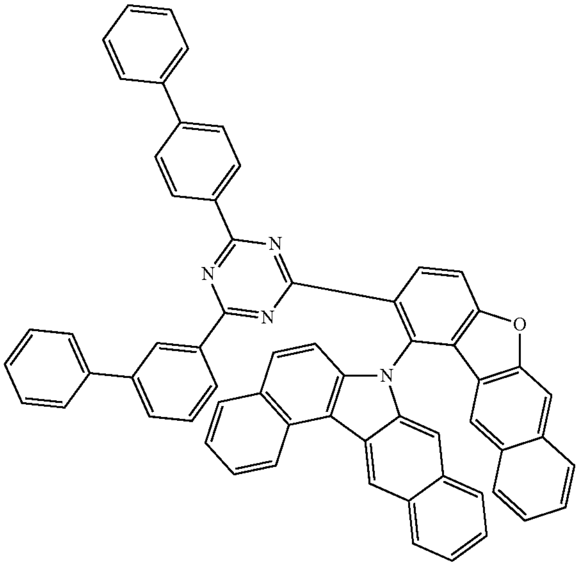
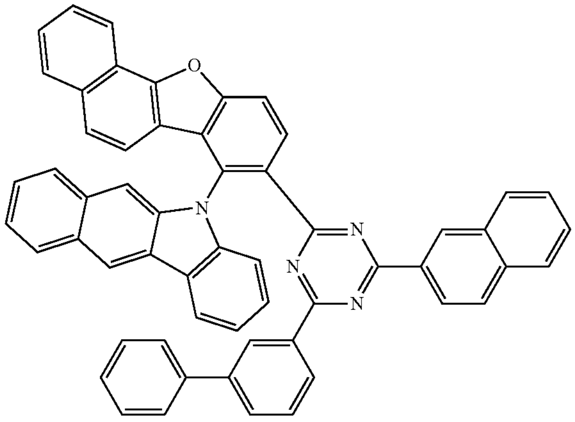
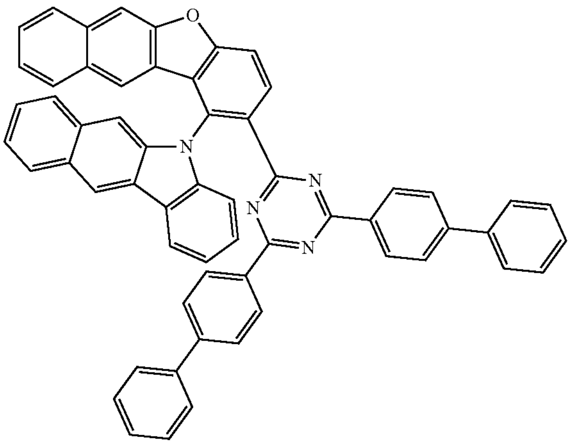
-continued
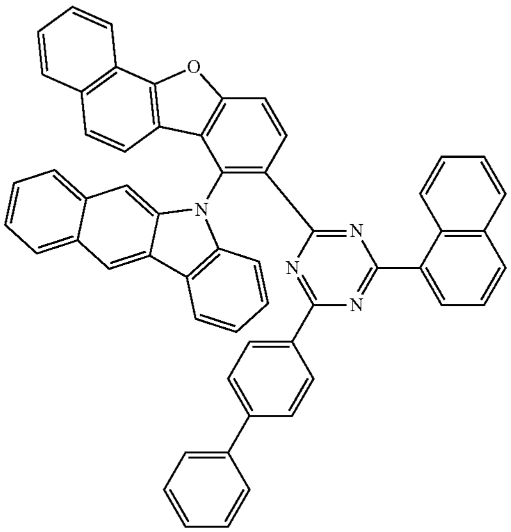
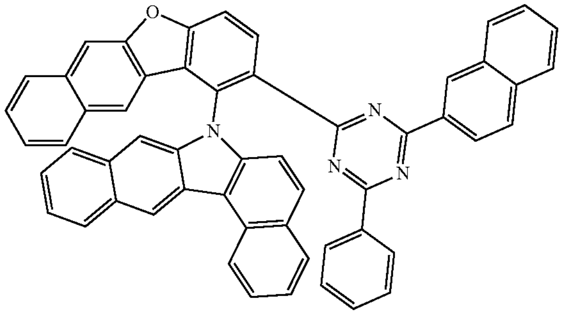
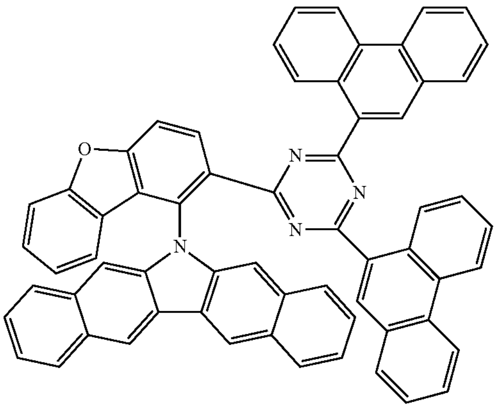
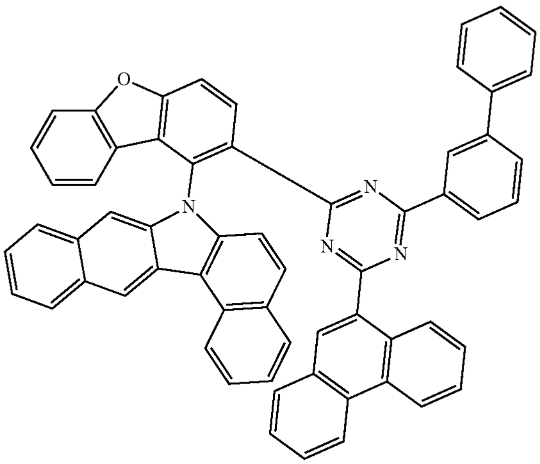

-continued
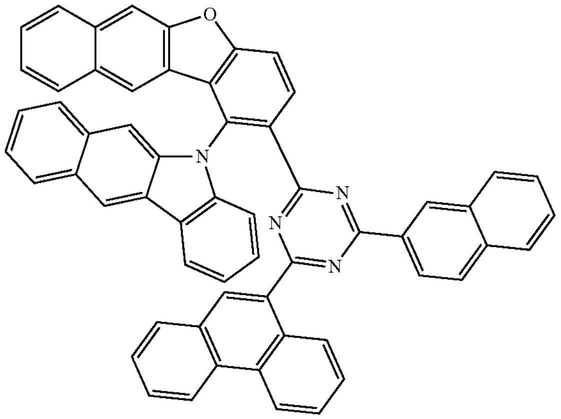
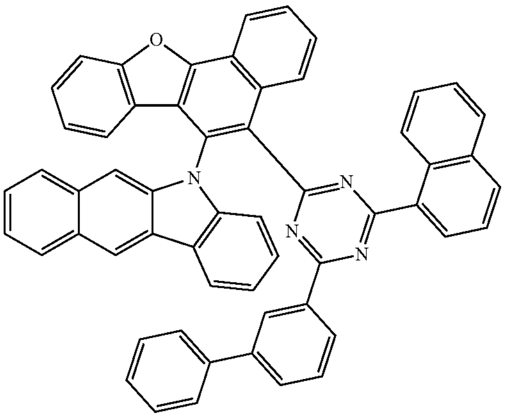
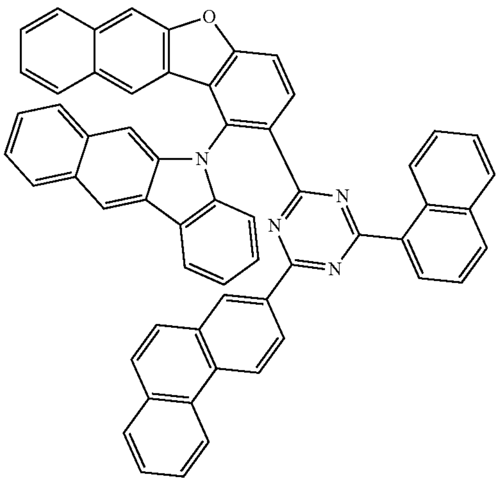
-continued
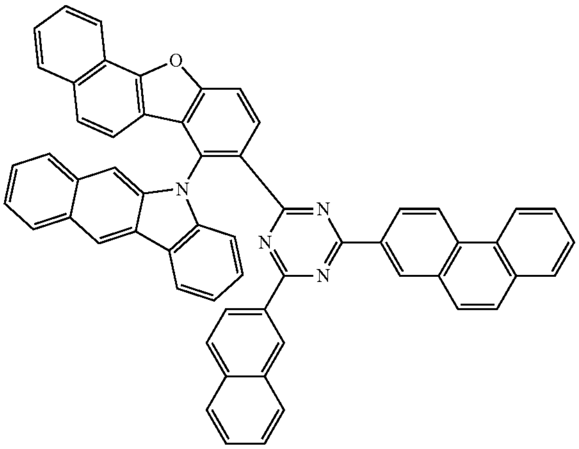
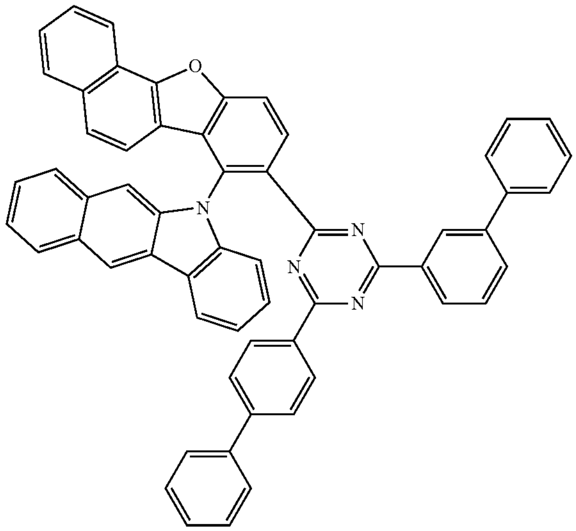
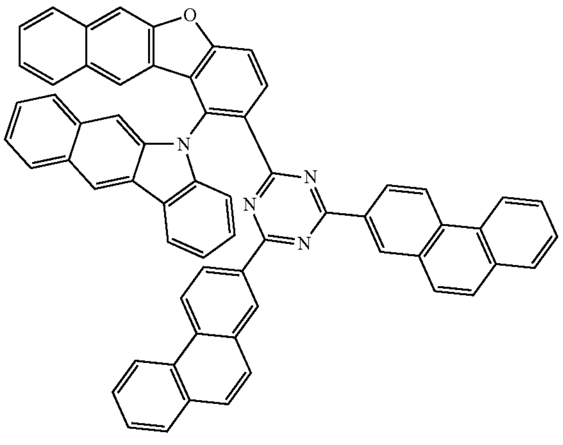

-continued
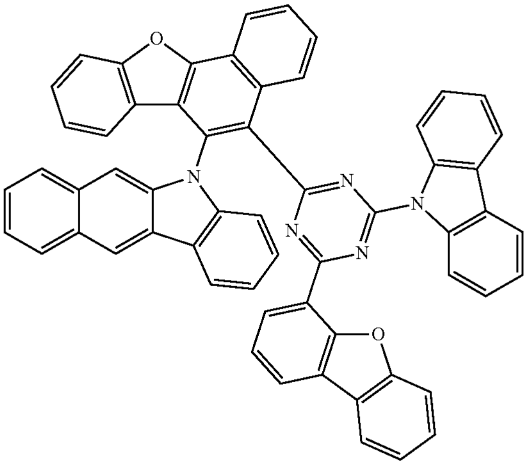
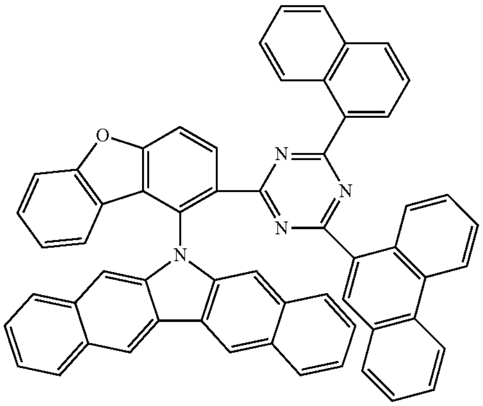
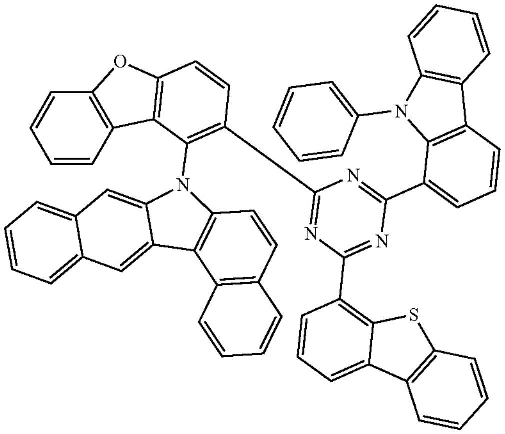
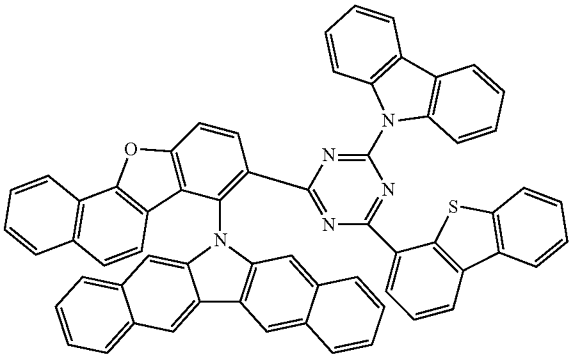
-continued
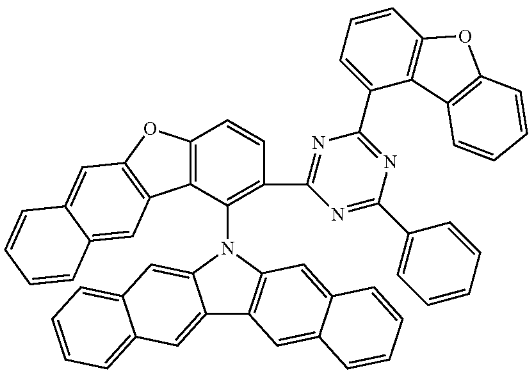
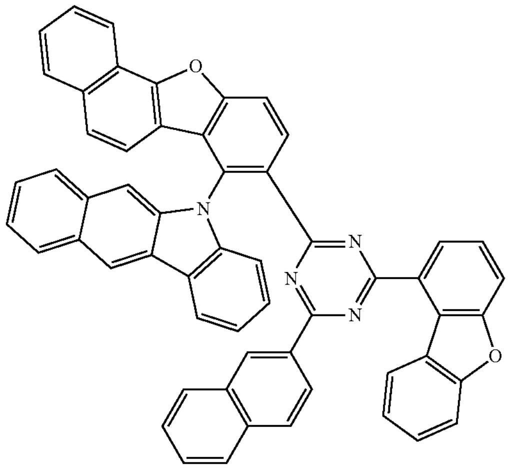
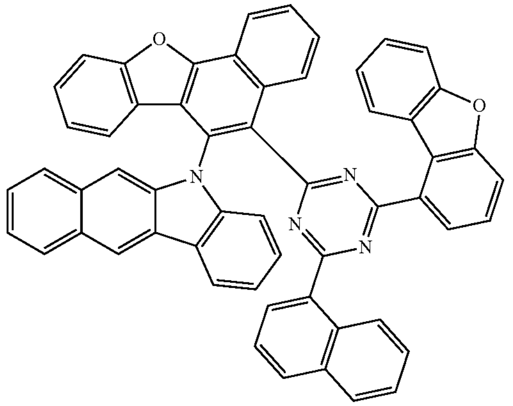
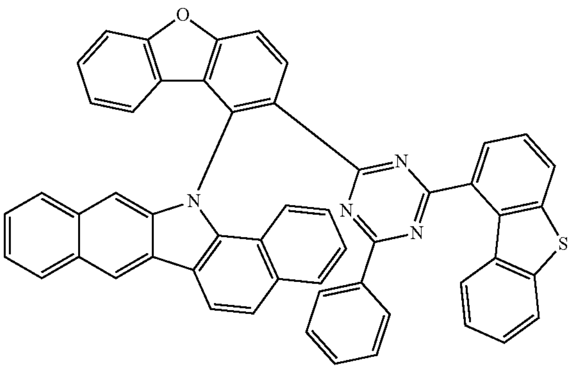

-continued
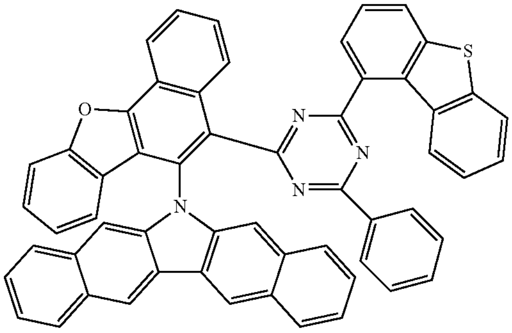
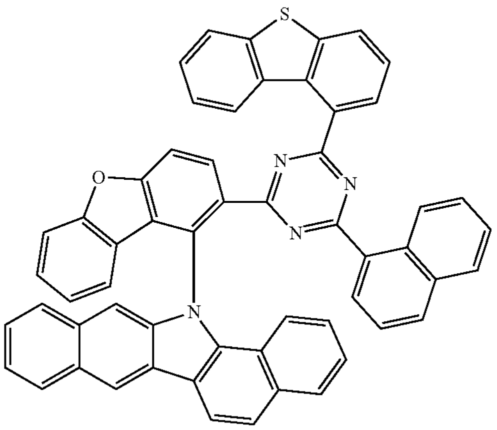
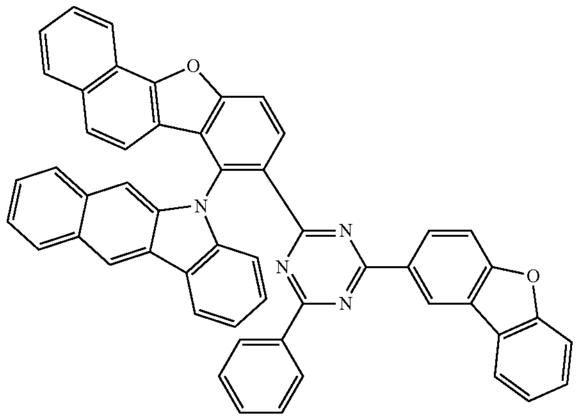
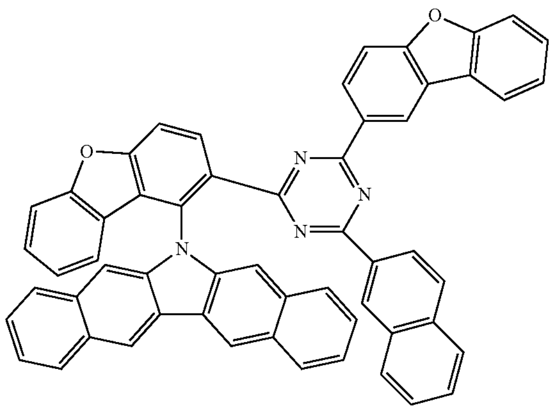
-continued
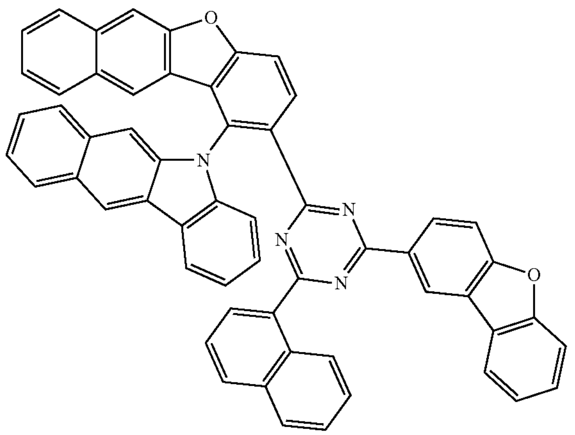
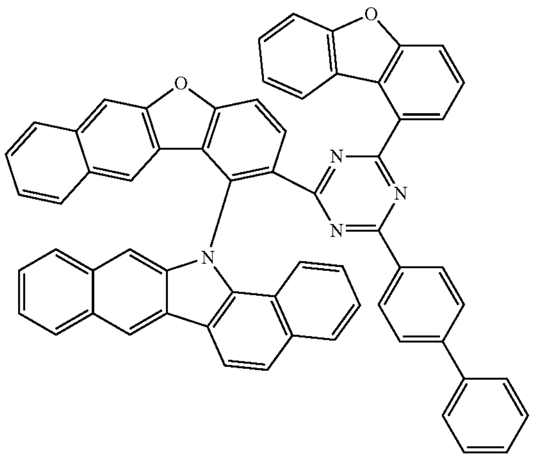
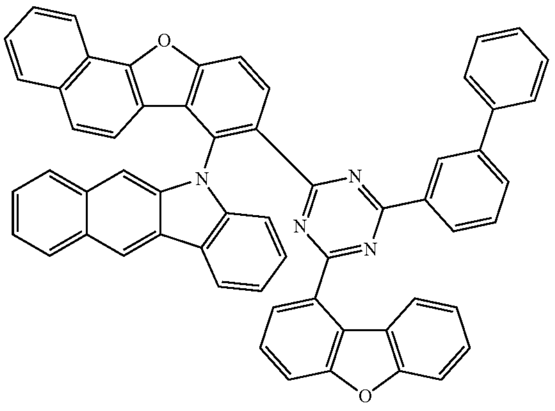
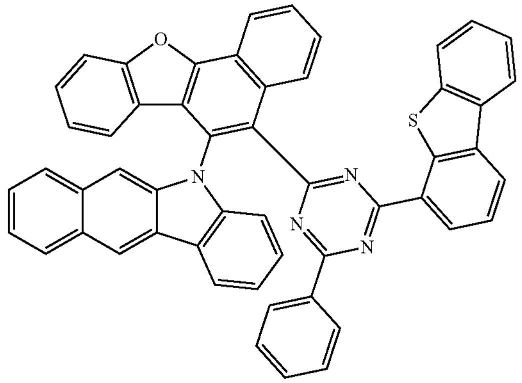

-continued
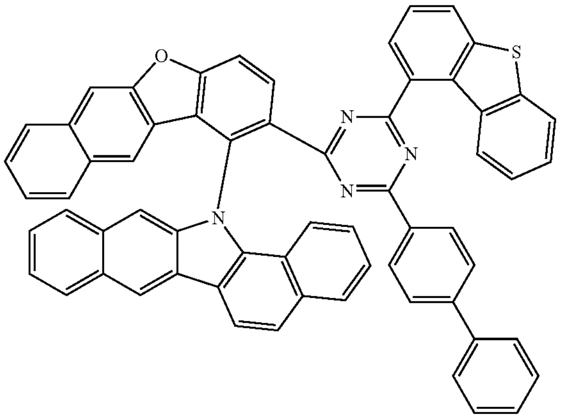
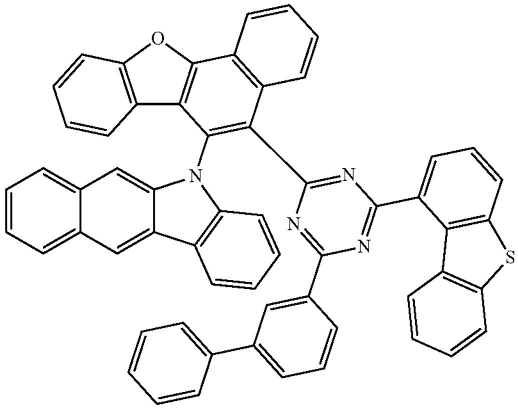
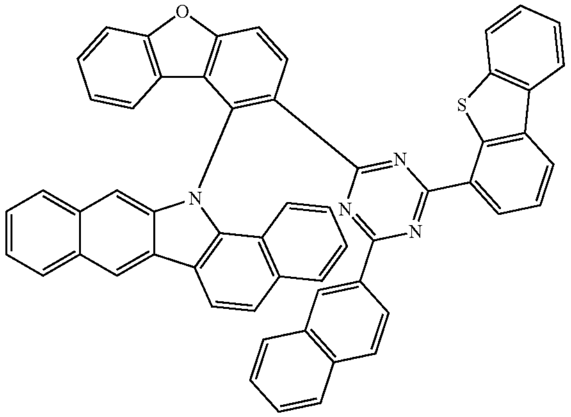
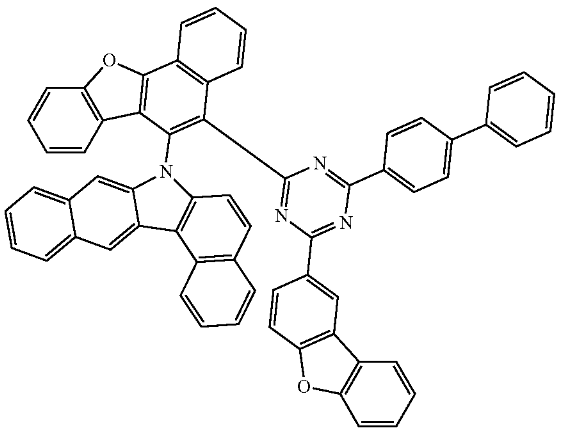
-continued
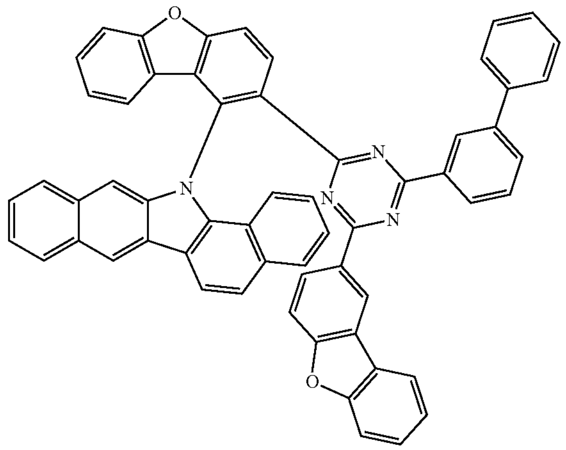
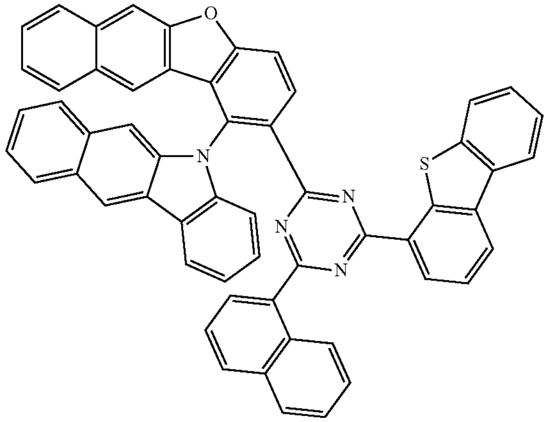
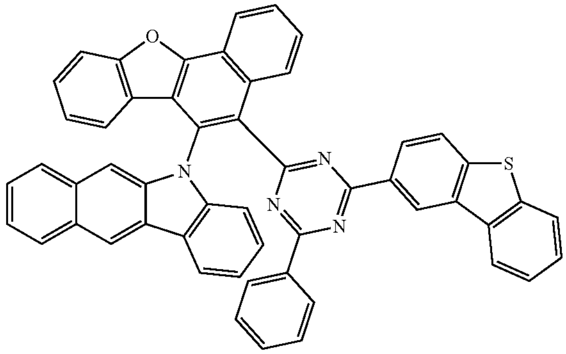
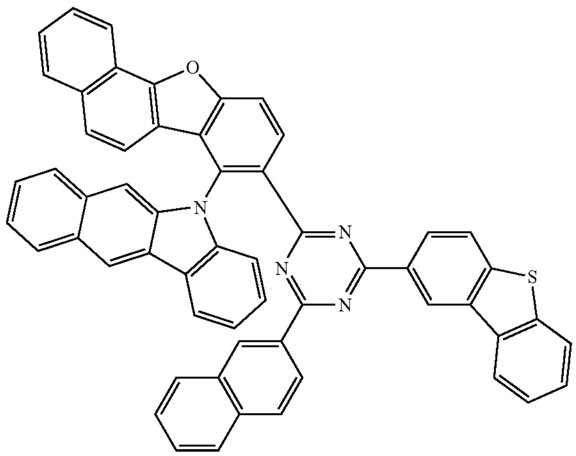

-continued
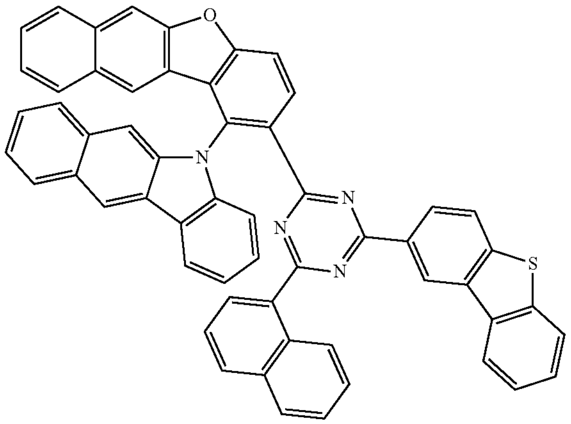
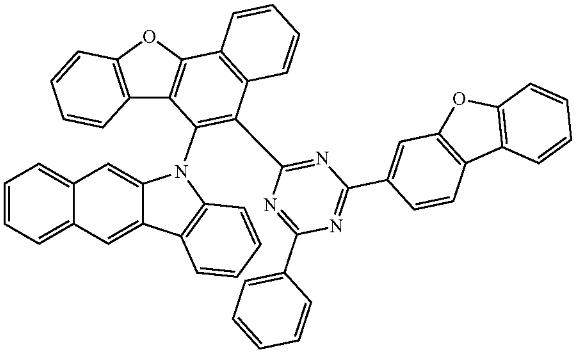
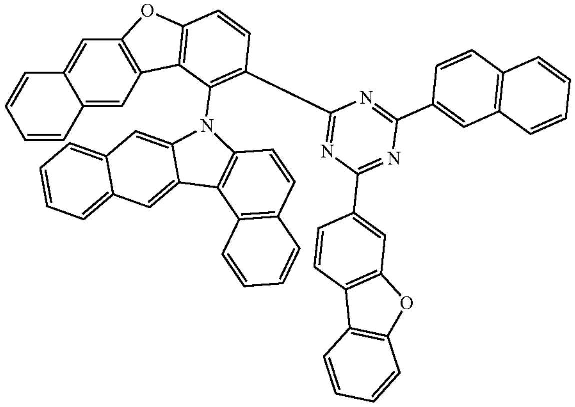
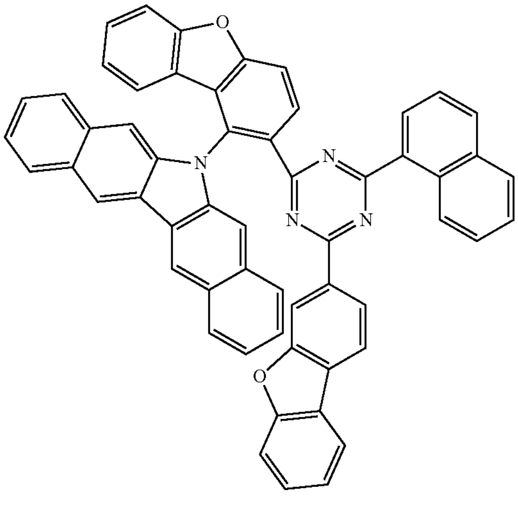
-continued
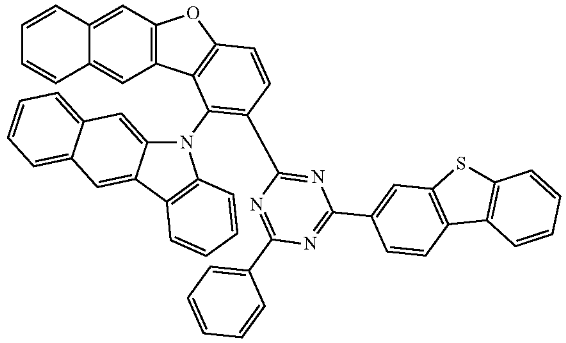
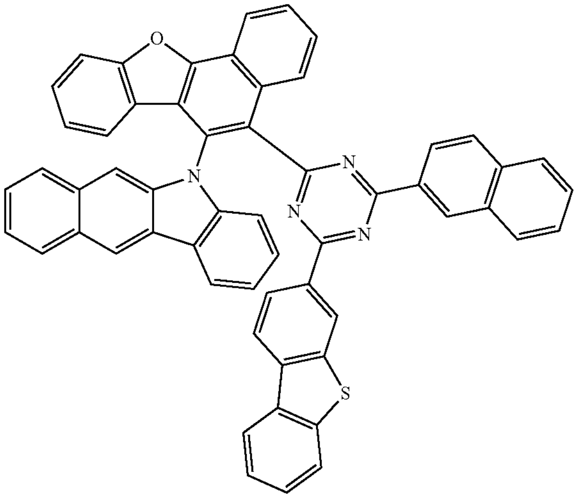
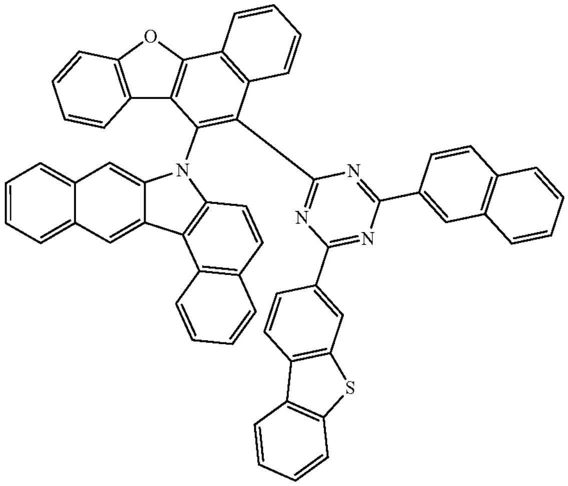
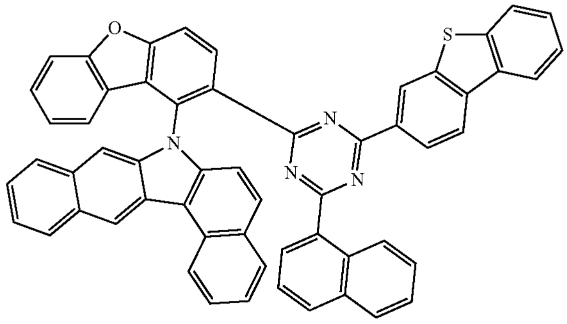

-continued
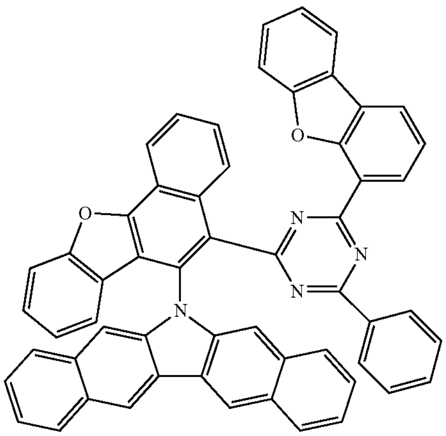
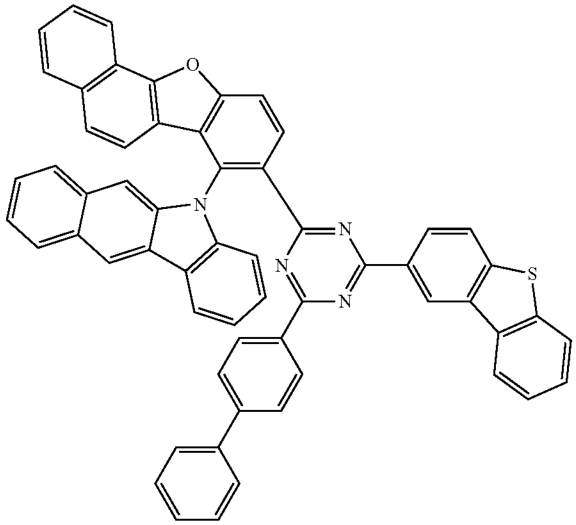
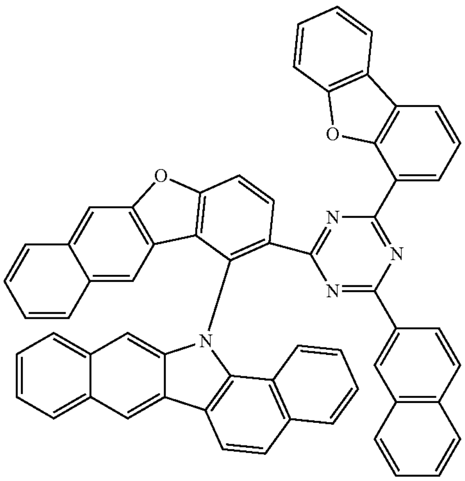
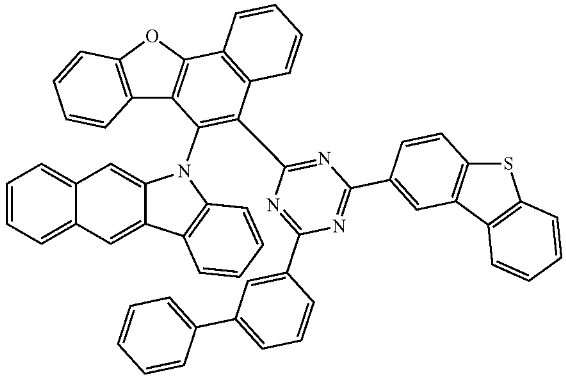
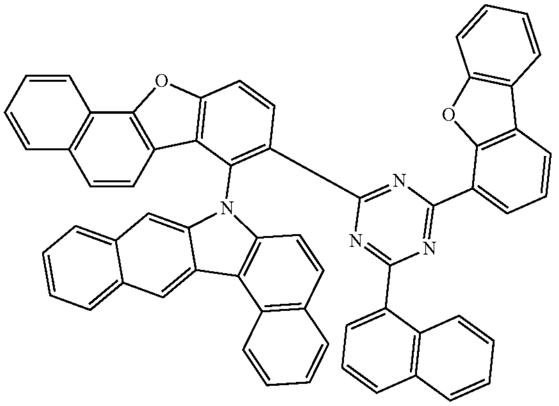
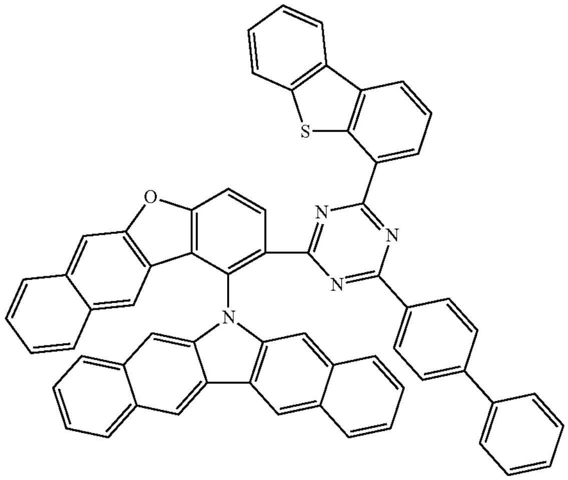

-continued
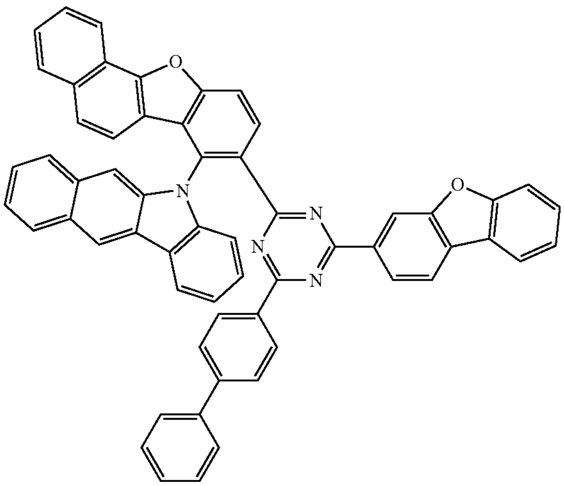
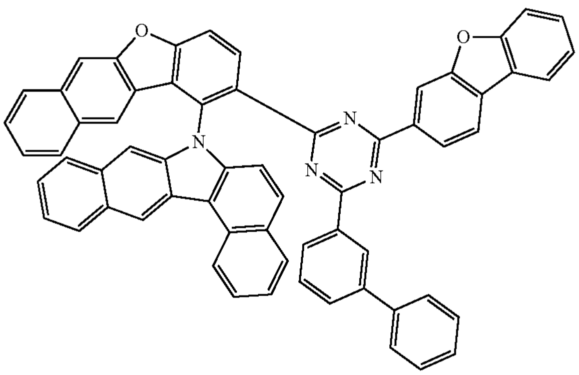
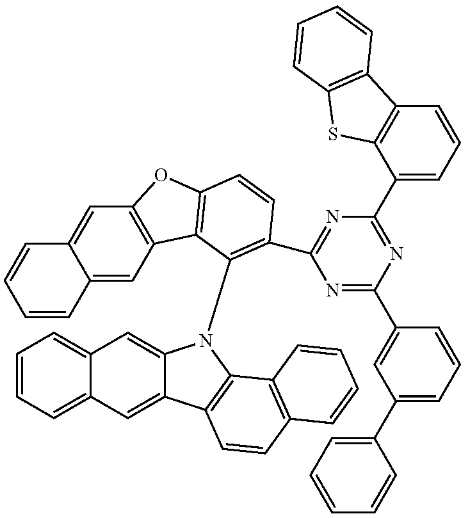
-continued
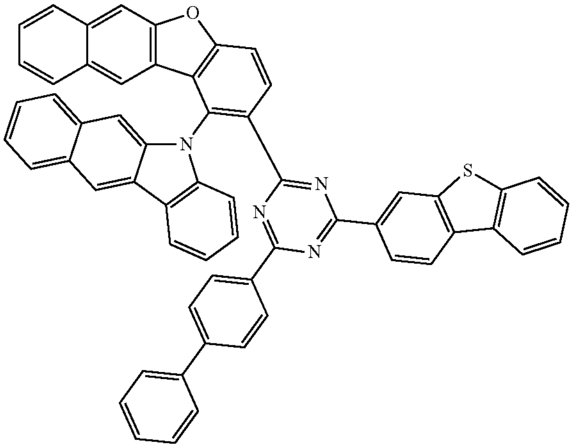
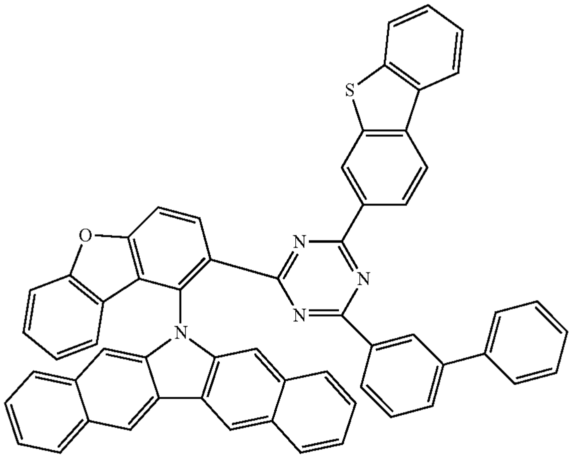
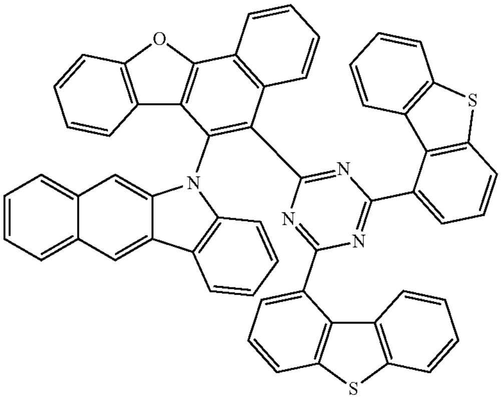

-continued
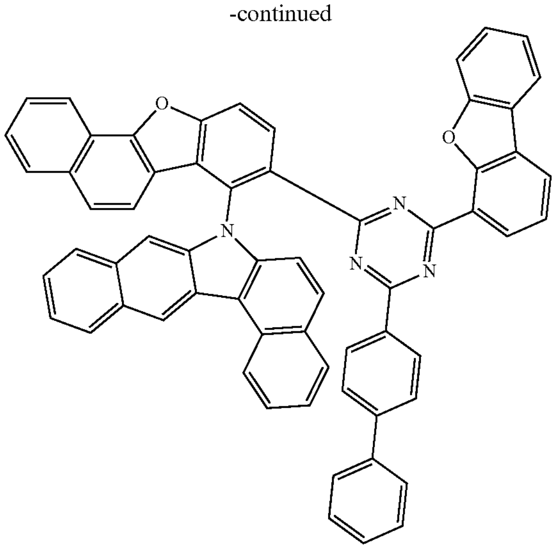
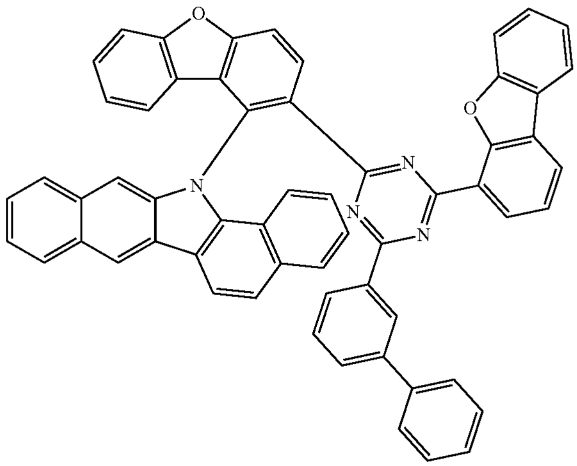
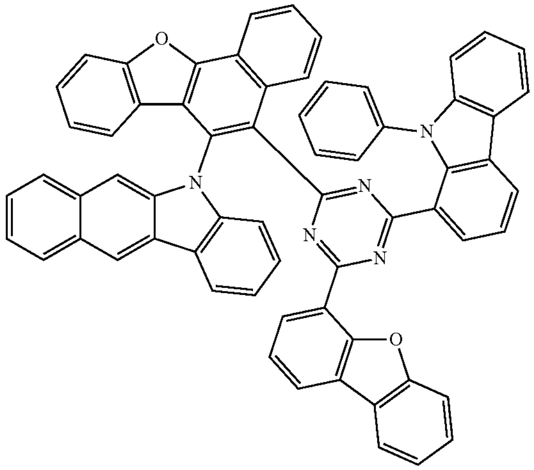
-continued
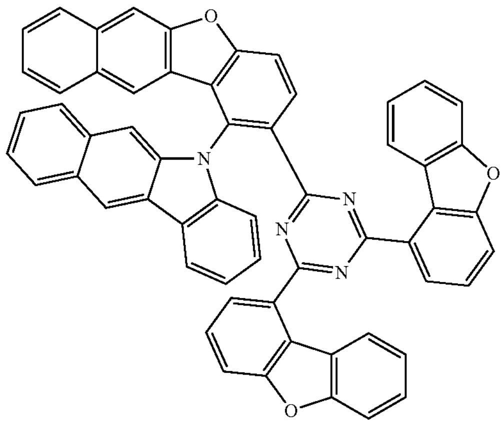
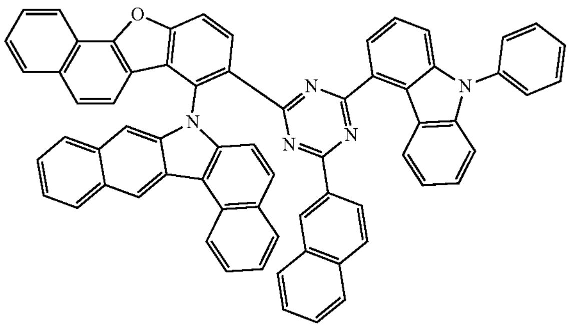
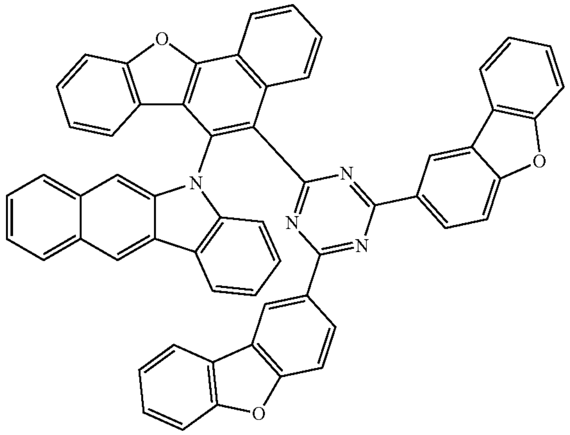
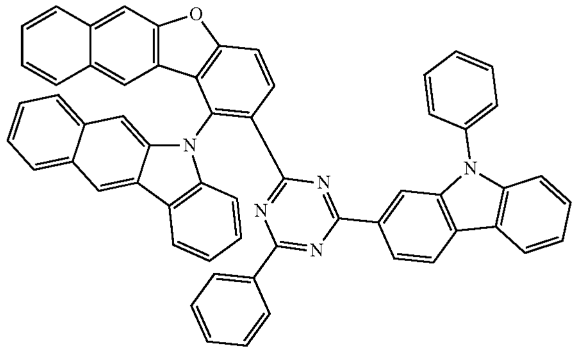

-continued
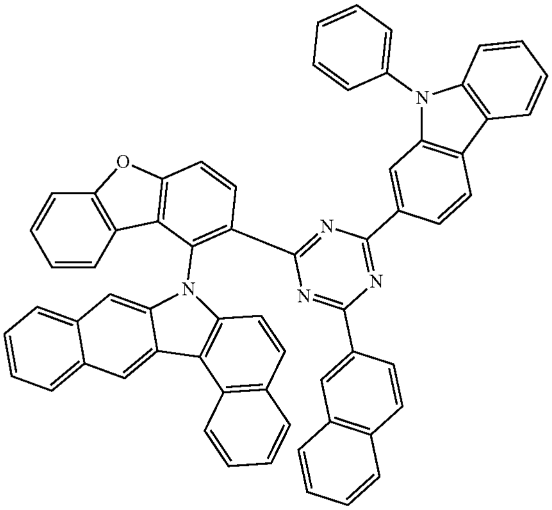
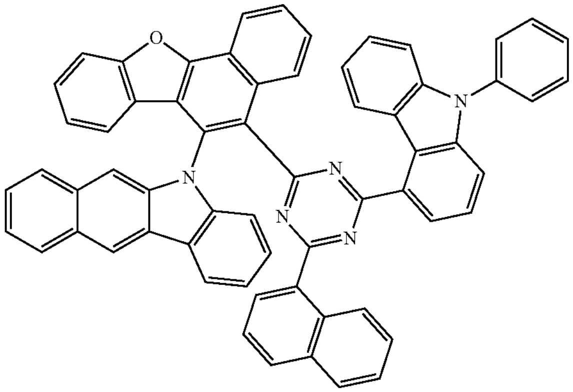
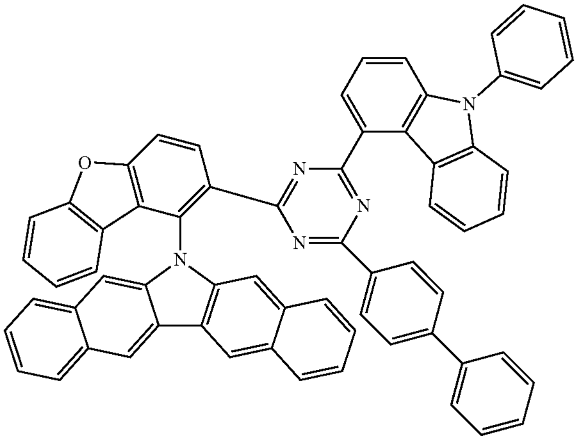
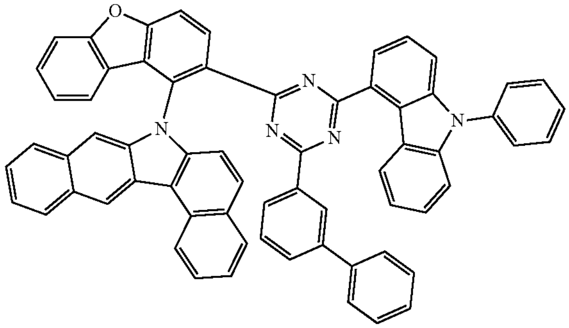
-continued
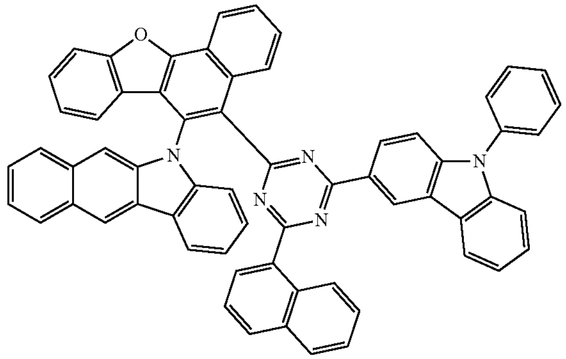
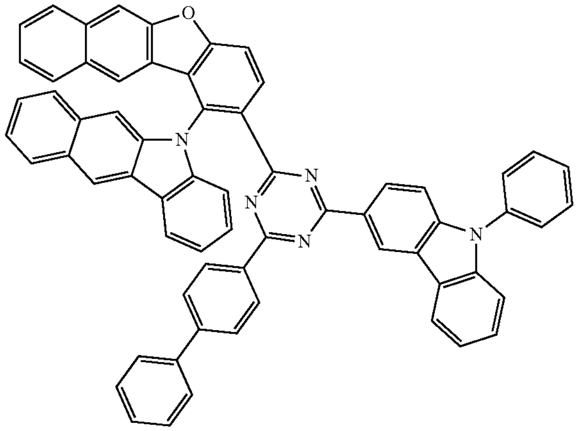
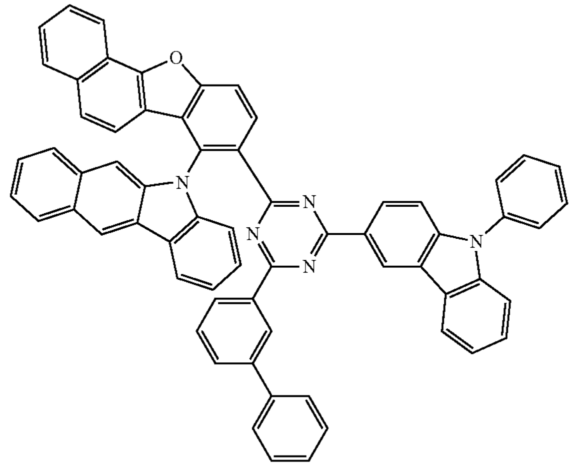
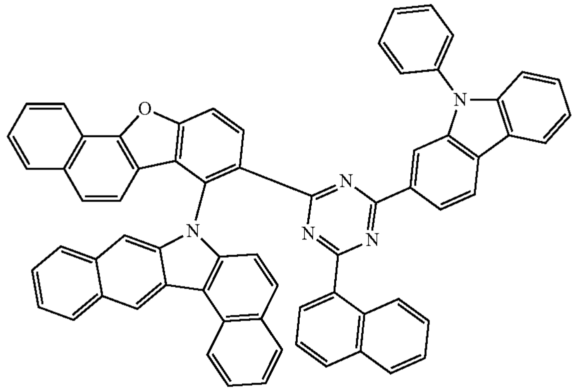

-continued
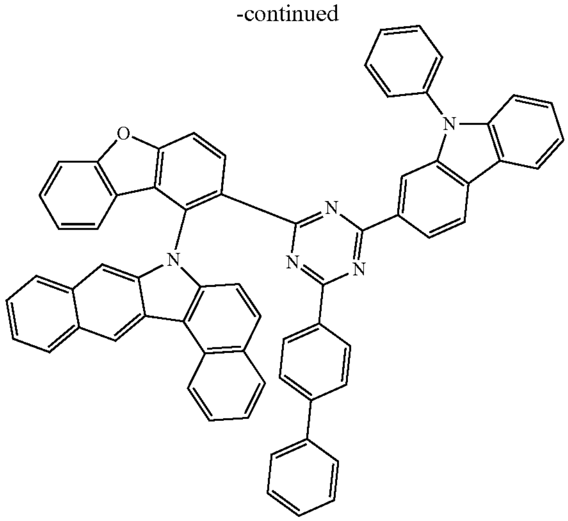
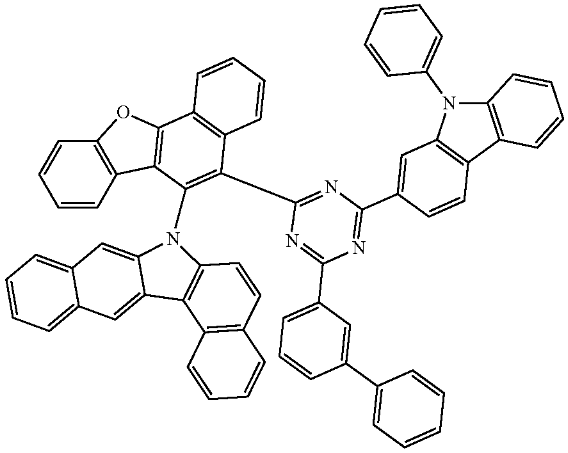
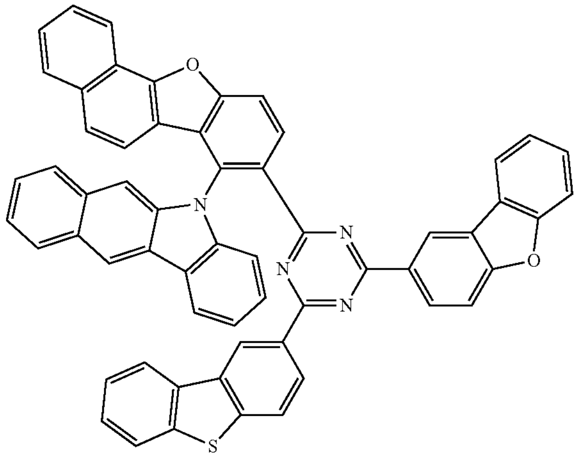
-continued
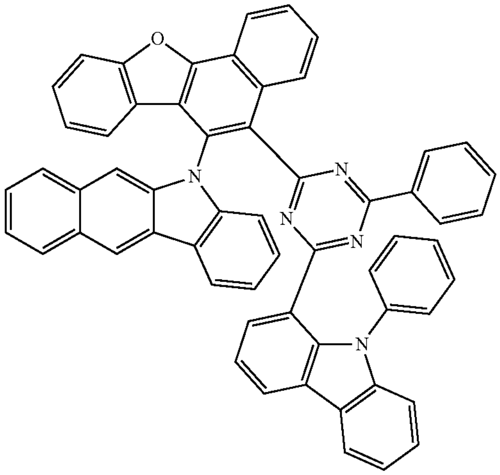
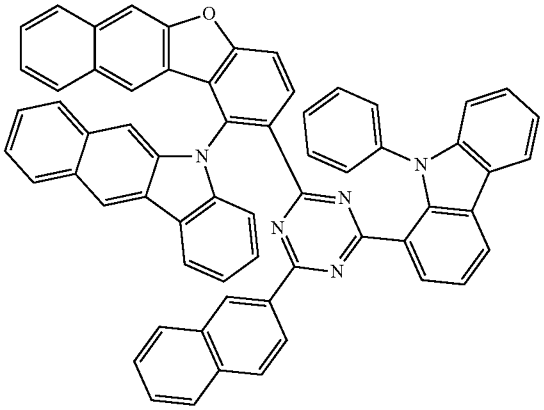
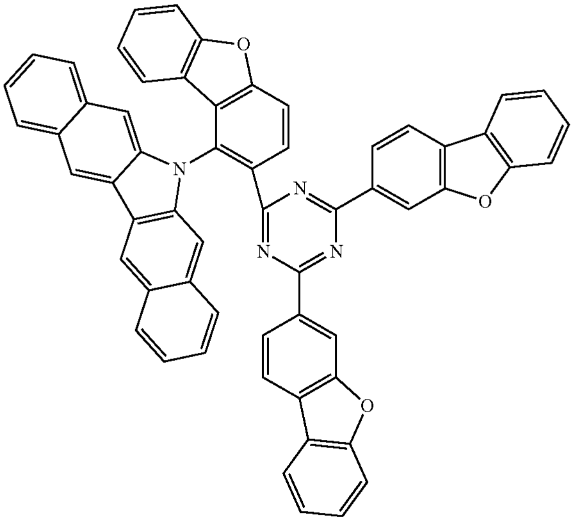

-continued
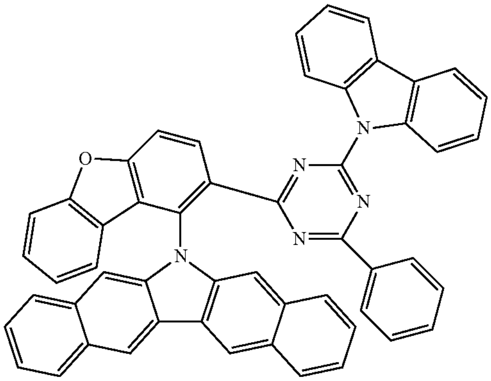
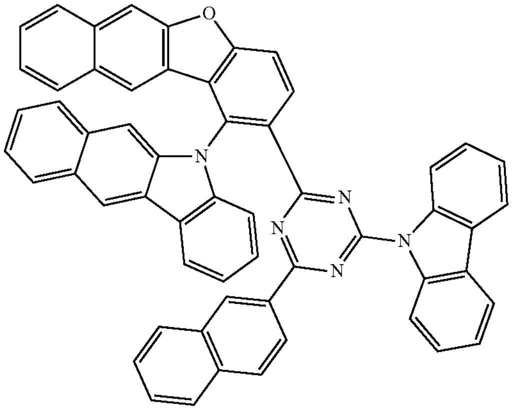
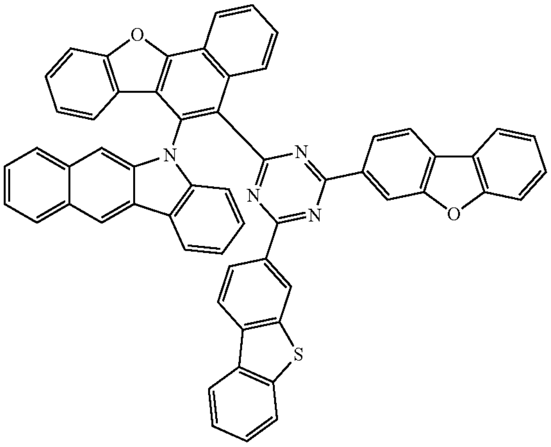
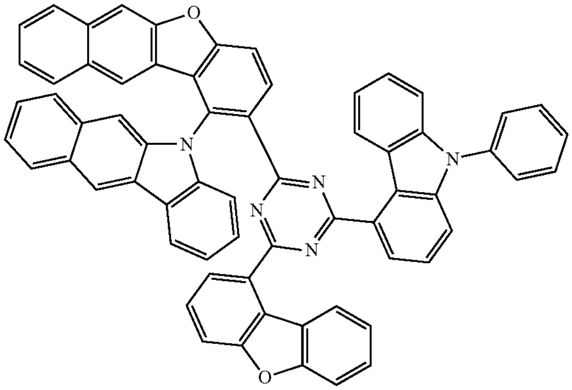
-continued
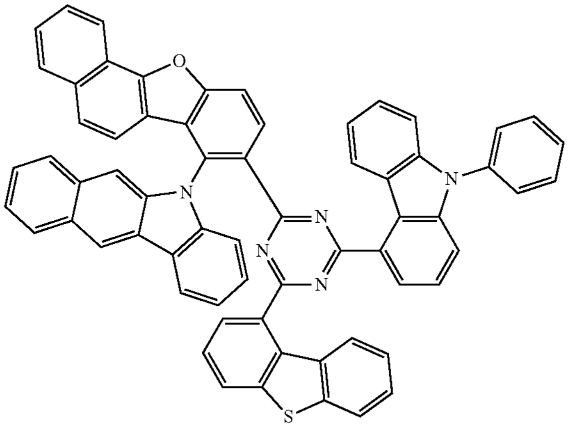
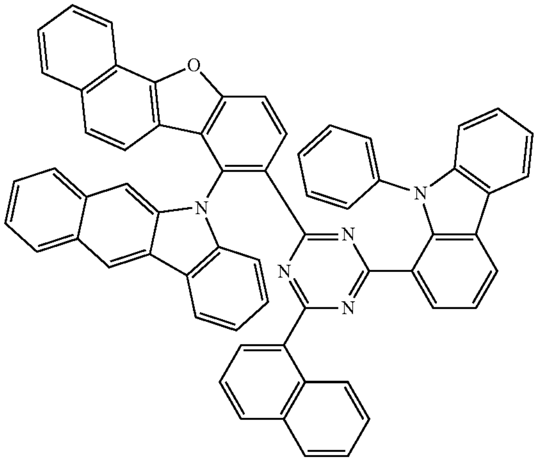
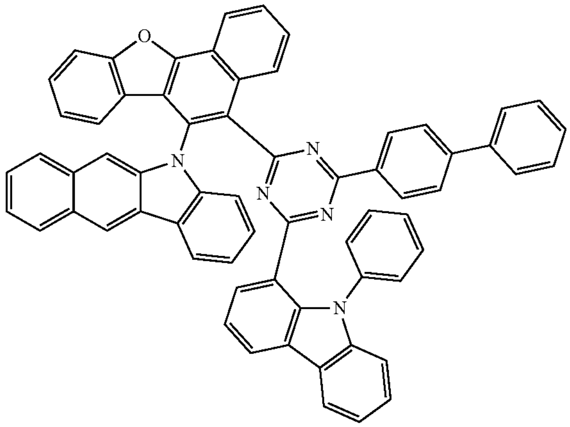

-continued
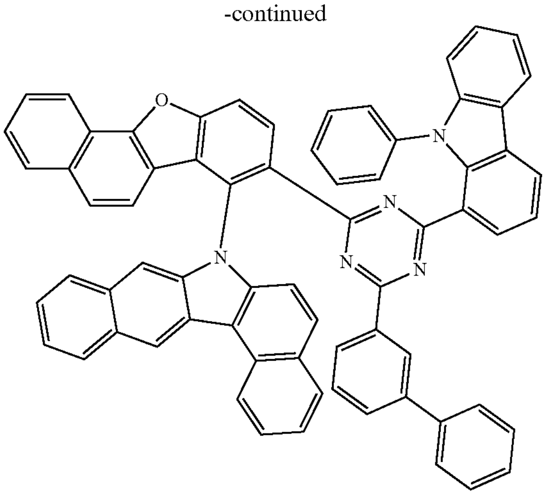
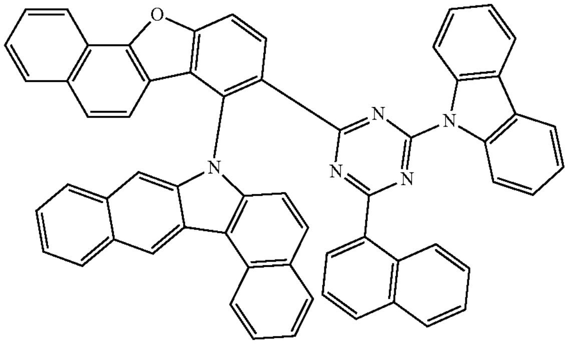
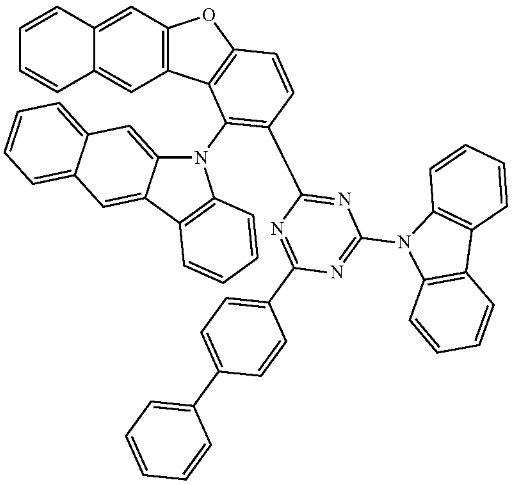
-continued
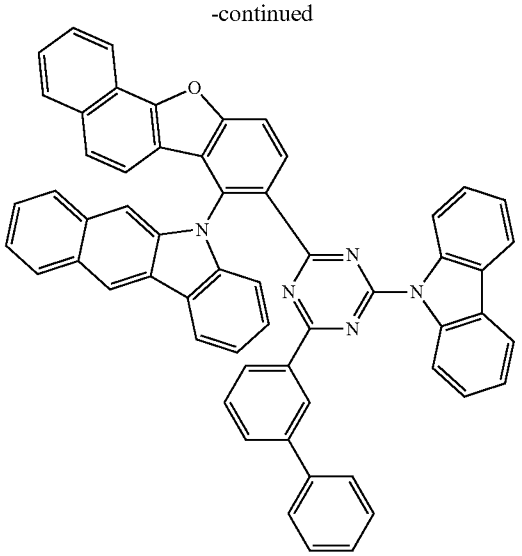
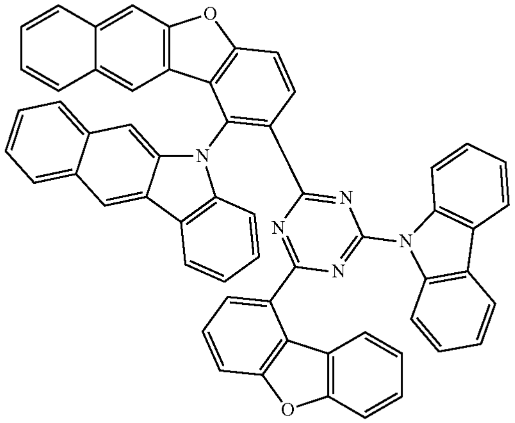
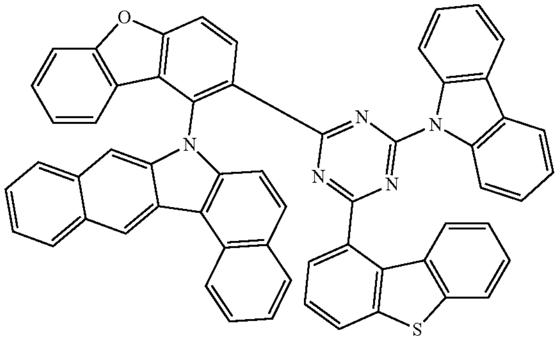
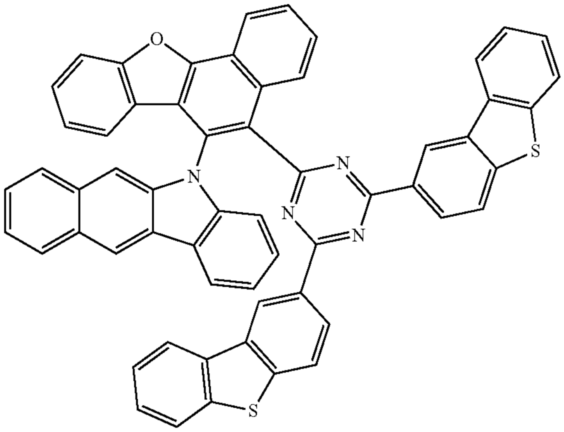

-continued
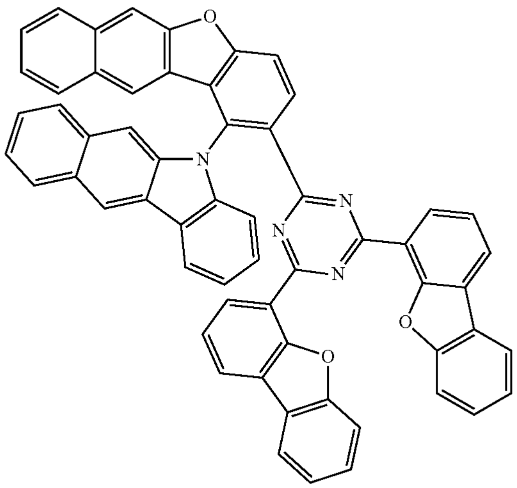
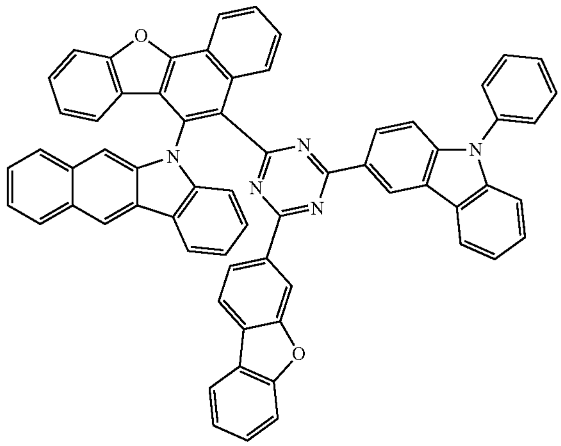
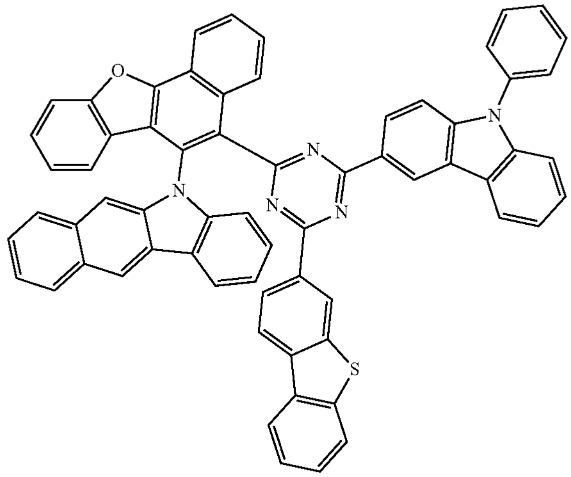
-continued
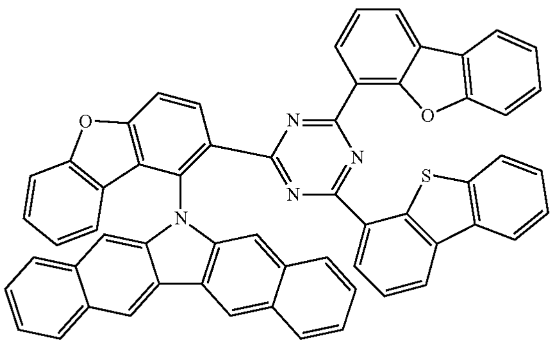
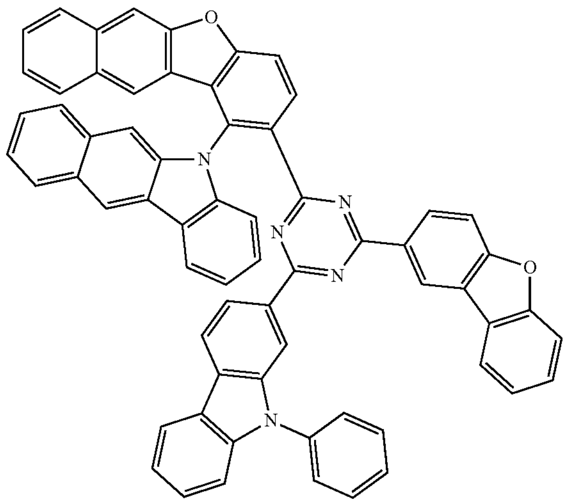
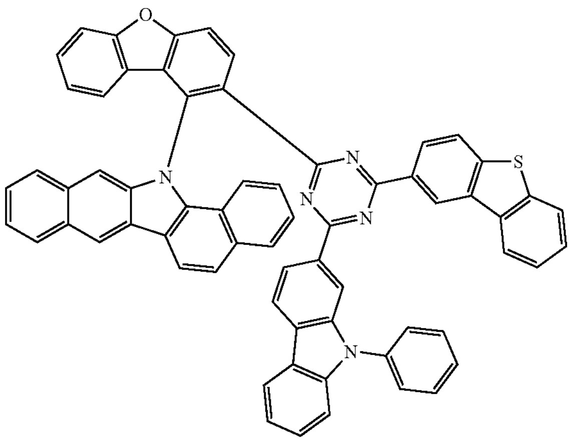
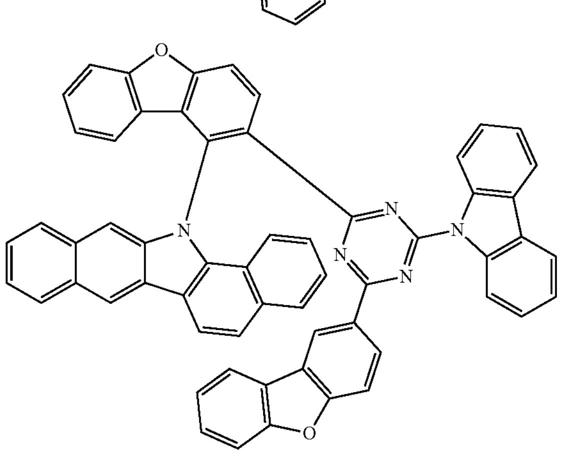

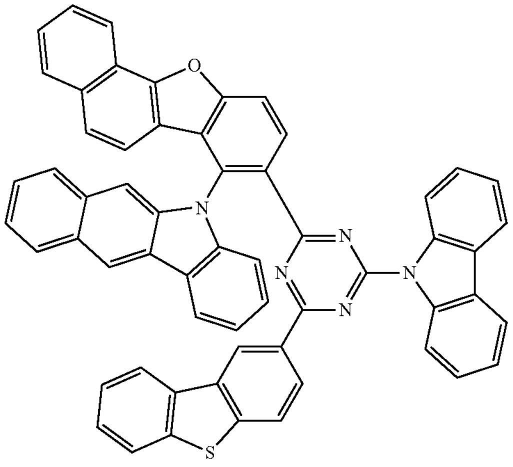
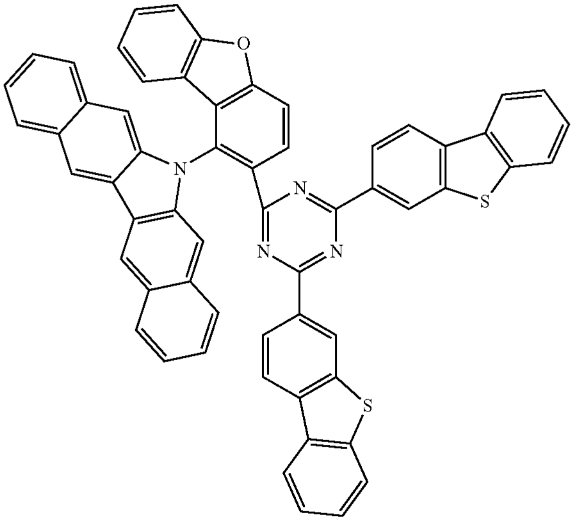
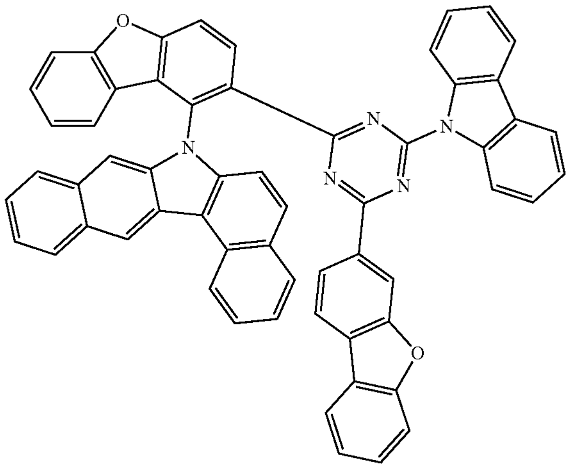
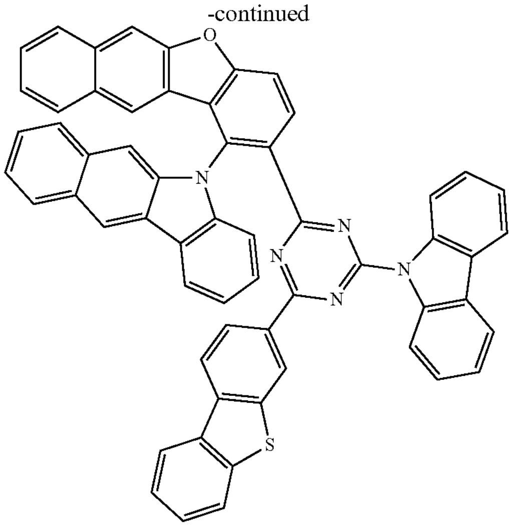
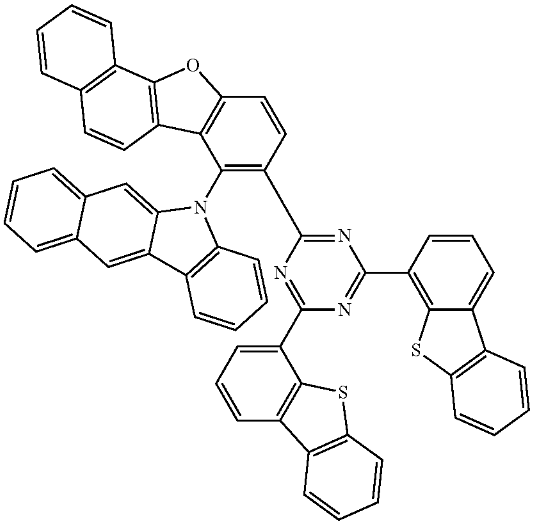
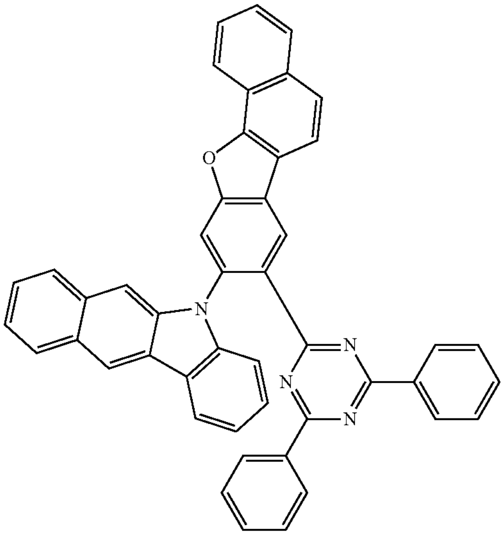

-continued
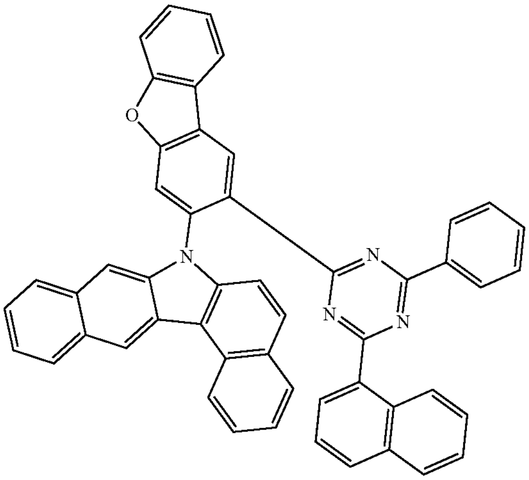
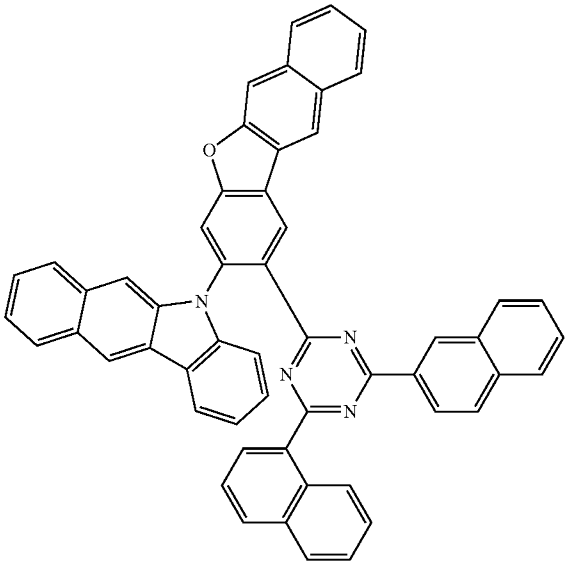
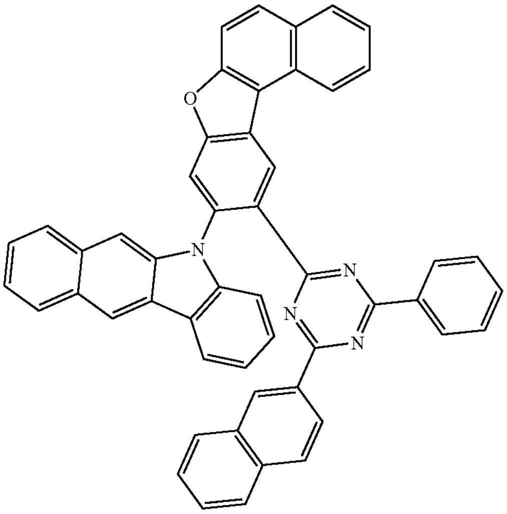
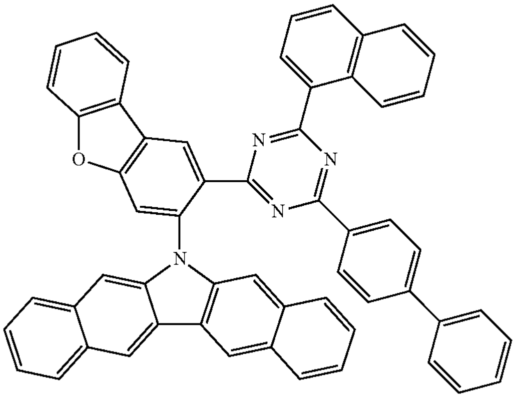
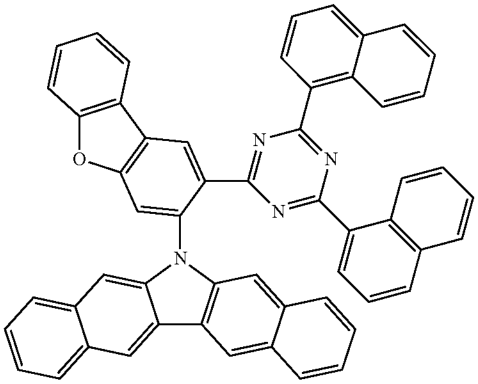
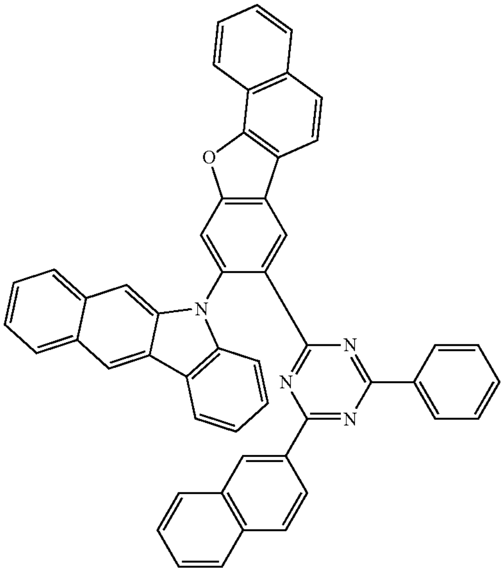

-continued
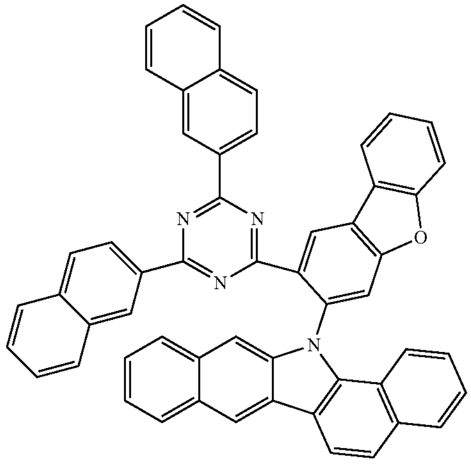
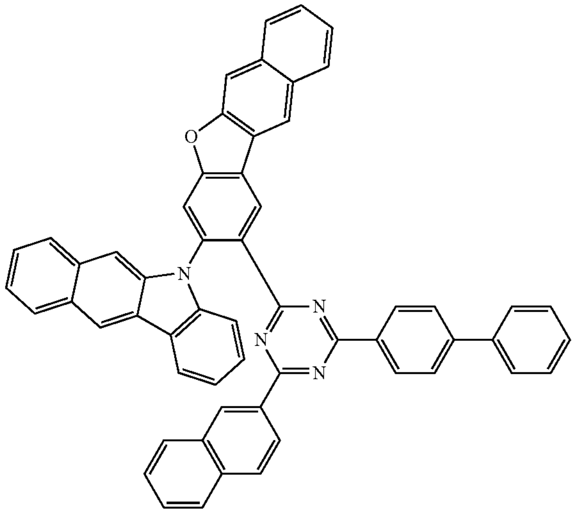
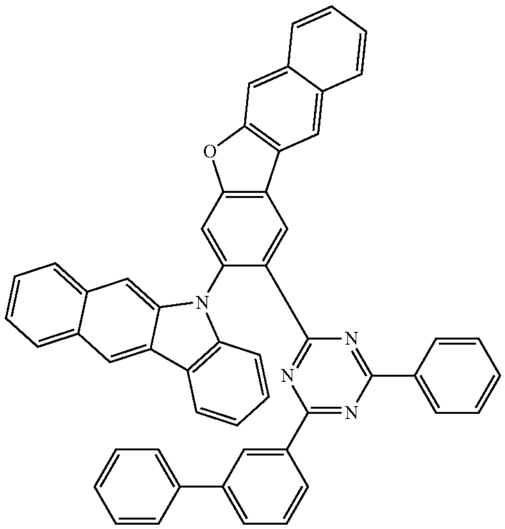
-continued
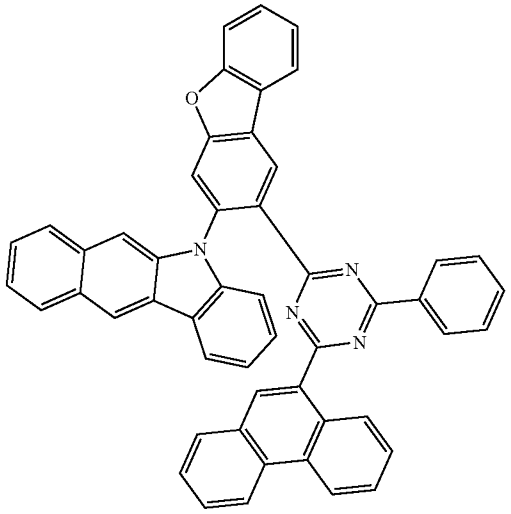
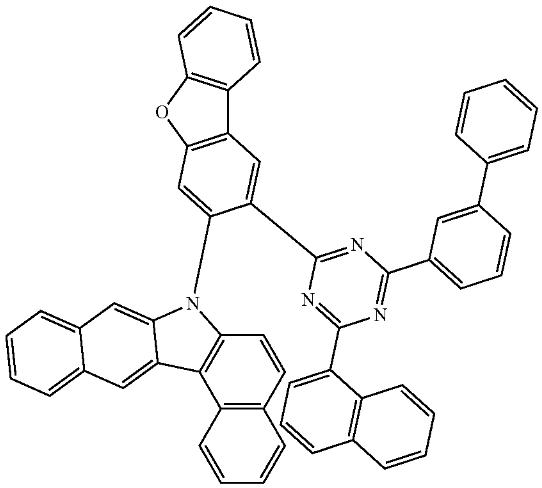
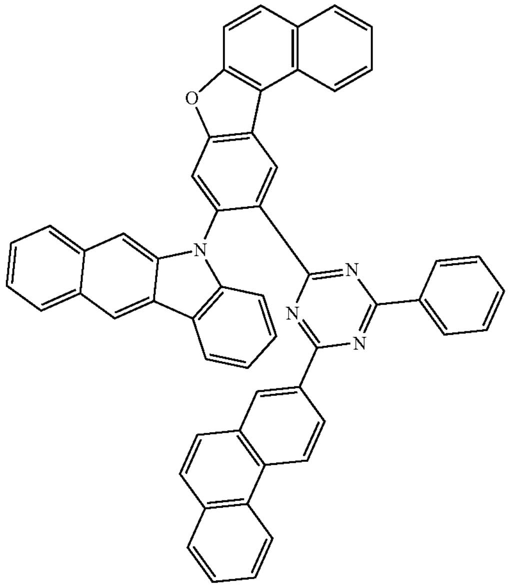

-continued
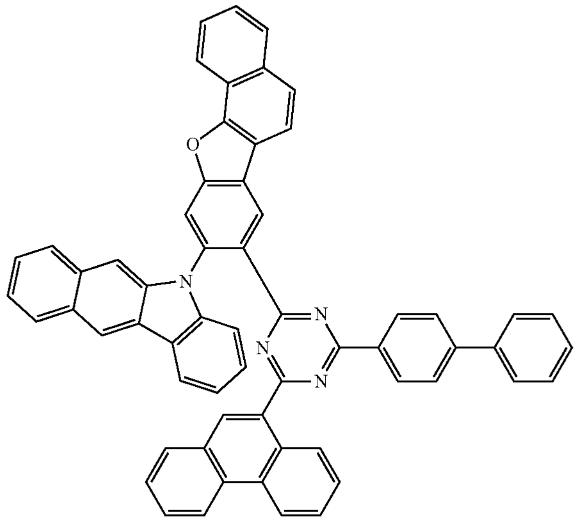
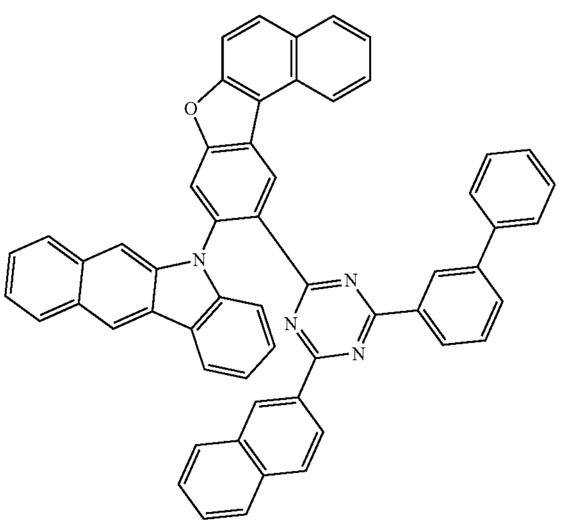
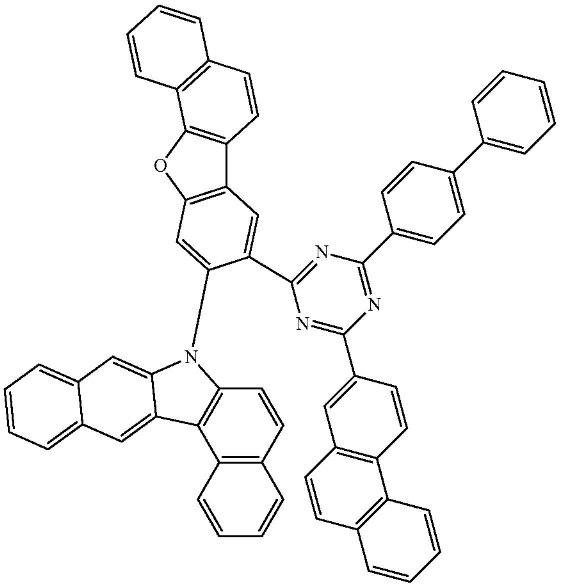
-continued
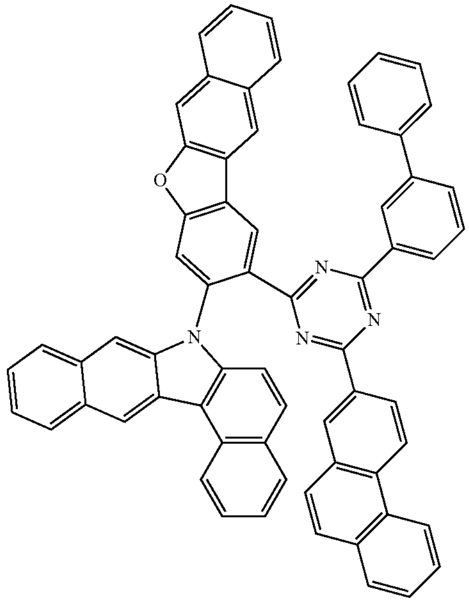
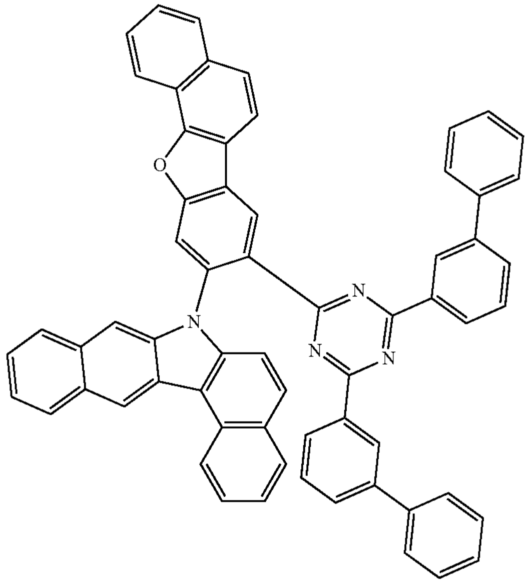
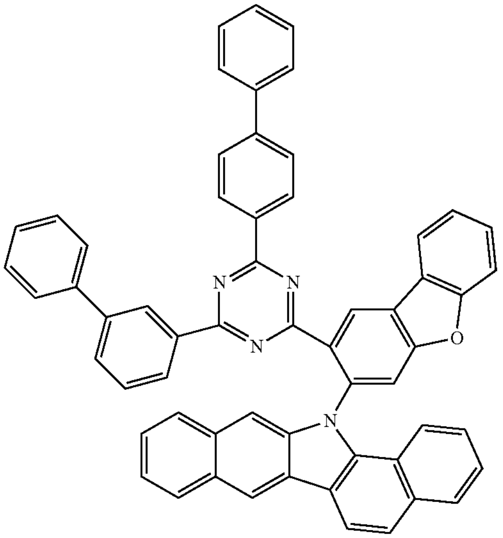

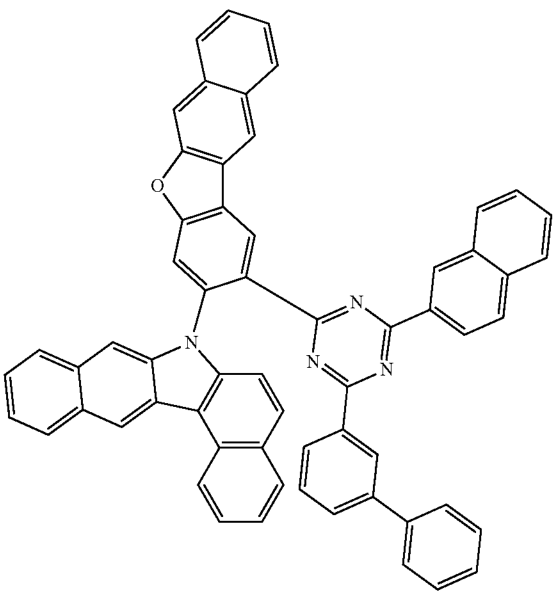
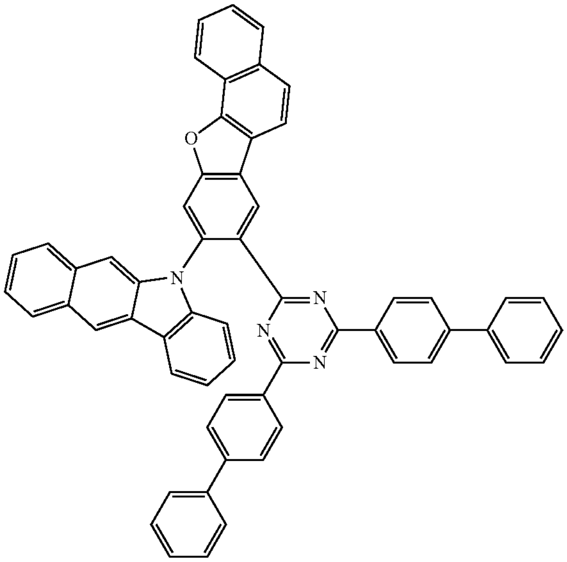
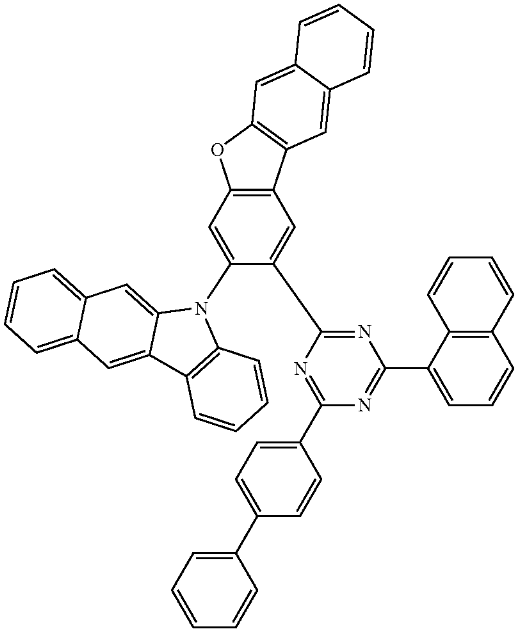
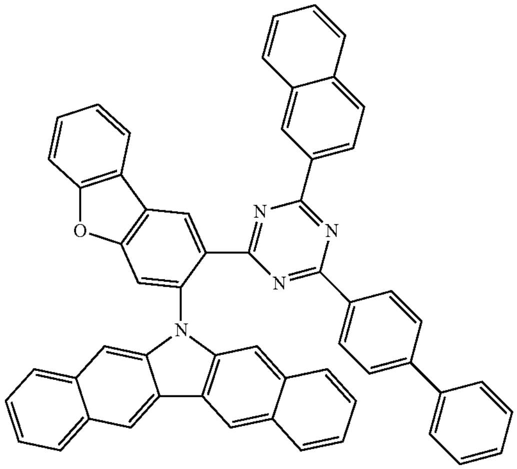
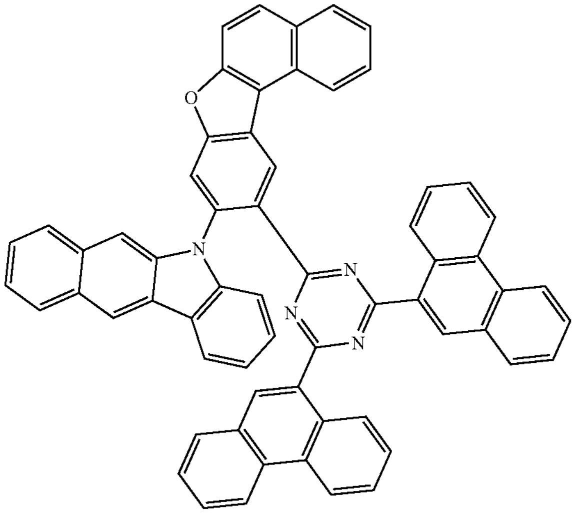

-continued
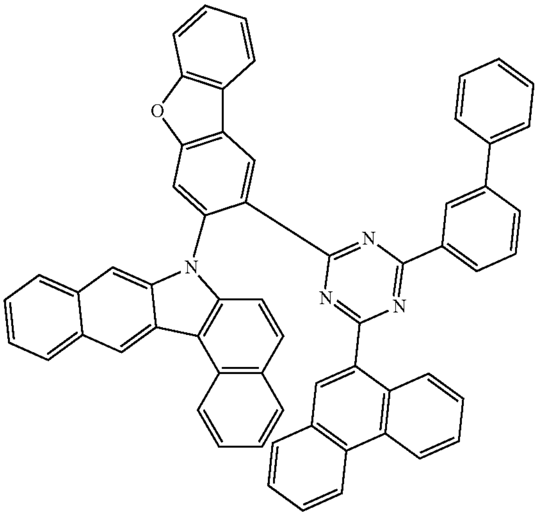
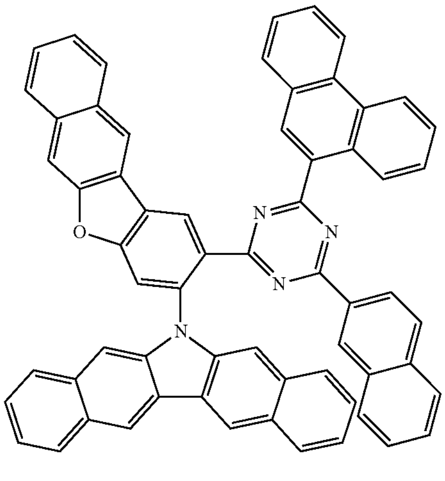 [SMILES: c1ccc2cc(-c3nc(-c4cc5c(cc4-n4c6cc7ccccc7cc6c6cc7ccccc7cc64)oc4cc6ccccc6cc45)nc(-c4cc5ccccc5c5ccccc45)n3)ccc2c1]
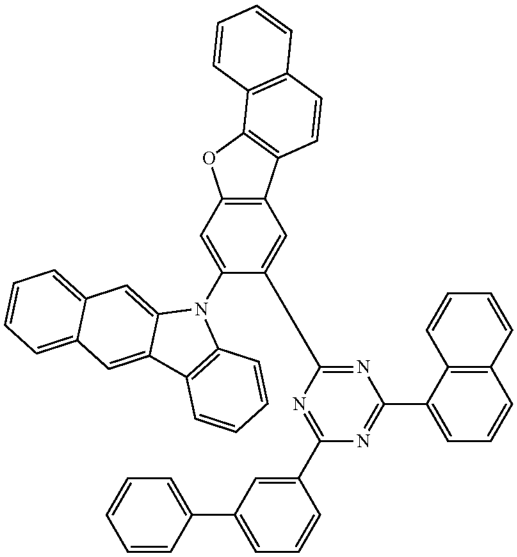
-continued
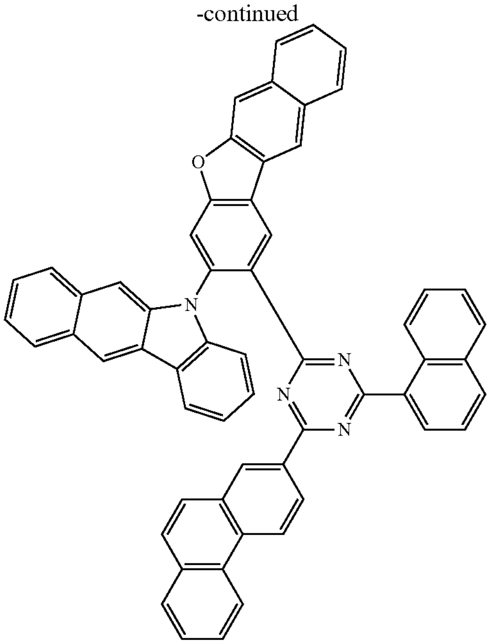
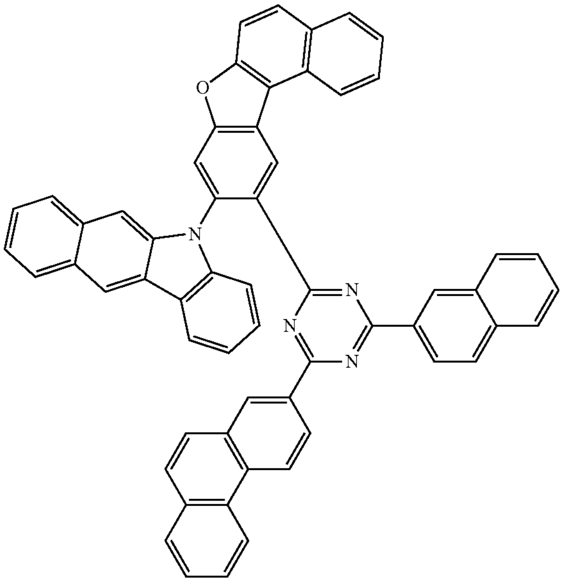

-continued
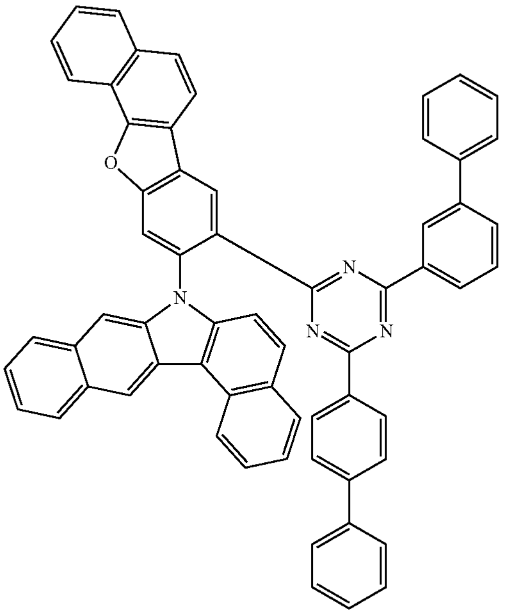
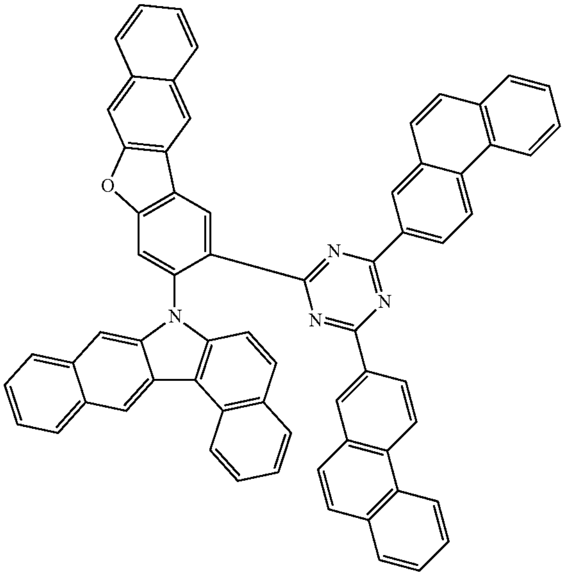
-continued
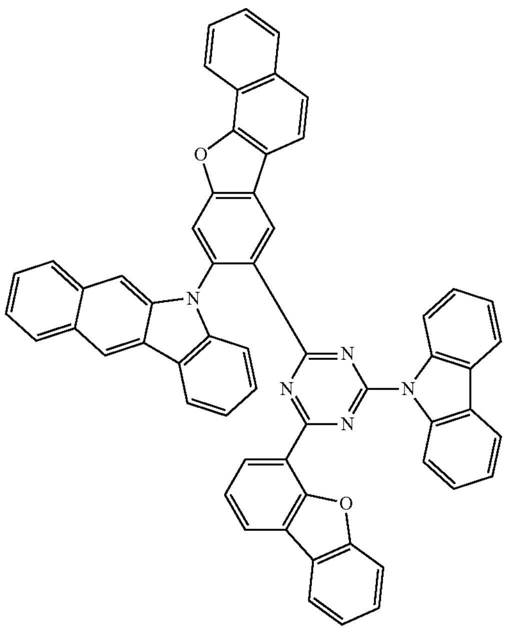
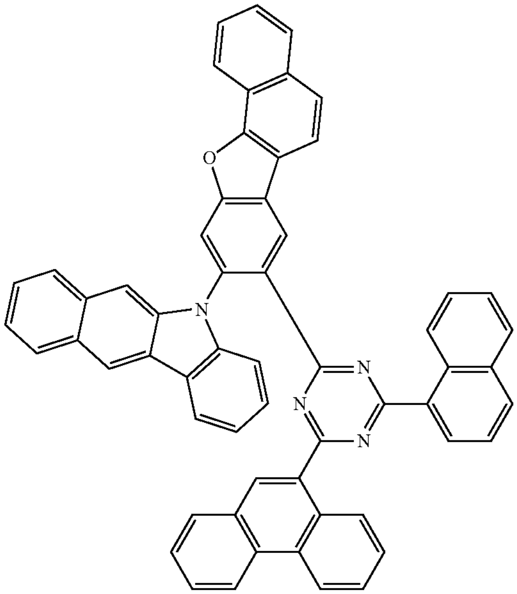
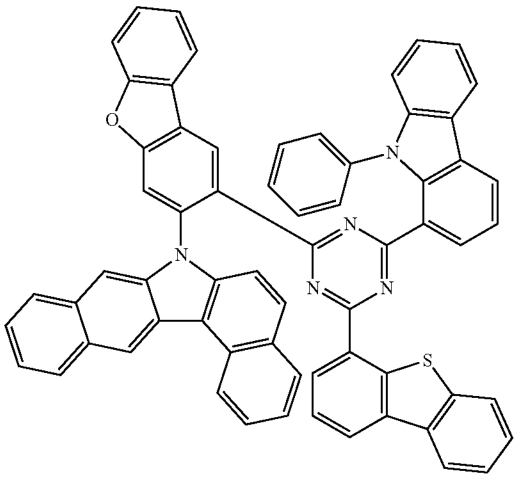

-continued
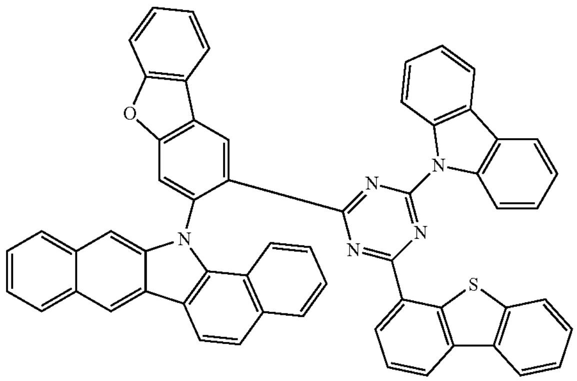
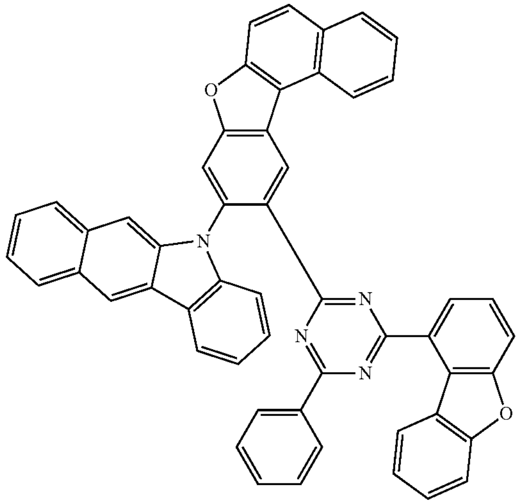
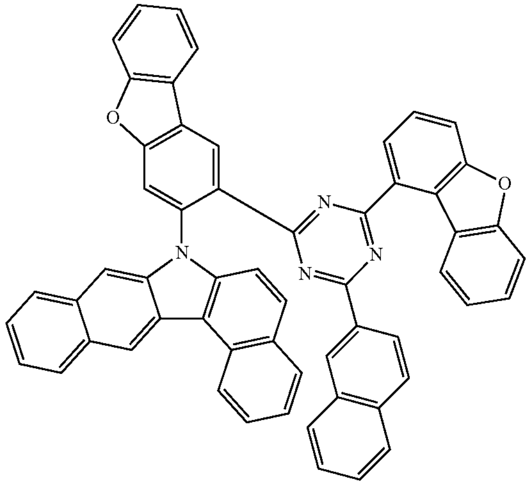
-continued
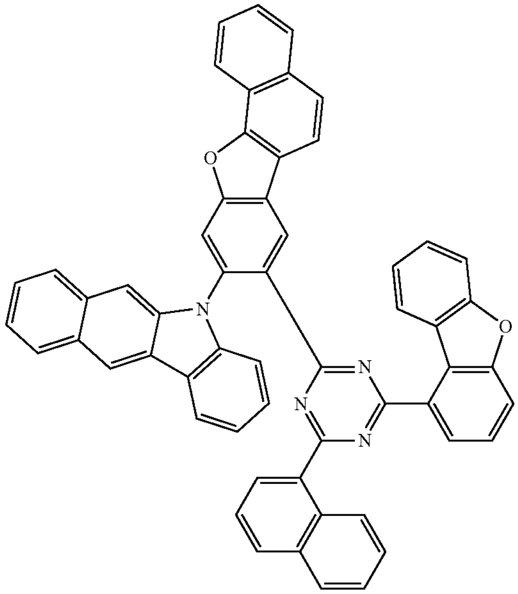
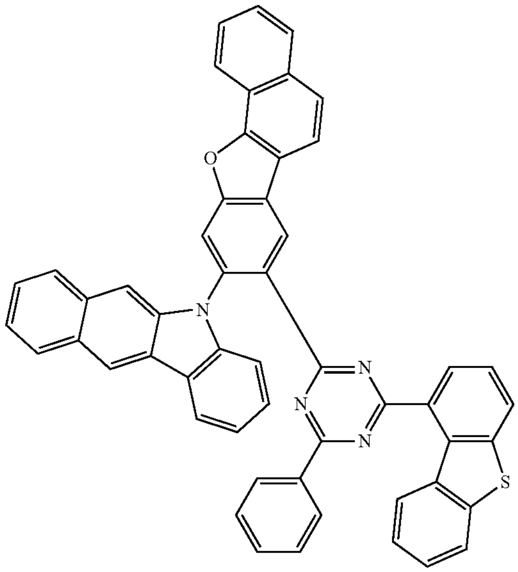

-continued
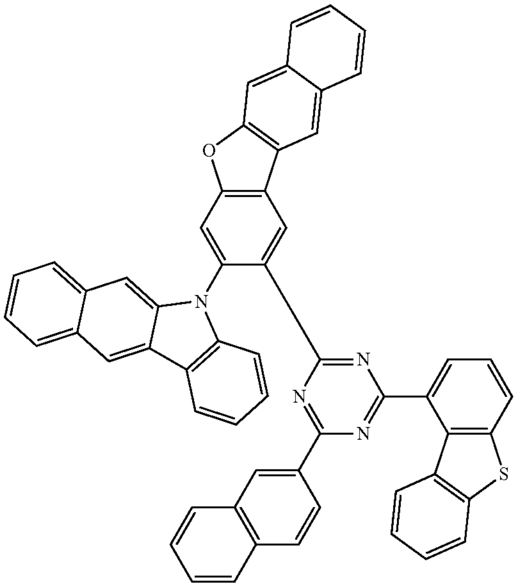
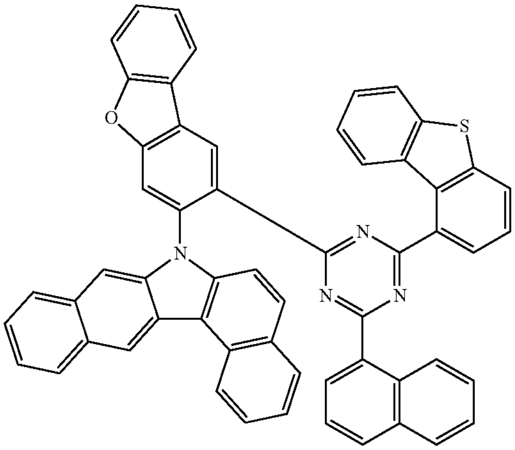
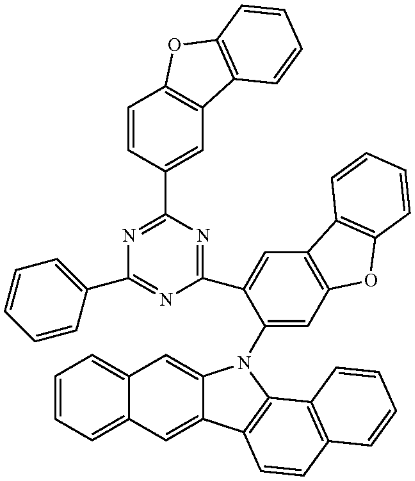
-continued
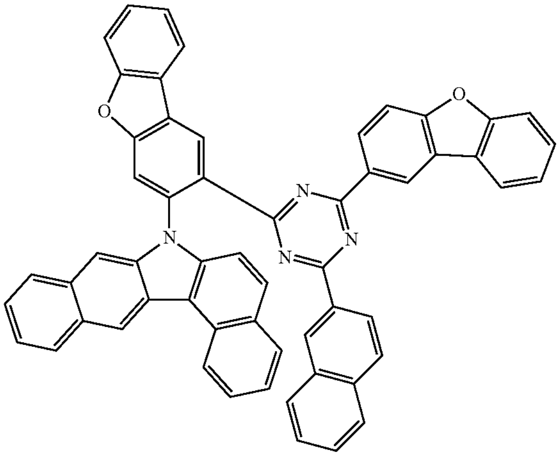
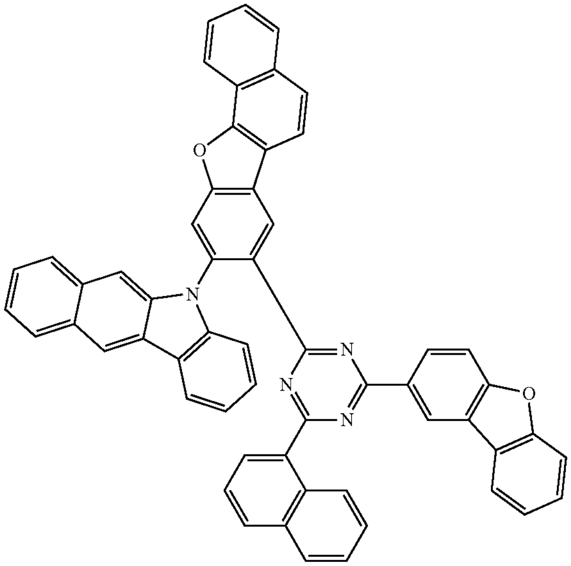
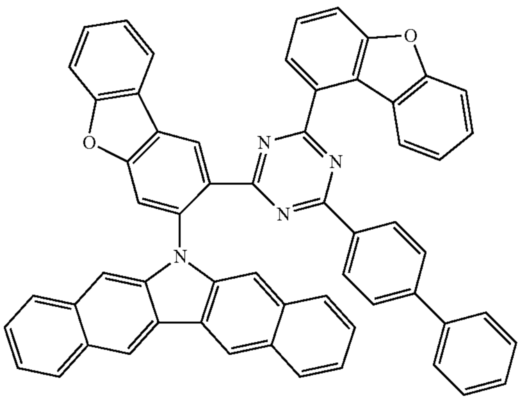

-continued
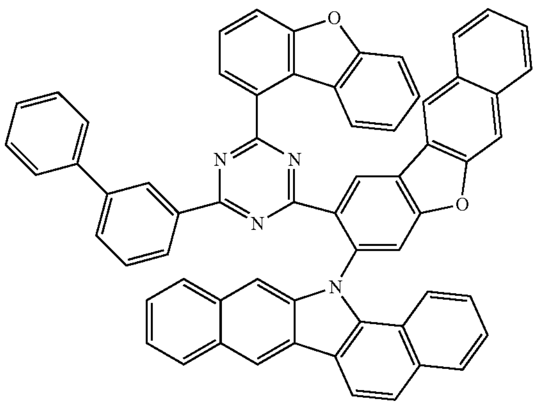
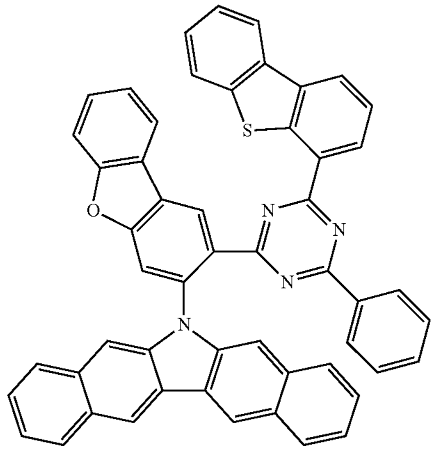
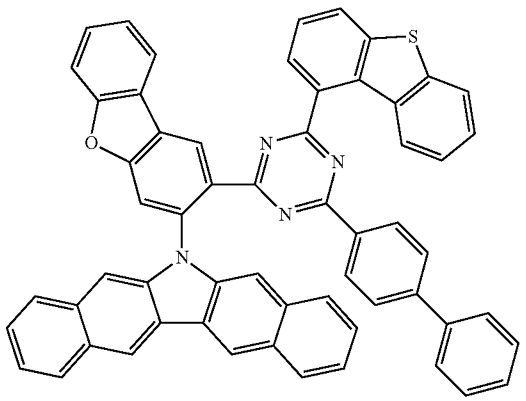
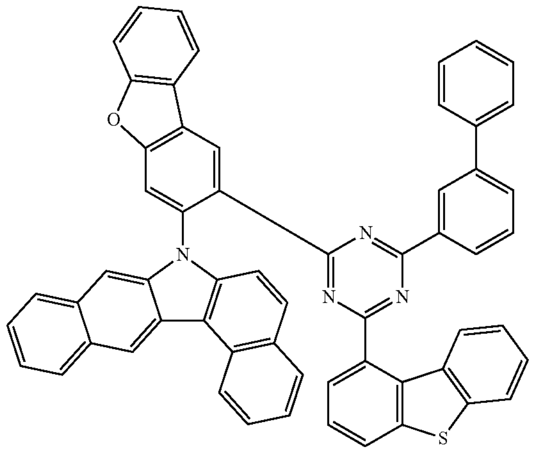
-continued
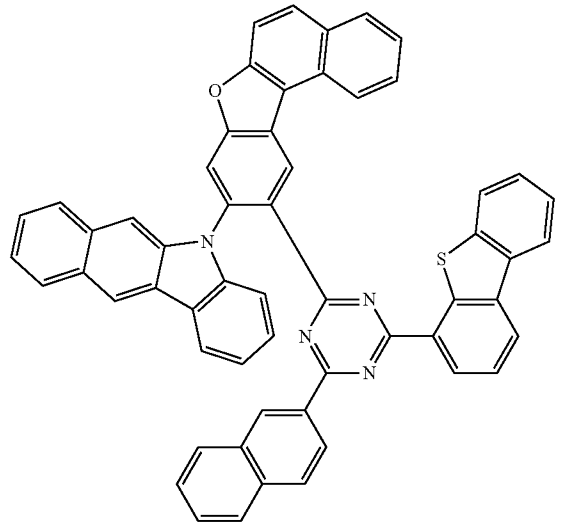
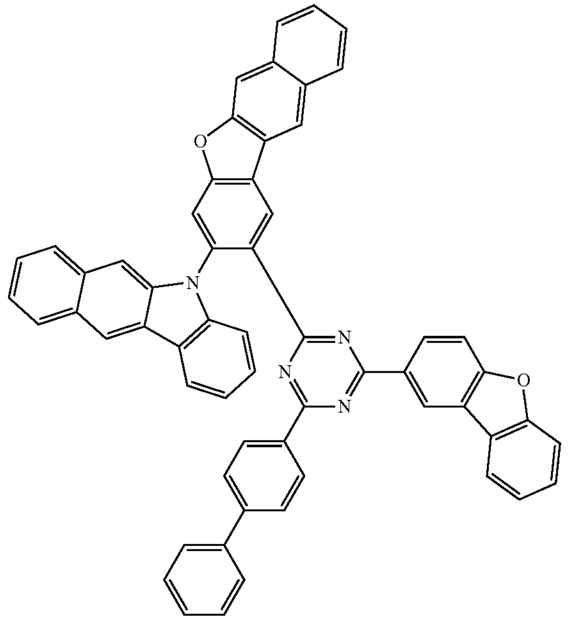
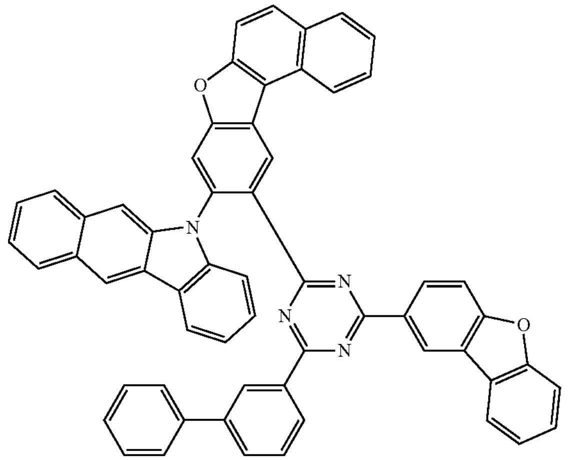

-continued
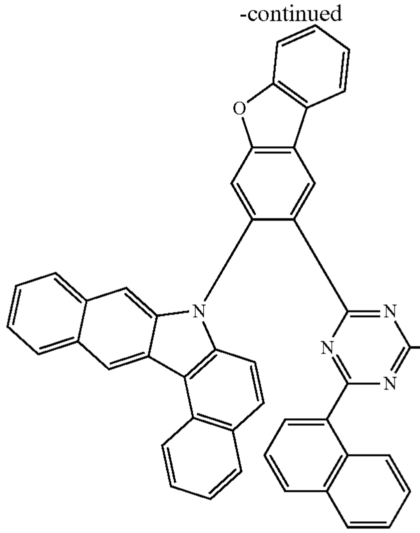
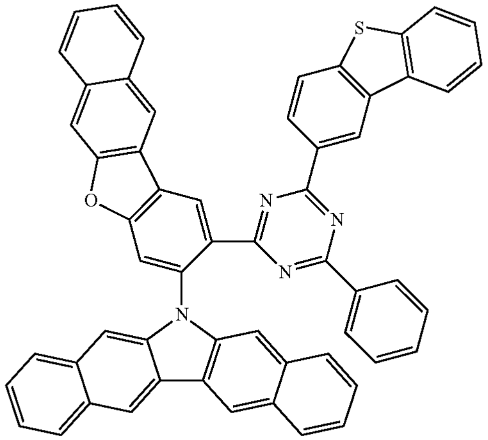
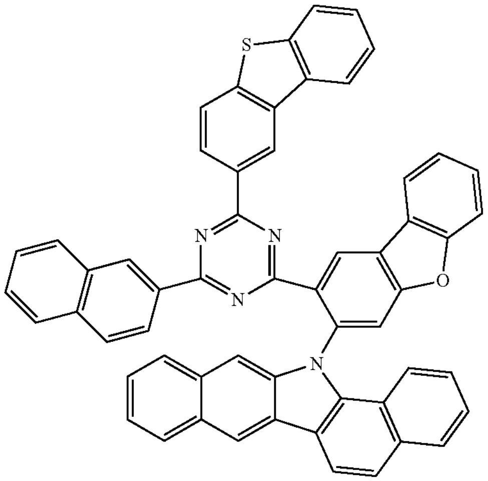
-continued
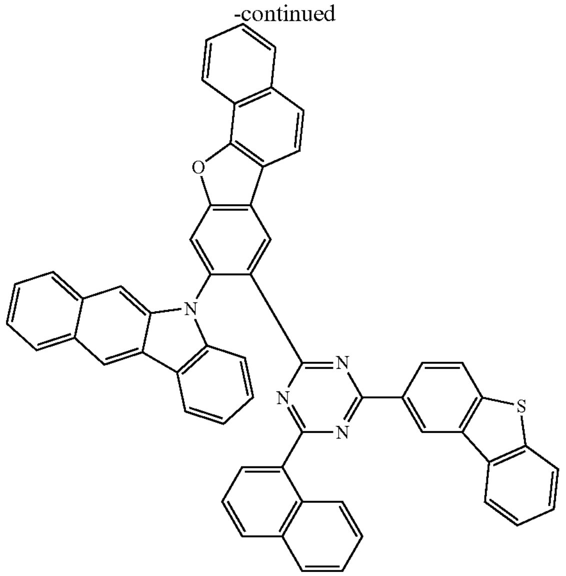
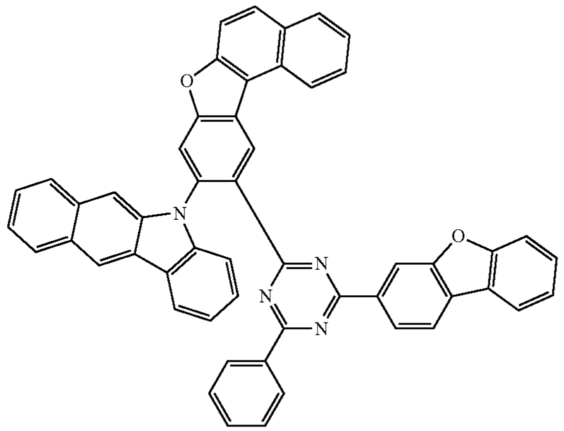
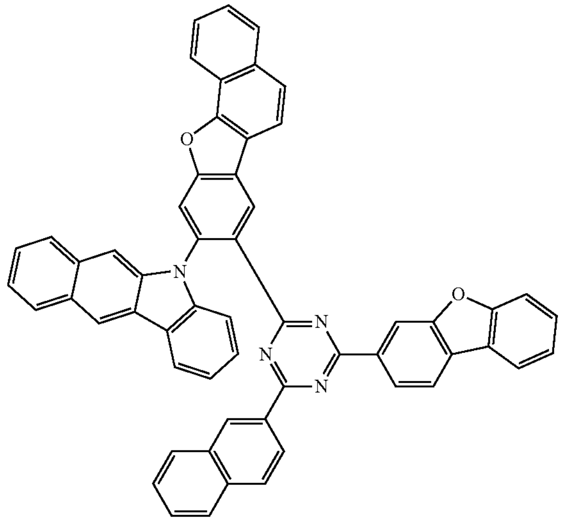

-continued
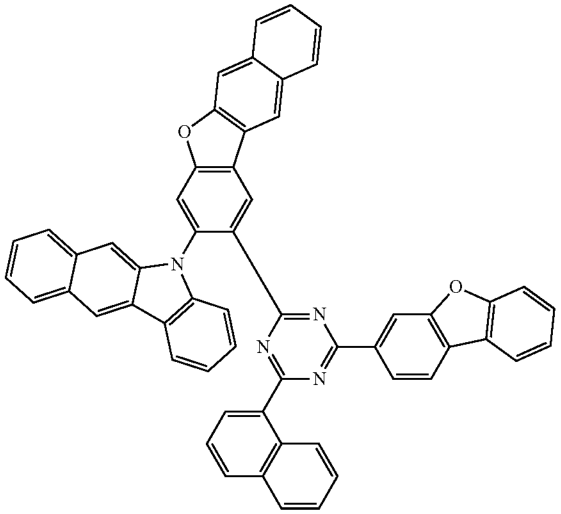
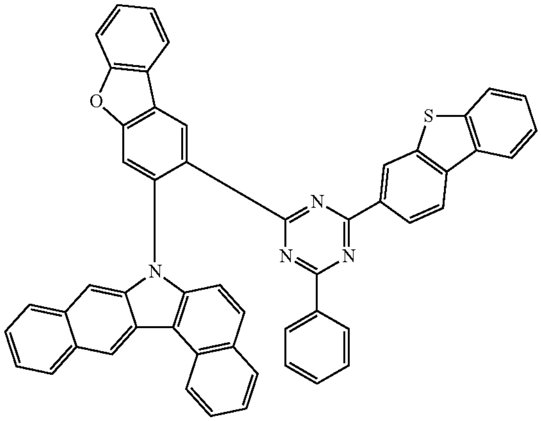
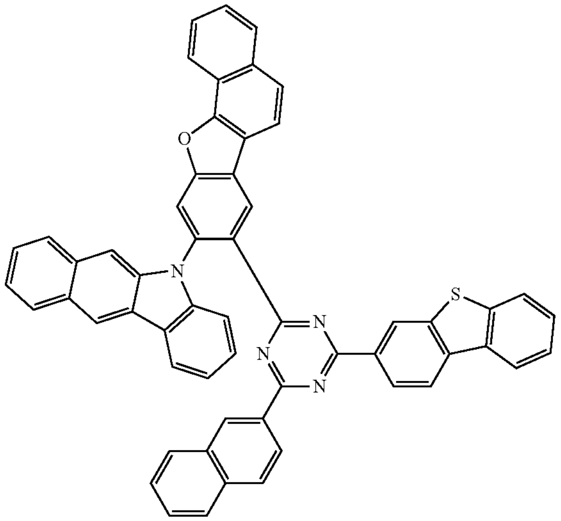
-continued
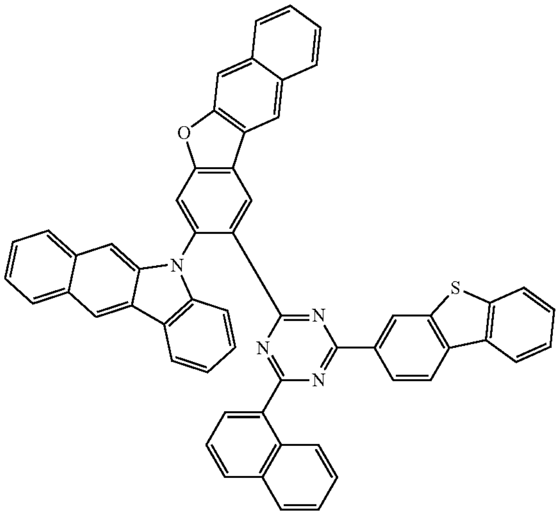
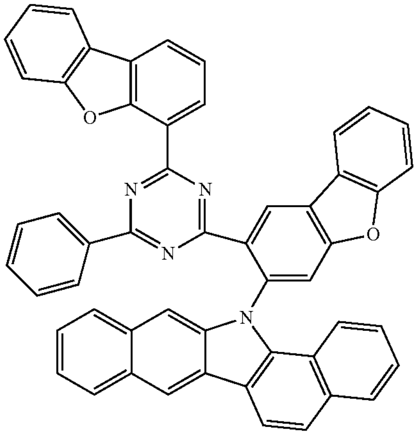
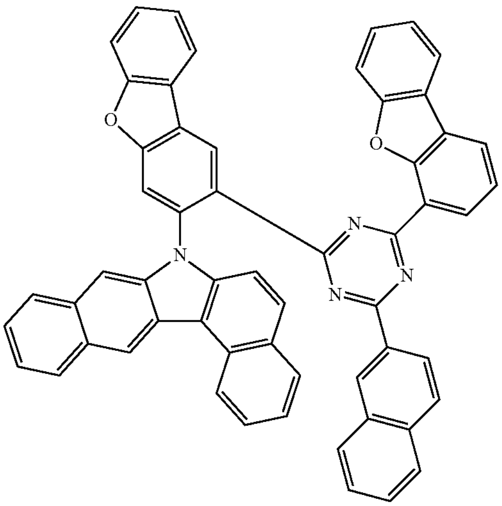

-continued
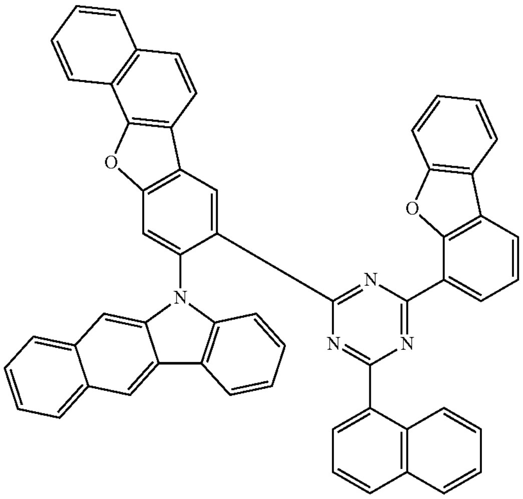
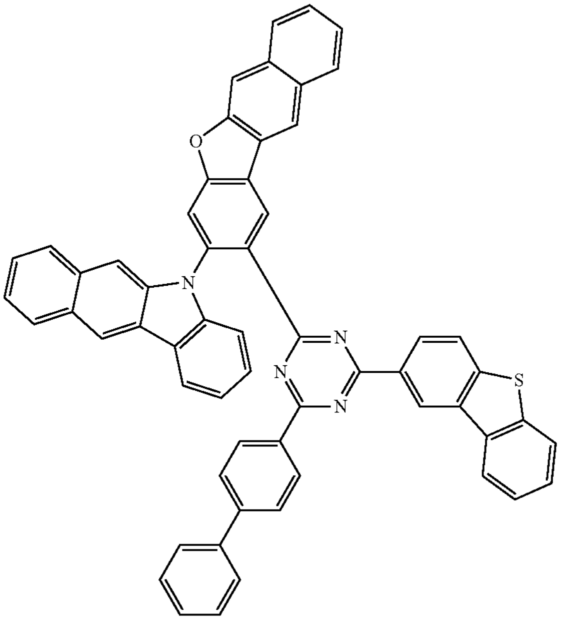
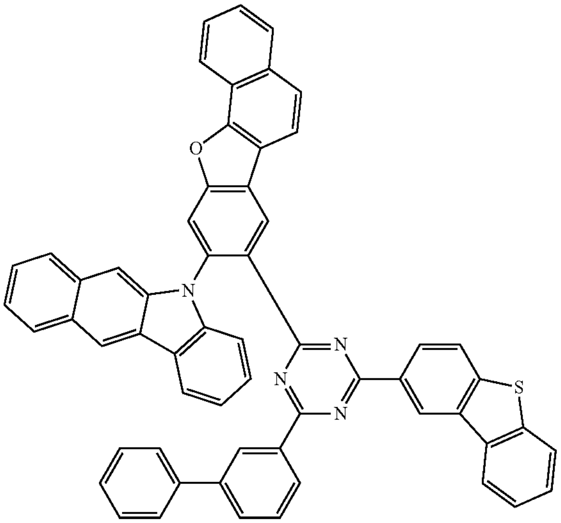
-continued
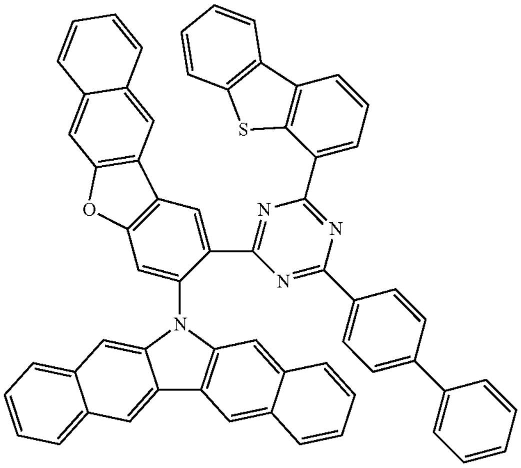
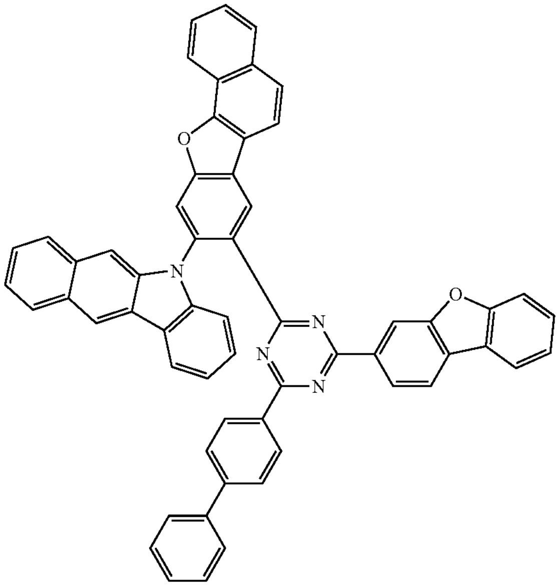
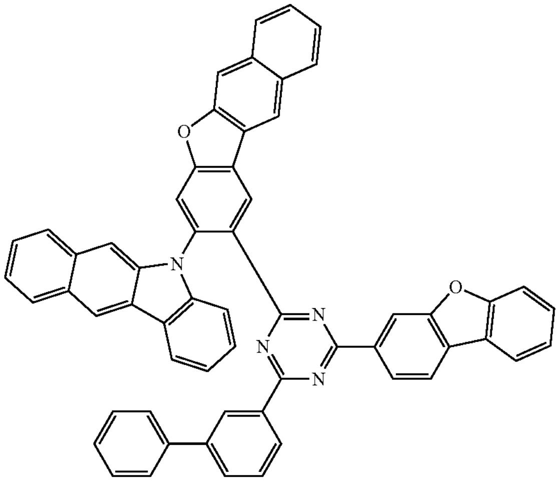

-continued
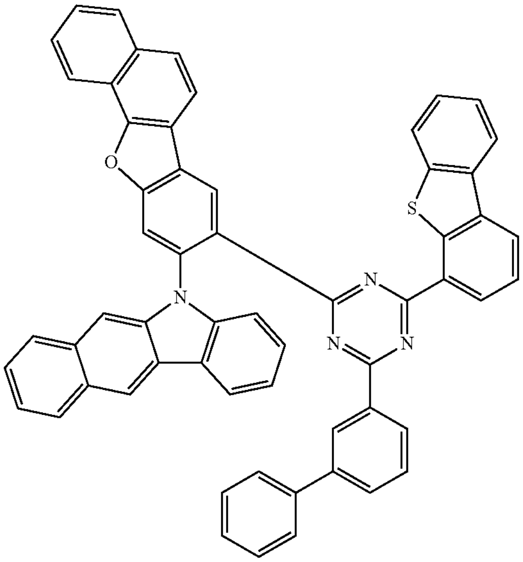
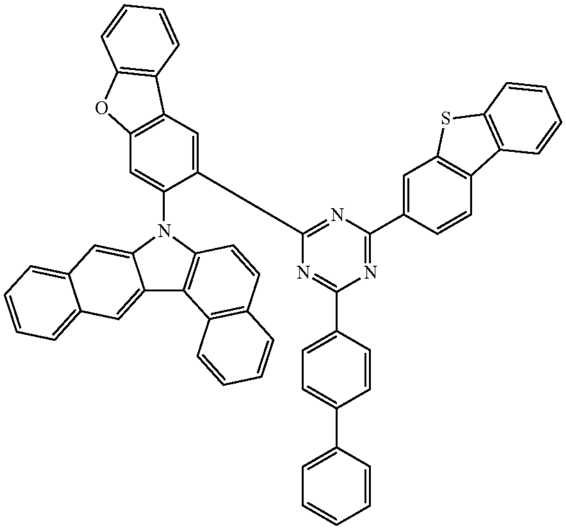
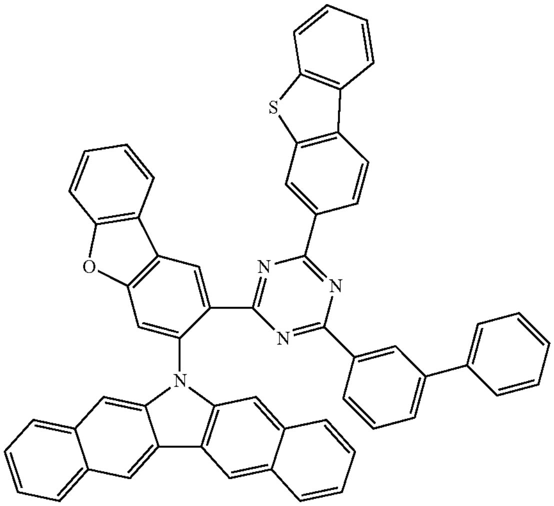
-continued
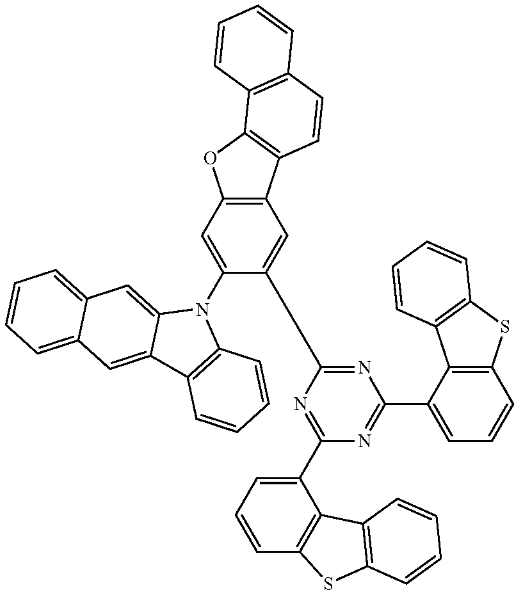
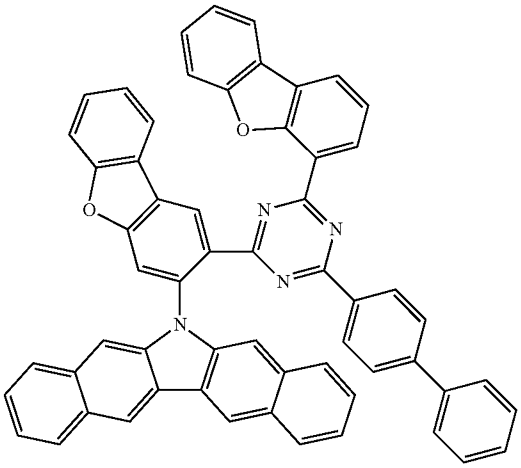
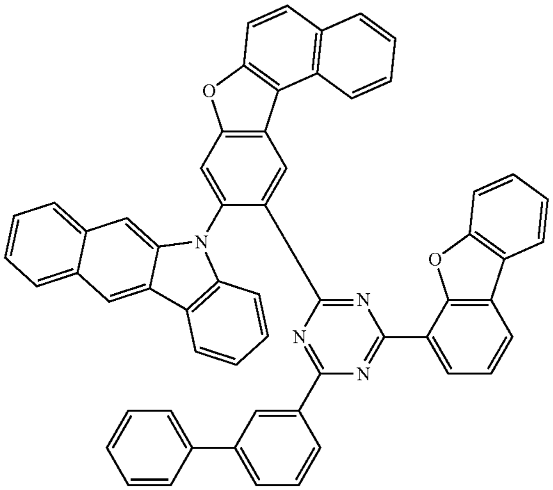

-continued
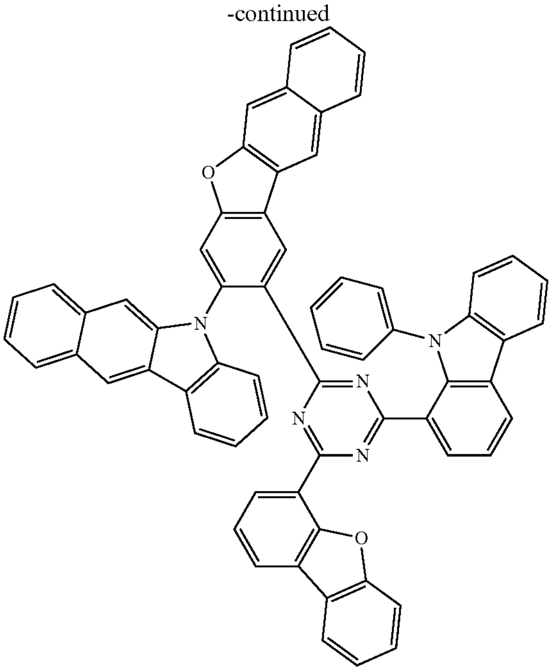
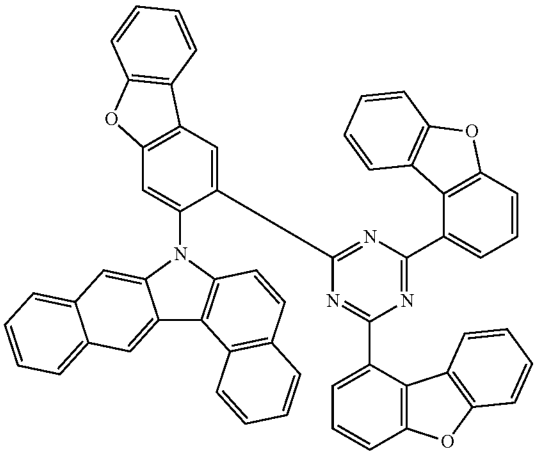
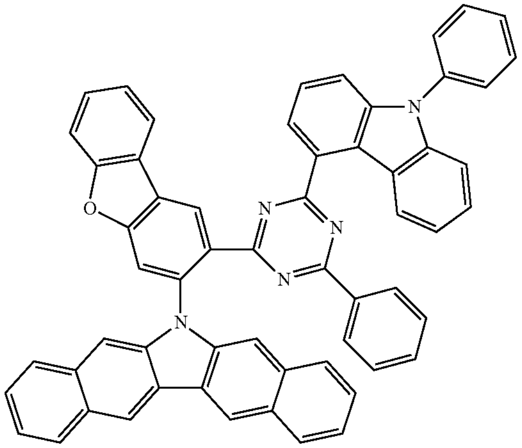
-continued
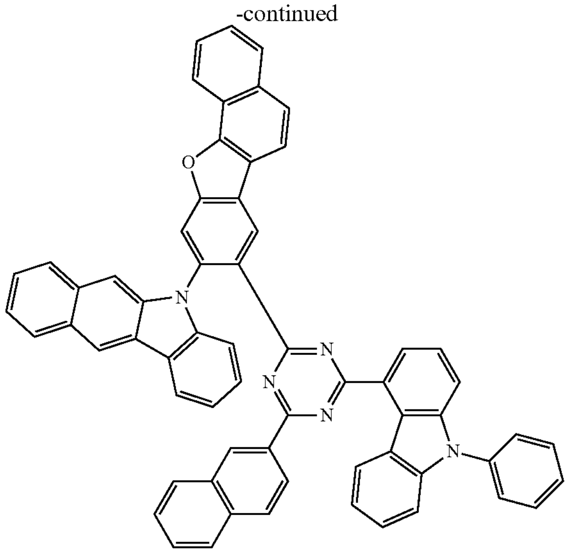
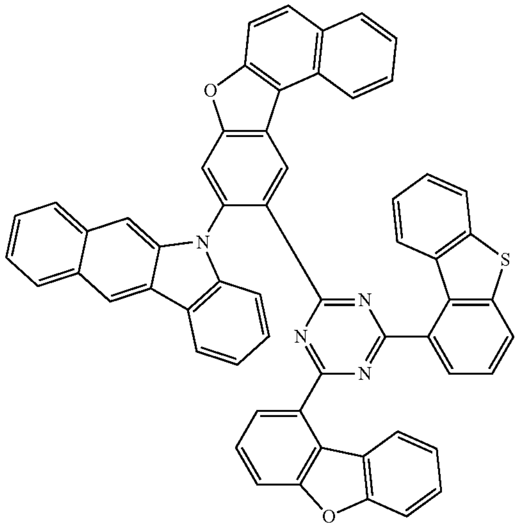
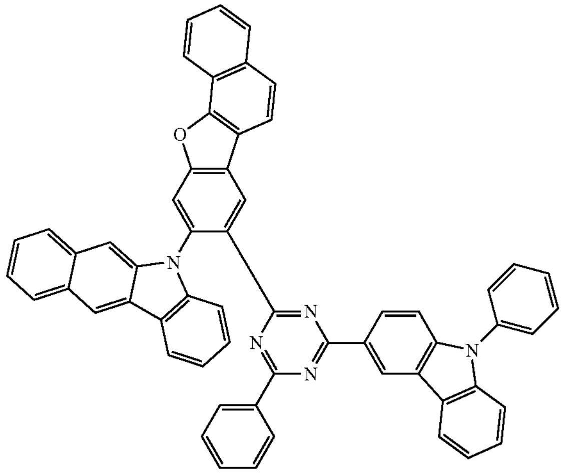

-continued
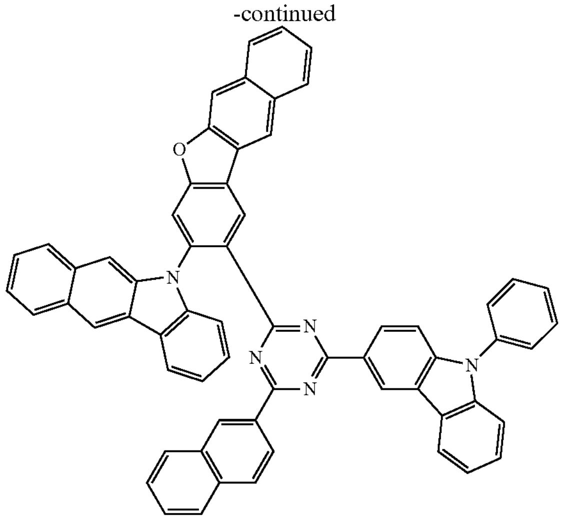
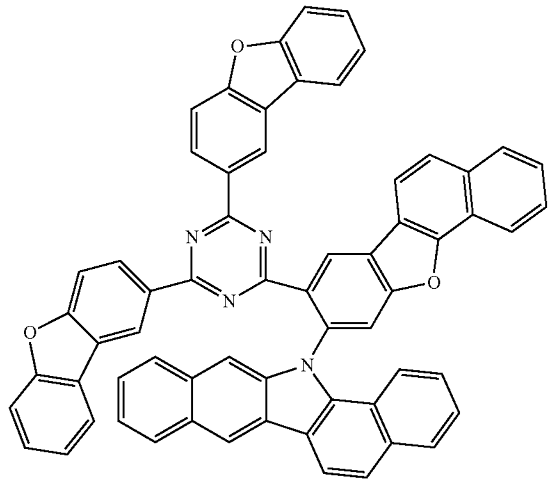
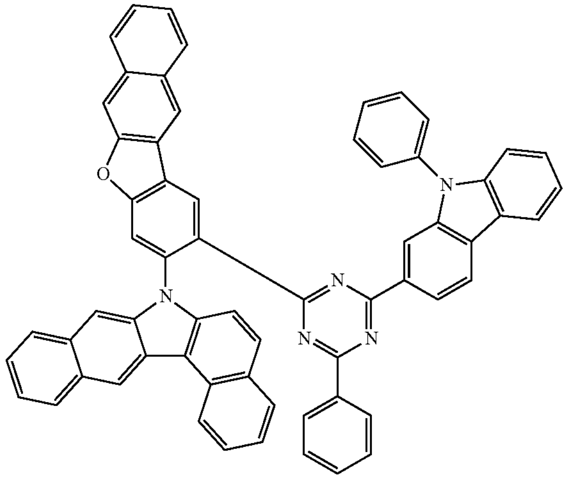
-continued
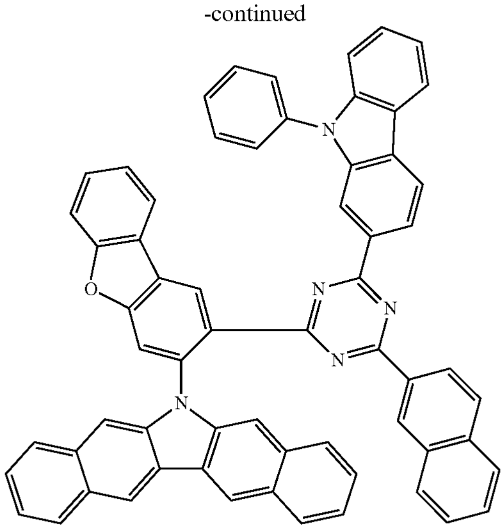
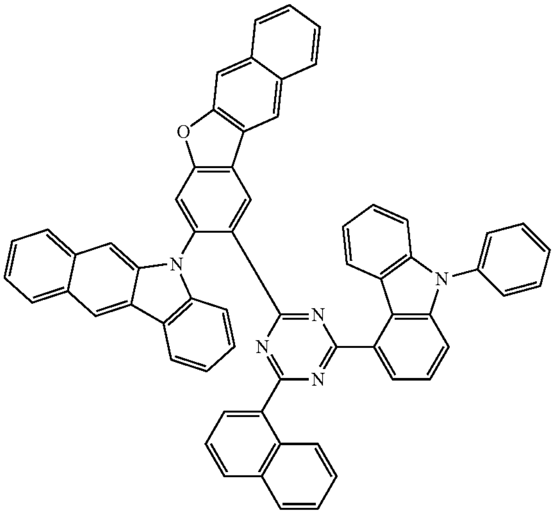
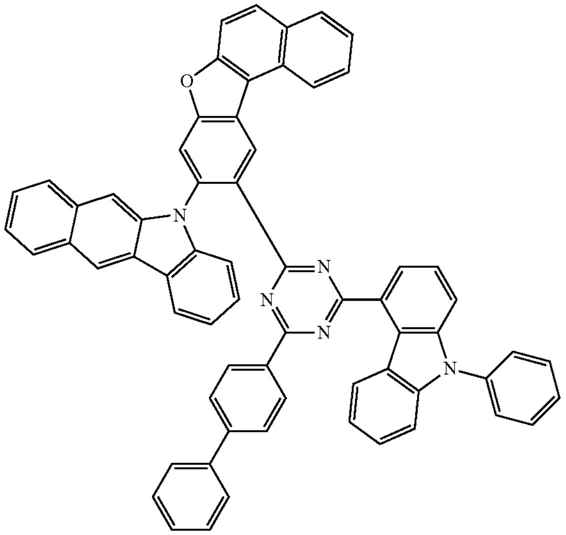

-continued
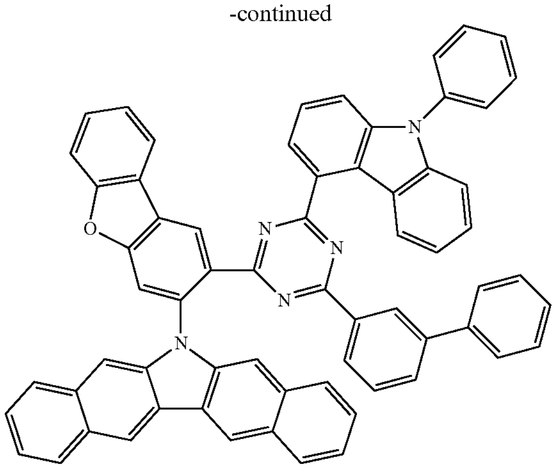
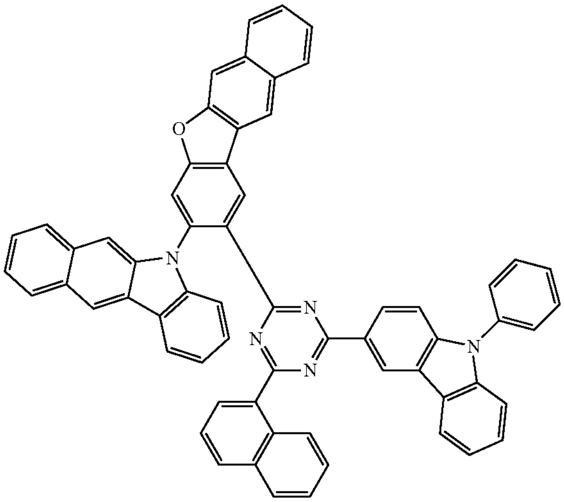
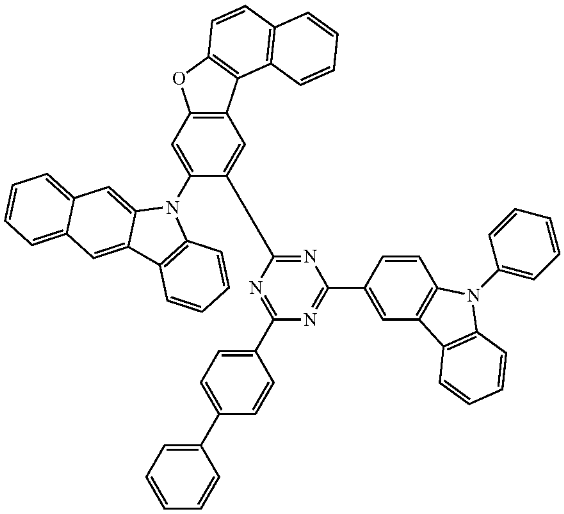
-continued
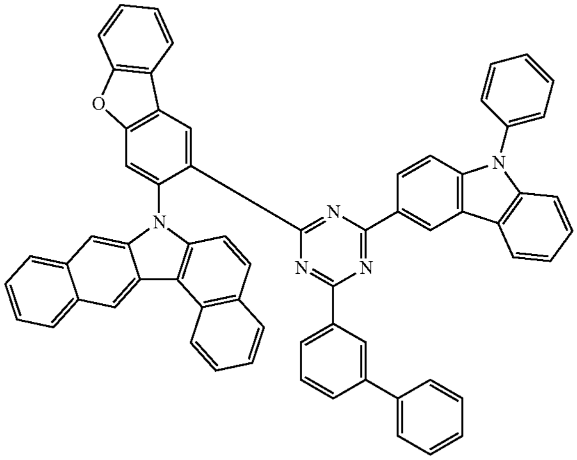
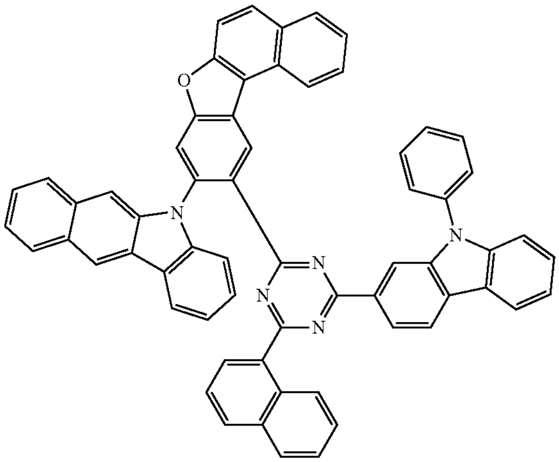
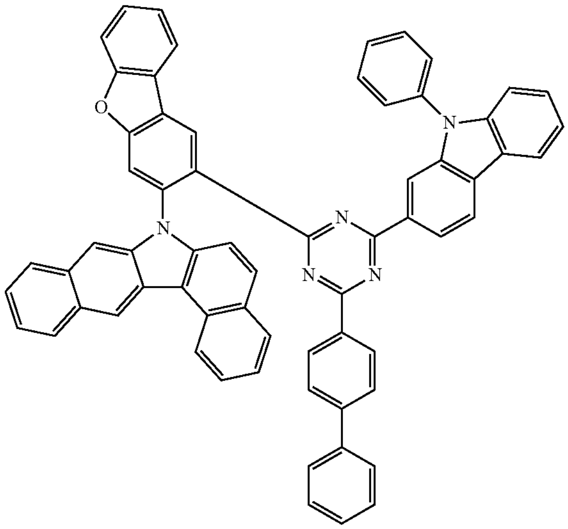

-continued
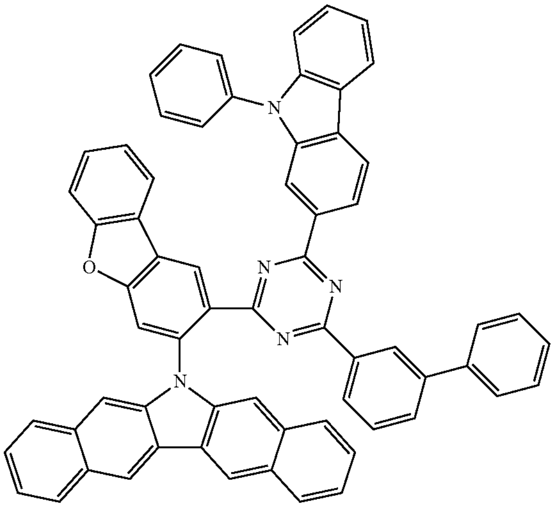
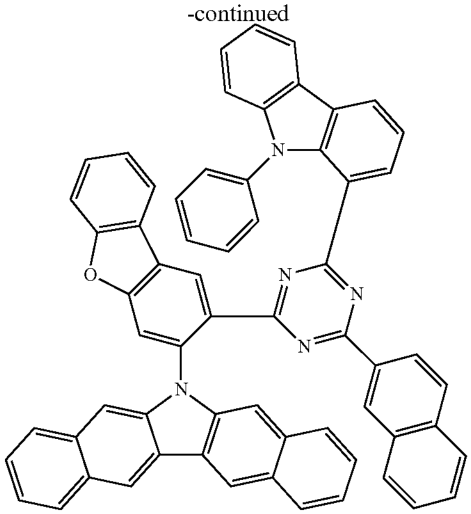
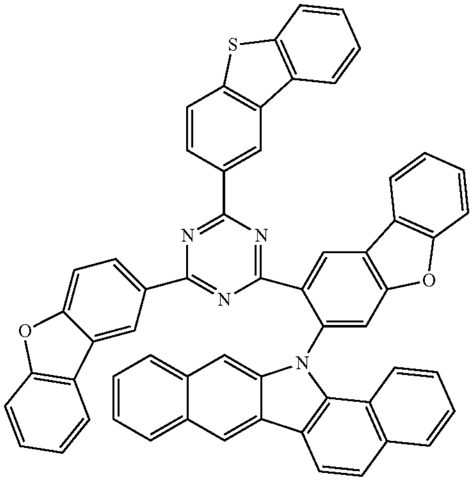
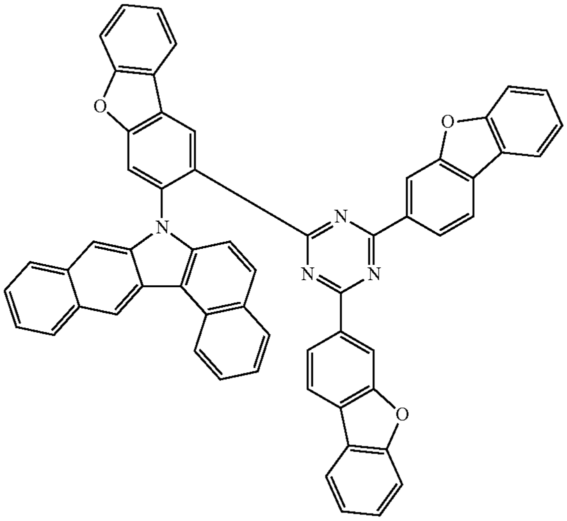
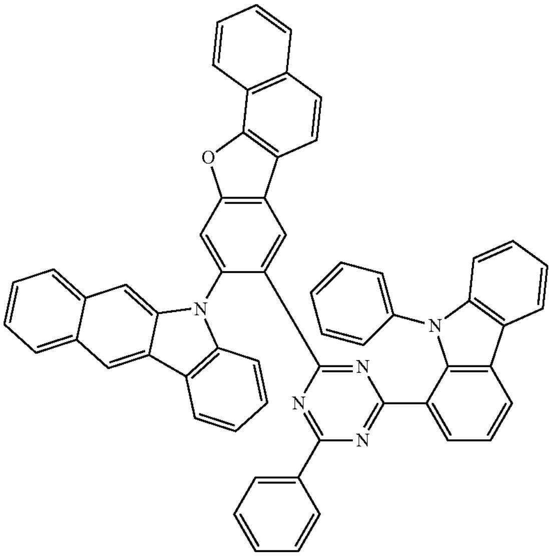
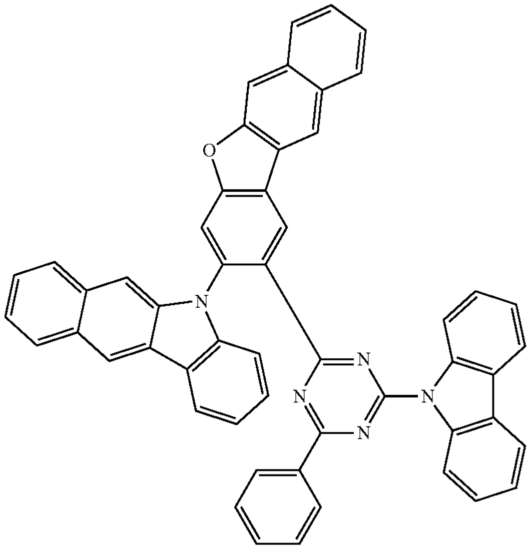
-continued -continued
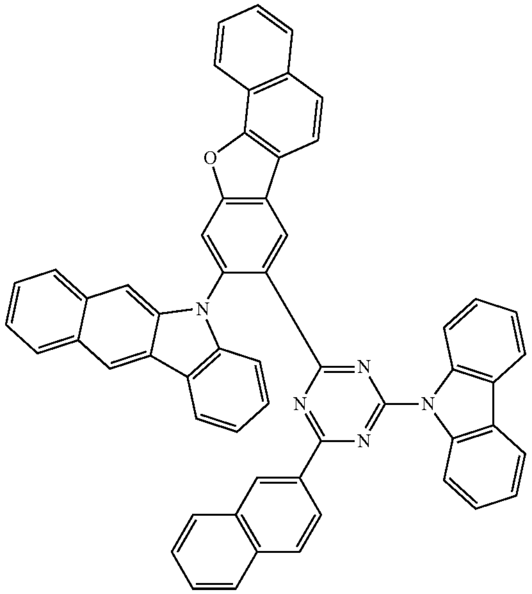
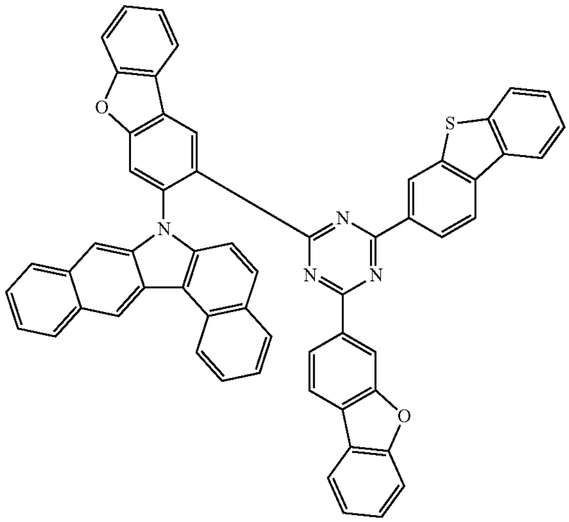
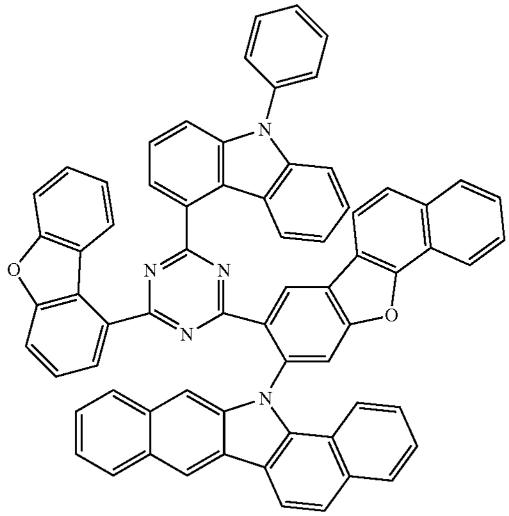
-continued
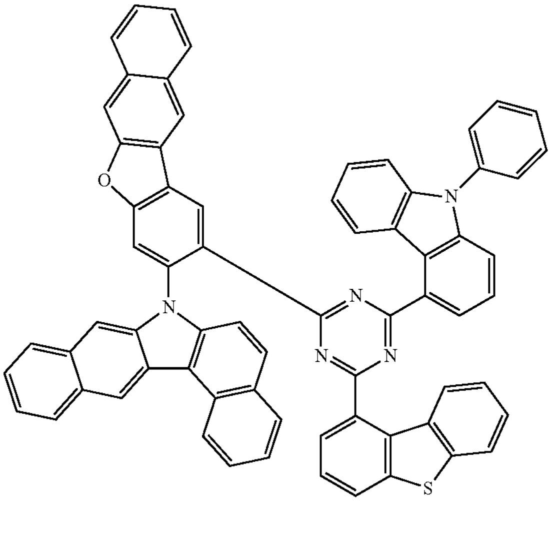
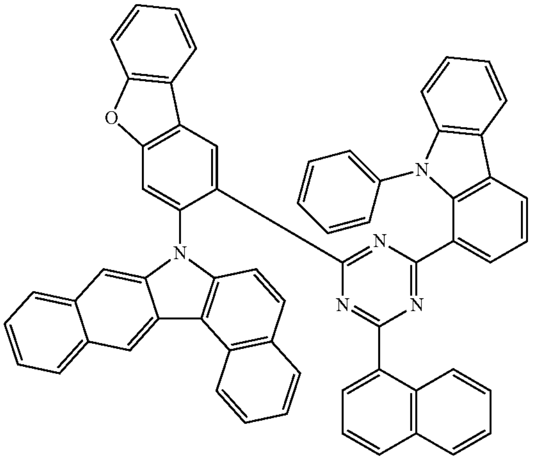
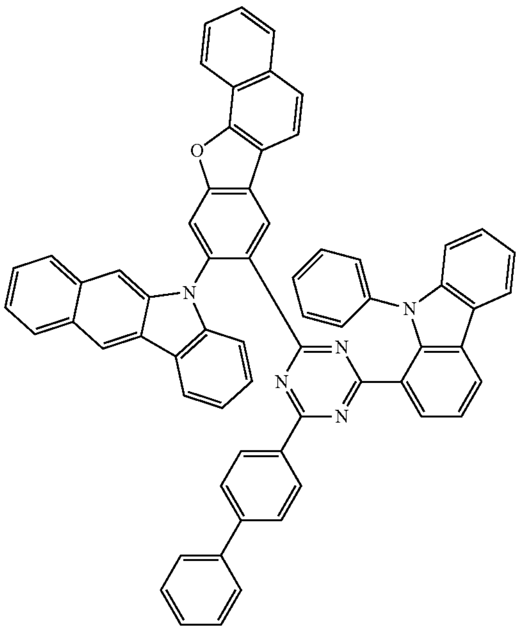

-continued
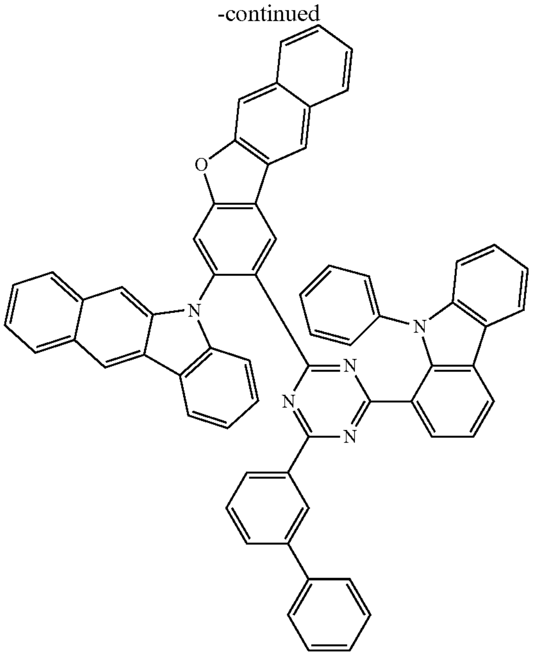
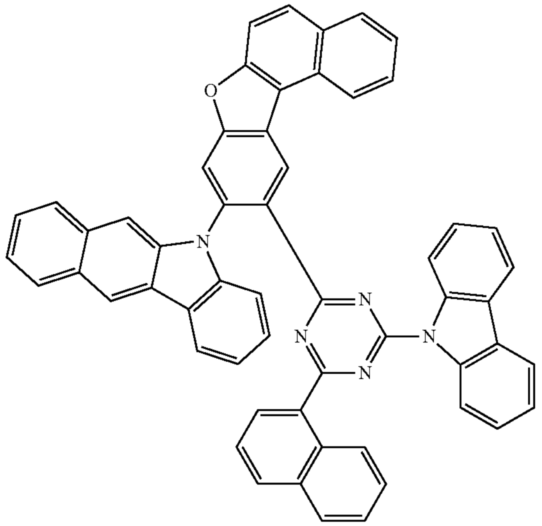
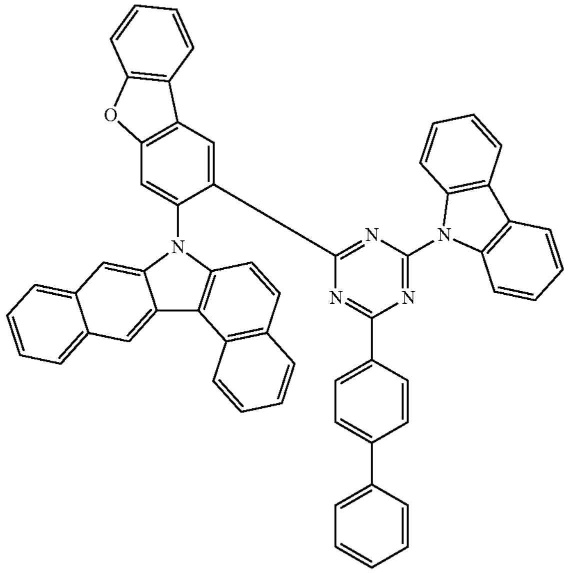
-continued
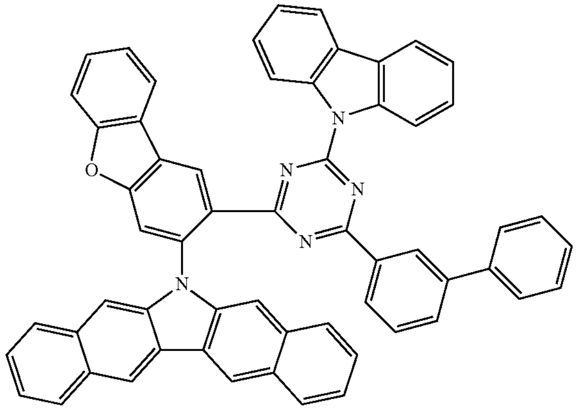
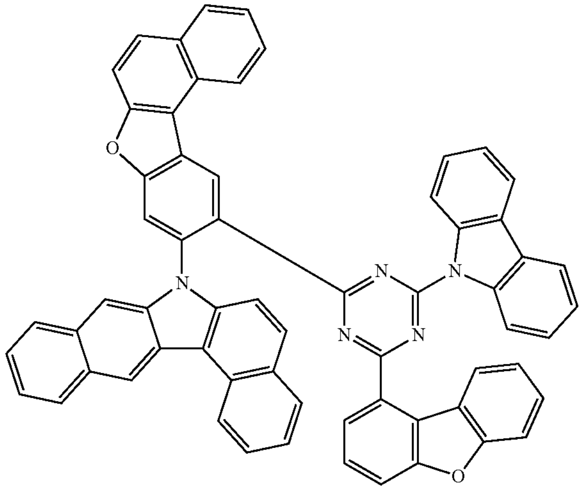
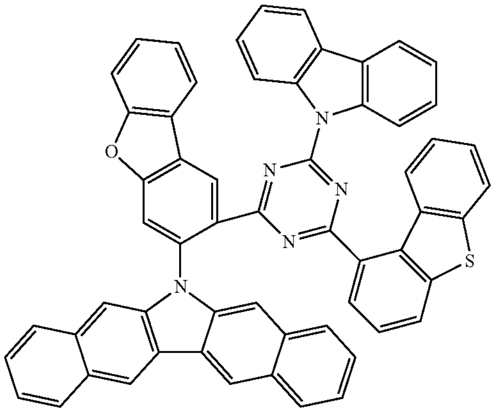

-continued
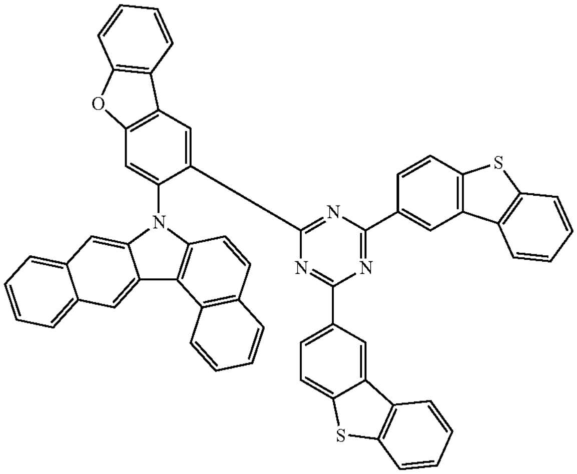
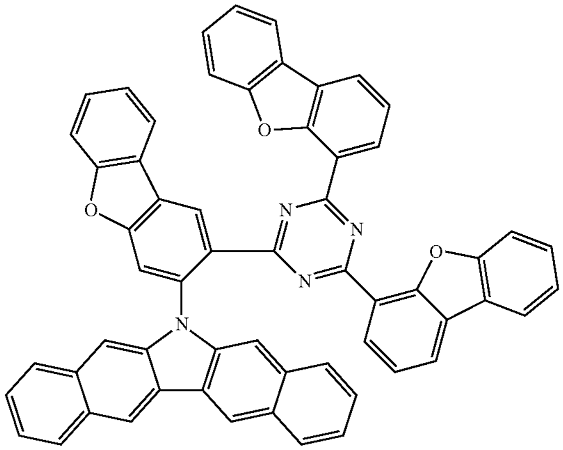
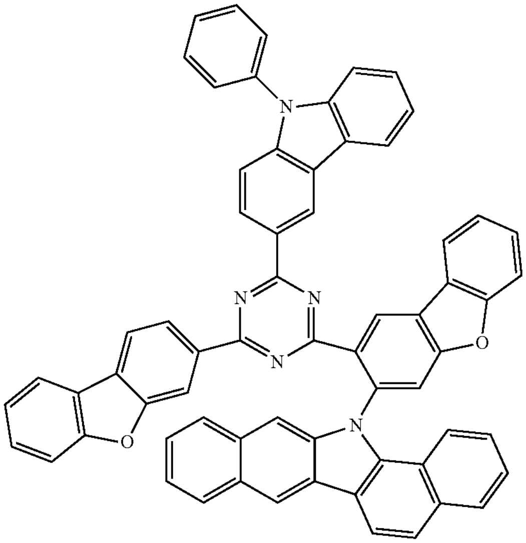
-continued
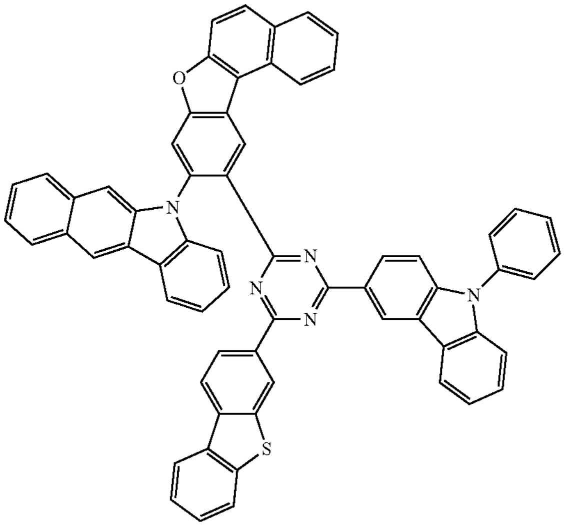
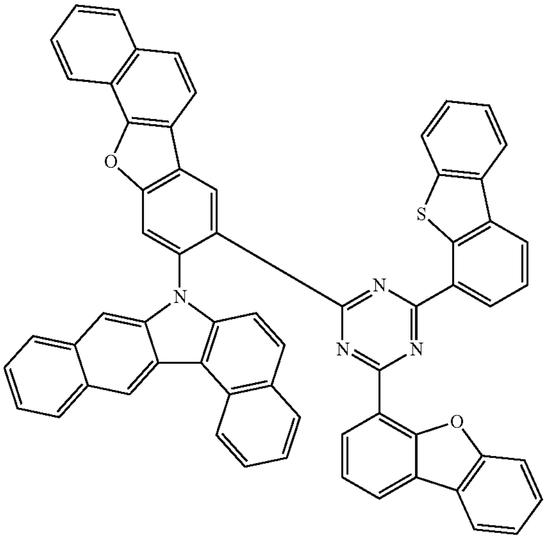
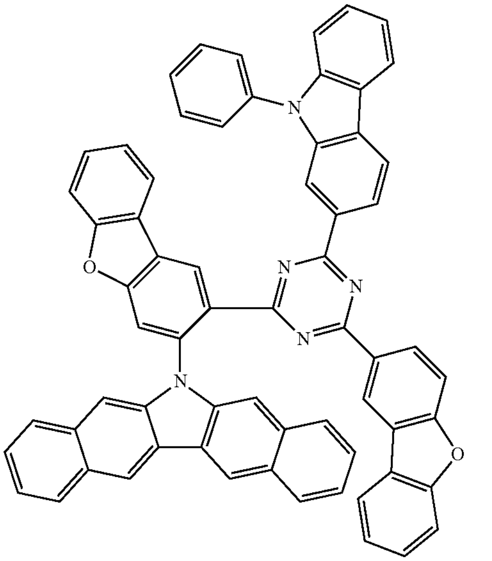

-continued
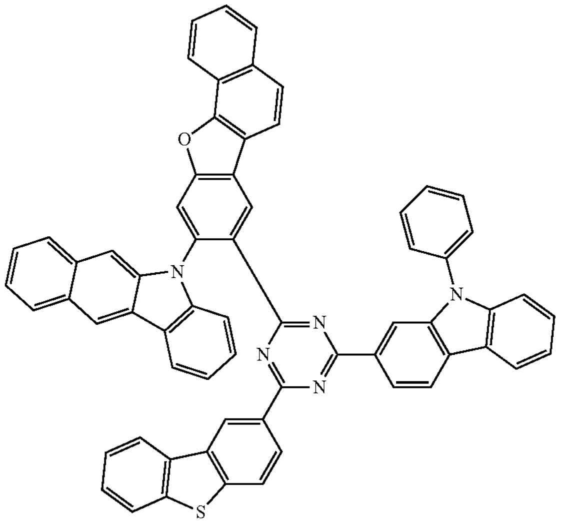
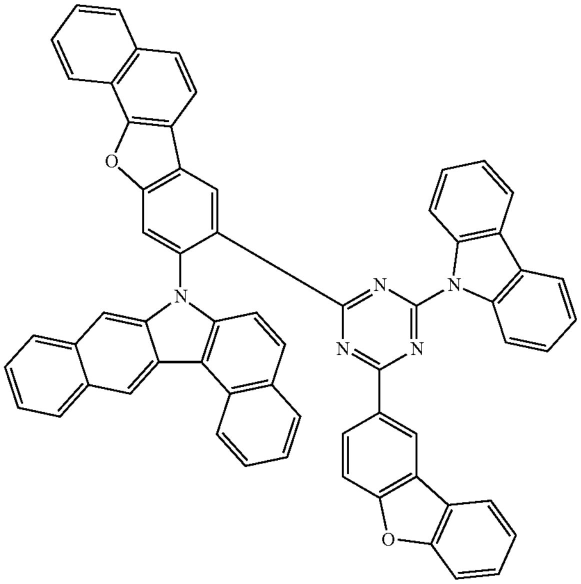
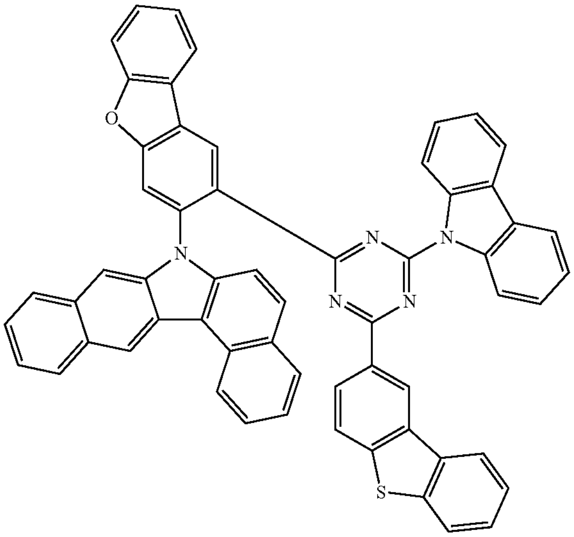
-continued
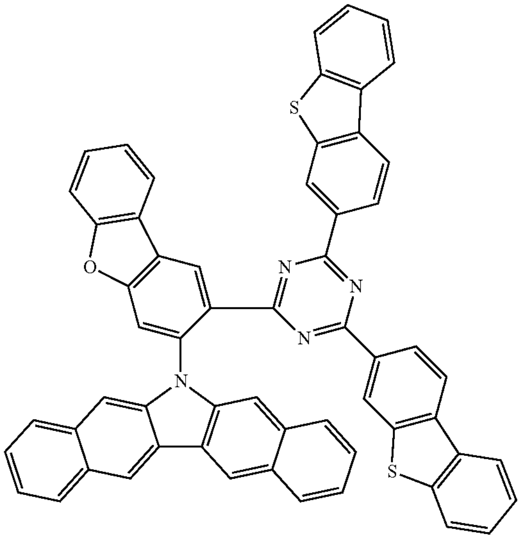
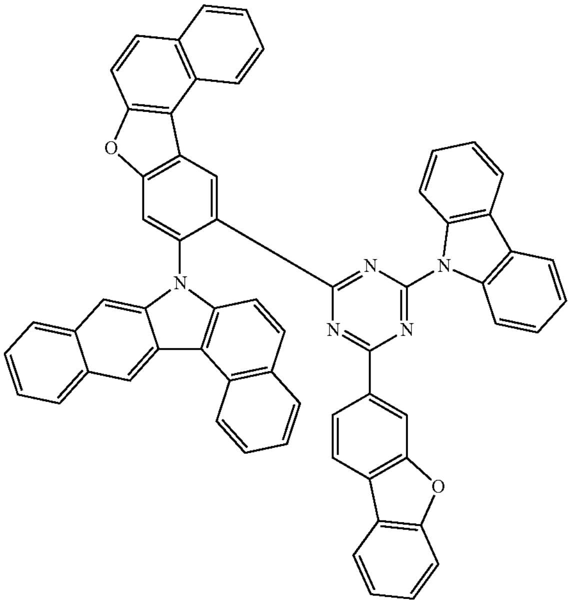

-continued
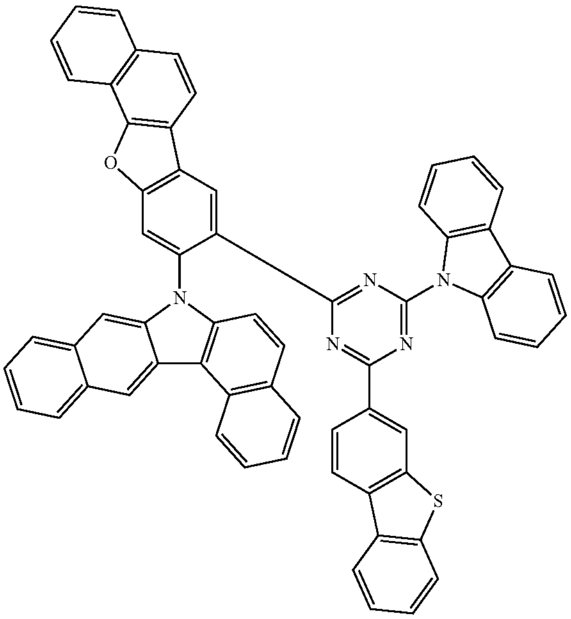
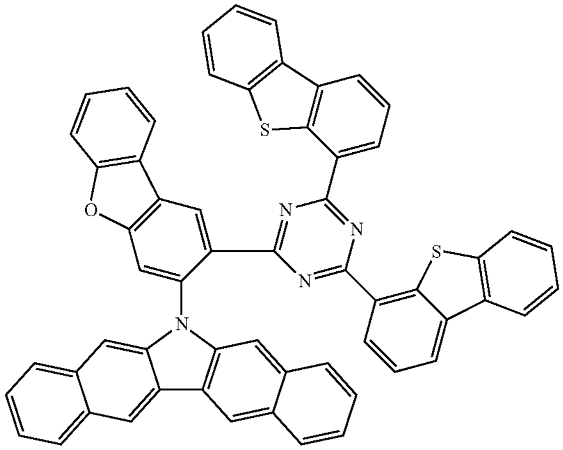
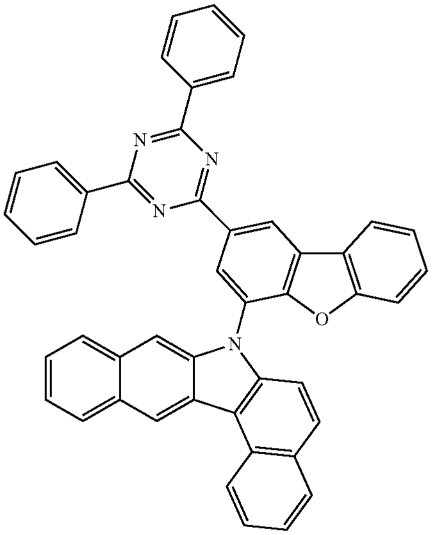
-continued
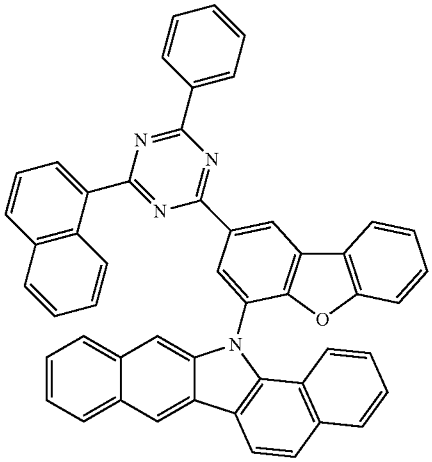
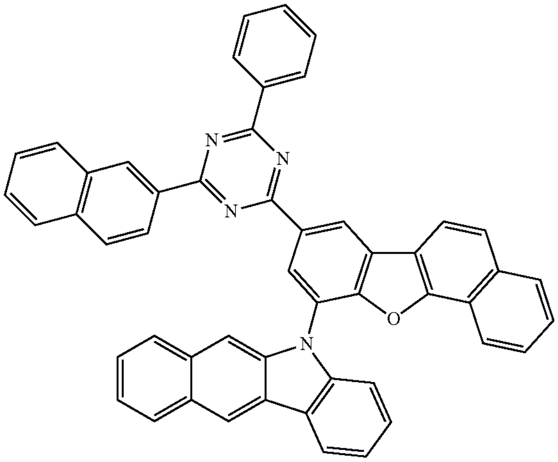
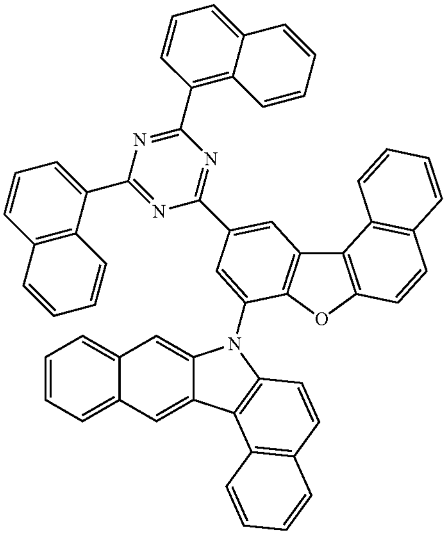

-continued
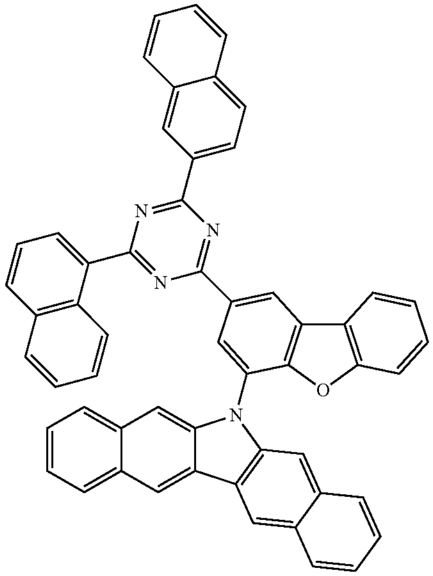
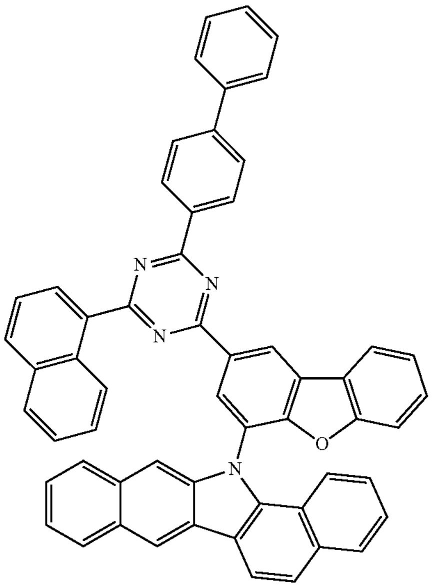
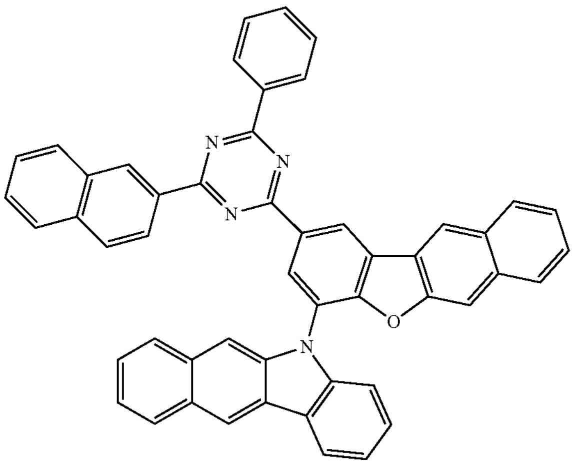
-continued
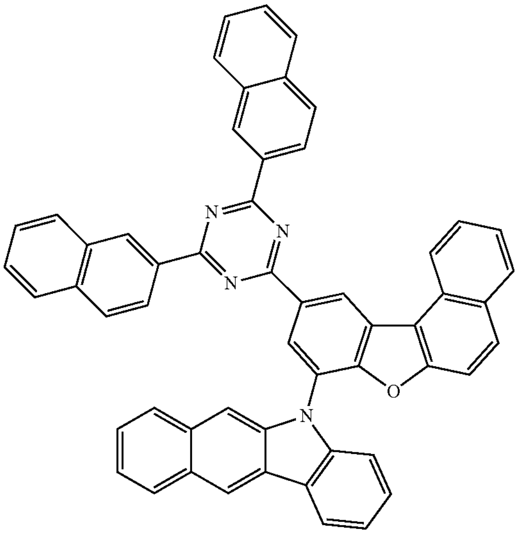
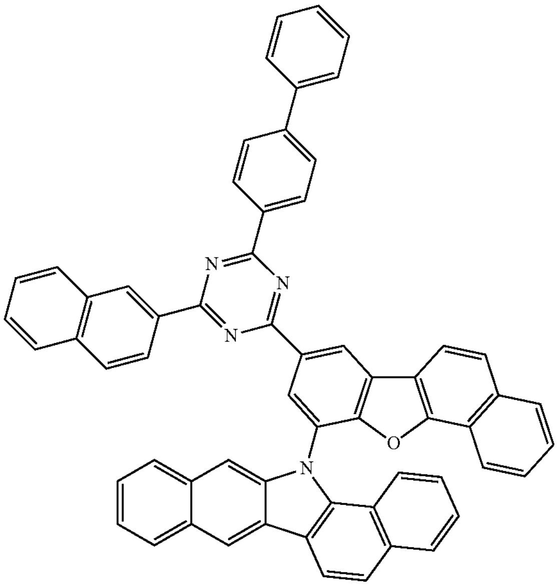
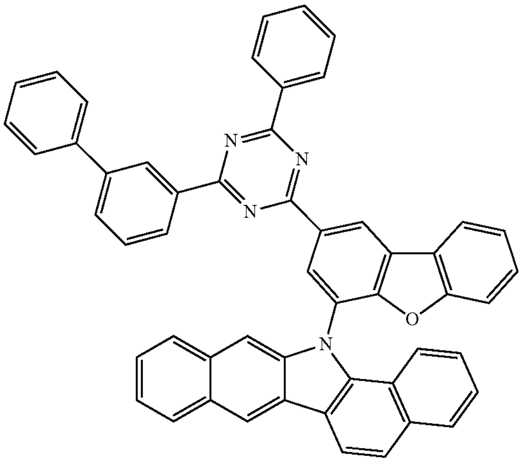

-continued
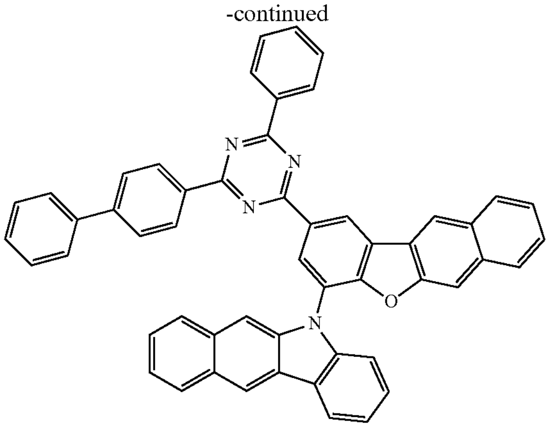
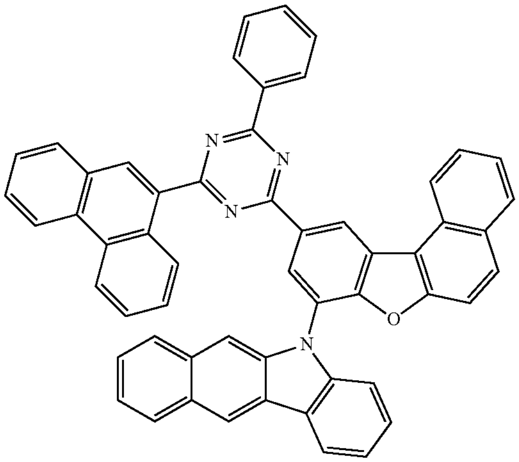
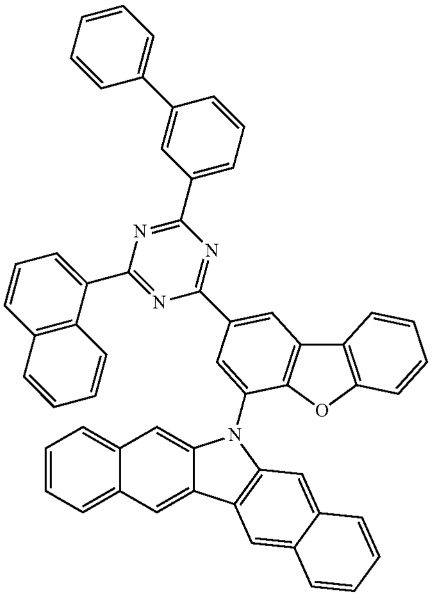
-continued
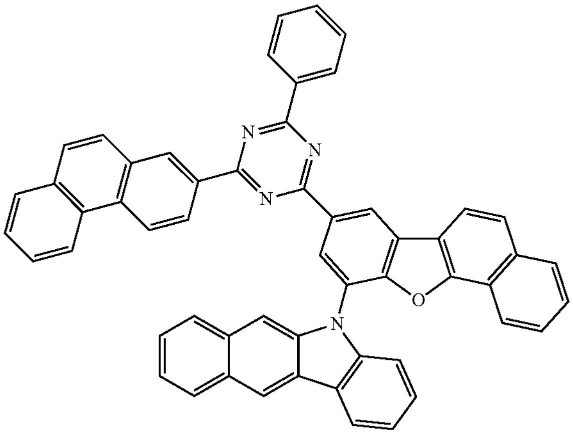
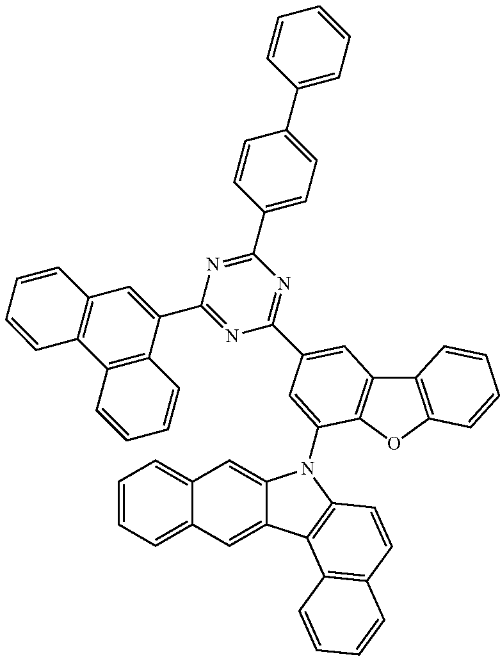
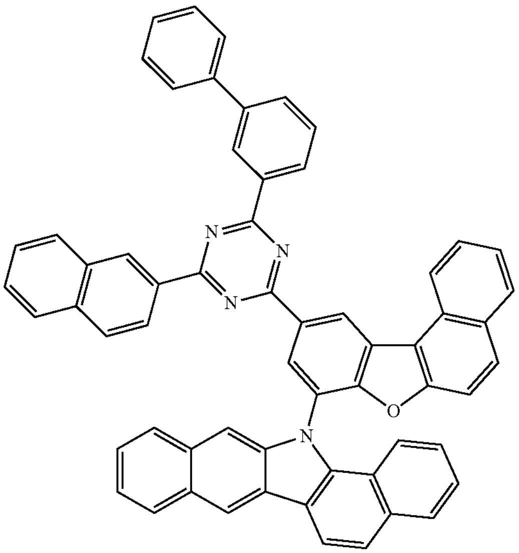

-continued
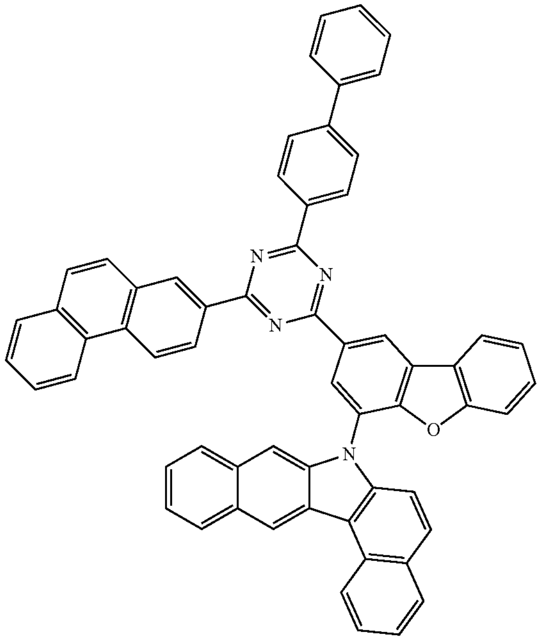
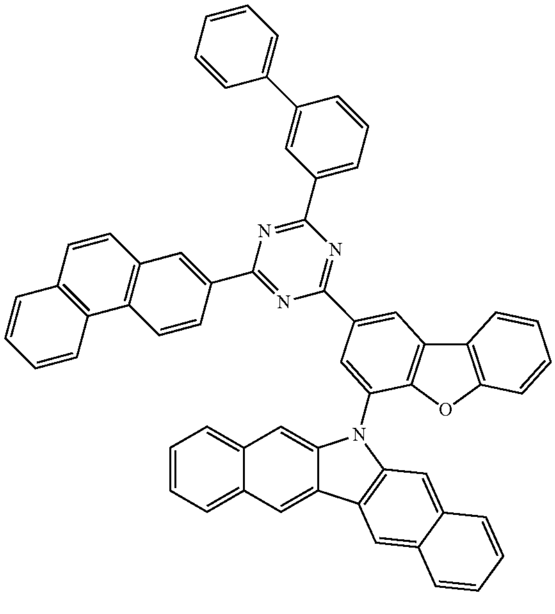
-continued
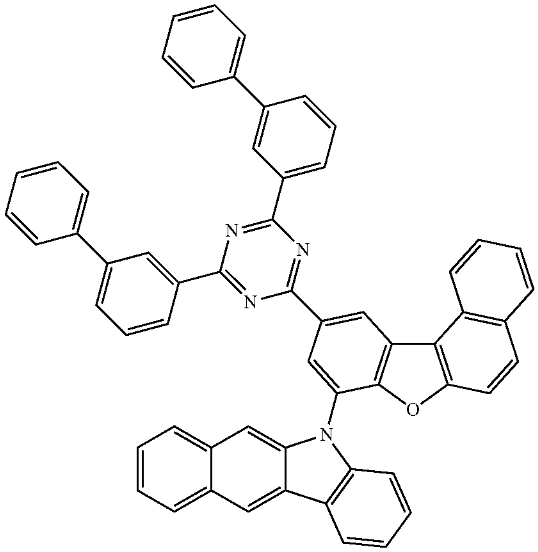
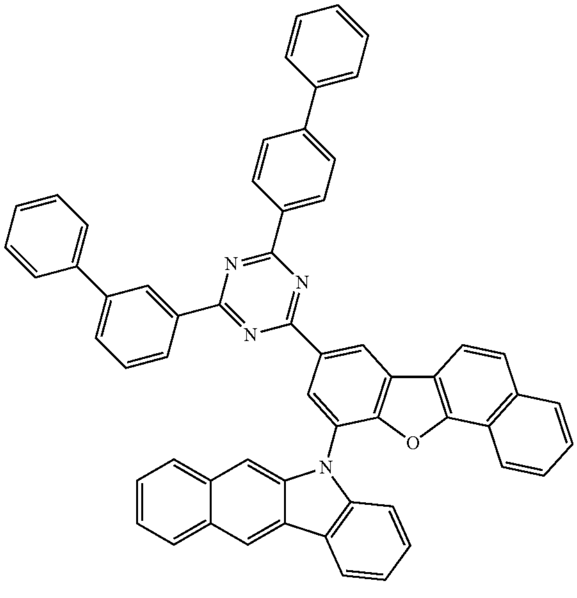

-continued
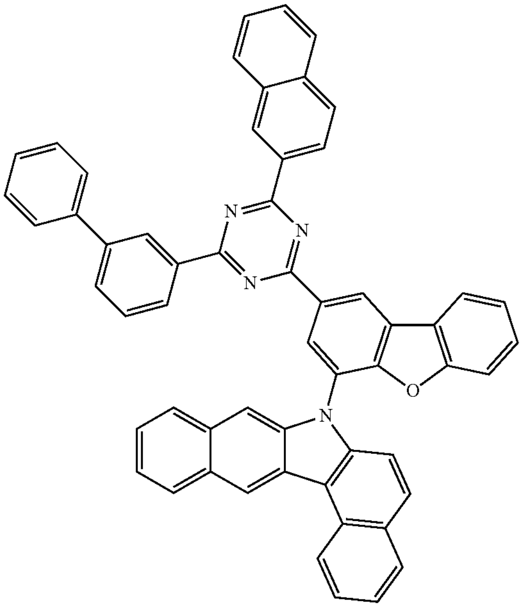
-continued
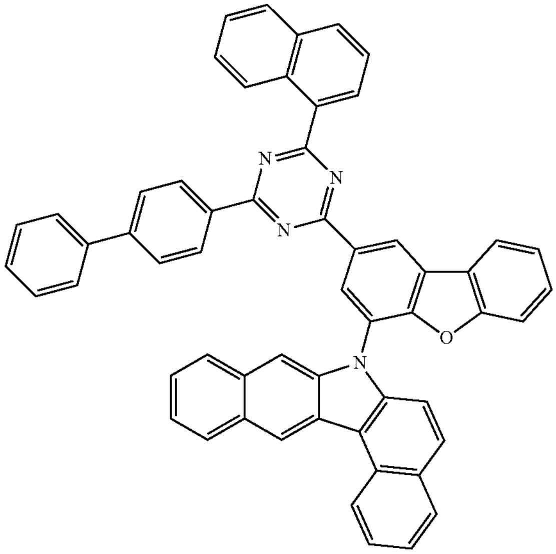
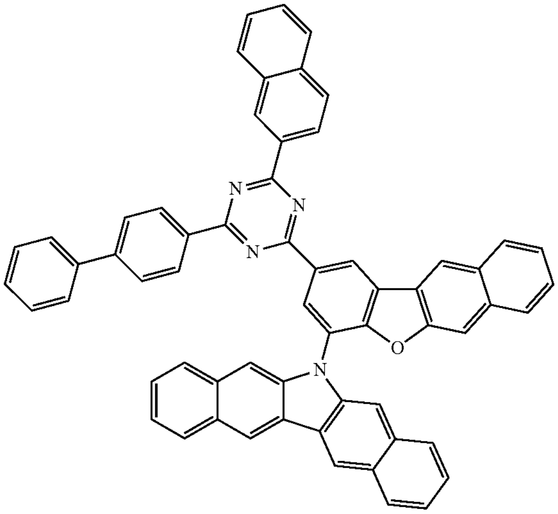
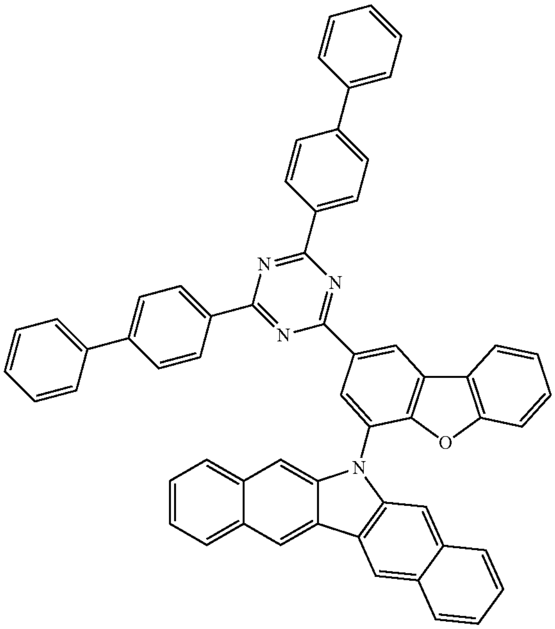
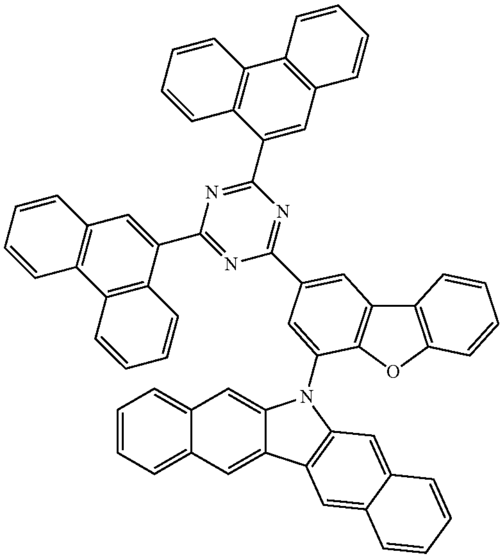

-continued
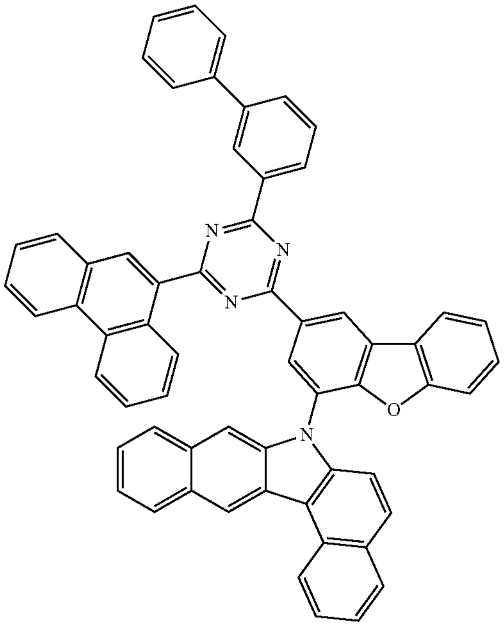
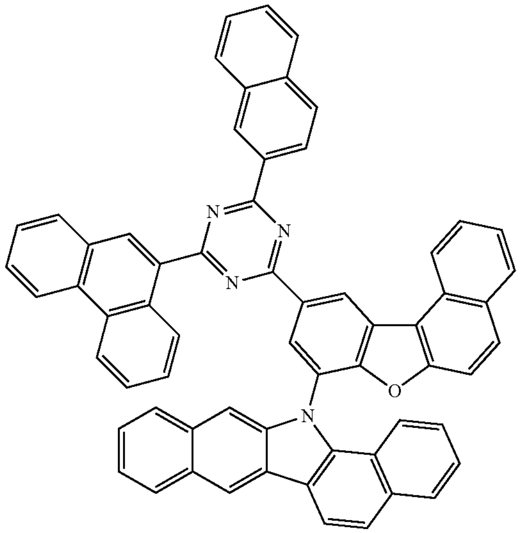
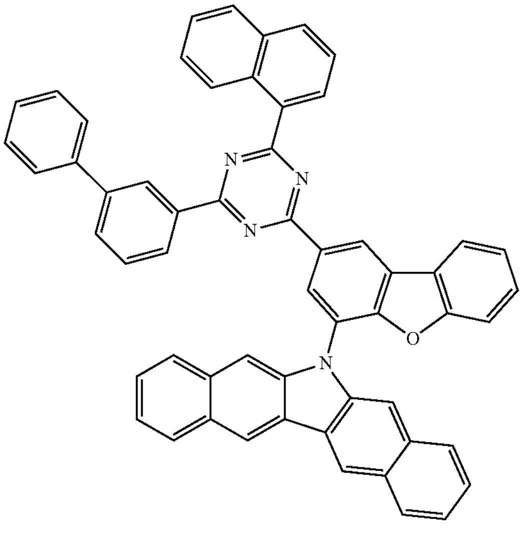
-continued
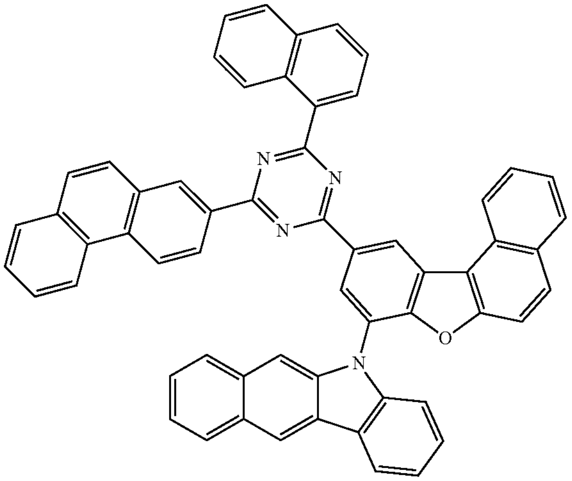
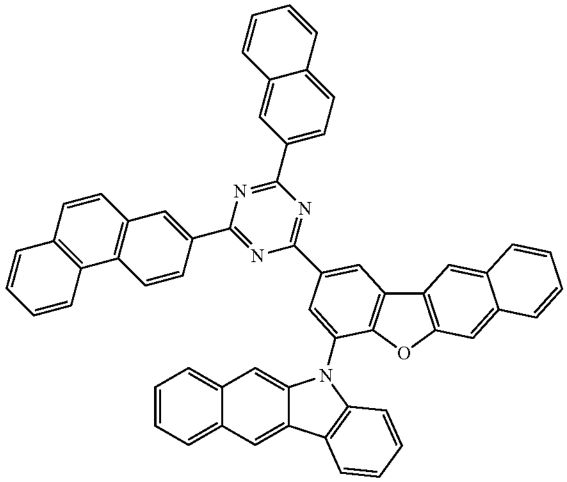
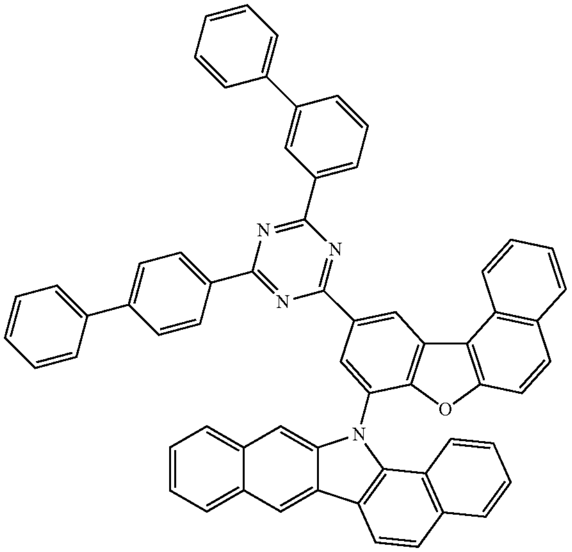

-continued
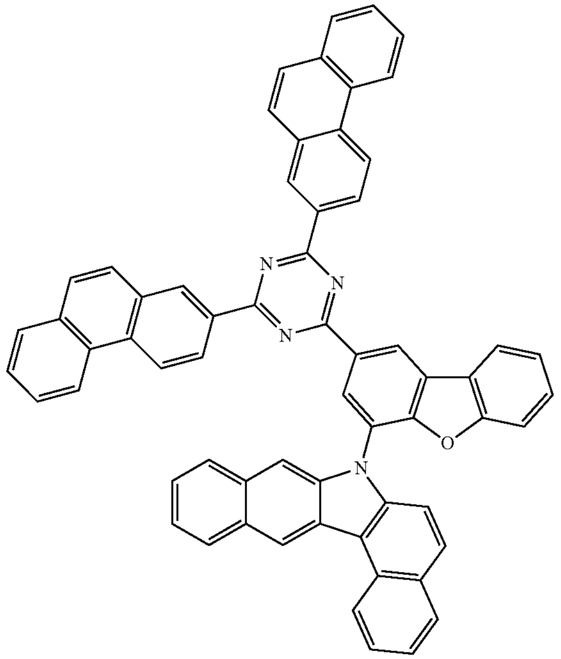
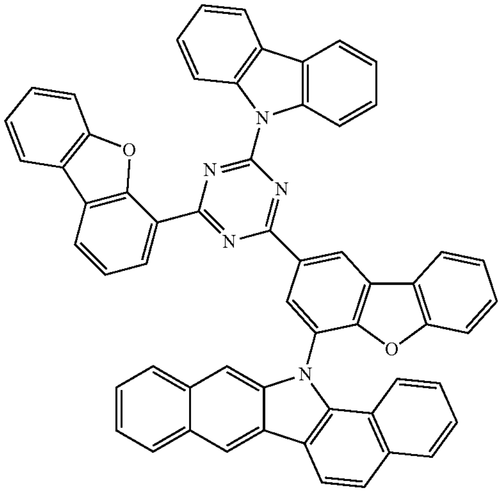
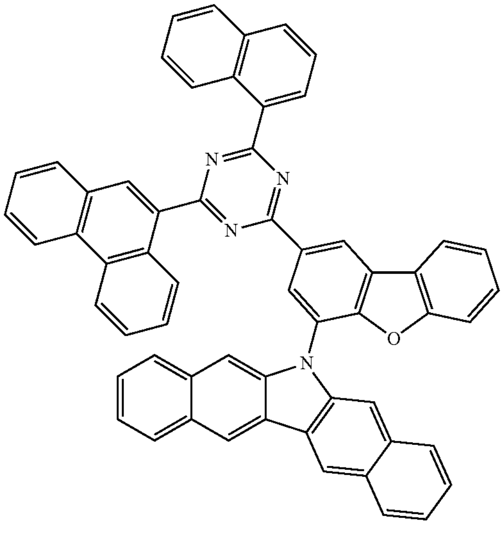
-continued
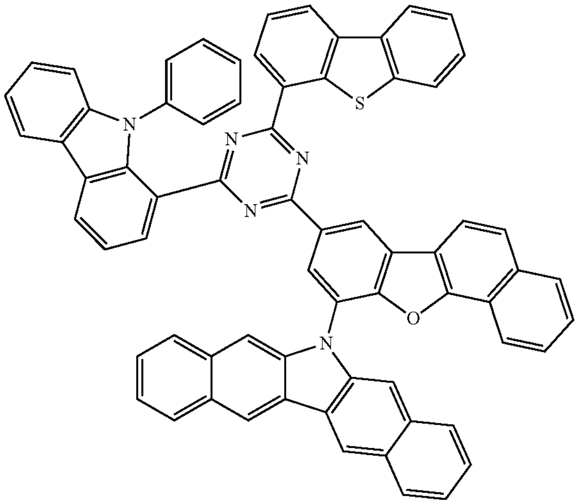
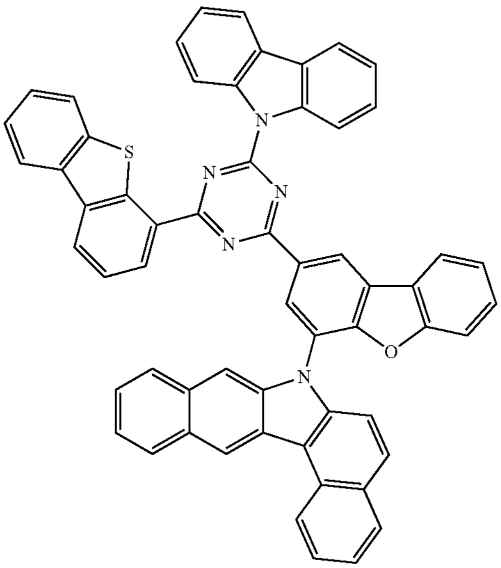
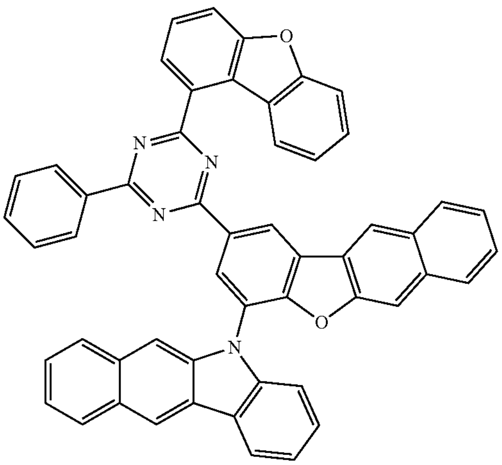

-continued
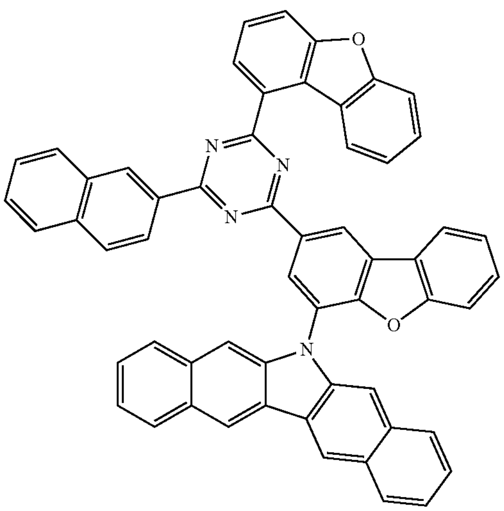
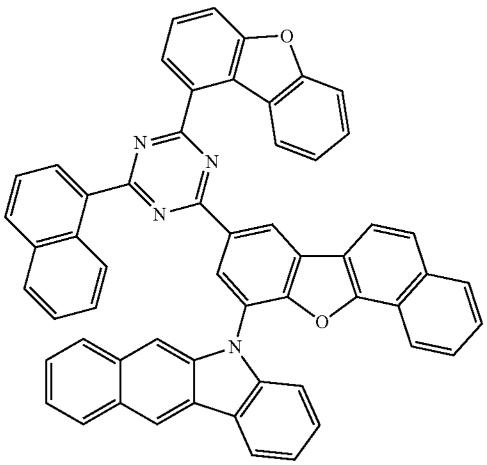
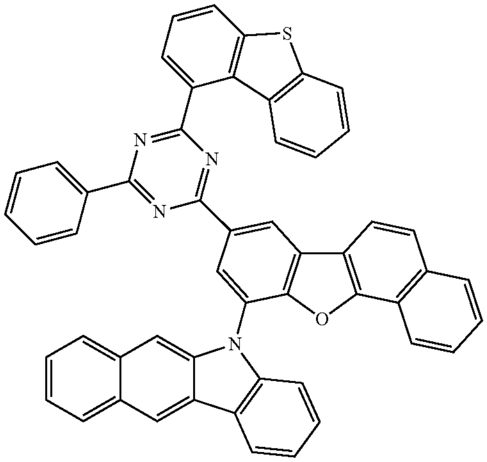
-continued
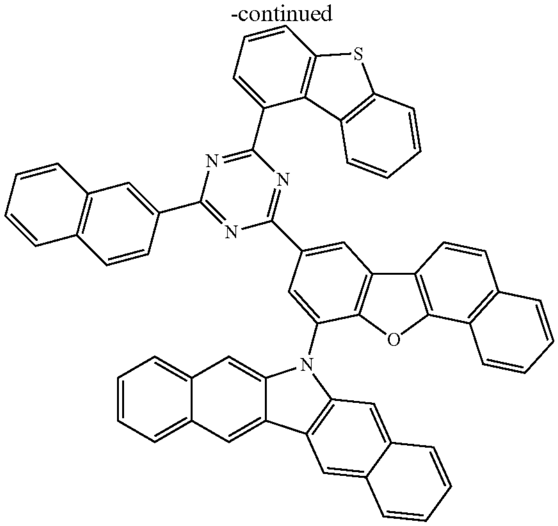
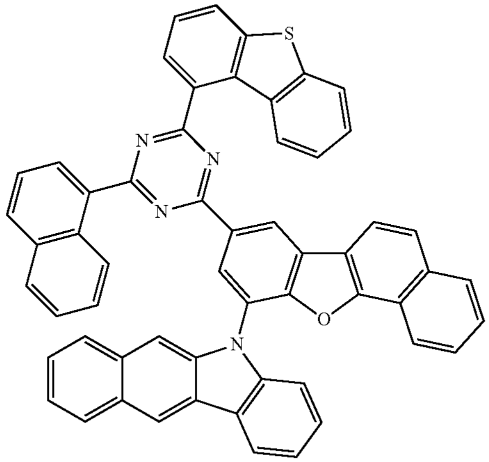
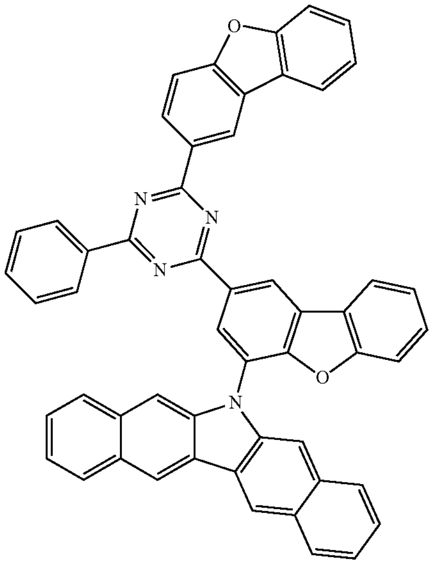

-continued
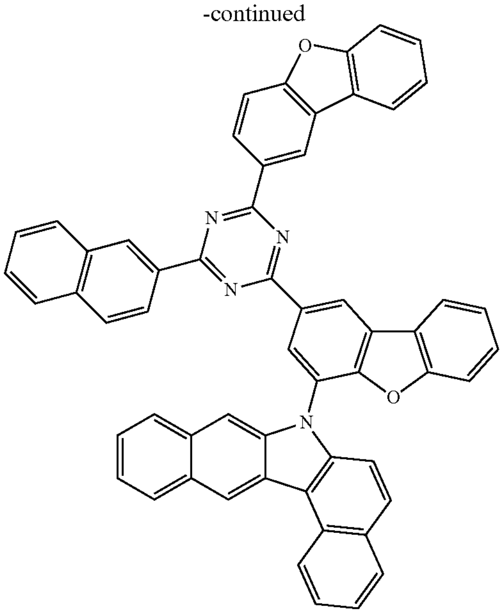
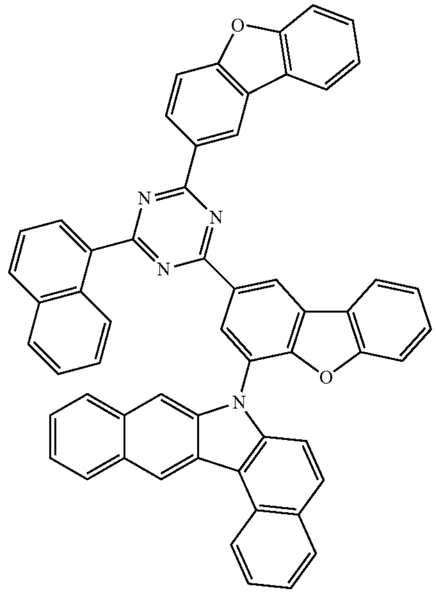
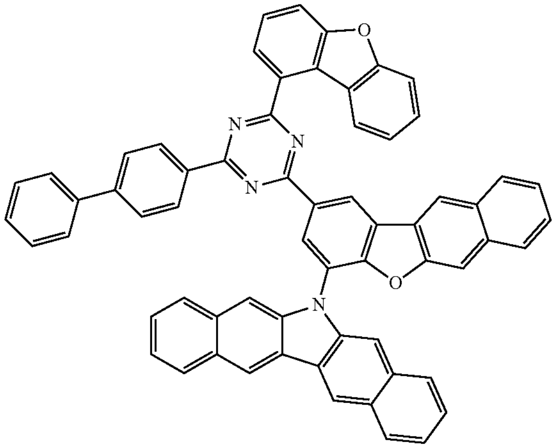
-continued
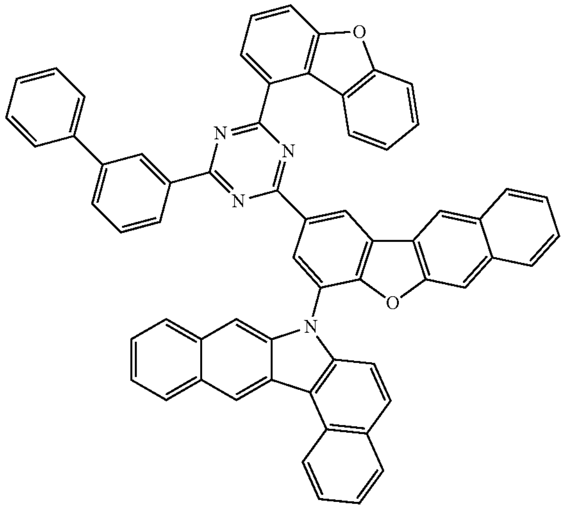
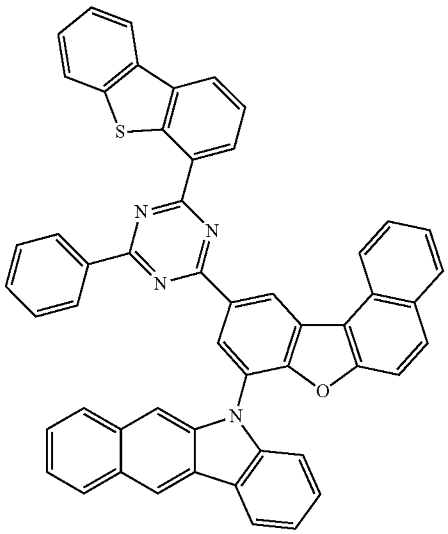
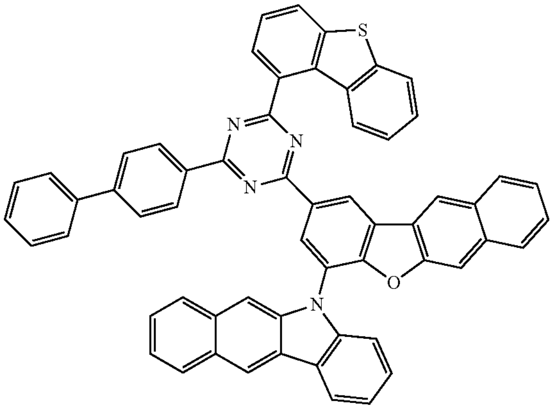

-continued
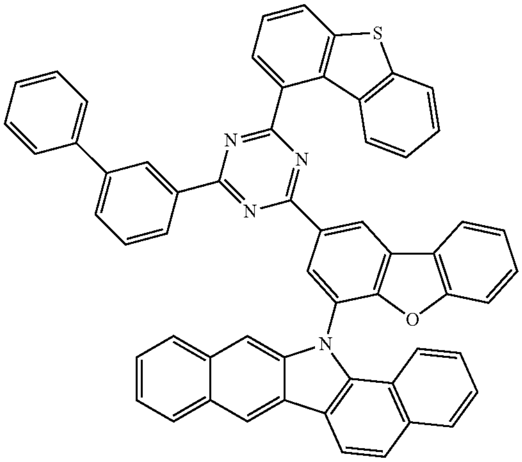
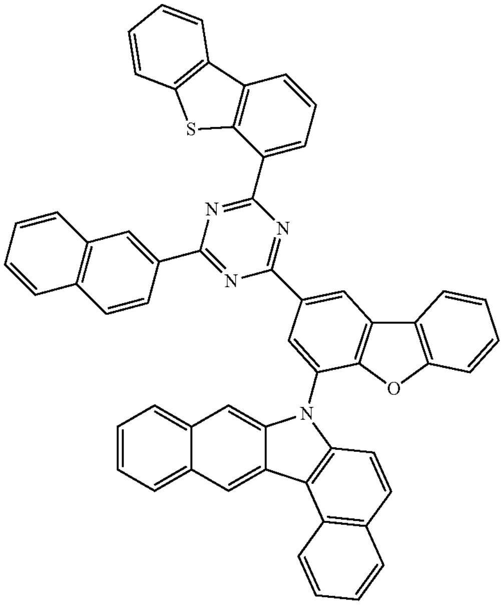
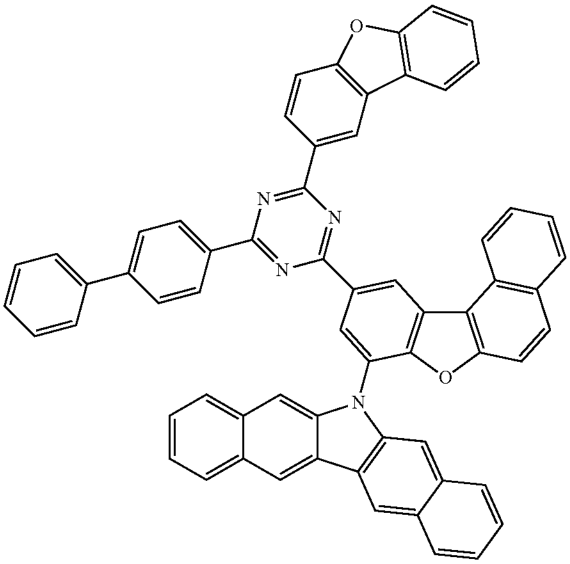
-continued
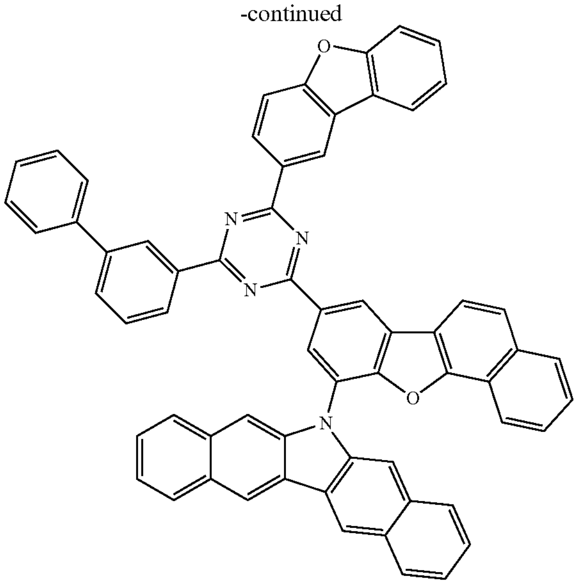
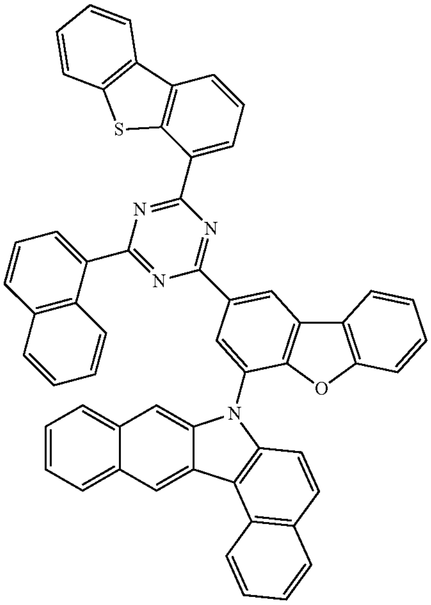
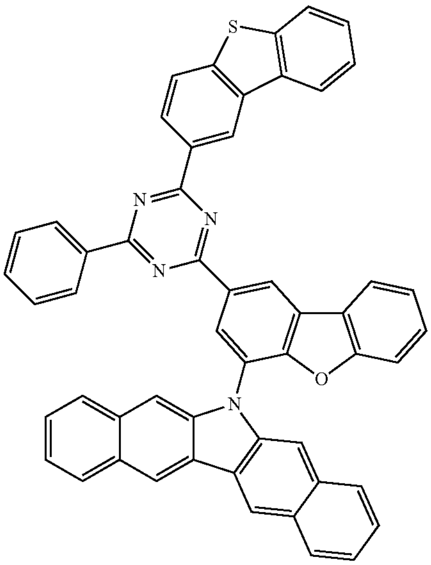

-continued
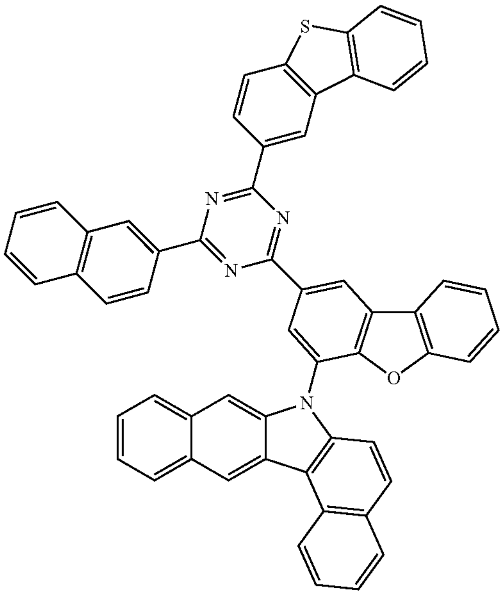
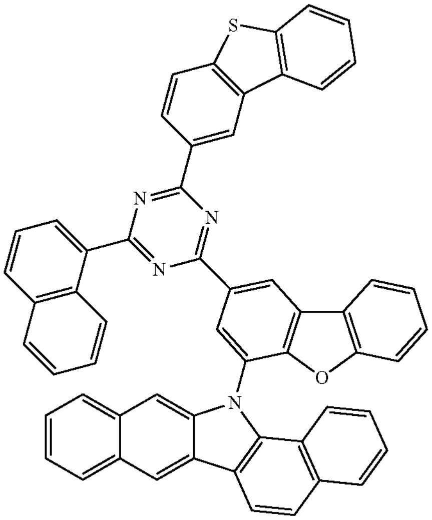
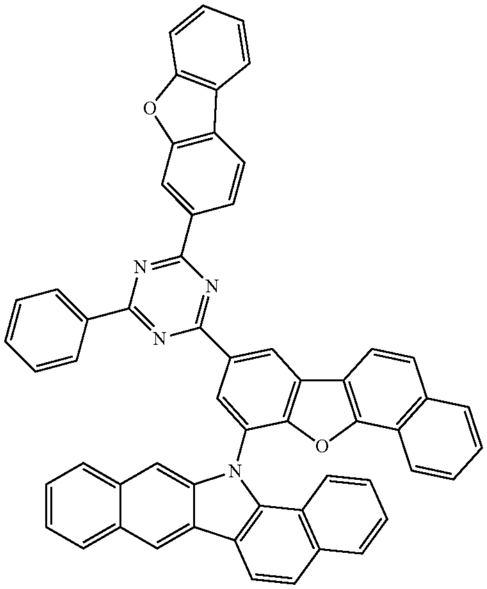
-continued
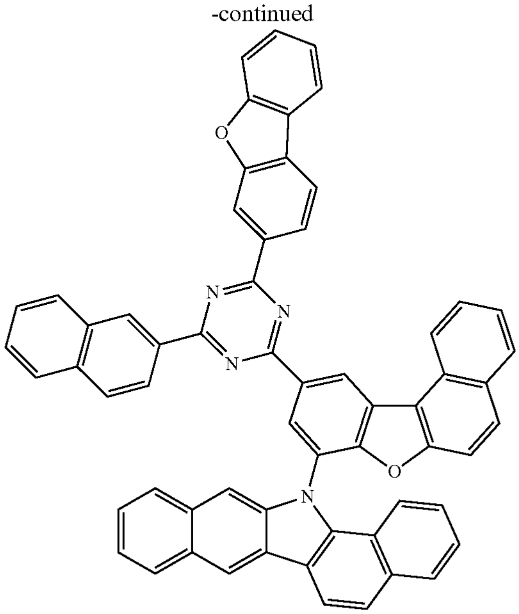
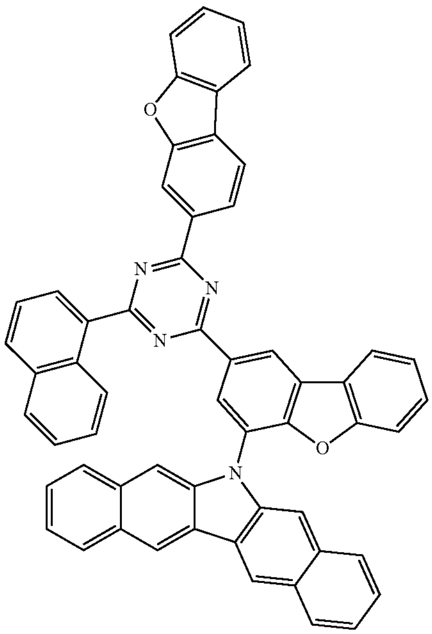

-continued
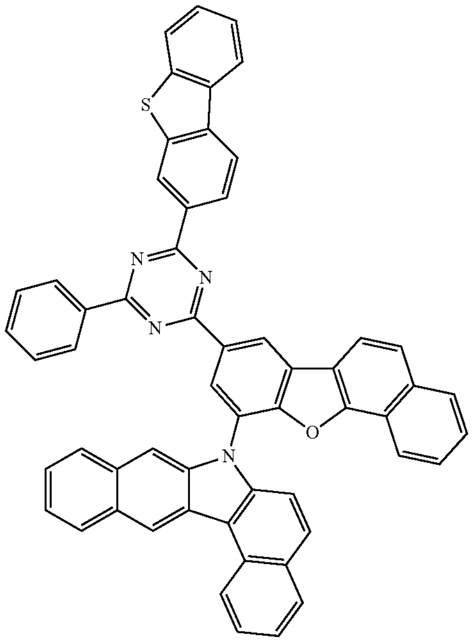
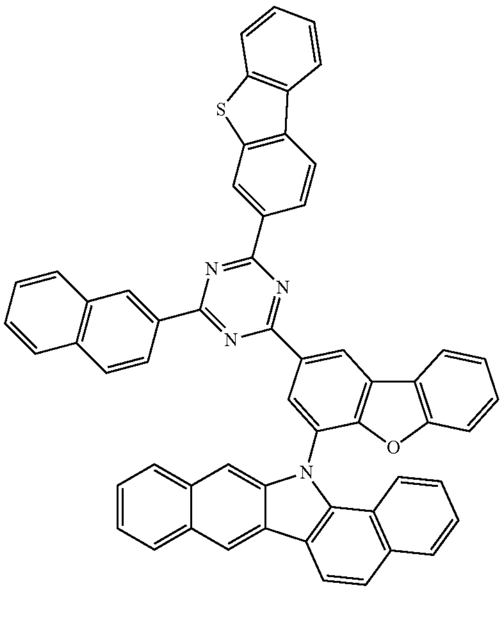
-continued
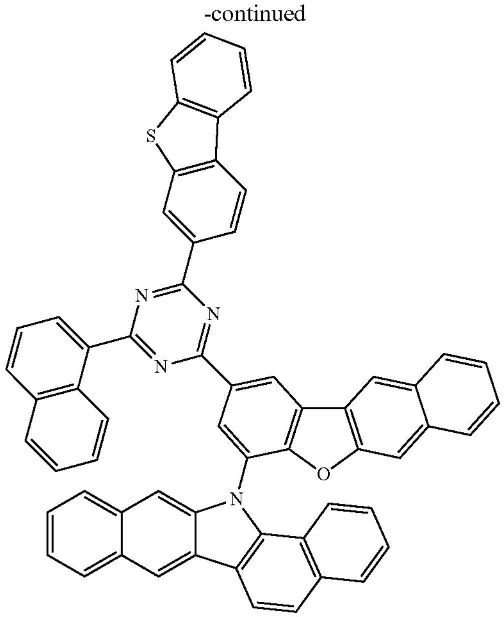
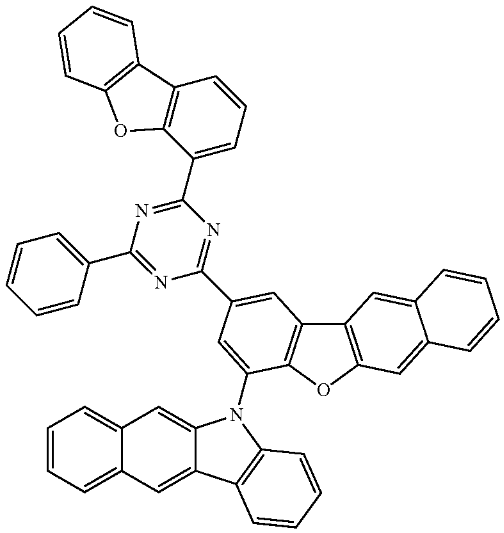
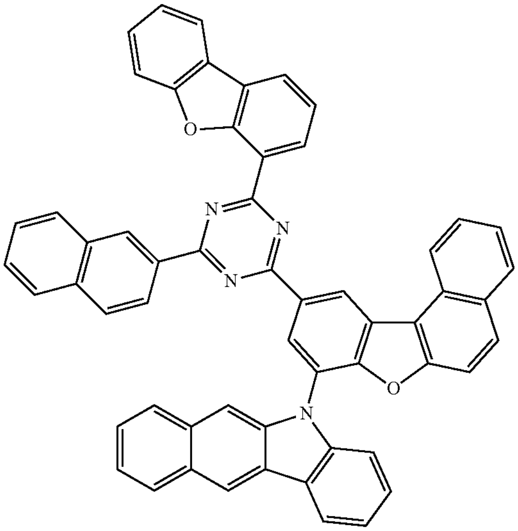

-continued
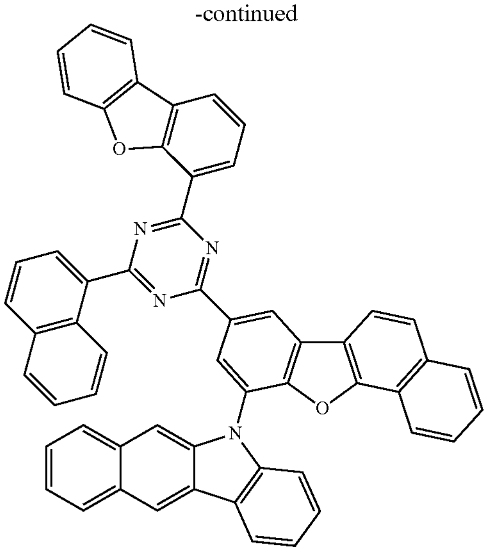
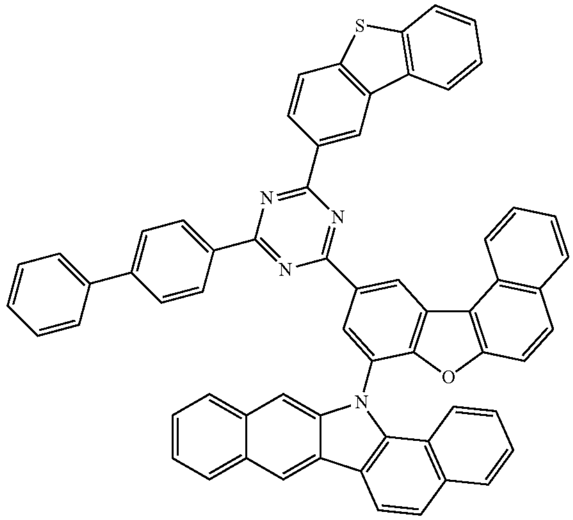
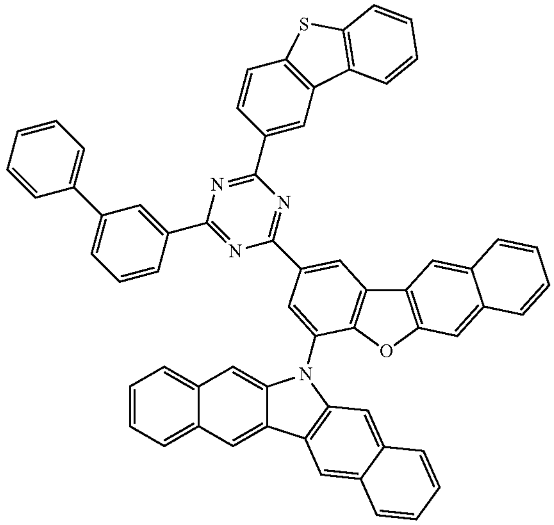
-continued
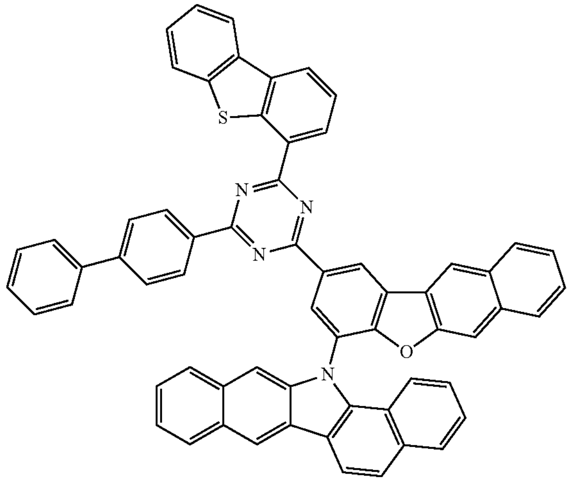
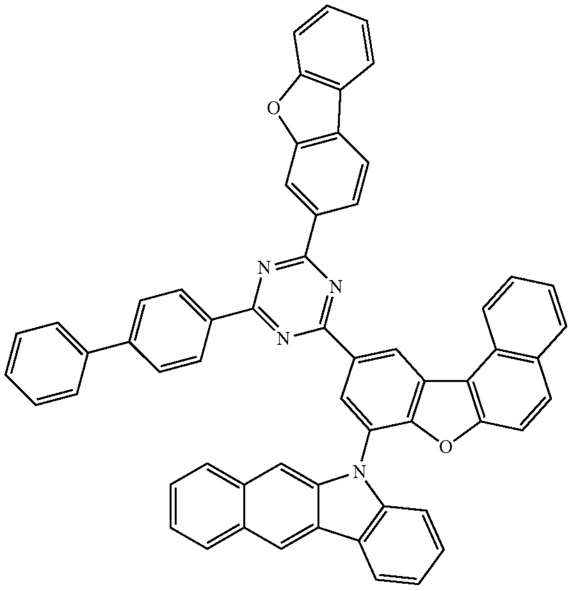
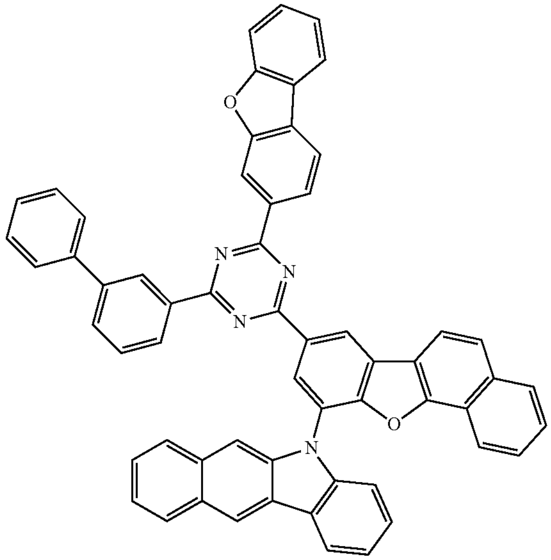

-continued
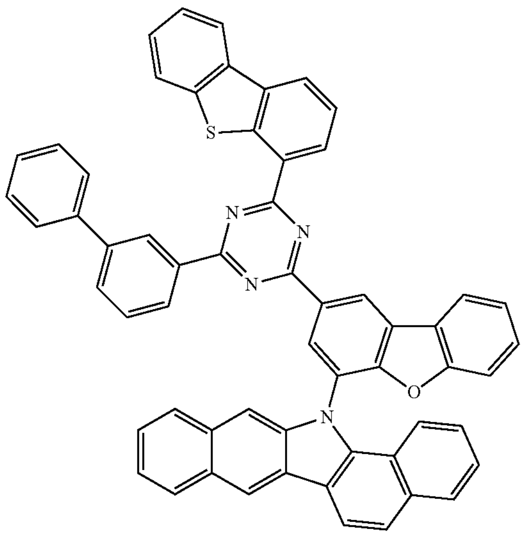
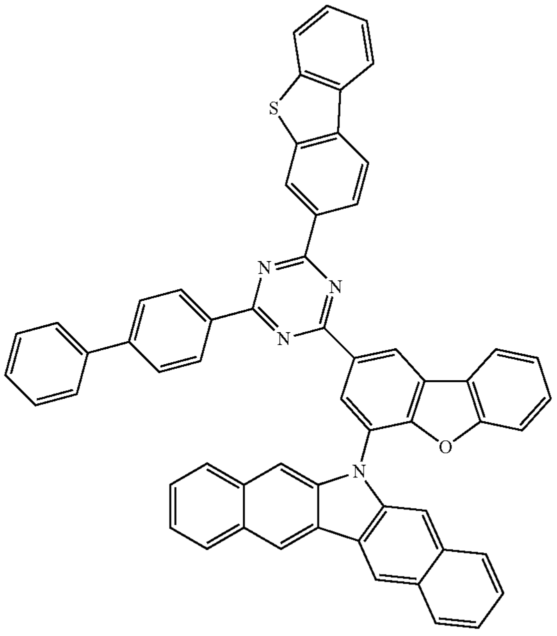
-continued
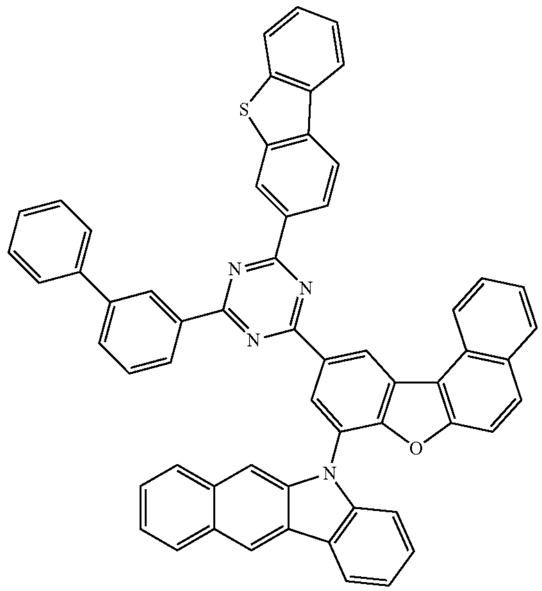
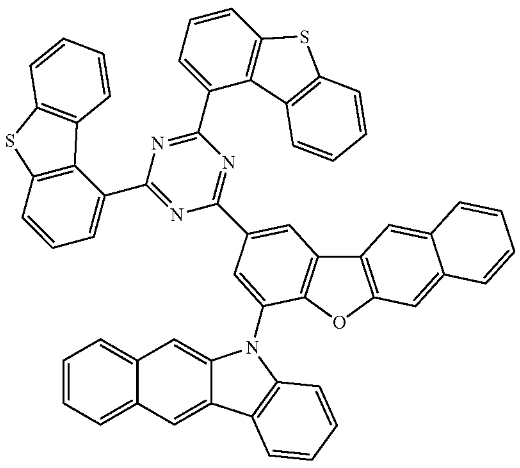
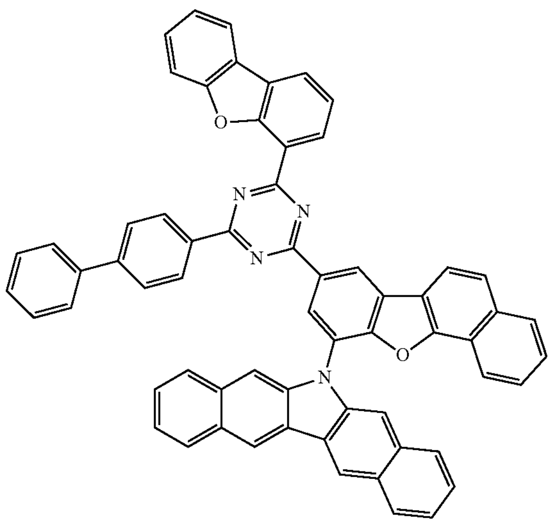

-continued
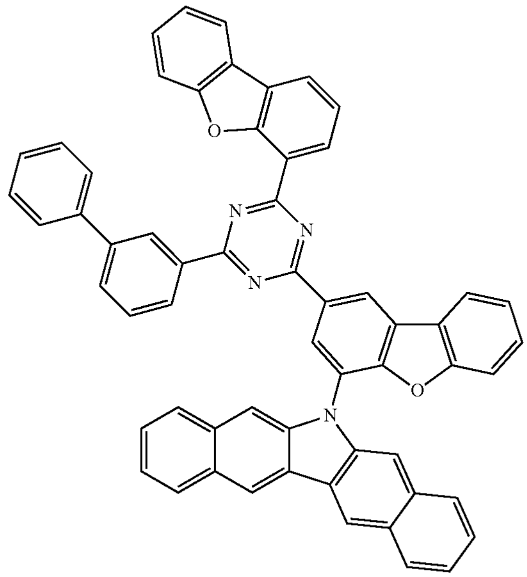
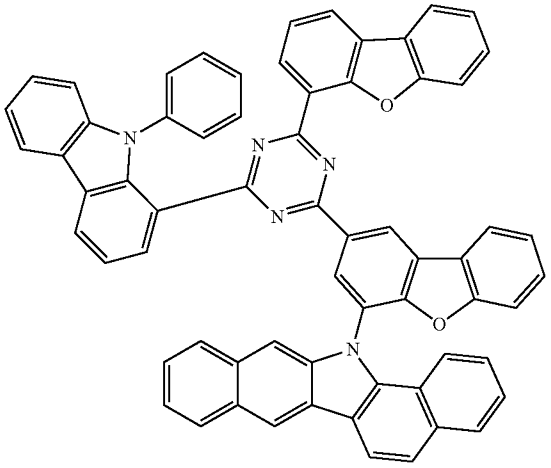
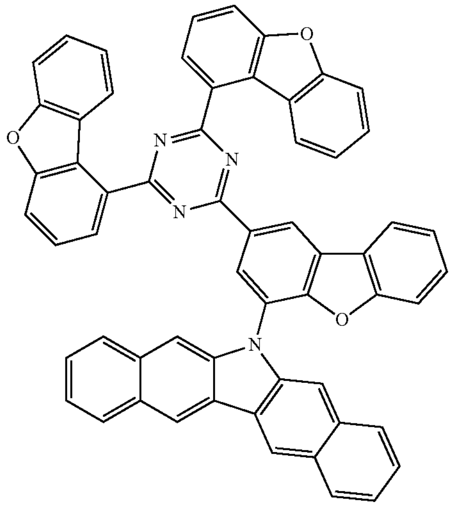
-continued
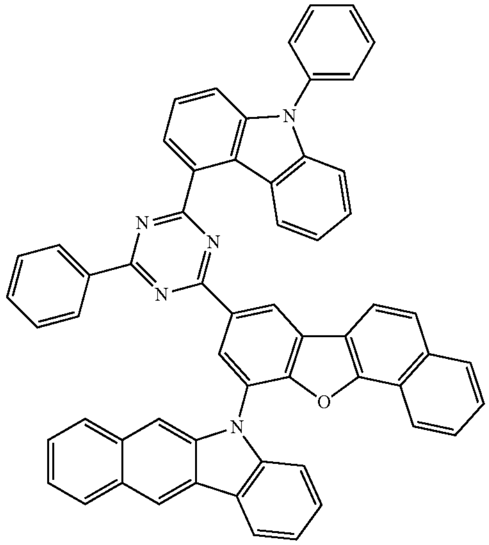
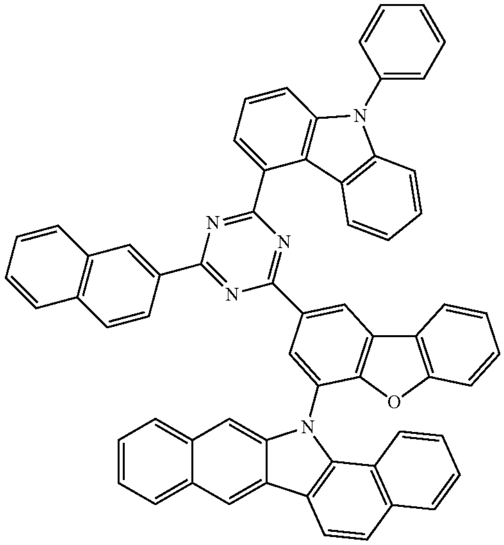
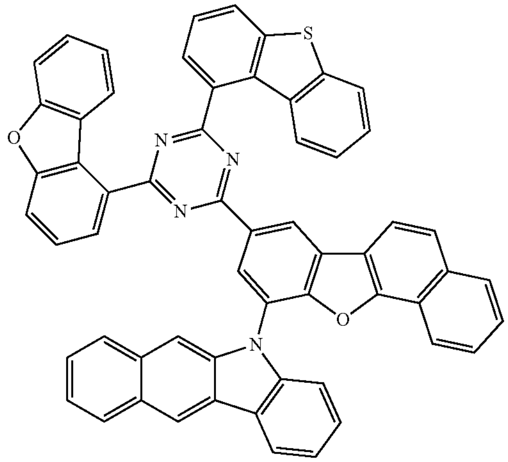

-continued
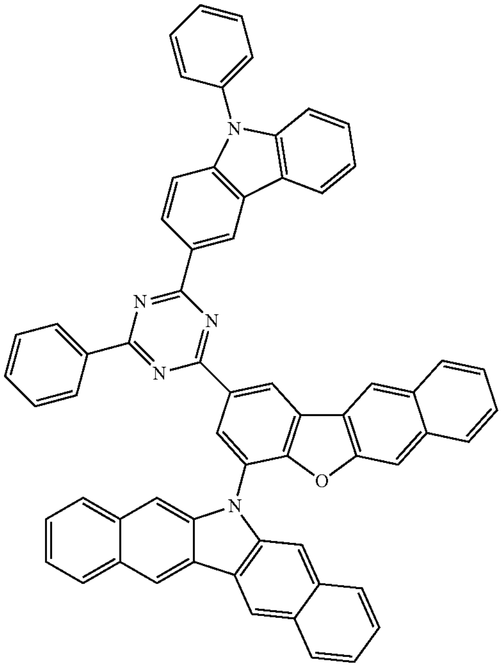
-continued
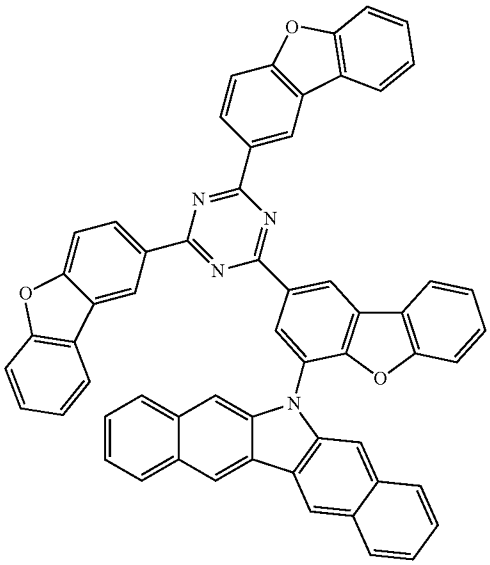
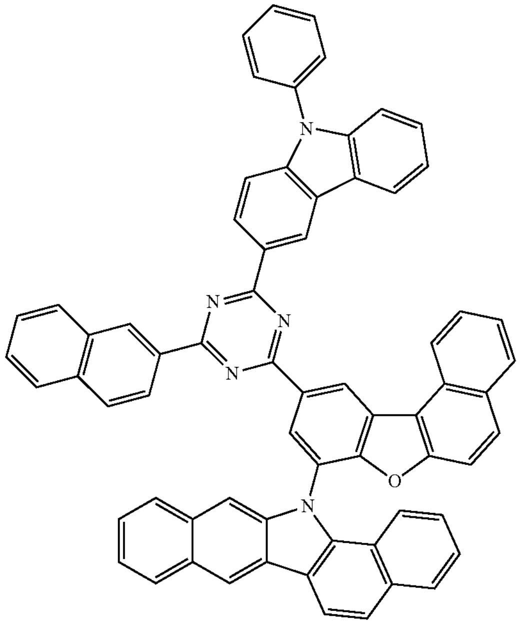
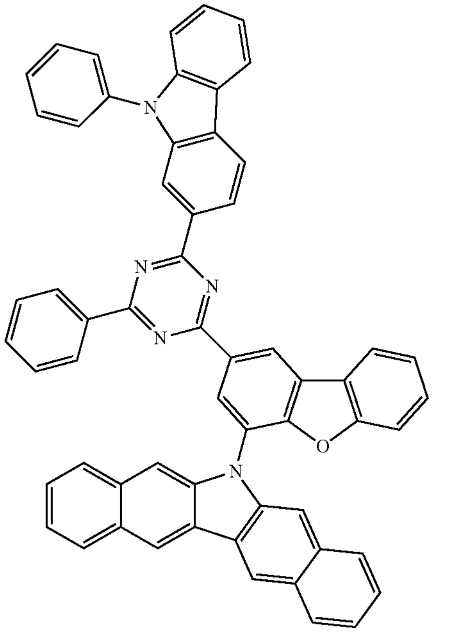

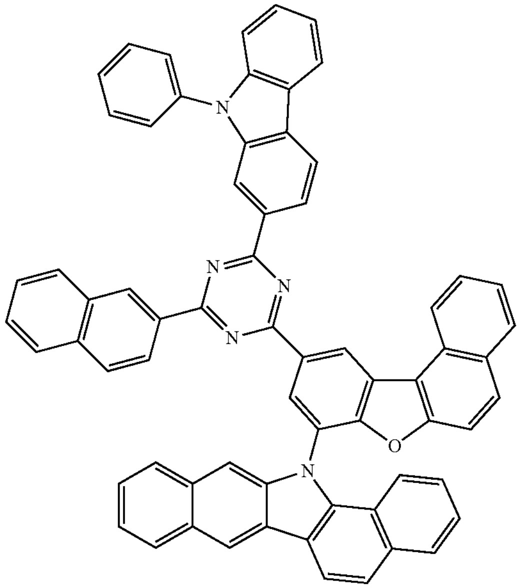
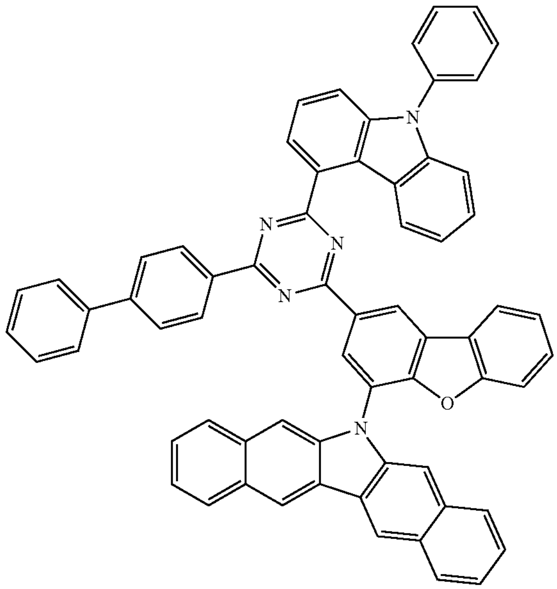
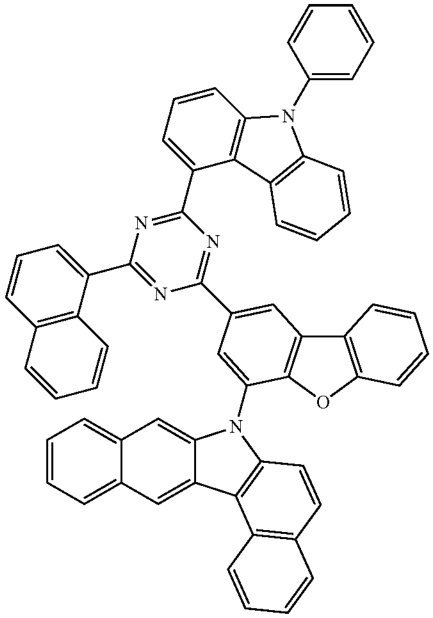
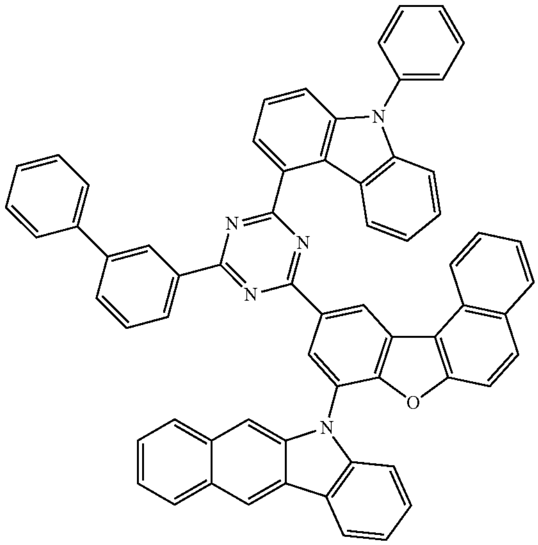

-continued
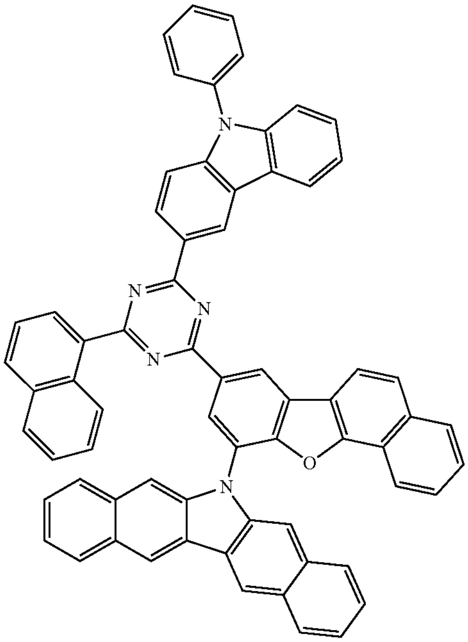
-continued
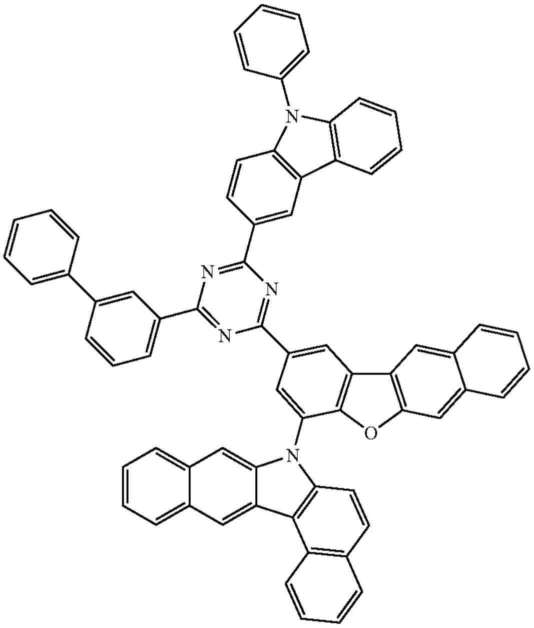
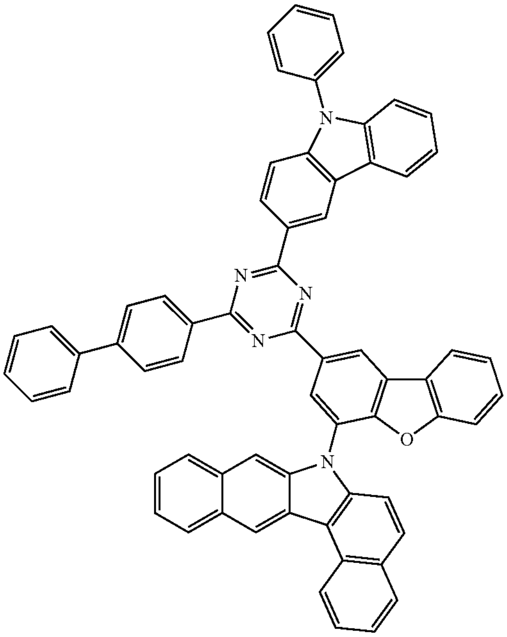
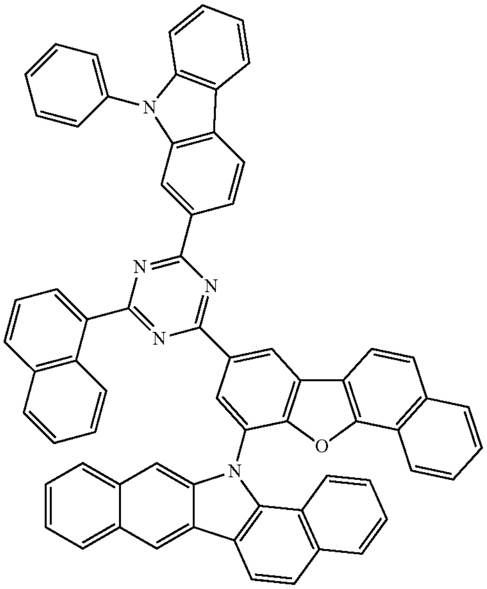

-continued
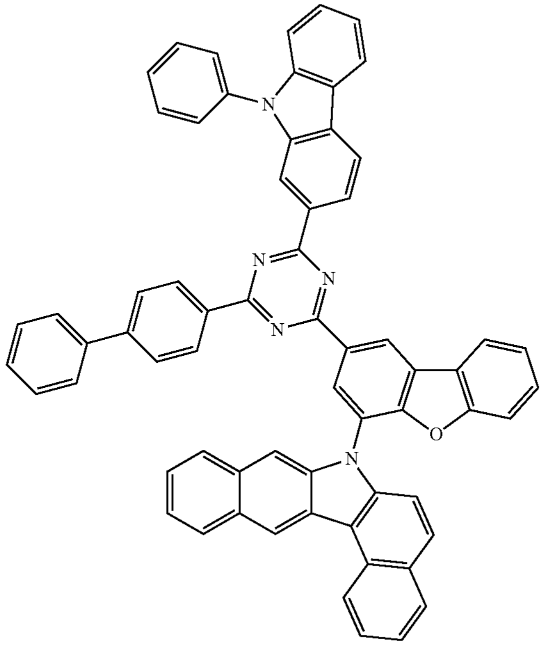
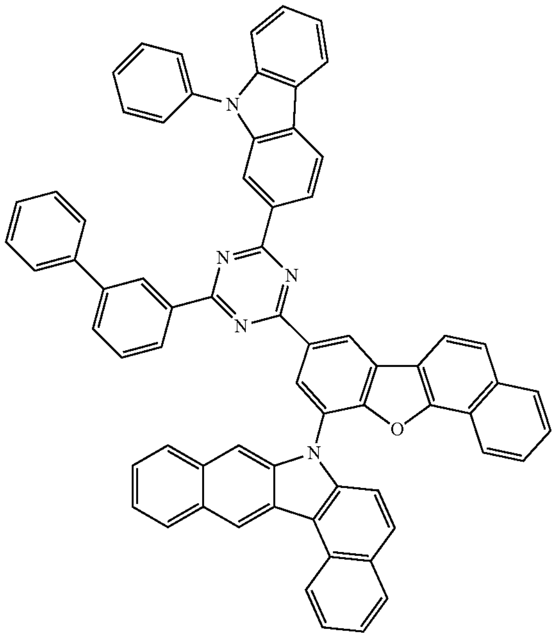
-continued
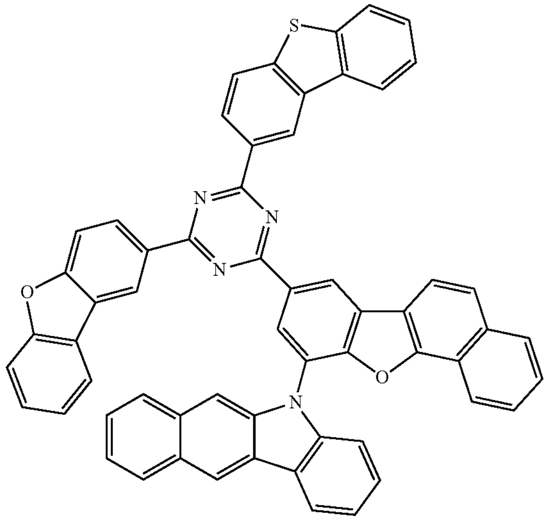
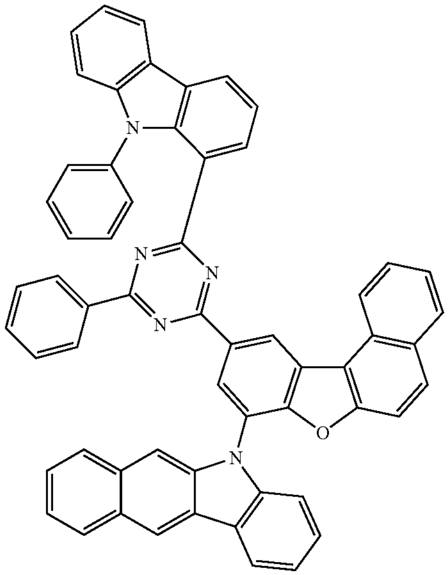
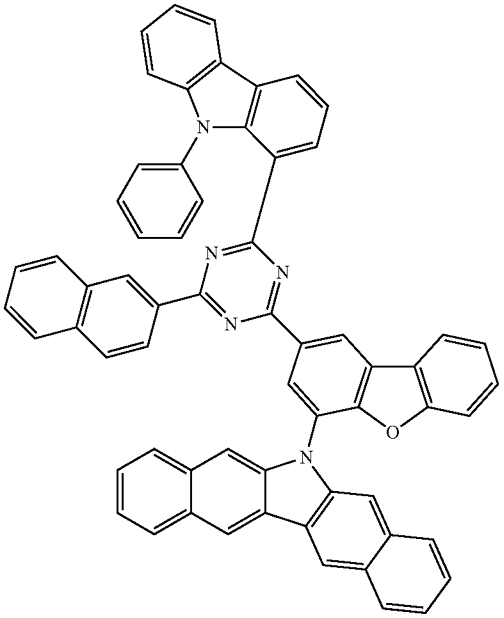

-continued
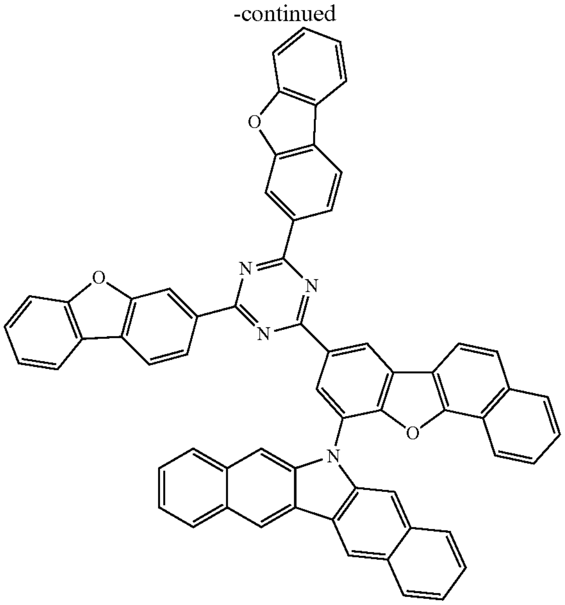
-continued
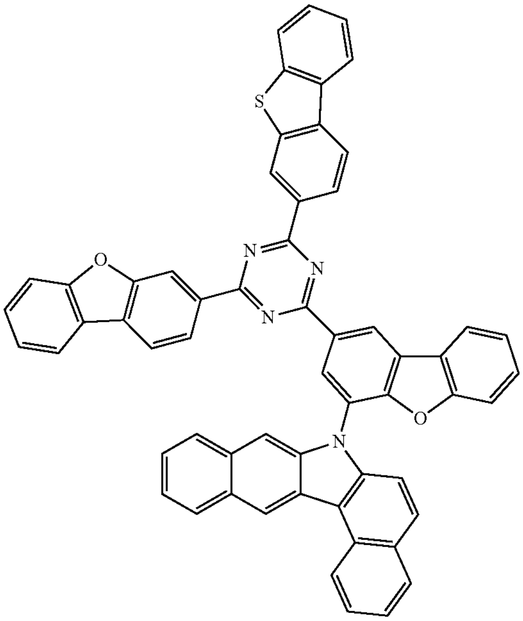
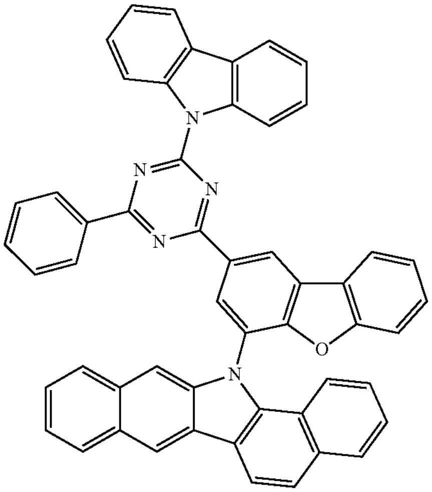
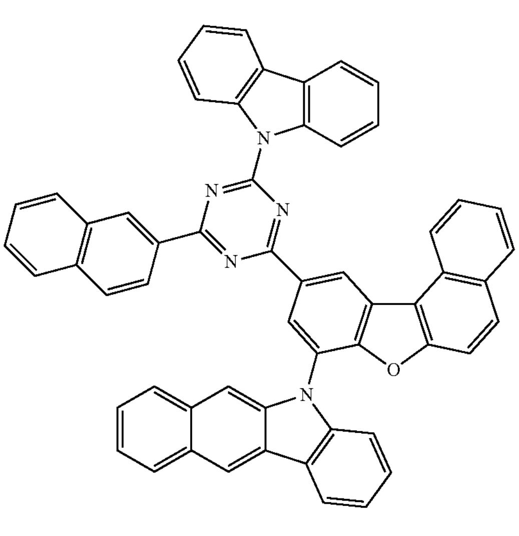
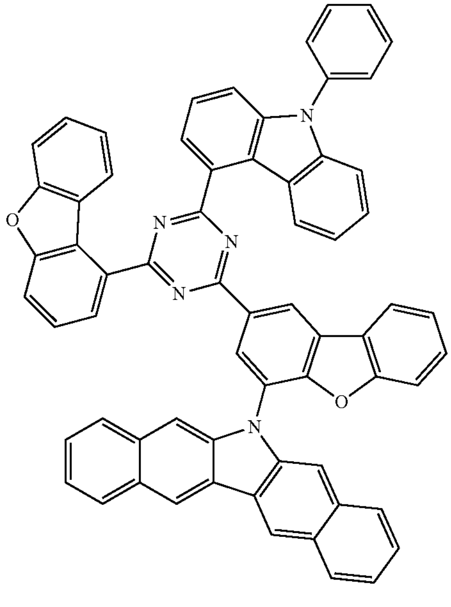

-continued
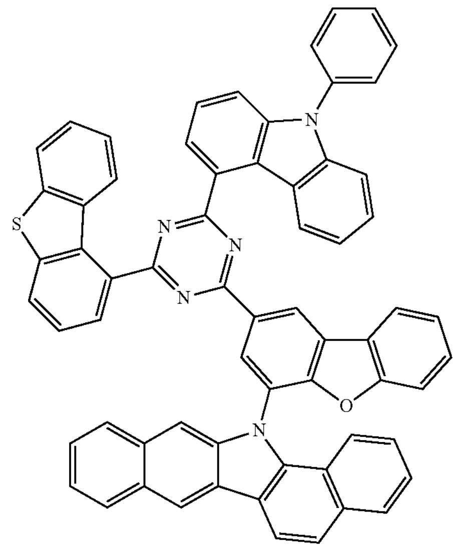
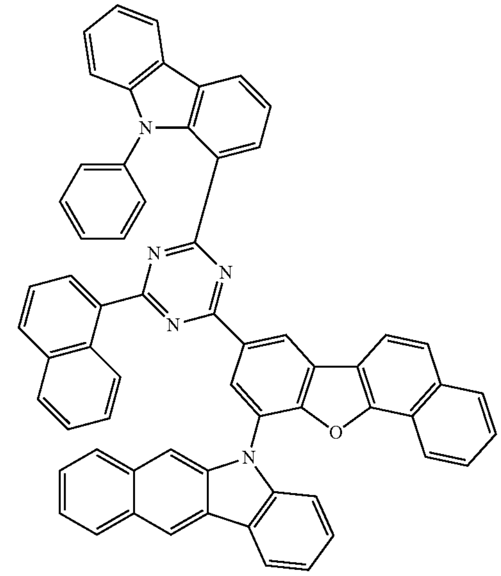
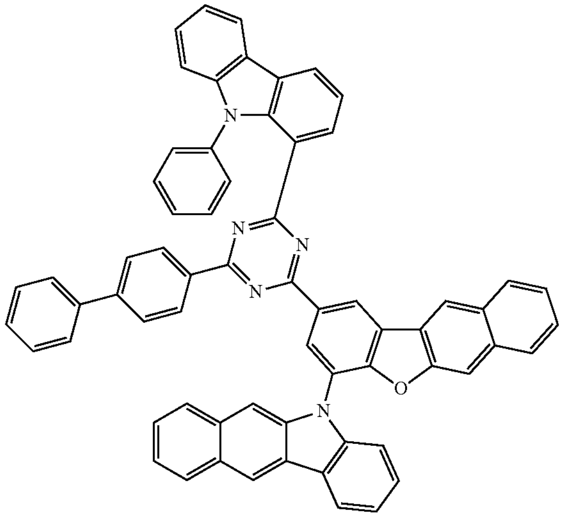
-continued
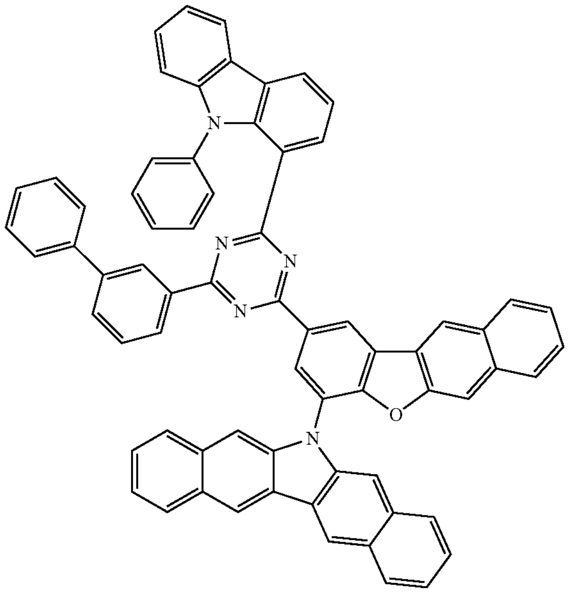
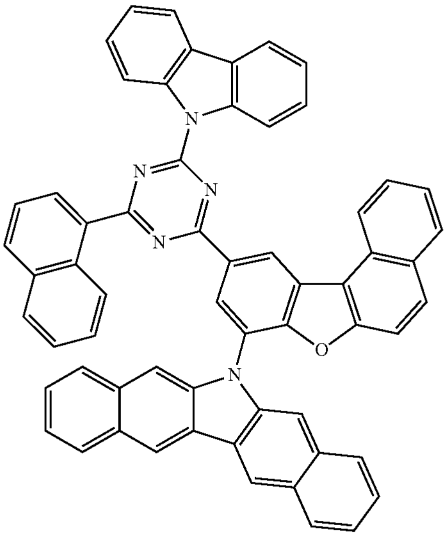
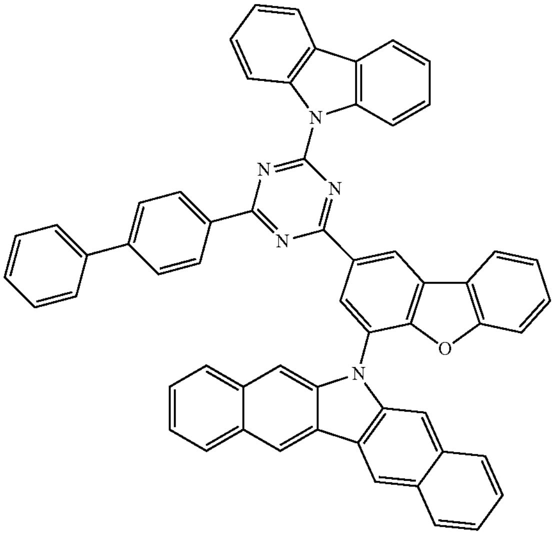

-continued
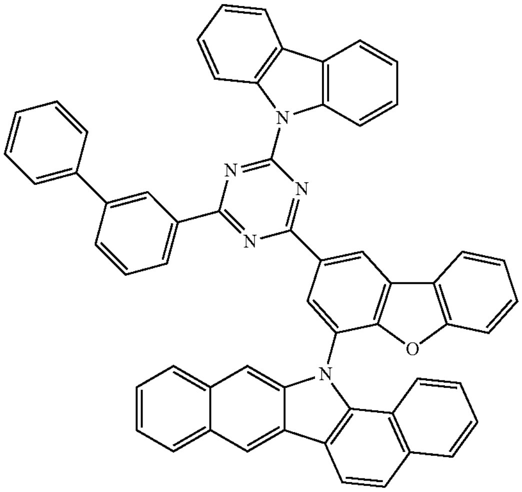
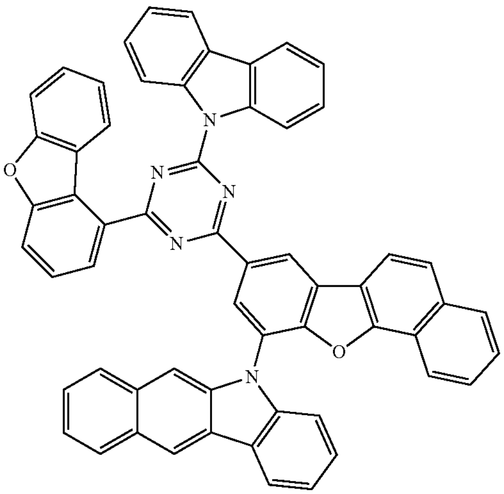
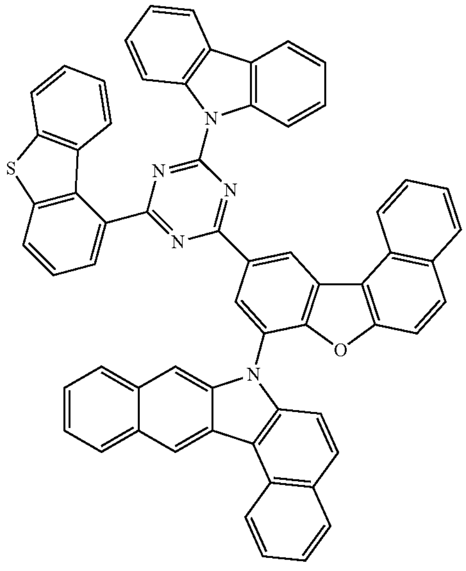
-continued
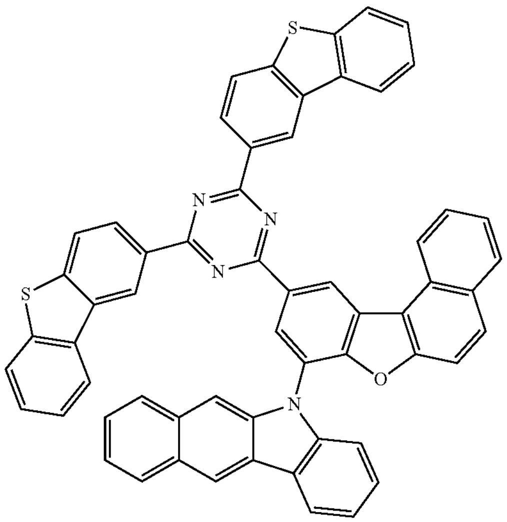
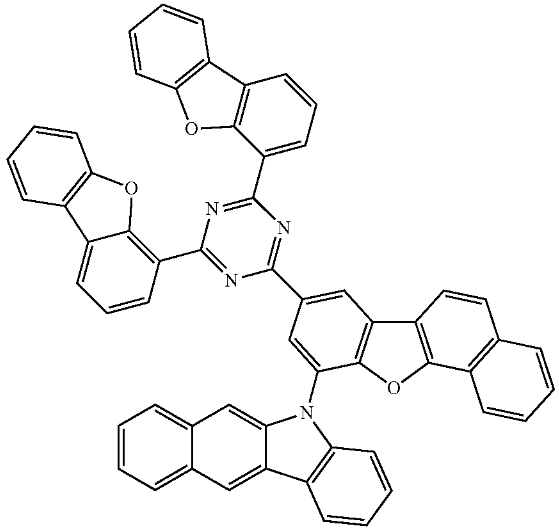
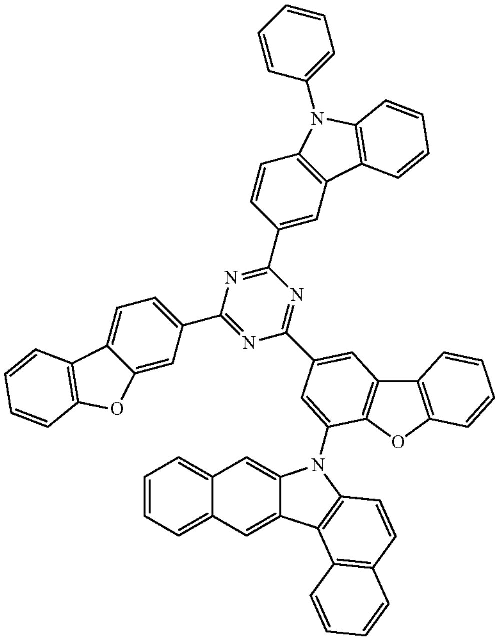

-continued
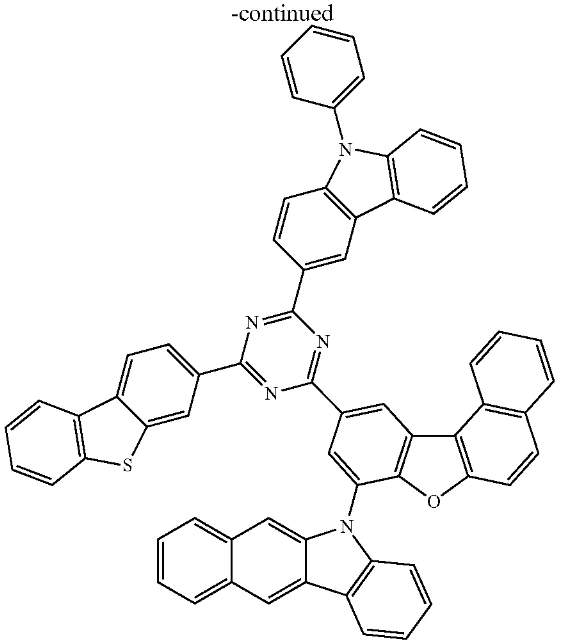
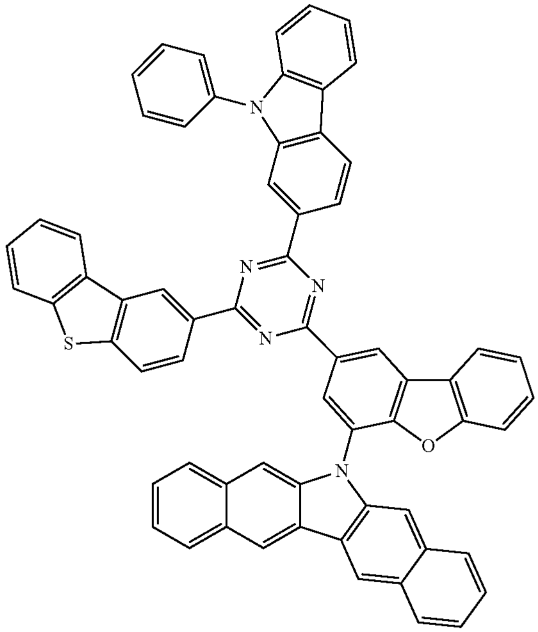
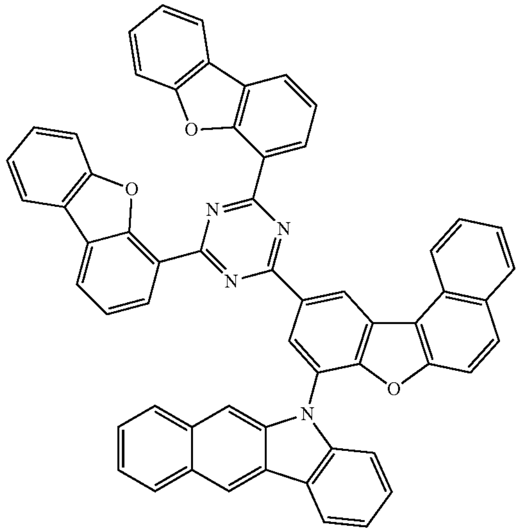
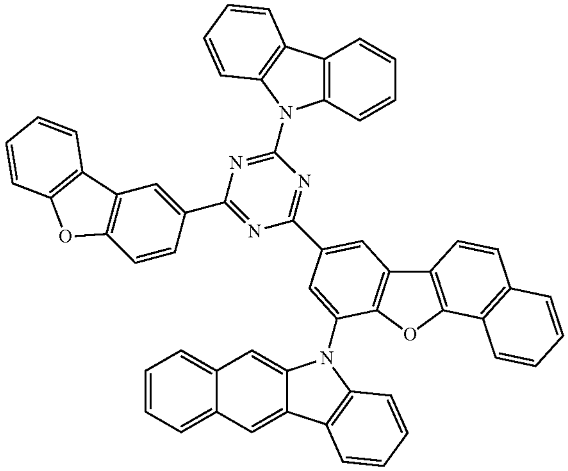
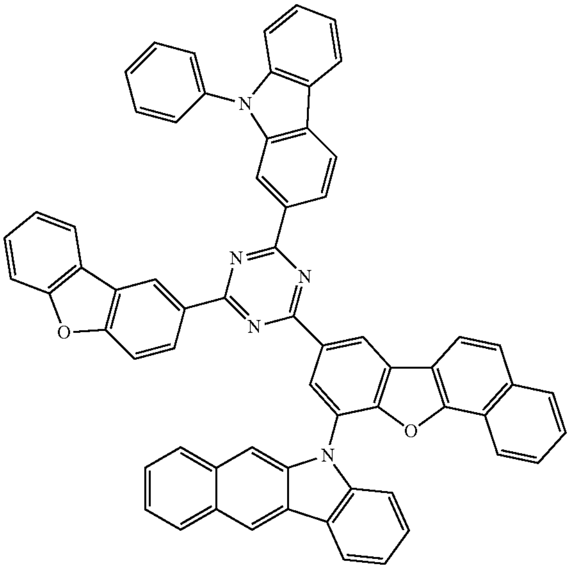
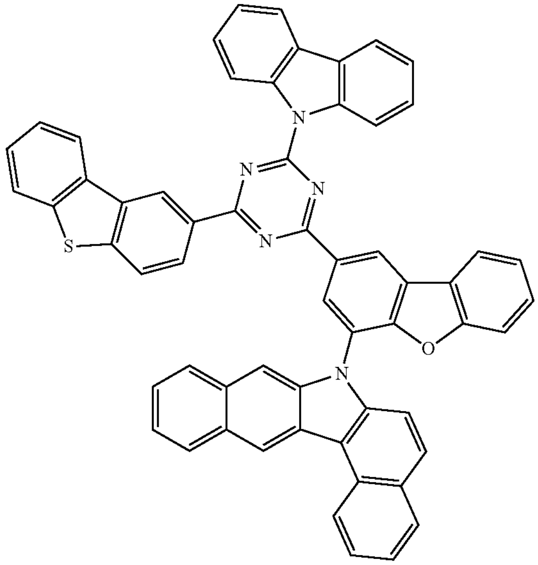
-continued -continued
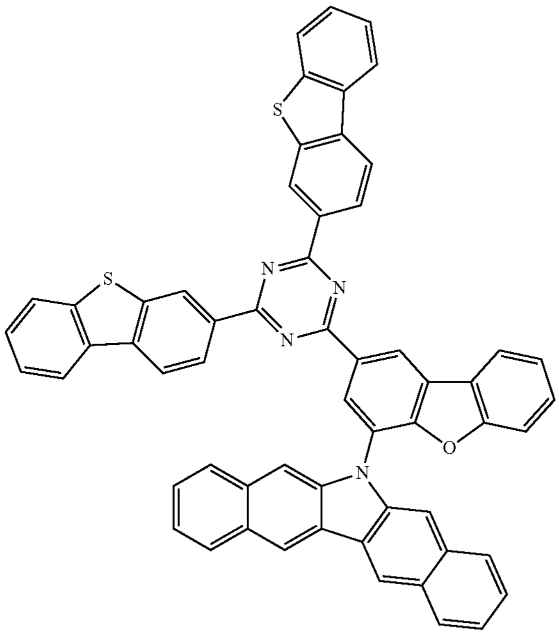
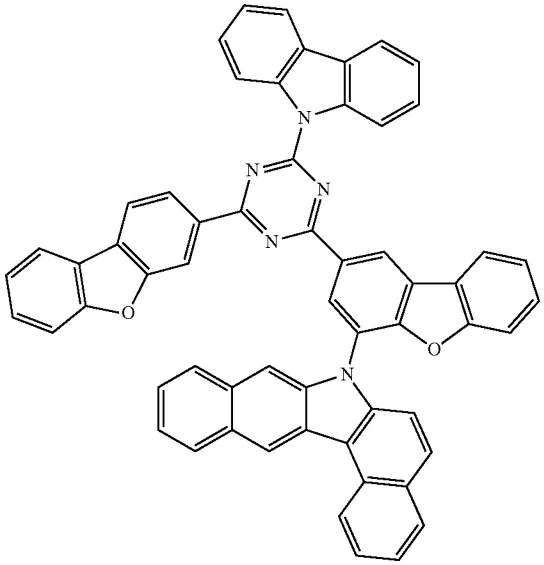
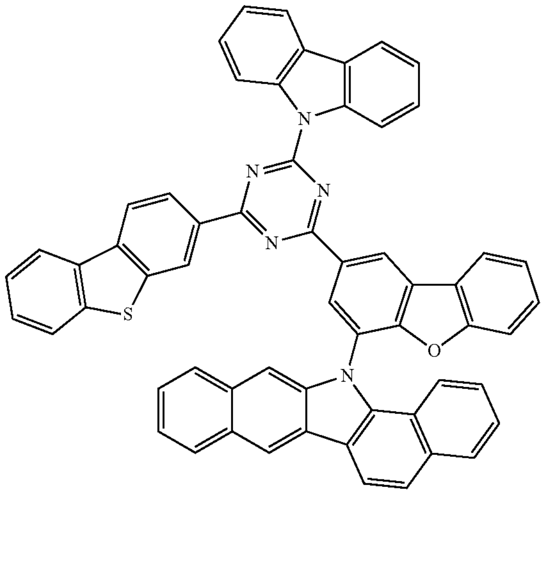
-continued
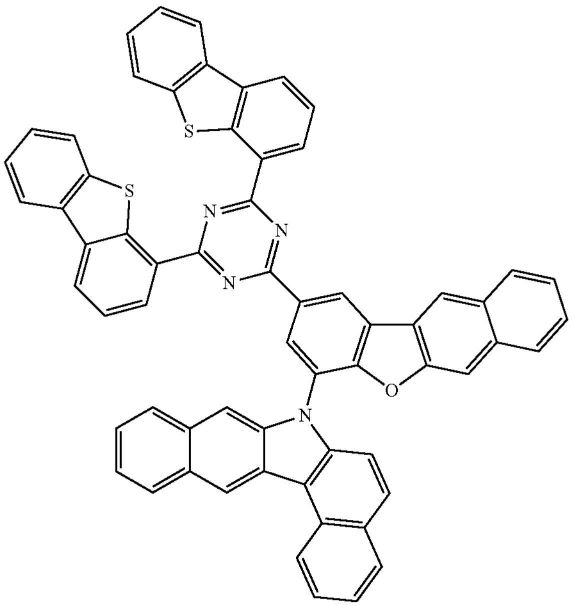
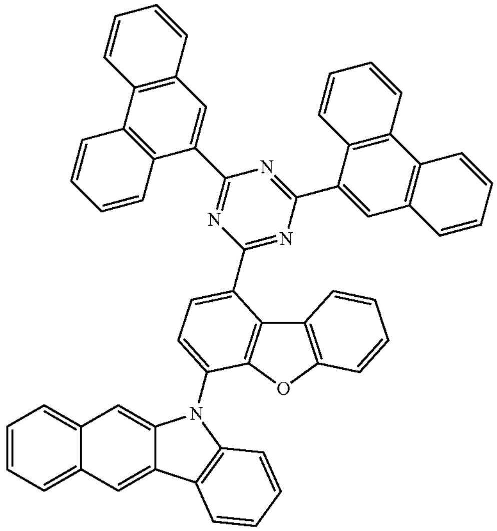
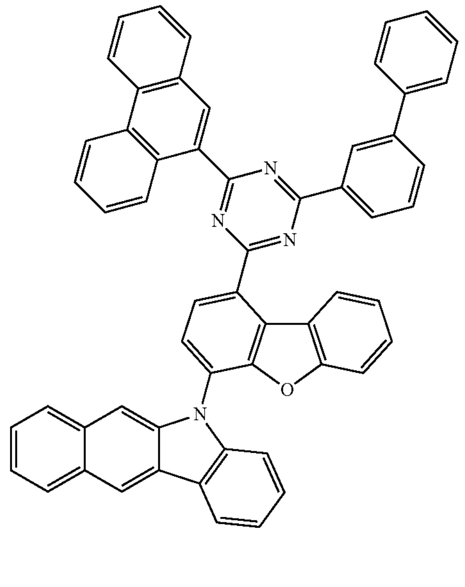

-continued
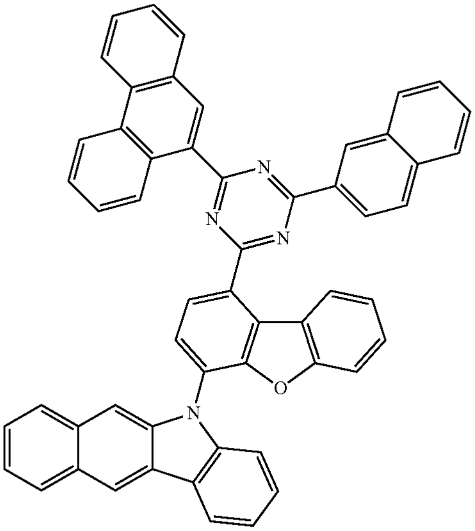
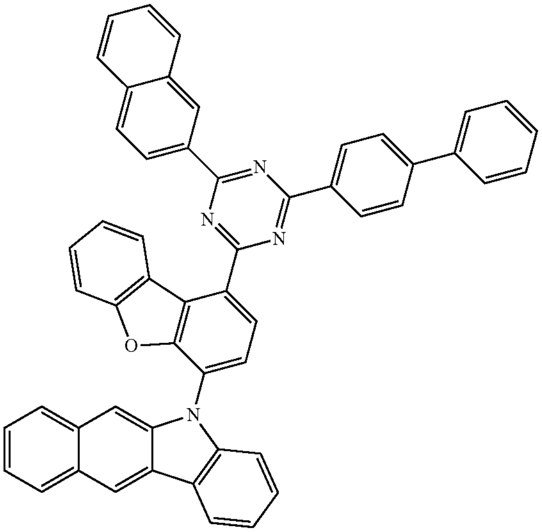
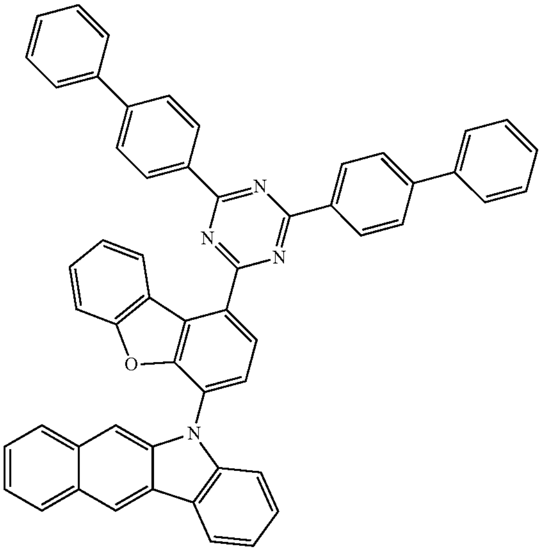
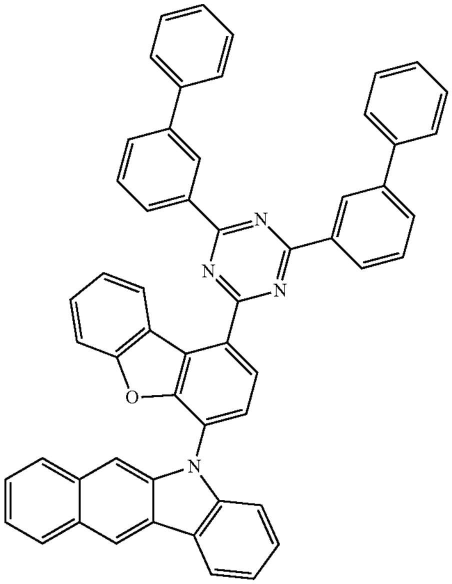
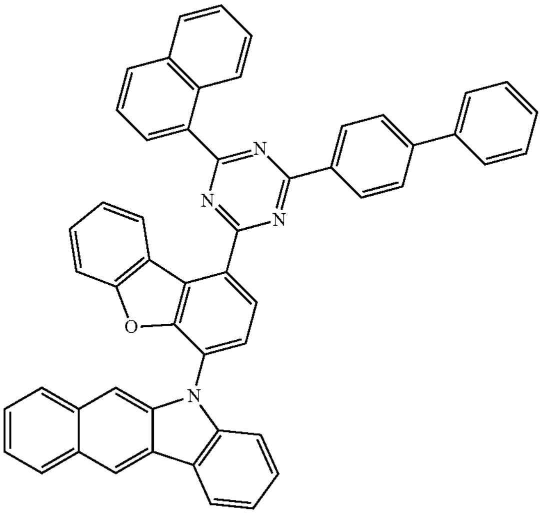
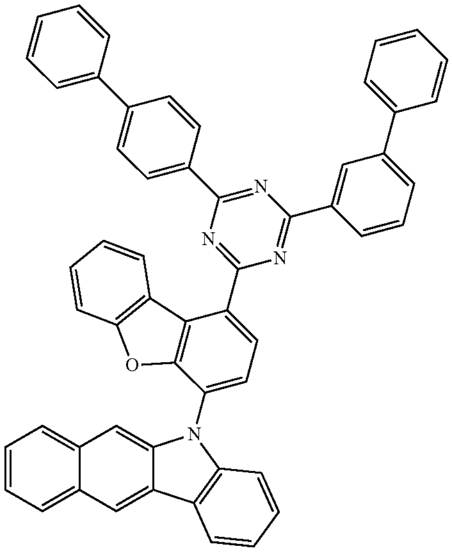
-continued -continued
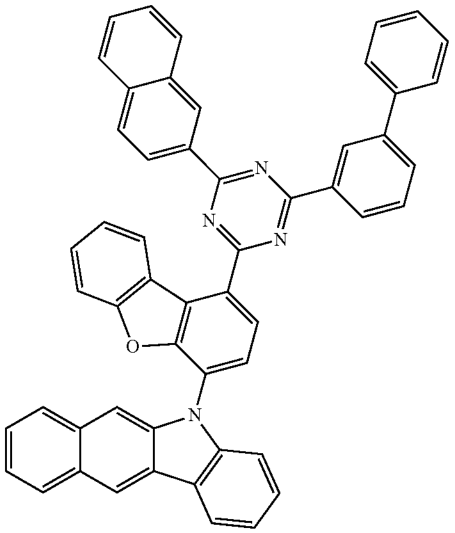
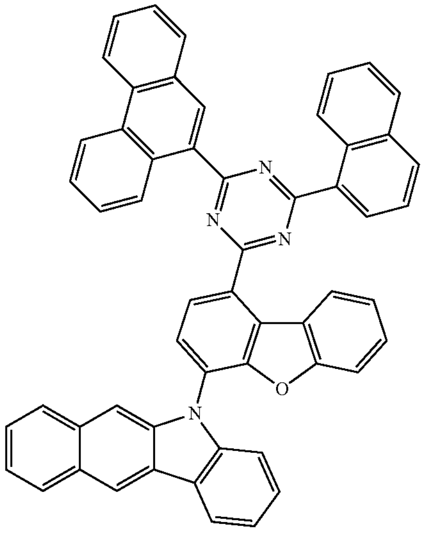
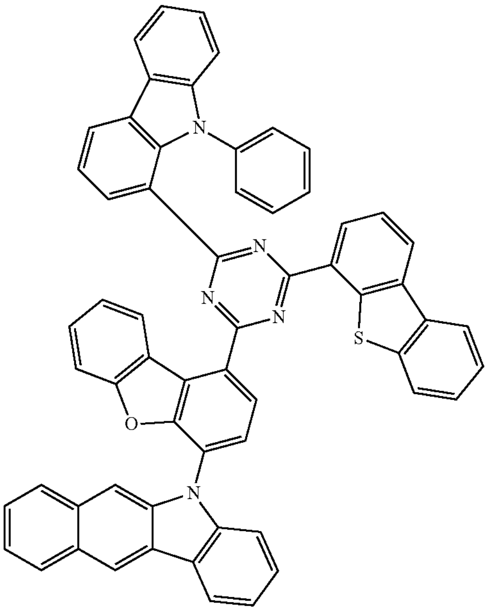
-continued
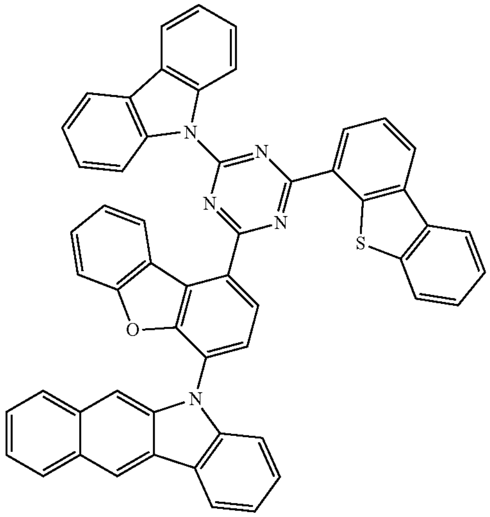
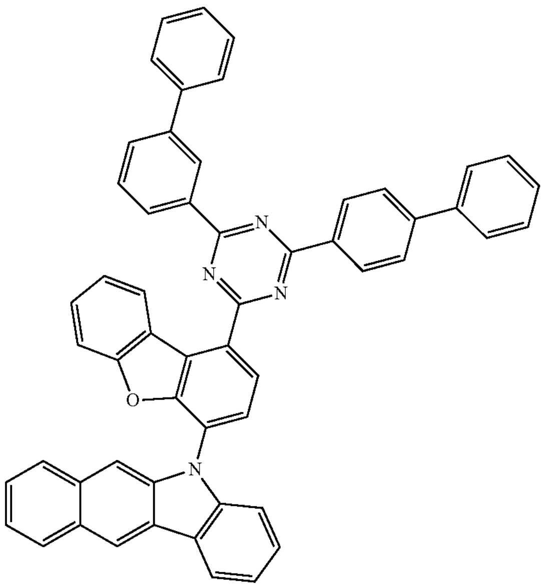
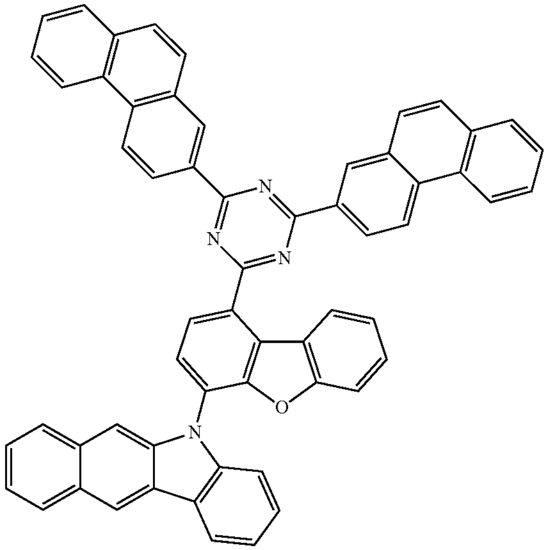

-continued
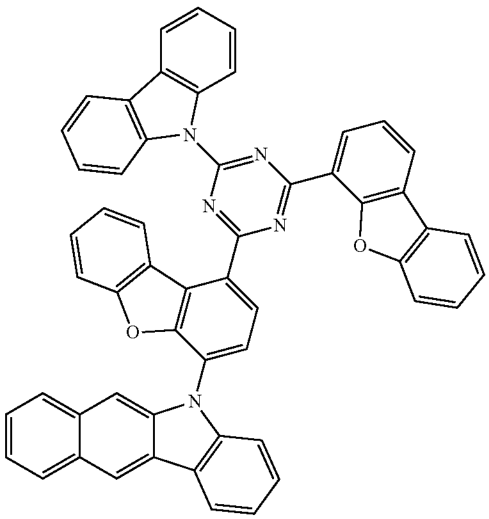
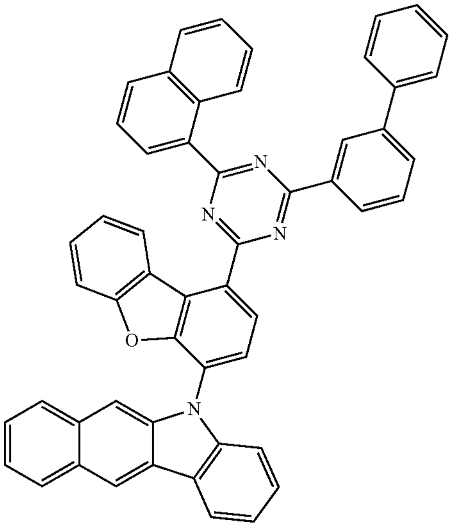
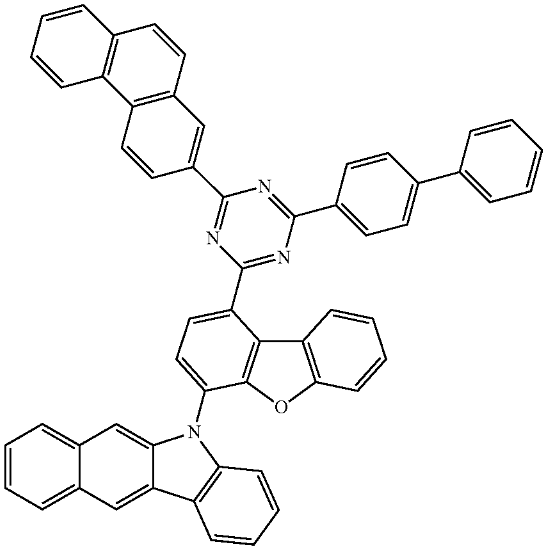
-continued
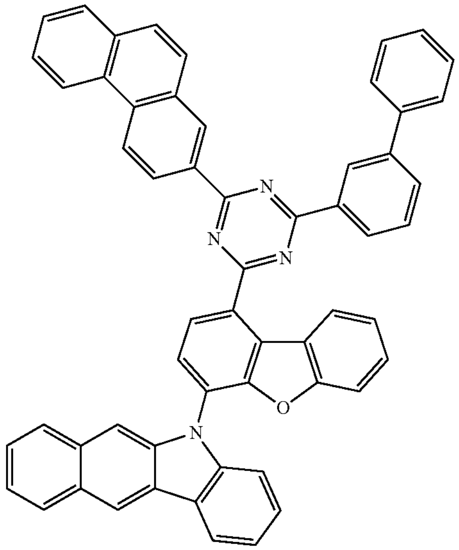
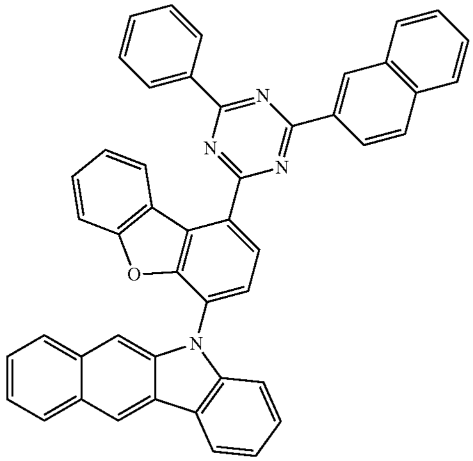
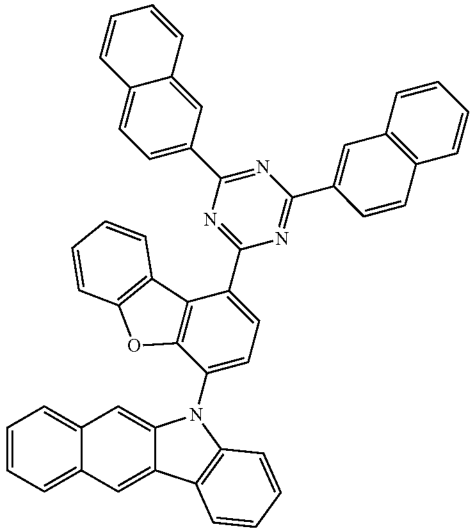

-continued
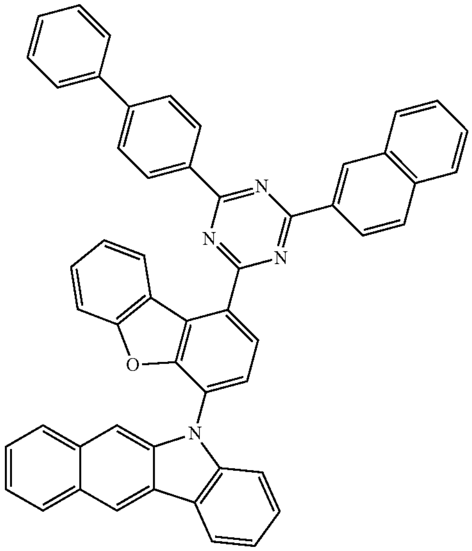
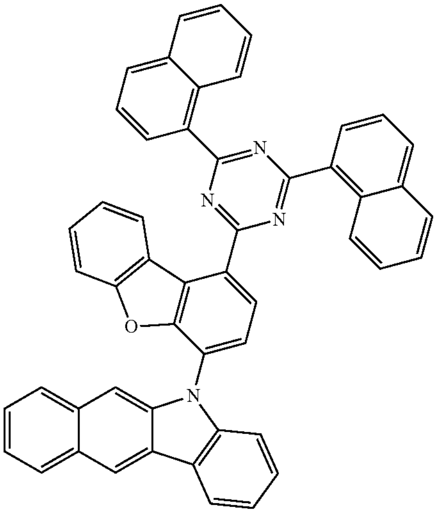
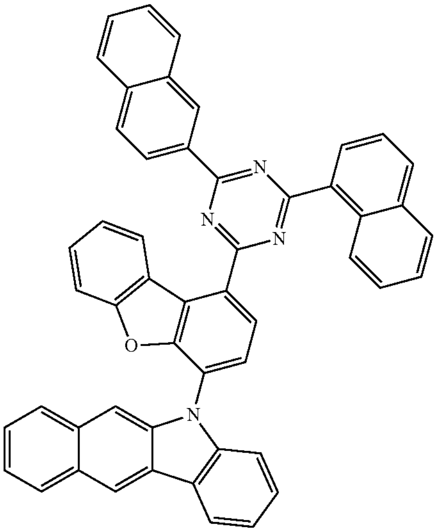
-continued
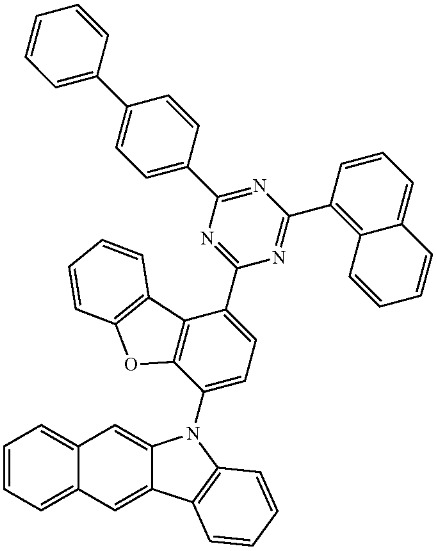
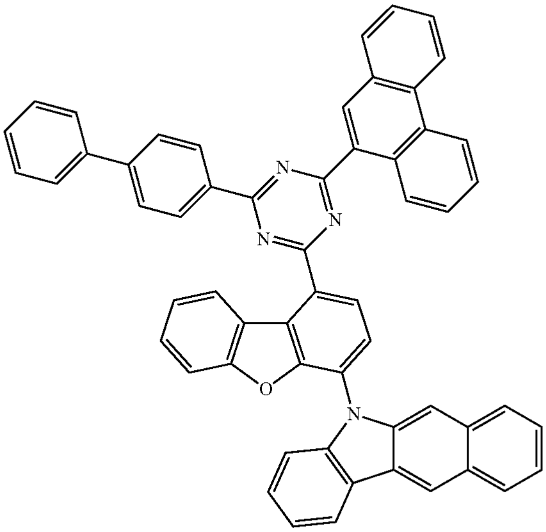
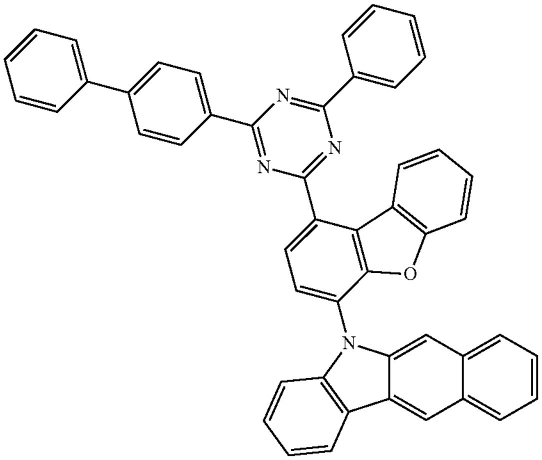

-continued
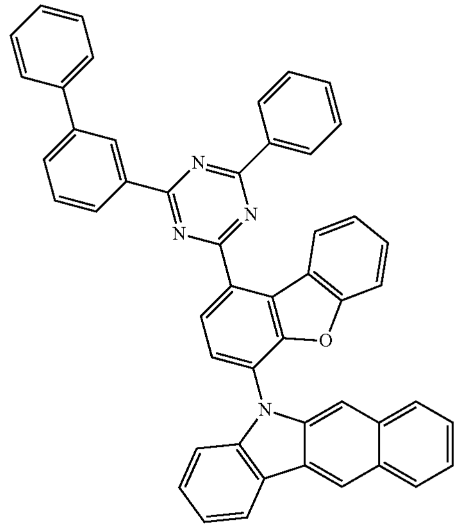
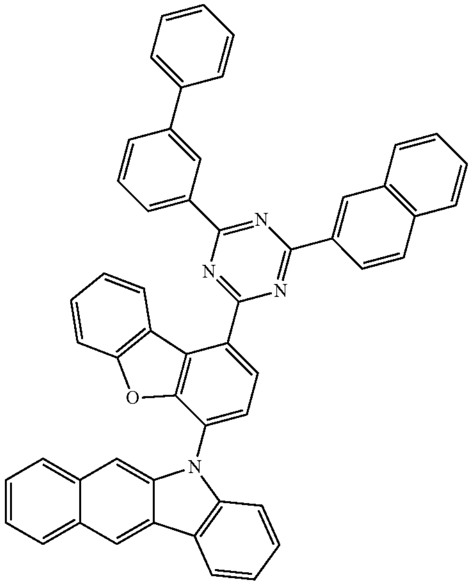
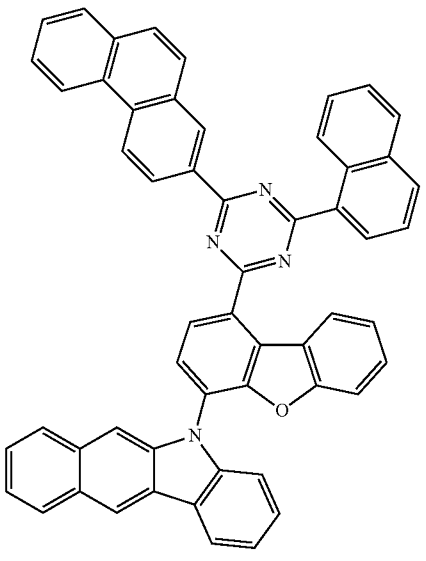
-continued
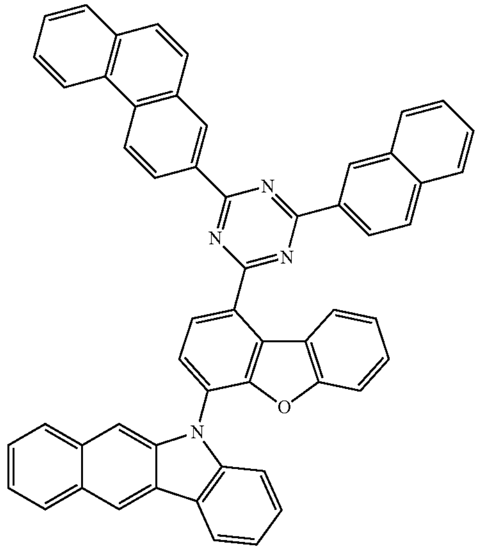
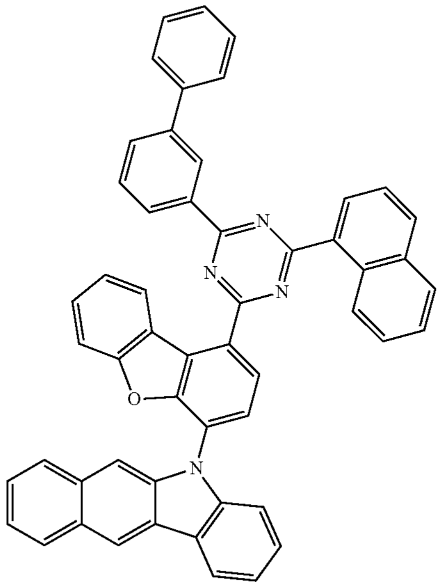
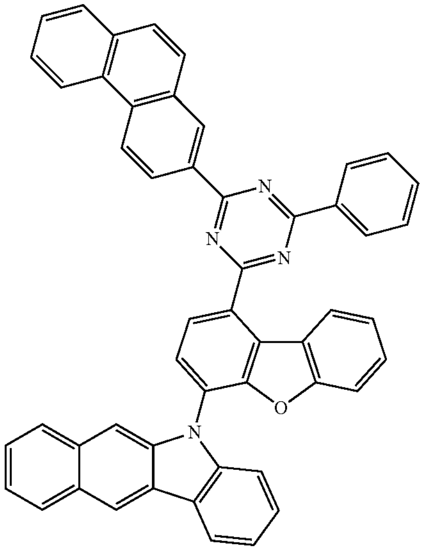

-continued
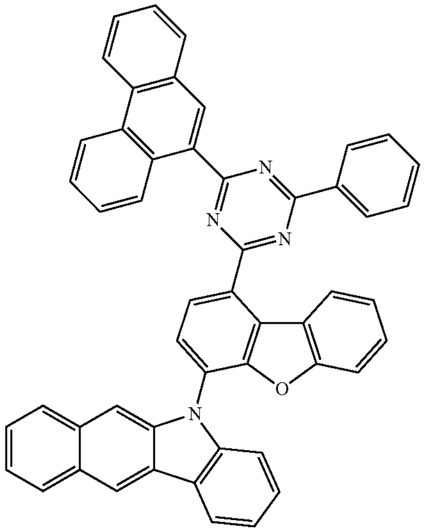
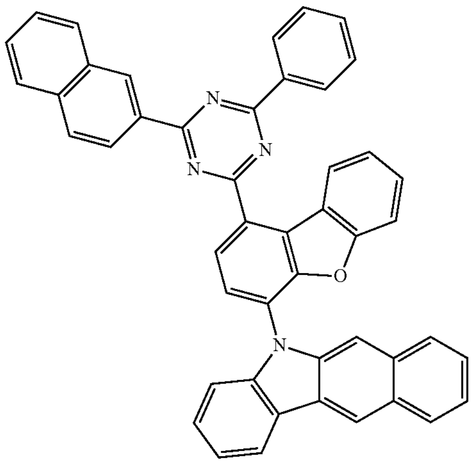
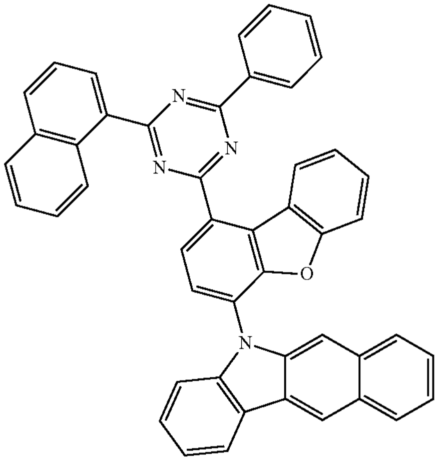
-continued
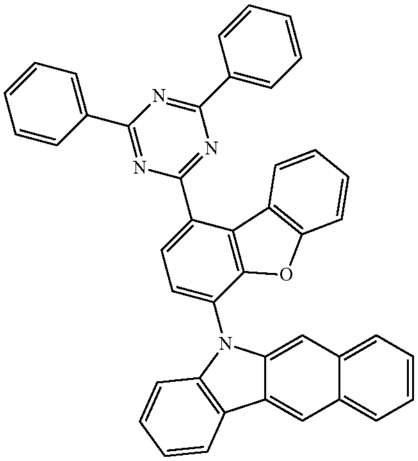
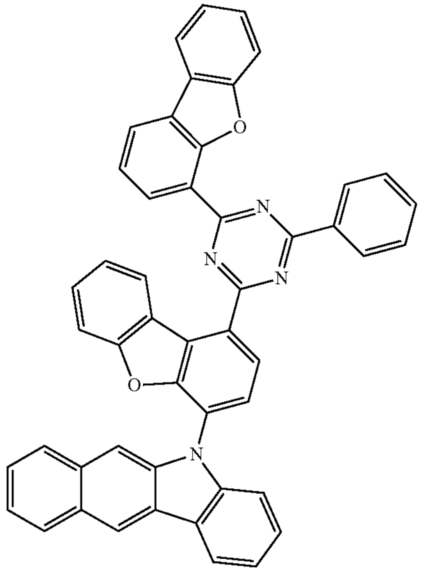
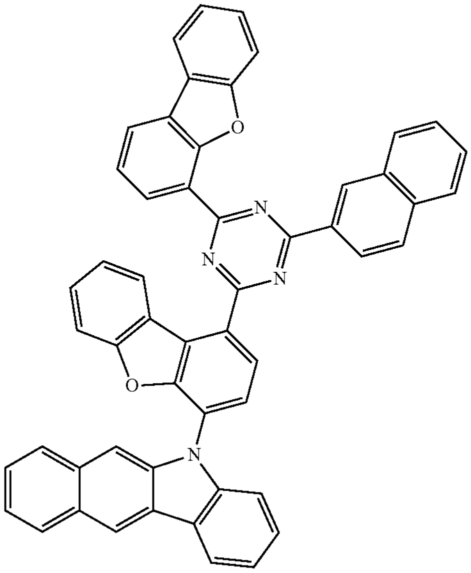

-continued
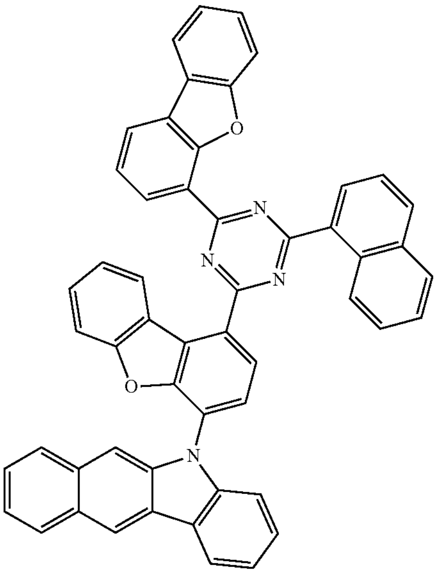
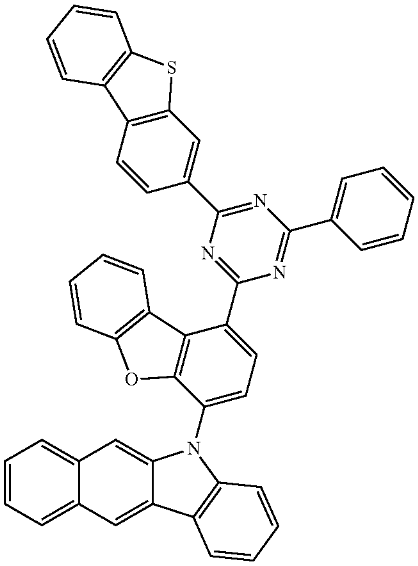
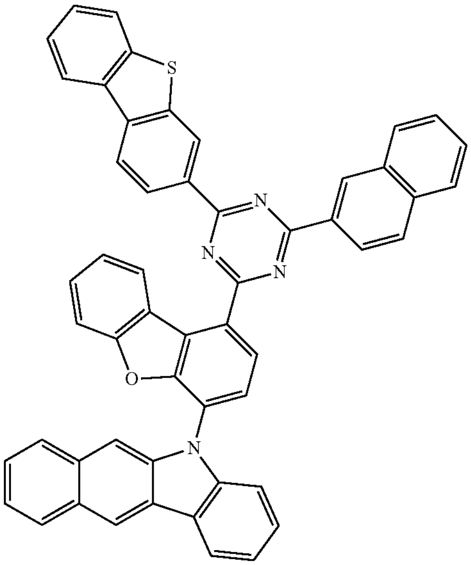
-continued
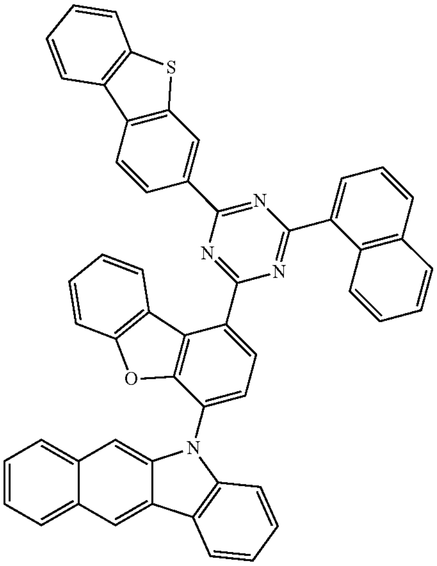
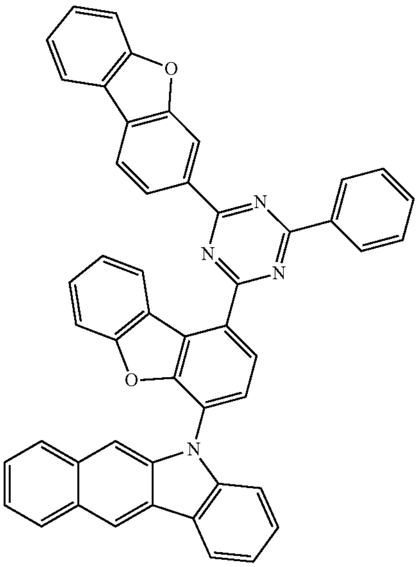
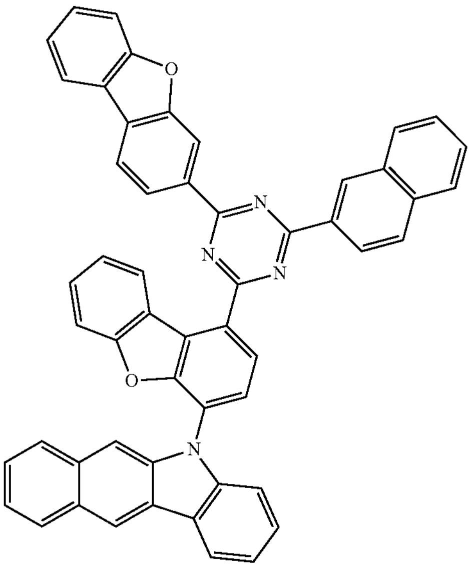

-continued
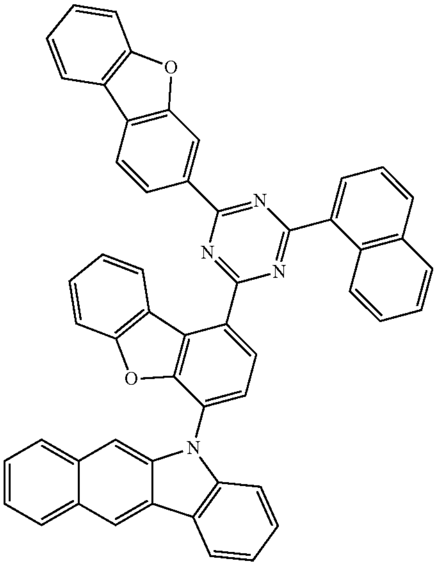
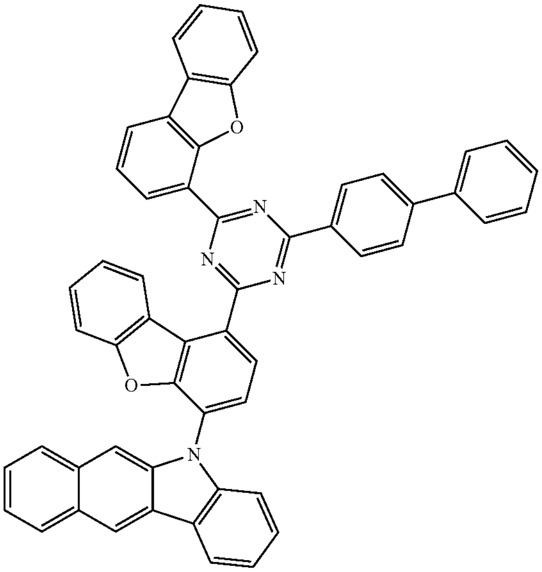
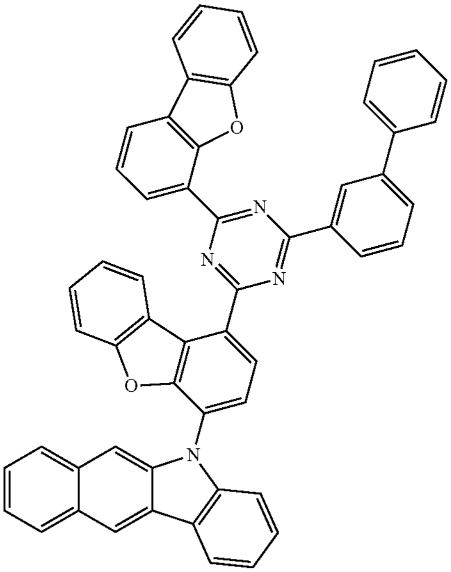
-continued
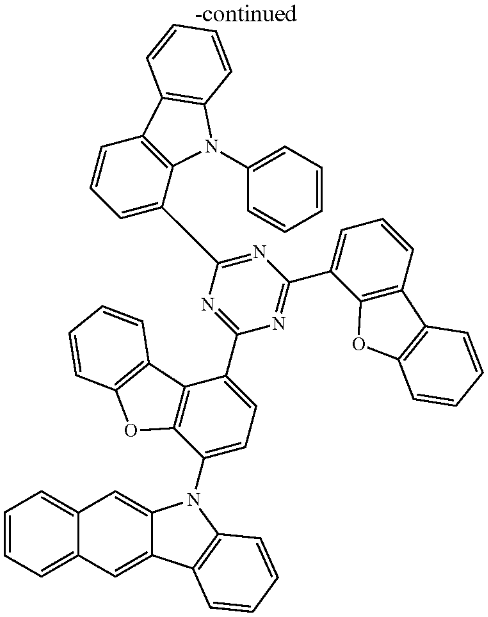
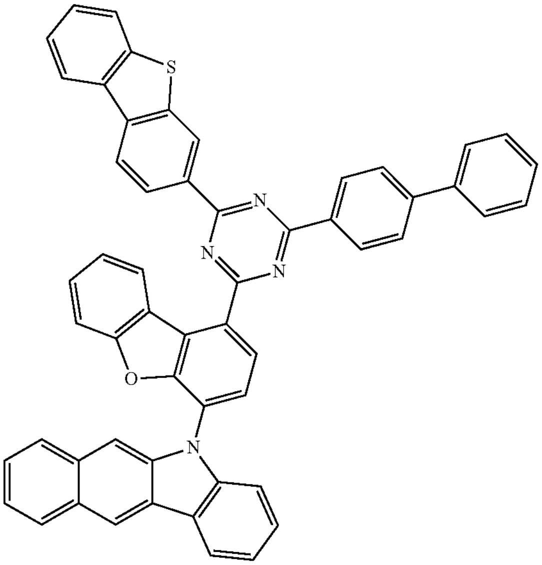
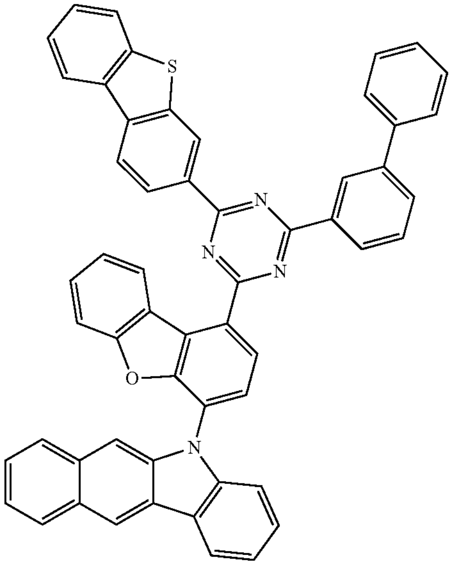

-continued
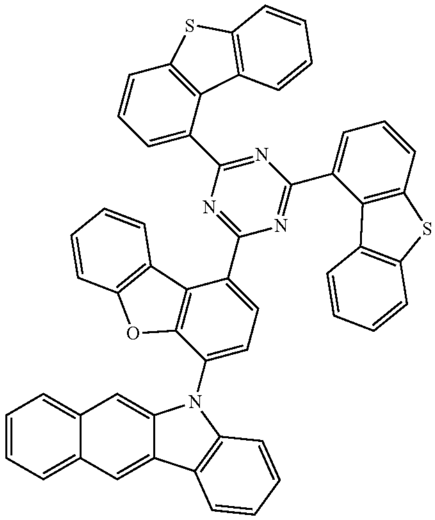
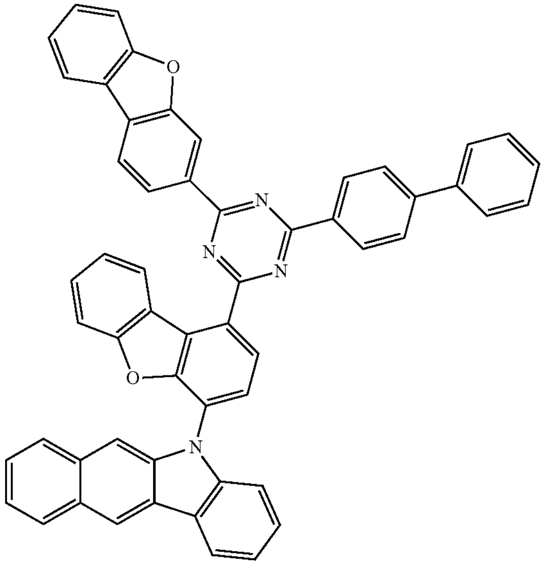
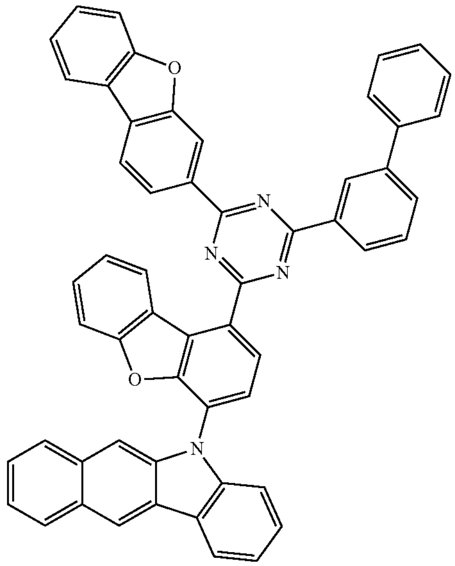
-continued
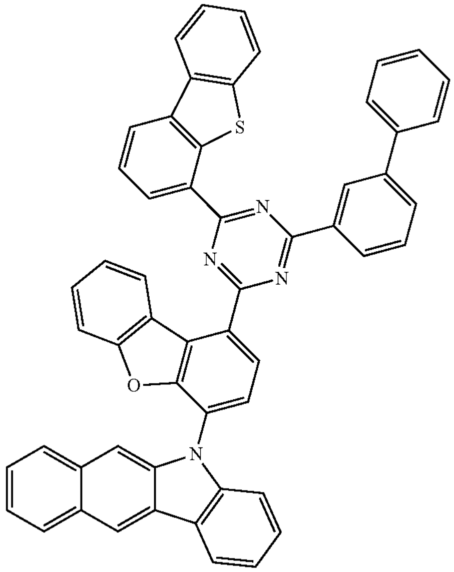
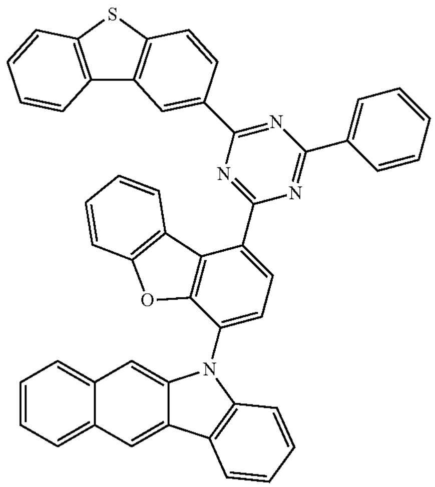
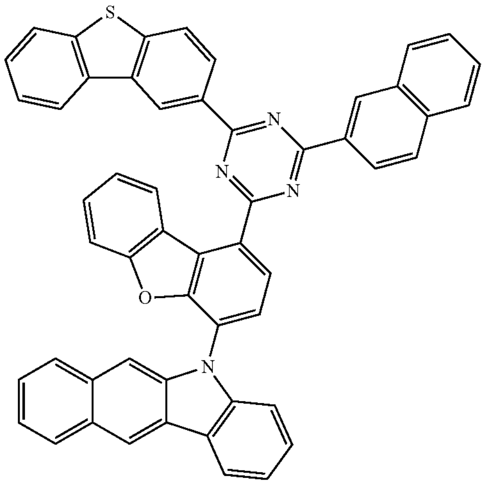

-continued
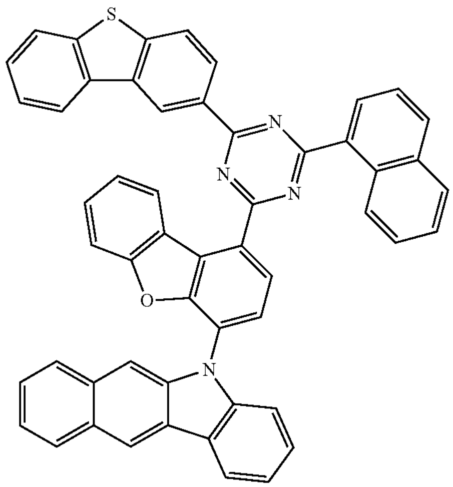
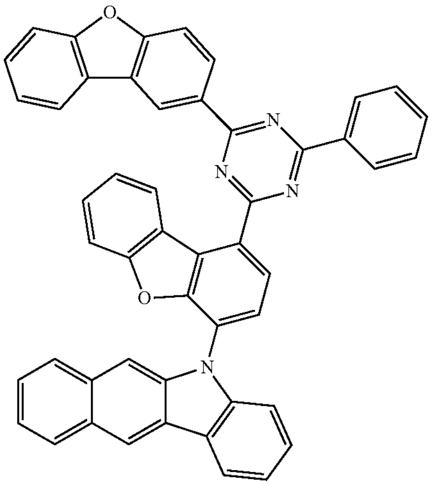
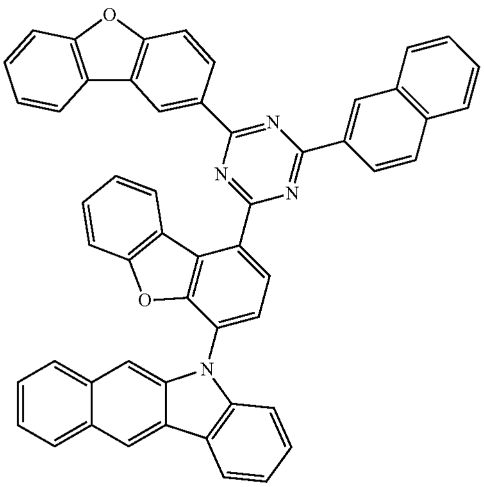
-continued
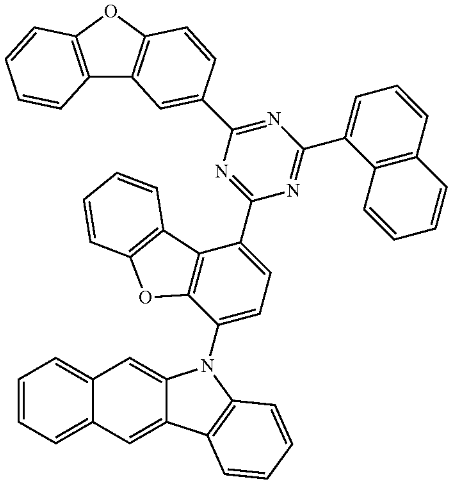
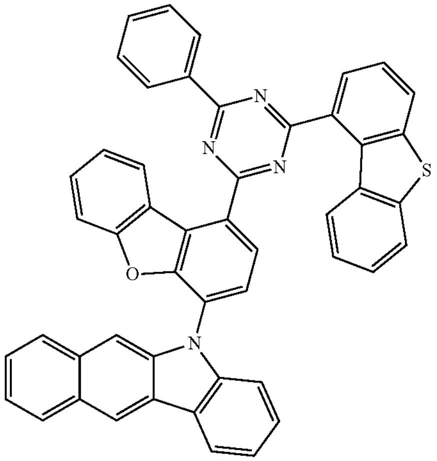
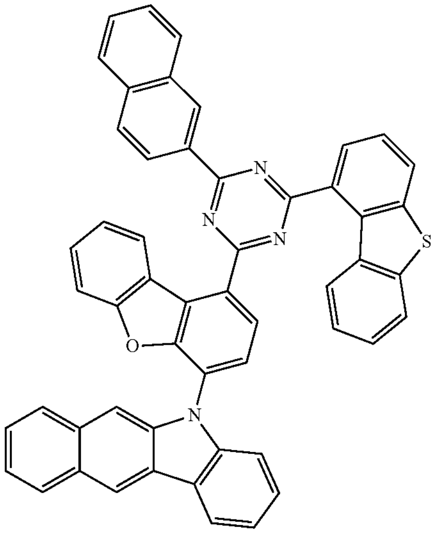

-continued
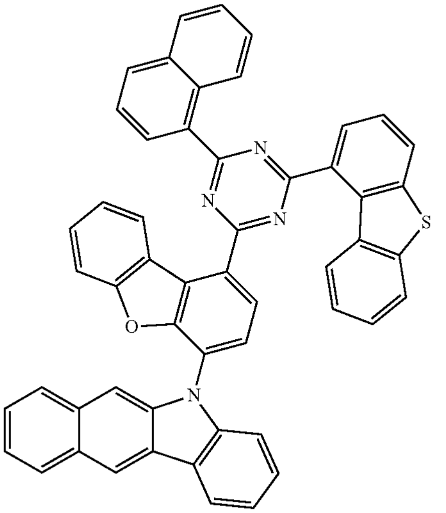
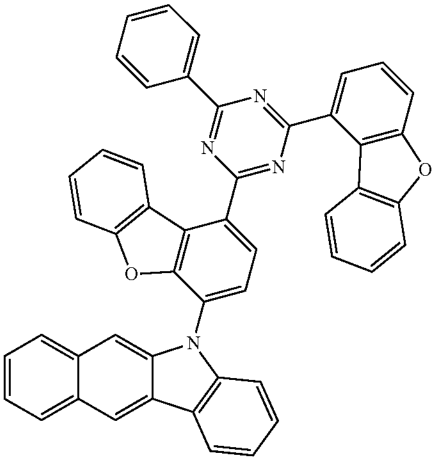
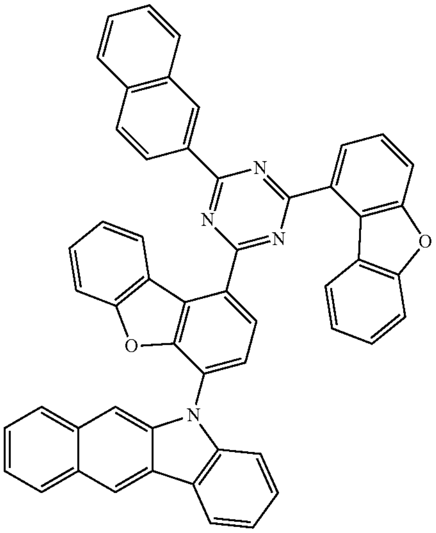
-continued
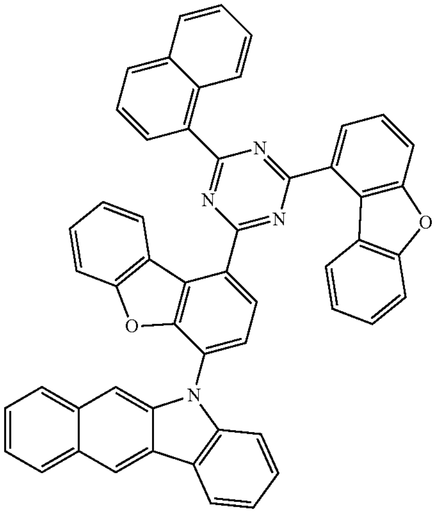
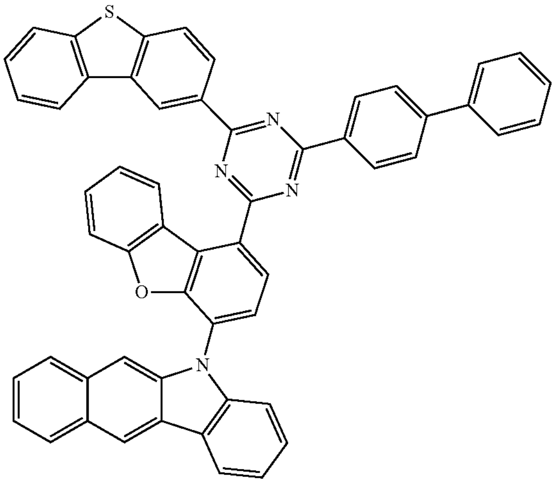
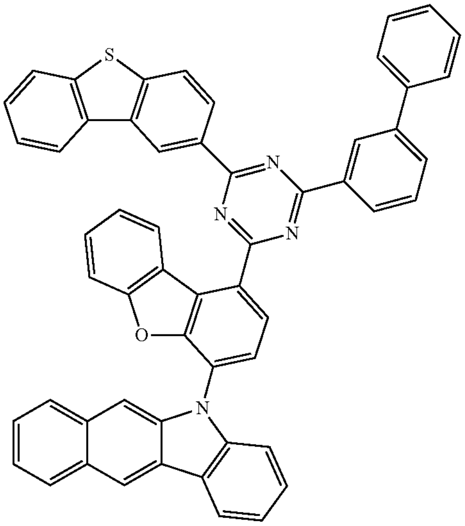

-continued
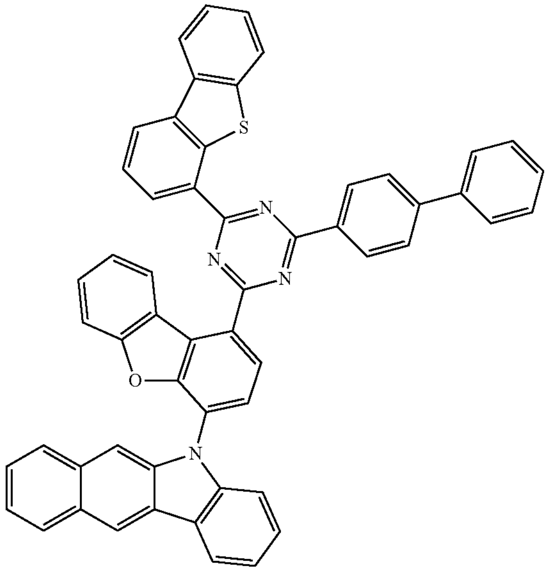
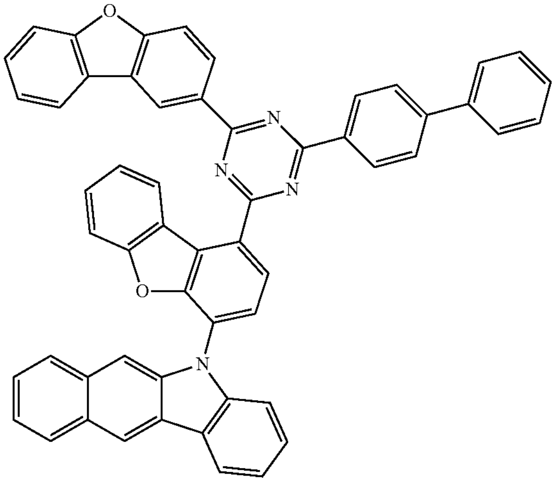
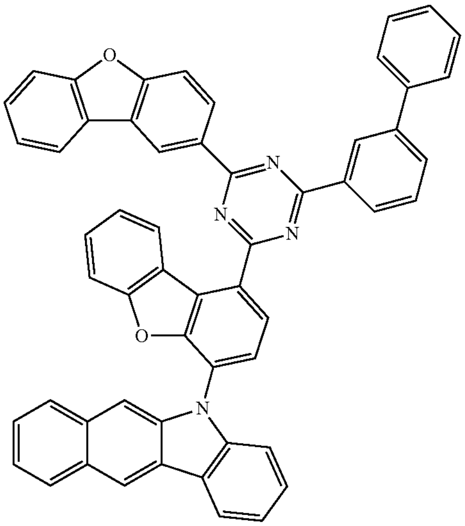
-continued
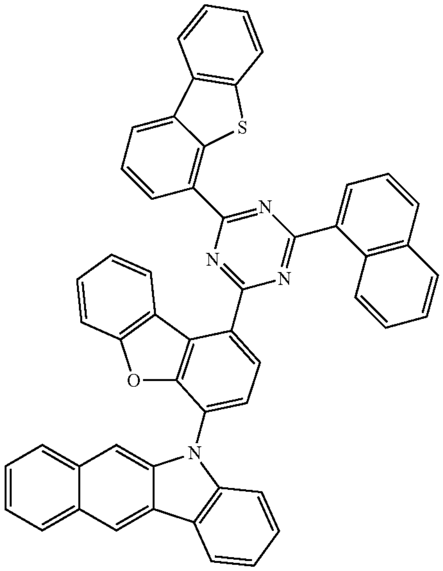
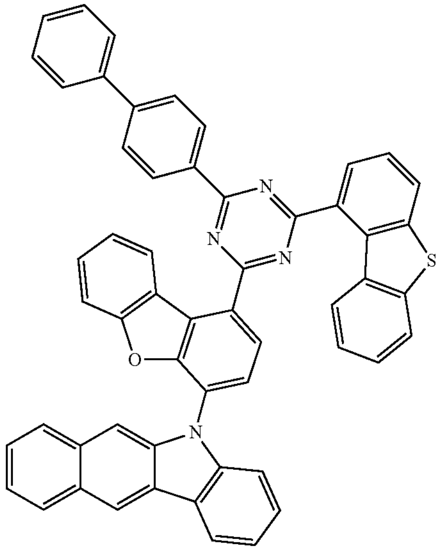
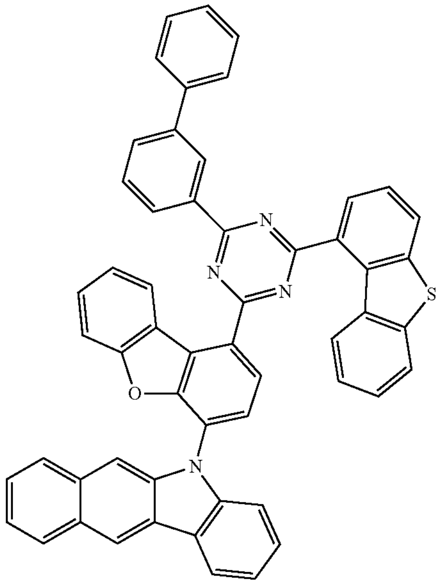

-continued
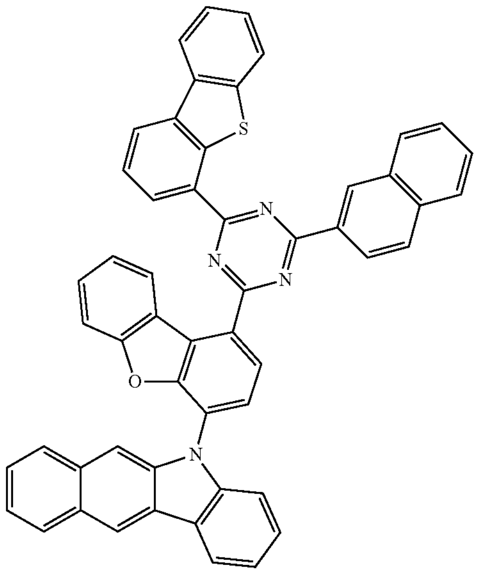
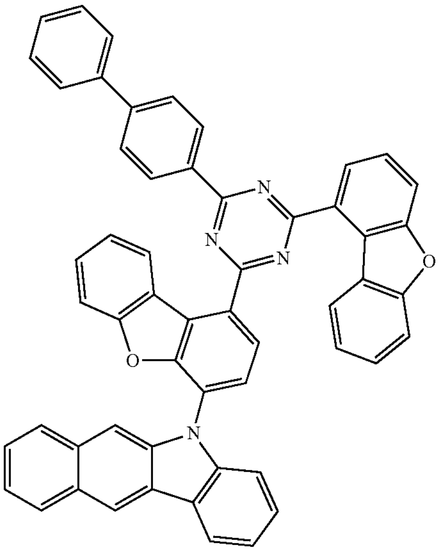
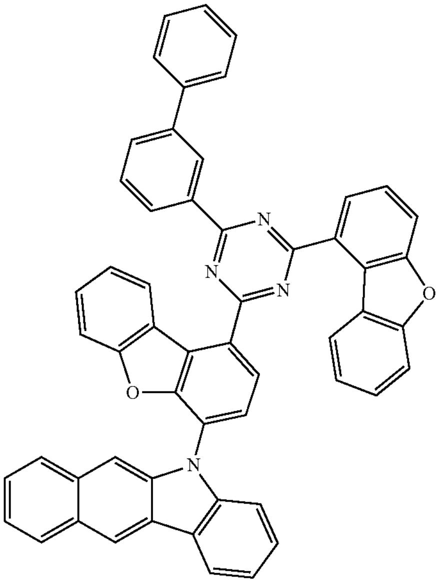
-continued
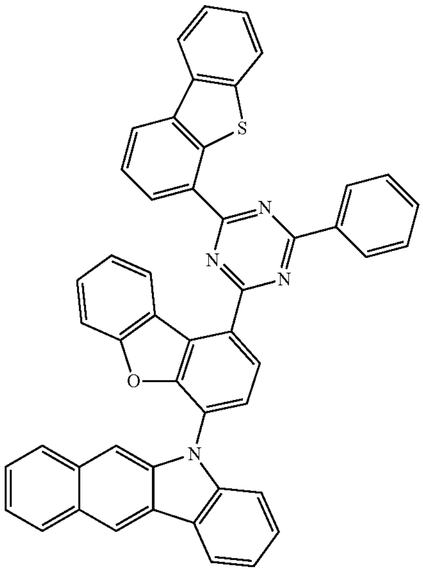
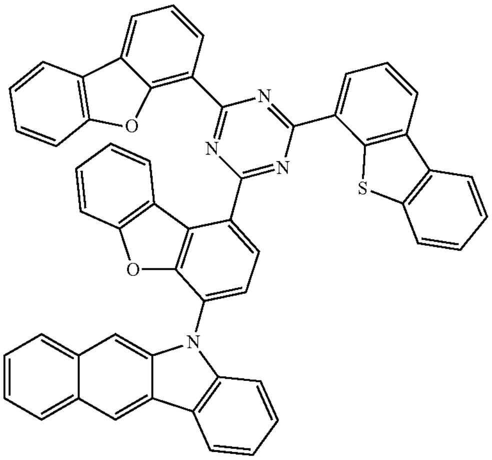
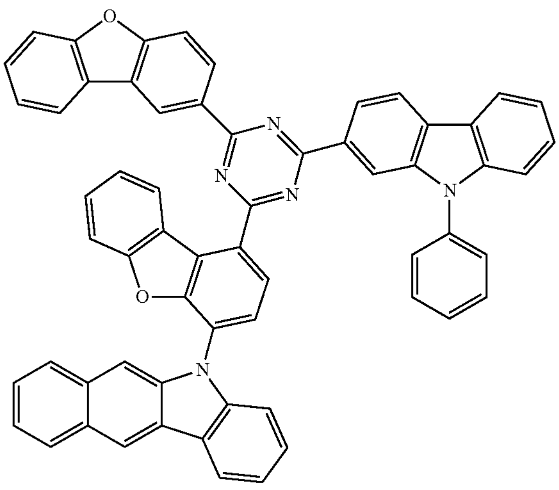

-continued
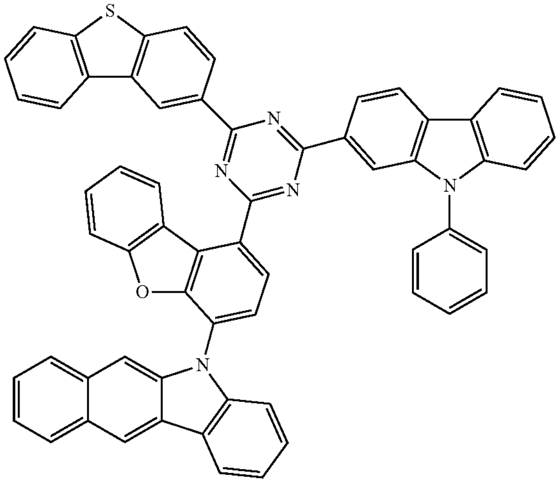
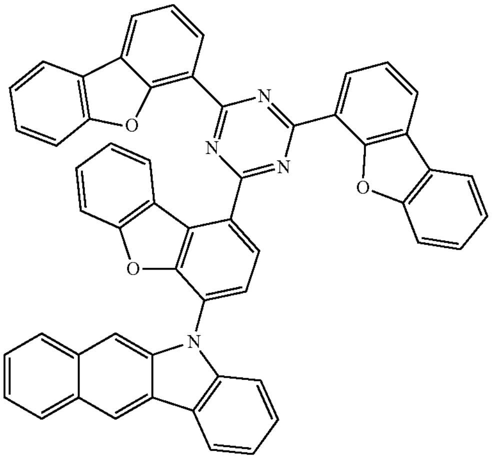
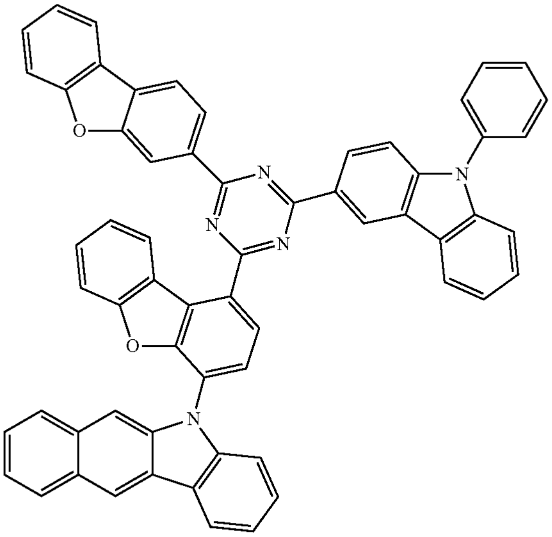
-continued
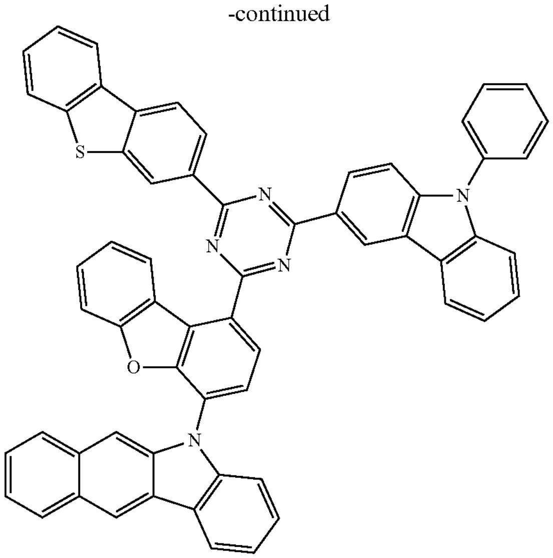
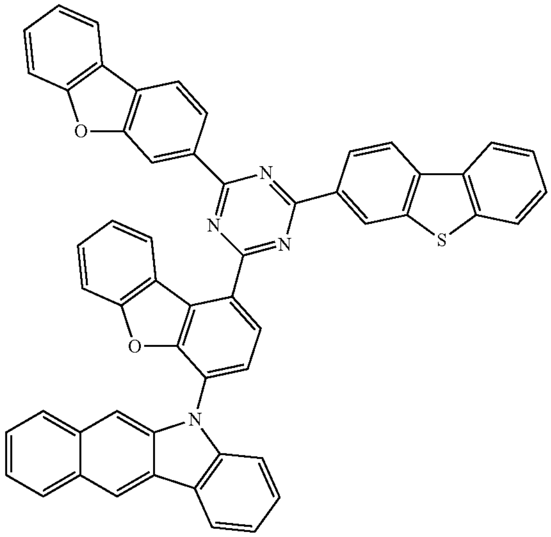
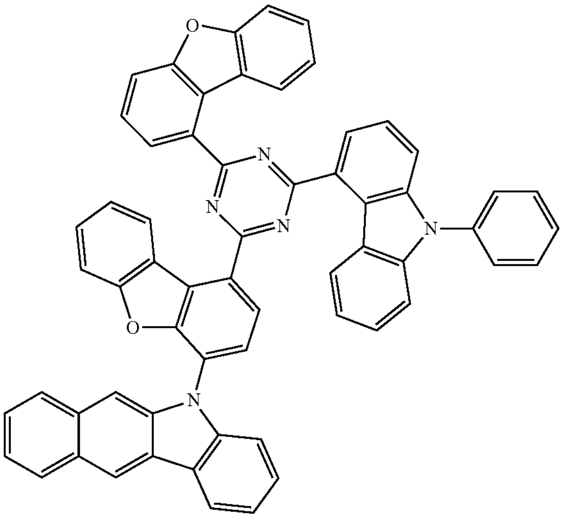

-continued
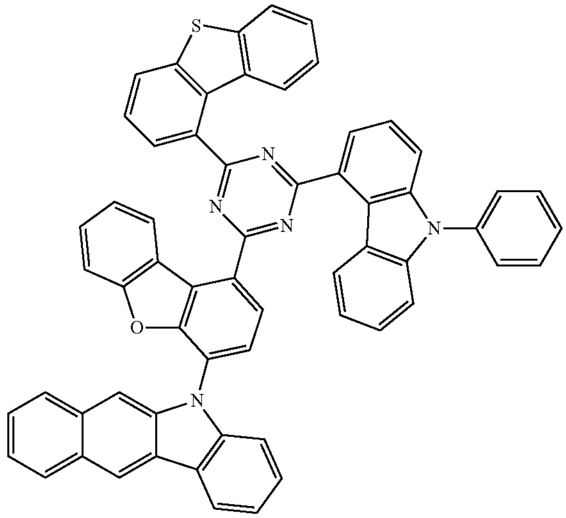
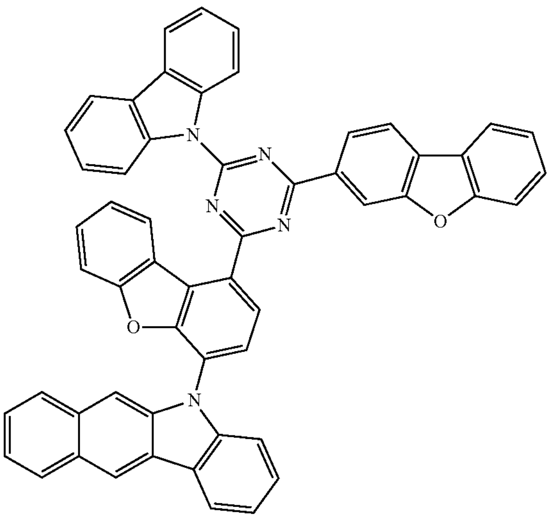
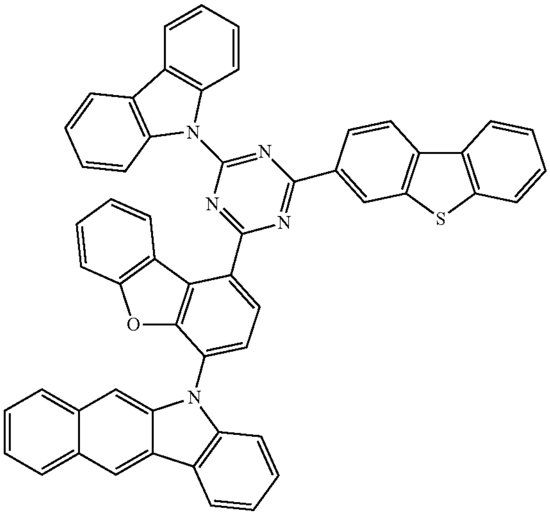
-continued
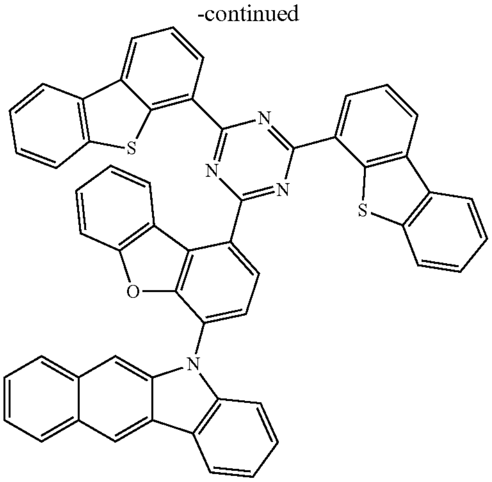
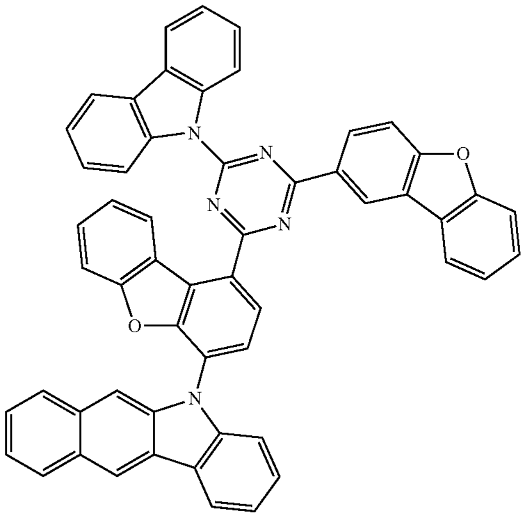
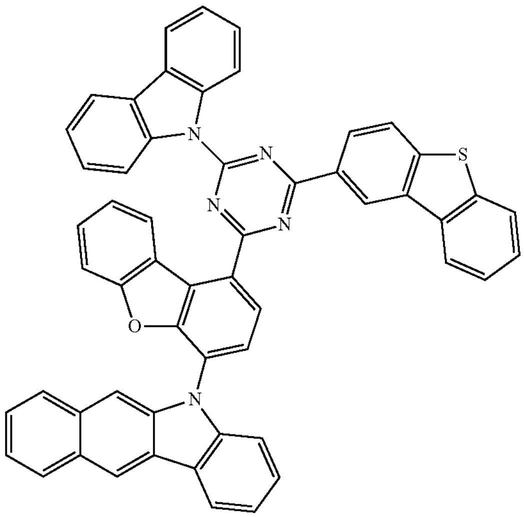

-continued
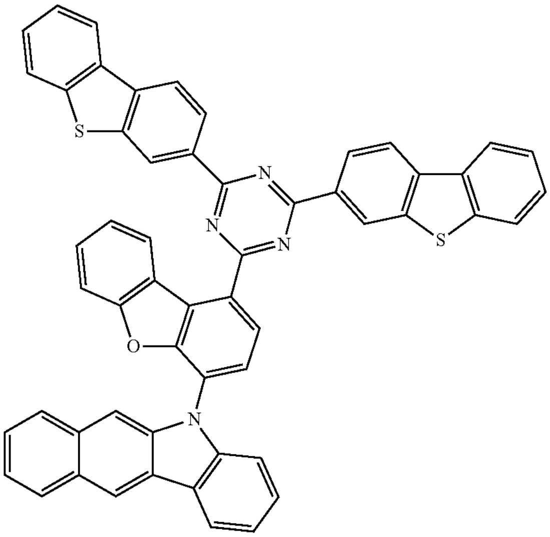
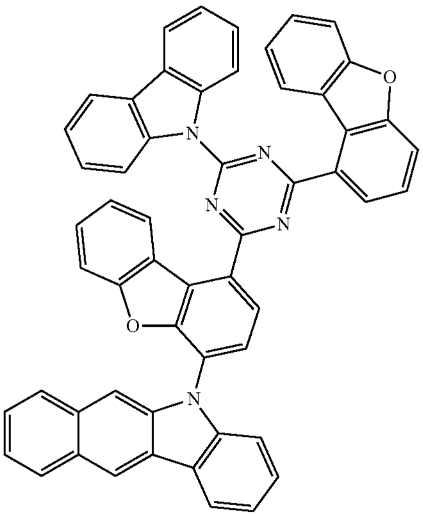
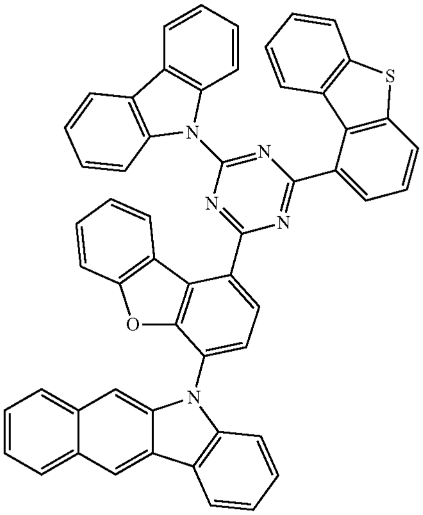
-continued
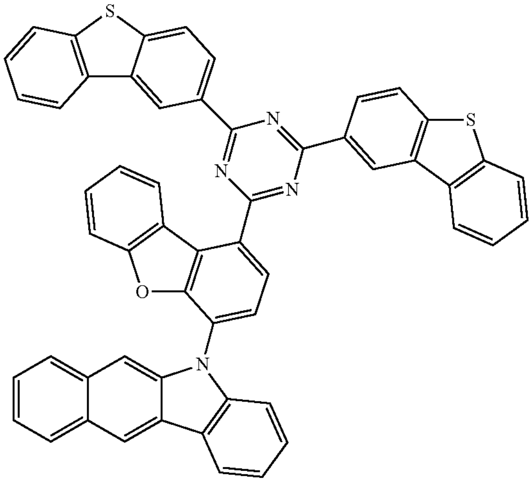
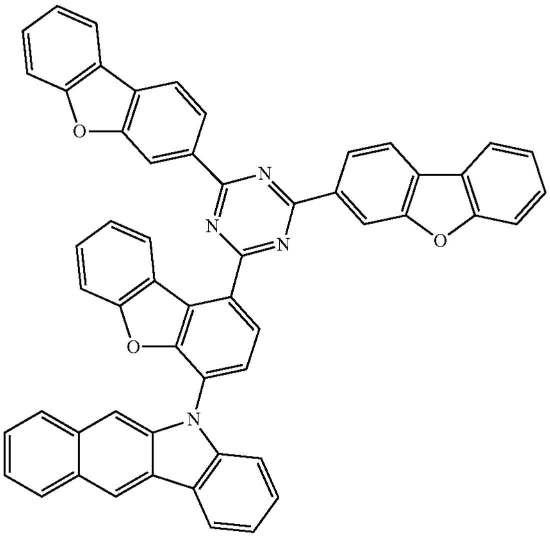
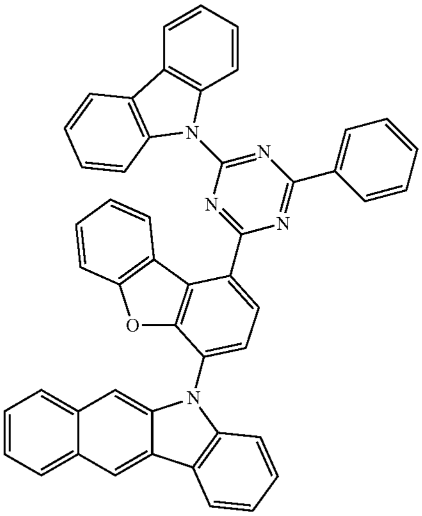

-continued
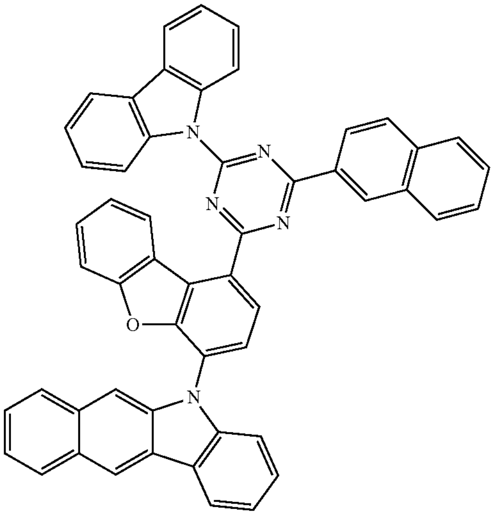
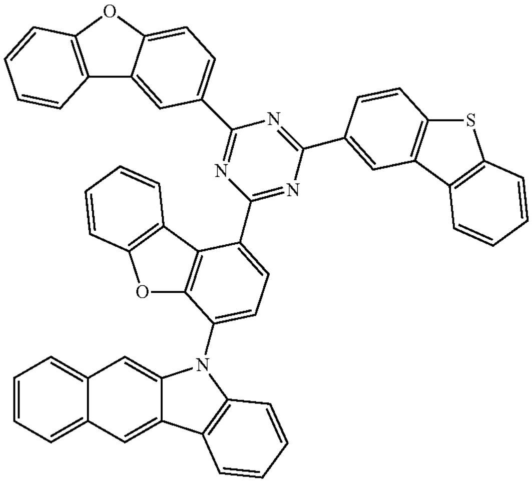
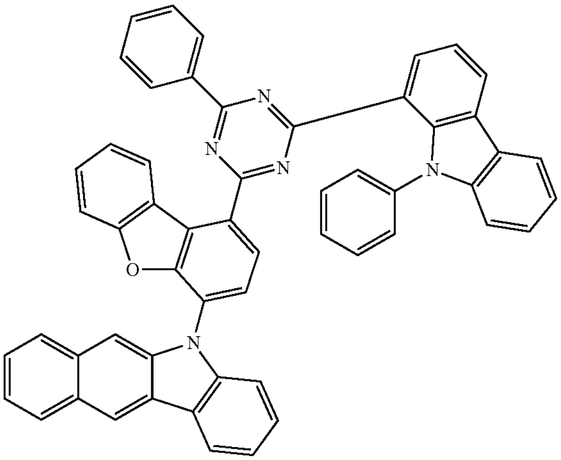
-continued
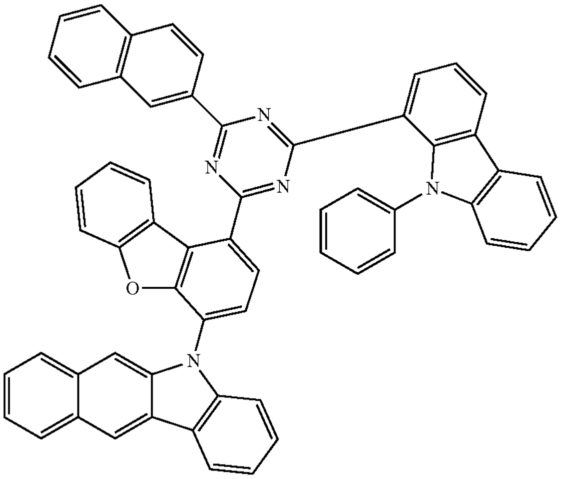
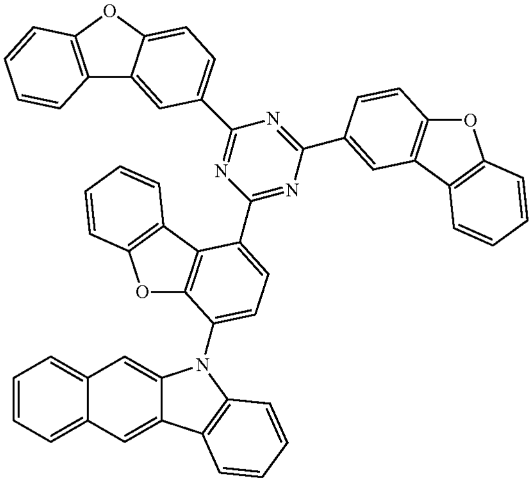
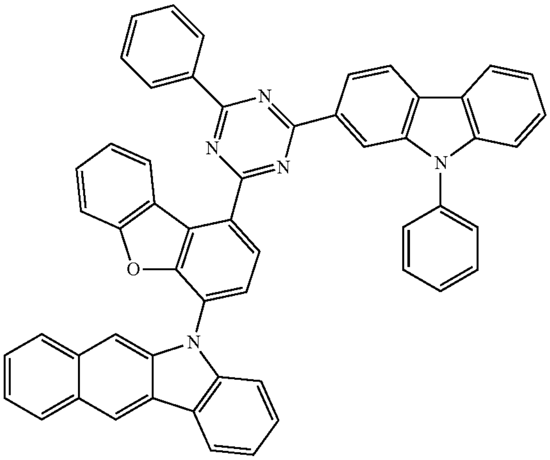

-continued
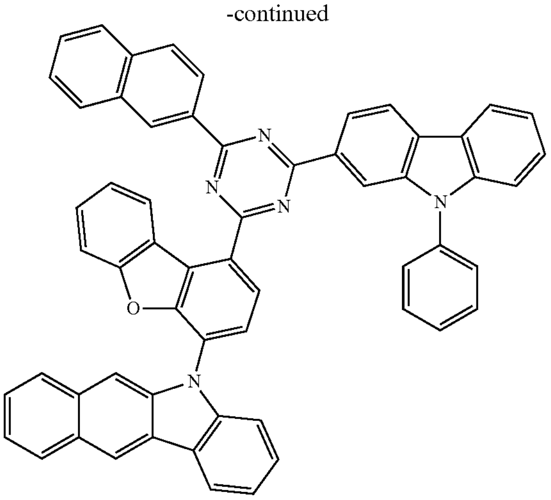
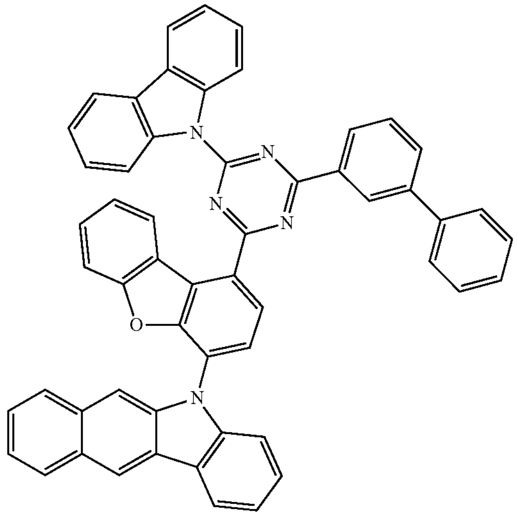
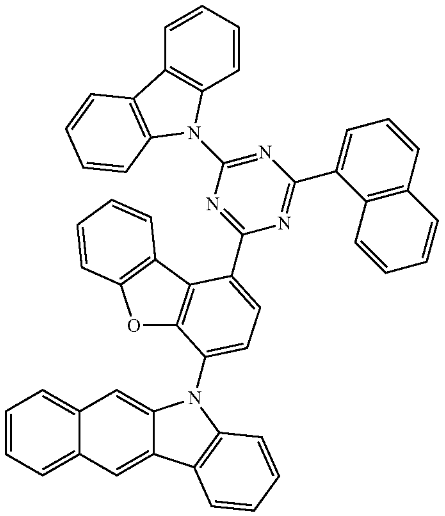
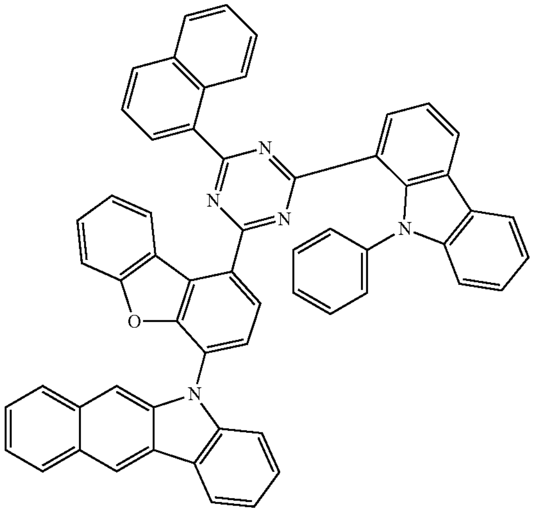
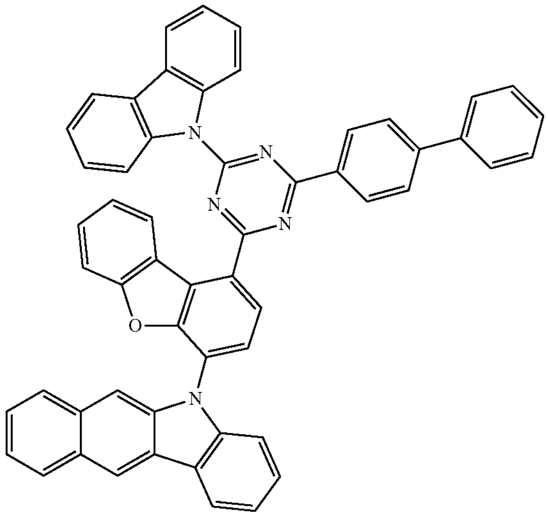
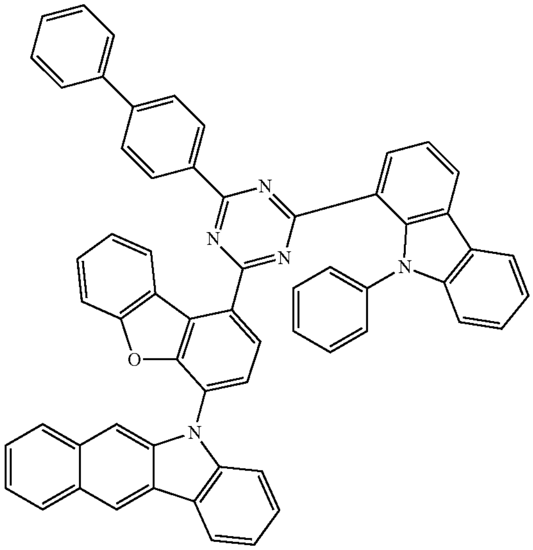

-continued
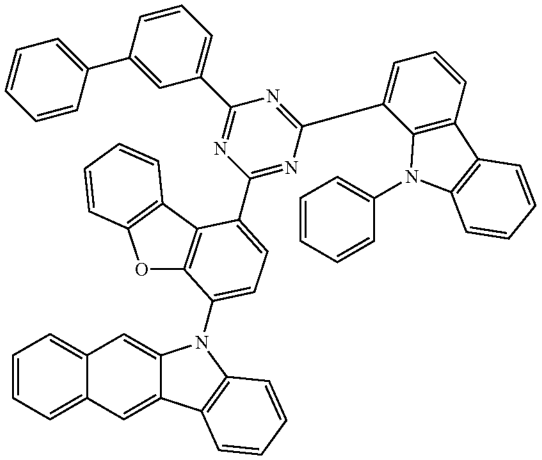
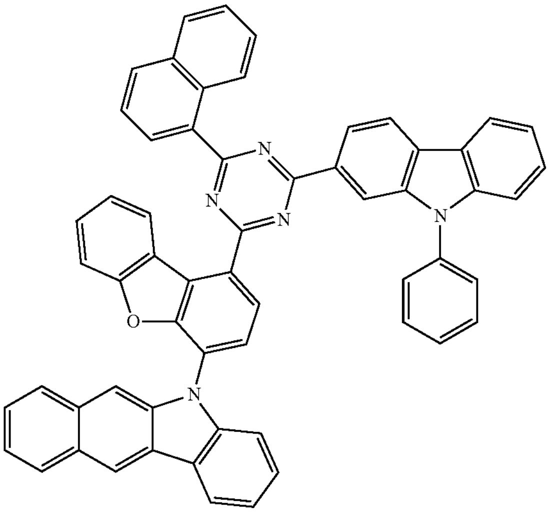
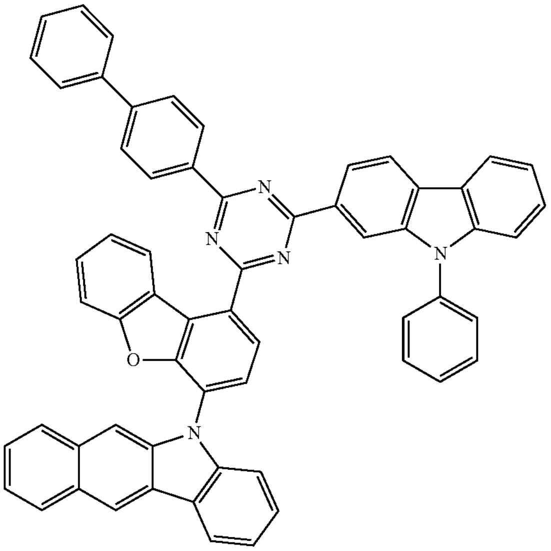
-continued
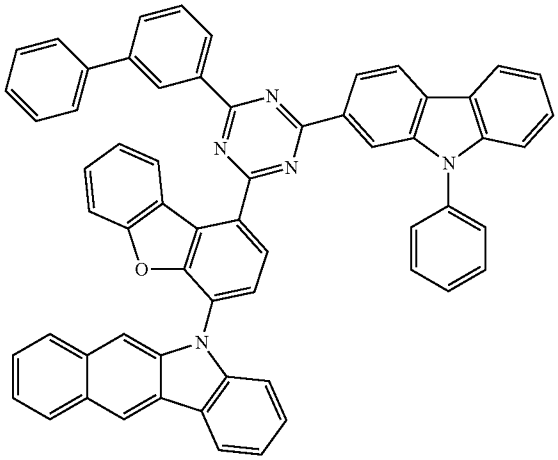
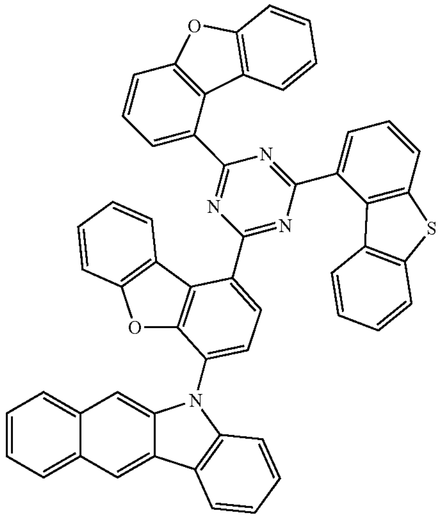
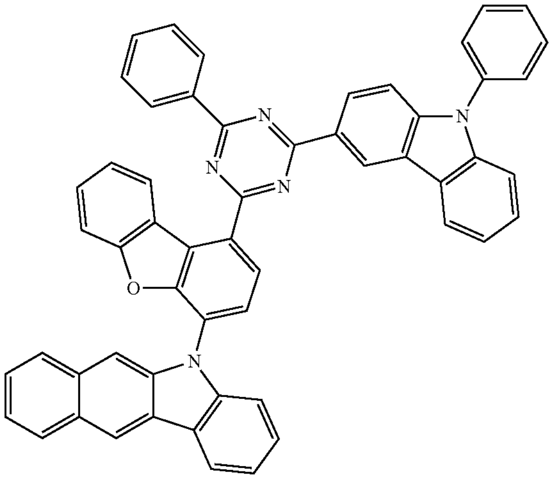

-continued
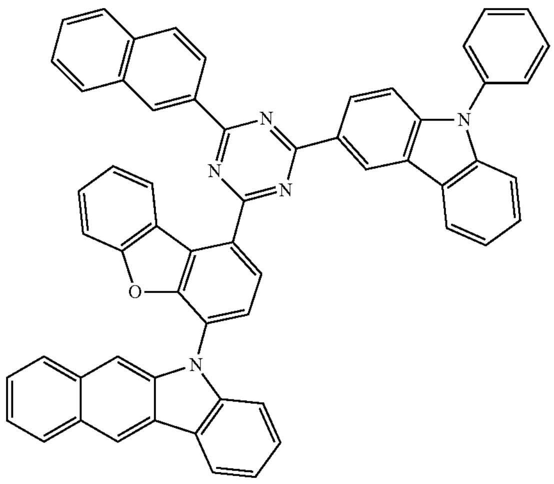
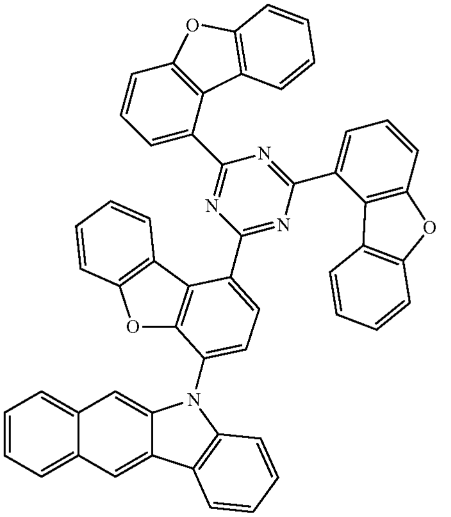
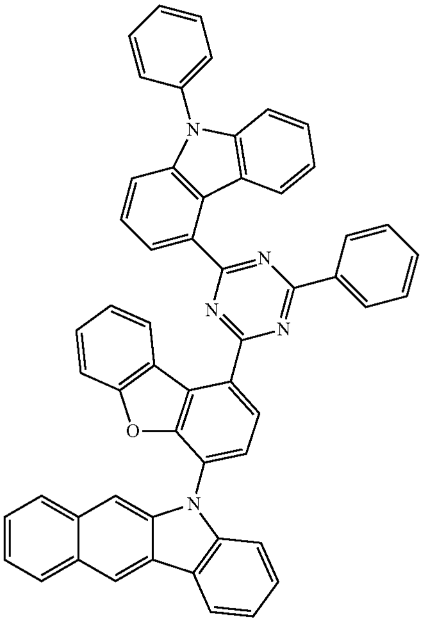
-continued
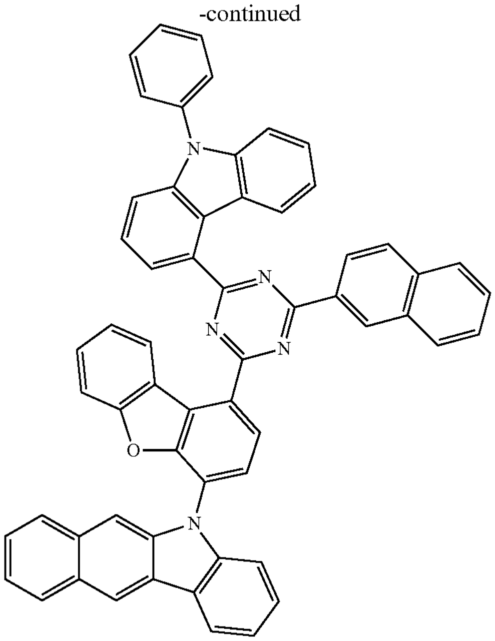
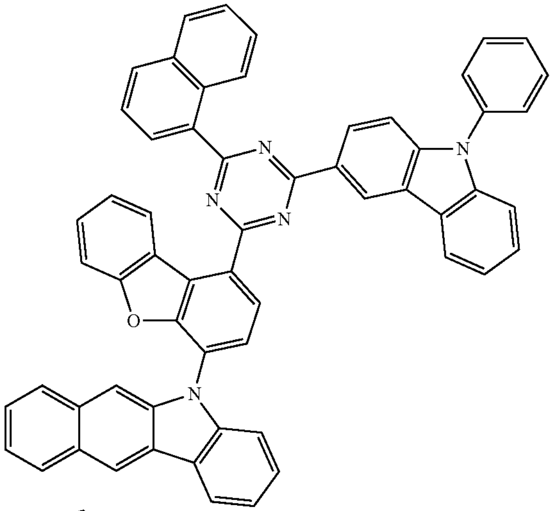
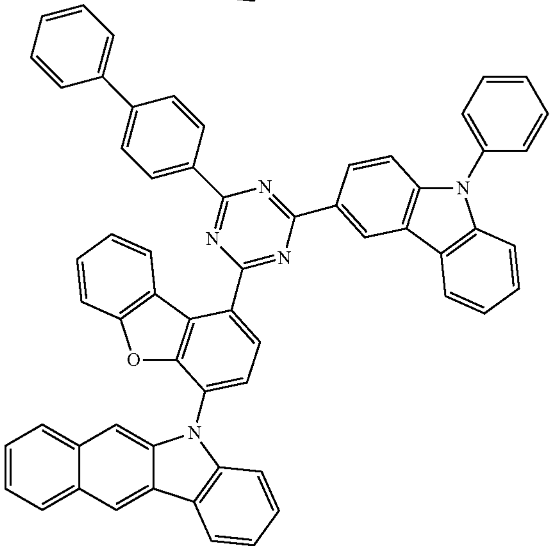

-continued
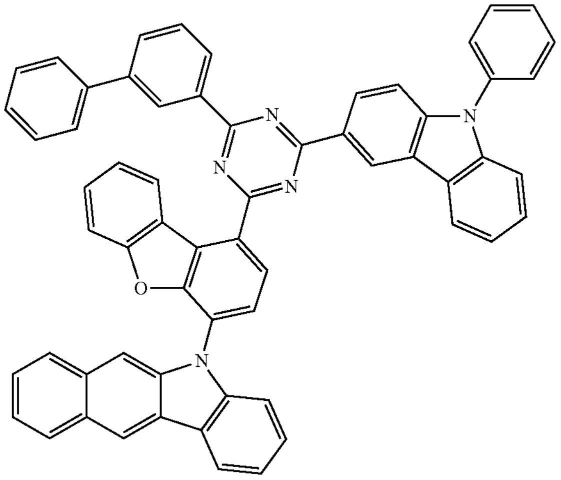
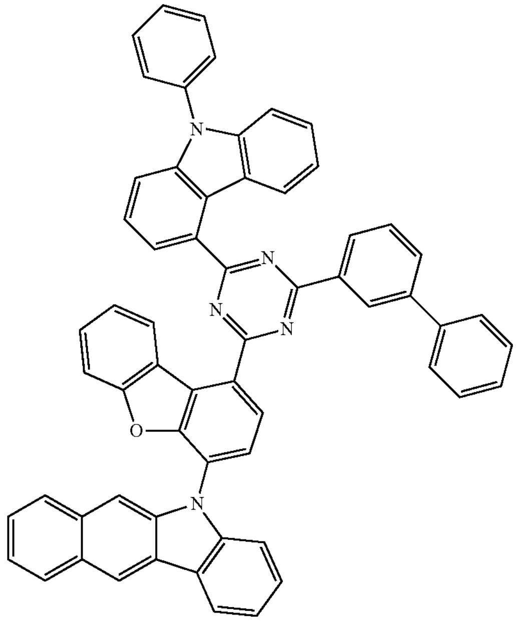
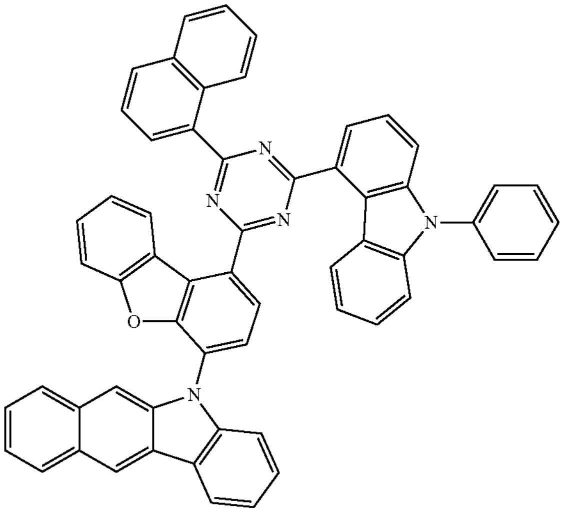
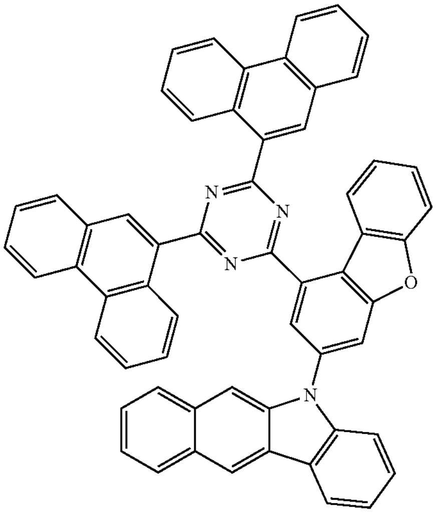
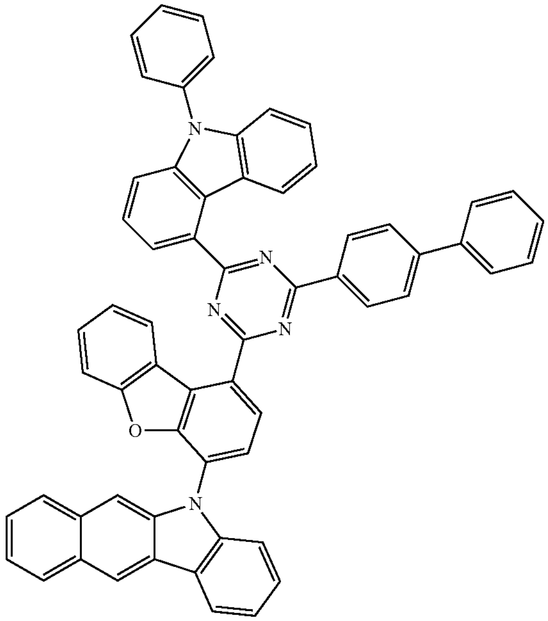
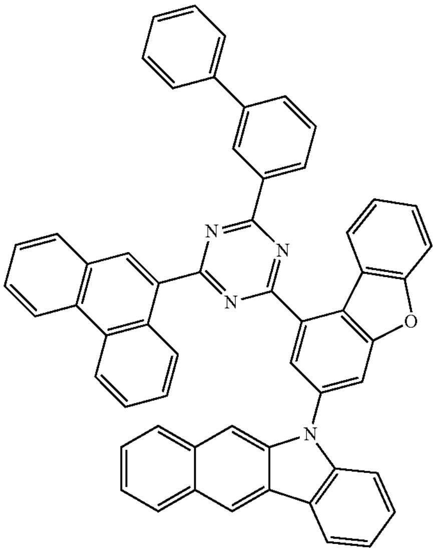
-continued -continued
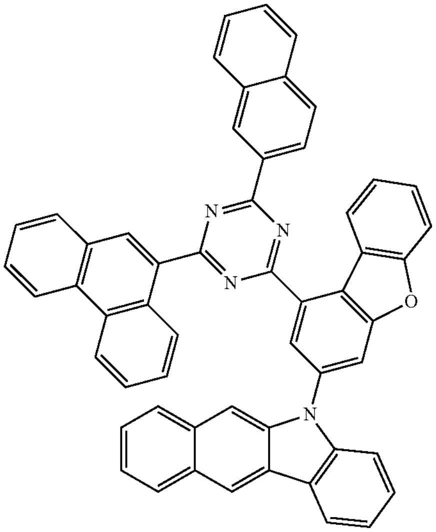
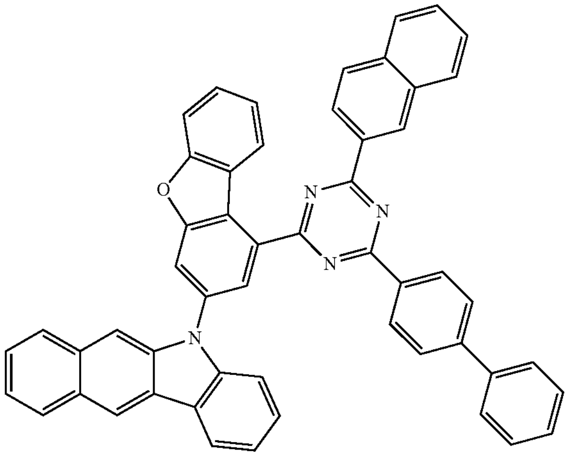
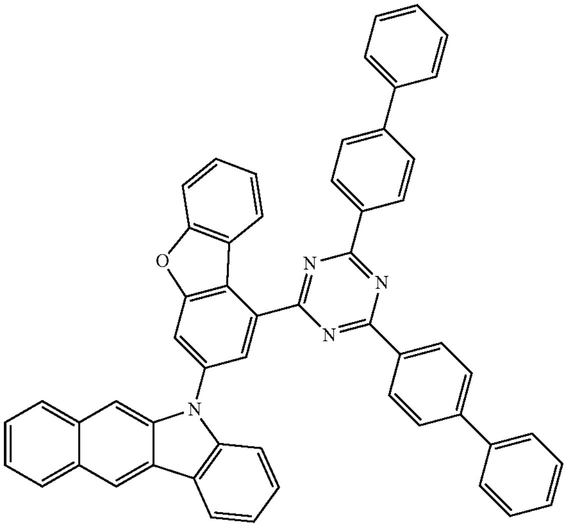
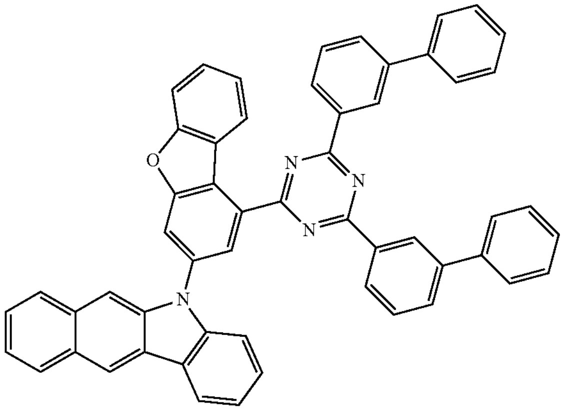
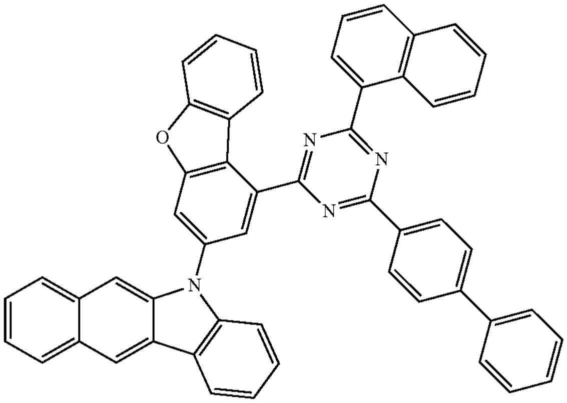
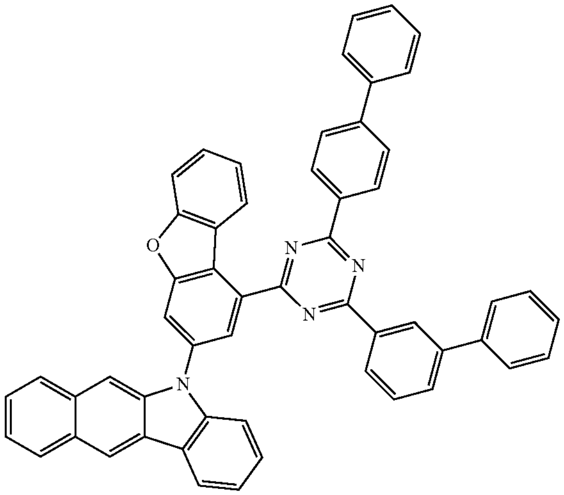
-continued -continued
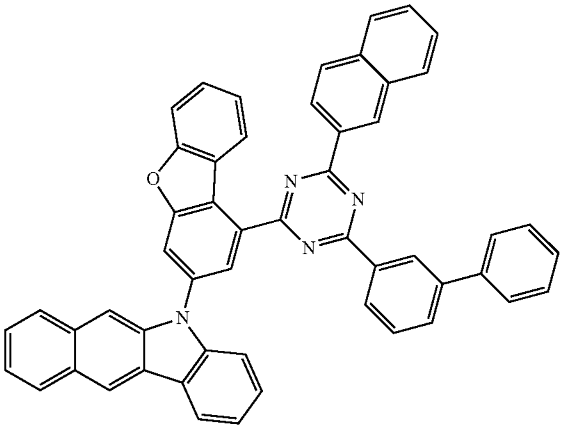
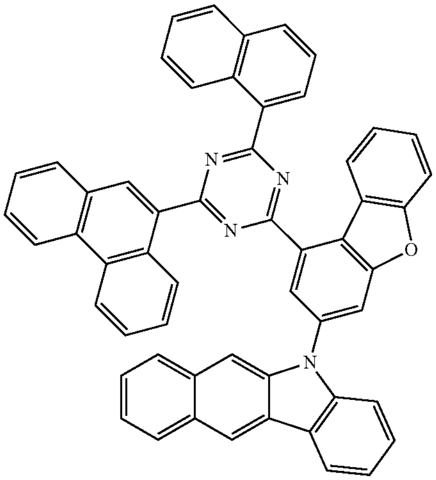
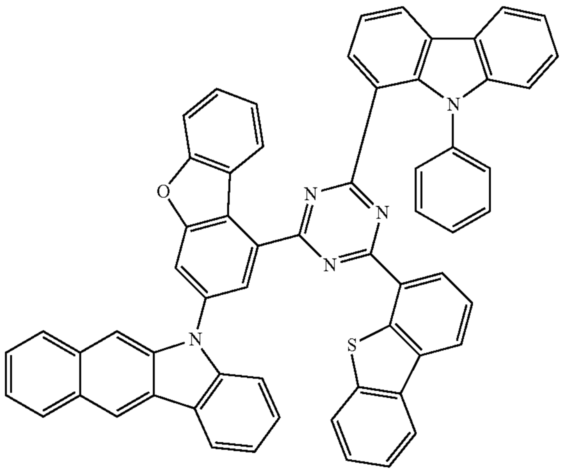
-continued
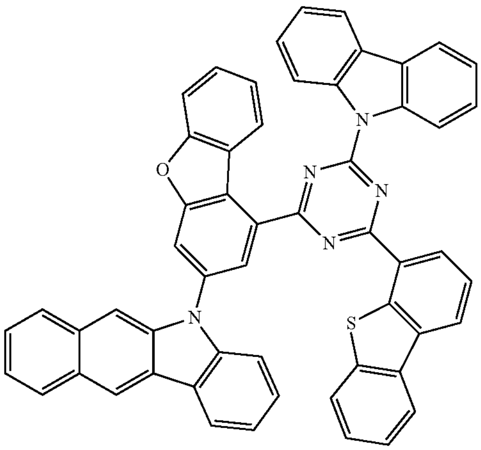
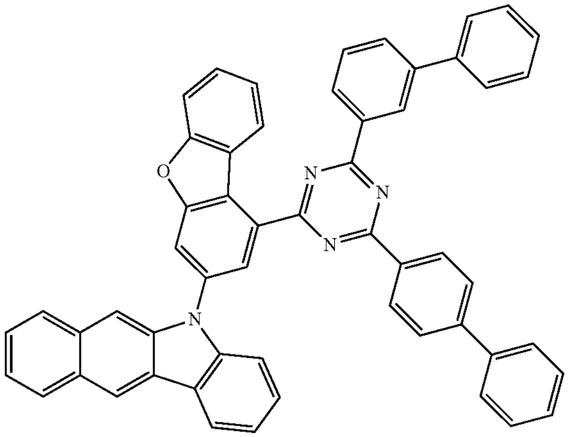
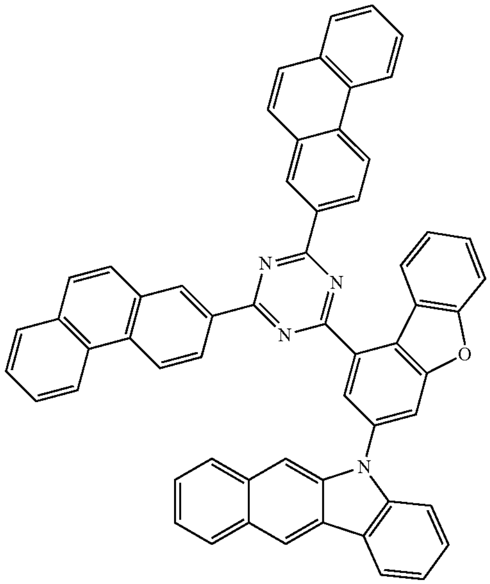

-continued
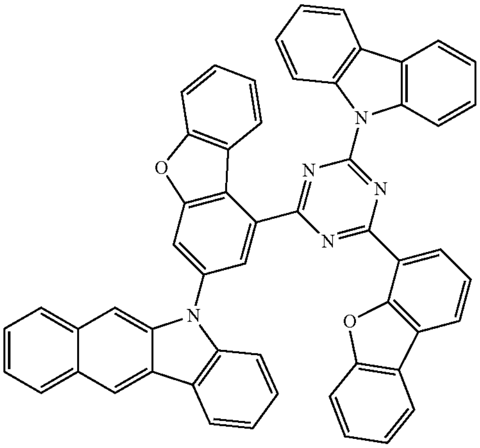
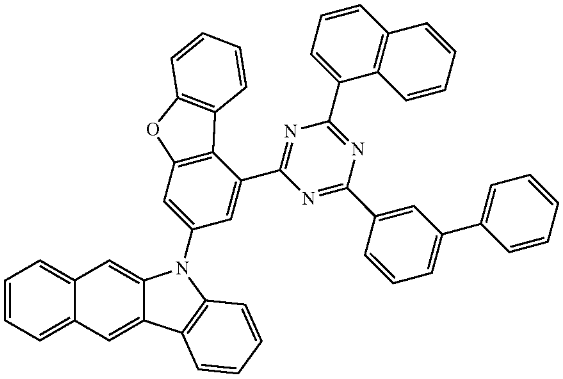
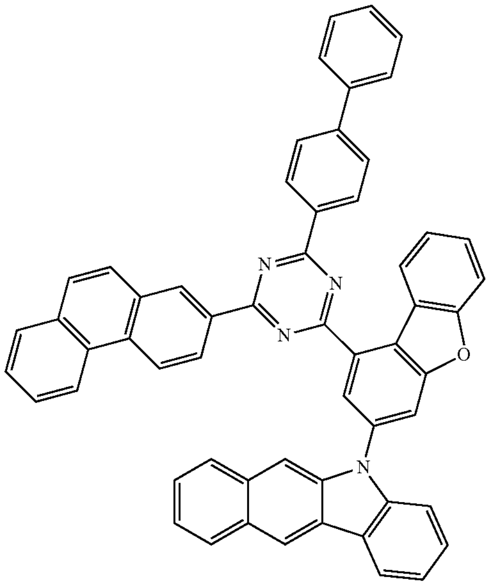
-continued
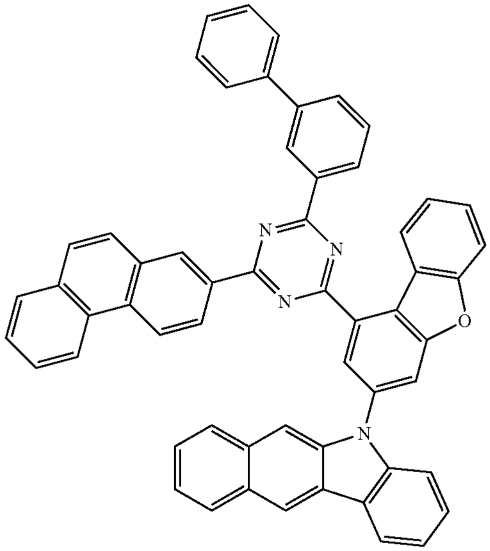
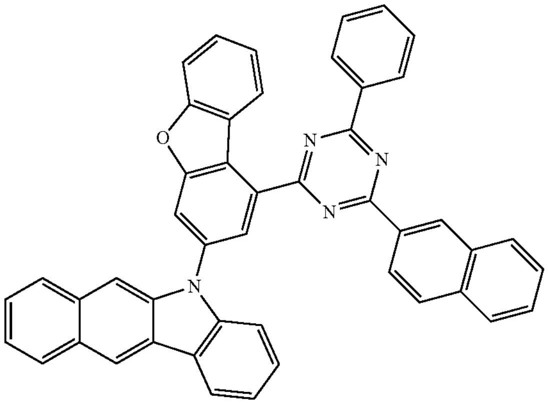
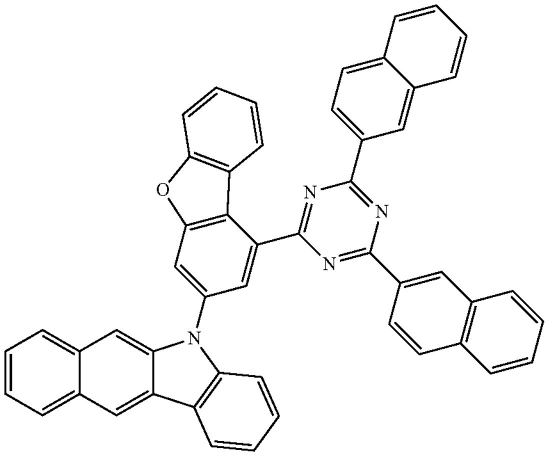

-continued
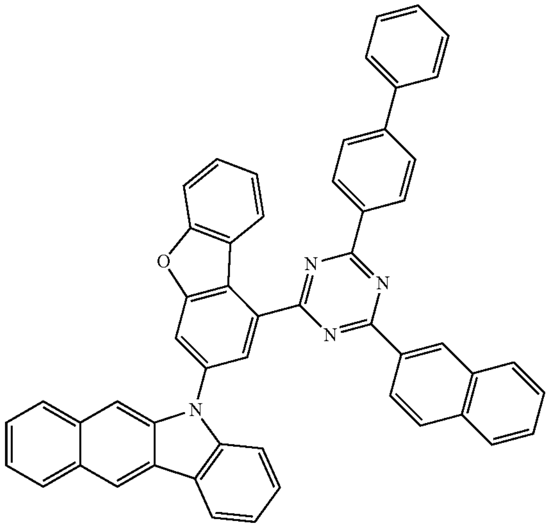
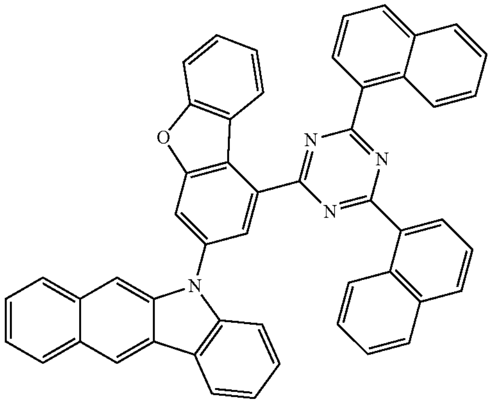
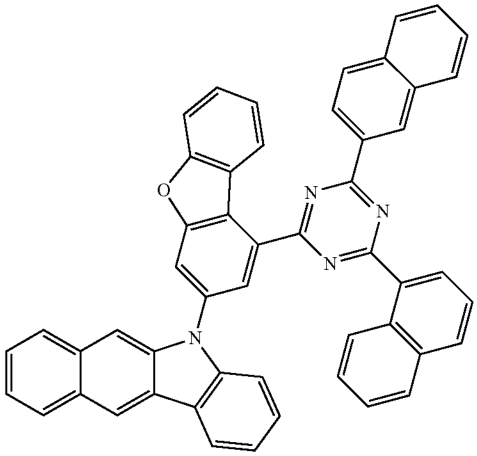
-continued
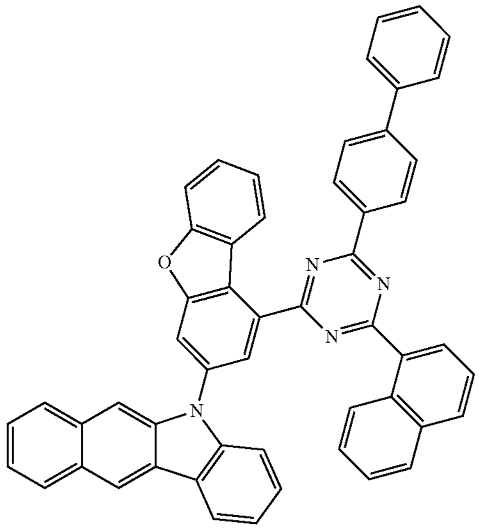
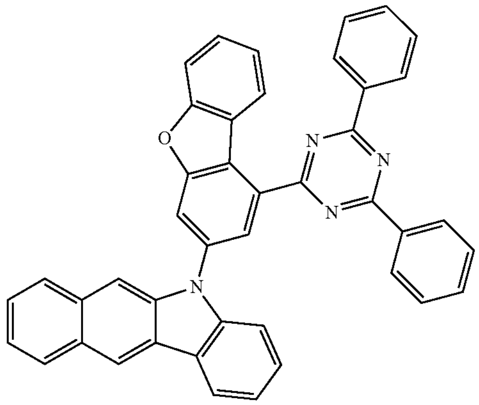
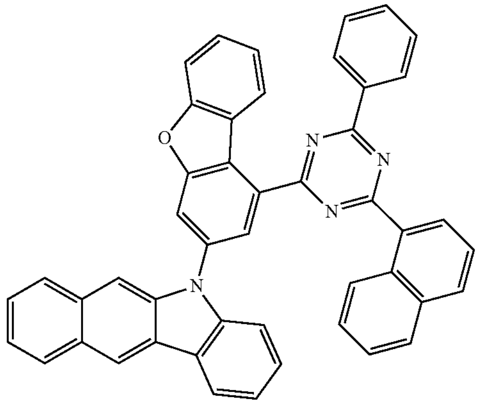

-continued
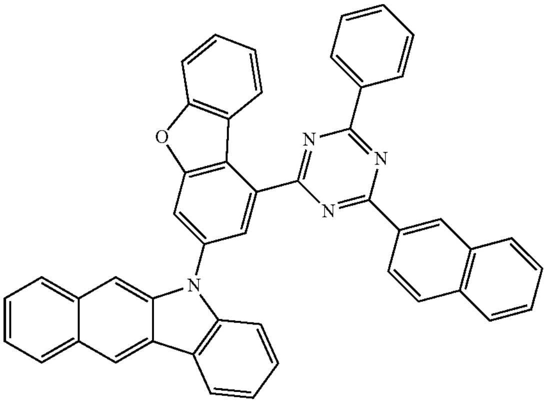
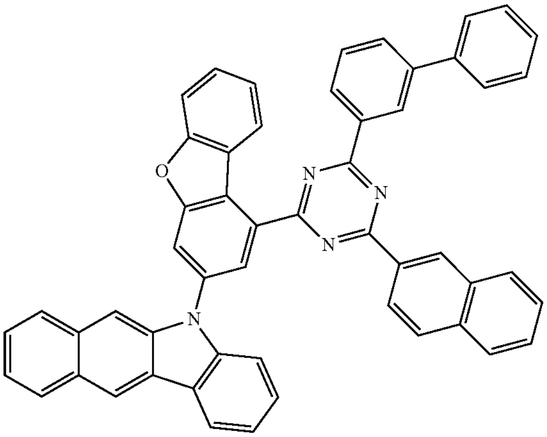
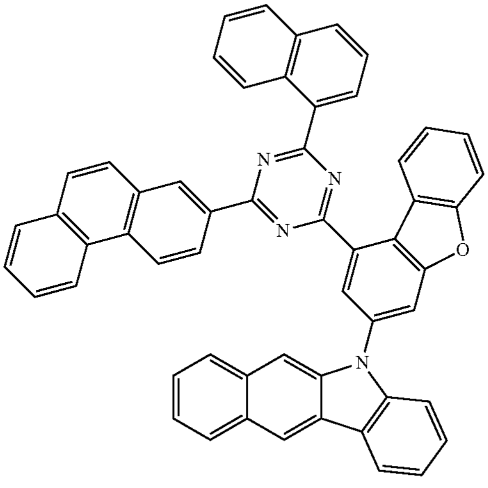
-continued
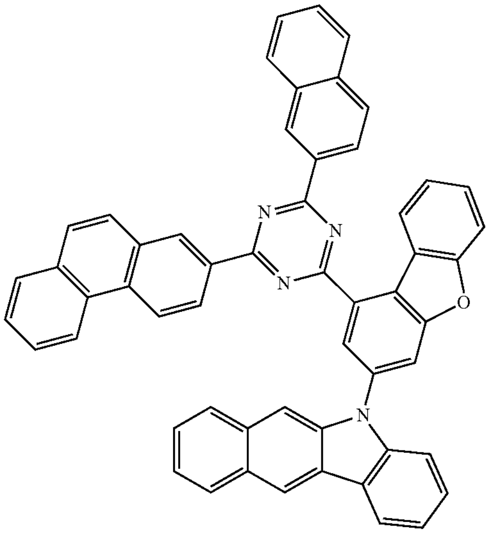
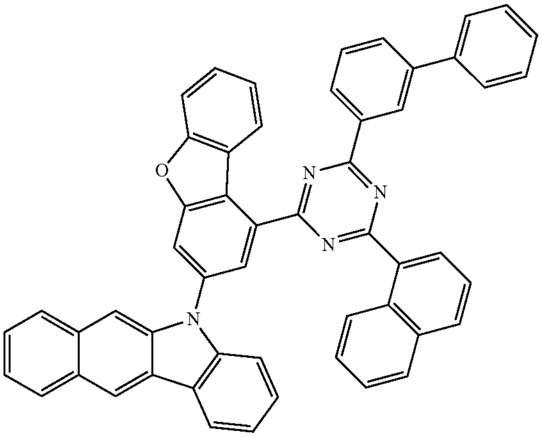
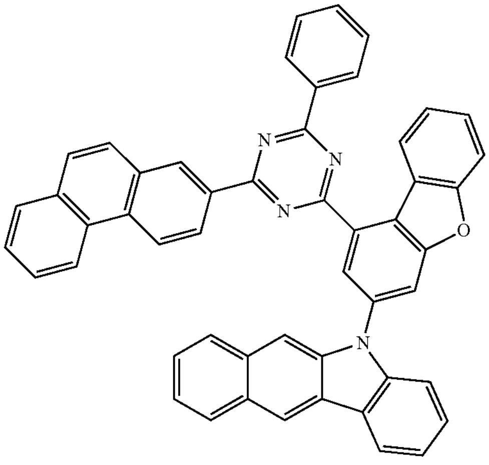

-continued
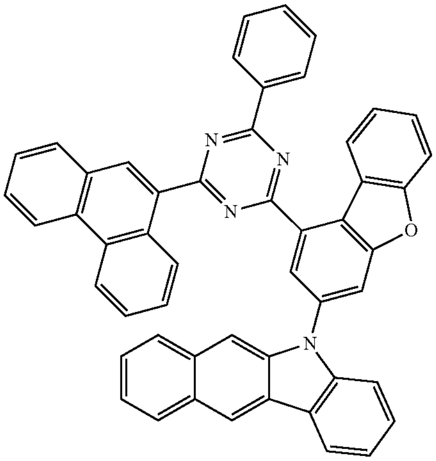
-continued
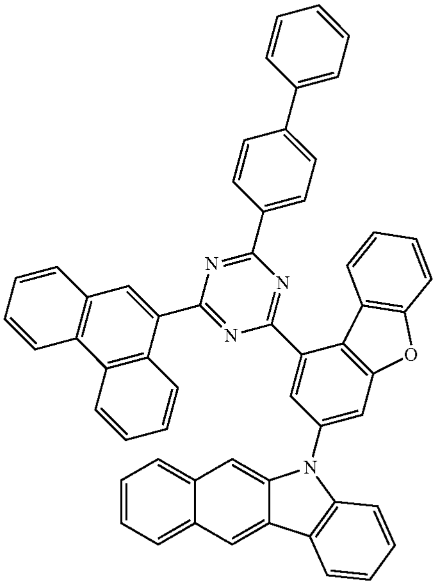
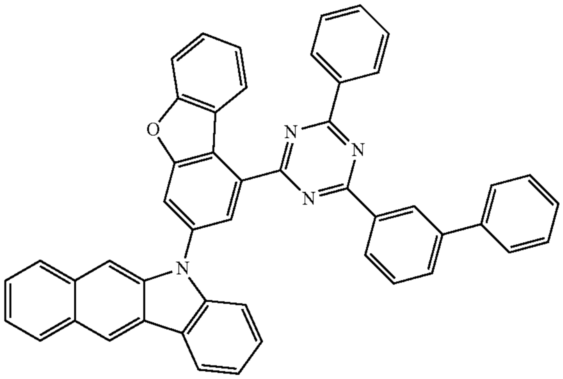
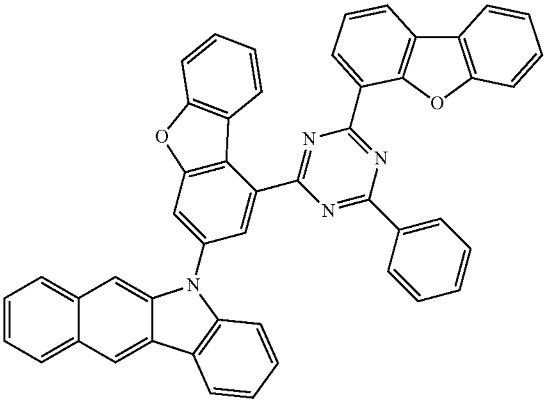
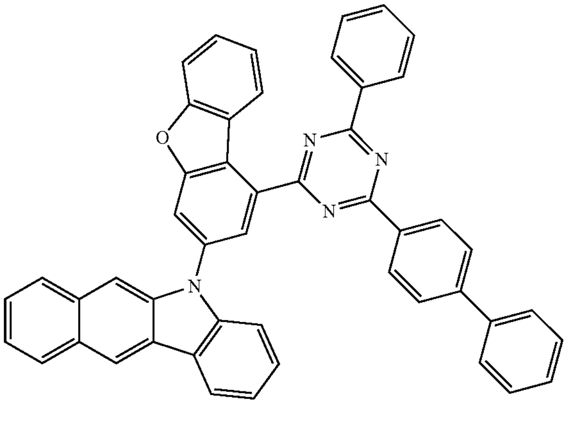
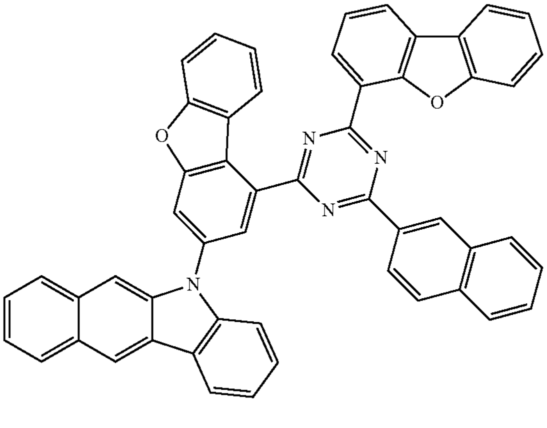

-continued
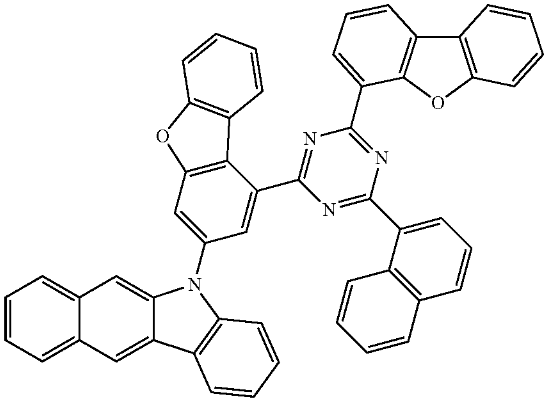
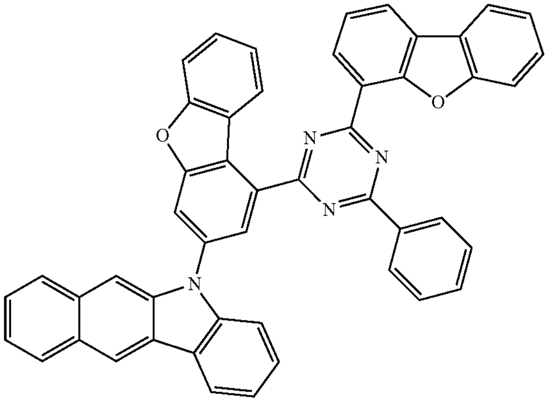
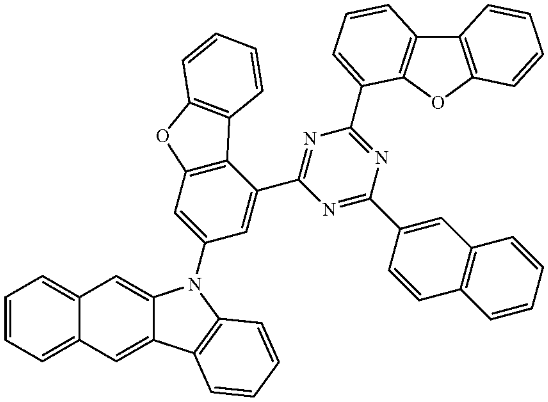
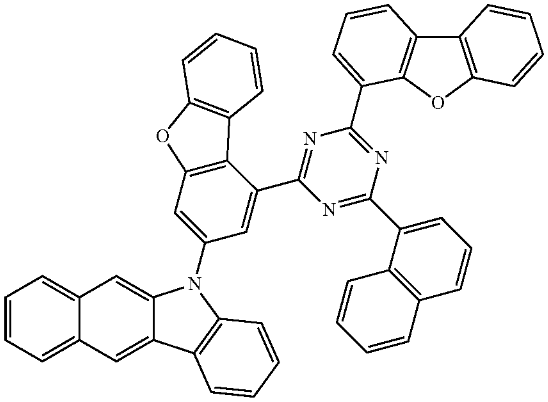
-continued
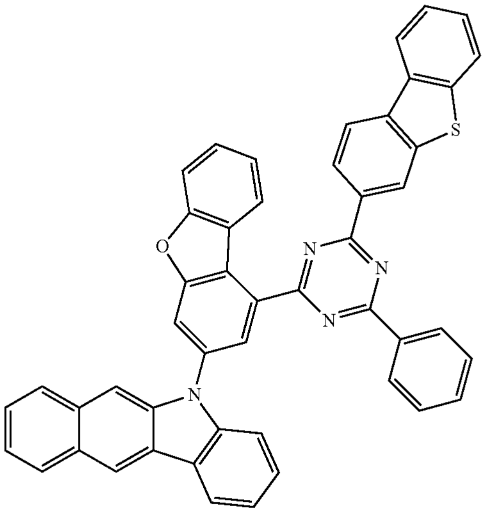
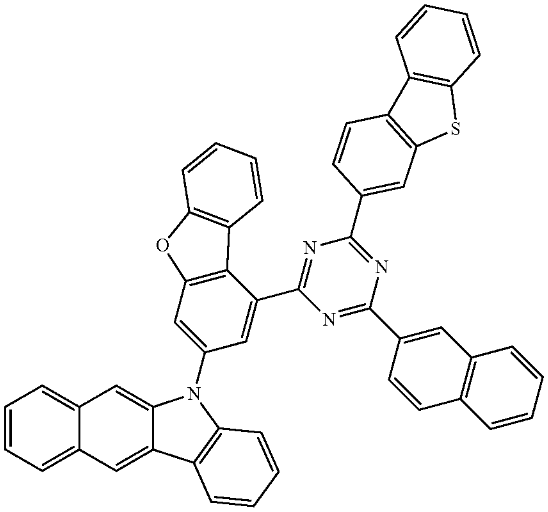
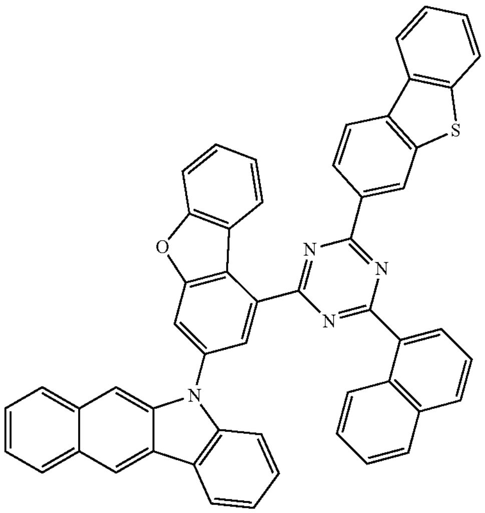

-continued
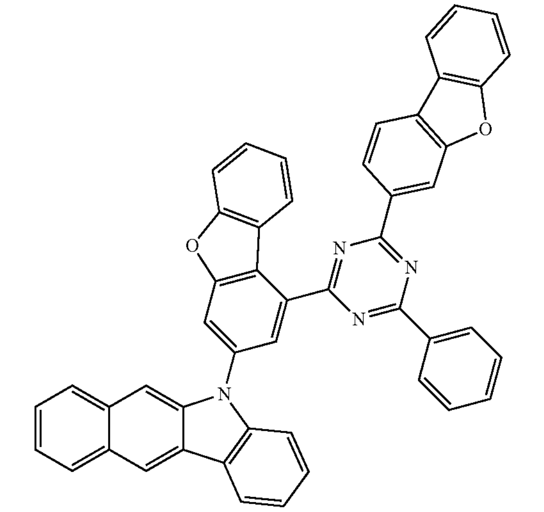
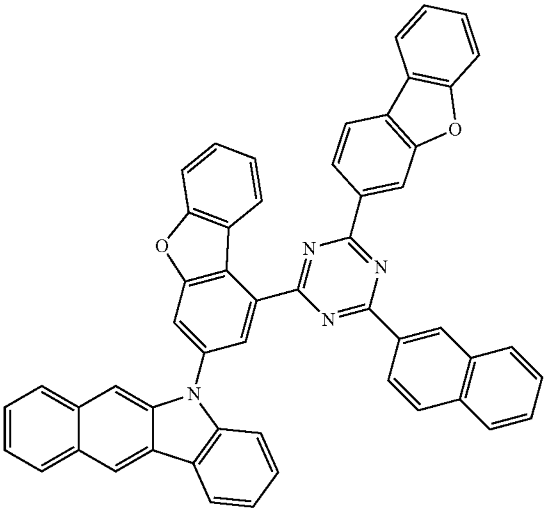
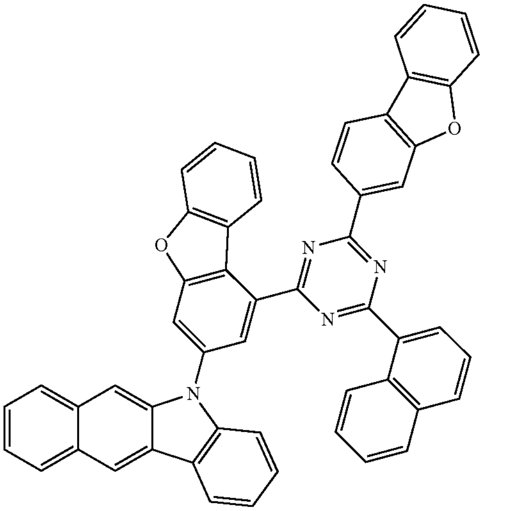
-continued
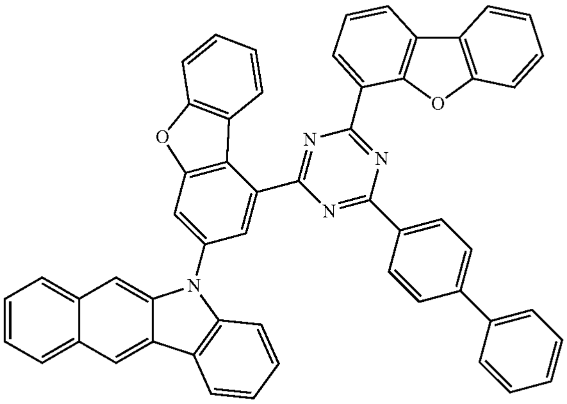
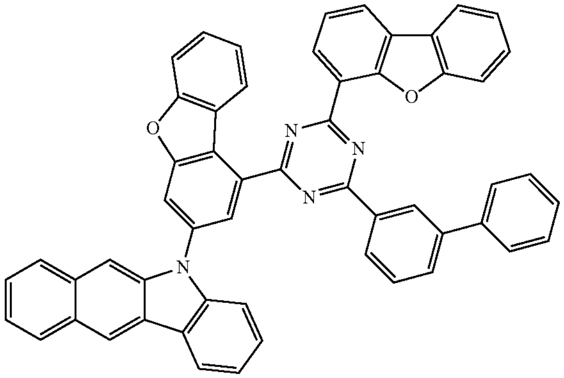
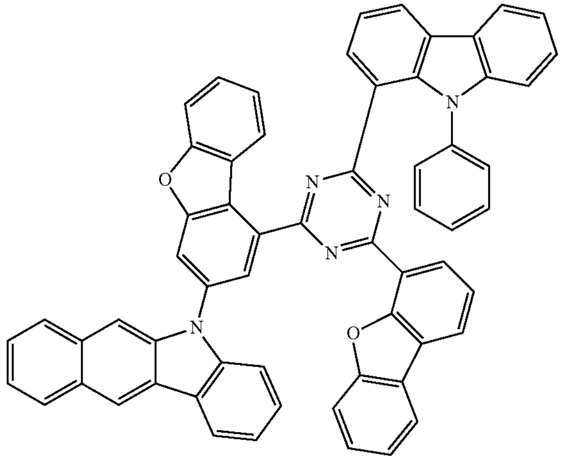

-continued
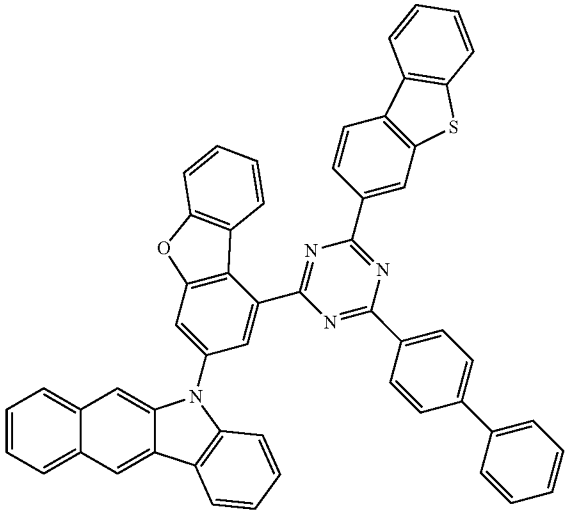
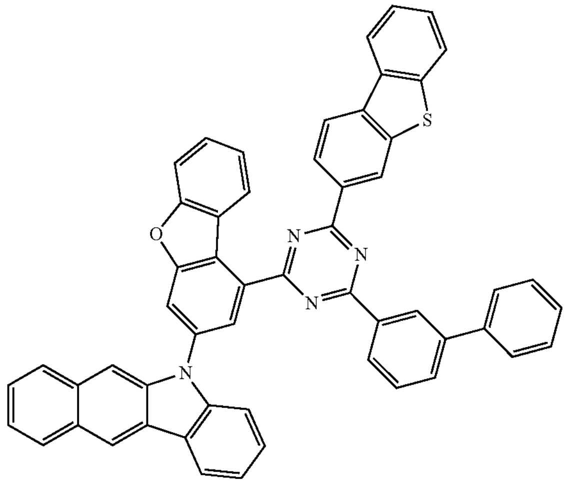
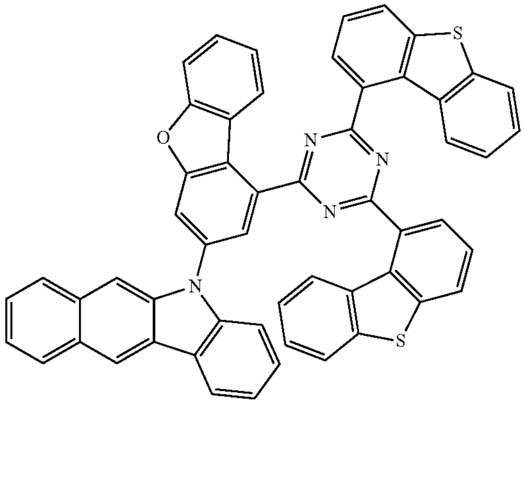
-continued
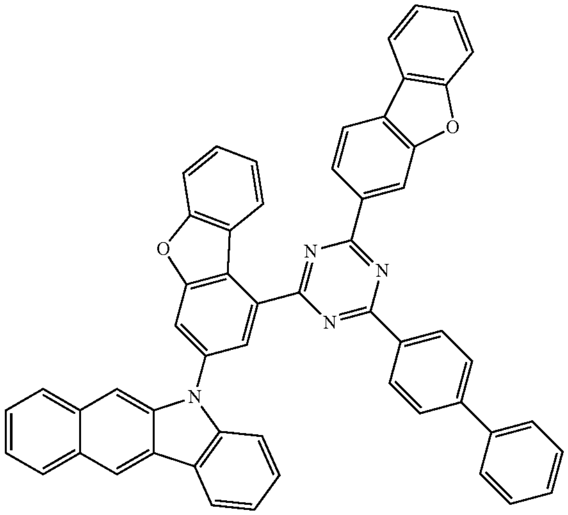
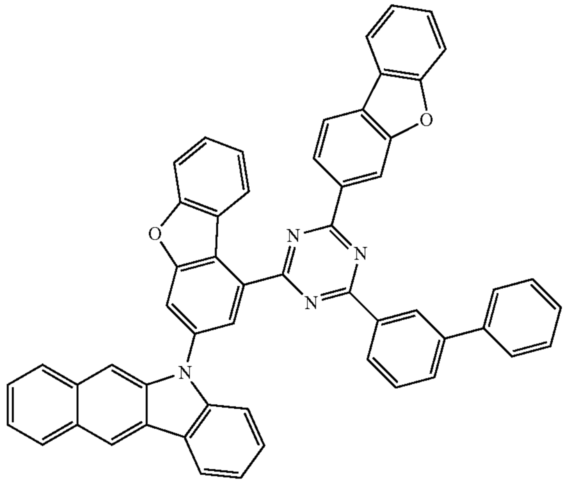
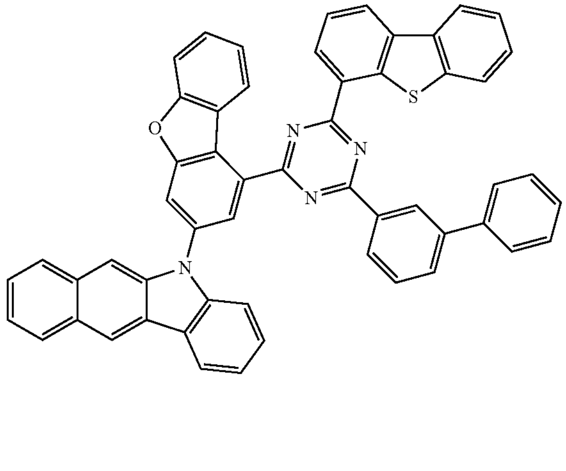

-continued
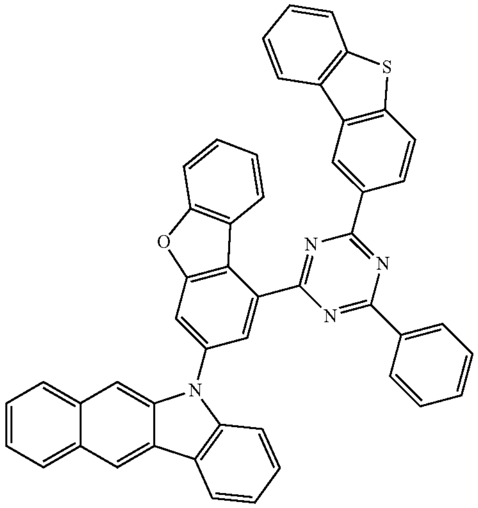
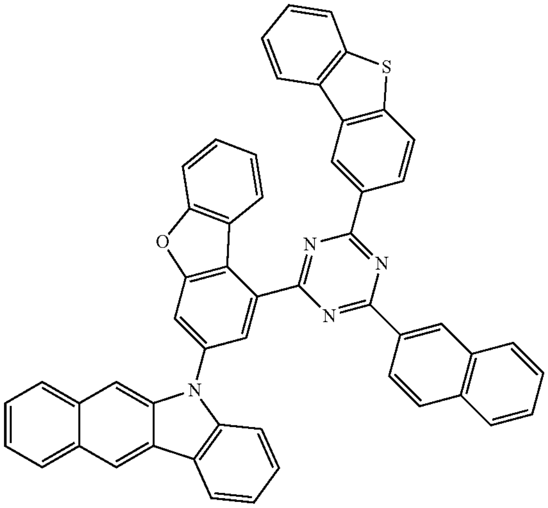
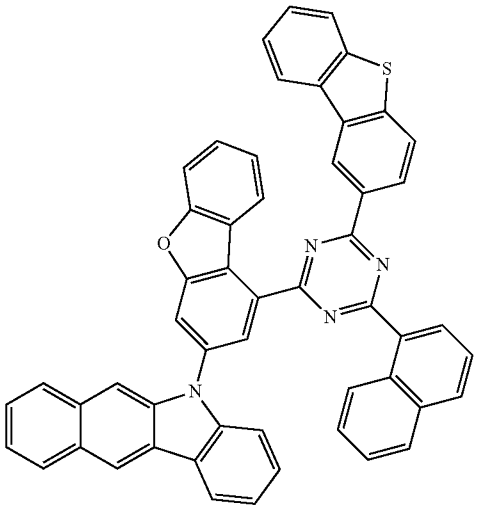
-continued
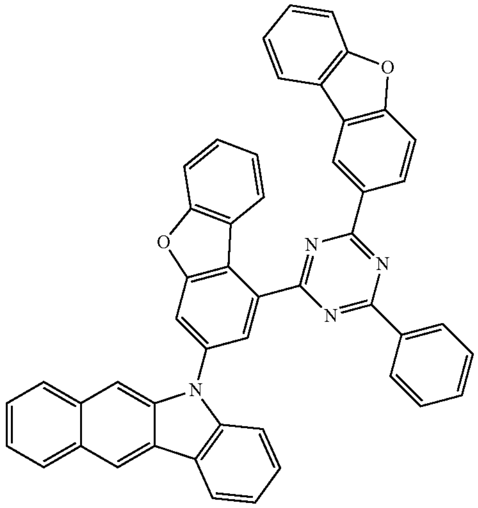
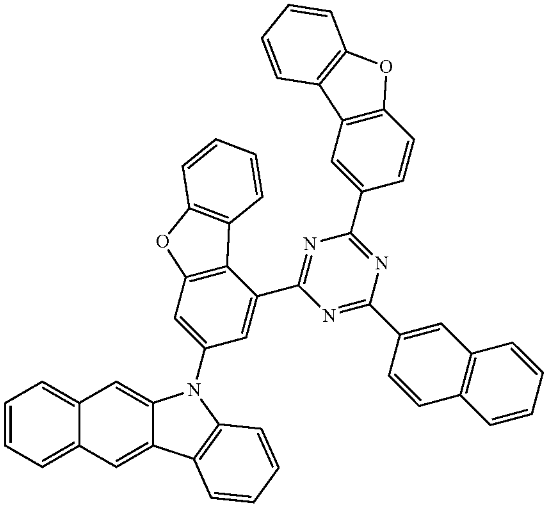
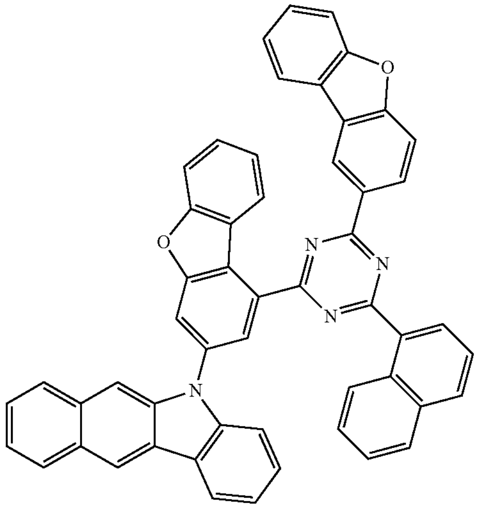

-continued
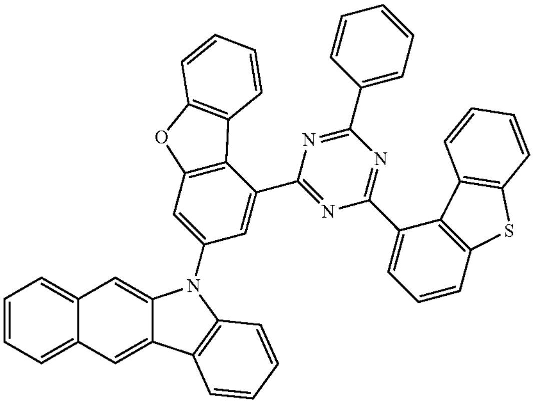
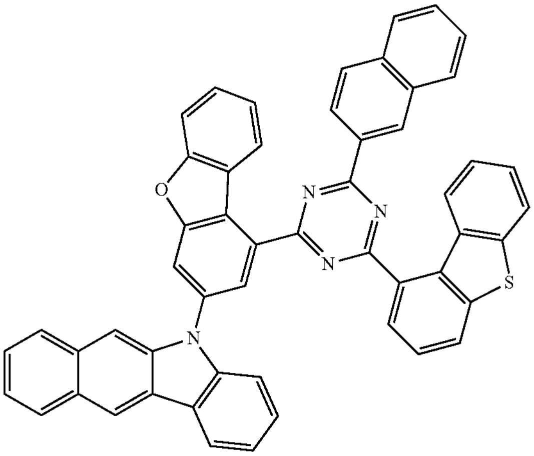
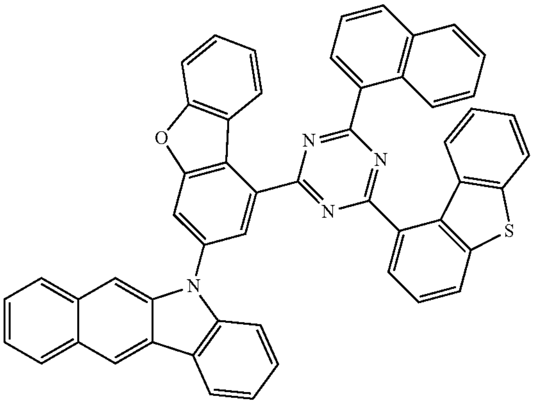
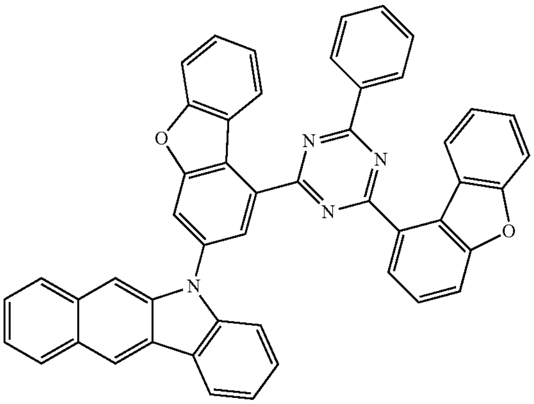
-continued
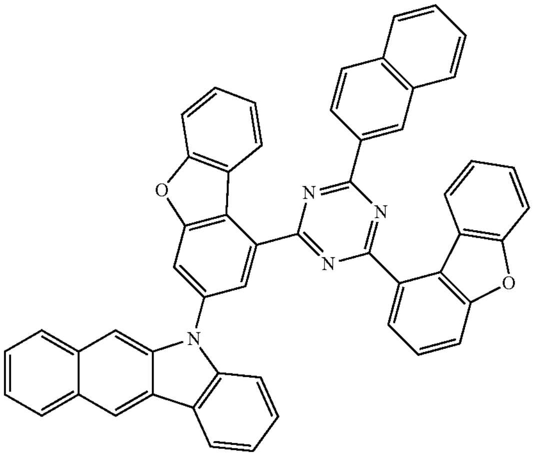
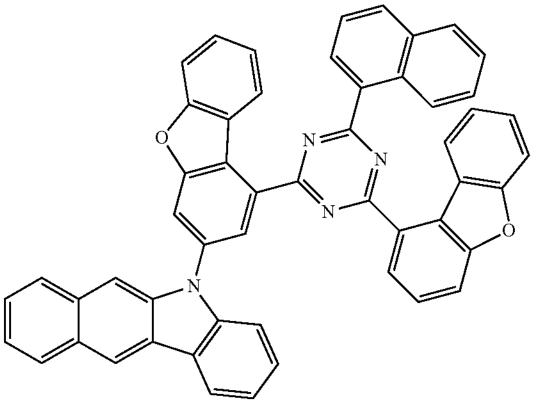
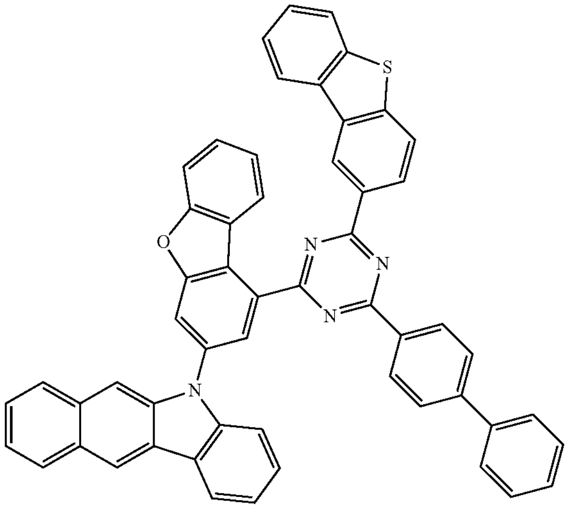

-continued
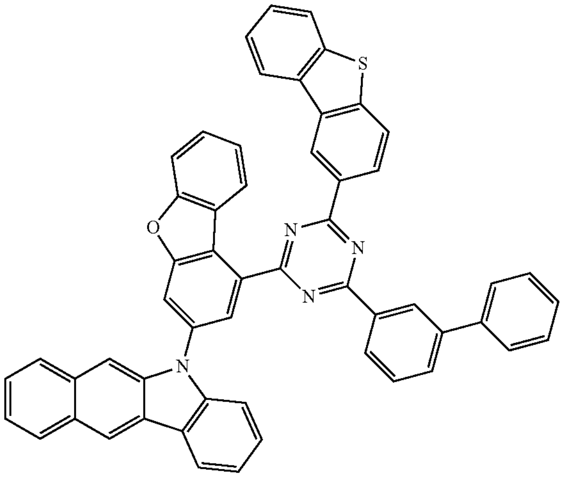
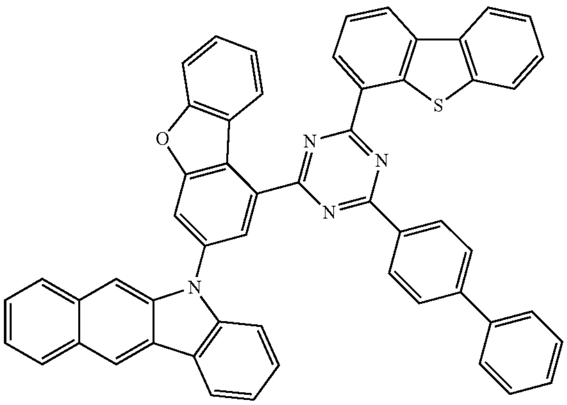
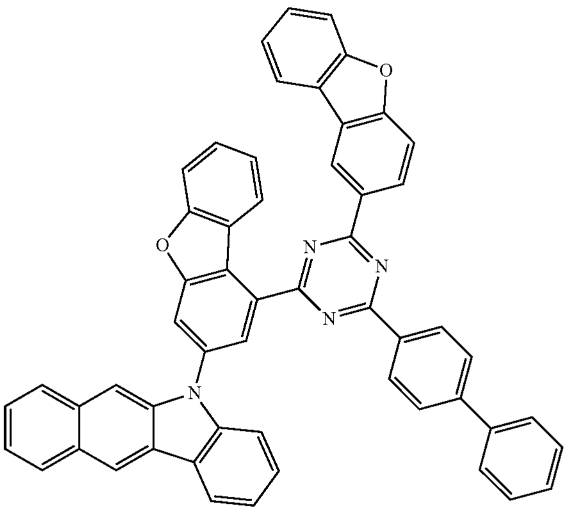
-continued
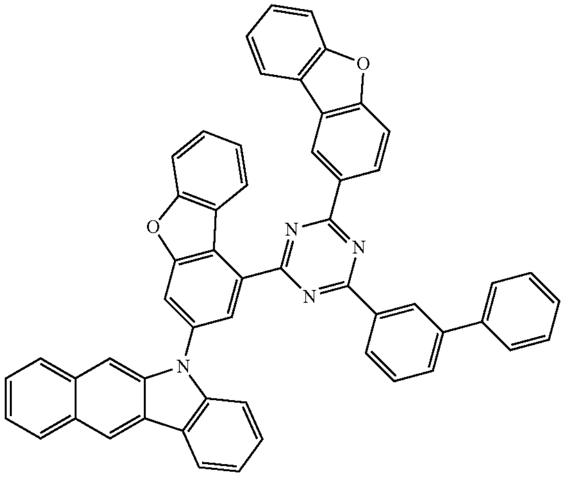
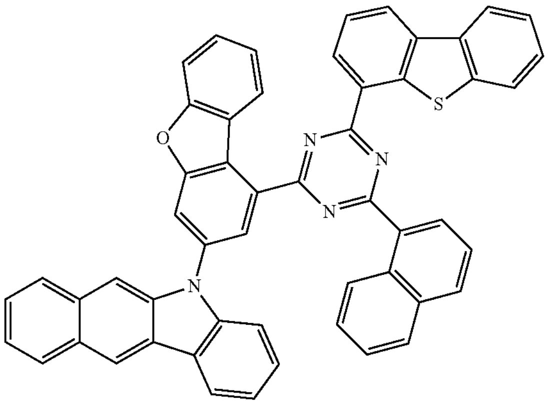
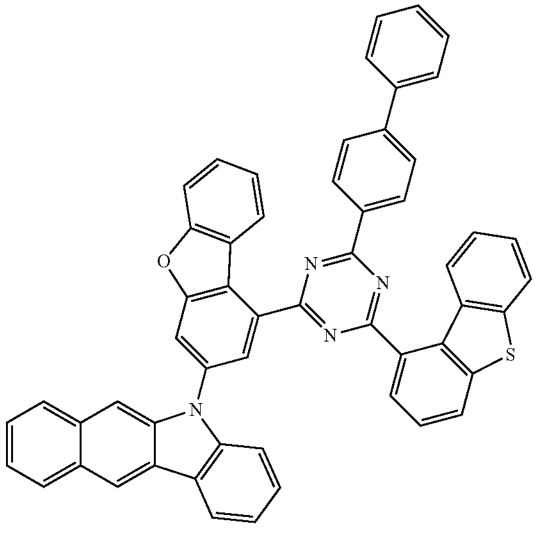

-continued
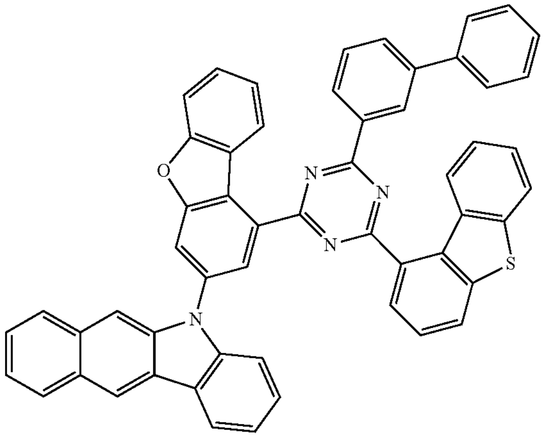
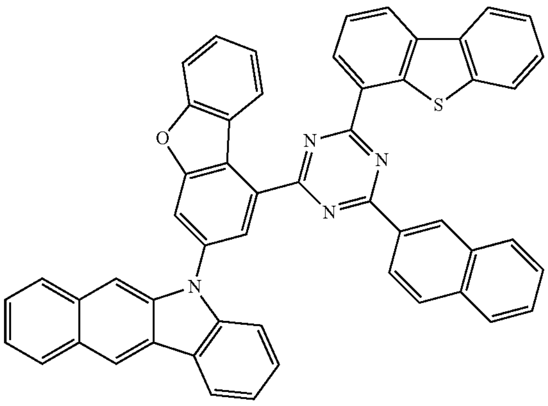
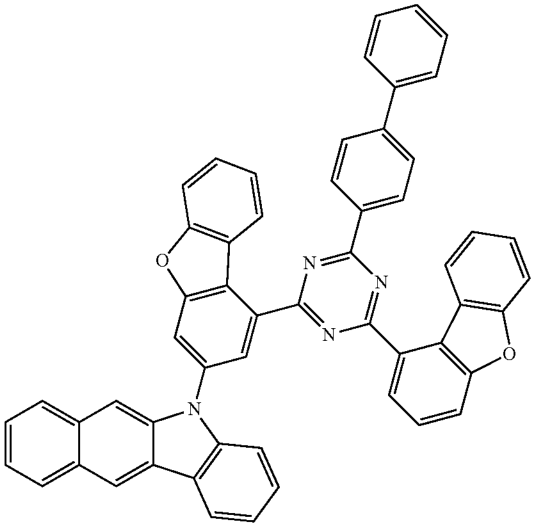
-continued
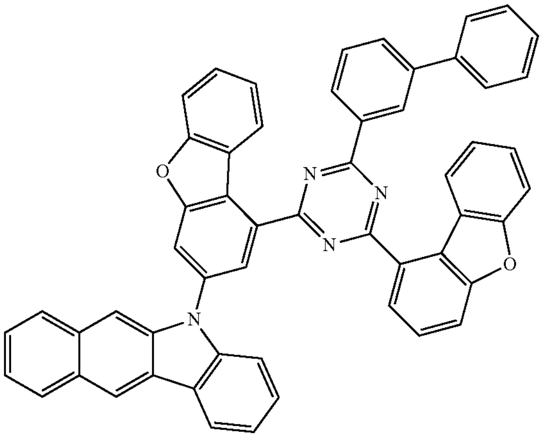
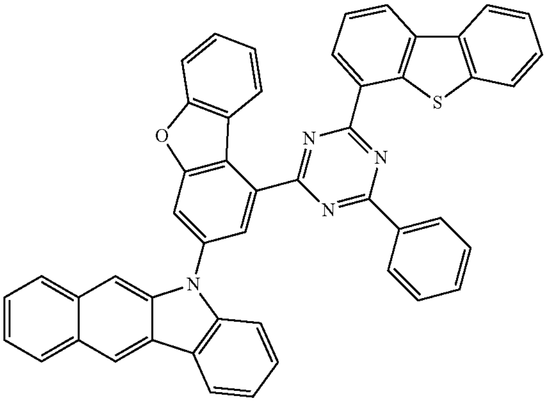
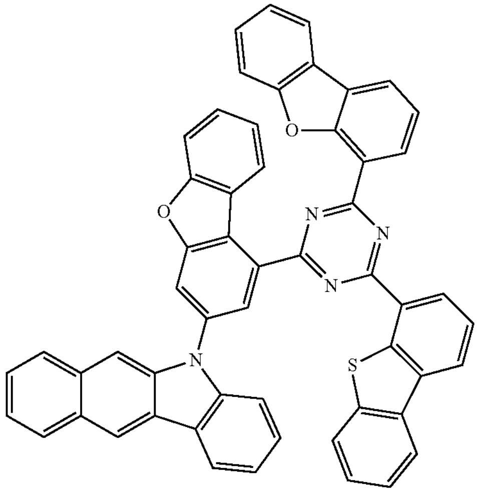

-continued
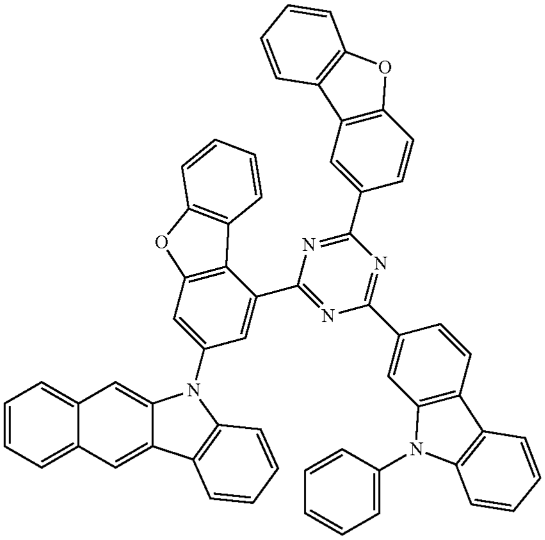
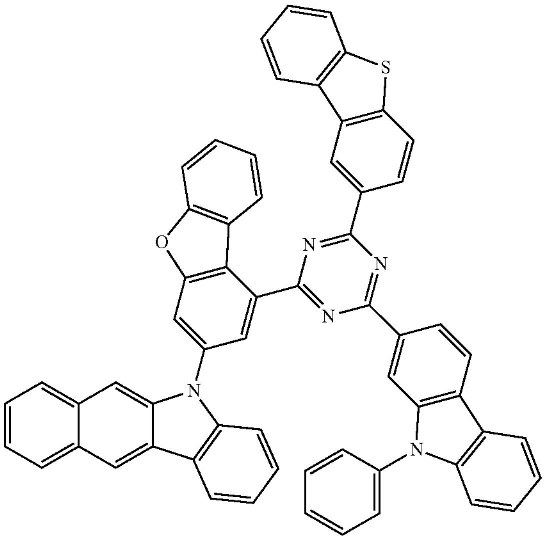
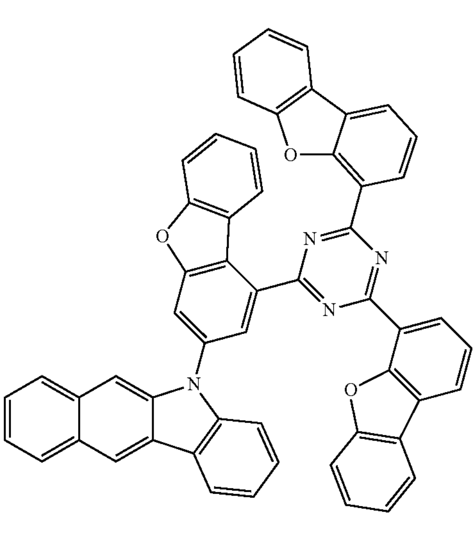
-continued
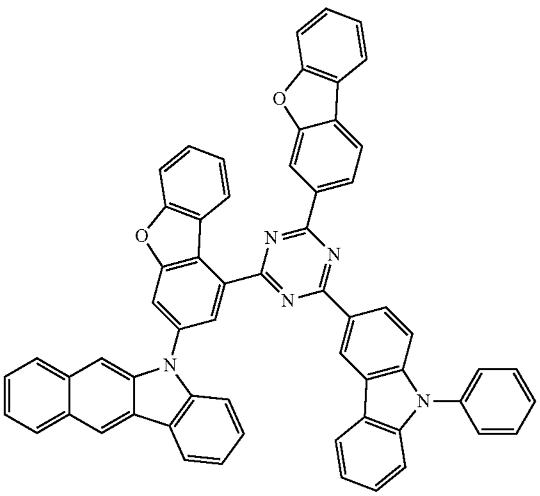
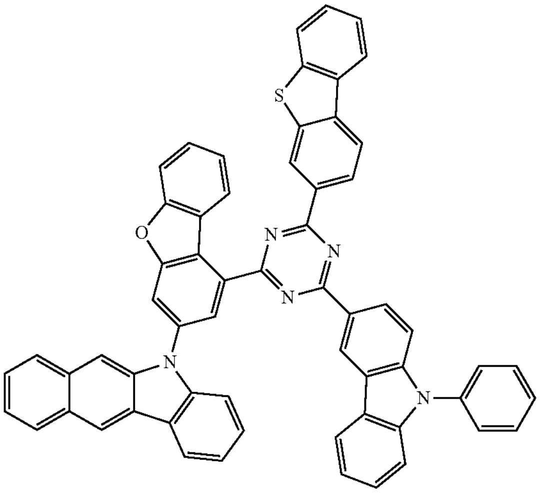
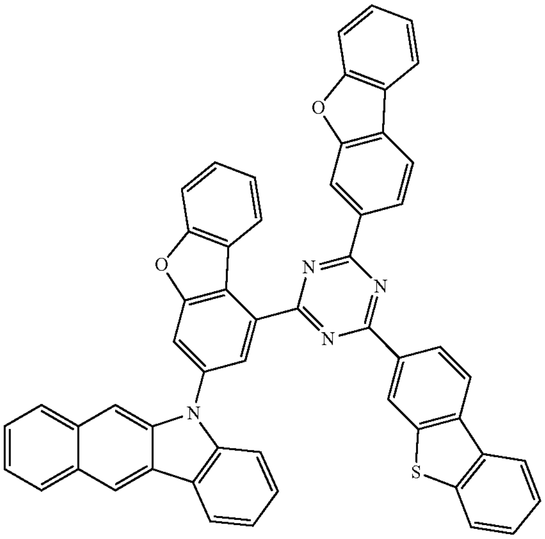

-continued
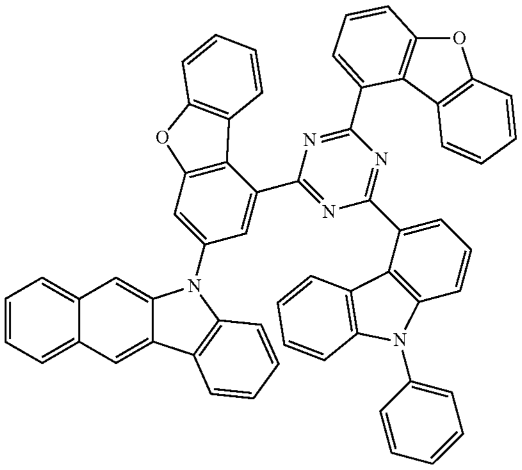
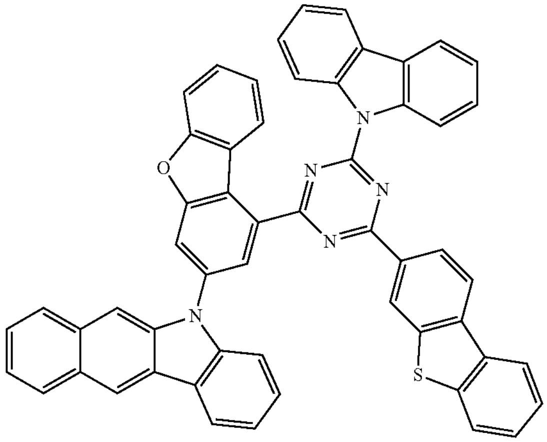
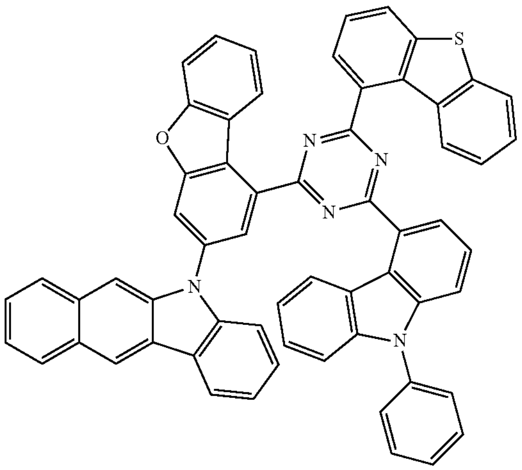
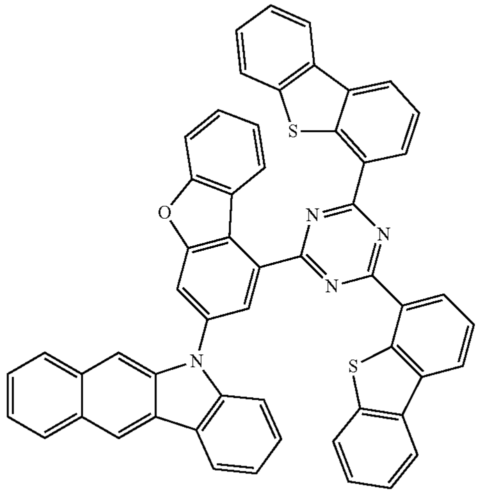
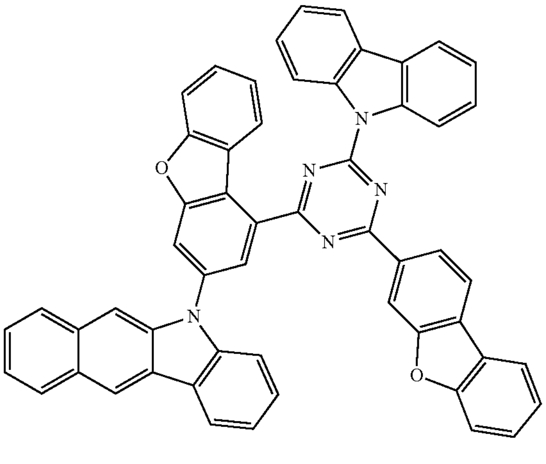
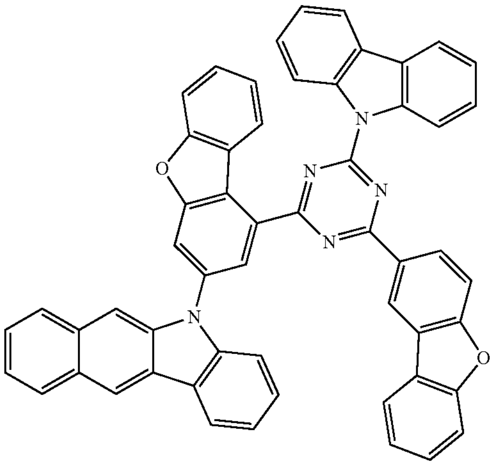
-continued -continued
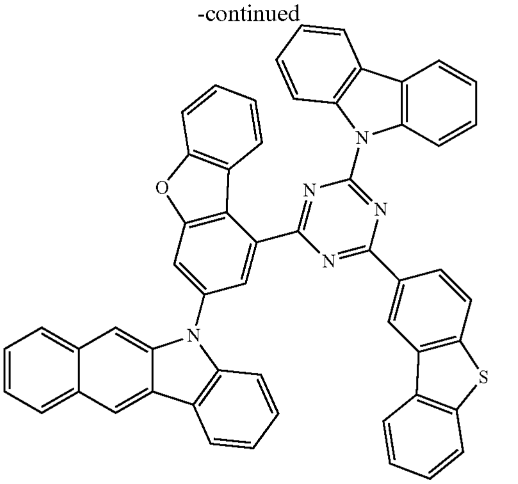
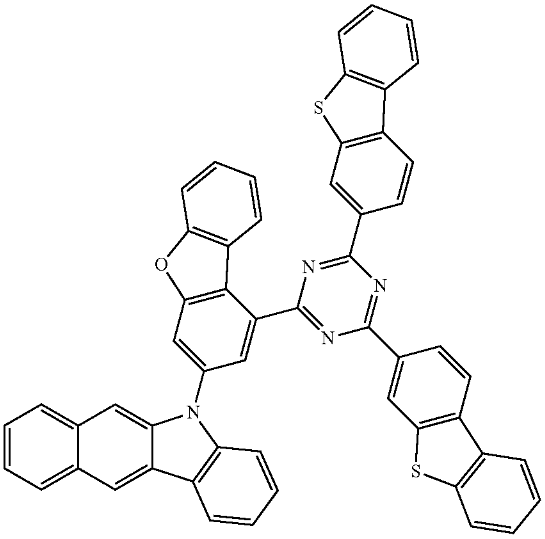
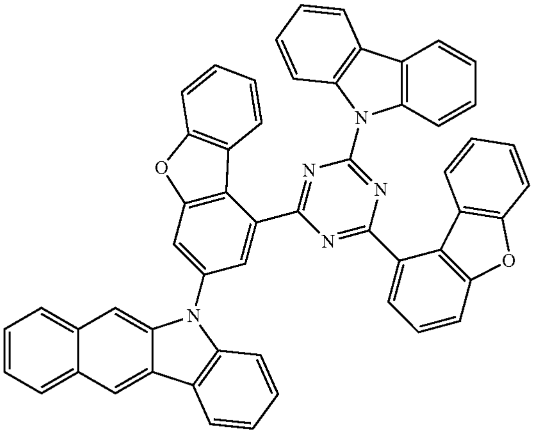
-continued
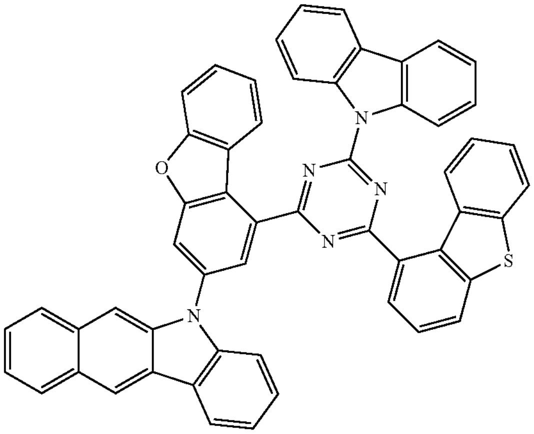
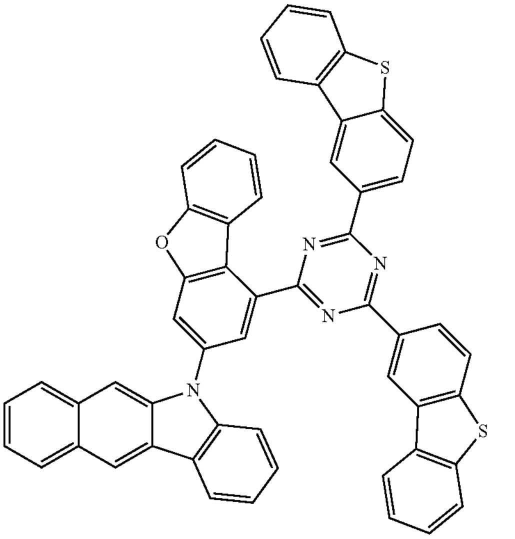
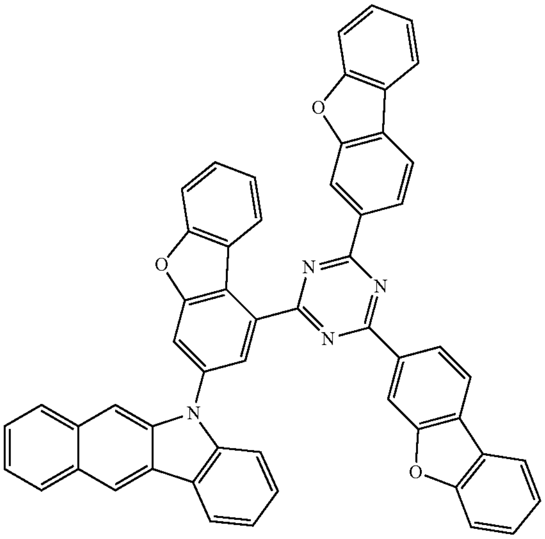

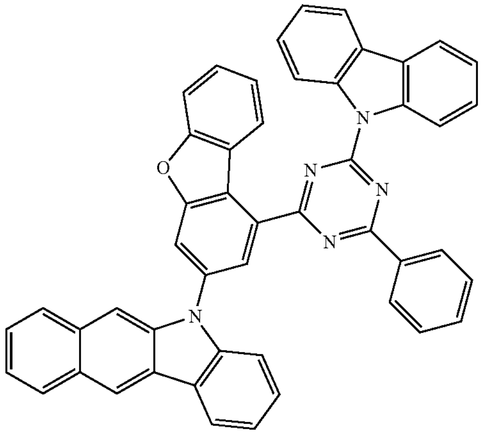
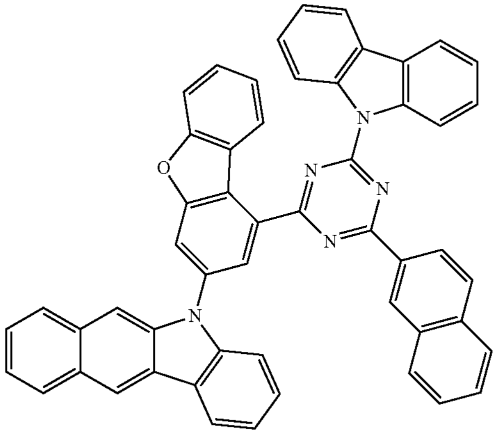
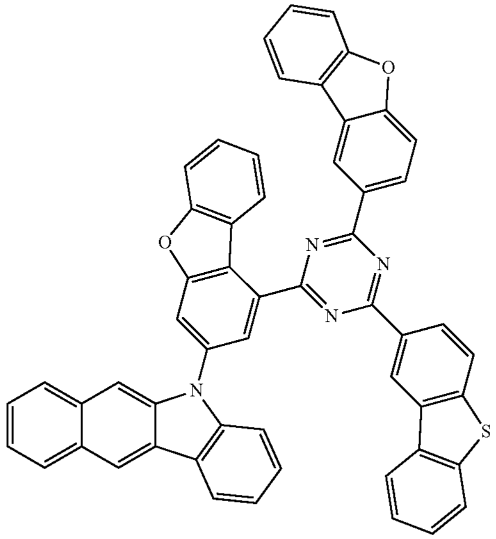
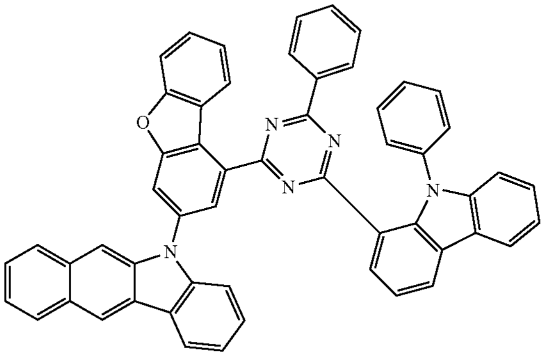
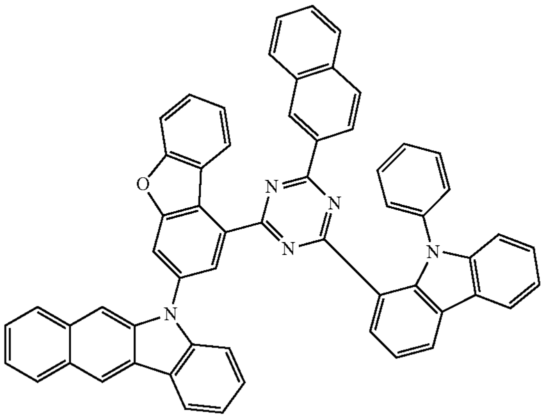
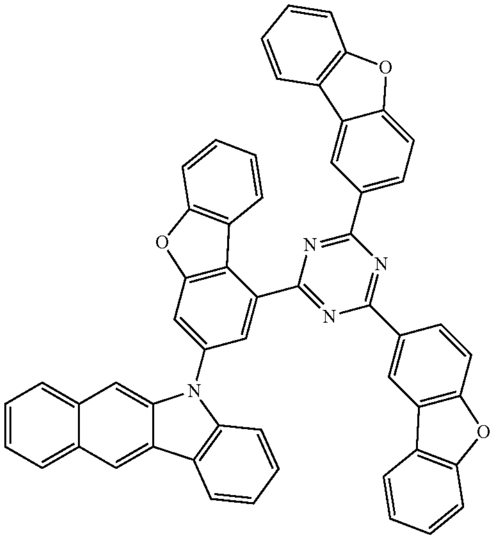

-continued
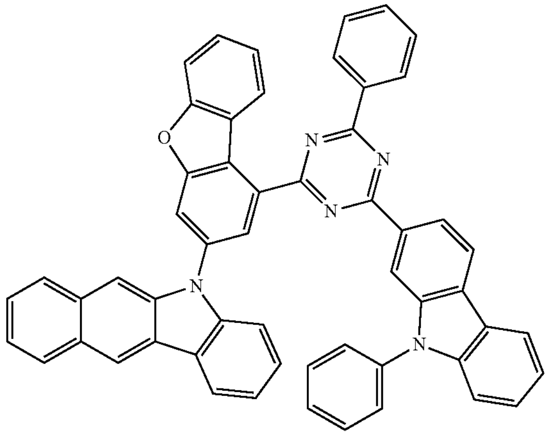
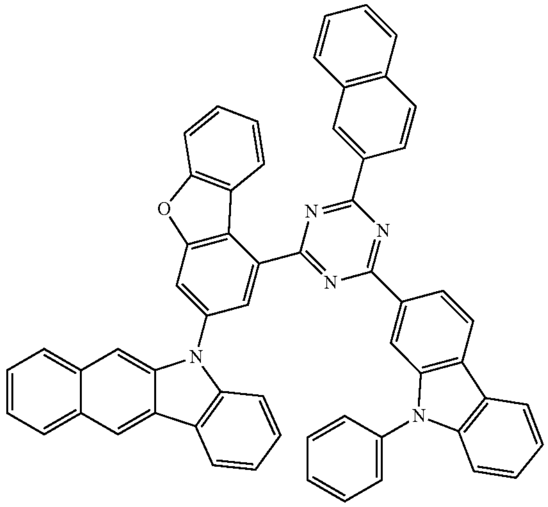
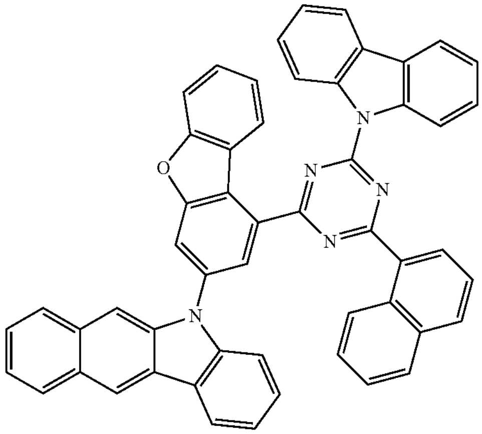
-continued
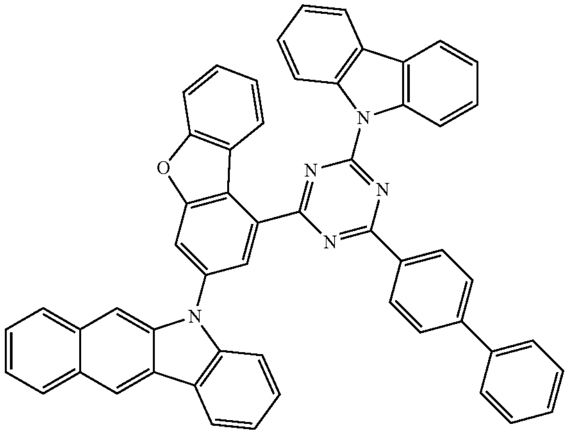
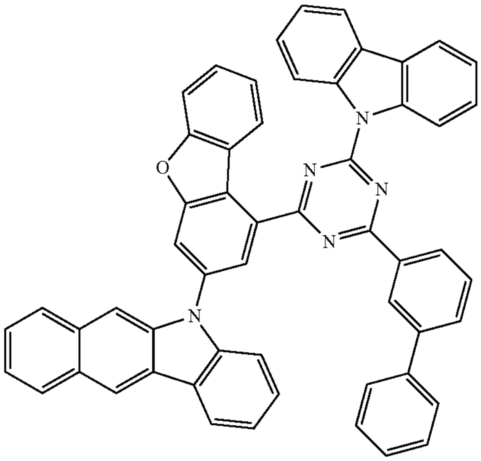
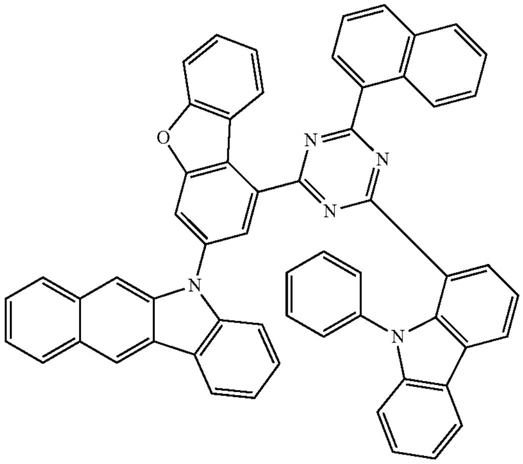

-continued
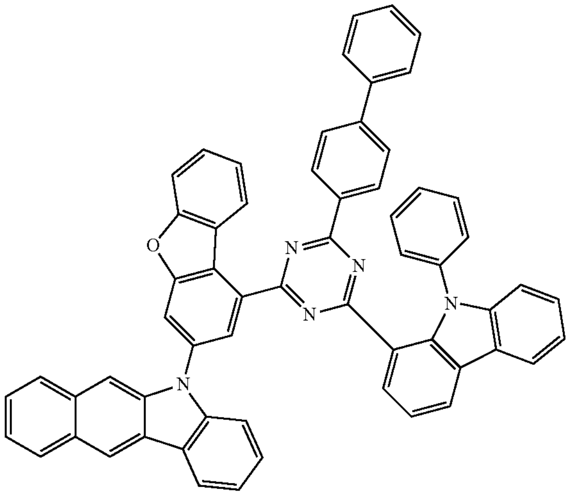
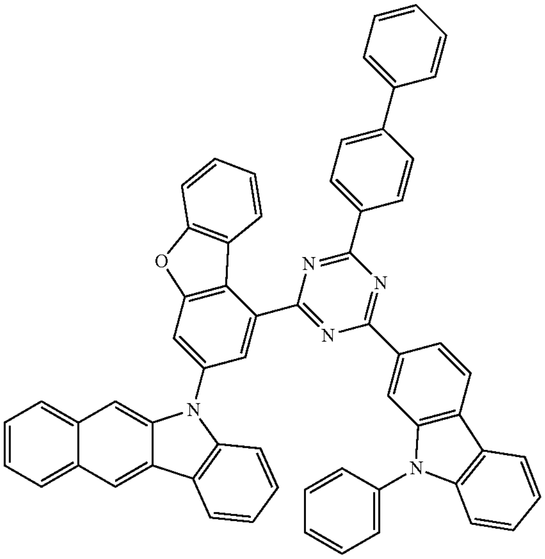
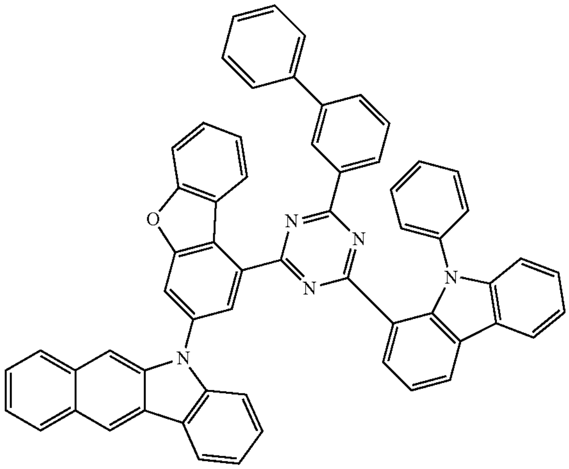
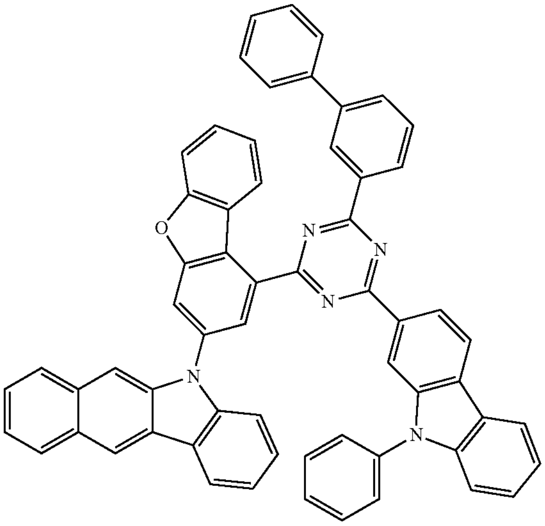
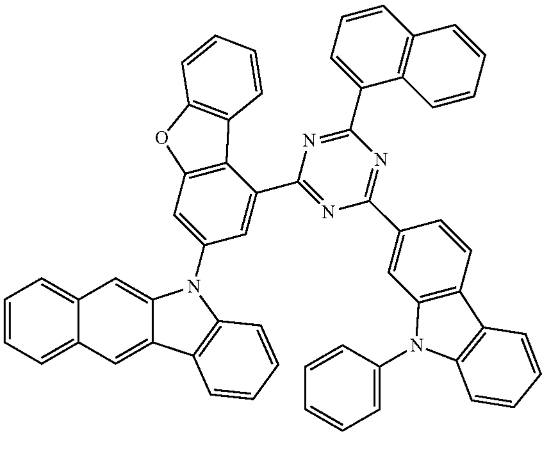
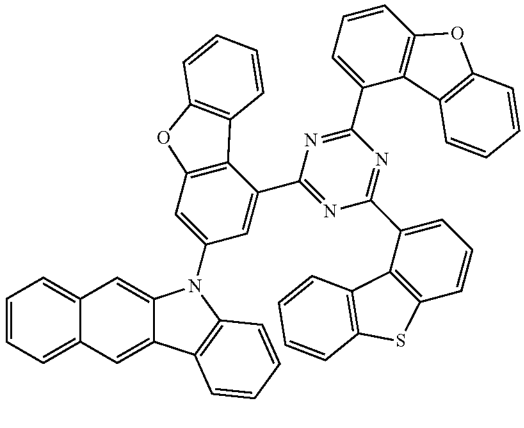
-continued -continued
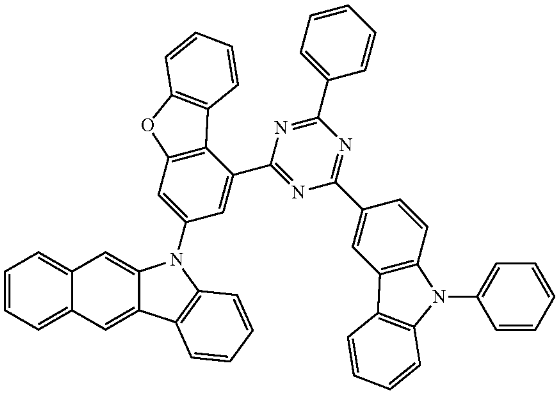
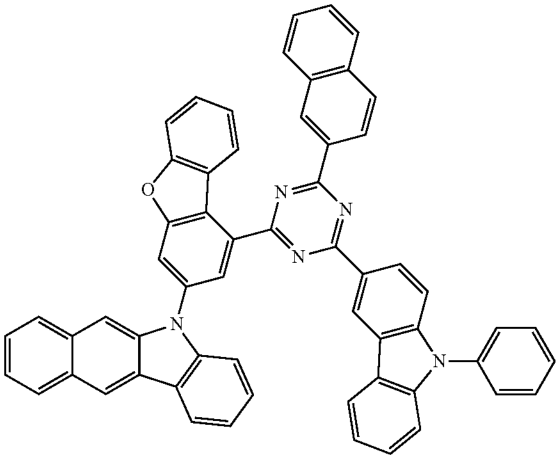
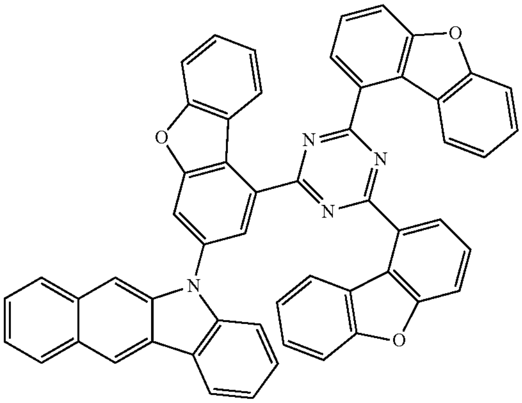
-continued
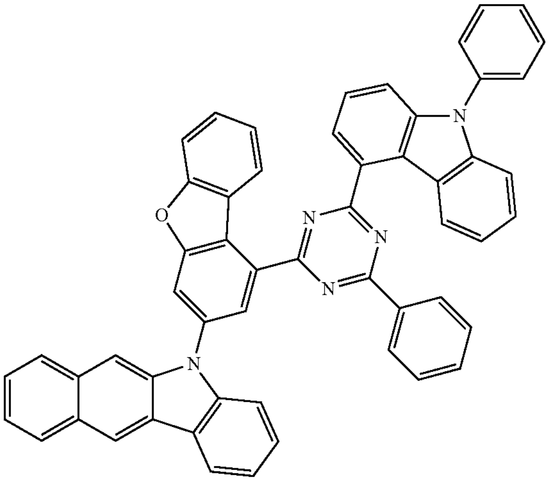
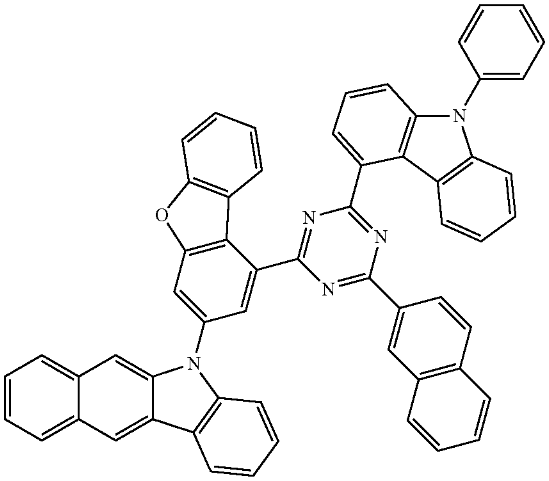
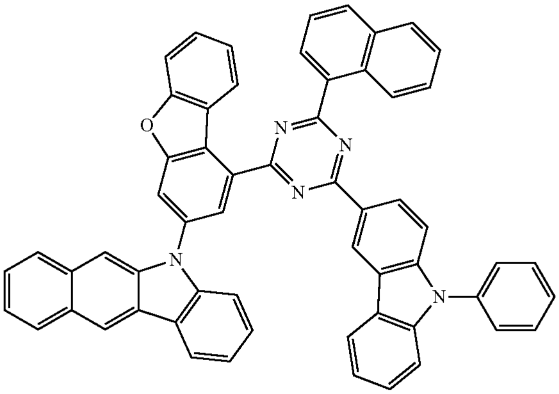

-continued
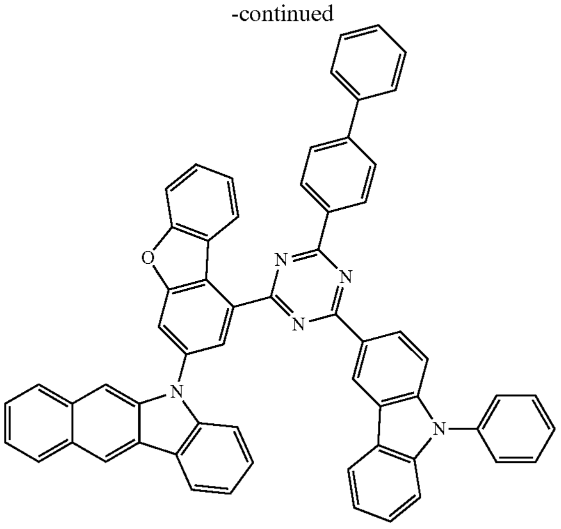
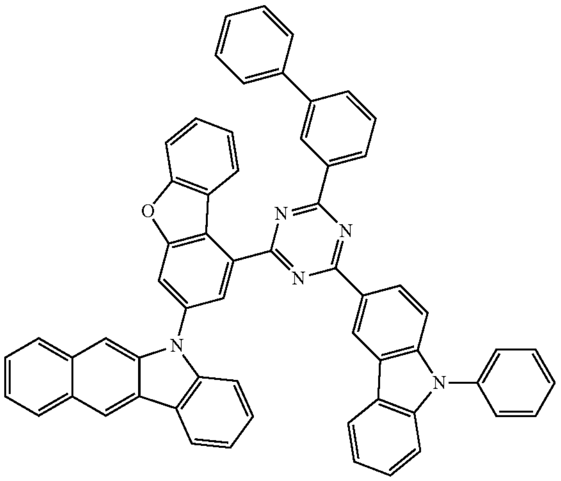
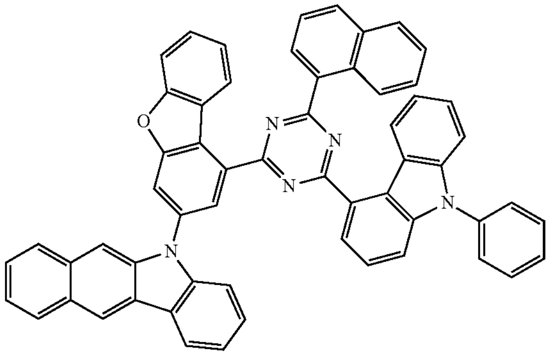
-continued
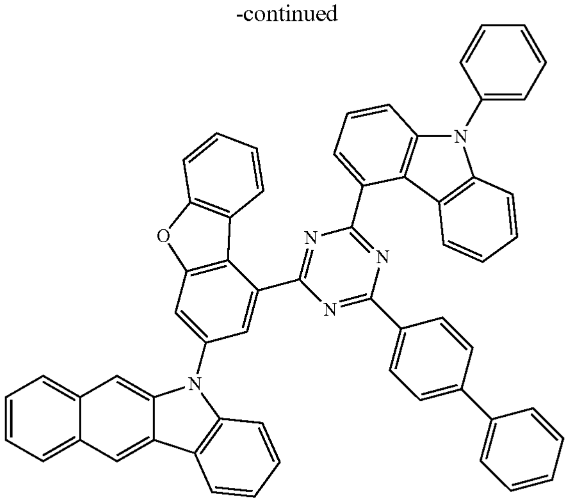
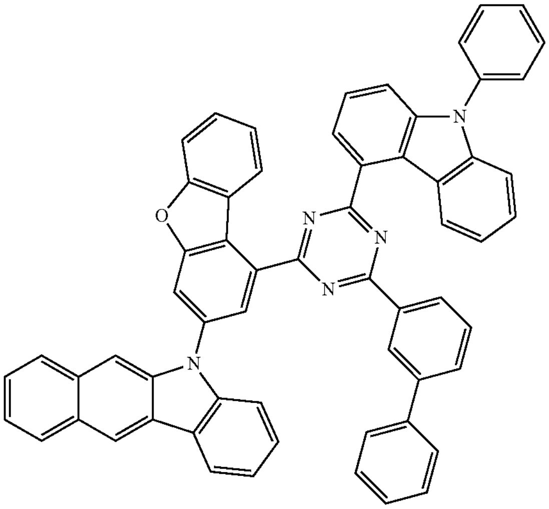
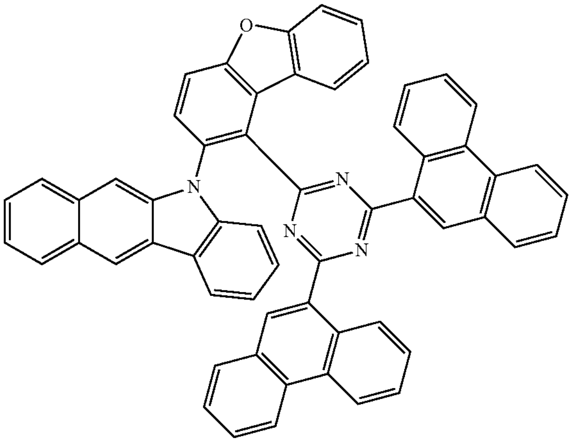

-continued
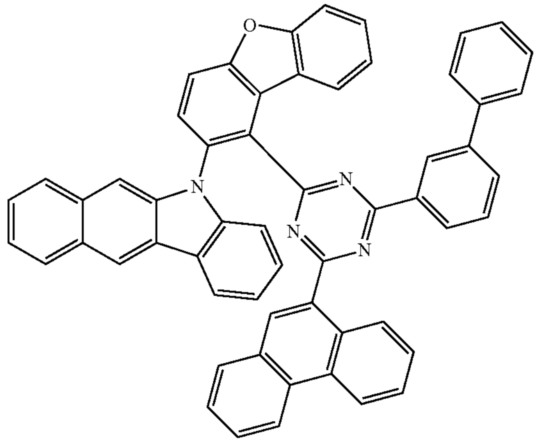
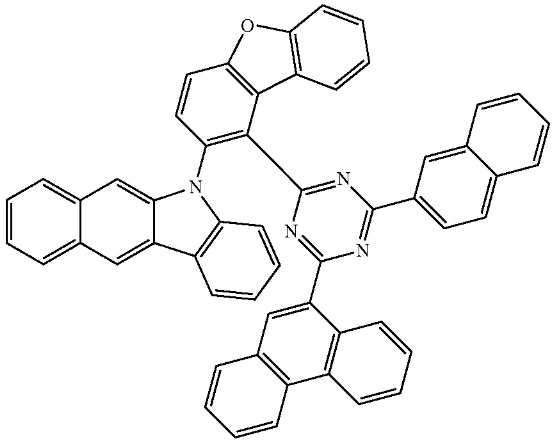
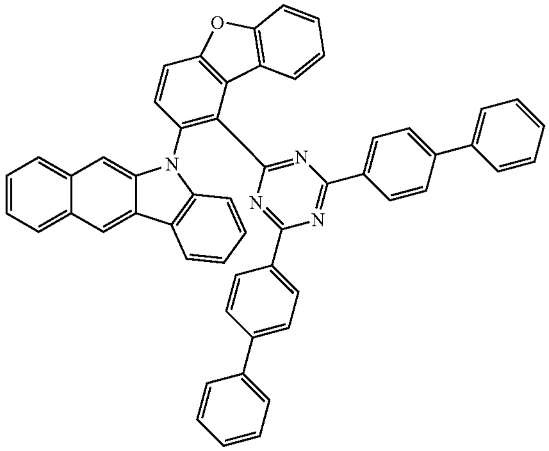
-continued
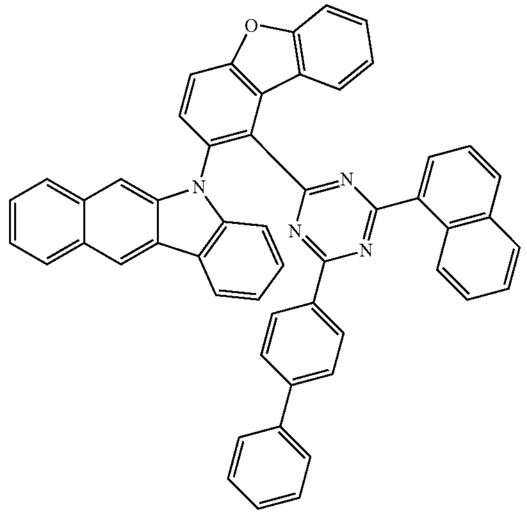
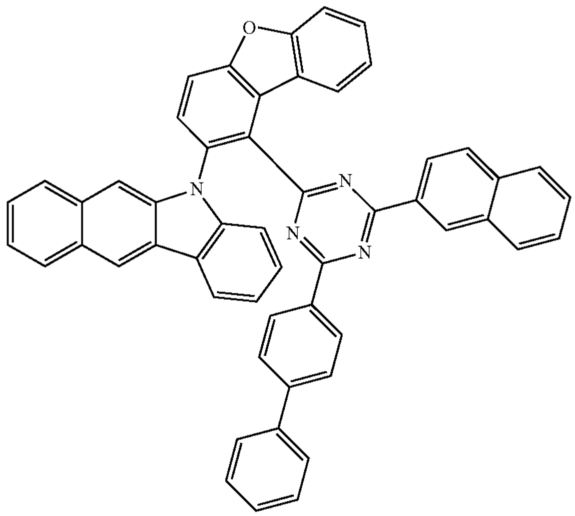
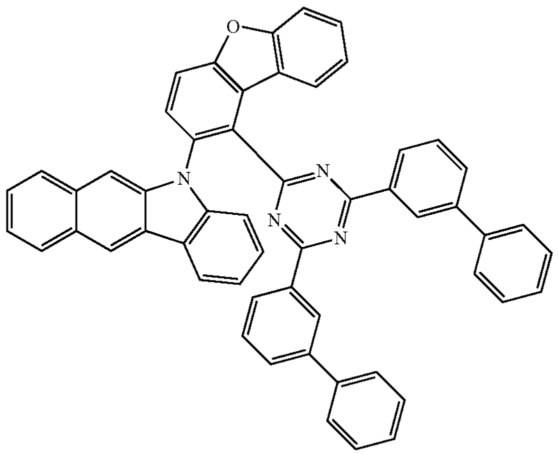

-continued
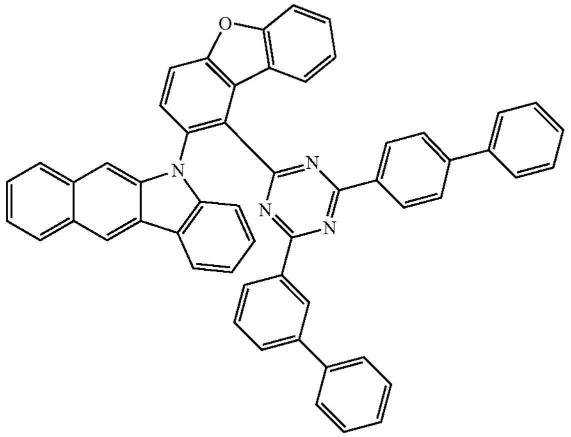
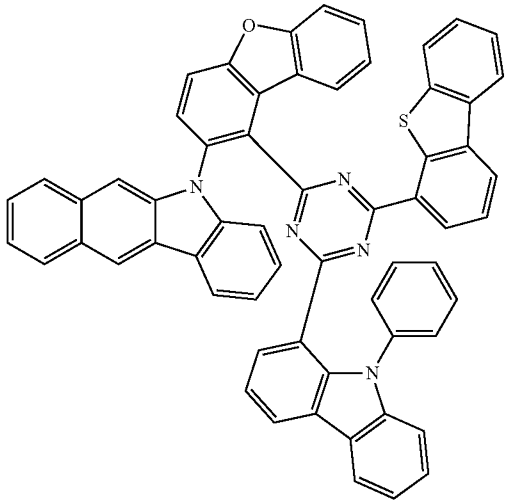
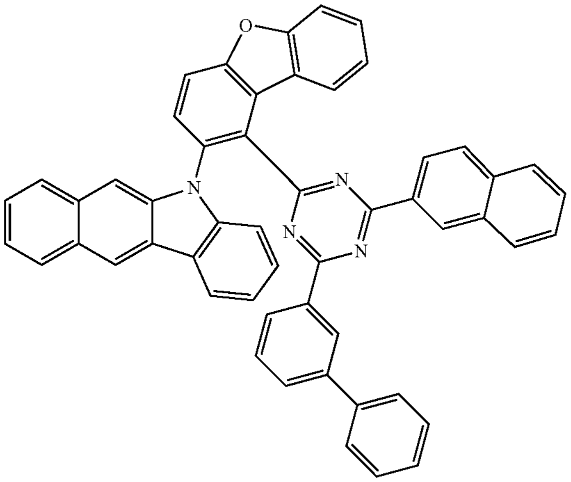
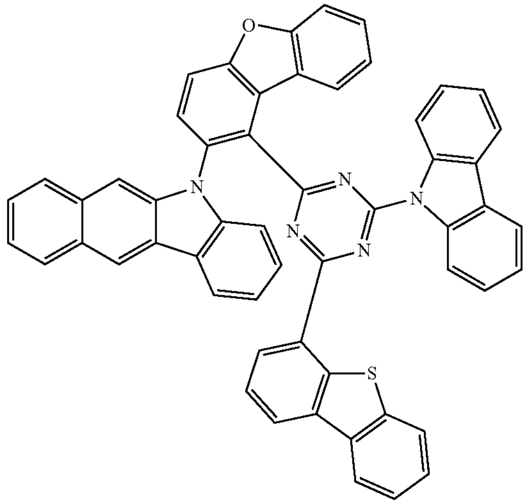
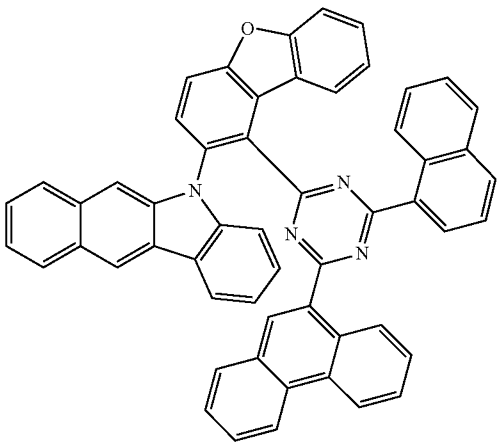
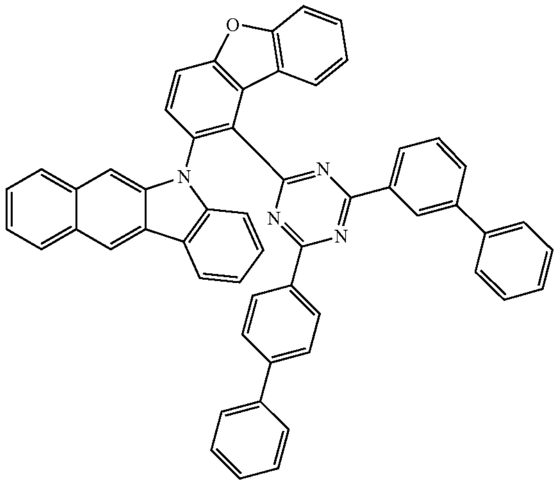

-continued
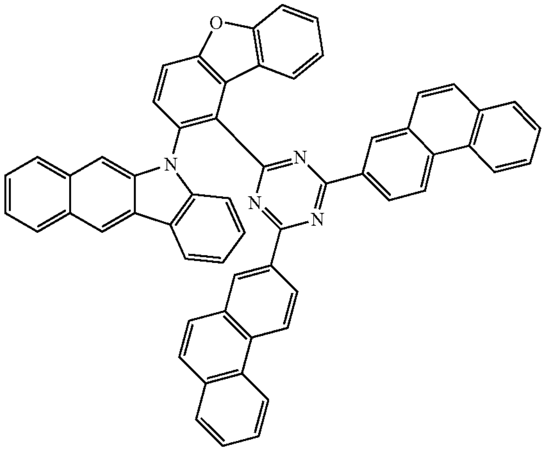
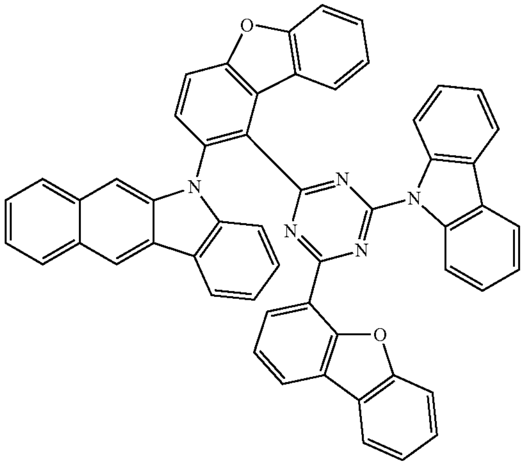
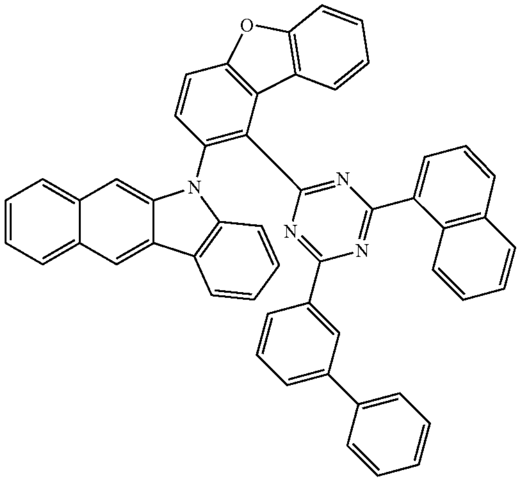
-continued
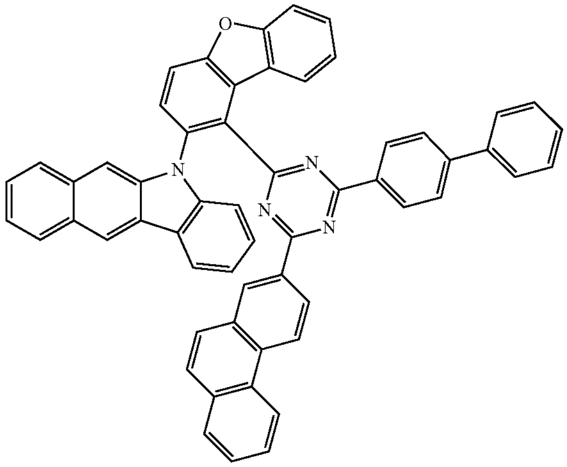
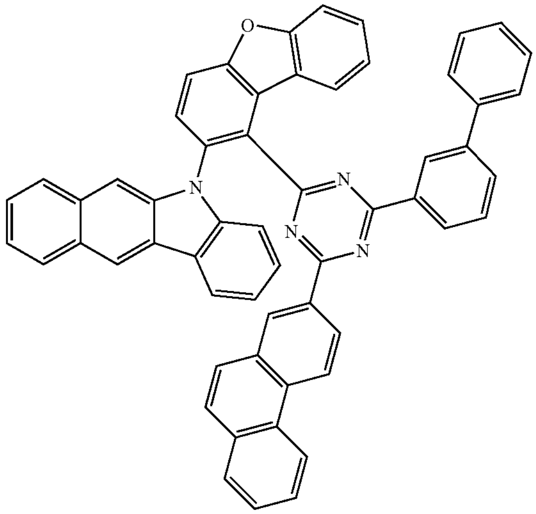
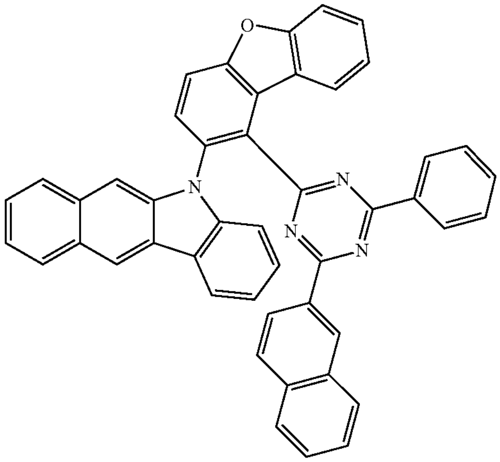

-continued
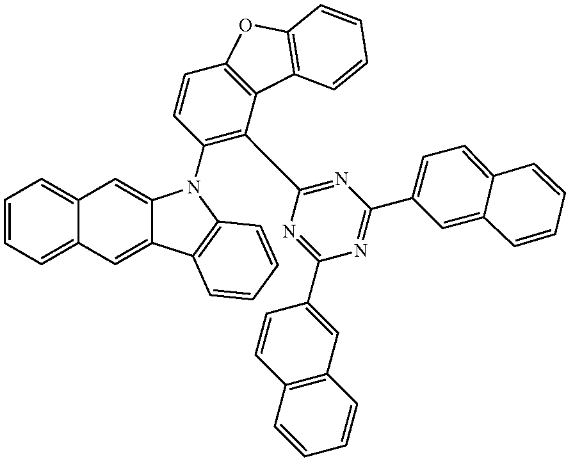
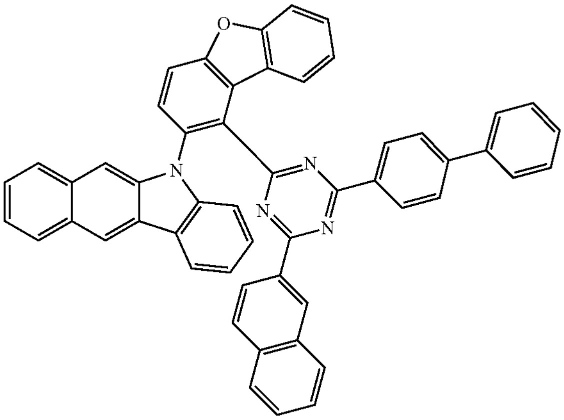
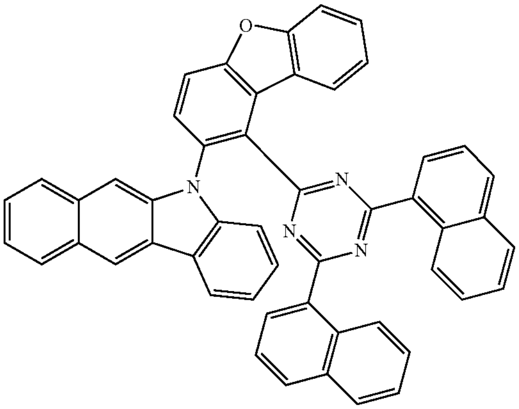
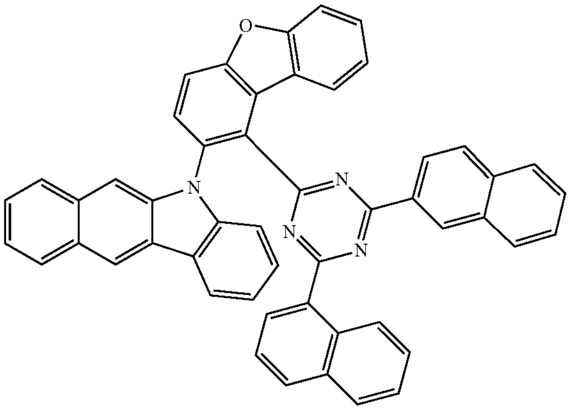
-continued
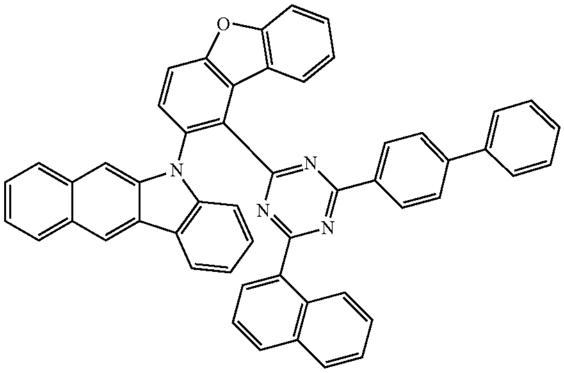
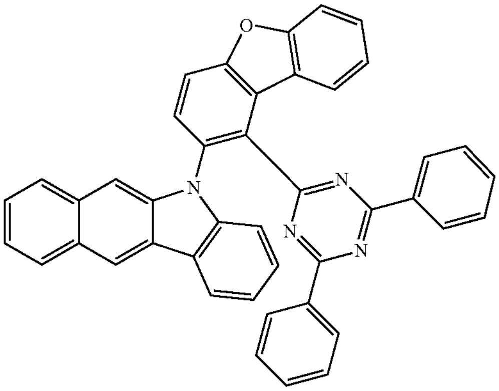
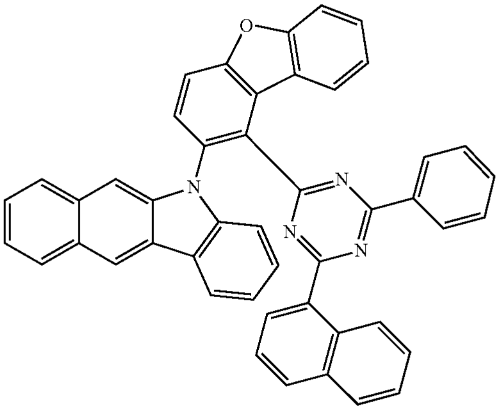
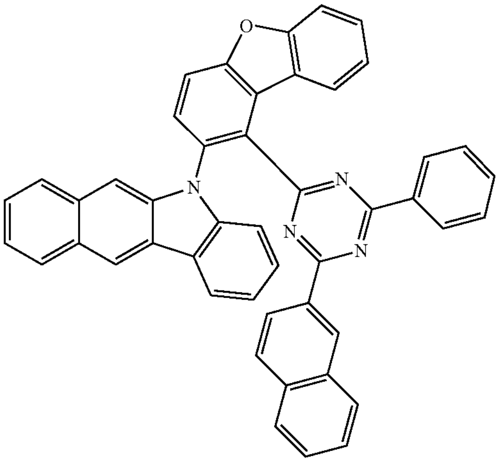

-continued
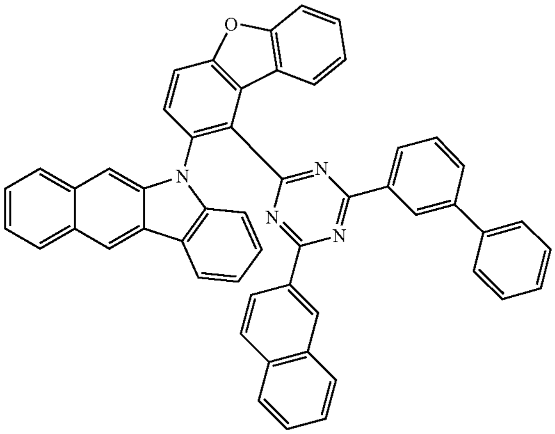
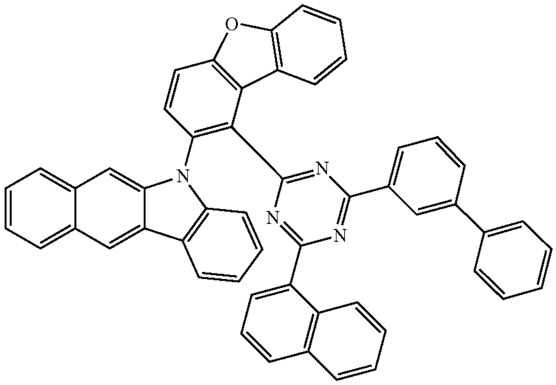
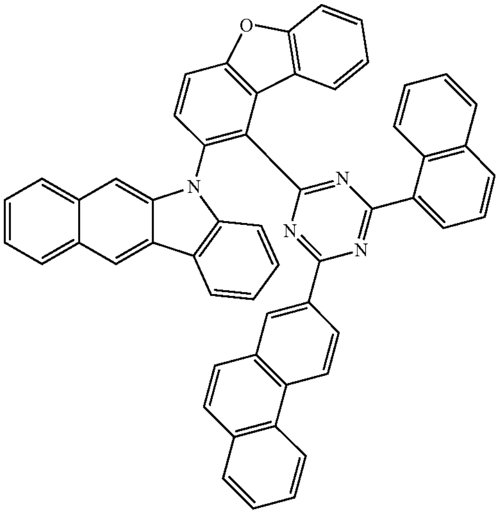
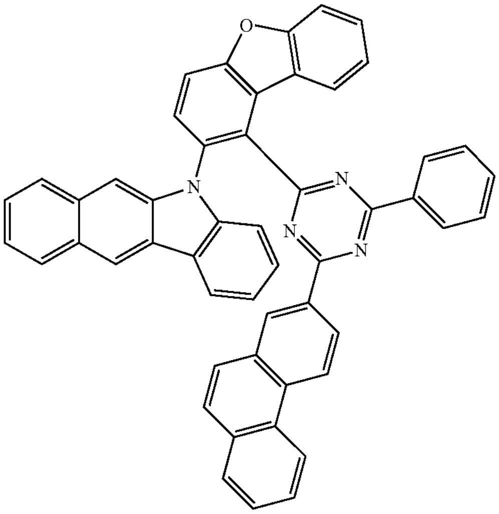
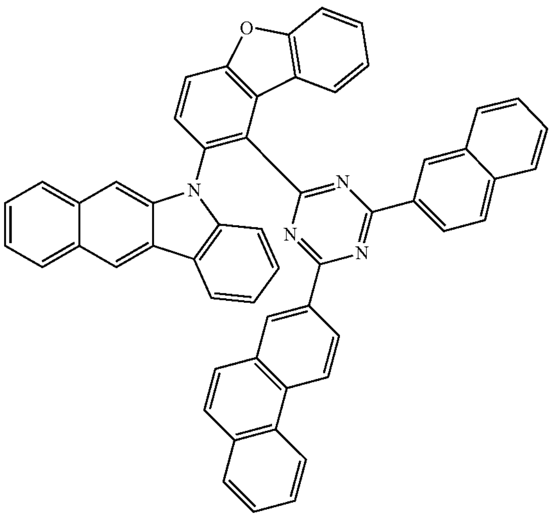
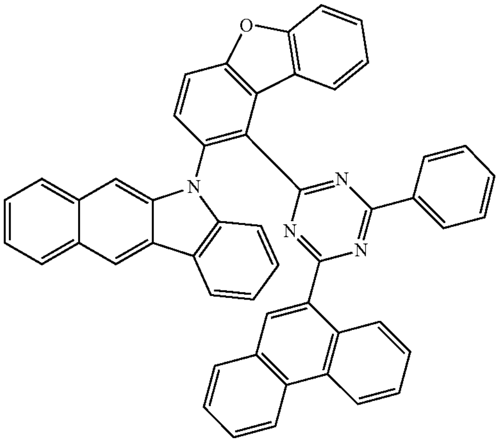
-continued -continued
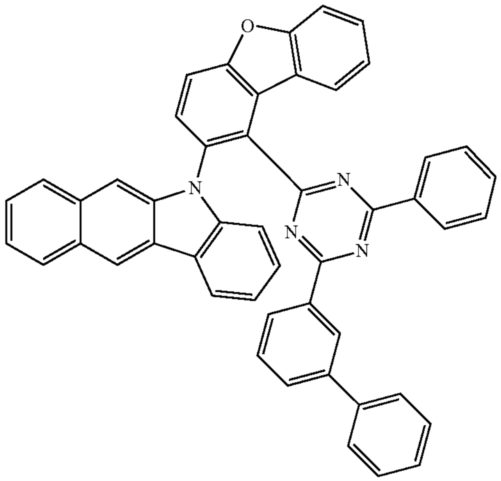
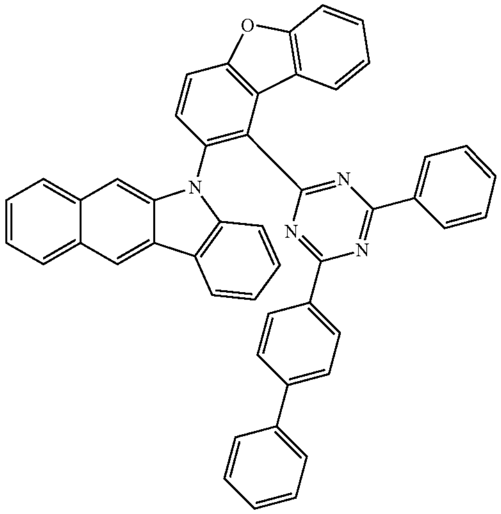
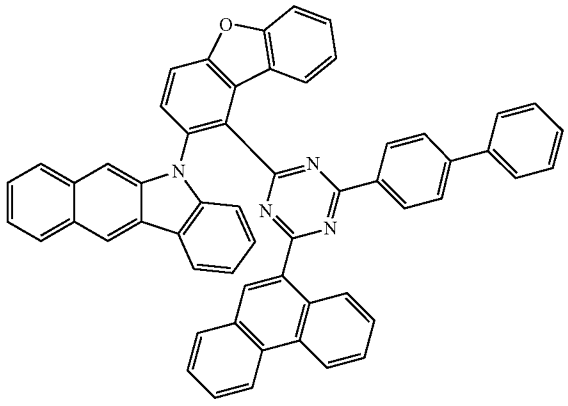
-continued
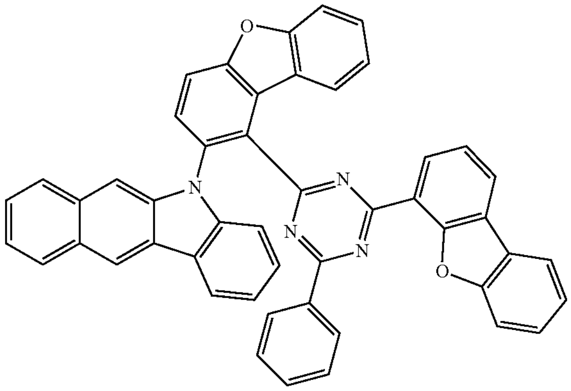
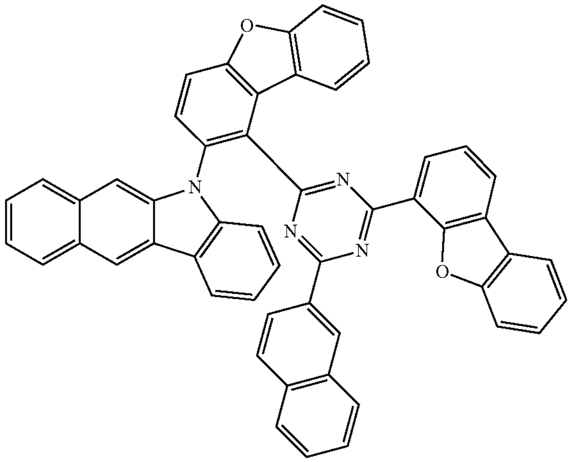
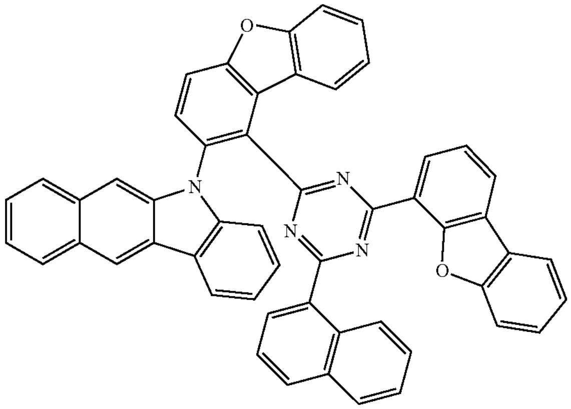
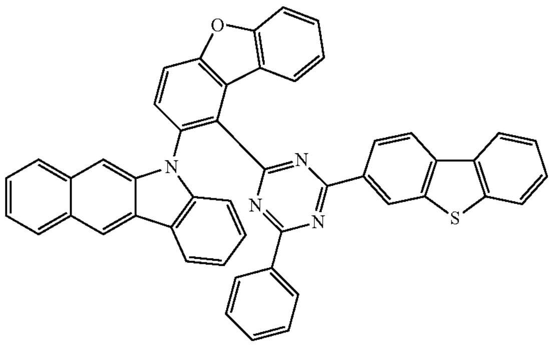

-continued
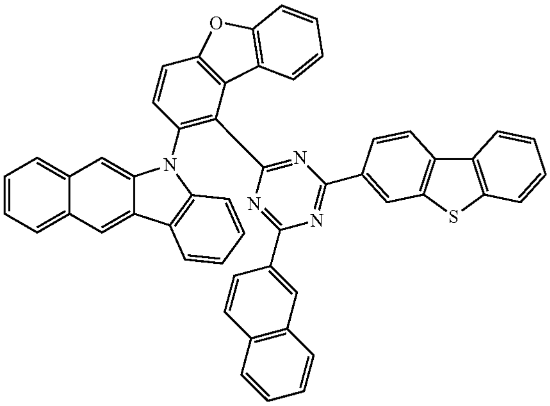
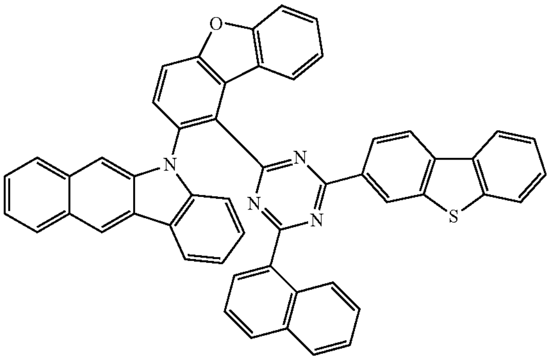
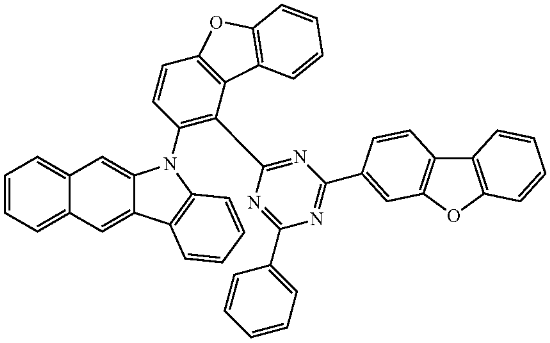
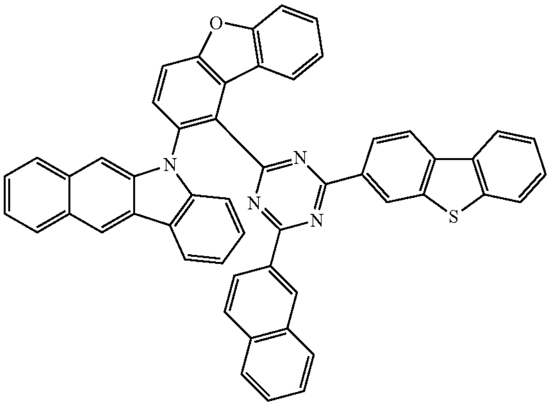
-continued
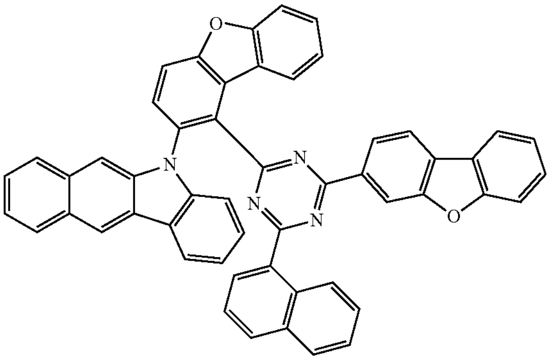
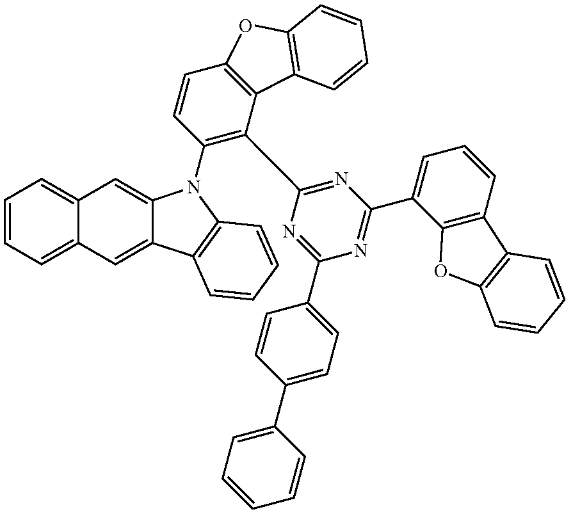
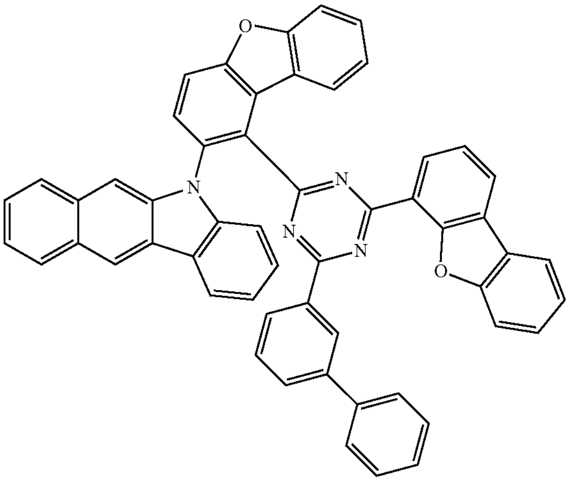

-continued
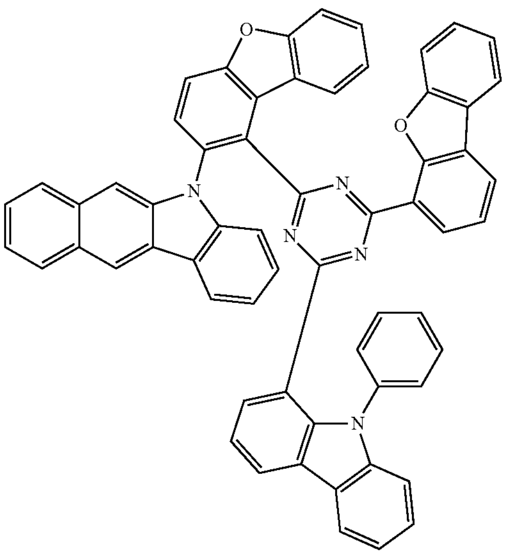
-continued
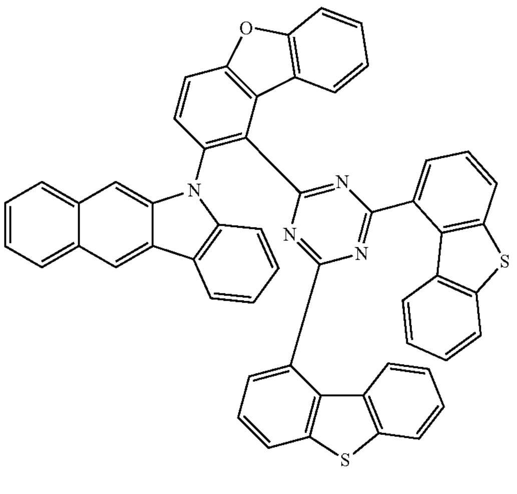
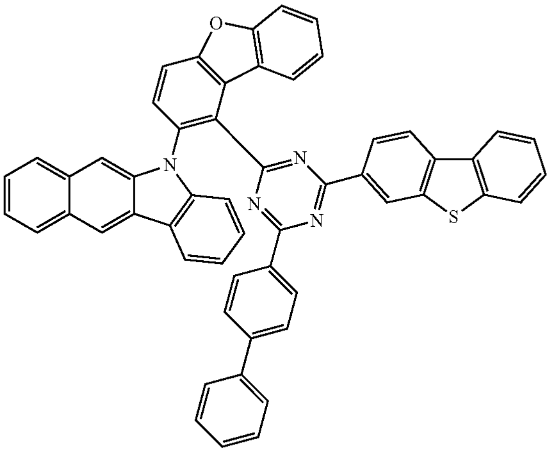
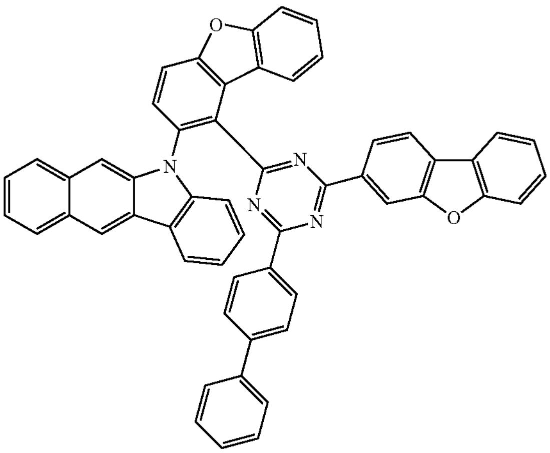
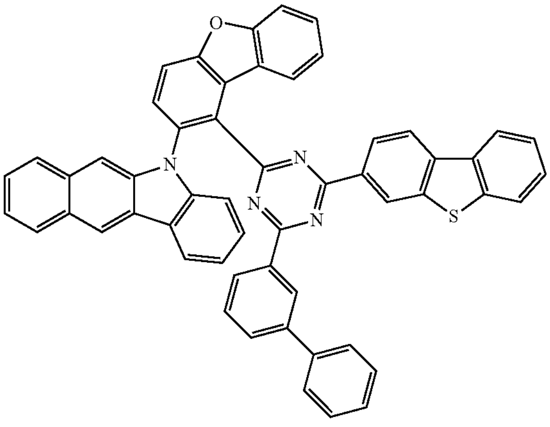
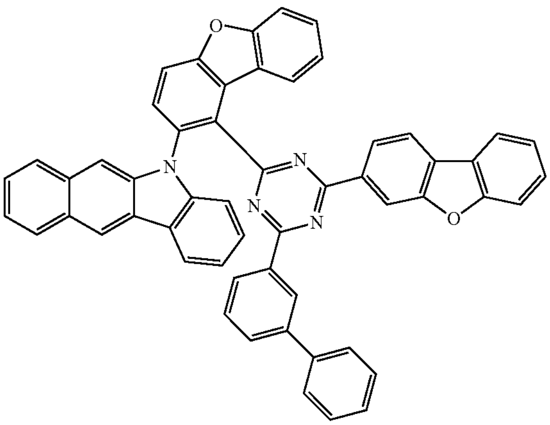

-continued
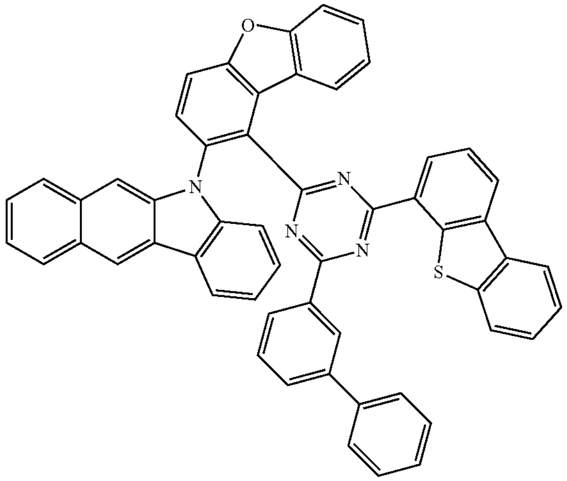
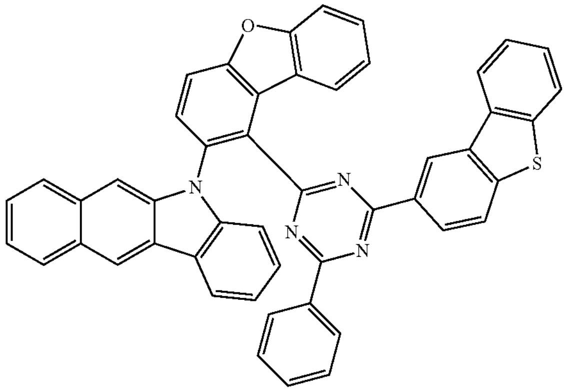
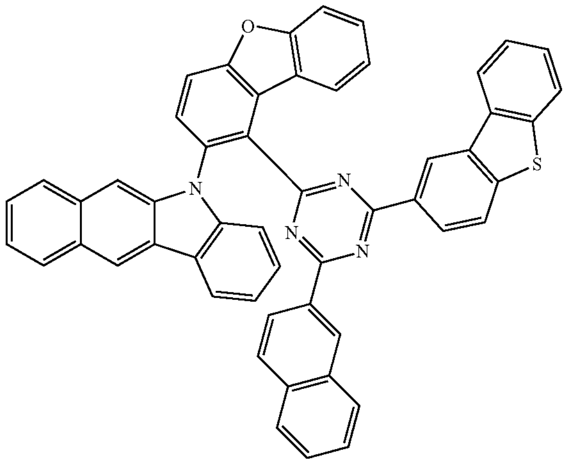
-continued
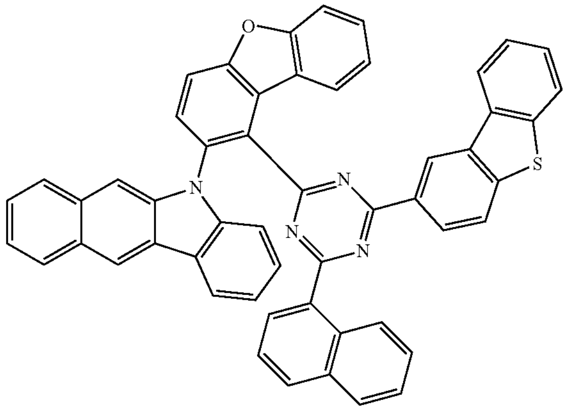
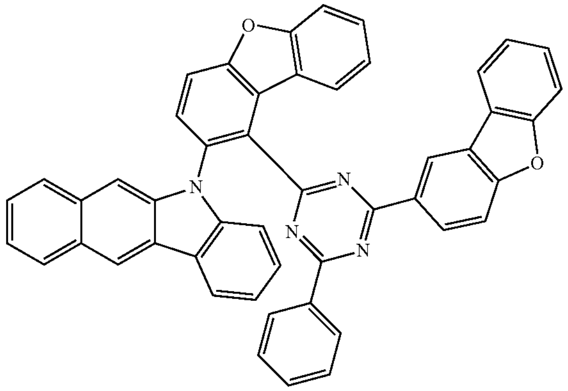
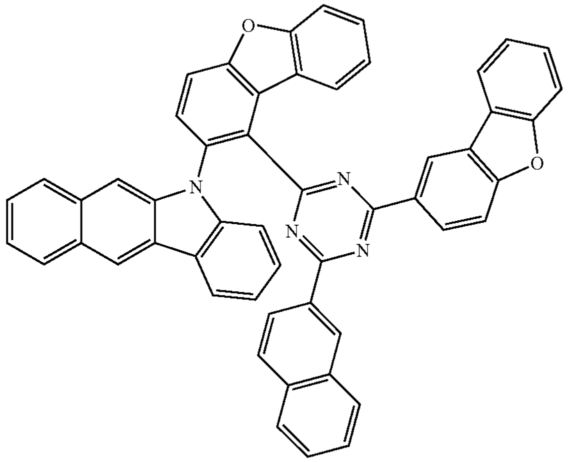
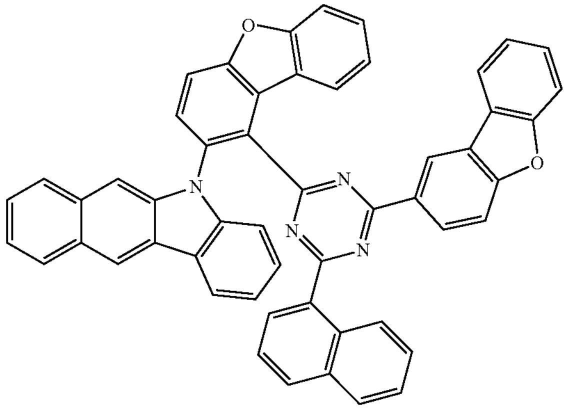

-continued
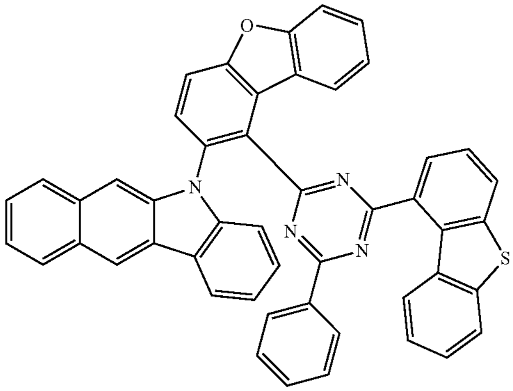
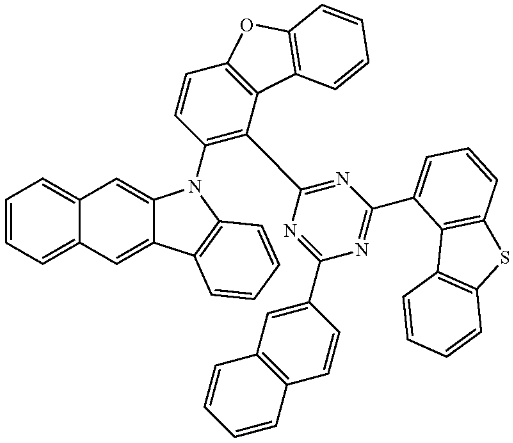
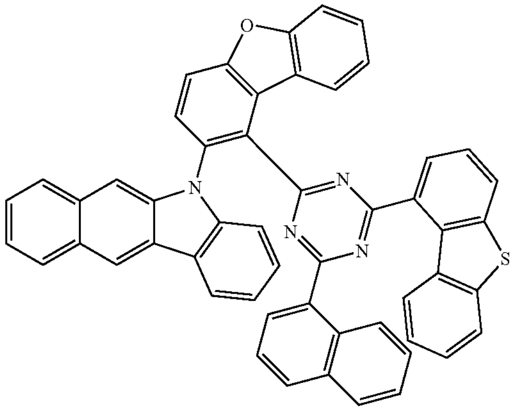
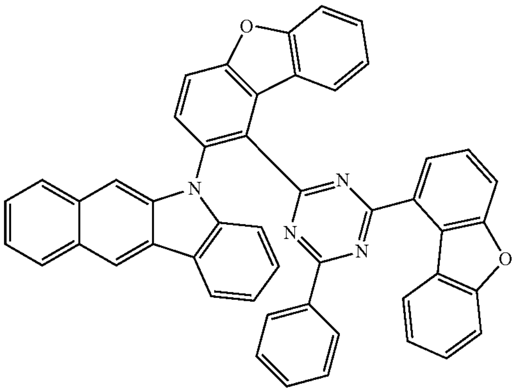
-continued
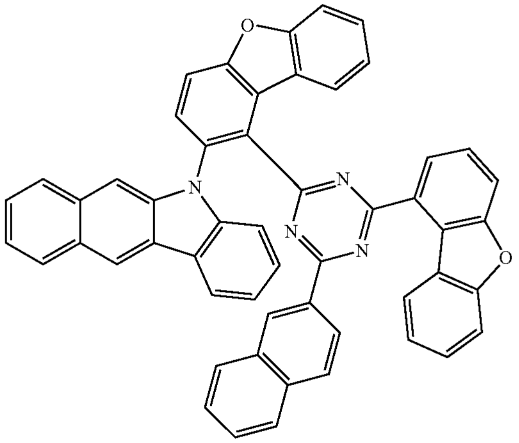
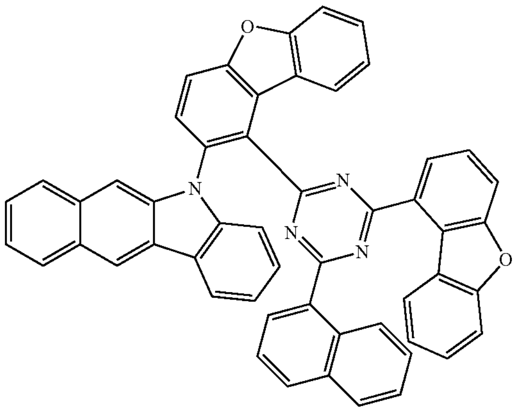
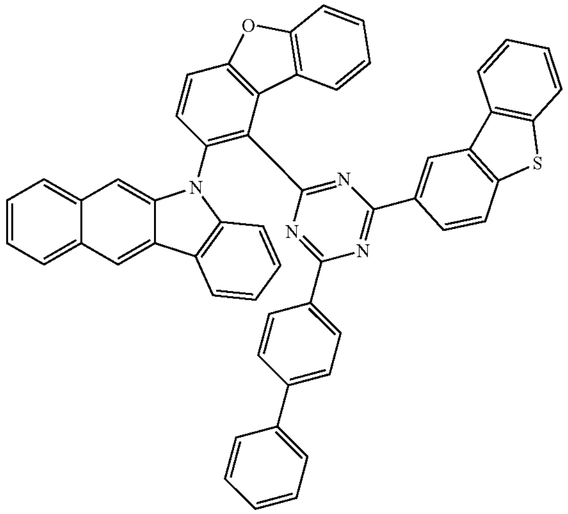

-continued
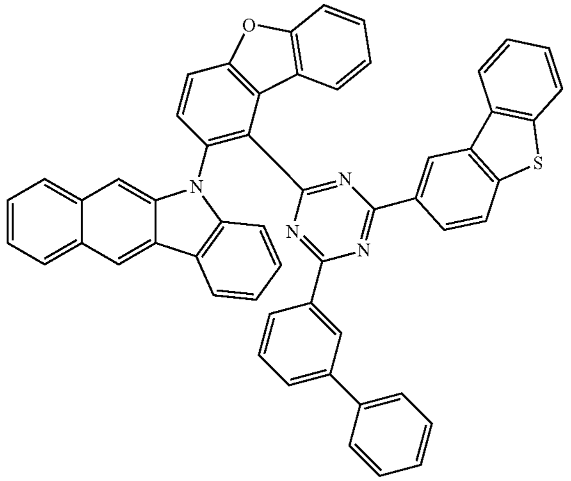
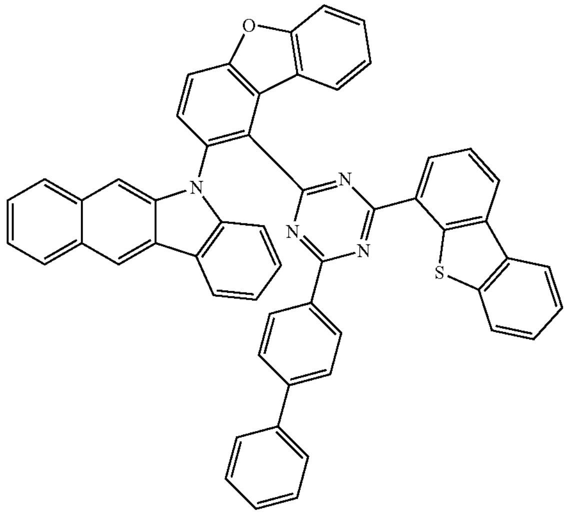
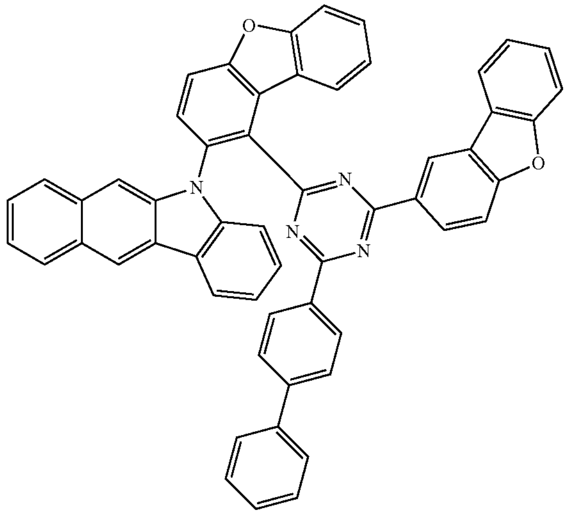
-continued
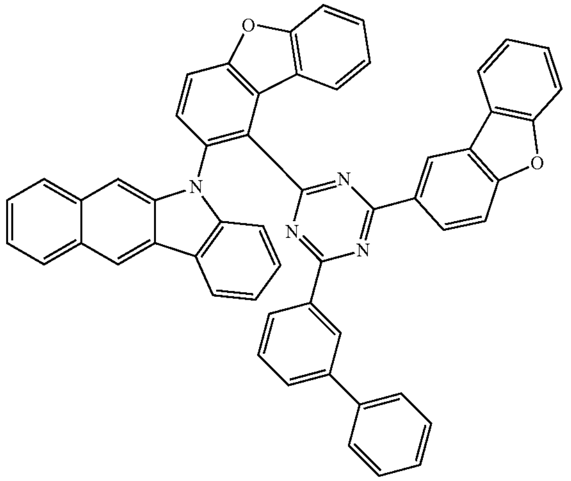
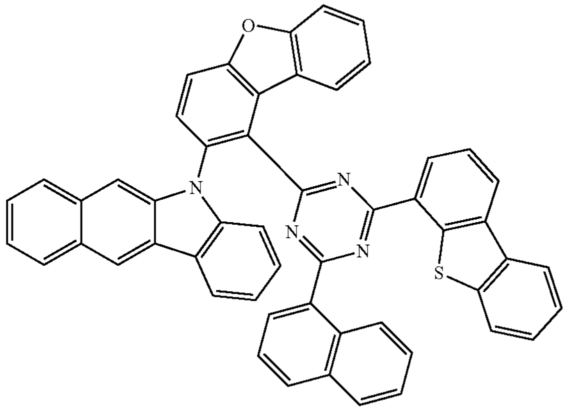
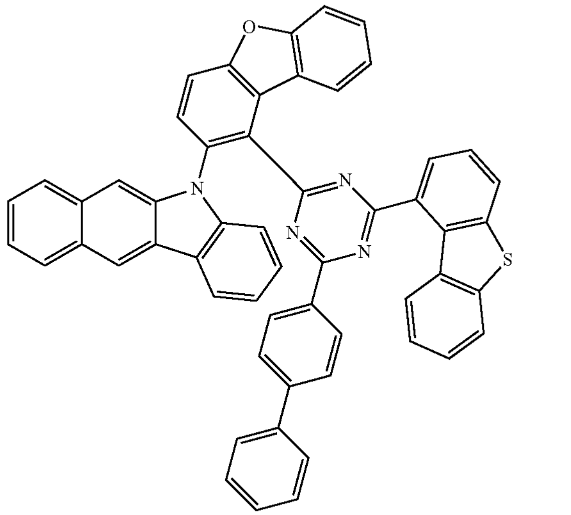

-continued
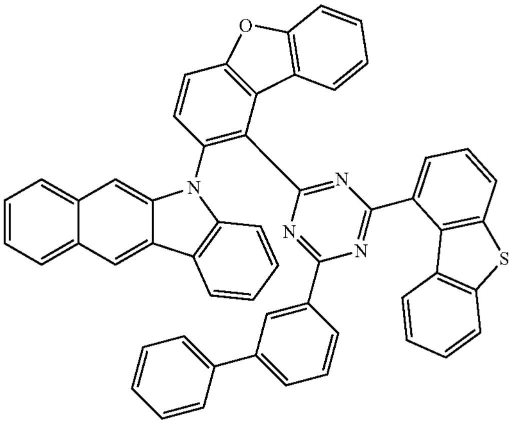
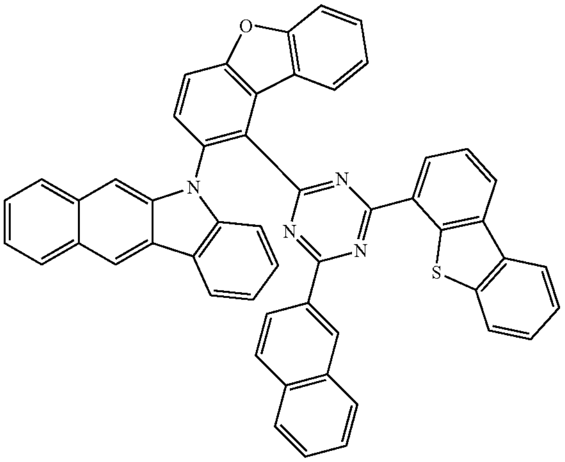
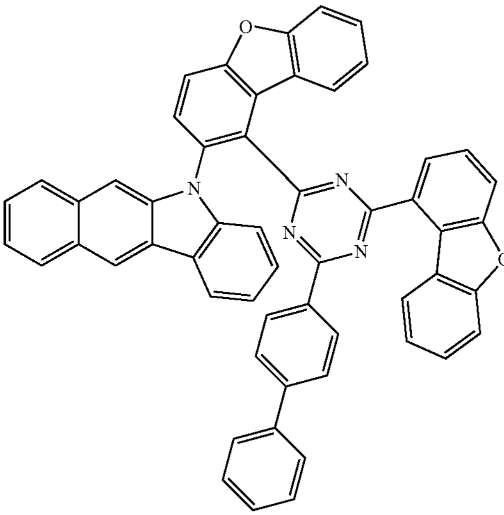
-continued
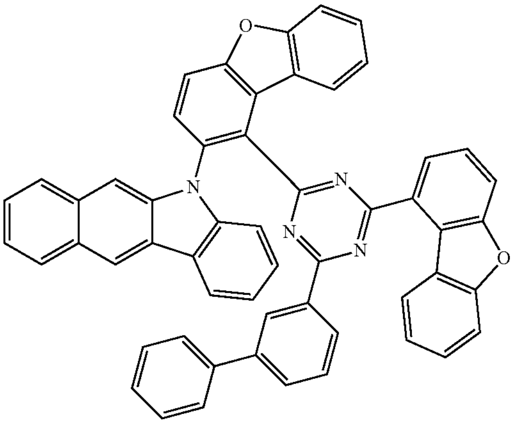
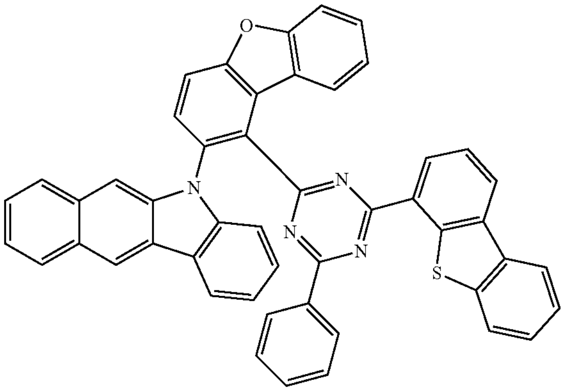
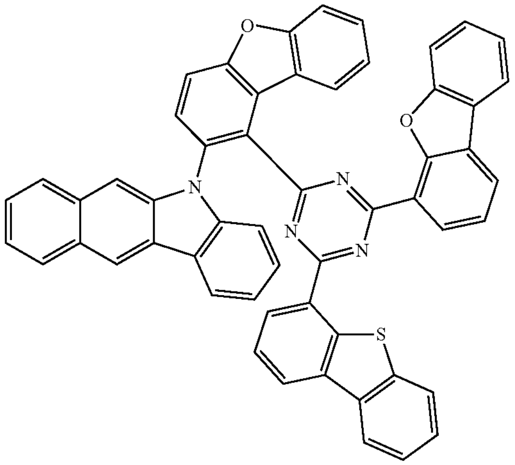

-continued
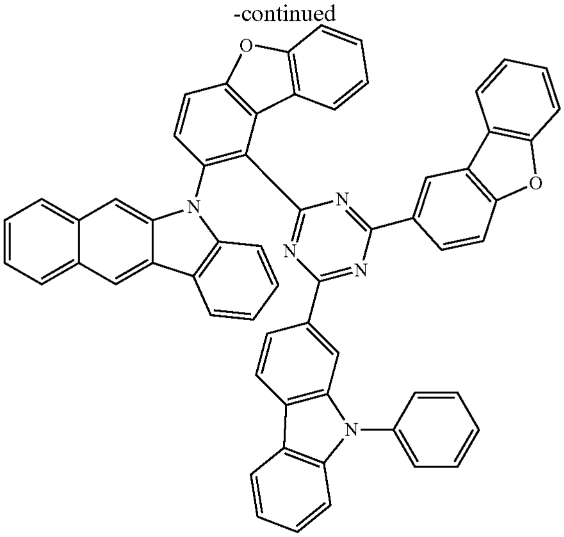
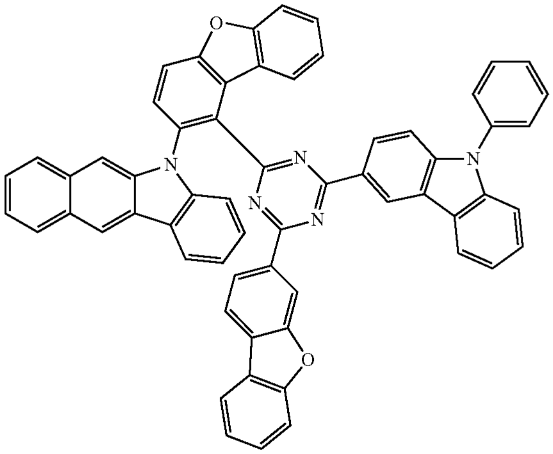
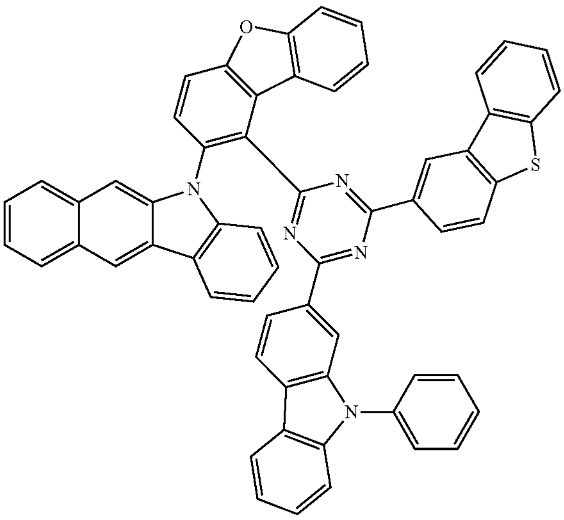
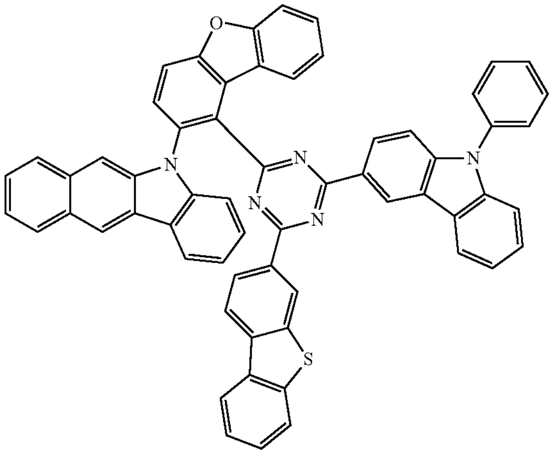
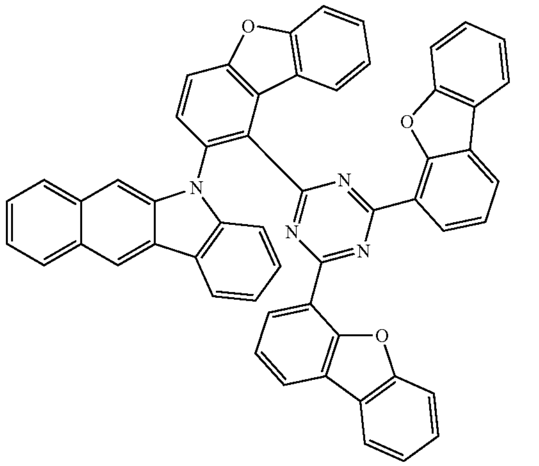
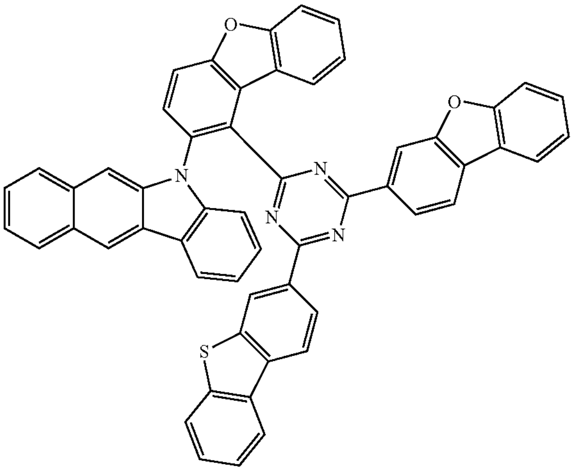
-continued -continued
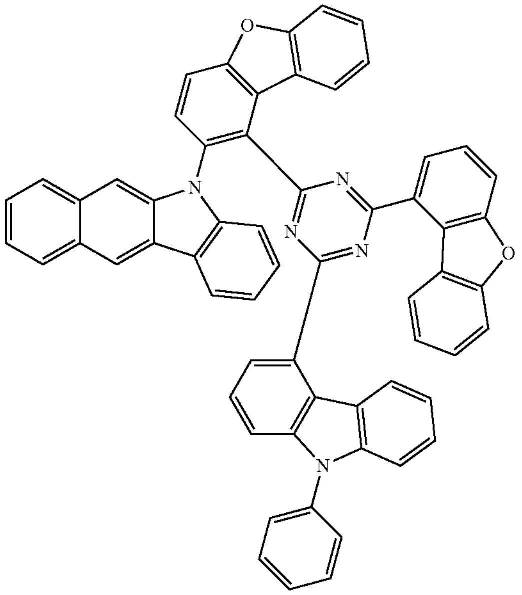
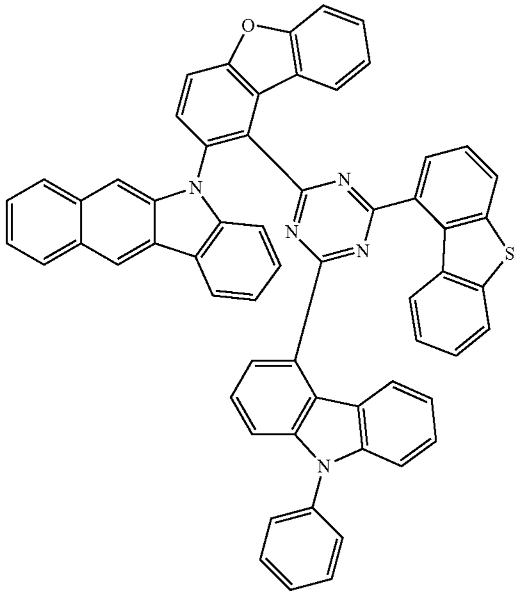
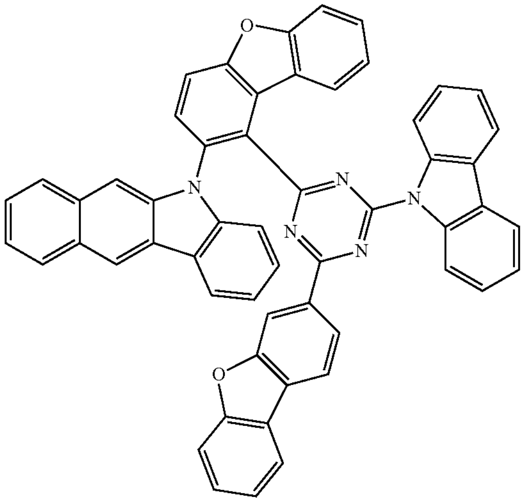
-continued
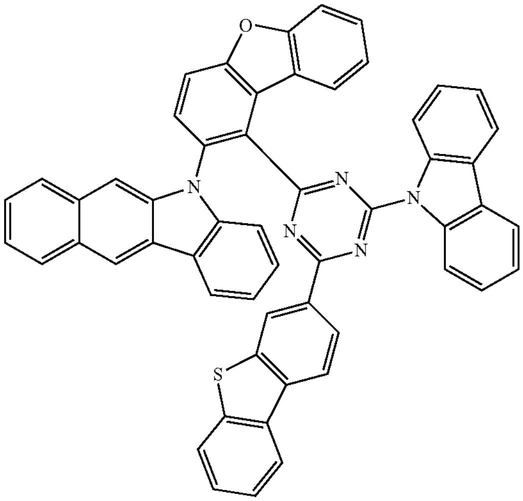
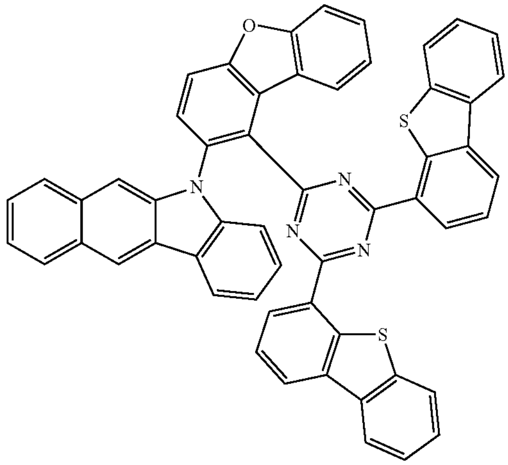
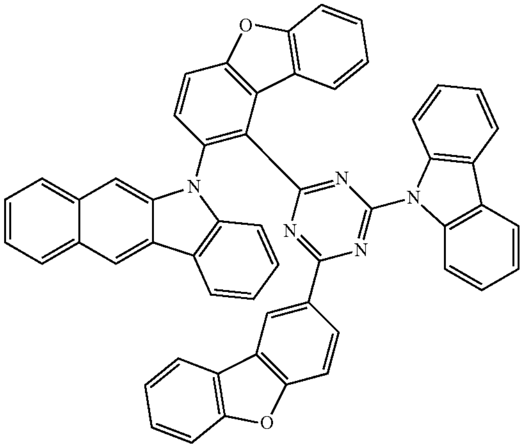

-continued
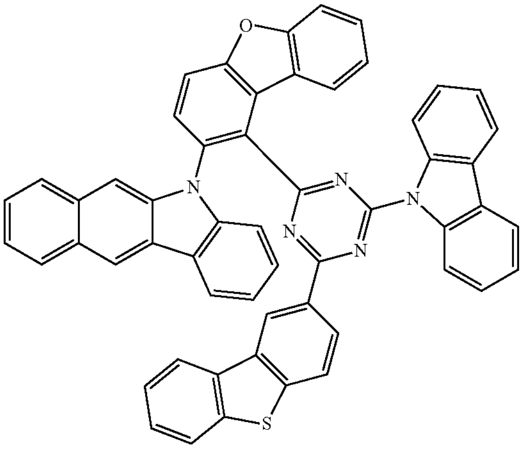
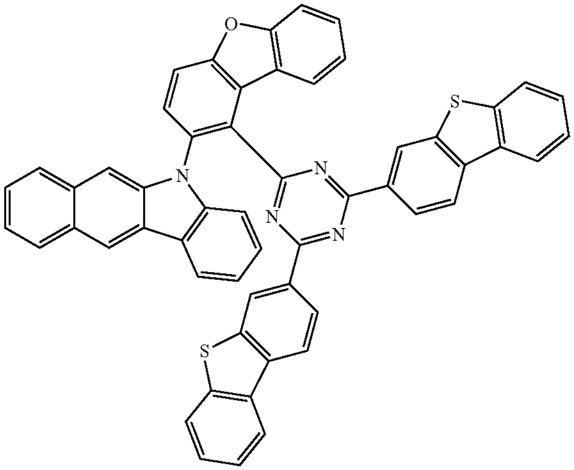
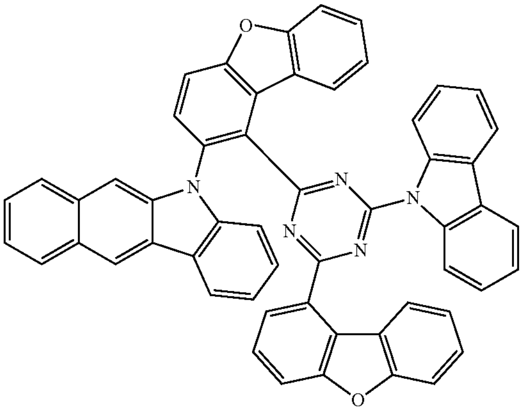
-continued
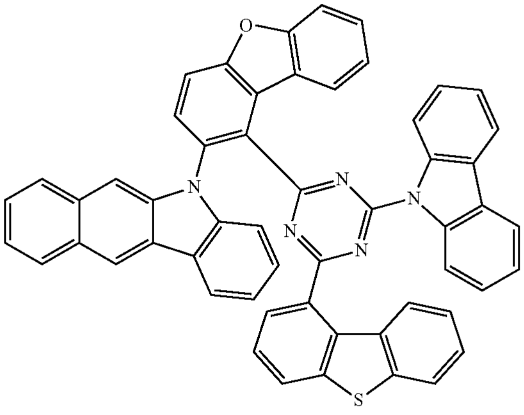
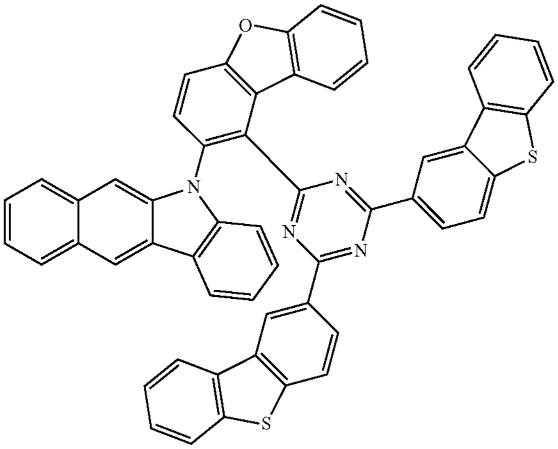
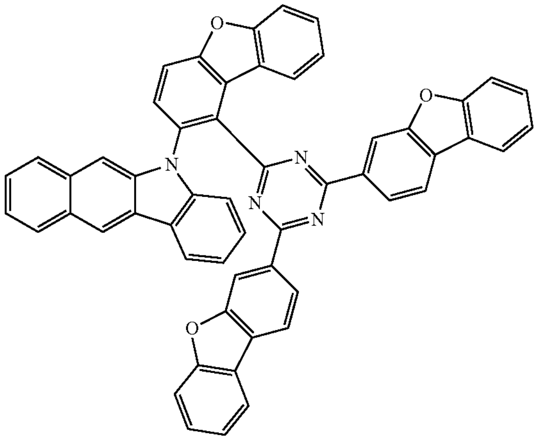
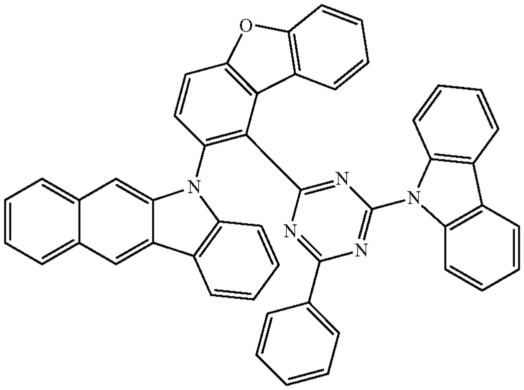

-continued
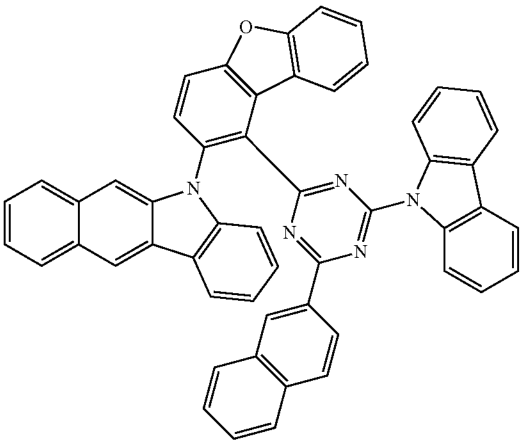
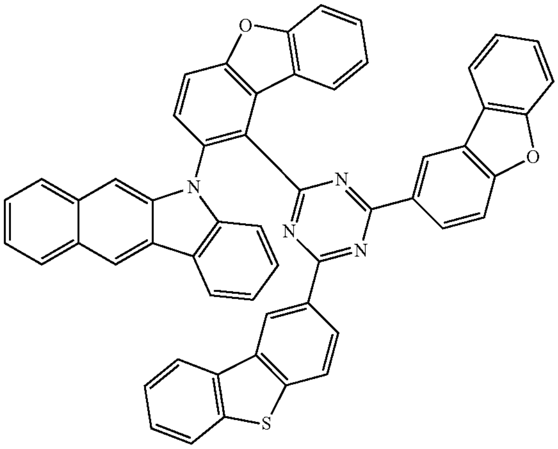
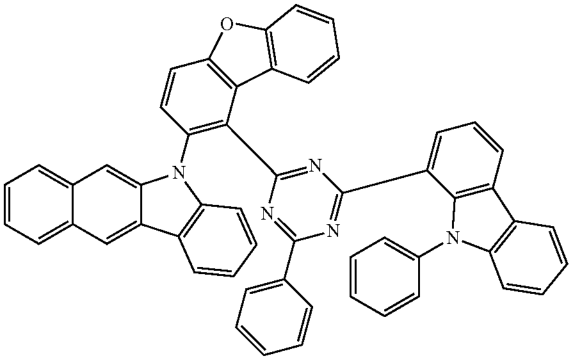
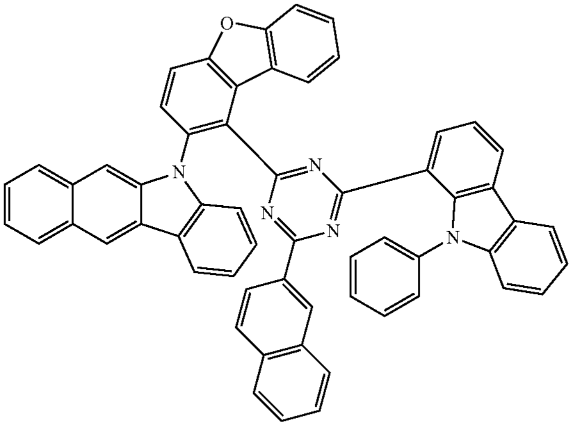
-continued
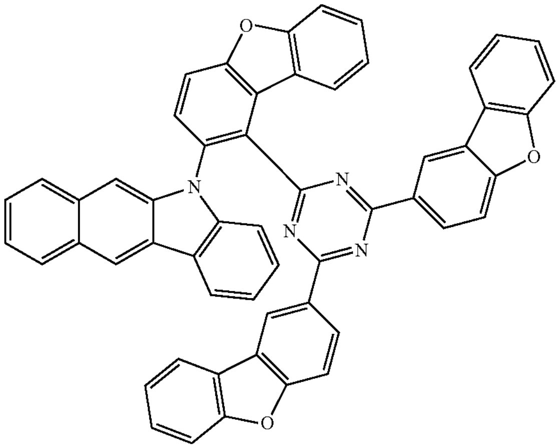
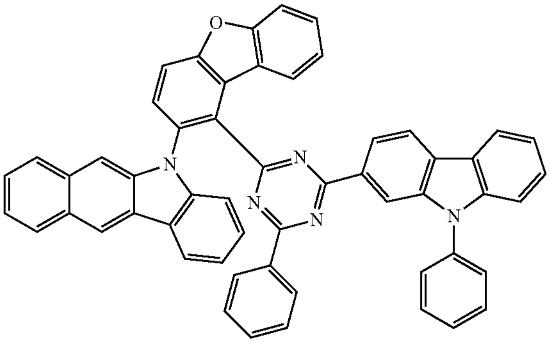
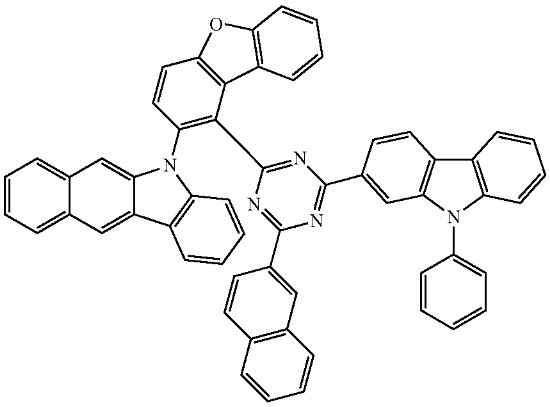
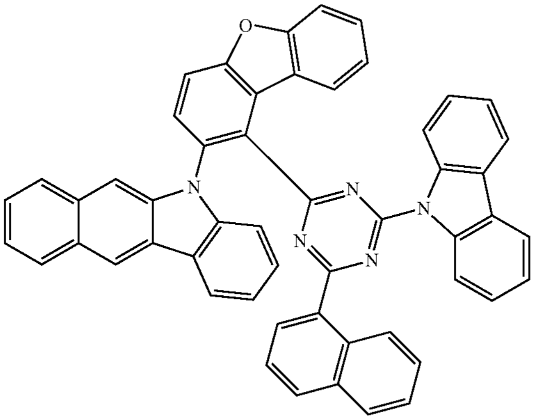

-continued
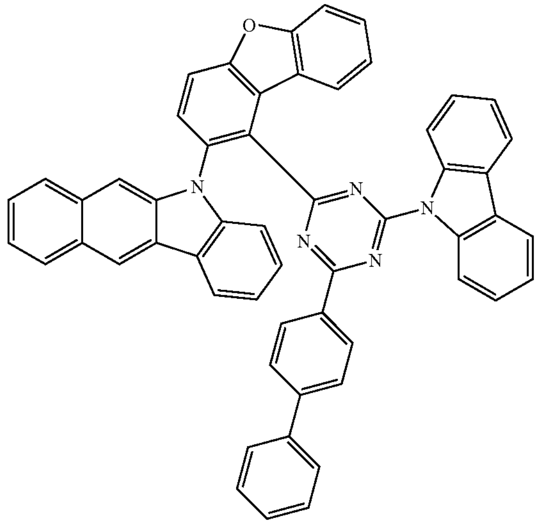
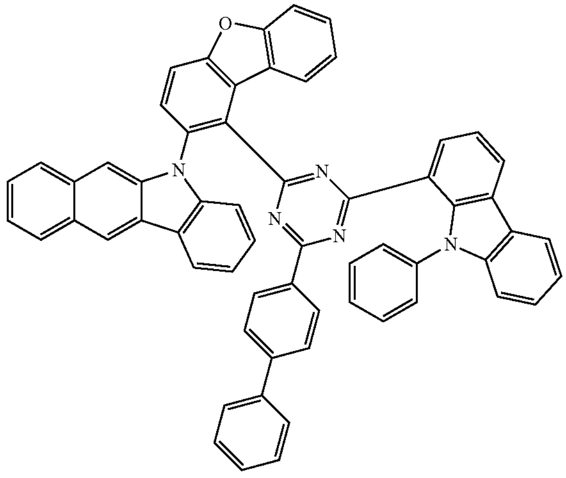
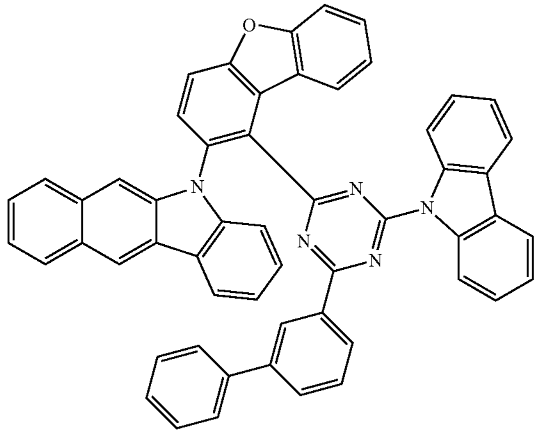
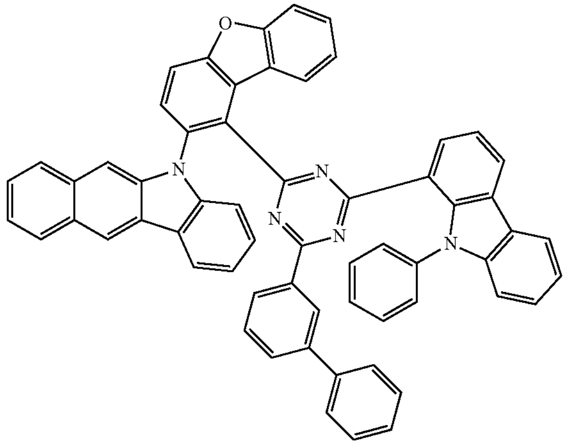
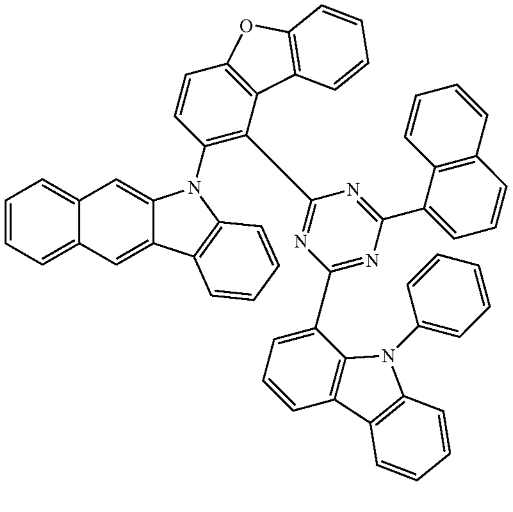
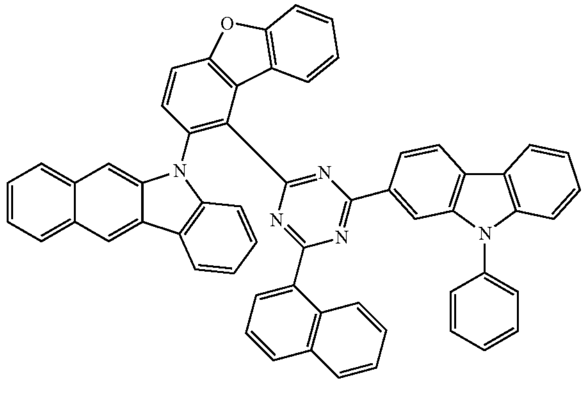
-continued -continued
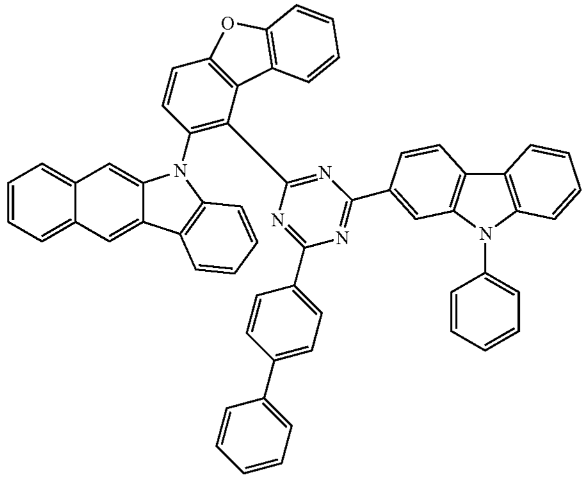
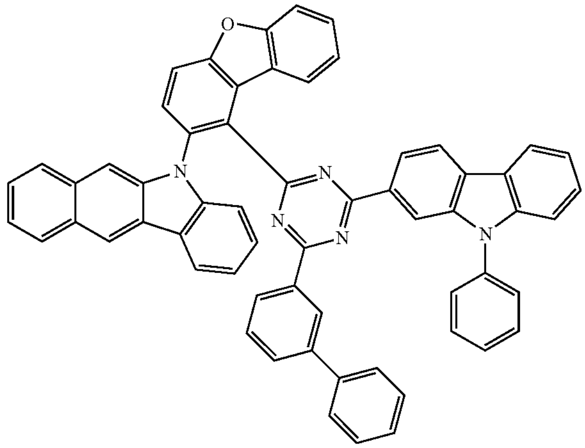
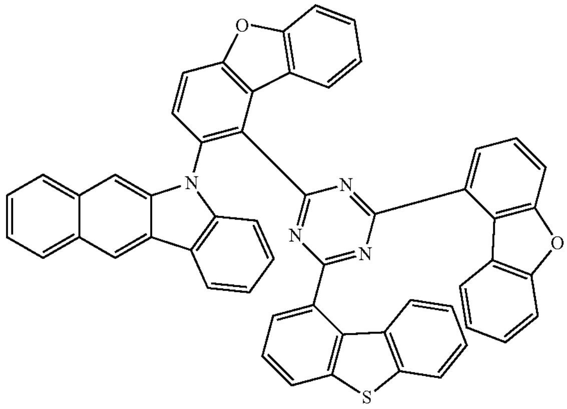
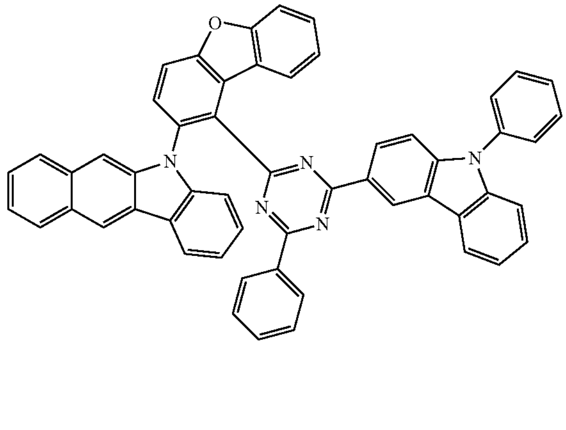
-continued
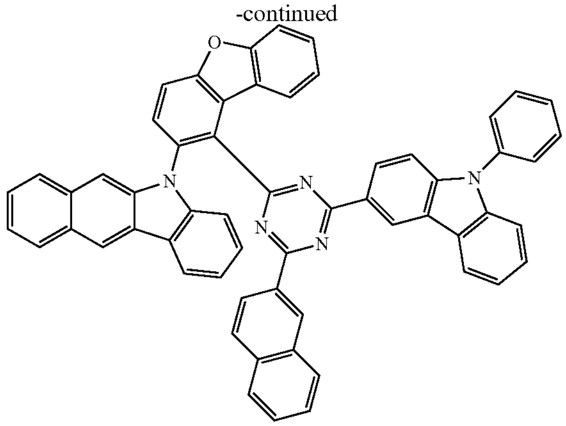
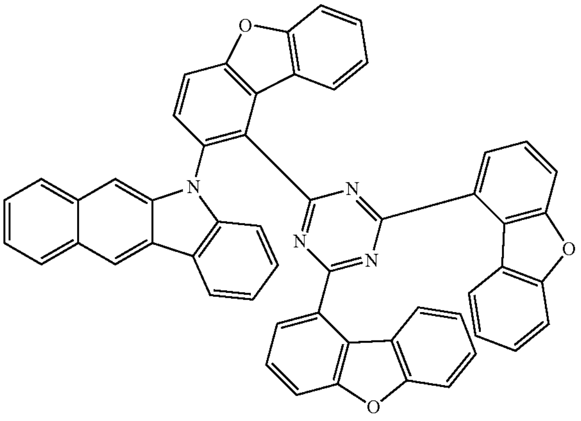
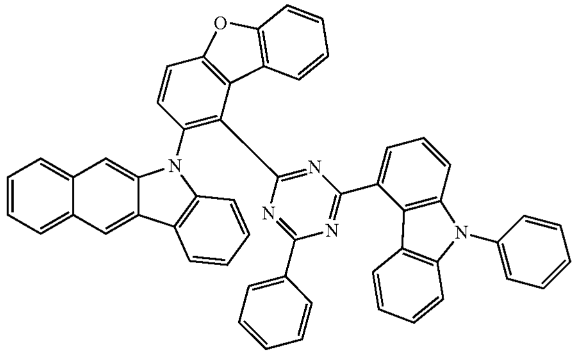
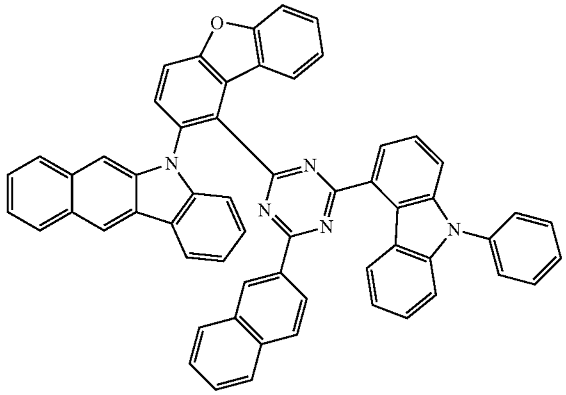

-continued
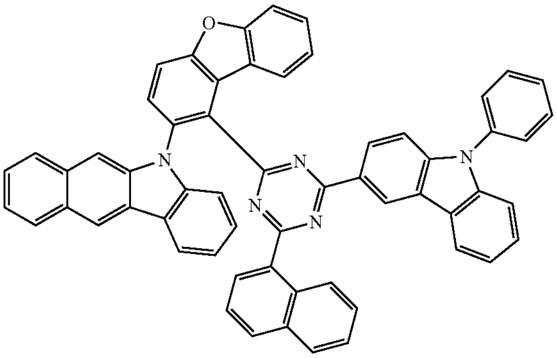
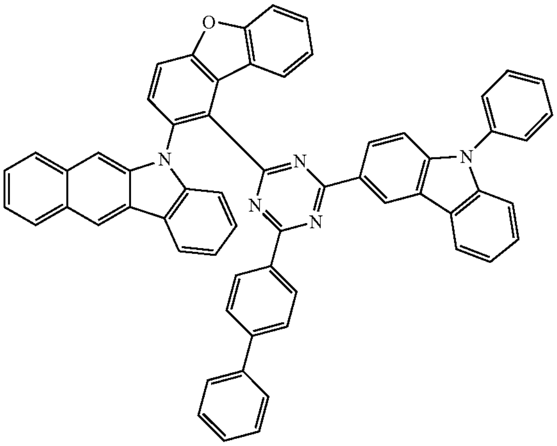
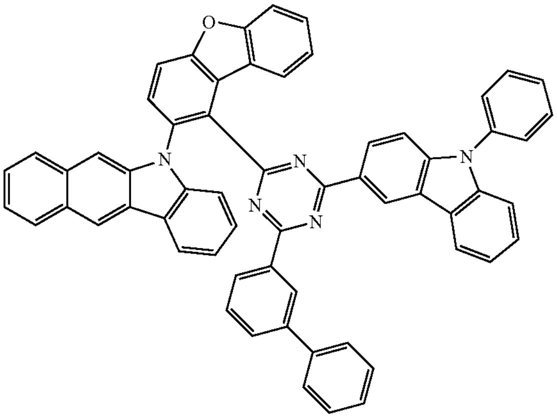
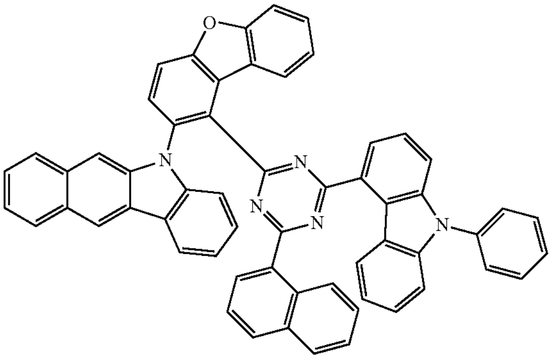
-continued
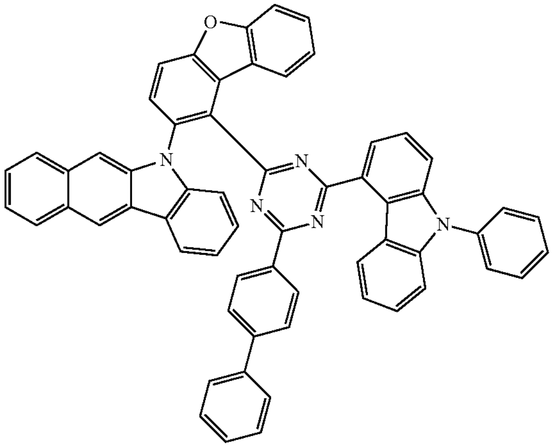
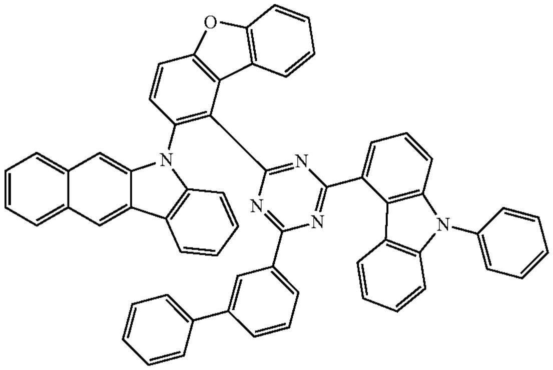
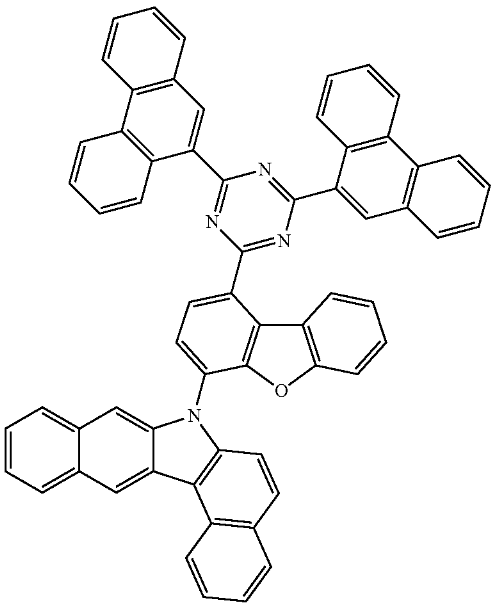

-continued
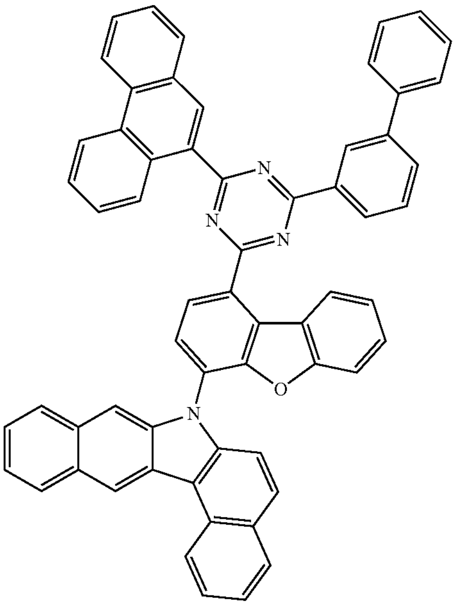
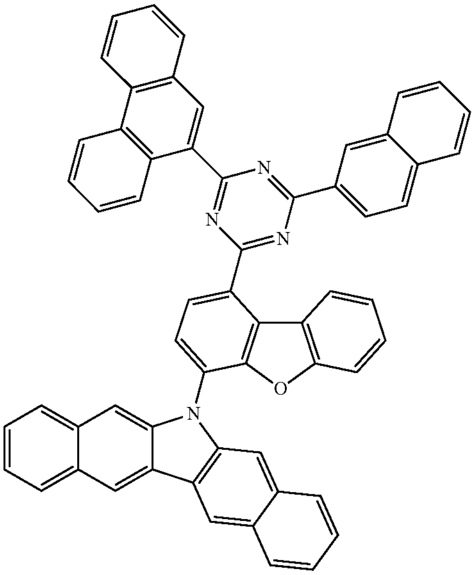
-continued
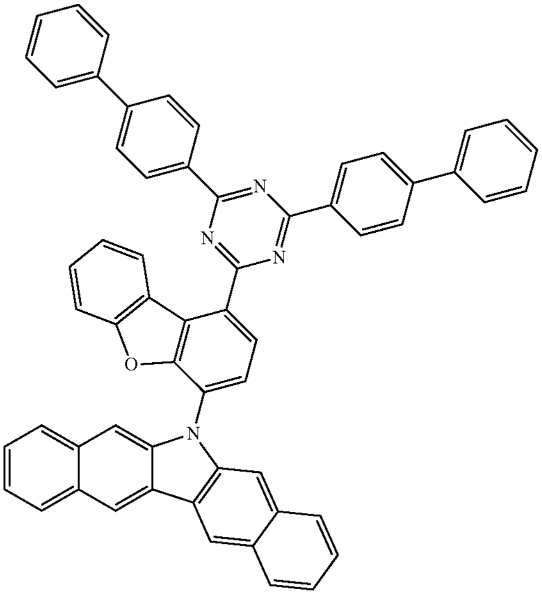
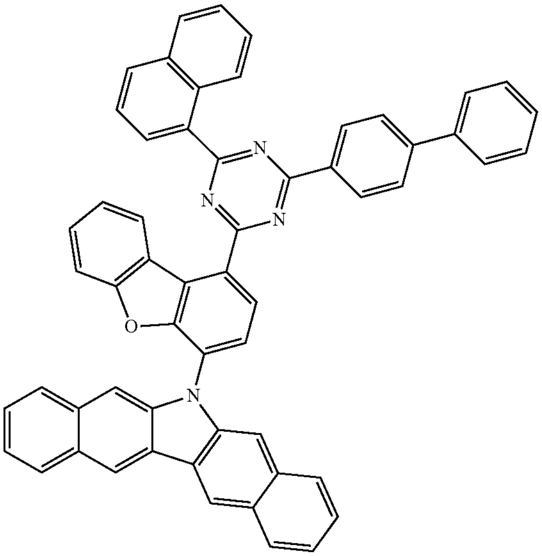
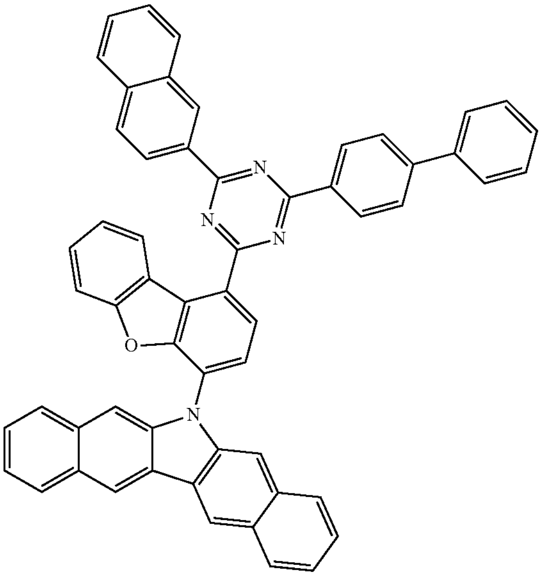

-continued
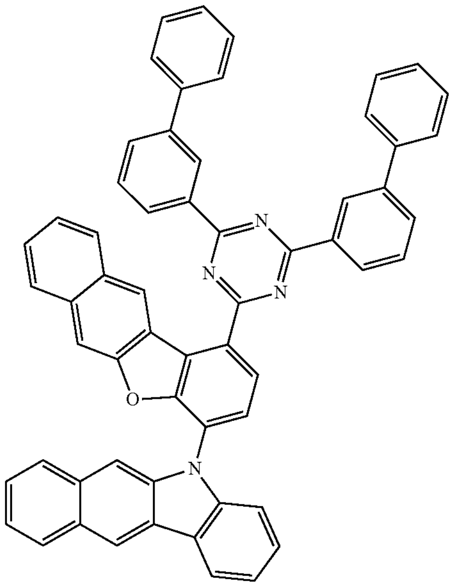
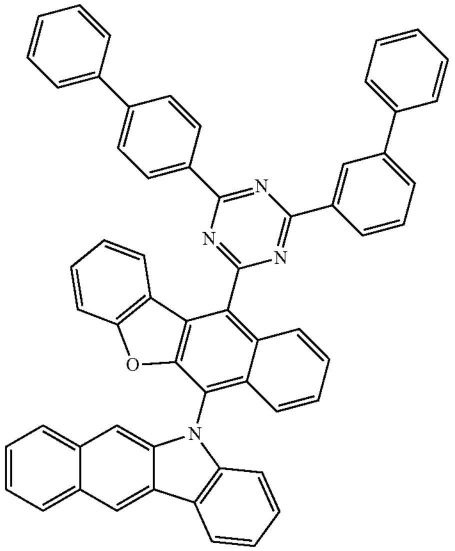
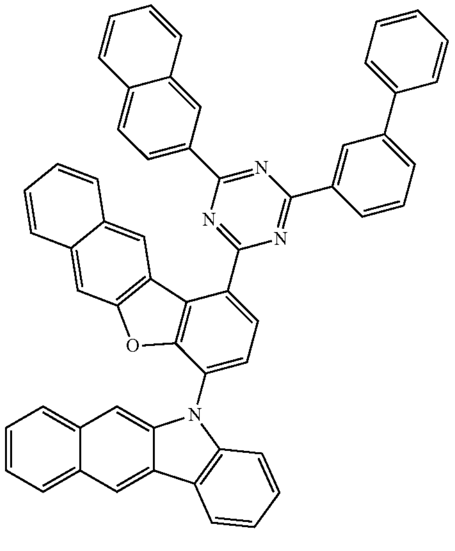
-continued
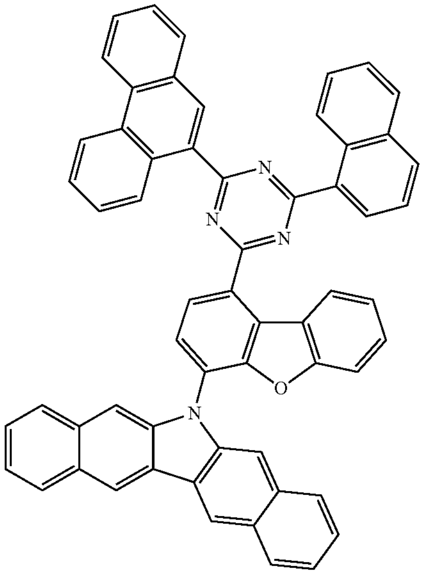
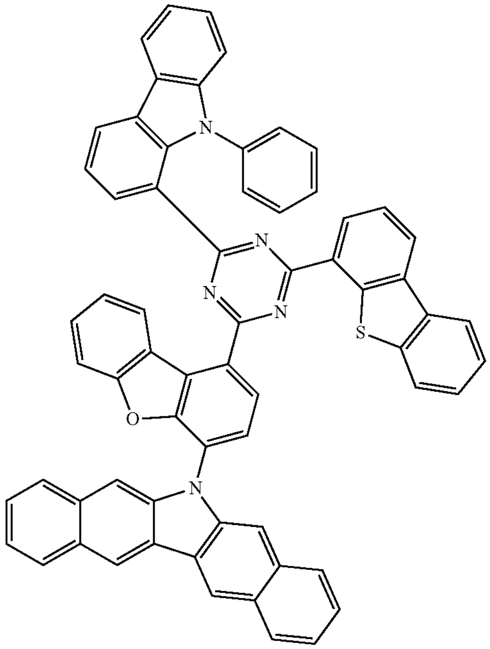

-continued
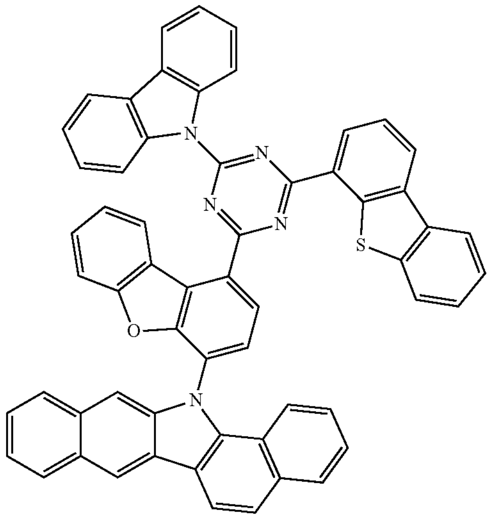
-continued
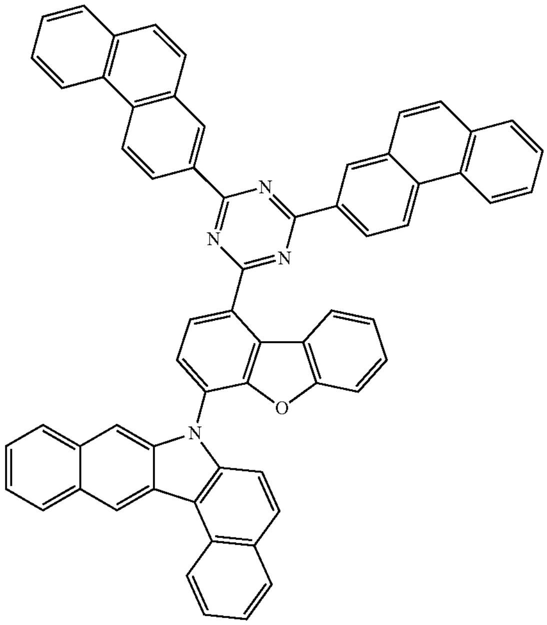
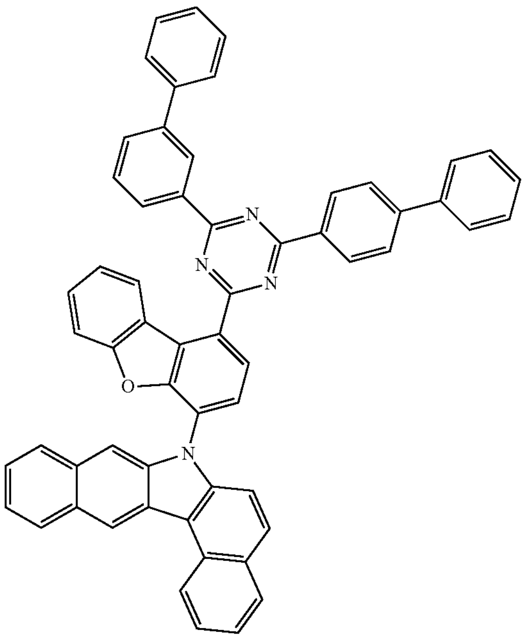
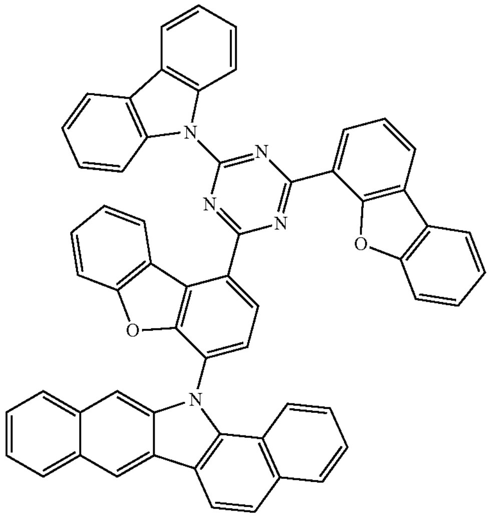

-continued
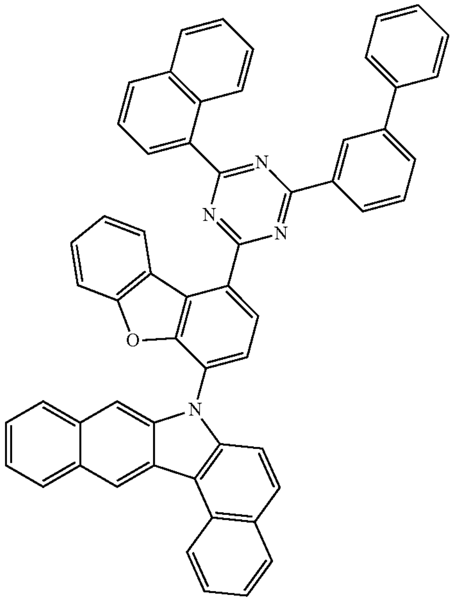
-continued
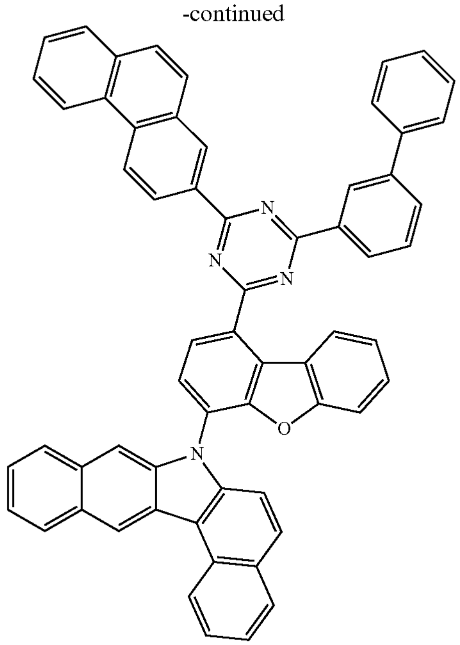
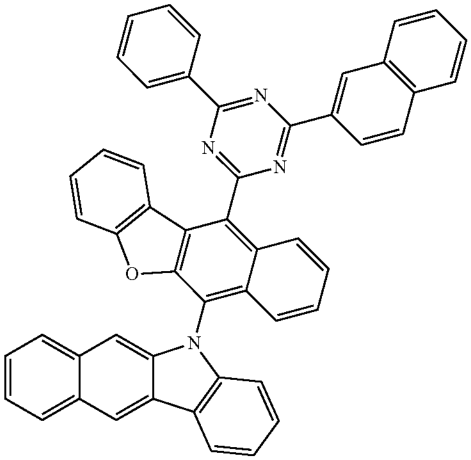
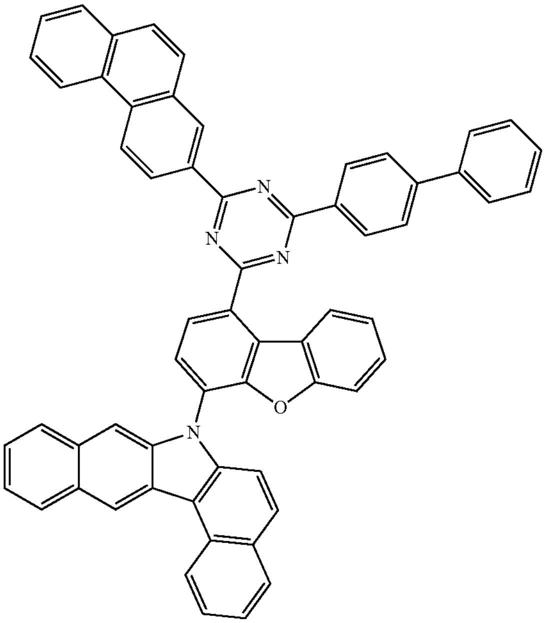
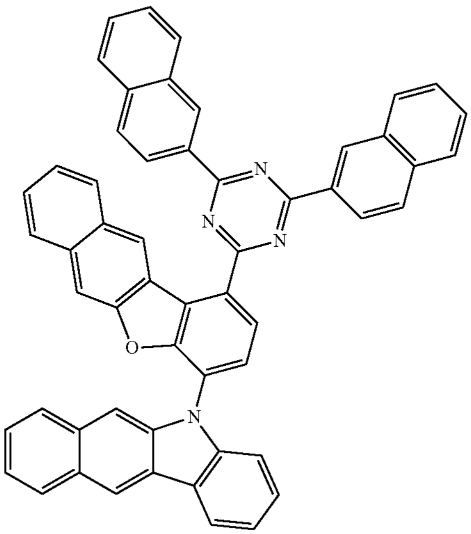

-continued
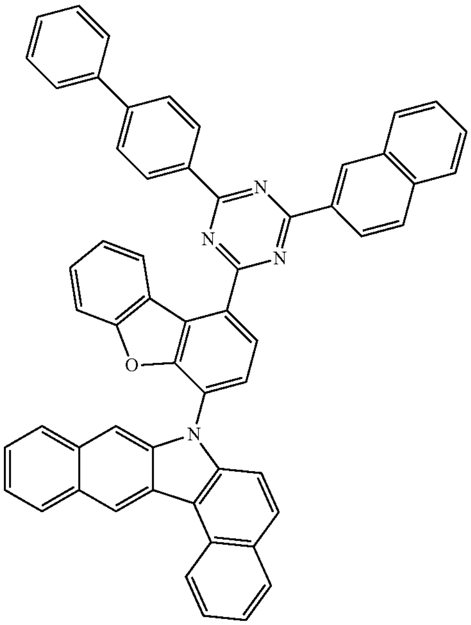
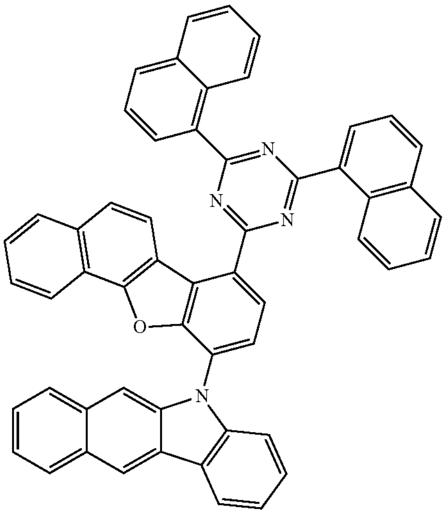
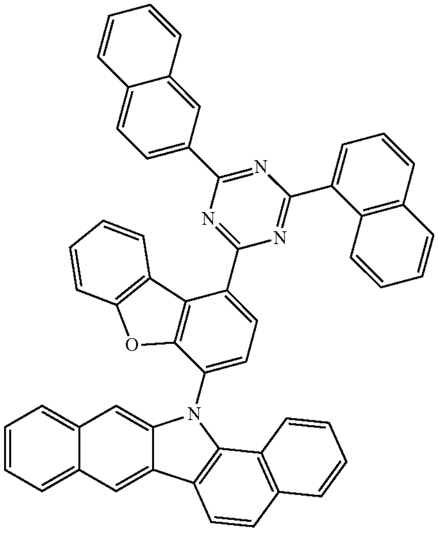
-continued
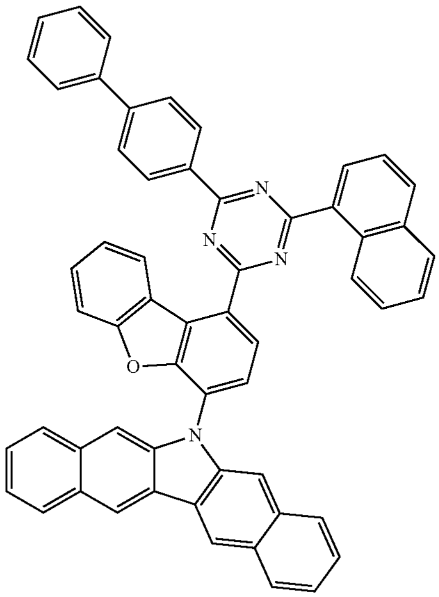
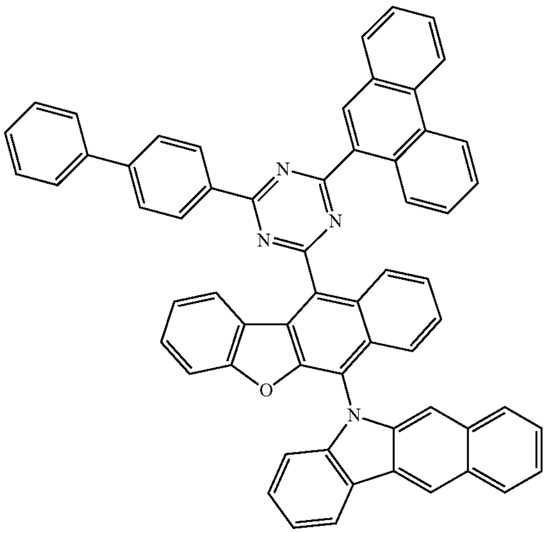
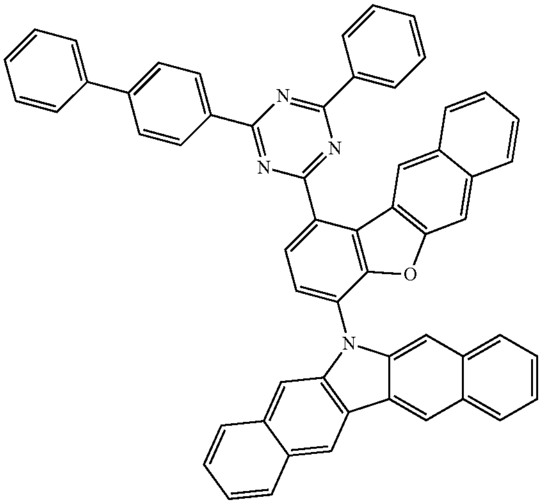

-continued
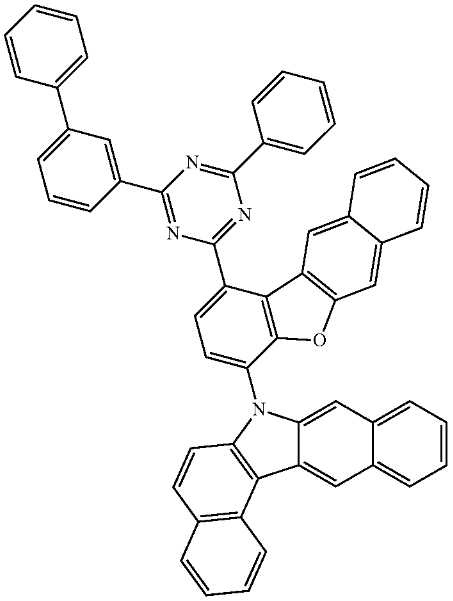
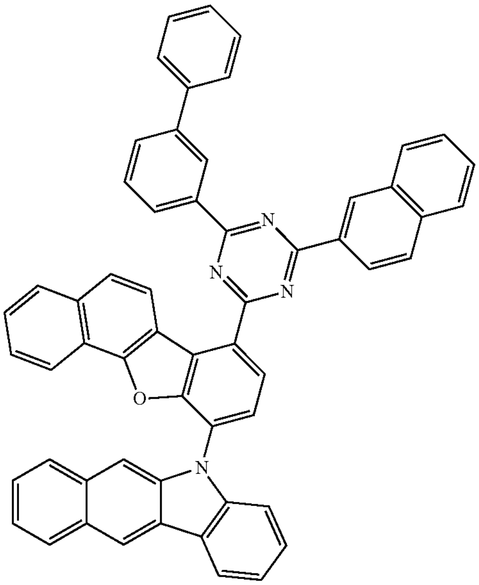
-continued
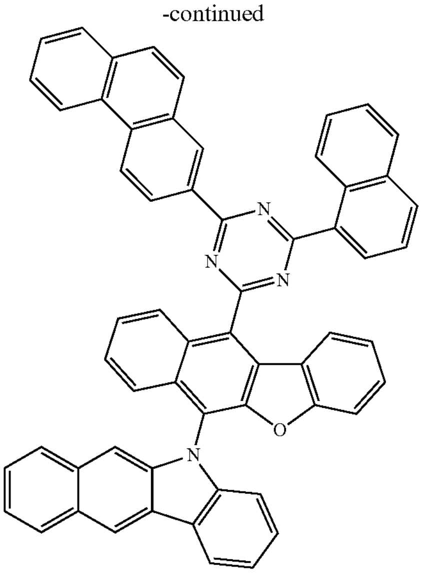
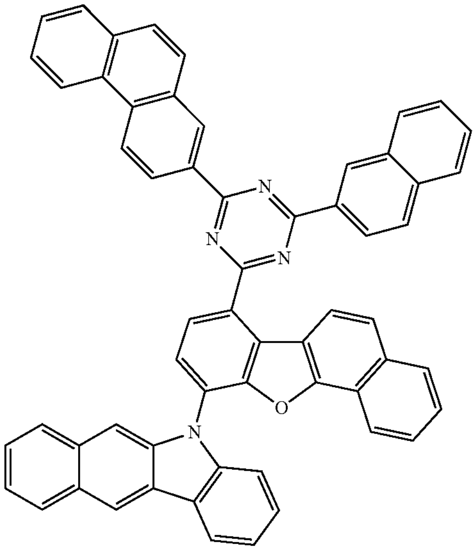
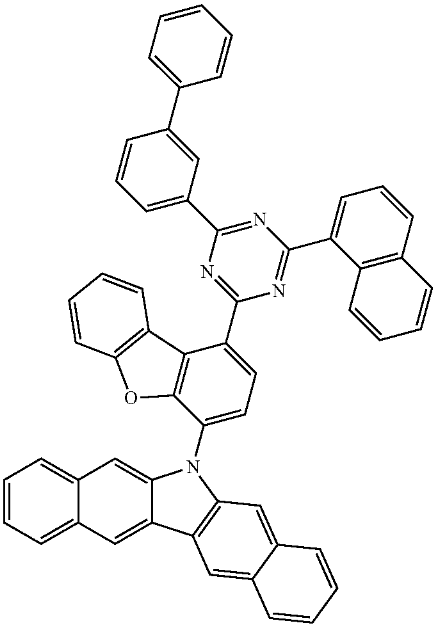

-continued
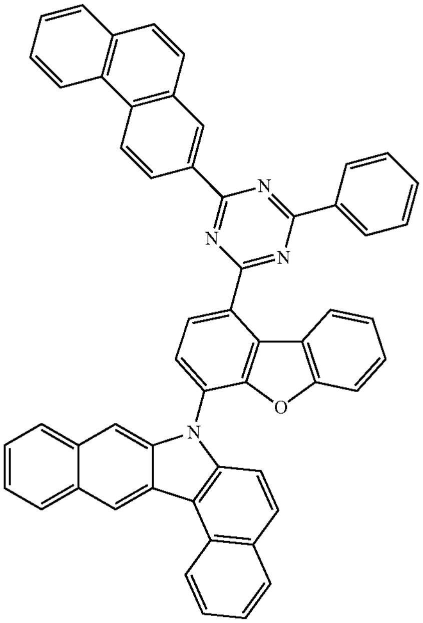
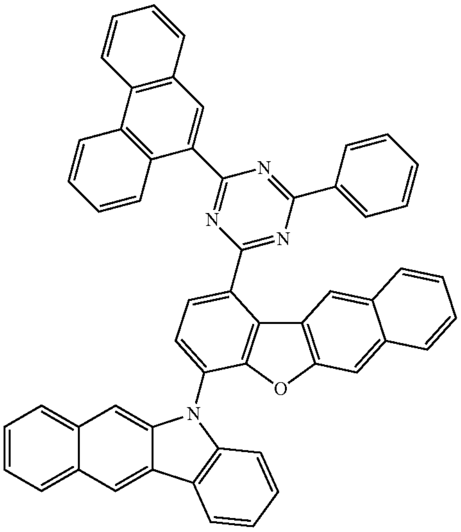
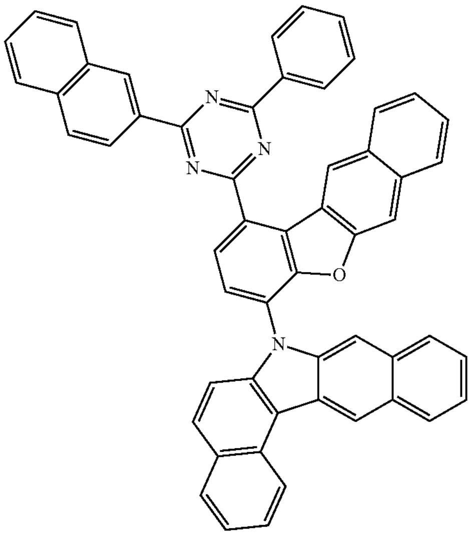
-continued
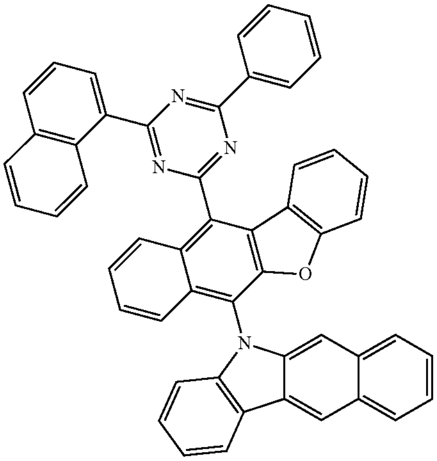
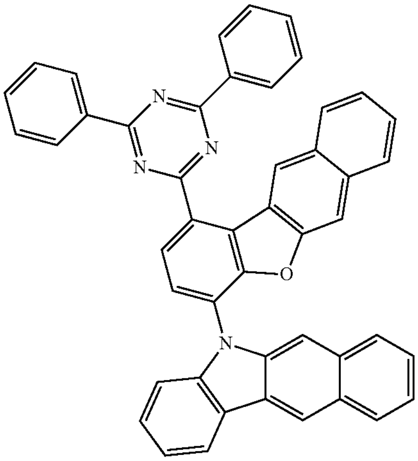
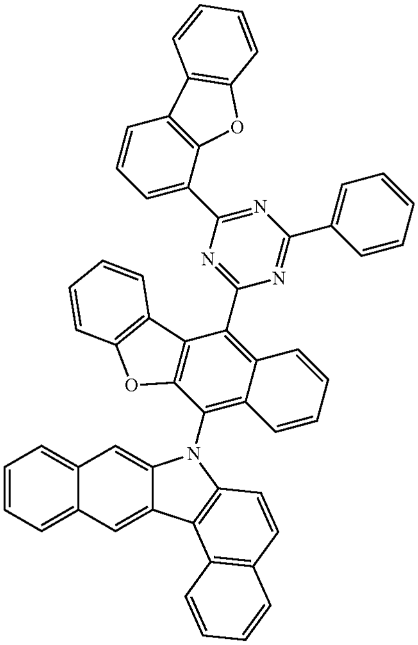

-continued
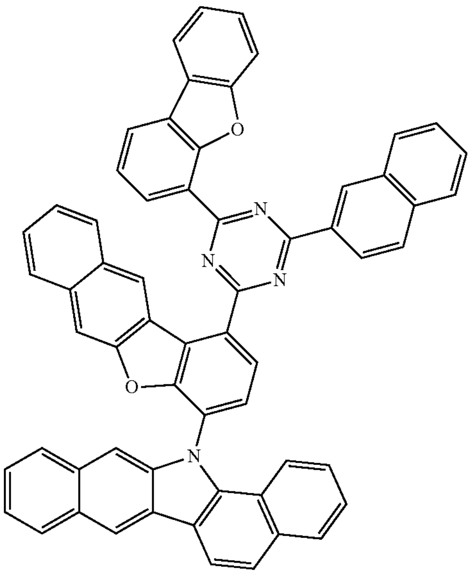
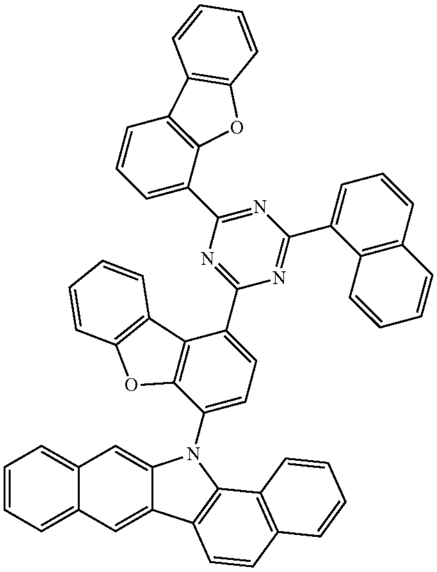
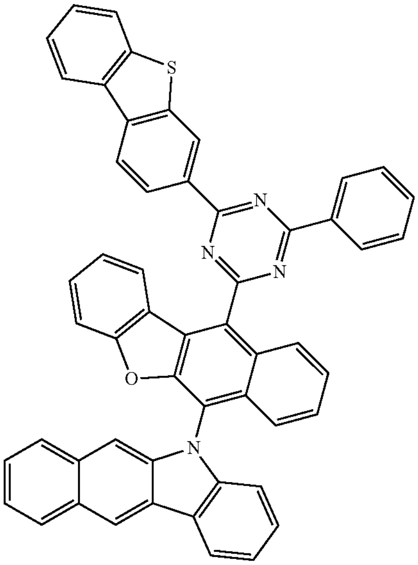
-continued
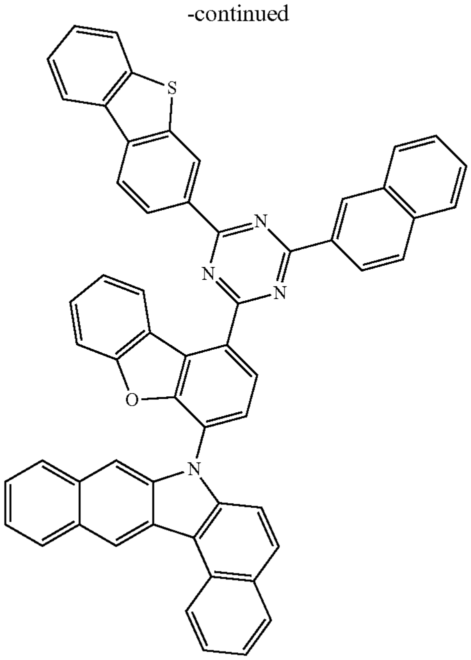
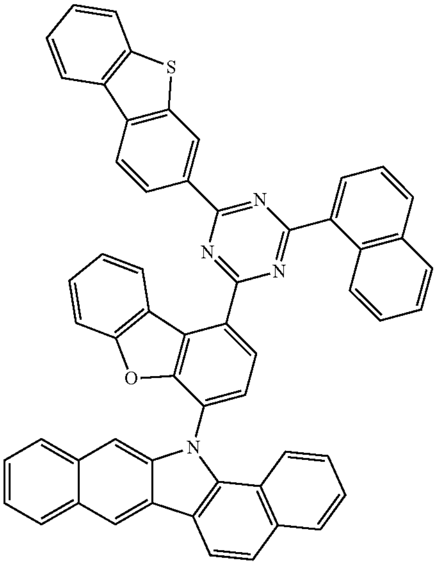

-continued
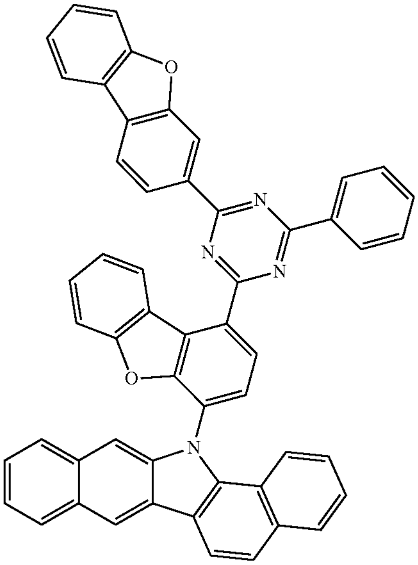
-continued
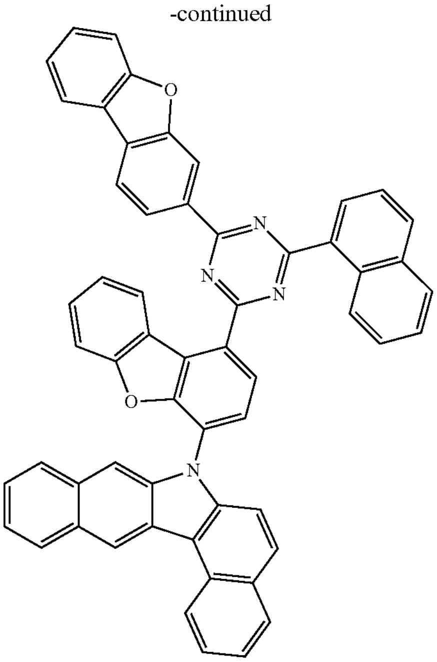
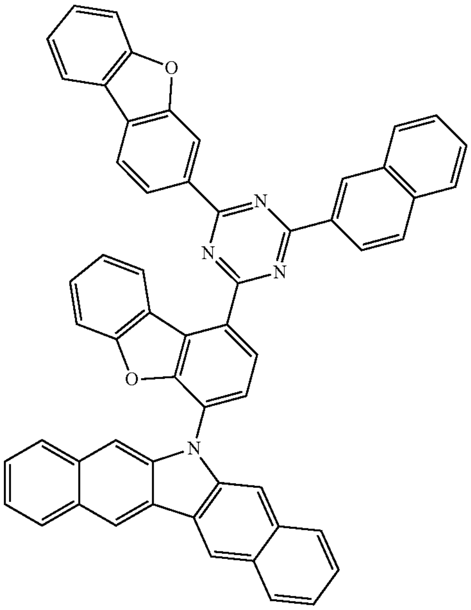
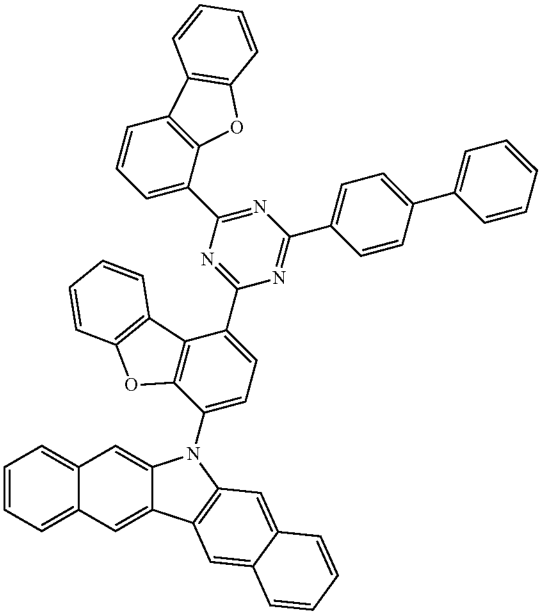

-continued
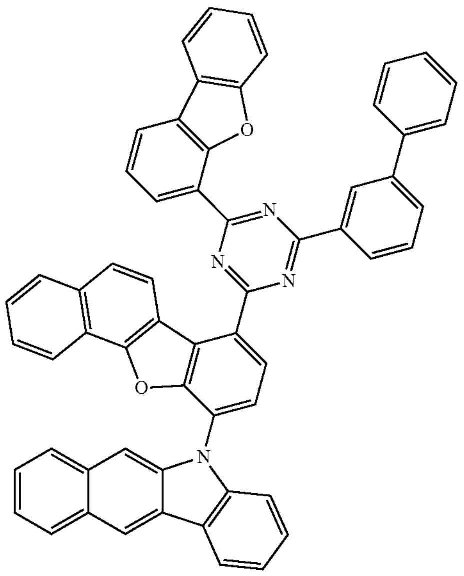
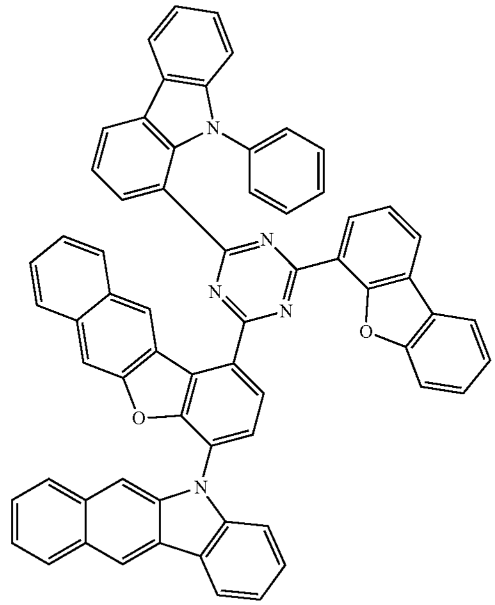
-continued
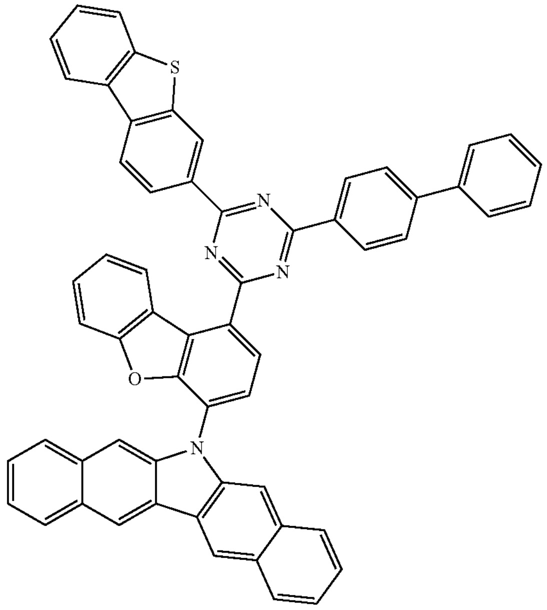
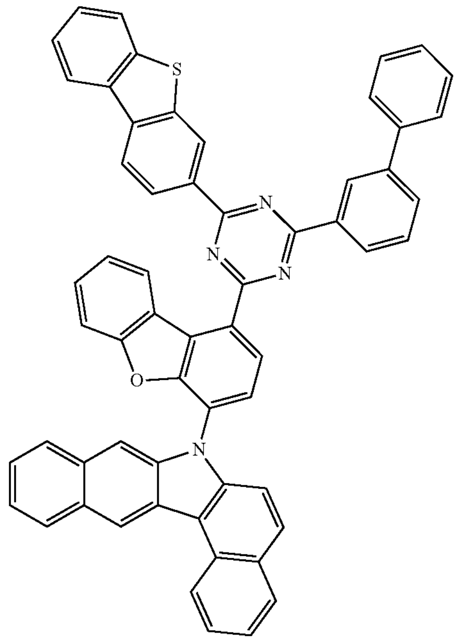

-continued
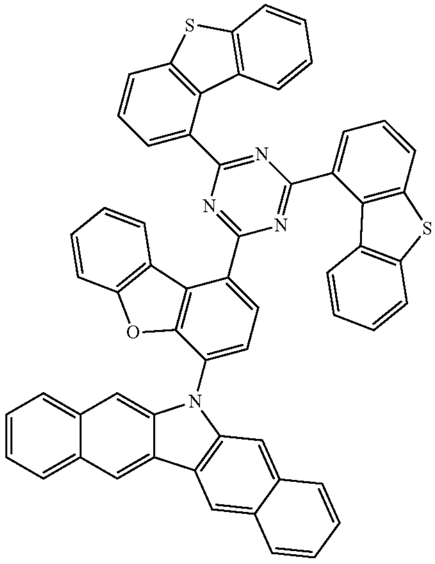
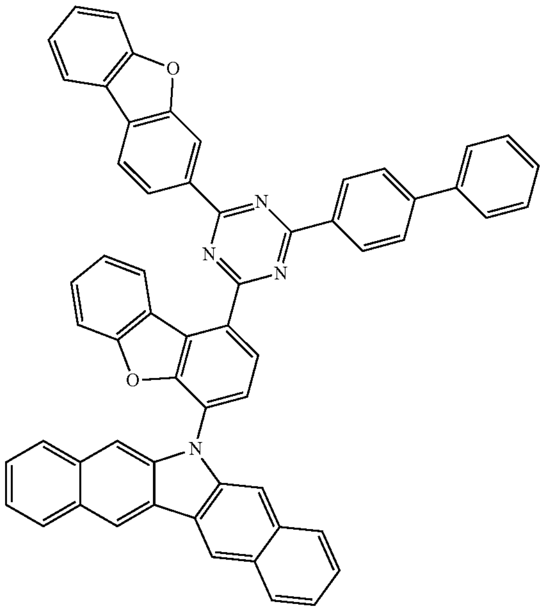
-continued
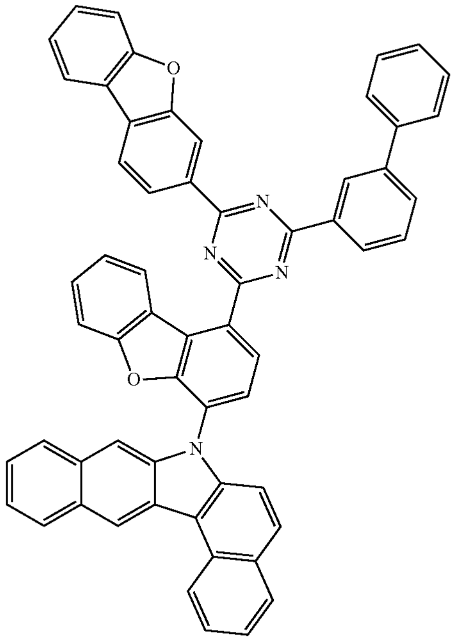
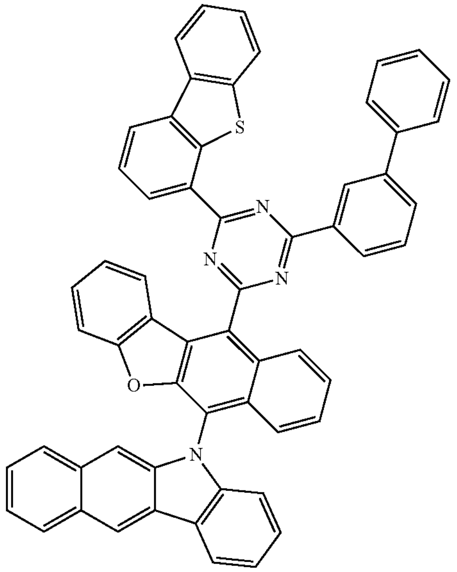
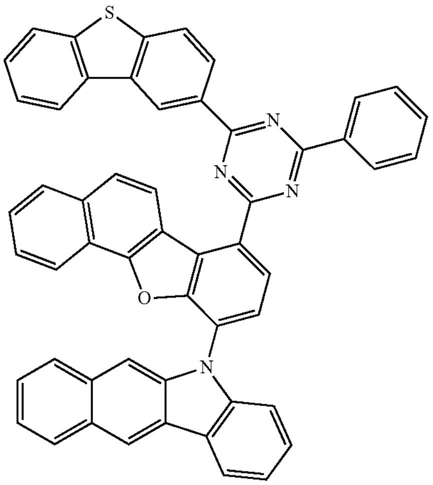

-continued
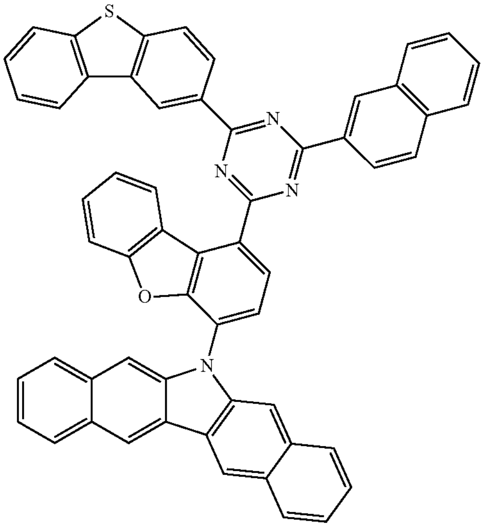
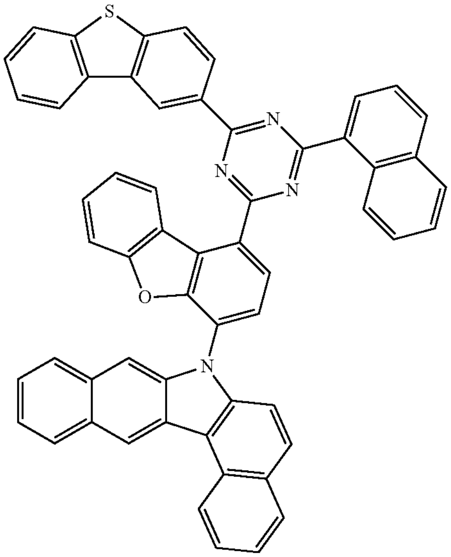
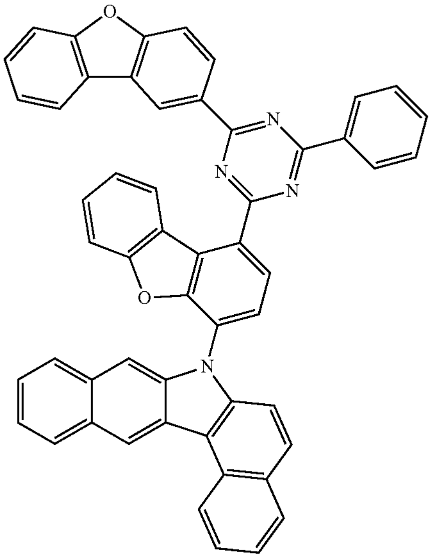
-continued
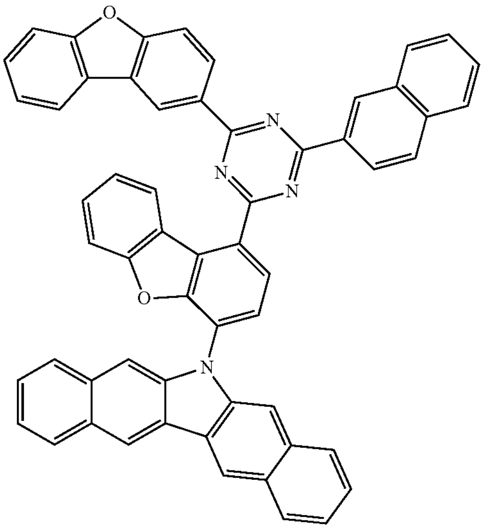
lp;1p
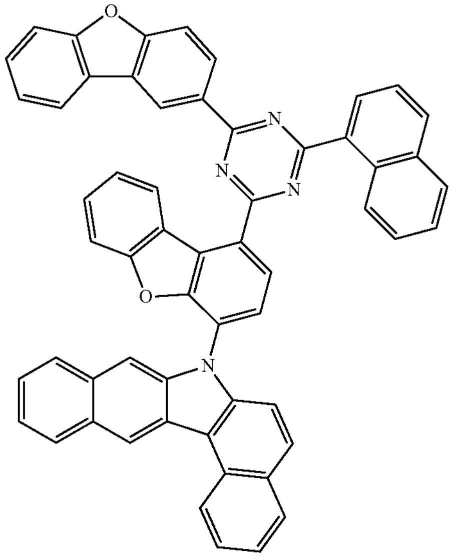
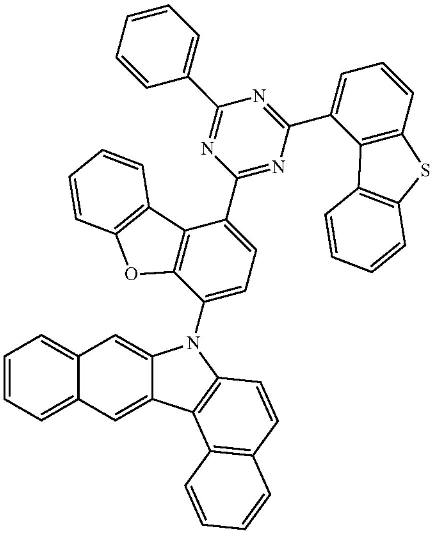

-continued
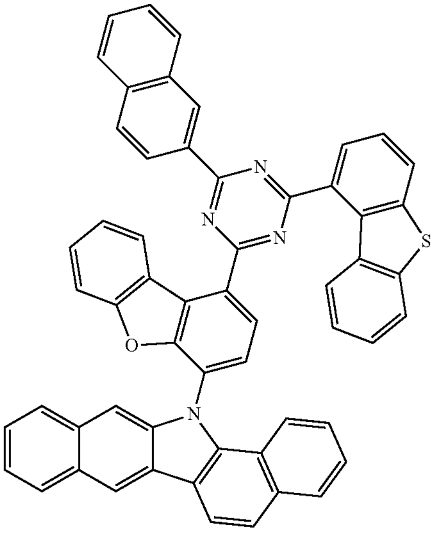
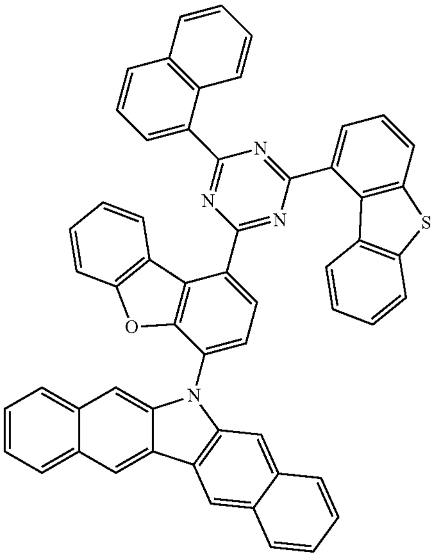
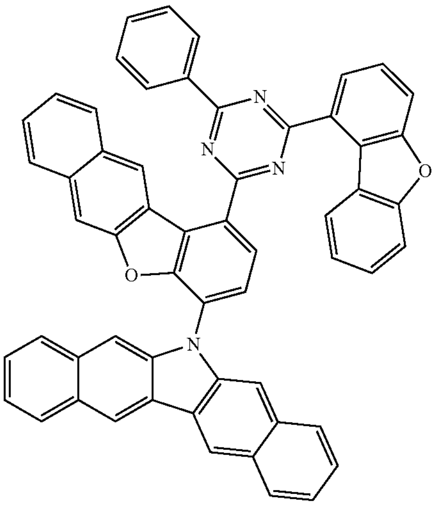
-continued
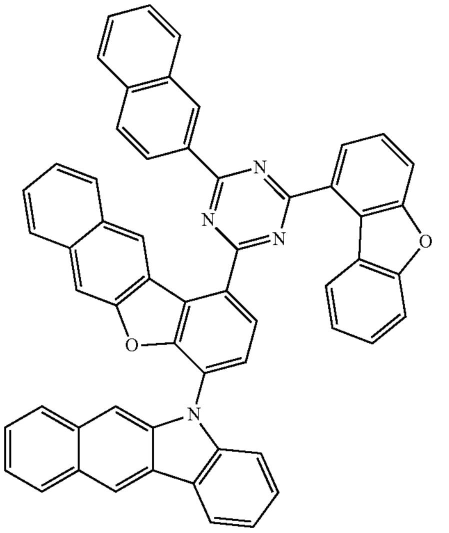
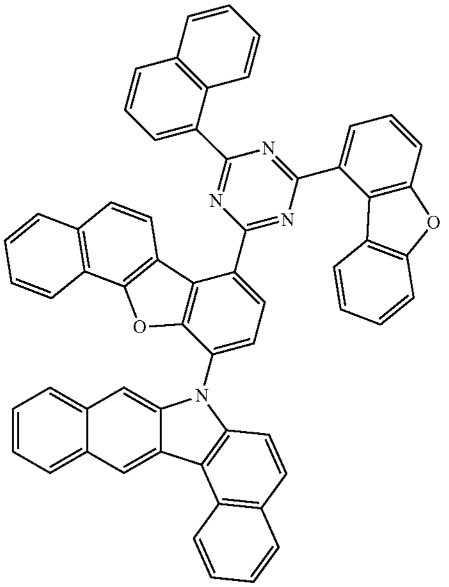
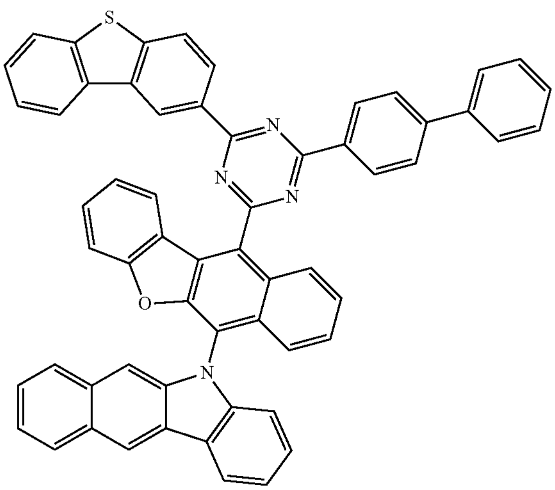

-continued
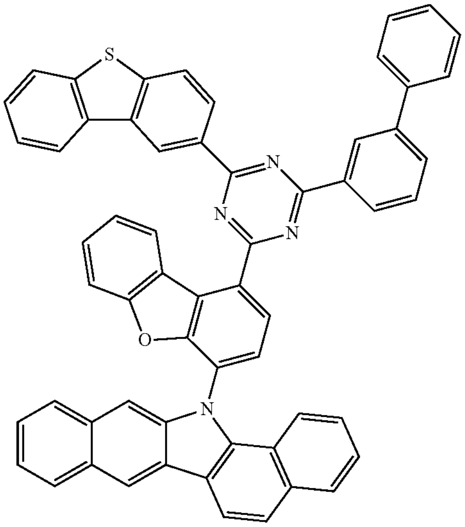
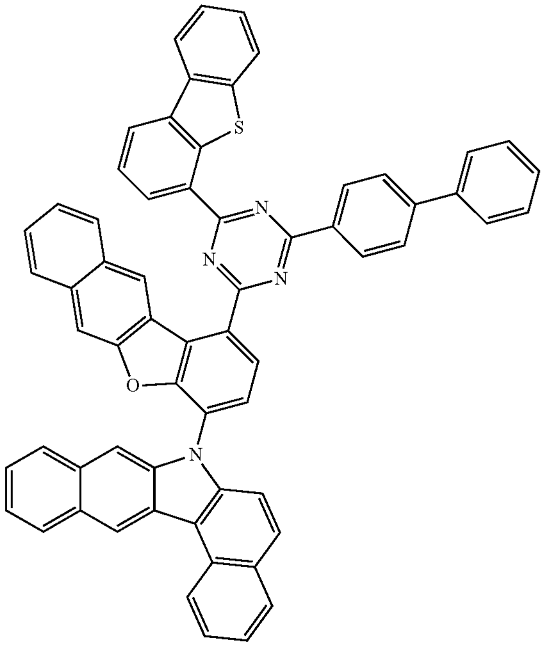
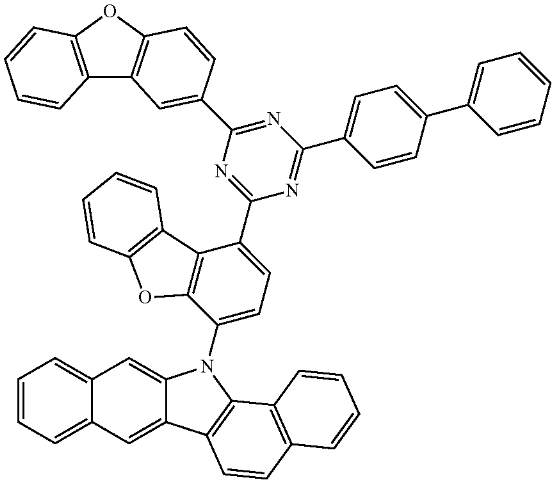
-continued
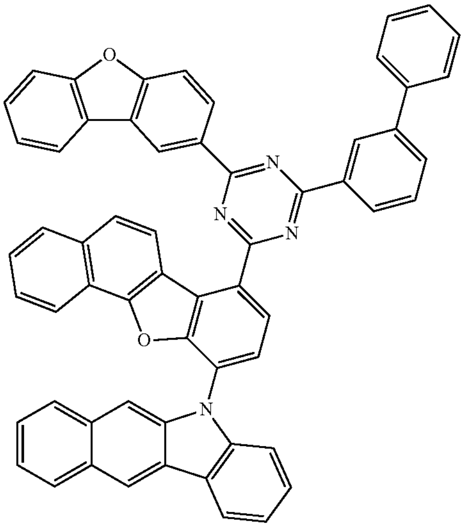
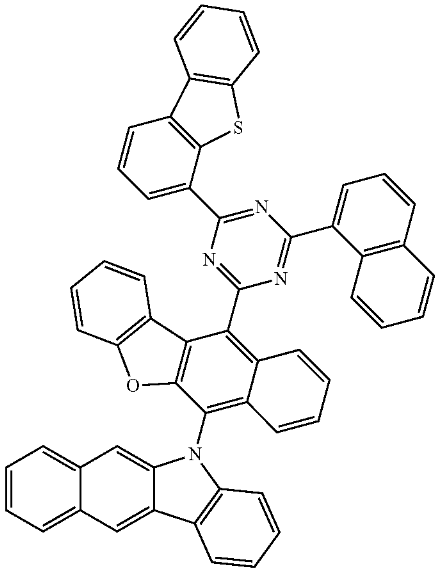
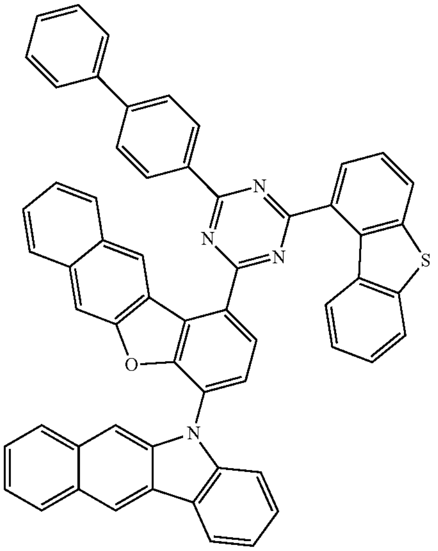

-continued
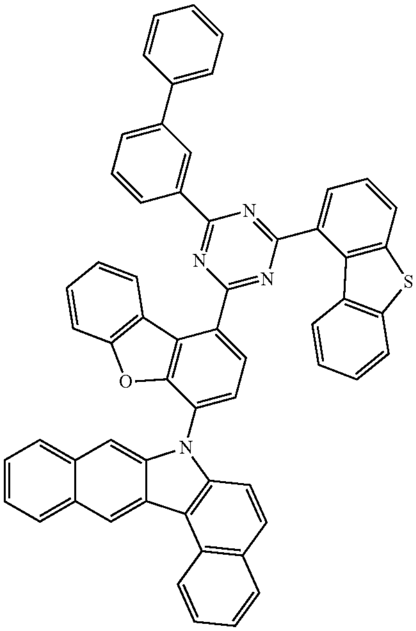
-continued
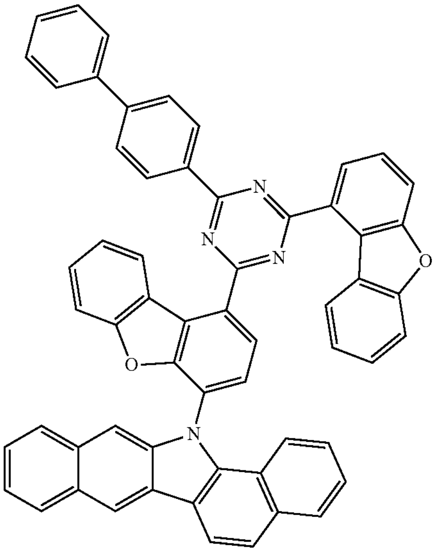
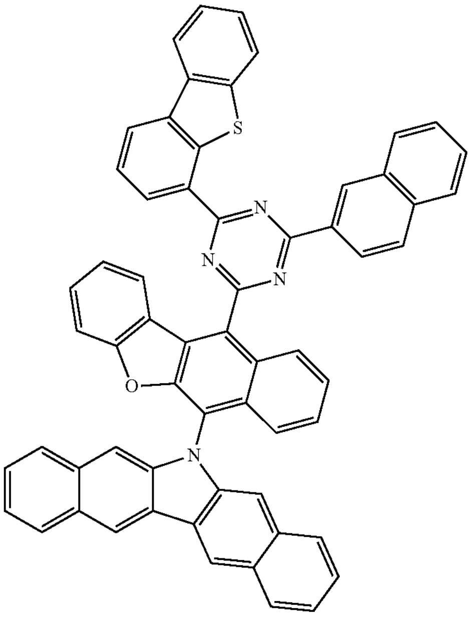
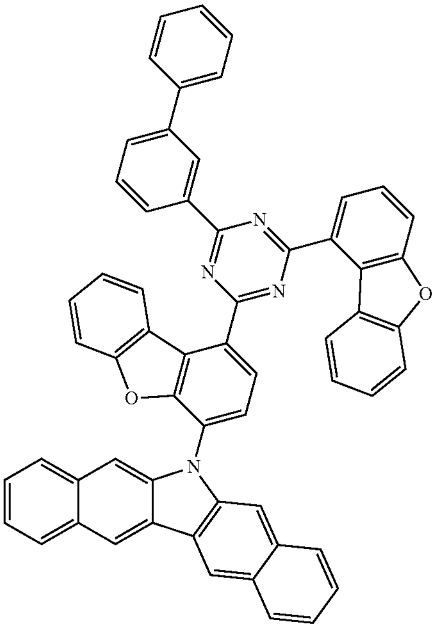

-continued
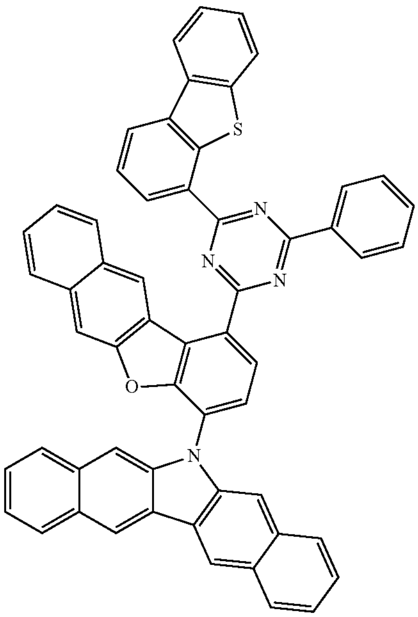
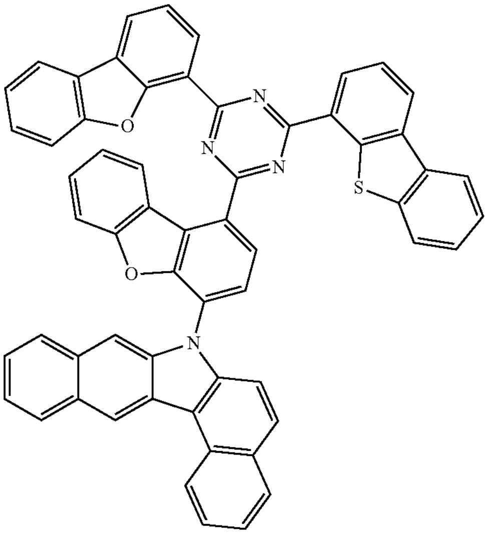
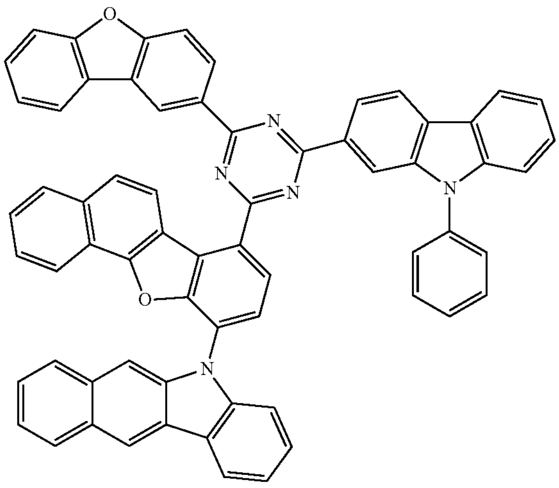
-continued
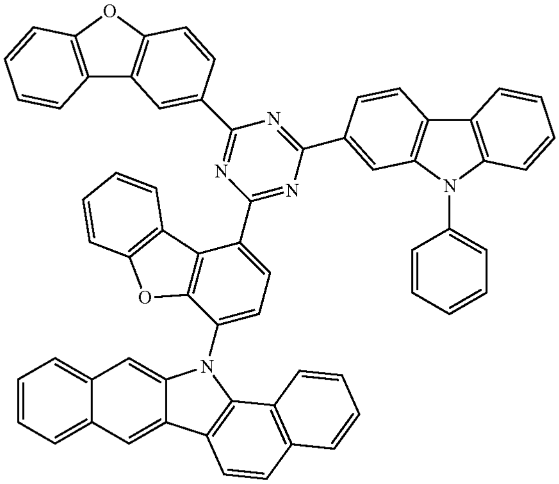
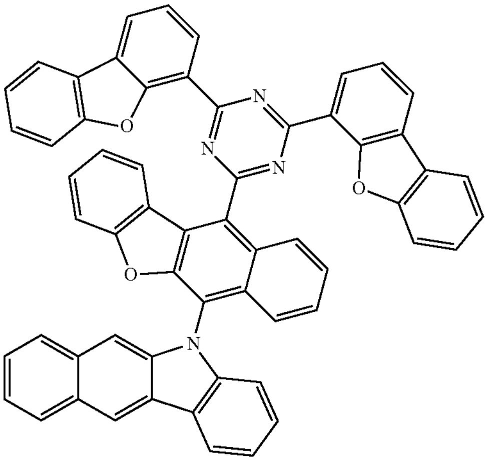
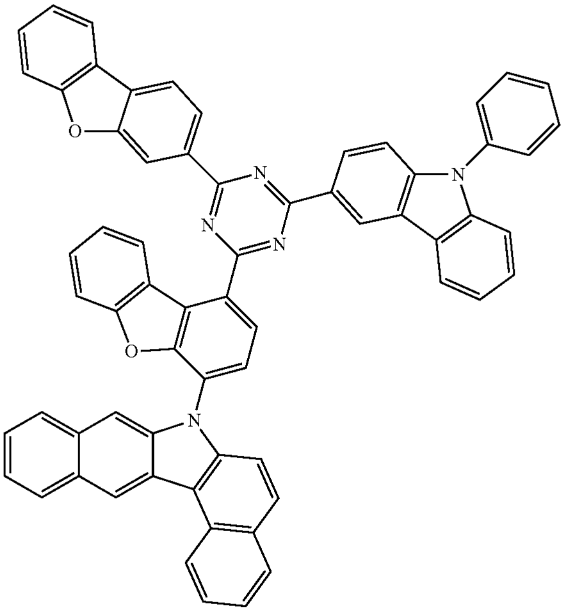

-continued
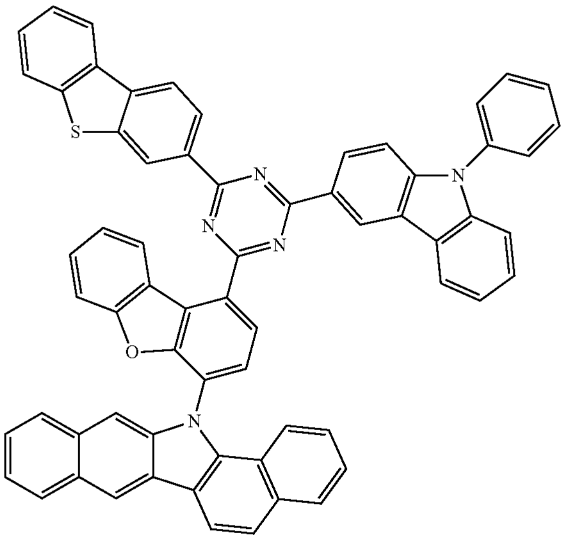
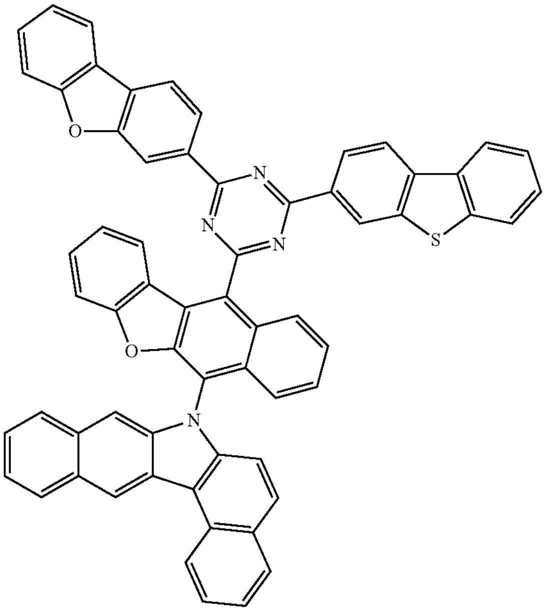
-continued
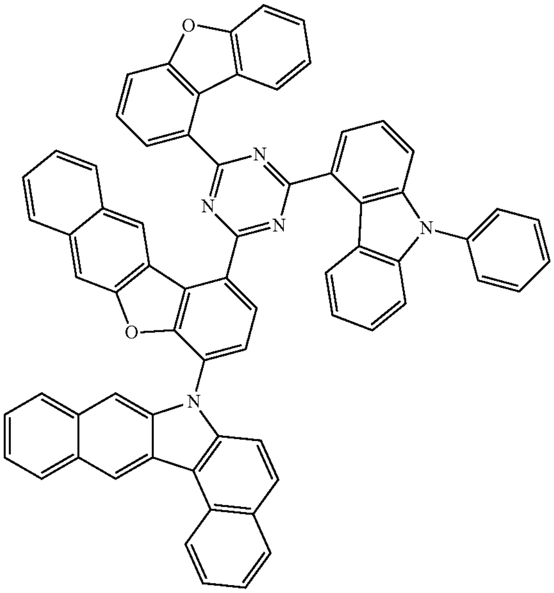
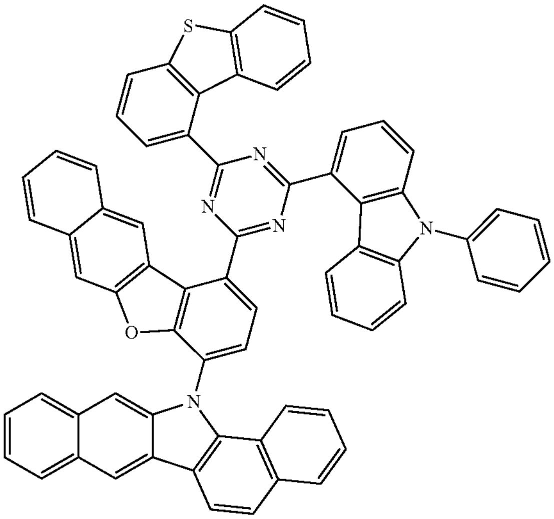
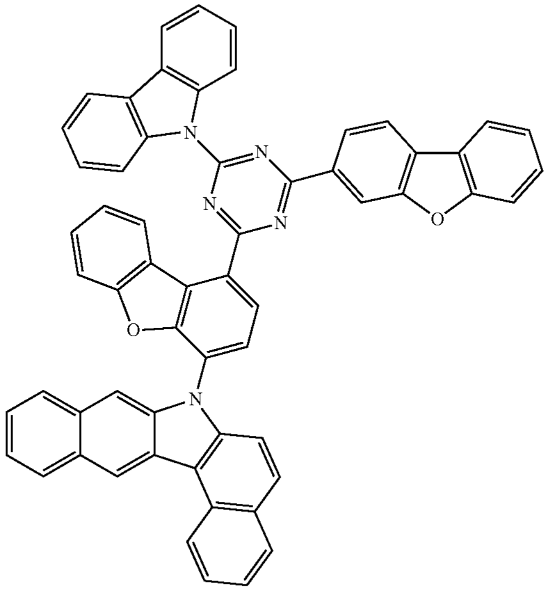

-continued
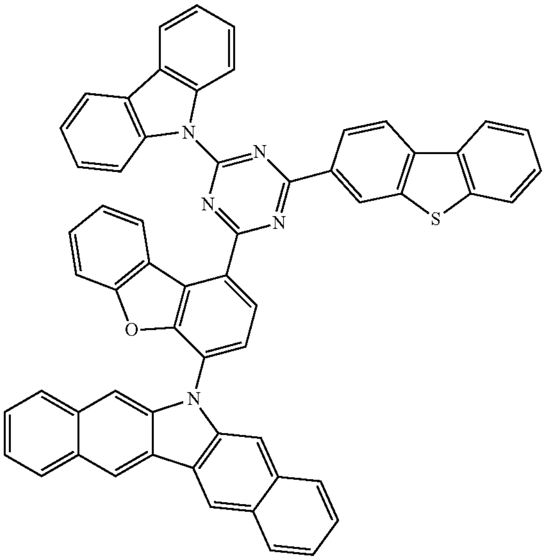
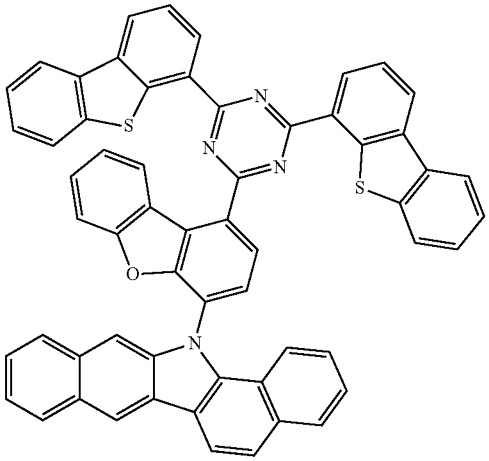
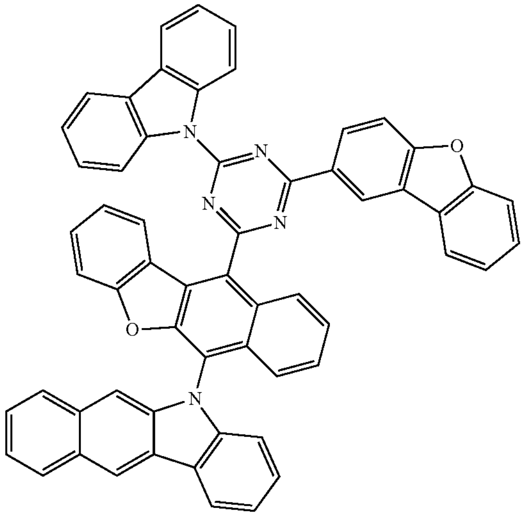
-continued
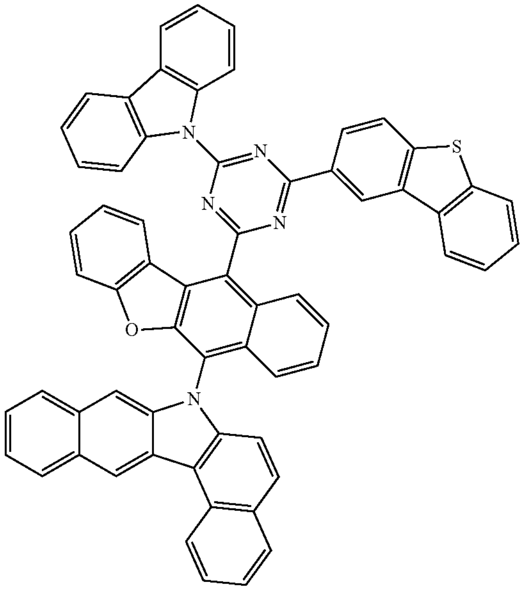
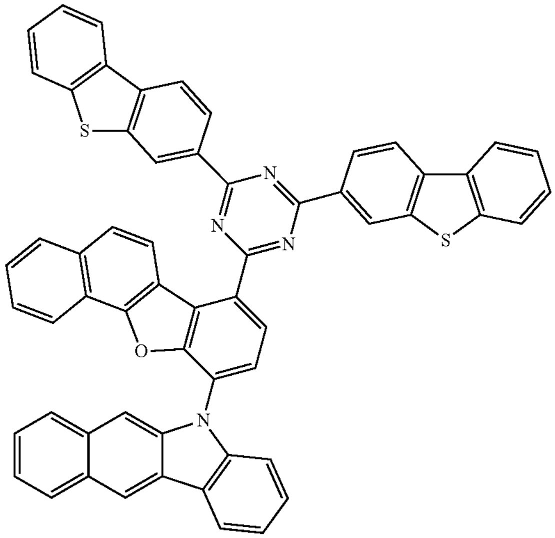
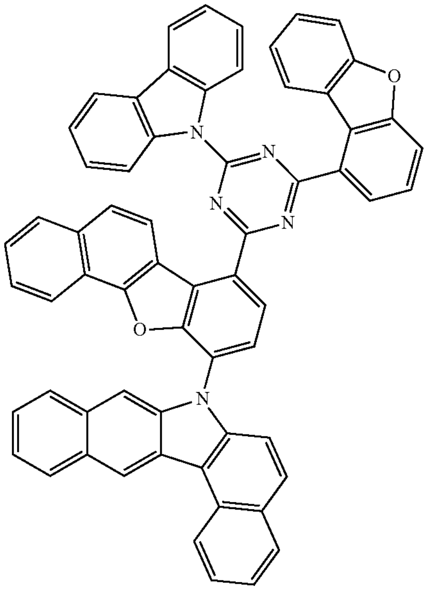

-continued
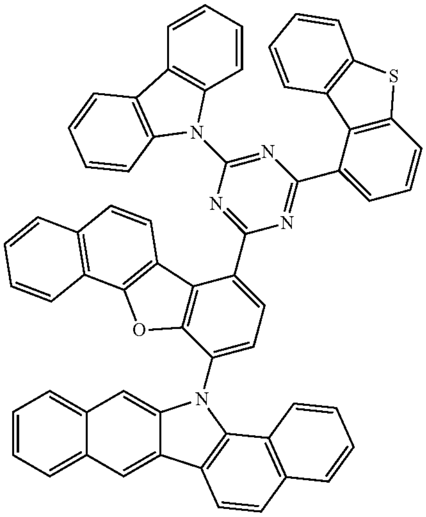
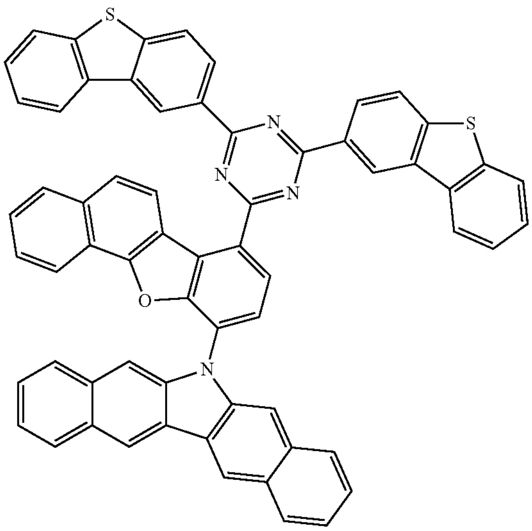
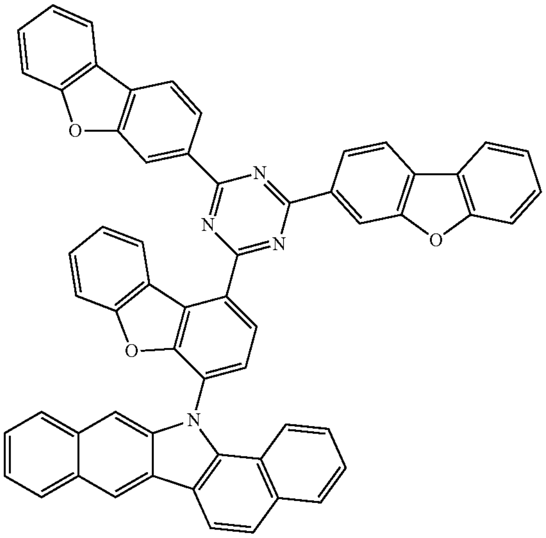
-continued
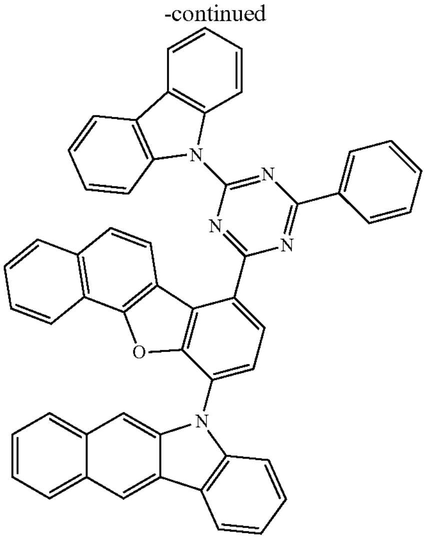
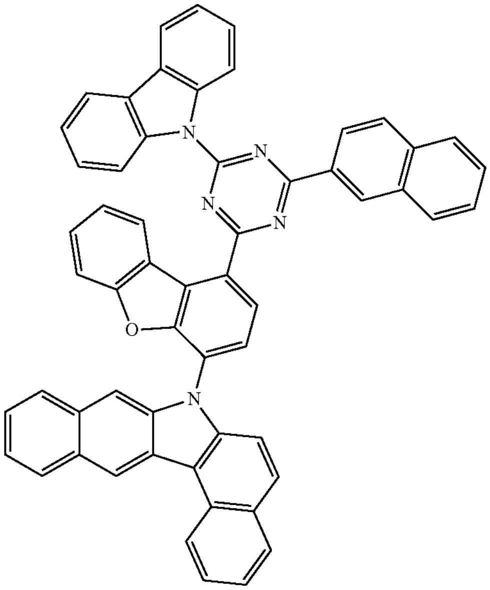
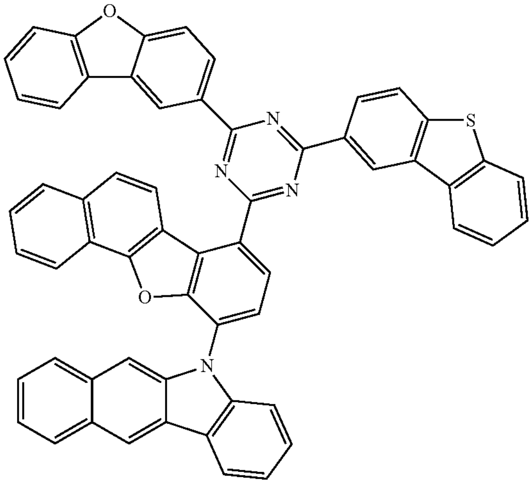

-continued
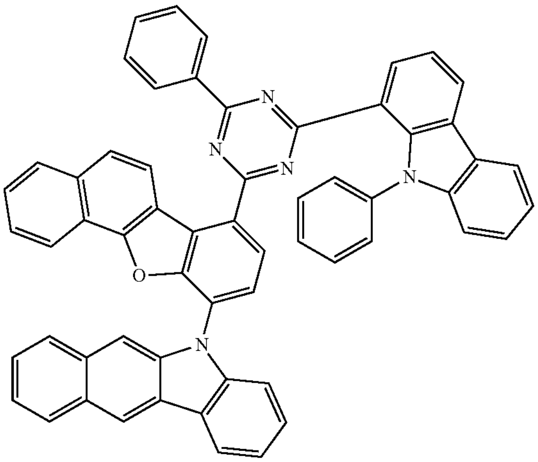
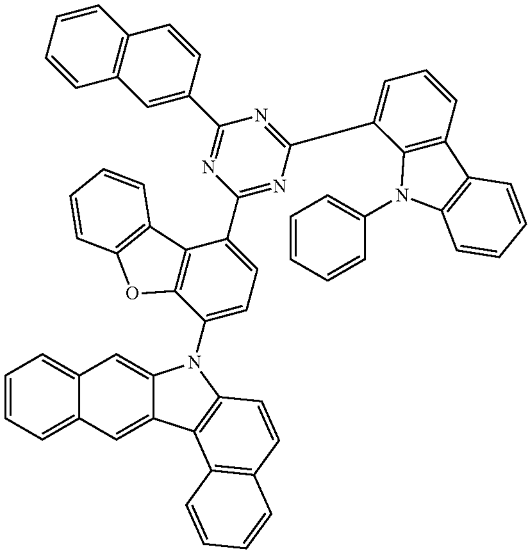
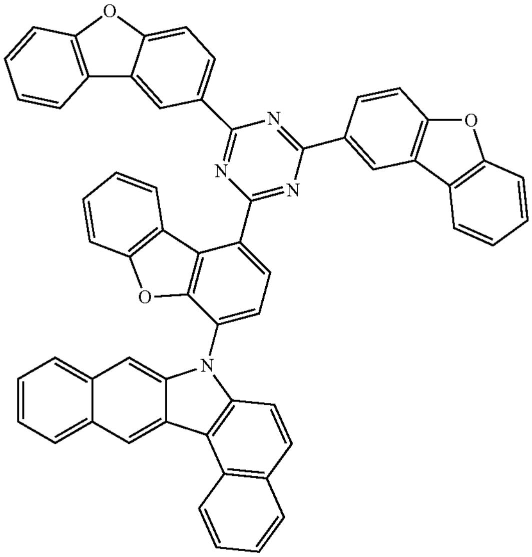
-continued
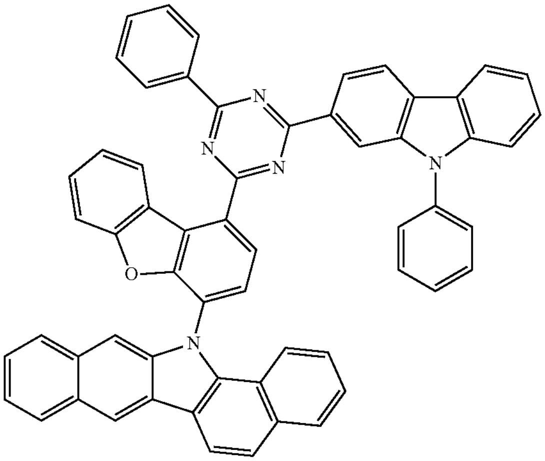
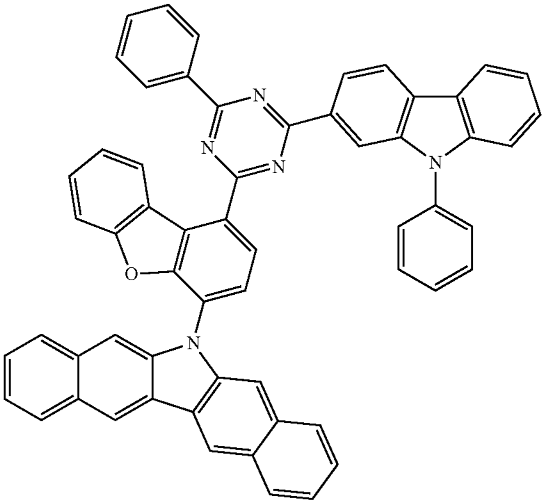
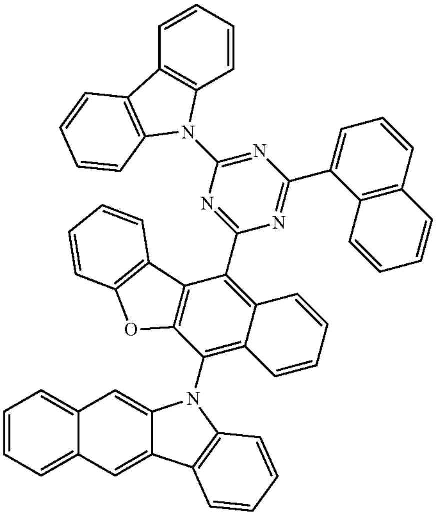

-continued
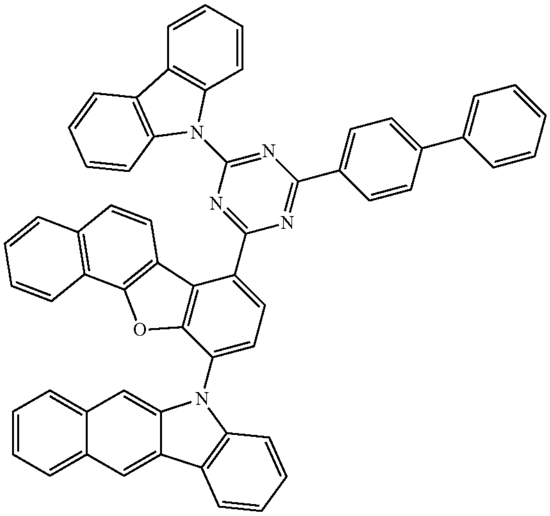
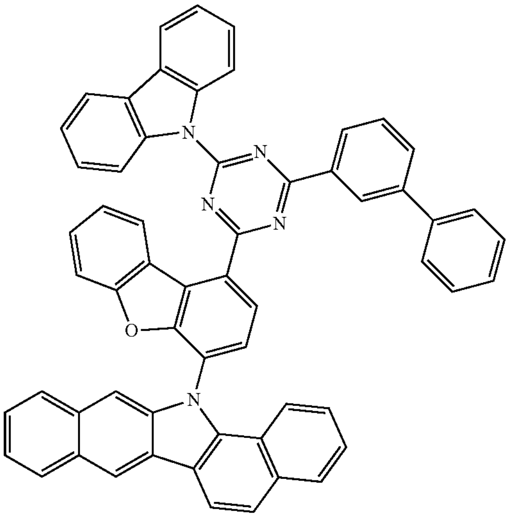
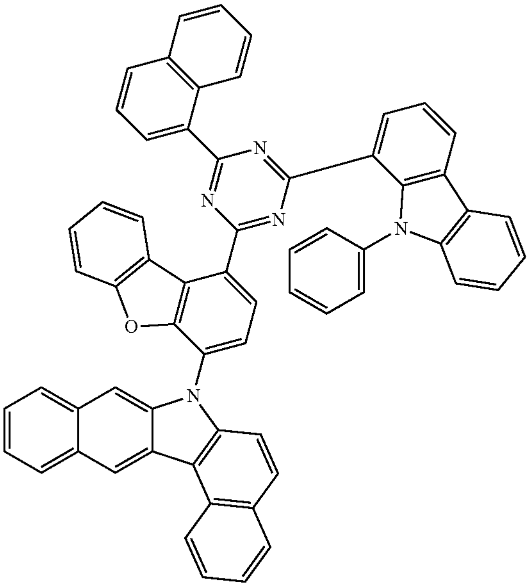
-continued
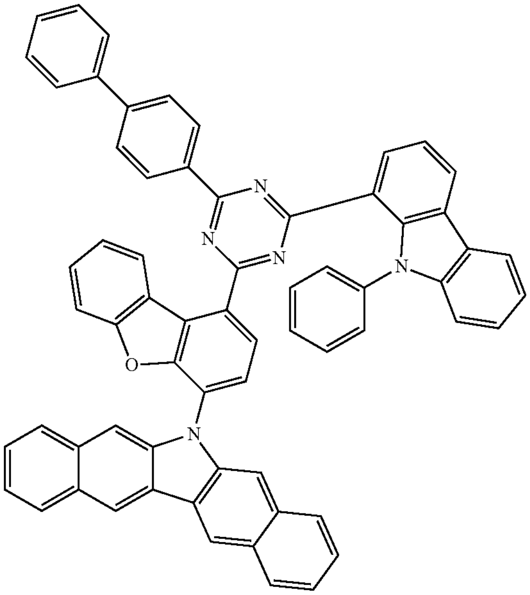
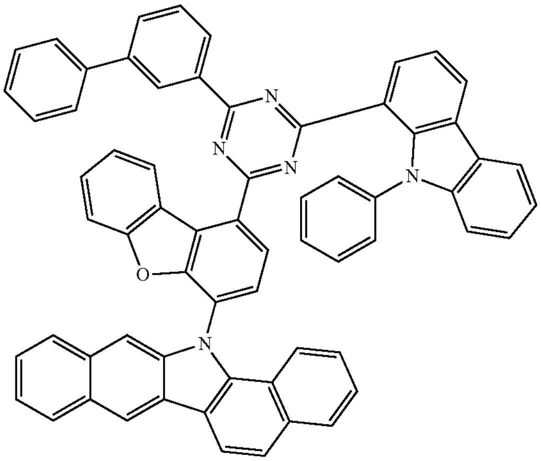
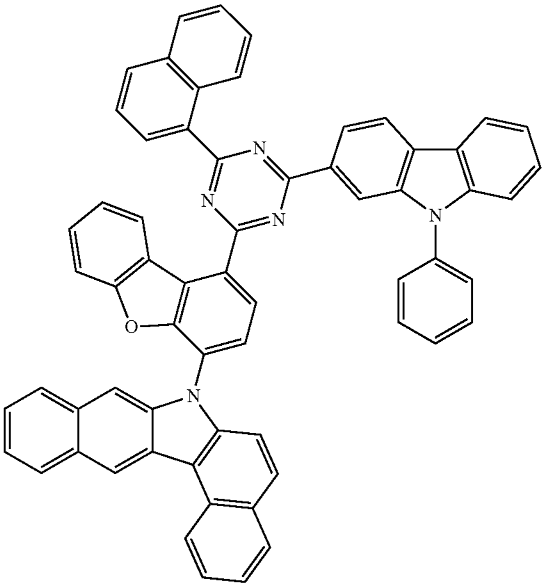

-continued
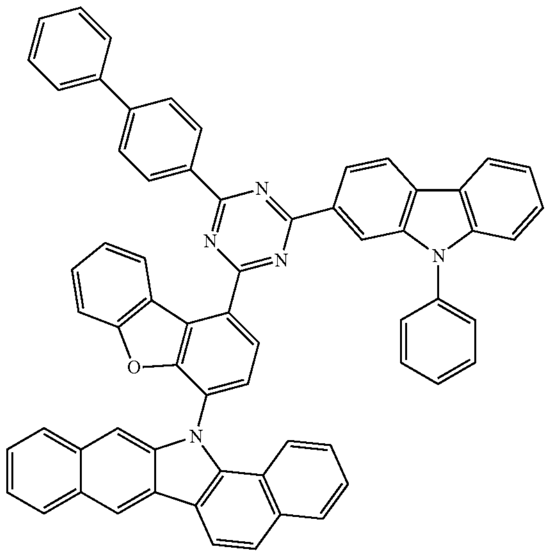
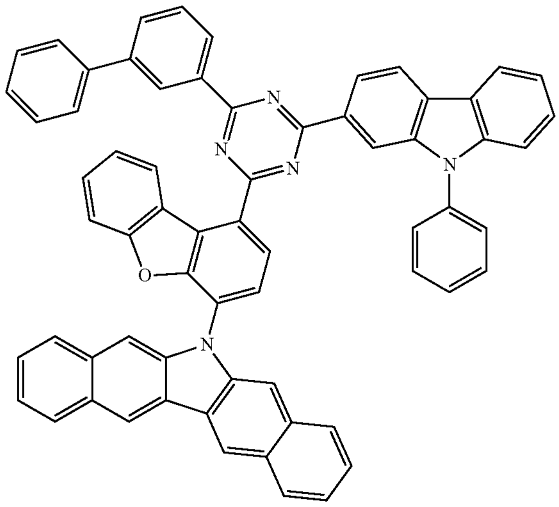
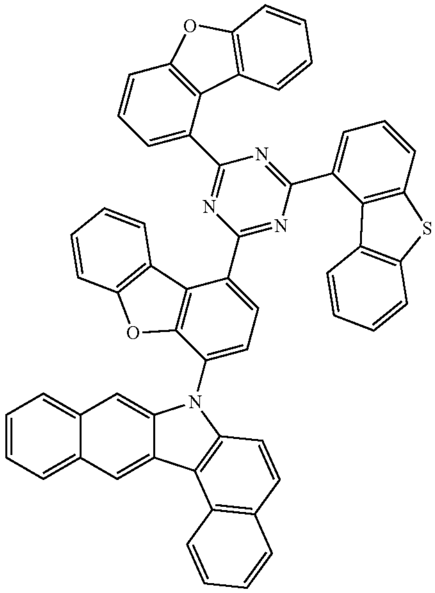
-continued
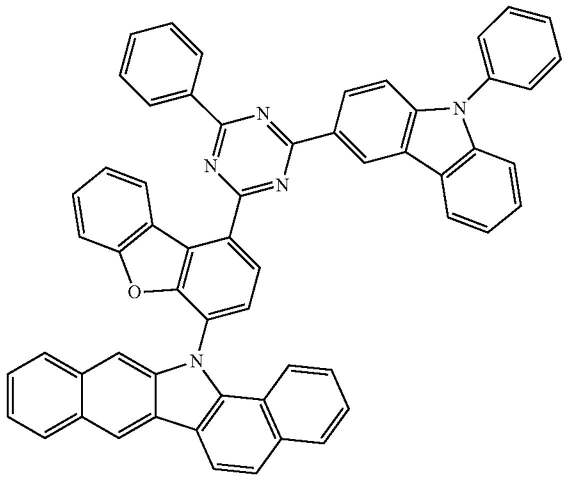
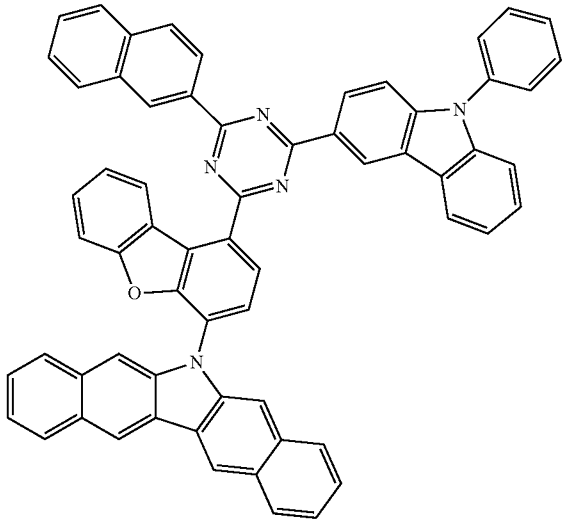
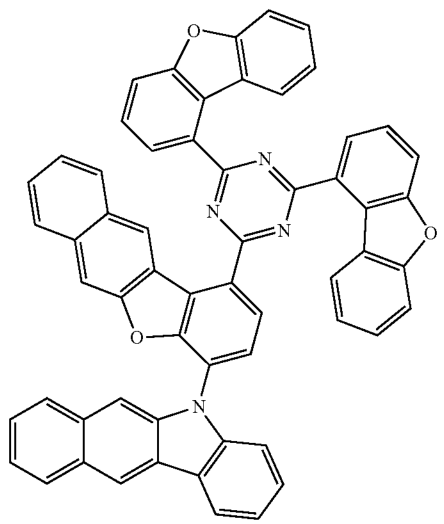

-continued
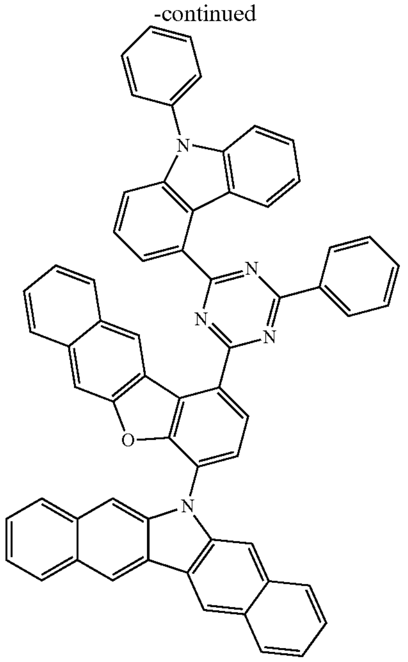
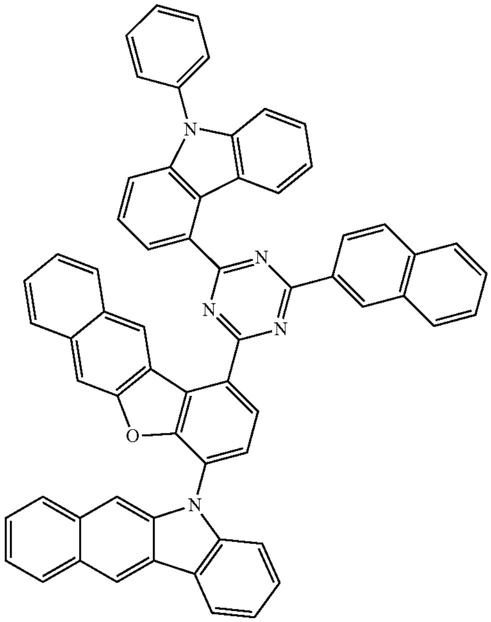
-continued
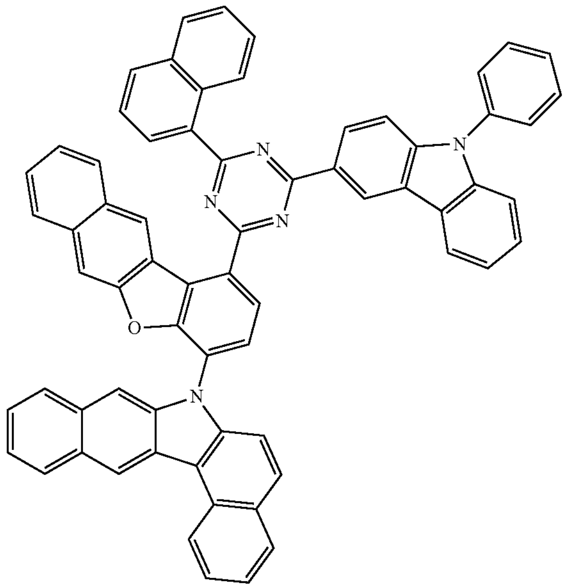
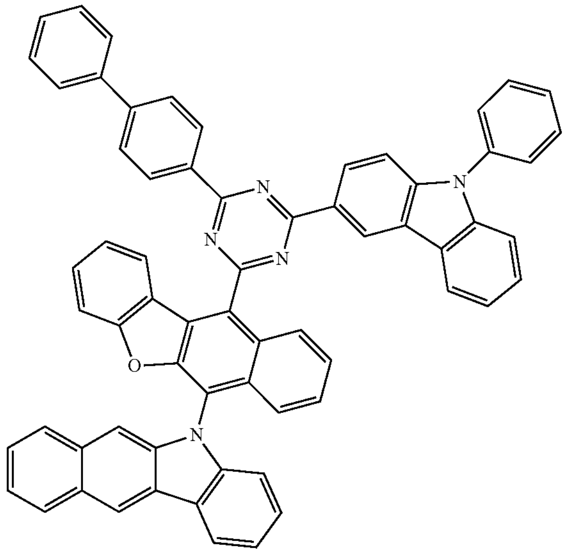
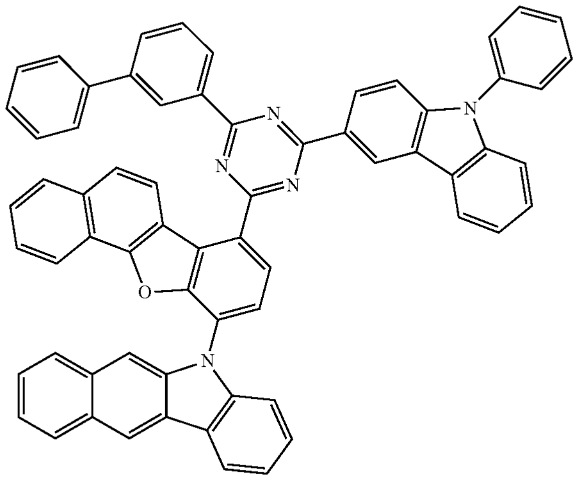

-continued
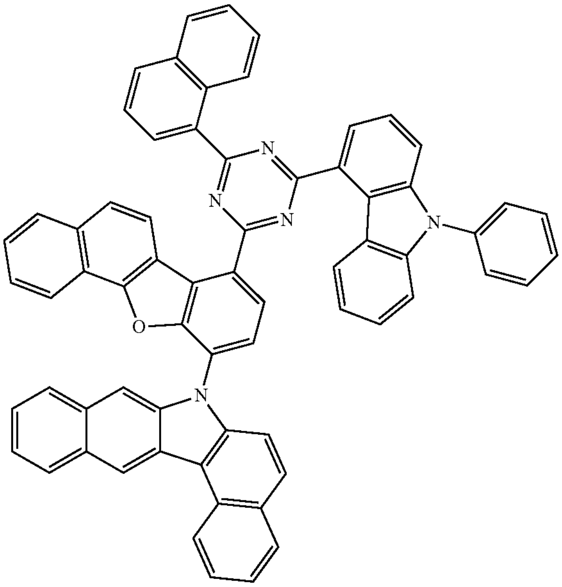
-continued
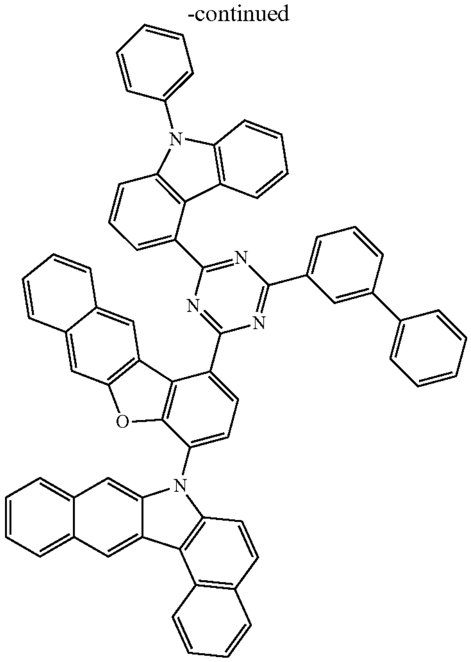
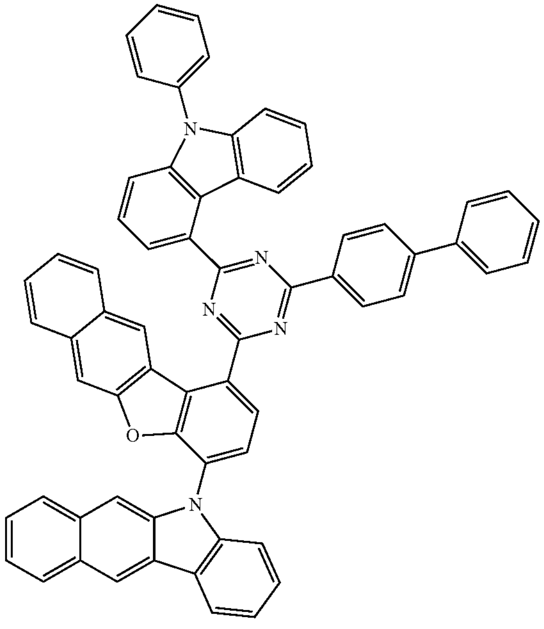
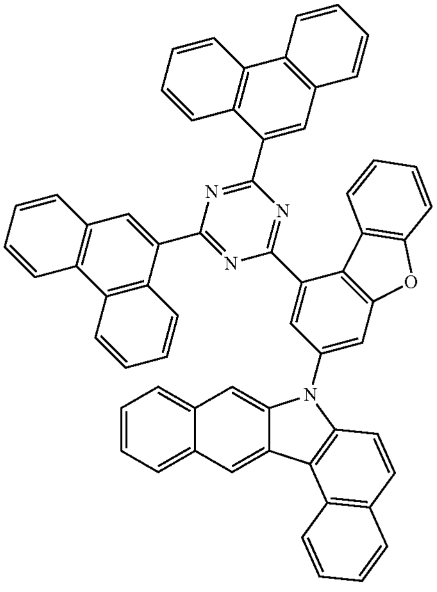

-continued
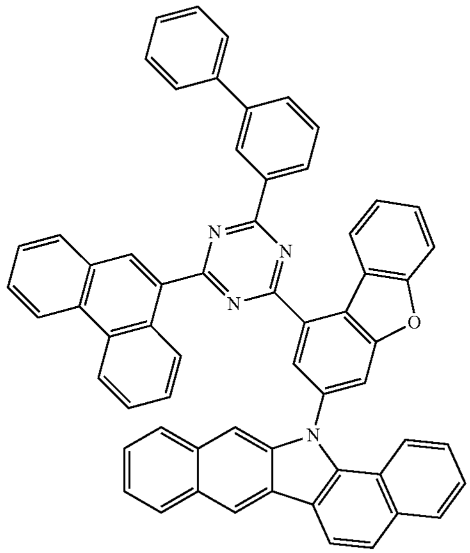
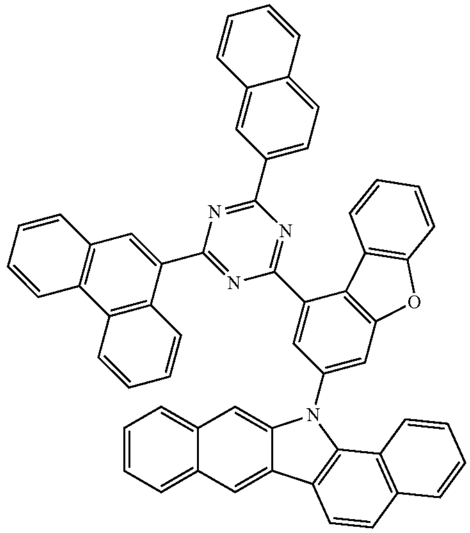
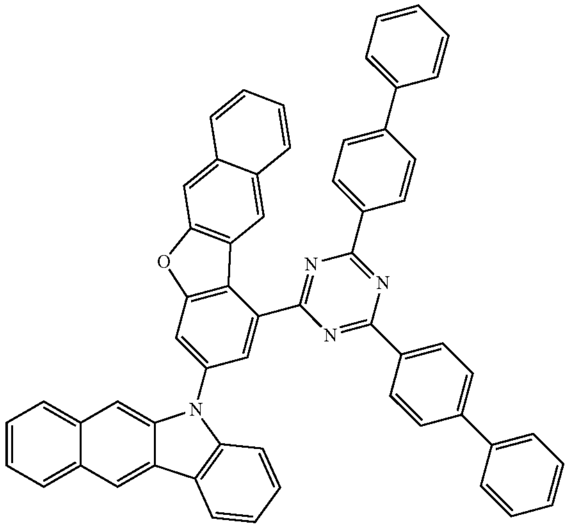
-continued
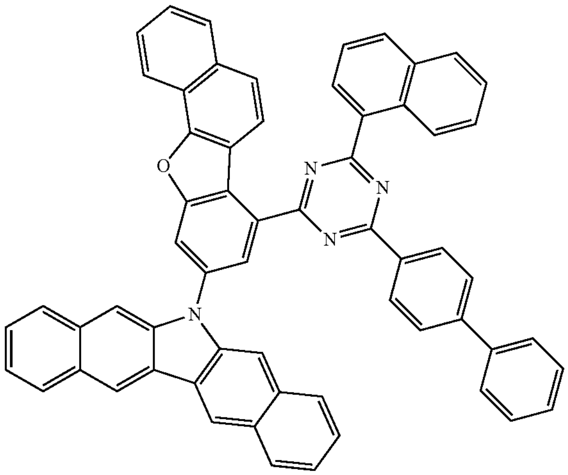
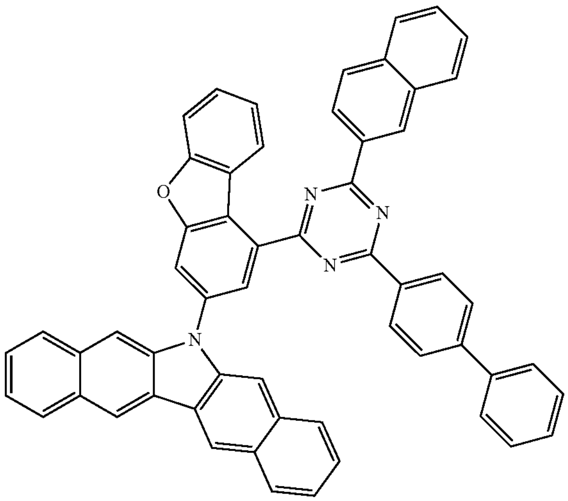
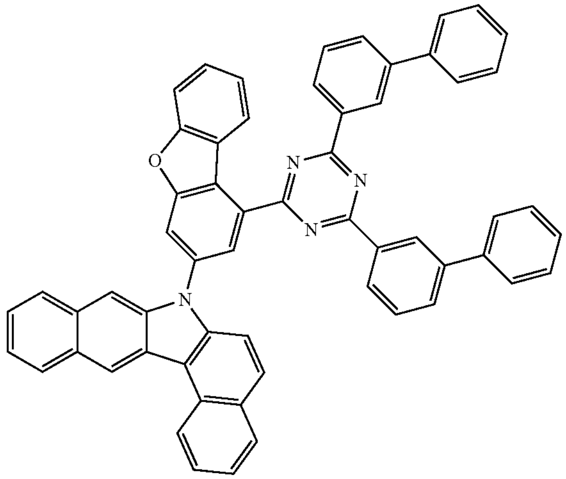

-continued
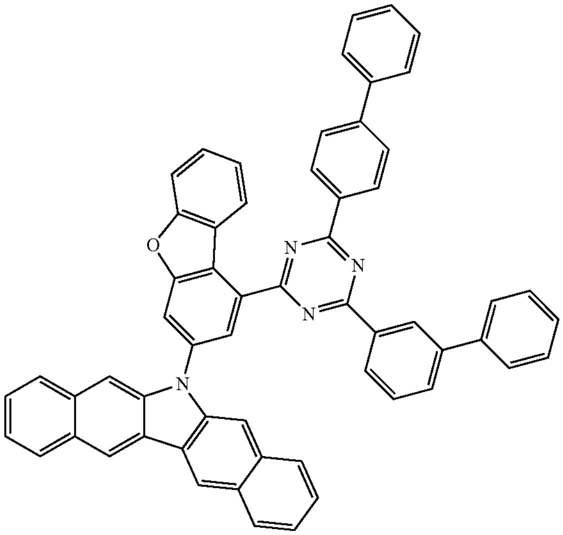
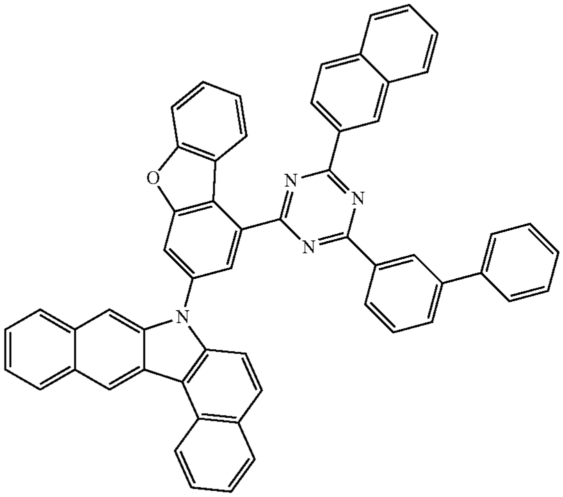
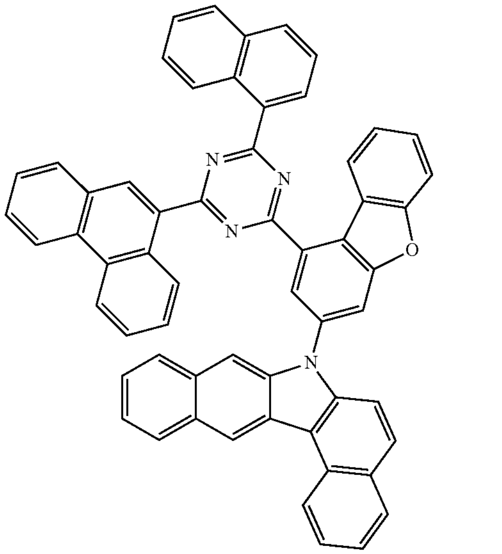
-continued
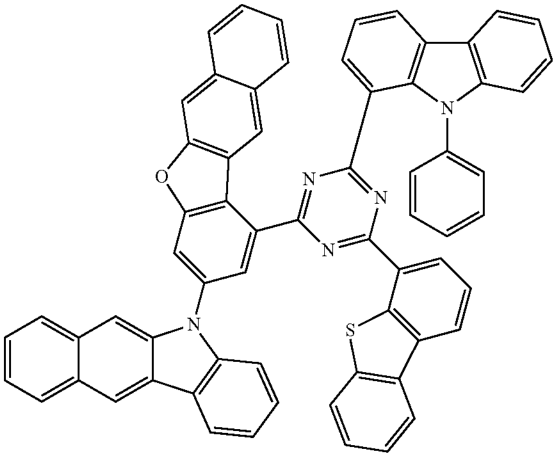
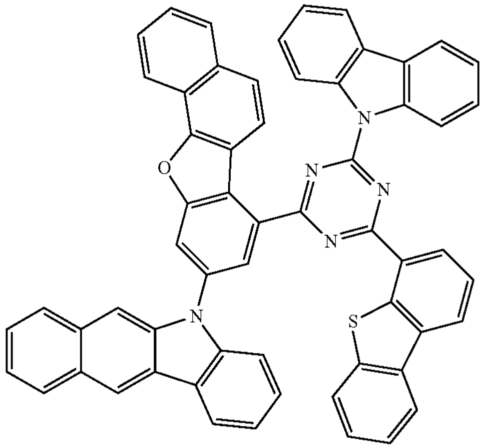
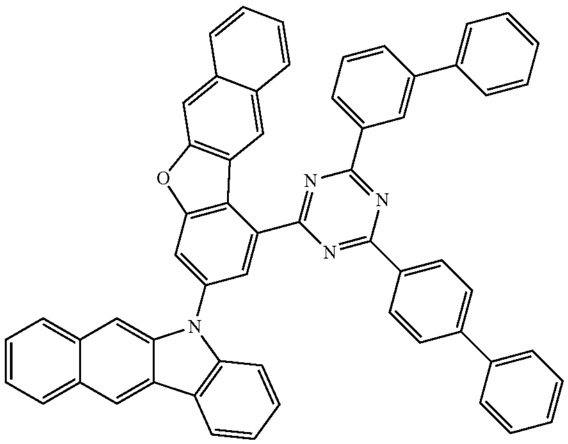

-continued
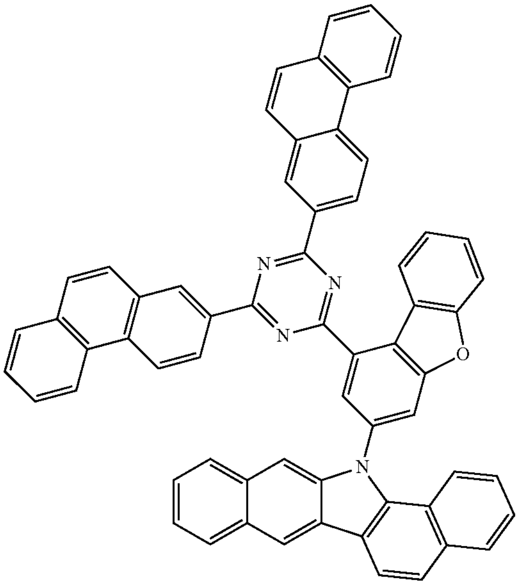
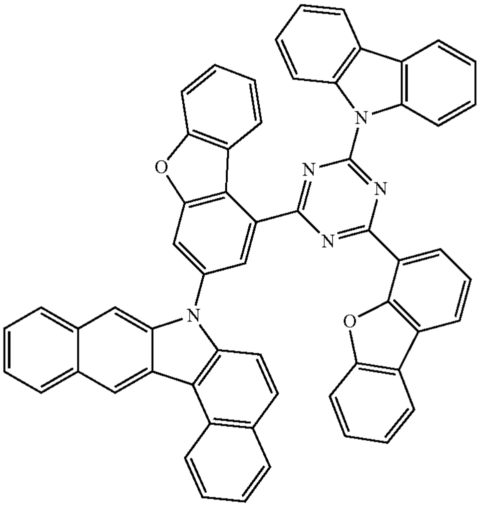
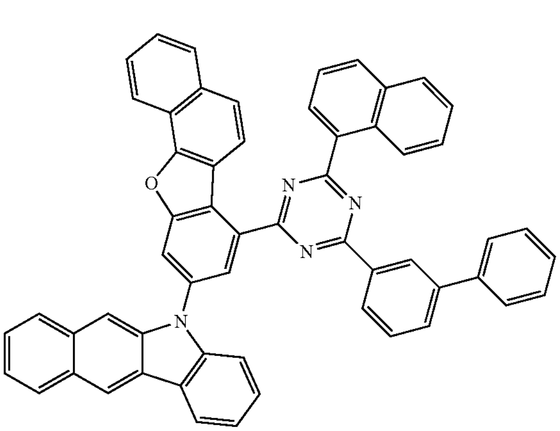
-continued
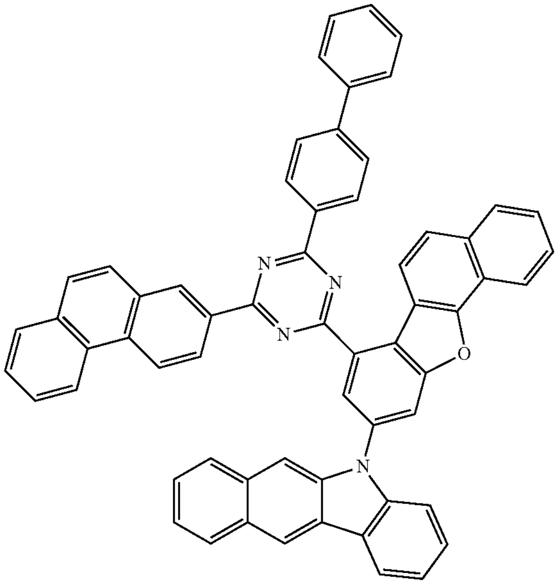
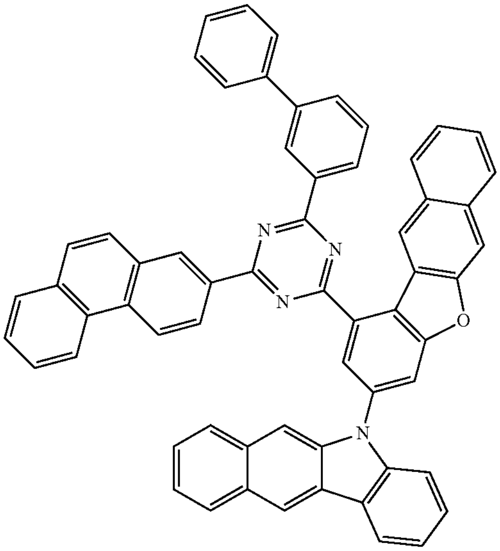
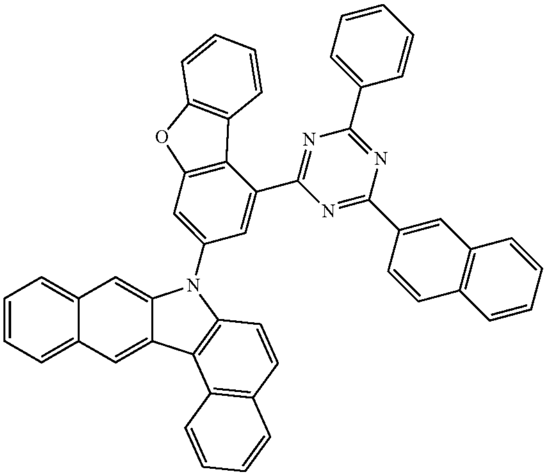

-continued
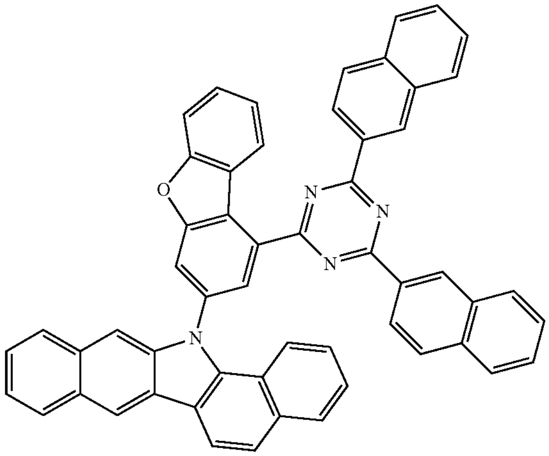
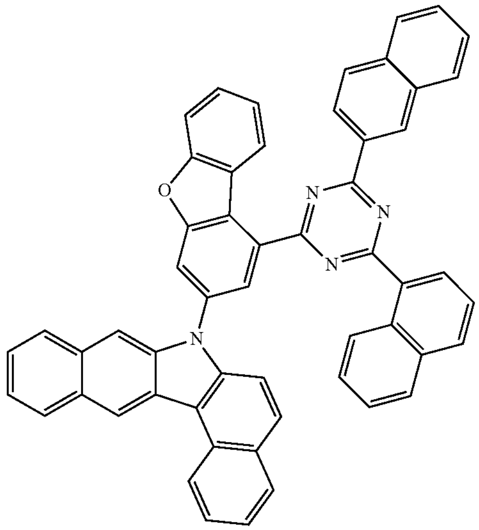
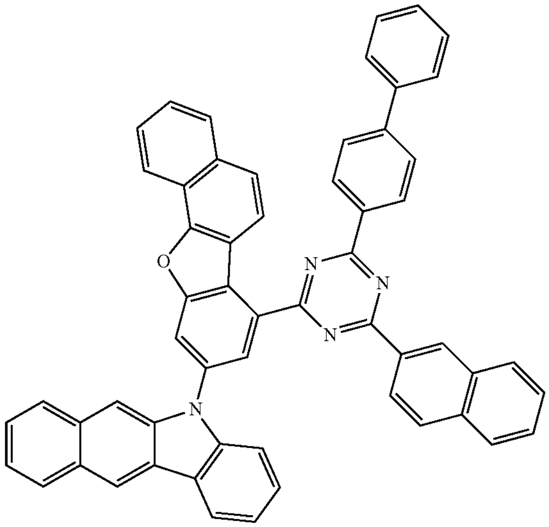
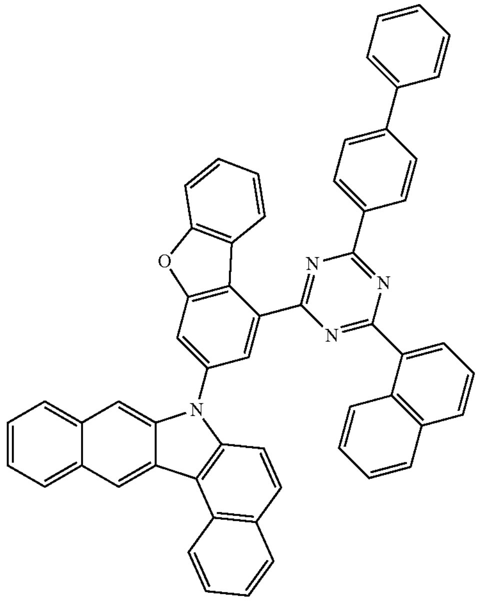
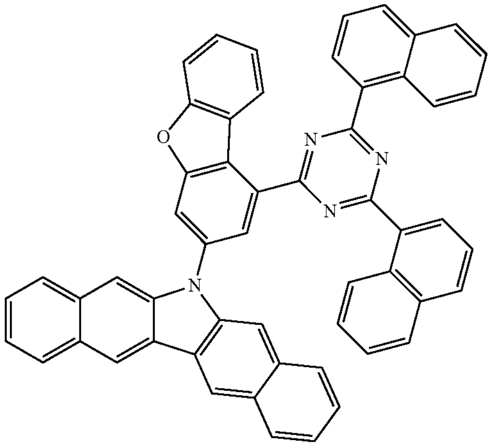
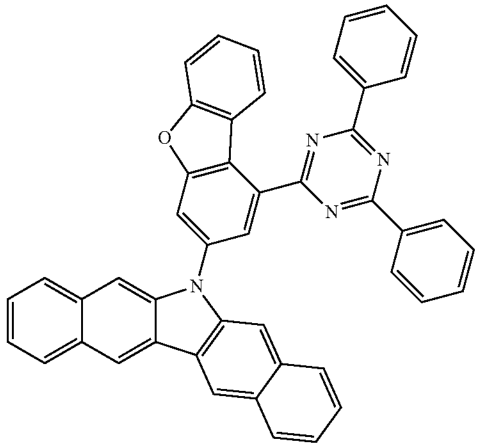
-continued -continued
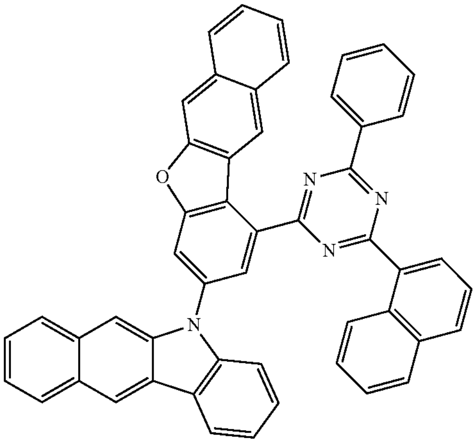
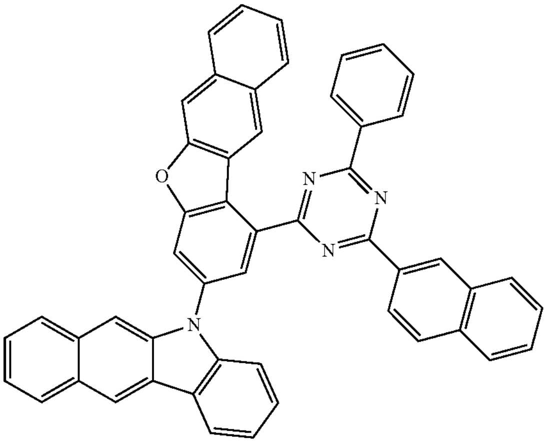
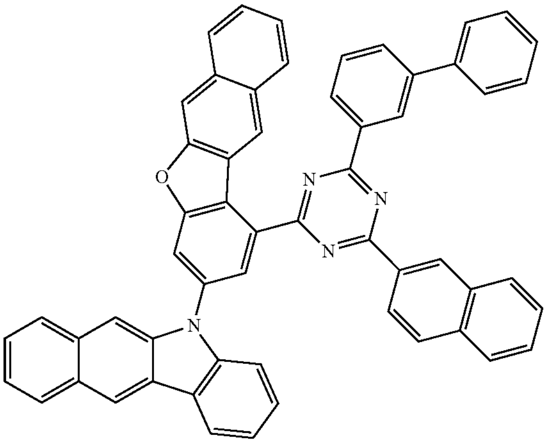
-continued
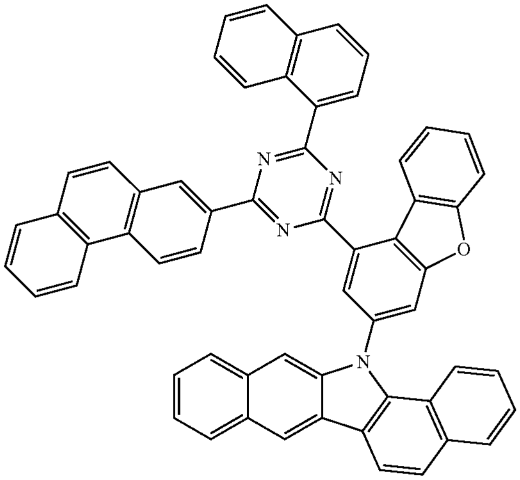
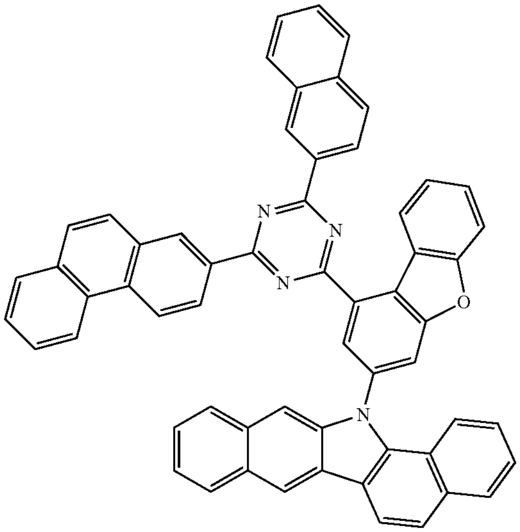
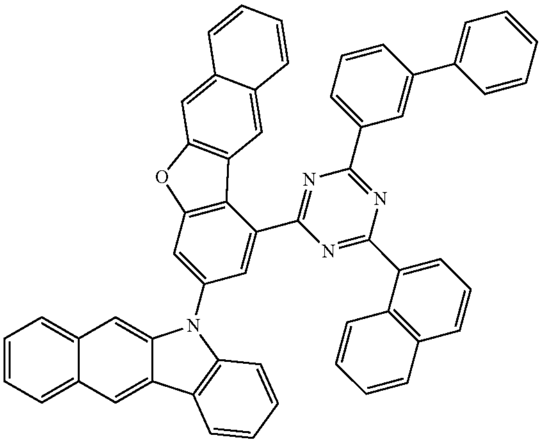

-continued
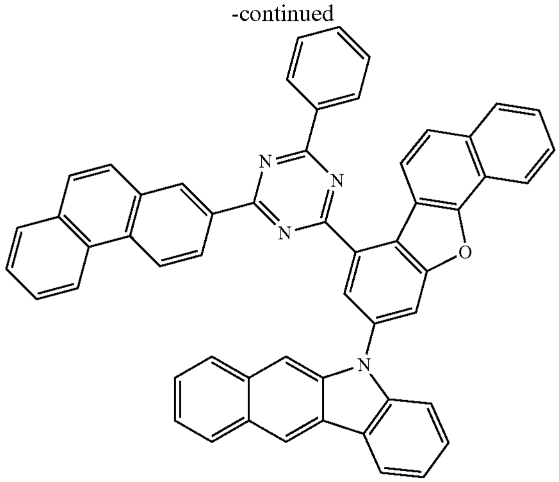
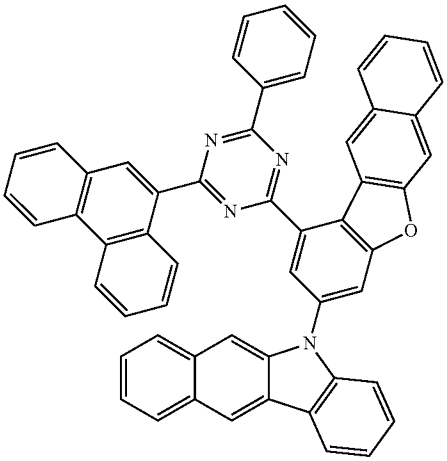
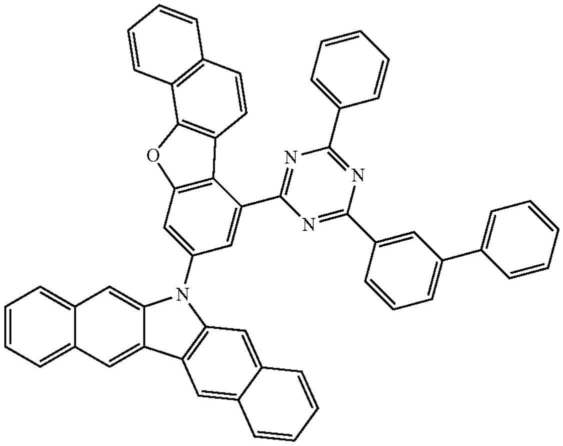
-continued
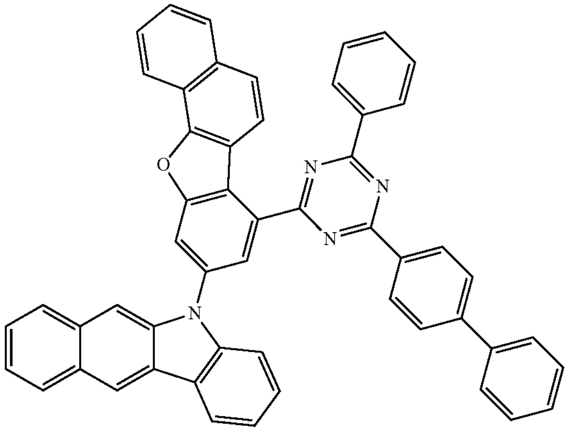
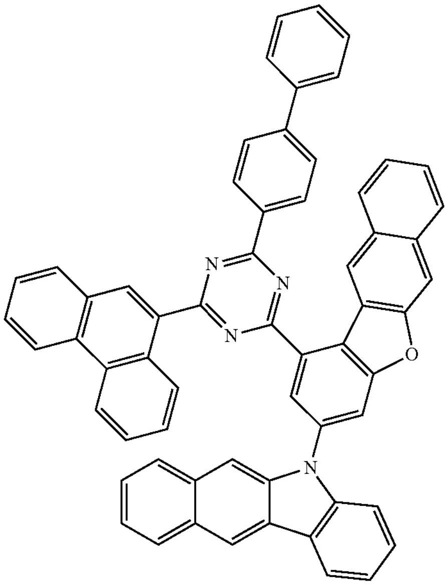
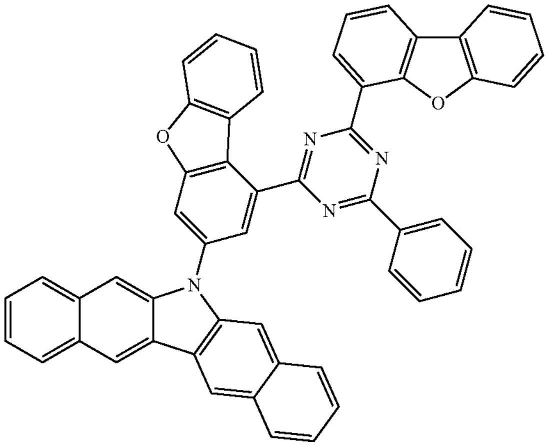

-continued
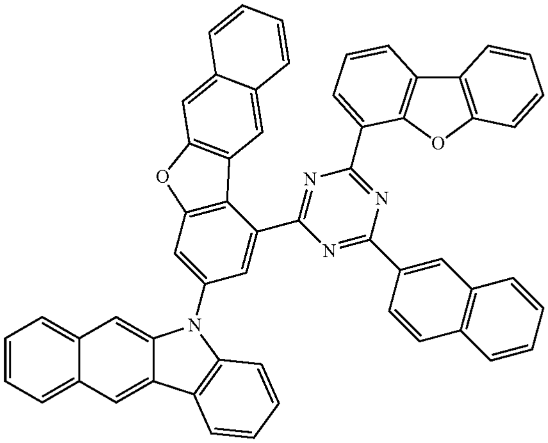
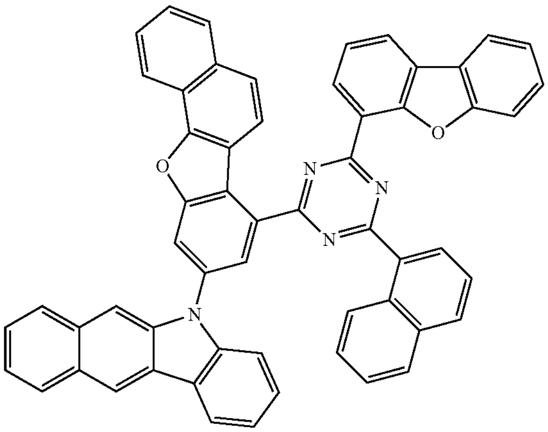
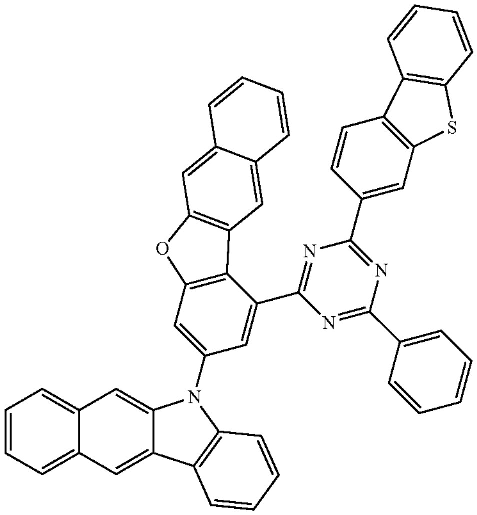
-continued
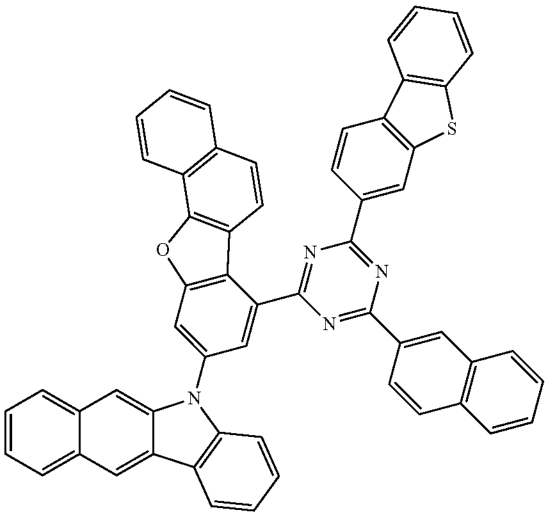
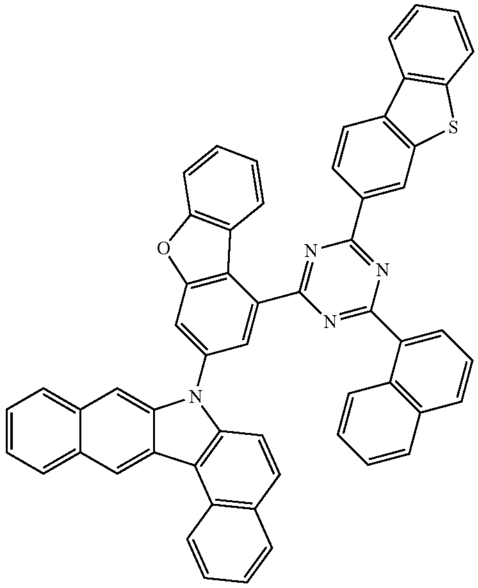
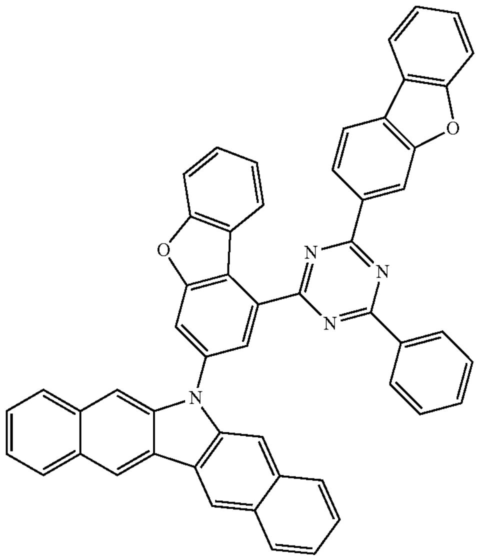

-continued
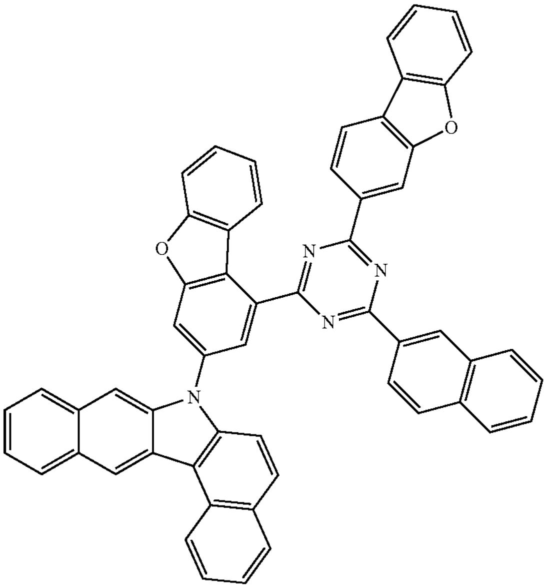
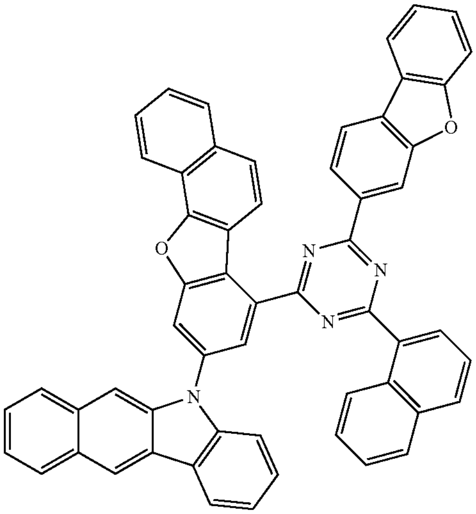
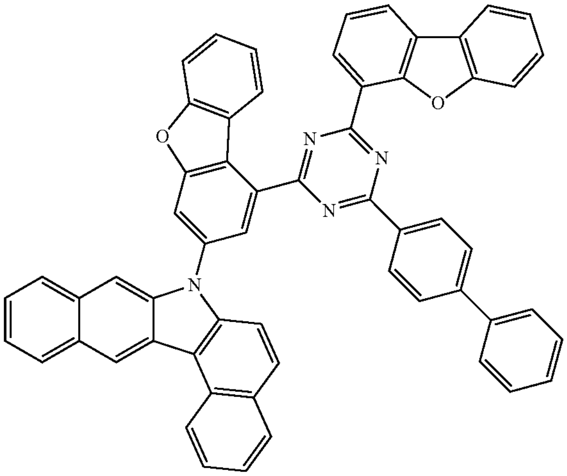
-continued
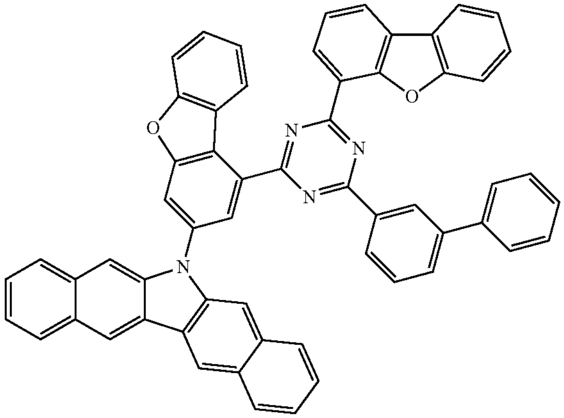
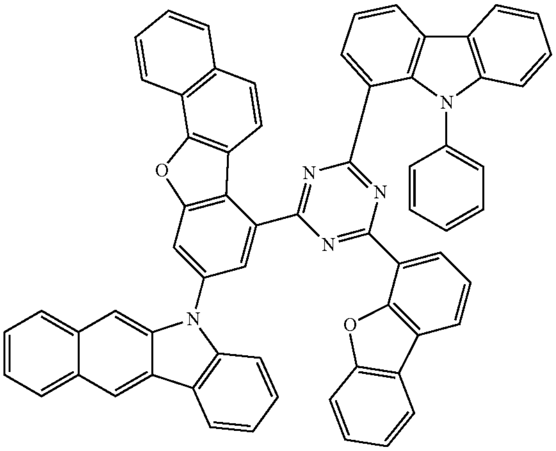
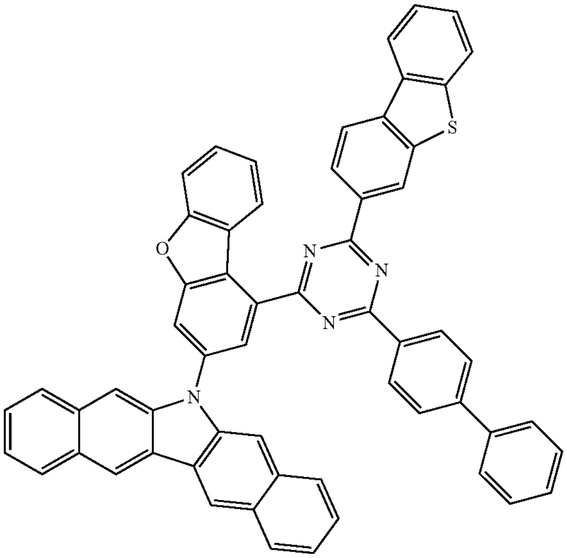

-continued
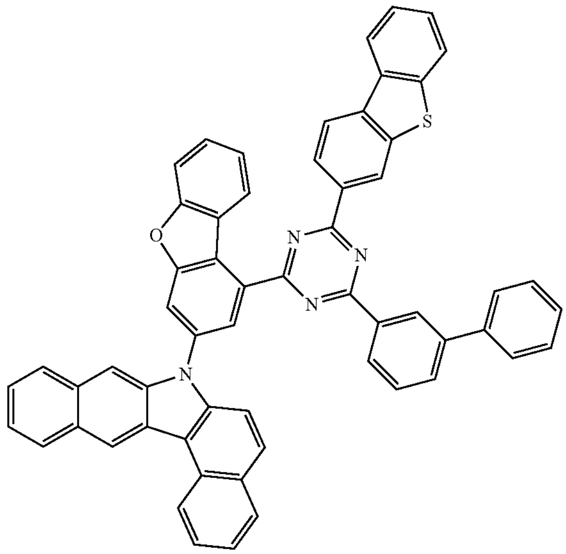
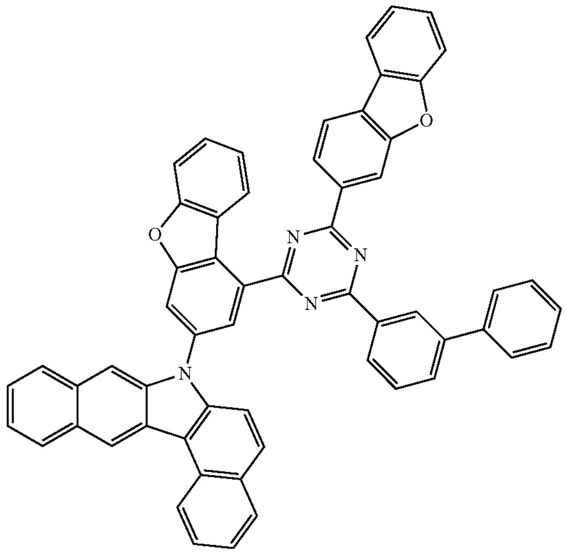
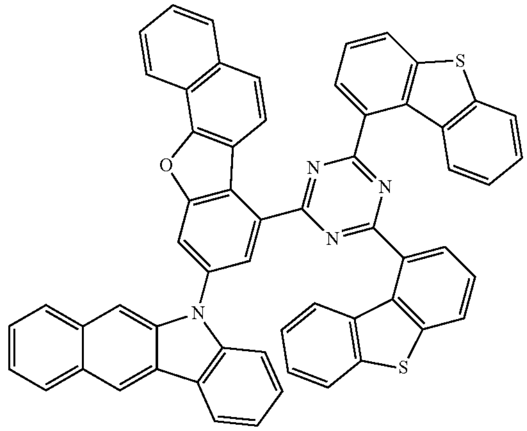
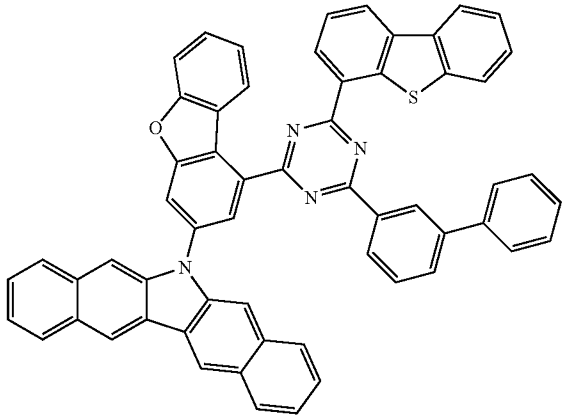
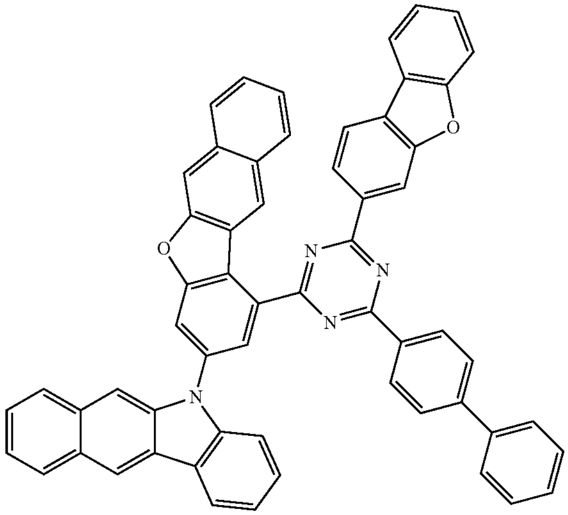
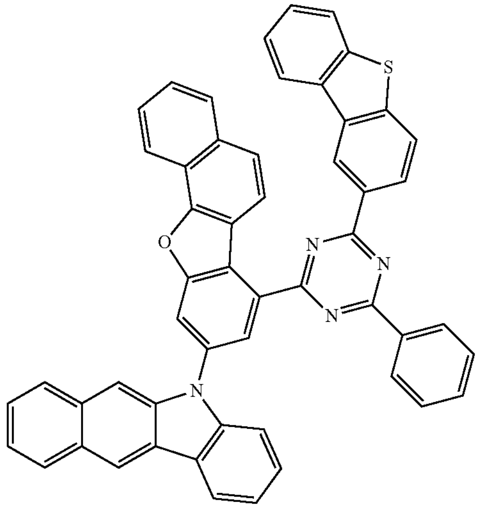
-continued -continued
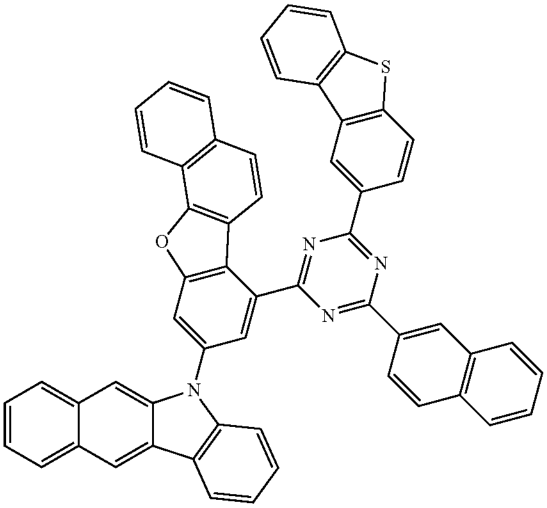
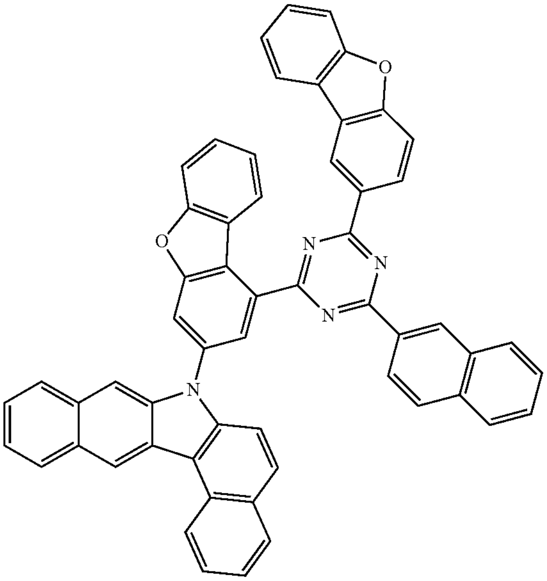
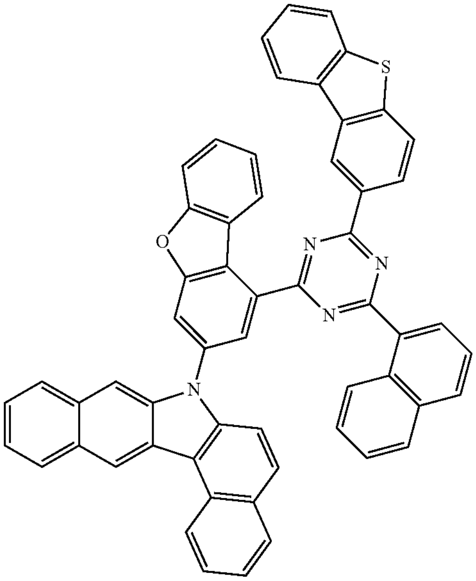
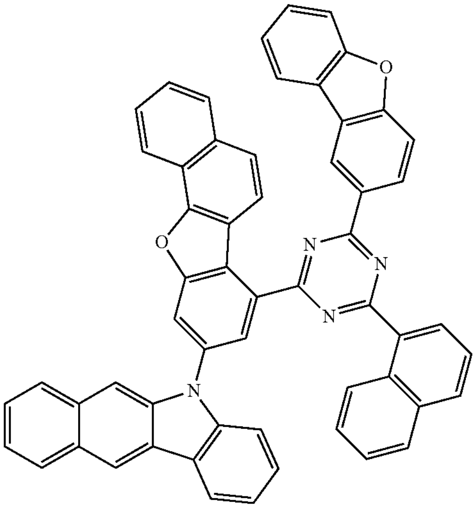
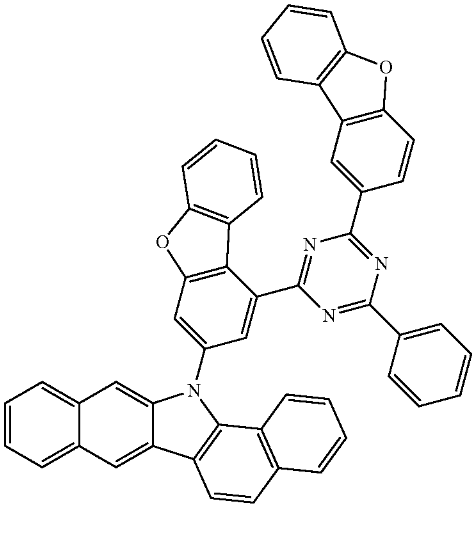
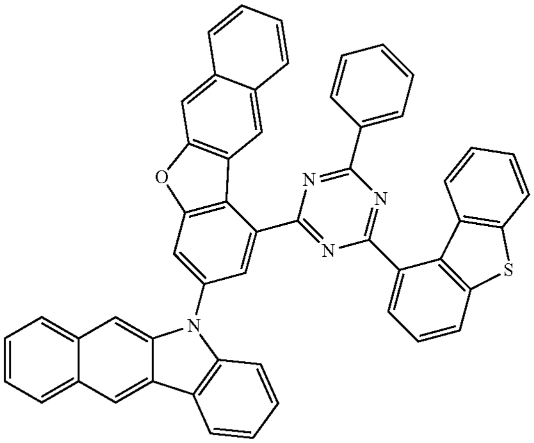

-continued
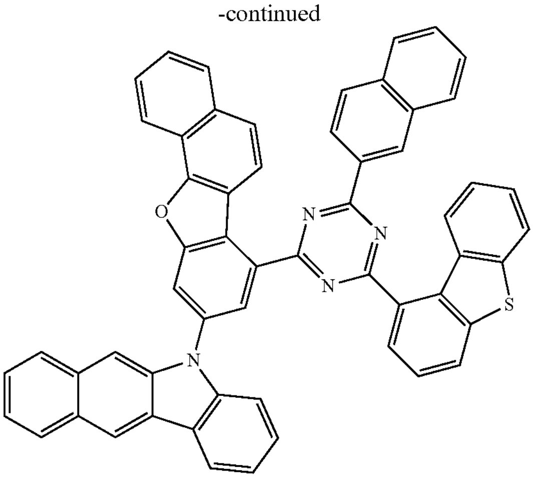
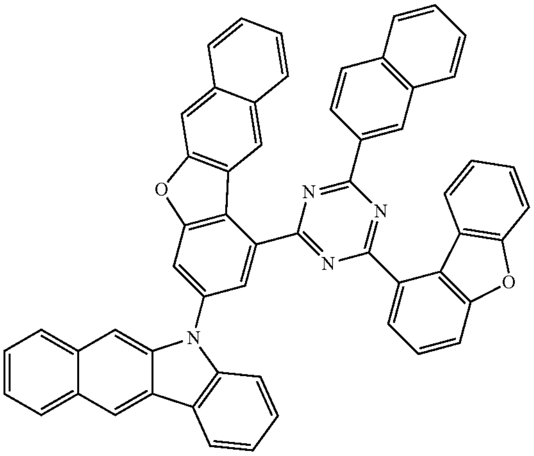
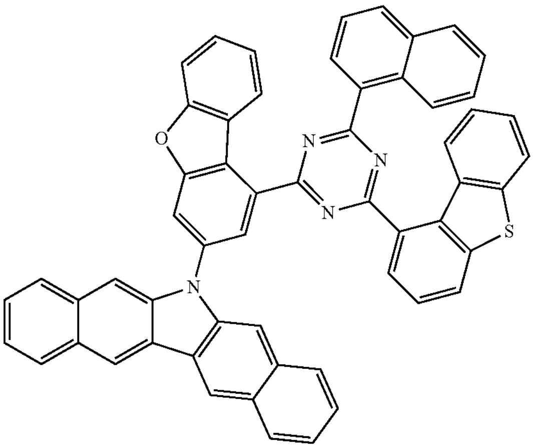
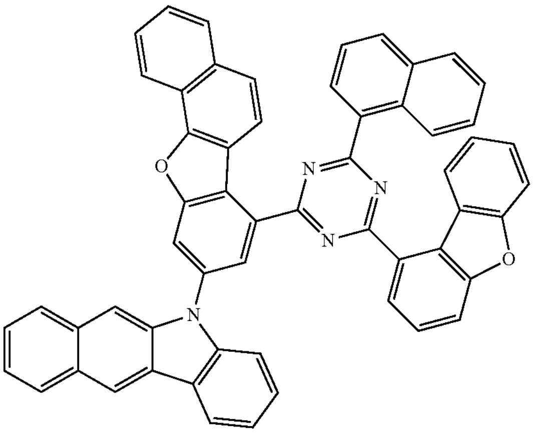
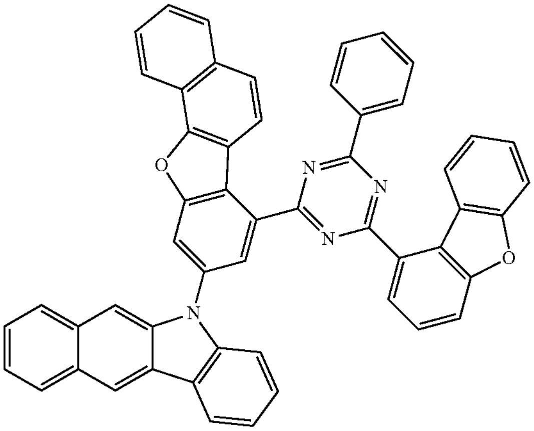
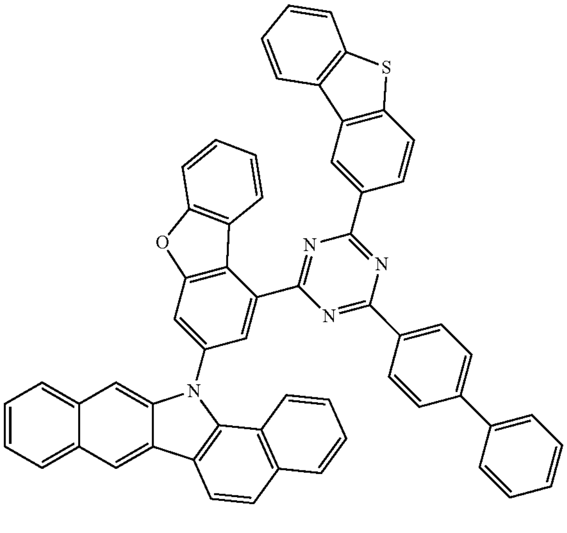
-continued -continued
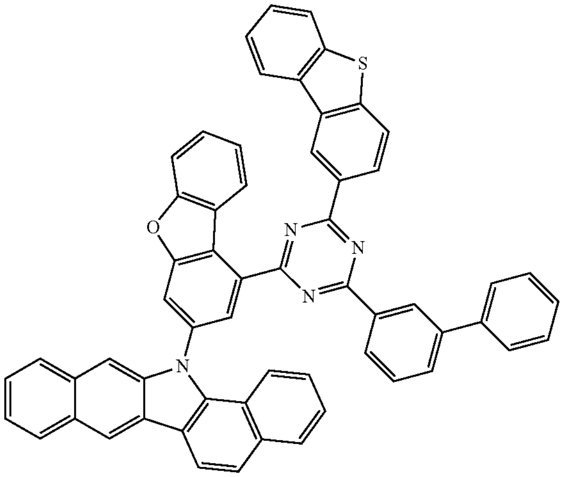
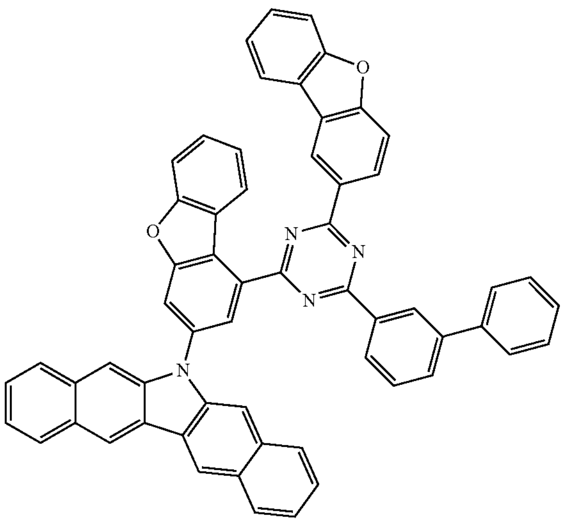
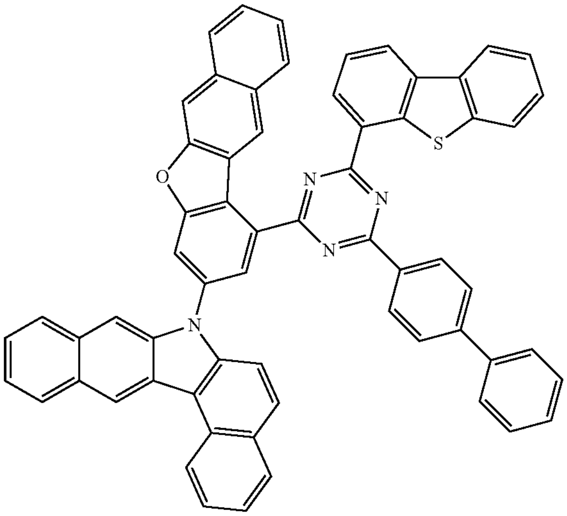
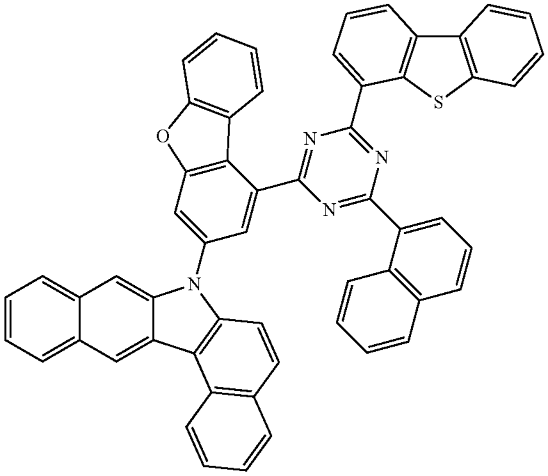
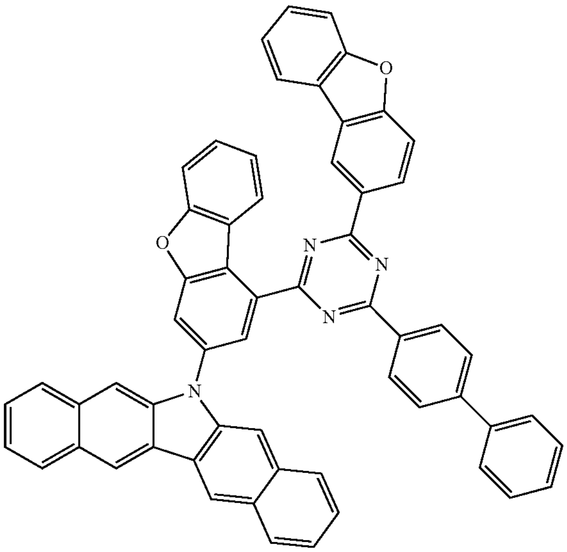
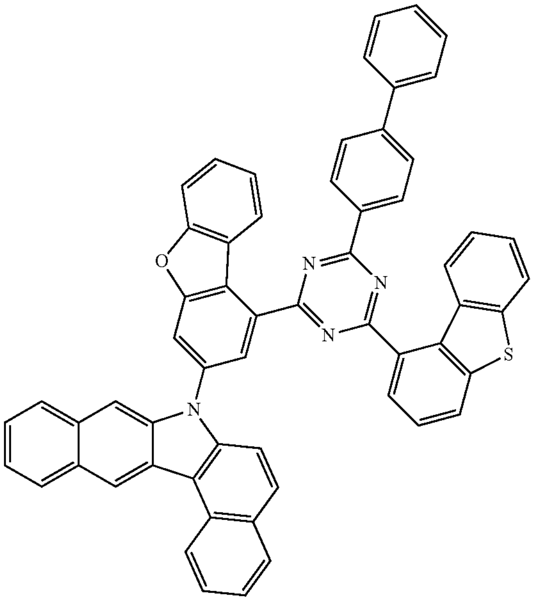
-continued -continued
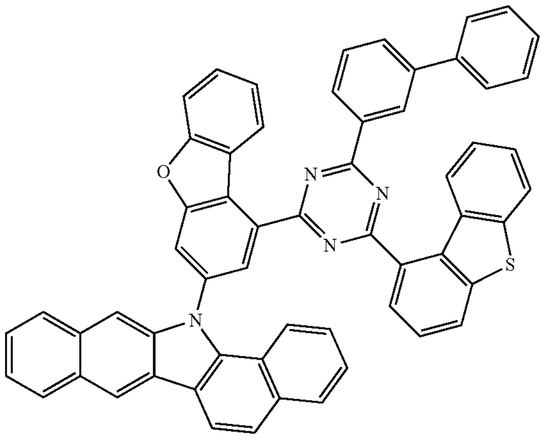
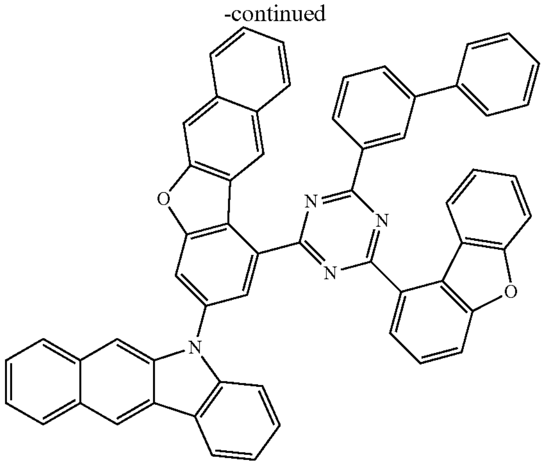
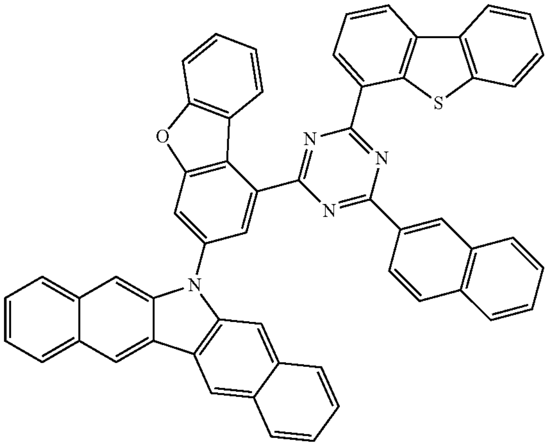
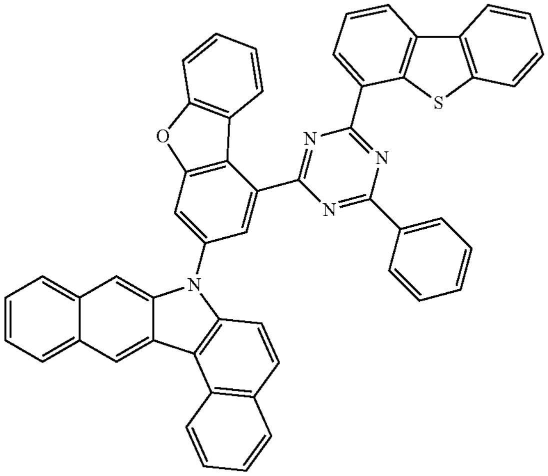
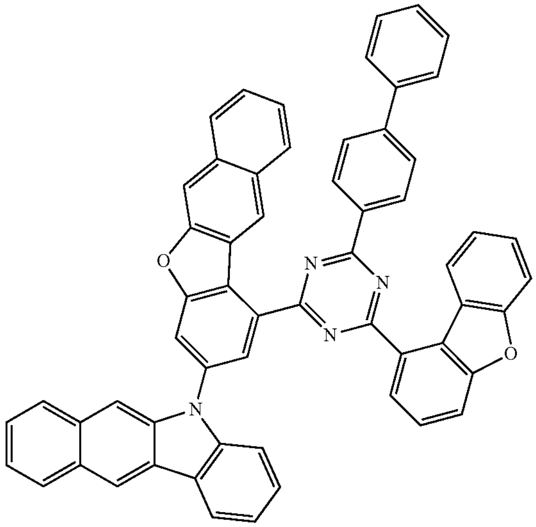
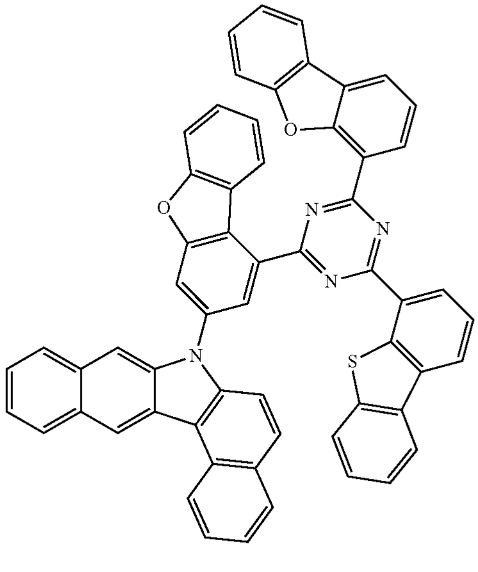

-continued
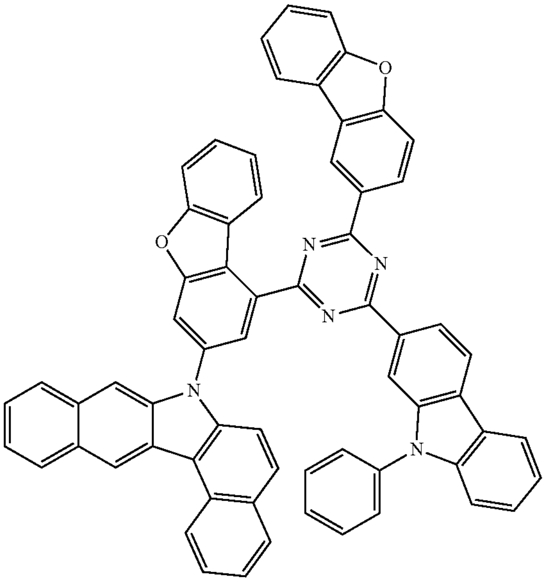
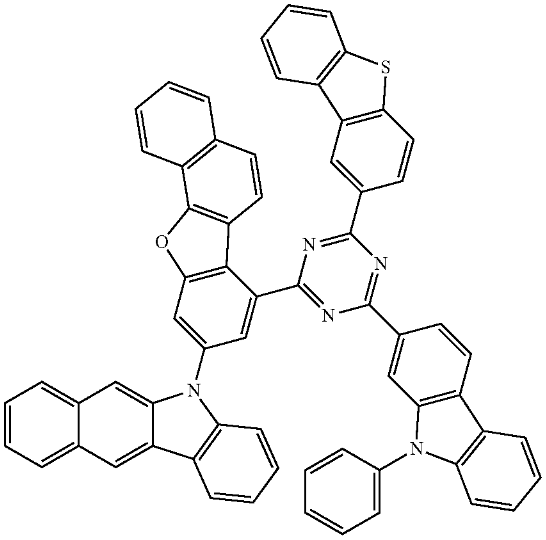
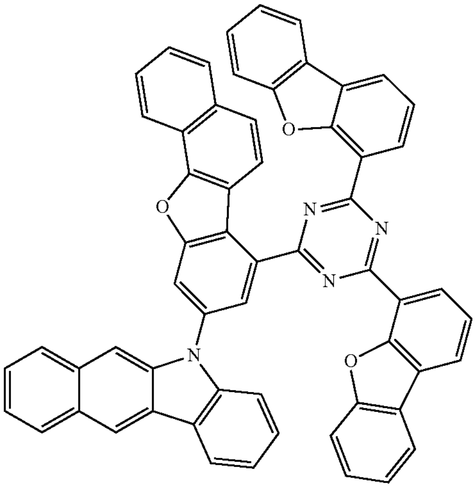
-continued
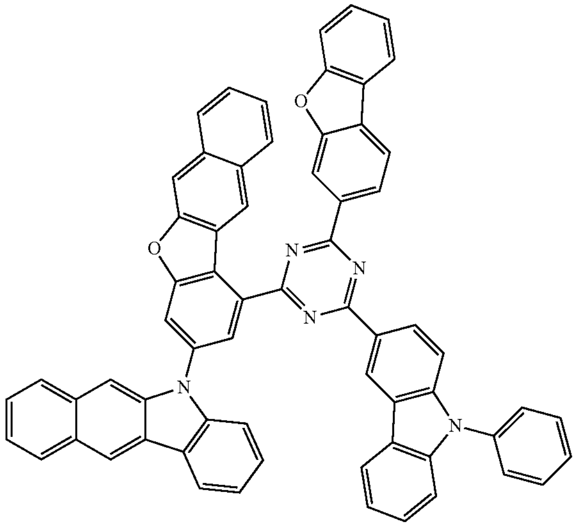
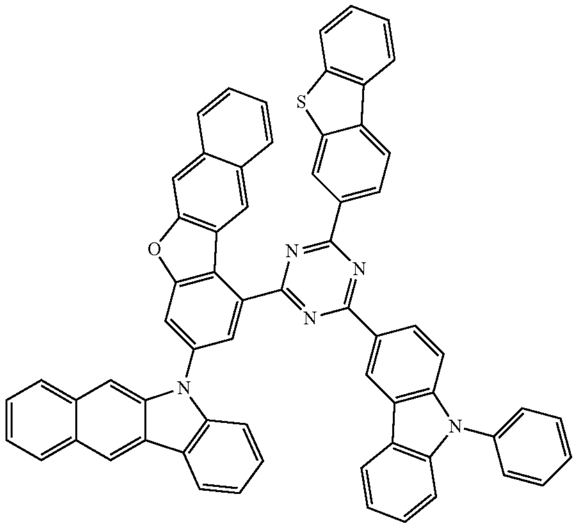
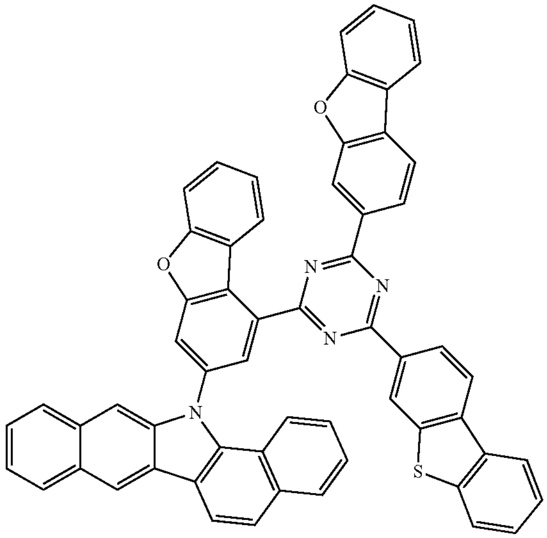

-continued
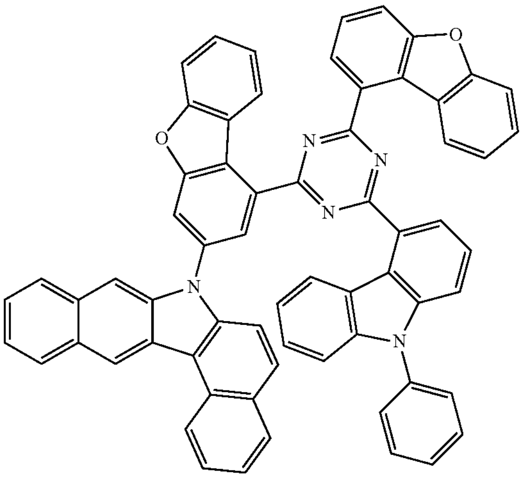
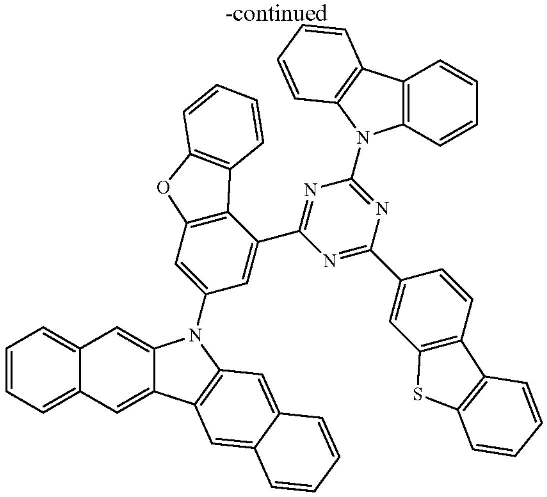
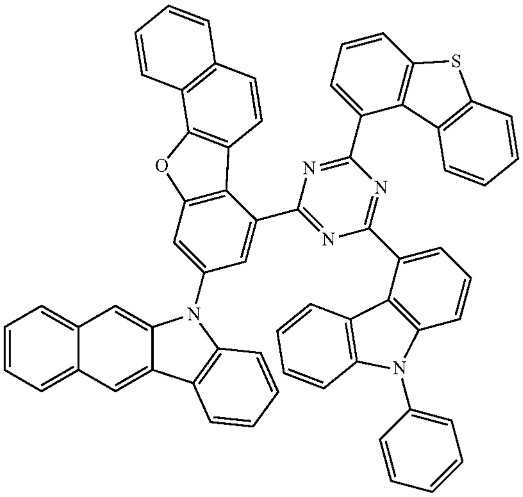
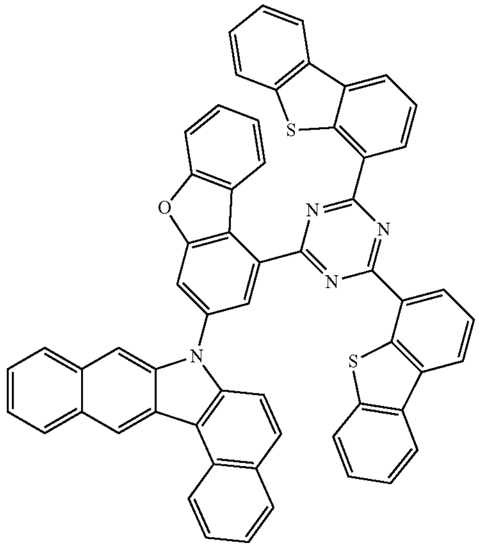
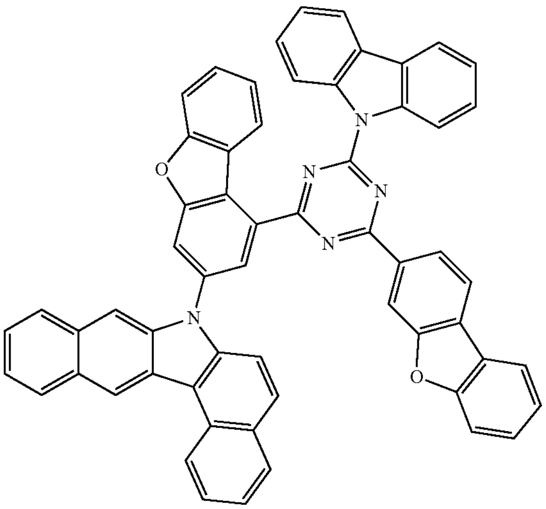
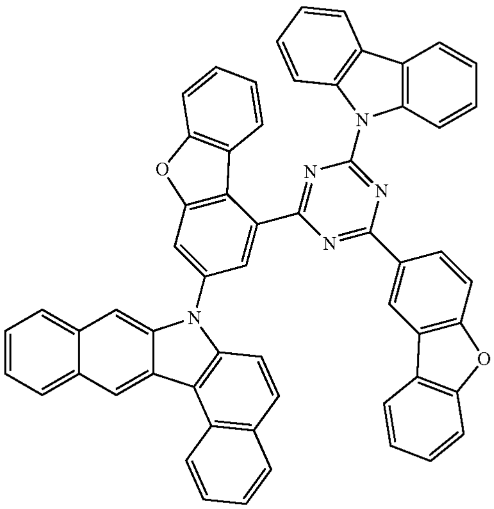
-continued -continued
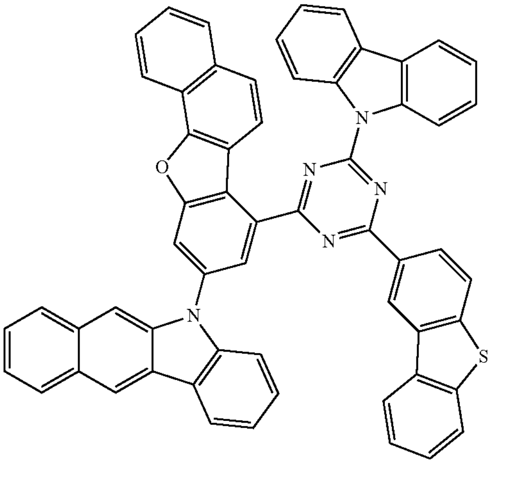
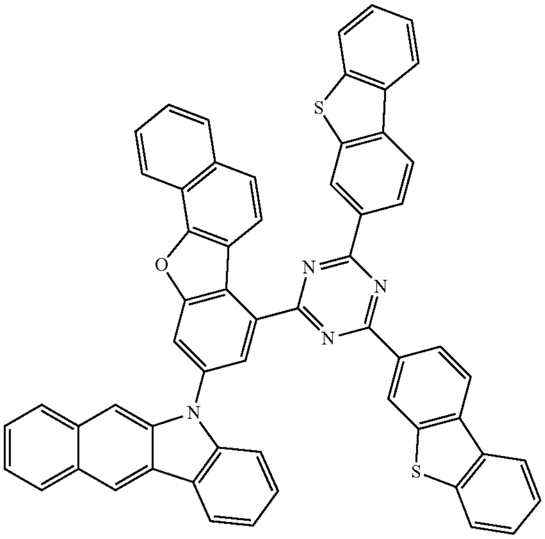
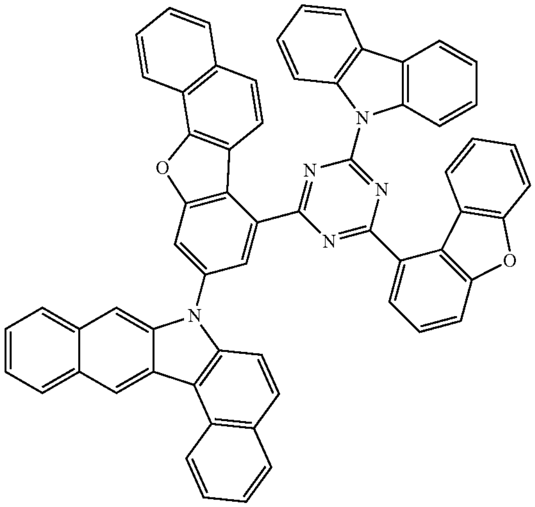
-continued
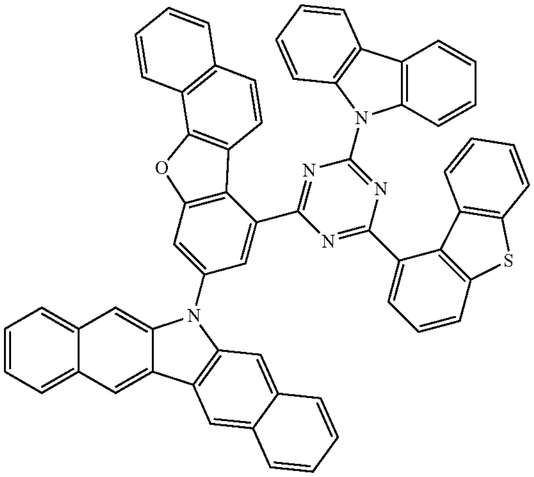
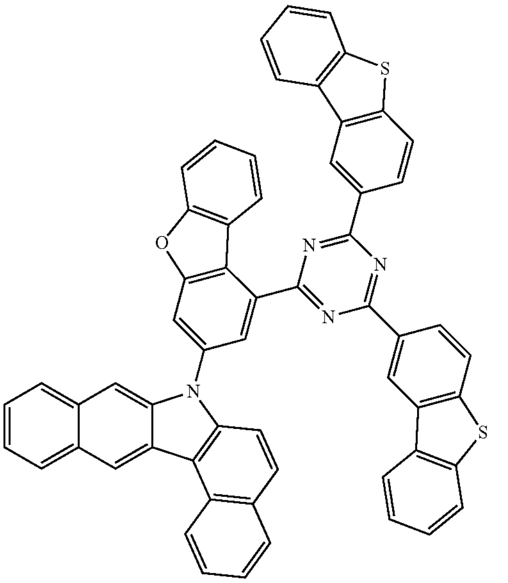
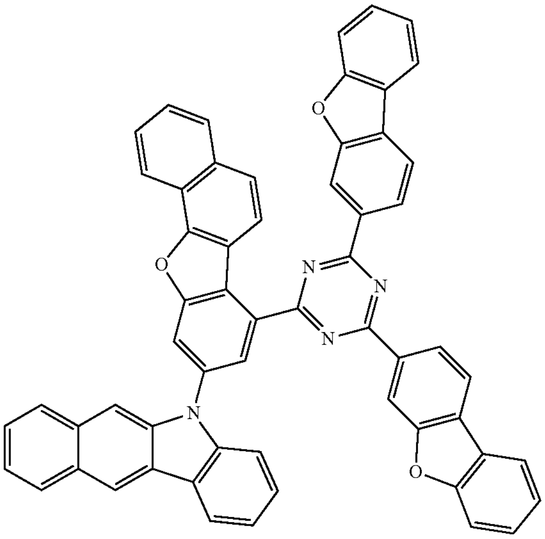

-continued
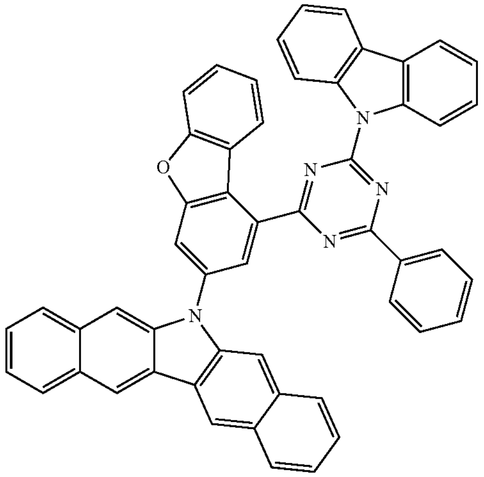
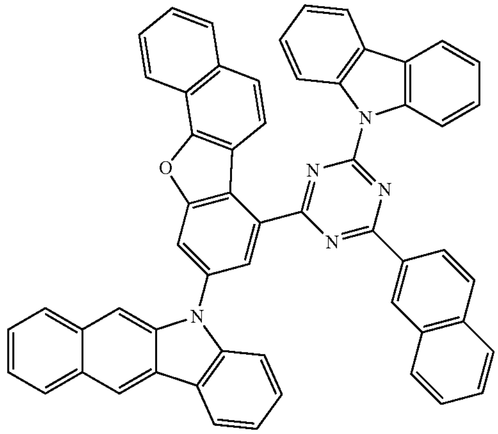
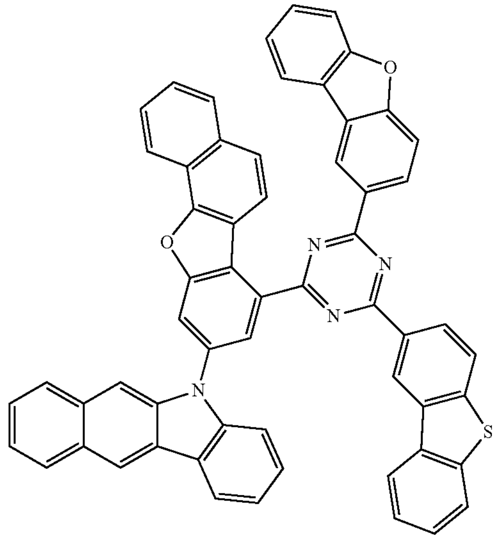
-continued
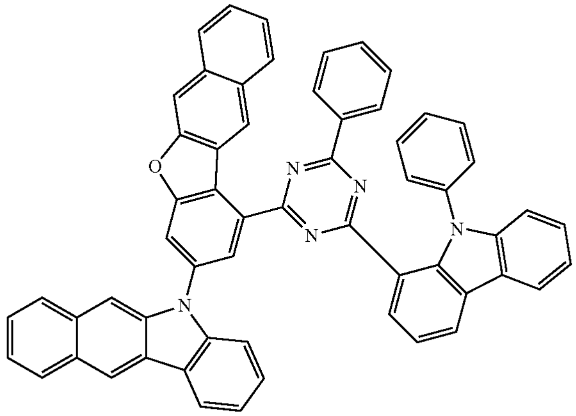
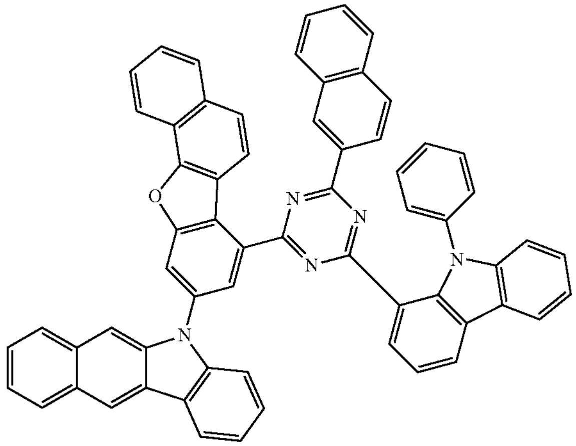
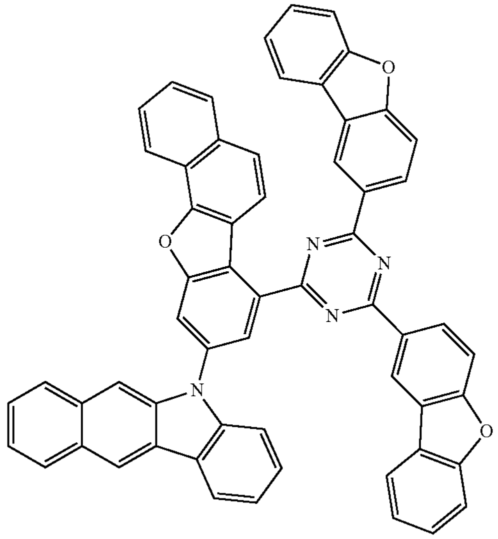

-continued
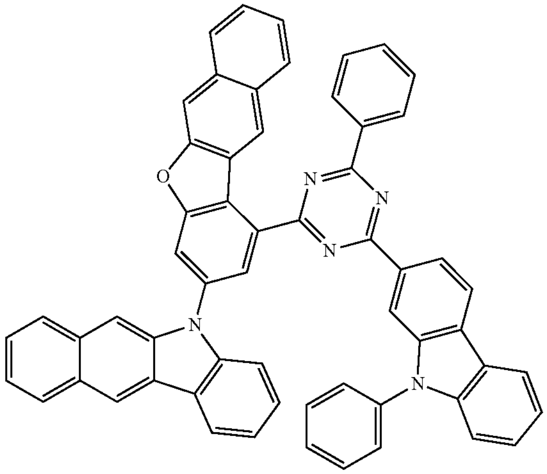
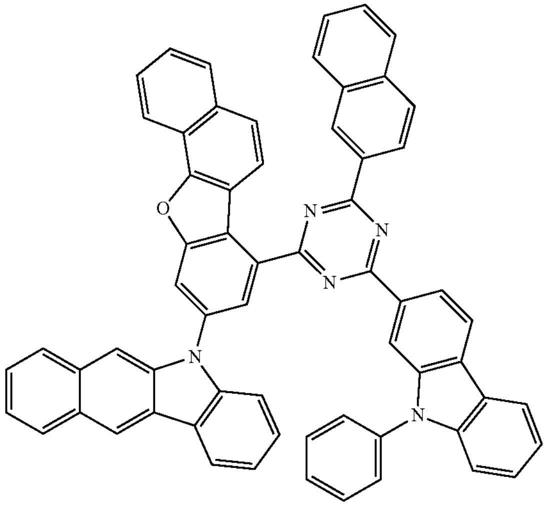
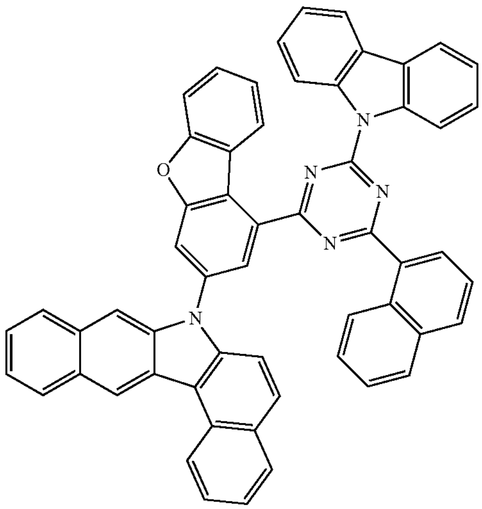
-continued
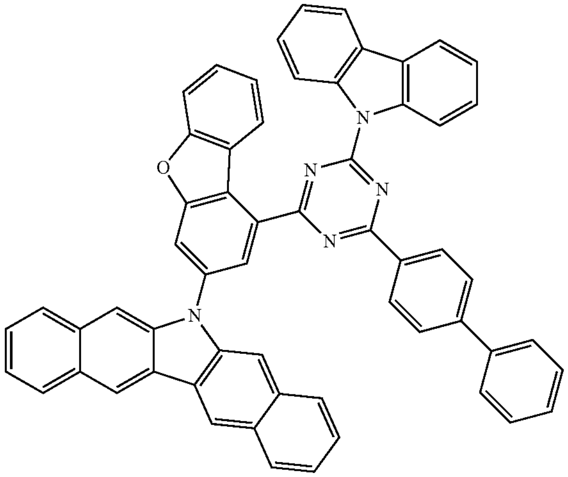
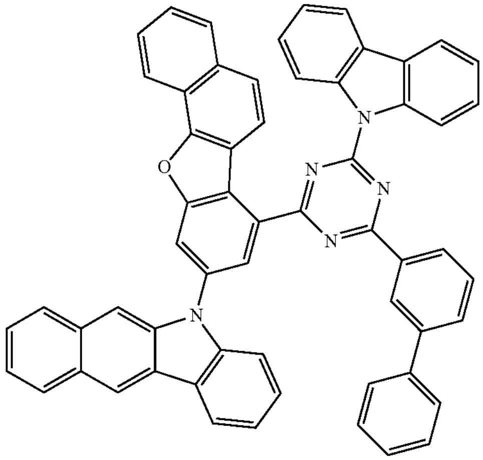
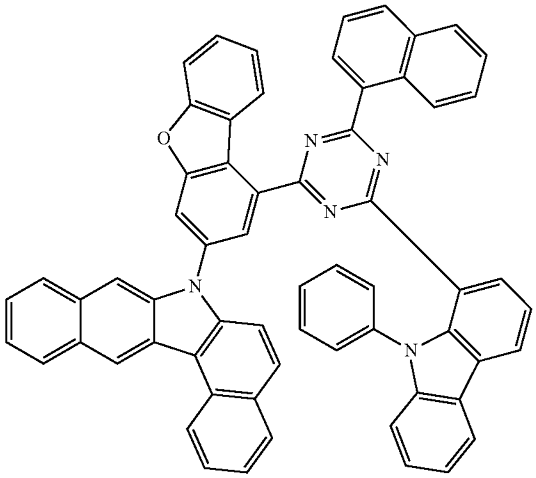

-continued
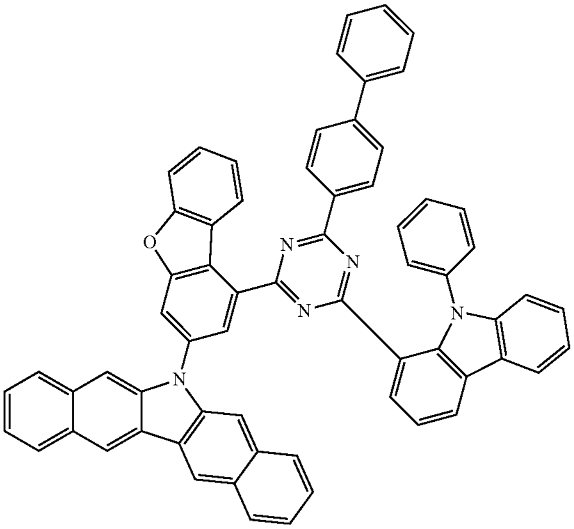
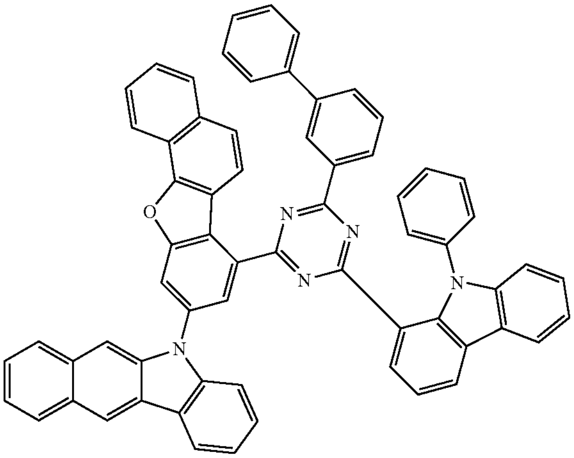
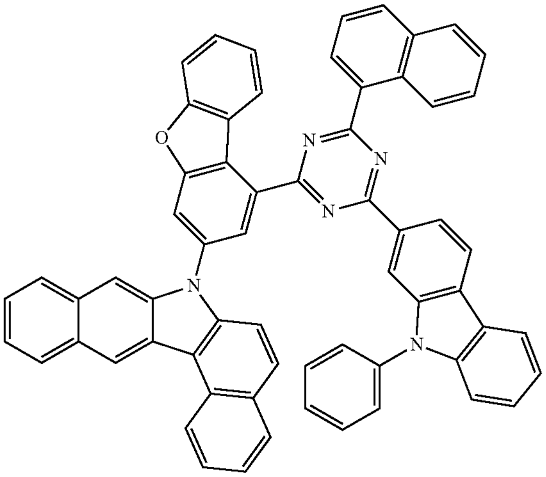
-continued
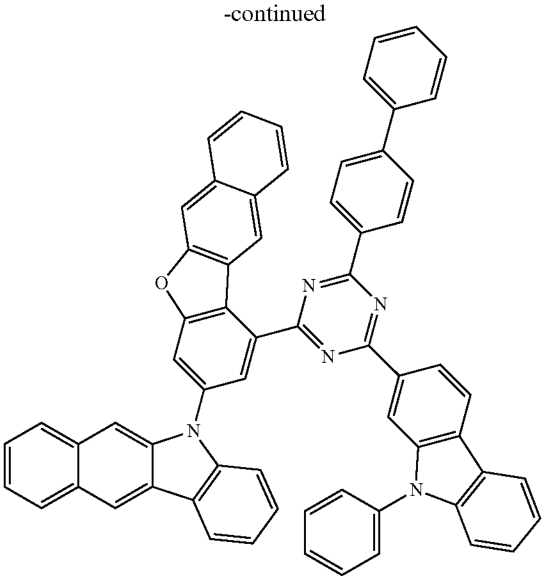
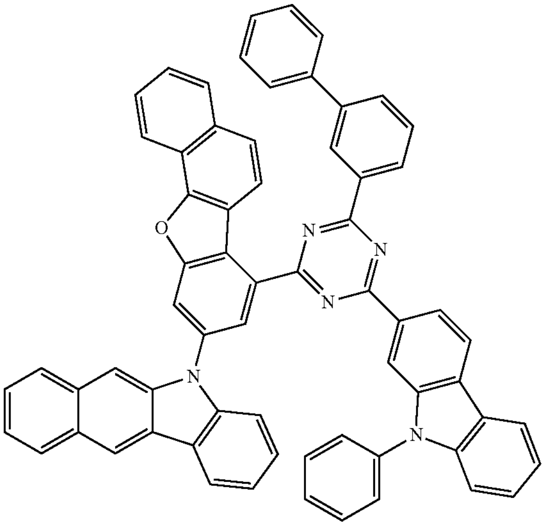
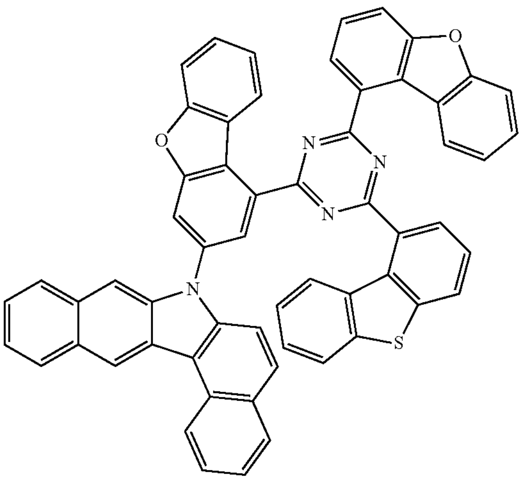

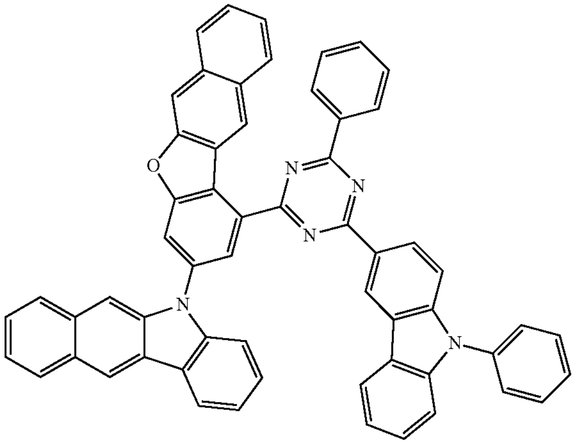
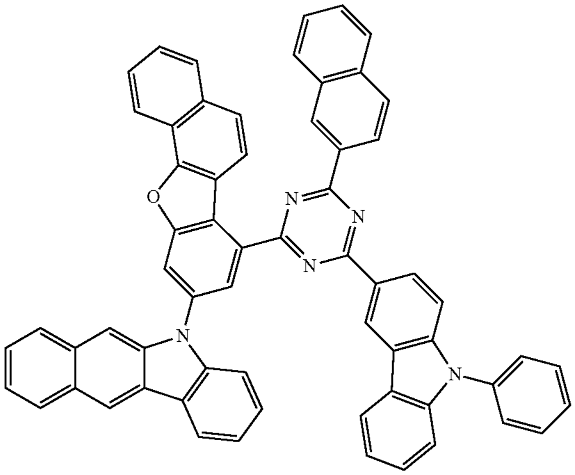
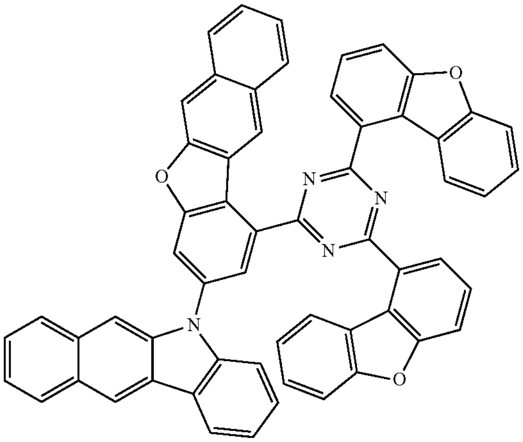
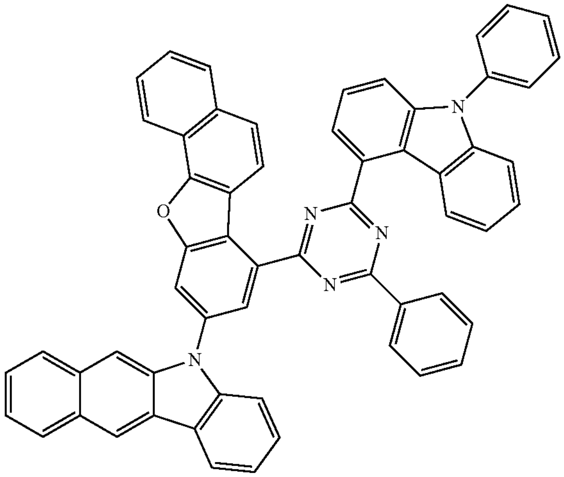
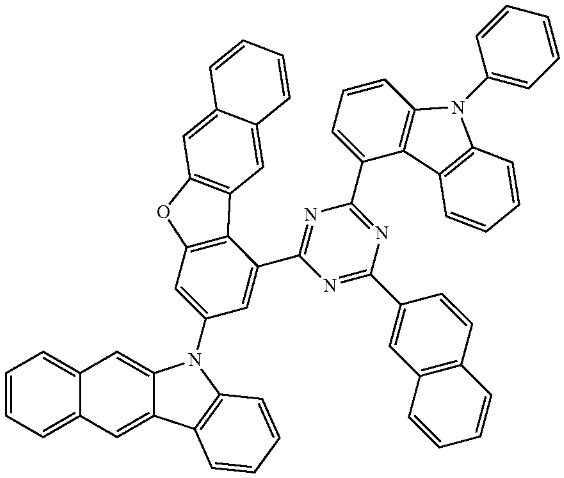
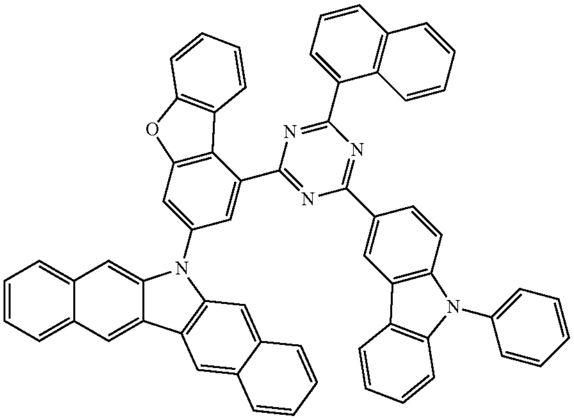

-continued
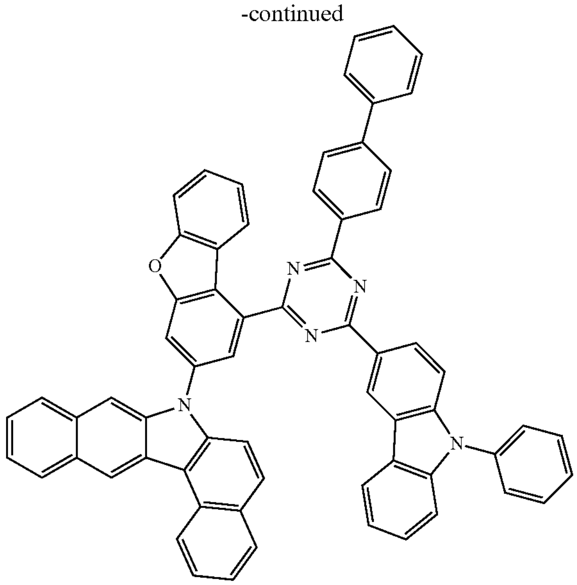
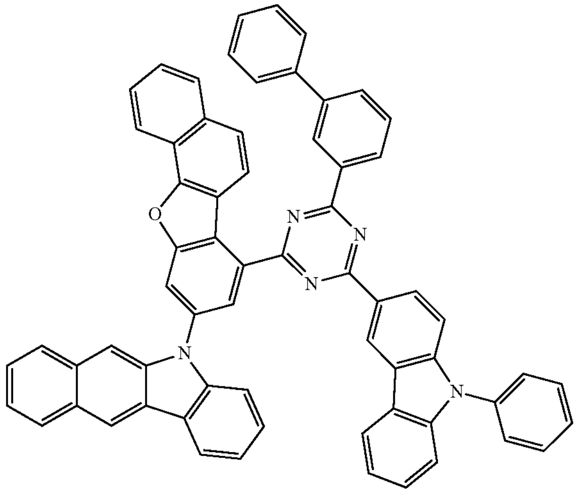
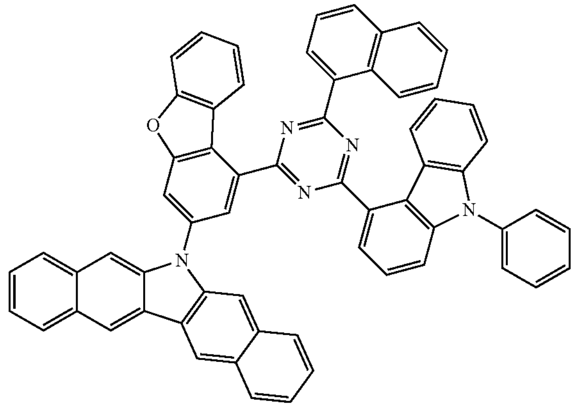
-continued
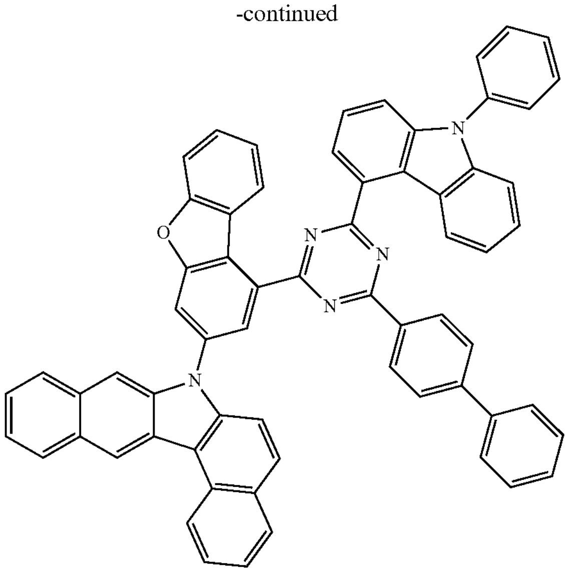
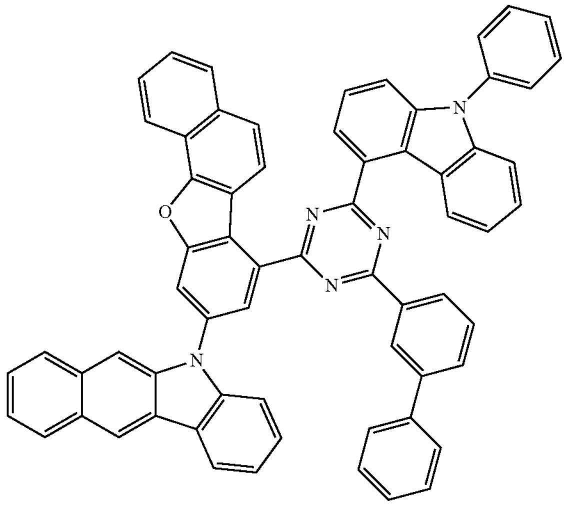
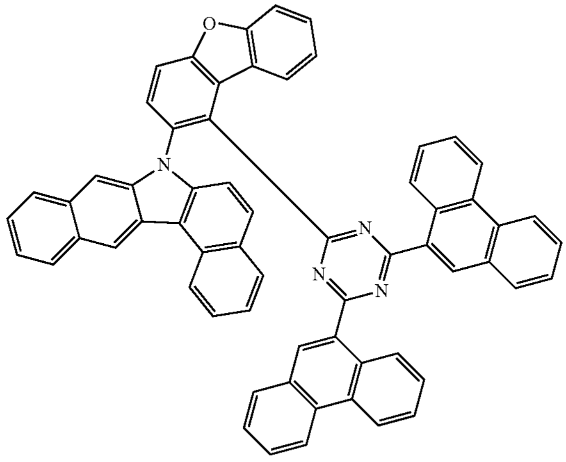

-continued
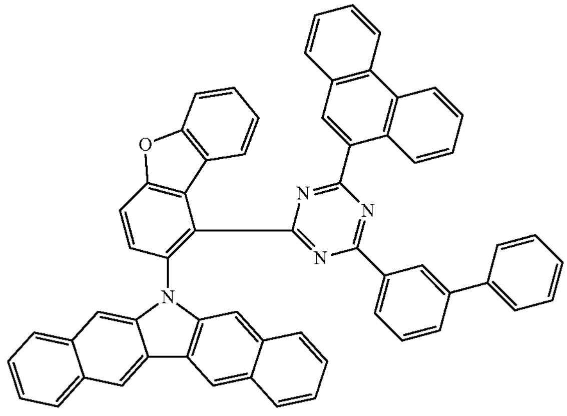
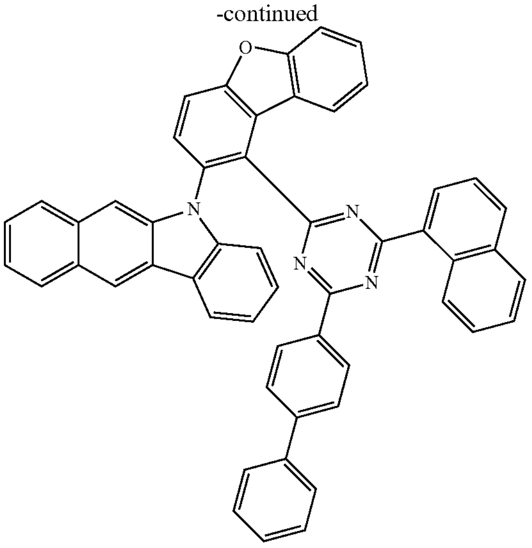
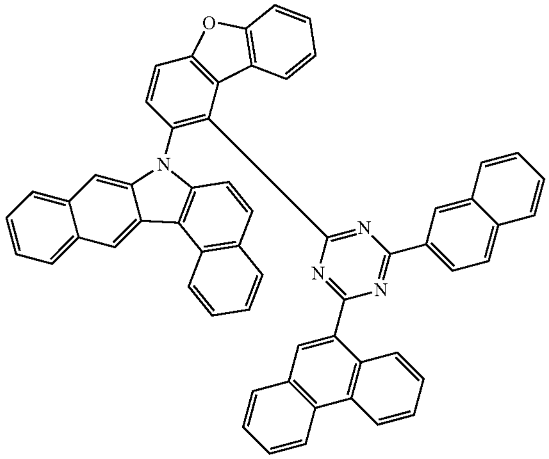
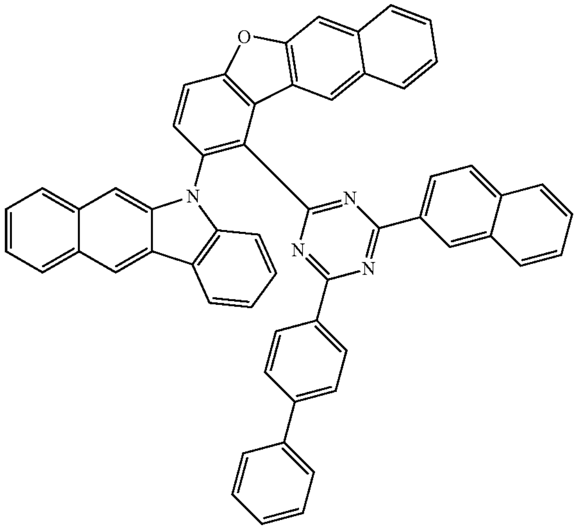
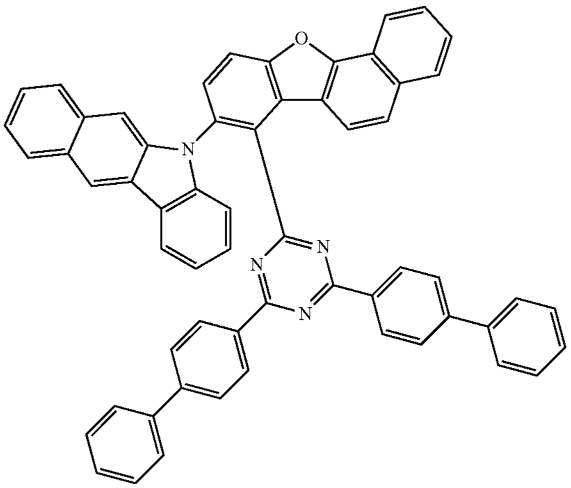
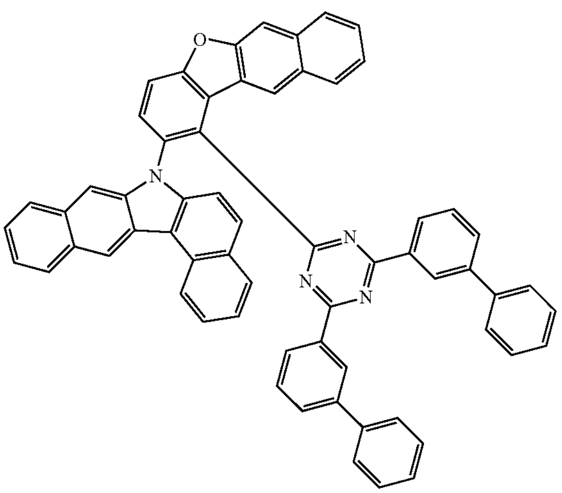
-continued -continued
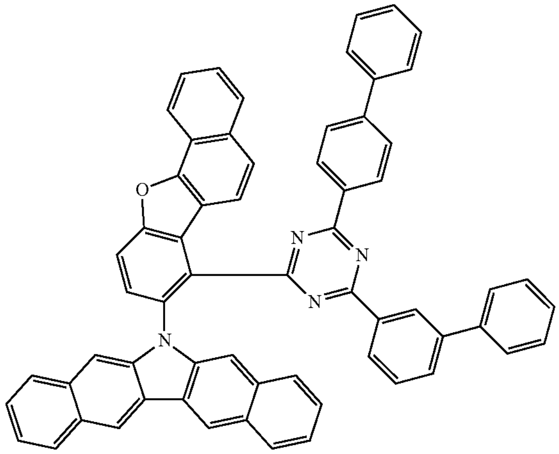
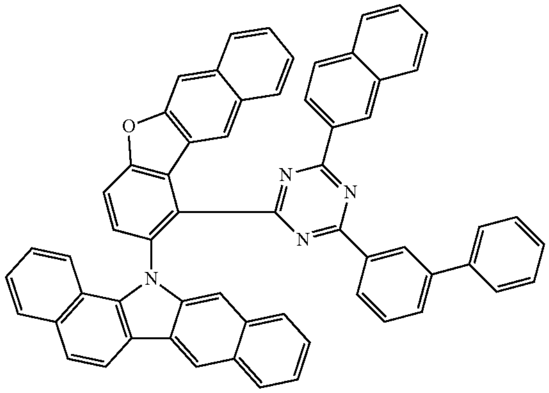
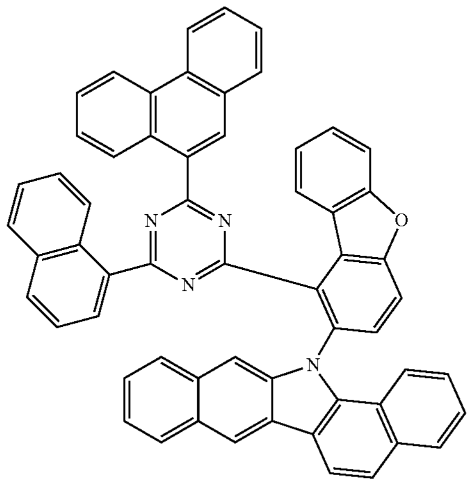
-continued
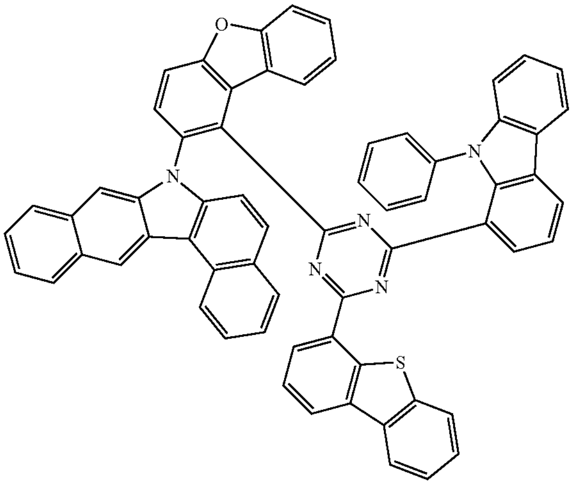
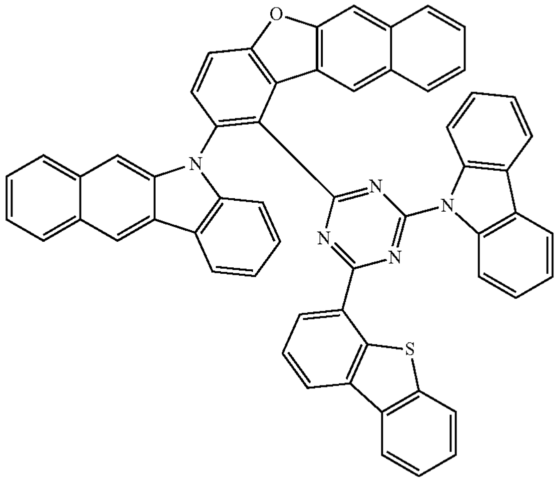
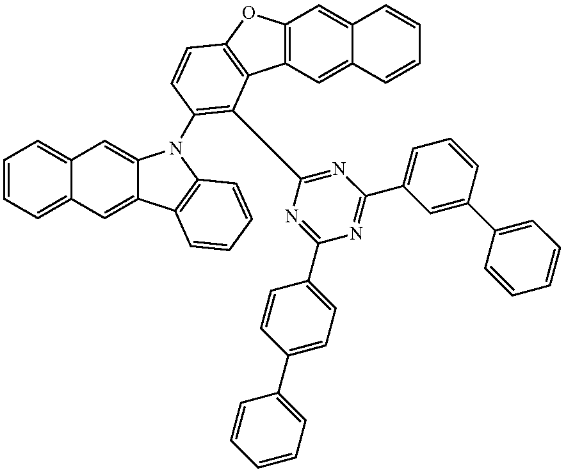

-continued
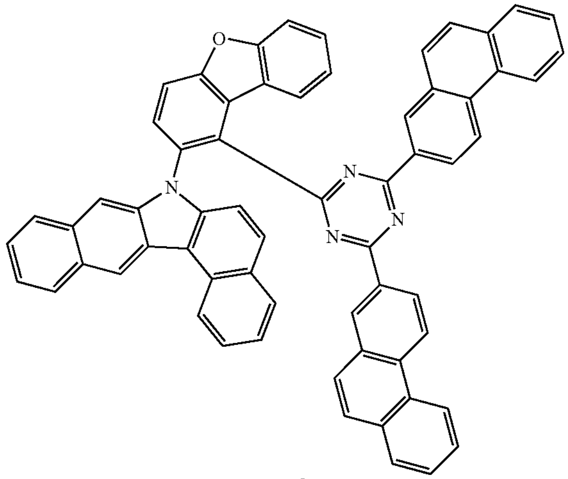
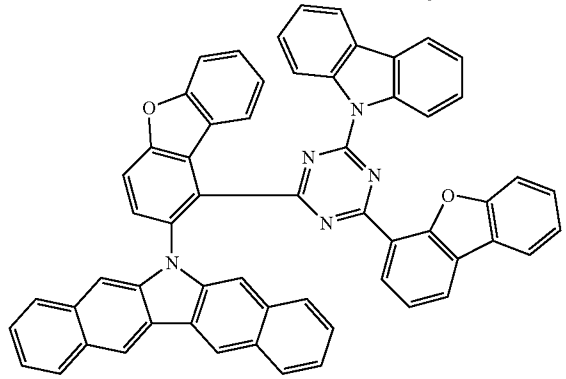
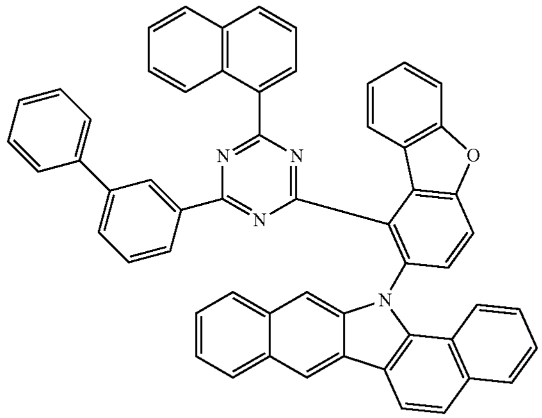
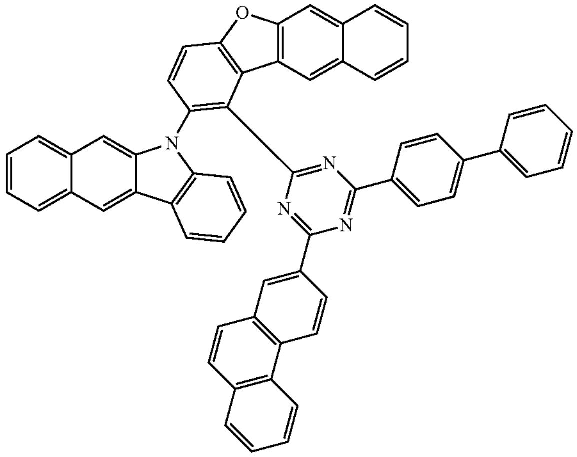
-continued
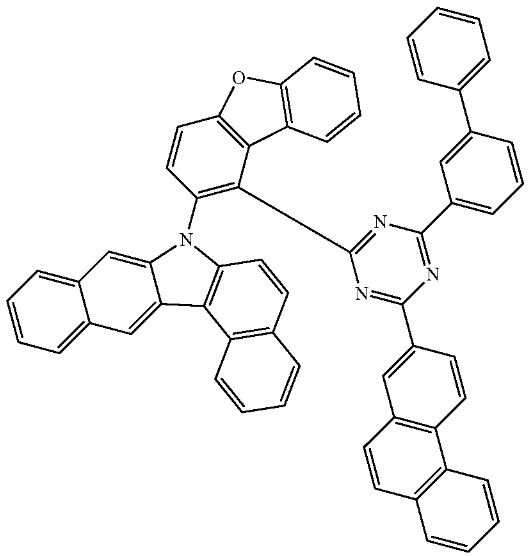
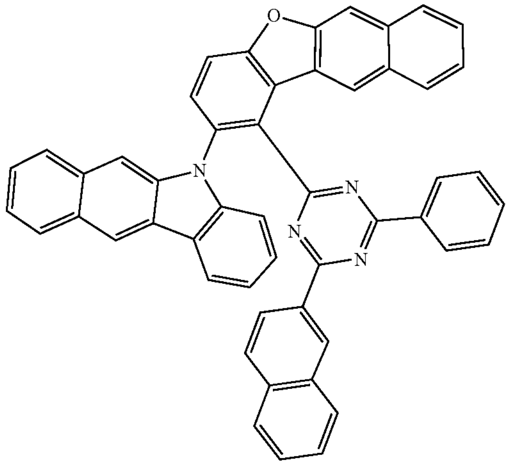
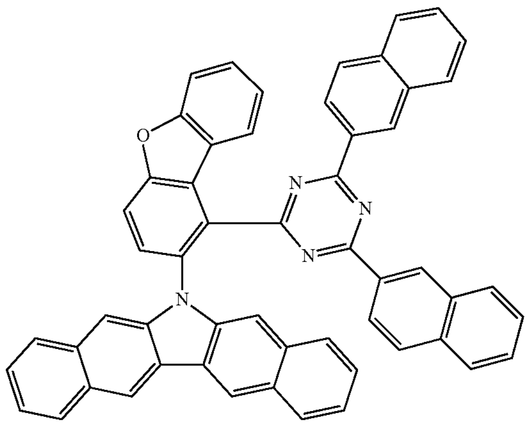

-continued
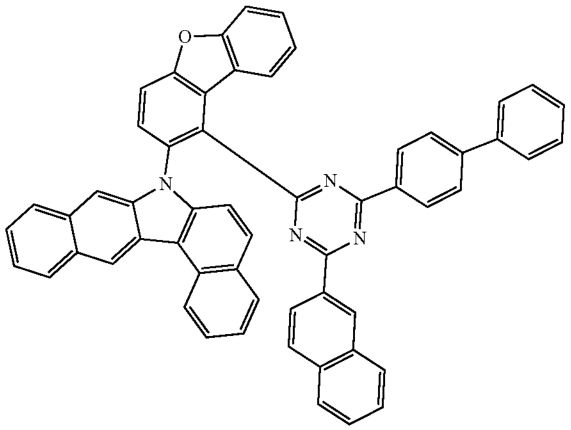
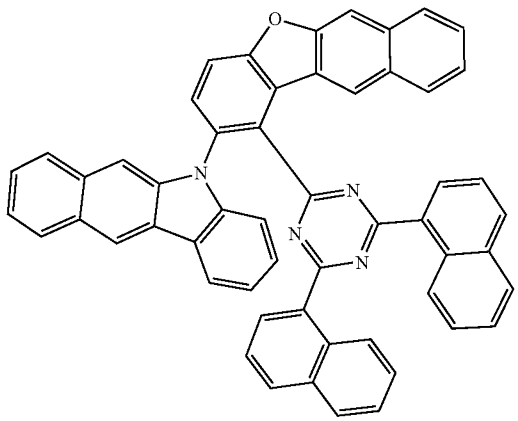
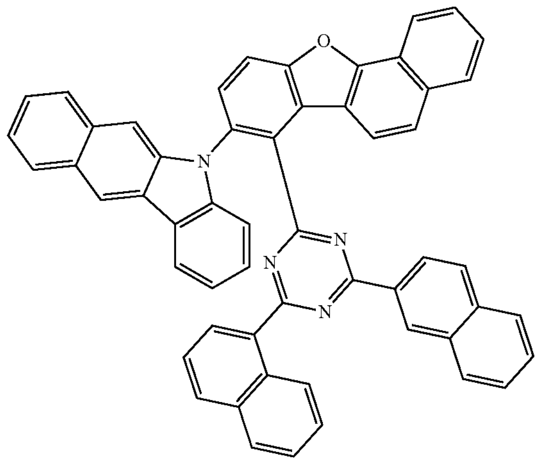
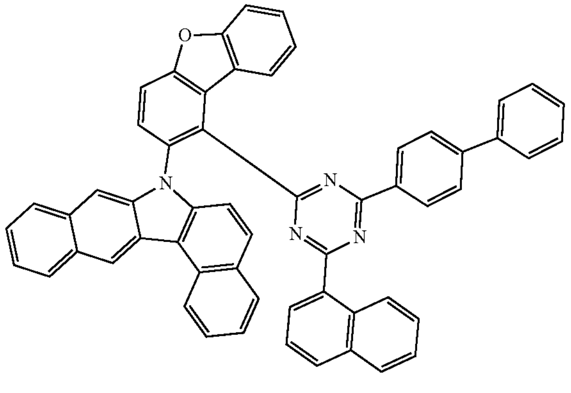
-continued
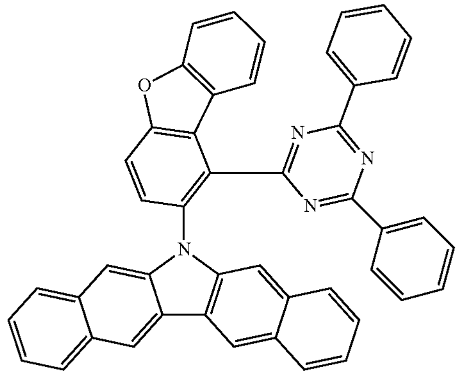
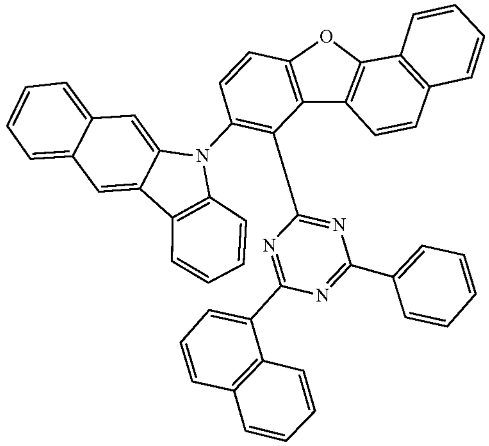
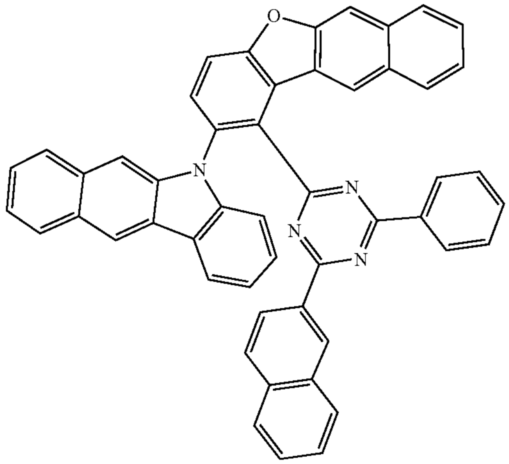
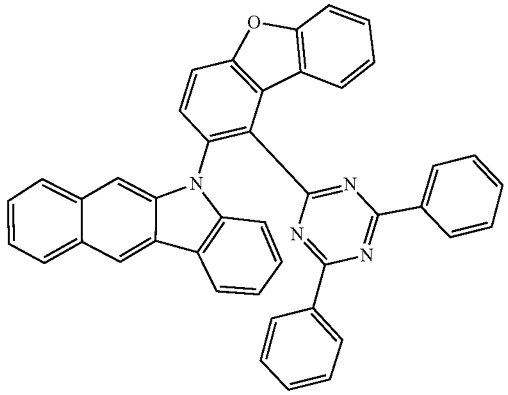

-continued
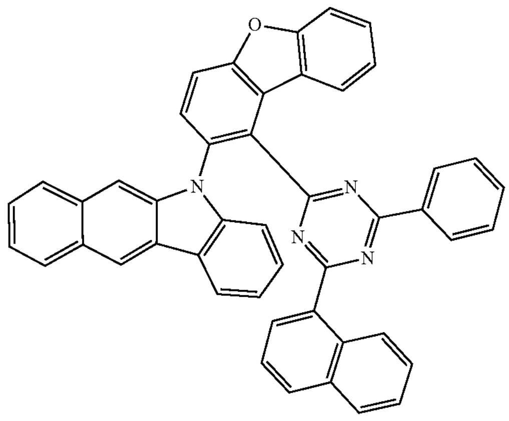
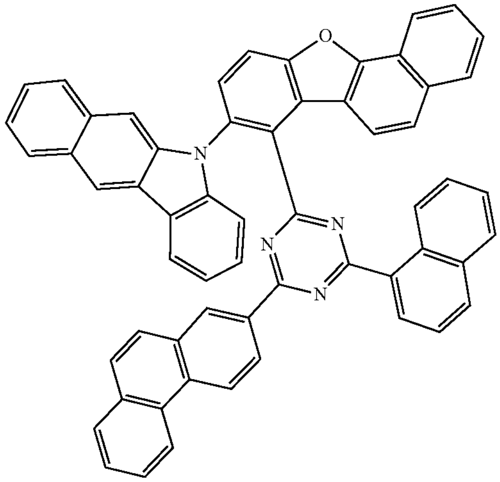
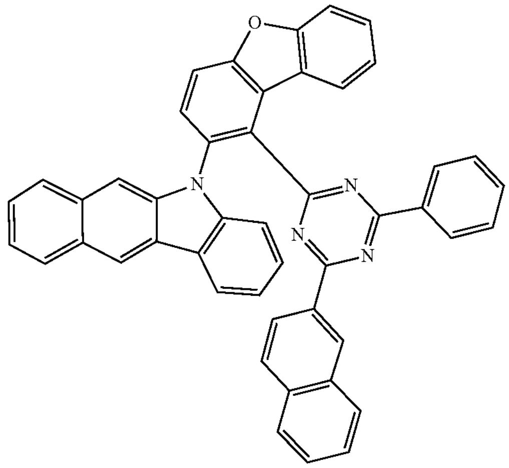
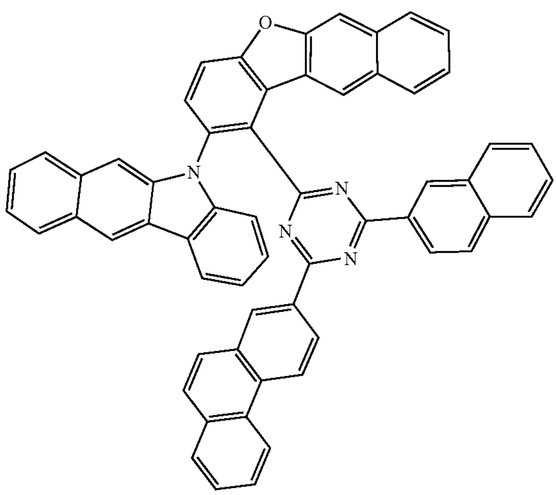
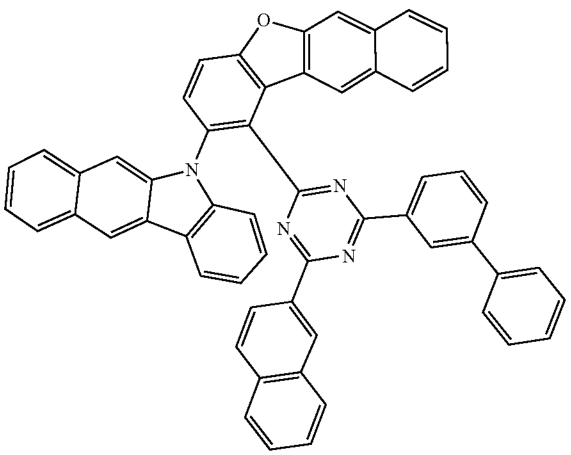
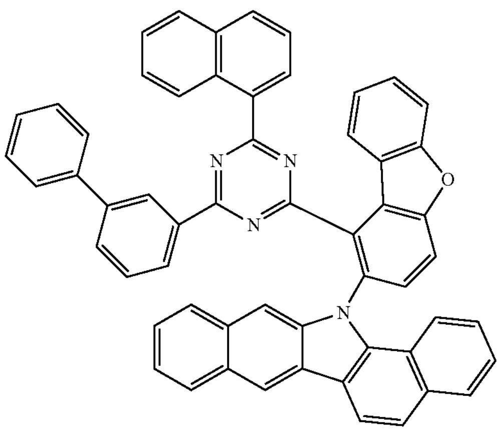
-continued -continued
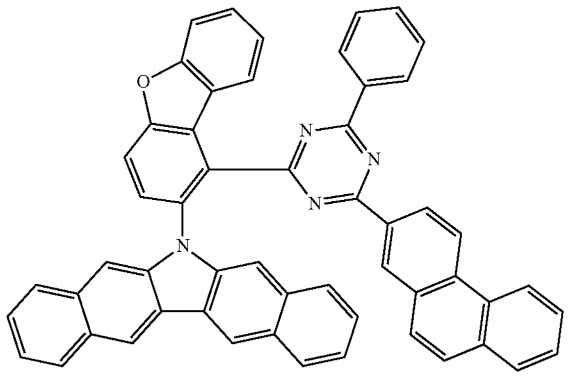
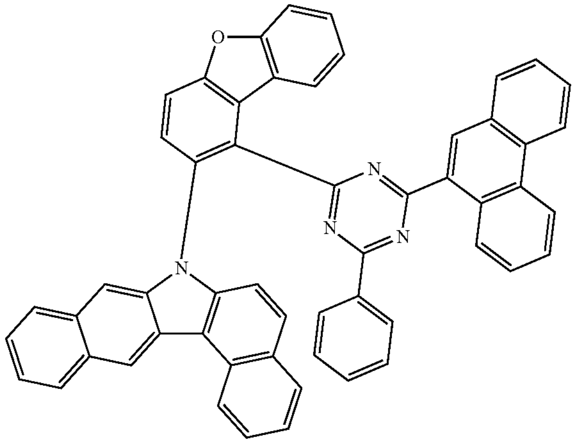
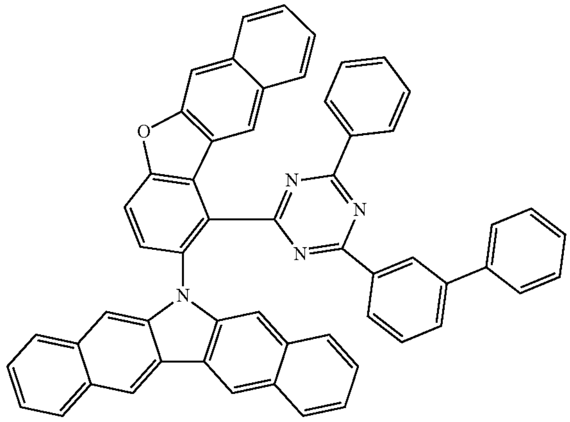
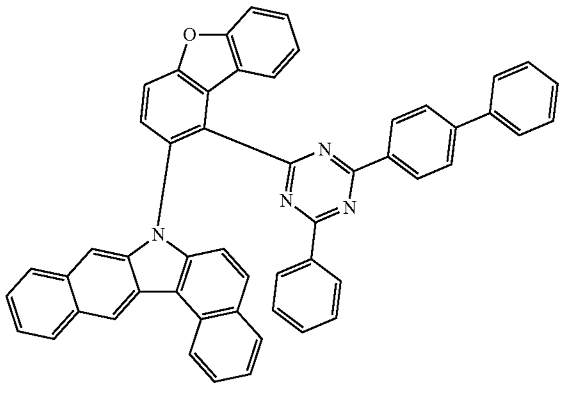
-continued
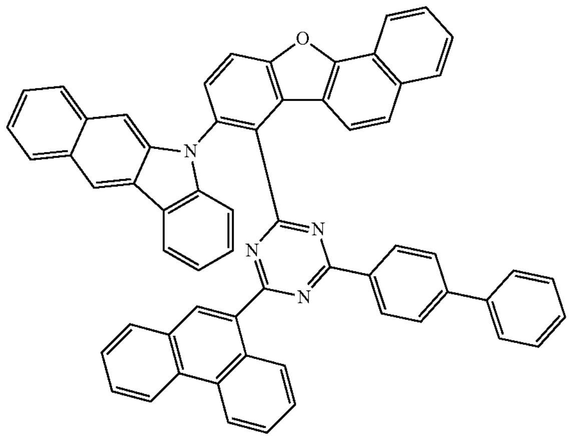
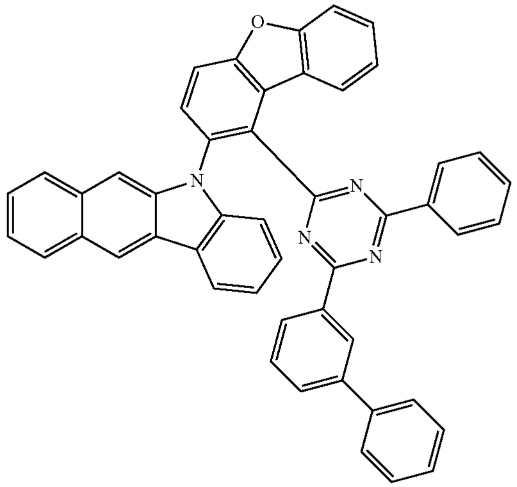
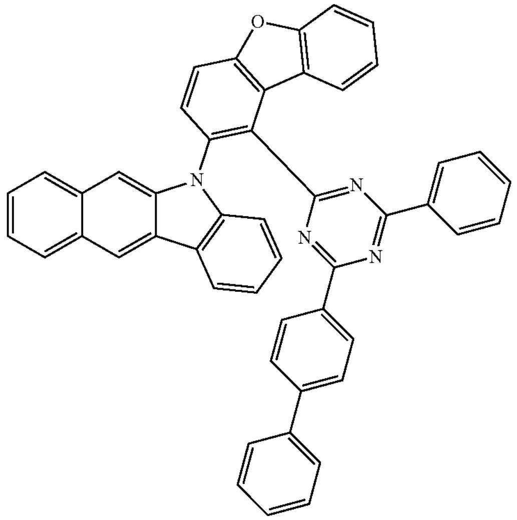

-continued
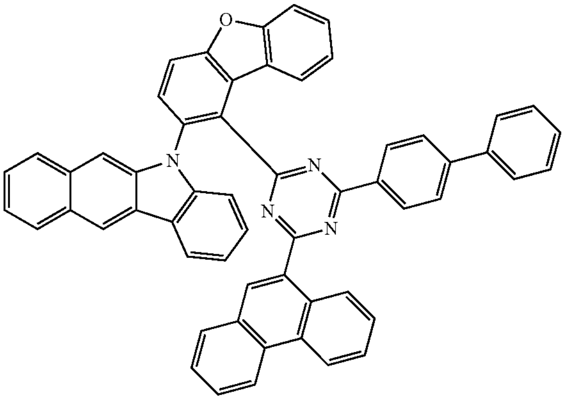
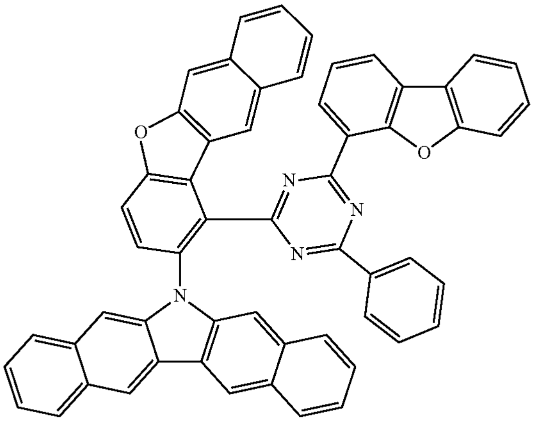
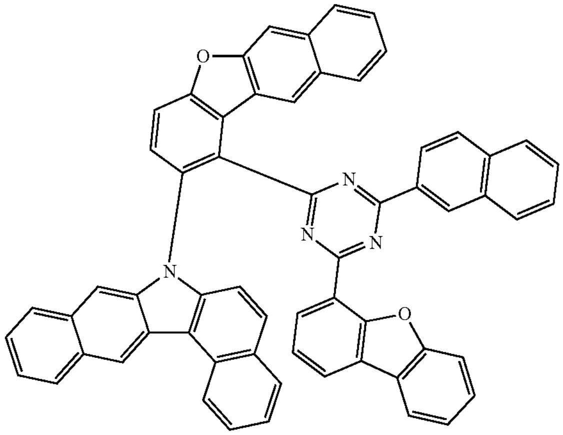
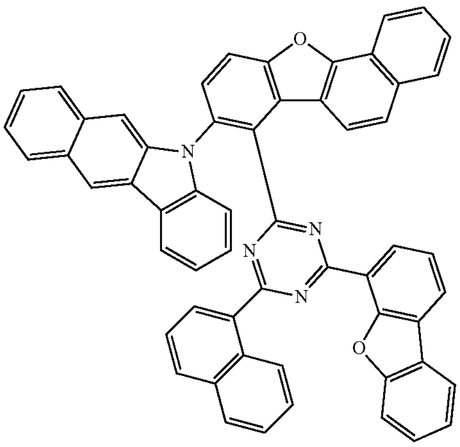
-continued
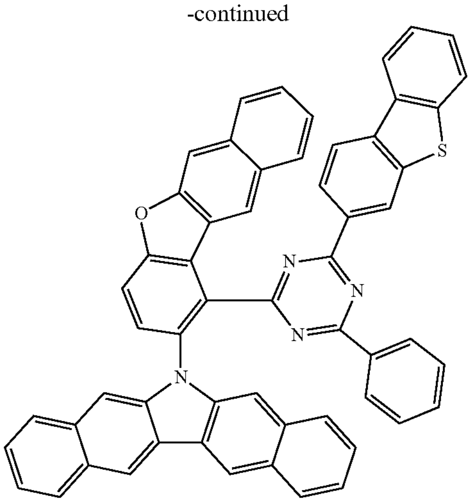
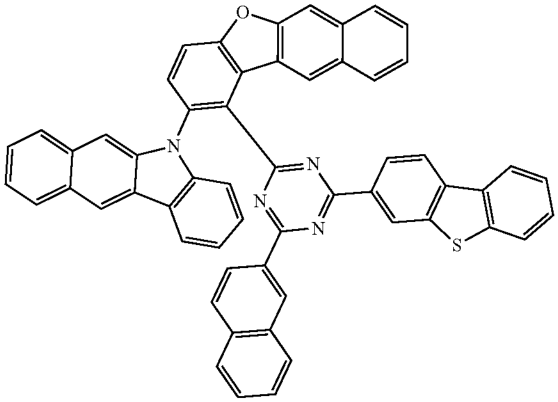
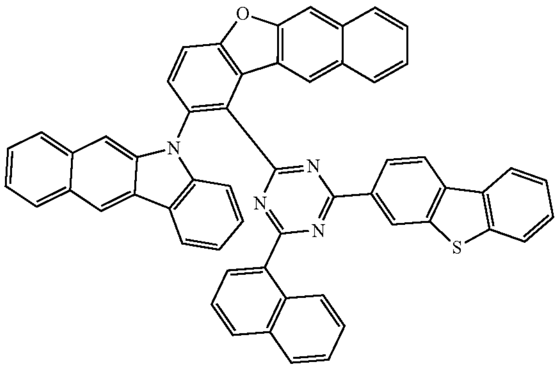
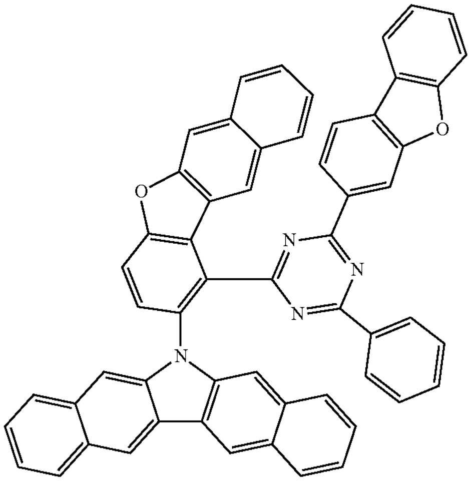

-continued
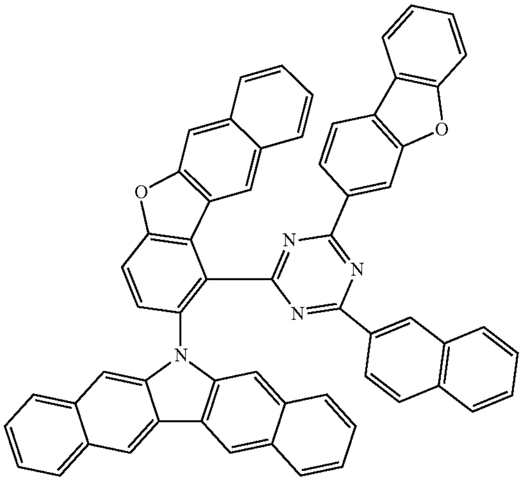
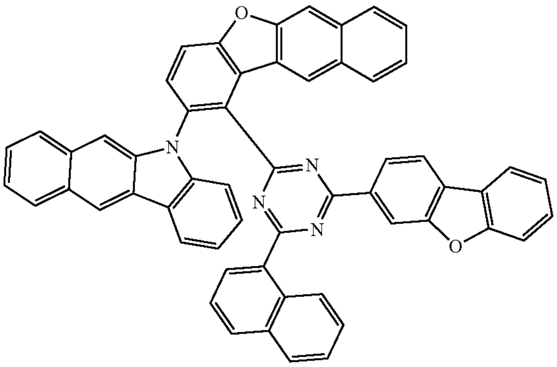
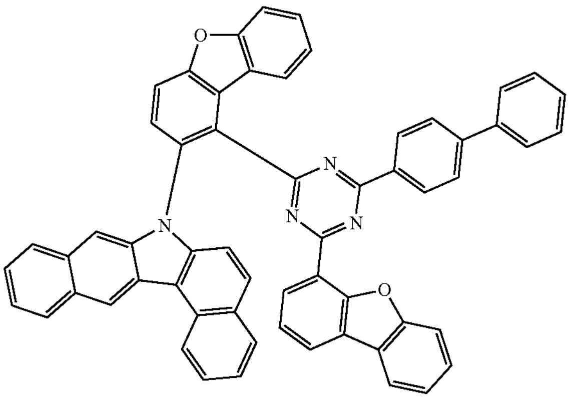
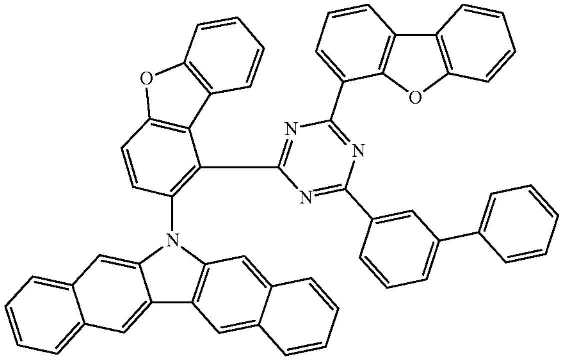
-continued
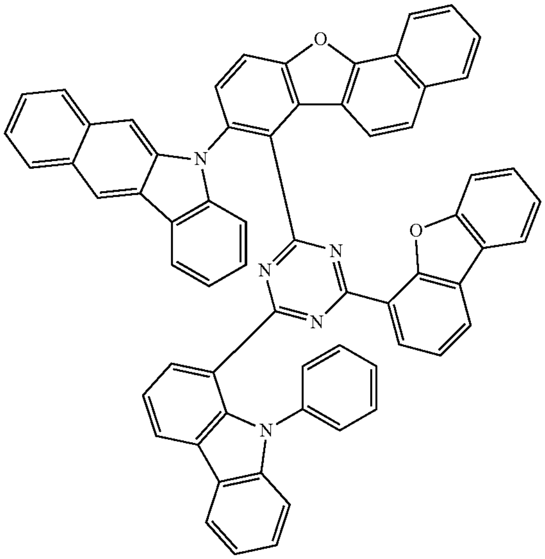
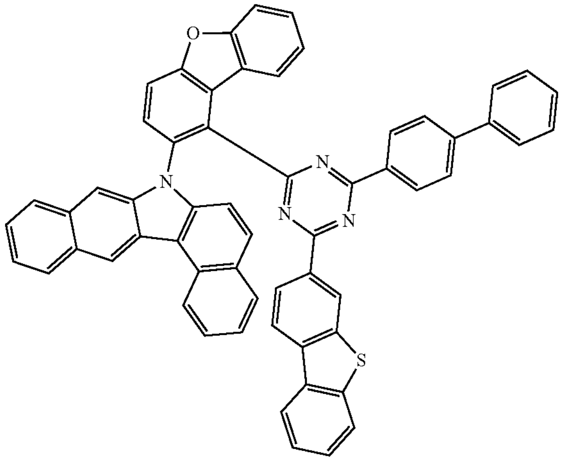
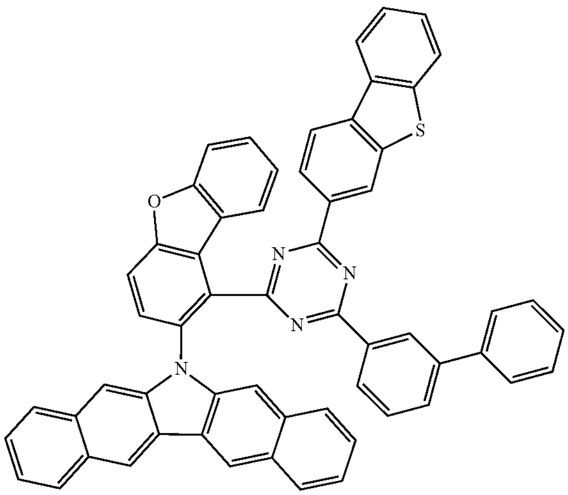

-continued
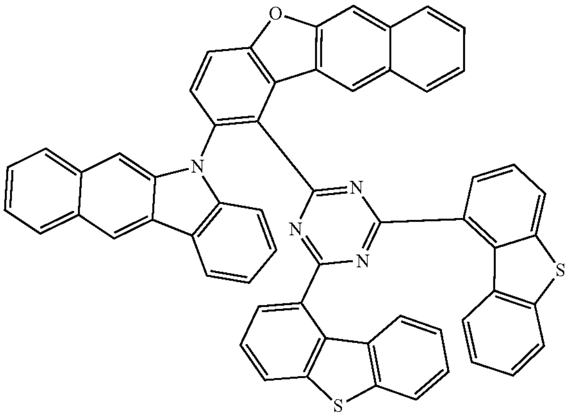
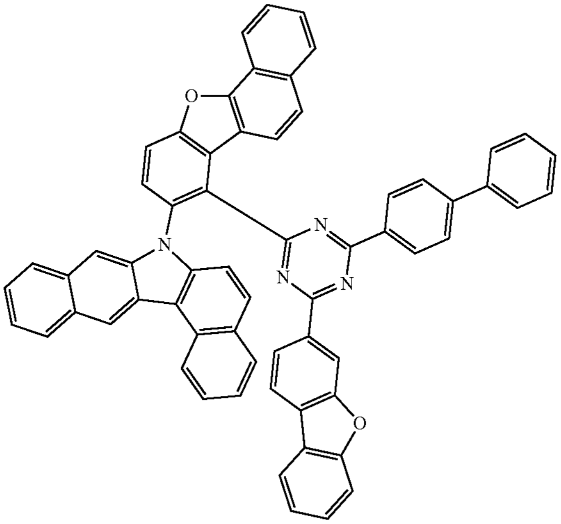
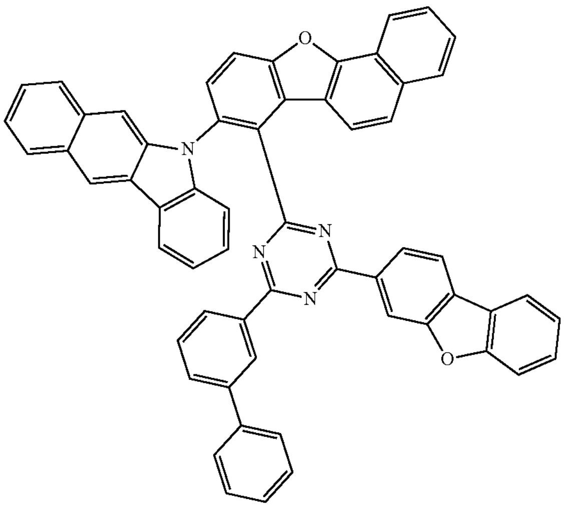
-continued
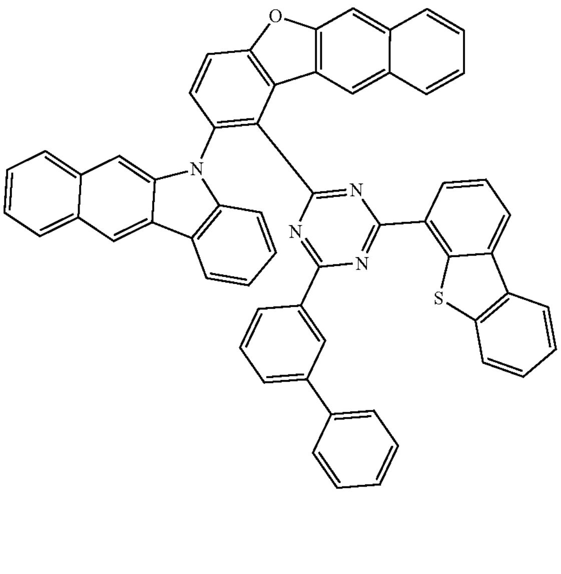
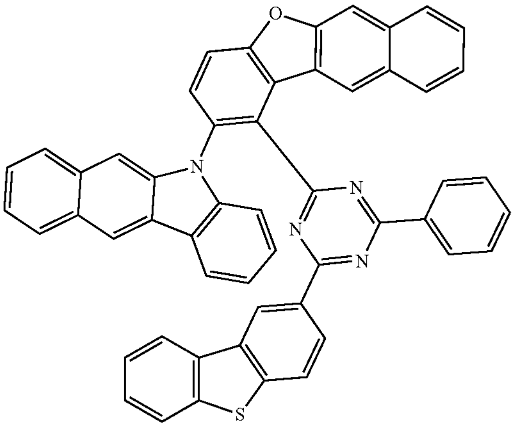
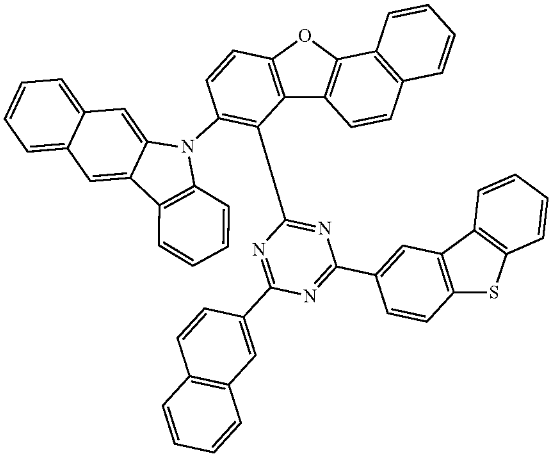

-continued
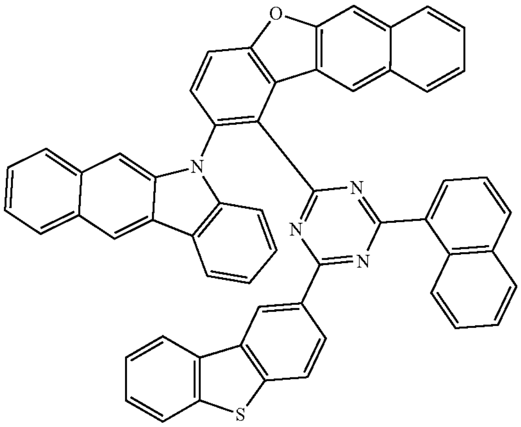
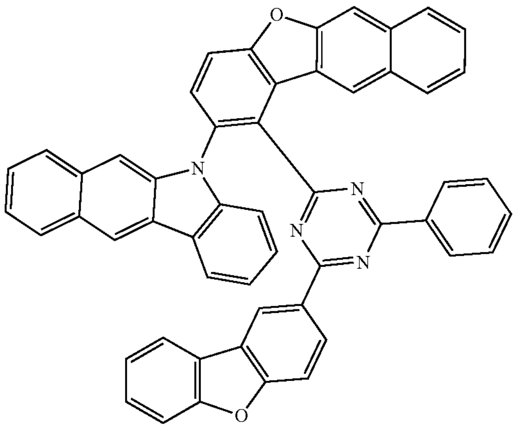
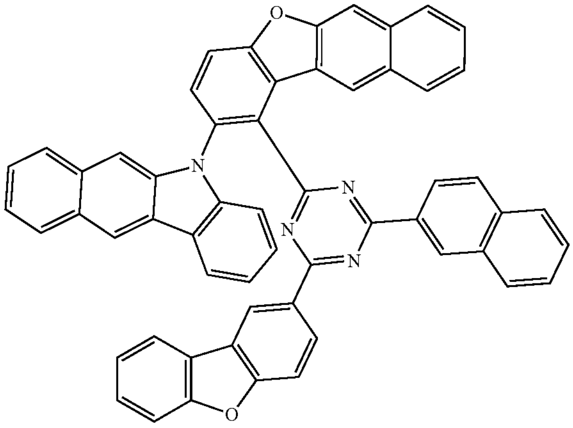
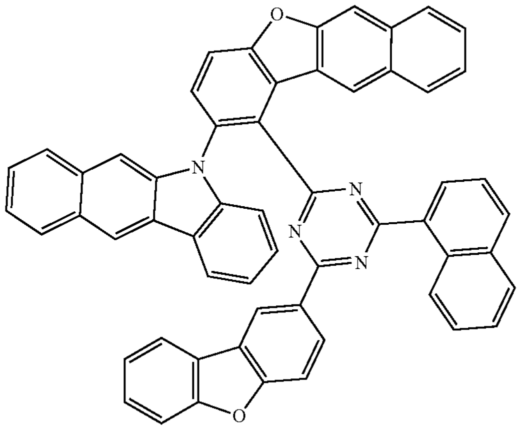
-continued
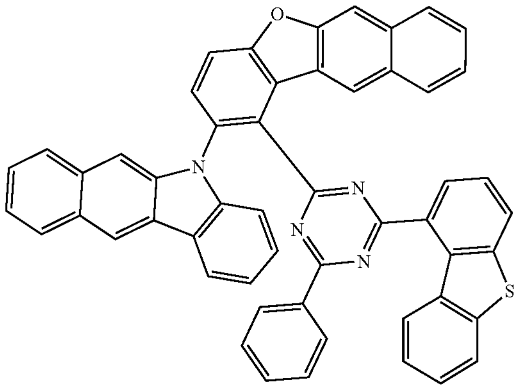
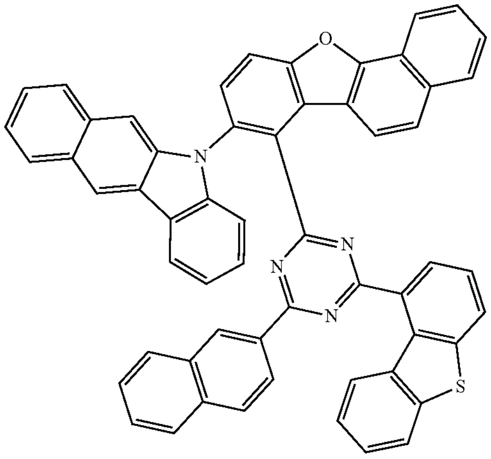
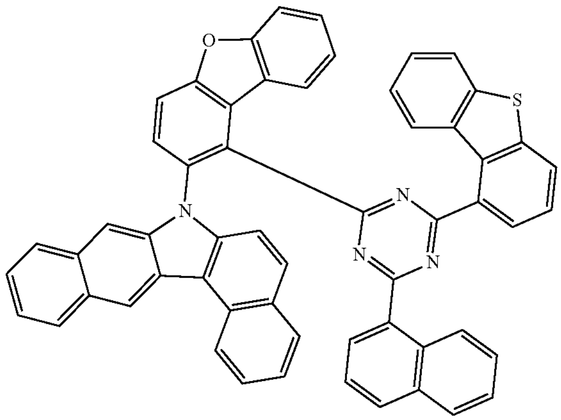
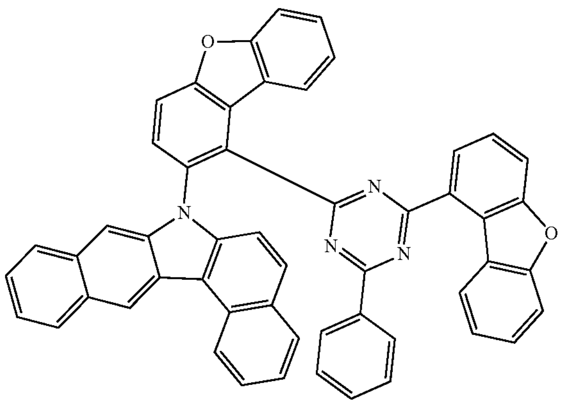

-continued
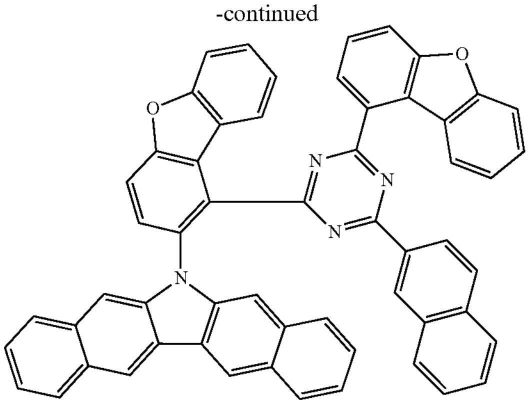
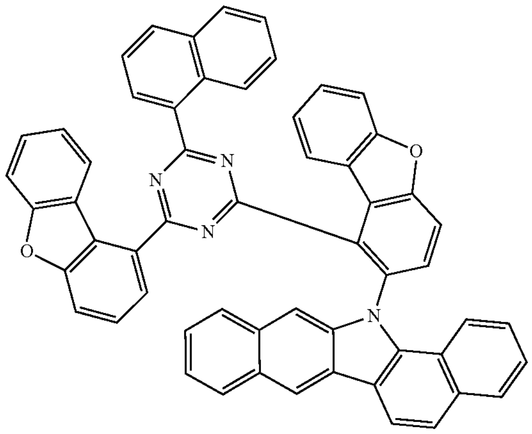
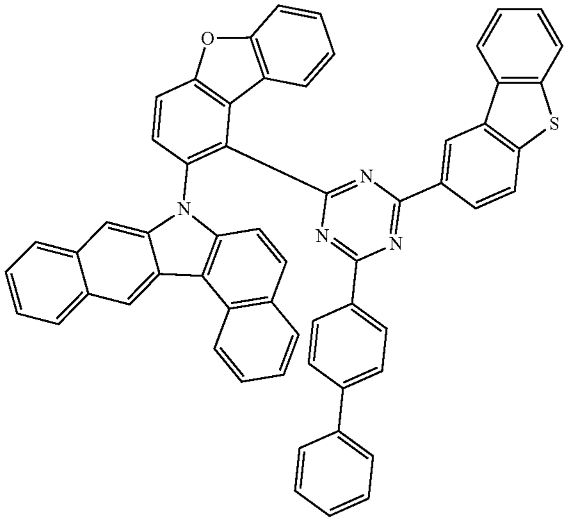
-continued
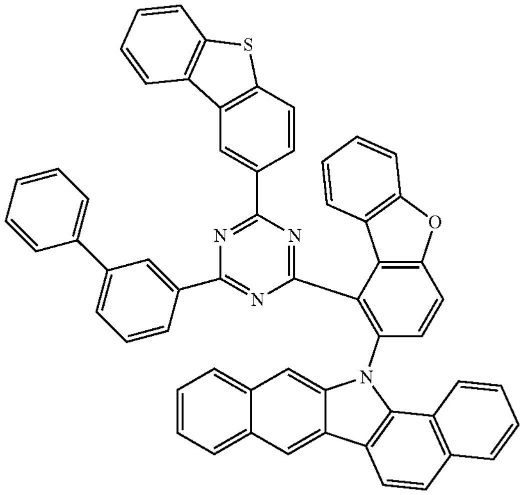
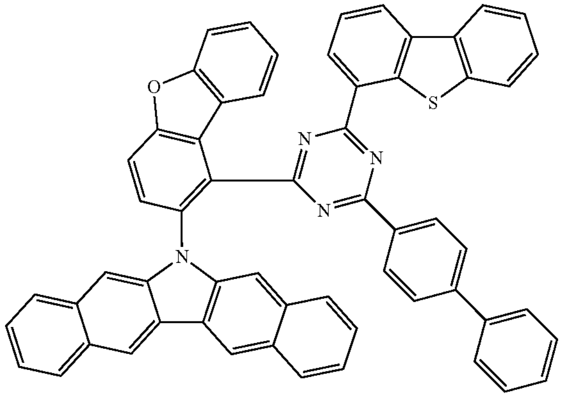
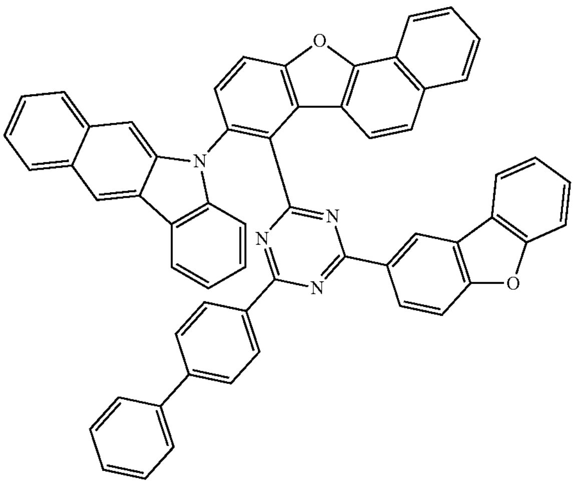

-continued
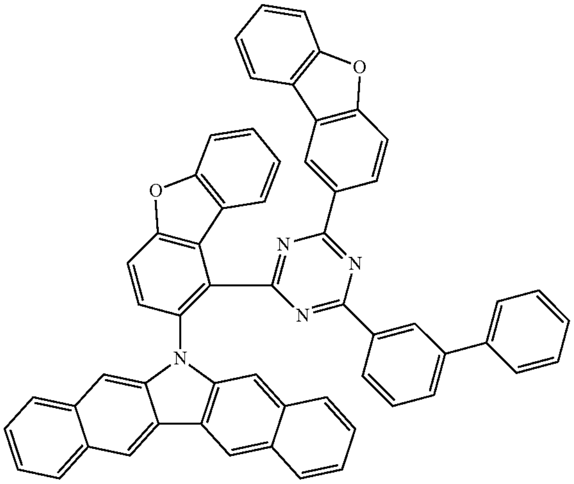
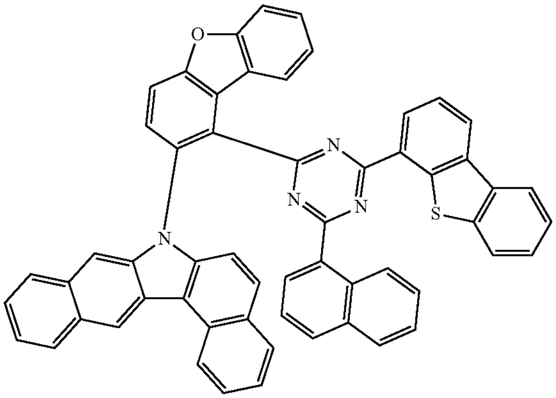
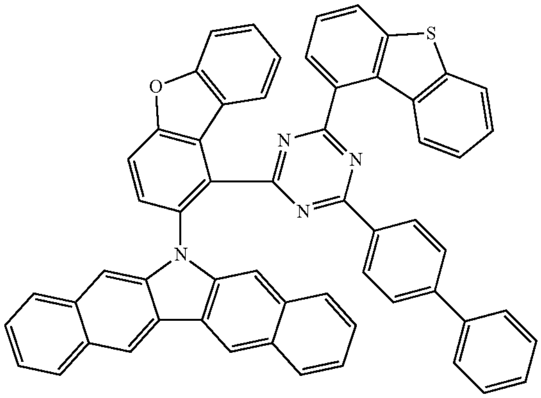
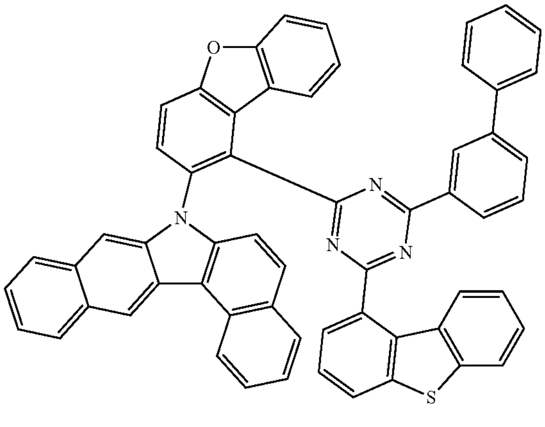
-continued
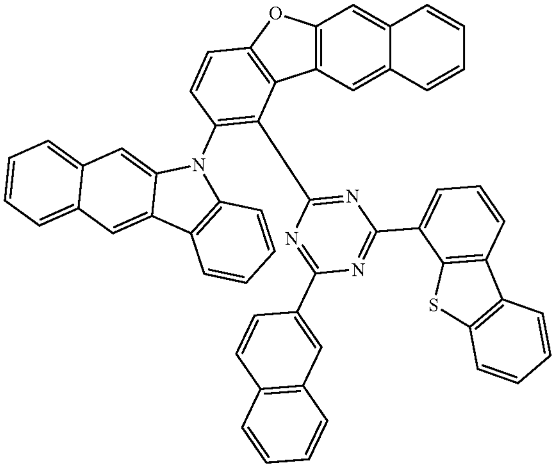
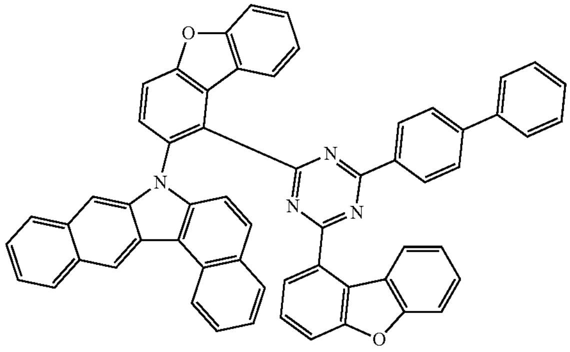
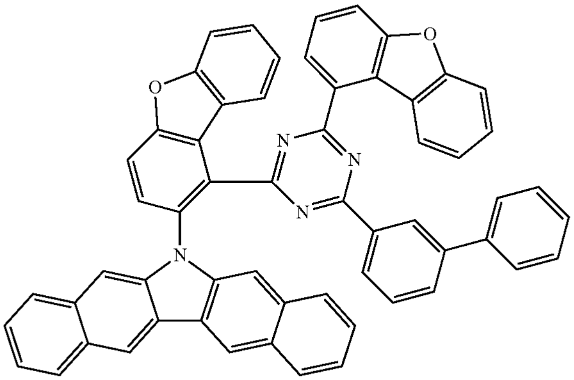
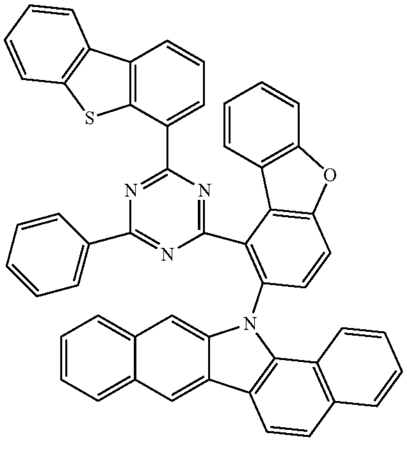

-continued
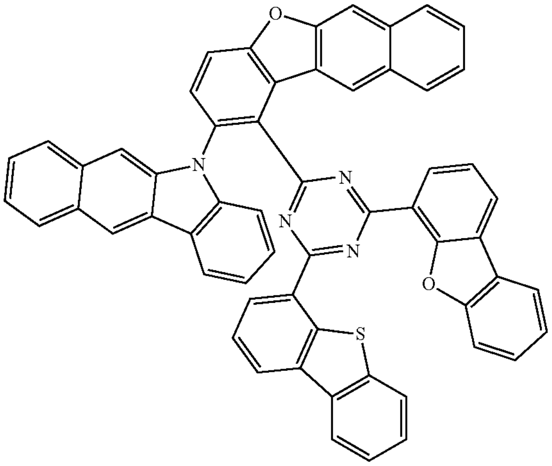
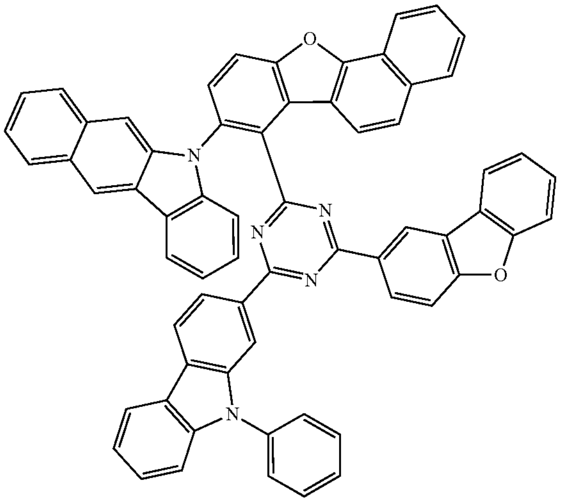
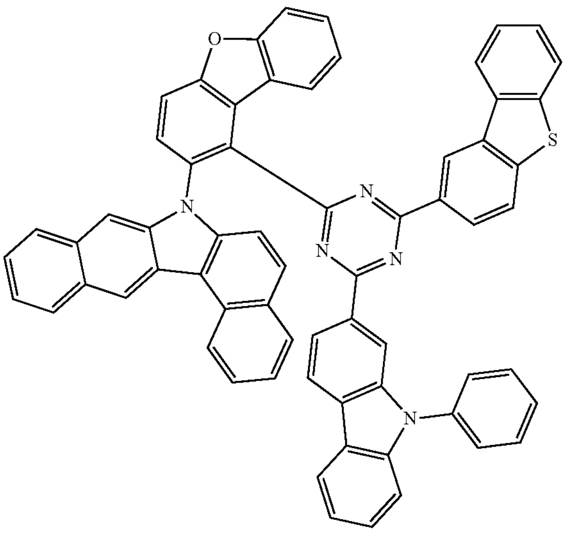
-continued
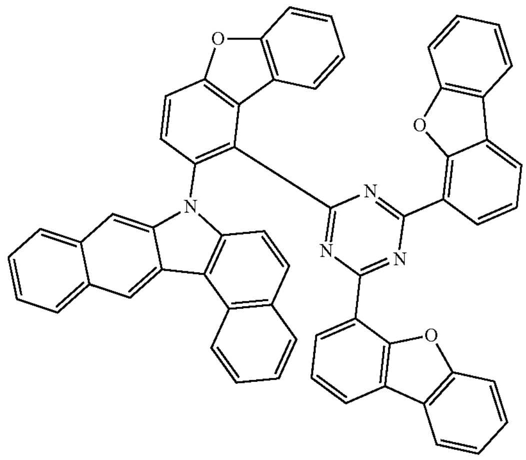
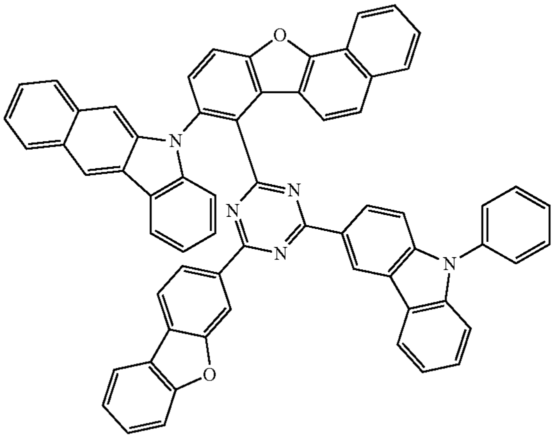
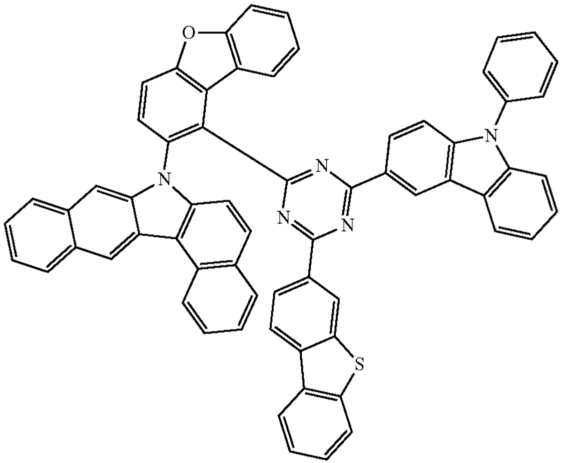

-continued
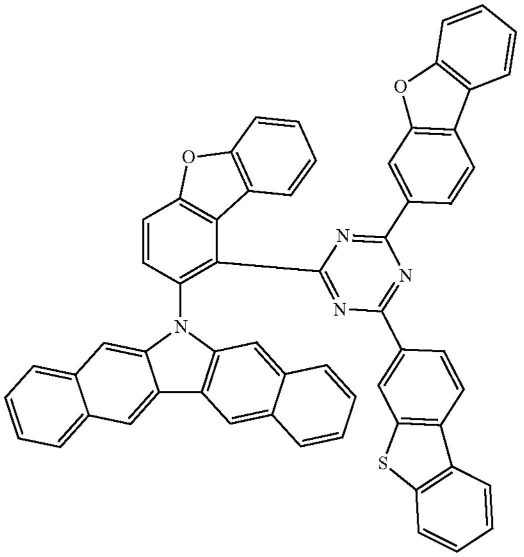
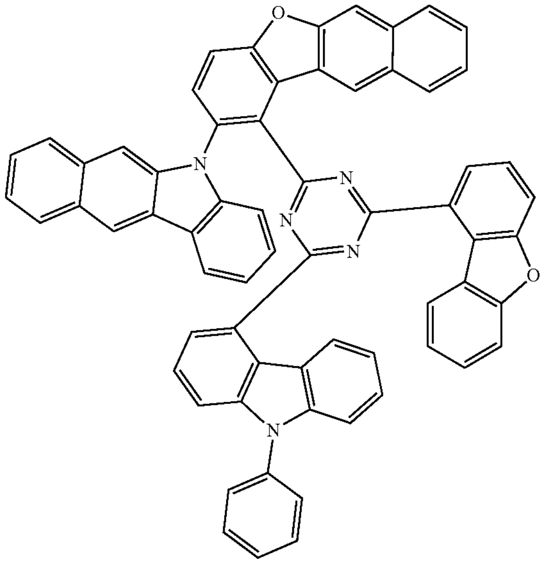
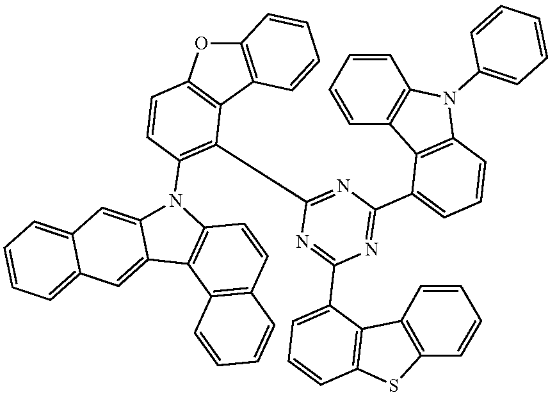
-continued
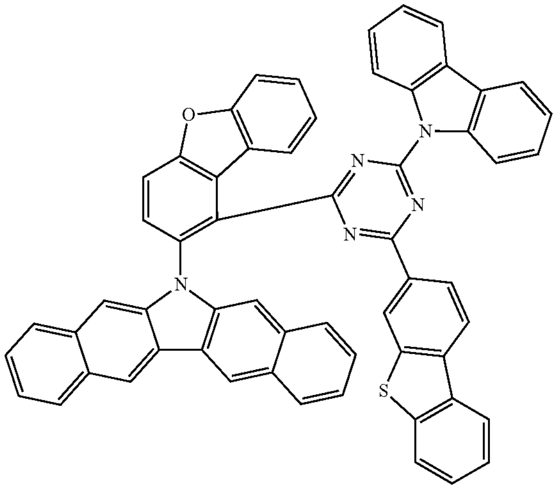
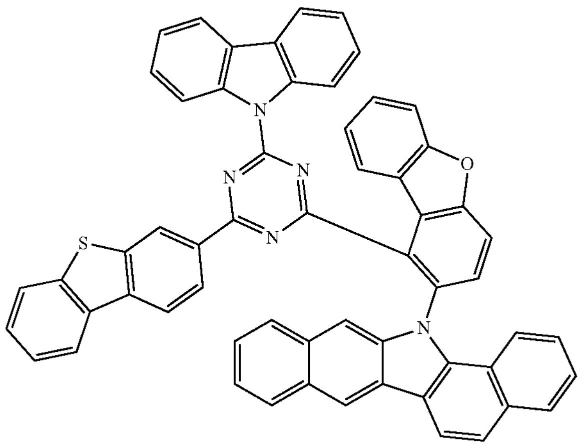
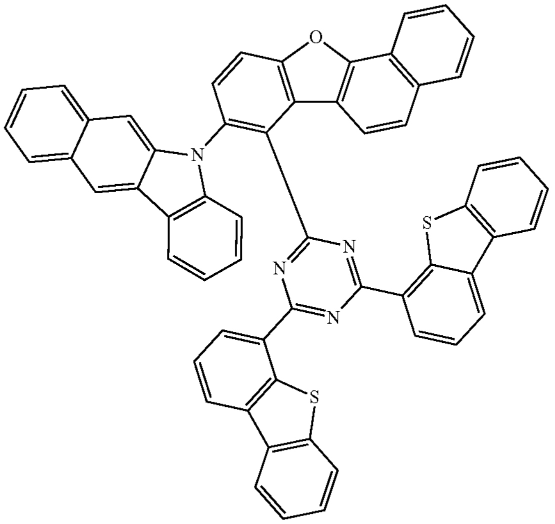

-continued
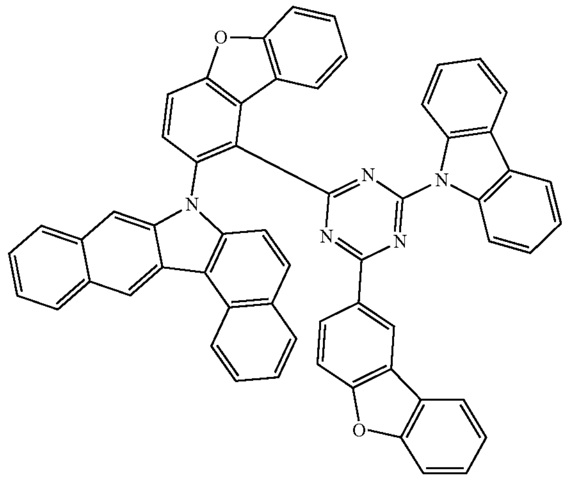
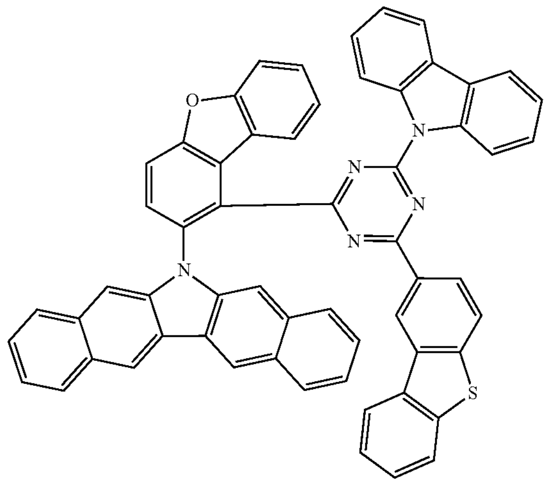
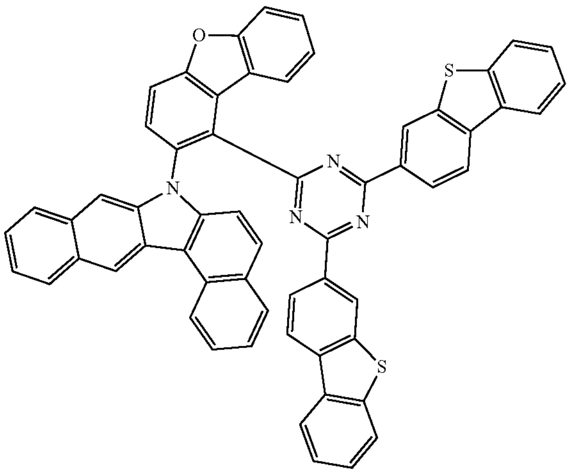
-continued
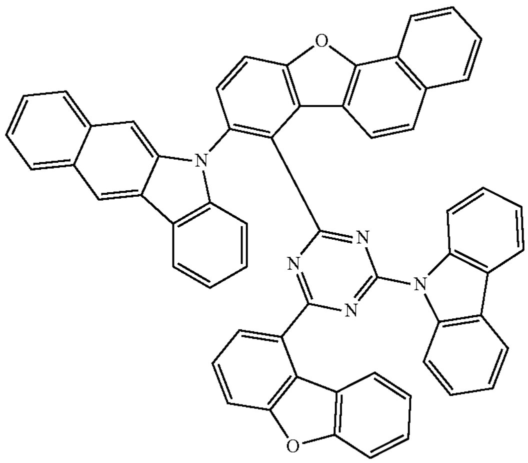
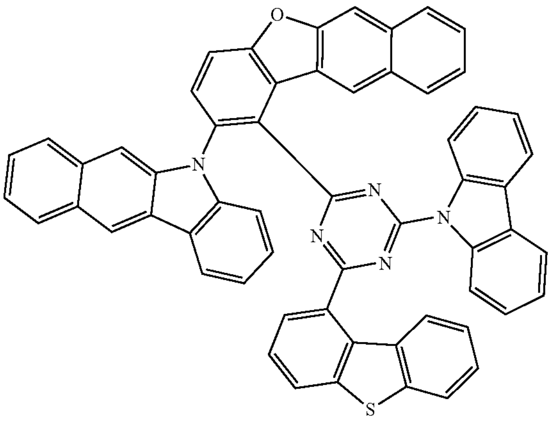
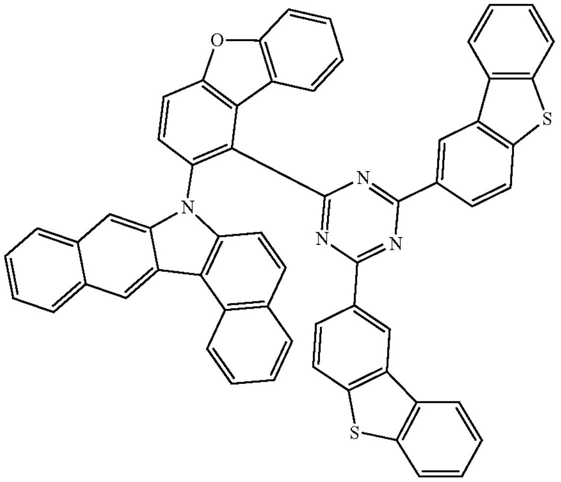

-continued
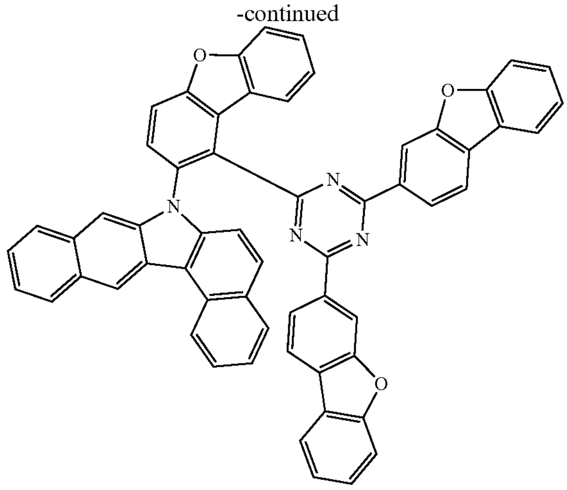
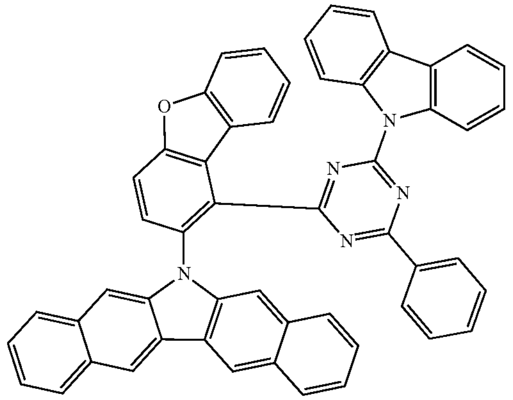
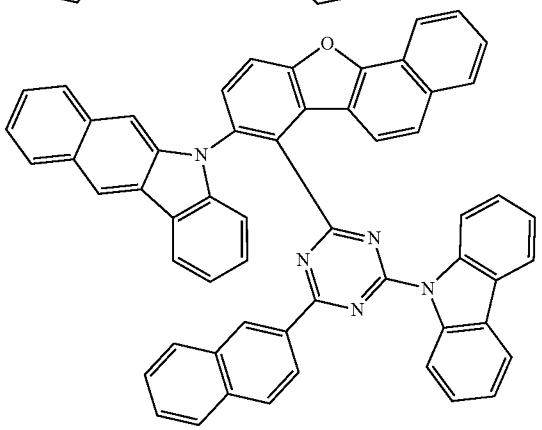
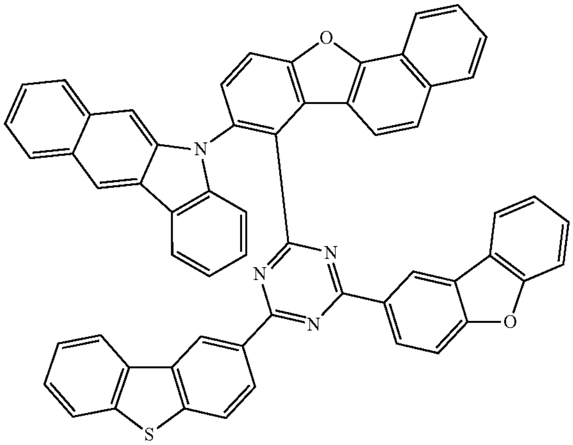
-continued
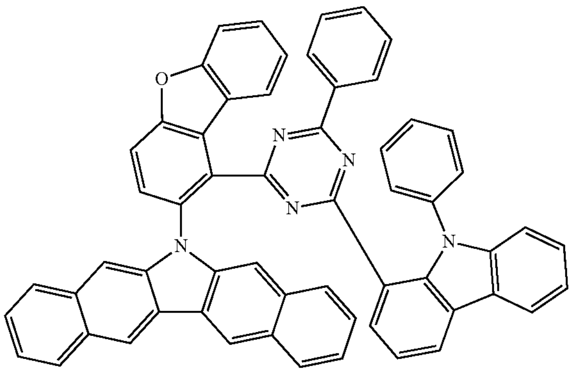
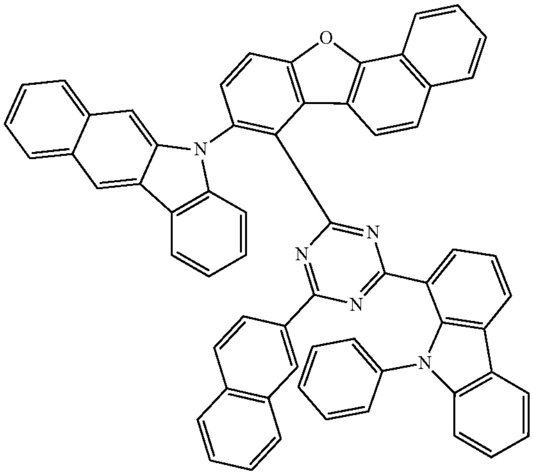
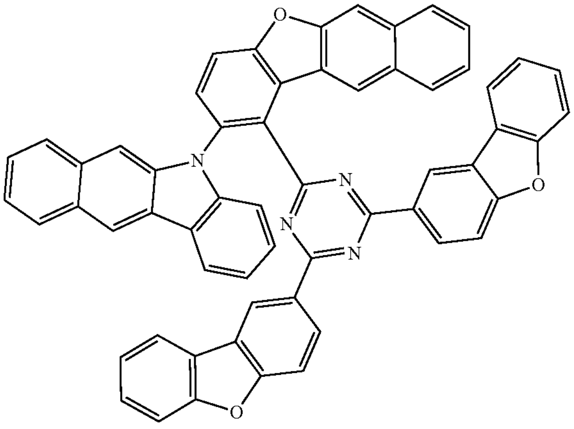
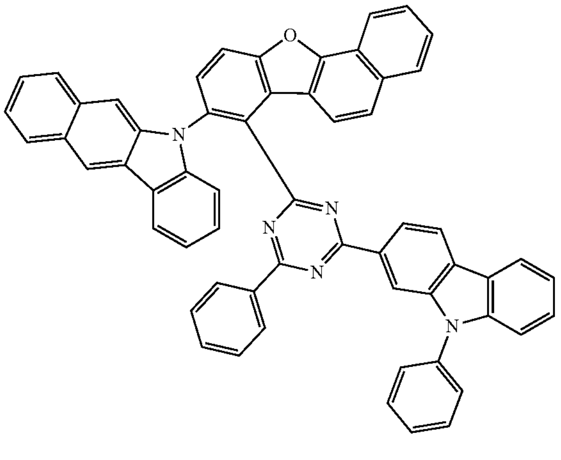

-continued
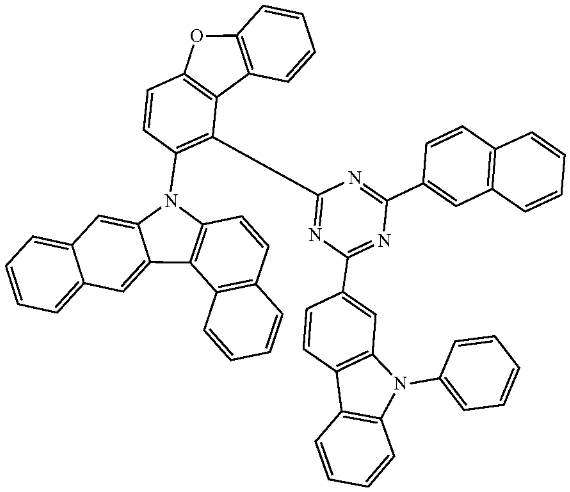
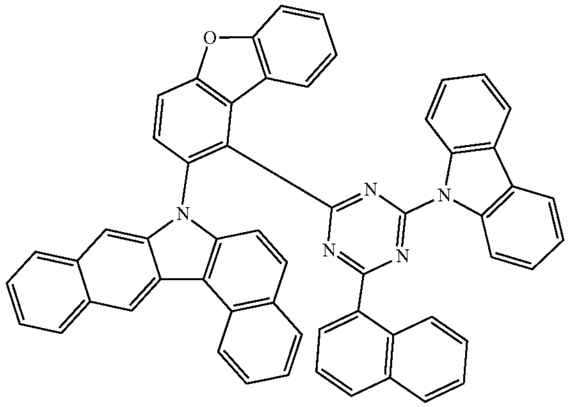
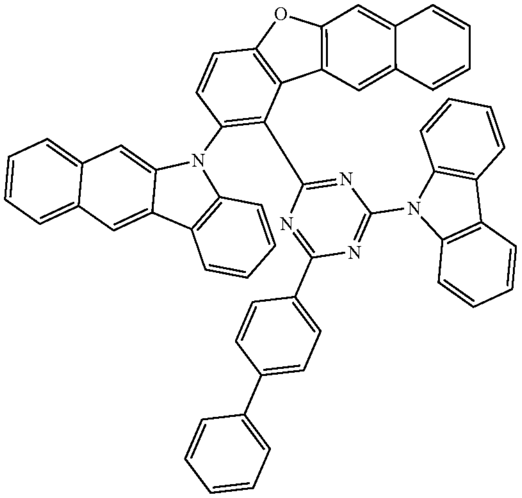
-continued
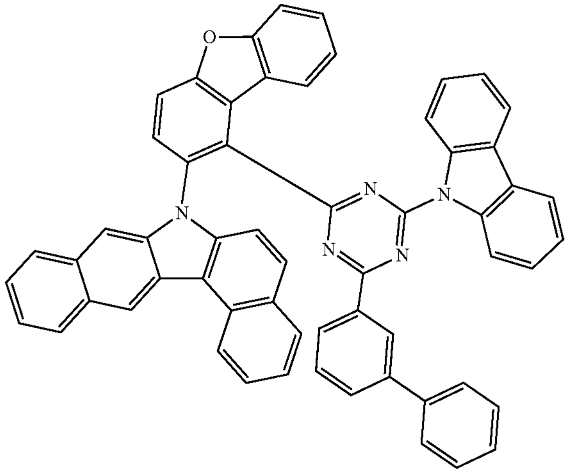
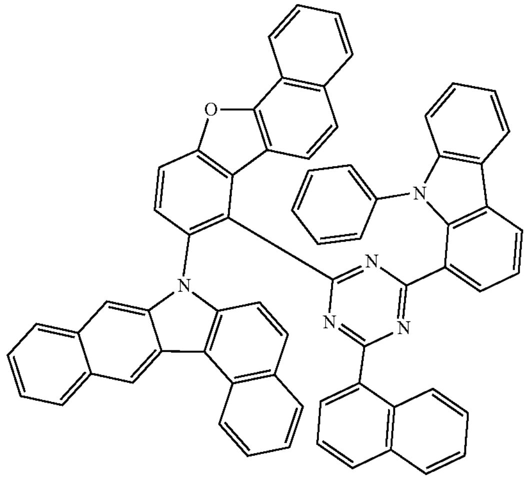
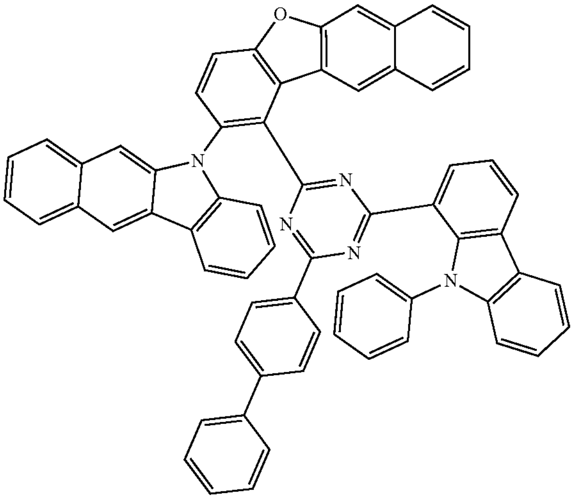

-continued
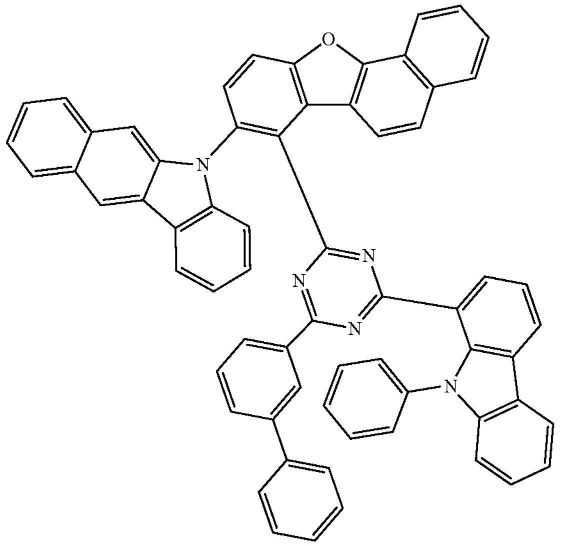
-continued
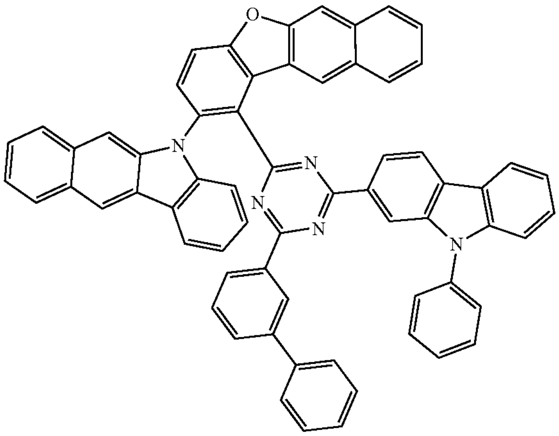
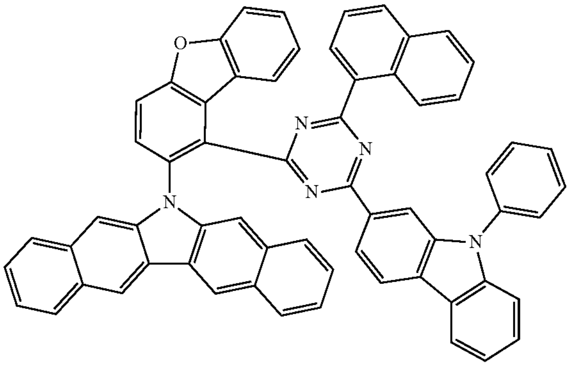
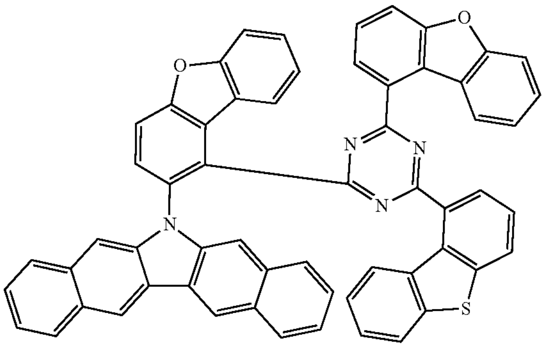
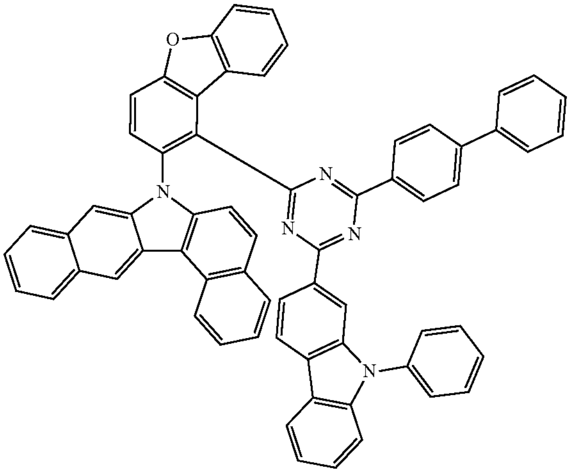
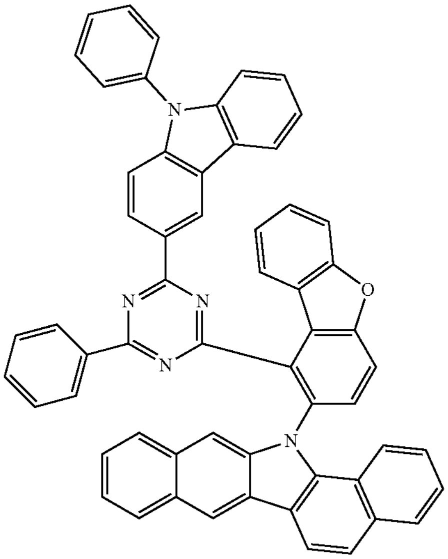

-continued
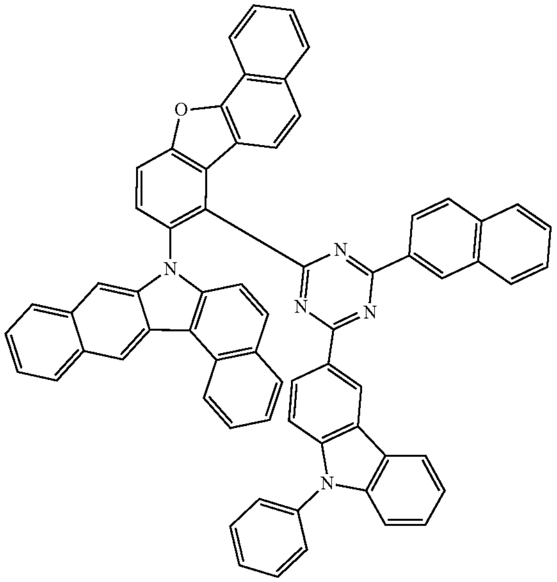
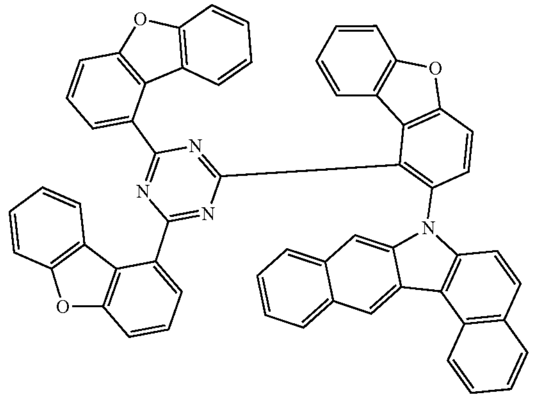
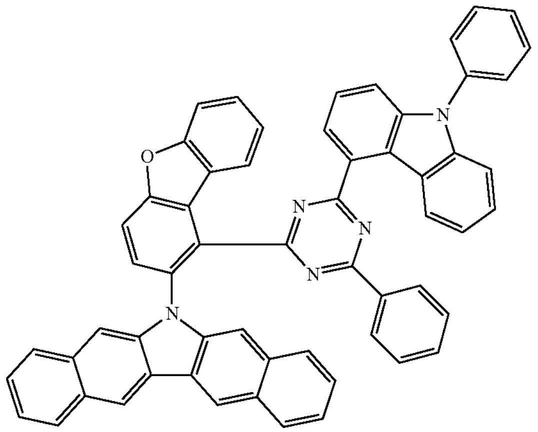
-continued
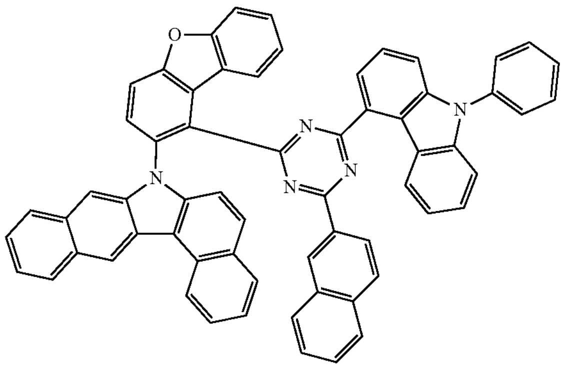
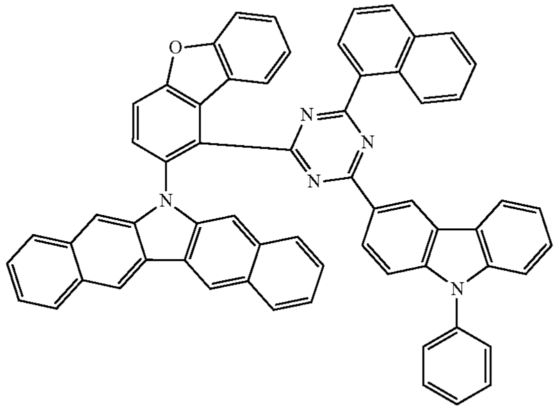
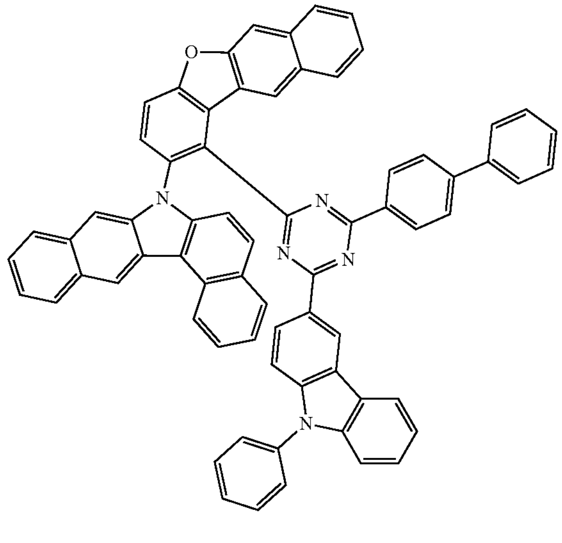

-continued

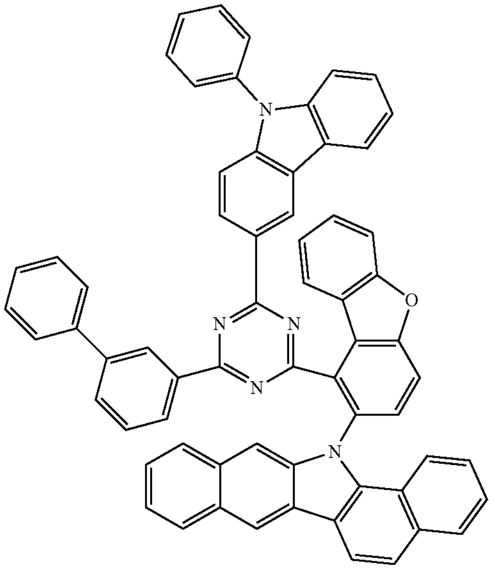

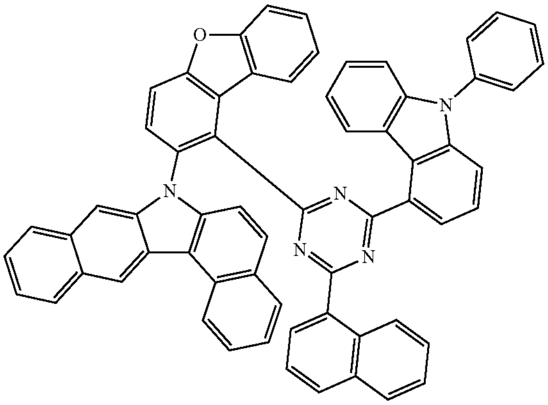

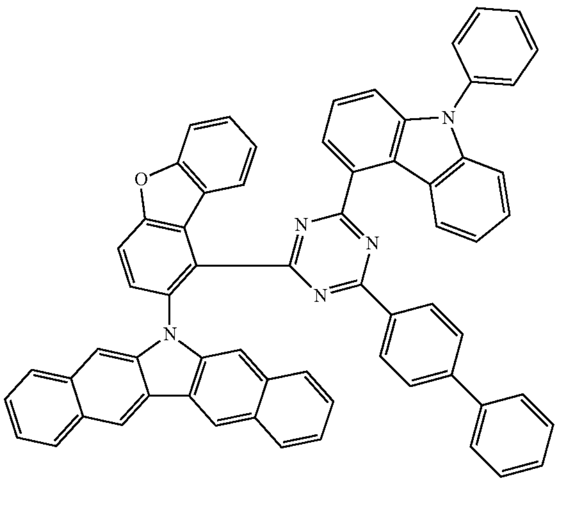

-continued

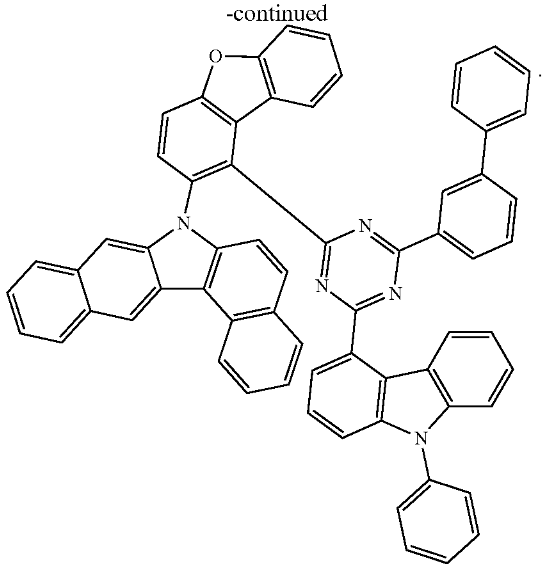

Meanwhile, the compound represented by Chemical Formula 1 may be prepared, for example, by the method as shown in Reaction Scheme 1 below.

[Reaction Scheme 1]

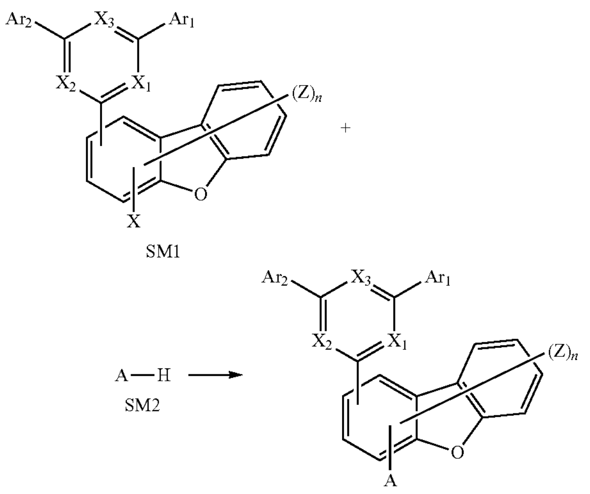

SM1 SM2 1 in the Reaction Scheme 1, each X is independently halogen, preferably bromo, or chloro, and the definitions of other substituents are the same as described above.

Specifically, the compound represented by the Chemical Formula 1 is prepared by combining the starting materials SM1 and SM2 through an amine substitution reaction. Such an amine substitution reaction is preferably performed in the presence of a palladium catalyst and a base. In addition, the reactive group for the amine substitution reaction may be appropriately changed, and the method for preparing the compound represented by the Chemical Formula 1 may be more specifically described in Preparation Examples described below.

Meanwhile, the second compound is a biscarbazole-based compound, preferably, has a structure in which $T_1$ to $T_4$ are each independently a $C_{6-20}$ aromatic ring. More preferably, $T_1$ to $T_4$ are a benzene ring unsubstituted or substituted with deuterium, or a naphthalene ring unsubstituted or substituted with deuterium.

Most preferably, $T_1$ to $T_4$ are each a benzene ring, wherein the second compound is represented by the following Chemical Formula 2-1:

[Chemical Formula 2-1]

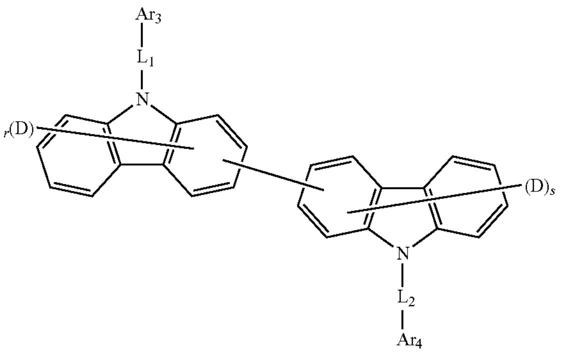

in the Chemical Formula 2-1,

D is deuterium, r and s are each independently an integer from 0 to 7, and the descriptions of each substituent are the same as defined in the Chemical Formula 2.

Preferably, $L_1$ and $L_2$ are each independently a single bond, or an unsubstituted $C_{6-20}$ arylene.

More preferably, $L_1$ and $L_2$ are each independently a single bond, phenylene, or naphthylene.

Preferably, $Ar_3$ and $Ar_4$ are each independently a $C_{6-20}$ aryl unsubstituted or substituted with $C_{1-10}$ alkyl or $C_{6-20}$ aryl; or a $C_{2-20}$ heteroaryl containing O or S.

More preferably, Ara and Ara are each independently phenyl, biphenylyl, terphenylyl, naphthyl, phenanthrenyl, triphenylenyl, fluorenyl, spirobifluorenyl, fluoranthenyl, dibenzothiophenyl, or dibenzofuranyl, where $Ar_3$ and $Ar_4$ may be unsubstituted or substituted 1 to 4 substituents each independently selected from the group consisting of $C_{1-10}$ alkyl and $C_{6-20}$ aryl.

Most preferably, Ara and Ara are each independently any one selected from the group consisting of the following:

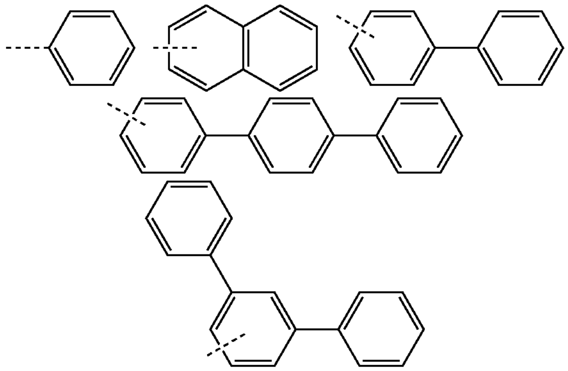

-continued

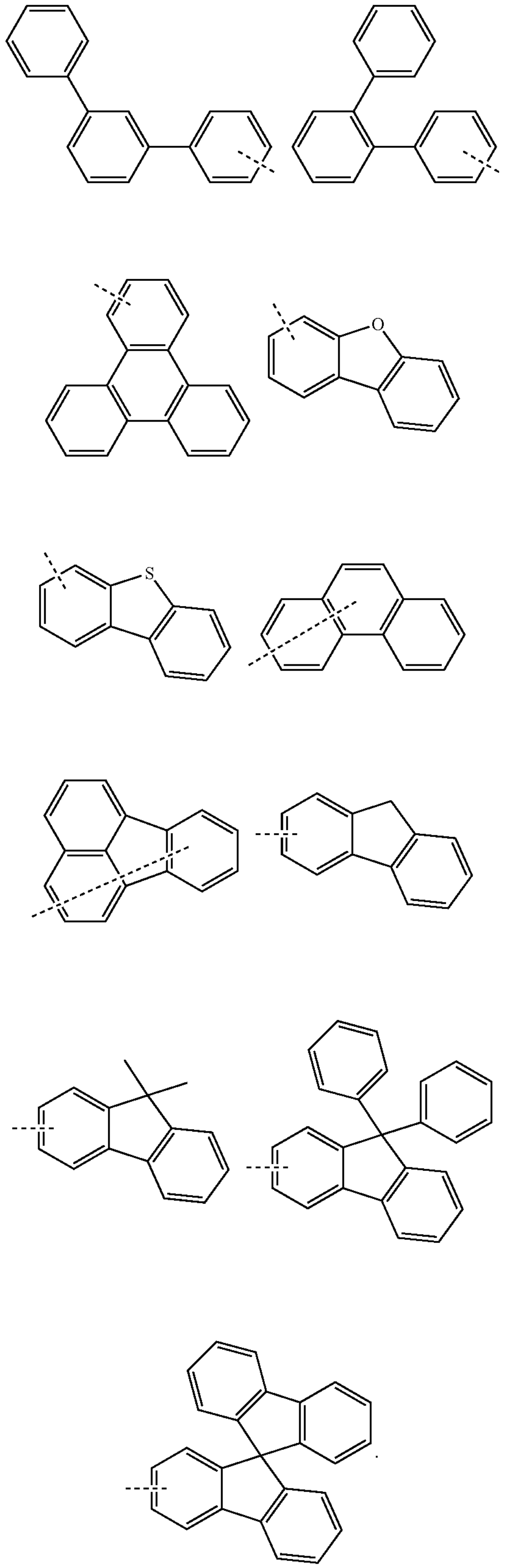

In this case, $Ar_3$ and $Ar_4$ may be the same as or different from each other.

Preferably, the second compound is represented by the following Chemical Formula 2-2:
[Chemical Formula 2-2]
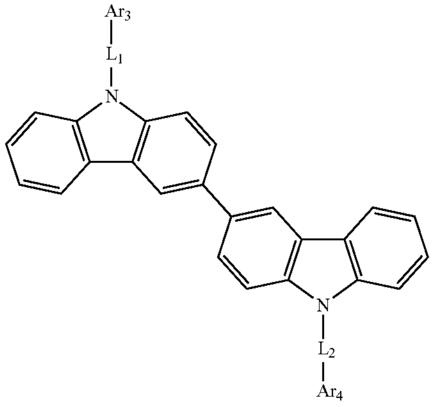
in the Chemical Formula 2-2,
$L_1$ and $L_2$ are each independently a single bond, phenylene, or naphthylene, and
$Ar_3$ and $Ar_4$ are the same as defined in the Chemical Formula 2.
Specific examples of the second compound are as follows:
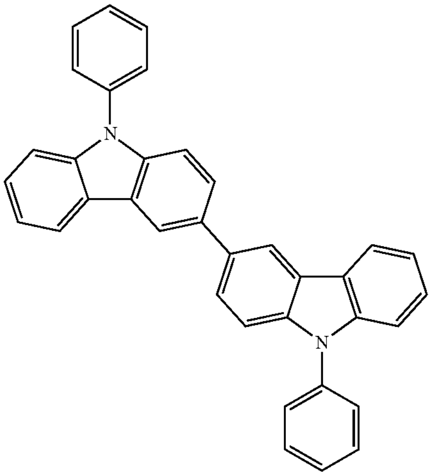
-continued
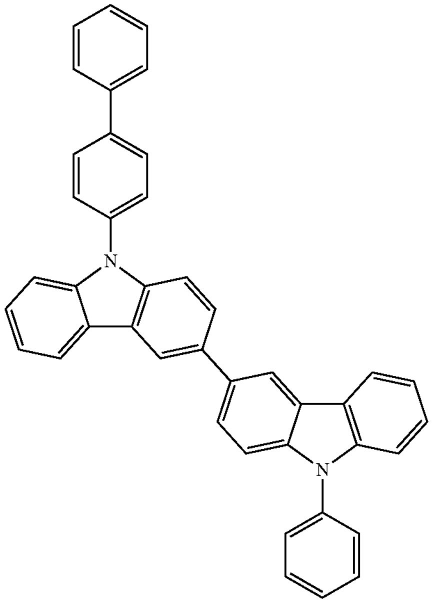
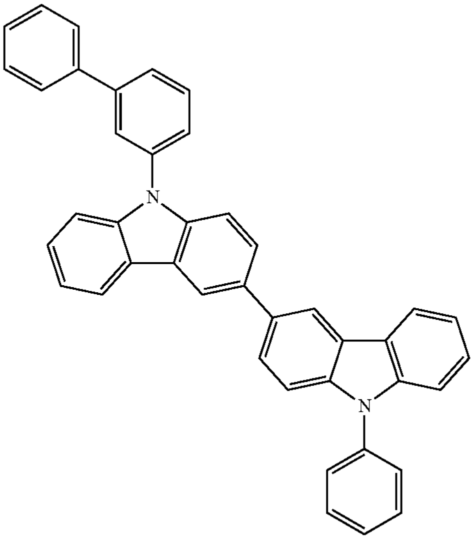
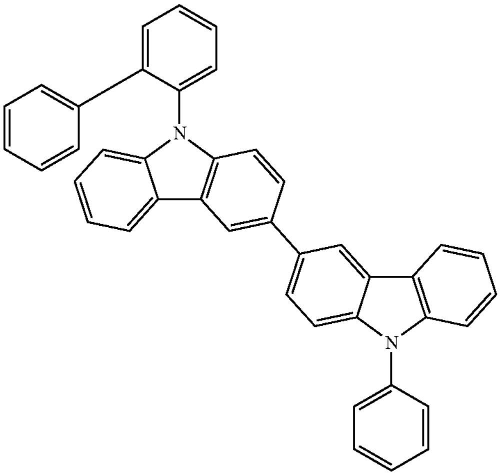

-continued
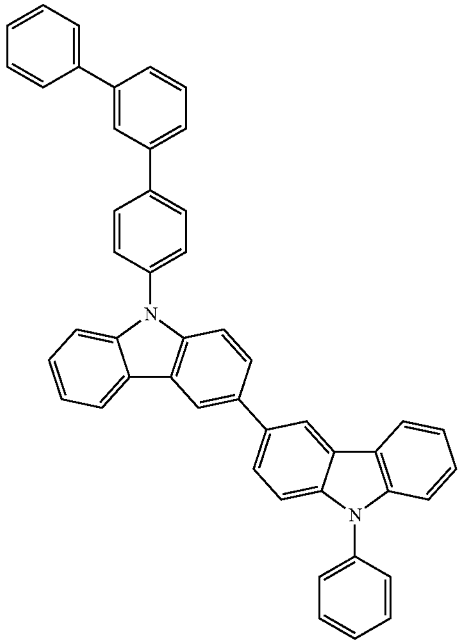
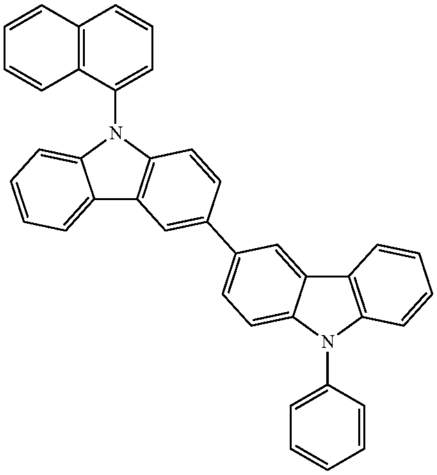
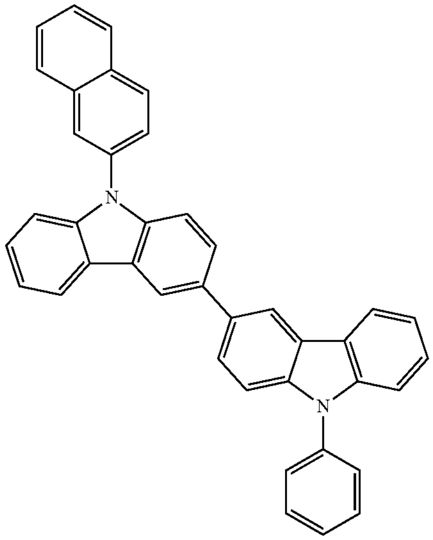
-continued
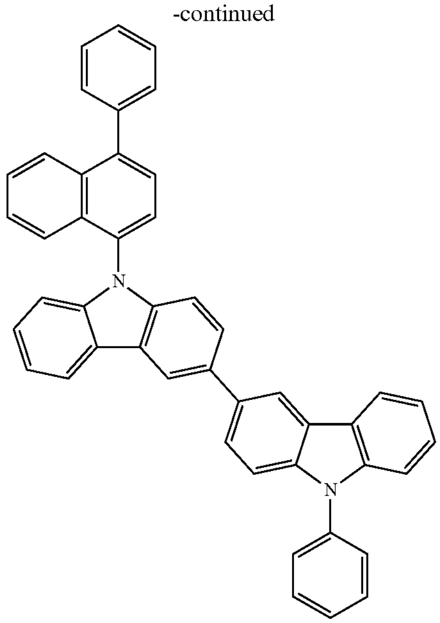
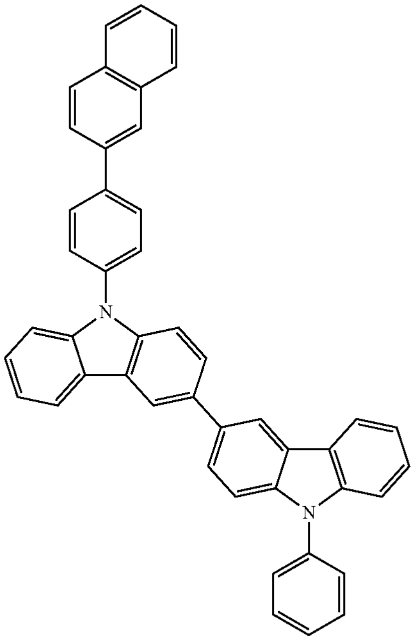

-continued
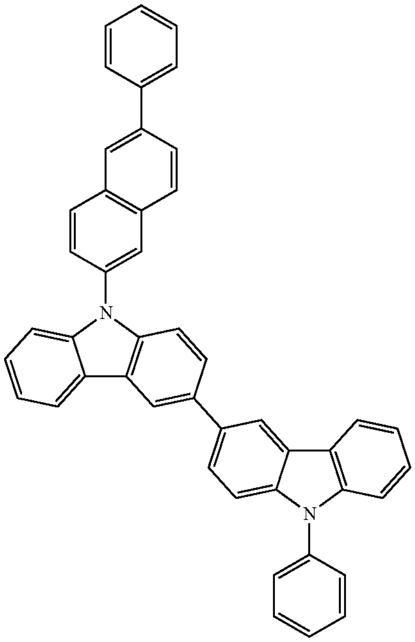
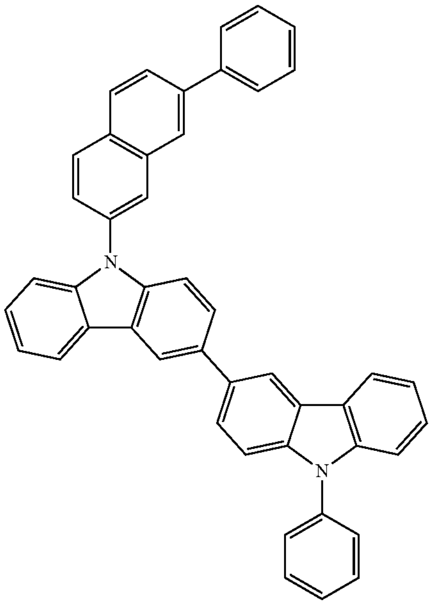
-continued
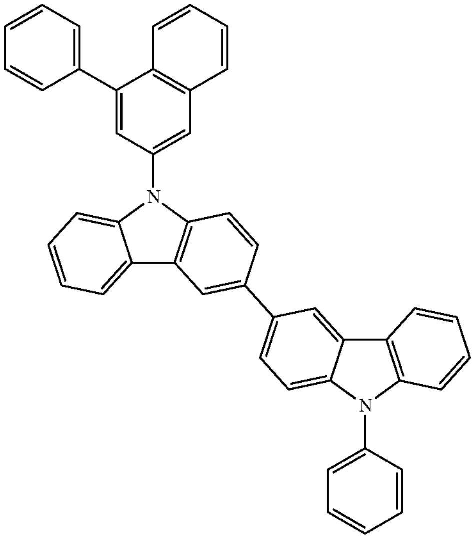
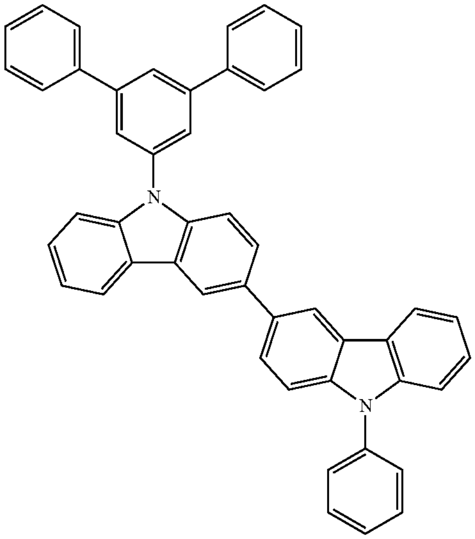
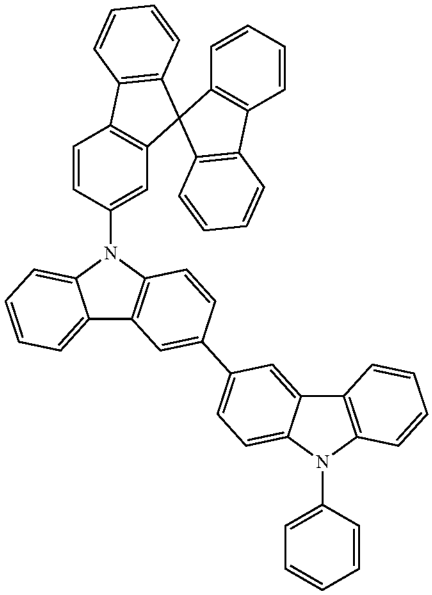

-continued
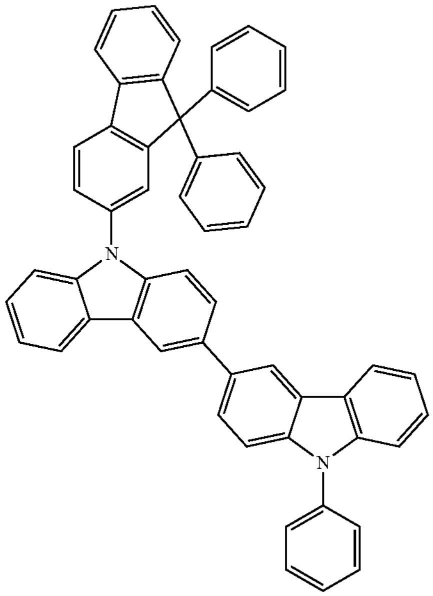
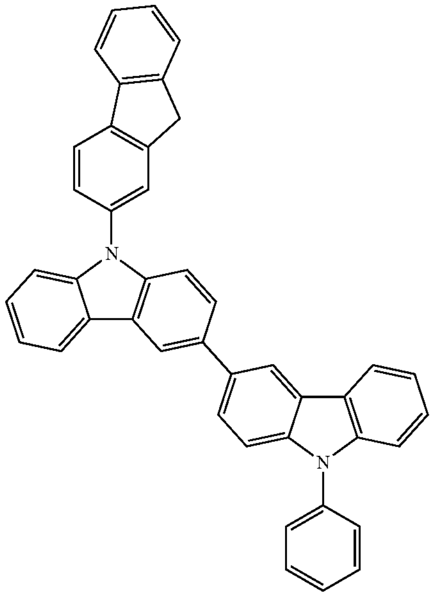
-continued
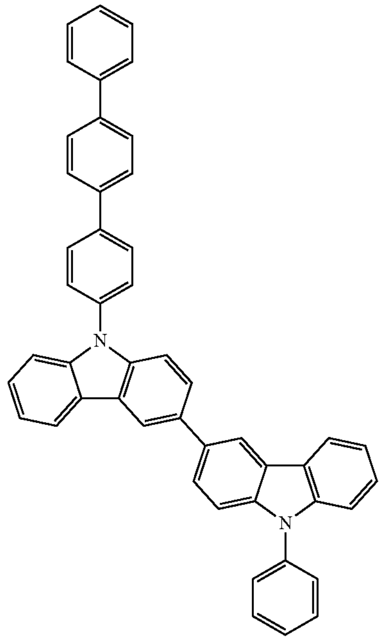
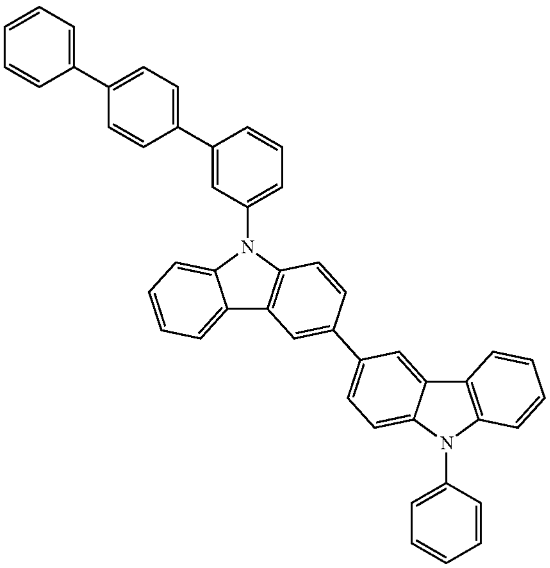

-continued
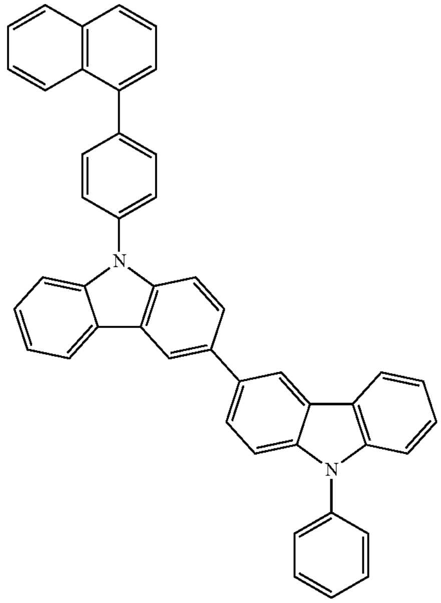
-continued
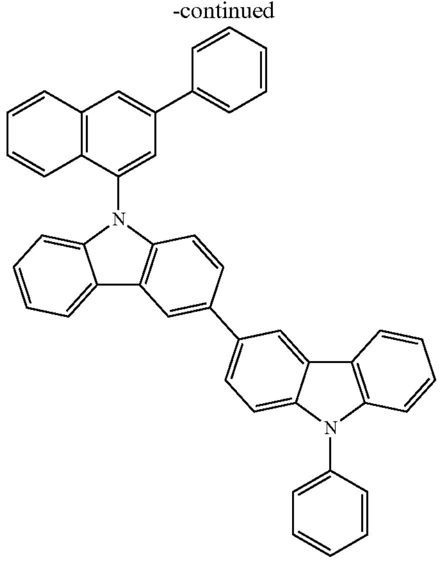
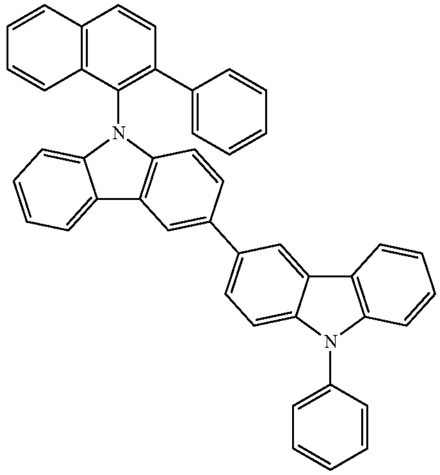
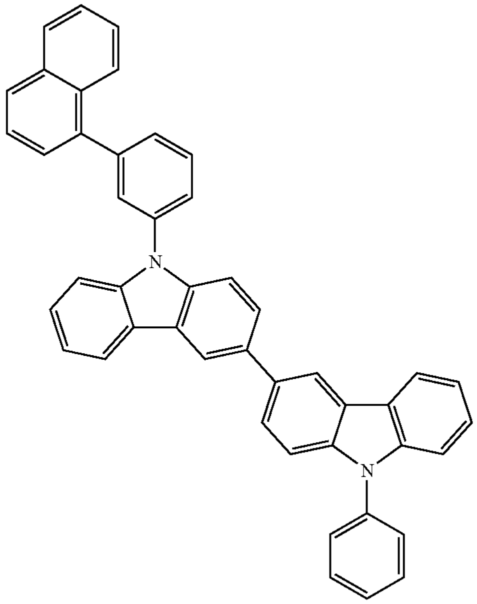
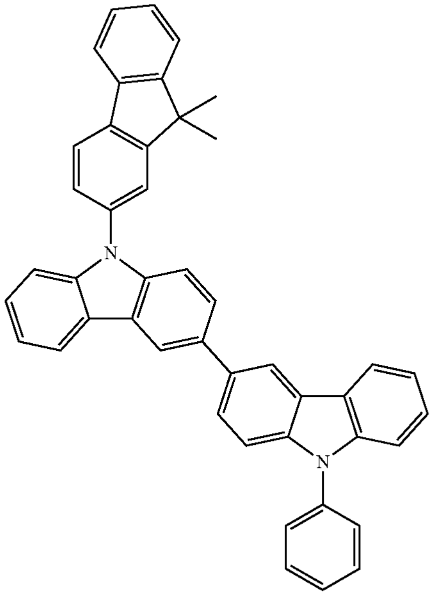

-continued
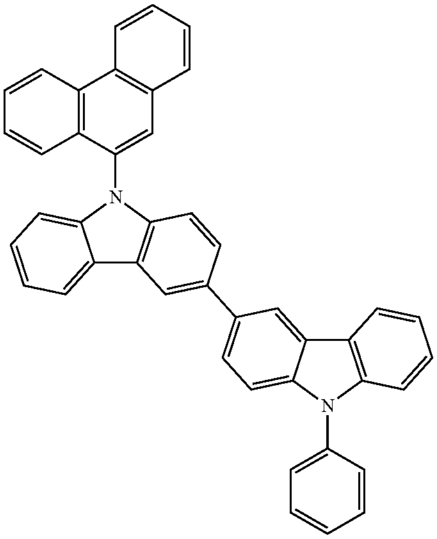
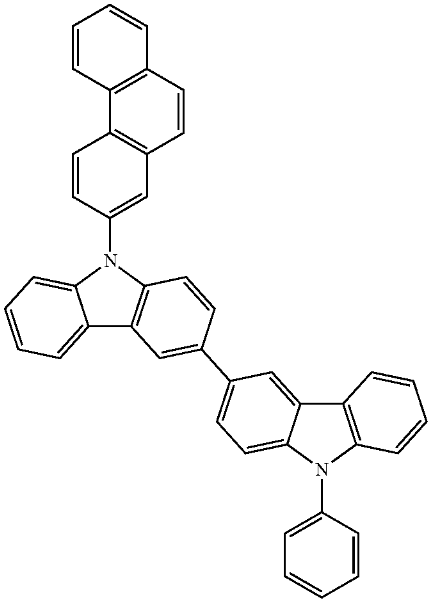
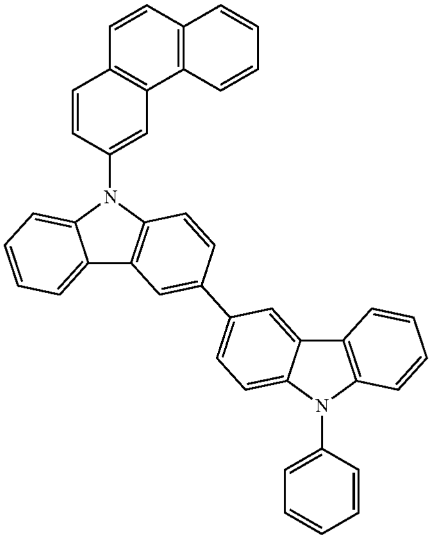
-continued
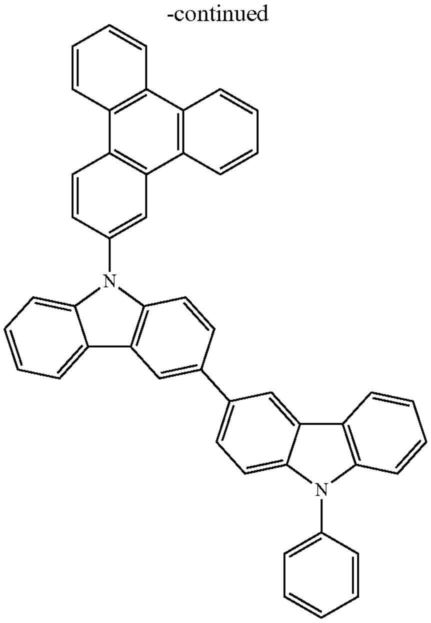
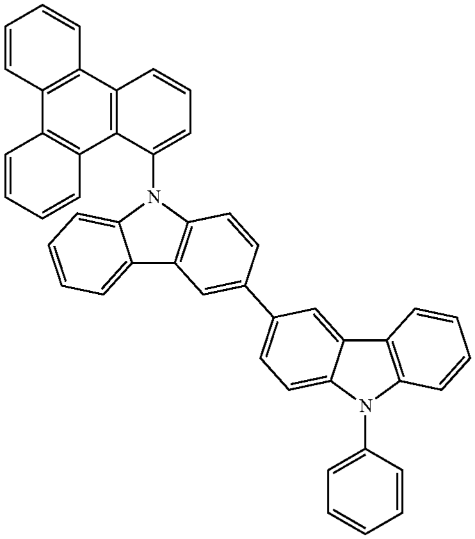
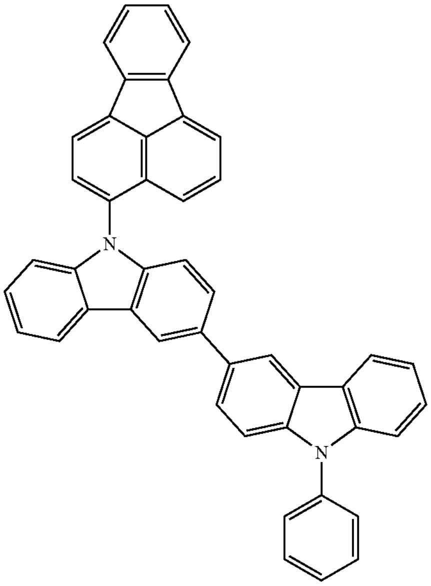

-continued
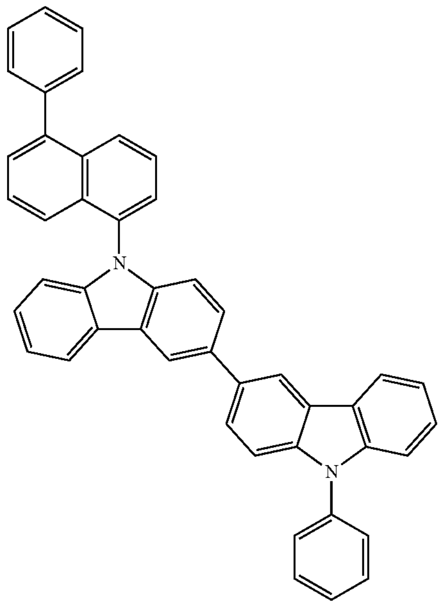
-continued
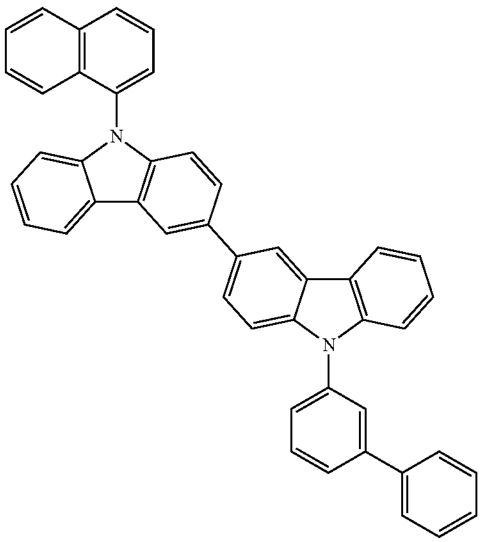
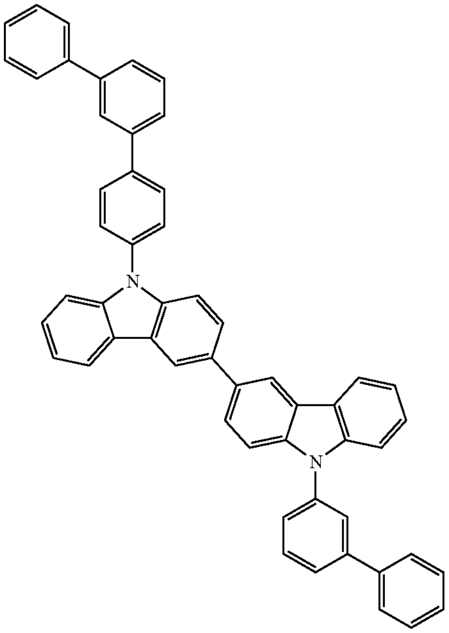
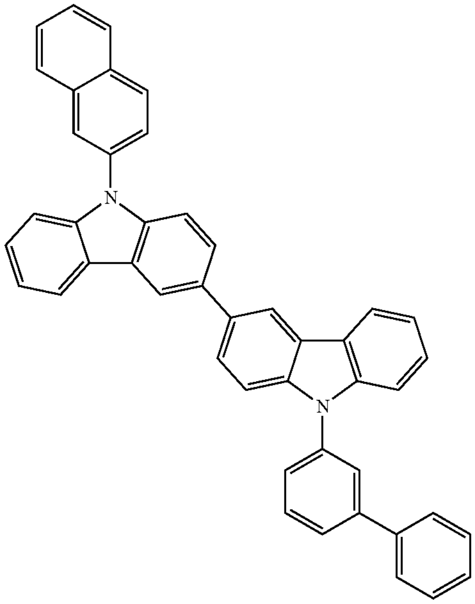

-continued
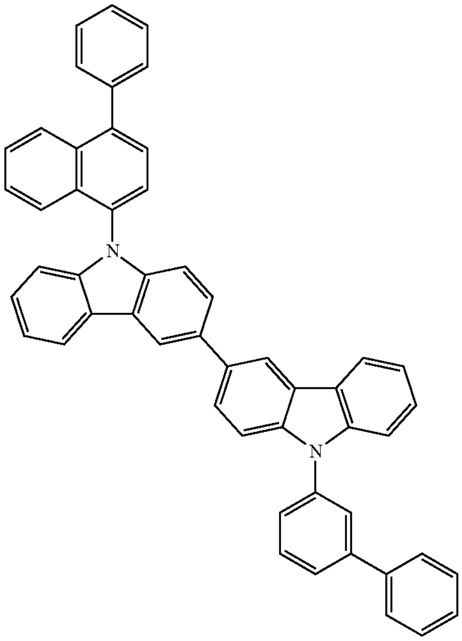
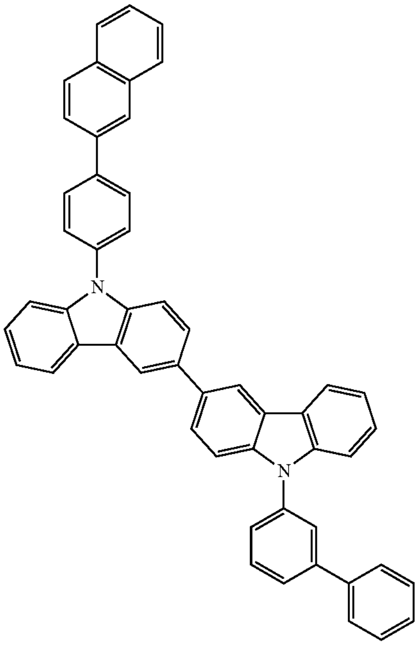
-continued
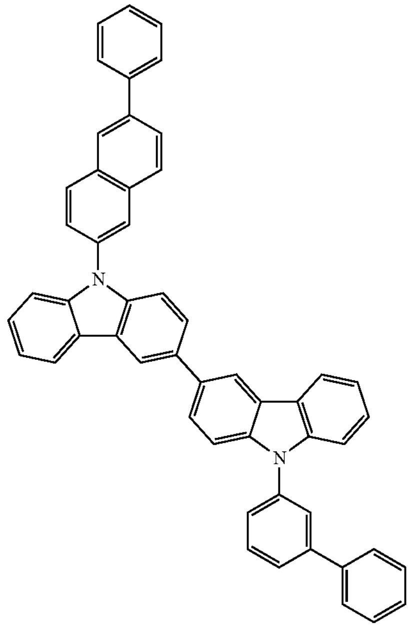
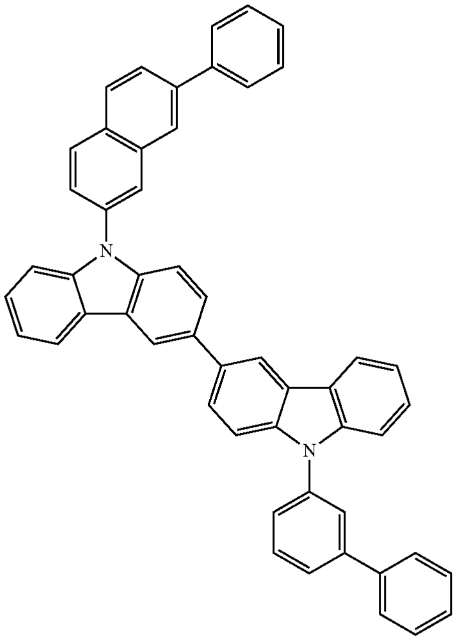

-continued
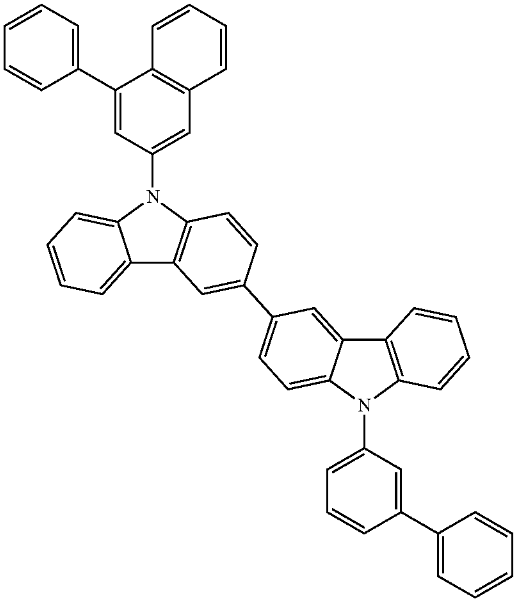
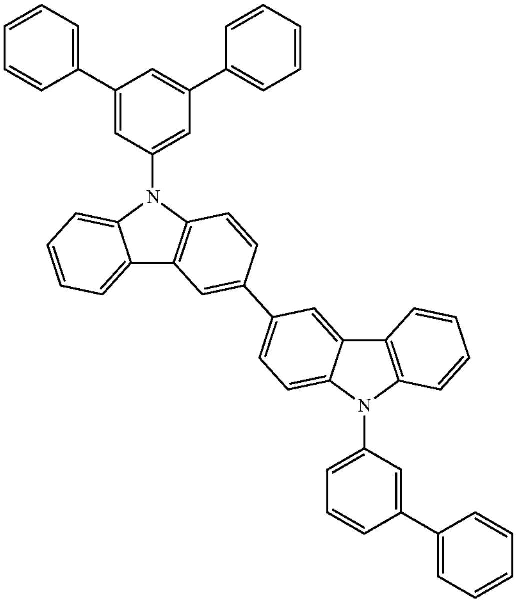
-continued
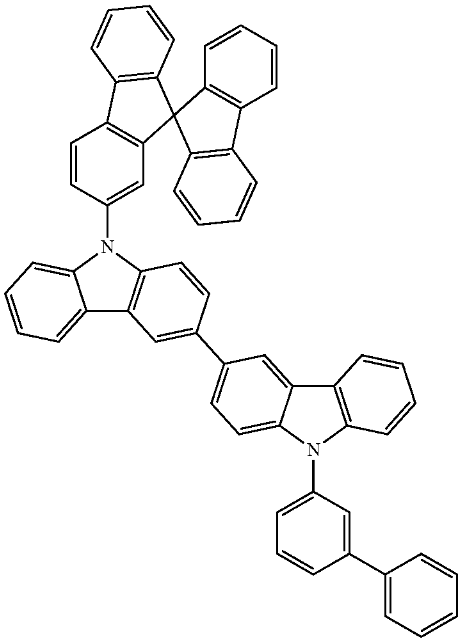
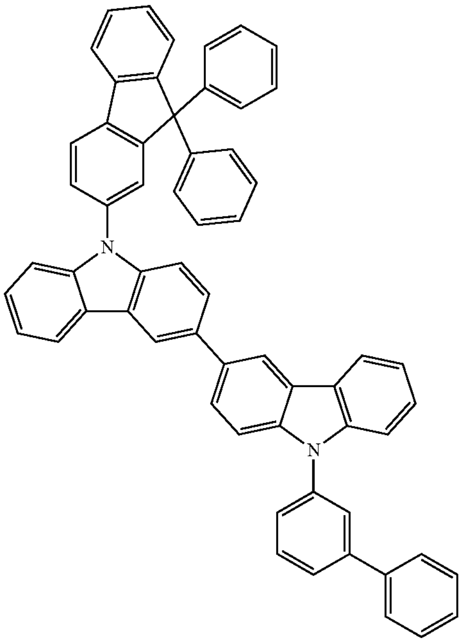

-continued
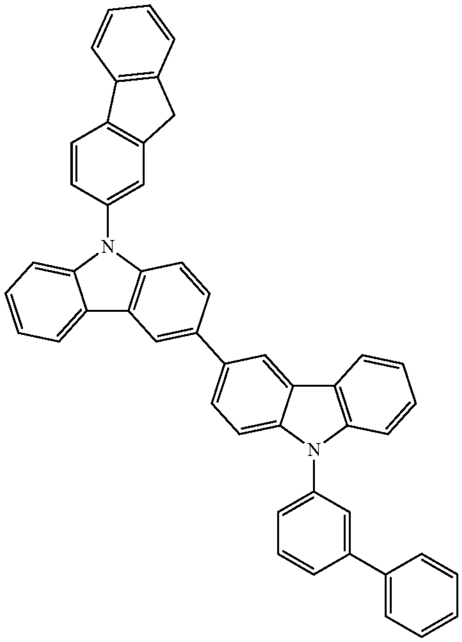
-continued
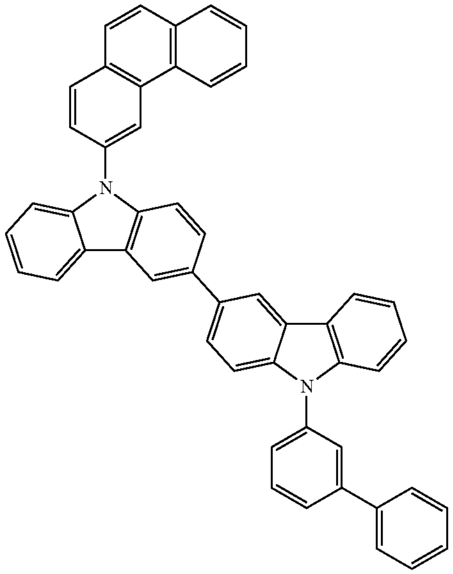
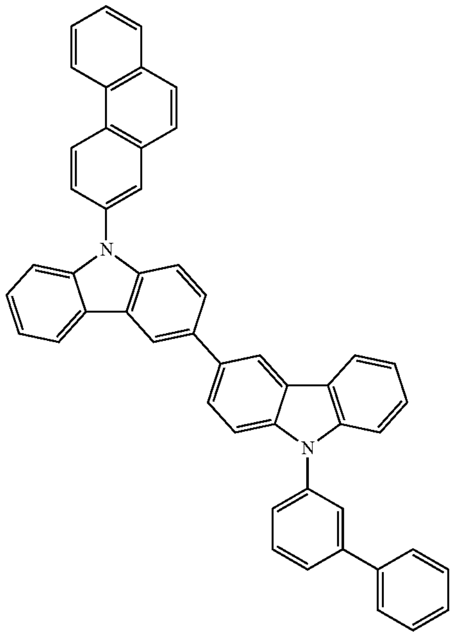
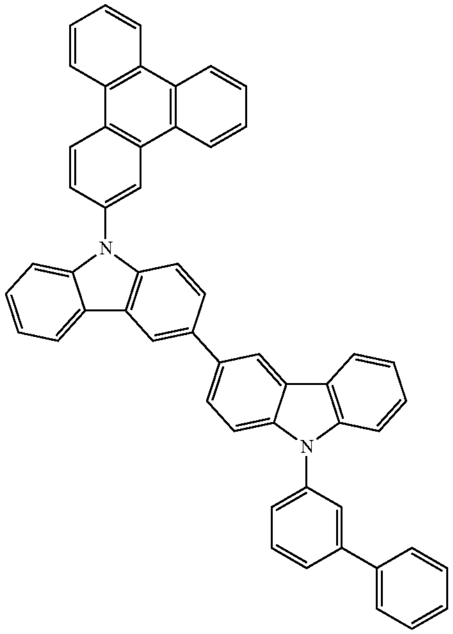

-continued
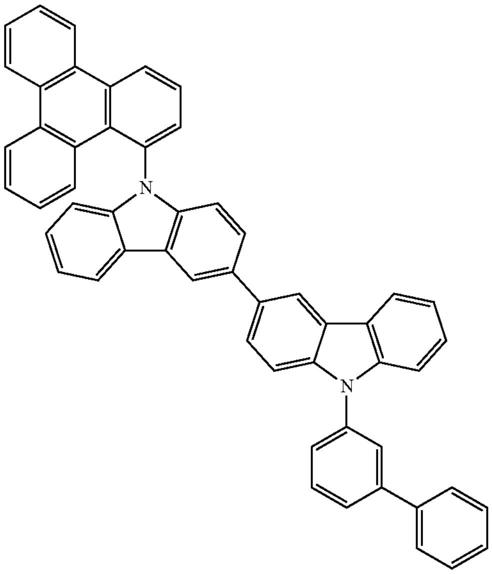
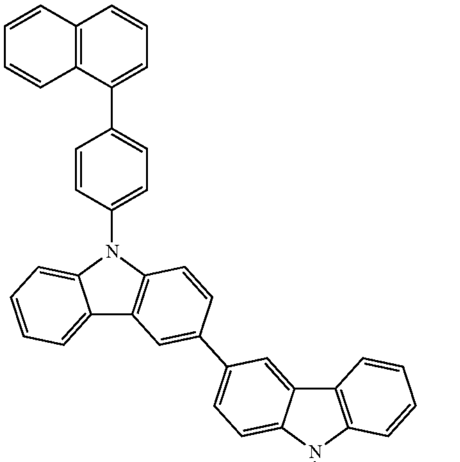
-continued
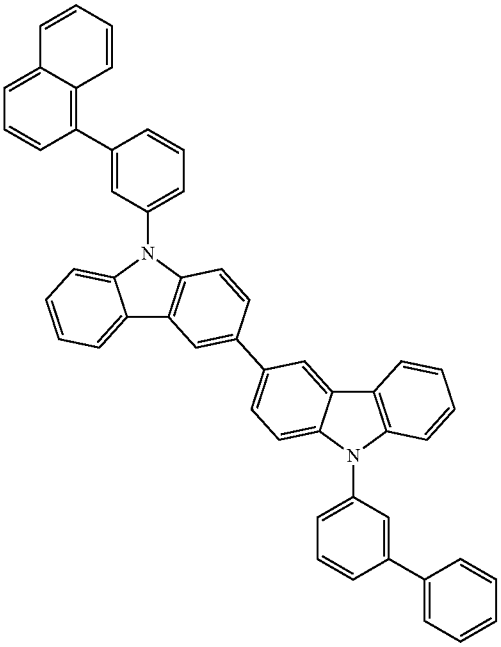
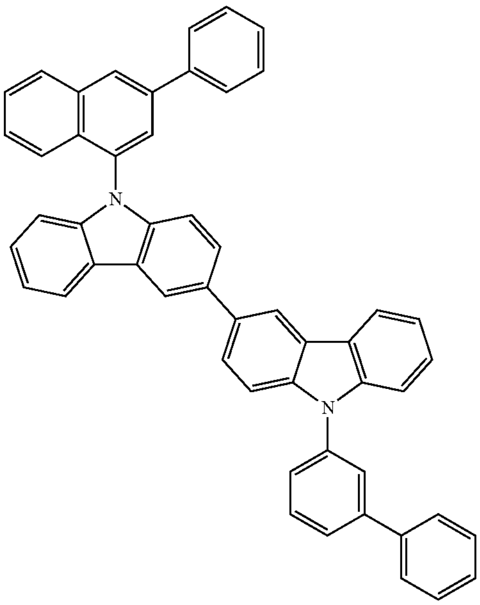

-continued
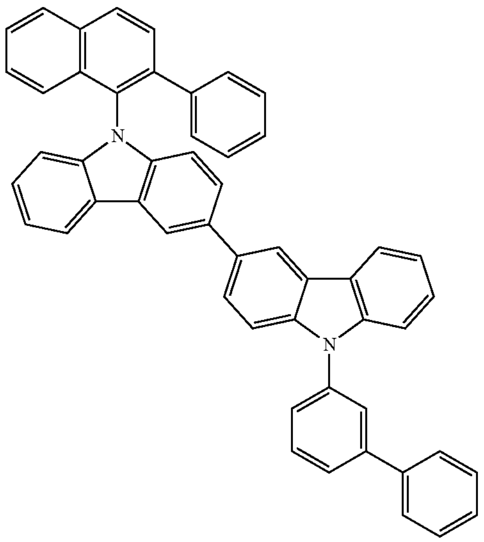
-continued
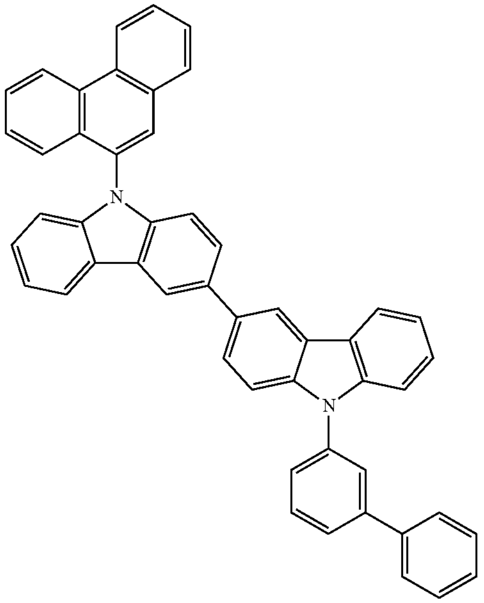
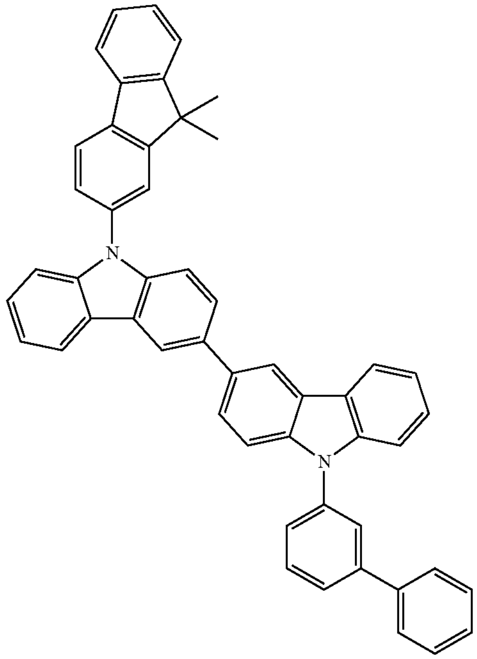
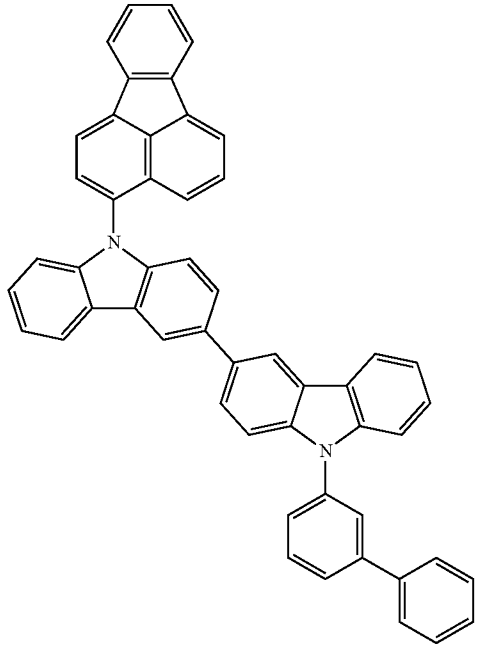

-continued
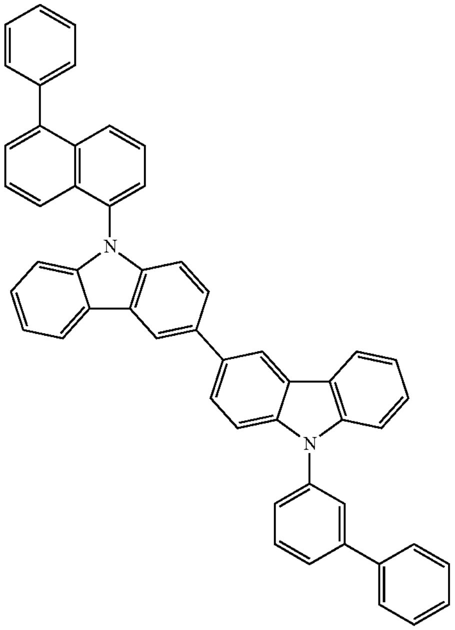
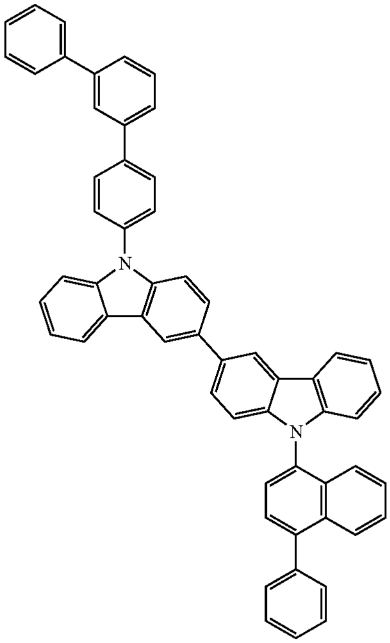
-continued
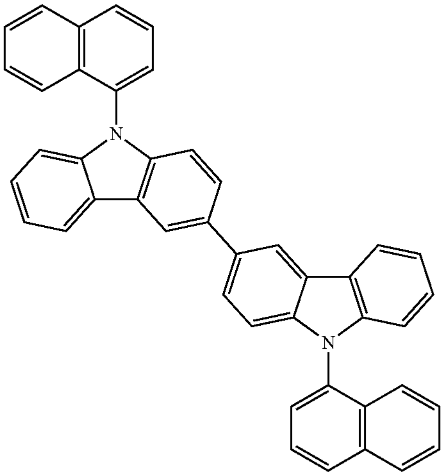
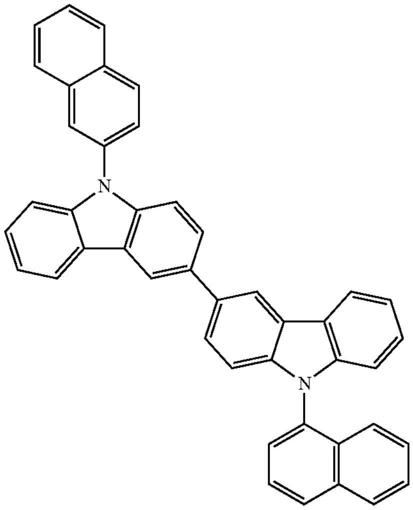
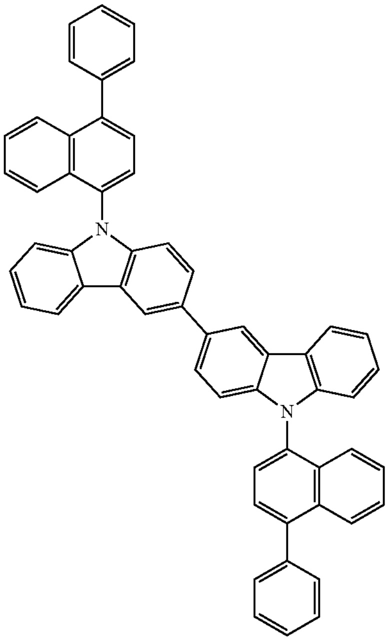

-continued
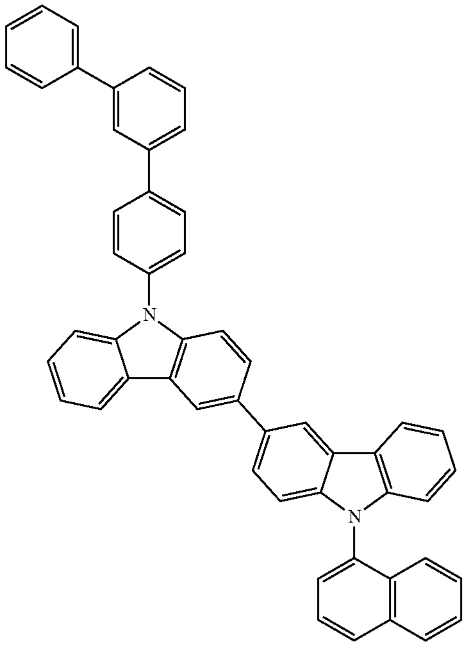
-continued
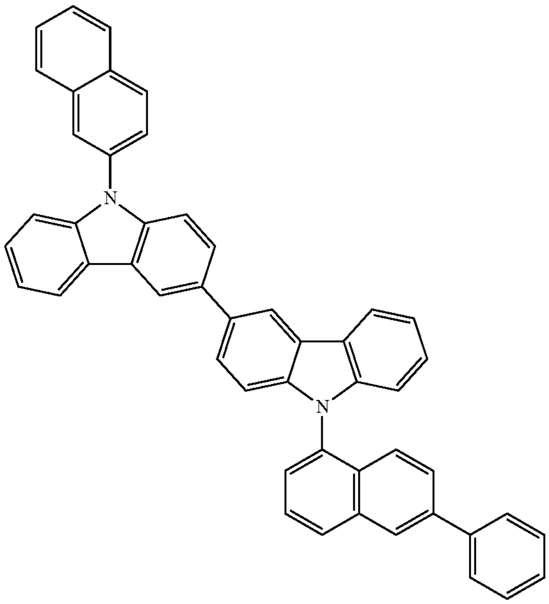
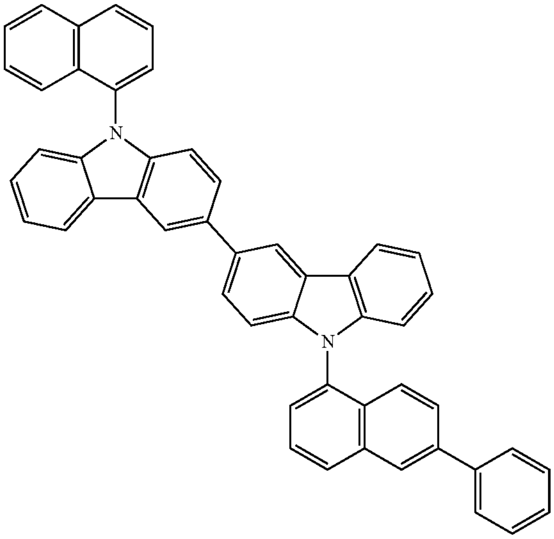
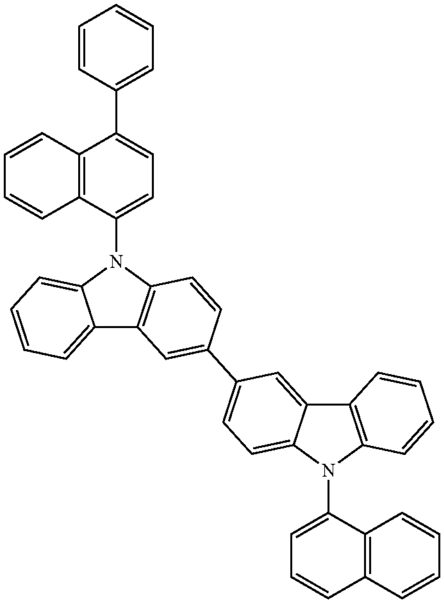

-continued
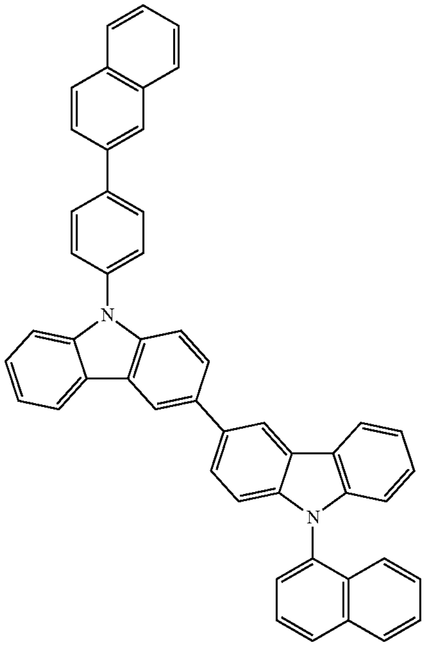
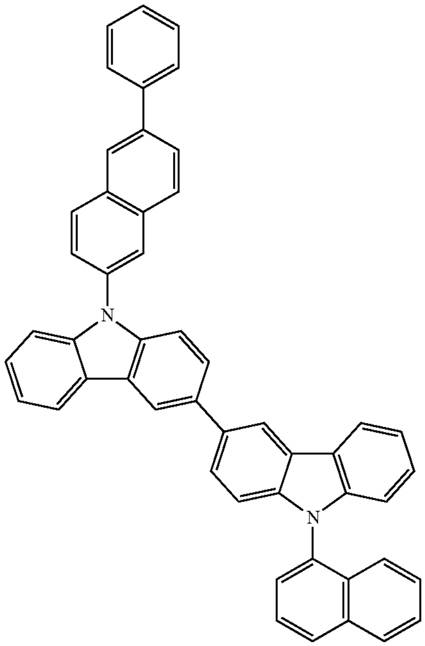
-continued
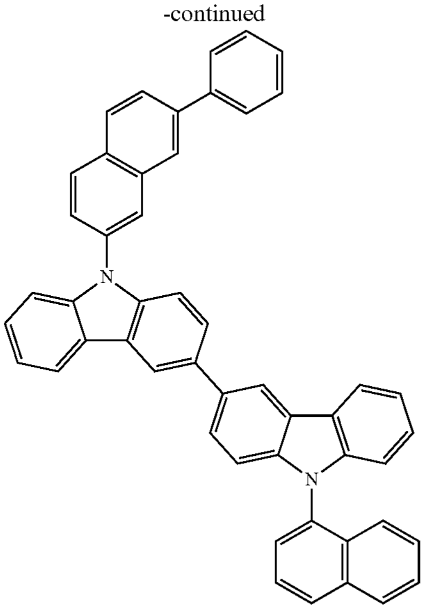
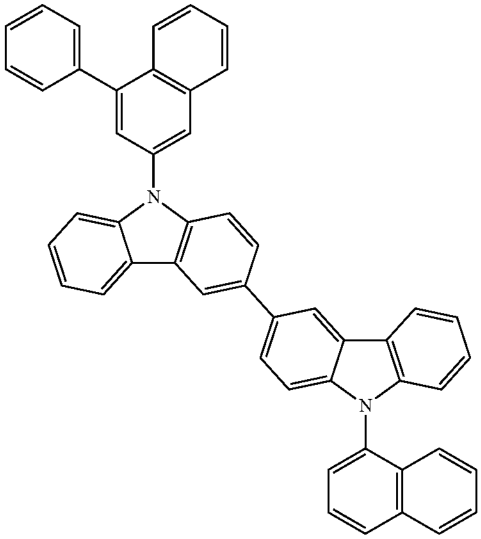
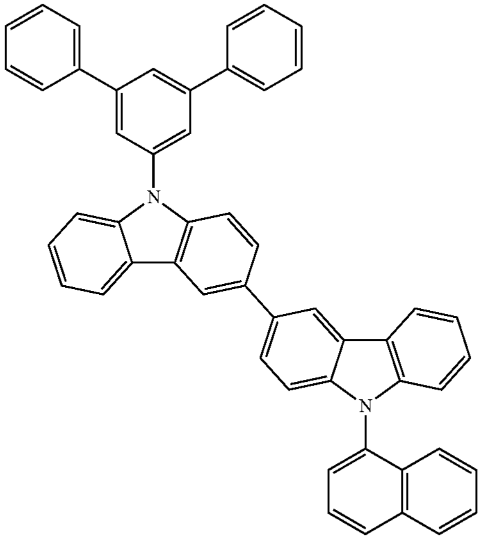

-continued
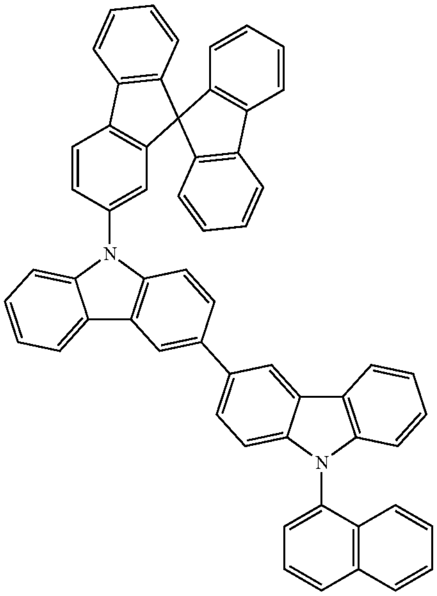
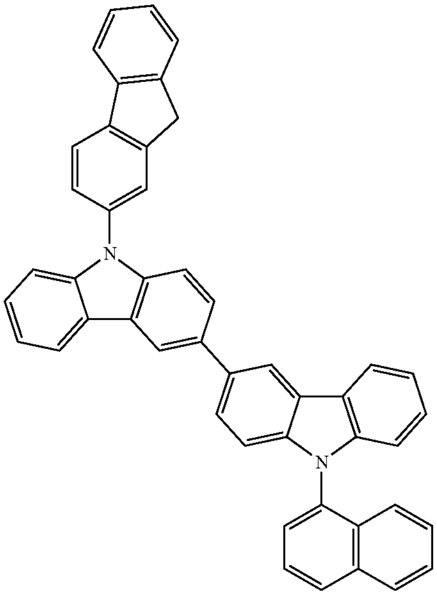
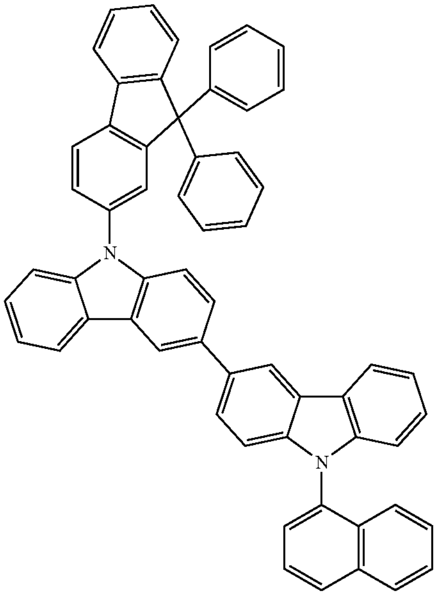
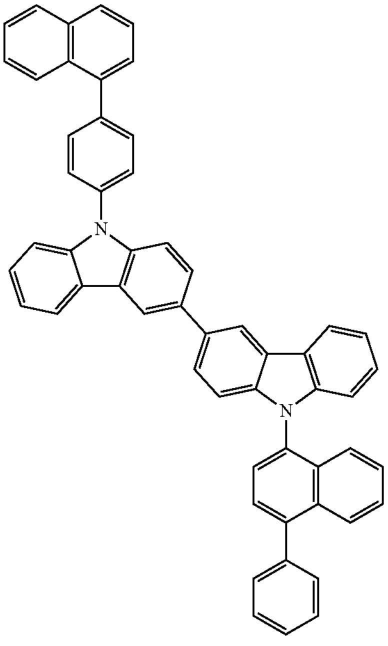
-continued

-continued
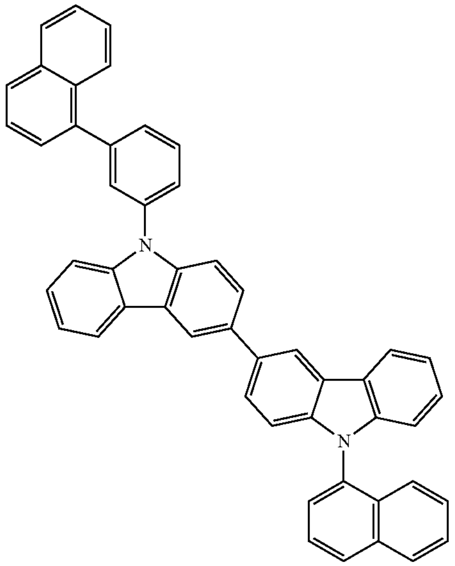
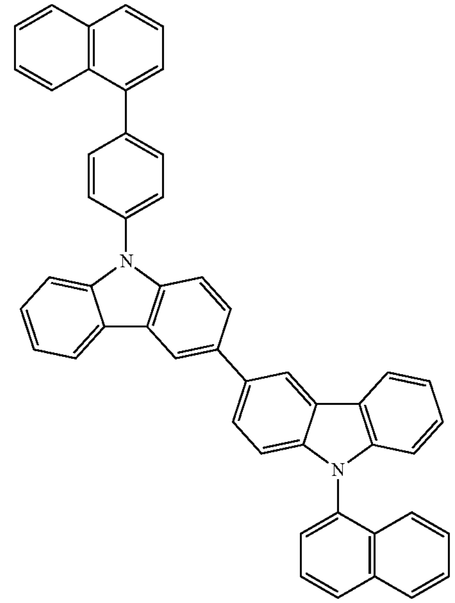
-continued
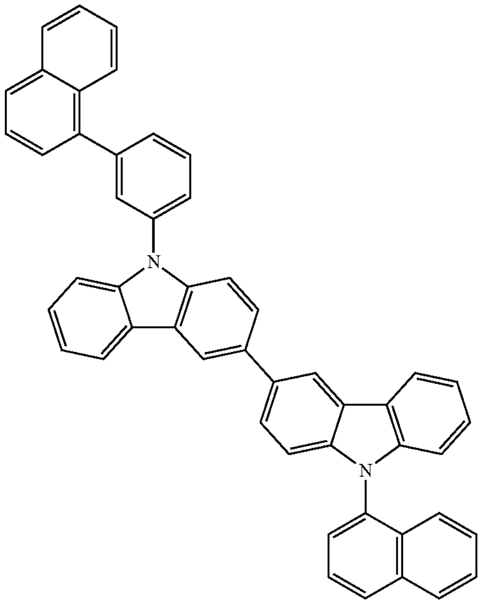
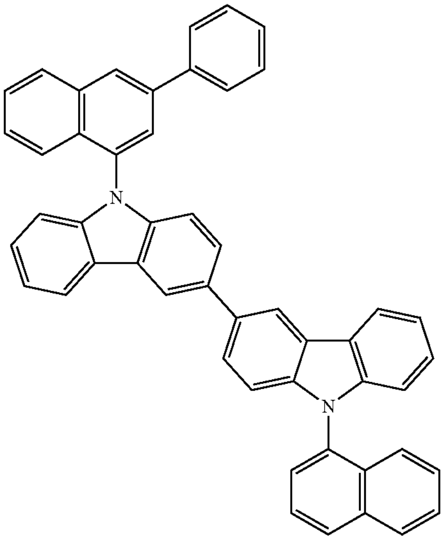
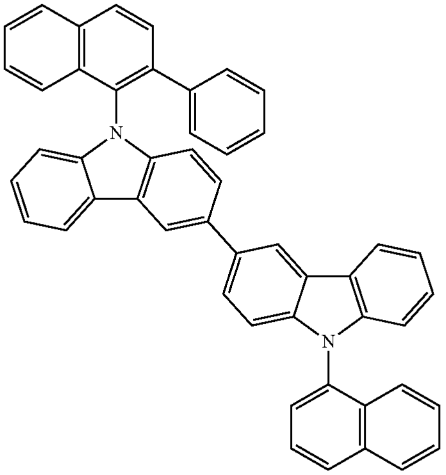

-continued
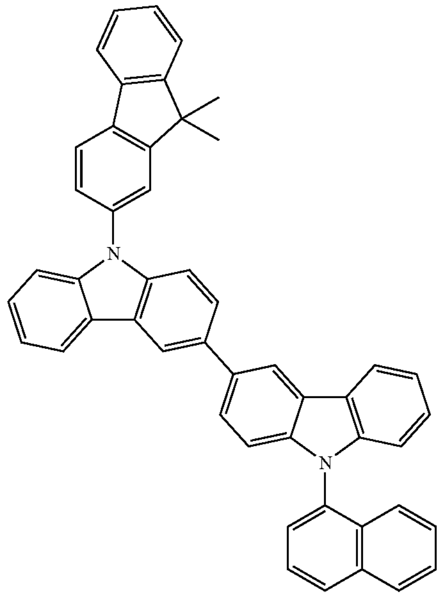
-continued
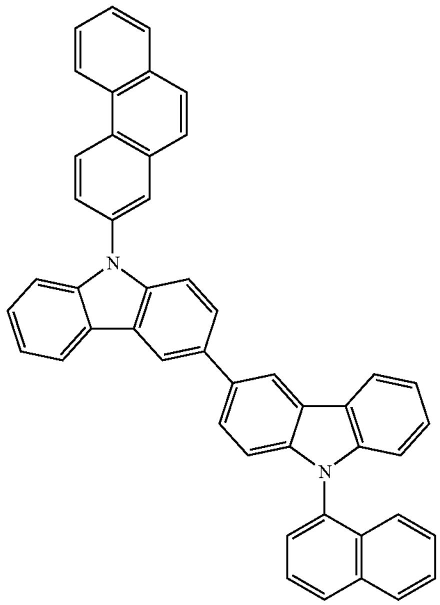
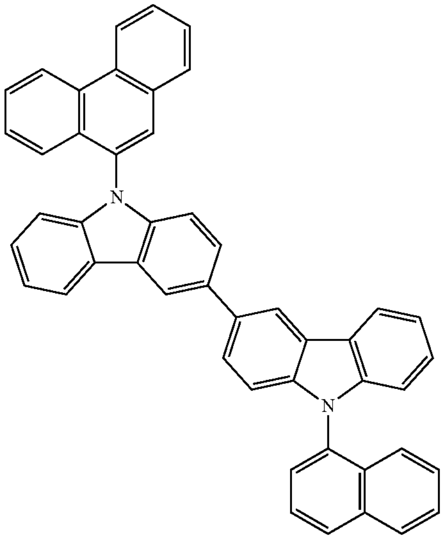
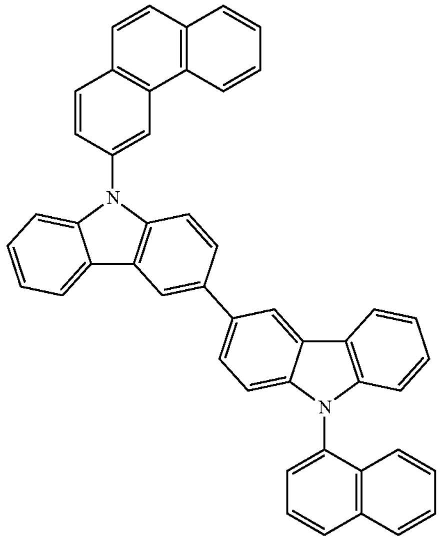

-continued
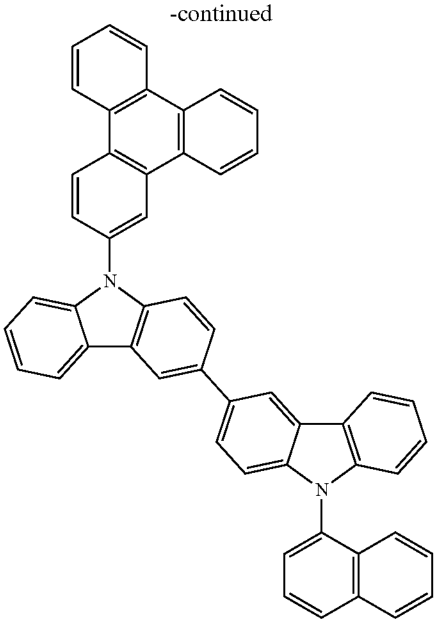
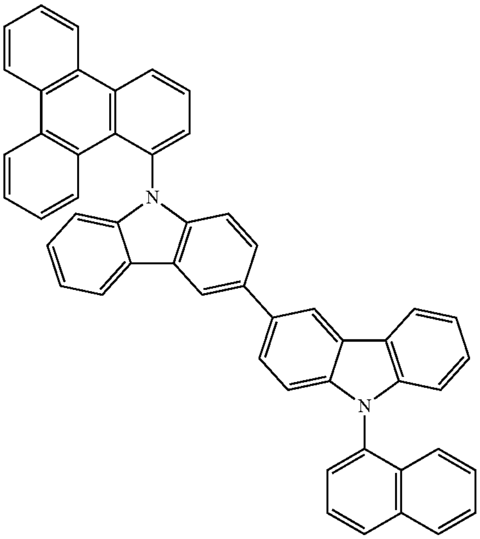
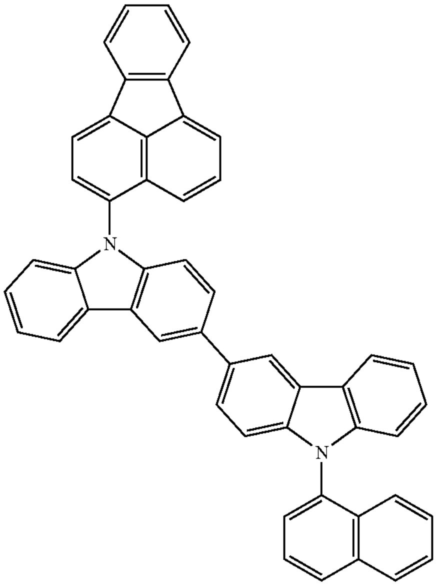
-continued
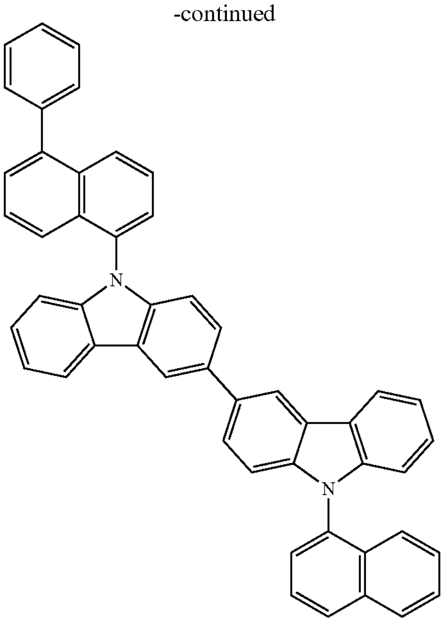
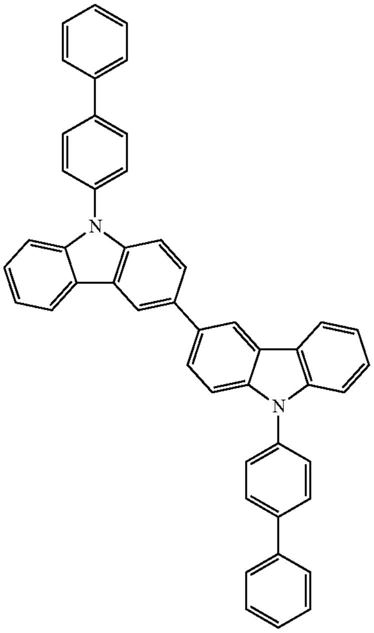

-continued
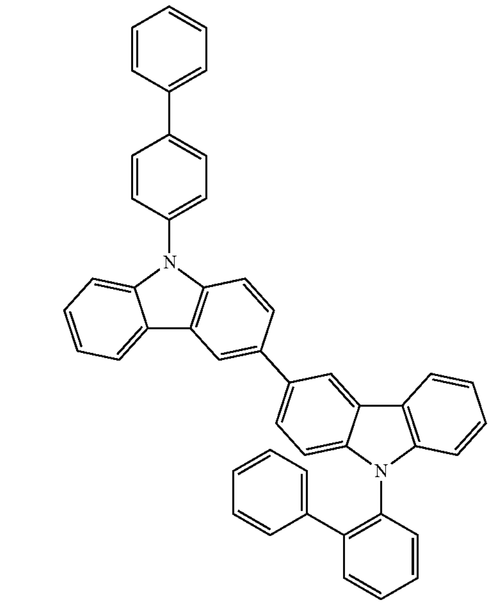
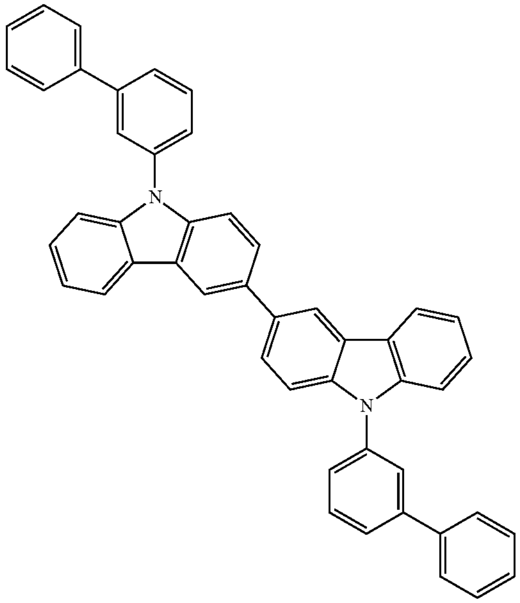
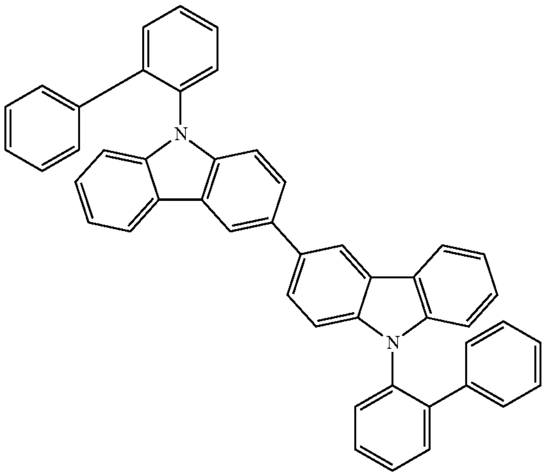
-continued
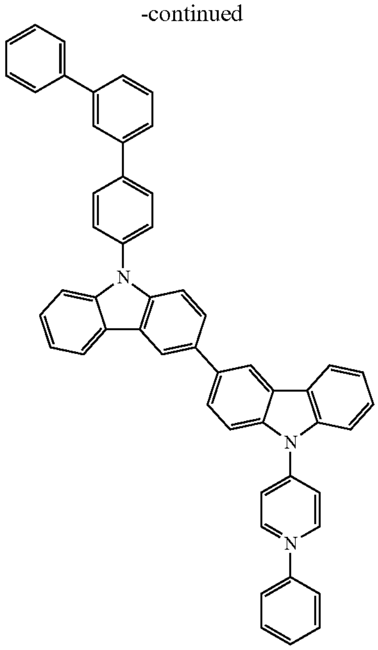
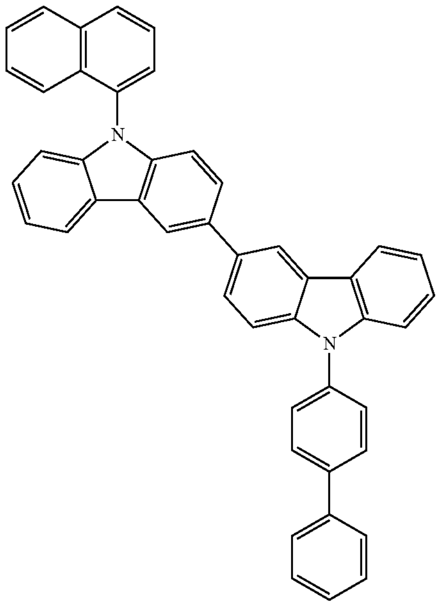

-continued
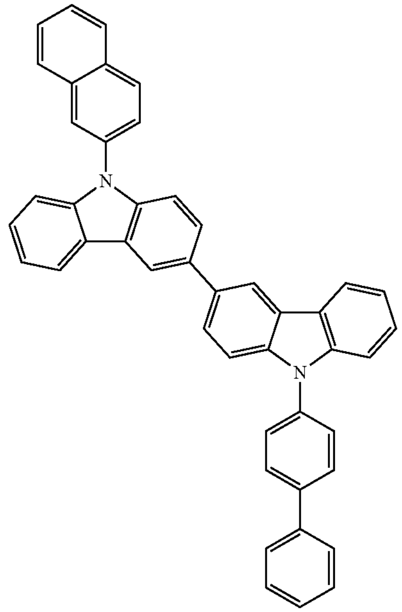
-continued
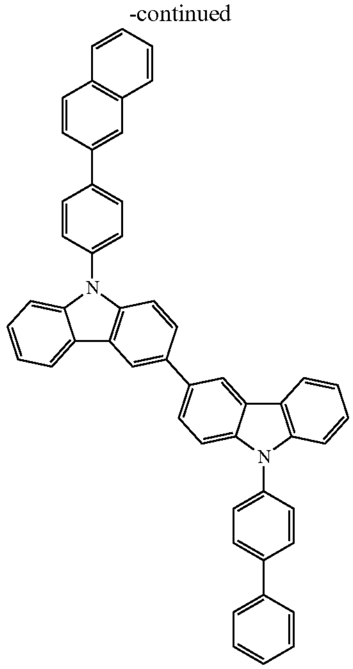
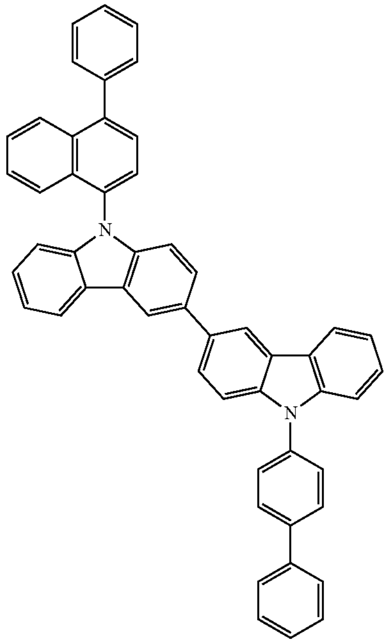
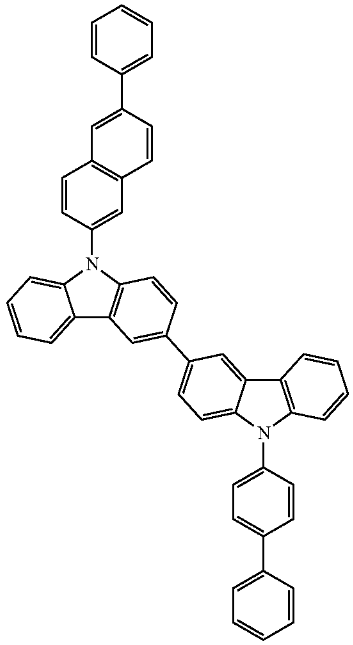

-continued
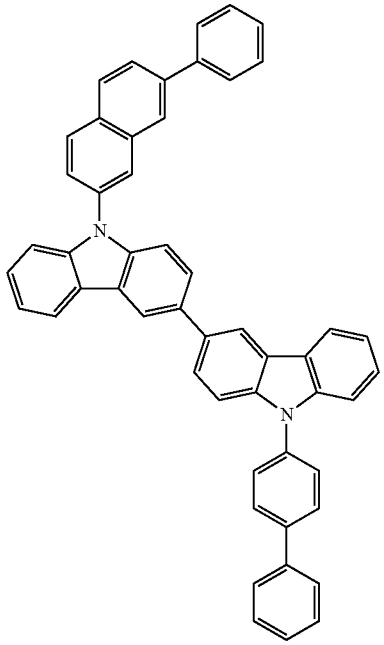
-continued
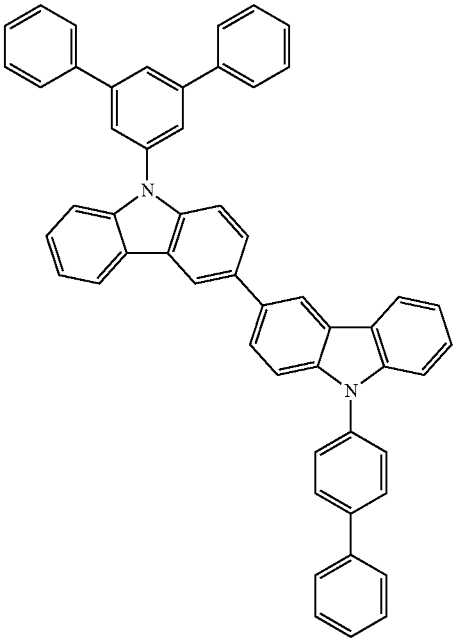
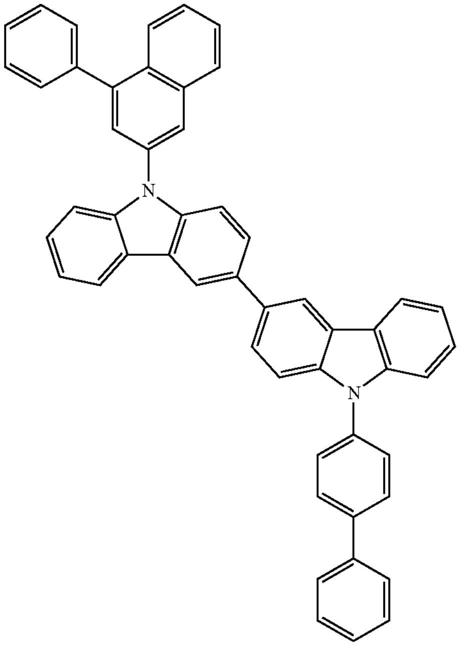
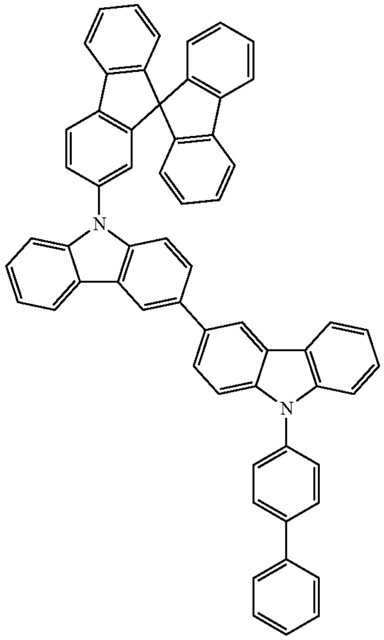

-continued
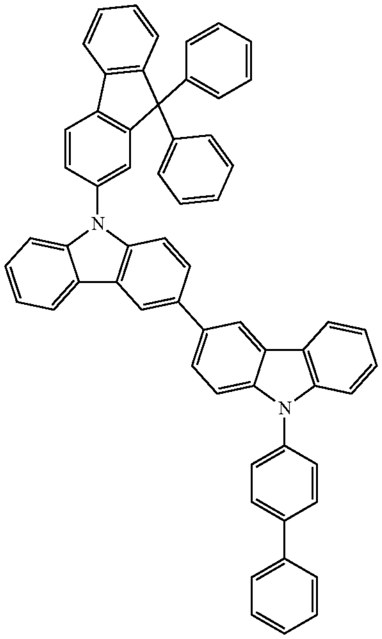
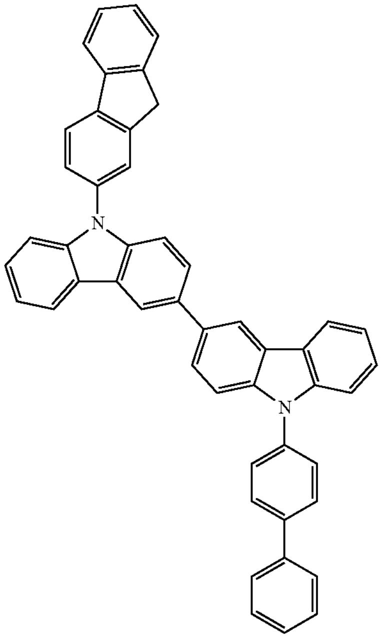
-continued
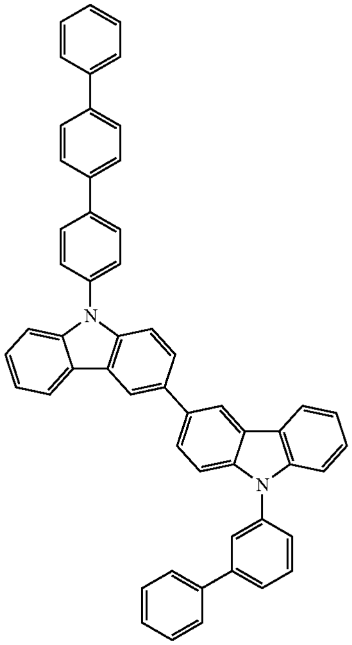
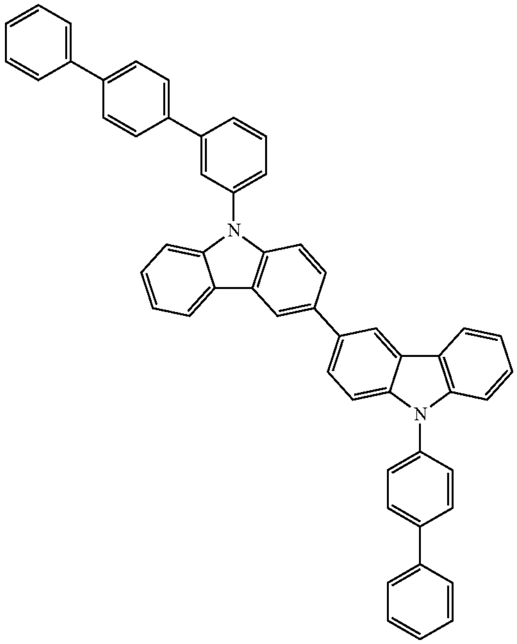

-continued
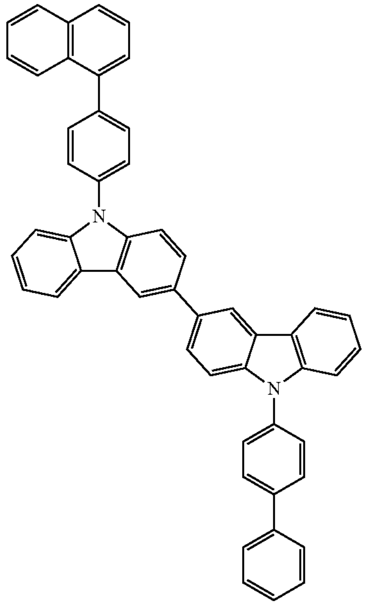
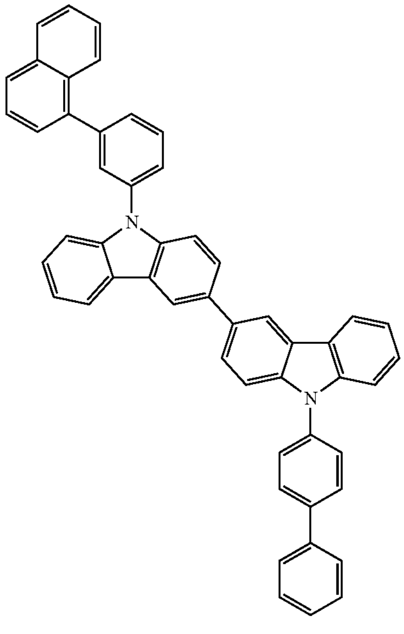
-continued
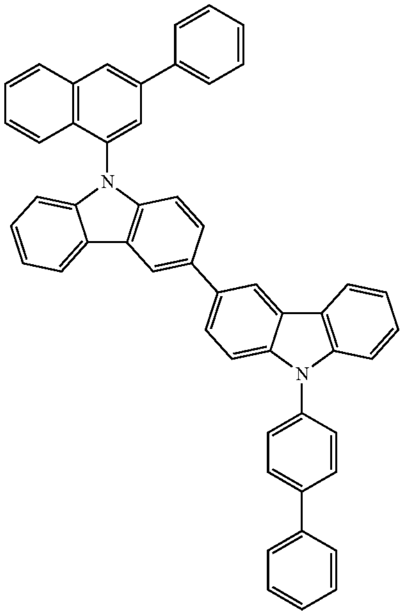
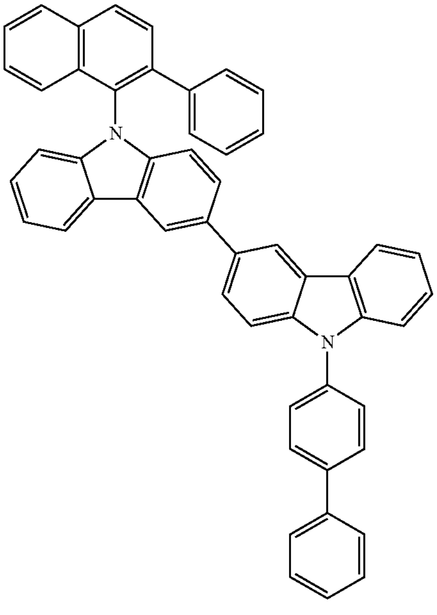

-continued
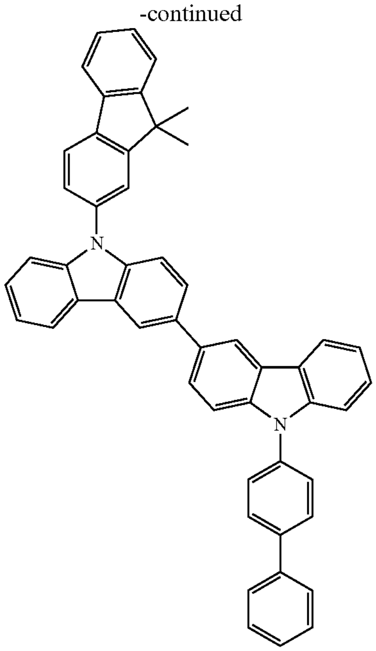
-continued
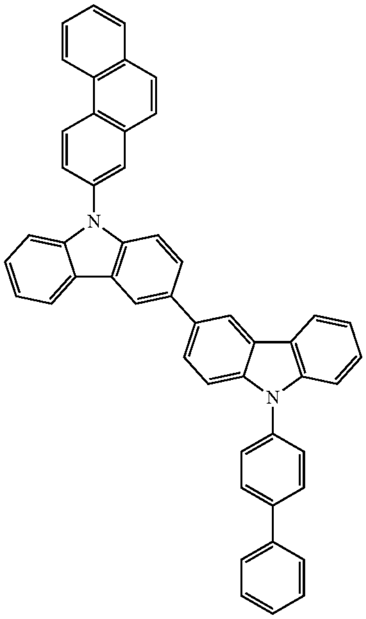
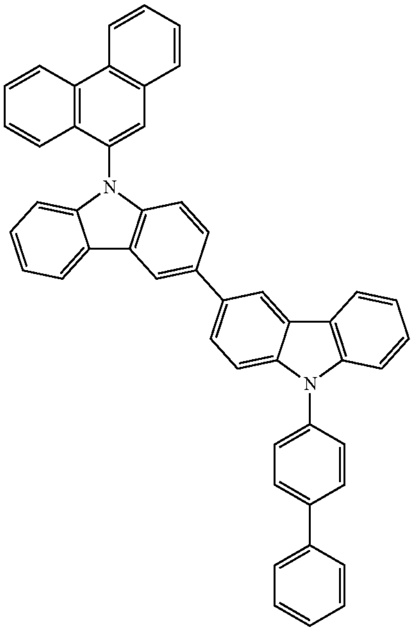
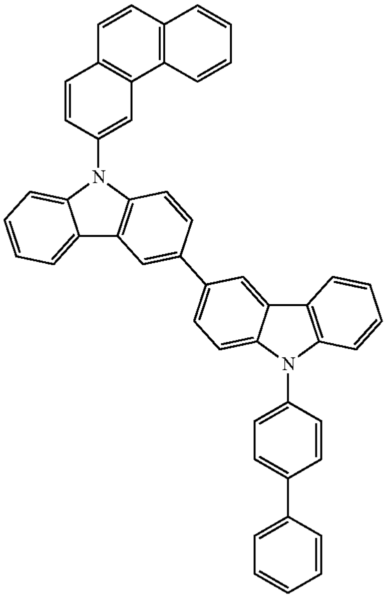

-continued
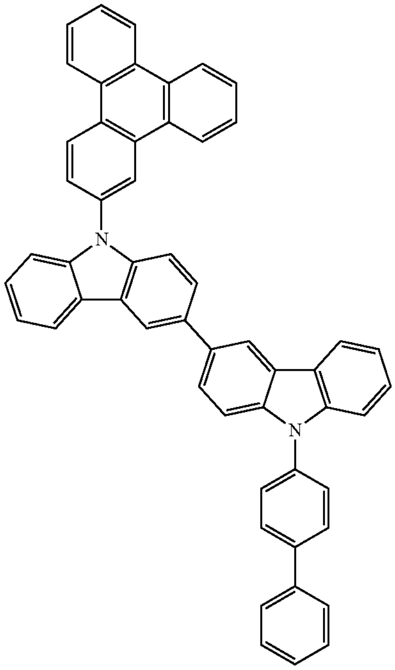
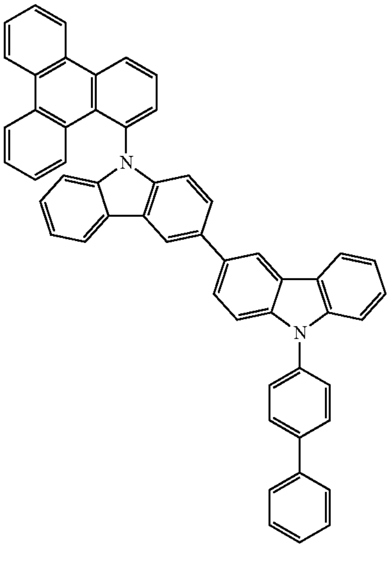
-continued
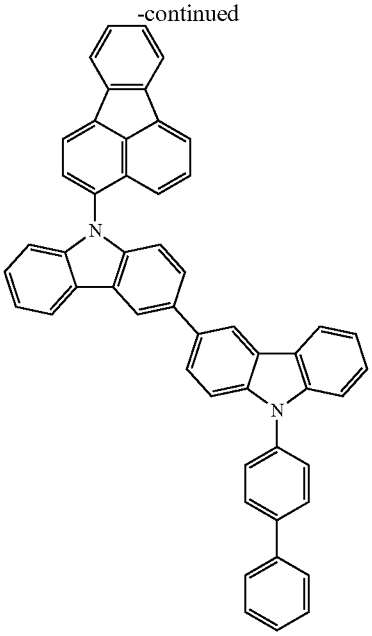
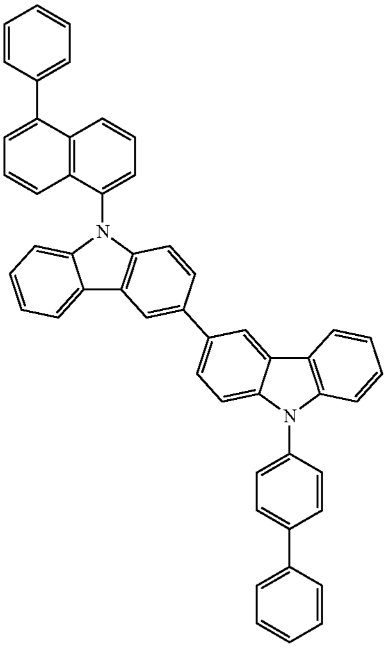

-continued
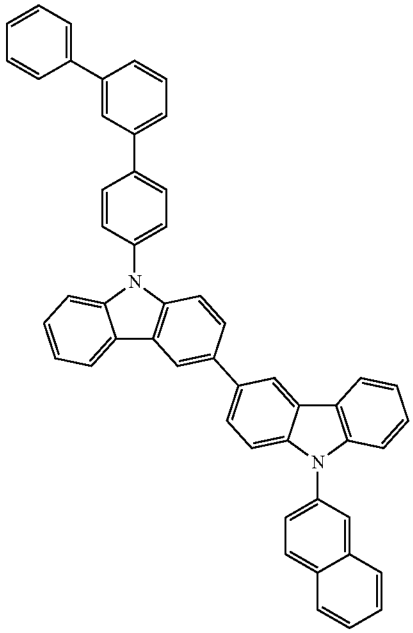
-continued
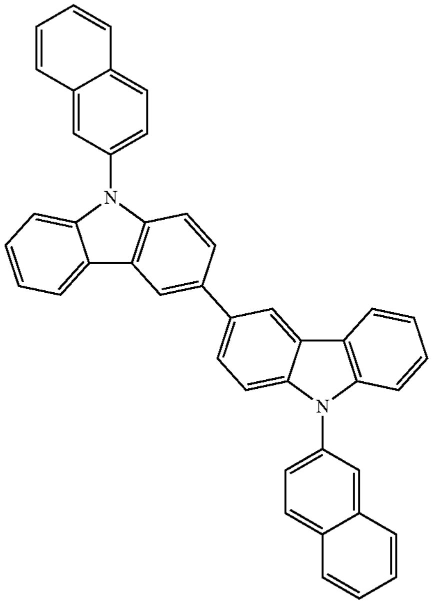
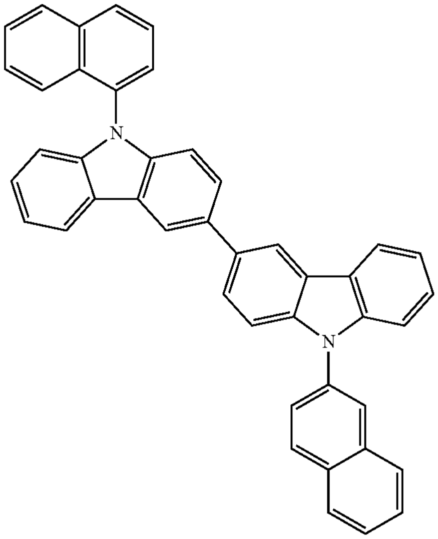
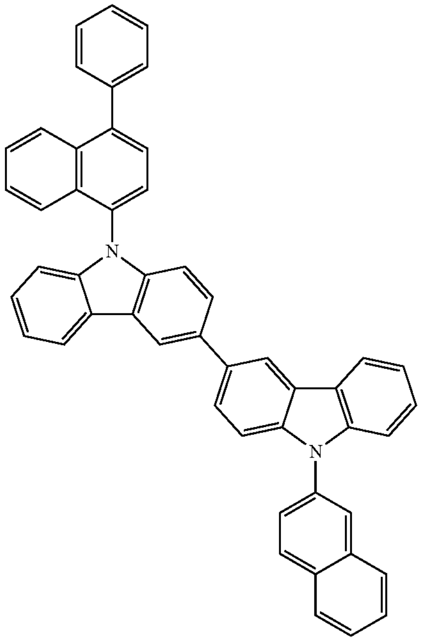

-continued
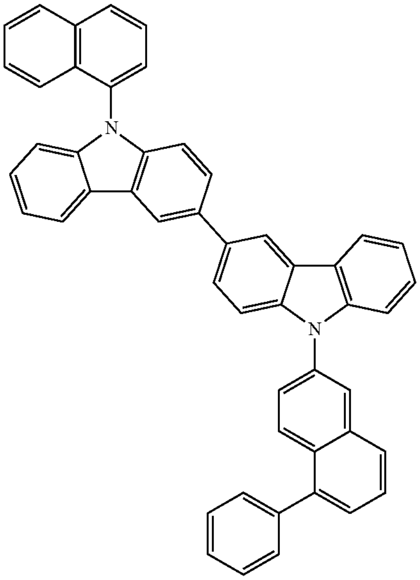
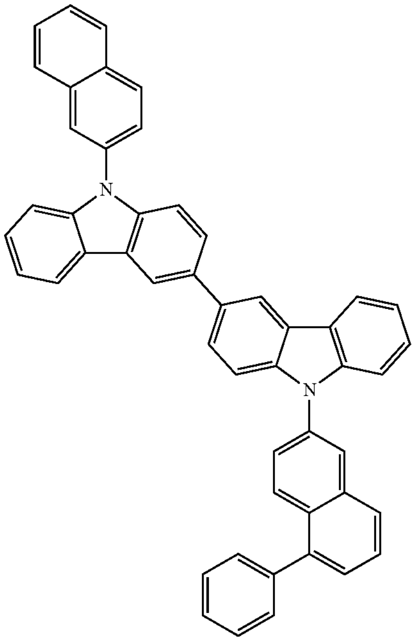
-continued
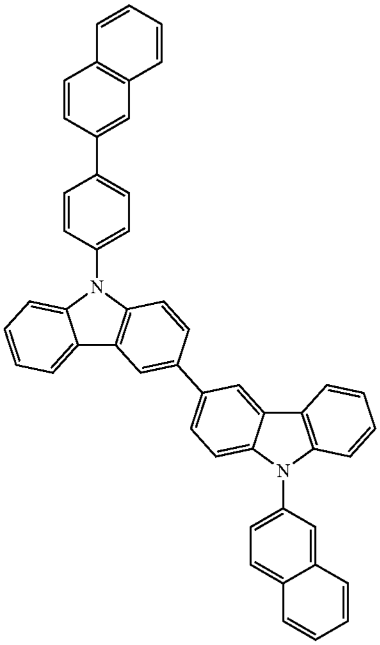 [SMILES: c1ccc2cc(-c3ccc(-n4c5ccccc5c5cc(-c6ccc7c(c6)c6ccccc6n7-c6ccc7ccccc7c6)ccc54)cc3)ccc2c1]
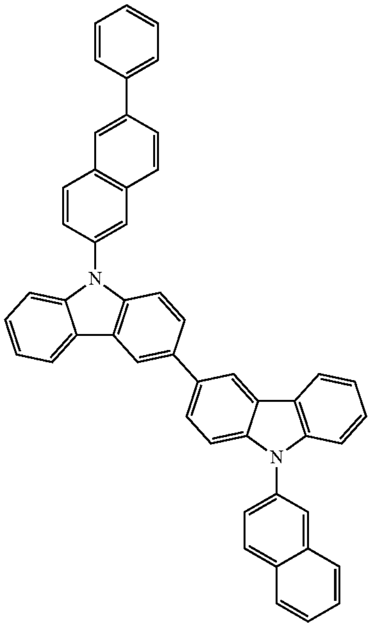

-continued
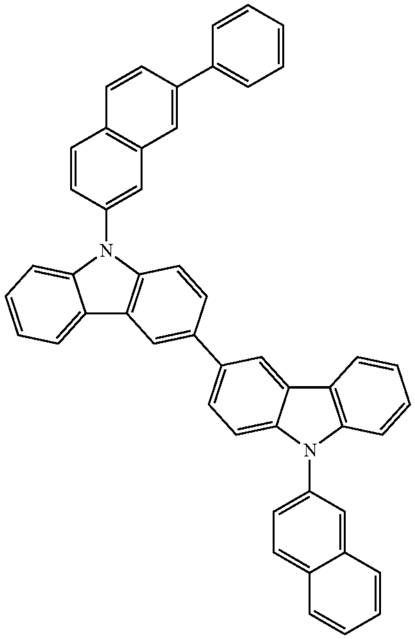
-continued
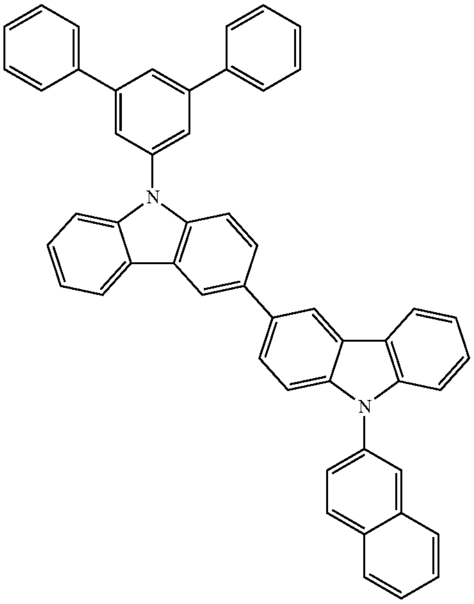
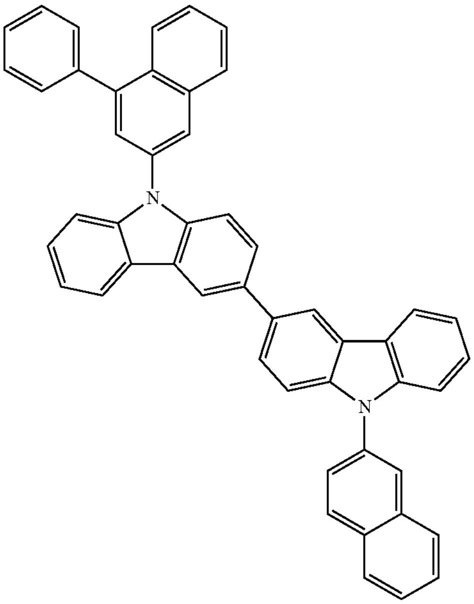
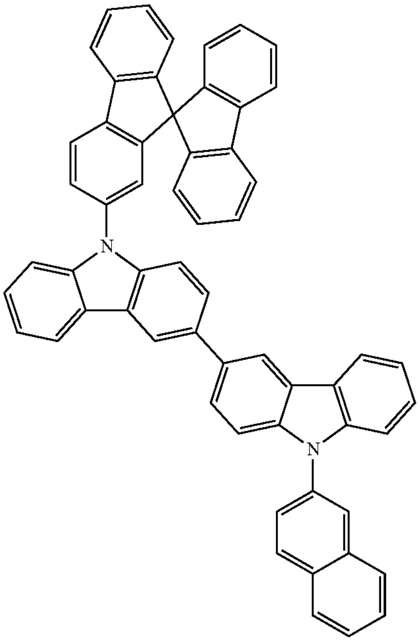

-continued
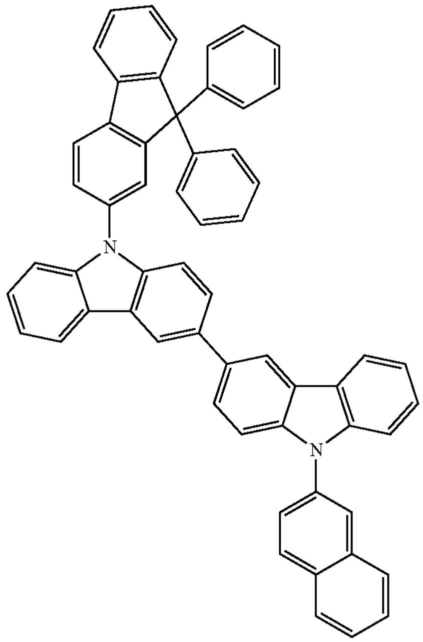
-continued
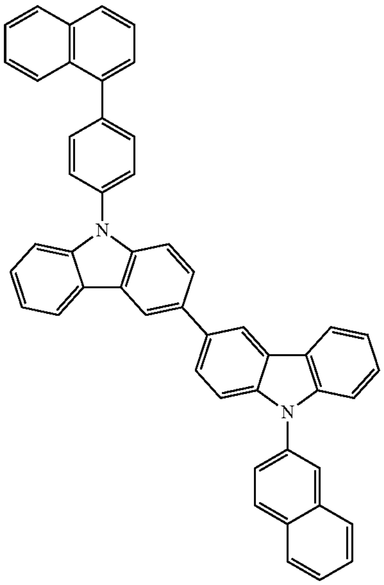
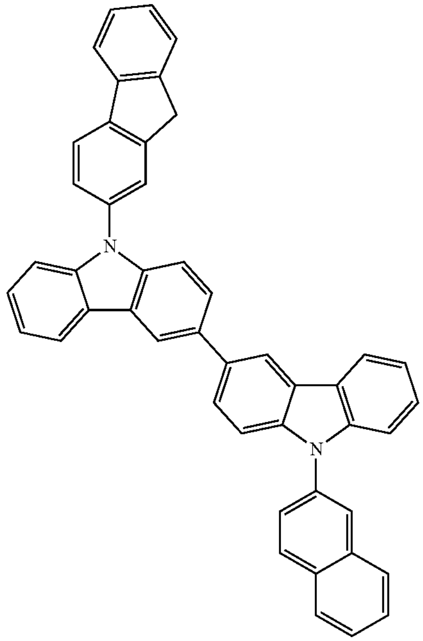
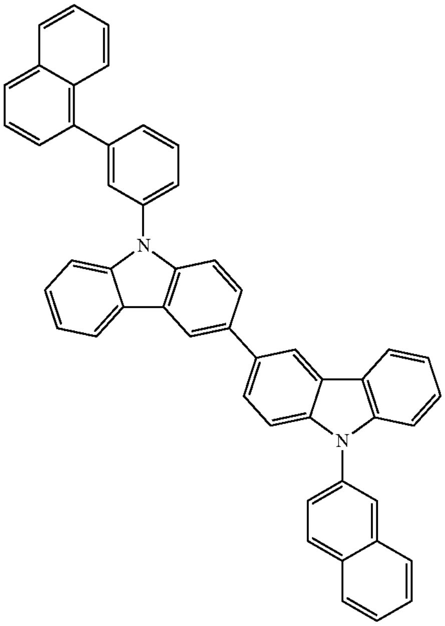

-continued
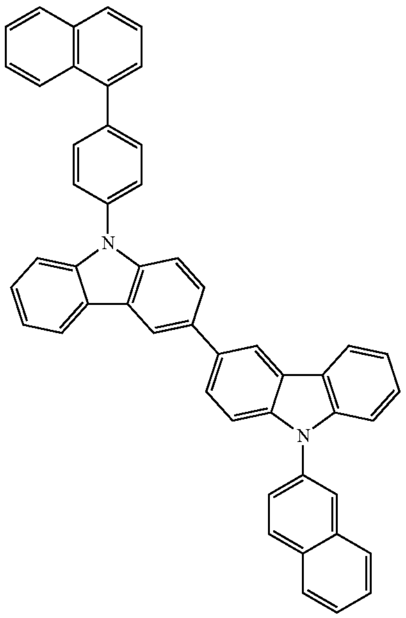
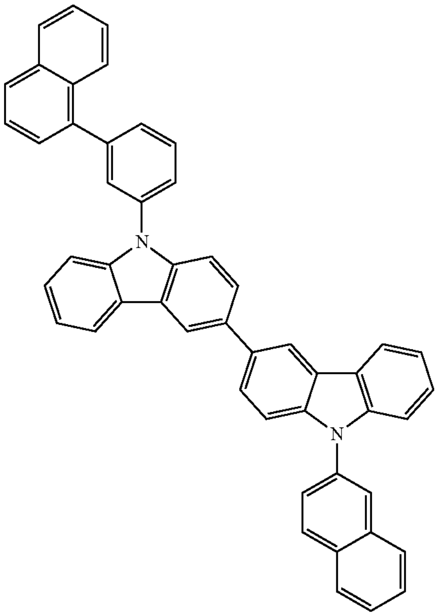
-continued
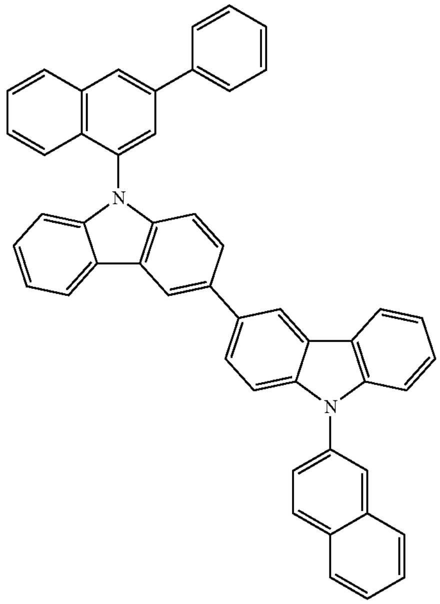
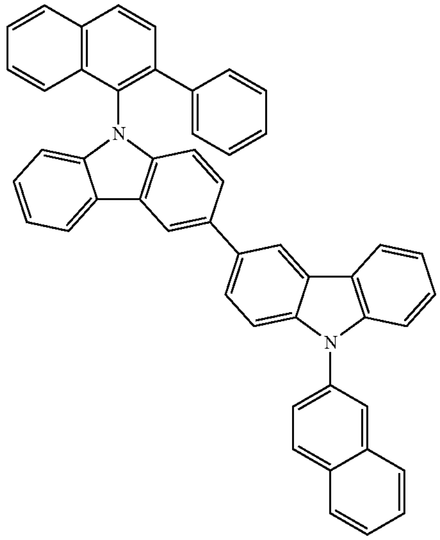

-continued
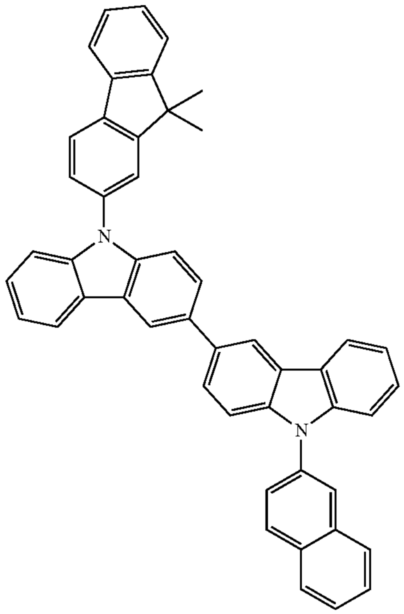
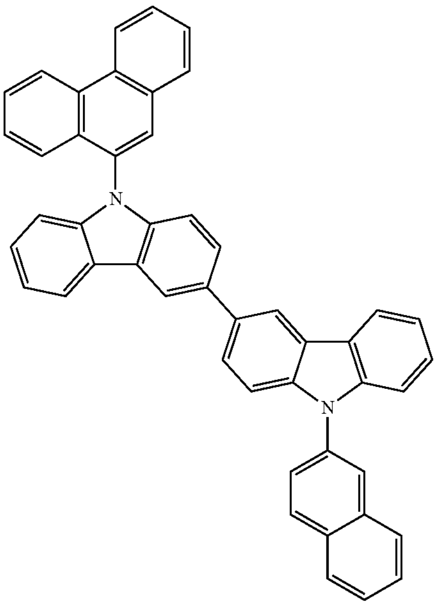
-continued
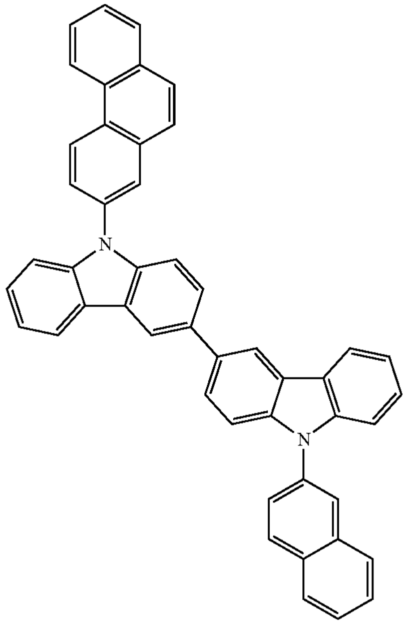
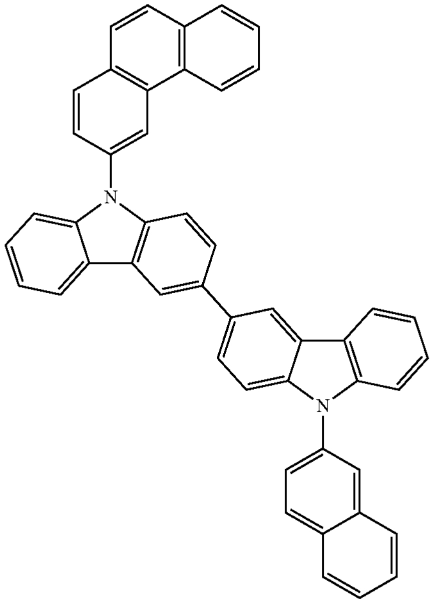

-continued
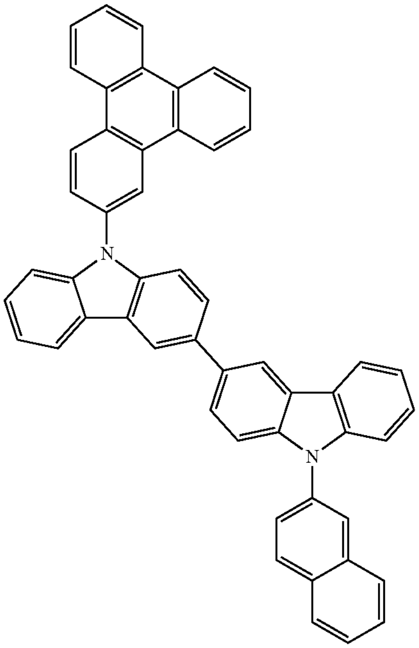
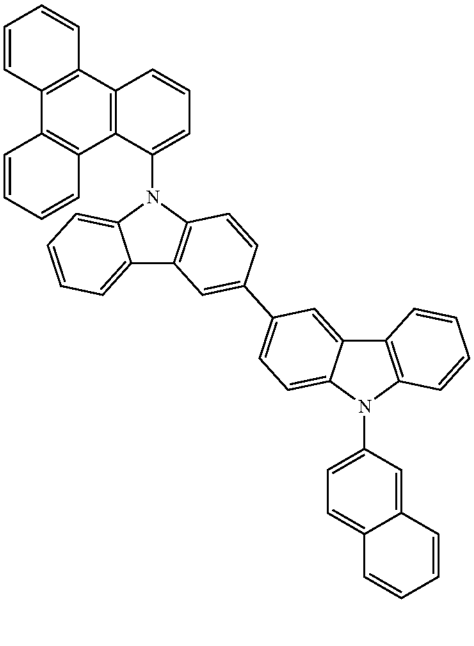
-continued
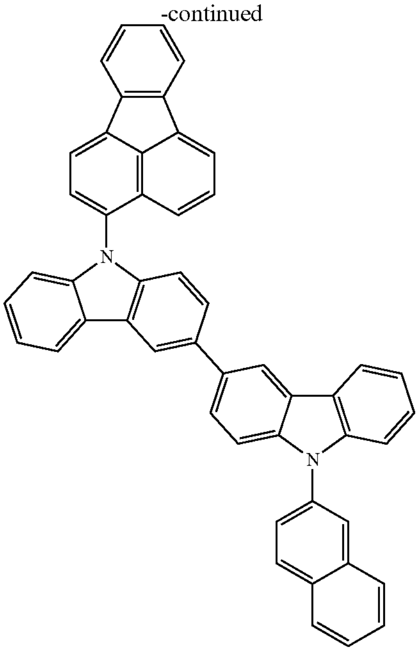
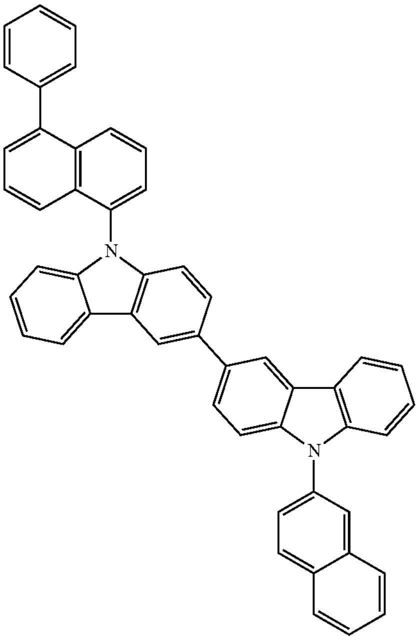

-continued
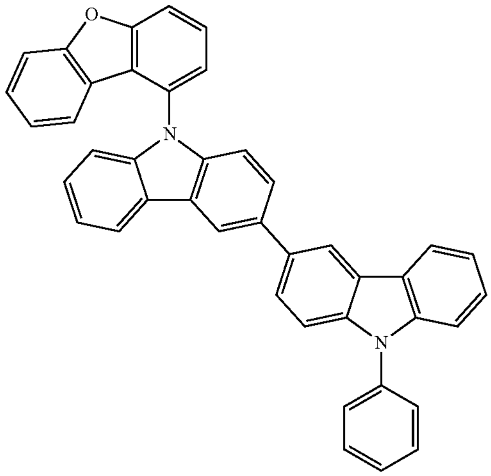
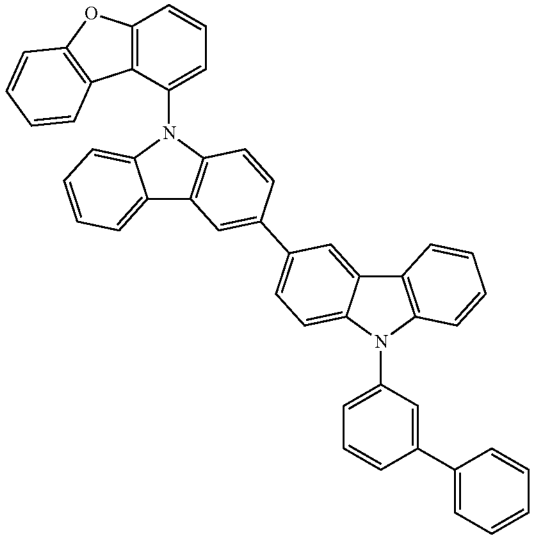
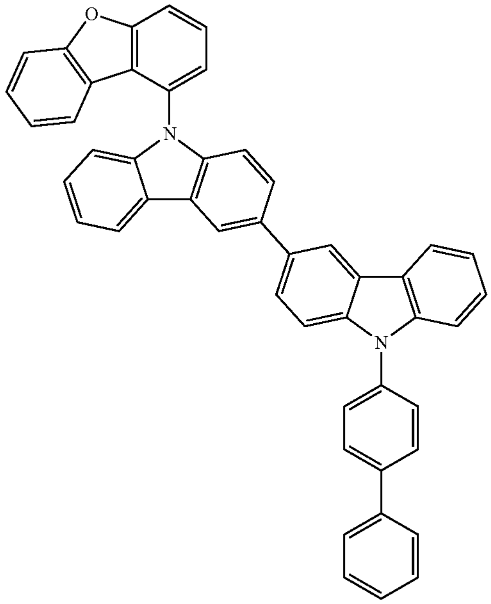
-continued
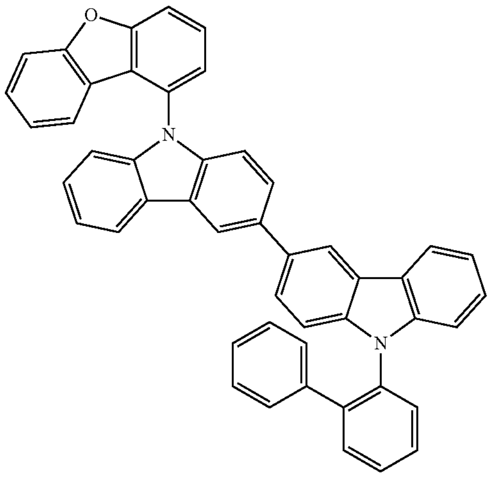
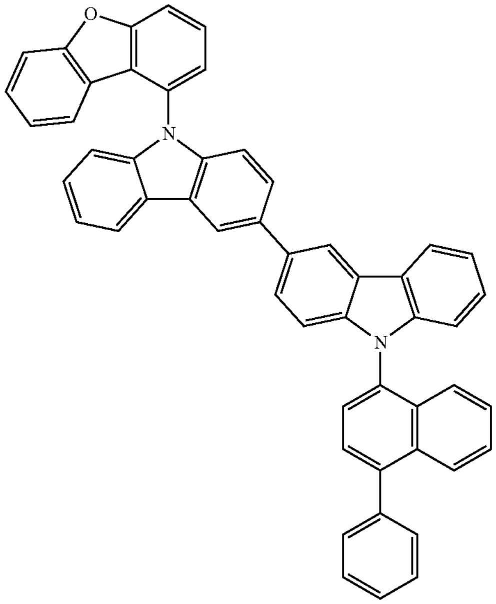
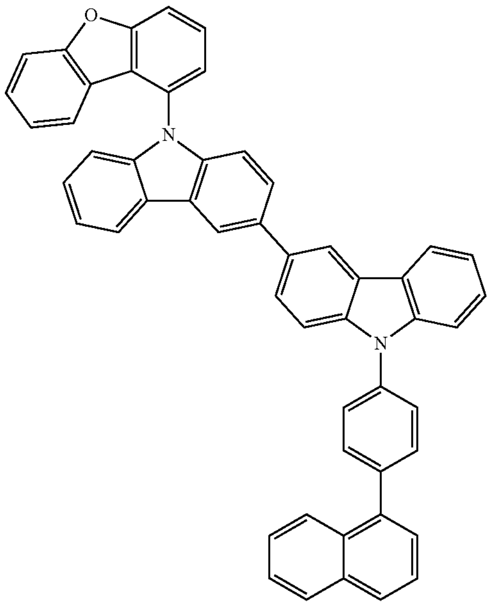

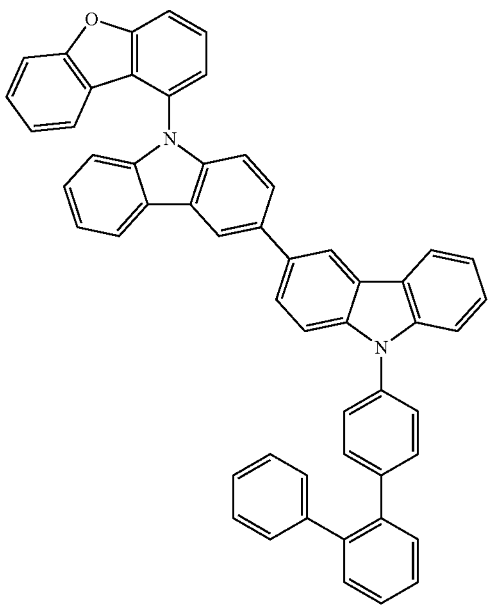
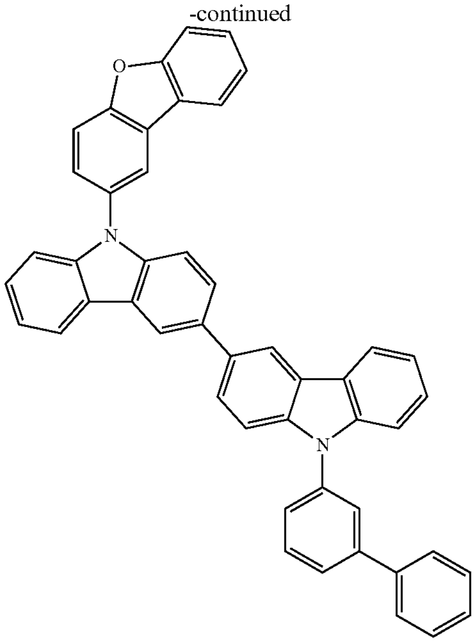
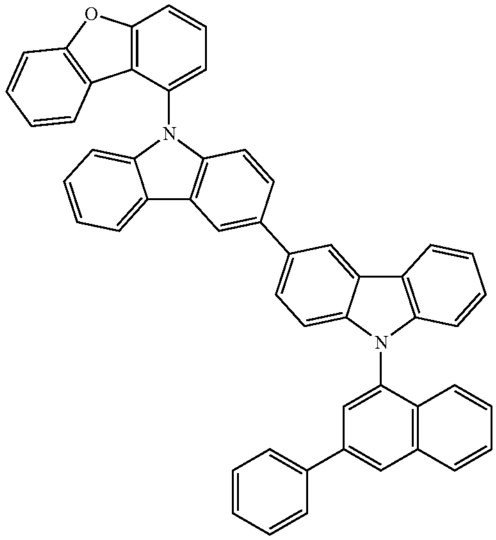
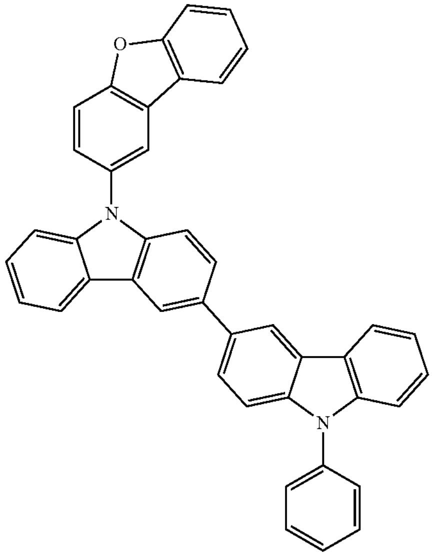
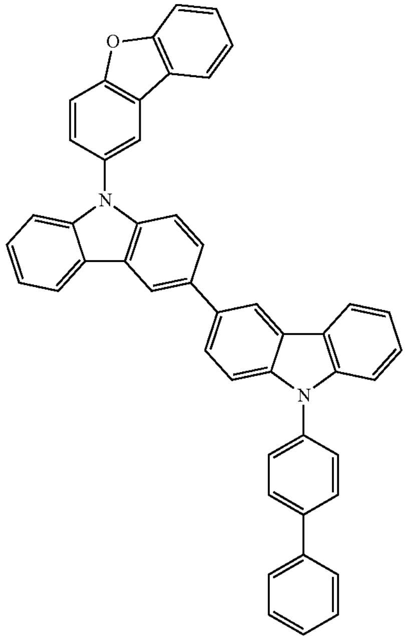

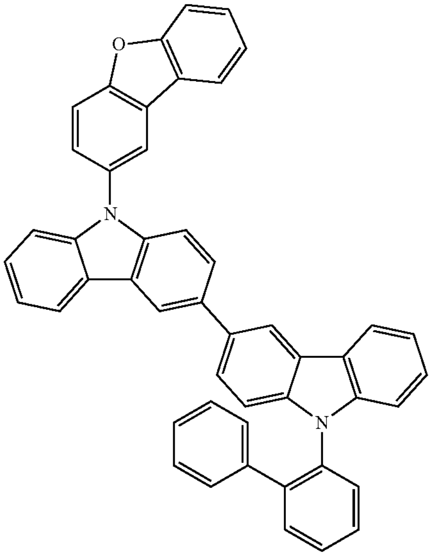
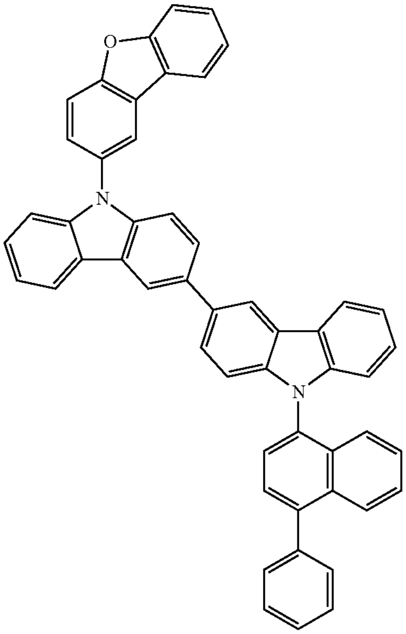
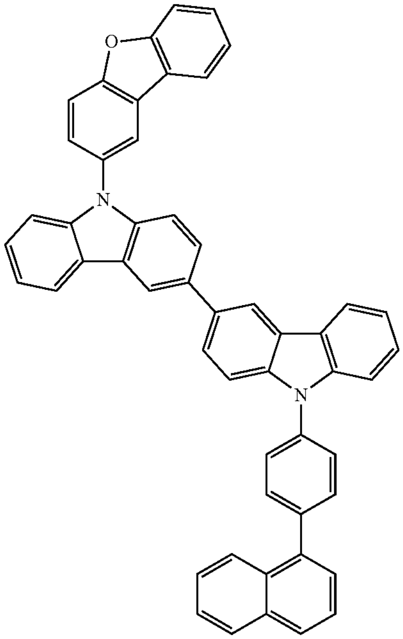
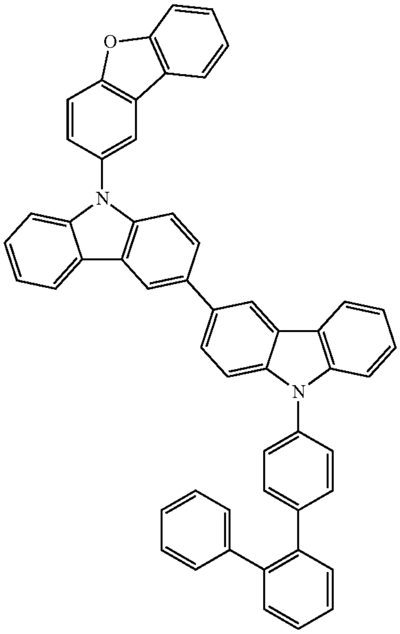

-continued
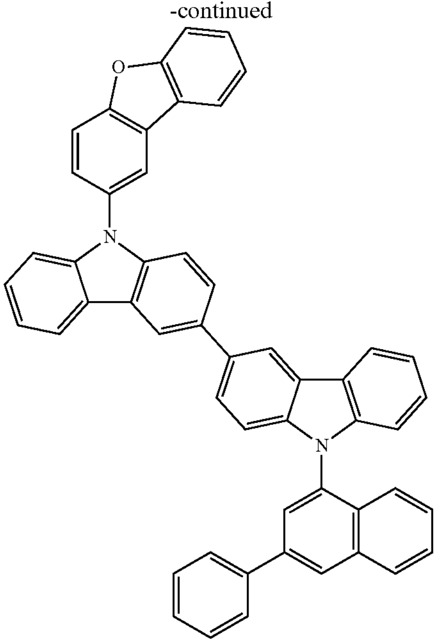
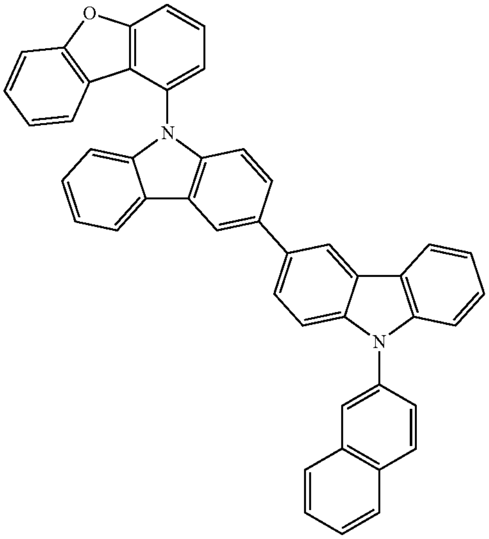
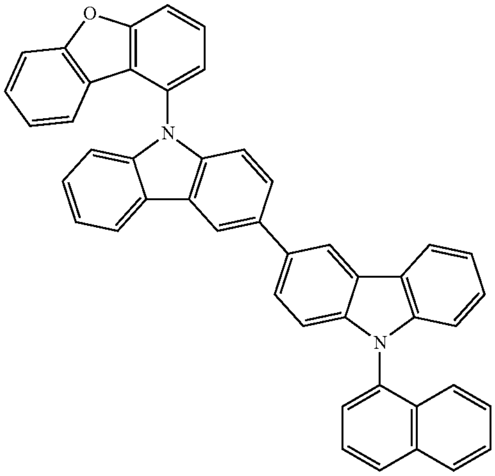
-continued
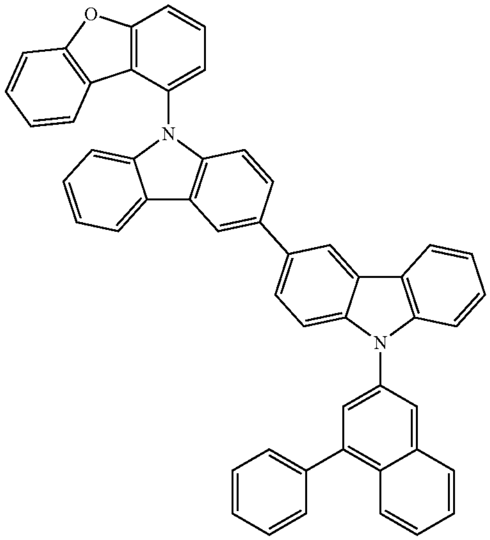
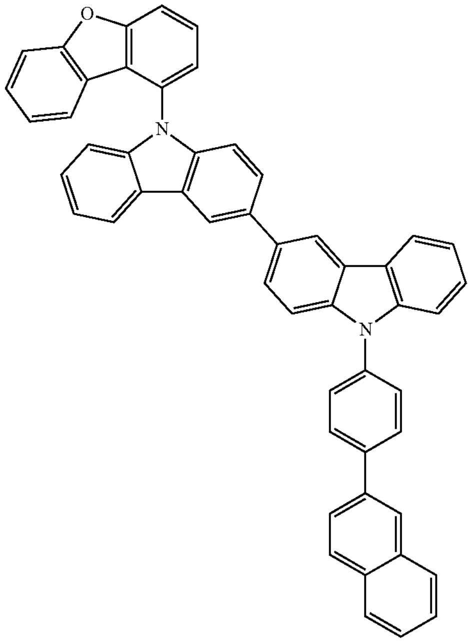 [SMILES: c1ccc2cc(-c3ccc(-n4c5ccccc5c5cc(-c6ccc7c(c6)c6ccccc6n7-c6cccc7oc8ccccc8c67)ccc54)cc3)ccc2c1]

-continued
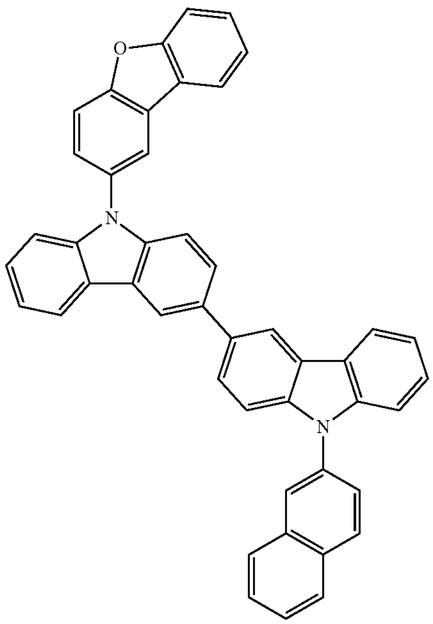
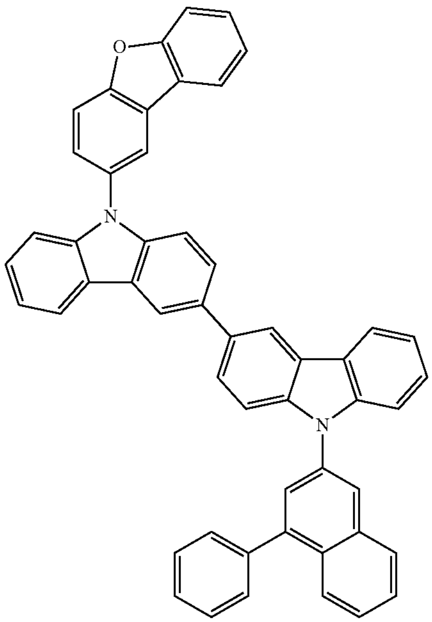
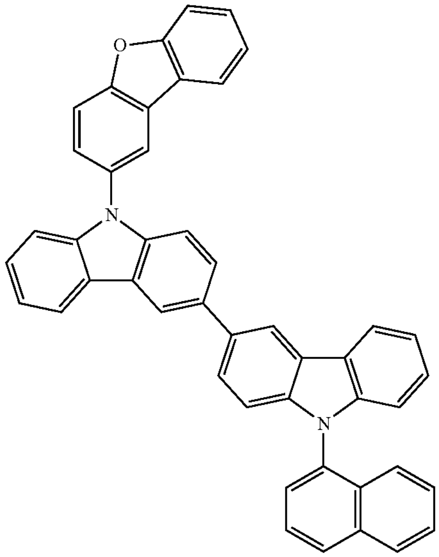
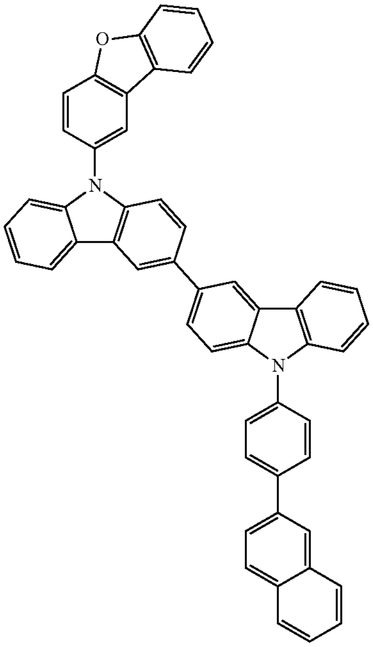 [SMILES: c1ccc2cc(-c3ccc(-n4c5ccccc5c5cc(-c6ccc7c(c6)c6ccccc6n7-c6ccc7oc8ccccc8c7c6)ccc54)cc3)ccc2c1]
-continued

-continued
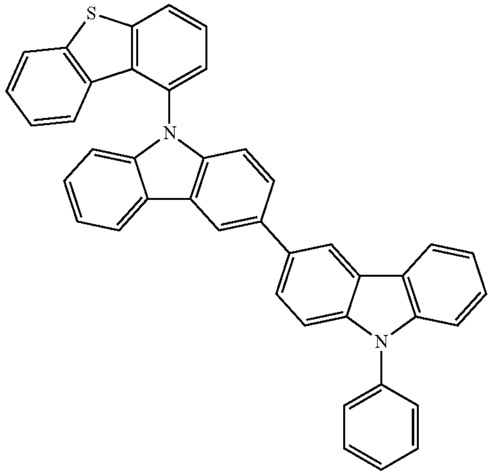
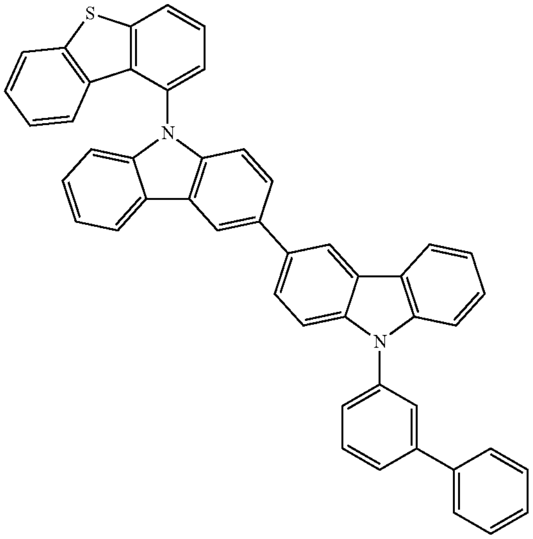
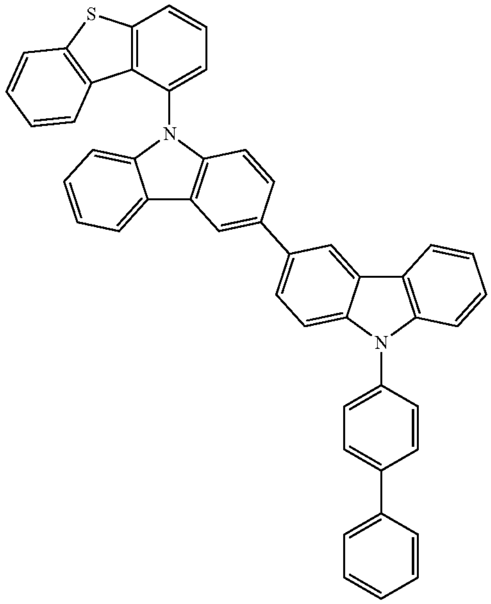
-continued
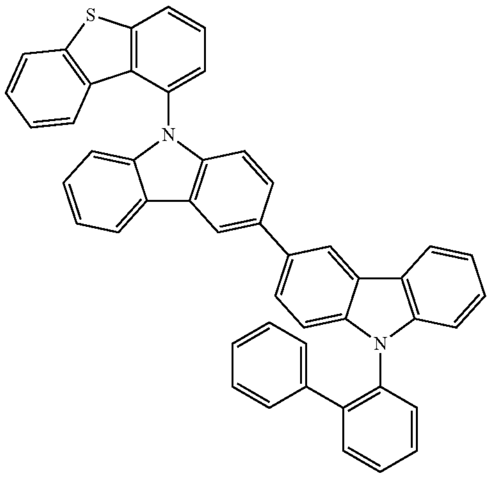
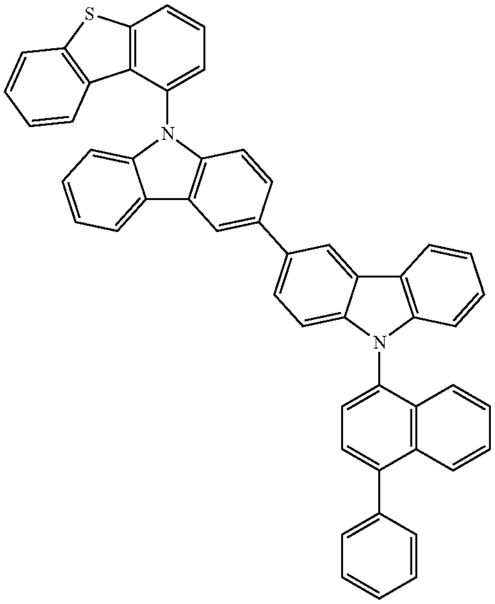
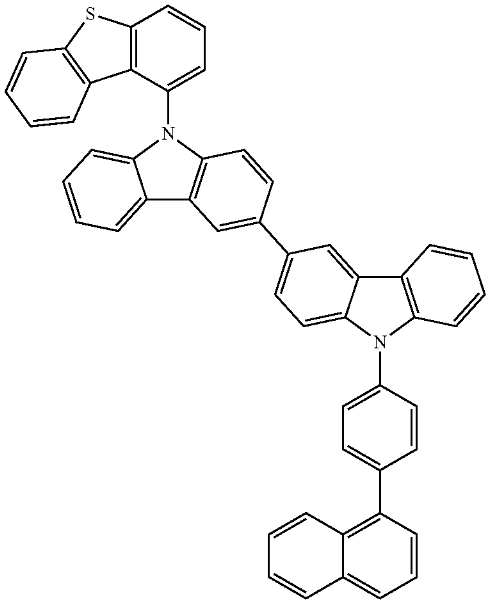

-continued
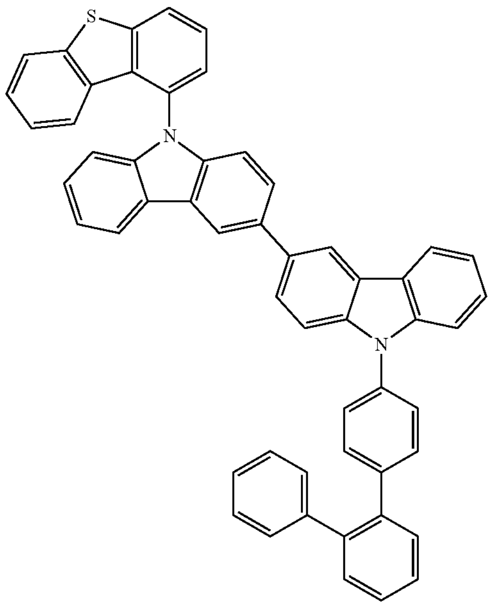
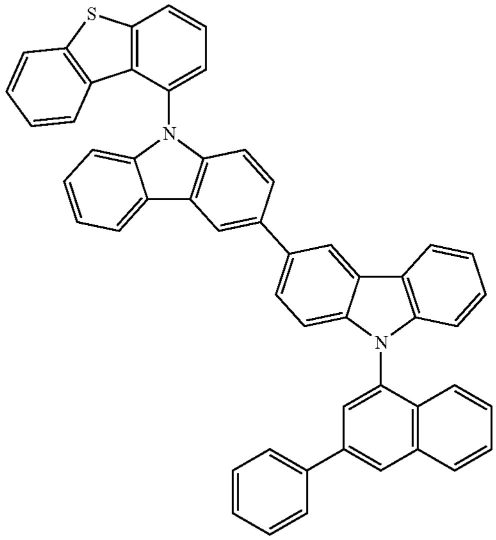
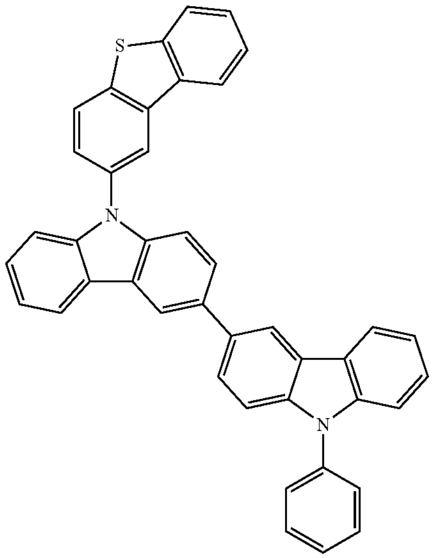
-continued
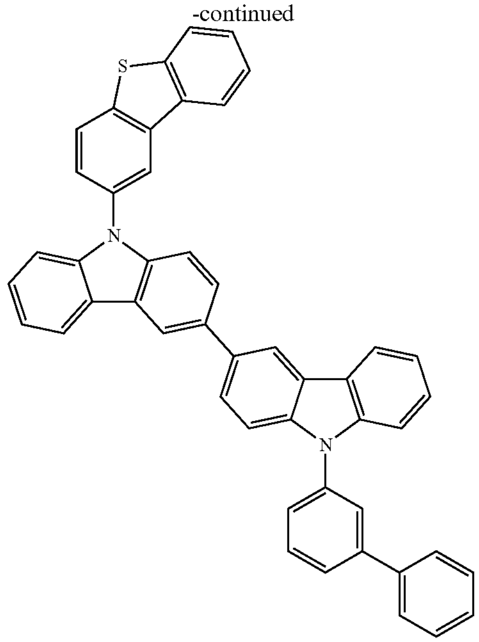
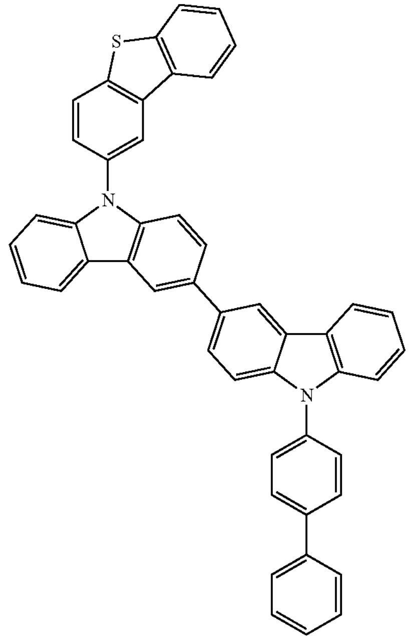

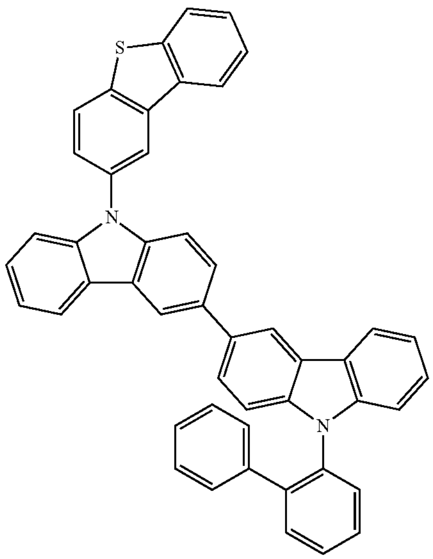
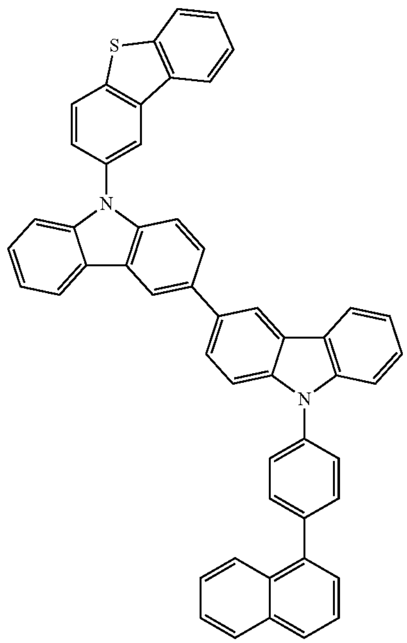
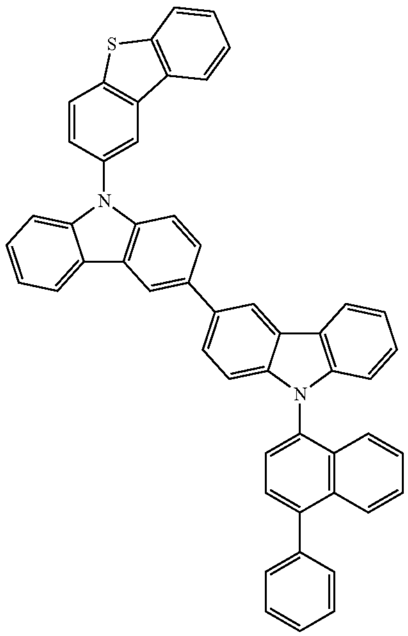
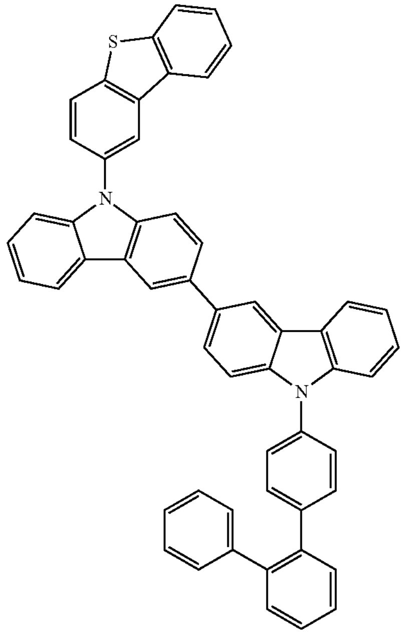

-continued
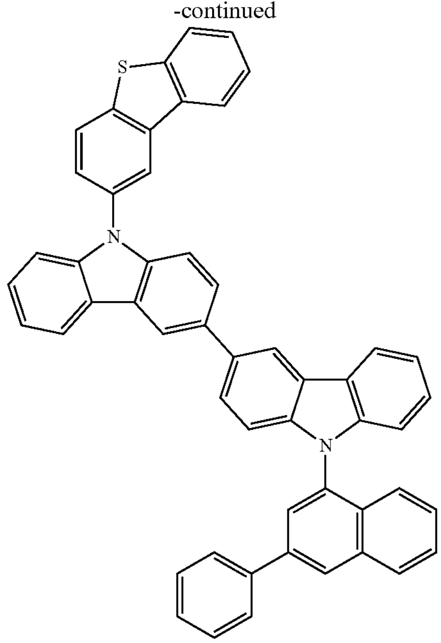
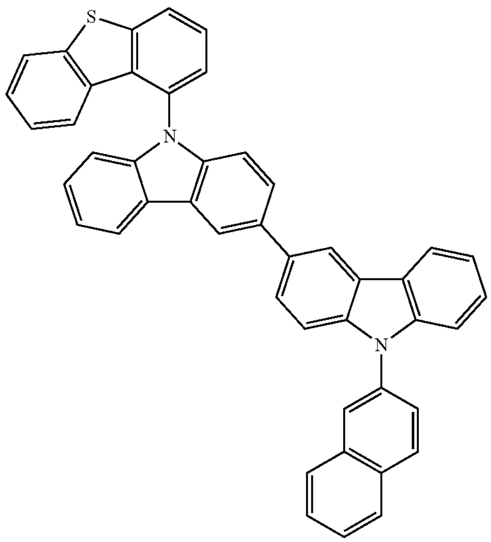
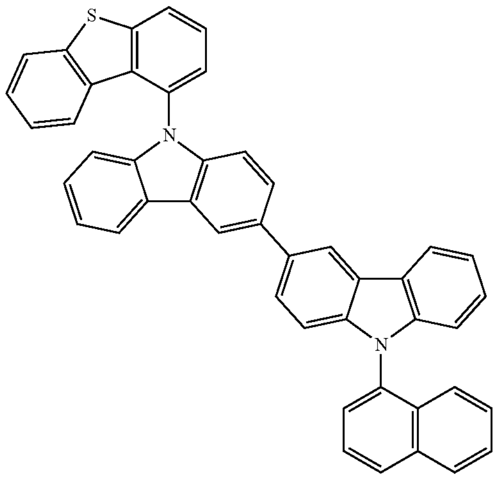
-continued
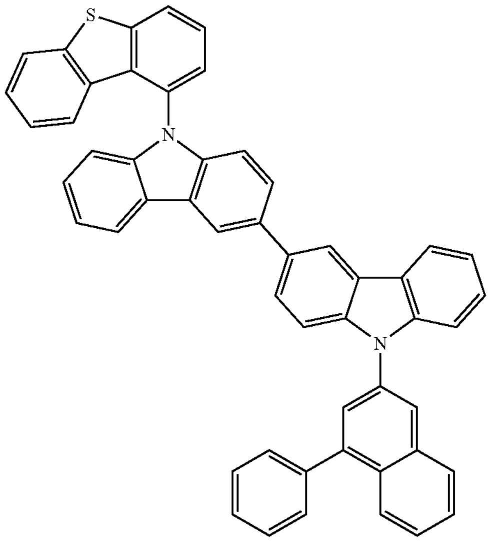
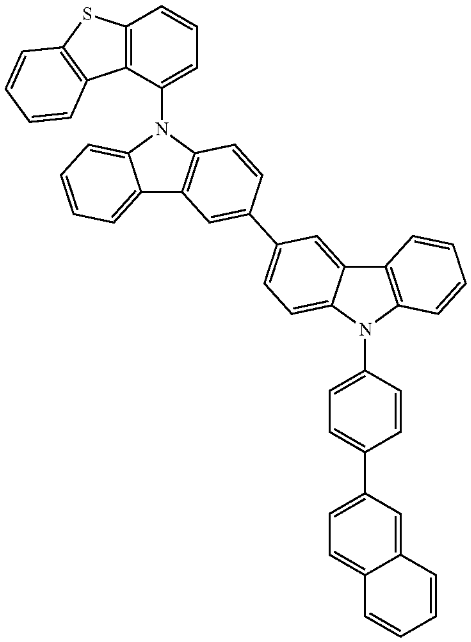 [SMILES: c1ccc2cc(-c3ccc(-n4c5ccccc5c5cc(-c6ccc7c(c6)c6ccccc6n7-c6cccc7sc8ccccc8c67)ccc54)cc3)ccc2c1]

-continued
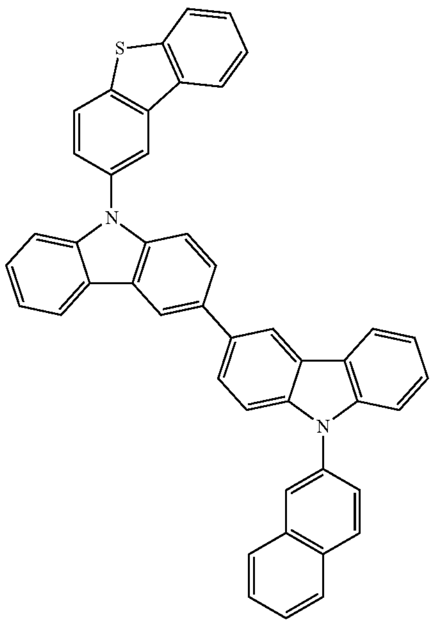
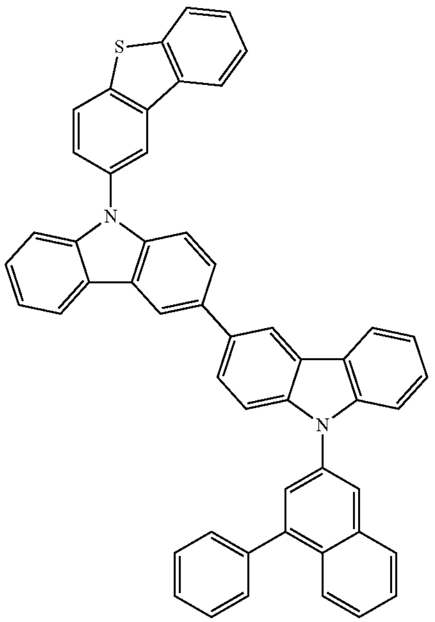
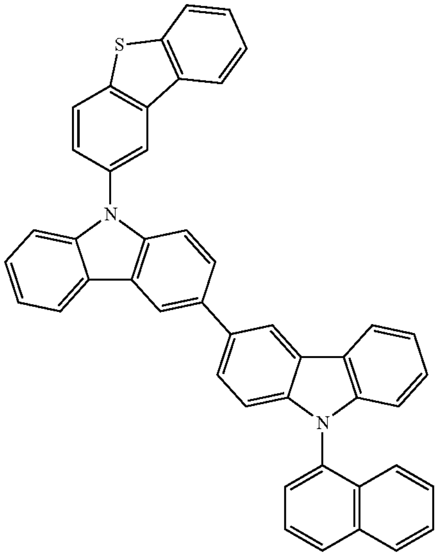
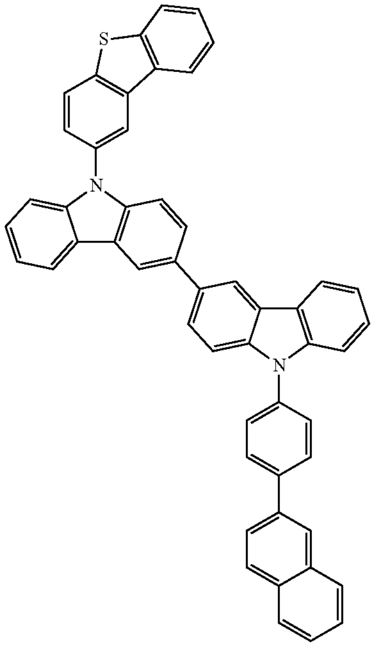 [SMILES: c1ccc2cc(-c3ccc(-n4c5ccccc5c5cc(-c6ccc7c(c6)c6ccccc6n7-c6ccc7sc8ccccc8c7c6)ccc54)cc3)ccc2c1]

-continued
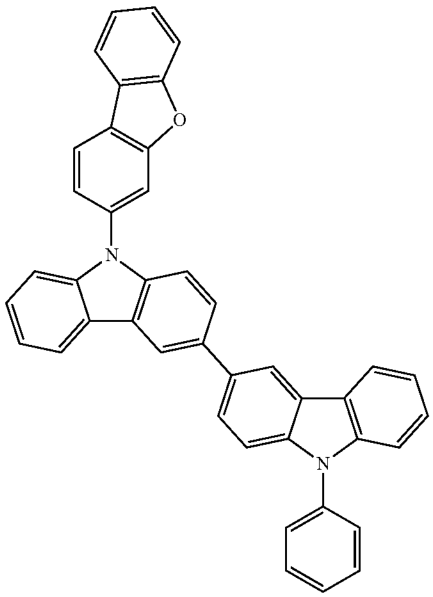
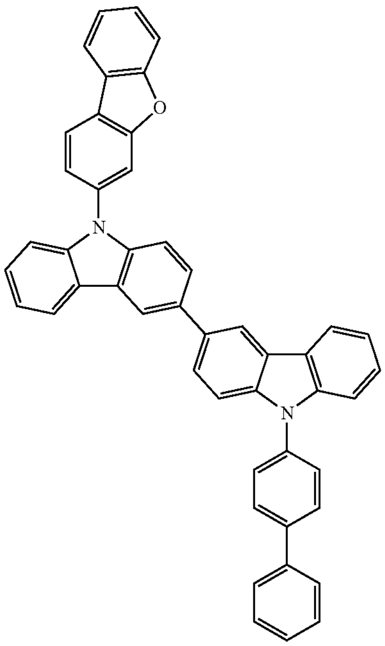
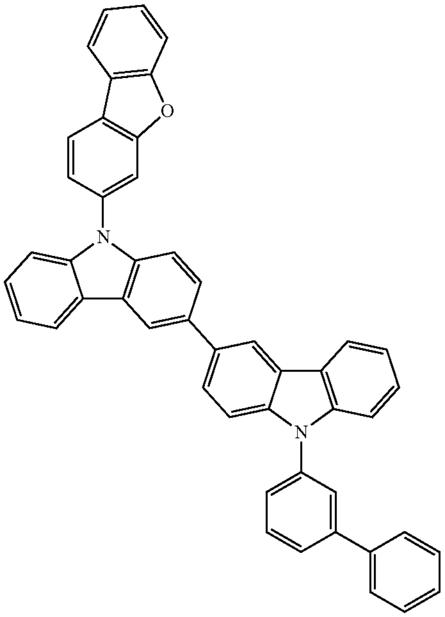
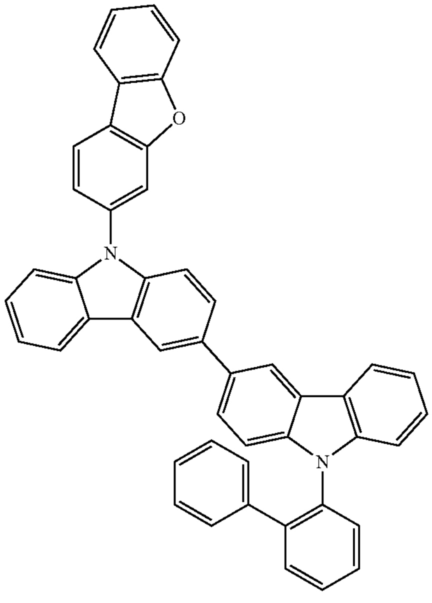
-continued

-continued
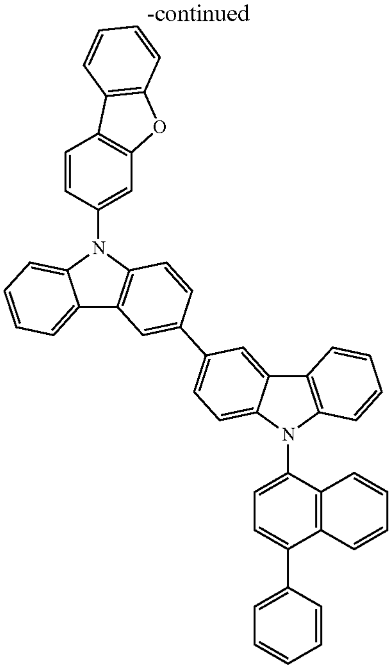
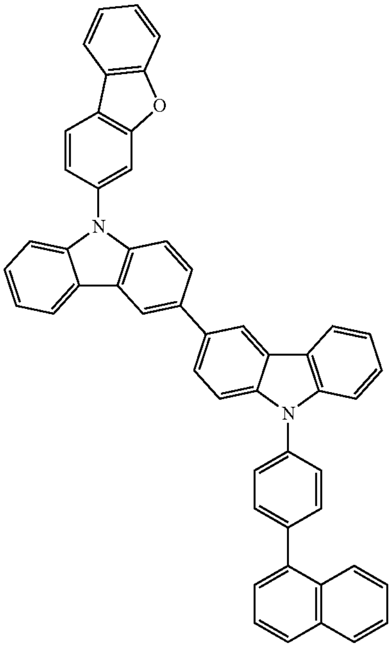
-continued
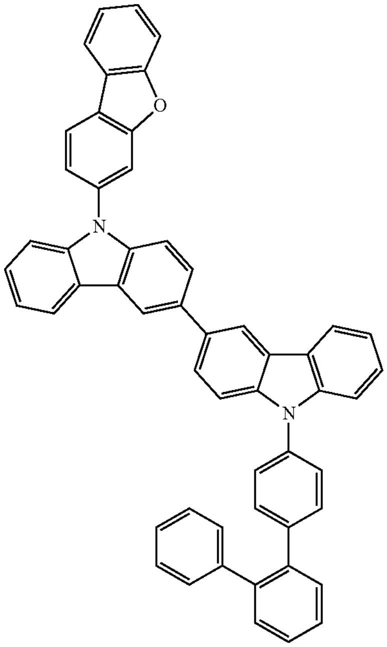
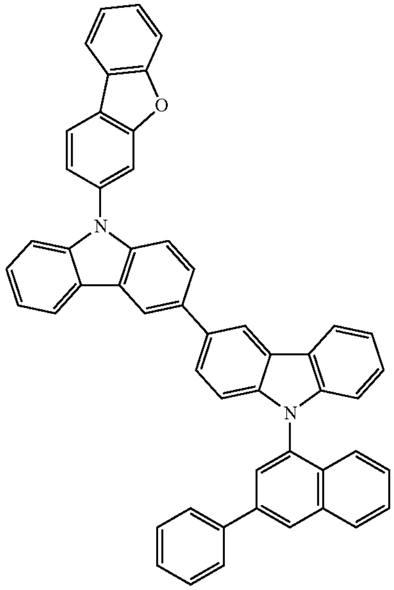 [SMILES: c1ccc(-c2cc(-n3c4ccccc4c4cc(-c5ccc6c(c5)c5ccccc5n6-c5ccc6c(c5)oc5ccccc56)ccc43)c3ccccc3c2)cc1]

-continued
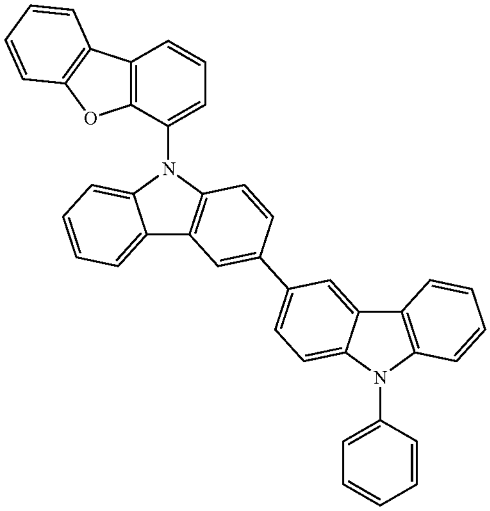
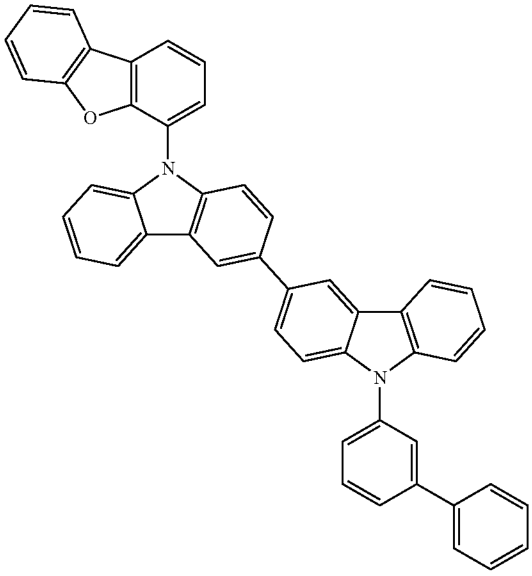
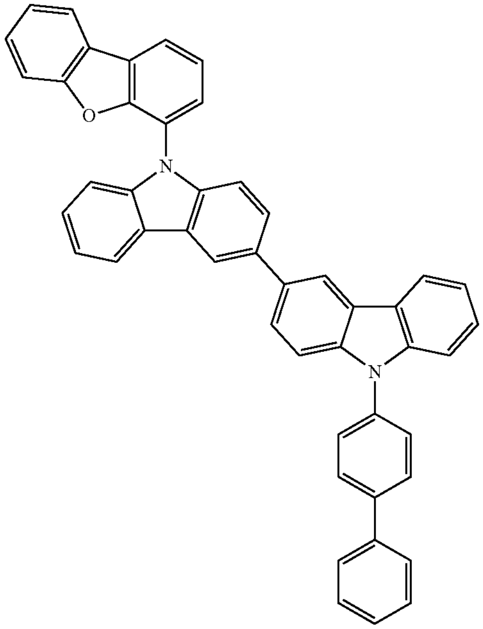
-continued
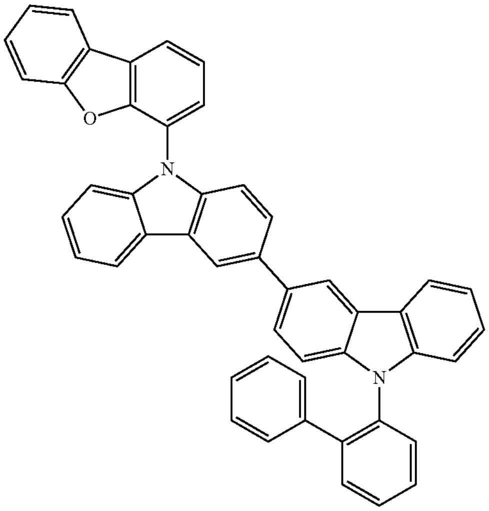
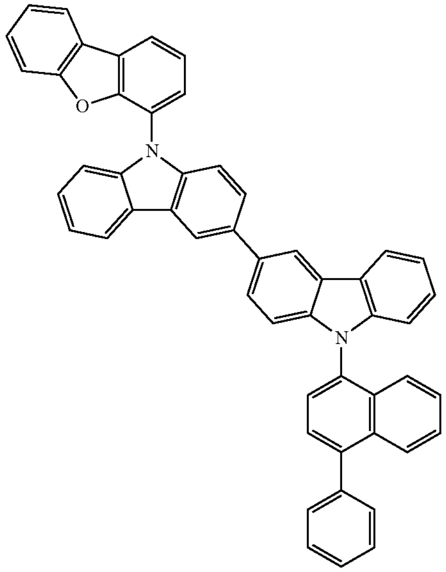
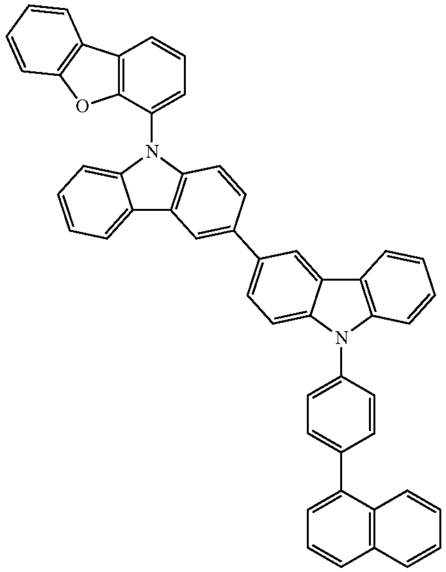

-continued
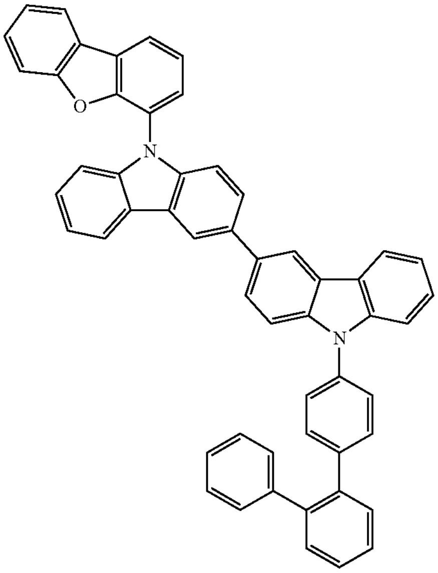
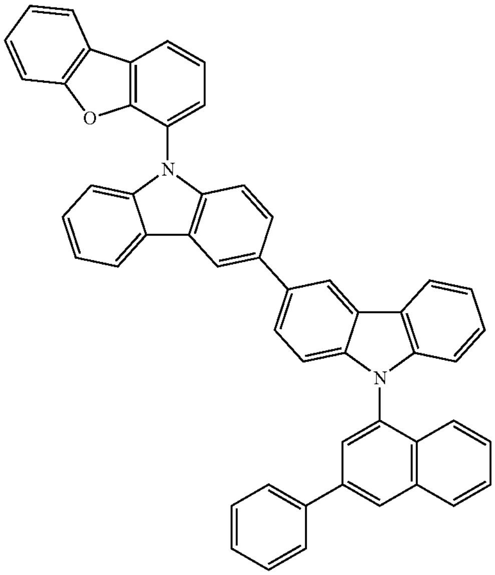 [SMILES: c1ccc(-c2cc(-n3c4ccccc4c4cc(-c5ccc6c(c5)c5ccccc5n6-c5cccc6c5oc5ccccc56)ccc43)c3ccccc3c2)cc1]
-continued
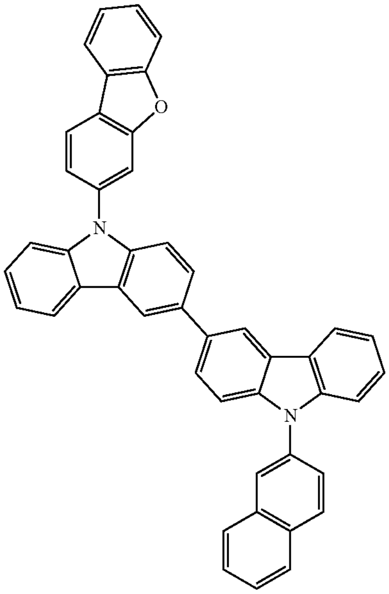
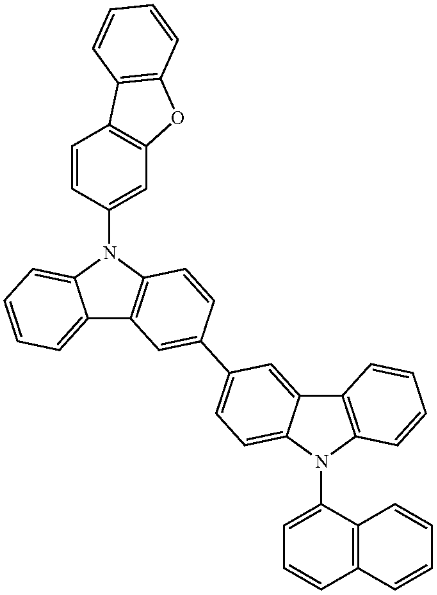

-continued
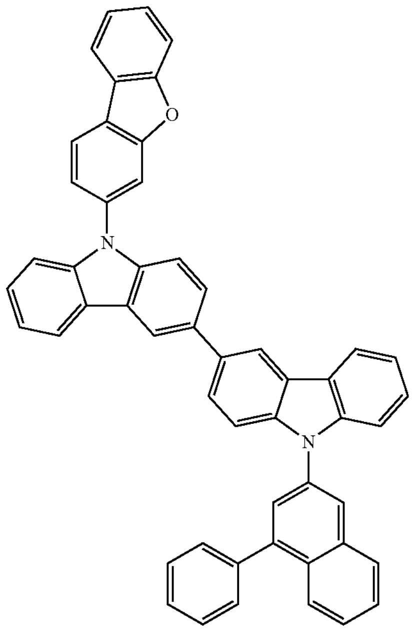
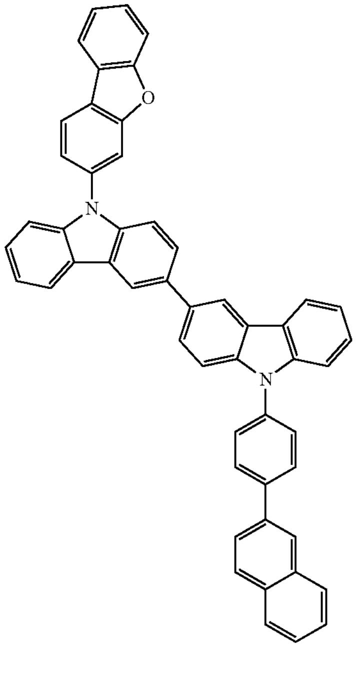 [SMILES: c1ccc2cc(-c3ccc(-n4c5ccccc5c5cc(-c6ccc7c(c6)c6ccccc6n7-c6ccc7c(c6)oc6ccccc67)ccc54)cc3)ccc2c1]
-continued
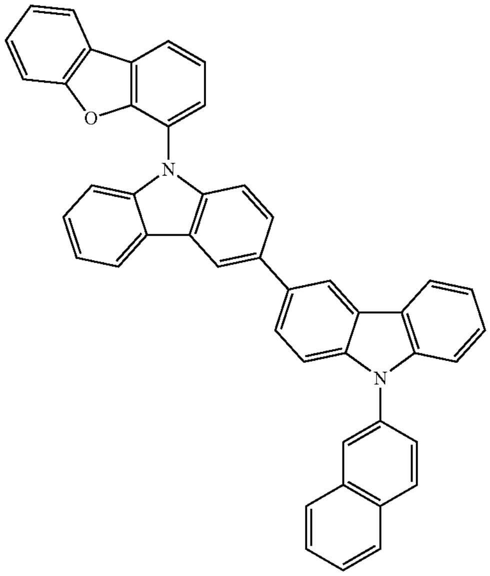
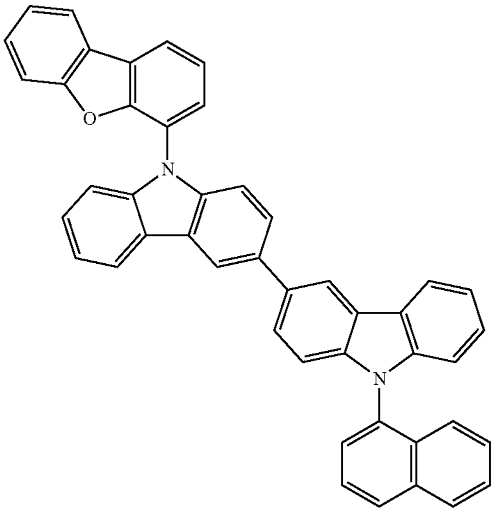
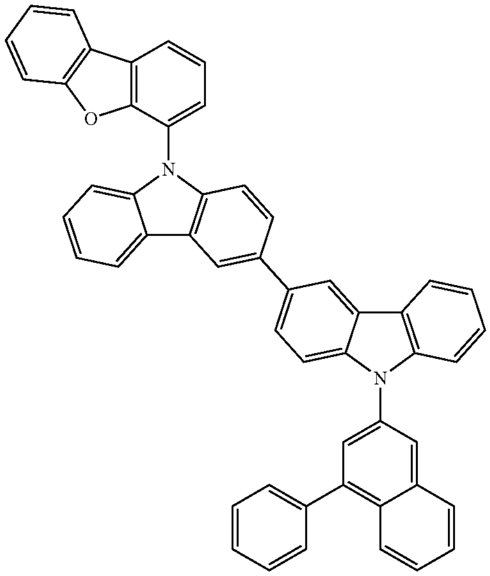

-continued
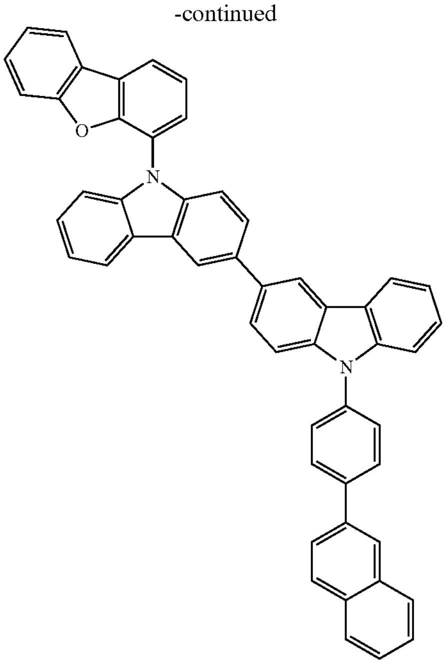
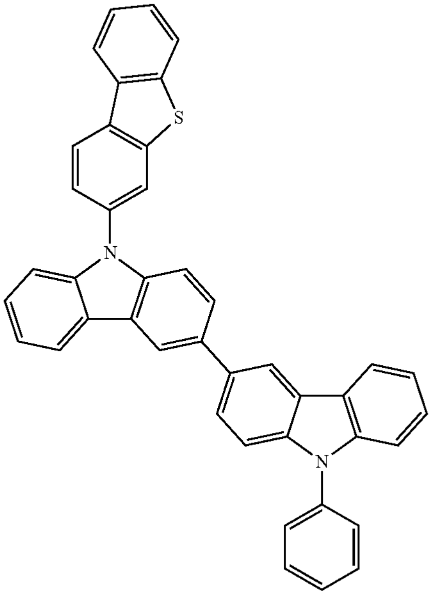
-continued
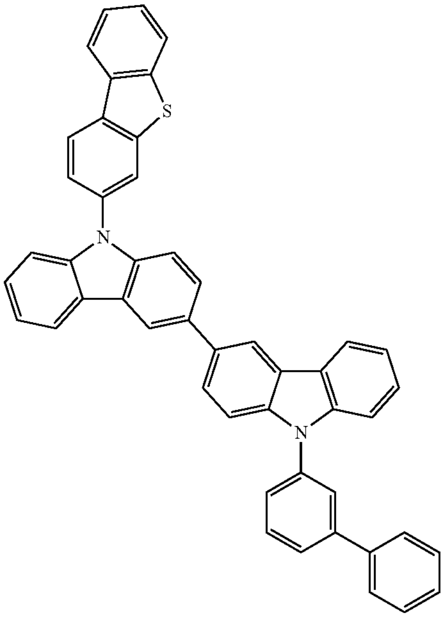
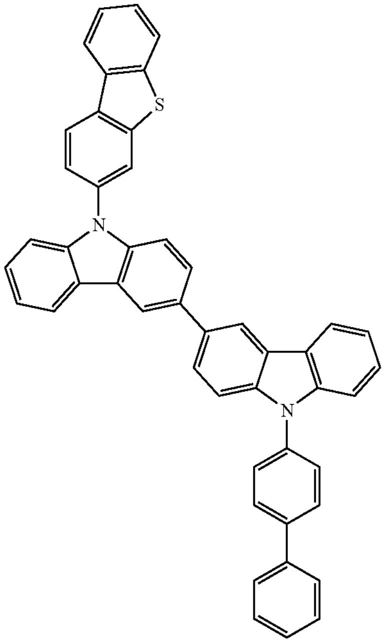

-continued
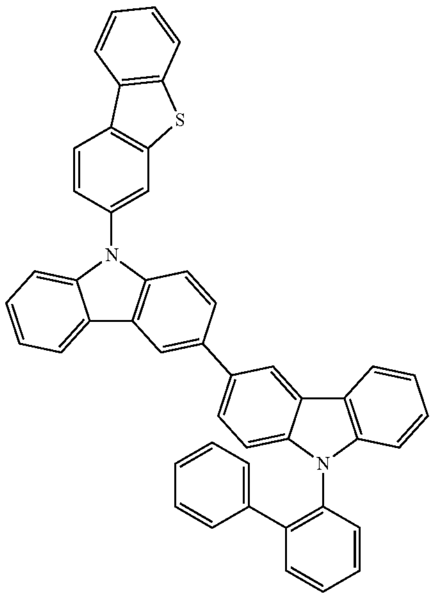
-continued
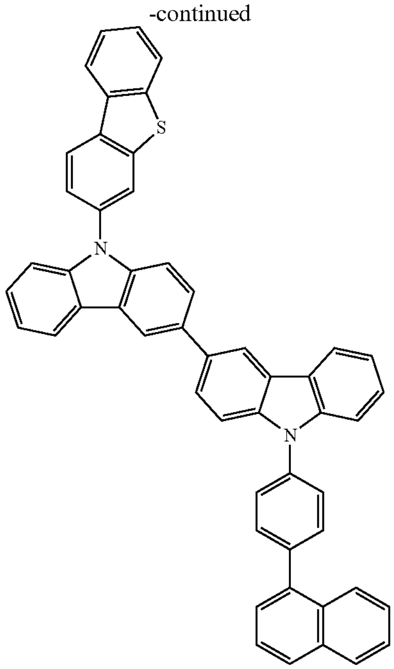
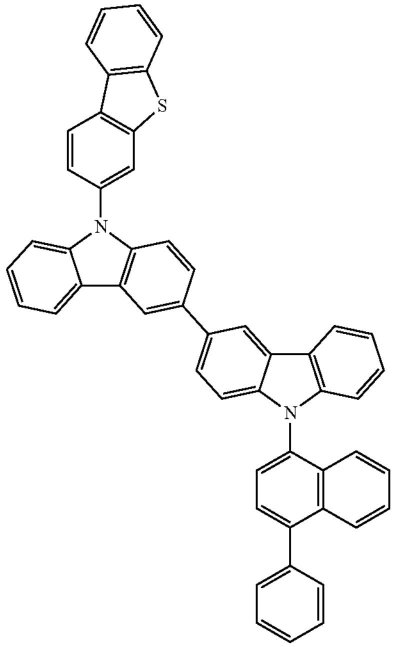
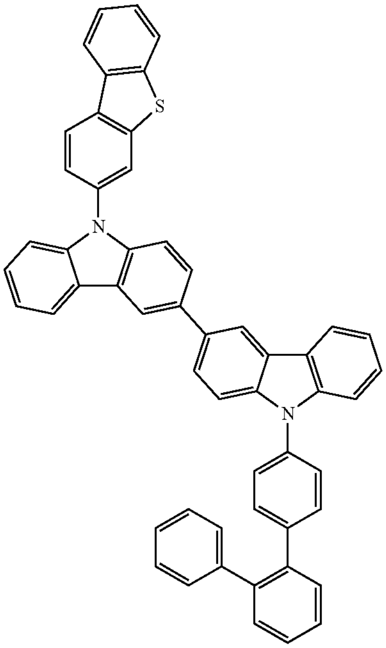

-continued
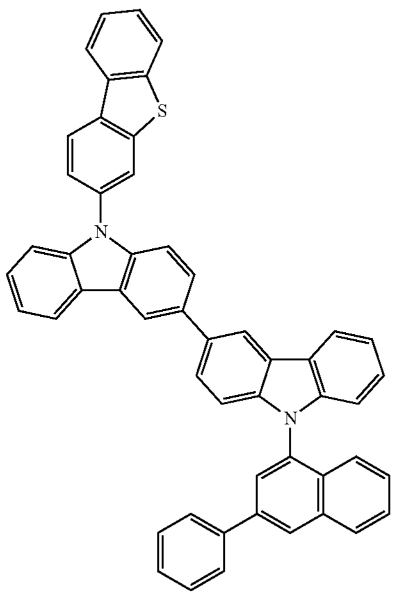 [SMILES: c1ccc(-c2cc(-n3c4ccccc4c4cc(-c5ccc6c(c5)c5ccccc5n6-c5ccc6c(c5)sc5ccccc56)ccc43)c3ccccc3c2)cc1]
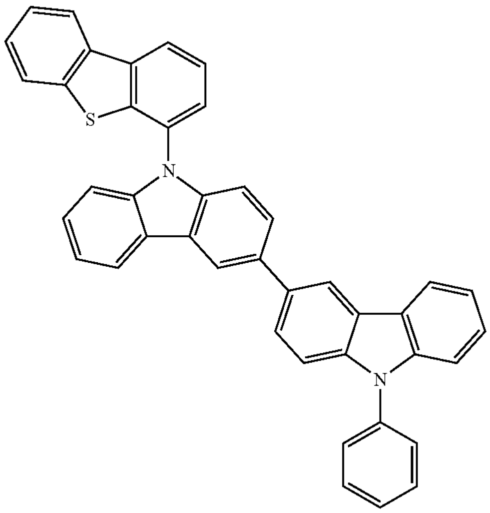
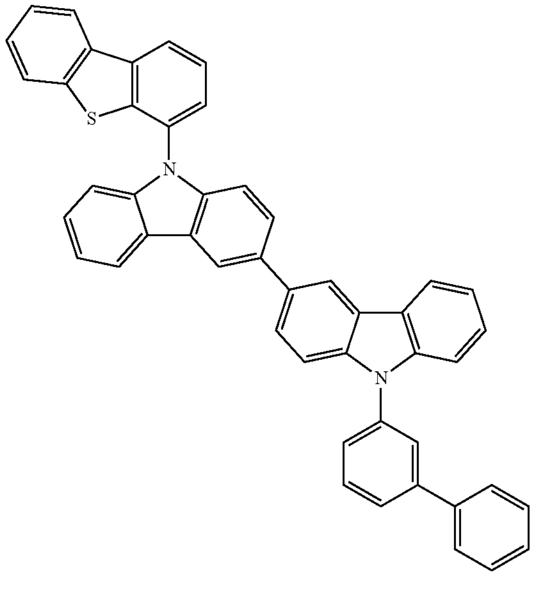
-continued
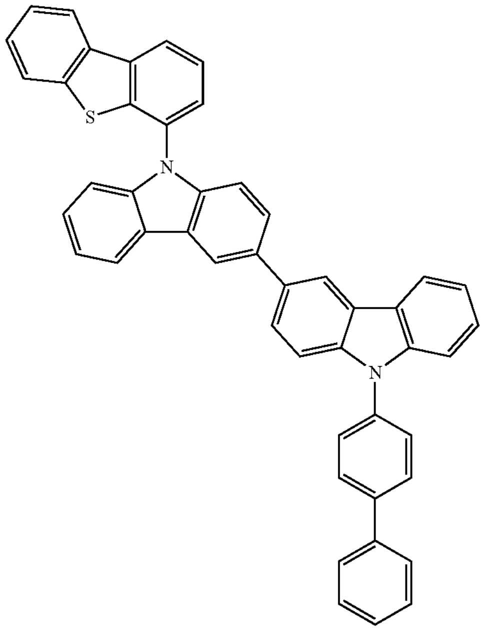
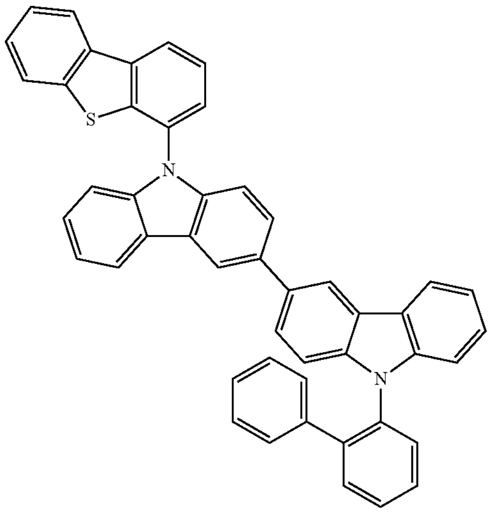
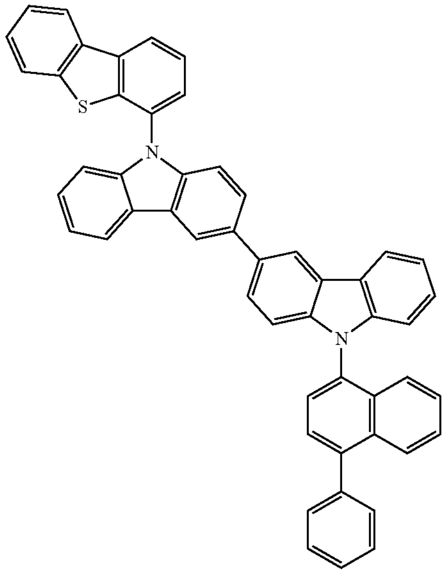

-continued
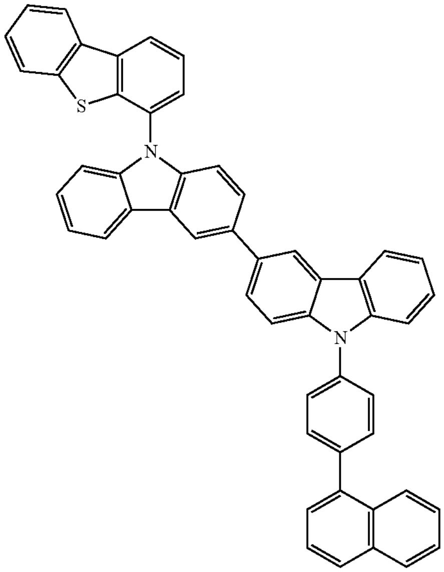
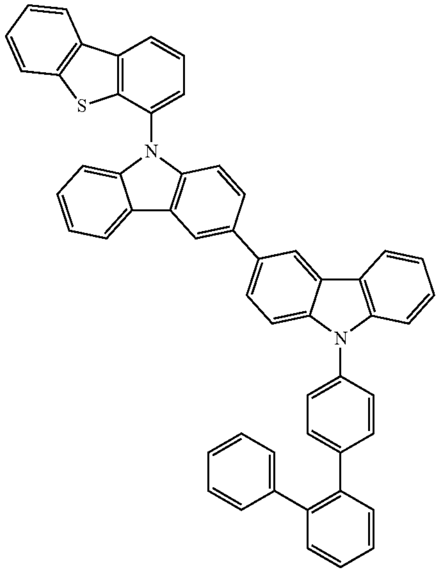
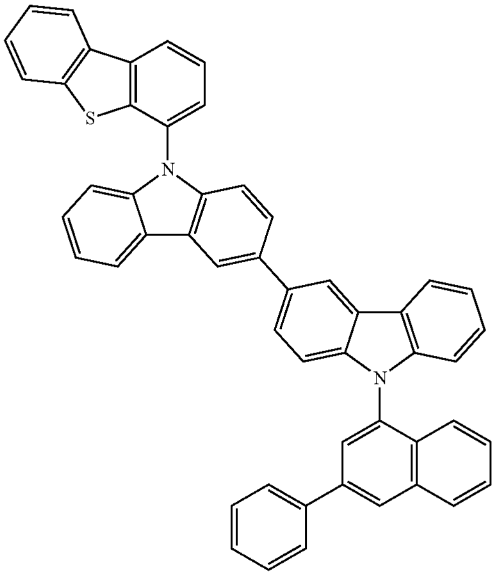 [SMILES: c1ccc(-c2cc(-n3c4ccccc4c4cc(-c5ccc6c(c5)c5ccccc5n6-c5cccc6c5sc5ccccc56)ccc43)c3ccccc3c2)cc1]
-continued
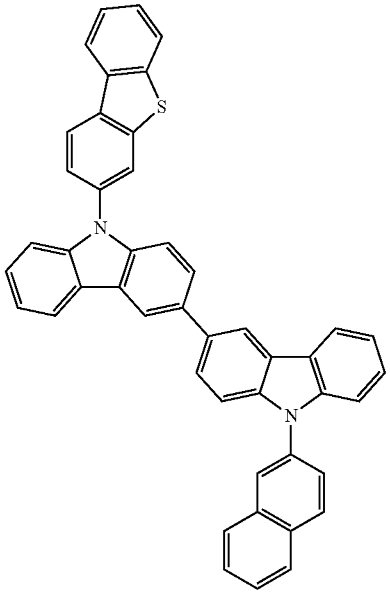
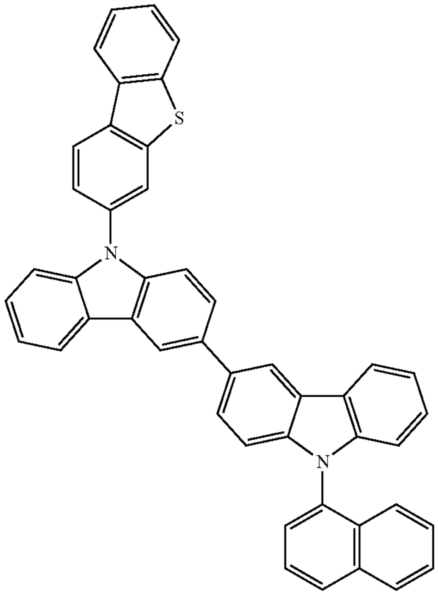

-continued
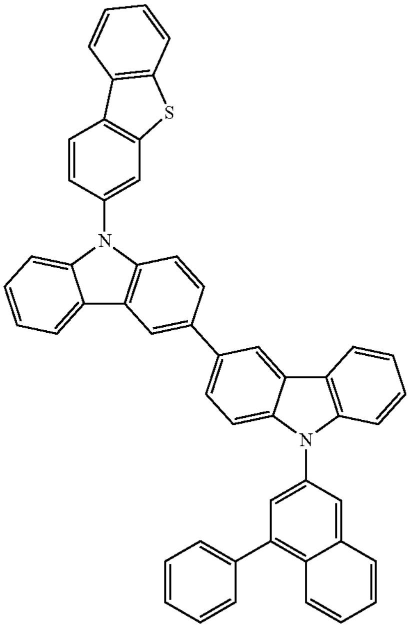
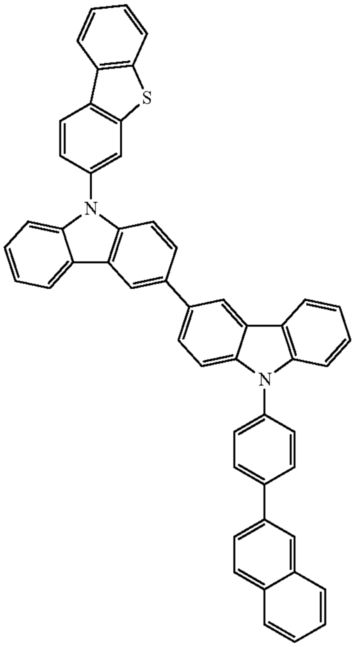 [SMILES: c1ccc2cc(-c3ccc(-n4c5ccccc5c5cc(-c6ccc7c(c6)c6ccccc6n7-c6ccc7c(c6)sc6ccccc67)ccc54)cc3)ccc2c1]
-continued
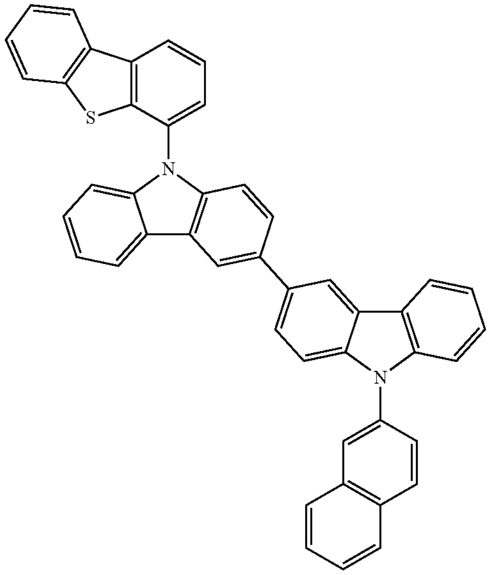
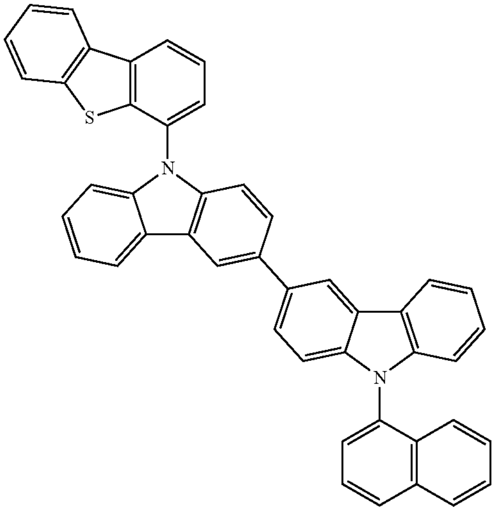
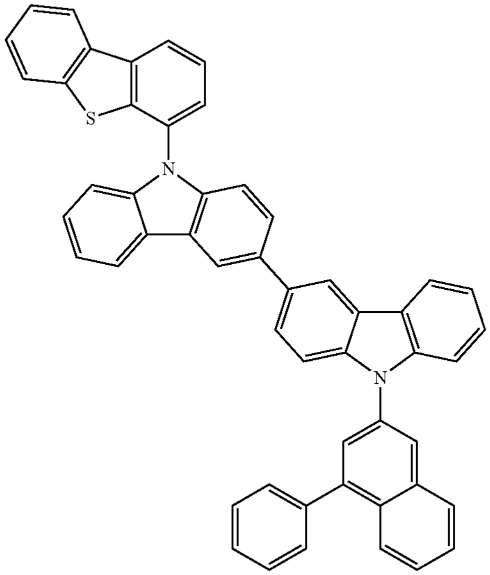

-continued
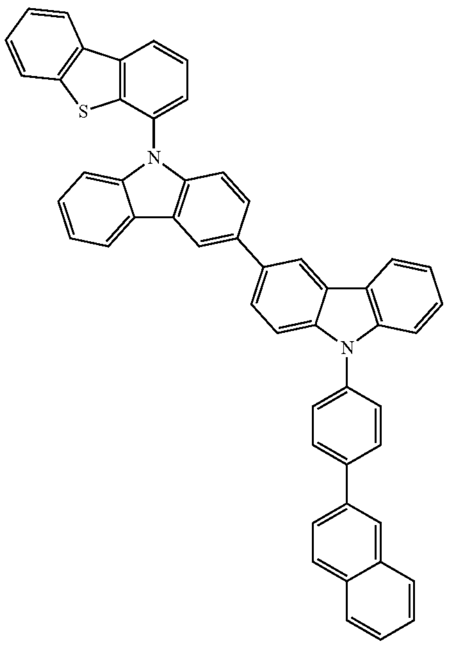 [SMILES: c1ccc2cc(-c3ccc(-n4c5ccccc5c5cc(-c6ccc7c(c6)c6ccccc6n7-c6cccc7c6sc6ccccc67)ccc54)cc3)ccc2c1]
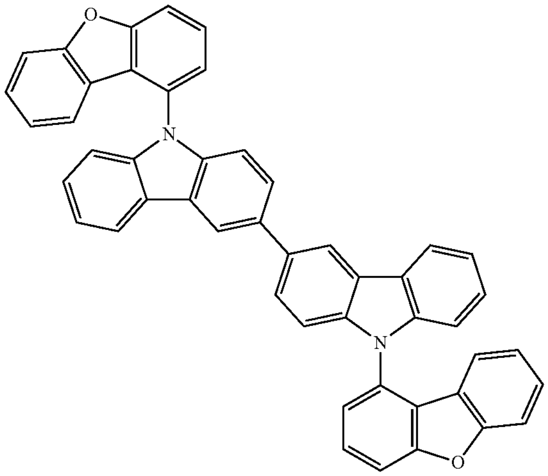
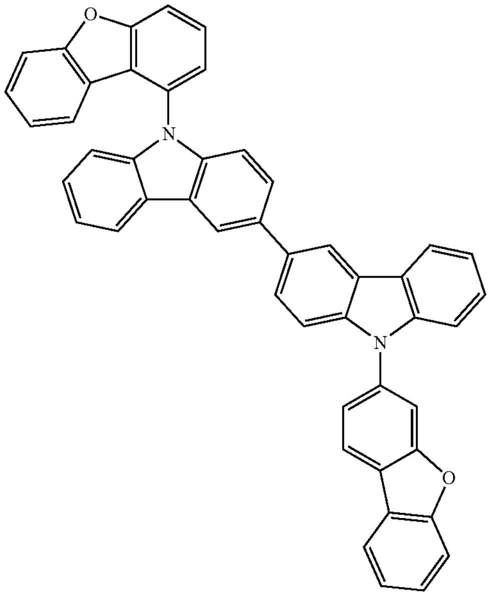
-continued
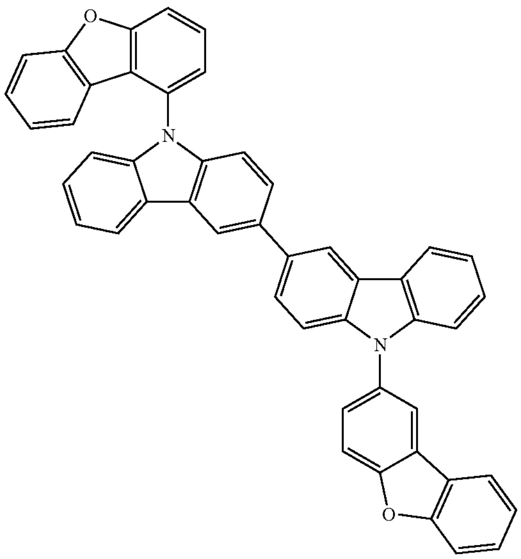
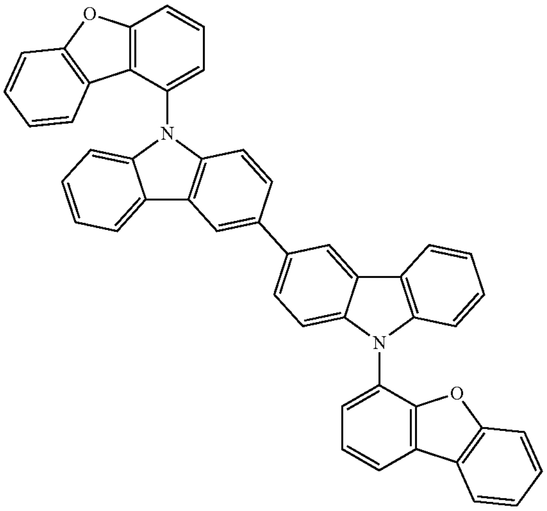
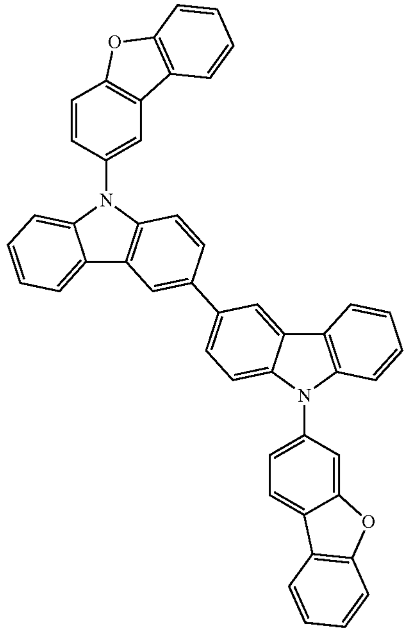

-continued
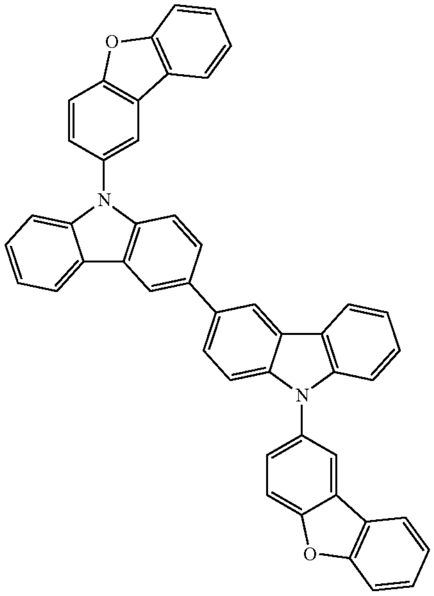
-continued
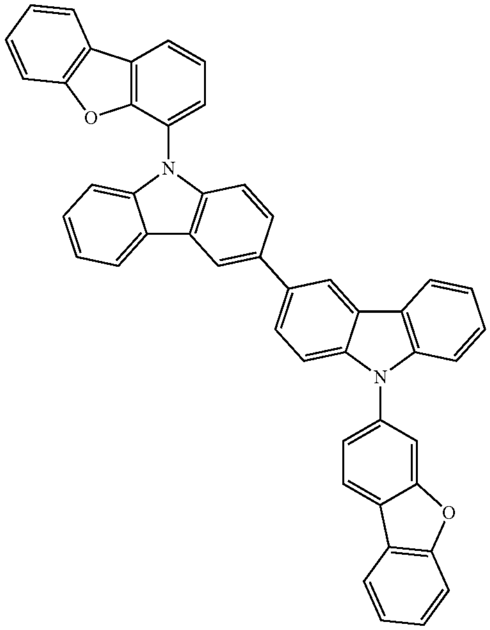
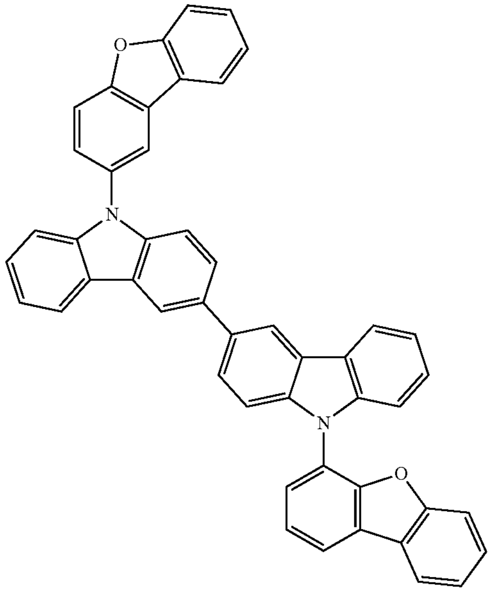
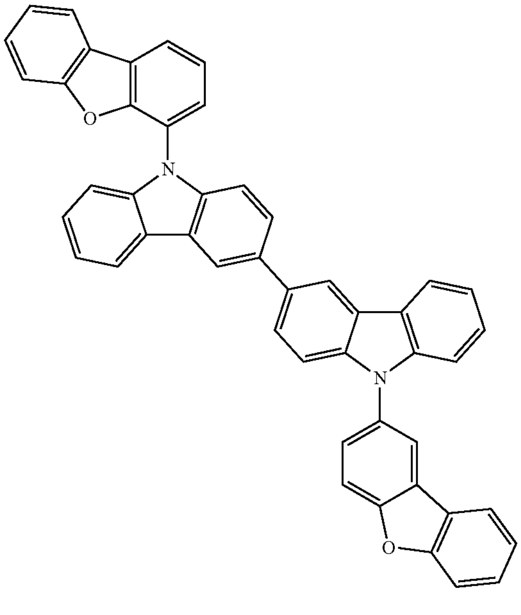

-continued
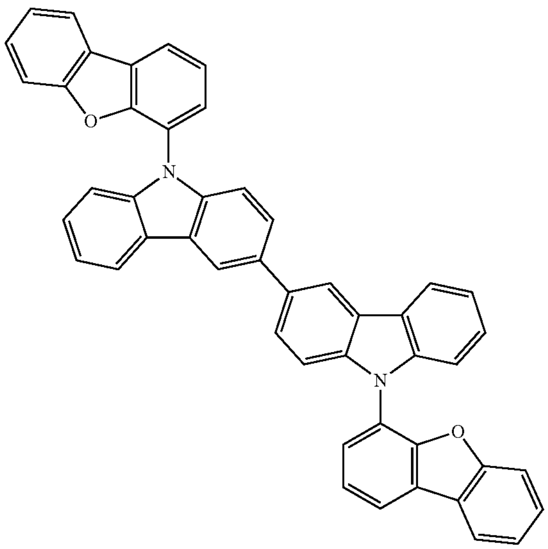
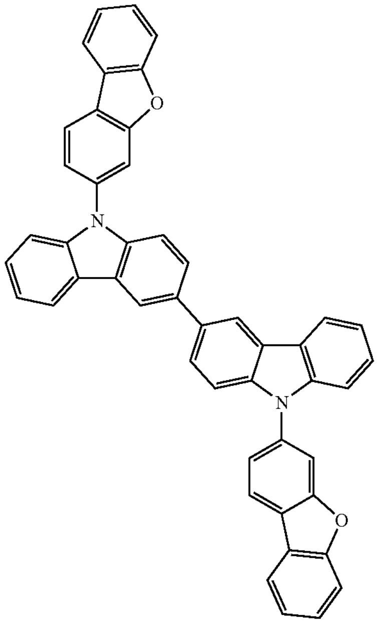
-continued
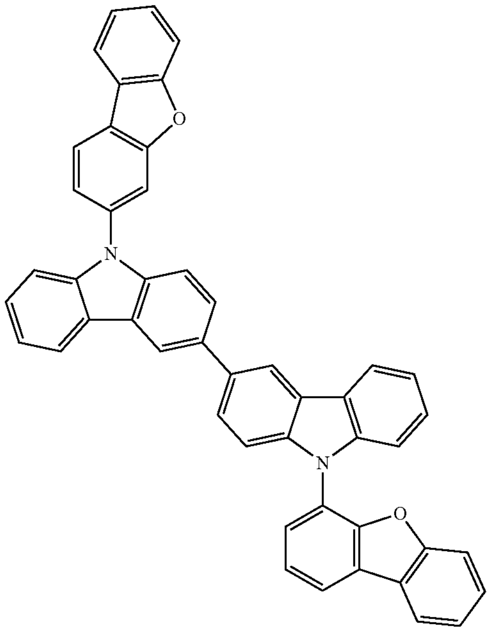
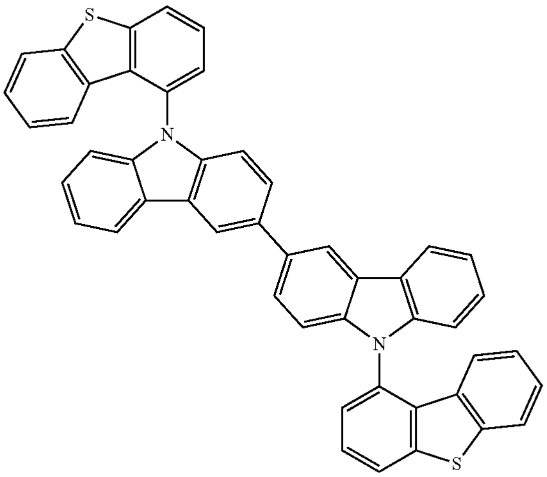
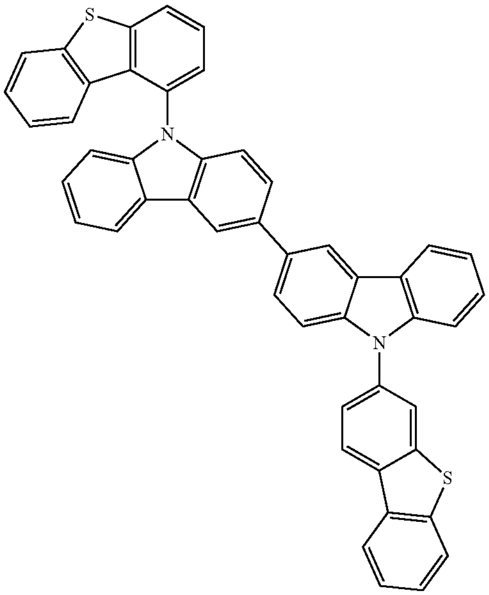

-continued
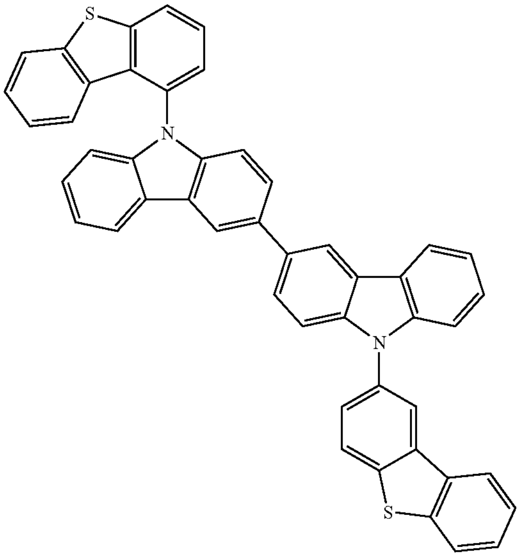
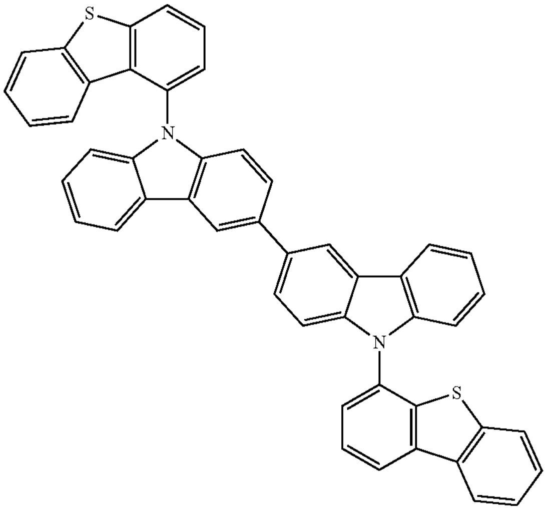
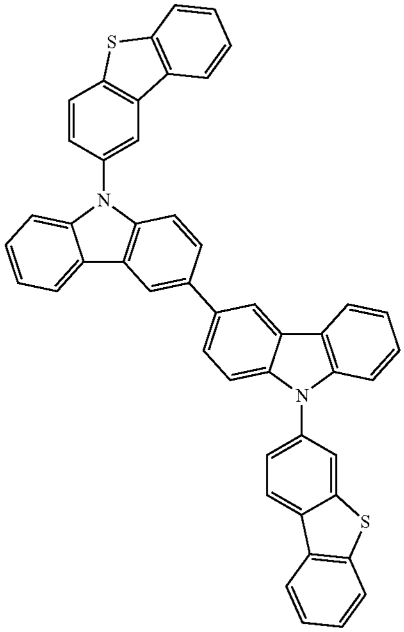
-continued
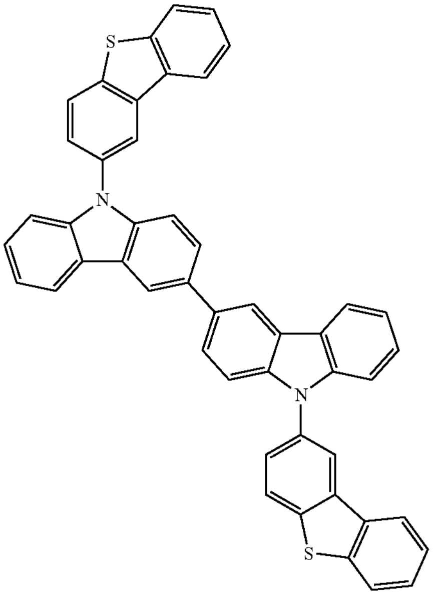
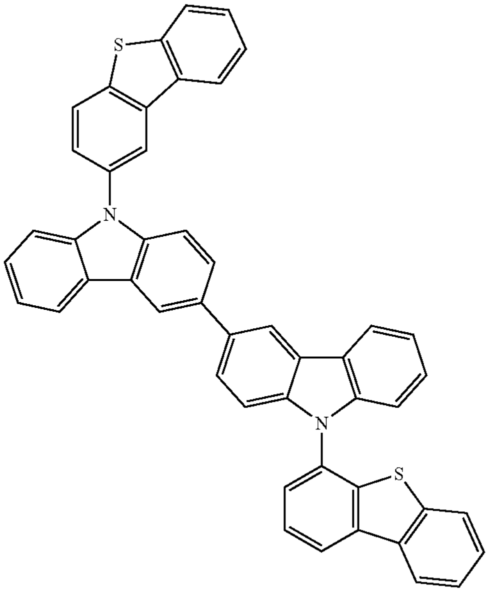

-continued
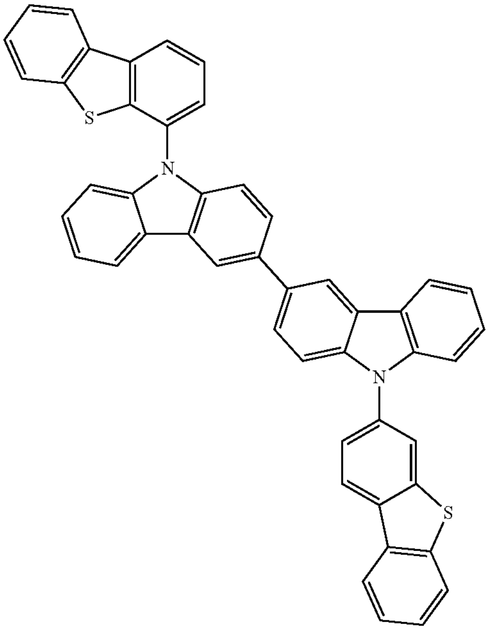
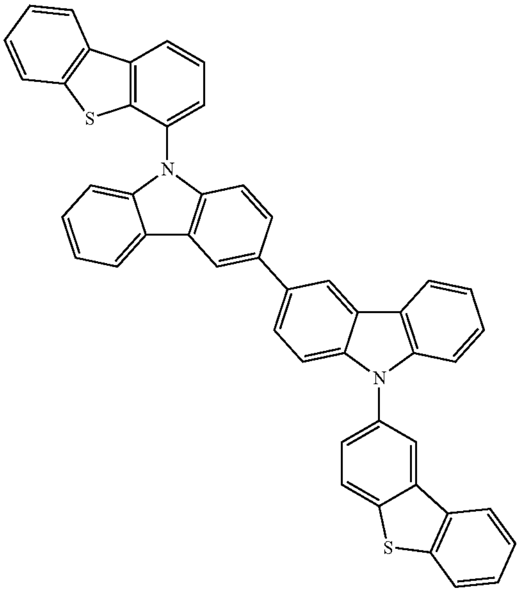
-continued
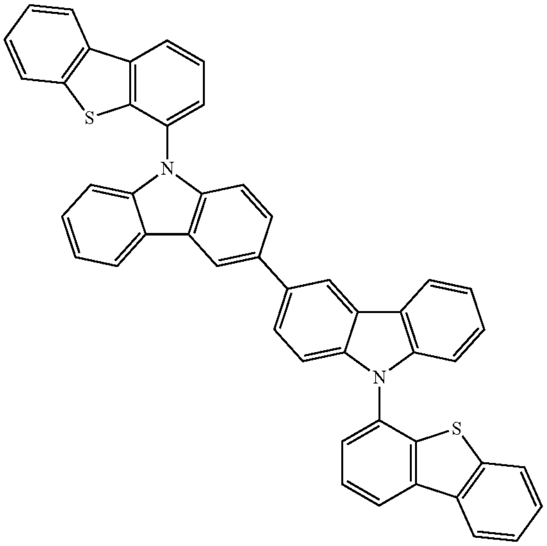
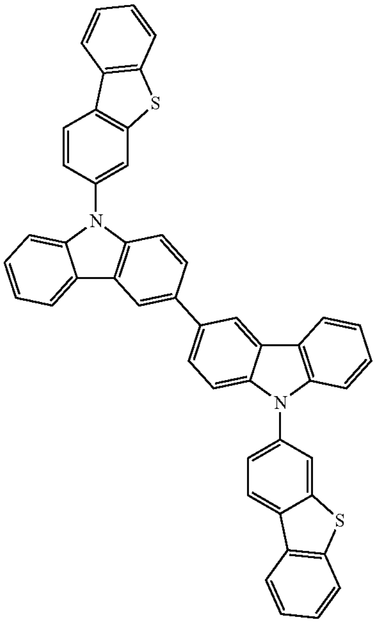

-continued
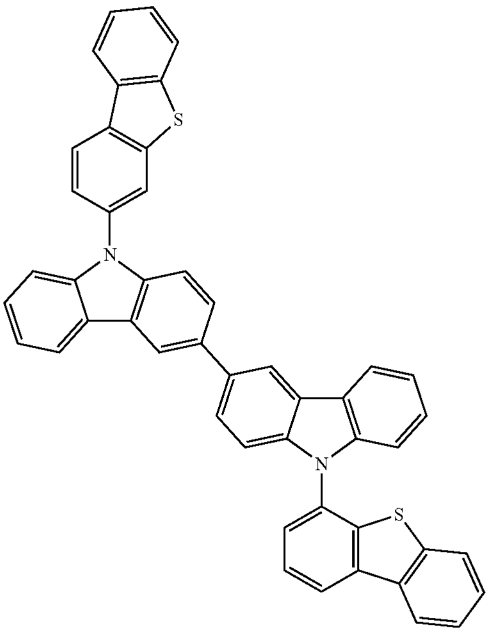
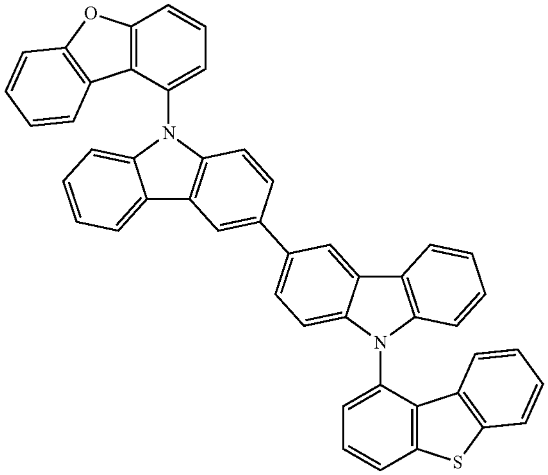
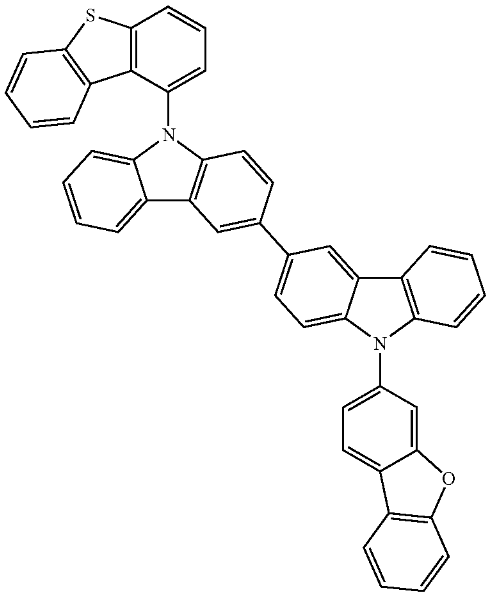
-continued
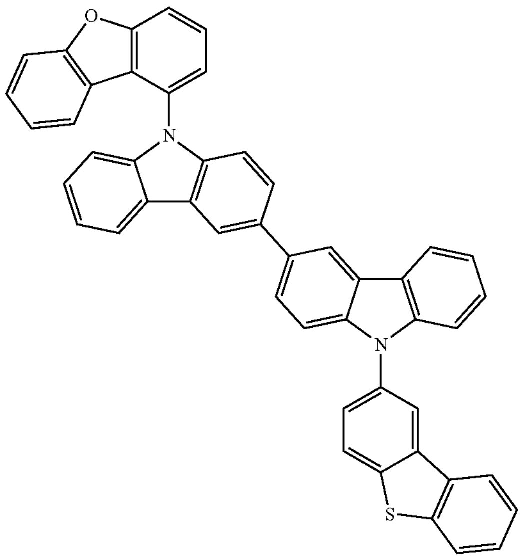
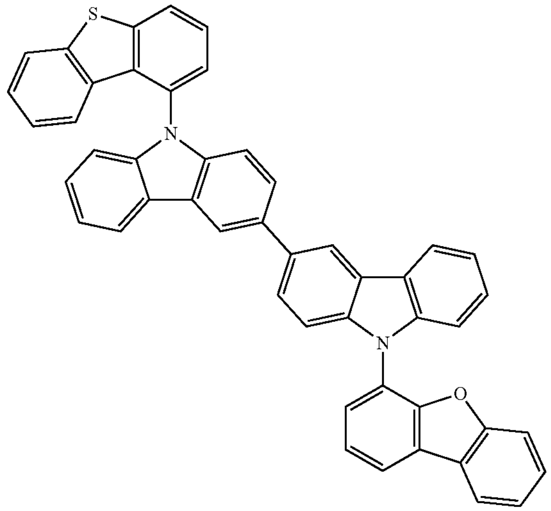
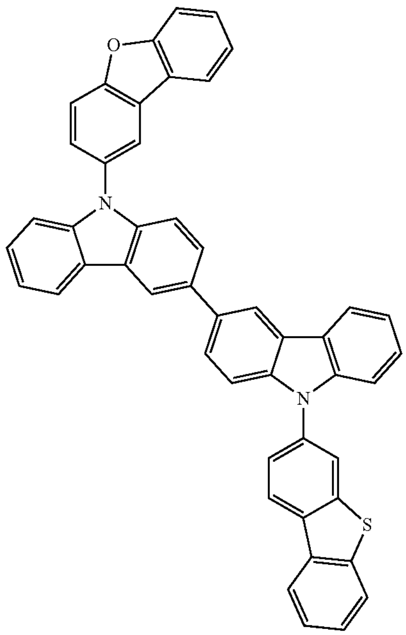

-continued
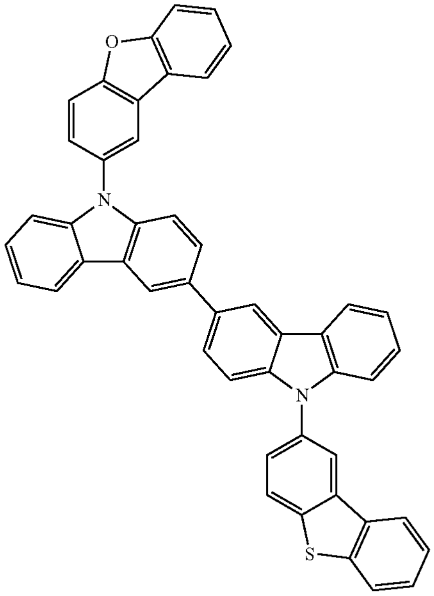
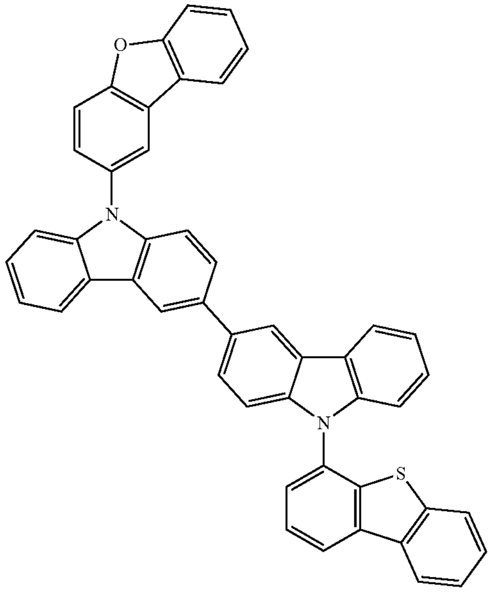
-continued
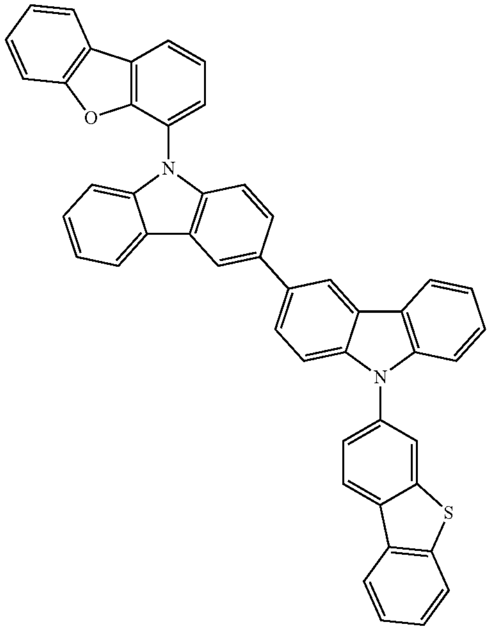
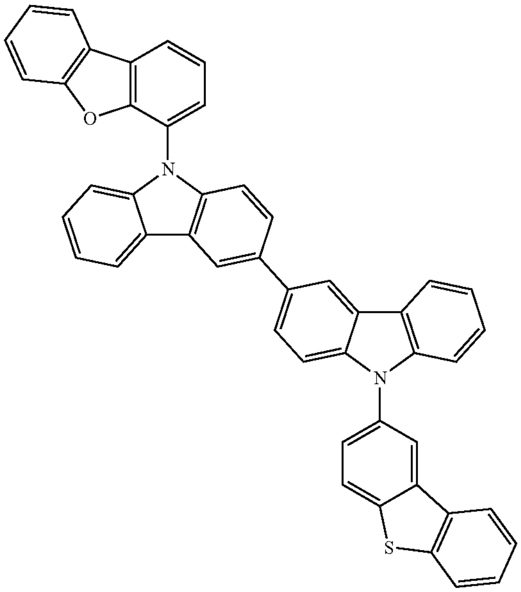

-continued
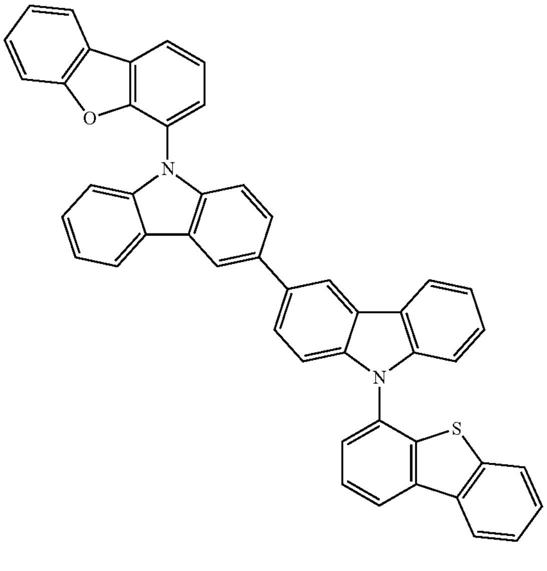
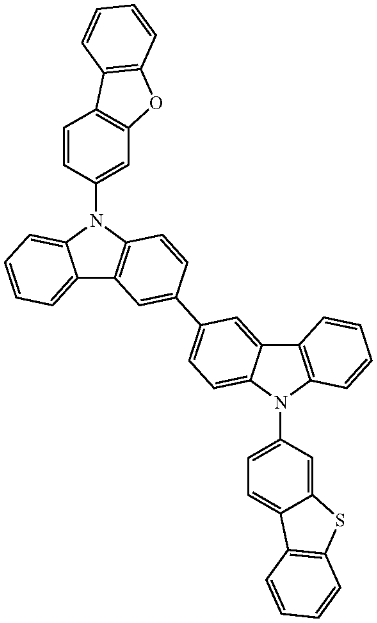
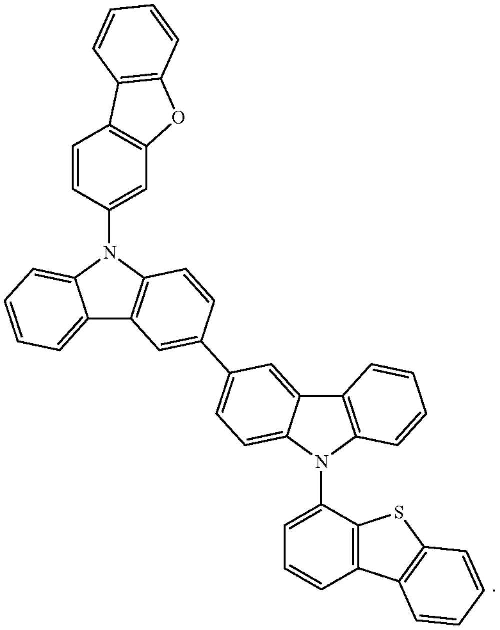
-continued
Meanwhile, the compound represented by the Chemical Formula 2 can be prepared, for example, by the preparation method as shown in Reaction Scheme 2 below.
[Reaction Scheme 2]
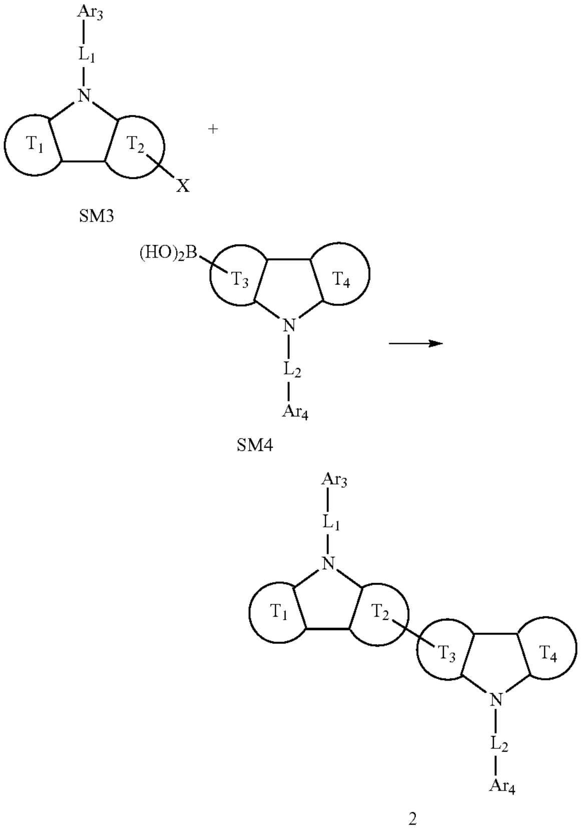

in the Reaction Scheme 2, each X is independently halogen, preferably bromo, or chloro, and the definitions of other substituents are the same as described above.

Specifically, the compound represented by the Chemical Formula 2 is prepared by combining the starting materials SM3 and SM4 through a Suzuki-coupling reaction. Such a Suzuki-coupling reaction is preferably performed in the presence of a palladium catalyst and a base. In addition, the reactive group for the Suzuki-coupling reaction may be appropriately changed, and the method for preparing the compound represented by the Chemical Formula 2 may be more specifically described in Preparation Examples described below.

The first compound and the second compound are preferably contained in the light emitting layer in a weight ratio of 99:1 to 1:99, and more preferably, in a weight ratio of 50:50, which is preferable in realizing a device with high efficiency and long lifespan.

Meanwhile, the light emitting layer further includes a dopant material other than the host material. Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

Preferably, the light emitting layer may include the following iridium complex compound as a dopant material, but is not limited thereto.

Dp-1

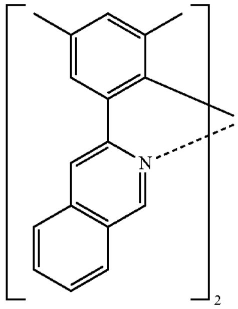

Dp-2

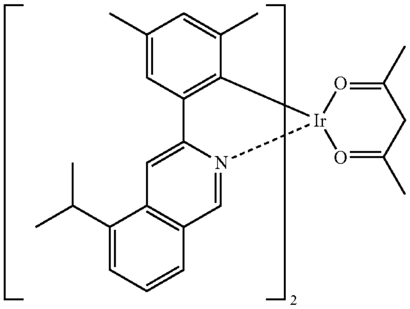

-continued

Dp-3

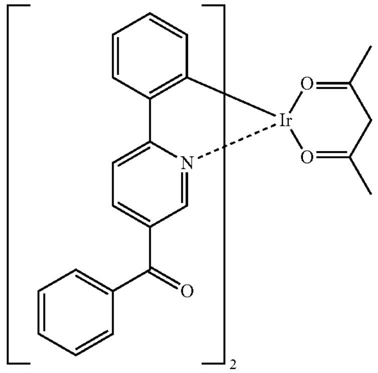

Dp-4

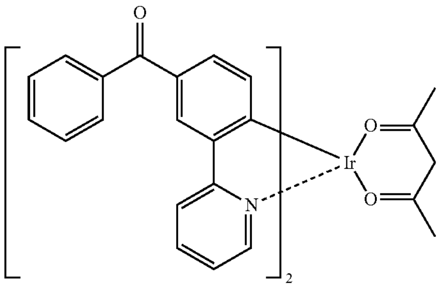

Dp-5

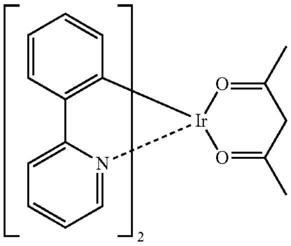

Dp-6

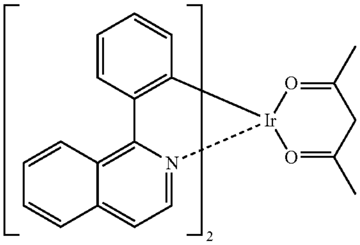

Dp-7

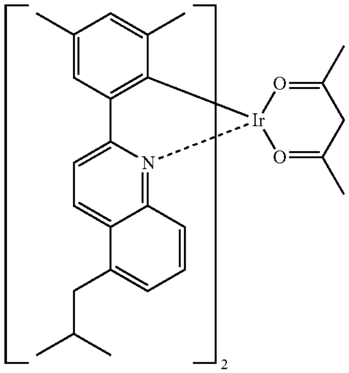

-continued
Dp-8
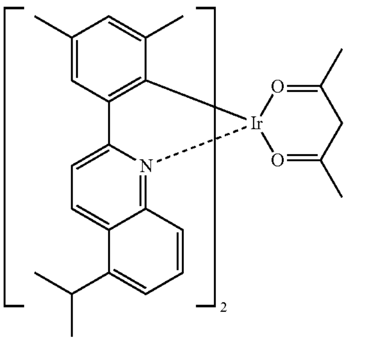
Dp-9
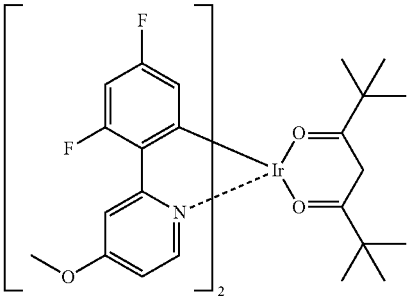
Dp-10
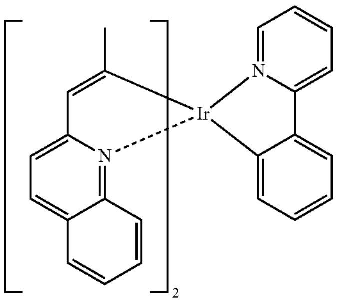
Dp-11
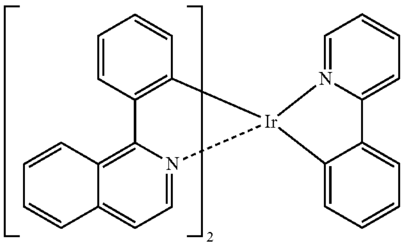
Dp-12
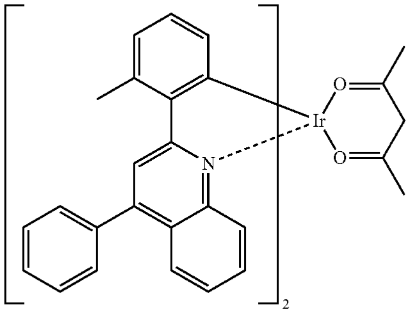
-continued
Dp-13
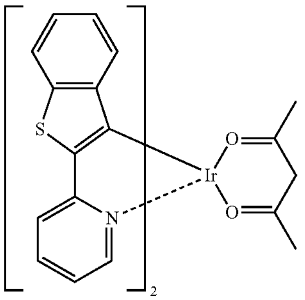
Dp-14
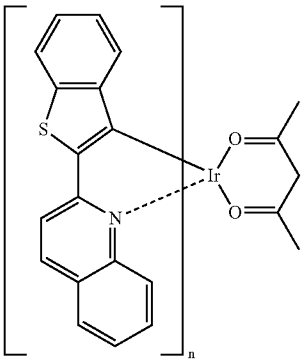
Dp-15
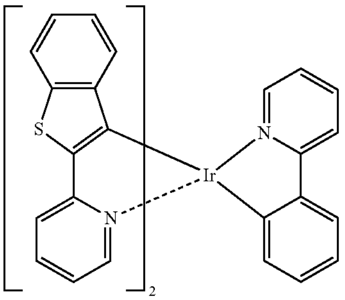
Dp-16
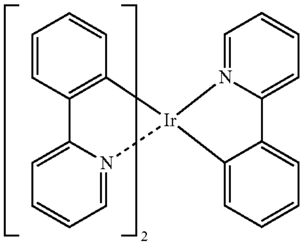
Dp-17
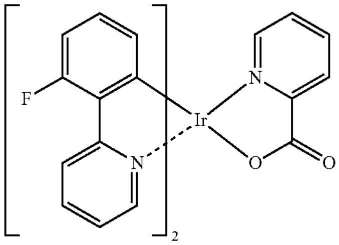

-continued
Dp-18
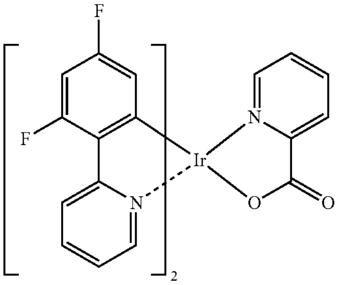
Dp-19
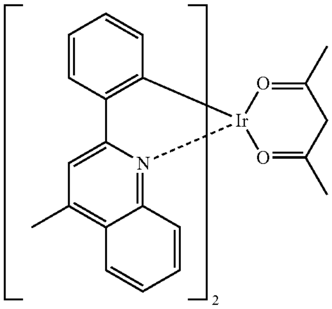
Dp-20
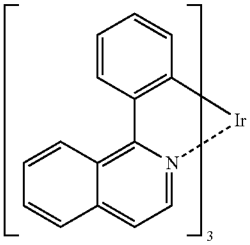
Dp-21
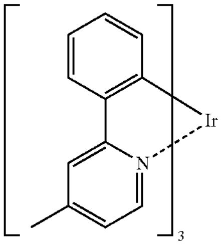
Dp-22
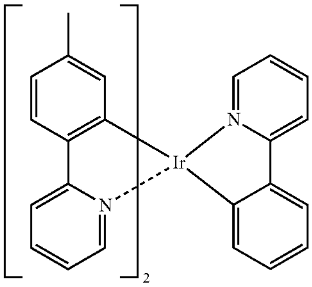
-continued
Dp-23
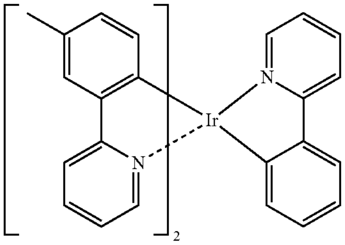
Dp-24
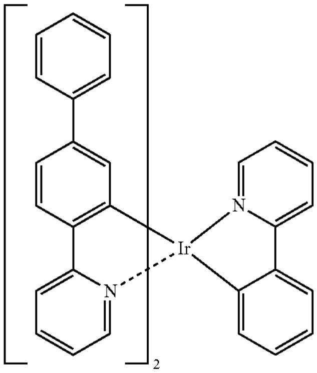
Dp-25
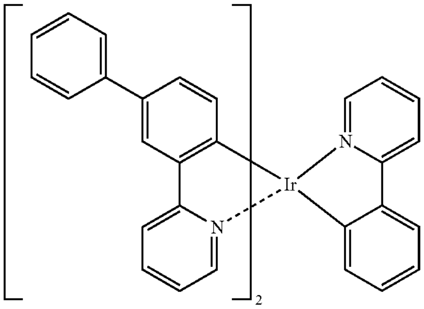
Dp-26
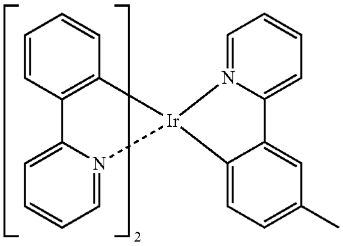
Dp-27
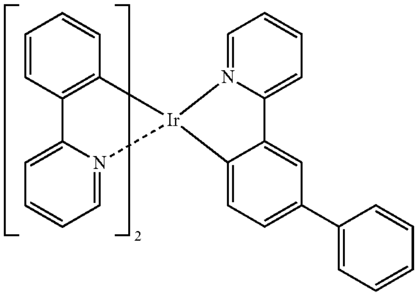

-continued
Dp-28
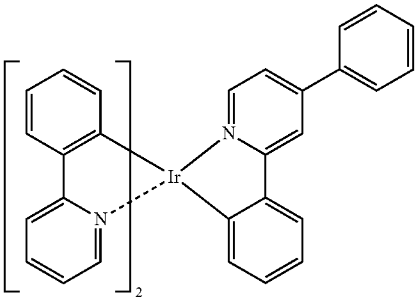
Dp-29
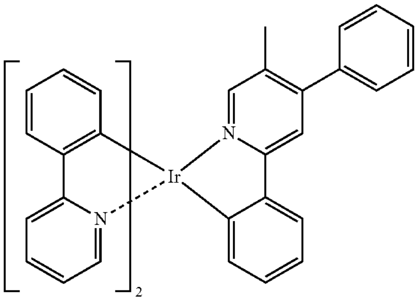
Dp-30
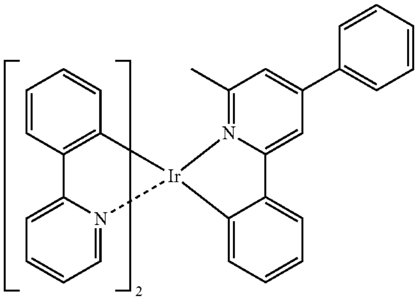
Dp-31
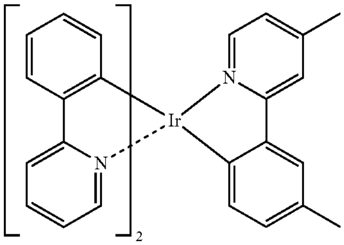
Dp-32
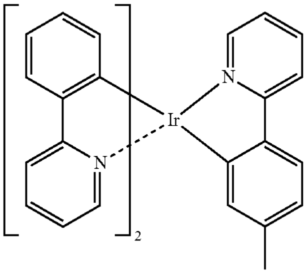
-continued
Dp-33
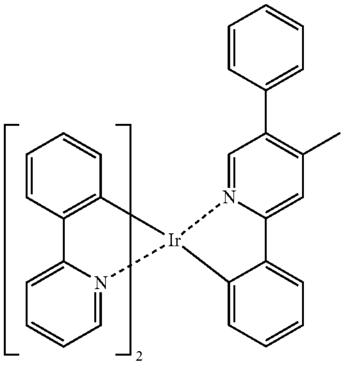
Dp-34
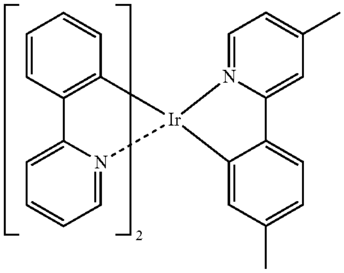
Dp-35
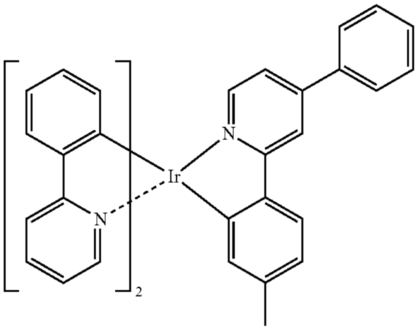
Dp-36
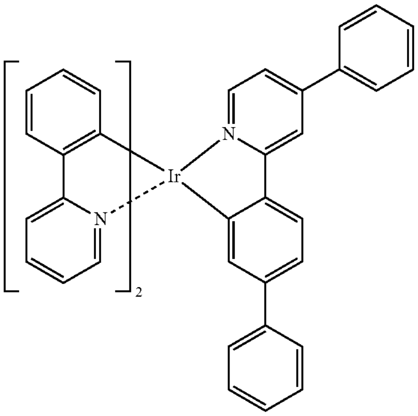

-continued

Dp-37

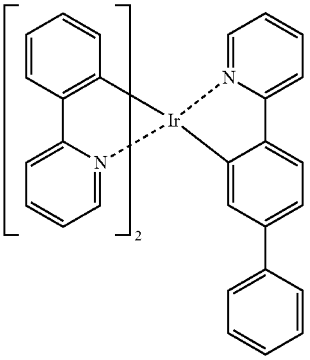

Dp-38

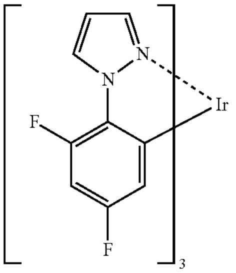

Hole Injection Layer

The organic light emitting device according to the one embodiment may further include a hole injection layer on an anode. The hole injection layer is composed of a hole injection material, and the hole injection material is preferably a compound which has an ability of transporting the holes, thus a hole injection effect in the anode and an excellent hole injection effect to the light emitting layer or the light emitting material, prevents movement of an exciton generated in the light emitting layer to the electron injection layer or the electron injection material, and has an excellent thin film forming ability.

Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

Hole Transport Layer

The organic light emitting device according to one embodiment may further include a hole transport layer on an anode or on the hole injection layer formed on the anode. The hole transport layer is a layer that receives holes from an anode or a hole injection layer formed on the anode and transports the holes to the light emitting layer. The hole transport material included in the hole transport layer is suitably a material having large mobility to the holes, which may receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

Electron Blocking Layer

The organic light emitting device according to the one embodiment may further include an electron blocking layer on the hole transport layer. The electron blocking layer means a layer which is formed on the hole transport layer, is preferably provided in contact with the light emitting layer, and thus serves to control hole mobility, to prevent excessive movement of electrons, and to increase the probability of hole-electron bonding, thereby improving the efficiency of the organic light emitting device. The electron blocking layer includes an electron blocking material, and as an example of such an electron blocking material, a compound represented by the Chemical Formula 1 may be used, or an arylamine-based organic material may be used, but is not limited thereto.

Hole Blocking Layer

The organic light emitting device according to the one embodiment may further include a hole blocking layer on the light emitting layer. The hole blocking layer means a layer which is formed on the light emitting layer, is preferably provided in contact with the light emitting layer, and thus serves to control electron mobility, to prevent excessive movement of holes, and to increase the probability of hole-electron bonding, thereby improving the efficiency of the organic light emitting device. The hole blocking layer includes an hole blocking material, and as an example of such an hole blocking material, compounds having introduced electron attracting groups, such as azine-based derivatives including triazine; triazole derivatives; oxadiazole derivatives; phenanthroline derivatives; phosphine oxide derivatives may be used, but is not limited thereto.

Electron Transport Layer

The organic light emitting device according to the one embodiment may include an electron transport layer on the light emitting layer or on the hole blocking layer. The electron transport layer is layer which receives electrons from a cathode or an electron injection layer described below and transports the electrons to a light emitting layer, and an electron transport material included in the electron transport layer is suitably a material which may receive electrons well from a cathode and transfer the electrons to a light emitting layer, and has a large mobility for electrons.

Specific examples of the electron transport material include: a pyridine derivative; a pyrimidine derivative; triazole derivative; an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

Electron Injection Layer

The organic light emitting device according to the one embodiment may further include an electron injection layer between the electron transport layer and the cathode. The electron injection layer is a layer which injects electrons from a cathode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples of materials that can be used as the electron injection layer include LiF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

Meanwhile, the electron transport layer and the electron injection layer may be provided in the form of an electron injection and transport layer that simultaneously perform the roles of the electron transport layer and the electron injection layer that transport the received electrons to the light emitting layer.

Organic Light Emitting Device

According to one embodiment, the structure of the organic light emitting device in which the first electrode is an anode and the second electrode is a cathode is illustrated in FIG. 1. FIG. 1 shows an example of an organic light emitting device comprising a substrate 1, an anode 2, a light emitting layer 3, and a cathode 4. In such a structure, the first compound and the second compound may be included in the light emitting layer.

According to another embodiment, the structure of the organic light emitting device in which the first electrode is an anode and the second electrode is a cathode is illustrated in FIG. 2. FIG. 2 shows an example of an organic light emitting device comprising a substrate 1, an anode 2, a hole injection layer 5, a hole transport layer 6, an electron blocking layer 7, a light emitting layer 3, a hole blocking layer 8, an electron injection and transport layer 9, and a cathode 4. In such a structure, the first compound and the second compound may be included in the light emitting layer.

The organic light emitting device according to the present disclosure may be manufactured by sequentially laminating the above-mentioned components. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming the above-mentioned respective layers thereon, and then depositing a material that can be used as the cathode thereon. In addition to such a method, the organic light emitting device may be manufactured by sequentially depositing a cathode material, an organic material layer and an anode material on a substrate. Further, the light emitting layer may be formed using the host and the dopant by a solution coating method as well as a vacuum deposition method. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO20031012890). However, the manufacturing method is not limited thereto.

Meanwhile, the organic light emitting device according to the present disclosure may be a front side emission type, a backside emission type, or a double-sided emission type according to the used material.

The preparation of the organic light emitting device will be described in detail in the following examples. However, these examples are presented for illustrative purposes only, and are not intended to limit the scope of the present disclosure.

Synthesis Example 1-1: Preparation of Compound 1-1

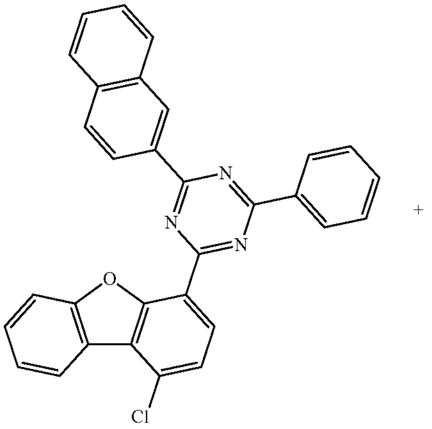

1-1-1

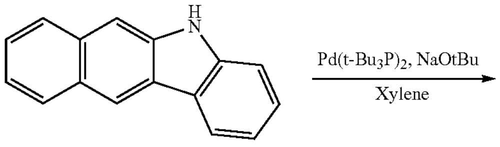

a

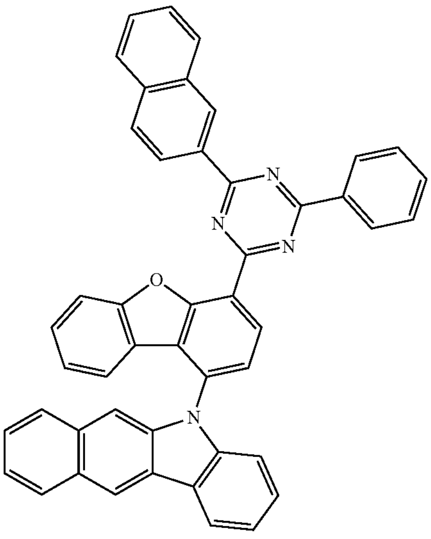

1-1

Intermediate 1-1-1 (10 g, 20.7 mmol), Compound a (4.9 g, 22.7 mmol) and sodium tert-butoxide (4 g, 41.3 mmol) were added to 200 ml of xylene under a nitrogen atmosphere, and the mixture was stirred and refluxed. Then, bis(tri-tert-butylphosphine)palladium(0) (0.2 g, 0.4 mmol)

was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8 g of Compound 1-1. (Yield: 58%, MS: [M+H]+=665)

Synthesis Example 1-2: Preparation of Compound 1-2

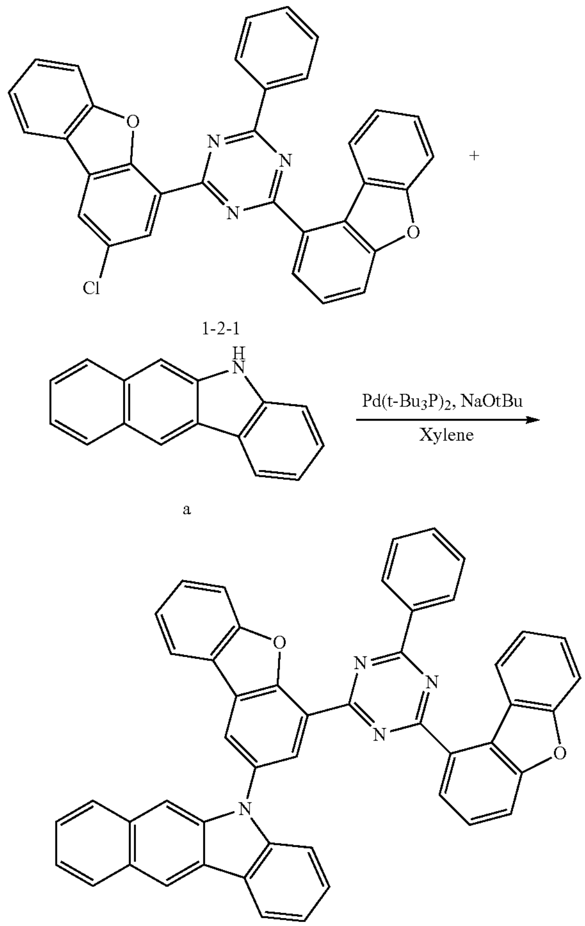

1-2-1 a 1-2

Intermediate 1-2-1 (10 g, 19.1 mmol), Compound a (4.6 g, 21 mmol) and sodium tert-butoxide (3.7 g, 38.2 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.5 g of Compound 1-2. (Yield: 63%, MS: [M+H]+=705)

Synthesis Example 1-3: Preparation of Compound 1-3

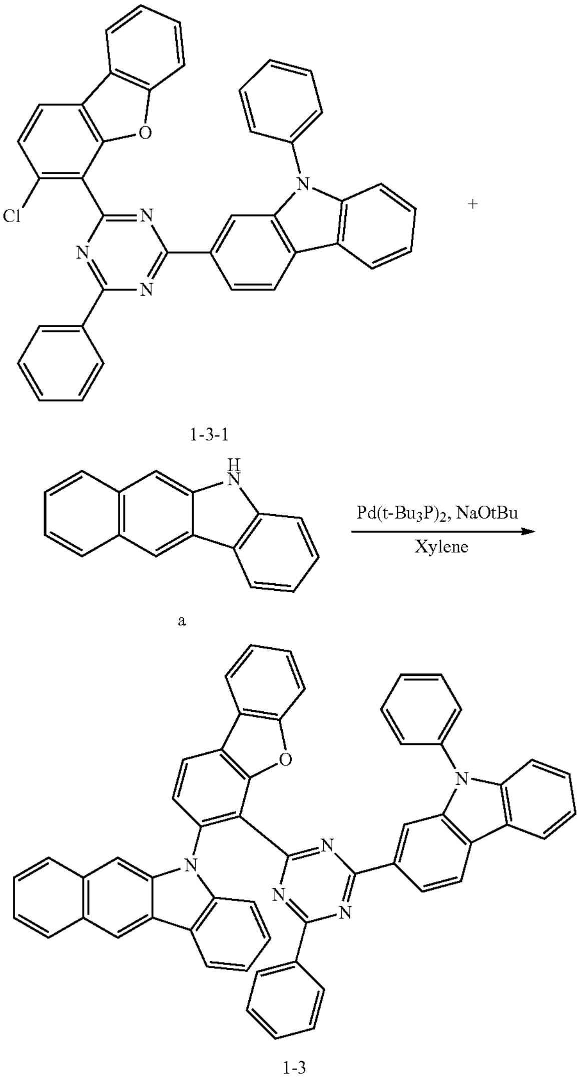 [SMILES: Clc1ccc2c(oc3ccccc32)c1-c1nc(-c2ccccc2)nc(-c2ccc3c4ccccc4n(-c4ccccc4)c3c2)n1 ; c1ccc2cc3c(cc2c1)[nH]c1ccccc13 ; c1ccc(-c2nc(-c3ccc4c5ccccc5n(-c5ccccc5)c4c3)nc(-c3c(-n4c5ccccc5c5cc6ccccc6cc54)ccc4c3oc3ccccc34)n2)cc1]

1-3-1 a 1-3

Intermediate 1-3-1 (10 g, 16.7 mmol), Compound a (4 g, 18.4 mmol) and sodium tert-butoxide (3.2 g, 33.4 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9 g of Compound 1-3. (Yield: 69%, MS: [M+H]+=780)

Synthesis Example 1-4: Preparation of Compound 1-4

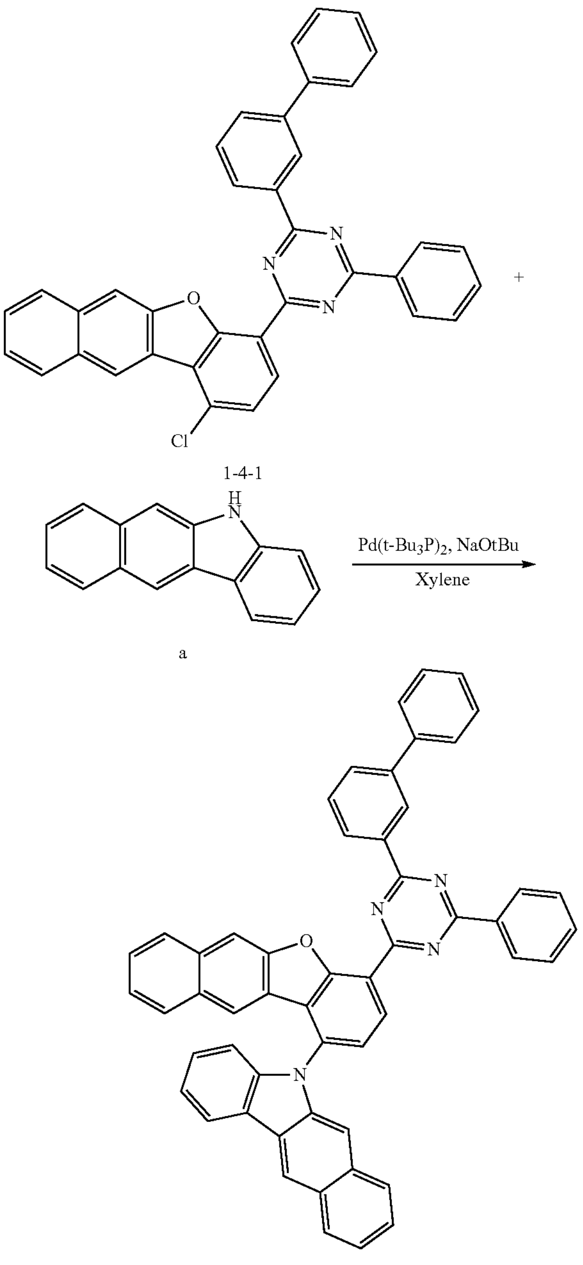

1-4-1 a 1-4

Intermediate 1-4-1 (10 g, 17.9 mmol), Compound a (4.3 g, 19.6 mmol) and sodium tert-butoxide (3.4 g, 35.7 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 7.7 g of Compound 1-4. (Yield: 58%, MS: [M+H]+=741).

Synthesis Example 1-5: Preparation of Compound 1-5

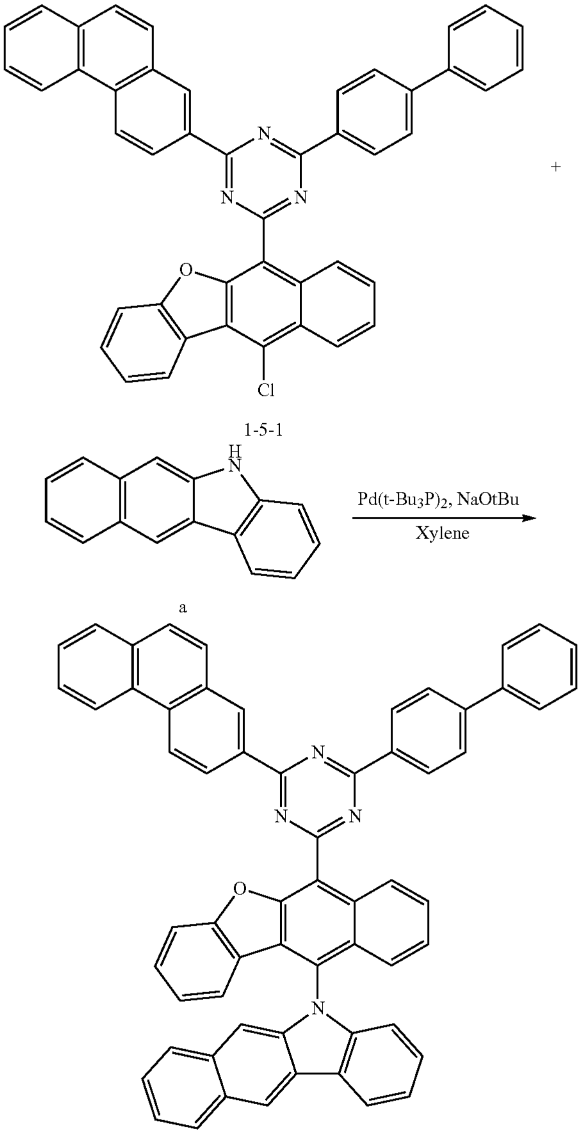

1-5-1 a 1-5

Intermediate 1-5-1 (10 g, 15.1 mmol), Compound a (3.6 g, 16.7 mmol) and sodium tert-butoxide (2.9 g, 30.3 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.7 g of Compound 1-5. (Yield: 68%, MS: [M+H]+=841)

Synthesis Example 1-6: Preparation of Compound 1-6

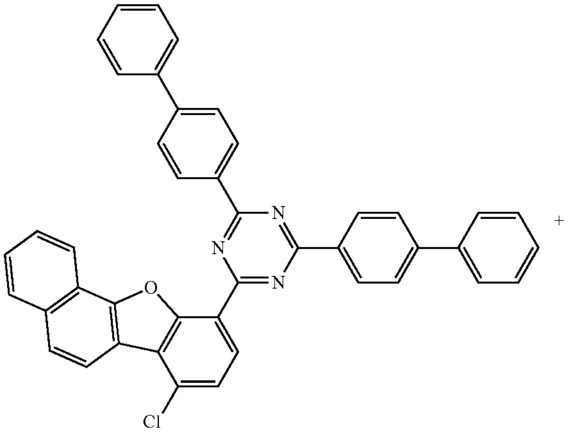

1-6-1

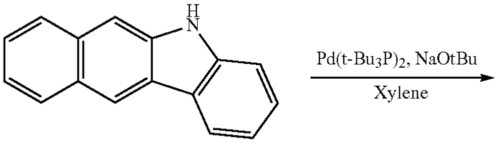

a

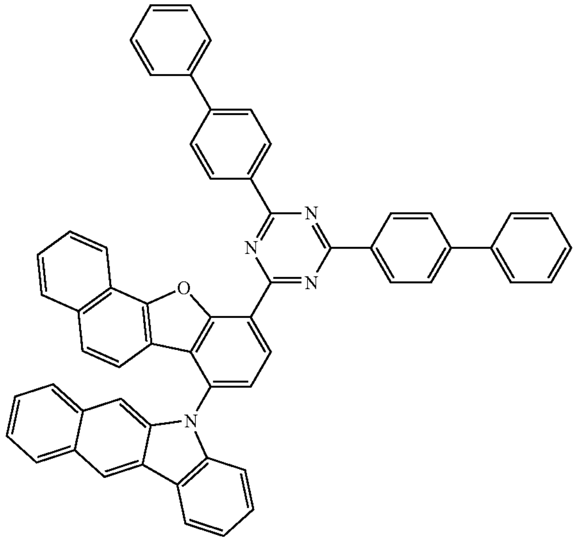

1-6

Intermediate 1-6-1 (10 g, 15.7 mmol), Compound a (3.8 g, 17.3 mmol) and sodium tert-butoxide (3 g, 31.4 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto.

After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.7 g of Compound 1-6. (Yield: 68%, MS: [M+H]+=817)

Synthesis Example 1-7: Preparation of Compound 1-7

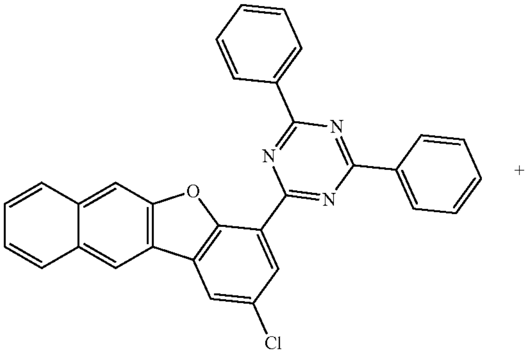

1-7-1

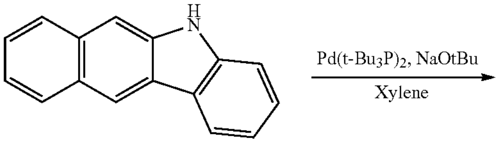

a

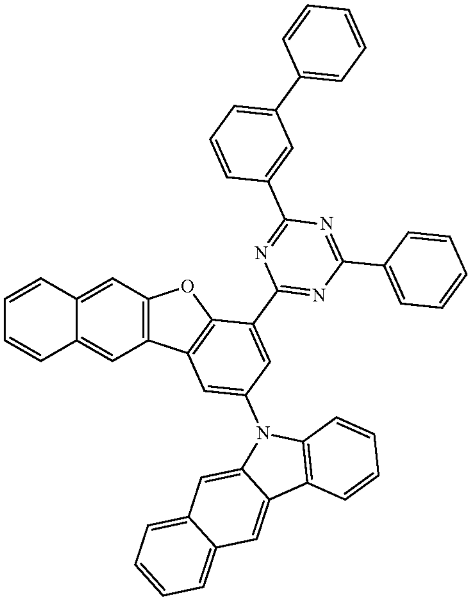

1-7

Intermediate 1-7-1 (10 g, 20.7 mmol), Compound a (4.9 g, 22.7 mmol) and sodium tert-butoxide (4 g, 41.3 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.6 g of Compound 1-7. (Yield: 63%, MS: [M+H]+=665)

Synthesis Example 1-8: Preparation of Compound 1-8

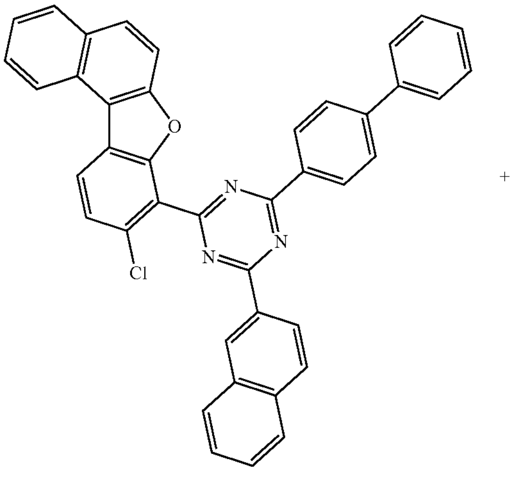

1-8-1

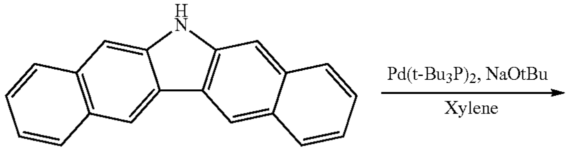

c

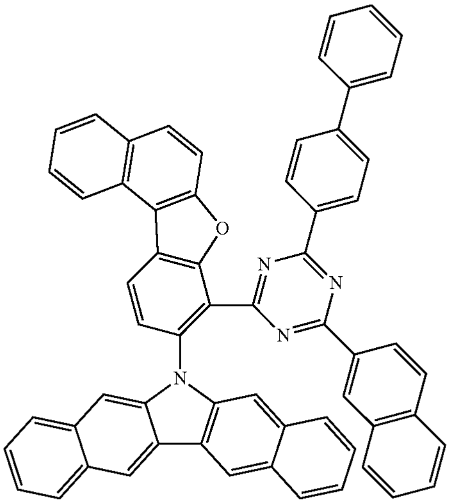

1-8

Intermediate 1-8-1 (10 g, 16.4 mmol), Compound c (4.8 g, 18 mmol) and sodium tert-butoxide (3.2 g, 32.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.9 g of Compound 1-8. (Yield: 50%, MS: [M+H]+=841)

Synthesis Example 1-9: Preparation of Compound 1-9

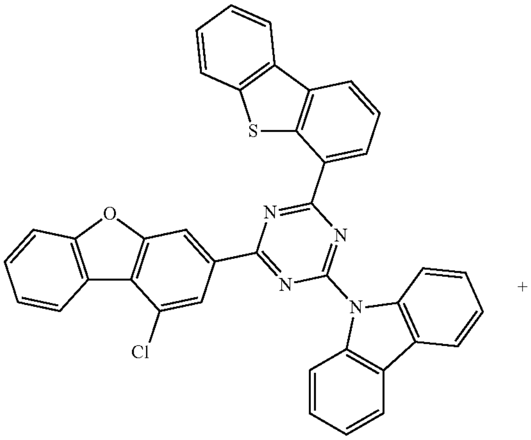

1-9-1

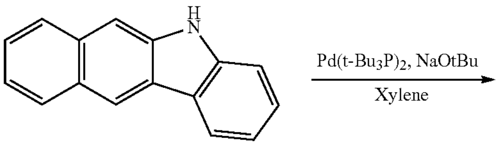

a

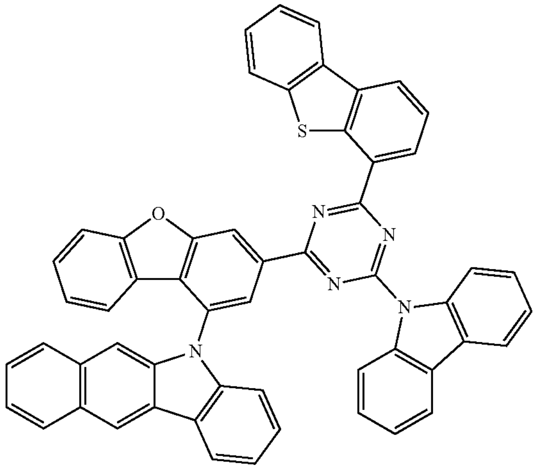

1-9

Intermediate 1-9-1 (10 g, 15.9 mmol), Compound a (3.8 g, 17.5 mmol) and sodium tert-butoxide (3.1 g, 31.8 mmol) were added to 200 ml of xylene under a nitrogen atmosphere, and the mixture was stirred and refluxed. Then, bis(tri-tert-butylphosphine)palladium(0) (0.2 g, 0.3 mmol)

was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 18.1 g of Compound 1-9. (Yield: 63%, MS: [M+H]+=810)

Synthesis Example 1-10: Preparation of Compound 1-10

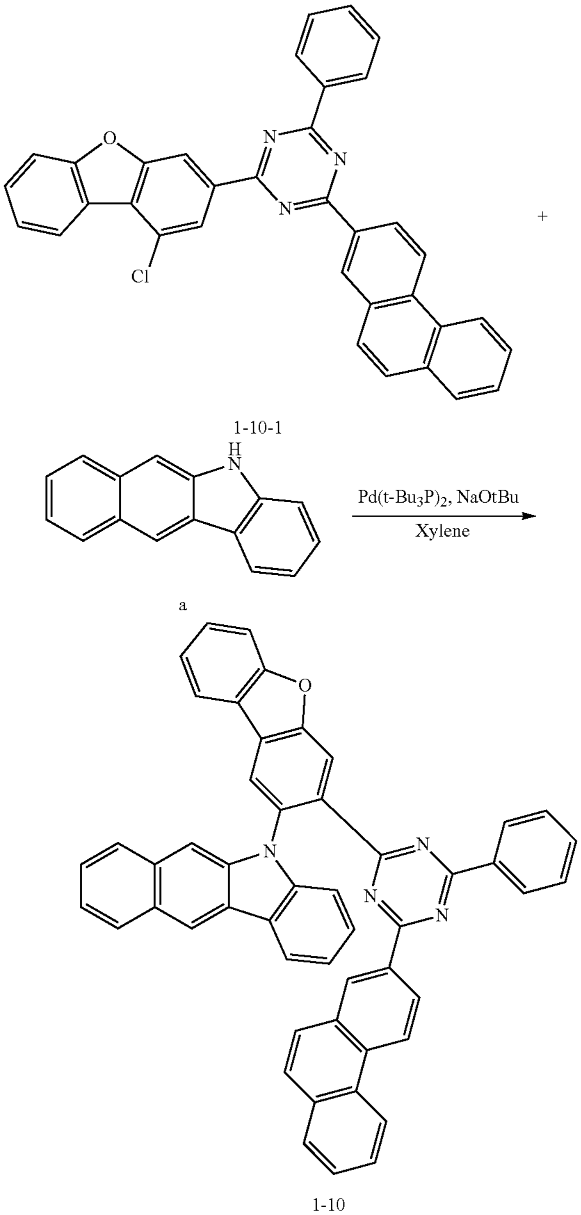

1-10-1 a 1-10

Intermediate 1-10-1 (10 g, 18.7 mmol), Compound a (4.5 g, 20.6 mmol) and sodium tert-butoxide (3.6 g, 37.5 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.1 g of Compound 1-10. (Yield: 68%, MS: [M+H]+=715)

Synthesis Example 1-11: Preparation of Compound 1-11

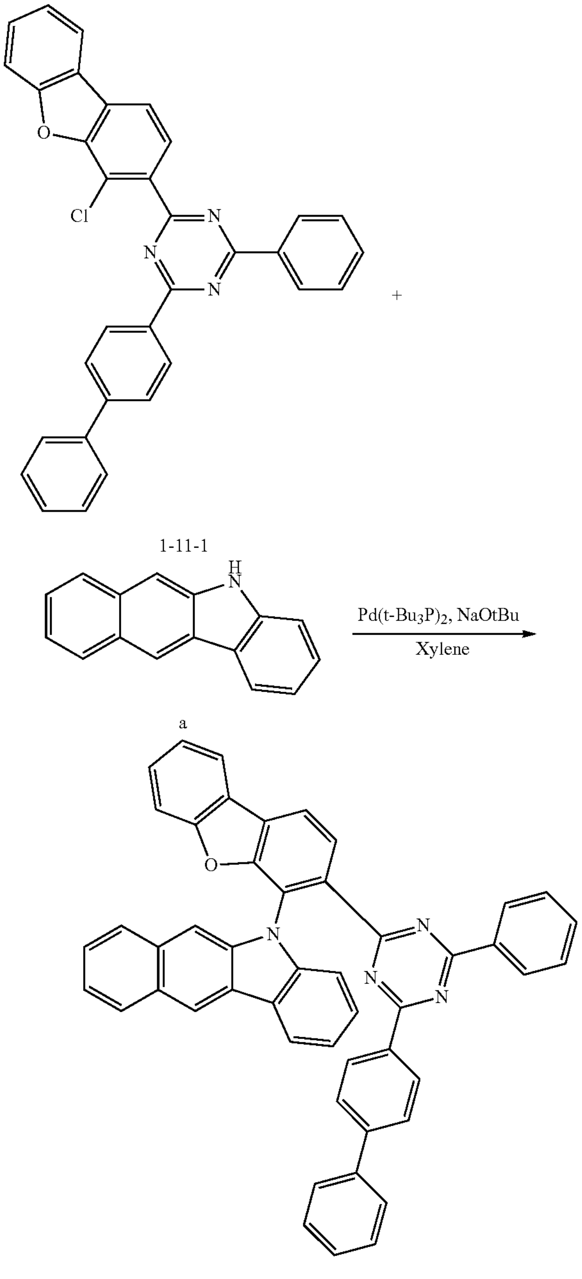

1-11-1 a 1-11

Intermediate 1-11-1 (10 g, 19.6 mmol), Compound a (4.7 g, 21.6 mmol) and sodium tert-butoxide (3.8 g, 39.2 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.5 g of Compound 1-11. (Yield: 70%, MS: [M+H]+=691)

Synthesis Example 1-12: Preparation of Compound 1-12

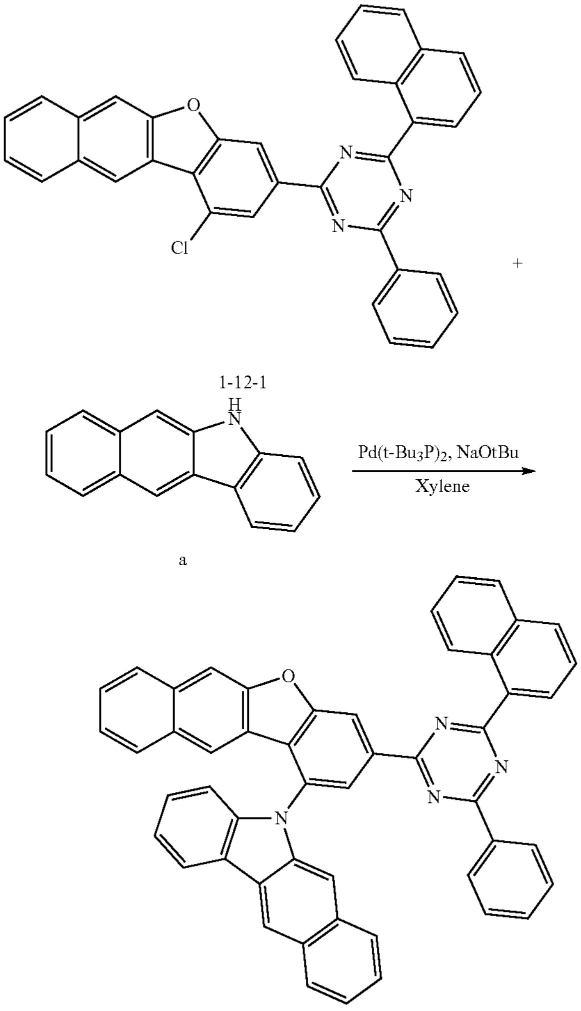

1-12-1 a 1-12

Intermediate 1-12-1 (10 g, 18.7 mmol), Compound a (4.5 g, 20.6 mmol) and sodium tert-butoxide (3.6 g, 37.5 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 7.5 g of Compound 1-12. (Yield: 56%, MS: [M+H]+=715)

Synthesis Example 1-13: Preparation of Compound 1-13

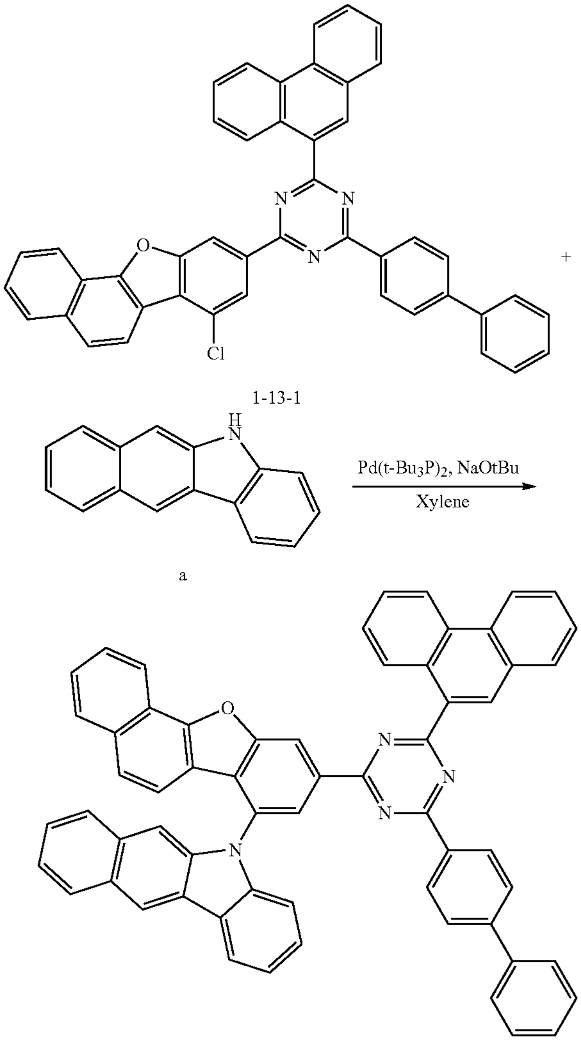

1-13-1 a 1-13

Intermediate 1-13-1 (10 g, 15.1 mmol), Compound a (3.6 g, 16.7 mmol) and sodium tert-butoxide (2.9 g, 30.3 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.7 g of Compound 1-13. (Yield: 53%, MS: [M+H]+=841)

Synthesis Example 1-14: Preparation of Compound 1-14

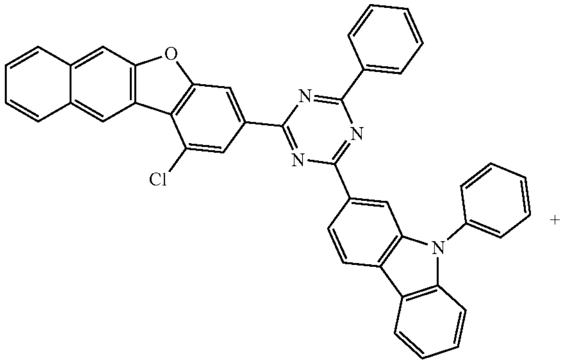

1-14-1

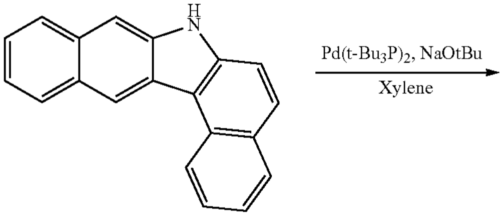

b

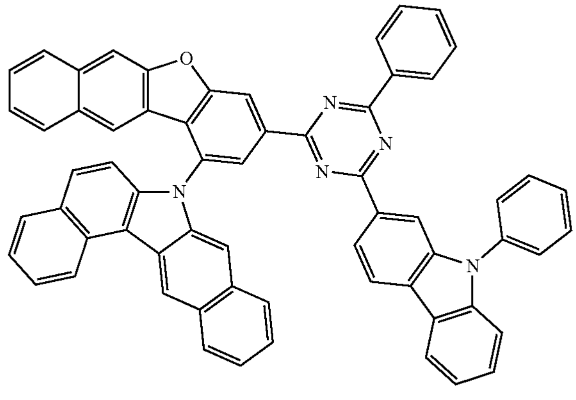

1-14

Intermediate 1-14-1 (10 g, 15.4 mmol), Compound b (4.5 g, 16.9 mmol) and sodium tert-butoxide (3 g, 30.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8 g of Compound 1-14. (Yield: 59%, MS: [M+H]+=880)

Synthesis Example 1-15: Preparation of Compound 1-15

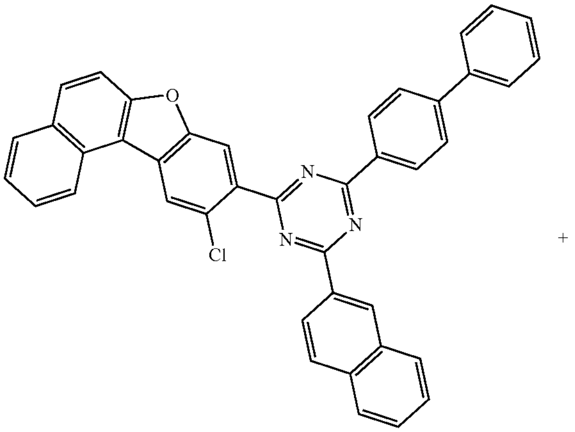

1-15-1

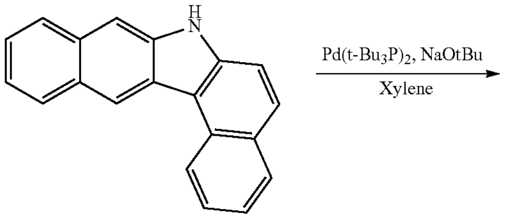

b

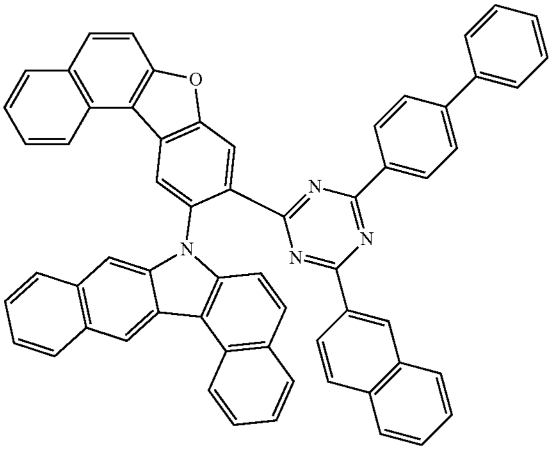

1-15

Intermediate 1-15-1 (10 g, 16.4 mmol), Compound b (4.8 g, 18 mmol) and sodium tert-butoxide (3.2 g, 32.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.5 g of Compound 1-15. (Yield: 69%, MS: [M+H]+=841)

Synthesis Example 1-16: Preparation of Compound 1-16

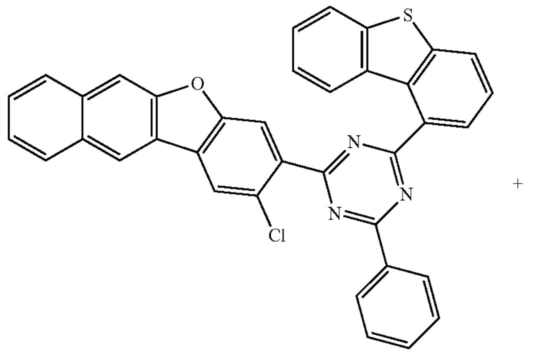

1-16-1

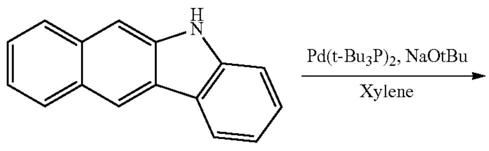

a

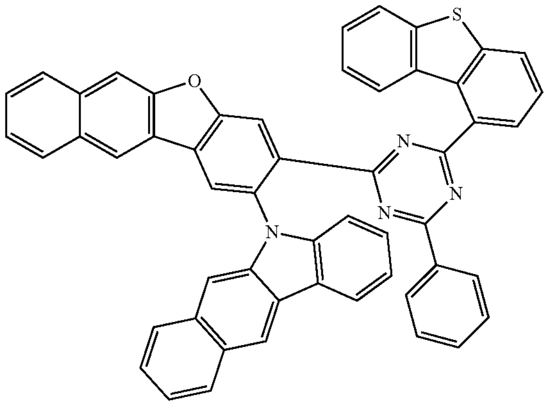

1-16

Intermediate 1-16-1 (10 g, 16.9 mmol), Compound a (4.1 g, 18.6 mmol) and sodium tert-butoxide (3.3 g, 33.9 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 7.2 g of Compound 1-16. (Yield: 55%, MS: [M+H]+=771)

Synthesis Example 1-17: Preparation of Compound 1-17

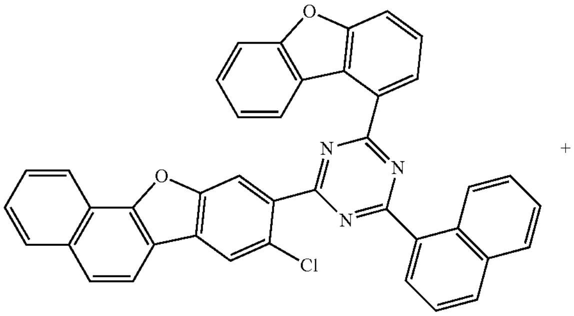

1-17-1

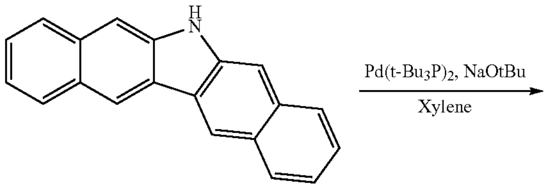

c

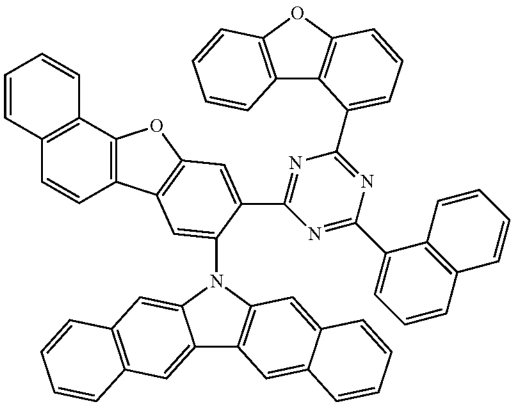

1-17

Intermediate 1-17-1 (10 g, 16 mmol), Compound c (4.7 g, 17.6 mmol) and sodium tert-butoxide (3.1 g, 32 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 7.8 g of Compound 1-17. (Yield: 57%, MS: [M+H]+=855)

Synthesis Example 1-18: Preparation of Compound 1-18

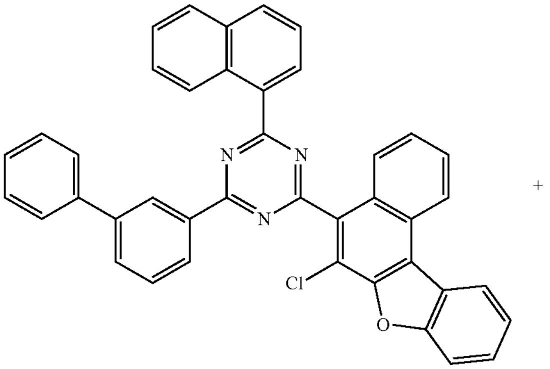

1-18-1

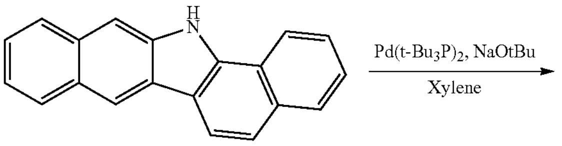

d

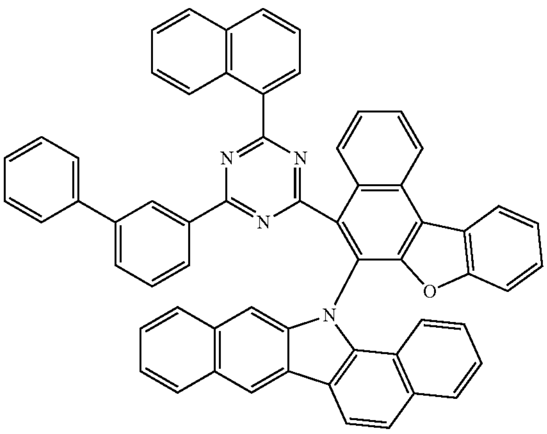

1-18

Intermediate 1-18-1 (10 g, 16.4 mmol), Compound d (4.8 g, 18 mmol) and sodium tert-butoxide (3.2 g, 32.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.9 g of Compound 1-18. (Yield: 50%, MS: [M+H]+=841)

Synthesis Example 1-19: Preparation of Compound 1-19

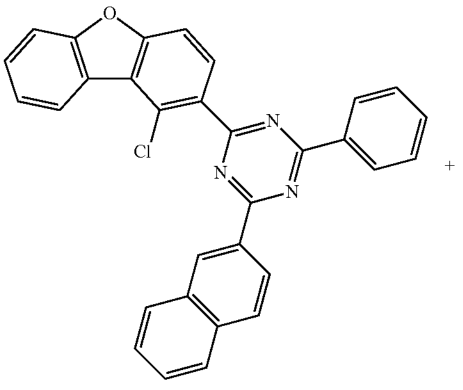

1-19-1

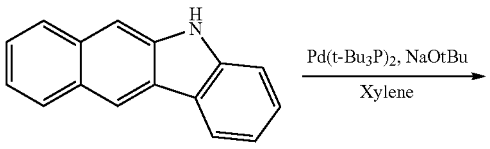

a

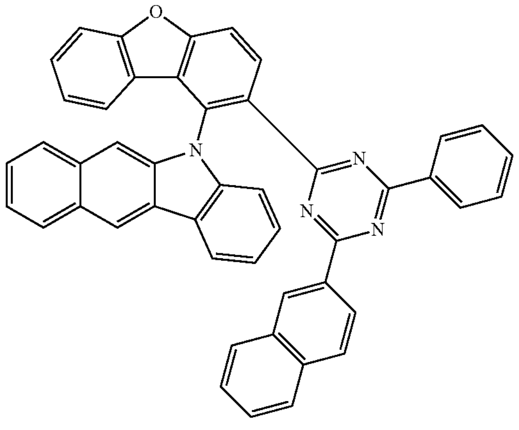

1-19

Intermediate 1-19-1 (10 g, 20.7 mmol), Compound a (4.9 g, 22.7 mmol) and sodium tert-butoxide (4 g, 41.3 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.2 g of Compound 1-19. (Yield: 67%, MS: [M+H]+=665)

Synthesis Example 1-20: Preparation of Compound 1-20

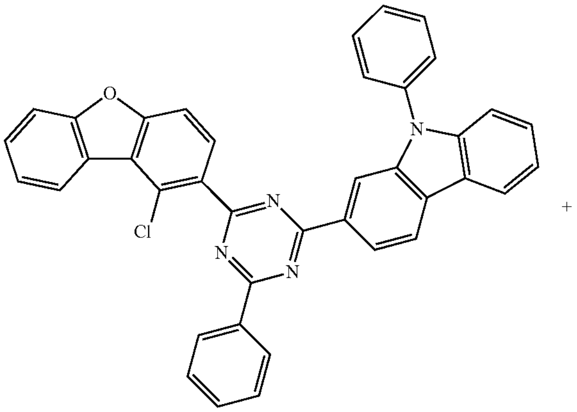

1-20-1

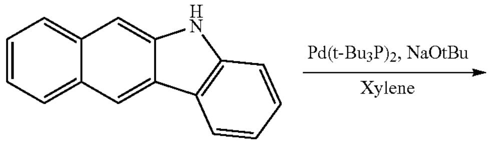

a

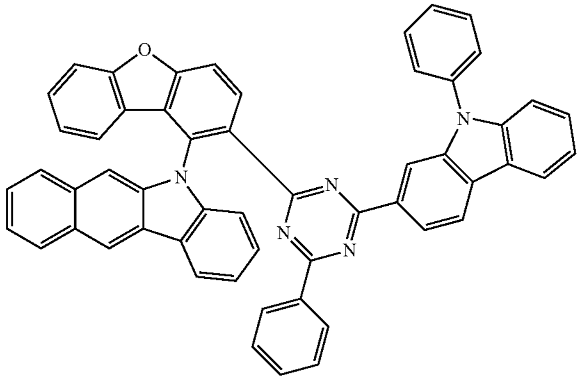

1-20

Intermediate 1-20-1 (10 g, 16.7 mmol), Compound a (4 g, 18.4 mmol) and sodium tert-butoxide (3.2 g, 33.4 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 7.9 g of Compound 1-20. (Yield: 61%, MS: [M+H]+=780)

Synthesis Example 1-21: Preparation of Compound 1-21

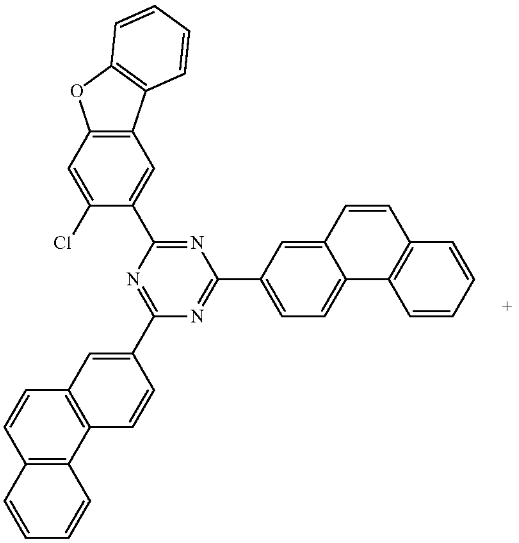

1-21-1

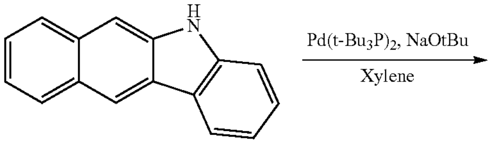

a

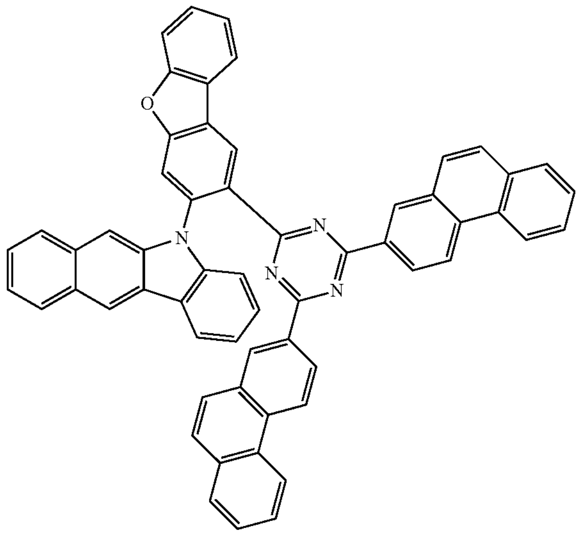

1-21

Intermediate 1-21-1 (10 g, 15.8 mmol), Compound a (3.8 g, 17.3 mmol) and sodium tert-butoxide (3 g, 31.5 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.5 g of Compound 1-21. (Yield: 51%, MS: [M+H]+=815)

Synthesis Example 1-22: Preparation of Compound 1-22

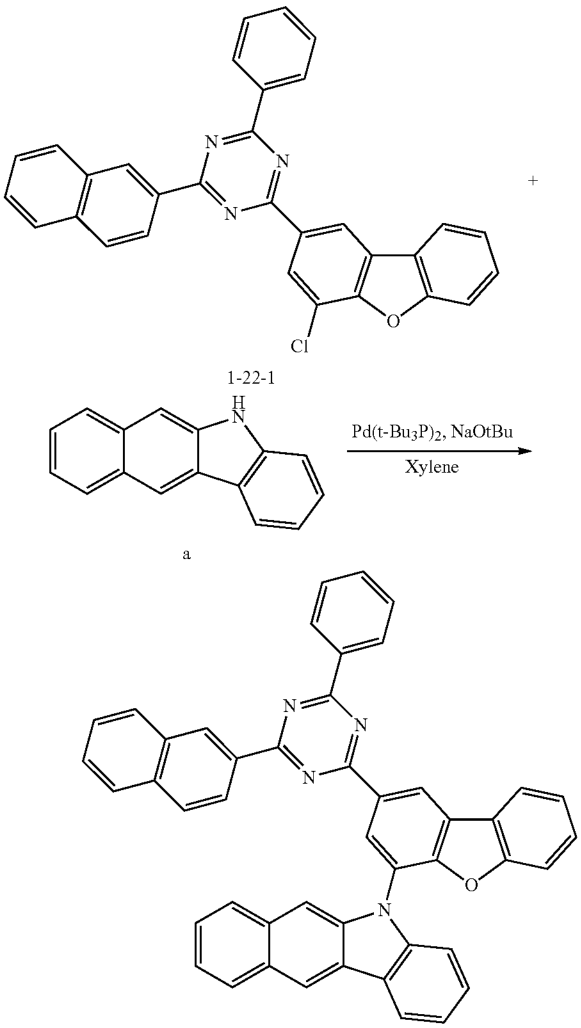

1-22-1 a 1-22

Intermediate 1-22-1 (10 g, 20.7 mmol), Compound a (4.9 g, 22.7 mmol) and sodium tert-butoxide (4 g, 41.3 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.6 g of Compound 1-22. (Yield: 63%, MS: [M+H]+=665)

Synthesis Example 1-23: Preparation of Compound 1-23

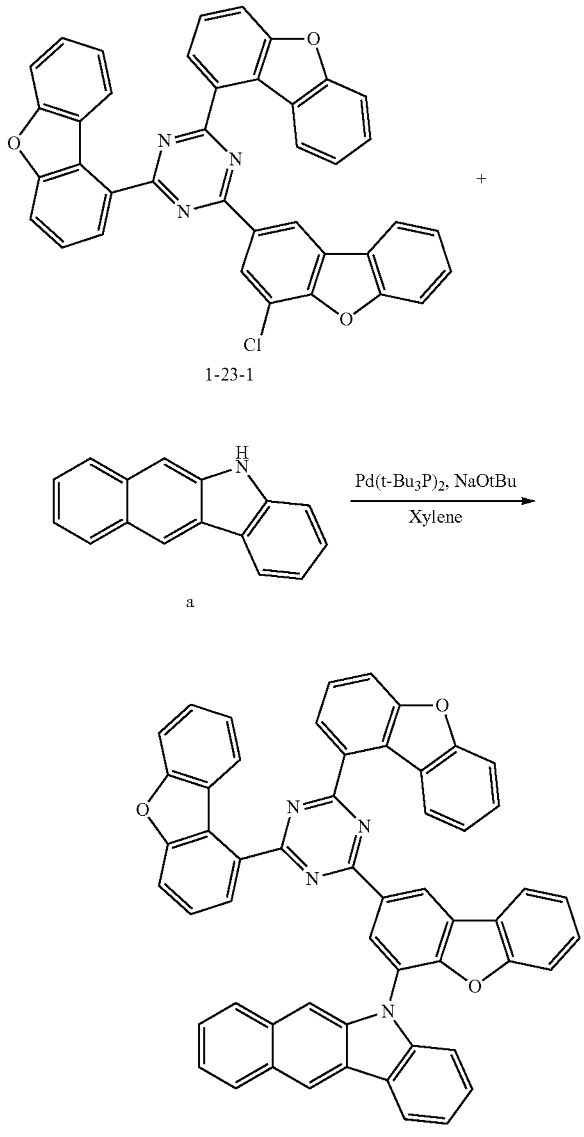

1-23-1 a 1-23

Intermediate 1-23-1 (10 g, 16.3 mmol), Compound a (3.9 g, 17.9 mmol) and sodium tert-butoxide (3.1 g, 32.6 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.5 g of Compound 1-23. (Yield: 66%, MS: [M+H]+=795)

Synthesis Example 1-24: Preparation of Compound 1-24

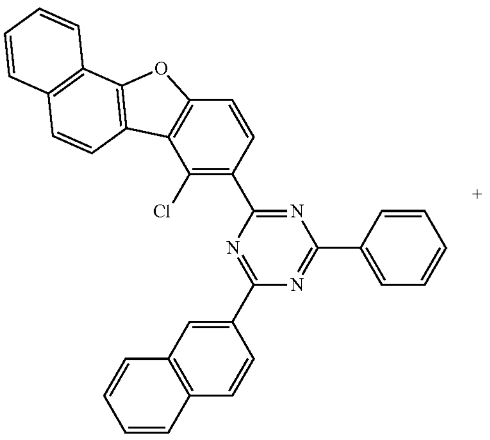

1-24-1

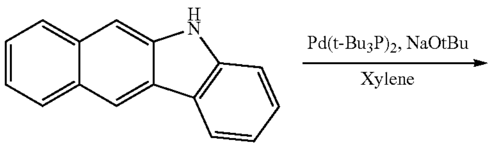

a

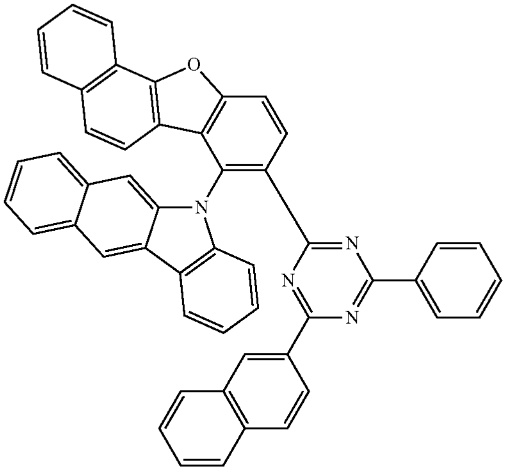

1-24

Intermediate 1-24-1 (10 g, 18.7 mmol), Compound a (4.5 g, 20.6 mmol) and sodium tert-butoxide (3.6 g, 37.5 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.8 g of Compound 1-24. (Yield: 51%, MS: [M+H]+=715)

Synthesis Example 1-25: Preparation of Compound 1-25

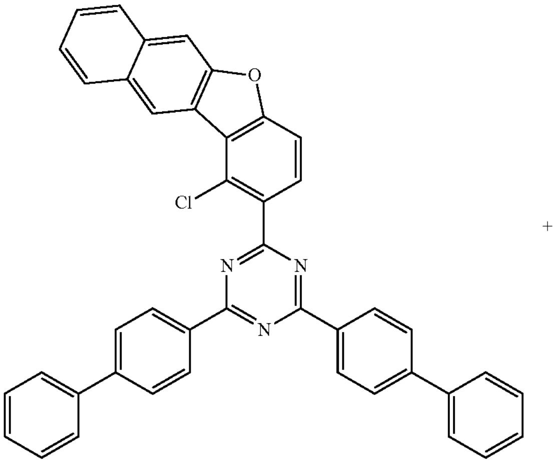

1-25-1

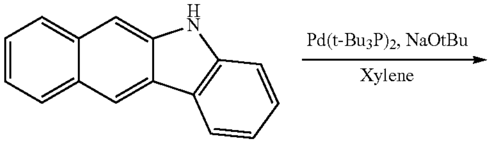

a

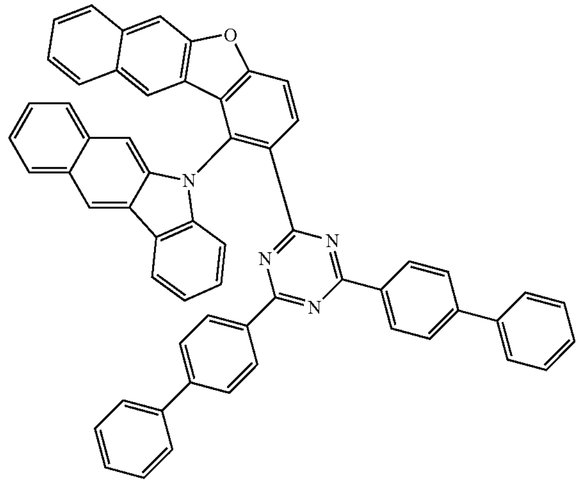

1-25

Intermediate 1-25-1 (10 g, 15.7 mmol), Compound a (3.8 g, 17.3 mmol) and sodium tert-butoxide (3 g, 31.4 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.7 g of Compound 1-25. (Yield: 68%, MS: [M+H]+=817)

Synthesis Example 1-26: Preparation of Compound 1-26

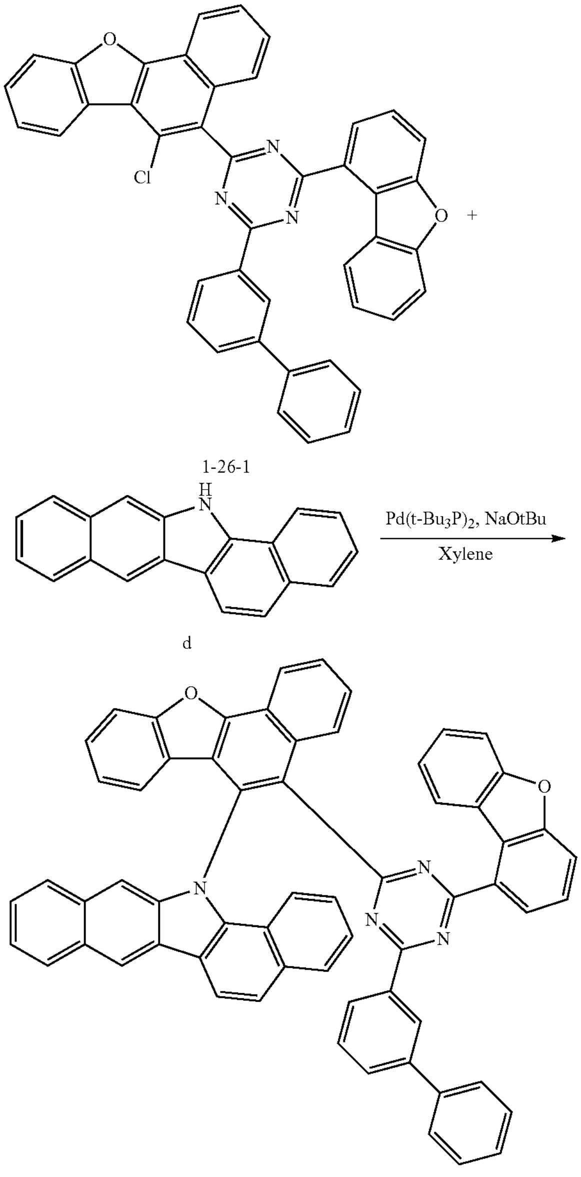

1-26-1 d 1-26

Intermediate 1-26-1 (10 g, 15.4 mmol), Compound d (4.5 g, 16.9 mmol) and sodium tert-butoxide (3 g, 30.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.1 g of Compound 1-26. (Yield: 60%, MS: [M+H]+=881)

Synthesis Example 1-27: Preparation of Compound 1-27

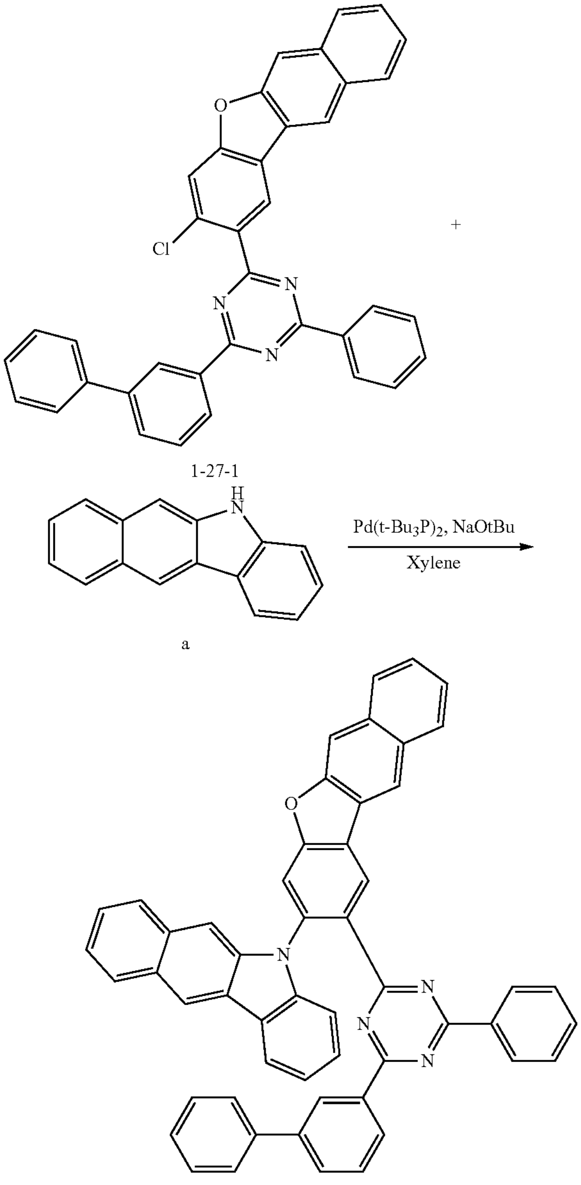

1-27-1 a 1-27

Intermediate 1-27-1 (10 g, 17.9 mmol), Compound a (4.3 g, 19.6 mmol) and sodium tert-butoxide (3.4 g, 35.7 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.3 g of Compound 1-27. (Yield: 63%, MS: [M+H]+=741)

Synthesis Example 1-28: Preparation of Compound 1-28

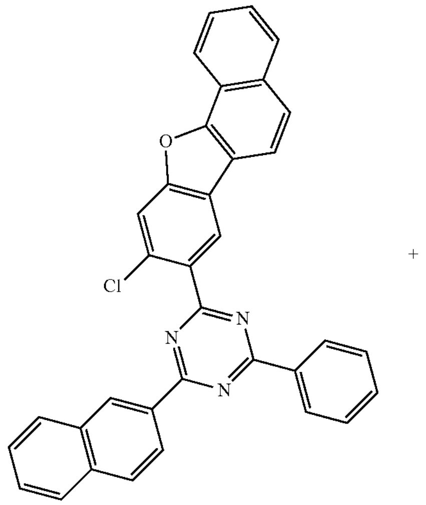

1-28-1

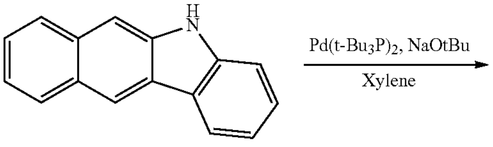

a

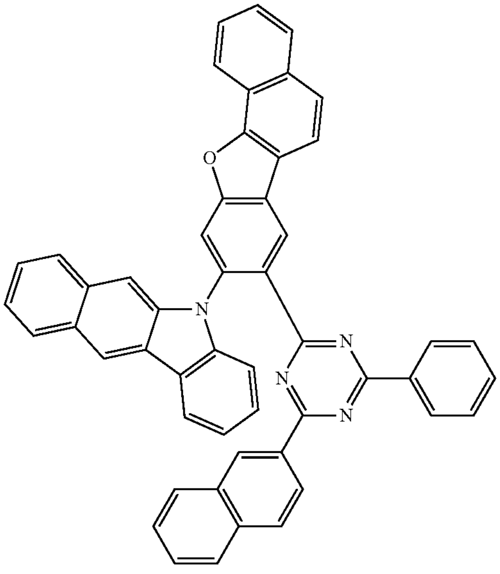

1-28

Intermediate 1-28-1 (10 g, 18.7 mmol), Compound a (4.5 g, 20.6 mmol) and sodium tert-butoxide (3.6 g, 37.5 mmol) were added to 200 ml of xylene under a nitrogen atmosphere, and the mixture was stirred and refluxed. Then, bis(tri-tert-butylphosphine)palladium(0) (0.2 g, 0.4 mmol) was added thereto. After 3 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9 g of Compound 1-28. (Yield: 67%, MS: [M+H]+=715)

Synthesis Example 1-29: Preparation of Compound 1-29

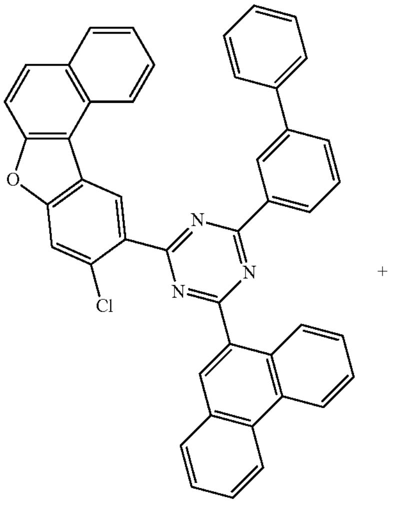

1-29-1

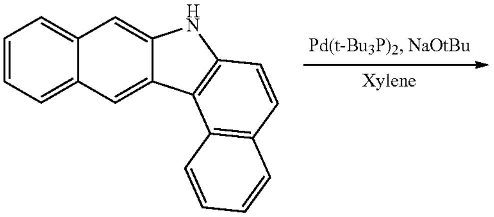

b

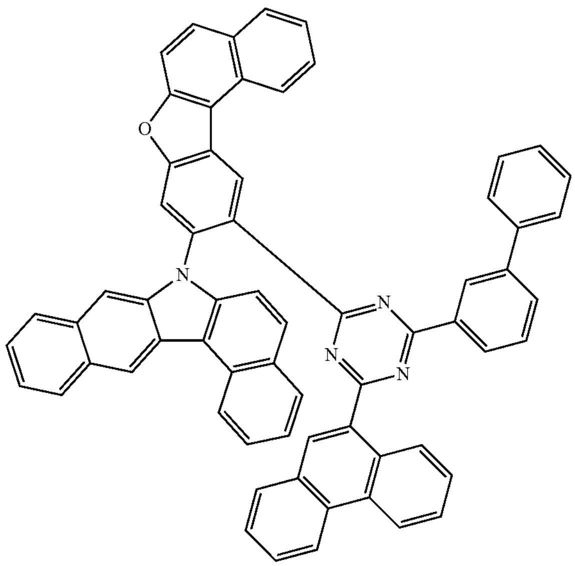

1-29

Intermediate 1-29-1 (10 g, 15.1 mmol), Compound b (4.5 g, 16.7 mmol) and sodium tert-butoxide (2.9 g, 30.3 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.3 g of Compound 1-29. (Yield: 69%, MS: [M+H]+=891)

Synthesis Example 1-30: Preparation of Compound 1-30

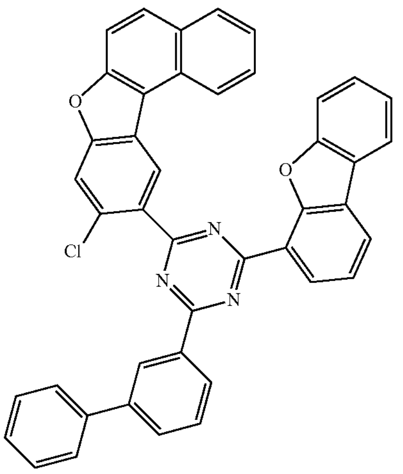

+

1-30-1

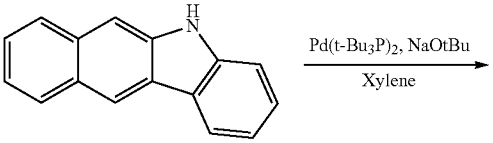

a

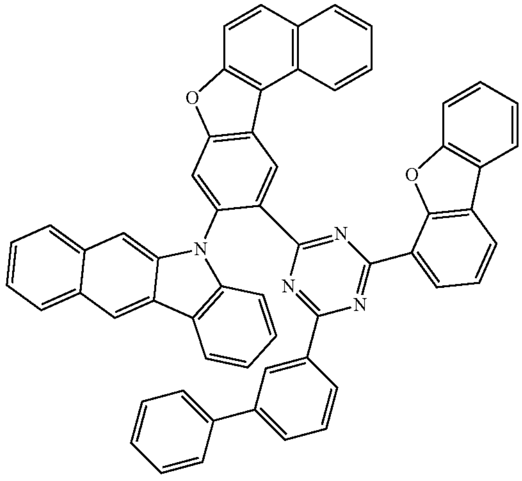

1-30

Intermediate 1-30-1 (10 g, 15.4 mmol), Compound a (3.7 g, 16.9 mmol) and sodium tert-butoxide (3 g, 30.8 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 6.4 g of Compound 1-30. (Yield: 50%, MS: [M+H]+=831)

Synthesis Example 1-31: Preparation of Compound 1-31

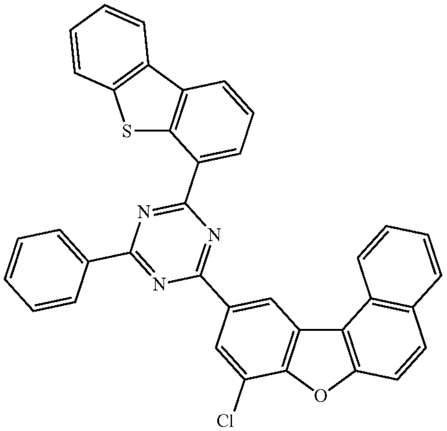

+

1-31-1

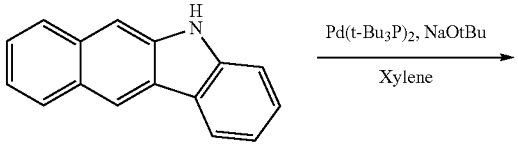

a

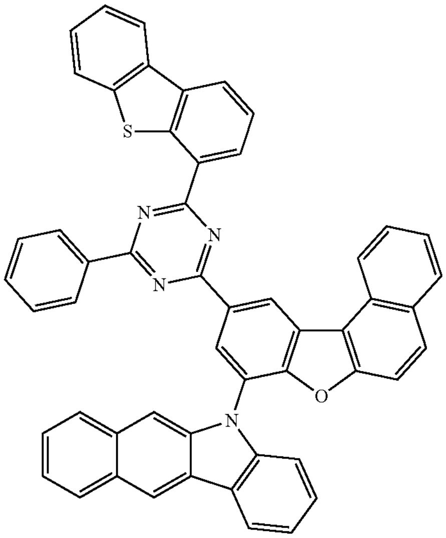

1-31

Intermediate 1-31-1 (10 g, 16.9 mmol), Compound a (4.1 g, 18.6 mmol) and sodium tert-butoxide (3.3 g, 33.9 mmol)

were added to 200 ml of xylene under a nitrogen atmosphere; and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 8.2 g of Compound 1-31. (Yield: 63%, MS: [M+H]+=771)

Synthesis Example 1-32: Preparation of Compound 1-32

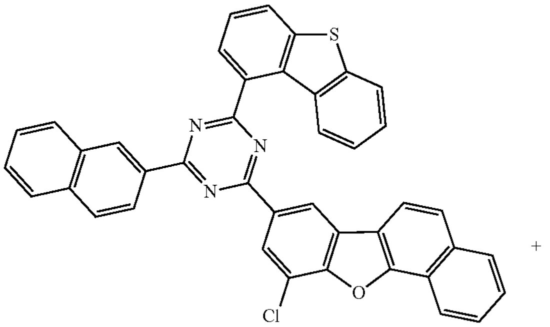

1-32-1

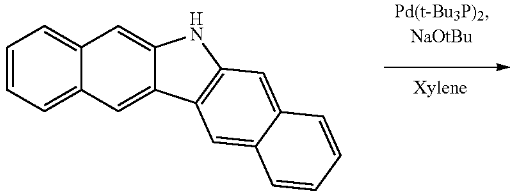

c

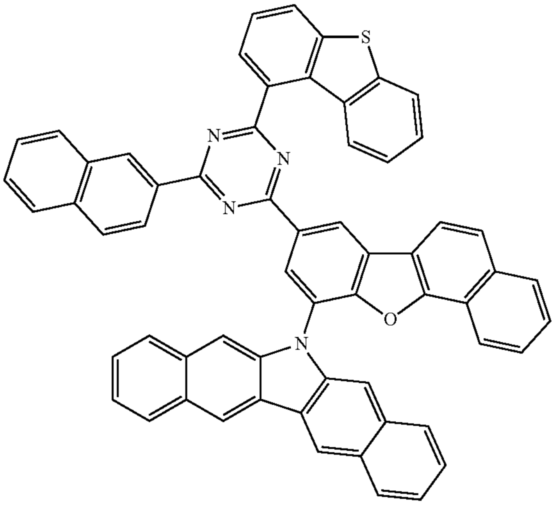

1-32

Intermediate 1-32-1 (10 g, 15.6 mmol), Compound c (4.6 g, 17.2 mmol) and sodium tert-butoxide (3 g, 31.2 mmol) were added to 200 ml of xylene under a nitrogen atmosphere, and the mixture was stirred and refluxed. Then, bis(tri-tert-butylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9.1 g of Compound 1-32. (Yield: 67%, MS: [M+H]+=871)

Synthesis Example 1-33: Preparation of Compound 1-33

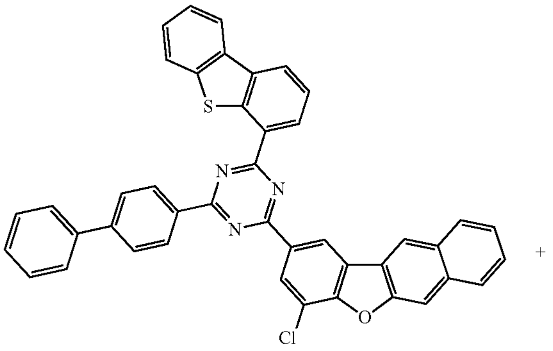

1-33-1

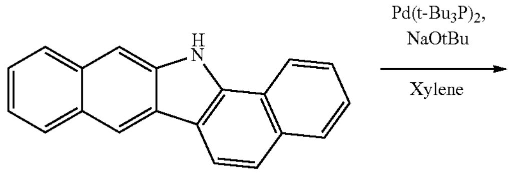

d

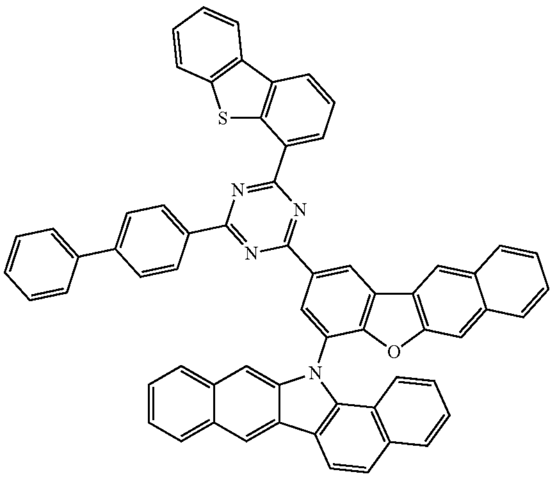

1-33

Intermediate 1-33-1 (10 g, 15 mmol), Compound d (4.4 g, 16.5 mmol) and sodium tert-butoxide (2.9 g, 30 mmol) were added to 200 ml of xylene under a nitrogen atmosphere, and the mixture was stirred and refluxed. Then, bis(tri-tertbutylphosphine)palladium(0) (0.2 g, 0.3 mmol) was added thereto. After 2 hours, when the reaction was completed, the reaction mixture was cooled to room temperature and the solvent was removed under reduced pressure. Then, the compound was completely dissolved again in chloroform, washed twice with water, and then the organic layer was separated, treated with anhydrous magnesium sulfate, then filtered, and the filtrate was distilled under reduced pressure. The concentrated compound was purified by silica gel column chromatography to give 9 g of Compound 1-33. (Yield: 67%, MS: [M+H]+=897)

Synthesis Example 1-34: Preparation of Compound 1-34

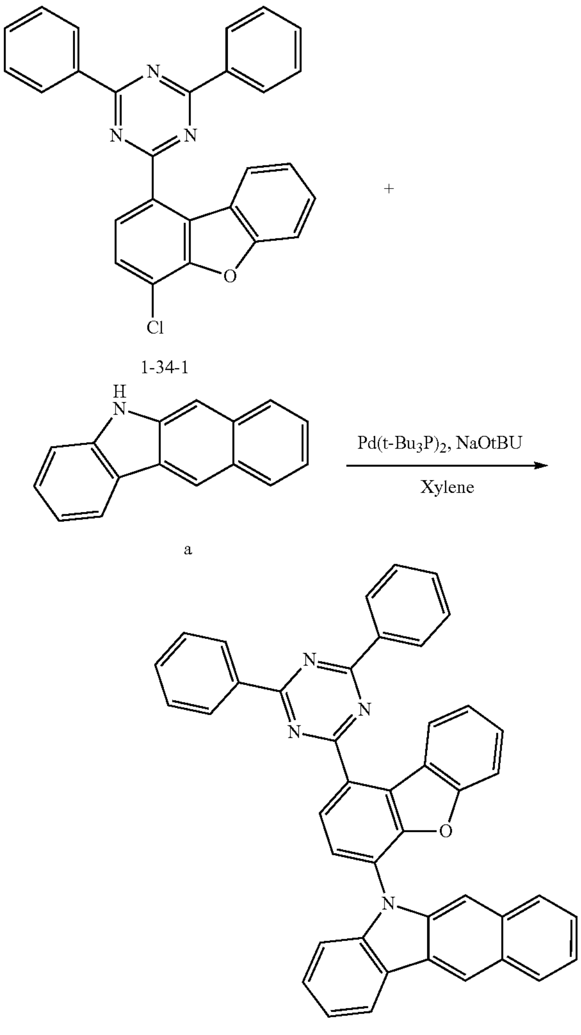

1-34-1 a 1-34

Intermediate 1-34-1 (10 g, 23 mmol) and Compound a (5 g, 23 mmol) were added to 200 ml of xylene under a nitrogen atmosphere, and the mixture was stirred and refluxed. Then, sodium tertiary-butoxide (6.6 g, 69.1 mmol) was added thereto, sufficiently stirred, and then bis(tri-tert-butylphosphine)palladium (0.2 g, 0.5 mmol) was added. After the reaction for 3 hours, the reaction mixture was cooled to room temperature and the organic layer was filtered to remove salt, and the filtered organic layer was distilled. This was again added to and dissolved in 425 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 9.9 g of Compound 1-34 as a yellow solid. (Yield: 70%, MS: [M+H]+=615.2)

Synthesis Example 1-35: Preparation of Compound 1-35

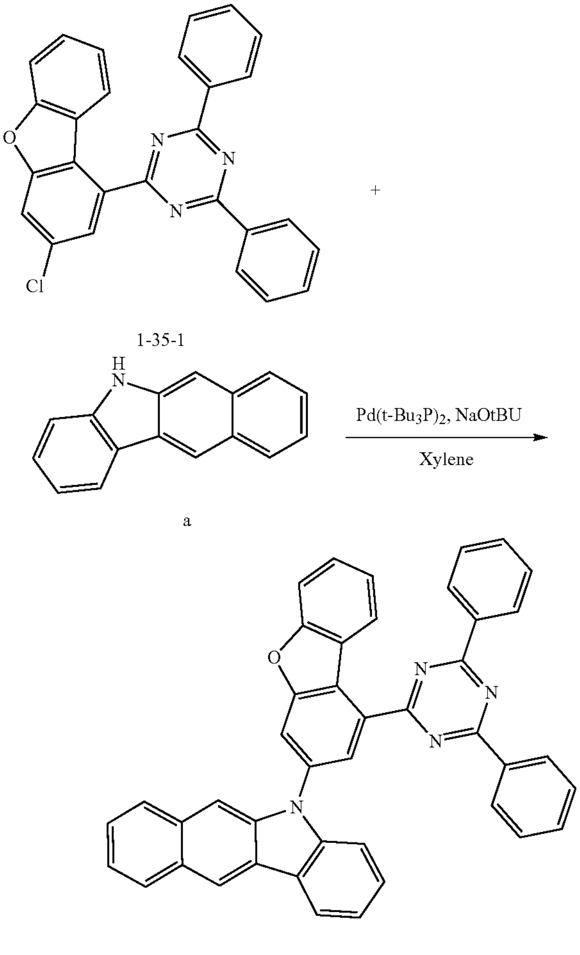

1-35-1 a 1-35

Intermediate 1-35-1 (10 g, 23 mmol) and Compound a (5 g, 23 mmol) were added to 200 ml of xylene under a nitrogen atmosphere, and the mixture was stirred and refluxed. Then, sodium tertiary-butoxide (6.6 g, 69.1 mmol) was added thereto, sufficiently stirred, and then bis(tri-tert-butylphosphine)palladium (0.2 g, 0.5 mmol) was added. After the reaction for 2 hours, the reaction mixture was cooled to room temperature and the organic layer was filtered to remove salt, and the filtered organic layer was distilled. This was again added to and dissolved in 425 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.5 g of Compound 1-35 as a yellow solid. (Yield: 60%, MS: [M+H]+=615.2)

Synthesis Example 1-36: Preparation of Compound 1-36

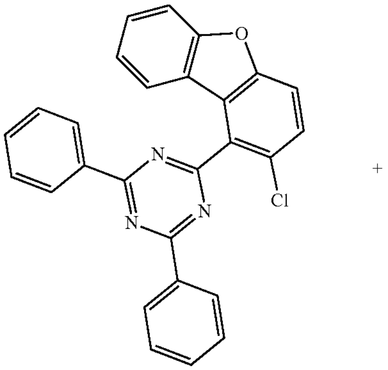

1-36-1

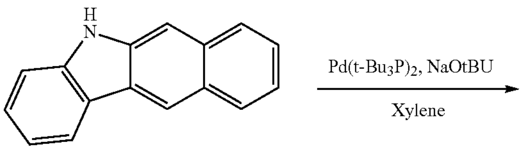

a

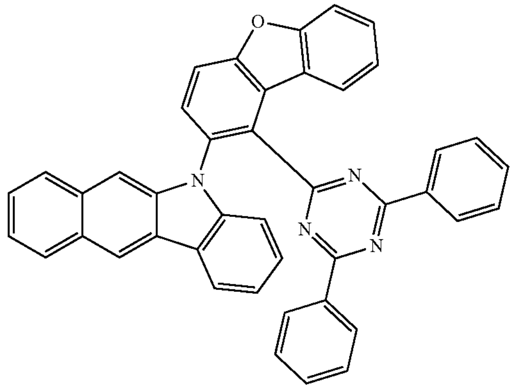

1-36

Intermediate 1-36-1 (10 g, 23 mmol) and Compound a (5 g, 23 mmol) were added to 200 ml of xylene under a nitrogen atmosphere, and the mixture was stirred and refluxed. Then, sodium tertiary-butoxide (6.6 g, 69.1 mmol) was added thereto, sufficiently stirred, and then bis(tri-tert-butylphosphine)palladium (0.2 g, 0.5 mmol) was added. After the reaction for 2 hours, the reaction mixture was cooled to room temperature and the organic layer was filtered to remove salt, and the filtered organic layer was distilled. This was again added to and dissolved in 425 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 9.1 g of Compound 1-36 as a yellow solid. (Yield: 64%, MS: [M+H]+=615.2)

Synthesis Example 1-37: Preparation of Compound 1-37

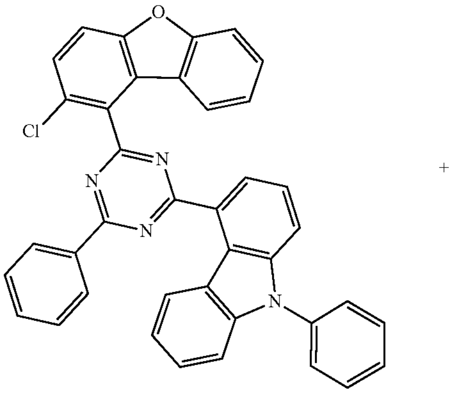

1-37-1

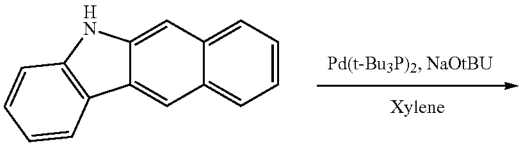

a

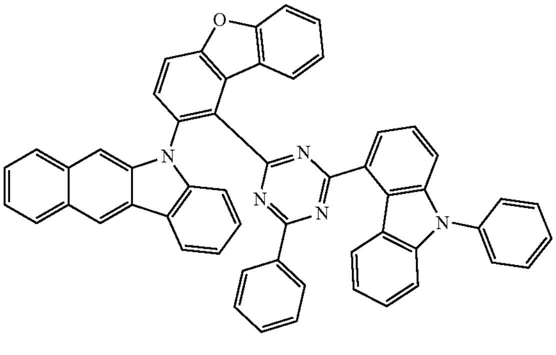

1-37

Intermediate 1-37-1 (10 g, 16.7 mmol) and Compound a (3.6 g, 16.7 mmol) were added to 200 ml of xylene under a nitrogen atmosphere, and the mixture was stirred and refluxed. Then, sodium tertiary-butoxide (4.8 g, 50.1 mmol) was added thereto, sufficiently stirred, and then bis(tri-tert-butylphosphine)palladium (0.2 g, 0.3 mmol) was added. After the reaction for 2 hours, the reaction mixture was cooled to room temperature and the organic layer was filtered to remove salt, and the filtered organic layer was distilled. This was again added to and dissolved in 390 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.6 g of Compound 1-37 as a yellow solid. (Yield: 66%, MS: [M+H]+=780.3)

Synthesis Example 1-38: Preparation of Compound 1-38

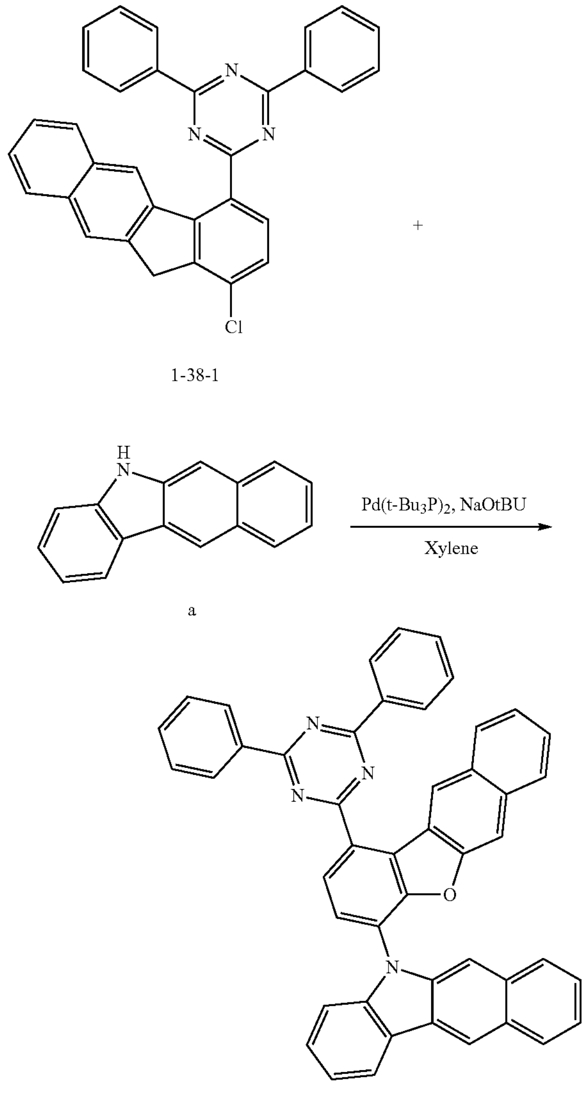

1-38-1 a 1-38

Intermediate 1-38-1 (10 g, 20.7 mmol) and Compound a (4.5 g, 20.7 mmol) were added to 200 ml of xylene under a nitrogen atmosphere, and the mixture was stirred and refluxed. Then, sodium tertiary-butoxide (6 g, 62 mmol) was added thereto, sufficiently stirred, and then bis(tri-tert-butylphosphine)palladium (0.2 g, 0.4 mmol) was added. After the reaction for 3 hours, the reaction mixture was cooled to room temperature and the organic layer was filtered to remove salt, and the filtered organic layer was distilled. This was again added to and dissolved in 412 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 9.1 g of Compound 1-38 as a yellow solid. (Yield: 66%, MS: [M+H]+=665.2)

Synthesis Example 1-39: Preparation of Compound 1-39

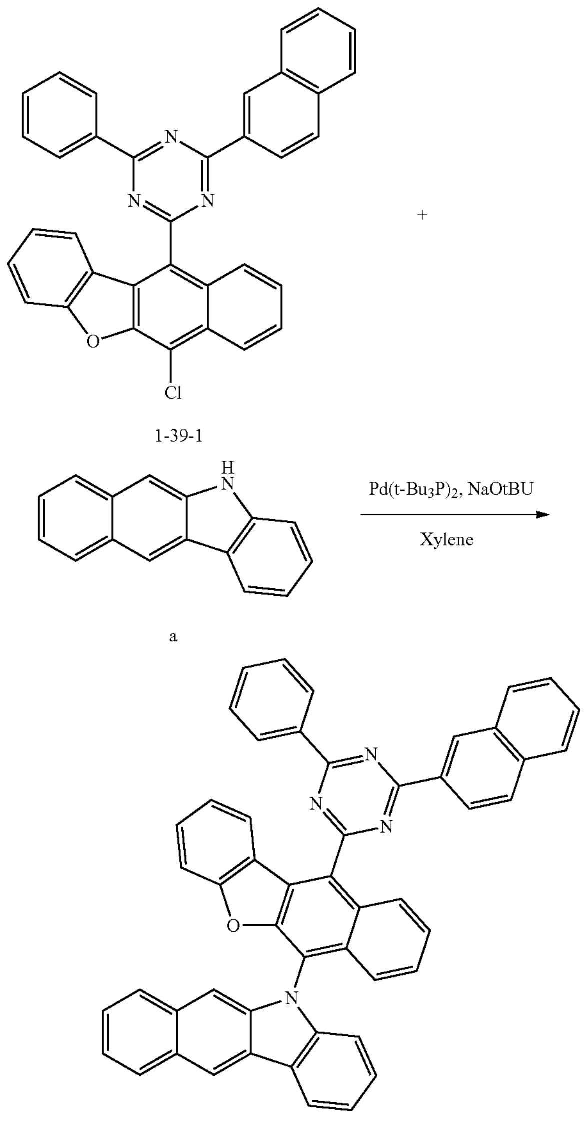

1-39-1 a 1-39

Intermediate 1-39-1 (10 g, 18.7 mmol) and Compound a (4.1 g, 18.7 mmol) were added to 200 ml of xylene under a nitrogen atmosphere, and the mixture was stirred and refluxed. Then, sodium tertiary-butoxide (5.4 g, 56.2 mmol) was added thereto, sufficiently stirred, and then bis(tri-tert-butylphosphine)palladium (0.2 g, 0.4 mmol) was added. After the reaction for 2 hours, the reaction mixture was cooled to room temperature and the organic layer was filtered to remove salt, and the filtered organic layer was distilled. This was again added to and dissolved in 401 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 7.8 g of Compound 1-39 as a yellow solid. (Yield: 58%, MS: [M+H]+=715.2)

Synthesis Example 1-40: Preparation of Compound 1-40

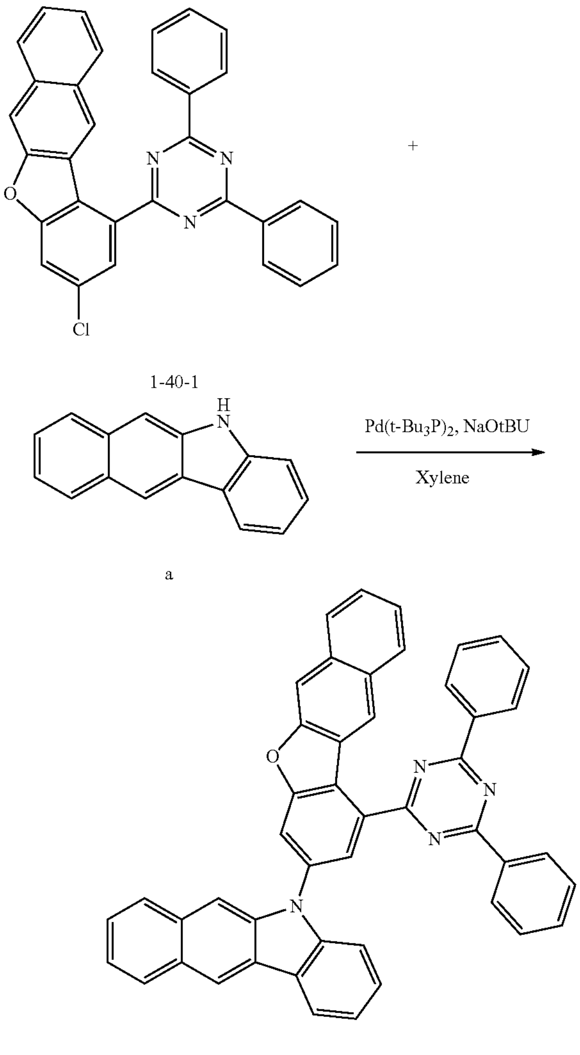

1-40-1 a 1-40

Intermediate 1-40-1 (10 g, 20.7 mmol) and Compound a (4.5 g, 20.7 mmol) were added to 200 ml of xylene under a nitrogen atmosphere, and the mixture was stirred and refluxed. Then, sodium tertiary-butoxide (6 g, 62 mmol) was added thereto, sufficiently stirred, and then bis(tri-tert-butylphosphine)palladium (0.2 g, 0.4 mmol) was added. After the reaction for 3 hours, the reaction mixture was cooled to room temperature and the organic layer was filtered to remove salt, and the filtered organic layer was distilled. This was again added to and dissolved in 412 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 7.8 g of Compound 1-40 as a yellow solid. (Yield: 57%, MS: [M+H]+=665.2)

Synthesis Example 1-41: Preparation of Compound 1-41

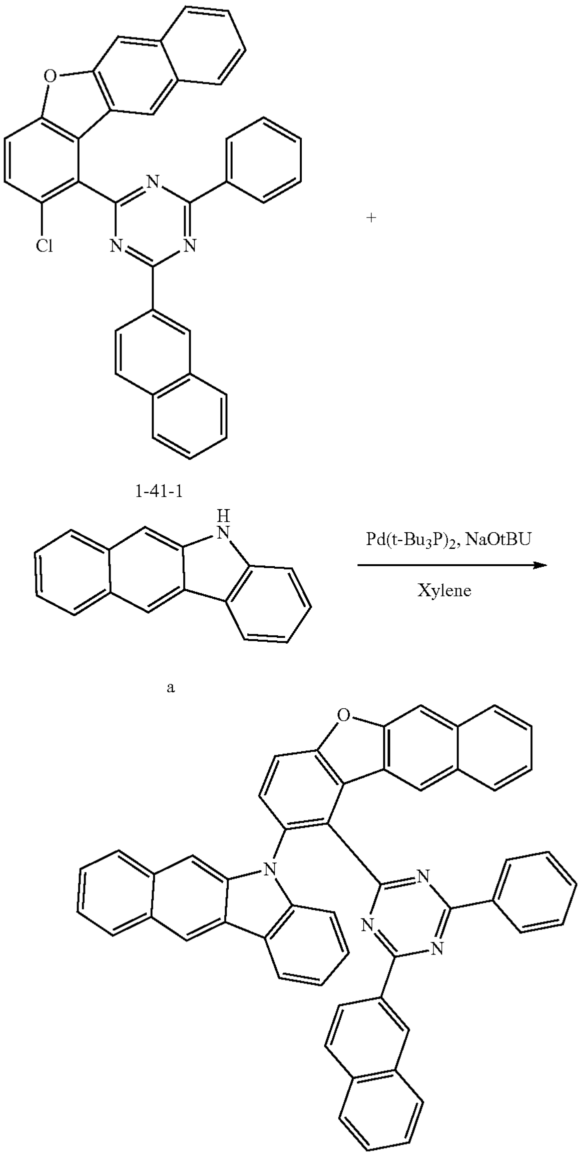

1-41-1 a 1-41

Intermediate 1-41-1 (10 g, 18.7 mmol) and Compound a (4.1 g, 18.7 mmol) were added to 200 ml of xylene under a nitrogen atmosphere, and the mixture was stirred and refluxed. Then, sodium tertiary-butoxide (5.4 g, 56.2 mmol) was added thereto, sufficiently stirred, and then bis(tri-tert-butylphosphine)palladium (0.2 g, 0.4 mmol) was added. After the reaction for 3 hours, the reaction mixture was cooled to room temperature and the organic layer was filtered to remove salt, and the filtered organic layer was distilled. This was again added and dissolved in to 401 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.7 g of Compound 1-41 as a yellow solid. (Yield: 65%, MS: [M+H]+=715.2)

Synthesis Example 1-42: Preparation of Compound 1-42

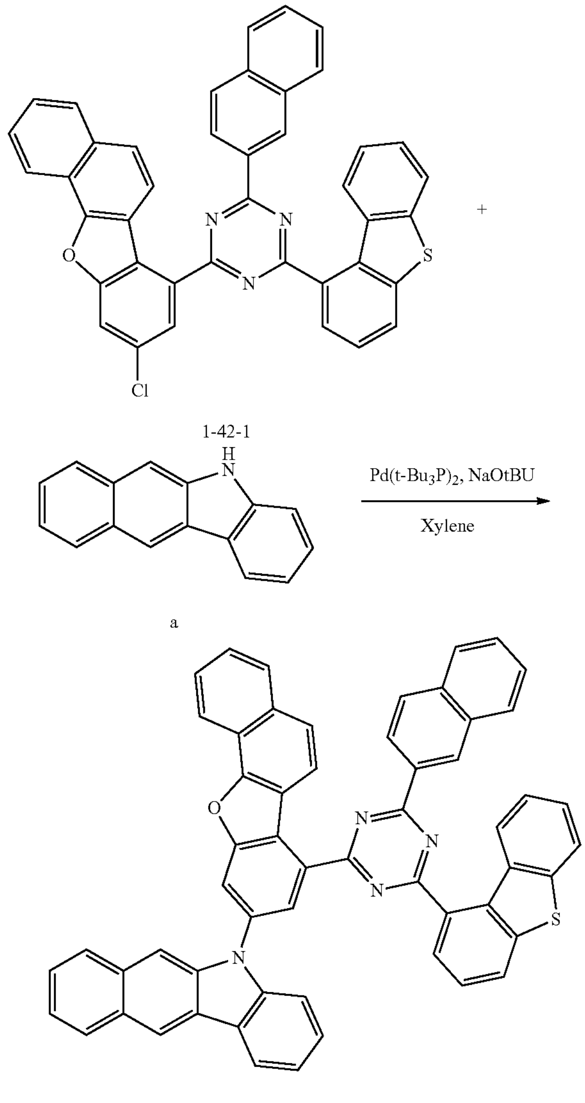

1-42-1 a 1-42

Intermediate 1-42-1 (10 g, 15.6 mmol) and Compound a (3.4 g, 15.6 mmol) were added to 200 ml of xylene under a nitrogen atmosphere, and the mixture was stirred and refluxed. Then, sodium tertiary-butoxide (4.5 g, 46.9 mmol) was added thereto, sufficiently stirred, and then bis(tri-tert-butylphosphine)palladium (0.2 g, 0.3 mmol) was added. After the reaction for 2 hours, the reaction mixture was cooled to room temperature and the organic layer was filtered to remove salt, and the filtered organic layer was distilled. This was again added to and dissolved in 384 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.2 g of Compound 1-42 as a yellow solid. (Yield: 64%, MS: [M+H]+=821.2)

Synthesis Example 1-43: Preparation of Compound 1-43

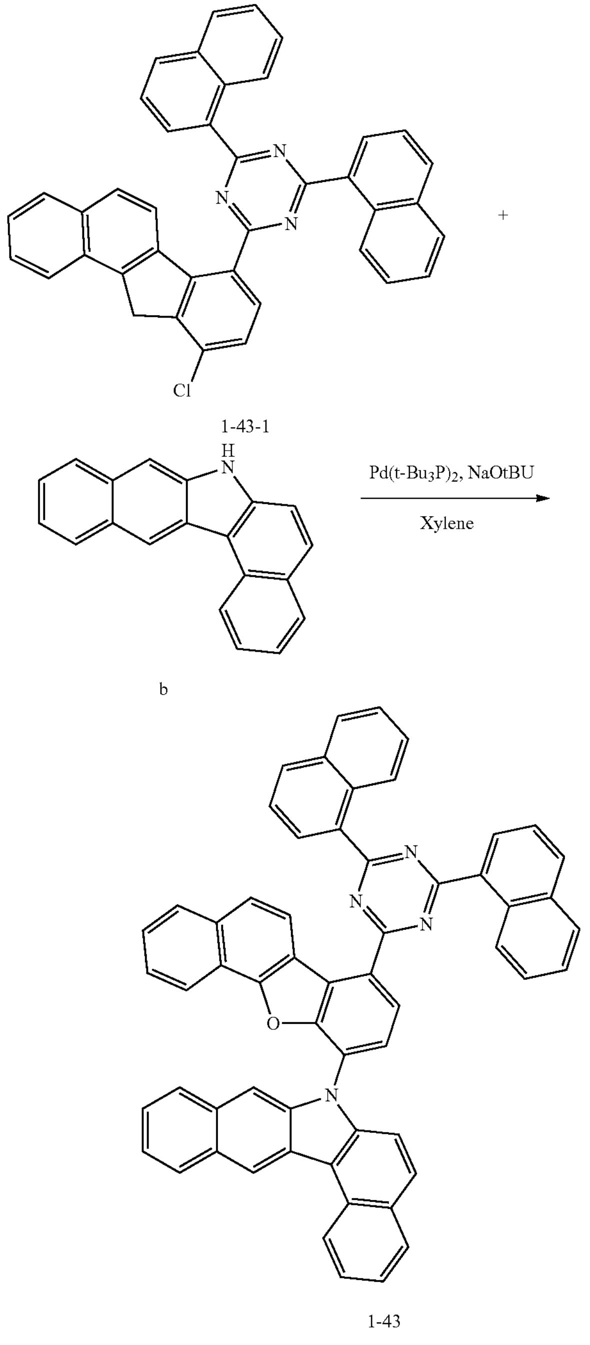

1-43-1 b 1-43

Intermediate 1-43-1 (10 g, 17.1 mmol) and Compound b (4.6 g, 17.1 mmol) were added to 200 ml of xylene under a nitrogen atmosphere, and the mixture was stirred and refluxed. Then, sodium tertiary-butoxide (4.9 g, 51.4 mmol) was added thereto, sufficiently stirred, and then bis(tri-tert-butylphosphine)palladium (0.2 g, 0.3 mmol) was added. After the reaction for 3 hours, the reaction mixture was cooled to room temperature and the organic layer was filtered to remove salt, and the filtered organic layer was distilled. This was again added to and dissolved in 418 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.8 g of Compound 1-43 as a yellow solid. (Yield: 63%, MS: [M+H]+=815.3)

Synthesis Example 1-44: Preparation of Compound 1-44

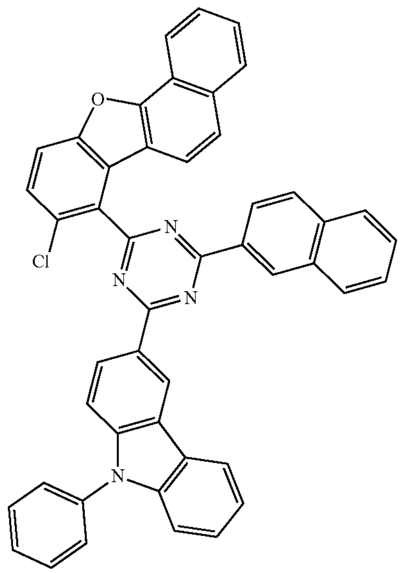

1-44-1

+

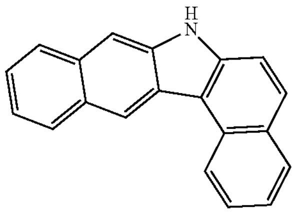

b

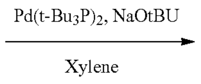

-continued

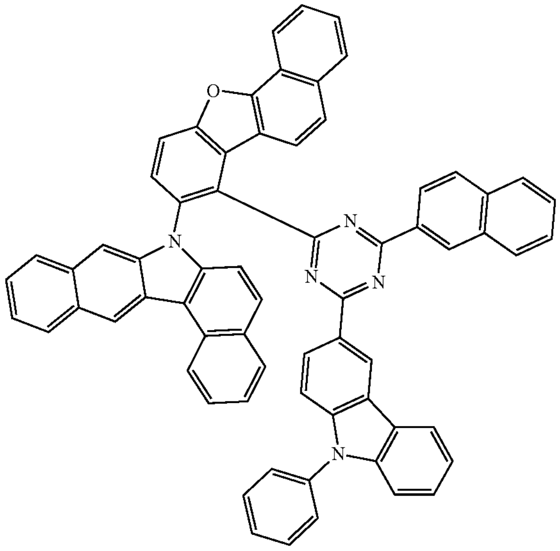

1-44

Intermediate 1-44-1 (10 g, 14.3 mmol) and Compound b (3.8 g, 14.3 mmol) were added to 200 ml of xylene under a nitrogen atmosphere, and the mixture was stirred and refluxed. Then, sodium tertiary-butoxide (4.1 g, 42.9 mmol) was added thereto, sufficiently stirred, and then bis(tri-tert-butylphosphine)palladium (0.1 g, 0.3 mmol) was added. After the reaction for 2 hours, the reaction mixture was cooled to room temperature and the organic layer was filtered to remove salt, and the filtered organic layer was distilled. This was again added to and dissolved in 399 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 7.3 g of Compound 1-44 as a yellow solid. (Yield: 55%, MS: [M+H]+=930.3)

Synthesis Example 1-45: Preparation of Compound 1-45

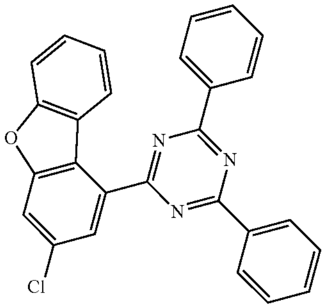

1-45-1

+

-continued

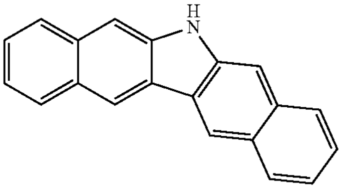

c

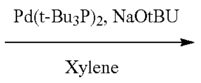

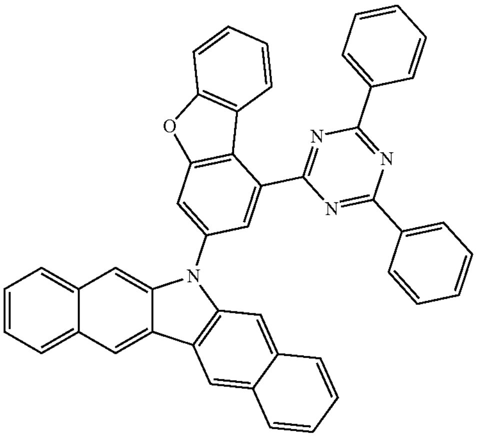

1-45

Intermediate 1-45-1 (10 g, 23 mmol) and Compound c (6.2 g, 23 mmol) were added to 200 ml of xylene under a nitrogen atmosphere, and the mixture was stirred and refluxed. Then, sodium tertiary-butoxide (6.6 g, 69.1 mmol) was added thereto, sufficiently stirred, and then bis(tri-tert-butylphosphine)palladium (0.2 g, 0.5 mmol) was added. After the reaction for 2 hours, the reaction mixture was cooled to room temperature and the organic layer was filtered to remove salt, and the filtered organic layer was distilled. This was again added to and dissolved in 459 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 9 g of Compound 1-45 as a yellow solid. (Yield: 59%, MS: [M+H]+=665.2)

Synthesis Example 1-46: Preparation of Compound 1-46

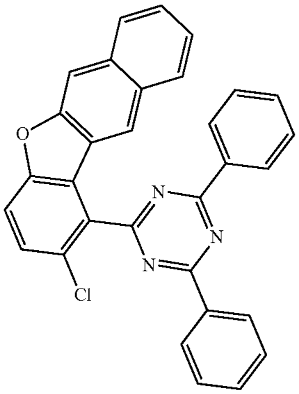

1-46-1

+

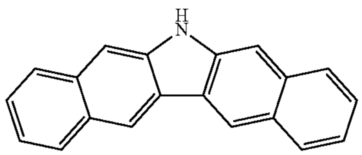

c

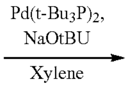

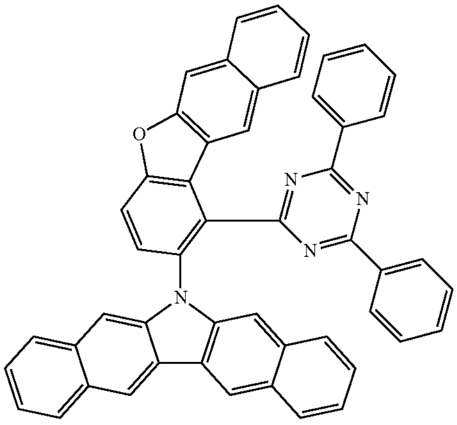

1-46

Intermediate 1-46-1 (10 g, 20.7 mmol) and Compound c (5.5 g, 20.7 mmol) were added to 200 ml of xylene under a nitrogen atmosphere, and the mixture was stirred and refluxed. Then, sodium tertiary-butoxide (6 g, 62 mmol) was added thereto, sufficiently stirred, and then bis(tri-tert-butylphosphine)palladium (0.2 g, 0.4 mmol) was added. After the reaction for 3 hours, the reaction mixture was cooled to room temperature and the organic layer was filtered to remove salt, and the filtered organic layer was distilled. This was again added to and dissolved in 443 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 10.2 g of Compound 1-46 as a yellow solid. (Yield: 69%, MS: [M+H]+=715.2)

Synthesis Example 1-47: Preparation of Compound 1-47

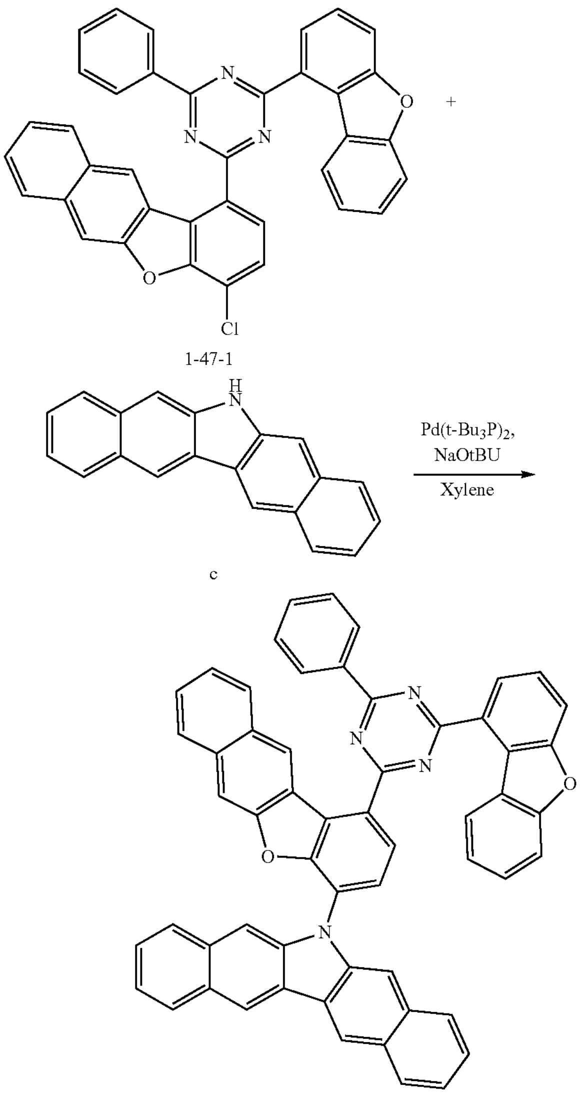

1-47-1 c 1-47

Intermediate 1-47-1 (10 g, 17.4 mmol) and Compound c (4.7 g, 17.4 mmol) were added to 200 ml of xylene under a nitrogen atmosphere, and the mixture was stirred and refluxed. Then, sodium tertiary-butoxide (5 g, 52.3 mmol) was added thereto, sufficiently stirred, and then bis(tri-tert-butylphosphine)palladium (0.2 g, 0.3 mmol) was added. After the reaction for 3 hours, the reaction mixture was cooled to room temperature and the organic layer was filtered to remove salt, and the filtered organic layer was distilled. This was again added to and dissolved in 420 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8 g of Compound 1-47 as a yellow solid. (Yield: 57%, MS: [M+H]+=805.2)

Synthesis Example 1-48: Preparation of Compound 1-48

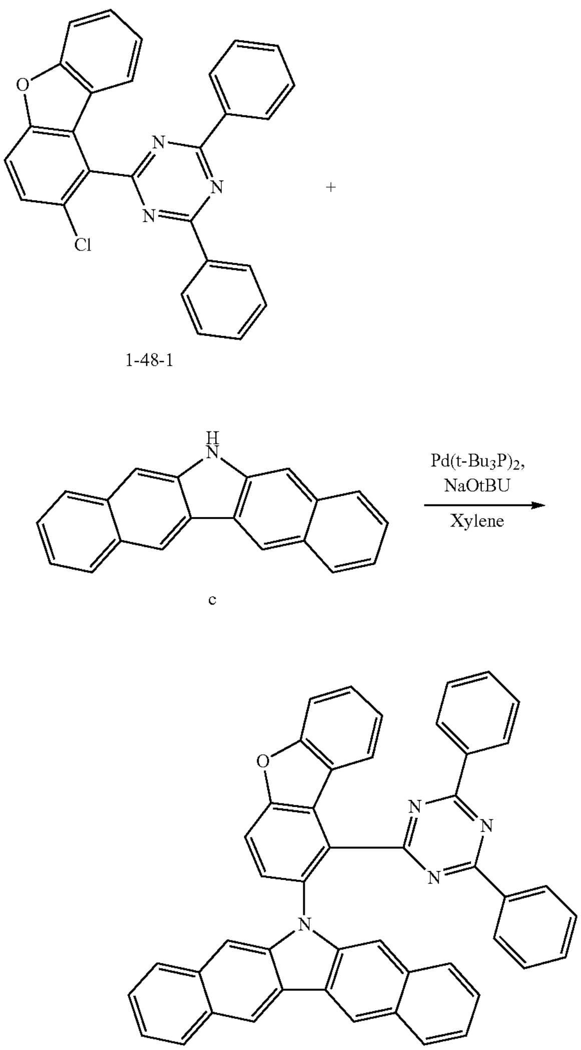

1-48-1 c 1-48

Intermediate 1-48-1 (10 g, 23 mmol) and Compound c (6.2 g, 23 mmol) were added to 200 ml of xylene under a nitrogen atmosphere, and the mixture was stirred and refluxed. Then, sodium tertiary-butoxide (6.6 g, 69.1 mmol) was added thereto, sufficiently stirred, and then bis(tri-tert-butylphosphine)palladium (0.2 g, 0.5 mmol) was added. After the reaction for 3 hours, the reaction mixture was cooled to room temperature and the organic layer was filtered to remove salt, and the filtered organic layer was distilled. This was again added to and dissolved in 459 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 0.4 g of Compound 1-48 as a yellow solid. (Yield: 68%, MS: [M+H]+=665.2)

Synthesis Example 1-49: Preparation of Compound 1-49

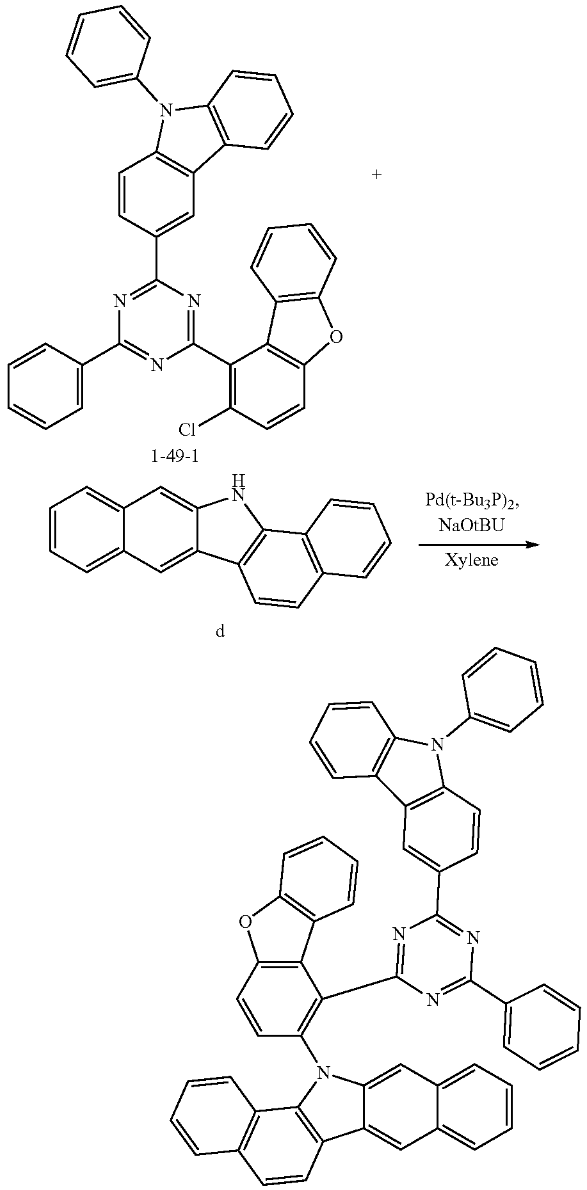

1-49-1 d 1-49

Intermediate 1-49-1 (10 g, 16.7 mmol) and Compound d (4.5 g, 16.7 mmol) were added to 200 ml of xylene under a nitrogen atmosphere, and the mixture was stirred and refluxed. Then, sodium tertiary-butoxide (4.8 g, 50.2 mmol) was added thereto, sufficiently stirred, and then bis(tri-tert-butylphosphine)palladium (0.2 g, 0.3 mmol) was added. After the reaction for 3 hours, the reaction mixture was cooled to room temperature and the organic layer was filtered to remove salt, and the filtered organic layer was distilled. This was again added to and dissolved in 416 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8 g of Compound 1-49 as a yellow solid. (Yield: 58%, MS: [M+H]+=830.3)

Synthesis Example 1-50: Preparation of Compound 1-50

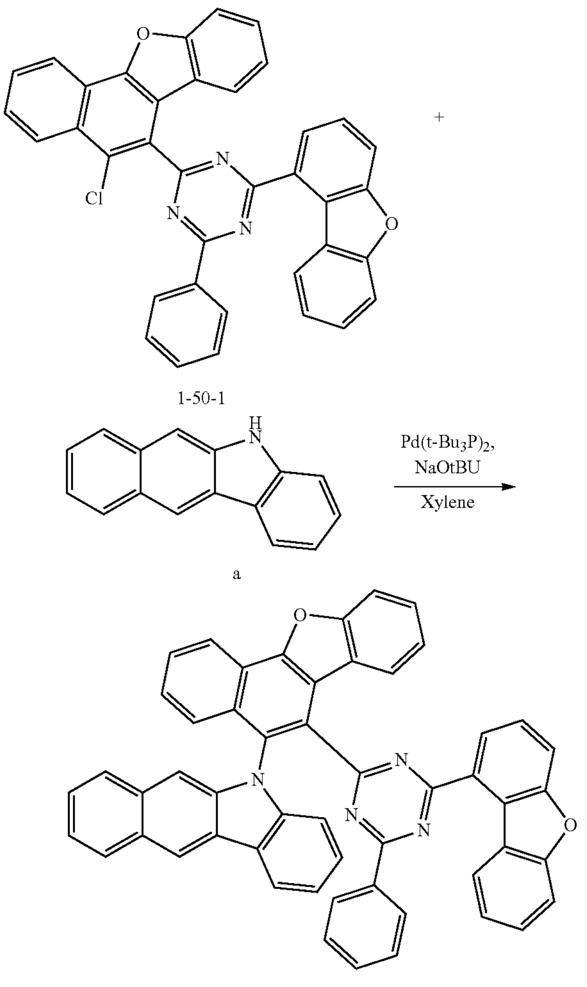

1-50-1 a 1-50

Intermediate 1-50-1 (10 g, 17.4 mmol) and Compound a (3.8 g, 17.4 mmol) were added to 200 ml of xylene under a nitrogen atmosphere, and the mixture was stirred and refluxed. Then, sodium tertiary-butoxide (5 g, 52.3 mmol) was added thereto, sufficiently stirred, and then bis(tri-tert-butylphosphine)palladium (0.2 g, 0.3 mmol) was added. After the reaction for 3 hours, the reaction mixture was cooled to room temperature and the organic layer was filtered to remove salt, and the filtered organic layer was distilled. This was again added to and dissolved in 394 mL (30 times the amount) of chloroform, and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give 8.3 g of Compound 1-50 as a yellow solid. (Yield: 63%, MS: [M+H]+=755.2)

Synthesis Example 2-1: Preparation of Compound 2-1

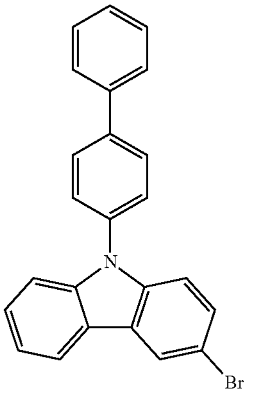

2-1-1

+

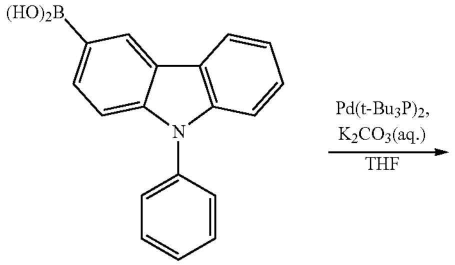

2-1-2

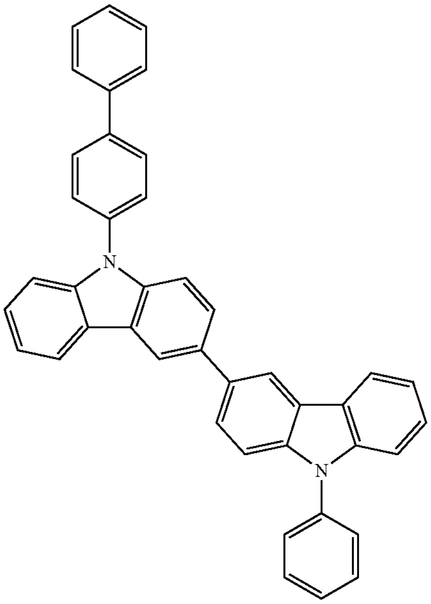

2-1

Intermediate 2-1-1 (10 g, 25.2 mmol) and Intermediate 2-1-2 (8 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9 g of Compound 2-1. (Yield: 64%, MS: [M+H]+=561)

Synthesis Example 2-2: Preparation of Compound 2-2

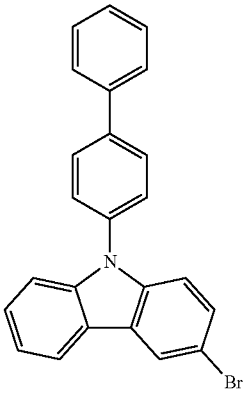

2-2-1

+

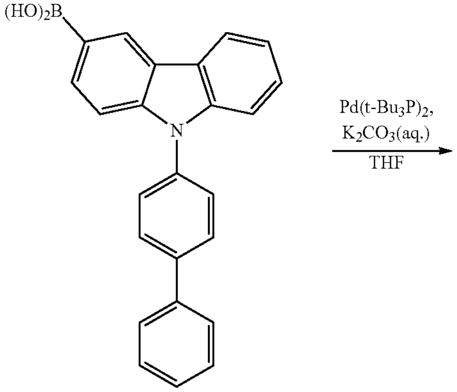

2-2-2

-continued

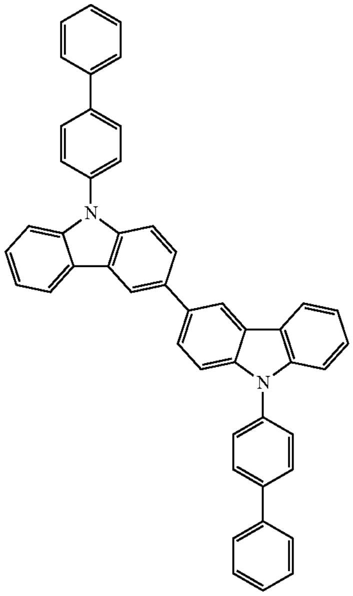

2-2

Intermediate 2-2-1 (10 g, 25.2 mmol) and Intermediate 2-2-2 (8 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10.6 g of Compound 2-2. (Yield: 66%, MS: [M+H]+=637)

Synthesis Example 2-3: Preparation of Compound 2-3

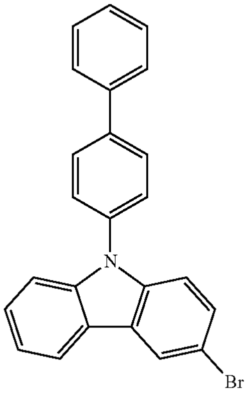

2-3-1

+

-continued

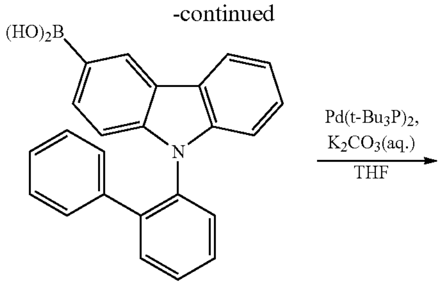

2-3-2

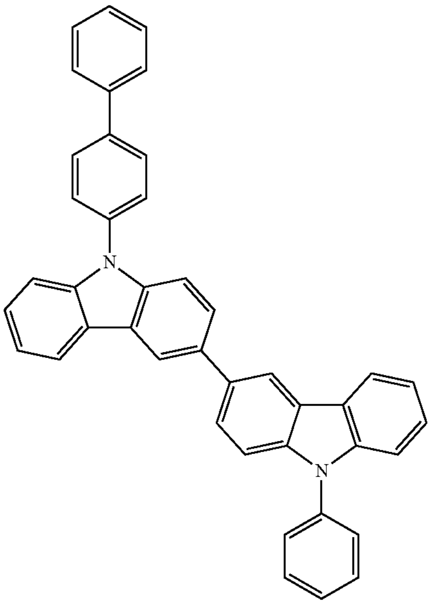

2-3

Intermediate 2-3-1 (10 g, 25.2 mmol) and Intermediate 2-3-2 (10.1 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9 g of Compound 2-3. (Yield: 56%, MS: [M+H]+=637)

Synthesis Example 2-4: Preparation of Compound 2-4

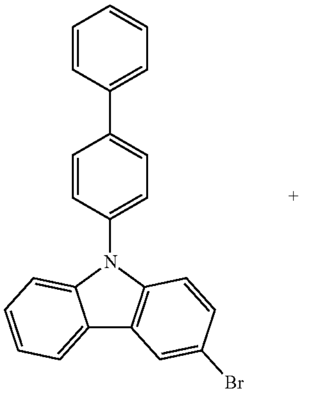

2-4-1

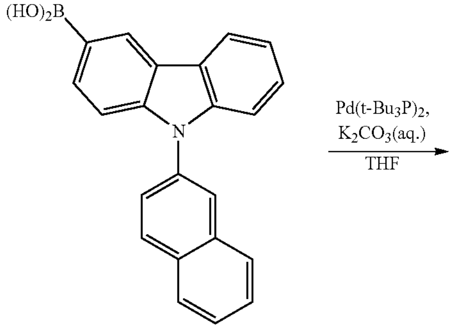

2-4-2

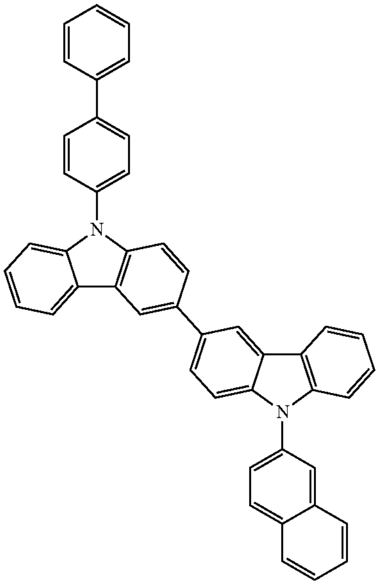

2-4

Intermediate 2-4-1 (10 g, 25.2 mmol) and Intermediate 2-4-2 (9.3 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 7.8 g of Compound 2-4. (Yield: 51%, MS: [M+H]+=611)

Synthesis Example 2-5: Preparation of Compound 2-5

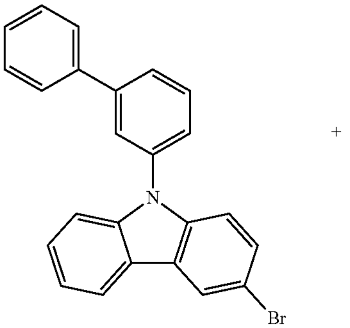

2-5-1

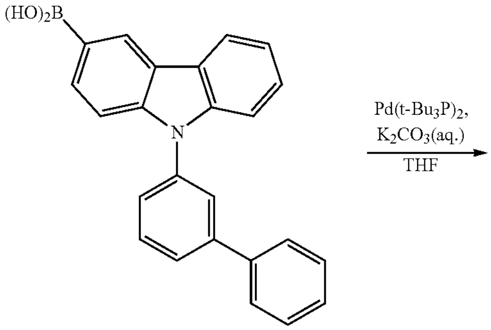

2-5-2

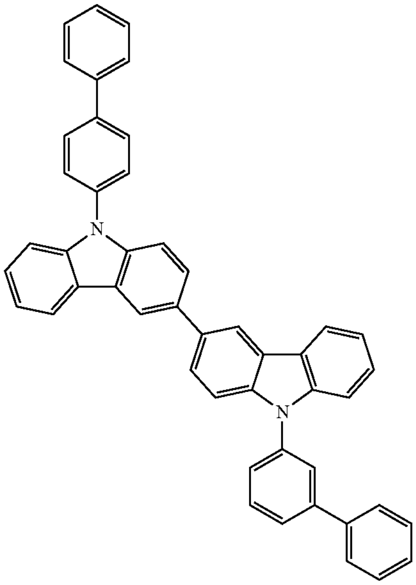

2-5

Intermediate 2-5-1 (10 g, 25.2 mmol) and Intermediate 2-5-2 (10.1 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10.4 g of Compound 2-5. (Yield: 65%, MS: [M+H]+=637)

Synthesis Example 2-6: Preparation of Compound 2-6

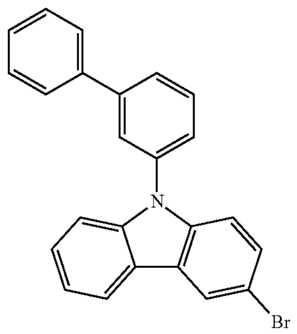

2-6-1

+

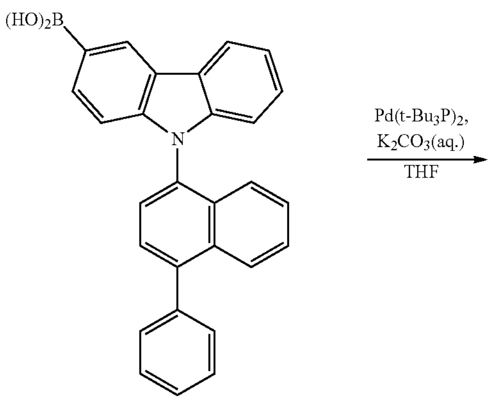

2-6-2

-continued

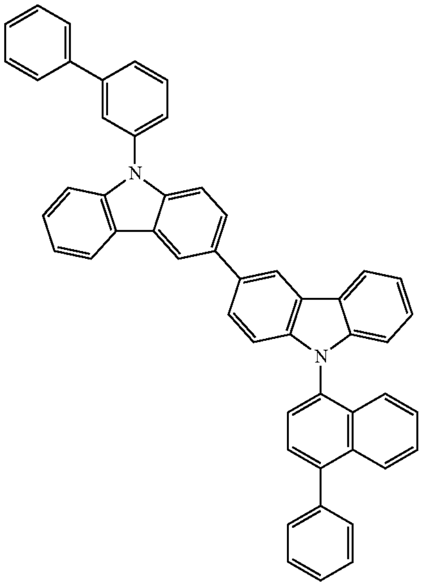

2-6

Intermediate 2-6-1 (10 g, 25.2 mmol) and Intermediate 2-6-2 (11.4 g, 27.7 mmol) were added to 200 ml of THF under a nitrogen atmosphere, stirred, and potassium carbonate (13.9 g, 100.7 mmol) was dissolved in water and added thereto. The mixture was sufficiently stirred and refluxed, and then bis(tri-tert-butylphosphine)palladium(0) (0.1 g, 0.3 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10.5 g of Compound 2-6. (Yield: 61%, MS: [M+H]+=687)

Synthesis Example 2-7: Preparation of Compound 2-7

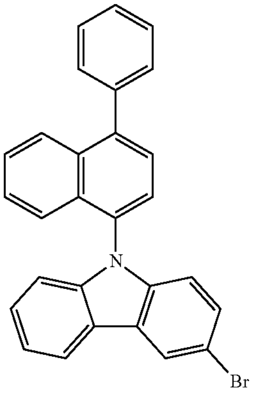

2-7-1

+

-continued

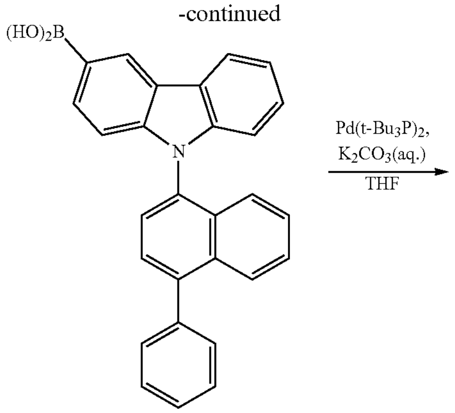

2-4-2

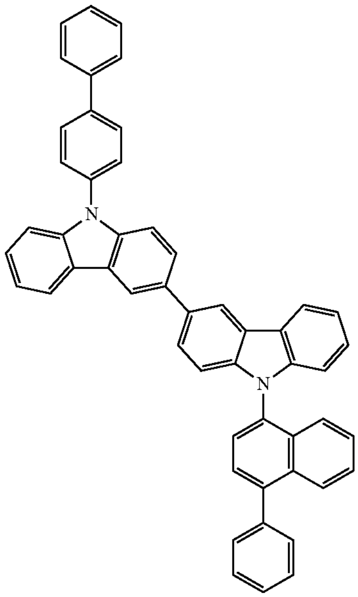

2-7

Intermediate 2-7-1 (10 g, 22.4 mmol) and Intermediate 2-7-2 (10.2 g, 24.6 mmol) were added to 200 ml of THF under a nitrogen atmosphere, stirred, and potassium carbonate (12.4 g, 89.5 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 11 g of Compound 2-7. (Yield: 67%, MS: [M+H]+=737)

Synthesis Example 2-8: Preparation of Compound 2-8

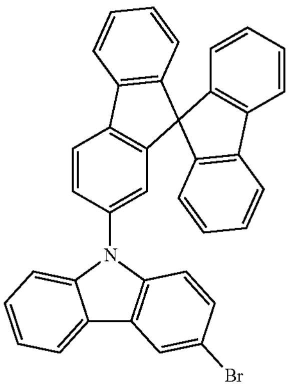

+

2-8-1

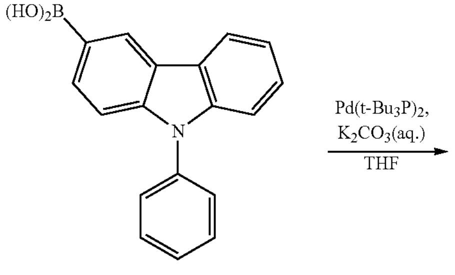

2-8-2

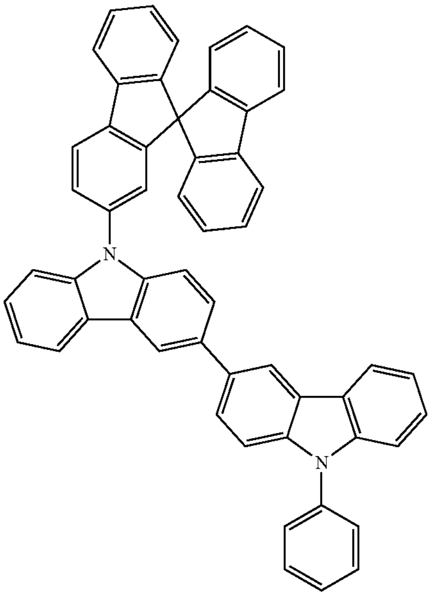

2-8

Intermediate 2-8-1 (10 g, 17.9 mmol) and Intermediate 2-8-2 (5.6 g, 19.7 mmol) were added to 200 ml of THF under a nitrogen atmosphere, stirred, and potassium carbonate (9.9 g, 71.5 mmol) was dissolved in water and added thereto. The mixture was sufficiently stirred and refluxed, and then bis (tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 7.8 g of Compound 2-8. (Yield: 60%, MS: [M+H]+=723)

Synthesis Example 2-9: Preparation of Compound 2-9

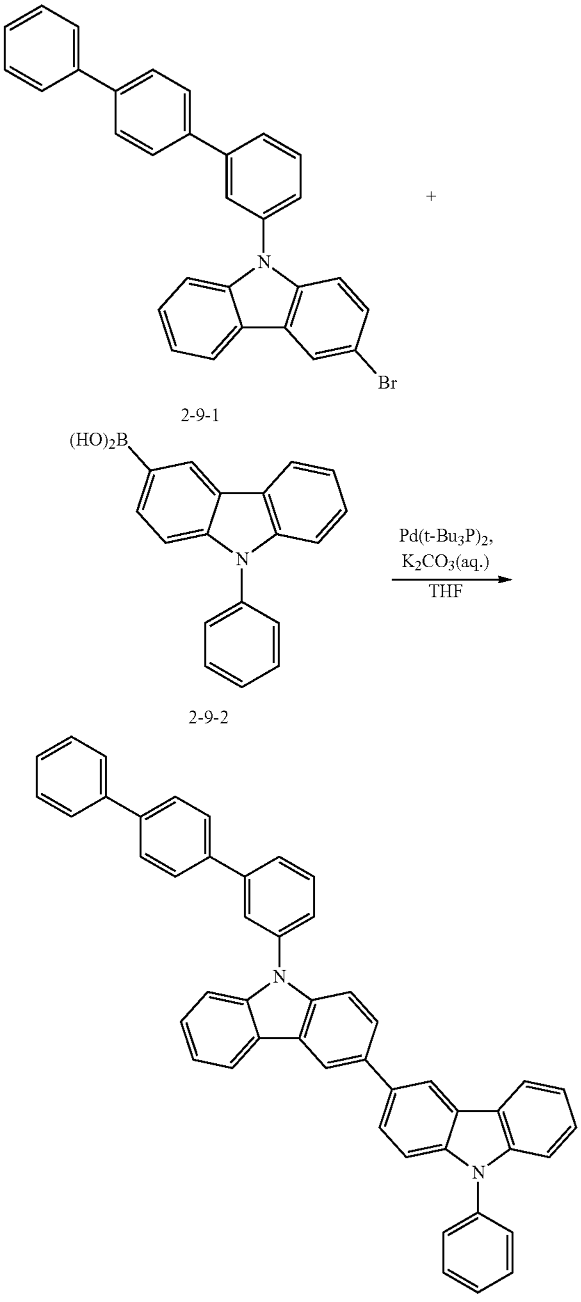

2-9-1

2-9-2

2-9

Intermediate 2-9-1 (10 g, 21.1 mmol) and Intermediate 2-9-2 (6.7 g, 23.3 mmol) were added to 200 ml of THF under a nitrogen atmosphere, stirred, and potassium carbonate (11.7 g, 84.6 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 7.4 g of Compound 2-9. (Yield: 55%, MS: [M+H]+=637)

Synthesis Example 2-10: Preparation of Compound 2-10

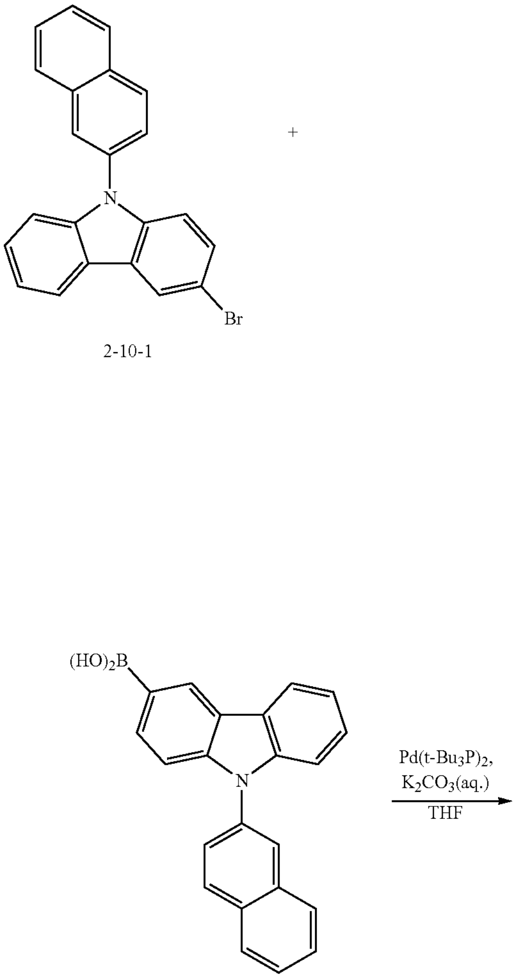

2-10-1

2-10-2

-continued

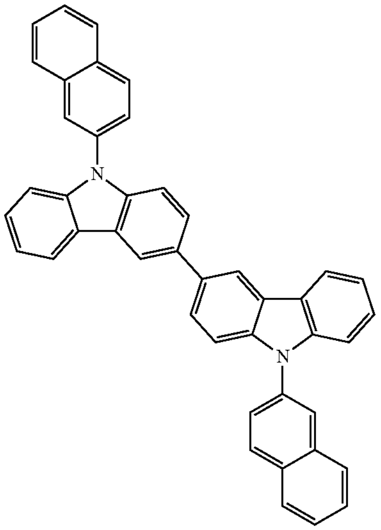

2-10

Intermediate 2-10-1 (10 g, 27 mmol) and Intermediate 2-10-2 (10 g, 29.6 mmol) were added to 200 ml of THF under a nitrogen atmosphere, stirred, and potassium carbonate (14.9 g, 107.8 mmol) was dissolved in water and added thereto. The mixture was sufficiently stirred and refluxed, and then bis(tri-tert-butylphosphine)palladium(0) (0.1 g, 0.3 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 11 g of Compound 2-10. (Yield: 70%, MS: [M+H]+=585)

Synthesis Example 2-11: Preparation of Compound 2-11

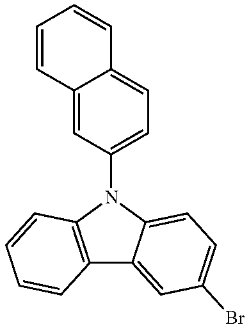

2-11-1

+

-continued

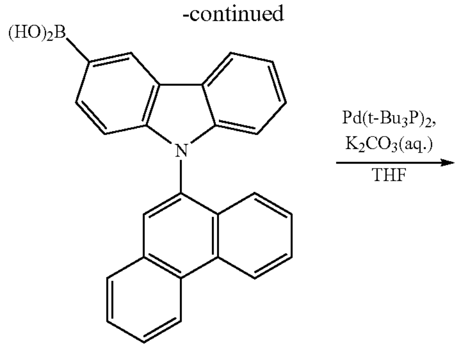

2-11-2

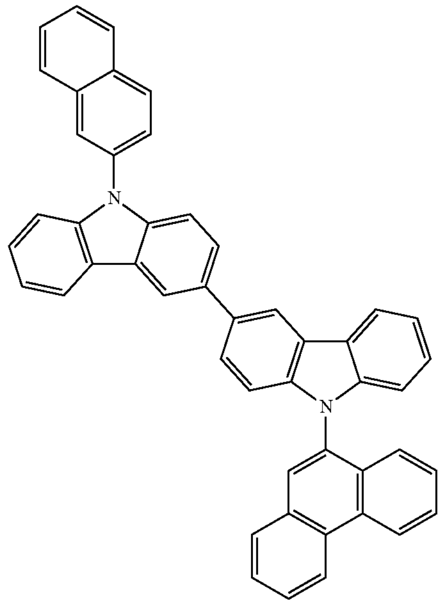

2-11

Intermediate 2-11-1 (10 g, 27 mmol) and Intermediate 2-11-2 (11.5 g, 29.6 mmol) were added to 200 ml of THF under a nitrogen atmosphere, stirred, and potassium carbonate (14.9 g, 107.8 mmol) was dissolved in water and added thereto. The mixture was sufficiently stirred and refluxed, and then bis(tri-tert-butylphosphine)palladium(0) (0.1 g, 0.3 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 11.5 g of Compound 2-11. (Yield: 67%, MS: [M+H]+=635)

Synthesis Example 2-12: Preparation of Compound 2-12

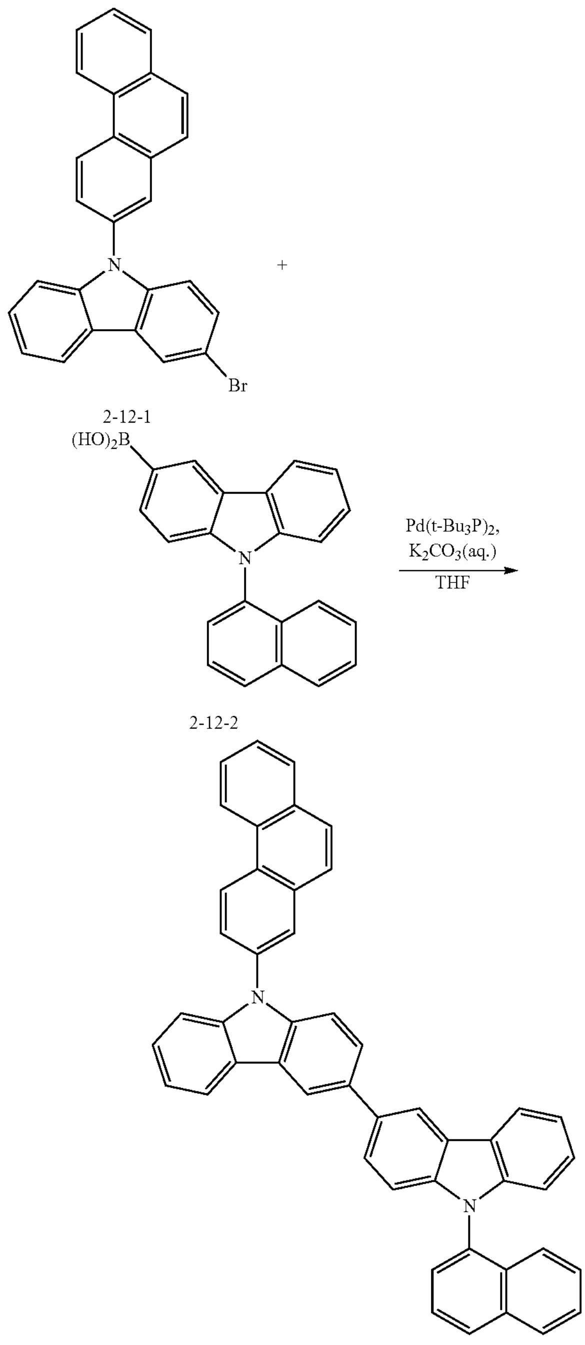

2-12-1

2-12-2

2-12

Intermediate 2-12-1 (10 g, 23.8 mmol) and Intermediate 2-12-2 (8.8 g, 26.1 mmol) were added to 200 ml of THF under a nitrogen atmosphere, stirred, and potassium carbonate (13.1 g, 95 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10.4 g of Compound 2-12. (Yield: 69%, MS: [M+H]+=635)

Synthesis Example 2-13: Preparation of Compound 2-13

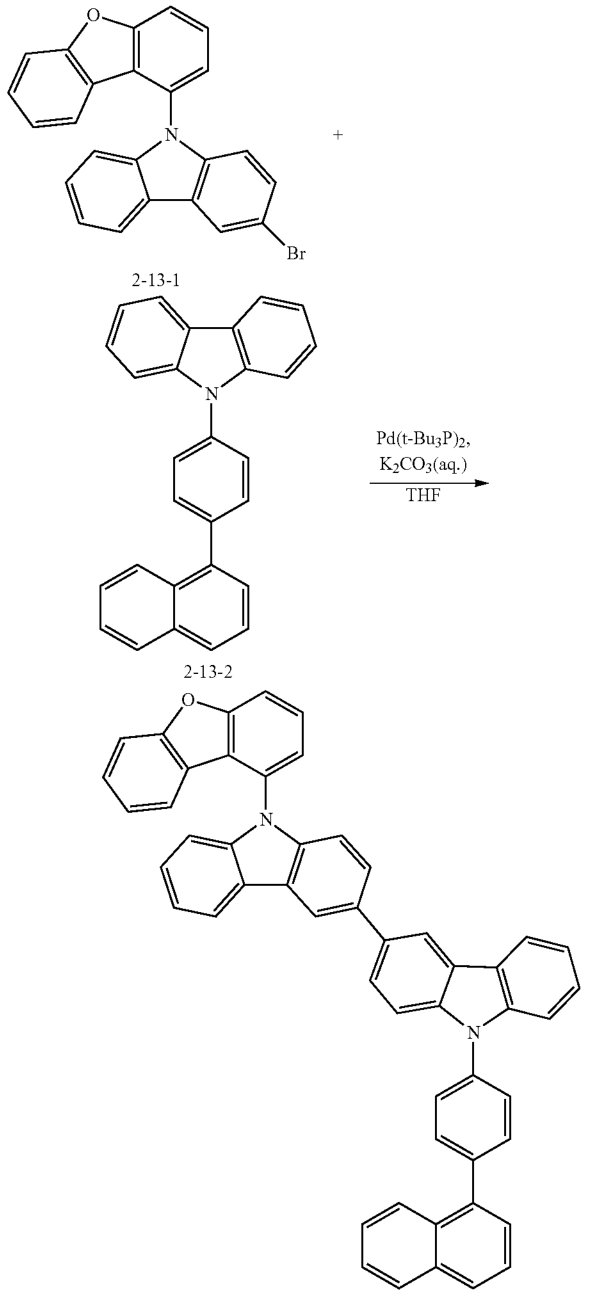

2-13-1

2-13-2

2-13

Intermediate 2-13-1 (10 g, 24.3 mmol) and Intermediate 2-13-2 (11.1 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9 g of Compound 2-13. (Yield: 53%, MS: [M+H]+=701)

Synthesis Example 2-14: Preparation of Compound 2-14

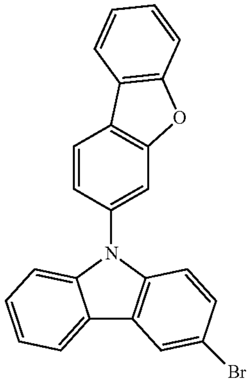

2-14-1

+

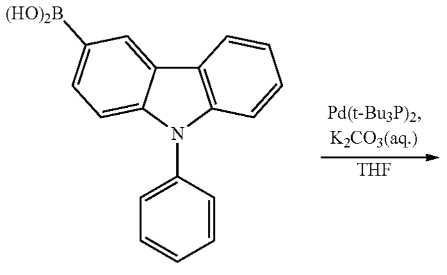

2-14-2

-continued

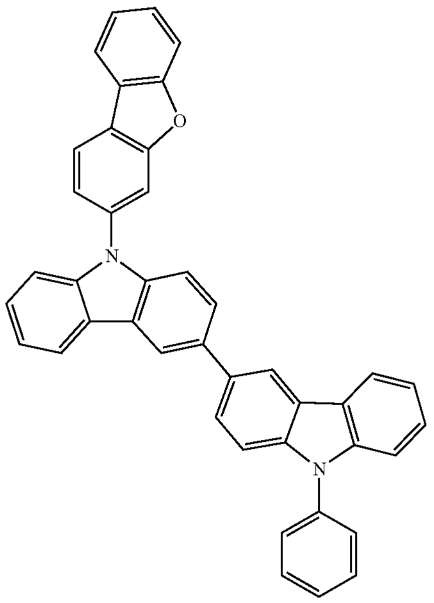

2-14

Intermediate 2-14-1 (10 g, 24.3 mmol) and Intermediate 2-14-2 (7.7 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 8.9 g of Compound 2-14. (Yield: 64%, MS: [M+H]+=575)

Synthesis Example 2-15: Preparation of Compound 2-15

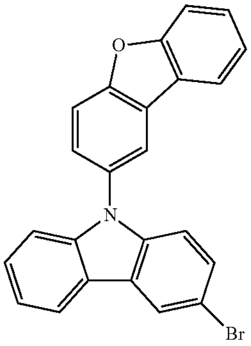

2-15-1

+

-continued

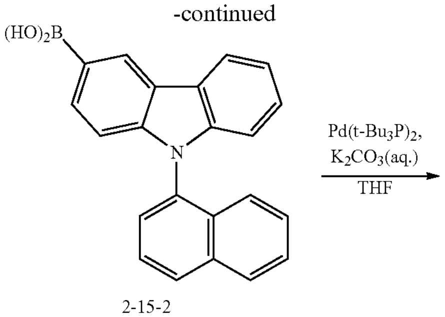

2-15-2

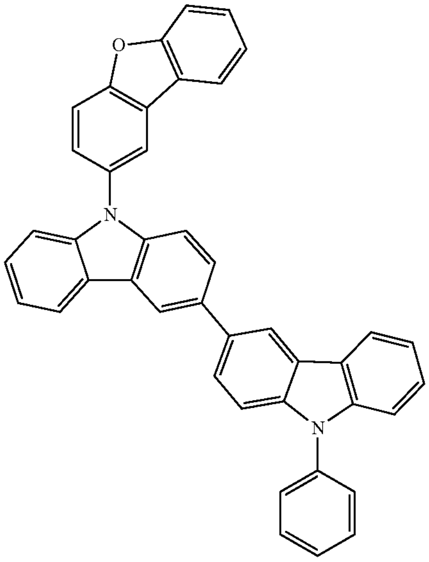

2-15

Intermediate 2-15-1 (10 g, 24.3 mmol) and Intermediate 2-15-2 (9 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 8.4 g of Compound 2-15. (Yield: 55%, MS: [M+H]+=625)

Synthesis Example 2-16: Preparation of Compound 2-16

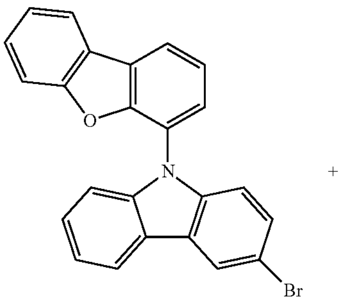

2-16-1

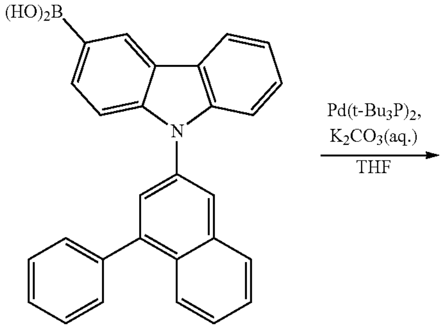

2-16-2

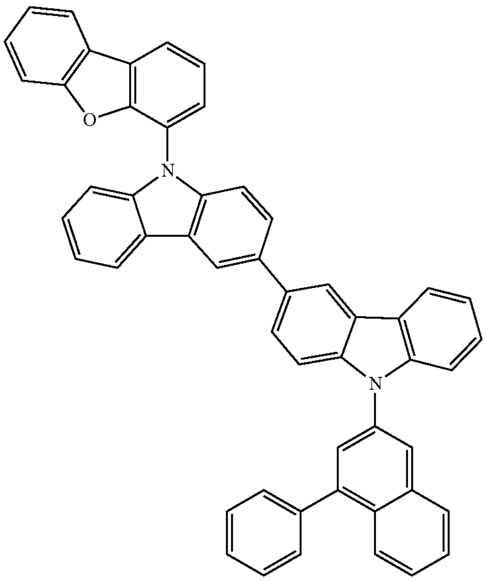

2-16

Intermediate 2-16-1 (10 g, 24.3 mmol) and Intermediate 2-16-2 (11.1 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 11.2 g of Compound 2-16. (Yield: 66%, MS: [M+M]+=701)

Synthesis Example 2-17: Preparation of Compound 2-17

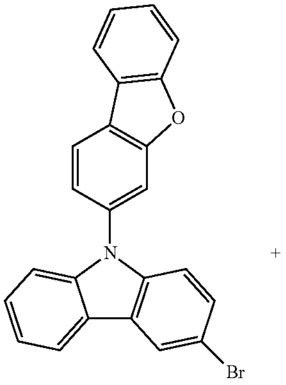

2-17-1

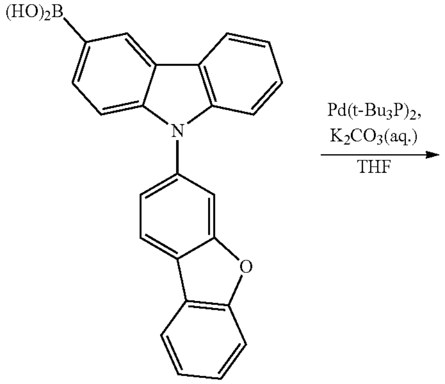

2-17-2

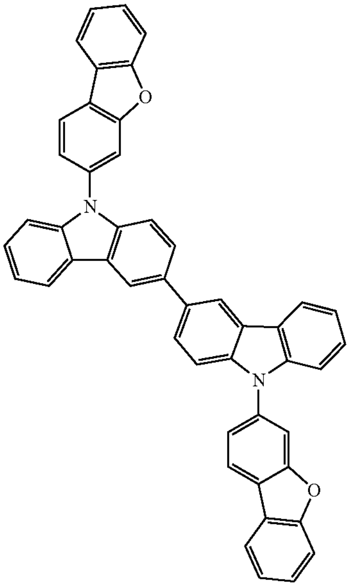

2-17

Intermediate 2-17-1 (10 g, 24.3 mmol) and Intermediate 2-17-2 (10.1 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10 g of Compound 2-17. (Yield: 62%, MS: [M+H]+=665)

Synthesis Example 2-18: Preparation of Compound 2-18

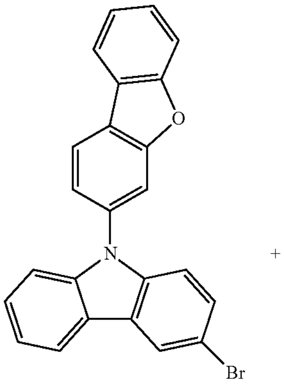

2-18-1

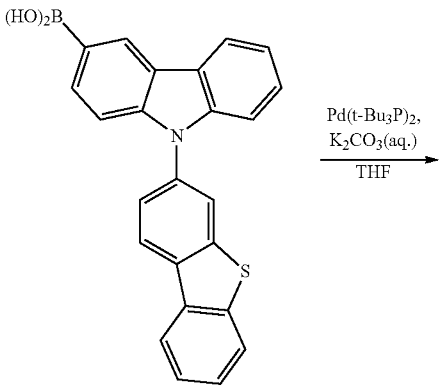

2-18-2

-continued

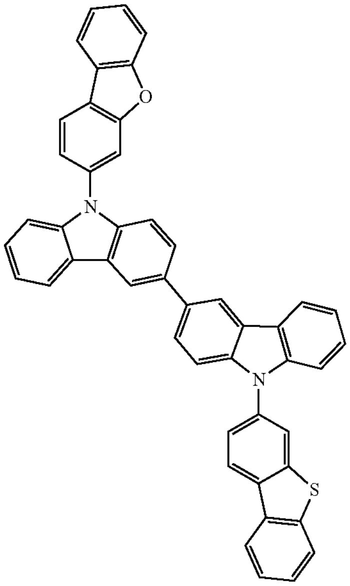

2-18

Intermediate 2-18-1 (10 g, 24.3 mmol) and Intermediate 2-18-2 (10.5 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9.8 g of Compound 2-18. (Yield: 59%, MS: [M+H]+=681)

Synthesis Example 2-19: Preparation of Compound 2-19

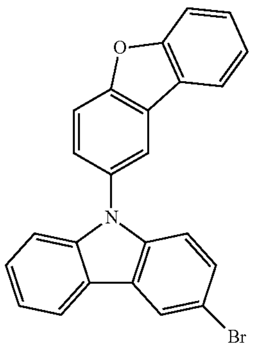

2-19-1

+

-continued

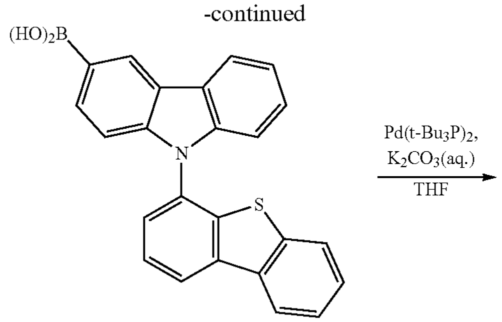

2-19-2

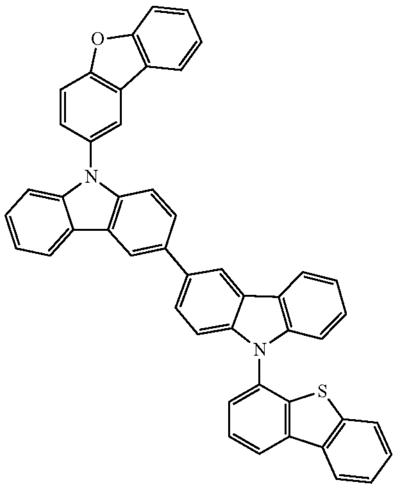

2-19

Intermediate 2-19-1 (10 g, 24.3 mmol) and Intermediate 2-19-2 (10.5 g, 26.8 mmol) were added to 200 ml of THF under a nitrogen atmosphere, stirred, and potassium carbonate (13.5 g, 97.3 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 11.4 g of Compound 2-19. (Yield: 69%, MS: [M+H]+=681)

Synthesis Example 2-20: Preparation of Compound 2-20

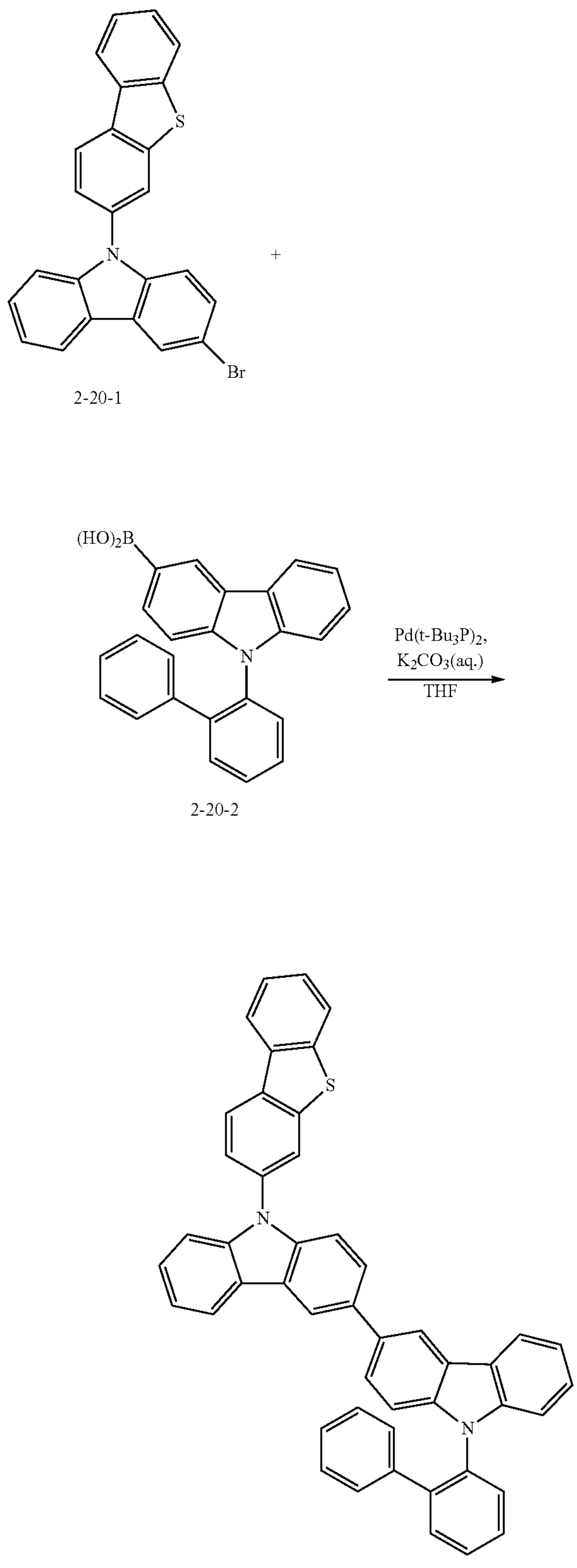

2-20-1

2-20-2

2-20

Intermediate 2-20-1 (10 g, 23.4 mmol) and Intermediate 2-20-2 (9.4 g, 25.8 mmol) were added to 200 ml of THF under a nitrogen atmosphere, stirred, and potassium carbonate (12.9 g, 93.7 mmol) was dissolved in water and added thereto. The mixture was sufficiently stirred and refluxed, and then bis(tri-tert-butylphosphine)palladium(0) (0.1 g, 0.2 mmol) was added. After the reaction for 2 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9 g of Compound 2-20. (Yield: 58%, MS: [M+H]+=667)

Synthesis Example 2-21: Preparation of Compound 2-21

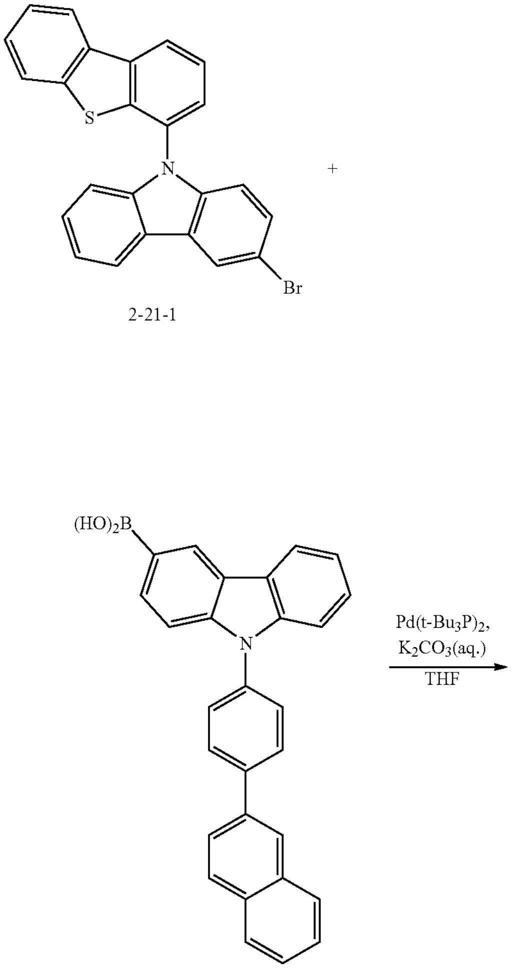

2-21-1

2-21-2

-continued

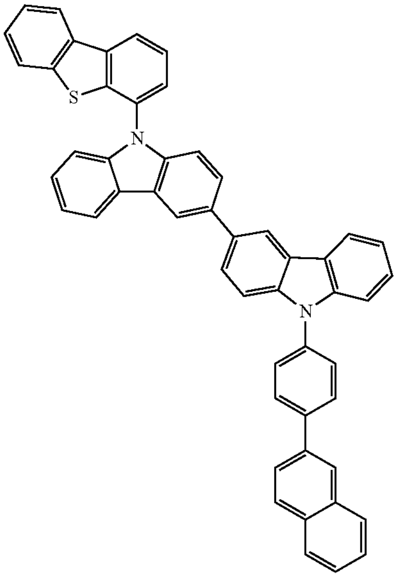

2-21

Intermediate 2-21-1 (10 g, 23.4 mmol) and Intermediate 2-21-2 (10.6 g, 25.8 mmol) were added to 200 ml of THF under a nitrogen atmosphere, stirred, and potassium carbonate (12.9 g, 93.7 mmol) was dissolved in water and added thereto. The mixture was sufficiently stirred and refluxed, and then bis(tri-tert-butylphosphine)palladium(0) (0.1 g, 0.2 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 10.7 g of Compound 2-21. (Yield: 64%, MS: [M+H]+=717)

Synthesis Example 2-22: Preparation of Compound 2-22

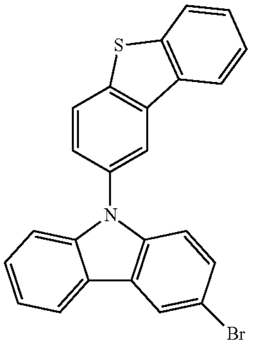

2-22-1

+

-continued

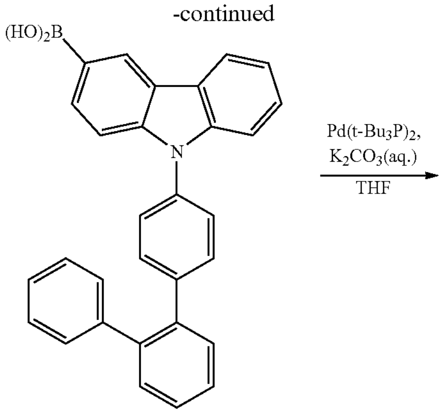

2-22-2

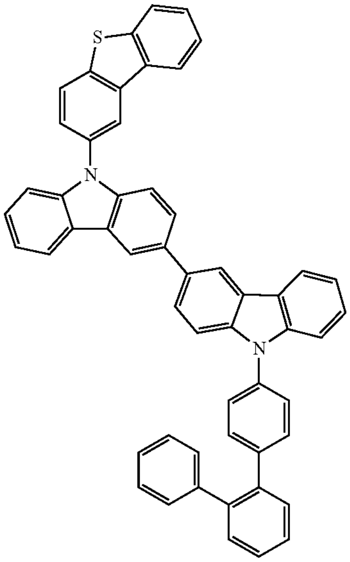

2-22

Intermediate 2-22-1 (10 g, 23.4 mmol) and Intermediate 2-22-2 (11.3 g, 25.8 mmol) were added to 200 ml of THF under a nitrogen atmosphere, stirred, and potassium carbonate (12.9 g, 93.7 mmol) was dissolved in water and added thereto. The mixture was sufficiently stirred and refluxed, and then bis(tri-tert-butylphosphine)palladium(0) (0.1 g, 0.2 mmol) was added. After the reaction for 3 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9 g of Compound 2-22. (Yield: 52%, MS: [M+H]+=743)

Synthesis Example 2-23: Preparation of Compound 2-23

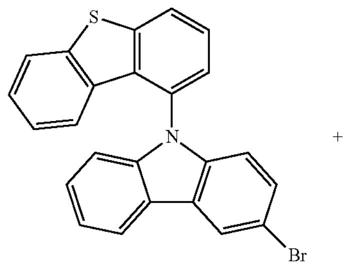

2-23-1

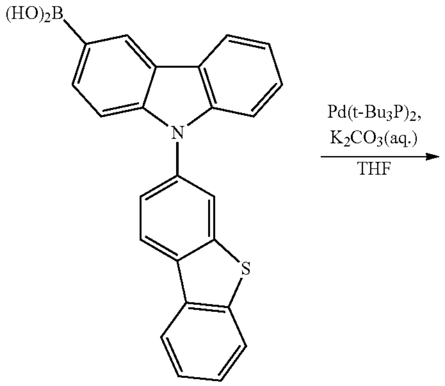

2-23-2

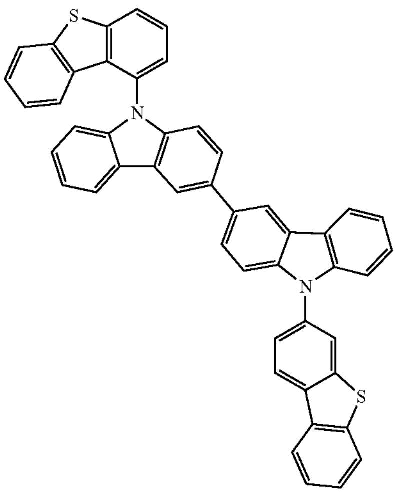

2-23

Intermediate 2-23-1 (10 g, 23.4 mmol) and Intermediate 2-23-2 (10.1 g, 25.8 mmol) were added to 200 ml of THF under a nitrogen atmosphere, stirred, and potassium carbonate (12.9 g, 93.7 mmol) was dissolved in water and added thereto. The mixture was sufficiently stirred and refluxed, and then bis(tri-tert-butylphosphine)palladium(0) (0.1 g, 0.2 mmol) was added. After the reaction for 4 hours, the reaction mixture was cooled to room temperature, the organic layer and the aqueous layer were separated and then the organic layer was distilled. This was again dissolved in chloroform and washed twice with water. The organic layer was then separated, anhydrous magnesium sulfate was added, stirred and then filtered. The filtrate was distilled under reduced pressure. The concentrated compound was purified by silica gel column chromatography to give 9.1 g of Compound 2-23. (Yield: 56%, MS: [M+H]+=697)

Comparative Example 1: Preparation of Organic Light Emitting

Device A glass substrate on which ITO (indium tin oxide) was coated as a thin film to a thickness of 1,000 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound HI-1 below was formed as a hole injection layer in a thickness of 1150 Å, wherein a compound A-1 below was p-doped at a concentration of 1.5%. A compound HT-1 below was vacuum-deposited on the hole to form a hole transport layer with a film thickness of 800 Å. Then, a compound EB-1 below was vacuum-deposited in a thickness of 150 Å on the hole transport layer to form an electron blocking layer.

Then, the compound 1-1 prepared in Preparation Example 1-1 and a compound Dp-7 below were vacuum-deposited at a weight ratio of 98:2 on the EB-1 deposition film to form red light emitting layer with a thickness of 400 Å.

A compound HB-1 below was vacuum-deposited on the light emitting layer in a film thickness of 30 Å to form a hole blocking layer. Then, a compound ET-1 below and a compound LiQ below were vacuum deposited on the hole blocking layer in a weight ratio of 2:1 to form an electron injection and transport layer with a thickness of 300 Å. Lithium fluoride (LiF) and aluminum were sequentially deposited to have a thickness of 12 Å and 1,000 Å, respectively, on the electron injection and transport layer, thereby forming a cathode.

HI-1
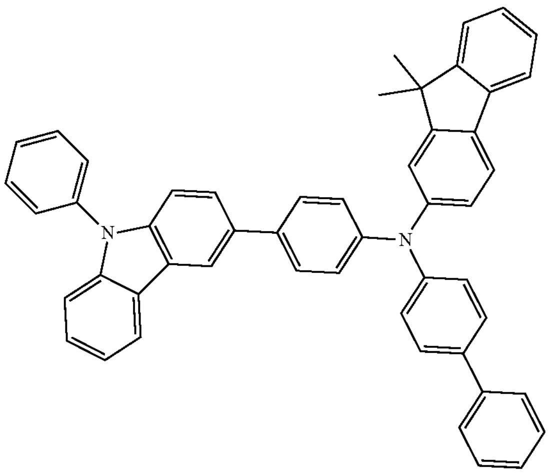
A-1
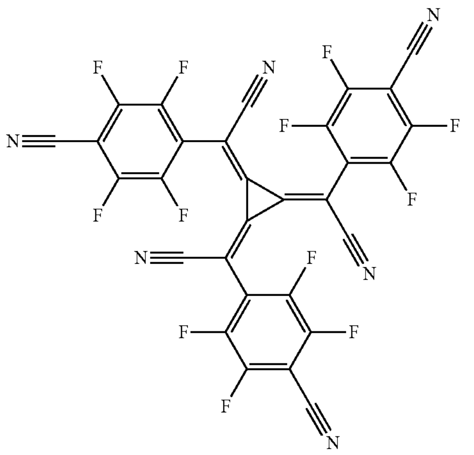
HT-1
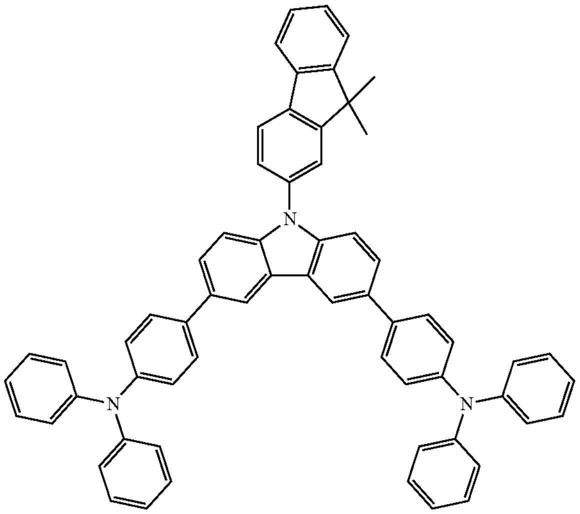

-continued
EB-1
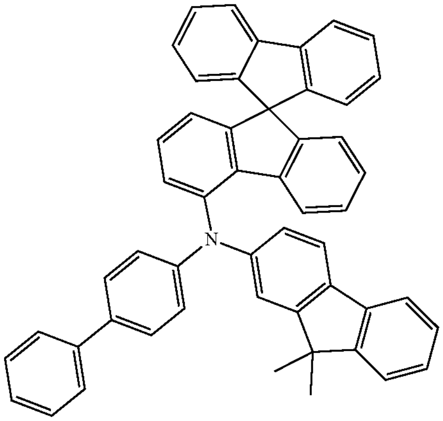
1-1
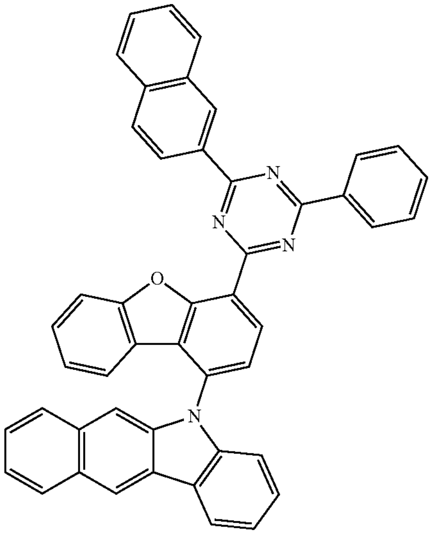
Dp-7
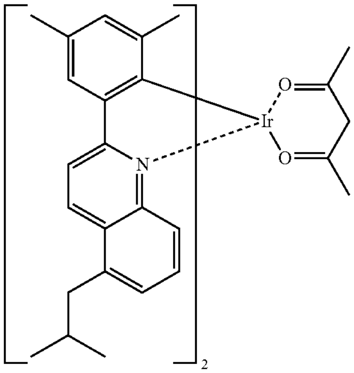

-continued

HB-1

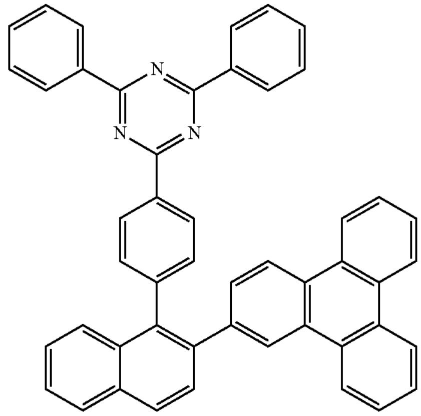

ET-1

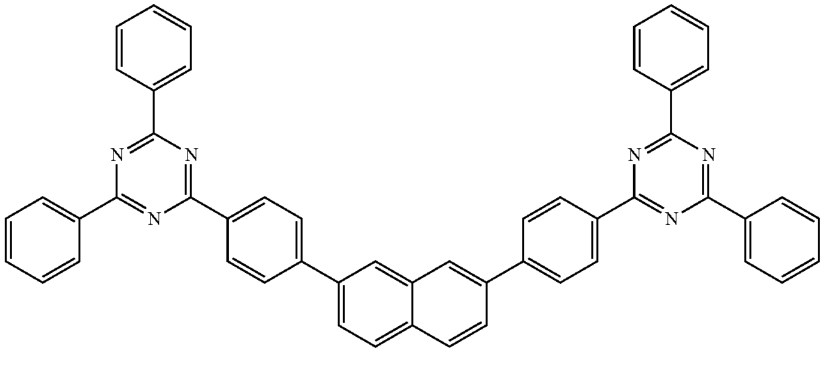

LiQ

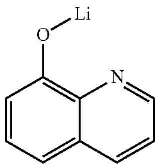

In the above-mentioned process, the vapor deposition rate of the organic material was maintained at 0.4 to 0.7 Å/sec, the deposition rate of lithium fluoride of the cathode was maintained at 0.3 Å/sec, the deposition rate of aluminum was maintained at 2 Å/sec, and the degree of vacuum during the deposition was maintained at $2\times10^{-7}$ to $5\times10^{-6}$ torr, thereby manufacturing the organic light emitting device.

Comparative Examples 2 to 15

An organic light emitting device was manufactured in the same manner as in Comparative Example 1, except that the compounds shown in Table 1 below were used instead of Compound 1-1 in the organic light emitting device of Comparative Example 1.

Examples 1 to 132

An organic light emitting device was manufactured in the same manner as in Comparative Example 1, except that a compound of Chemical Formula 1 as the first host and a compound of Chemical Formula 2 as the second host as shown in Tables 2 to 5 below were co-deposited and used at a weight ratio of 1:1, instead of Compound 1-1 in the organic light emitting device of Comparative Example 1.

Comparative Examples 16 to 63

An organic light emitting device was manufactured in the same manner as in Comparative Example 1, except that comparative compounds C-1 to C-12 as the first host and a compound of Chemical Formula 2 as the second host as shown in Tables 6 and 7 below were co-deposited and used at a weight ratio of 1:1, instead of Compound 1-1 in the organic light emitting device of Comparative Example 1.

-continued
C-1
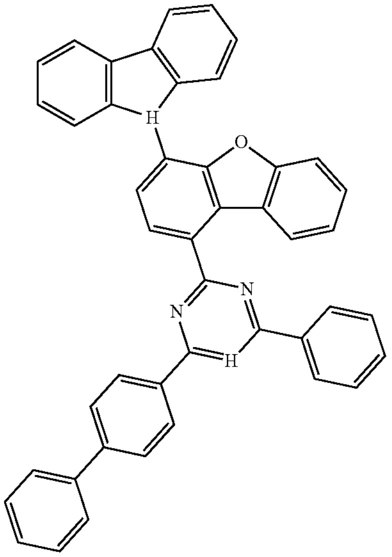
C-2
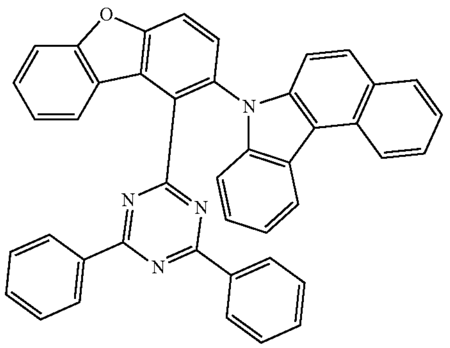
C-3
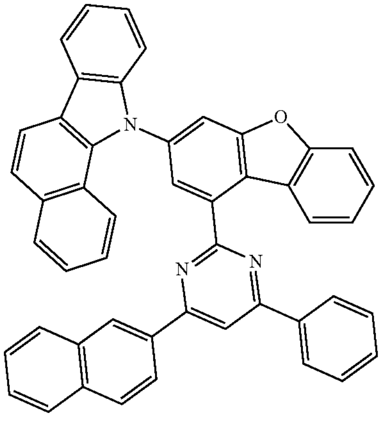
C-4
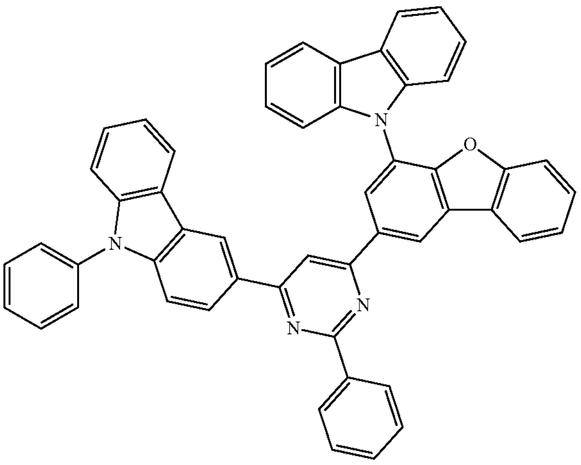
C-5
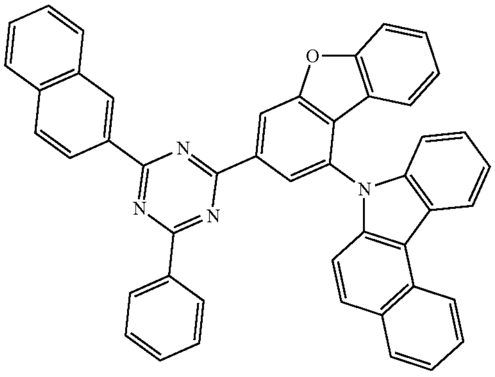
C-6
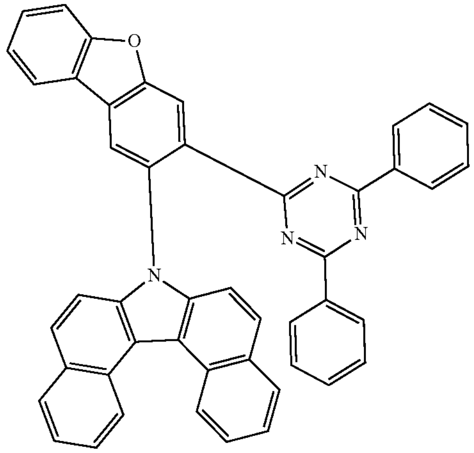

-continued
C-7
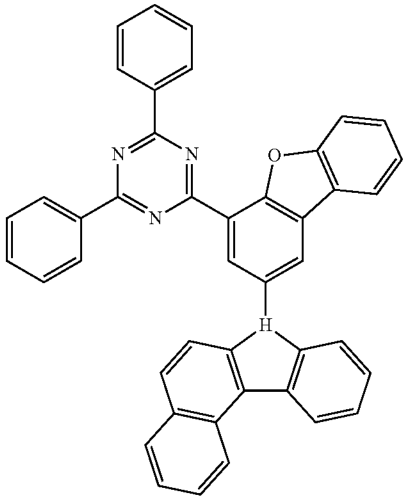
C-8
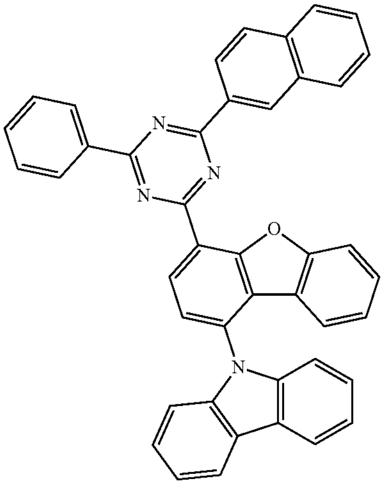
C-9
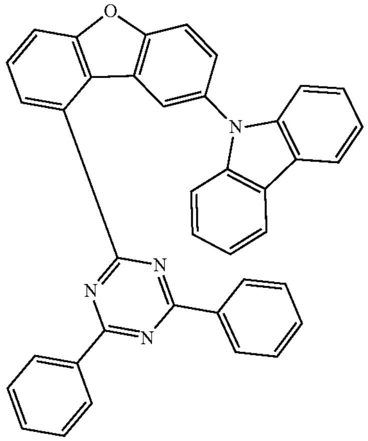
-continued
C-10
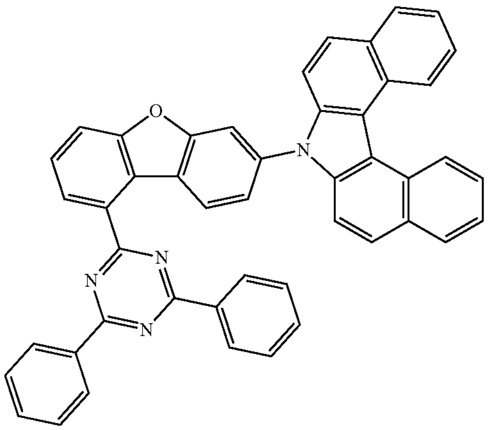
C-11
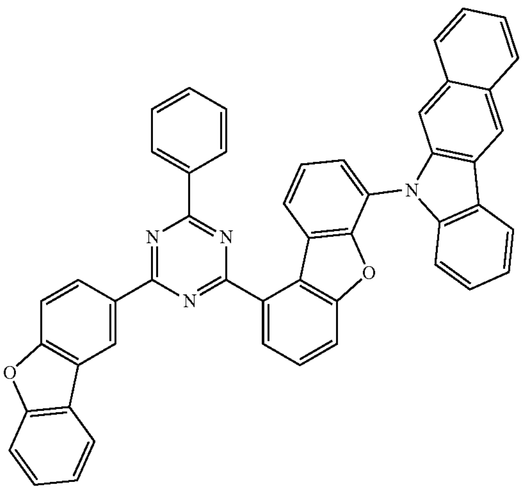
C-12
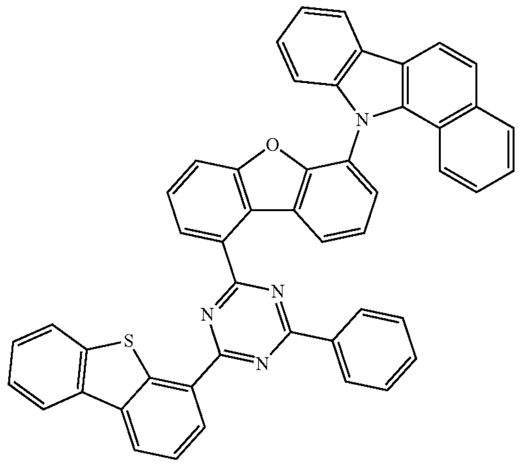
Experimental Example 1: Evaluation of Device Characteristics
The voltage, efficiency and lifespan were measured (based on 15 mA/cm$^2$) by applying a current to the organic light emitting devices manufactured in the Examples 1 to 132 and Comparative Examples 1 to 63, and the results are shown in Tables 1 to 7 below. Lifespan T95 means the time required for the luminance to be reduced to 95% of the initial luminance (10,000 nit).

TABLE 1

| Category | Host | Driving voltage(V) | Efficiency(cd/A) | Lifespan T95(hr) | Light emitting color |
|---|---|---|---|---|---|
| Comparative Example 1 | Compound 1-1 | 3.73 | 17.2 | 162 | Red |
| Comparative Example 2 | Compound 1-2 | 3.62 | 17.8 | 157 | Red |
| Comparative Example 3 | Compound 1-3 | 3.68 | 18.6 | 163 | Red |
| Comparative Example 4 | Compound 1-9 | 3.86 | 17.4 | 168 | Red |
| Comparative Example 5 | Compound 1-10 | 3.82 | 17.0 | 164 | Red |
| Comparative Example 6 | Compound 1-11 | 3.84 | 17.9 | 160 | Red |
| Comparative Example 7 | Compound 1-19 | 3.92 | 17.7 | 164 | Red |
| Comparative Example 8 | Compound 1-21 | 3.88 | 17.0 | 158 | Red |
| Comparative Example 9 | Compound 1-22 | 3.95 | 17.5 | 155 | Red |
| Comparative Example 10 | Compound 1-34 | 3.69 | 18.5 | 161 | Red |
| Comparative Example 11 | Compound 1-35 | 3.72 | 18.1 | 178 | Red |
| Comparative Example 12 | Compound 1-36 | 3.58 | 18.0 | 184 | Red |
| Comparative Example 13 | Compound 1-41 | 3.53 | 18.5 | 183 | Red |
| Comparative Example 14 | Compound 1-44 | 3.71 | 19.1 | 187 | Red |
| Comparative Example 15 | Compound 1-48 | 3.51 | 18.7 | 181 | Red |

TABLE 2

| Category | First host | Second host | Driving voltage(V) | Efficiency (cd/A) | Lifespan T95(hr) | Light emitting color |
|---|---|---|---|---|---|---|
| Example 1 | Compound 1-1 | Compound 2-1 | 3.76 | 21.5 | 263 | Red |
| Example 2 | | Compound 2-2 | 3.78 | 21.2 | 247 | Red |
| Example 3 | | Compound 2-8 | 3.77 | 21.9 | 238 | Red |
| Example 4 | | Compound 2-19 | 3.76 | 21.4 | 245 | Red |
| Example 5 | Compound 1-2 | Compound 2-1 | 3.68 | 20.4 | 243 | Red |
| Example 6 | | Compound 2-2 | 3.71 | 21.3 | 236 | Red |
| Example 7 | | Compound 2-8 | 3.70 | 20.7 | 227 | Red |
| Example 8 | | Compound 2-19 | 3.72 | 20.5 | 241 | Red |
| Example 8 | Compound 1-3 | Compound 2-1 | 3.78 | 20.4 | 233 | Red |
| Example 10 | | Compound 2-2 | 3.72 | 20.8 | 242 | Red |
| Example 11 | | Compound 2-8 | 3.74 | 20.9 | 237 | Red |
| Example 12 | | Compound 2-19 | 3.76 | 21.4 | 251 | Red |
| Example 13 | Compound 1-5 | Compound 2-1 | 3.65 | 20.1 | 233 | Red |
| Example 14 | | Compound 2-2 | 3.70 | 22.3 | 239 | Red |
| Example 15 | | Compound 2-8 | 3.74 | 20.4 | 247 | Red |
| Example 16 | | Compound 2-19 | 3.73 | 21.5 | 231 | Red |
| Example 17 | Compound 1-7 | Compound 2-1 | 3.75 | 21.1 | 233 | Red |
| Example 18 | | Compound 2-2 | 3.71 | 20.3 | 247 | Red |
| Example 19 | | Compound 2-8 | 3.70 | 21.8 | 252 | Red |
| Example 20 | | Compound 2-19 | 3.78 | 21.6 | 243 | Red |
| Example 21 | Compound 1-8 | Compound 2-1 | 3.77 | 20.1 | 213 | Red |
| Example 22 | | Compound 2-2 | 3.76 | 20.5 | 215 | Red |
| Example 23 | | Compound 2-8 | 3.81 | 21.2 | 201 | Red |
| Example 24 | | Compound 2-19 | 3.84 | 21.1 | 217 | Red |
| Example 25 | Compound 1-9 | Compound 2-1 | 3.89 | 20.3 | 208 | Red |
| Example 26 | | Compound 2-2 | 3.92 | 21.2 | 221 | Red |
| Example 27 | | Compound 2-8 | 3.91 | 21.7 | 213 | Red |
| Example 28 | | Compound 2-19 | 3.95 | 20.8 | 204 | Red |
| Example 29 | Compound 1-10 | Compound 2-1 | 3.88 | 19.9 | 221 | Red |
| Example 30 | | Compound 2-2 | 3.85 | 20.1 | 216 | Red |
| Example 31 | | Compound 2-8 | 3.92 | 20.9 | 220 | Red |
| Example 32 | | Compound 2-19 | 3.96 | 21.4 | 209 | Red |

TABLE 2-continued

| Category | First host | Second host | Driving voltage(V) | Efficiency (cd/A) | Lifespan T95(hr) | Light emitting color |
|---|---|---|---|---|---|---|
| Example 33 | Compound 1-13 | Compound 2-1 | 3.90 | 19.7 | 211 | Red |
| Example 34 | | Compound 2-2 | 3.91 | 20.5 | 204 | Red |
| Example 35 | | Compound 2-8 | 3.84 | 20.3 | 207 | Red |
| Example 36 | | Compound 2-19 | 3.93 | 20.7 | 198 | Red |
| Example 37 | Compound 1-15 | Compound 2-1 | 3.94 | 19.1 | 211 | Red |
| Example 38 | | Compound 2-2 | 3.91 | 20.1 | 218 | Red |
| Example 39 | | Compound 2-8 | 3.97 | 20.0 | 213 | Red |
| Example 40 | | Compound 2-19 | 3.90 | 20.3 | 204 | Red |

TABLE 3

| Category | First host | Second host | Driving voltage(V) | Efficiency (cd/A) | Lifespan T95(hr) | Light emitting color |
|---|---|---|---|---|---|---|
| Example 41 | Compound | Compound 2-1 | 3.89 | 19.9 | 192 | Red |
| Example 42 | 1-18 | Compound 2-2 | 3.87 | 20.3 | 203 | Red |
| Example 43 | | Compound 2-8 | 3.90 | 20.9 | 211 | Red |
| Example 44 | | Compound 2-19 | 3.99 | 20.4 | 184 | Red |
| Example 45 | Compound | Compound 2-9 | 3.95 | 21.7 | 191 | Red |
| Example 46 | 1-19 | Compound 2-10 | 3.99 | 21.3 | 192 | Red |
| Example 47 | | Compound 2-12 | 4.02 | 20.1 | 198 | Red |
| Example 48 | | Compound 2-16 | 4.00 | 20.9 | 203 | Red |
| Example 49 | Compound | Compound 2-9 | 3.92 | 21.5 | 191 | Red |
| Example 50 | 1-21 | Compound 2-10 | 3.91 | 20.3 | 194 | Red |
| Example 51 | | Compound 2-12 | 3.98 | 21.2 | 190 | Red |
| Example 52 | | Compound 2-16 | 4.01 | 20.5 | 198 | Red |
| Example 53 | Compound | Compound 2-9 | 3.97 | 20.5 | 191 | Red |
| Example 54 | 1-23 | Compound 2-10 | 4.03 | 21.8 | 198 | Red |
| Example 55 | | Compound 2-12 | 4.01 | 20.4 | 191 | Red |
| Example 56 | | Compound 2-16 | 4.05 | 20.1 | 199 | Red |
| Example 57 | Compound | Compound 2-9 | 3.98 | 20.0 | 196 | Red |
| Example 58 | 1-24 | Compound 2-10 | 4.05 | 20.2 | 198 | Red |
| Example 59 | | Compound 2-12 | 4.07 | 20.0 | 204 | Red |
| Example 60 | | Compound 2-16 | 4.04 | 20.3 | 192 | Red |
| Example 61 | Compound | Compound 2-9 | 3.91 | 20.8 | 201 | Red |
| Example 62 | 1-26 | Compound 2-10 | 3.98 | 20.1 | 194 | Red |
| Example 63 | | Compound 2-12 | 3.84 | 20.4 | 193 | Red |
| Example 64 | | Compound 2-16 | 3.90 | 20.2 | 208 | Red |
| Example 65 | Compound | Compound 2-9 | 3.94 | 20.8 | 203 | Red |
| Example 66 | 1-27 | Compound 2-10 | 4.02 | 20.1 | 205 | Red |
| Example 67 | | Compound 2-12 | 4.05 | 20.4 | 199 | Red |
| Example 68 | | Compound 2-16 | 3.96 | 21.2 | 211 | Red |
| Example 69 | Compound | Compound 2-9 | 3.90 | 21.3 | 195 | Red |
| Example 70 | 1-29 | Compound 2-10 | 4.01 | 20.5 | 191 | Red |
| Example 71 | | Compound 2-12 | 3.88 | 20.2 | 204 | Red |
| Example 72 | | Compound 2-16 | 4.05 | 20.4 | 208 | Red |
| Example 73 | Compound | Compound 2-9 | 3.81 | 20.7 | 195 | Red |
| Example 74 | 1-32 | Compound 2-10 | 3.84 | 20.1 | 183 | Red |
| Example 75 | | Compound 2-12 | 3.80 | 20.7 | 201 | Red |
| Example 76 | | Compound 2-16 | 3.92 | 21.0 | 199 | Red |
| Example 77 | Compound | Compound 2-9 | 3.79 | 20.0 | 205 | Red |
| Example 78 | 1-33 | Compound 2-10 | 3.81 | 21.5 | 191 | Red |
| Example 79 | | Compound 2-12 | 3.85 | 20.4 | 208 | Red |
| Example 80 | | Compound 2-16 | 3.88 | 20.8 | 214 | Red |

TABLE 4

| Category | First host | Second host | Driving voltage(V) | Efficiency (cd/A) | Lifespan T95(hr) | Light emitting color |
|---|---|---|---|---|---|---|
| Example 81 | Compound | Compound 2-3 | 3.74 | 21.5 | 257 | Red |
| Example 82 | 1-34 | Compound 2-4 | 3.78 | 23.0 | 242 | Red |
| Example 83 | | Compound 2-14 | 3.72 | 24.4 | 263 | Red |
| Example 84 | | Compound 2-21 | 3.75 | 21.8 | 254 | Red |
| Example 85 | Compound | Compound 2-3 | 3.78 | 23.1 | 274 | Red |
| Example 86 | 1-35 | Compound 2-4 | 3.80 | 22.8 | 283 | Red |
| Example 87 | | Compound 2-14 | 3.84 | 22.6 | 270 | Red |
| Example 88 | | Compound 2-21 | 3.81 | 22.7 | 291 | Red |
| Example 89 | Compound | Compound 2-3 | 3.61 | 25.8 | 259 | Red |

TABLE 4-continued

| Category | First host | Second host | Driving voltage(V) | Efficiency (cd/A) | Lifespan T95(hr) | Light emitting color |
|---|---|---|---|---|---|---|
| Example 90 | 1-36 | Compound 2-4 | 3.60 | 24.9 | 247 | Red |
| Example 91 | | Compound 2-14 | 3.63 | 25.0 | 239 | Red |
| Example 92 | | Compound 2-21 | 3.61 | 25.4 | 250 | Red |
| Example 93 | Compound | Compound 2-3 | 3.73 | 23.6 | 247 | Red |
| Example 94 | 1-38 | Compound 2-4 | 3.76 | 22.8 | 237 | Red |
| Example 95 | | Compound 2-14 | 3.74 | 24.7 | 253 | Red |
| Example 96 | | Compound 2-21 | 3.73 | 21.4 | 238 | Red |
| Example 97 | Compound | Compound 2-3 | 3.60 | 23.8 | 257 | Red |
| Example 98 | 1-39 | Compound 2-4 | 3.61 | 23.1 | 210 | Red |
| Example 99 | | Compound 2-14 | 3.60 | 24.3 | 243 | Red |
| Example 100 | | Compound 2-21 | 3.53 | 22.4 | 258 | Red |
| Example 101 | Compound | Compound 2-3 | 3.76 | 23.3 | 283 | Red |
| Example 102 | 1-40 | Compound 2-4 | 3.77 | 22.9 | 289 | Red |
| Example 103 | | Compound 2-14 | 3.81 | 22.8 | 278 | Red |
| Example 104 | | Compound 2-21 | 3.80 | 23.2 | 308 | Red |
| Example 105 | Compound | Compound 2-3 | 3.55 | 26.5 | 273 | Red |
| Example 106 | 1-41 | Compound 2-4 | 3.57 | 26.3 | 264 | Red |
| Example 107 | | Compound 2-14 | 3.54 | 26.9 | 268 | Red |
| Example 108 | | Compound 2-21 | 3.90 | 25.8 | 241 | Red |
| Example 109 | Compound | Compound 2-3 | 3.79 | 23.0 | 205 | Red |
| Example 110 | 1-43 | Compound 2-4 | 3.82 | 21.7 | 212 | Red |
| Example 111 | | Compound 2-14 | 3.90 | 21.4 | 203 | Red |
| Example 112 | | Compound 2-21 | 3.94 | 20.8 | 211 | Red |
| Example 113 | Compound | Compound 2-3 | 3.77 | 24.1 | 243 | Red |
| Example 114 | 1-45 | Compound 2-4 | 3.81 | 23.4 | 290 | Red |
| Example 115 | | Compound 2-14 | 3.85 | 24.5 | 303 | Red |
| Example 116 | | Compound 2-21 | 3.80 | 23.9 | 317 | Red |
| Example 117 | Compound | Compound 2-3 | 3.63 | 25.1 | 279 | Red |
| Example 118 | 1-46 | Compound 2-4 | 3.61 | 24.5 | 261 | Red |
| Example 119 | | Compound 2-14 | 3.60 | 25.1 | 264 | Red |
| Example 120 | | Compound 2-21 | 3.65 | 25.3 | 268 | Red |

TABLE 5

| Category | First host | Second host | Driving voltage(V) | Efficiency (cd/A) | Lifespan T95(hr) | Light emitting color |
|---|---|---|---|---|---|---|
| Example 121 | Compound | Compound 2-3 | 3.56 | 25.7 | 294 | Red |
| Example 122 | 1-48 | Compound 2-4 | 3.58 | 25.8 | 293 | Red |
| Example 123 | | Compound 2-14 | 3.61 | 26.1 | 303 | Red |
| Example 124 | | Compound 2-21 | 3.60 | 25.6 | 307 | Red |
| Example 125 | Compound | Compound 2-3 | 3.73 | 23.7 | 238 | Red |
| Example 126 | 1-49 | Compound 2-4 | 3.77 | 23.1 | 220 | Red |
| Example 127 | | Compound 2-14 | 3.69 | 24.4 | 241 | Red |
| Example 128 | | Compound 2-21 | 3.71 | 23.8 | 237 | Red |
| Example 129 | Compound | Compound 2-3 | 3.60 | 26.8 | 249 | Red |
| Example 130 | 1-50 | Compound 2-4 | 3.62 | 26.1 | 244 | Red |
| Example 131 | | Compound 2-14 | 3.61 | 26.4 | 248 | Red |
| Example 132 | | Compound 2-21 | 3.65 | 25.0 | 250 | Red |

TABLE 6

| Category | First host | Second host | Driving voltage(V) | Efficiency (cd/A) | Lifespan T95(hr) | Light emitting color |
|---|---|---|---|---|---|---|
| Comparative Example 16 | Compound C-1 | Compound 2-1 | 4.25 | 14.1 | 131 | Red |
| Comparative Example 17 | | Compound 2-2 | 4.24 | 14.3 | 133 | Red |
| Comparative Example 18 | | Compound 2-8 | 4.22 | 15.8 | 137 | Red |
| Comparative Example 19 | | Compound 2-19 | 4.23 | 15.5 | 132 | Red |
| Comparative Example 20 | Compound C-2 | Compound 2-1 | 4.20 | 15.0 | 144 | Red |
| Comparative Example 21 | | Compound 2-2 | 4.22 | 15.7 | 133 | Red |
| Comparative Example 22 | | Compound 2-8 | 4.25 | 15.2 | 144 | Red |

TABLE 6-continued

| Category | First host | Second host | Driving voltage(V) | Efficiency (cd/A) | Lifespan T95(hr) | Light emitting color |
|---|---|---|---|---|---|---|
| Comparative Example 23 | | Compound 2-19 | 4.21 | 15.4 | 137 | Red |
| Comparative Example 24 | Compound C-3 | Compound 2-1 | 4.21 | 16.2 | 138 | Red |
| Comparative Example 25 | | Compound 2-2 | 4.23 | 15.8 | 127 | Red |
| Comparative Example 26 | | Compound 2-8 | 4.22 | 15.4 | 121 | Red |
| Comparative Example 27 | | Compound 2-19 | 4.08 | 15.0 | 134 | Red |
| Comparative Example 28 | Compound C-4 | Compound 2-1 | 4.05 | 15.8 | 125 | Red |
| Comparative Example 29 | | Compound 2-2 | 4.04 | 15.5 | 113 | Red |
| Comparative Example 30 | | Compound 2-8 | 4.17 | 15.2 | 111 | Red |
| Comparative Example 31 | | Compound 2-19 | 4.10 | 14.3 | 119 | Red |
| Comparative Example 32 | Compound C-5 | Compound 2-9 | 4.23 | 15.0 | 128 | Red |
| Comparative Example 33 | | Compound 2-10 | 4.10 | 13.8 | 123 | Red |
| Comparative Example 34 | | Compound 2-12 | 4.17 | 15.1 | 120 | Red |
| Comparative Example 35 | | Compound 2-16 | 4.12 | 14.5 | 111 | Red |
| Comparative Example 36 | Compound C-6 | Compound 2-9 | 4.20 | 15.1 | 116 | Red |
| Comparative Example 37 | | Compound 2-10 | 4.25 | 15.4 | 120 | Red |
| Comparative Example 38 | | Compound 2-12 | 4.21 | 15.3 | 127 | Red |
| Comparative Example 39 | | Compound 2-16 | 4.18 | 14.0 | 104 | Red |
| Comparative Example 40 | Compound C-7 | Compound 2-9 | 4.12 | 13.6 | 119 | Red |
| Comparative Example 41 | | Compound 2-10 | 4.25 | 14.1 | 121 | Red |
| Comparative Example 42 | | Compound 2-12 | 4.13 | 15.5 | 115 | Red |
| Comparative Example 43 | | Compound 2-16 | 4.17 | 13.4 | 118 | Red |
| Comparative Example 44 | Compound C-8 | Compound 2-9 | 4.05 | 14.0 | 122 | Red |
| Comparative Example 45 | | Compound 2-10 | 4.03 | 13.4 | 118 | Red |
| Comparative Example 46 | | Compound 2-12 | 4.08 | 13.1 | 125 | Red |
| Comparative Example 47 | | Compound 2-16 | 4.09 | 14.2 | 111 | Red |
| Comparative Example 48 | Compound C-9 | Compound 2-3 | 4.11 | 13.5 | 117 | Red |
| Comparative Example 49 | | Compound 2-4 | 4.13 | 15.9 | 119 | Red |
| Comparative Example 50 | | Compound 2-14 | 4.15 | 15.3 | 117 | Red |
| Comparative Example 51 | | Compound 2-21 | 4.14 | 14.5 | 110 | Red |
| Comparative Example 52 | Compound C-10 | Compound 2-3 | 4.06 | 15.3 | 127 | Red |
| Comparative Example 53 | | Compound 2-4 | 4.09 | 16.0 | 131 | Red |
| Comparative Example 54 | | Compound 2-14 | 4.05 | 16.4 | 128 | Red |
| Comparative Example 55 | | Compound 2-21 | 4.02 | 16.1 | 120 | Red |

TABLE 7

| Category | First host | Second host | Driving voltage(V) | Efficiency (cd/A) | Lifespan T95(hr) | Light emitting color |
|---|---|---|---|---|---|---|
| Comparative Example 56 | Compound C-11 | Compound 2-3 | 4.11 | 16.0 | 121 | Red |
| Comparative Example 57 | | Compound 2-4 | 4.18 | 16.1 | 127 | Red |
| Comparative Example 58 | | Compound 2-14 | 4.21 | 17.3 | 138 | Red |
| Comparative Example 59 | | Compound 2-21 | 4.18 | 16.0 | 121 | Red |
| Comparative Example 60 | Compound C-12 | Compound 2-9 | 4.10 | 16.2 | 131 | Red |
| Comparative Example 61 | | Compound 2-10 | 4.11 | 15.5 | 129 | Red |
| Comparative Example 62 | | Compound 2-12 | 4.10 | 16.8 | 124 | Red |
| Comparative Example 63 | | Compound 2-16 | 4.14 | 15.9 | 136 | Red |

As shown in Tables above, the organic light emitting device of the Examples which simultaneously use the first compound represented by the Chemical Formula 1 and the second compound represented by the Chemical Formula 2 as the host material in the light emitting layer exhibited equivalent or superior emission efficiency, low driving voltage and significantly improved lifespan characteristics, as compared with the organic light emitting devices of the Comparative Examples which either employ only one of the compounds represented by the Chemical Formulae 1 and 2, or do not employ both of them.

Specifically, the devices according to the Examples exhibited high efficiency and long lifespan as compared with the devices of the Comparative Examples employing the compound represented by the Chemical Formula 1 as a single host. In addition, the devices according to the Examples exhibited improved efficiency and lifespan characteristics as compared with the devices of the Comparative Examples employing the Comparative compounds C-1 to C-12 as the first host and the compound represented by the Chemical Formula 2 as the second host. Thereby, when the combination of the first compound represented by Chemical Formula 1 and the second compound represented by Chemical Formula 2 was used as a co-host, it was confirmed that energy transfer to the red dopant was effectively performed in the red light emitting layer. This is considered to be because the first compound has high stability to electrons and holes, and also to be because using it in combination with the second compound increased the amount of holes and maintained a more stable balance between electrons and holes in the red light emitting layer.

Accordingly, when the first compound and the second compound are simultaneously employed as the host materials of the organic light emitting device, it was confirmed that the driving voltage, emission efficiency, and/or lifespan characteristics of the organic light emitting device can be improved. In consideration of the fact that the emission efficiency and lifespan characteristics of the organic light emitting device generally have a trade-off relationship with each other, this can be seen that the organic light emitting device employing the combination between the compounds of the present disclosure exhibits a significantly improved device characteristic as compared with the devices of the Comparative Examples.

| [Description of Reference Numerals] | |
|---|---|
| 1: substrate | 2: anode |
| 3: light emitting layer | 4: cathode |
| 5: hole injection layer | |
| 6: hole transport layer | |
| 7: electron blocking layer | |
| 8. hole blocking layer | |
| 9: electron injection and transport layer | |

The invention claimed is:

1. An organic light emitting device comprising:

a first electrode;

a second electrode provided to face the first electrode; and a light emitting layer provided between the first electrode and the second electrode, wherein the light emitting layer includes a first compound represented by Chemical Formula 1 and a second compound represented by Chemical Formula 2:

[Chemical Formula 1]

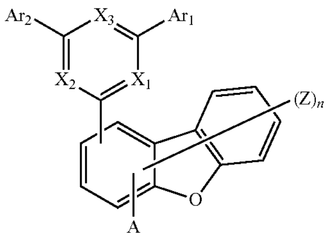

wherein, in Chemical Formula 1, $X_1$ to $X_3$ are each independently N or CH, and at least two of $X_1$ to $X_3$ are N, $A_1$ and $Ar_2$ are each independently deuterium; a substituted or unsubstituted $C_{6-60}$ aryl; or a substituted or unsubstituted $C_{2-60}$ heteroaryl containing any one or more heteroatoms selected from the group consisting of N, O and S, each Z is independently hydrogen or deuterium, or two adjacent groups of Zs may combine with each other to form a $C_{6-60}$ aromatic ring unsubstituted or substituted with deuterium; or to form a $C_{2-60}$ heteroaromatic ring unsubstituted or substituted with deuterium and containing any one or more heteroatoms selected from the group consisting of N, O and S, n is an integer from 0 to 6, and A is a substituent represented by Chemical Formula 1-1,

[Chemical Formula 1-1]

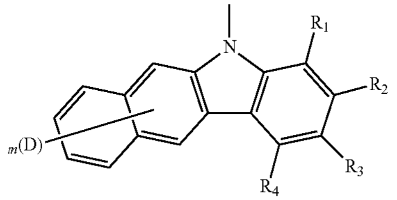

wherein, in Chemical Formula 1-1, $R_1$ to $R_4$ are each independently hydrogen or deuterium, or two adjacent groups of $R_1$ to $R_4$ combine with each other to form a $C_{6-60}$ aromatic ring unsubstituted or substituted with deuterium; or to form a $C_{2-60}$ heteroaromatic ring unsubstituted or substituted with deuterium and containing any one or more heteroatoms selected from the group consisting of N, O and S, D is deuterium, and m is an integer from 0 to 6,

[Chemical Formula 2]

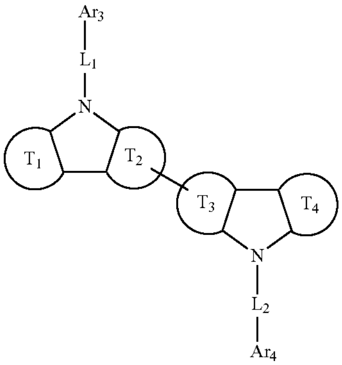

wherein, in Chemical Formula 2, $T_1$ to $T_4$ are each independently a substituted or unsubstituted $C_{6-60}$ aromatic ring; or a substituted or unsubstituted $C_{2-60}$ heteroaromatic ring containing any one or more heteroatoms selected from the group consisting of N, O and S, $L_1$ and $L_2$ are each independently a single bond; a substituted or unsubstituted $C_{6-60}$ arylene; or a substituted or unsubstituted $C_{2-60}$ heteroarylene containing any one or more heteroatoms selected from the group consisting of N, O and S, and $Ar_3$ and $Ar_4$ are each independently a substituted or unsubstituted $C_{6-60}$ aryl; or a substituted or unsubstituted $C_{2-60}$ heteroaryl containing any one or more heteroatoms selected from the group consisting of N, O and S.

2. The organic light emitting device according to claim 1, wherein $X_1$ to $X_3$ are N.

3. The organic light emitting device according to claim 1, wherein the first compound is represented by any one of the following Chemical Formulae 3-1 to 3-7:

3-1

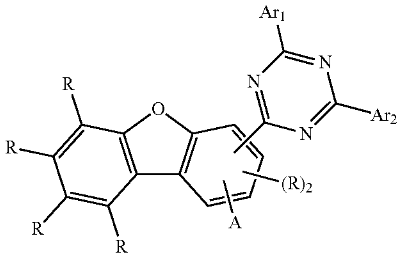

3-2

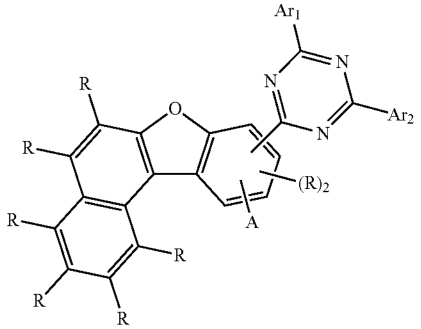

3-3

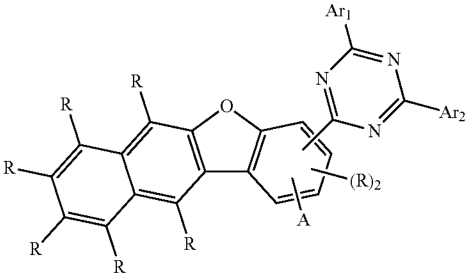

3-4

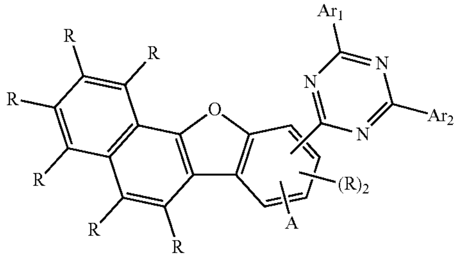

3-5

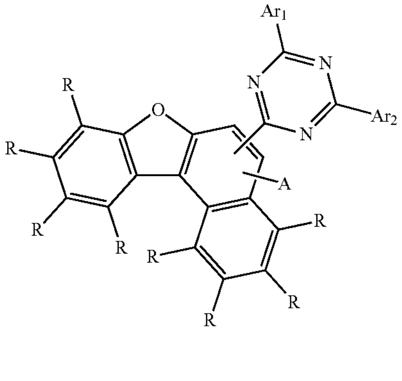

-continued 3-6

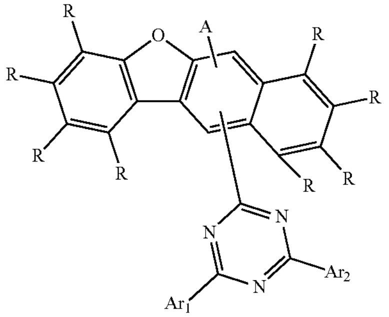

3-7

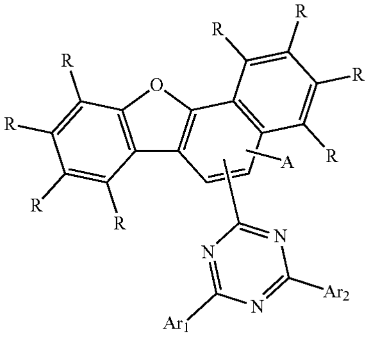

wherein, in Chemical Formulae 3-1 to 3-7, each R is independently hydrogen or deuterium, and A, $Ar_1$ and $Ar_2$ are the same as defined in claim 1.

4. The organic light emitting device according to claim 1, wherein $Ar_1$ and $Ar_2$ are each independently any one selected from the group consisting of the following:

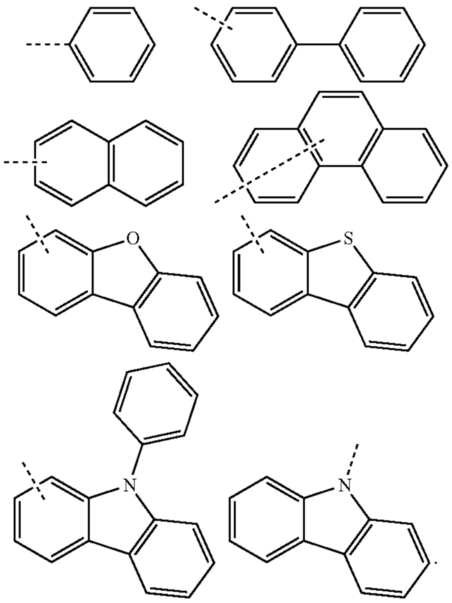

5. The organic light emitting device according to claim 1, wherein A is any one of the substituents represented by the following Chemical Formulae a1 to a4:

a1

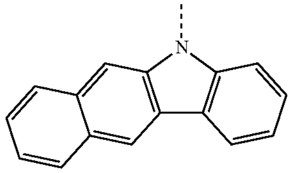

a2

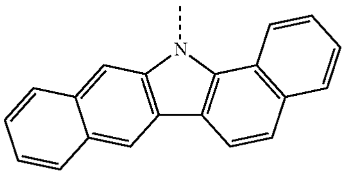

a3

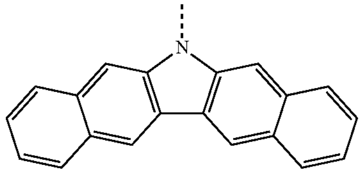

a4

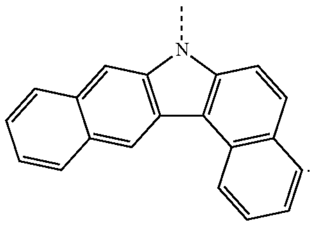

6. The organic light emitting device according to claim 1, wherein the first compound is any one selected from the group consisting of the following:

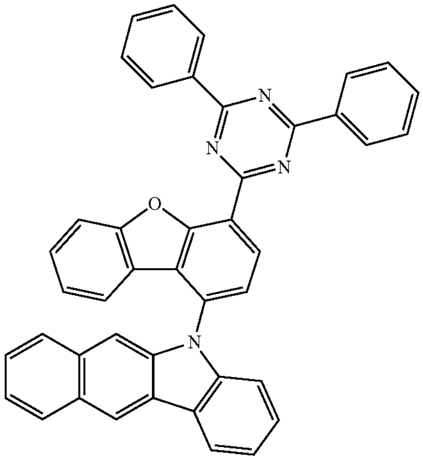

-continued
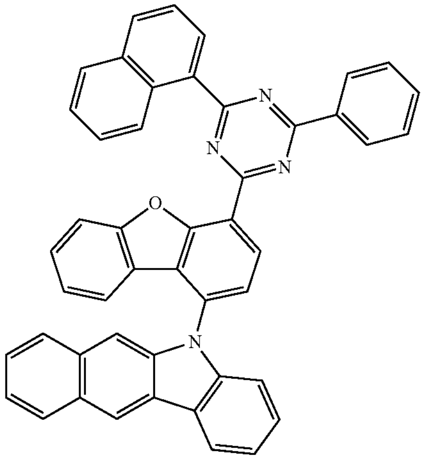
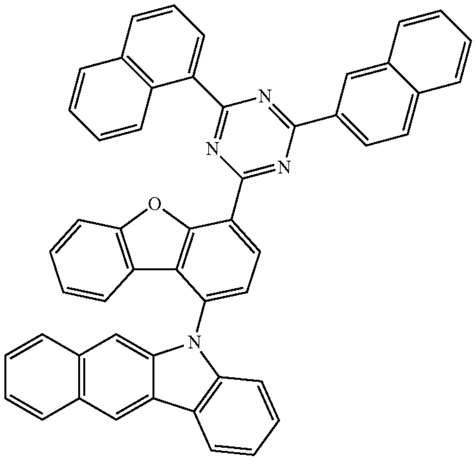
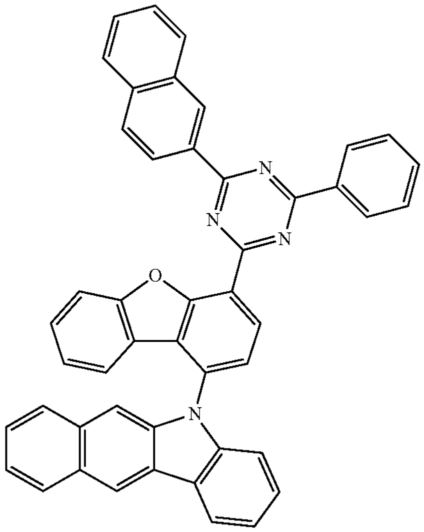
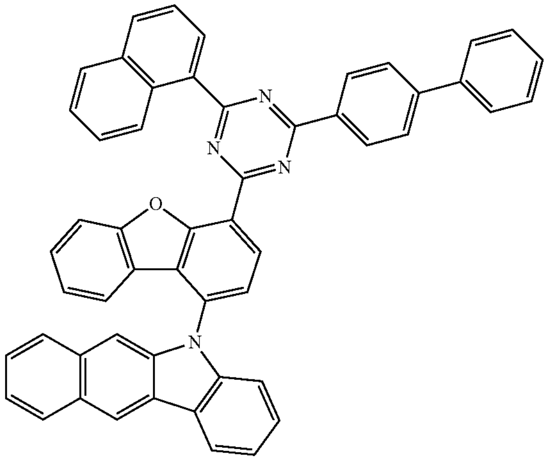
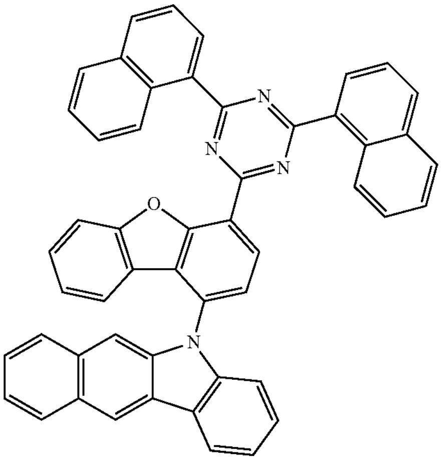
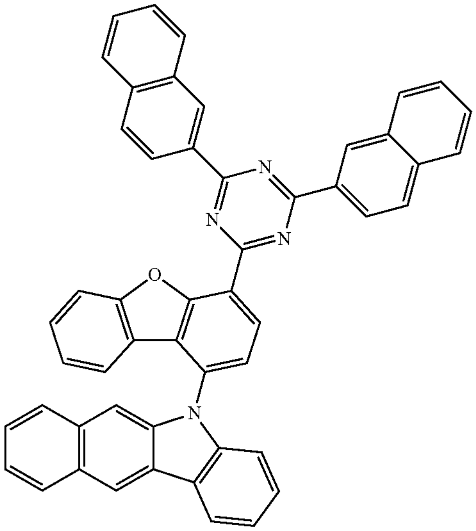
-continued -continued
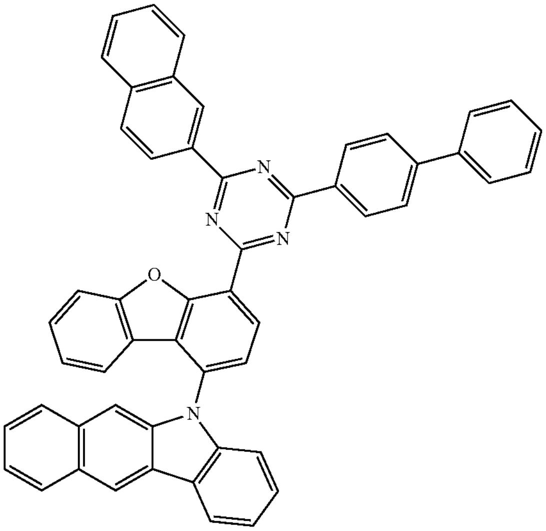
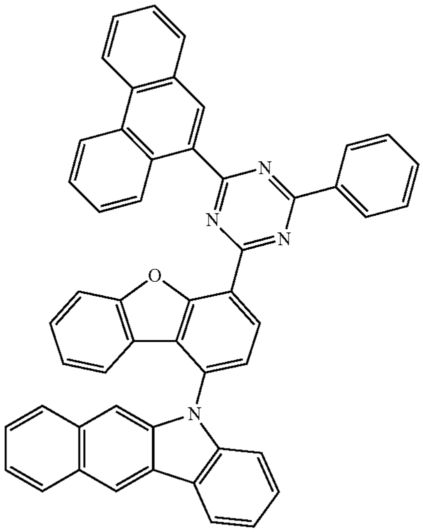
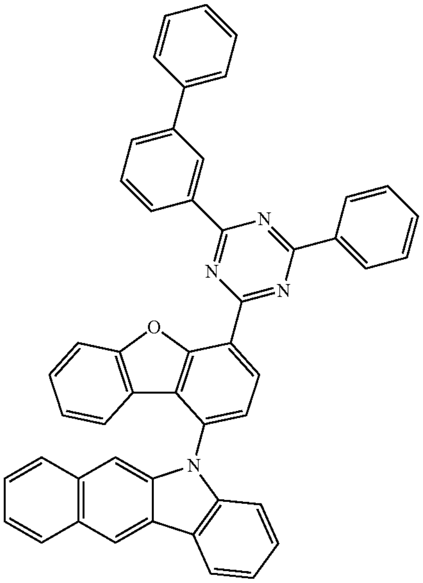
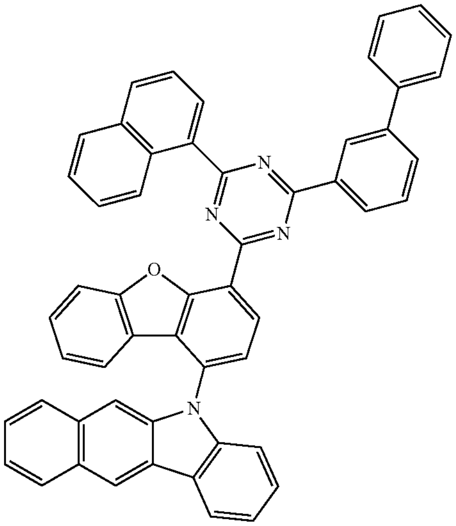
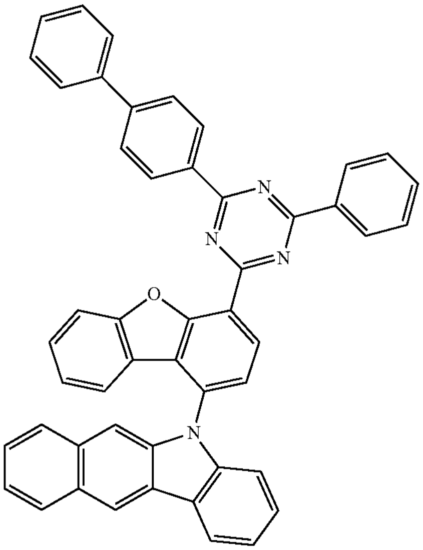
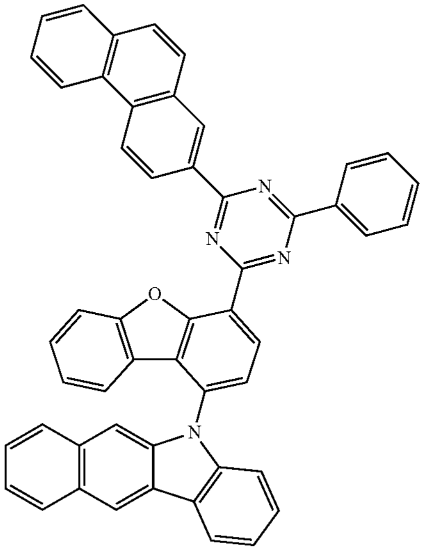

-continued
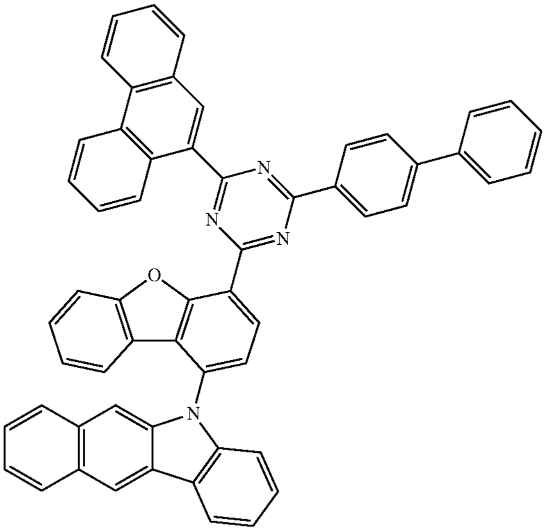
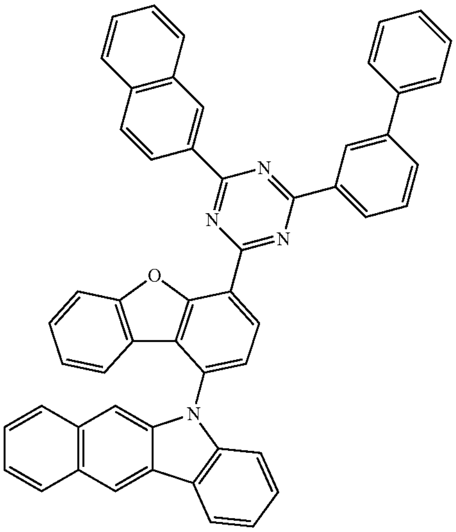
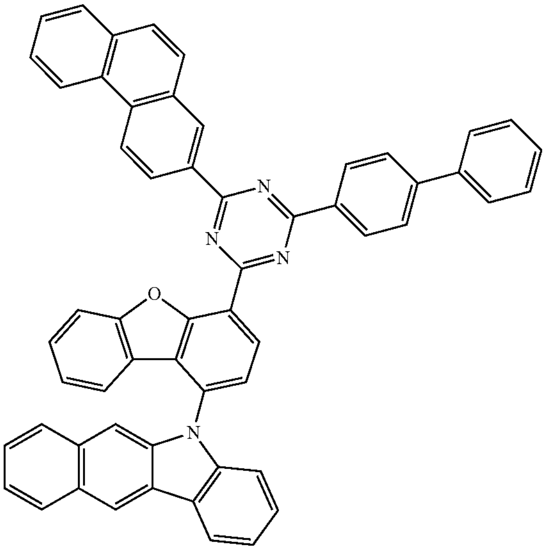
-continued
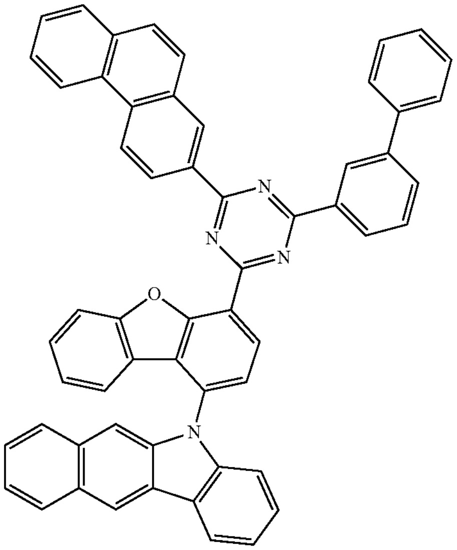
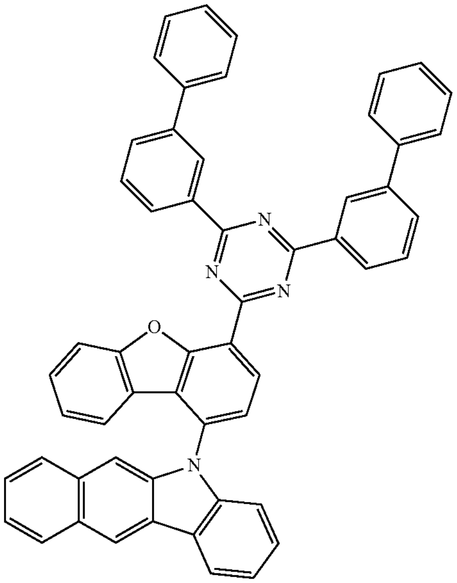
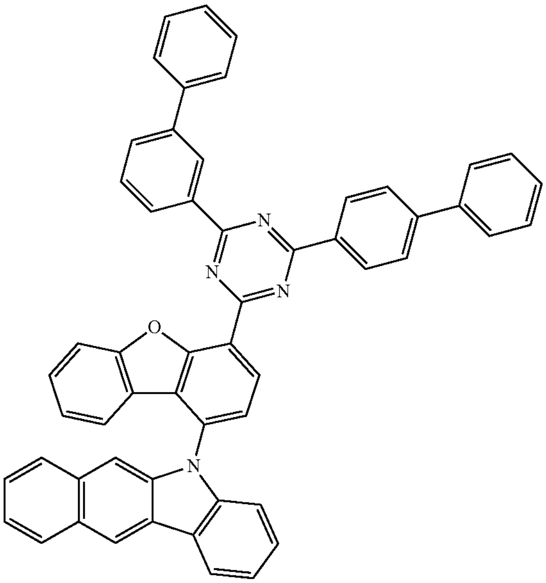

-continued
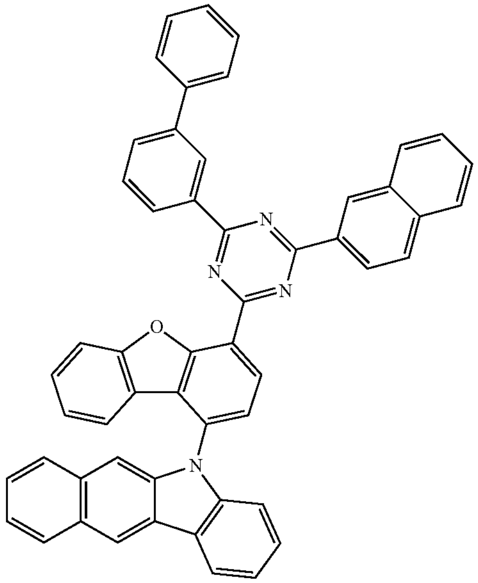
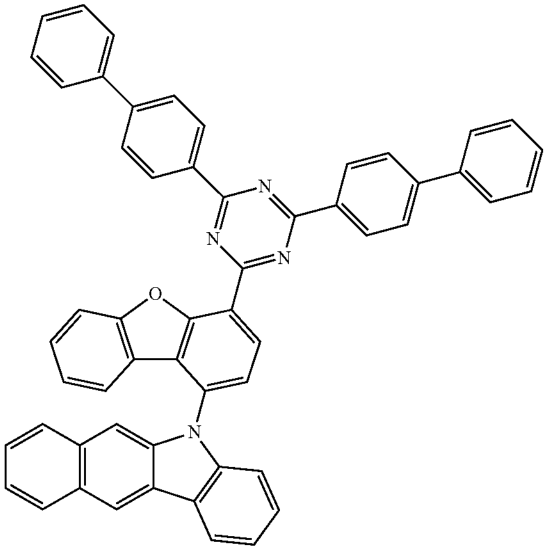
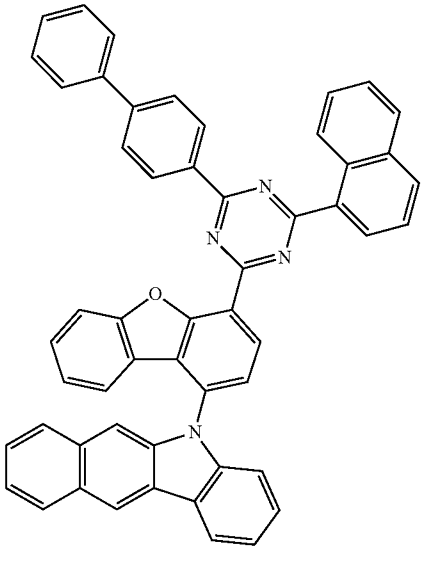
-continued
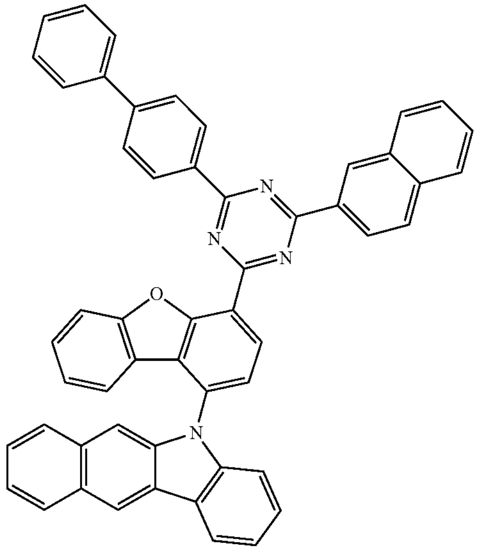
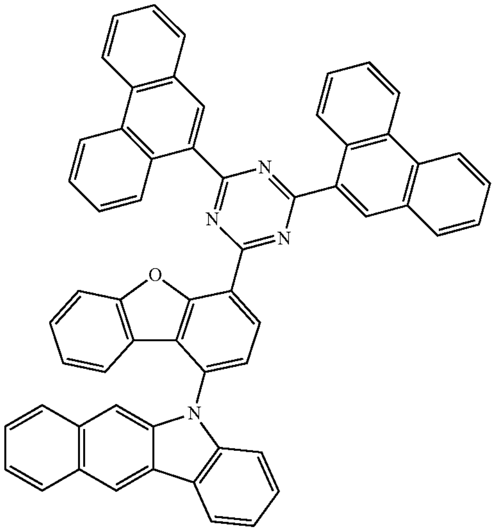
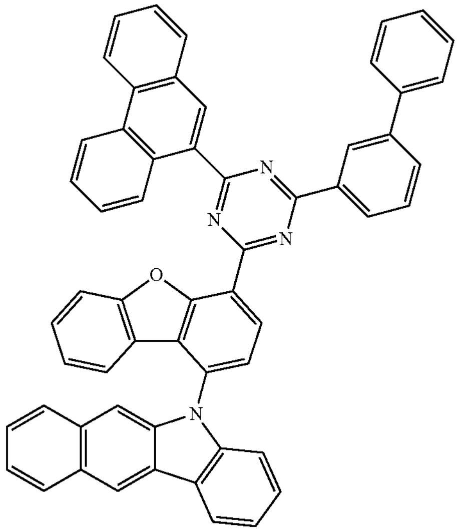

-continued
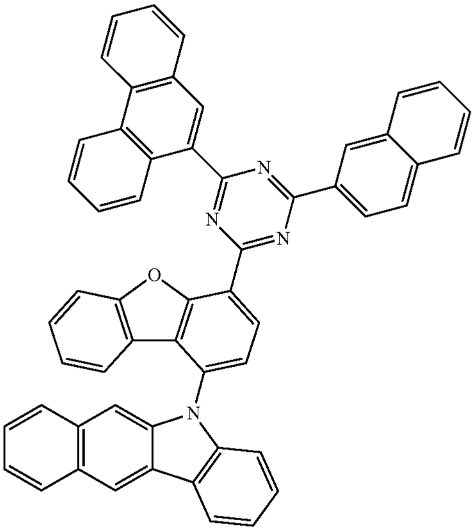
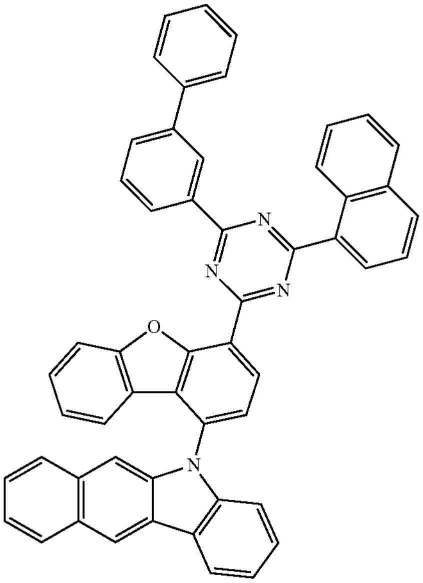
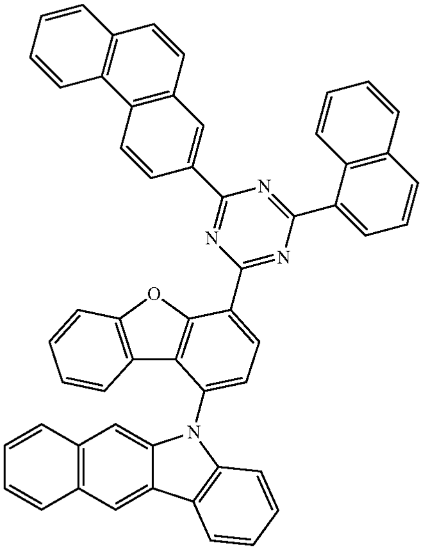
-continued
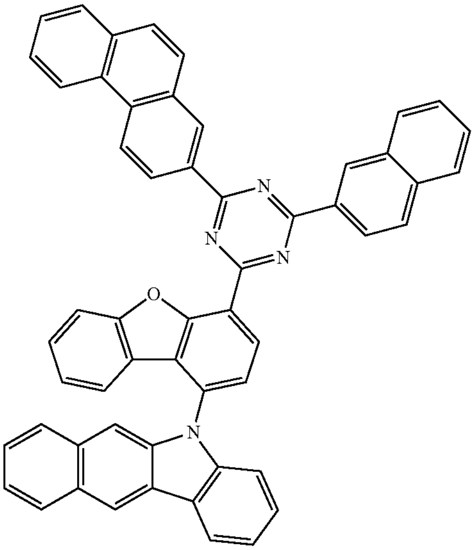
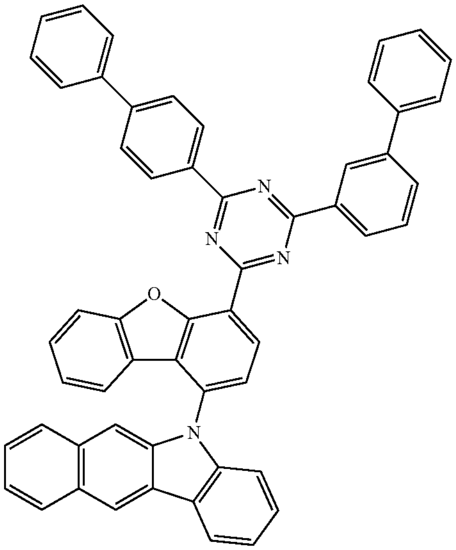
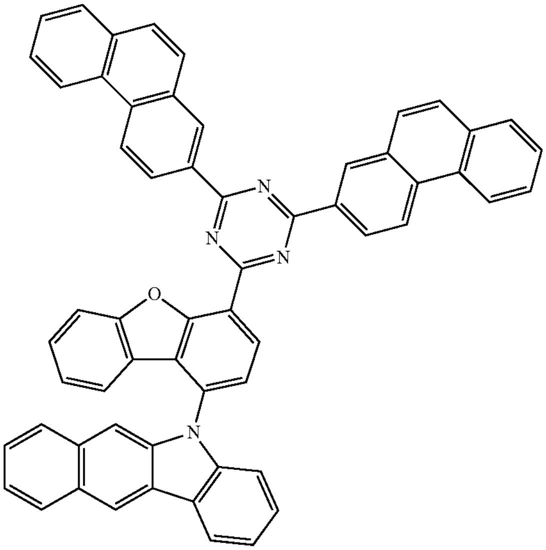

-continued
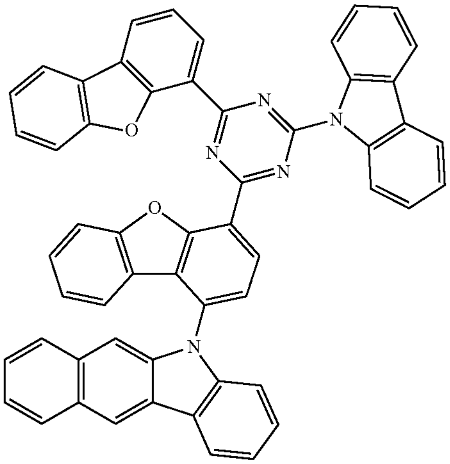
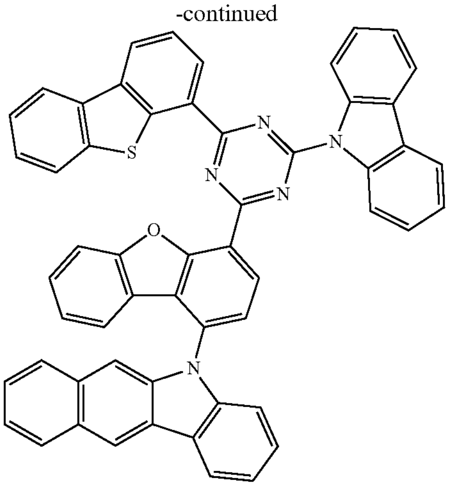
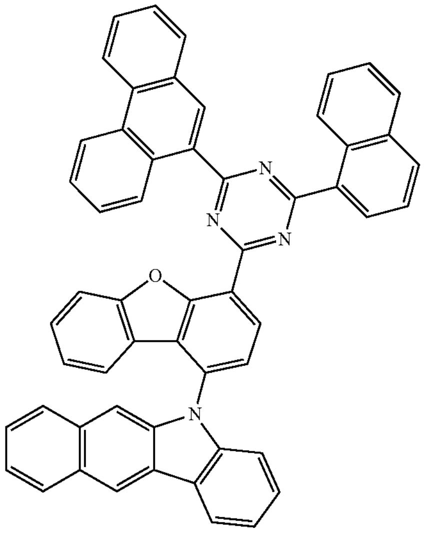
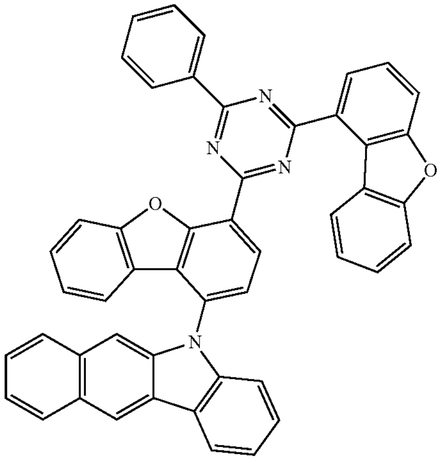
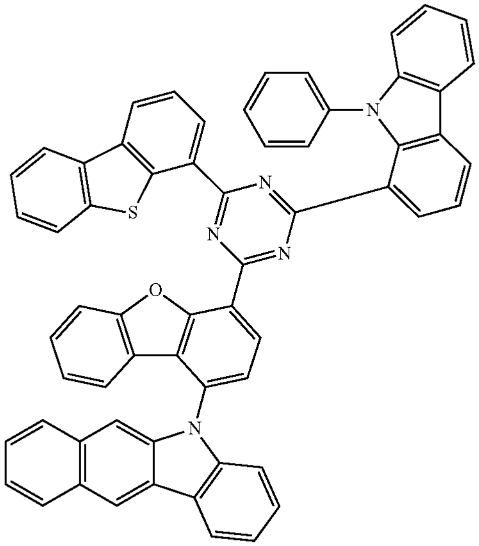
-continued
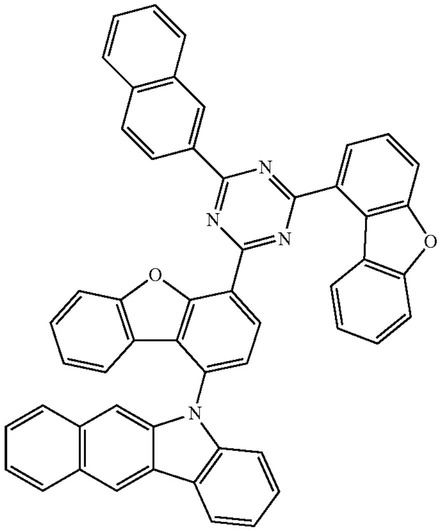

-continued
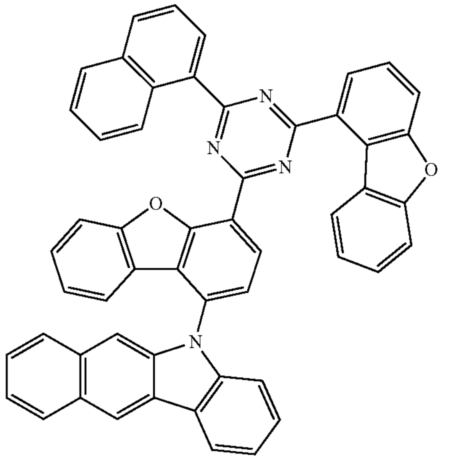
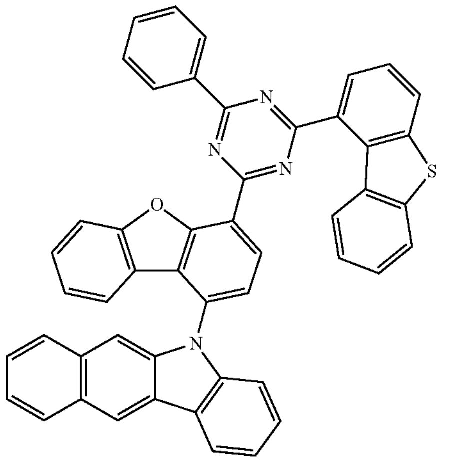
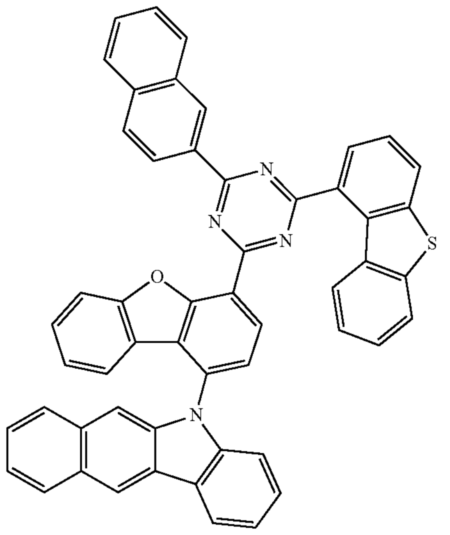
-continued
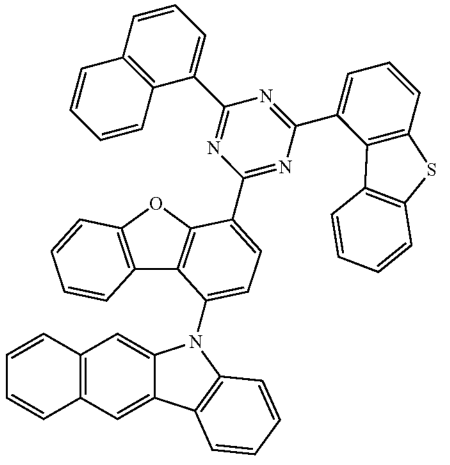
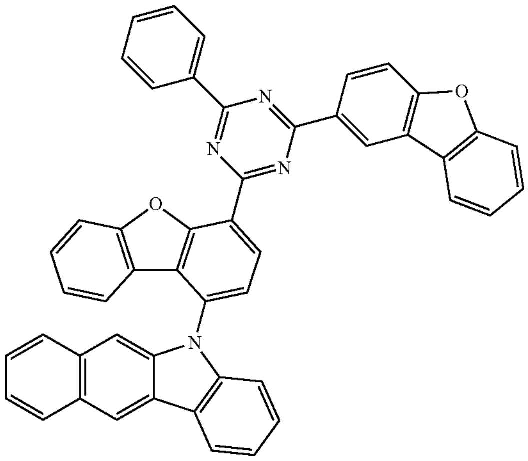
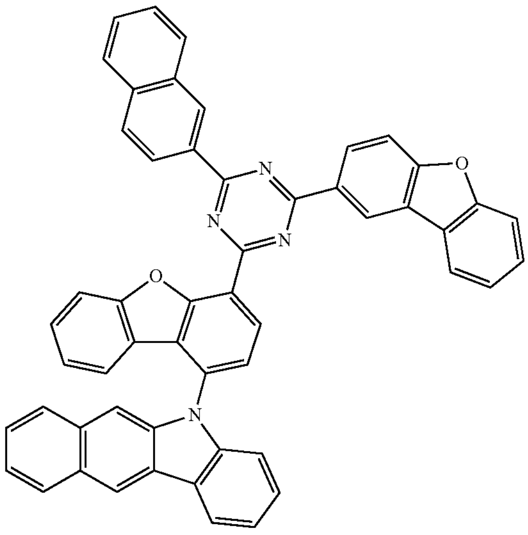

-continued
-continued
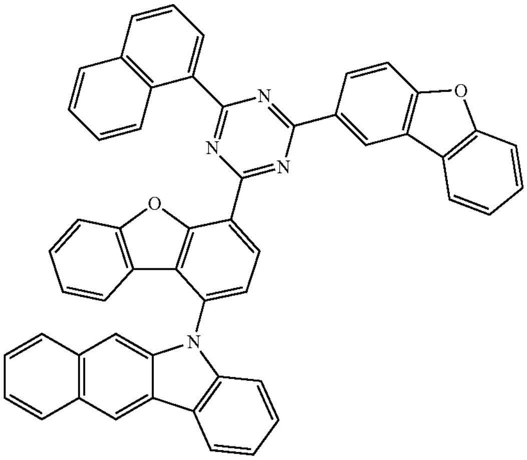
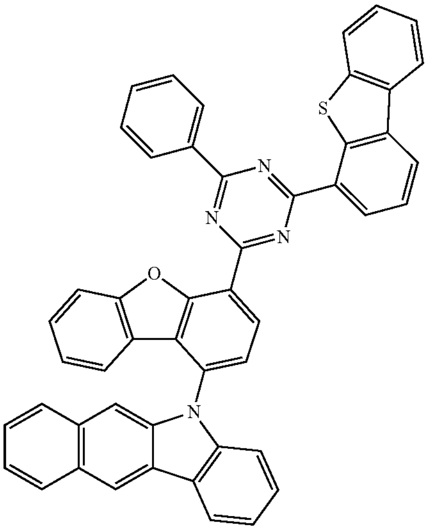
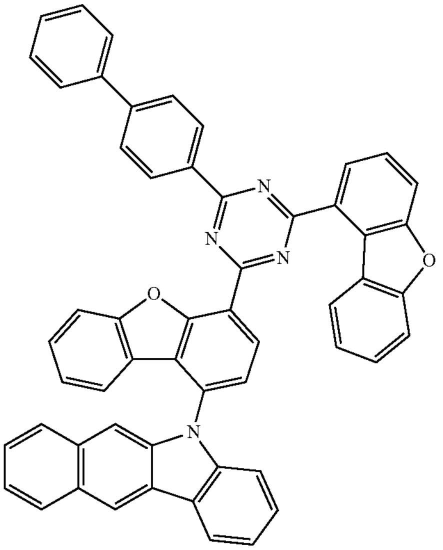
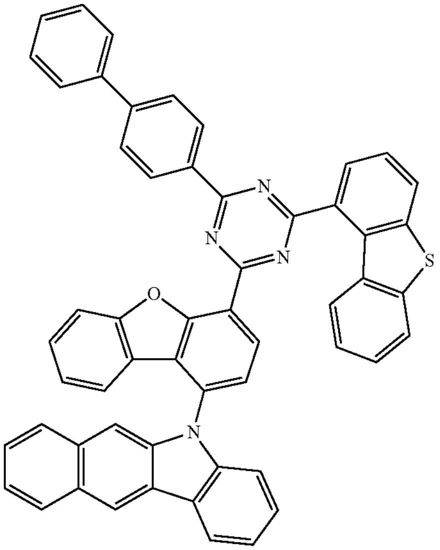
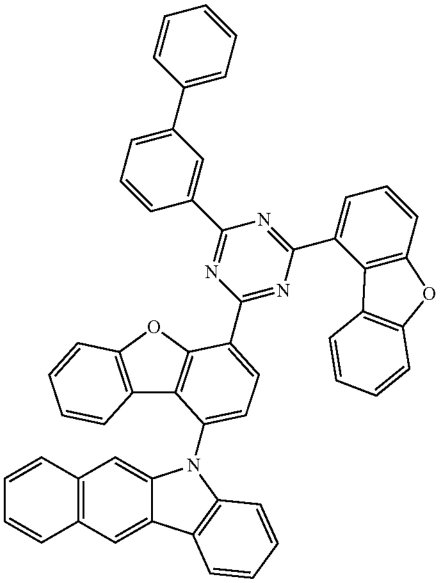
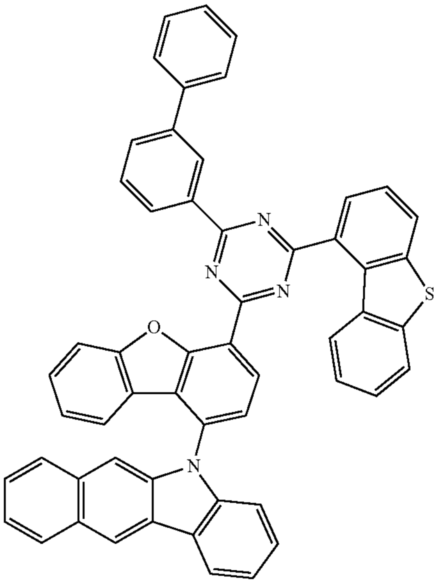

-continued
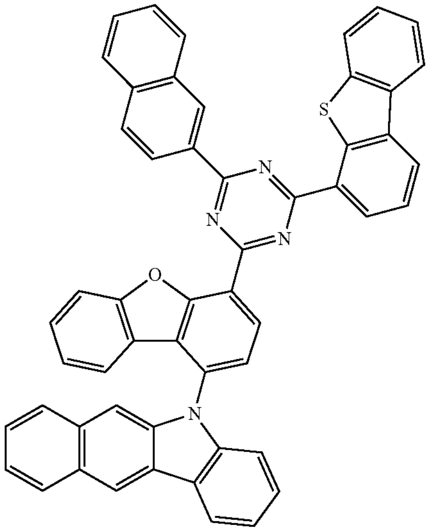
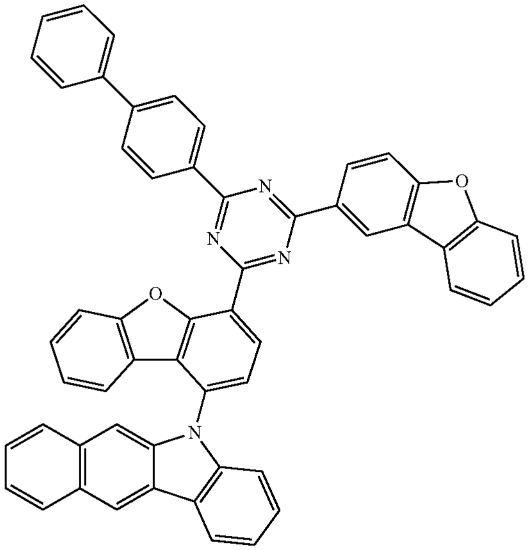
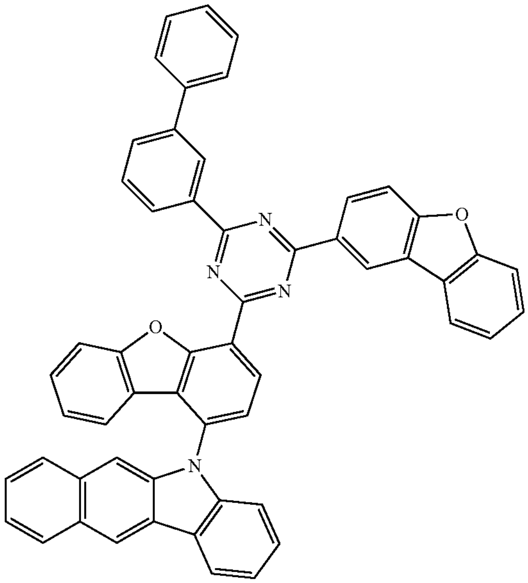
-continued
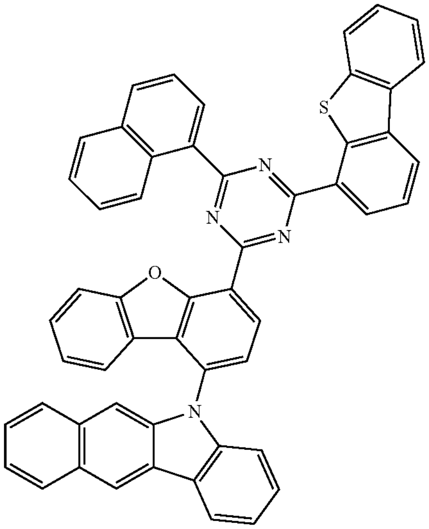
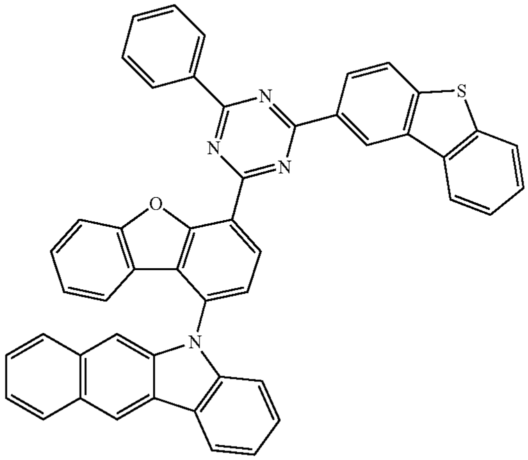
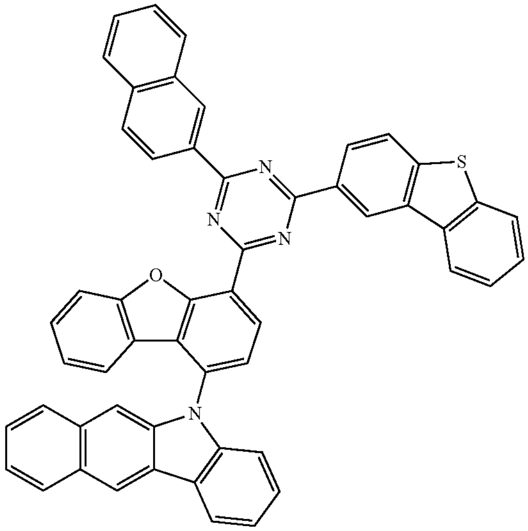

-continued
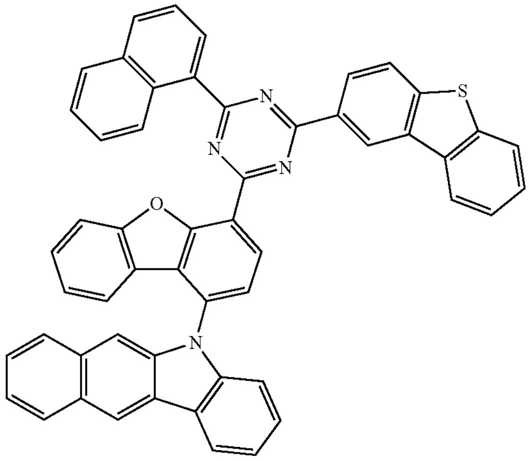
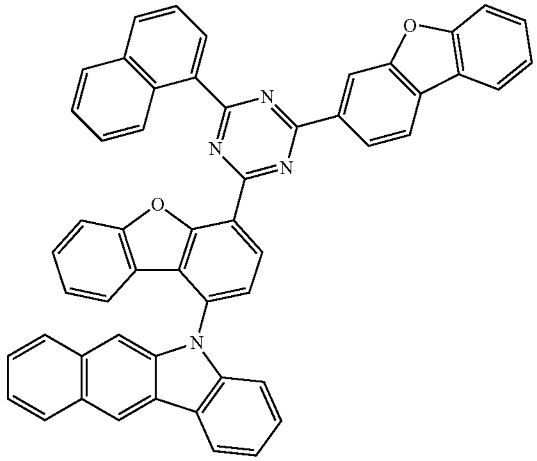
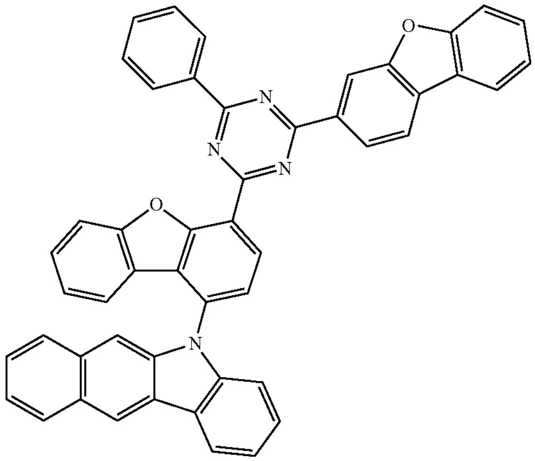
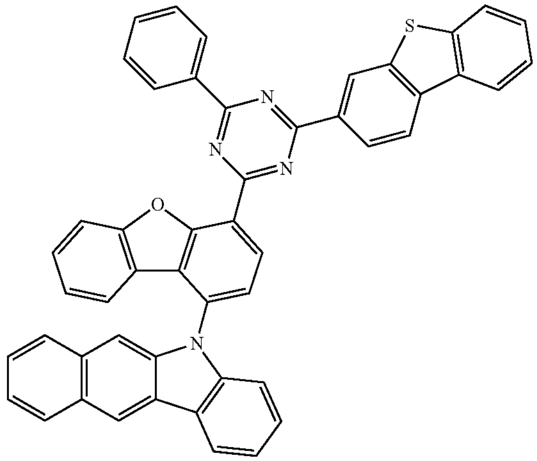
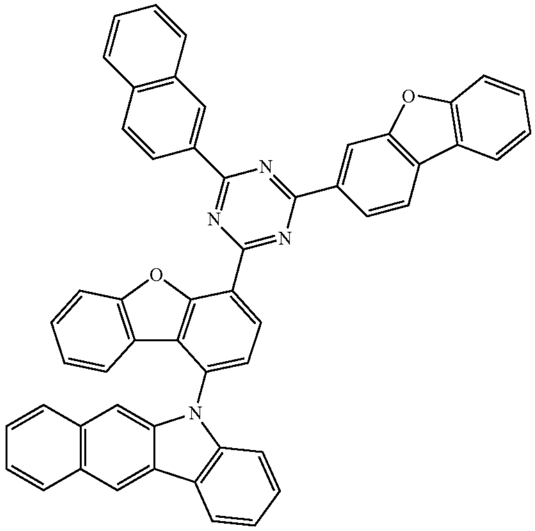
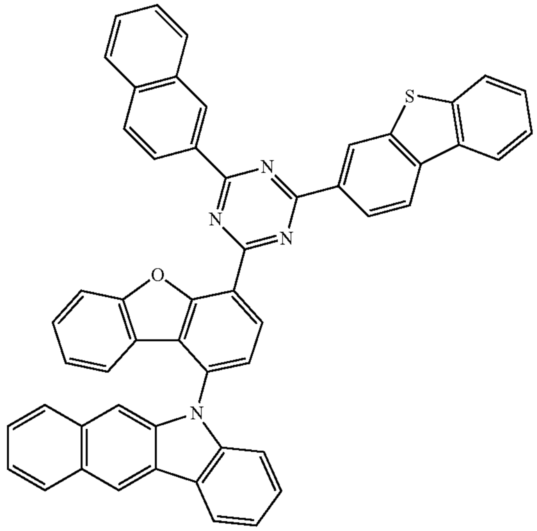

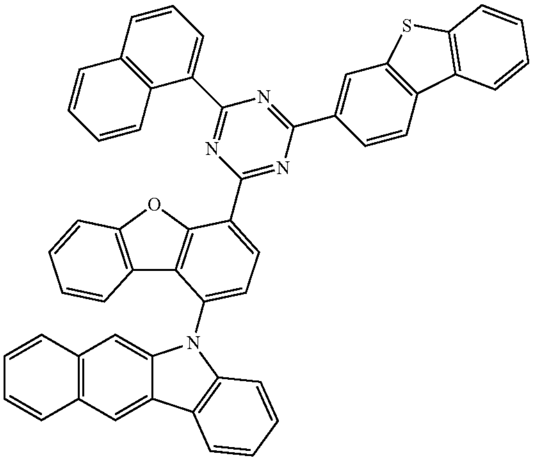
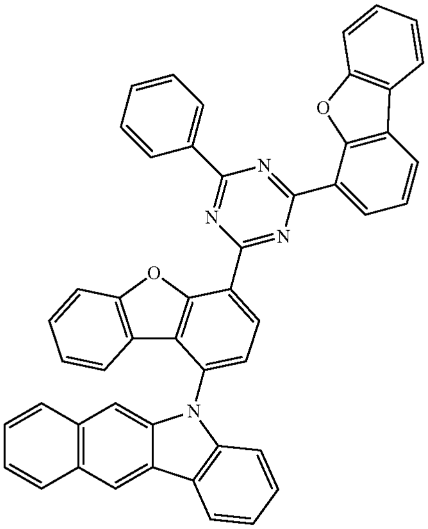
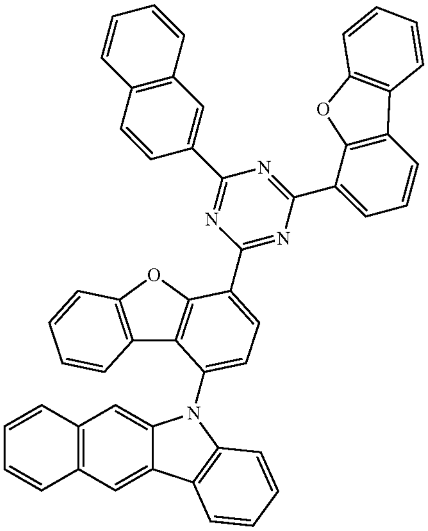
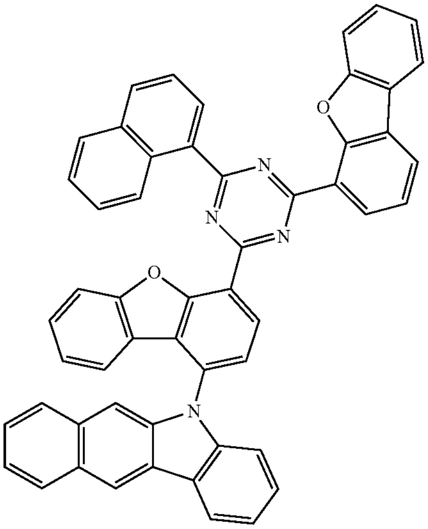
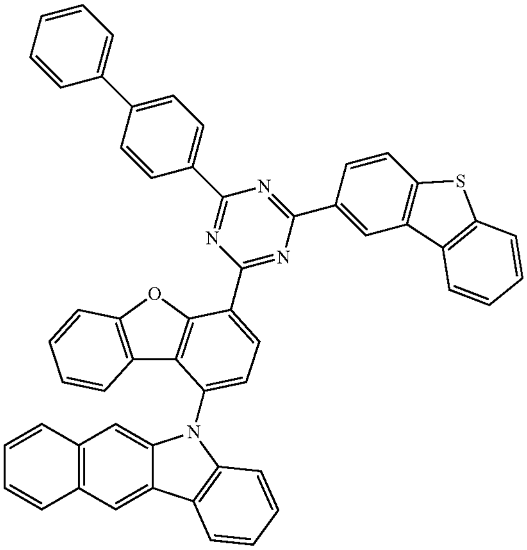
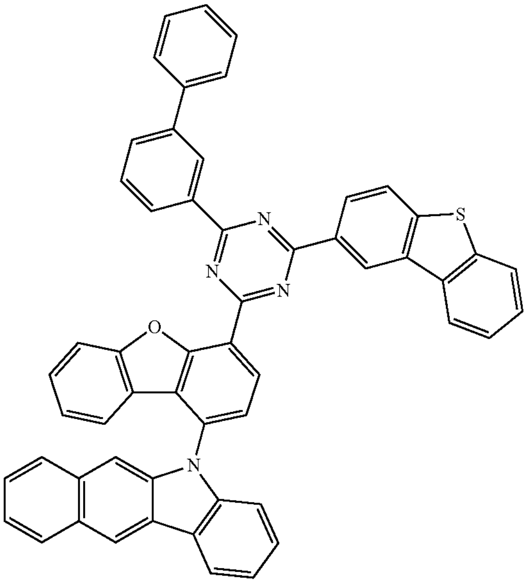

-continued
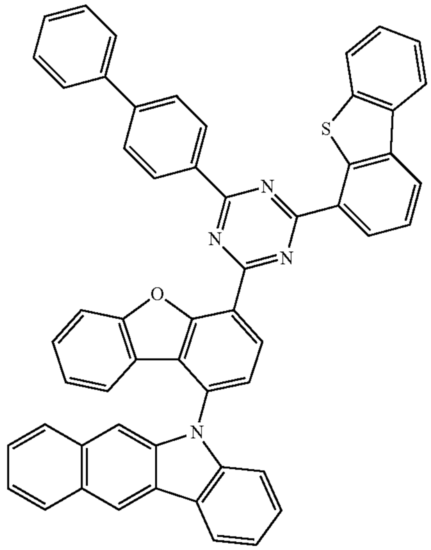
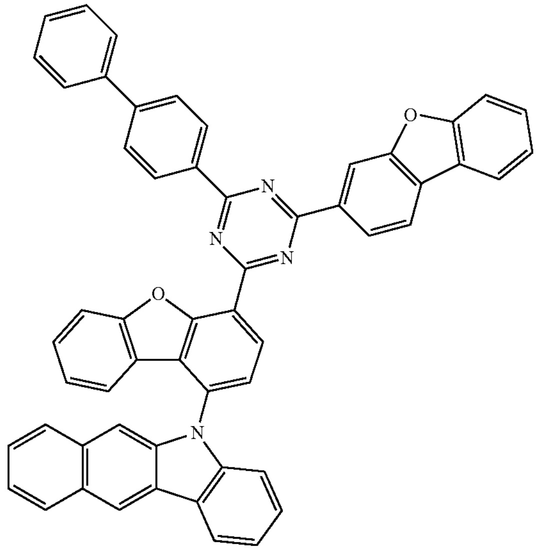
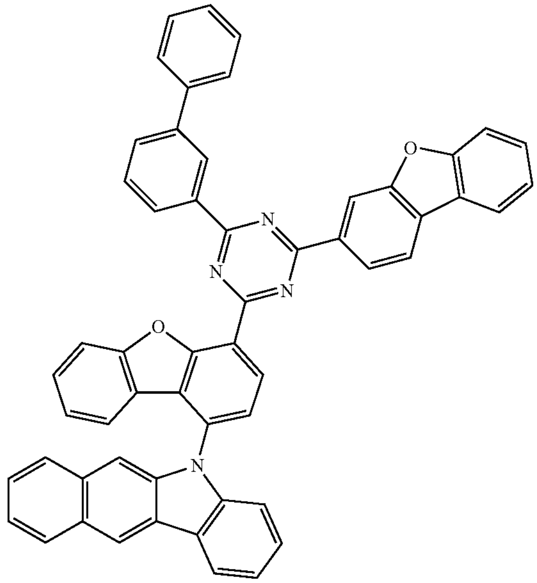
-continued
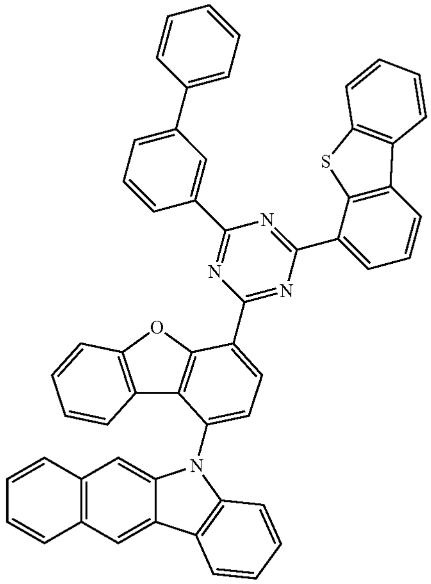
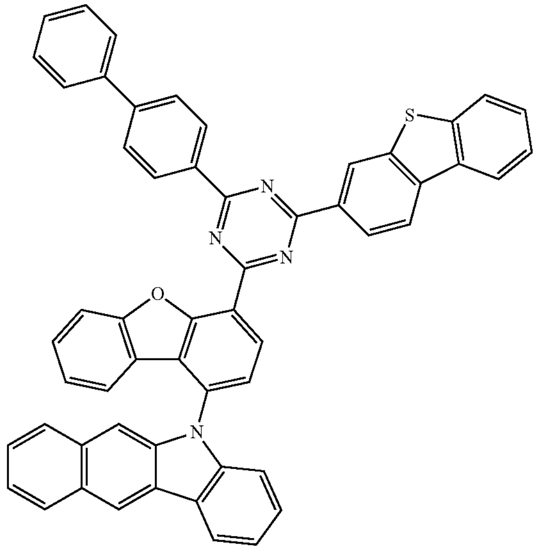
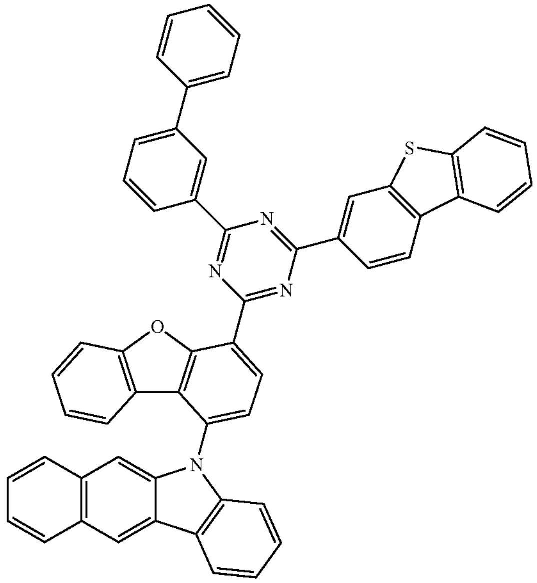

-continued
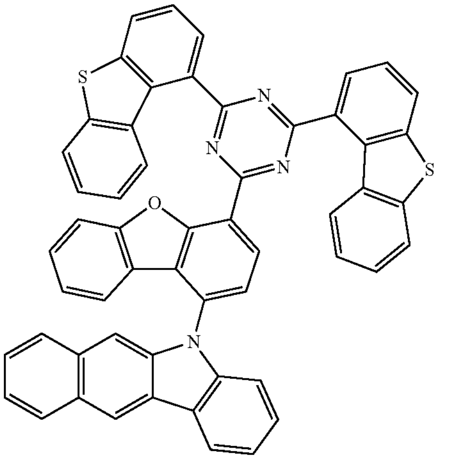
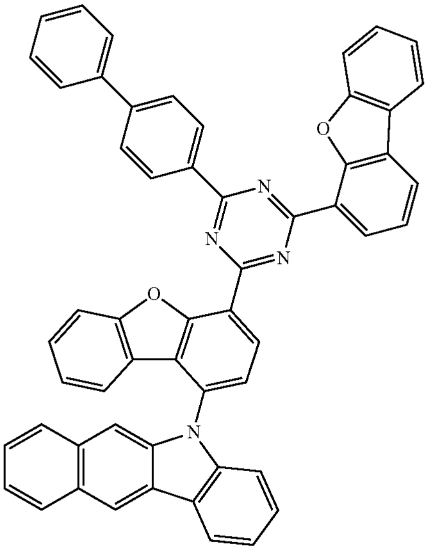
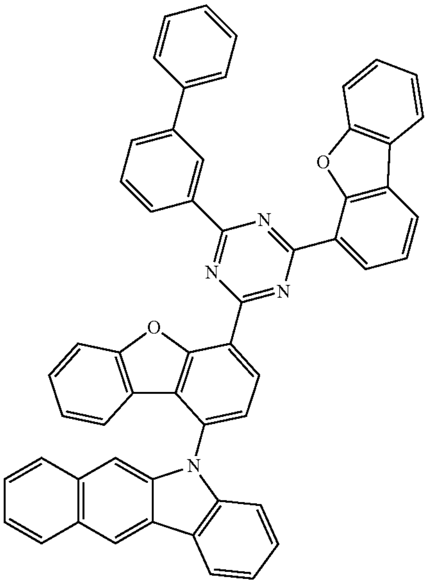
-continued
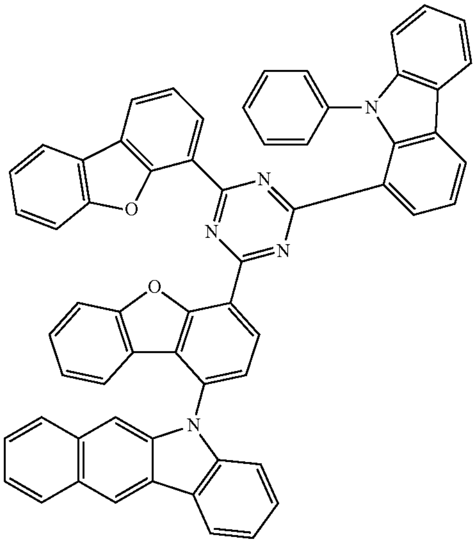
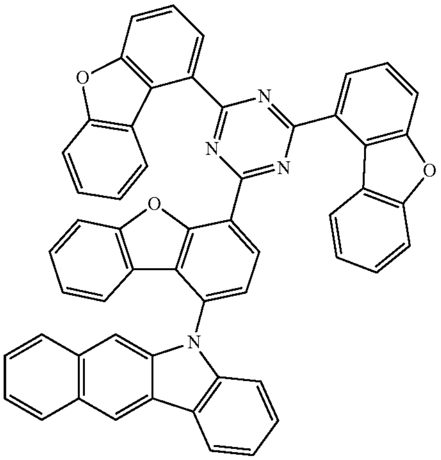
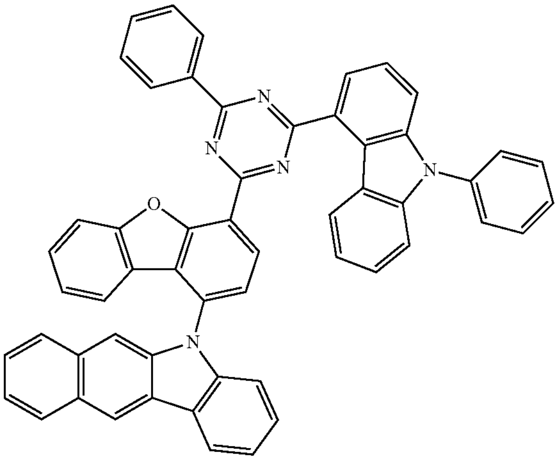

-continued
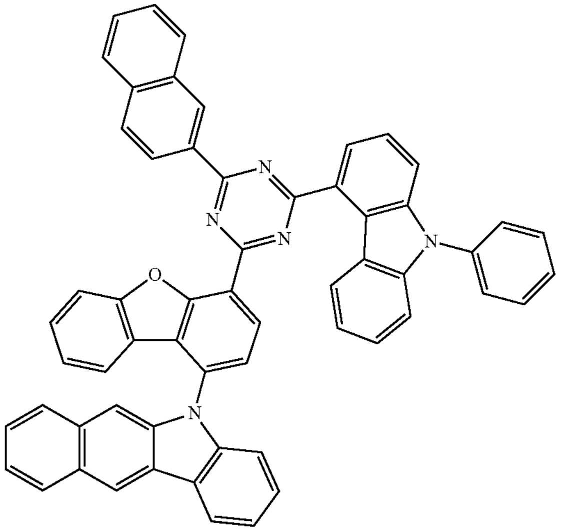
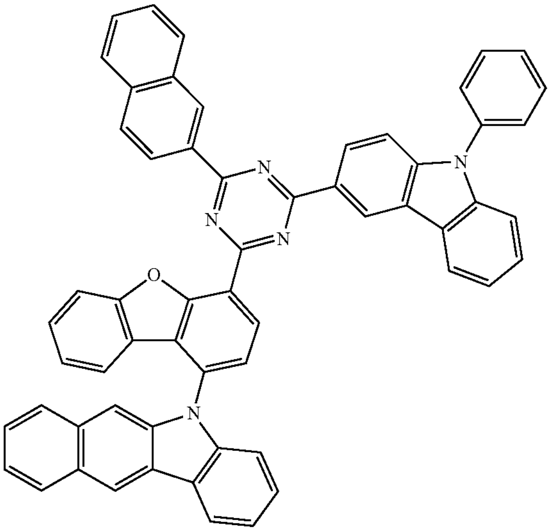
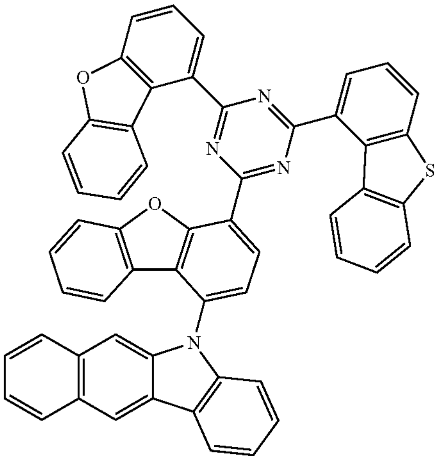
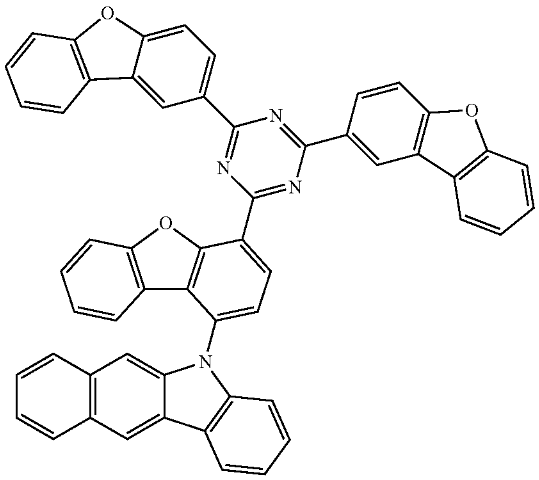
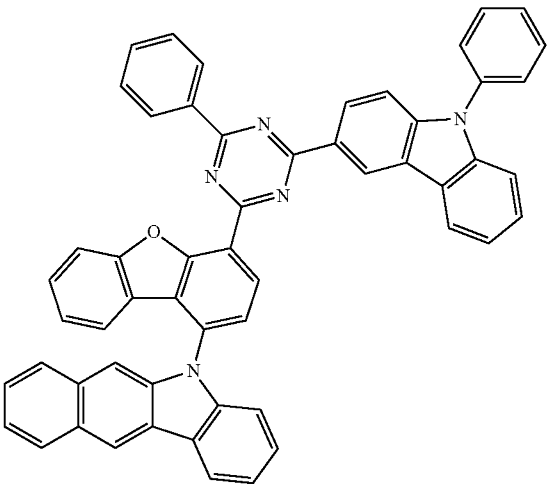
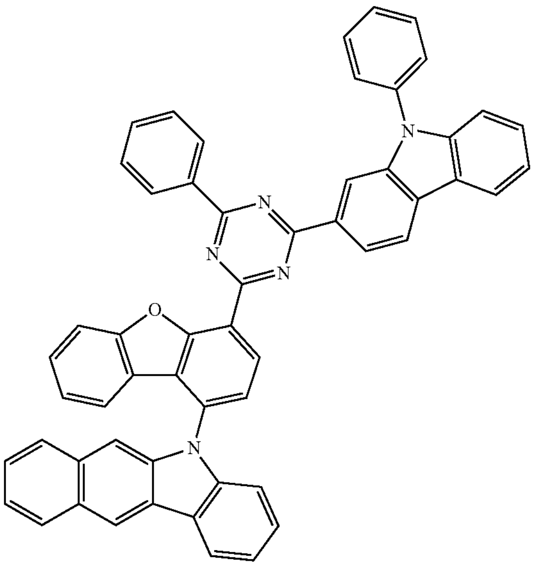
-continued -continued
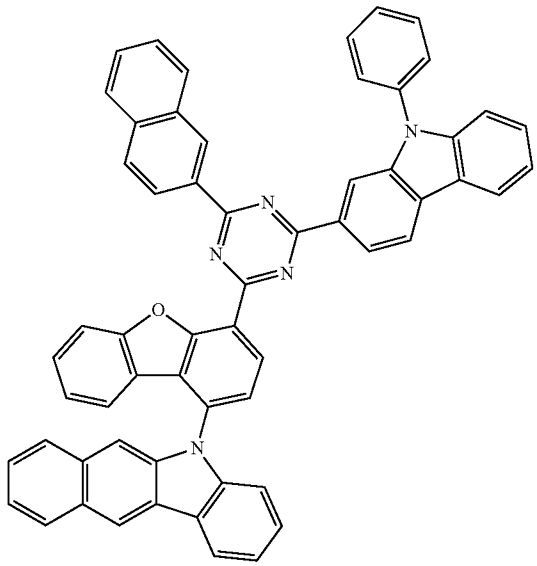
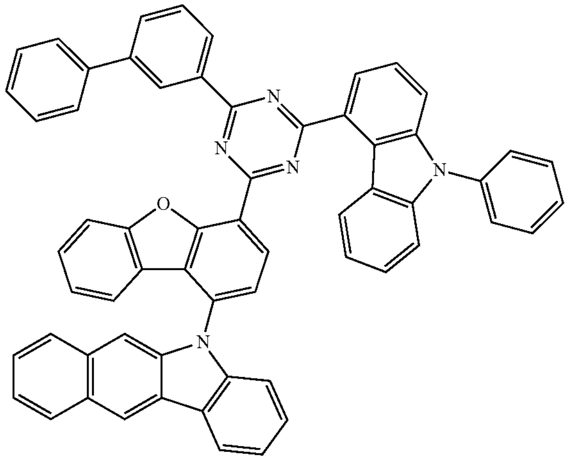
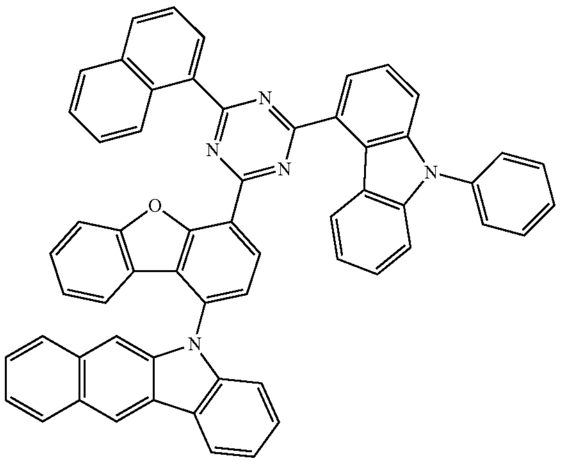
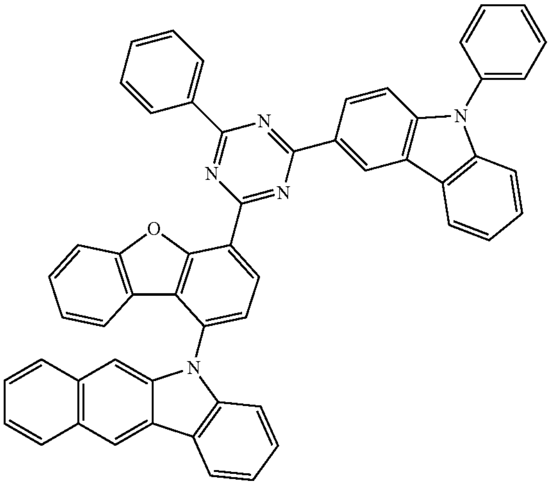
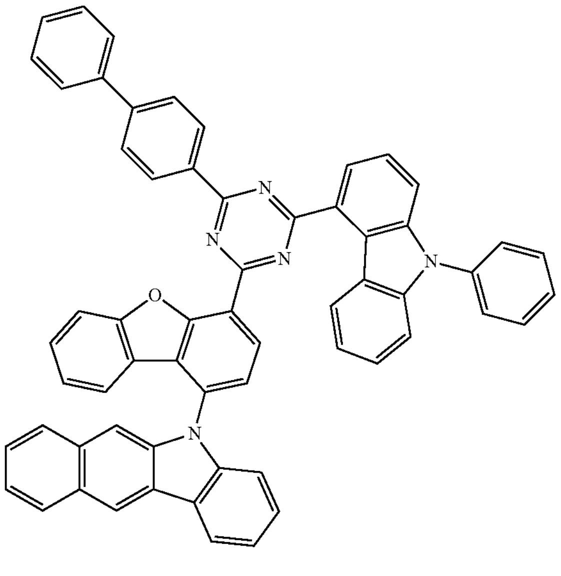
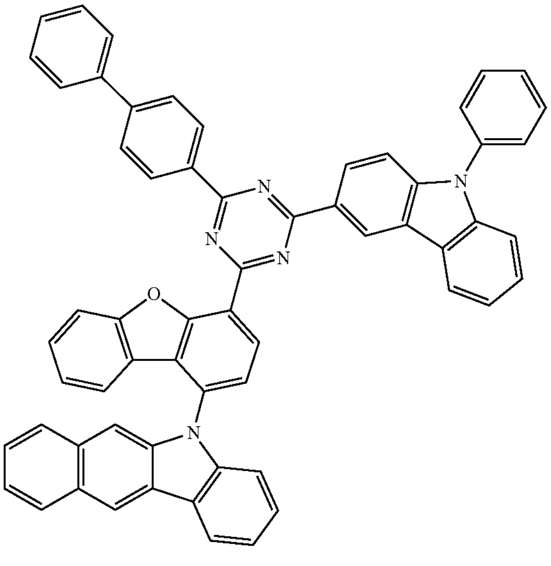
-continued -continued
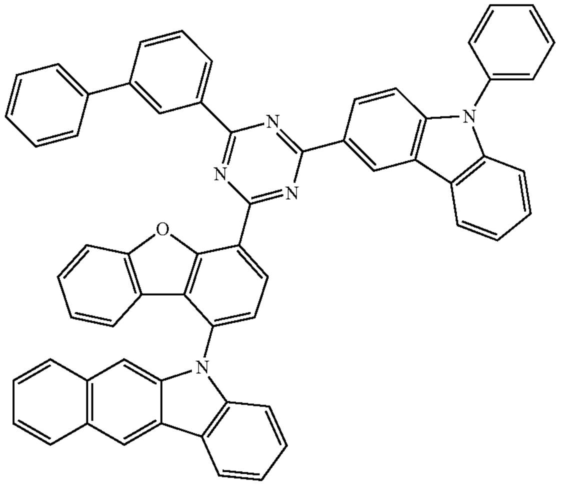
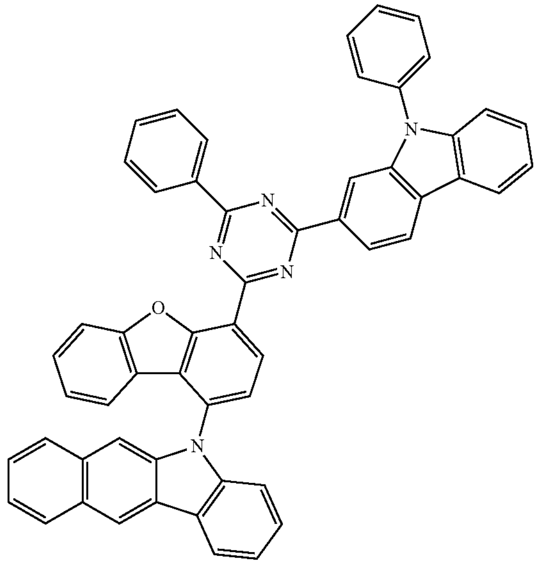
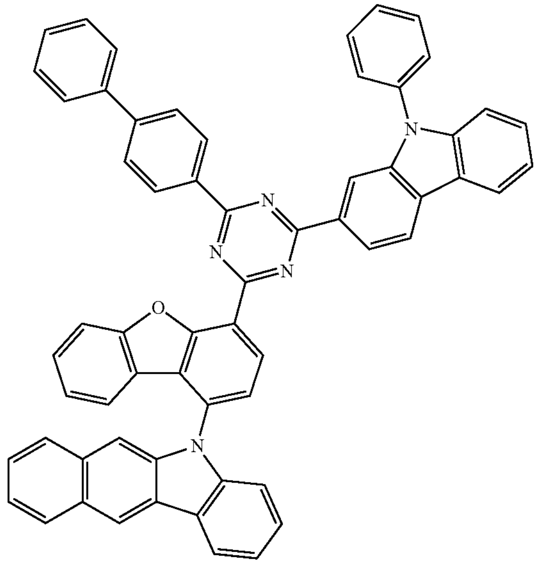
-continued
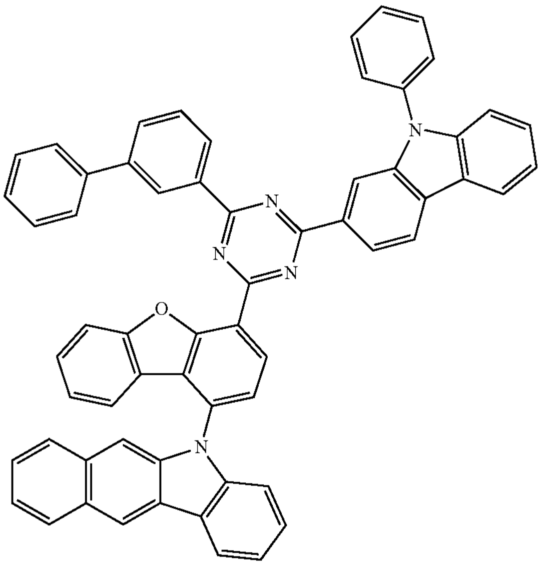
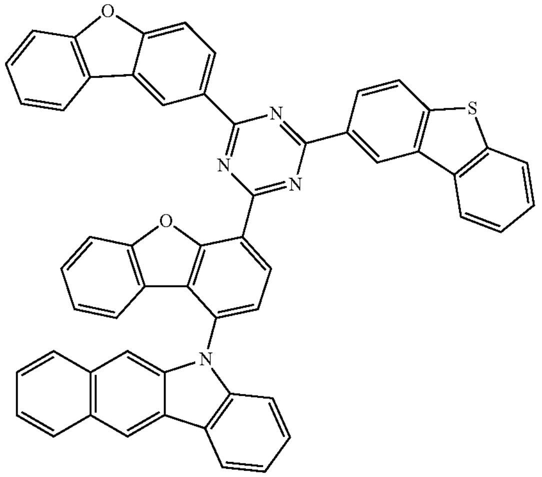
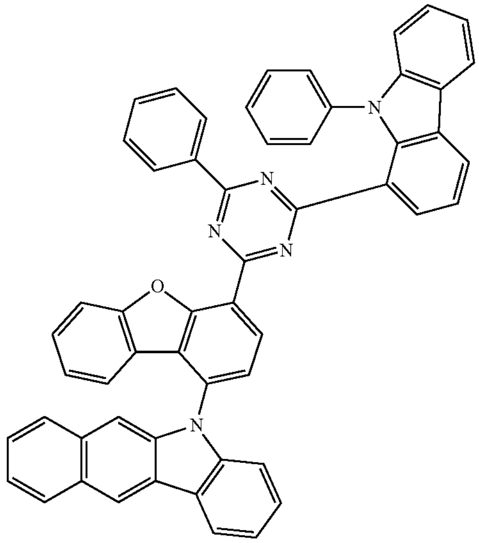

-continued
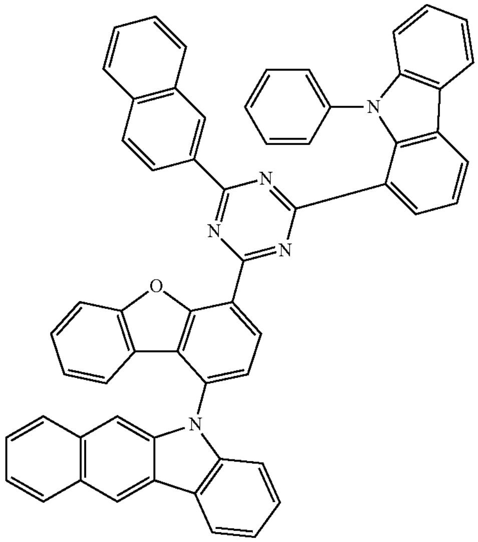
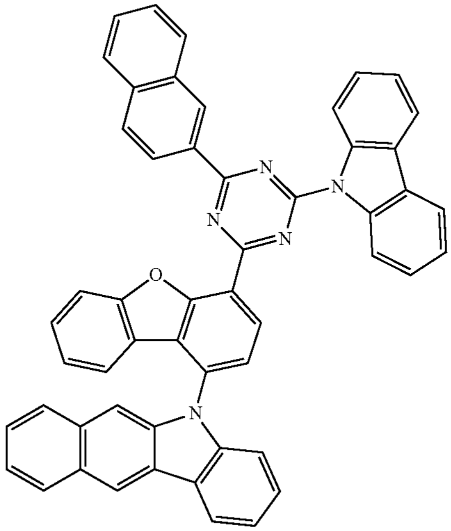
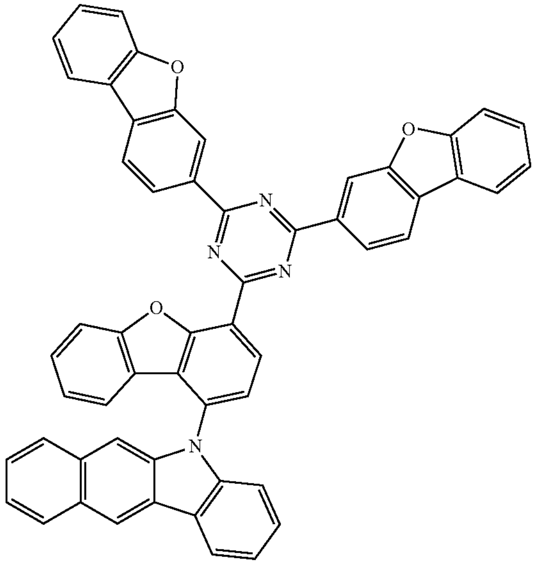
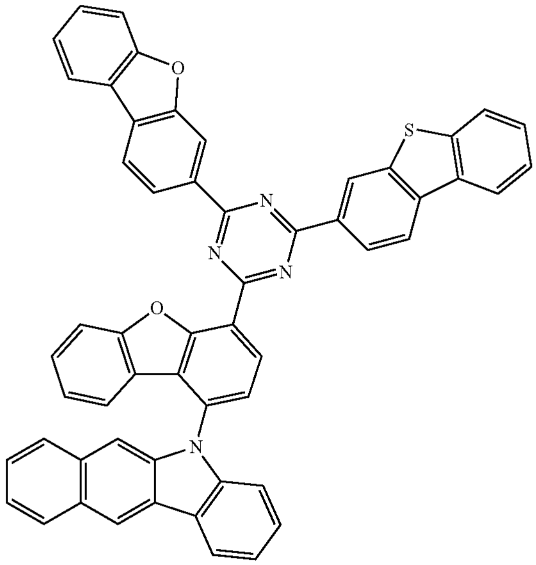
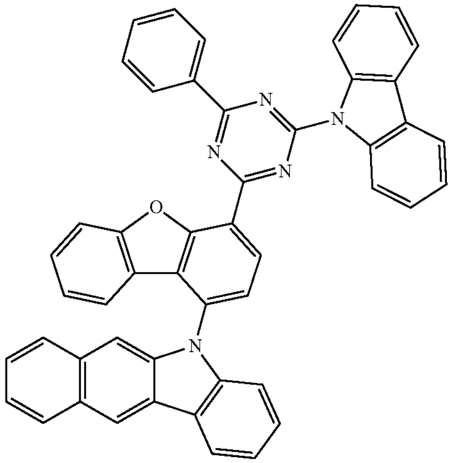
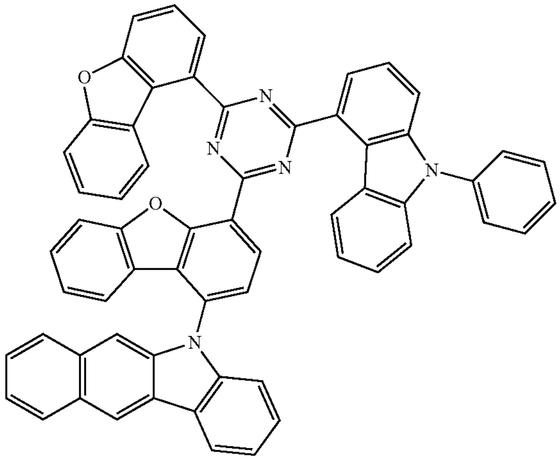

-continued
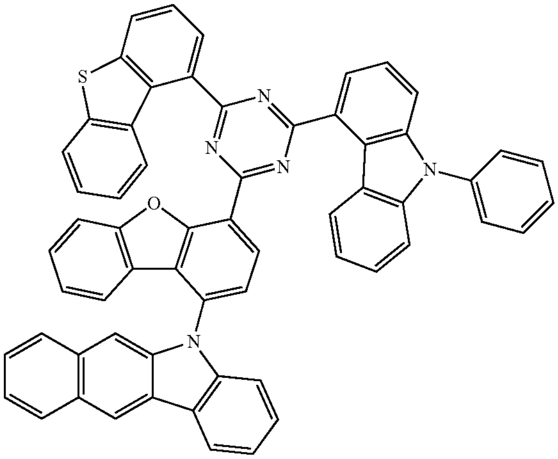
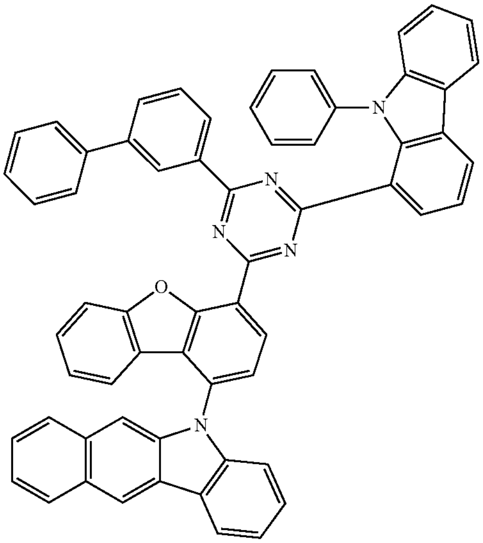
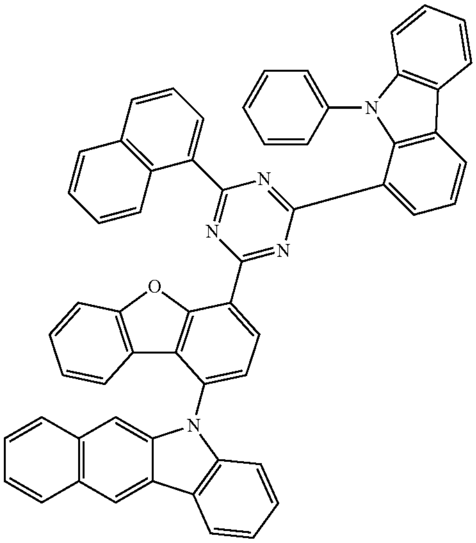
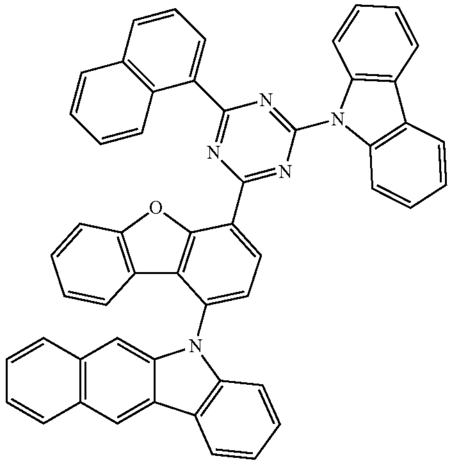
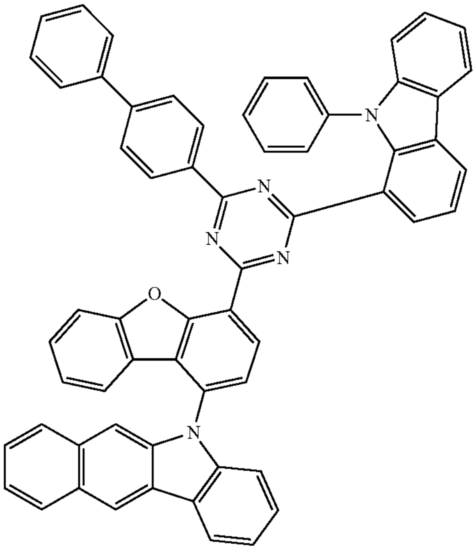
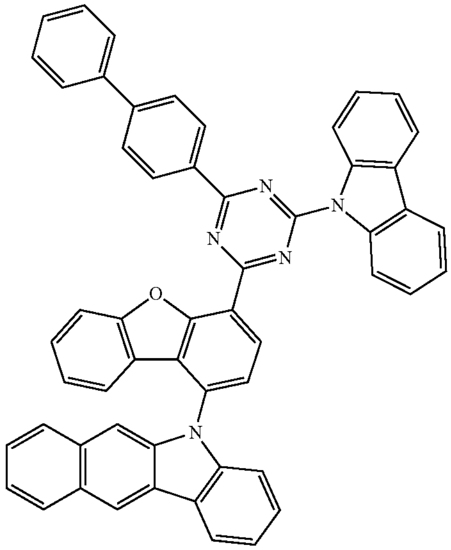
-continued -continued
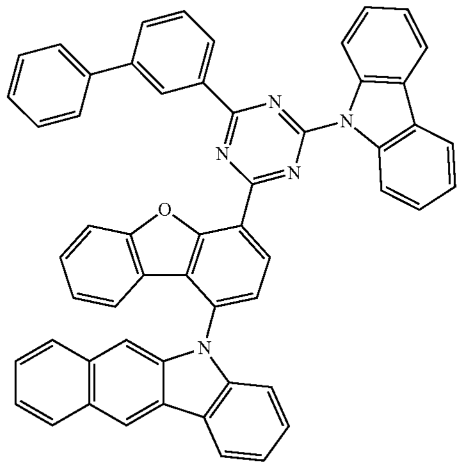
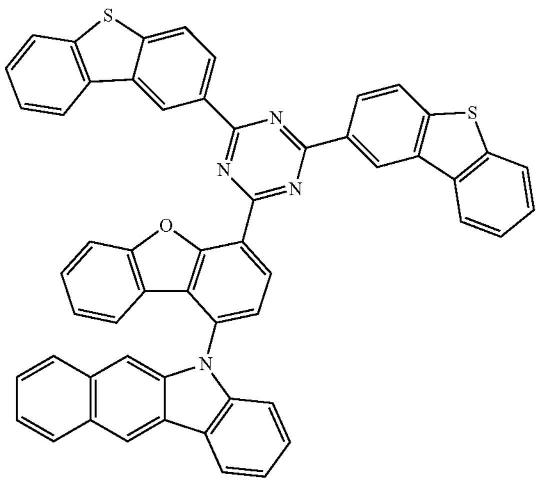
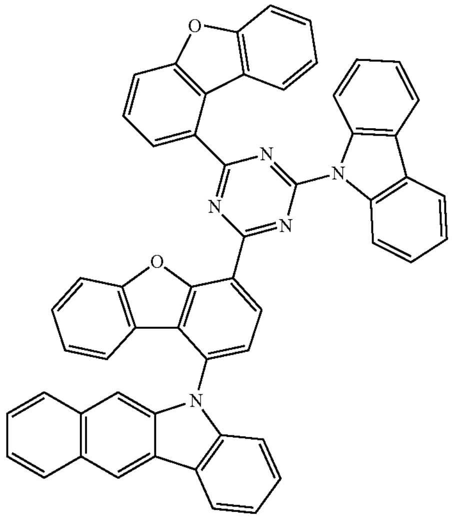
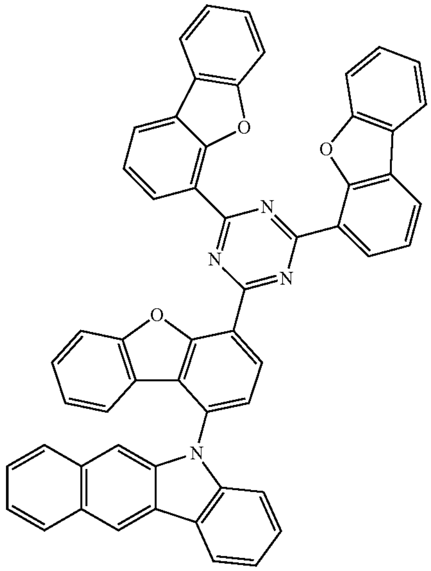
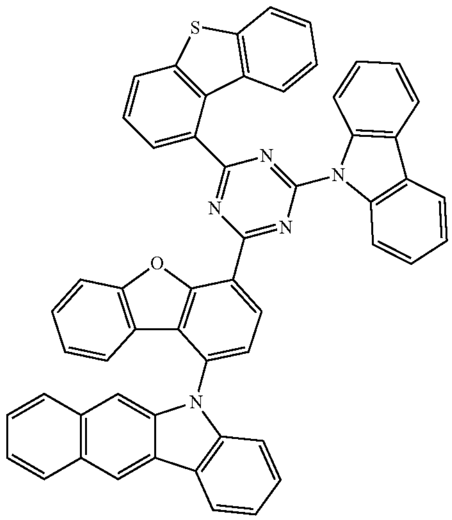
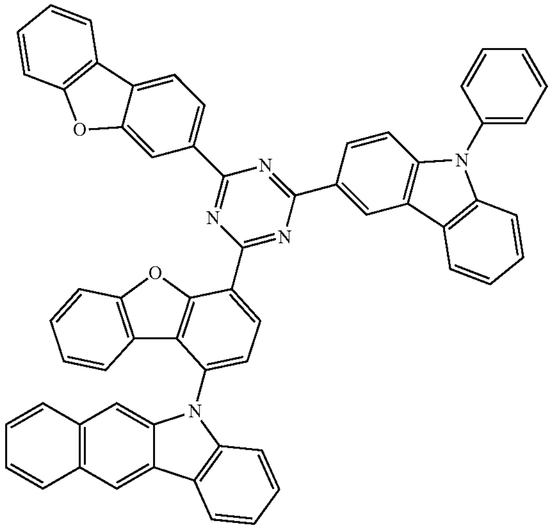

-continued
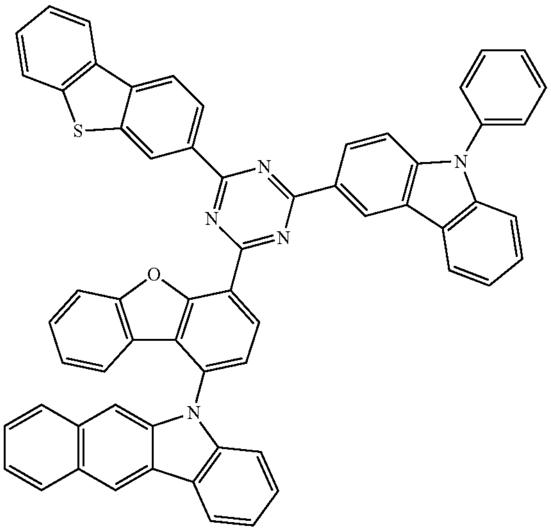
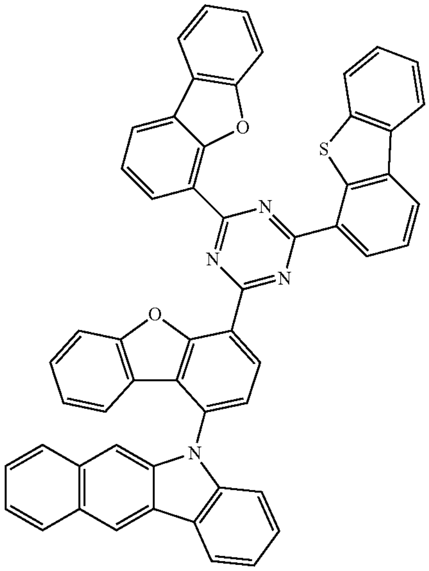
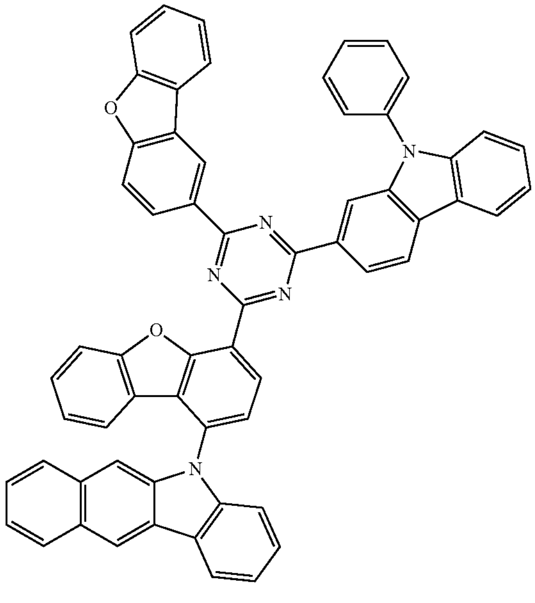
-continued
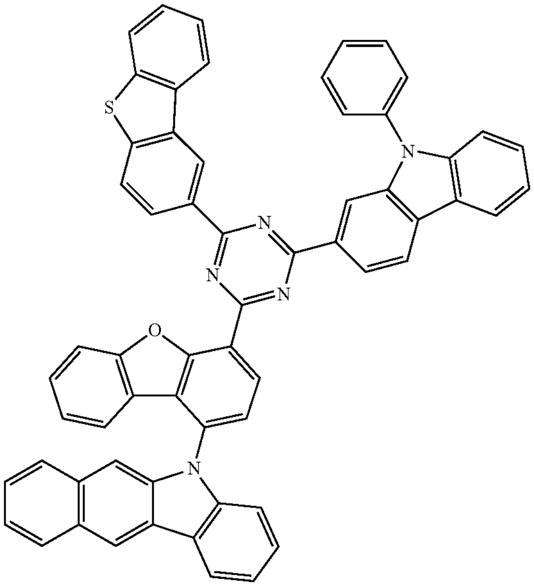
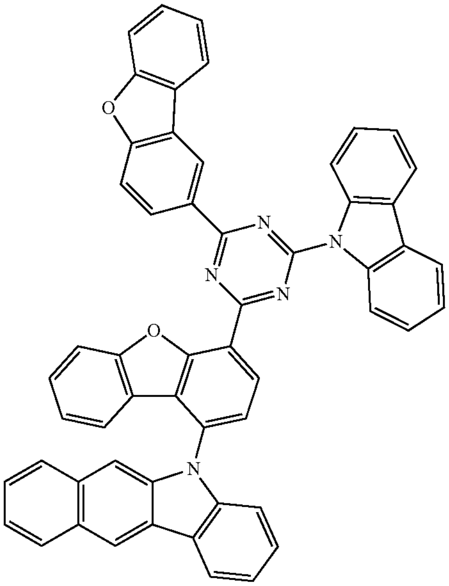

-continued
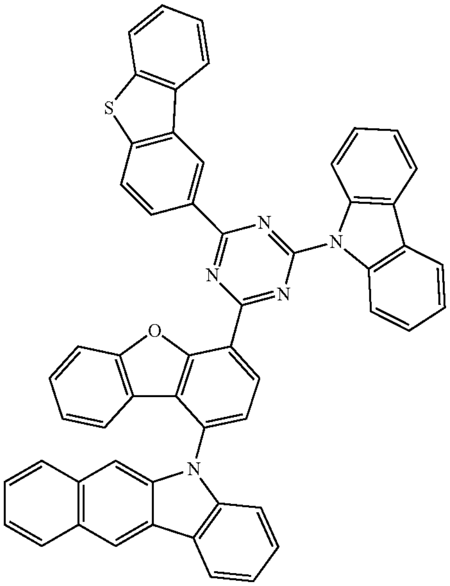
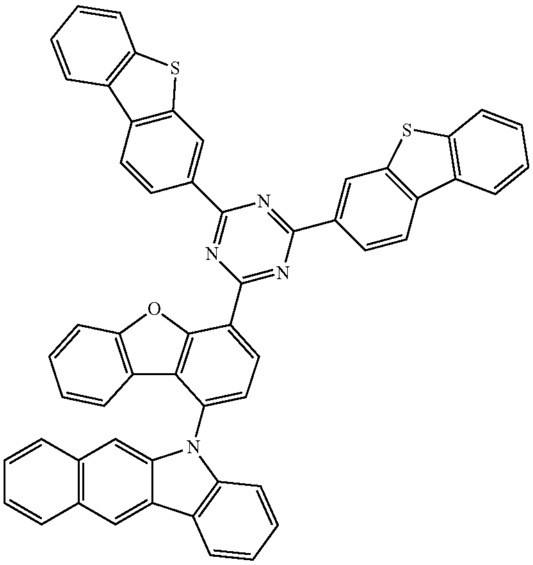
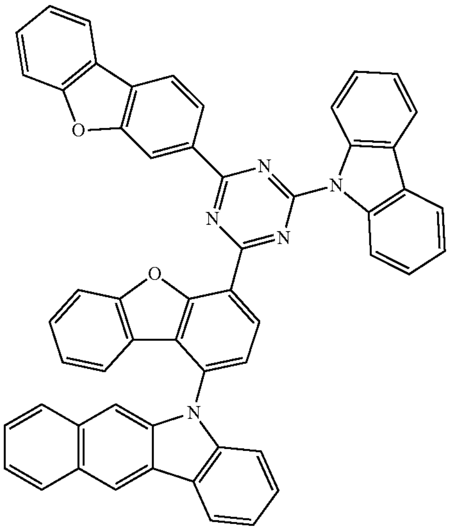
-continued
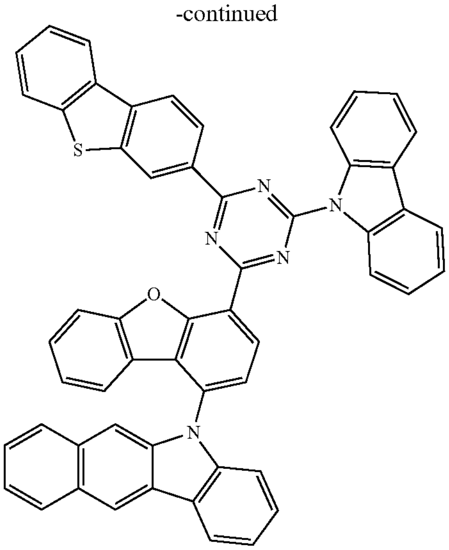
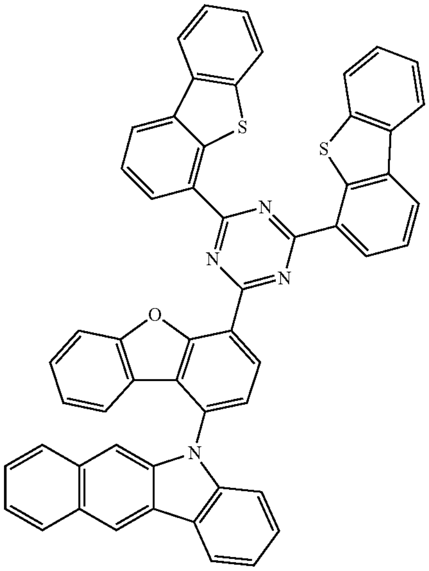
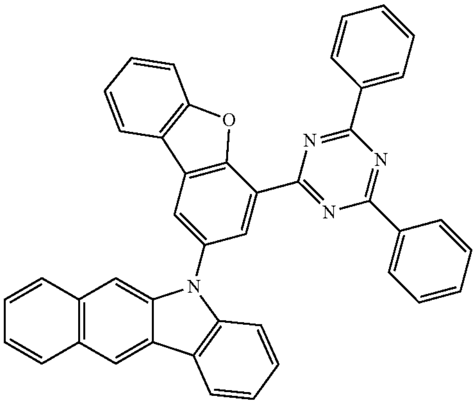

-continued
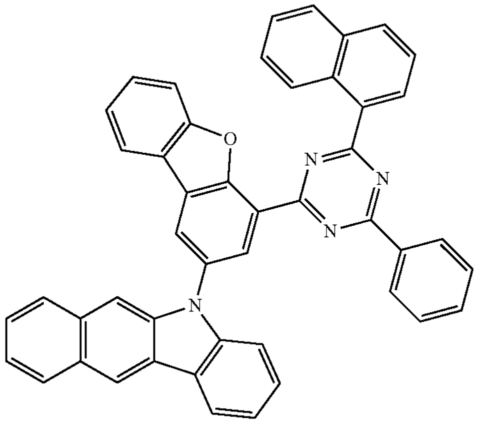
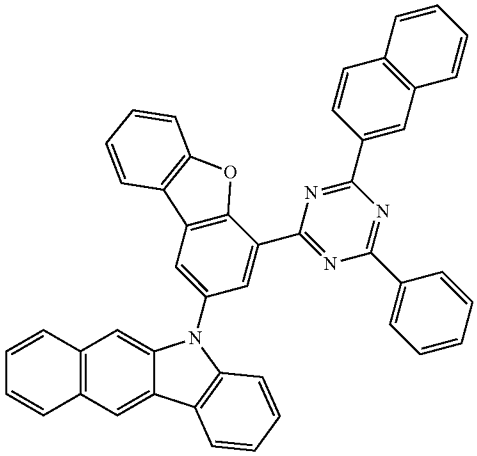
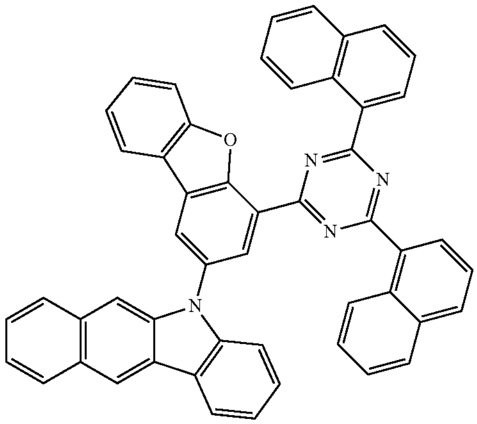
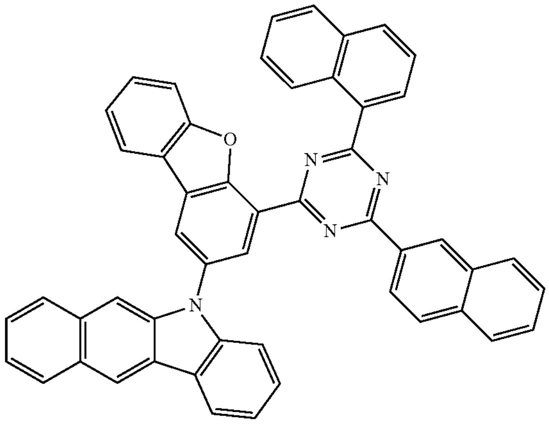
-continued
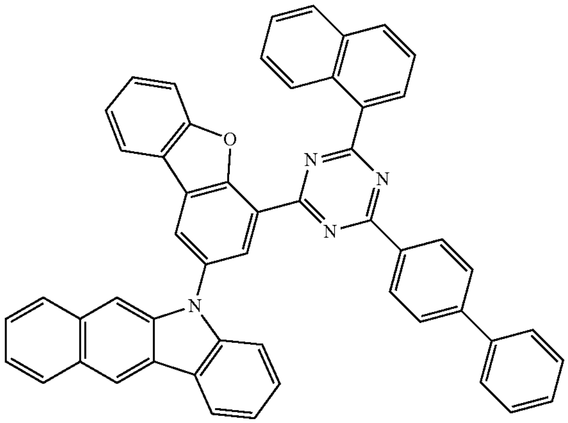
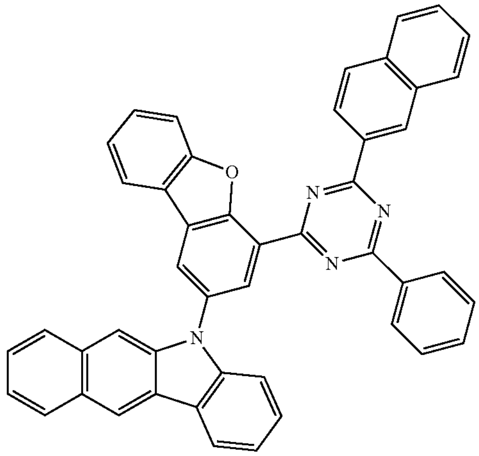
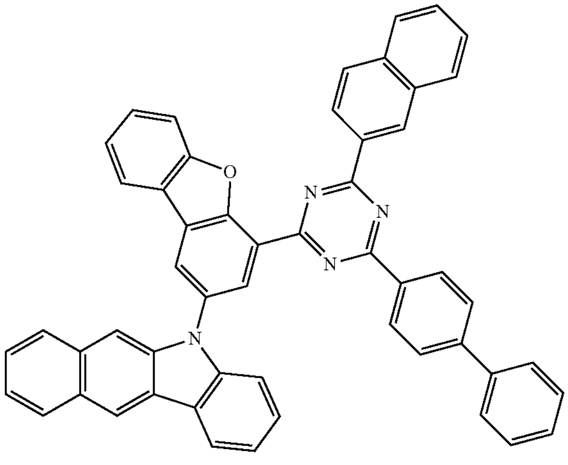

-continued
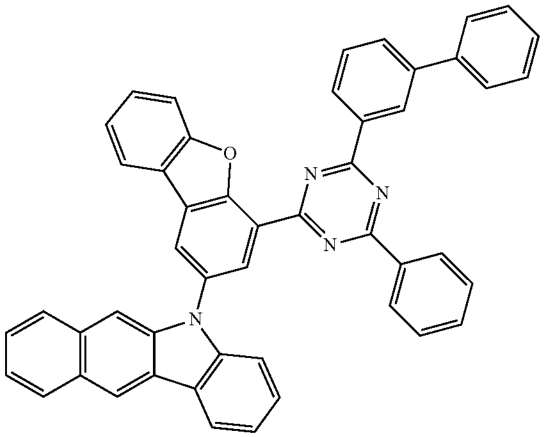
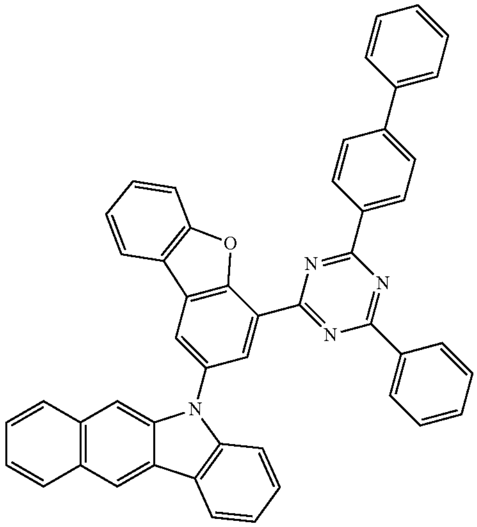
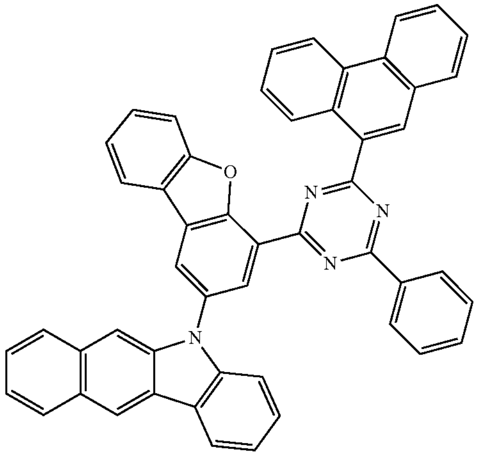
-continued
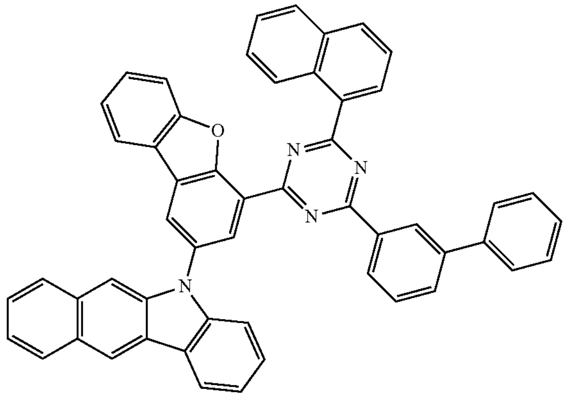
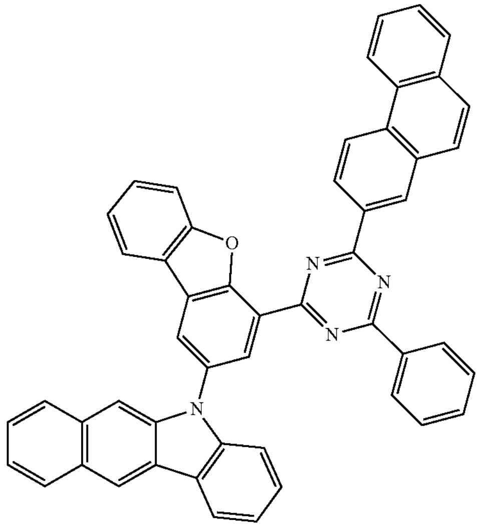
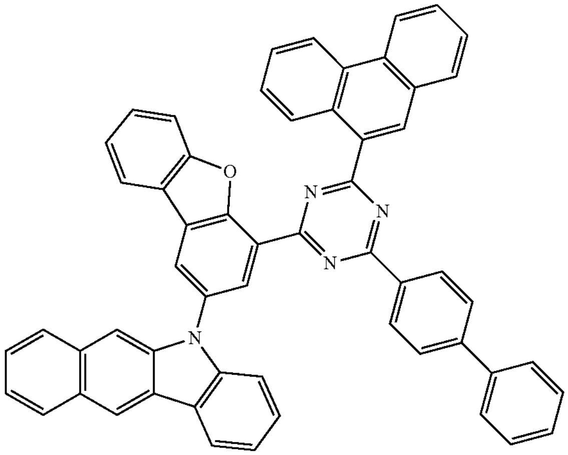

-continued
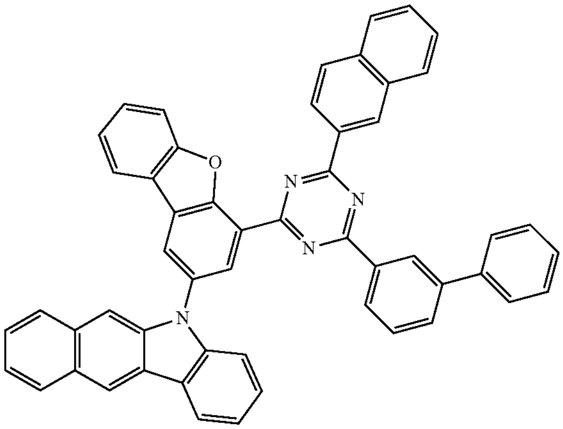
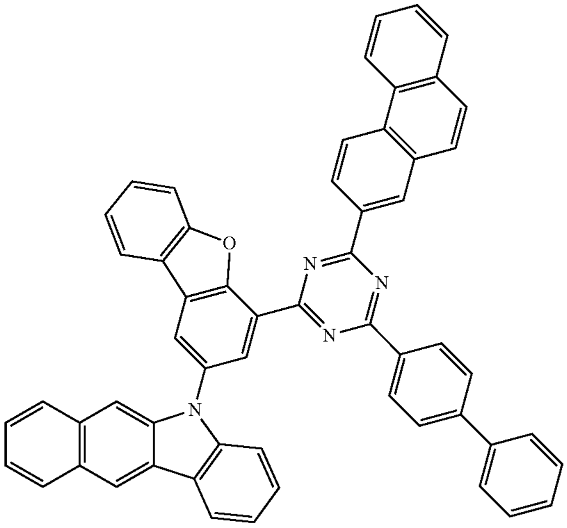
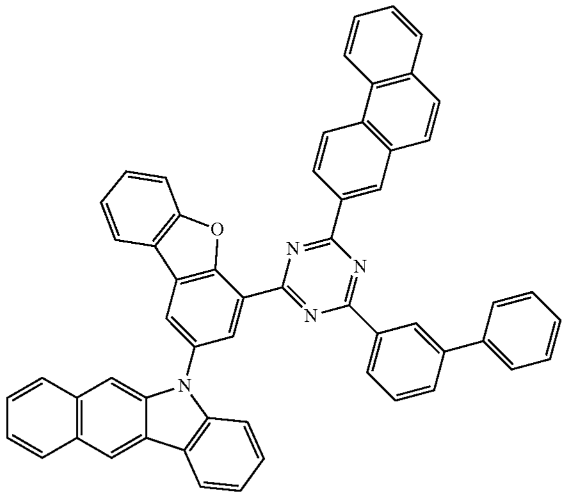
-continued
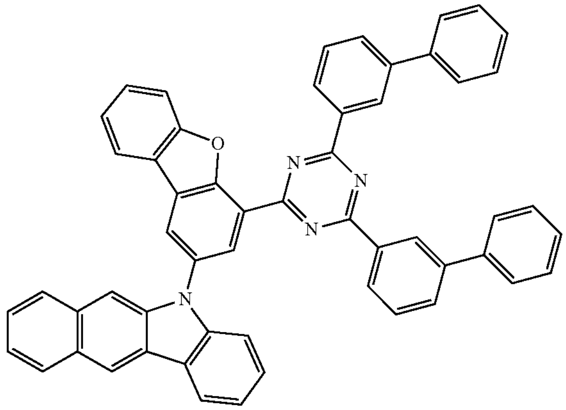
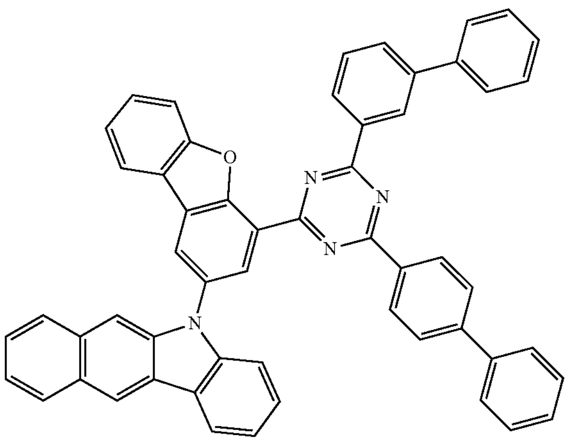
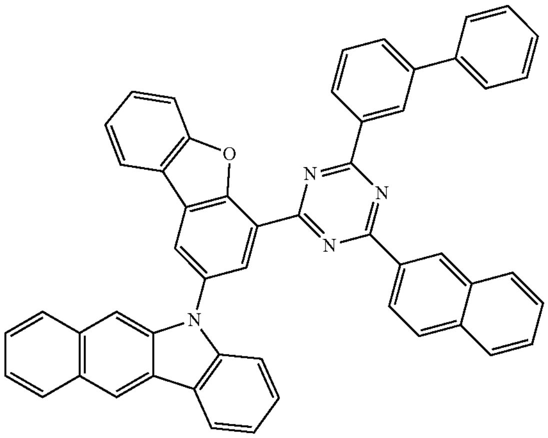

-continued
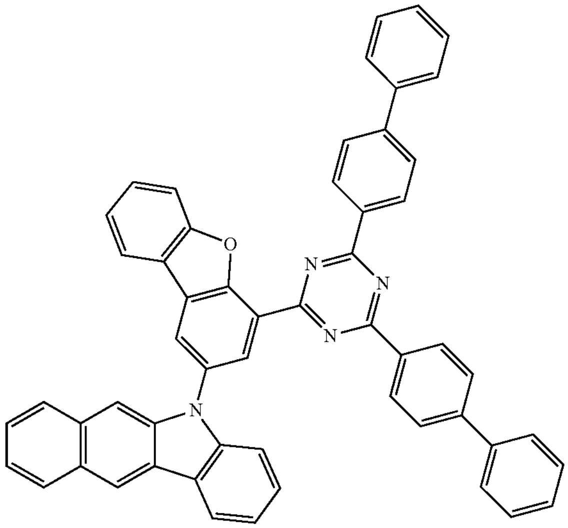
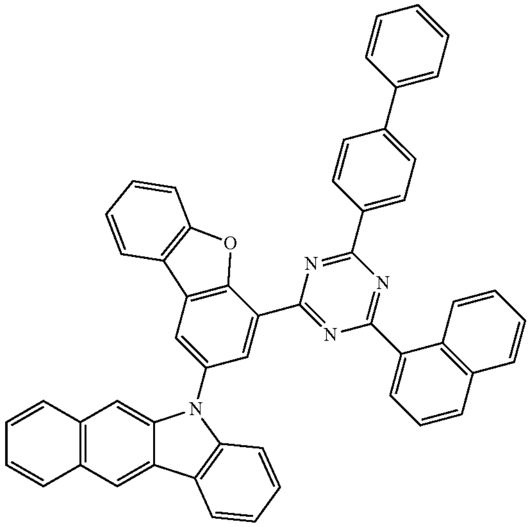
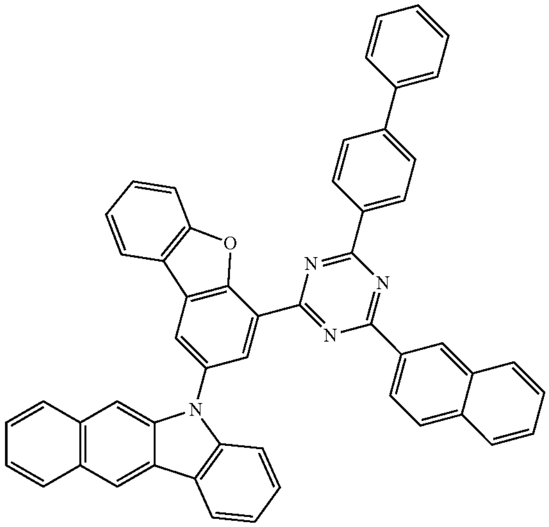
-continued
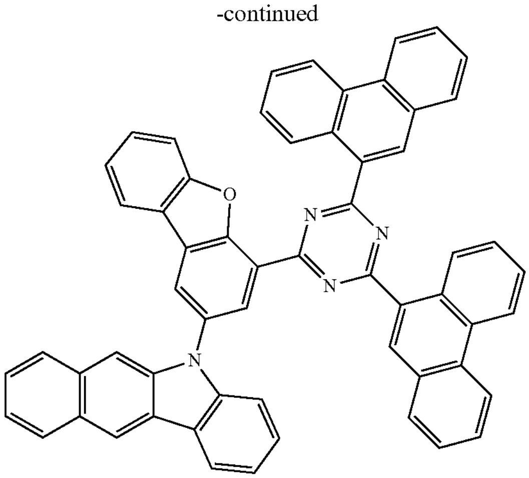
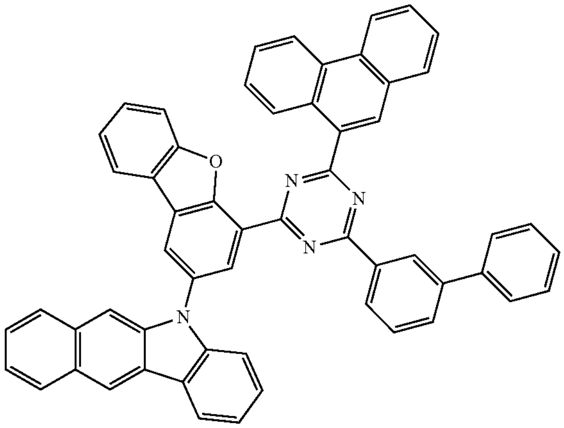
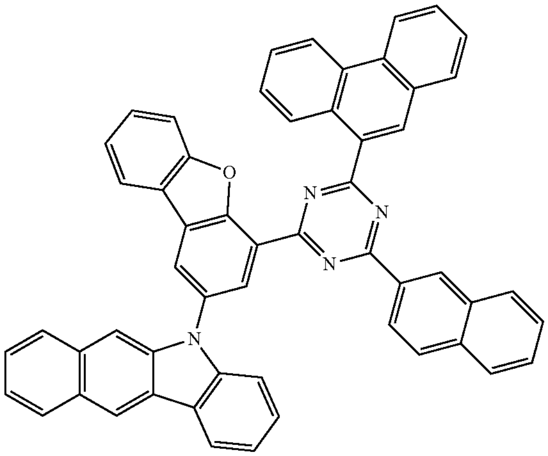

-continued
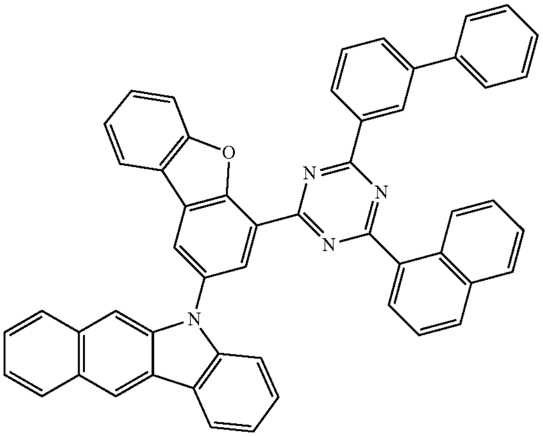
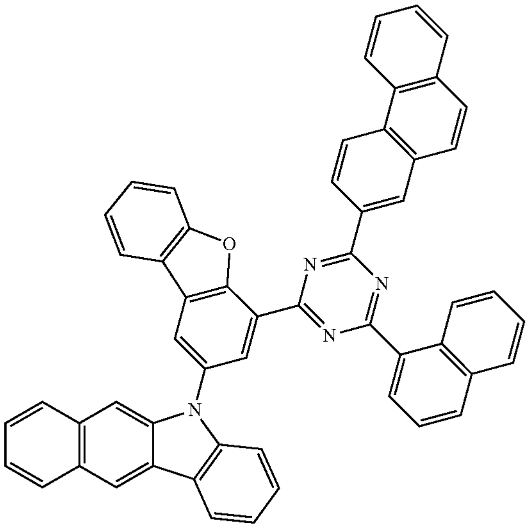
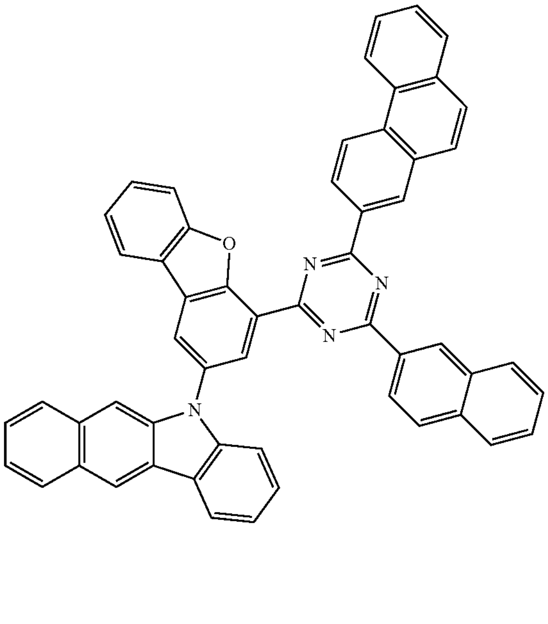
-continued
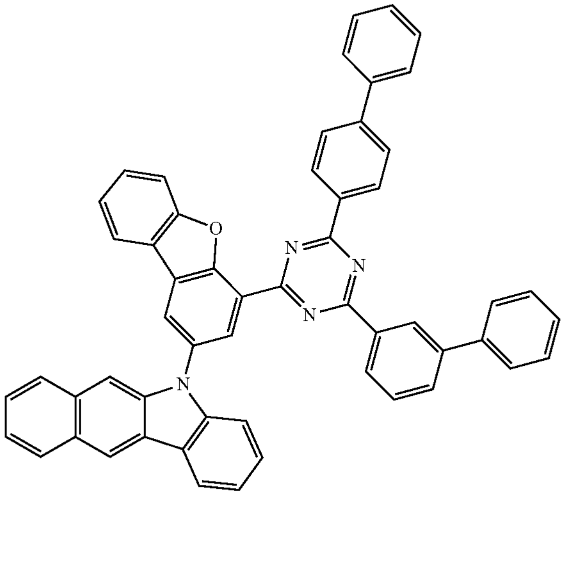
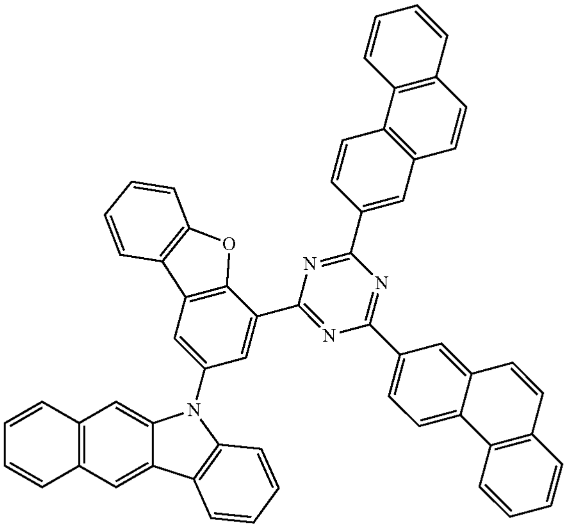
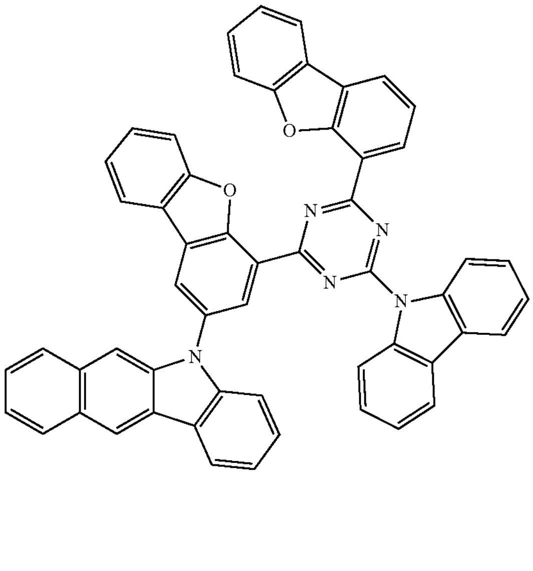

-continued
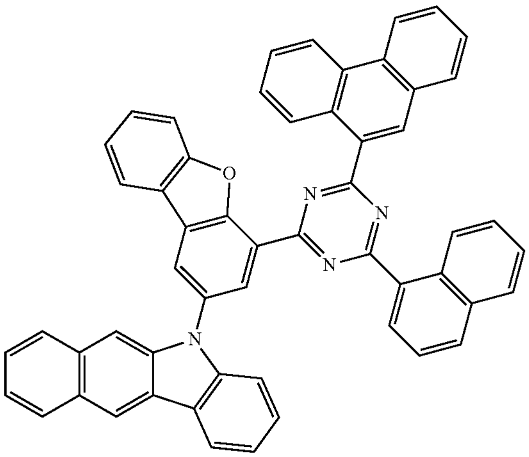
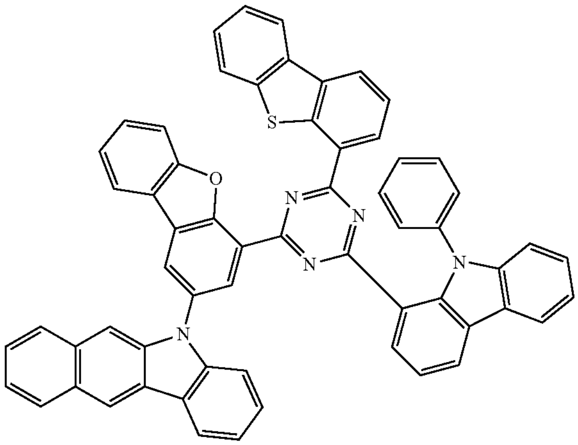
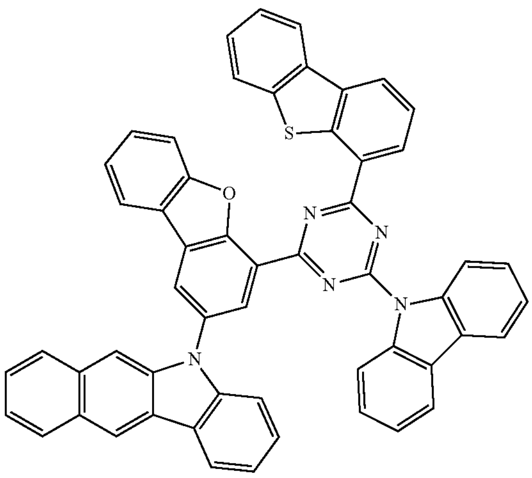
-continued
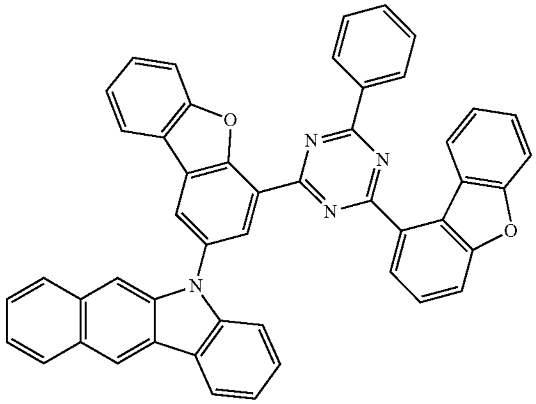
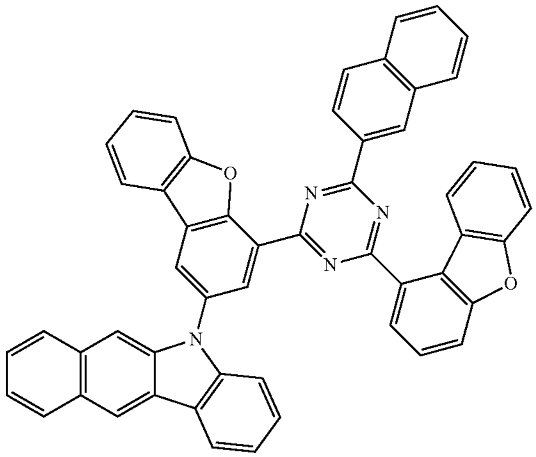
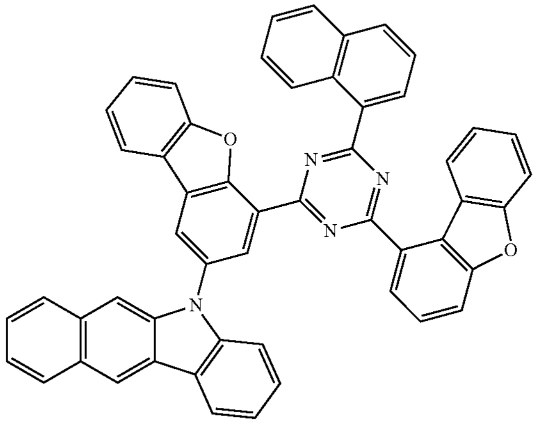
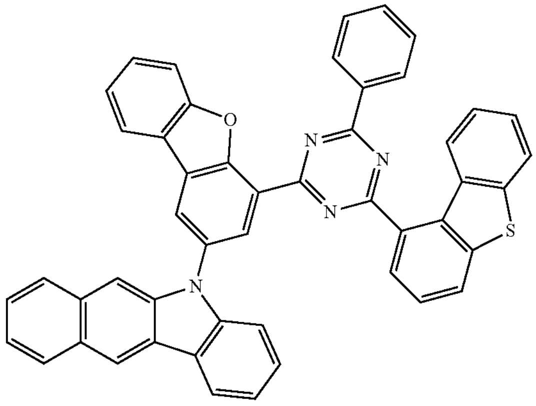

-continued
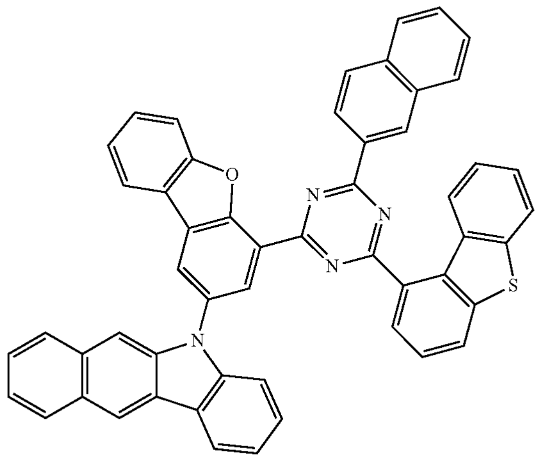
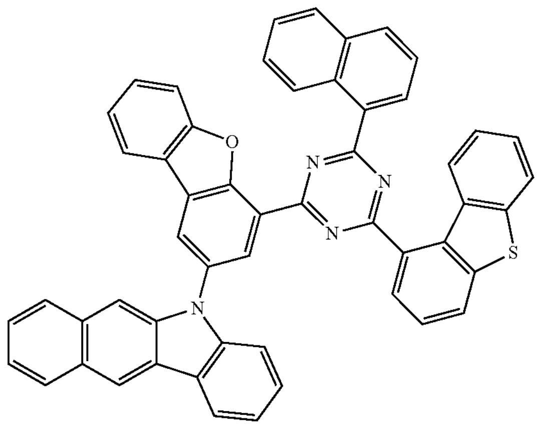
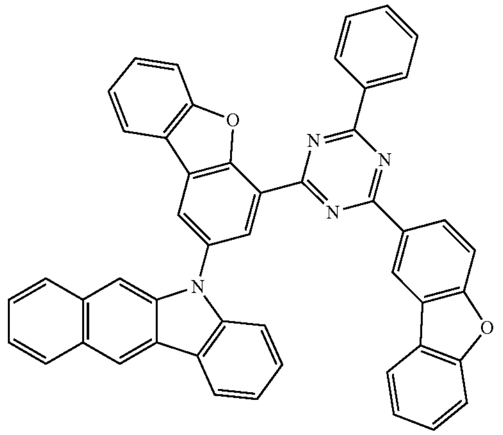
-continued
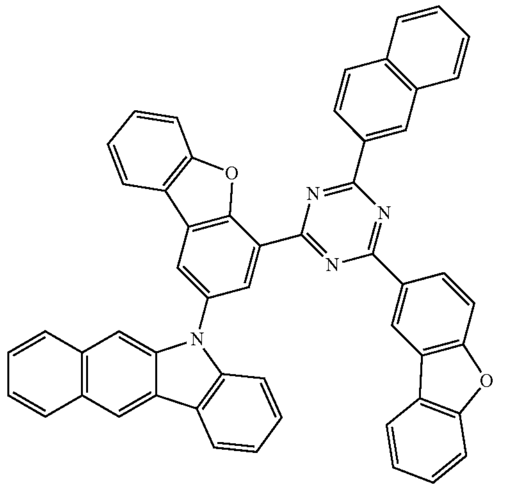
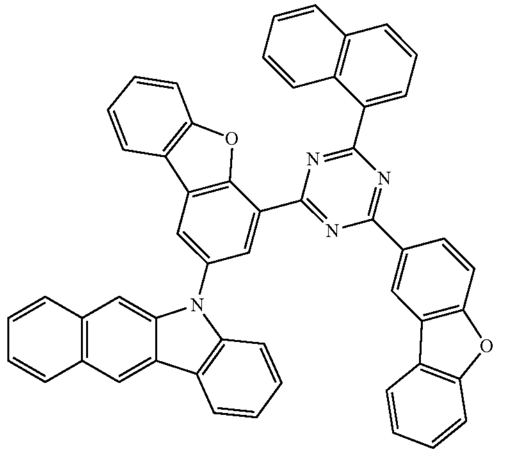
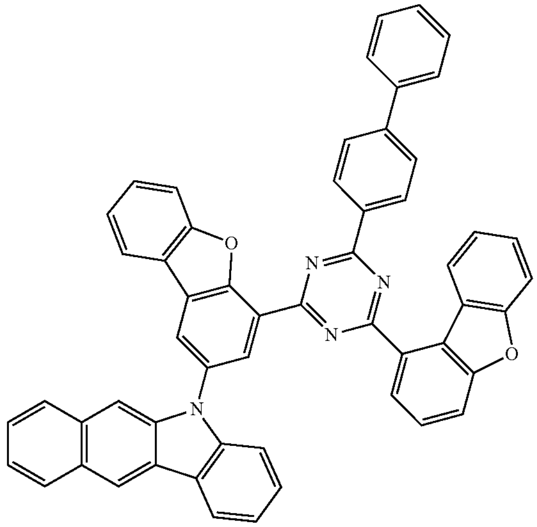

-continued
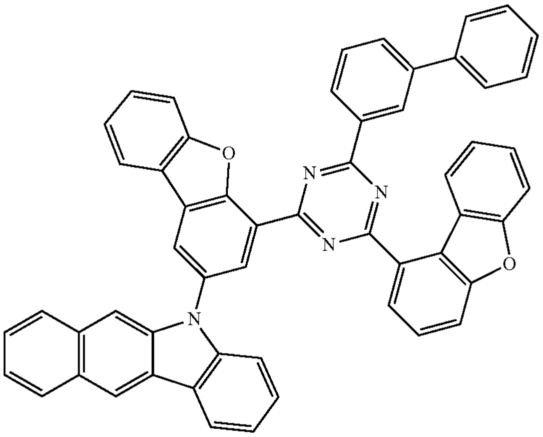
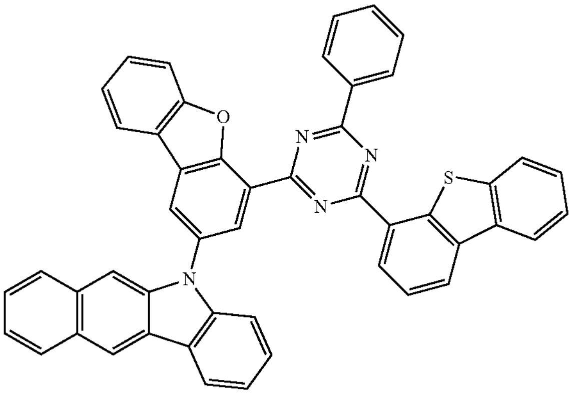
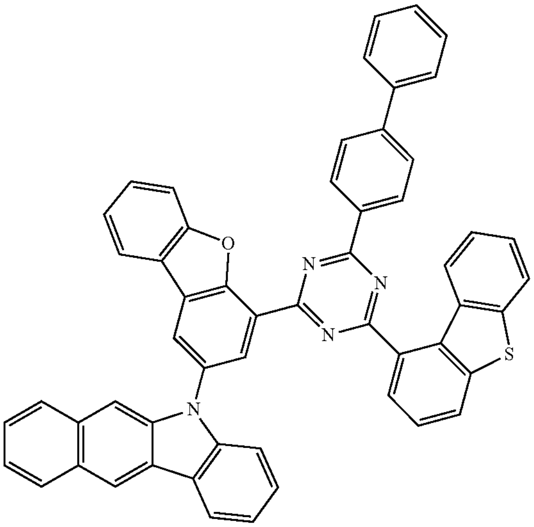
-continued
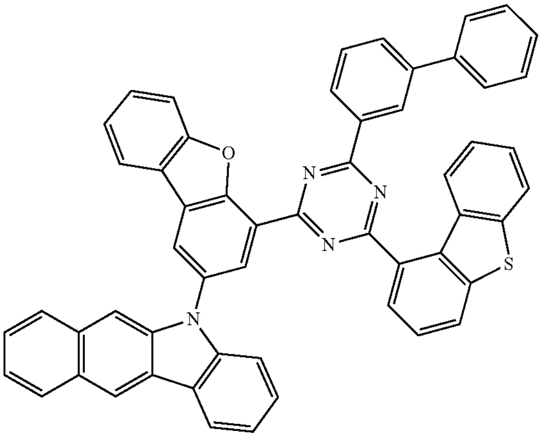
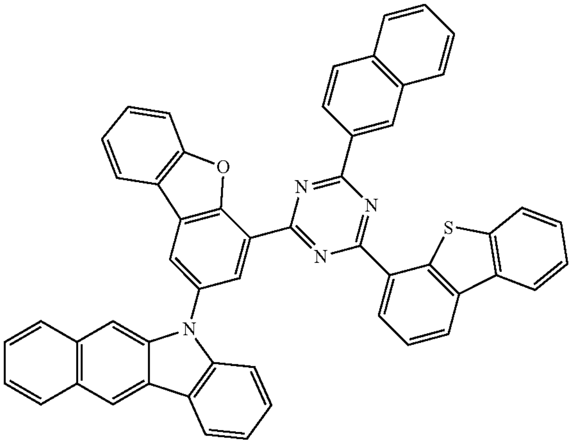
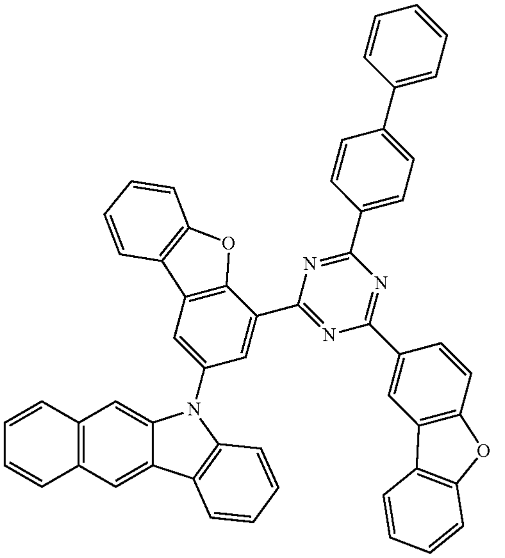

-continued
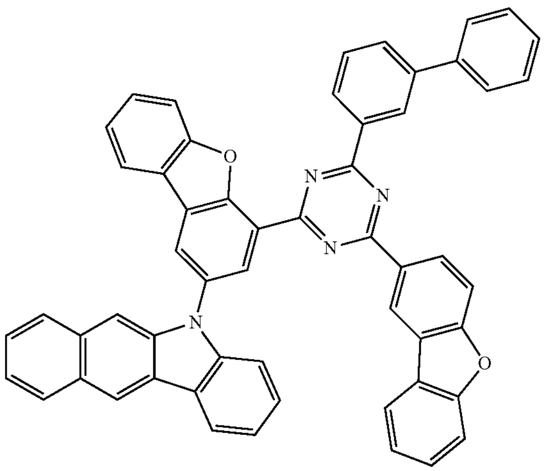
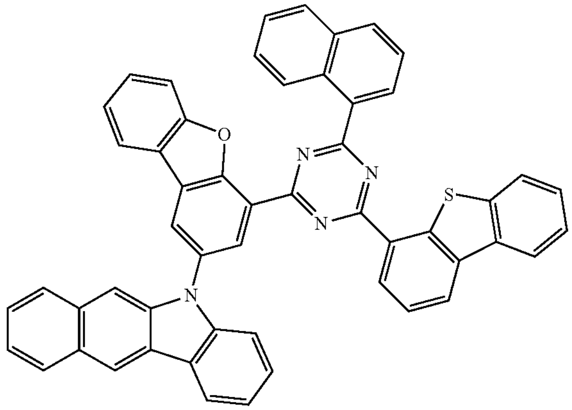
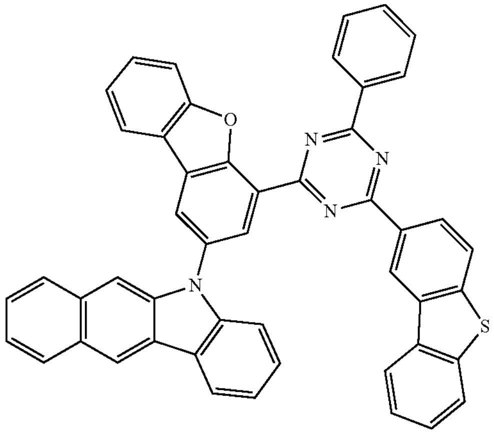
-continued
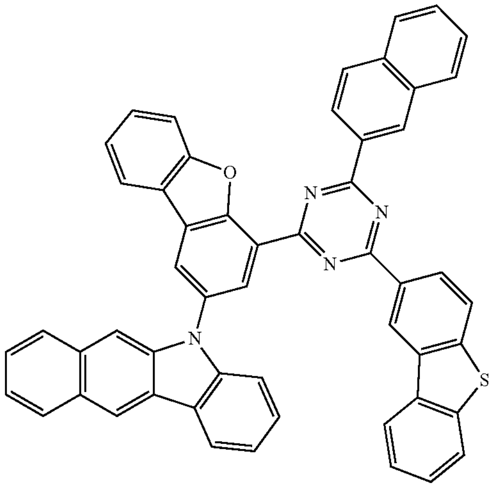
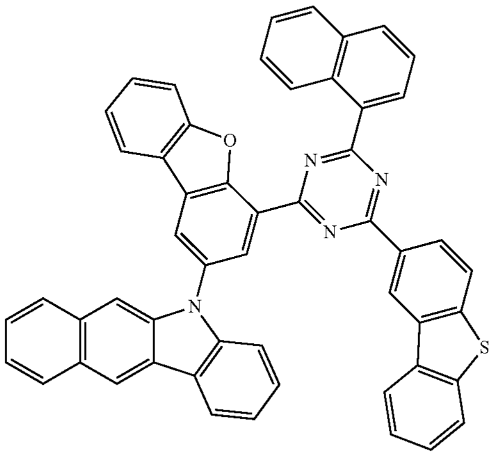
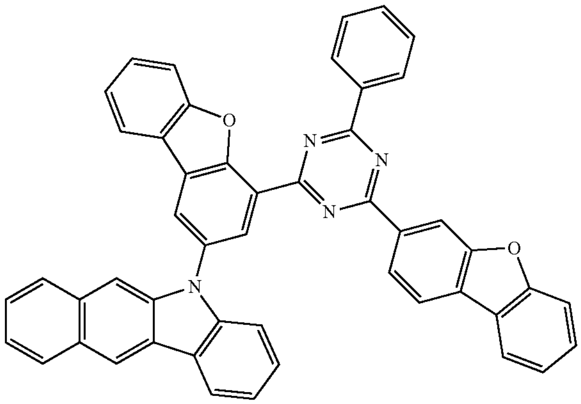

-continued
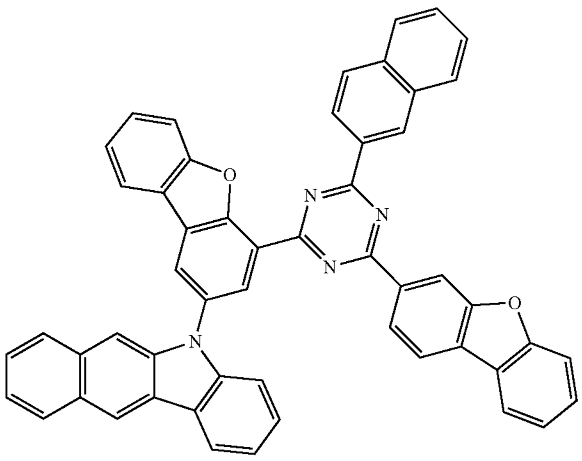
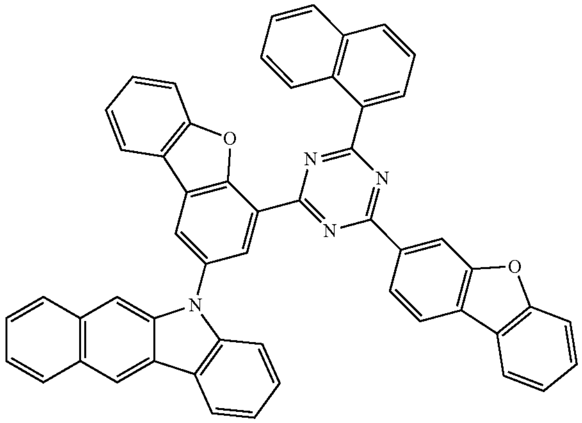
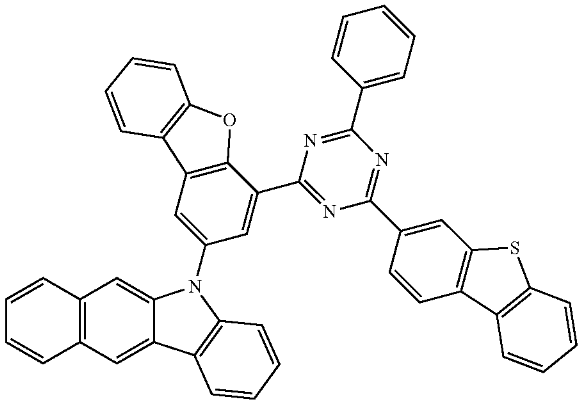
-continued
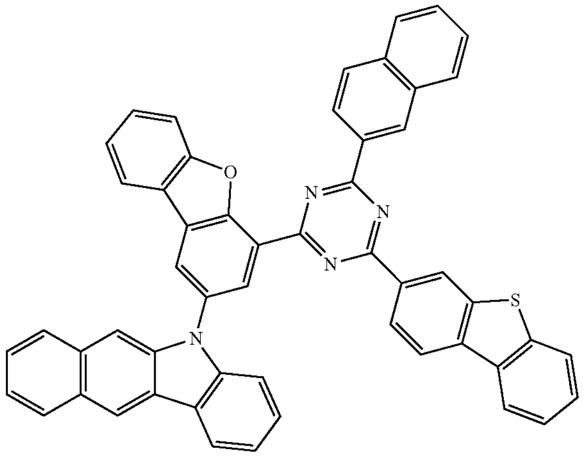
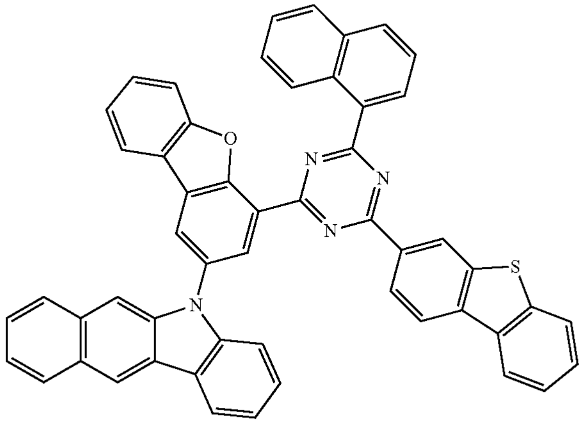
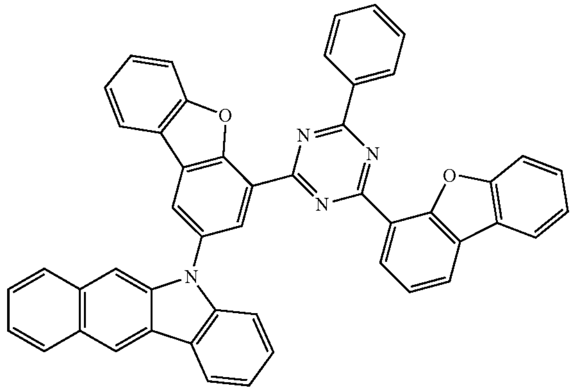
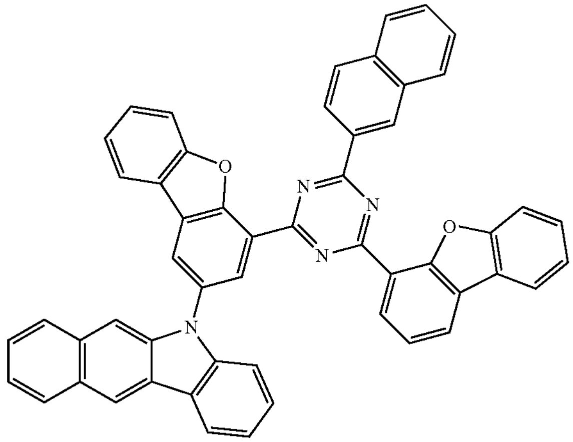

-continued
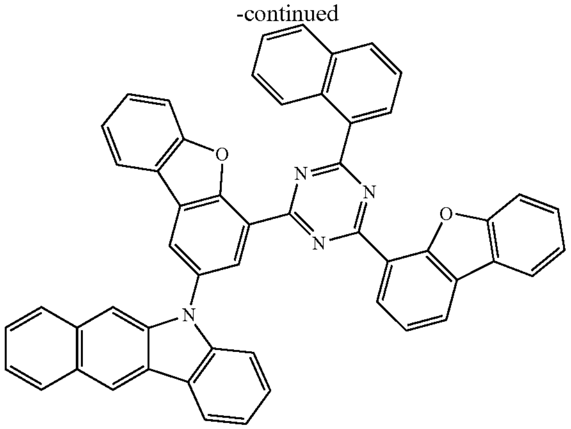
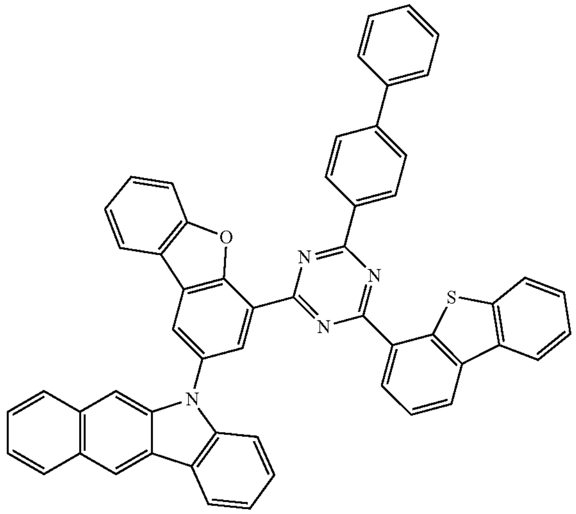
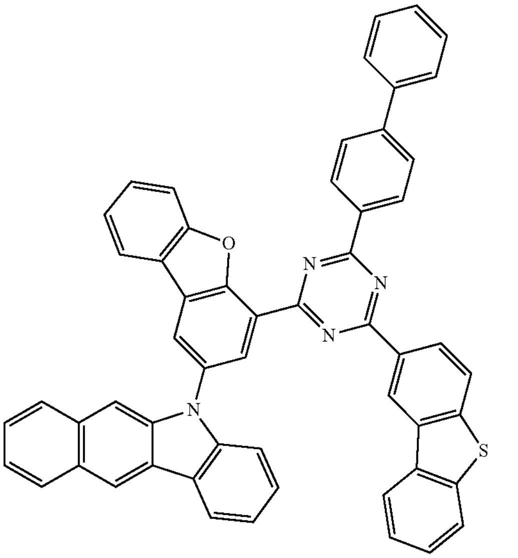
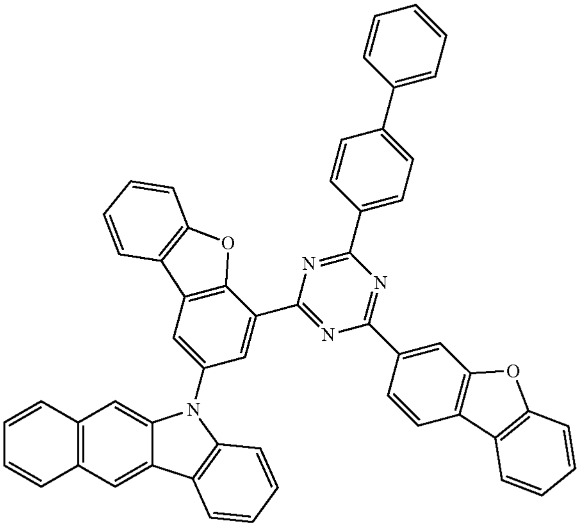
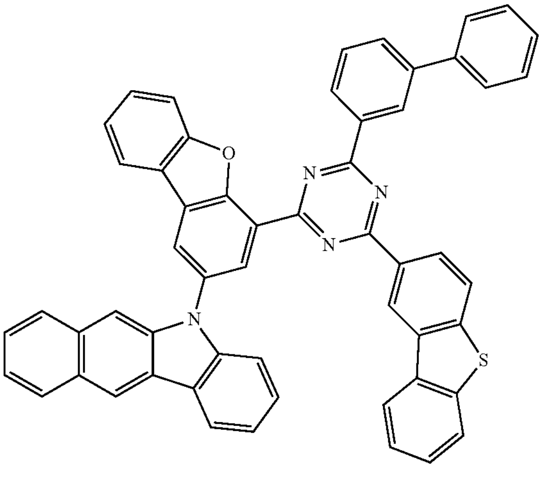
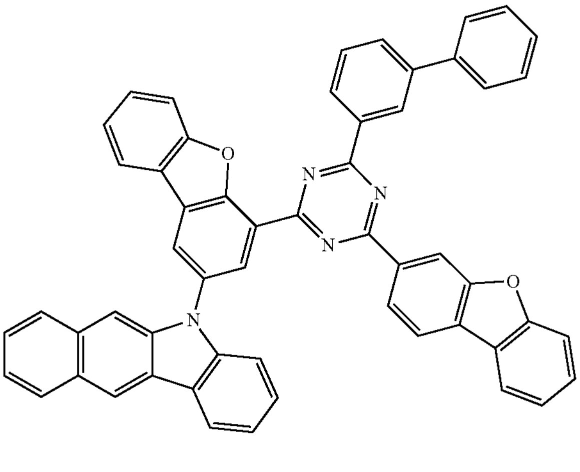
-continued -continued
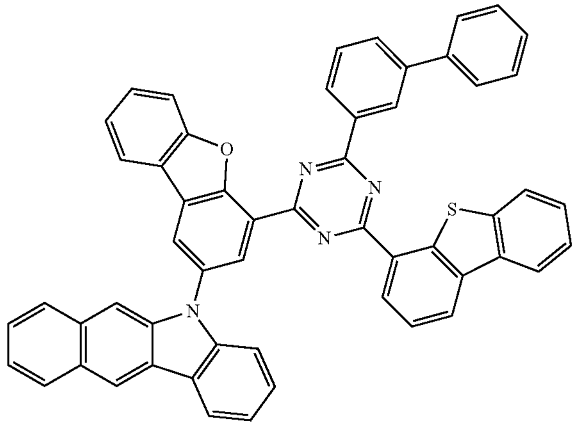
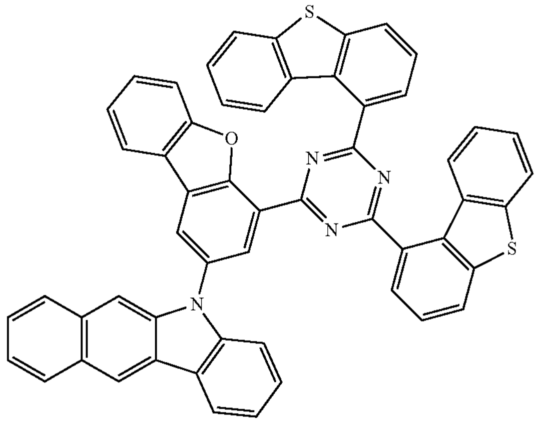
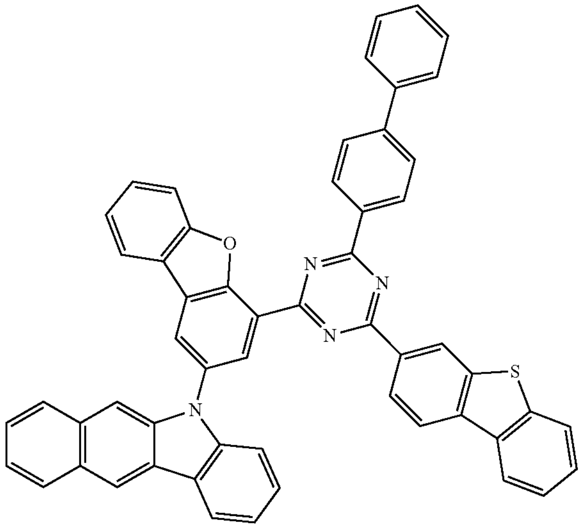
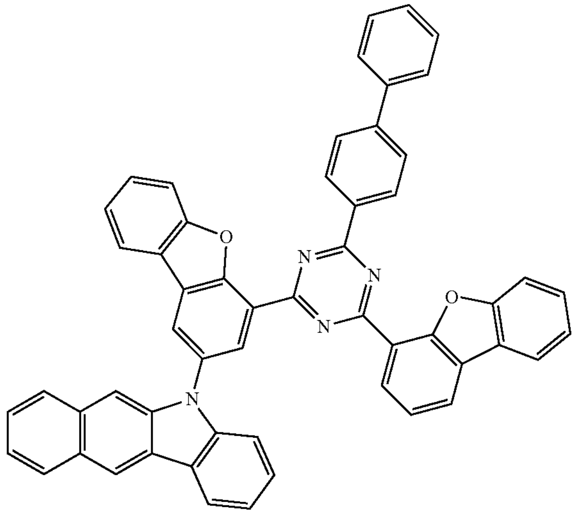
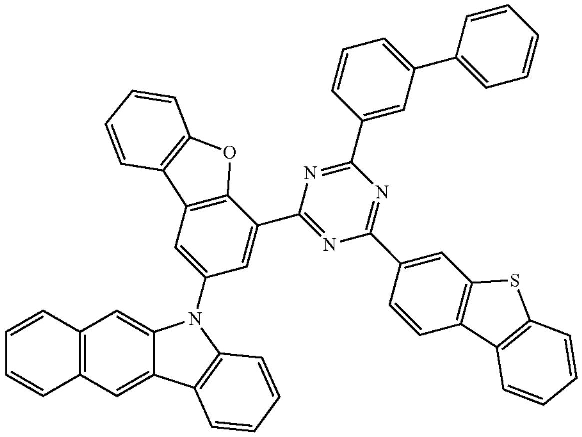
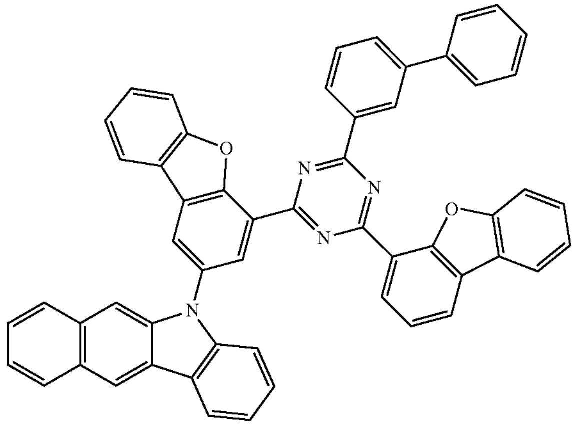
-continued -continued
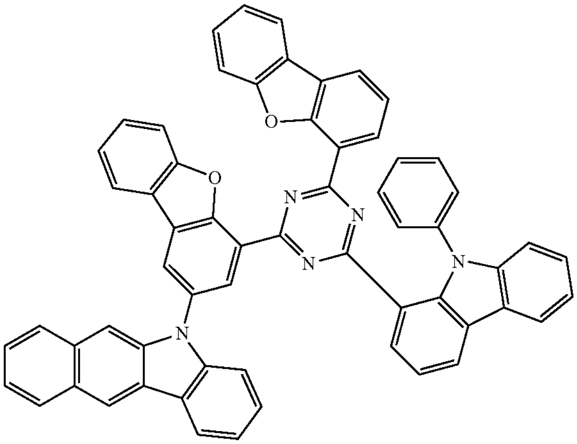
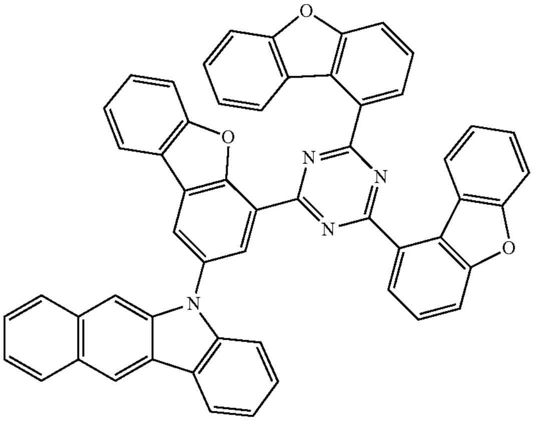
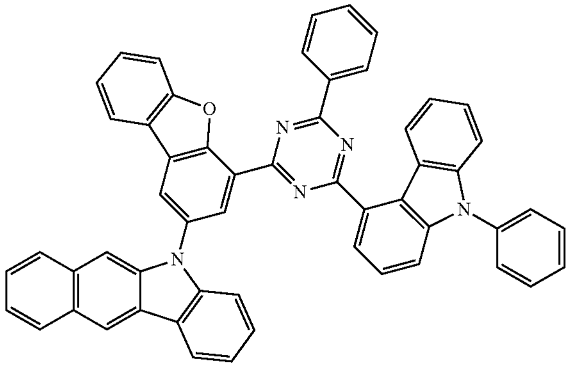
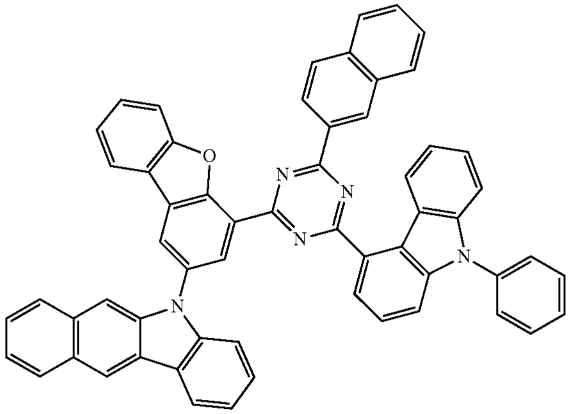
-continued
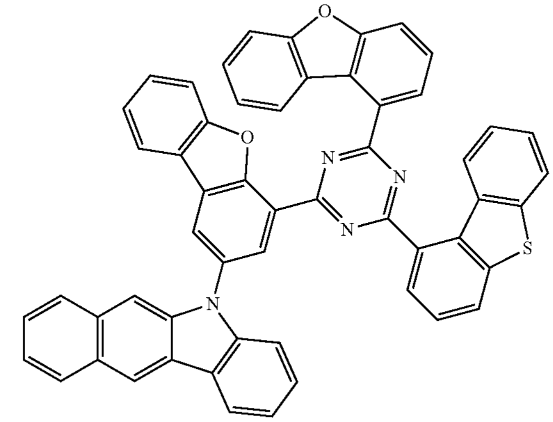
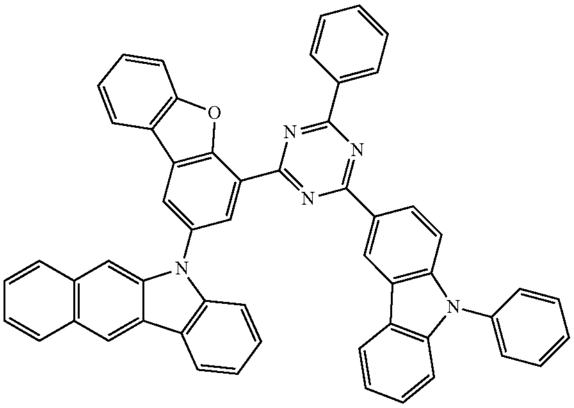
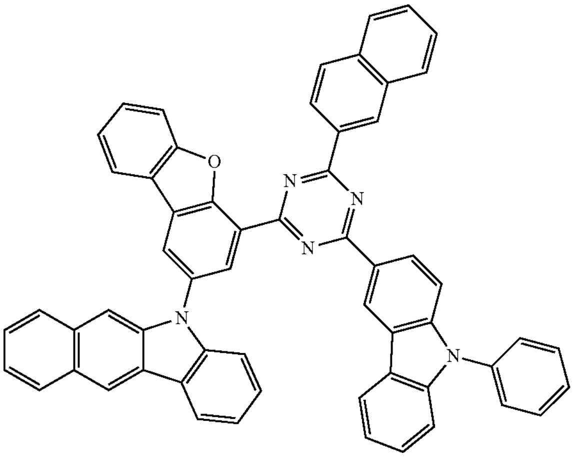

-continued
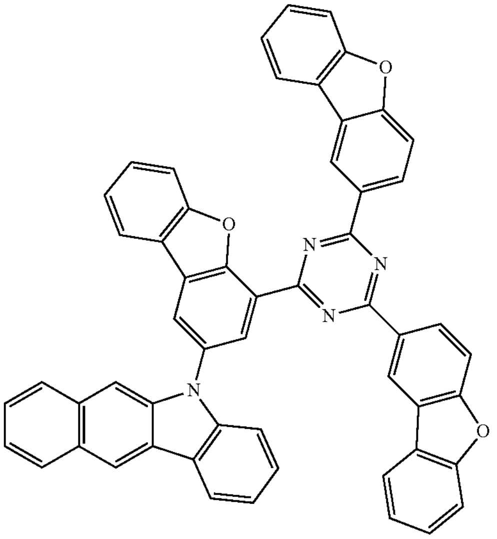
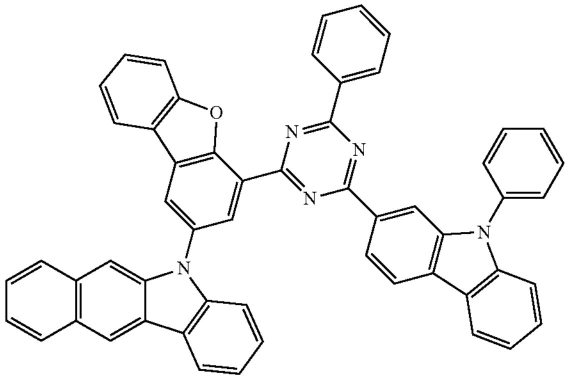
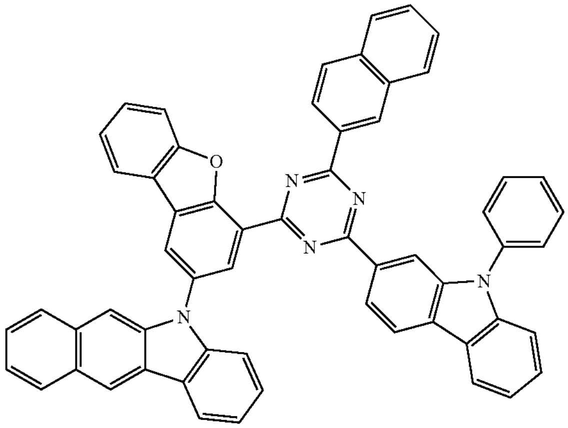
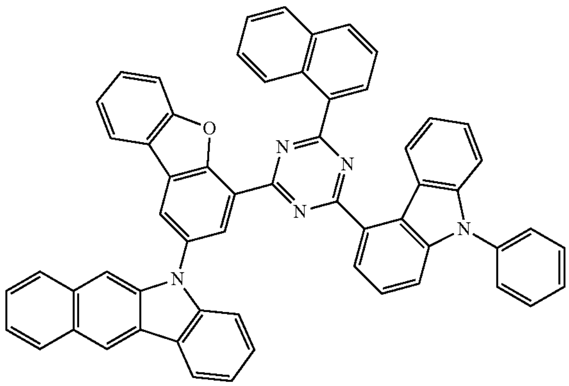
-continued
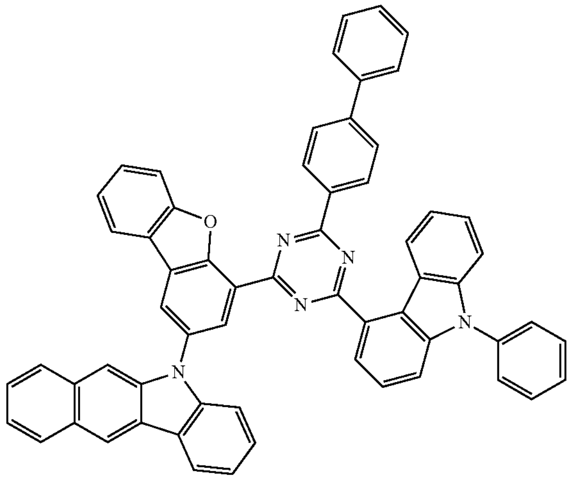
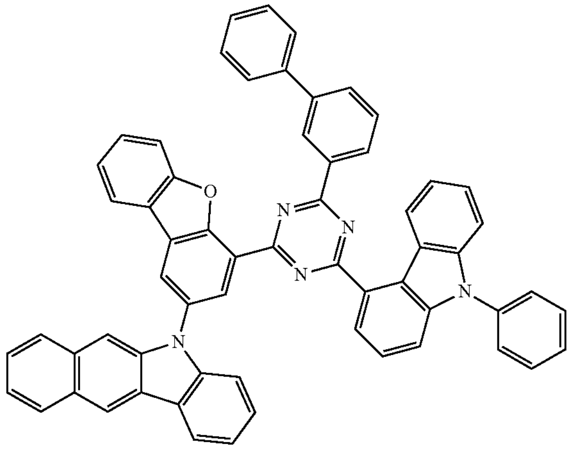
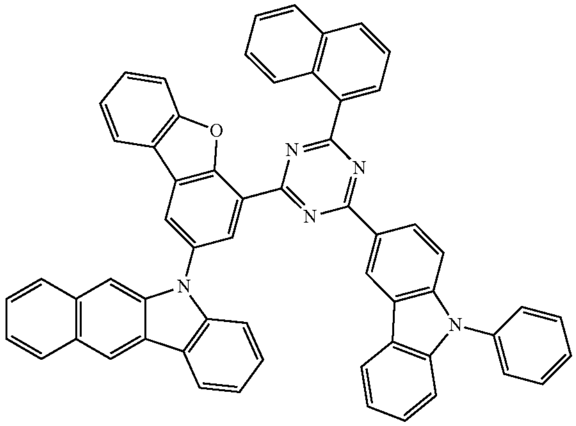

-continued
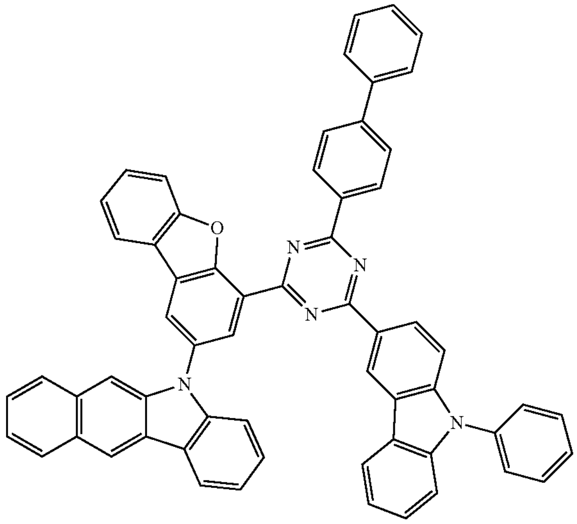
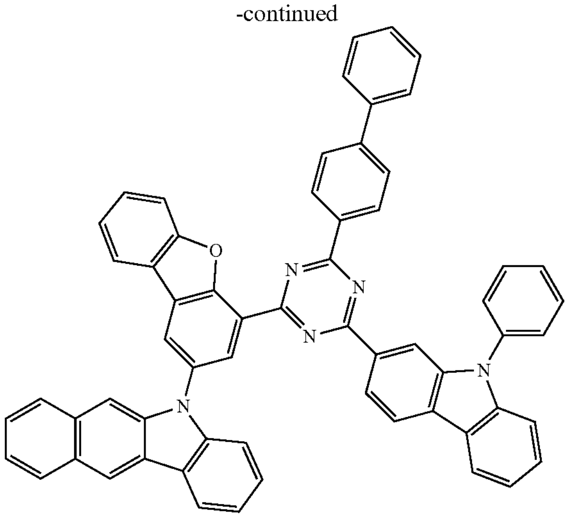
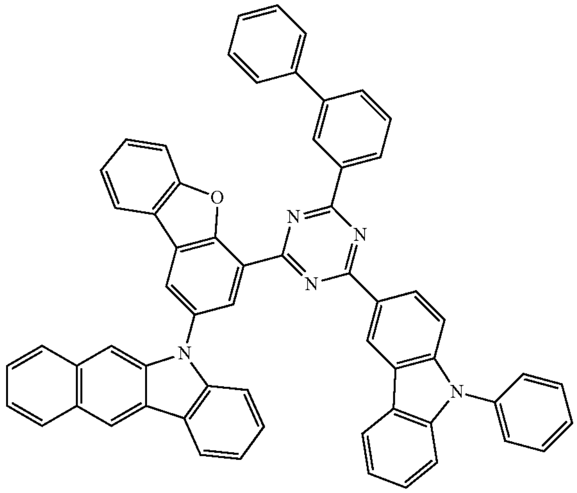
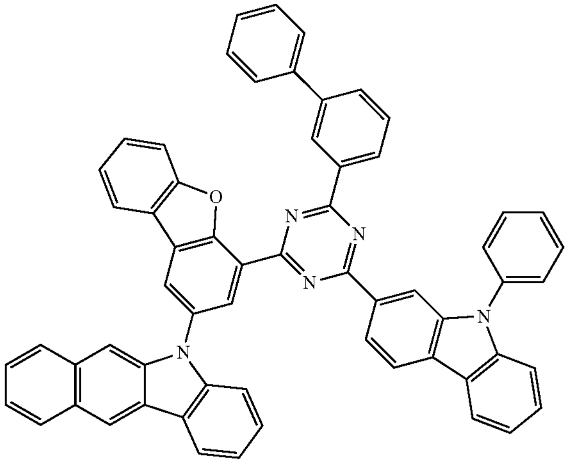
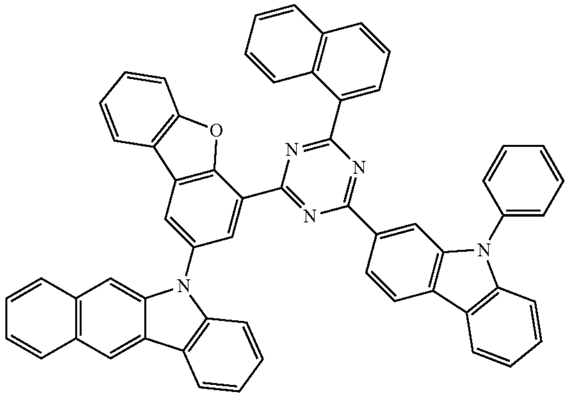
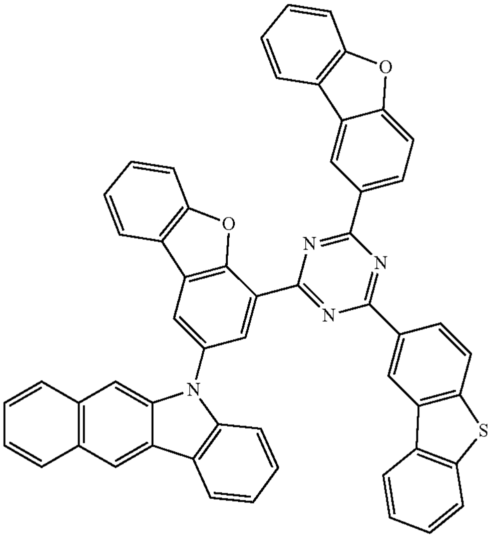
-continued -continued
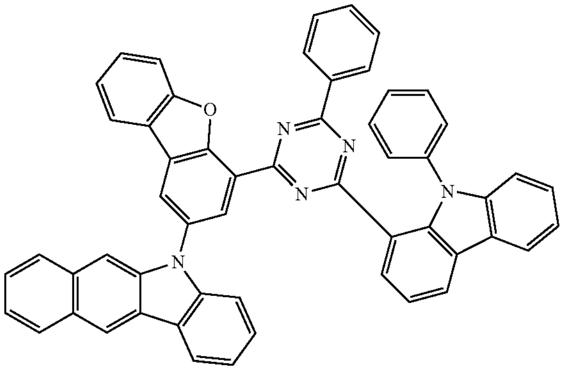
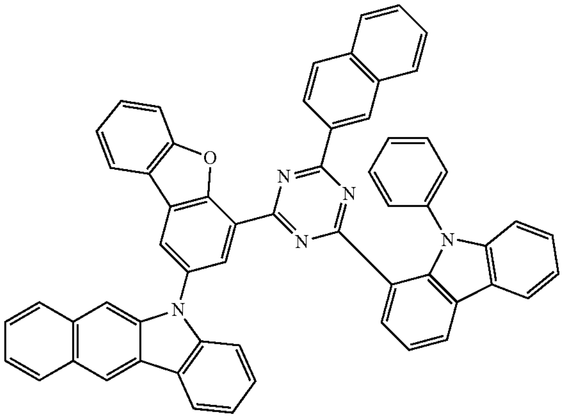
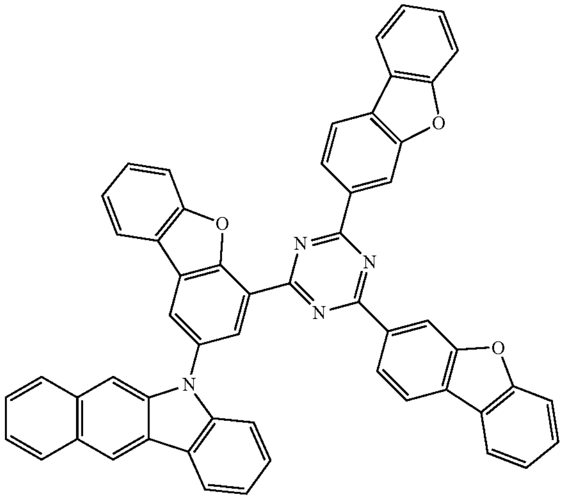
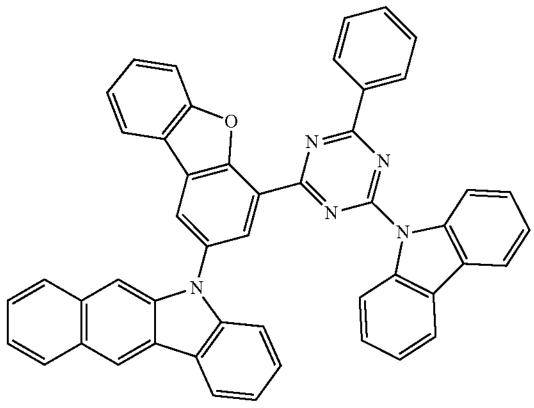
-continued
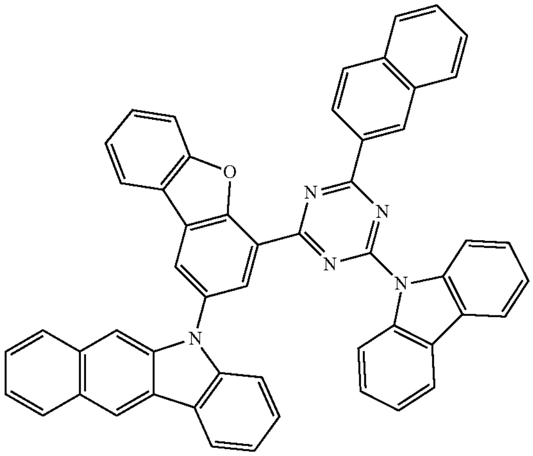
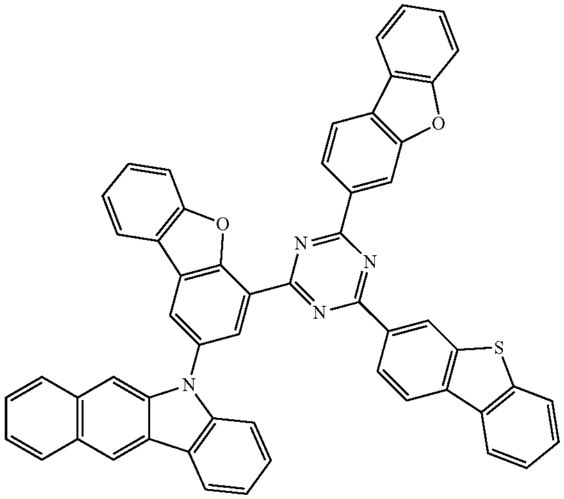
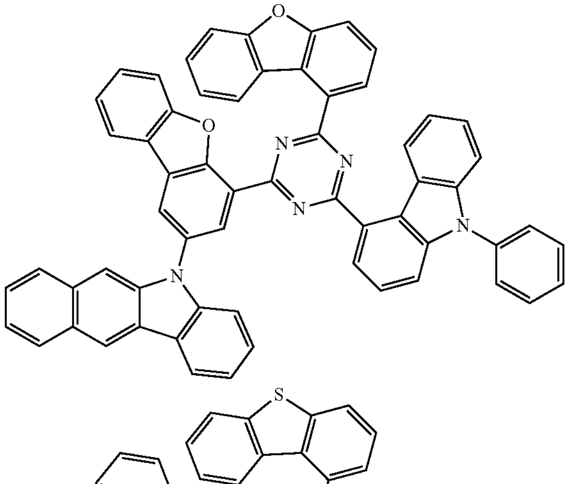
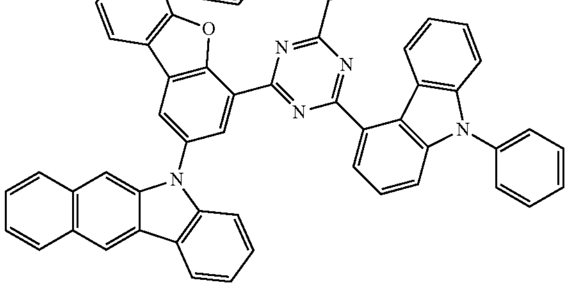

-continued
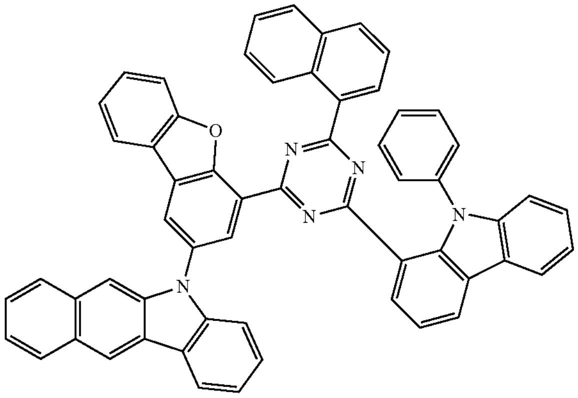
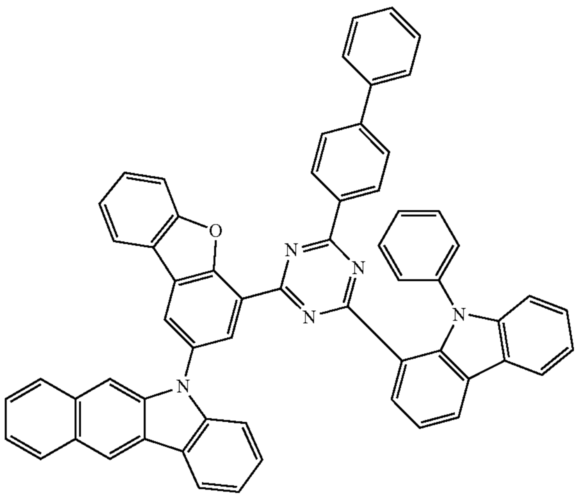
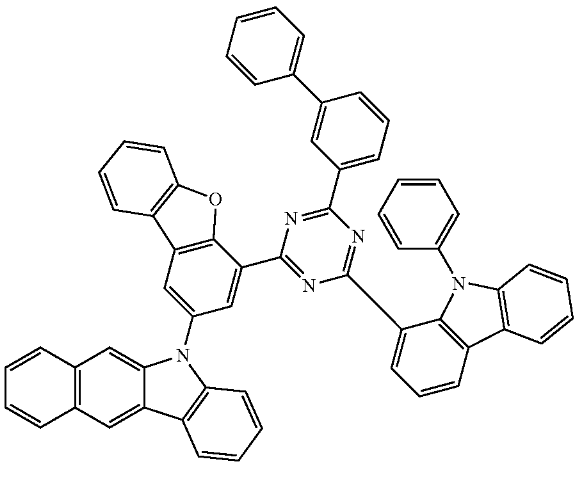
-continued
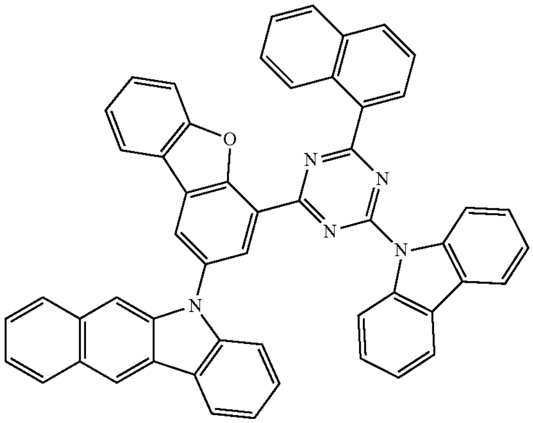
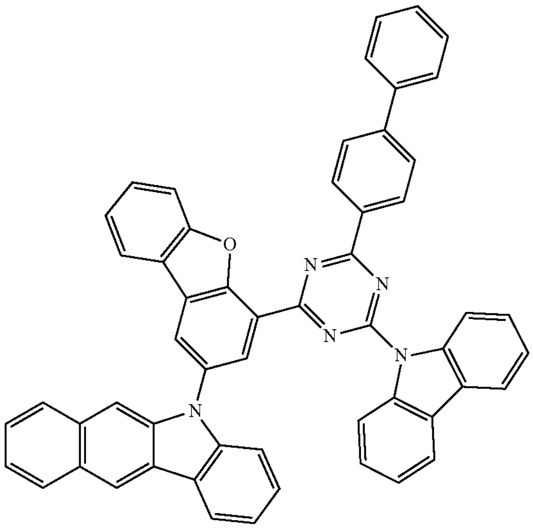
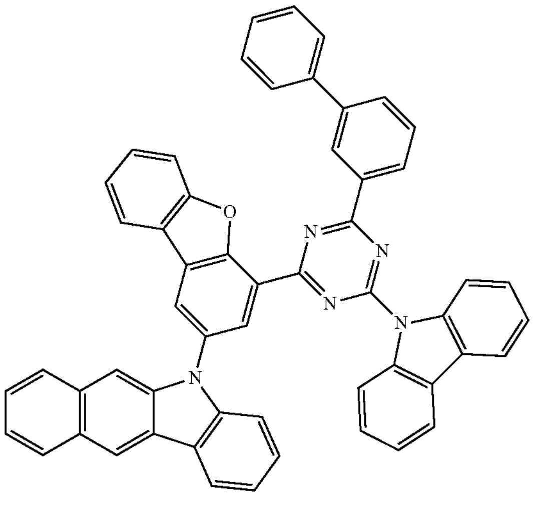

1323
-continued
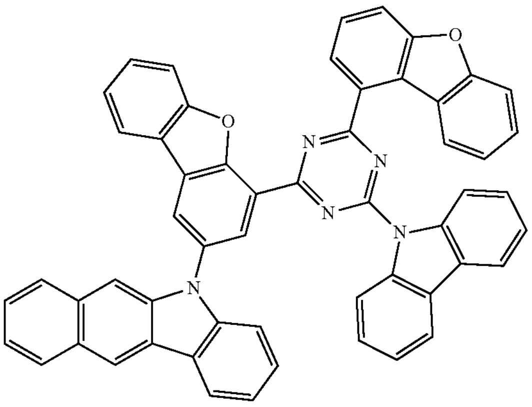
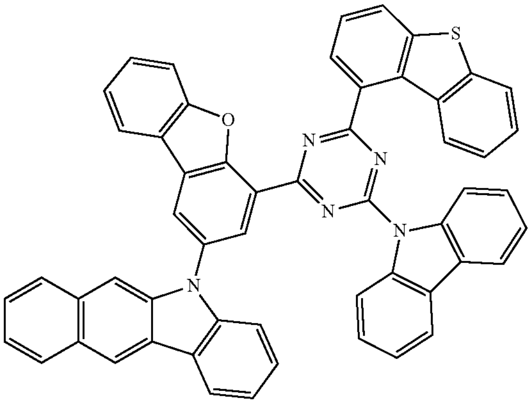
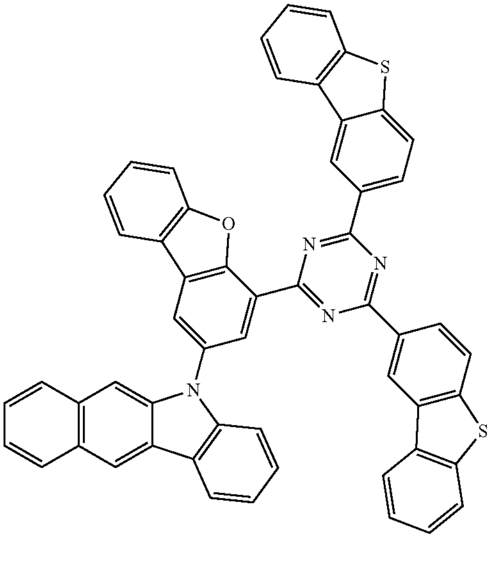
1324
-continued
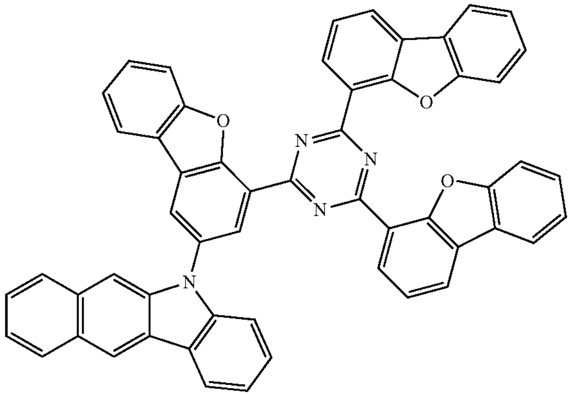
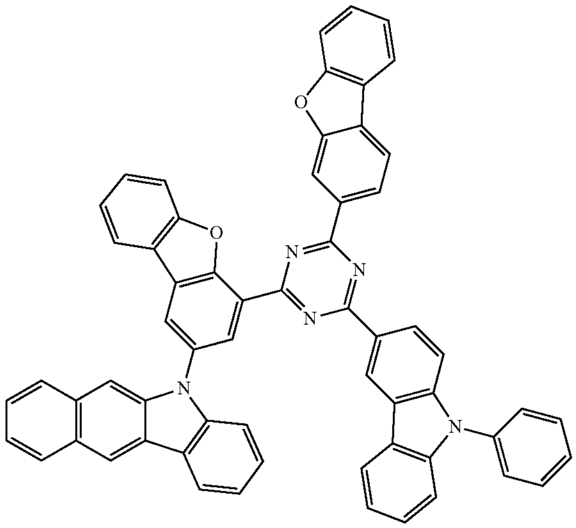
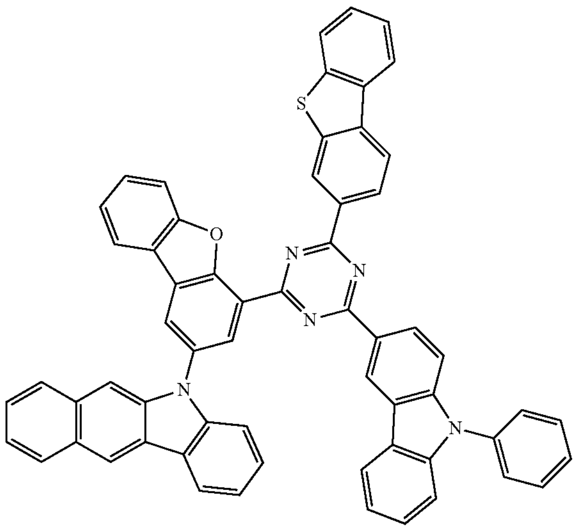

-continued
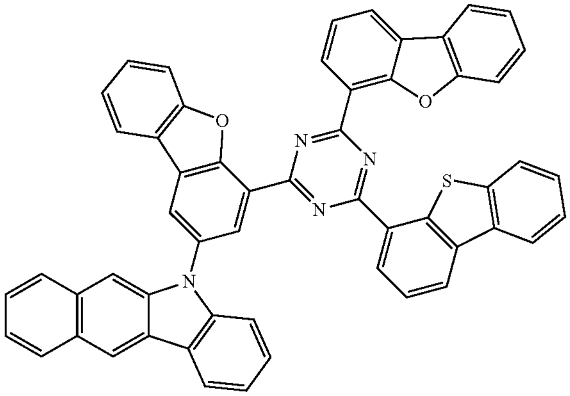
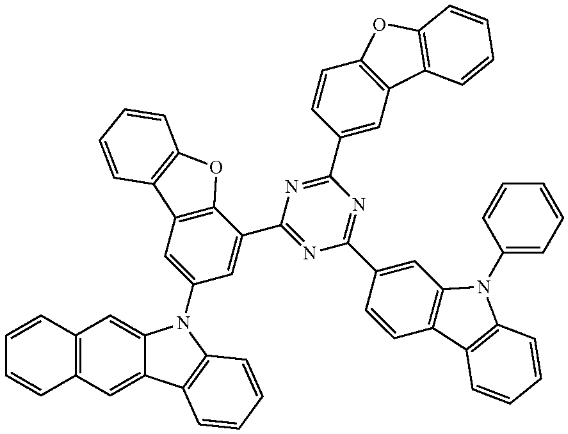
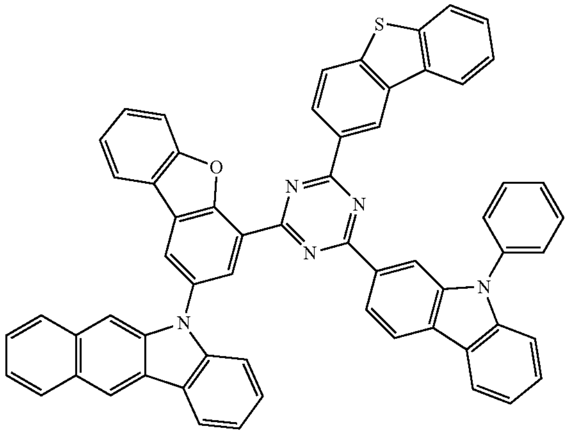
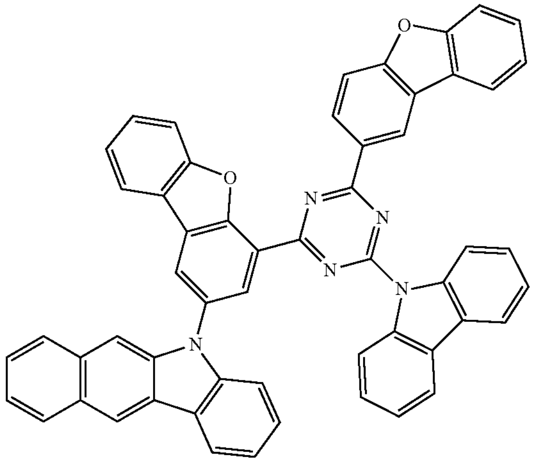
-continued
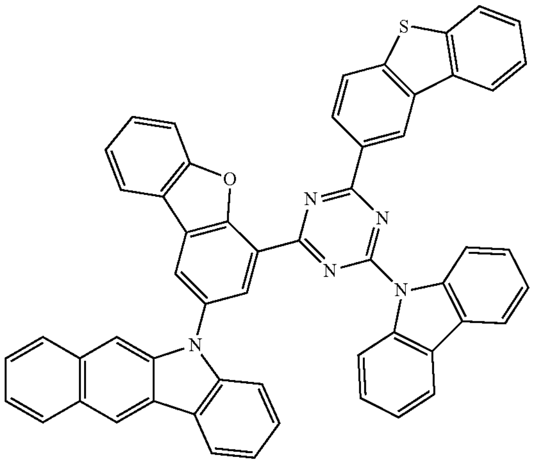
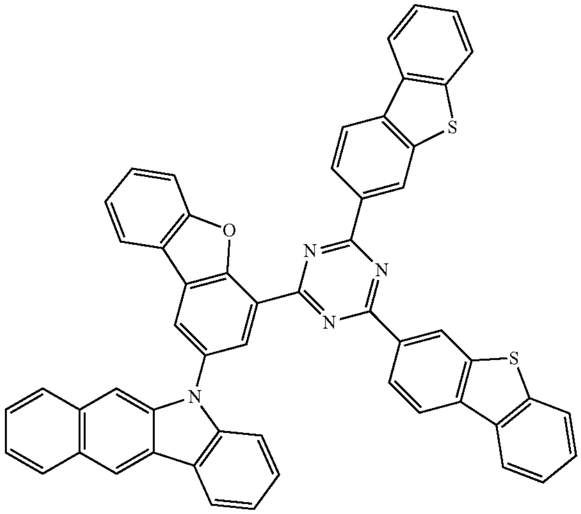
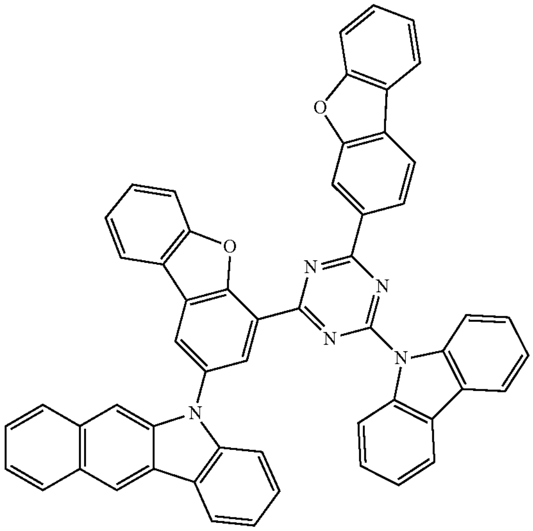

-continued
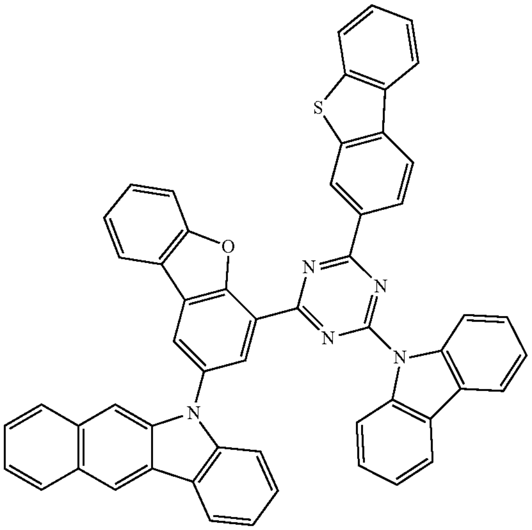
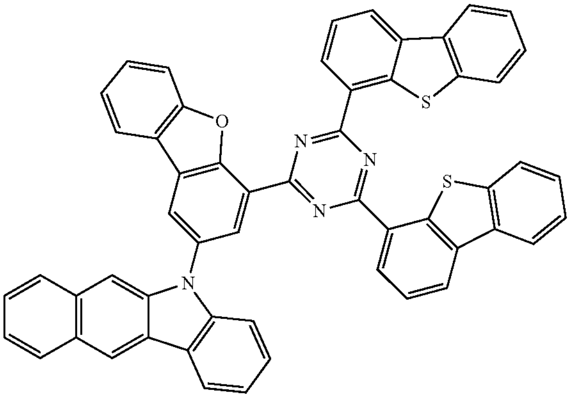
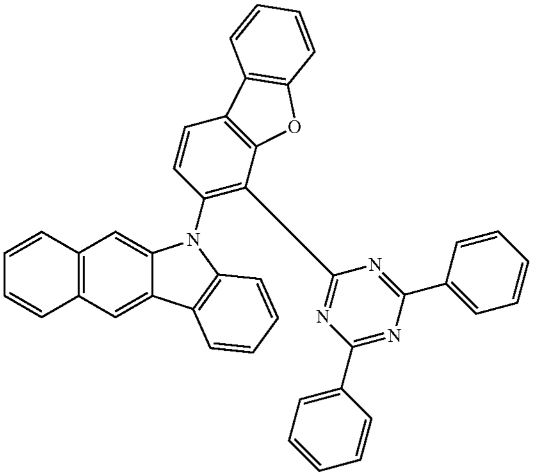
-continued
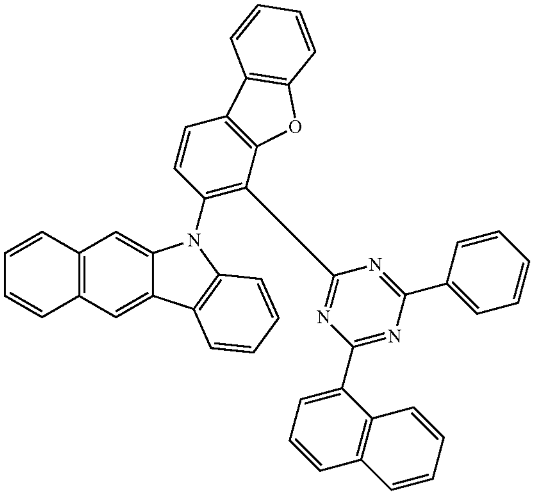
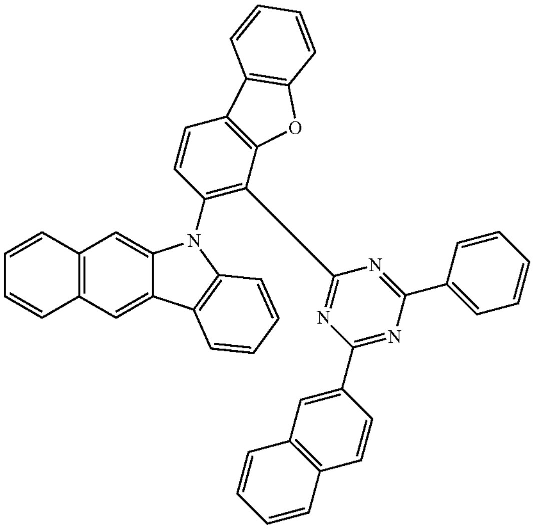
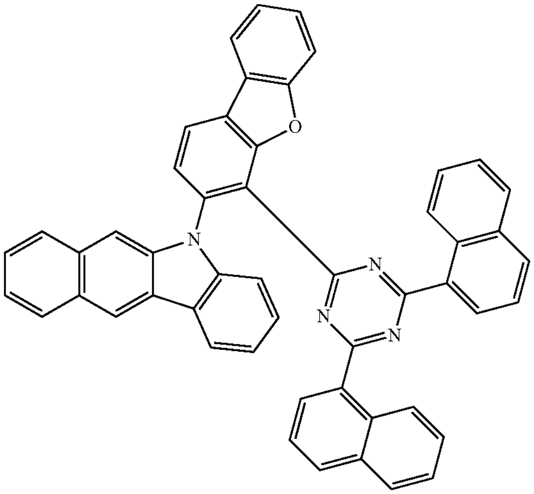

-continued
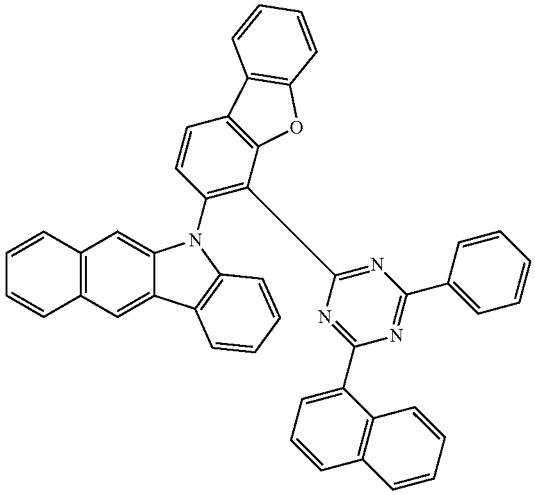
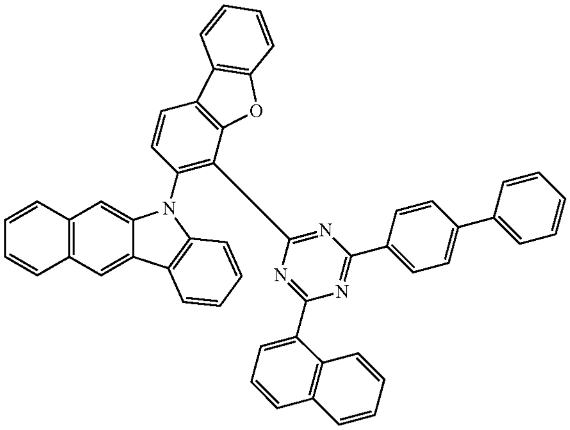
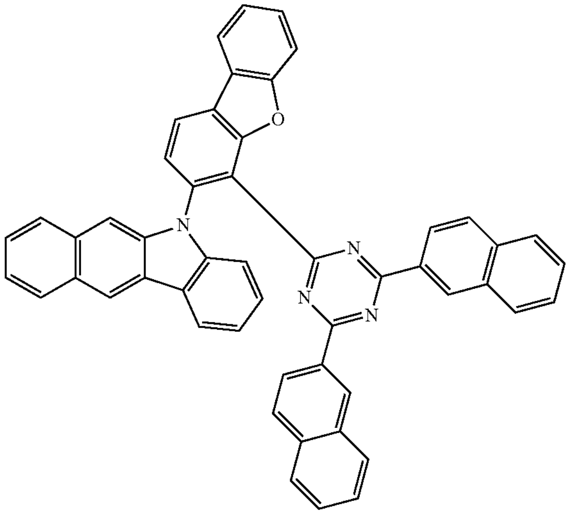
-continued
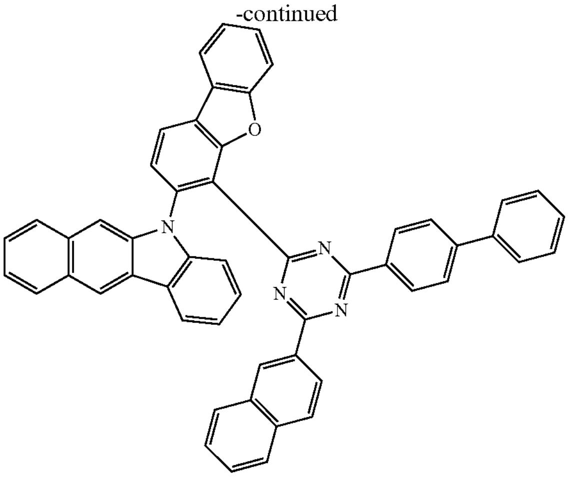
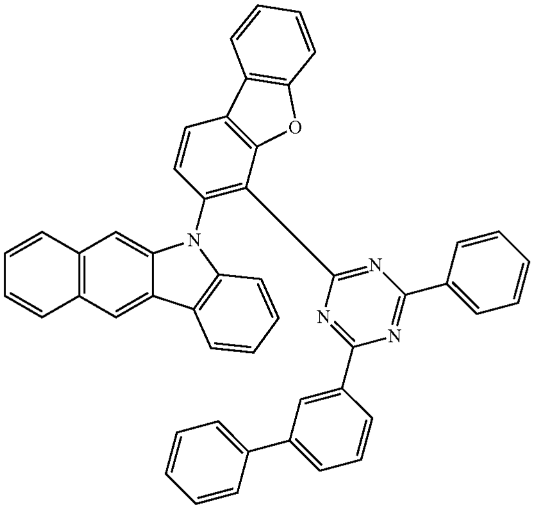
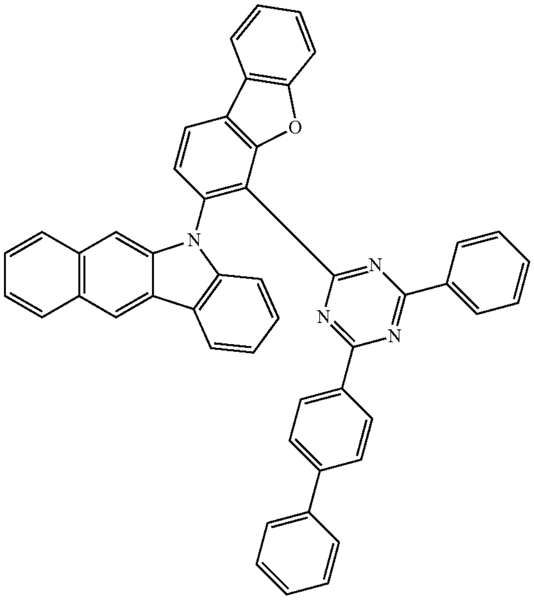

-continued
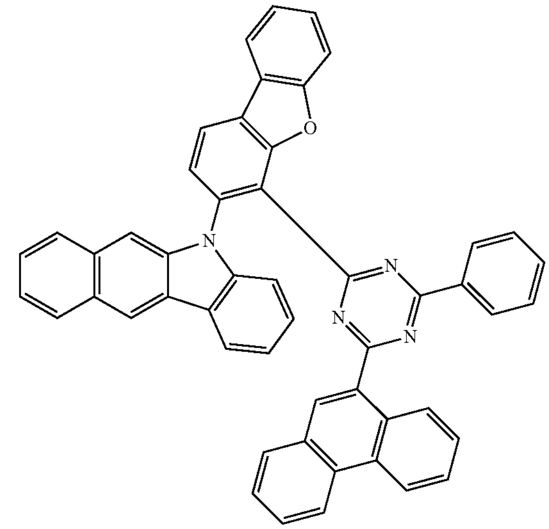
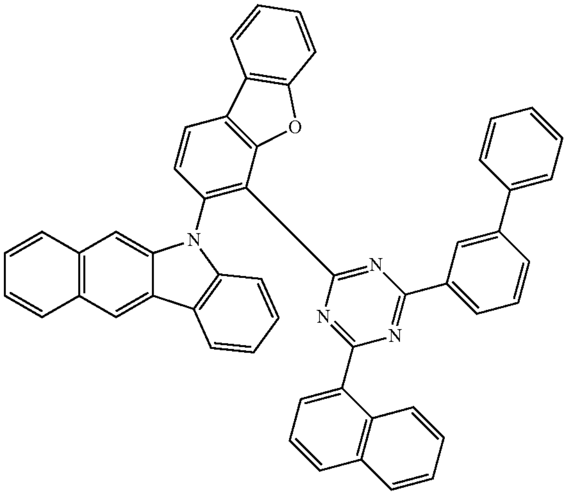
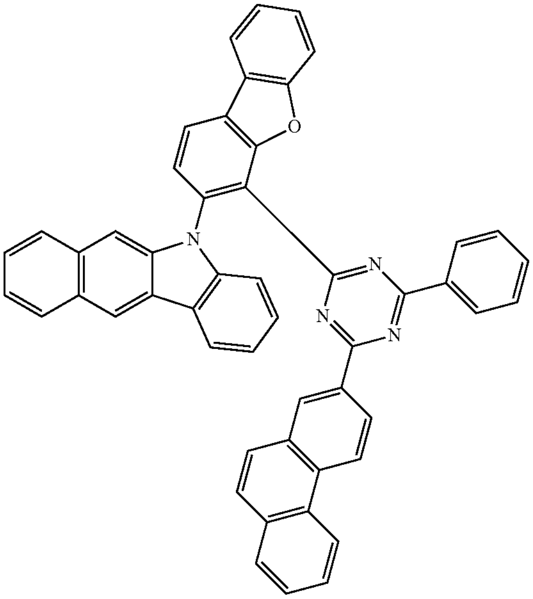
-continued
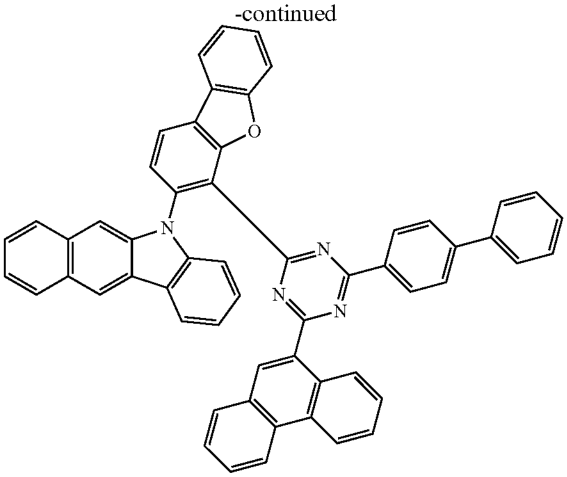
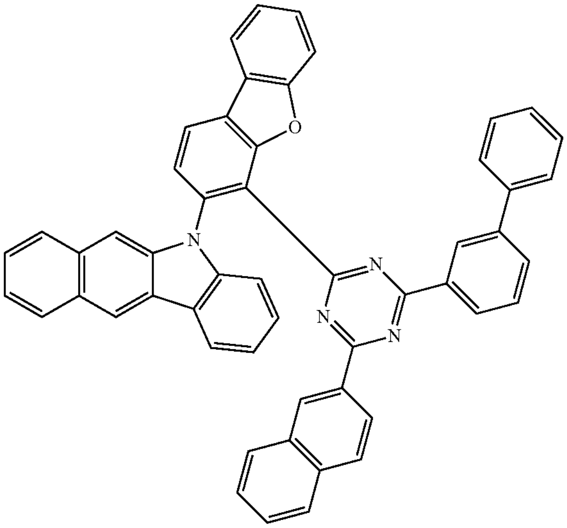
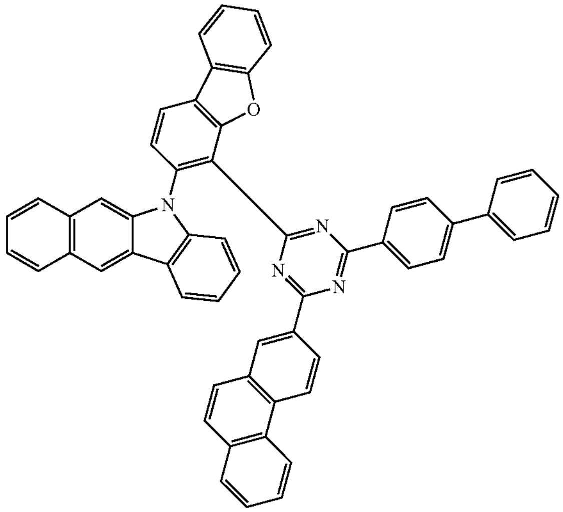

-continued
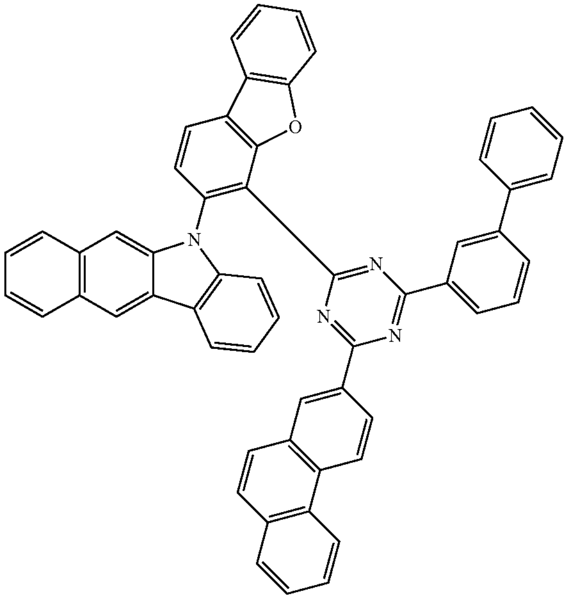
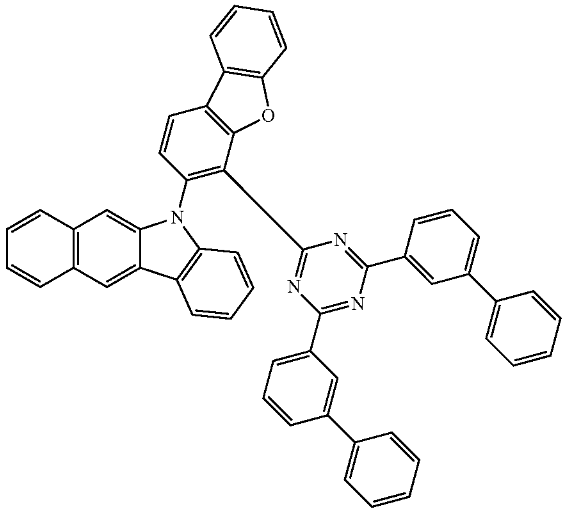
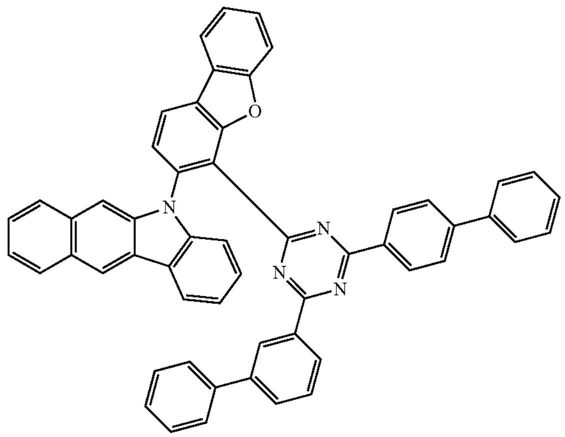
-continued
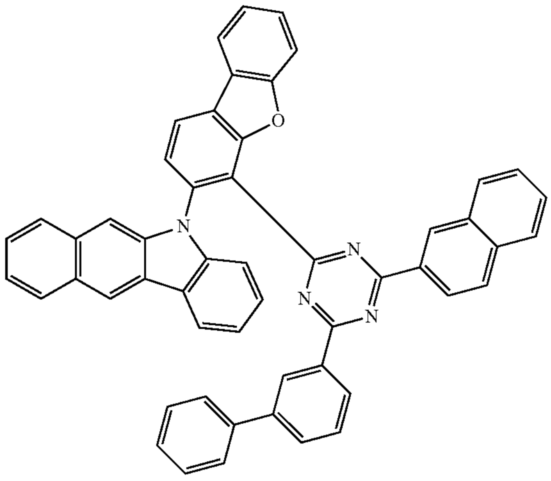
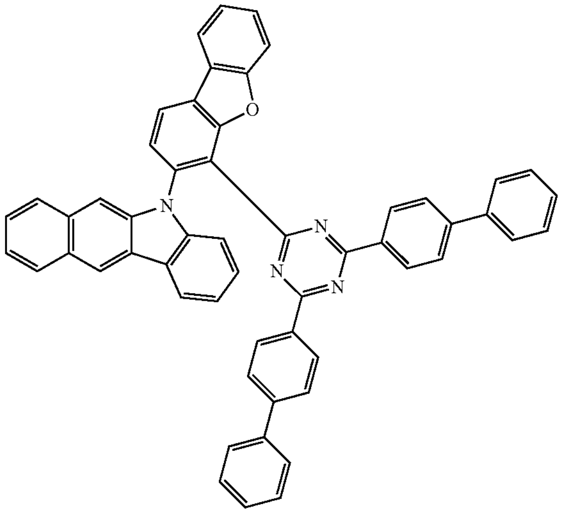
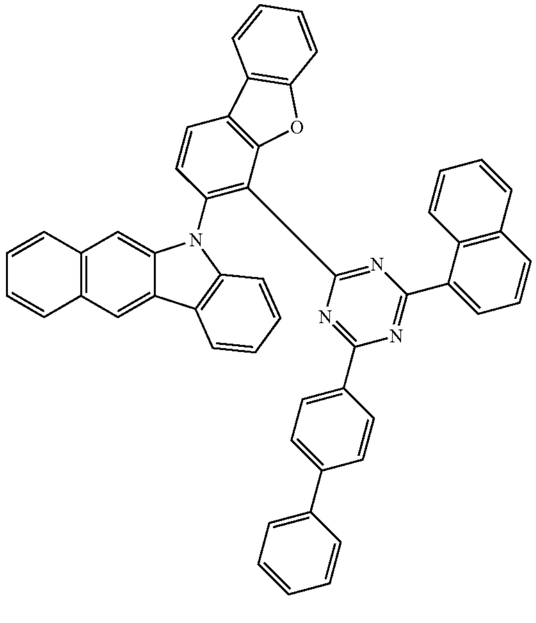

-continued
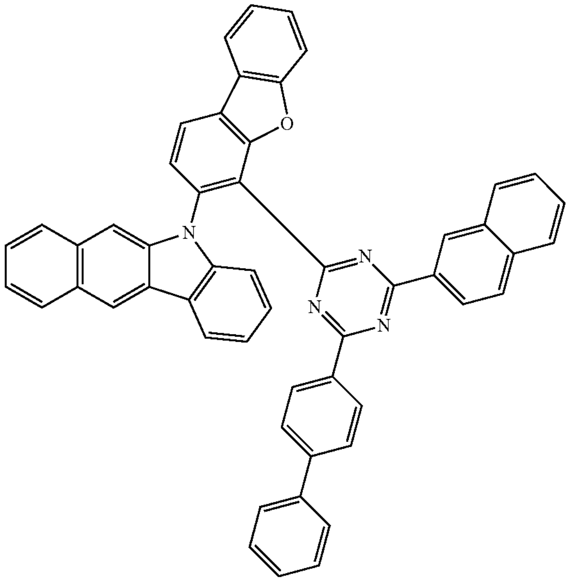
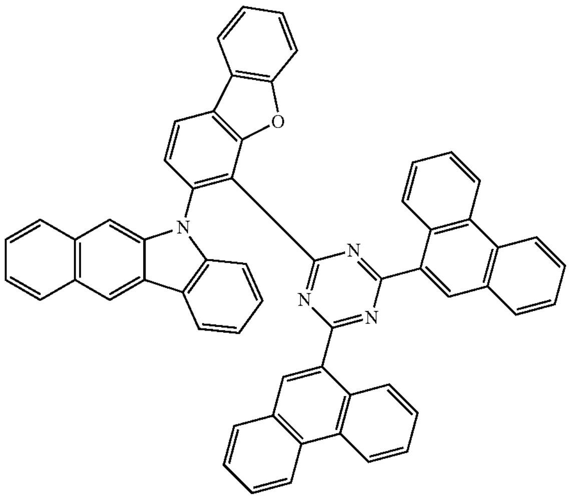
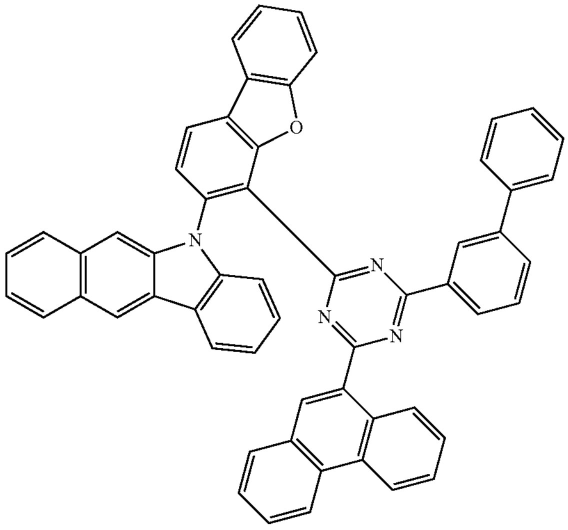
-continued
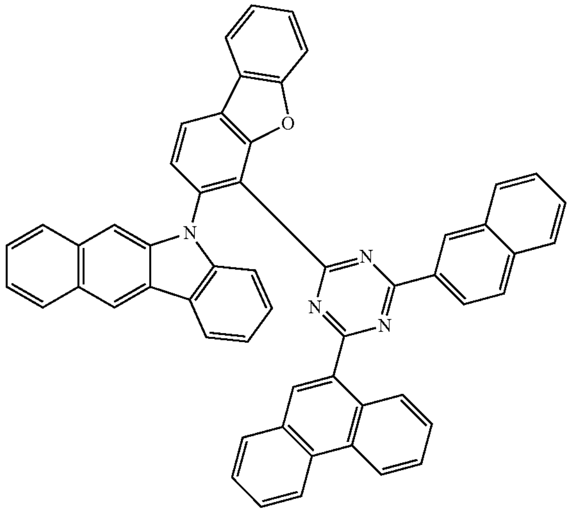
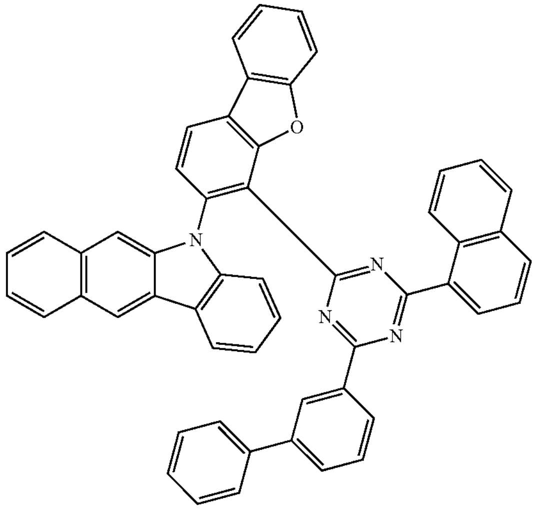
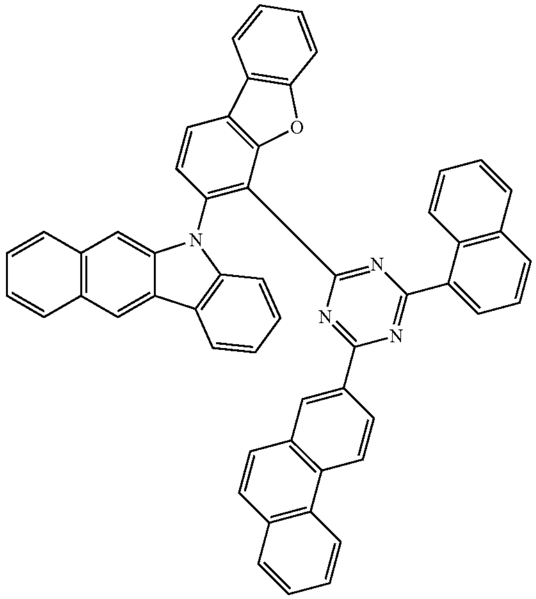

-continued
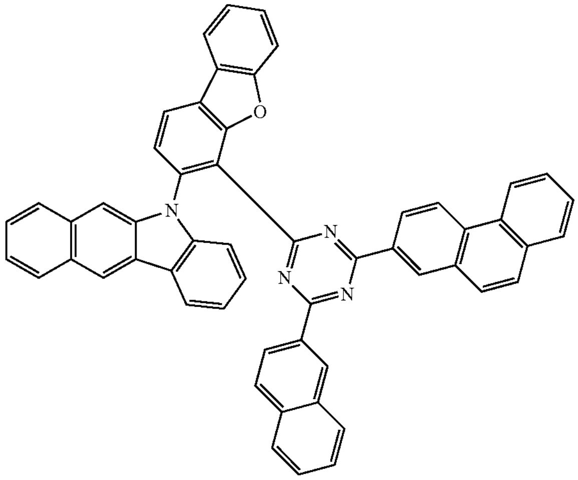
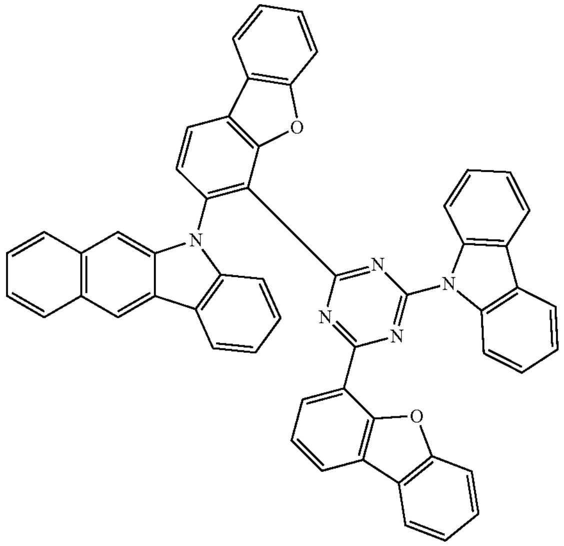
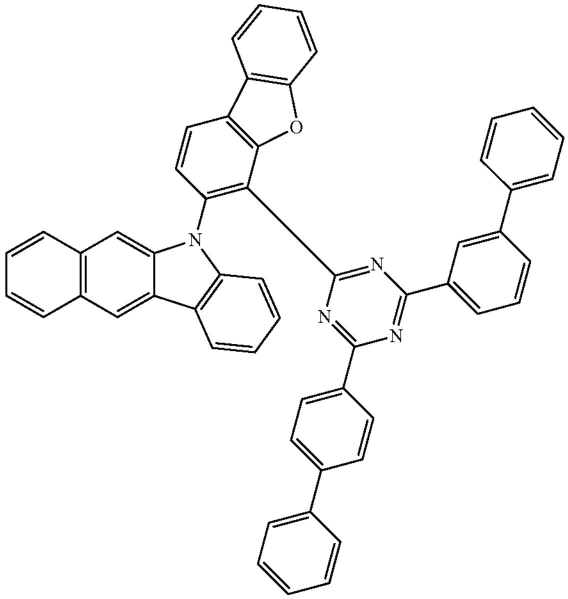
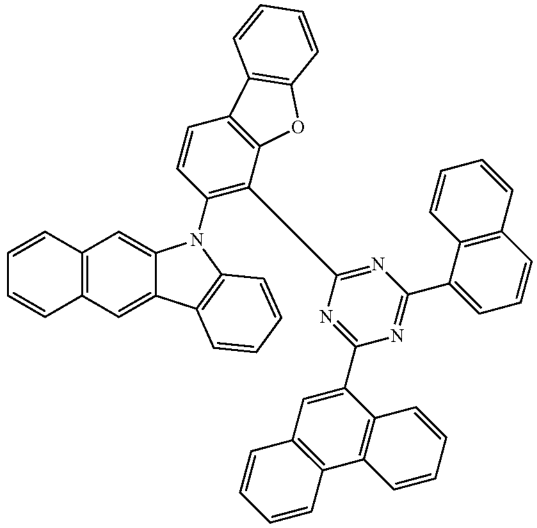
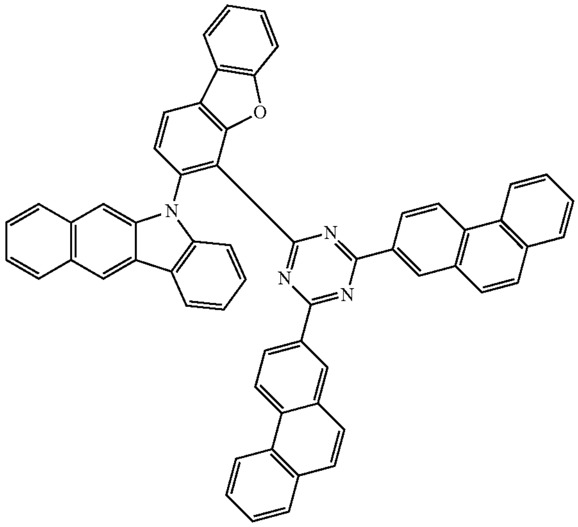
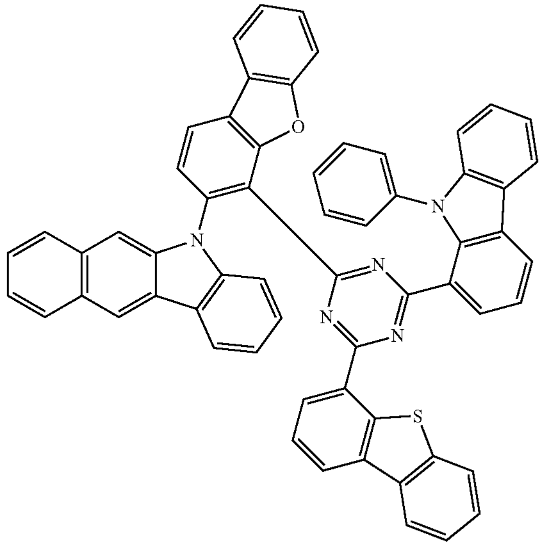
-continued -continued
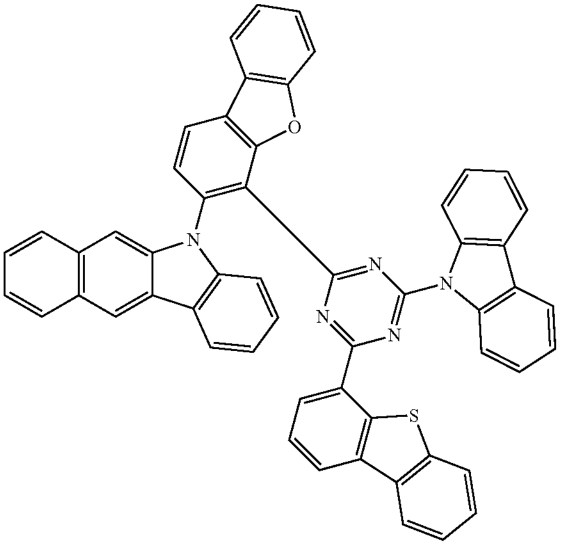
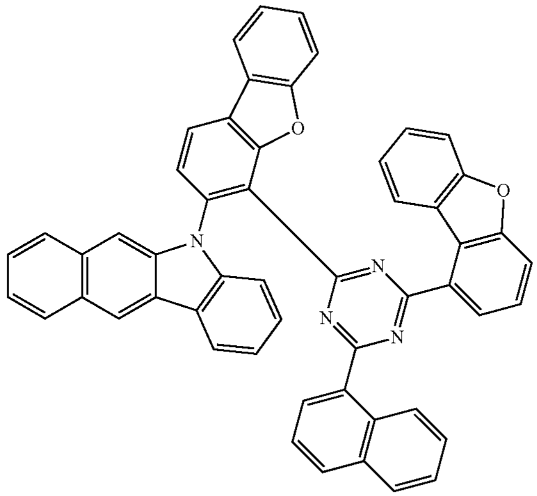
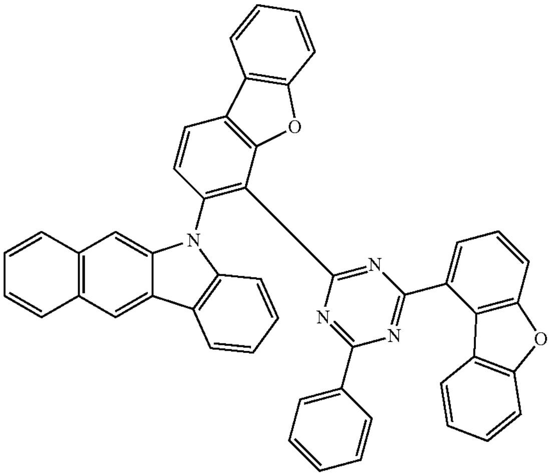
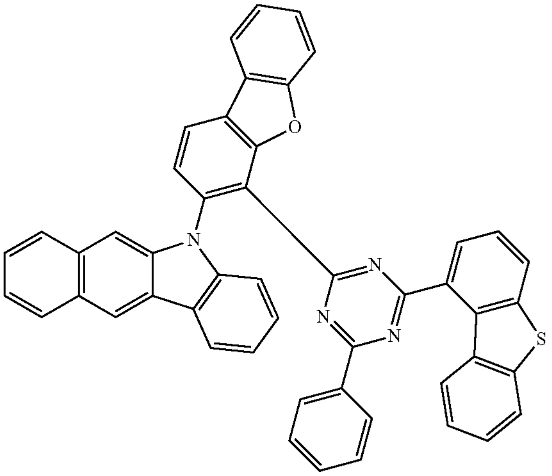
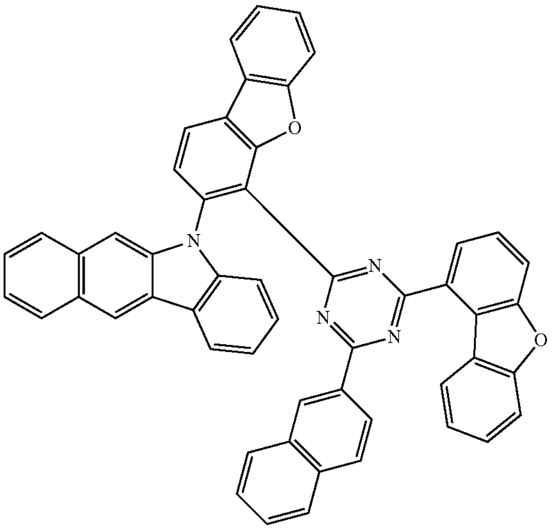
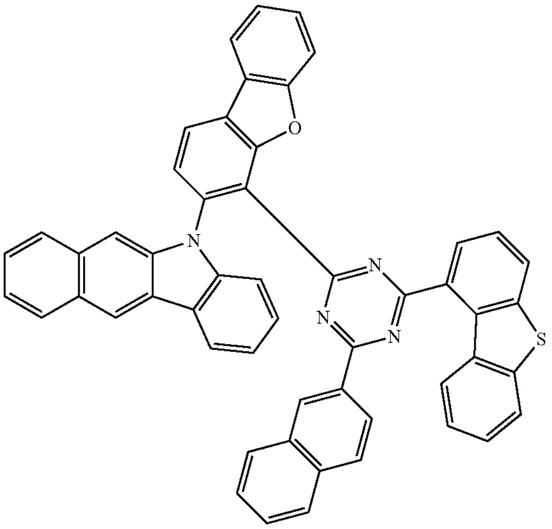
-continued -continued
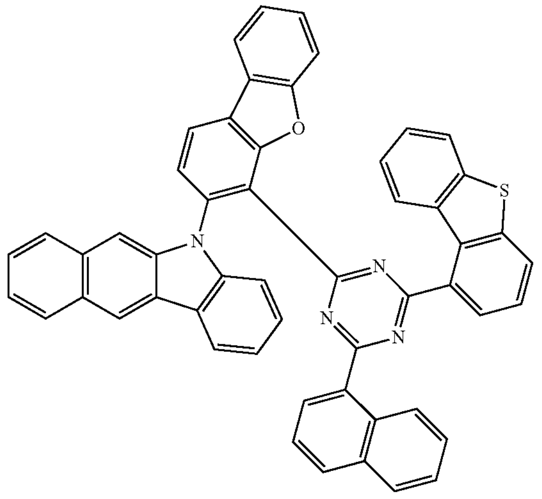
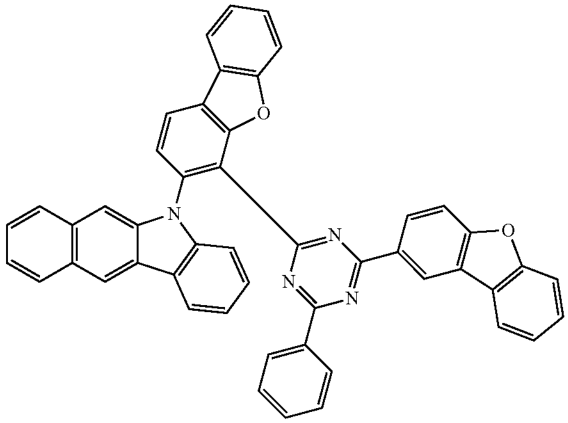
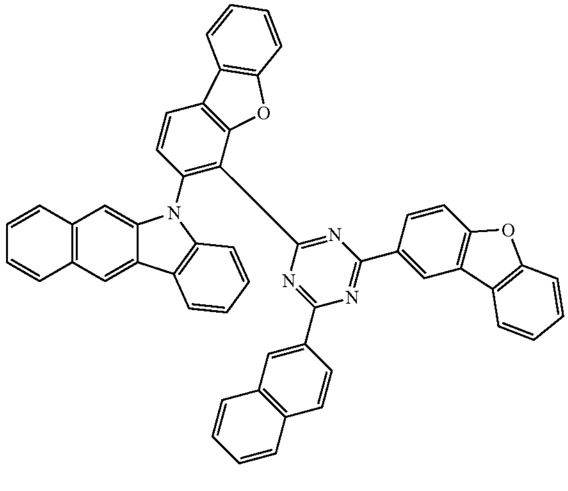
-continued
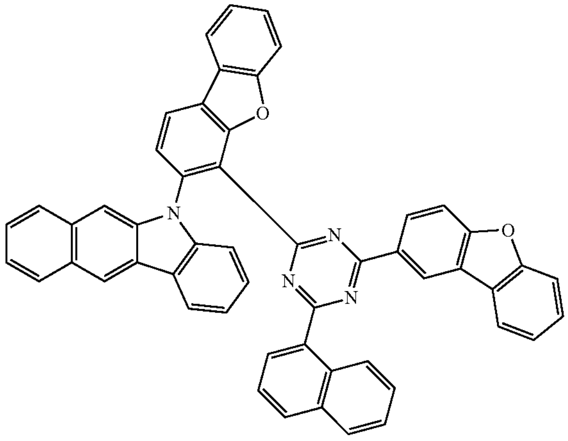
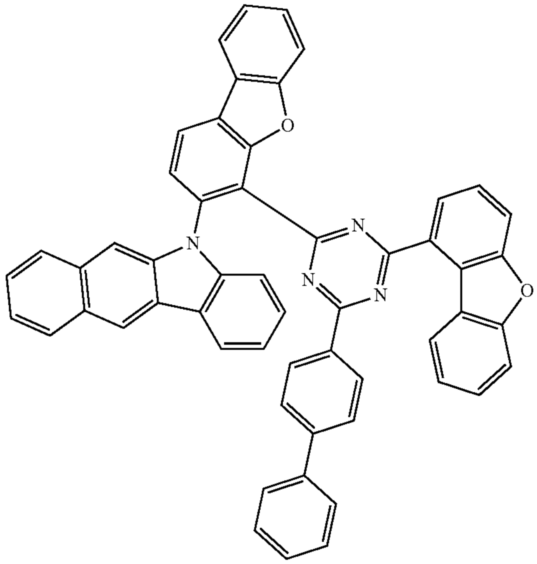
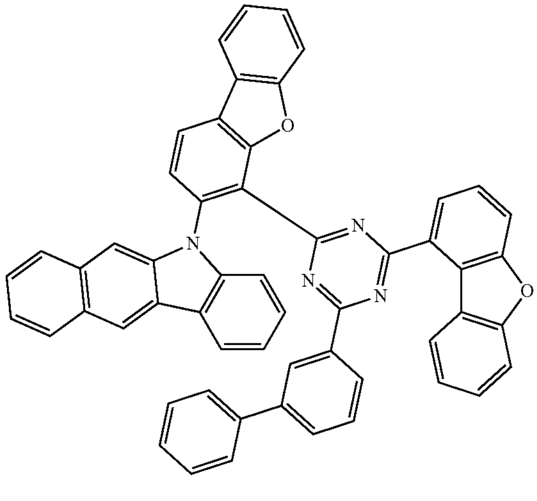

-continued
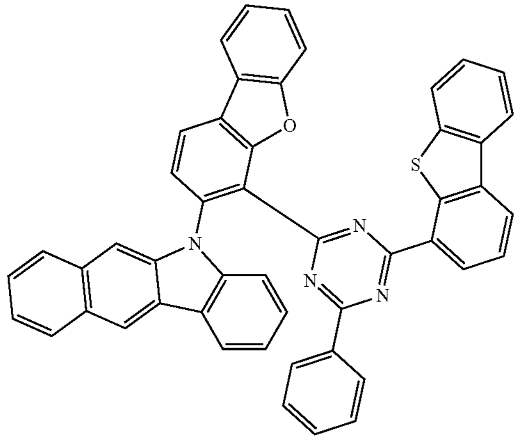
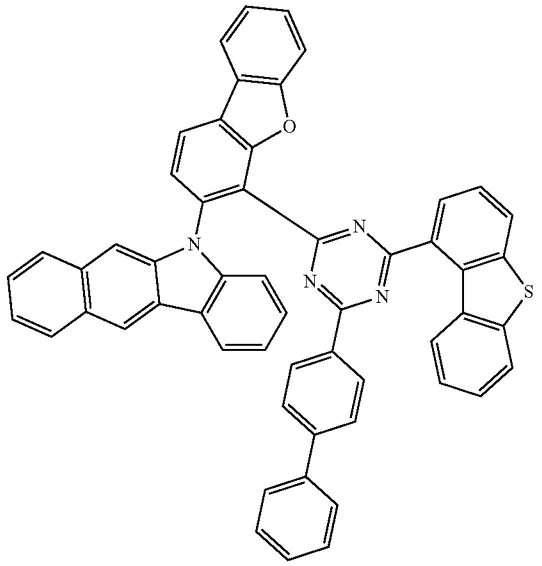
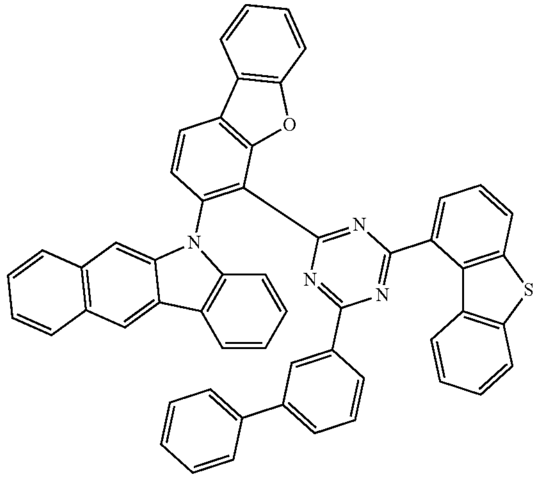
-continued
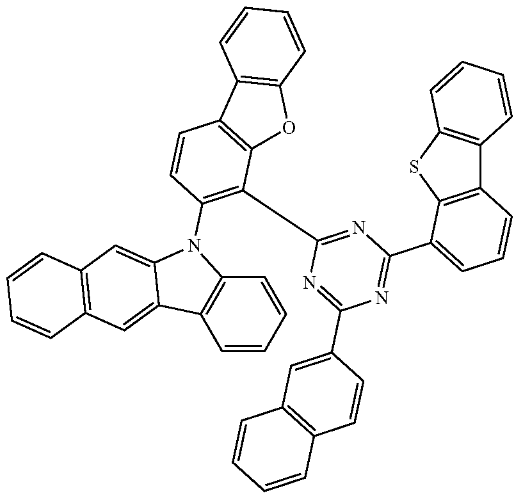
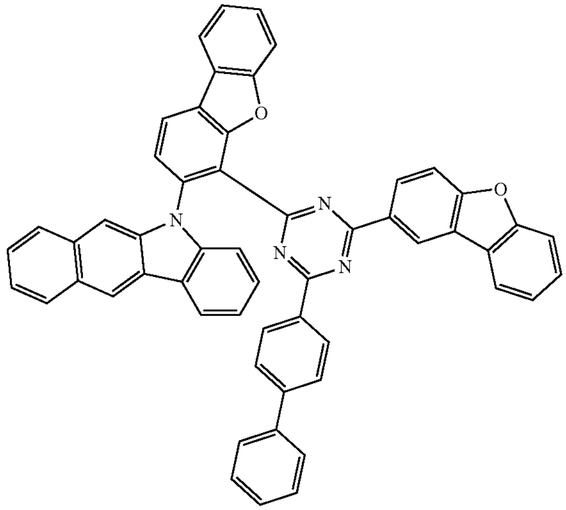
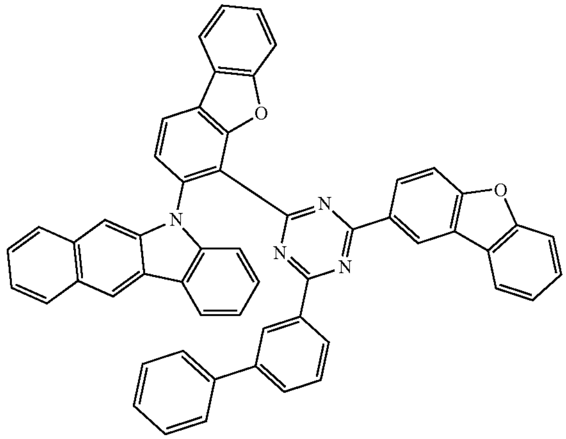

-continued
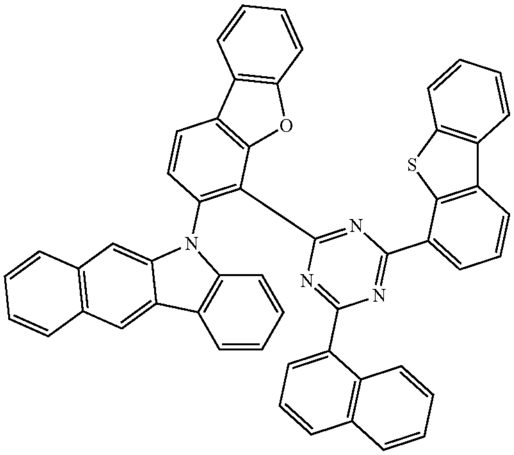
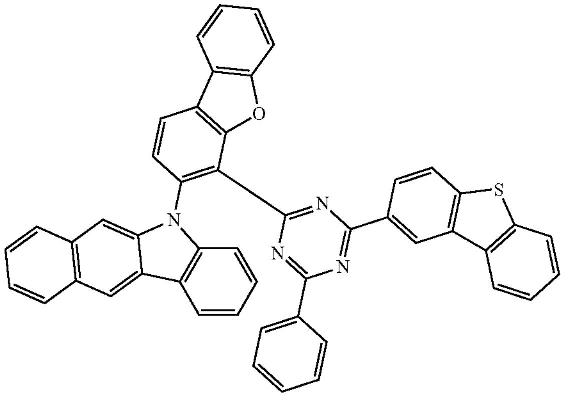
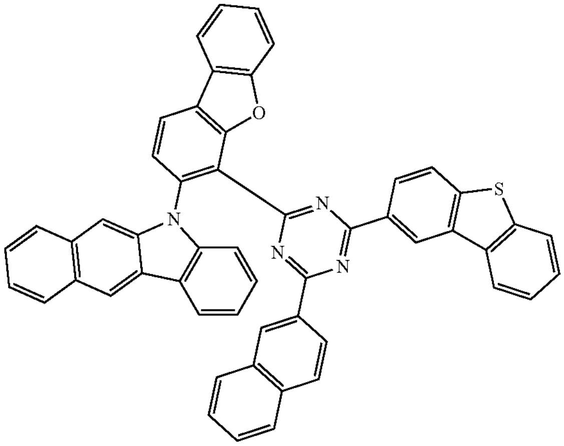
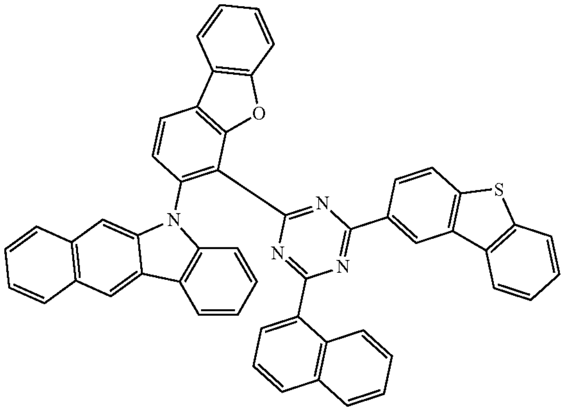
-continued
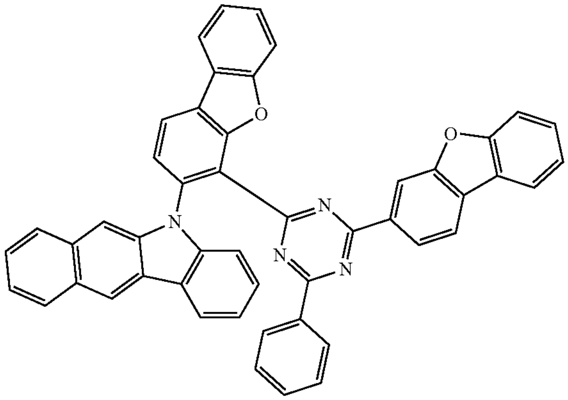
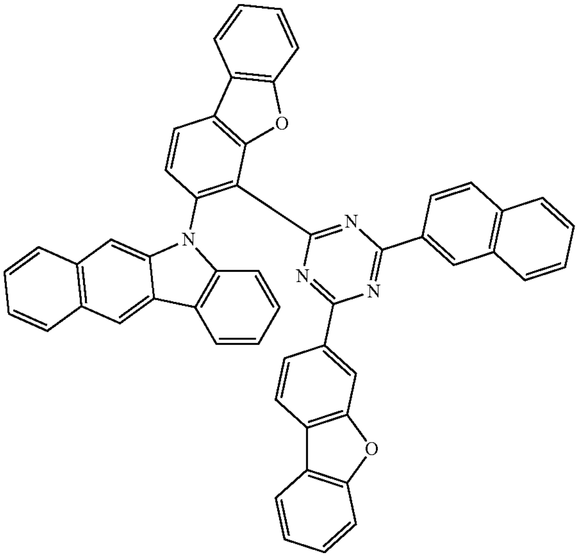
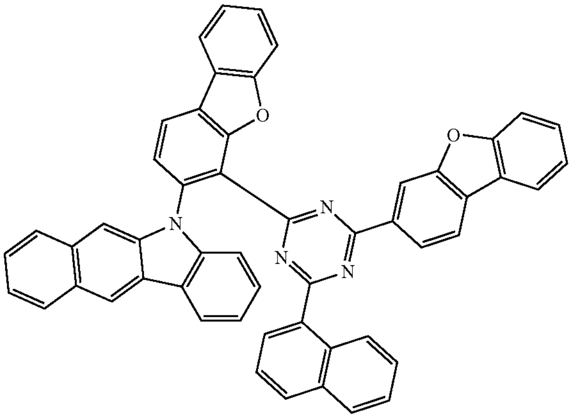

-continued
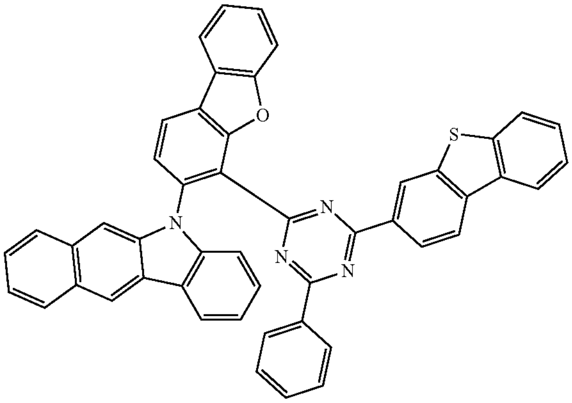
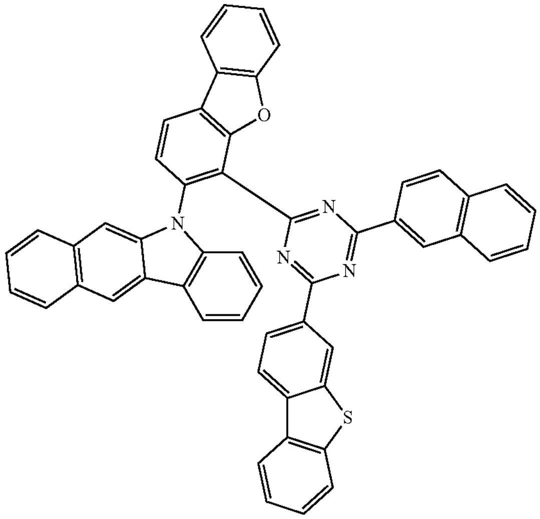
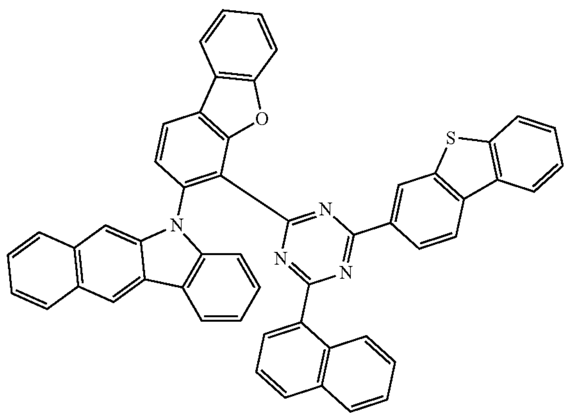
-continued
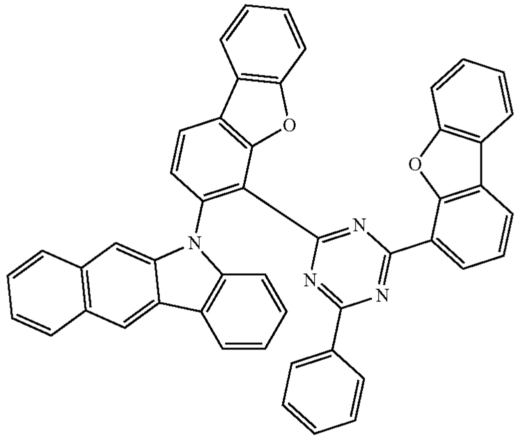
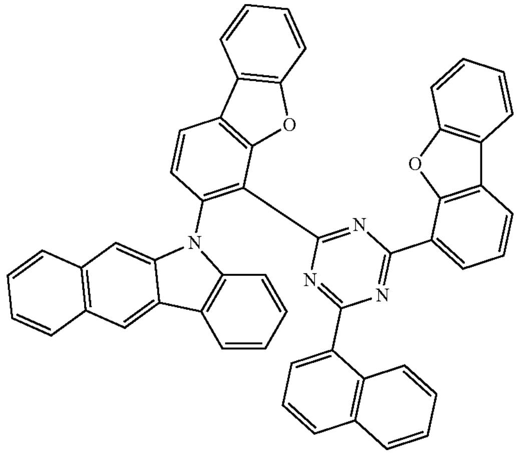
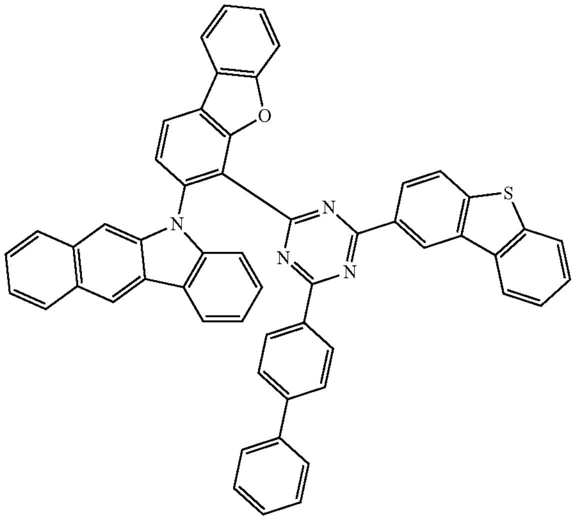

-continued
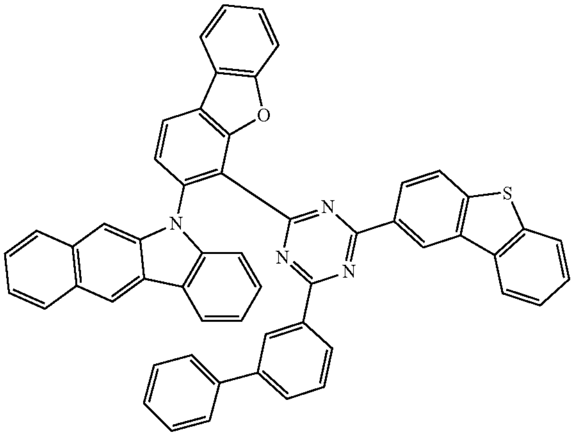
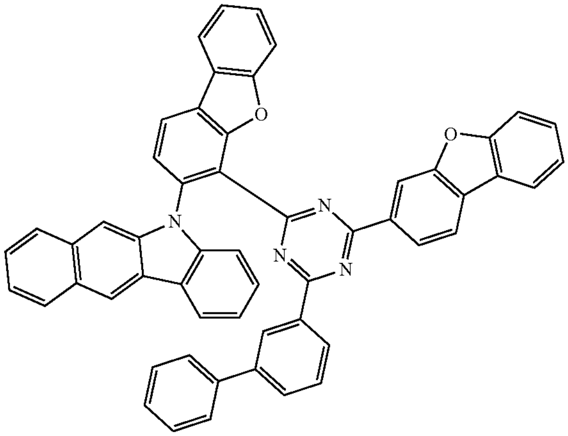
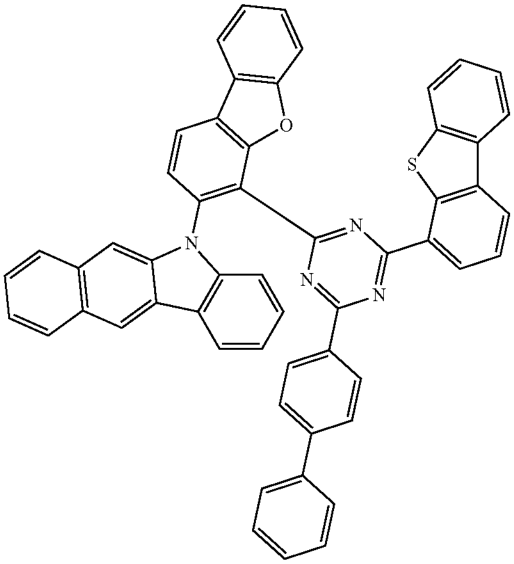
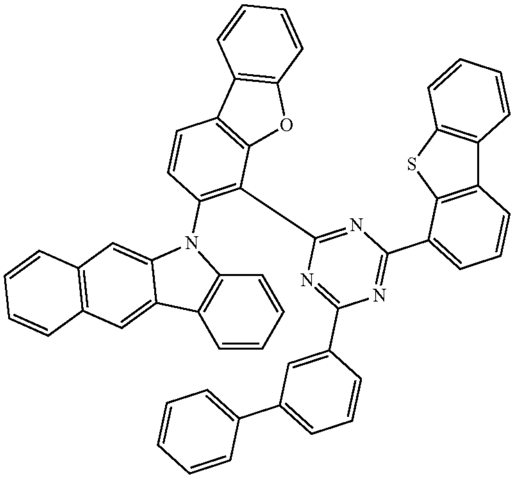
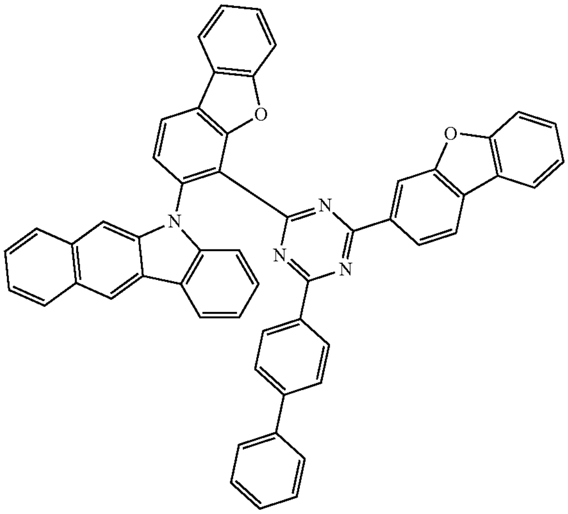
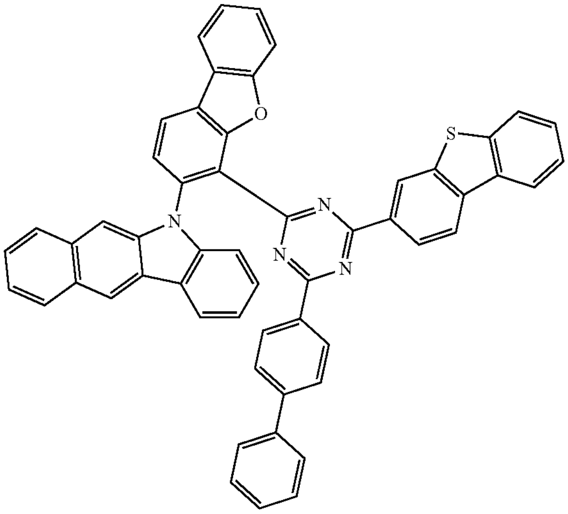
-continued -continued
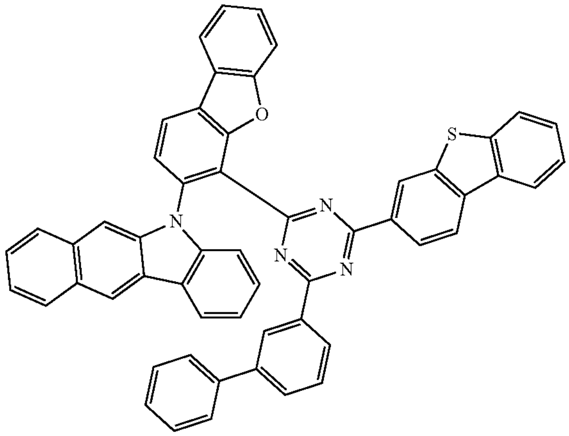
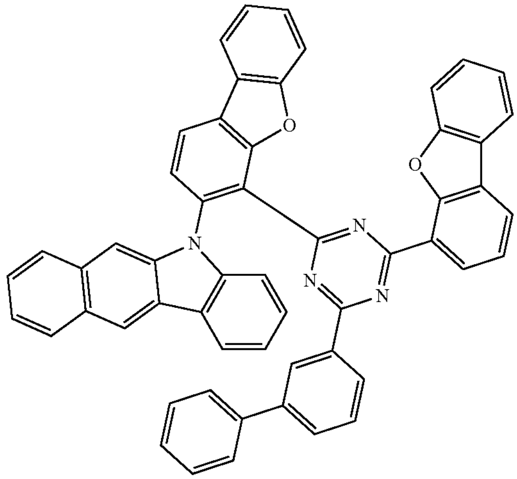
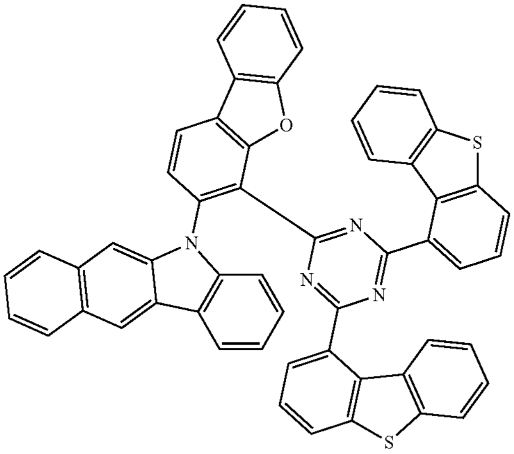
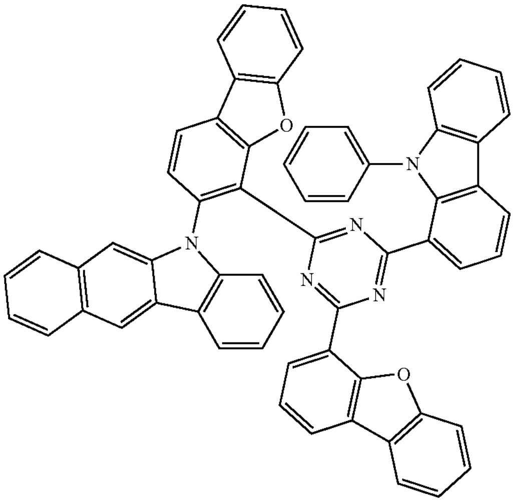
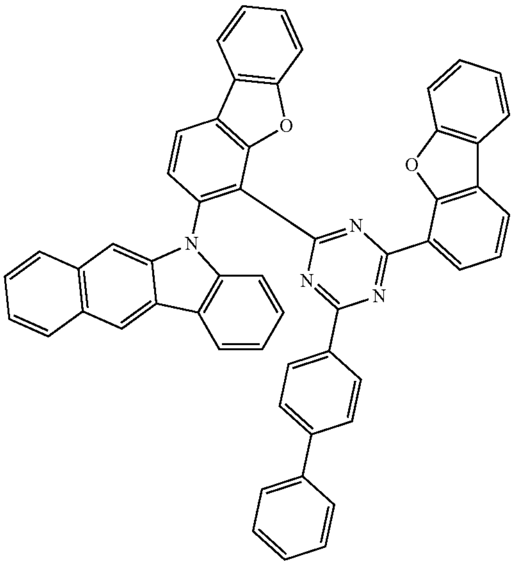
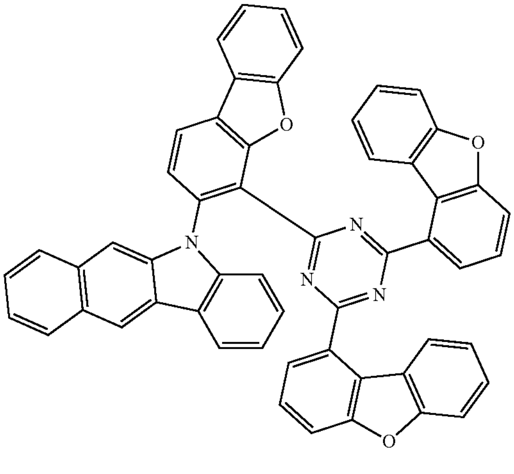
-continued -continued
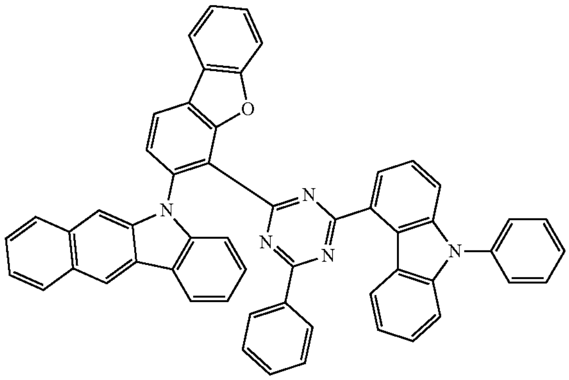
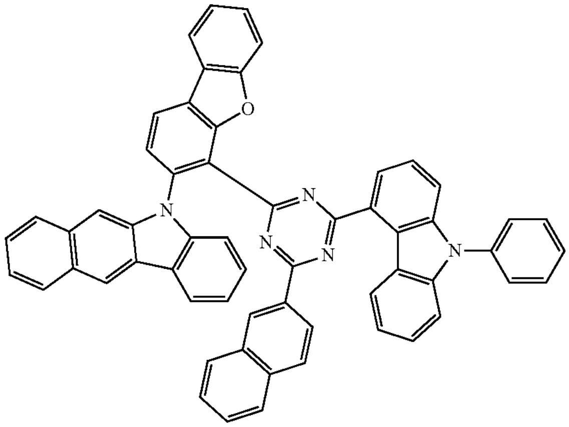
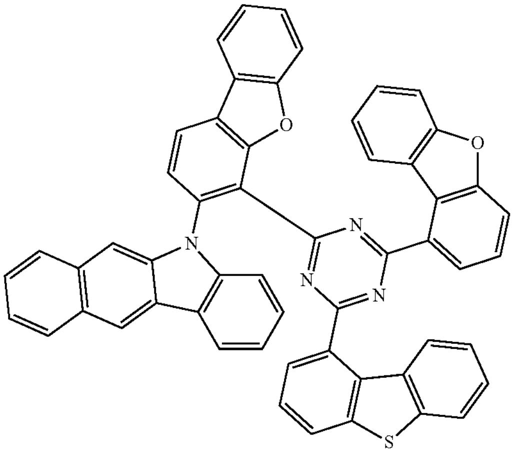
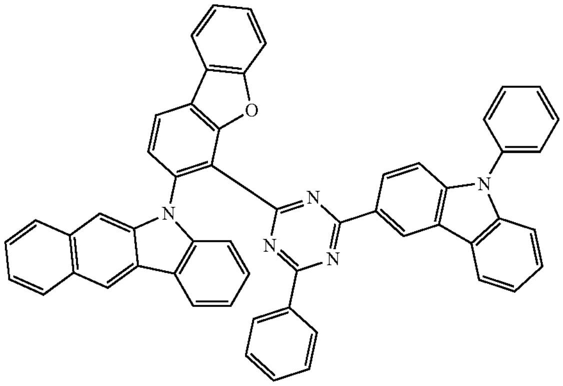
-continued
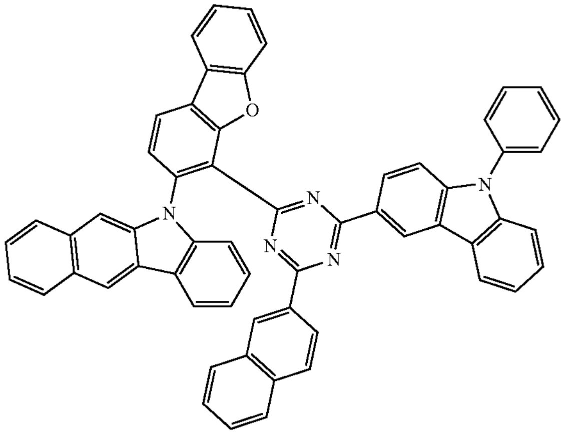
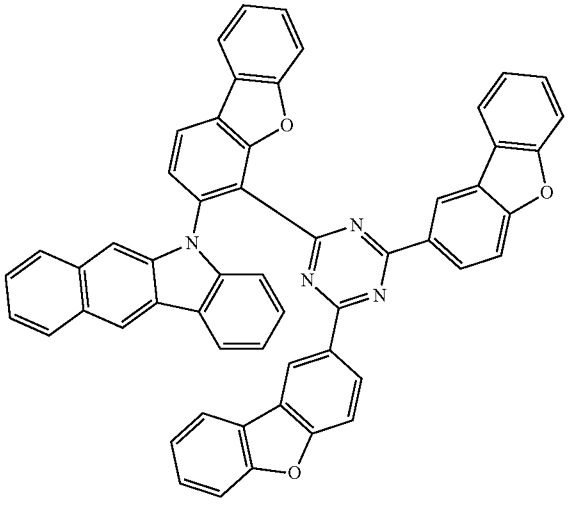
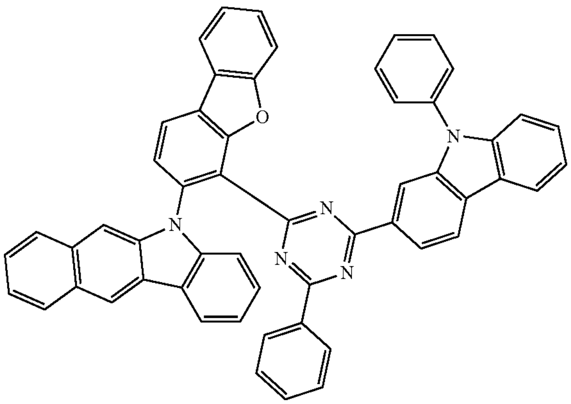

-continued
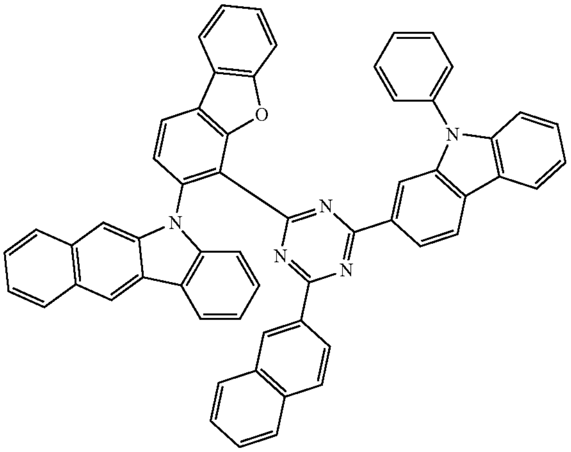
-continued
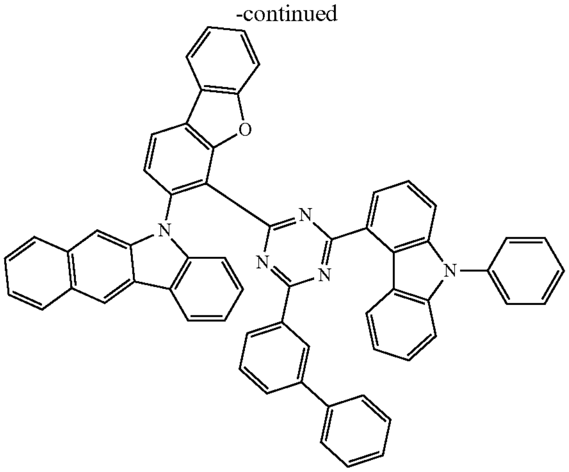
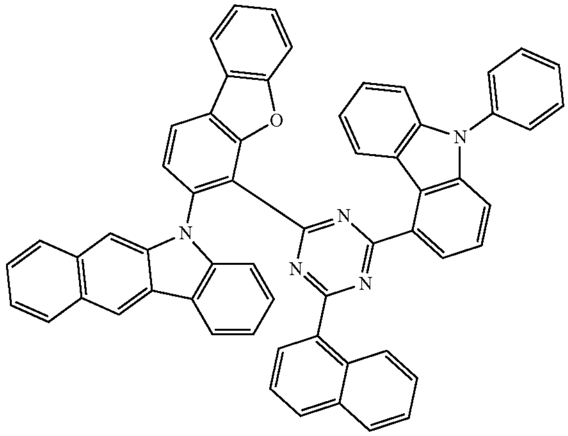
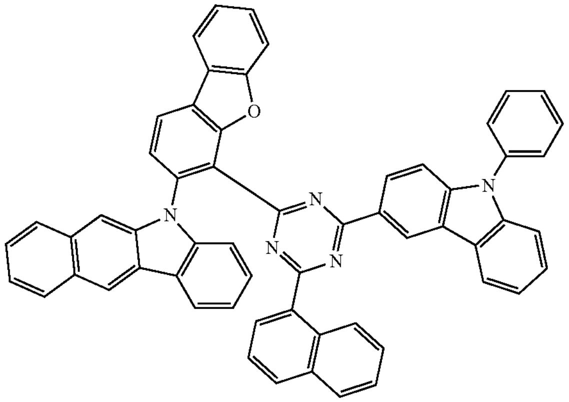
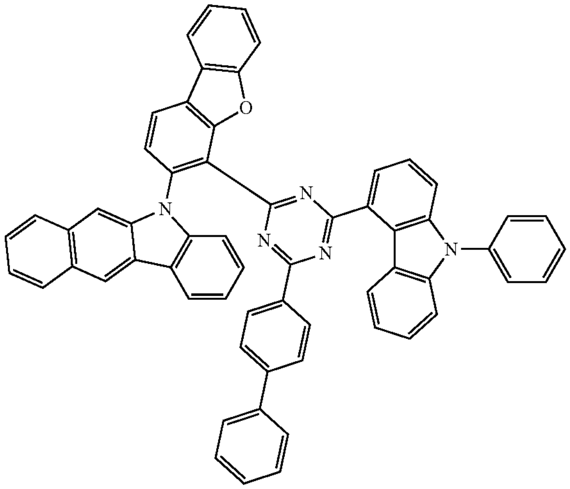
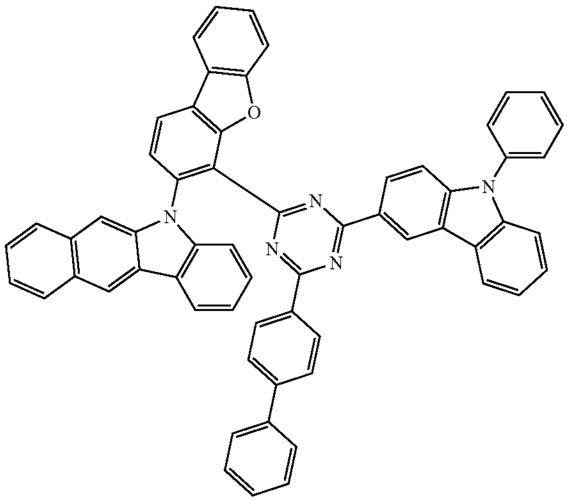

-continued
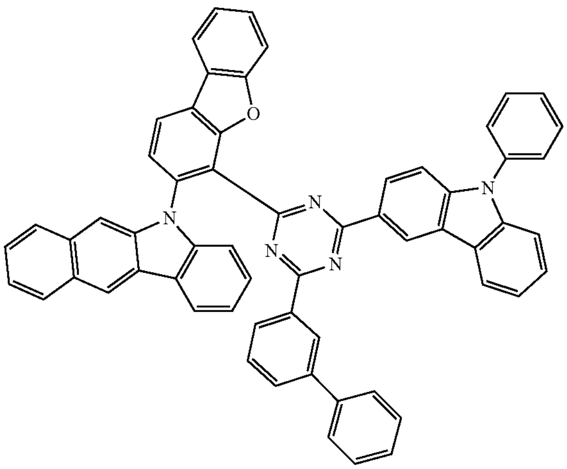
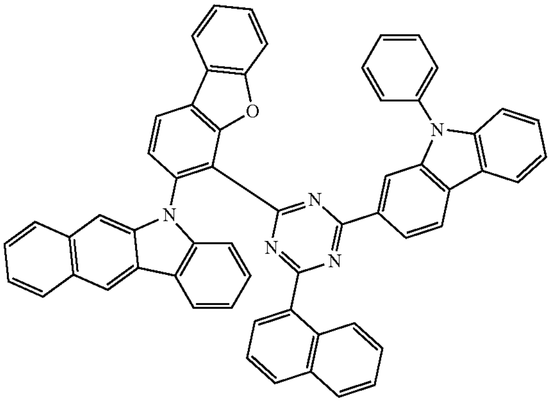
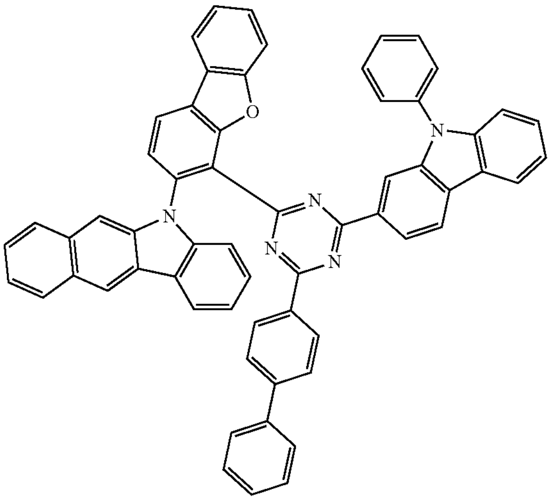
-continued
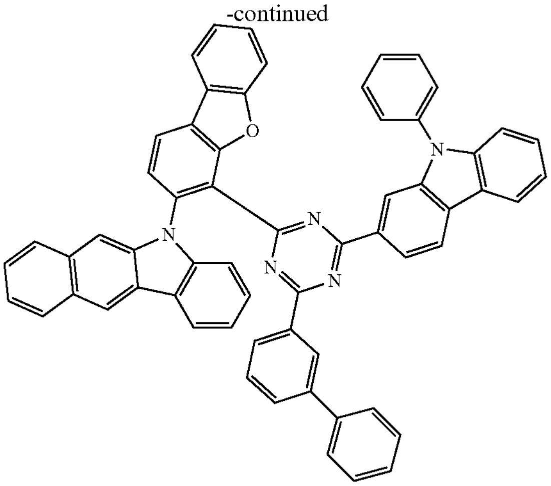
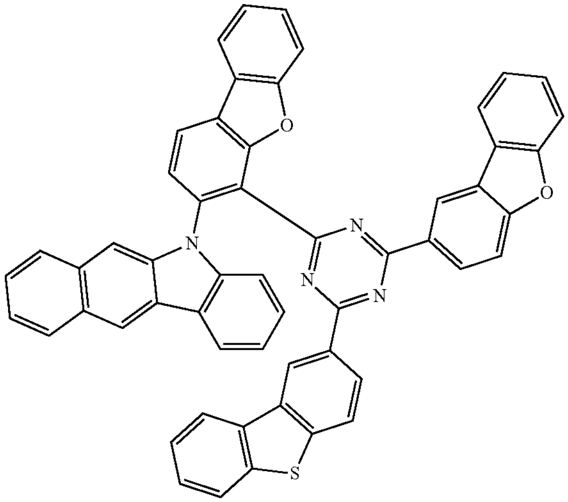
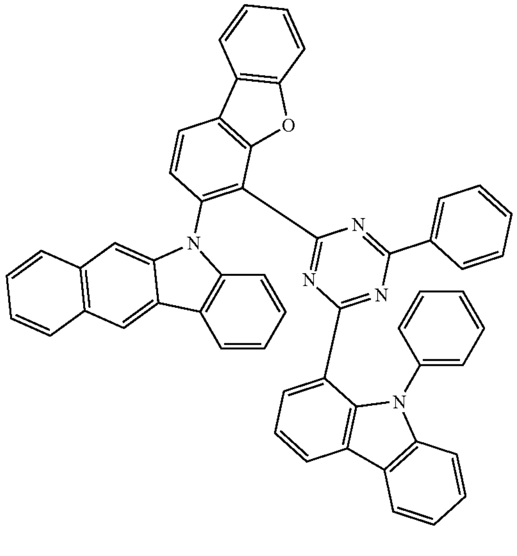

-continued
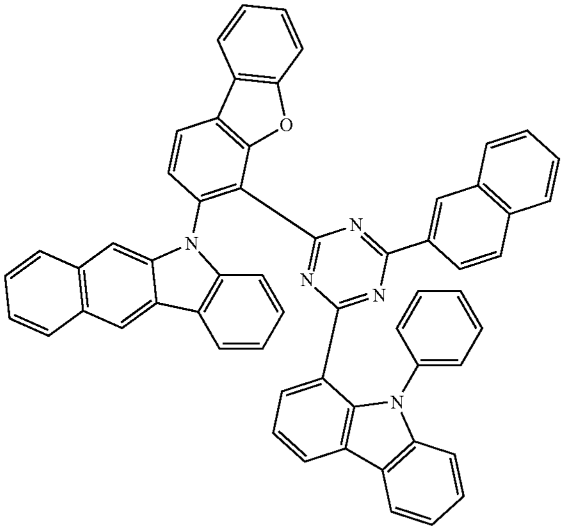
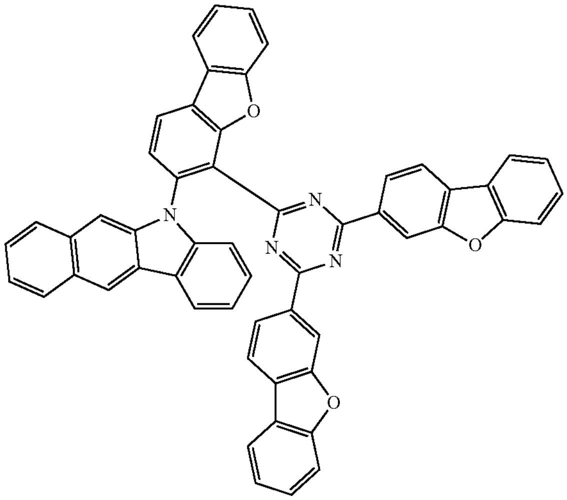
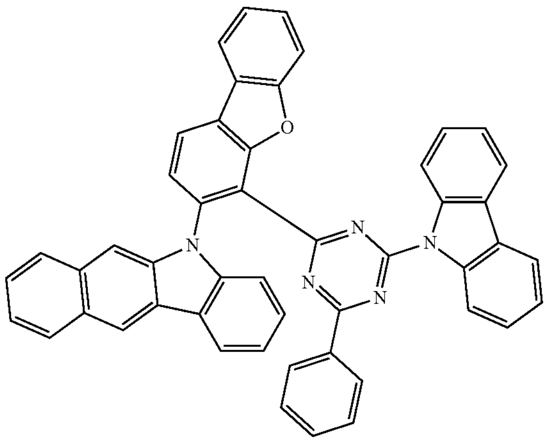
-continued
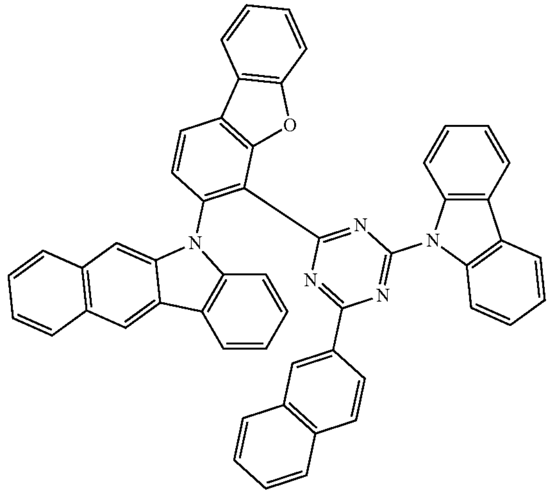
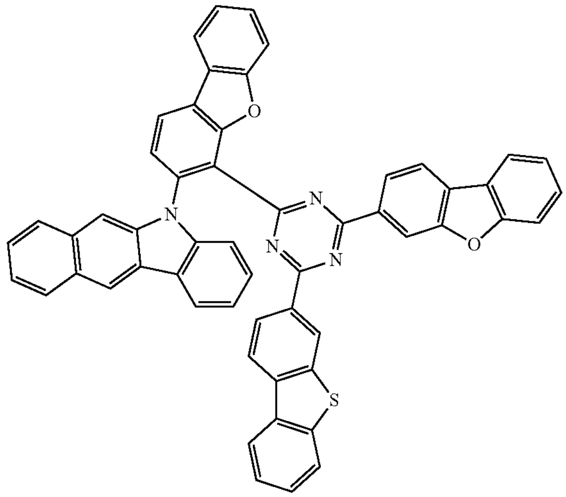
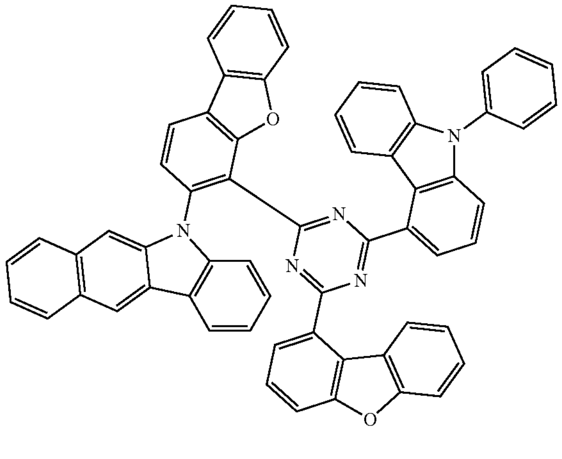

-continued
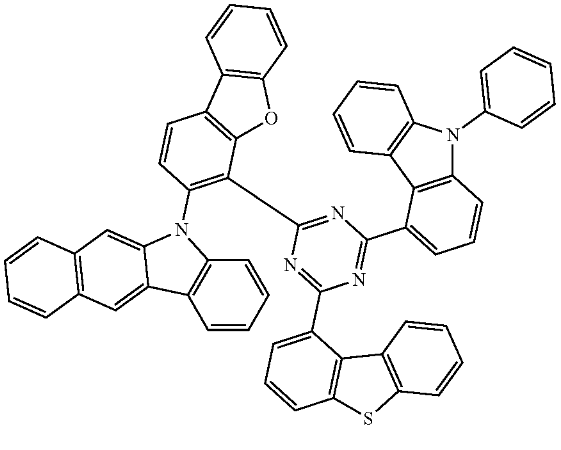
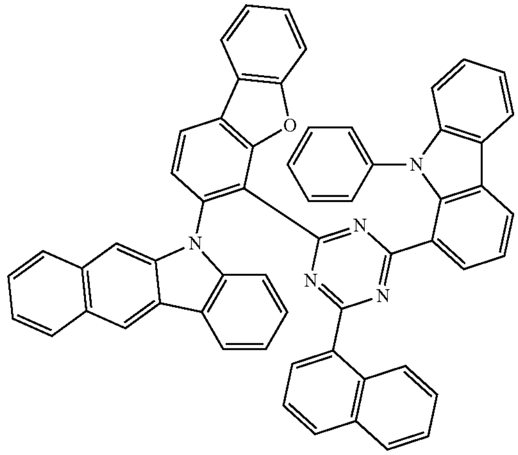
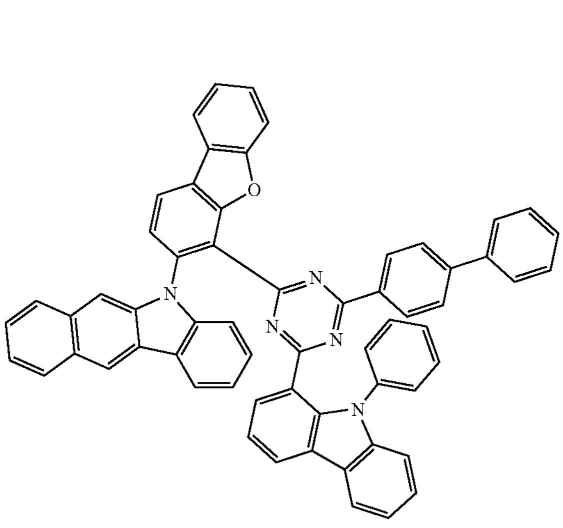
-continued
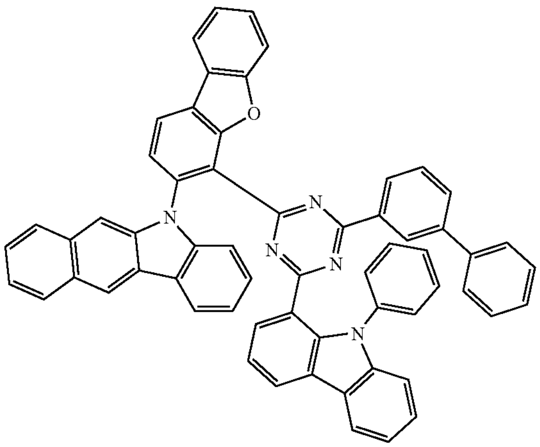
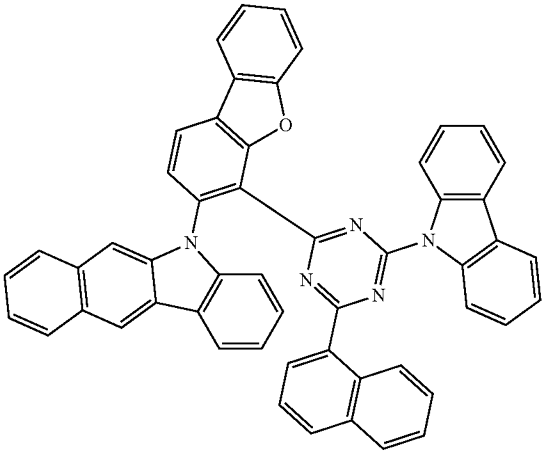
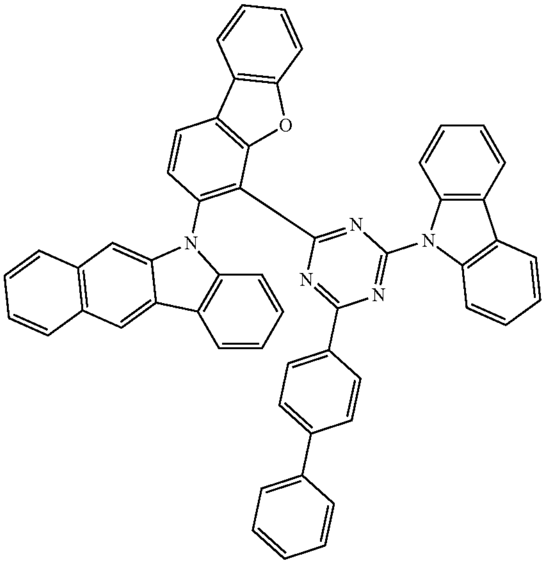

-continued
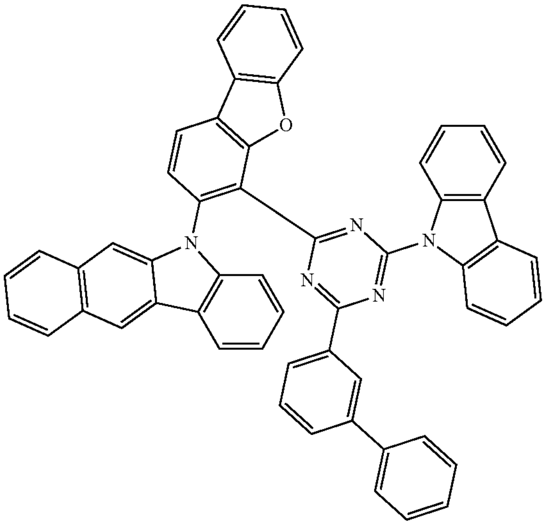
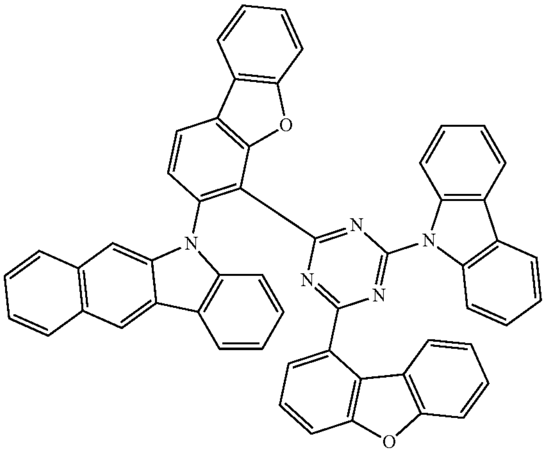
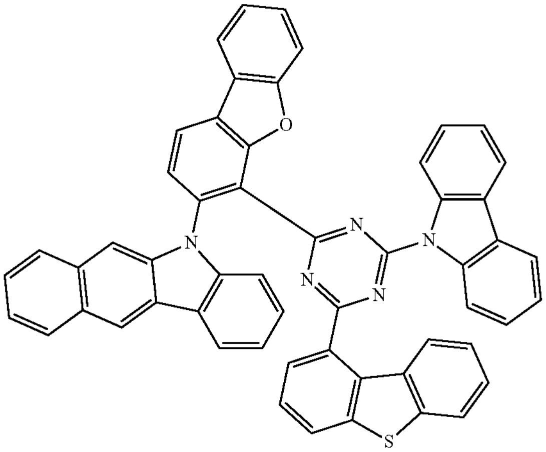
-continued
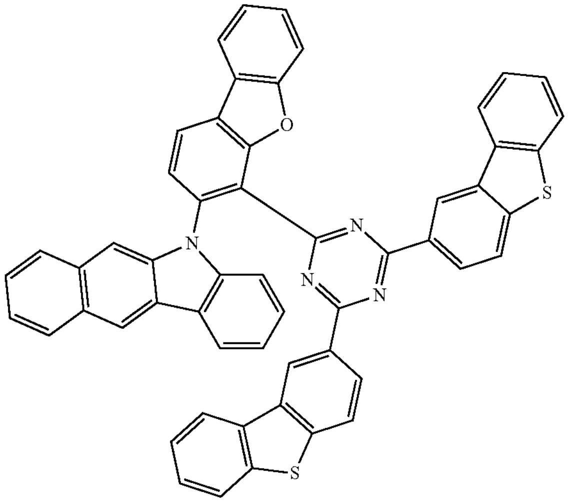
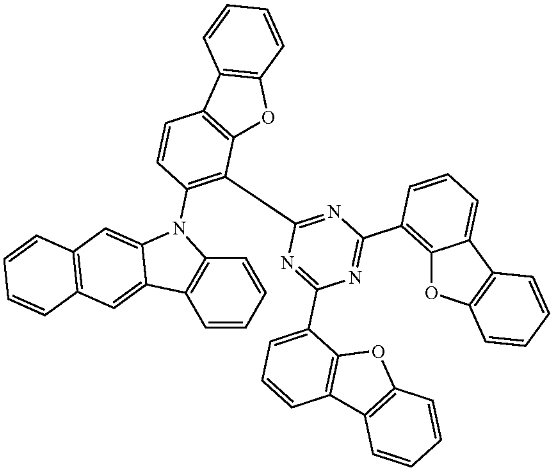
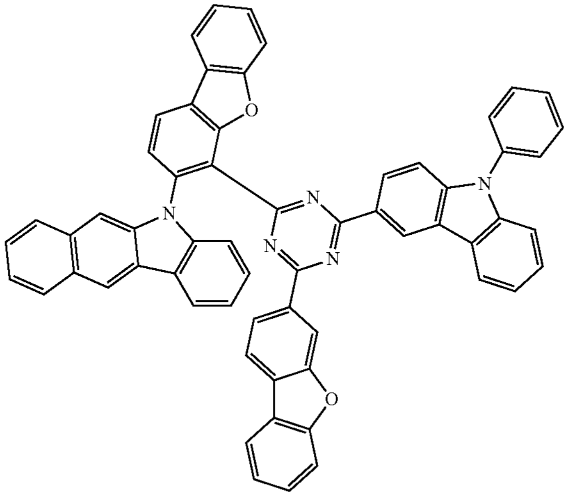

-continued
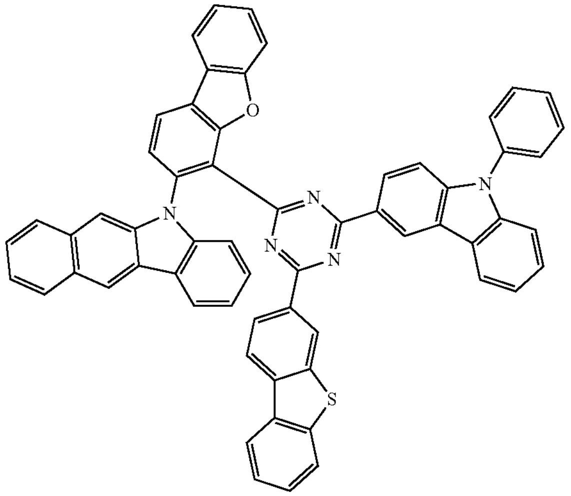
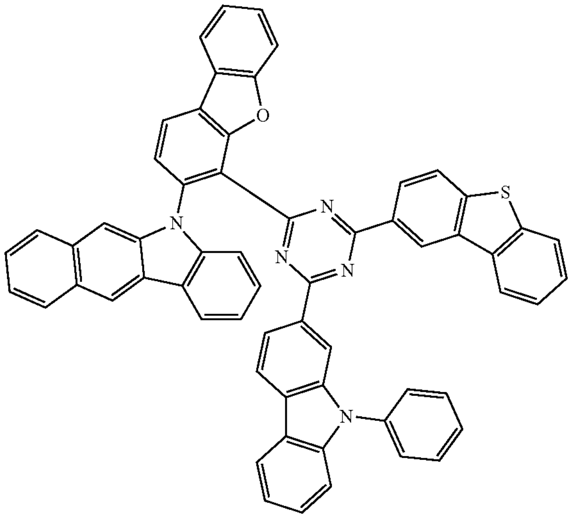
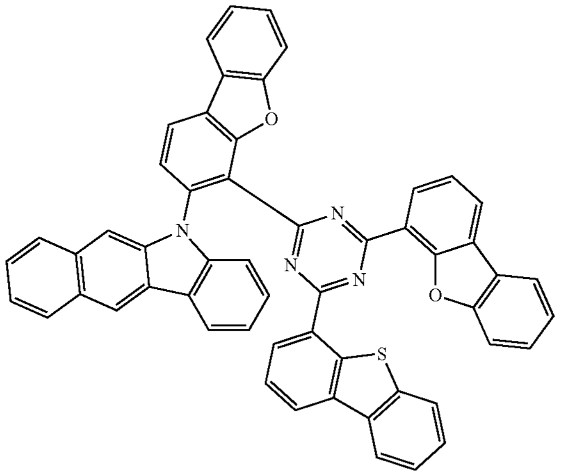
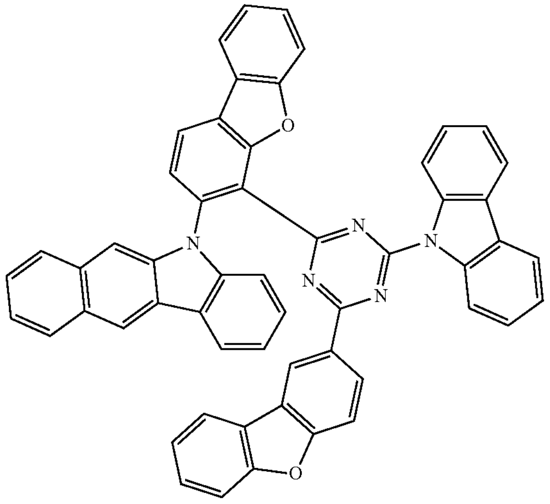
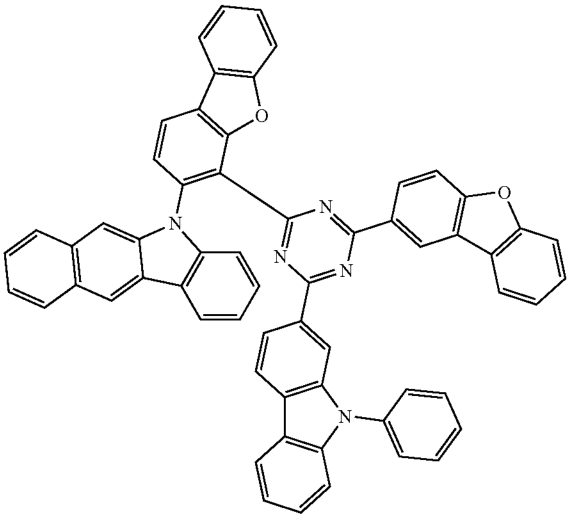
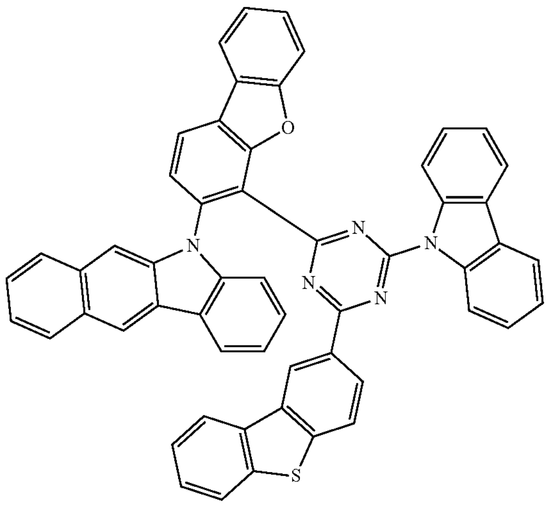
-continued -continued
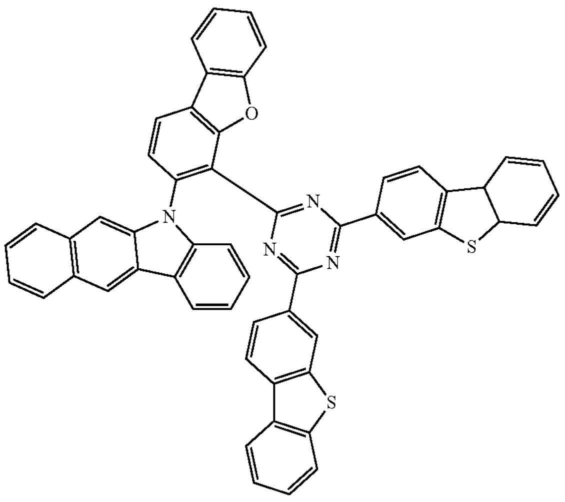
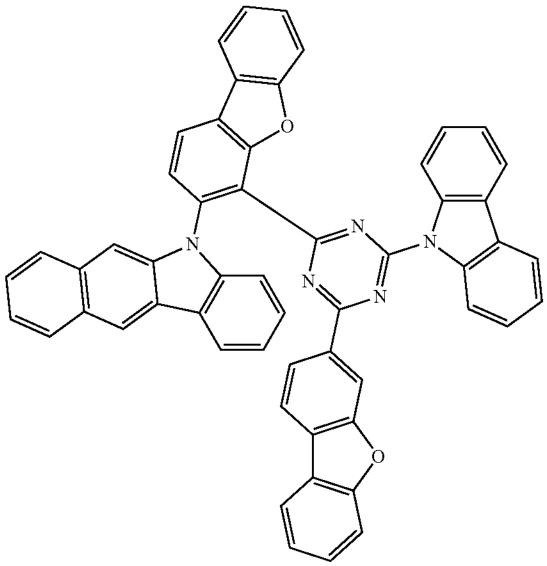
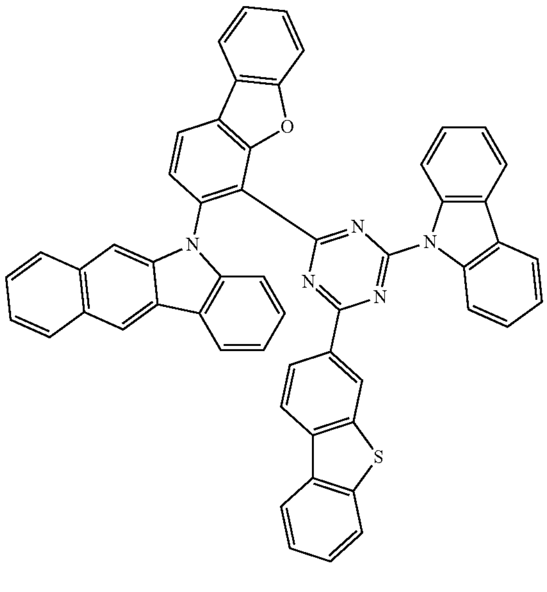
-continued
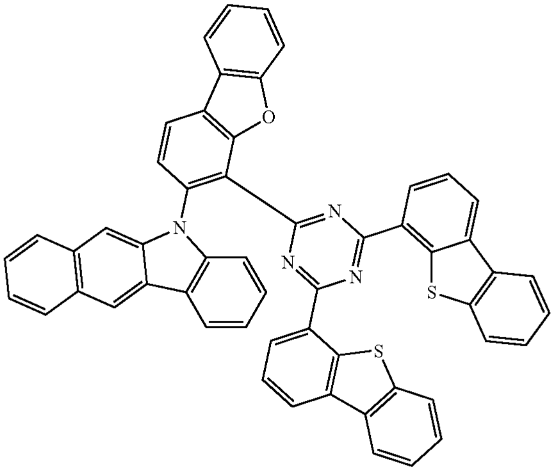
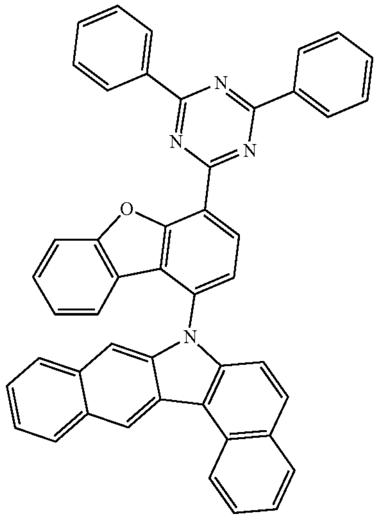
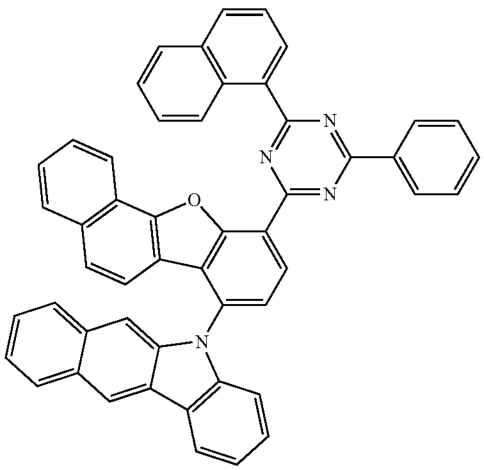

-continued
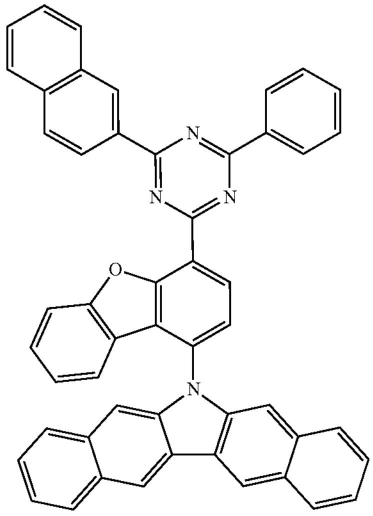
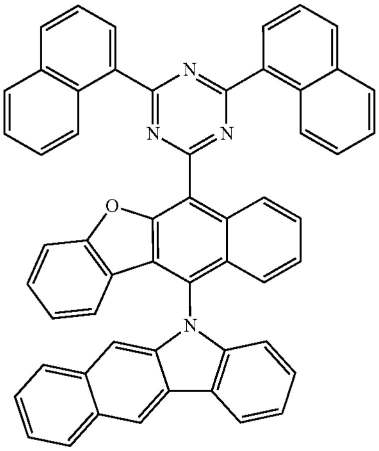
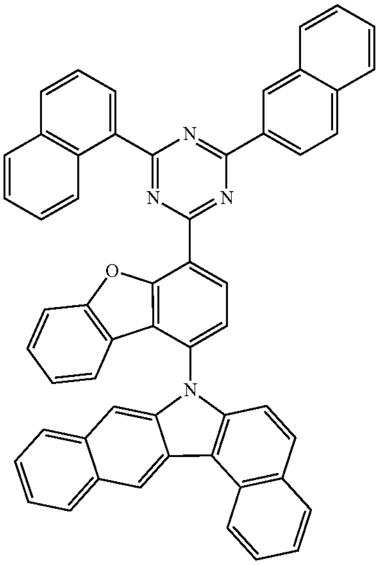
-continued
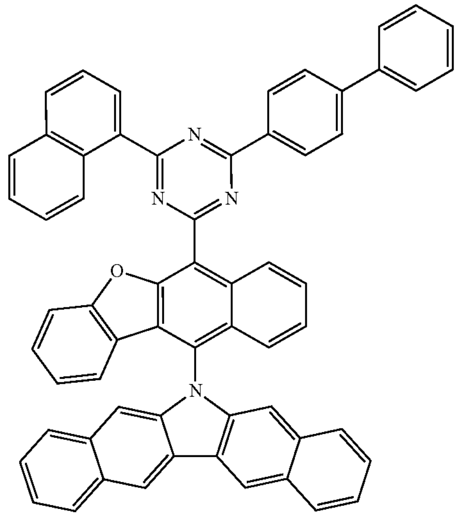
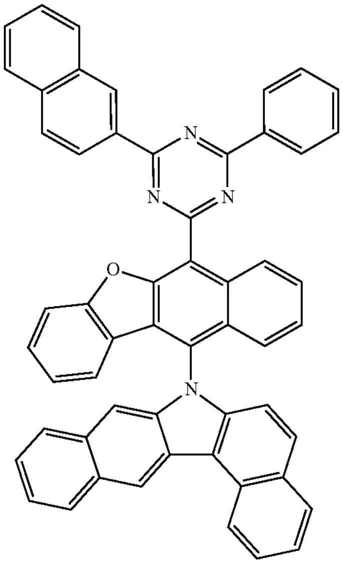
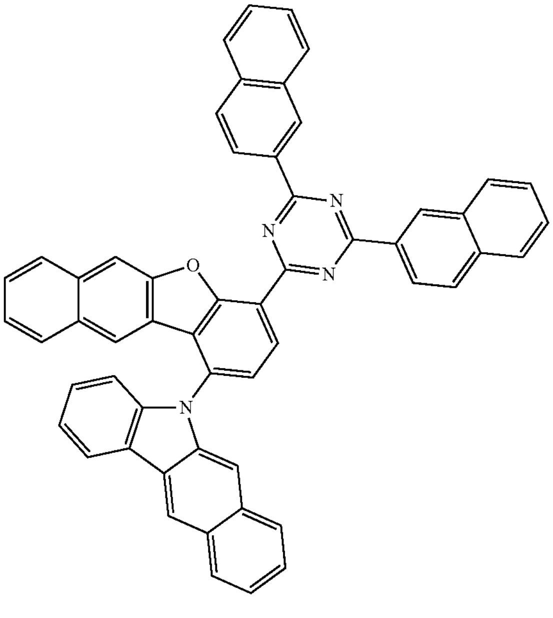

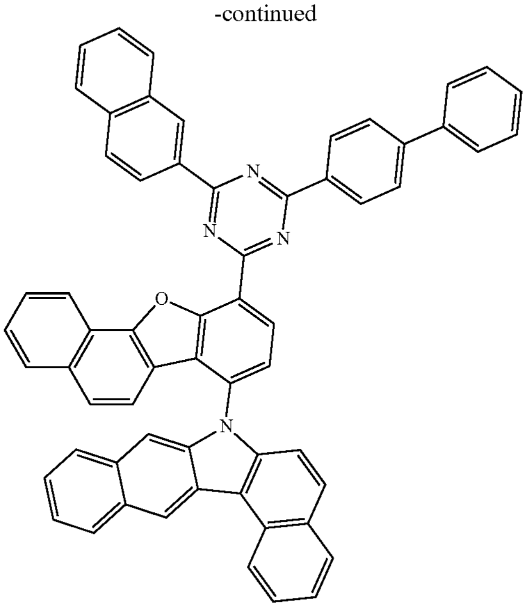
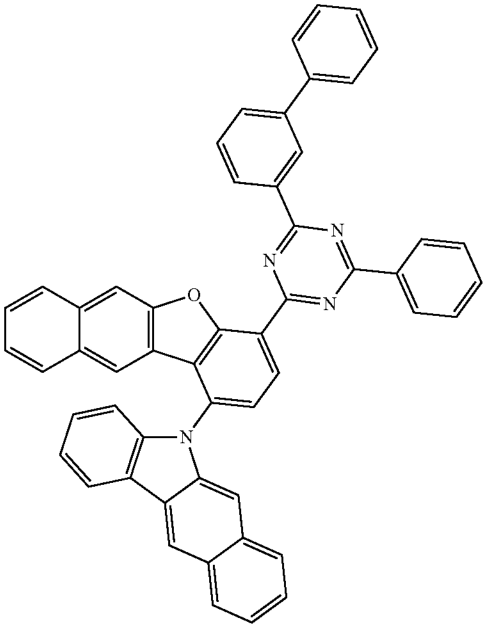
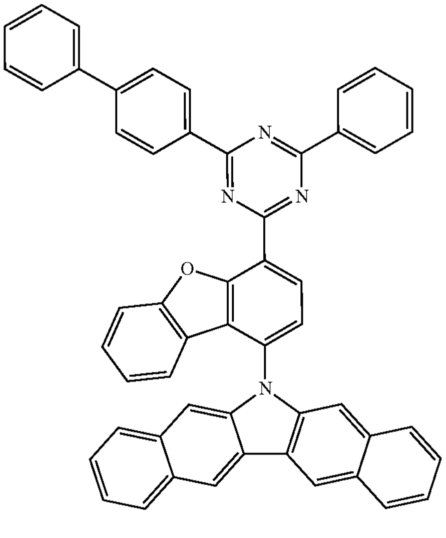
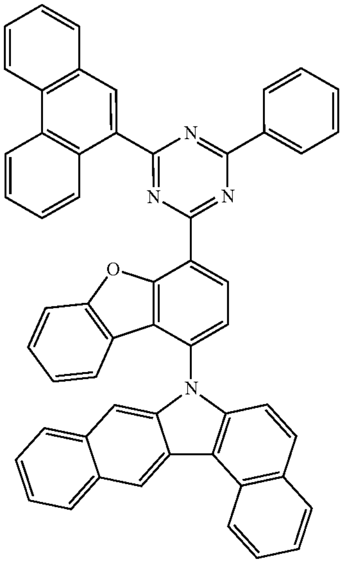
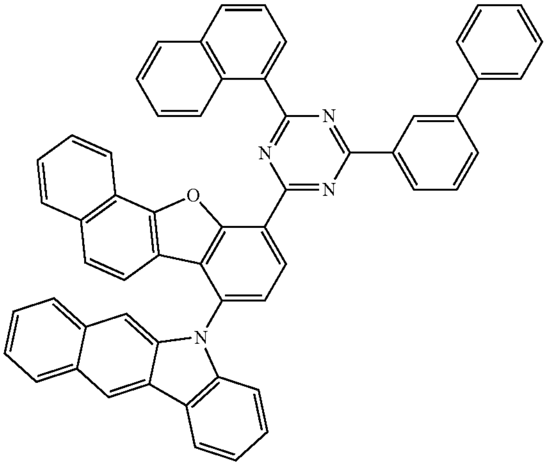
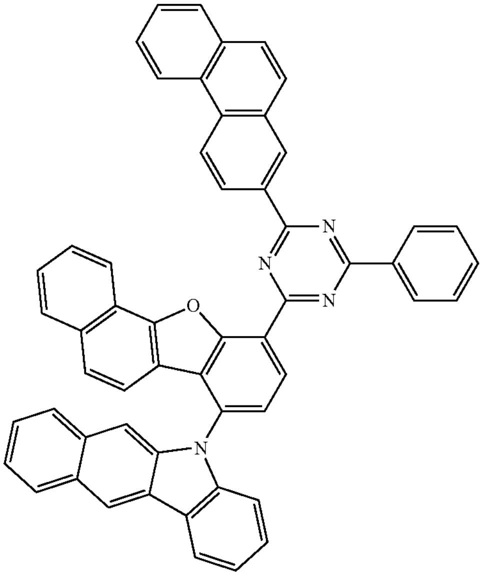

-continued
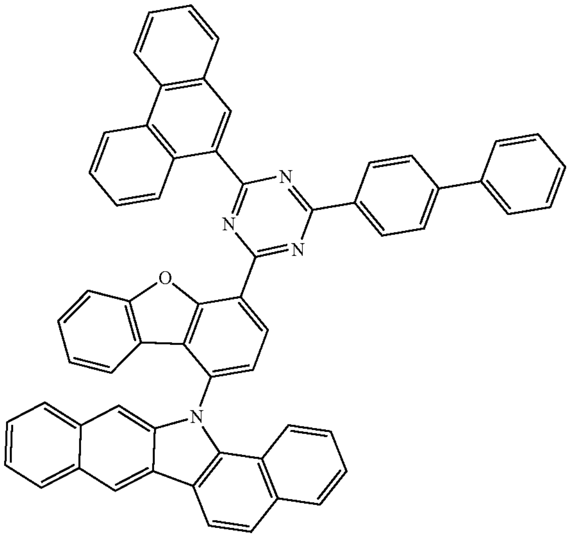
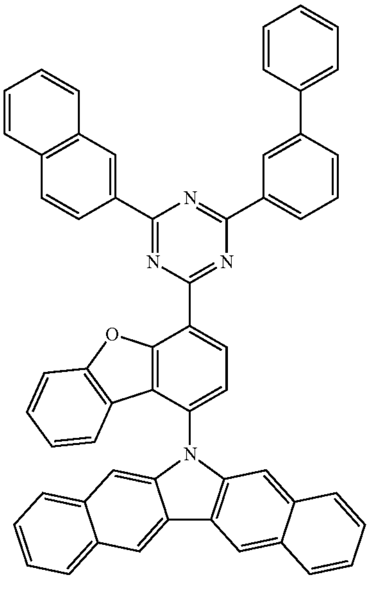
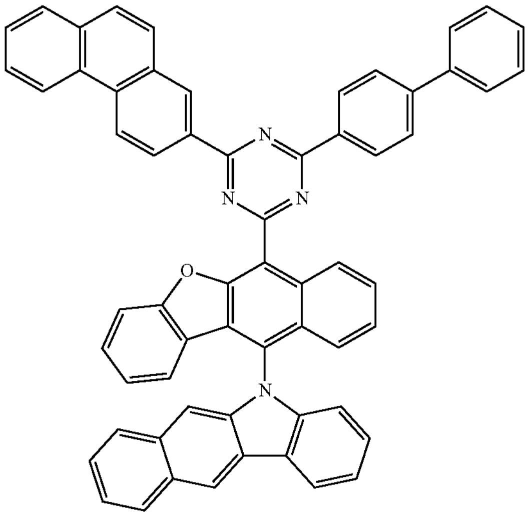
-continued
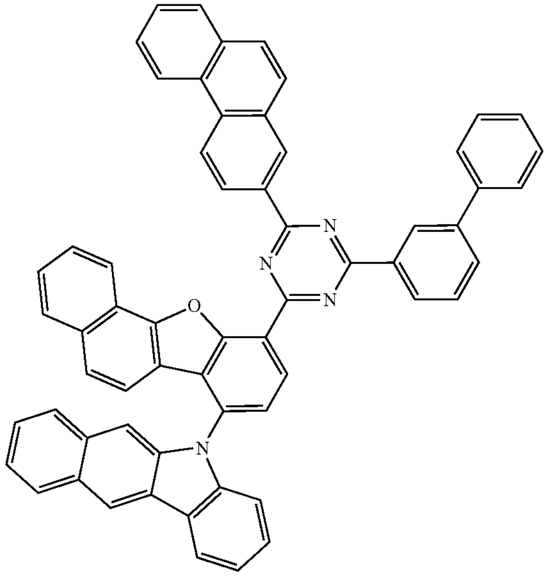
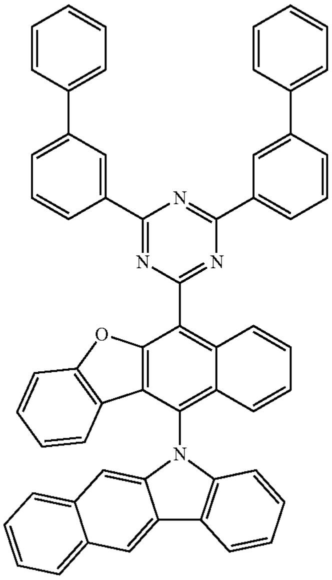
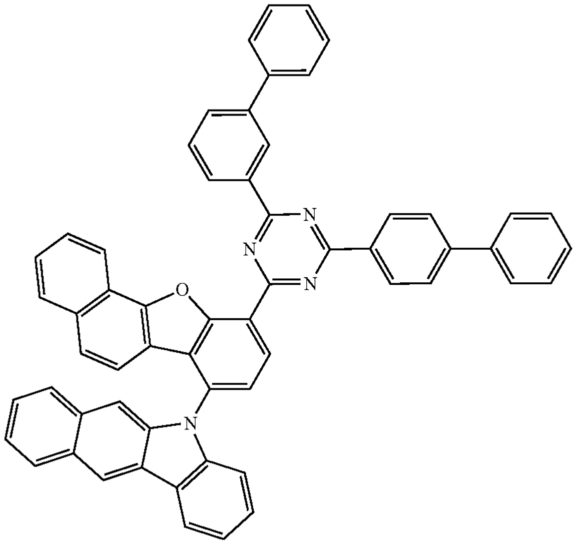

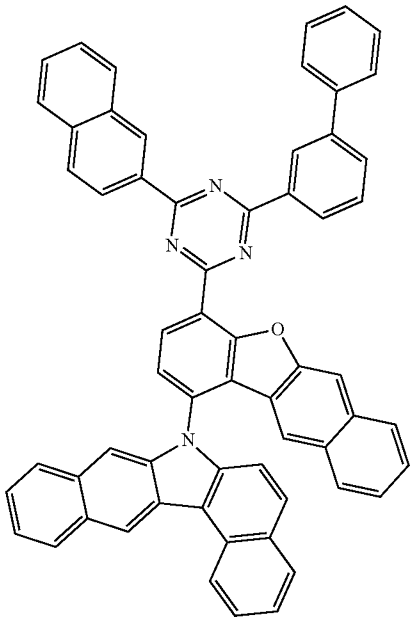
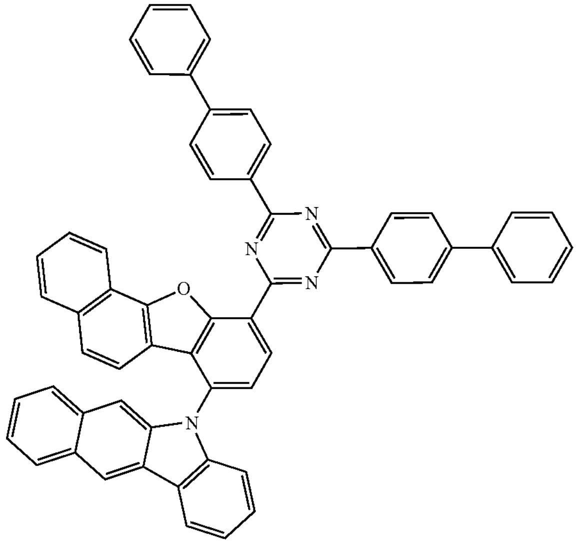
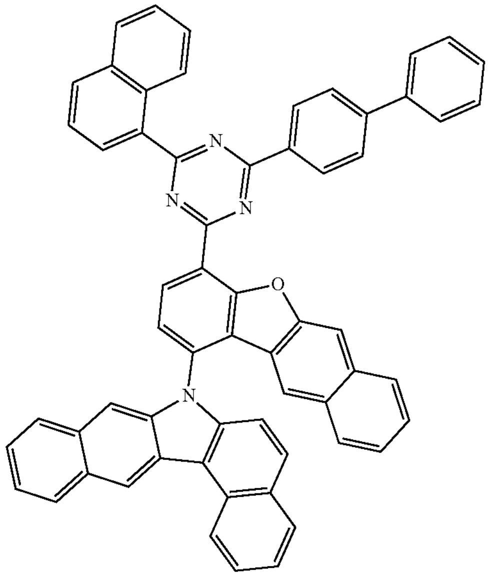
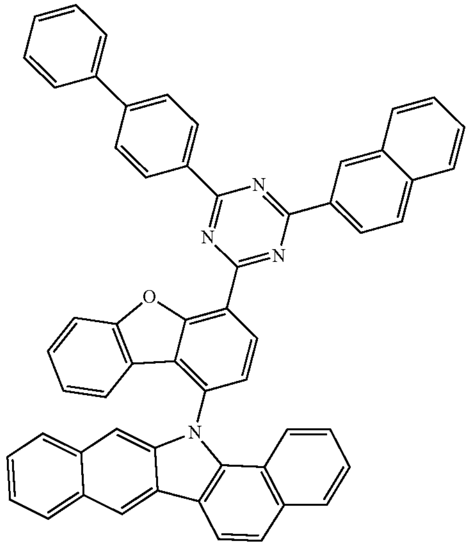
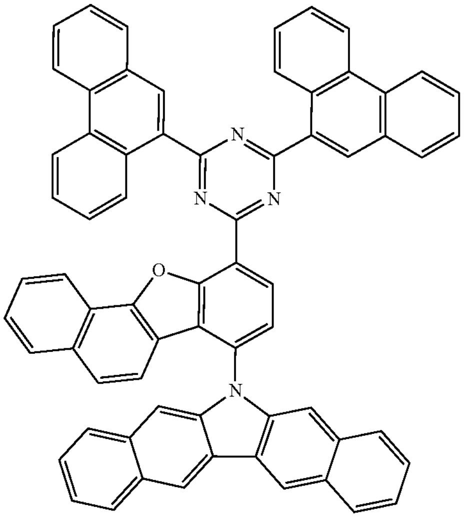

-continued
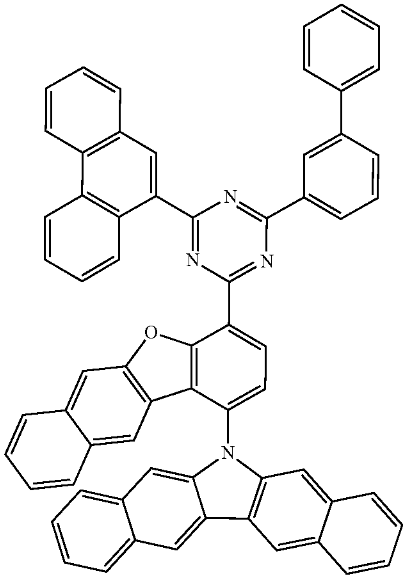
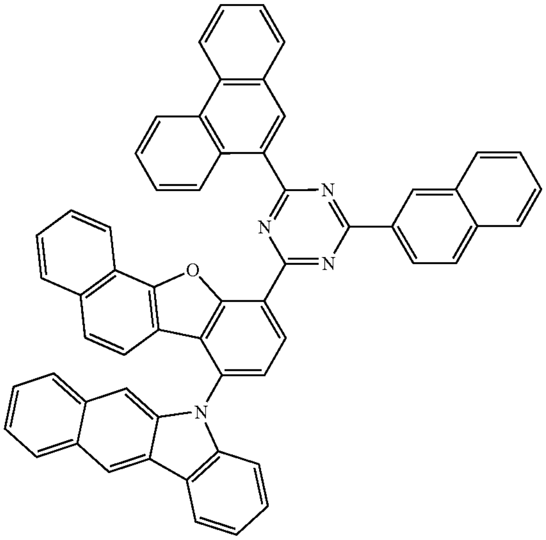
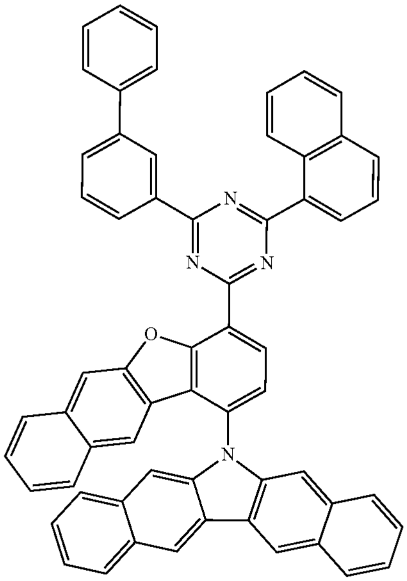
-continued
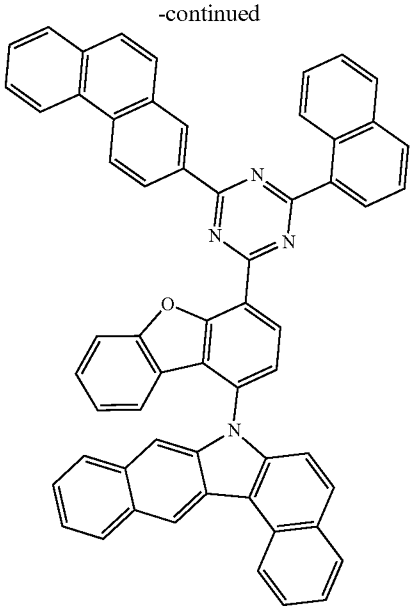
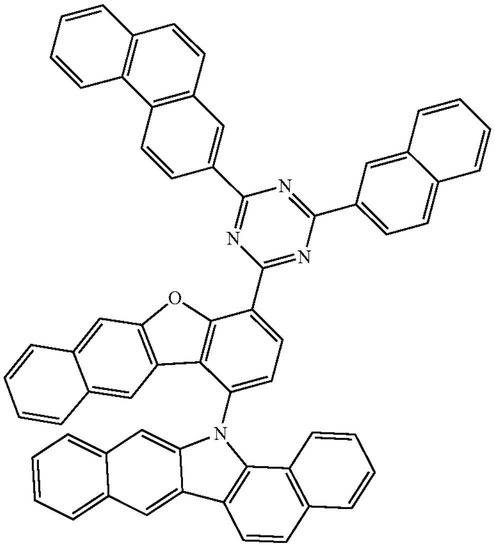

-continued
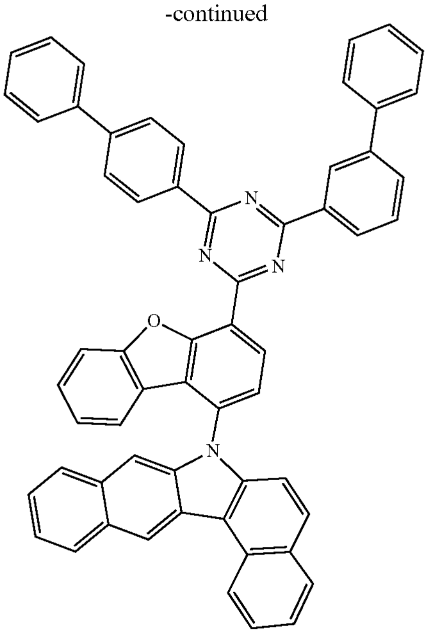
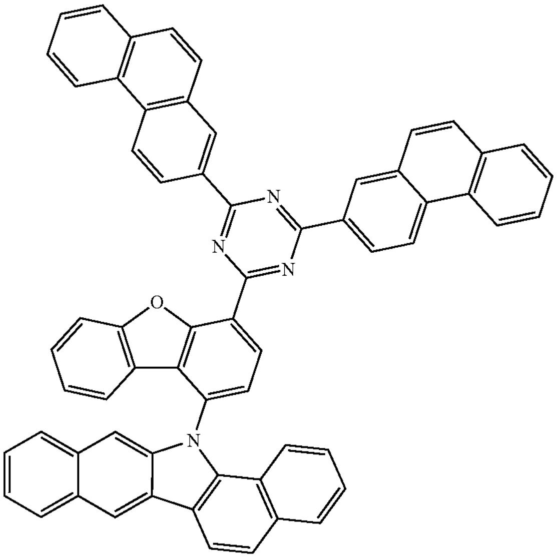
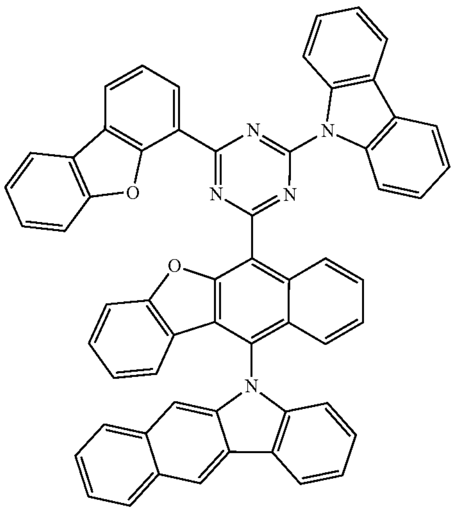
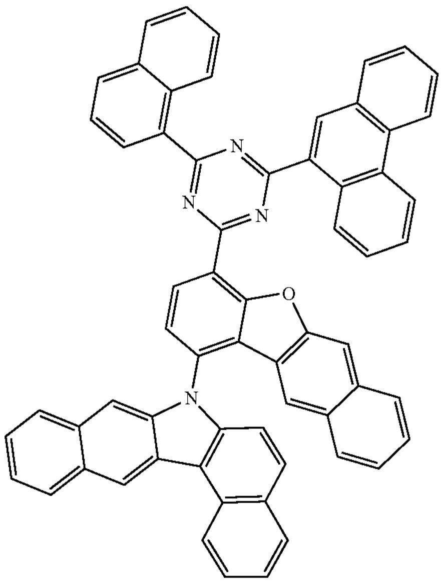
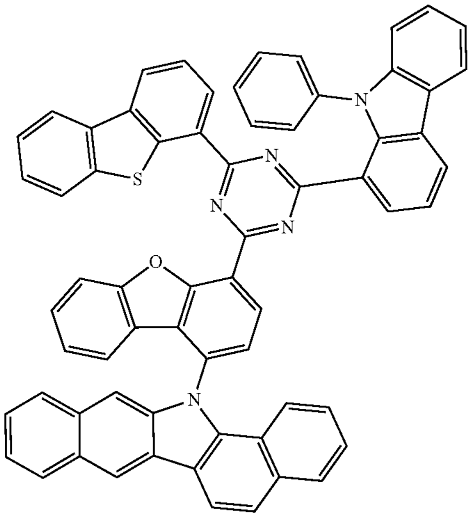
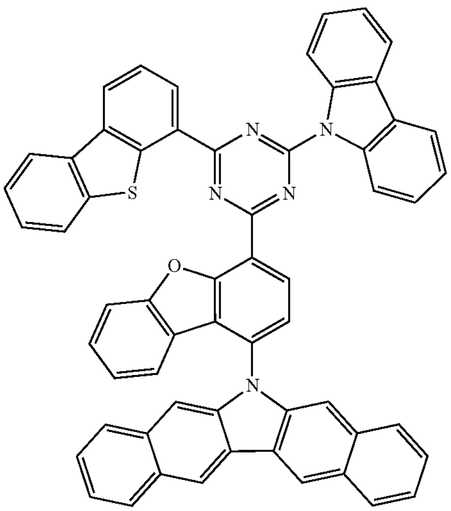
-continued -continued
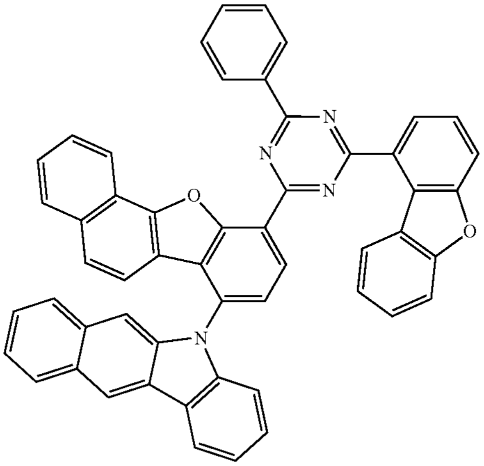
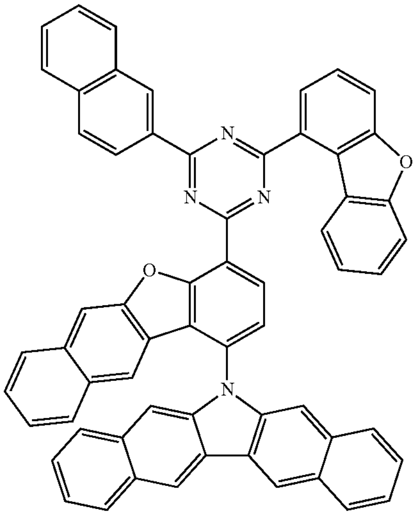
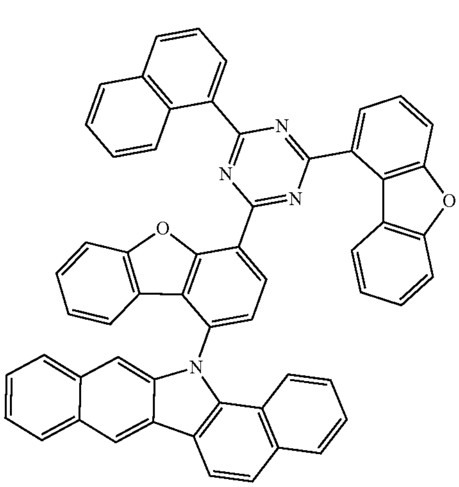
-continued
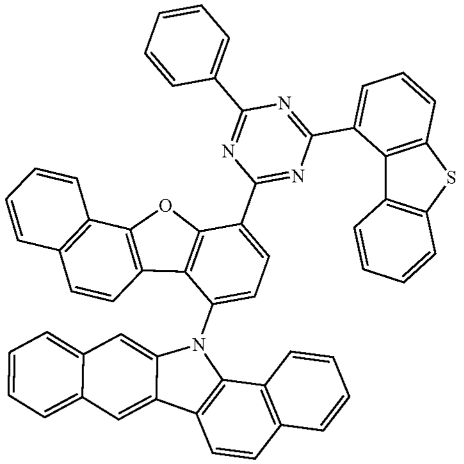
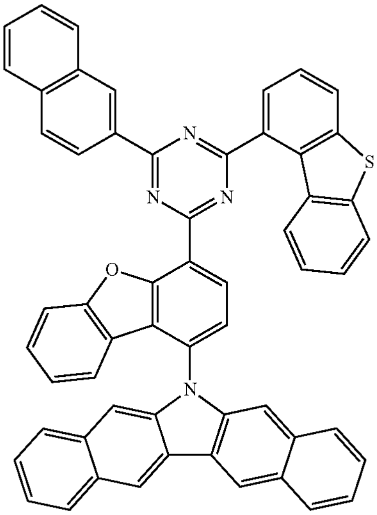
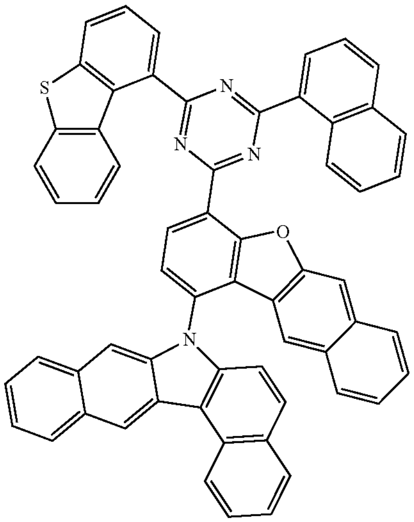

-continued
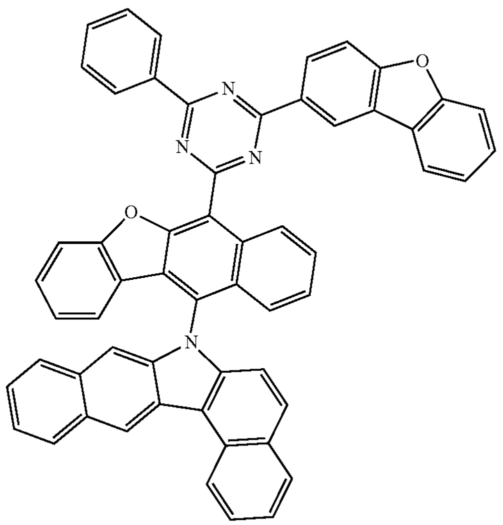
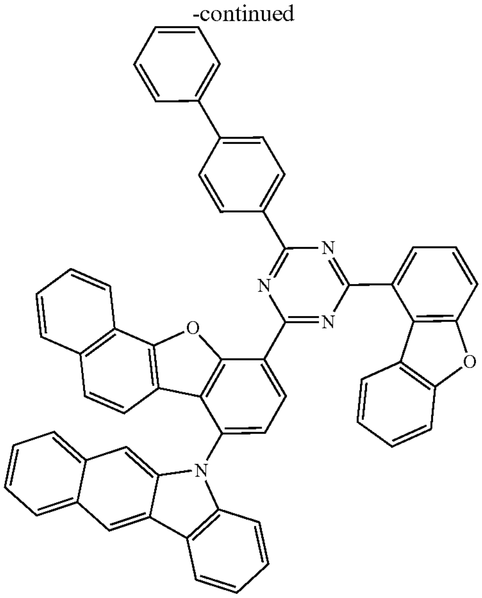
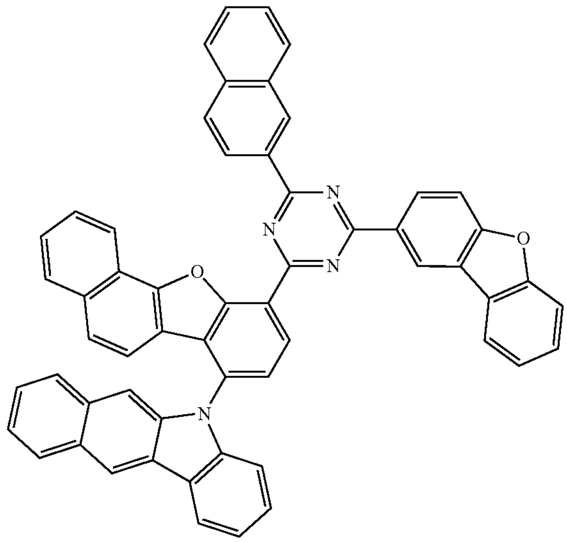
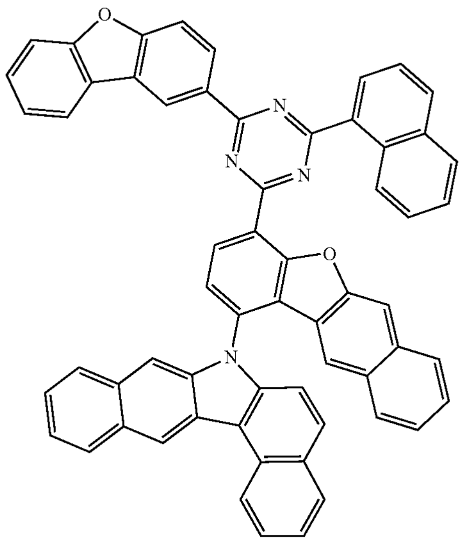
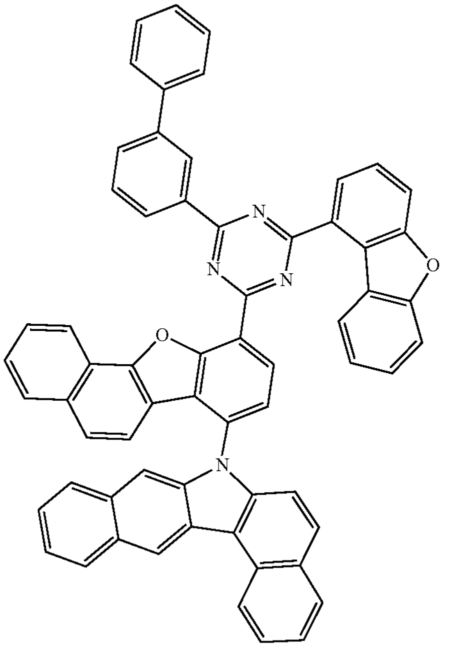
-continued -continued
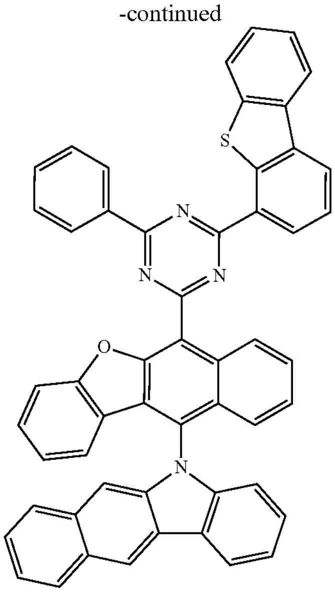
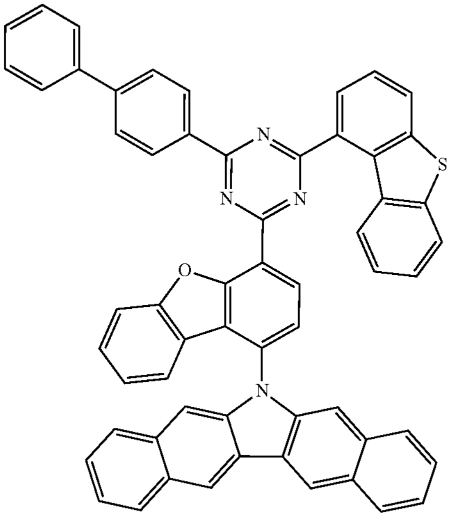
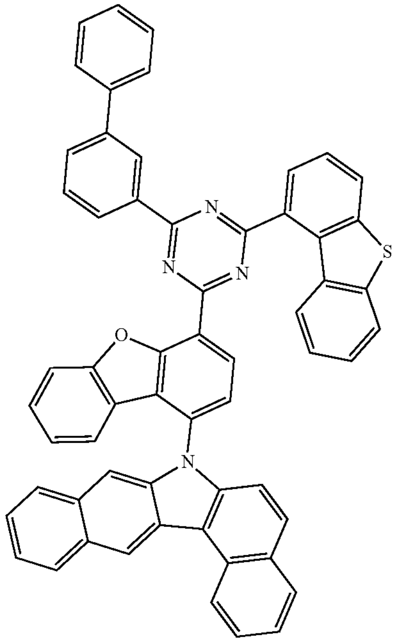
-continued
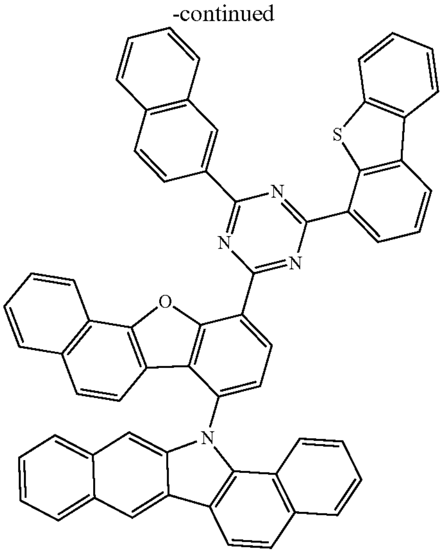
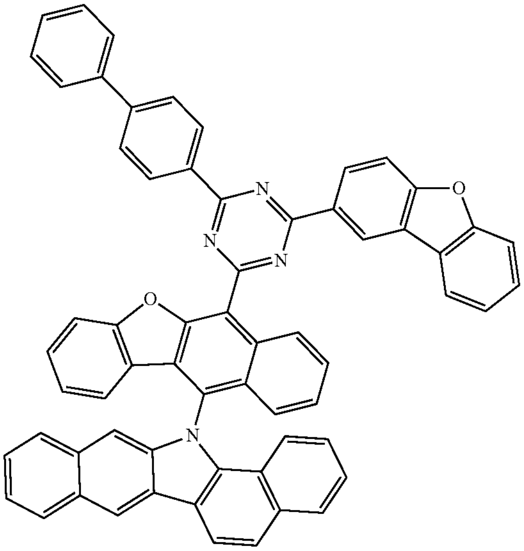
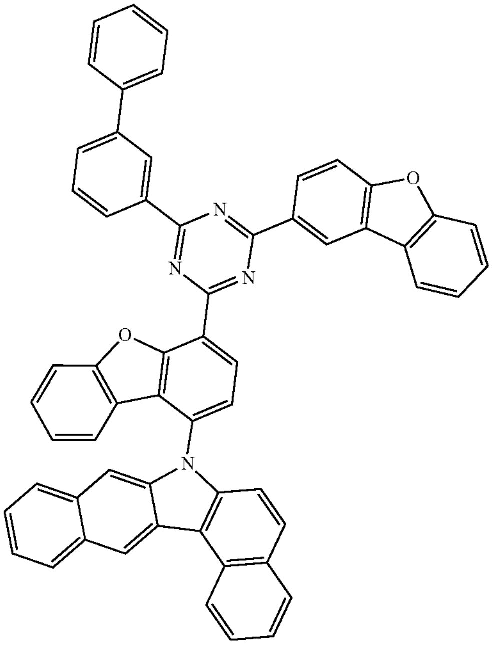

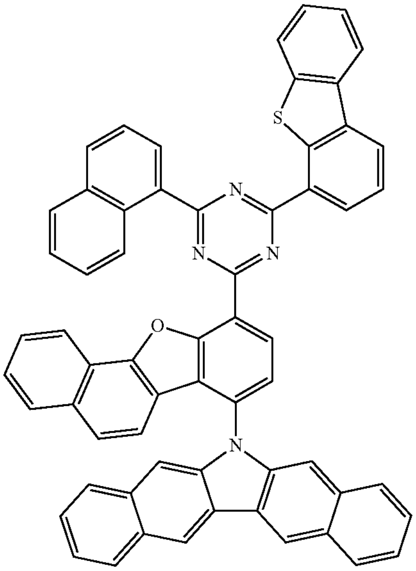
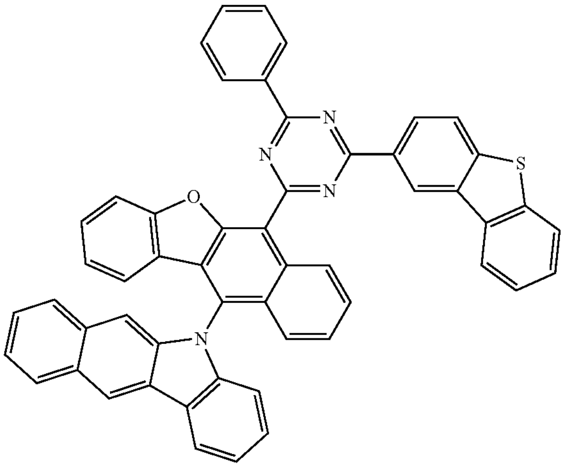
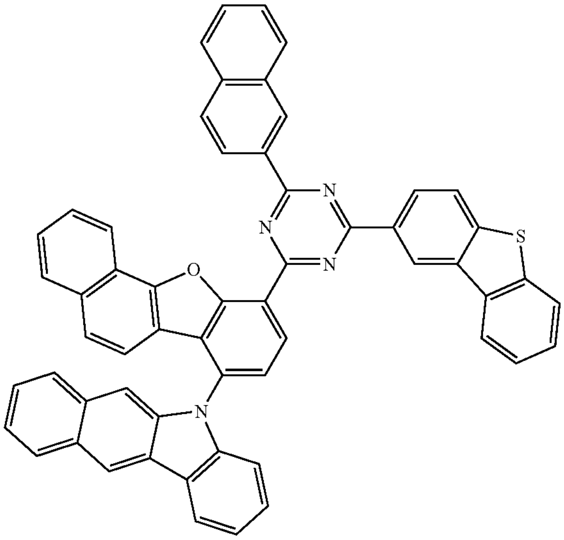
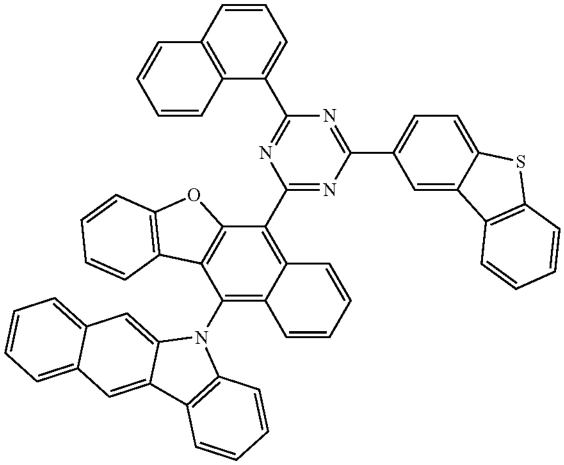
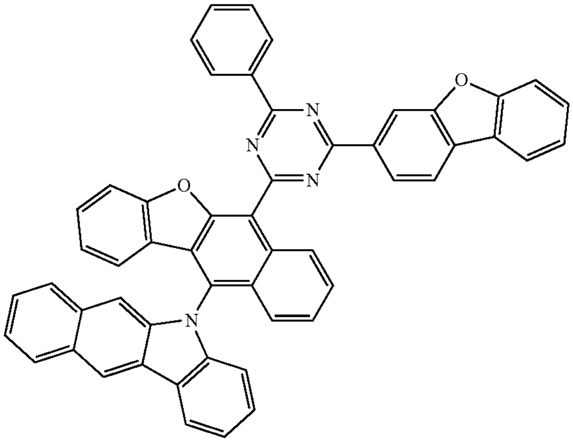
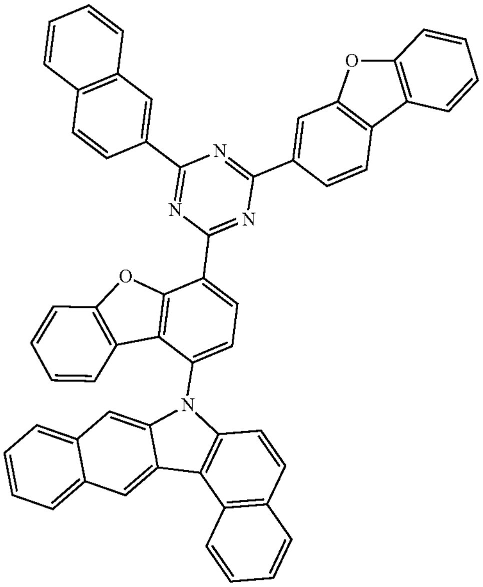

-continued
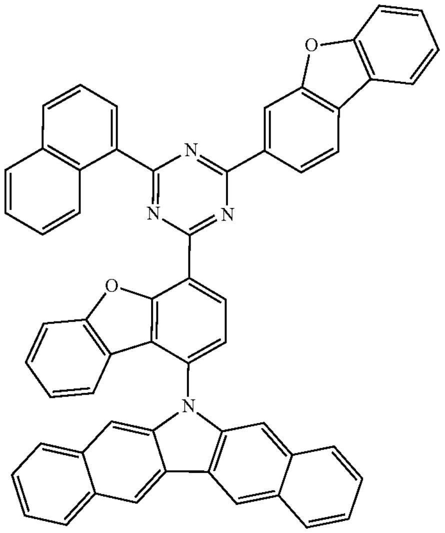
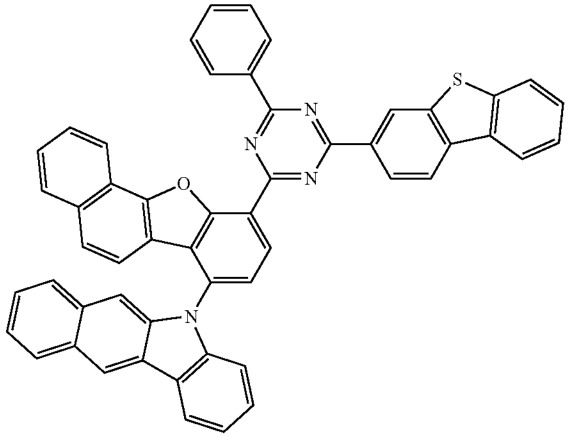
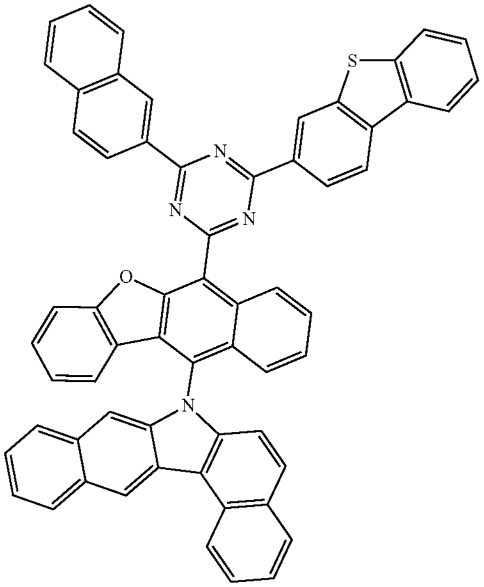
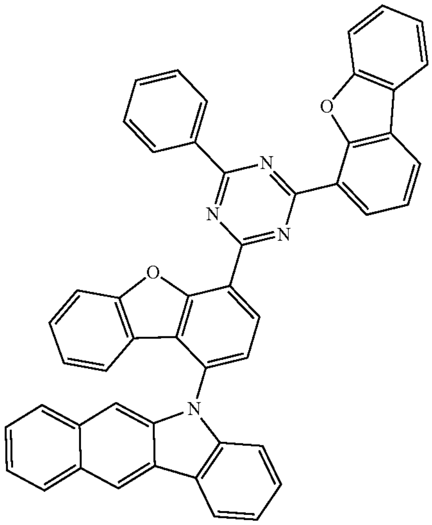
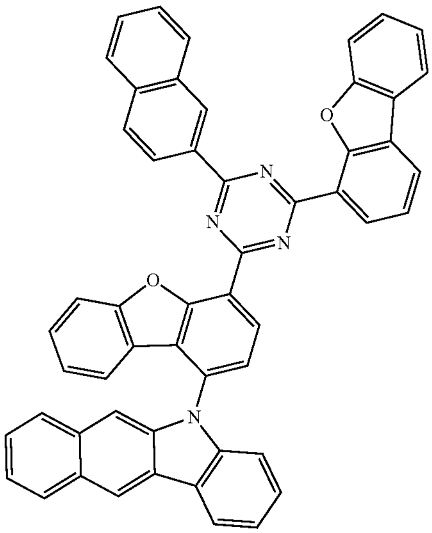
-continued
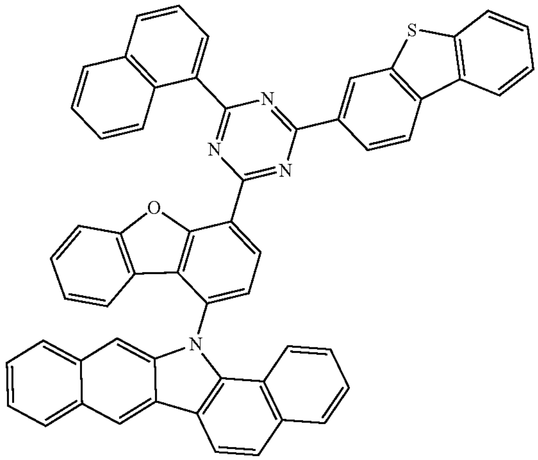

-continued
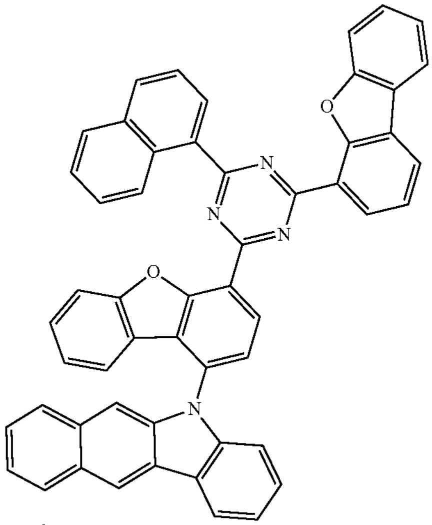
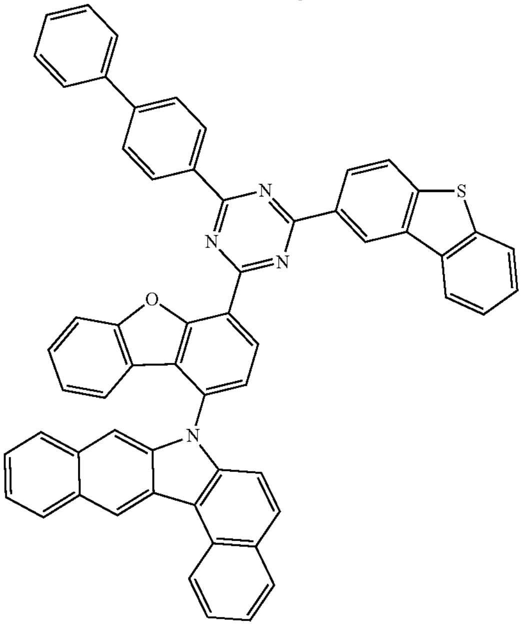
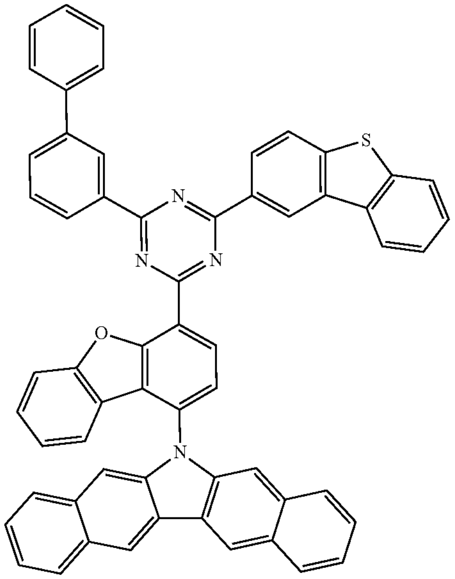
-continued
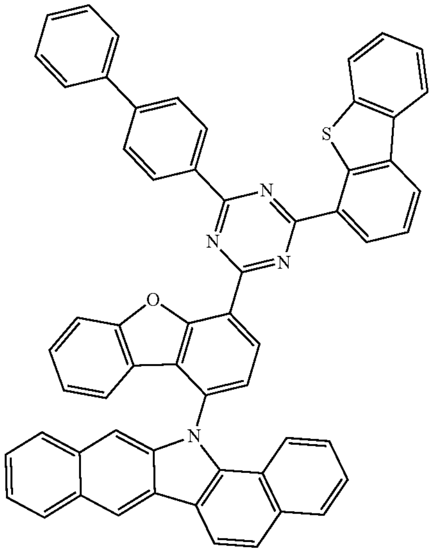
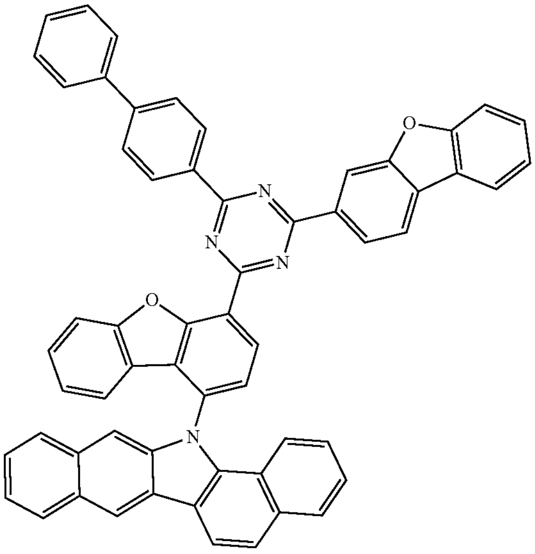
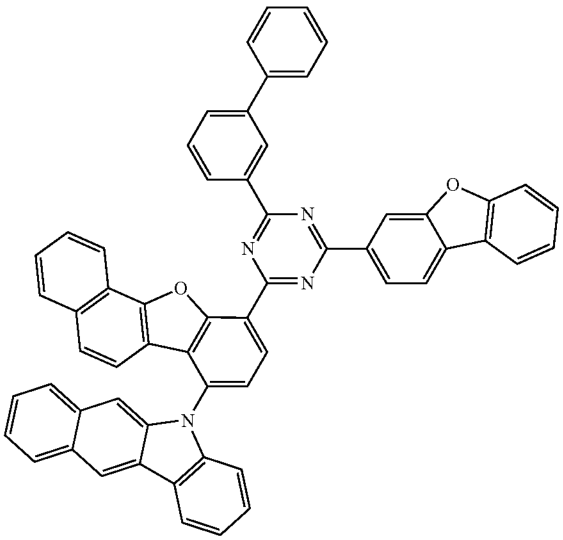

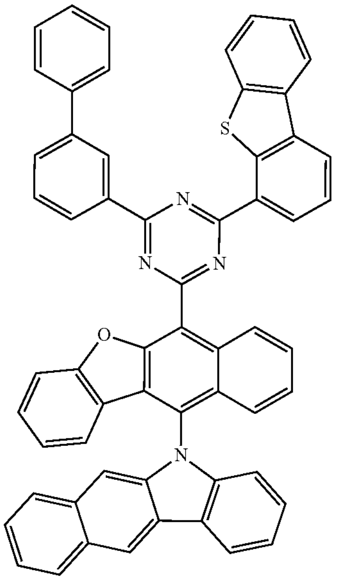
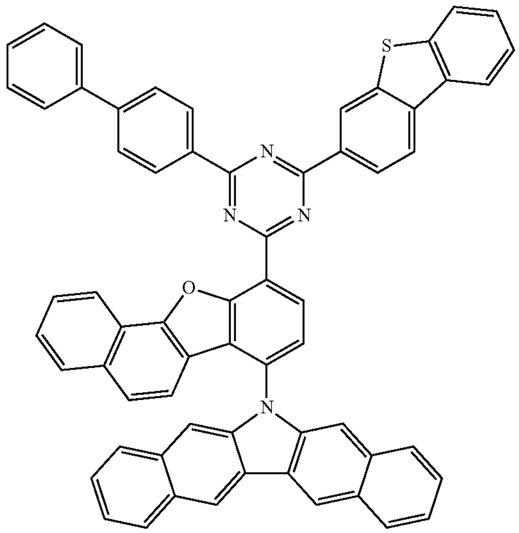
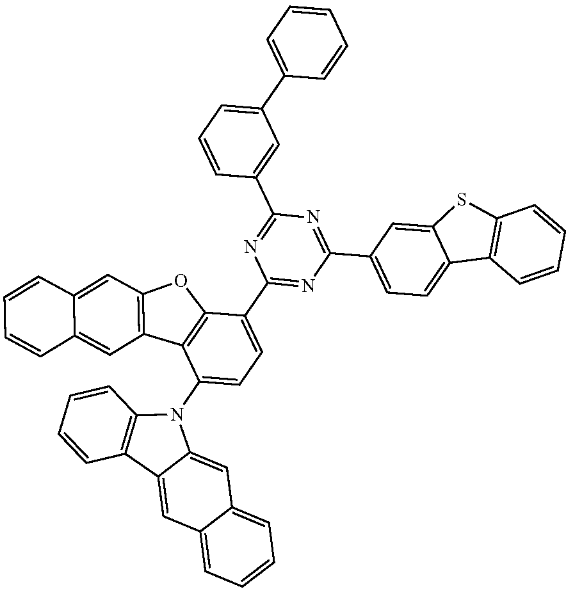
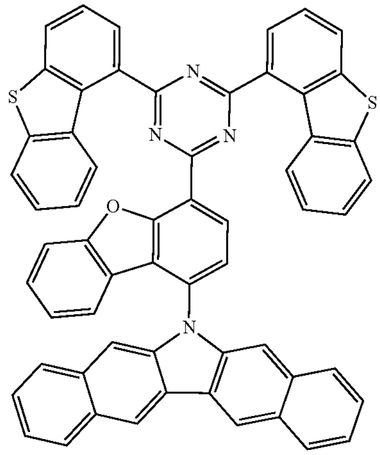
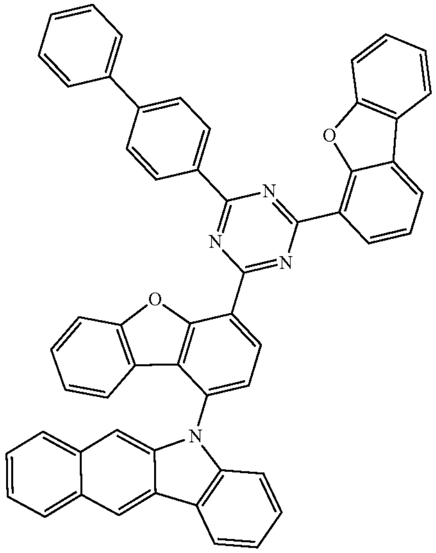
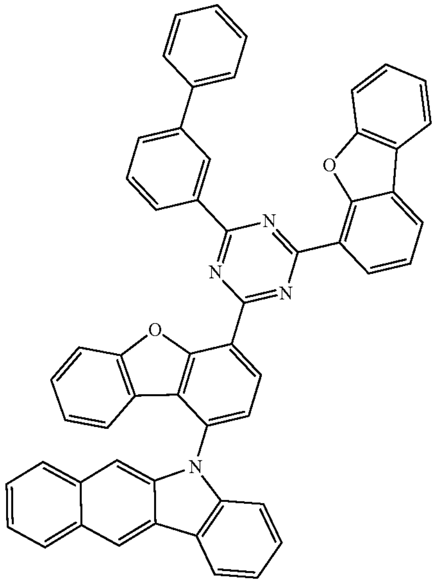

-continued
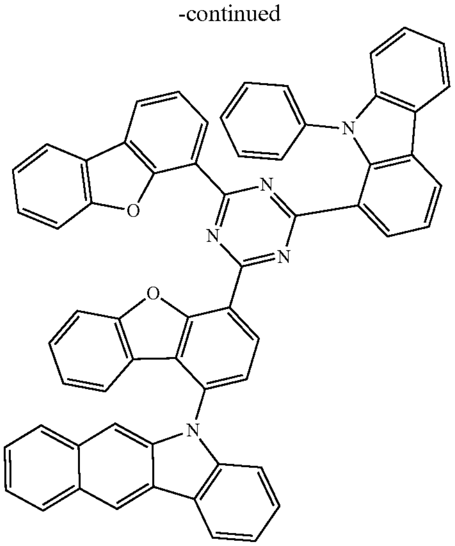
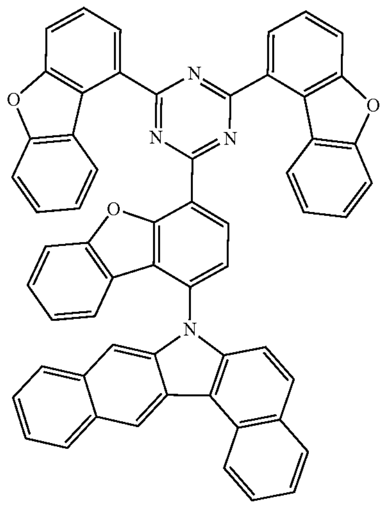
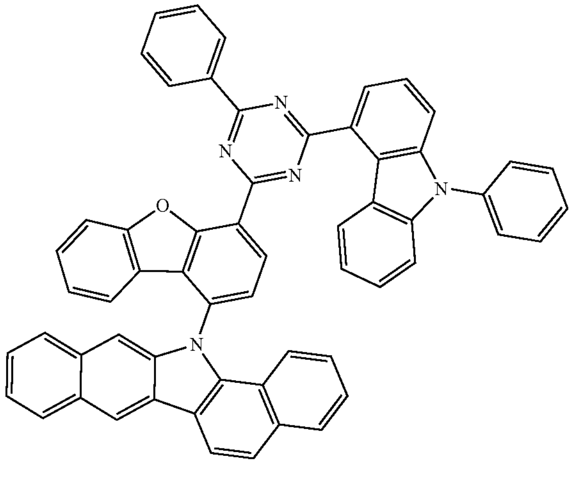
-continued
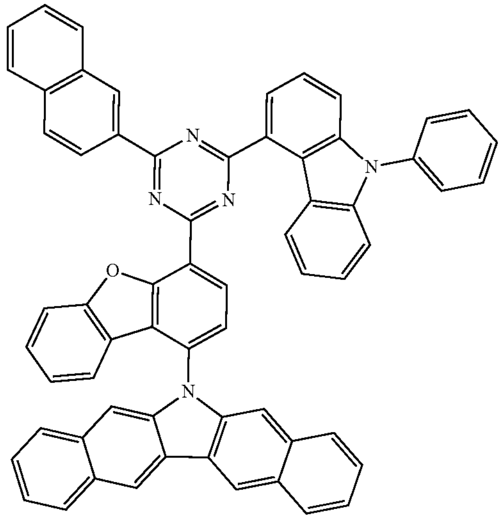
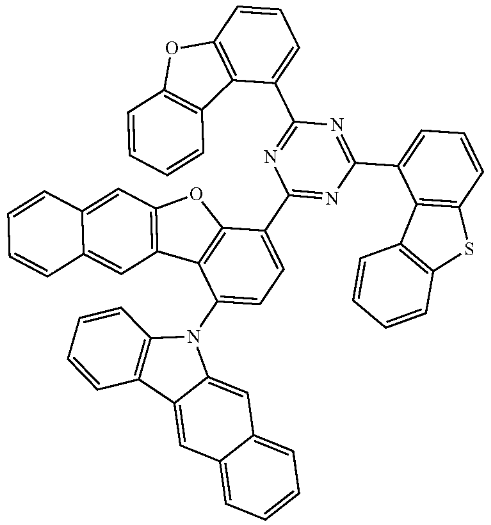
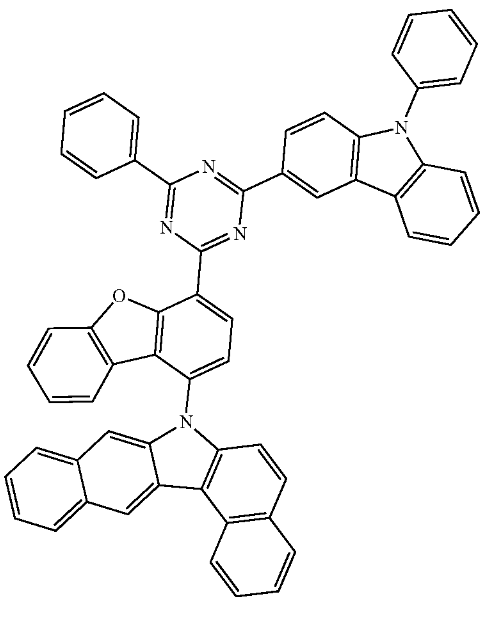

-continued
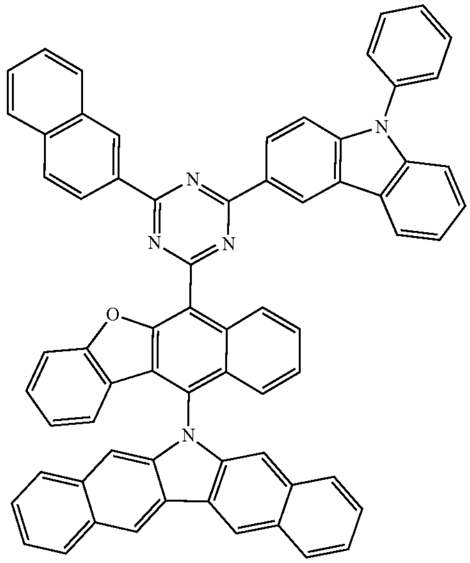
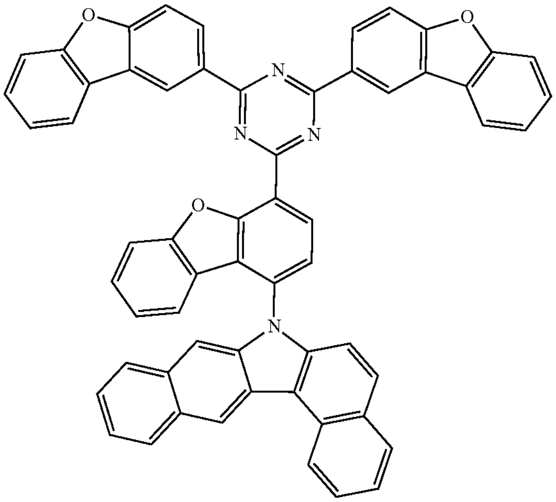
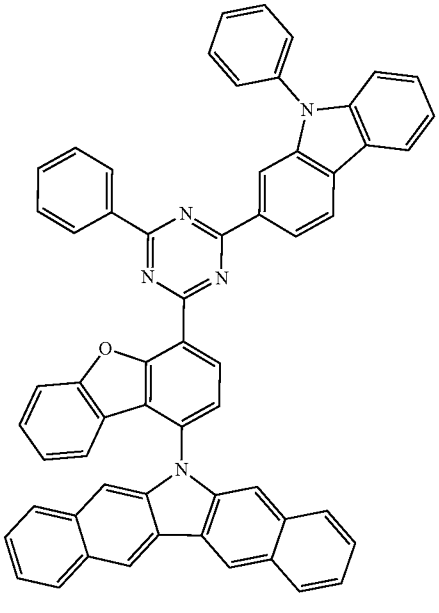
-continued
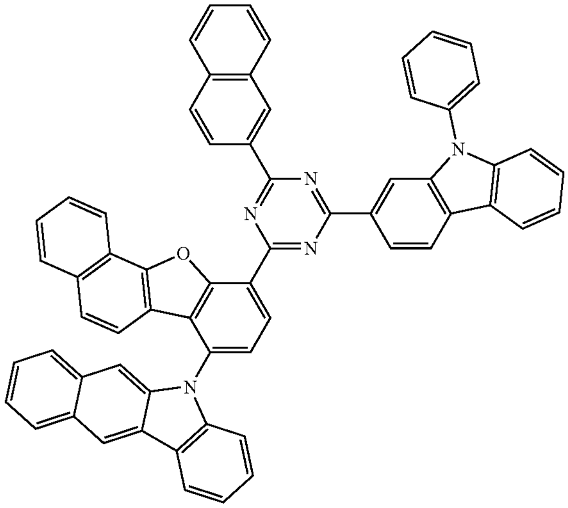
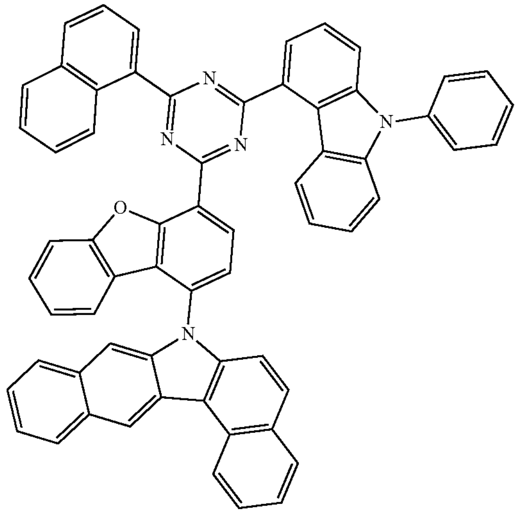
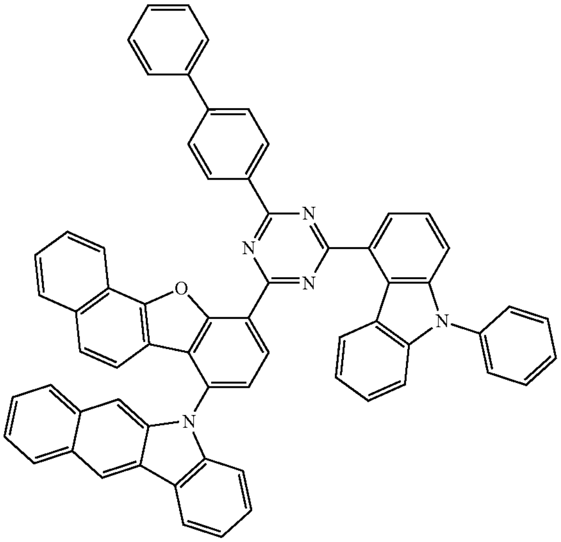

-continued
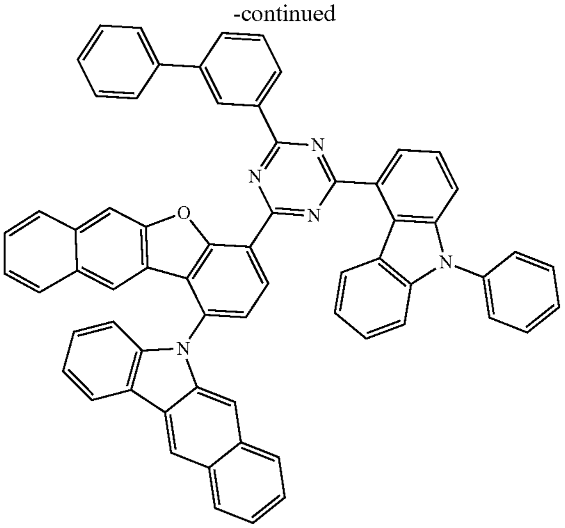
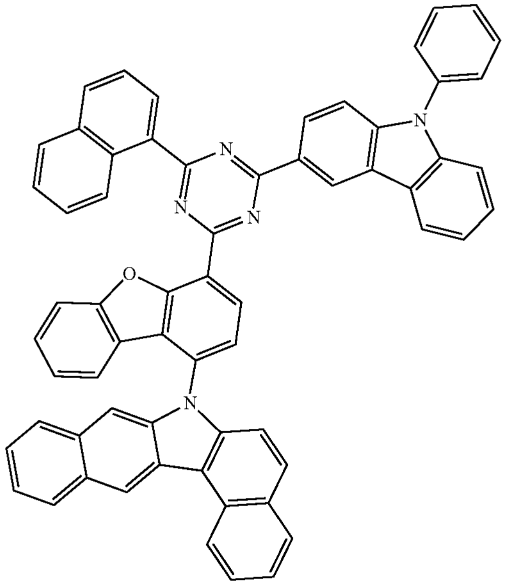
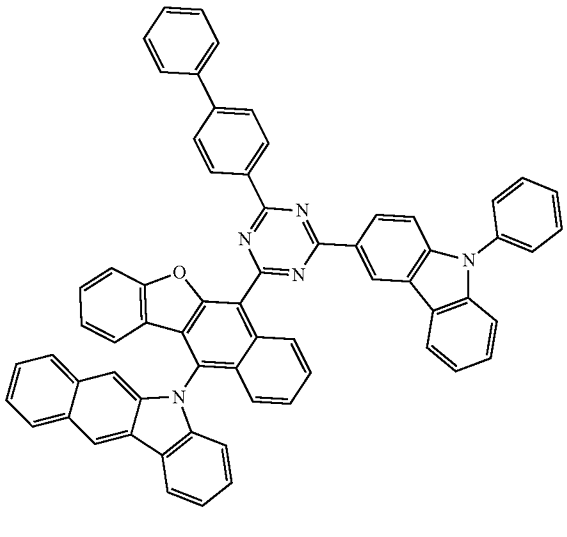
-continued
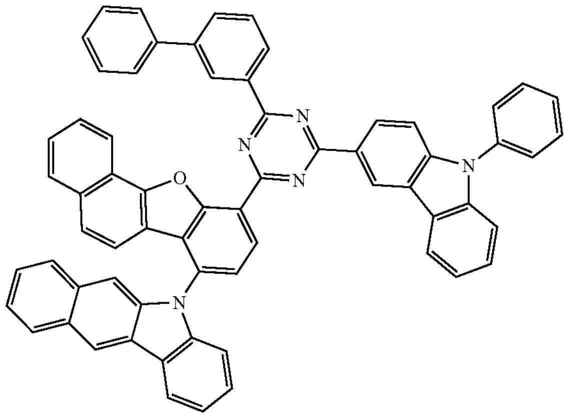
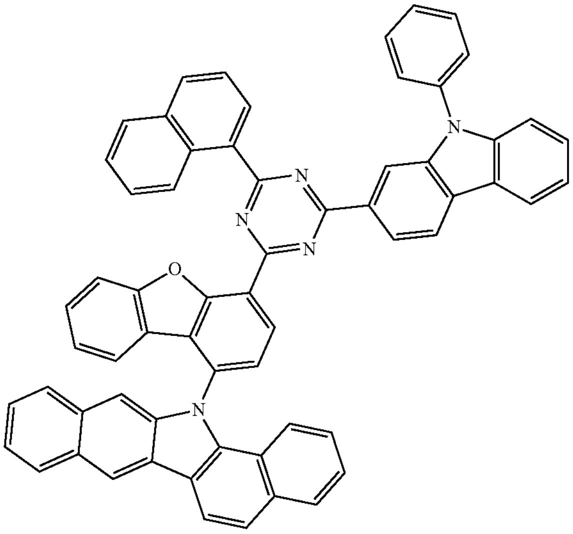
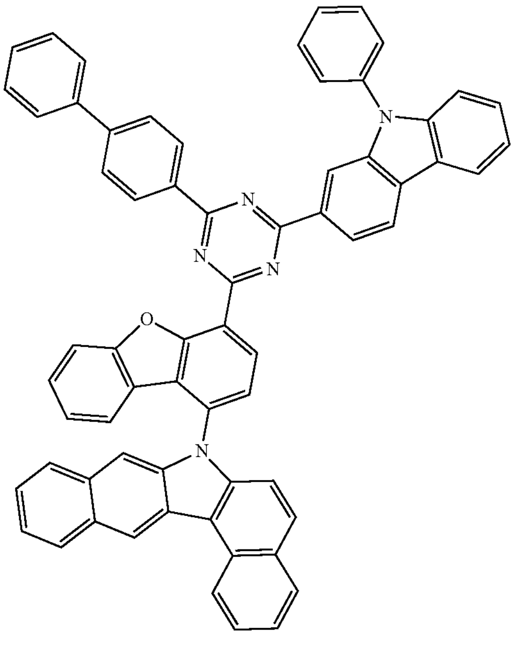

-continued
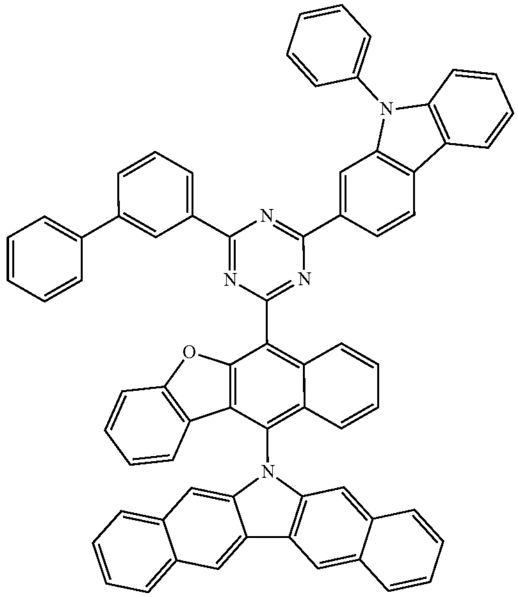
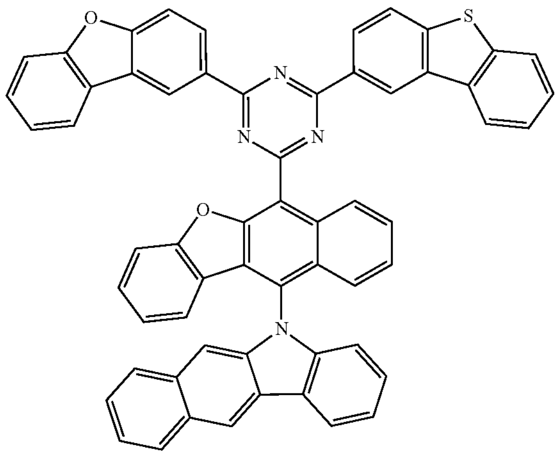
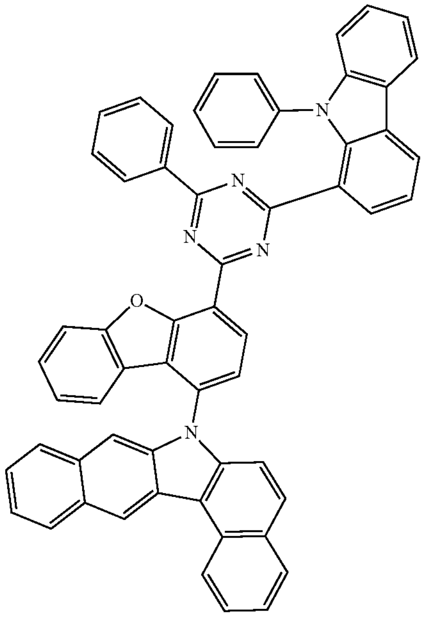
-continued
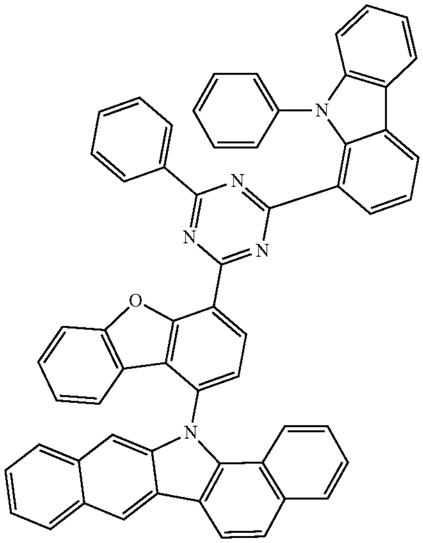
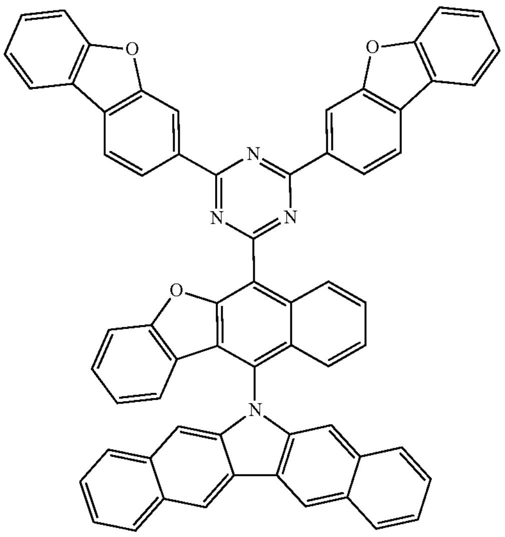
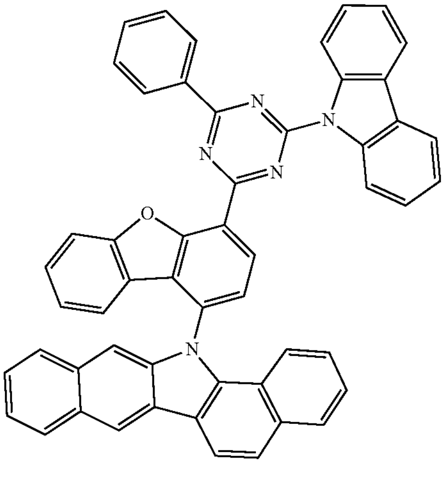

-continued
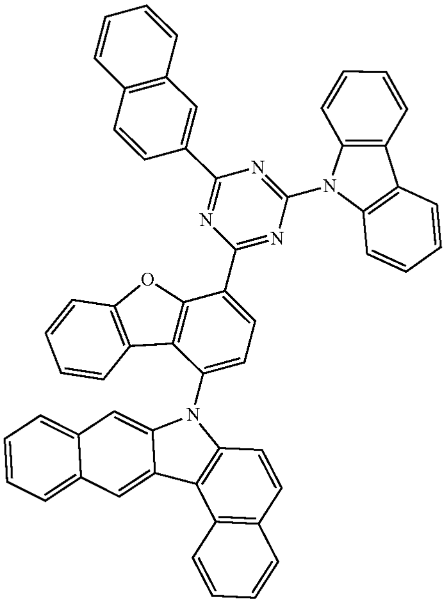
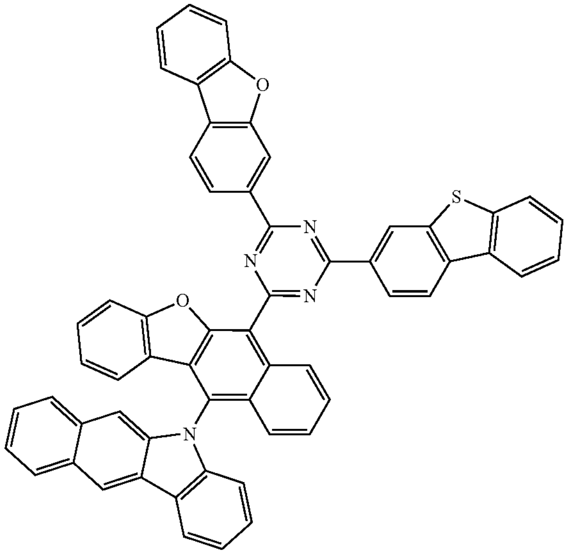
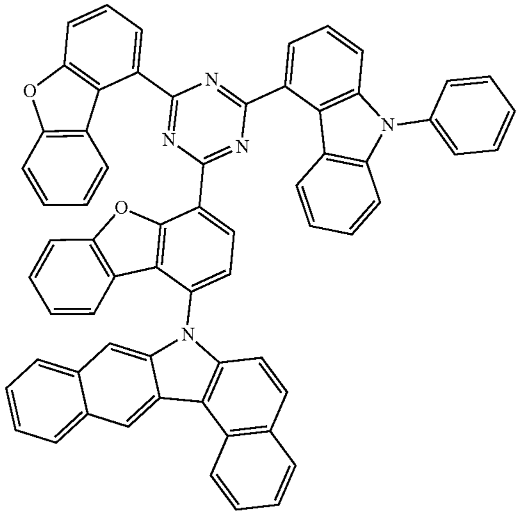
-continued
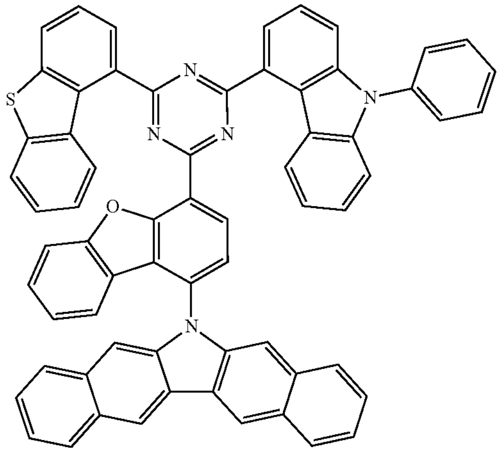
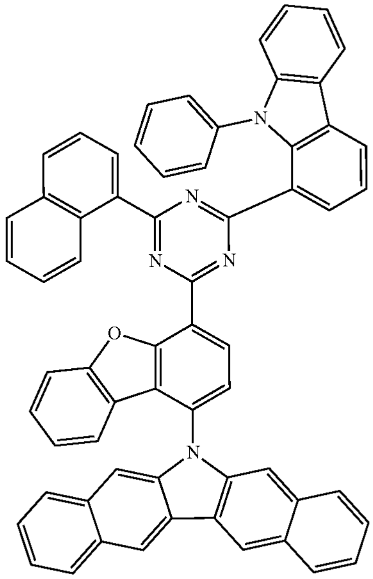
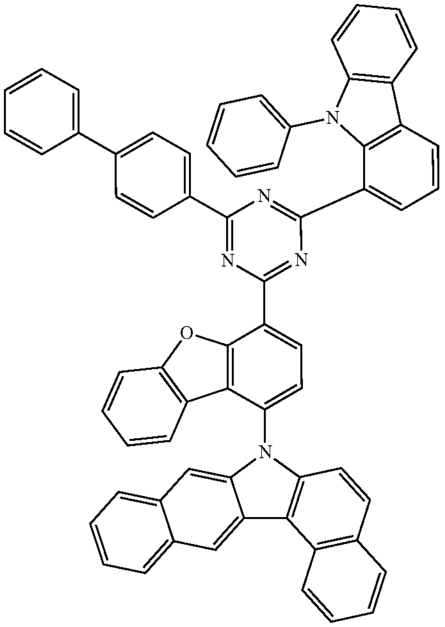

-continued
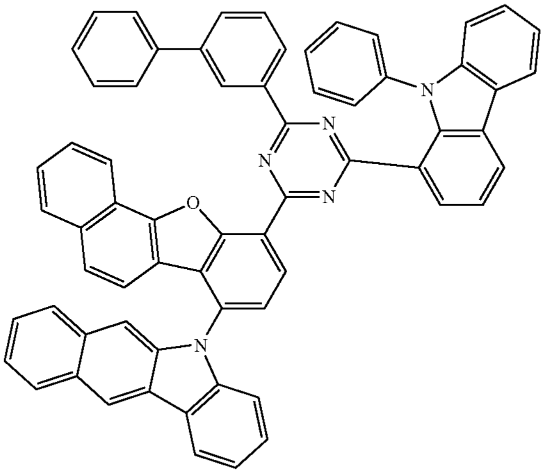
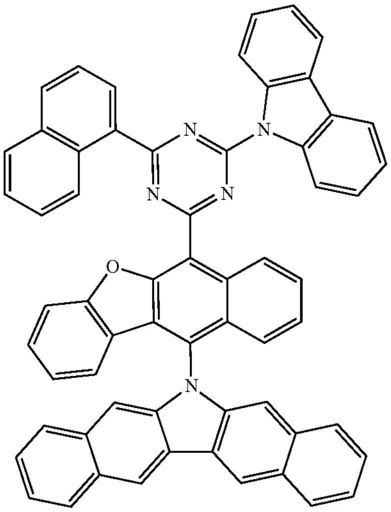
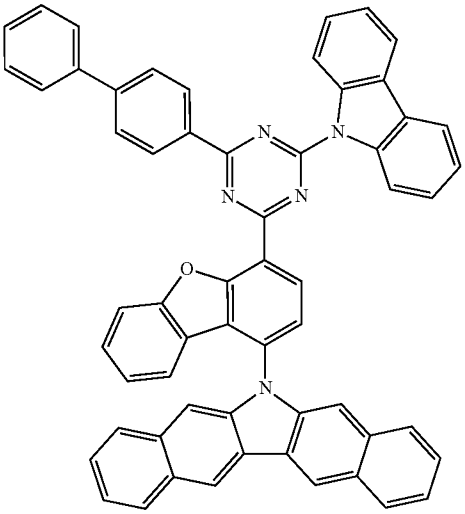
-continued
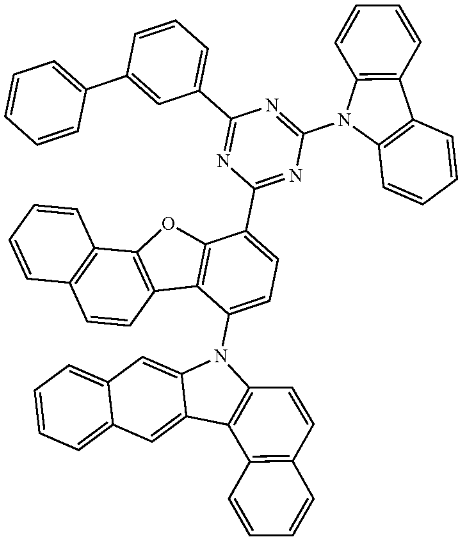
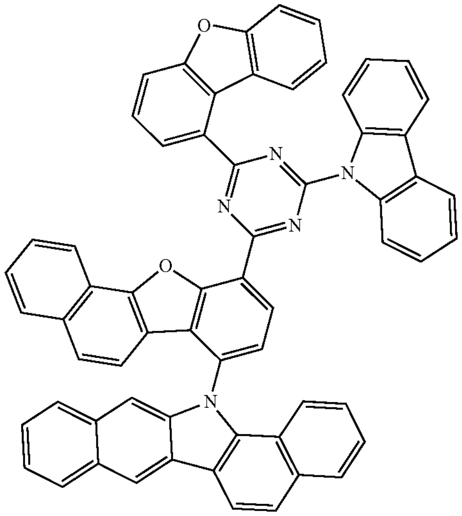
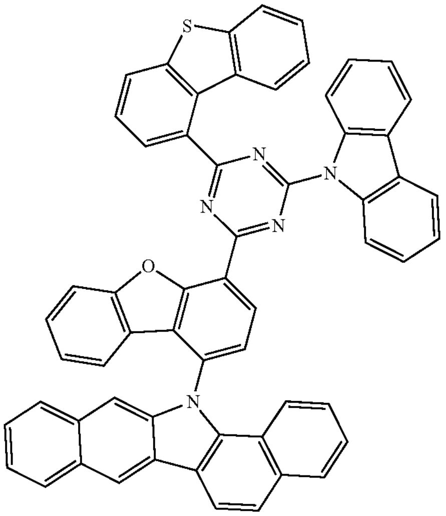

-continued
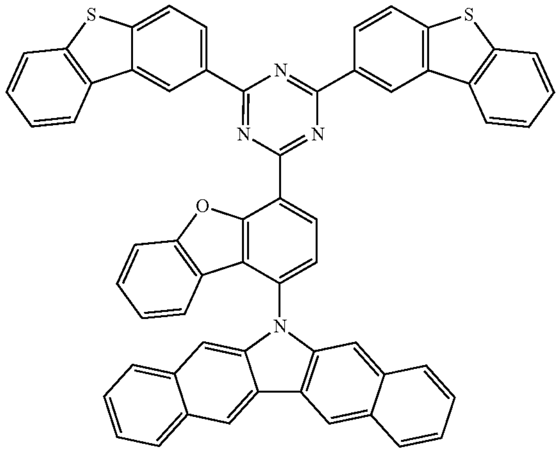
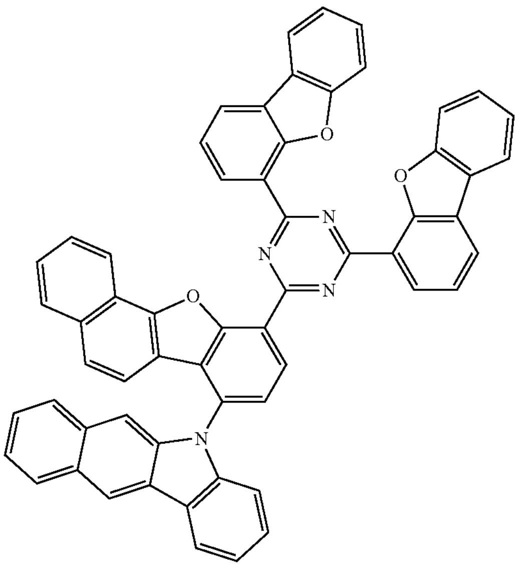
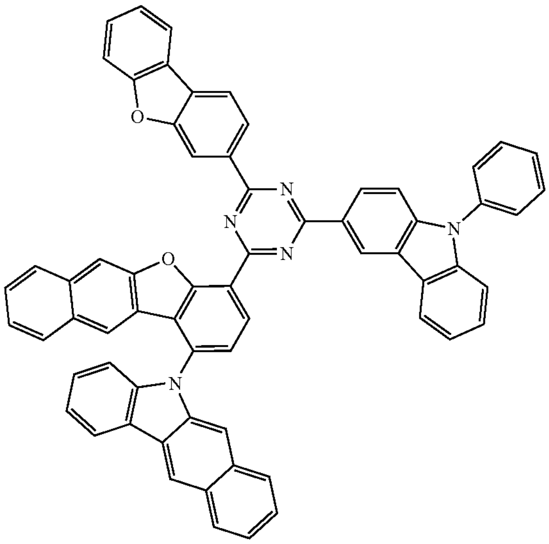
-continued
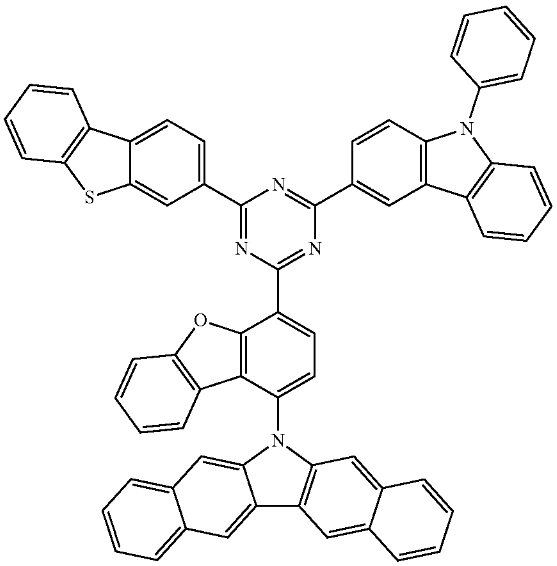
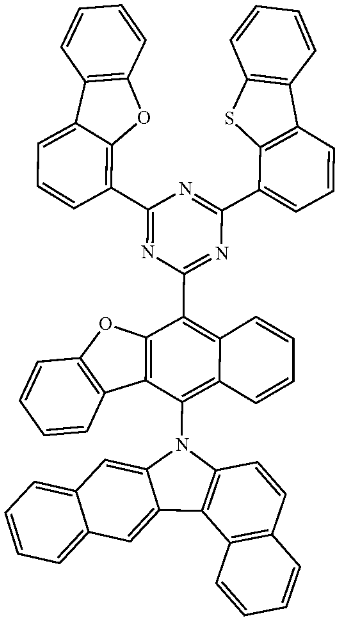

-continued
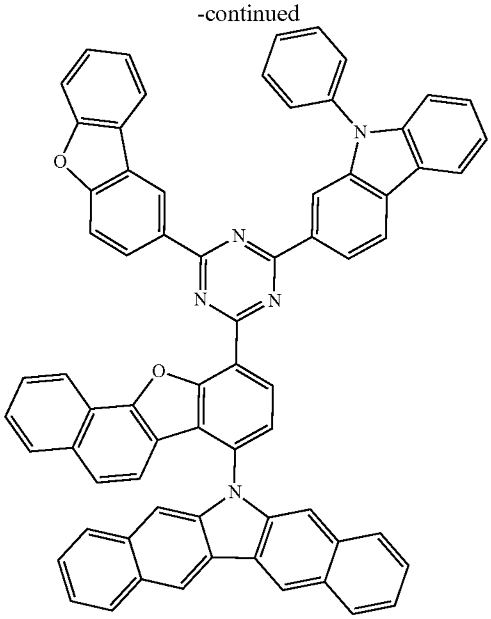
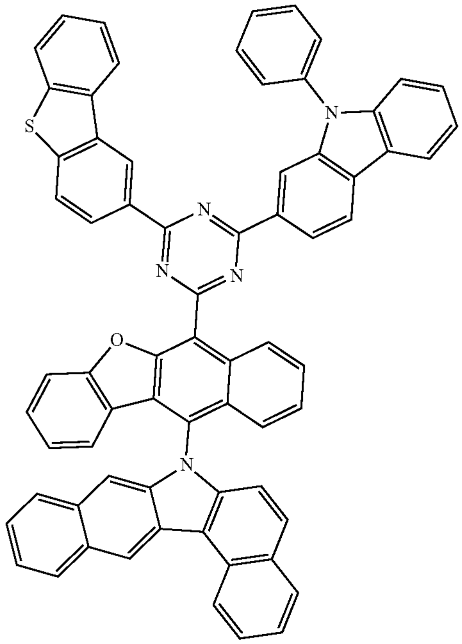
-continued
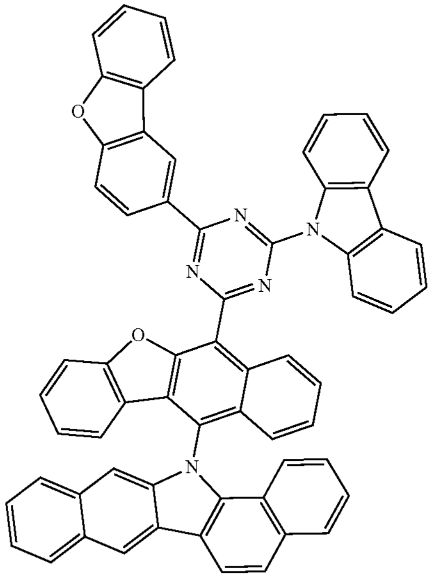
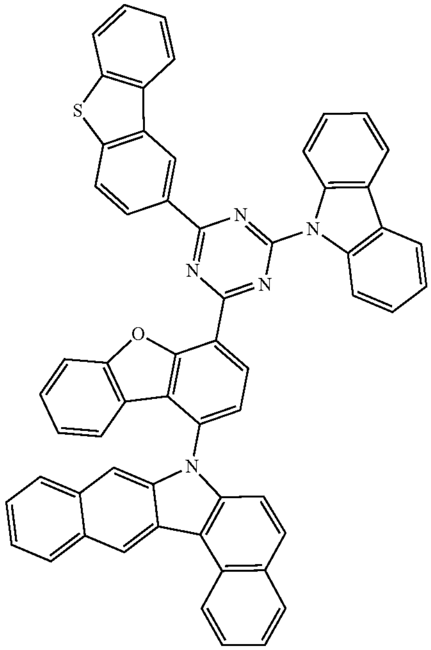

-continued
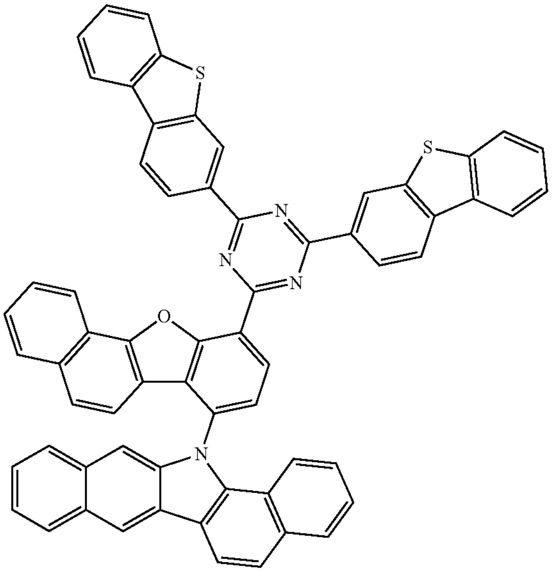
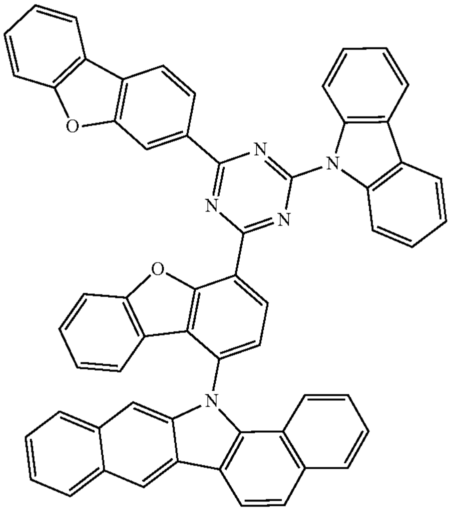
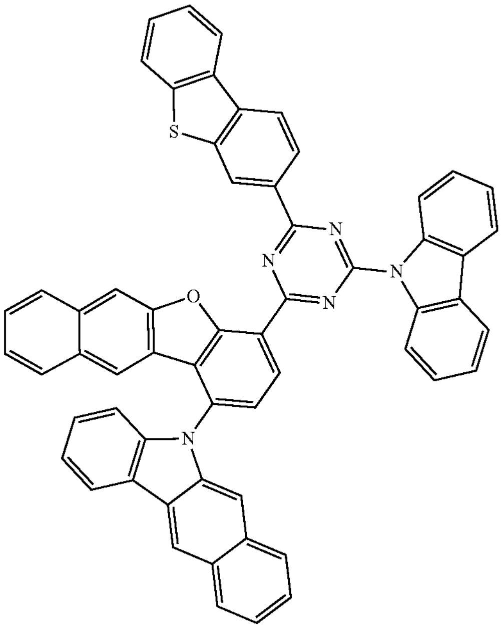
-continued
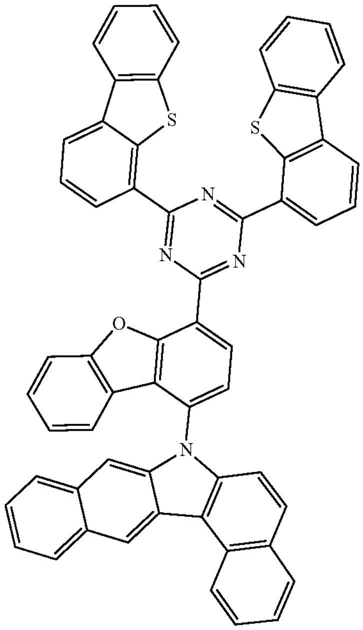
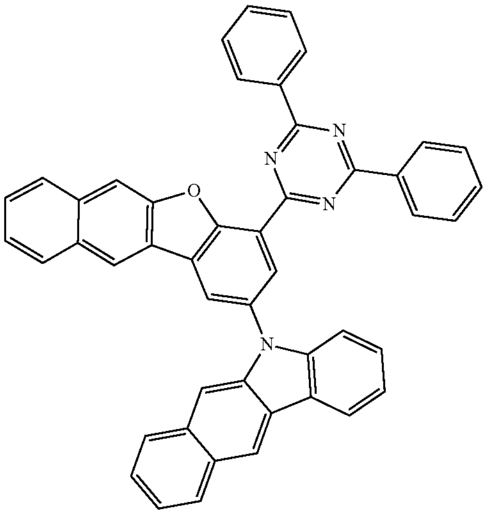
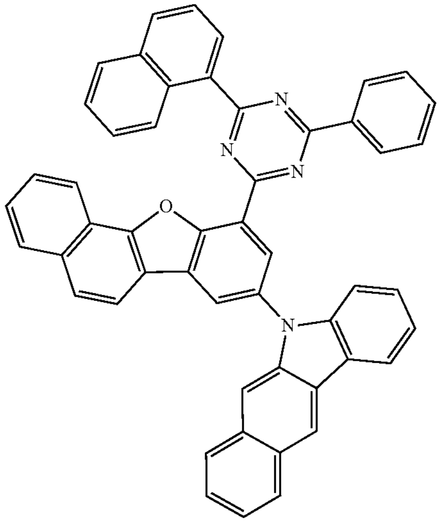

-continued
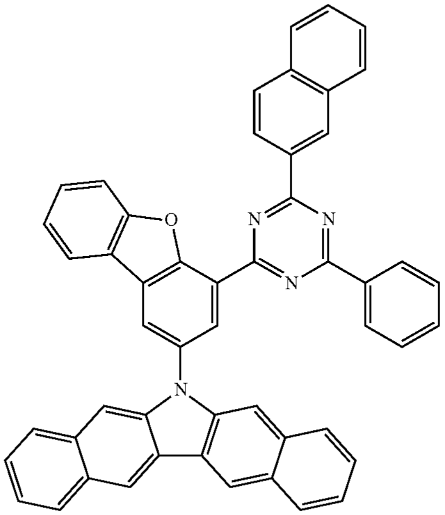
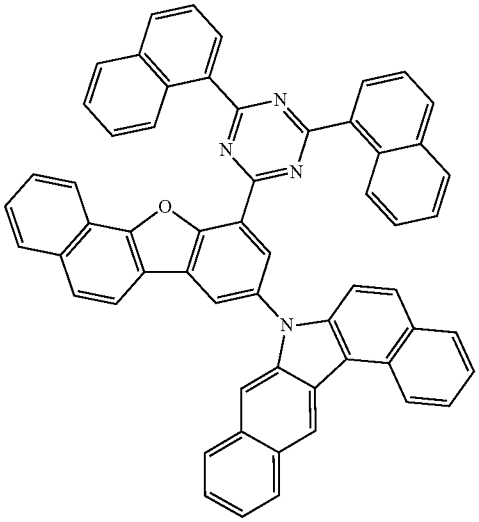
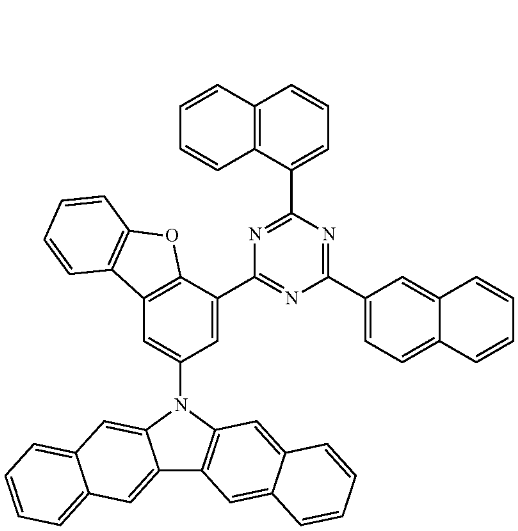
-continued
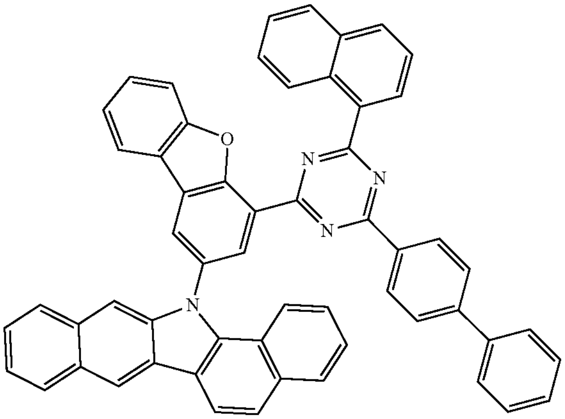
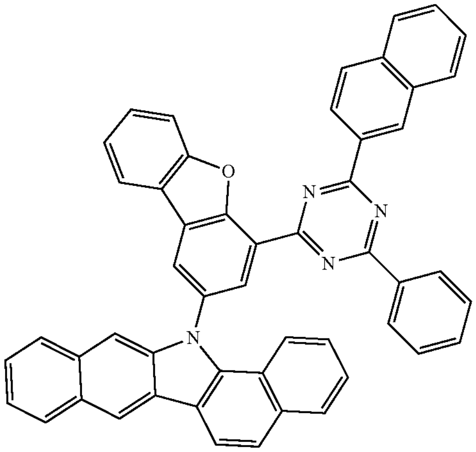
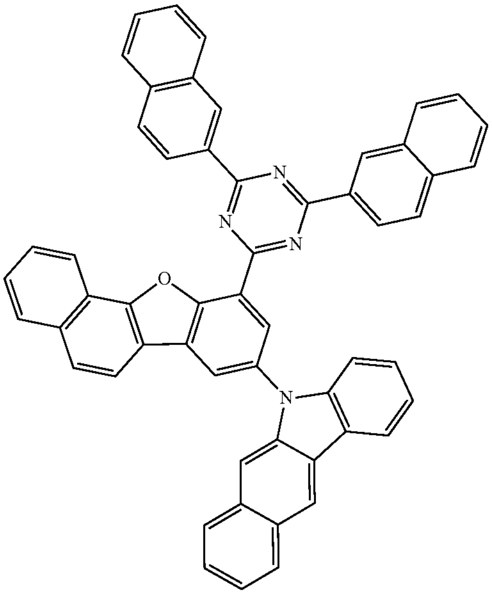

-continued
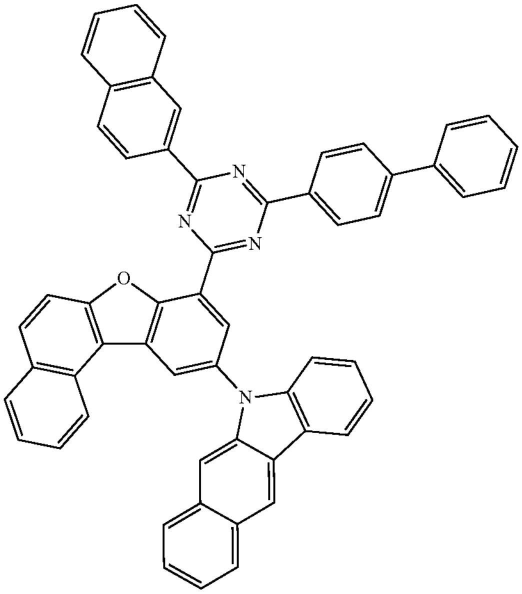
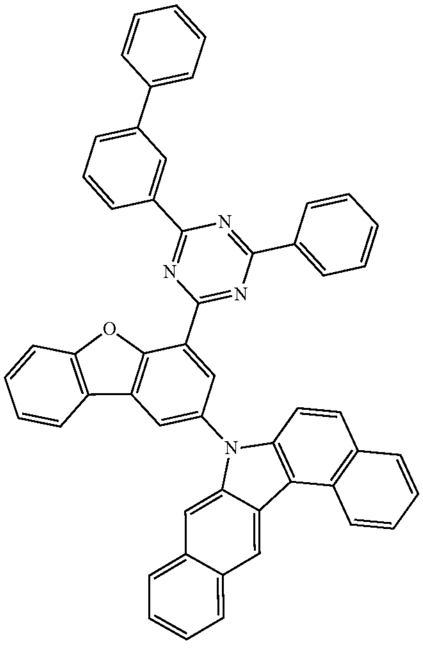
-continued
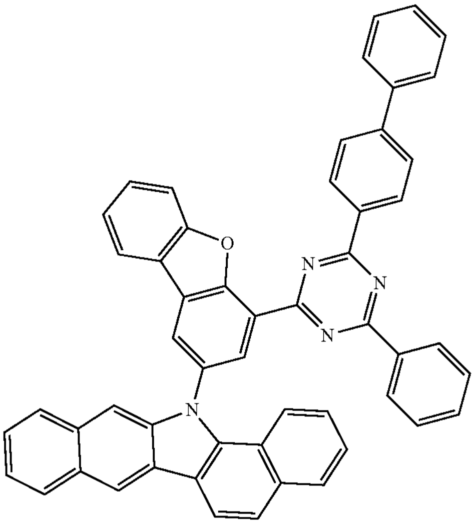
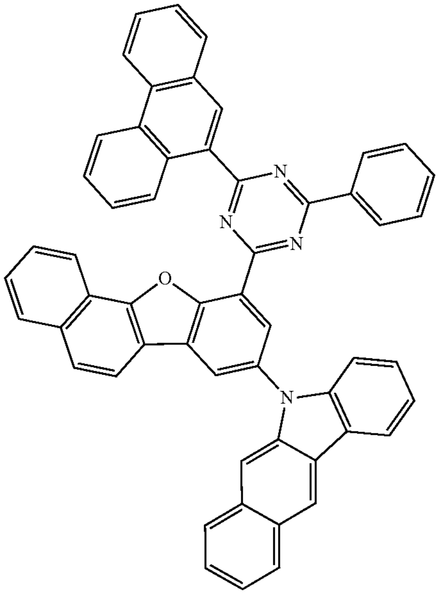
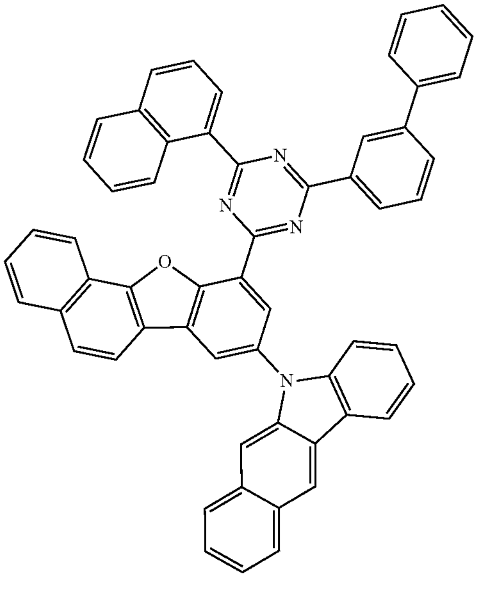

-continued
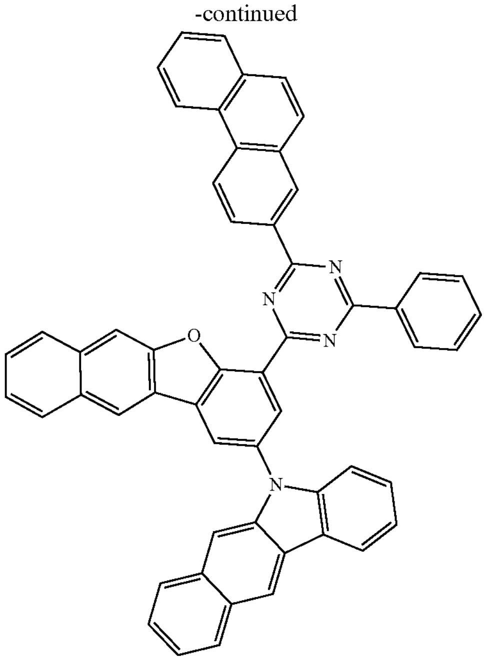
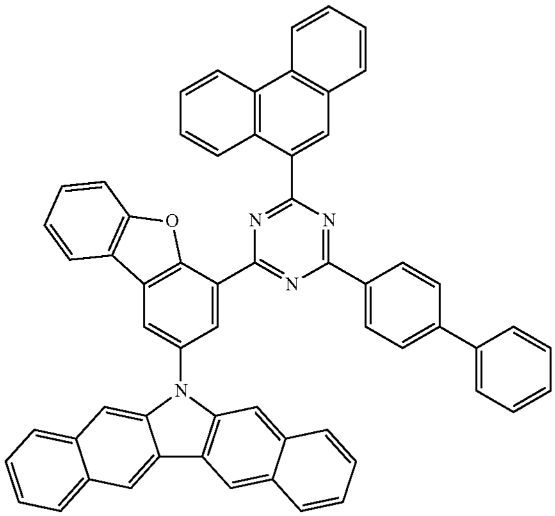
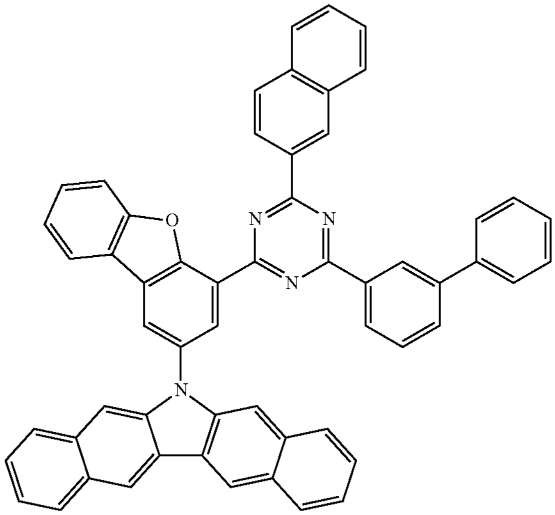
-continued
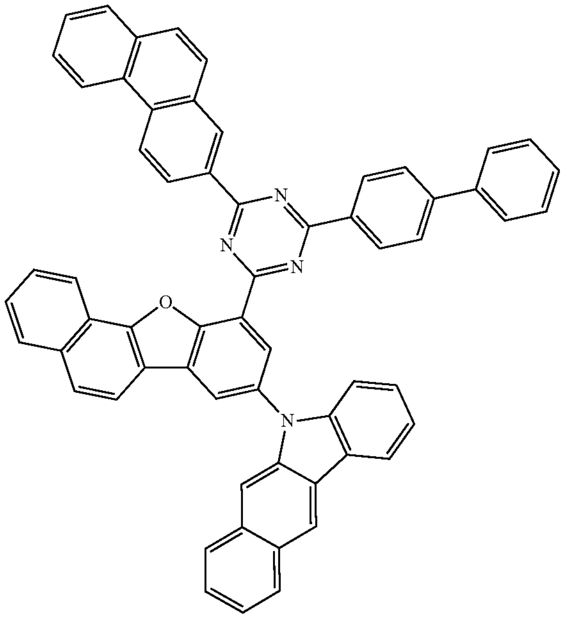
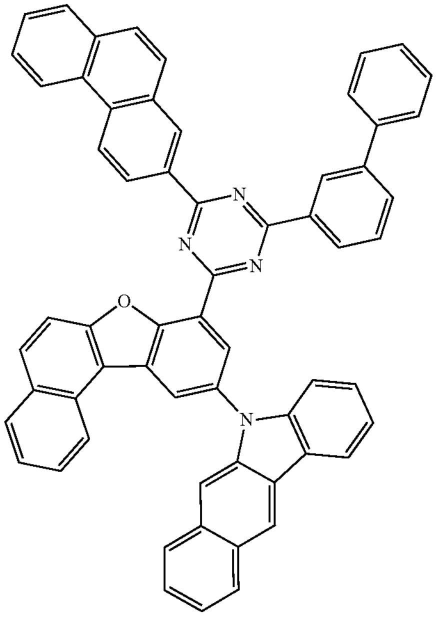

-continued
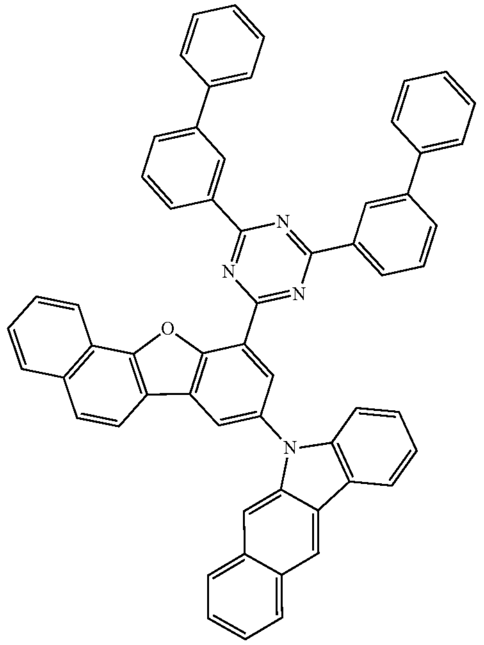
-continued
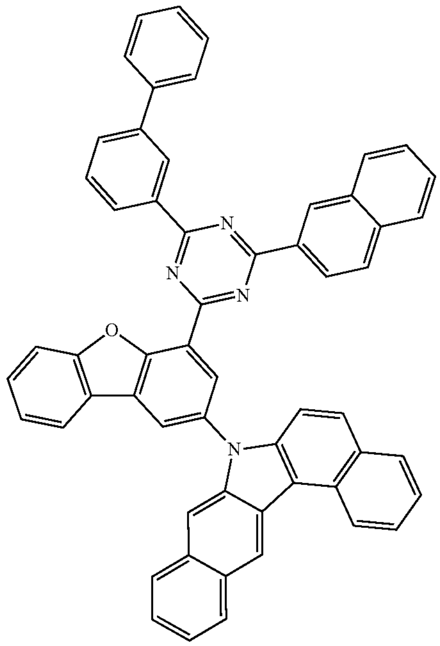
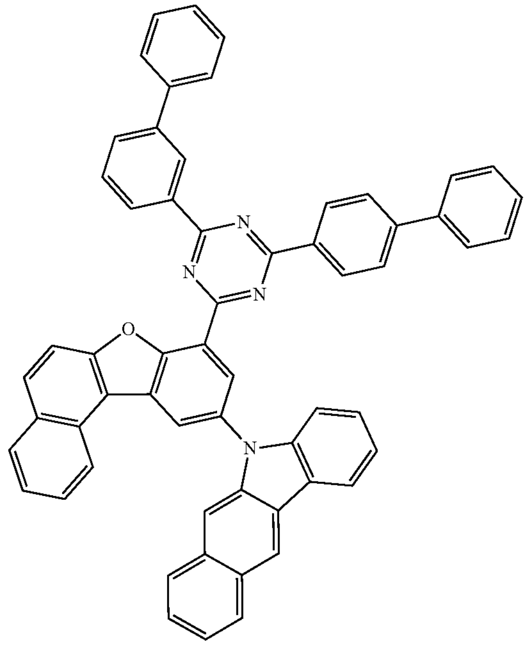
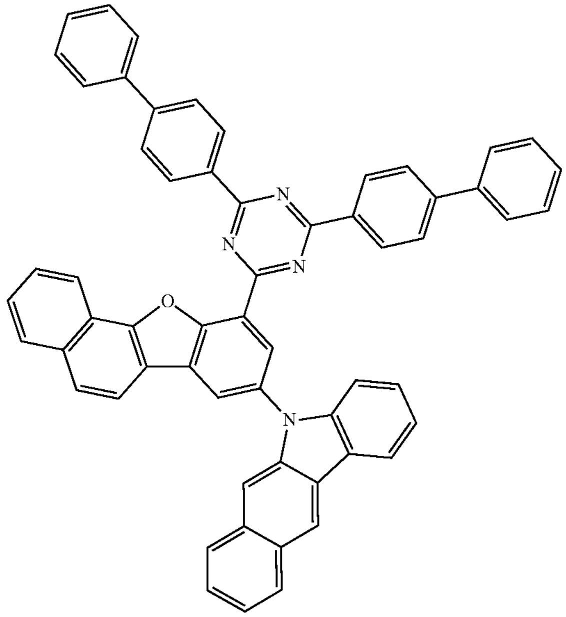

-continued
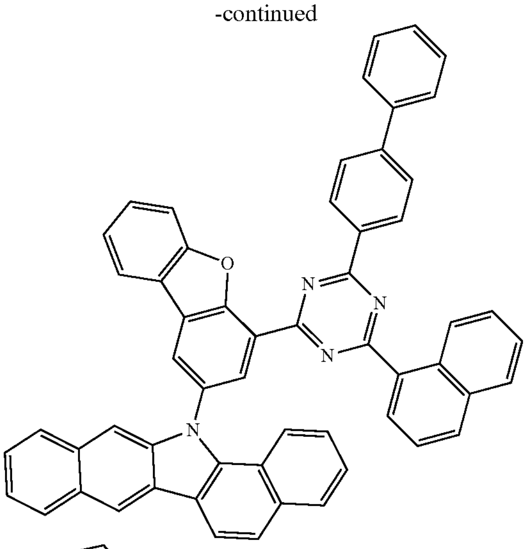
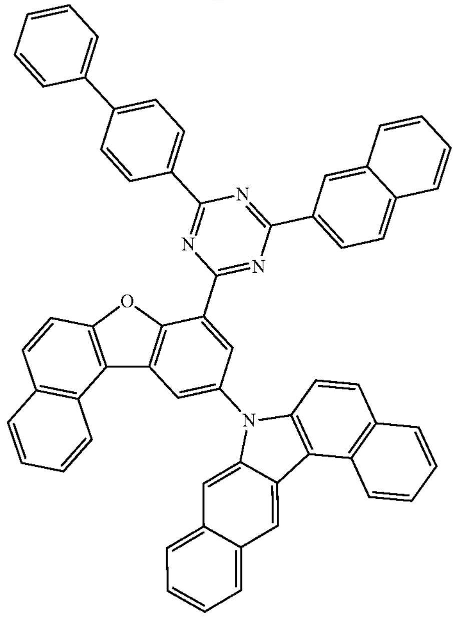
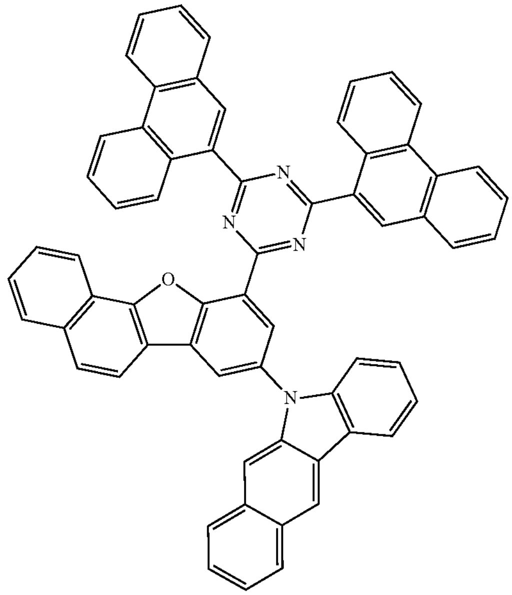
-continued
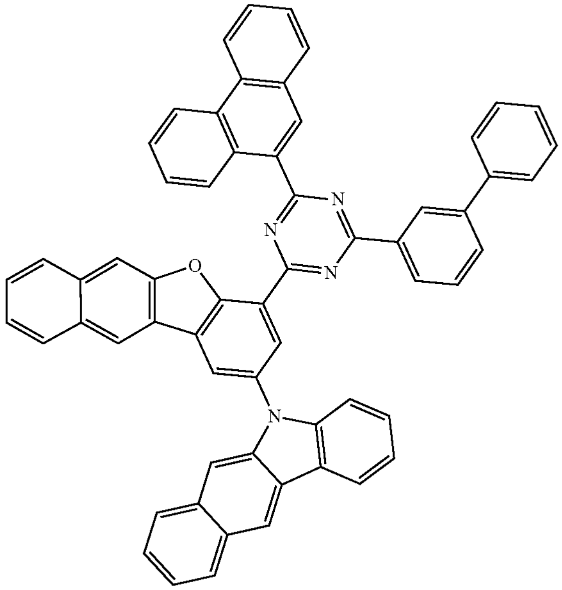
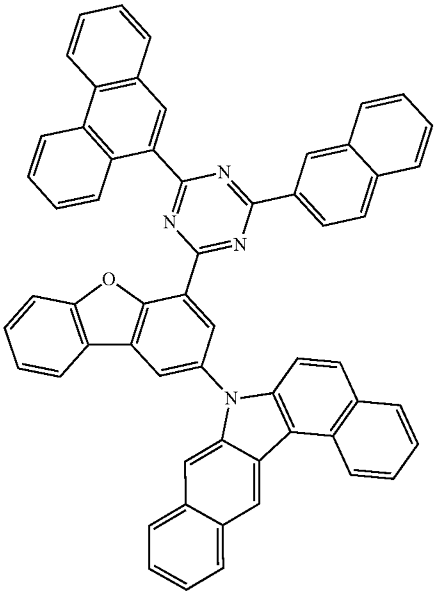
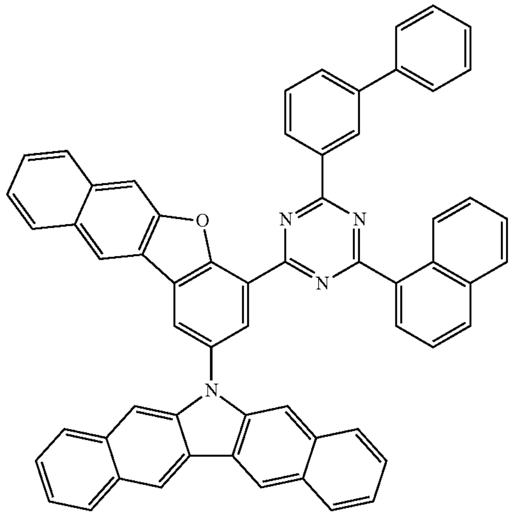

-continued
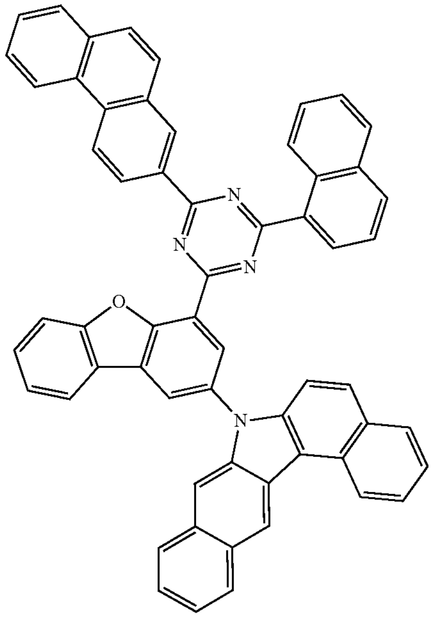
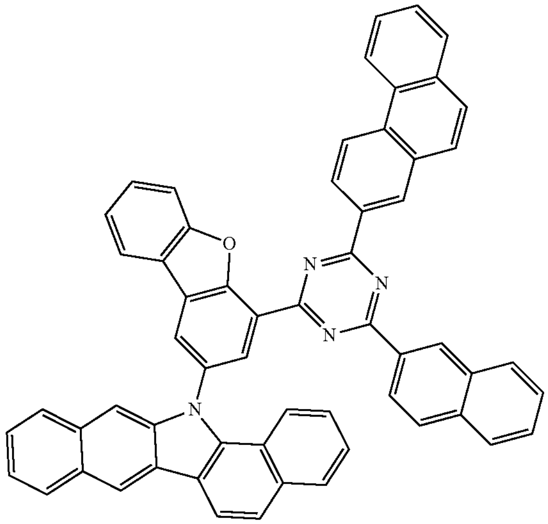
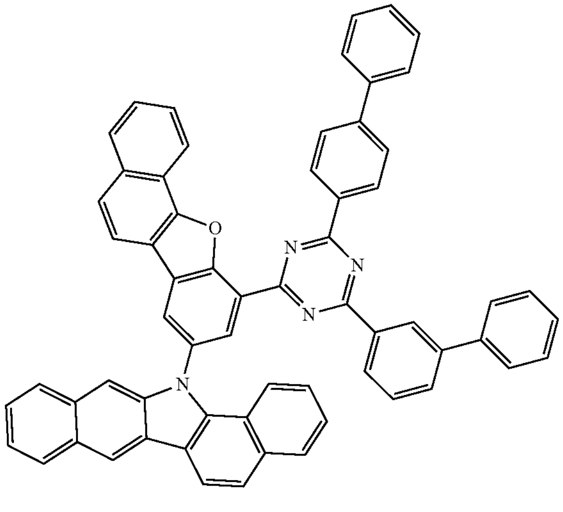
-continued
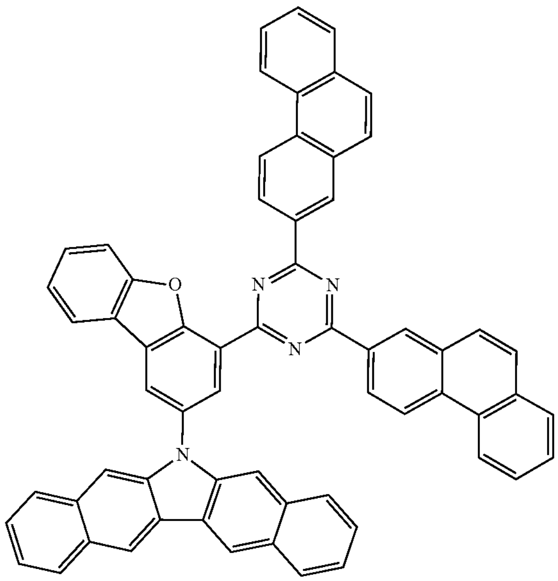
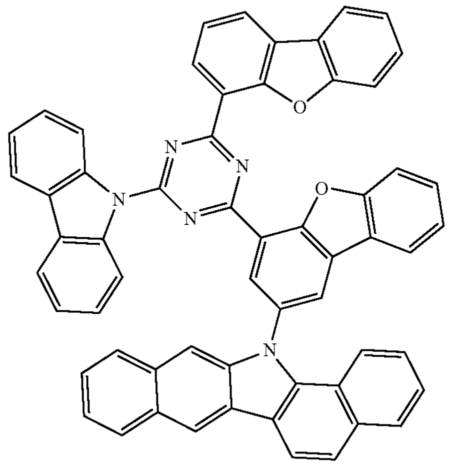
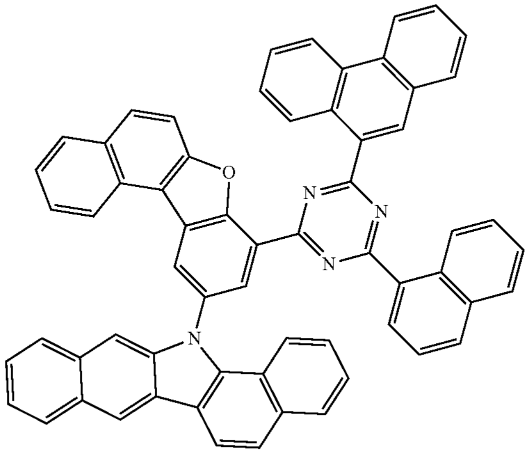

-continued
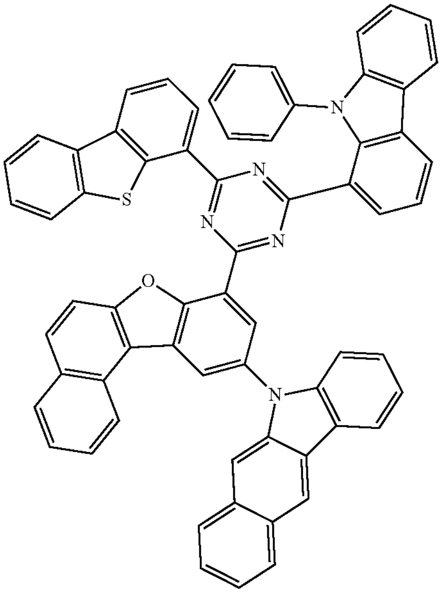
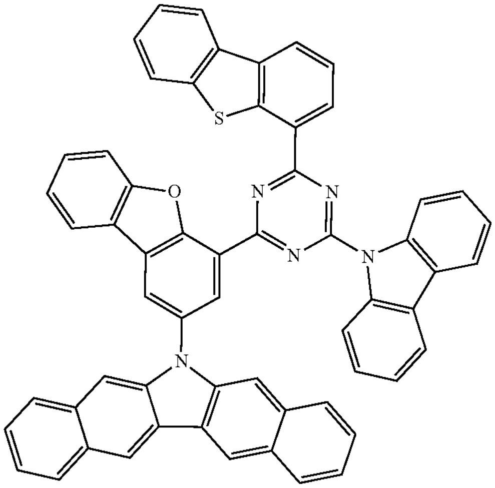
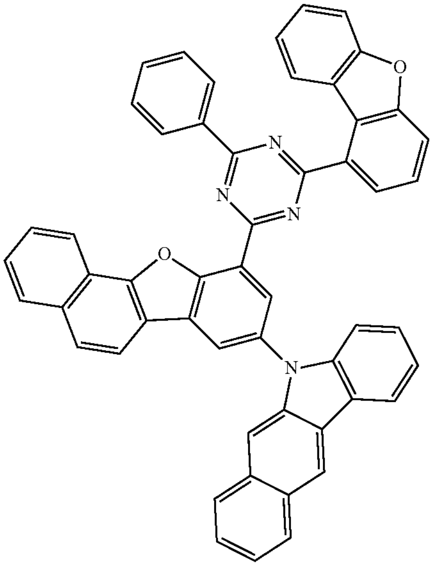
-continued
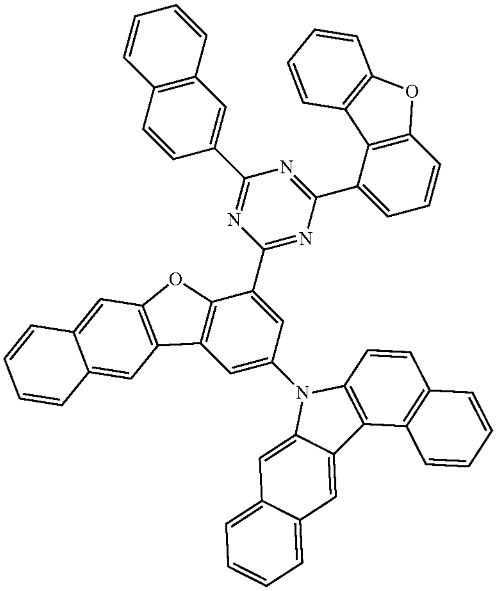
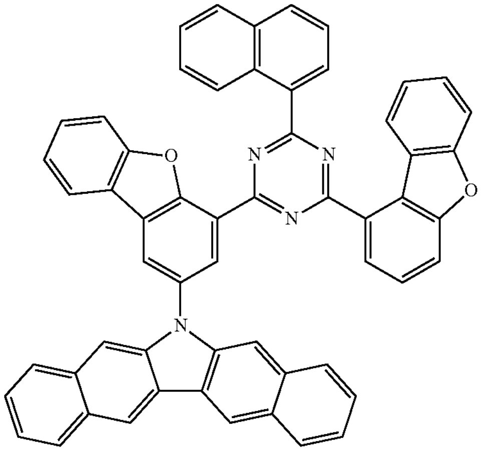
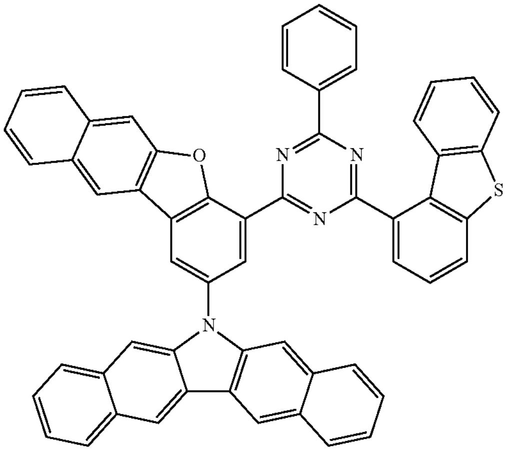

-continued
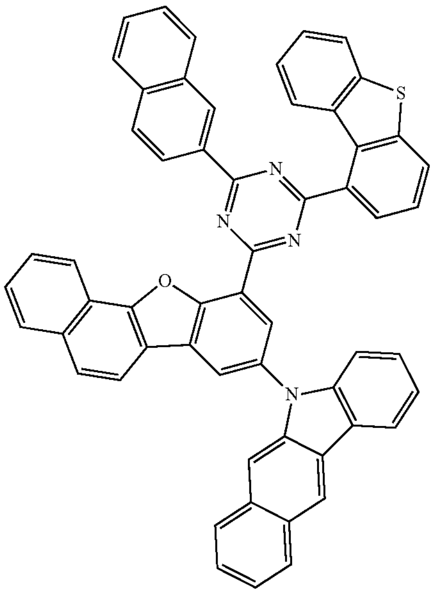
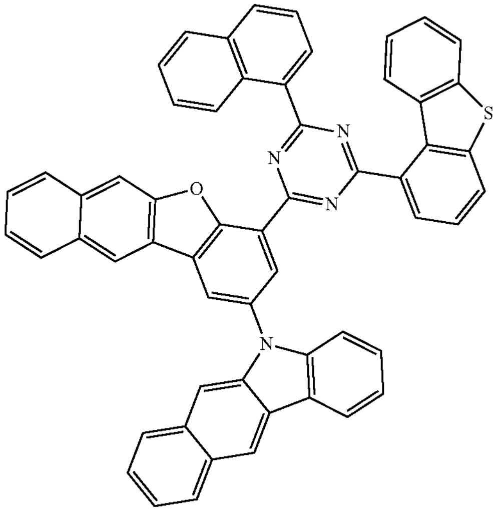
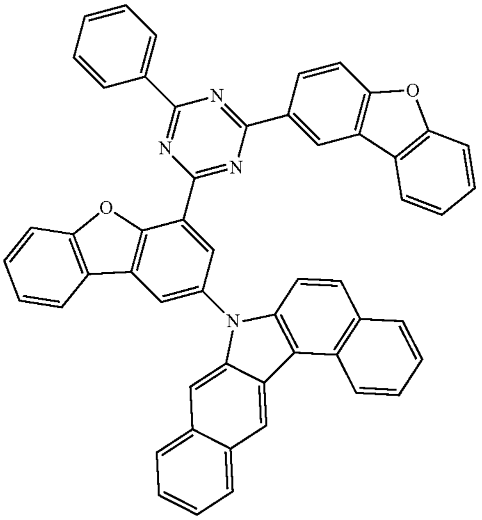
-continued
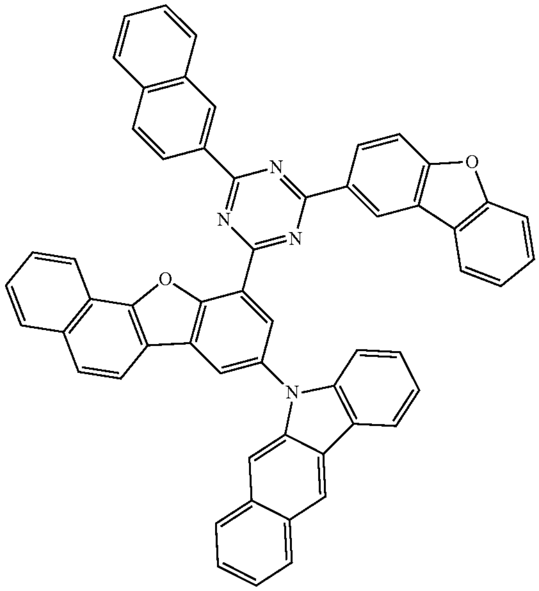
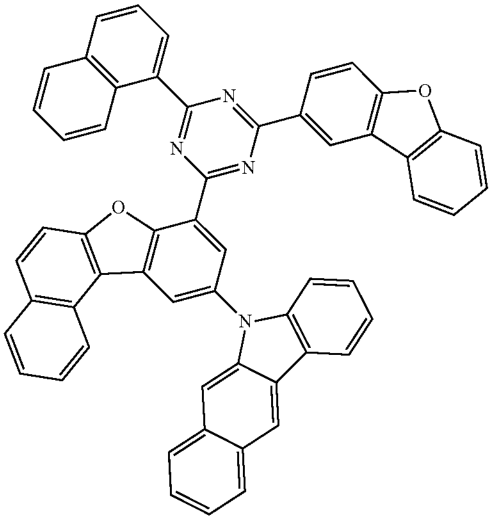
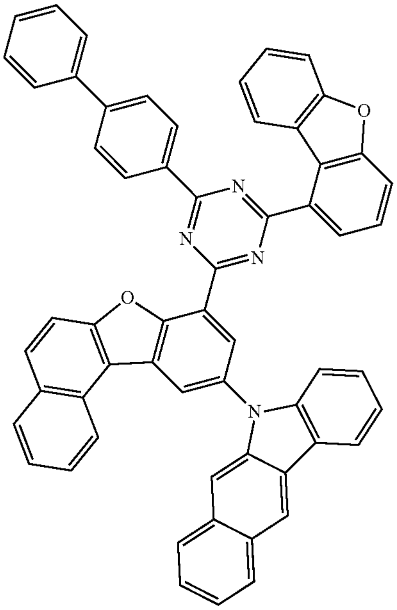

-continued
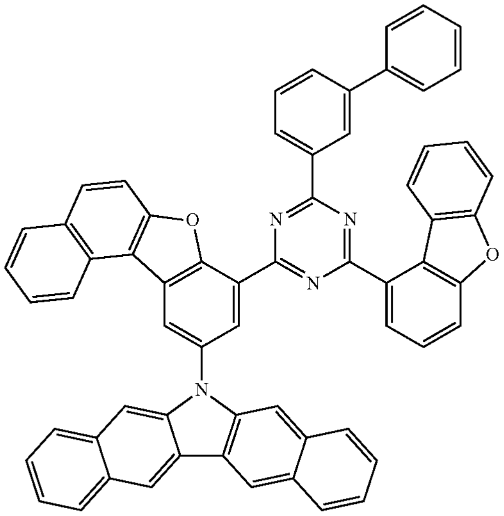
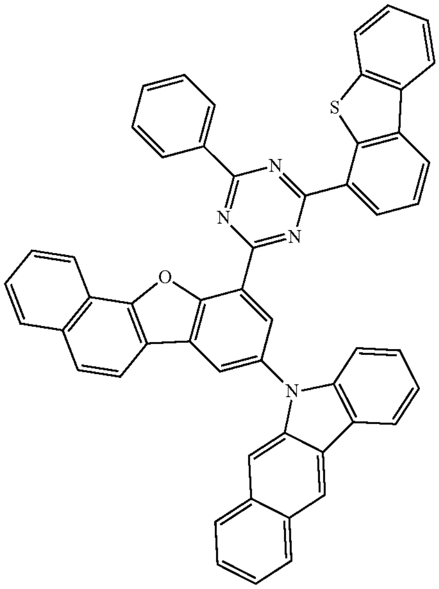
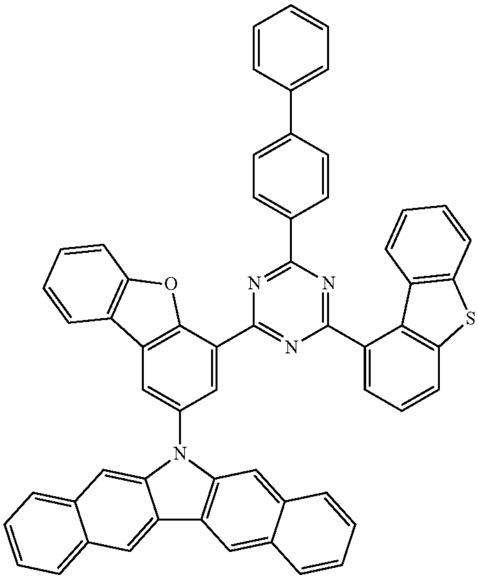
-continued
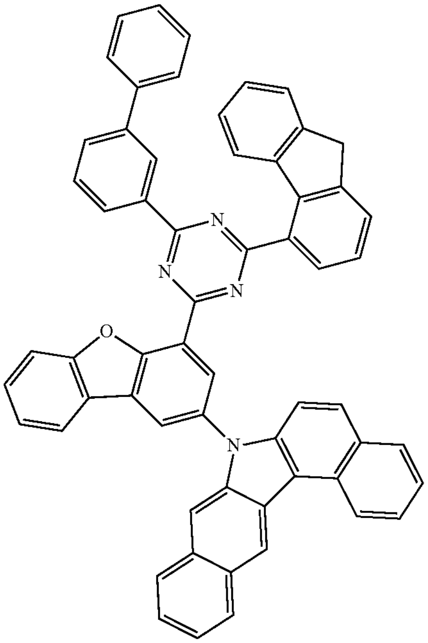
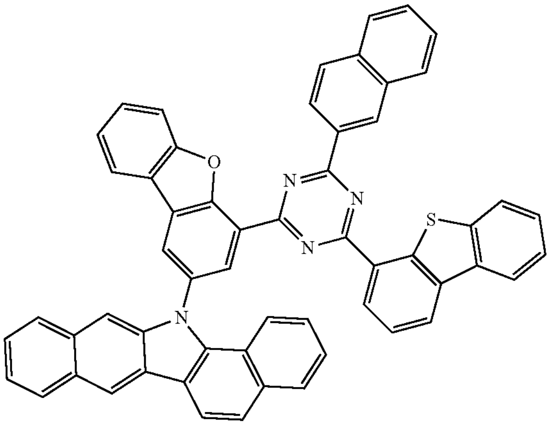
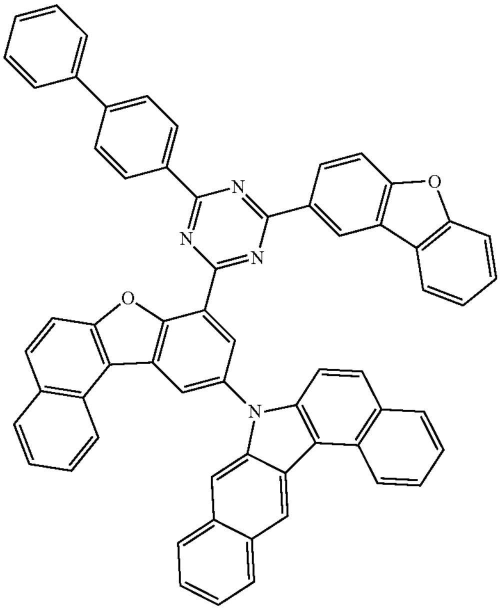

-continued
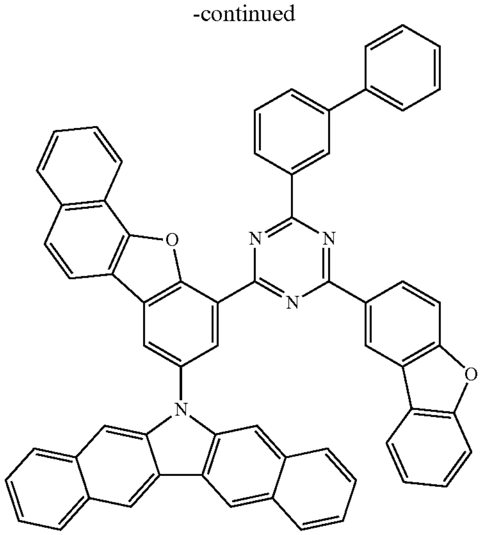
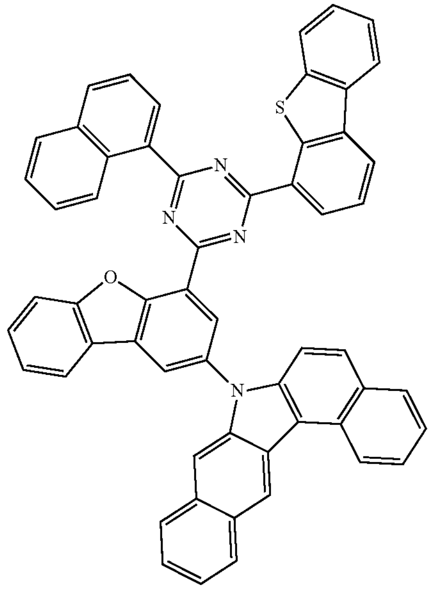
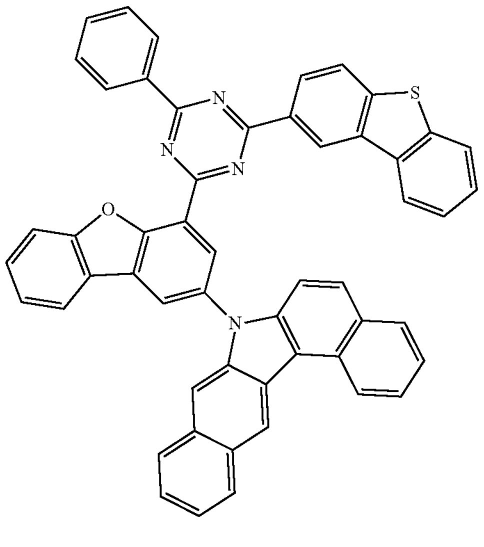
-continued
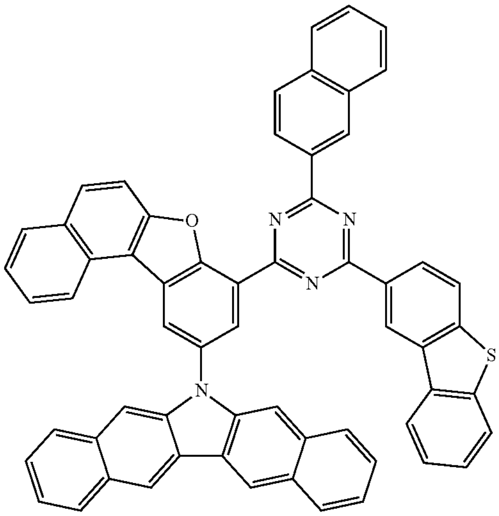
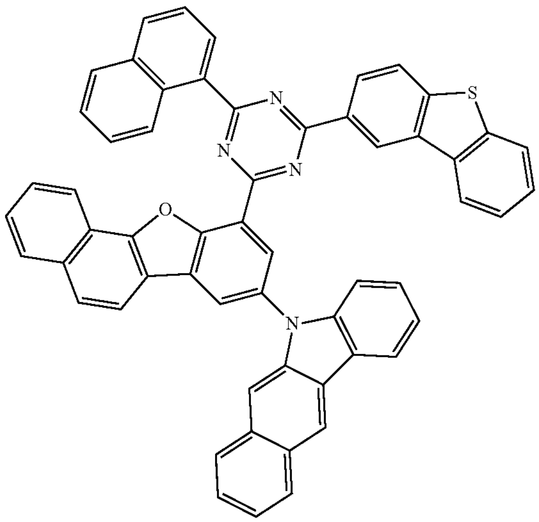
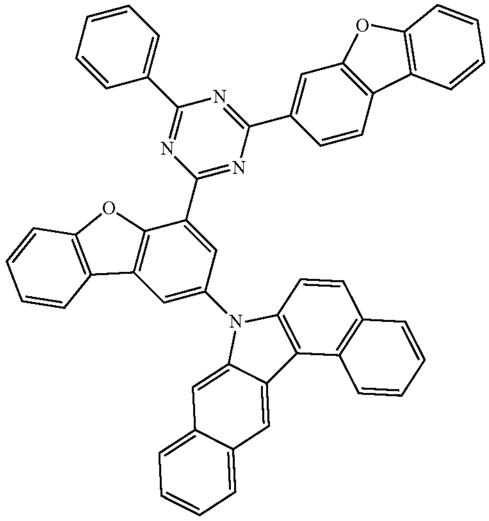

-continued
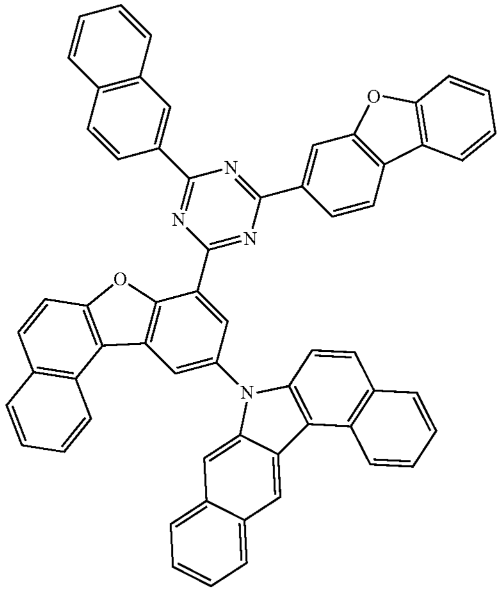
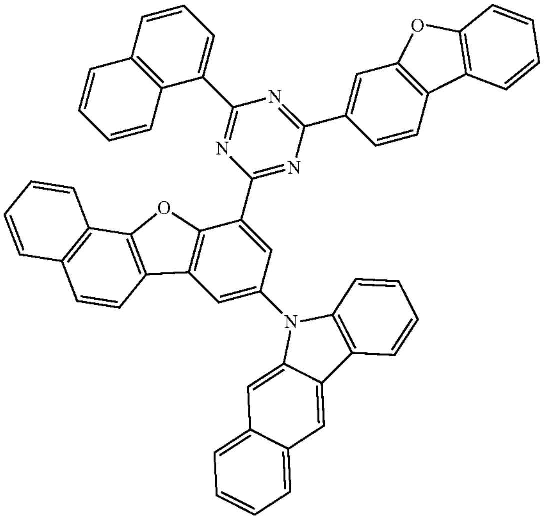
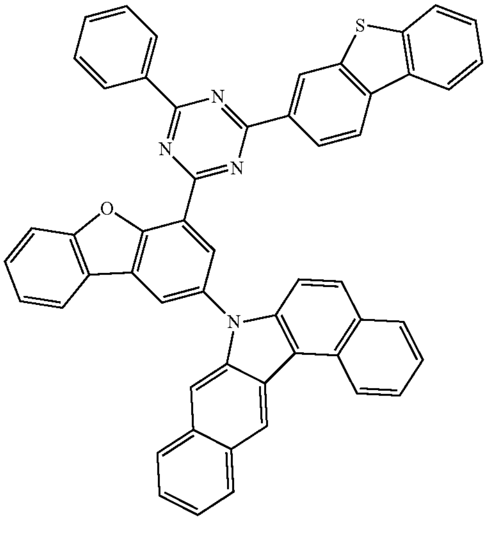
-continued
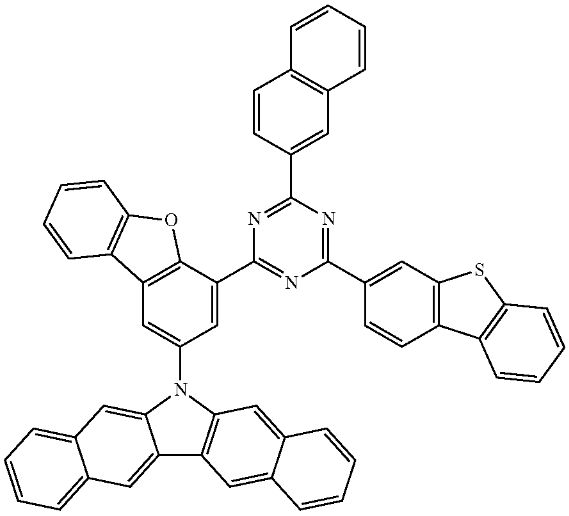
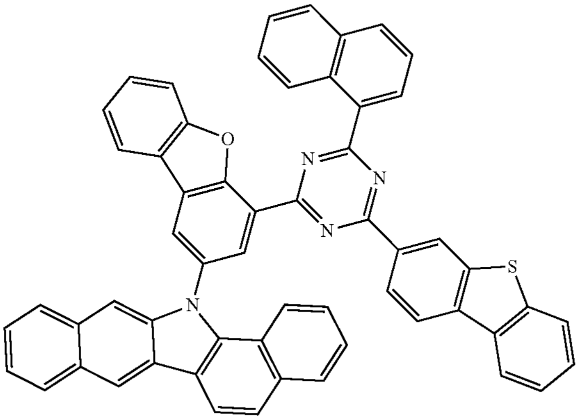
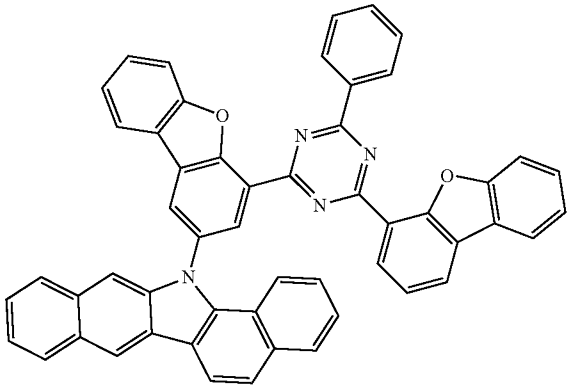

-continued
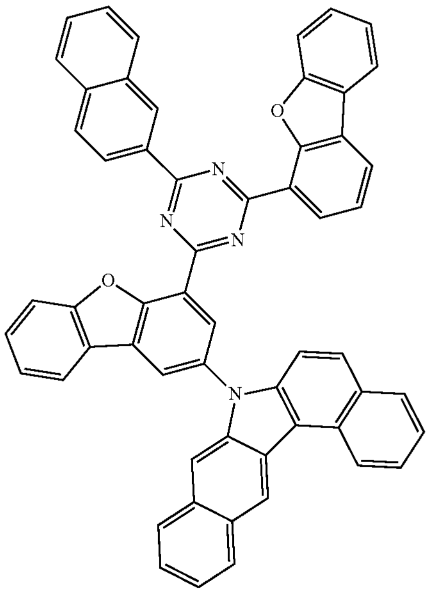
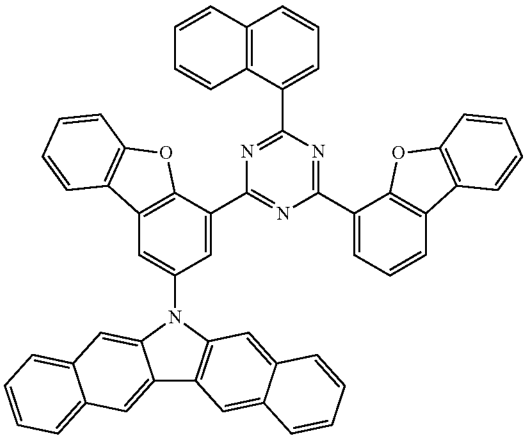
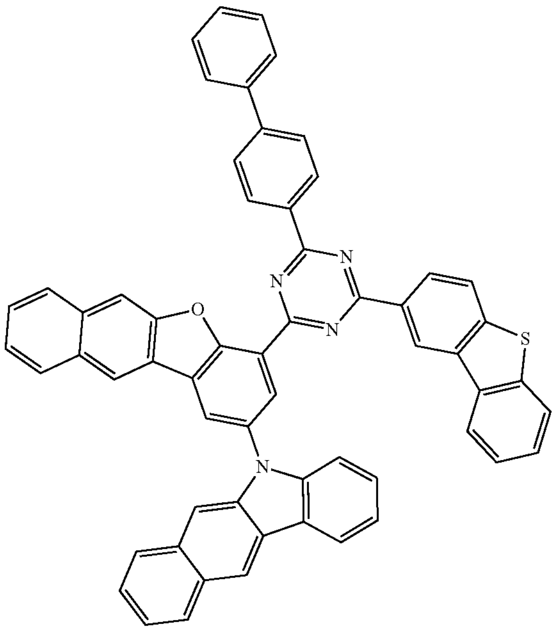
-continued
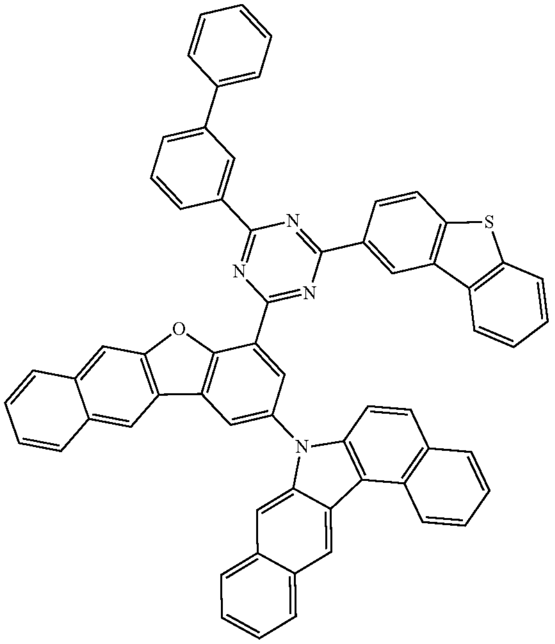
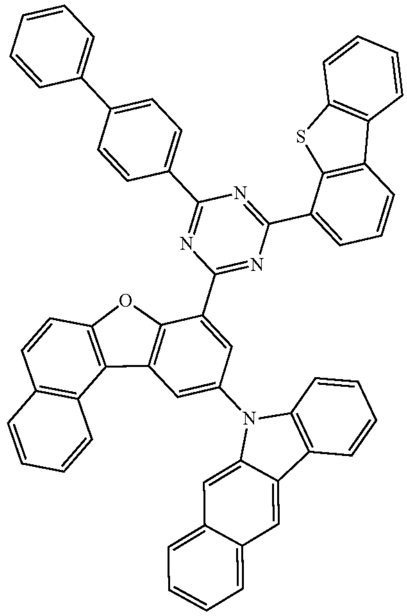

-continued
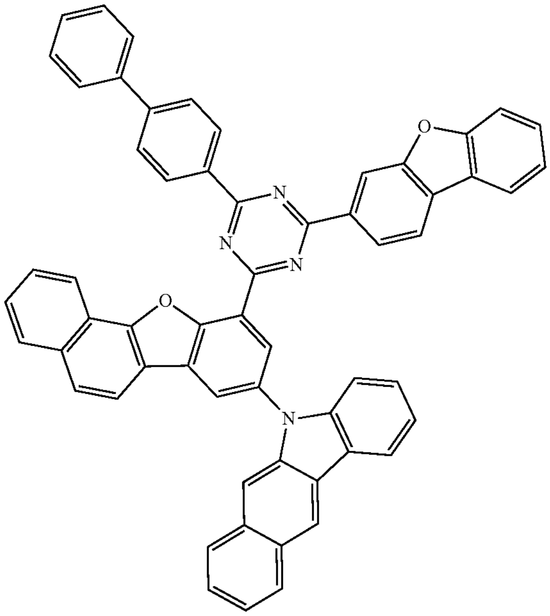
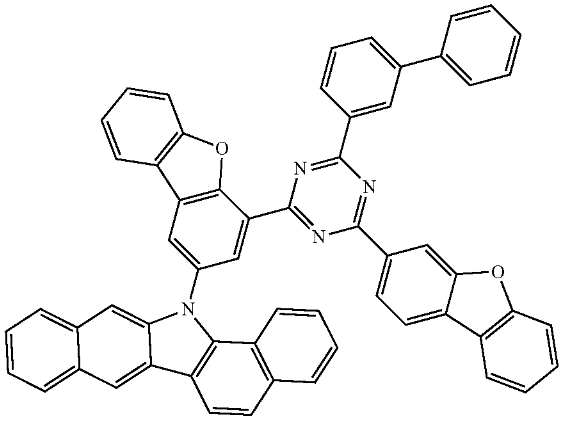
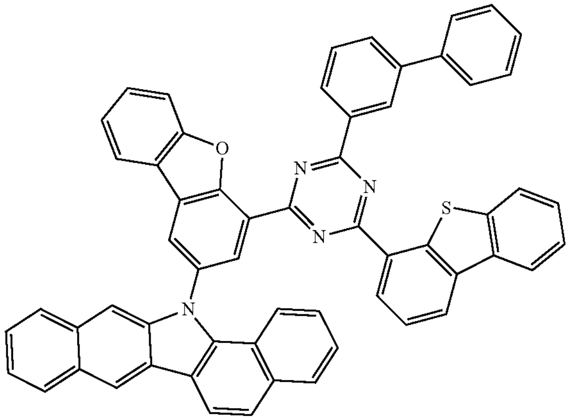
-continued
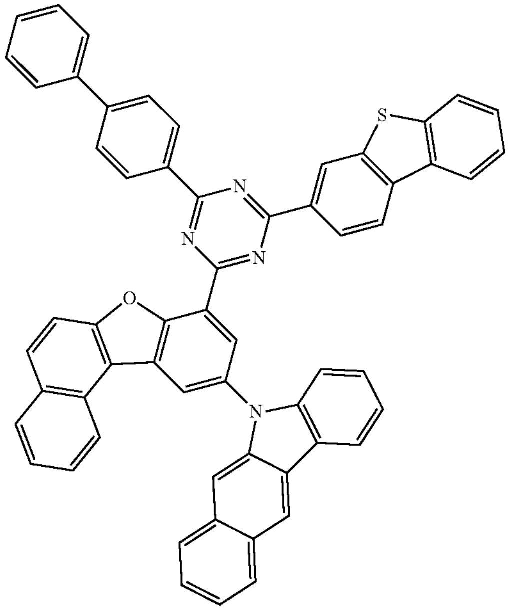
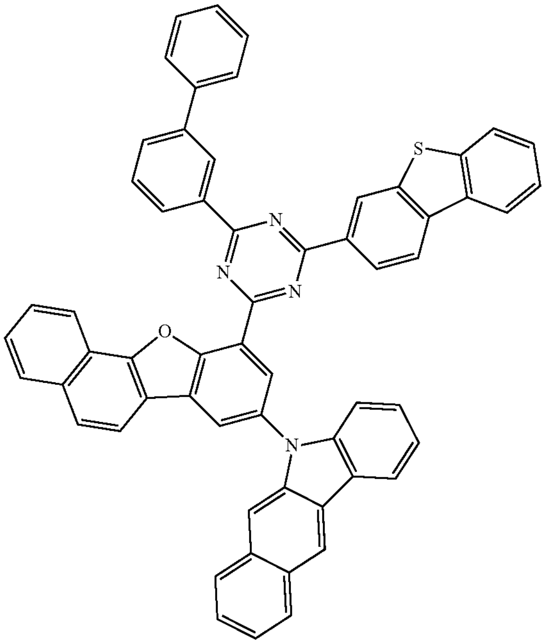

-continued
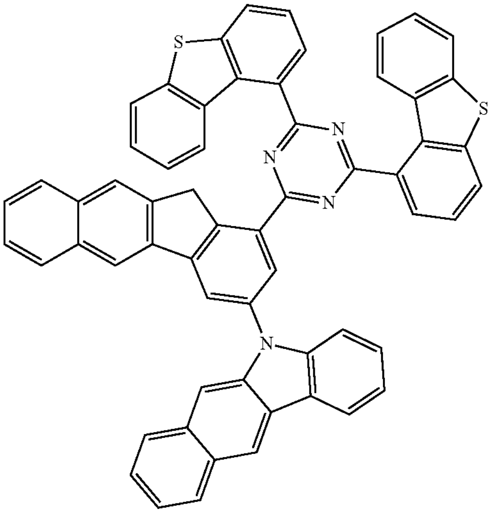
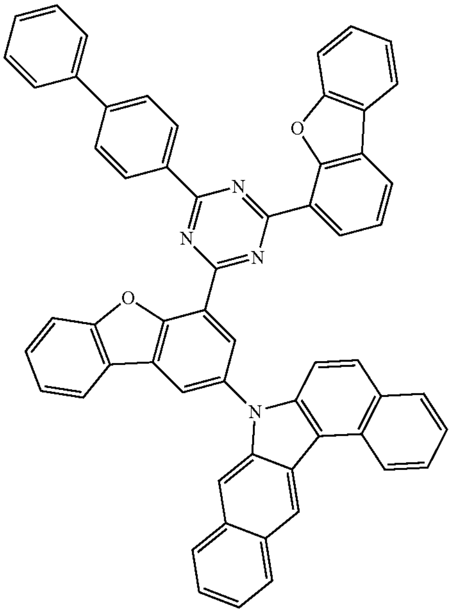
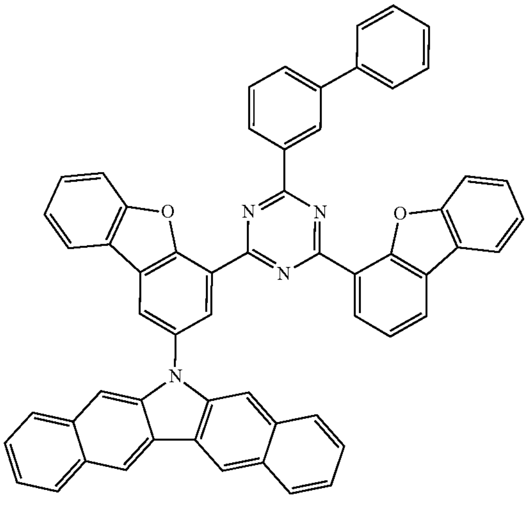
-continued
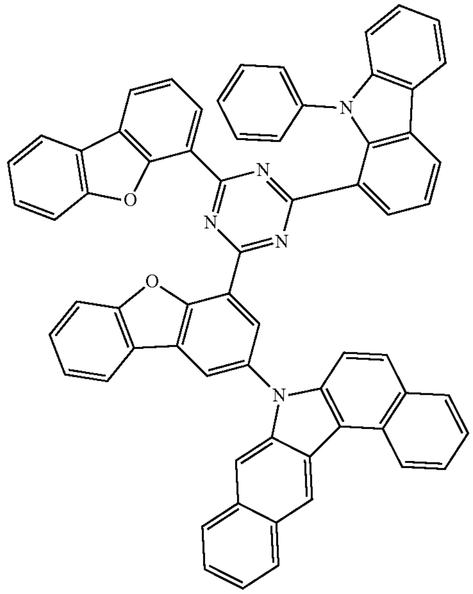
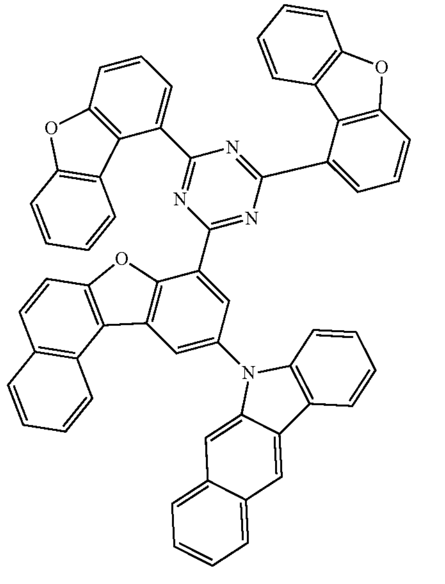

-continued
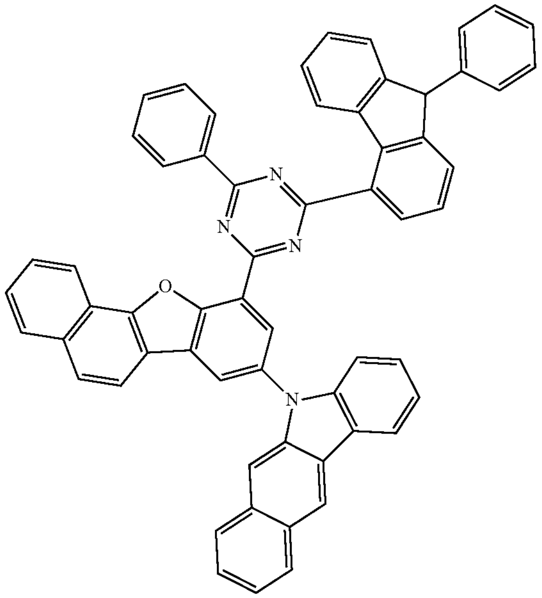
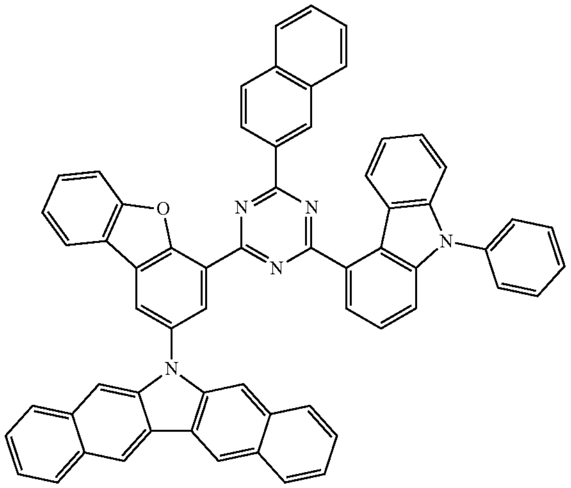
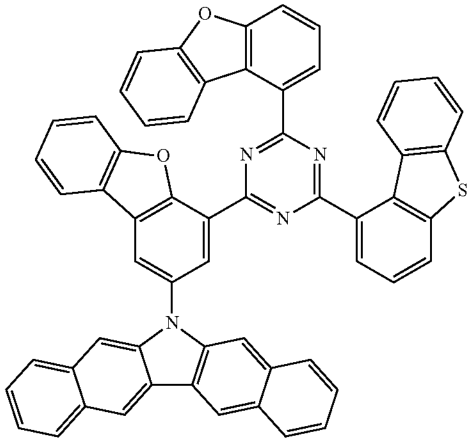
-continued
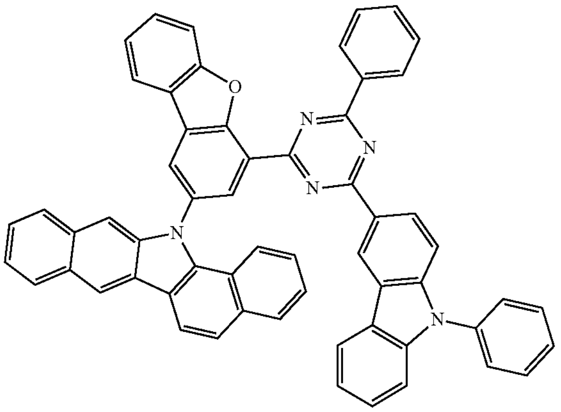
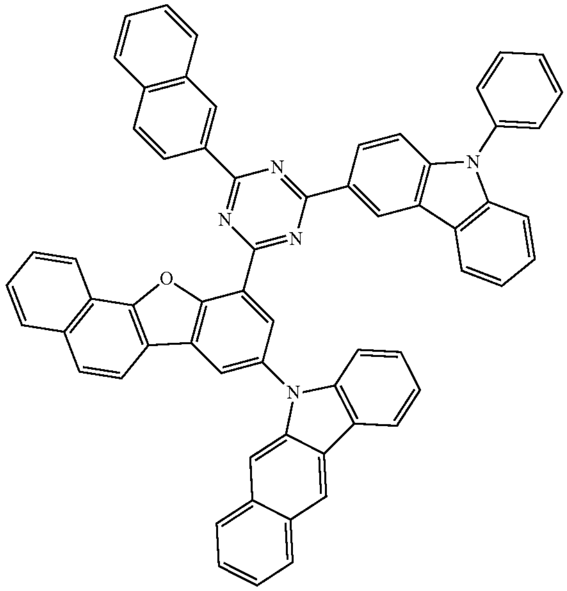
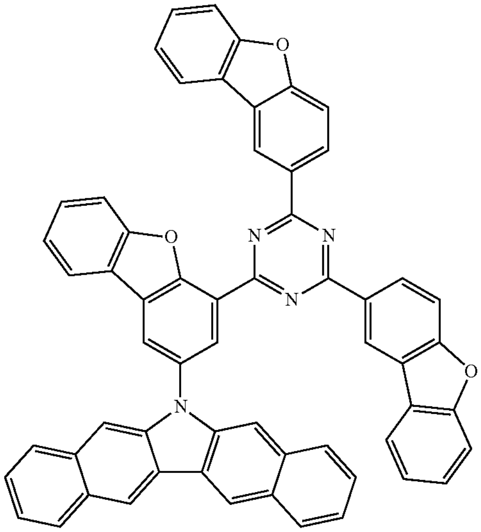

-continued
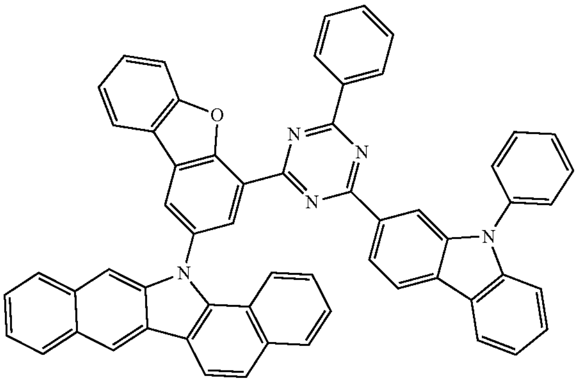
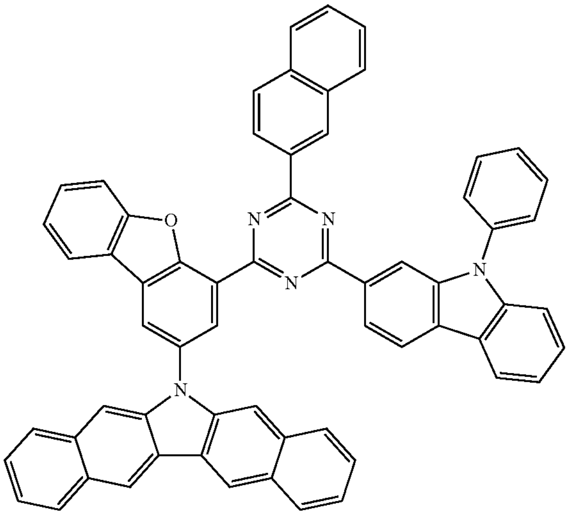 [SMILES: c1ccc(-n2c3ccccc3c3ccc(-c4nc(-c5ccc6ccccc6c5)nc(-c5cc(-n6c7cc8ccccc8cc7c7cc8ccccc8cc76)cc6c5oc5ccccc56)n4)cc32)cc1]
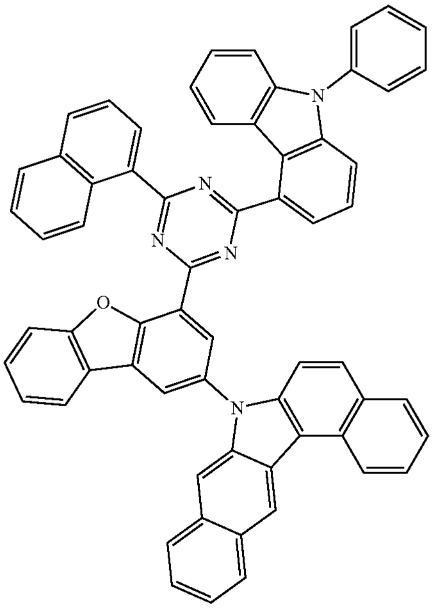
-continued
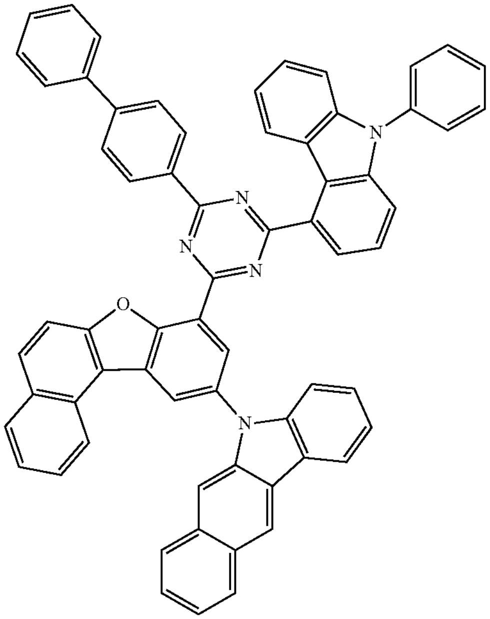
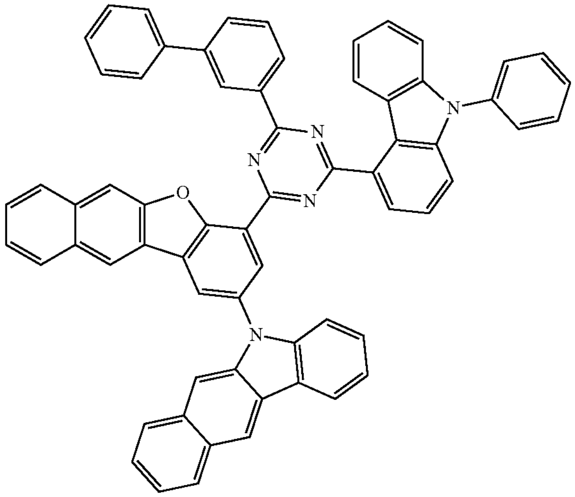
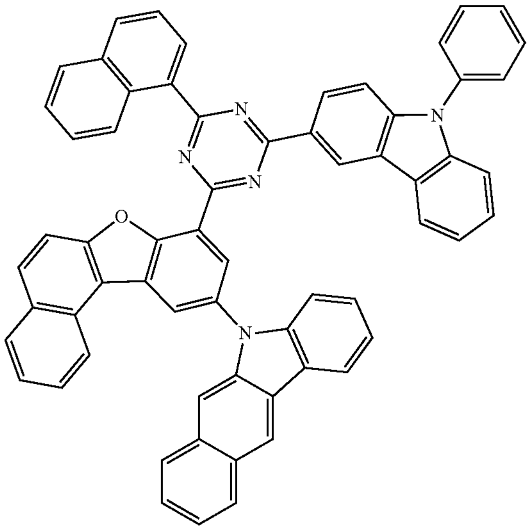

-continued
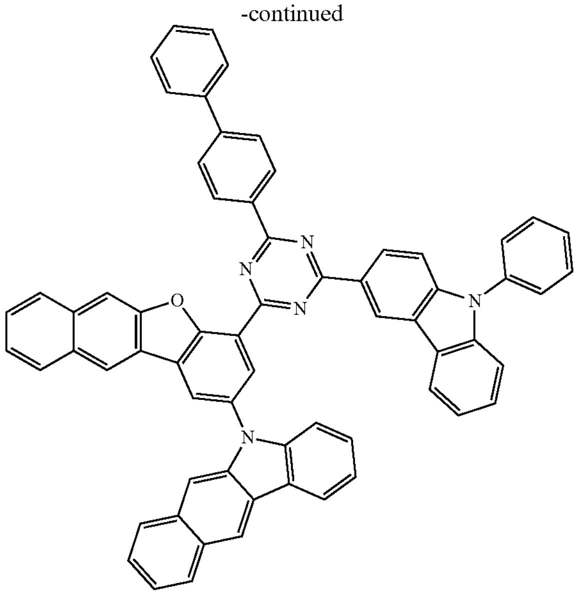
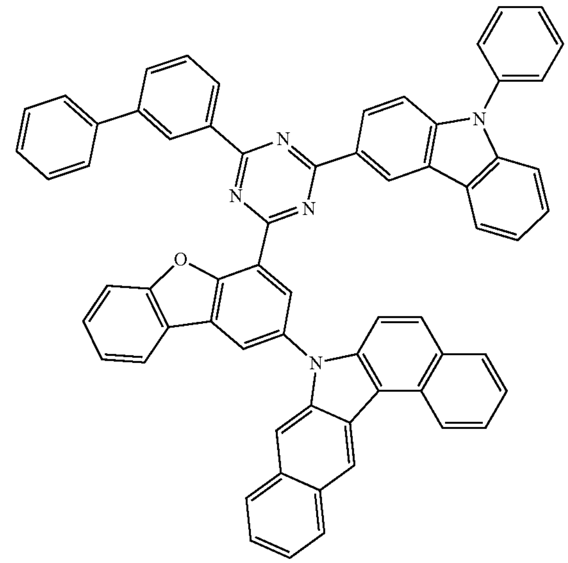
-continued
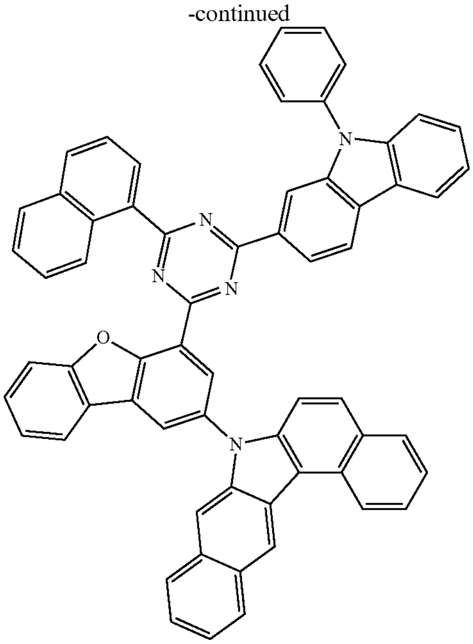
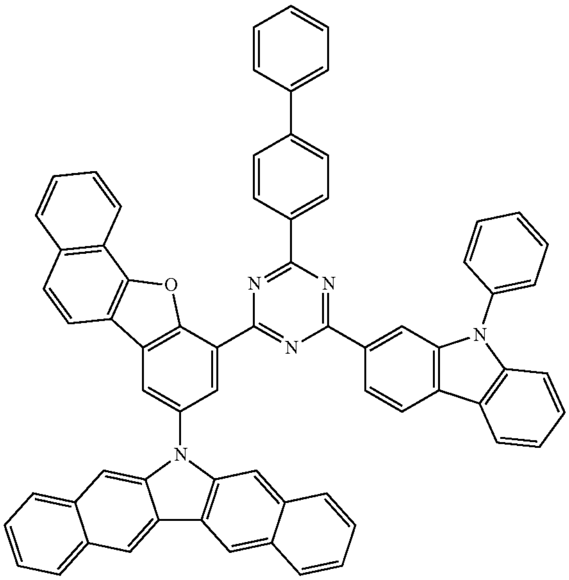

-continued
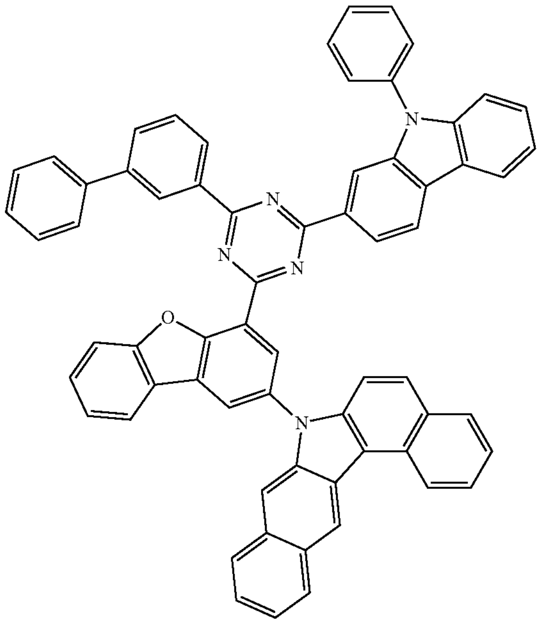
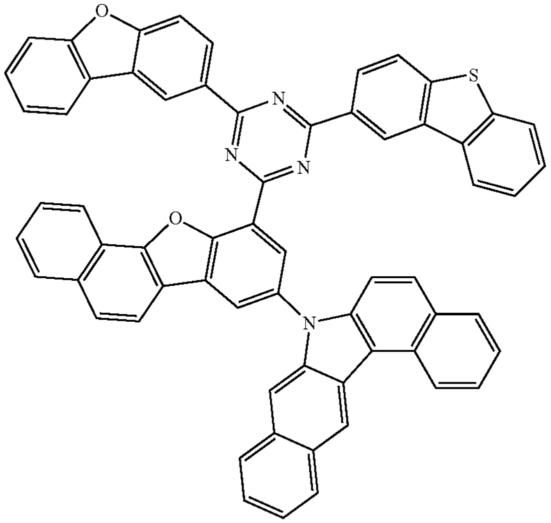
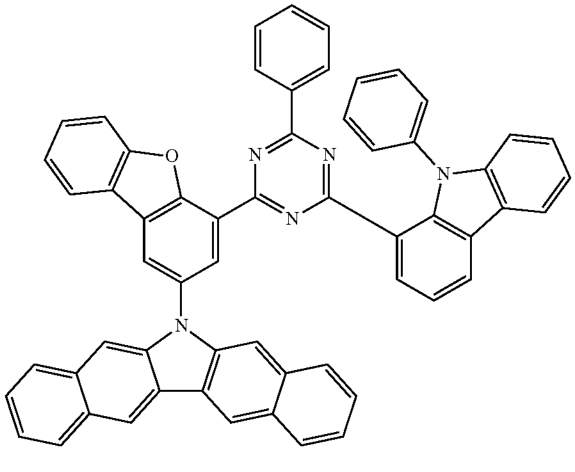
-continued
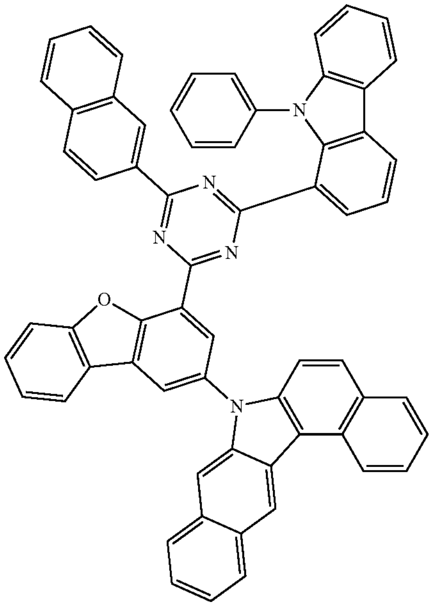
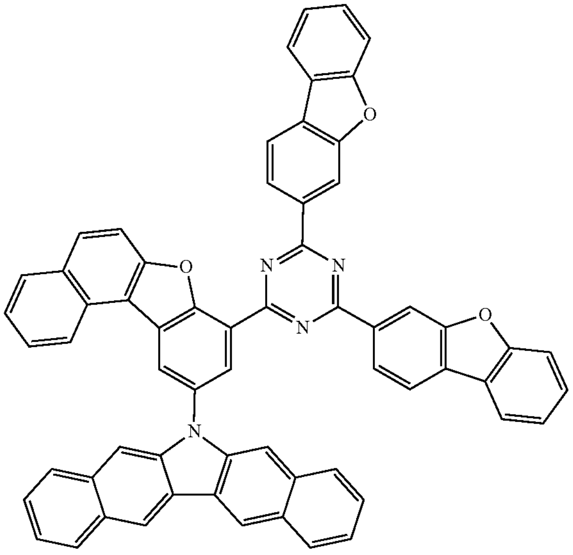
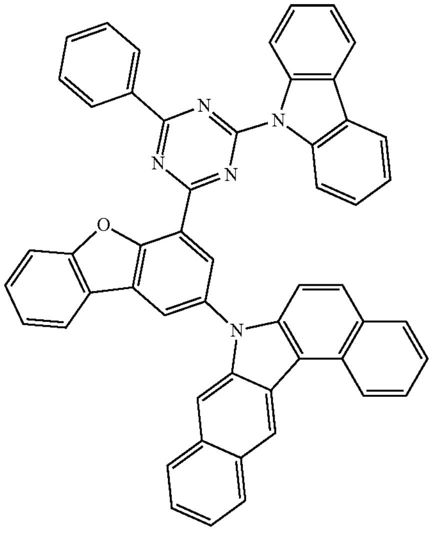

-continued
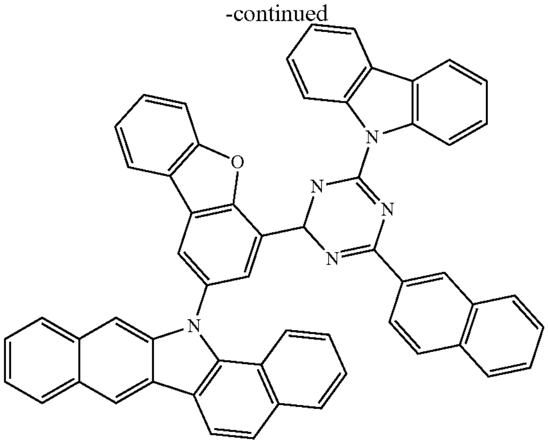
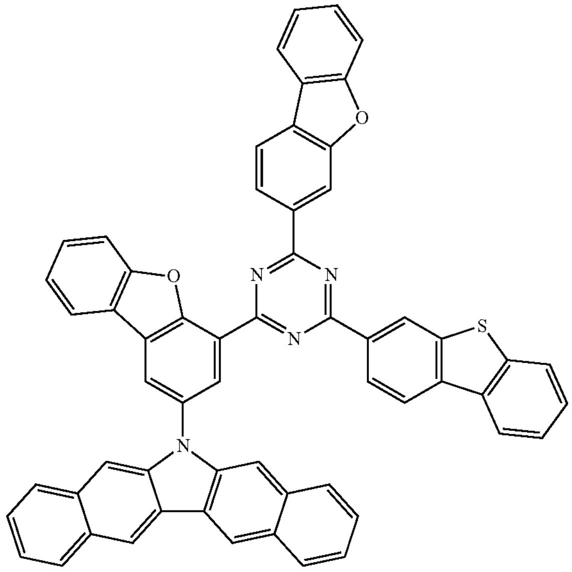
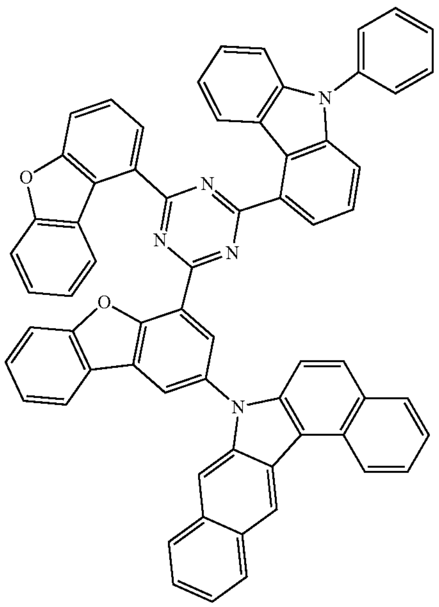
-continued
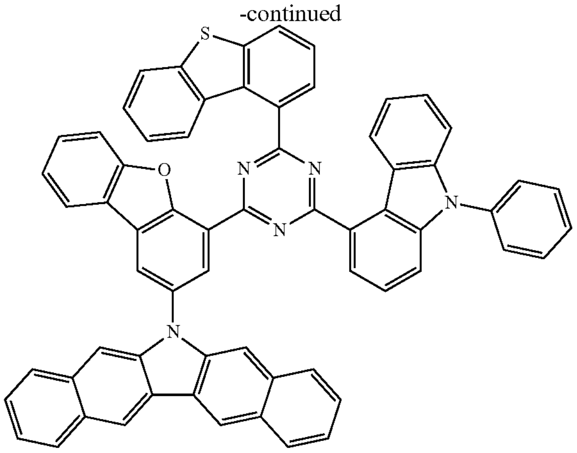
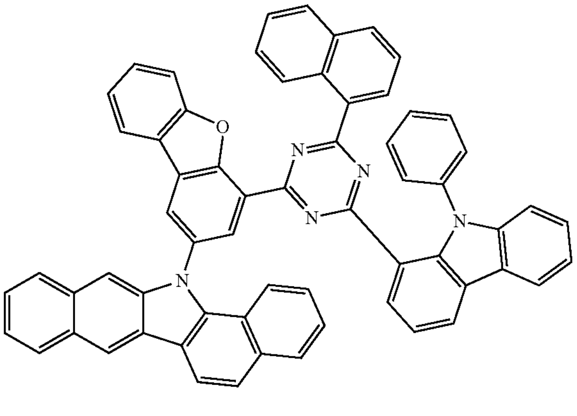
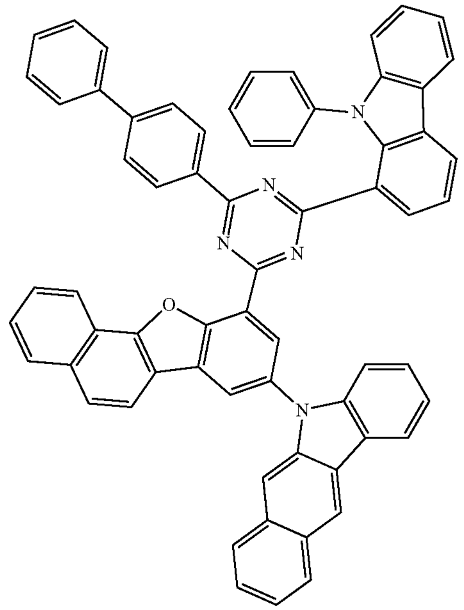

-continued
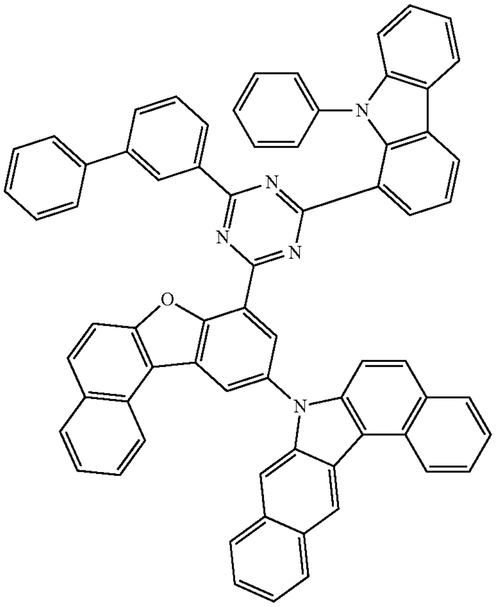
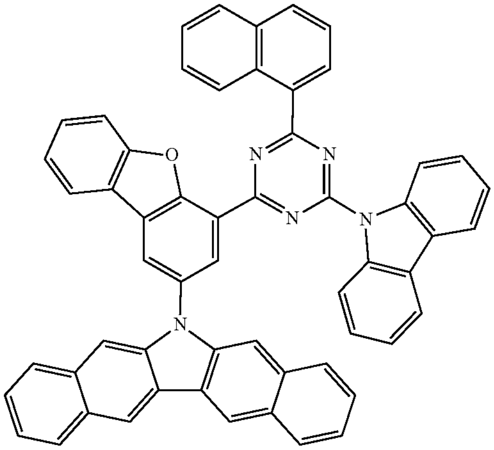
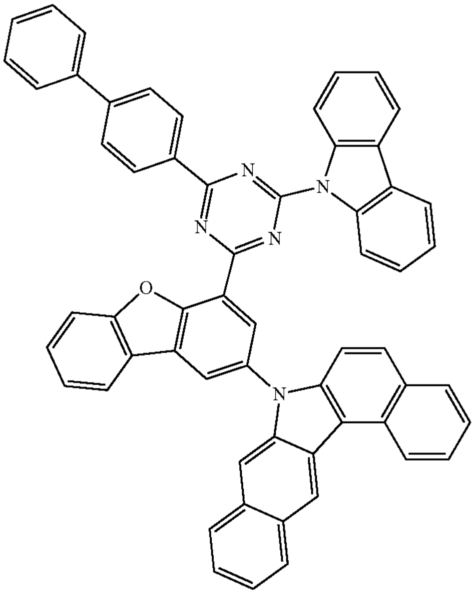
-continued
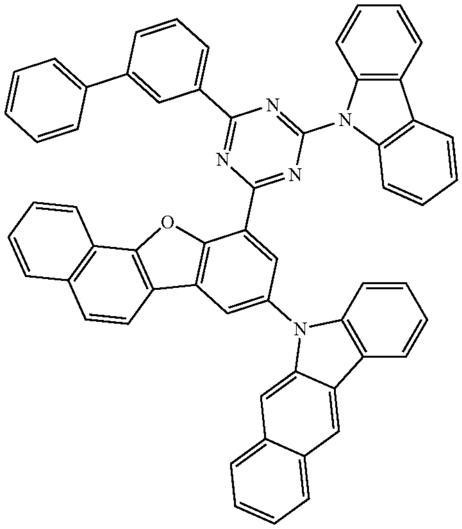
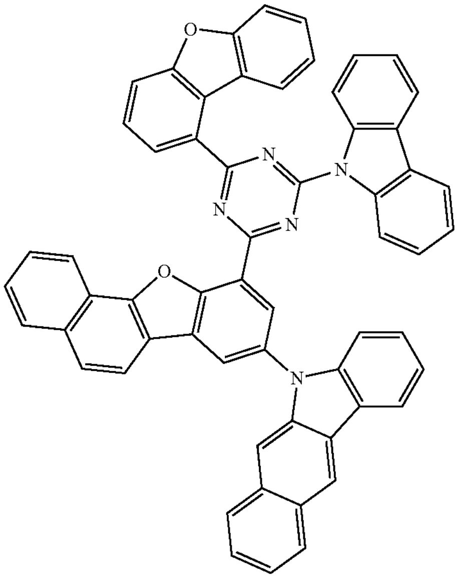
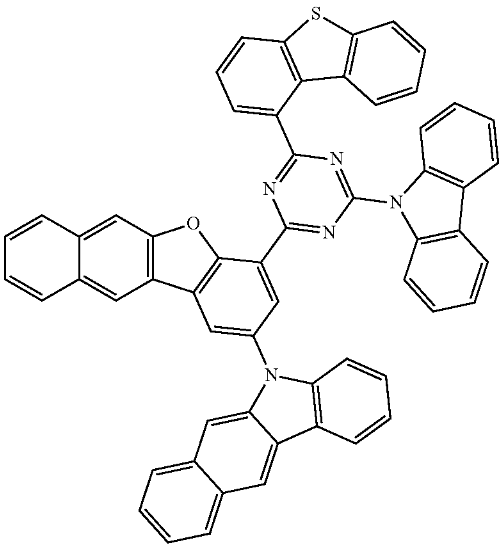

-continued
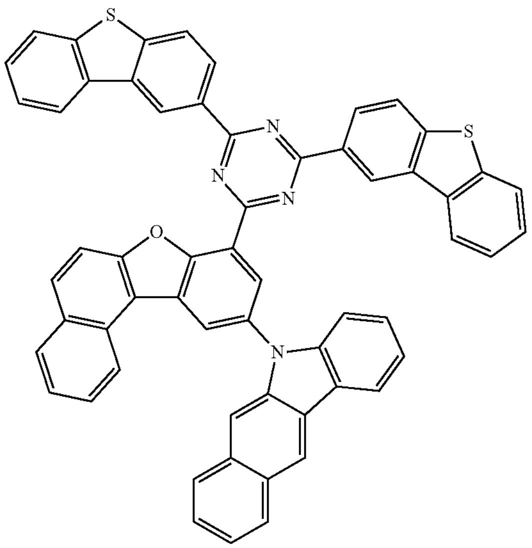
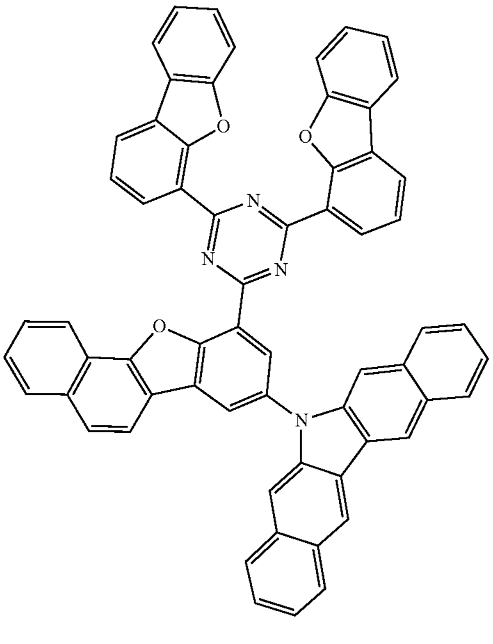
-continued
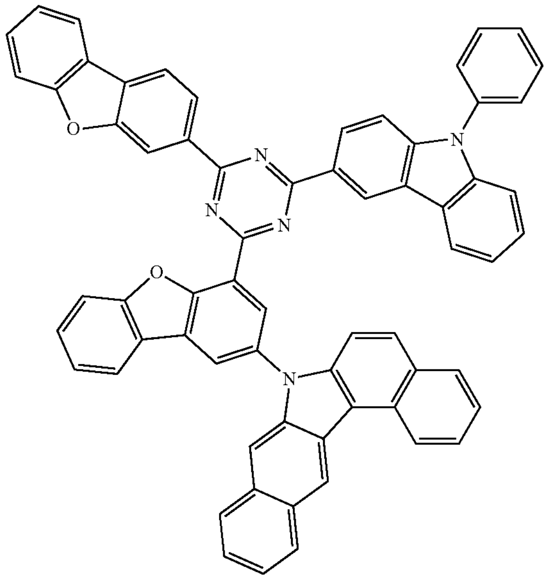
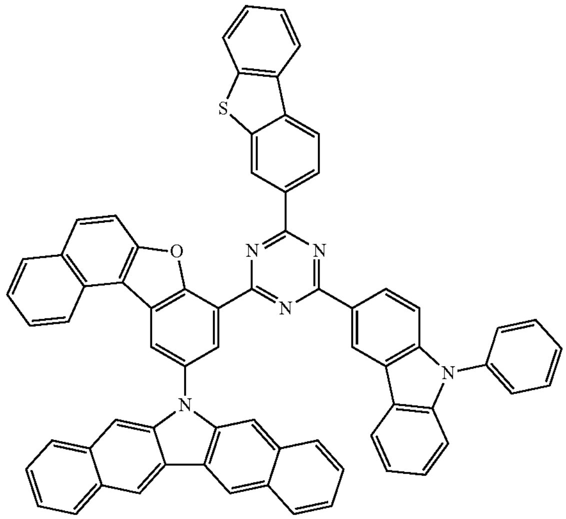
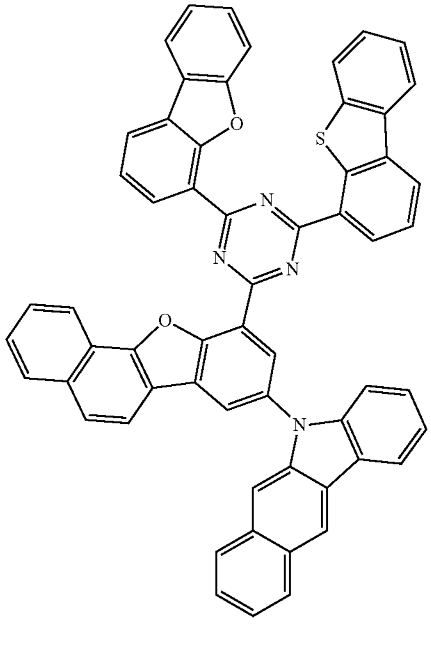

-continued
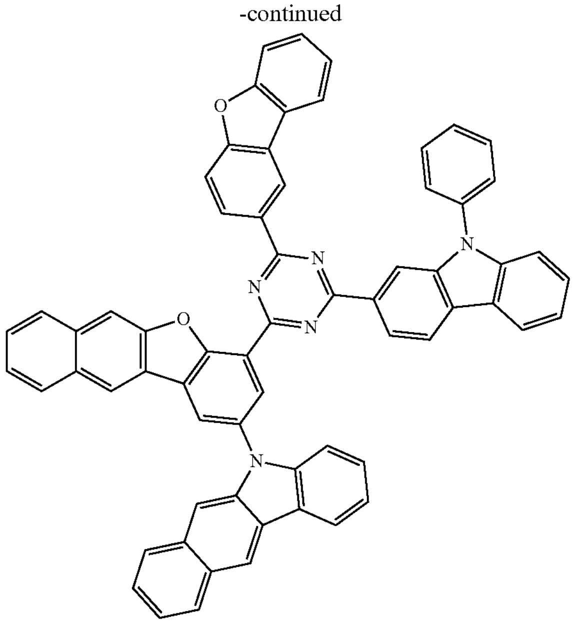
-continued
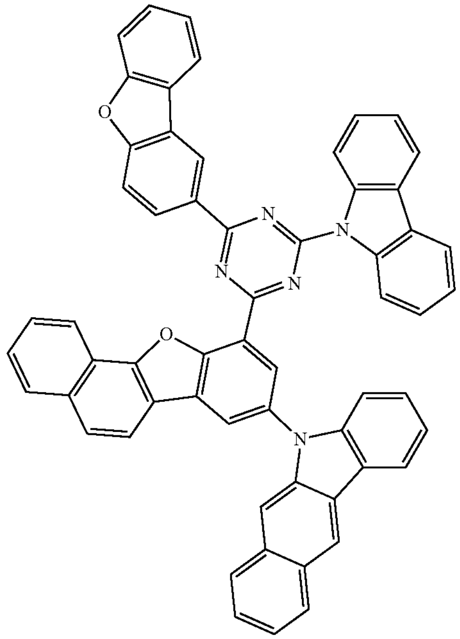
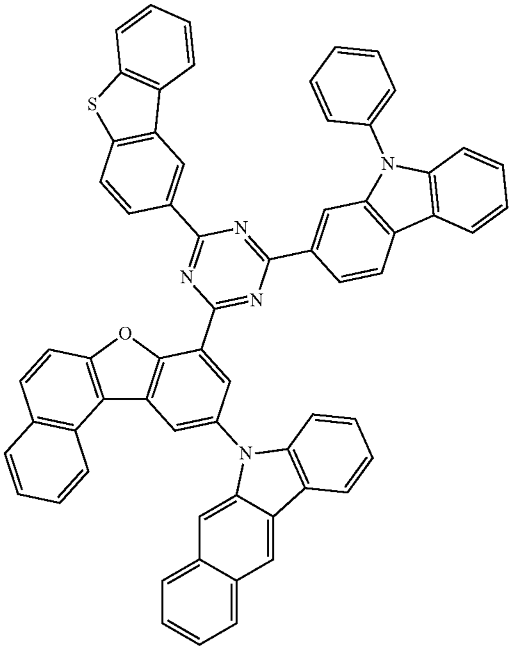
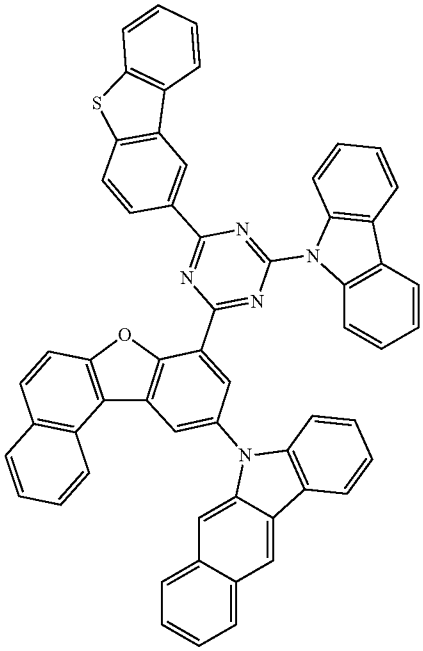

-continued
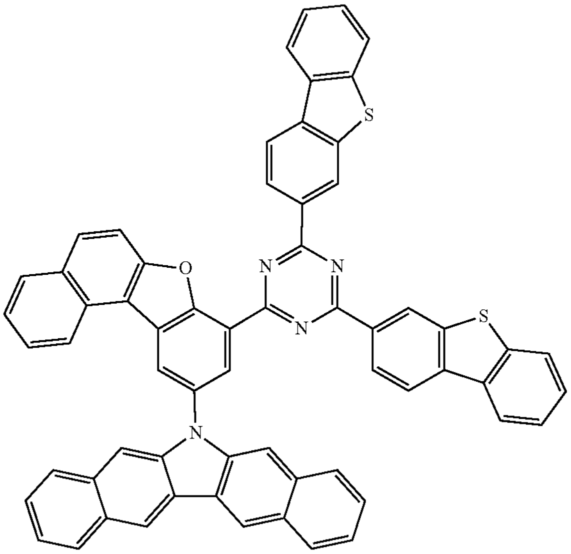
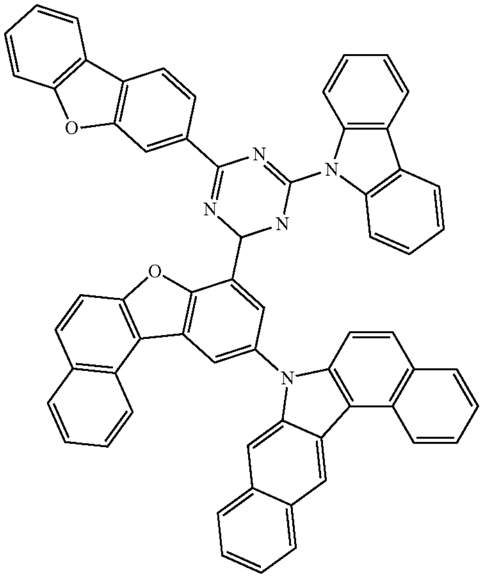
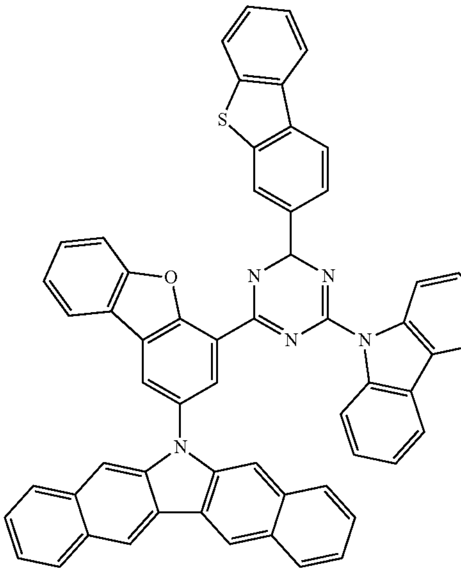
-continued
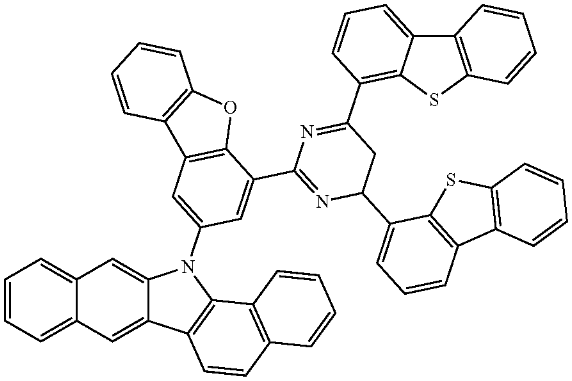
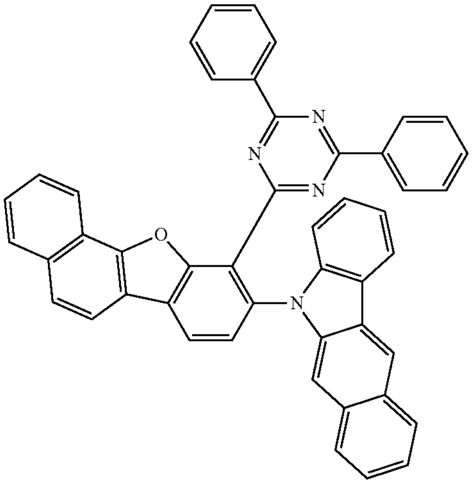
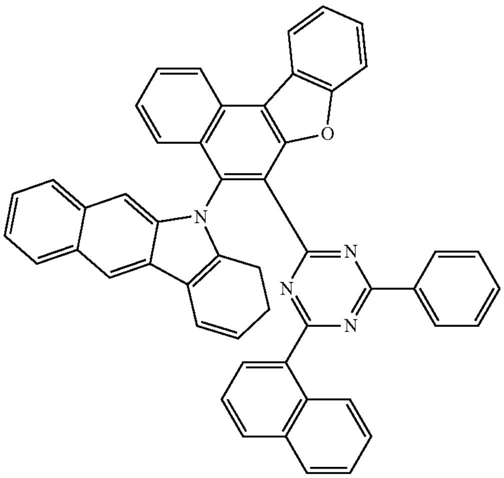

-continued
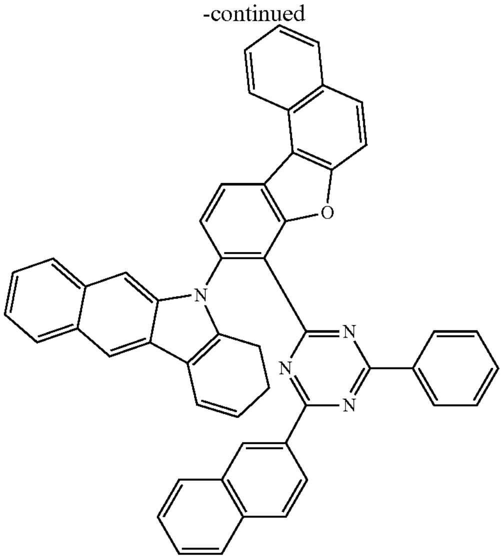
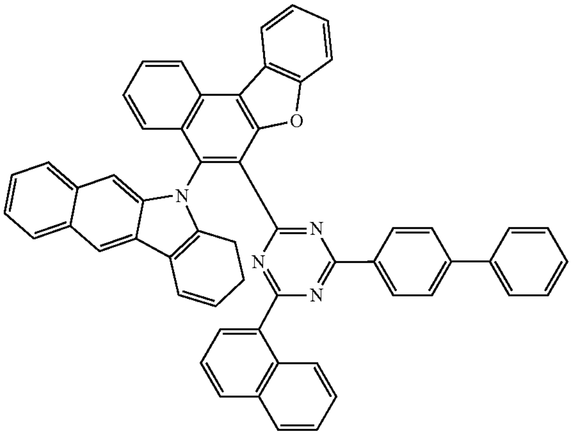
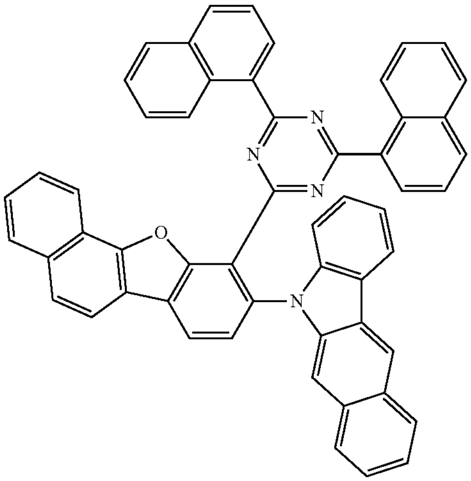
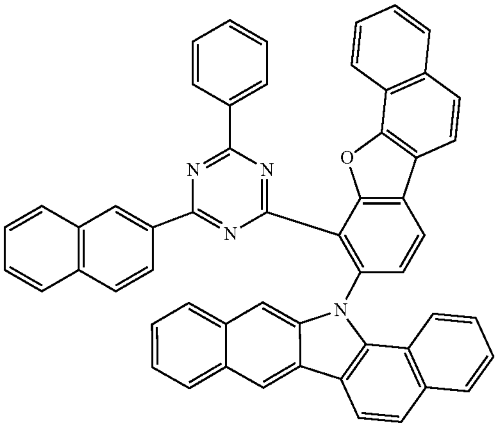
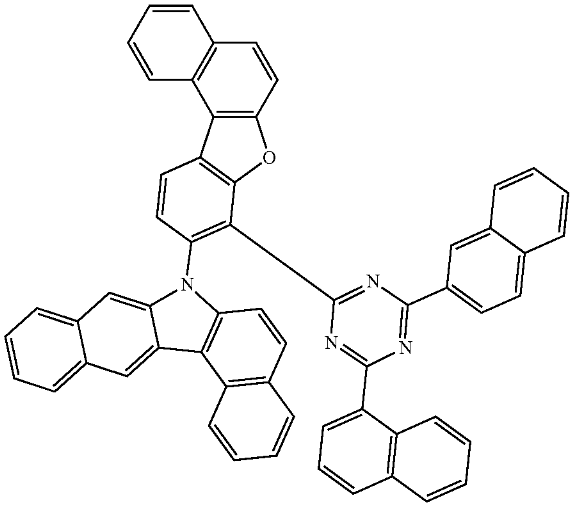
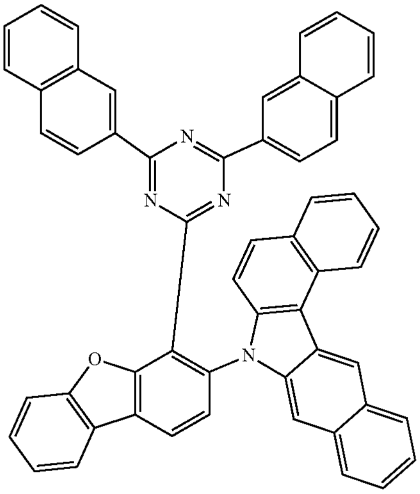
-continued -continued
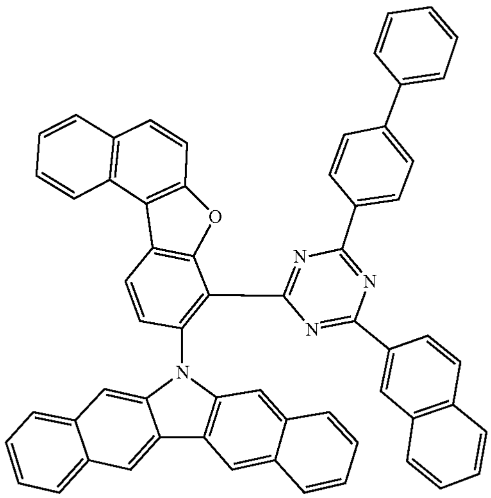
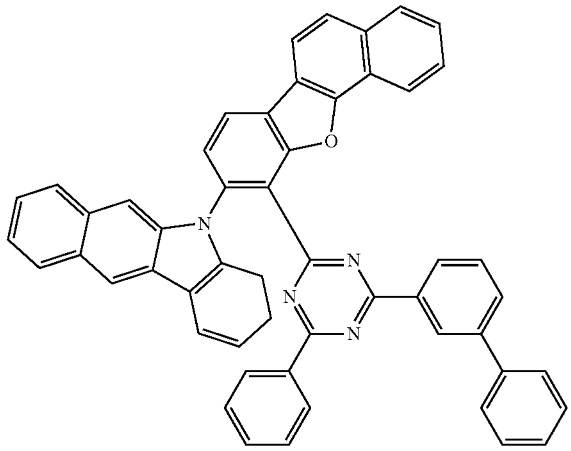
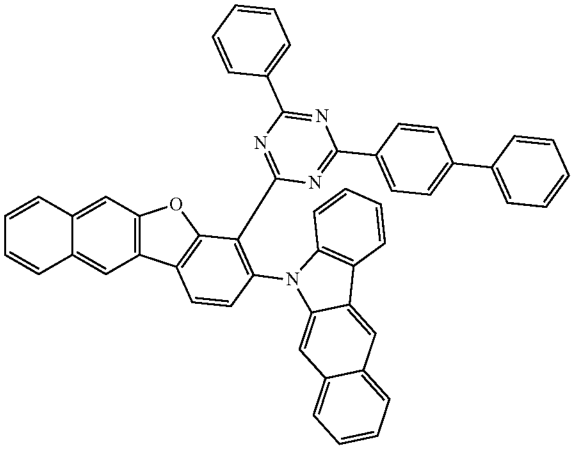
-continued
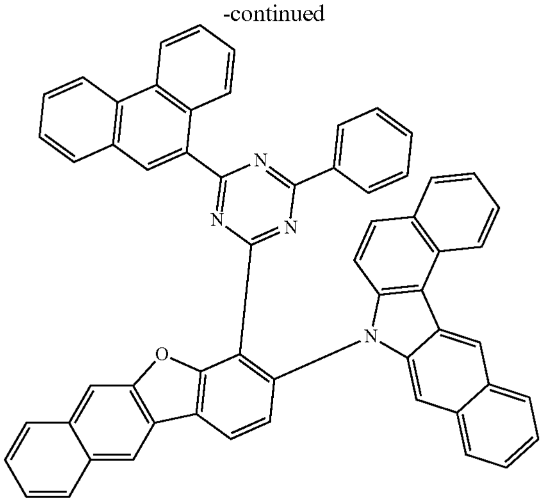
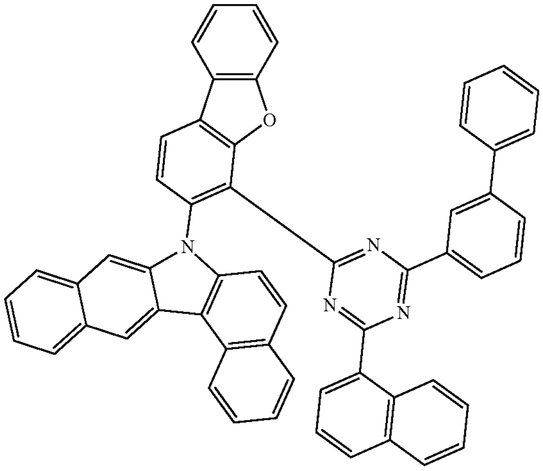
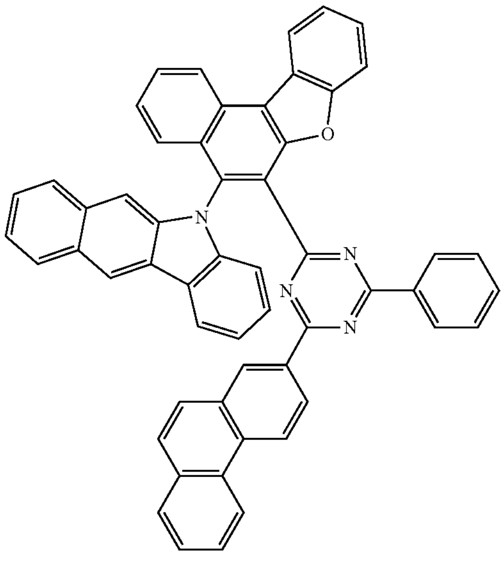

-continued
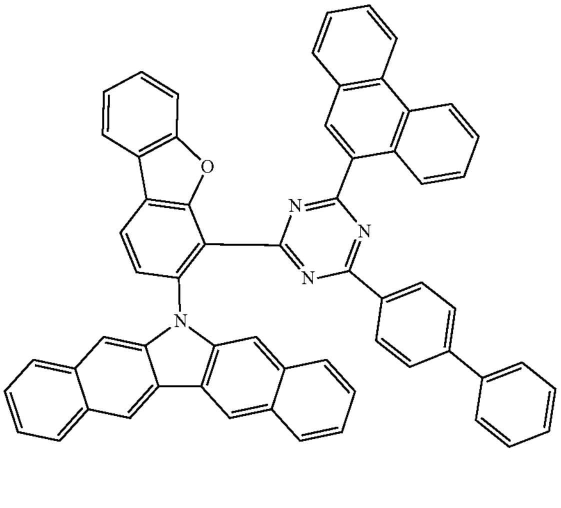
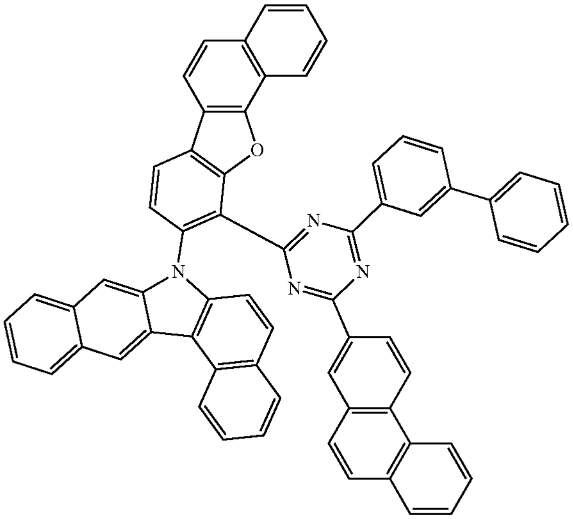
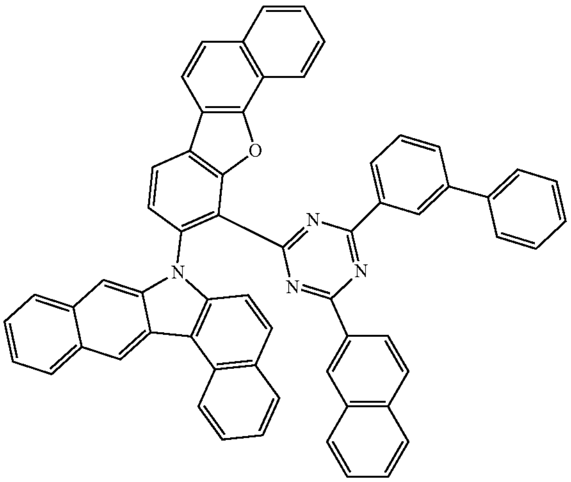
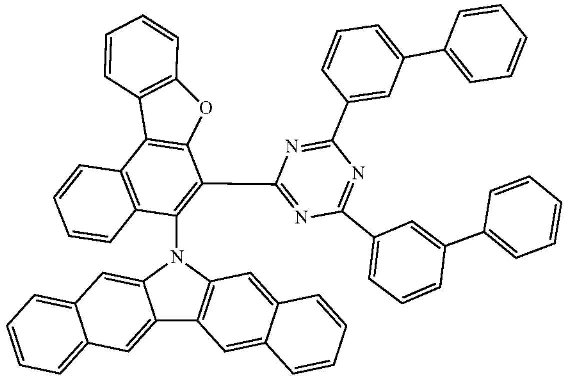
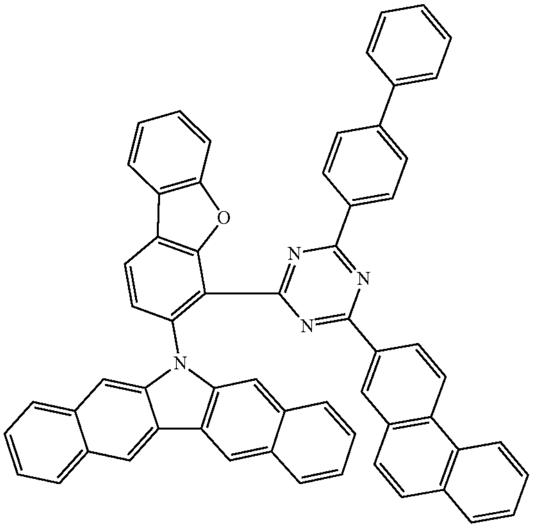
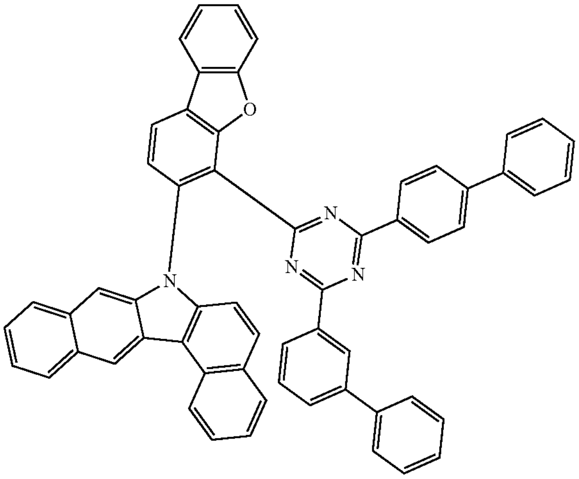
-continued -continued
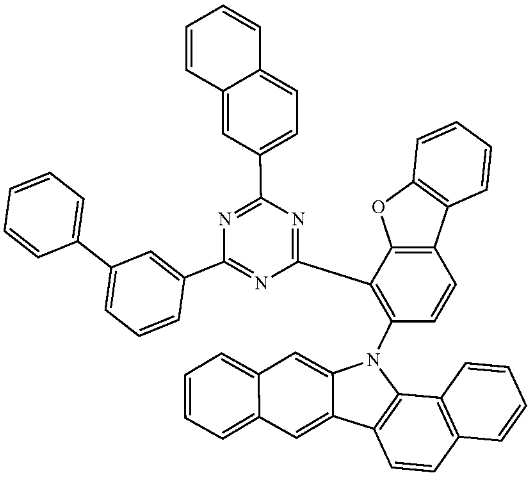
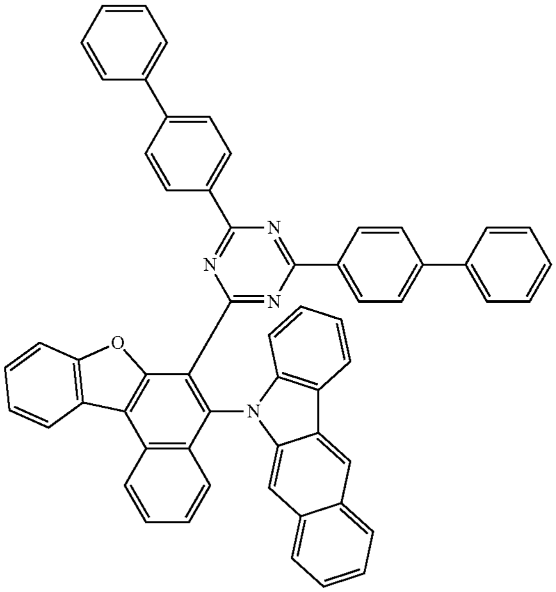
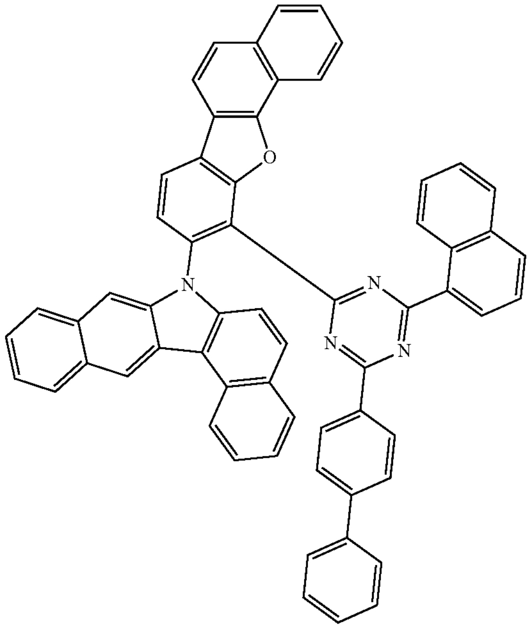
-continued
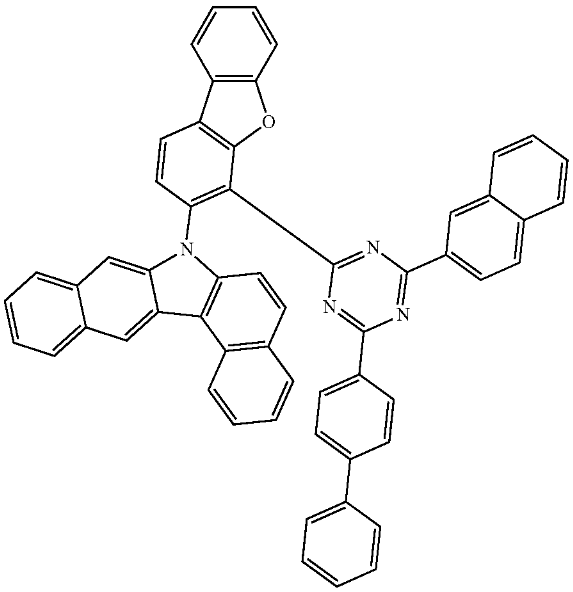
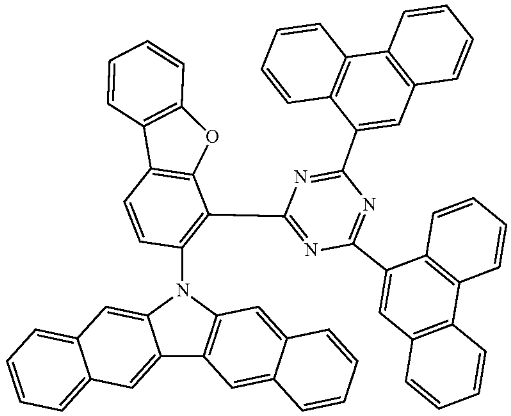
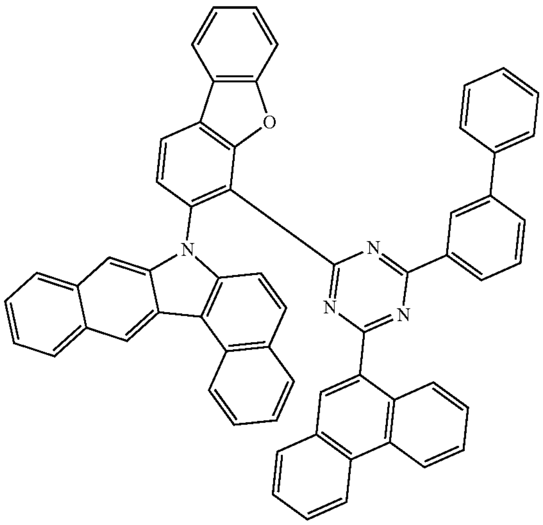

-continued
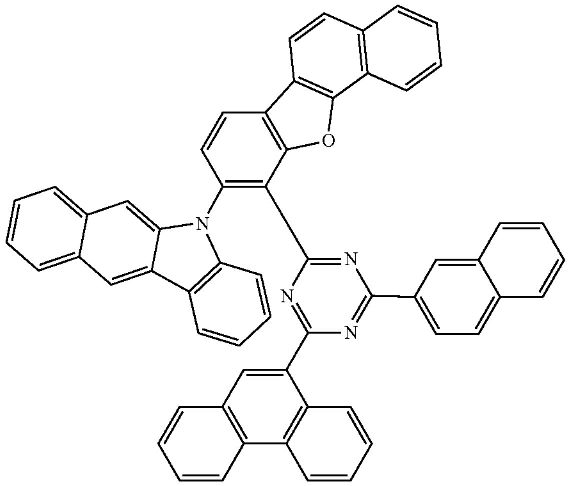
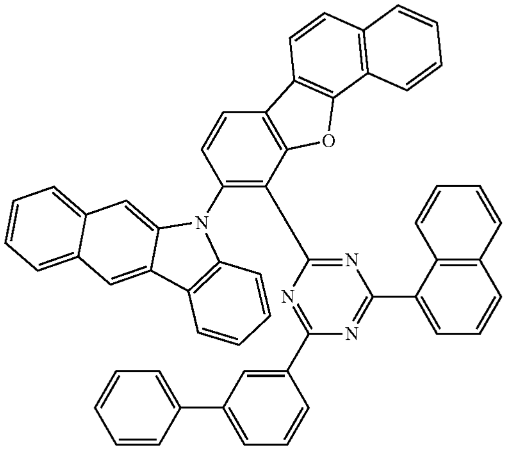
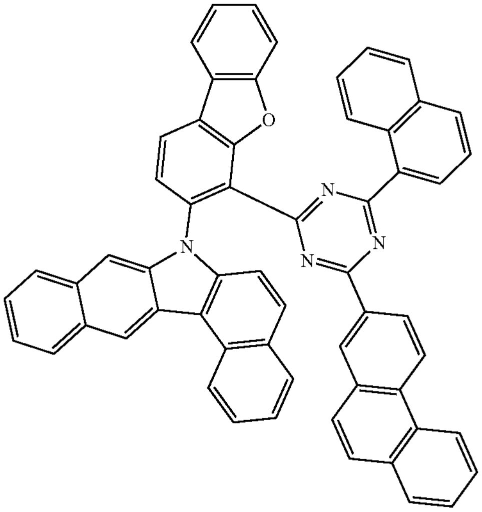
-continued
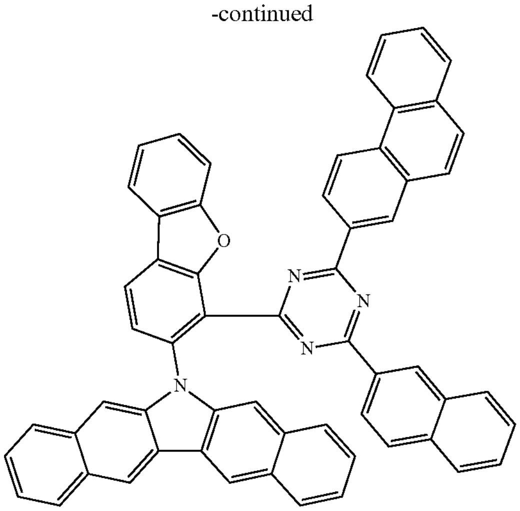
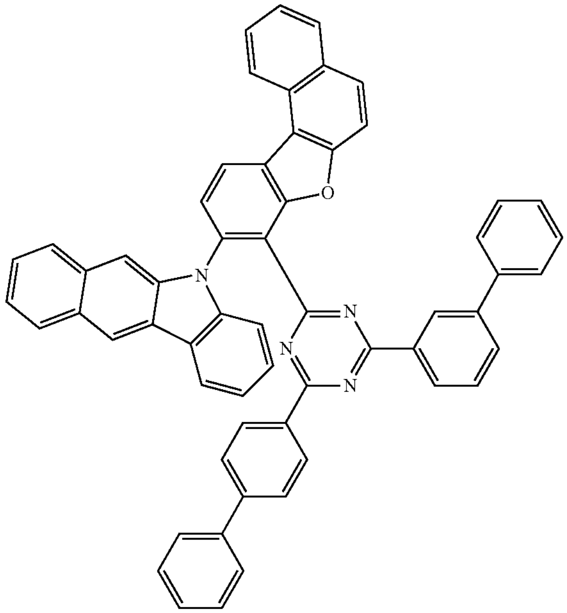
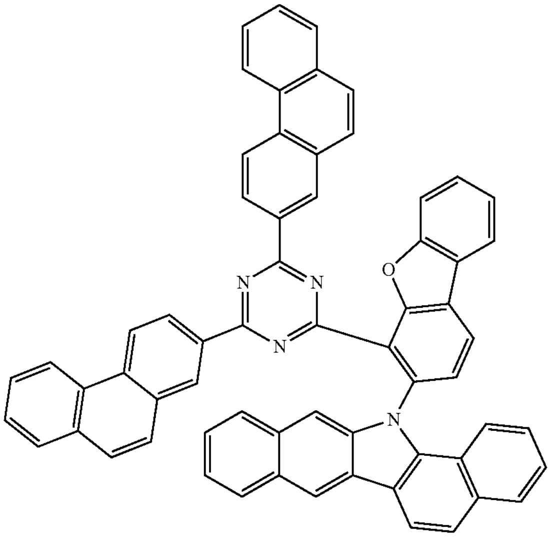

-continued
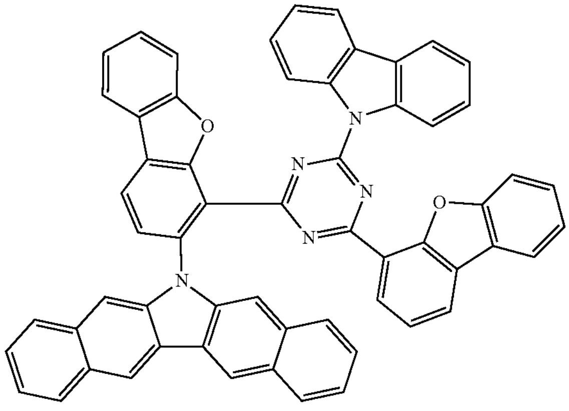
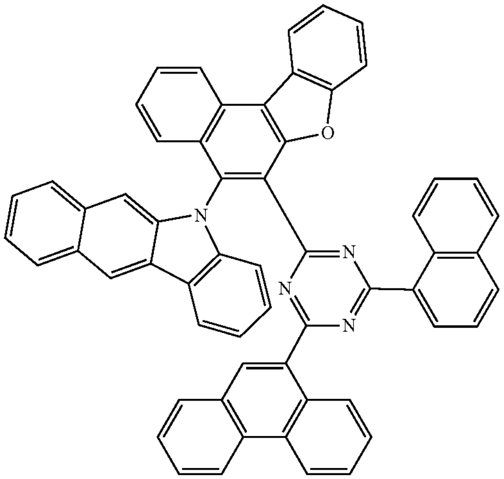
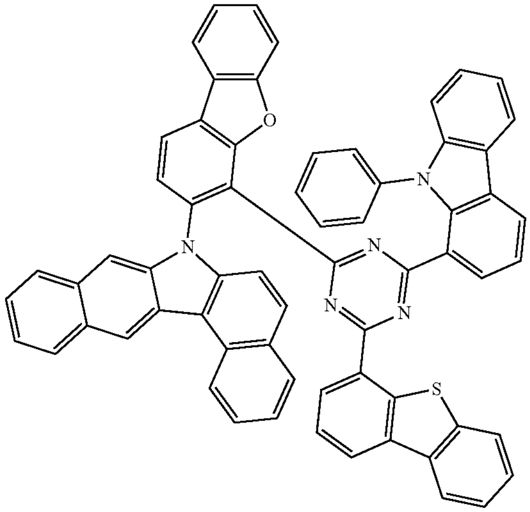
-continued
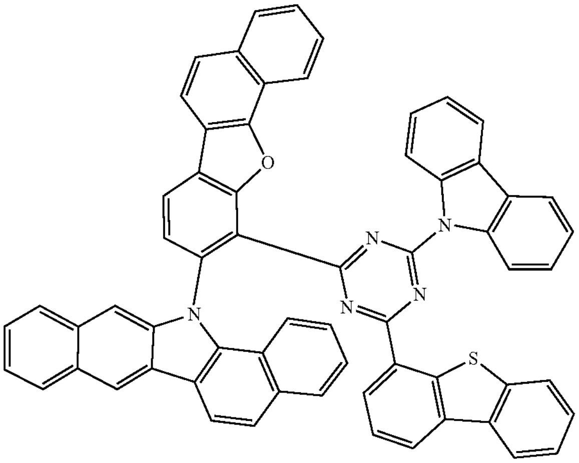
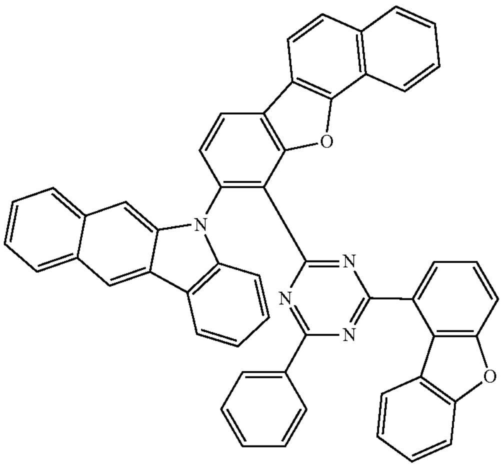
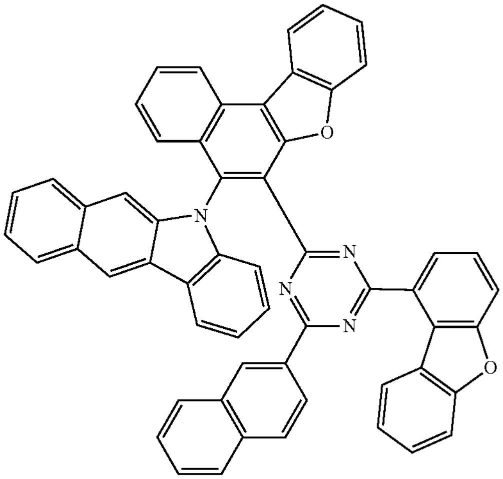

-continued
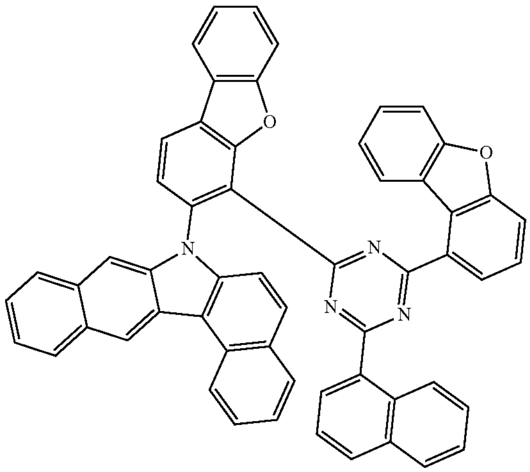
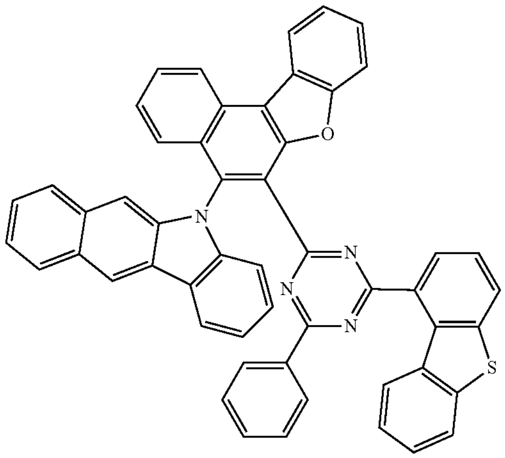
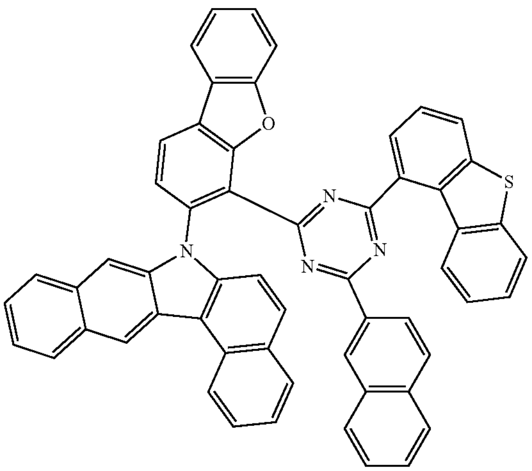
-continued
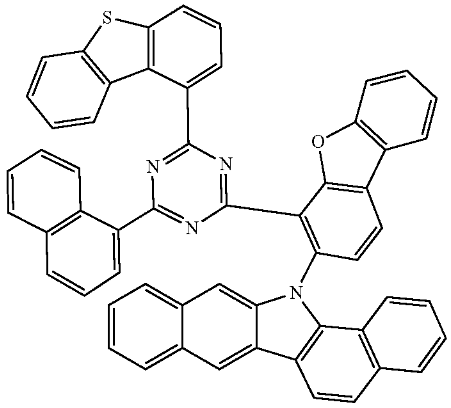
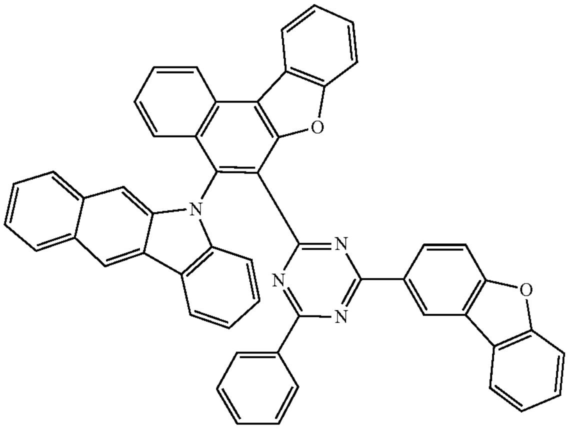
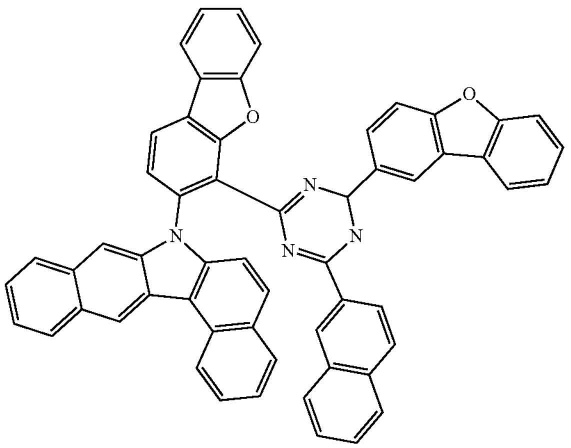

-continued
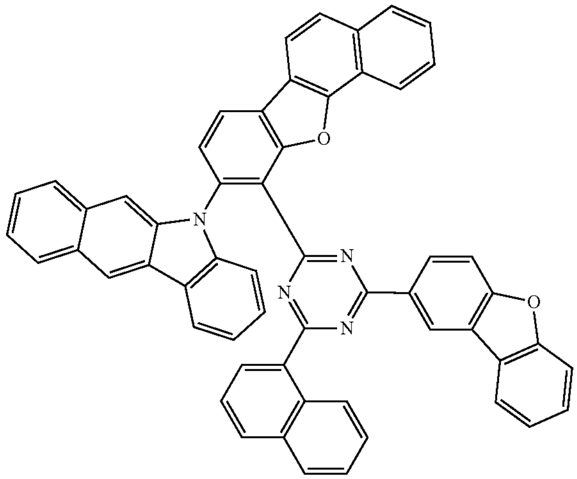
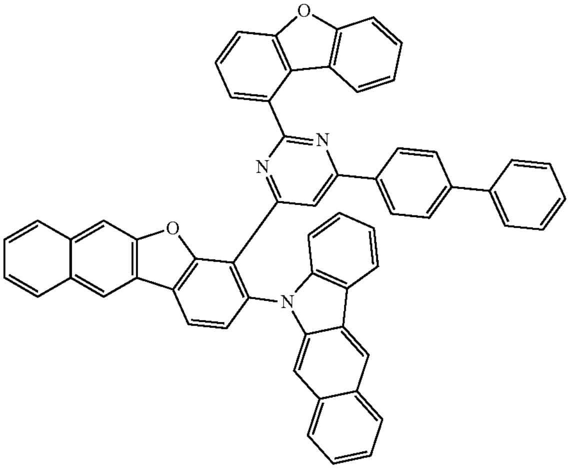
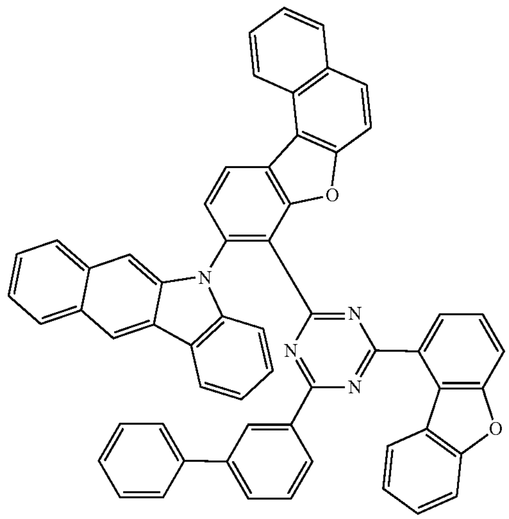
-continued
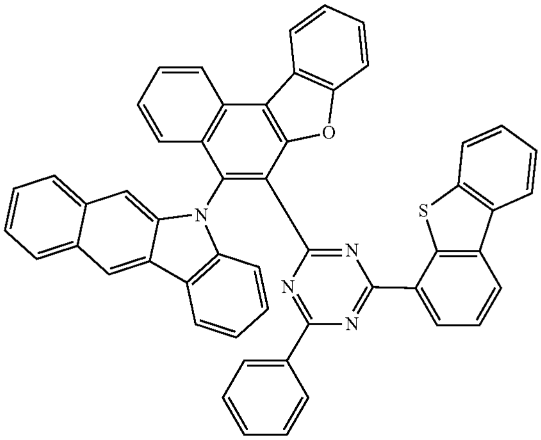
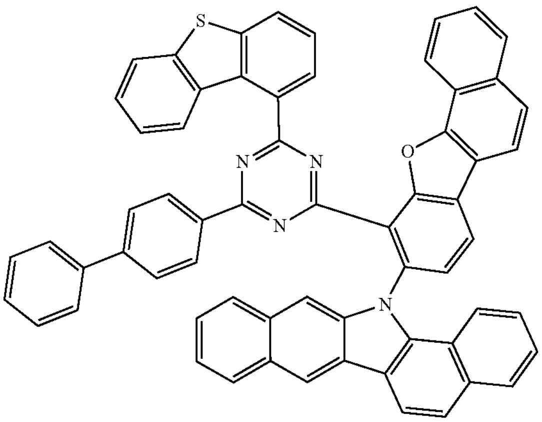
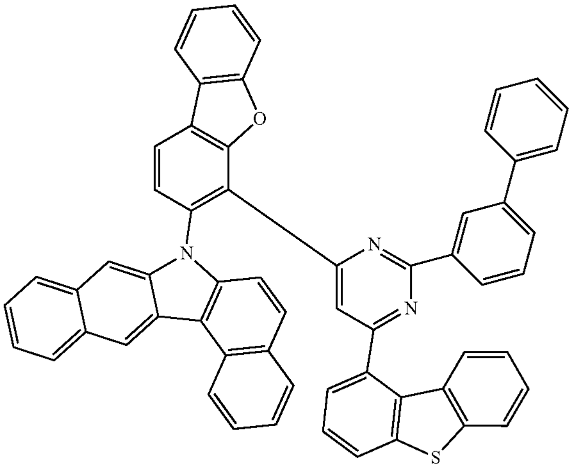

-continued
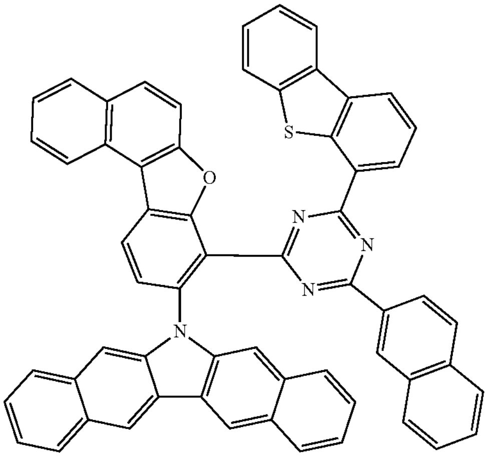
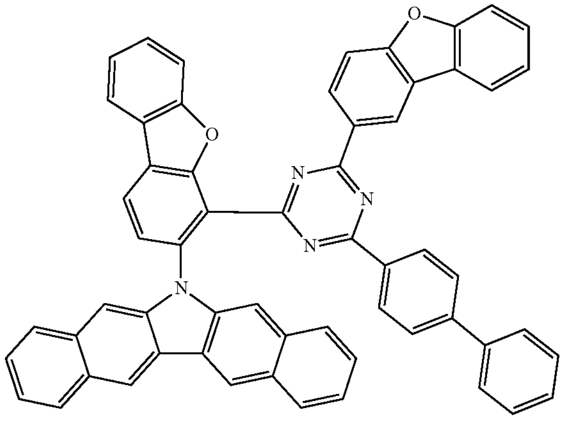
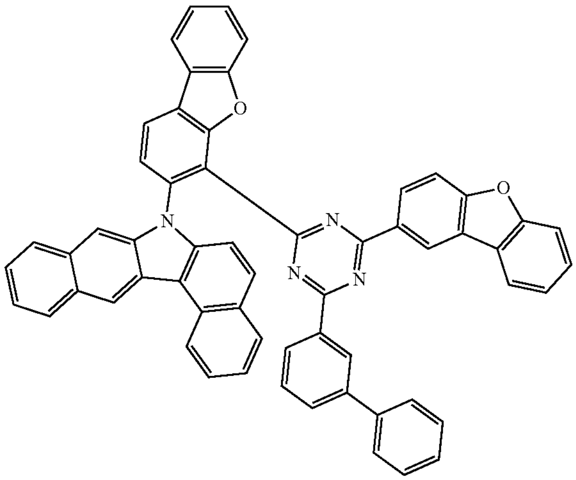
-continued
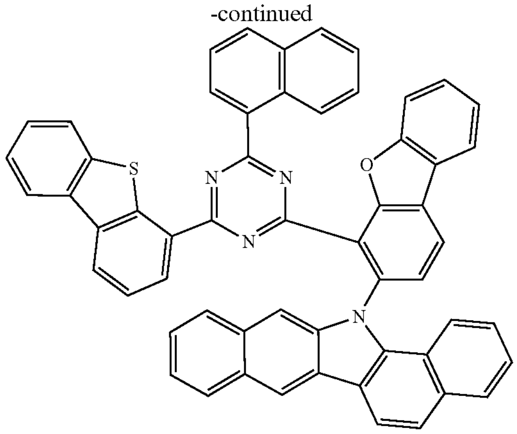
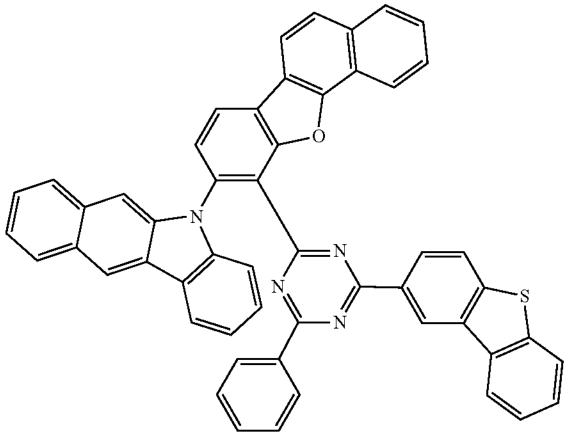
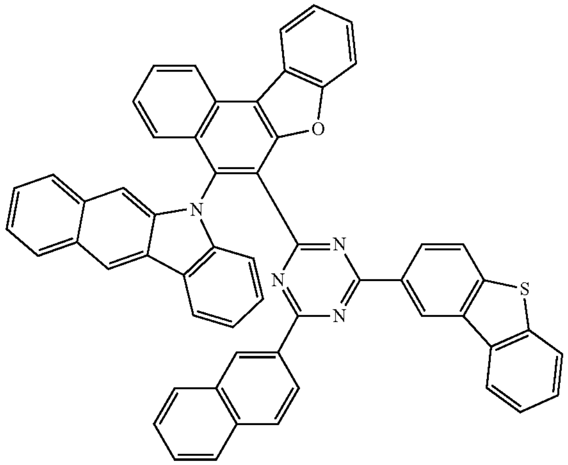
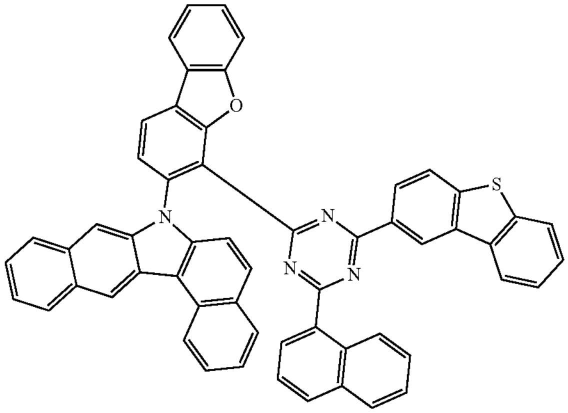

-continued
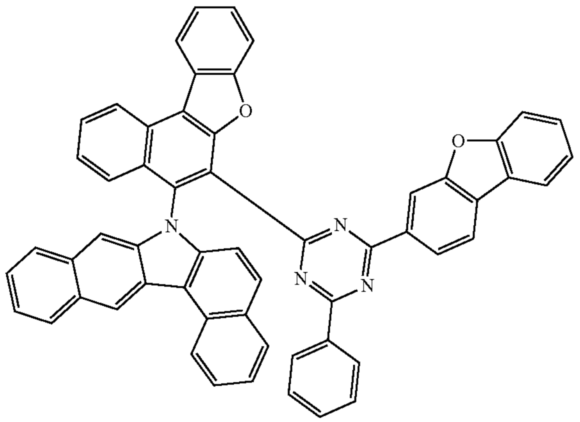
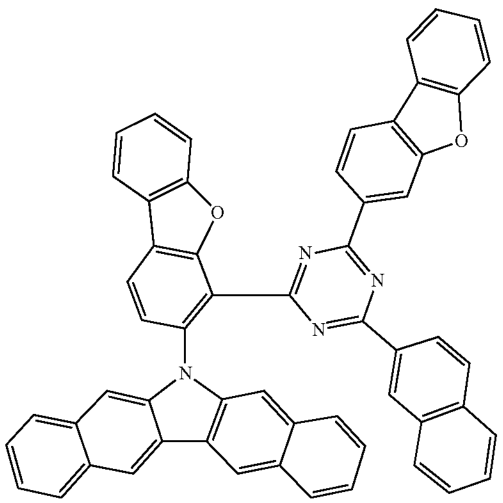
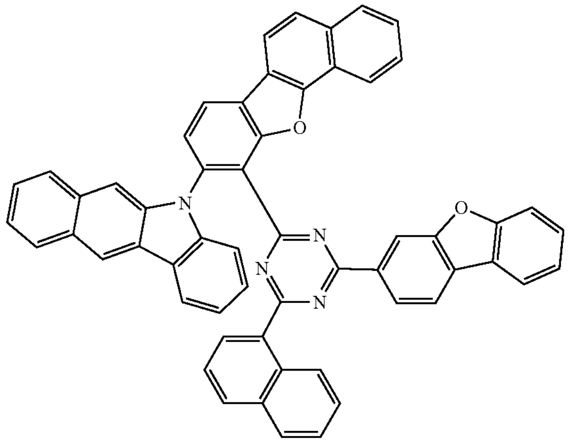
-continued
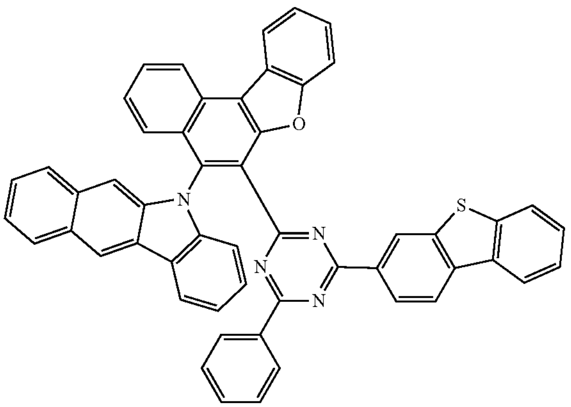
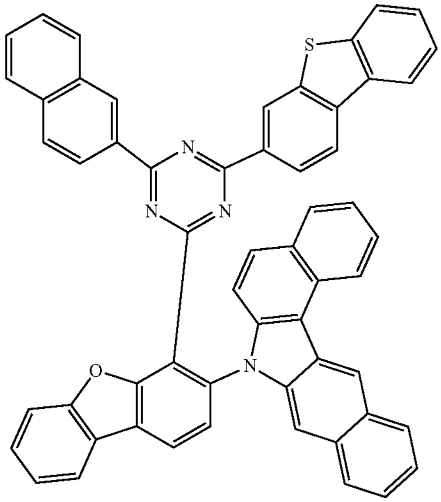
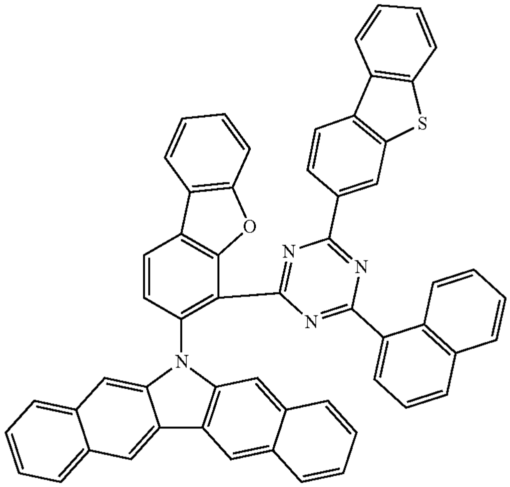

-continued
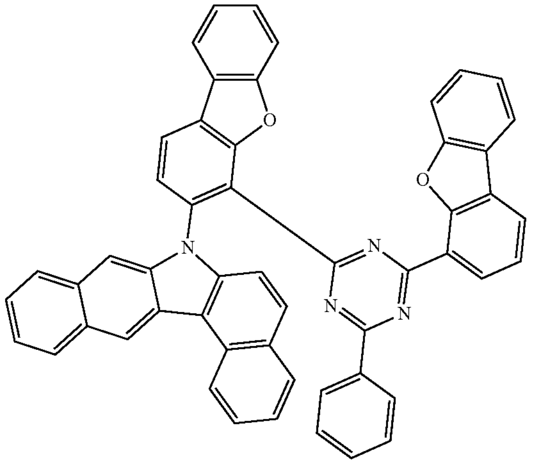
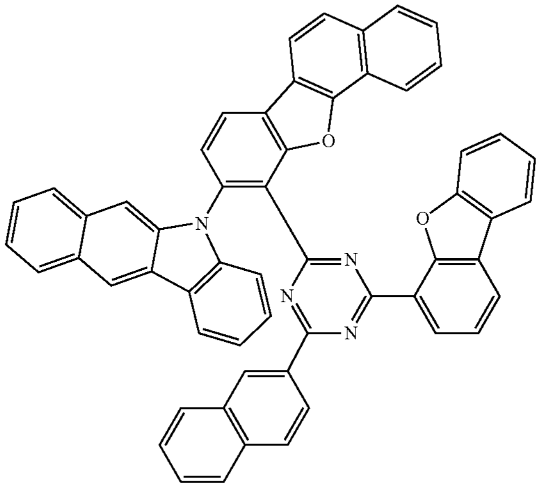
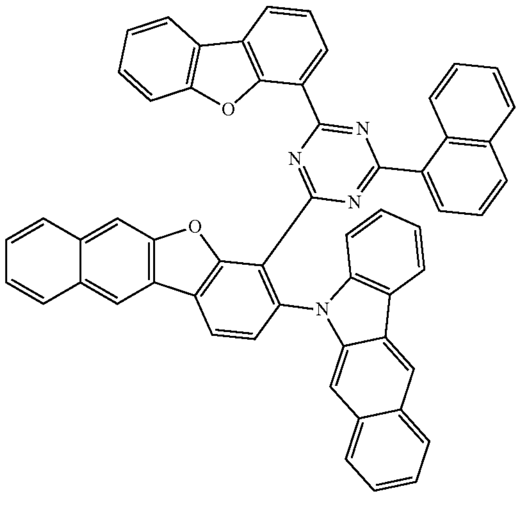
-continued
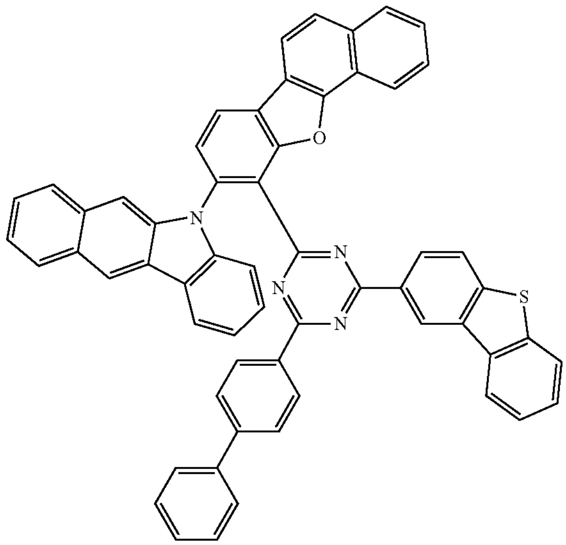
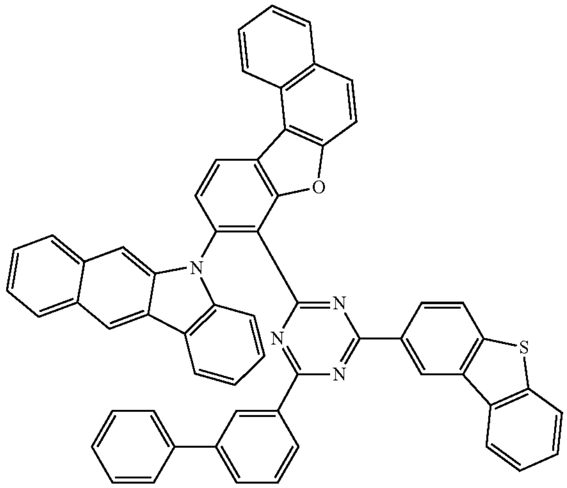
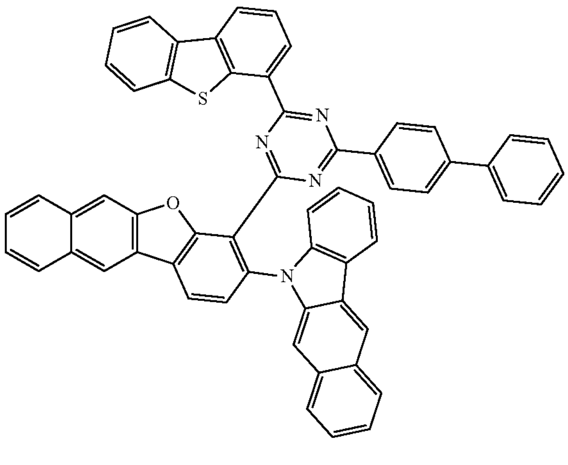

-continued
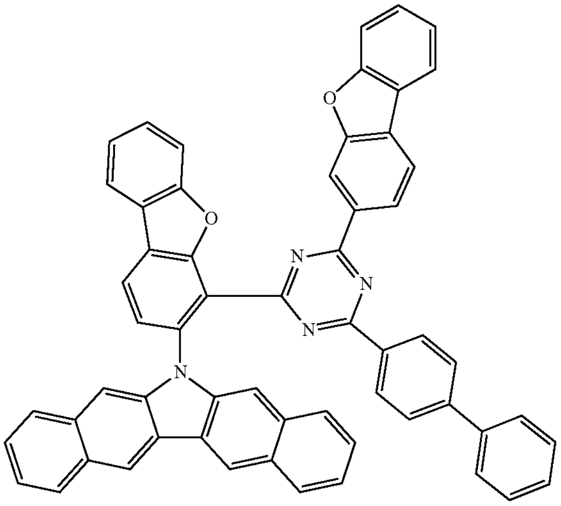
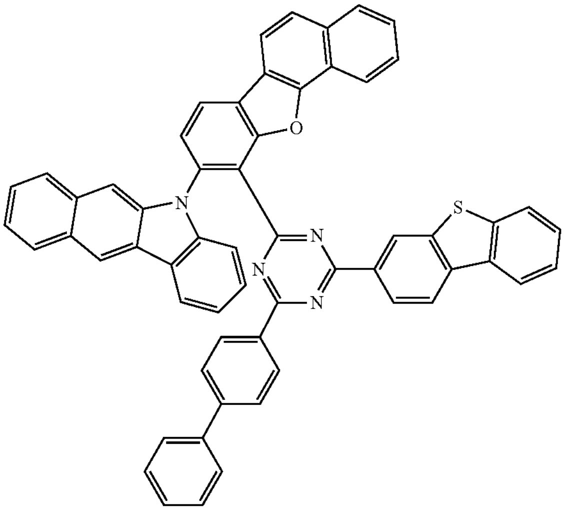
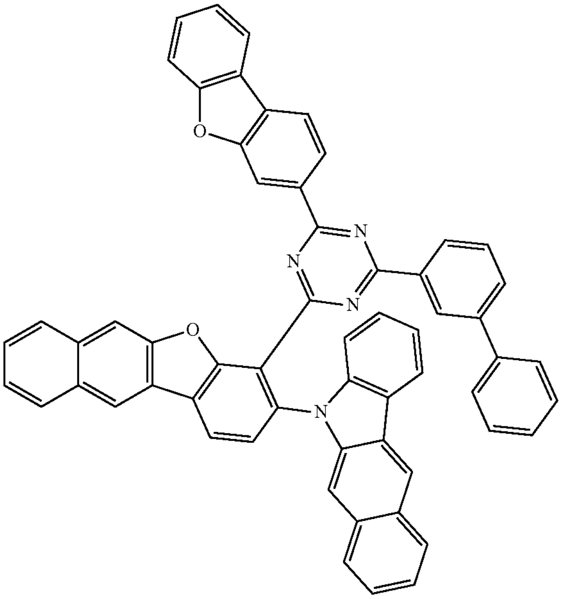
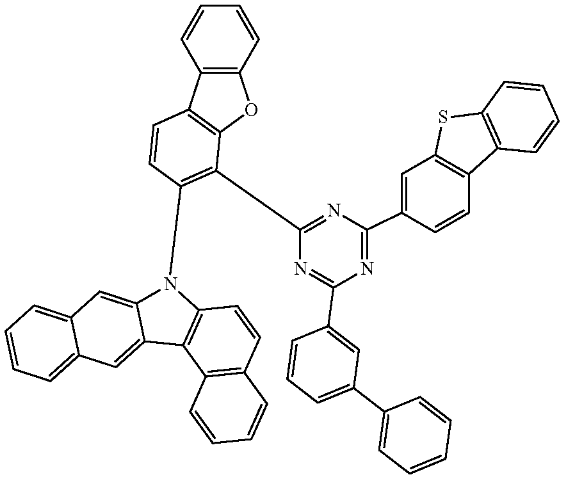
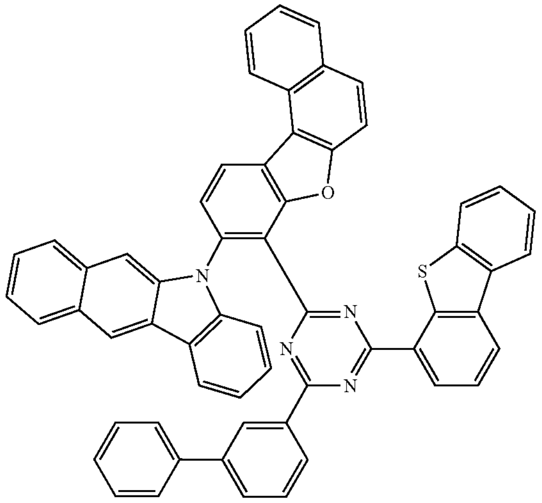
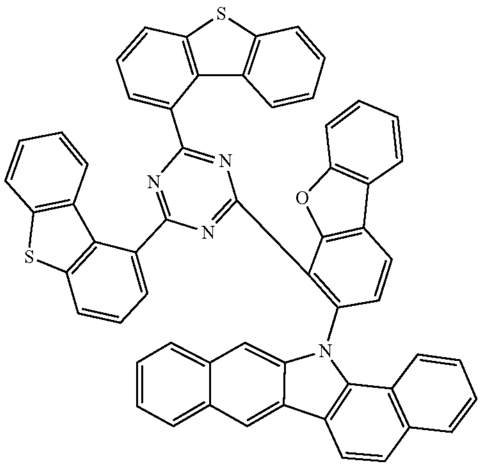
-continued -continued
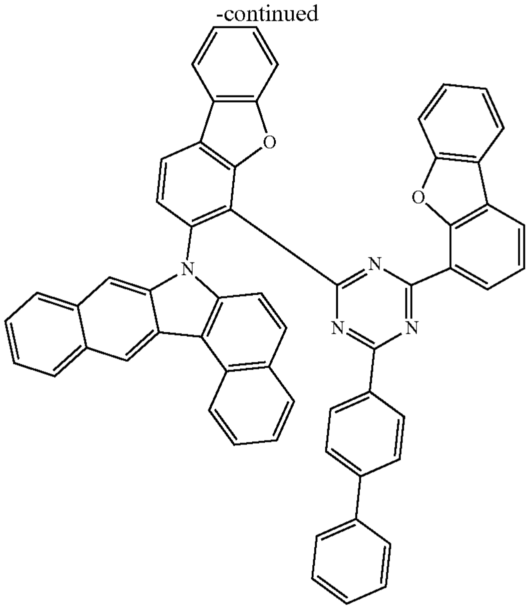
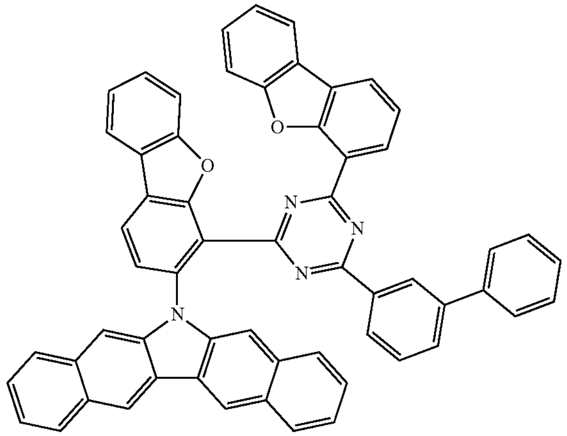
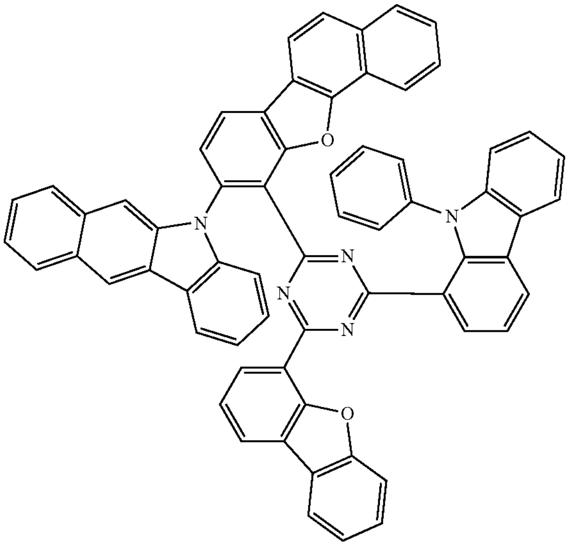
-continued
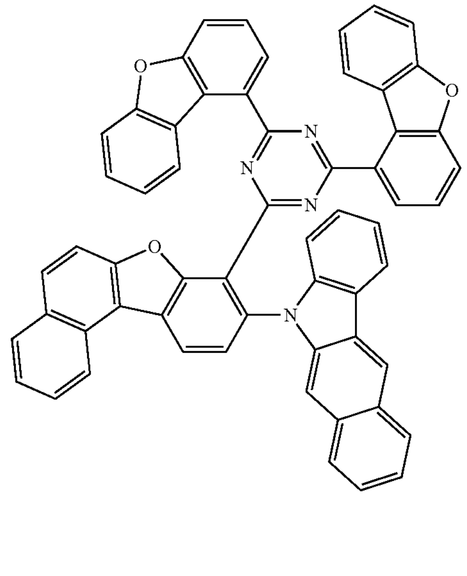
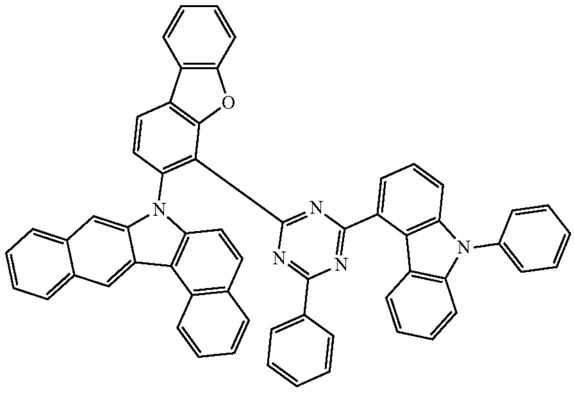
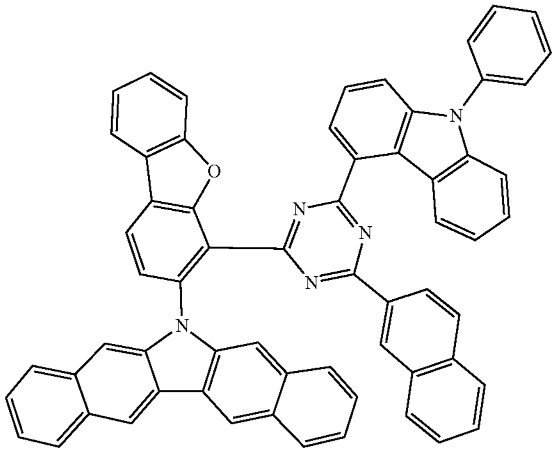

-continued
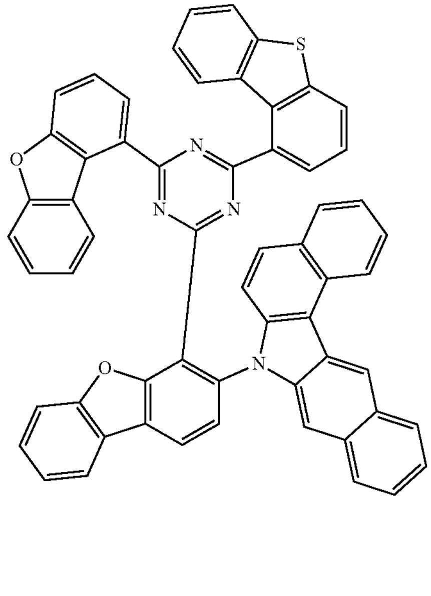
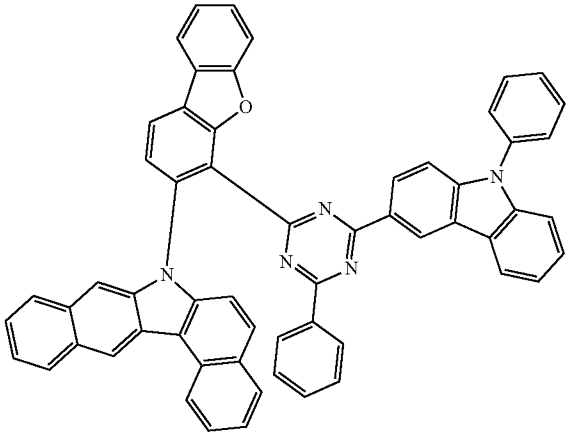
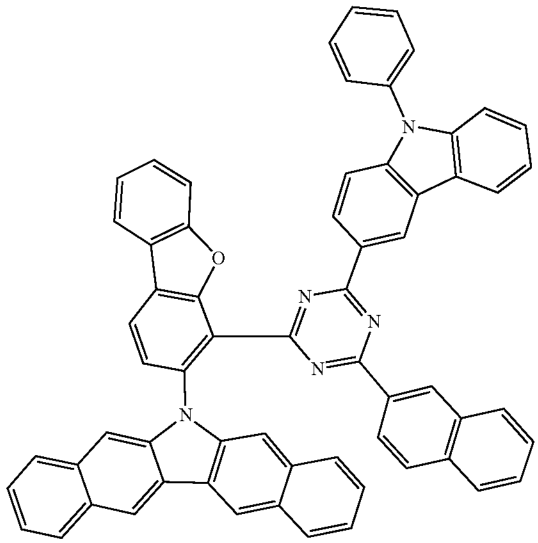
-continued
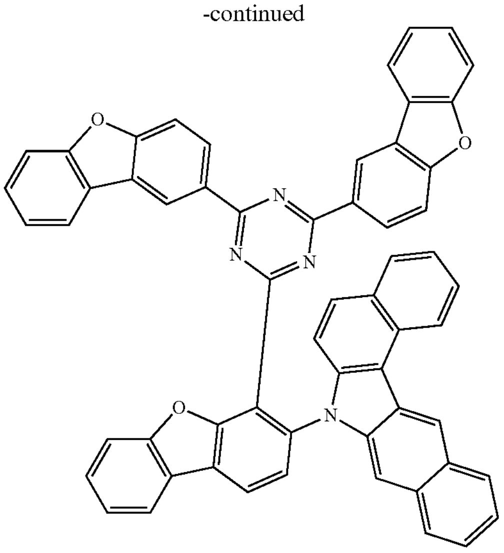
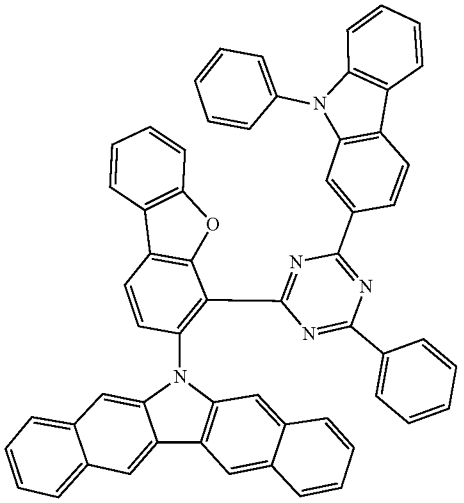
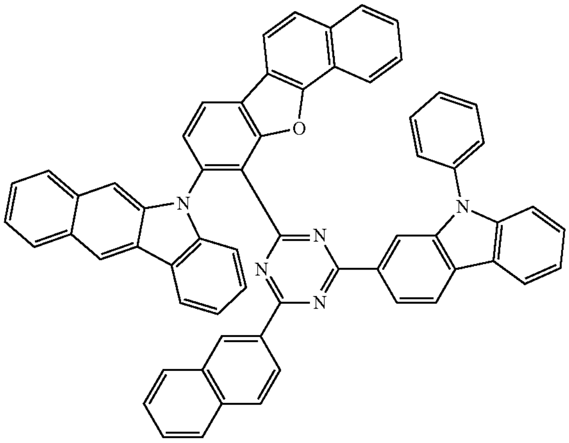

-continued
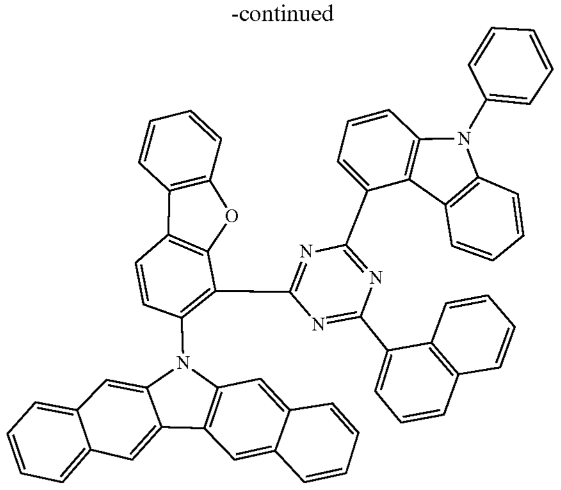
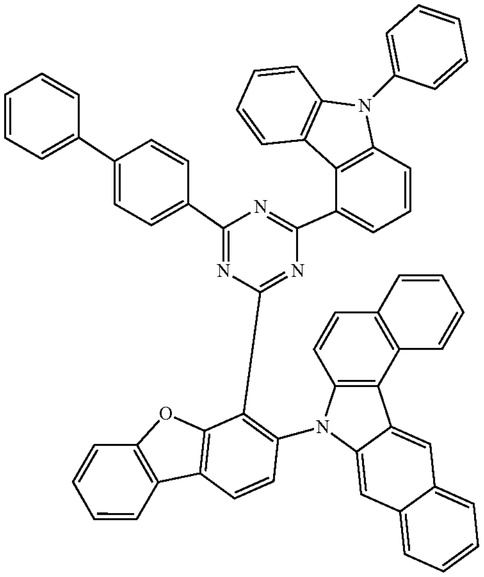
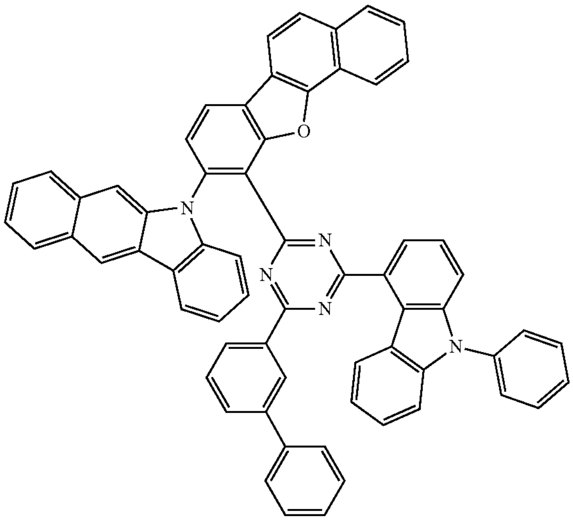
-continued
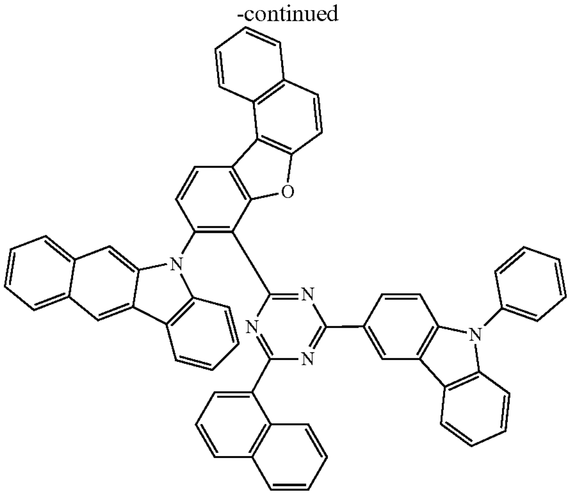
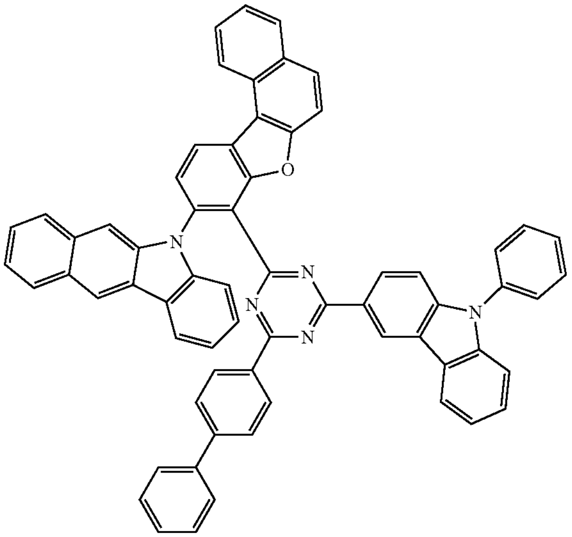
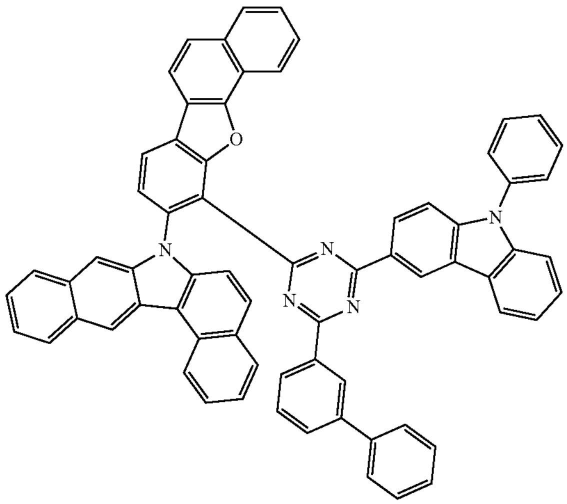

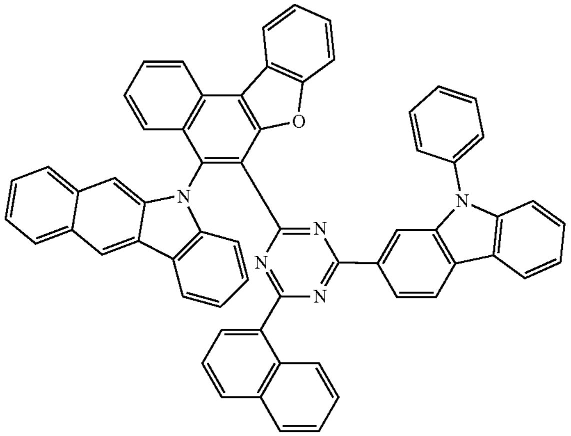
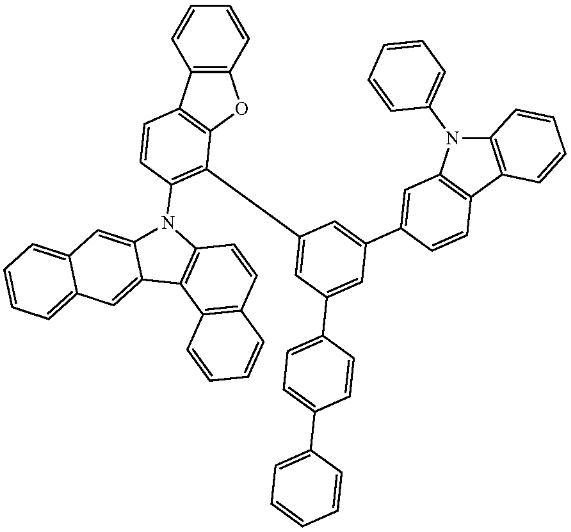
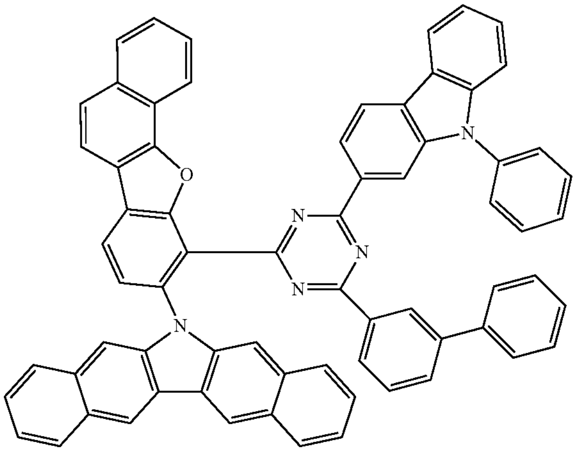
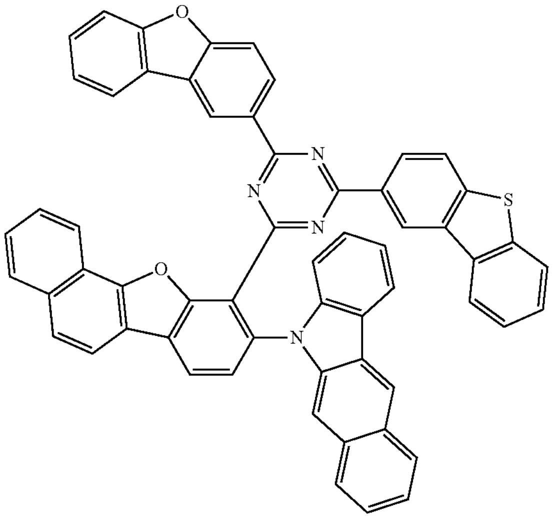
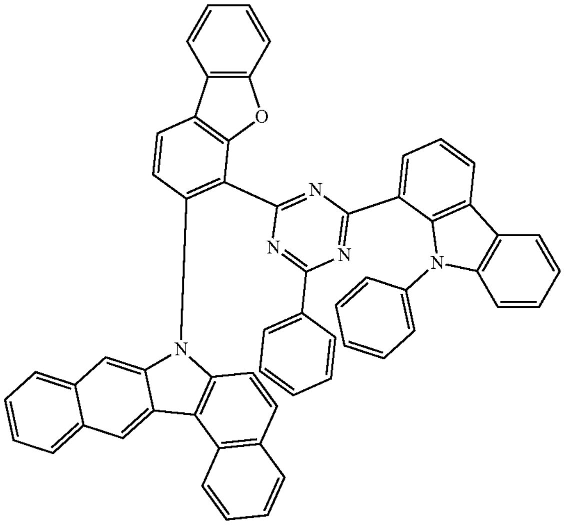
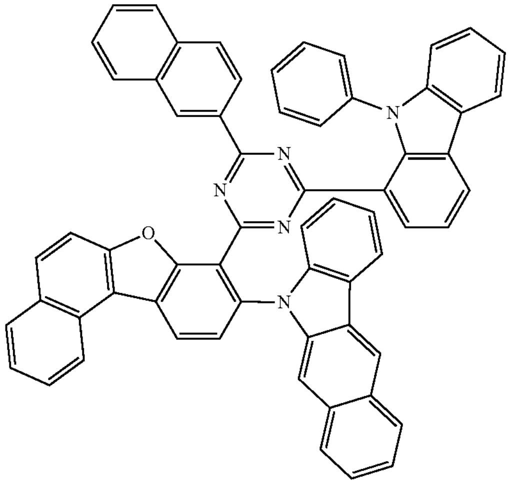

-continued
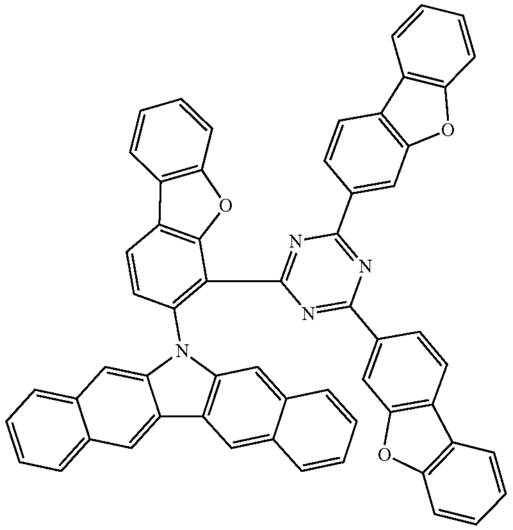
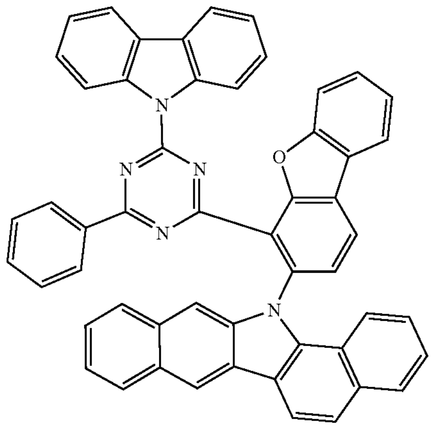
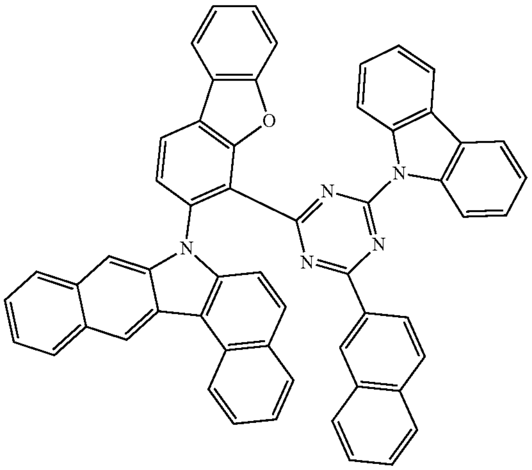
-continued
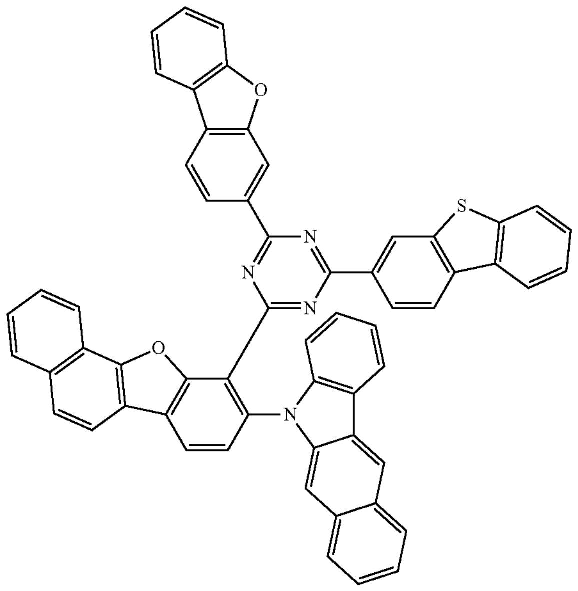
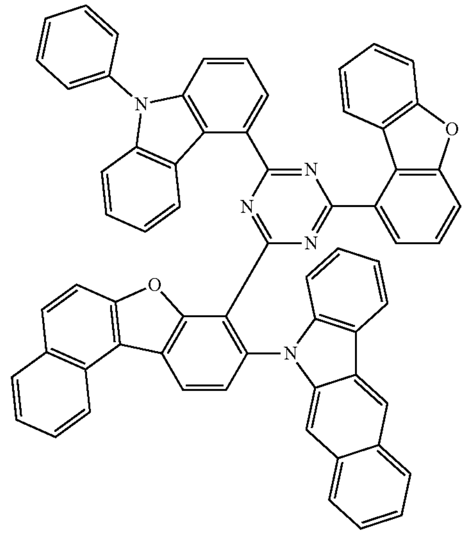
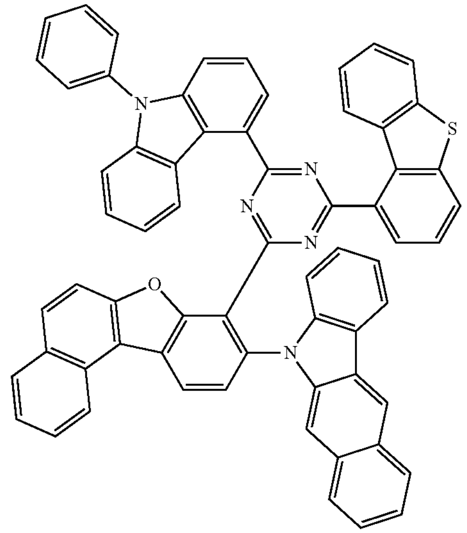

-continued
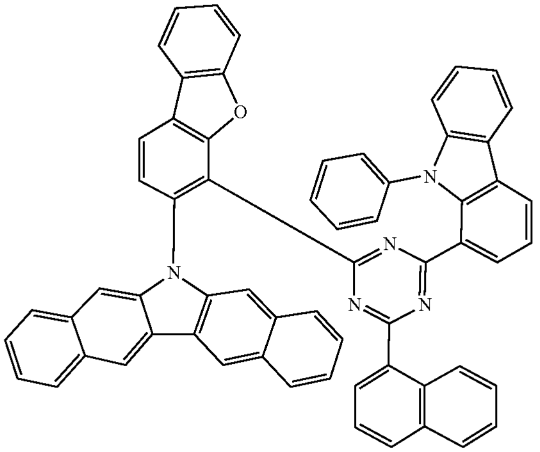
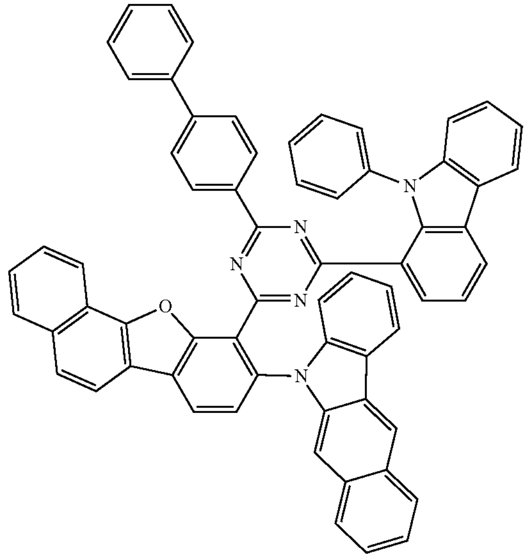
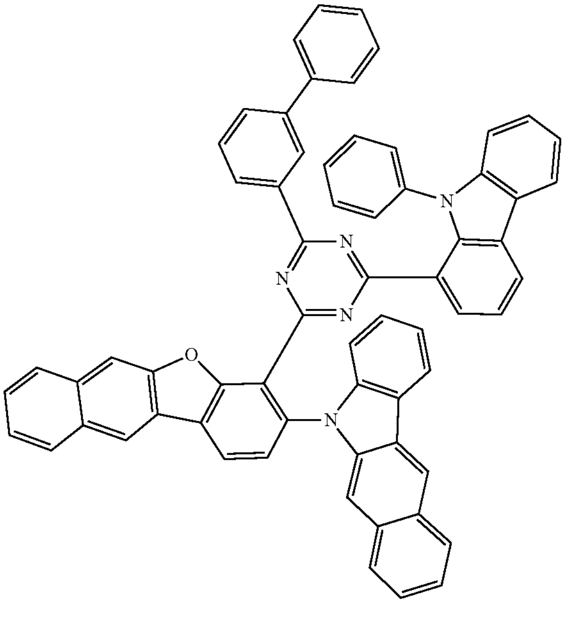
-continued
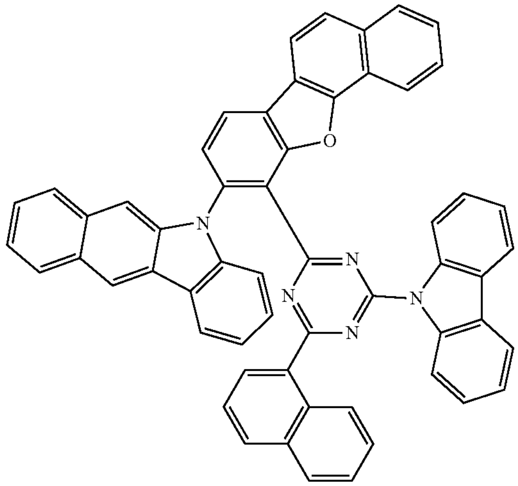
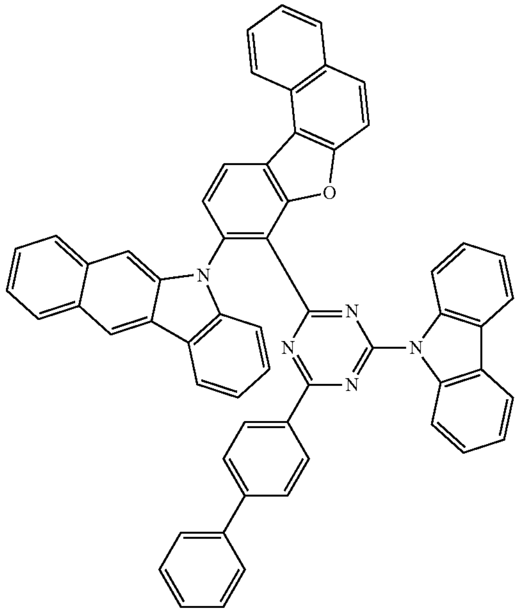
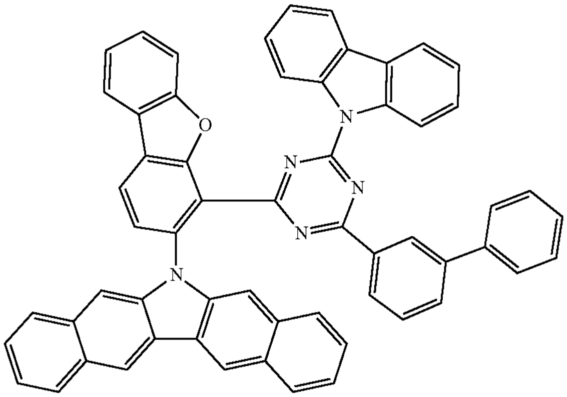

-continued
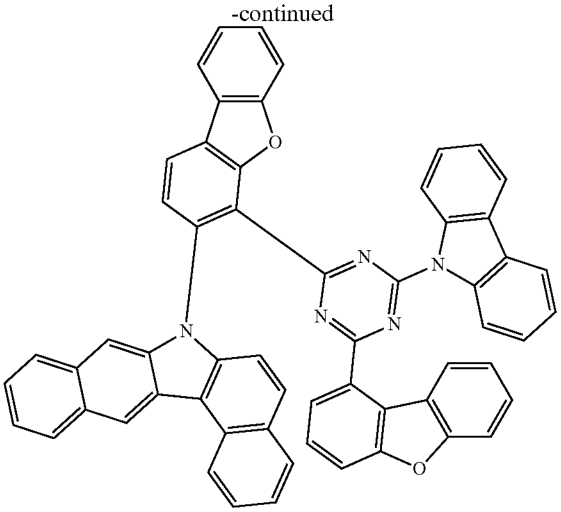
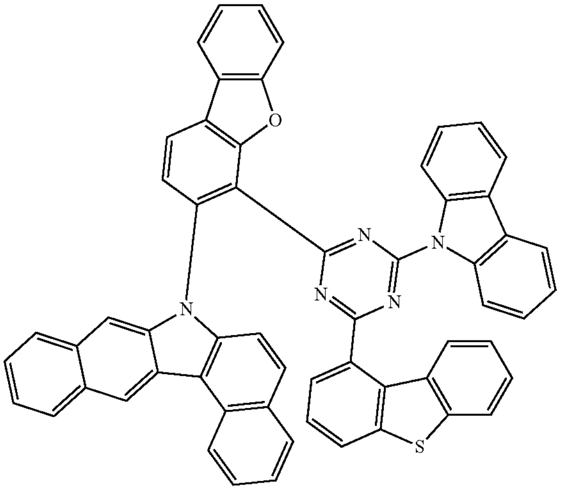
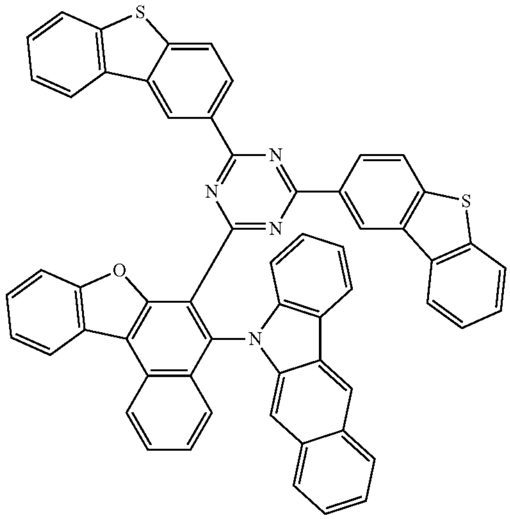
-continued
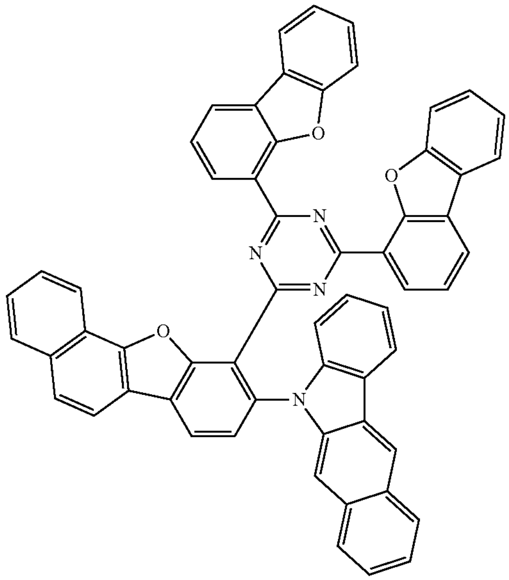
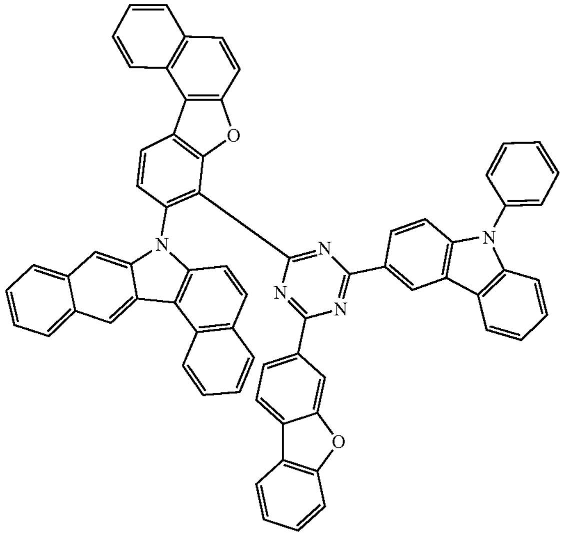
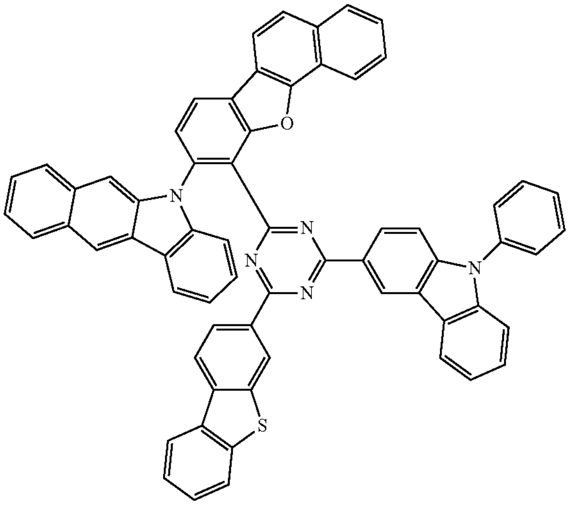

-continued
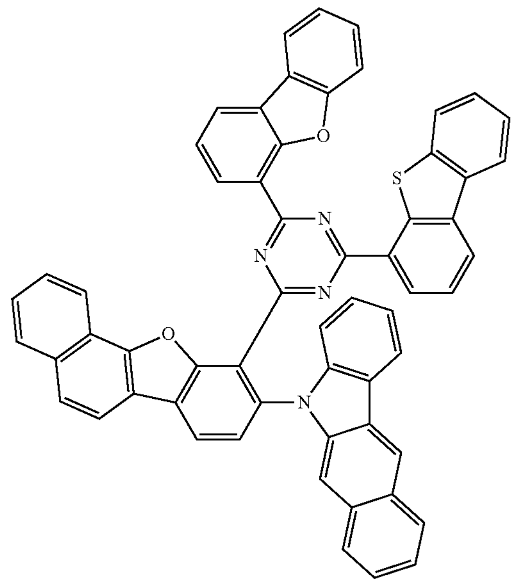
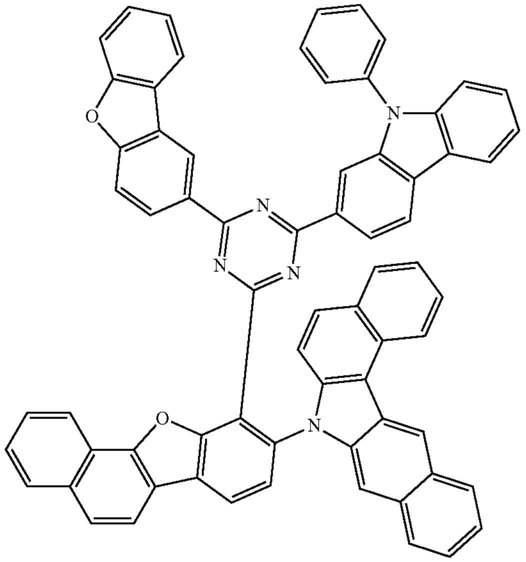
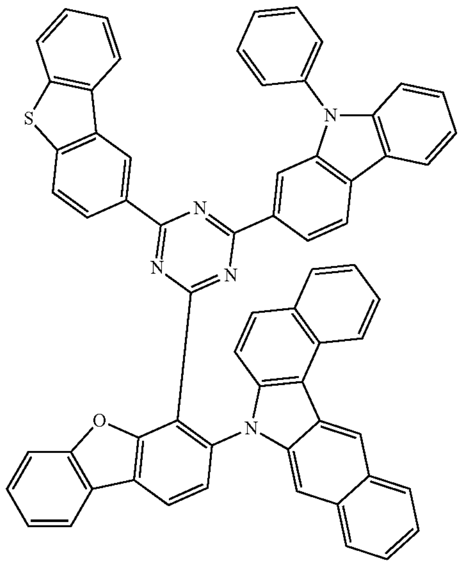
-continued
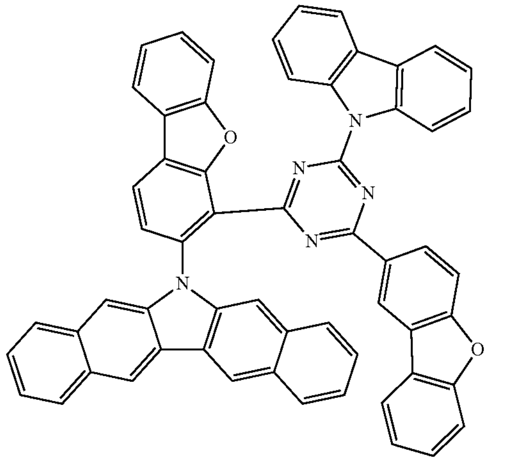
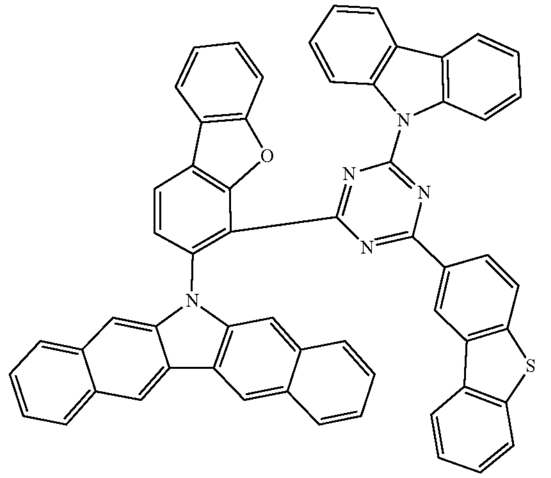
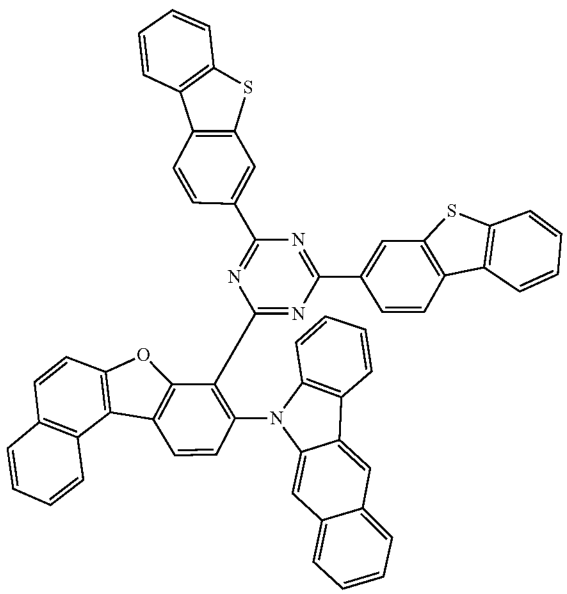

-continued
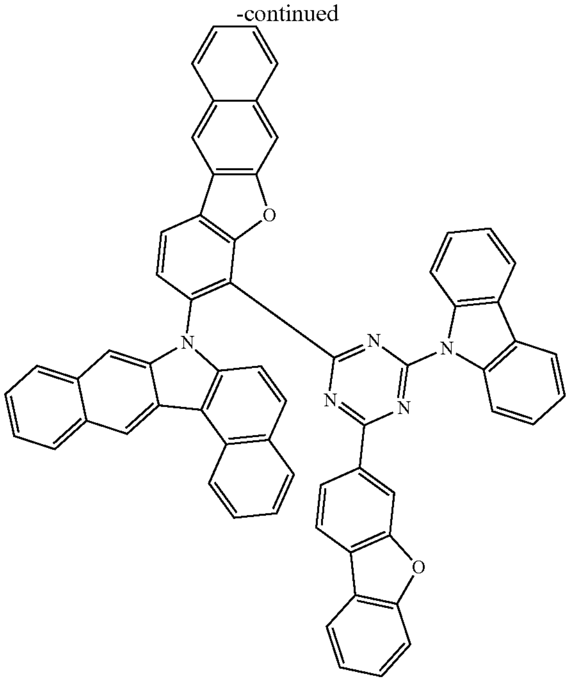
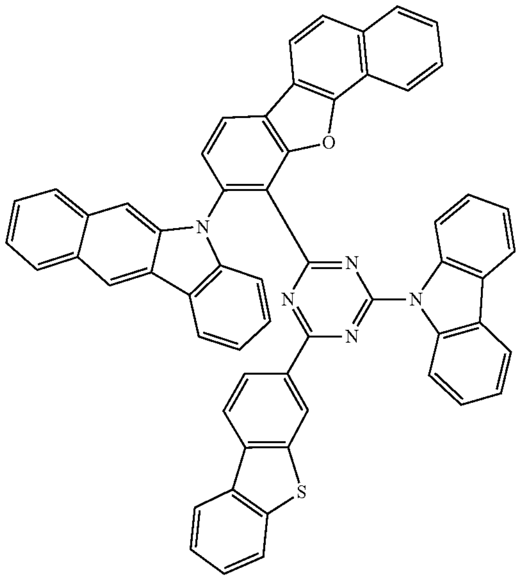
-continued
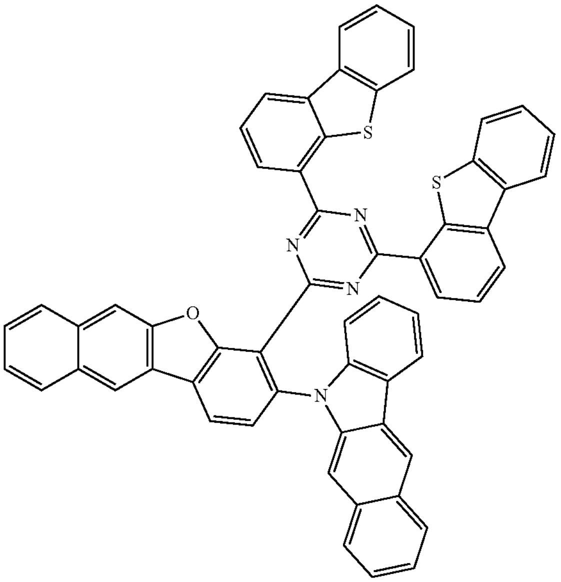
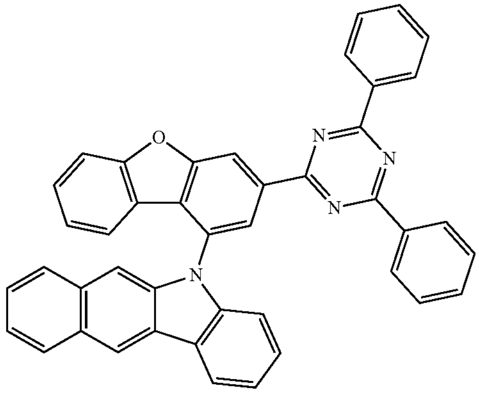
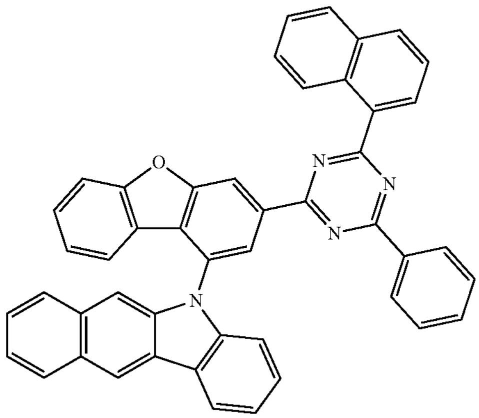

-continued
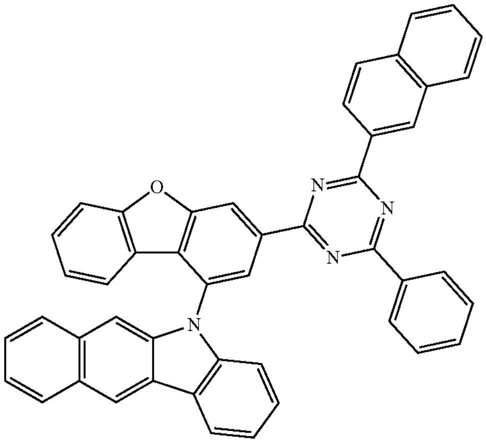
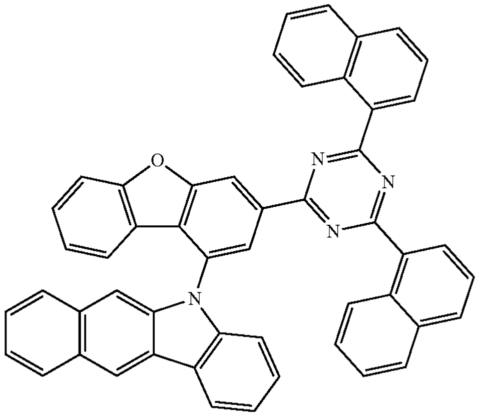
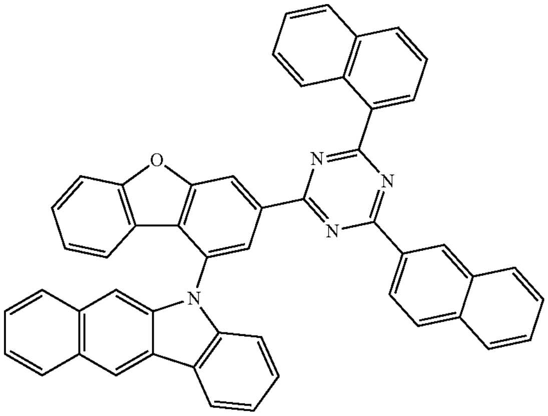
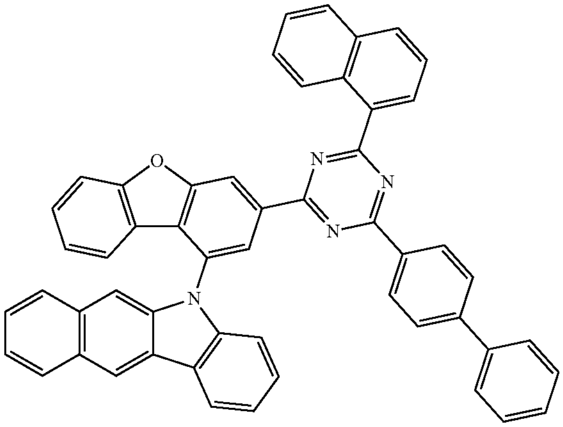
-continued
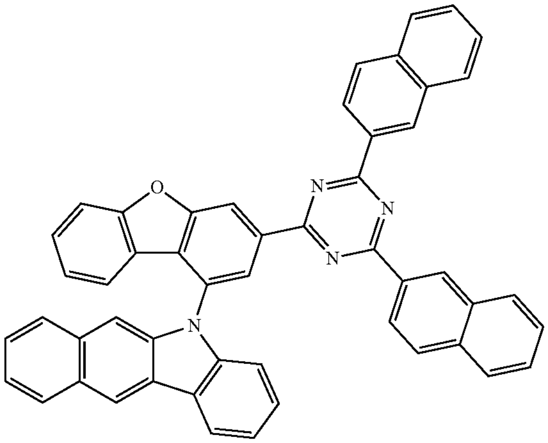
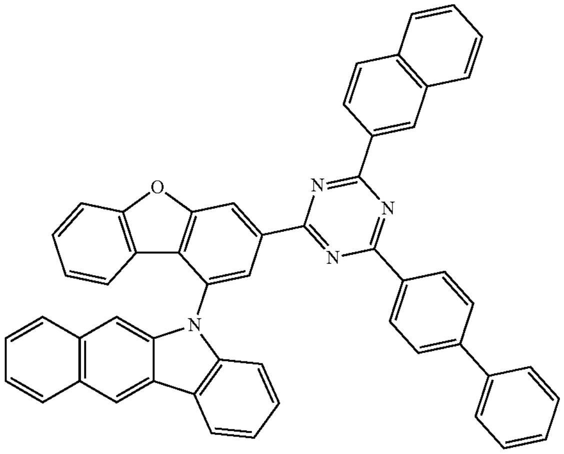
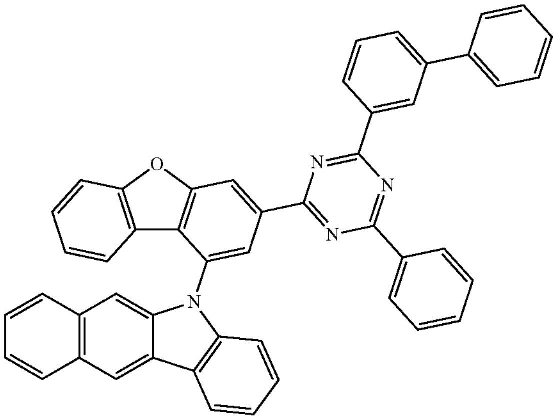

-continued
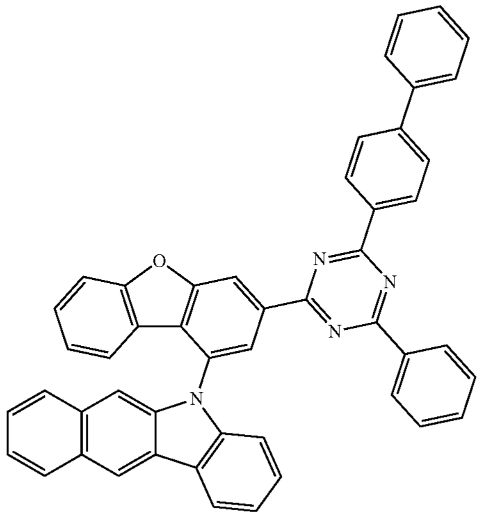
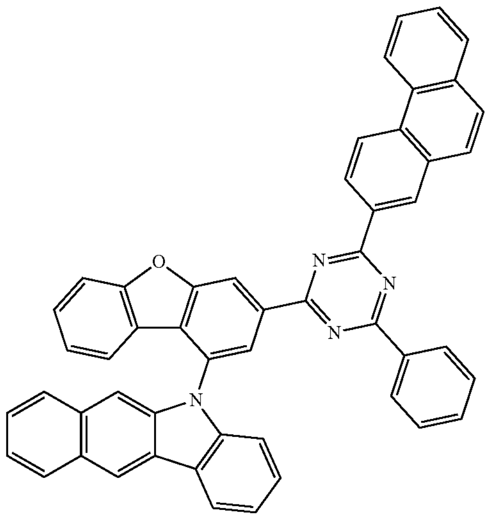
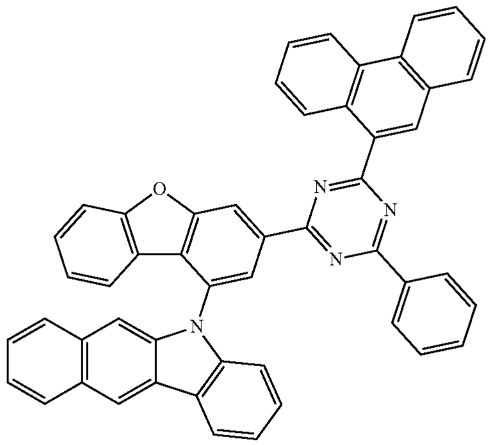
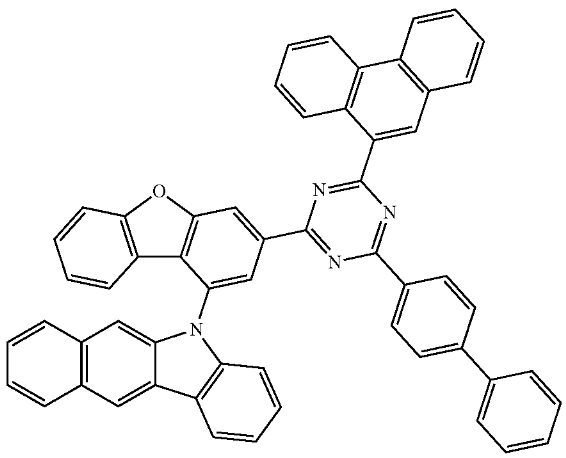
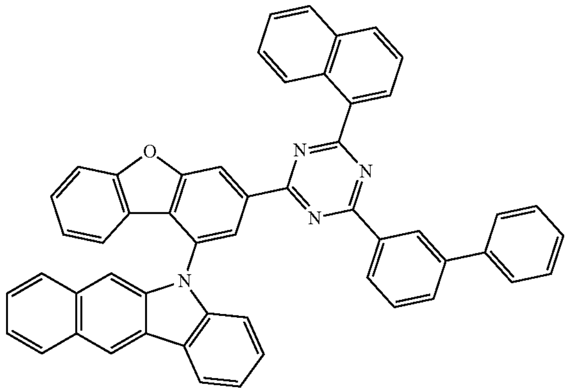
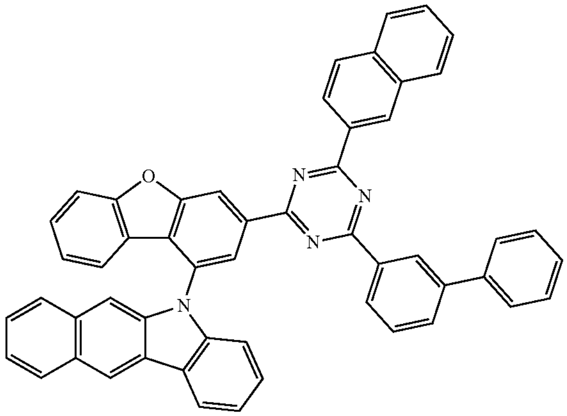
-continued -continued
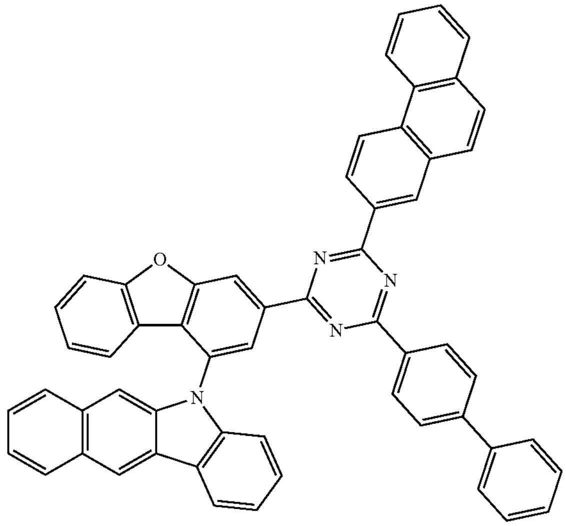
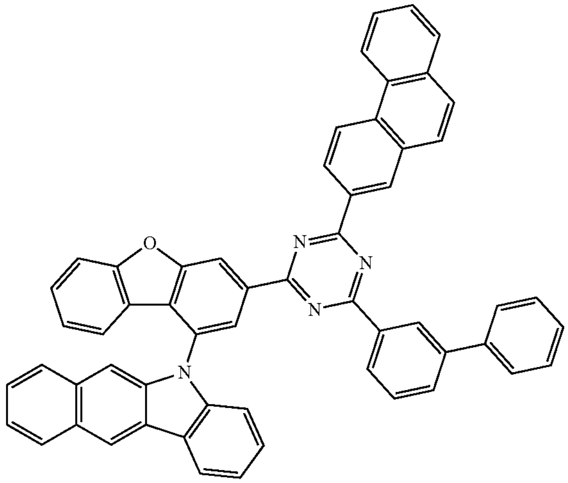
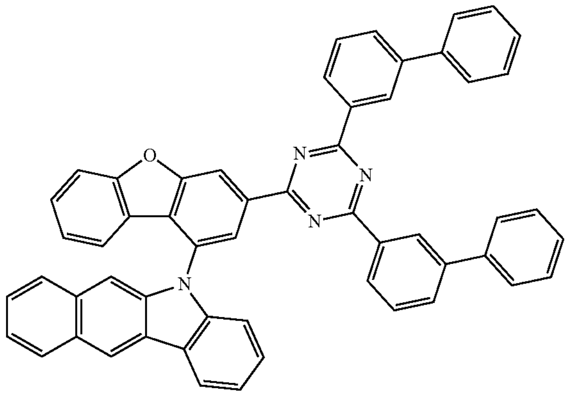
-continued
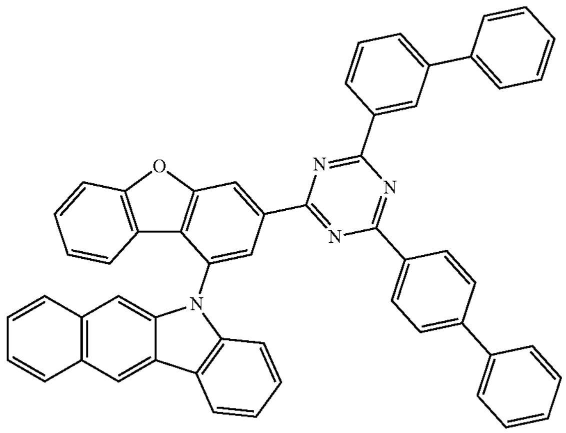
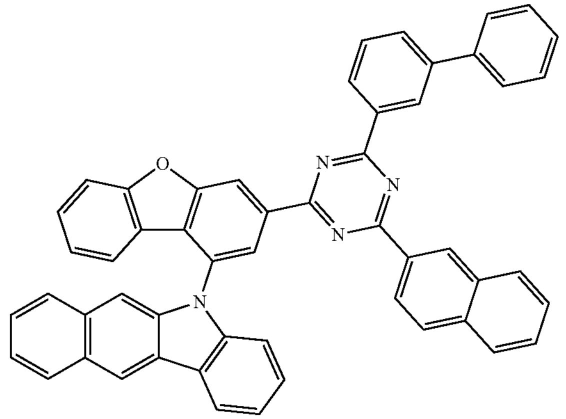
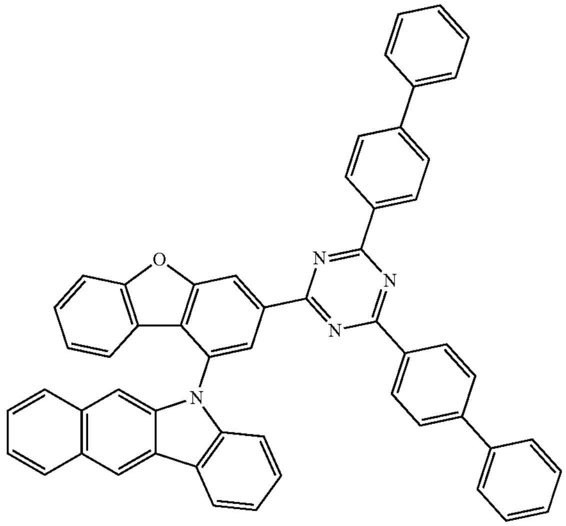

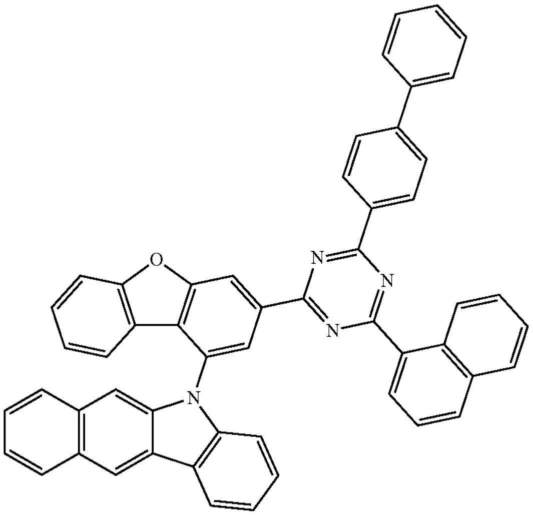
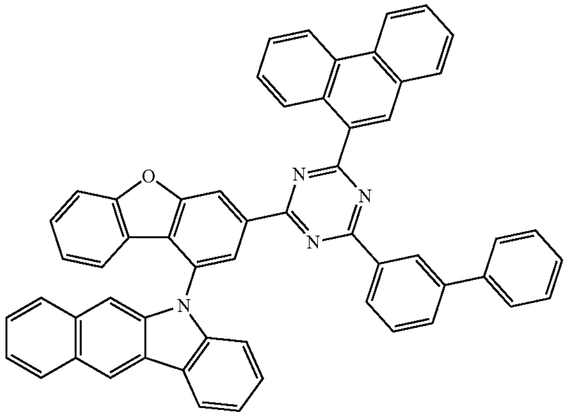
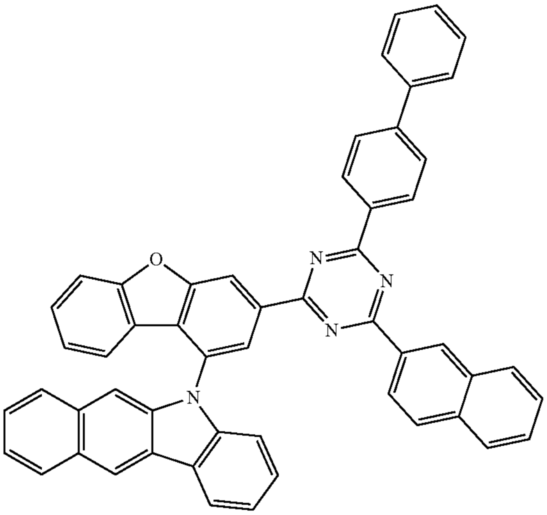
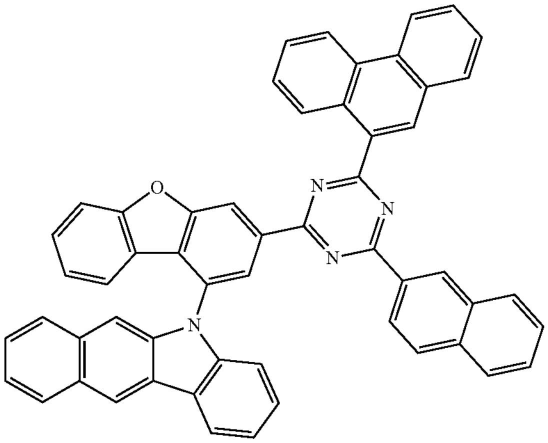
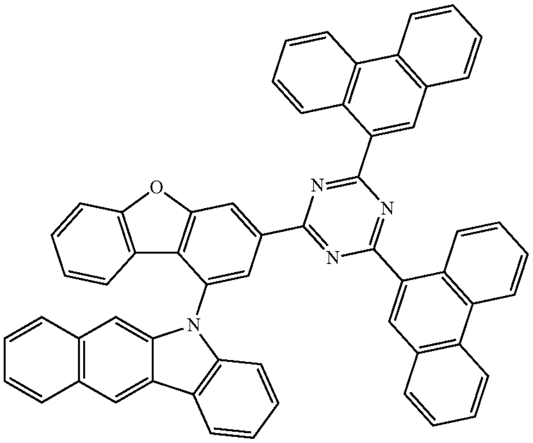
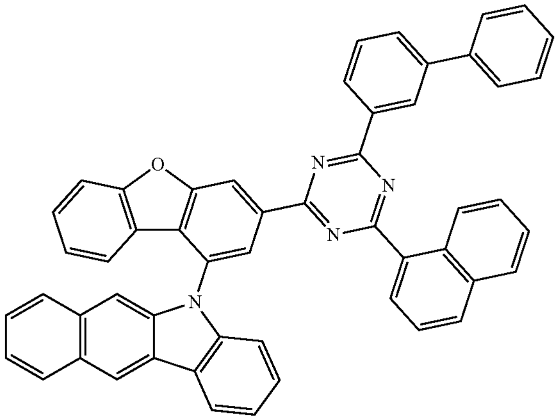

-continued
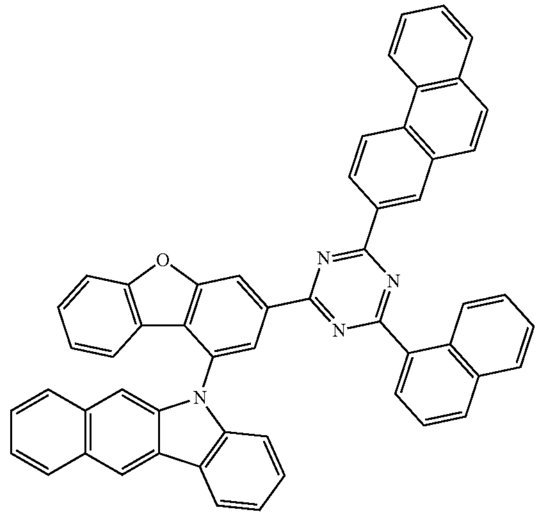
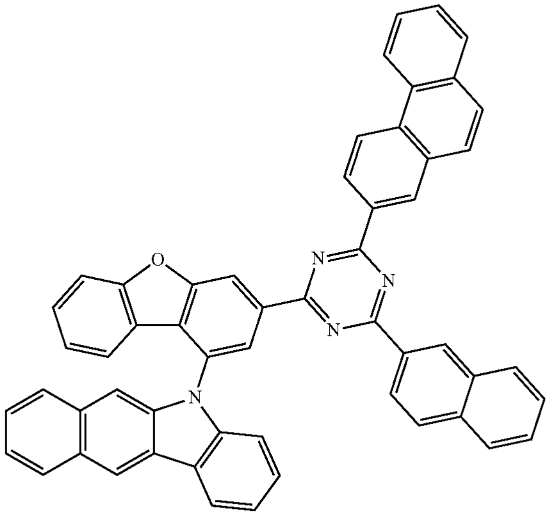
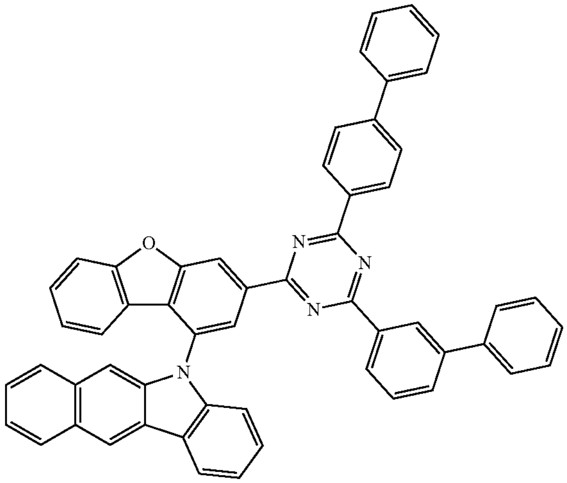
-continued
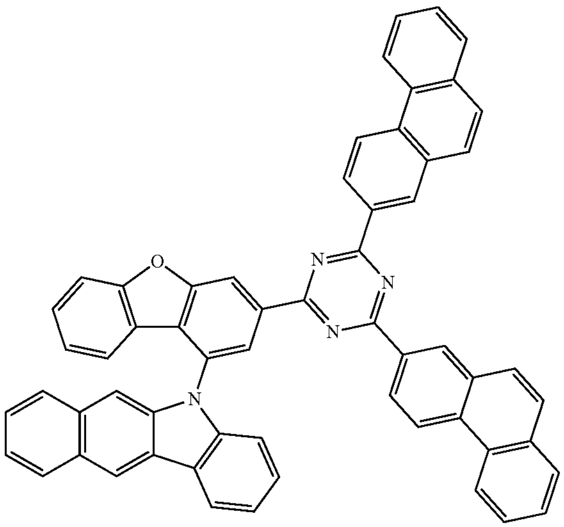
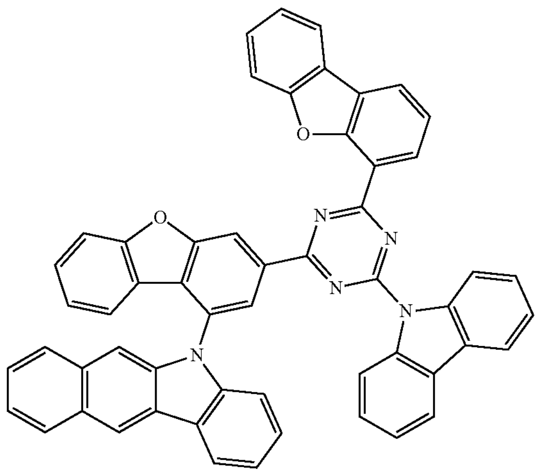
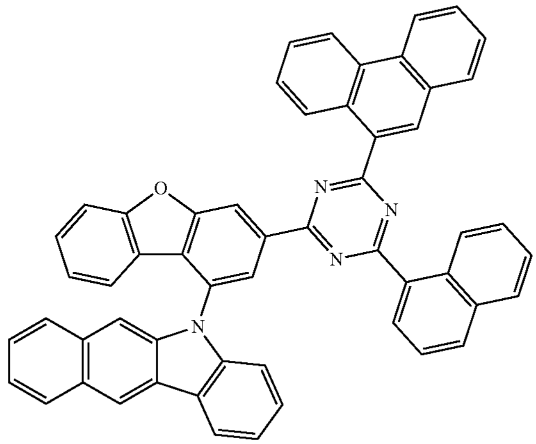

-continued
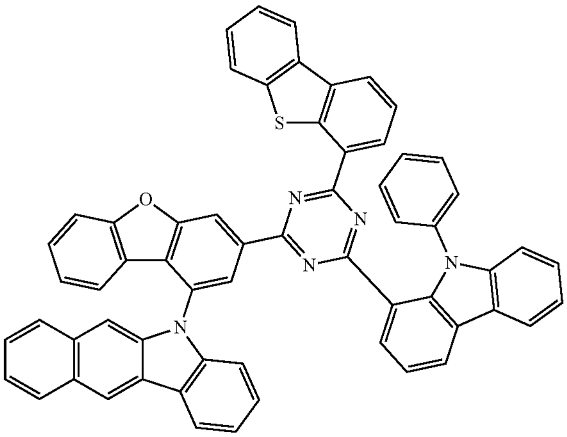
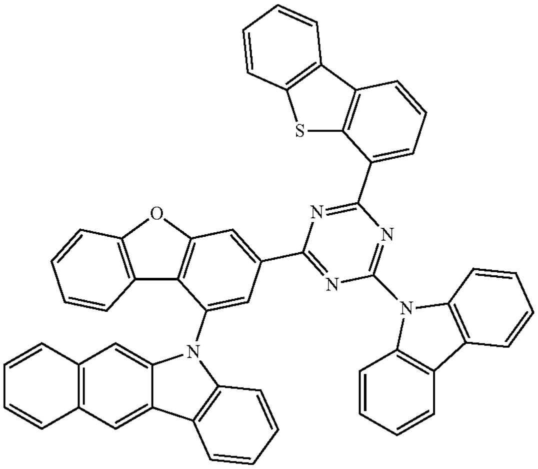
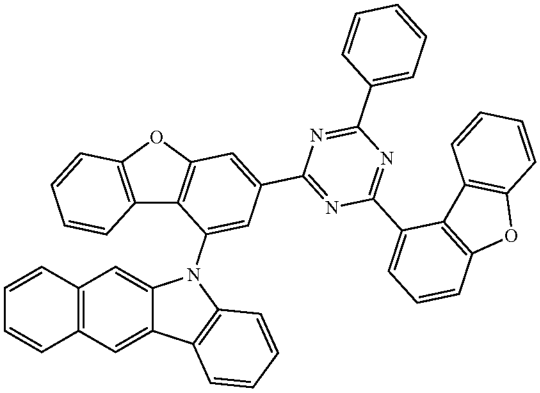
-continued
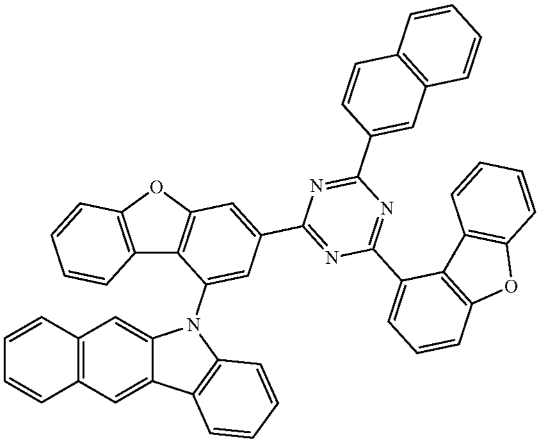
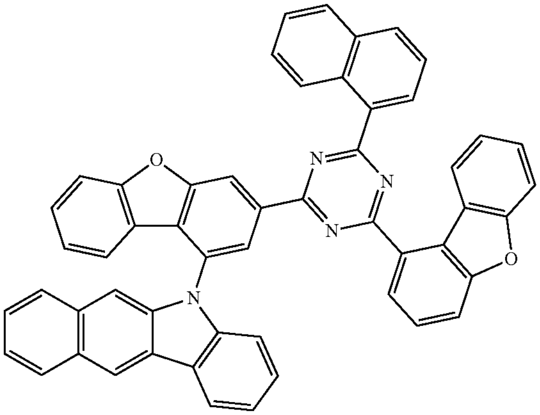
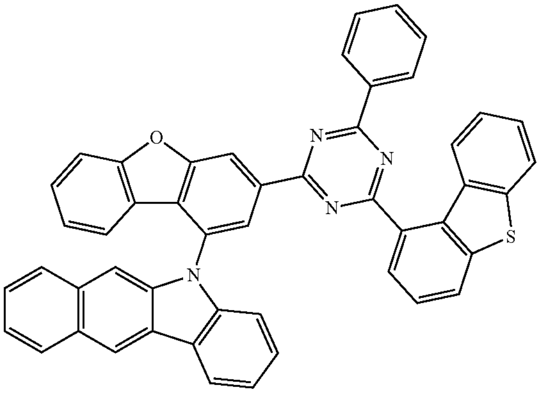
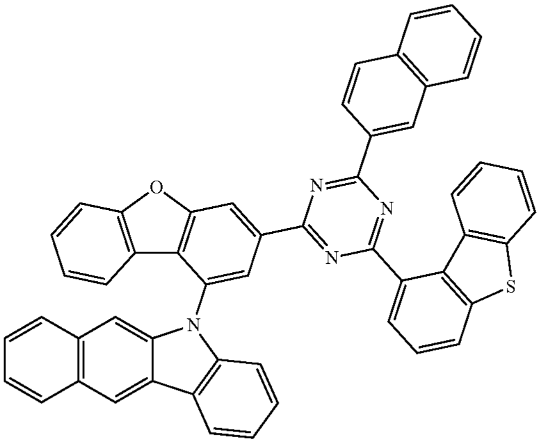

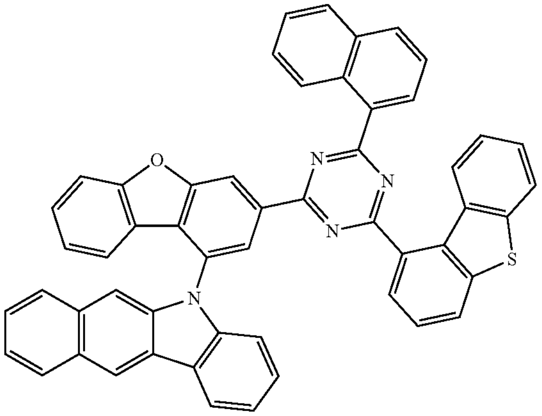
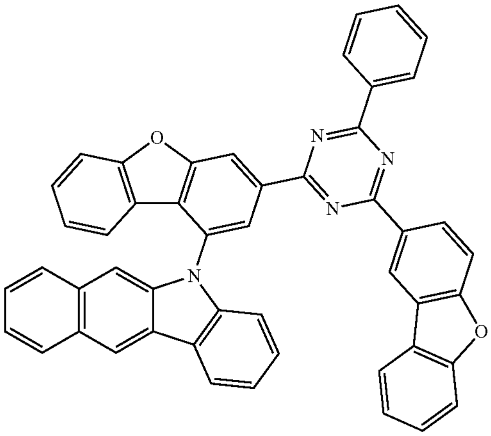
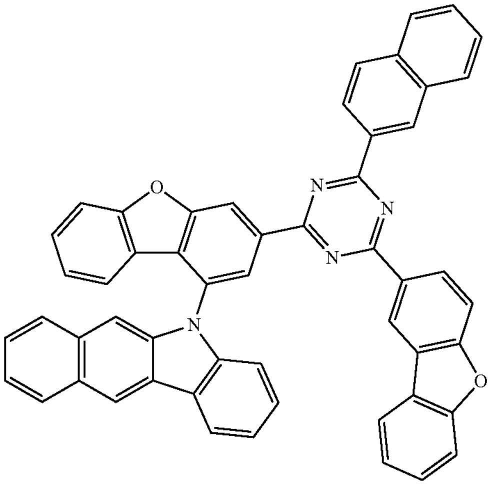
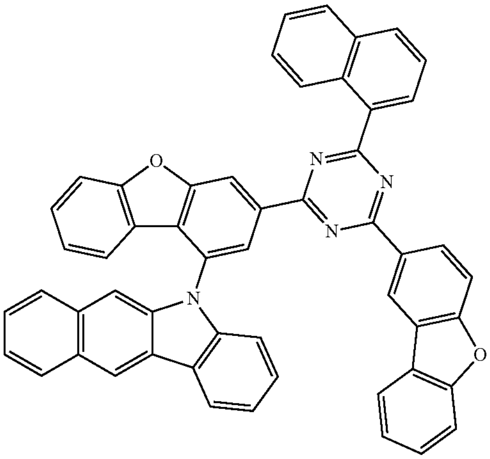
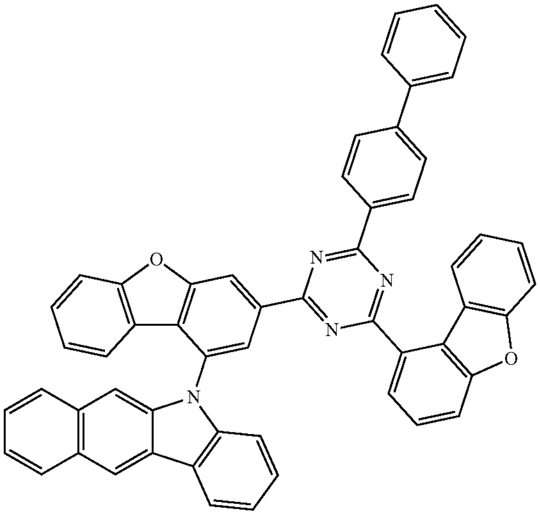
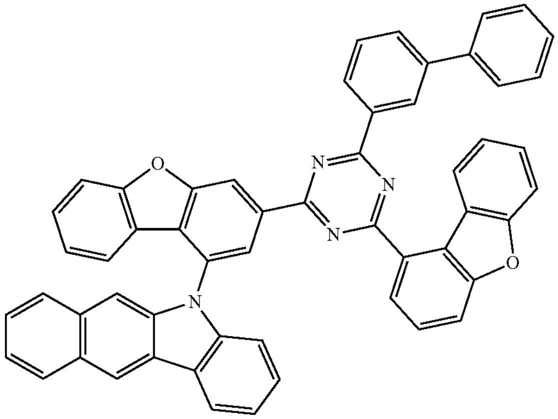

-continued
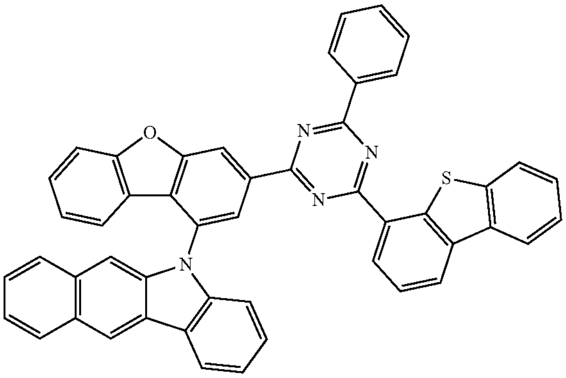
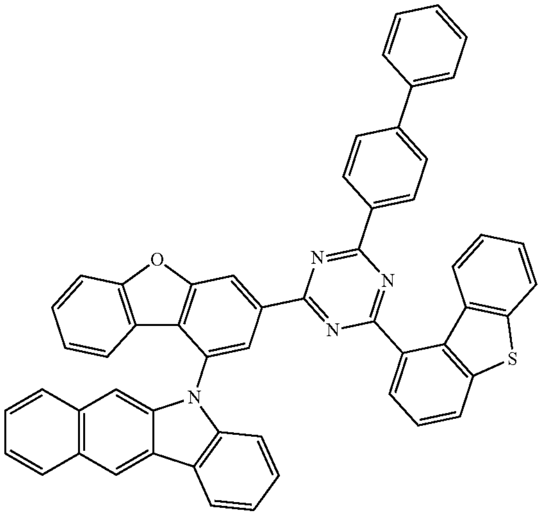
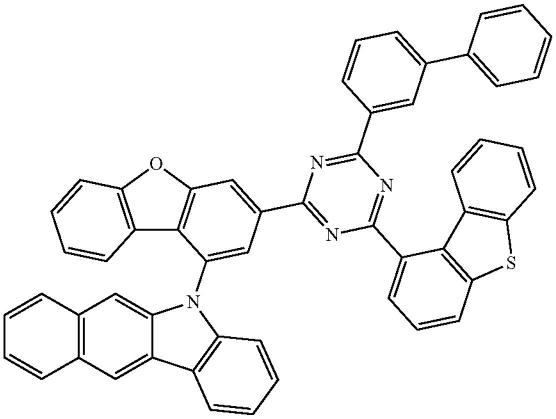
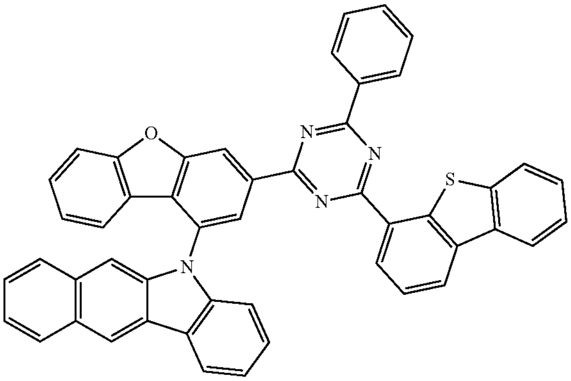
-continued
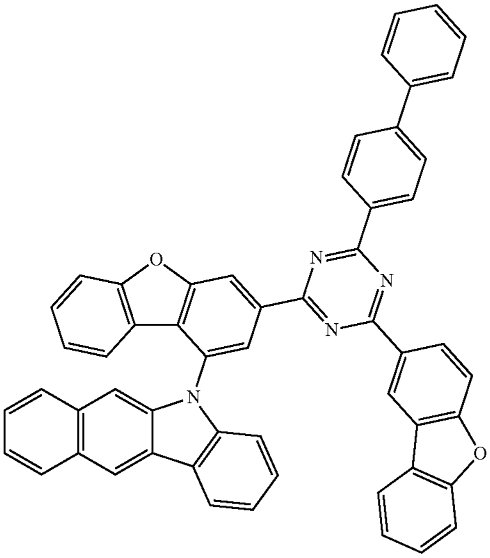
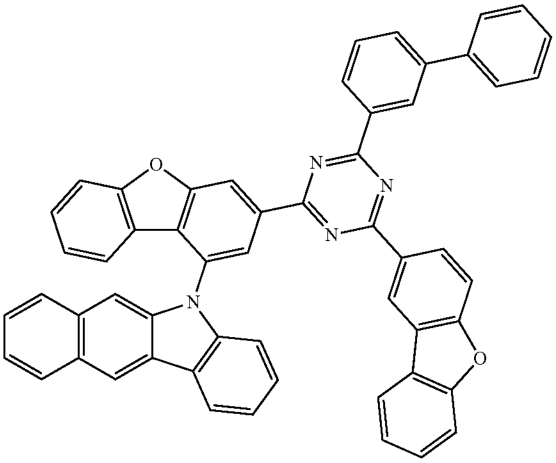
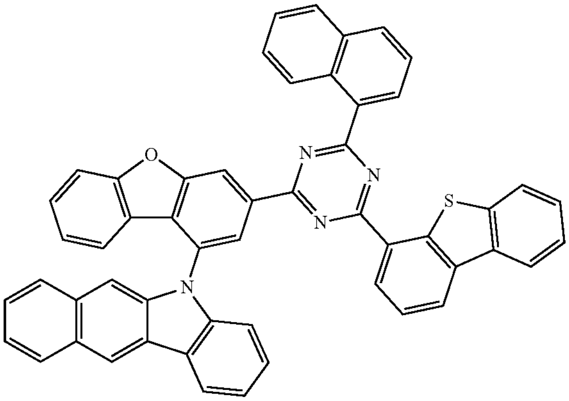

-continued
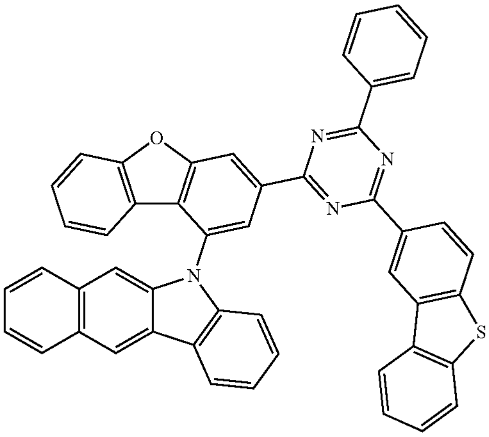
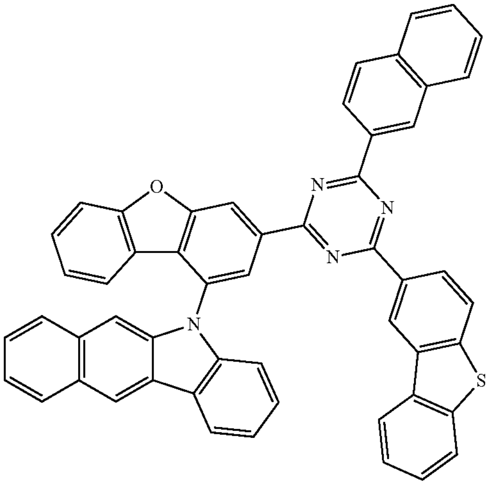
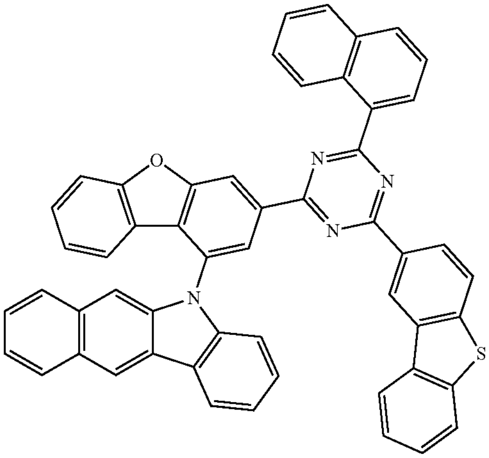
-continued
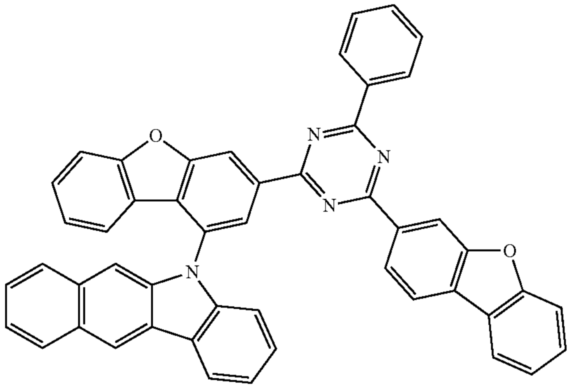
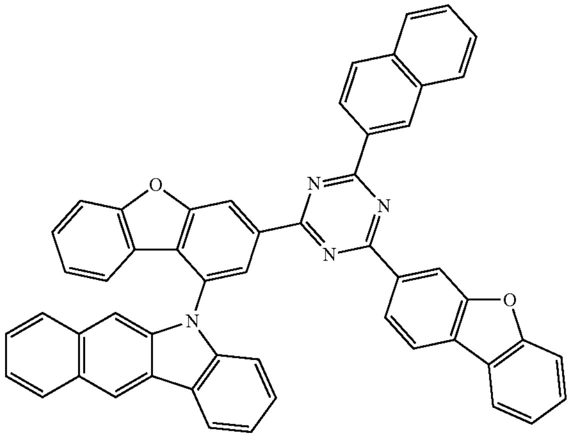
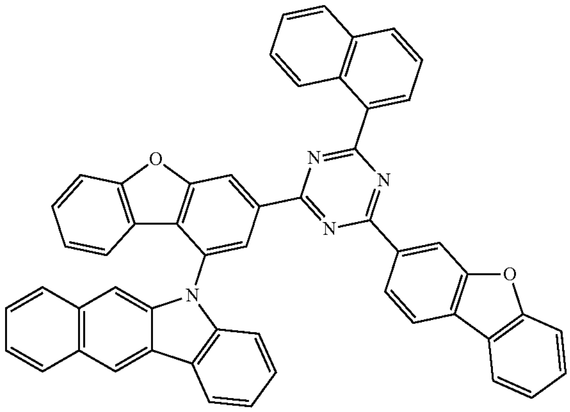
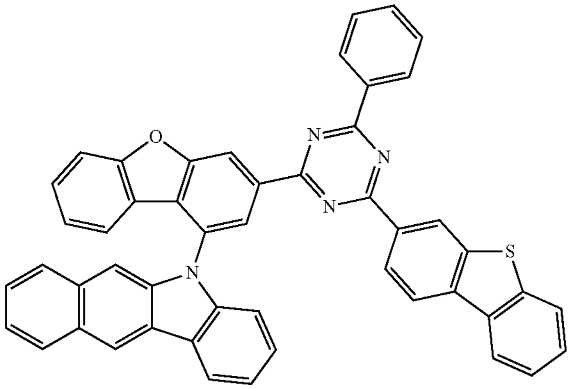

-continued
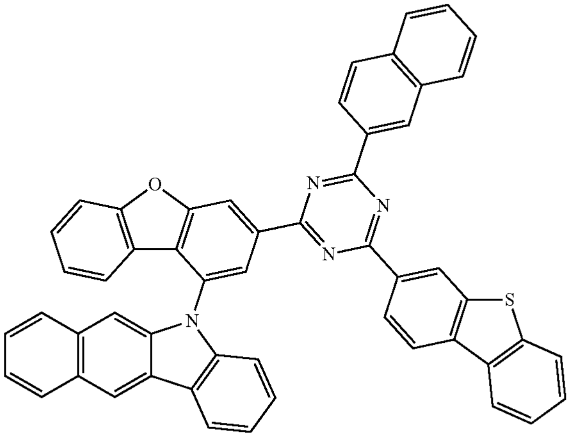
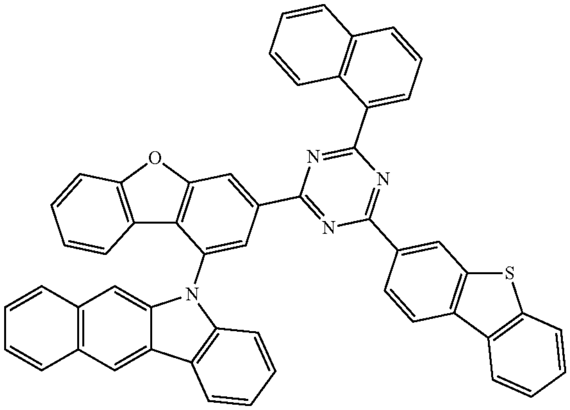
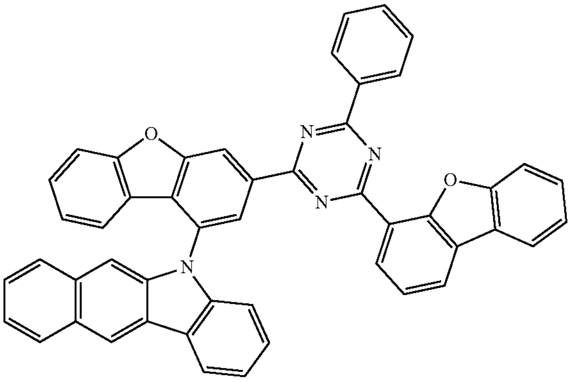
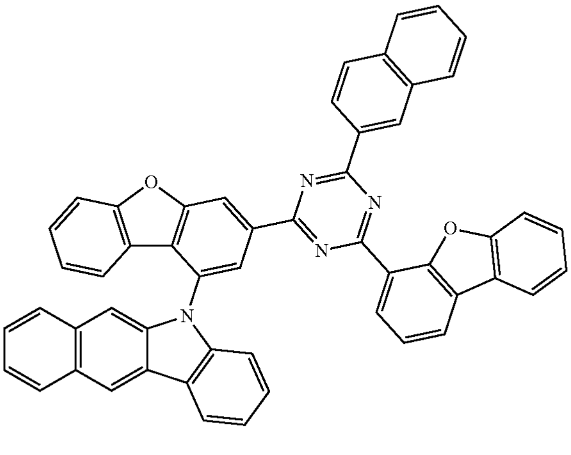
-continued
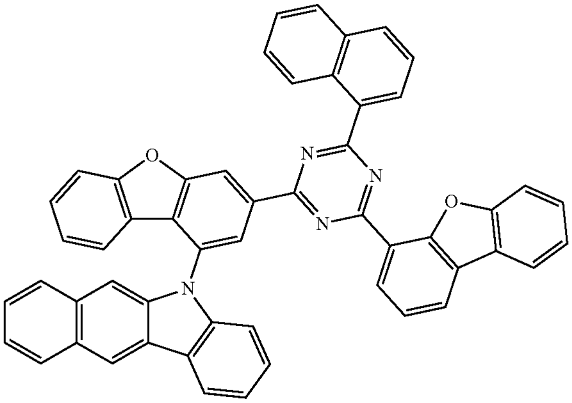
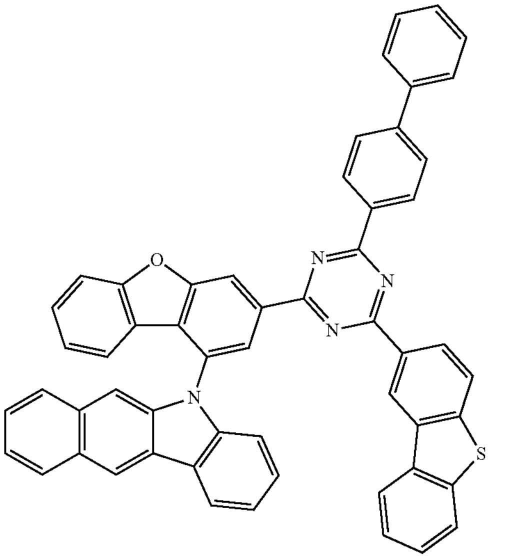
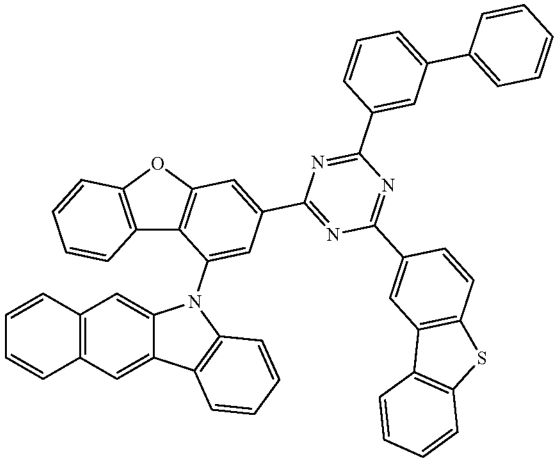

-continued
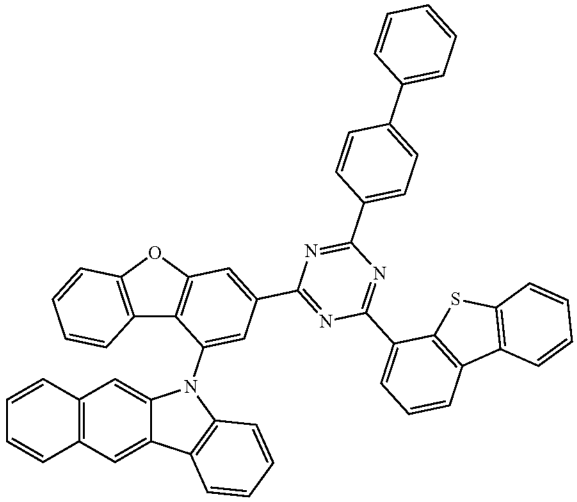
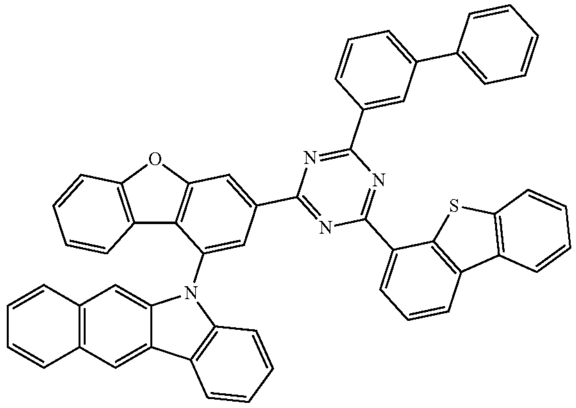
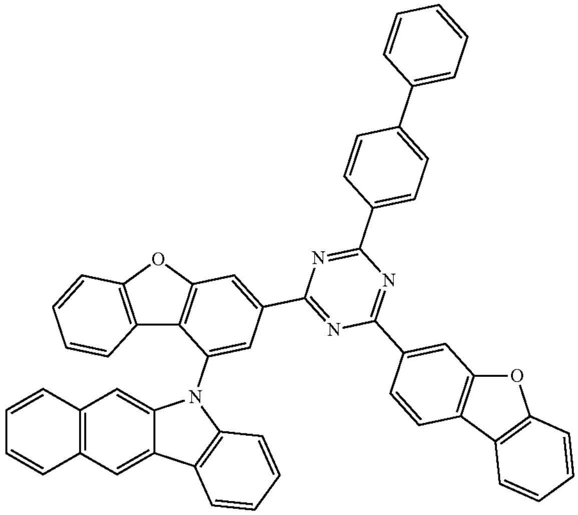
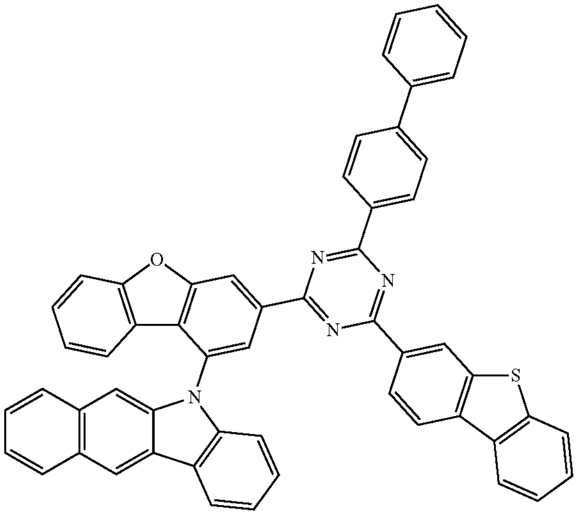
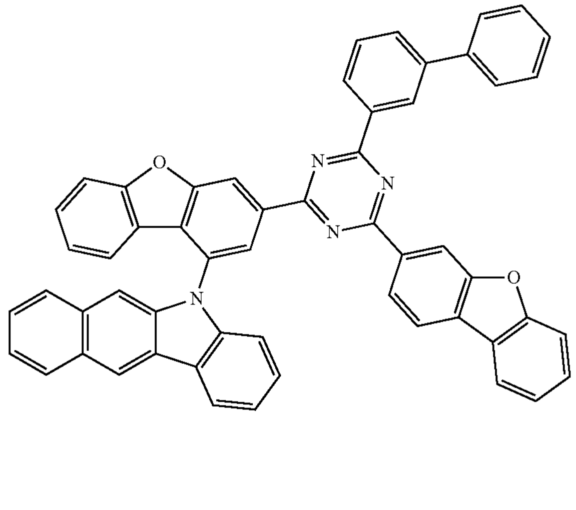
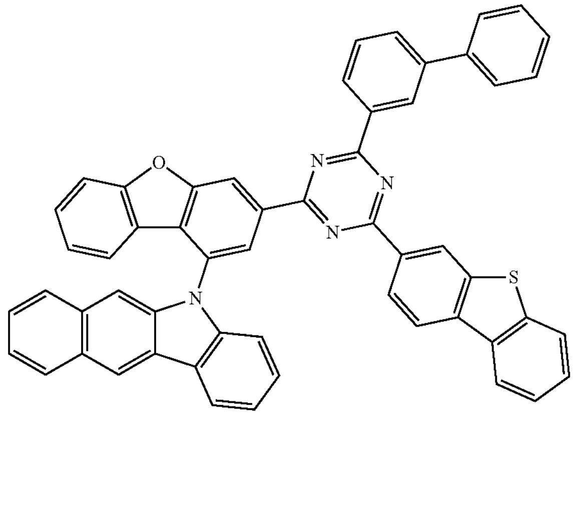

-continued
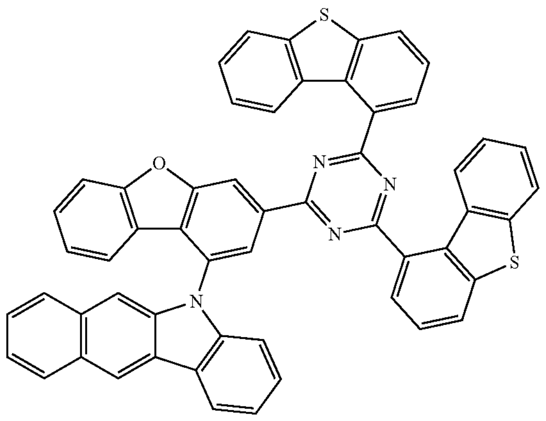
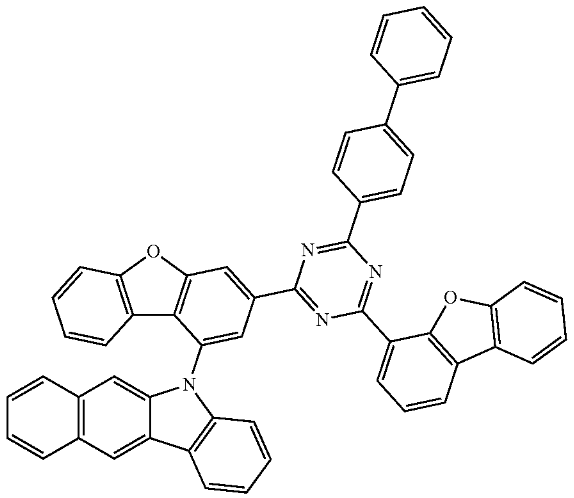
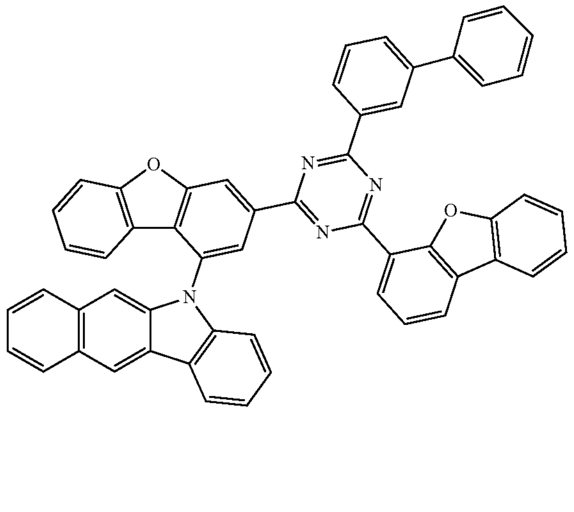
-continued
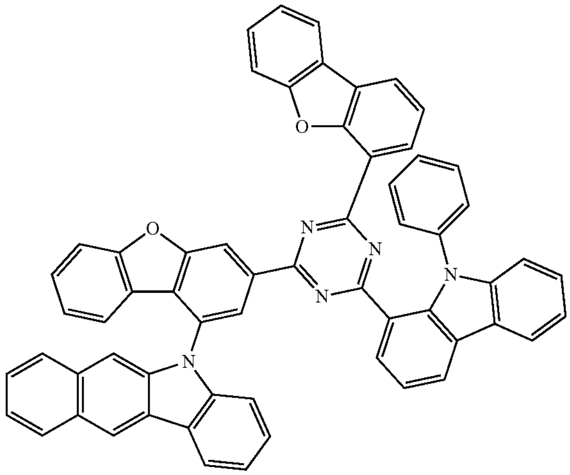
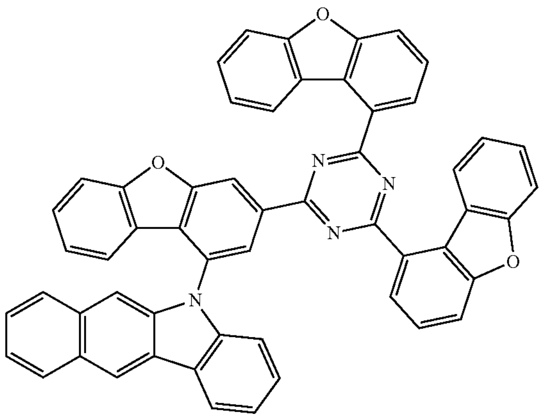
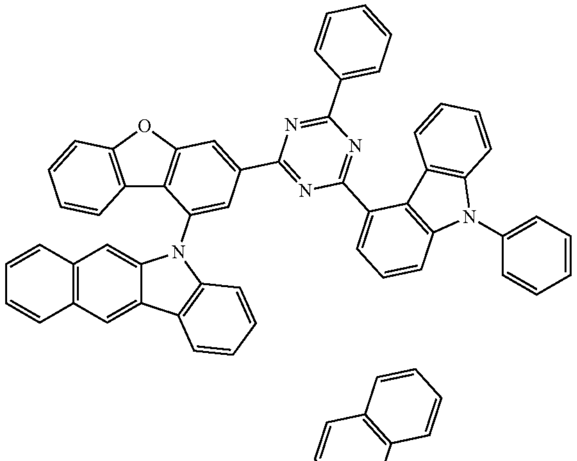
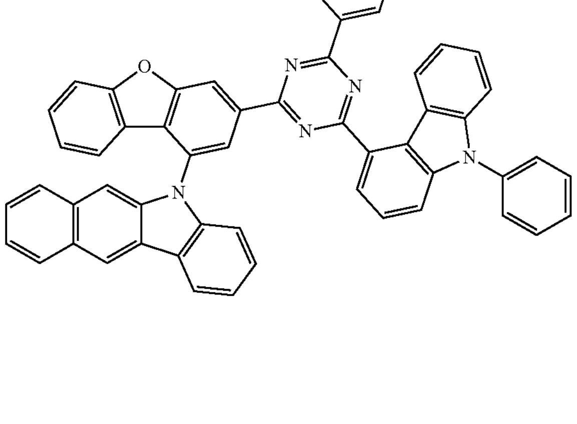

-continued
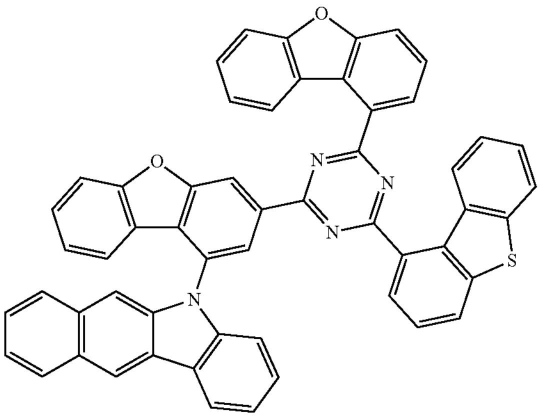
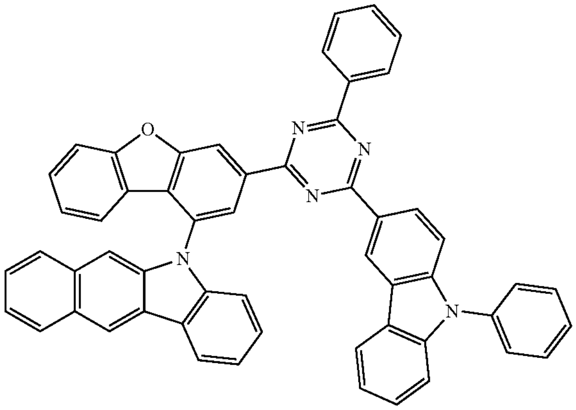
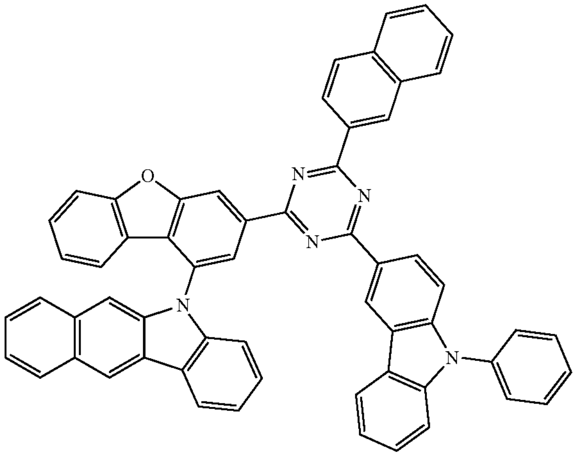
-continued
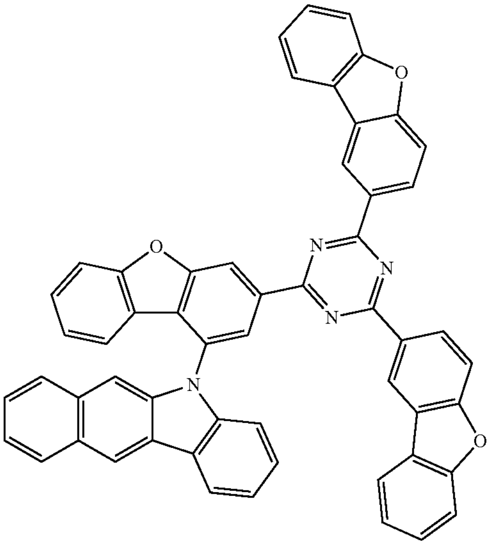
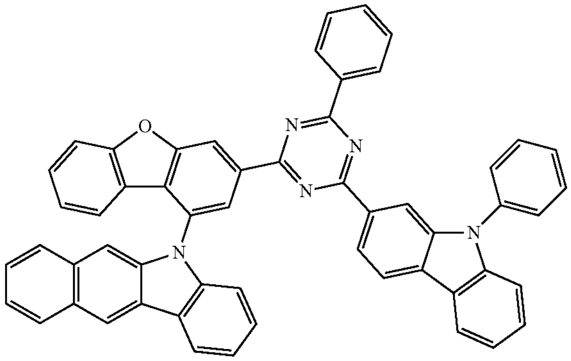
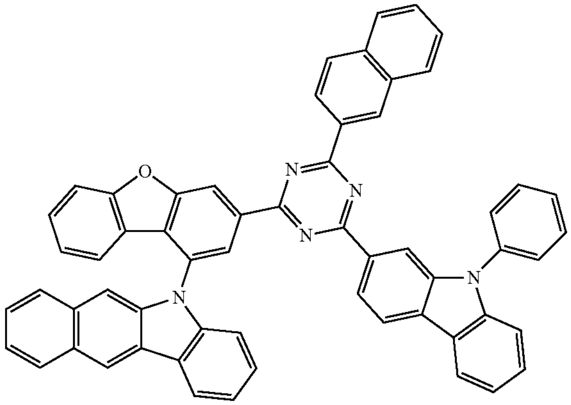
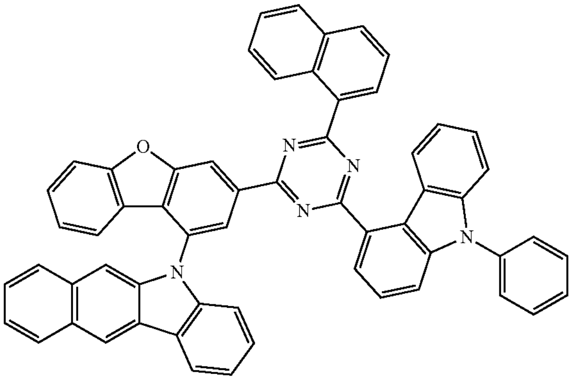

-continued
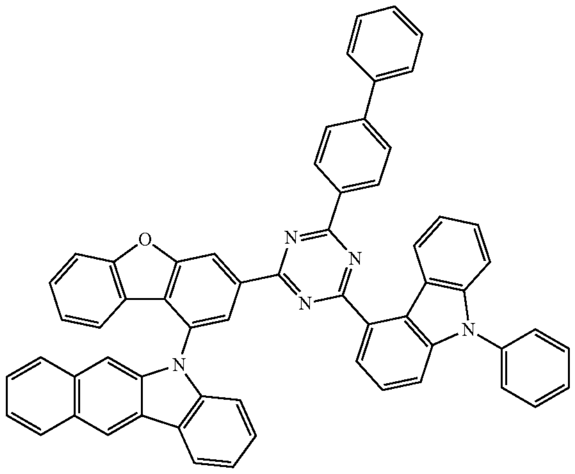
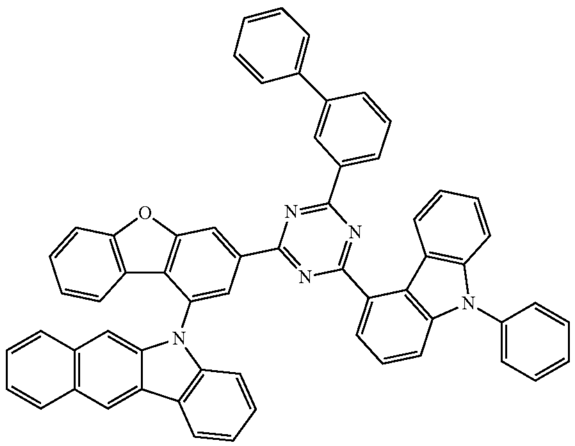
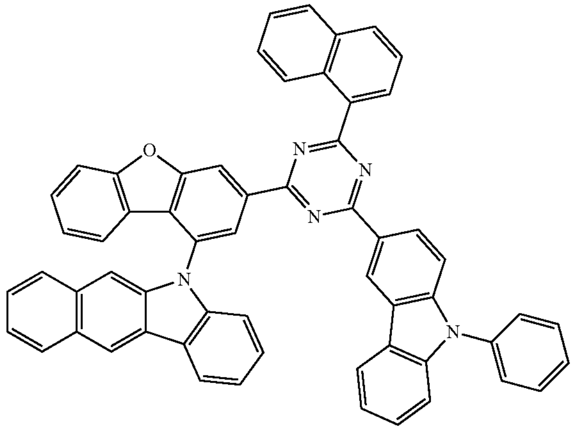
-continued
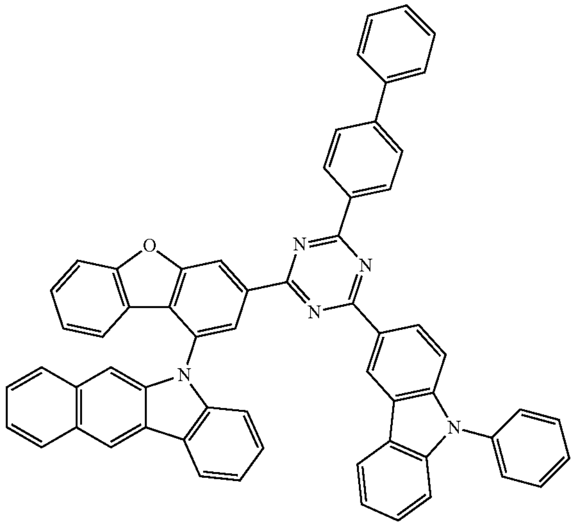
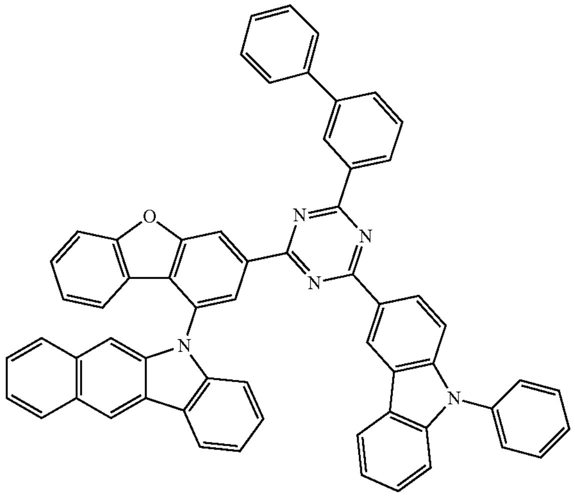
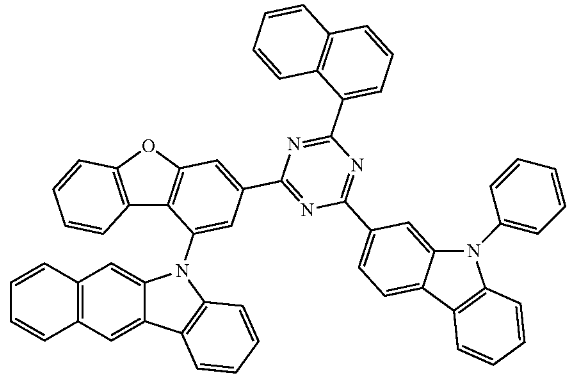

-continued
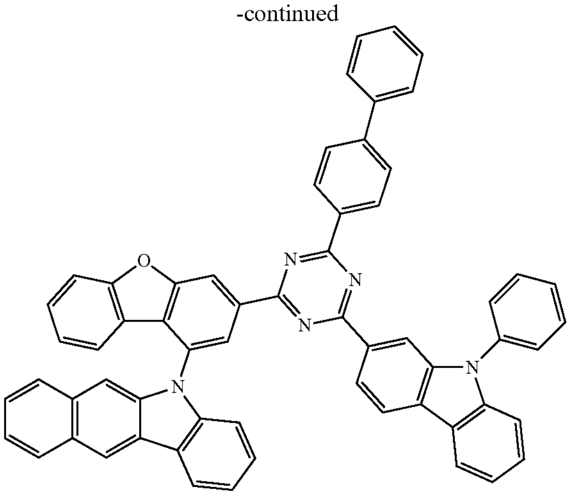
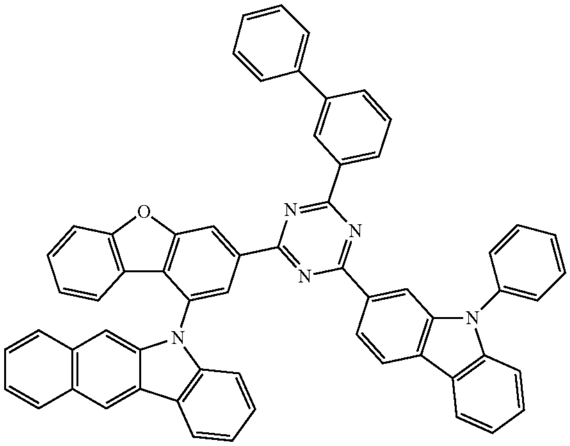
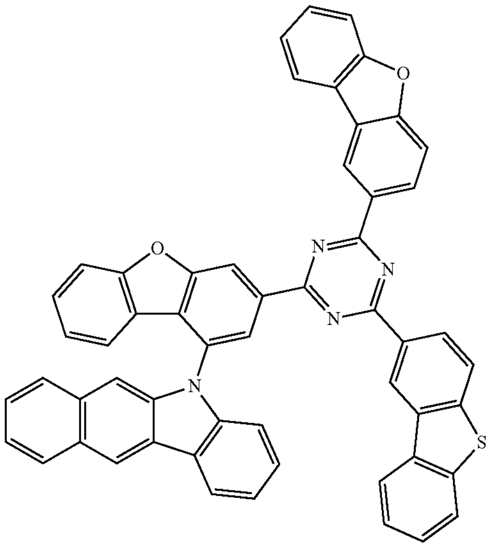
-continued
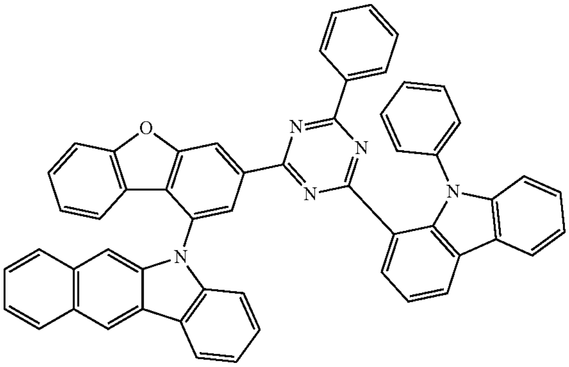
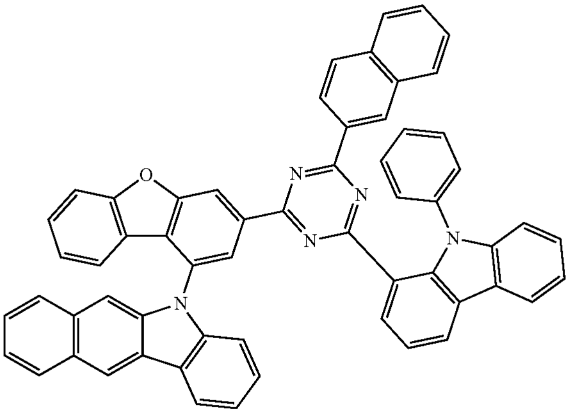
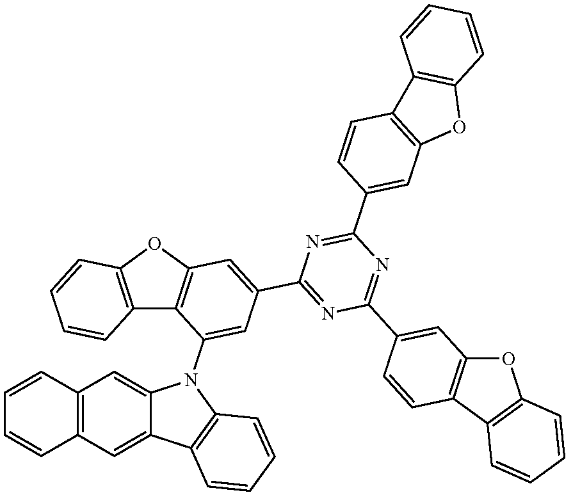
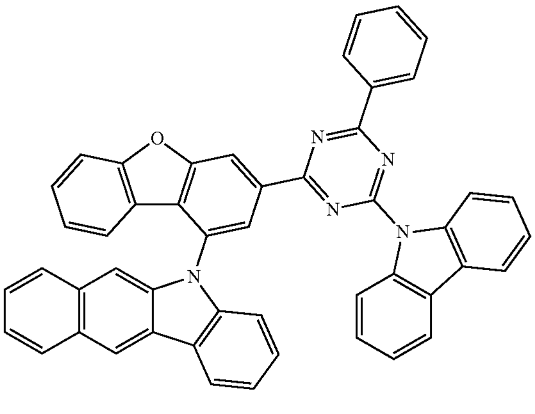

-continued
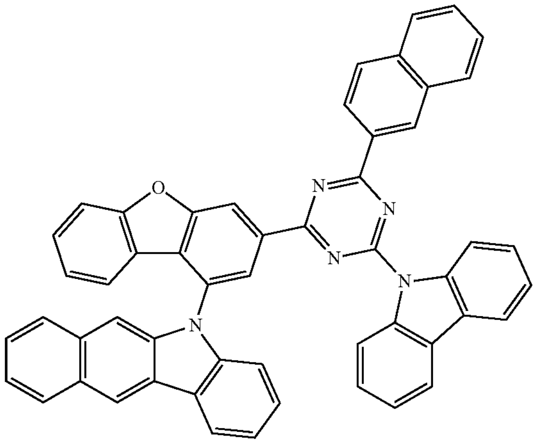
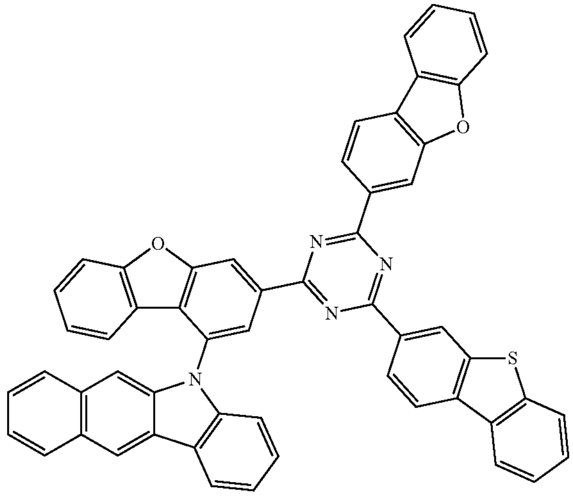
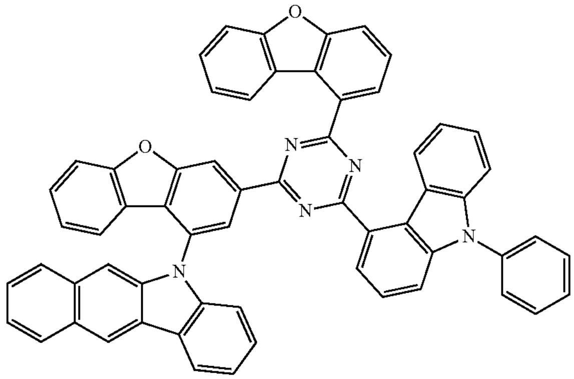
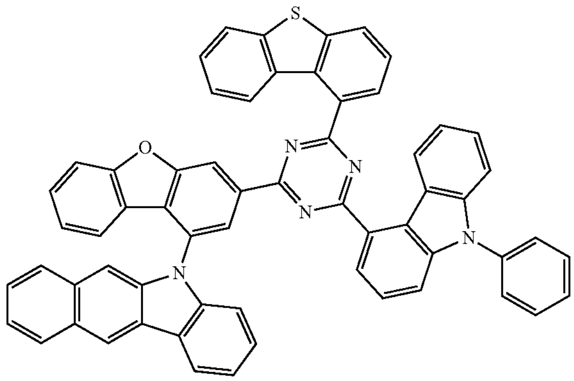
-continued
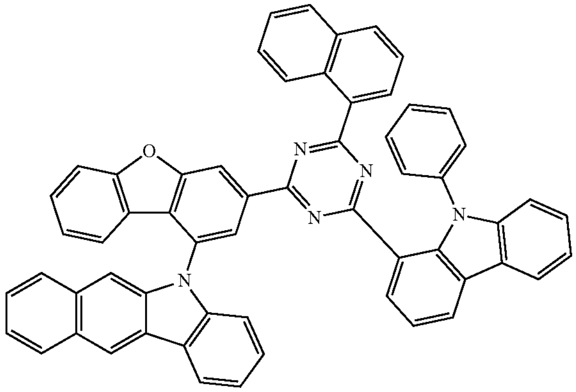
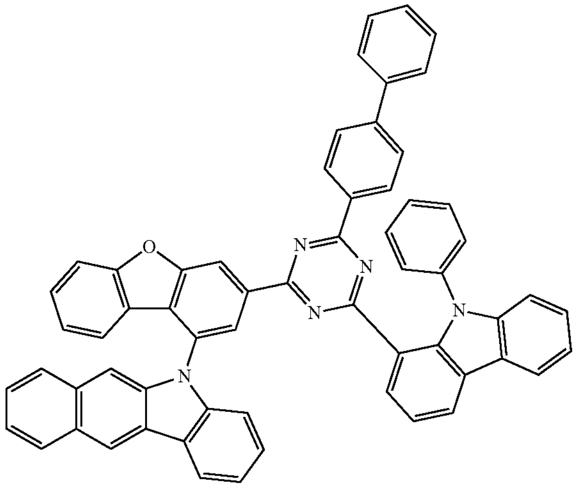
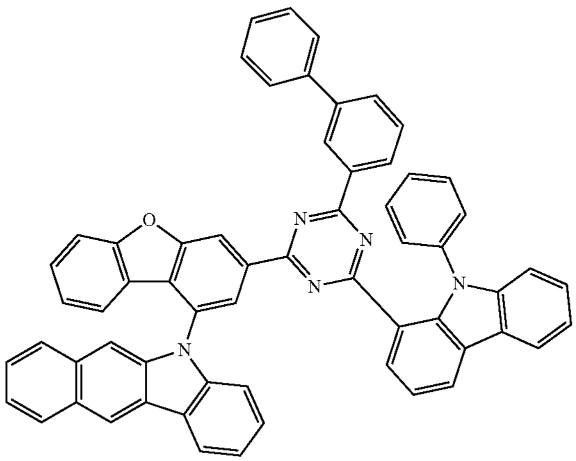

-continued
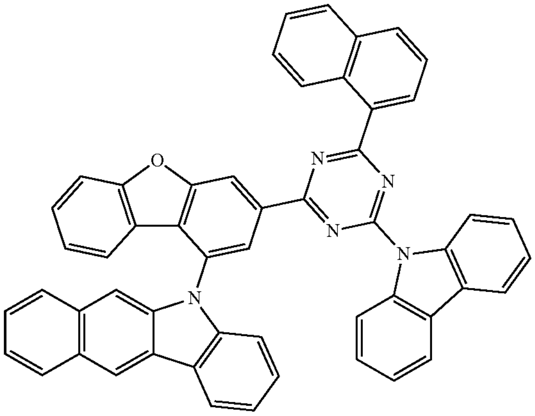
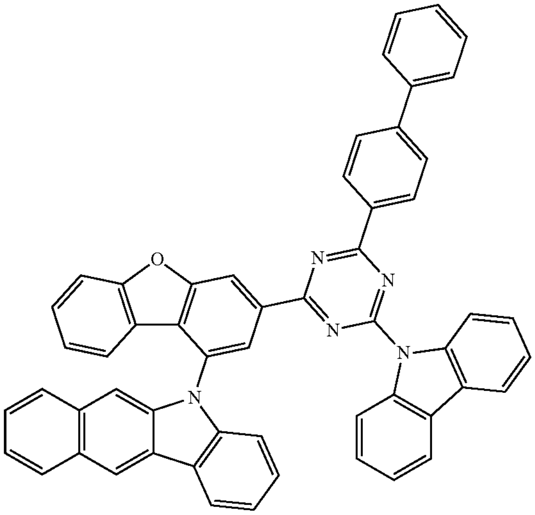
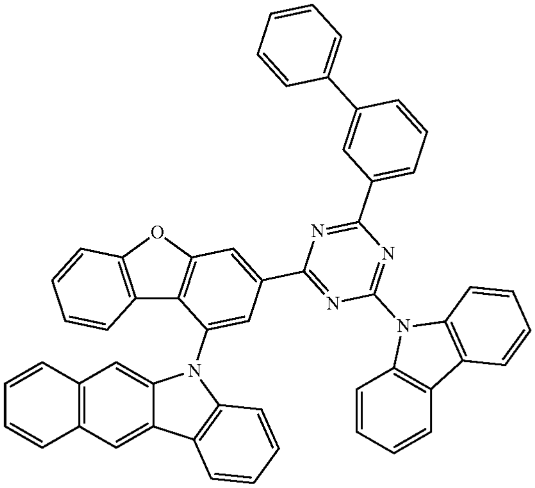
-continued
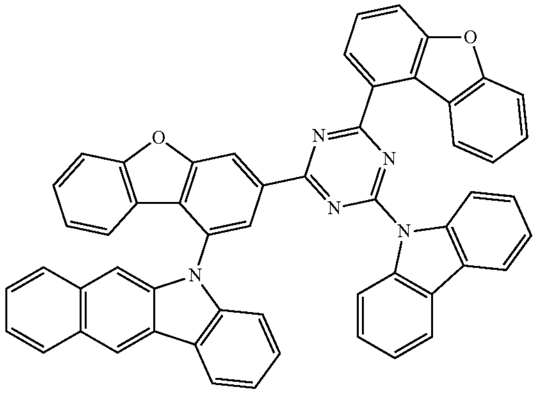
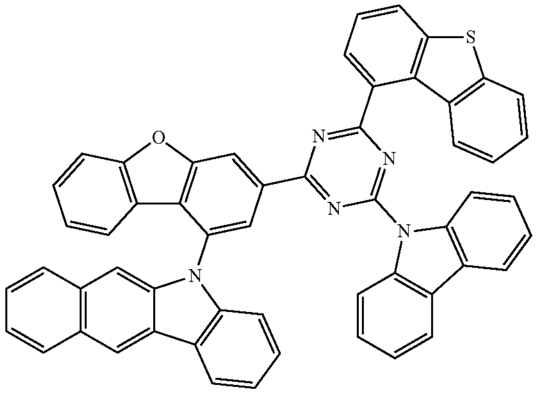
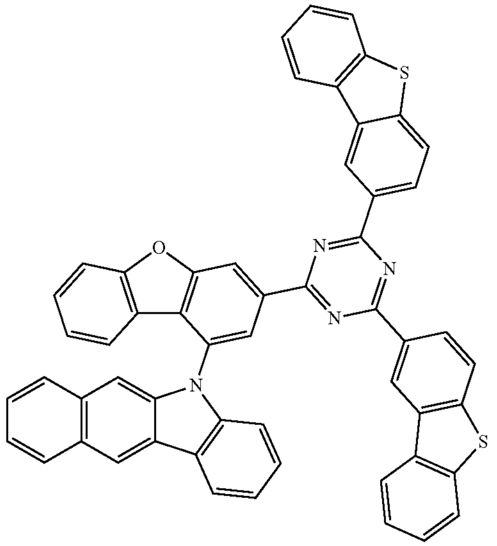
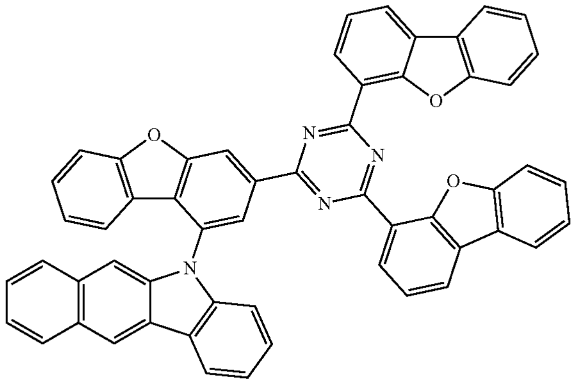

-continued
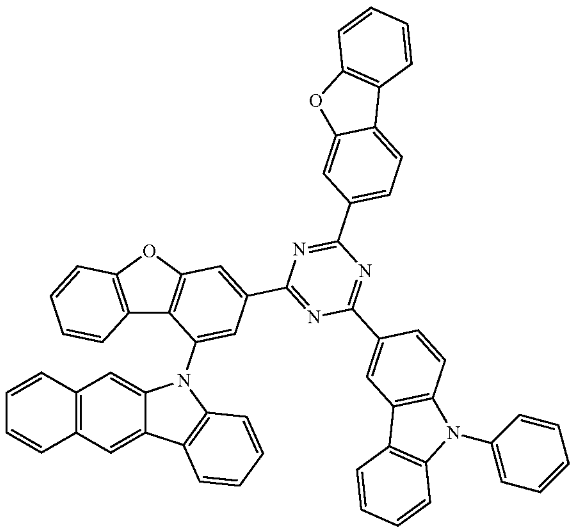
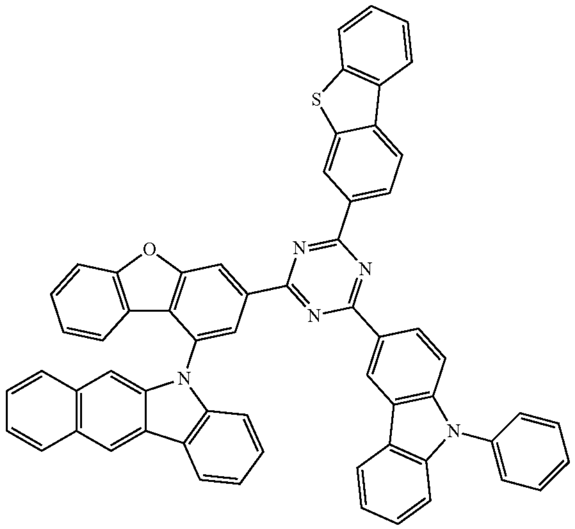
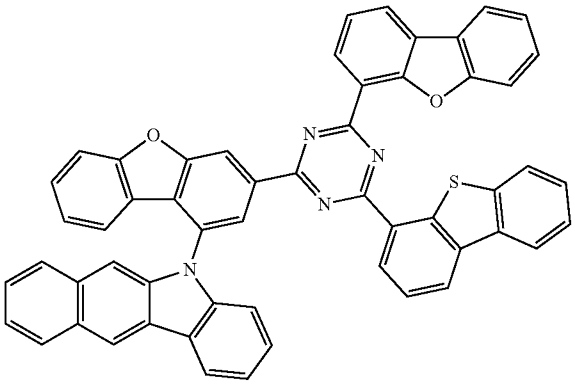
-continued
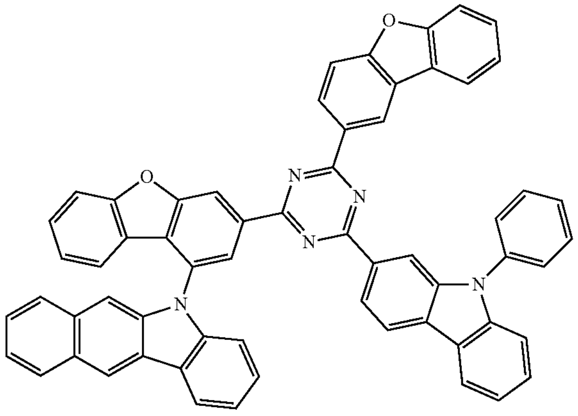
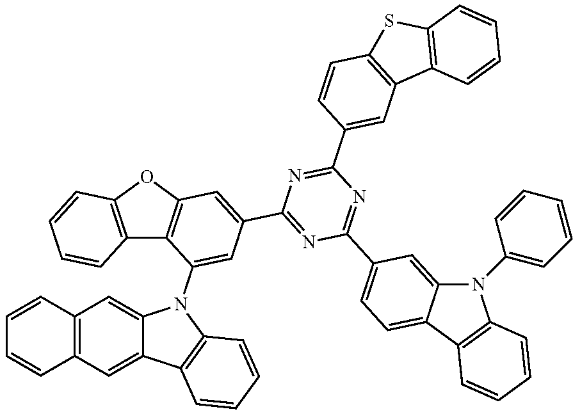
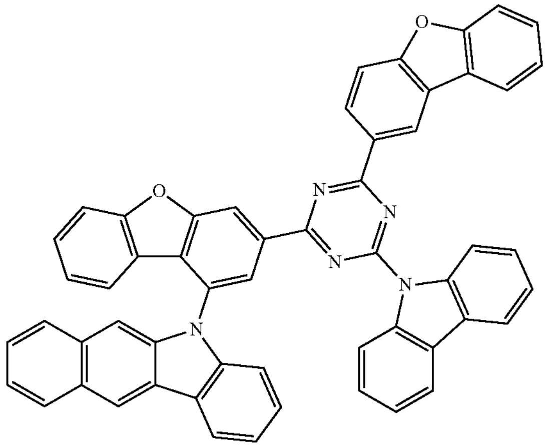
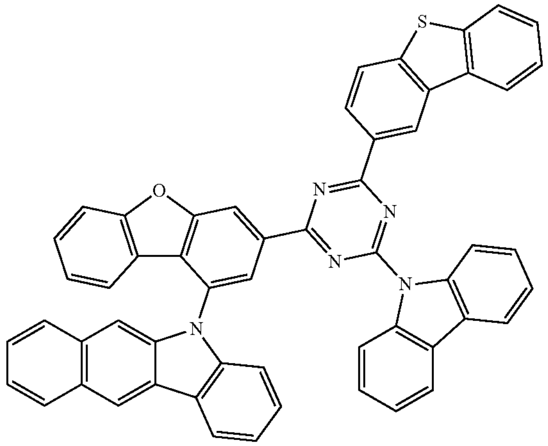

-continued
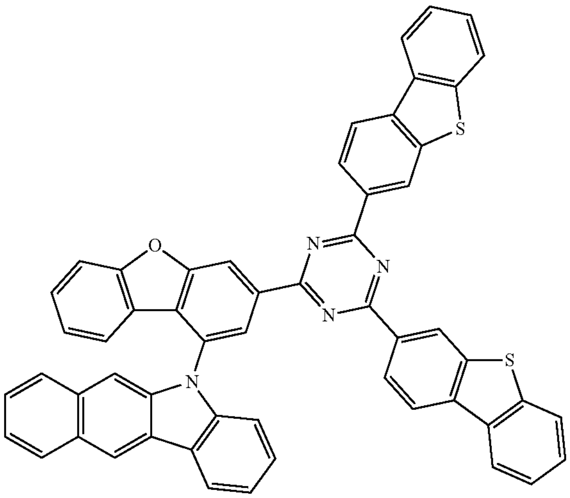
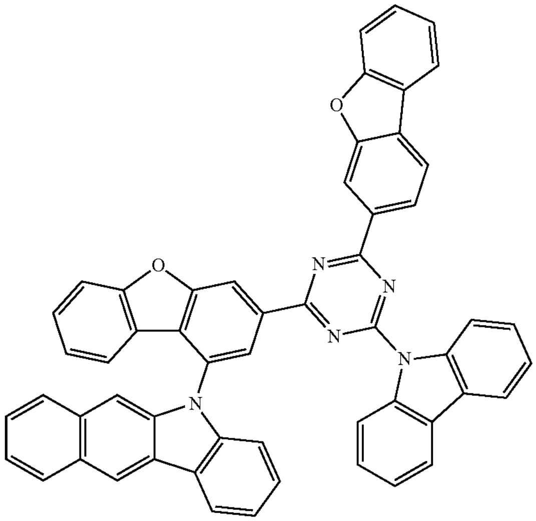
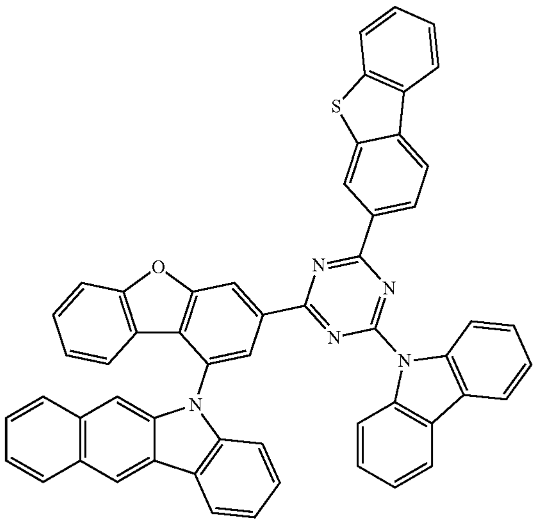
-continued
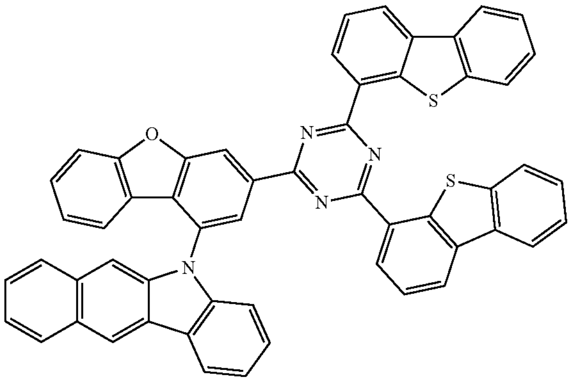
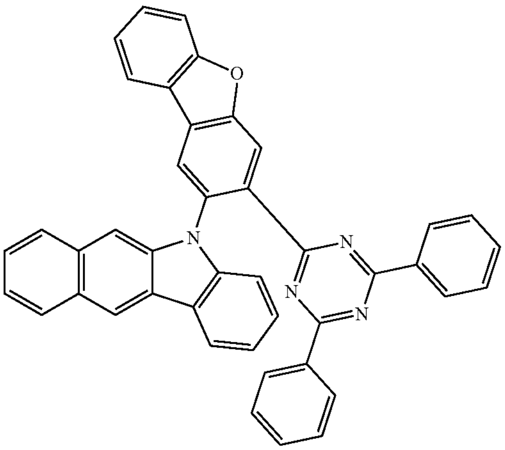
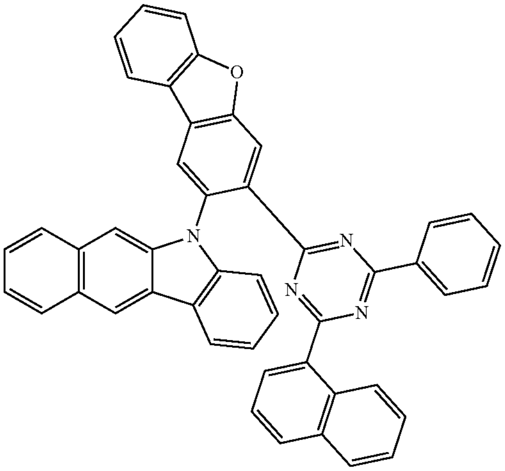

-continued
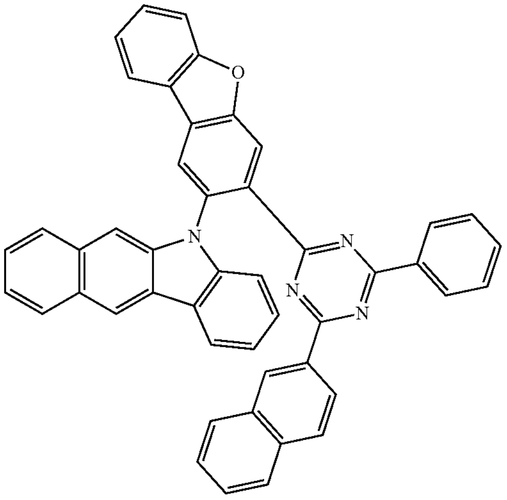
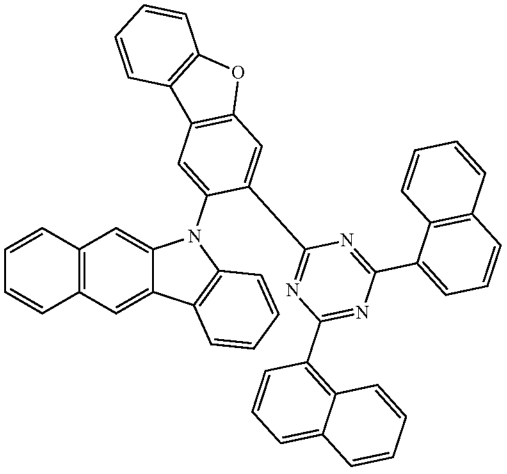
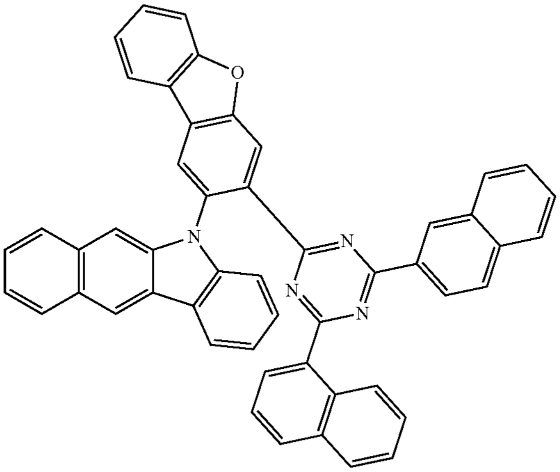
-continued
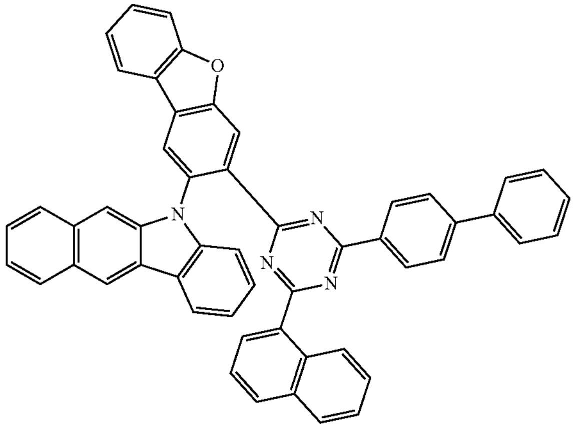
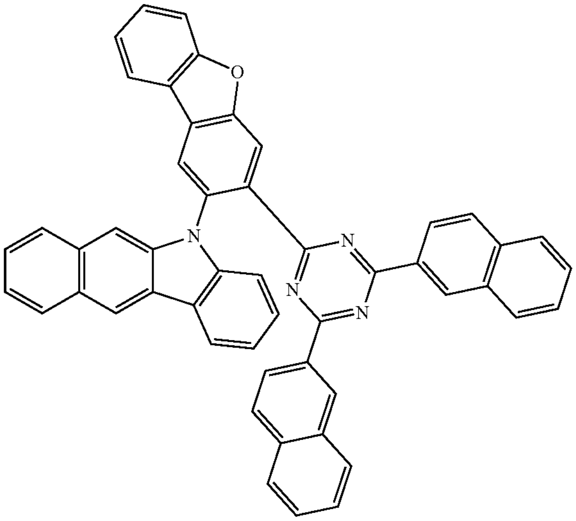
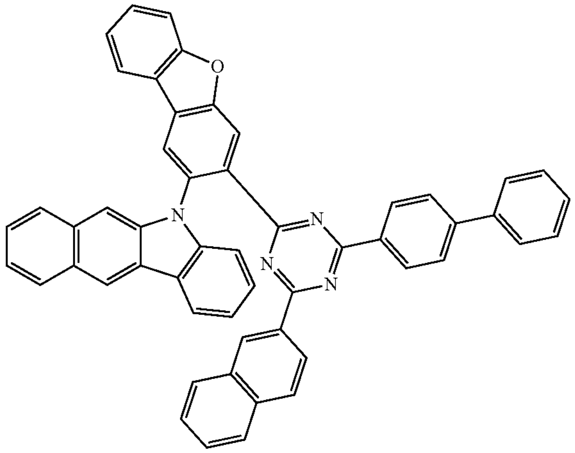

-continued
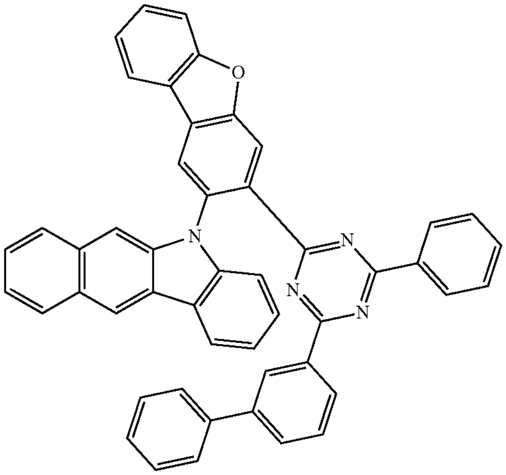
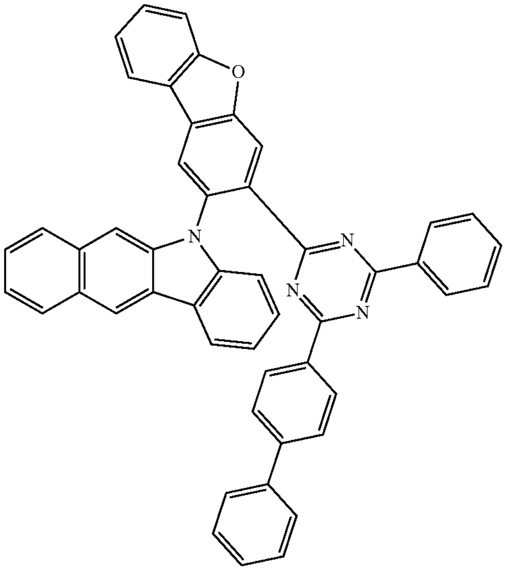
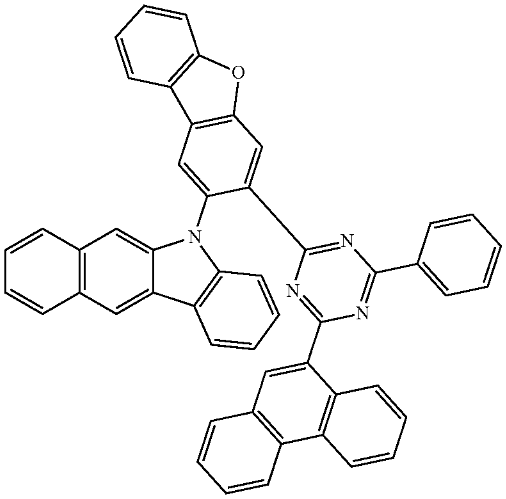
-continued
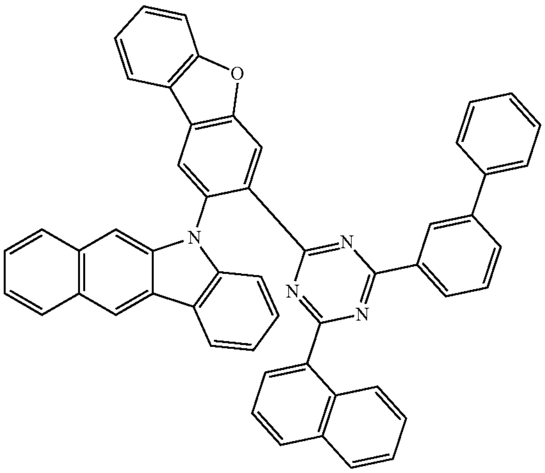
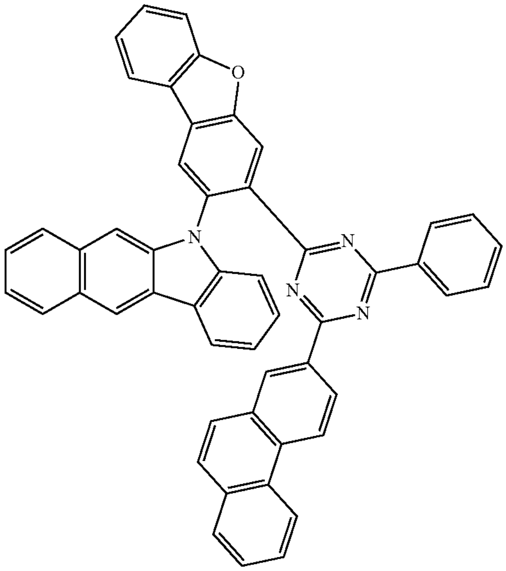
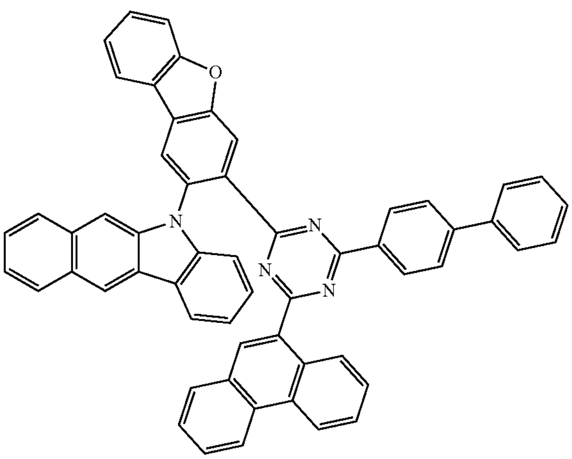

-continued
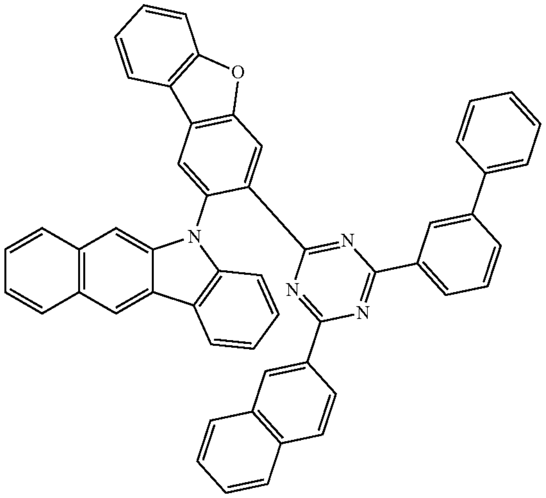
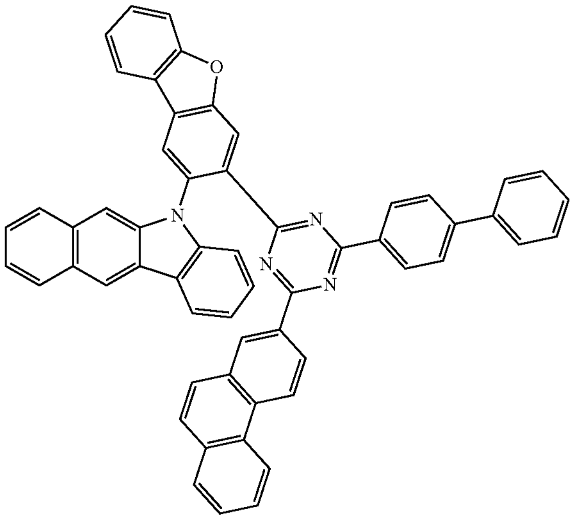
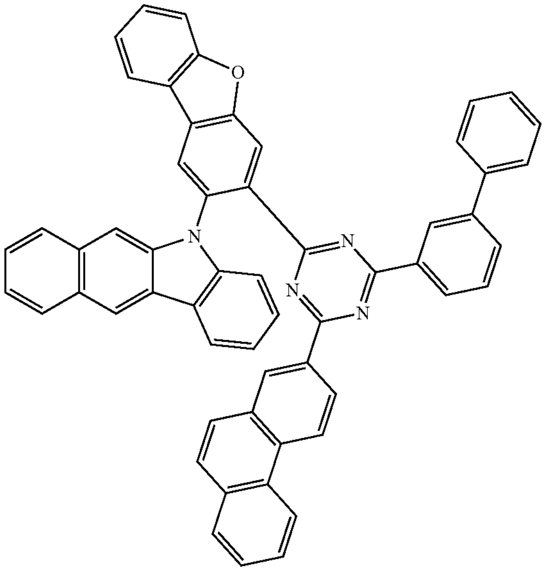
-continued
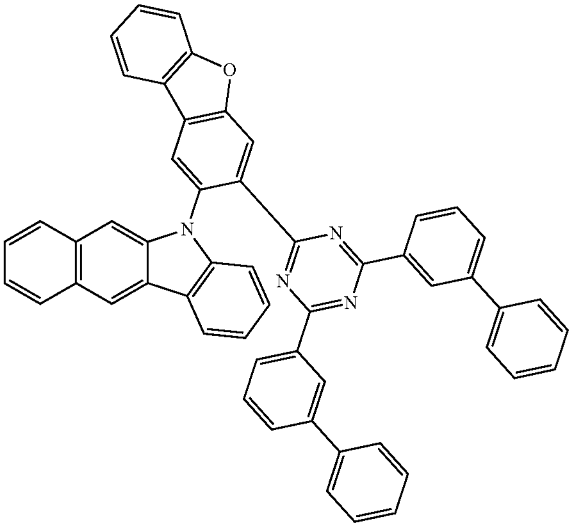
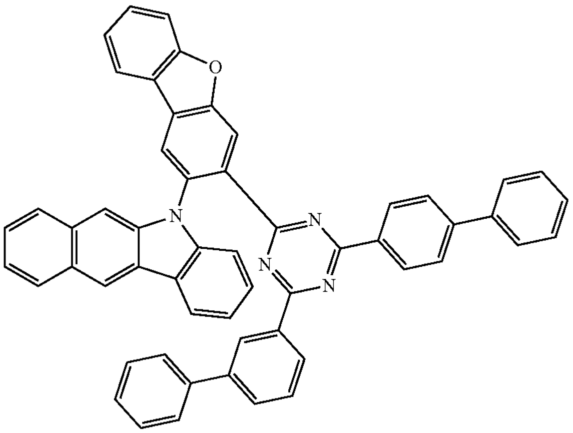
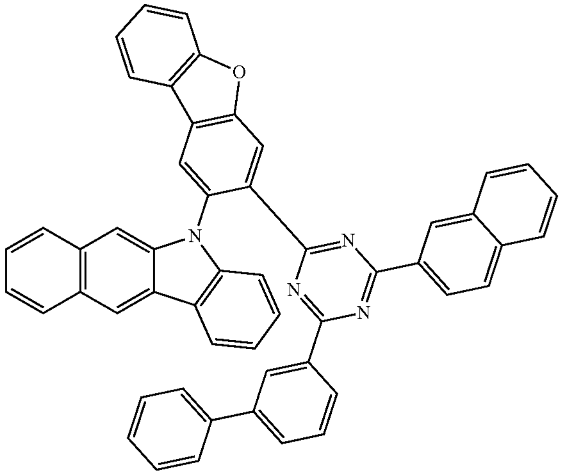

-continued
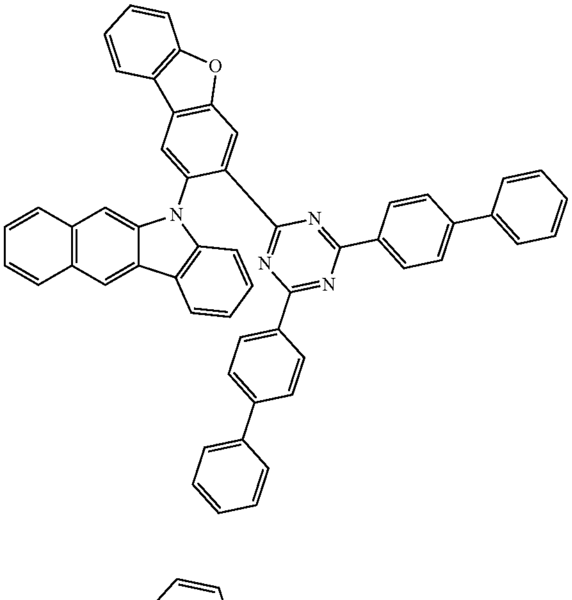
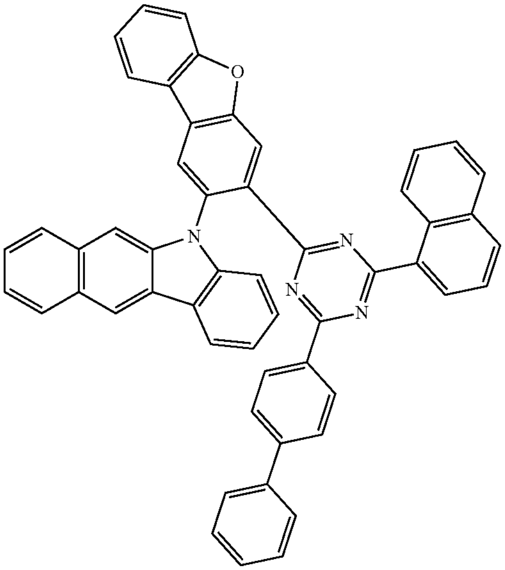
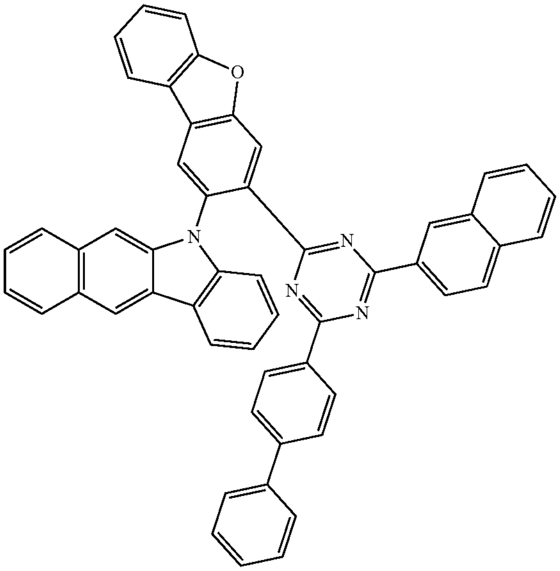
-continued
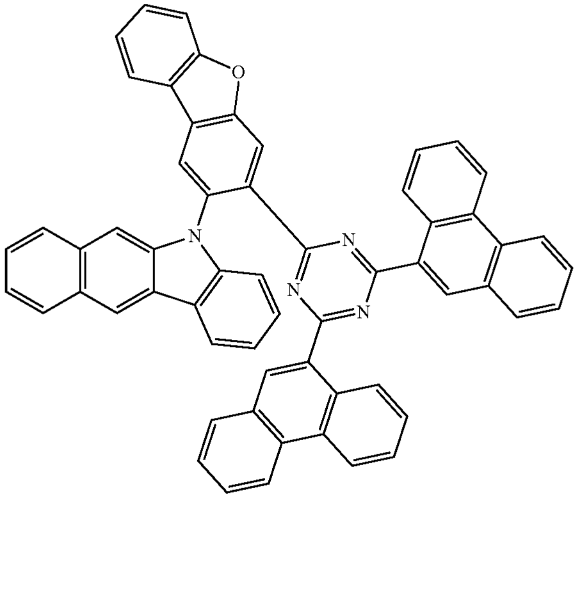
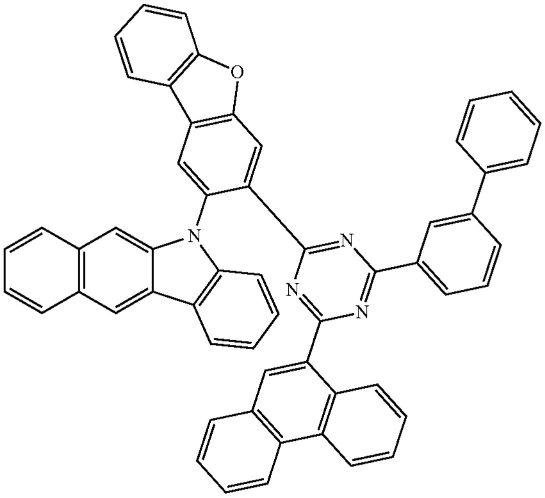
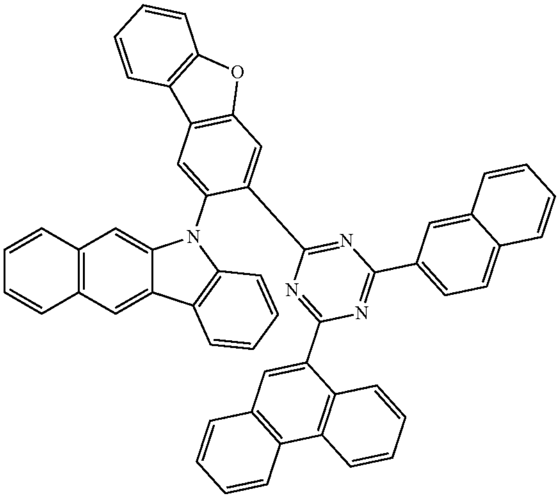

-continued
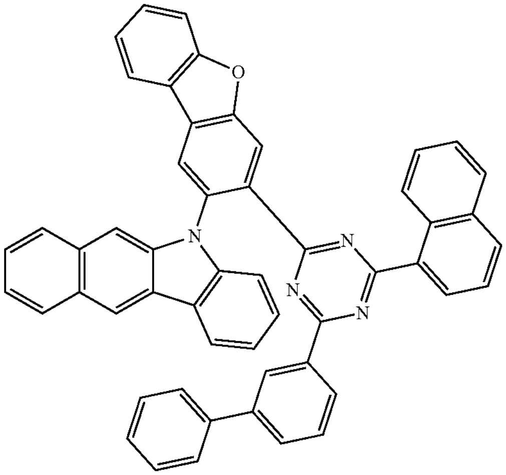
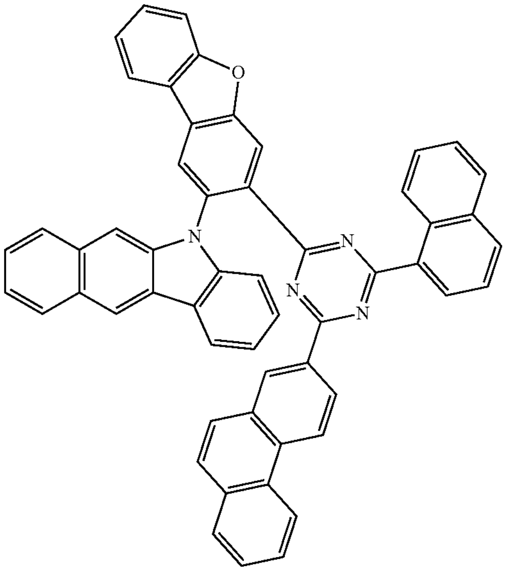
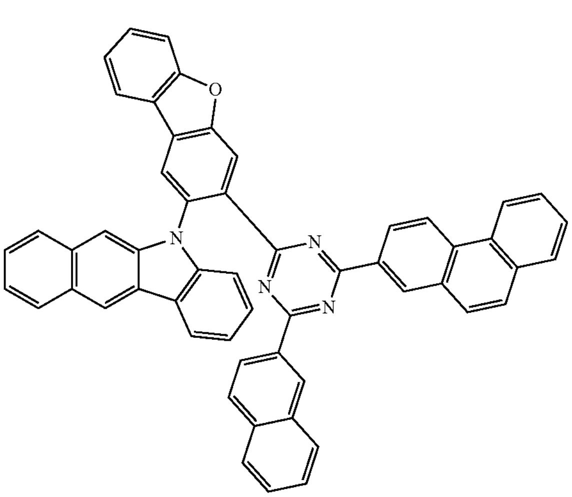
-continued
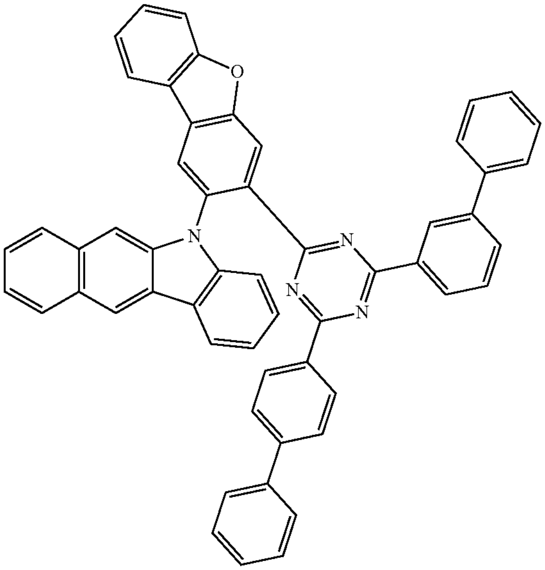
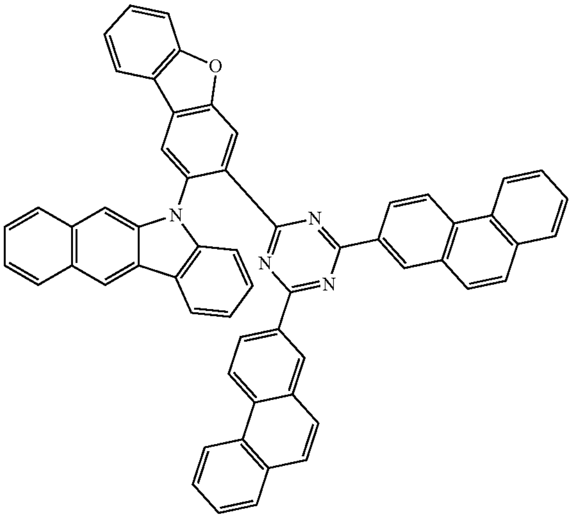
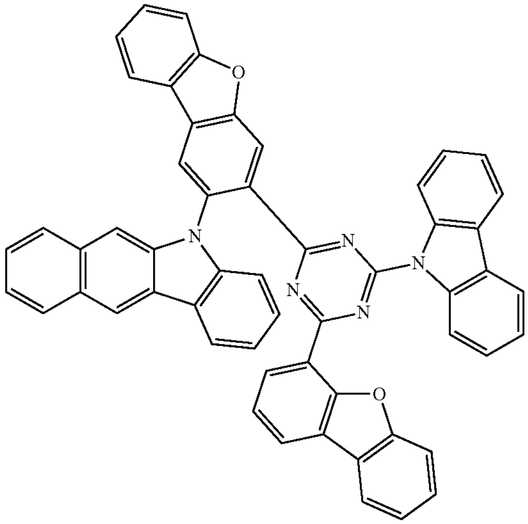

-continued
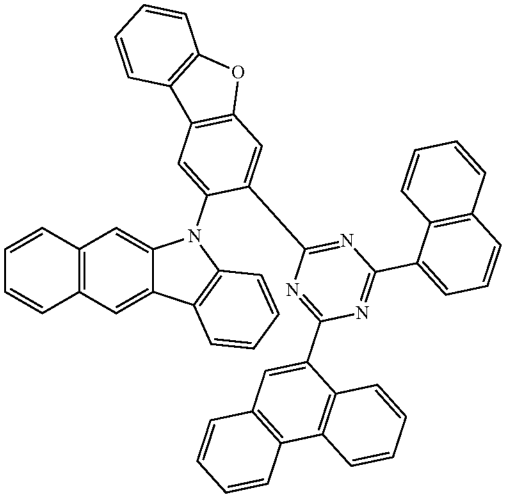
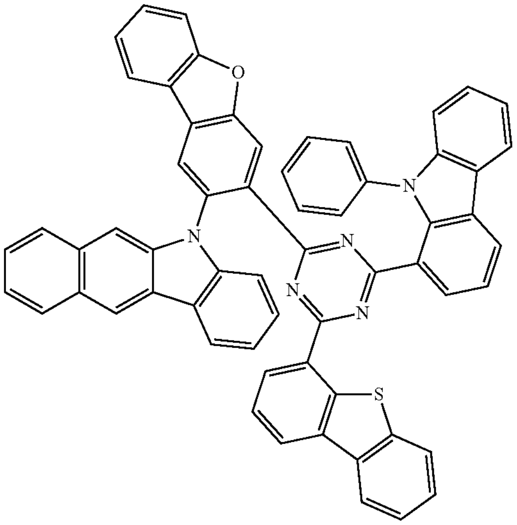
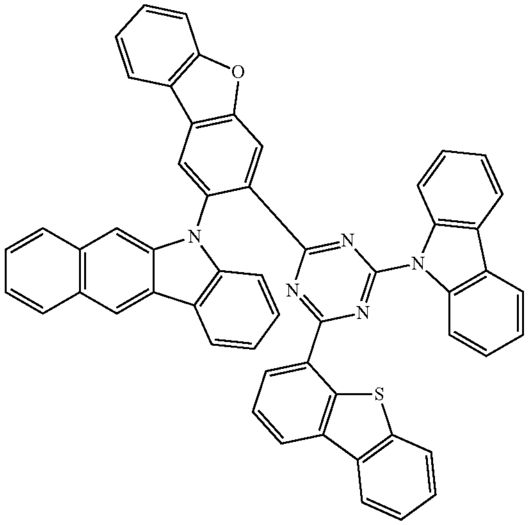
-continued
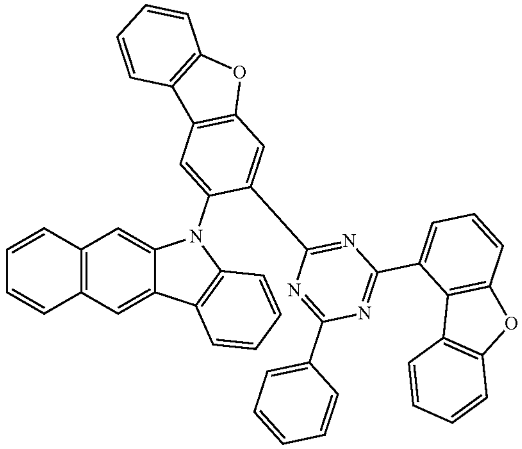
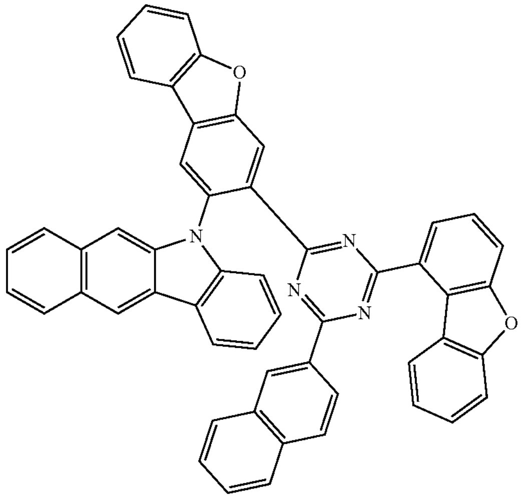
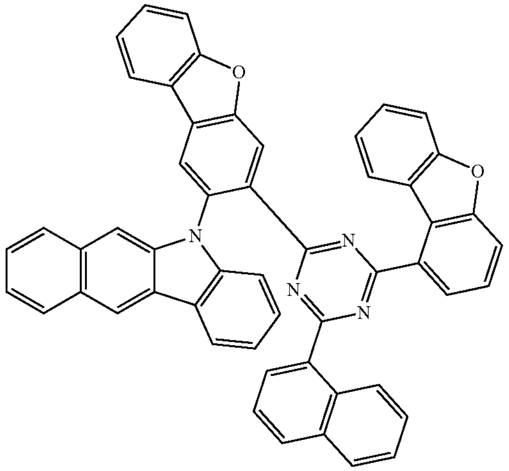

-continued
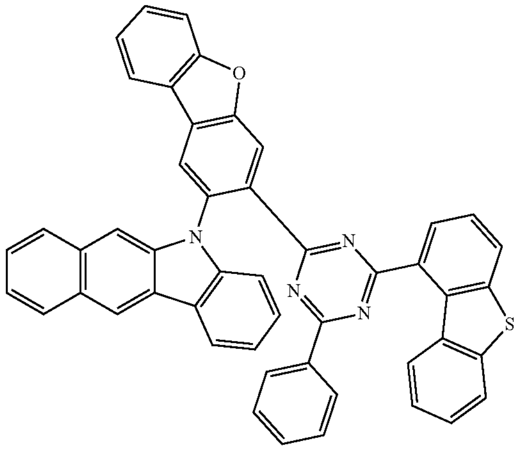
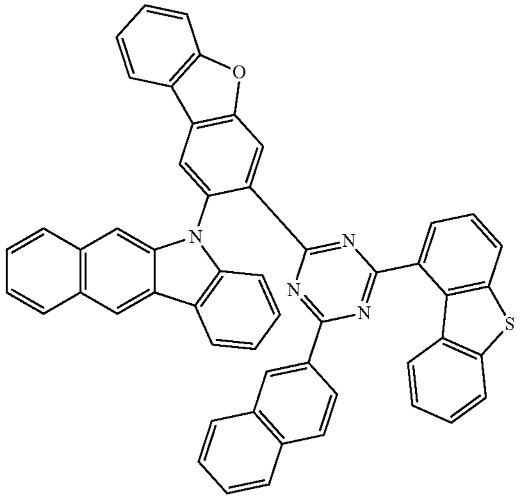
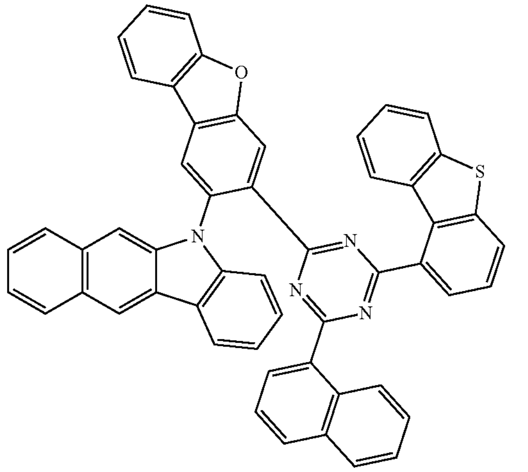
-continued
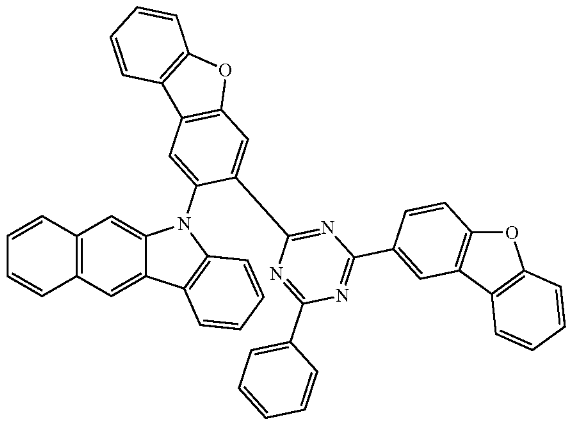
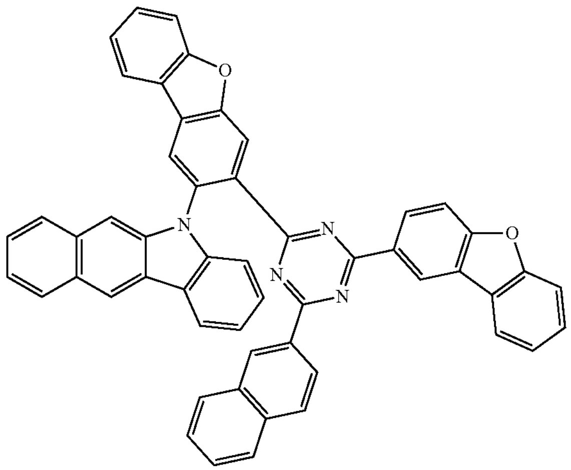
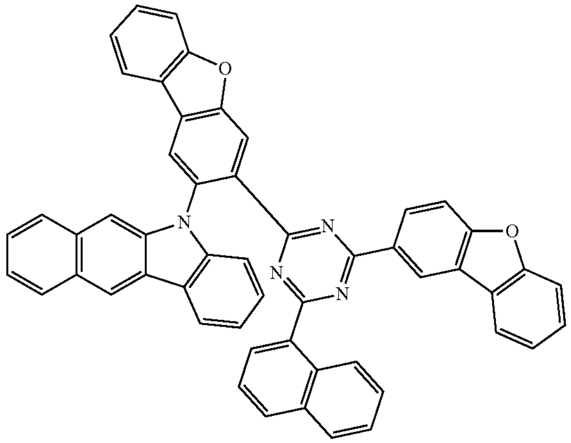

-continued
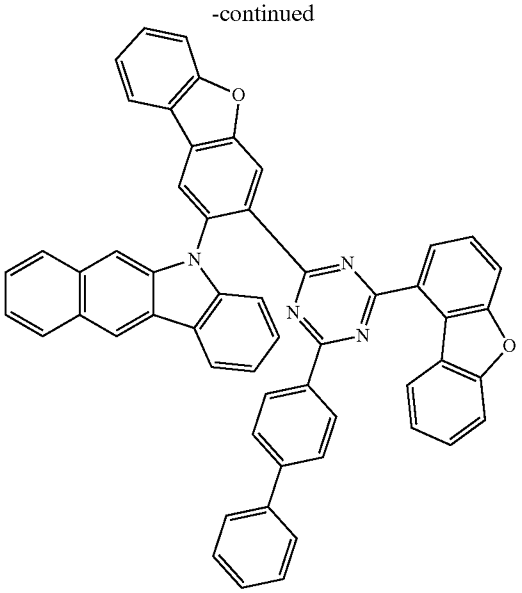
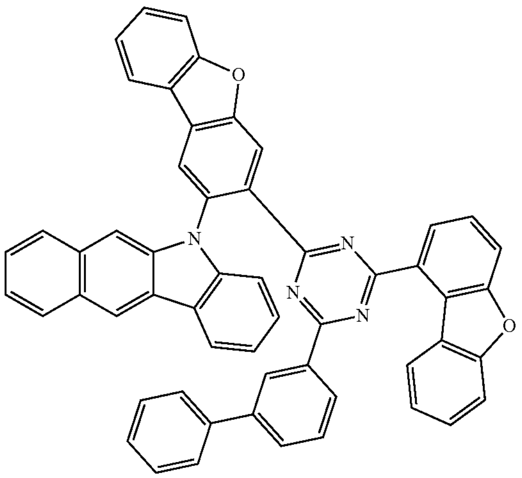
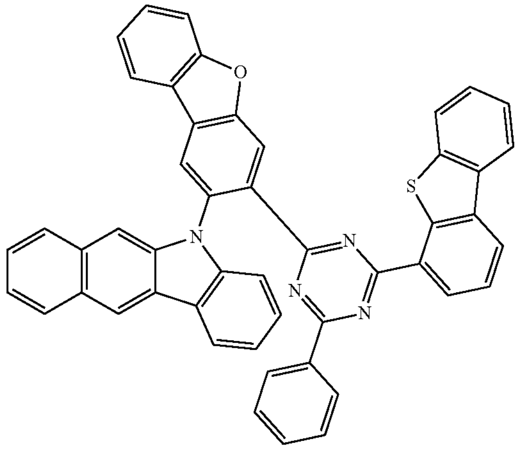
-continued
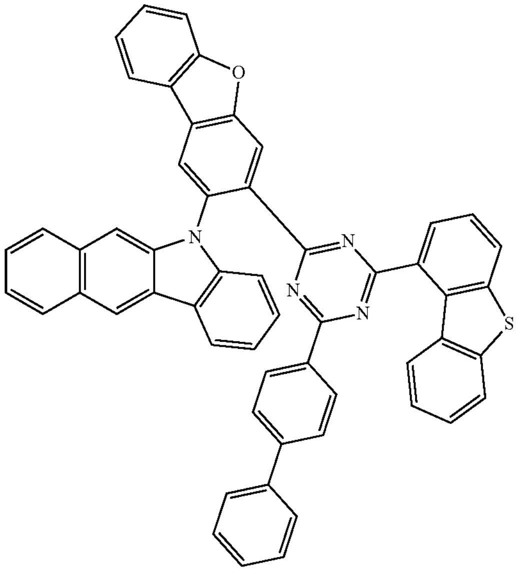
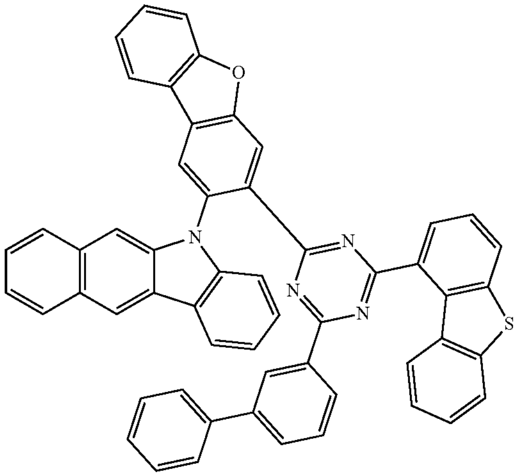
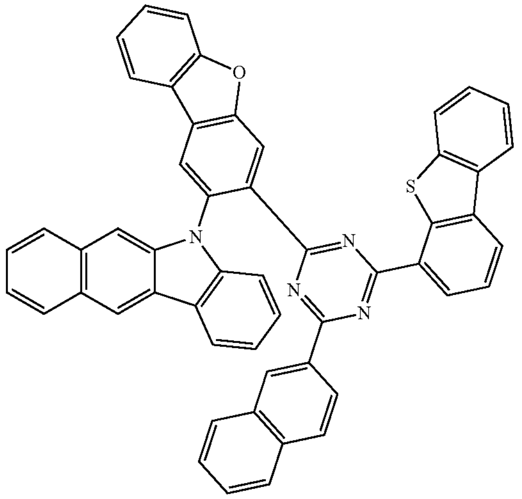

-continued
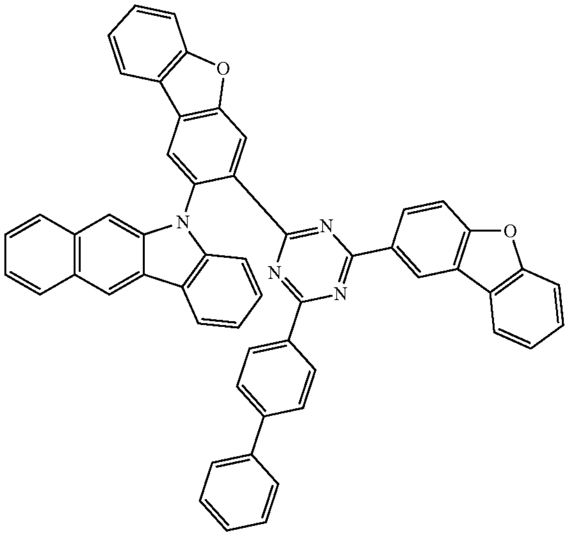
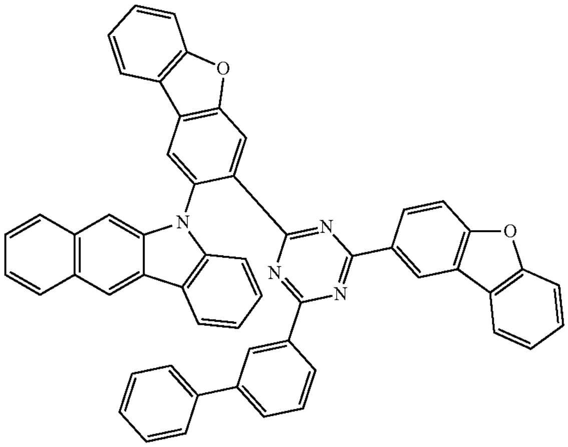
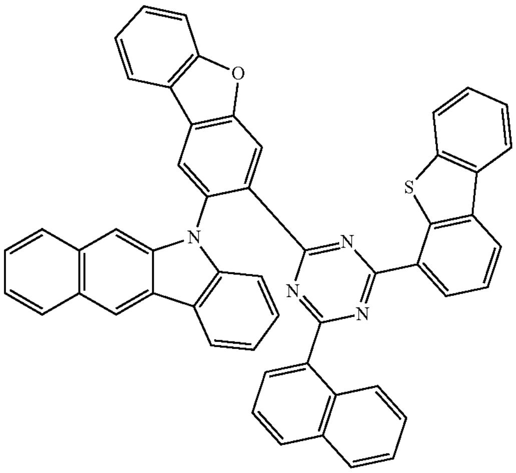
-continued
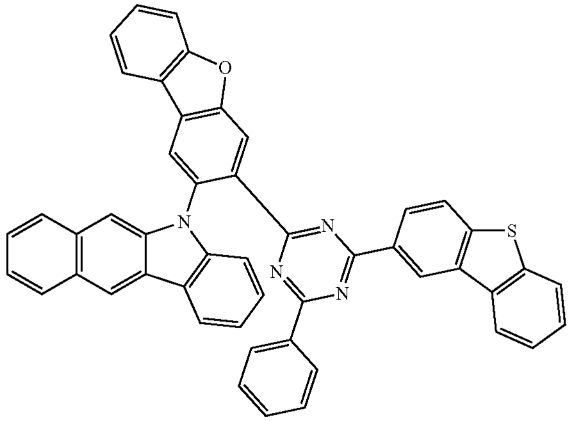
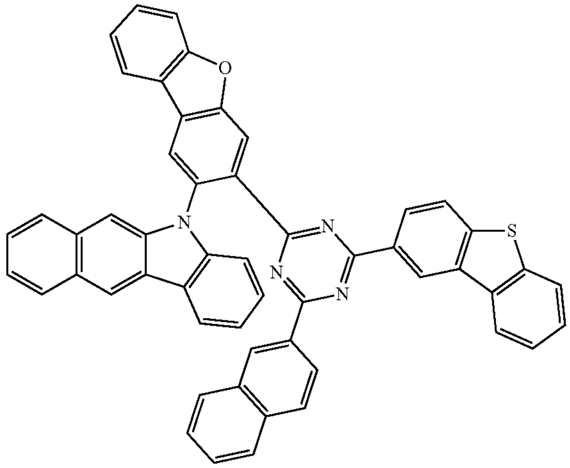
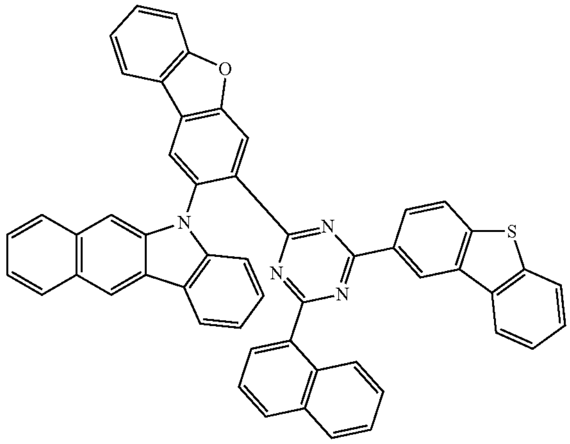

-continued
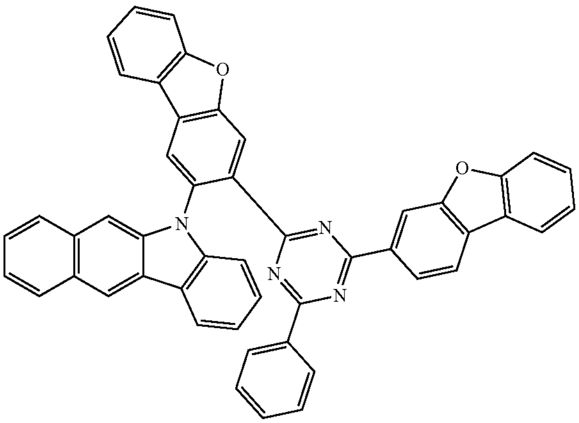
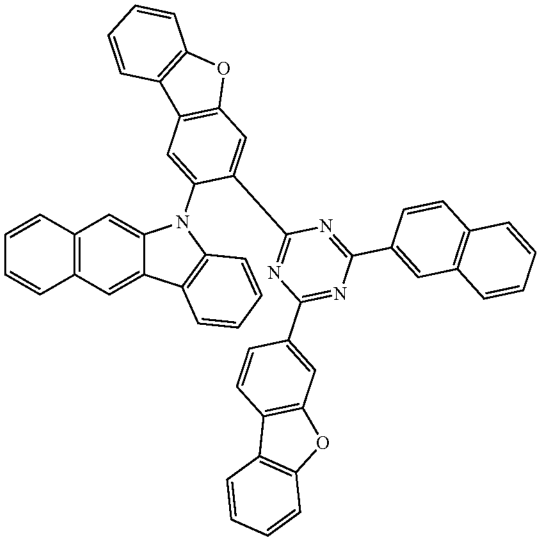
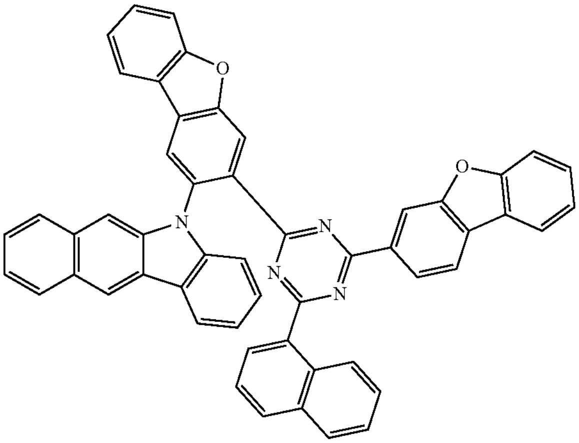
-continued
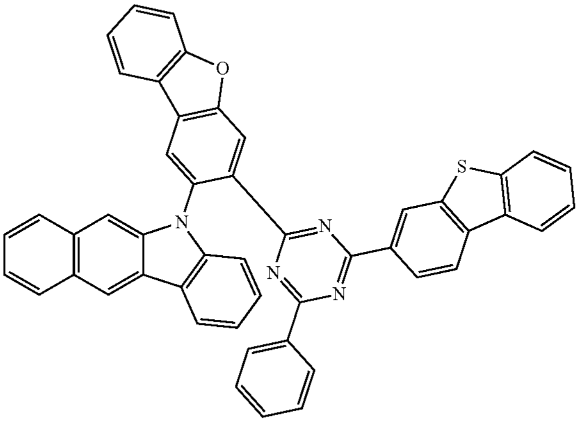
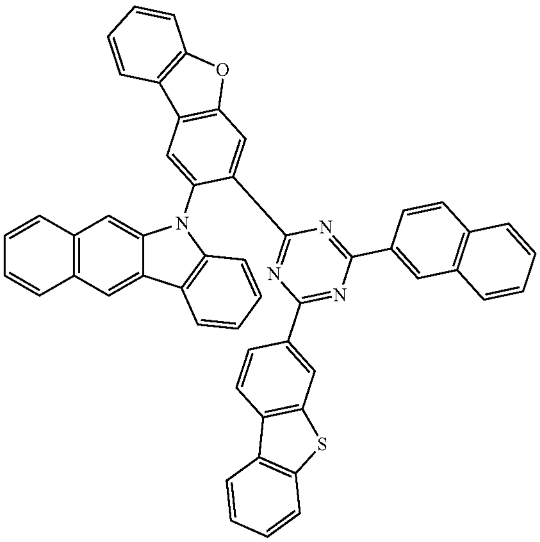
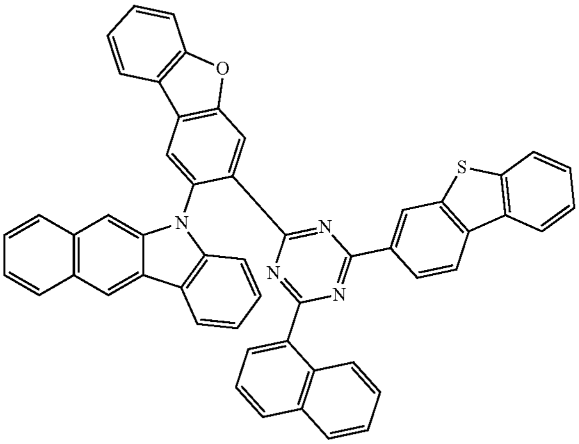

-continued
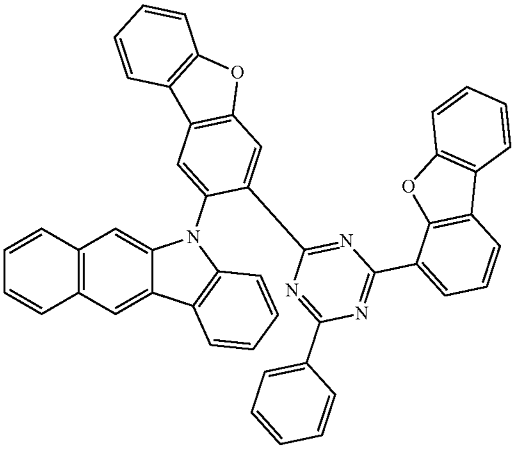
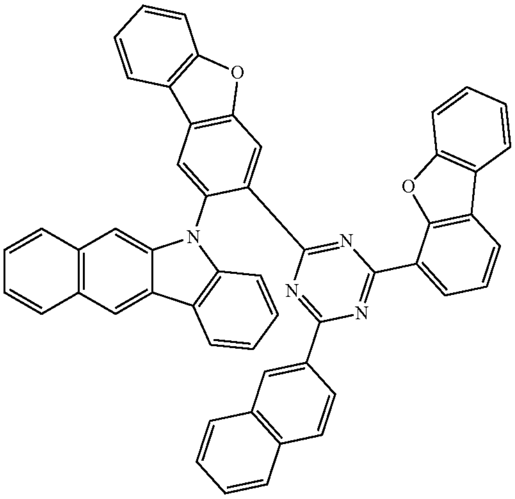
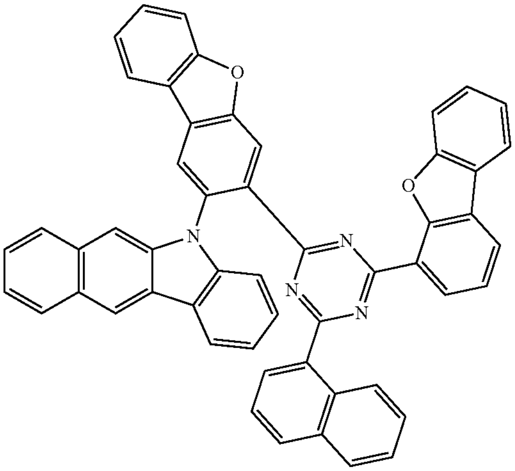
-continued
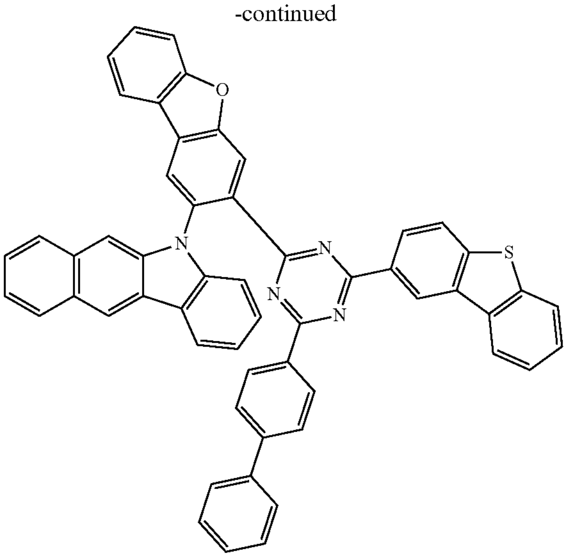
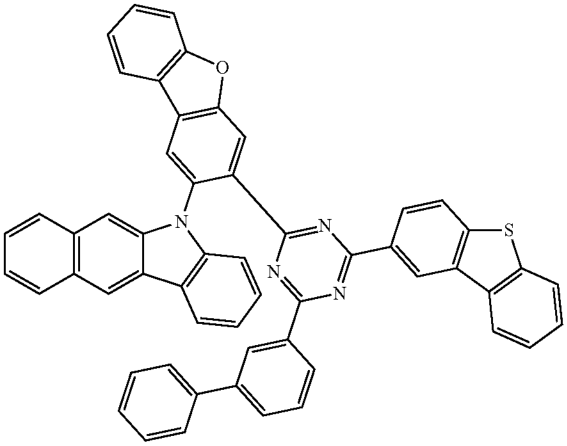
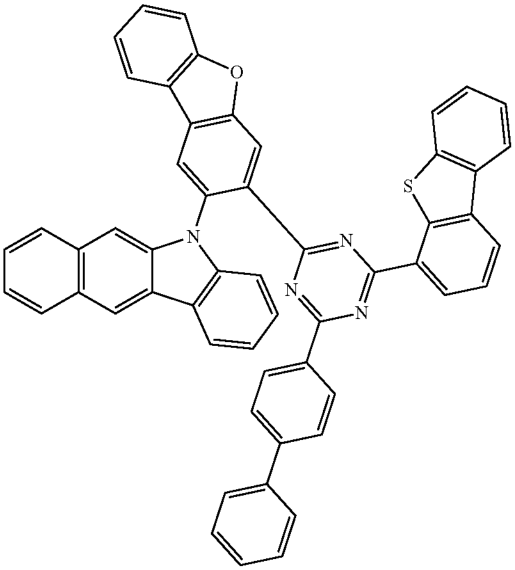

-continued
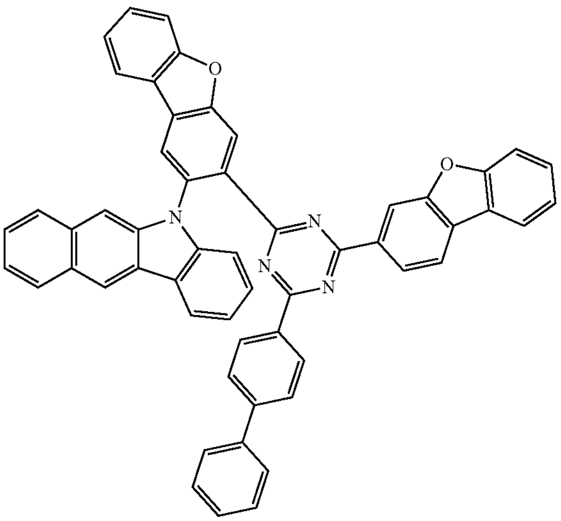
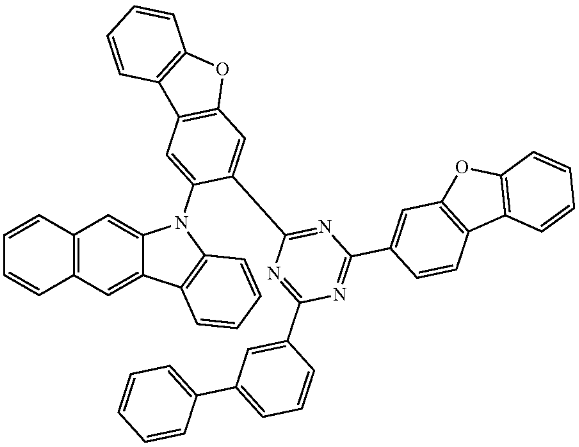
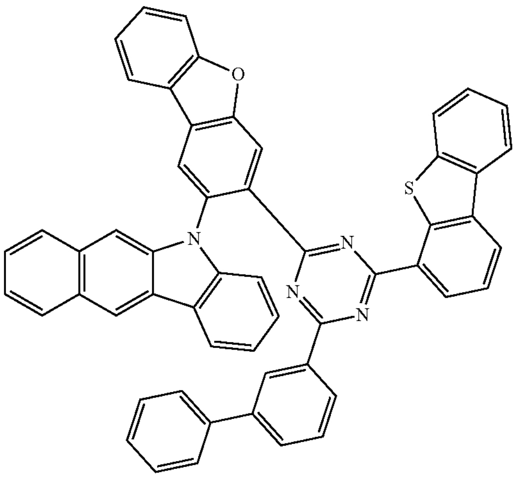
-continued
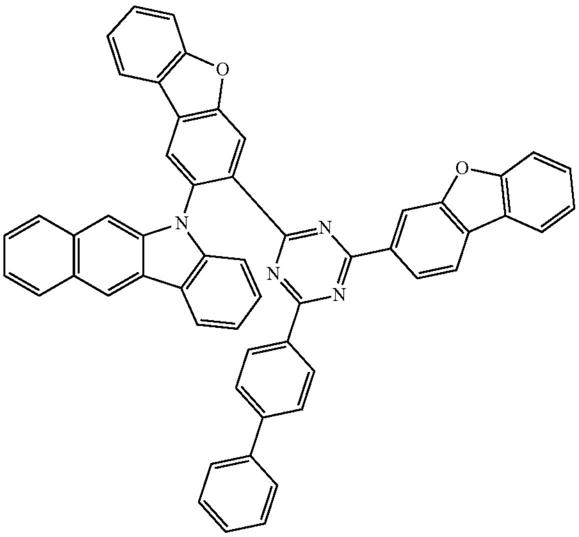
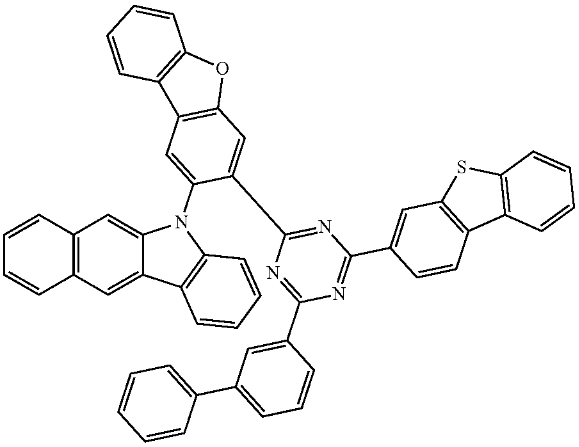
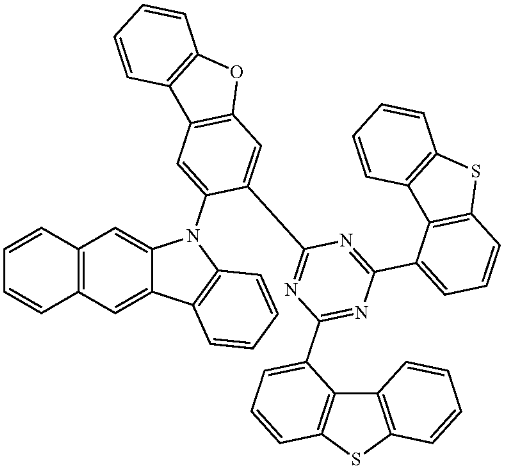

-continued
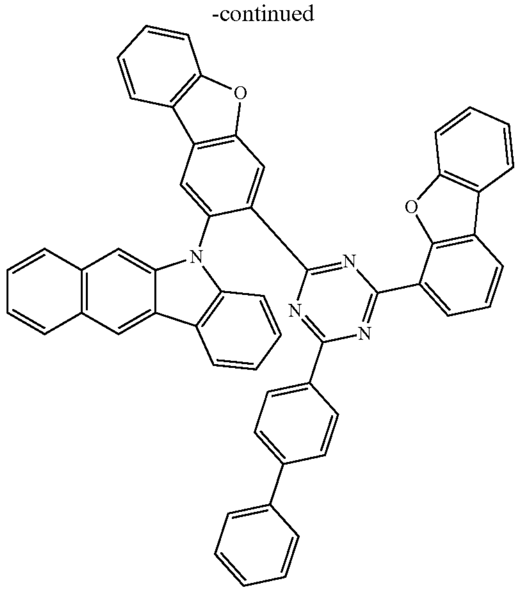
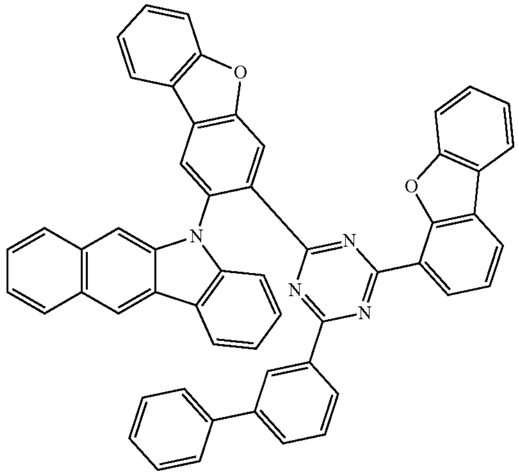
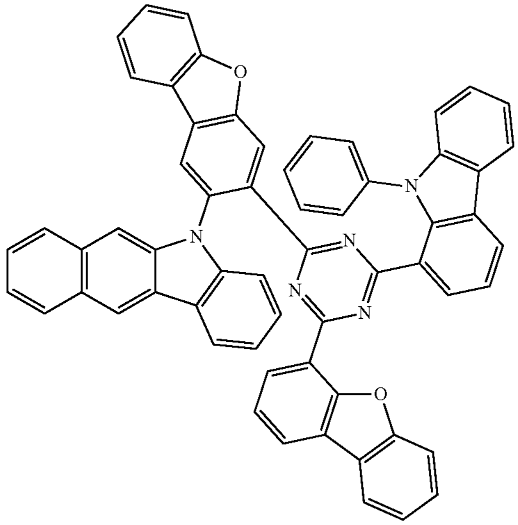
-continued
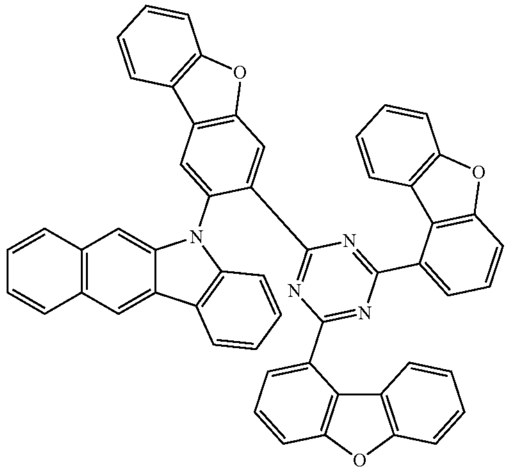
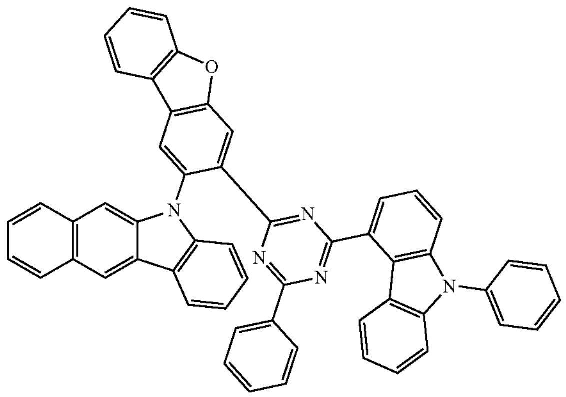
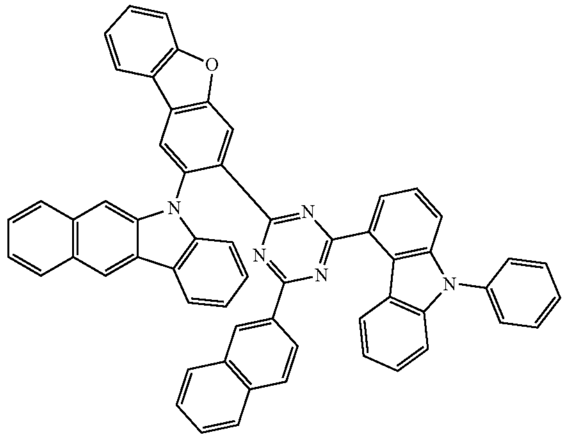

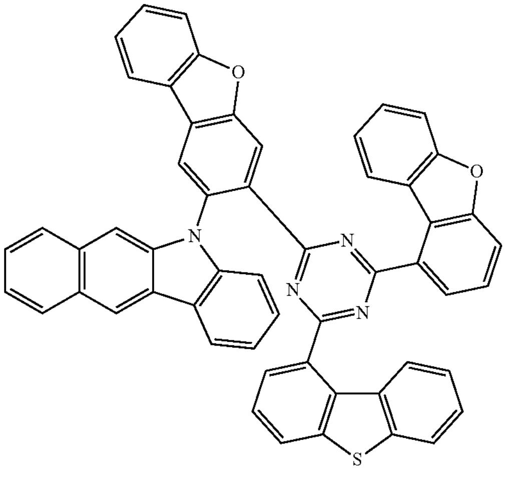
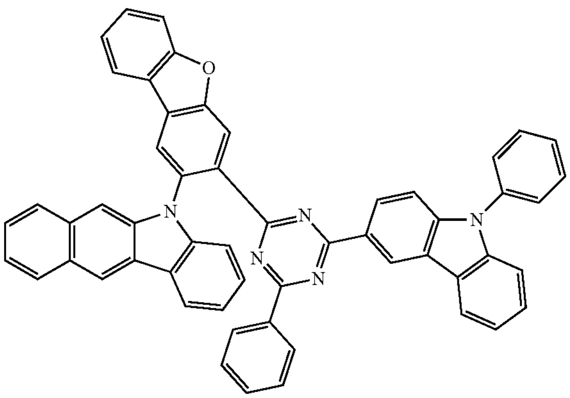
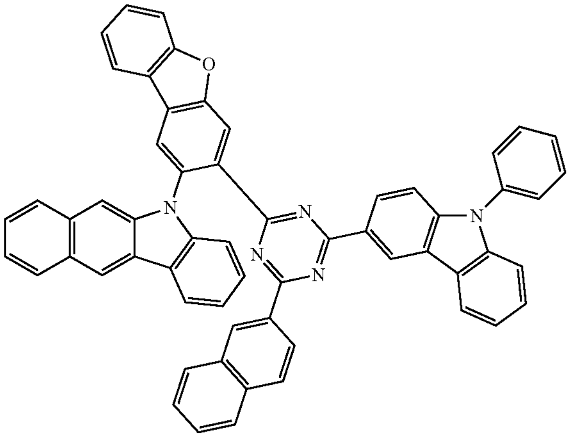
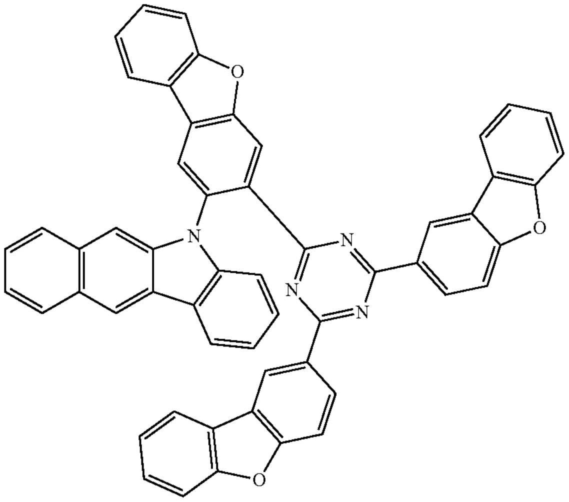
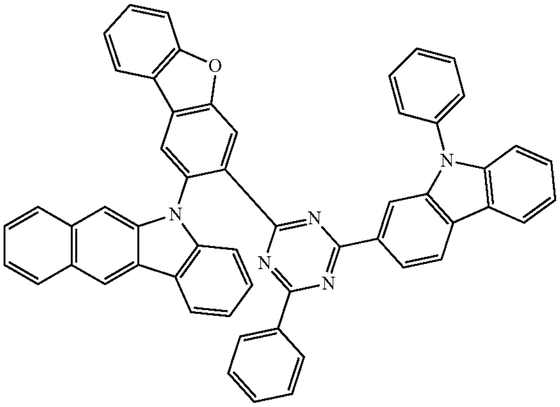
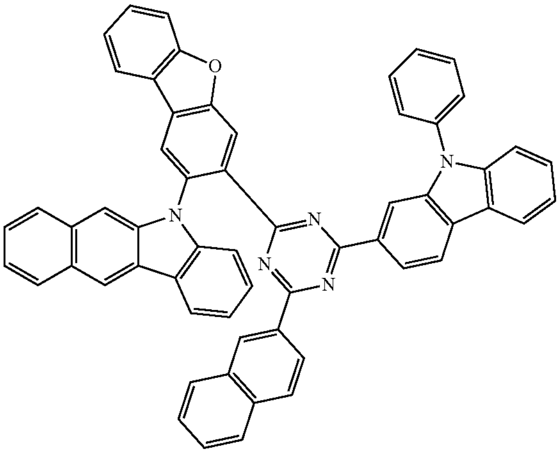

-continued
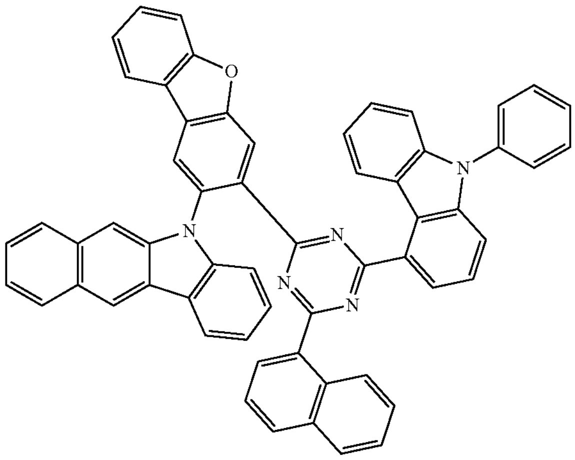
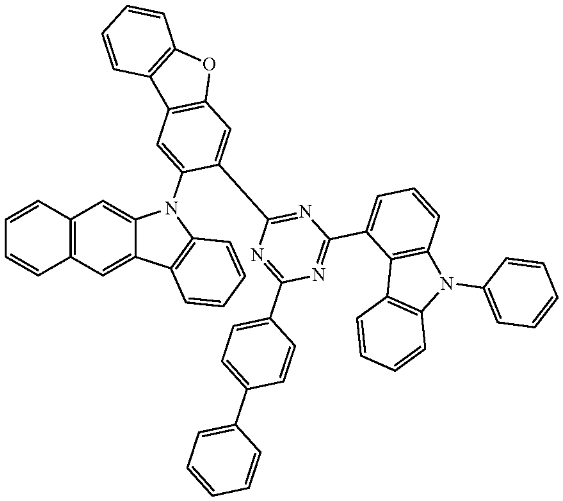
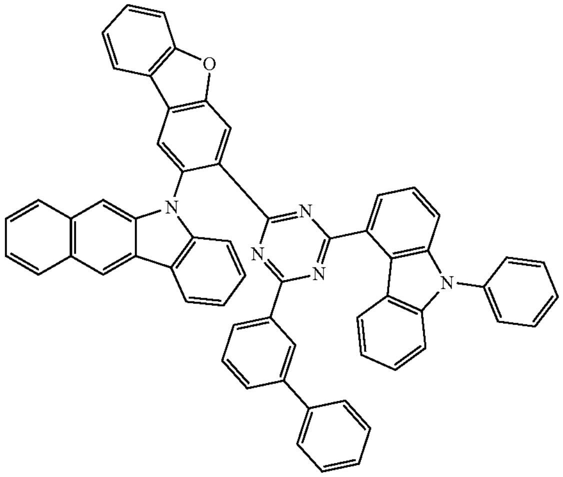
-continued
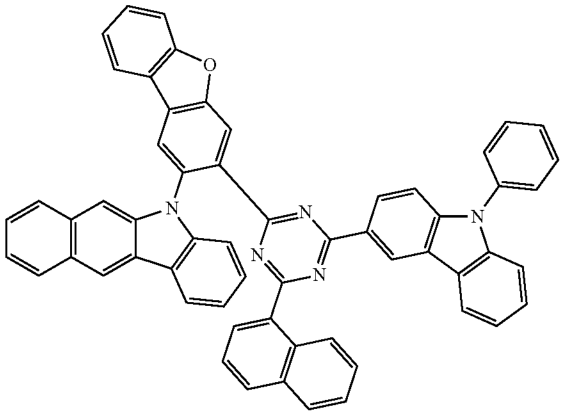
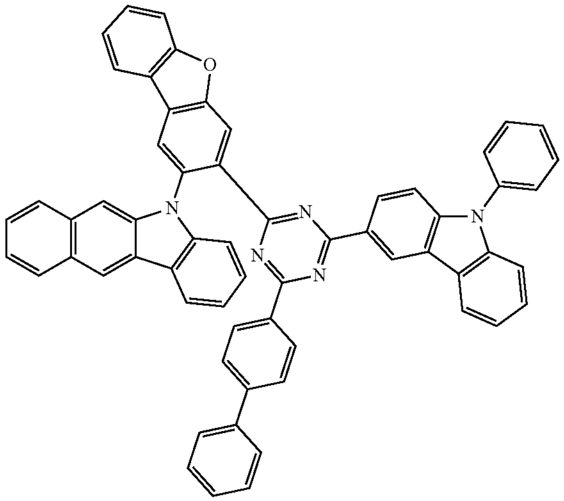
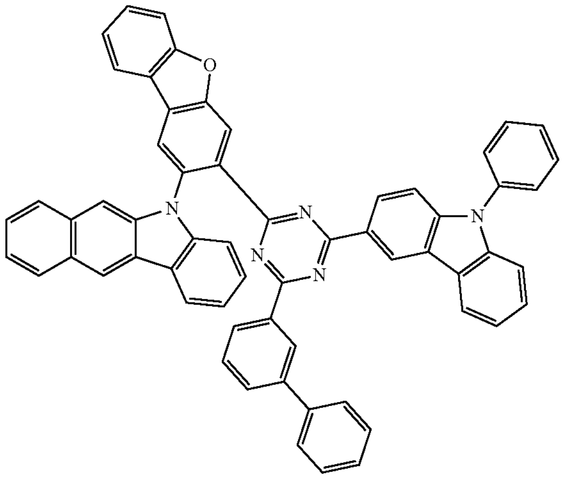

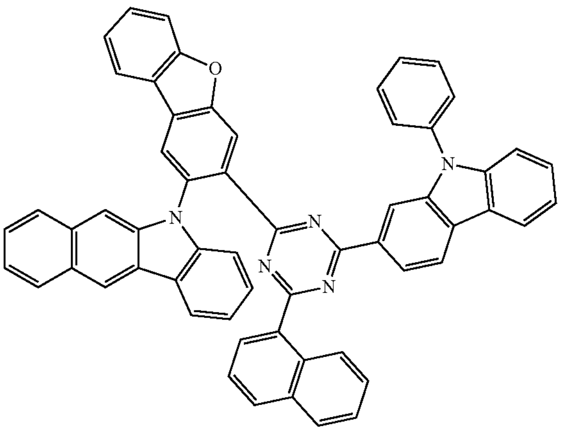
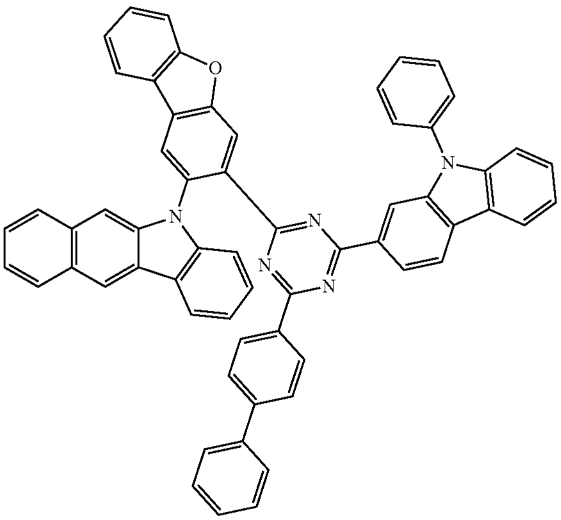
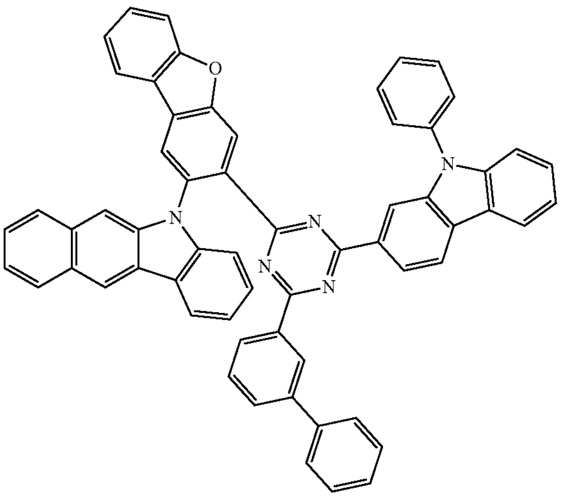
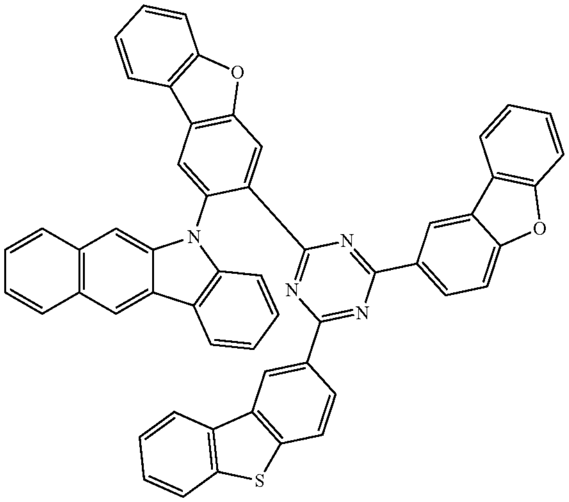
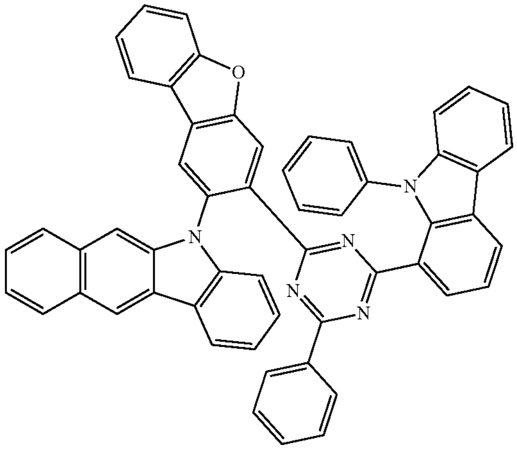
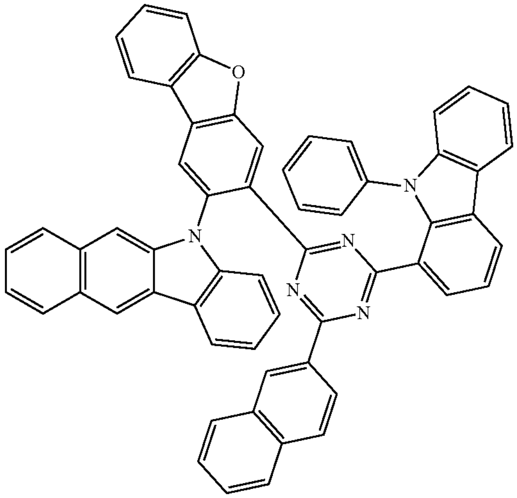

-continued
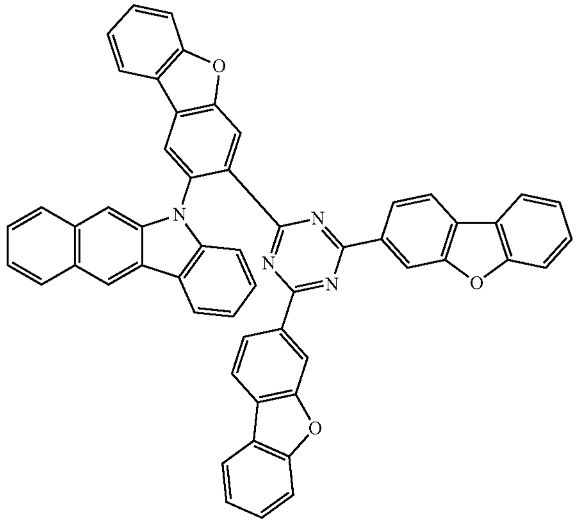
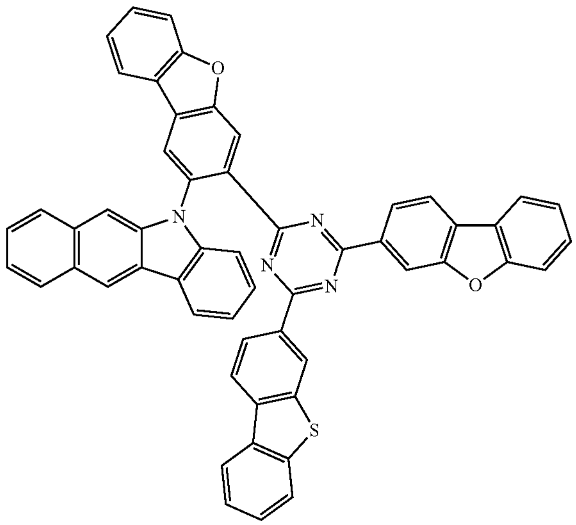
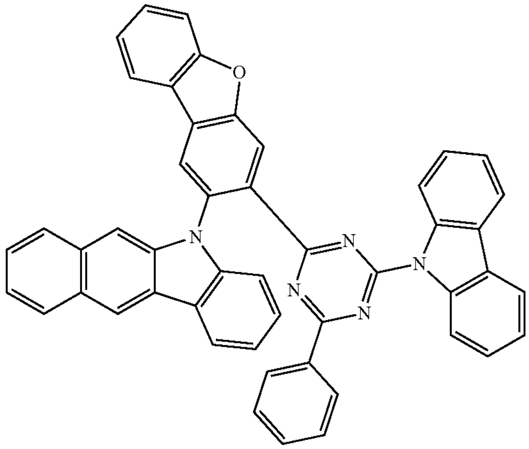
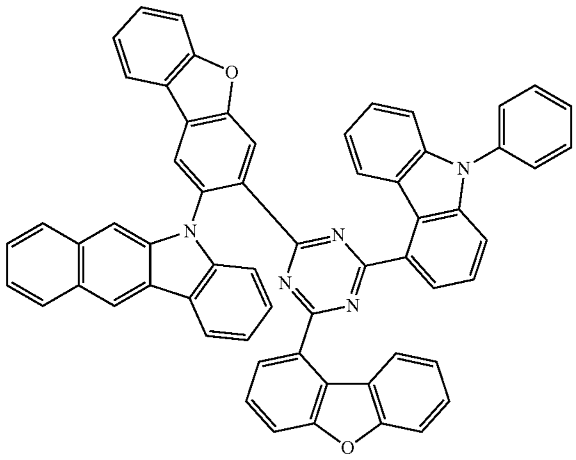
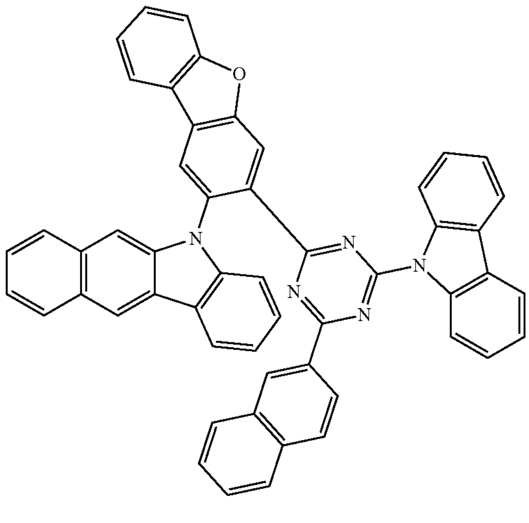
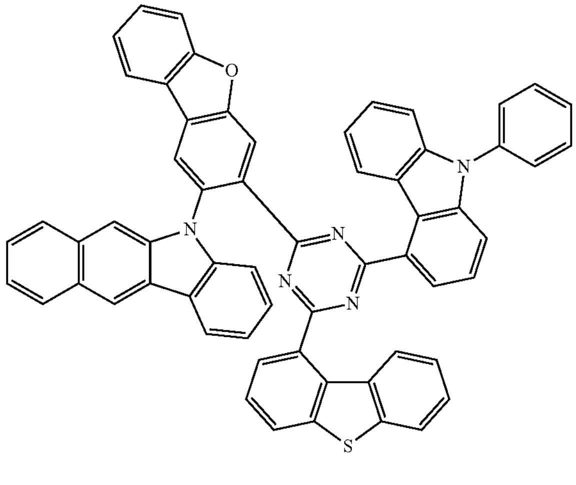
-continued -continued
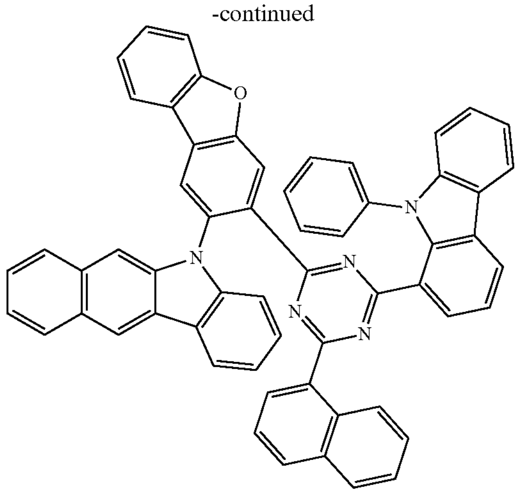
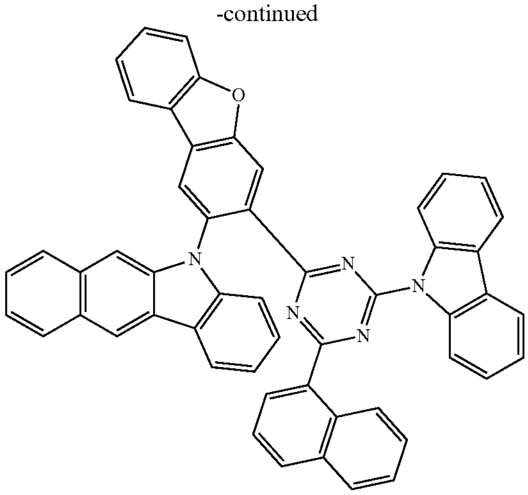
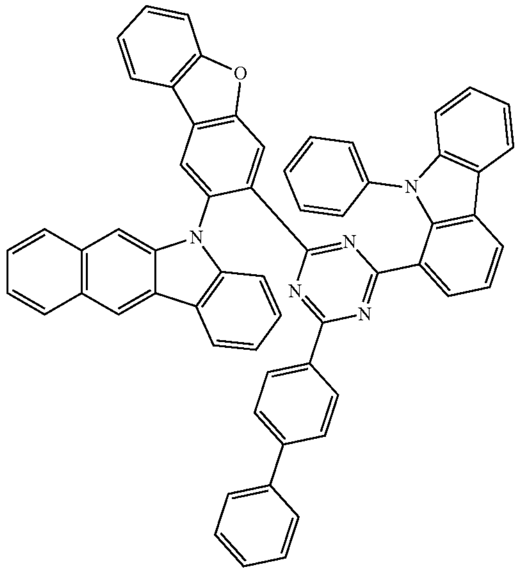
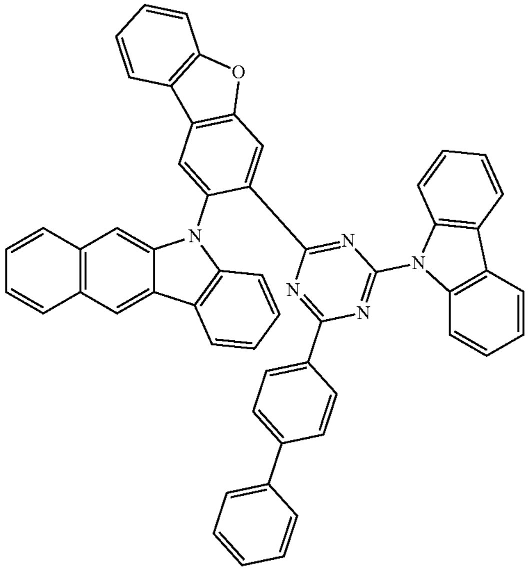
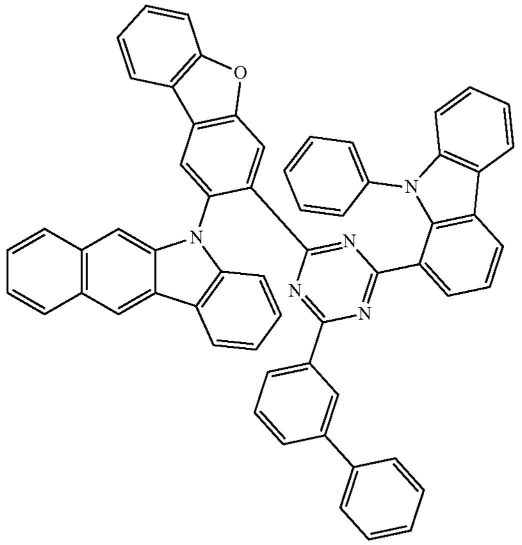
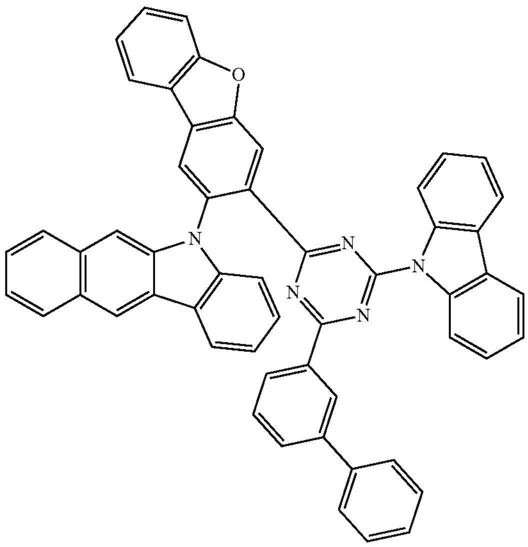
-continued -continued
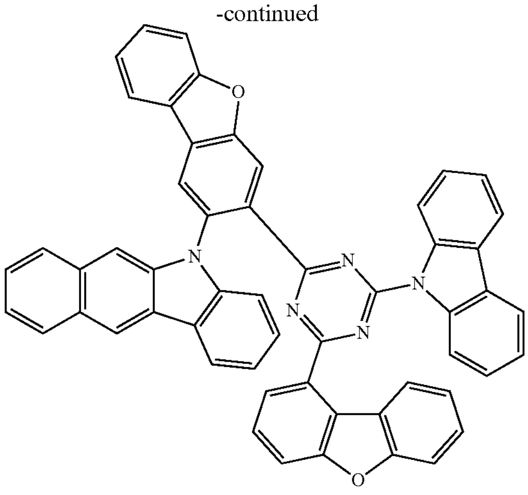
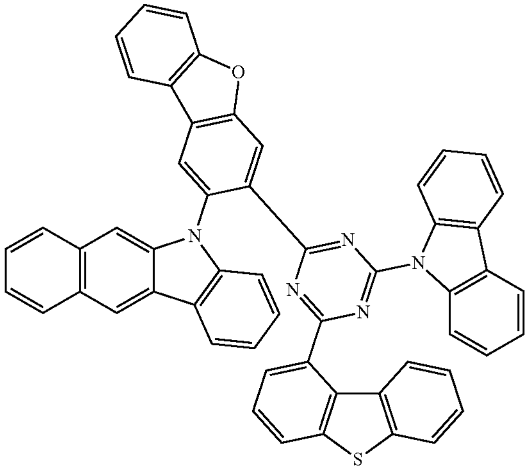
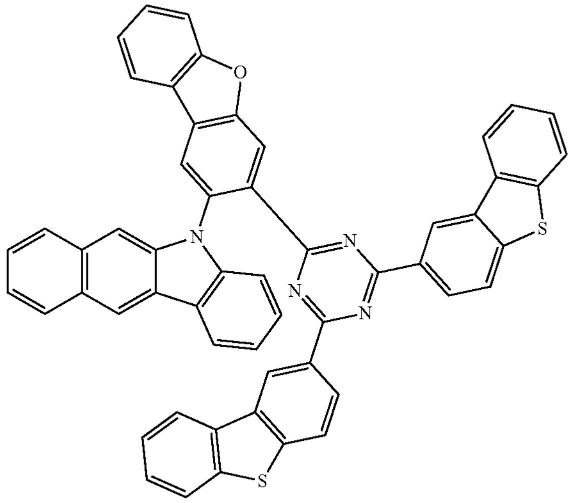
-continued
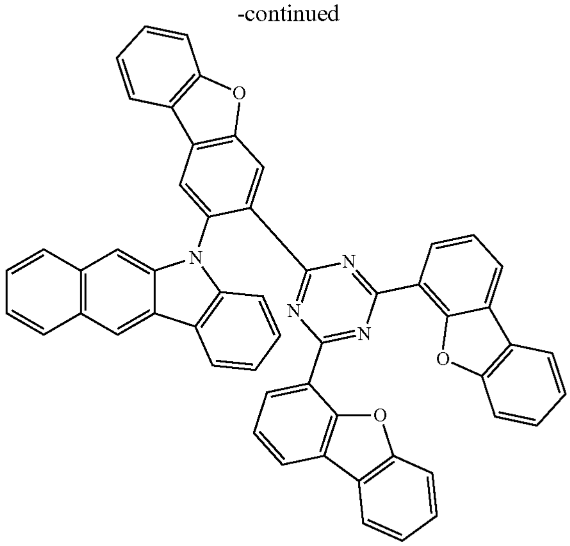
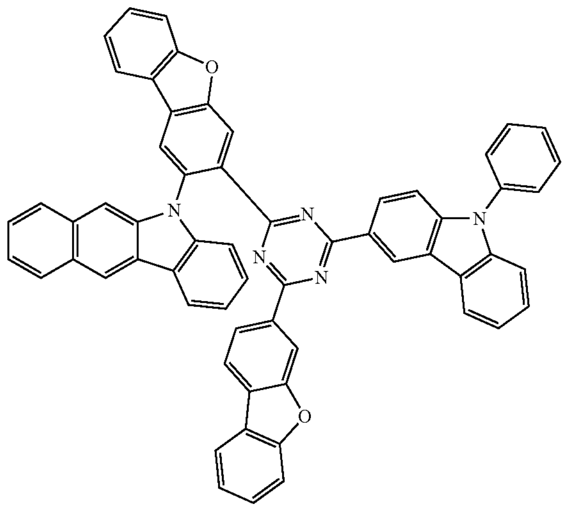
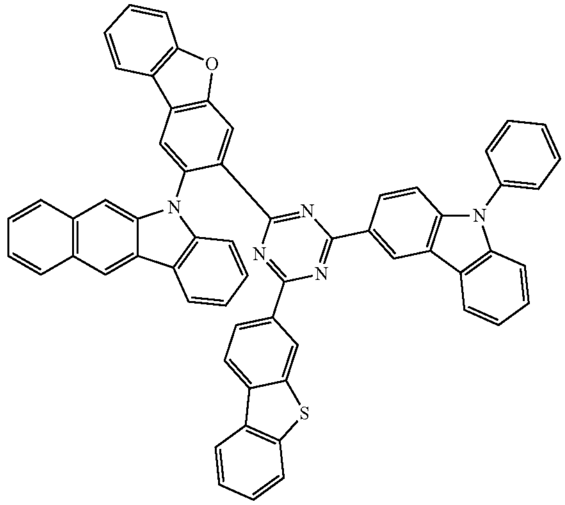

-continued
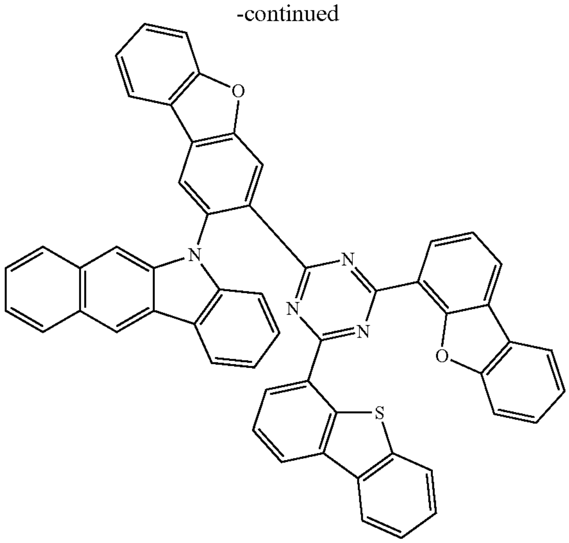
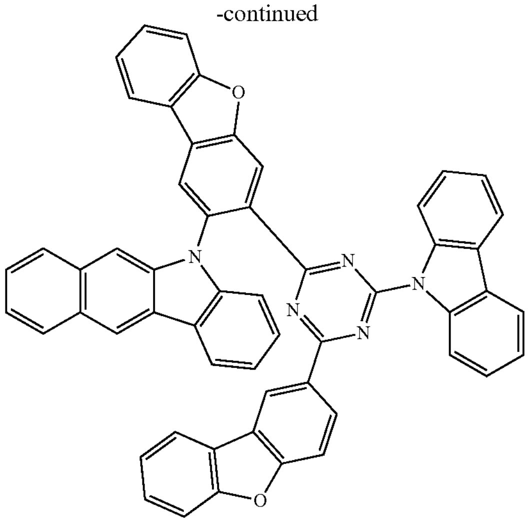
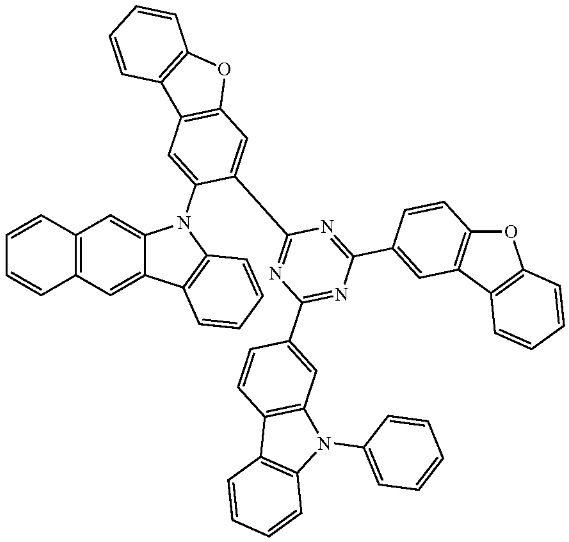
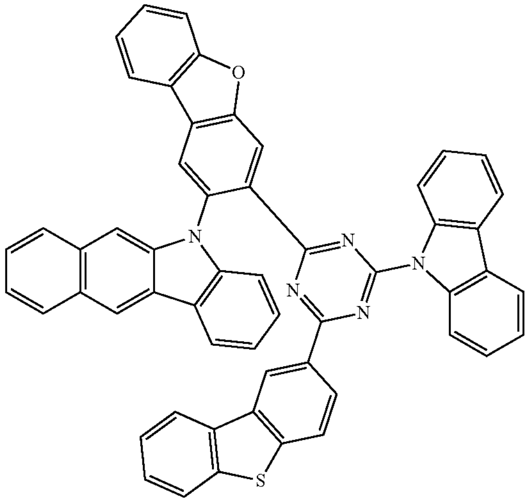
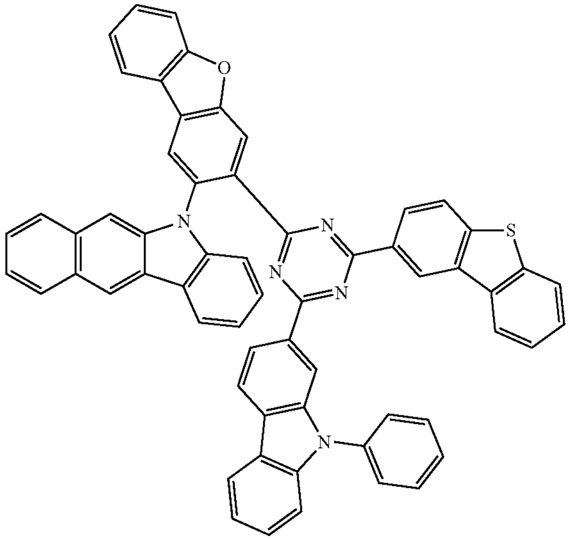
-continued
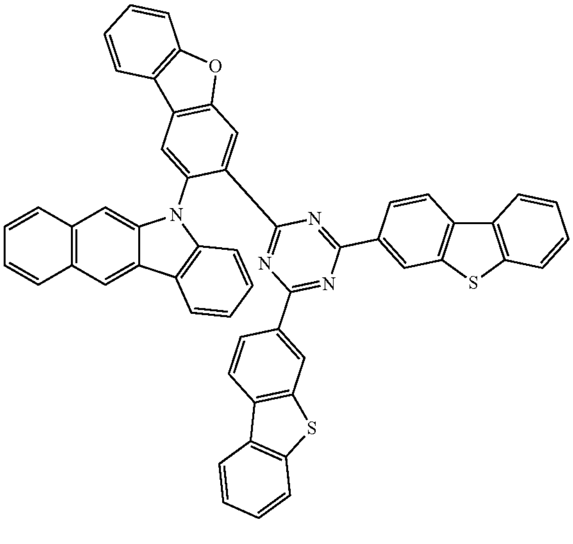

-continued
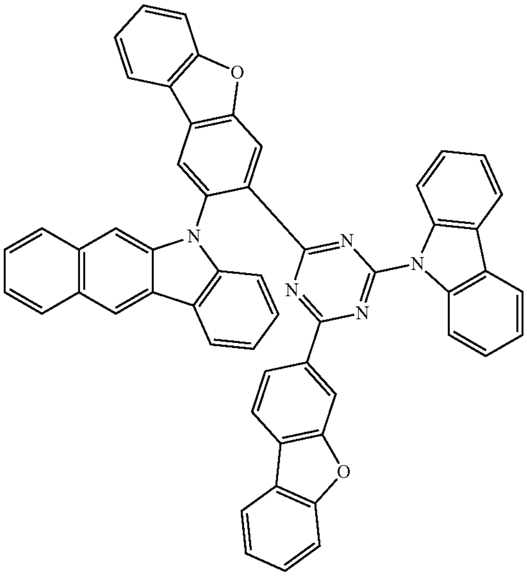
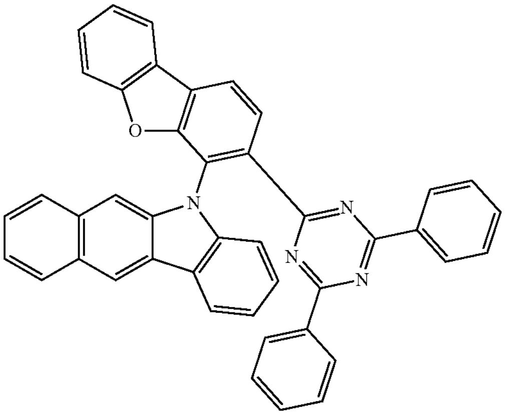
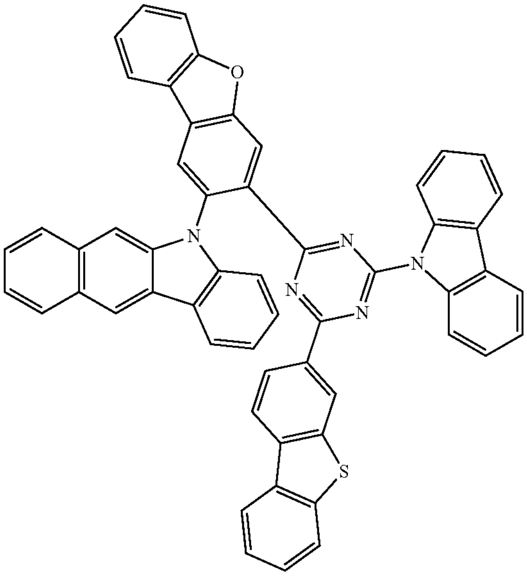
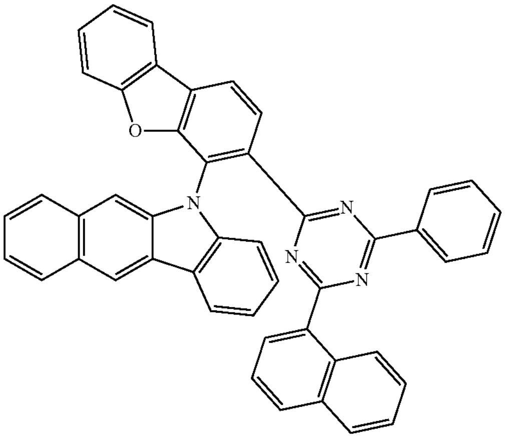
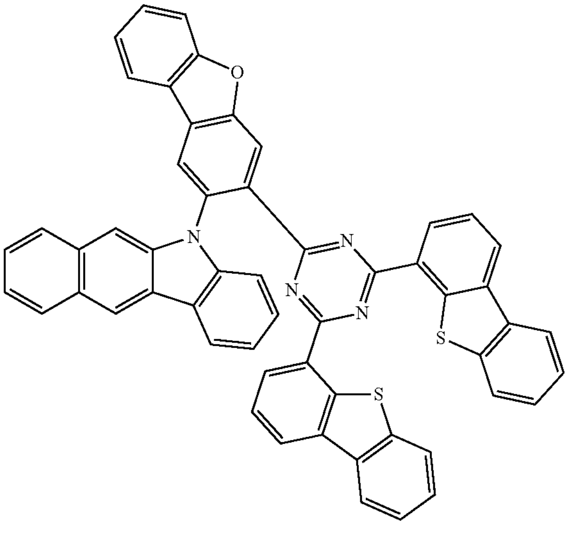
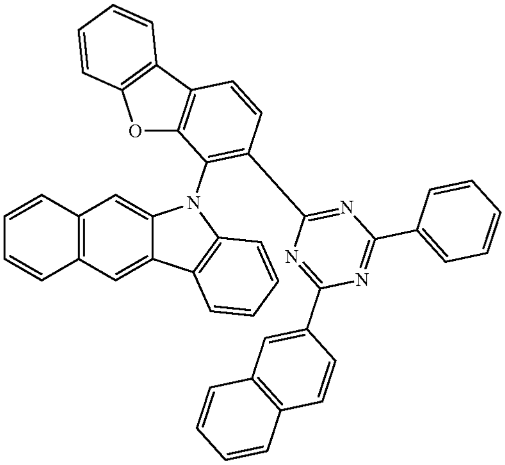
-continued -continued
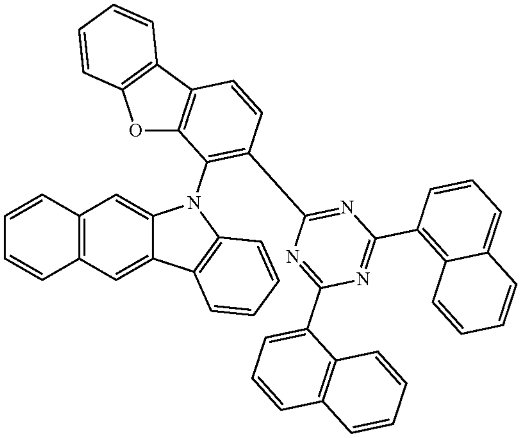
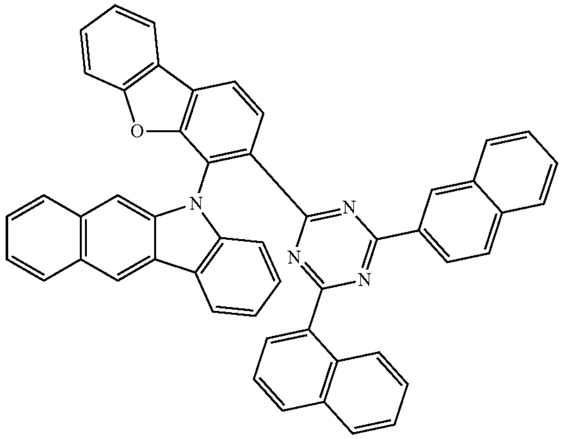
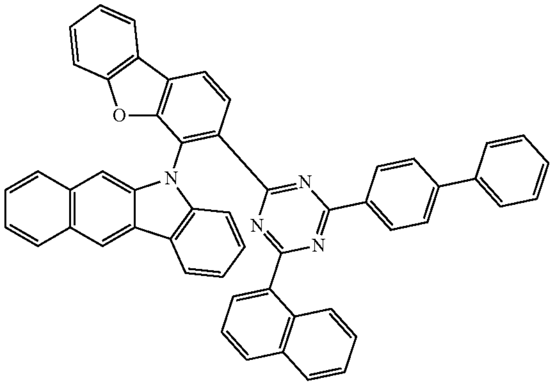
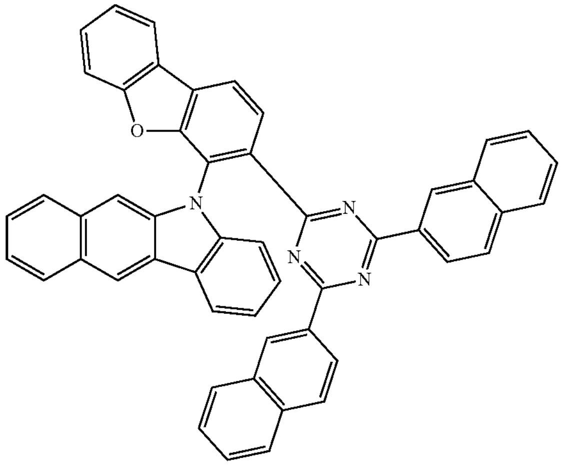
-continued
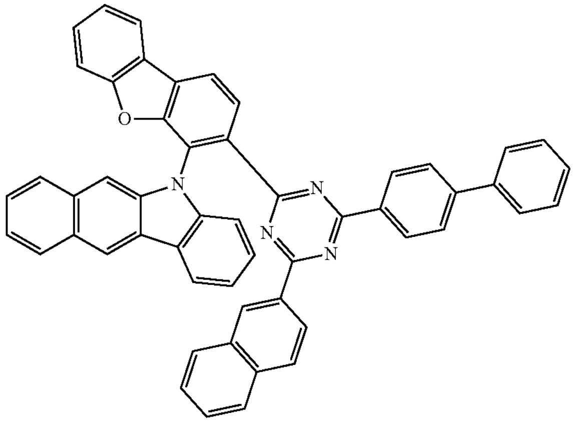
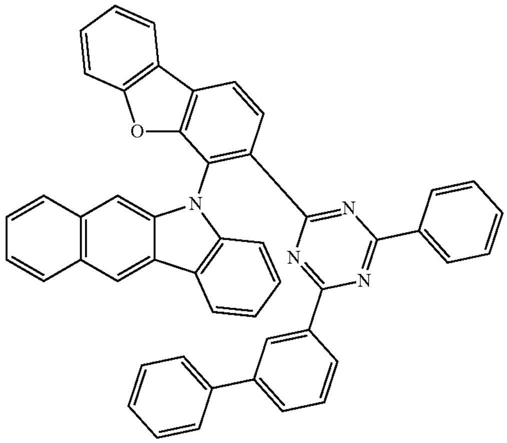
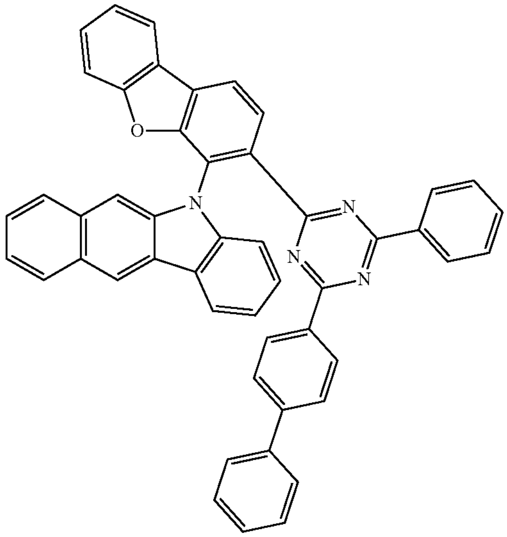

-continued
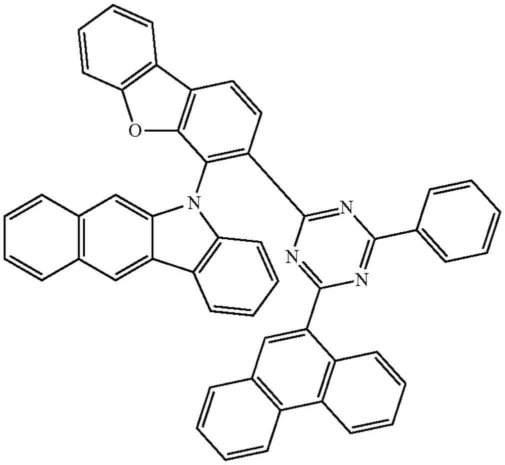
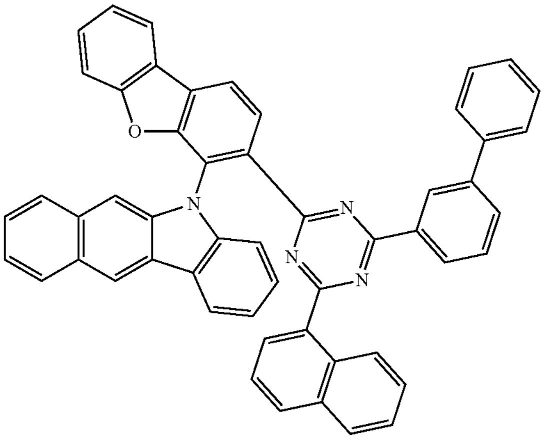
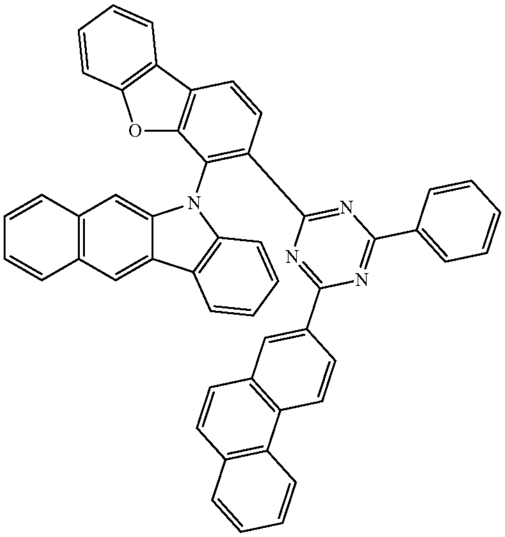
-continued
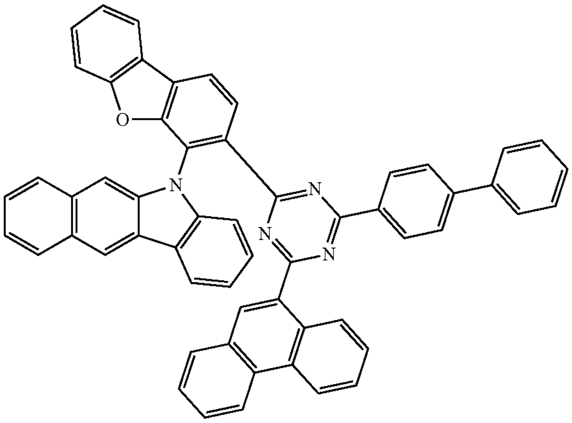
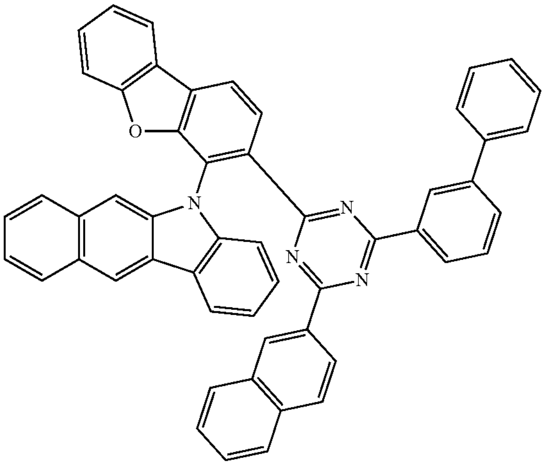
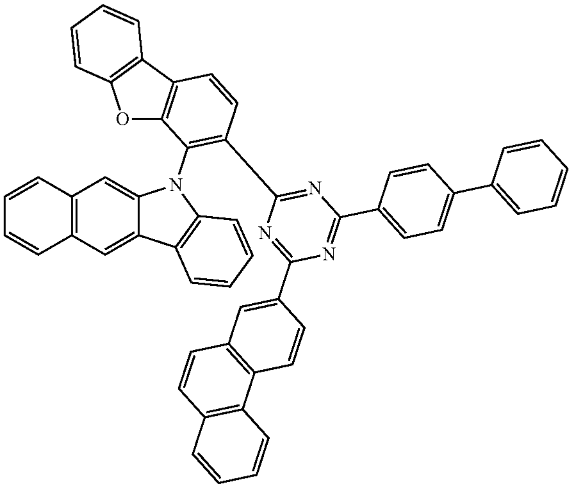

-continued
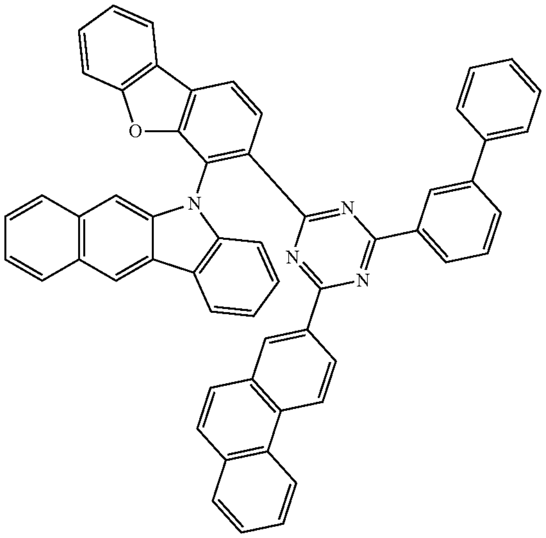
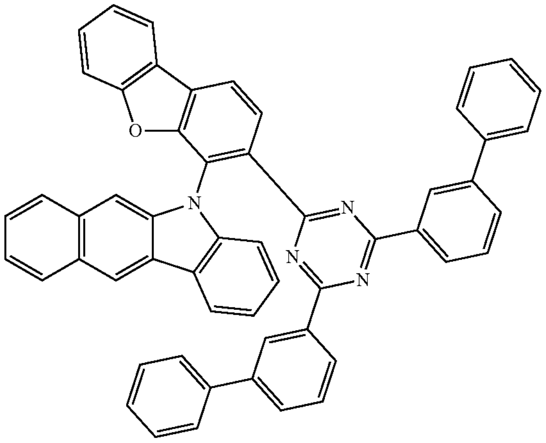
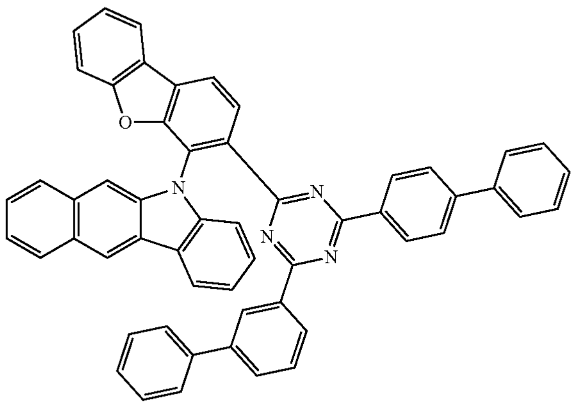
-continued
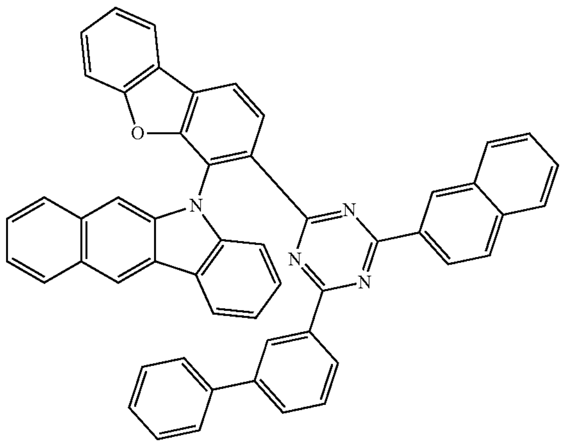
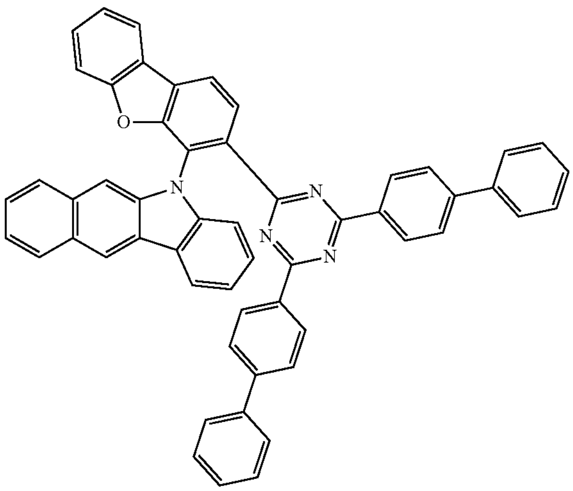
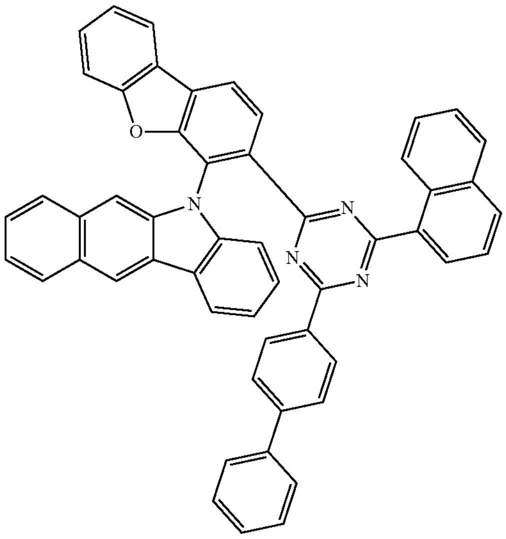

-continued
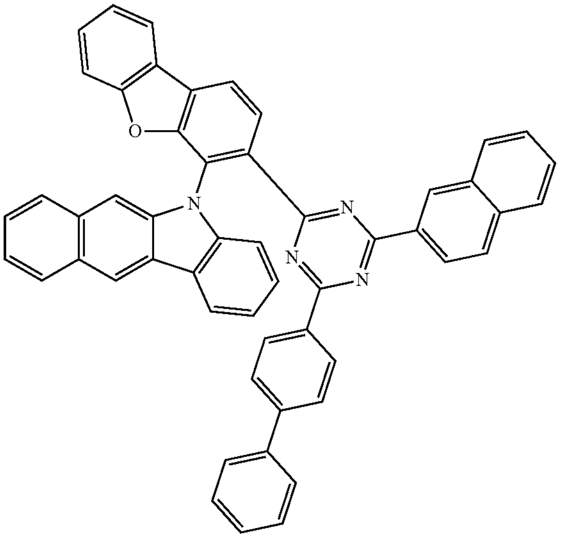
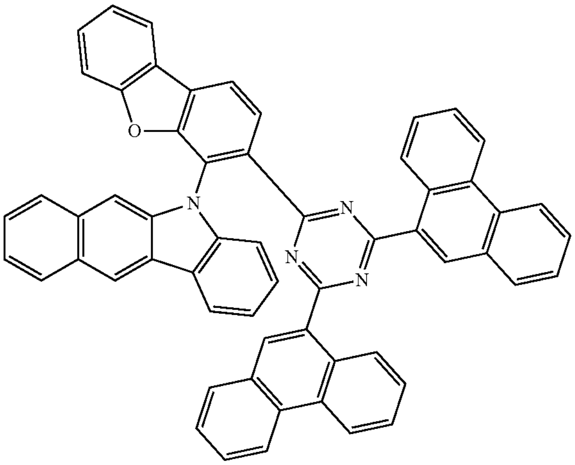
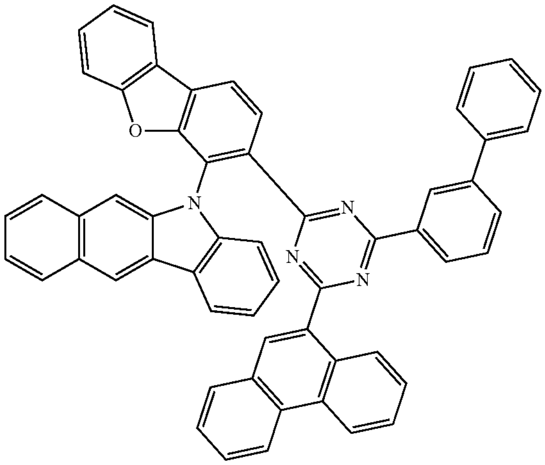
-continued
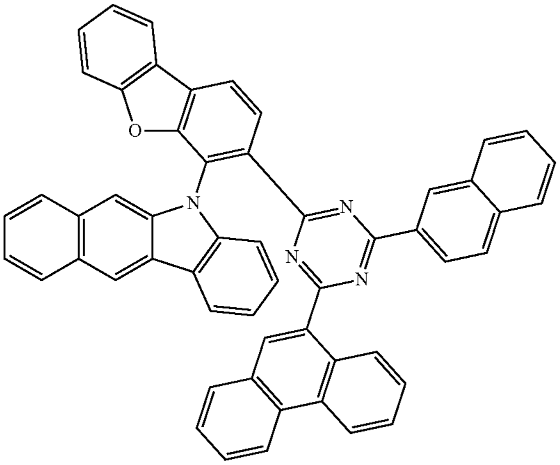
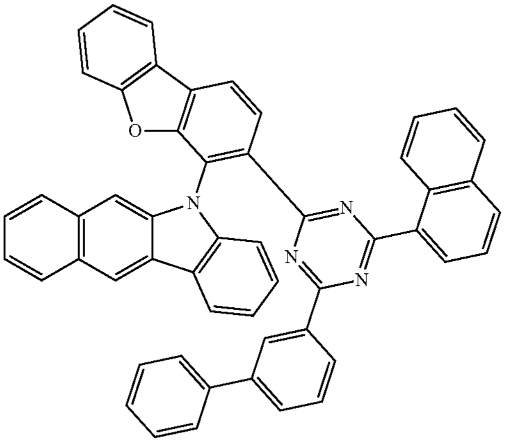
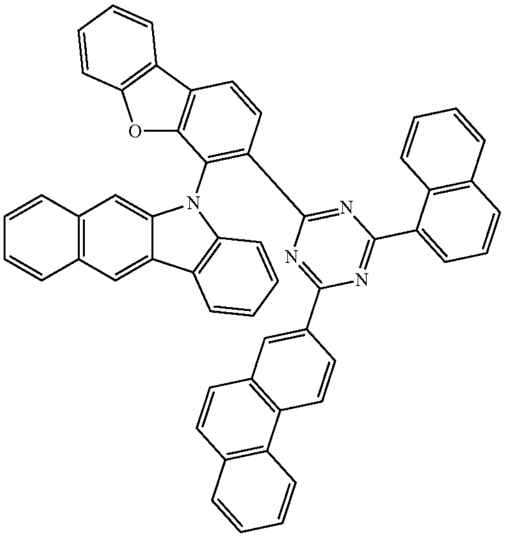

-continued
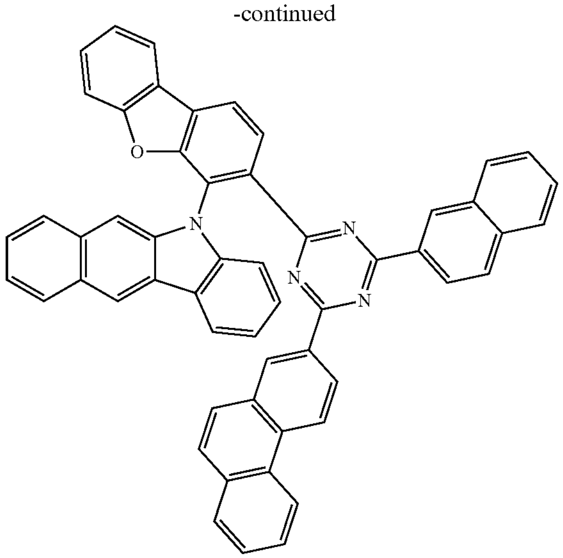
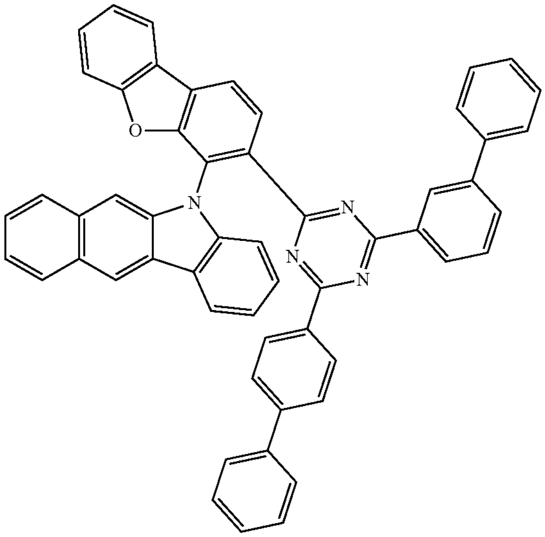
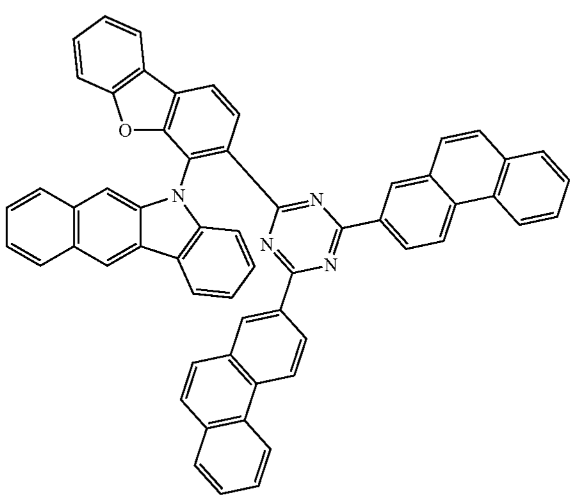
-continued
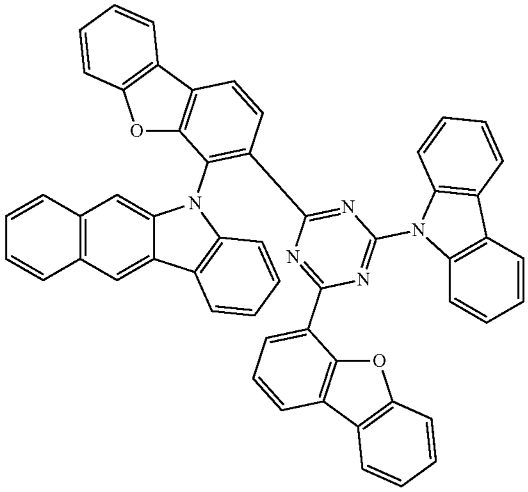
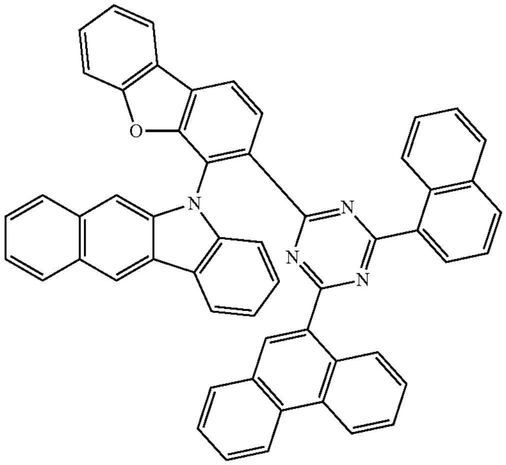
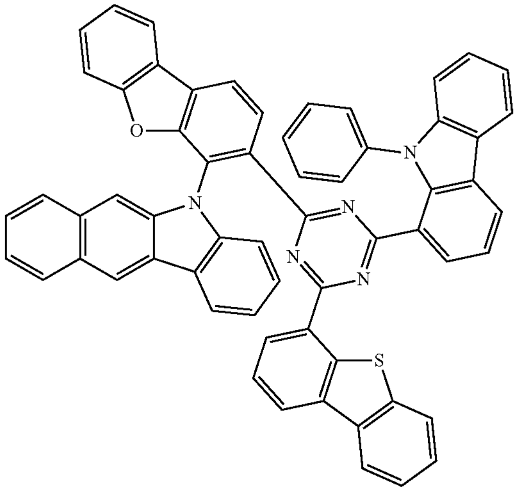

-continued
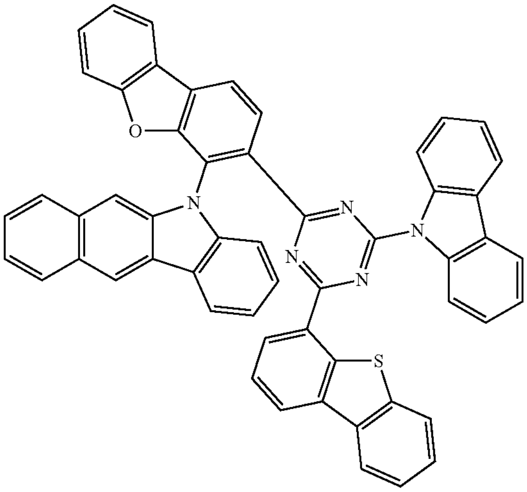
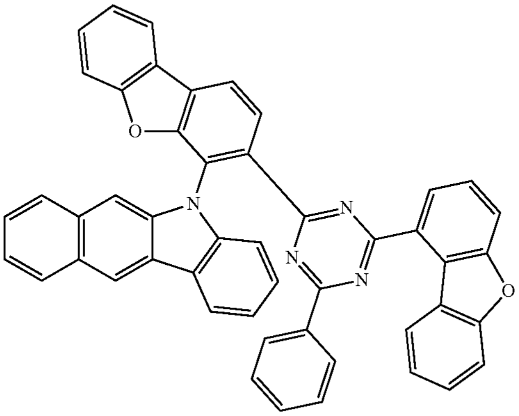
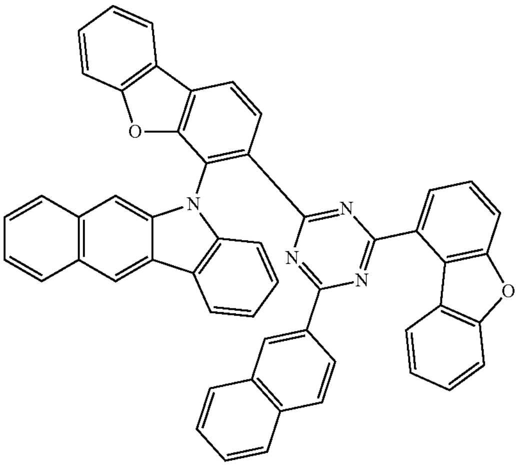
-continued
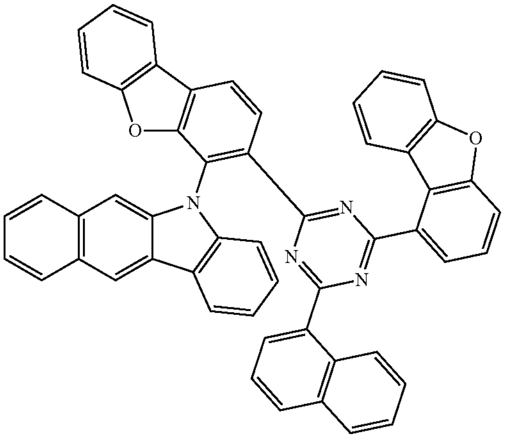
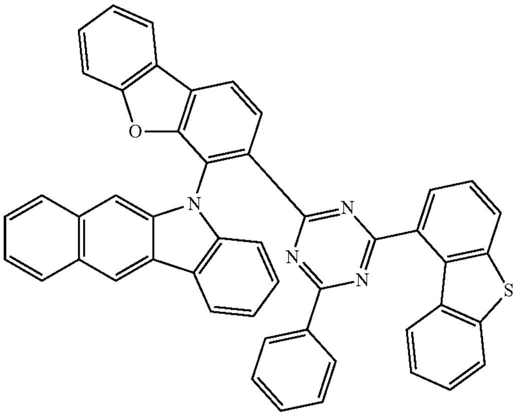
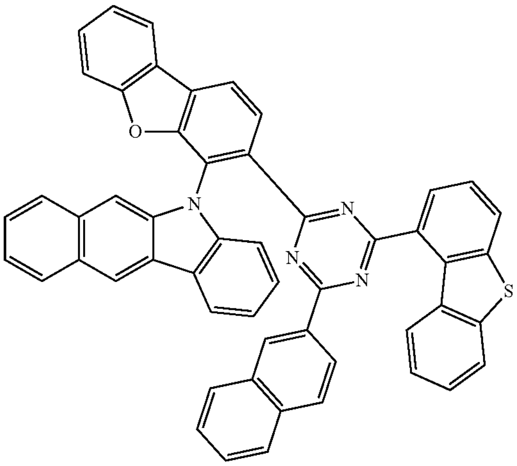

-continued
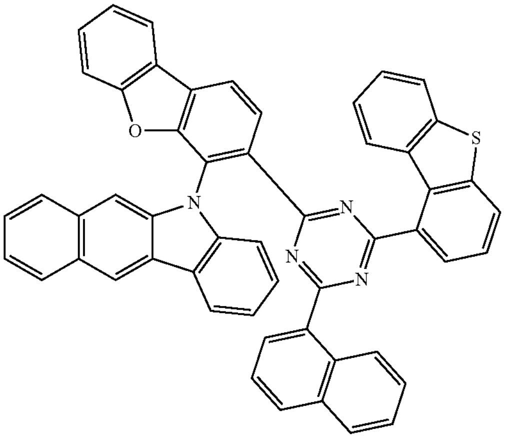
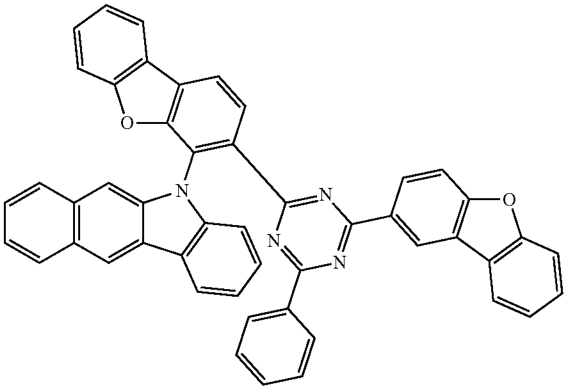
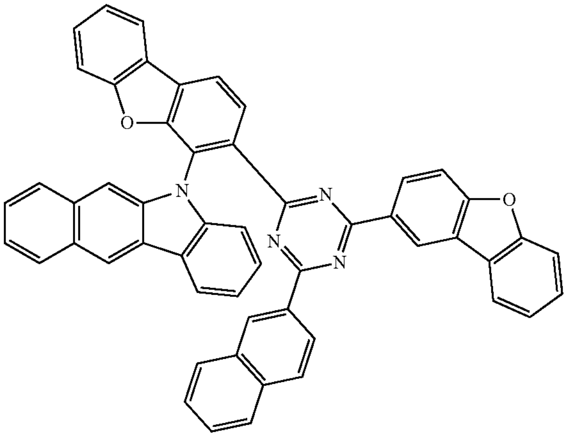
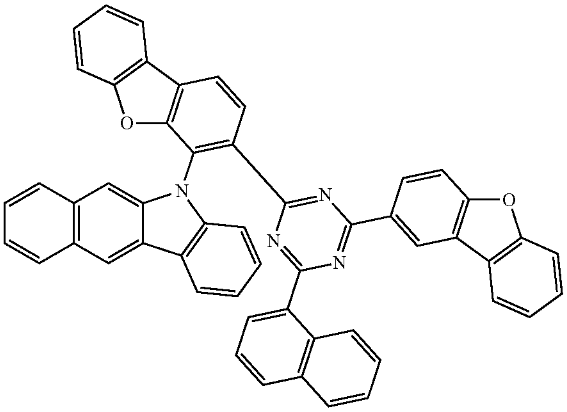
-continued
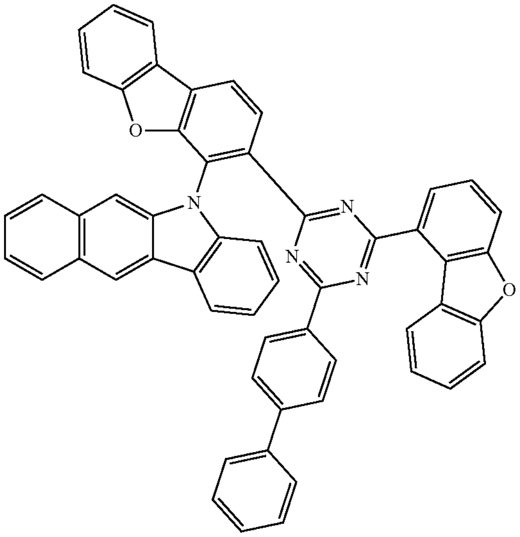
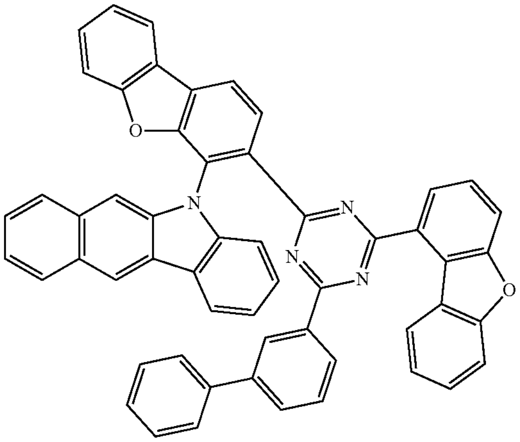
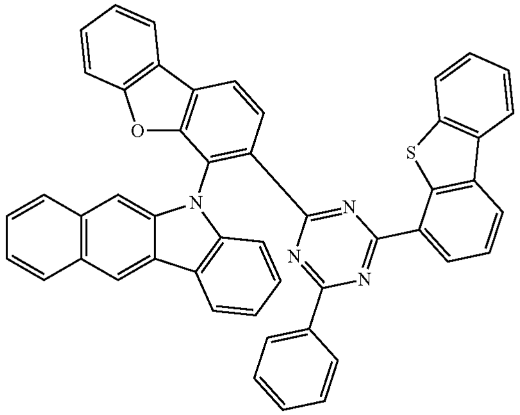

-continued
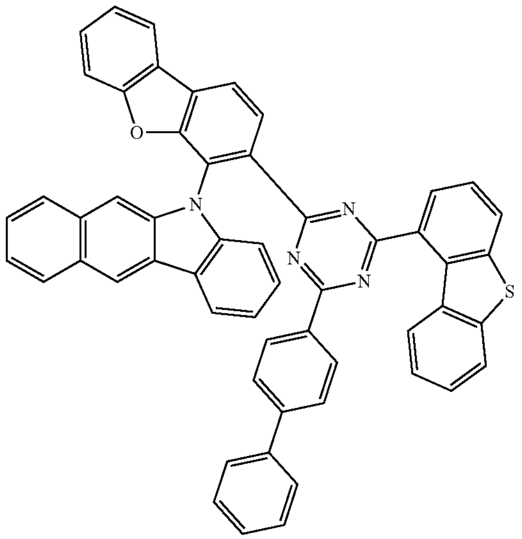
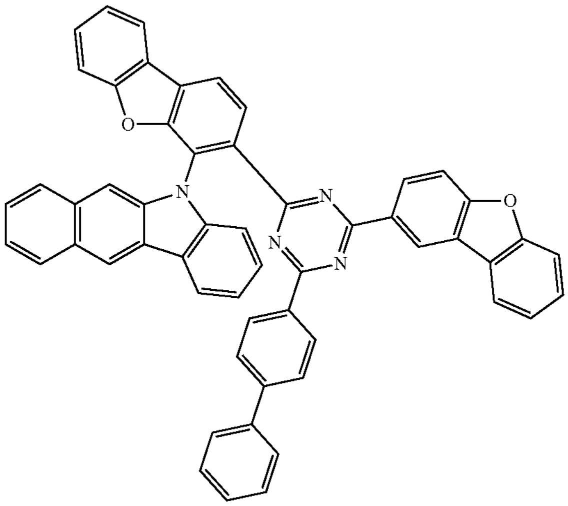
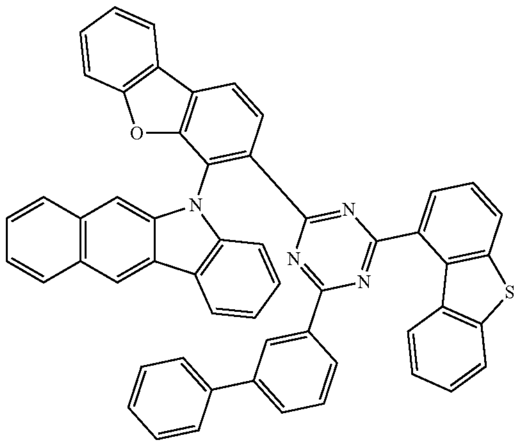
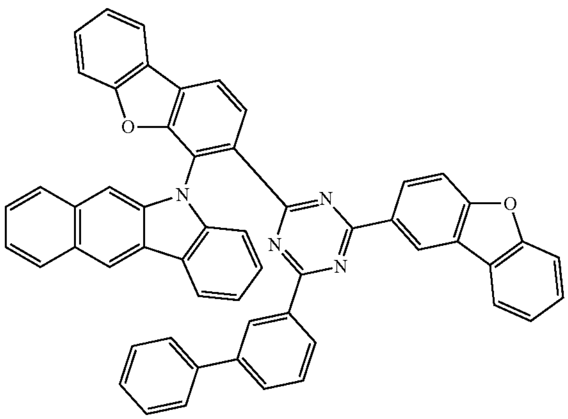
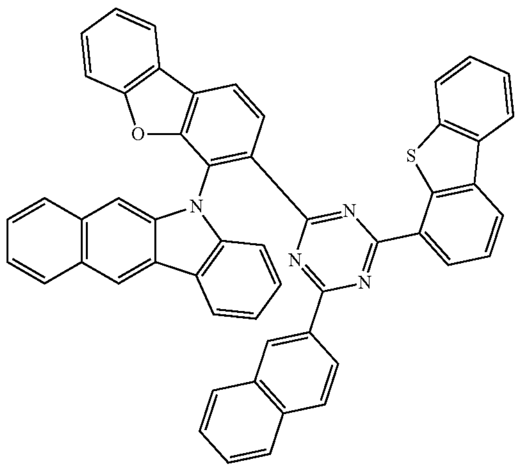
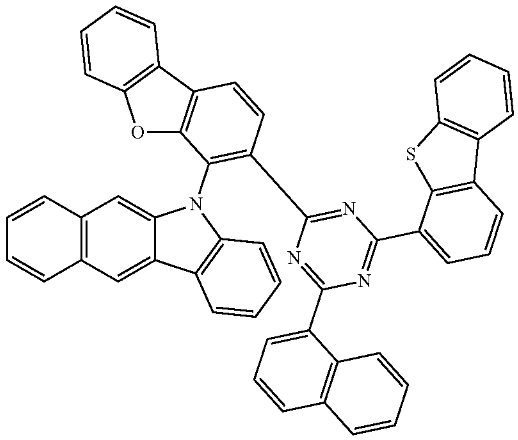
-continued -continued
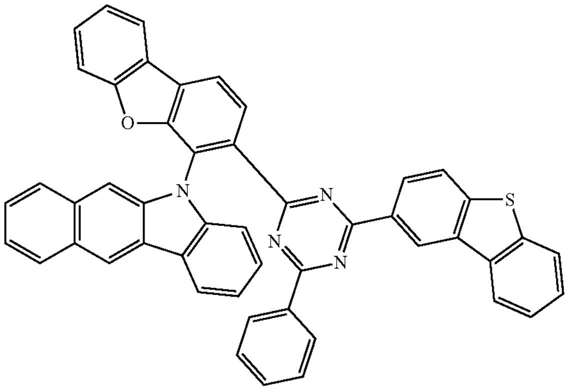
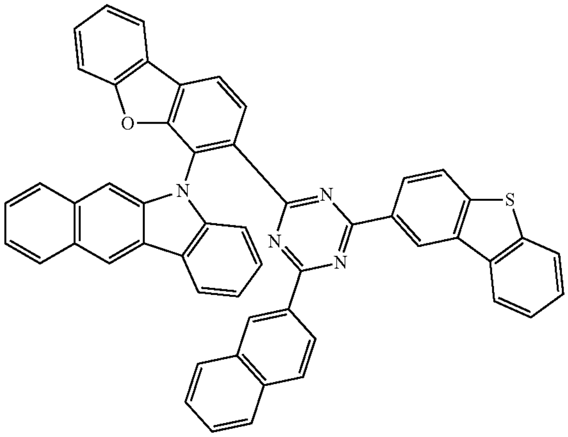
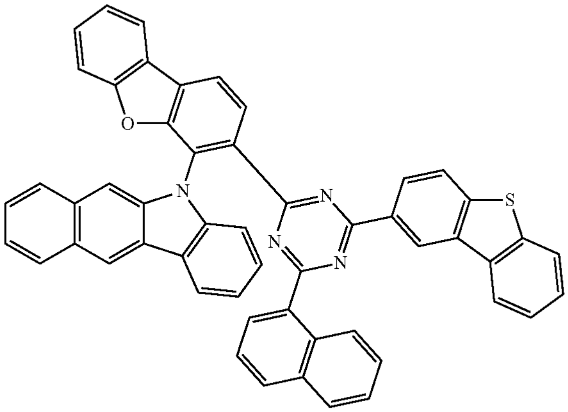
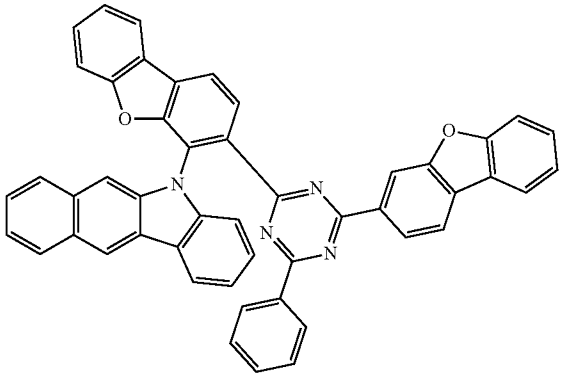
-continued
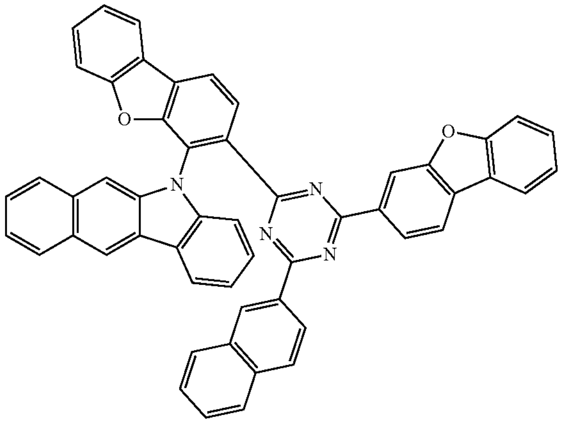
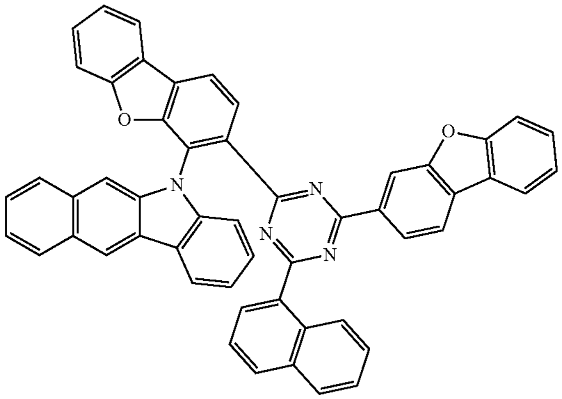
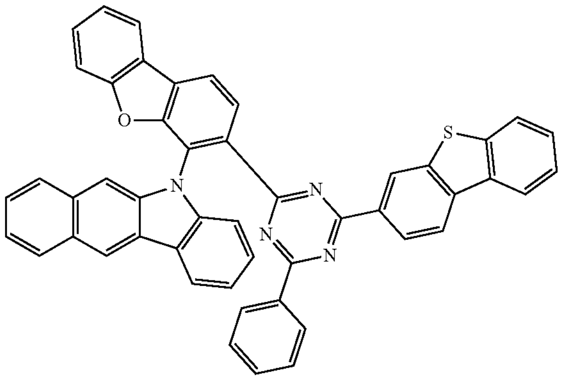
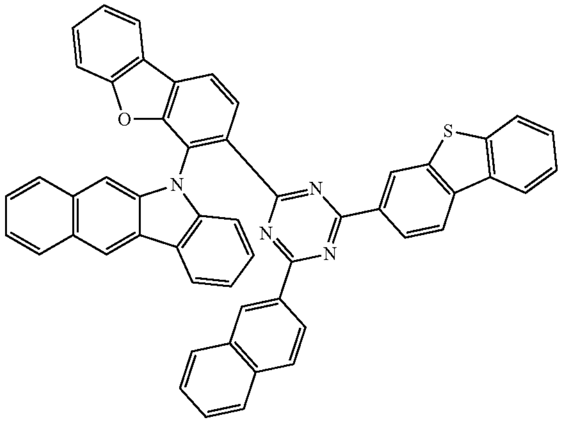

-continued
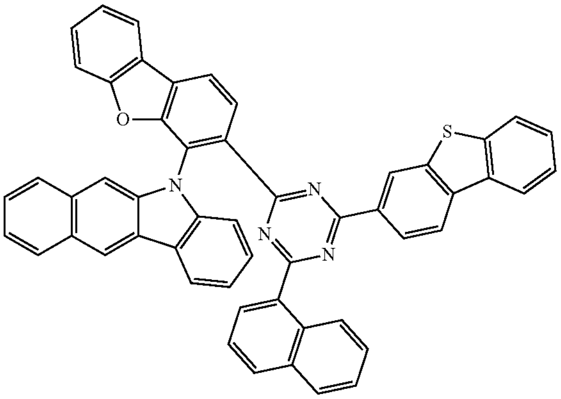
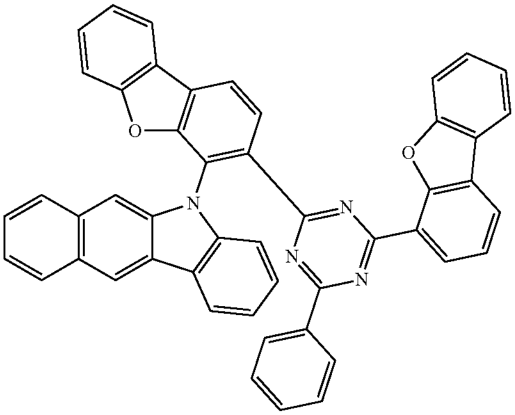
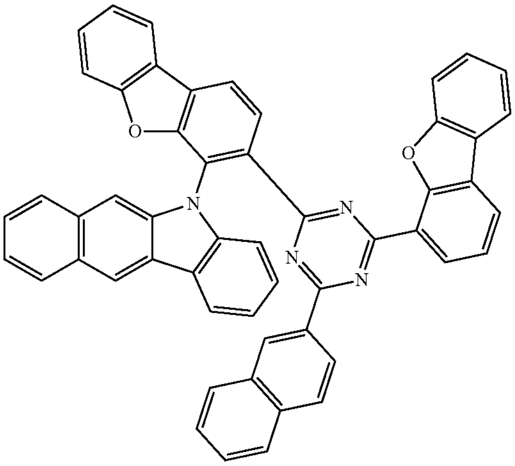
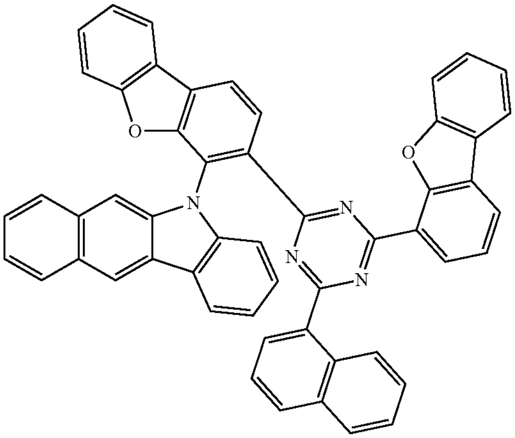
-continued
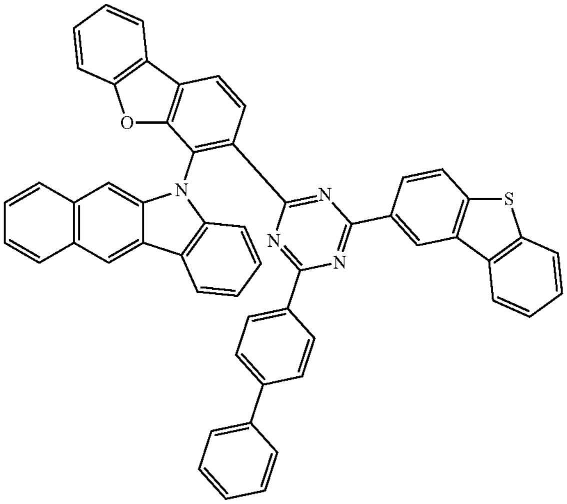
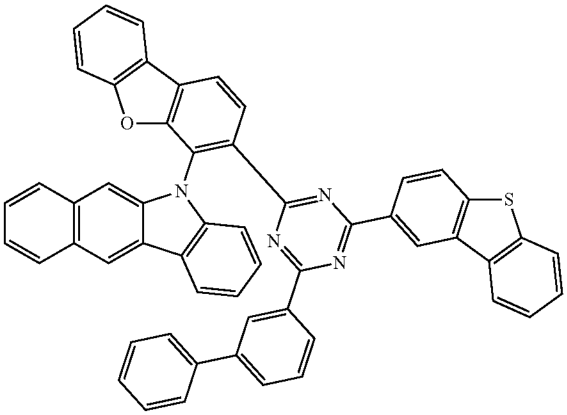
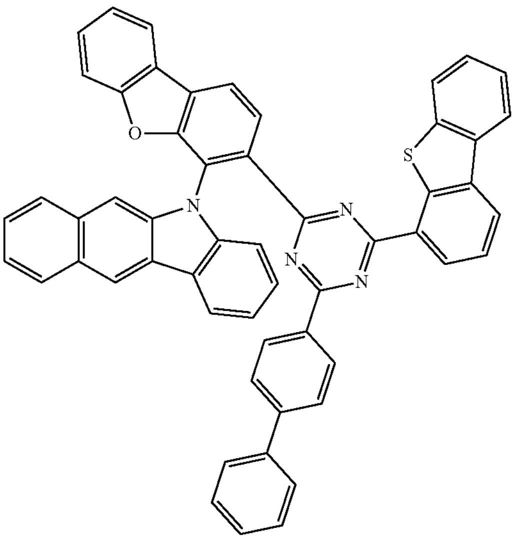

-continued
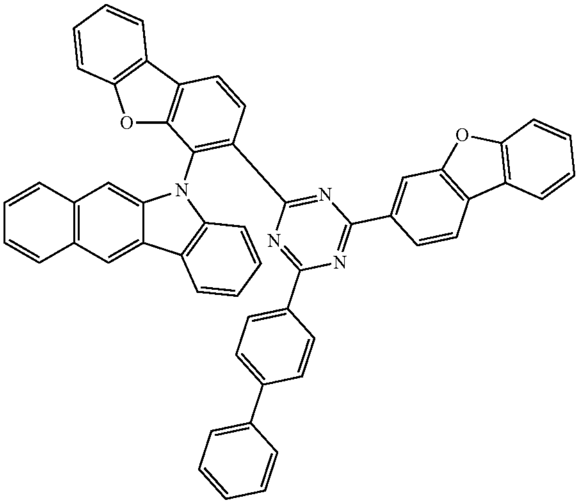
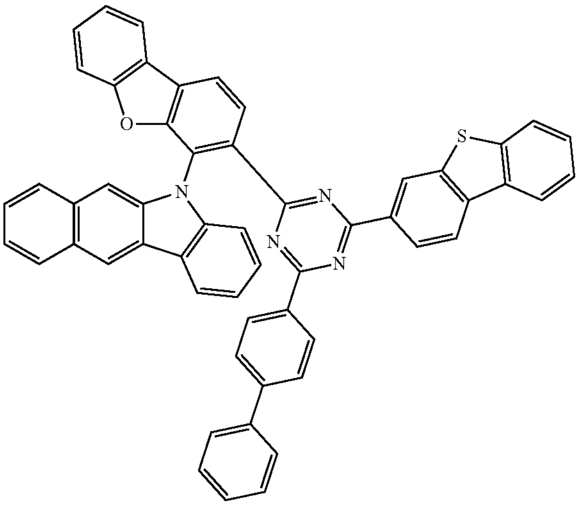
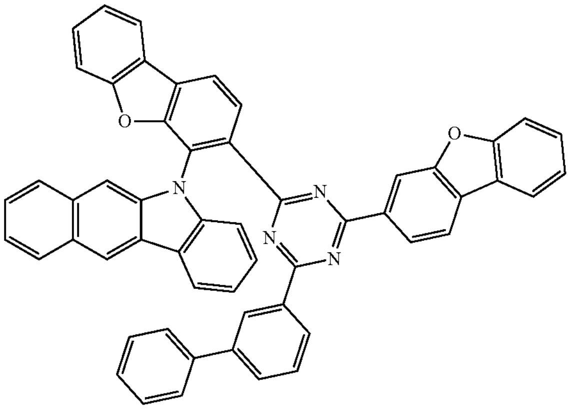
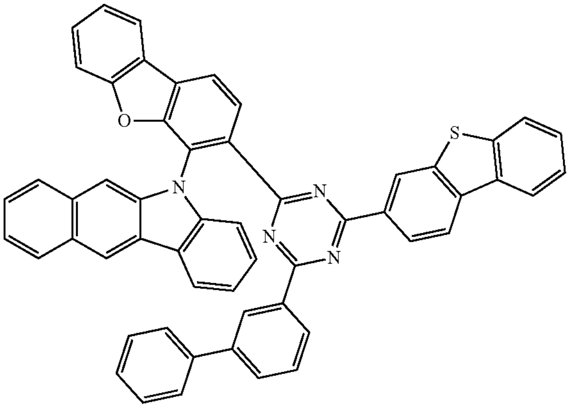
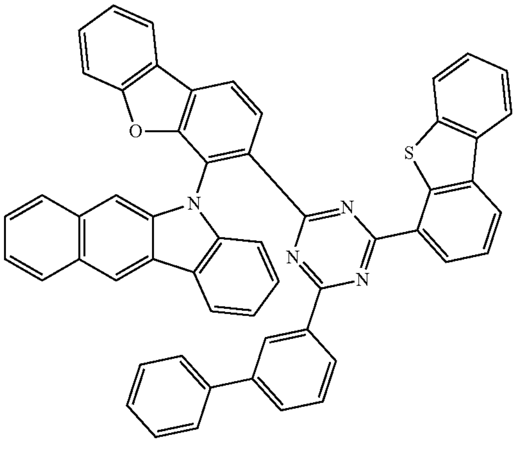
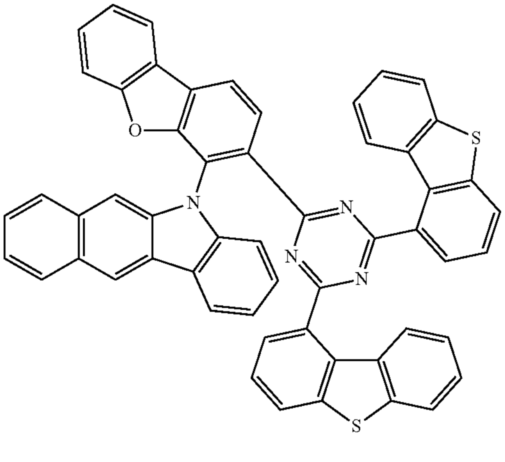
-continued -continued
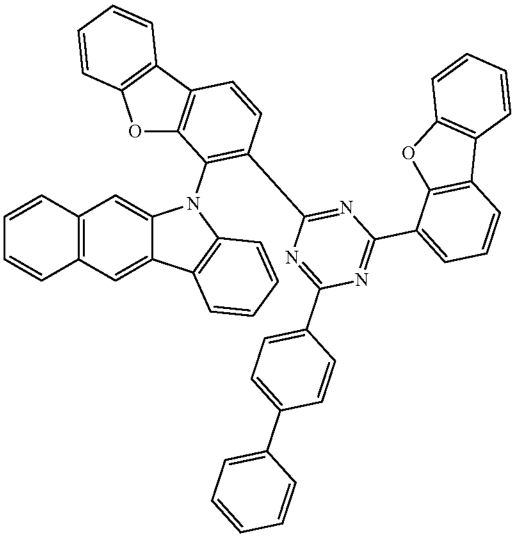
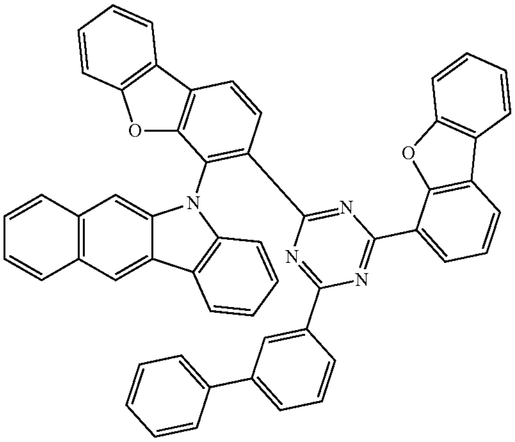
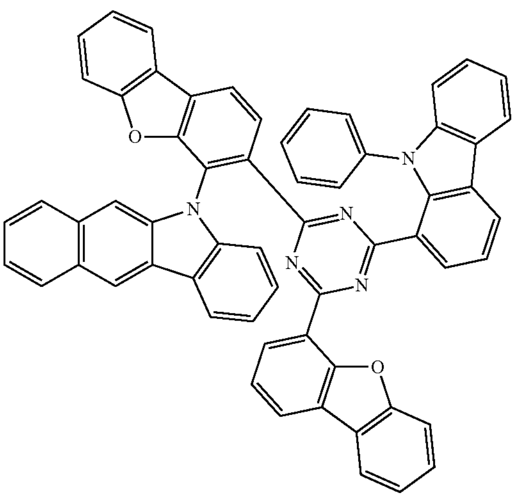
-continued
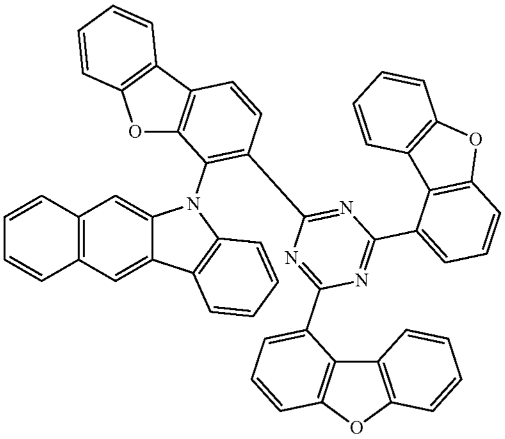
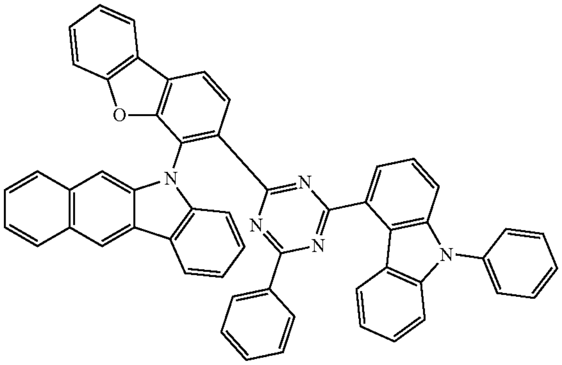
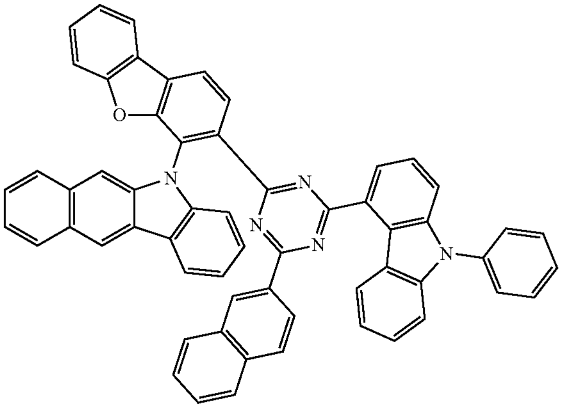
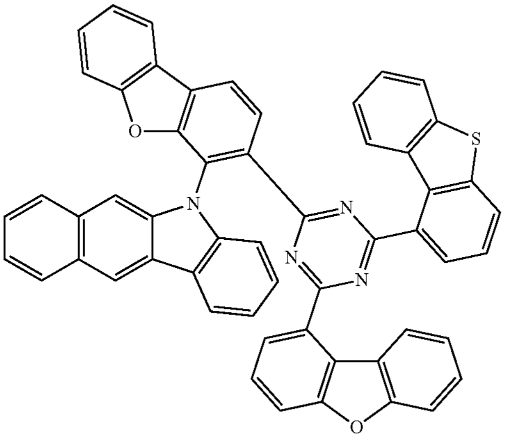

-continued
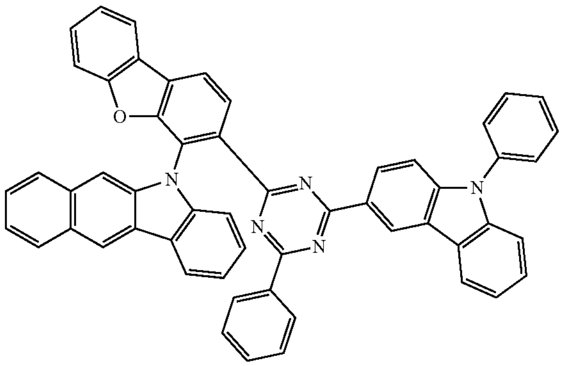
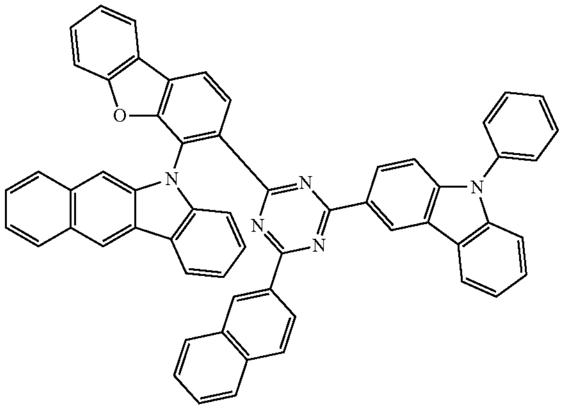
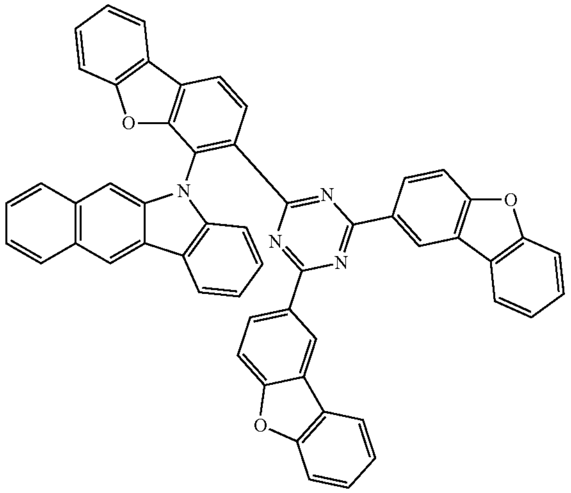
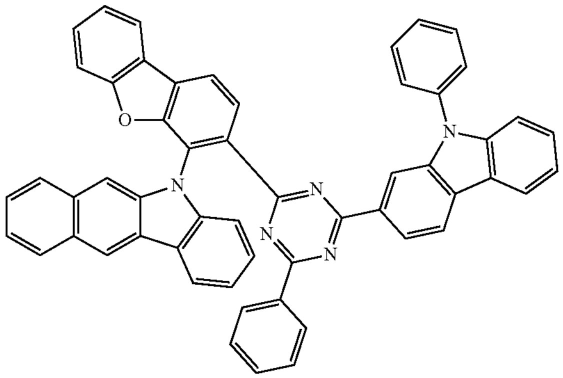
-continued
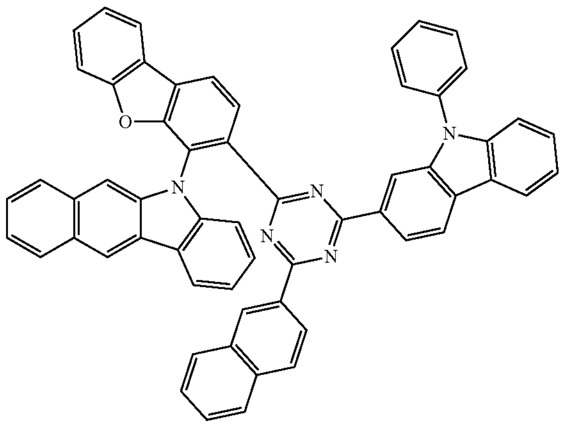
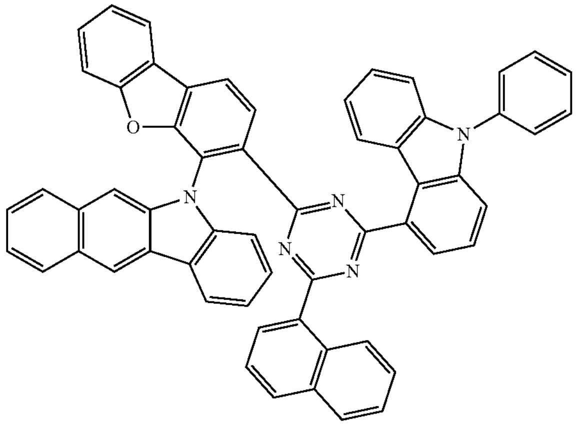
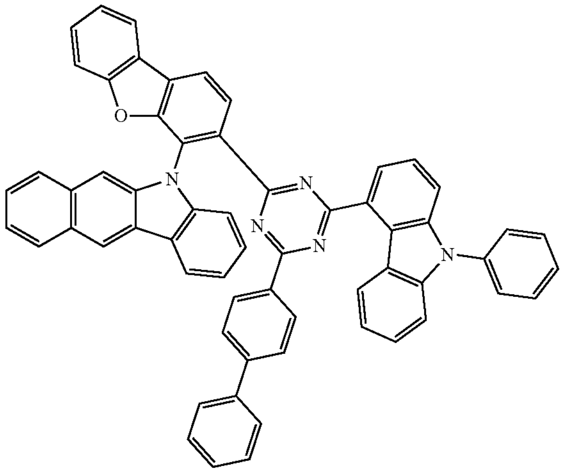

-continued
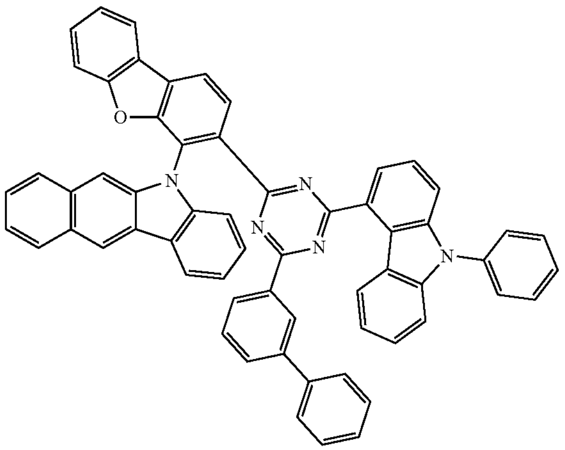
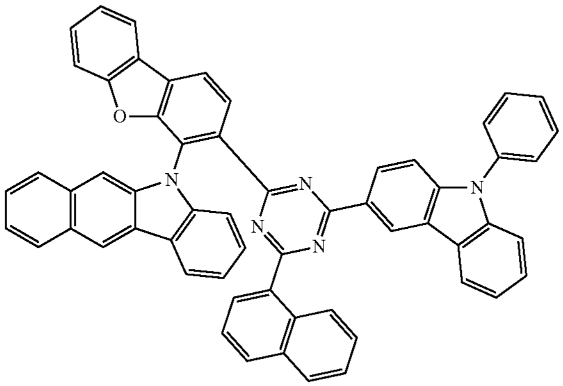
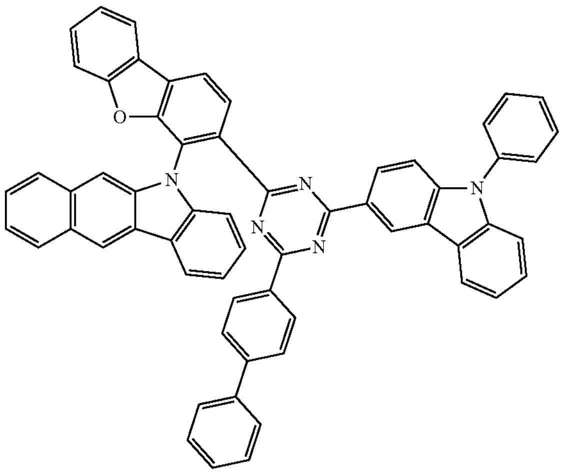
-continued
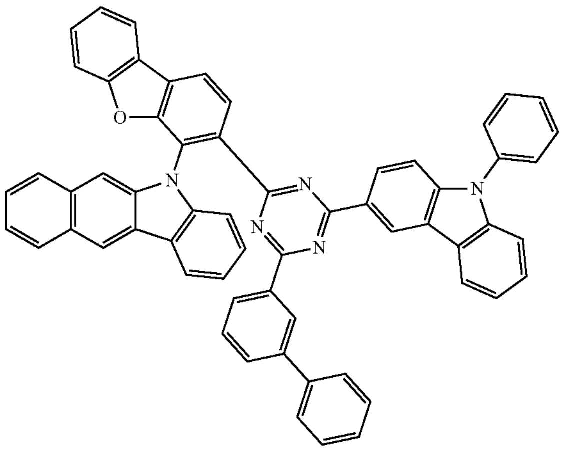
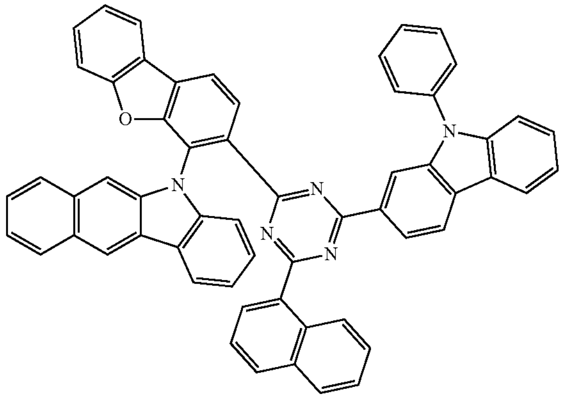
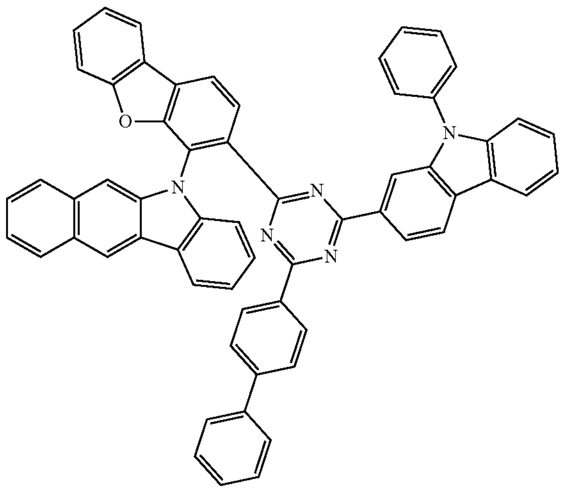

-continued
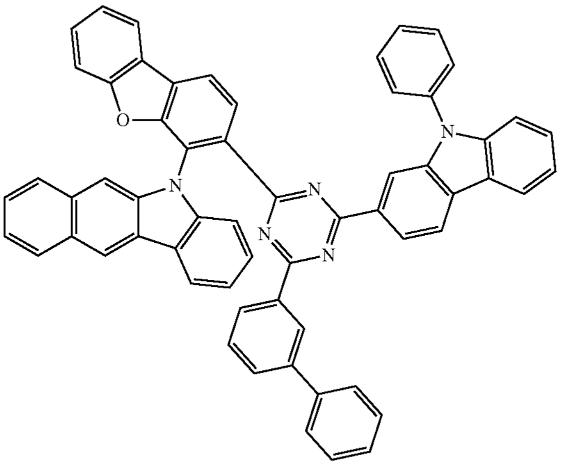
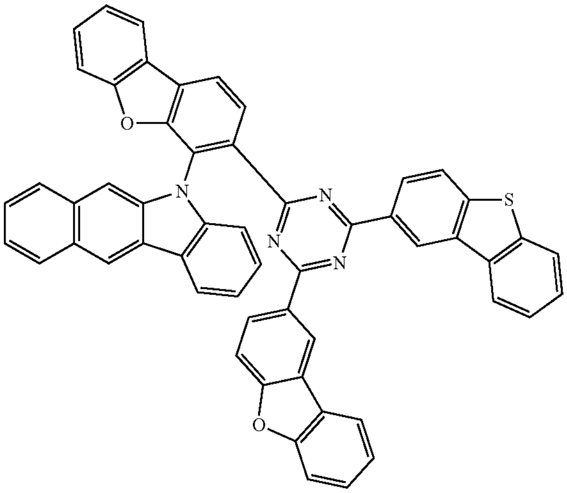
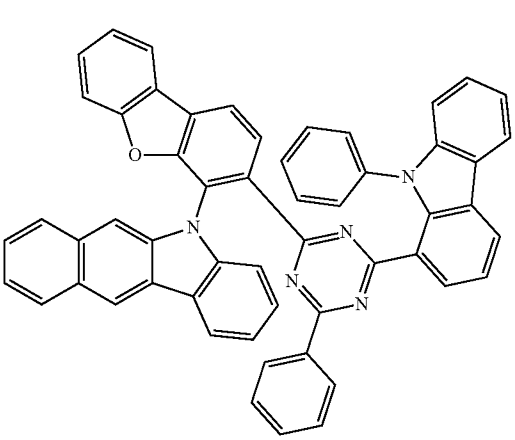
-continued
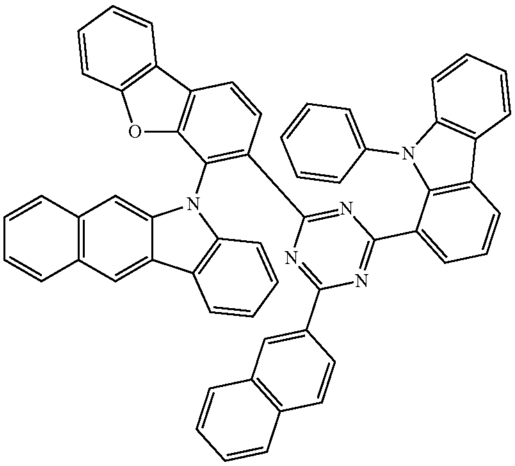
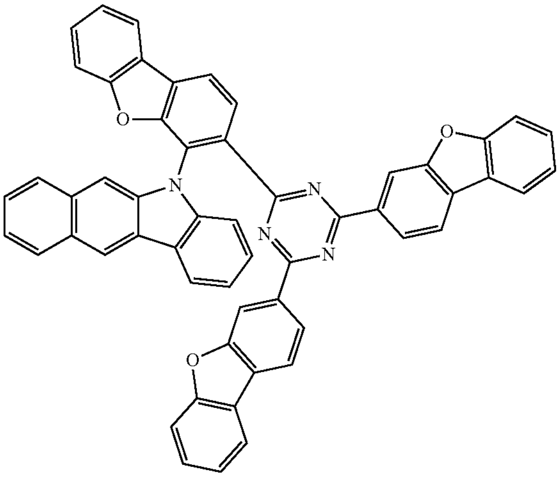
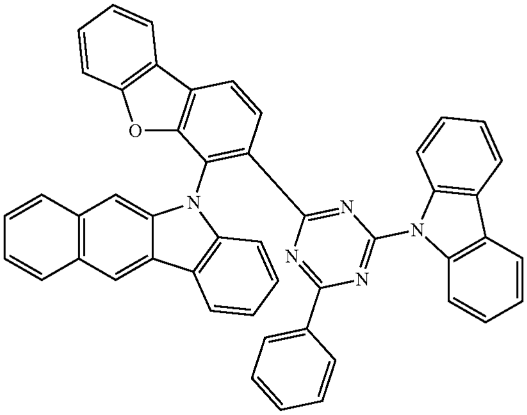

-continued
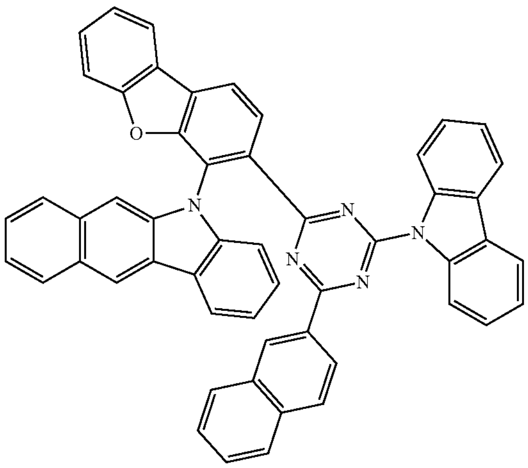
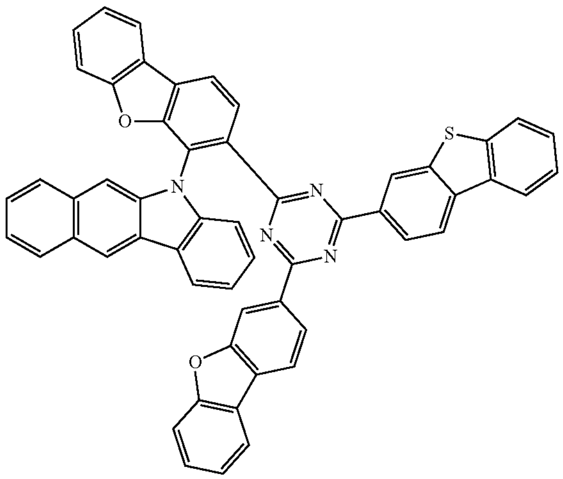
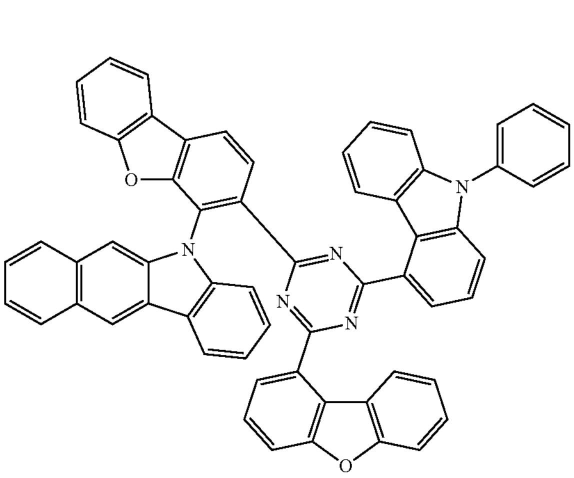
-continued
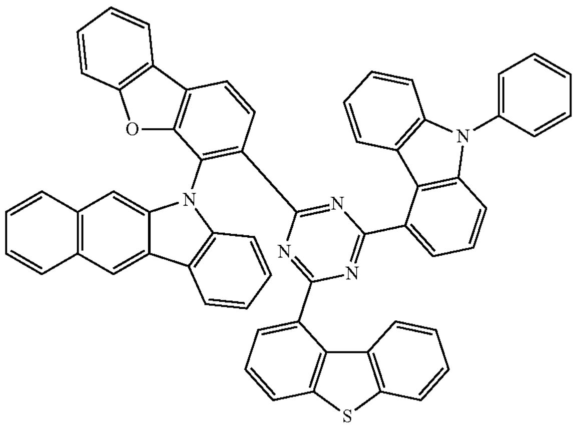
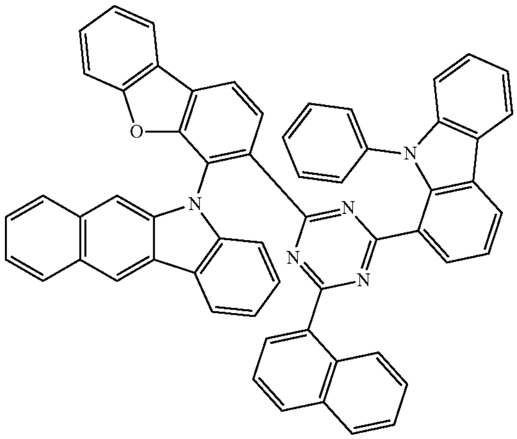
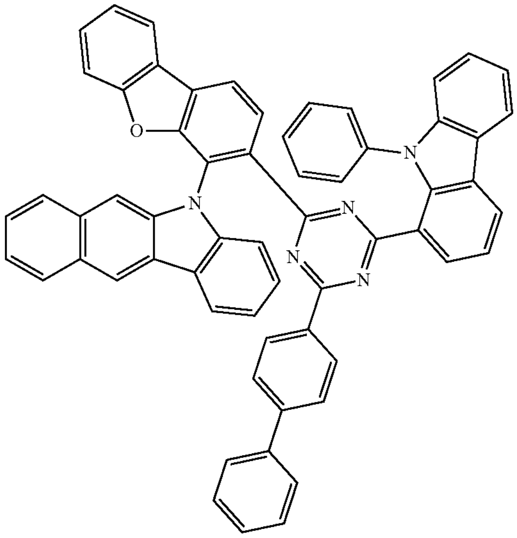

-continued
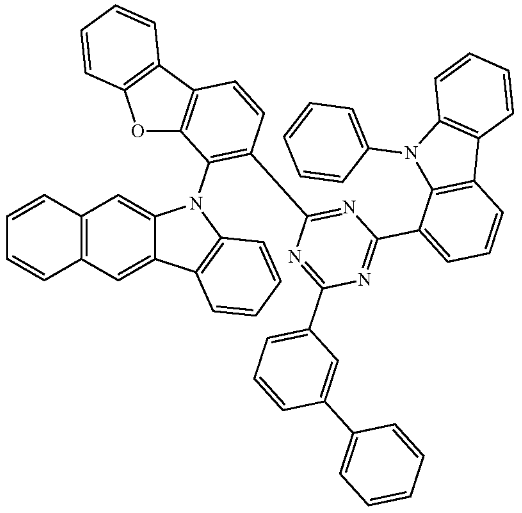
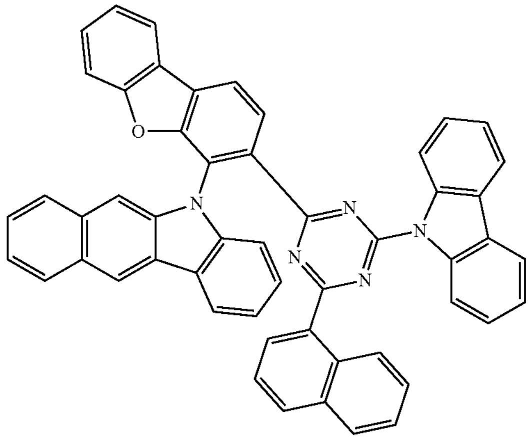
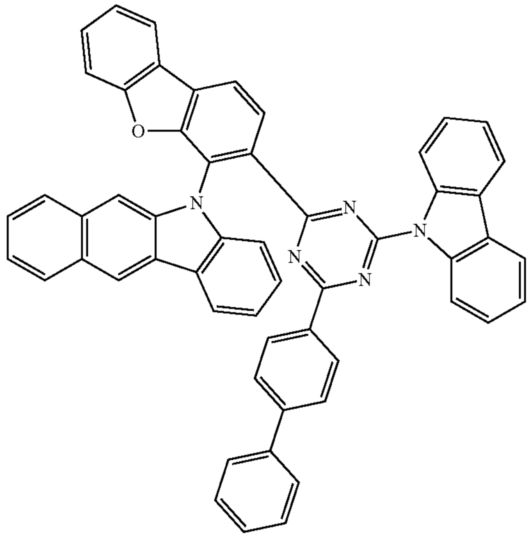
-continued
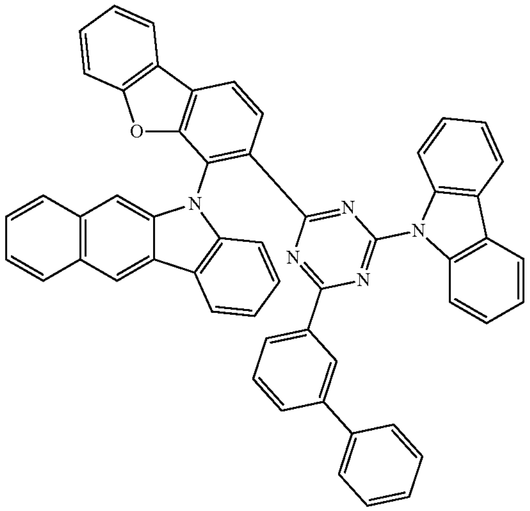
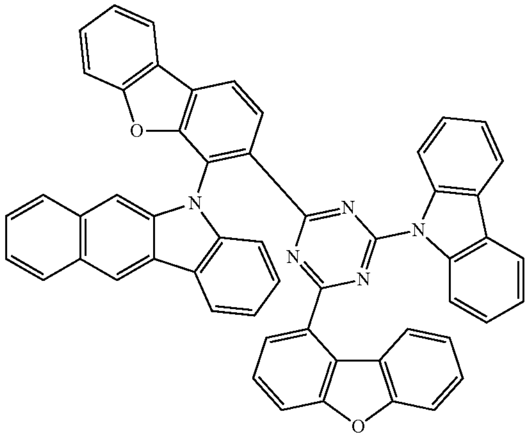
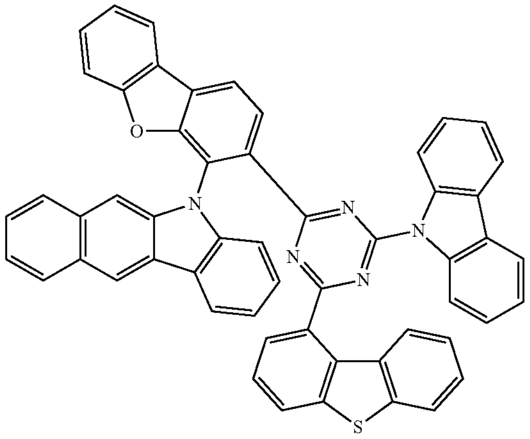

-continued
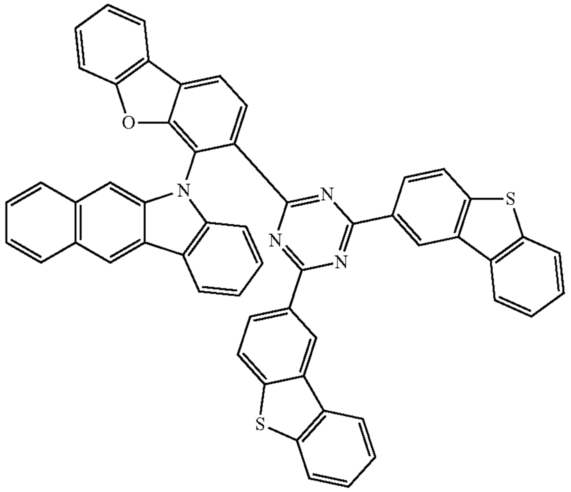
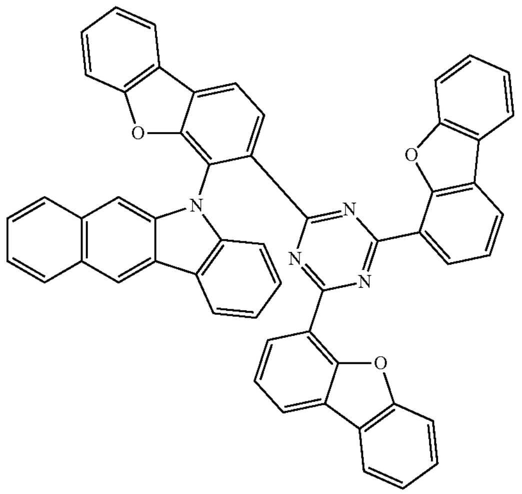
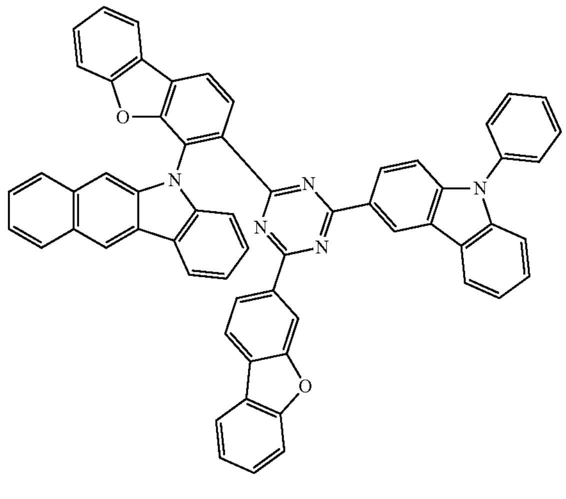
-continued
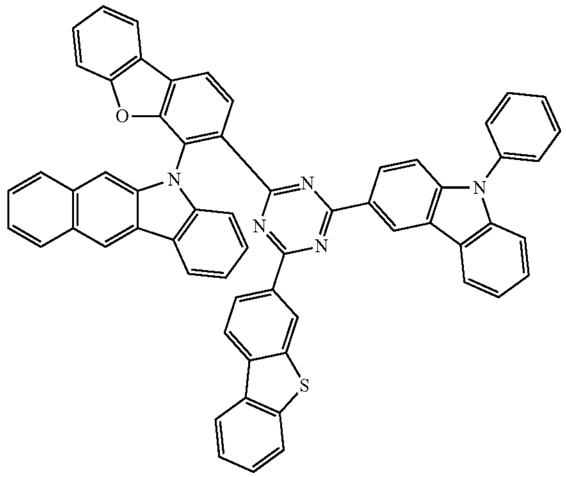
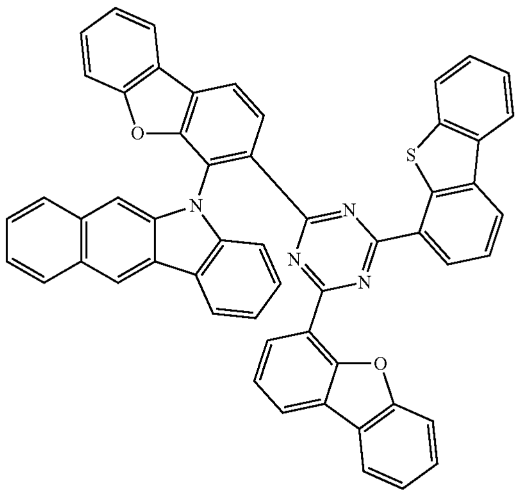
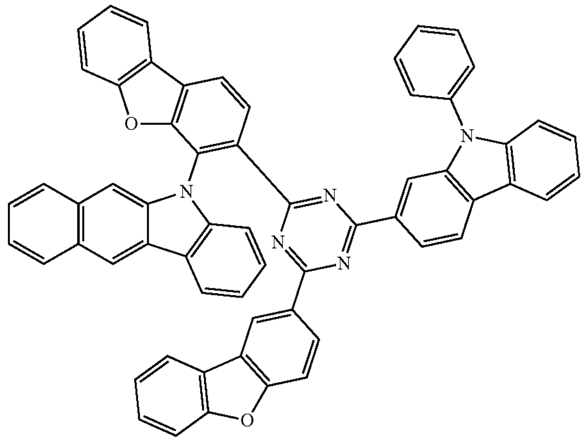

-continued
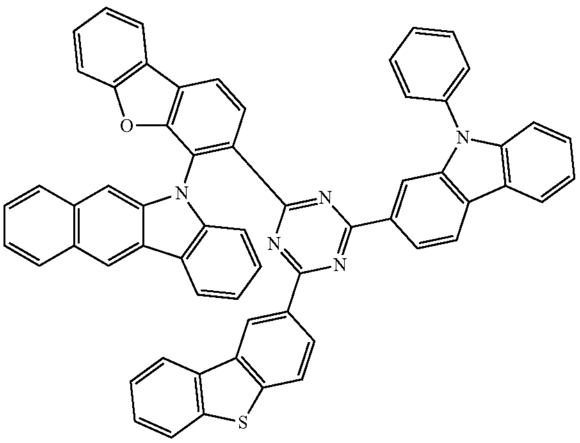
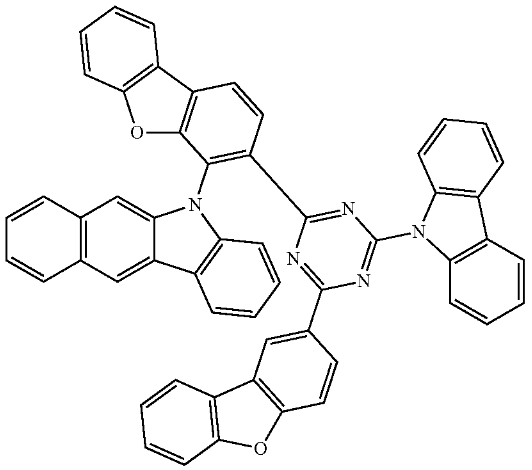
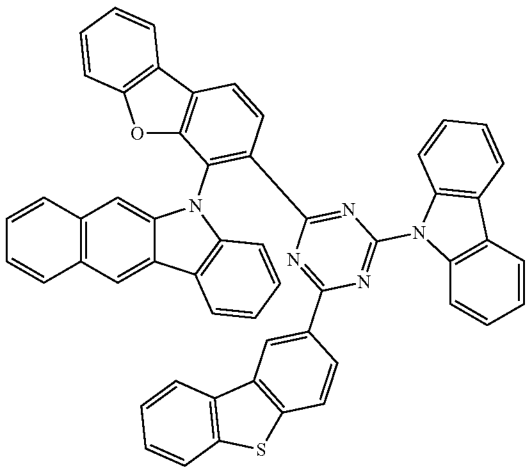
-continued
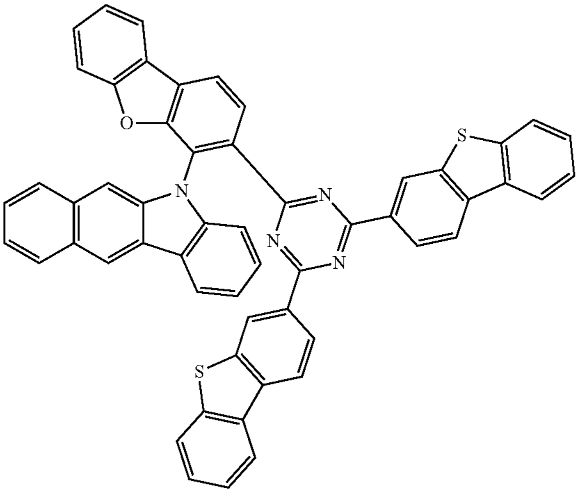
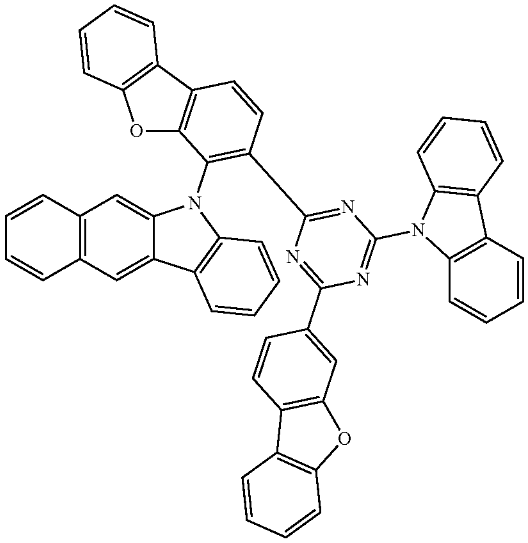
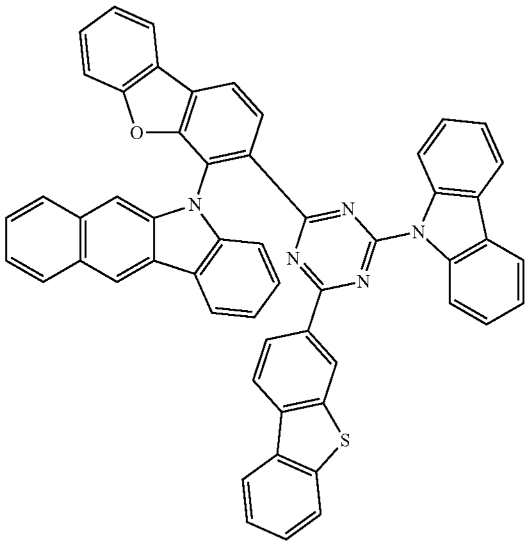

-continued
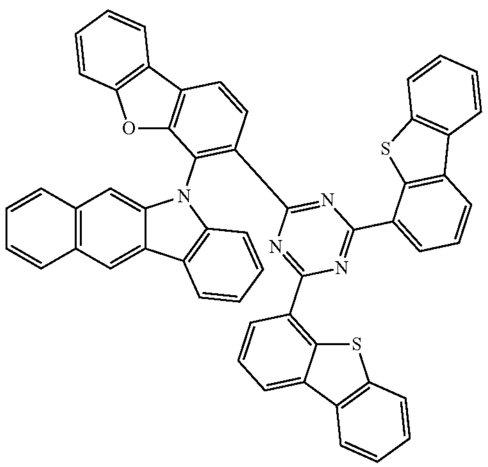
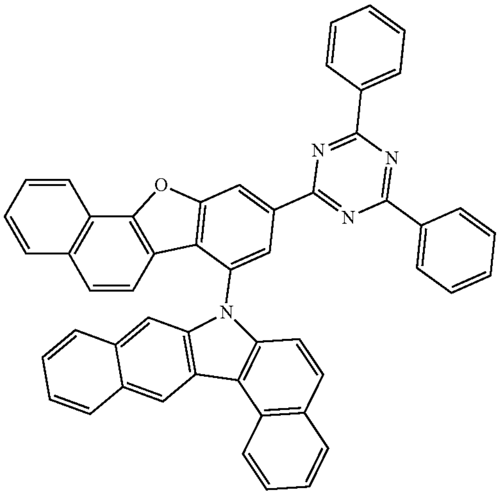
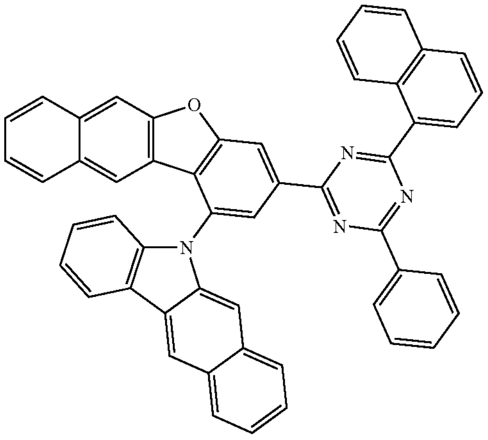
-continued
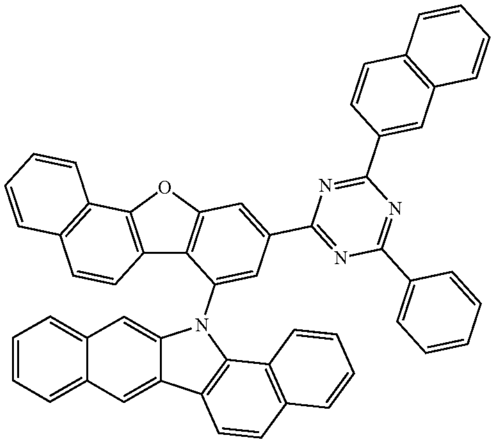
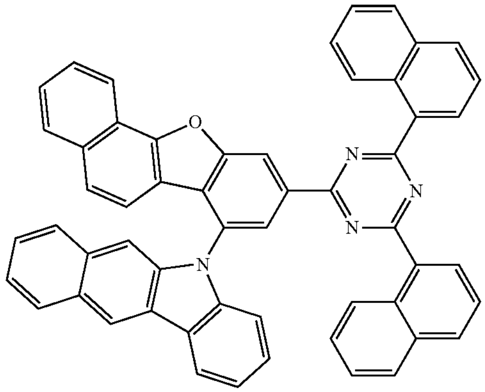
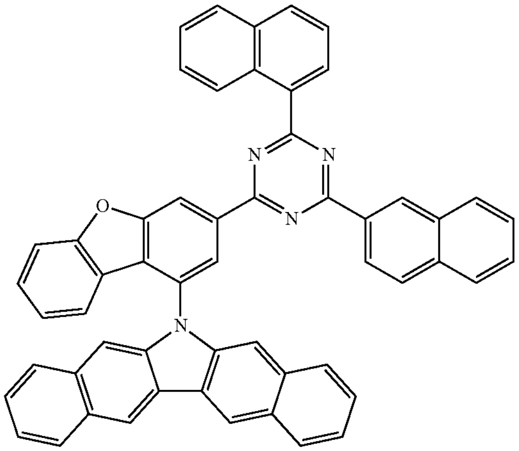
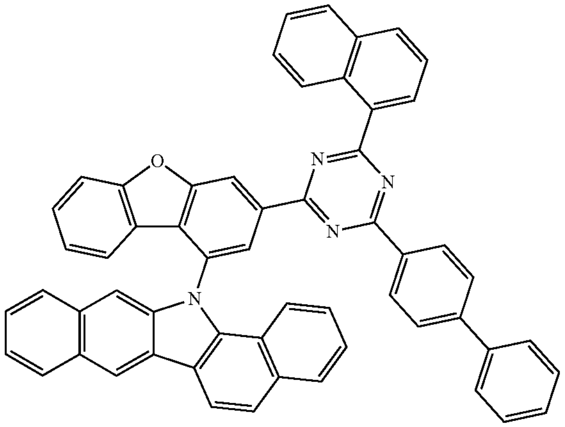

-continued
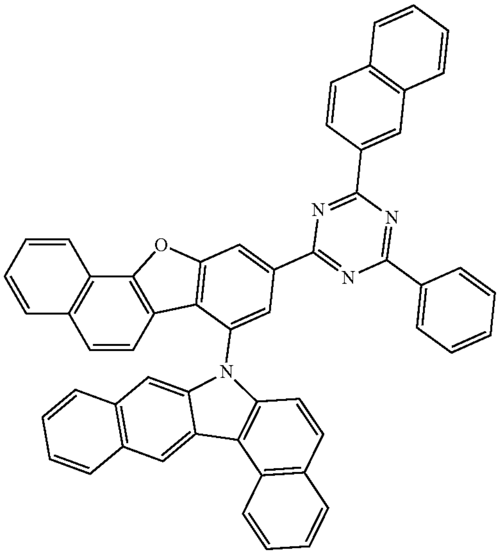
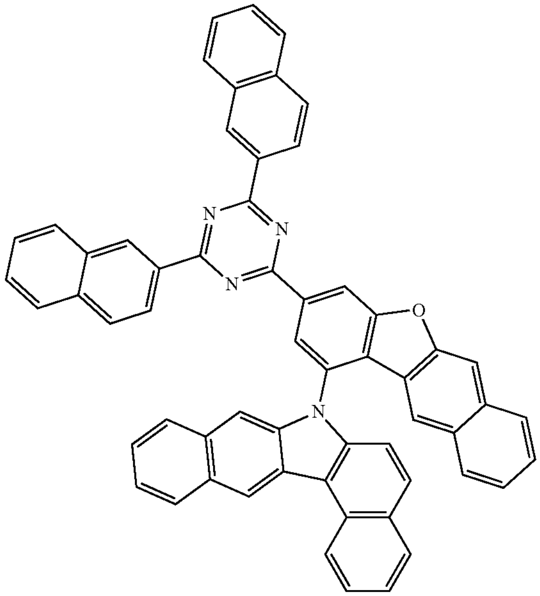
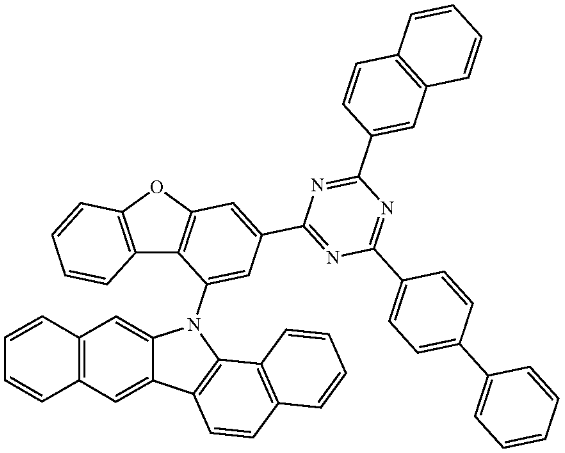
-continued
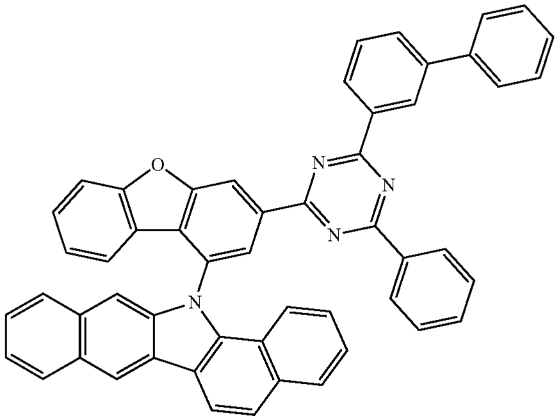
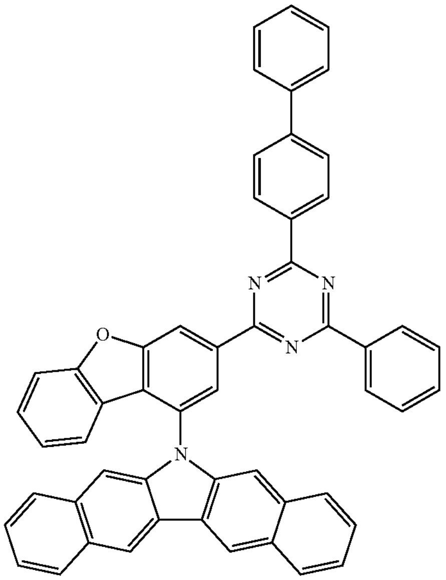
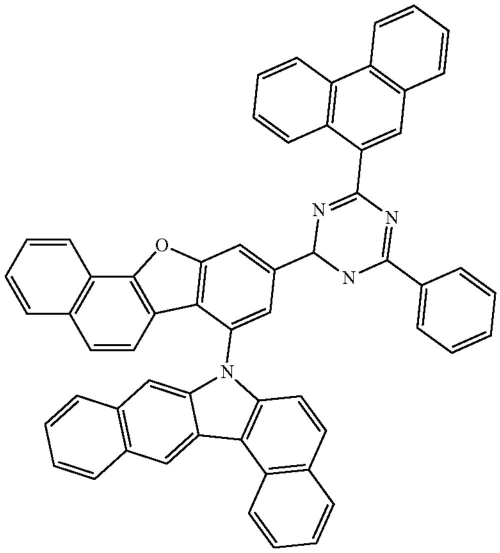

-continued
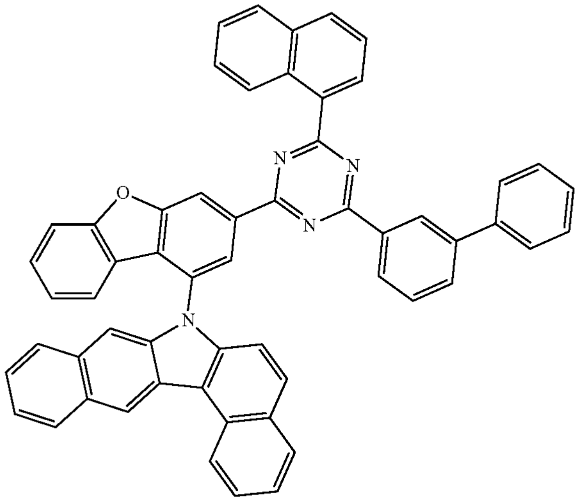
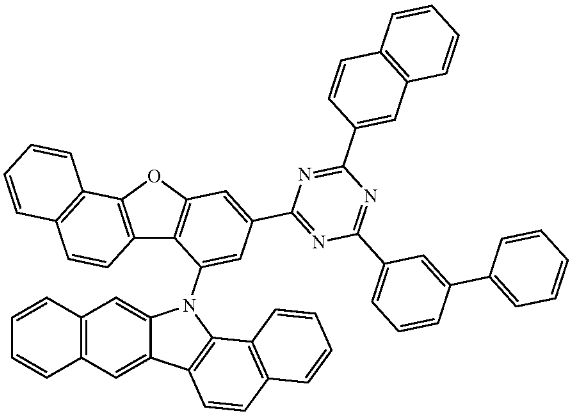
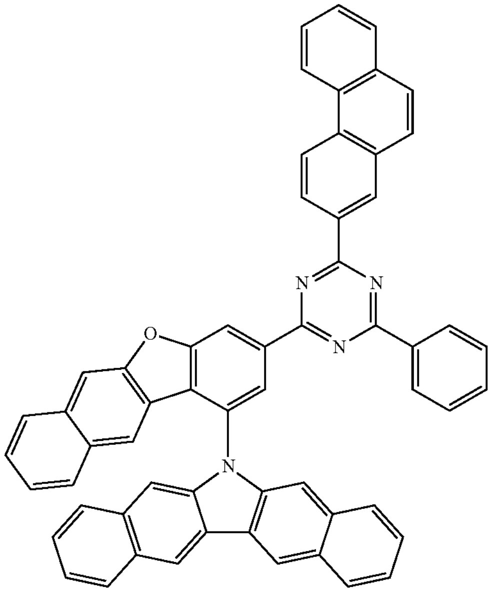
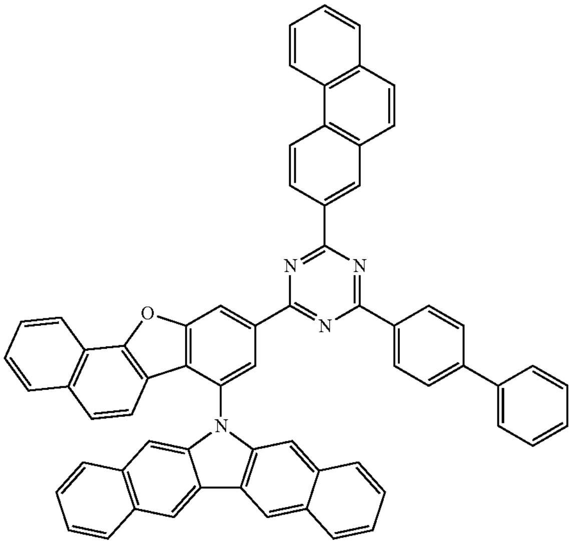
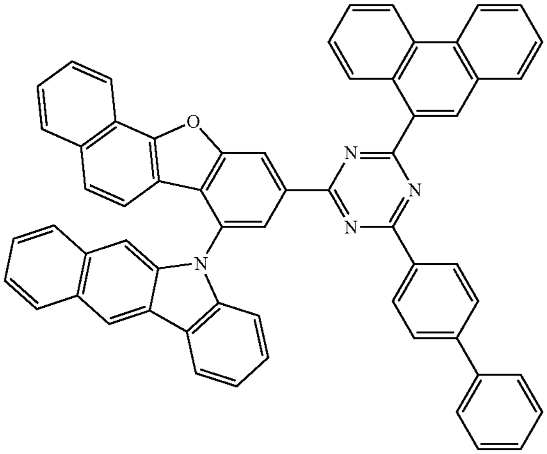
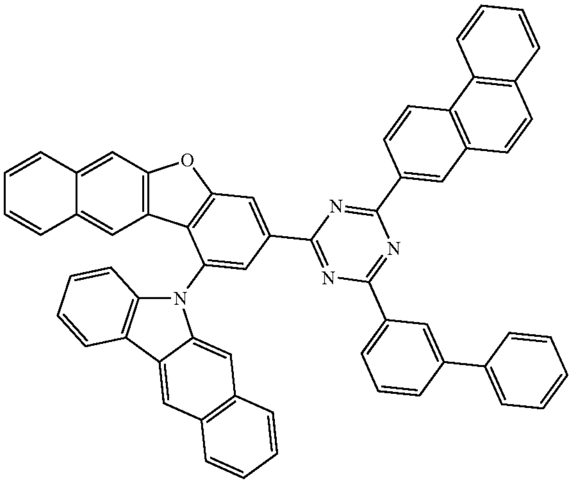
-continued -continued
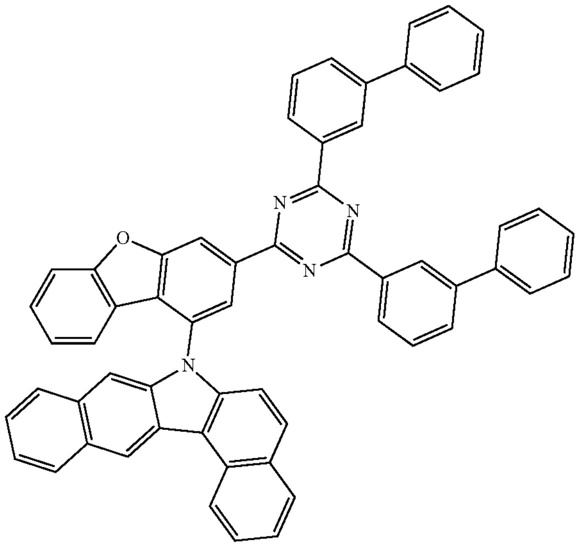
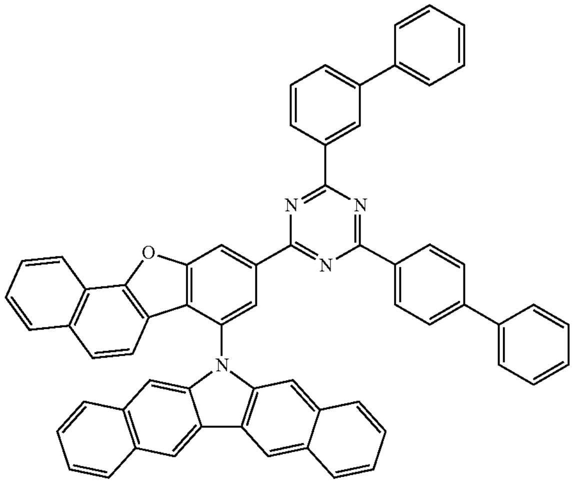
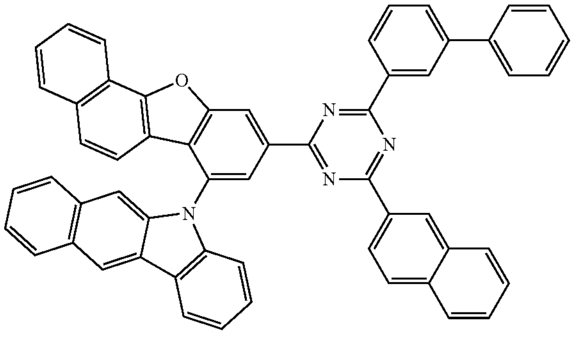
-continued
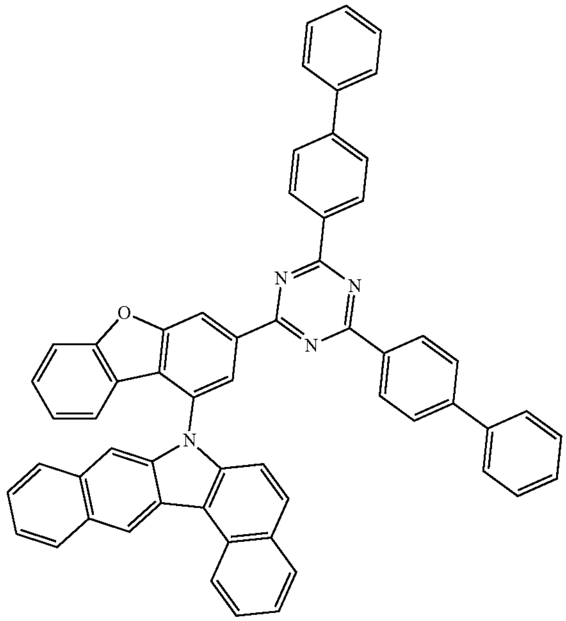
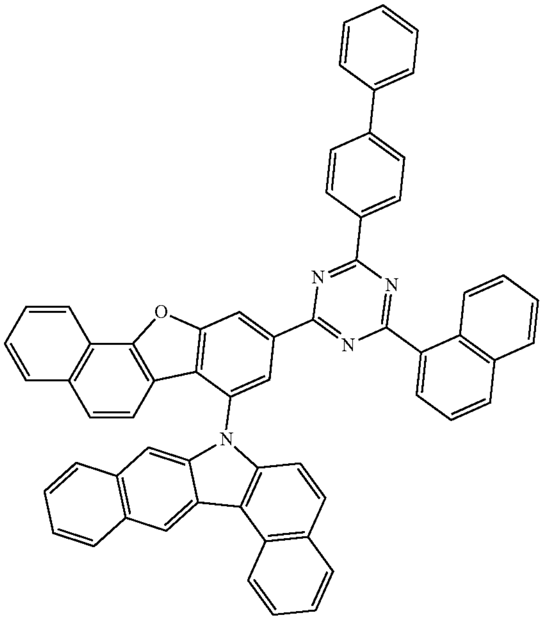

-continued
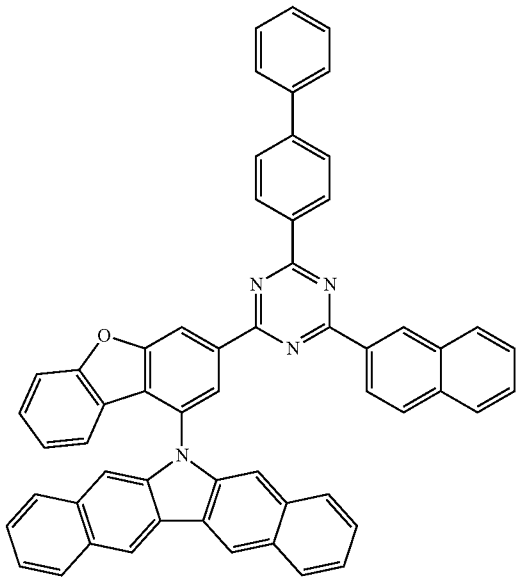
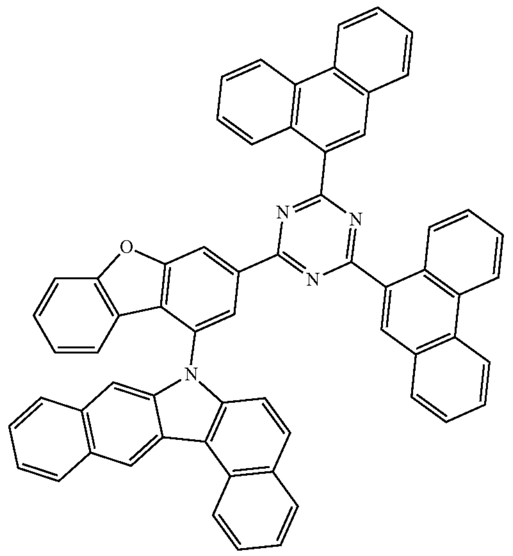
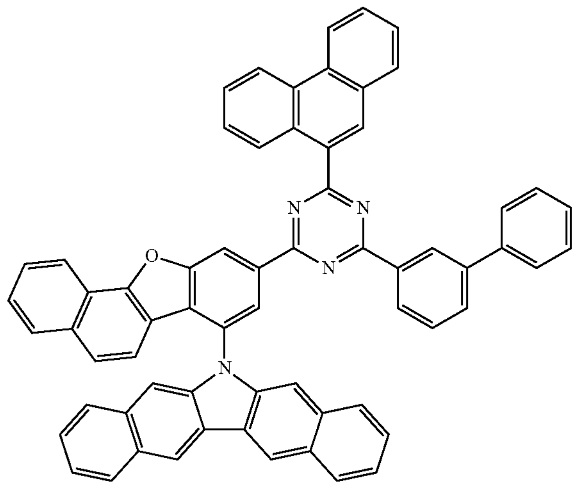
-continued
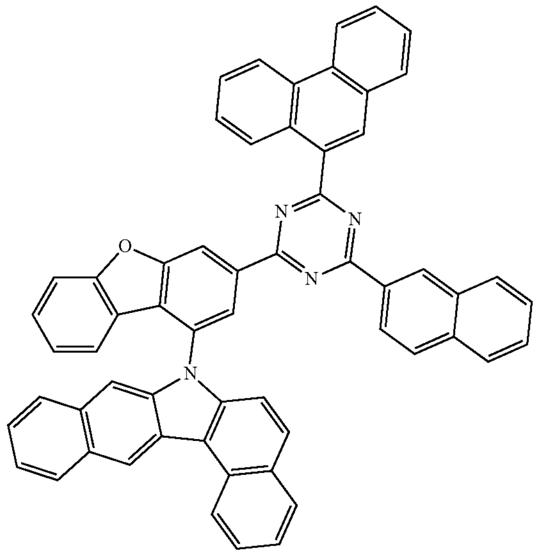
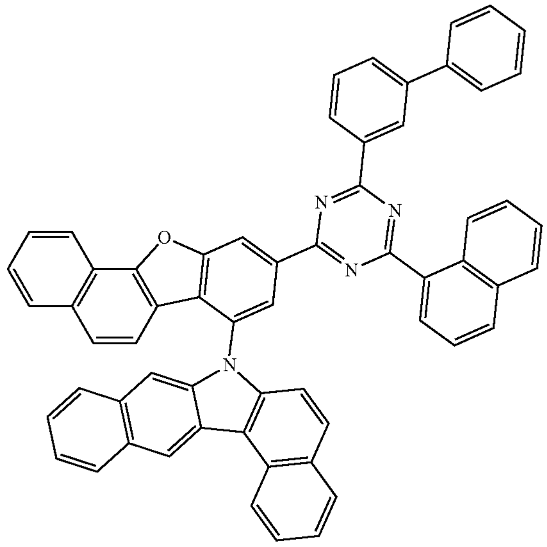
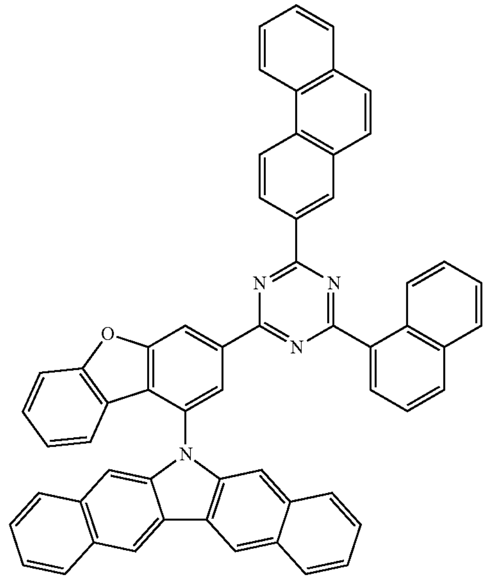

-continued
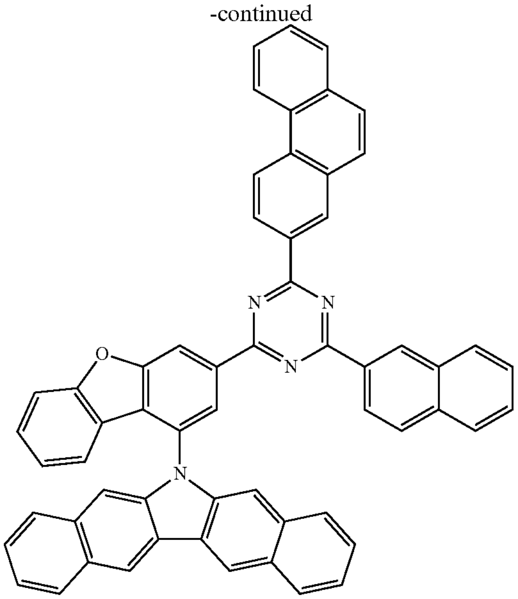
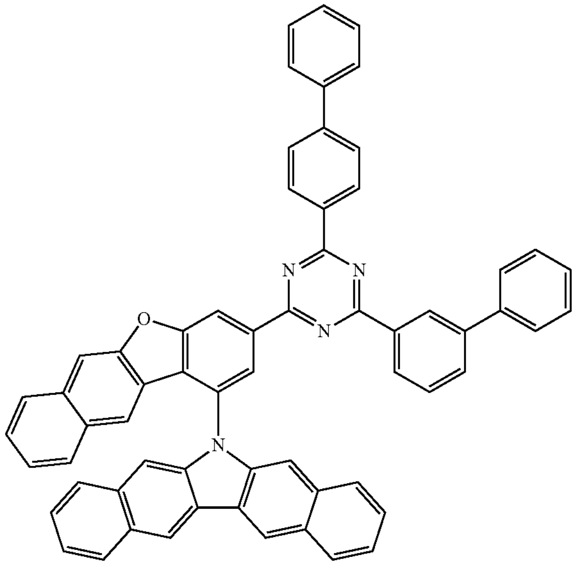
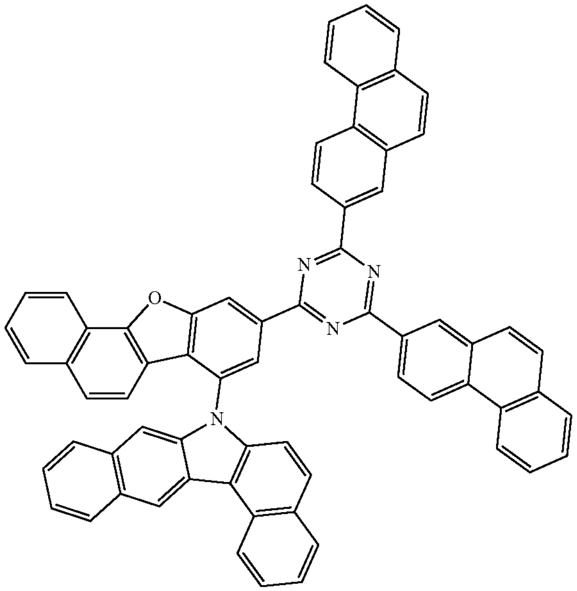
-continued
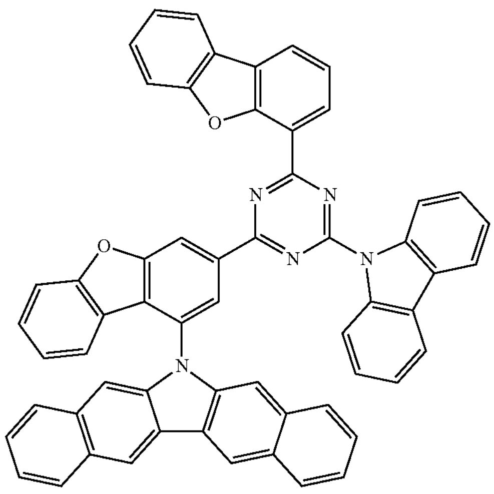
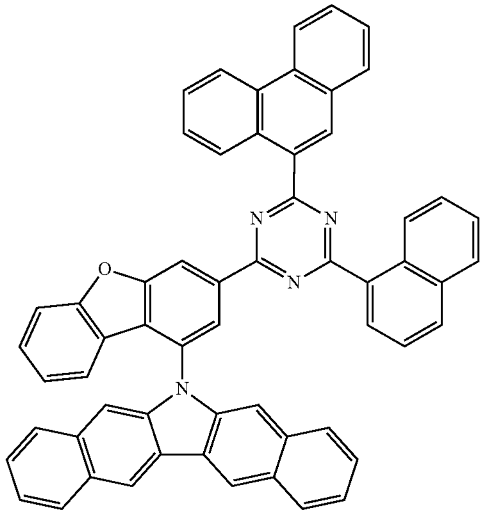
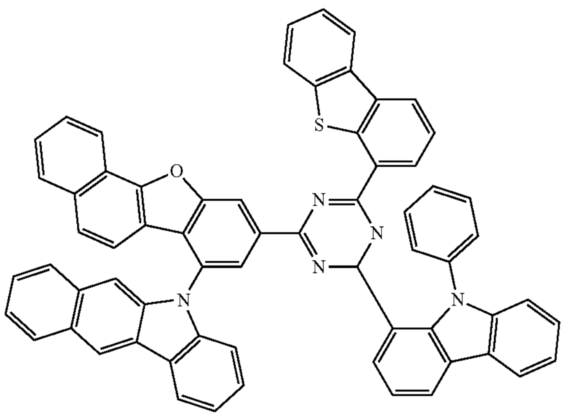

-continued
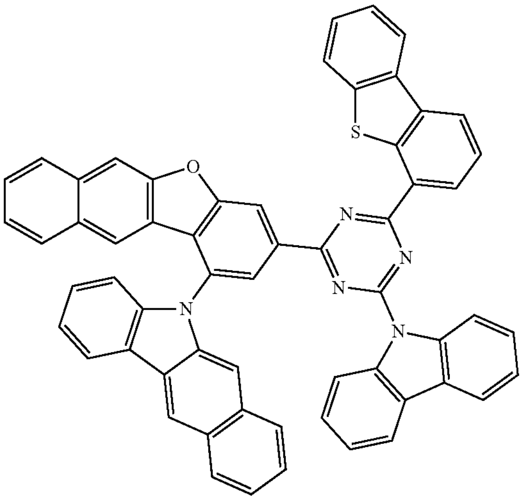
-continued
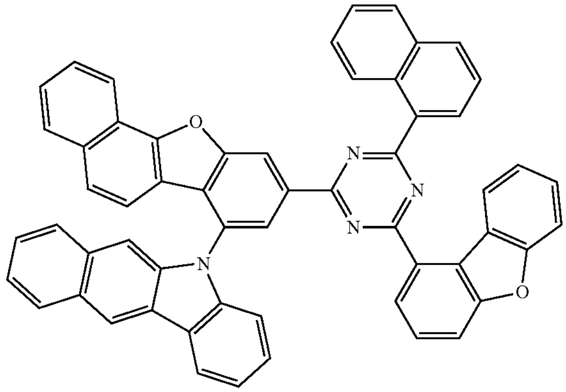
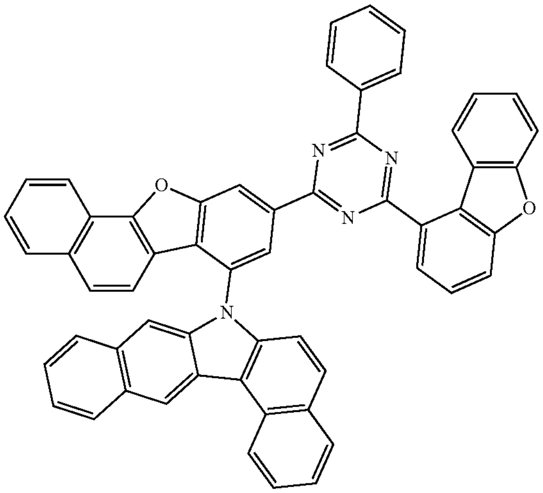
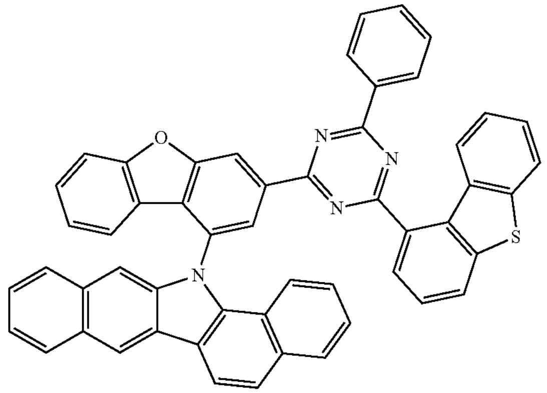
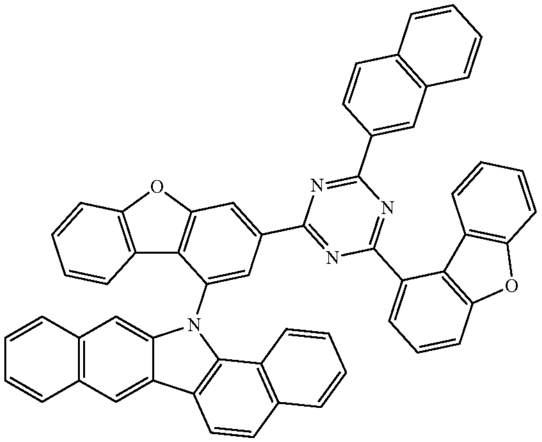
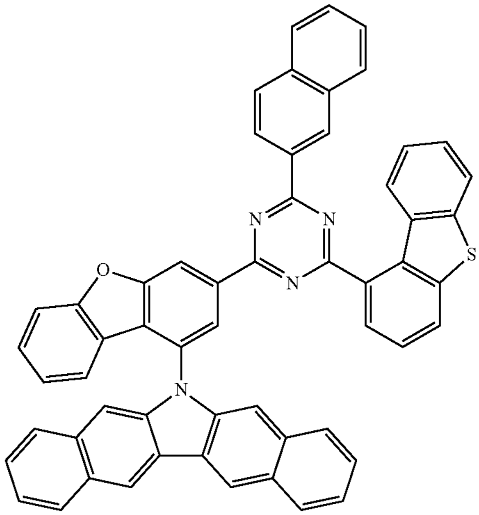

-continued
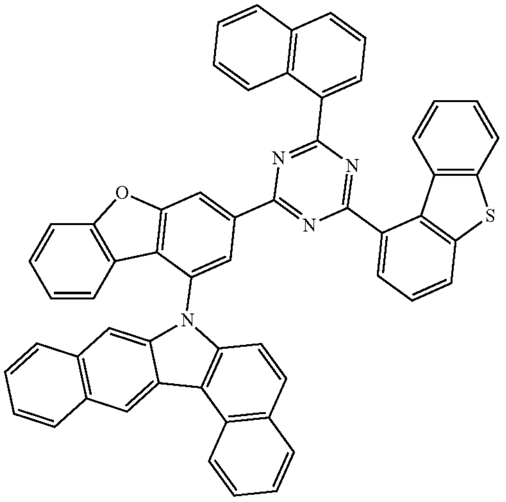
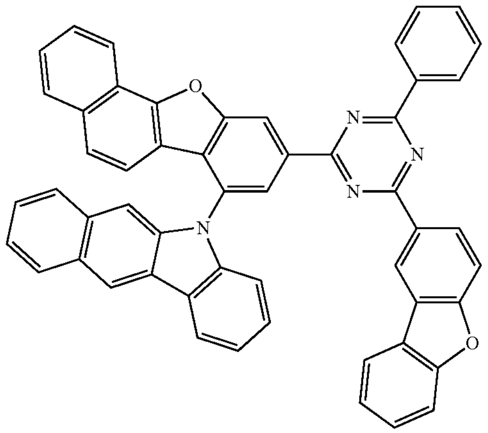
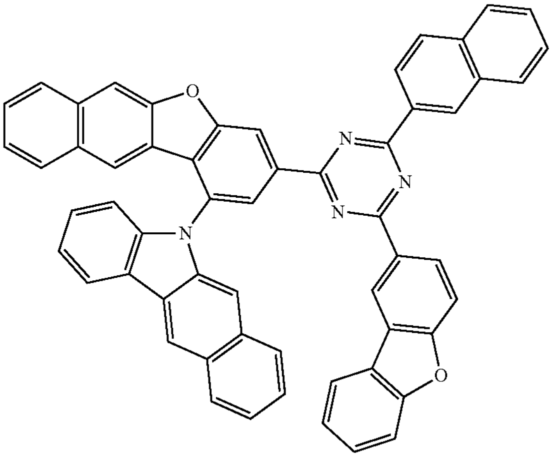
-continued
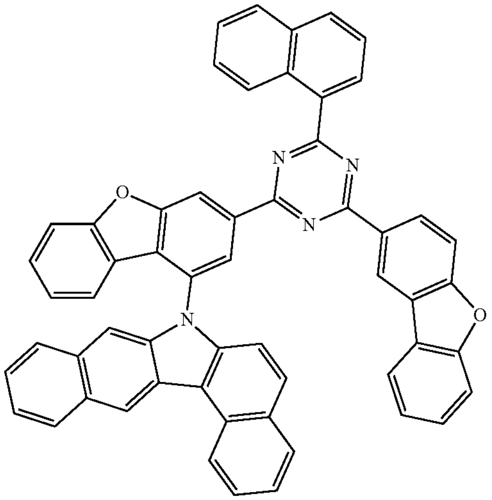
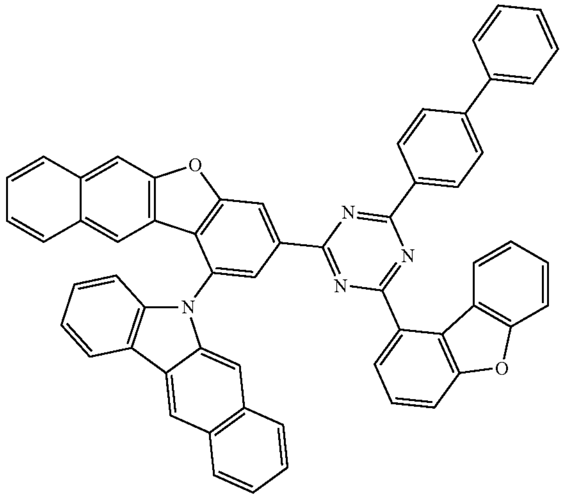
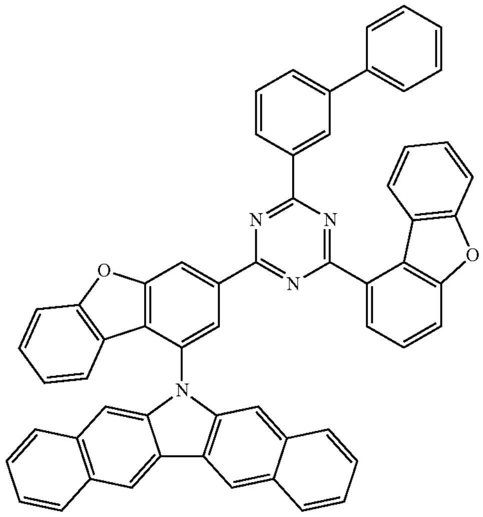

-continued
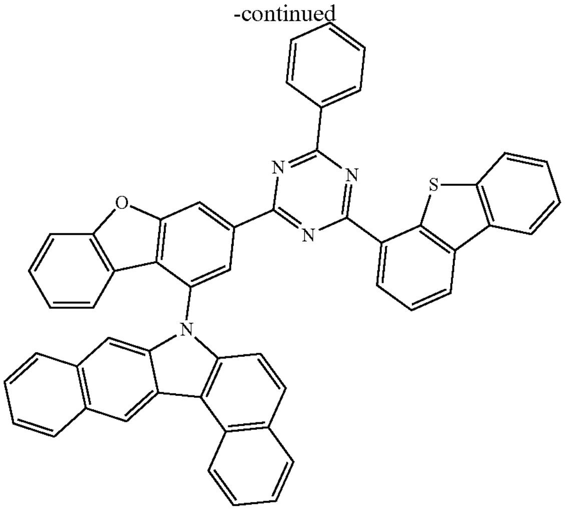
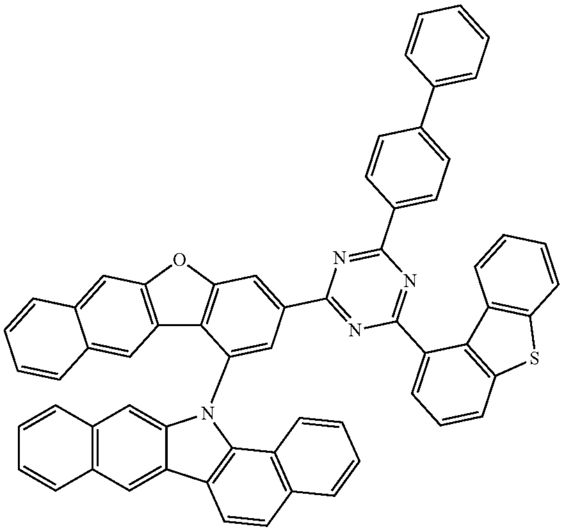
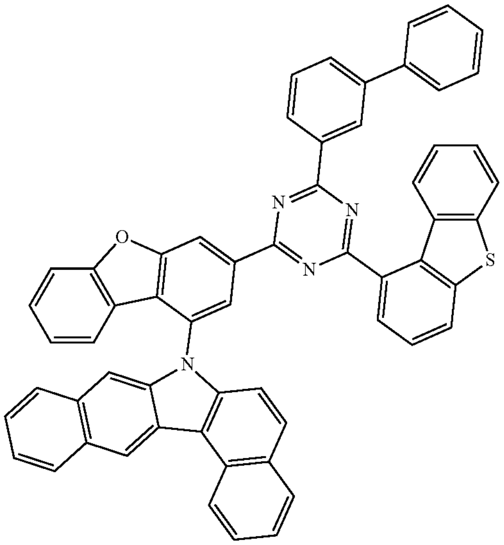
-continued
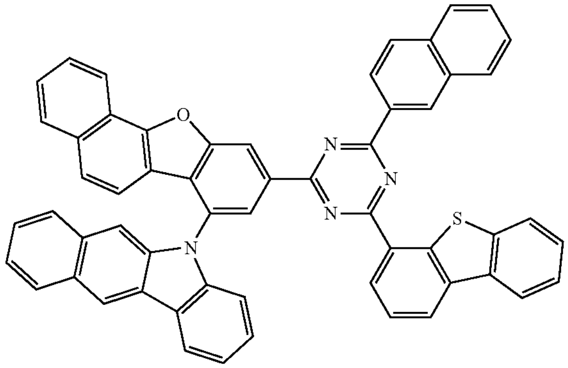
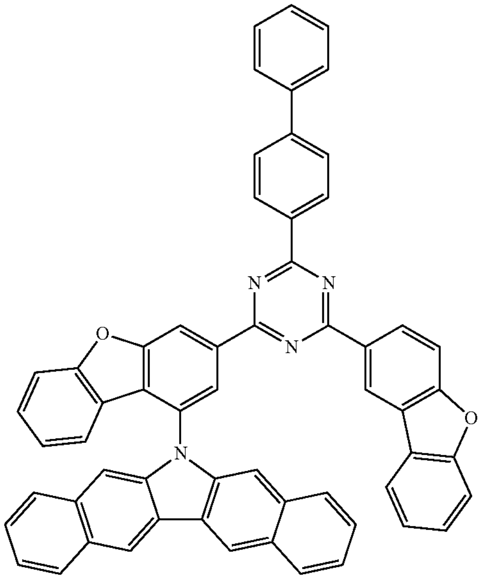
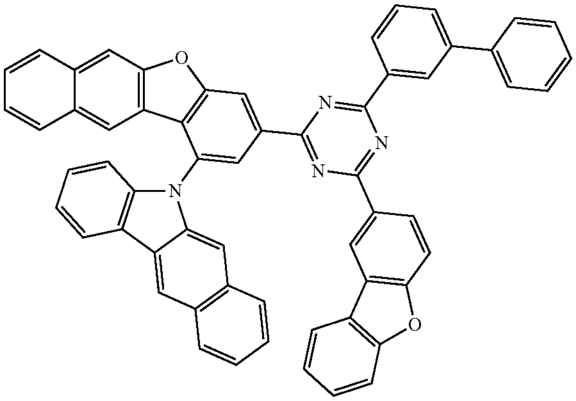

-continued
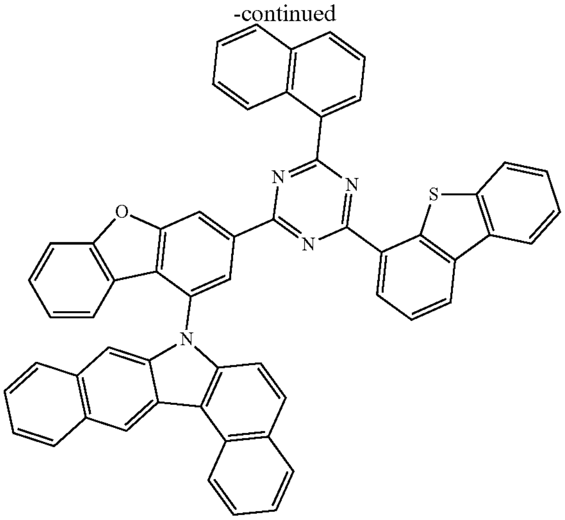
-continued
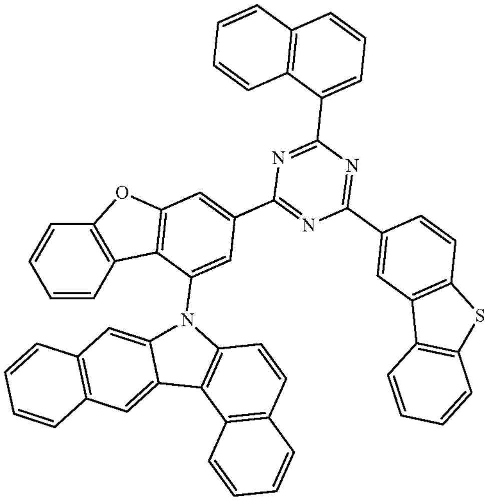
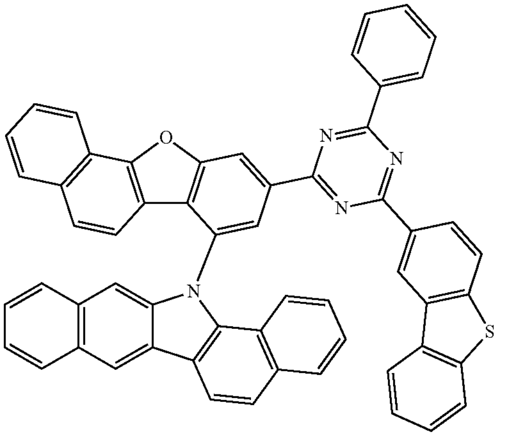
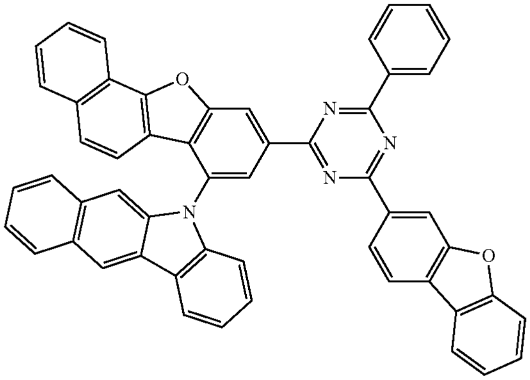
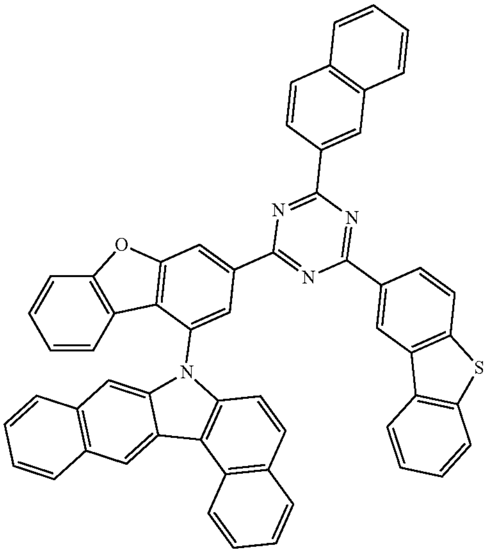
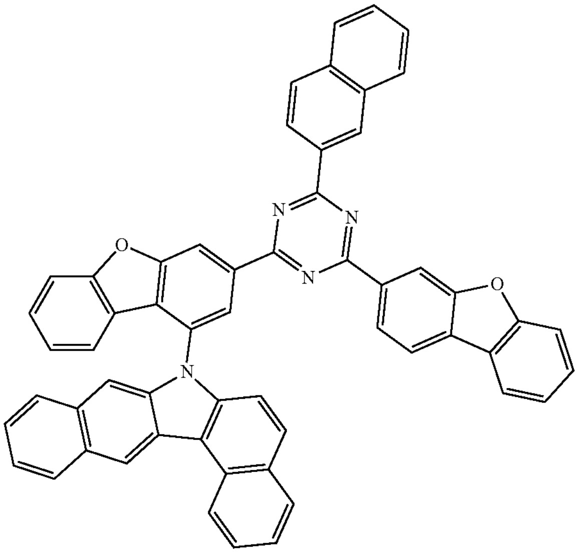

-continued
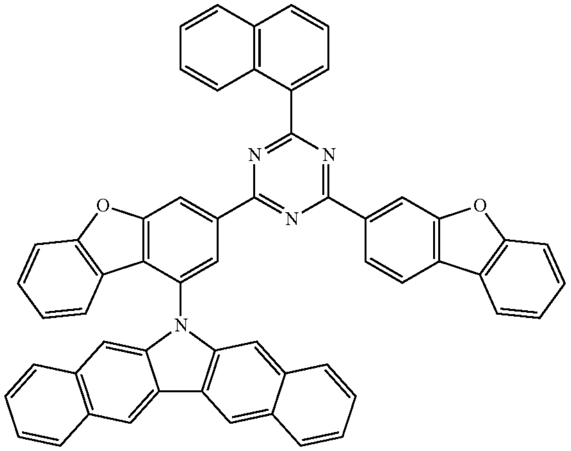
-continued
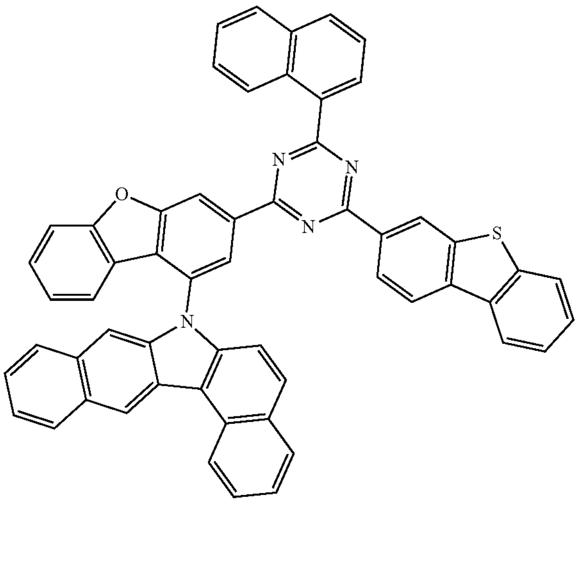
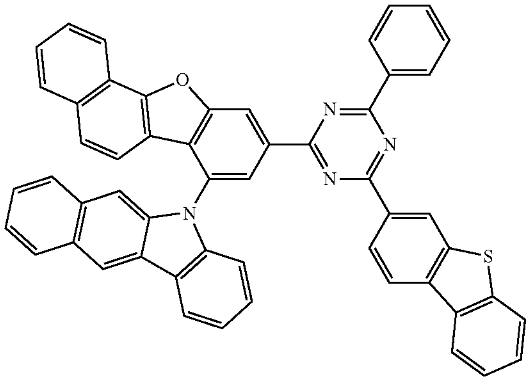
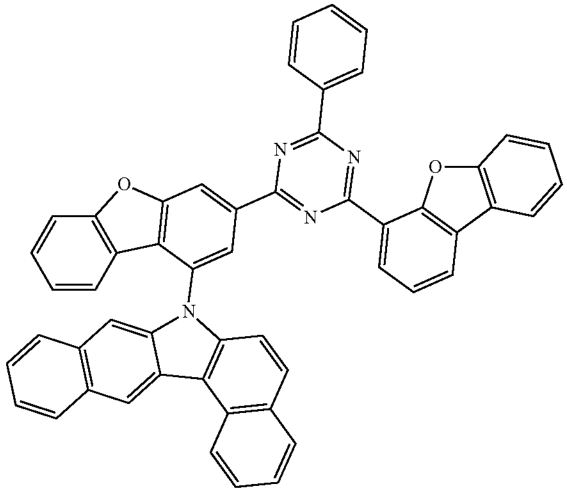
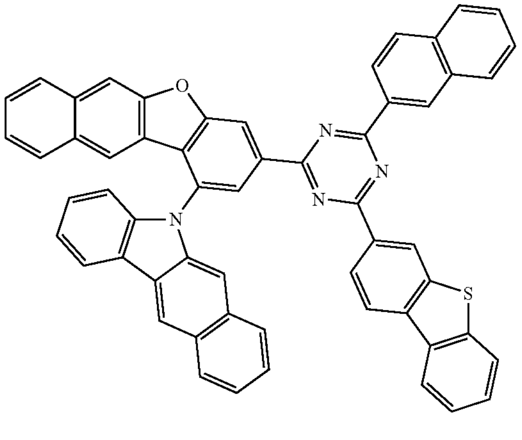
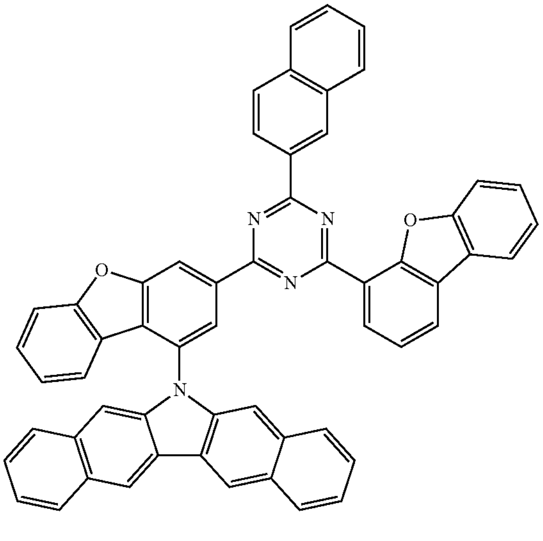

-continued
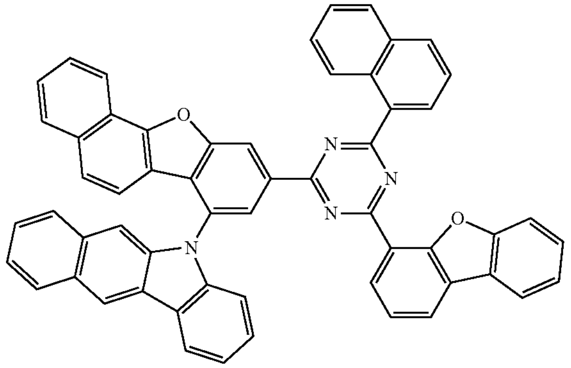
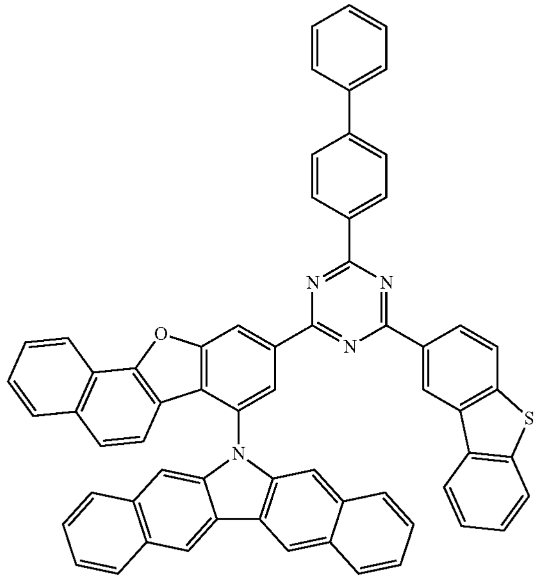
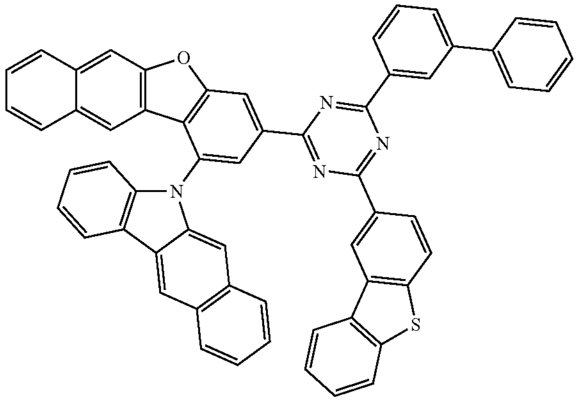
-continued
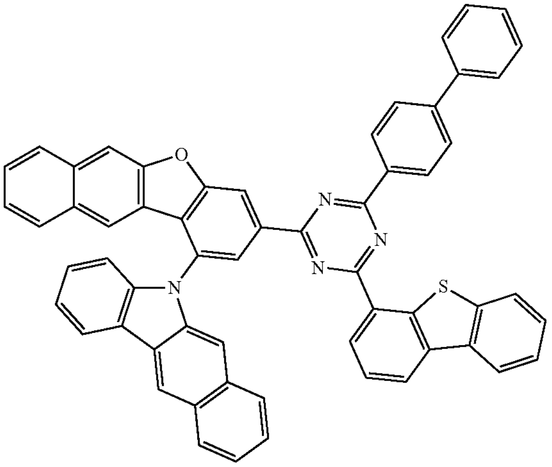
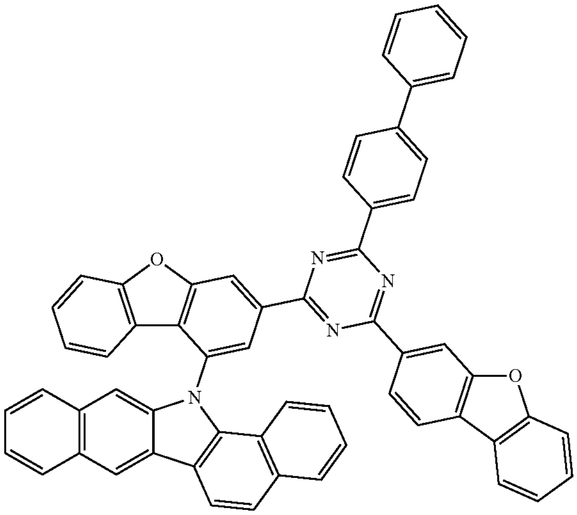
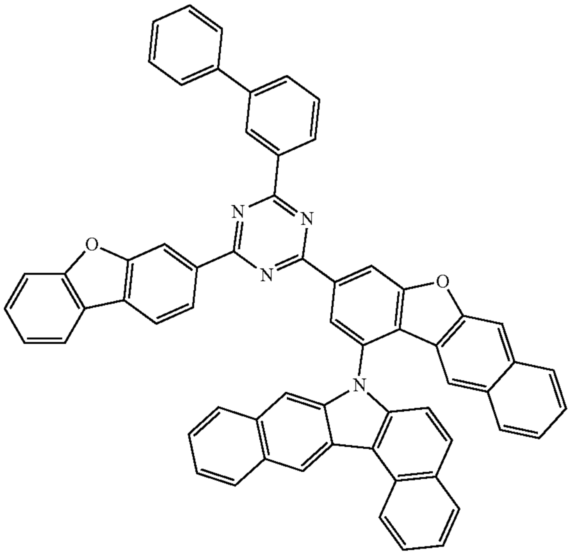

-continued
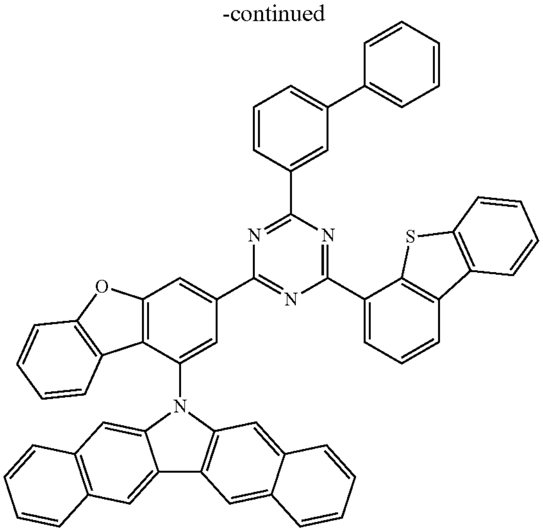
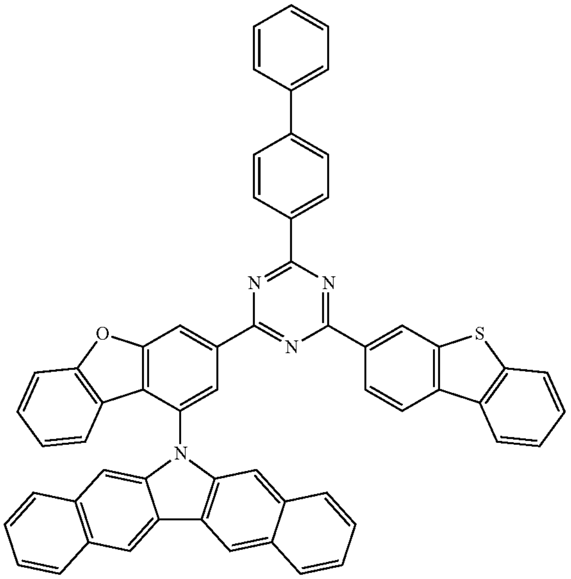
-continued
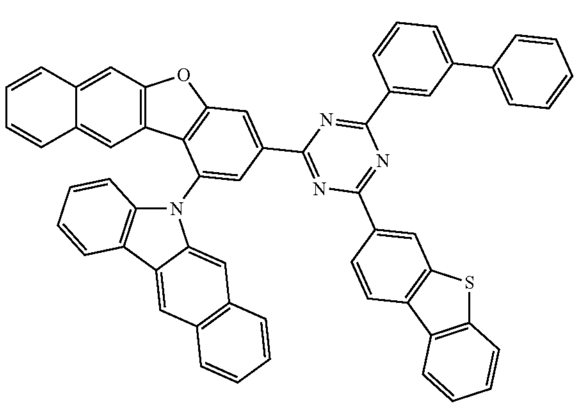
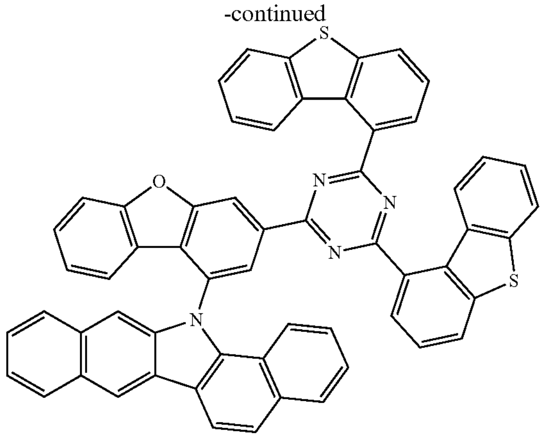
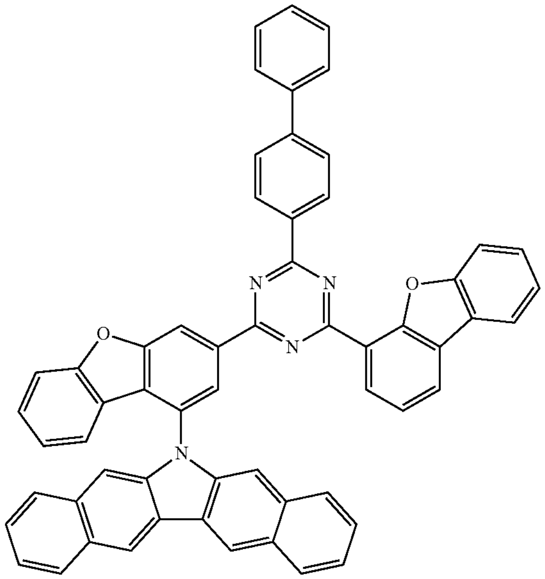
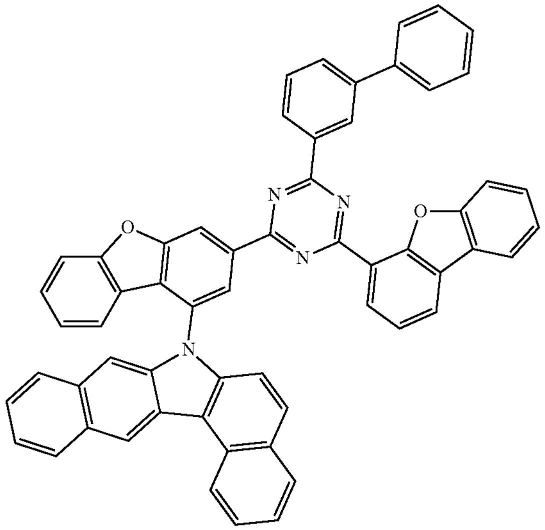

-continued
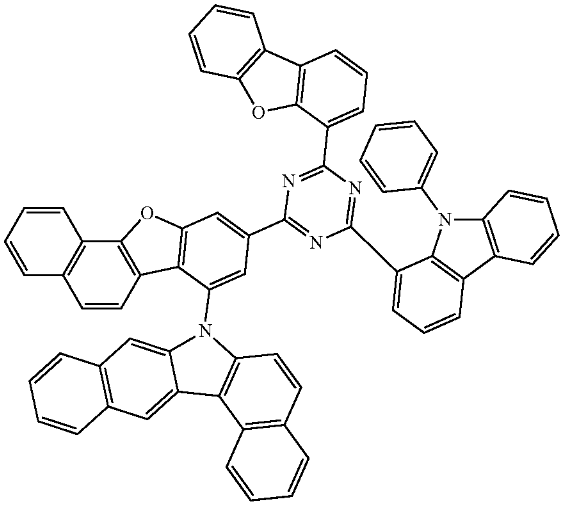
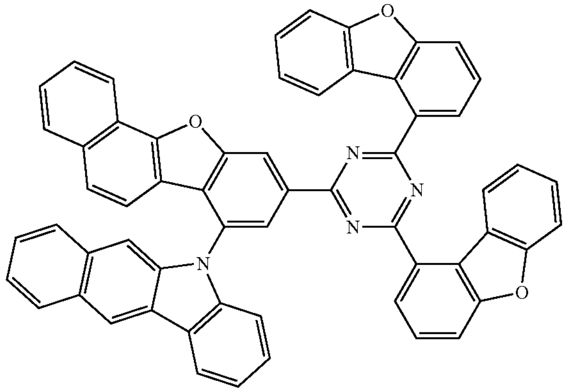
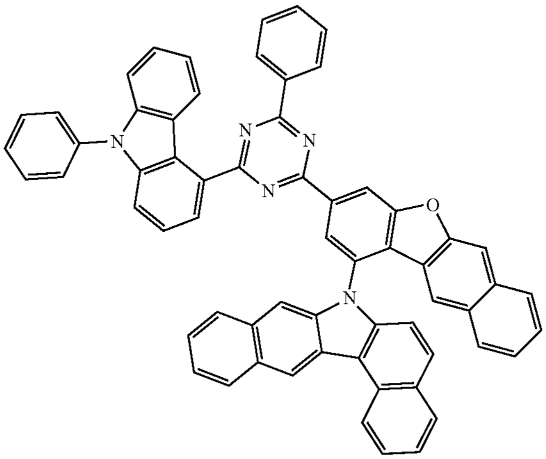
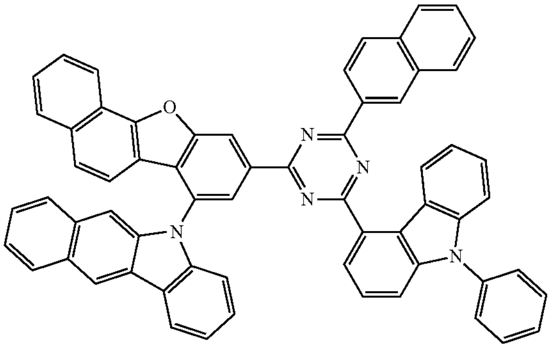
-continued
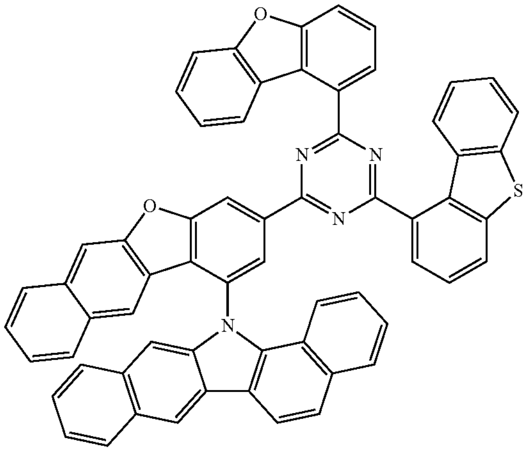
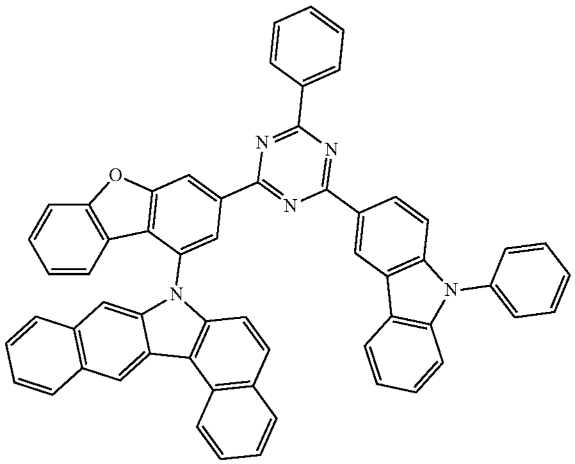
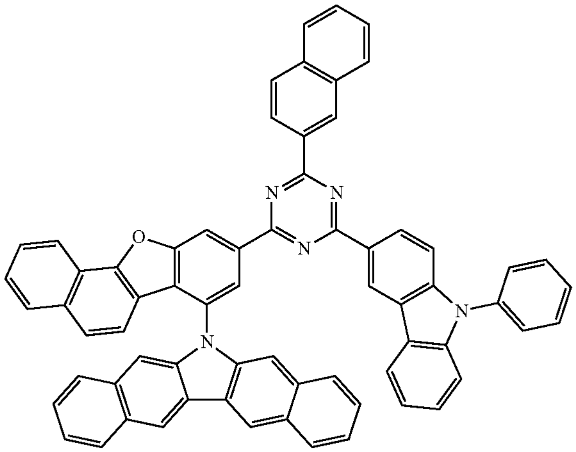

-continued
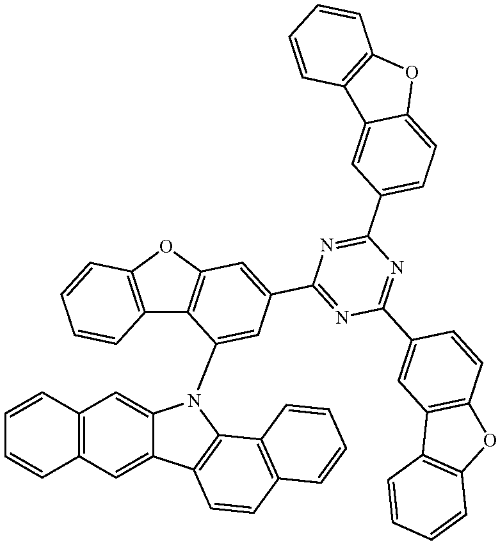
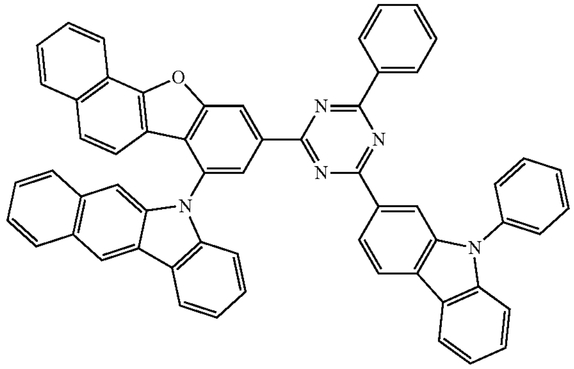
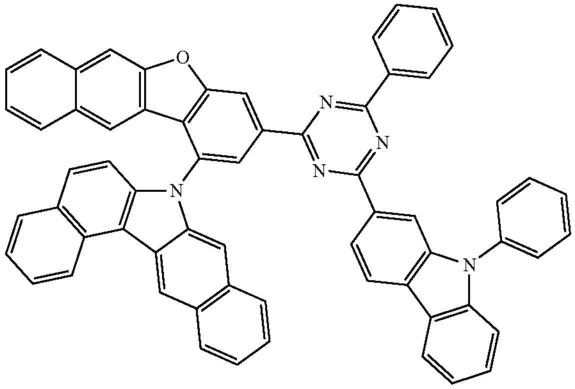
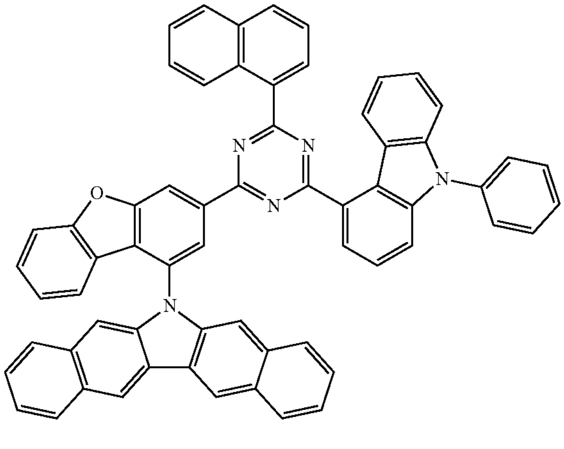
-continued
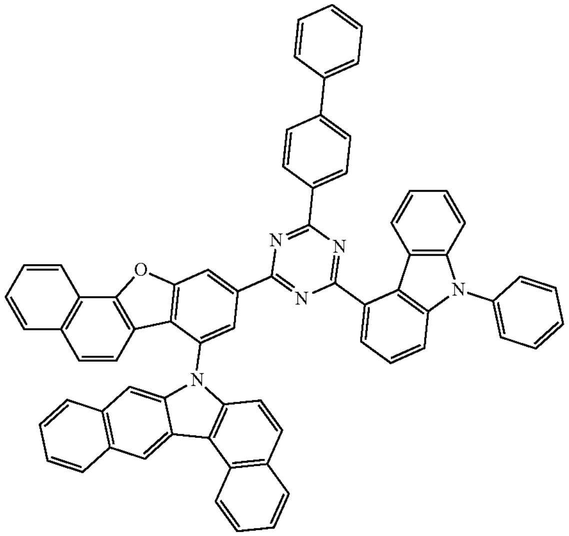
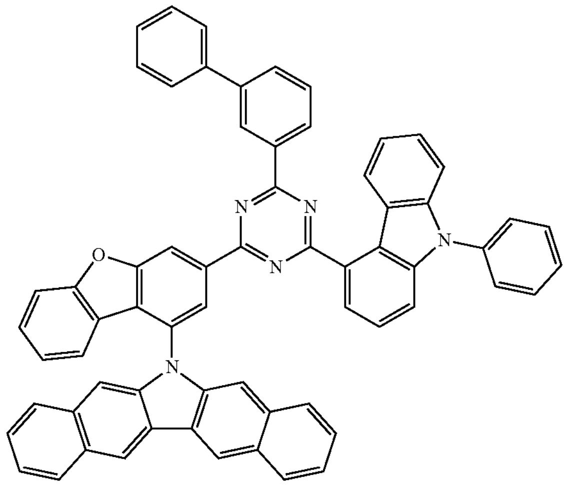
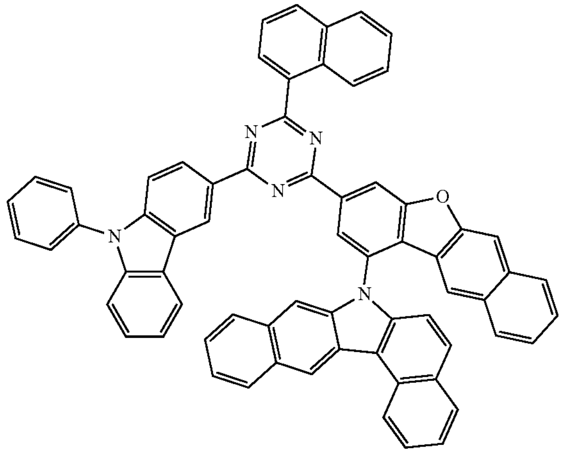

-continued
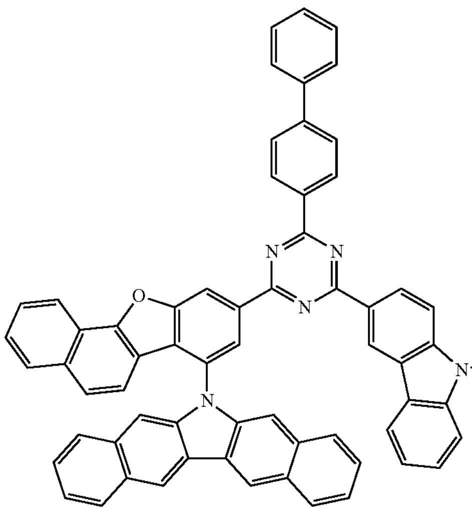
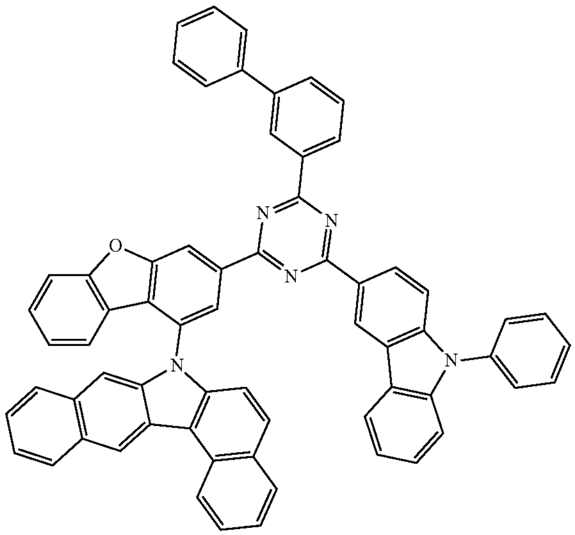
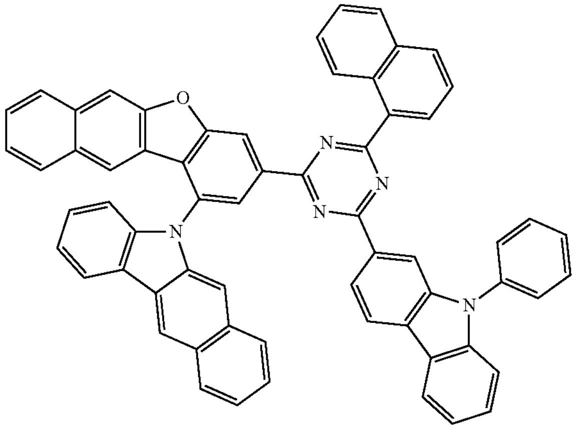
-continued
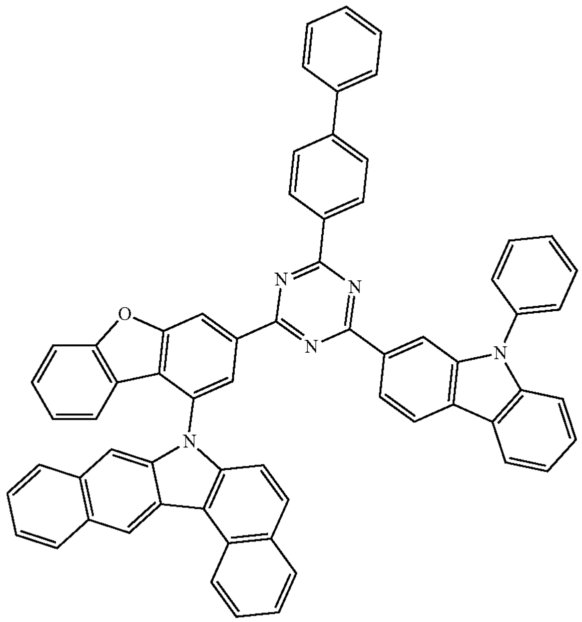
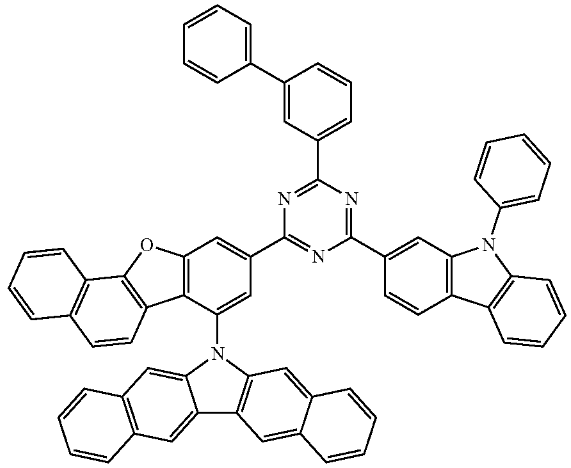
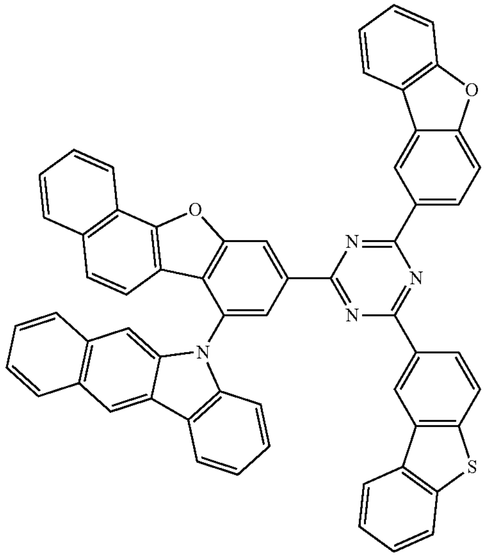

-continued
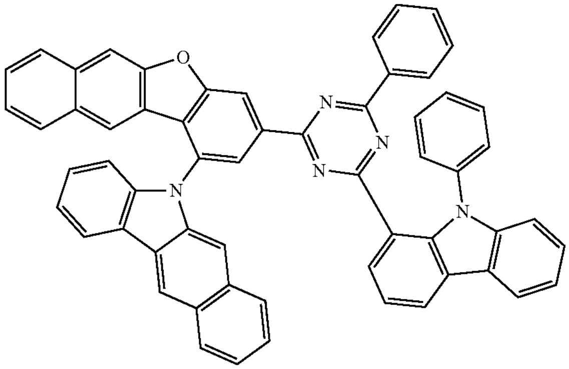
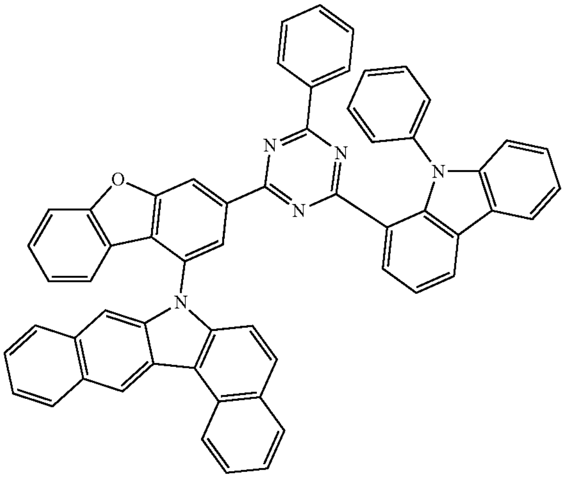
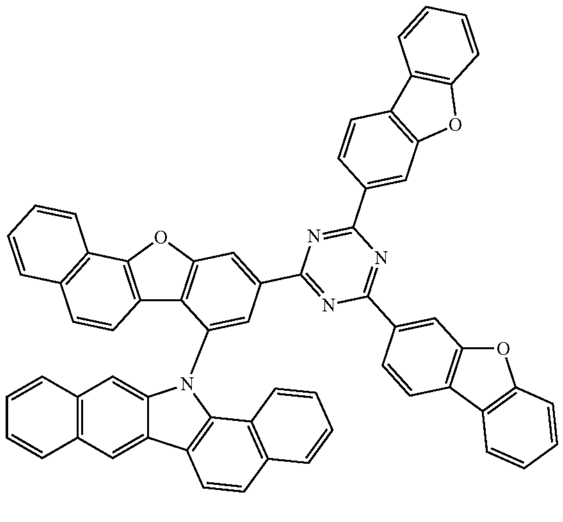
-continued
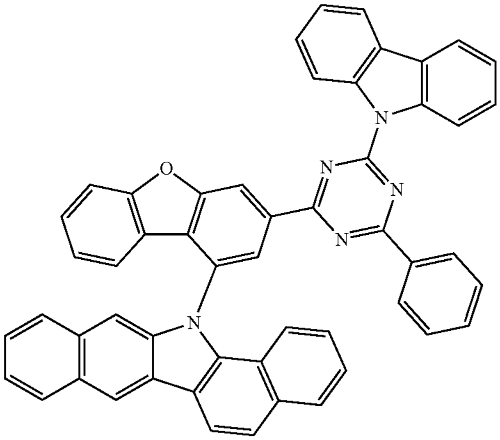
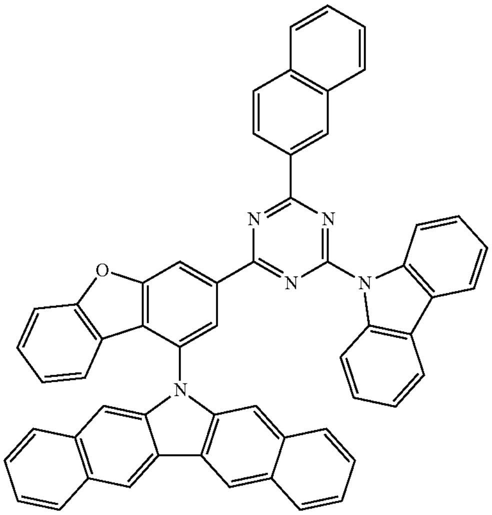
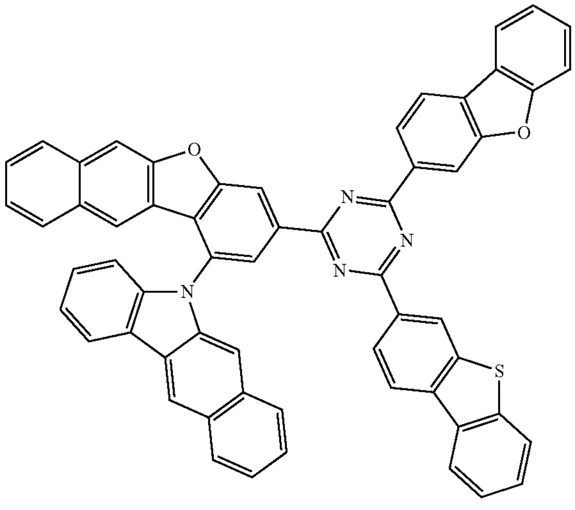

-continued
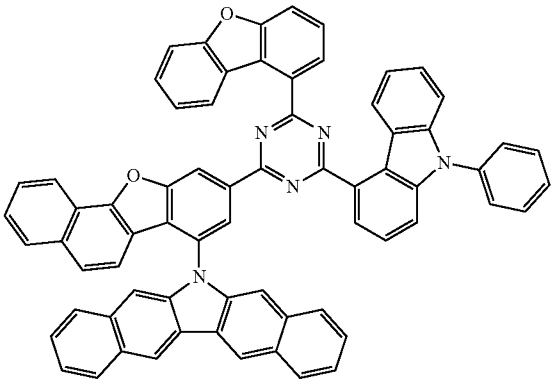
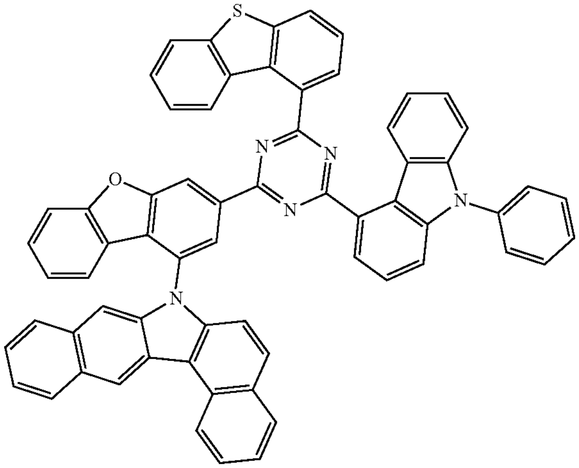
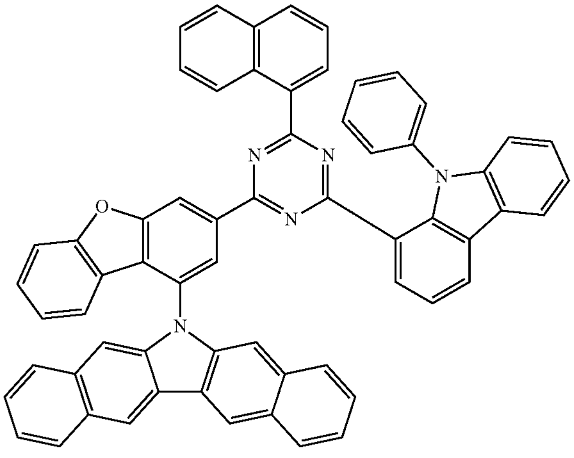
-continued
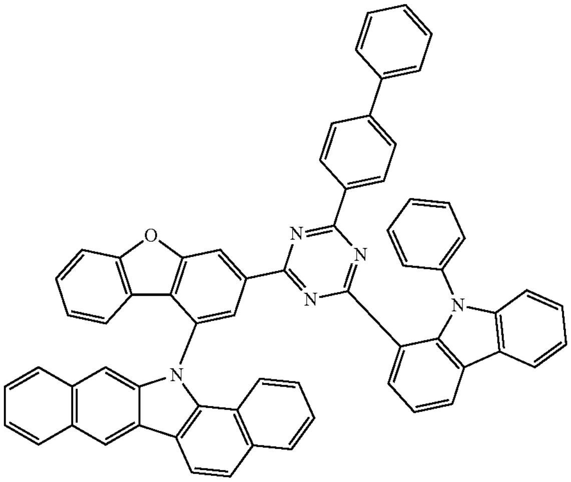
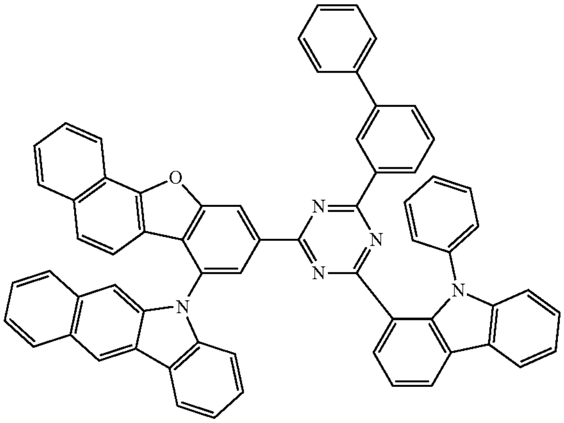
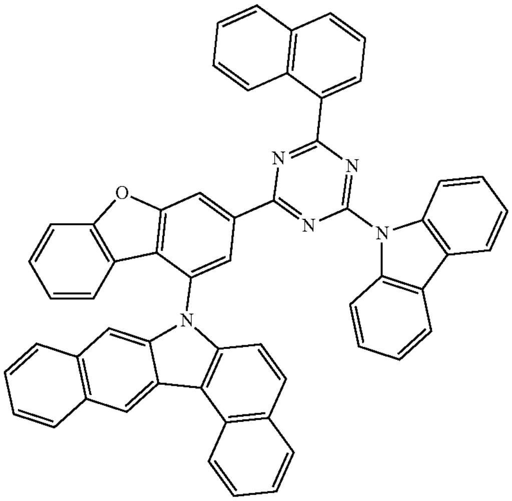

-continued
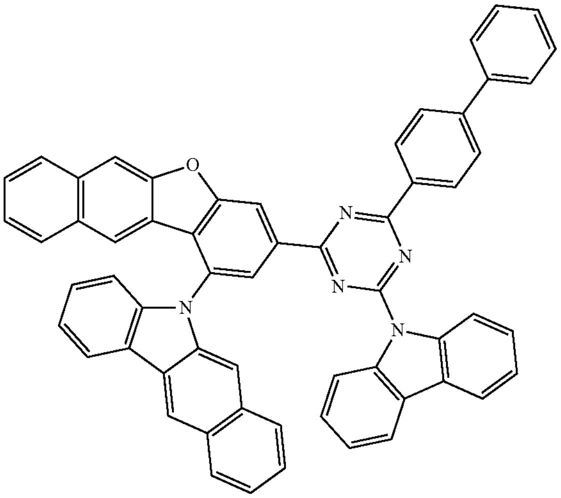
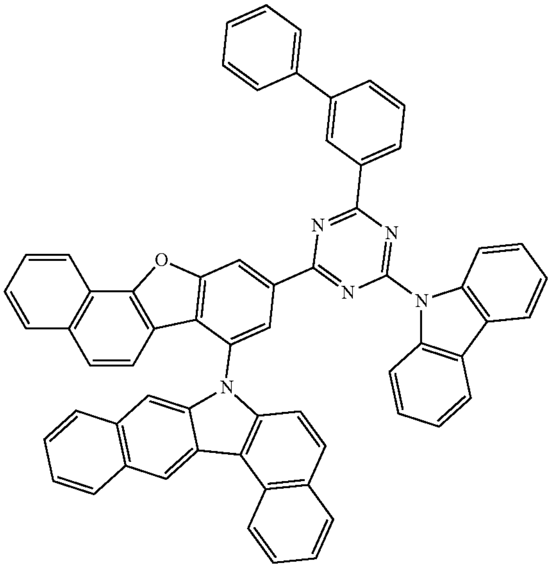
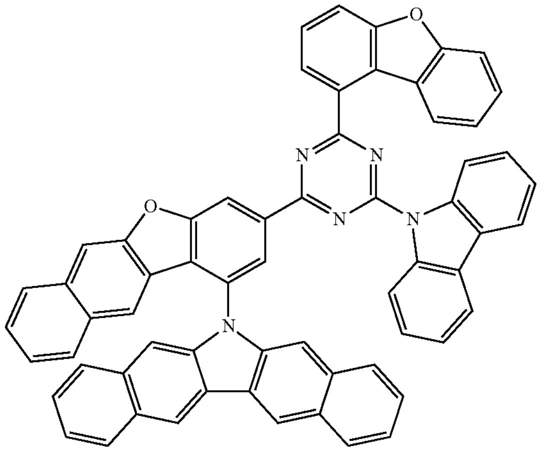
-continued
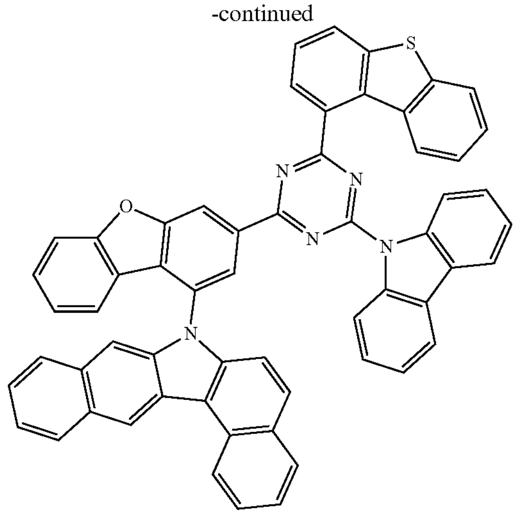
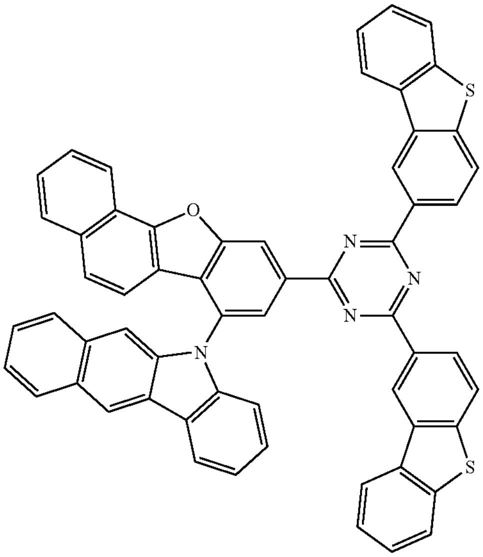
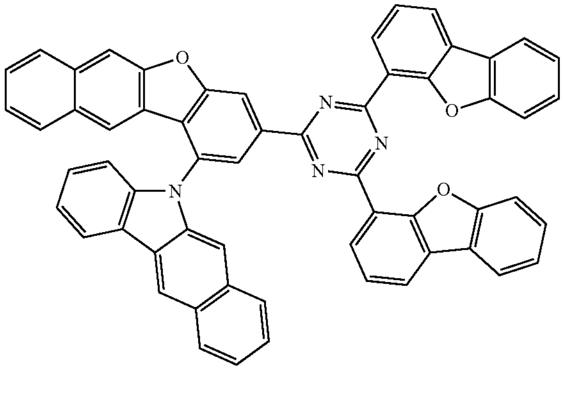

-continued
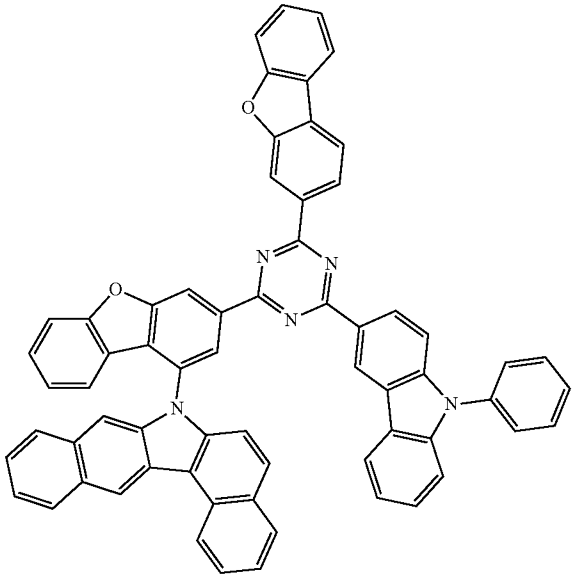
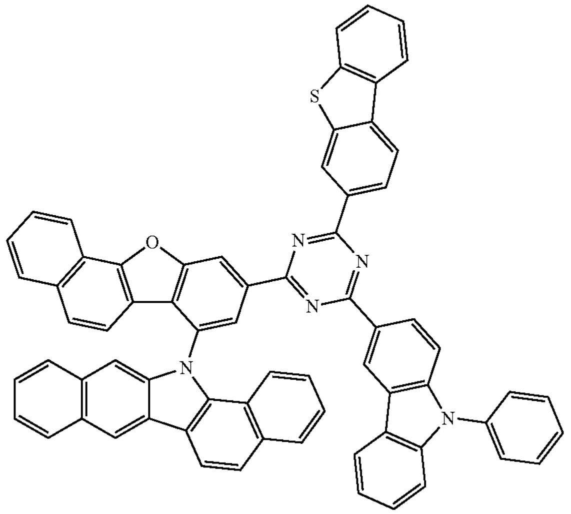
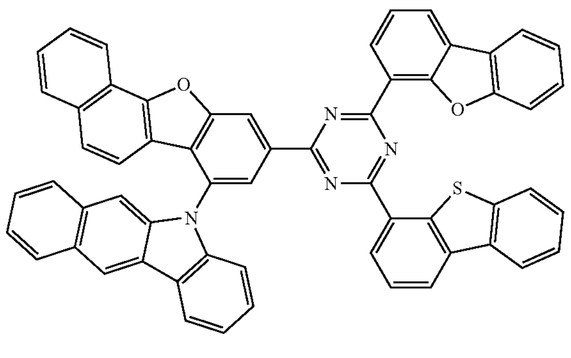
-continued
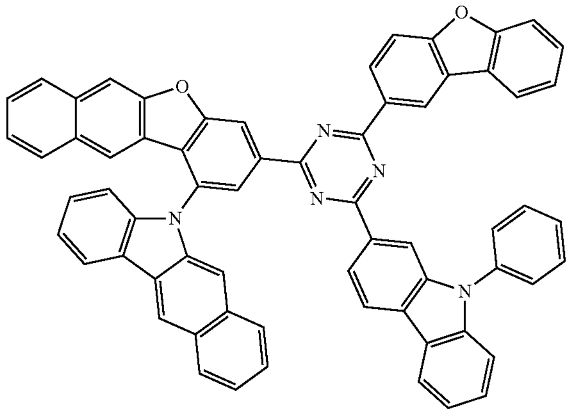
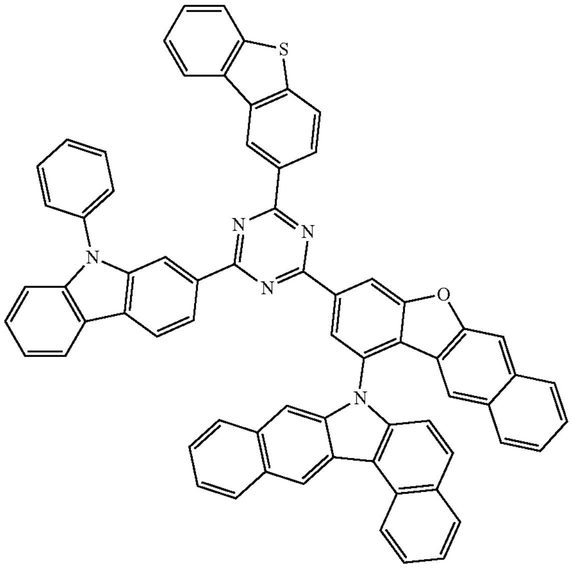
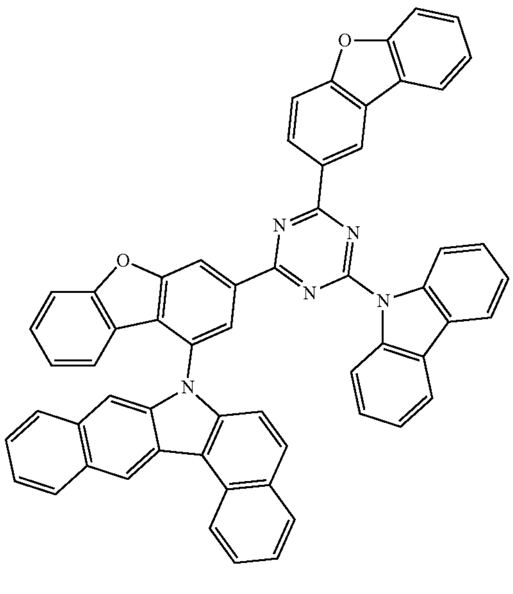

-continued
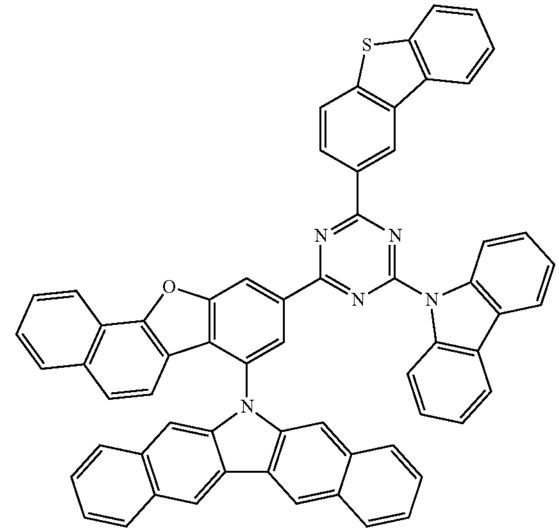
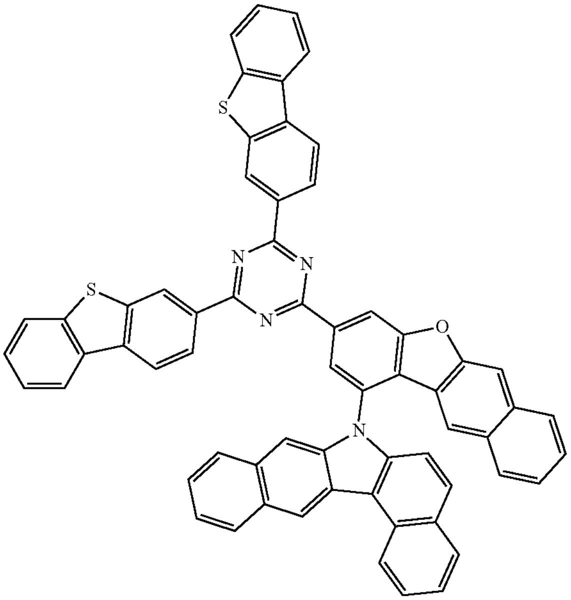
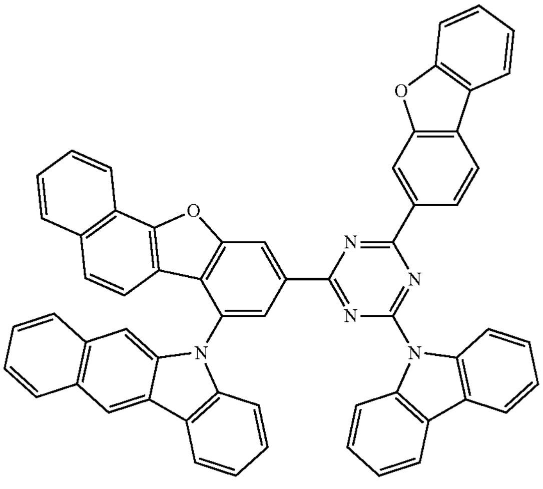
-continued
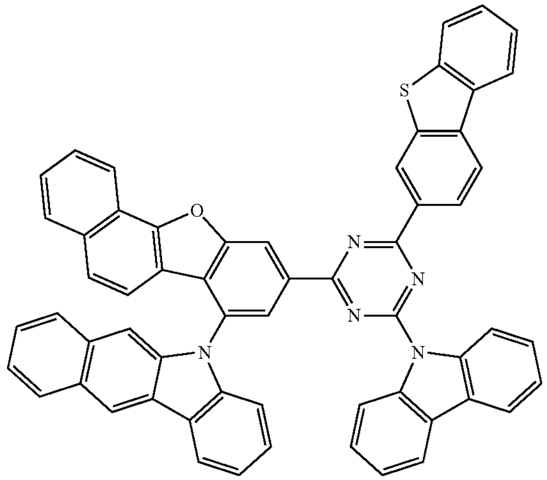
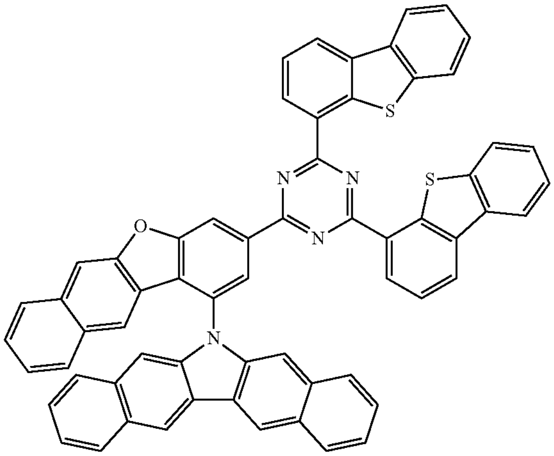
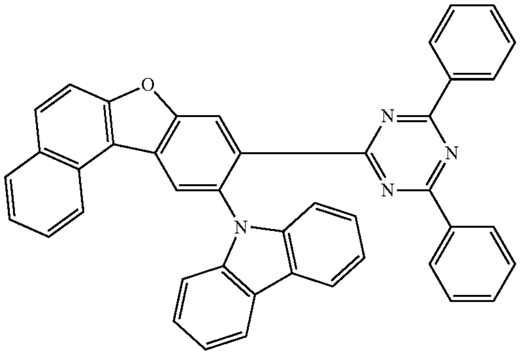
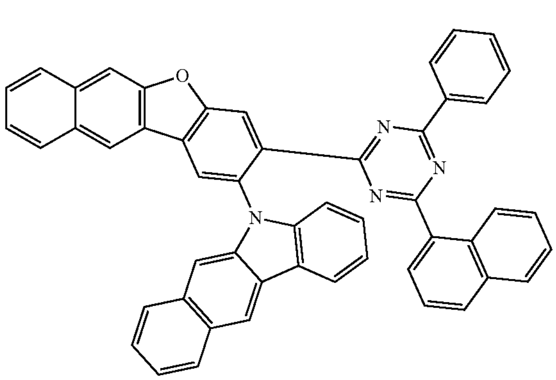

-continued
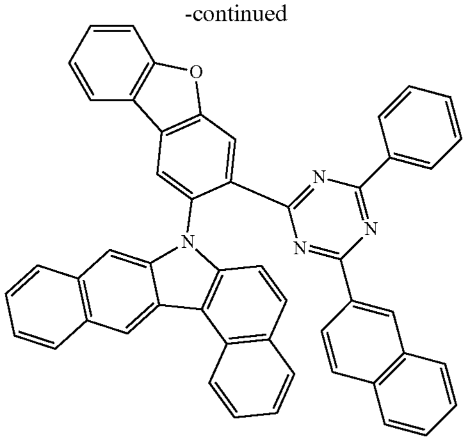
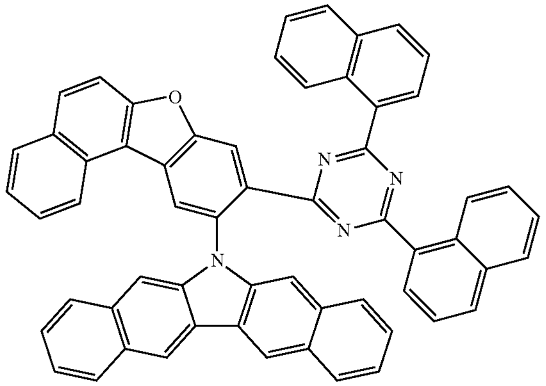
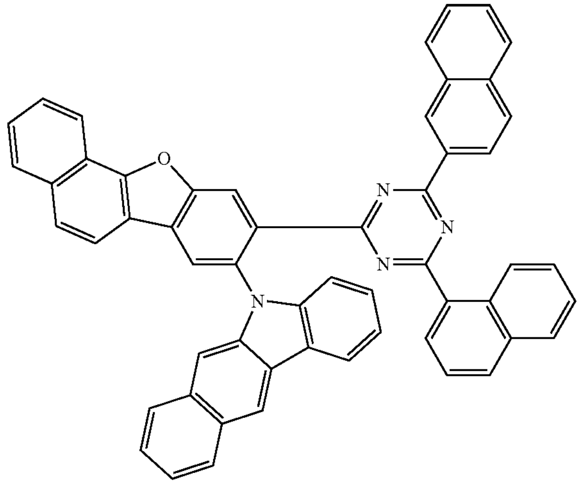
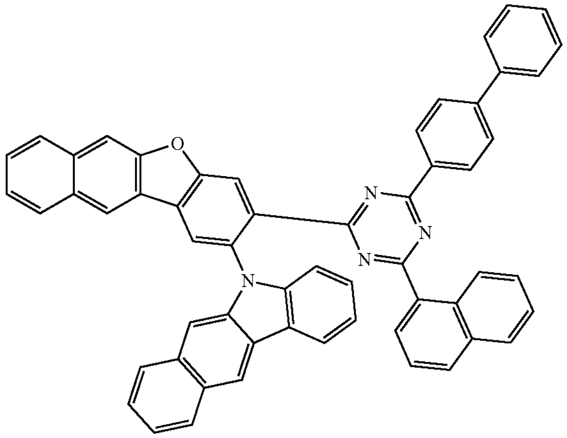
-continued
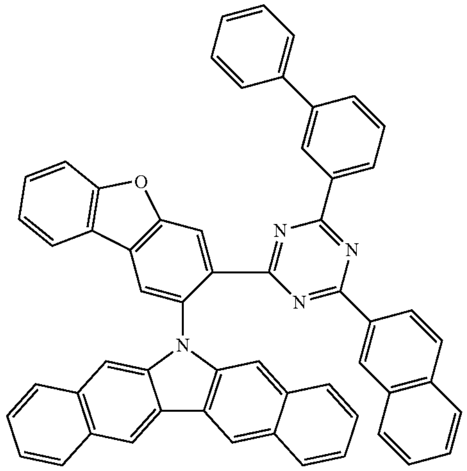
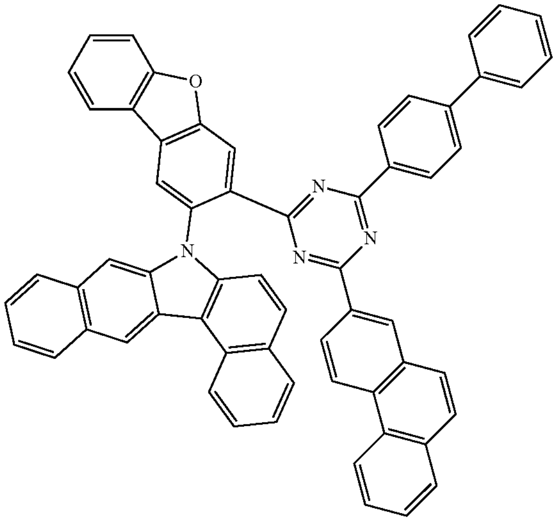
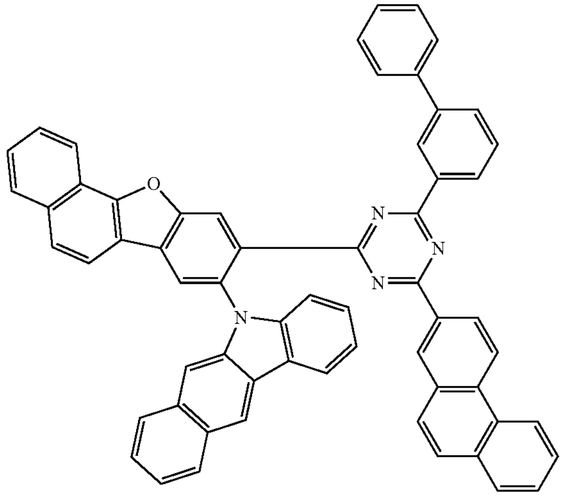

-continued
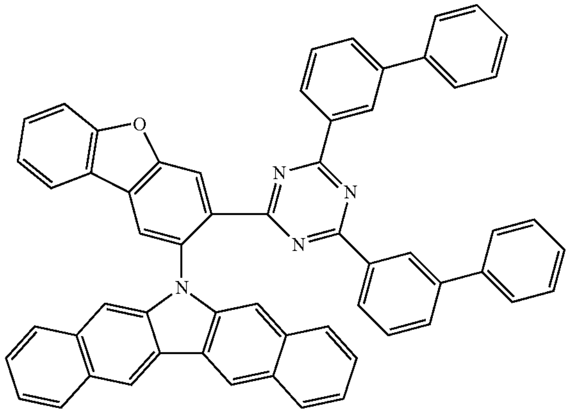
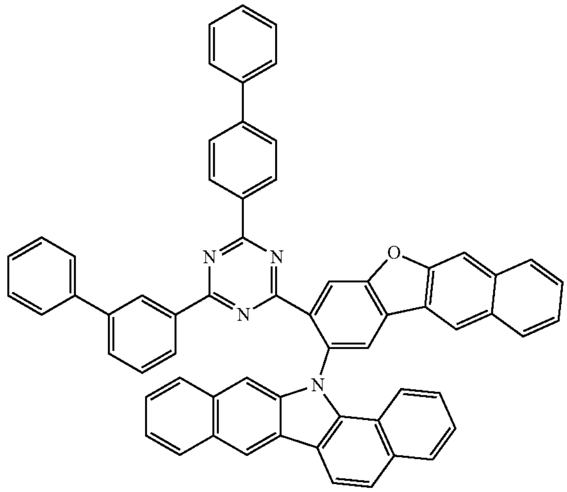
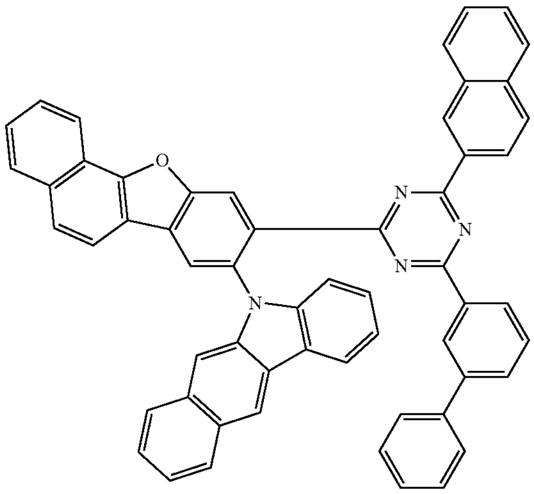
-continued
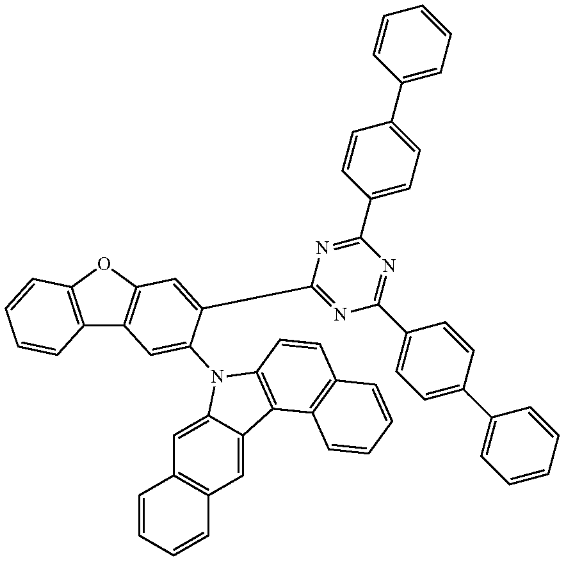
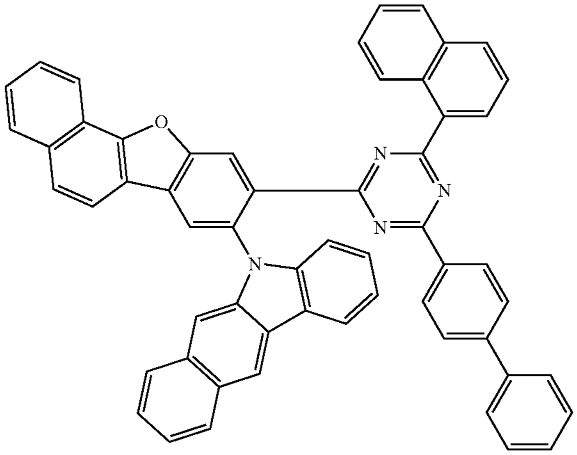
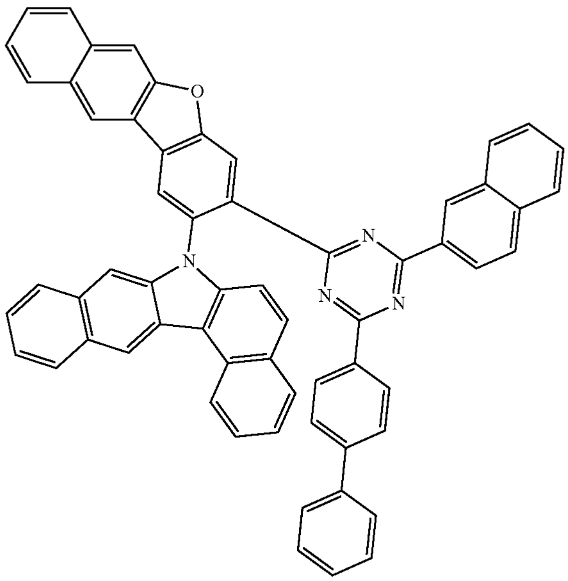

-continued
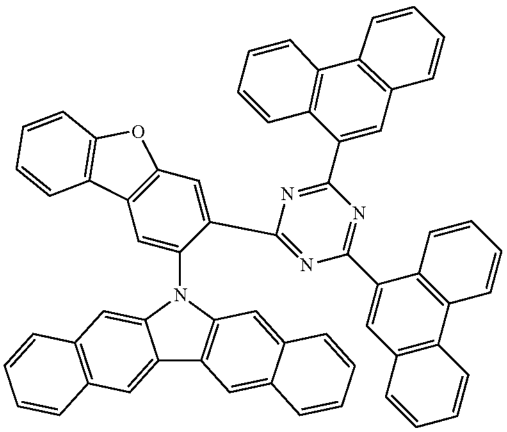
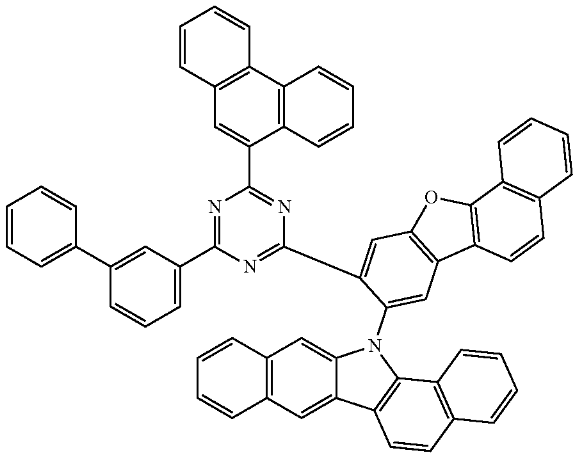
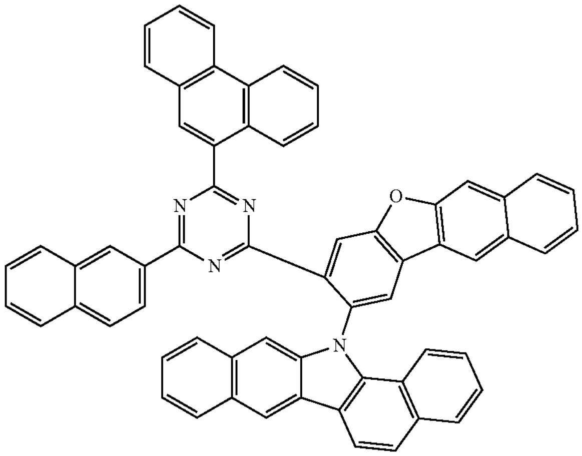
-continued
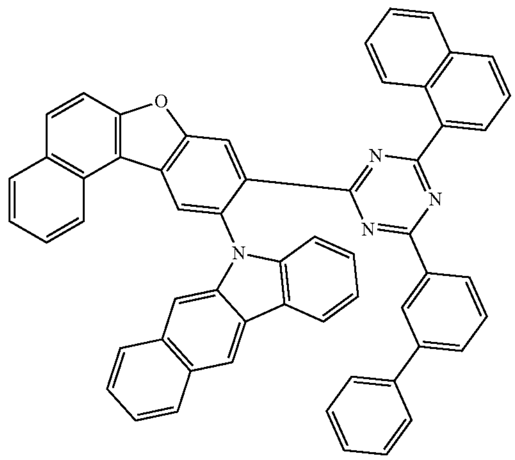
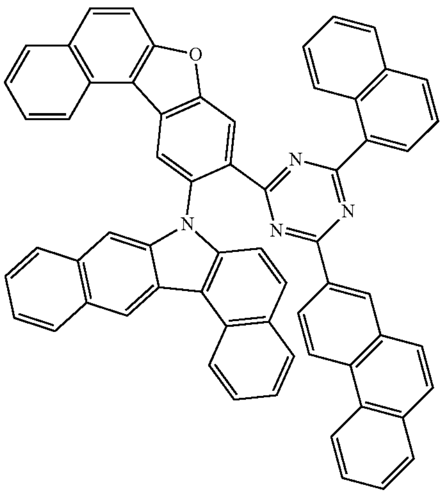
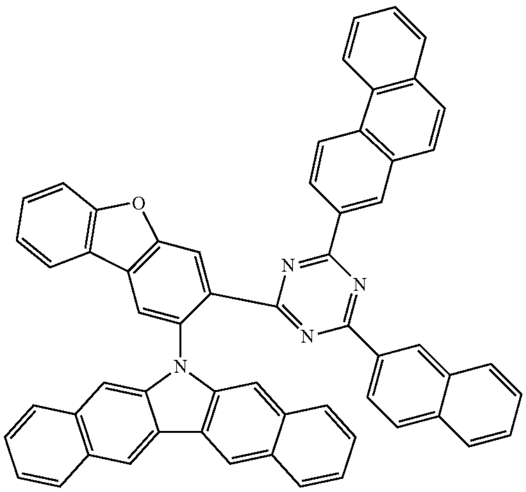

-continued
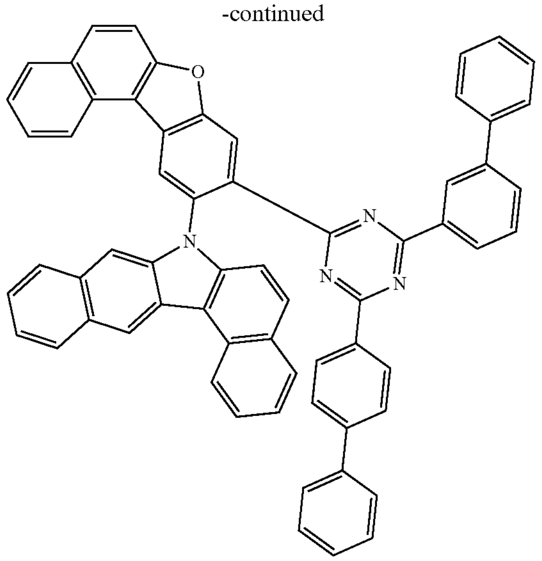
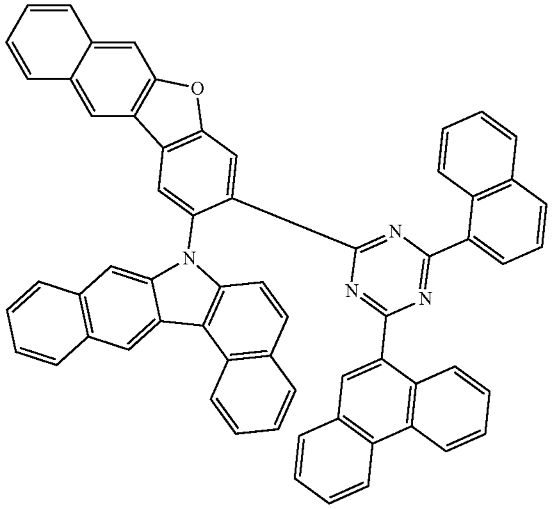
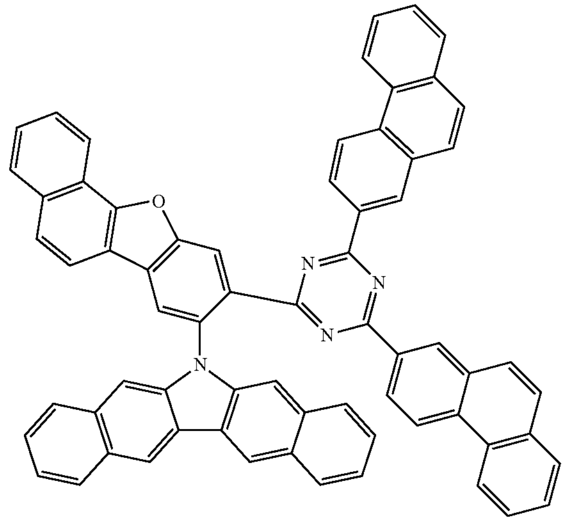
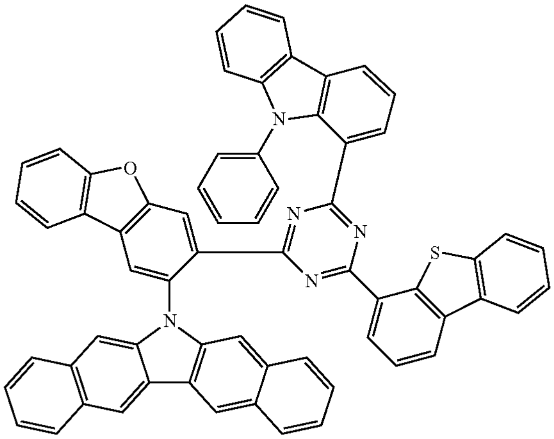
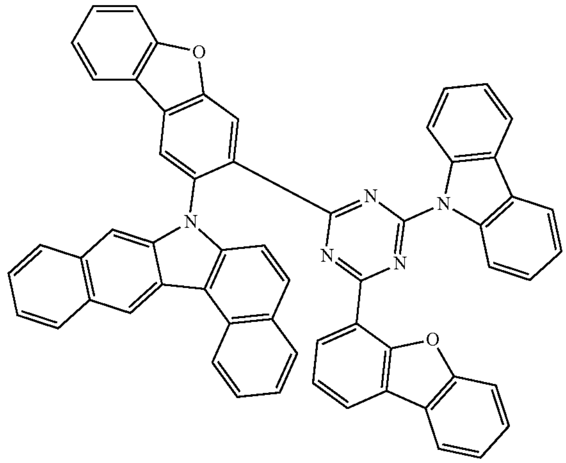
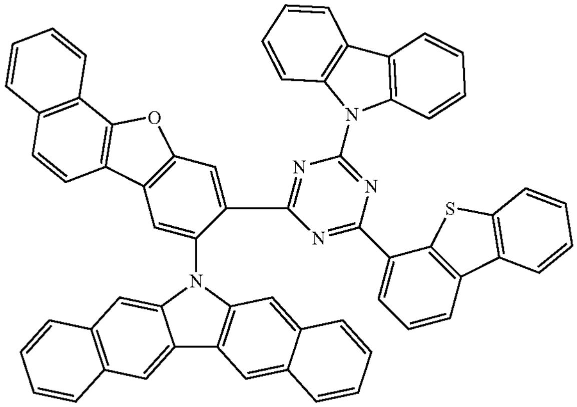

-continued
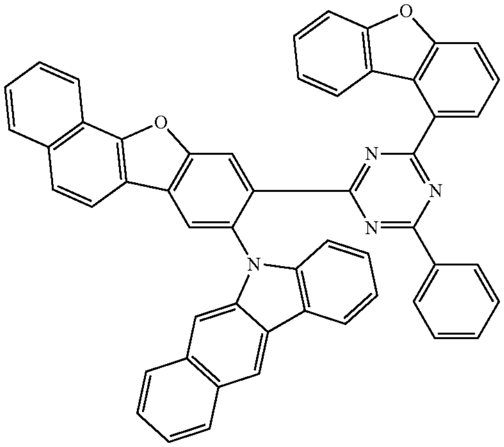
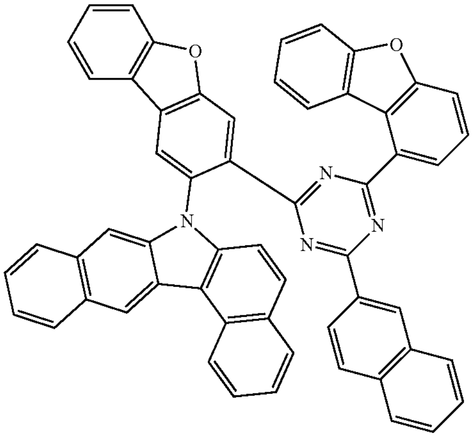
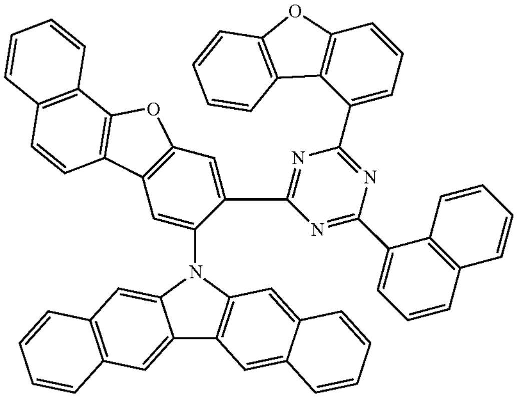
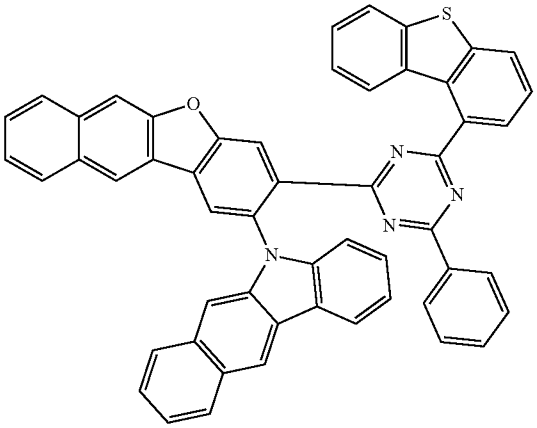
-continued
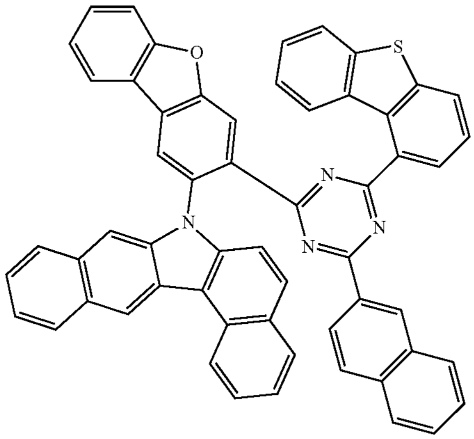
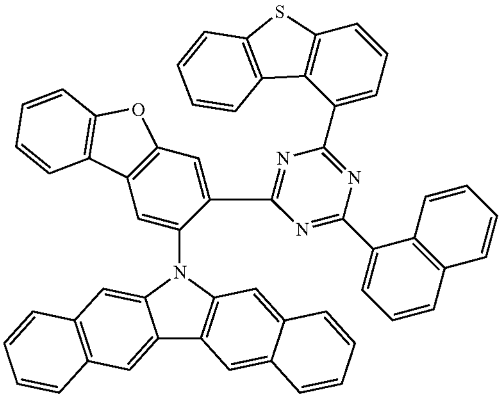
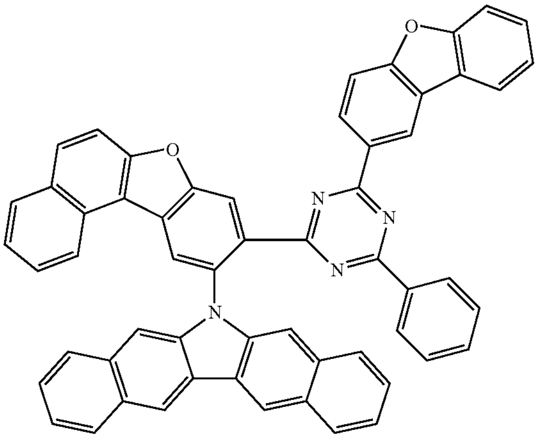
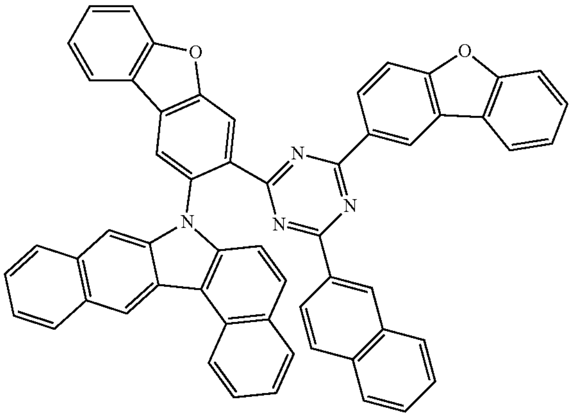

-continued
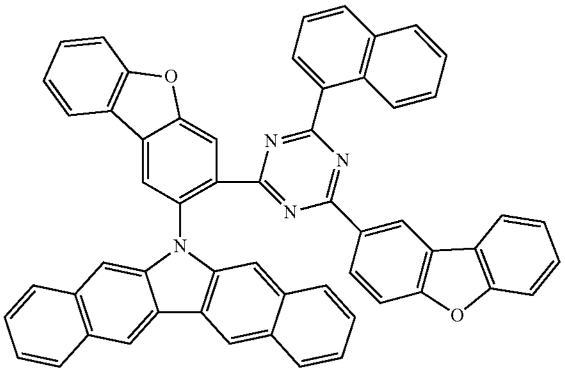
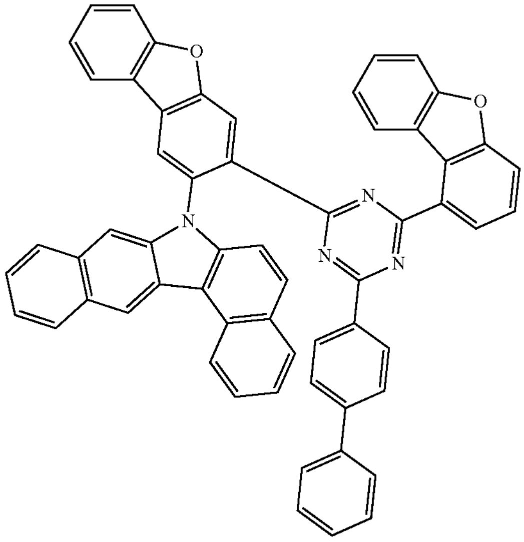
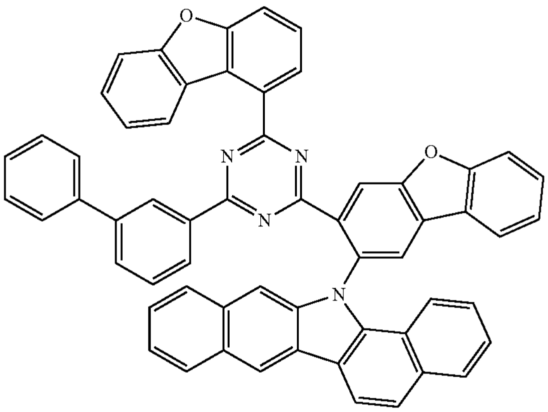
-continued
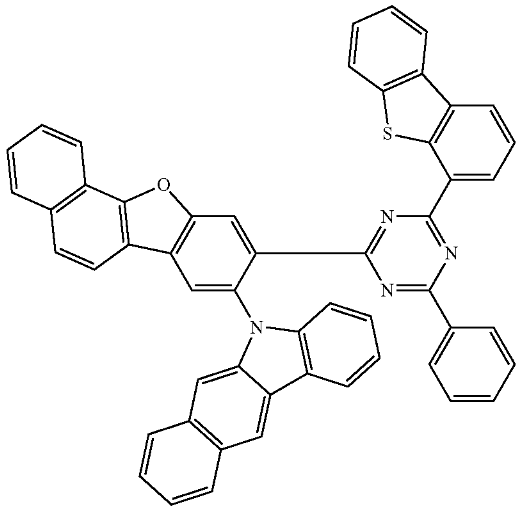
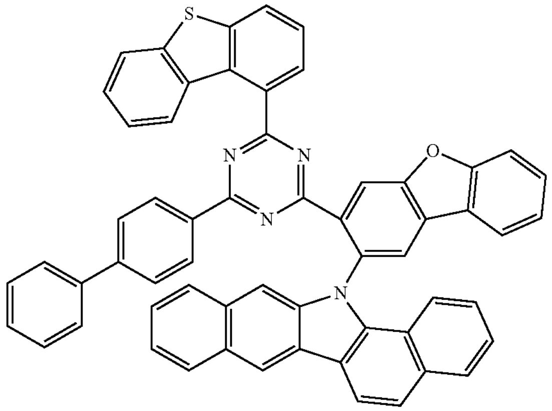
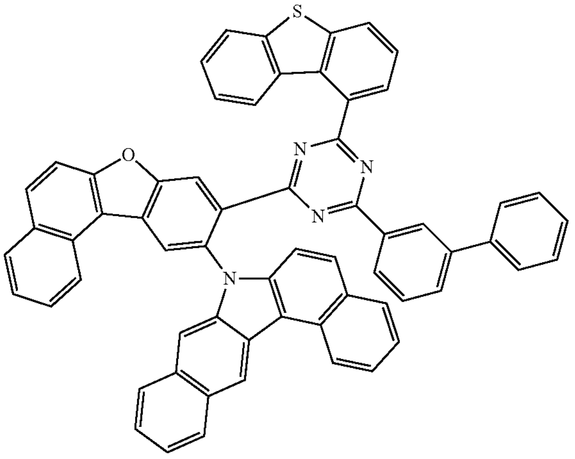

-continued
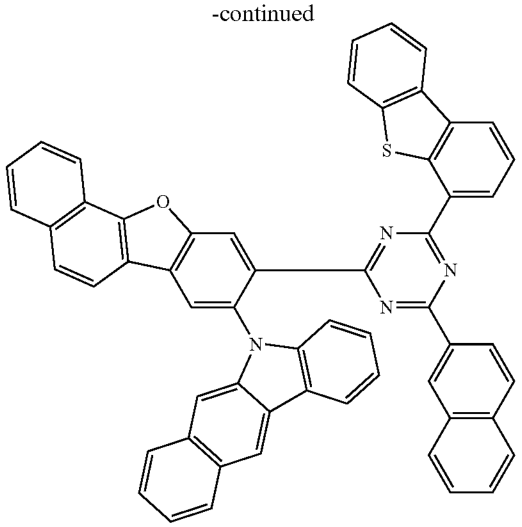
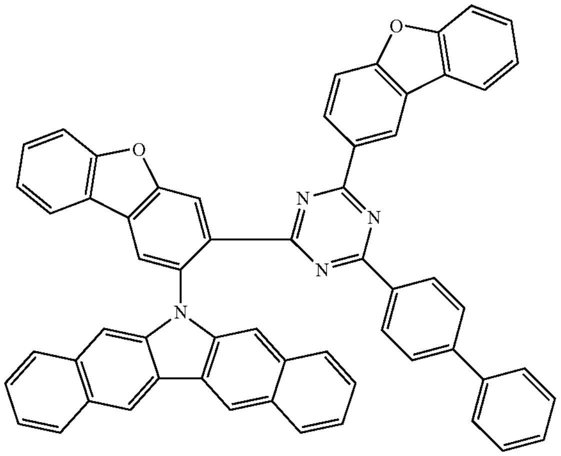
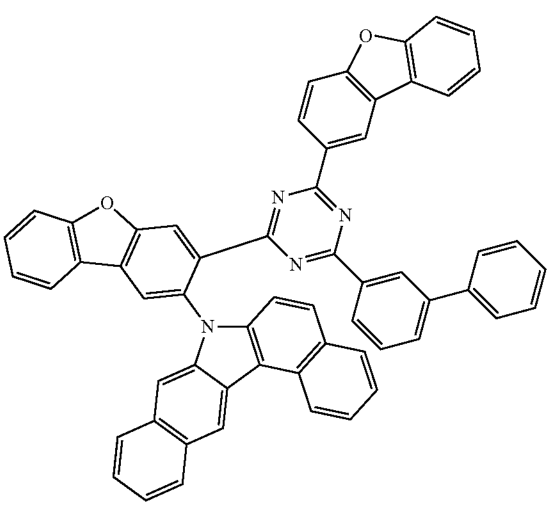
-continued
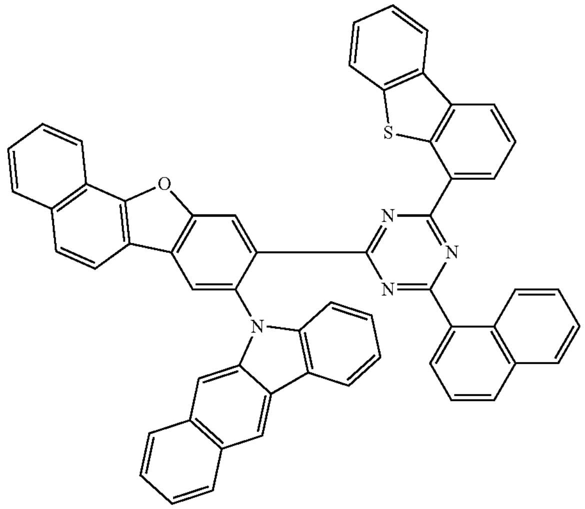
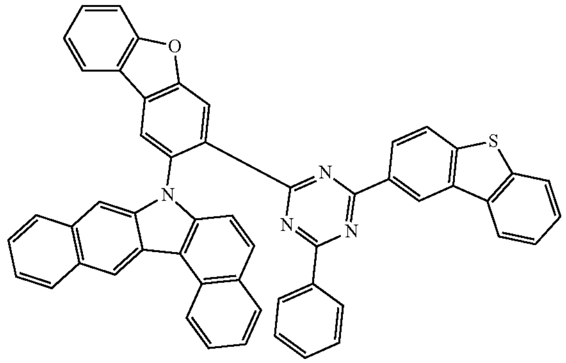
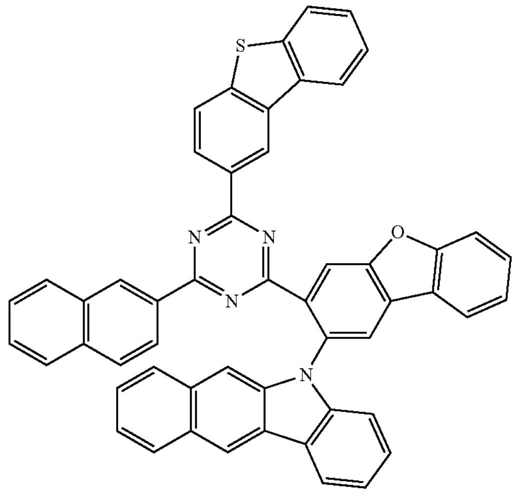

-continued
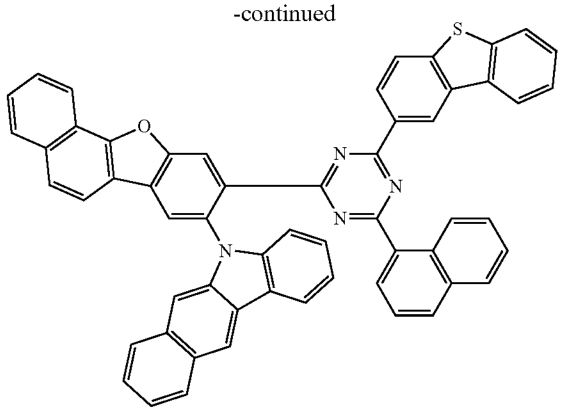
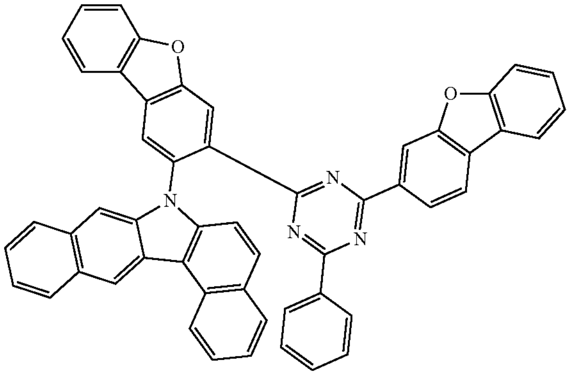
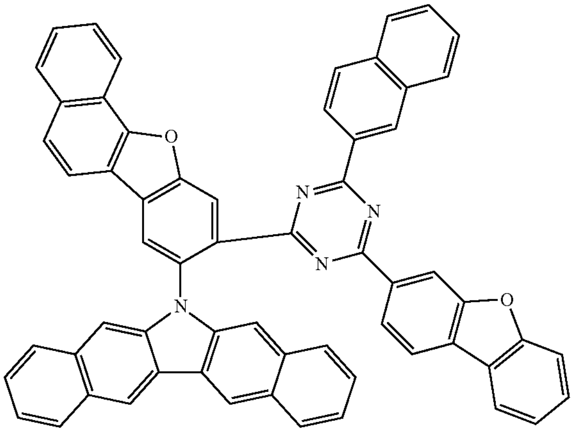
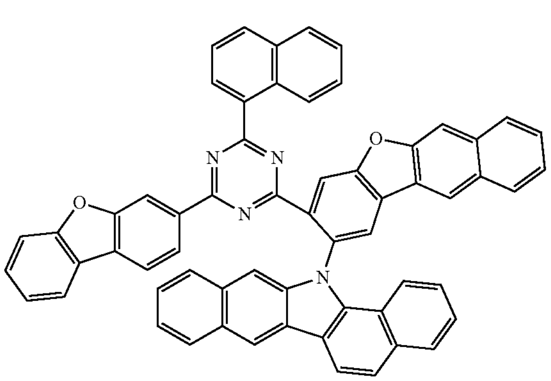
-continued
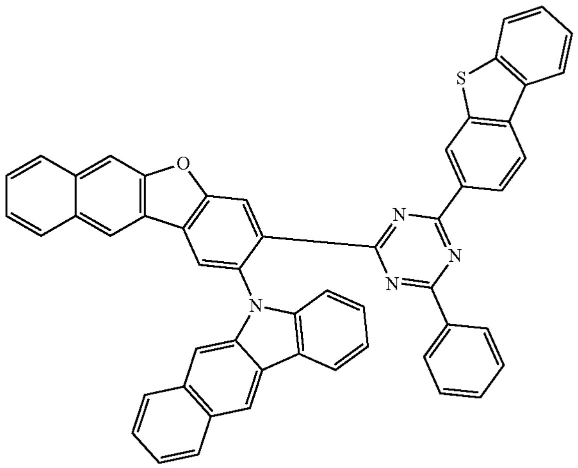
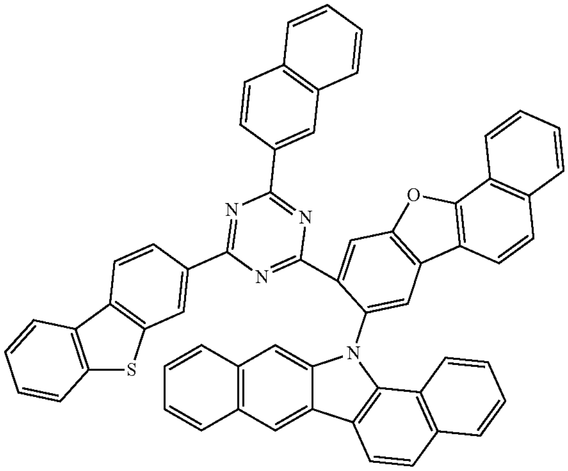
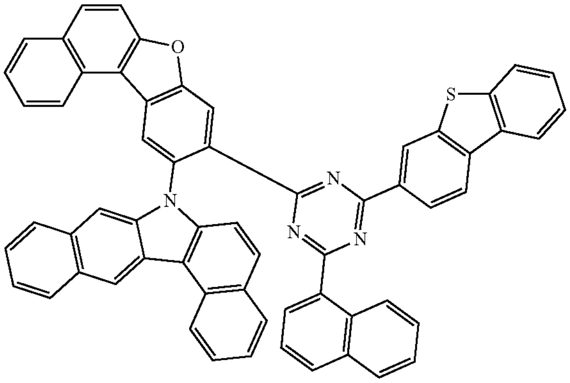

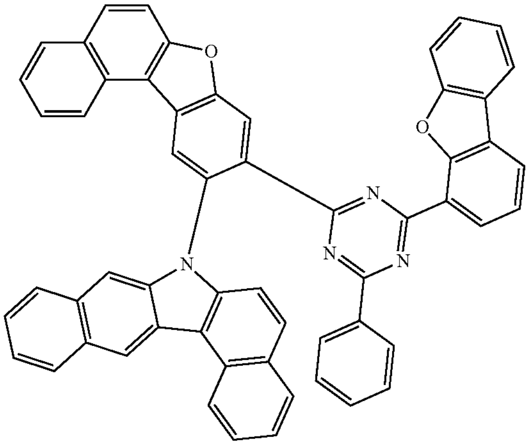
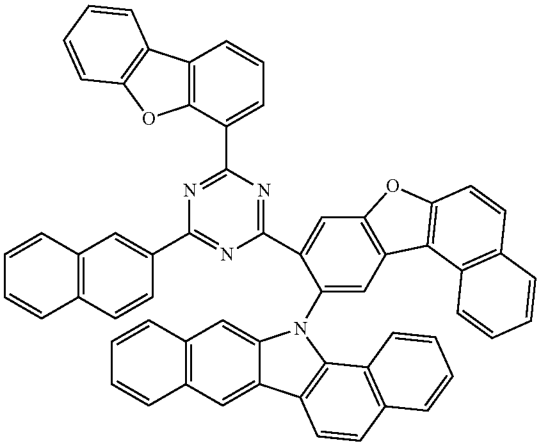
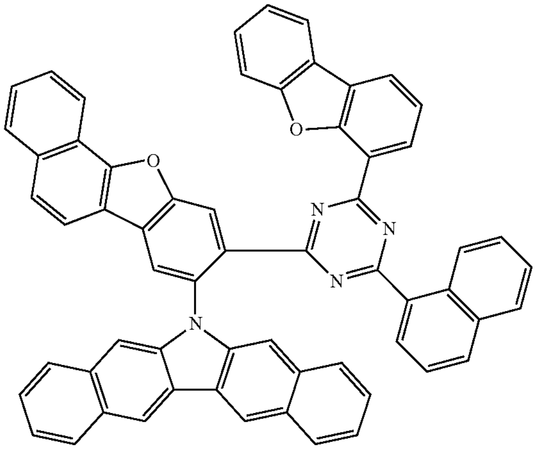
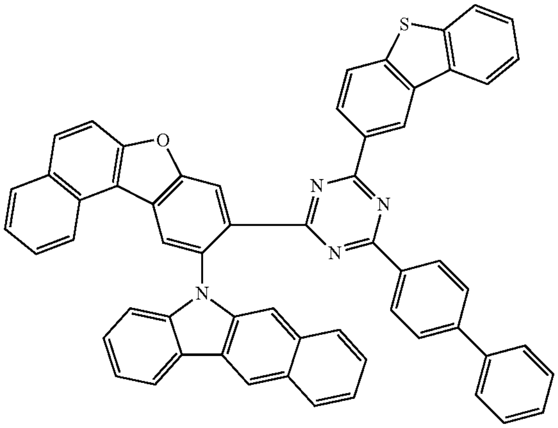
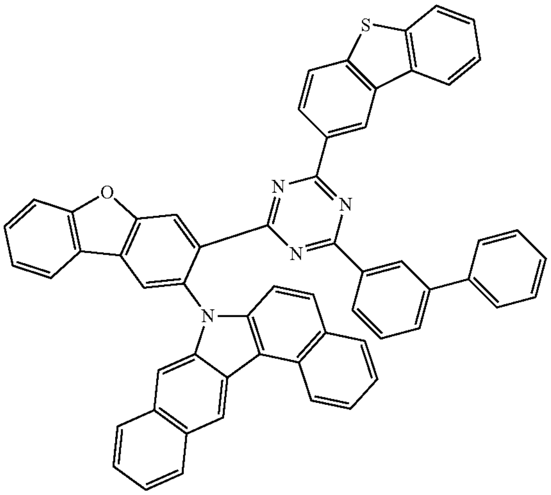
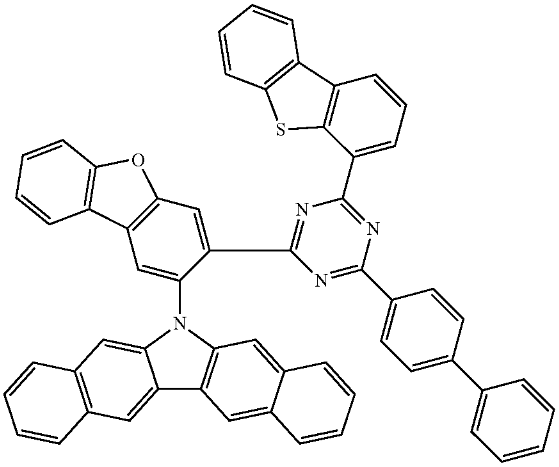

-continued
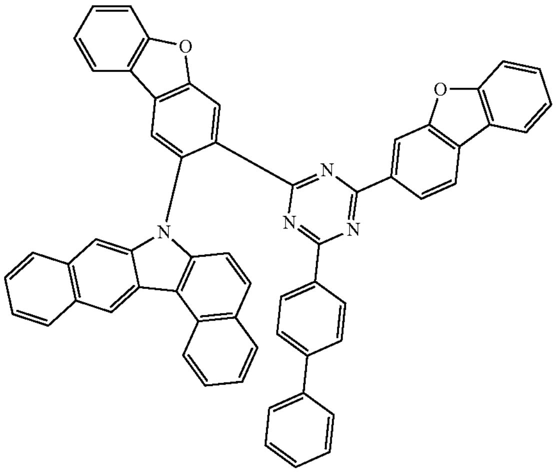
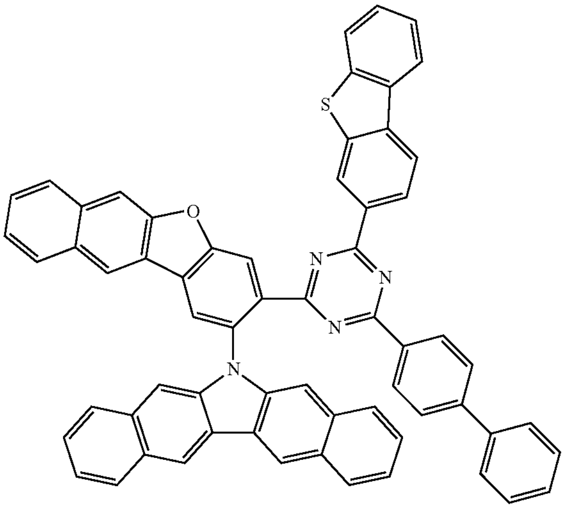
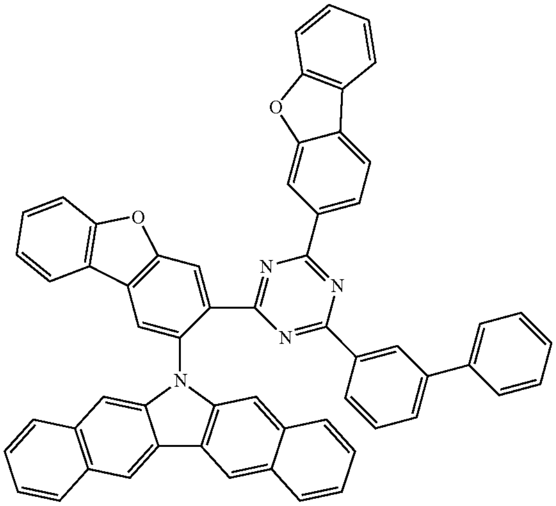
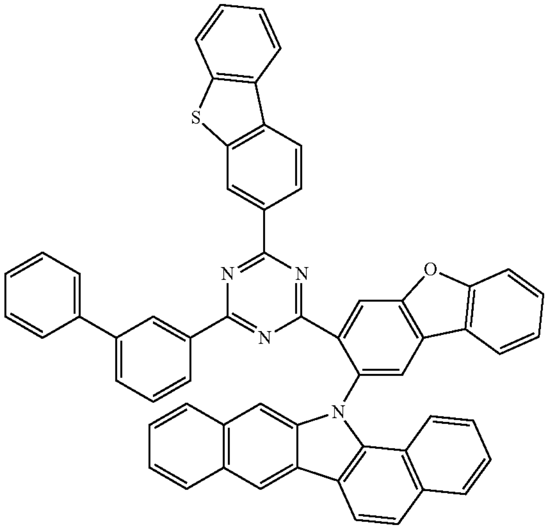
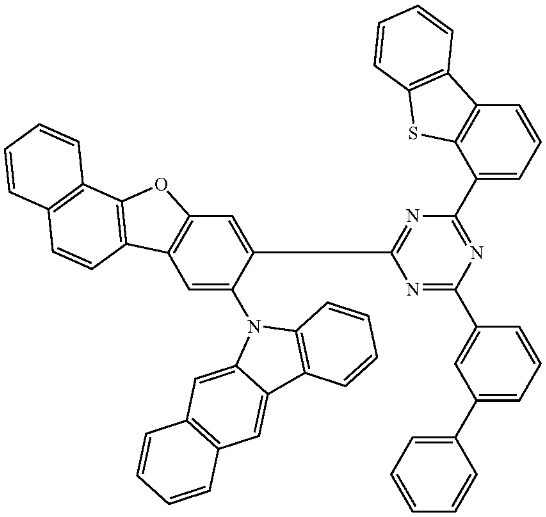
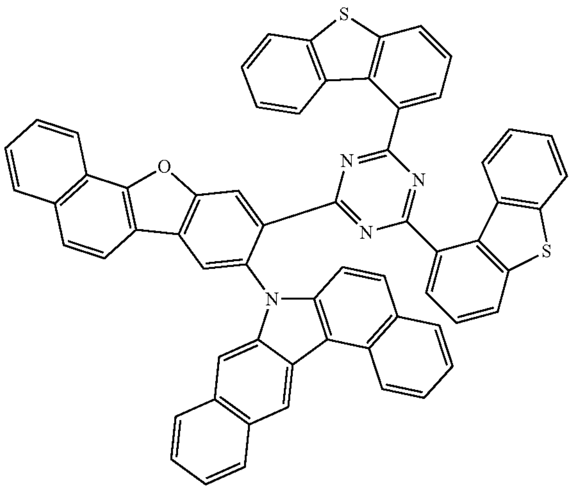
-continued -continued
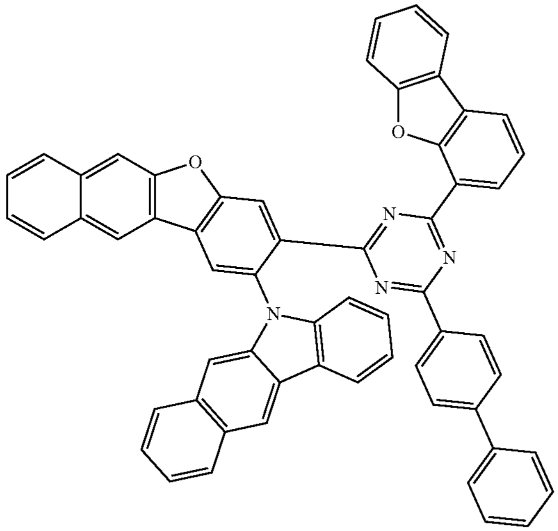
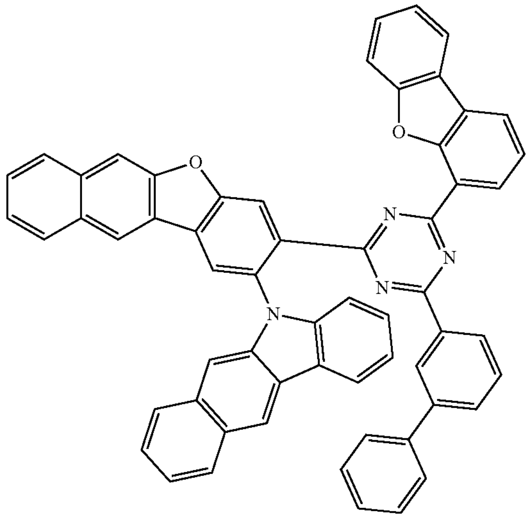
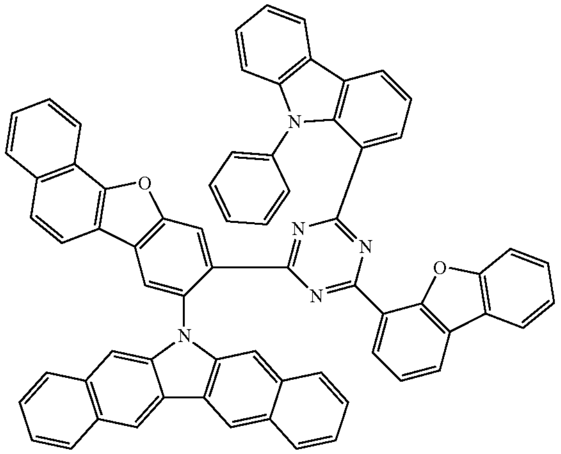
-continued
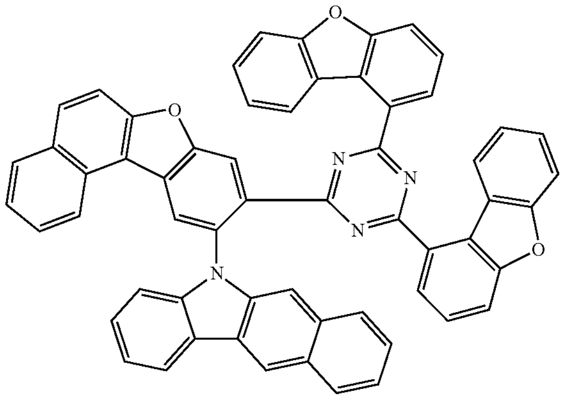
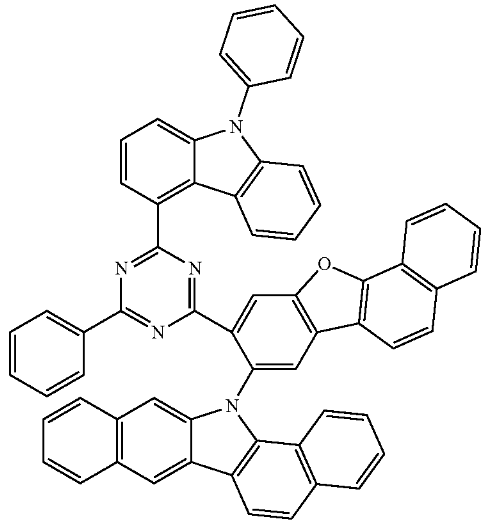
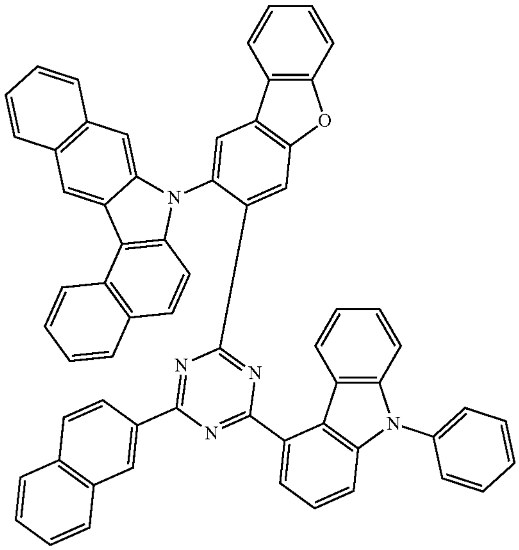

-continued
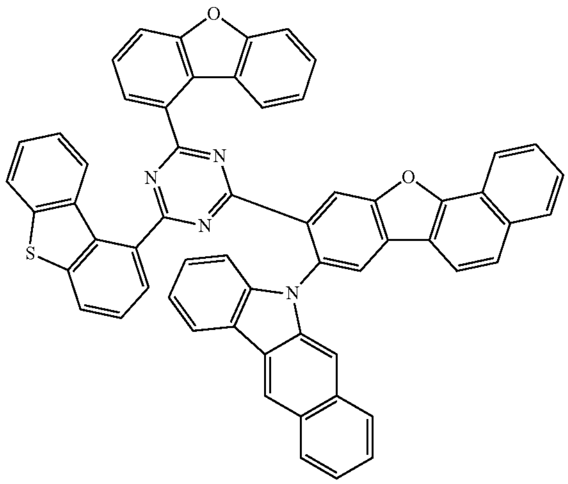
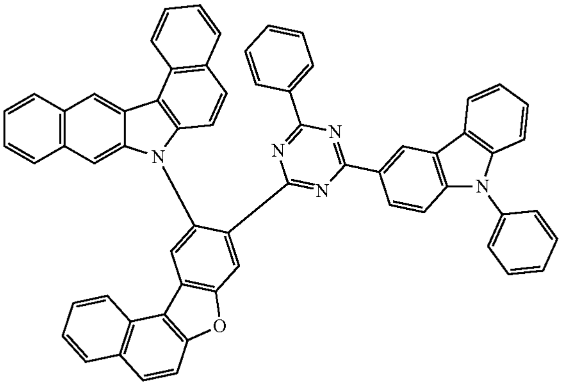
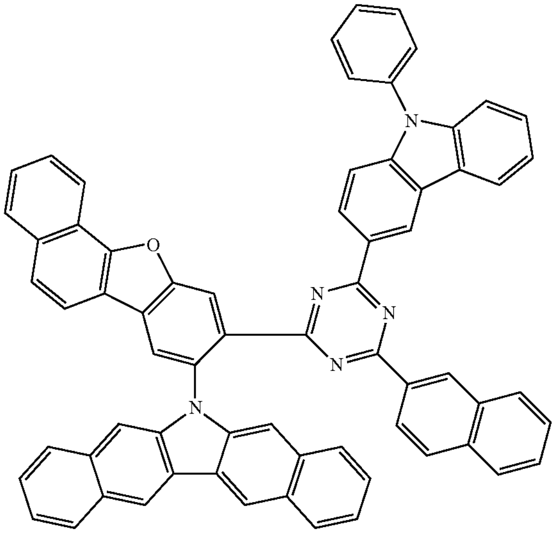
-continued
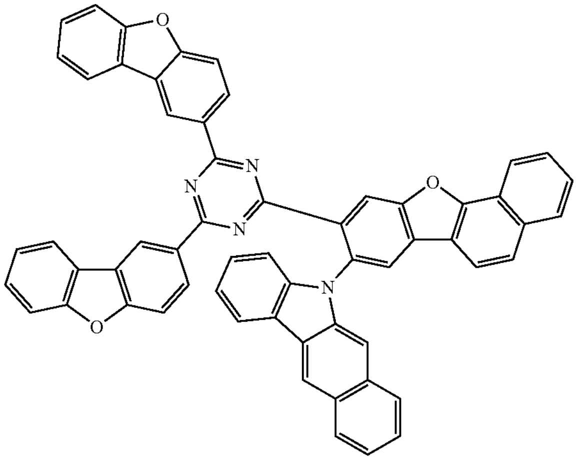
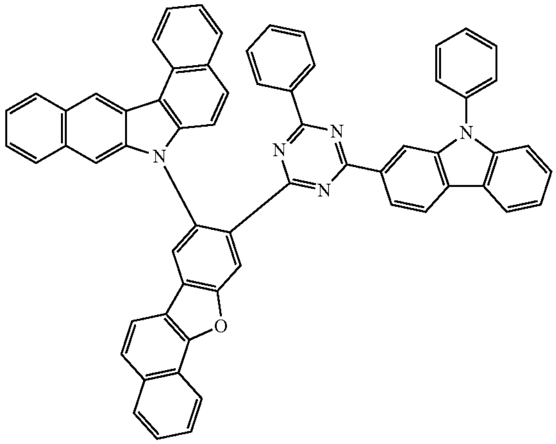
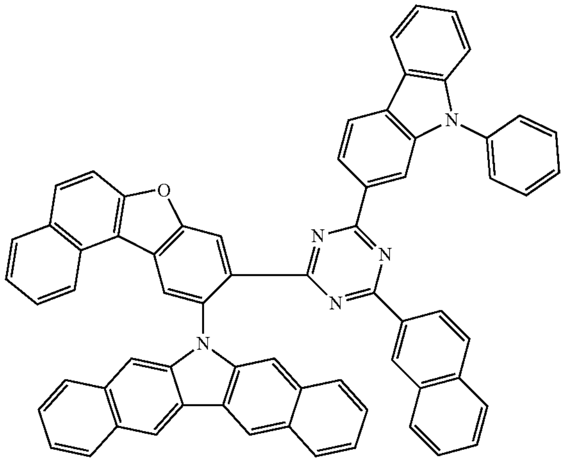

-continued
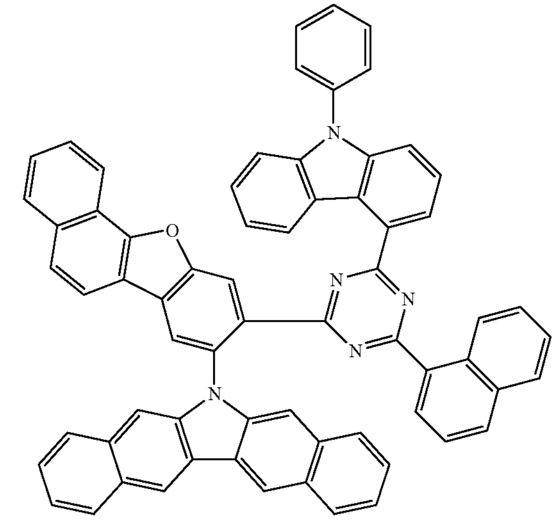
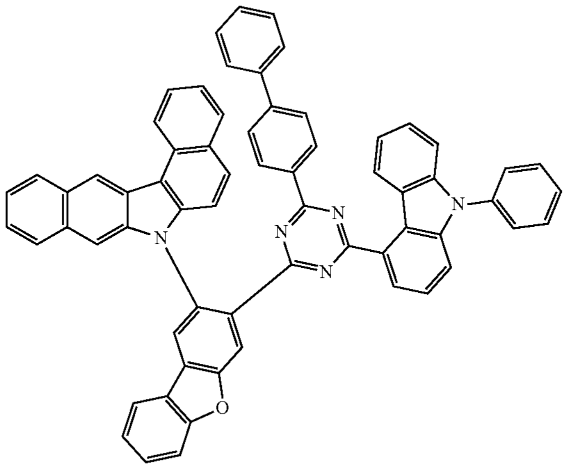
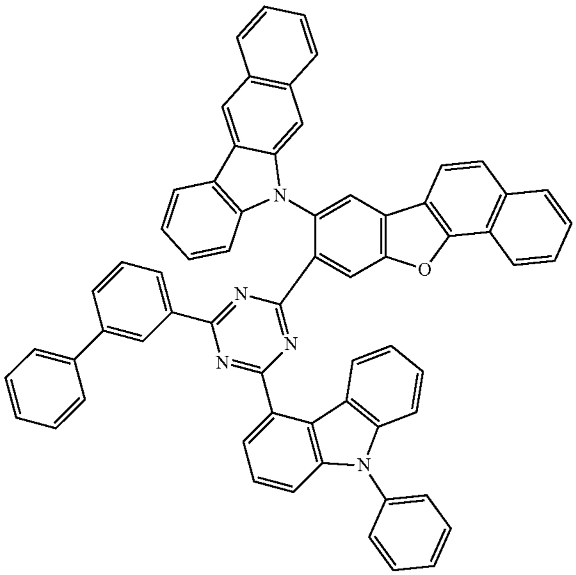
-continued
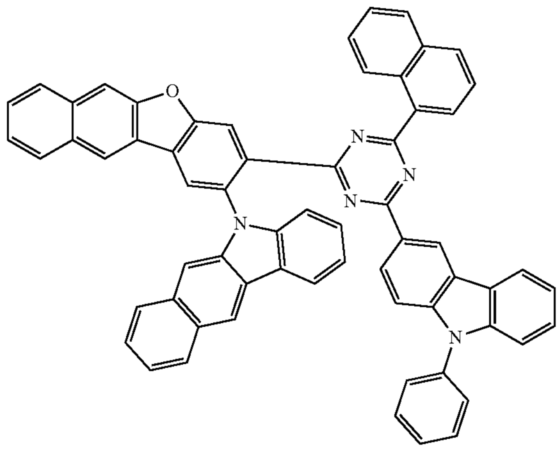
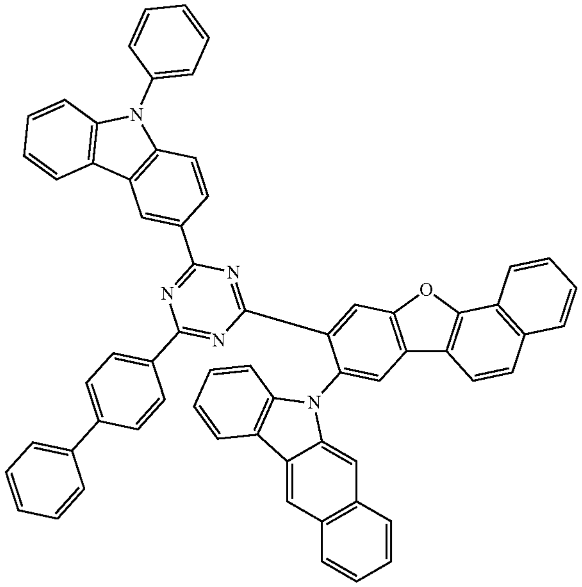
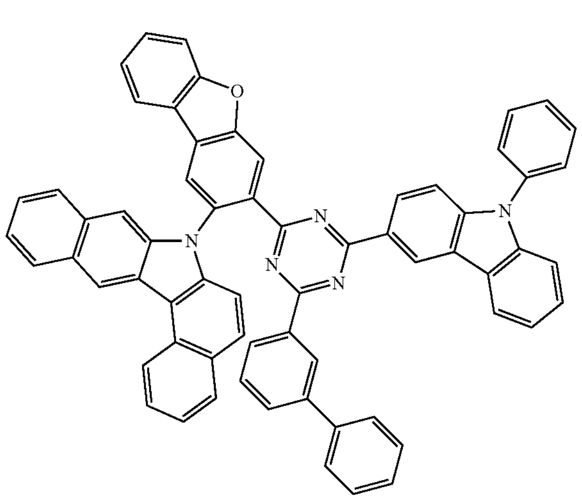

-continued
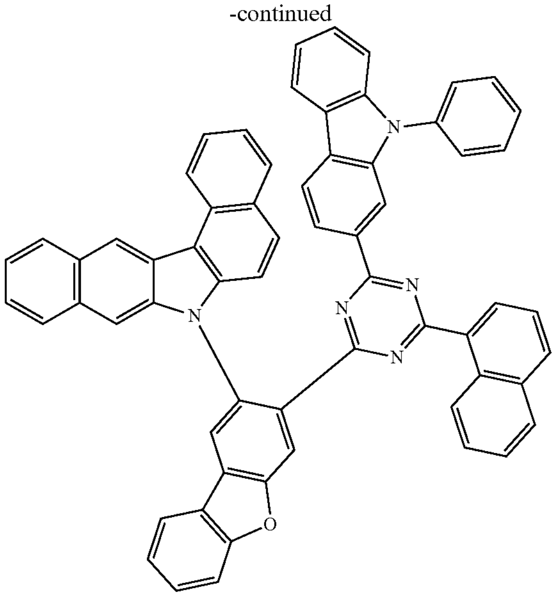
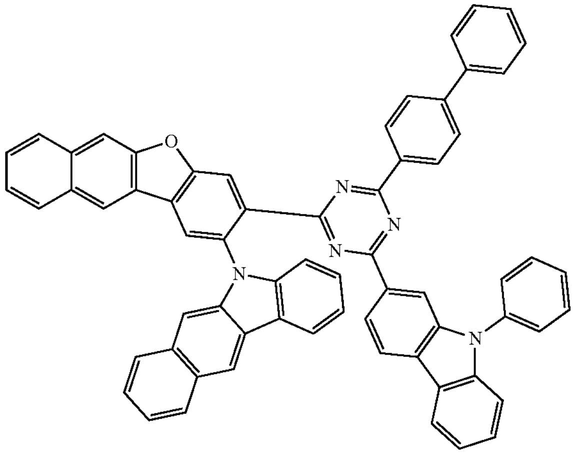
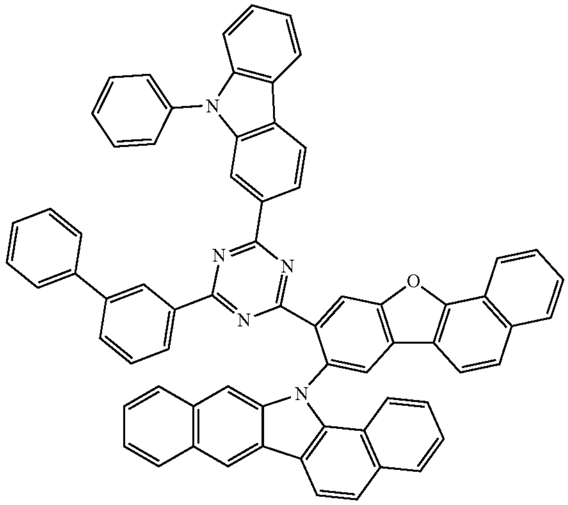
-continued
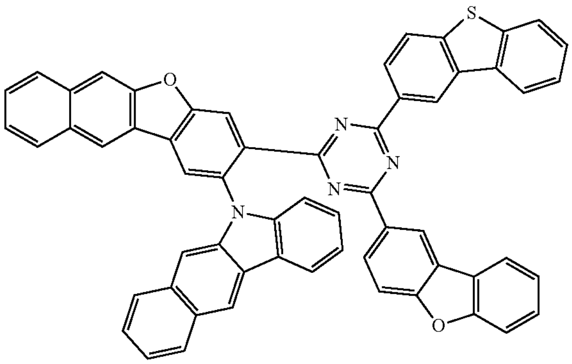
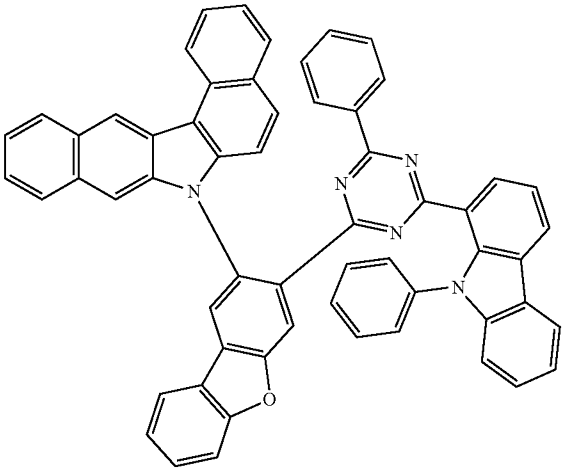
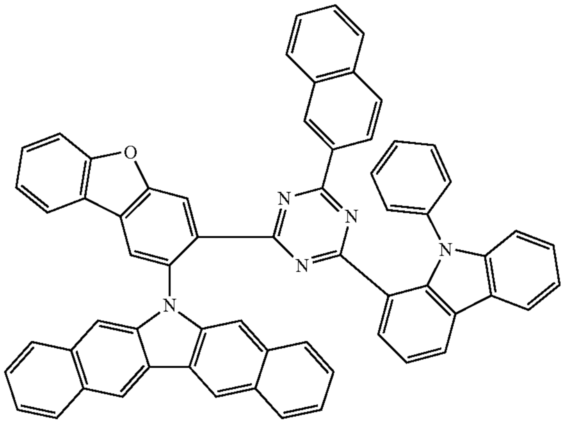

-continued
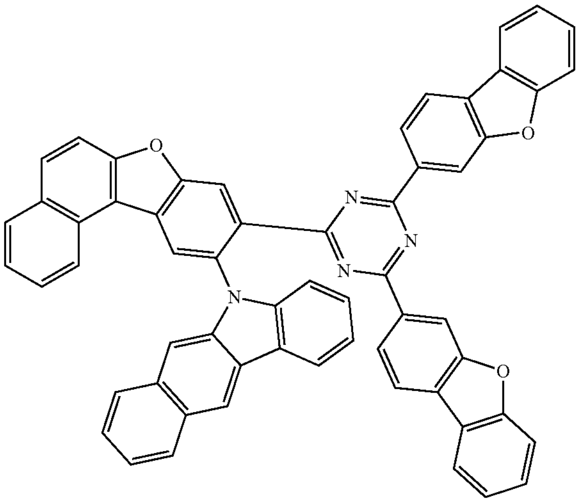
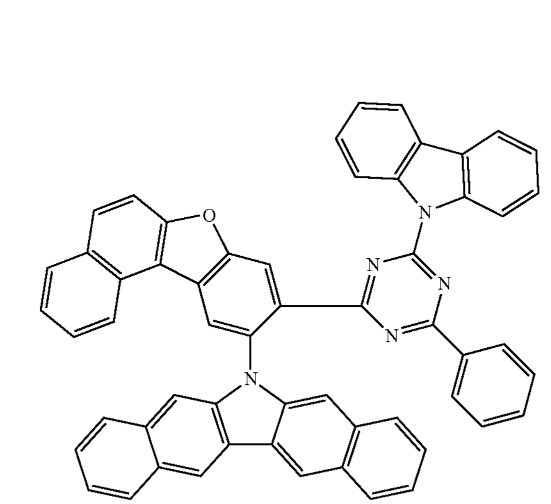
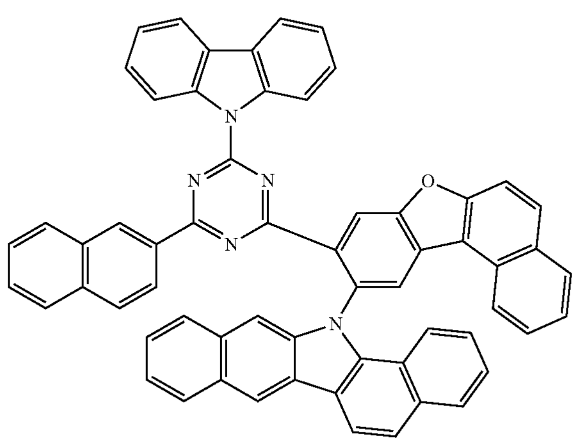
-continued
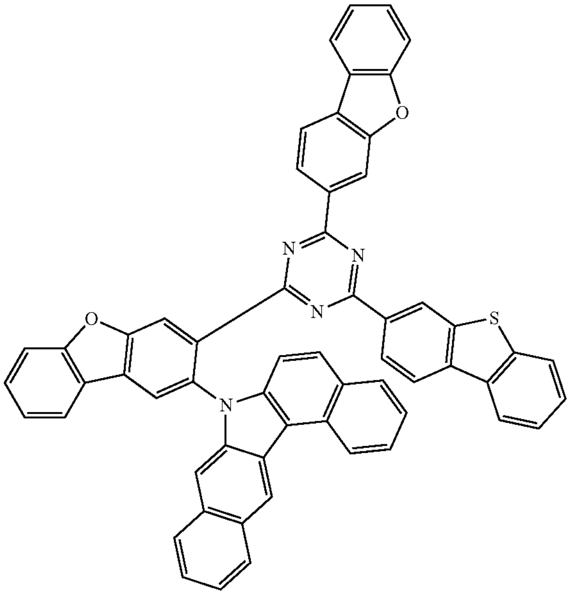
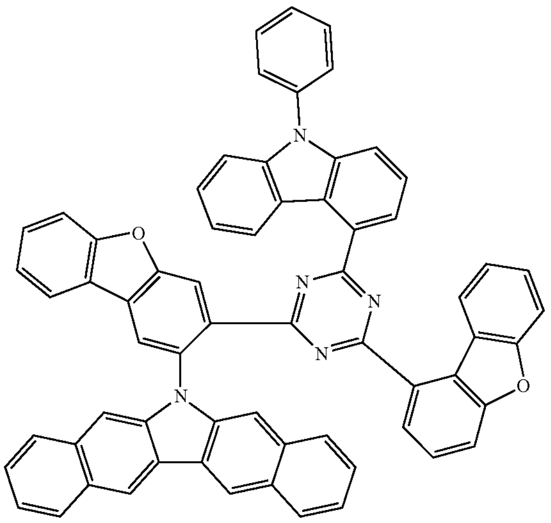
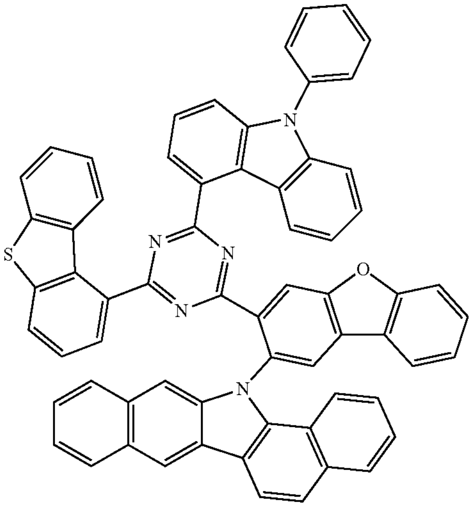

-continued
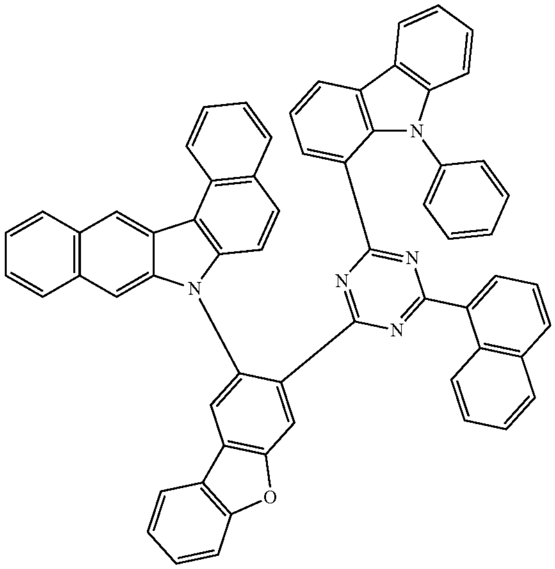
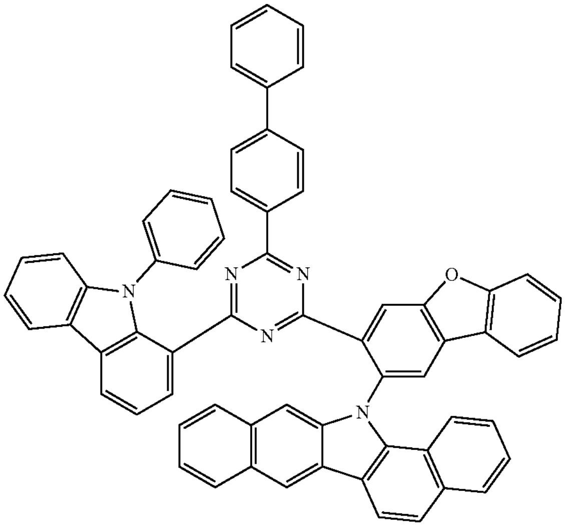
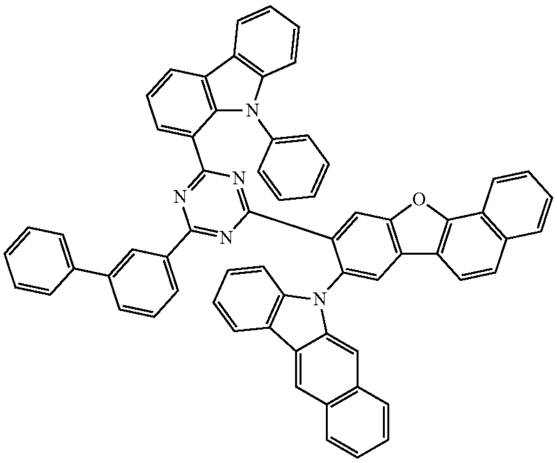
-continued
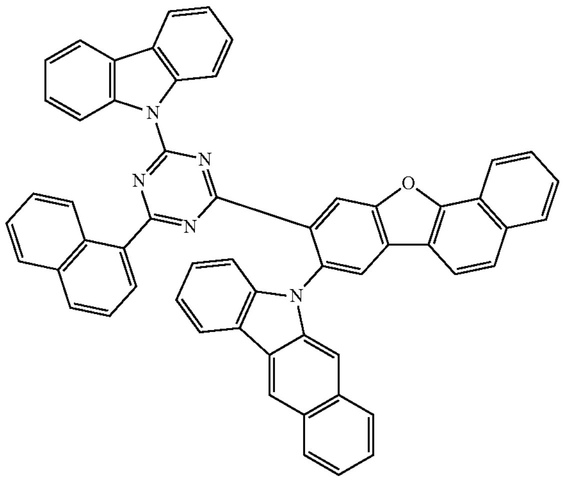
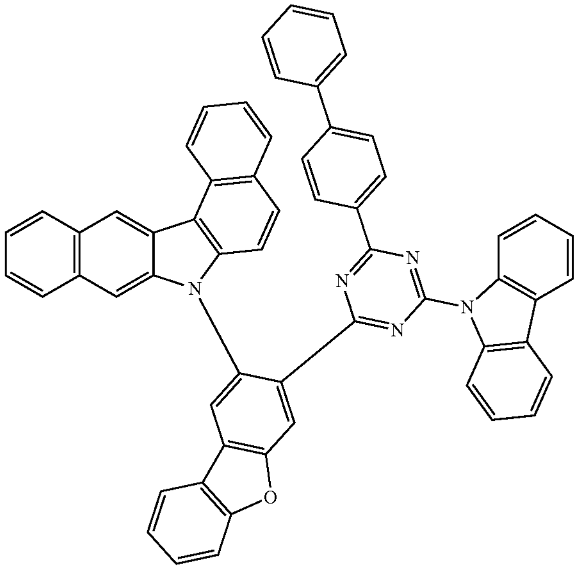
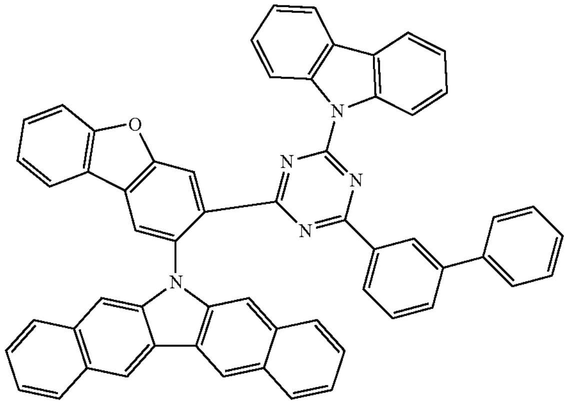

-continued
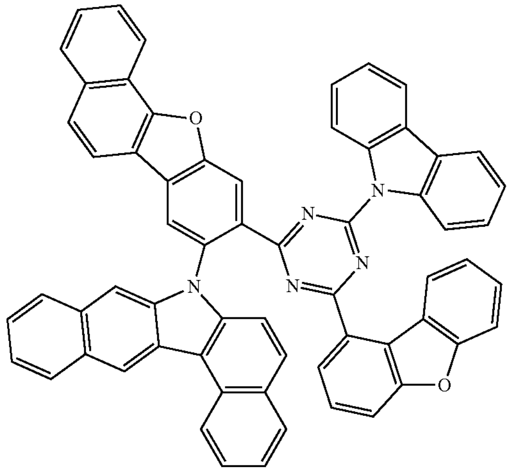
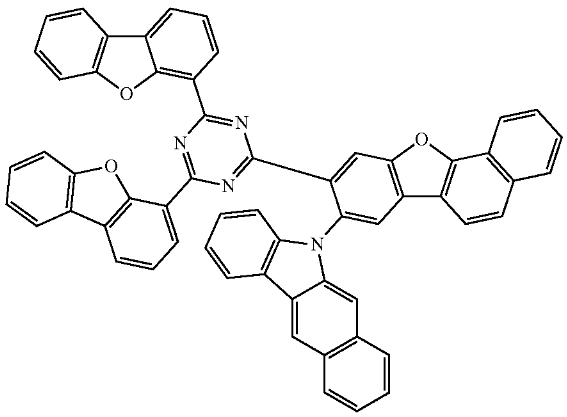
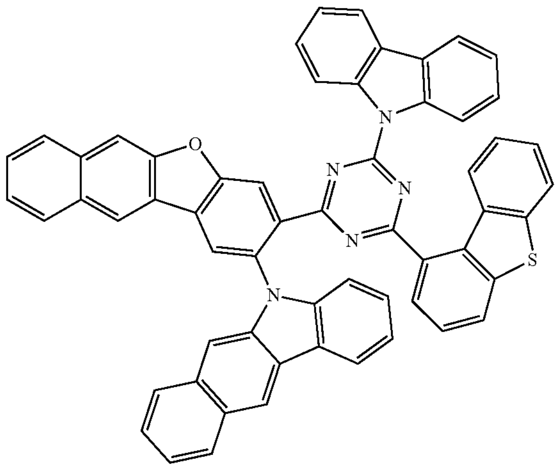
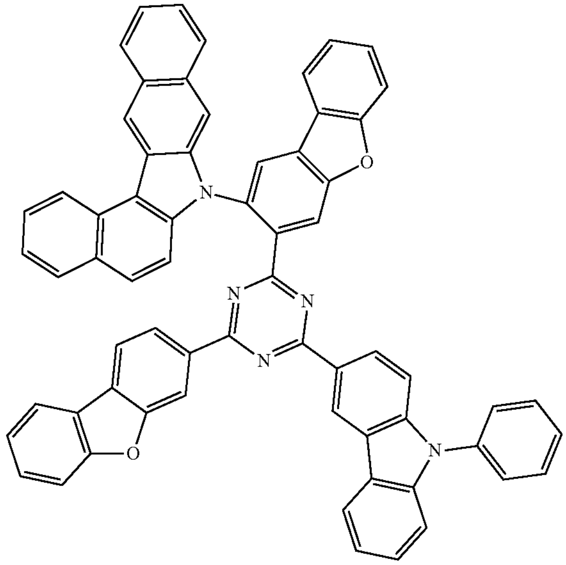
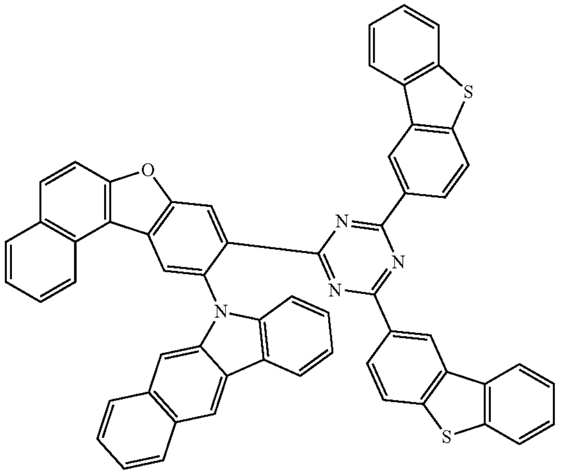
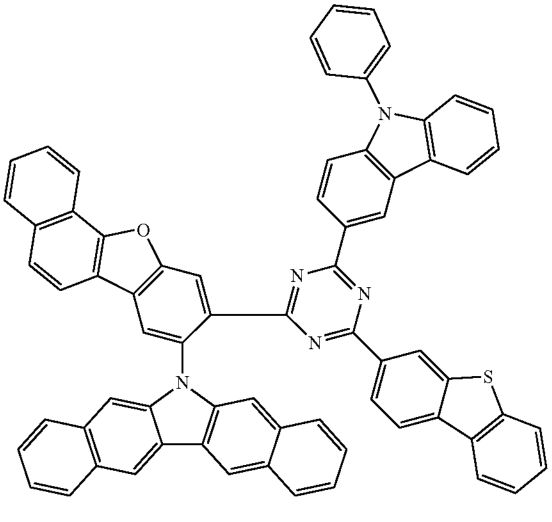
-continued -continued
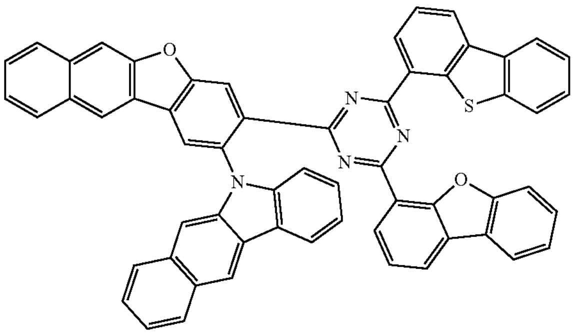
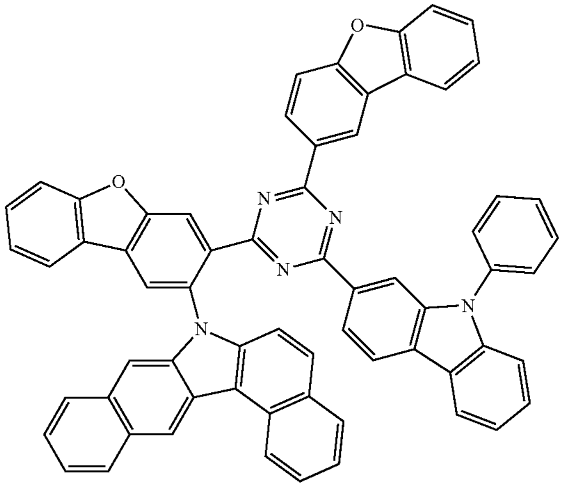
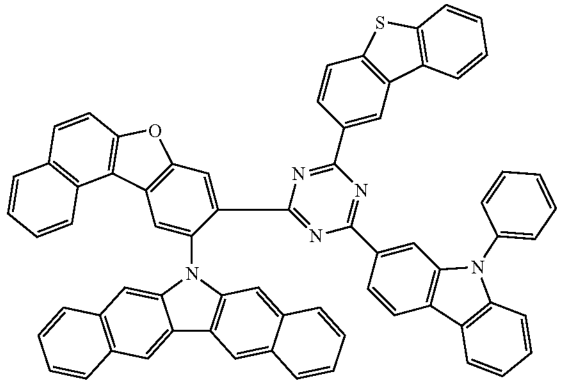
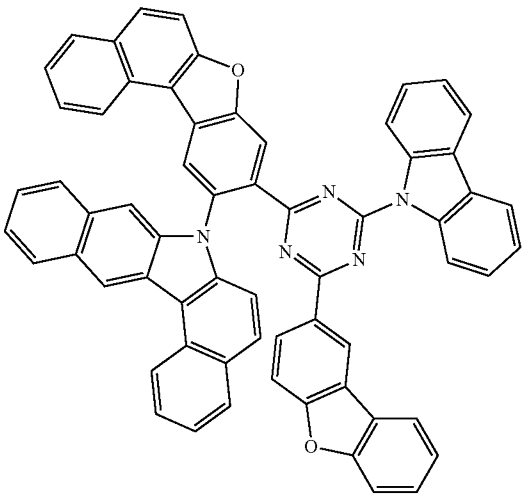
-continued
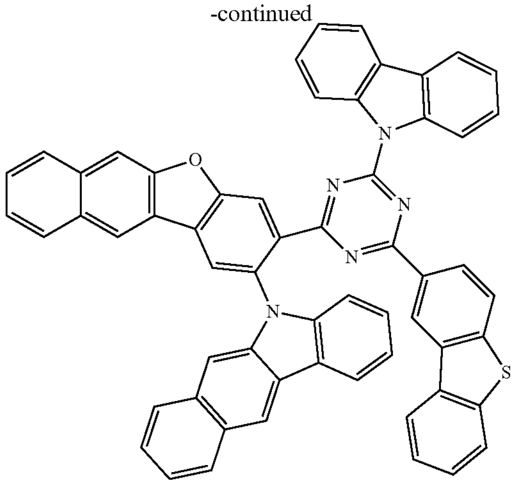
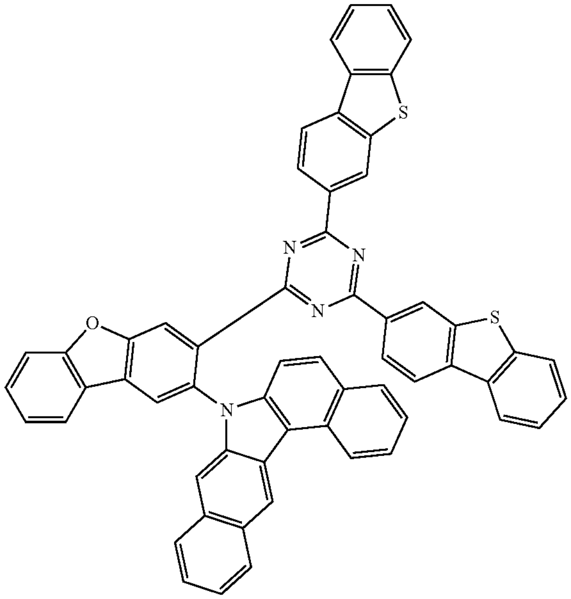
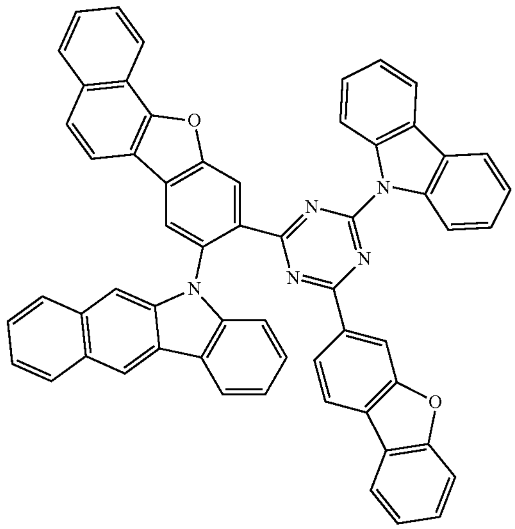

-continued
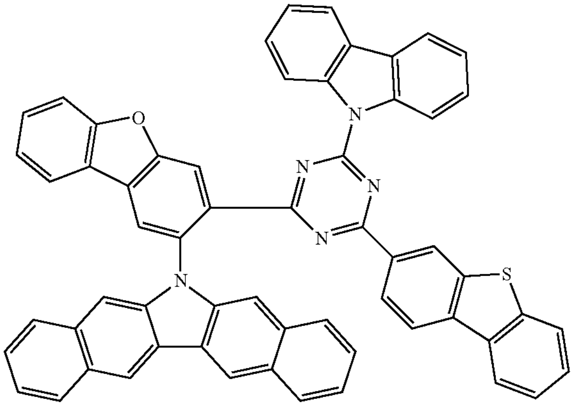
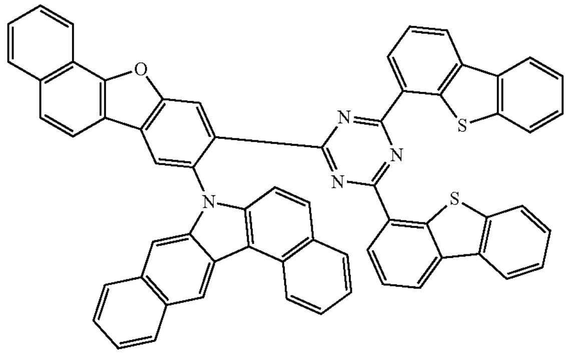
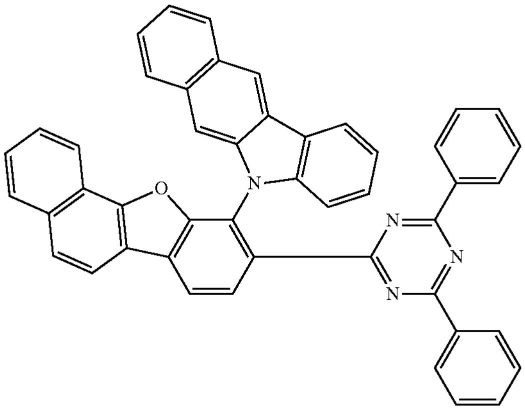
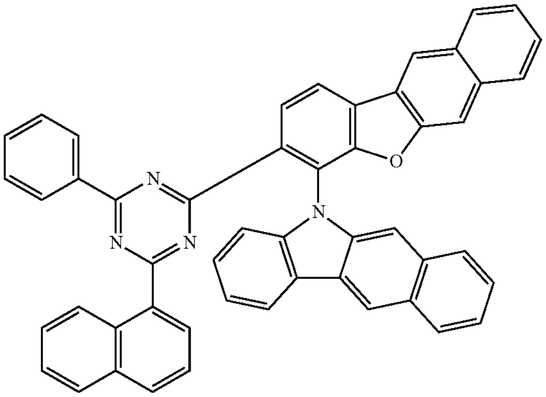
-continued
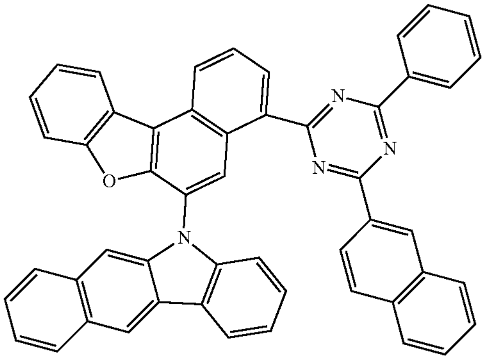
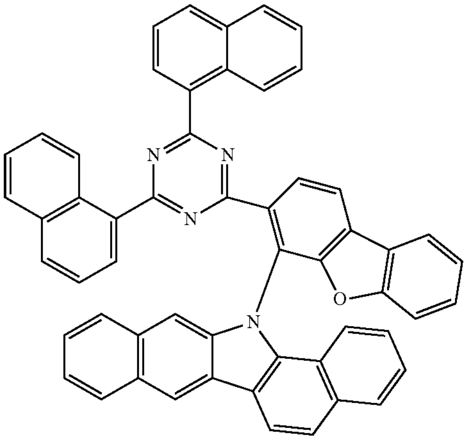
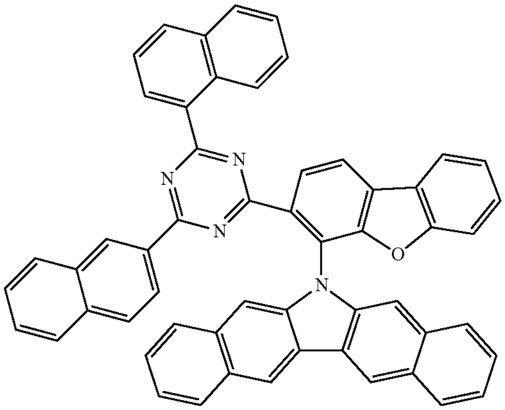
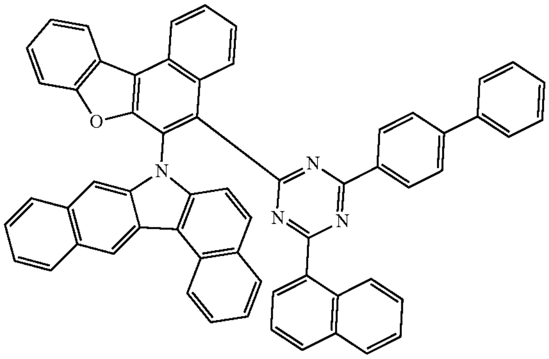

-continued
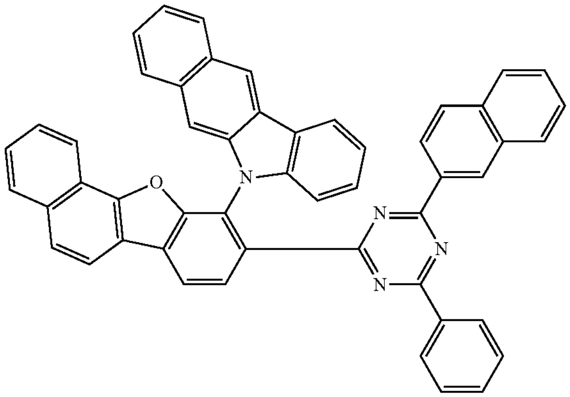
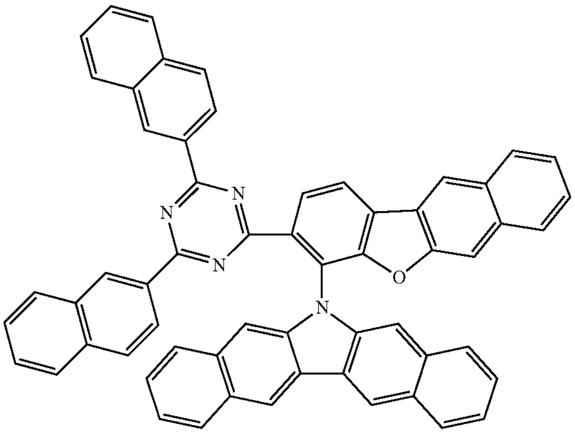
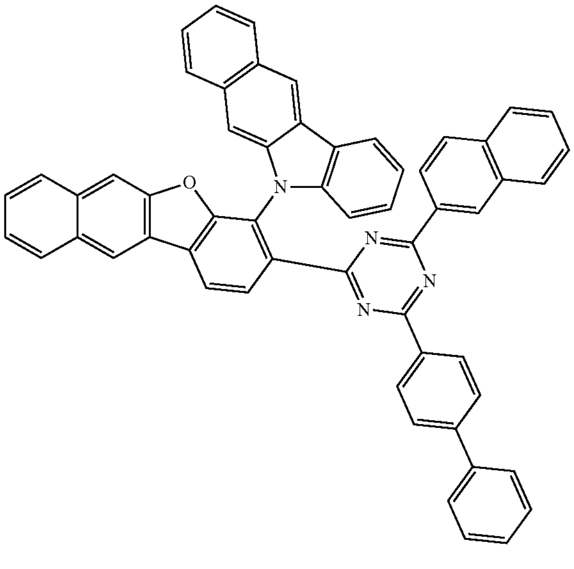
-continued
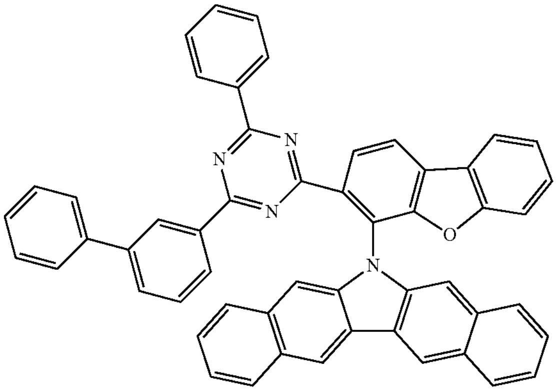
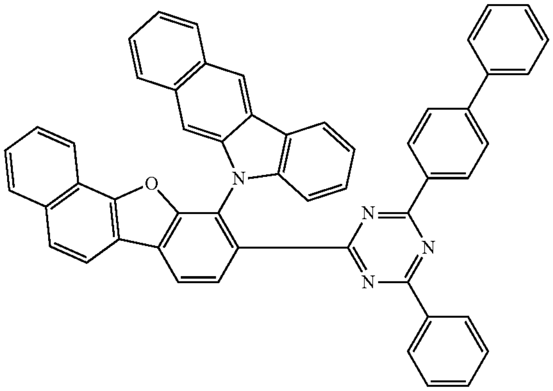
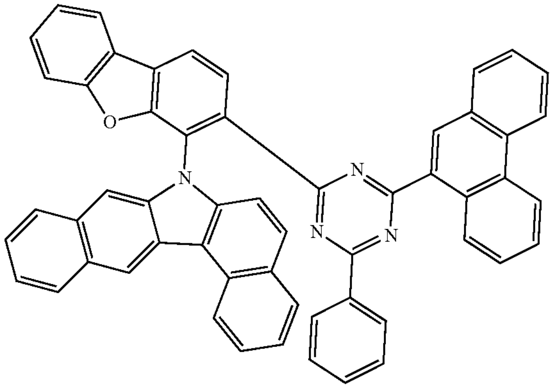
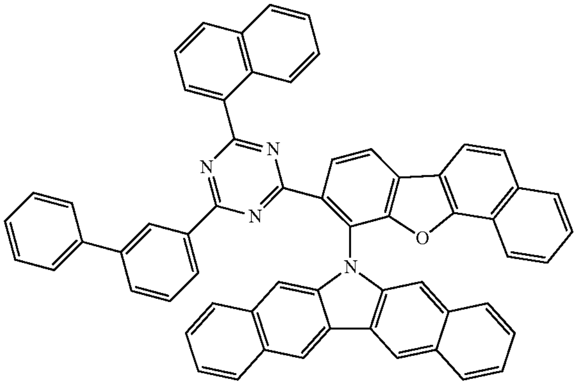

-continued
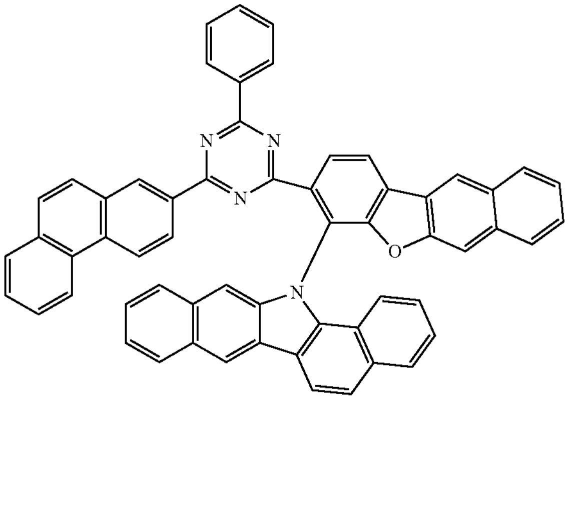
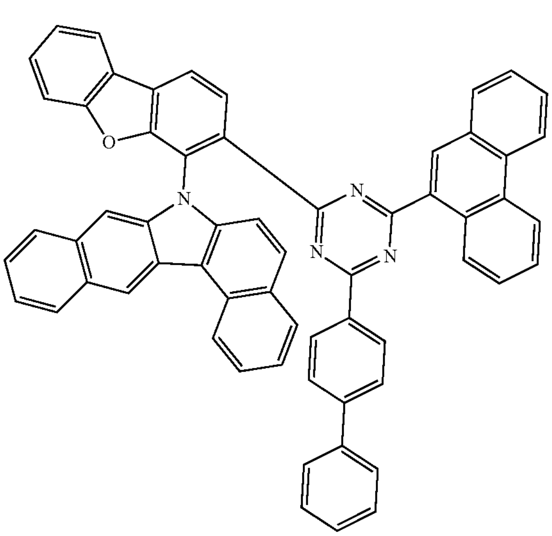
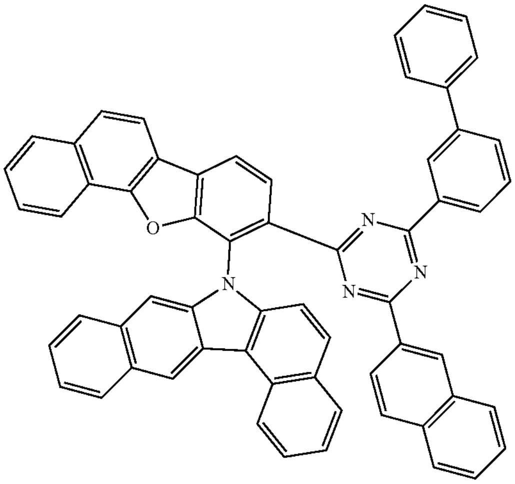
-continued
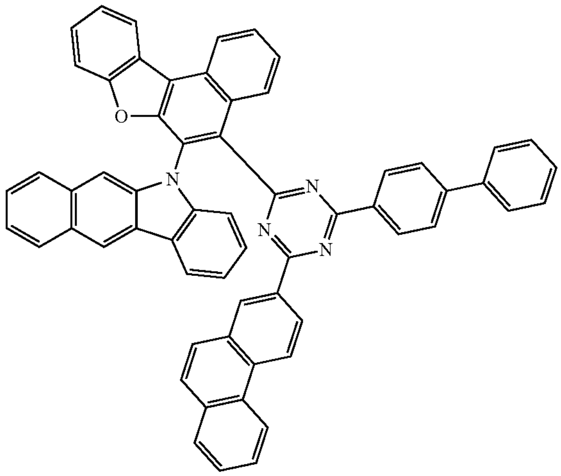
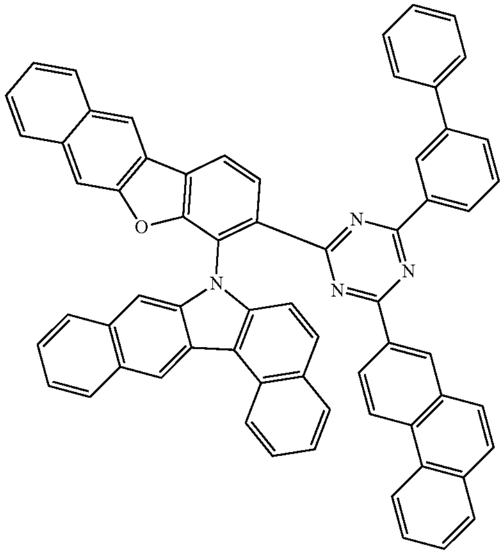
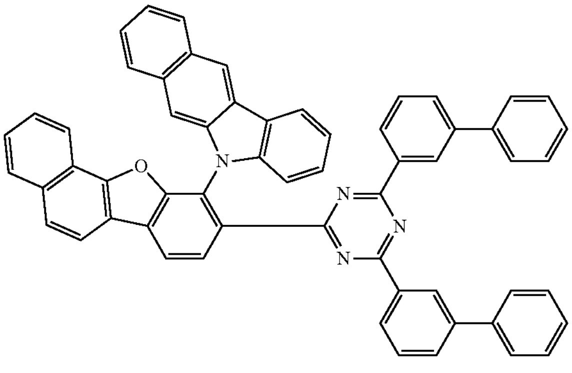

-continued
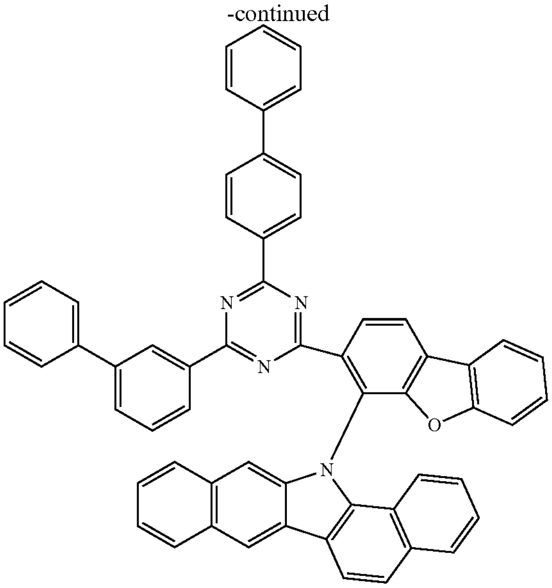
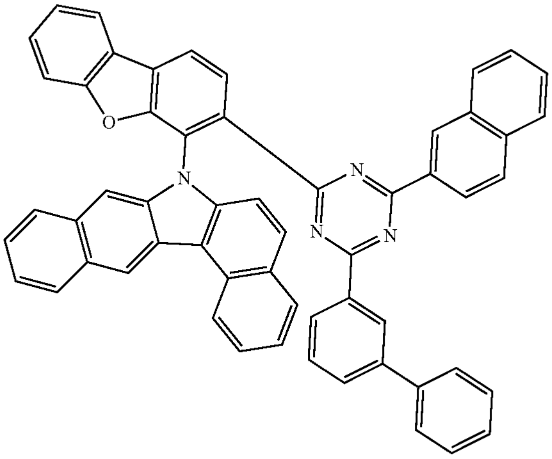
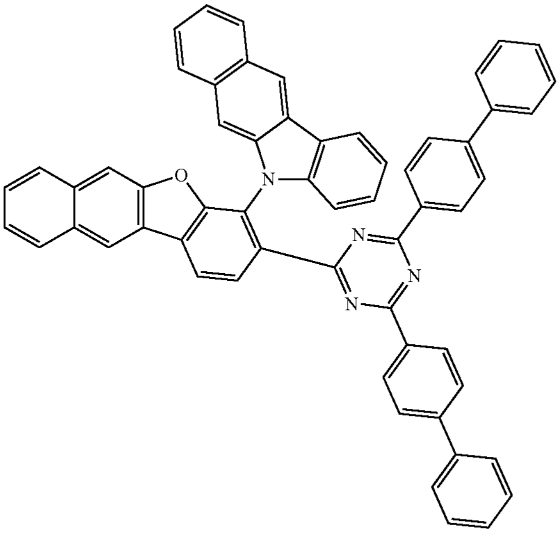
-continued
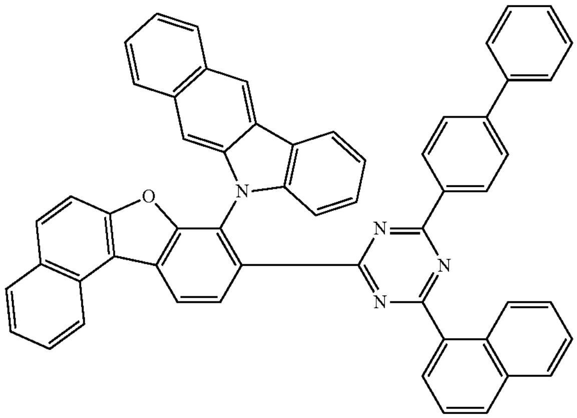
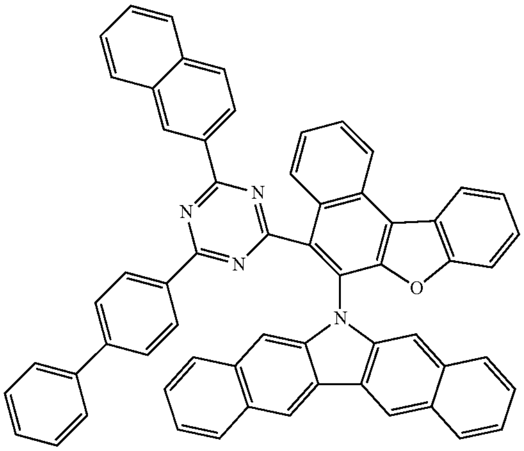
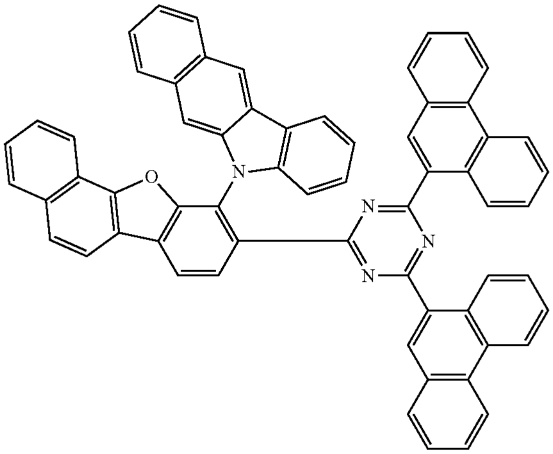
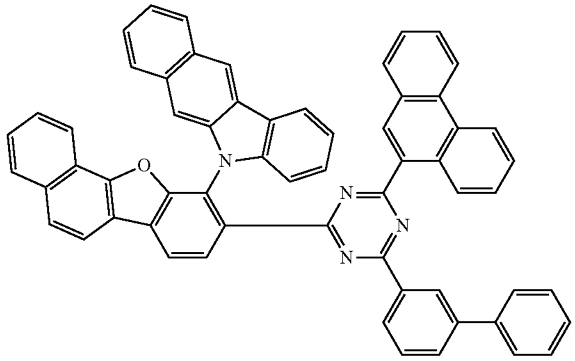

-continued
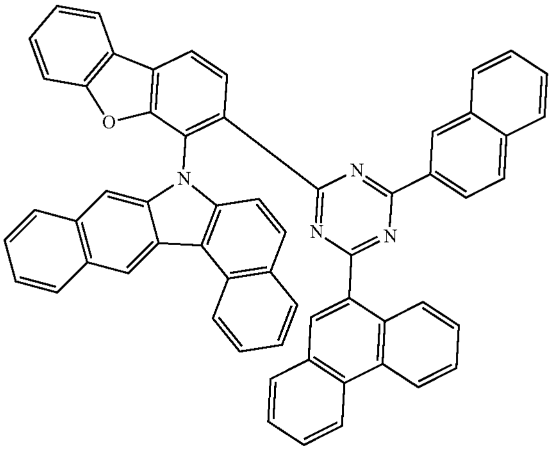
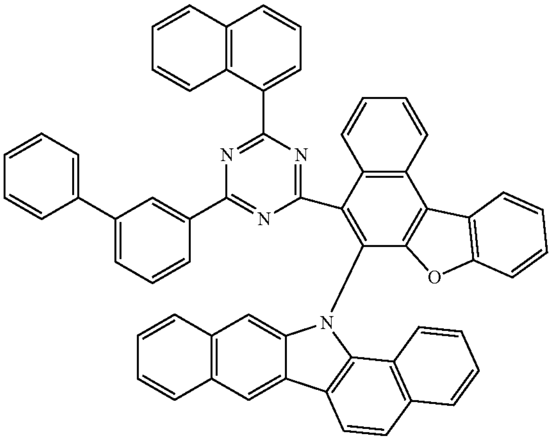
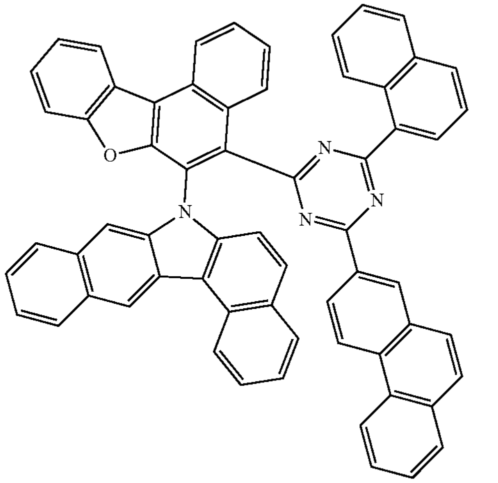
-continued
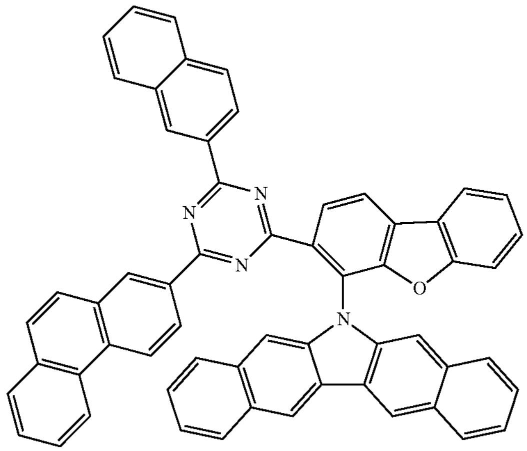
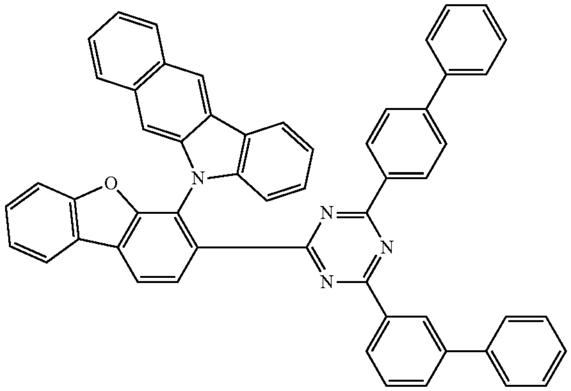
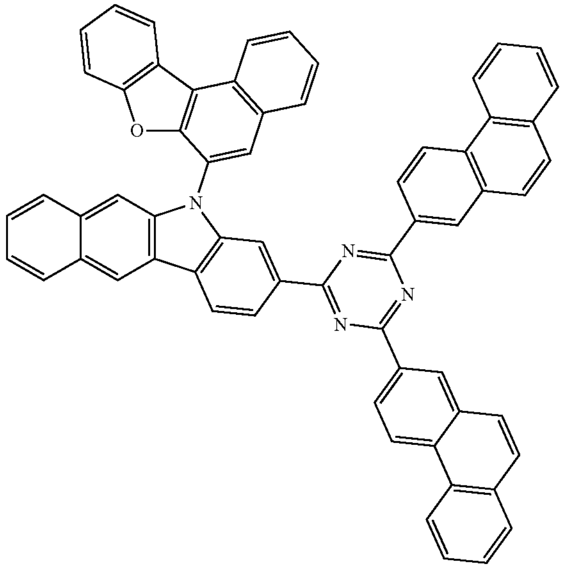

-continued
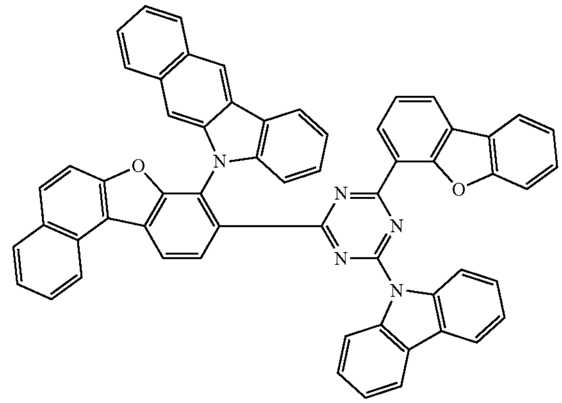
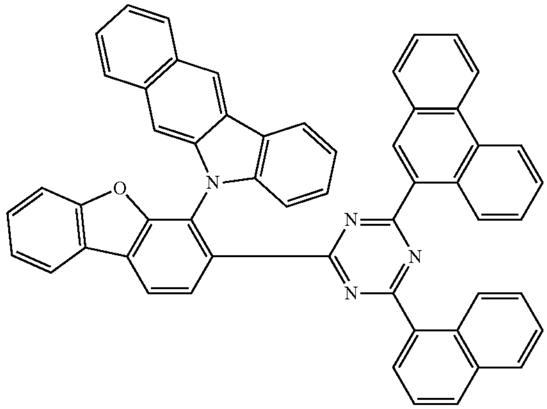
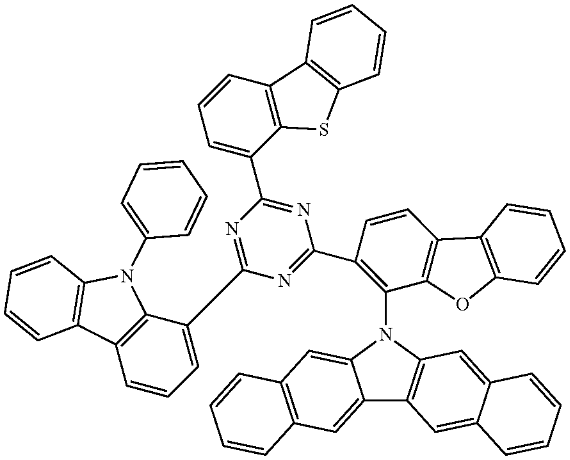
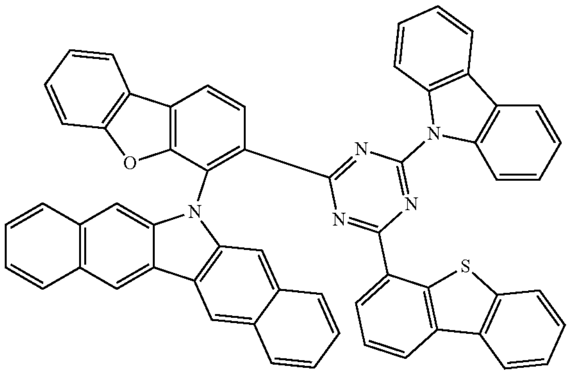
-continued
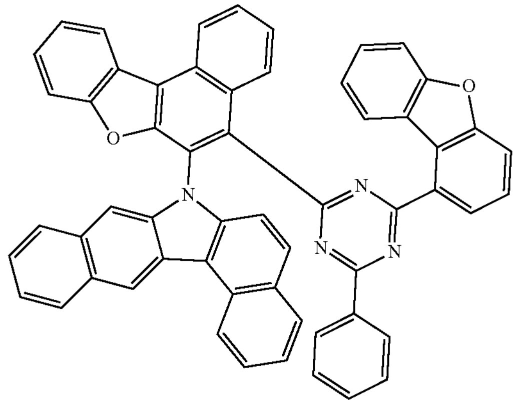
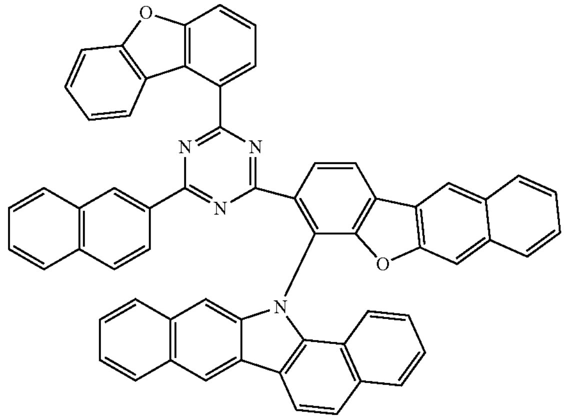
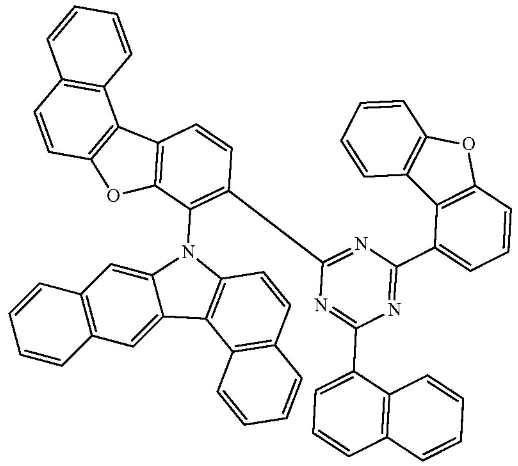
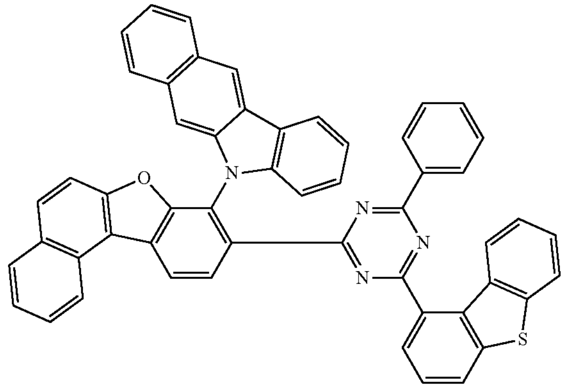

-continued
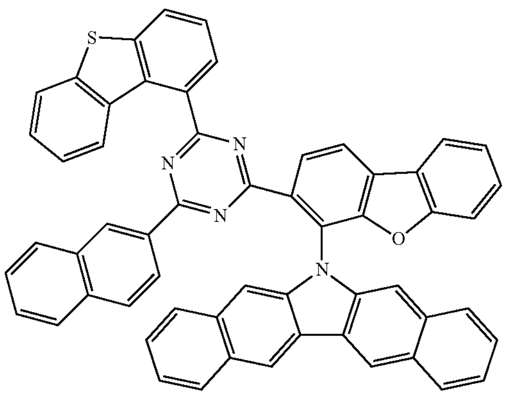
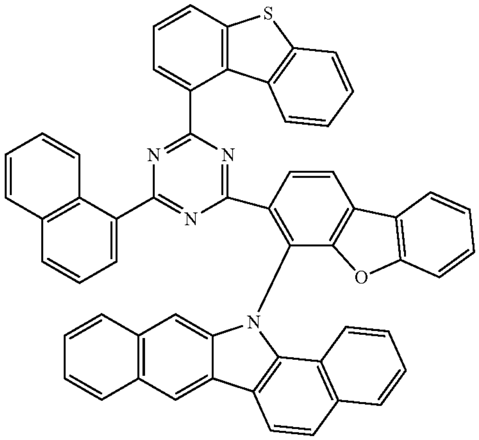
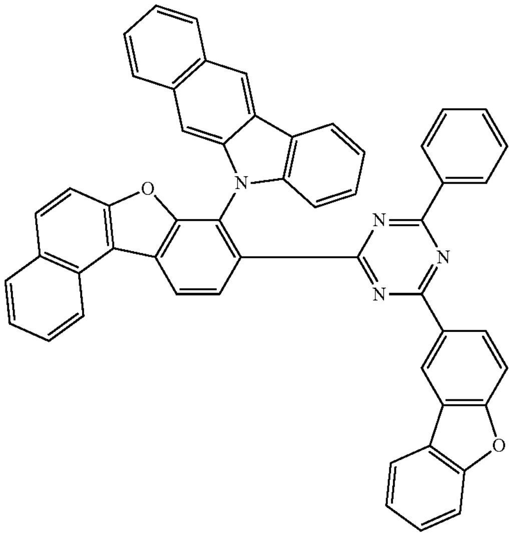
-continued
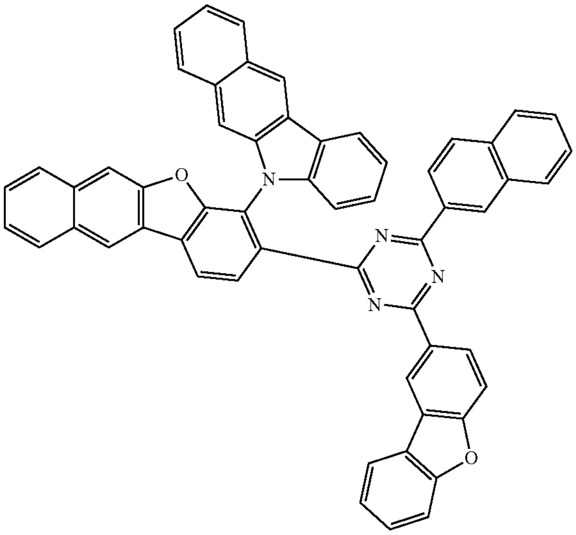
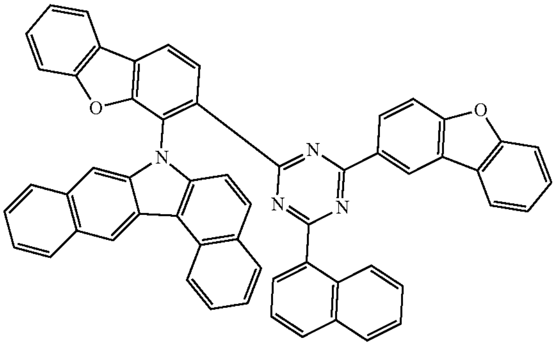
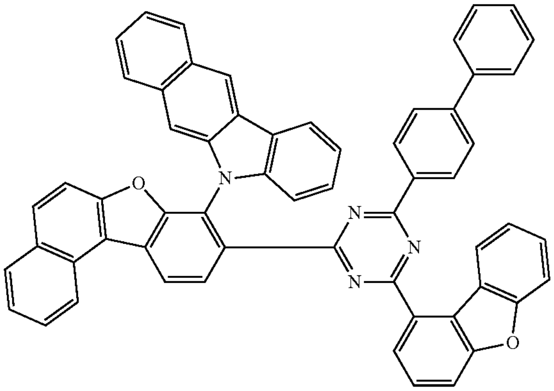
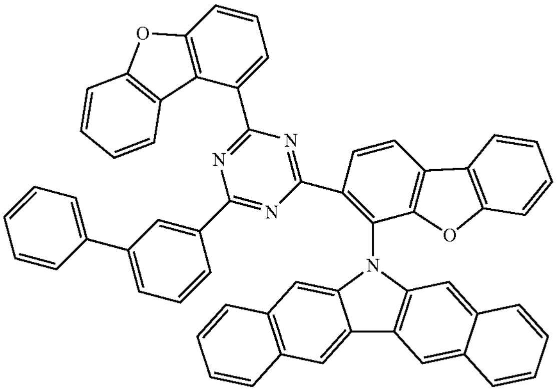

-continued
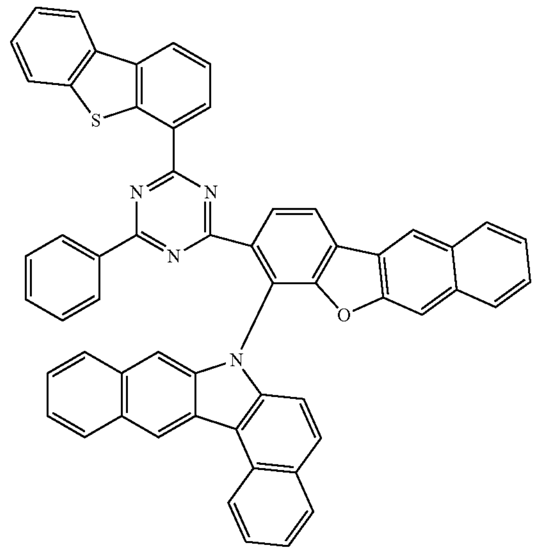
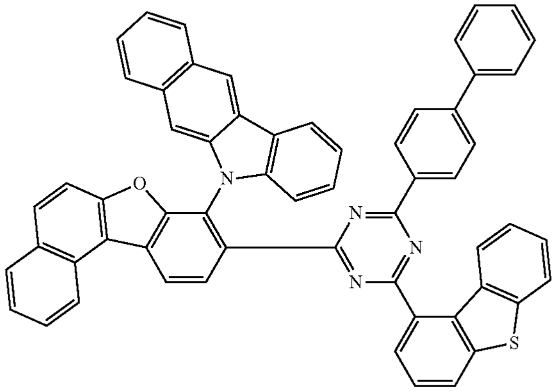
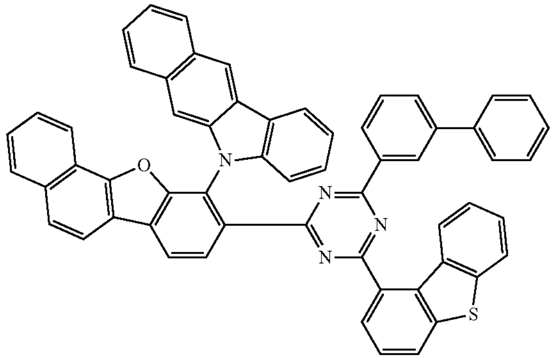
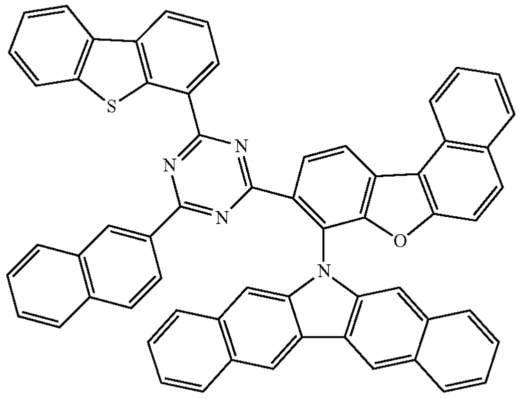
-continued
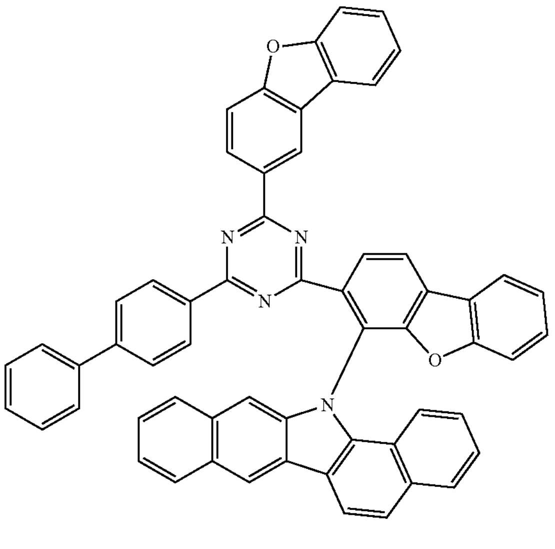
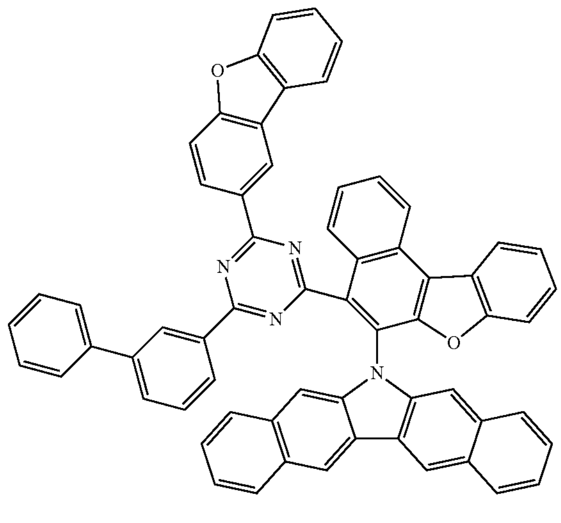
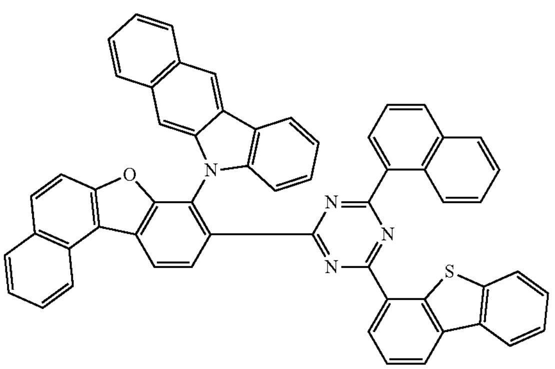

-continued
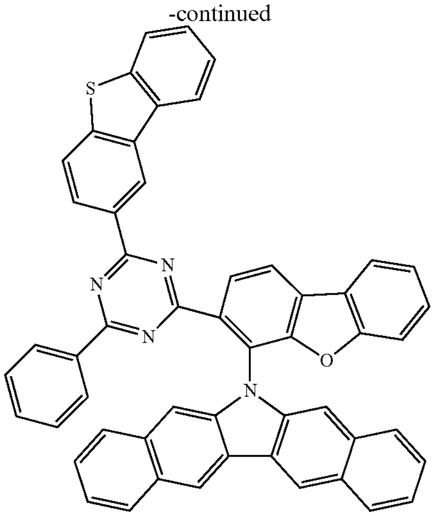
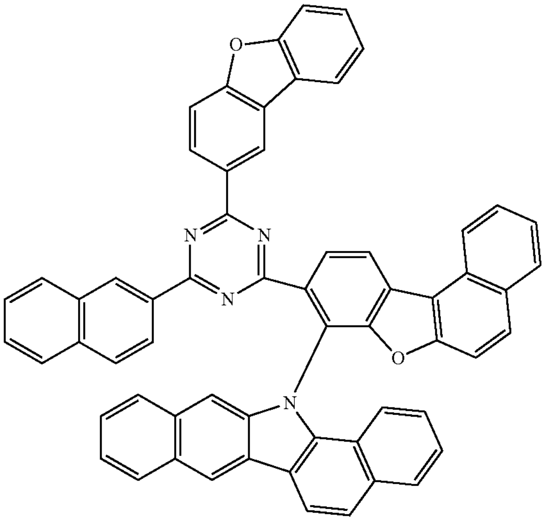
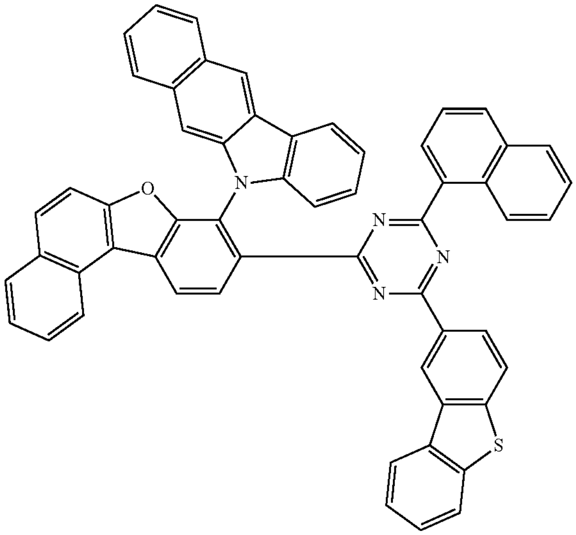
-continued
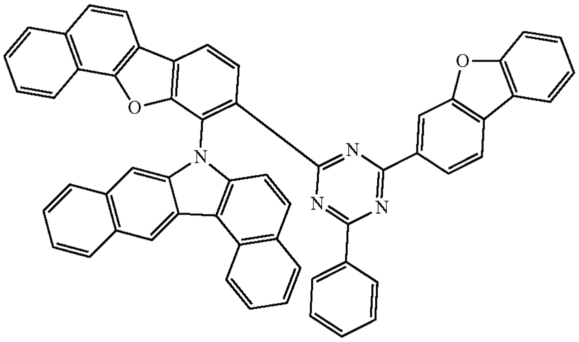
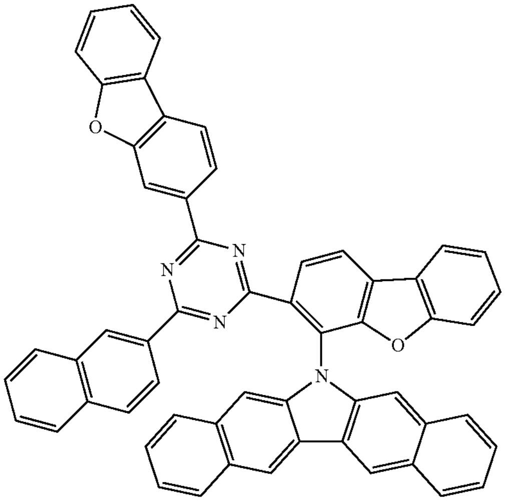
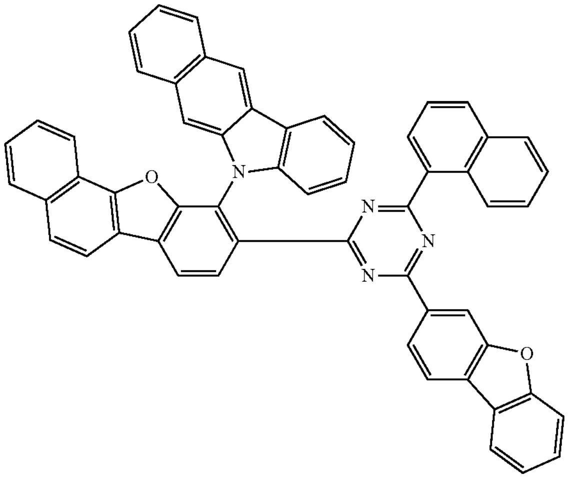

-continued
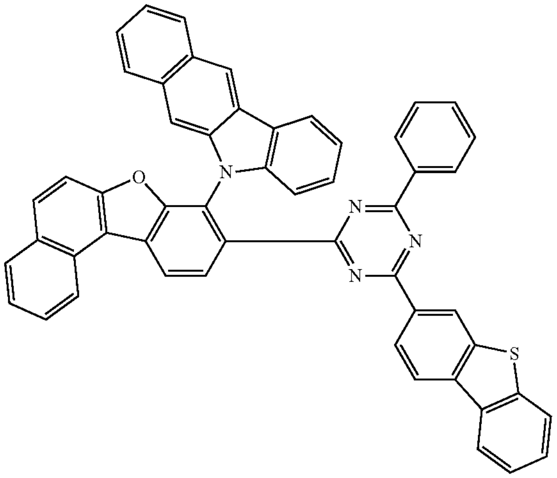
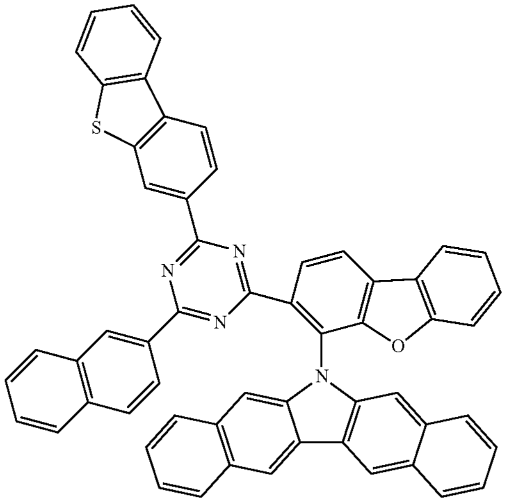
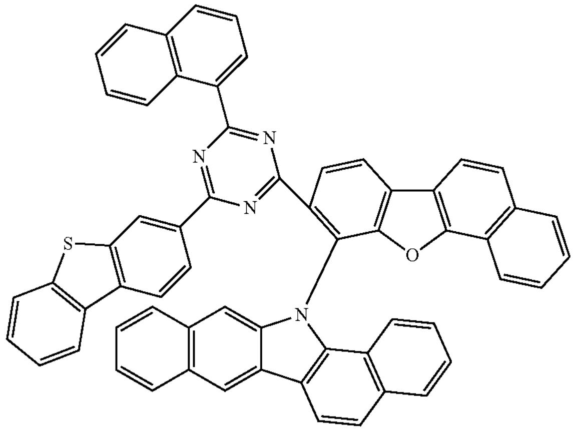
-continued
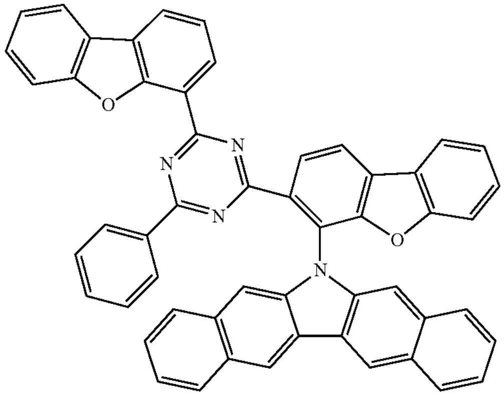
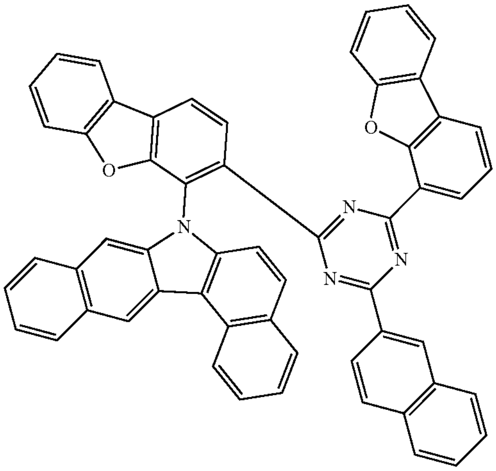
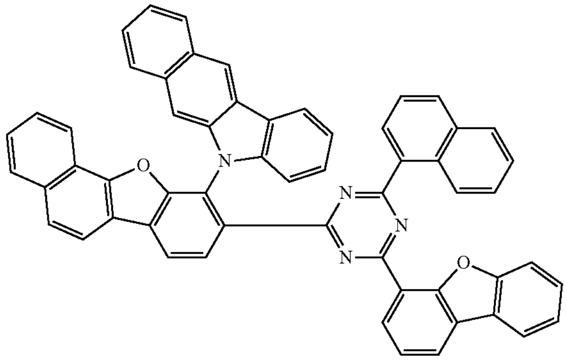
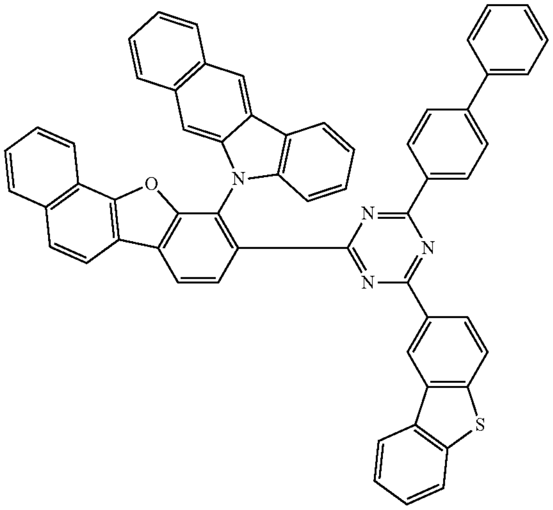

-continued
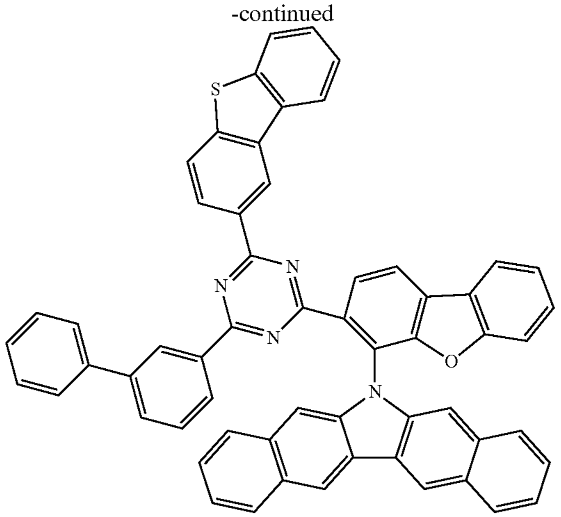
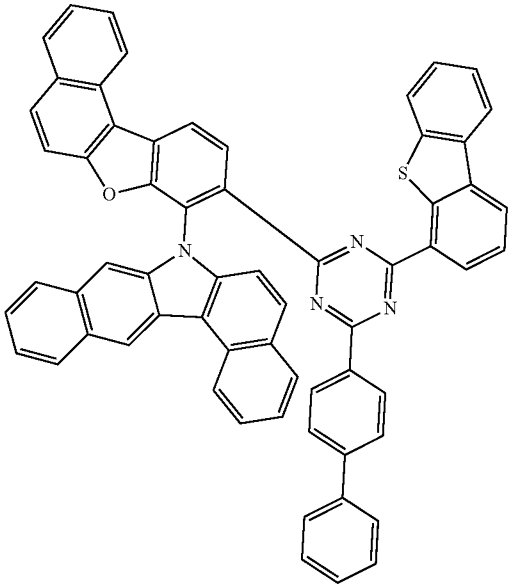
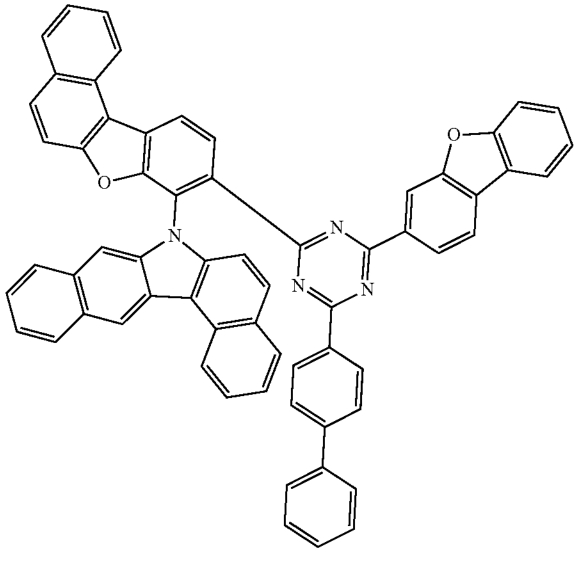
-continued
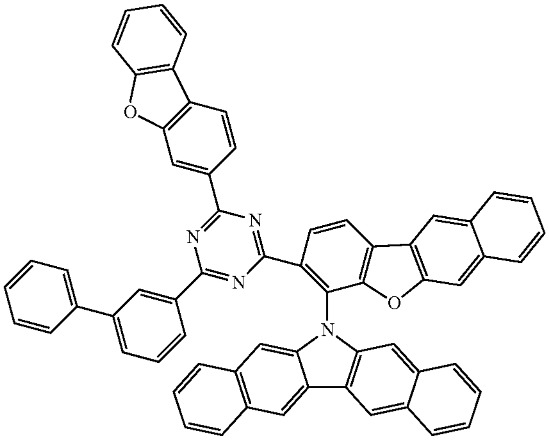
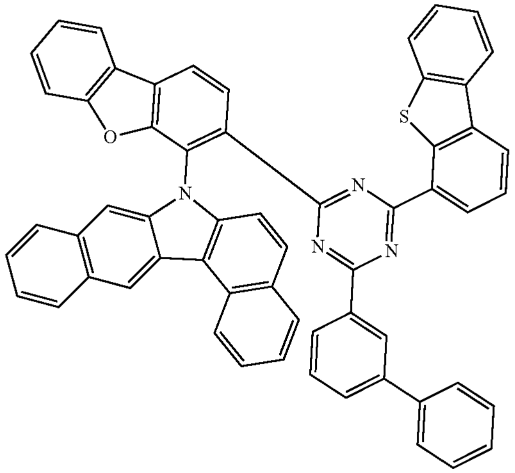
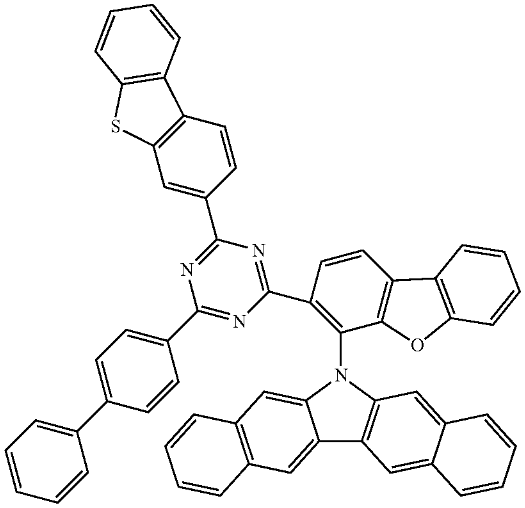

-continued
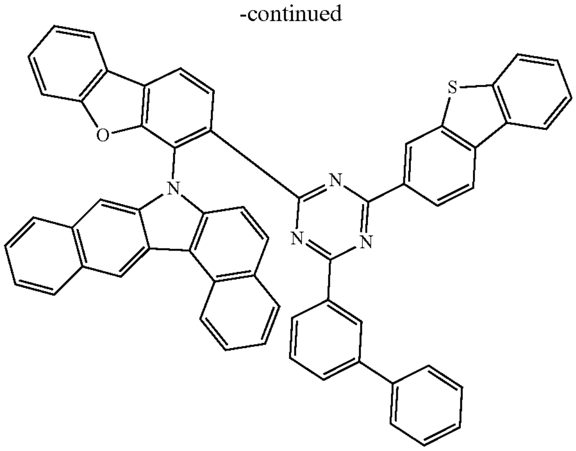
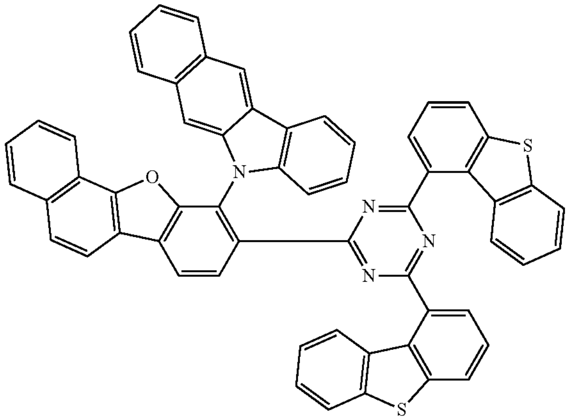
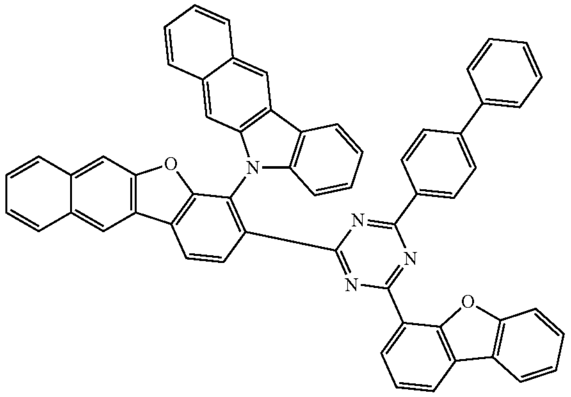
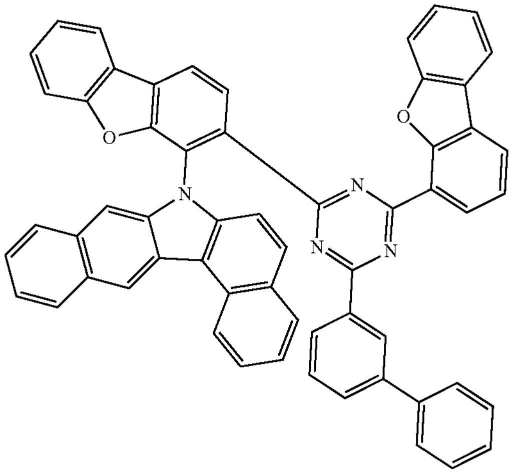
-continued
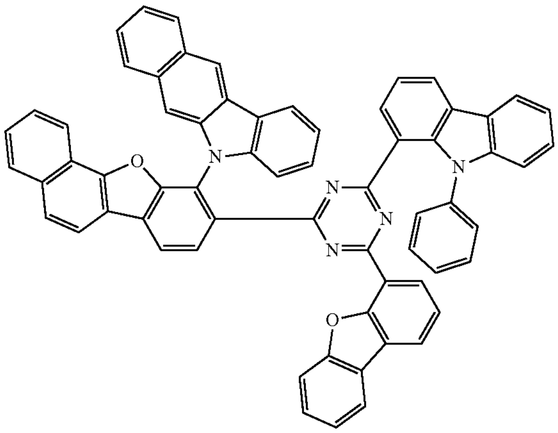
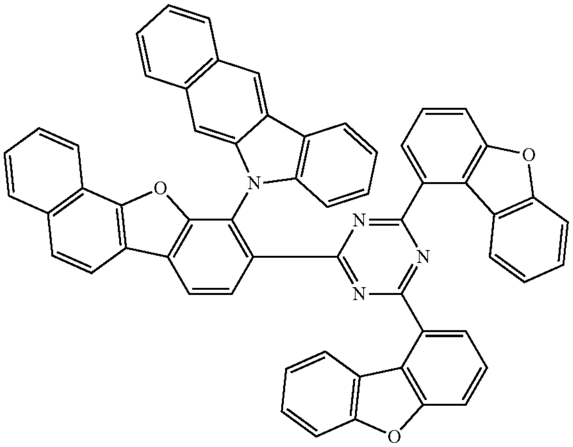
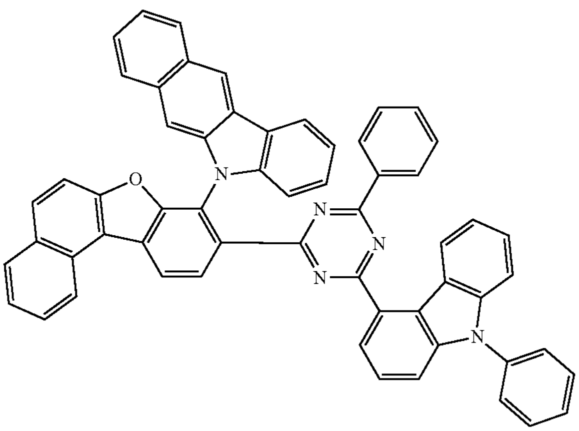

-continued
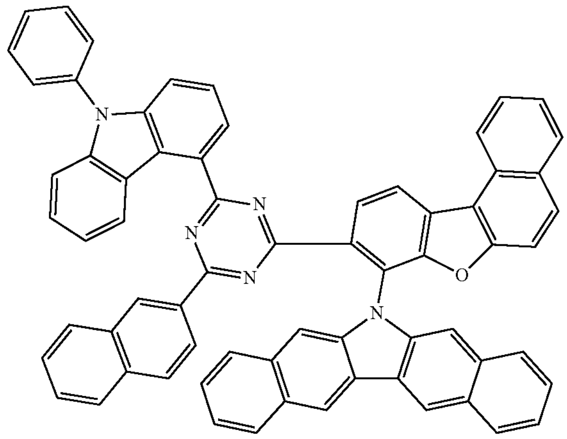
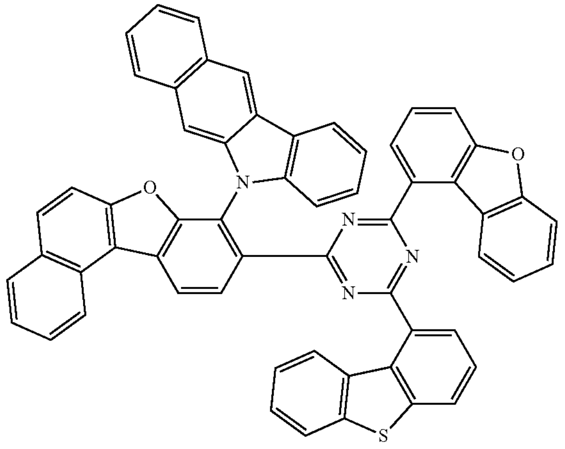
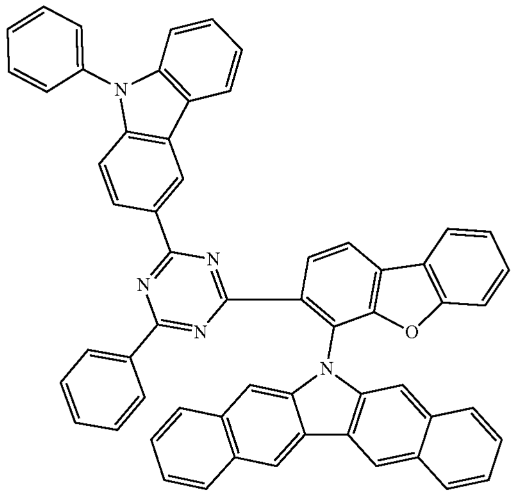
-continued
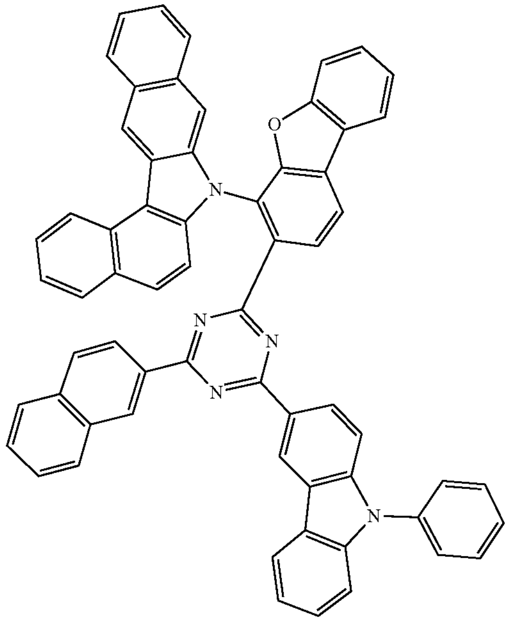
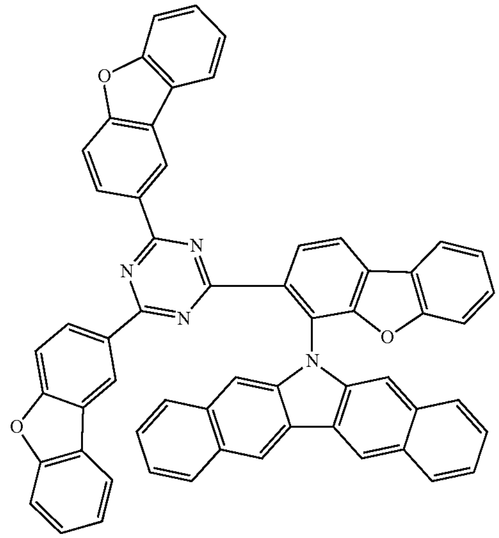
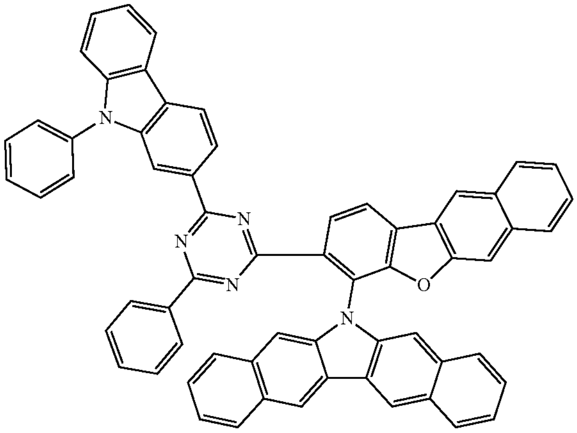

-continued
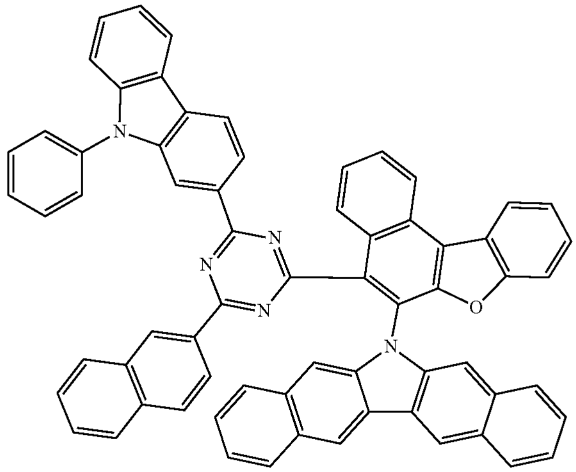
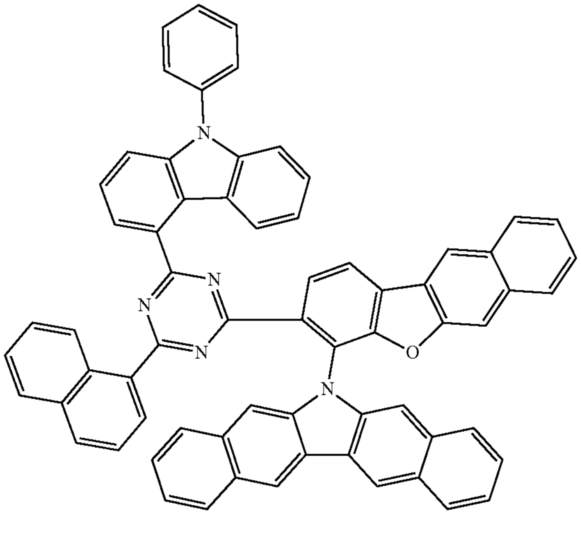
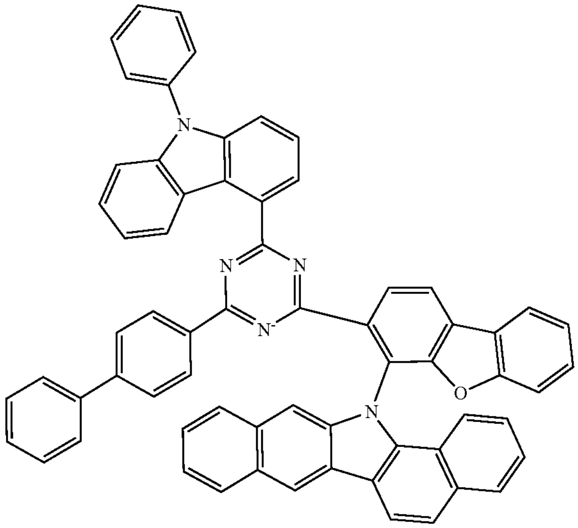
-continued
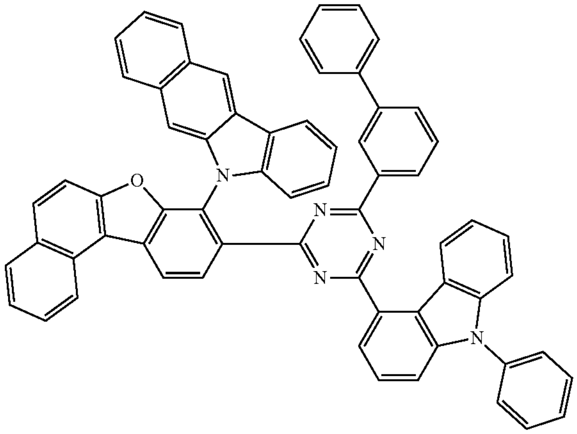
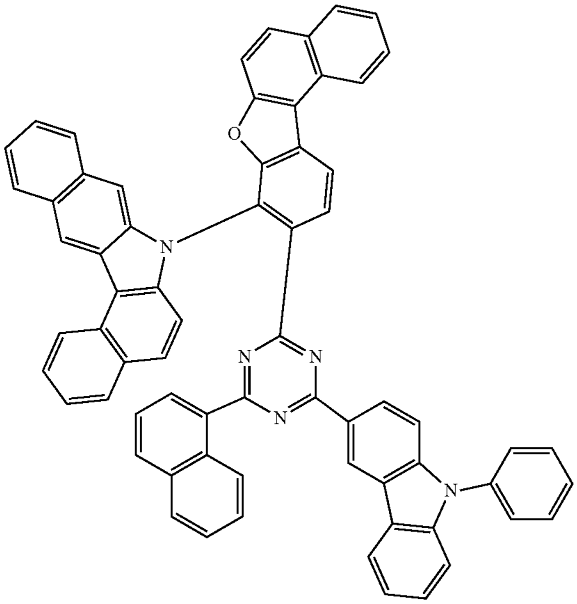
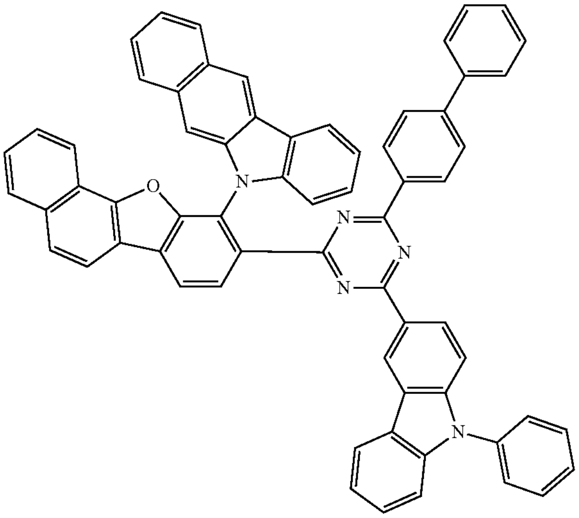

-continued
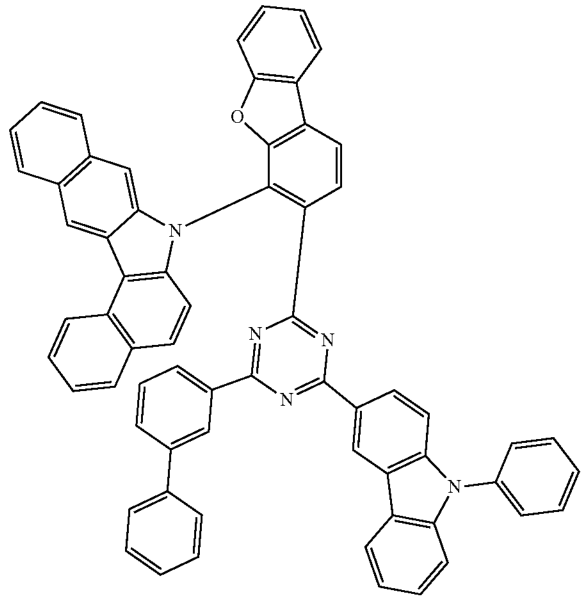
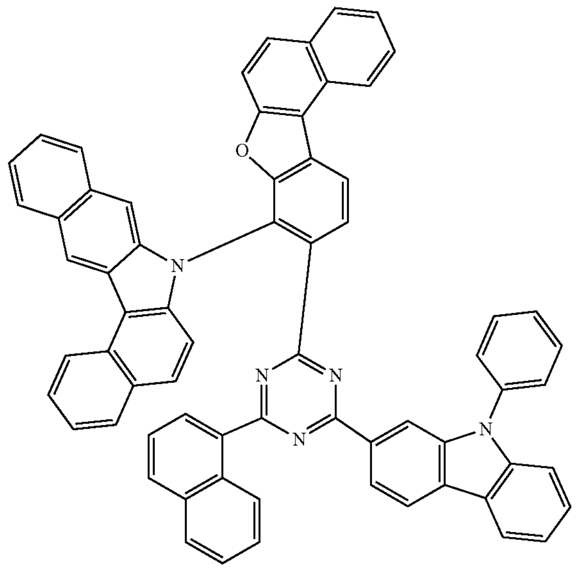
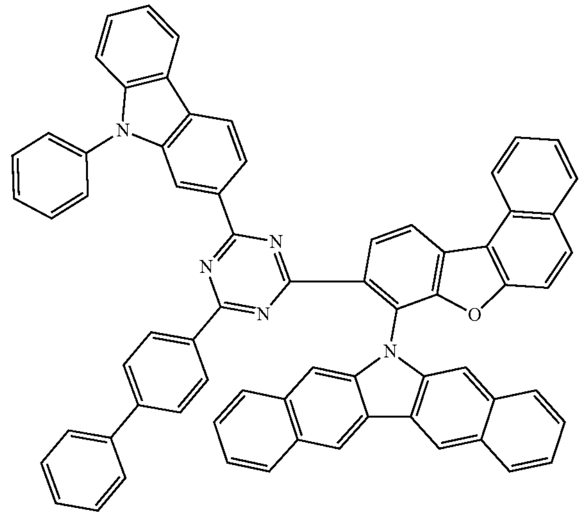
-continued
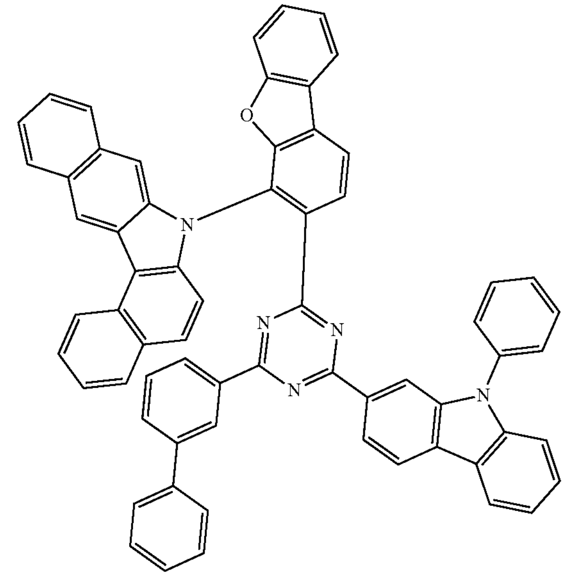
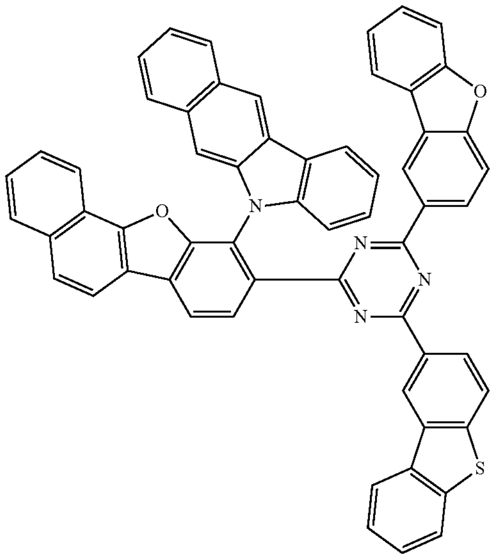
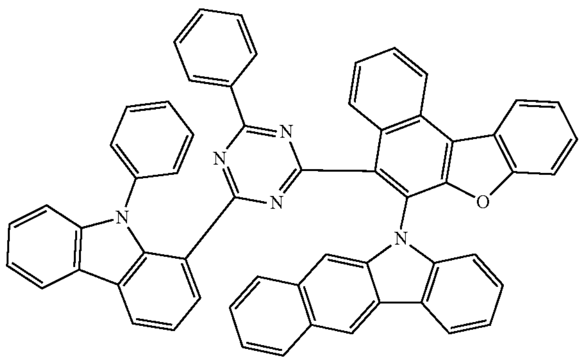

-continued
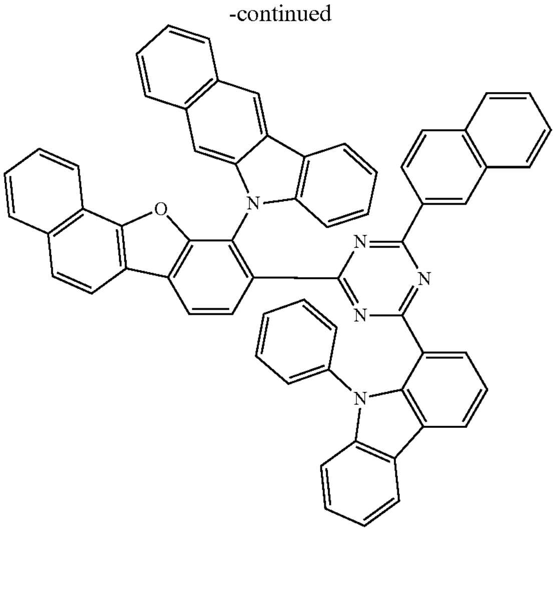
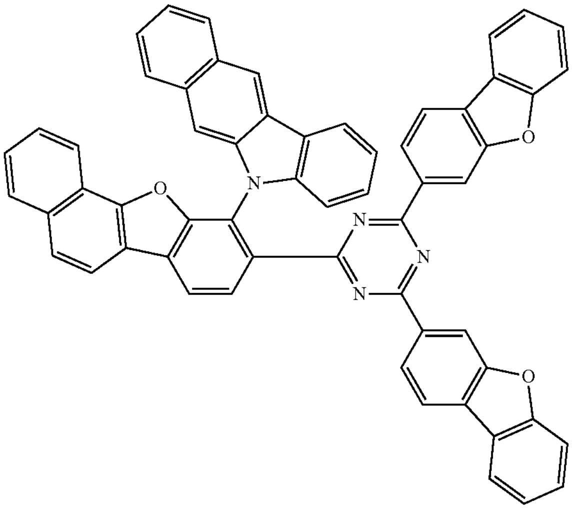
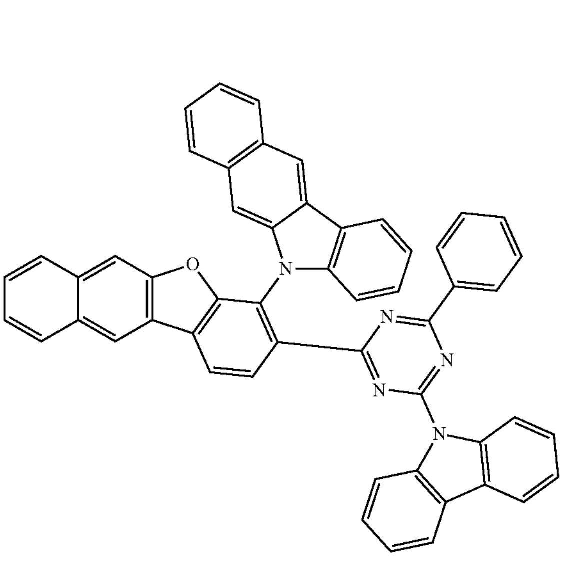
-continued
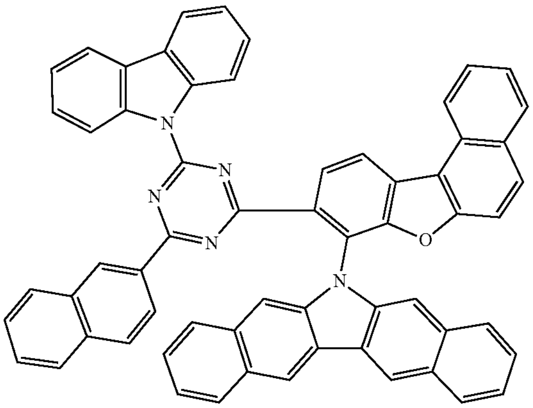
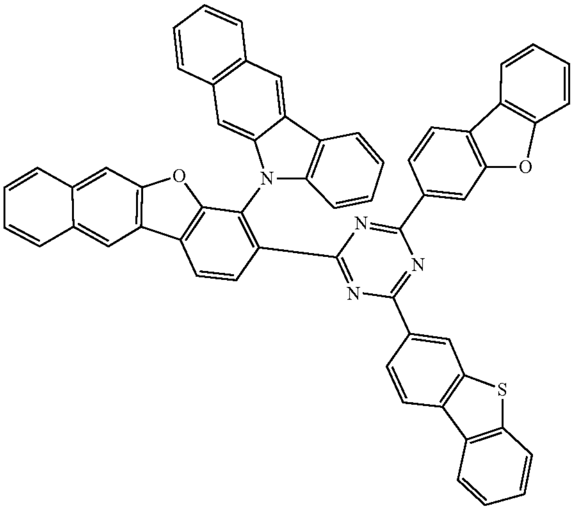
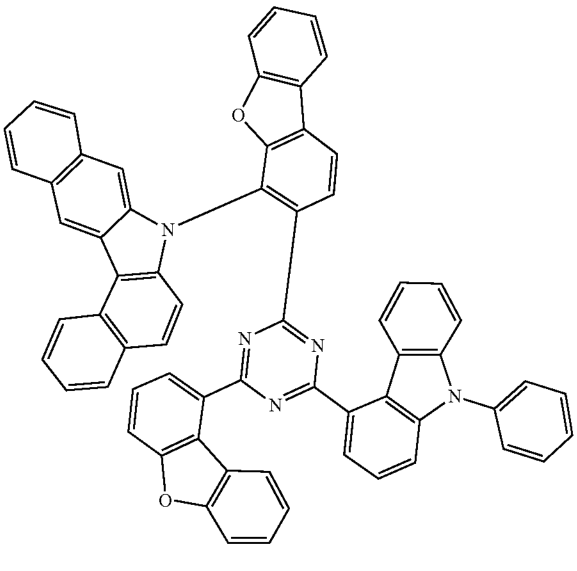

-continued
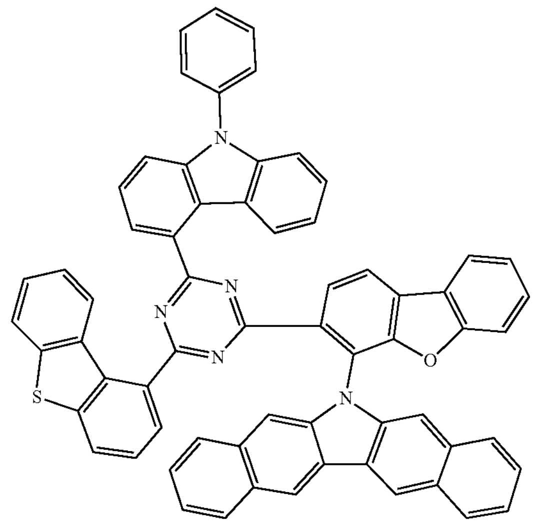
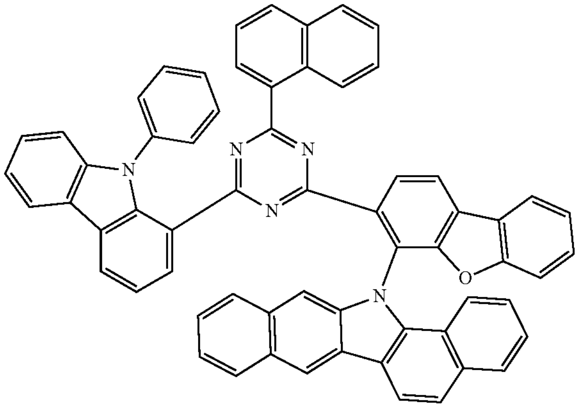
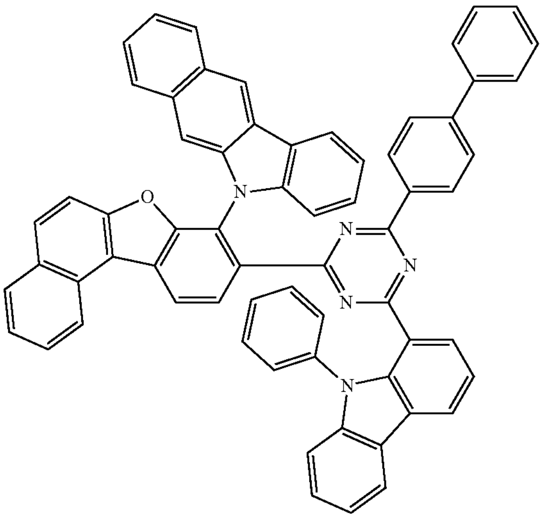
-continued
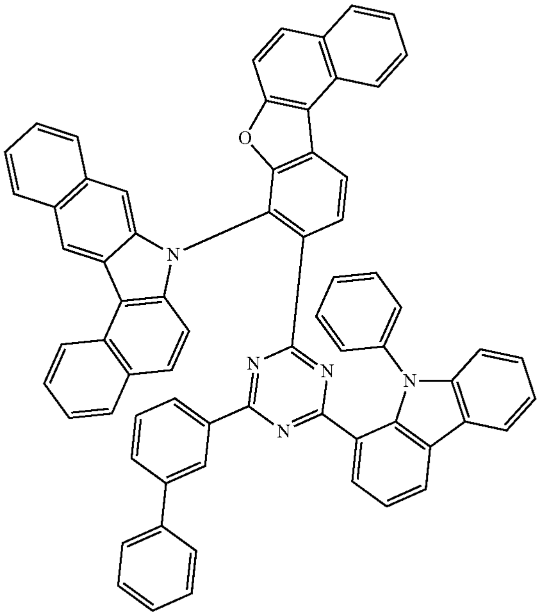
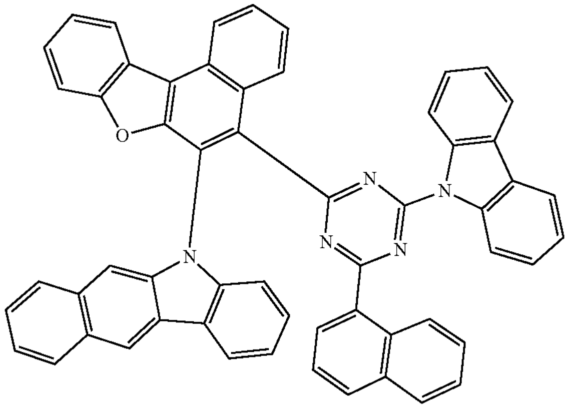
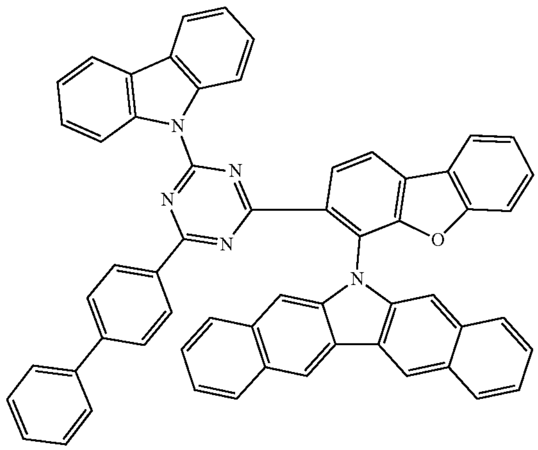

-continued
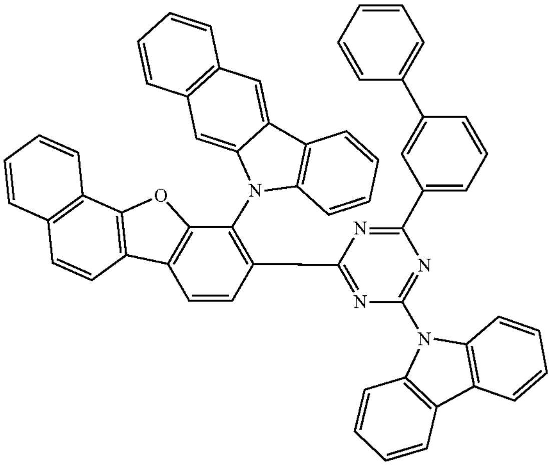
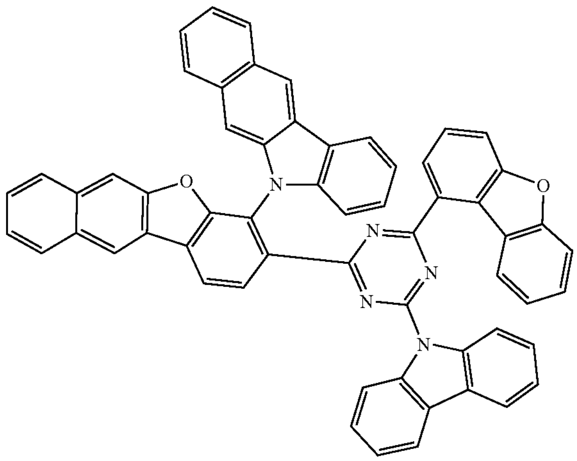
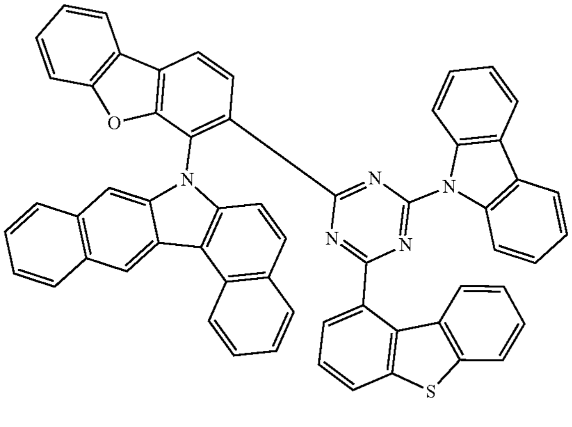
-continued
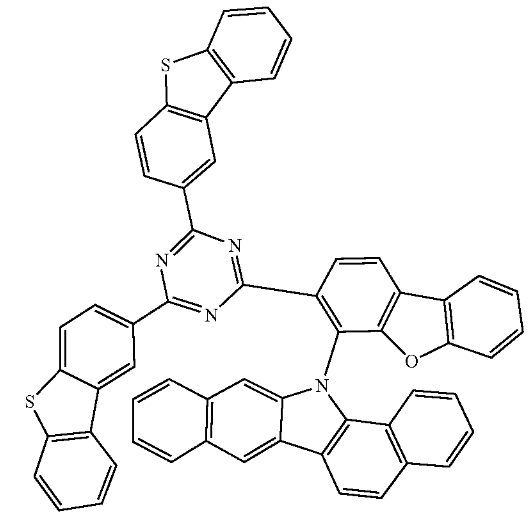
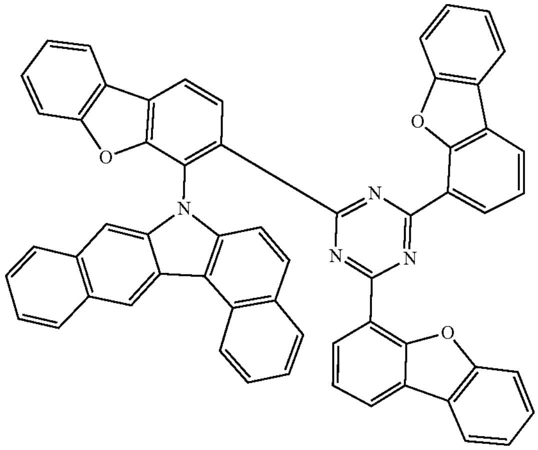
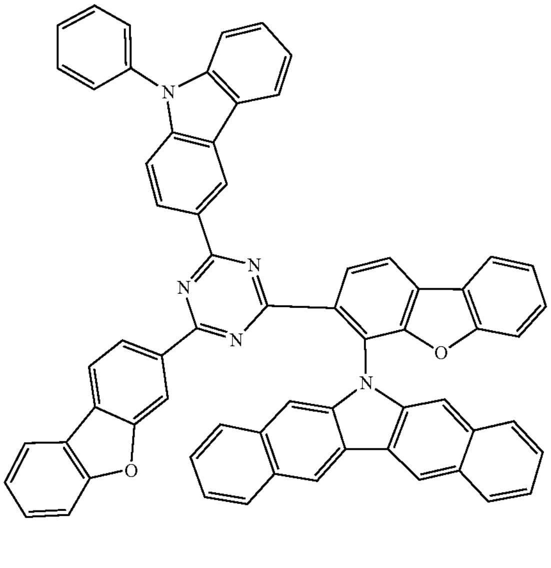

-continued
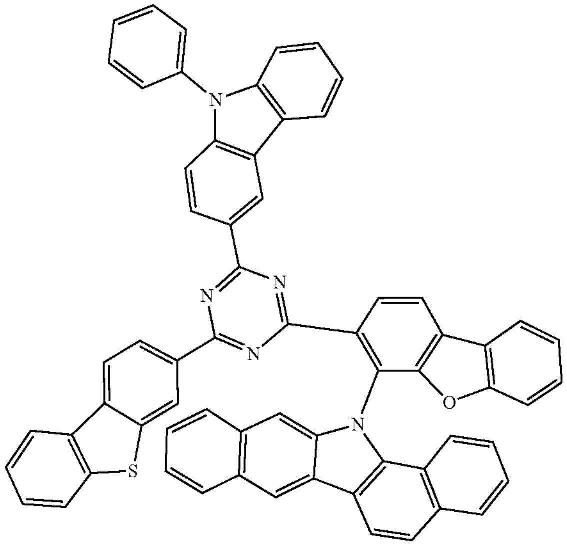
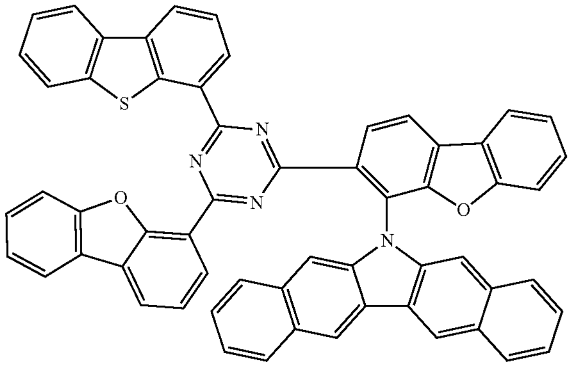
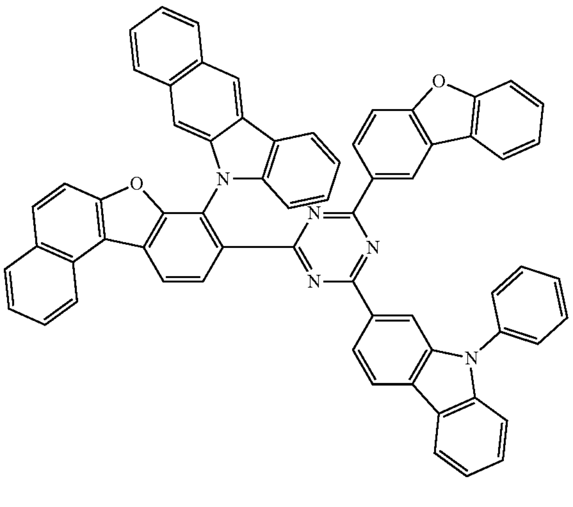
-continued
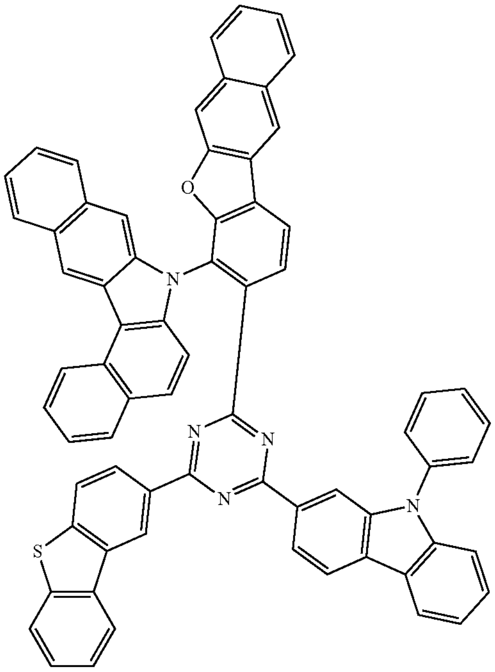
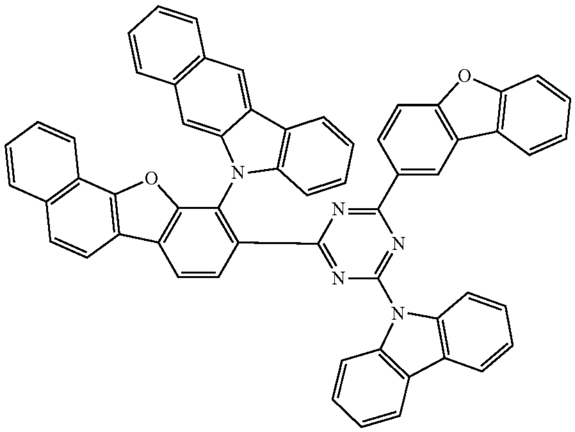
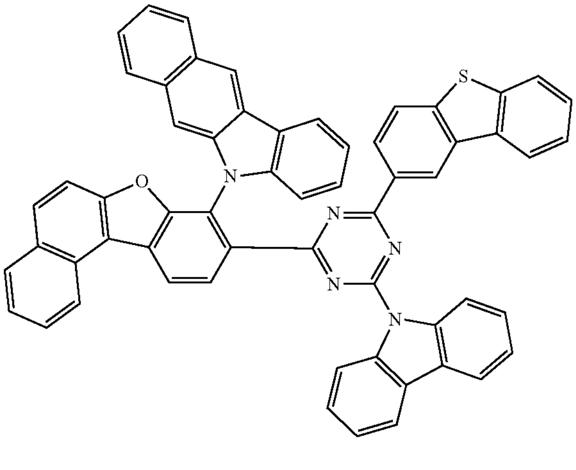

-continued
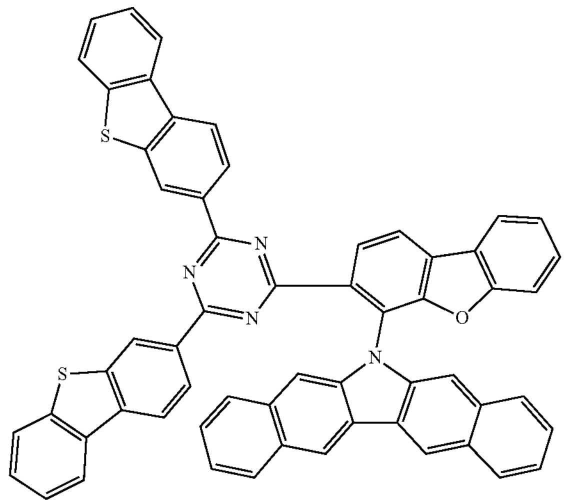
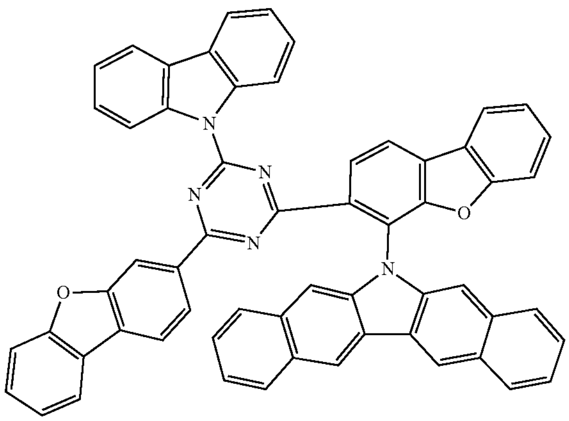
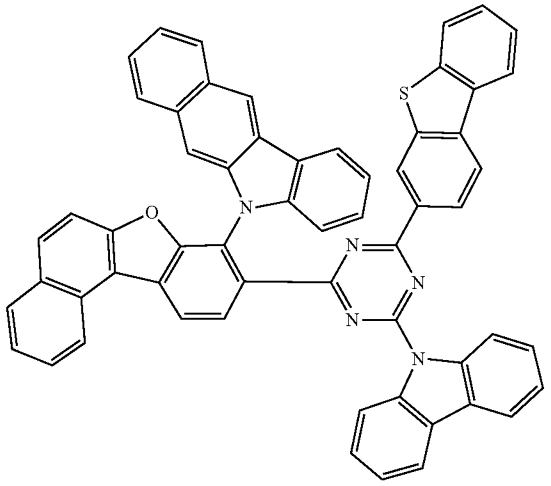
-continued
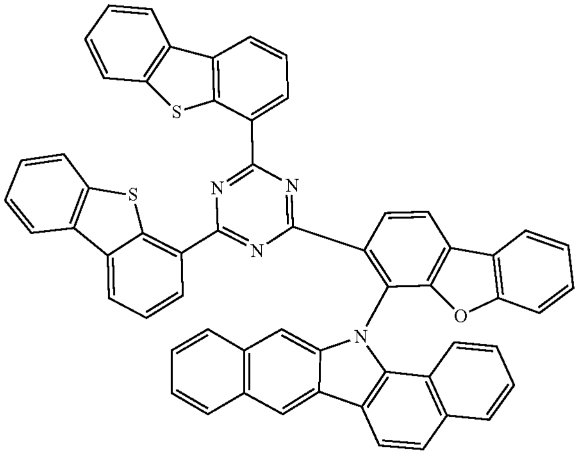
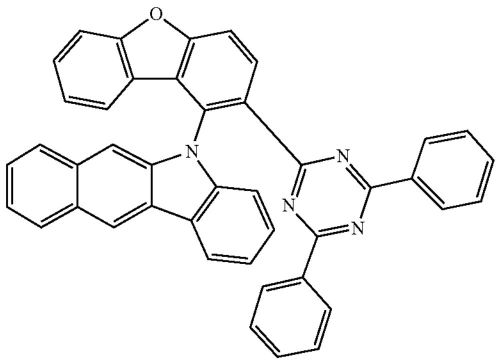
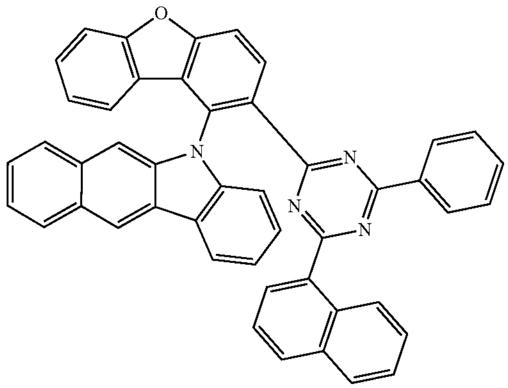
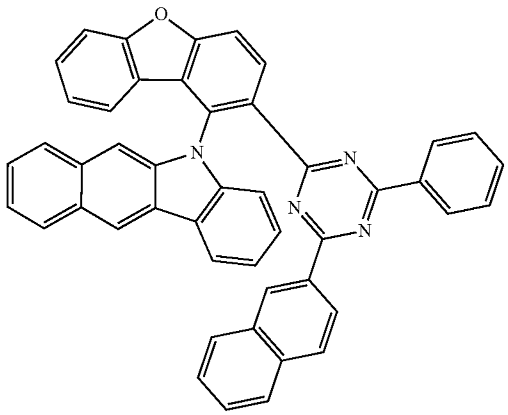

-continued
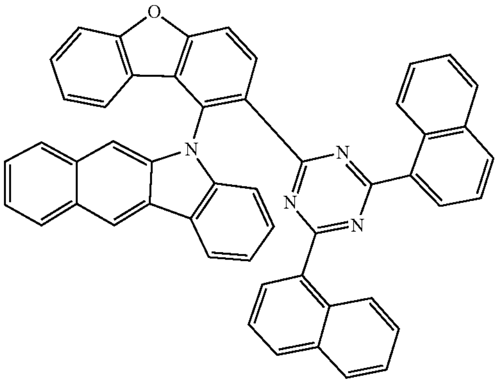
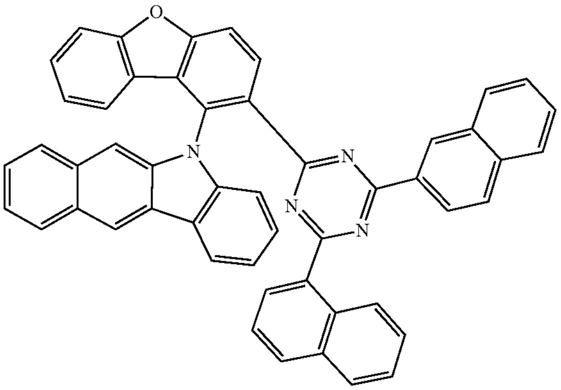
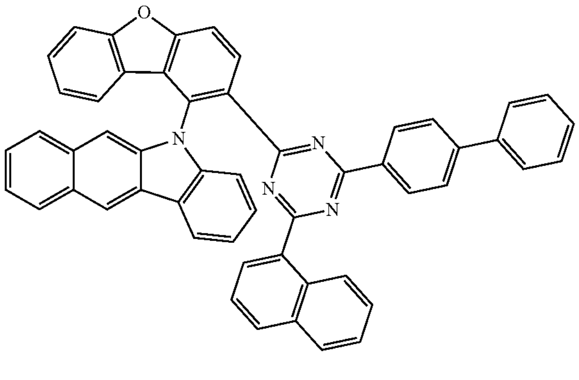
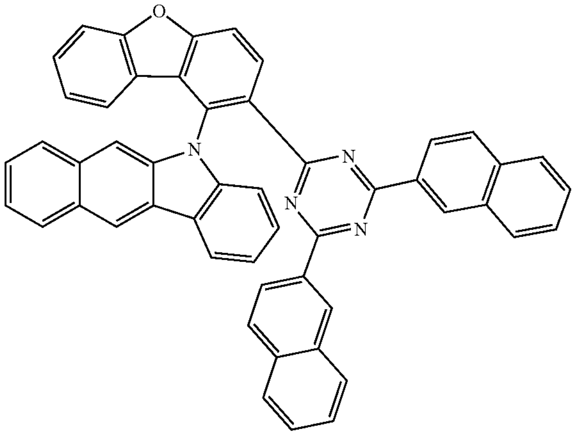
-continued
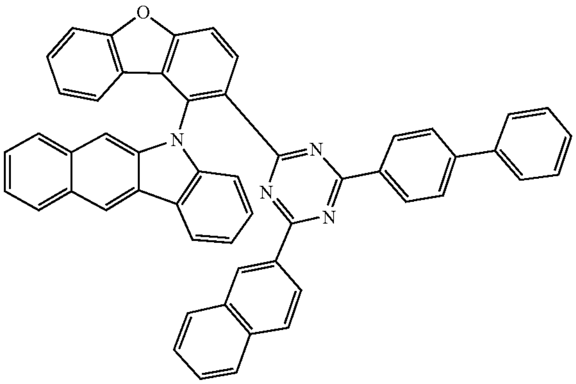
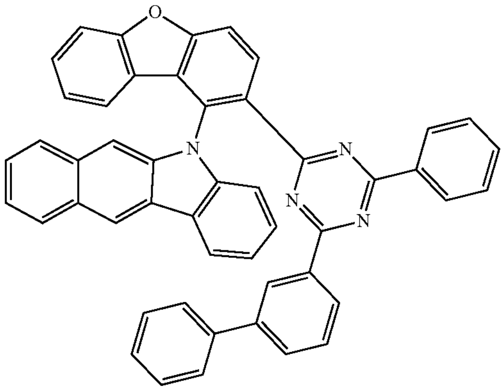
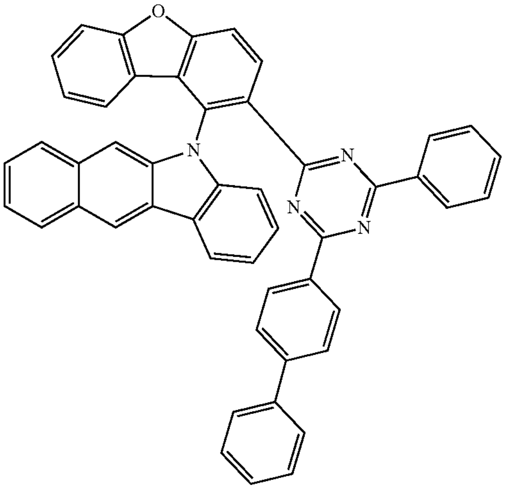
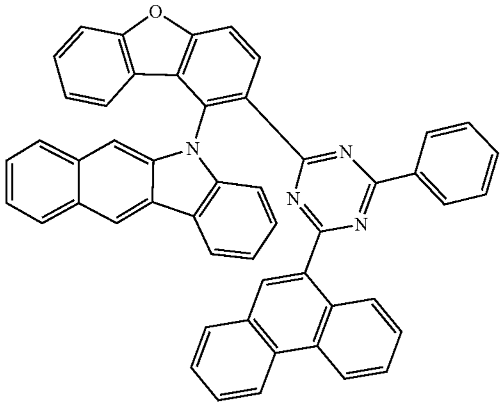

-continued
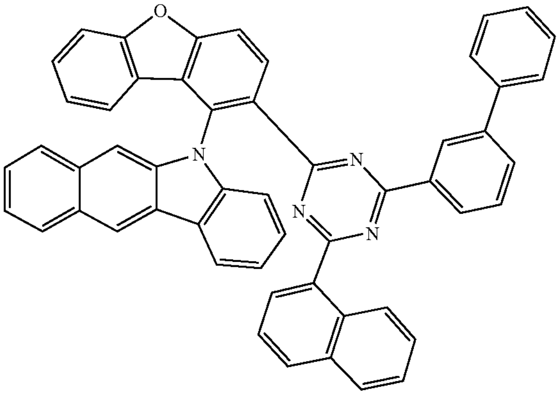
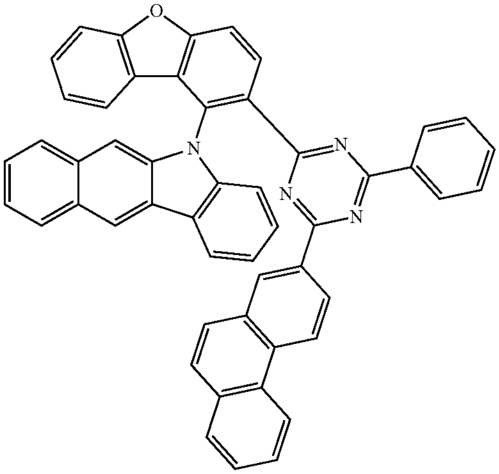
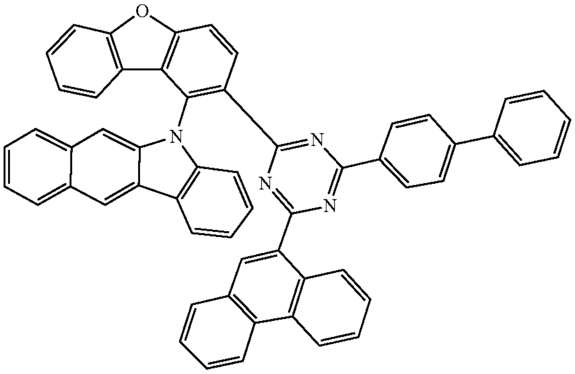
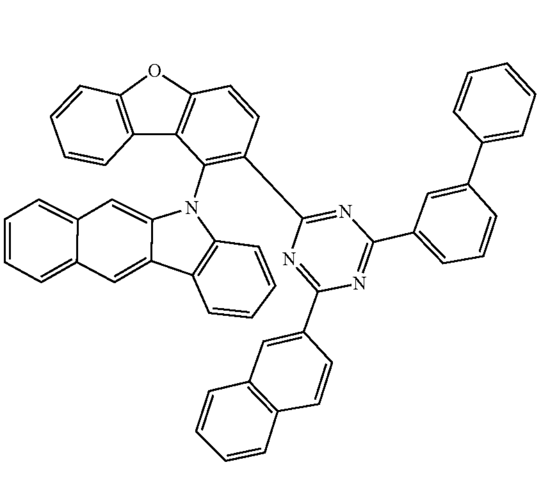
-continued
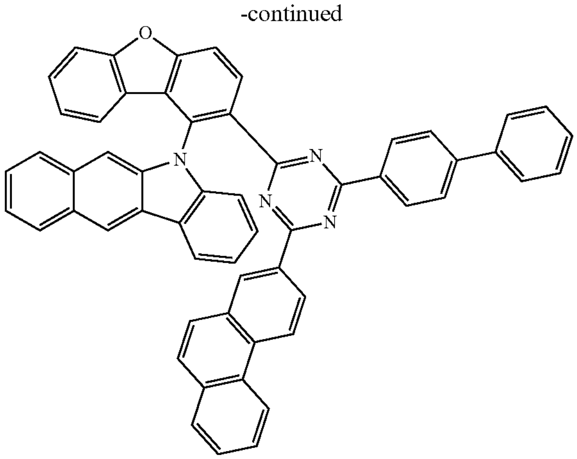
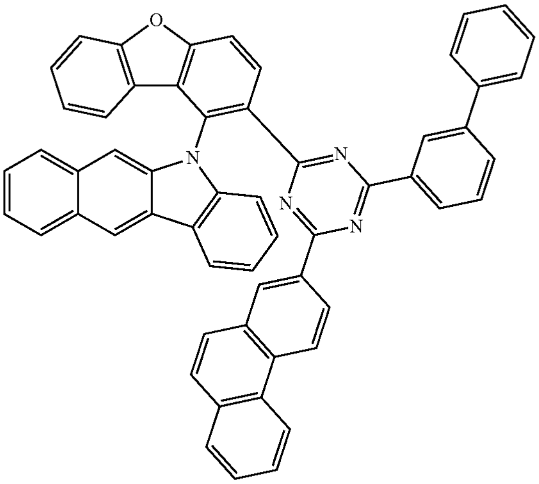
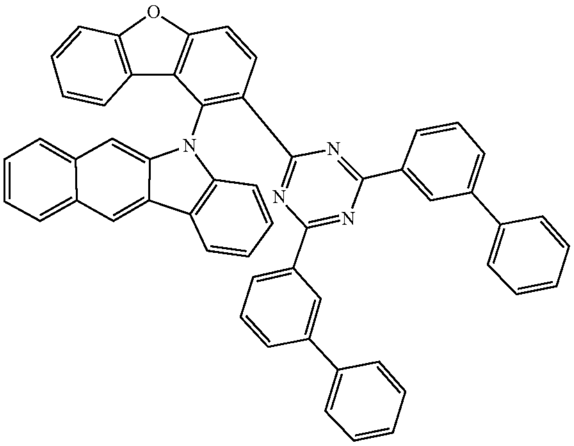
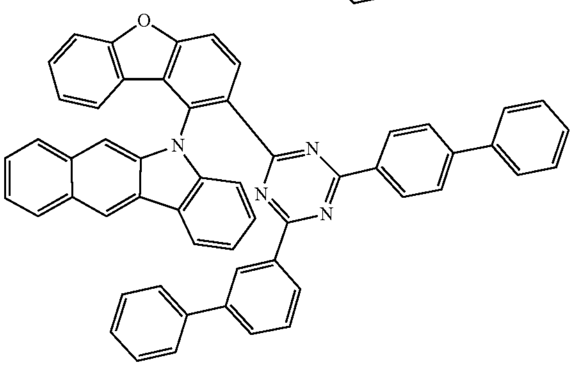

-continued
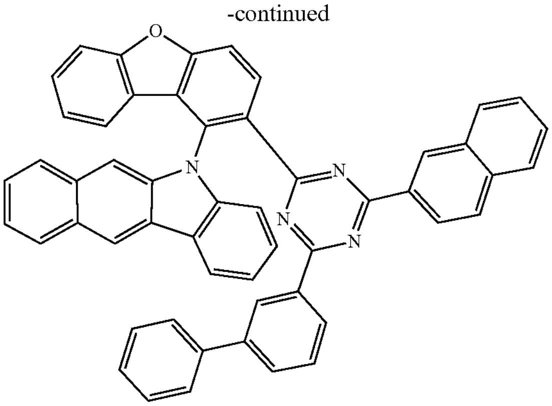
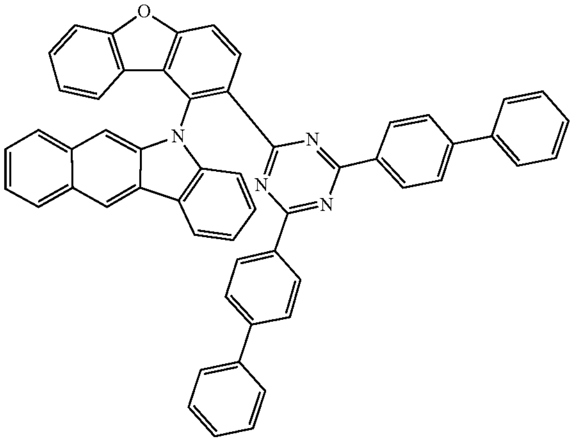
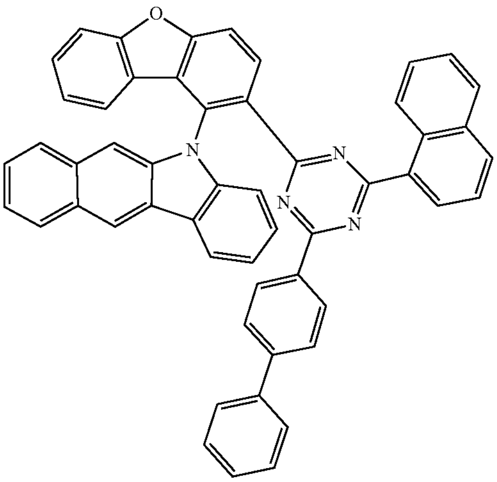
-continued
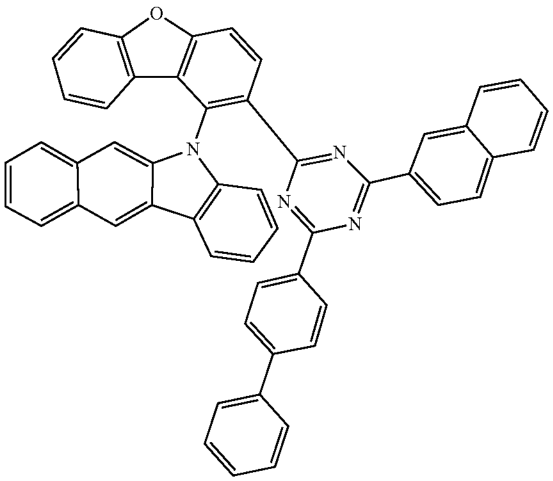
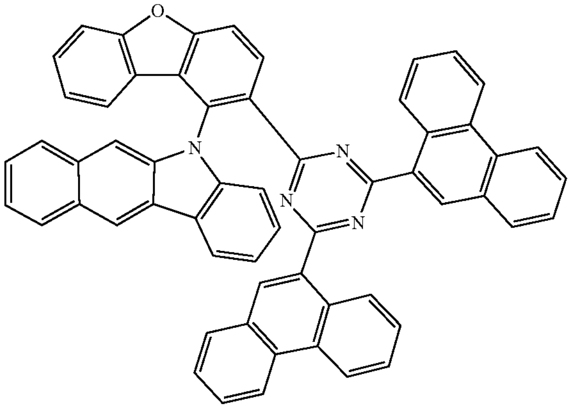
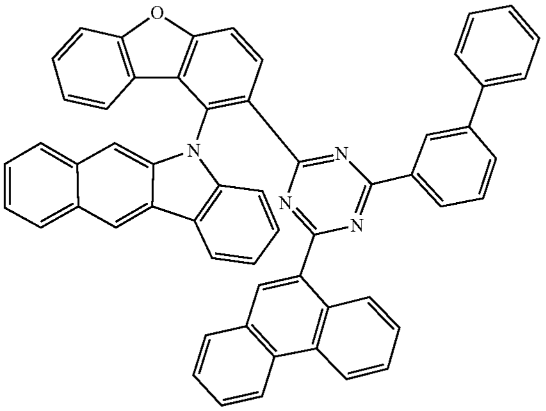
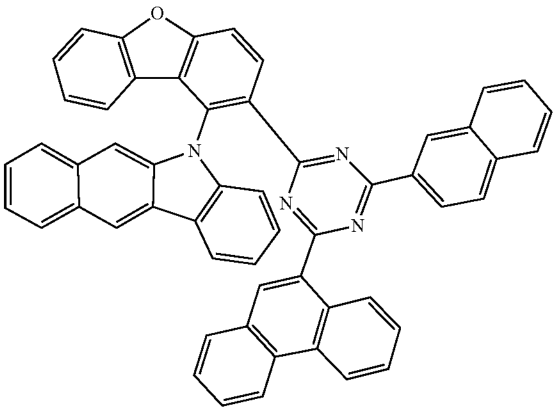

-continued
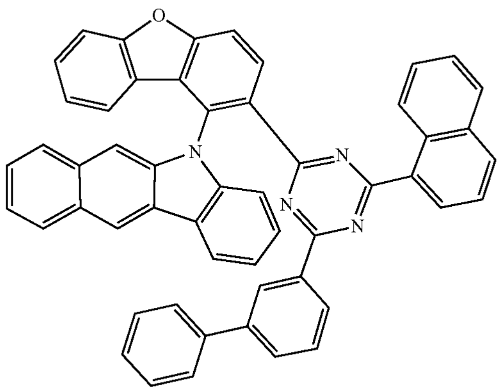
-continued
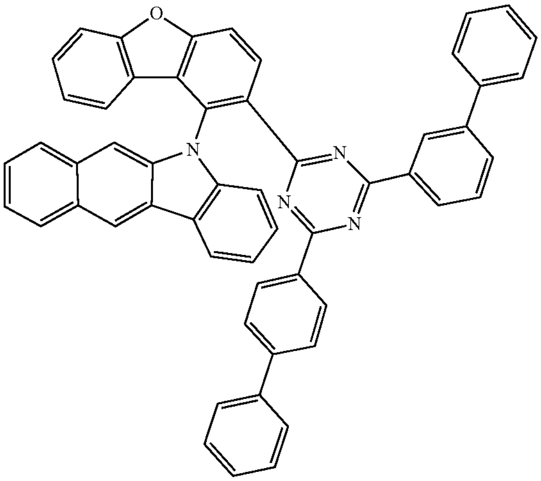
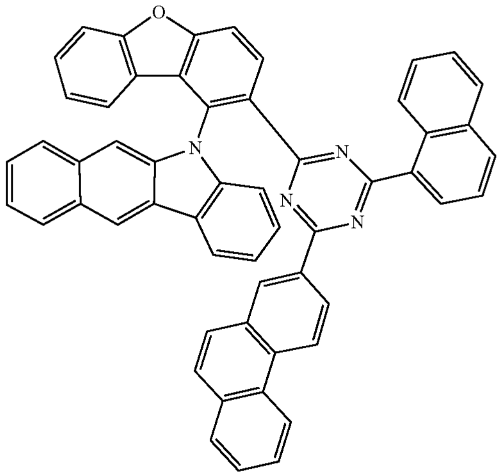
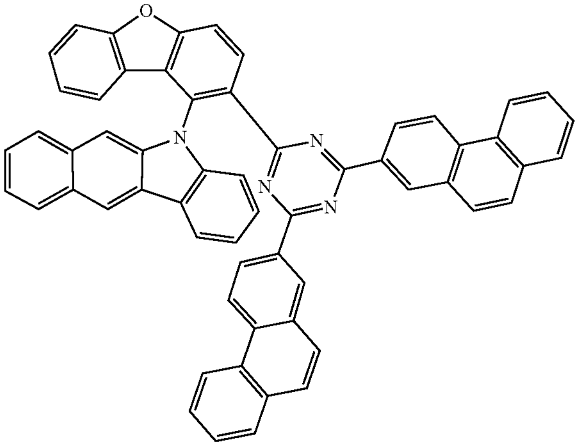
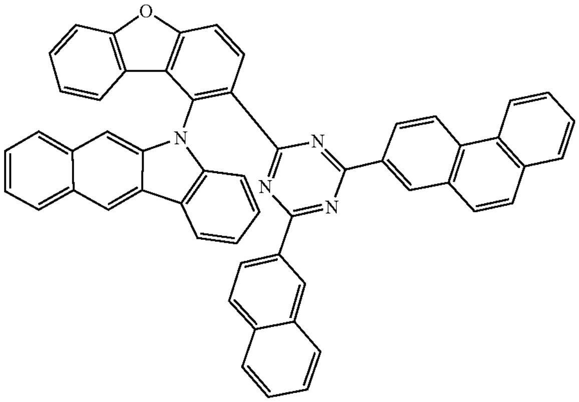
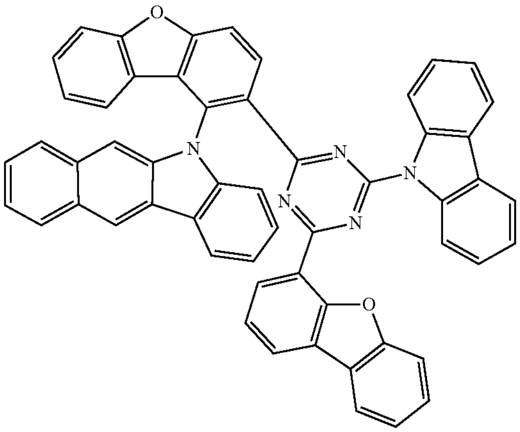

-continued
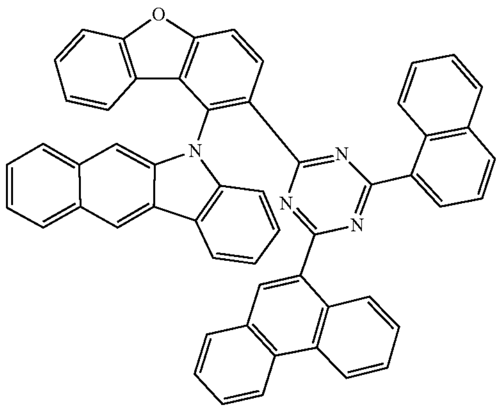
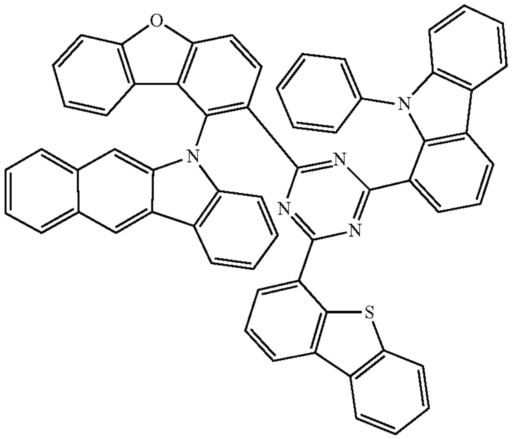
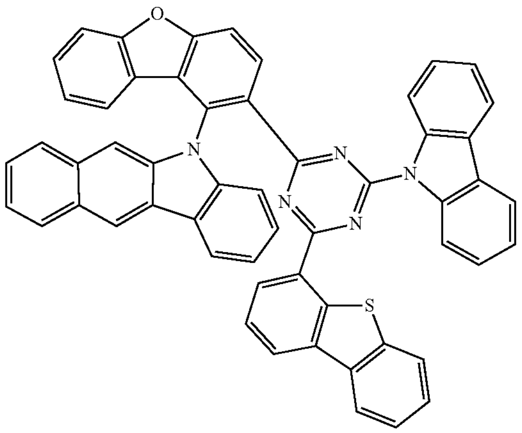
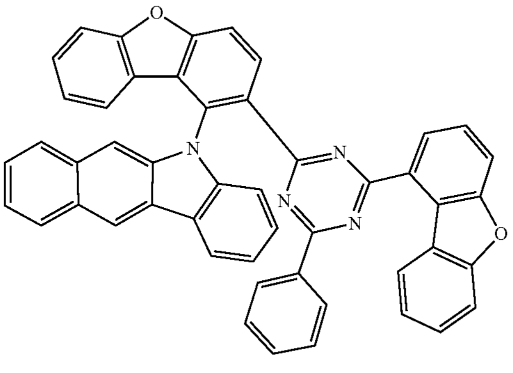
-continued
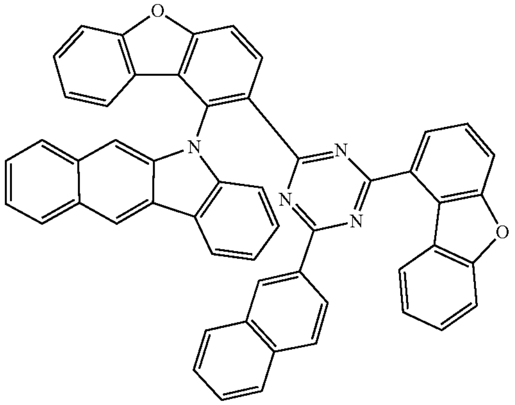
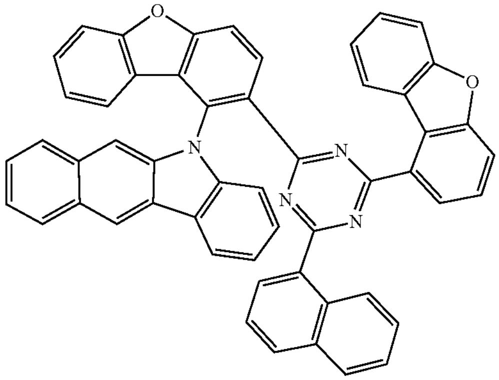
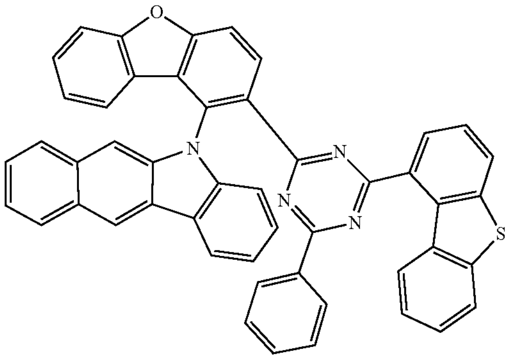
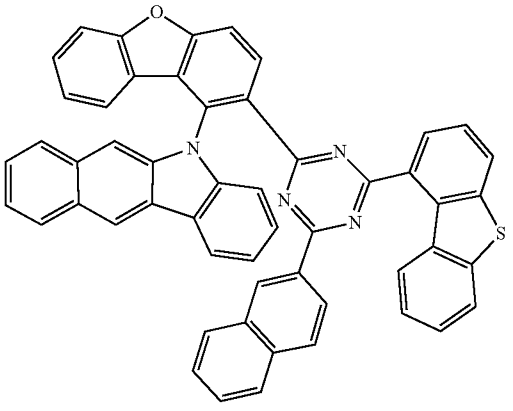

-continued
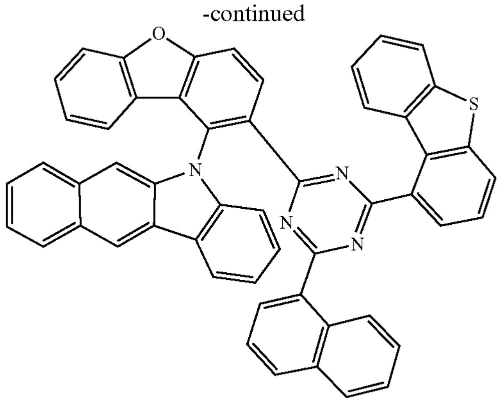
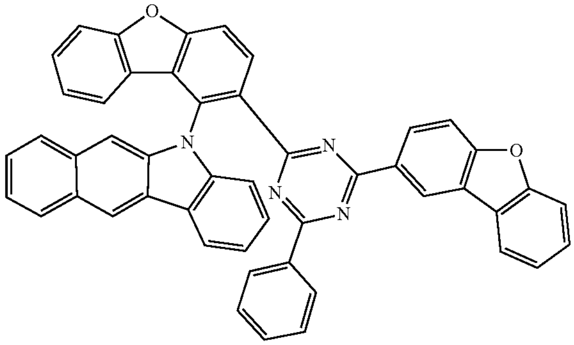
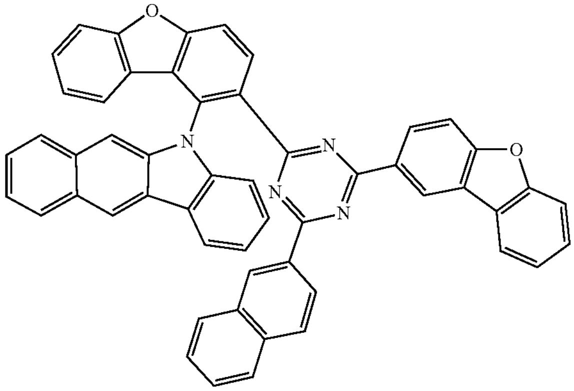
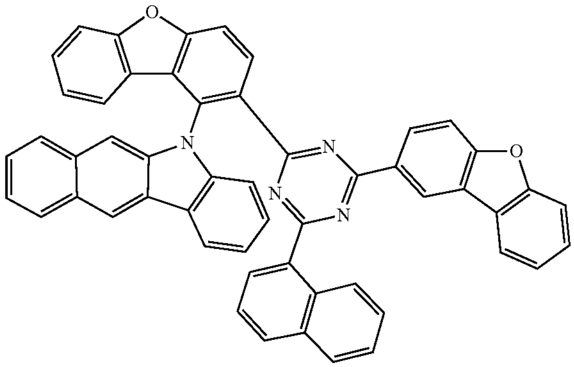
-continued
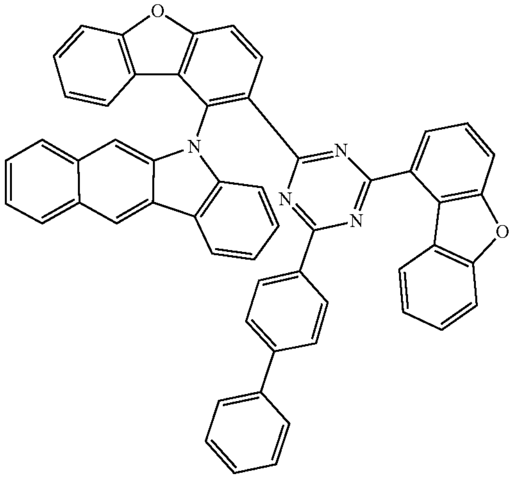
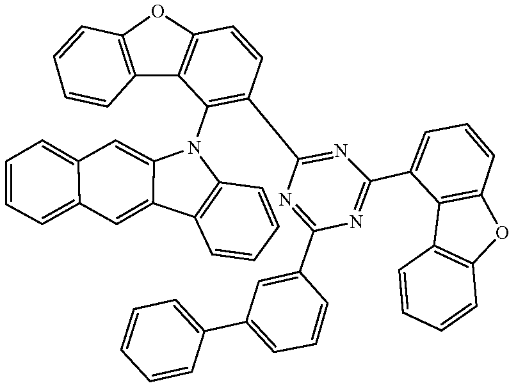
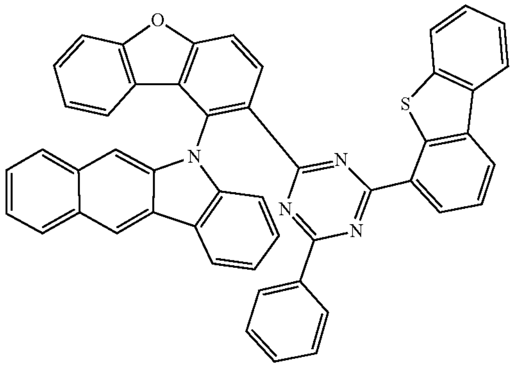
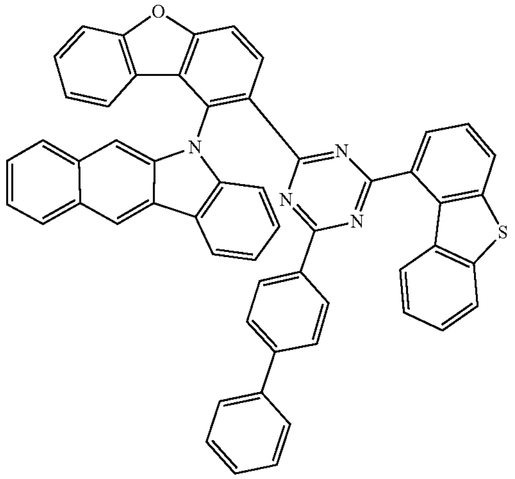

-continued
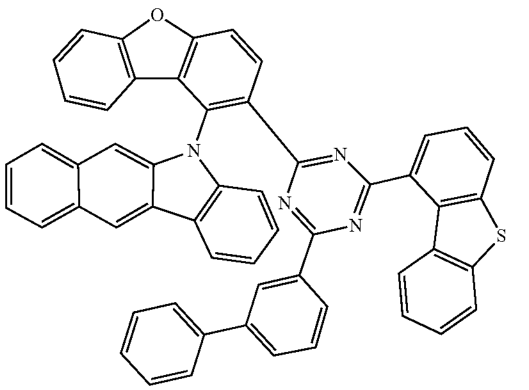
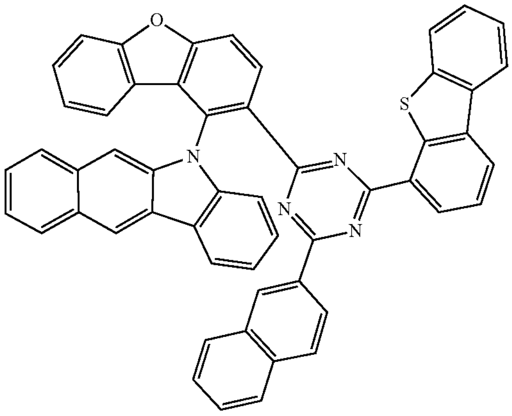
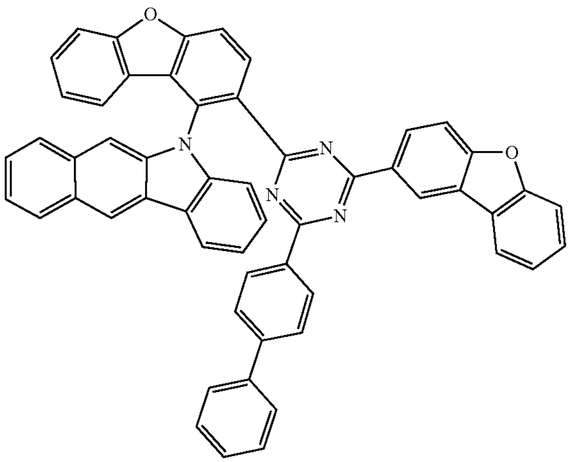
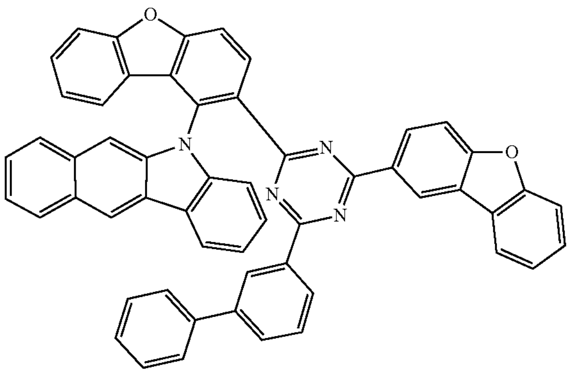
-continued
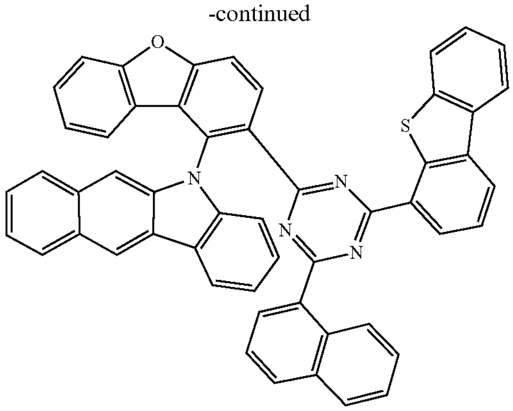
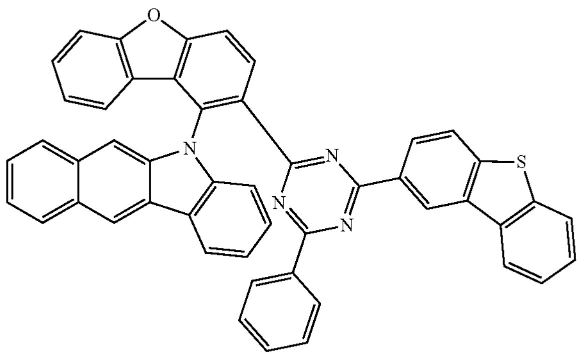
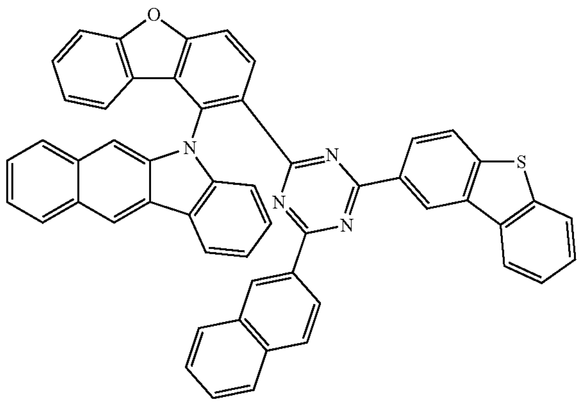
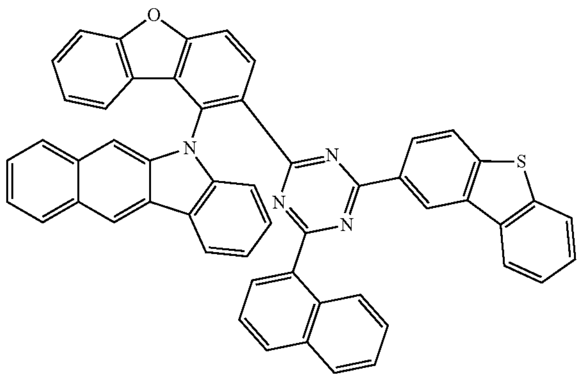

-continued
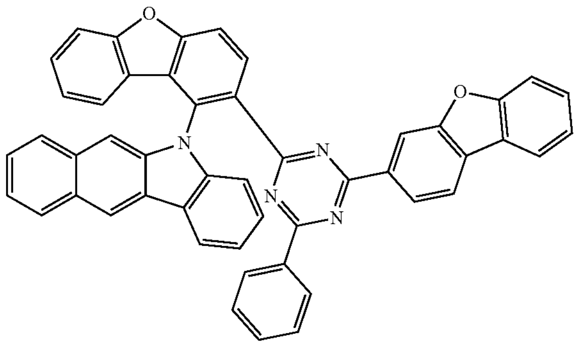
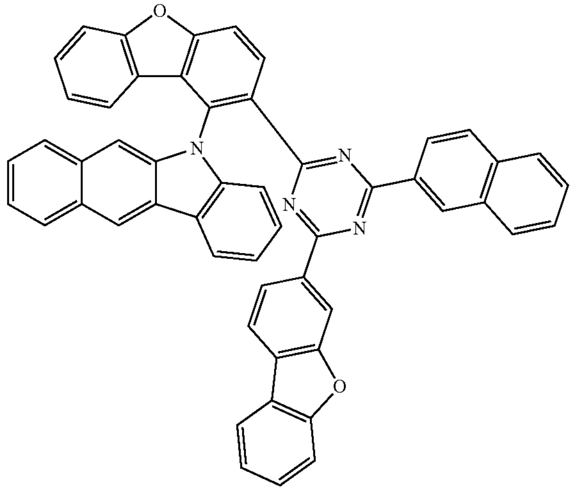
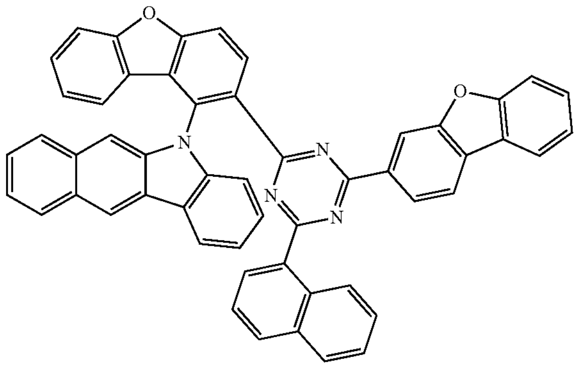
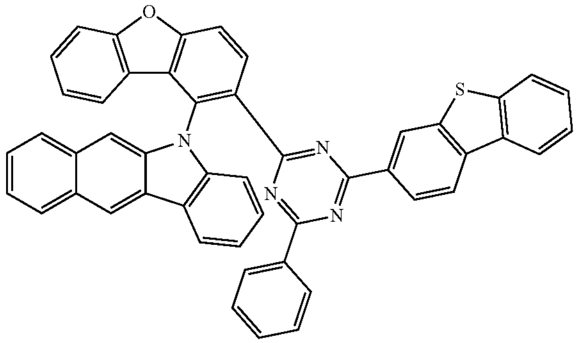
-continued
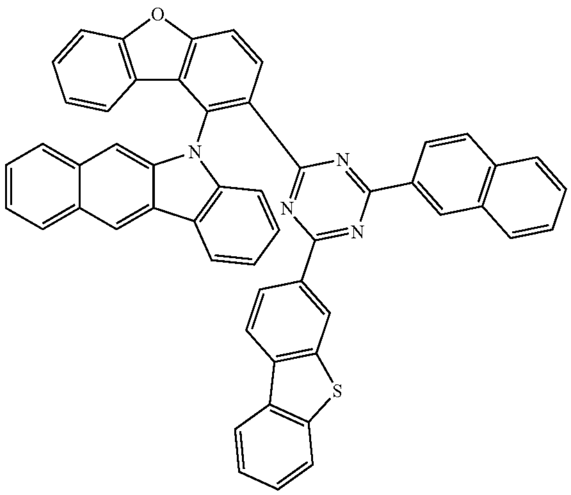
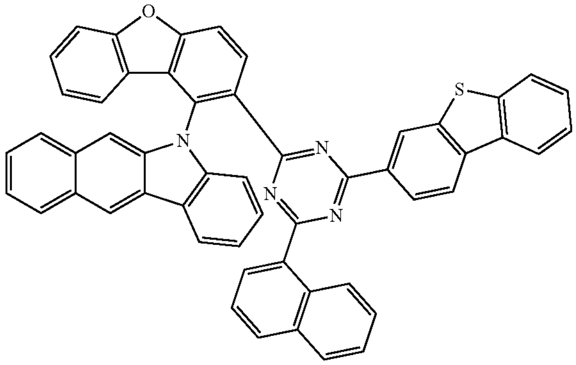
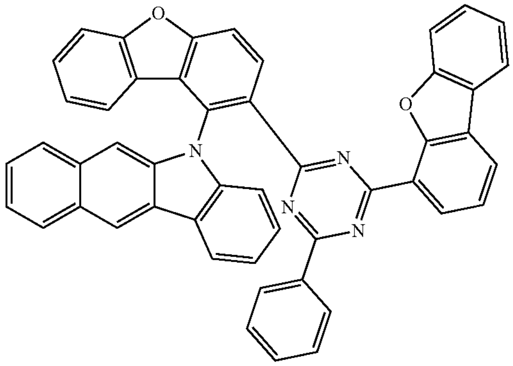
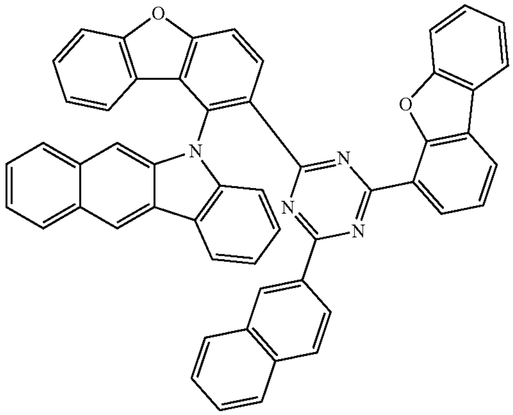

-continued
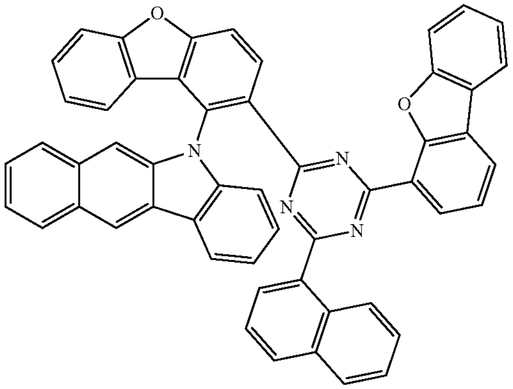
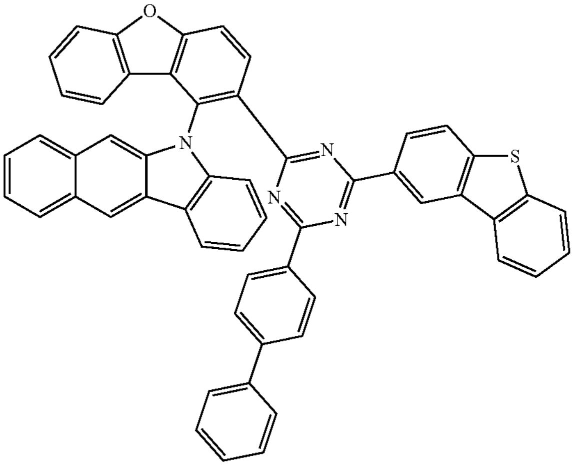
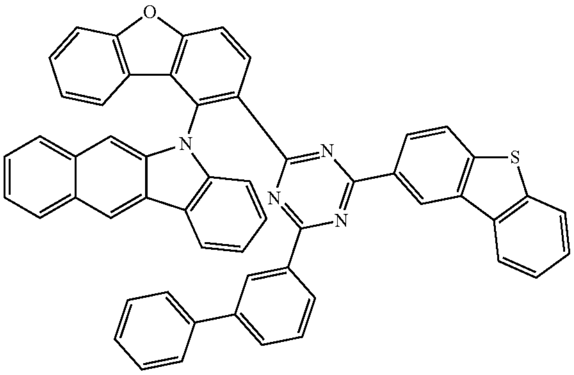
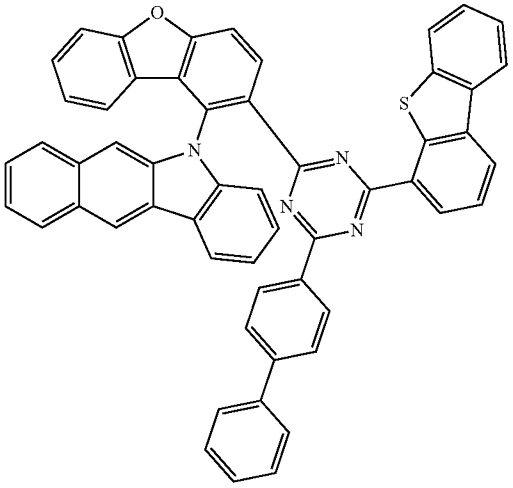
-continued
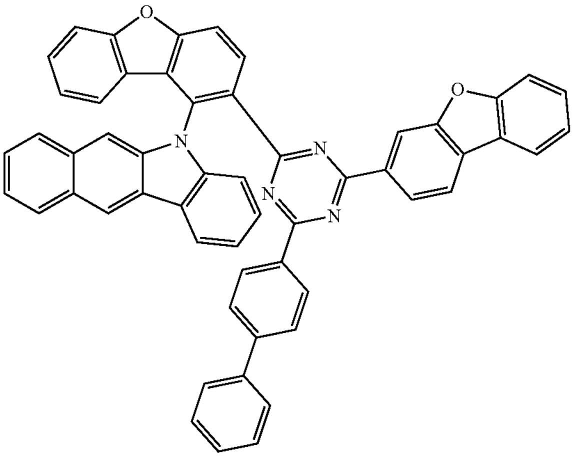
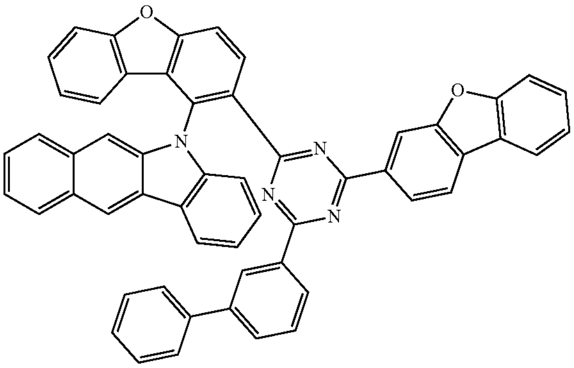
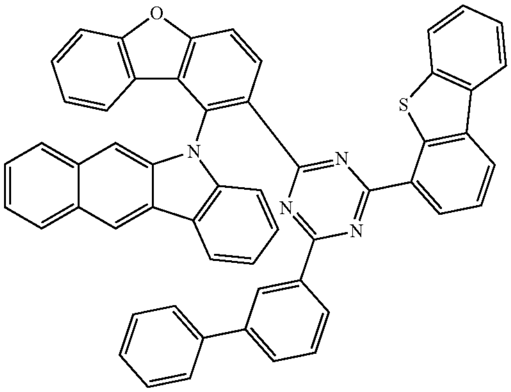
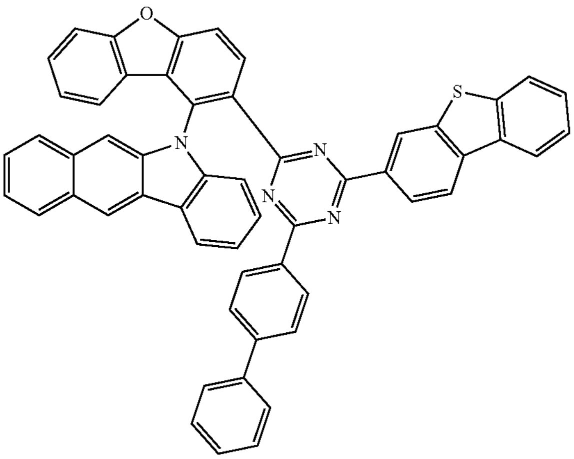

-continued
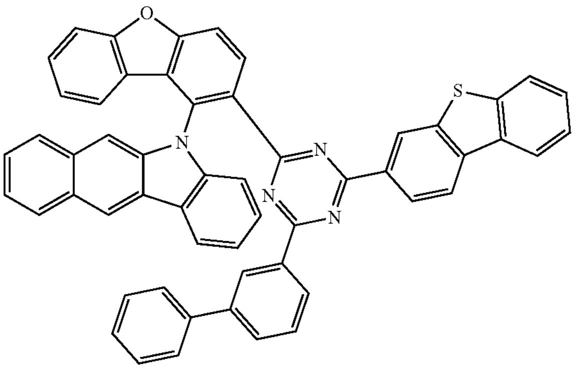
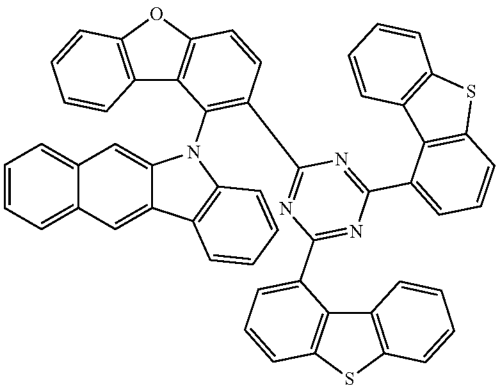
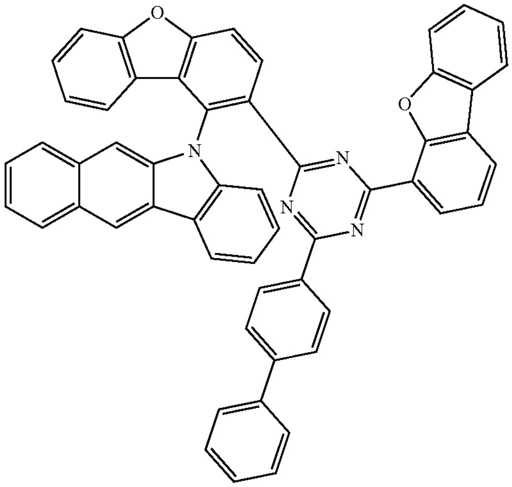
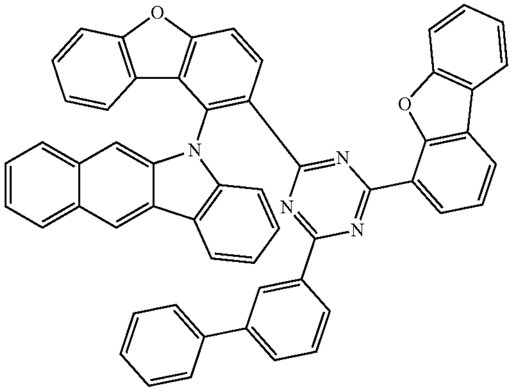
-continued
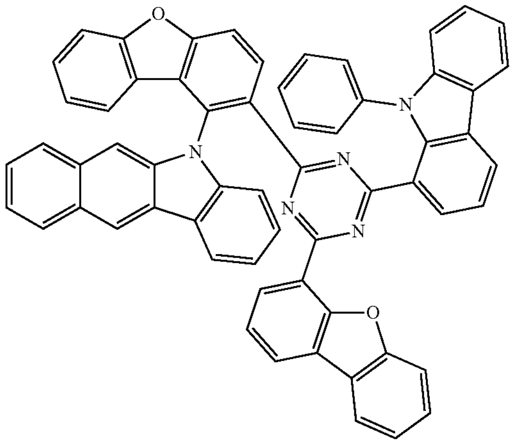
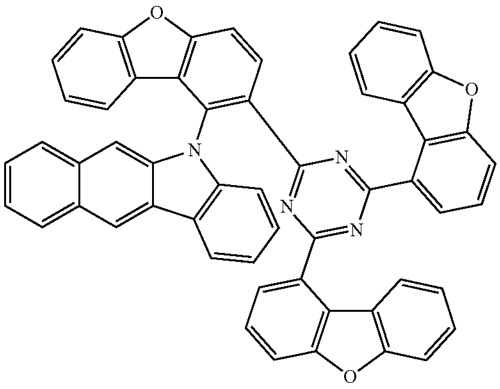
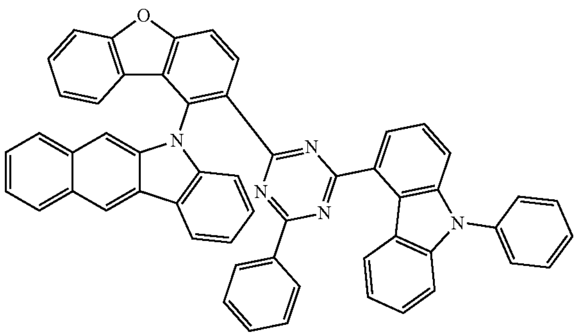
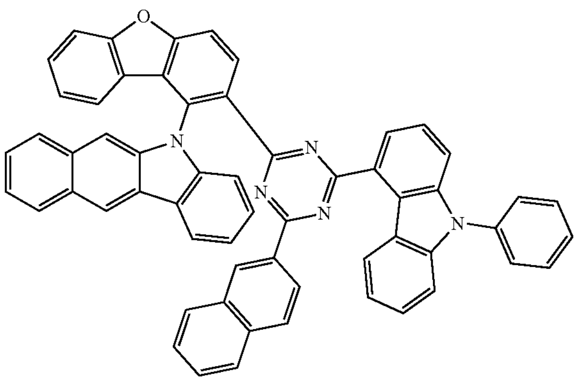

-continued
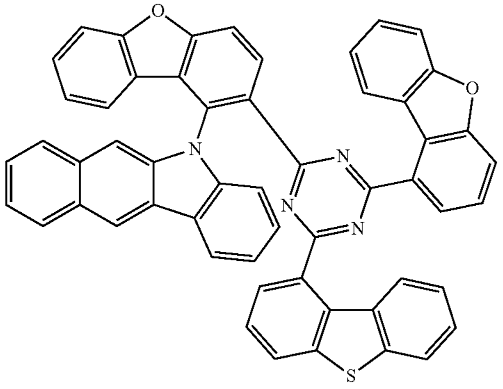
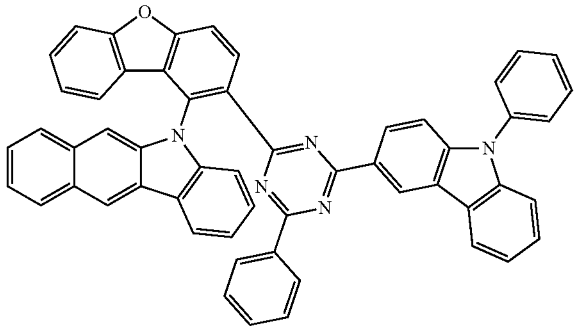
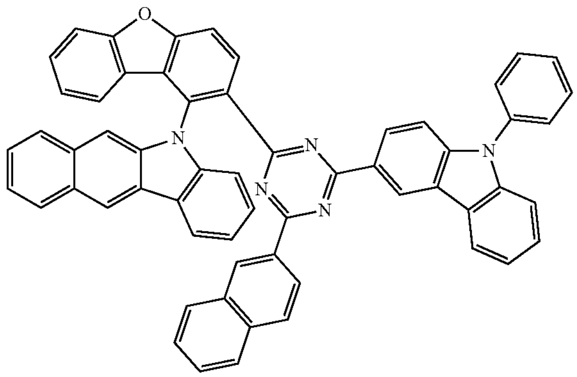
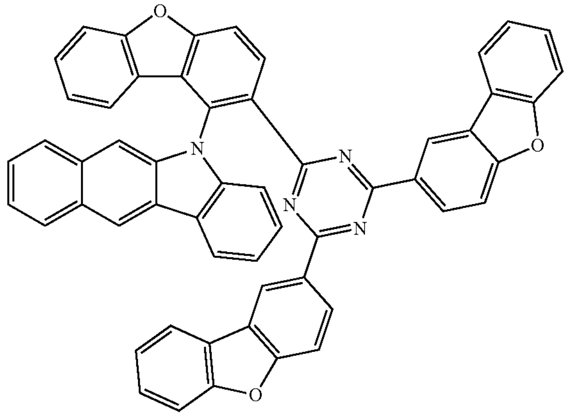
-continued
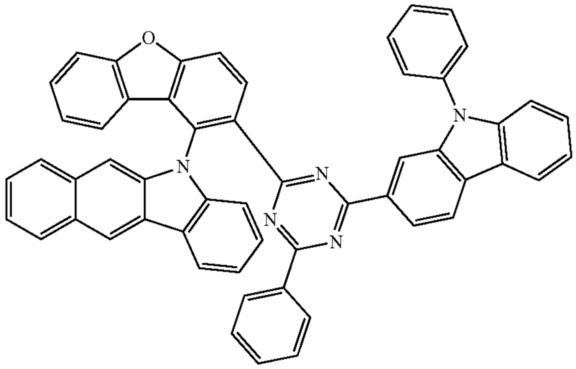
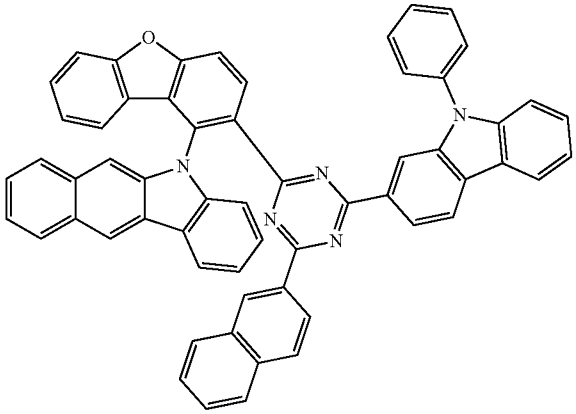
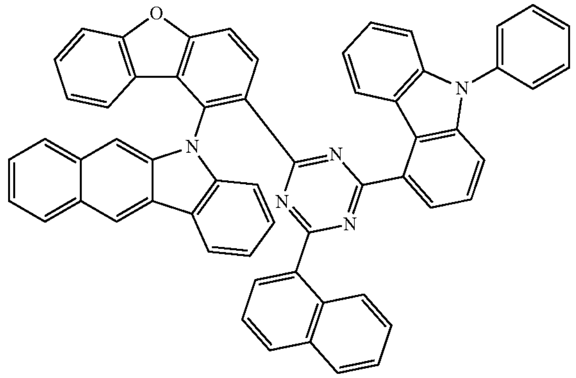
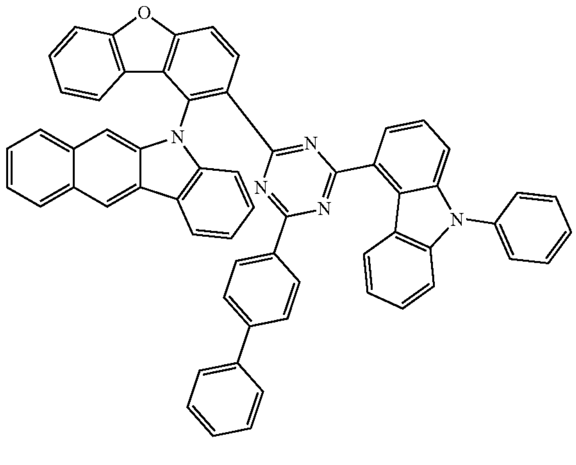

-continued
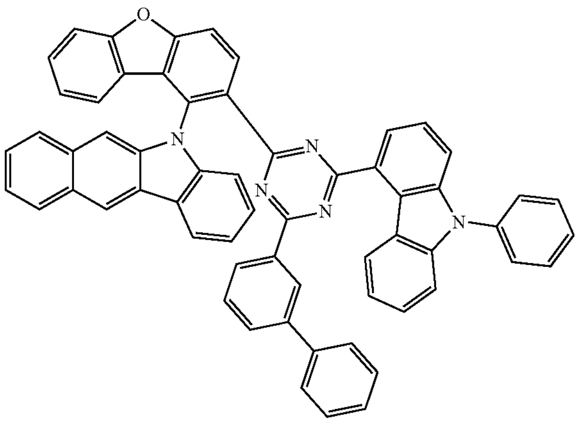
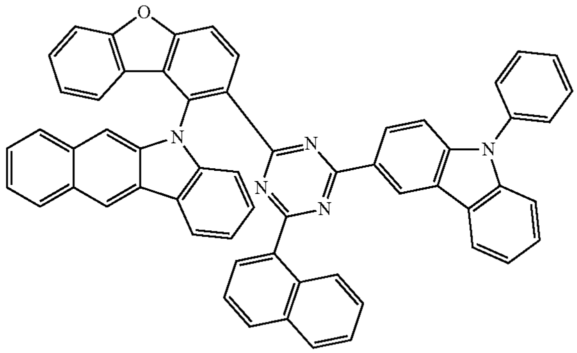
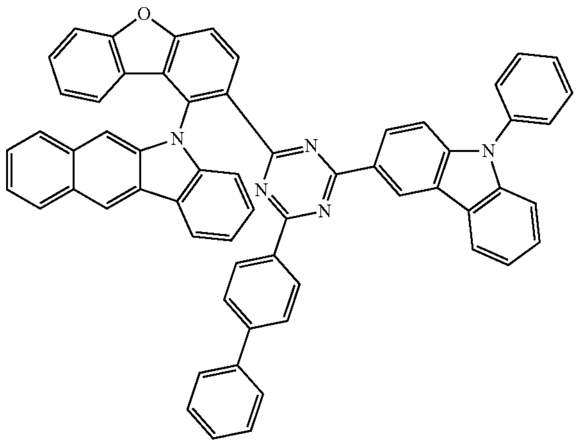
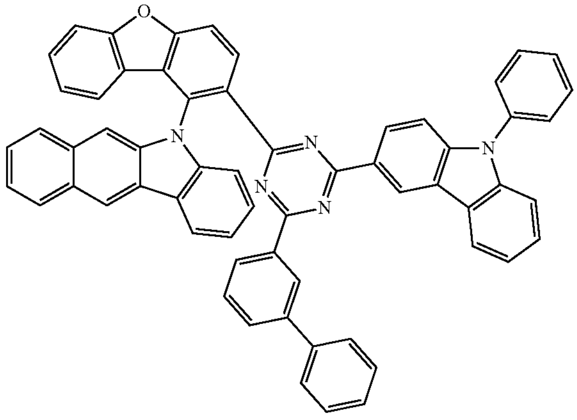
-continued
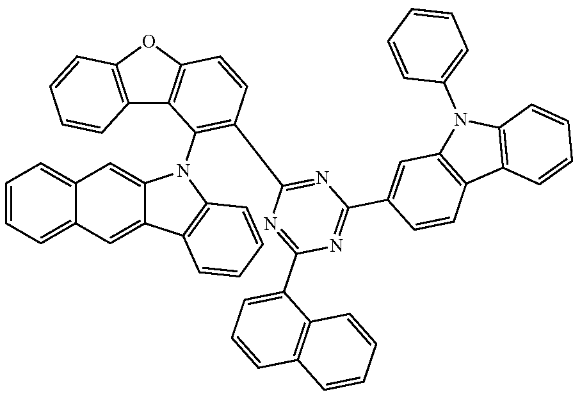
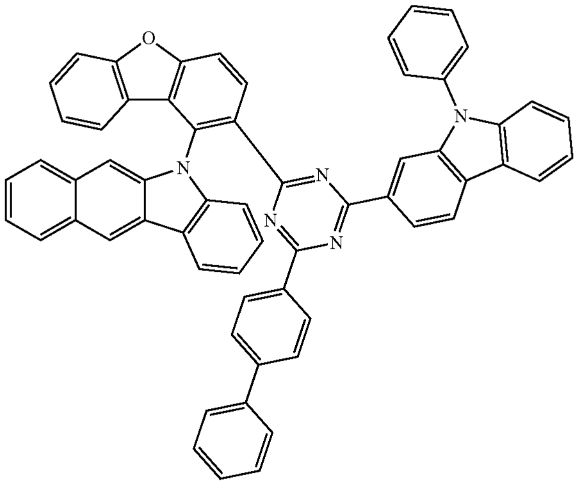
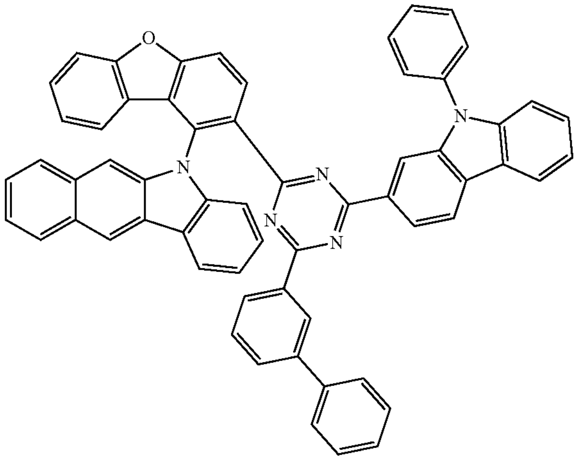

-continued
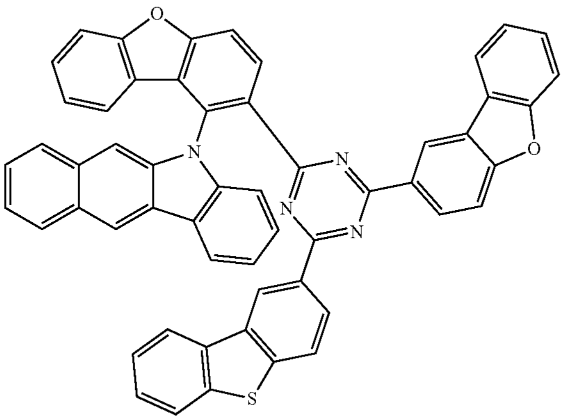
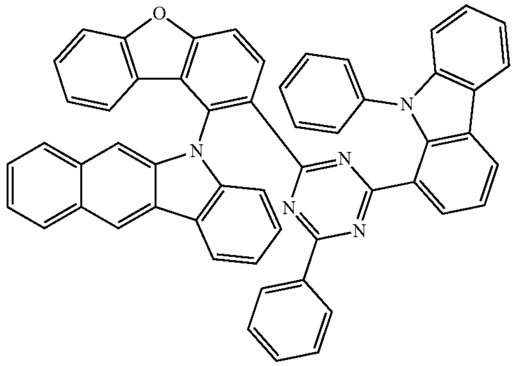
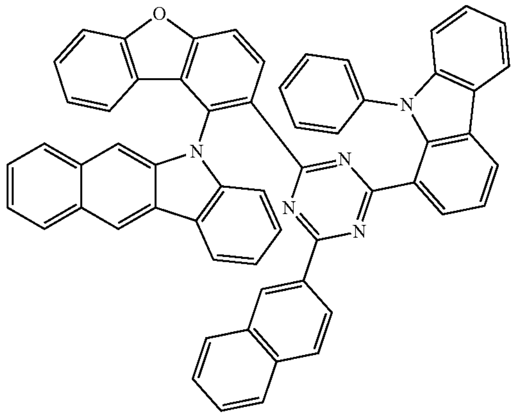
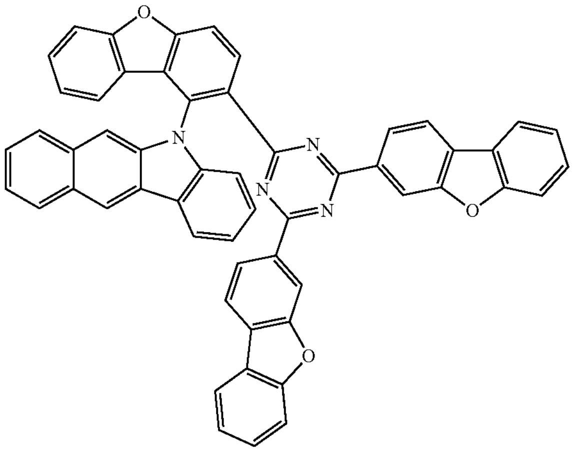
-continued
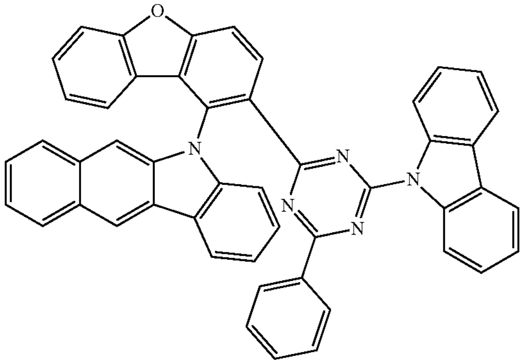
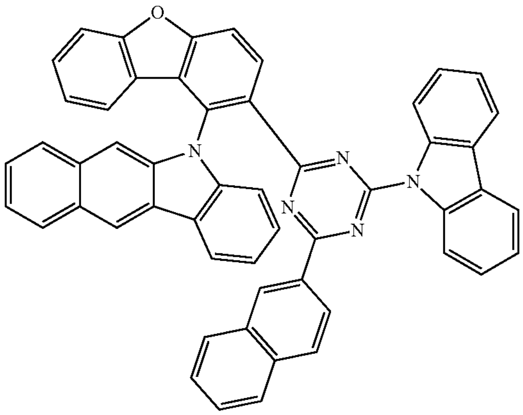
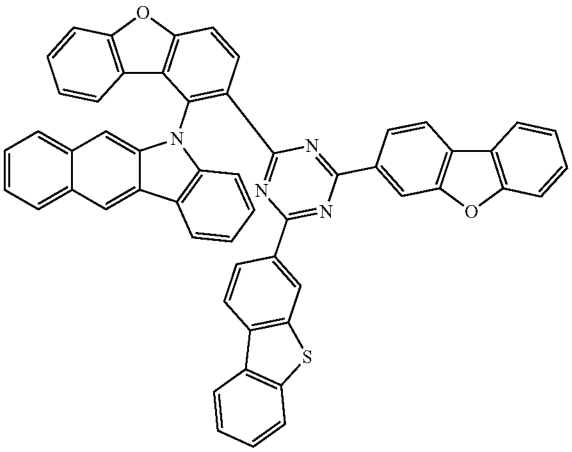
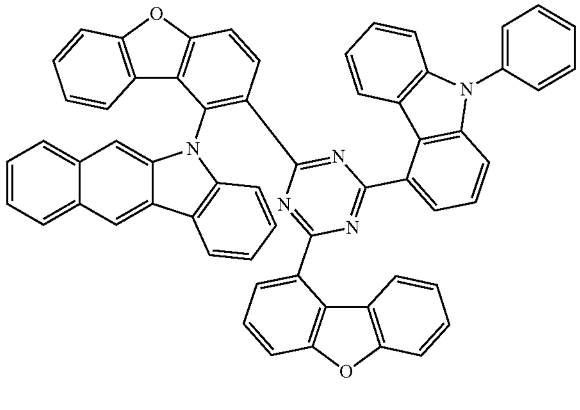

-continued
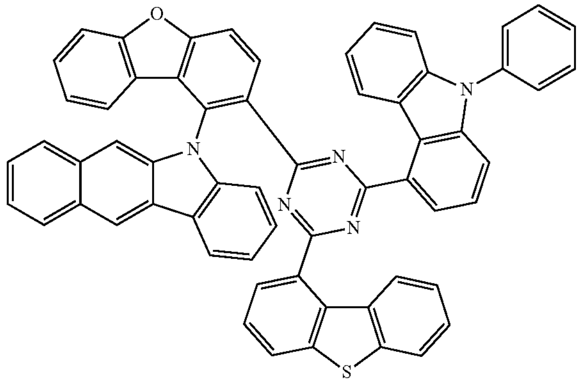
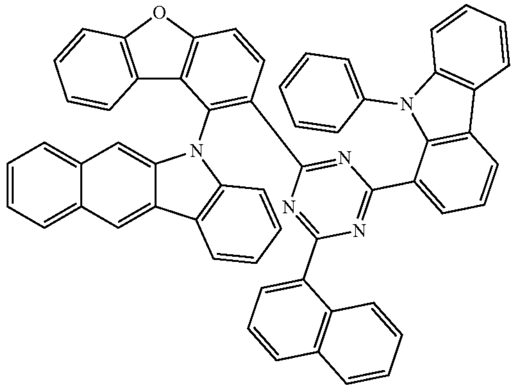
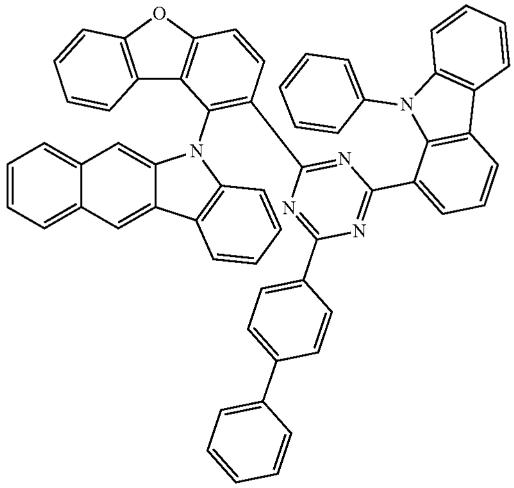
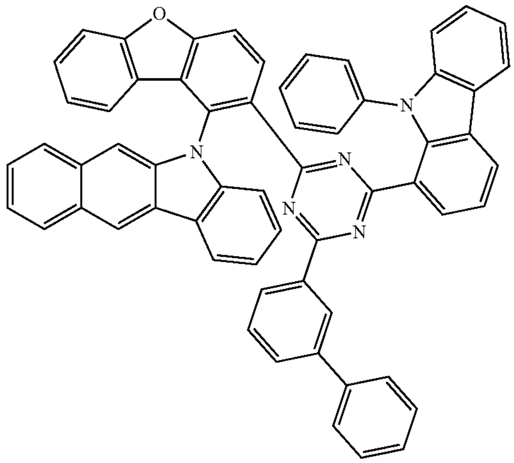
-continued
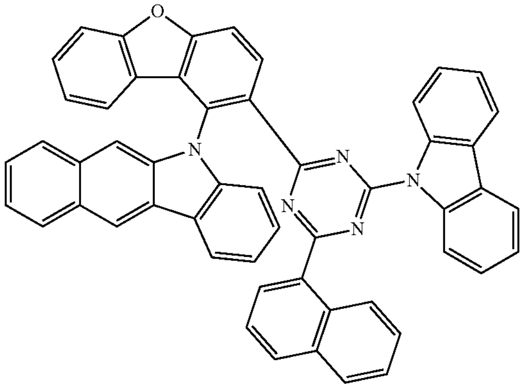
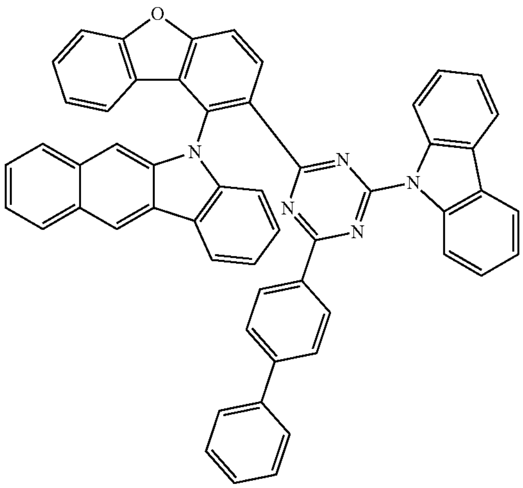
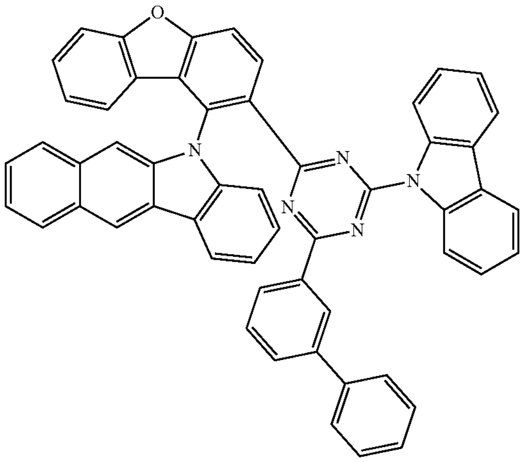
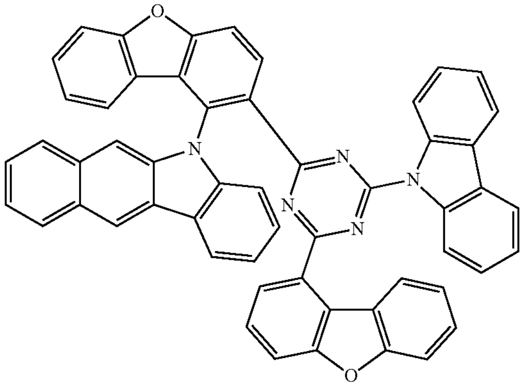

-continued
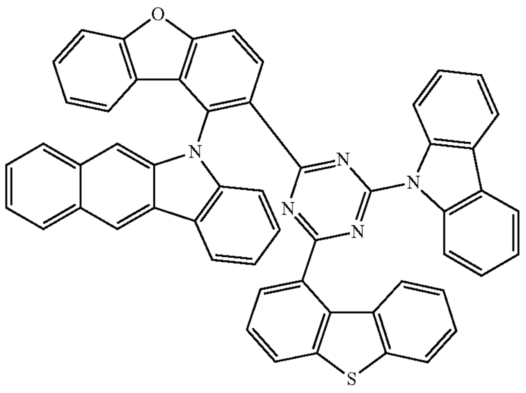
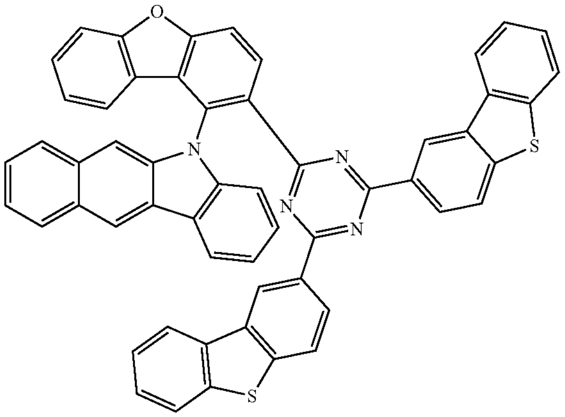
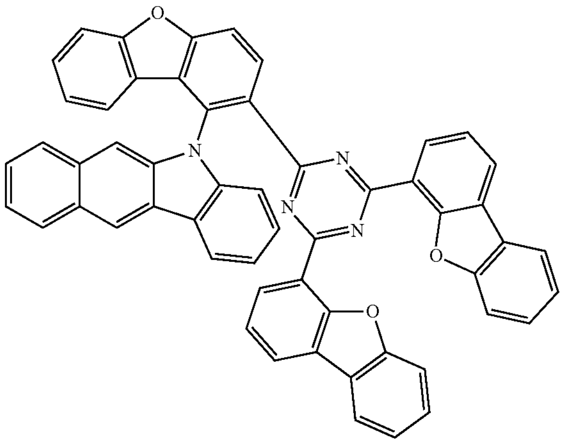
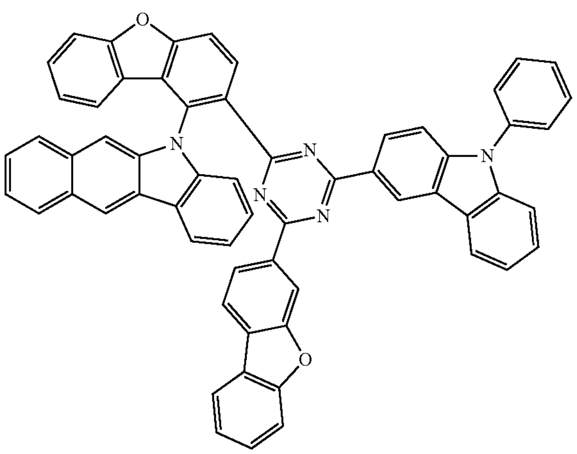
-continued
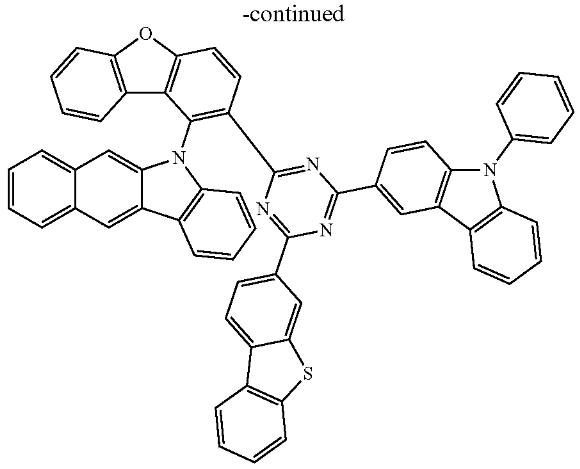
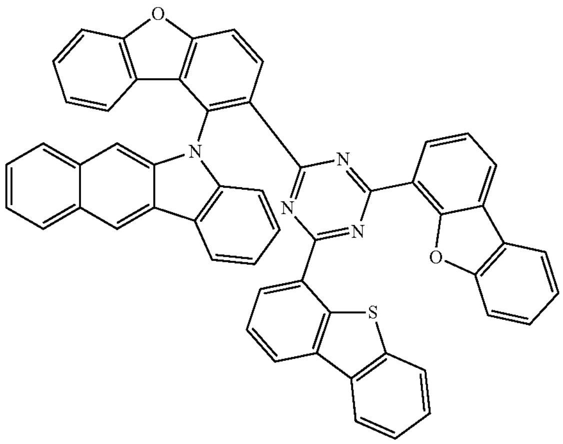
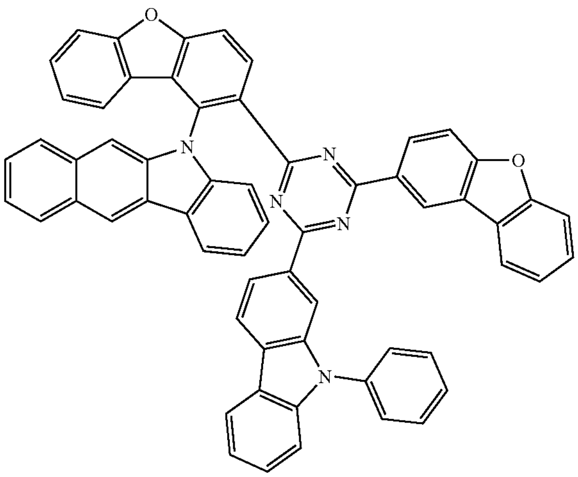

-continued
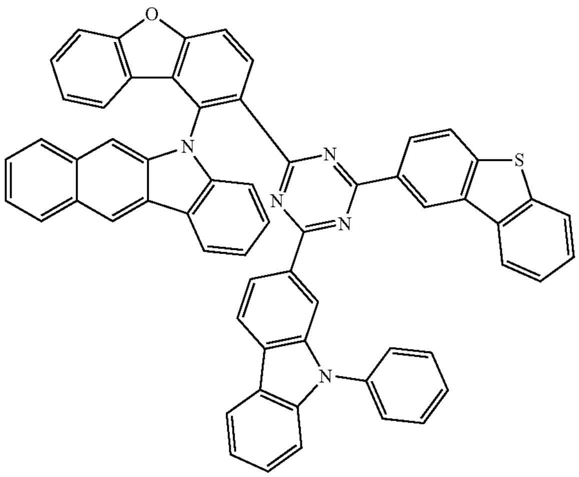
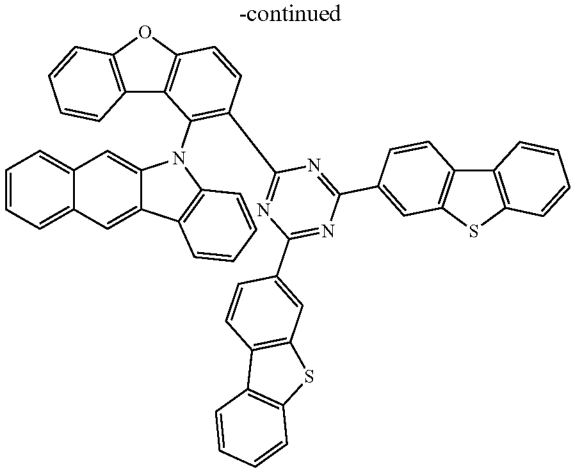
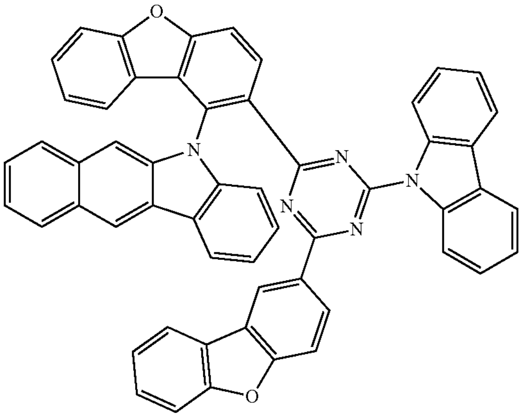
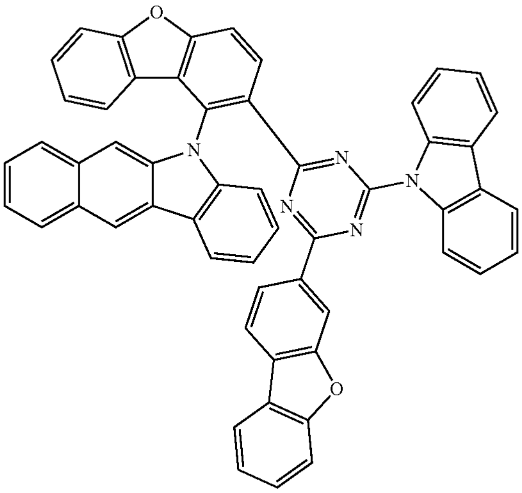
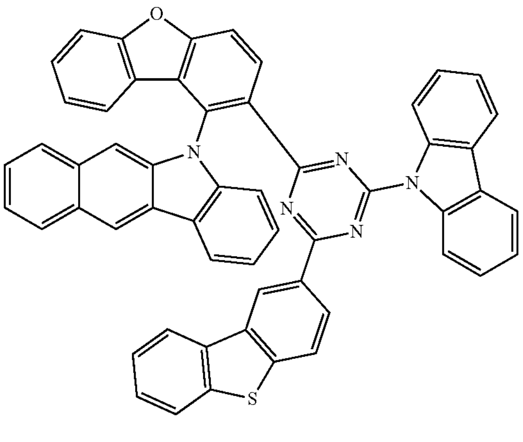
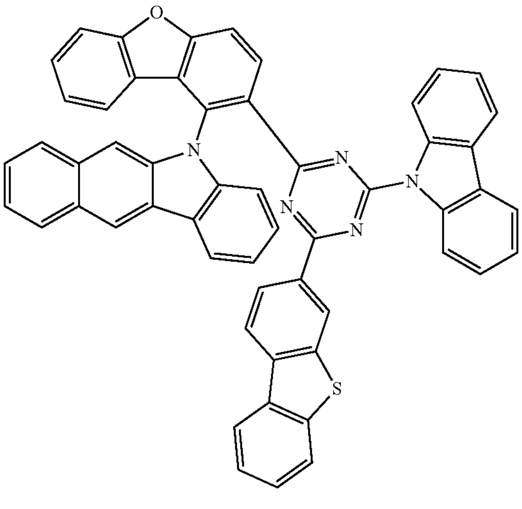

-continued
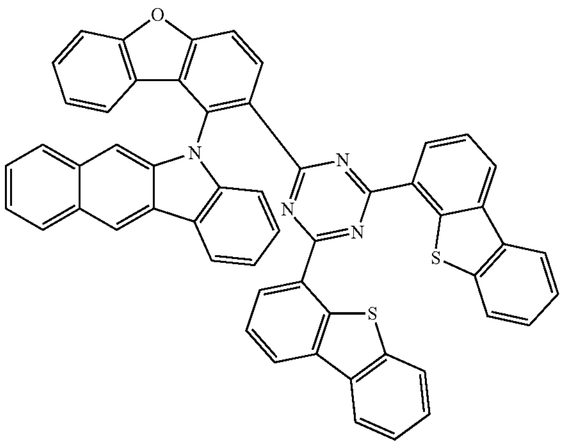
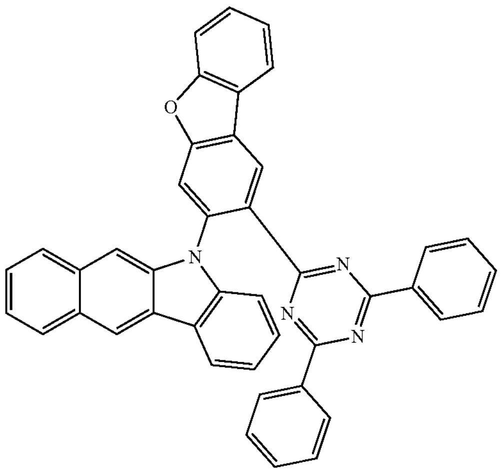
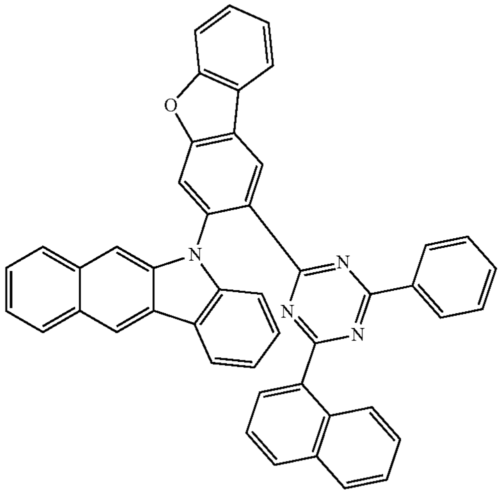
-continued
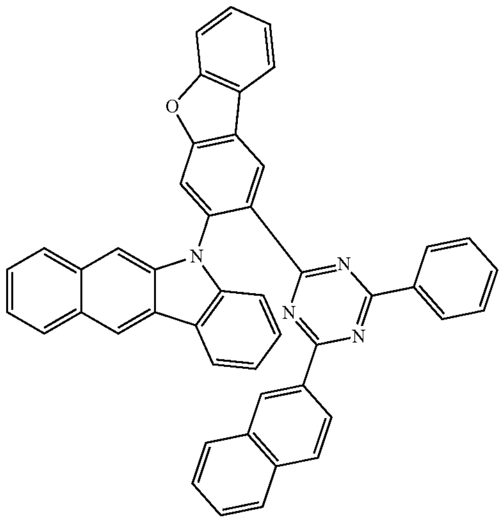
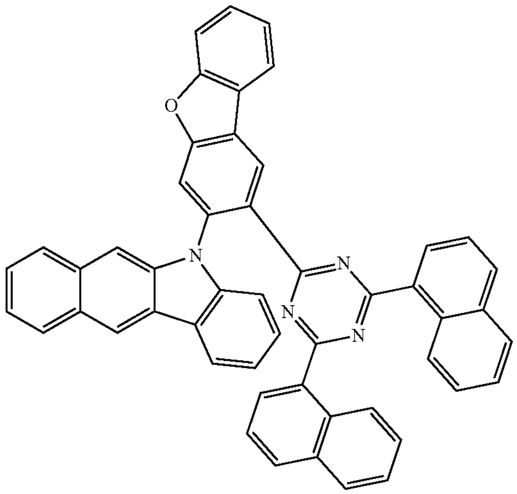
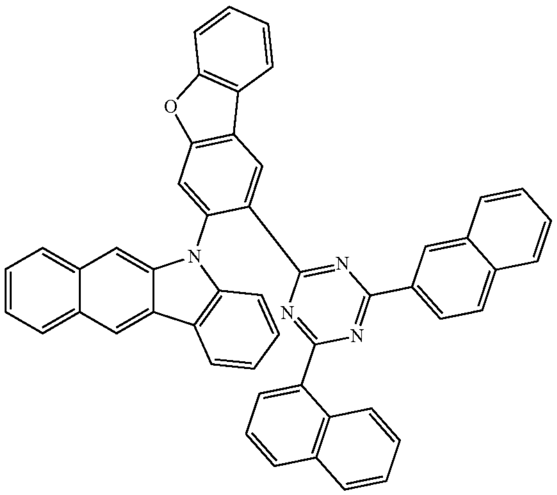

-continued
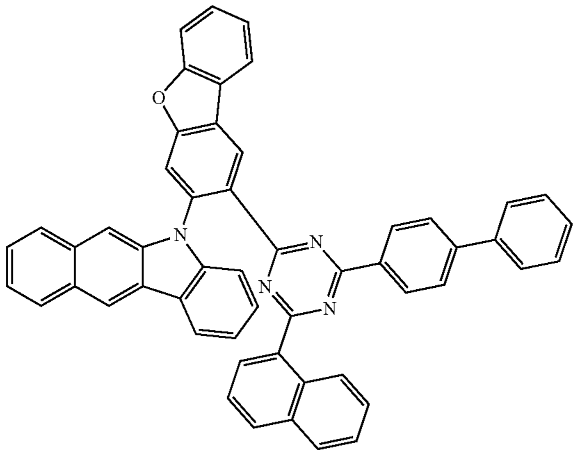
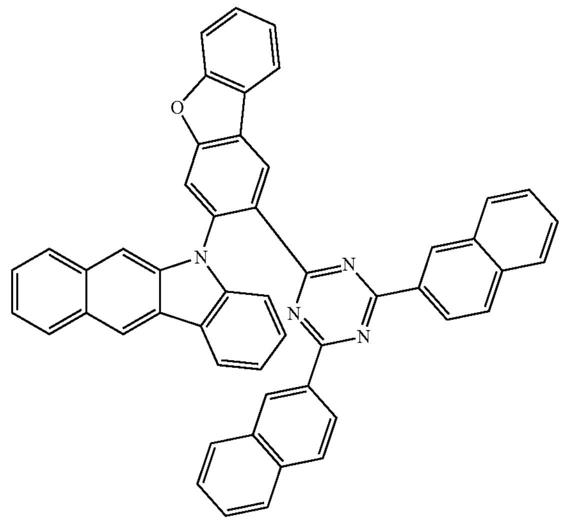
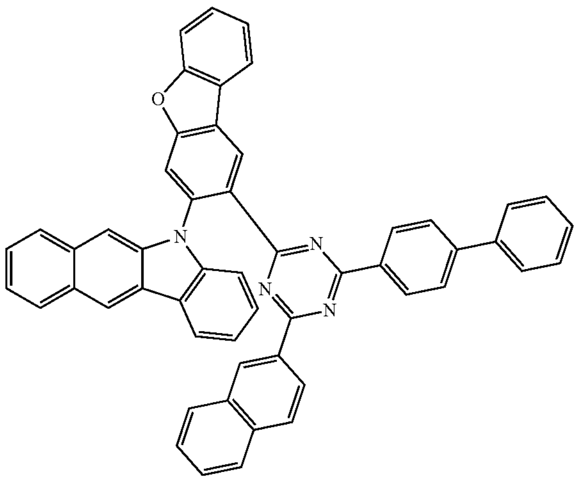
-continued
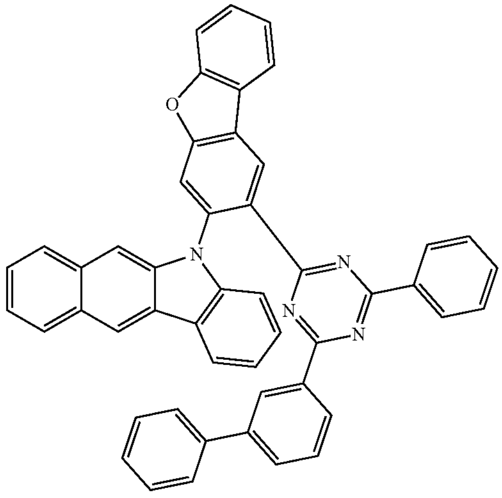
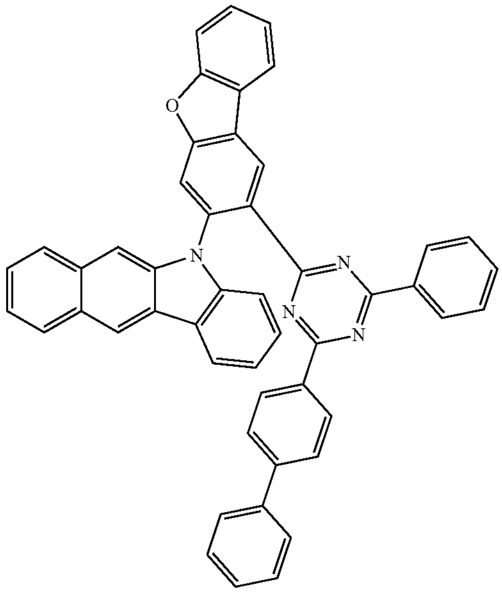
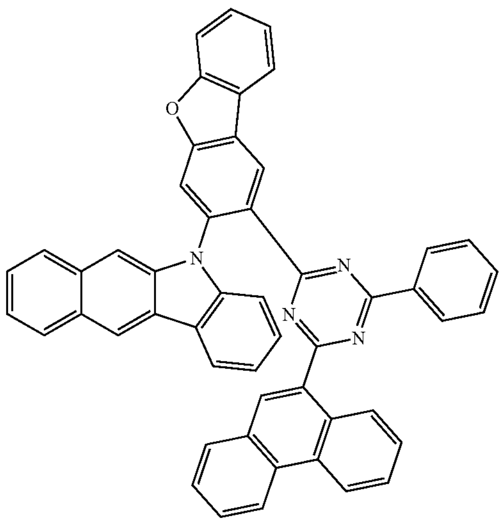

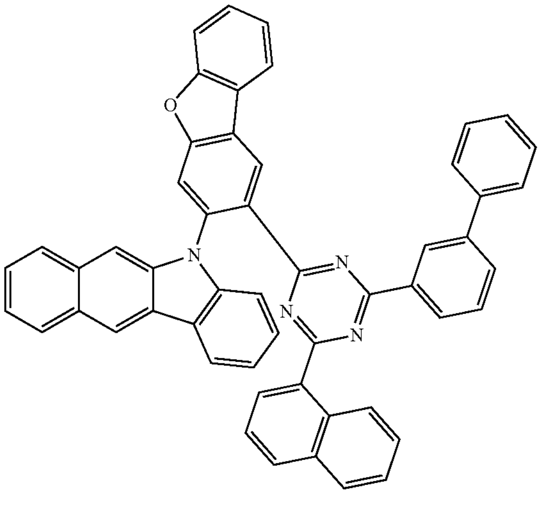
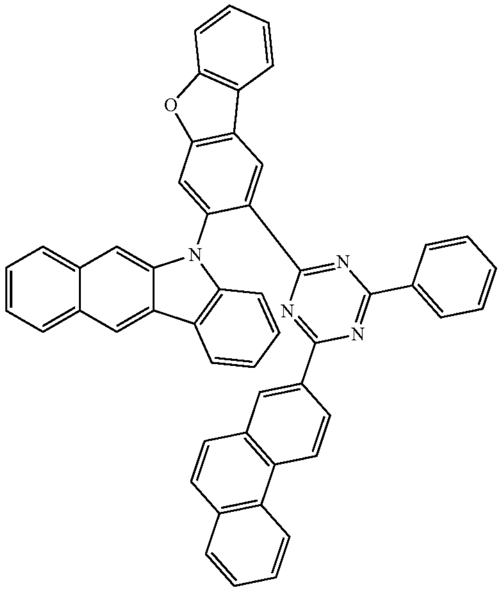
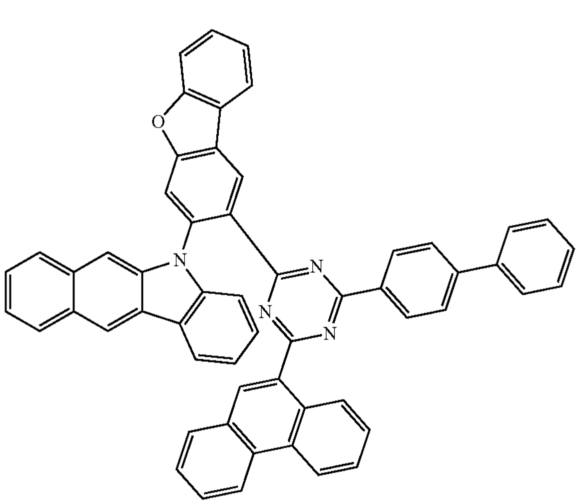
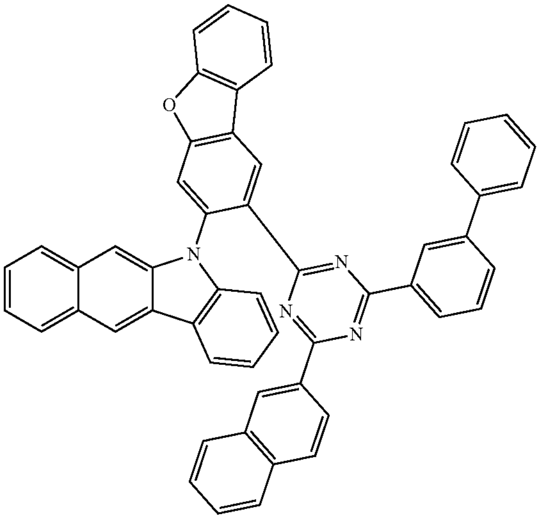
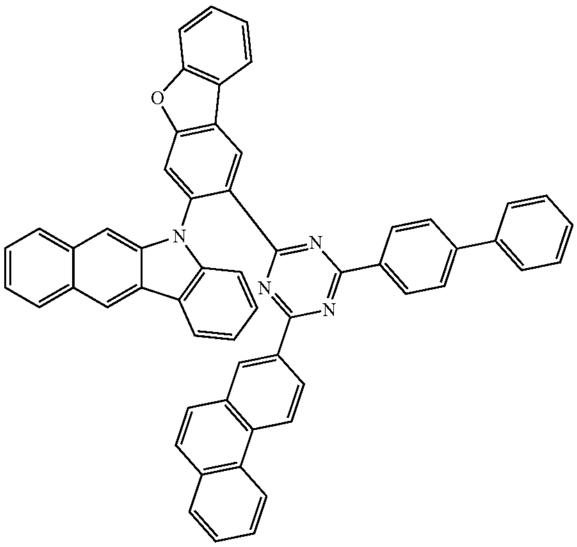
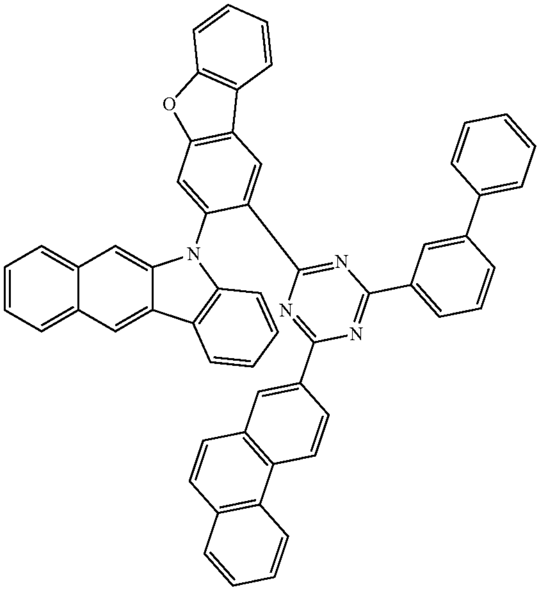

-continued
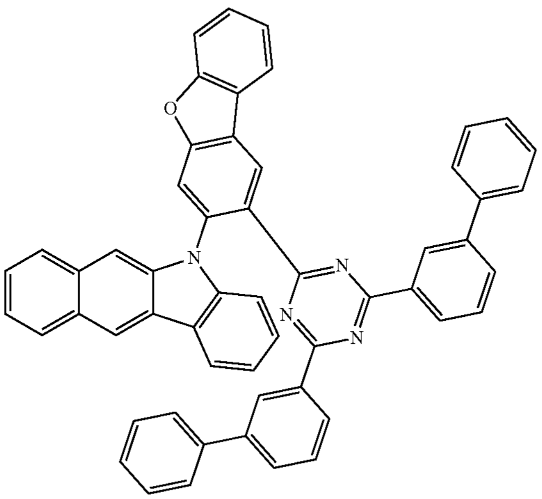
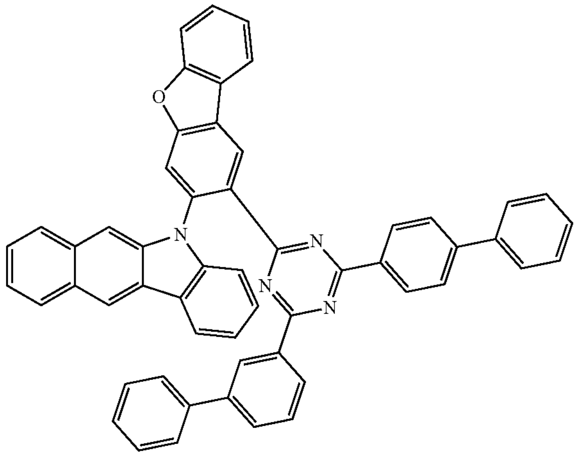
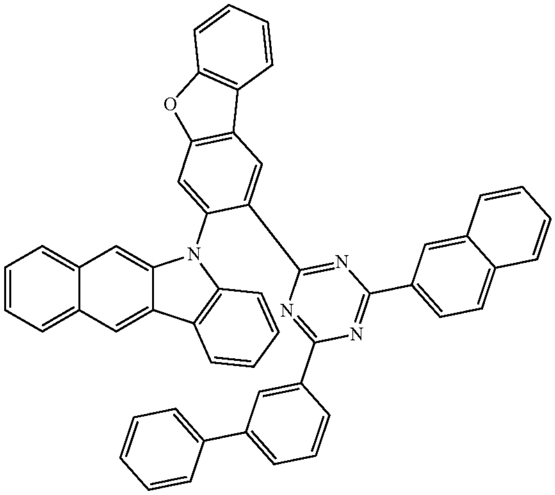
-continued
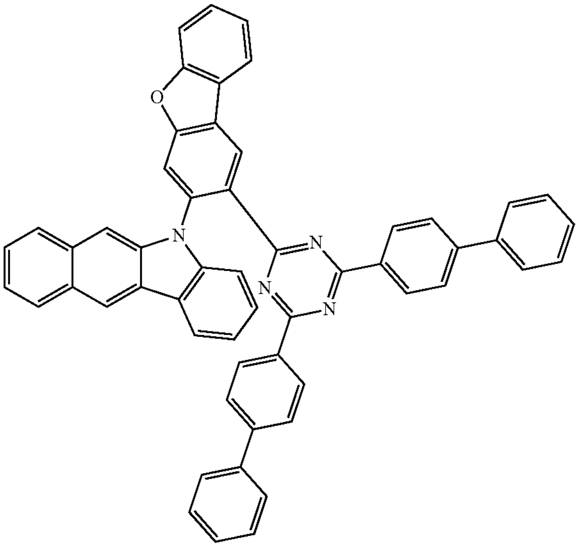
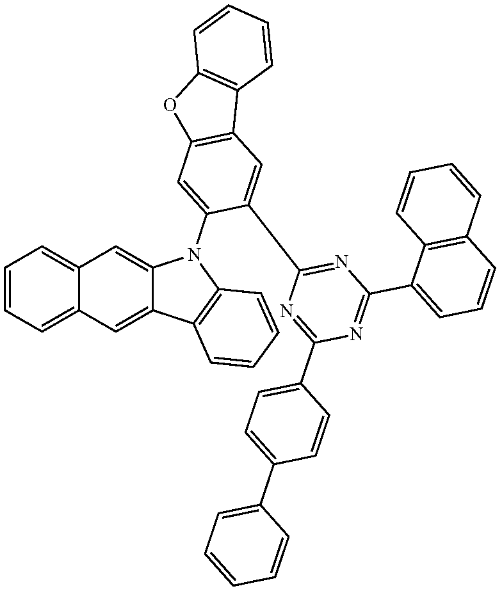
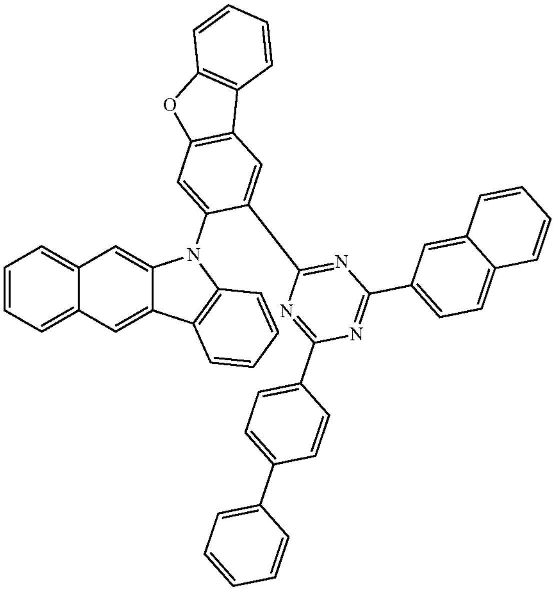

-continued
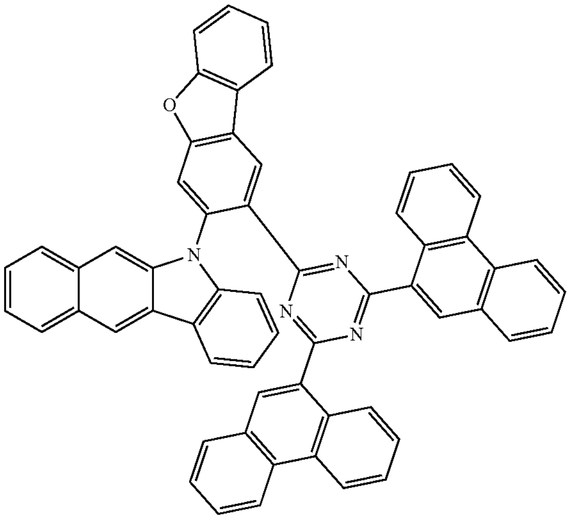
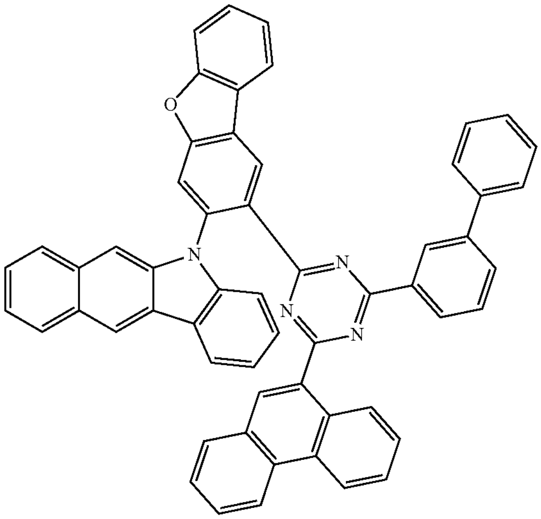
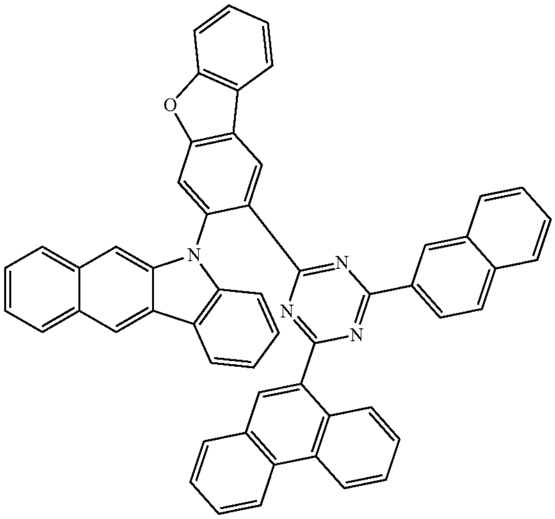
-continued
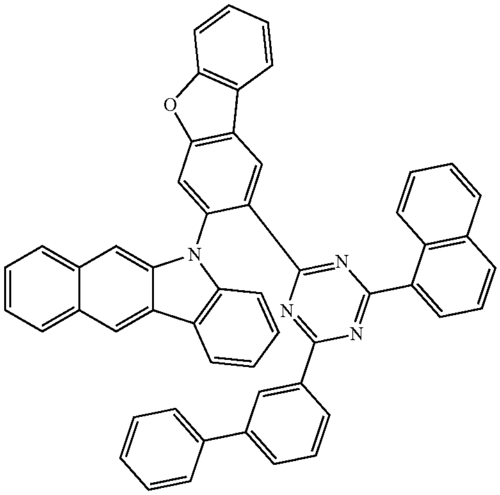
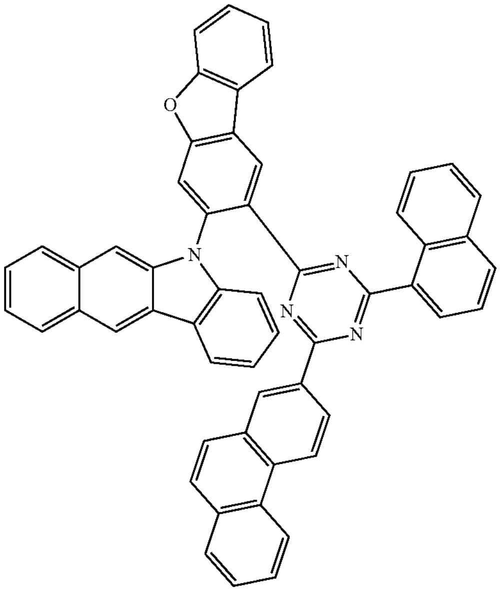
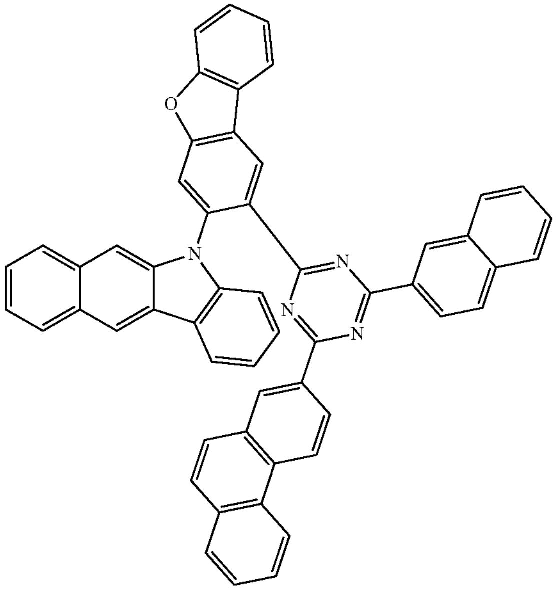

-continued
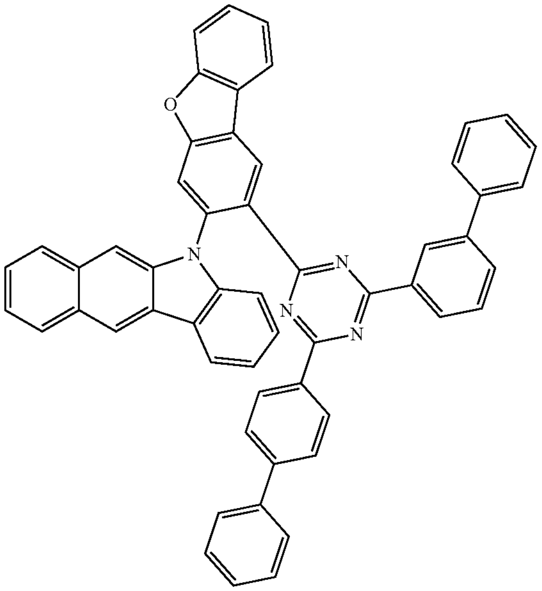
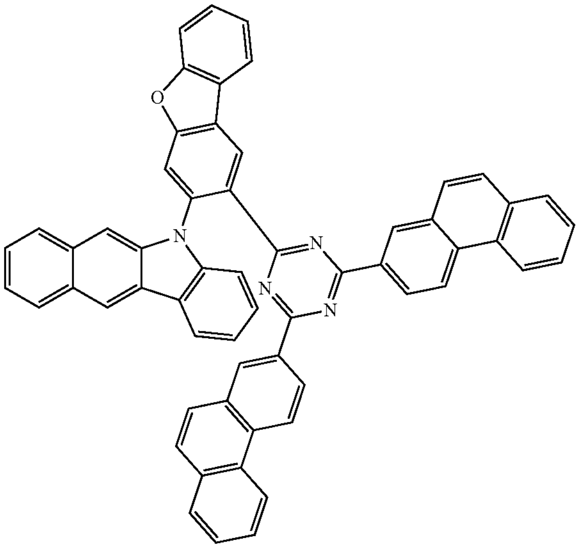
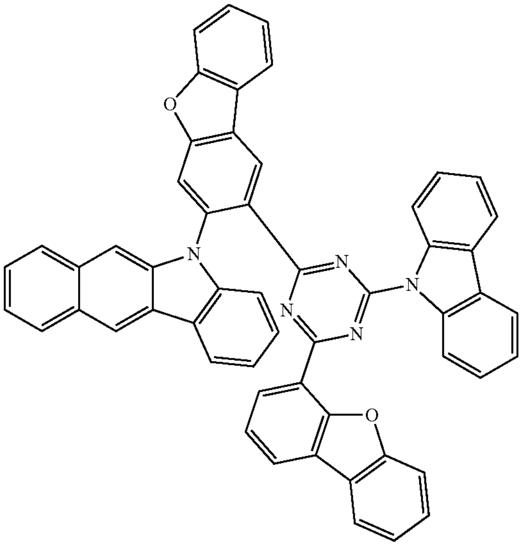
-continued
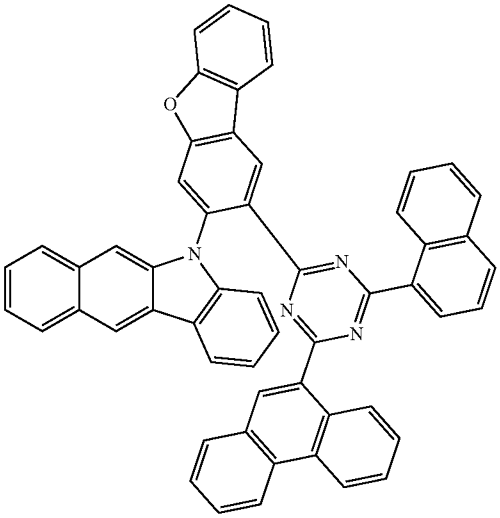
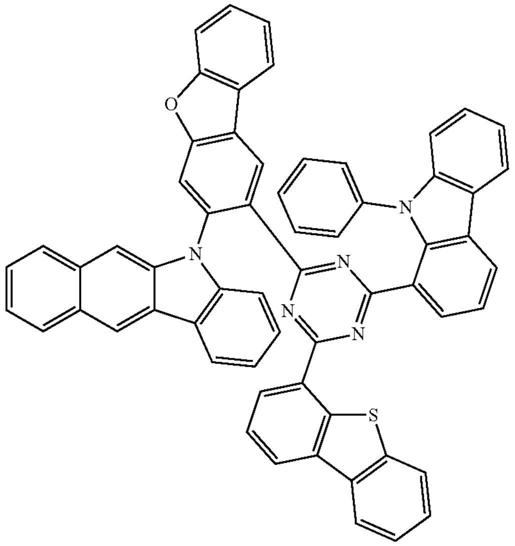
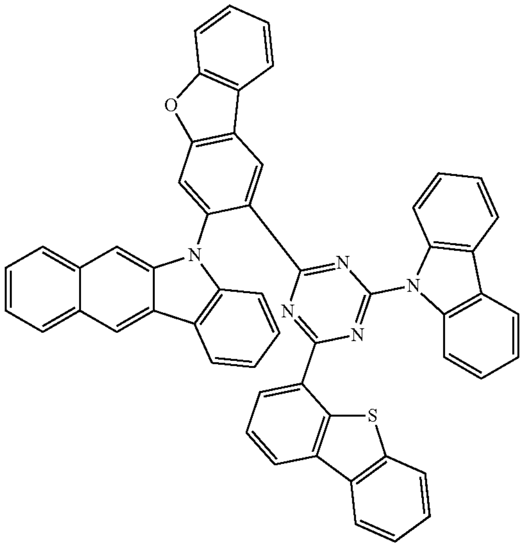

-continued
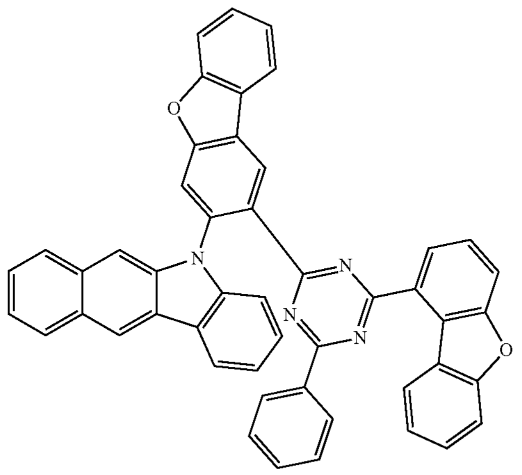
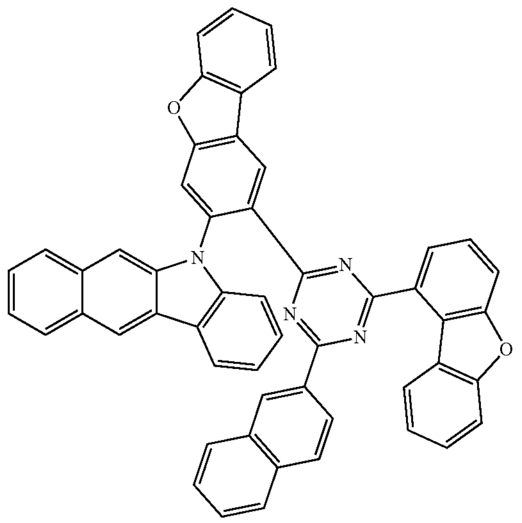
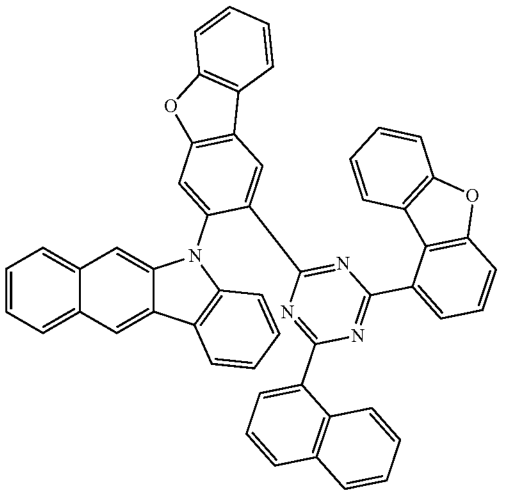
-continued
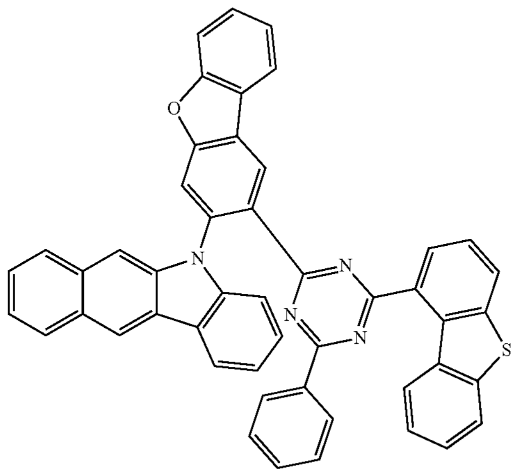
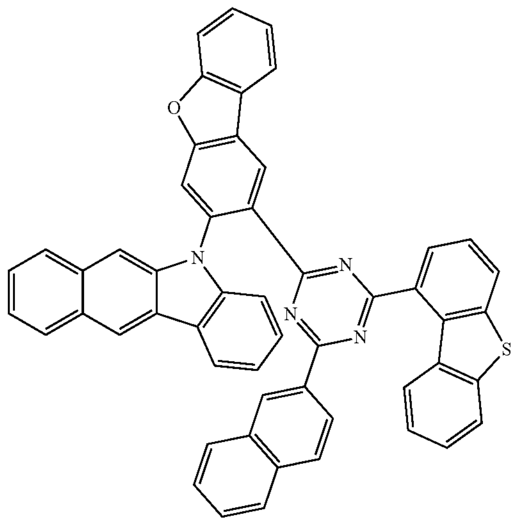
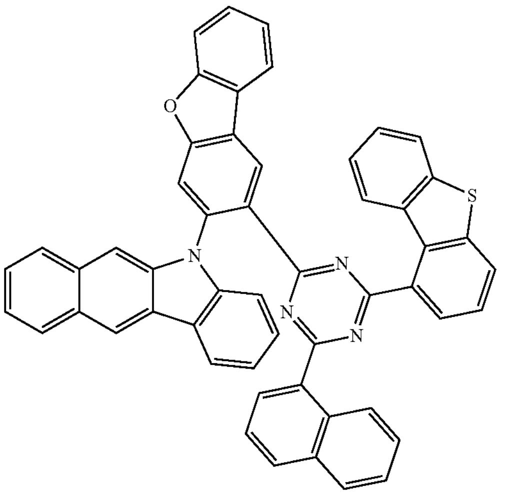

-continued
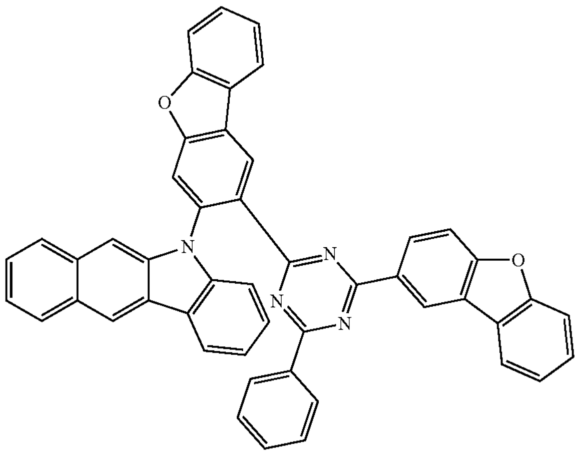
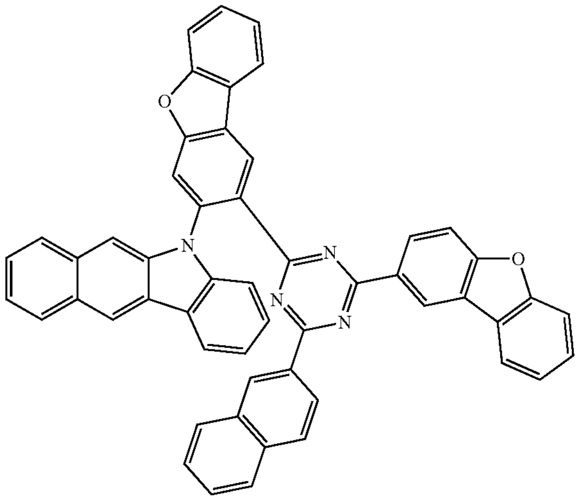
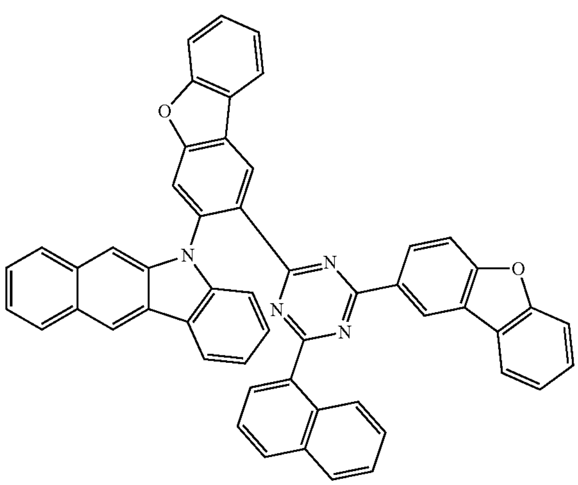
-continued
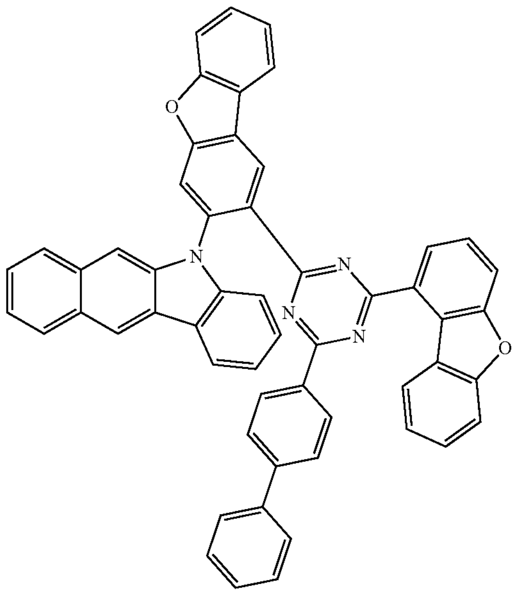
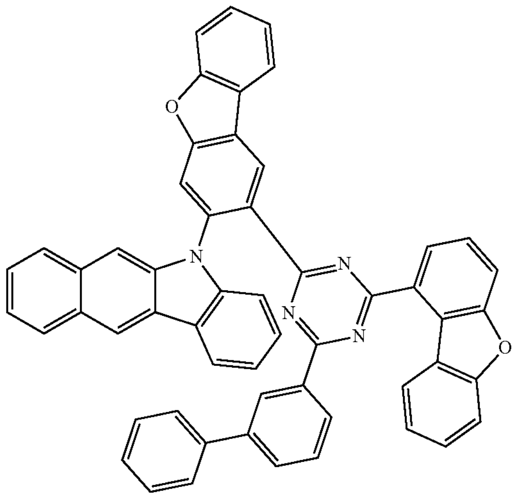
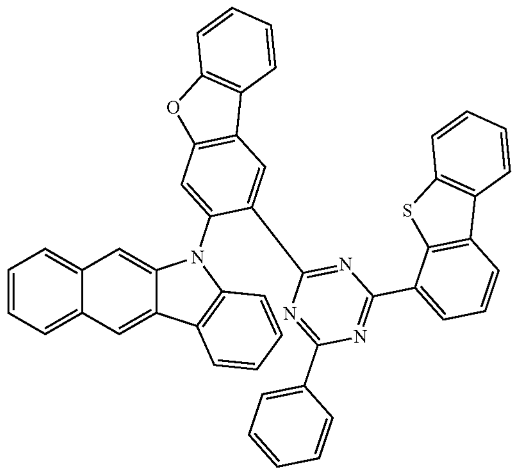

-continued
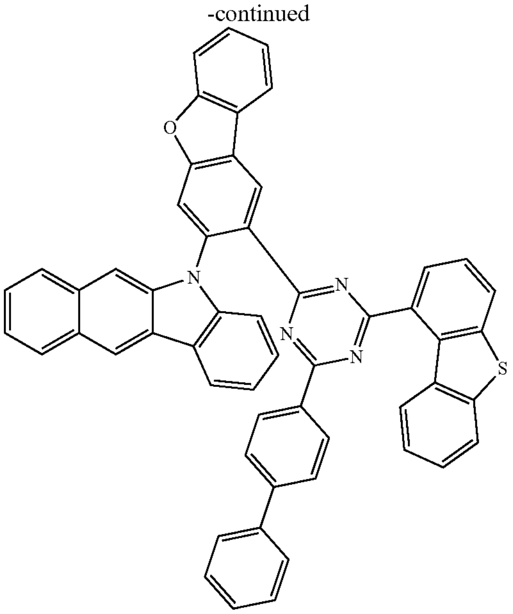
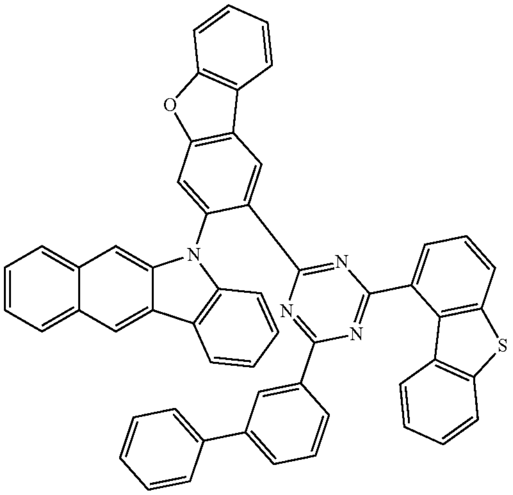
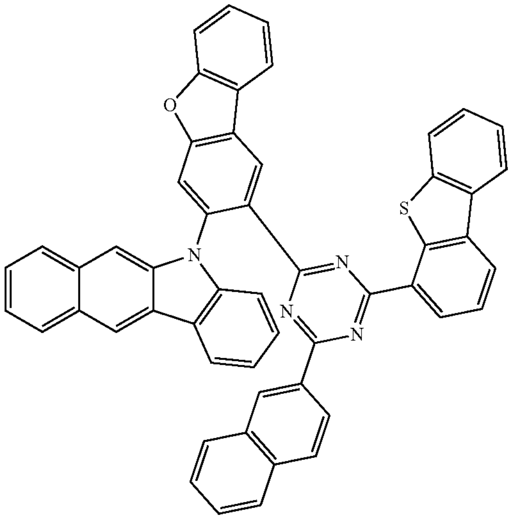
-continued
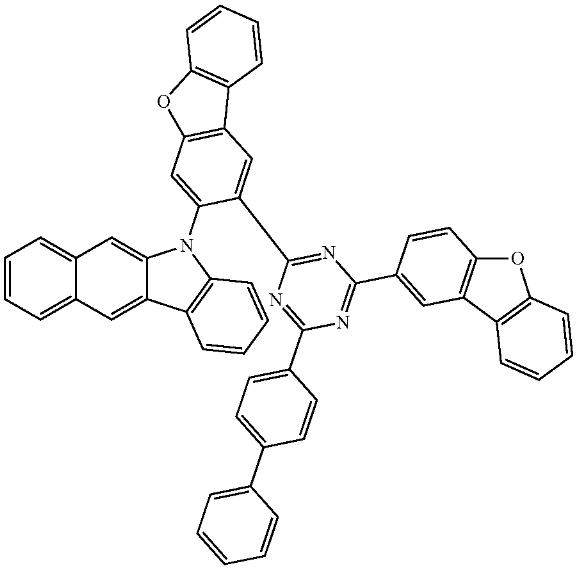
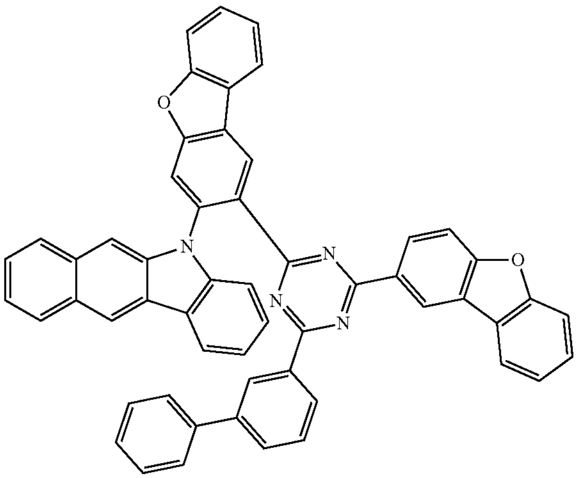
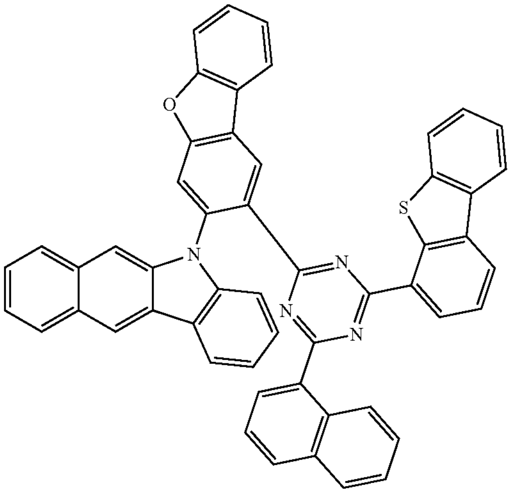

-continued
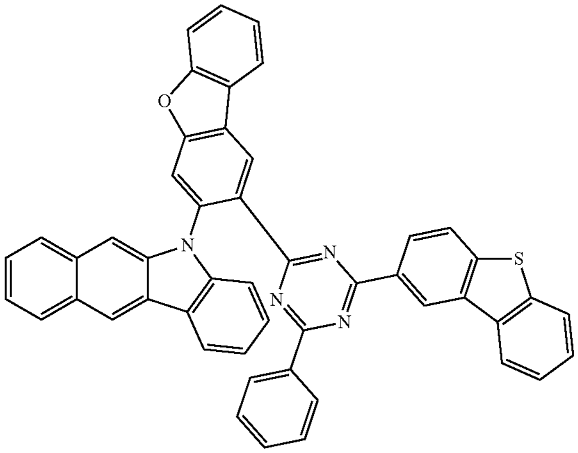
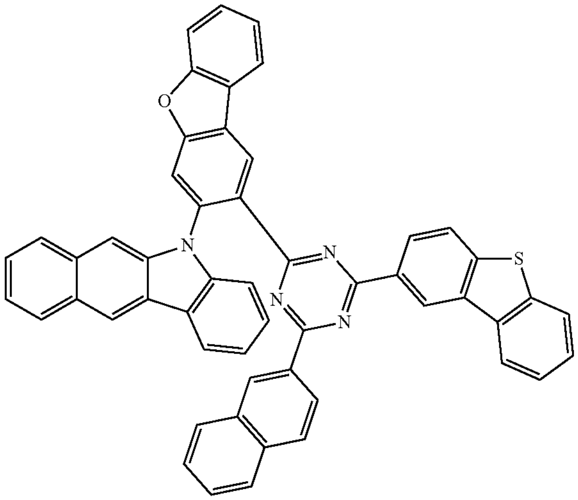
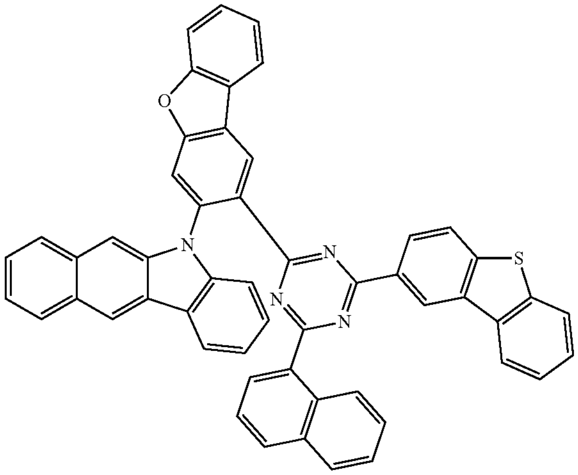
-continued
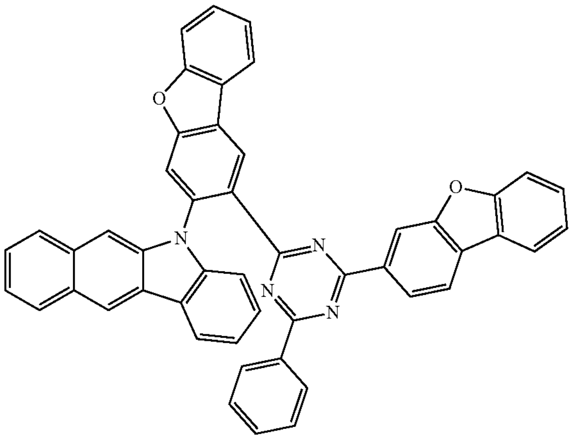
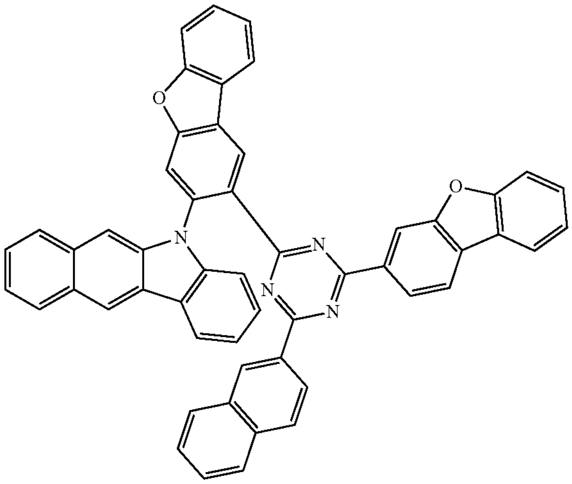
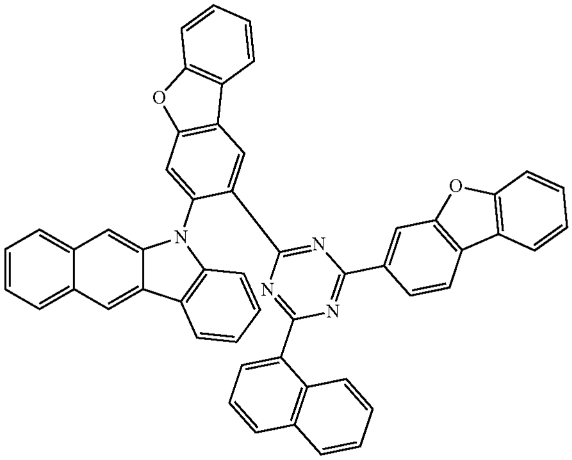

-continued
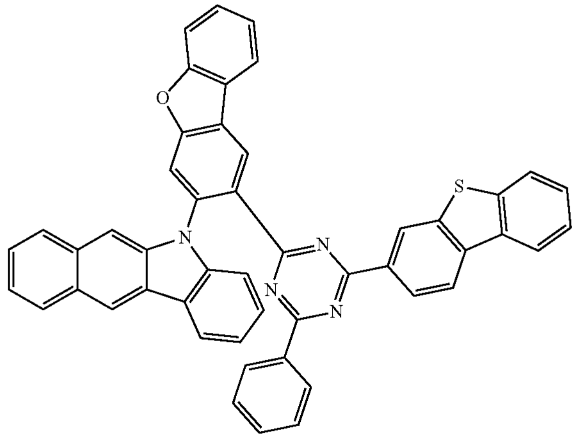
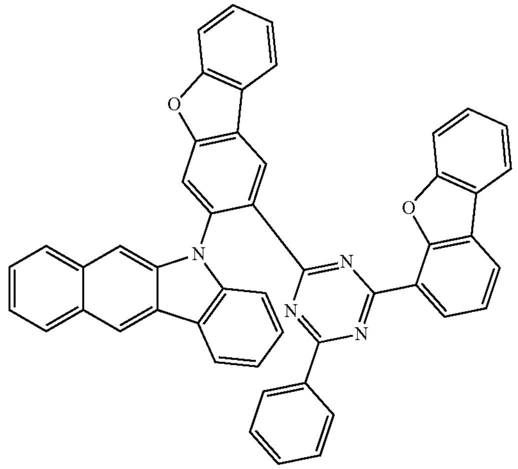
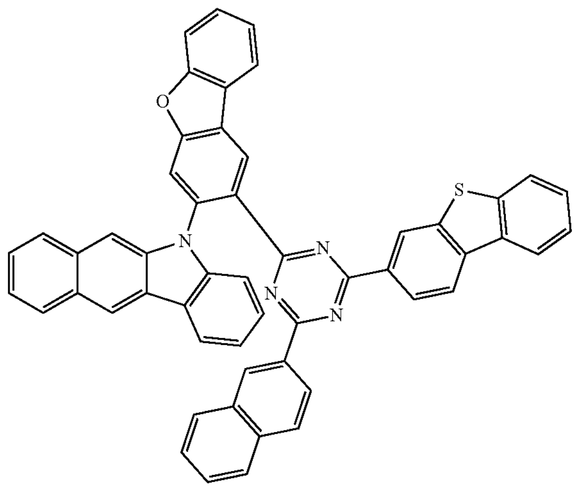
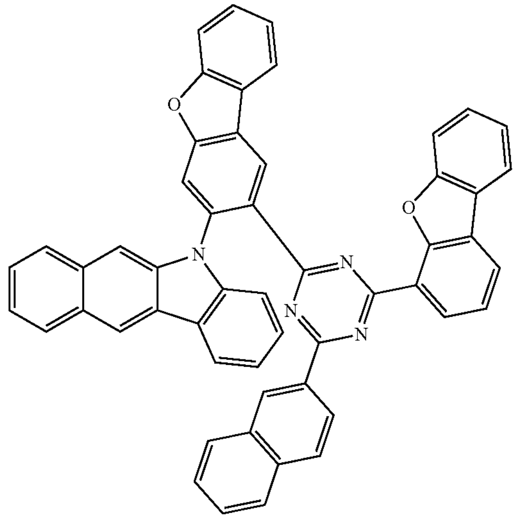
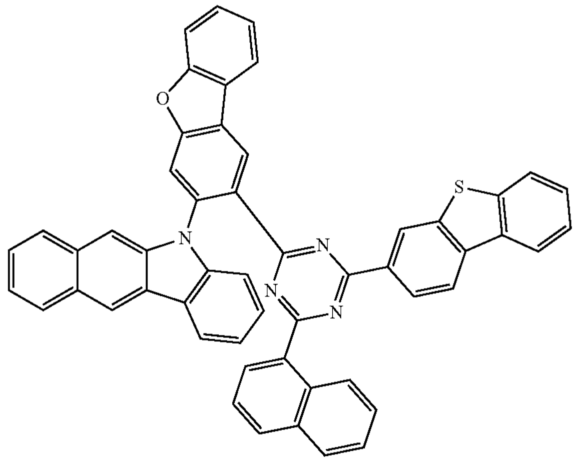
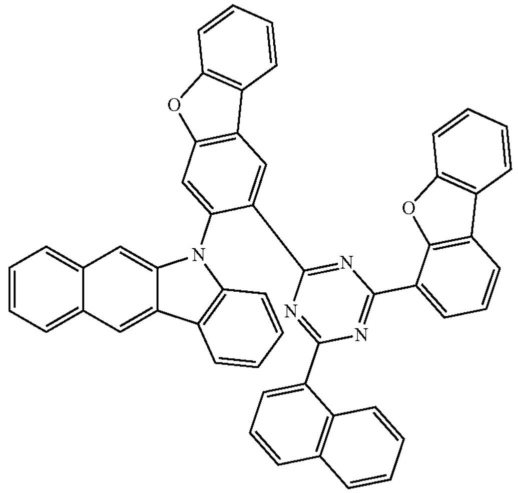
-continued -continued
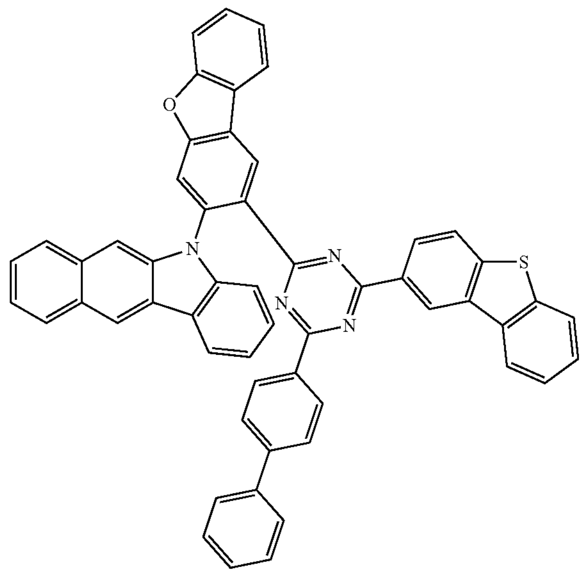
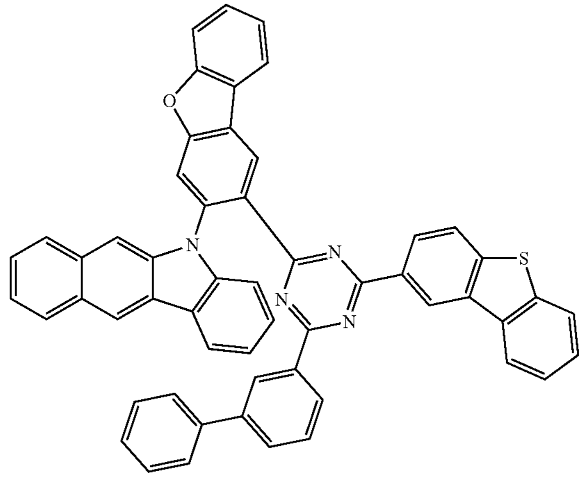
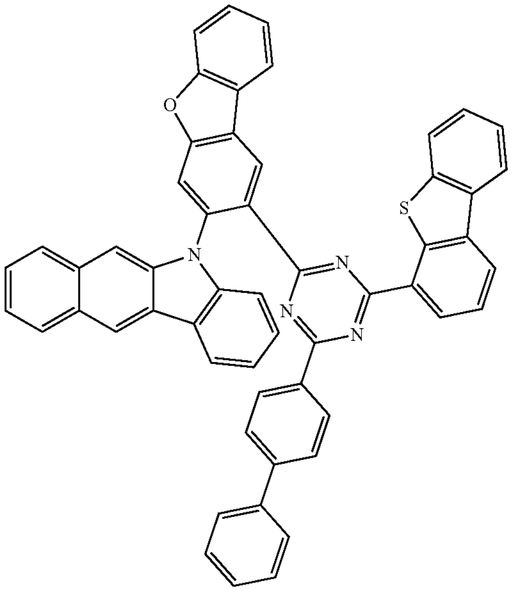
-continued
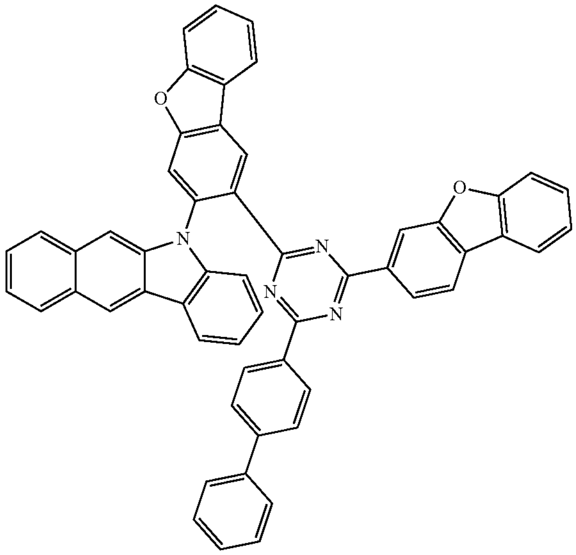
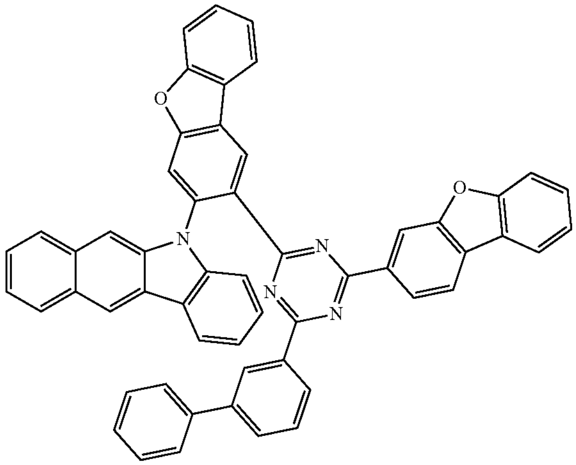
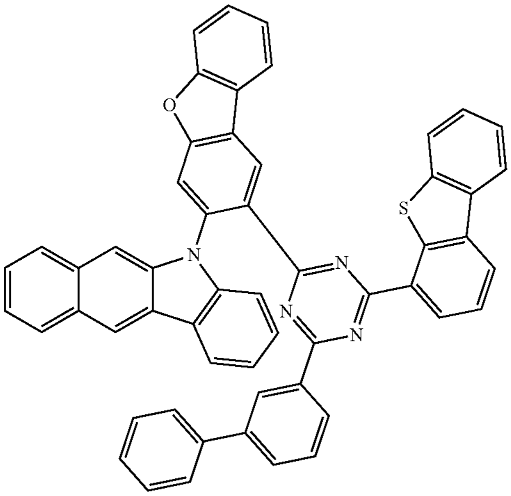

-continued
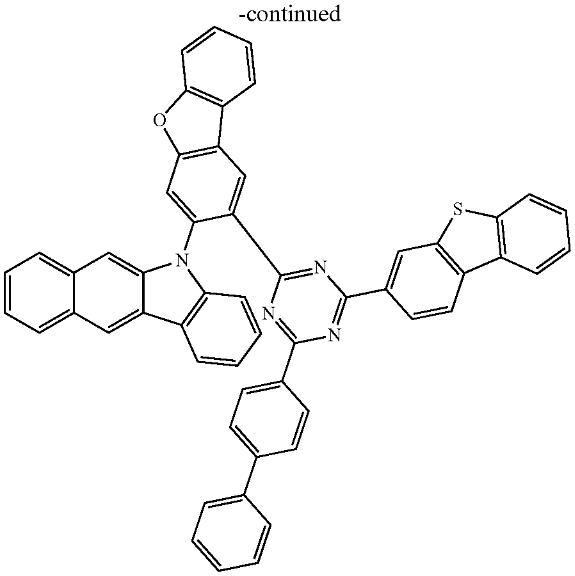
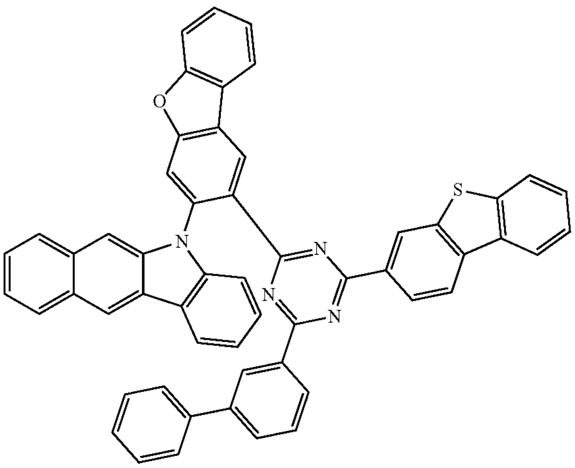
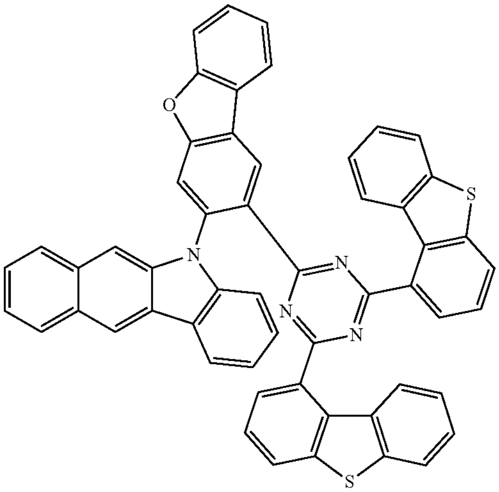
-continued
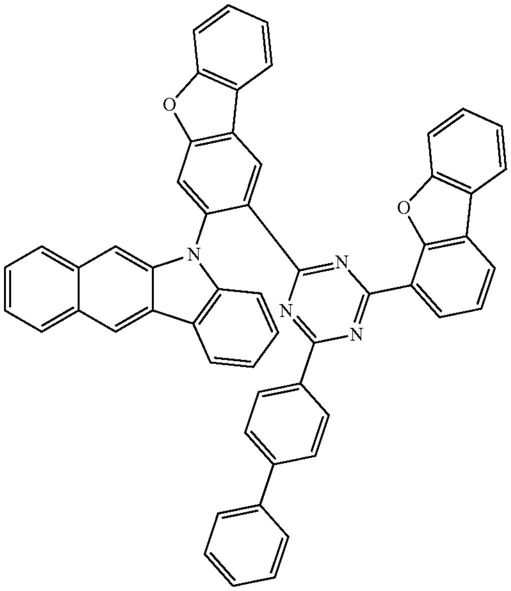
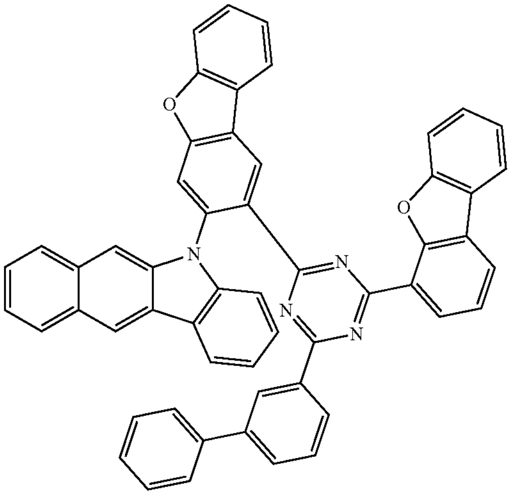
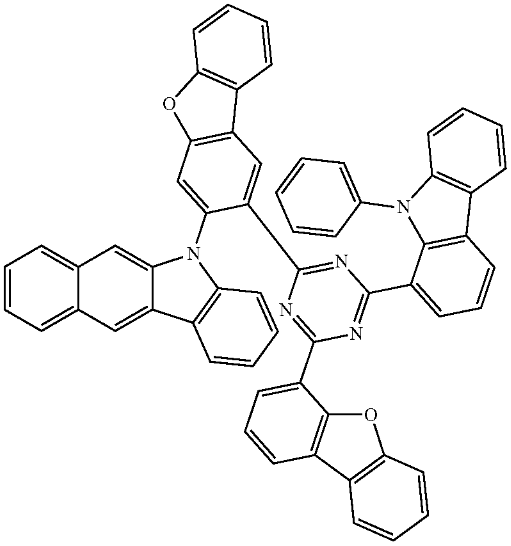

-continued
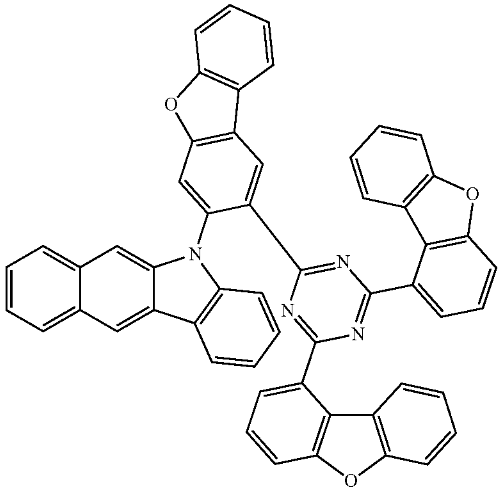
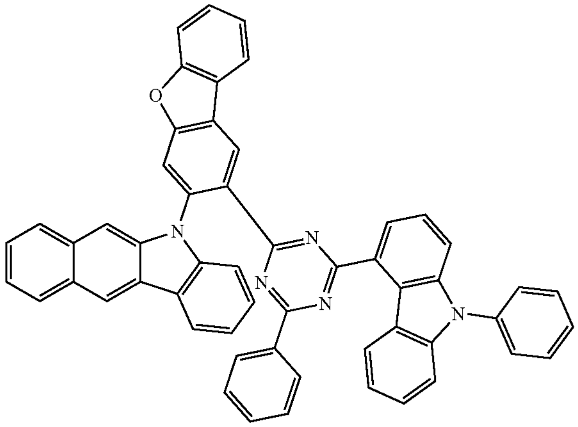
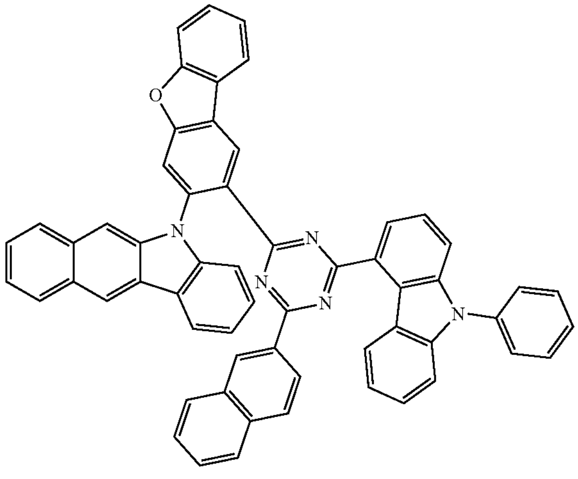
-continued
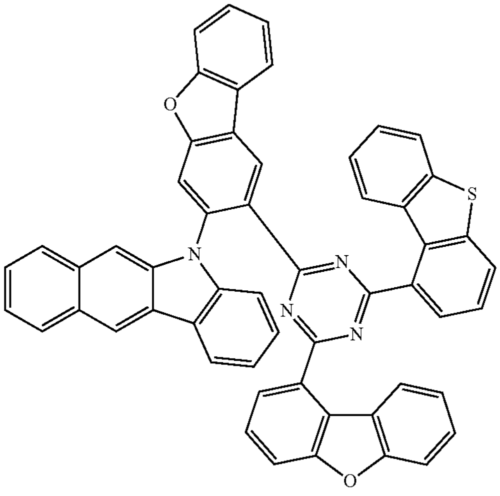
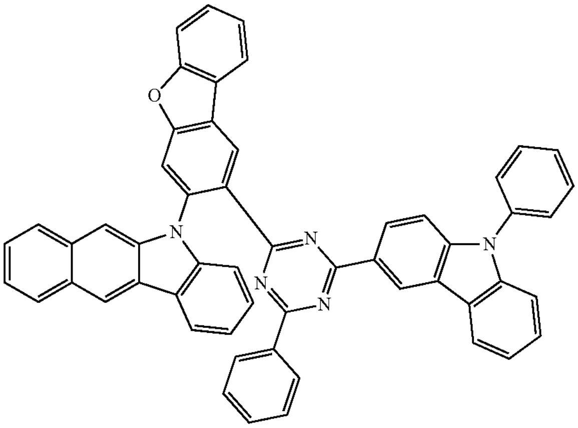
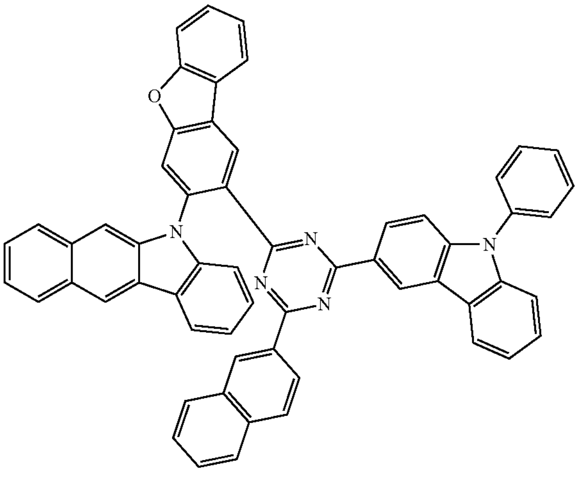

-continued
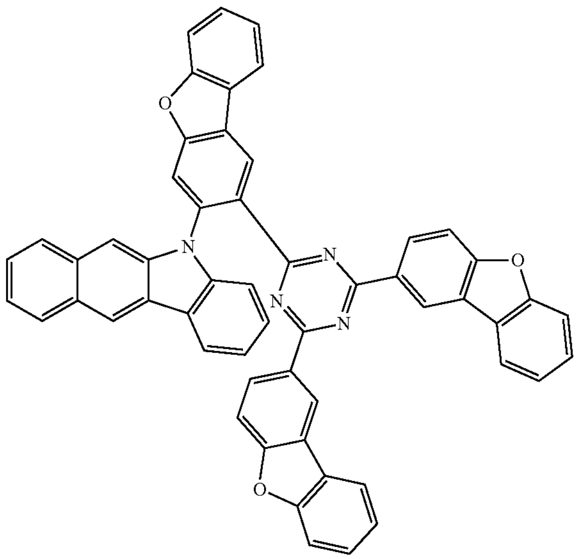
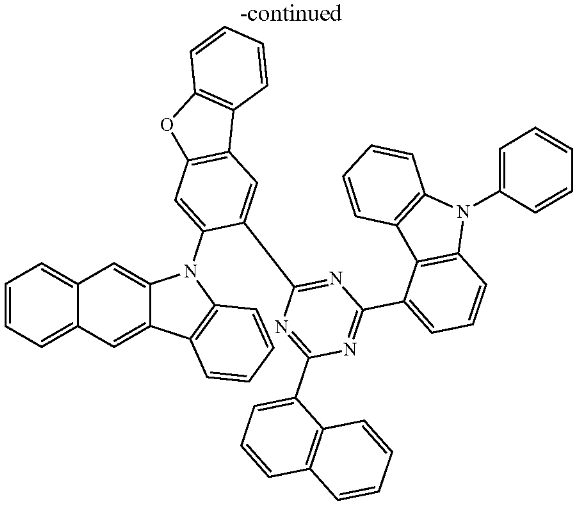
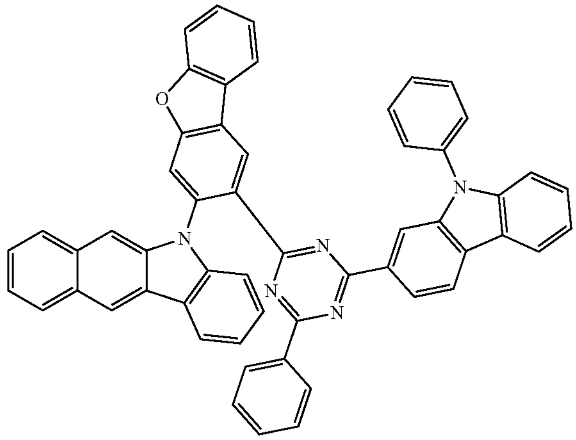
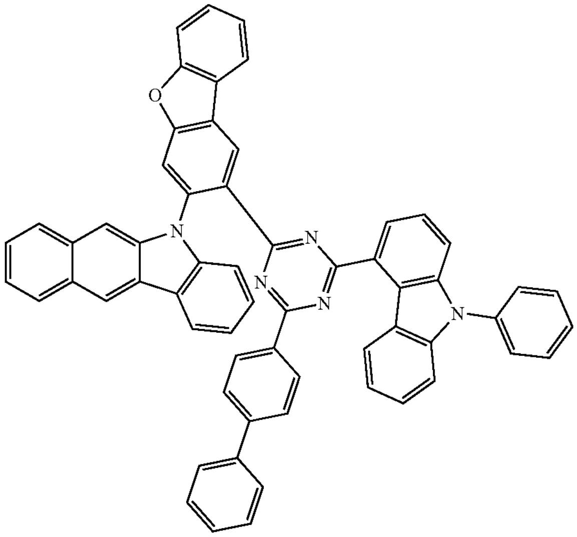
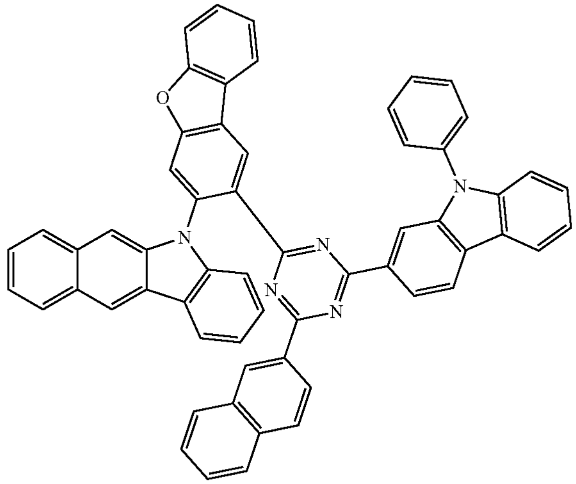
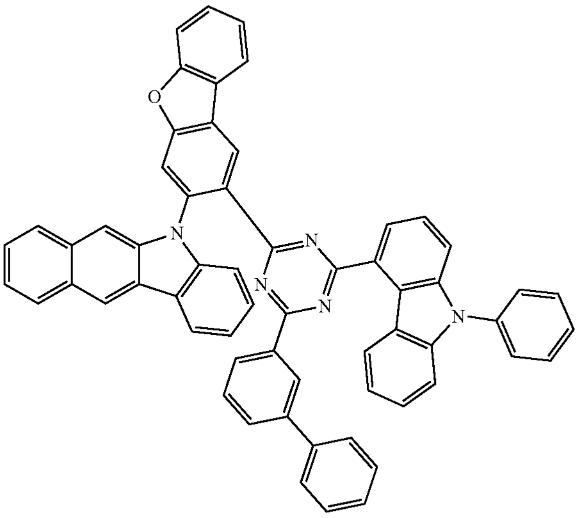

-continued
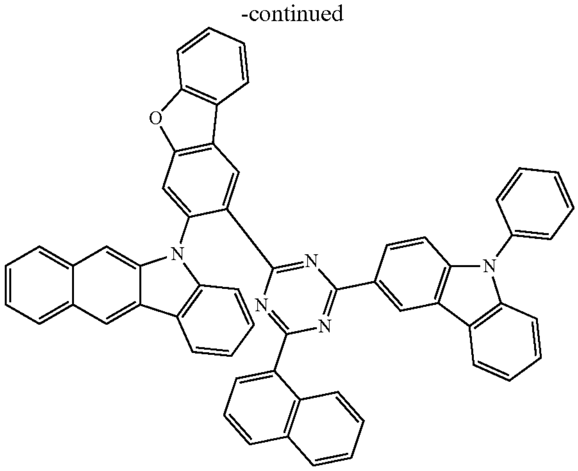
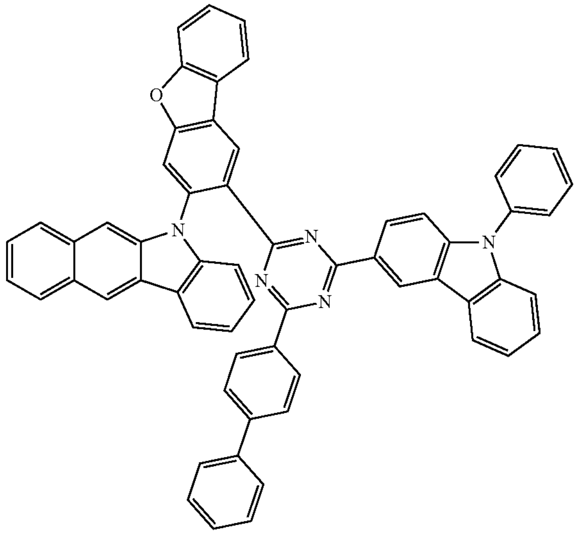
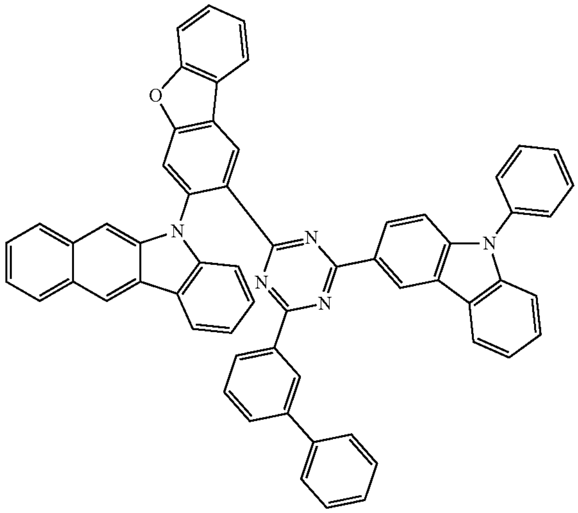
-continued
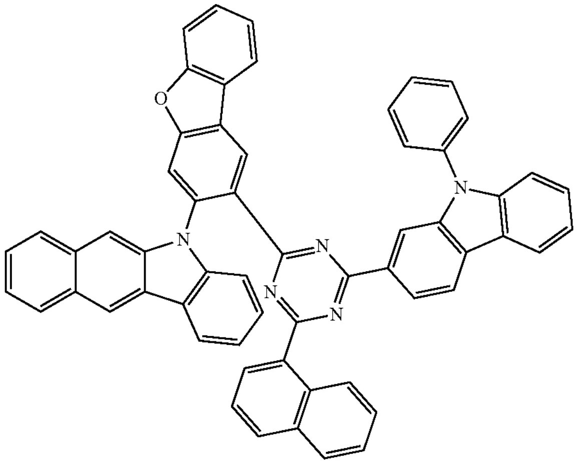
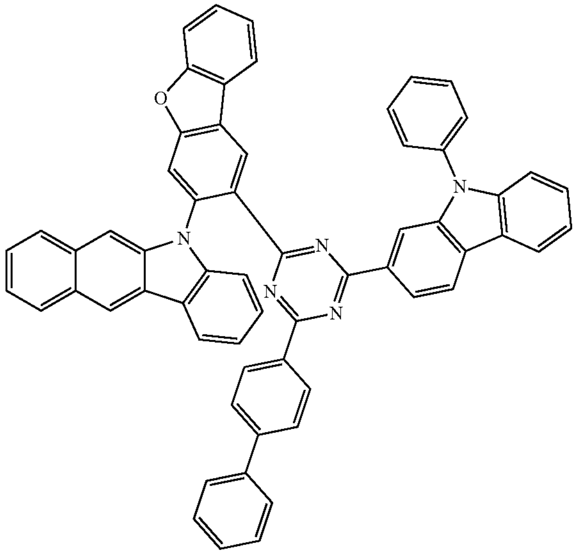
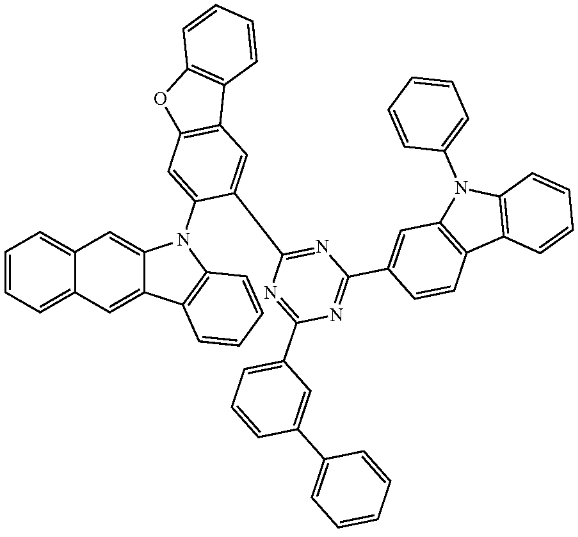

-continued
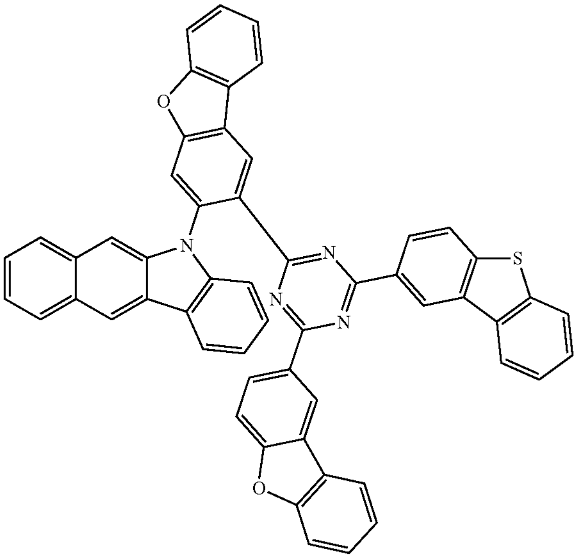
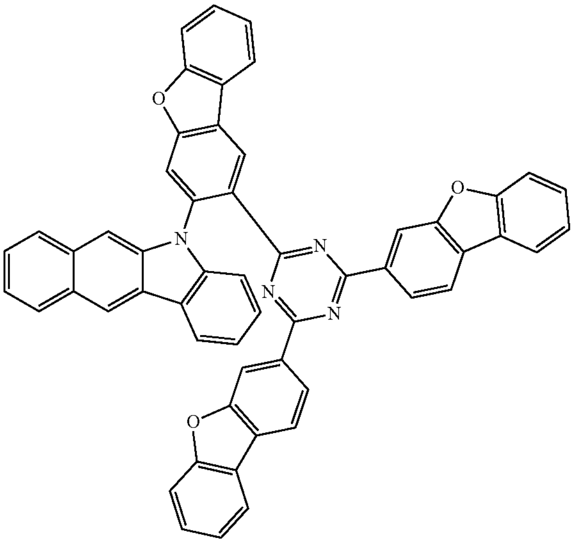
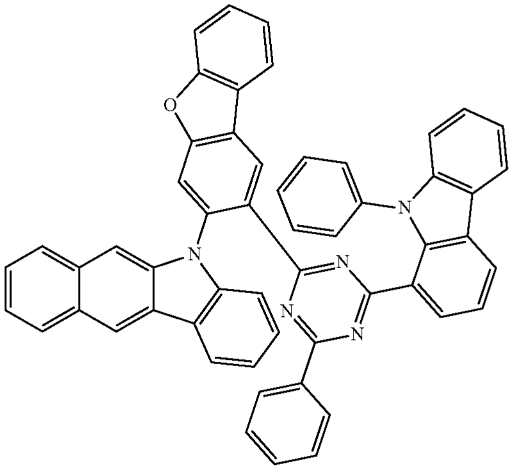
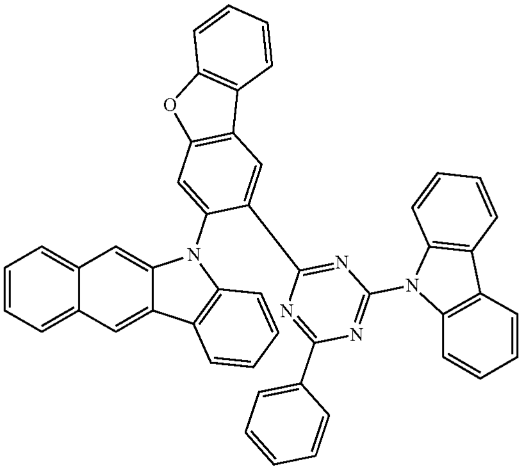
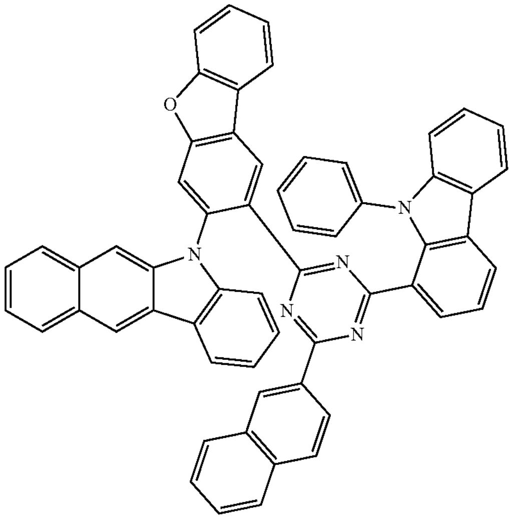
-continued
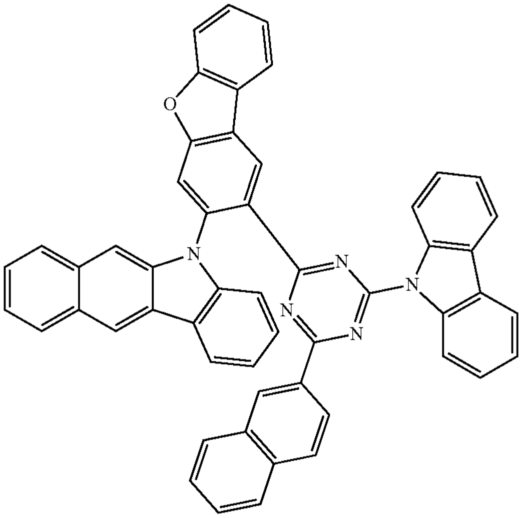

-continued
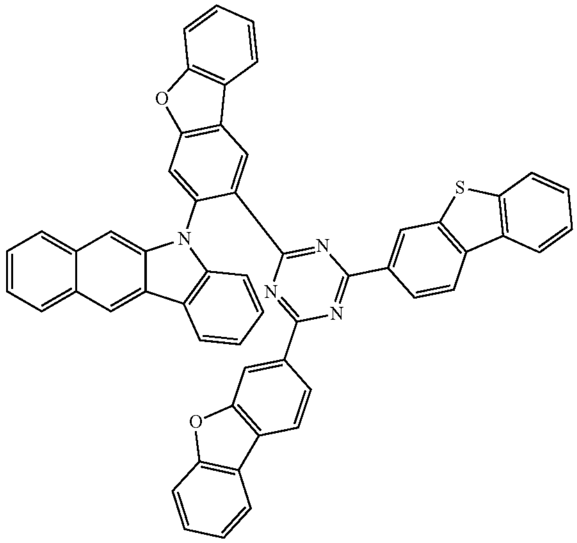
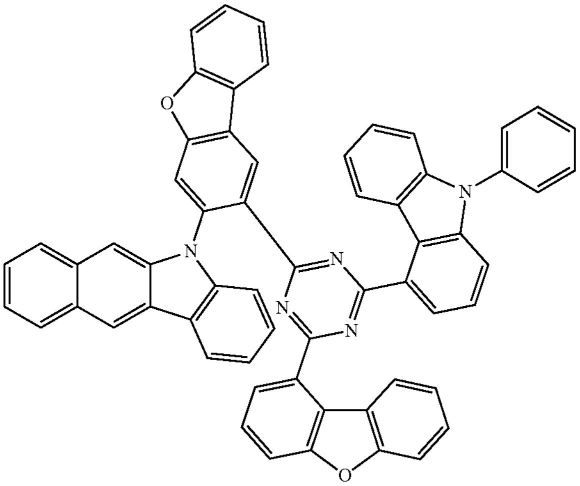
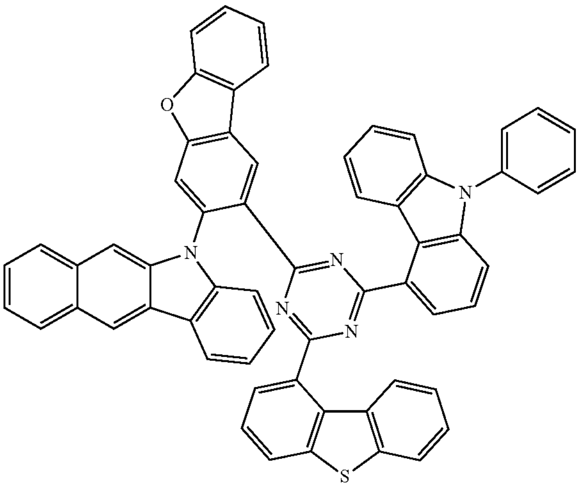
-continued
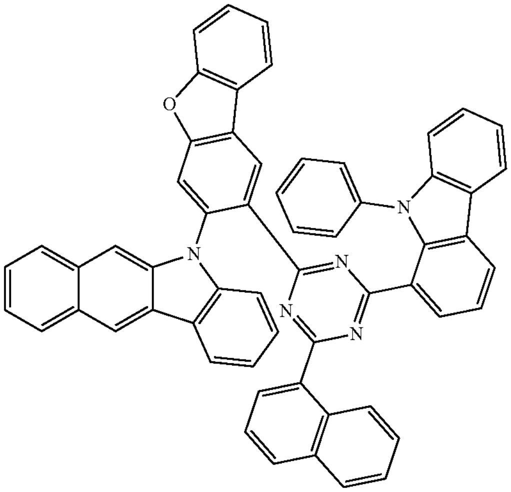
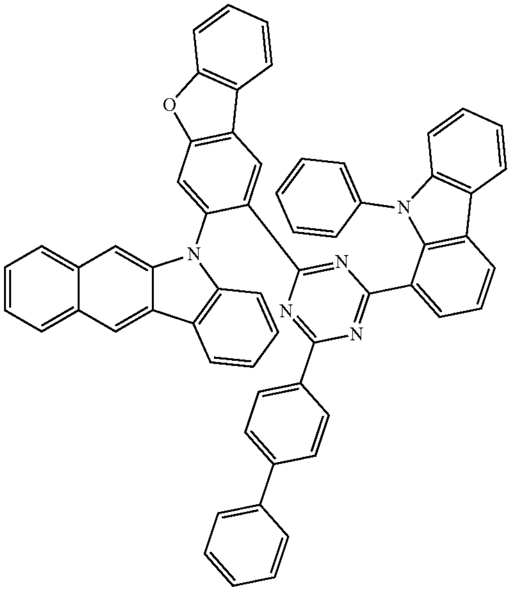
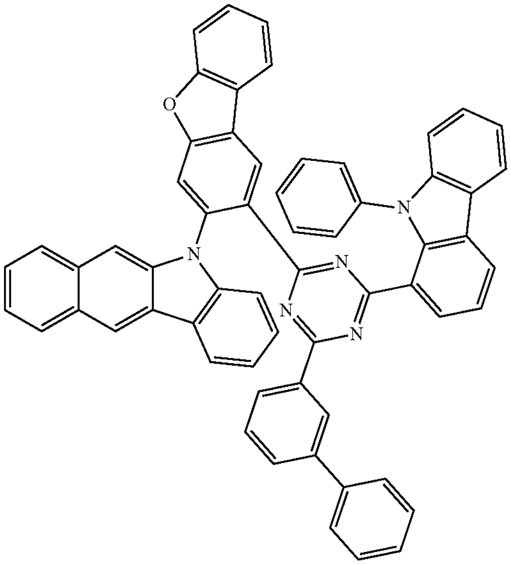

-continued
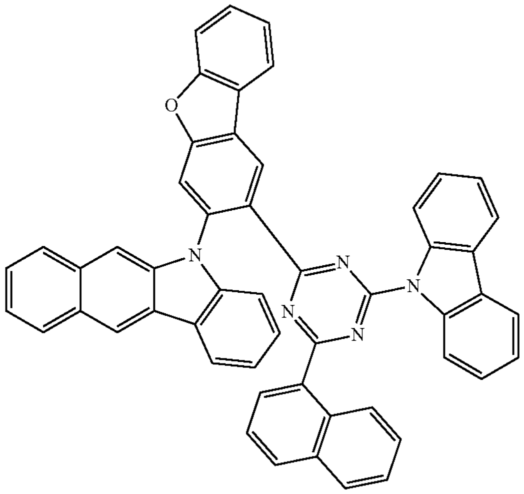
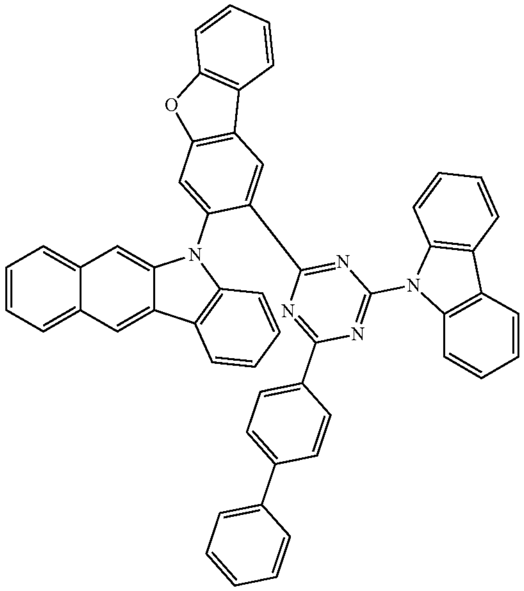
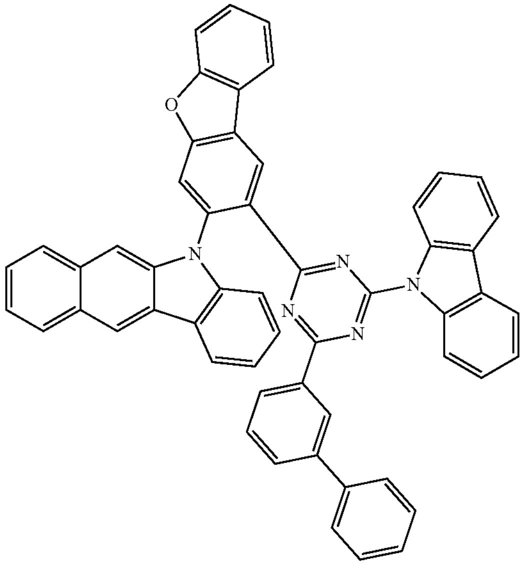
-continued
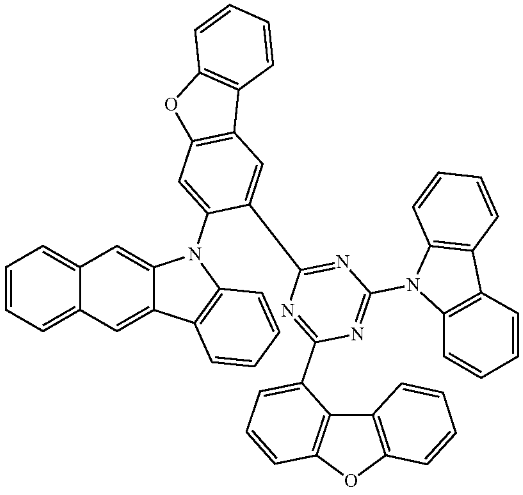
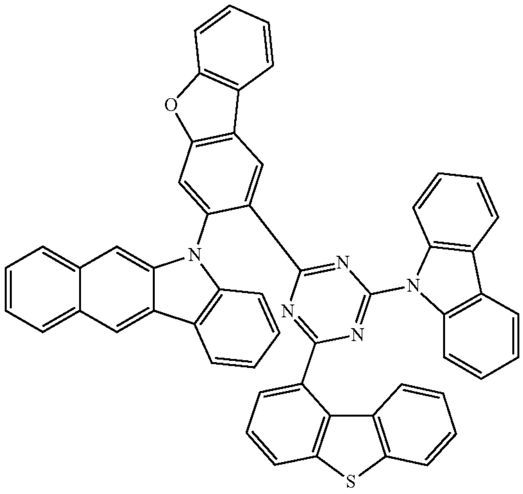
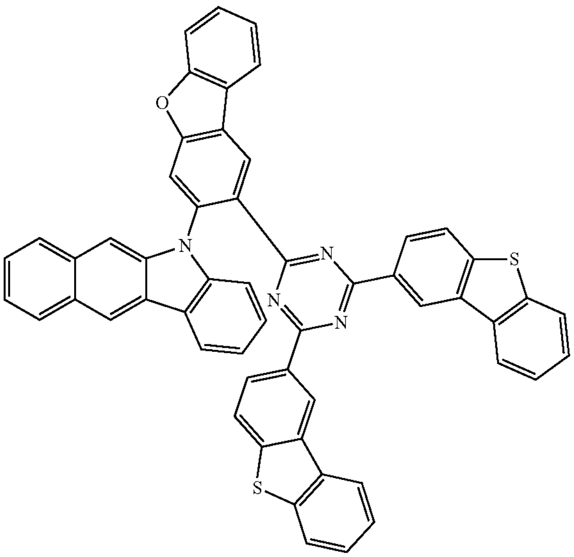

-continued
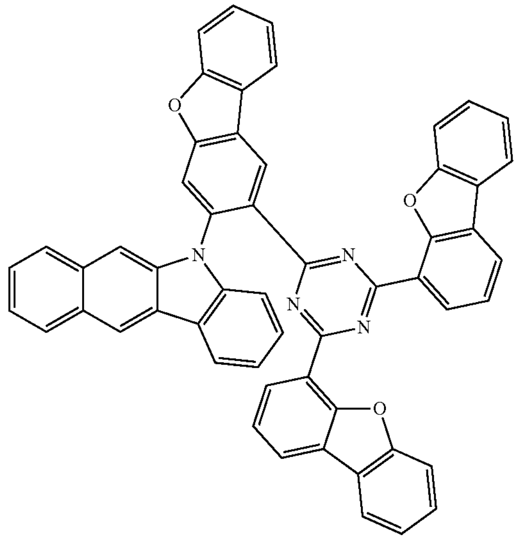
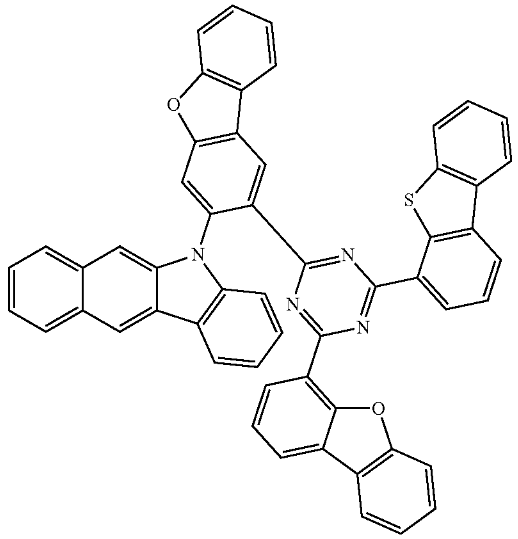
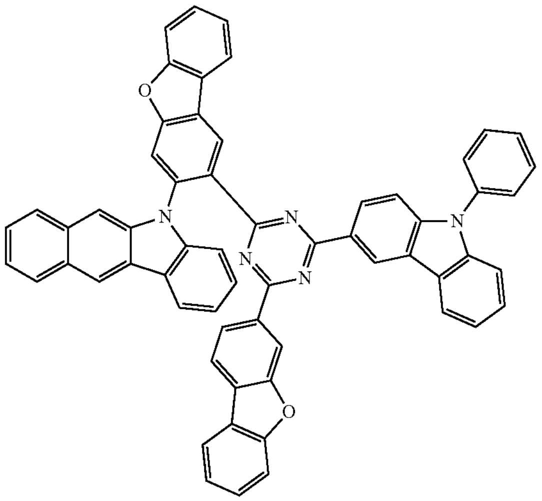
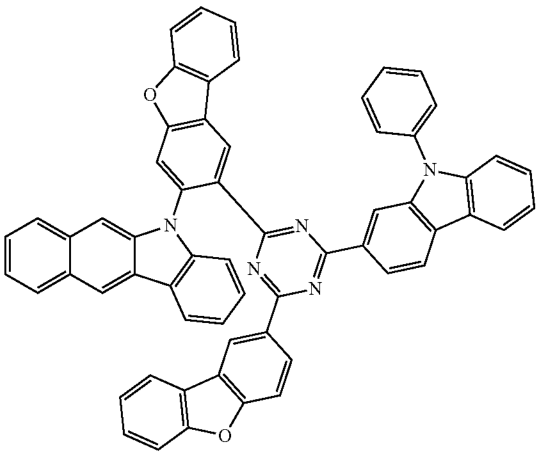
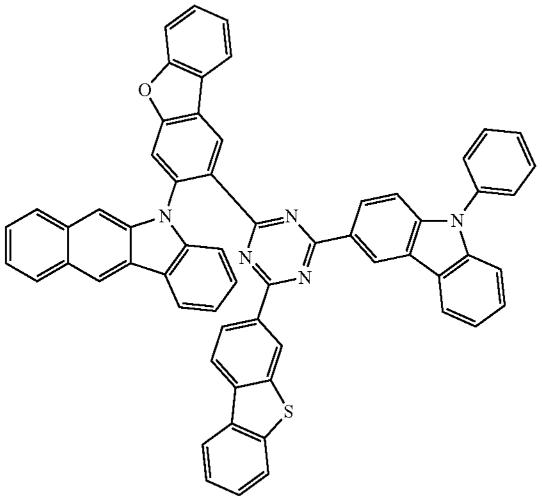
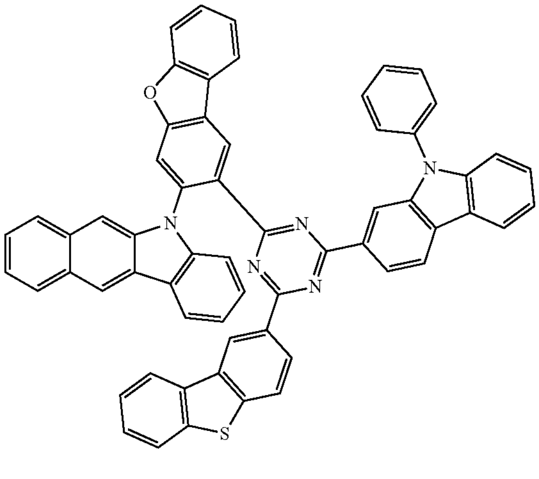

-continued
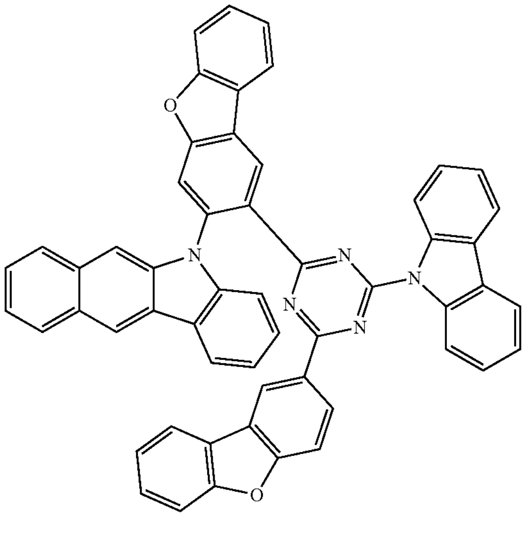
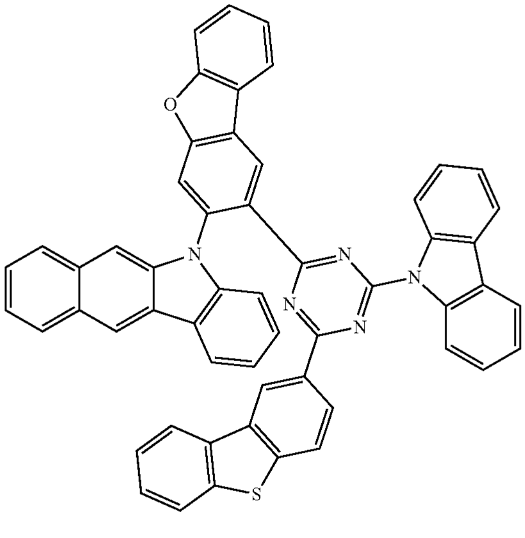
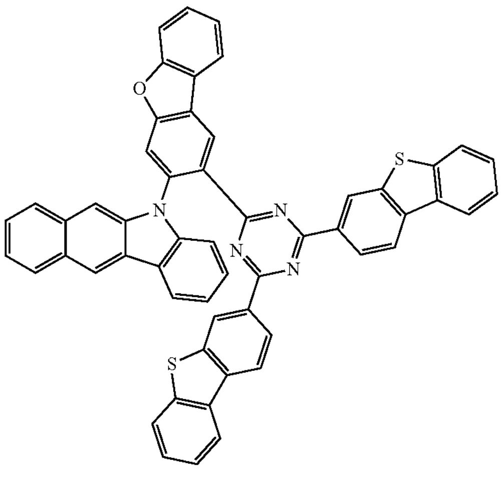
-continued
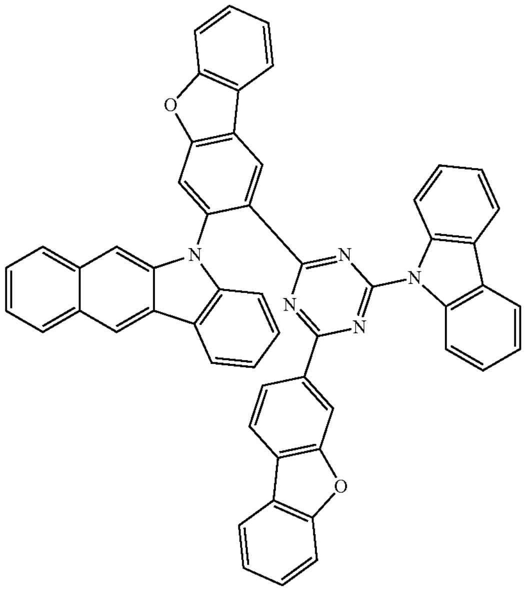
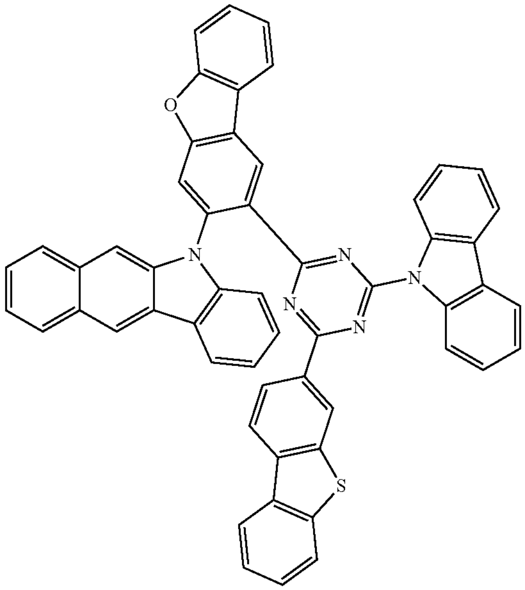
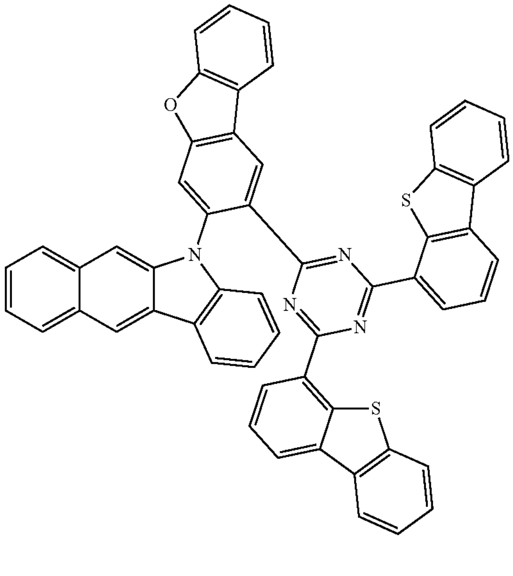

1812
-continued
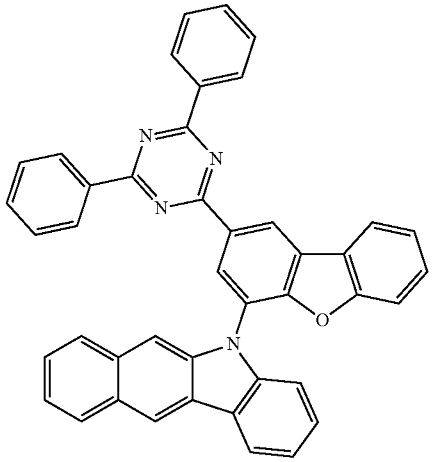
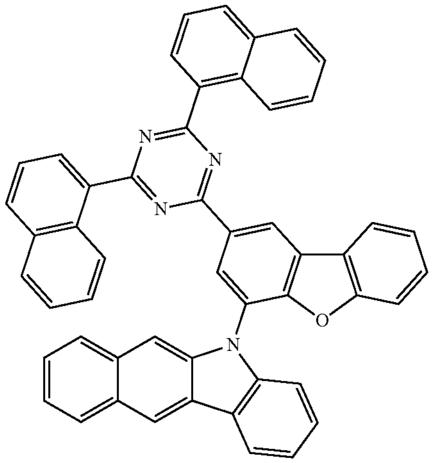
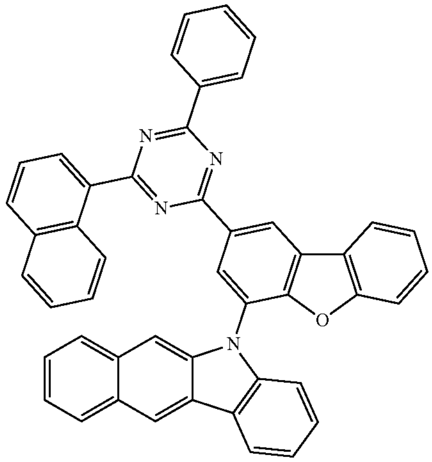
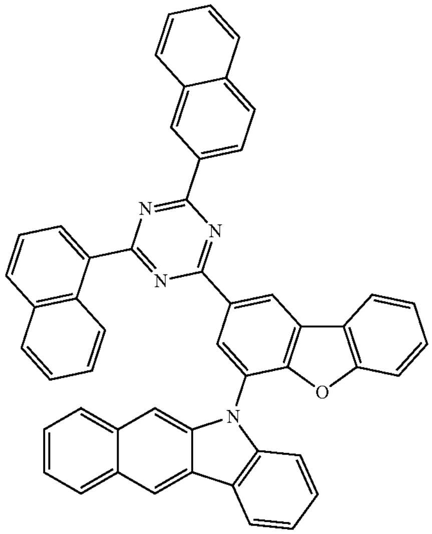
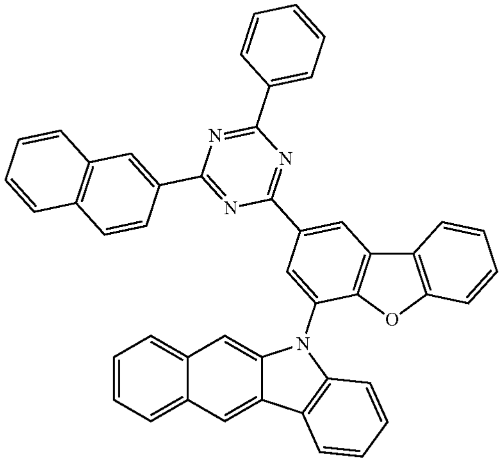
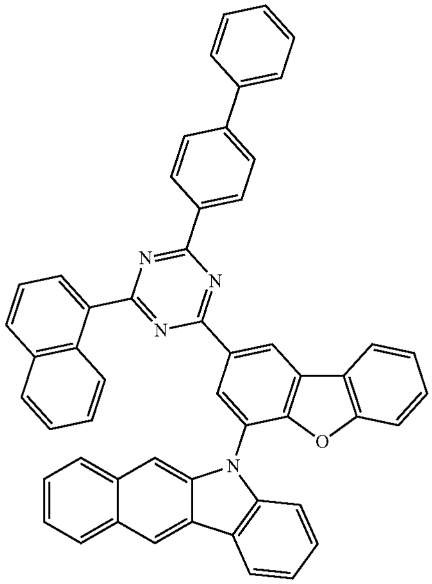

-continued
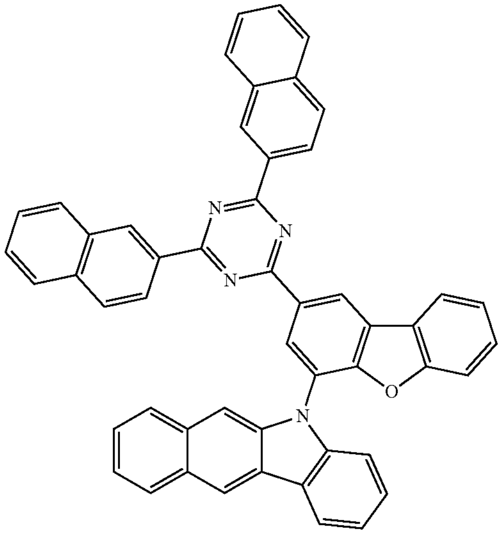
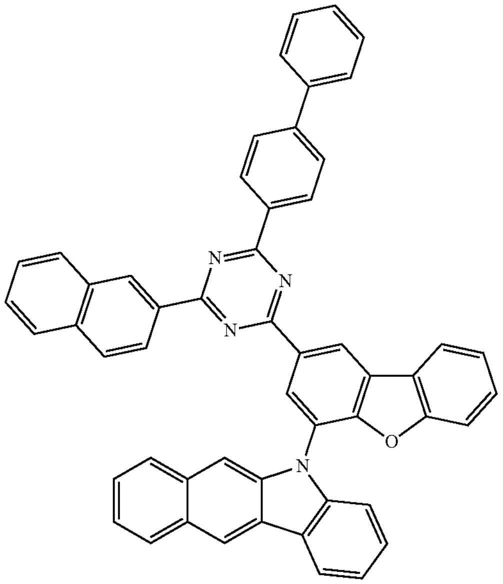
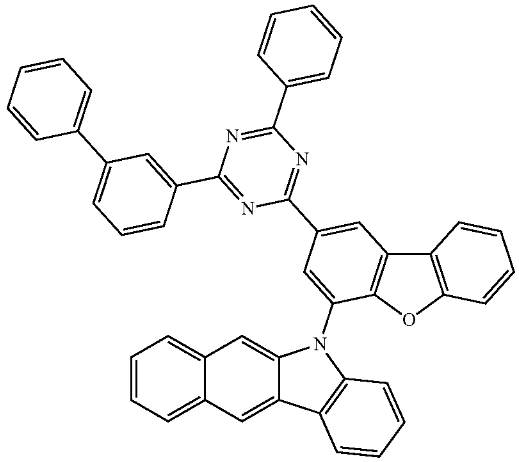
-continued
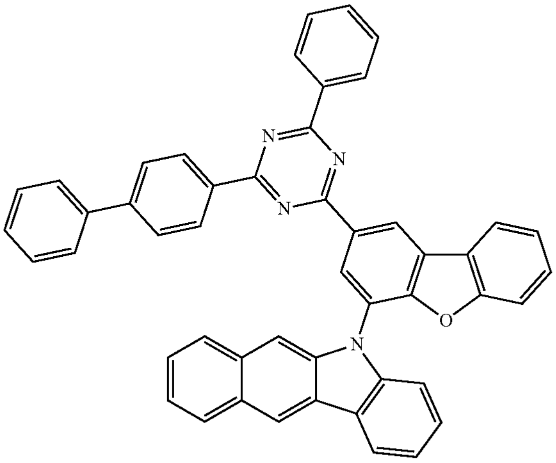
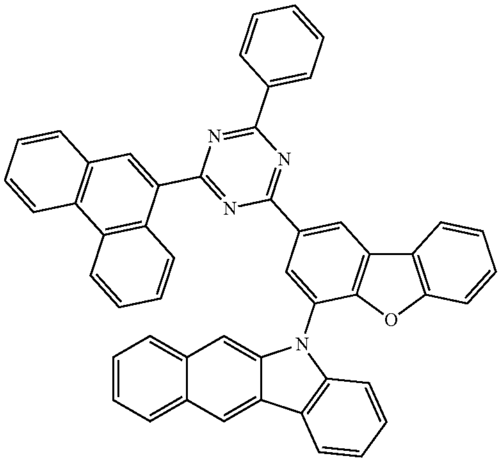
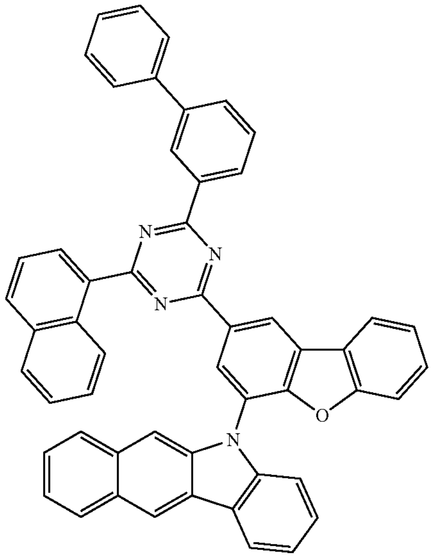

-continued
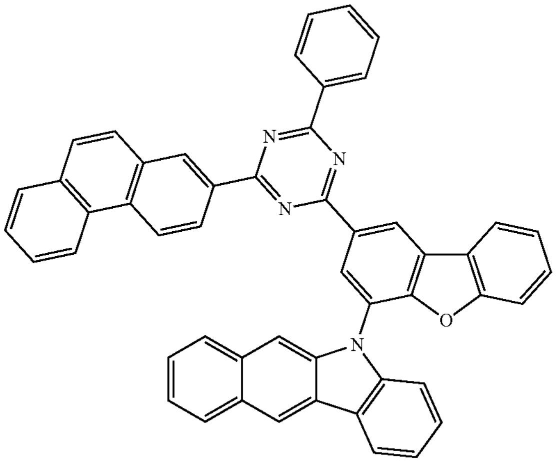
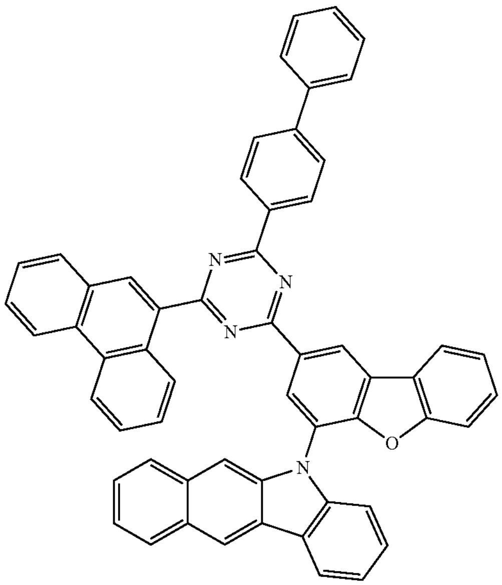
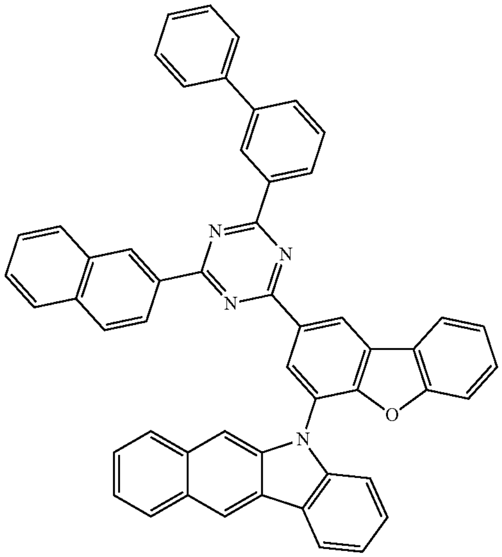
-continued
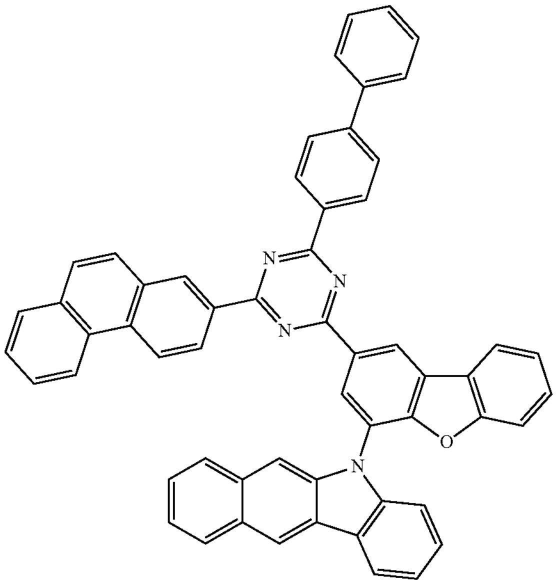
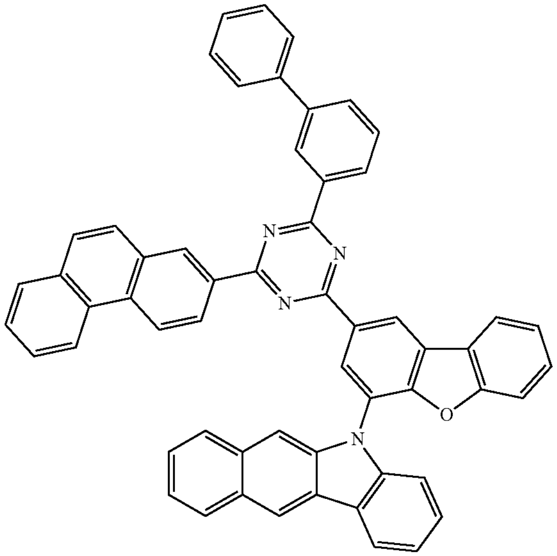
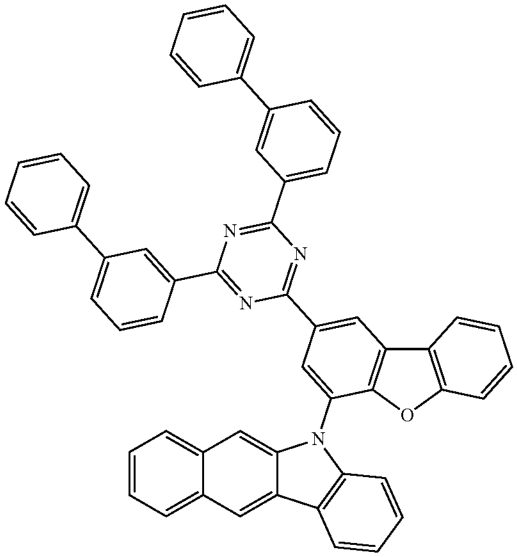

-continued
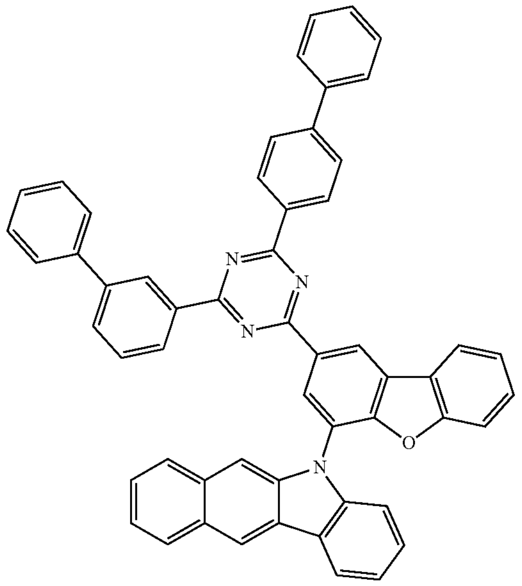
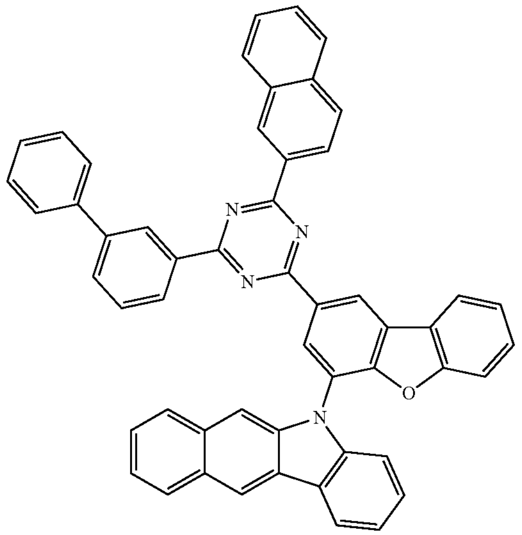
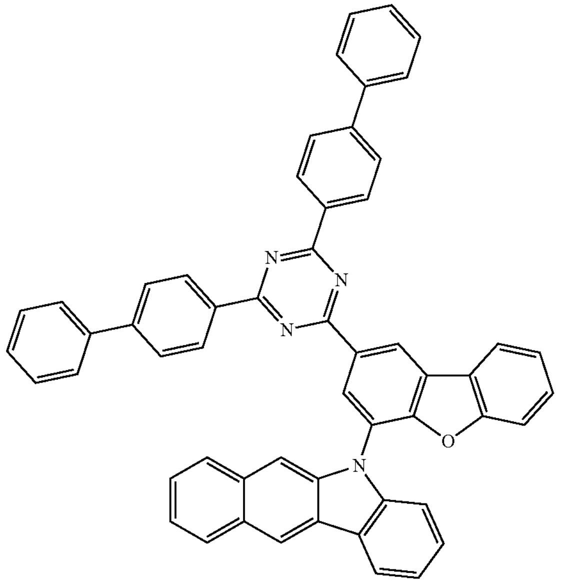
-continued
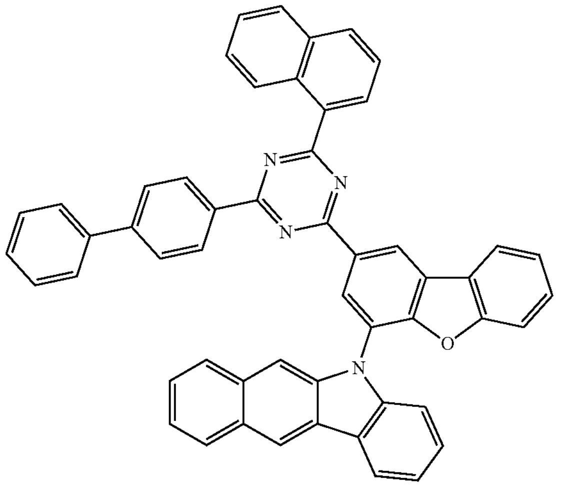
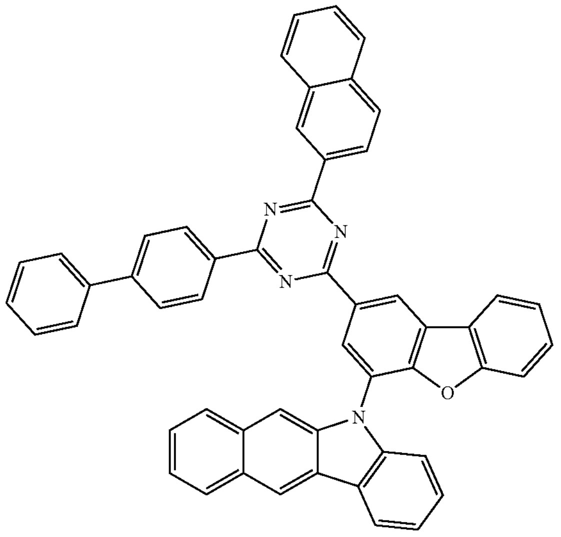
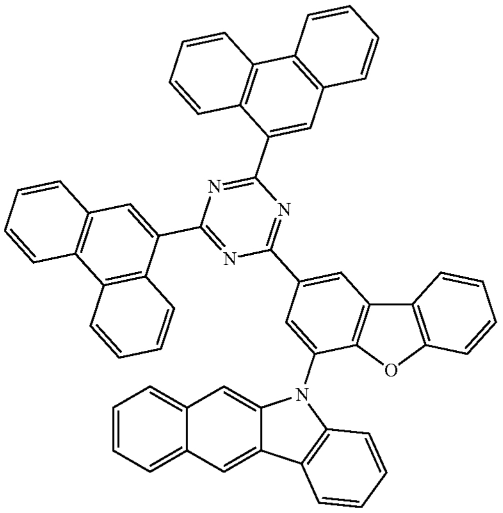

-continued
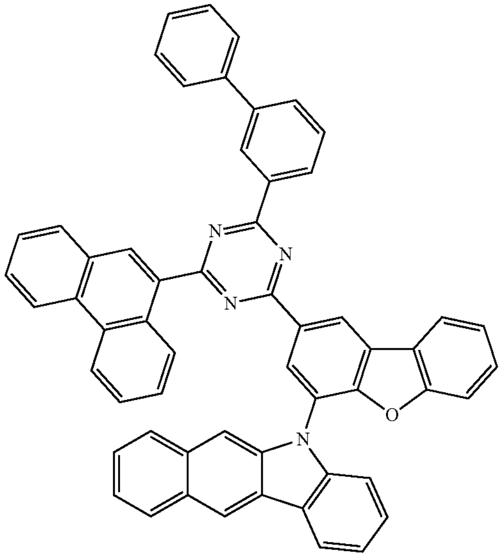
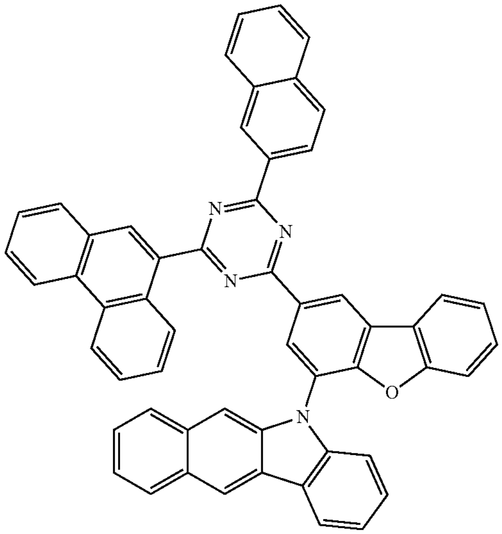
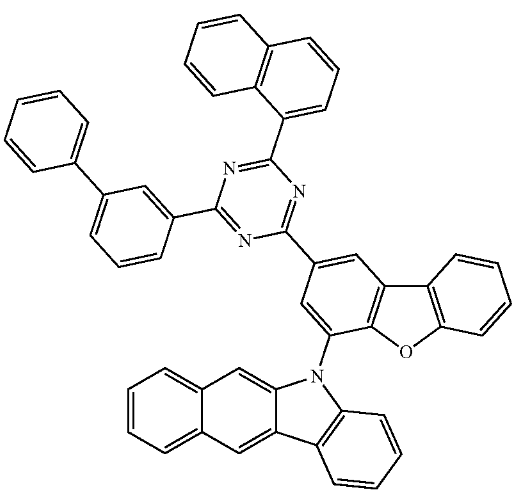
-continued
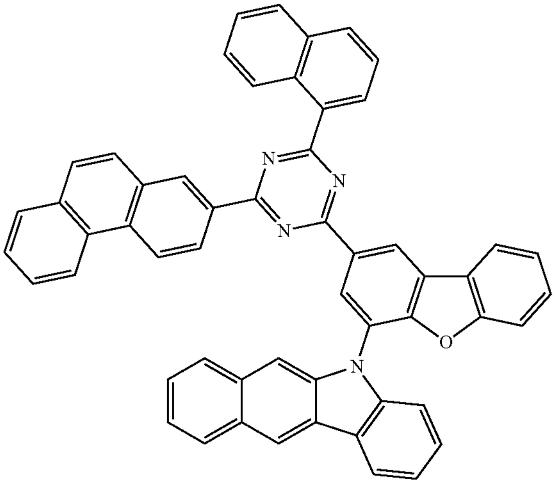
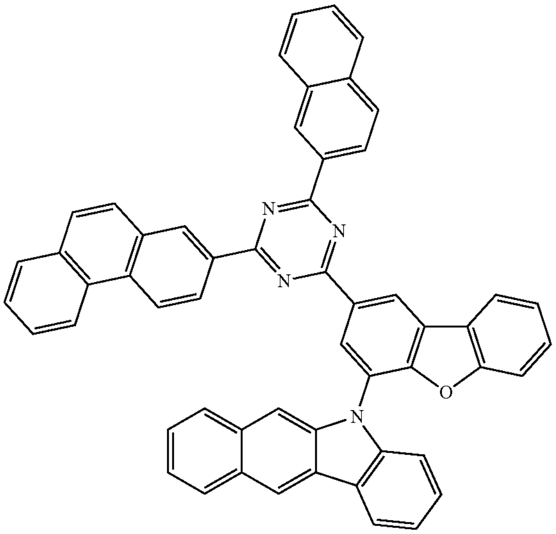
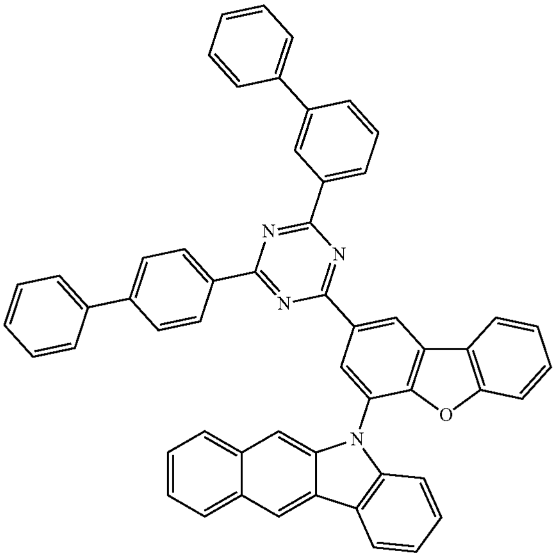

-continued
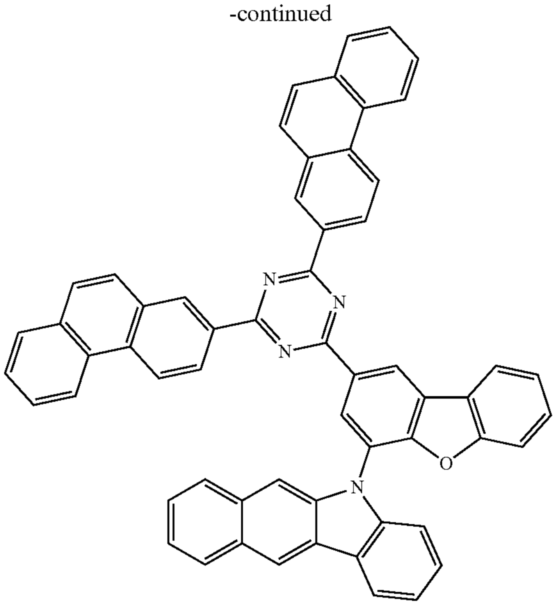
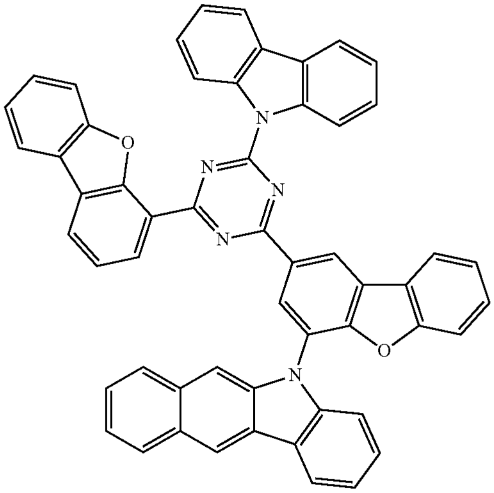
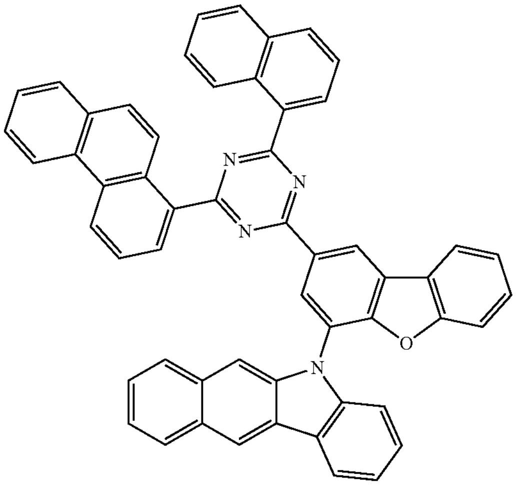
-continued
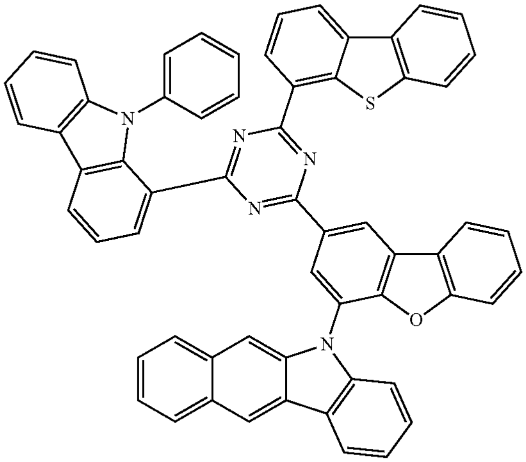
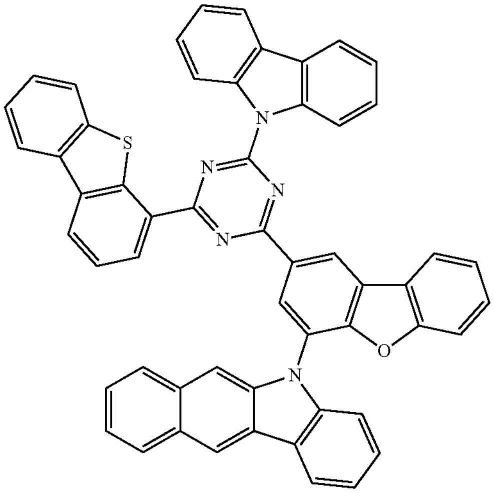
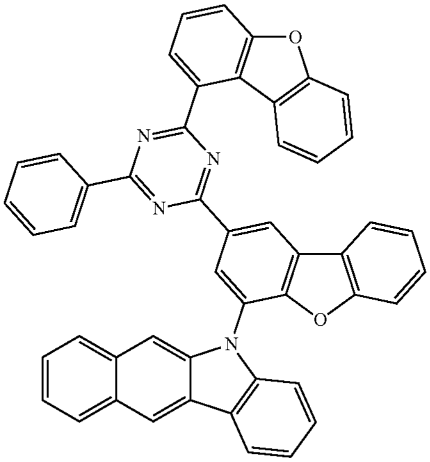

-continued
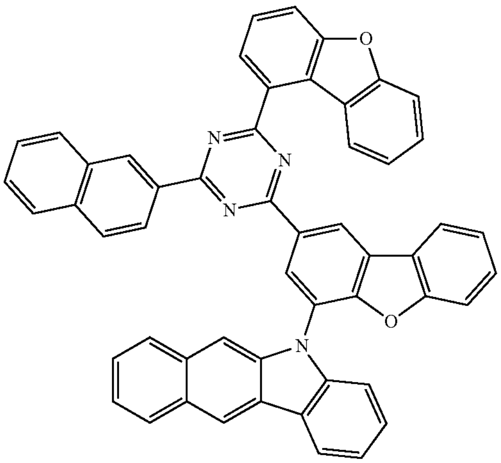
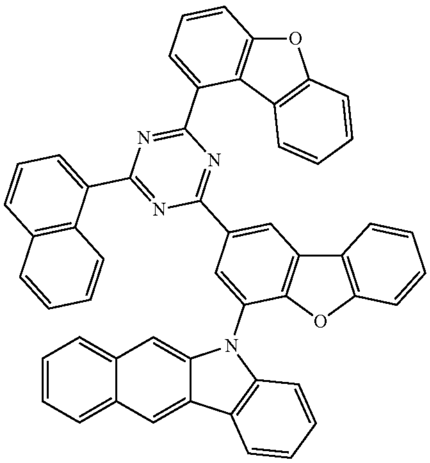
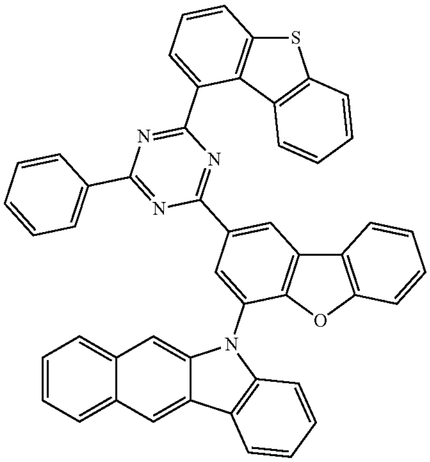
-continued
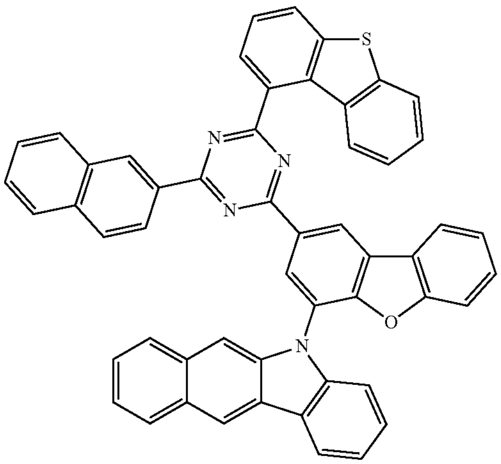
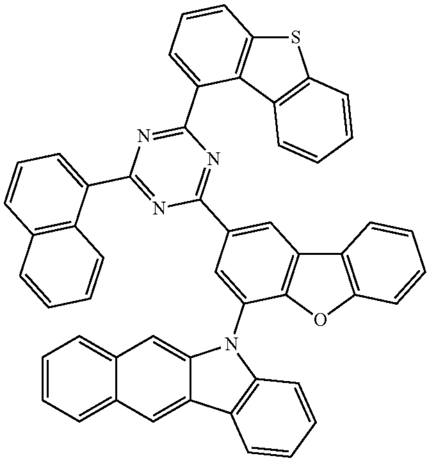
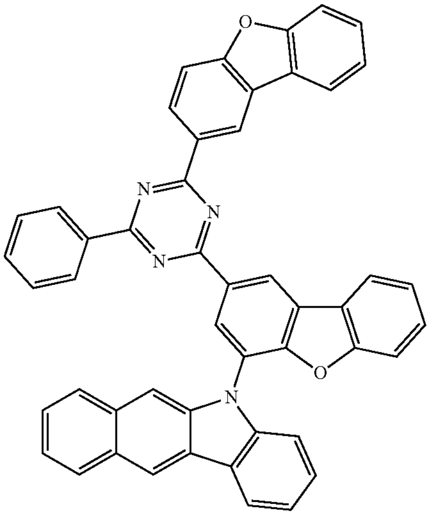

-continued
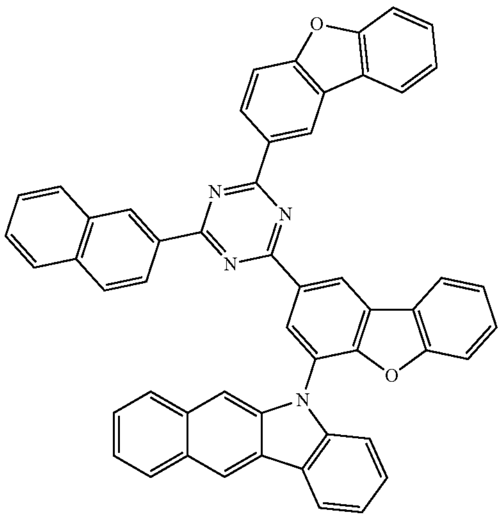
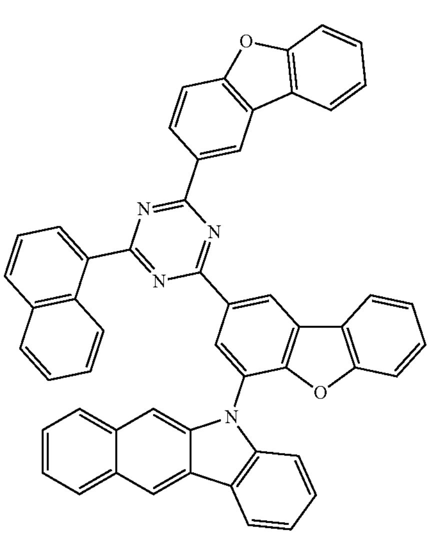
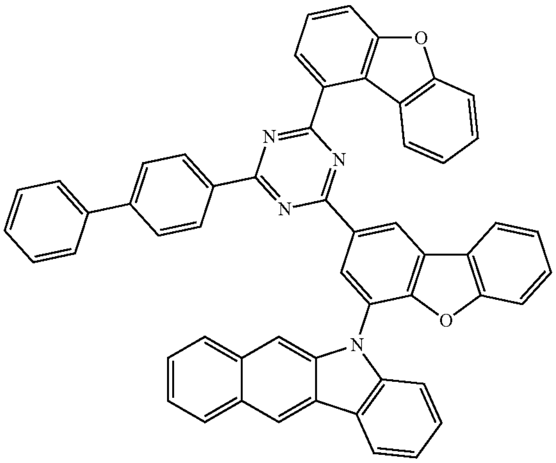
-continued
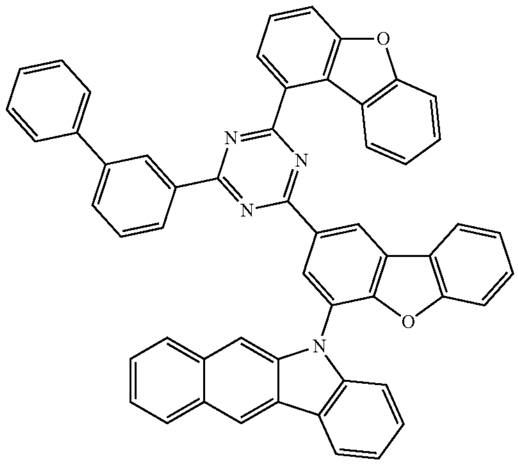
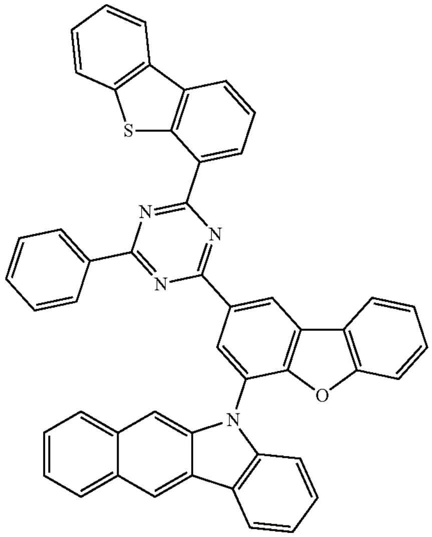
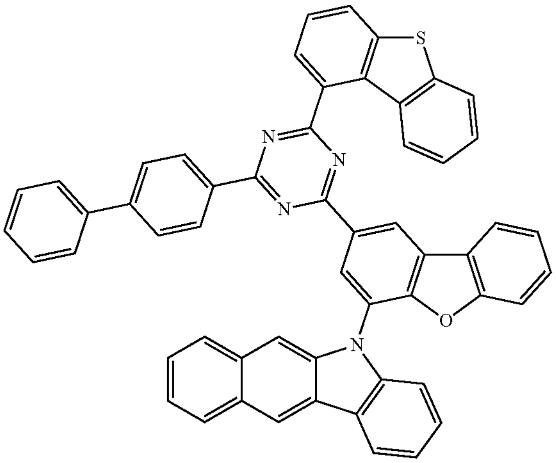

-continued
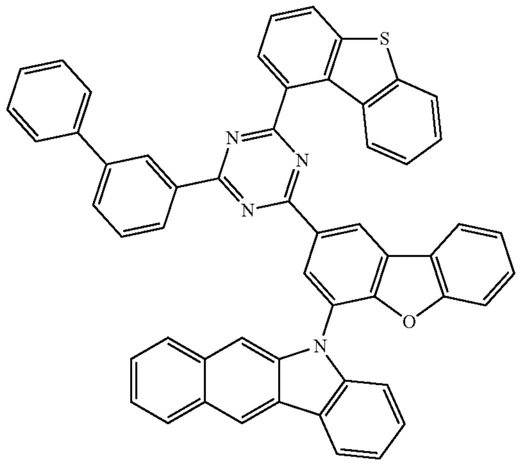
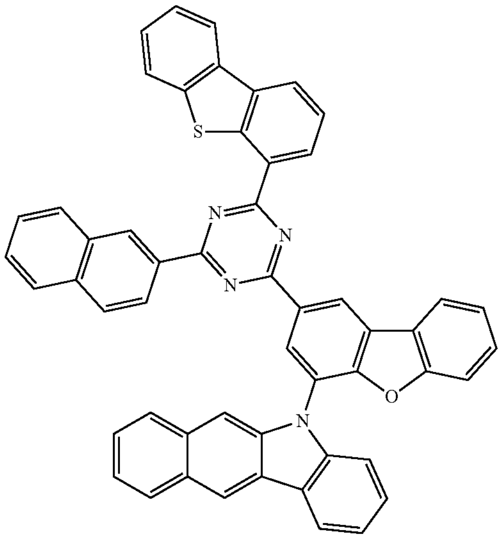
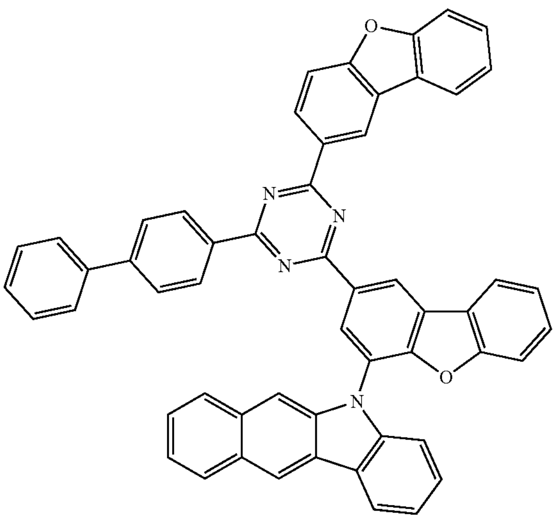
-continued
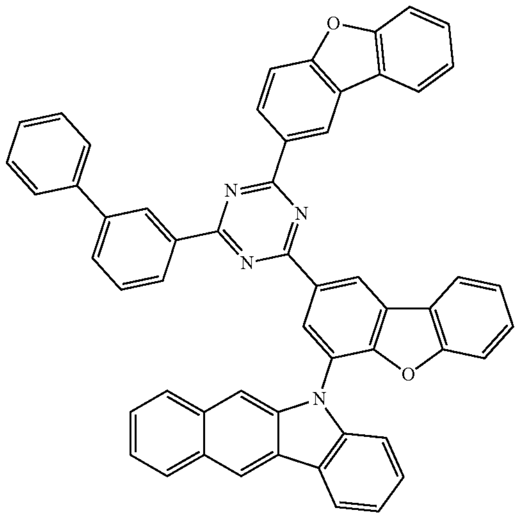
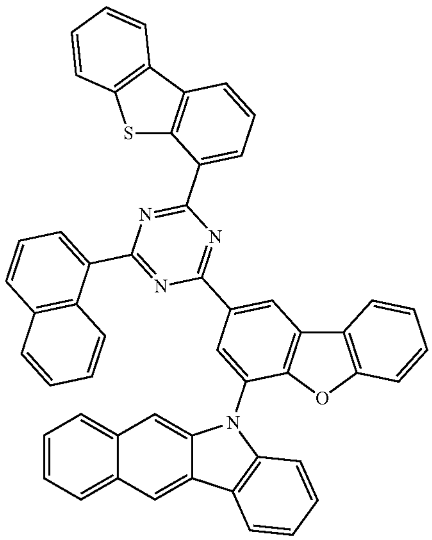
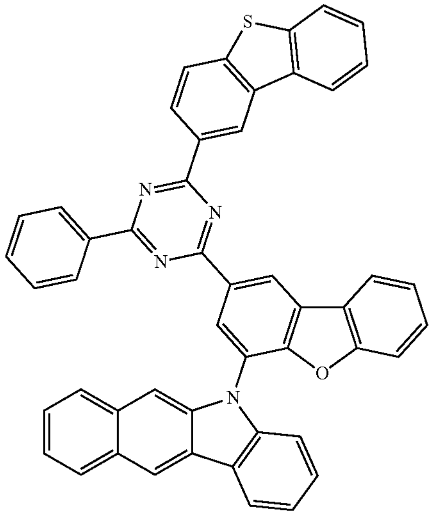

-continued
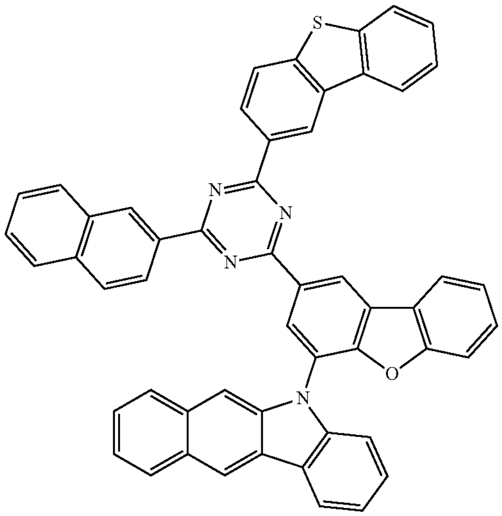
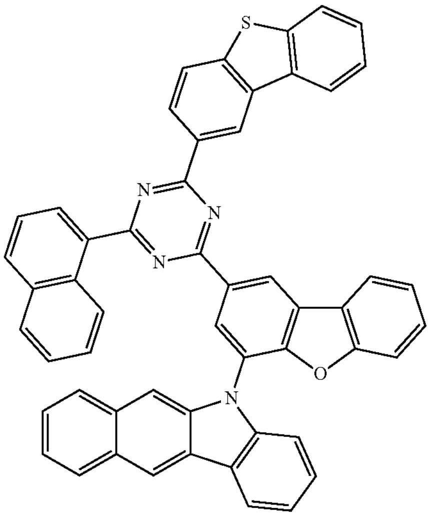
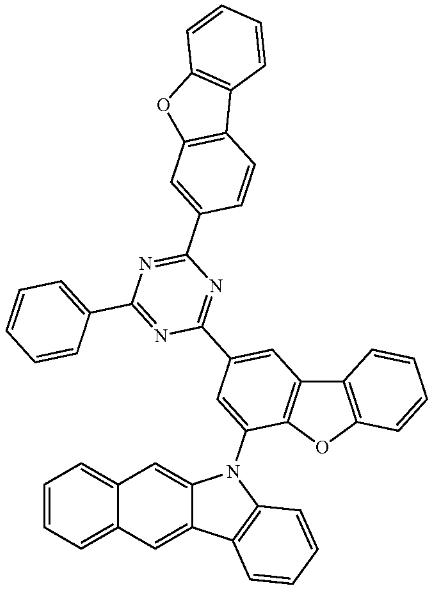
-continued
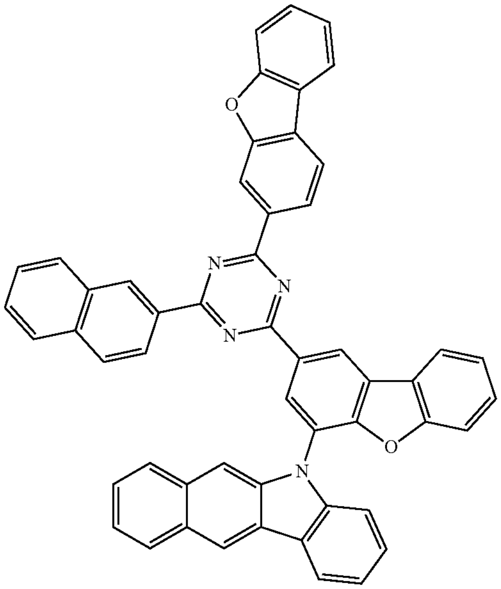
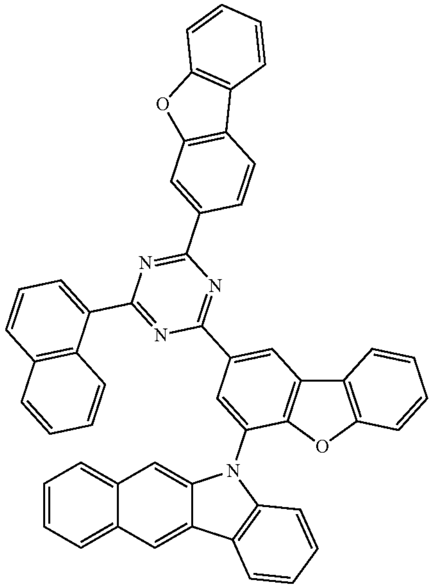

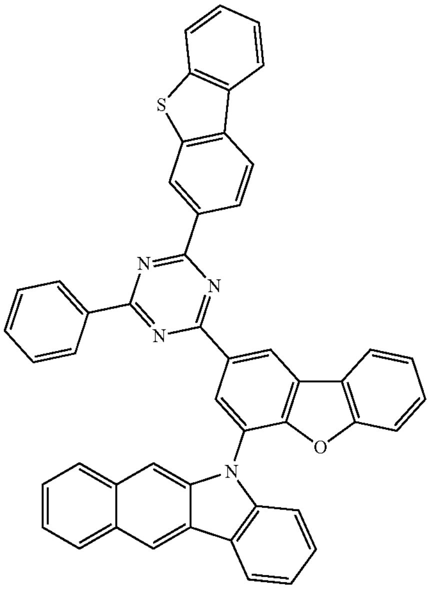
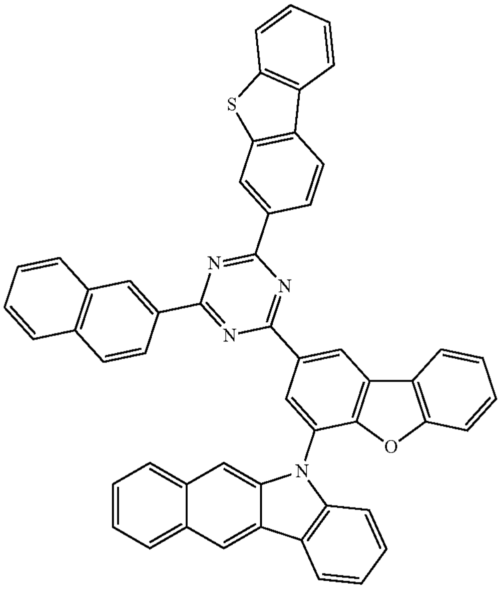
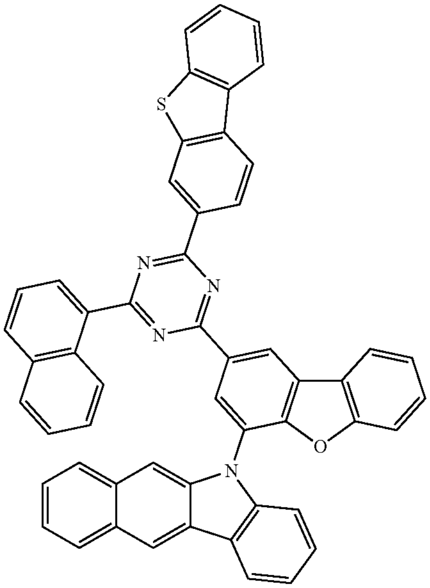
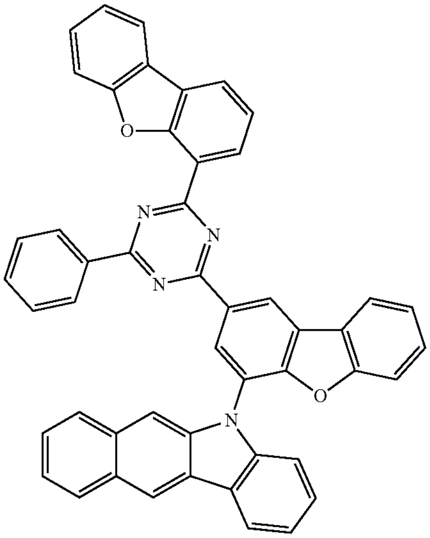
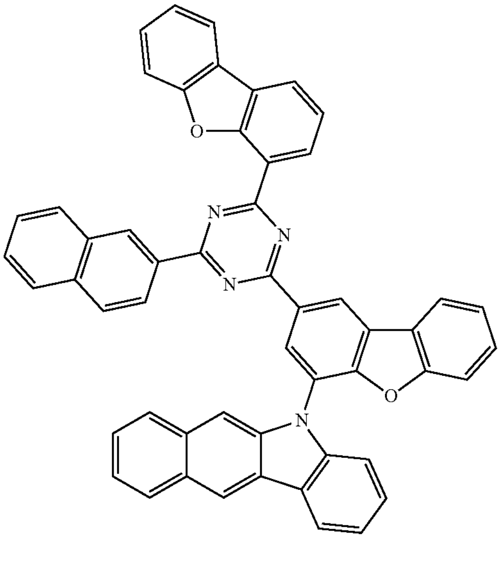

-continued
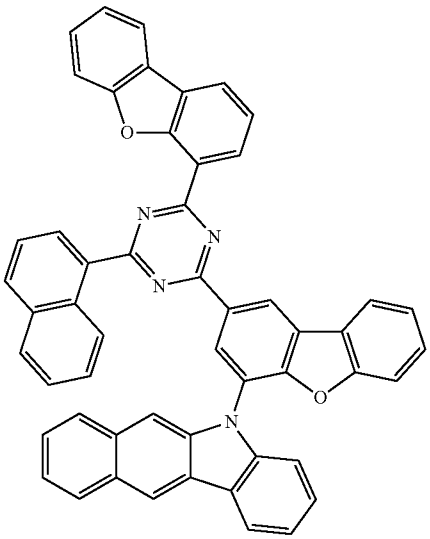
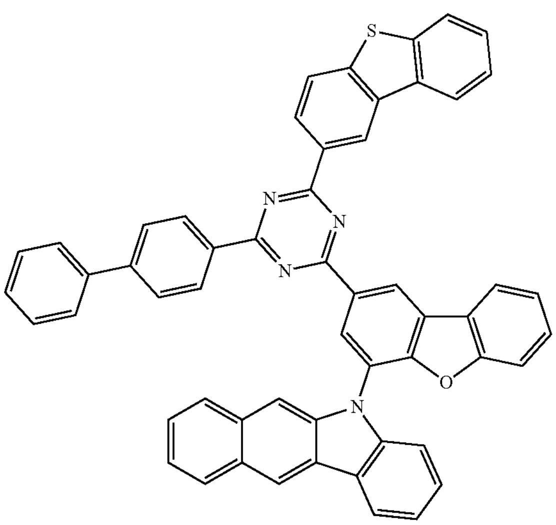
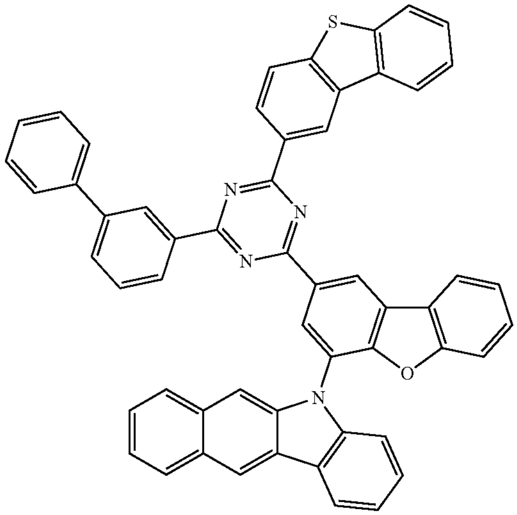
-continued
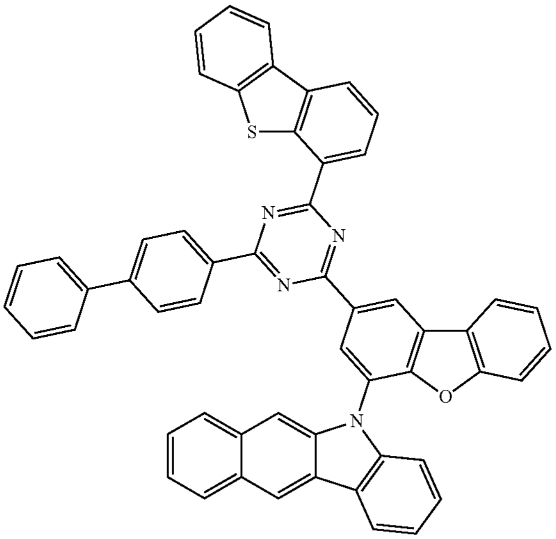
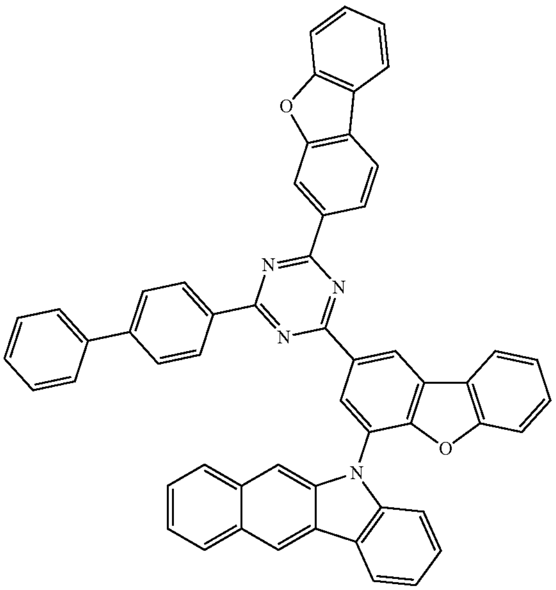
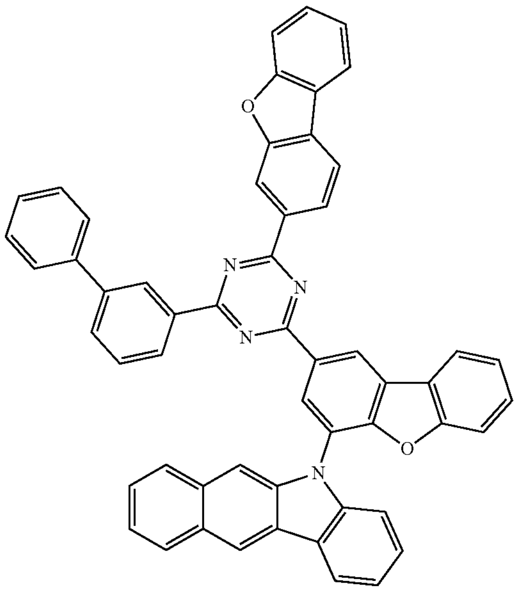

-continued
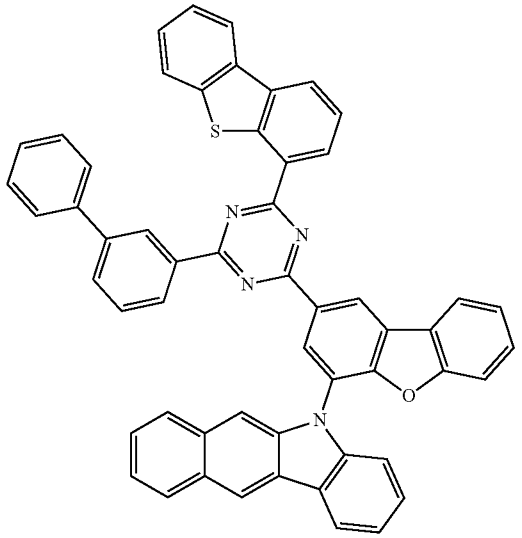
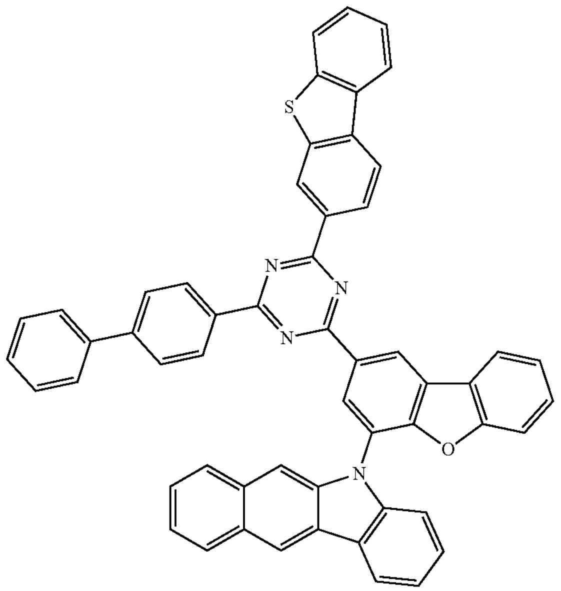
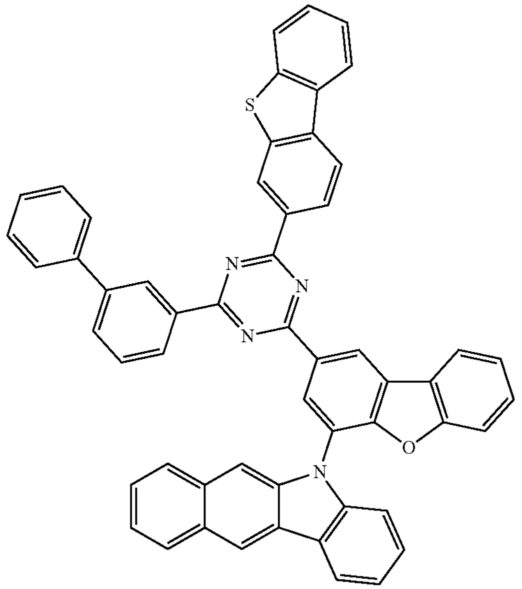
-continued
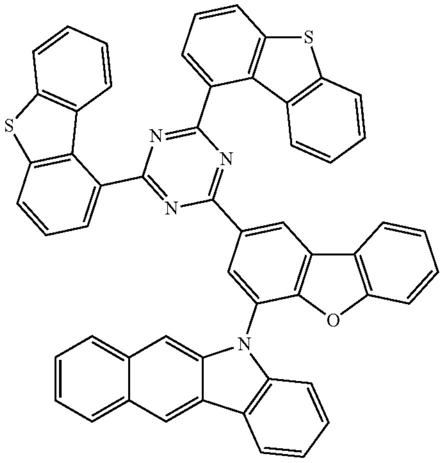
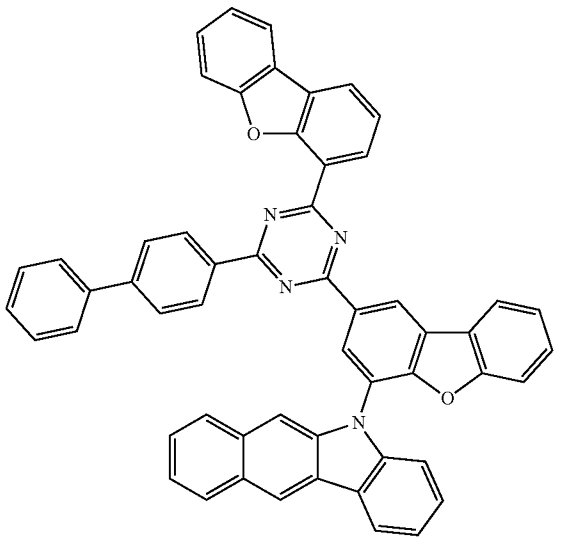
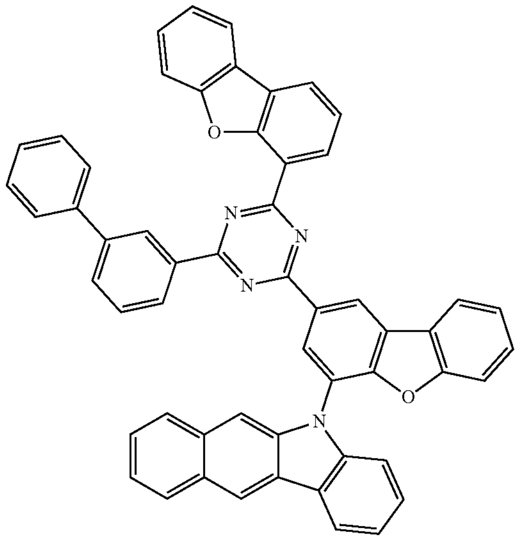

-continued
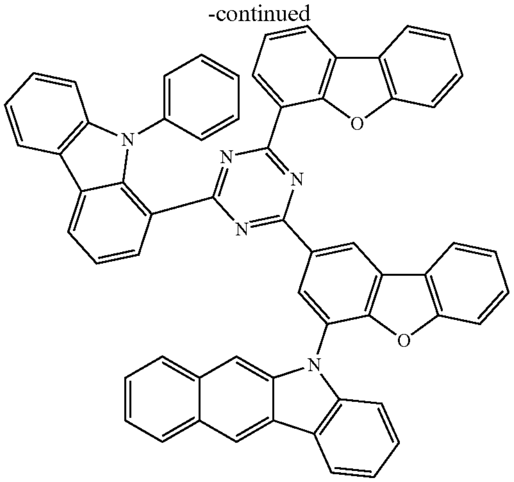
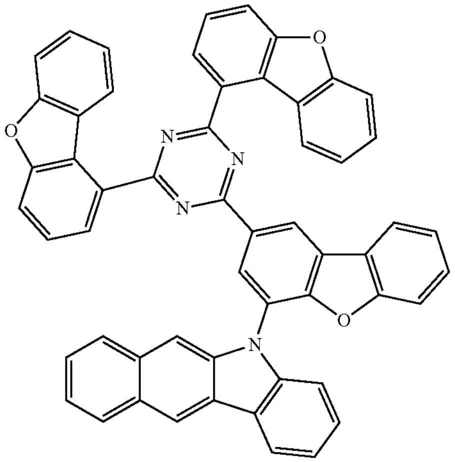
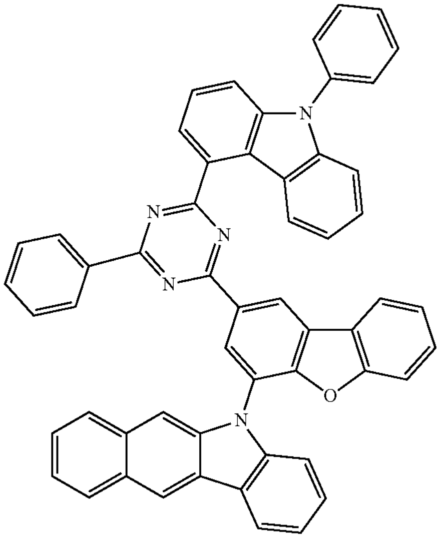
-continued
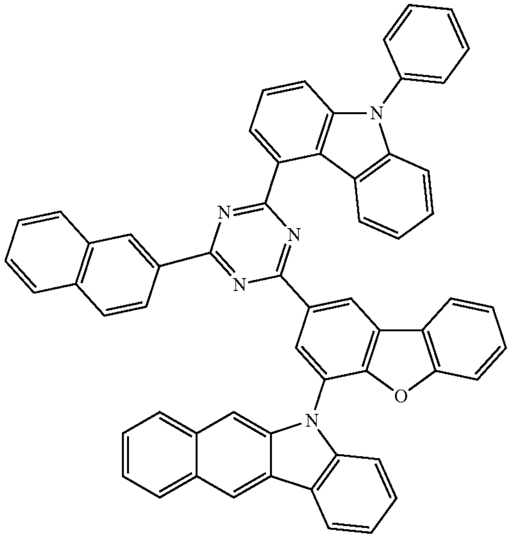
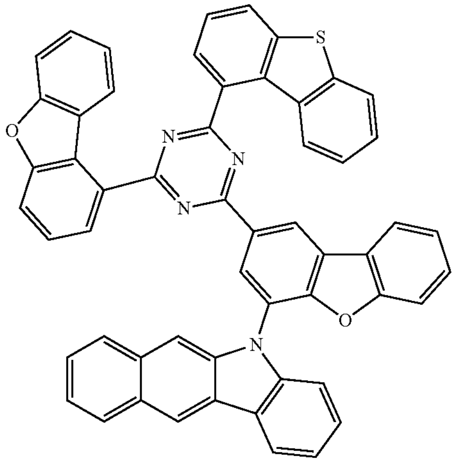
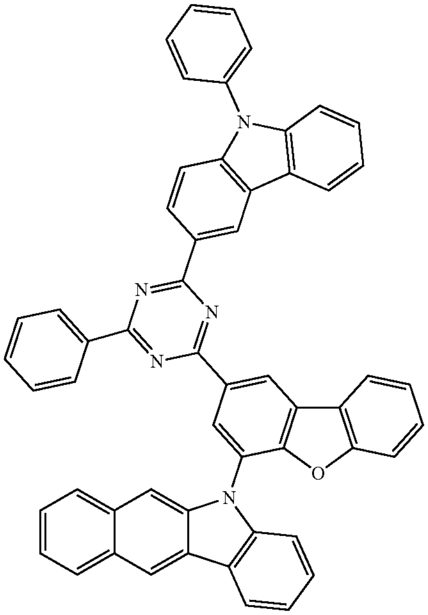

-continued
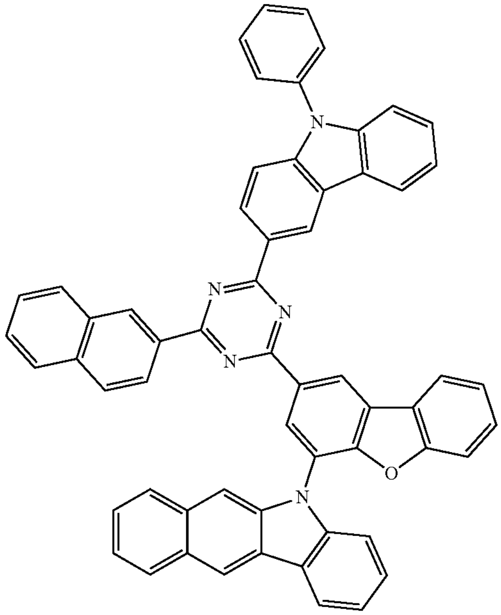
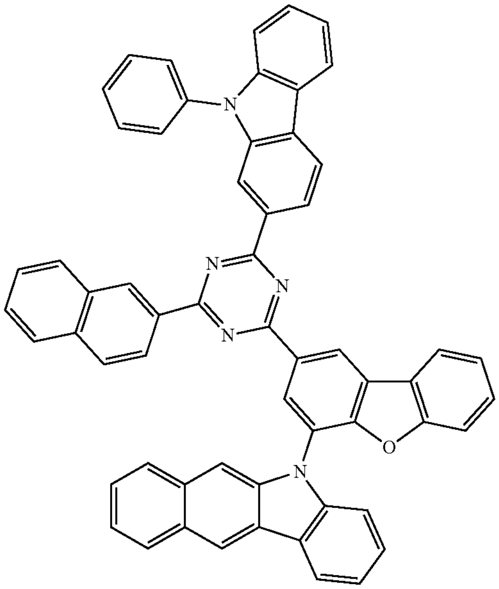
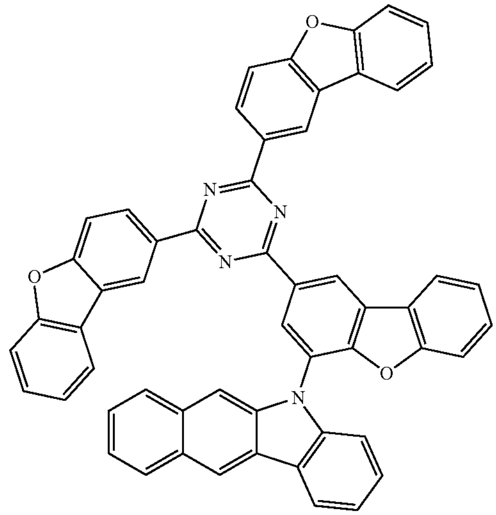
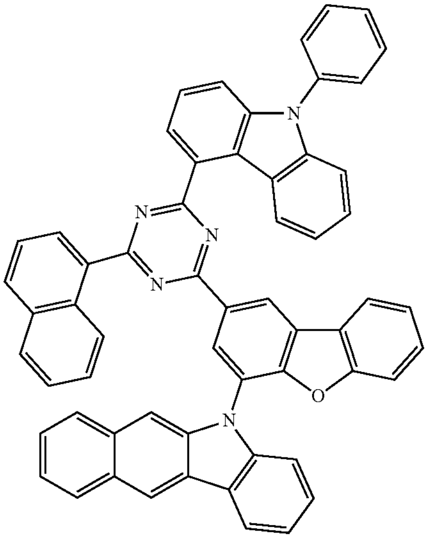
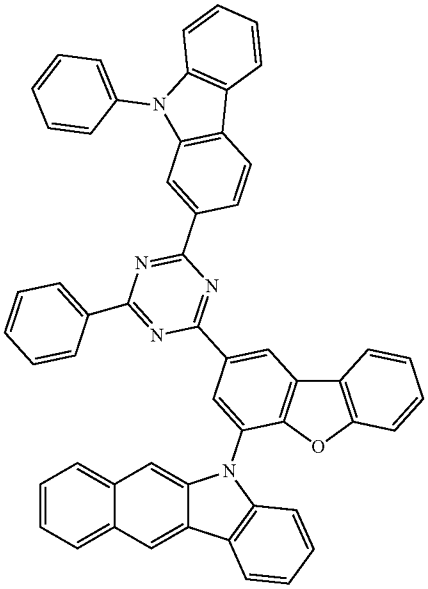
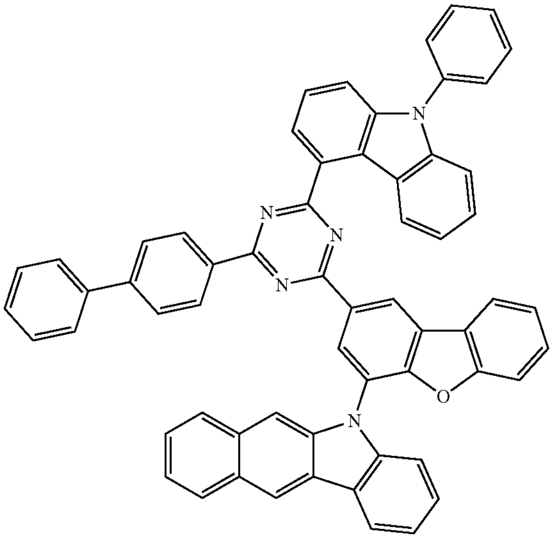
-continued -continued
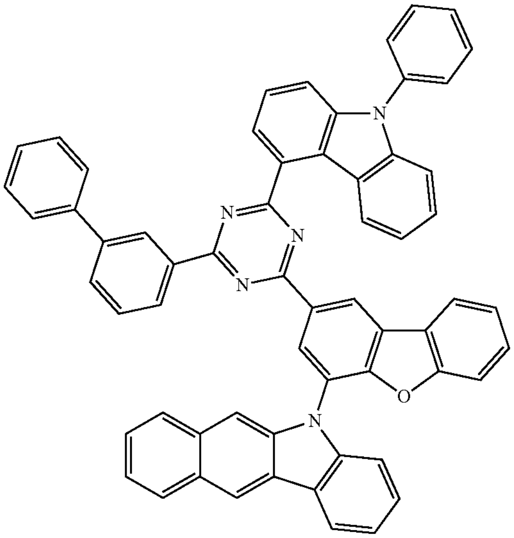
-continued
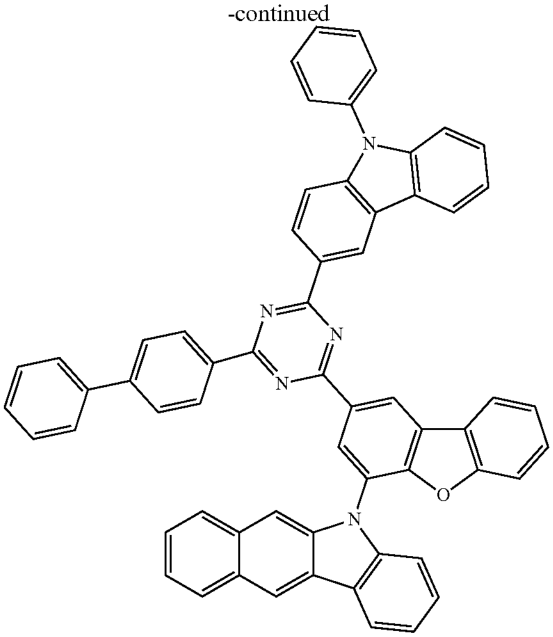
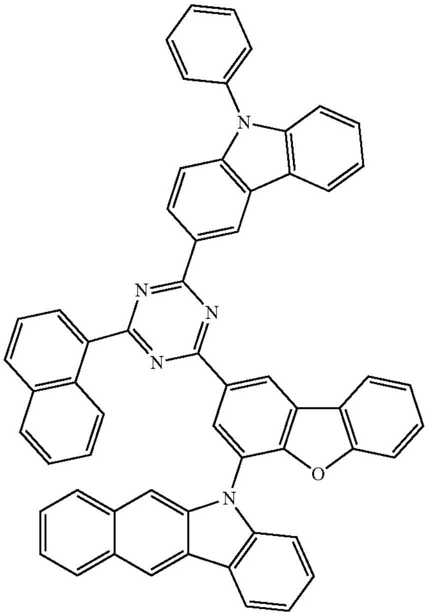
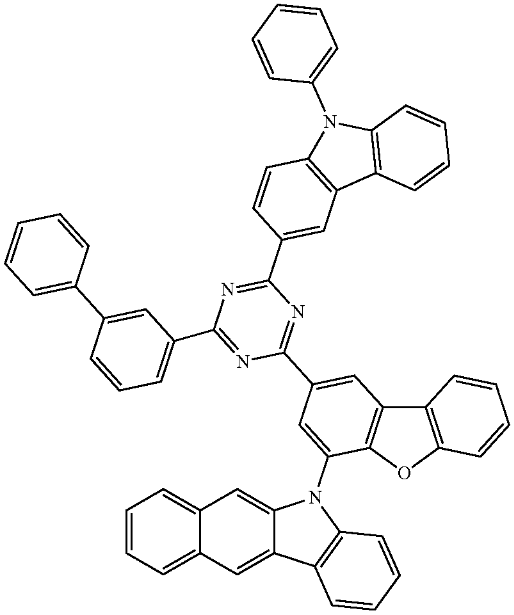

-continued
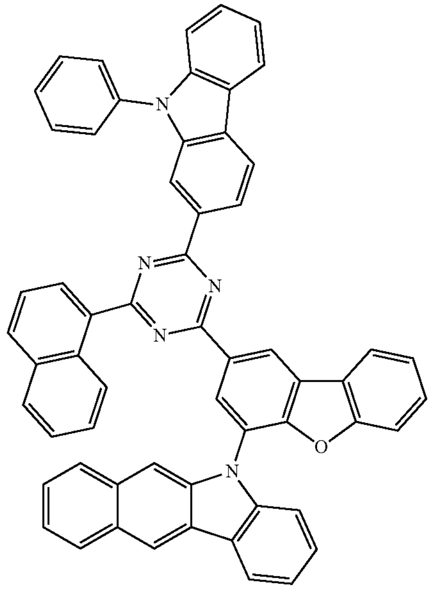
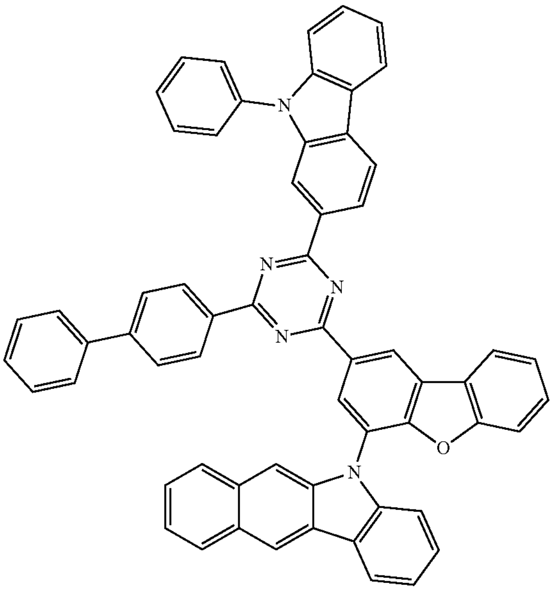
-continued
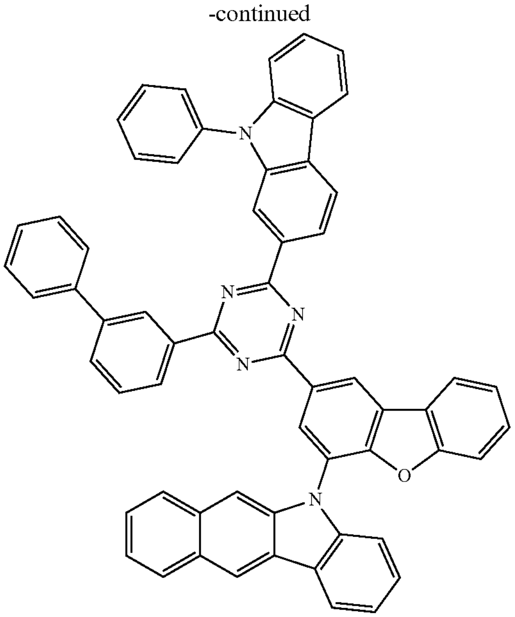
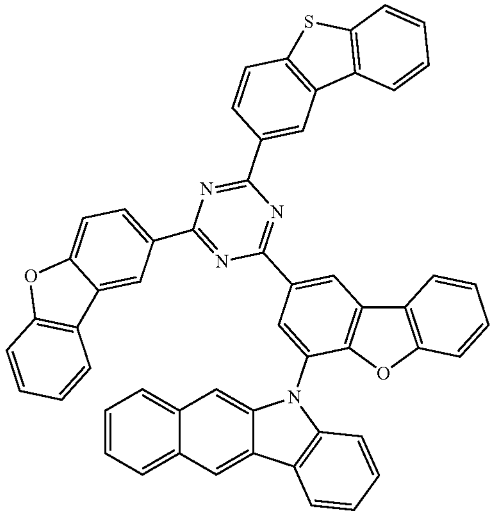
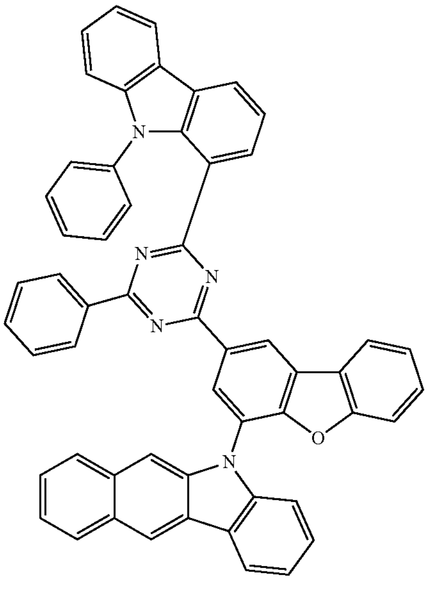

-continued
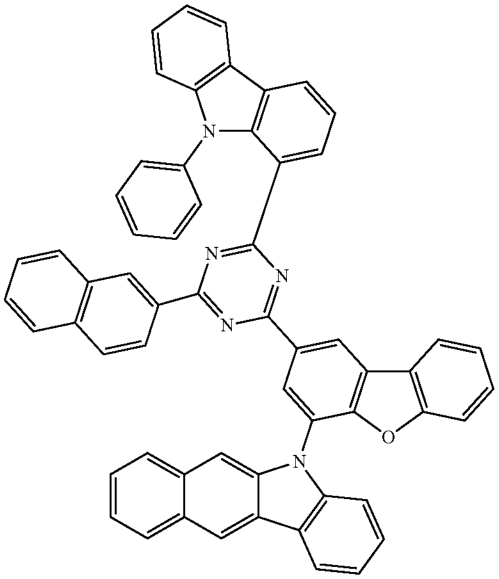
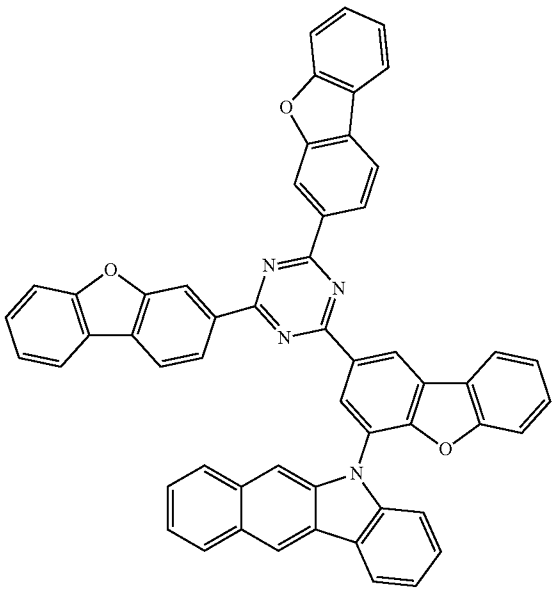
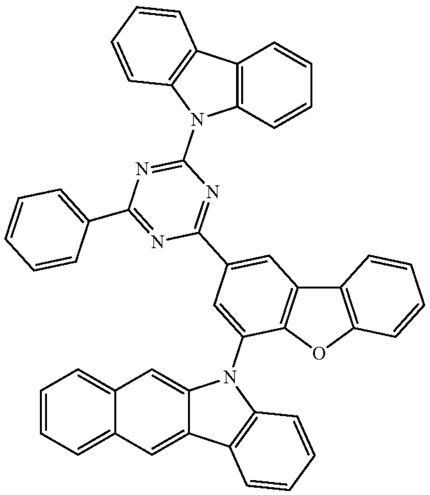
-continued
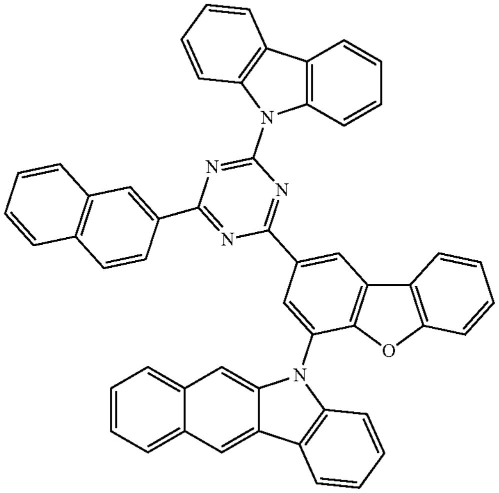
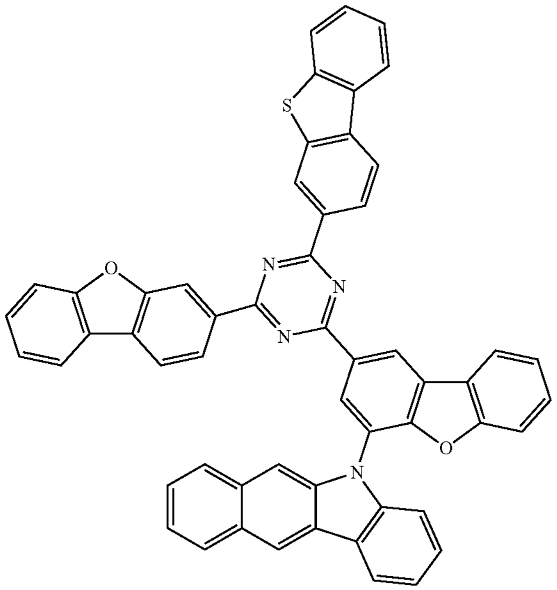
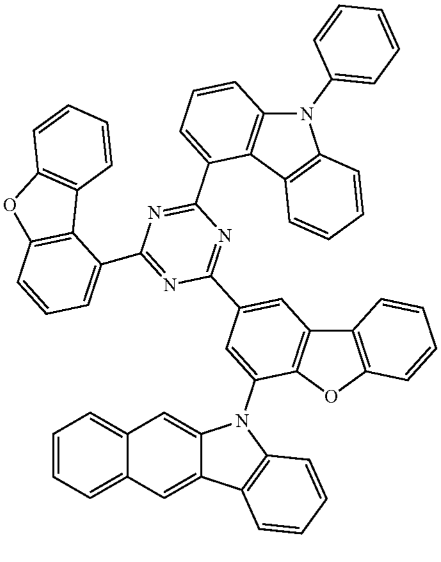

-continued
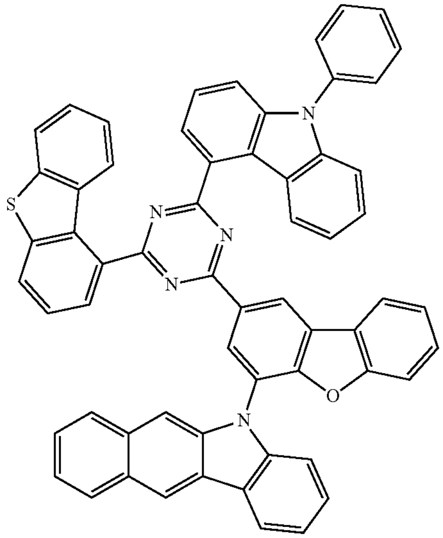
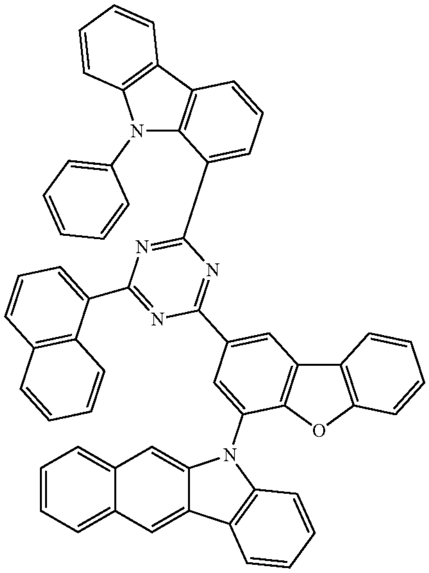
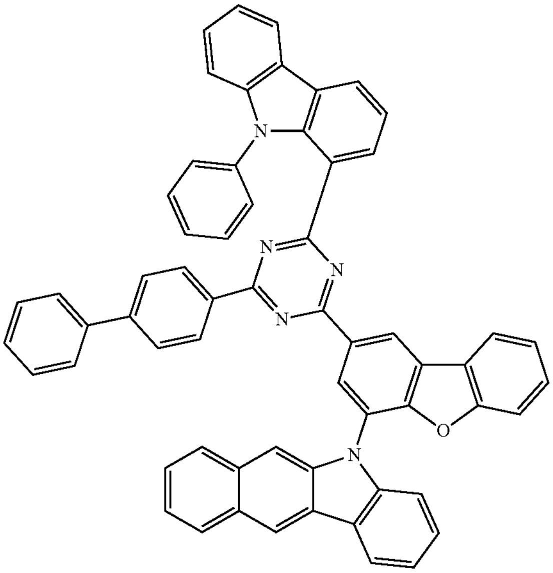
-continued
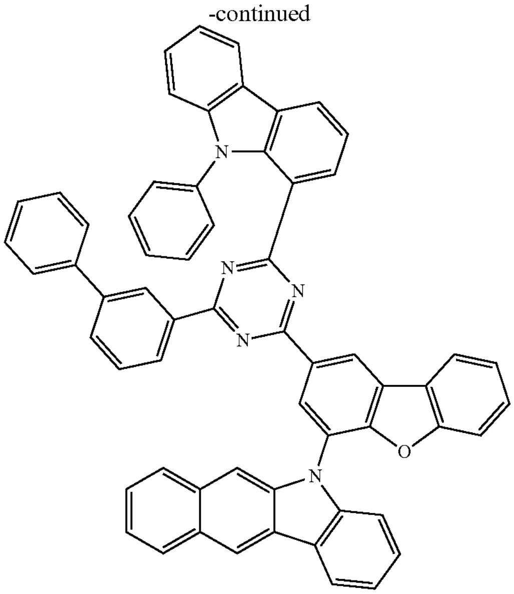
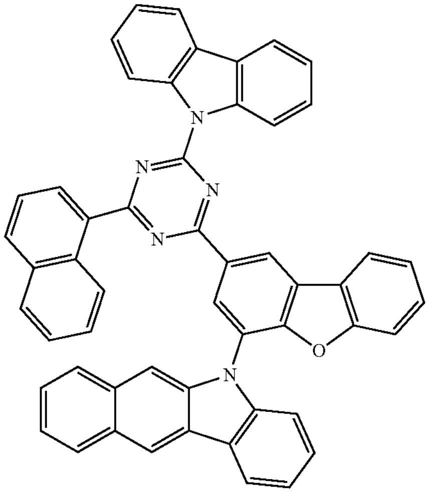
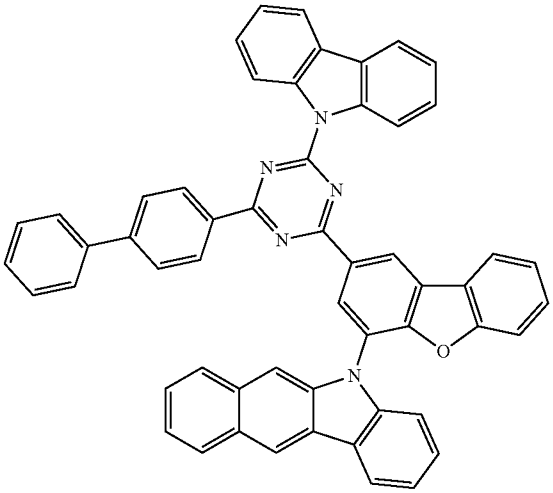

-continued
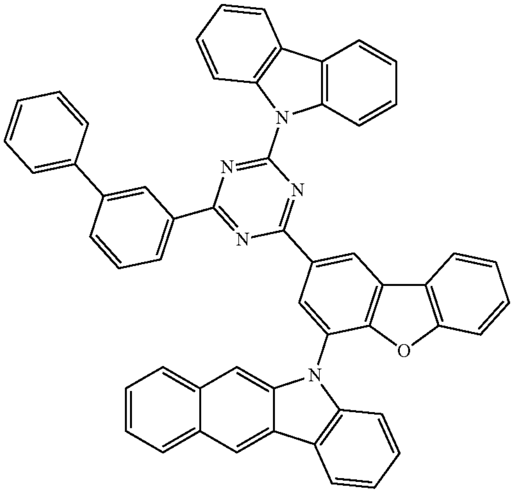
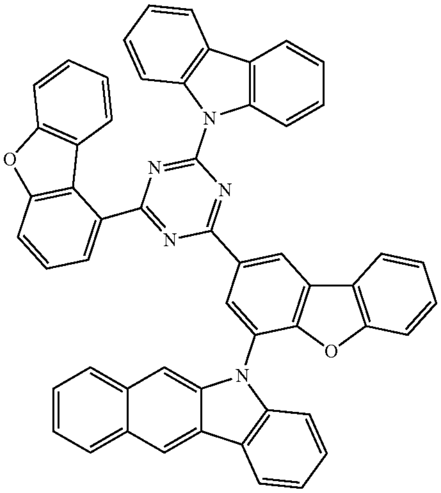
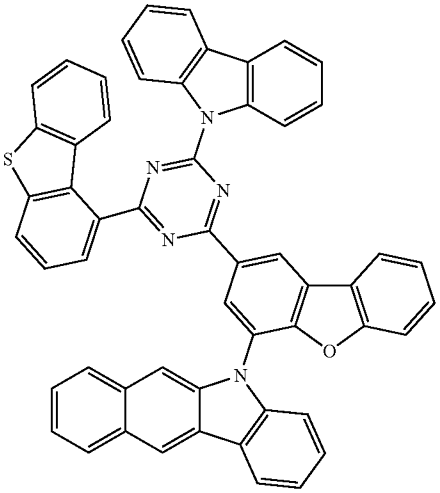
-continued
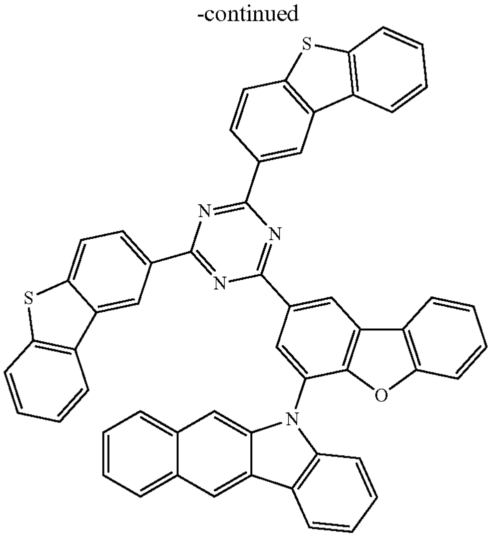
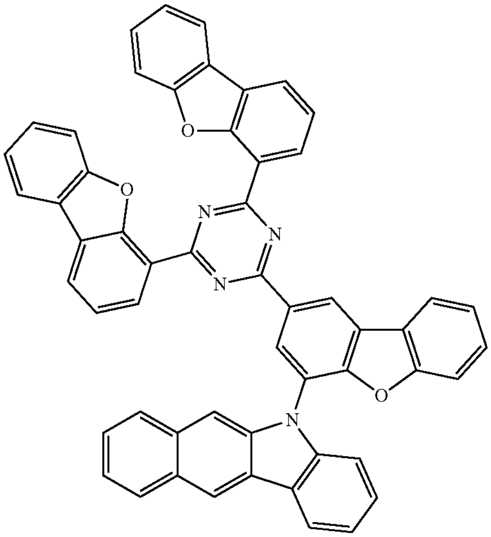
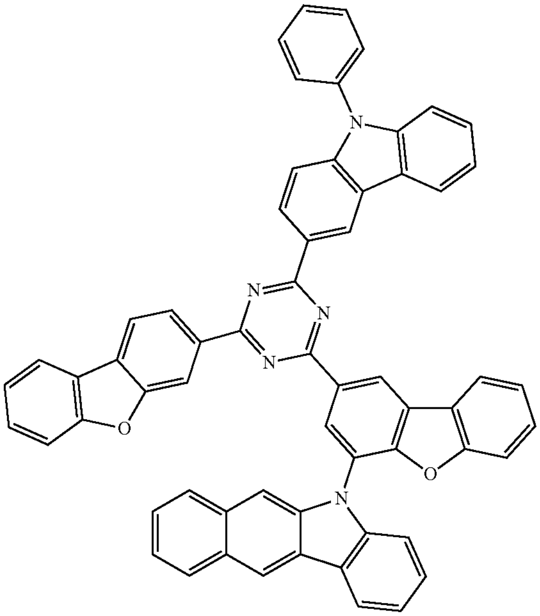

-continued
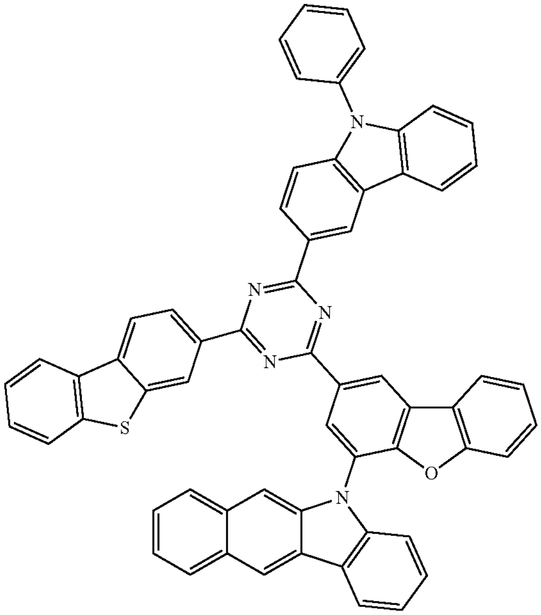
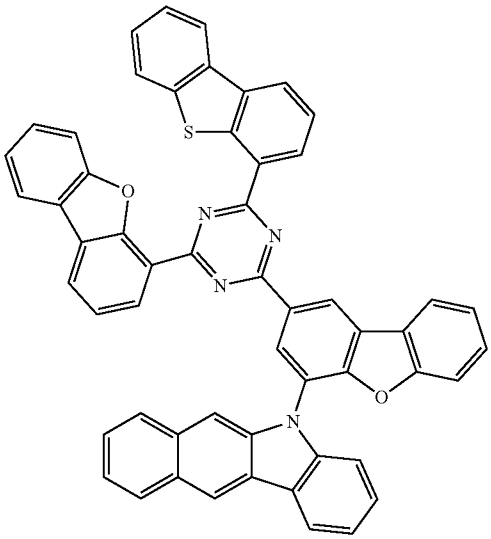
-continued
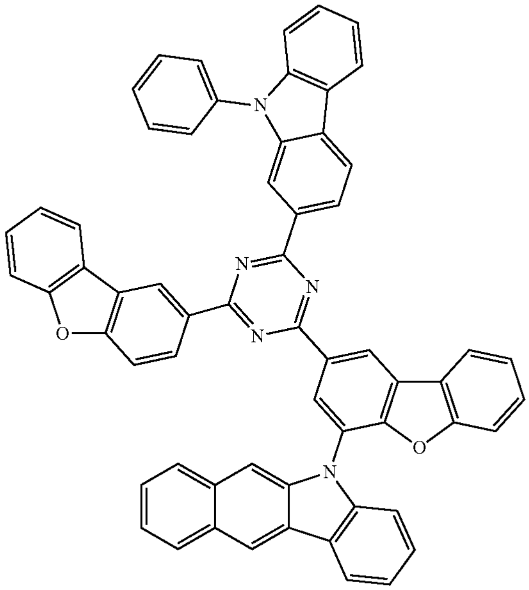
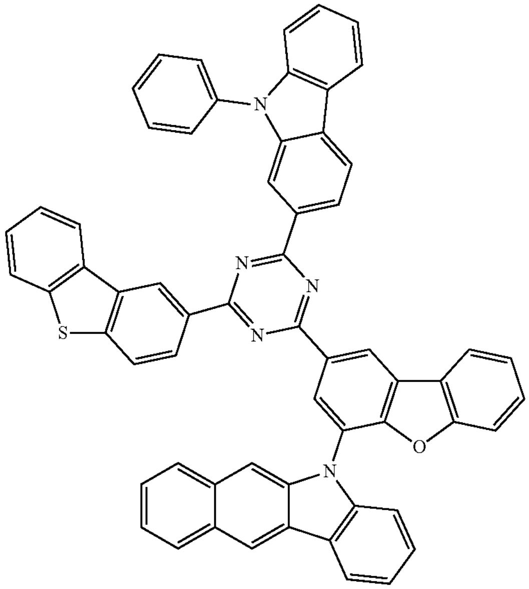
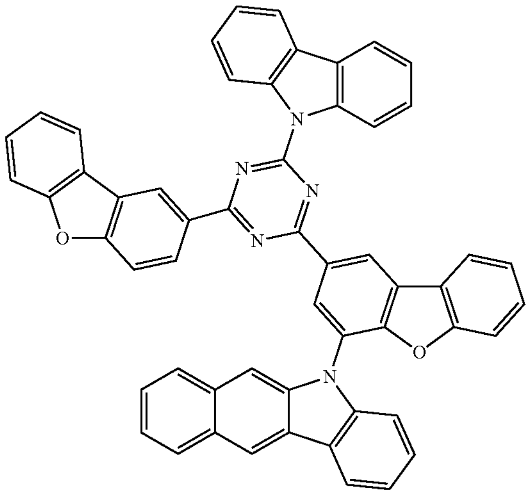

-continued
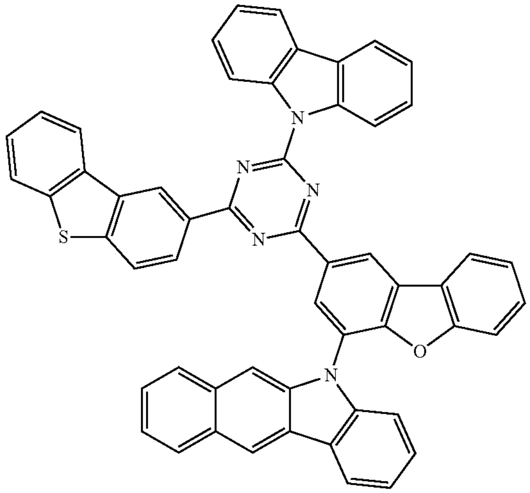
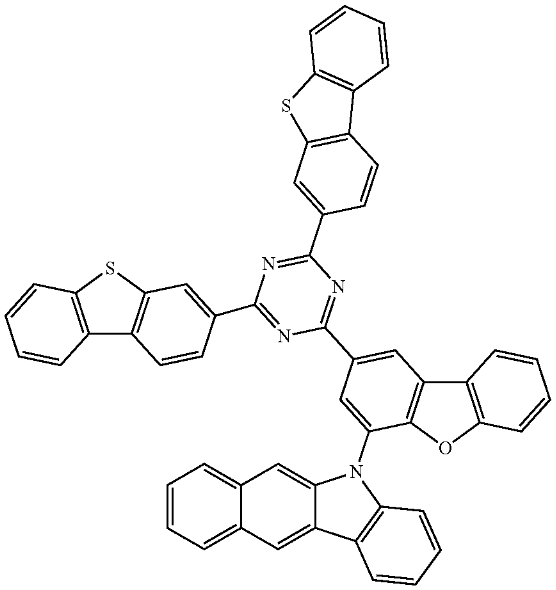
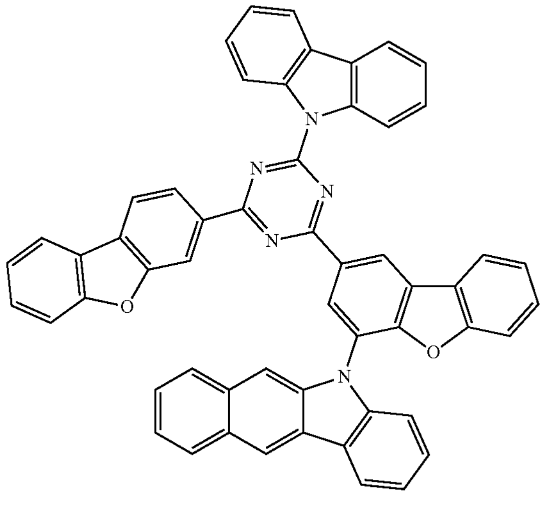
-continued
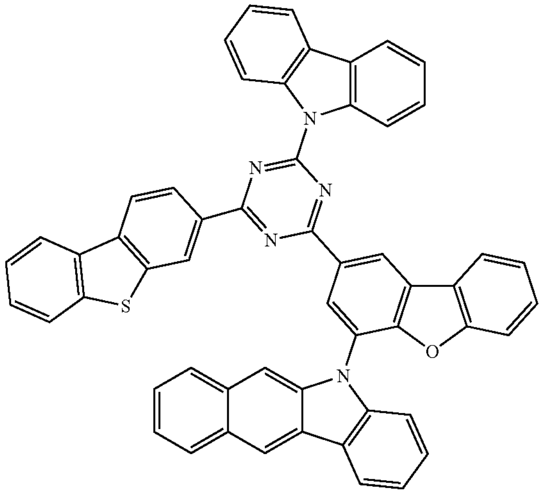
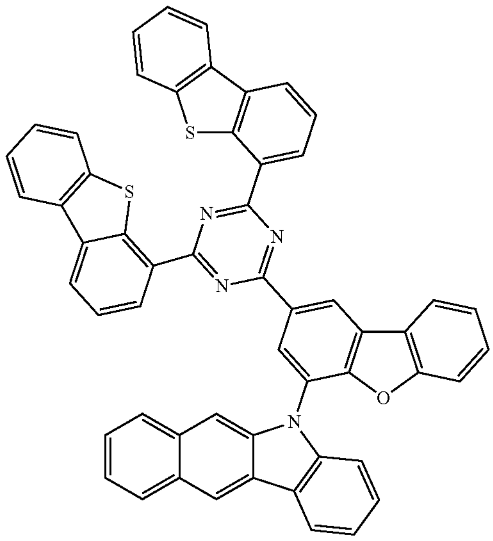
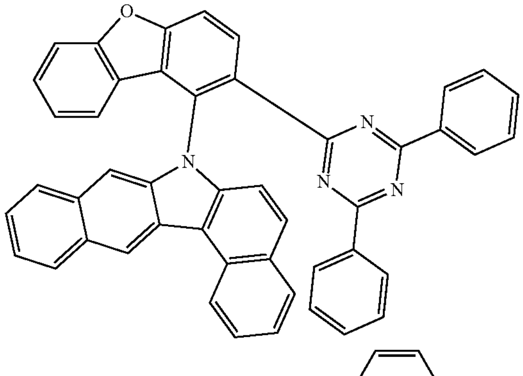
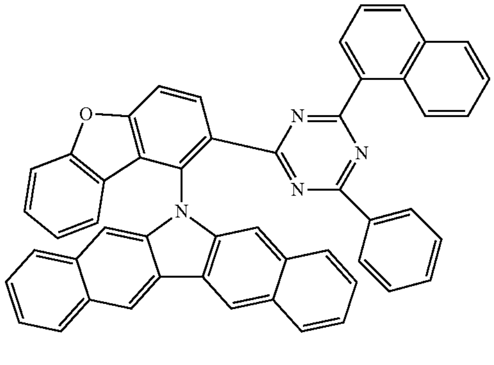

-continued
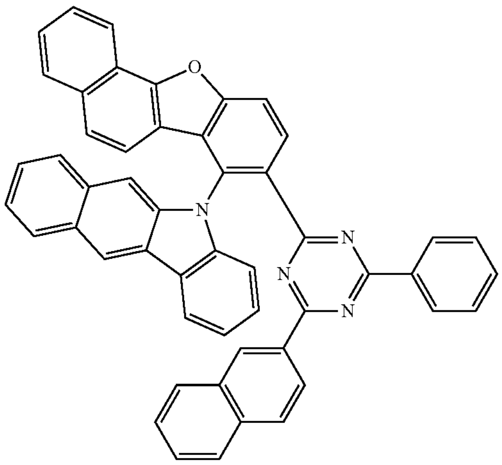
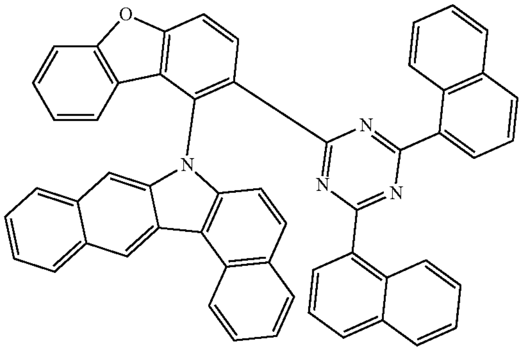
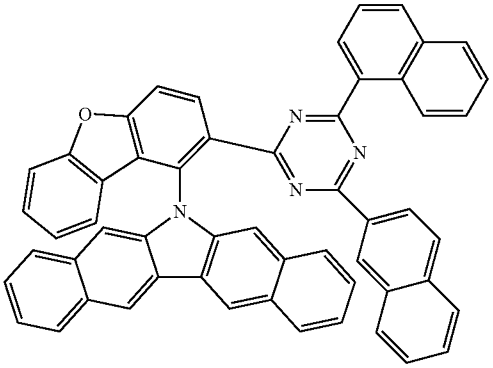
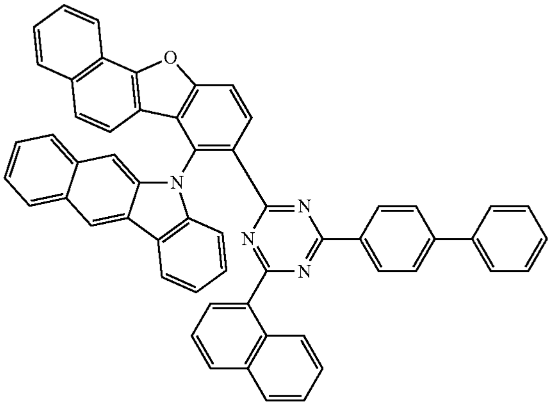
-continued
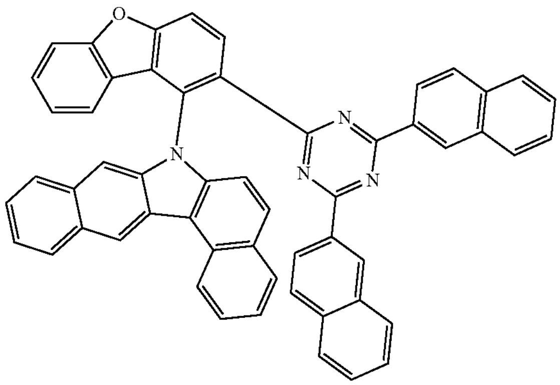
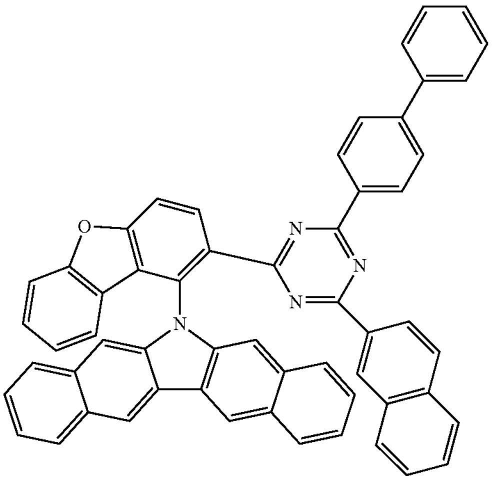
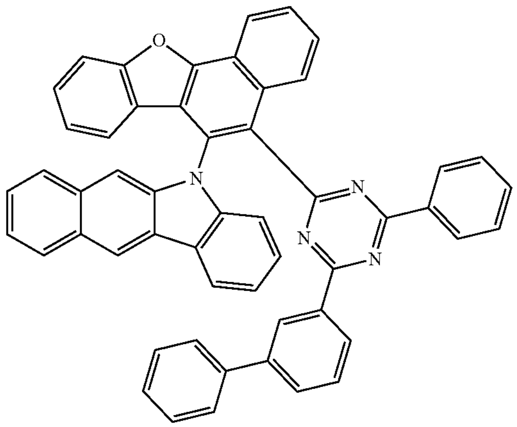
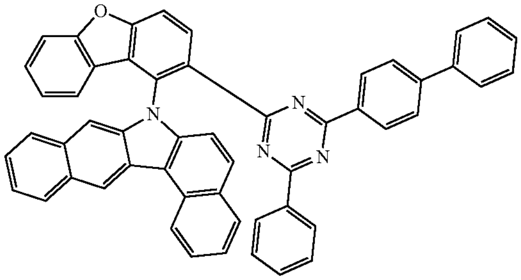

-continued
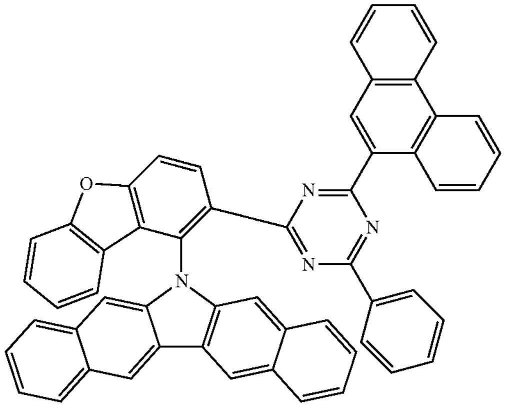
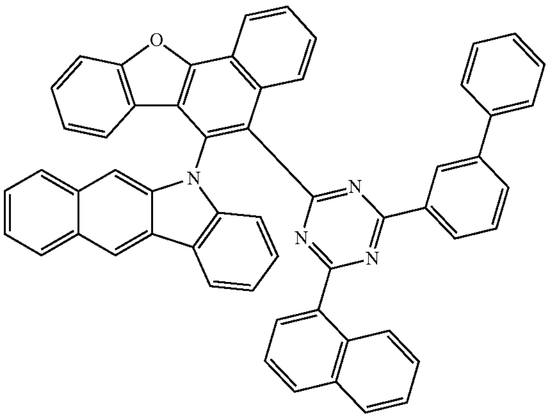
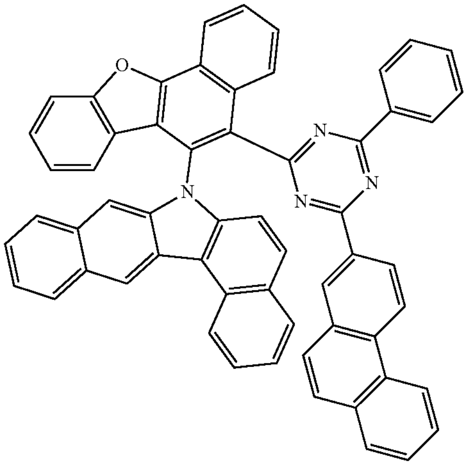
-continued
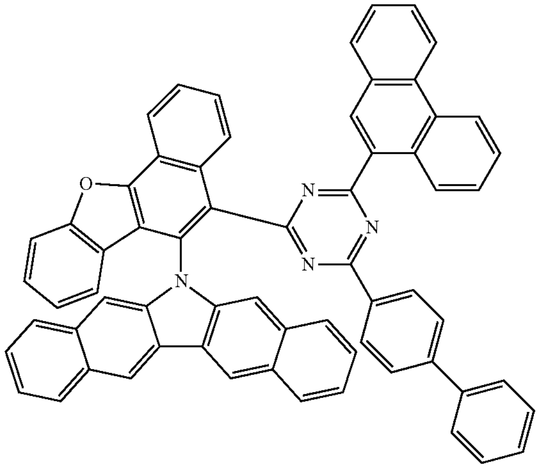
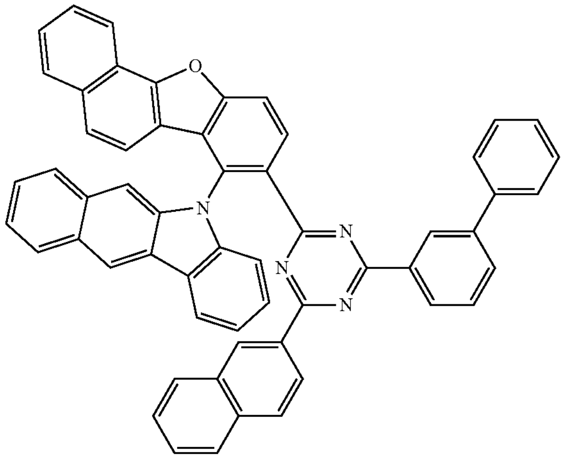
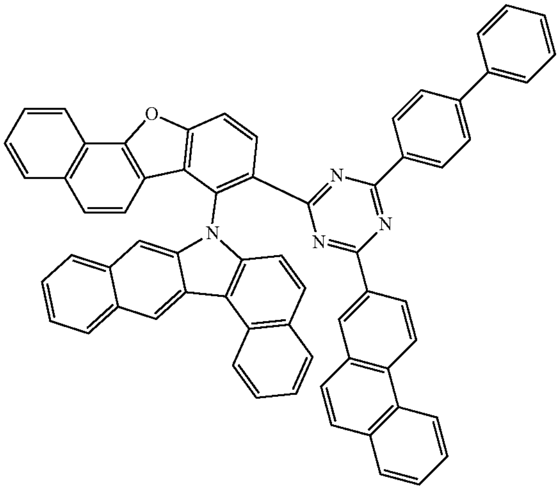

-continued
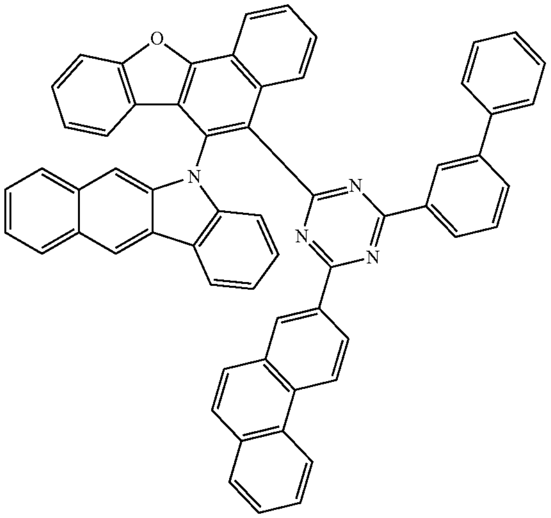
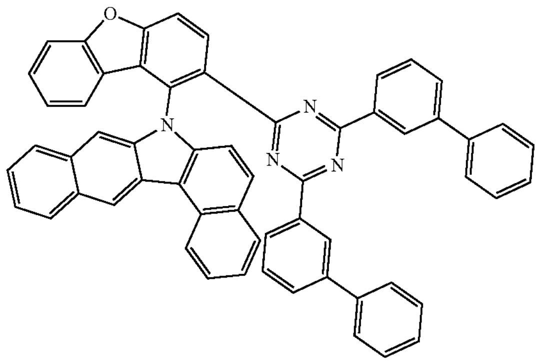
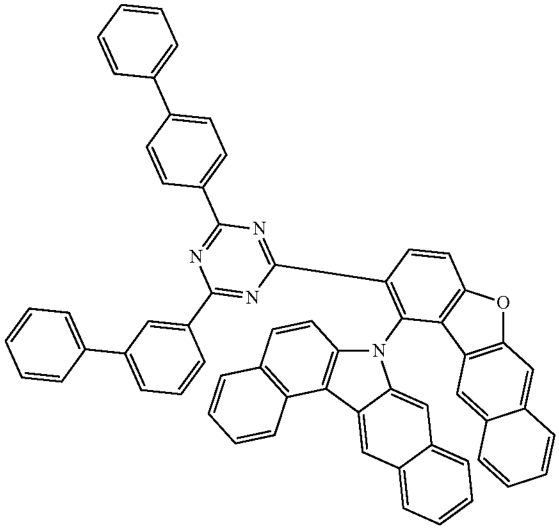
-continued
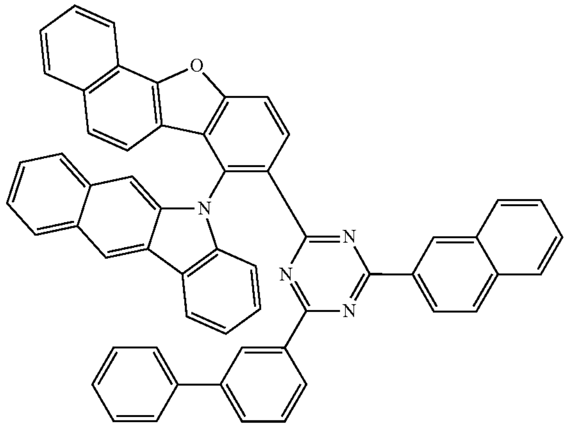
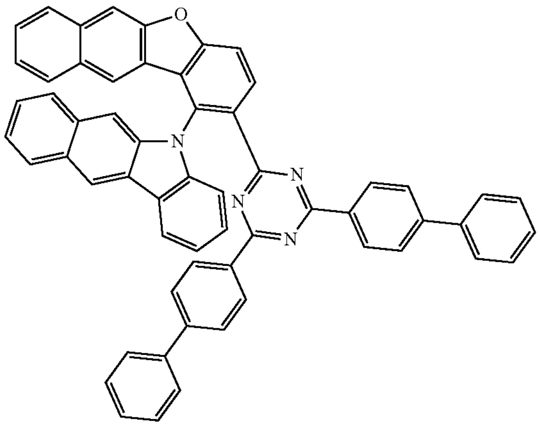
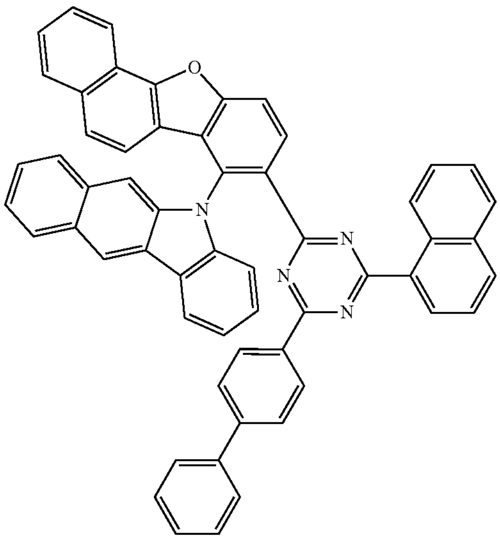

-continued
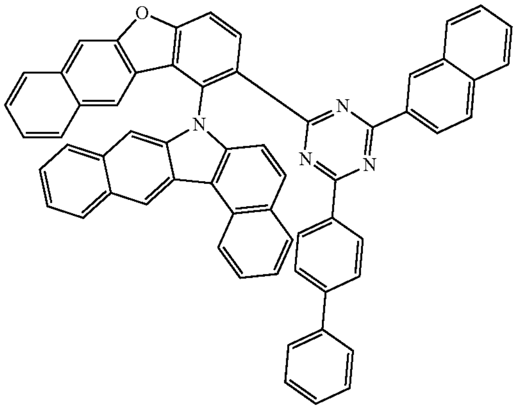
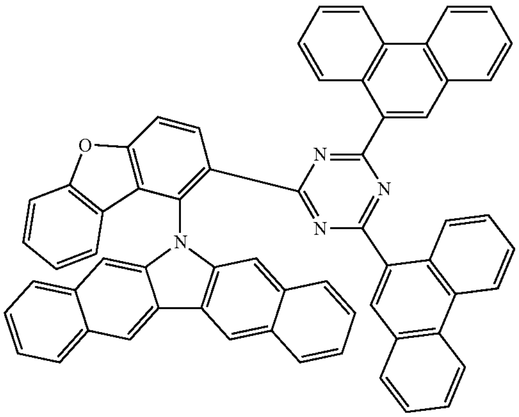
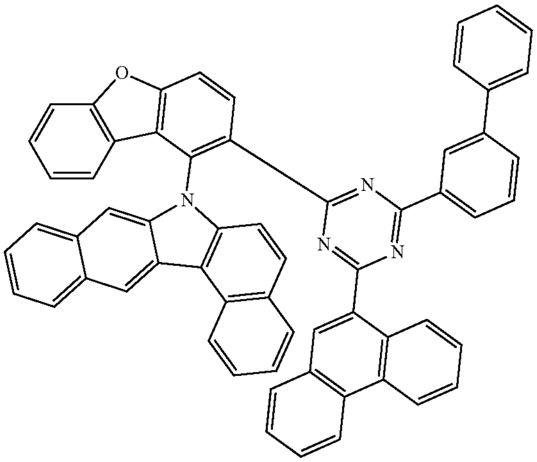
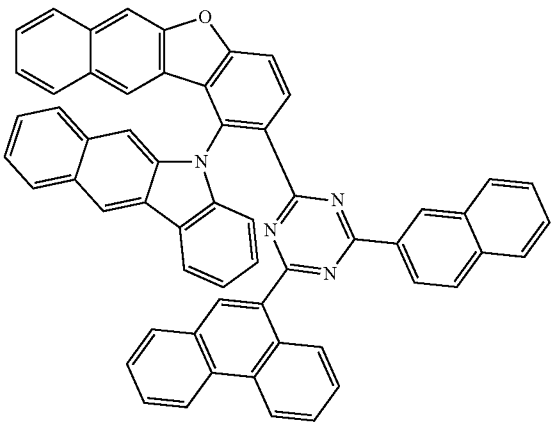
-continued
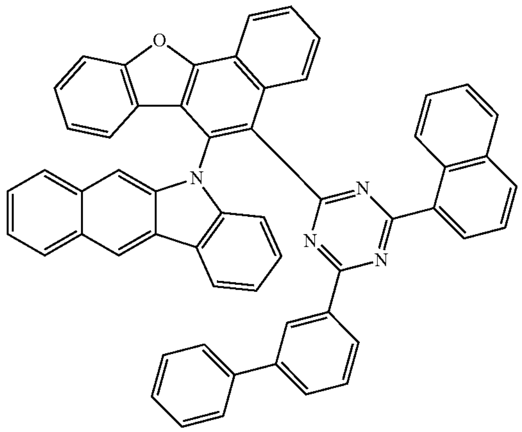
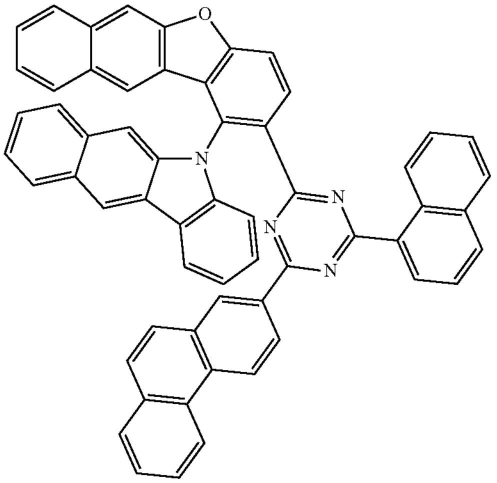
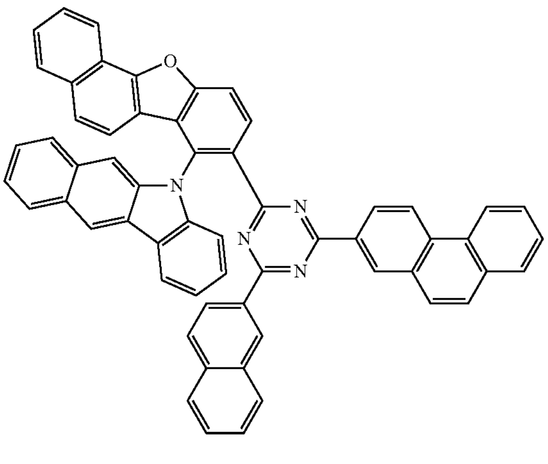

-continued
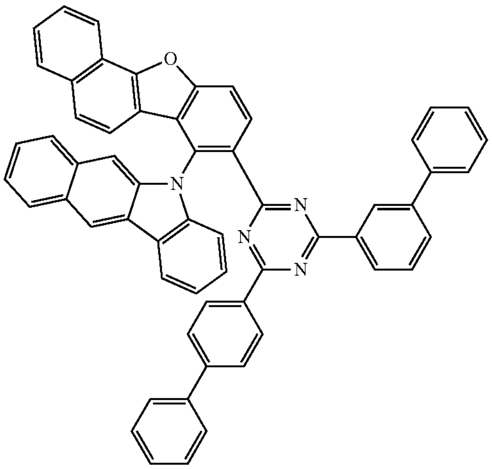
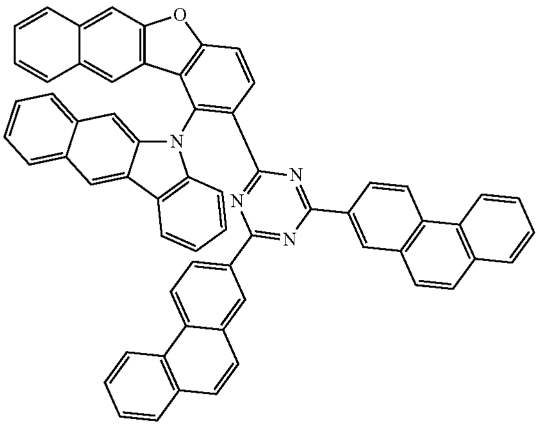
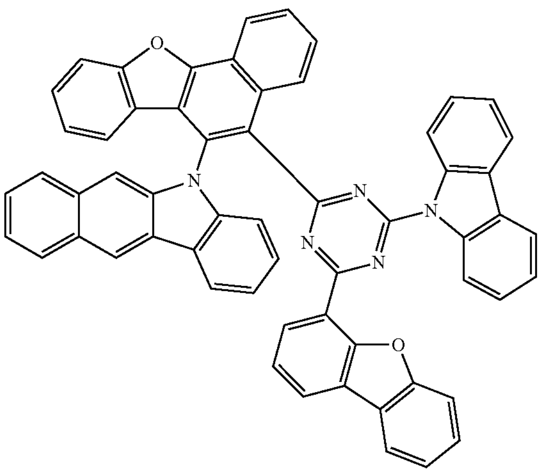
-continued
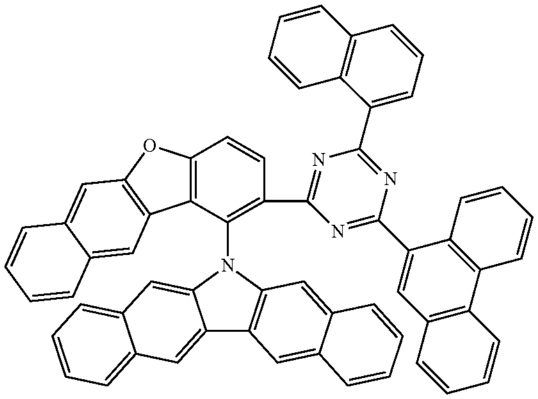
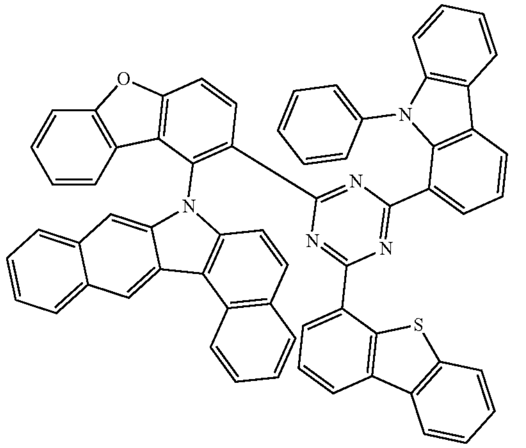
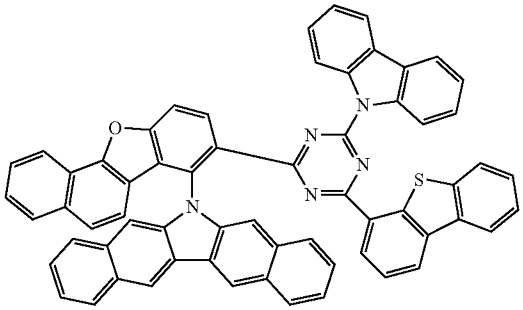
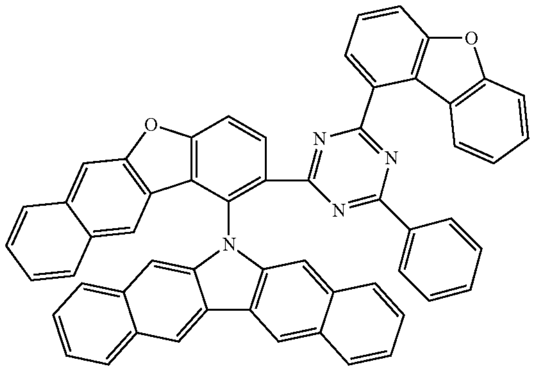

-continued
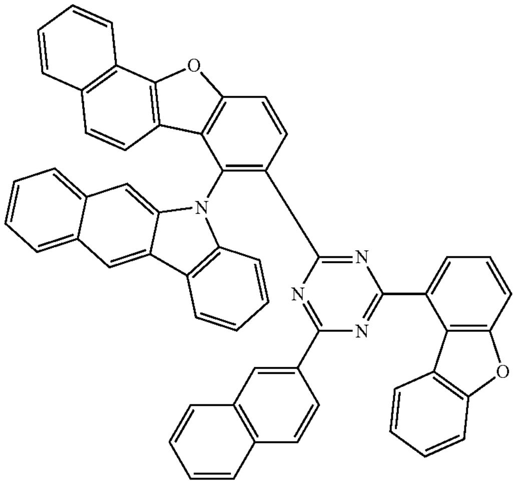
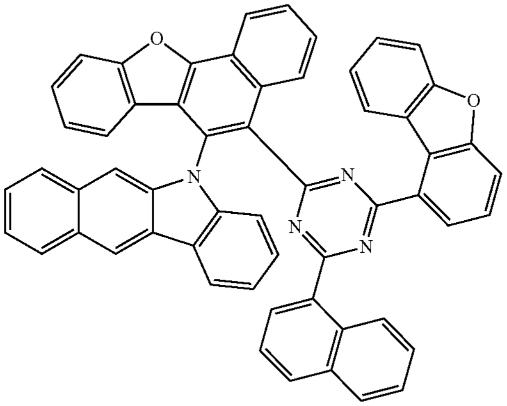
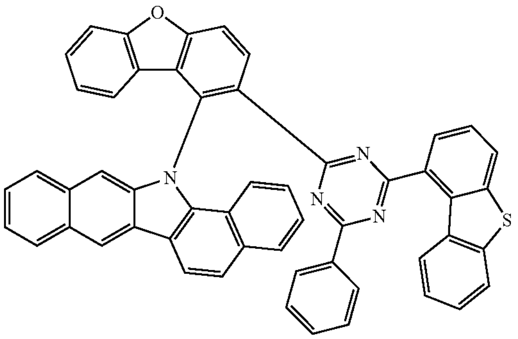
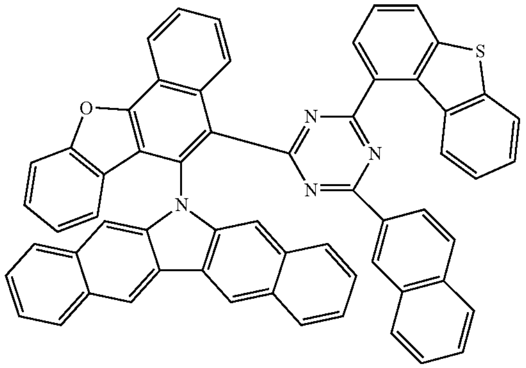
-continued
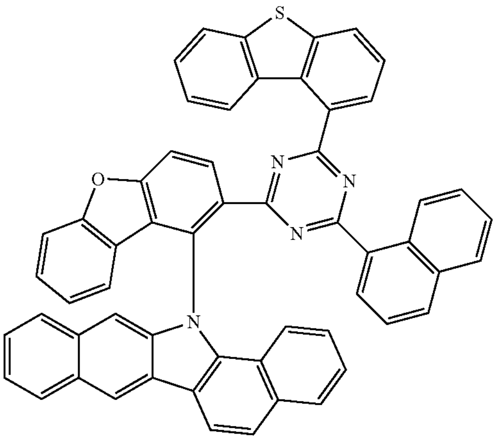
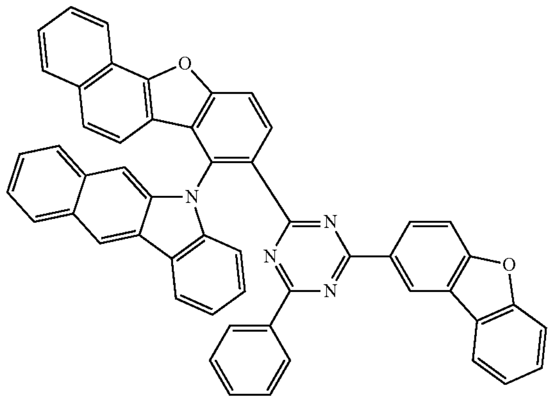
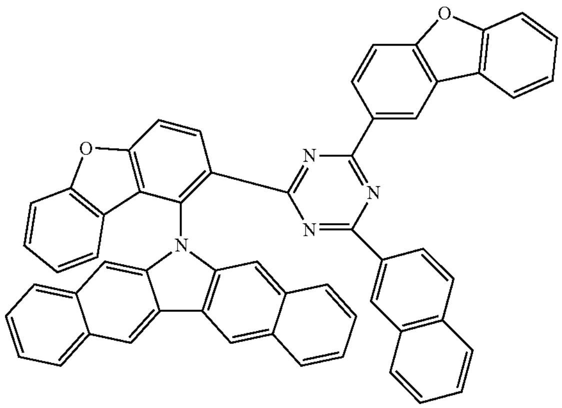
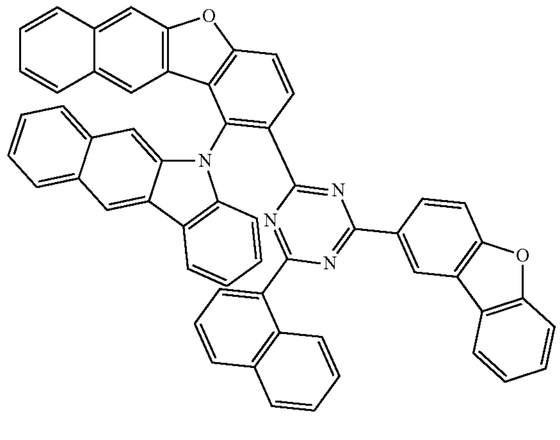

-continued
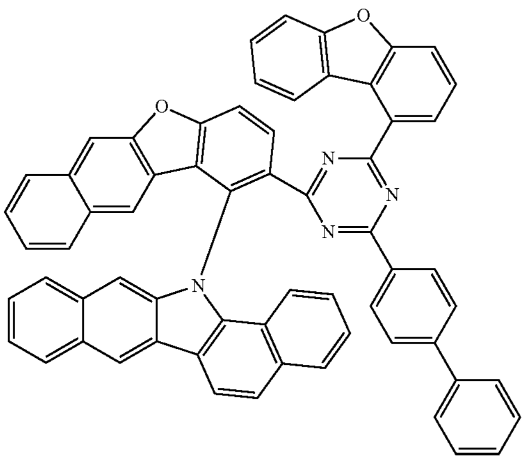
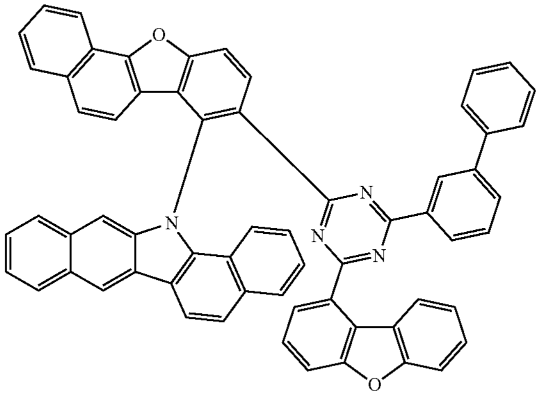
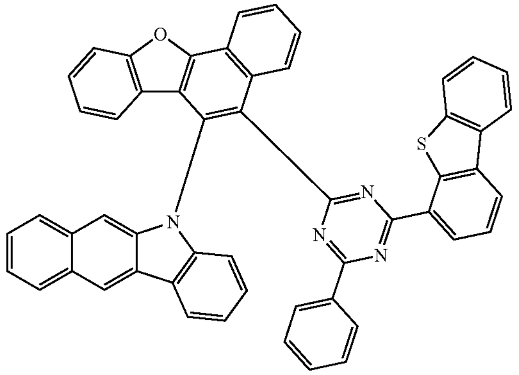
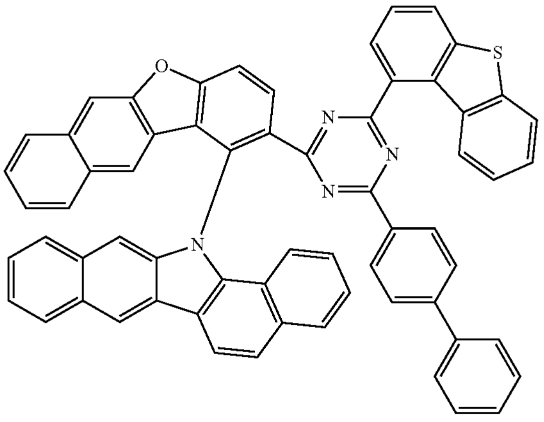
-continued
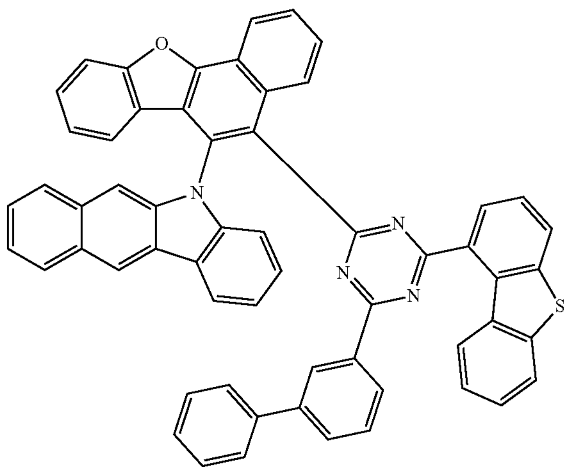
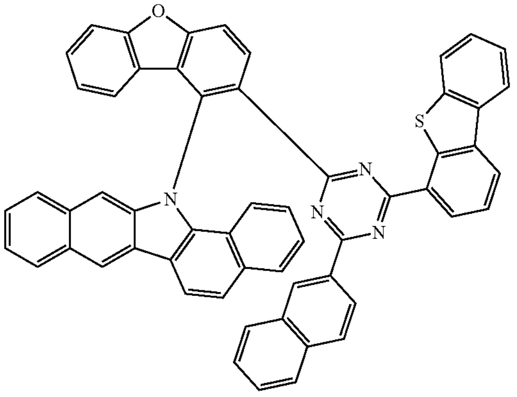
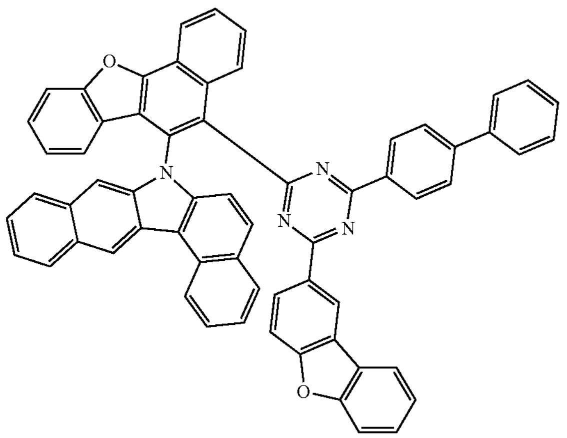

-continued
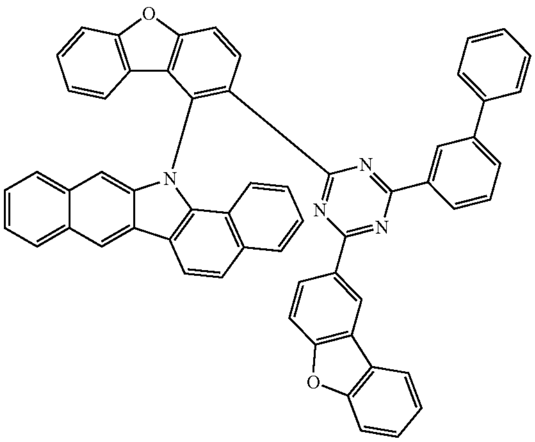
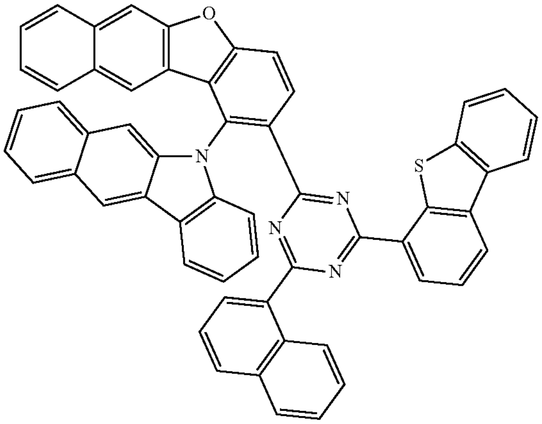
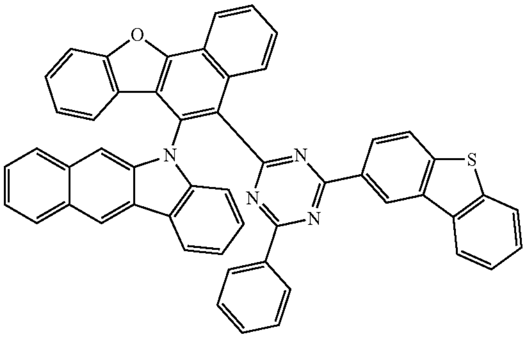
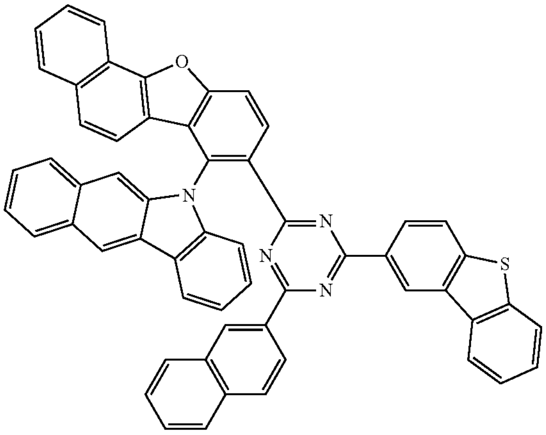
-continued
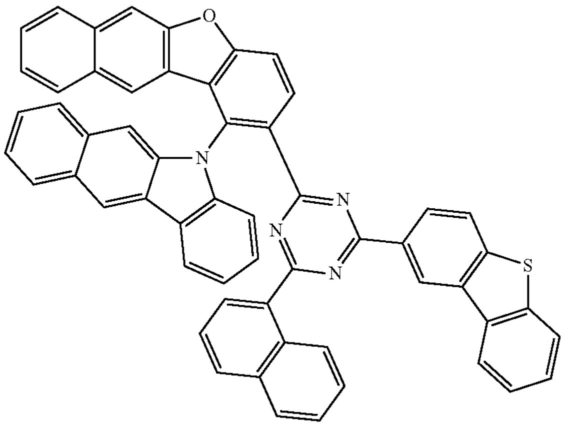
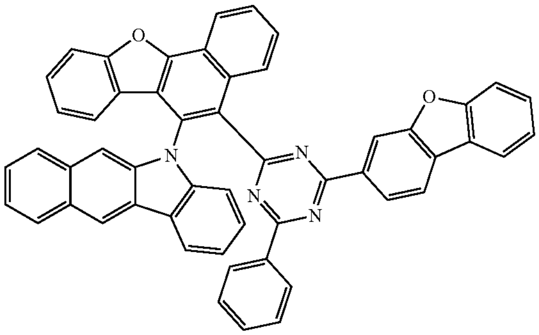
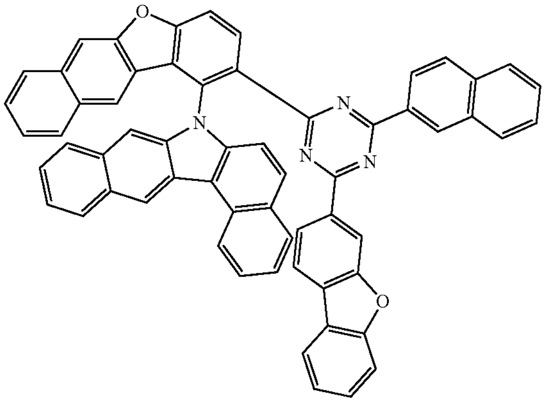
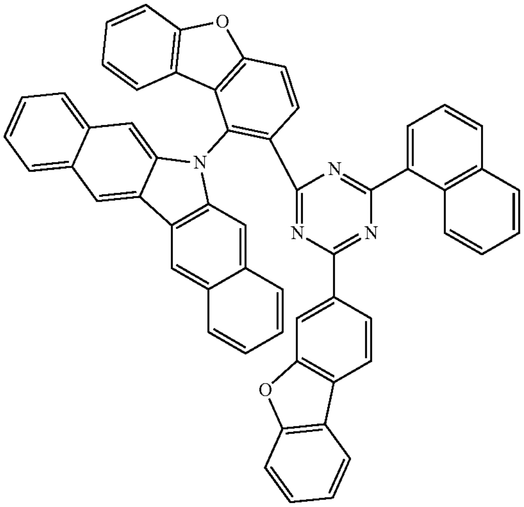

-continued
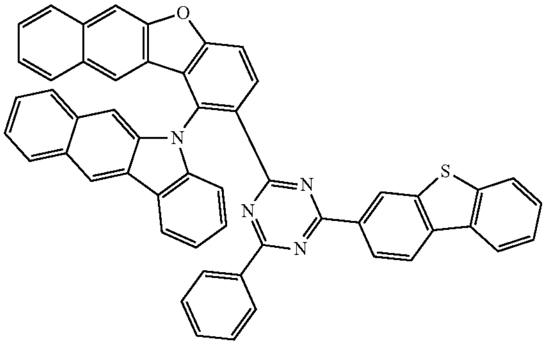
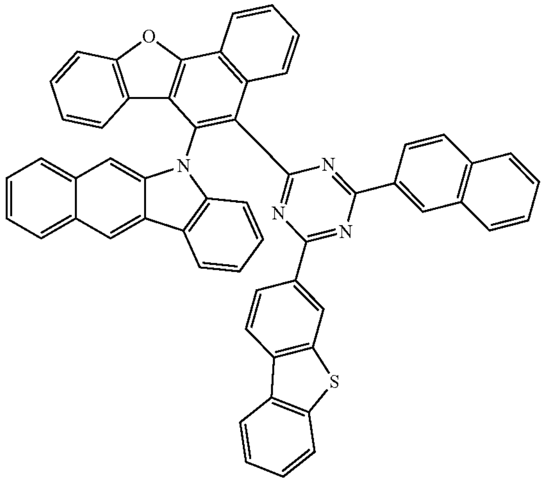
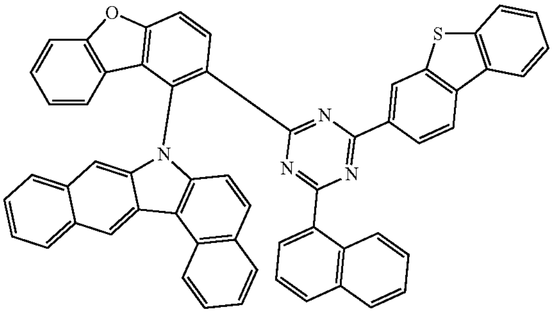
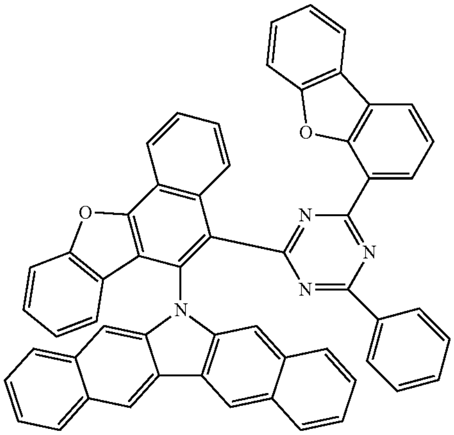
-continued
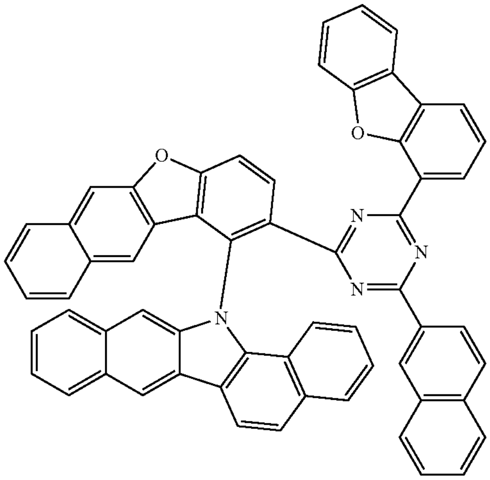
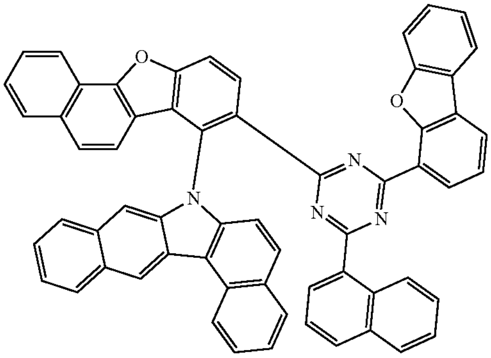
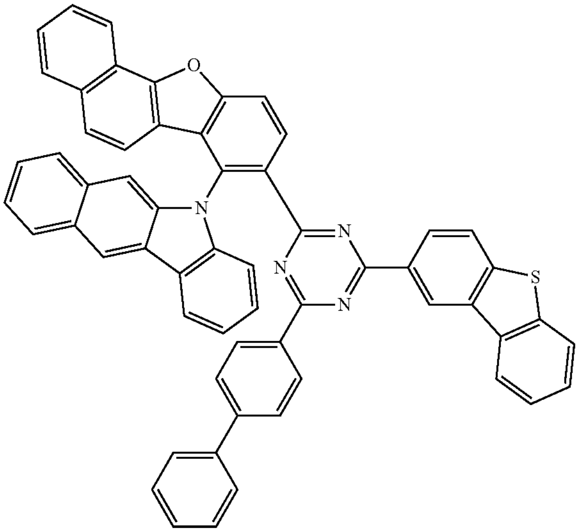

-continued
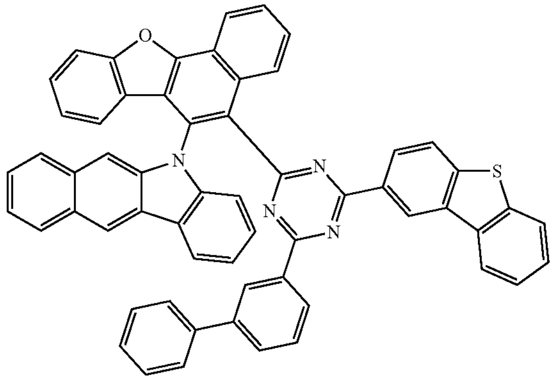
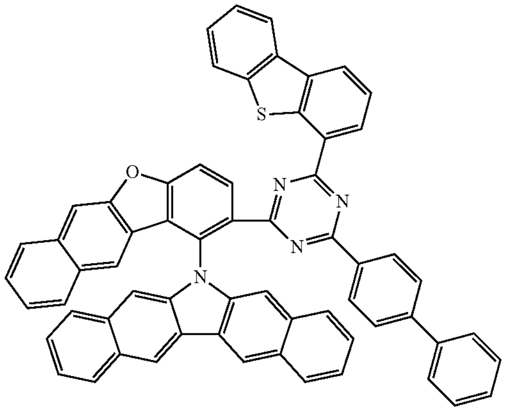
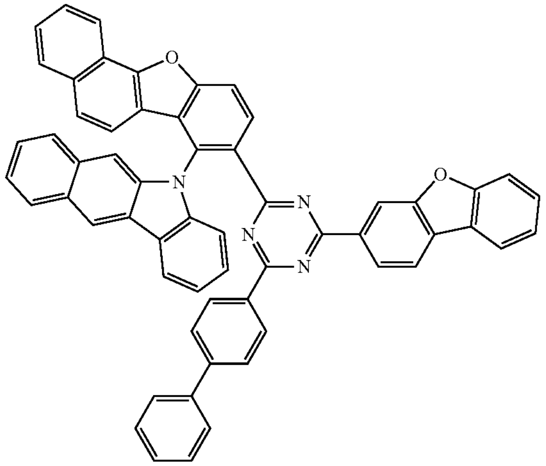
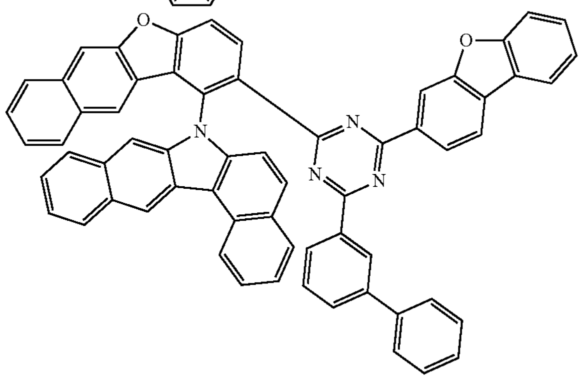
-continued
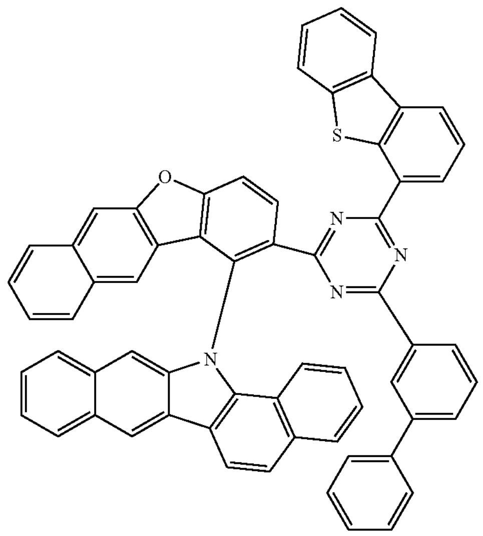
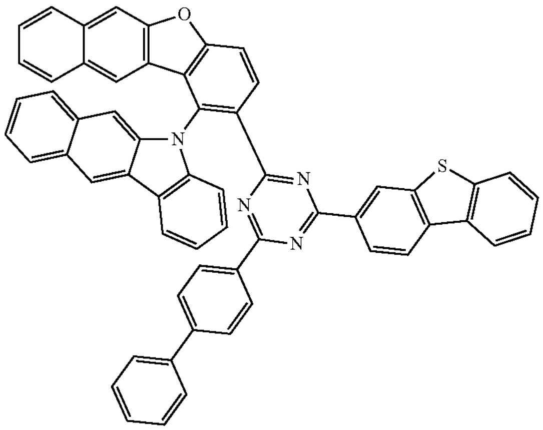
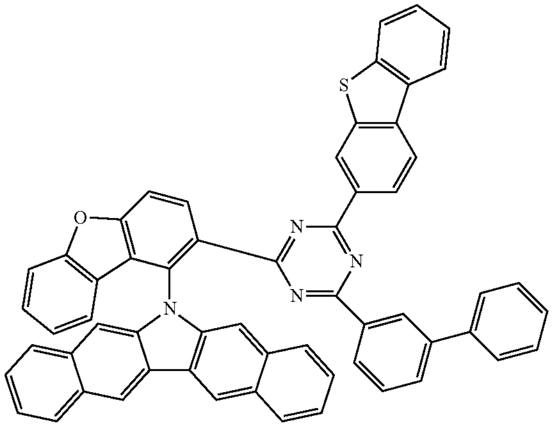

-continued
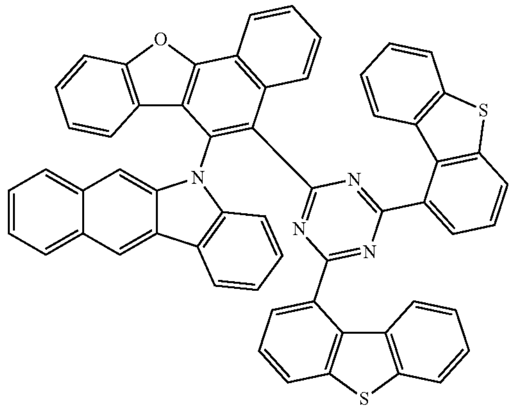
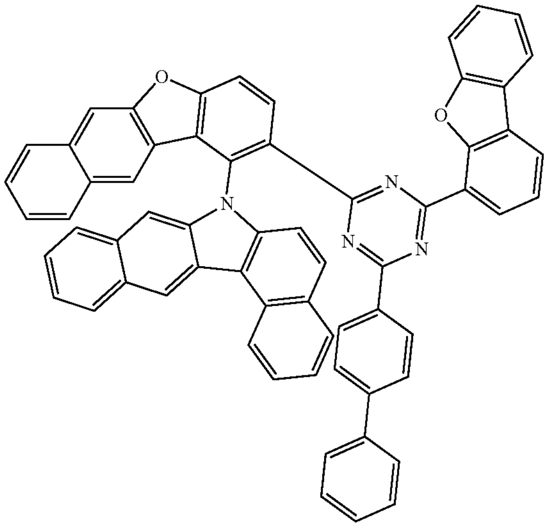
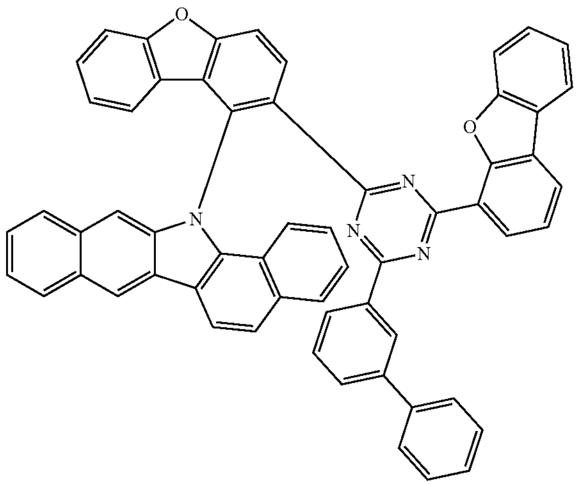
-continued
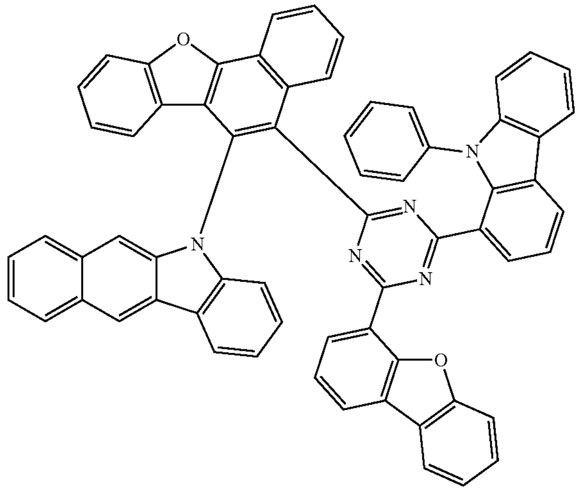
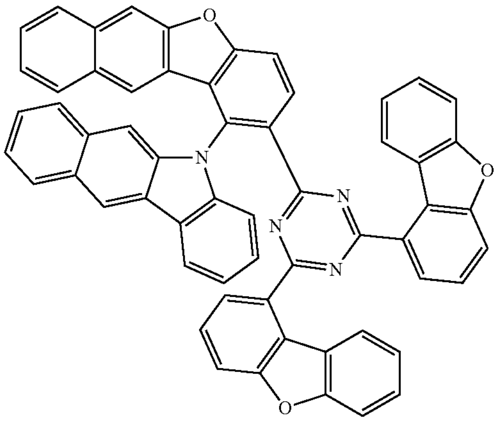
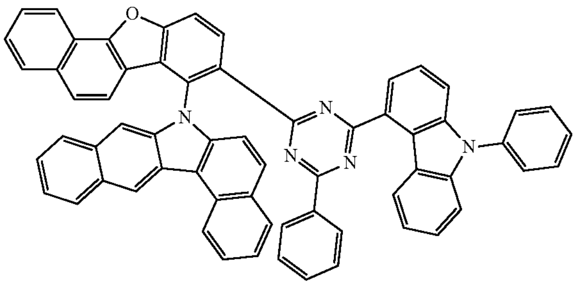
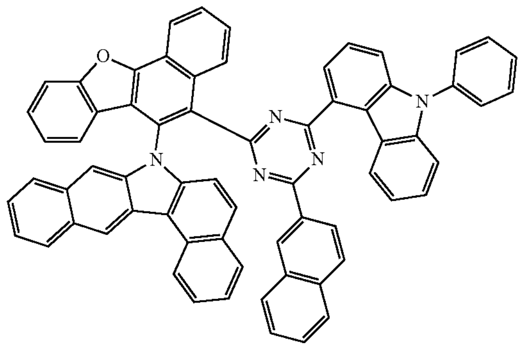

-continued
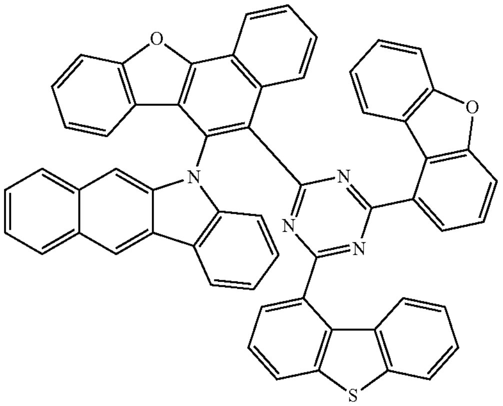
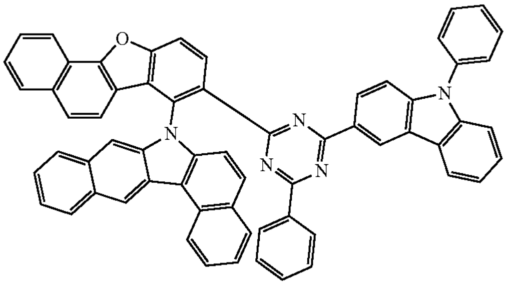
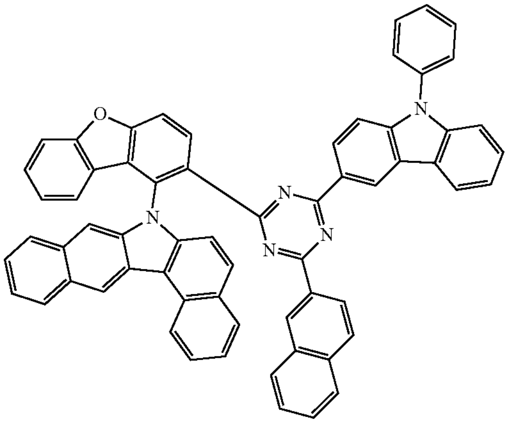
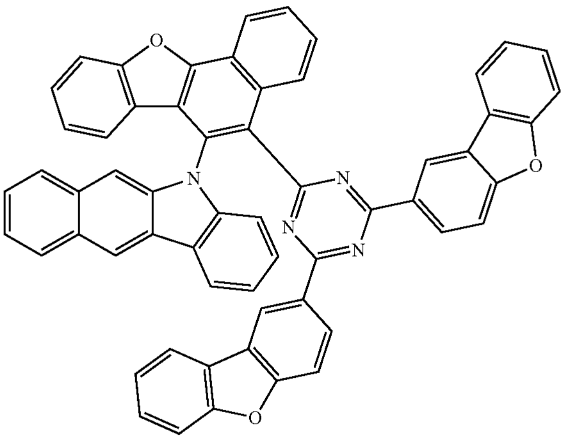
-continued
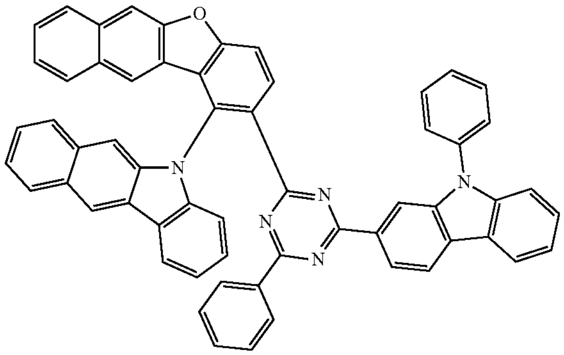
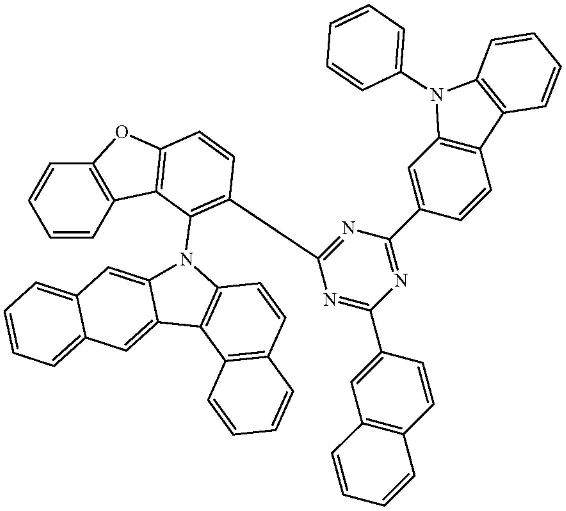
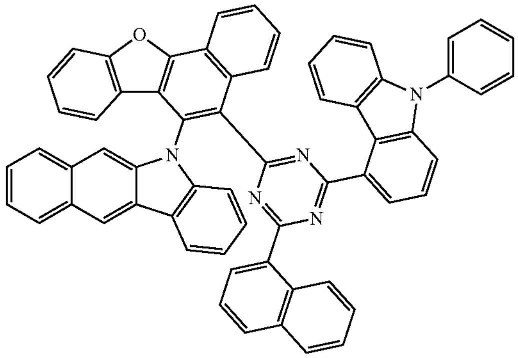
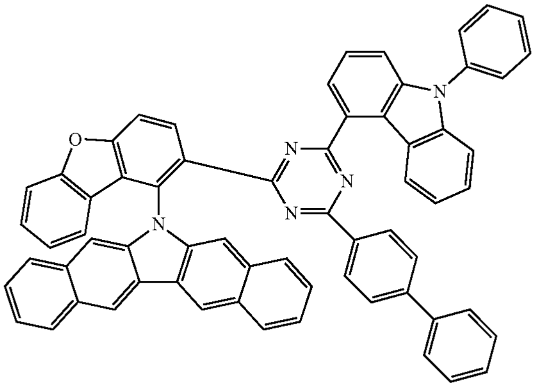

-continued
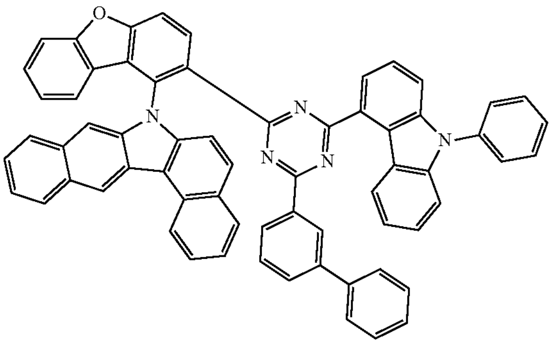
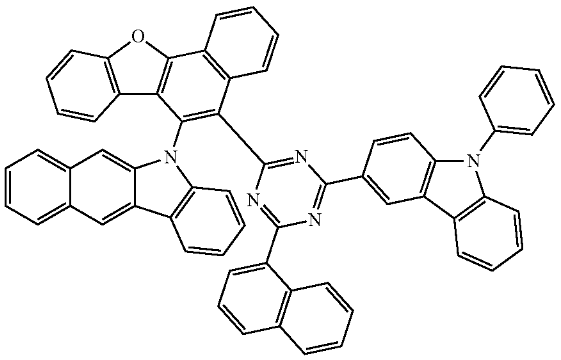
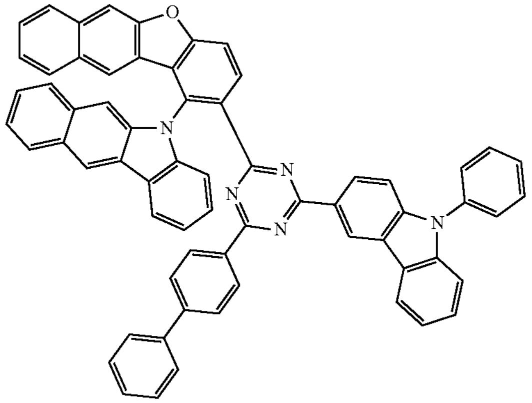
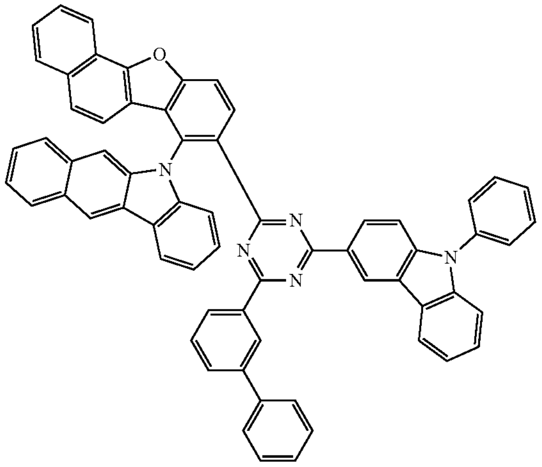
-continued
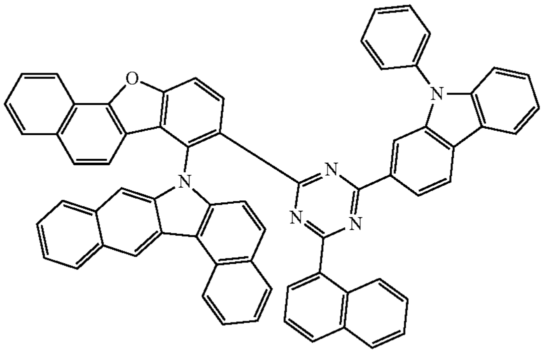
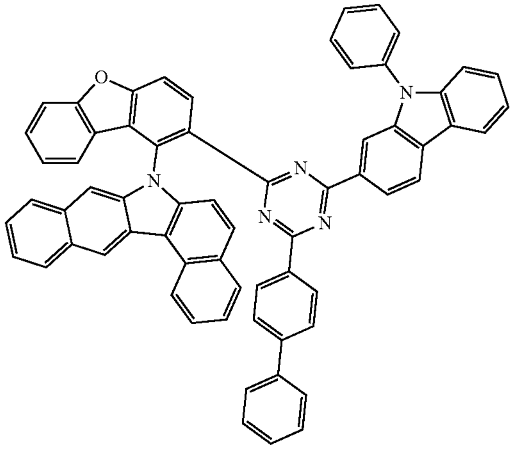
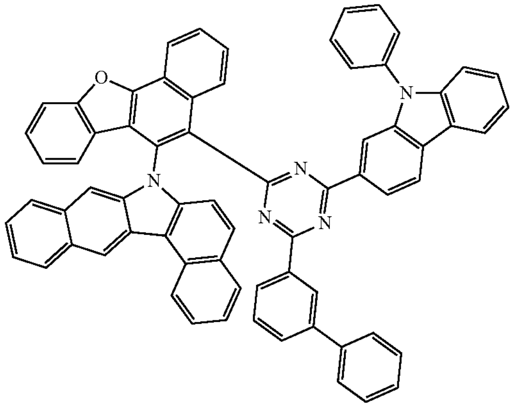
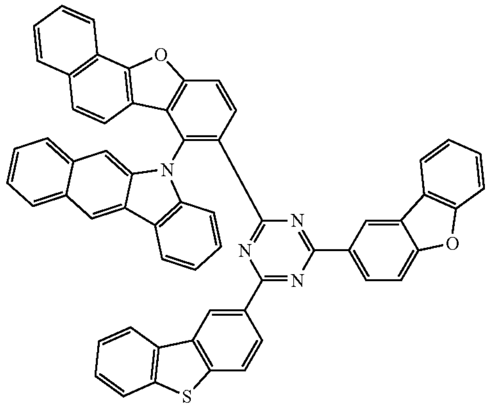

-continued
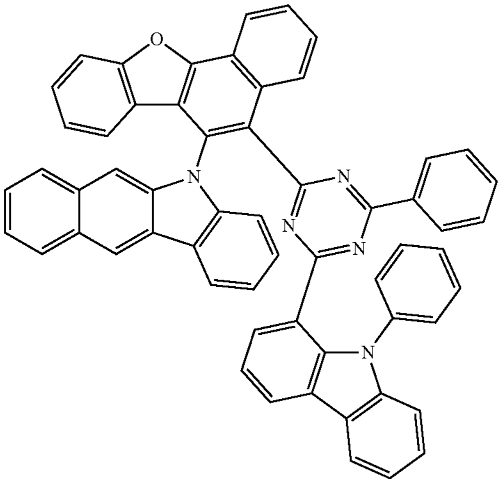
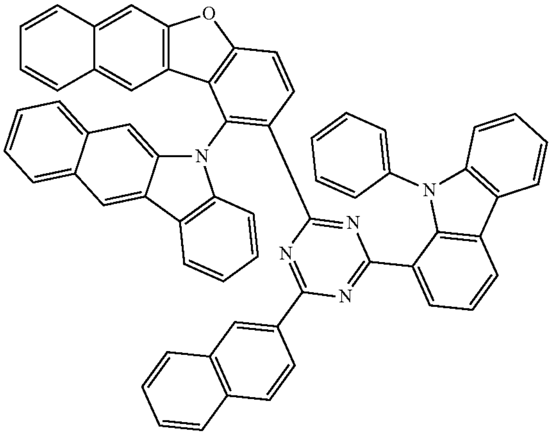
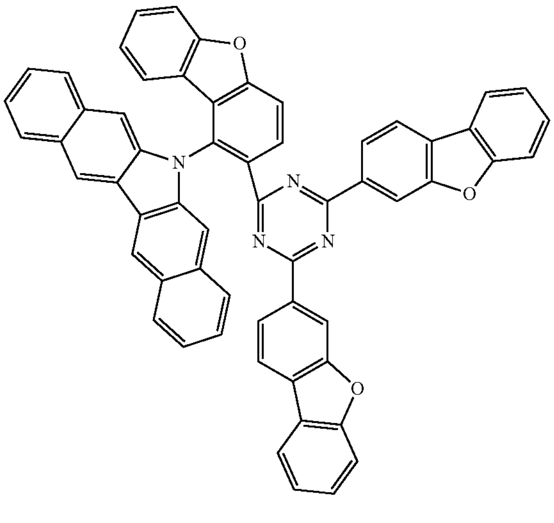
-continued
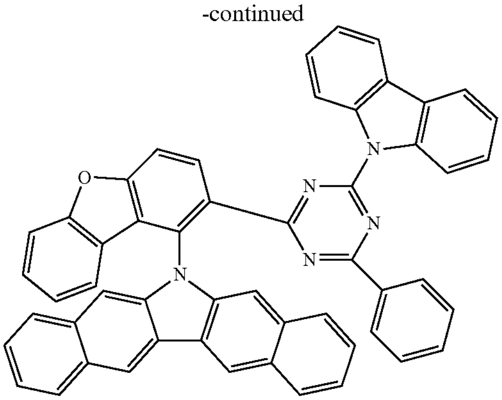
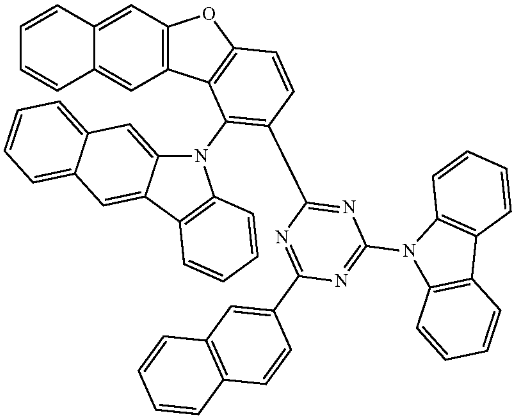
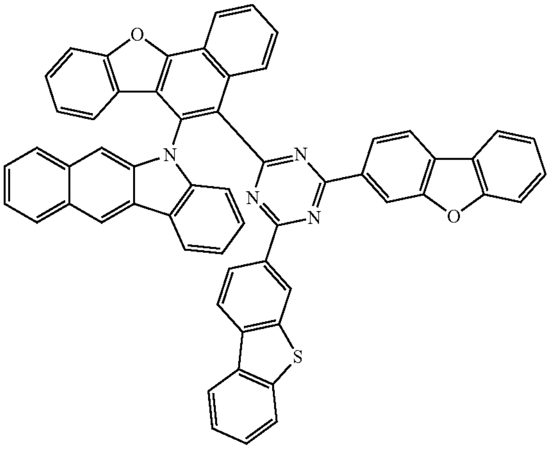
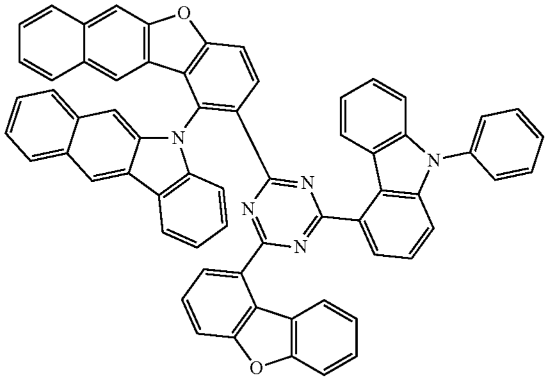

-continued
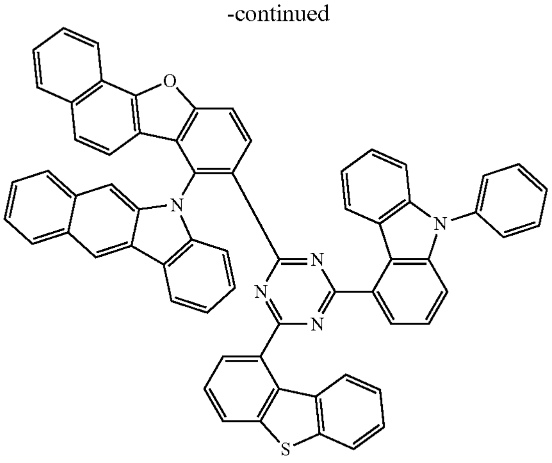
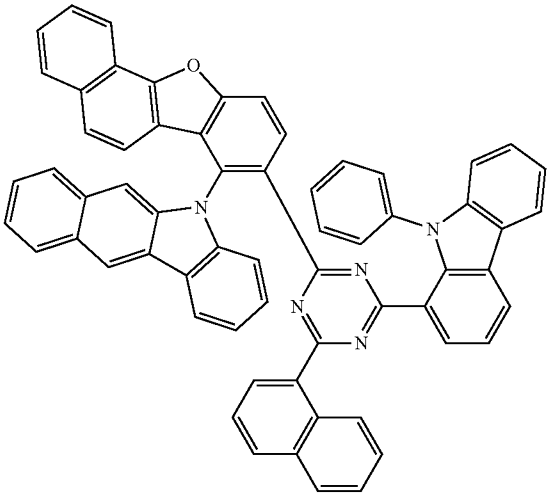
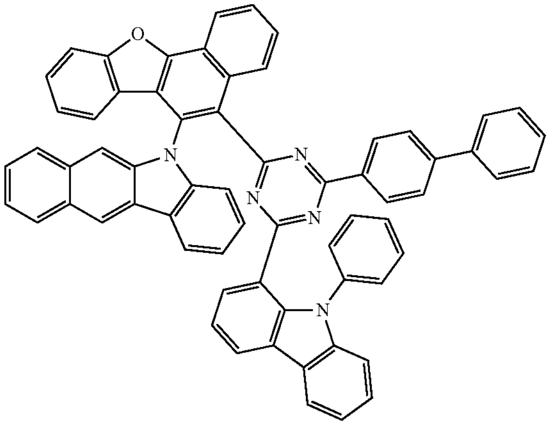
-continued
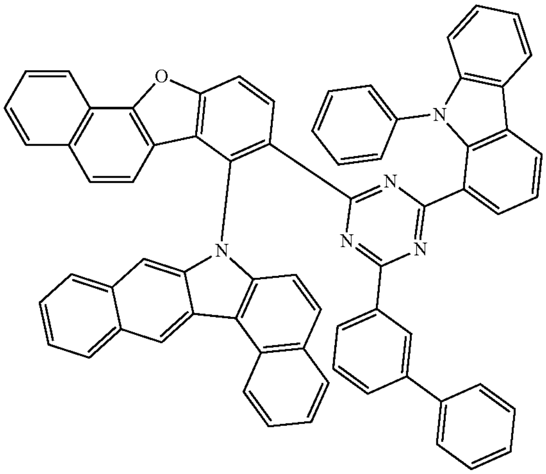
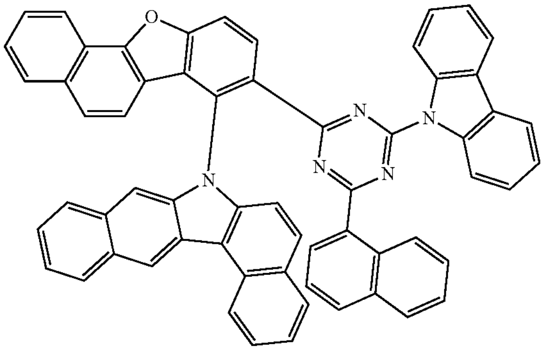
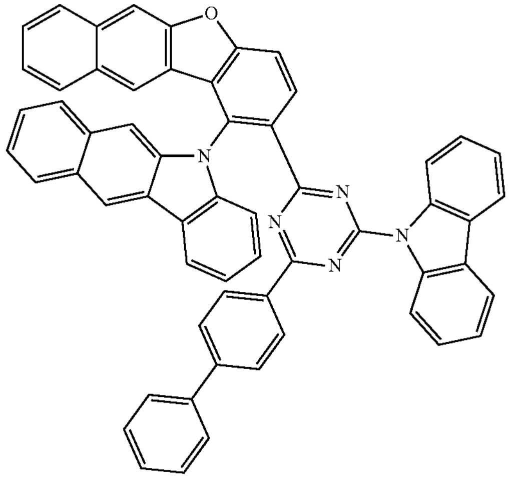

-continued
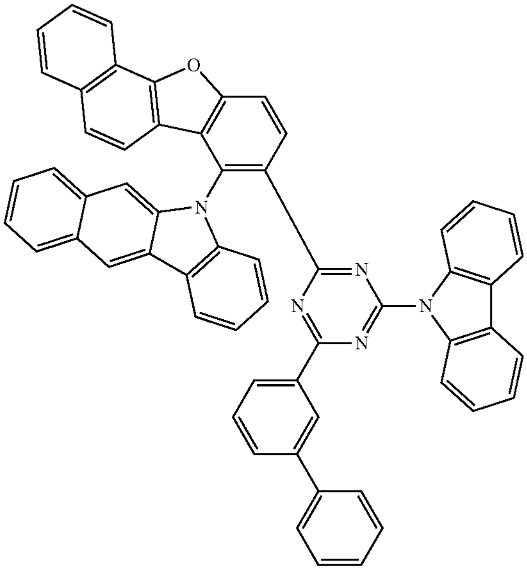
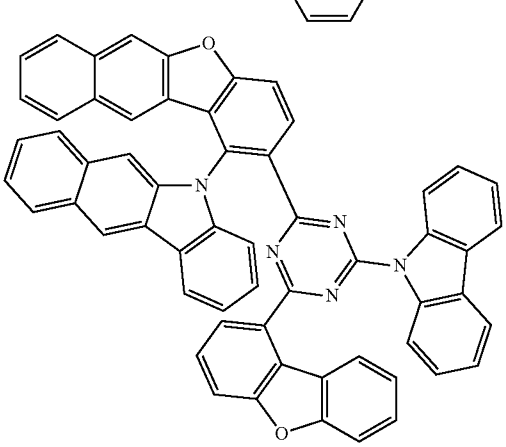
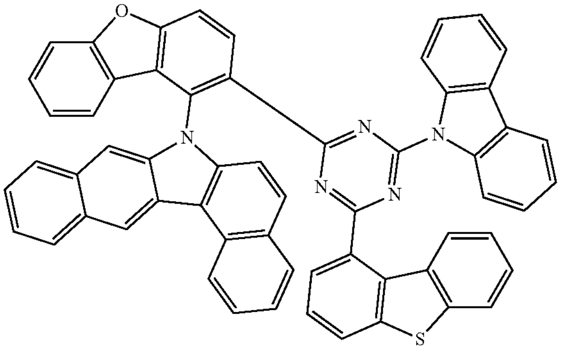
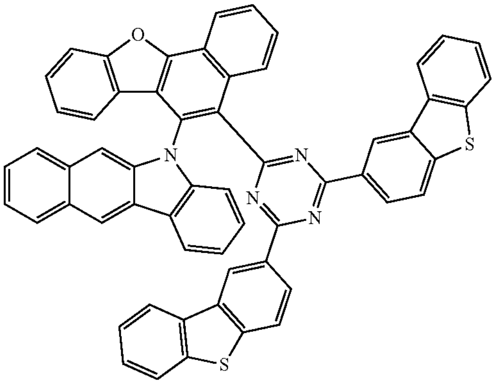
-continued
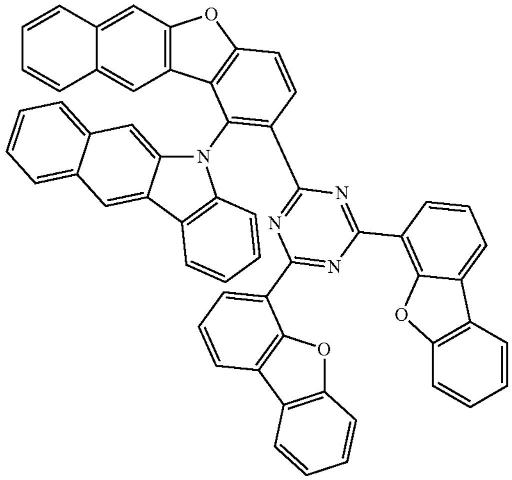
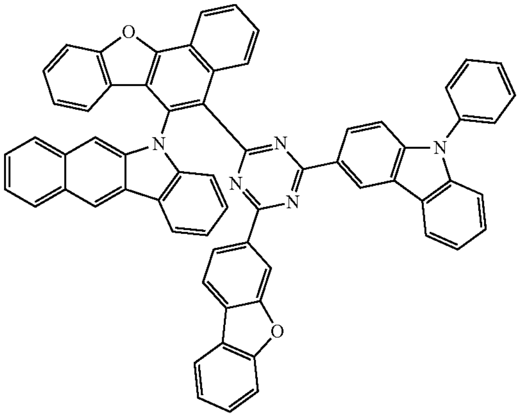
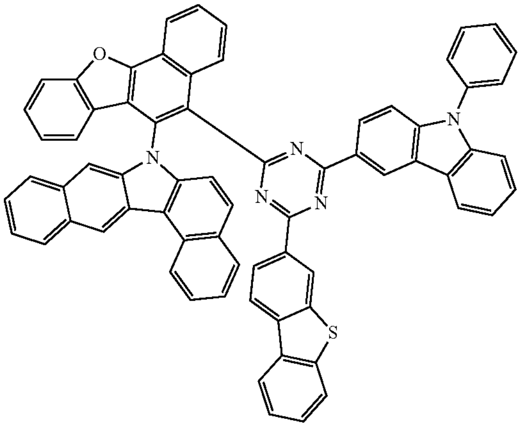
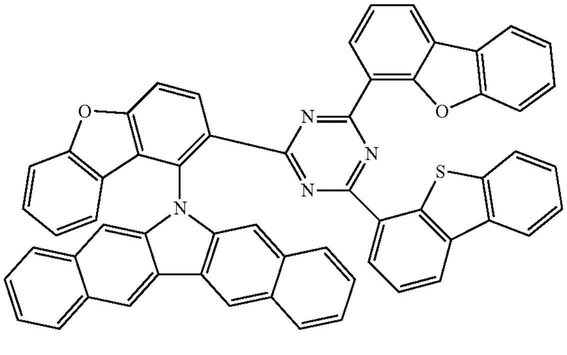

-continued
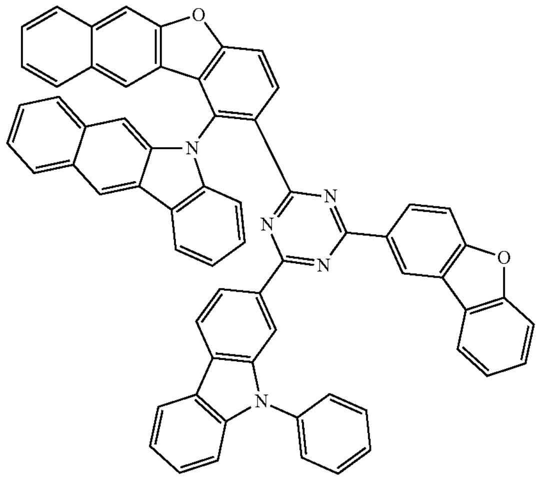
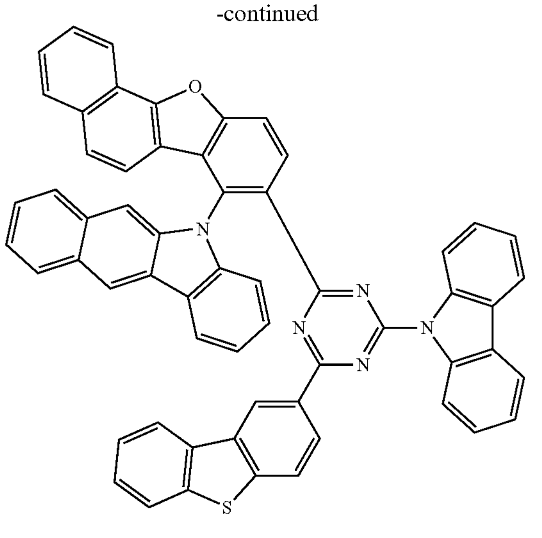
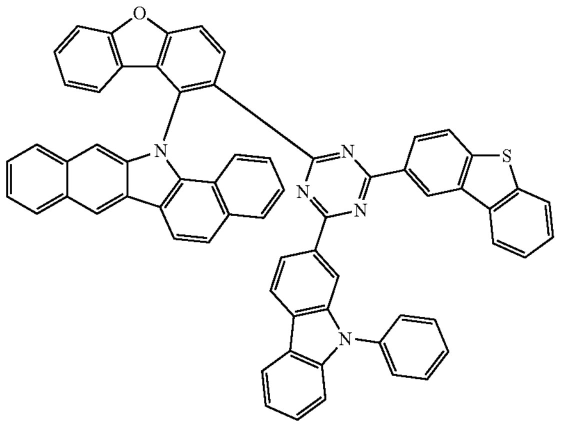
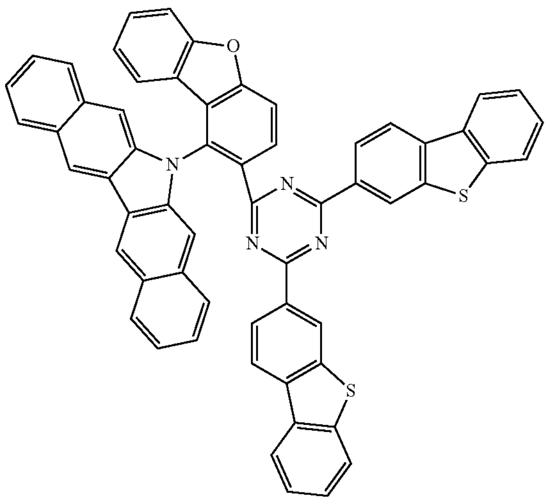
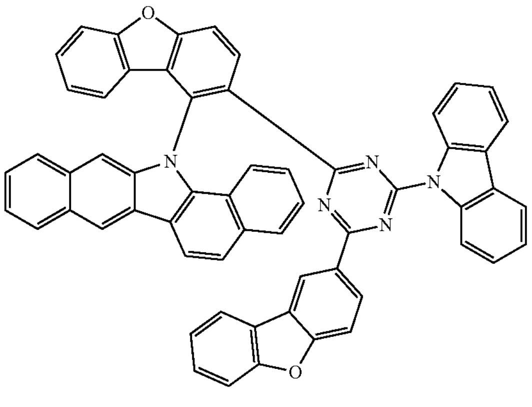
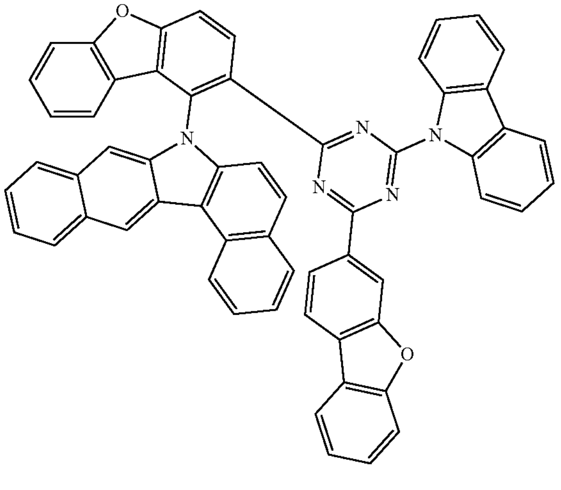
-continued -continued
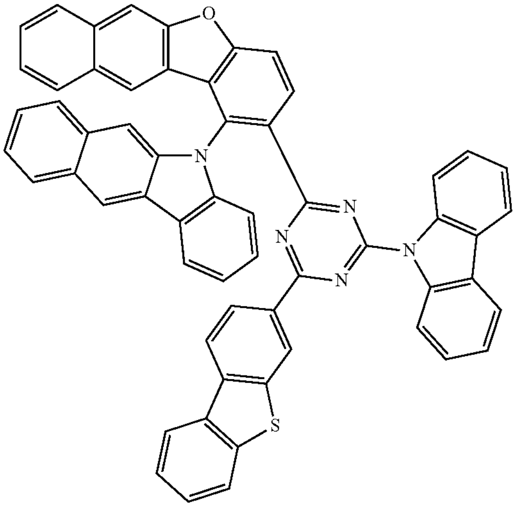
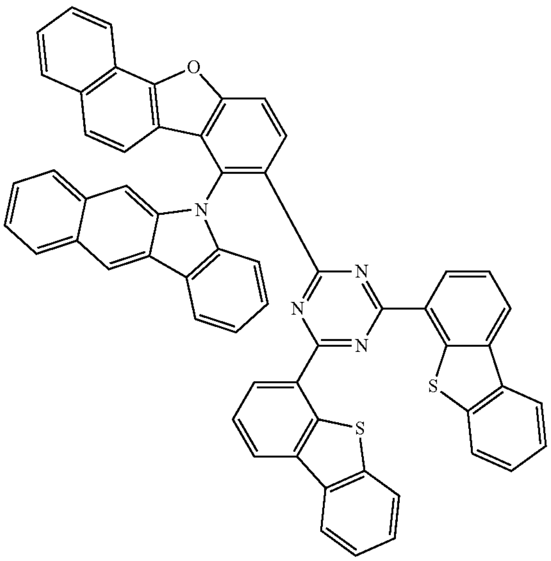
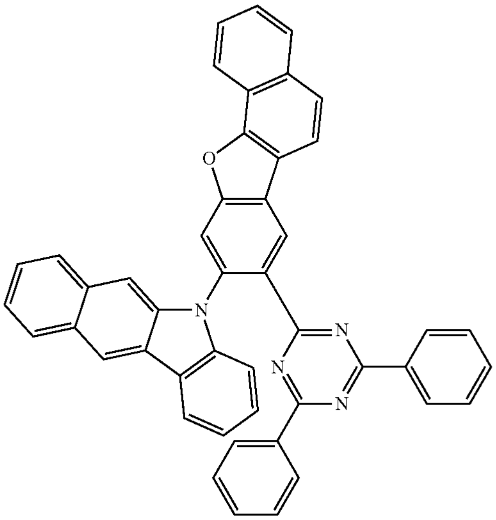
-continued
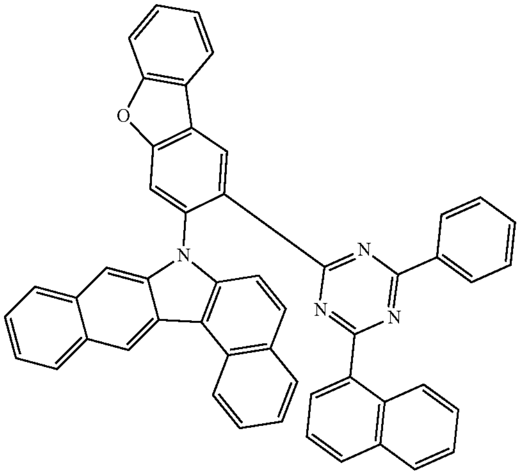
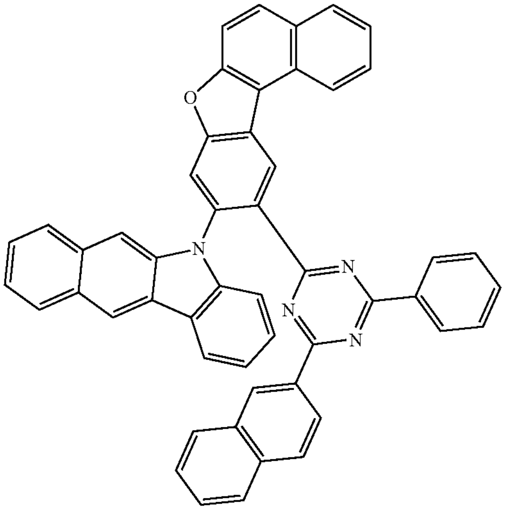
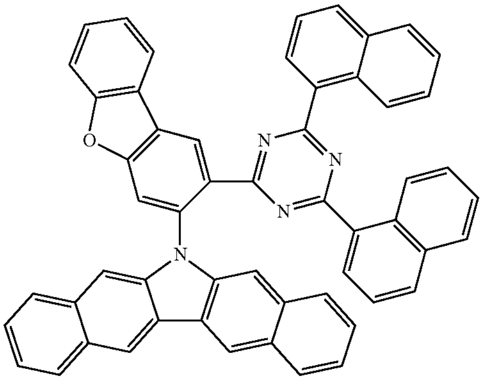

-continued
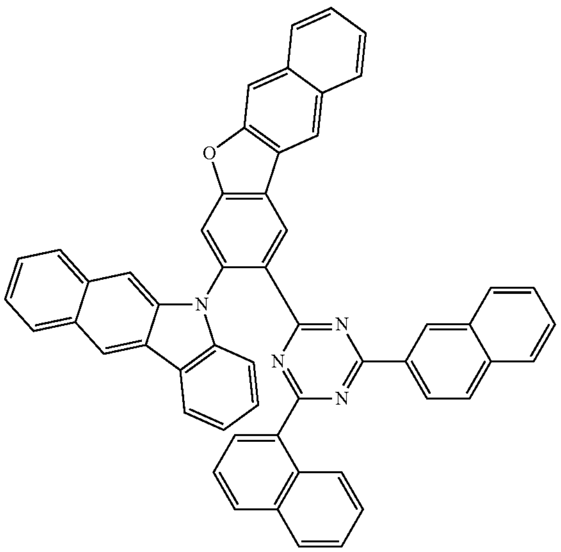
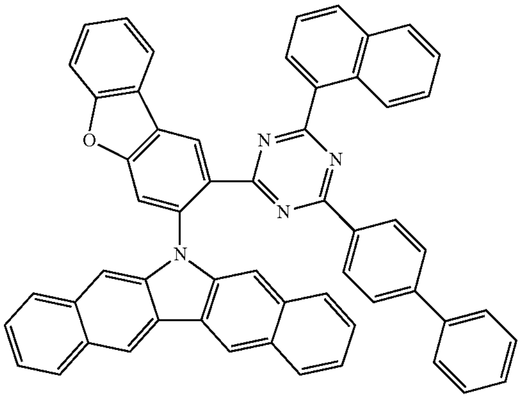
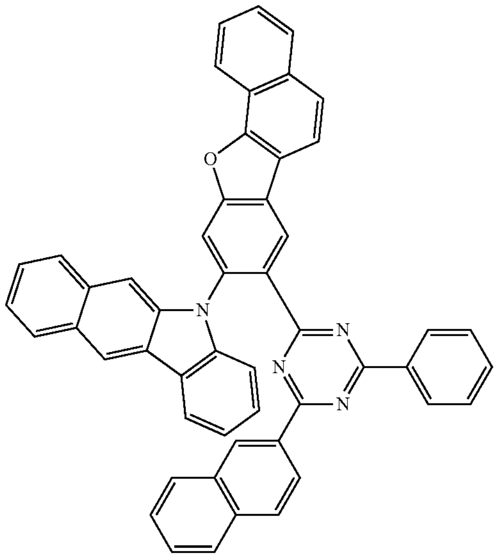
-continued
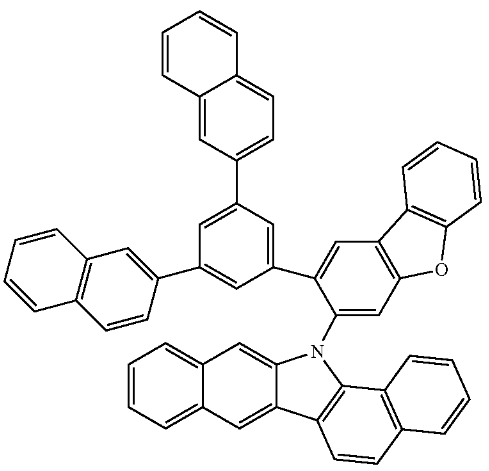
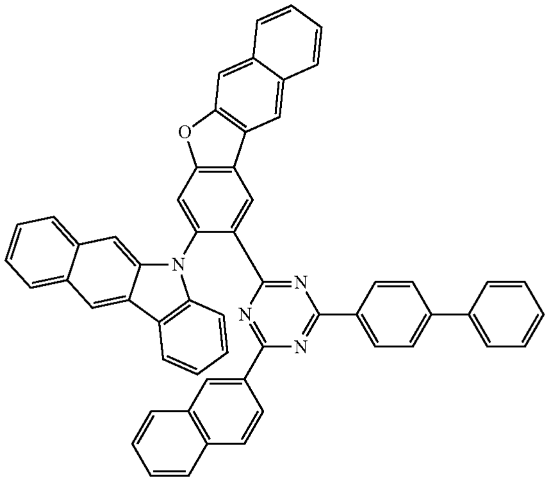
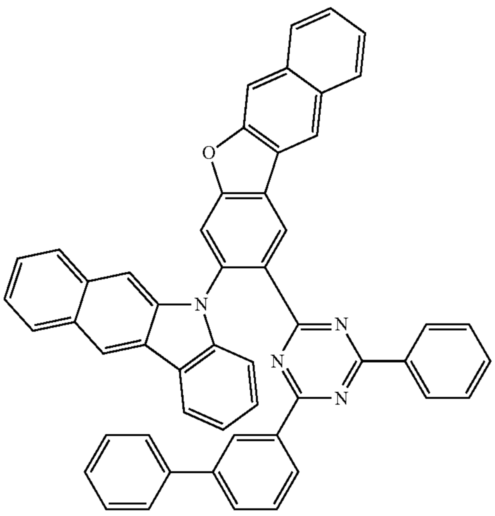

-continued
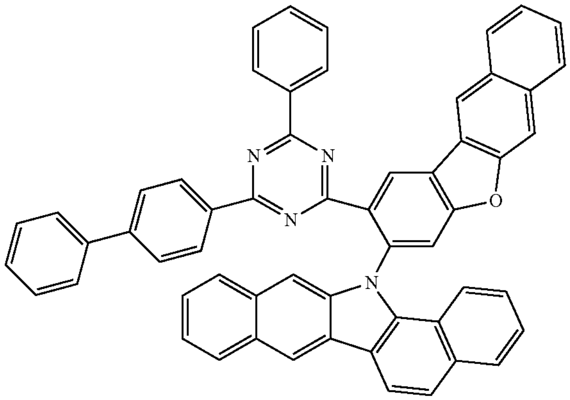
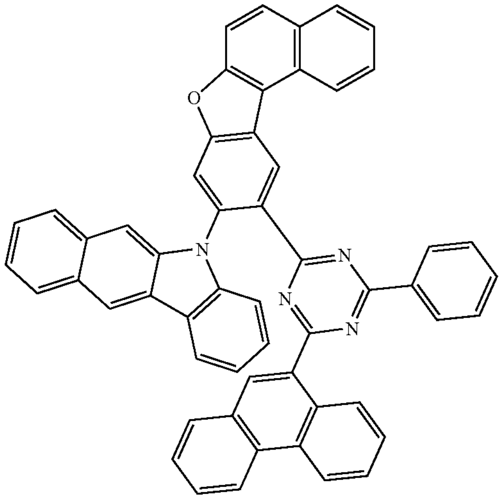
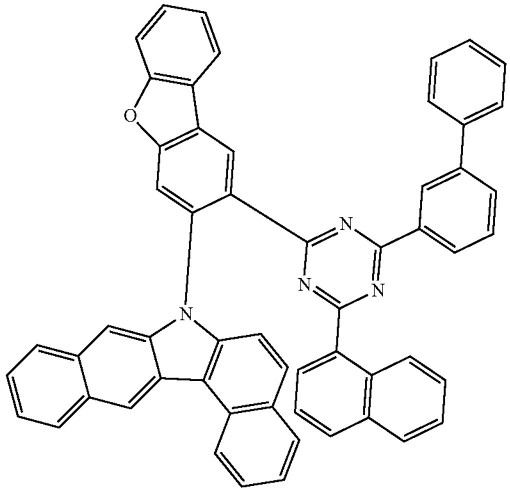
-continued
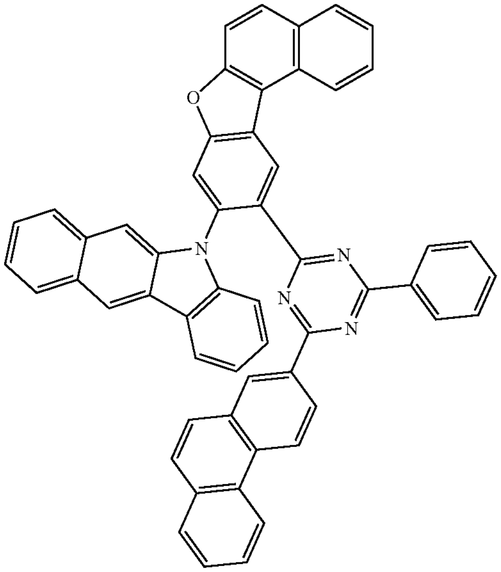
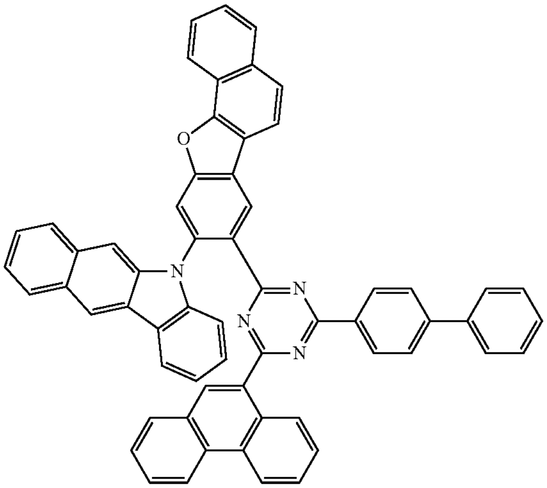
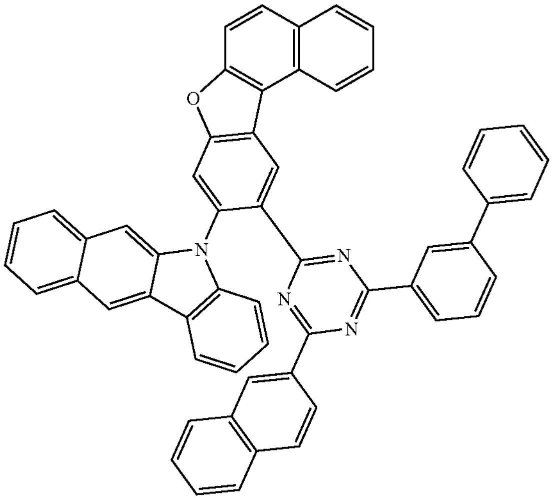

-continued
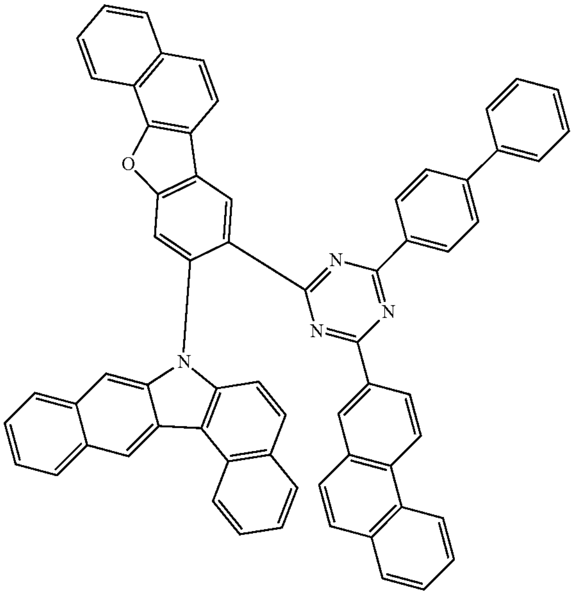
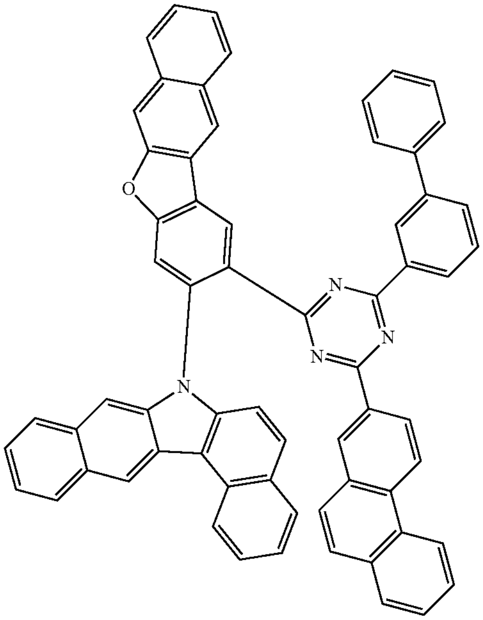
-continued
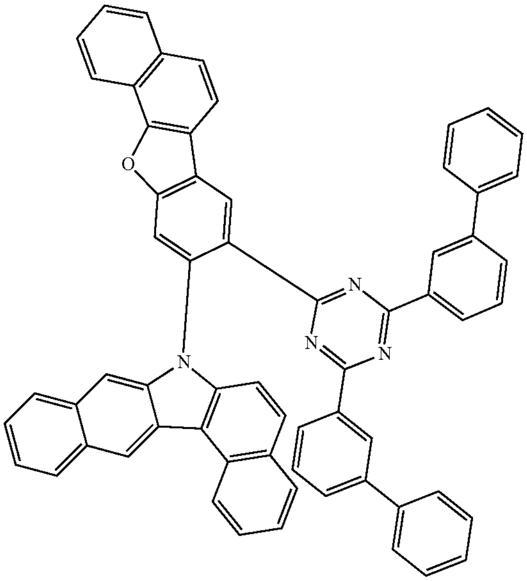
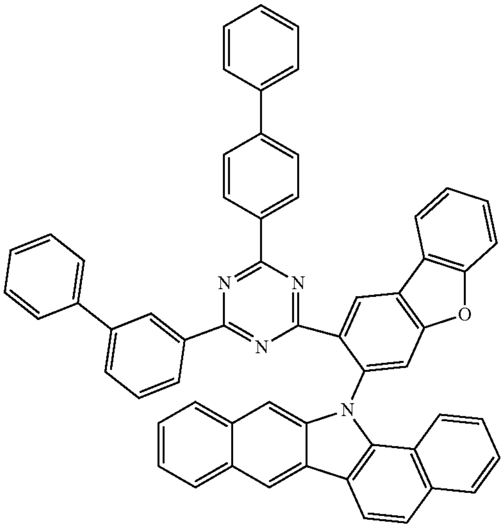
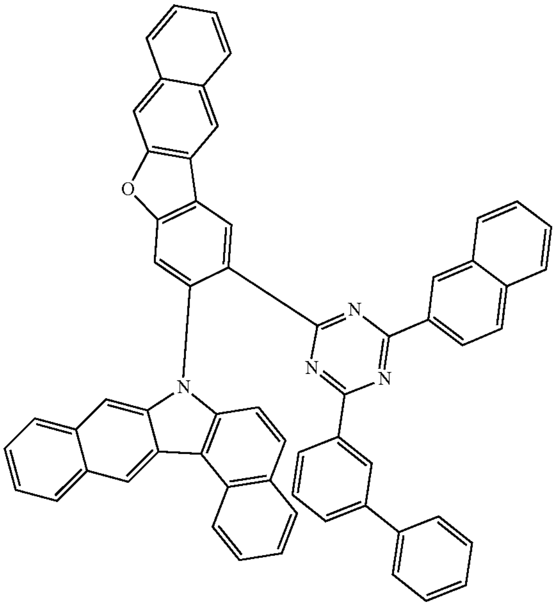

-continued
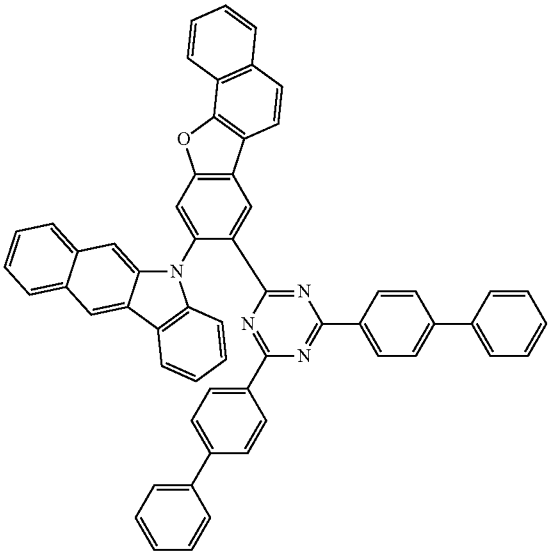
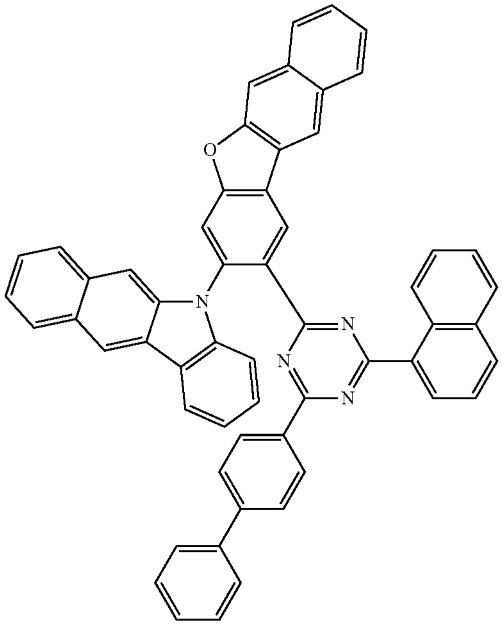
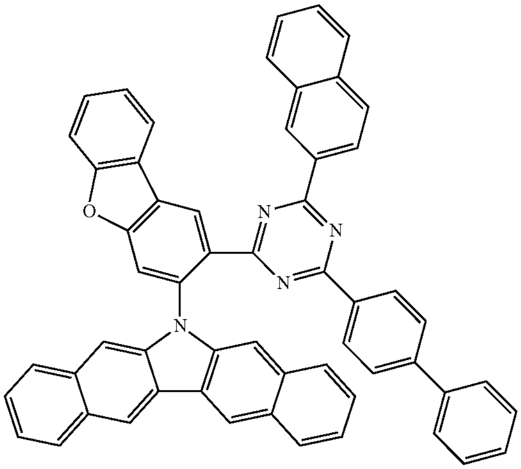
-continued
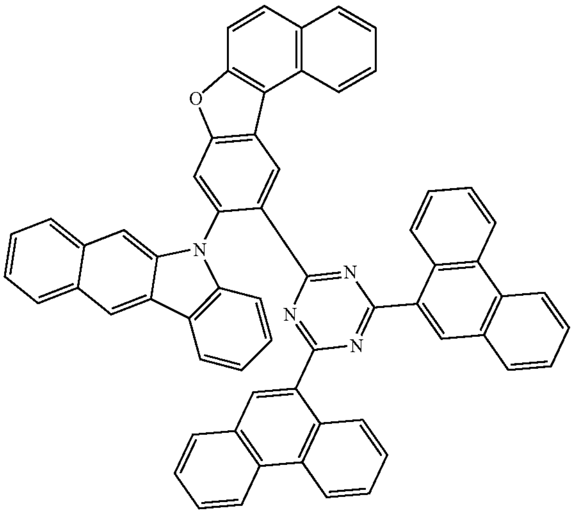
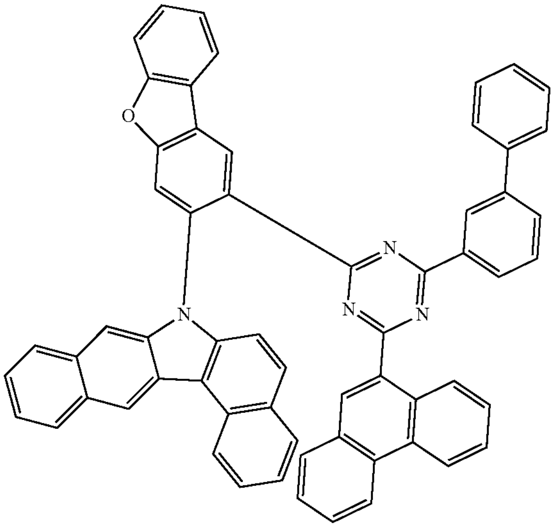
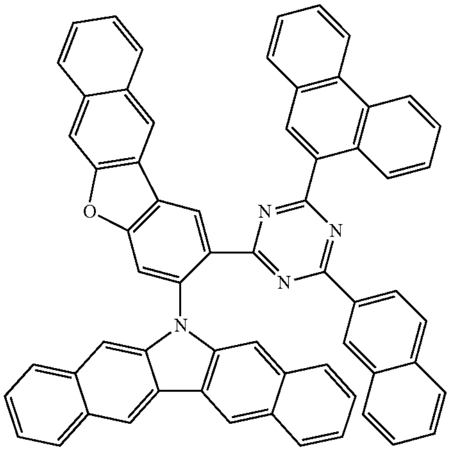

-continued
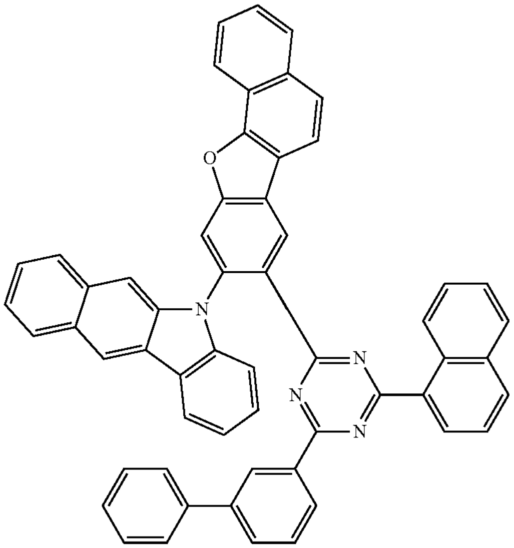
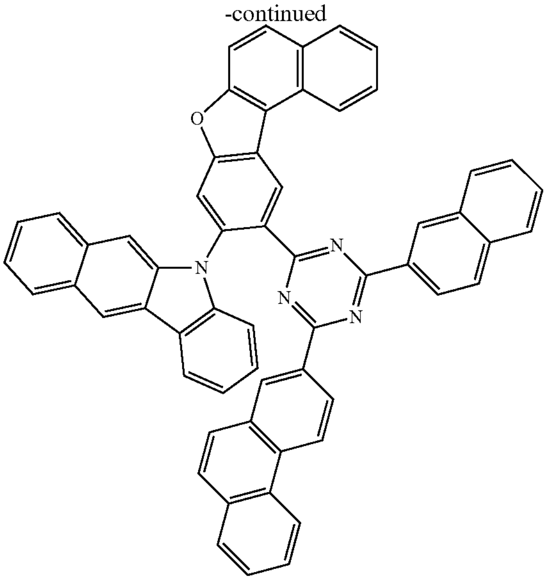
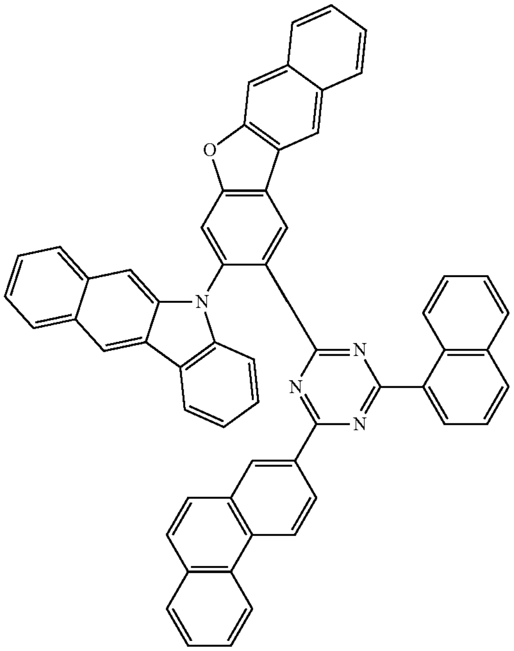
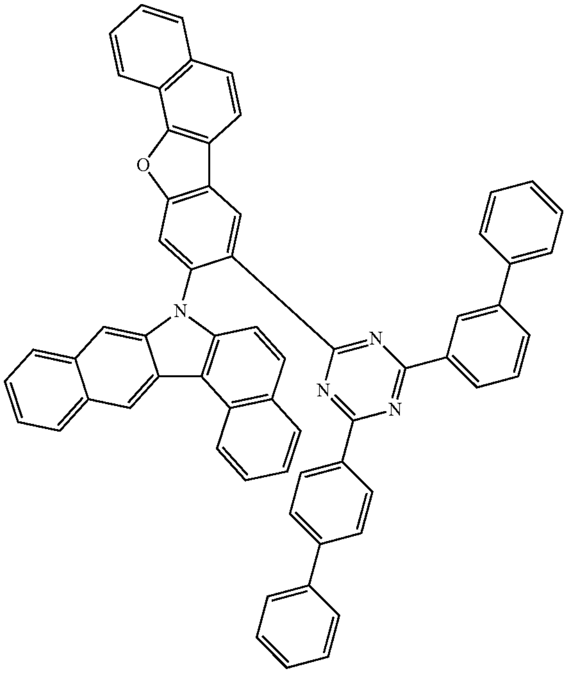

-continued
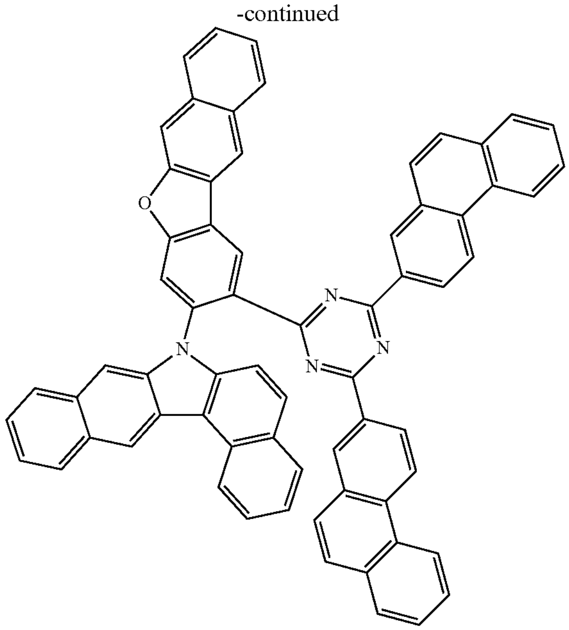
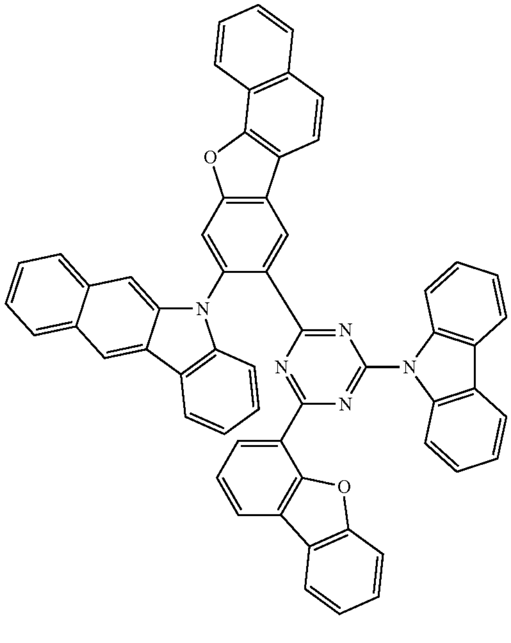
-continued
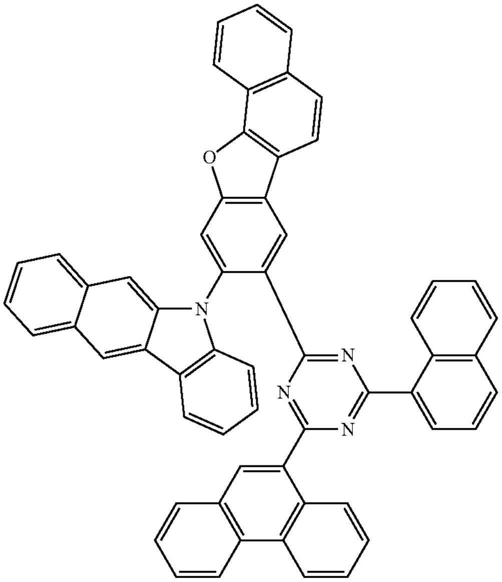
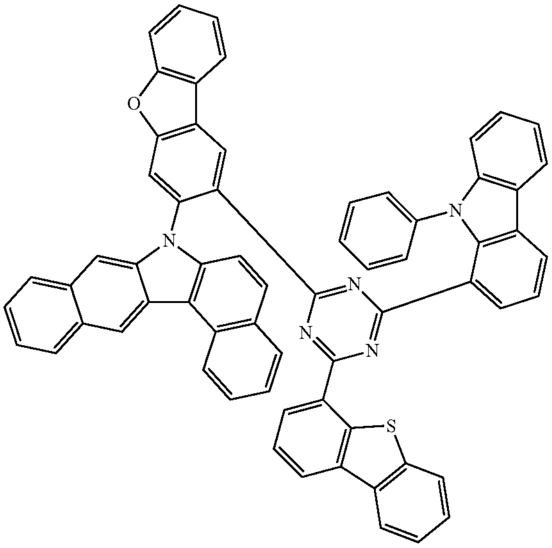
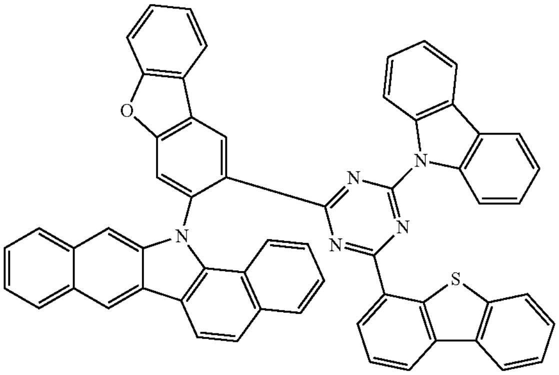

-continued
-continued
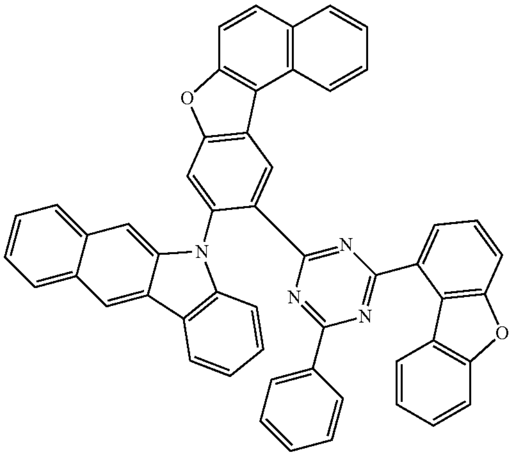
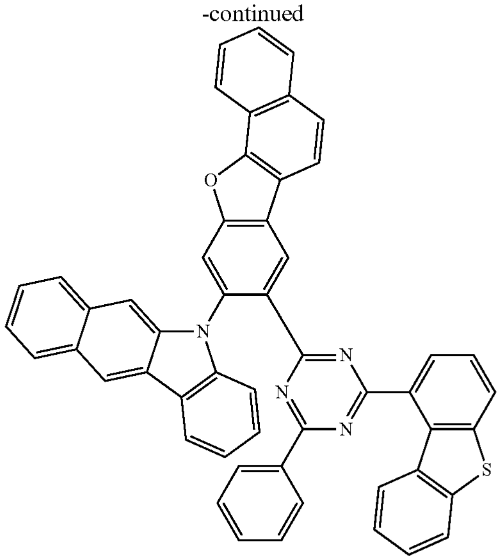
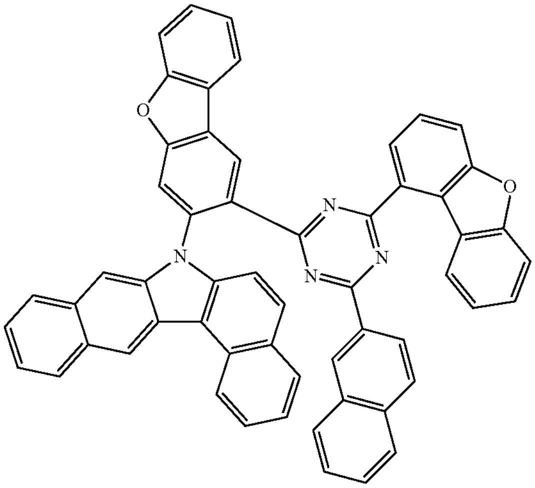
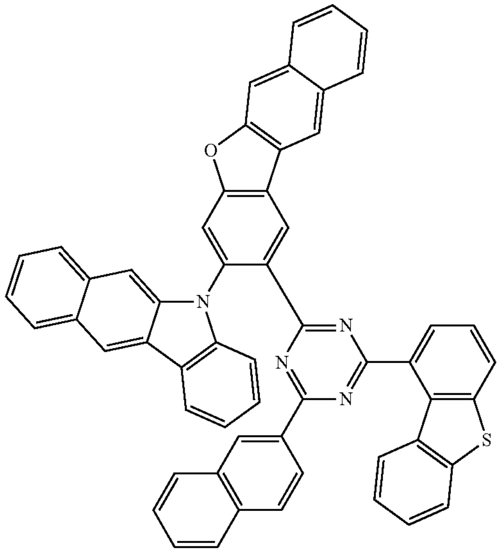
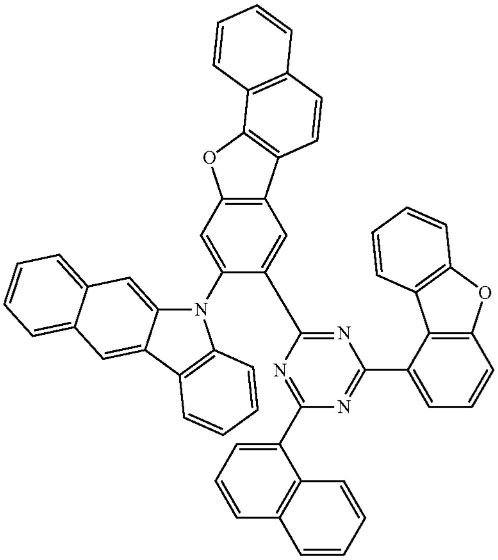
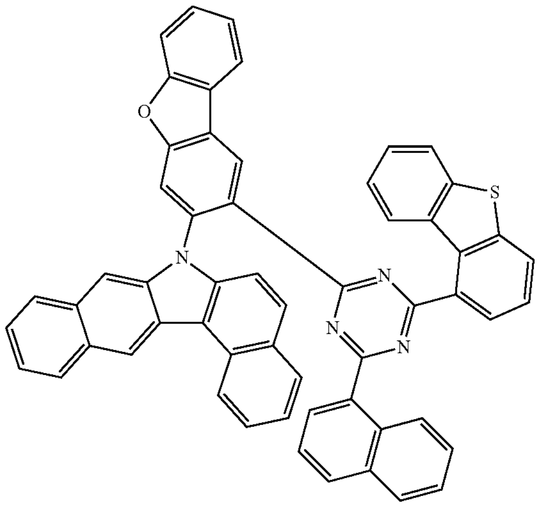

-continued
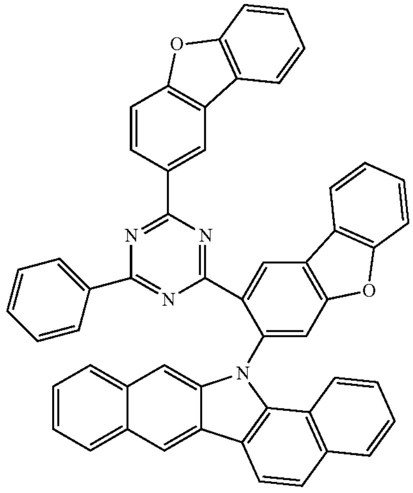
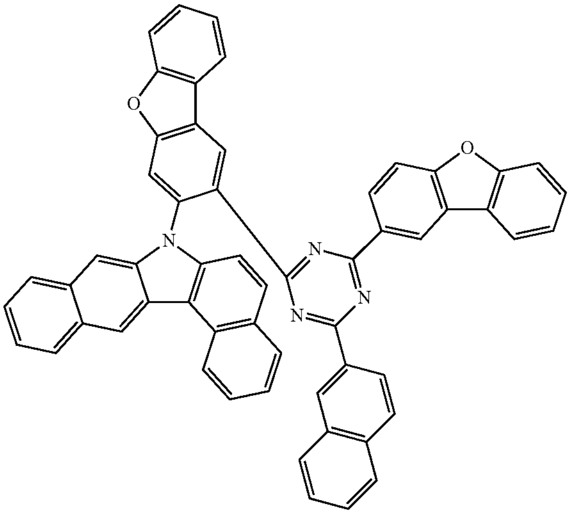
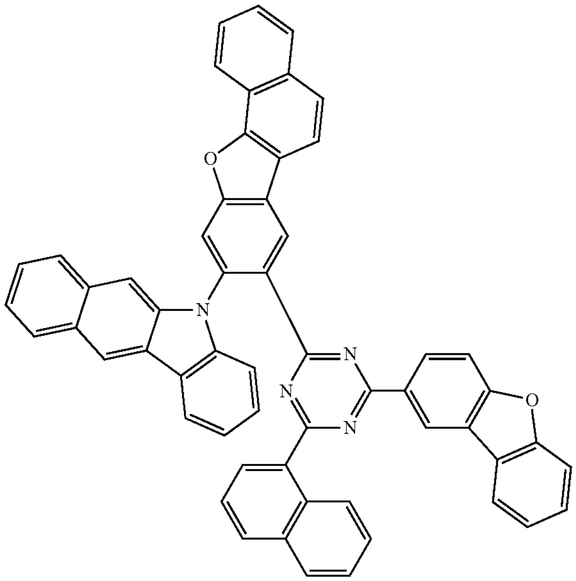
-continued
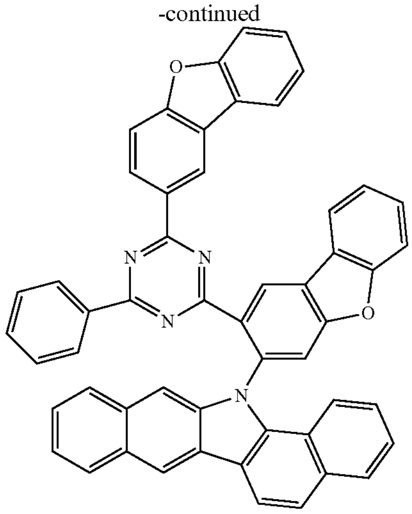
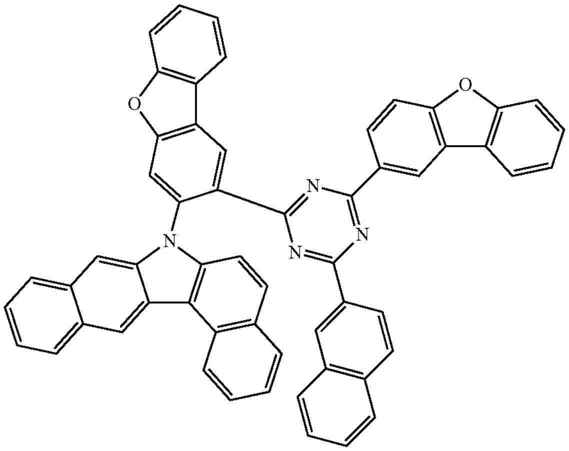
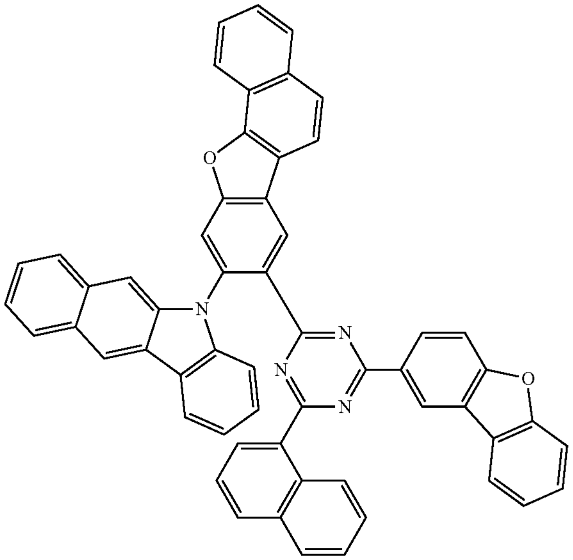

-continued
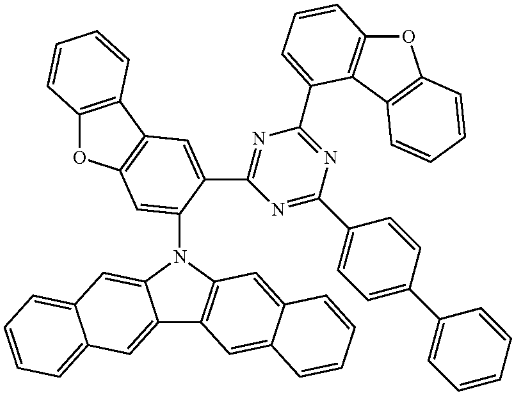
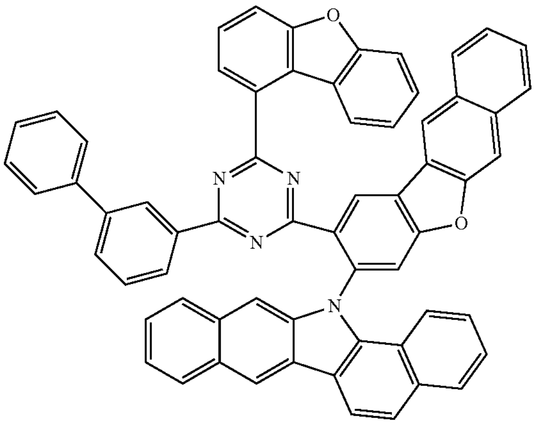
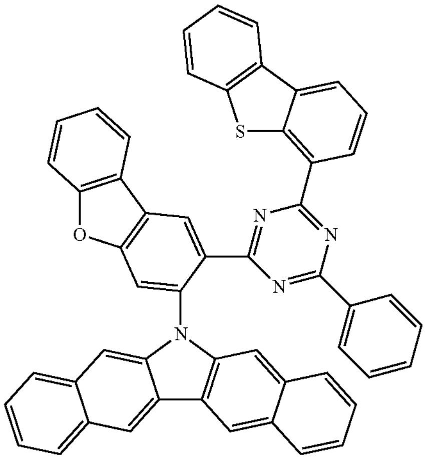
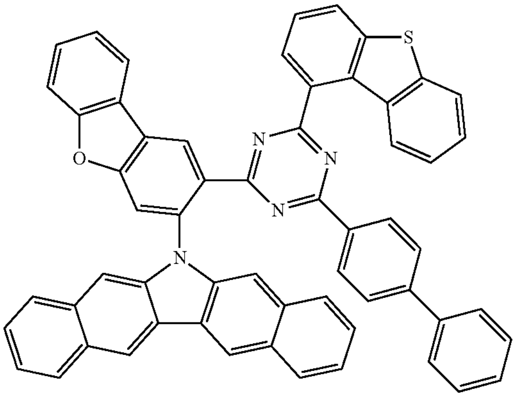
-continued
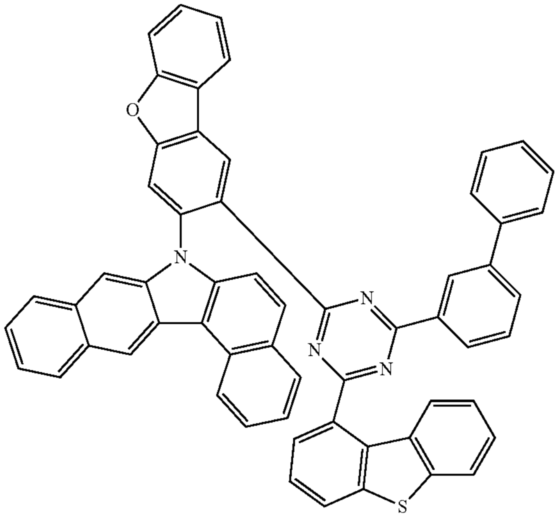
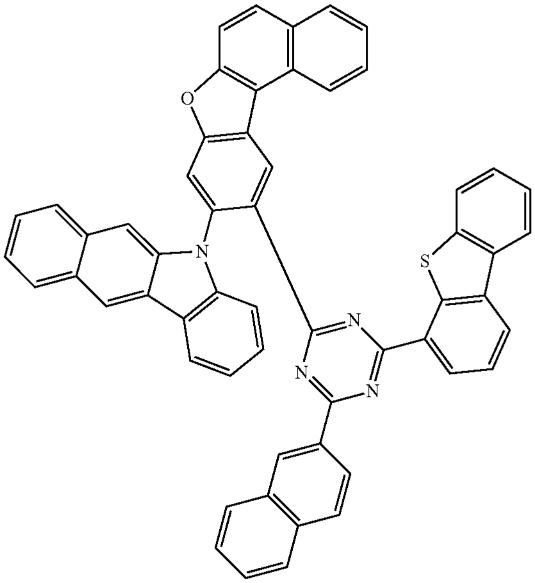
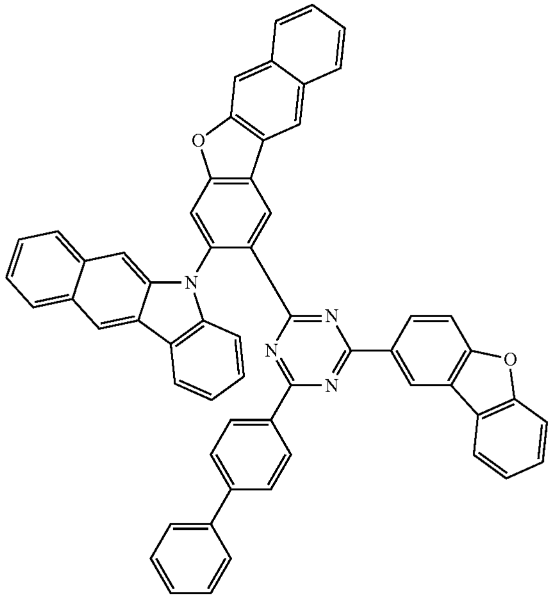

-continued
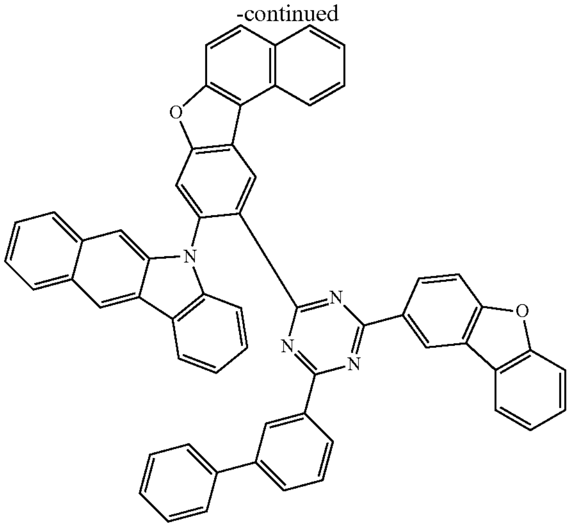
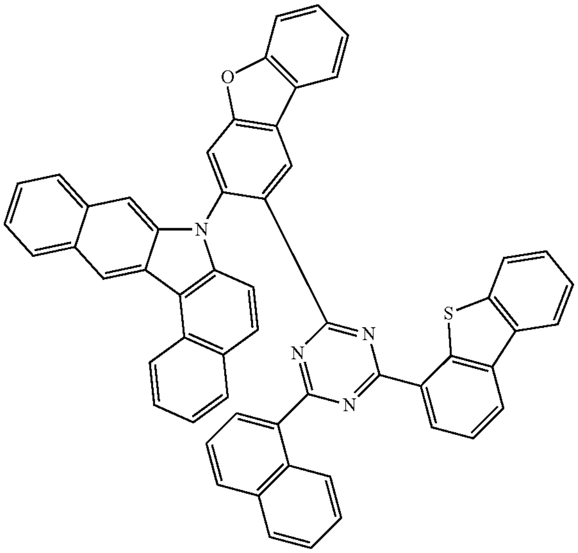
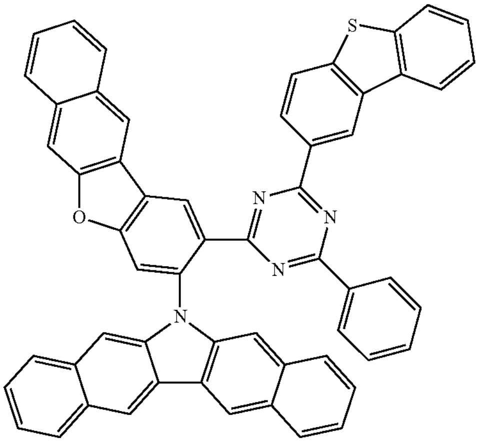
-continued
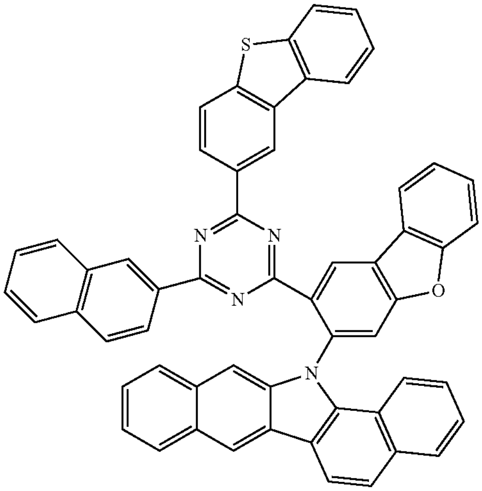
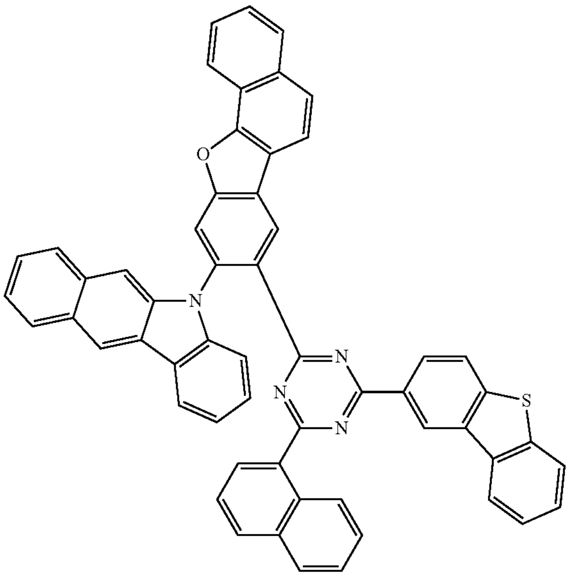
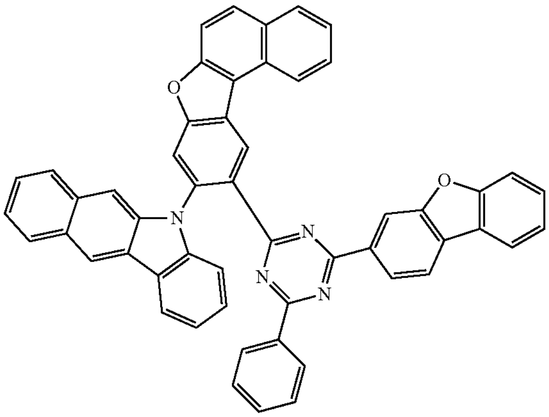

-continued
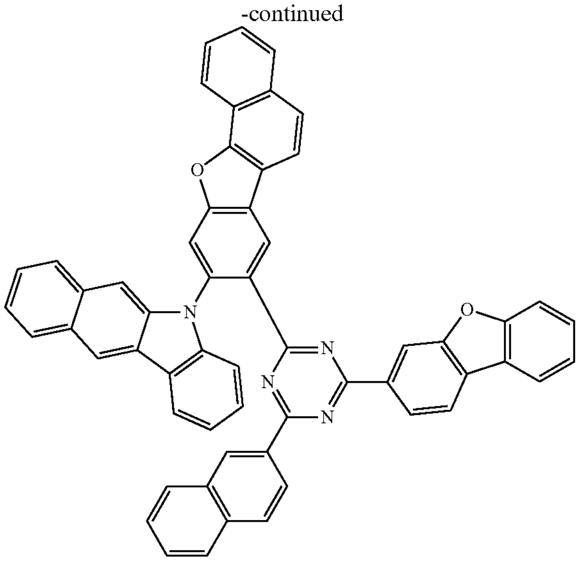
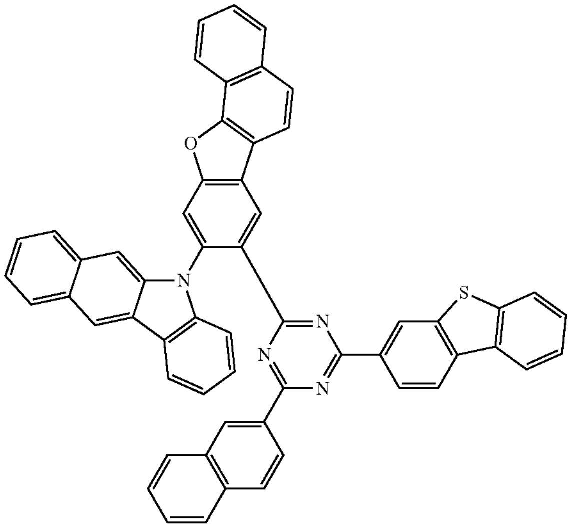
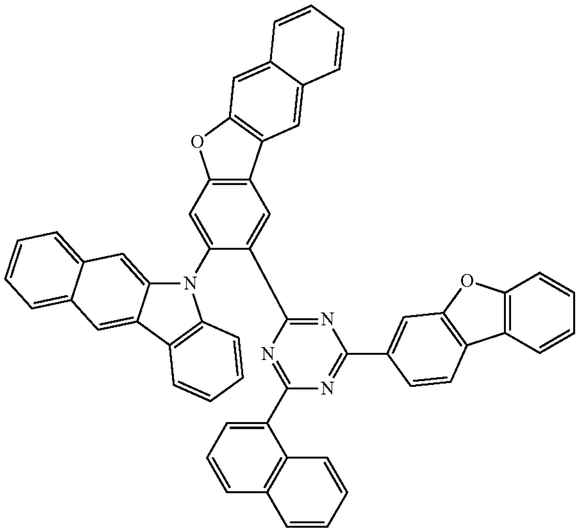
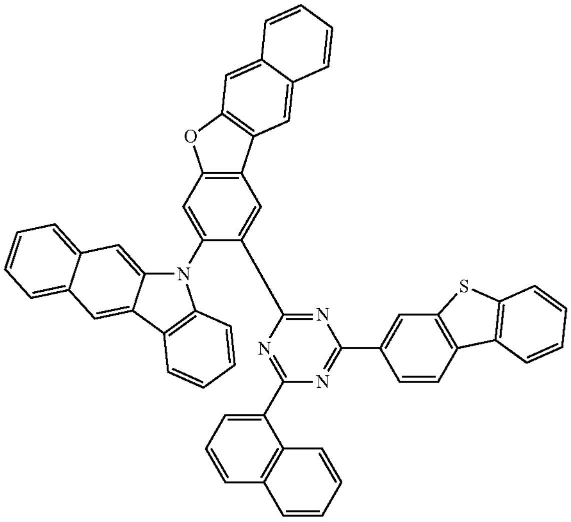
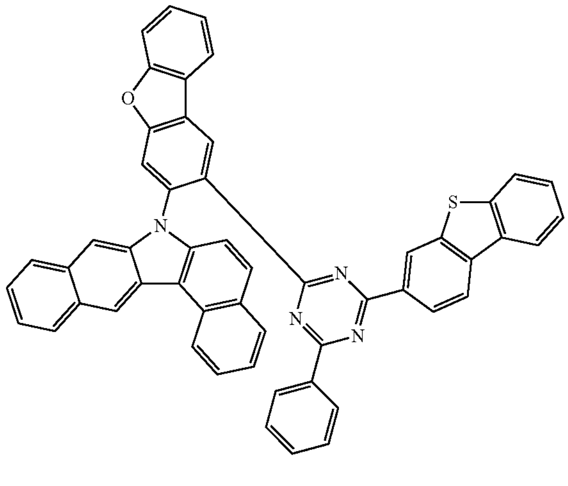
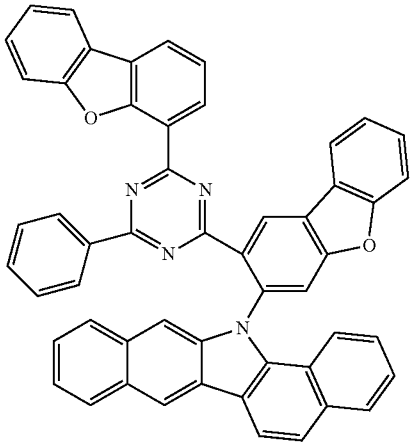
-continued -continued
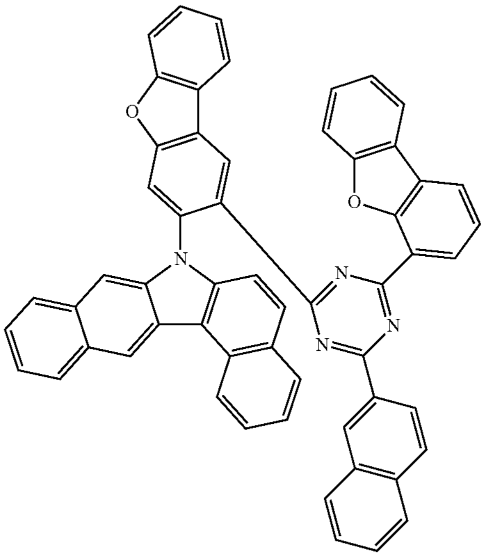
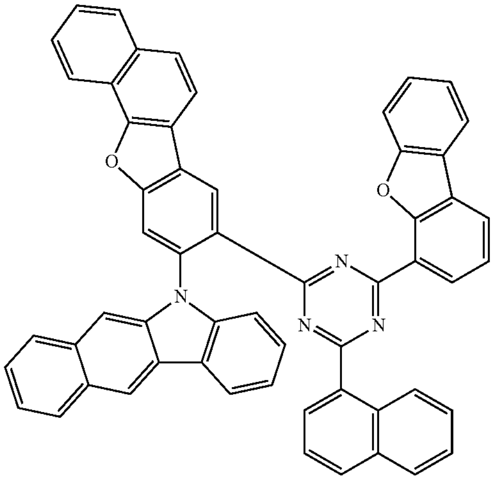
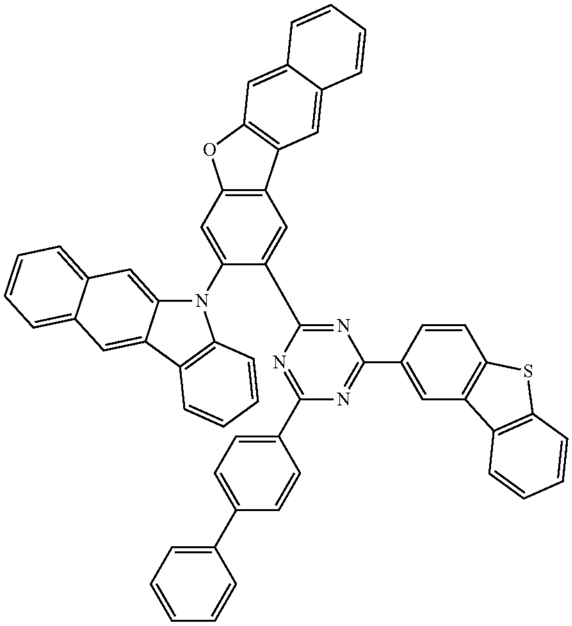
-continued
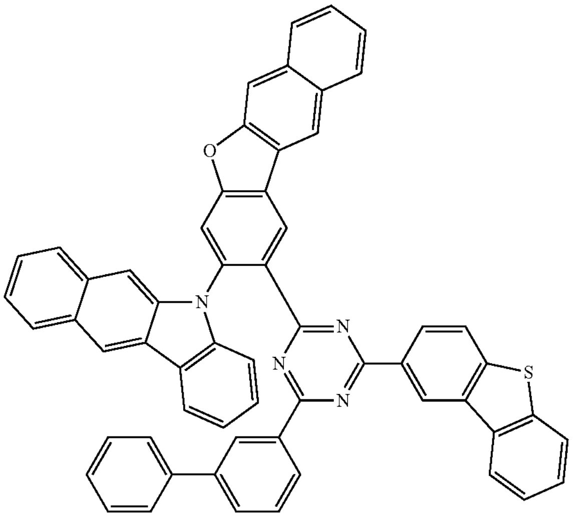
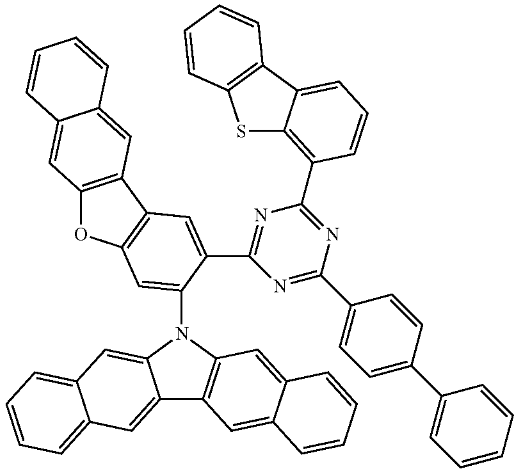
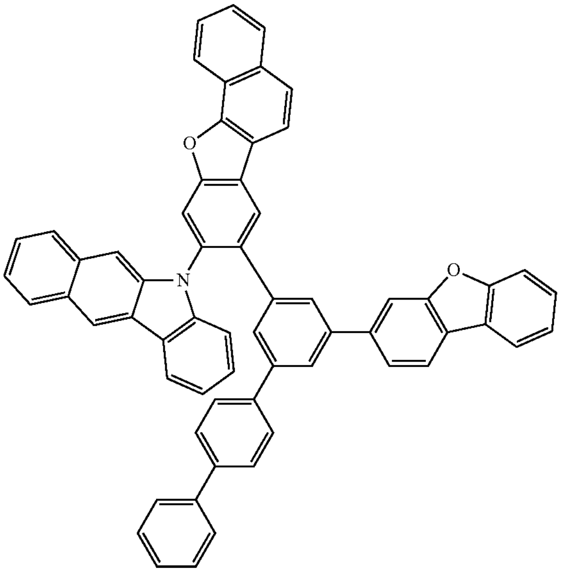

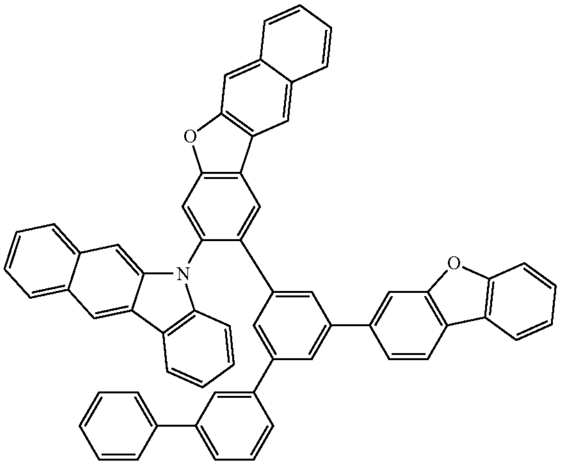
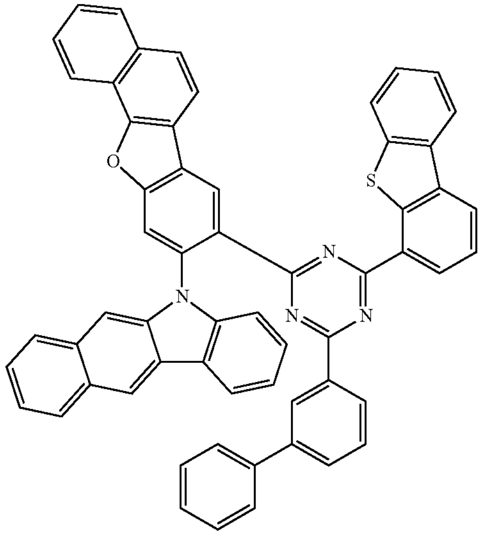
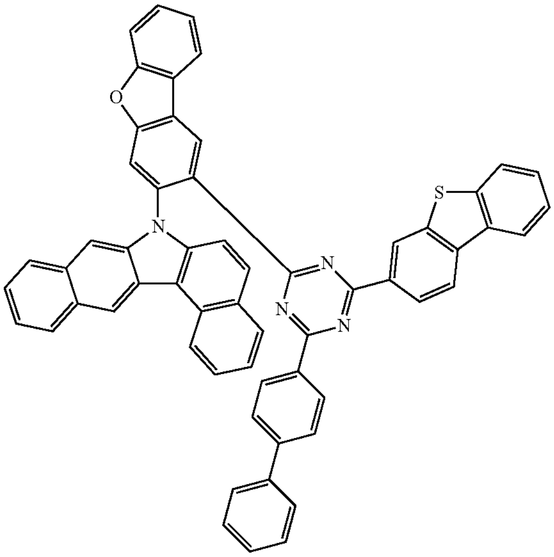
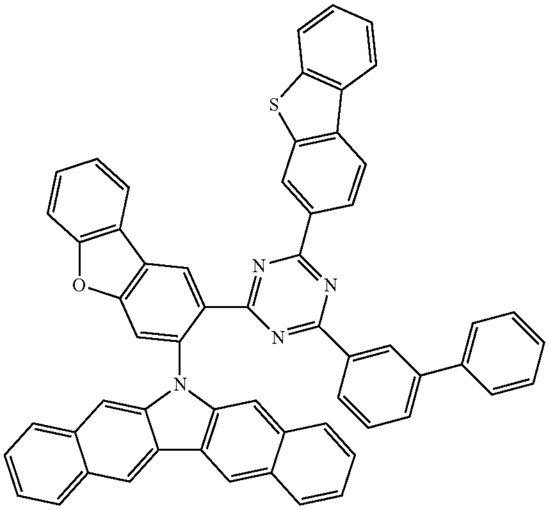
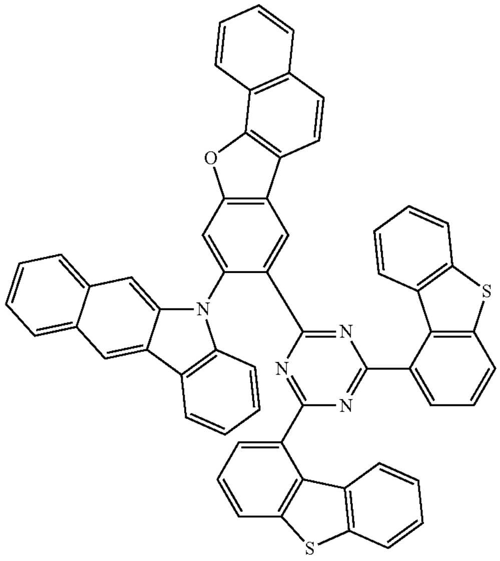
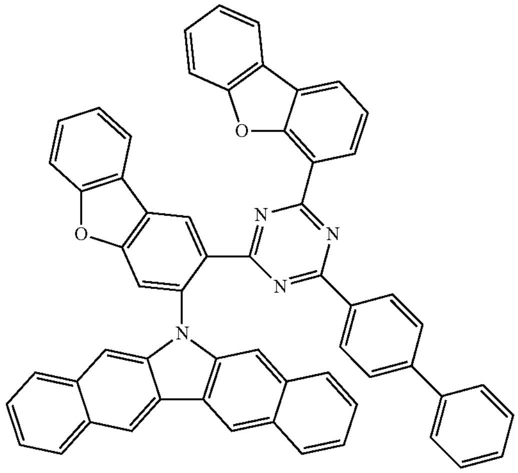

-continued
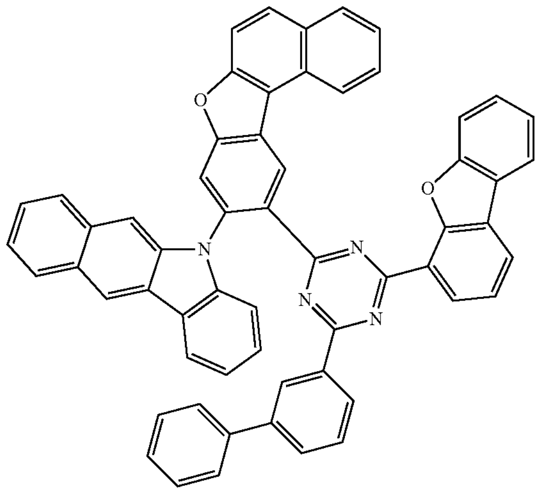
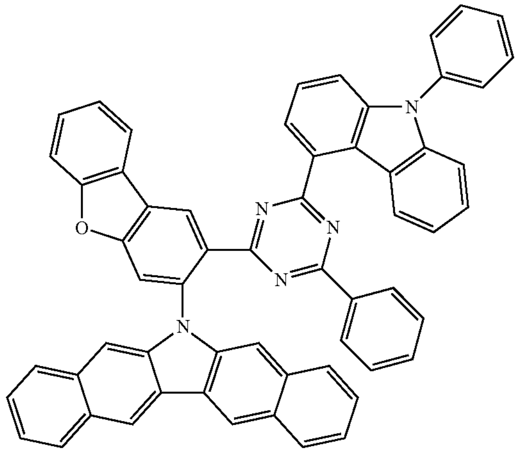
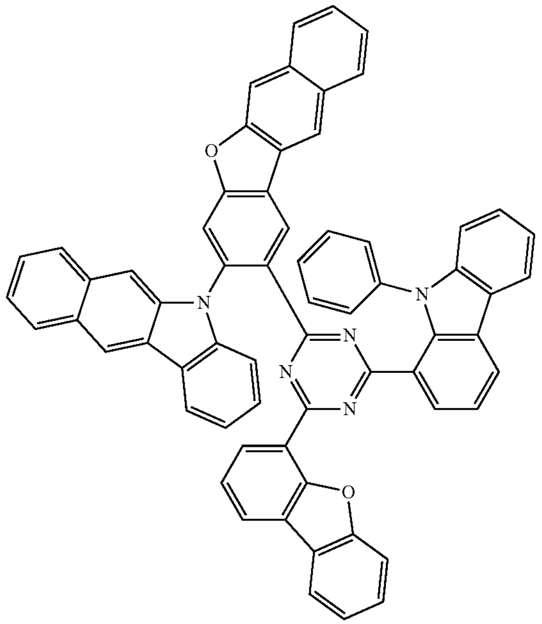
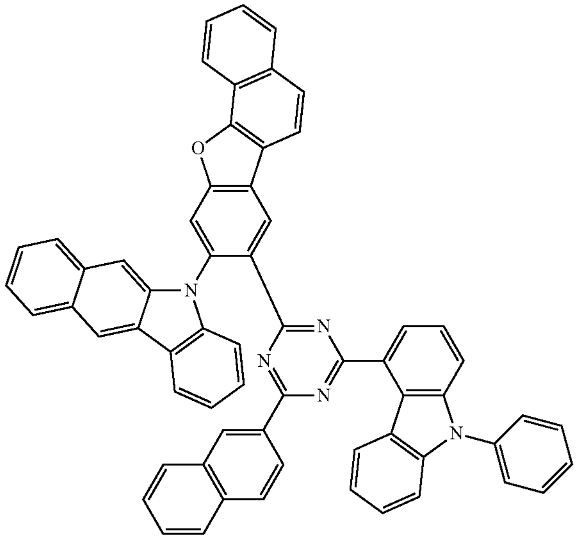
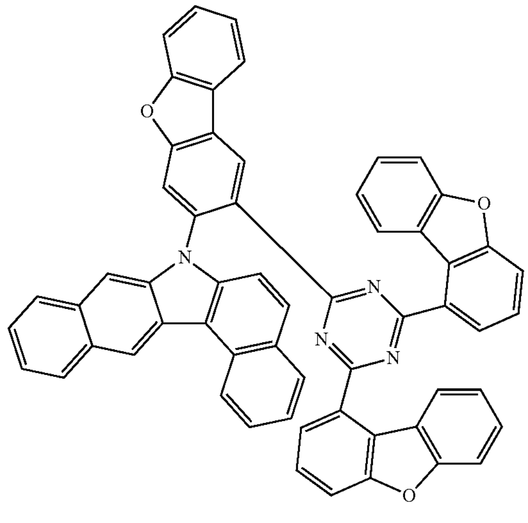
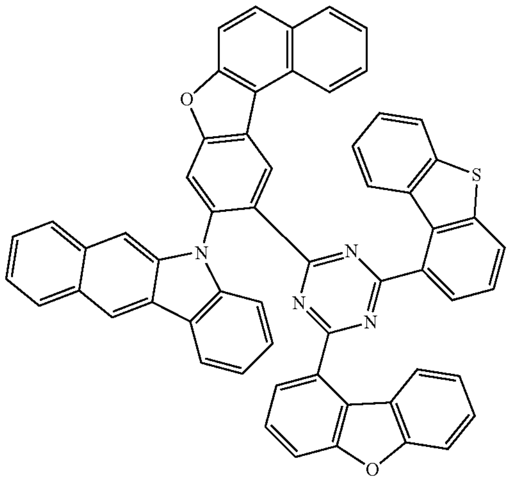
-continued -continued
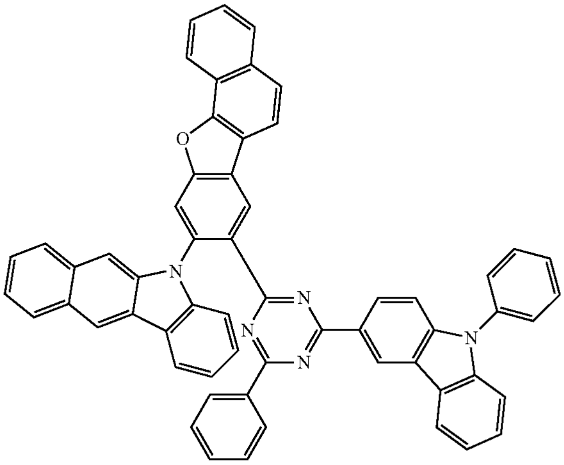
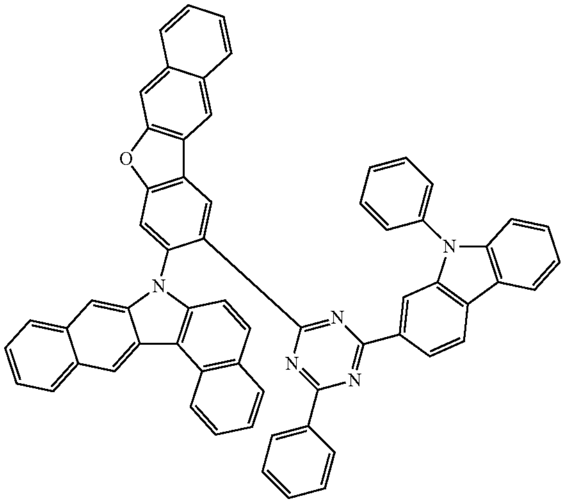
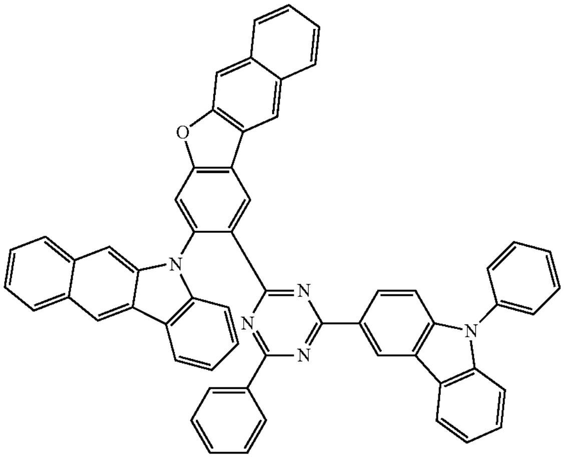
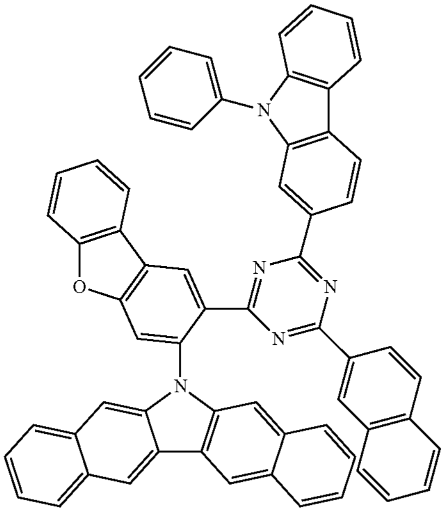
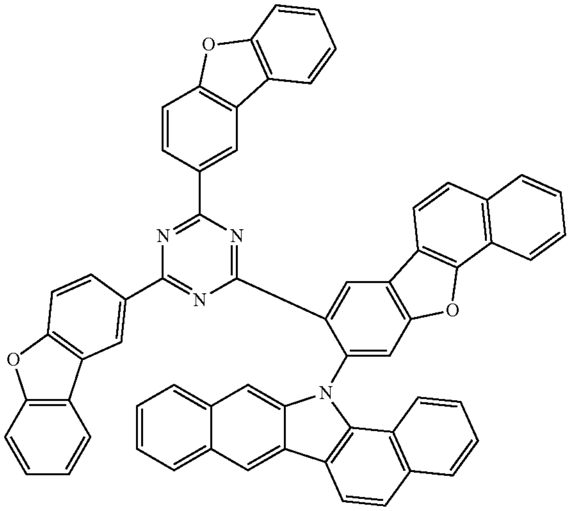
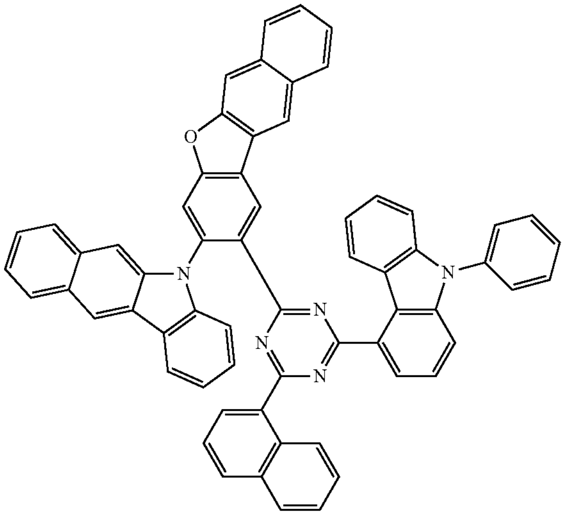
-continued -continued
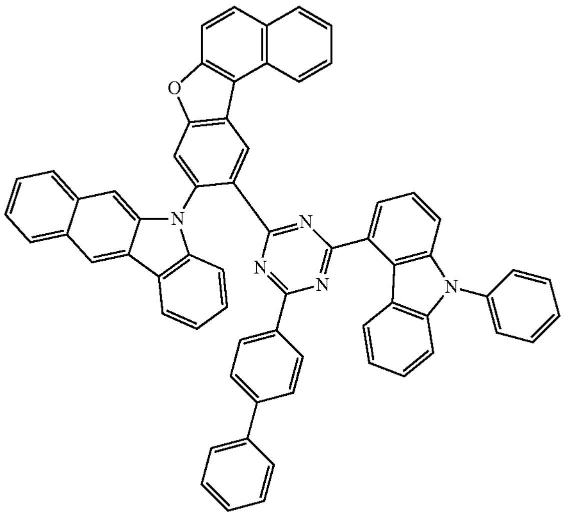
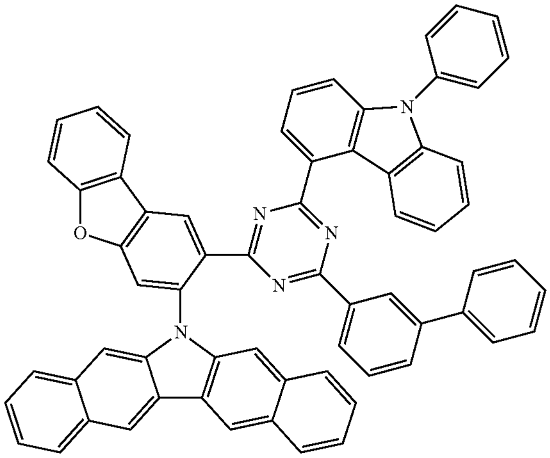
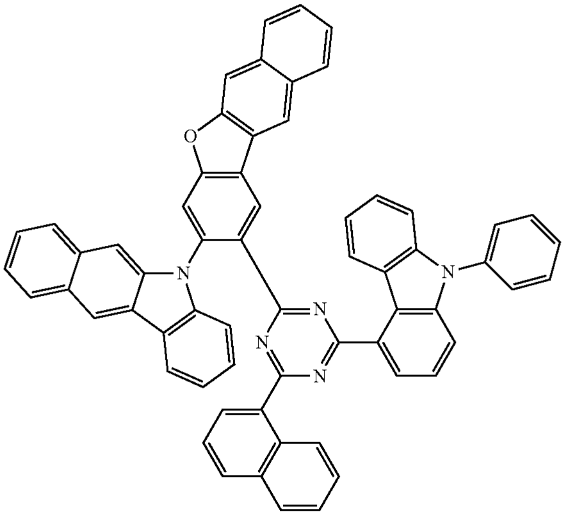
-continued
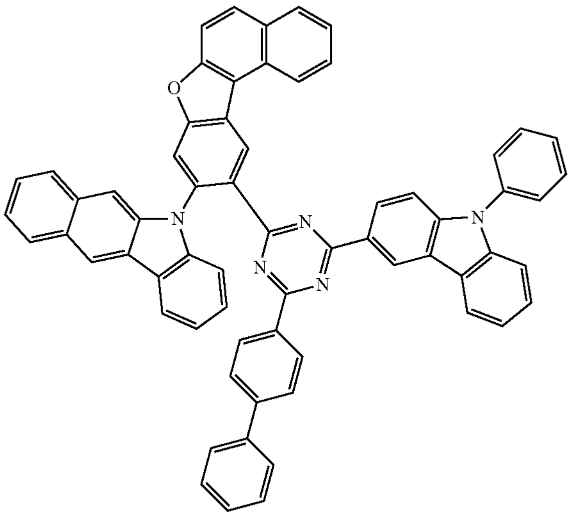
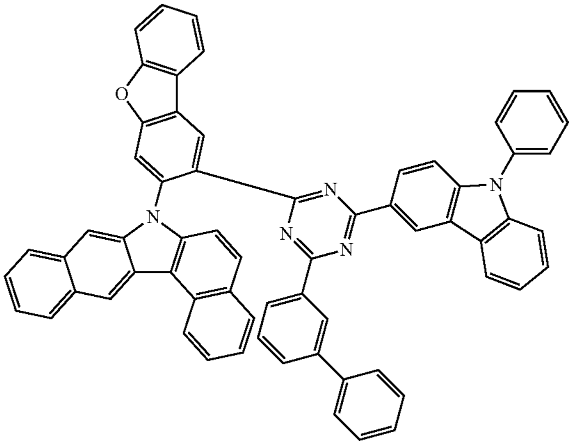
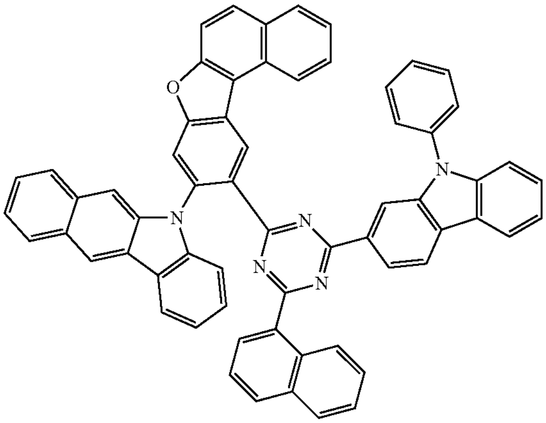

-continued
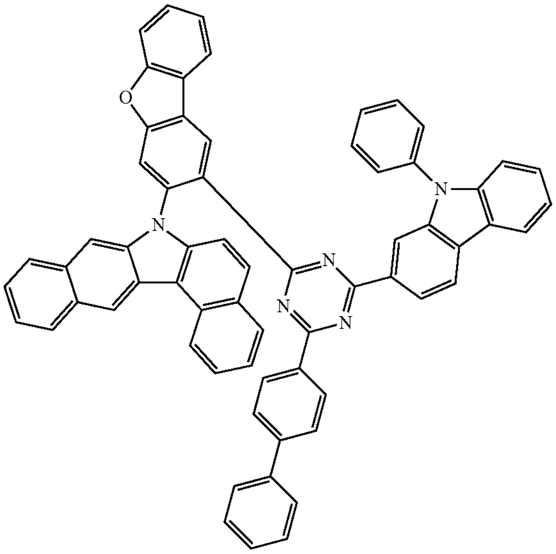
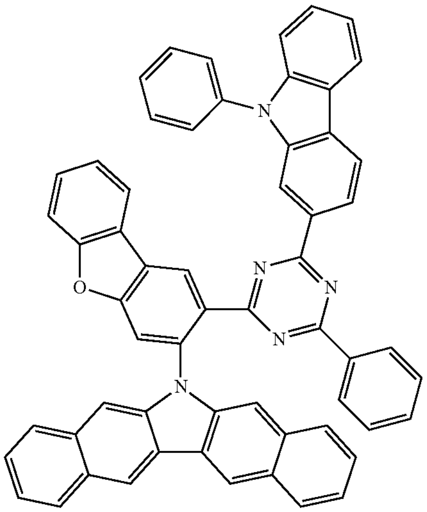
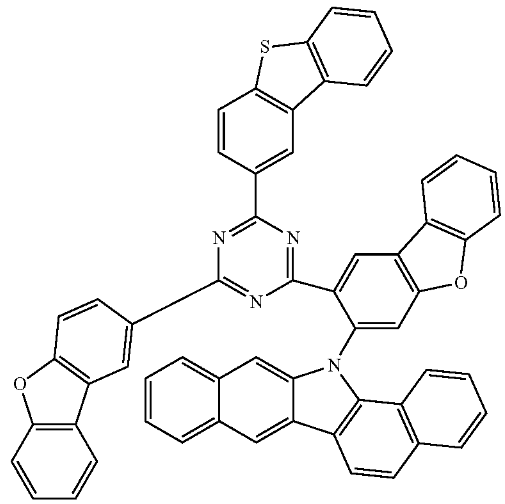
-continued
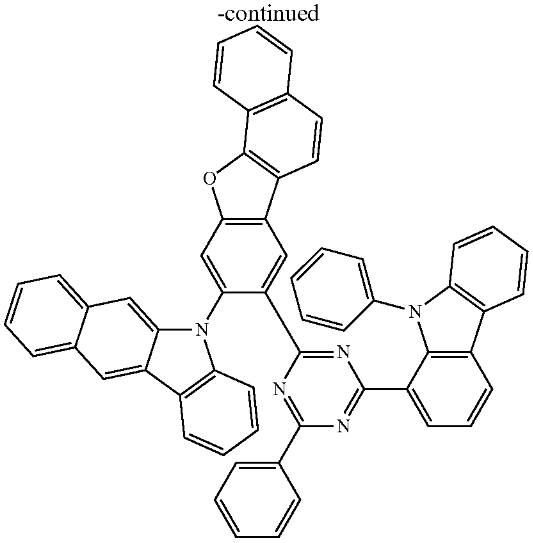
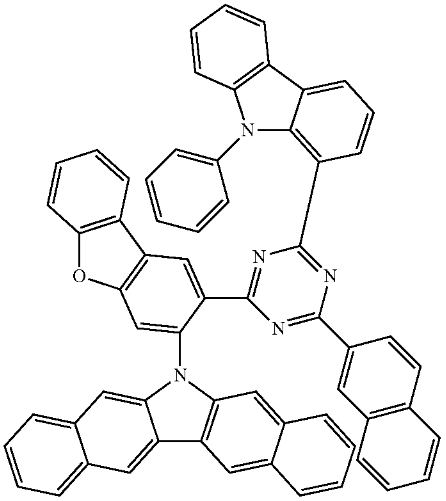
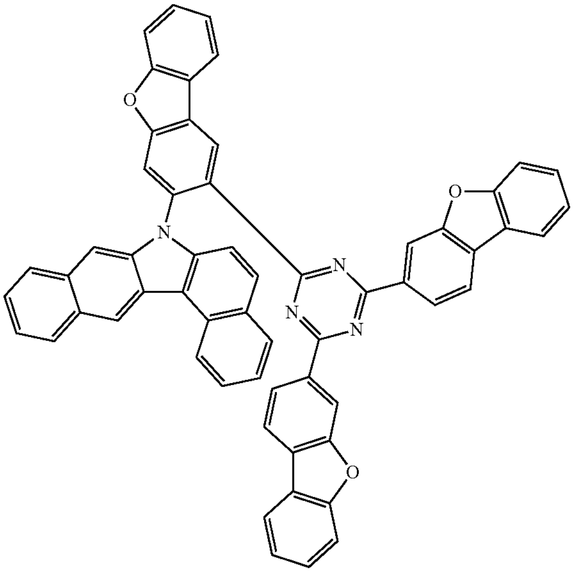

-continued
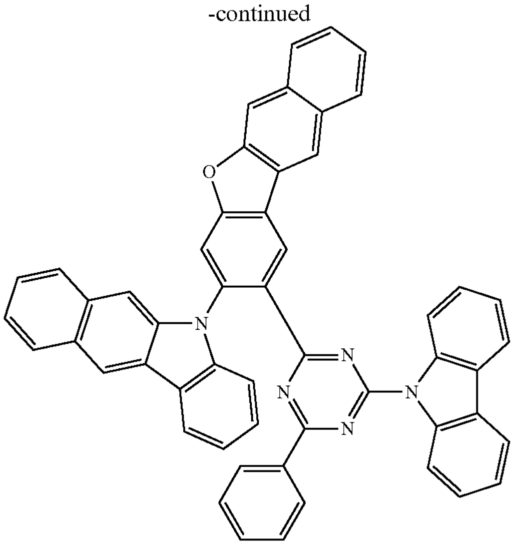
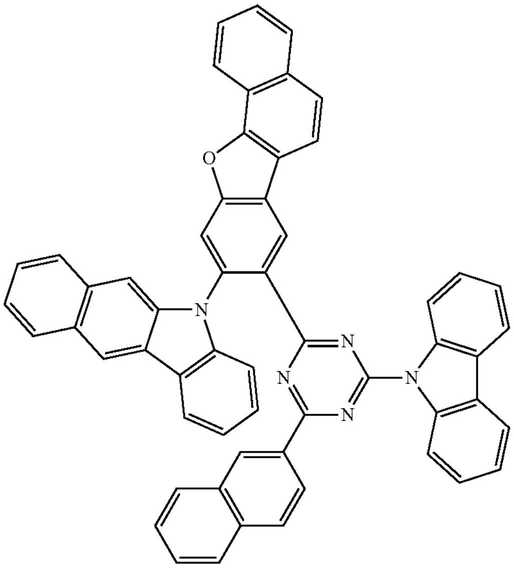
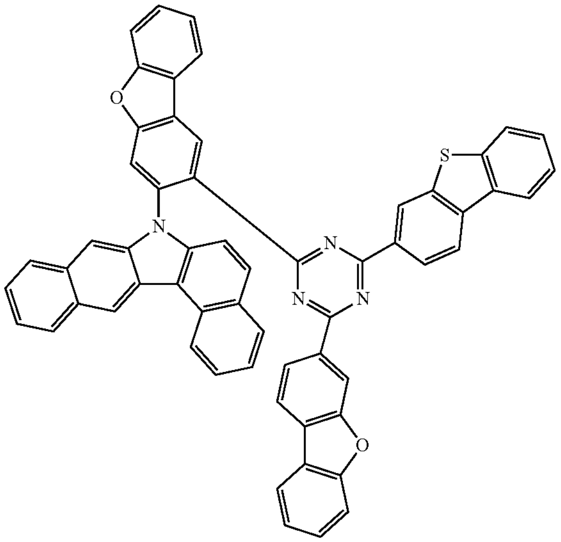
-continued
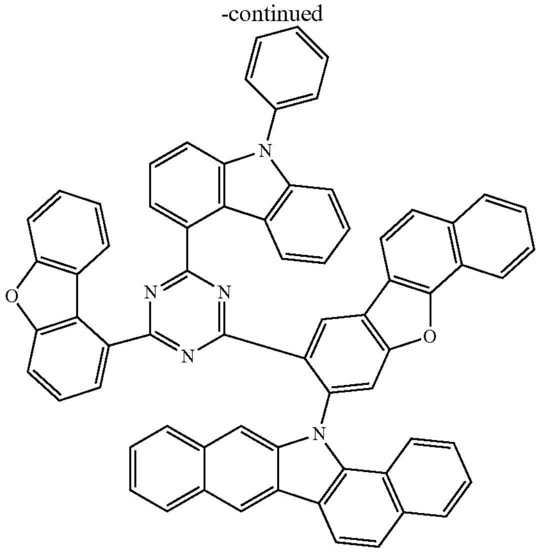
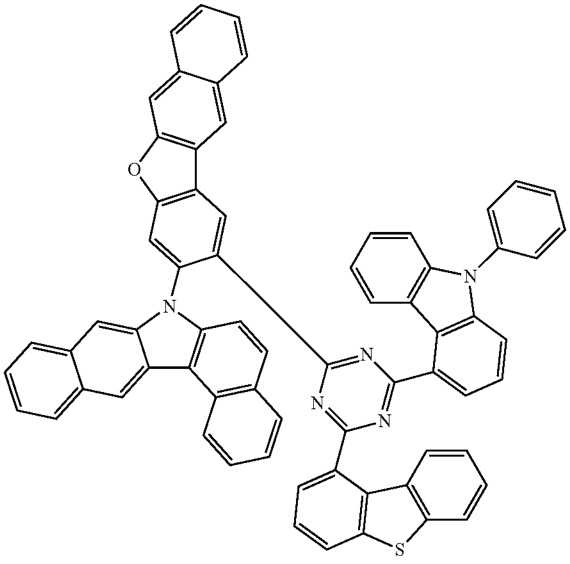
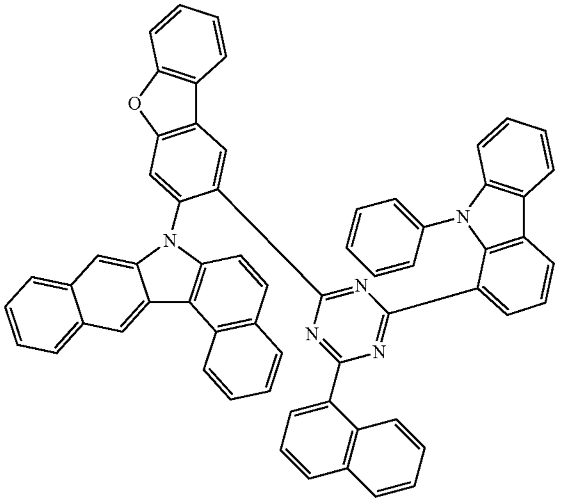

-continued
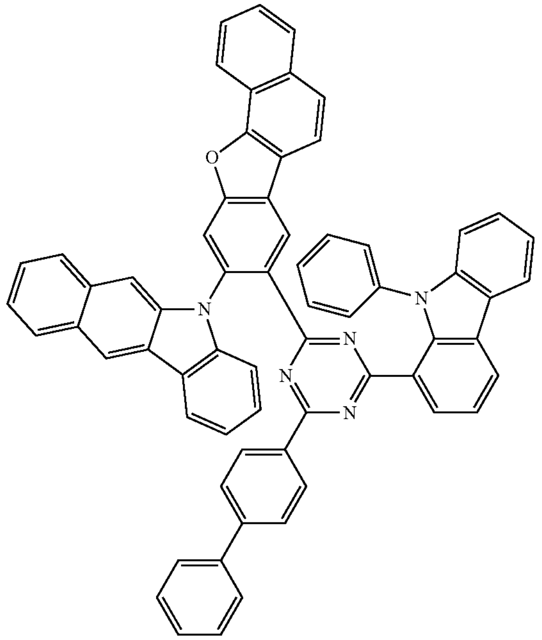
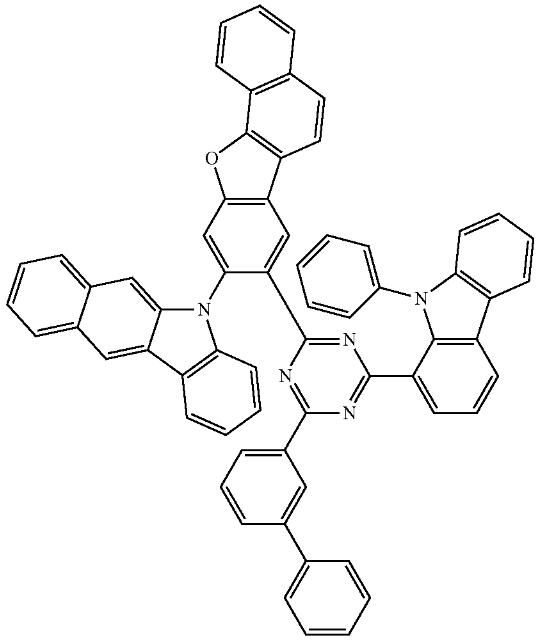
-continued
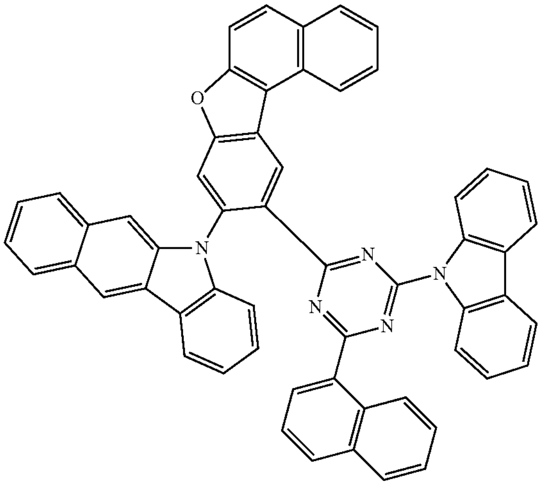
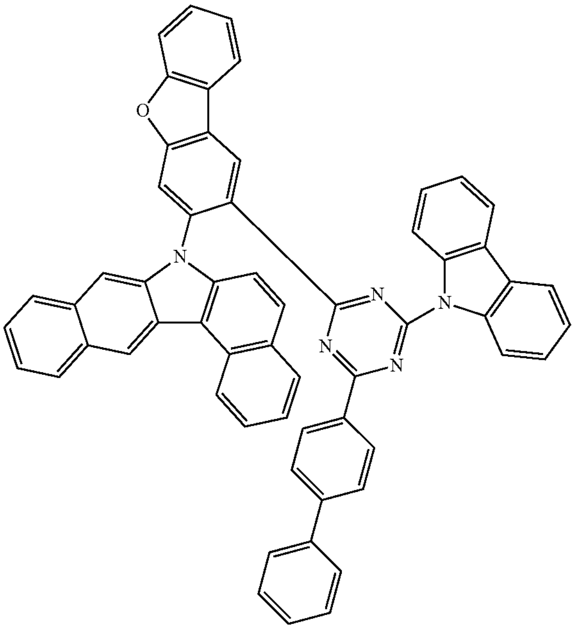
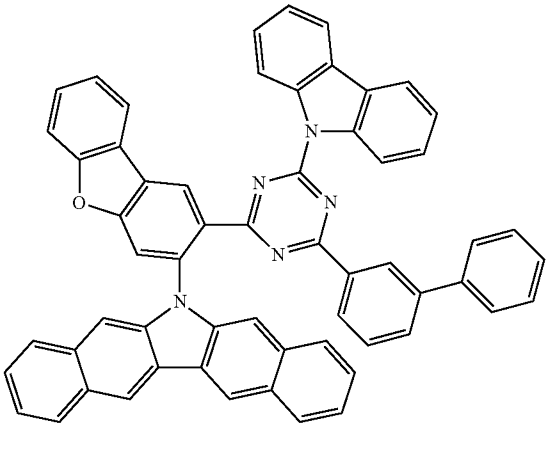

-continued
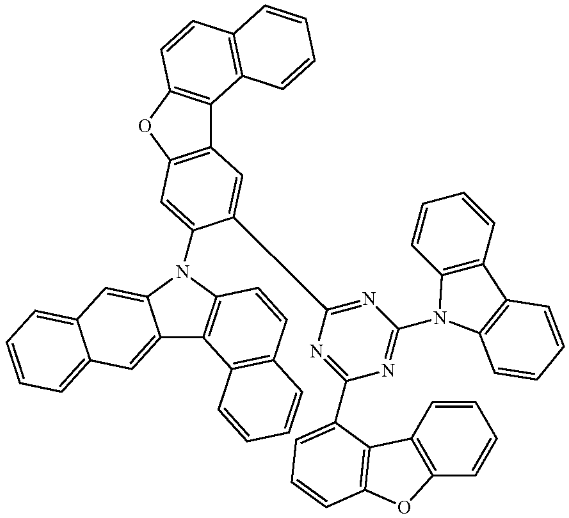
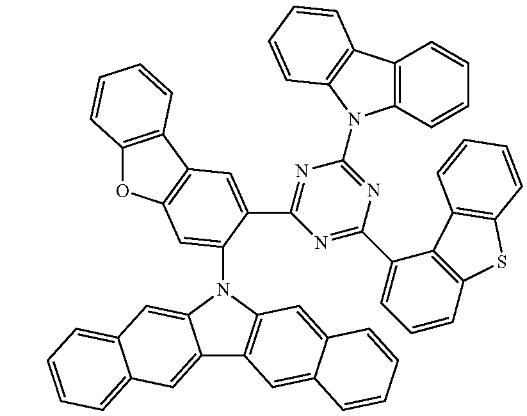
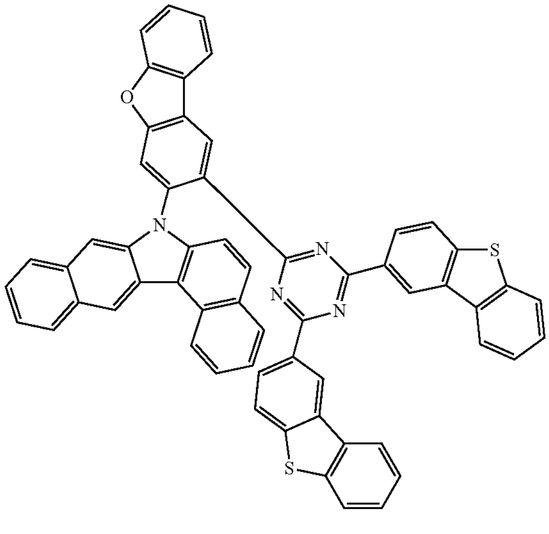
-continued
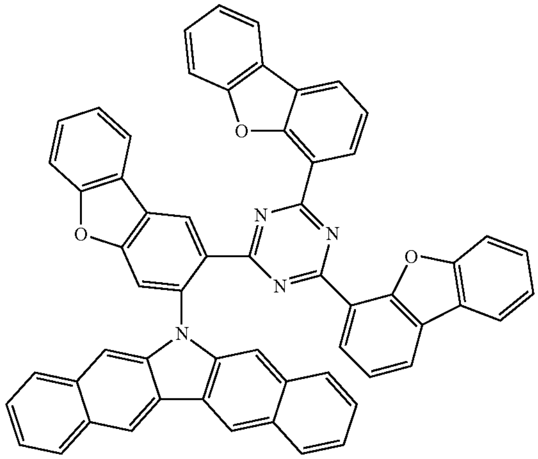
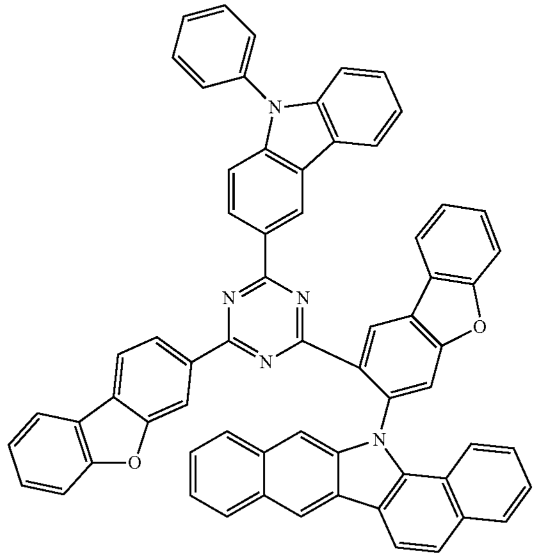
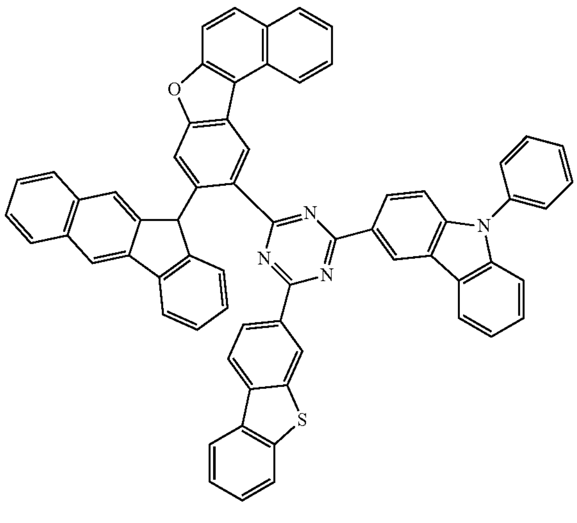

-continued
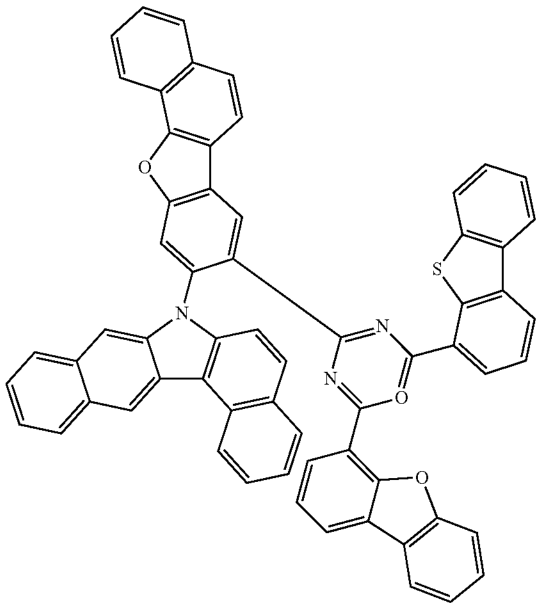
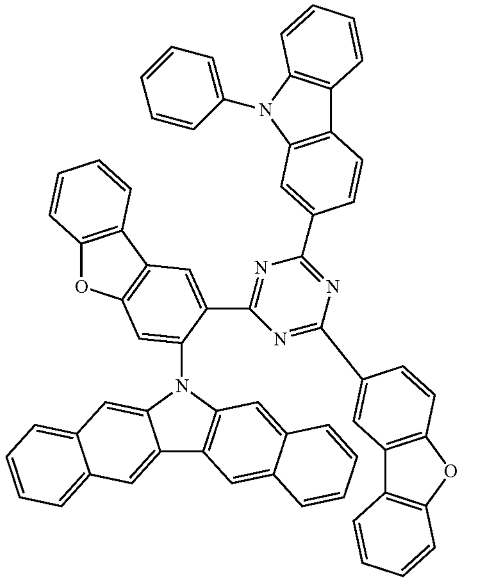
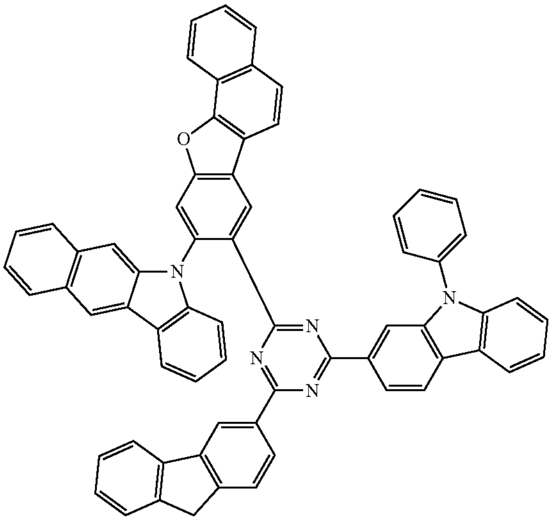
-continued
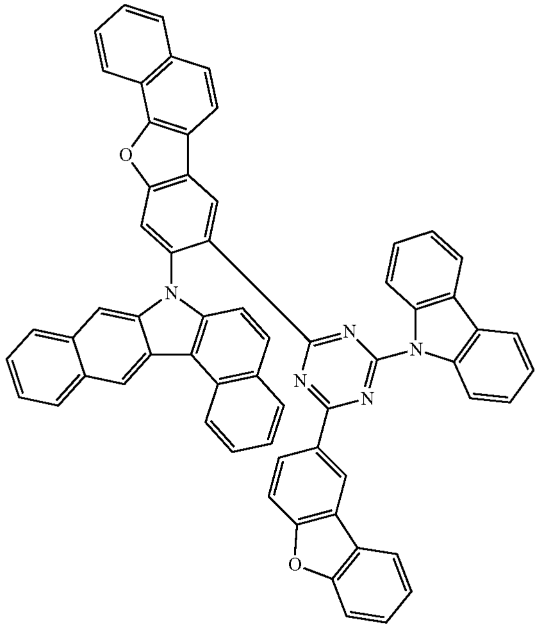
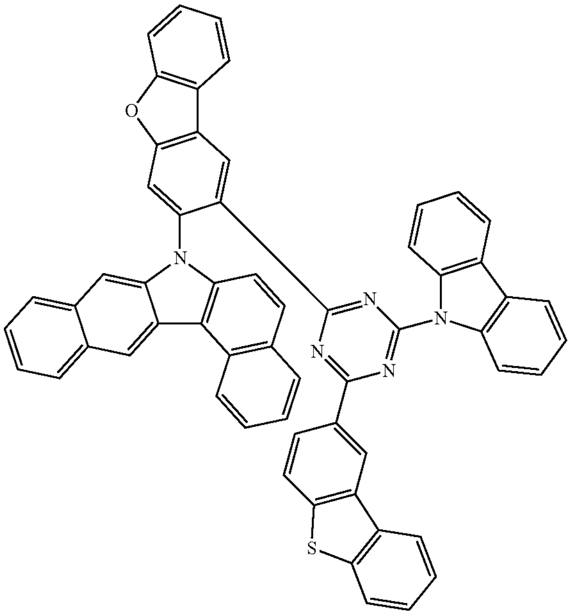

-continued
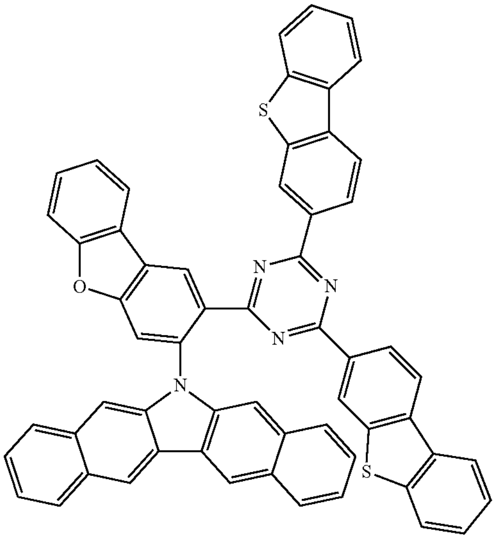
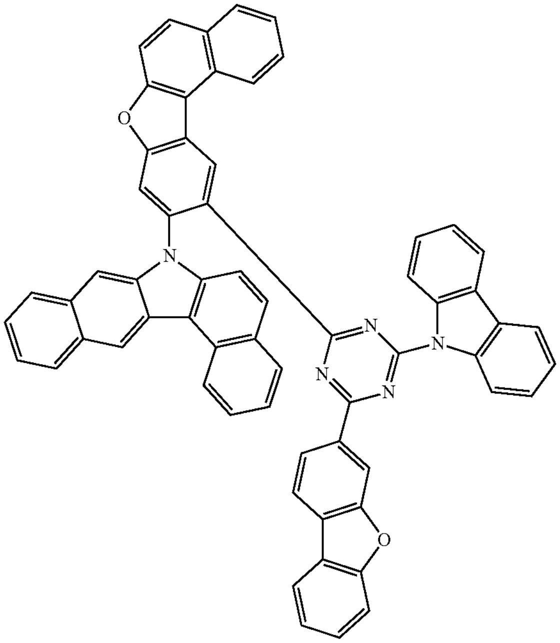
-continued
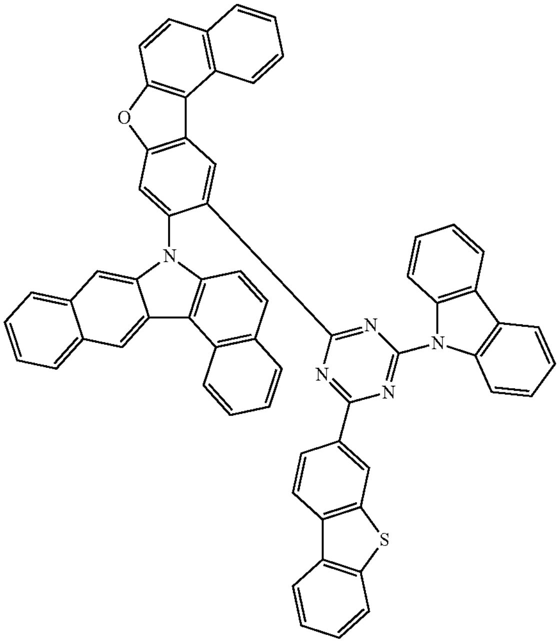
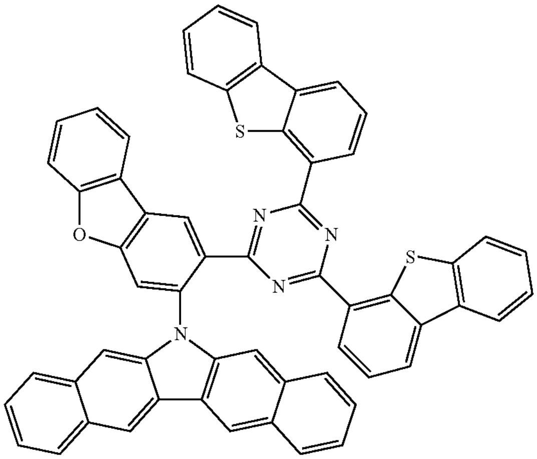
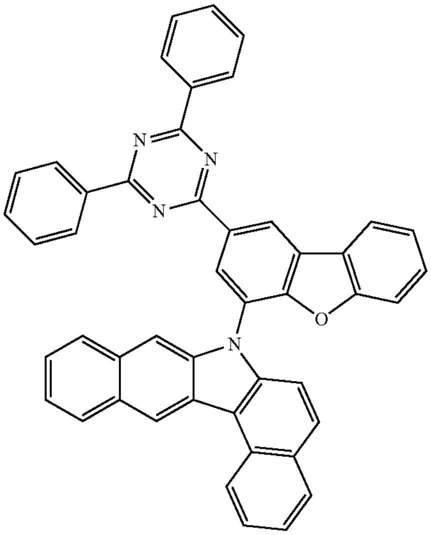

-continued
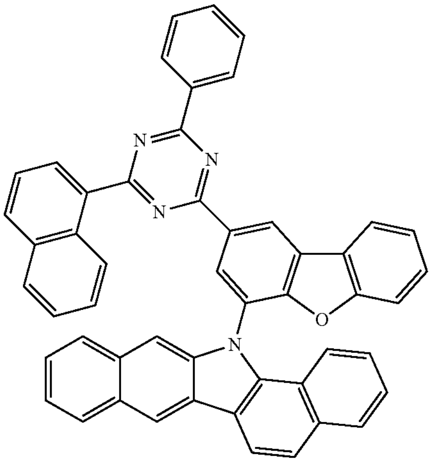
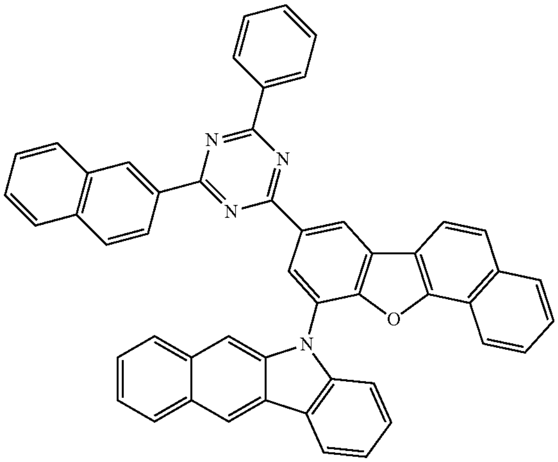
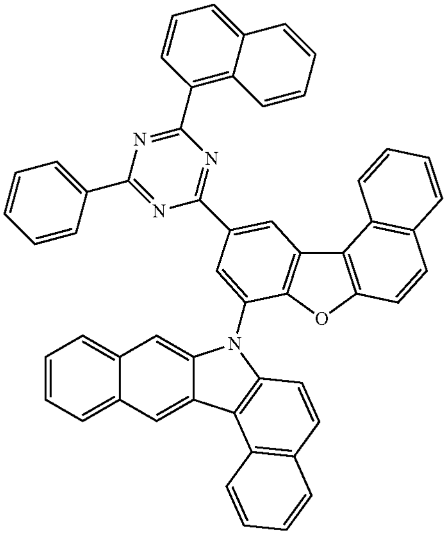
-continued
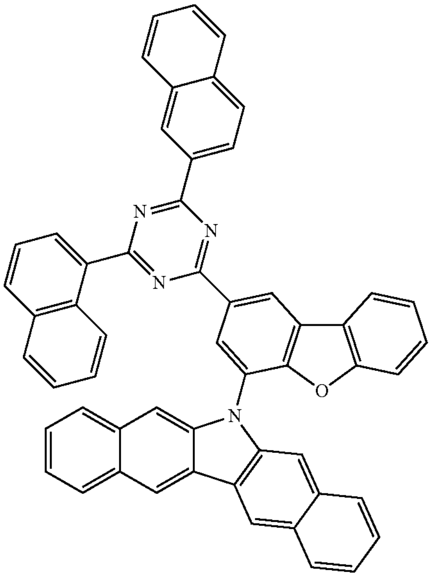
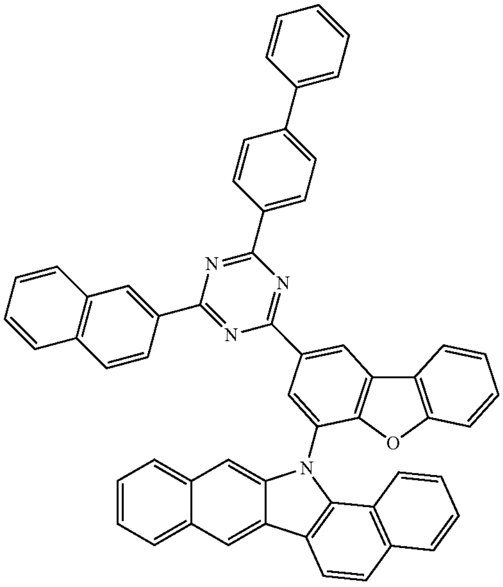
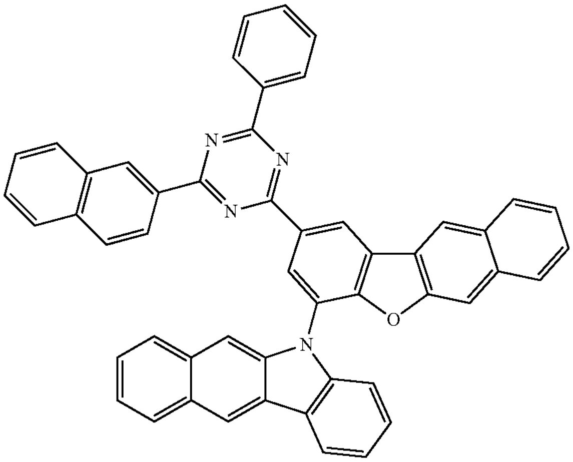

-continued
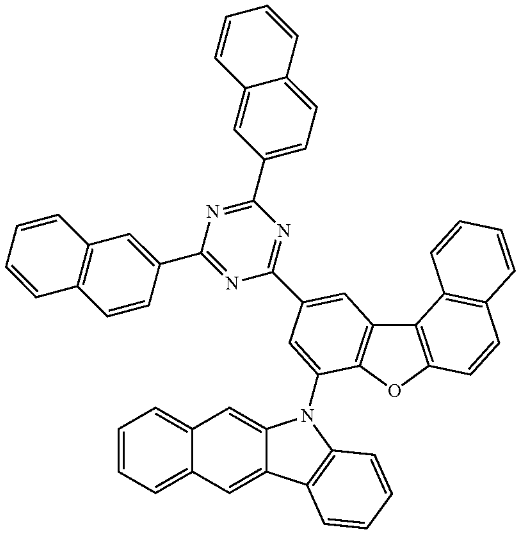
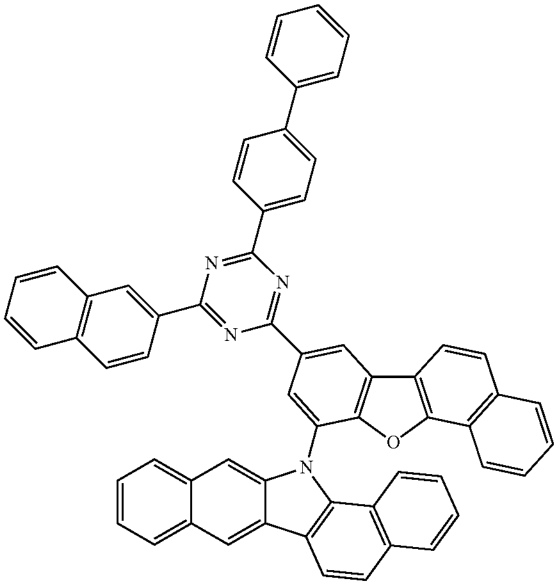
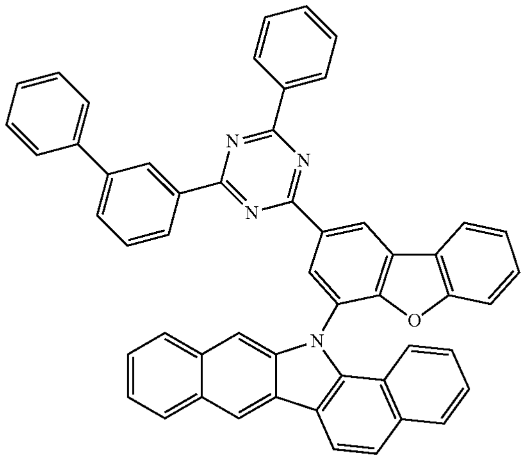
-continued
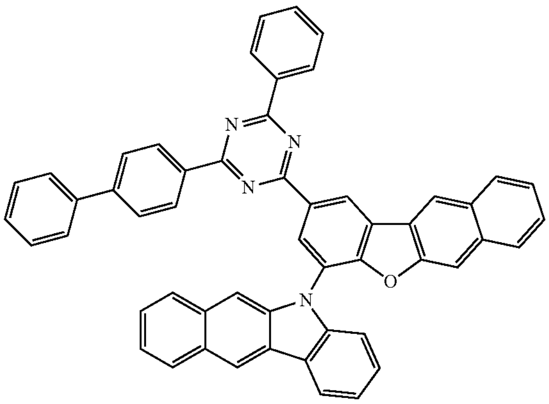
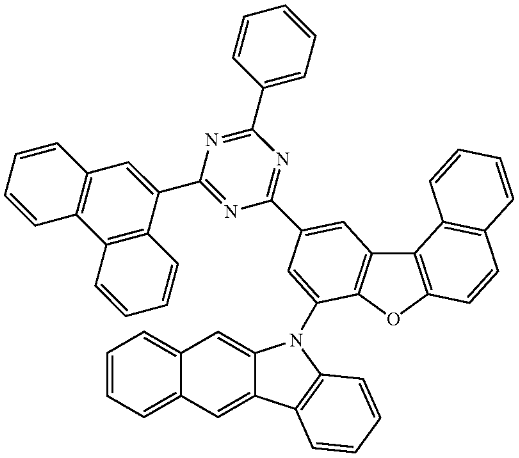
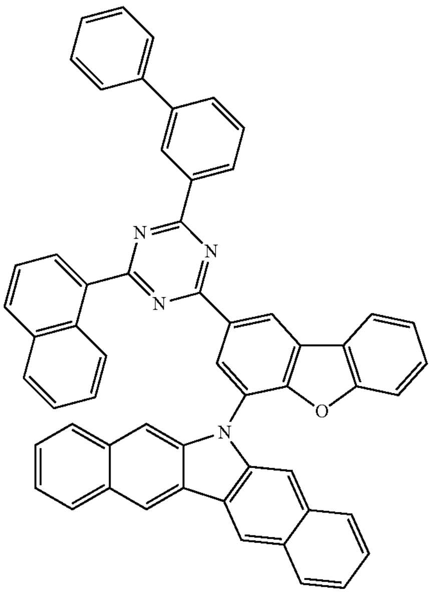

-continued
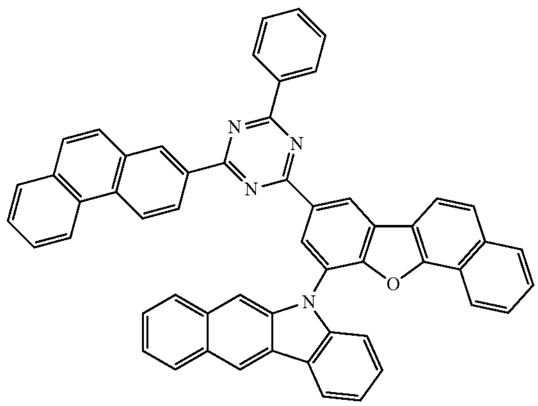
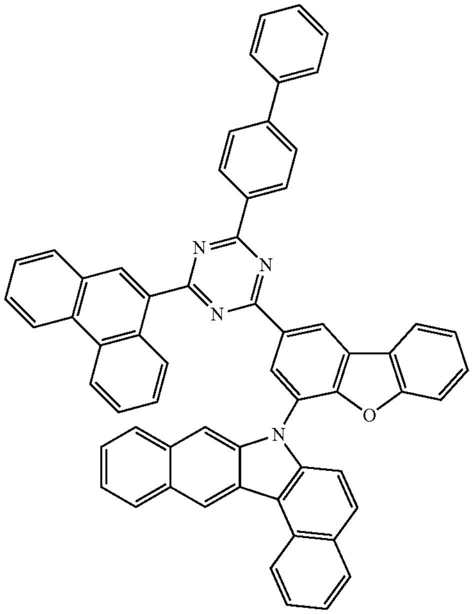
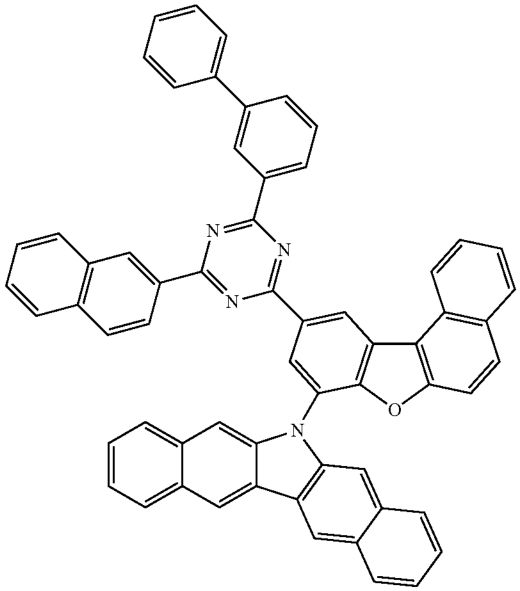
-continued
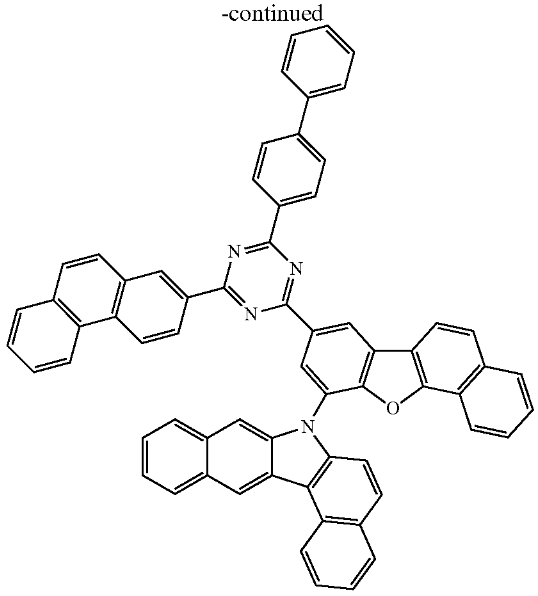
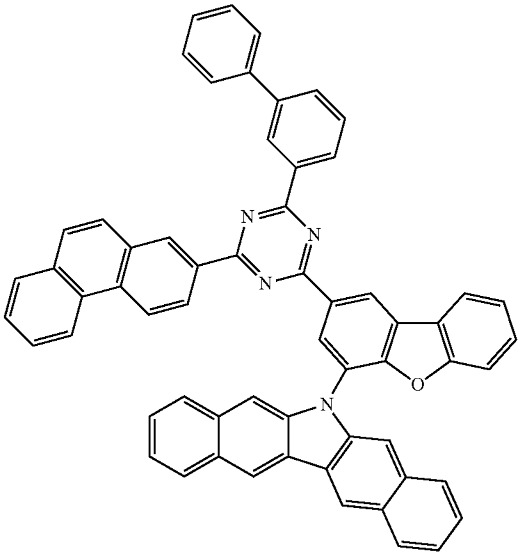
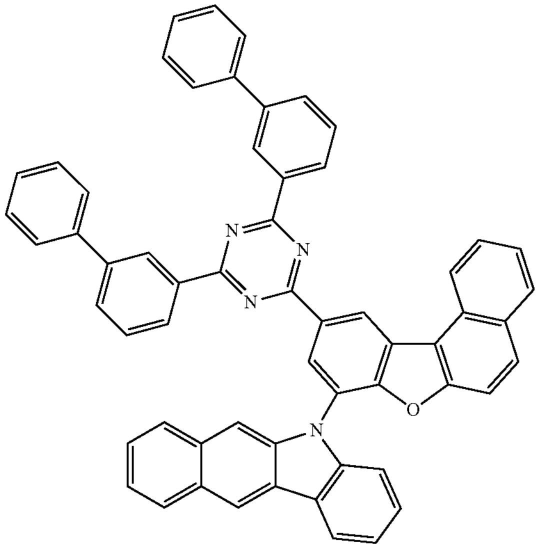

-continued
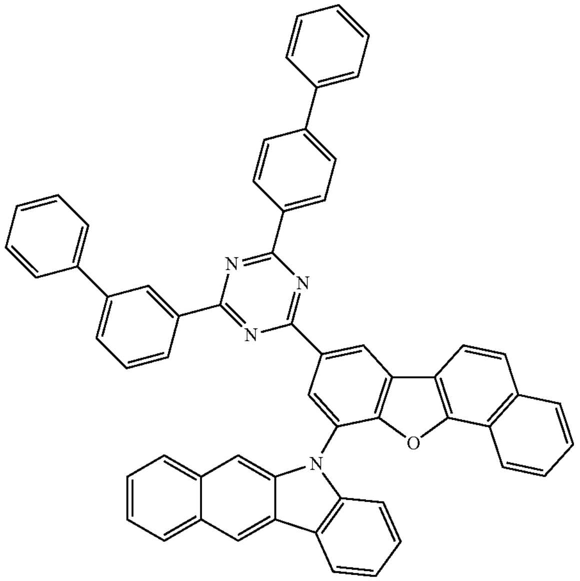
-continued
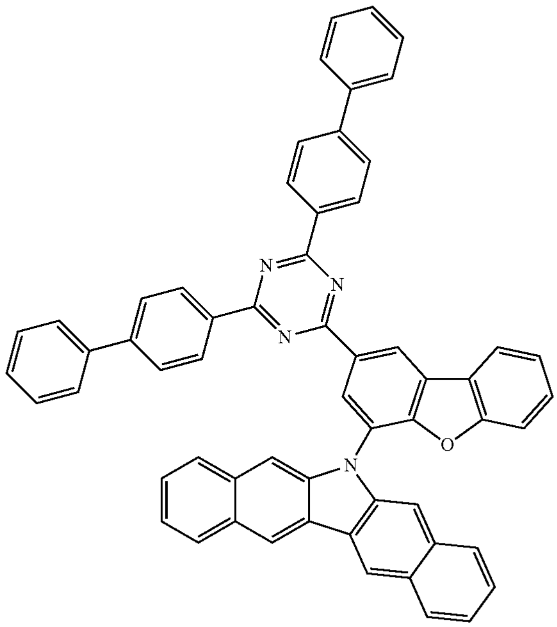
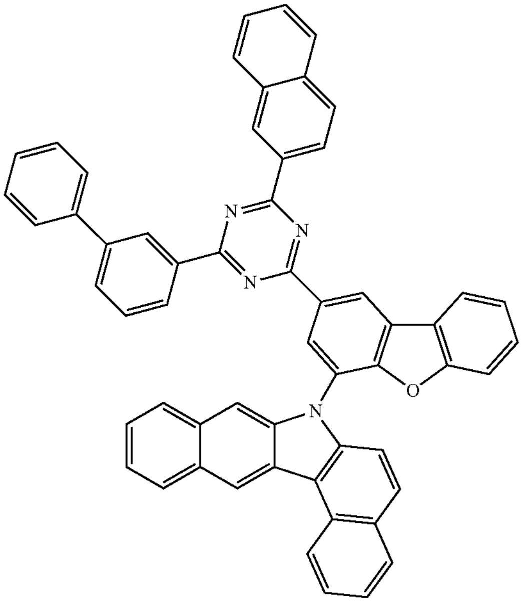
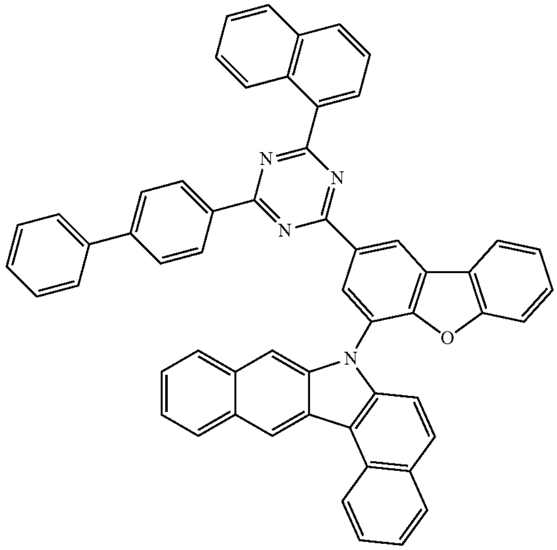

-continued
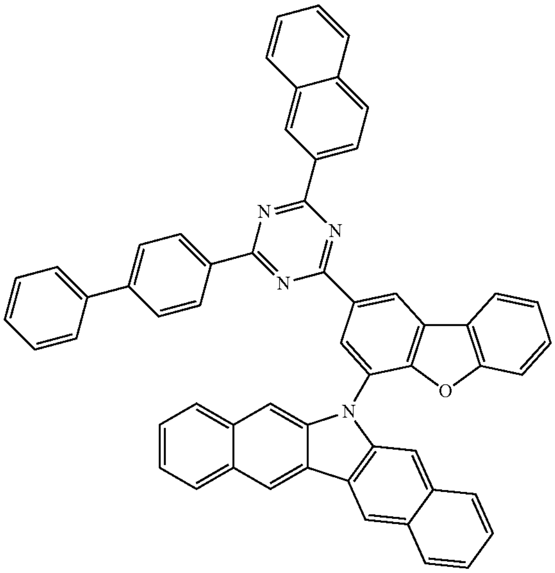
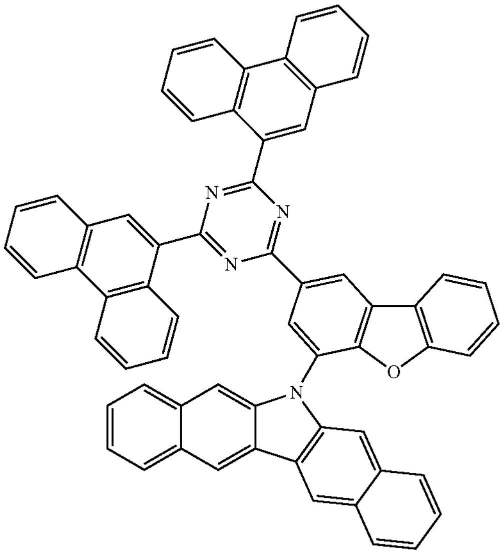
-continued
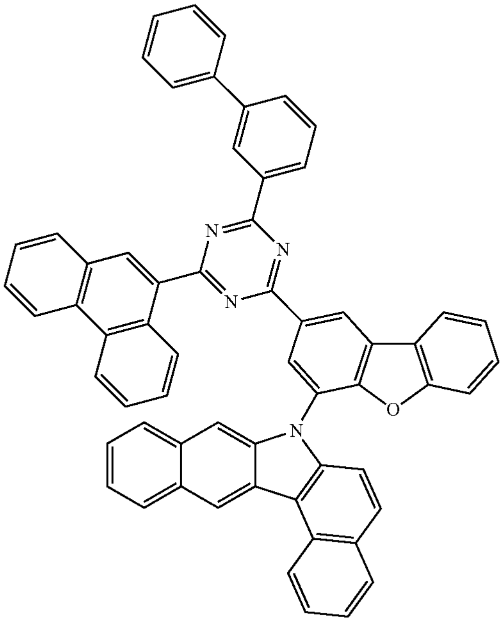
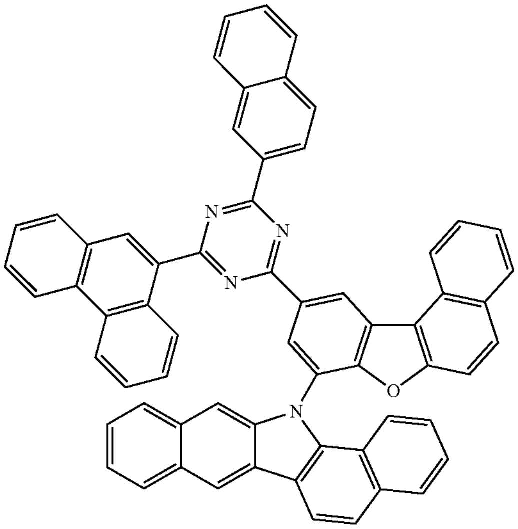
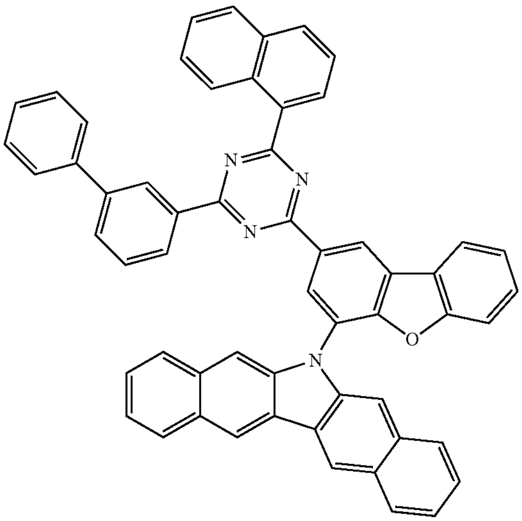

-continued
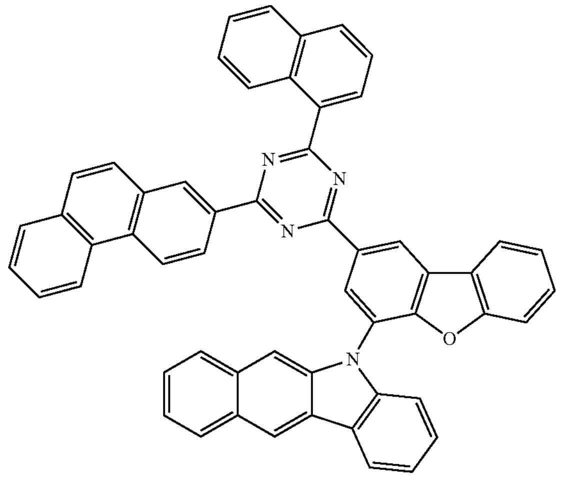
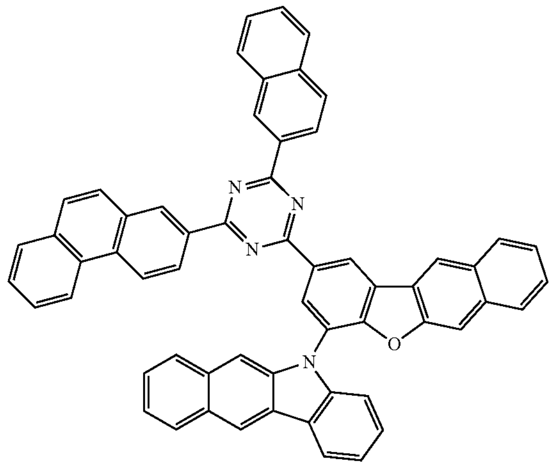
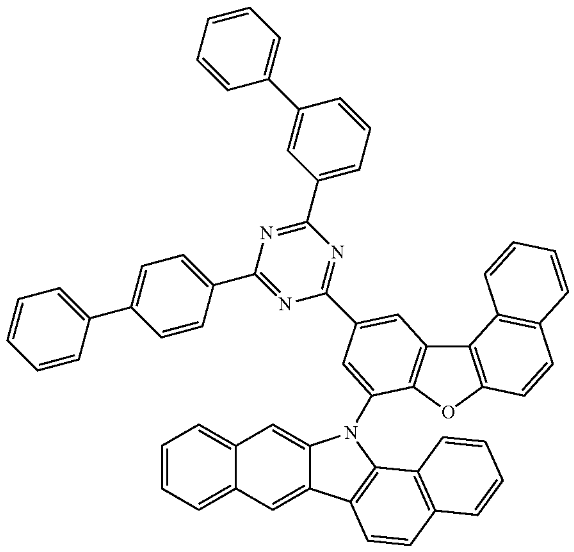
-continued
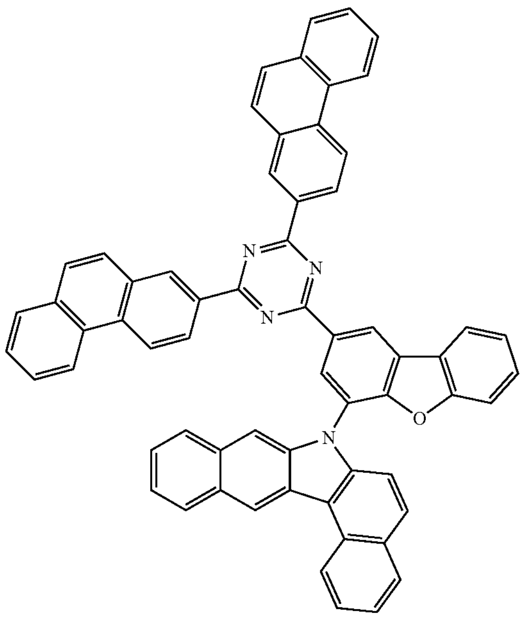
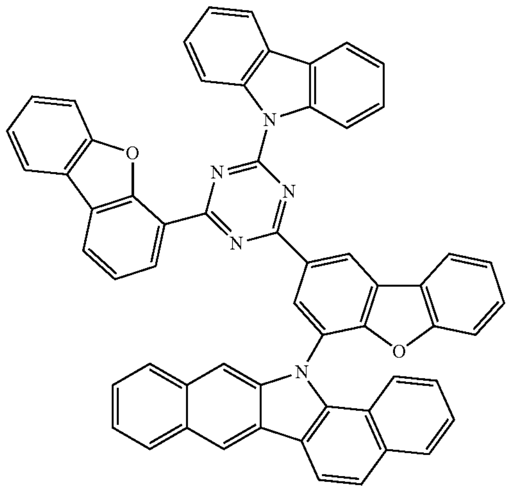
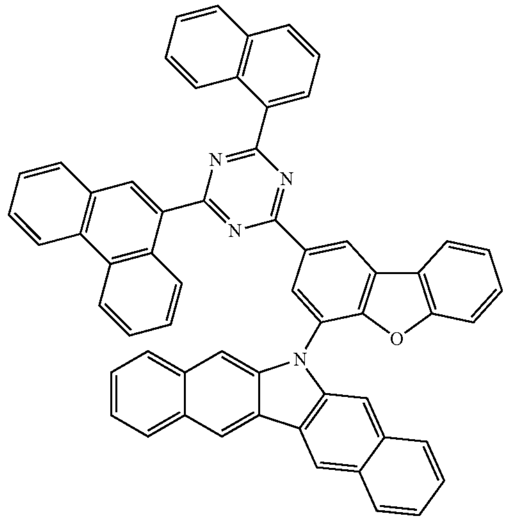

-continued
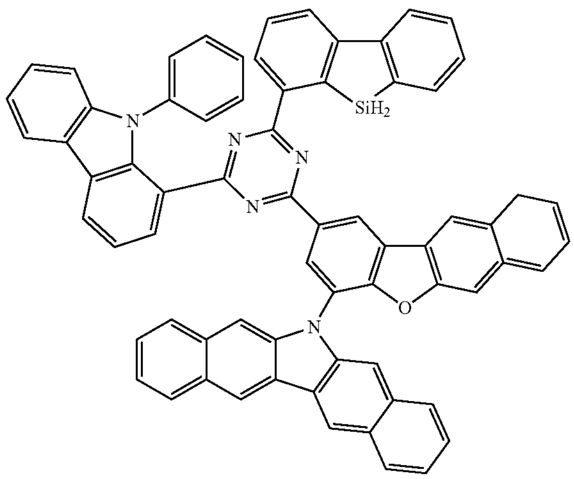
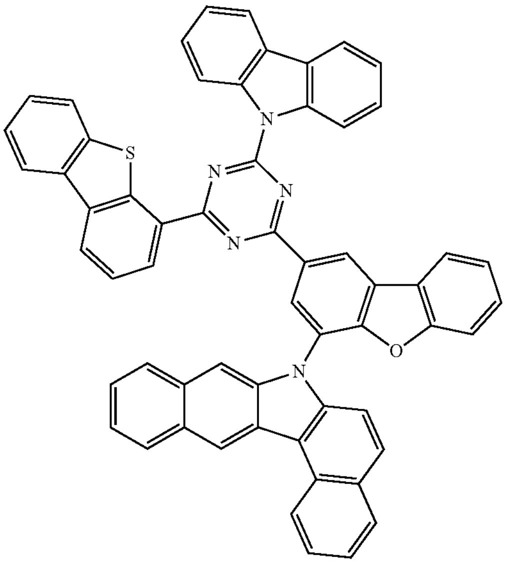
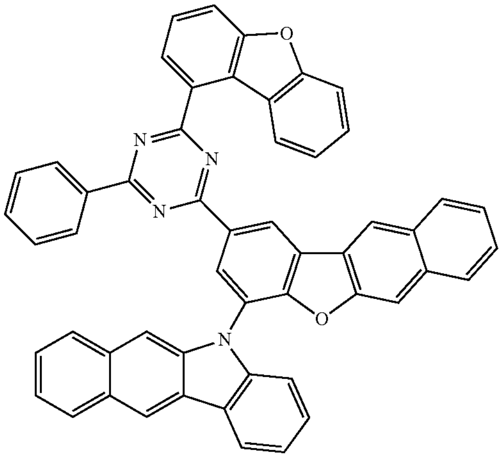
-continued
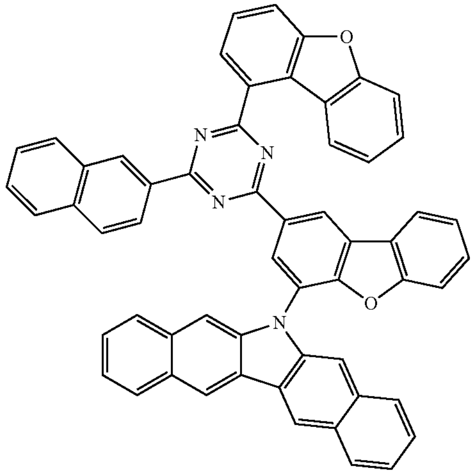
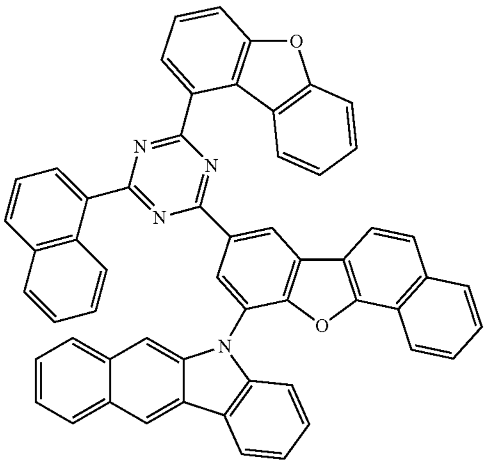
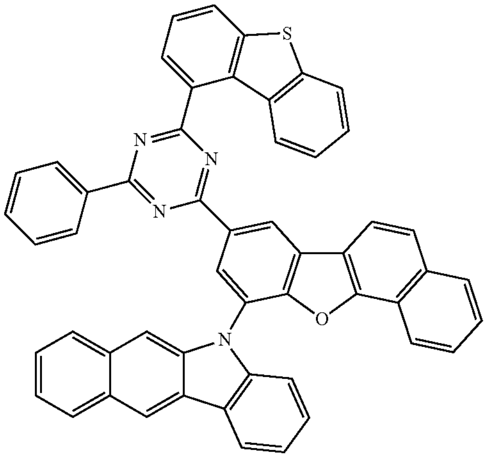

-continued
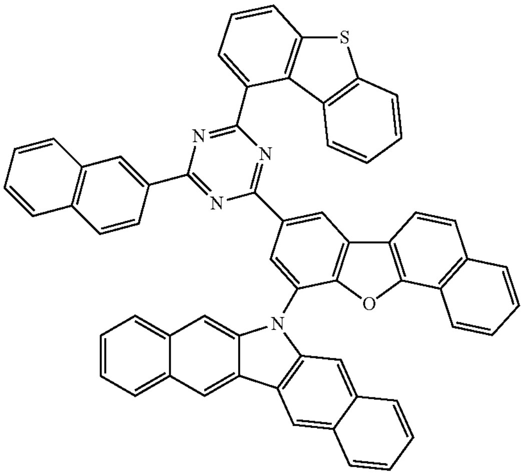
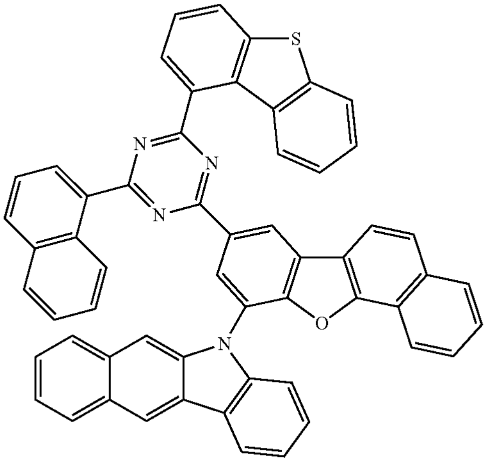
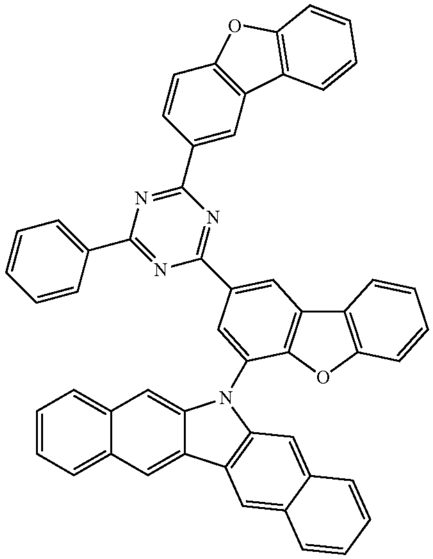
-continued
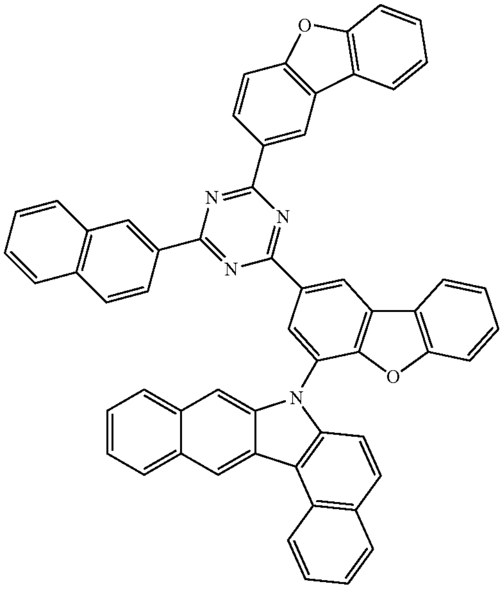
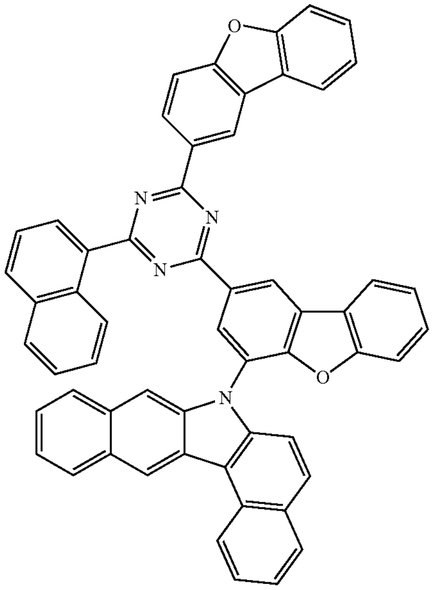
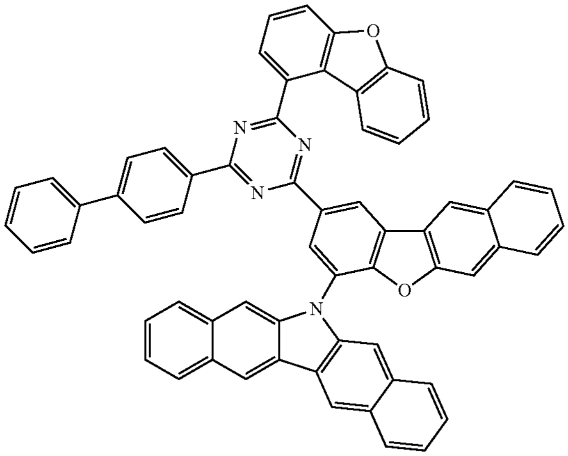

-continued
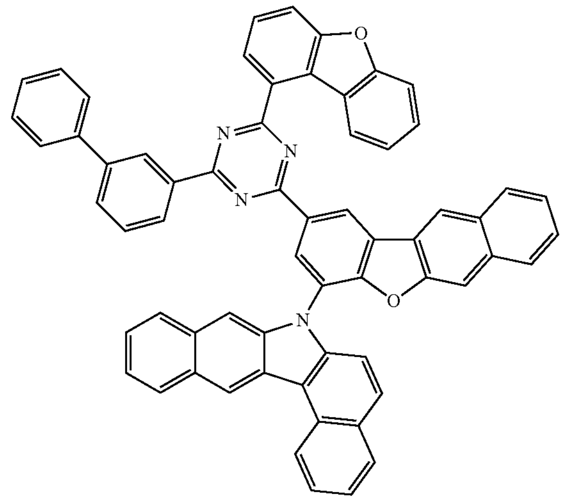
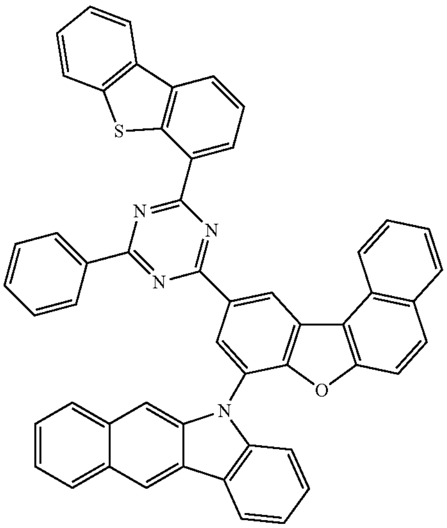
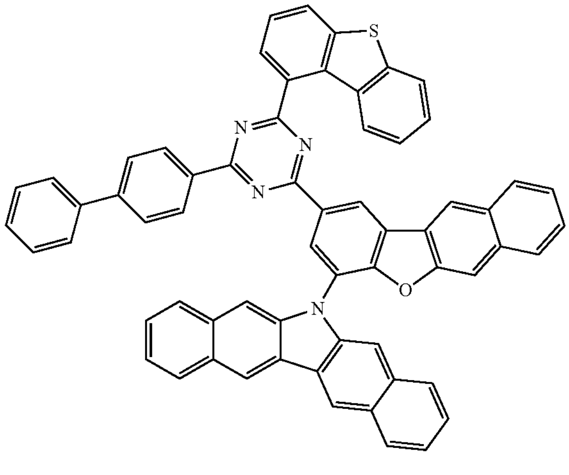
-continued
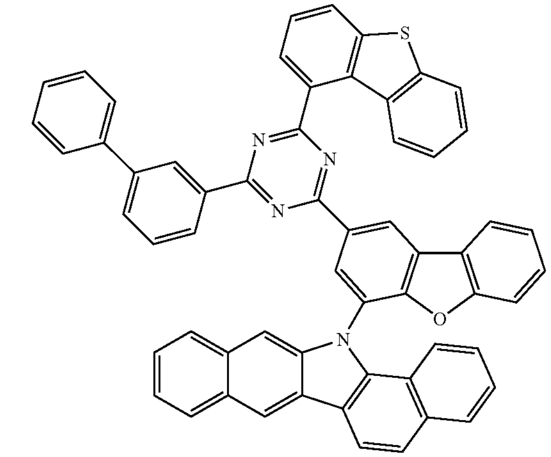
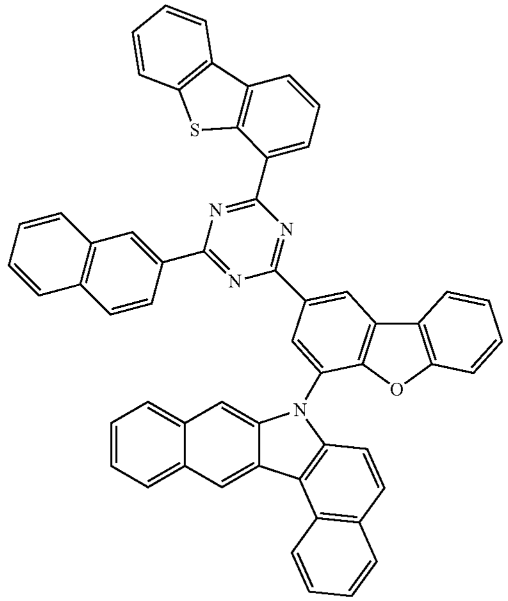
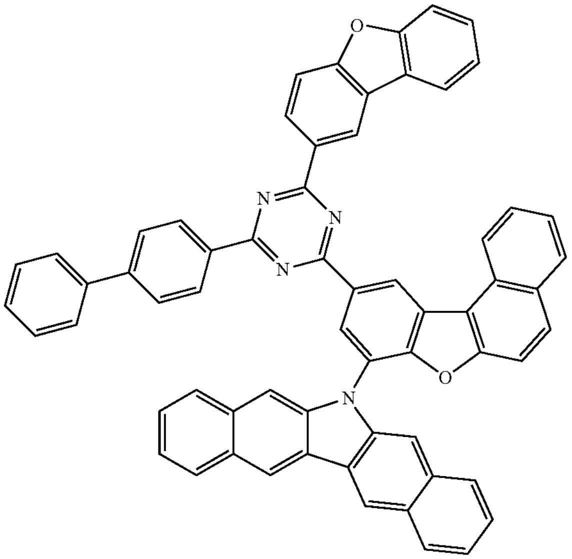

-continued
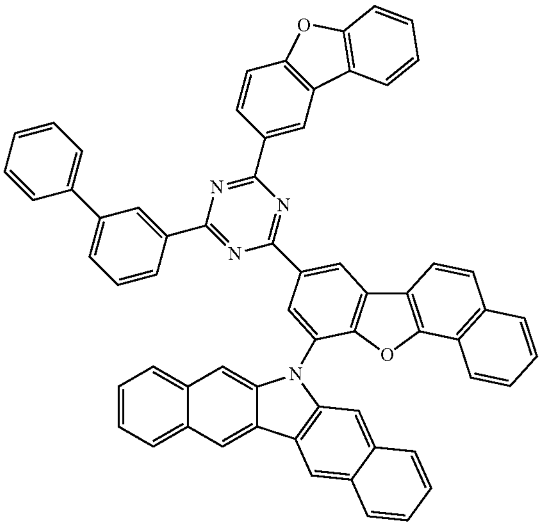
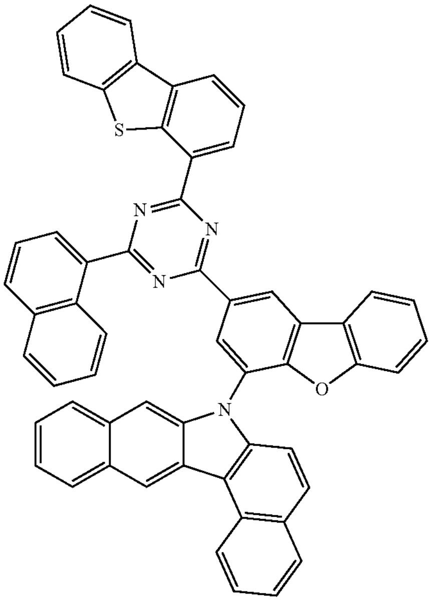
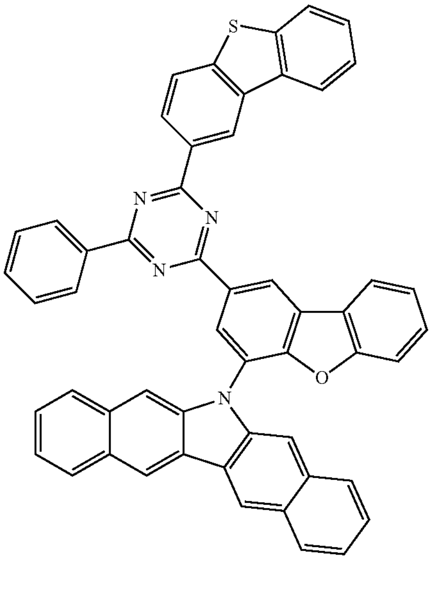
-continued
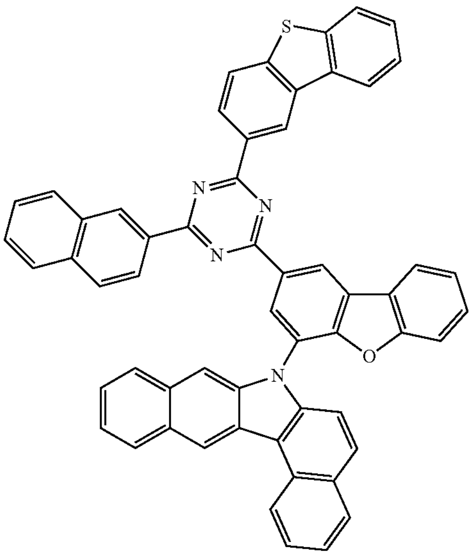
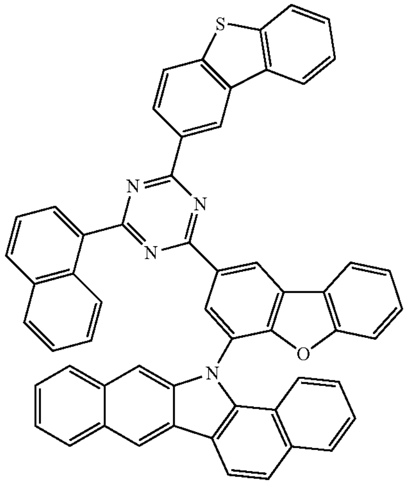
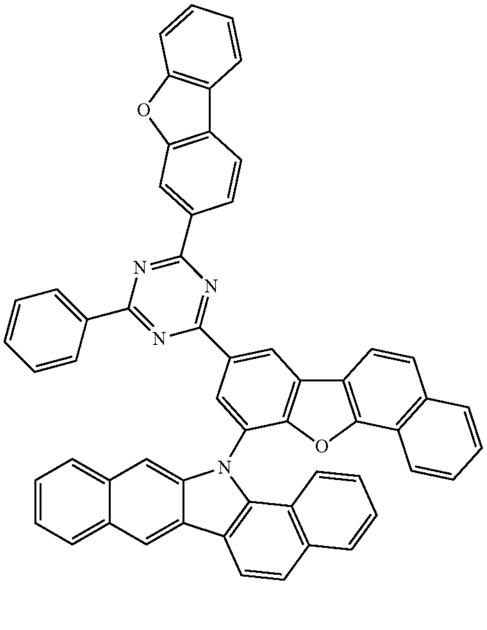

-continued
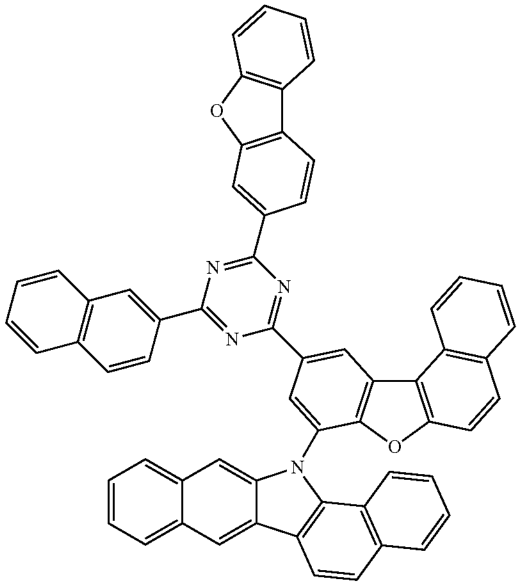
-continued
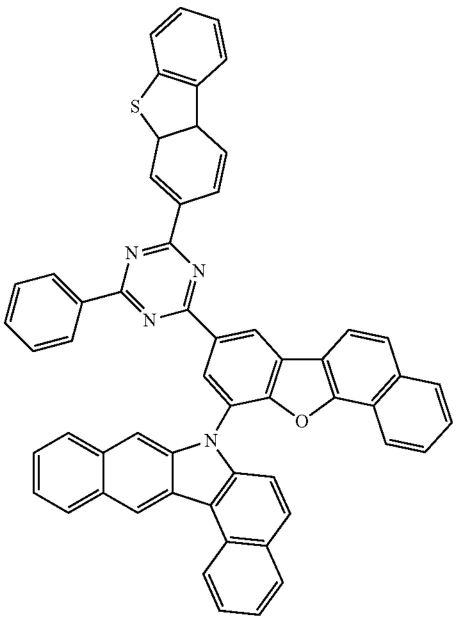
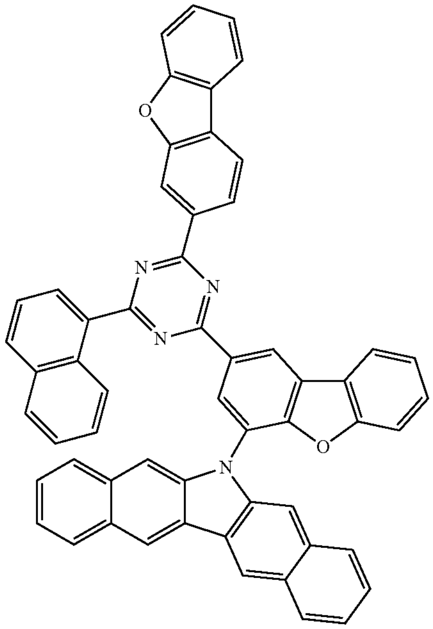
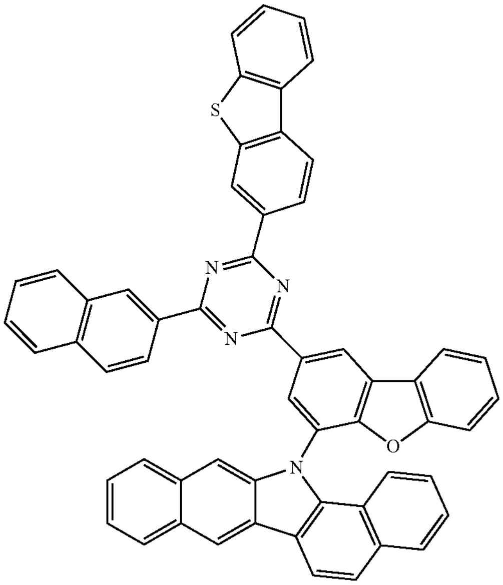

-continued
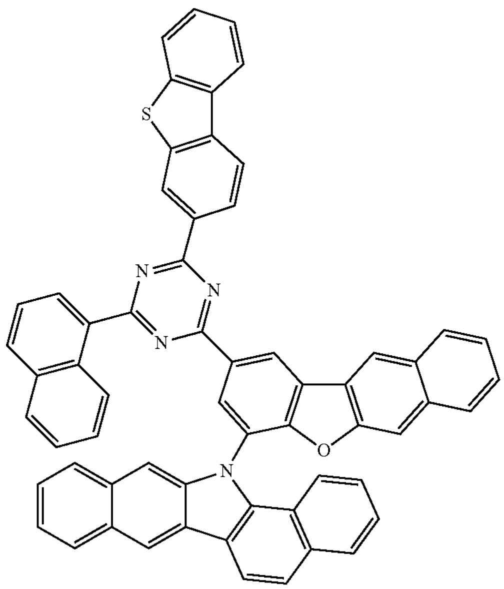
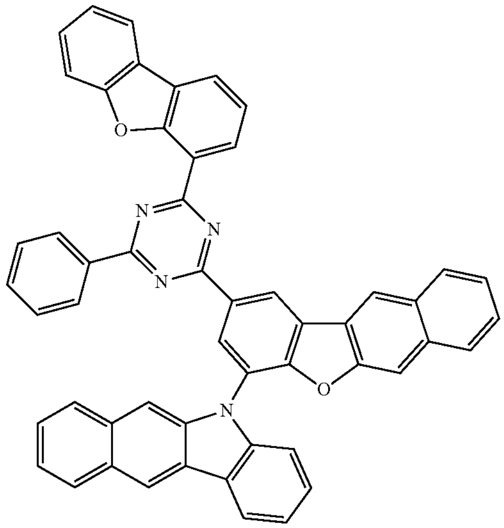
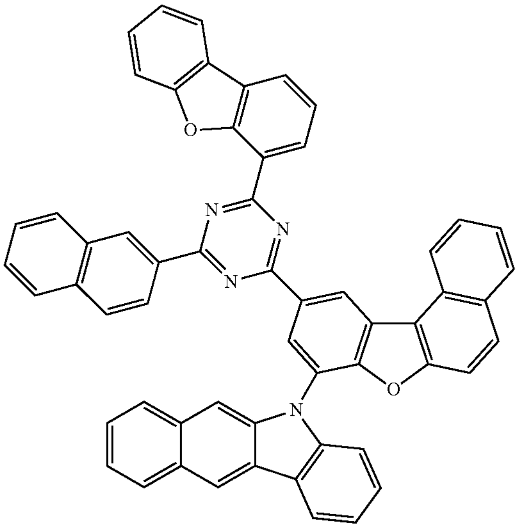
-continued
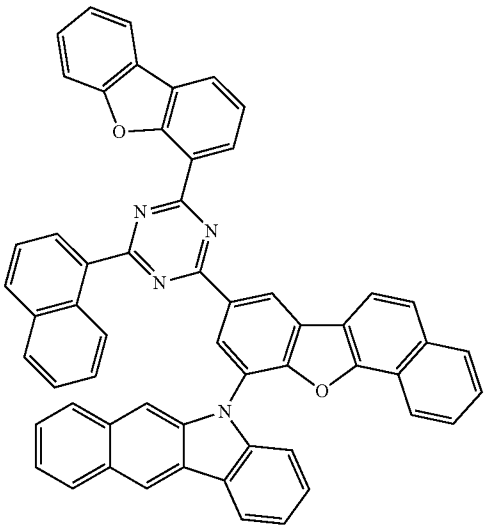
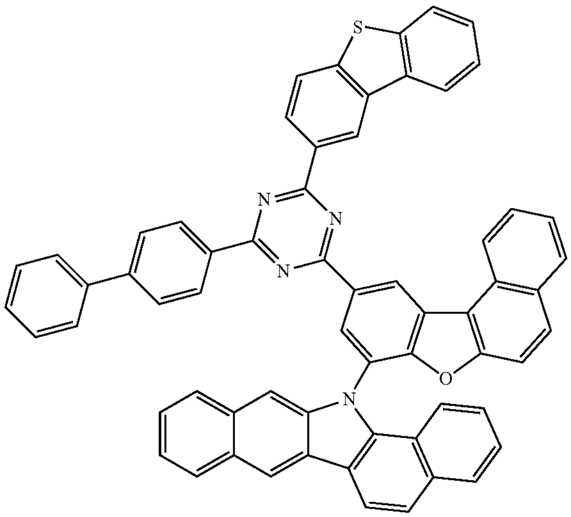
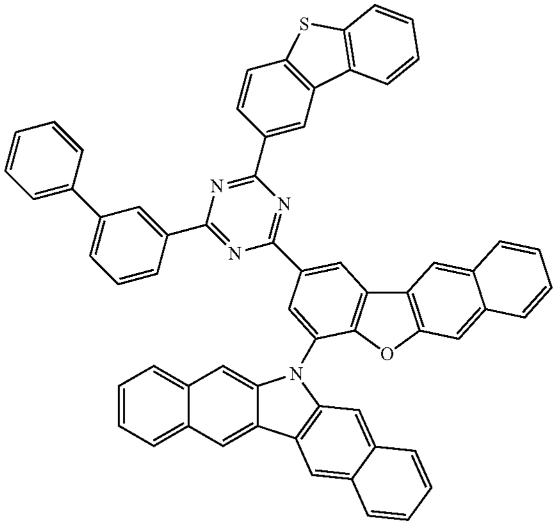

-continued
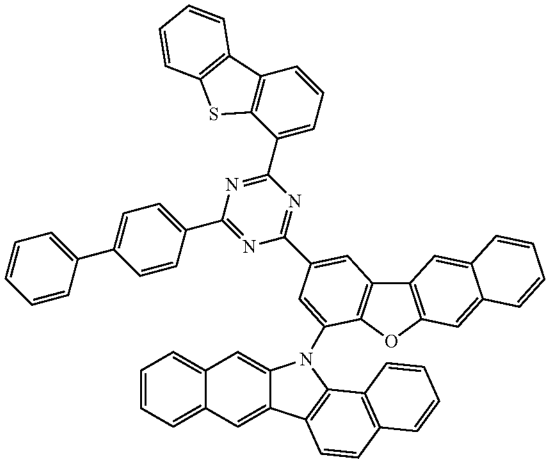
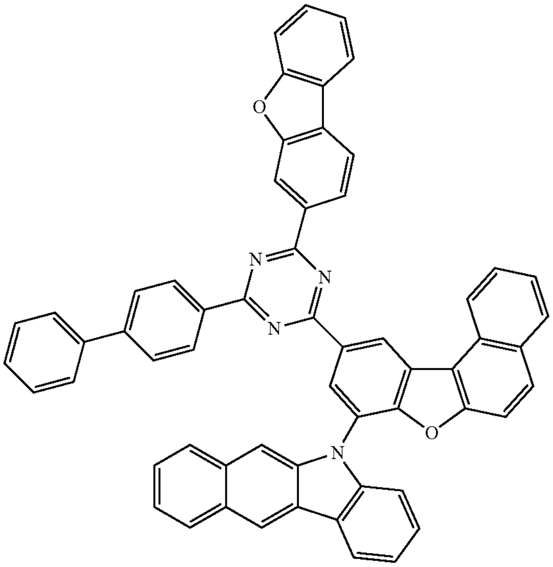
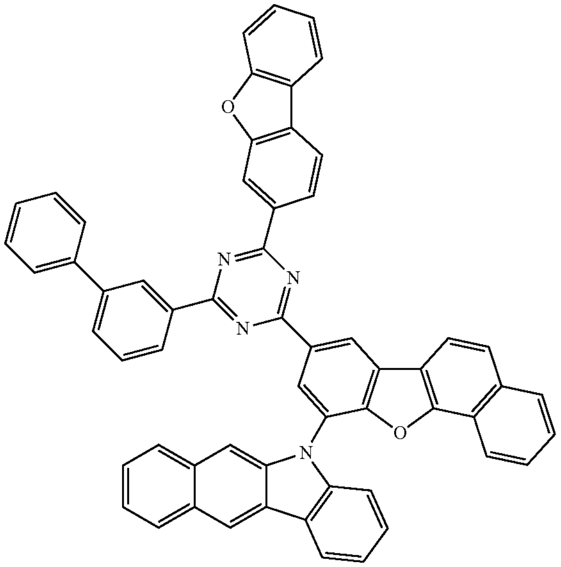
-continued
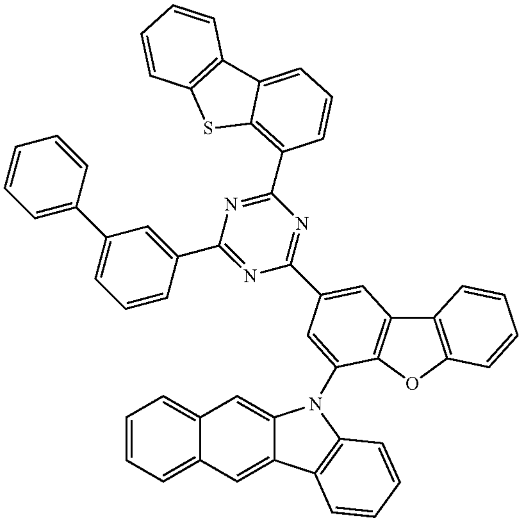
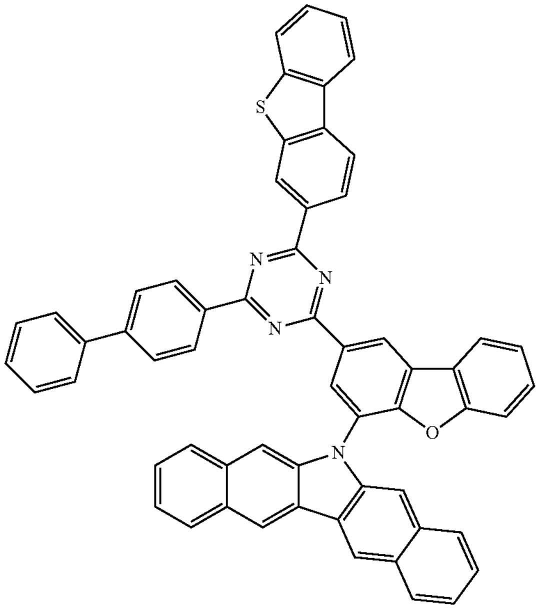
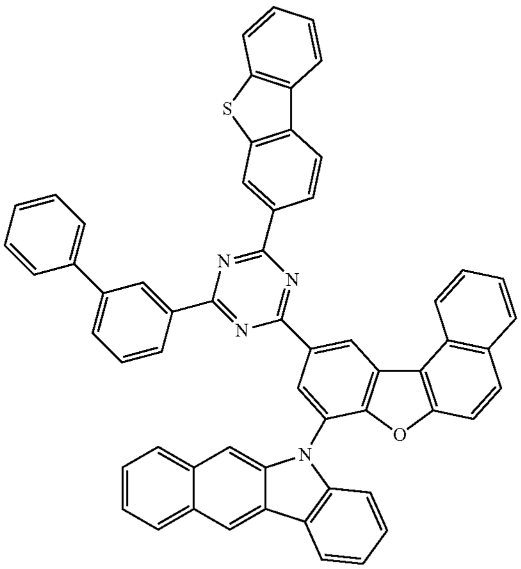

-continued
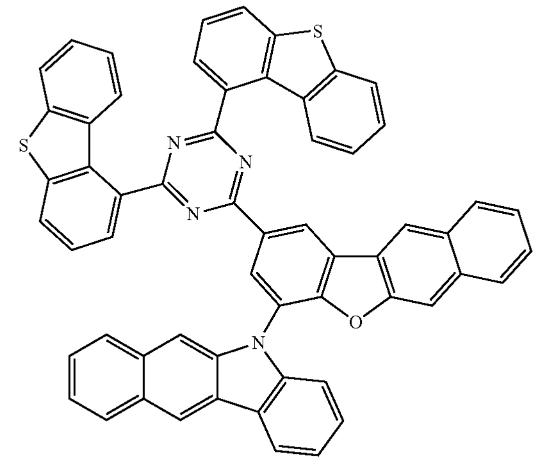
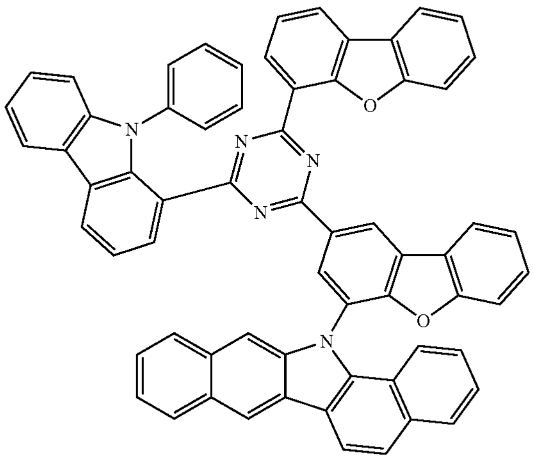
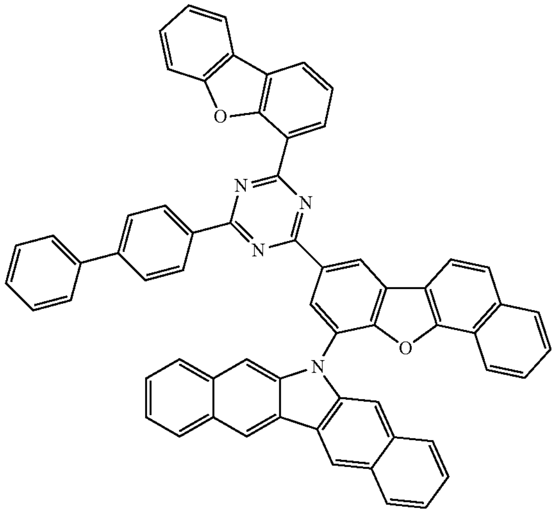
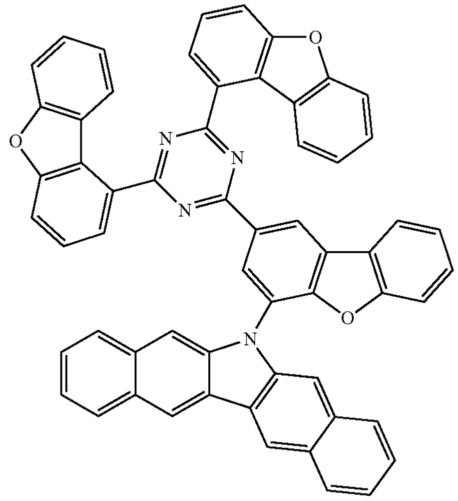
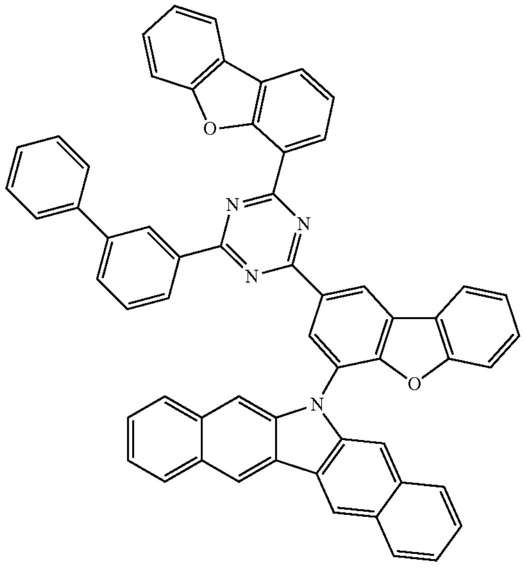
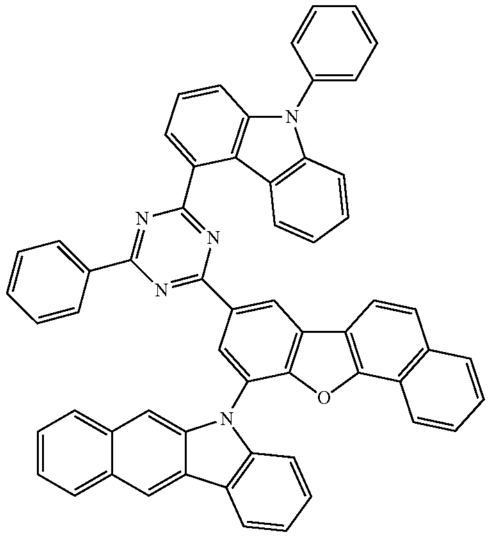
-continued -continued
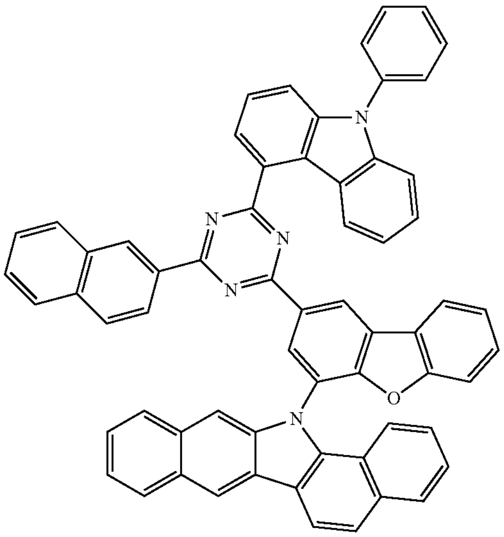
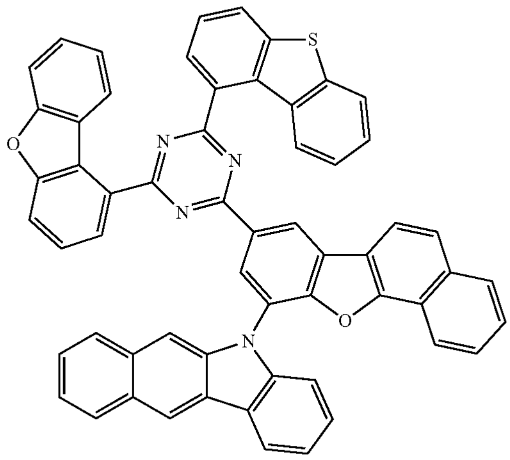
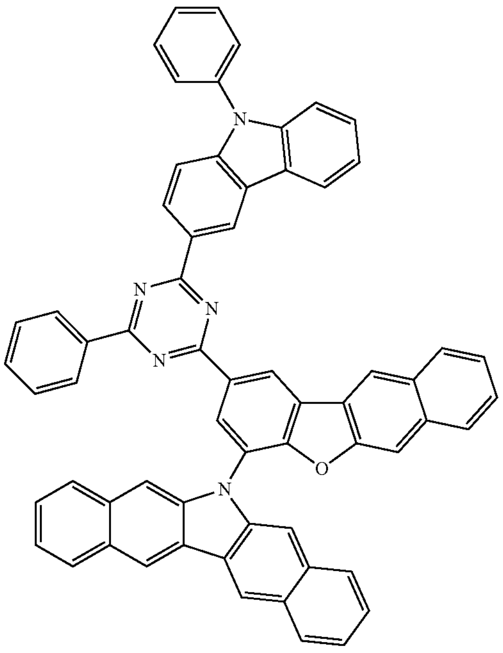
-continued
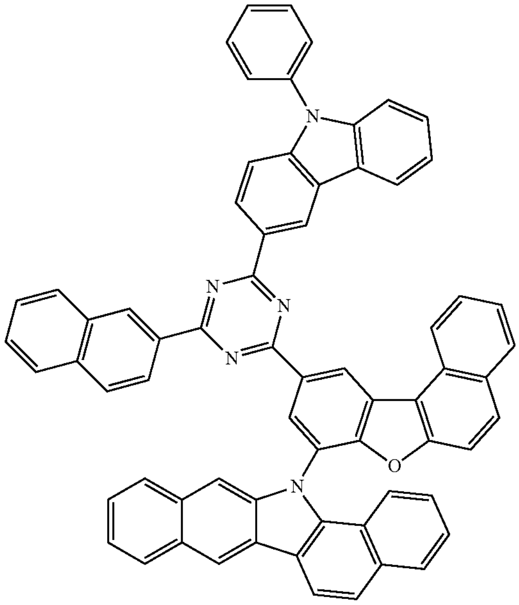
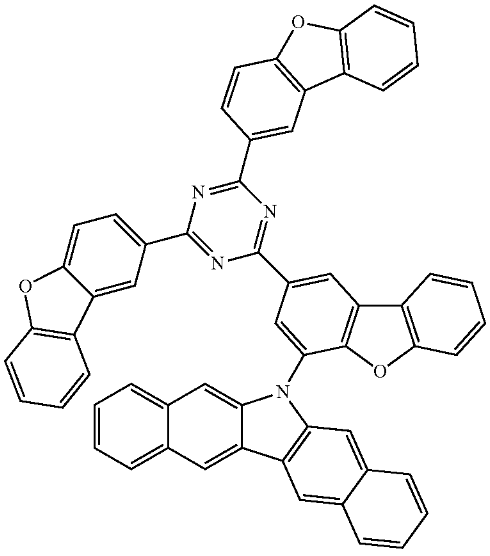

-continued
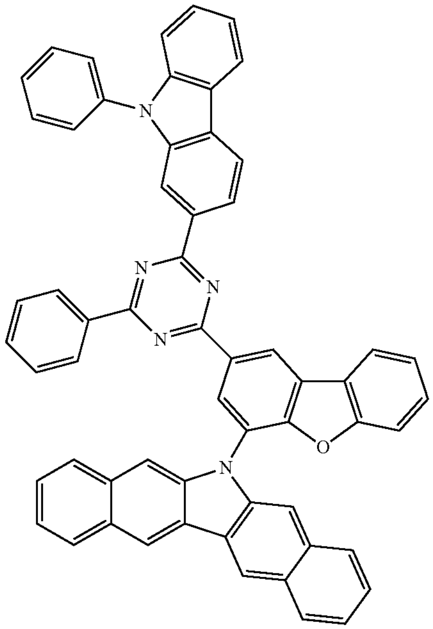
-continued
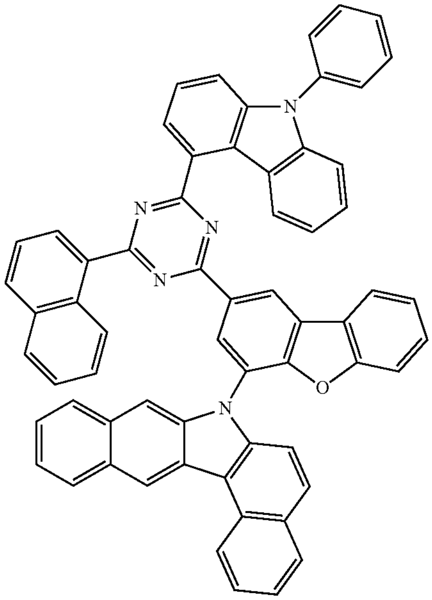
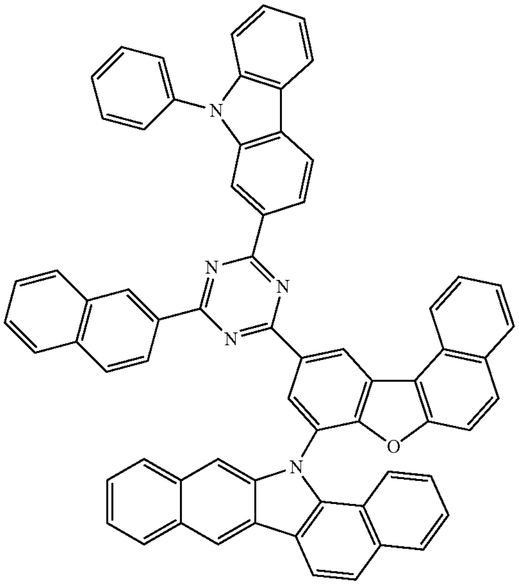
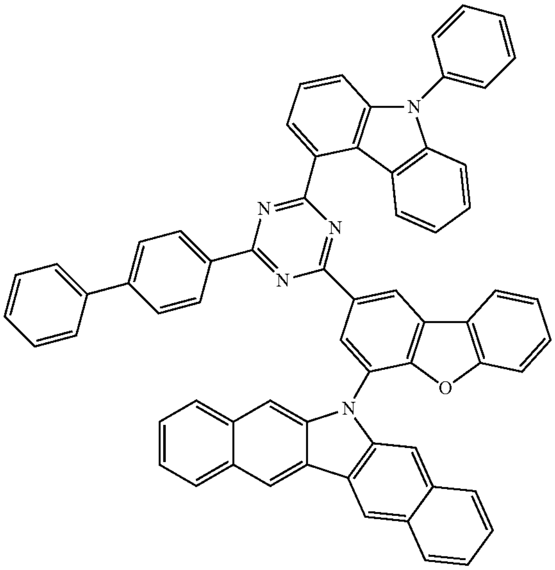

-continued
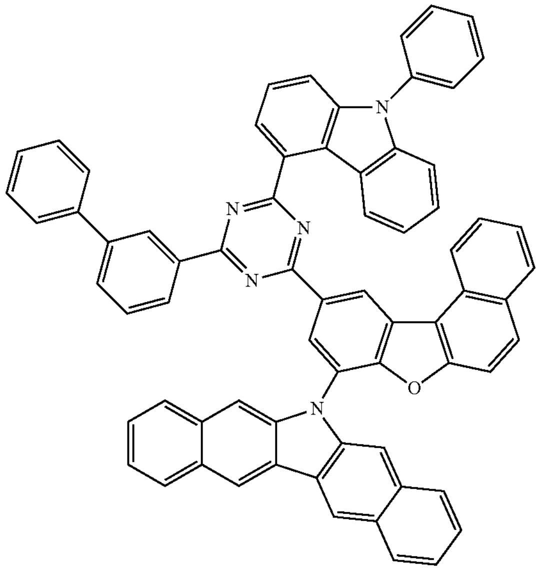
-continued
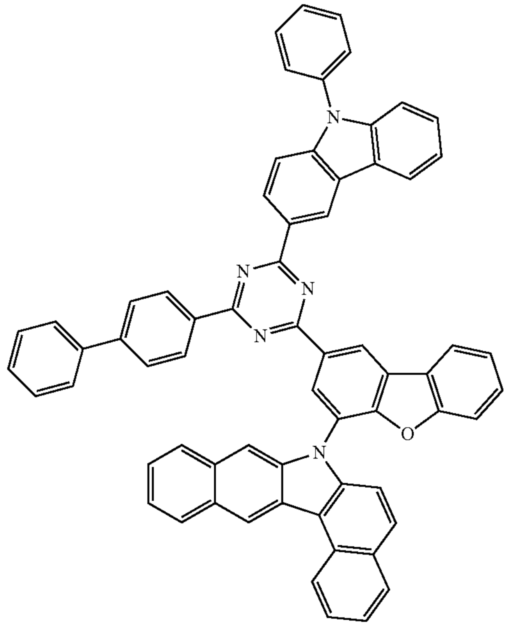
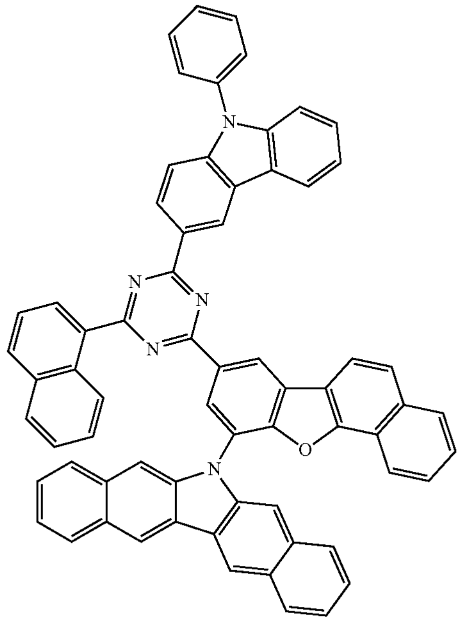
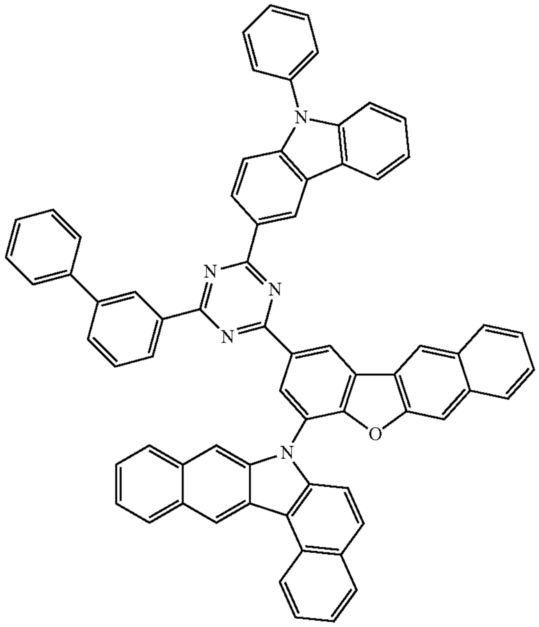

-continued
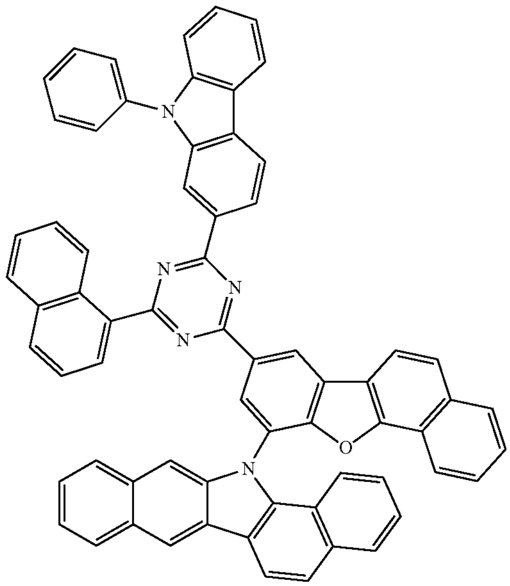
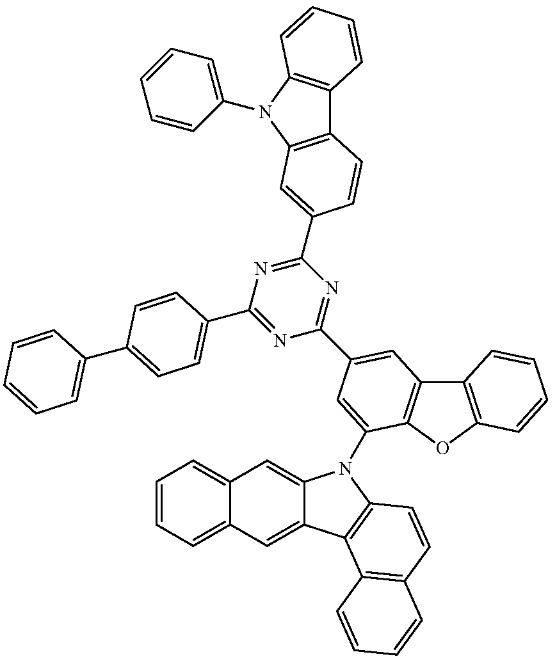
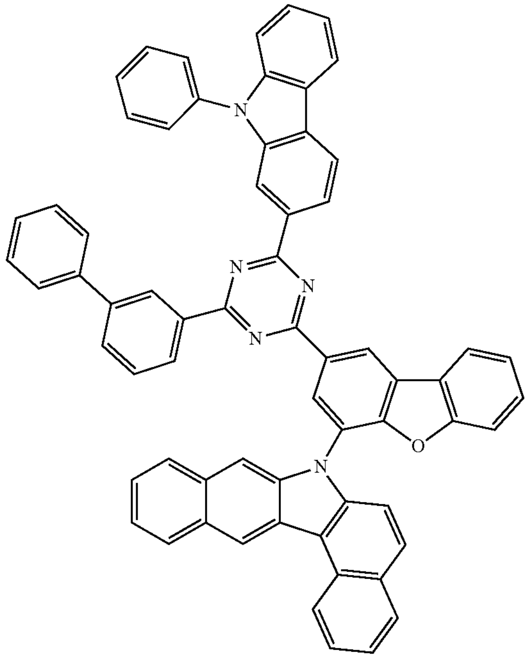
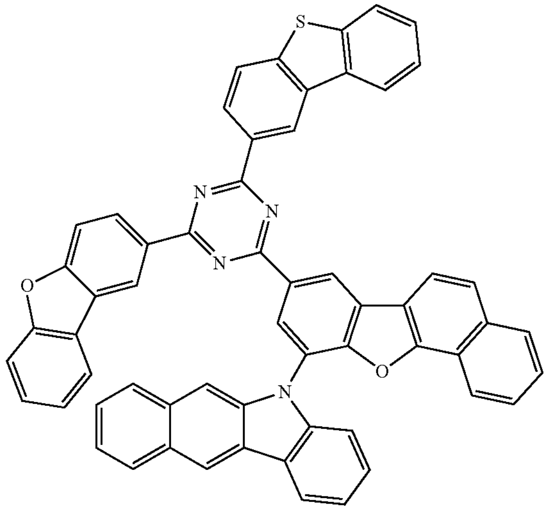
-continued
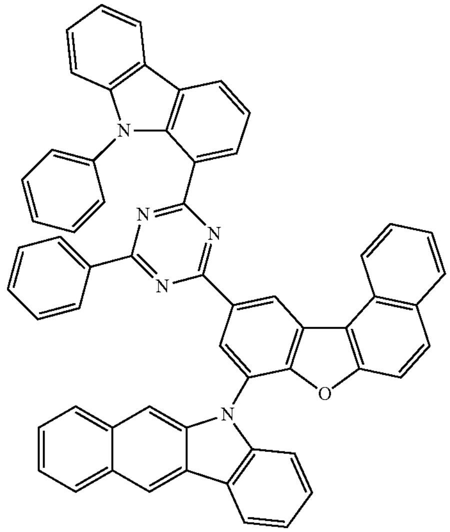

-continued
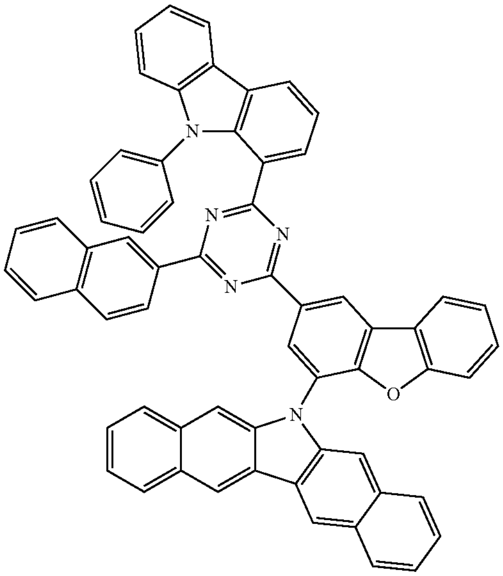
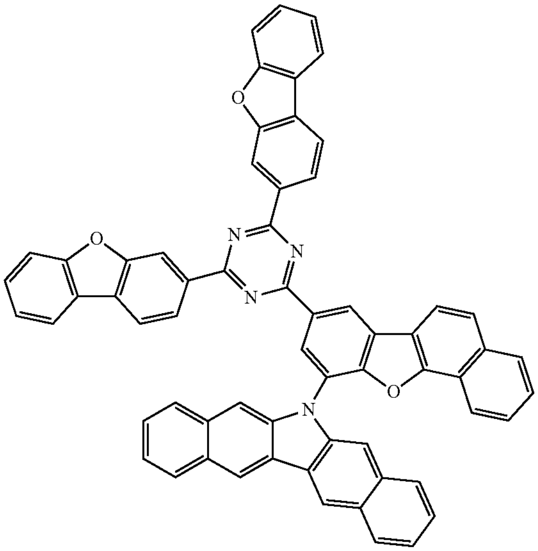
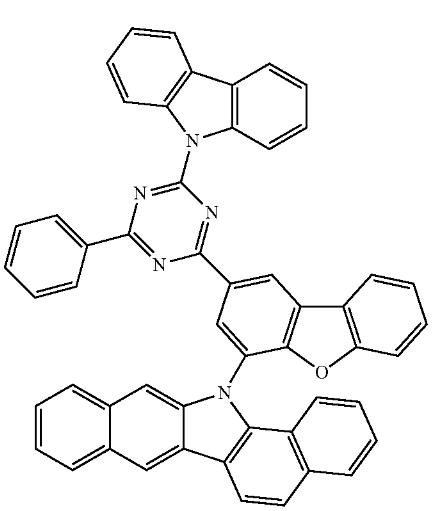
-continued
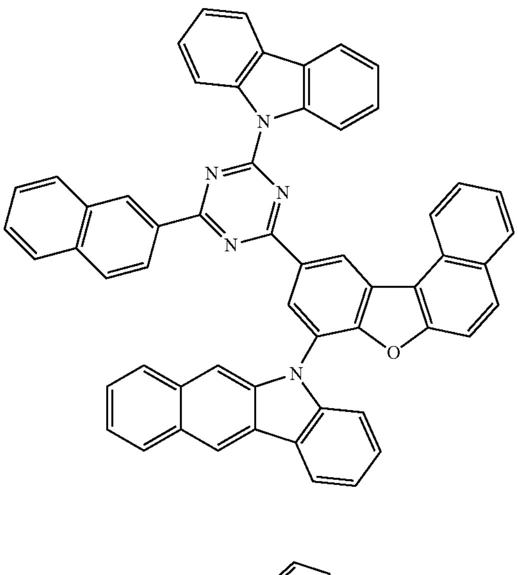
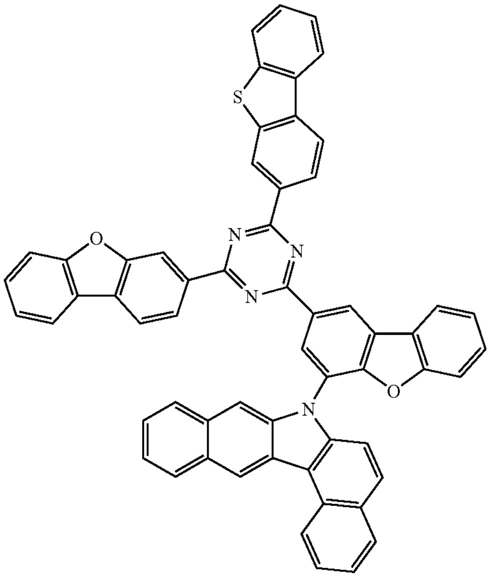
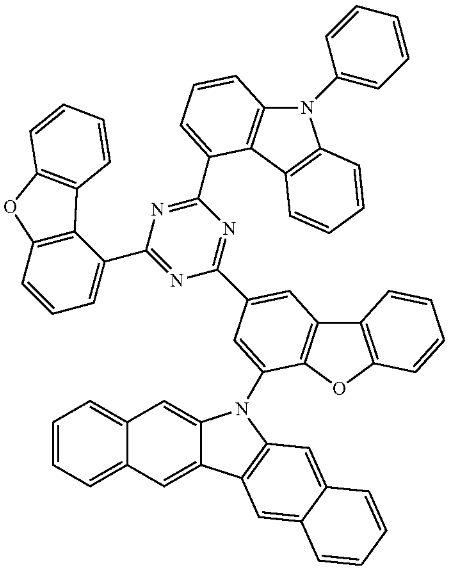

-continued
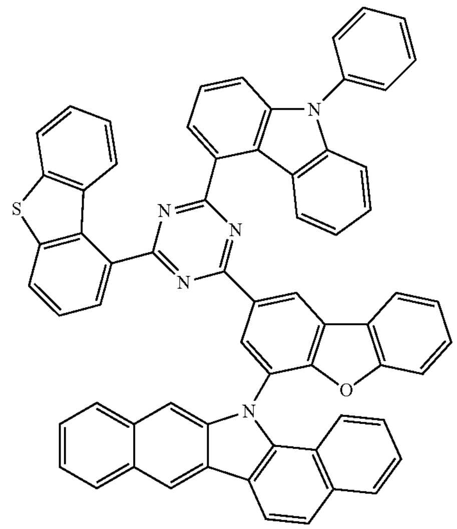
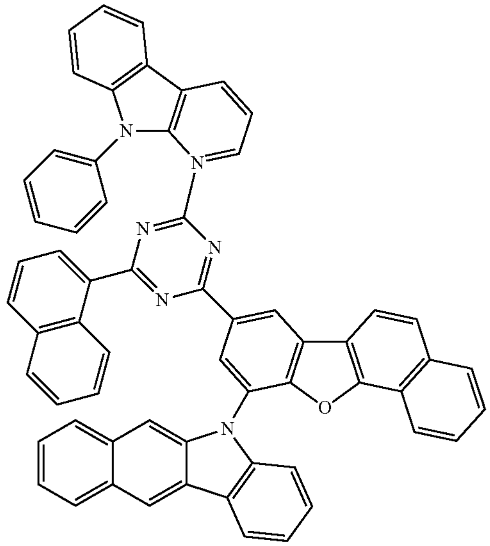
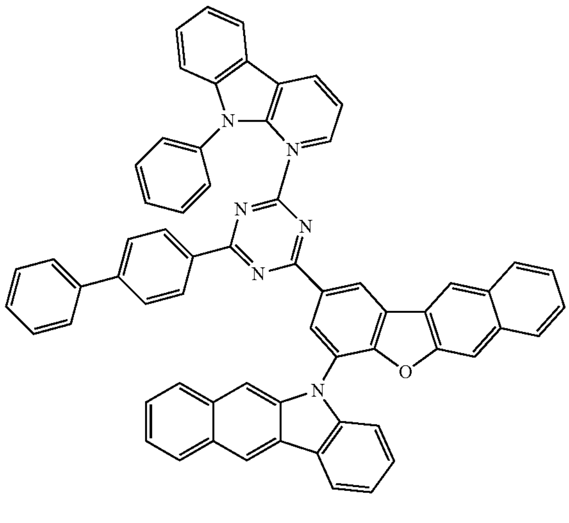
-continued
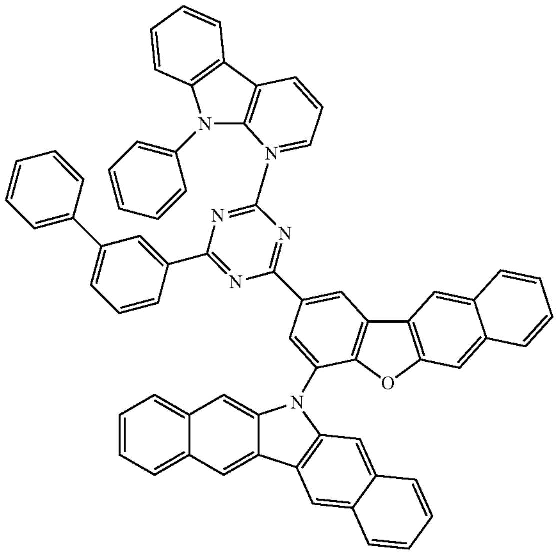
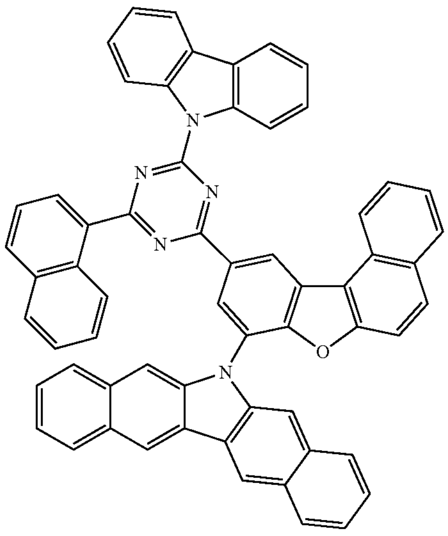
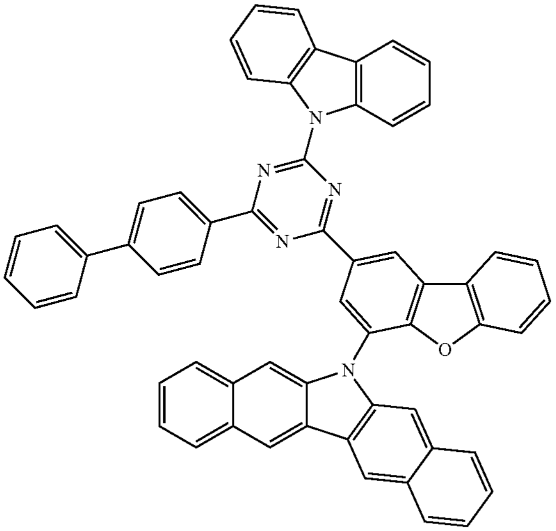

-continued
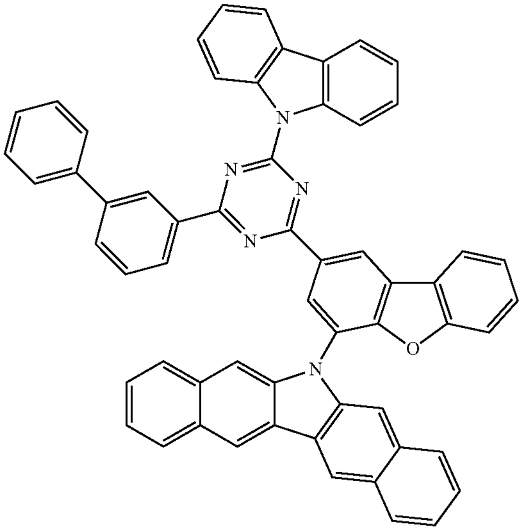
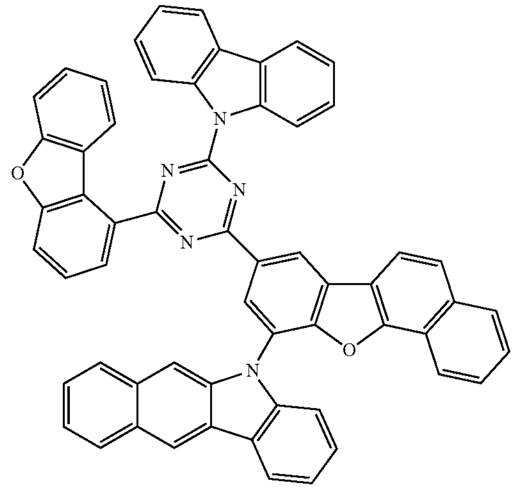
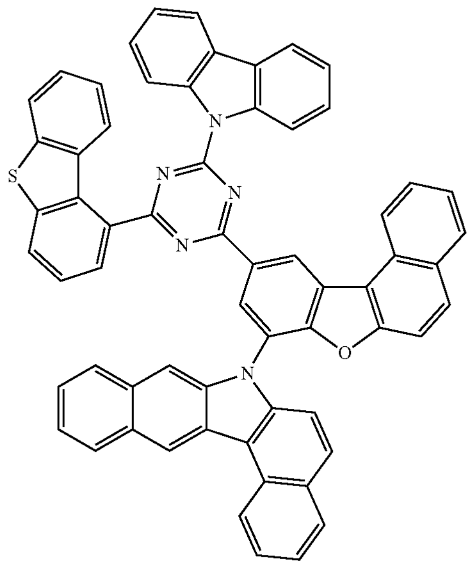
-continued
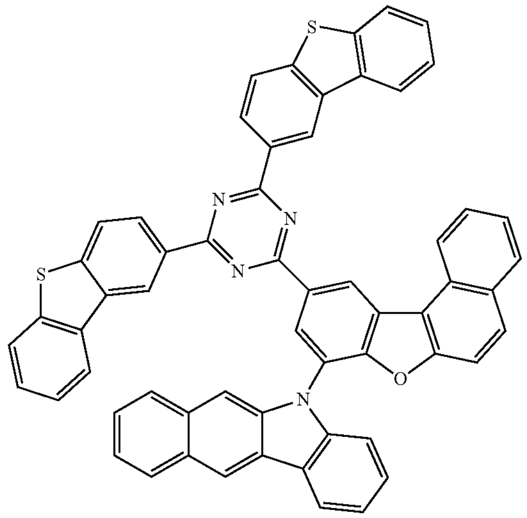
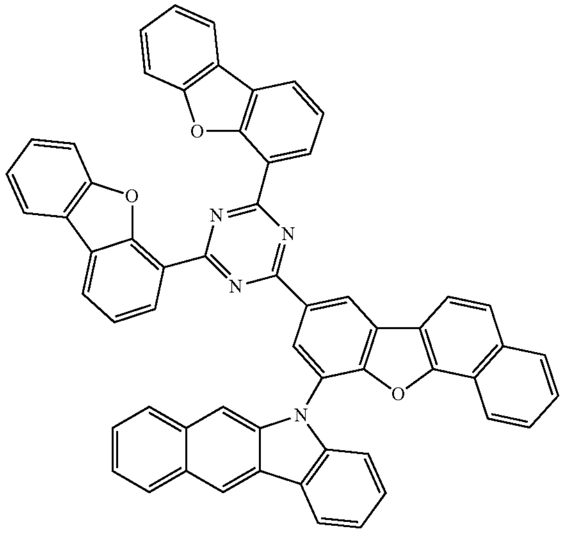
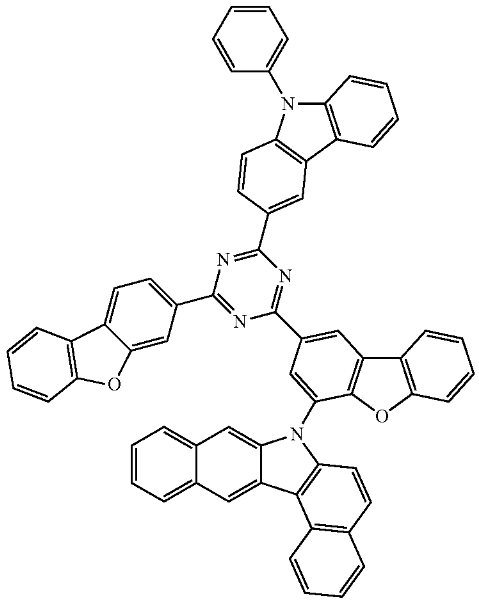

-continued
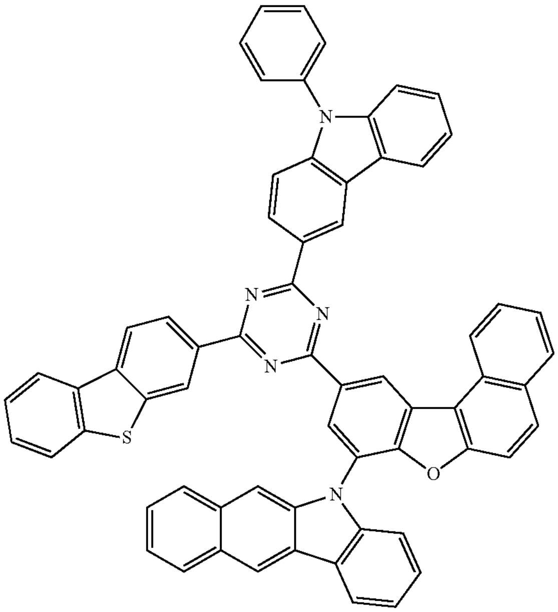
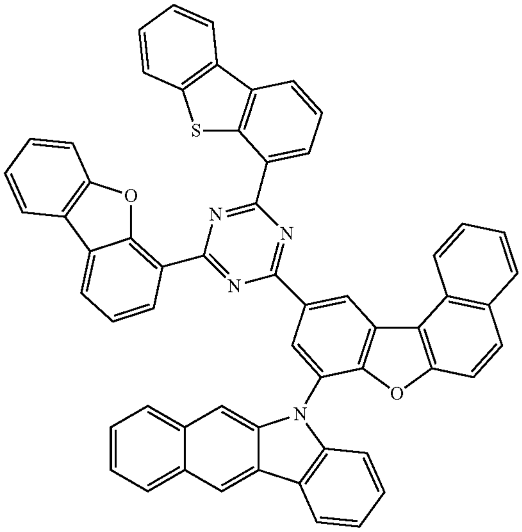
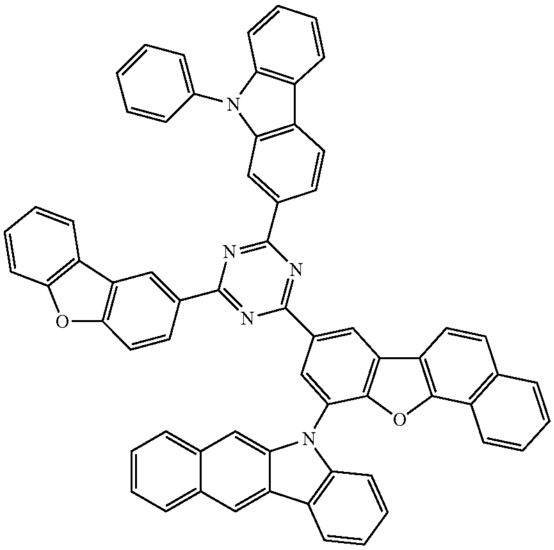
-continued
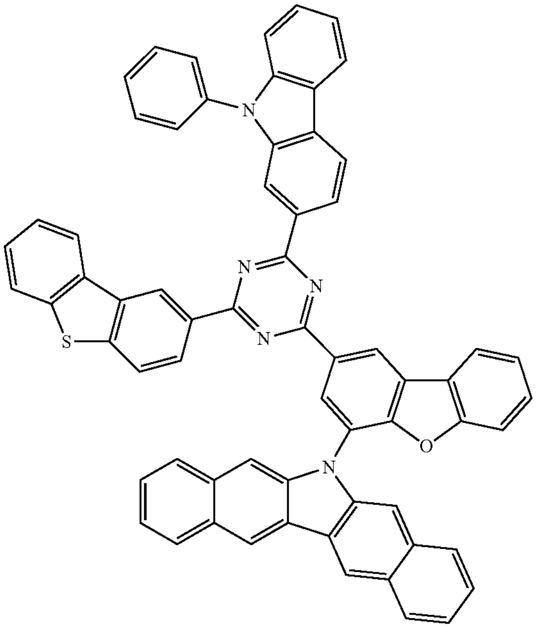
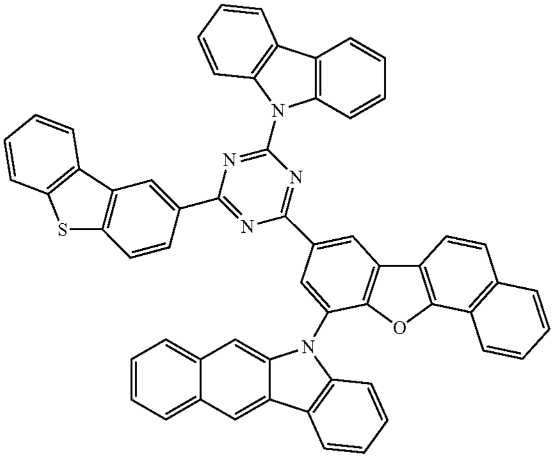
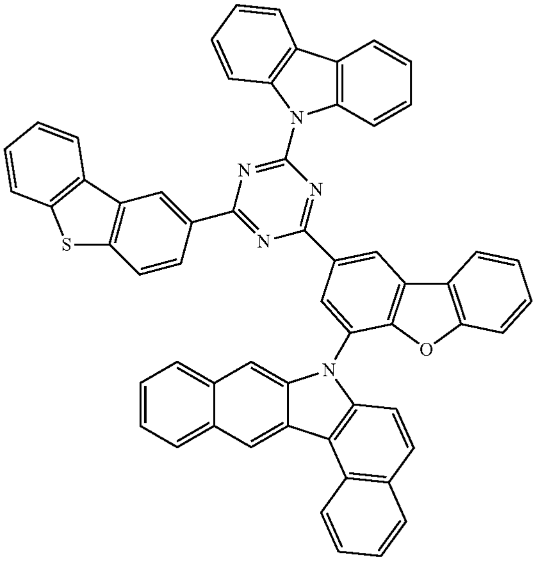

-continued
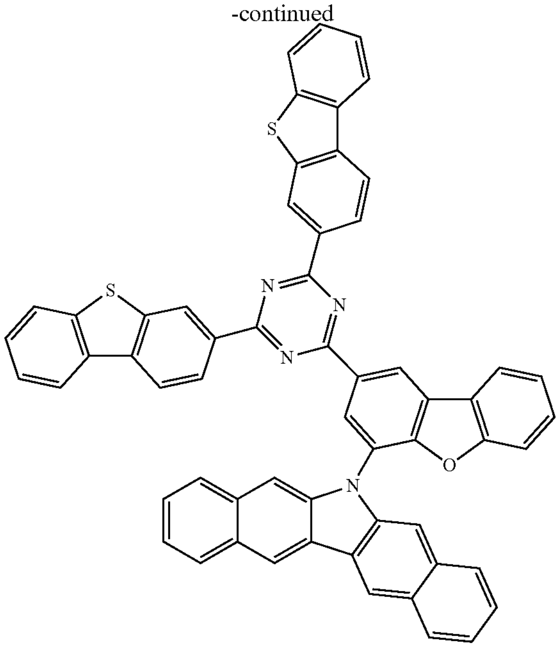
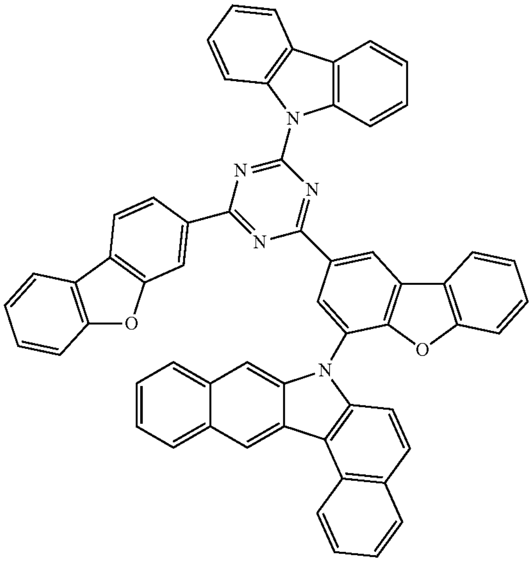
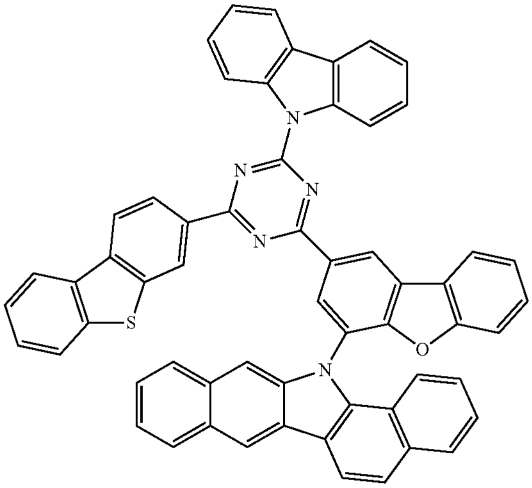
-continued
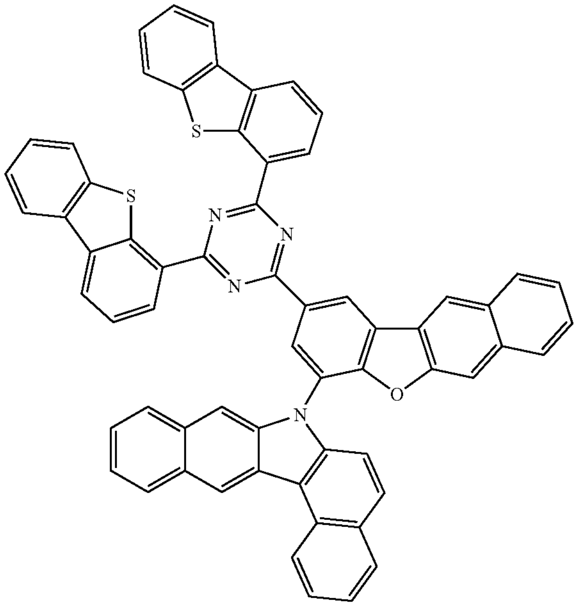
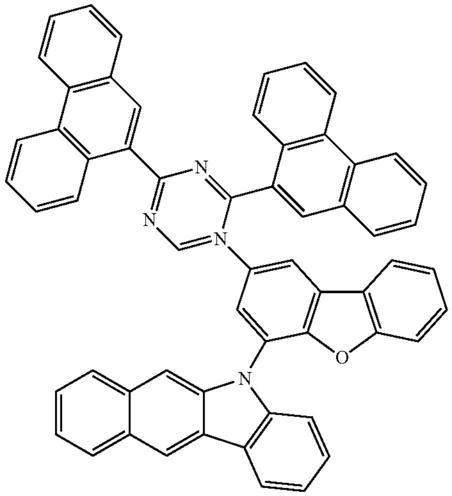
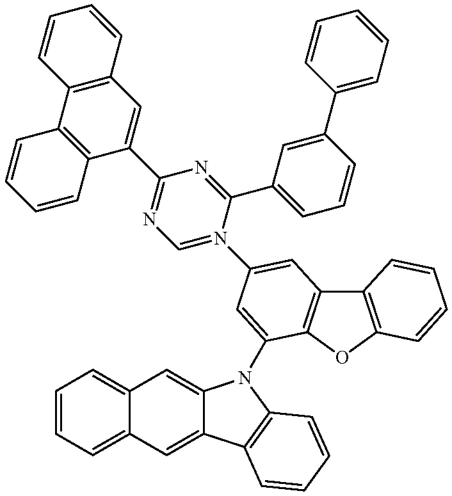

-continued
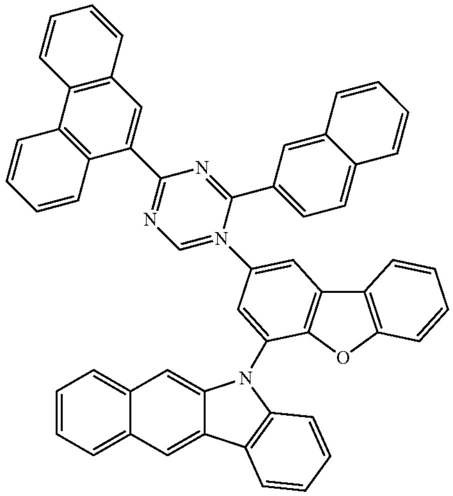
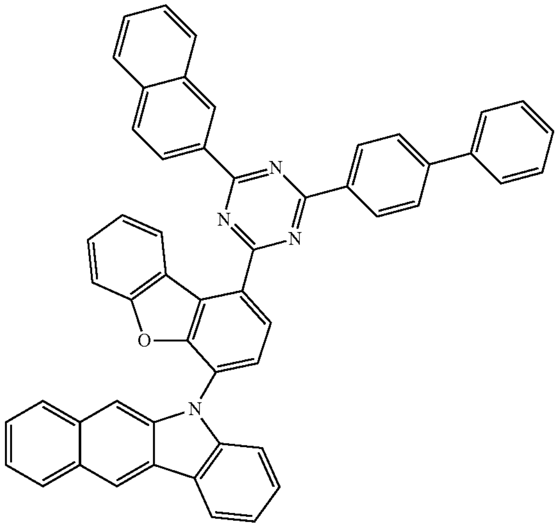
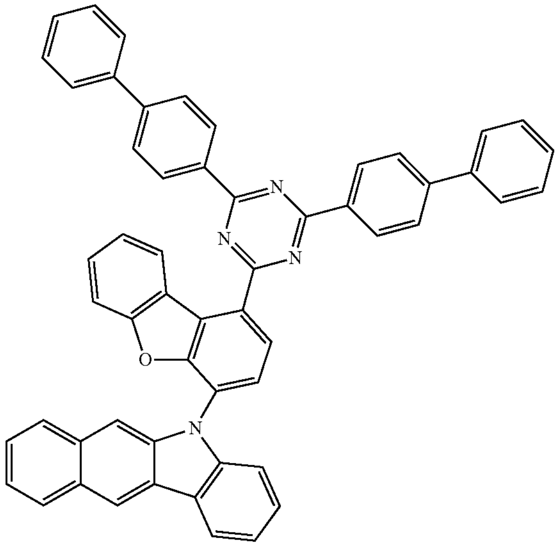
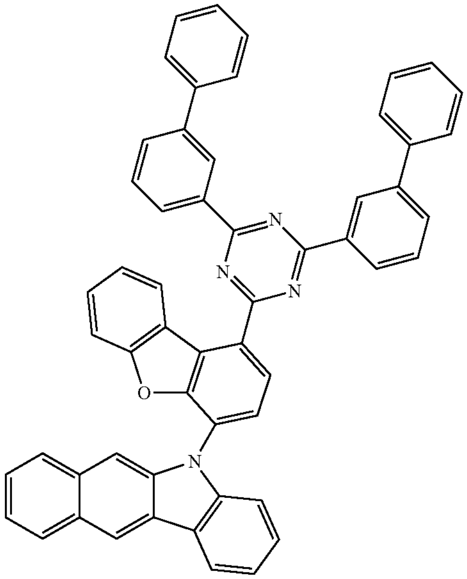
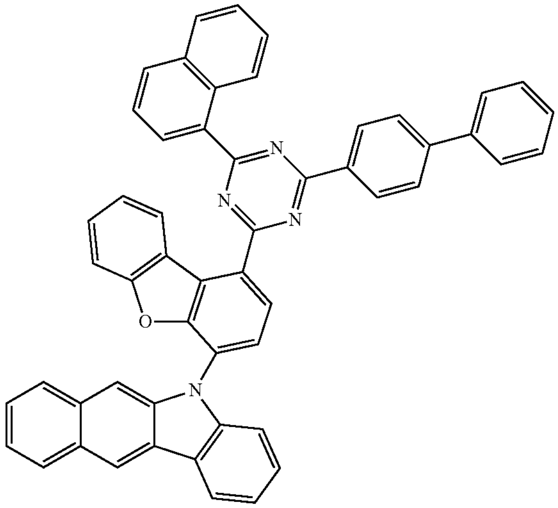
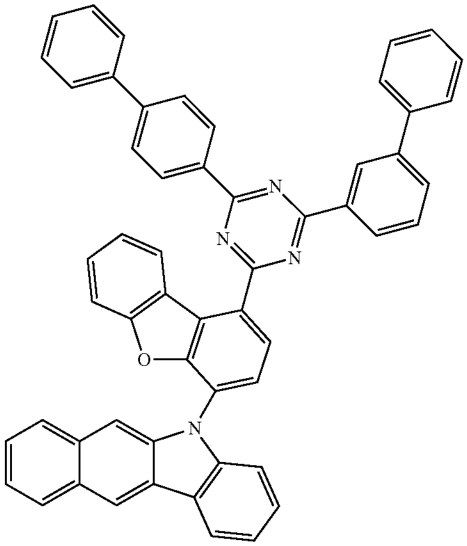
-continued -continued
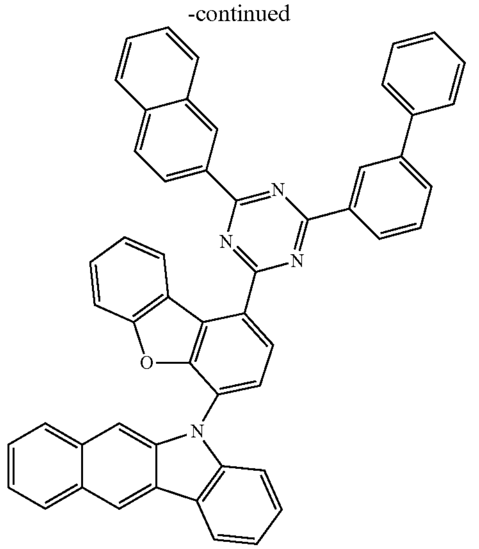
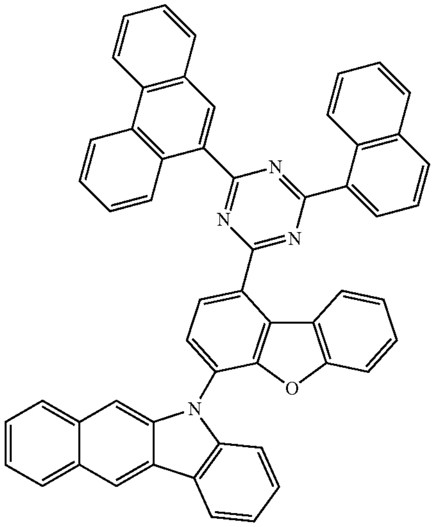
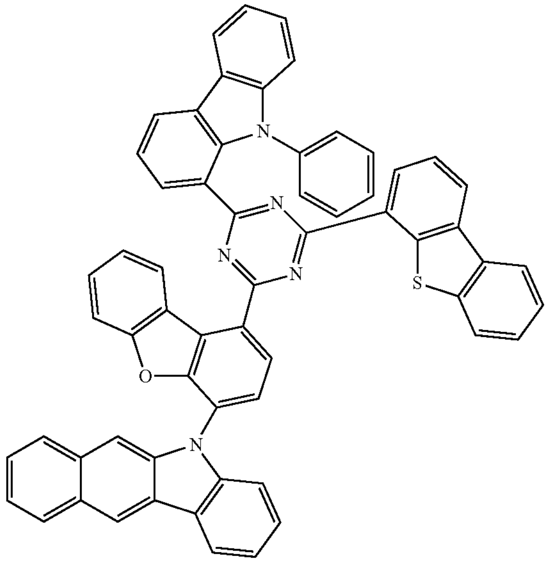
-continued
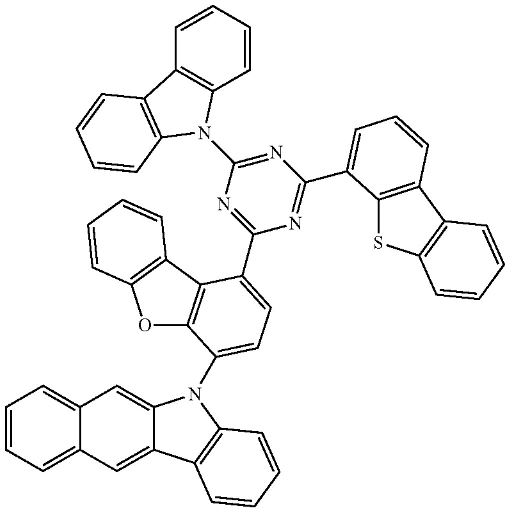
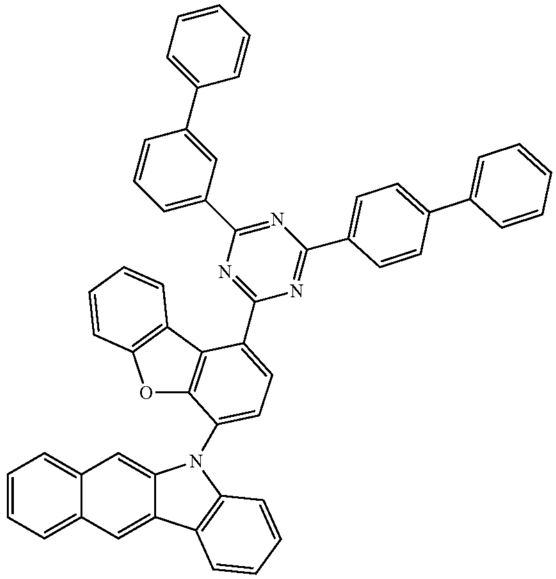
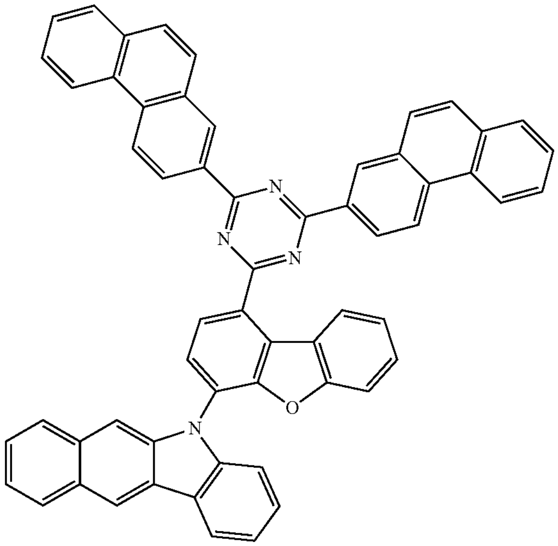

-continued
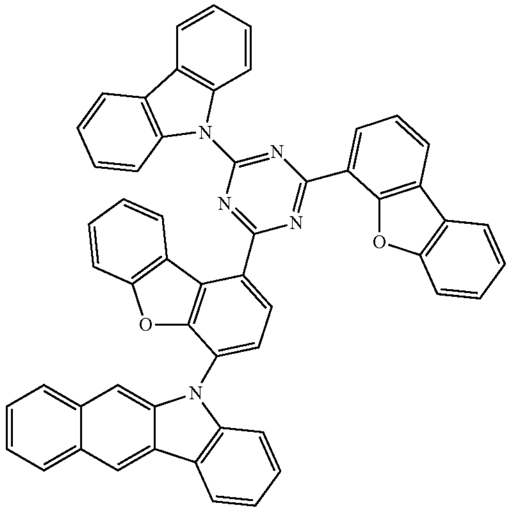
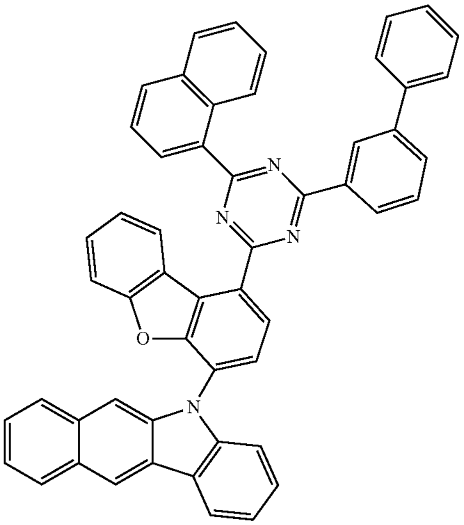
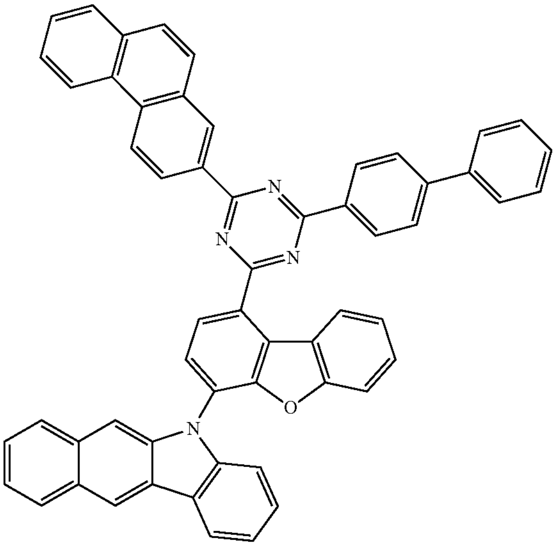
-continued
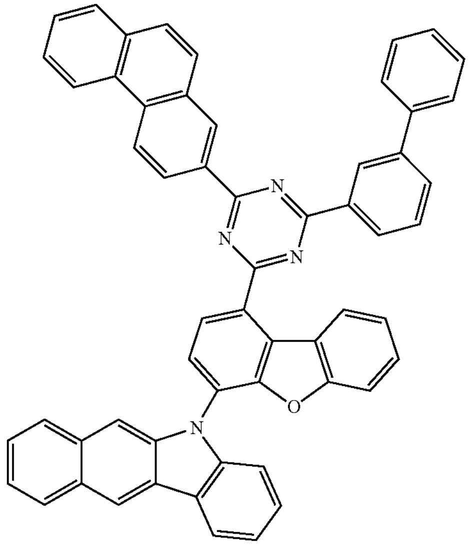
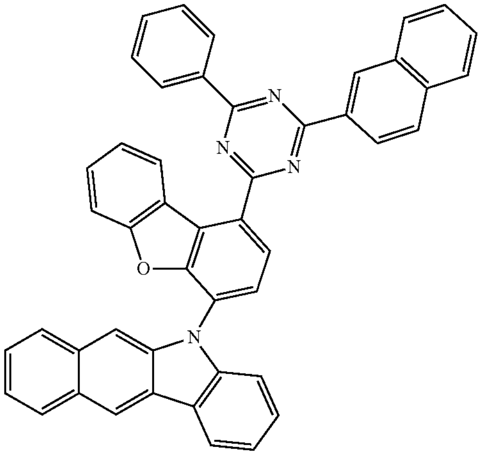
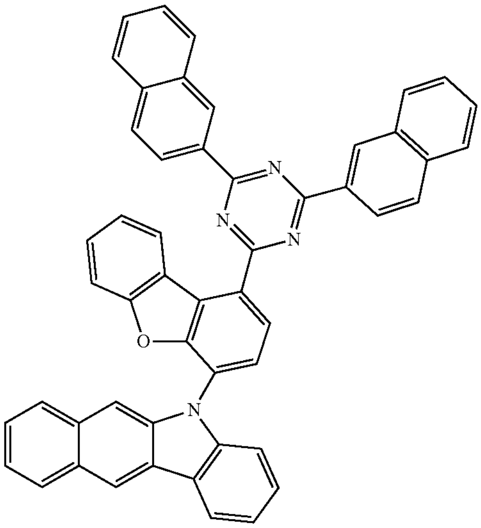

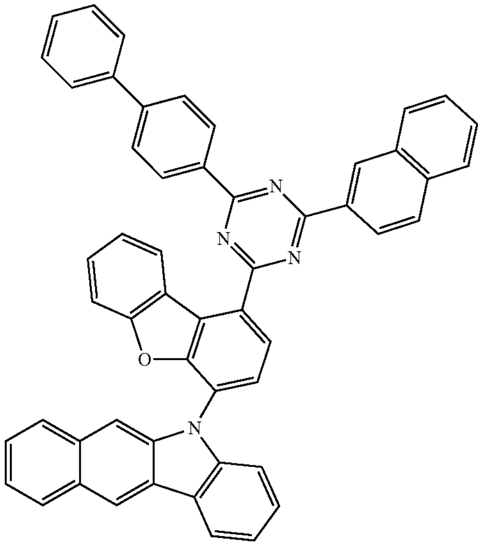
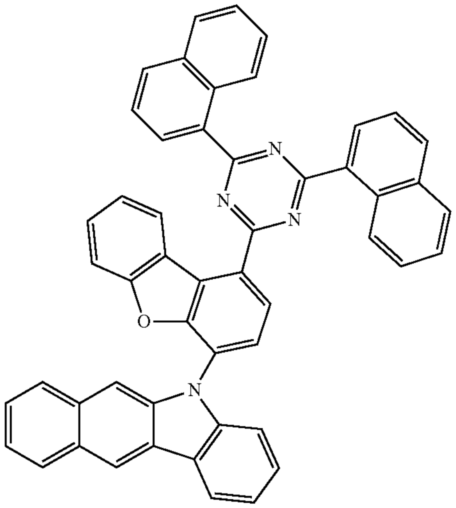
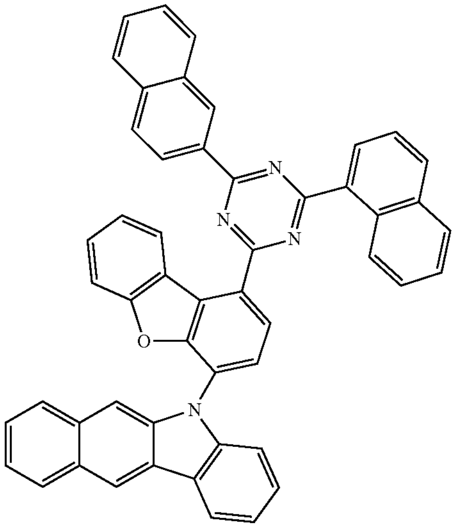
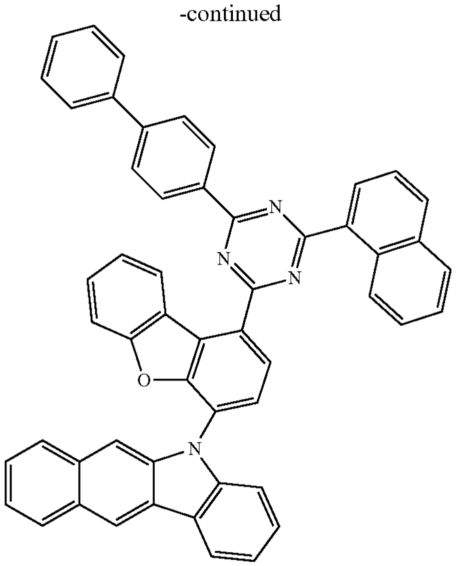
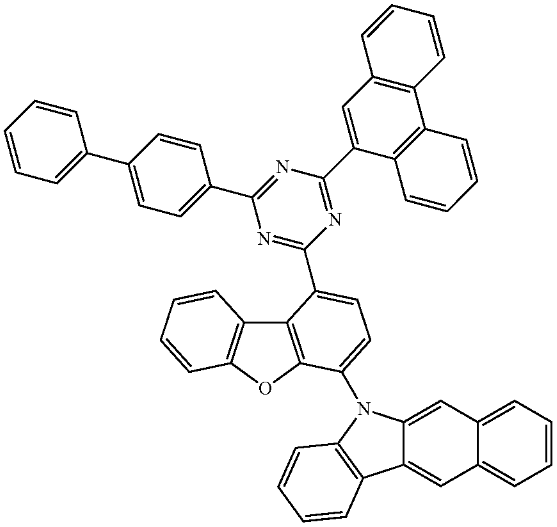
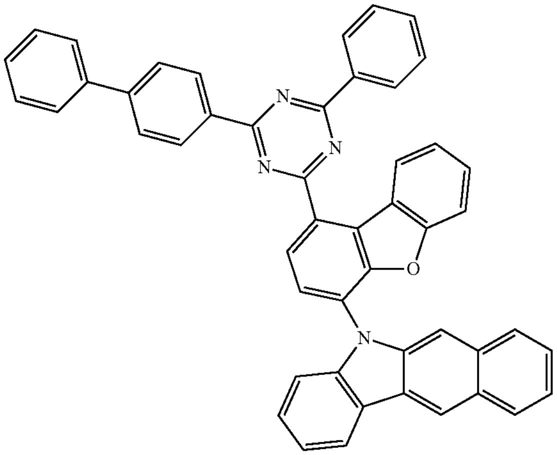

-continued
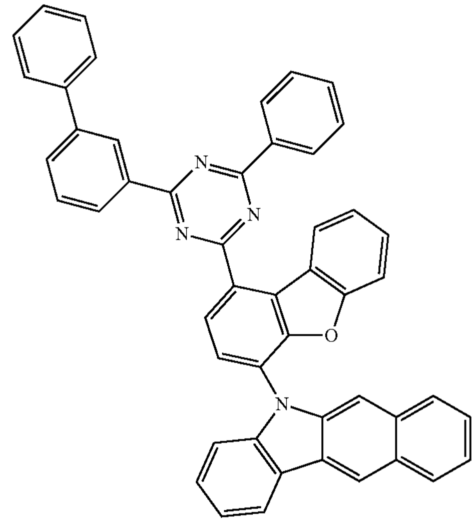
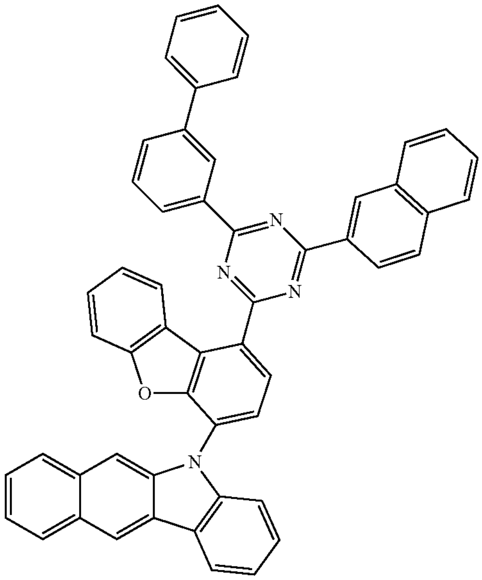
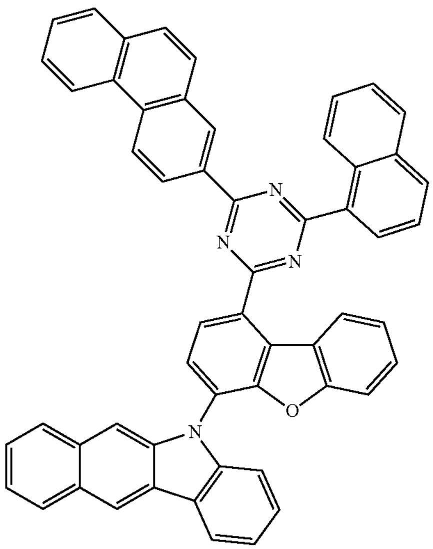
-continued
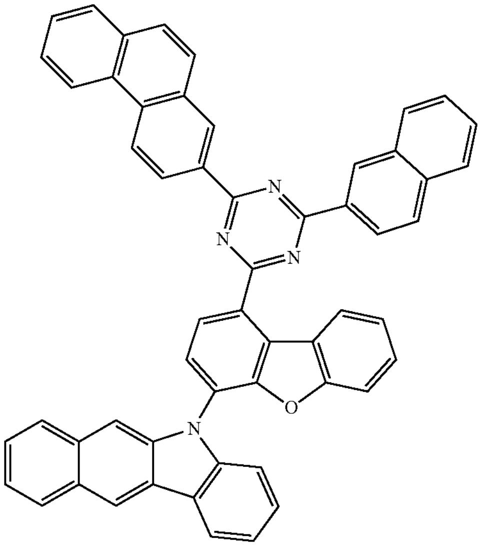
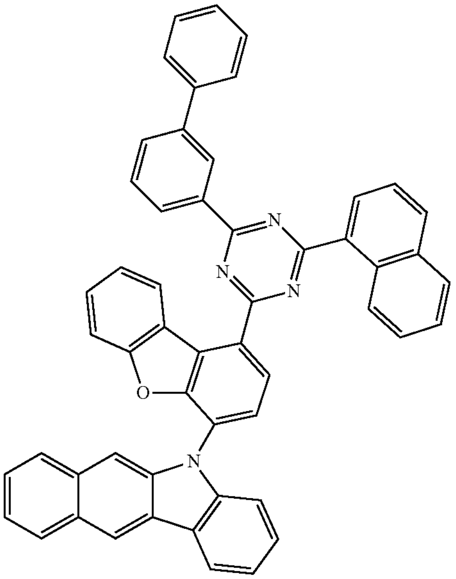
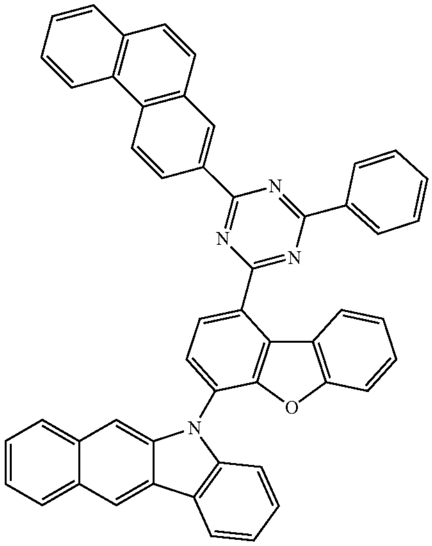

-continued
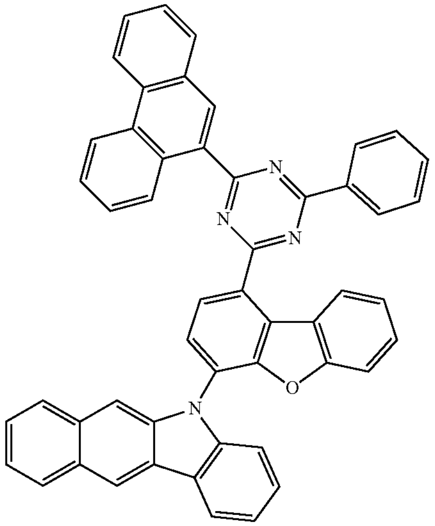
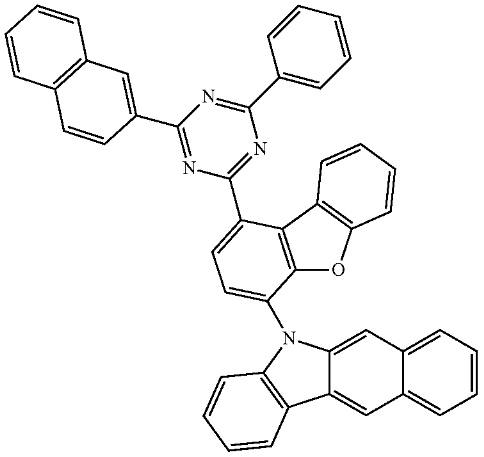
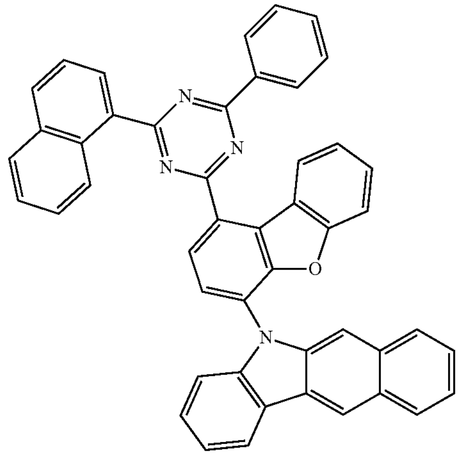
-continued
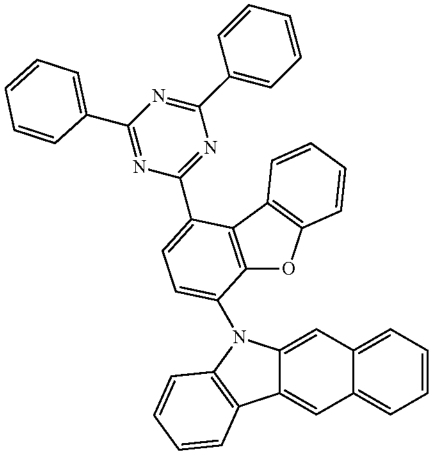
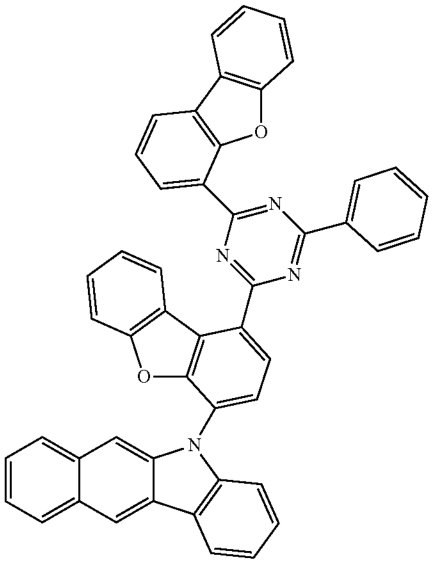
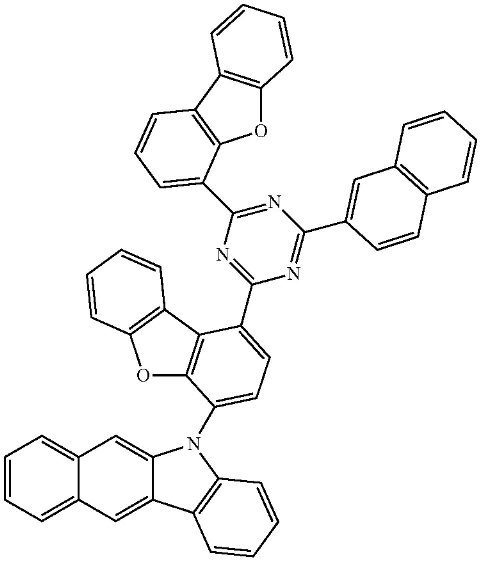

-continued
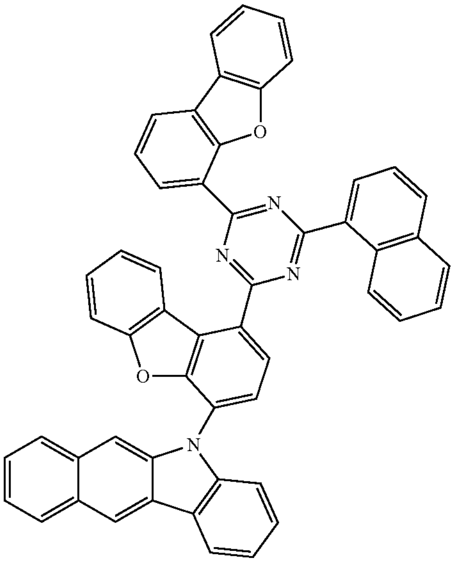
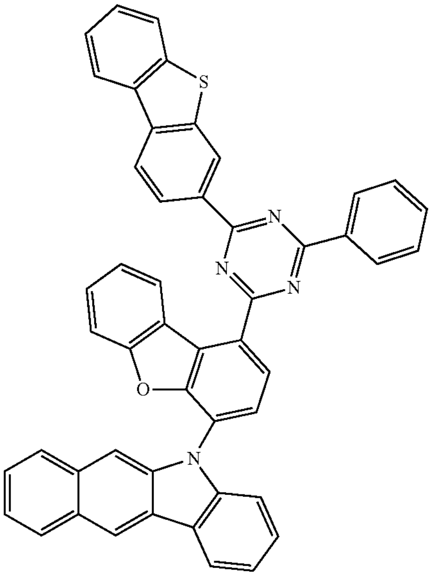
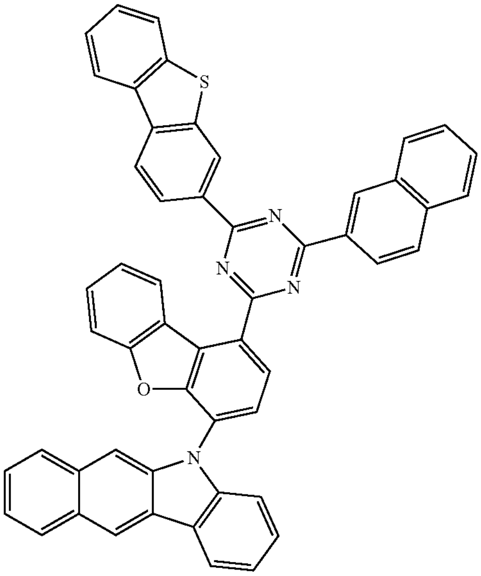
-continued
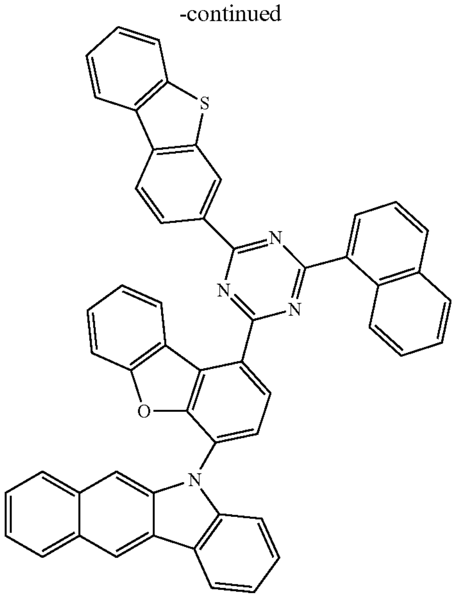
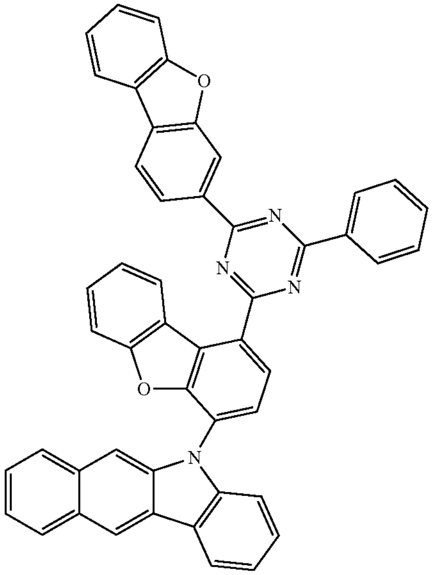
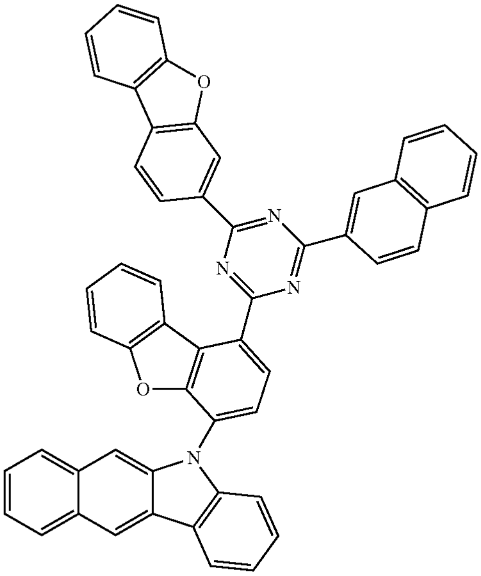

-continued
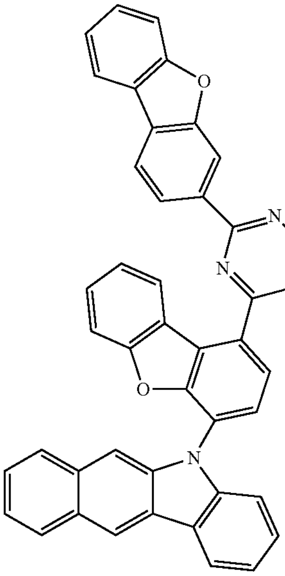
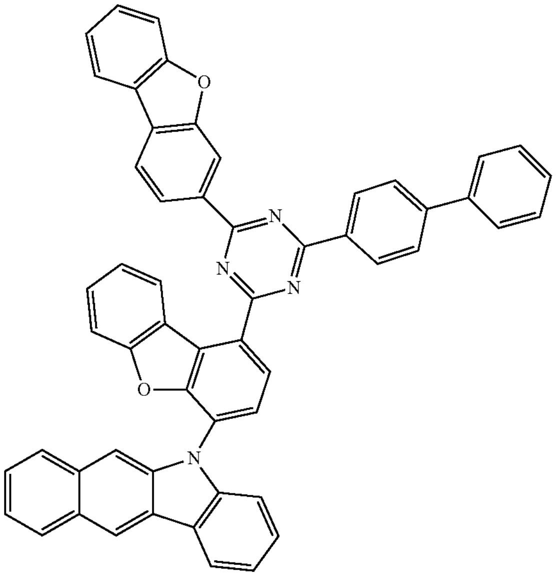
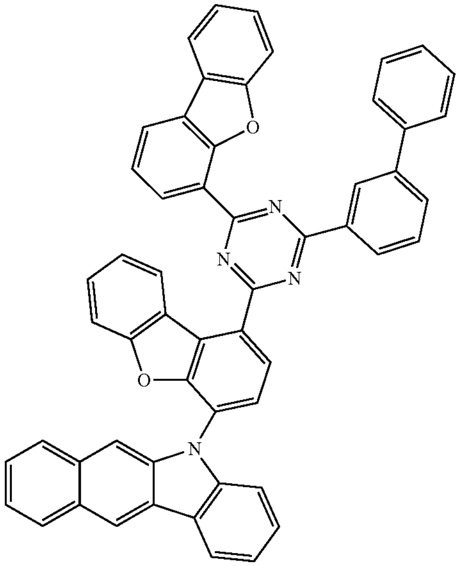
-continued
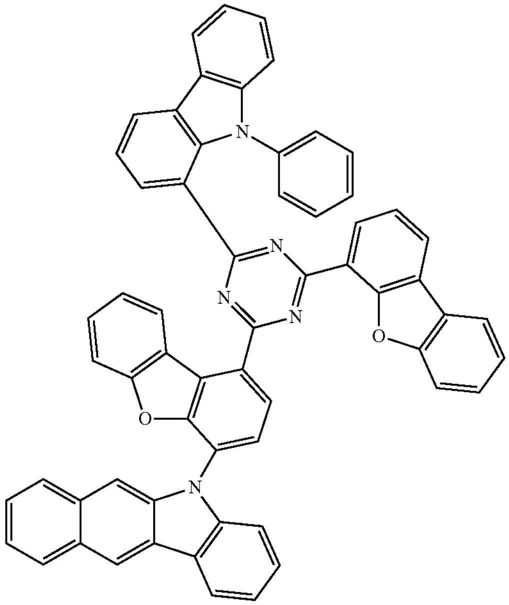
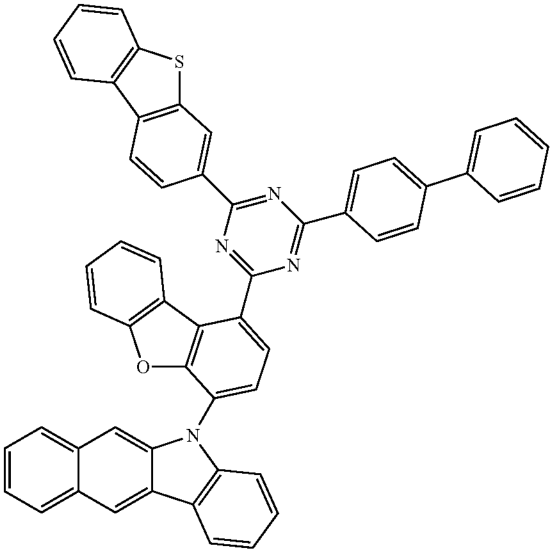
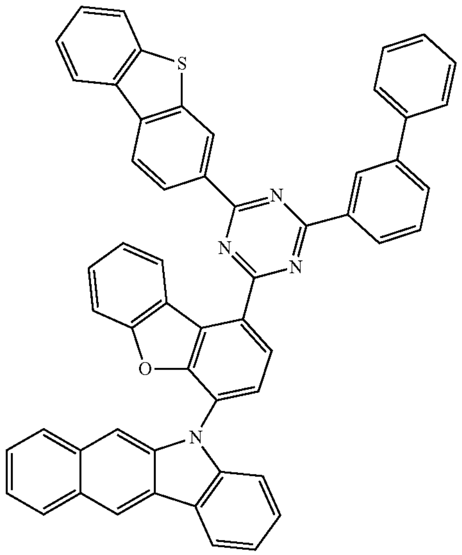

-continued
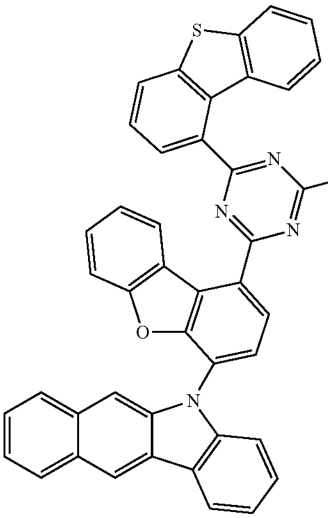
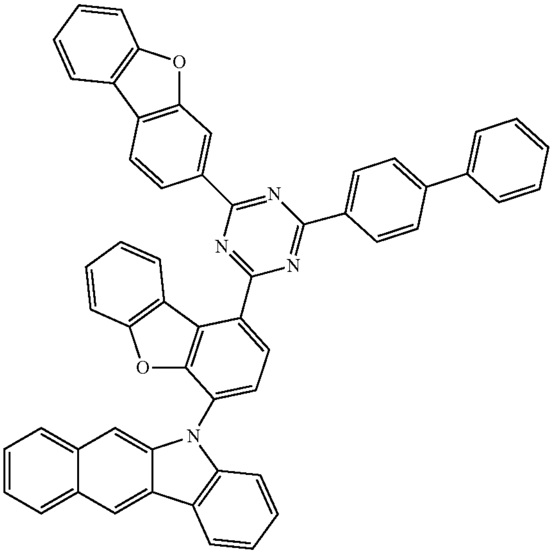
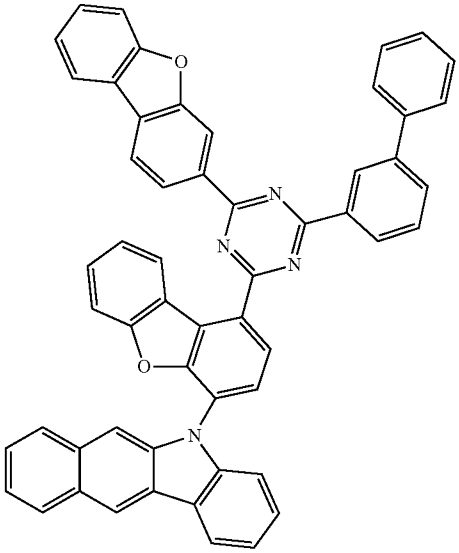
-continued
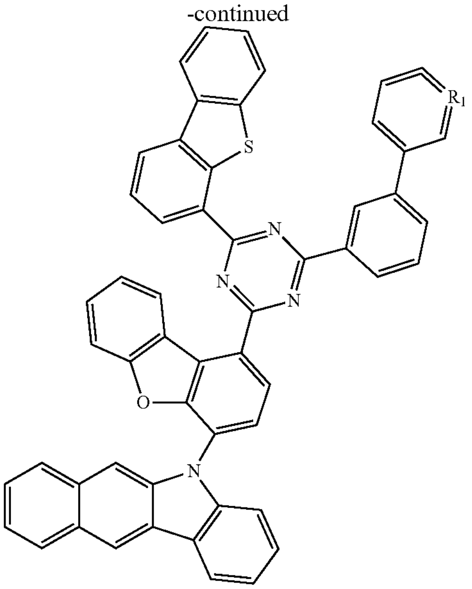
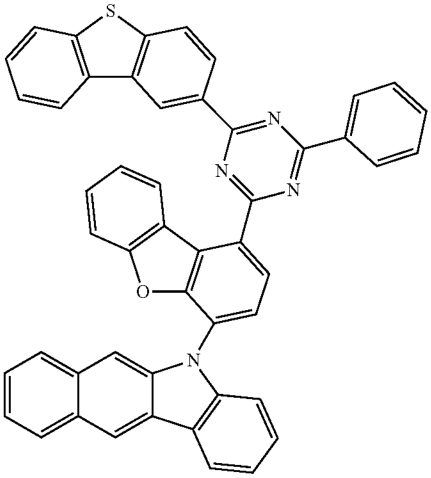
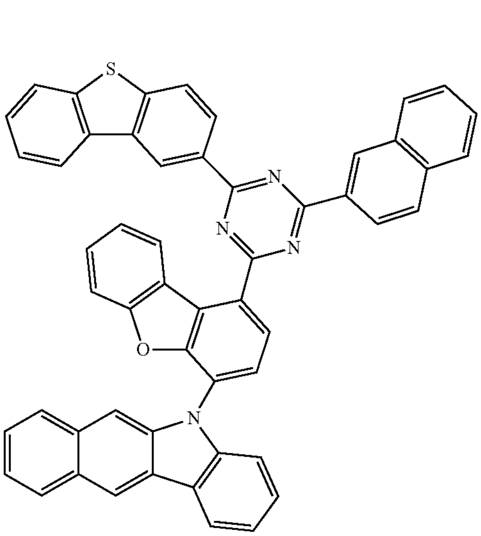

-continued
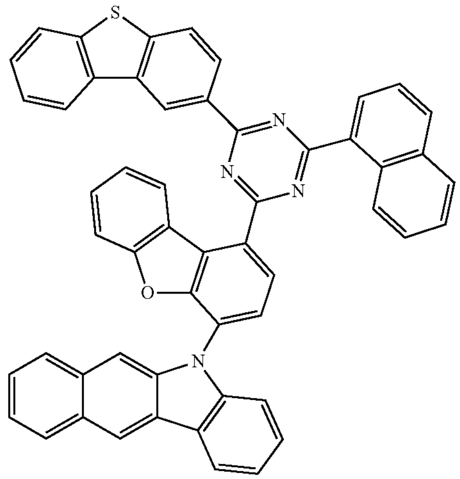
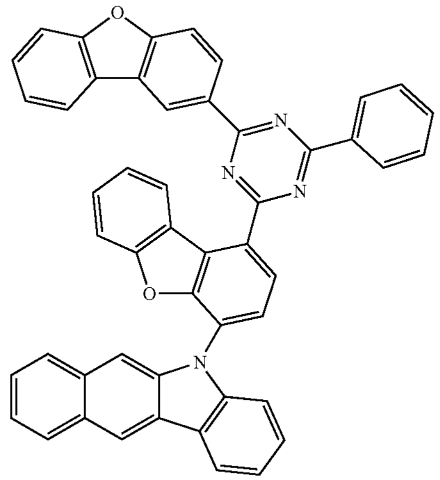
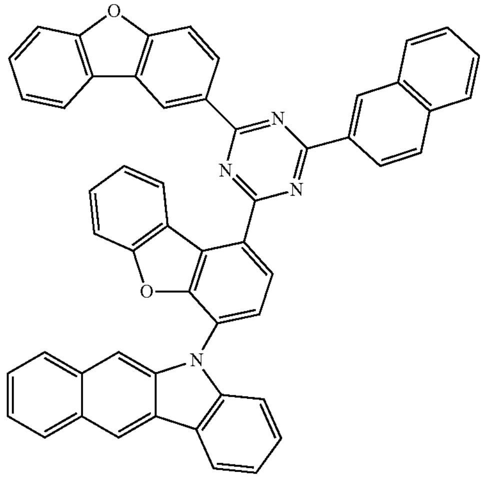
-continued
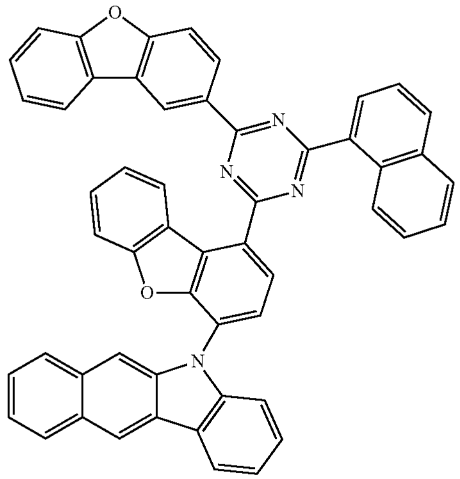
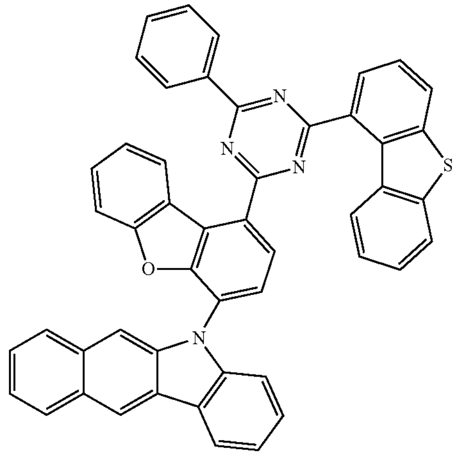
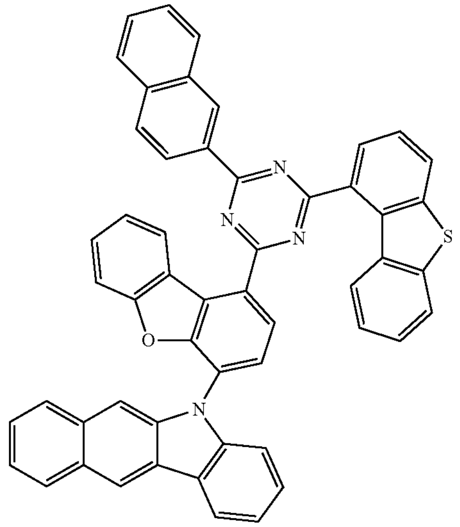

-continued
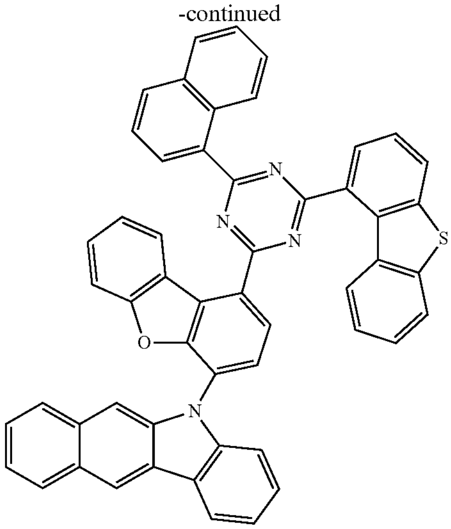
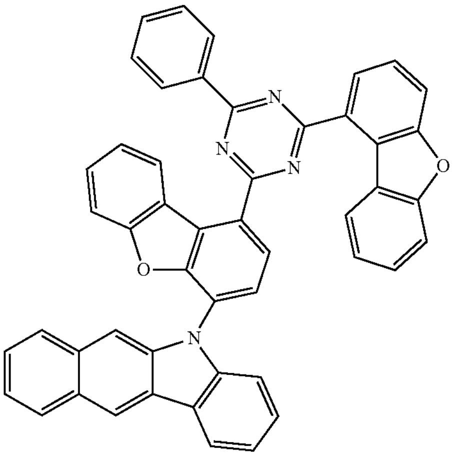
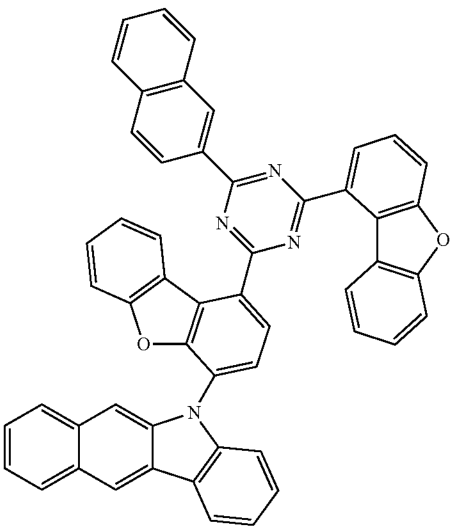
-continued
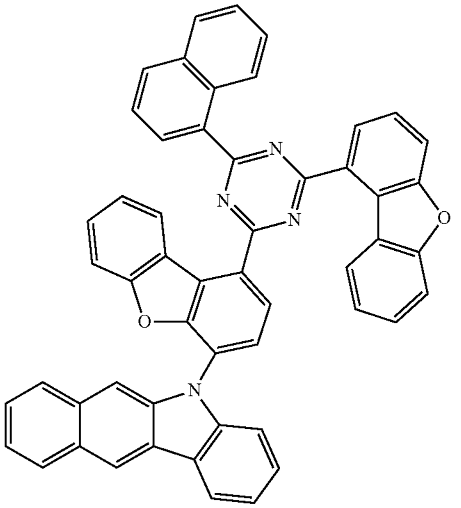
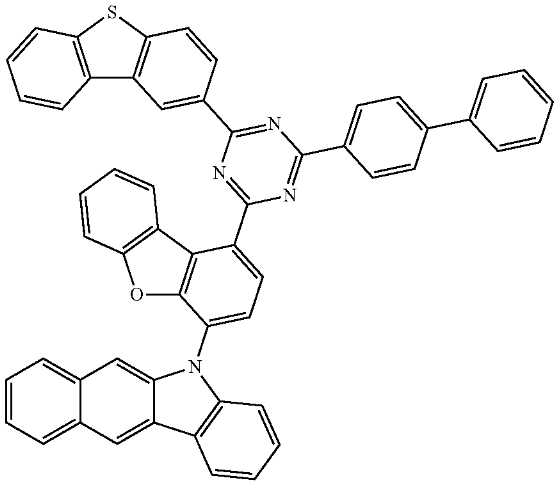
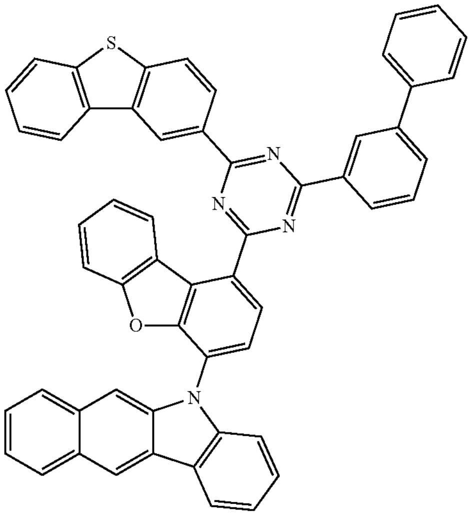

-continued
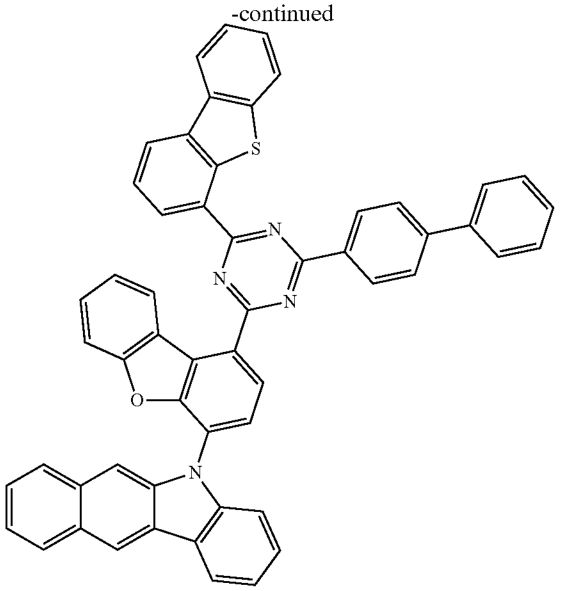
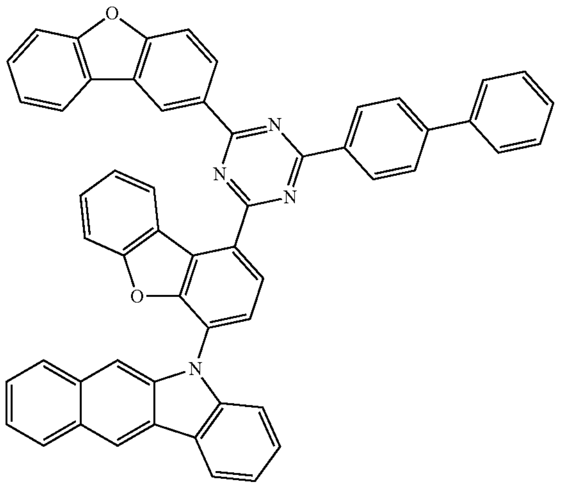
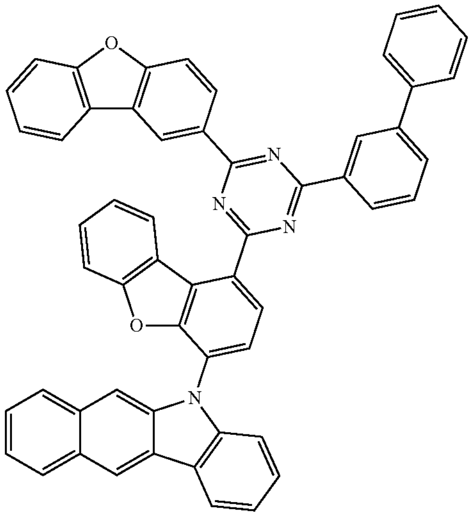
-continued
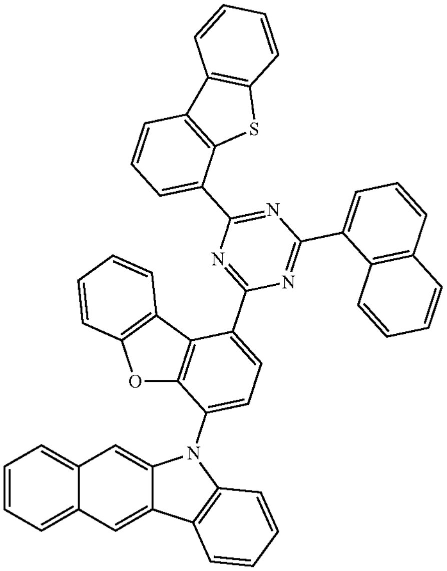
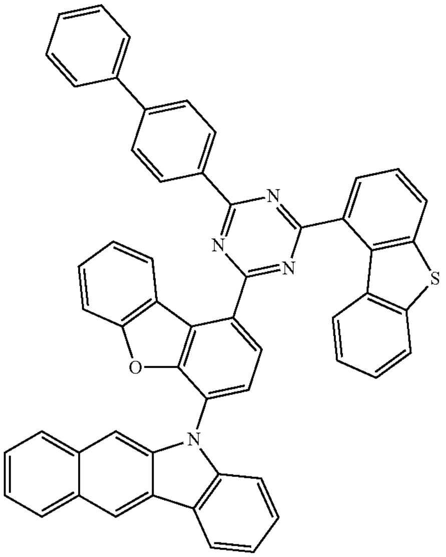
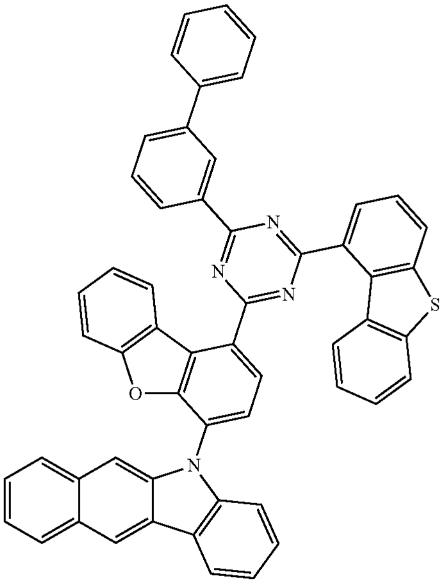

-continued
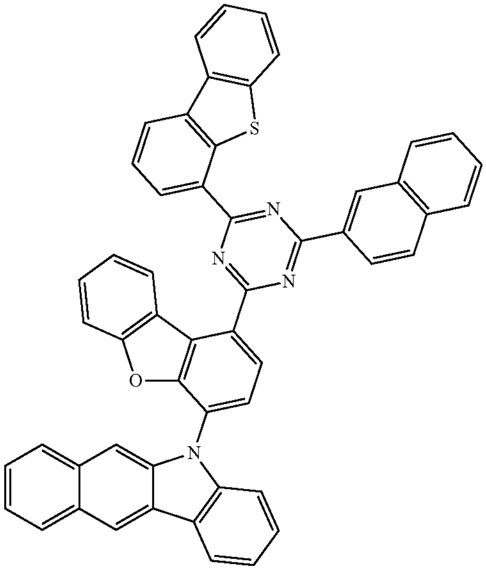
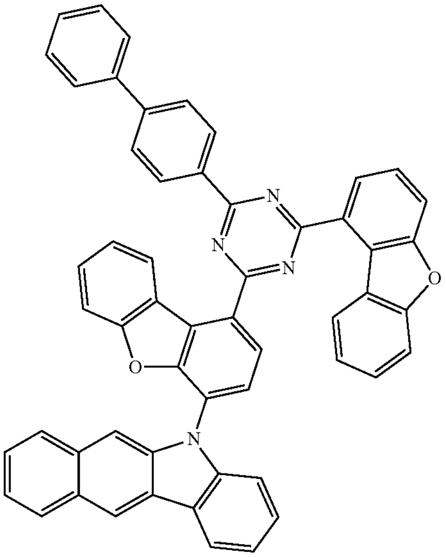
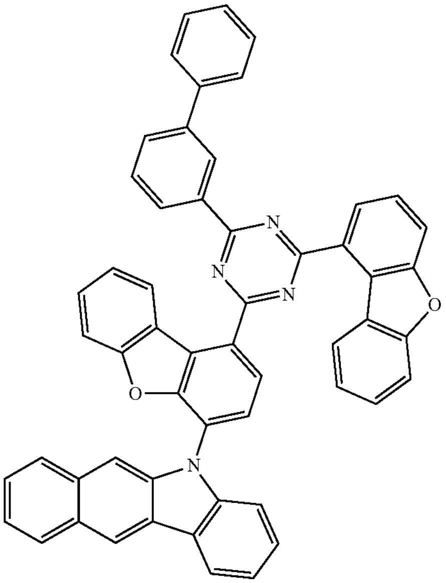
-continued
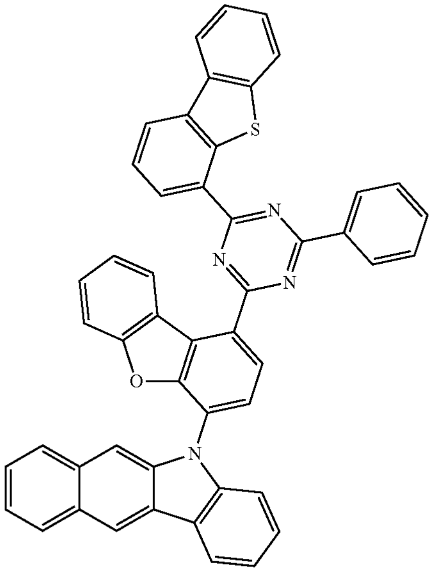
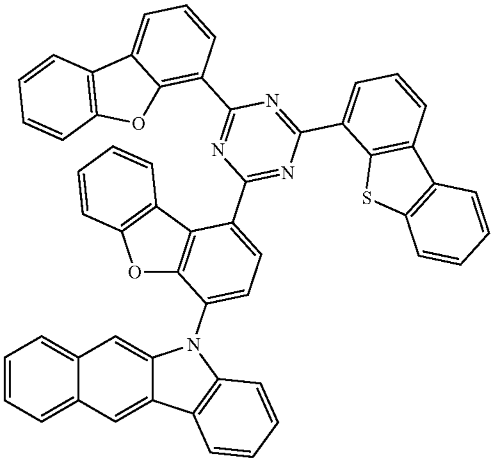
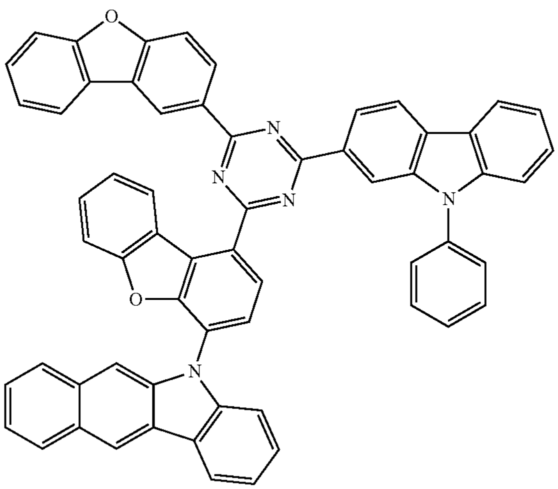

-continued
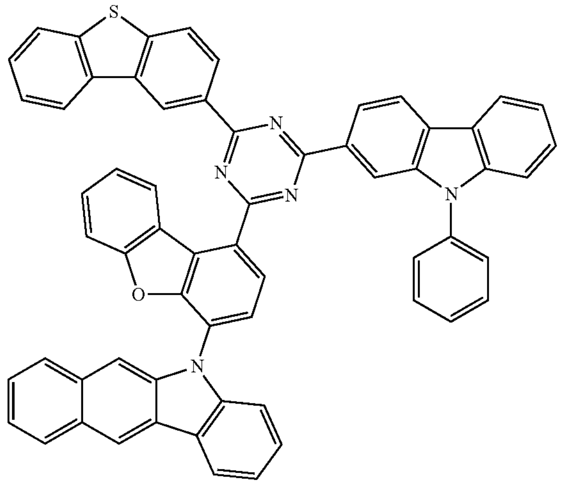
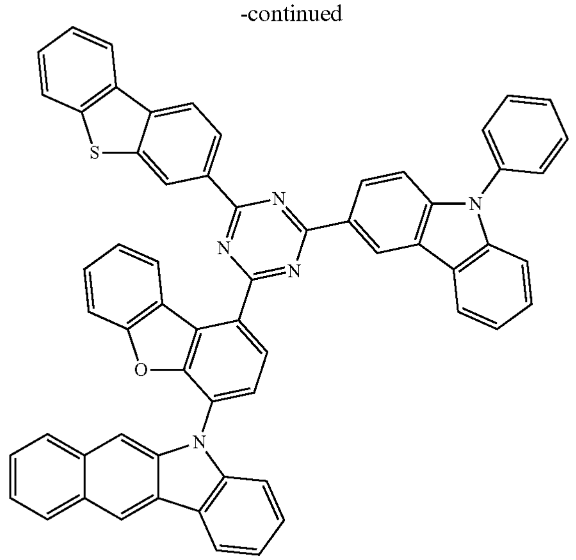
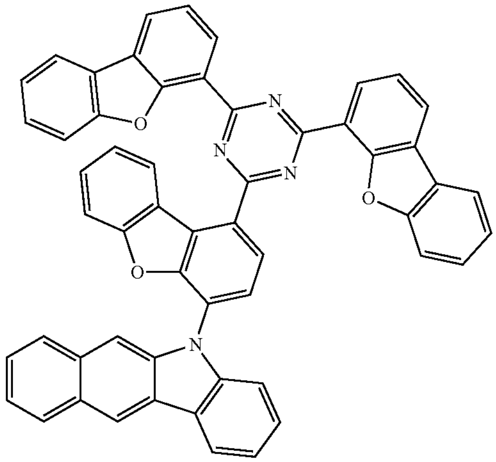
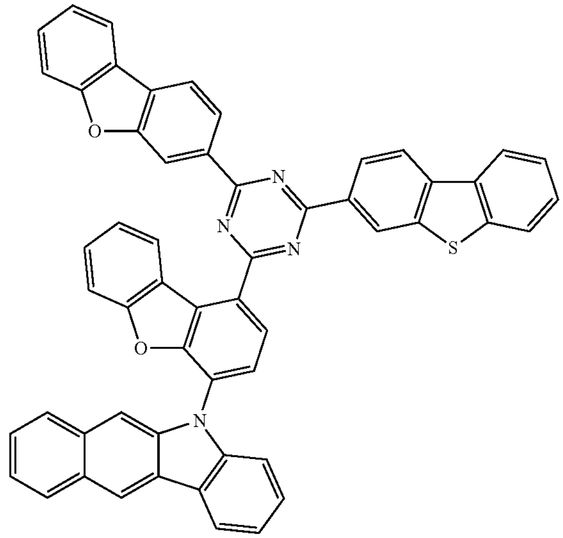
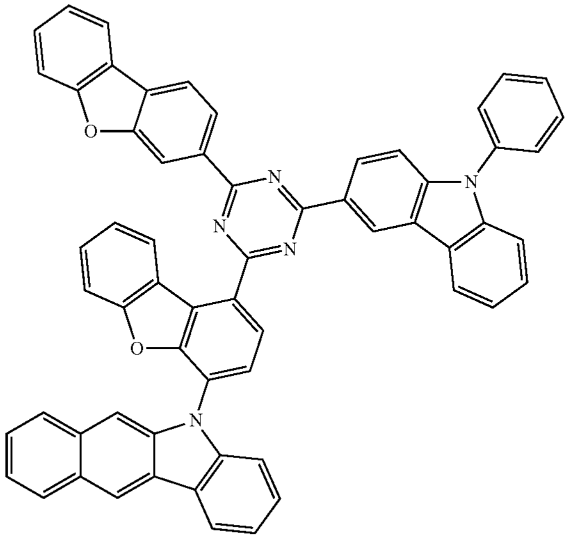
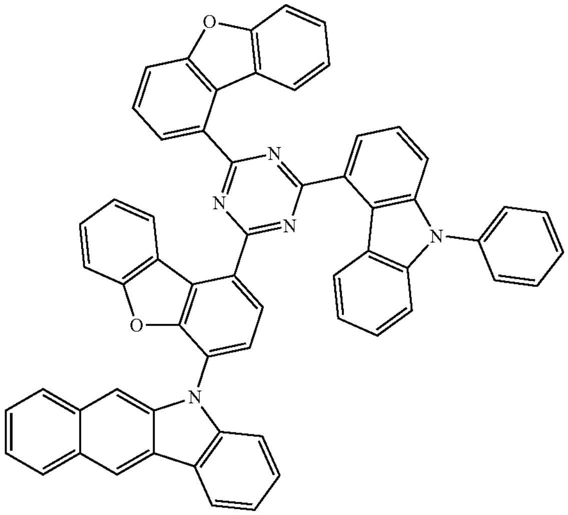
-continued -continued
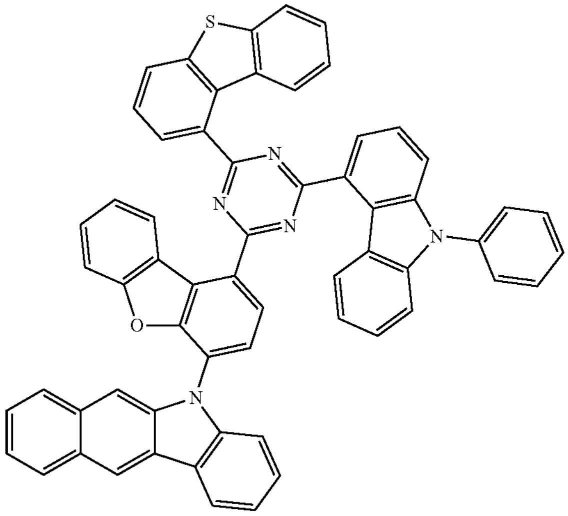
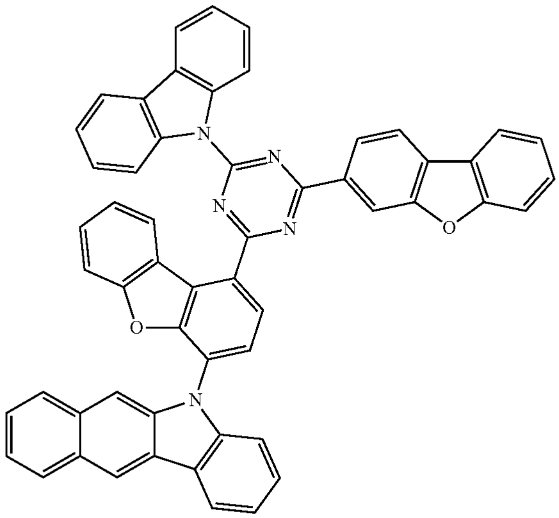
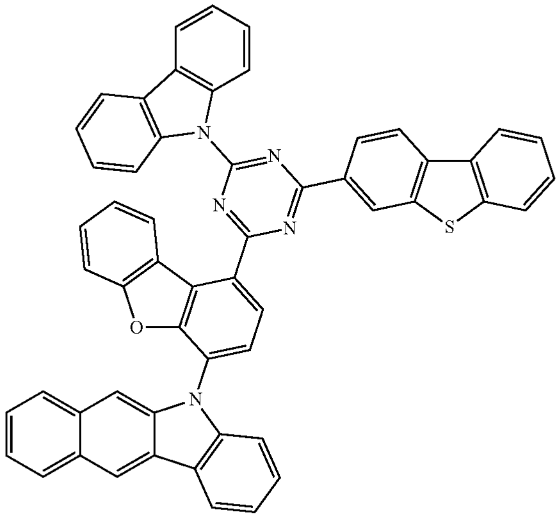
-continued
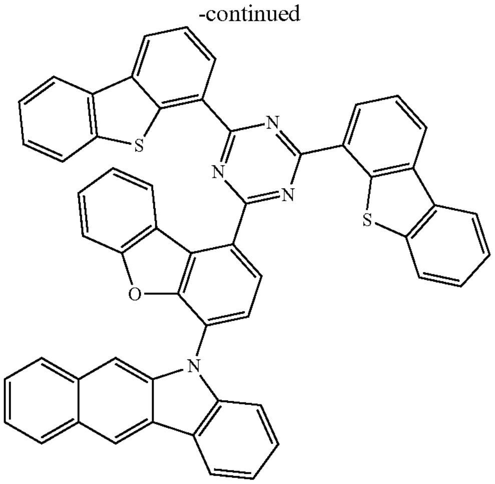
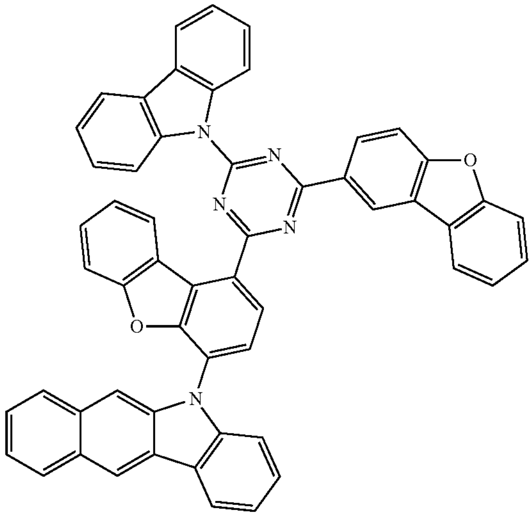
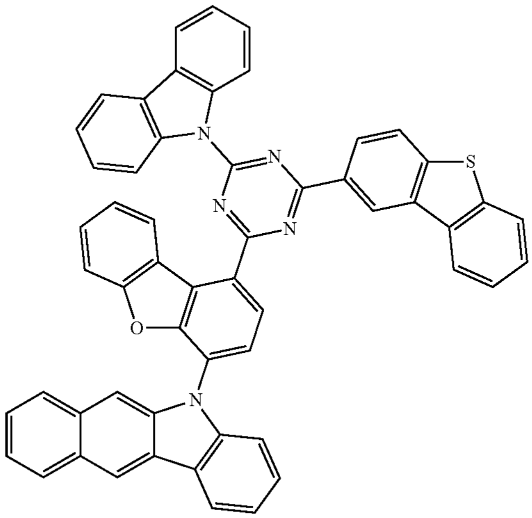

-continued
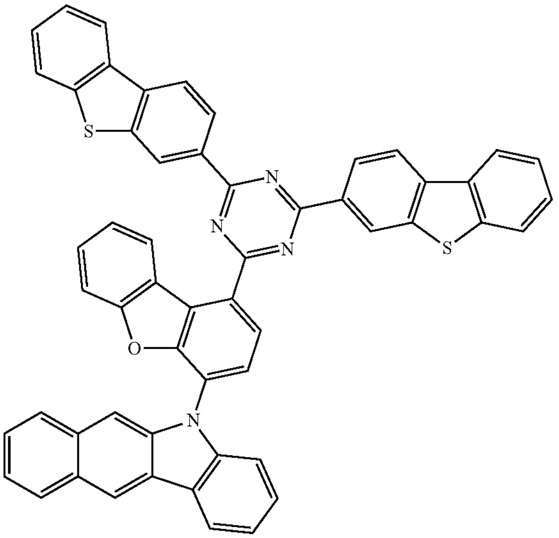
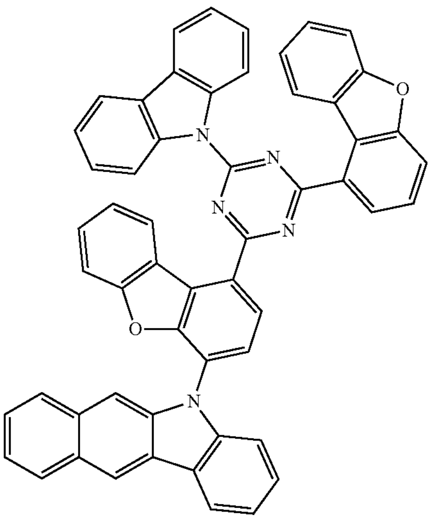
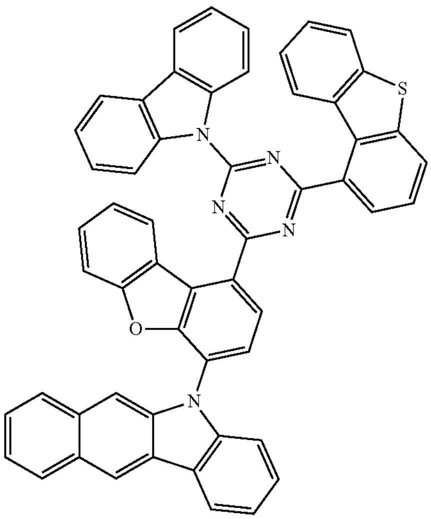
-continued
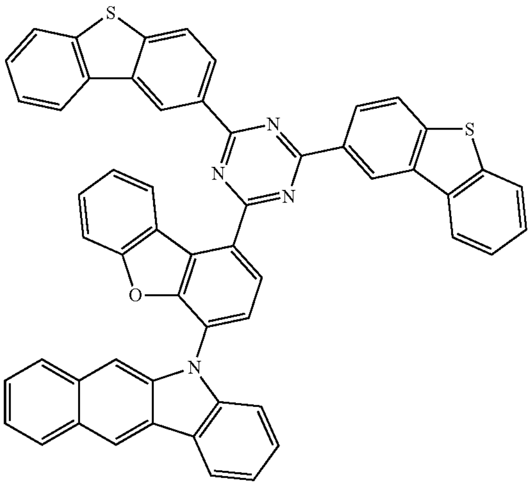
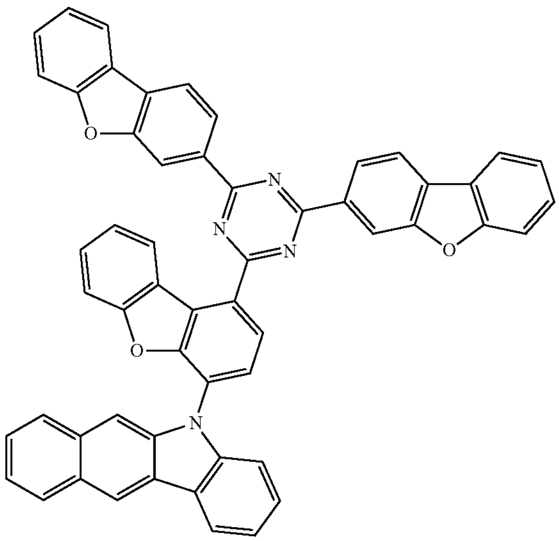
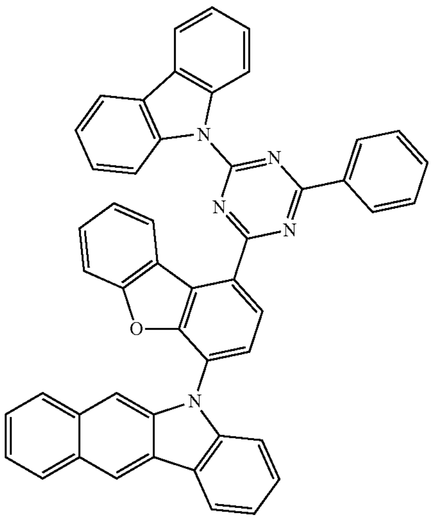

-continued
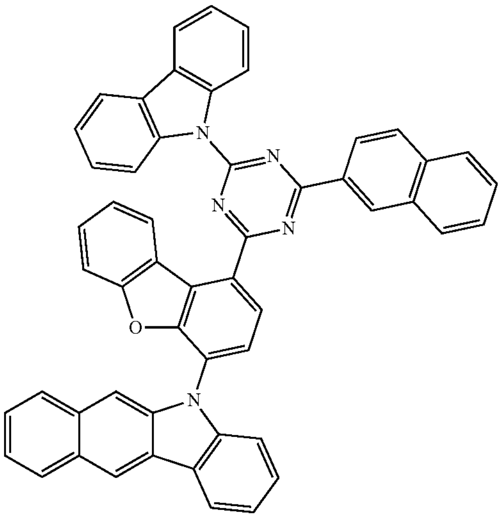
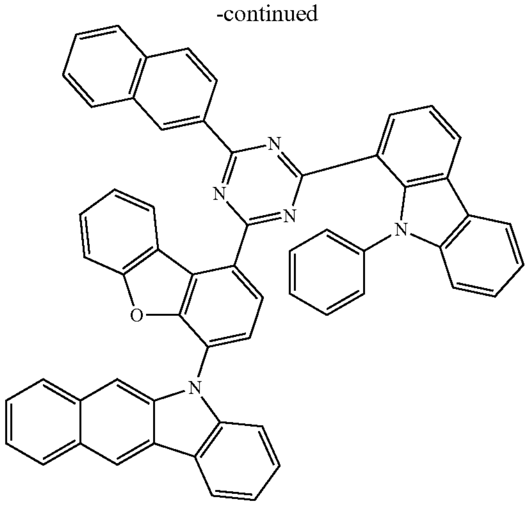
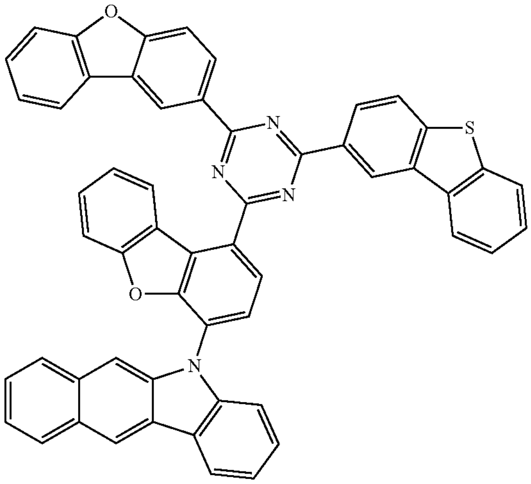
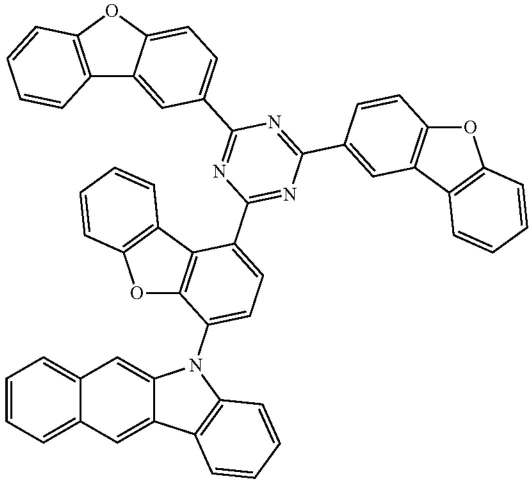
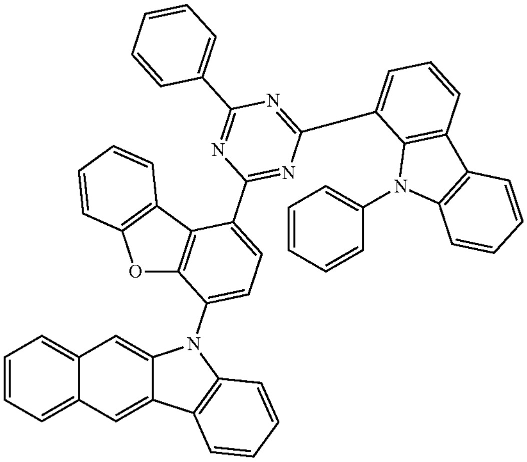
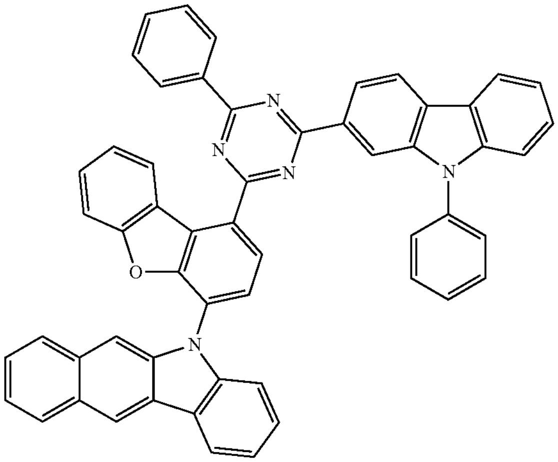
-continued -continued
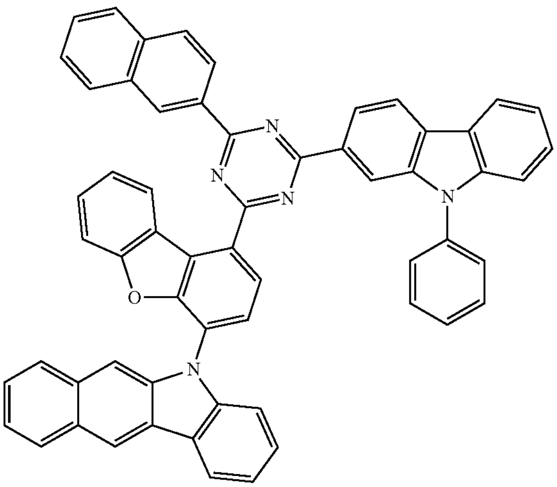
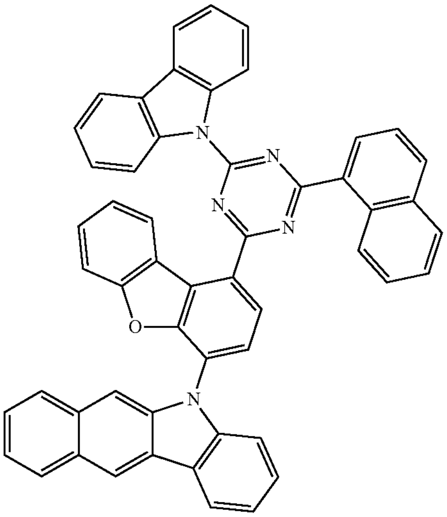
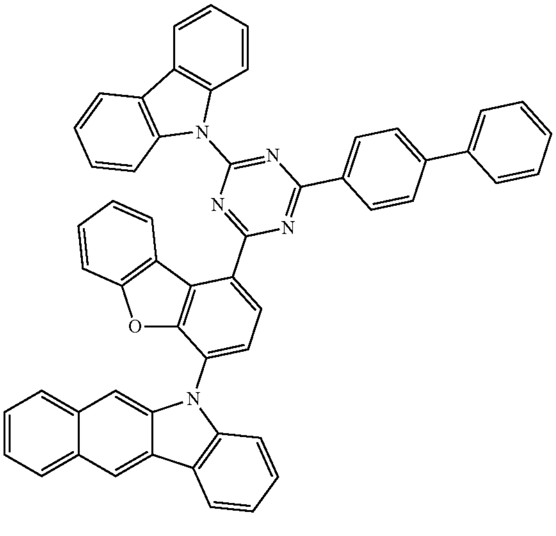
-continued
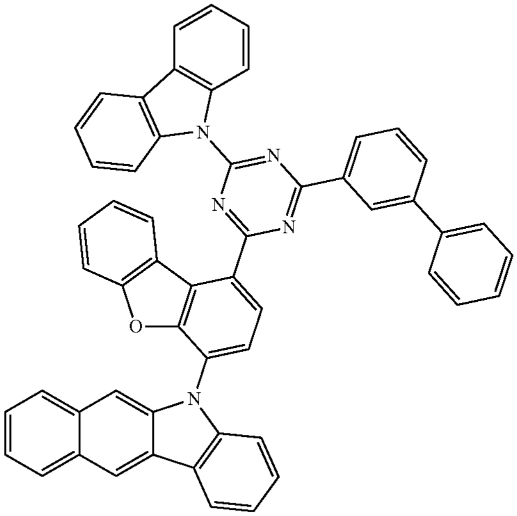
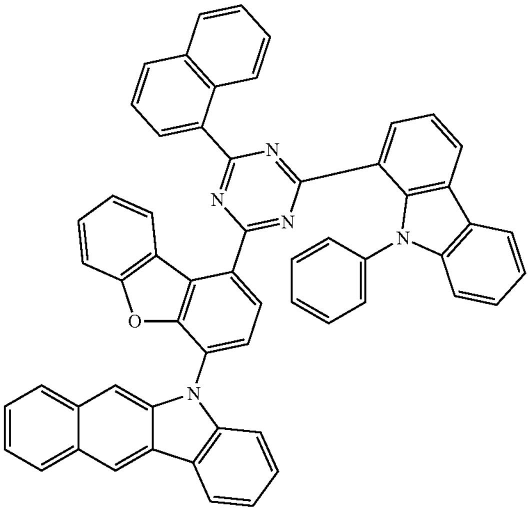
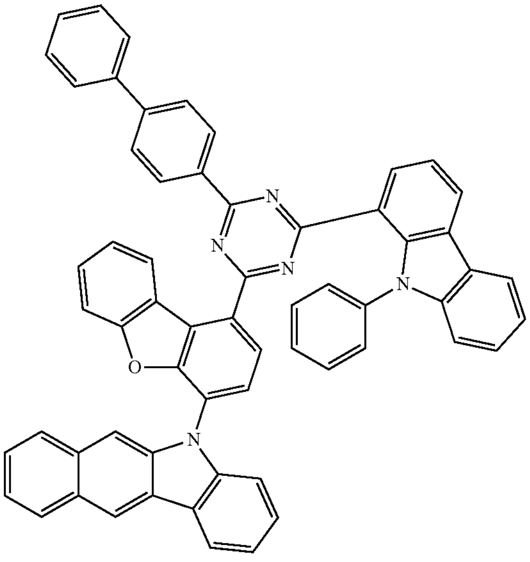

-continued
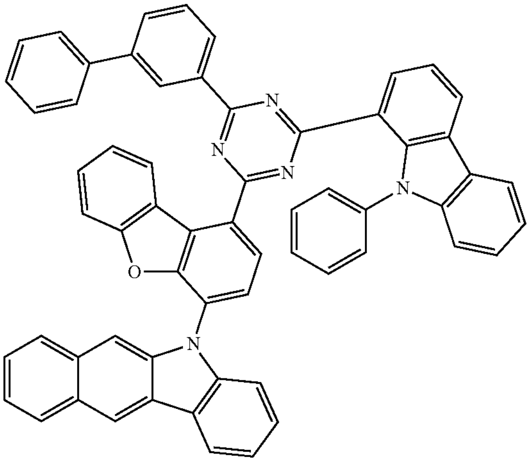
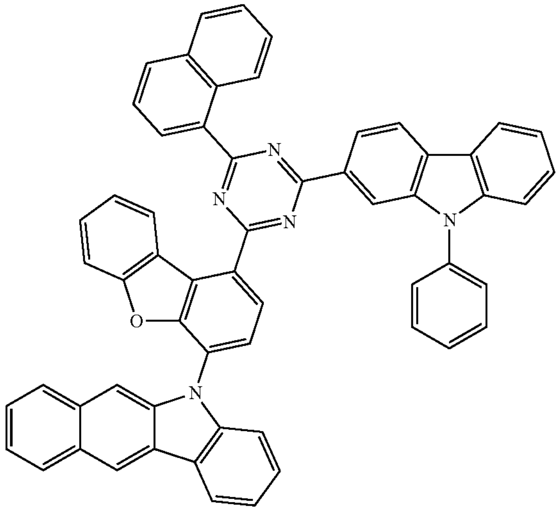
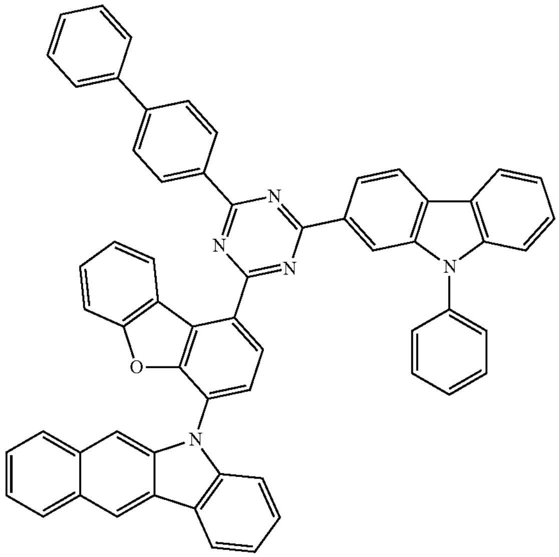
-continued
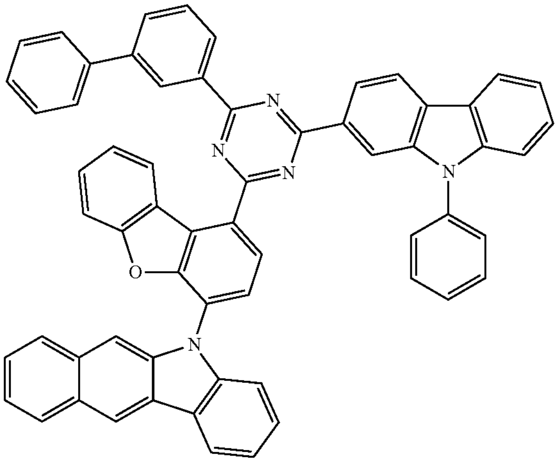
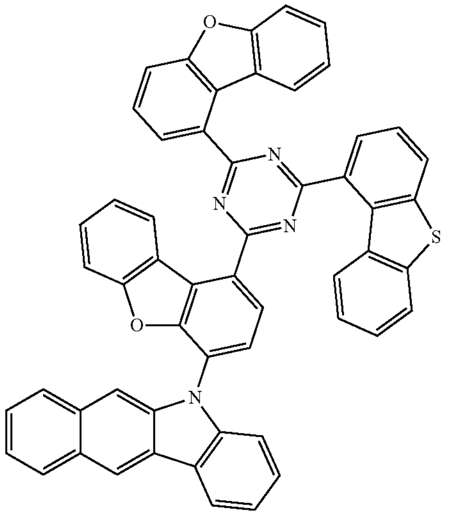
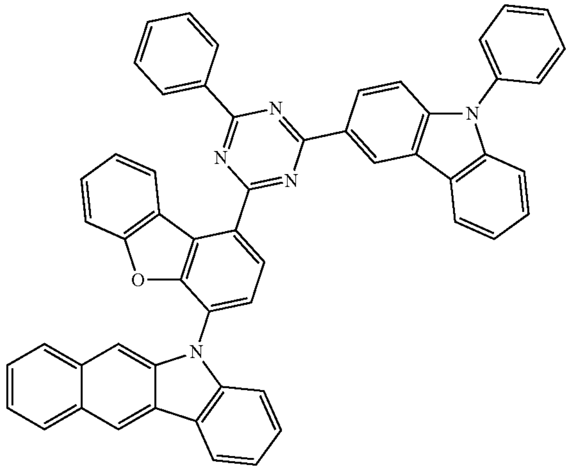

-continued
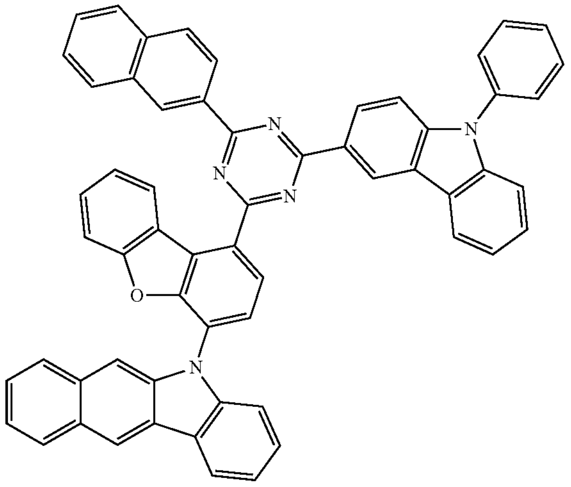
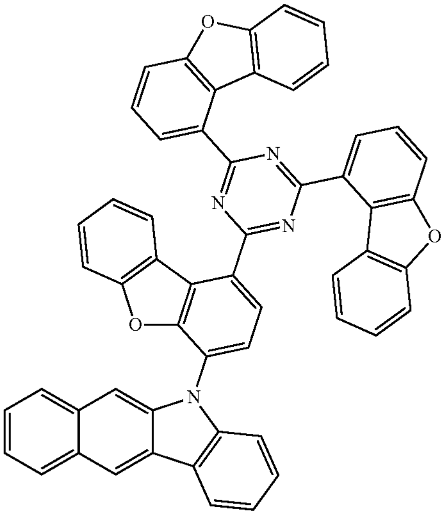
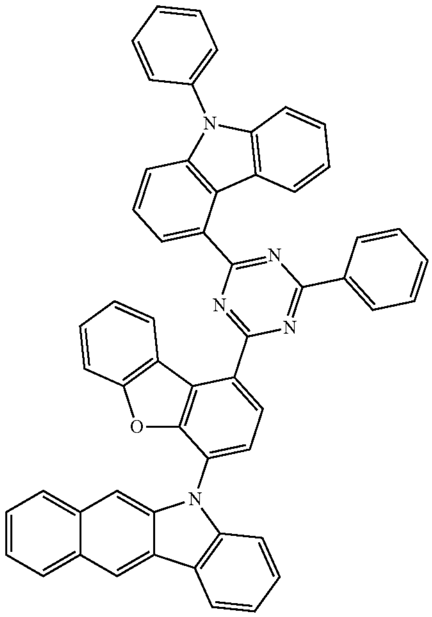
-continued
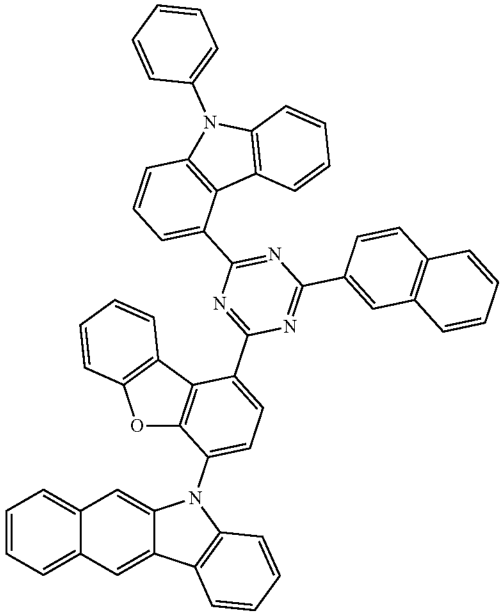
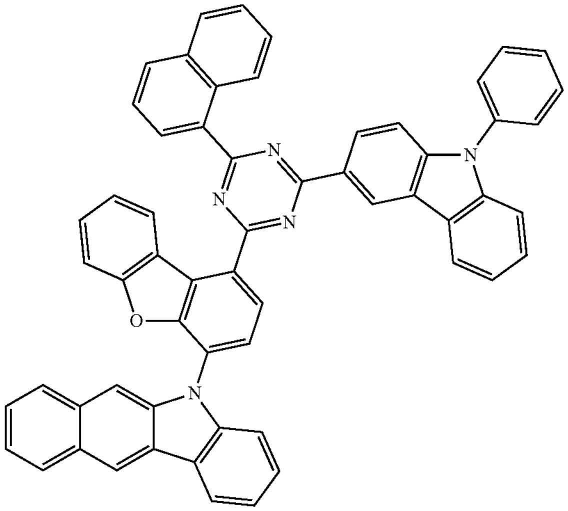
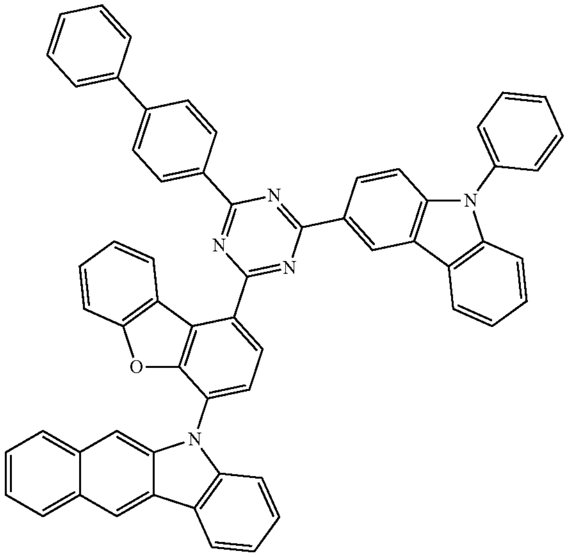

-continued
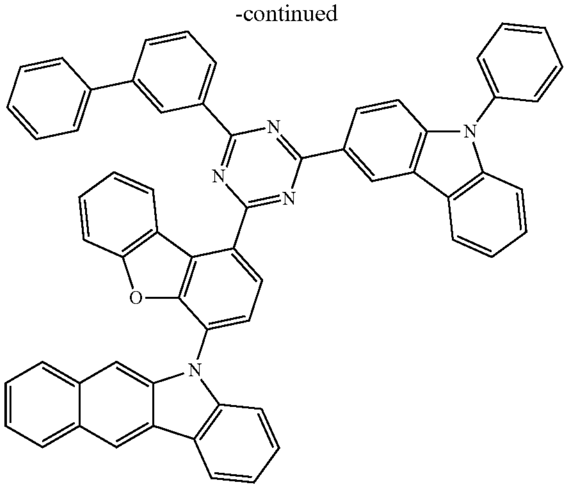
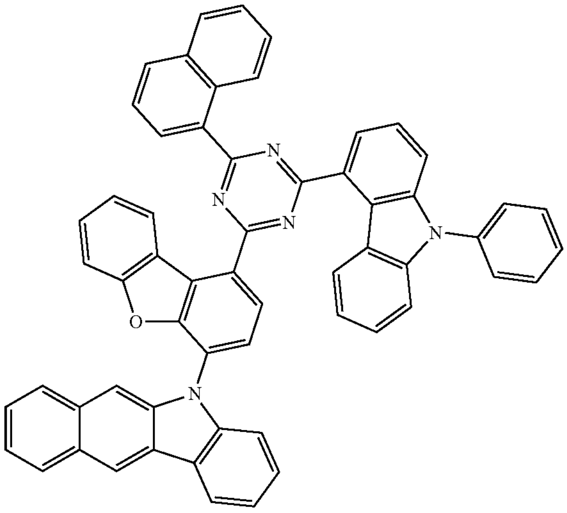
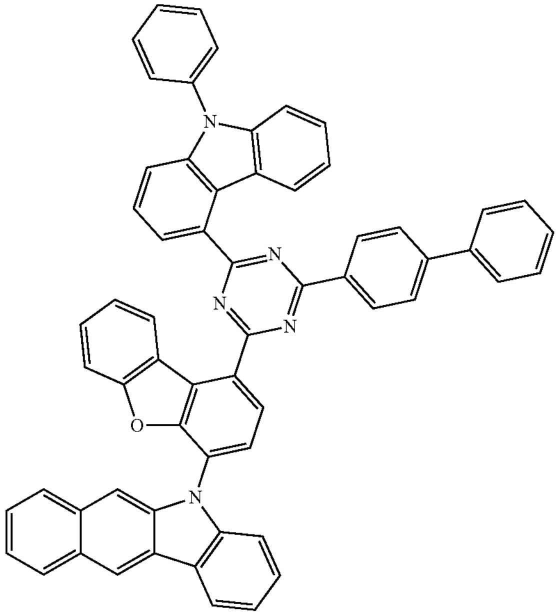
-continued
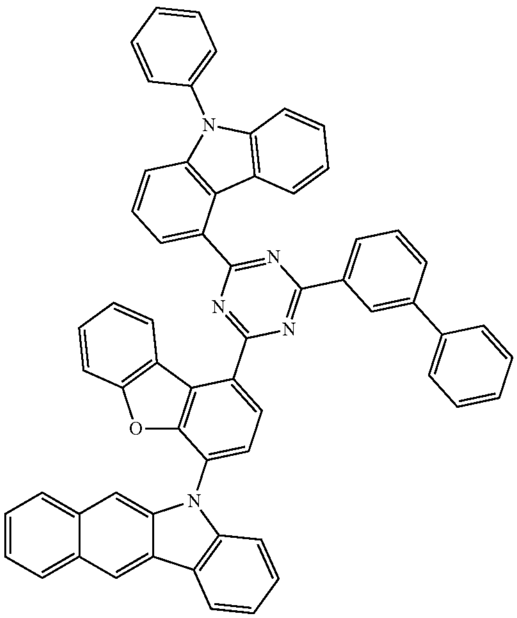
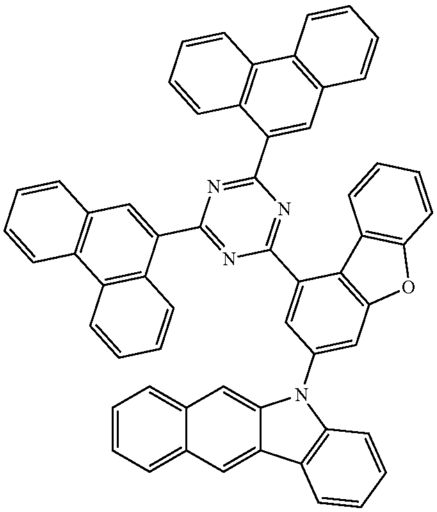
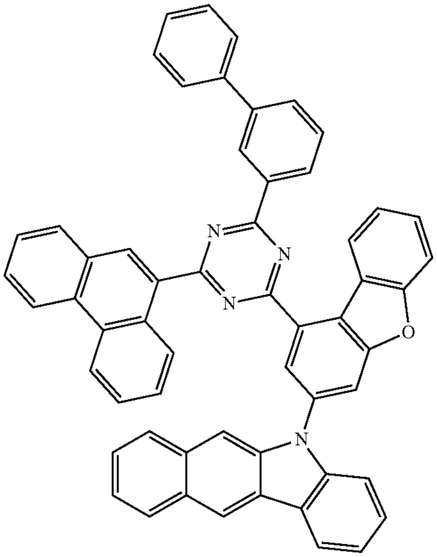

-continued
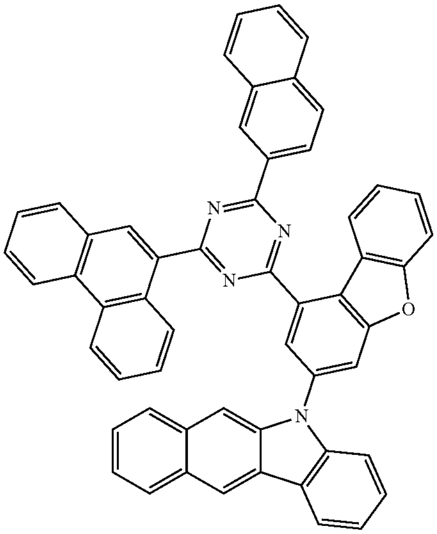
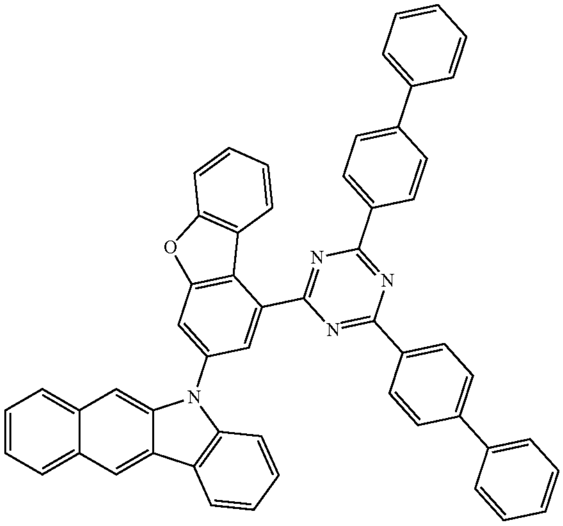
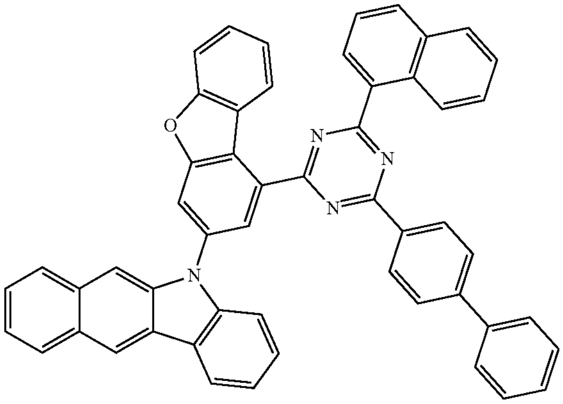
-continued
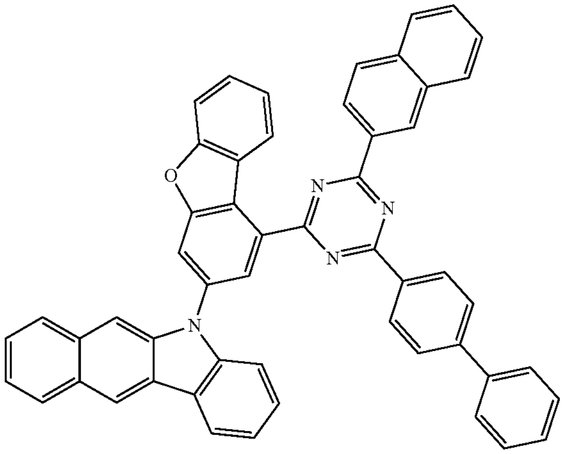
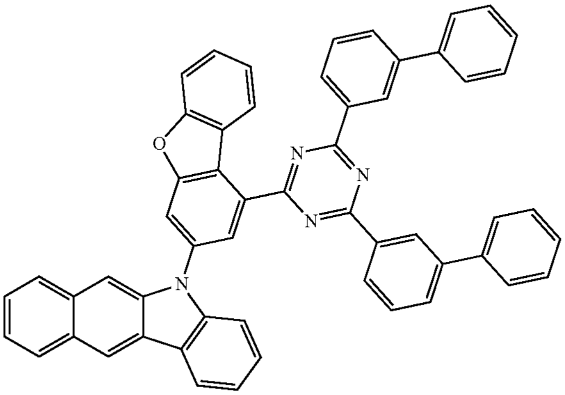
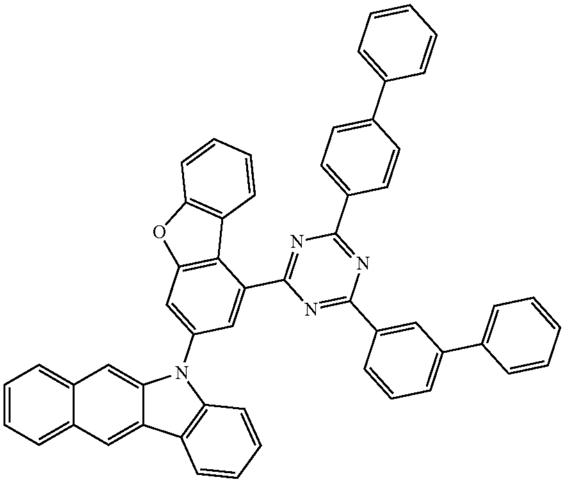

-continued
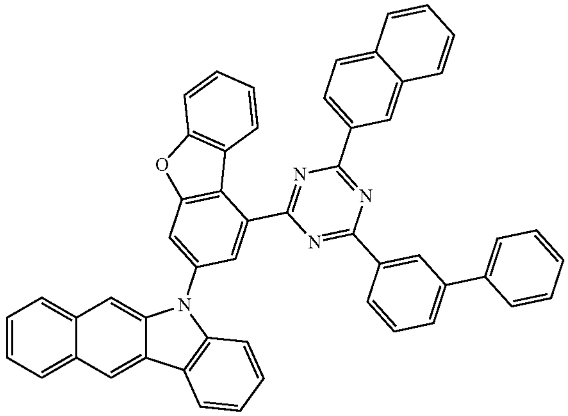
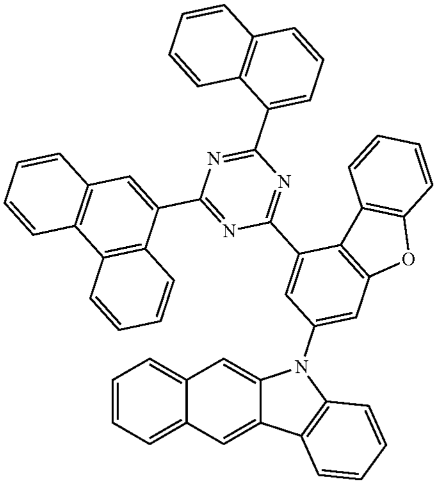
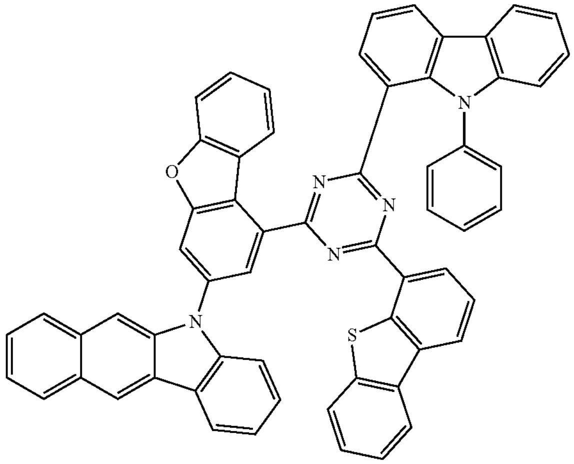
-continued
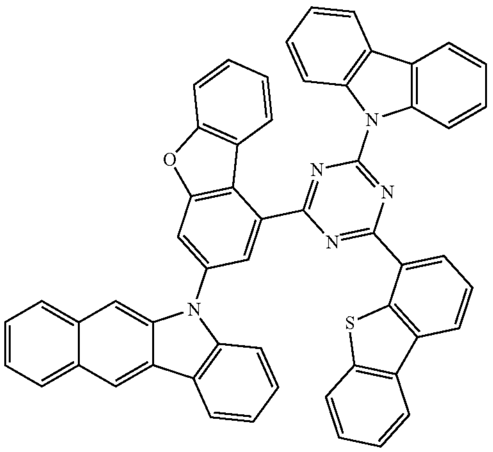
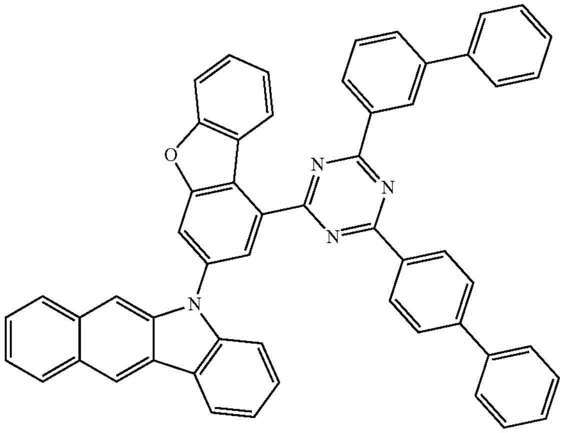
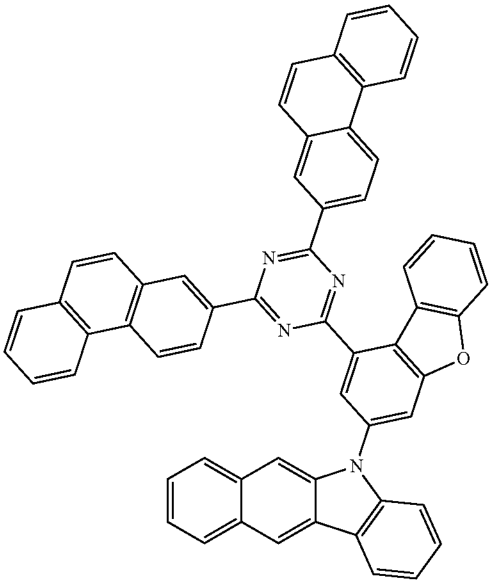

-continued
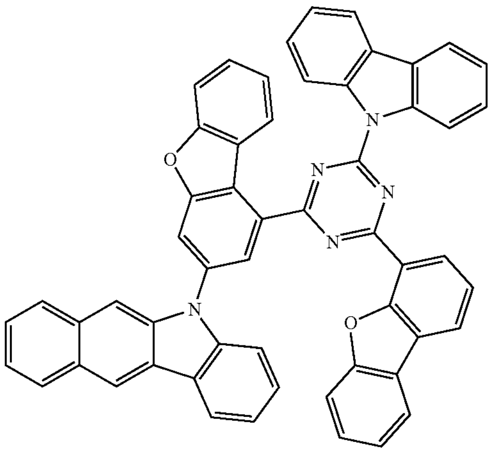
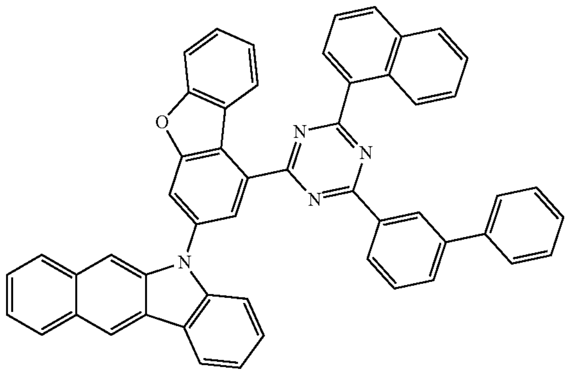
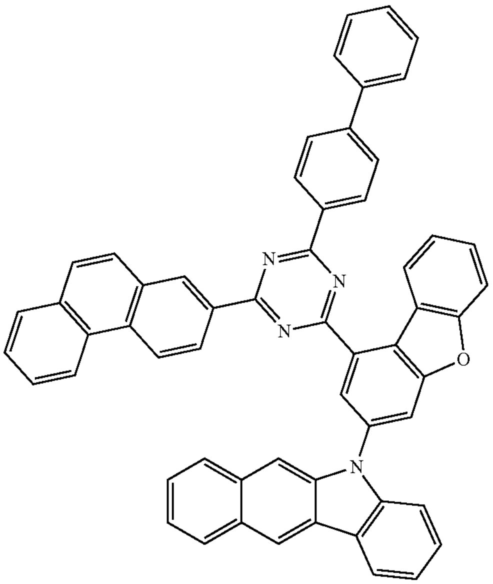
-continued
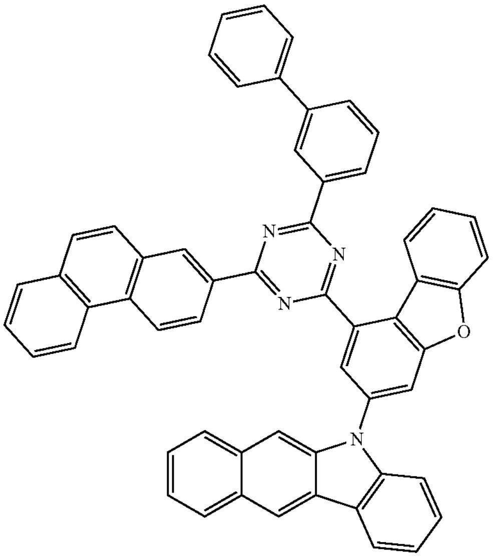
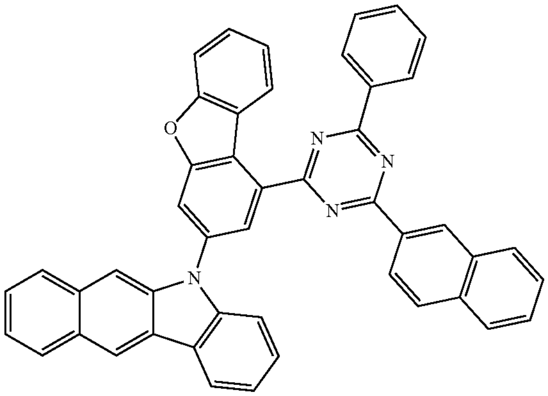
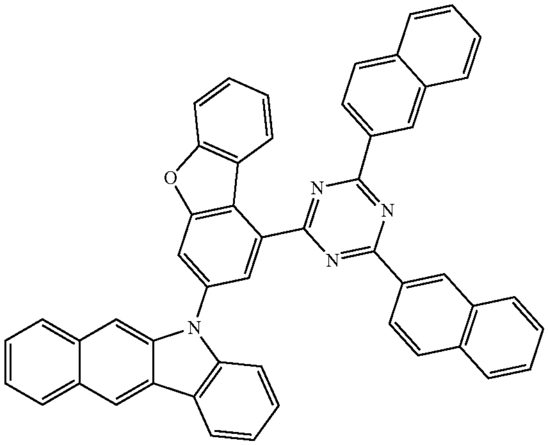

-continued
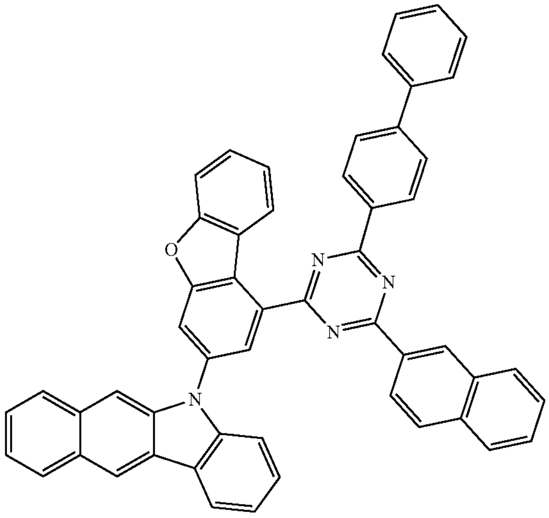
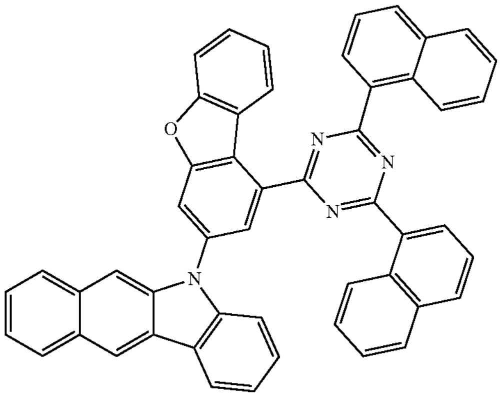
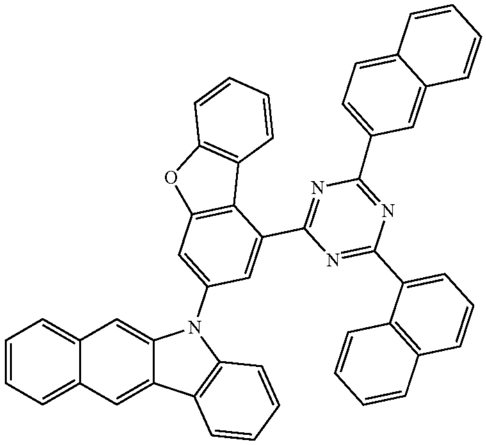
-continued
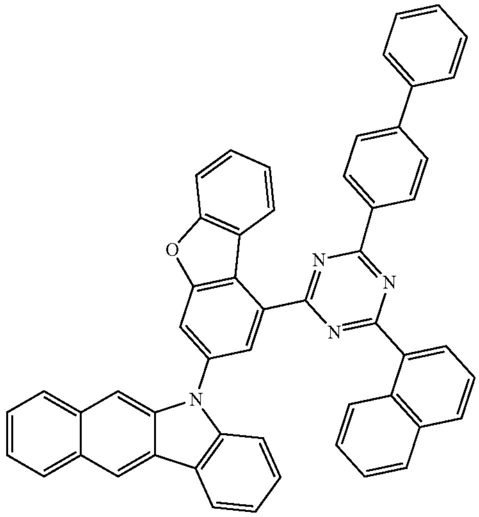
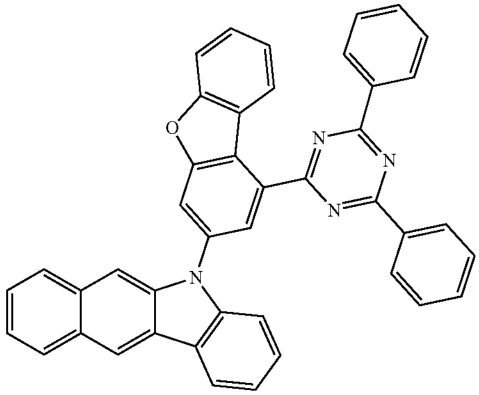
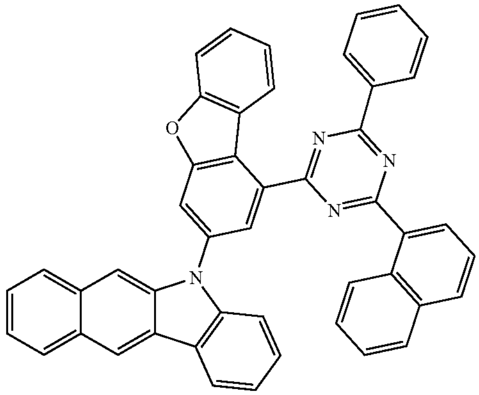
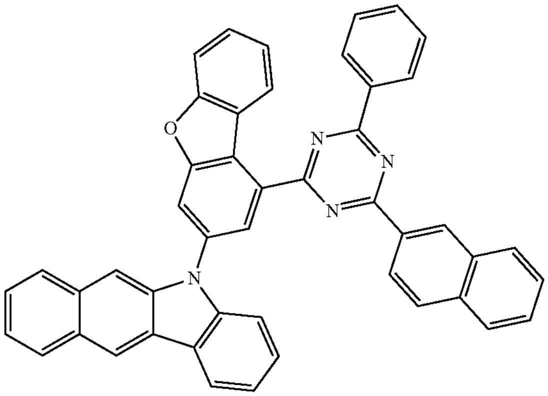

-continued
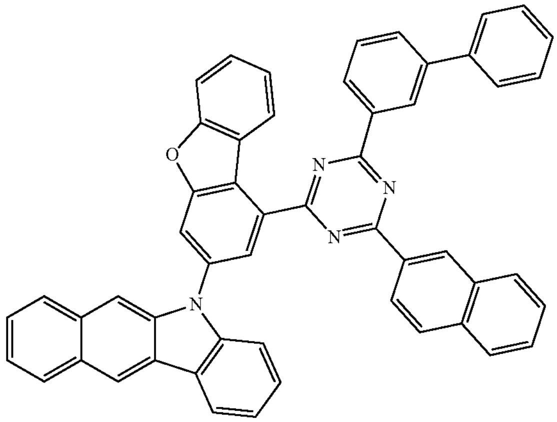
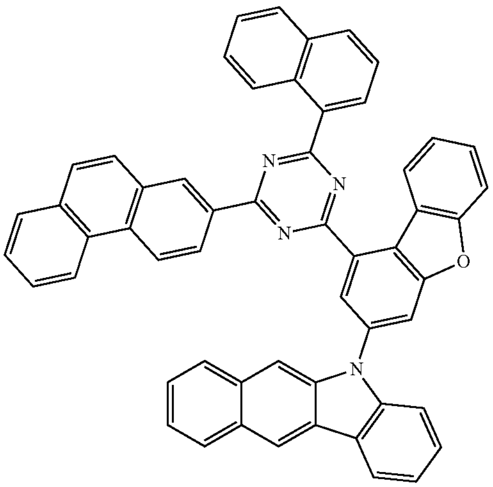
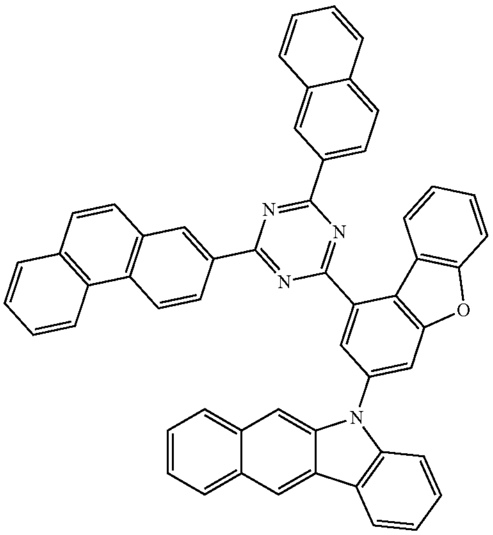
-continued
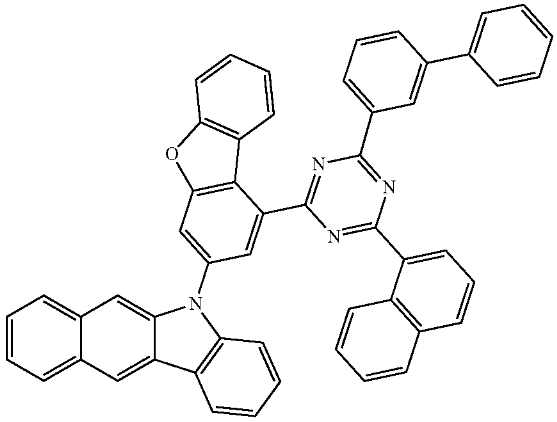
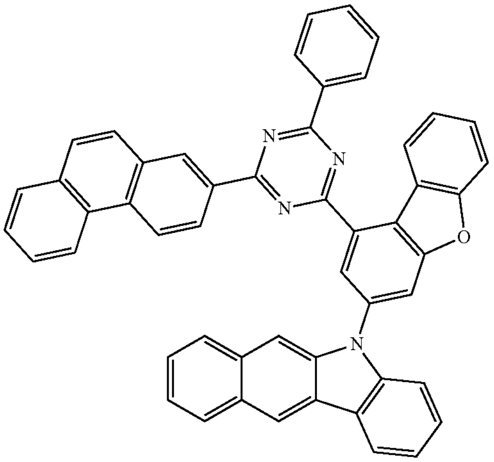
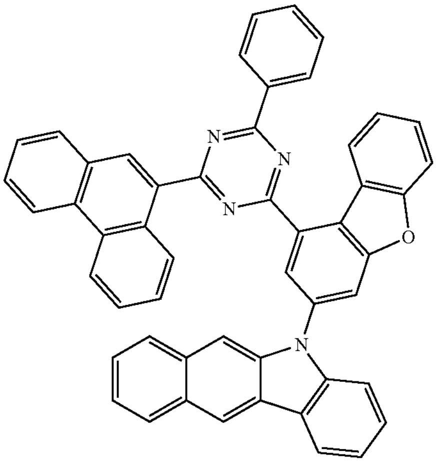
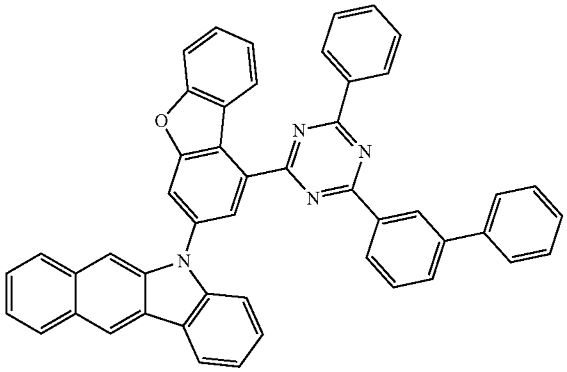

-continued
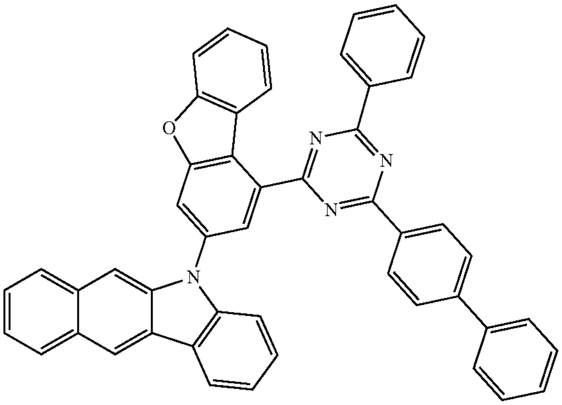
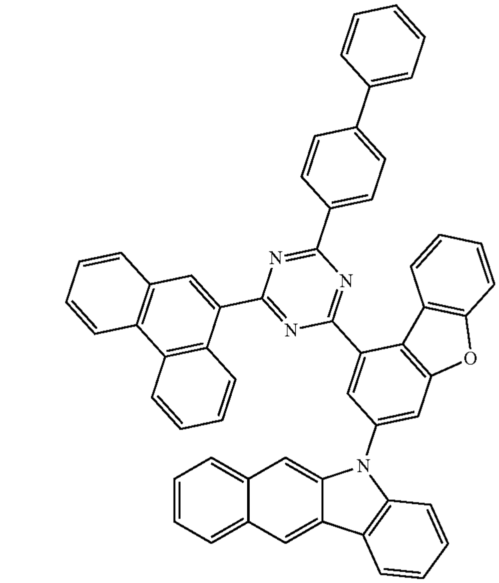
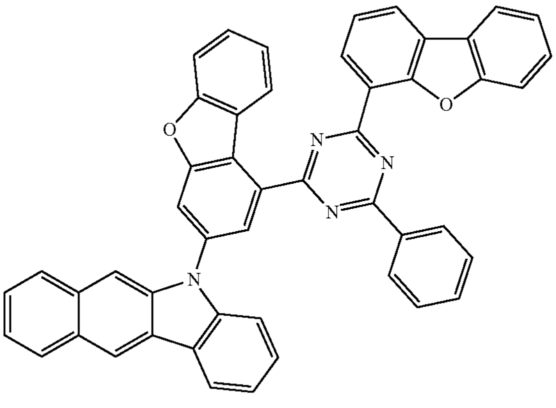
-continued
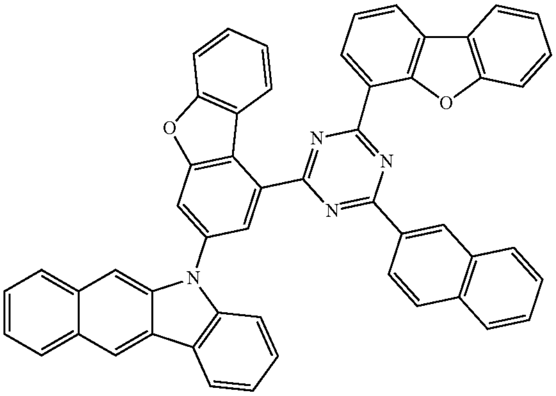
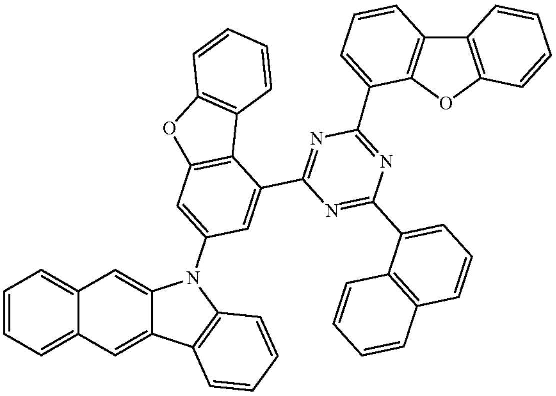
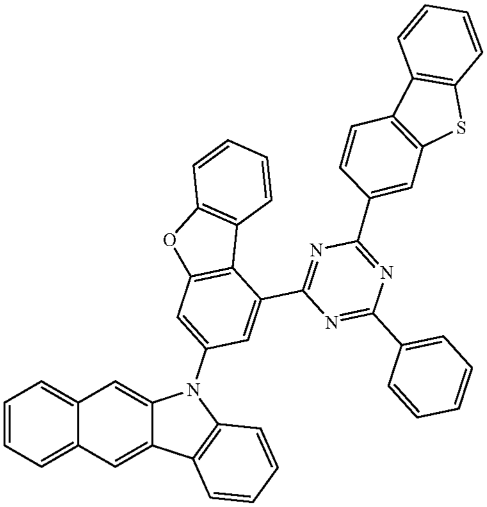

-continued
-continued
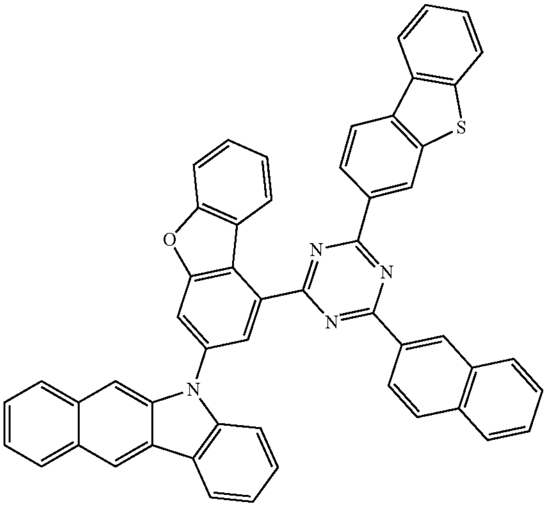
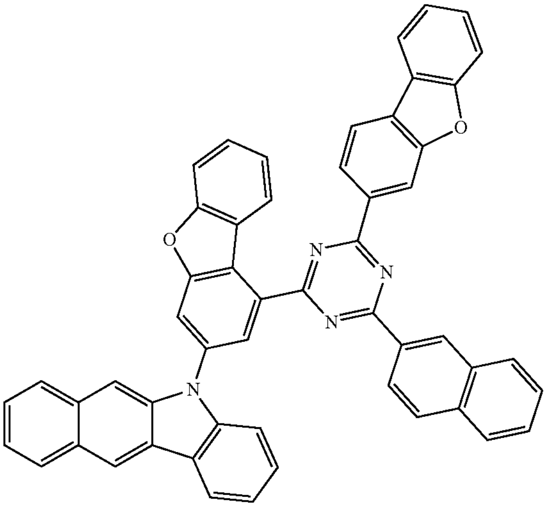
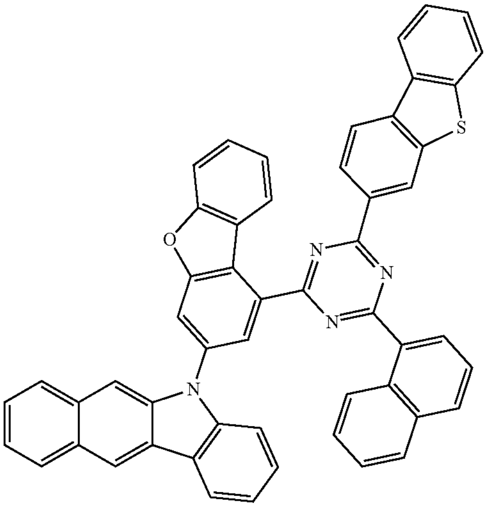
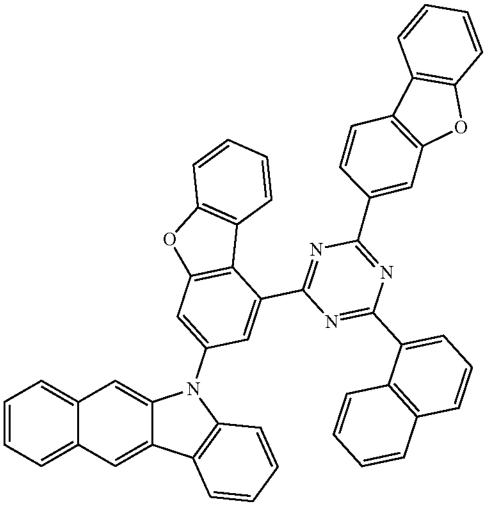
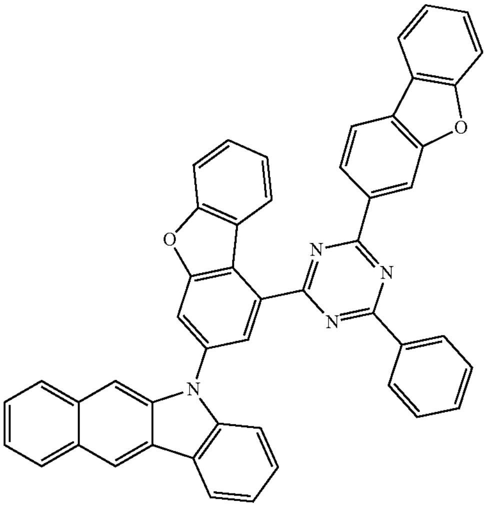
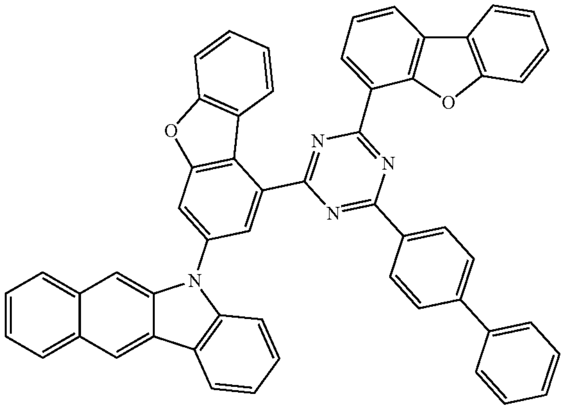

-continued
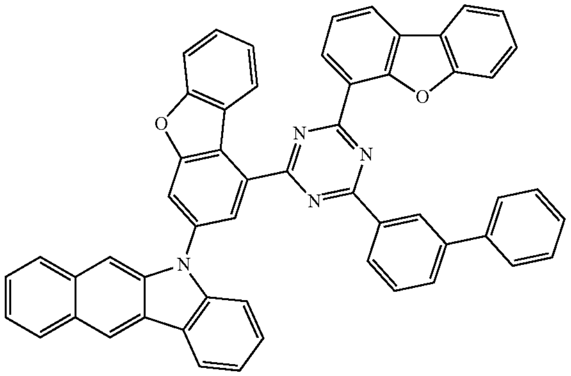
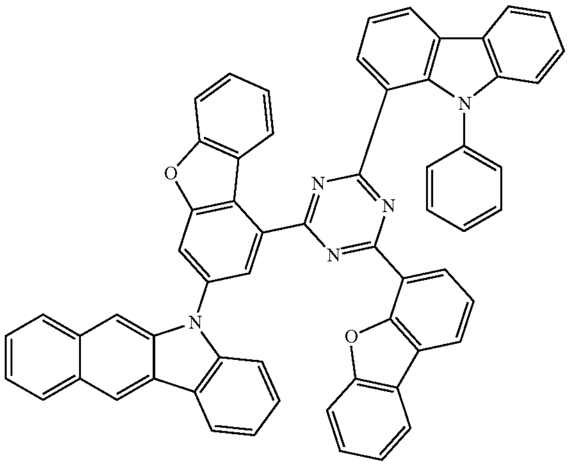
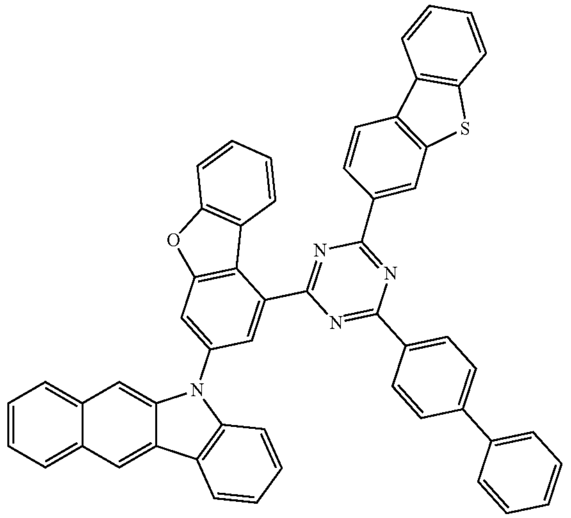
-continued
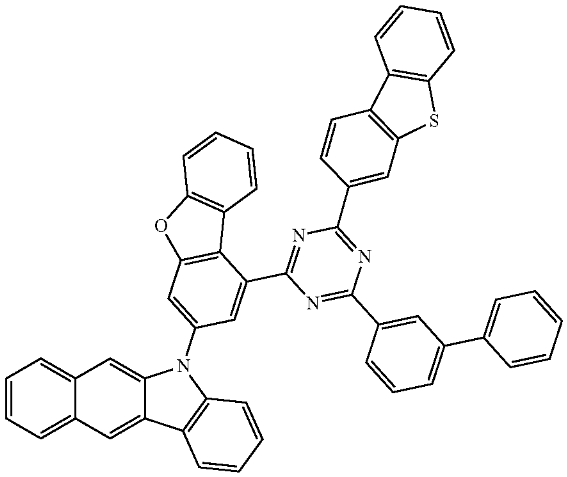
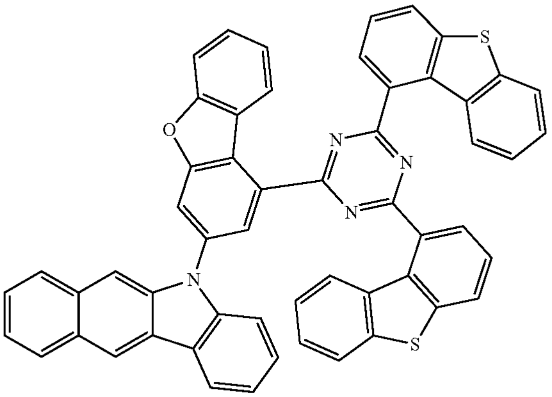
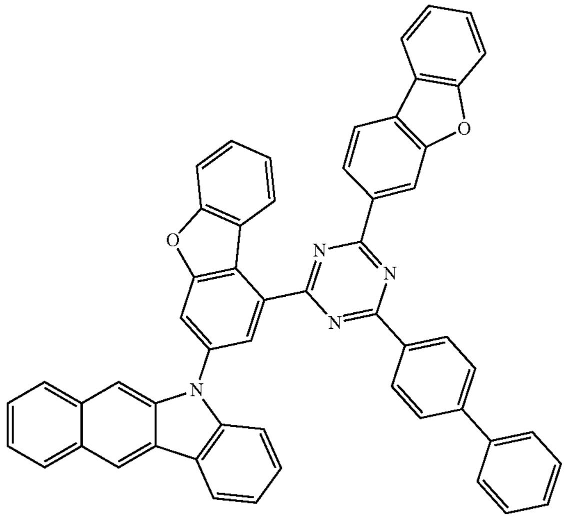

-continued
-continued
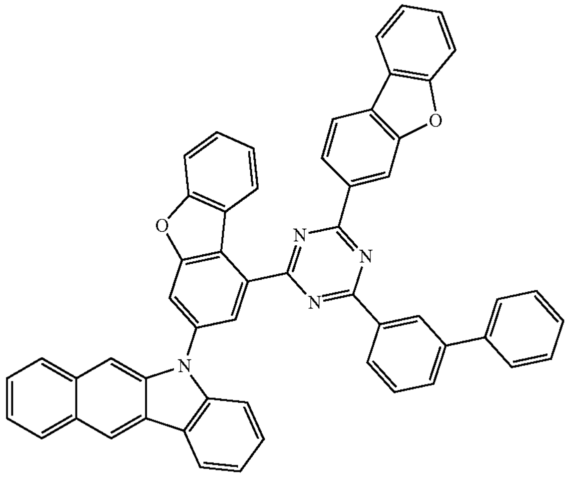
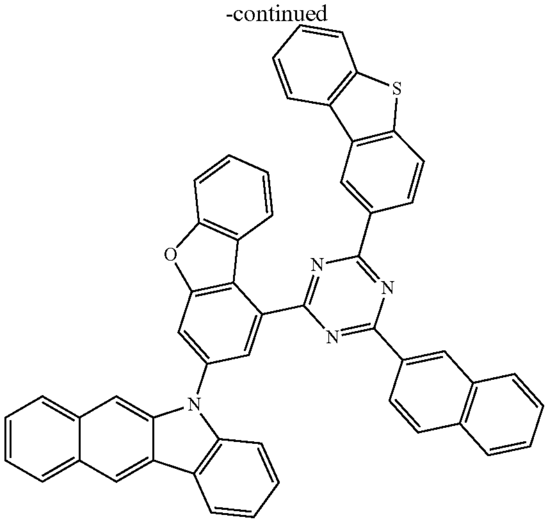
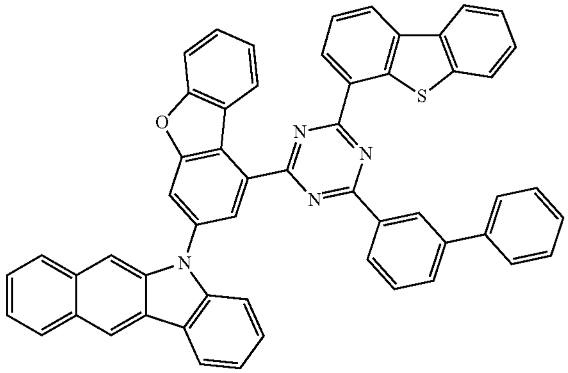
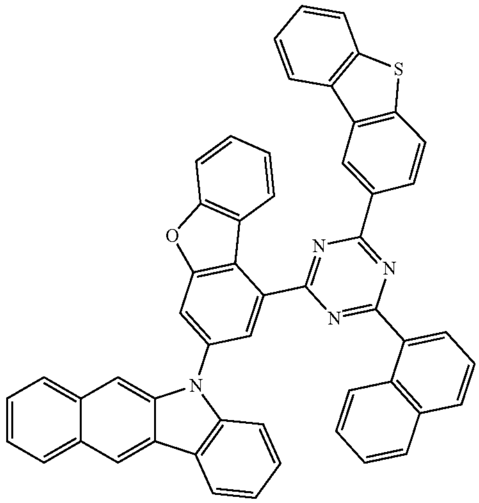
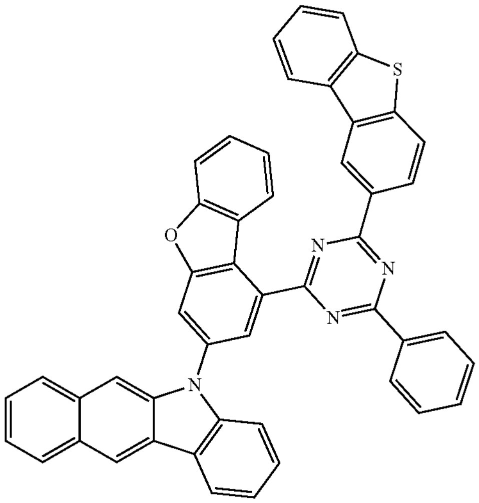
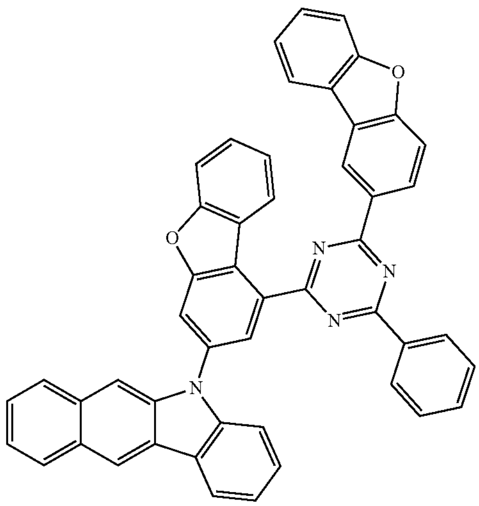

-continued
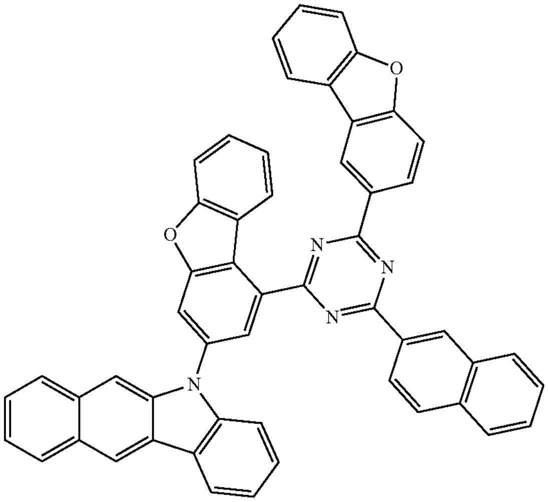
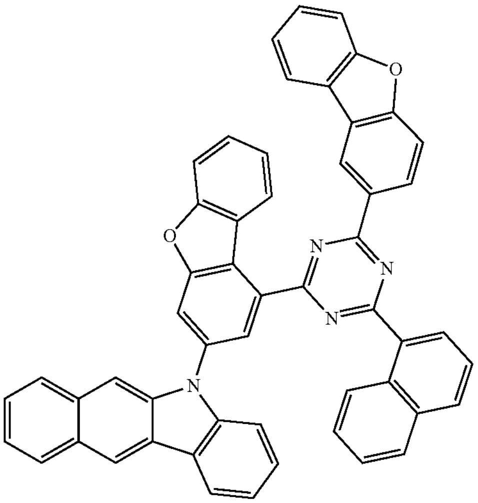
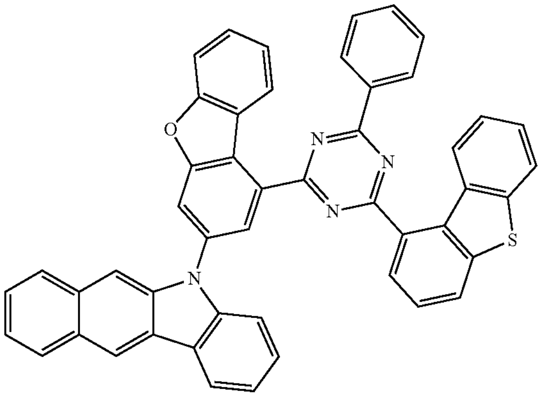
-continued
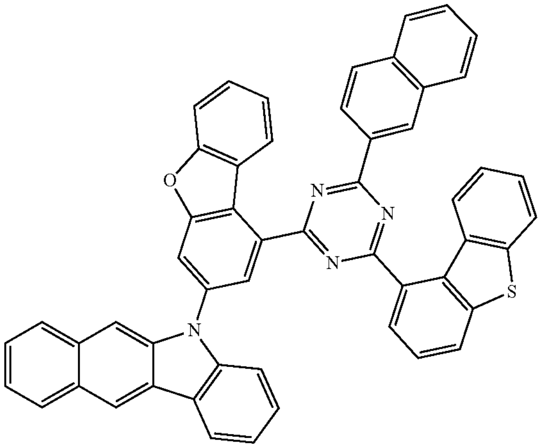
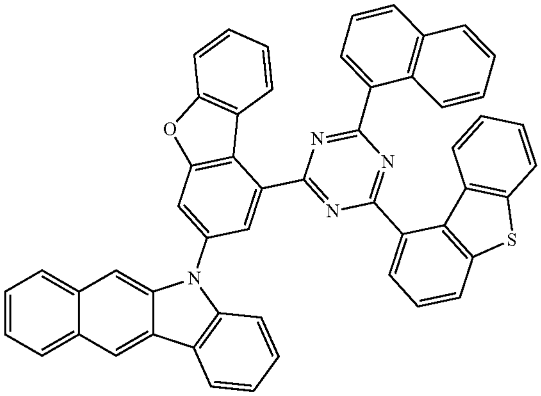
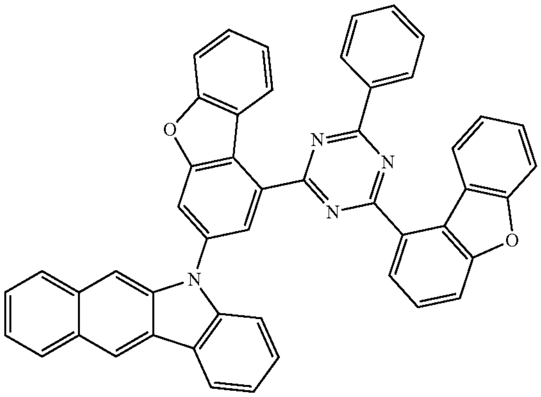
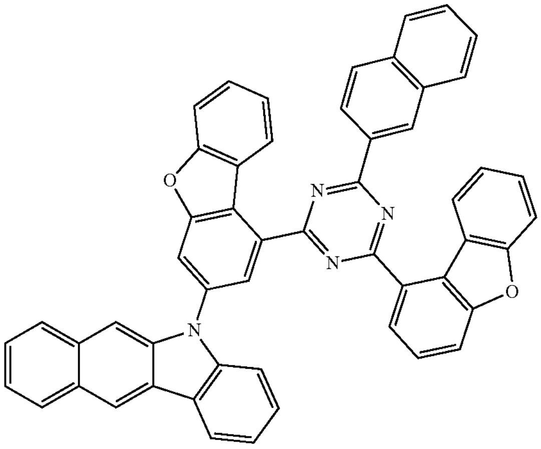

-continued
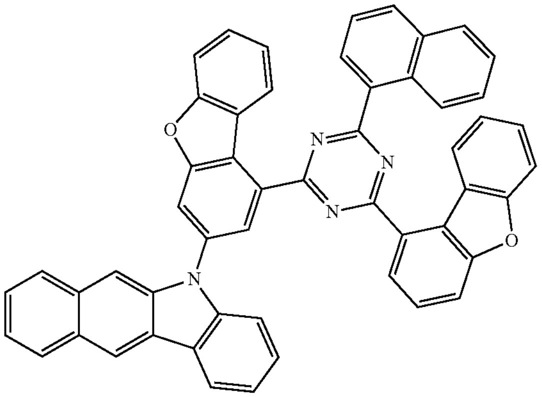
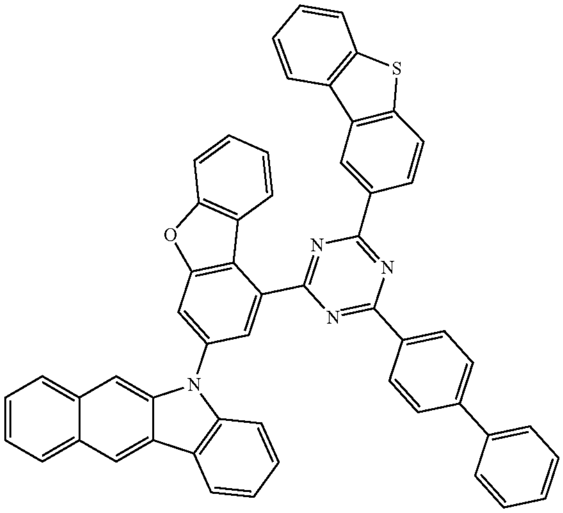
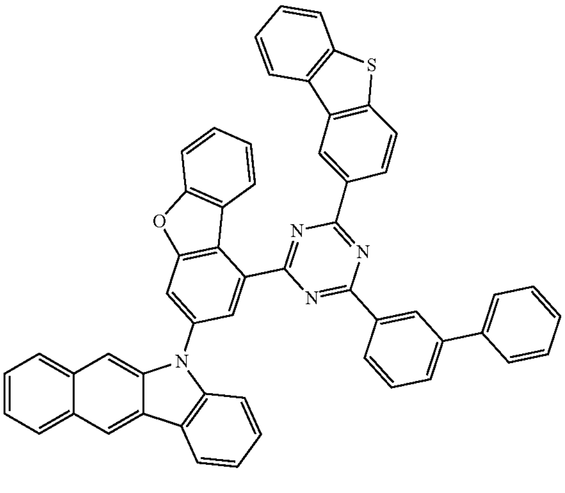
-continued
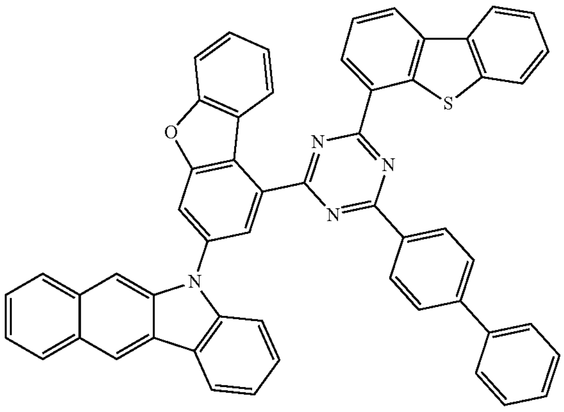
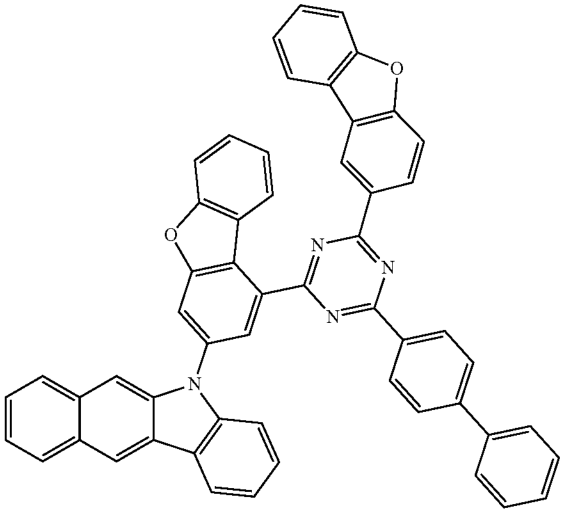
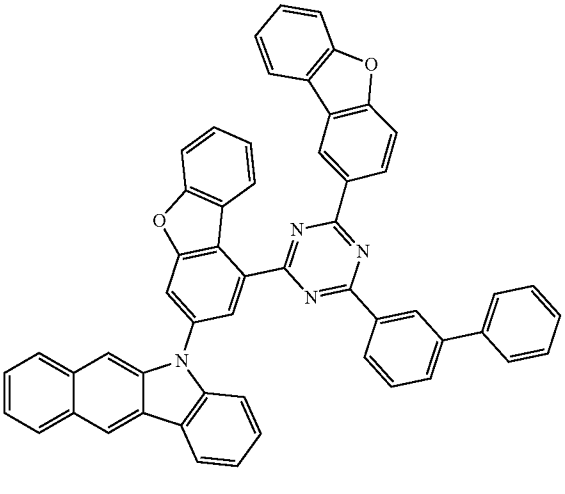

-continued
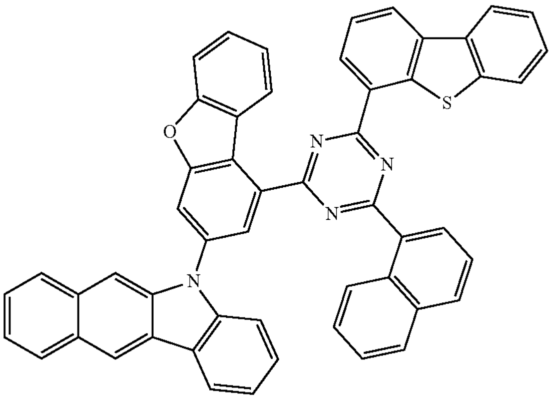
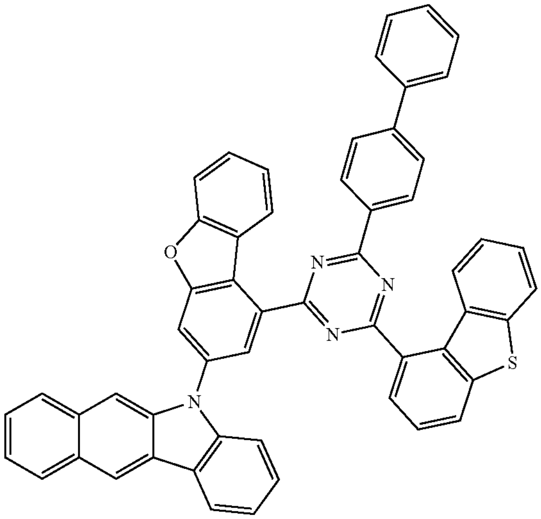
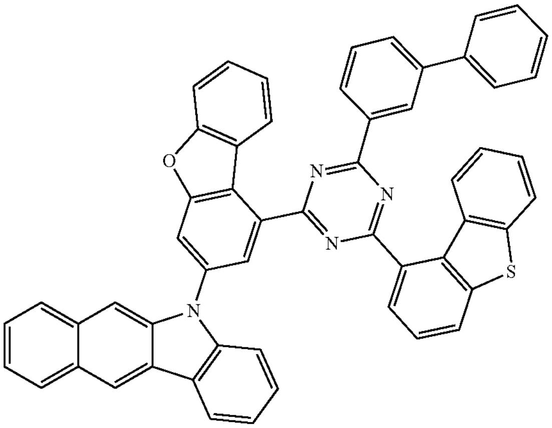
-continued
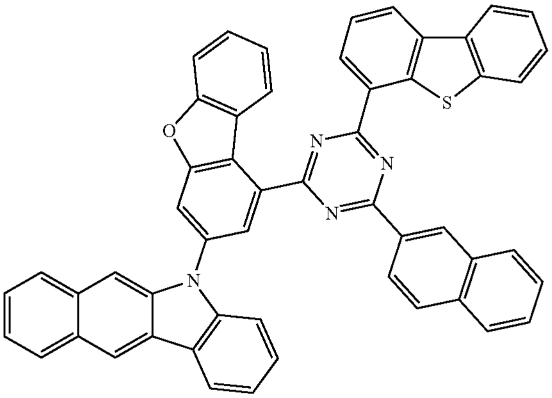
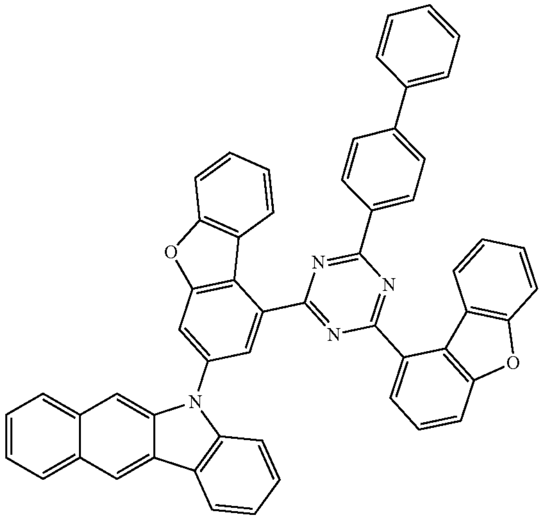
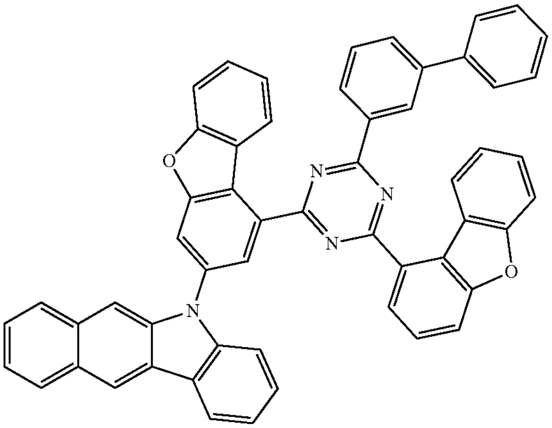

-continued
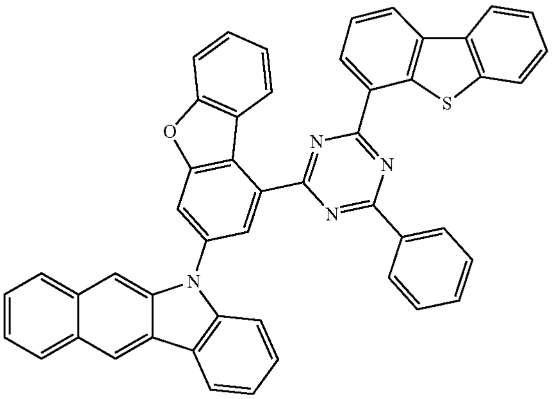
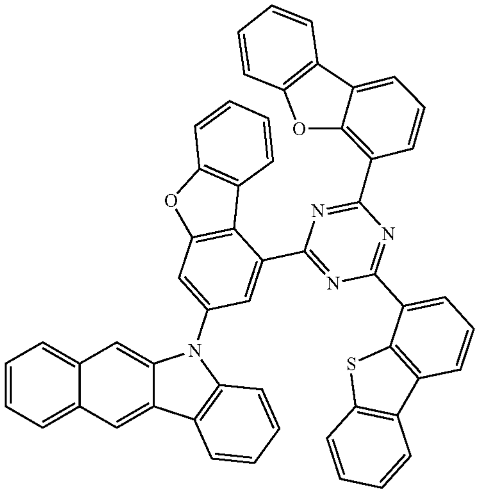
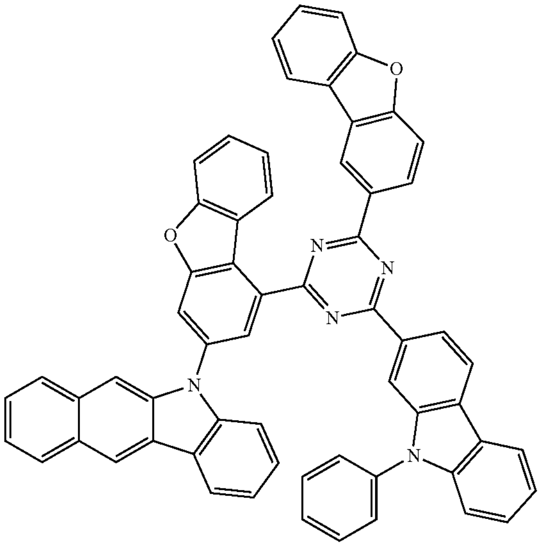
-continued
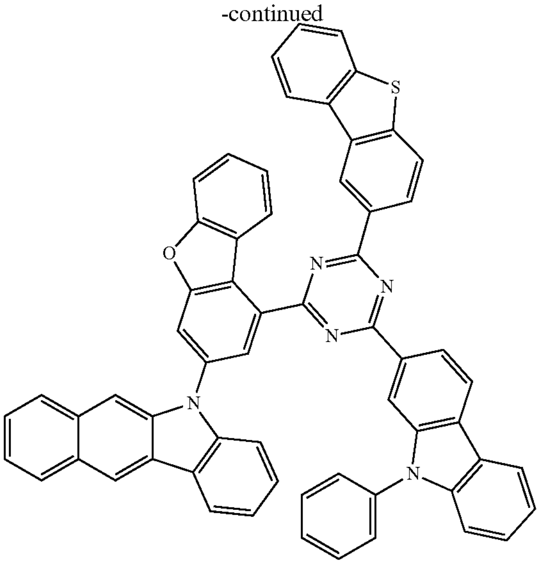
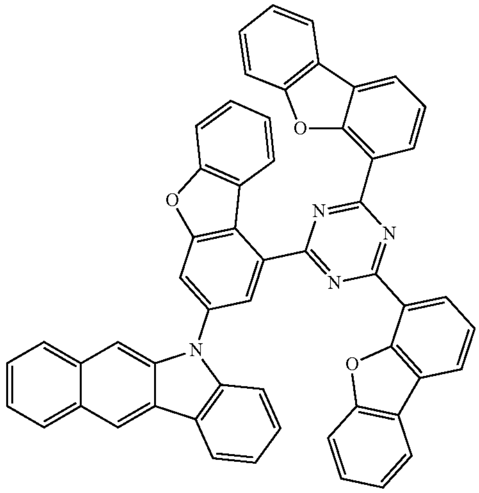
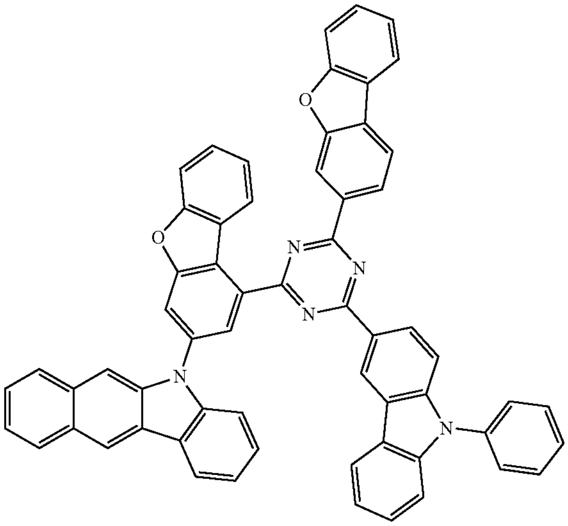

-continued
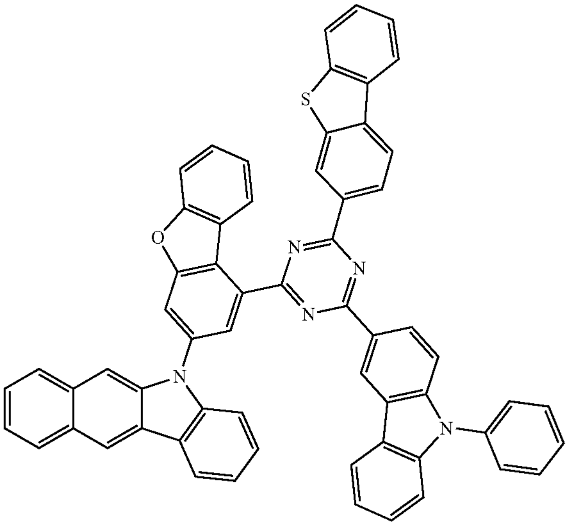
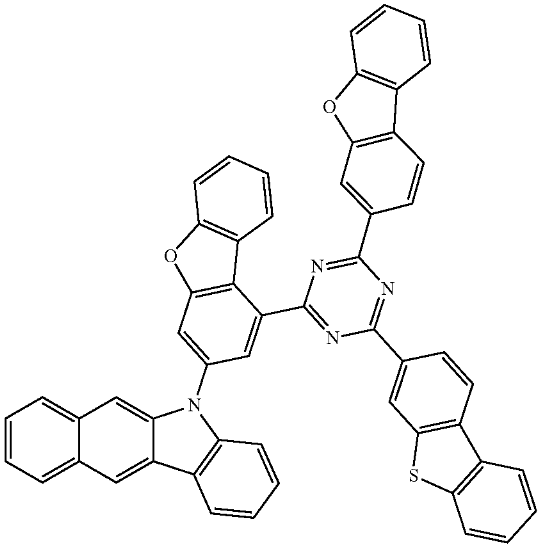
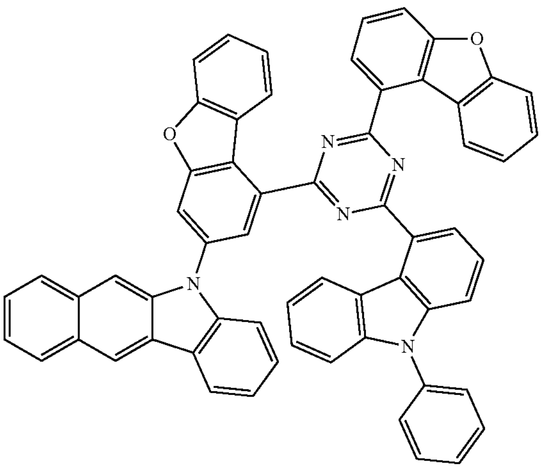
-continued
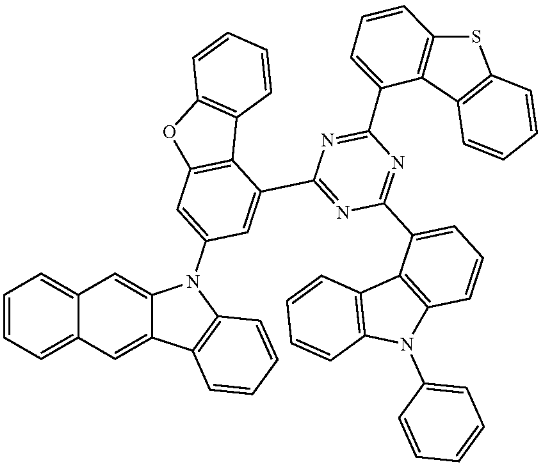
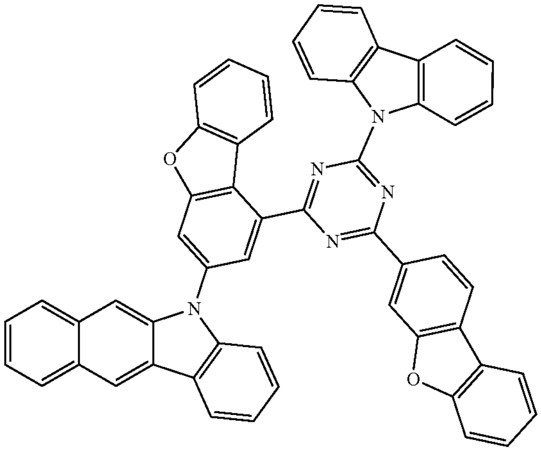
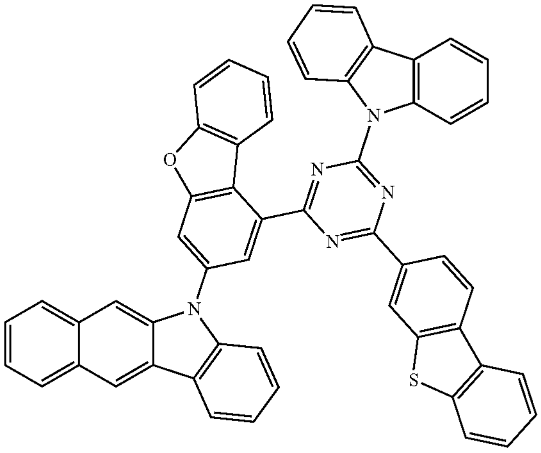

-continued
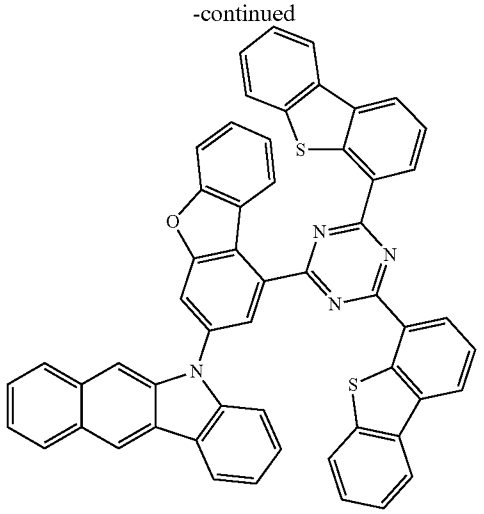
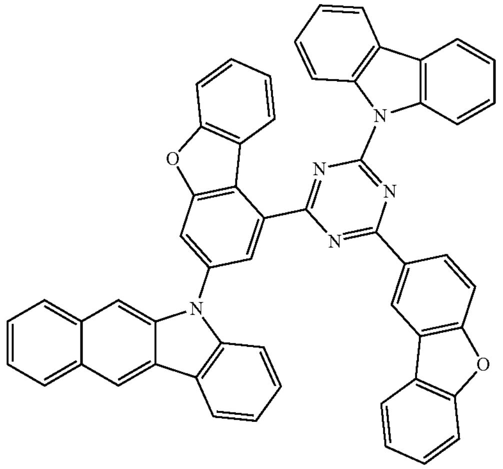
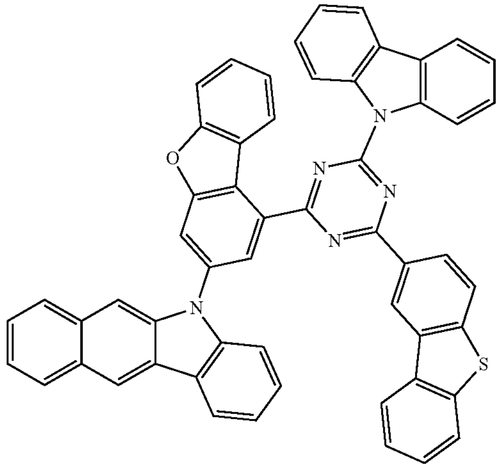
-continued
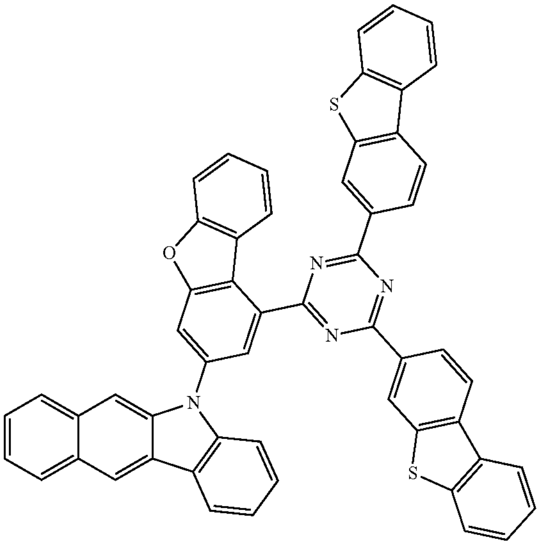
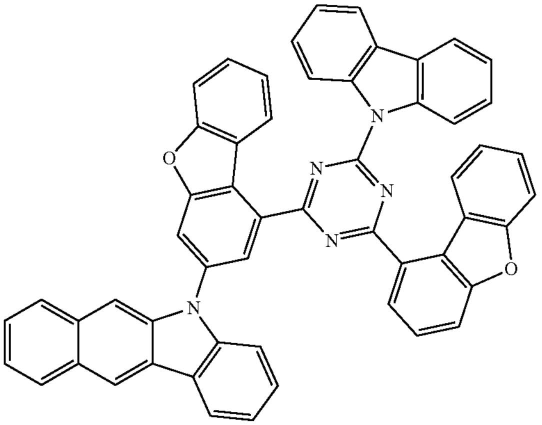
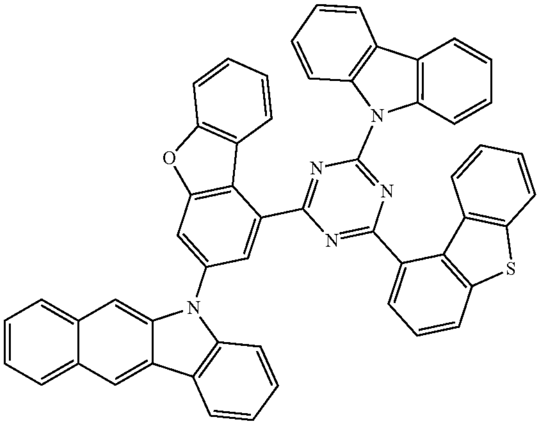

-continued
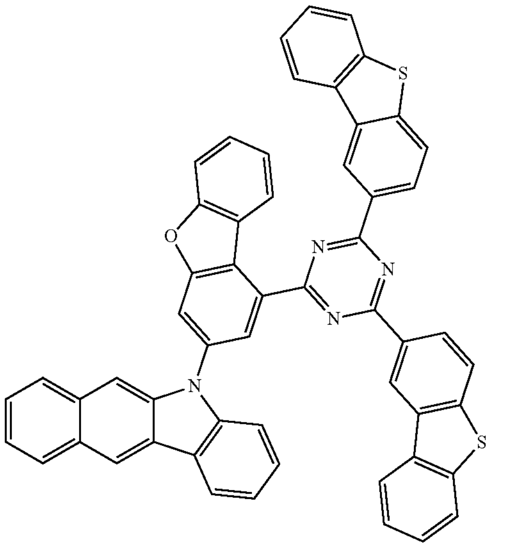
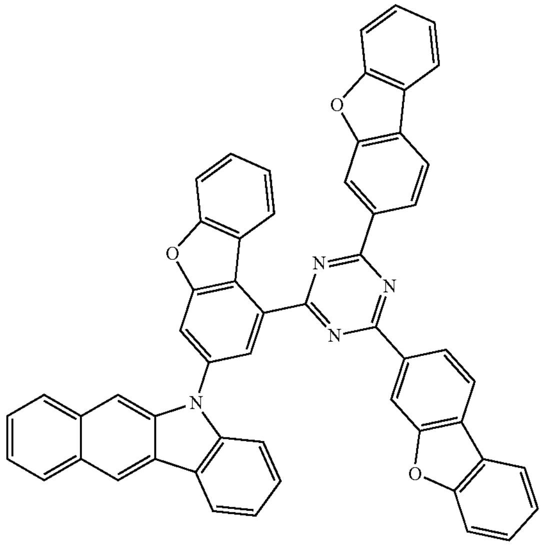
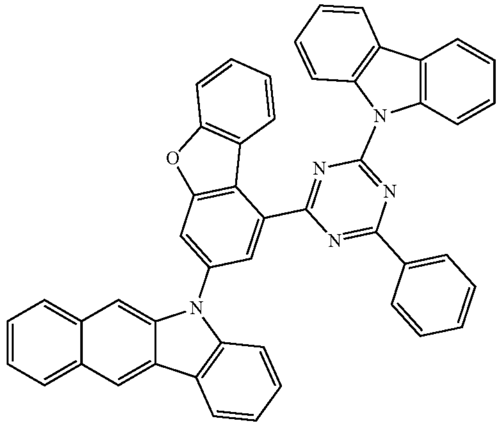
-continued
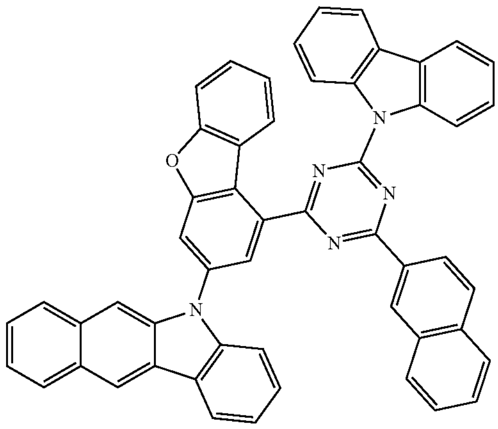
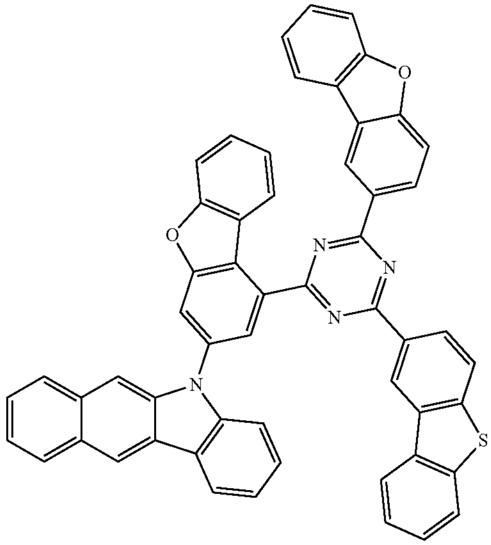
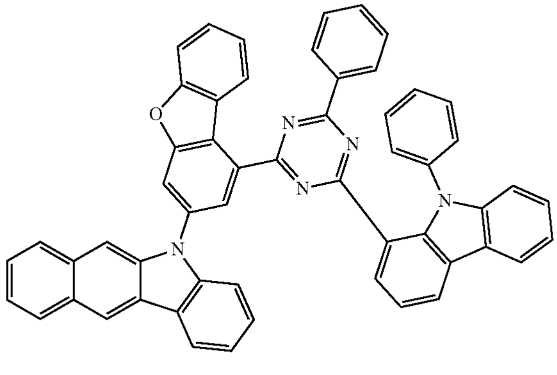

-continued
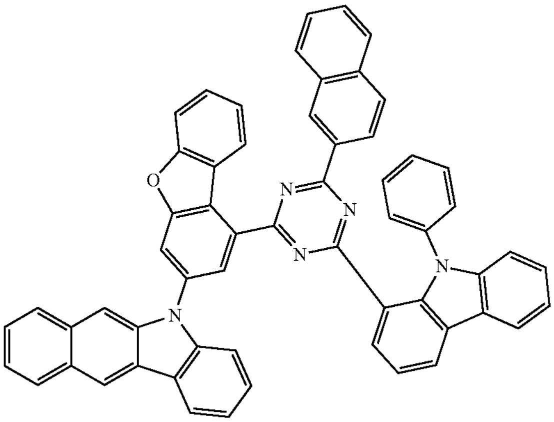
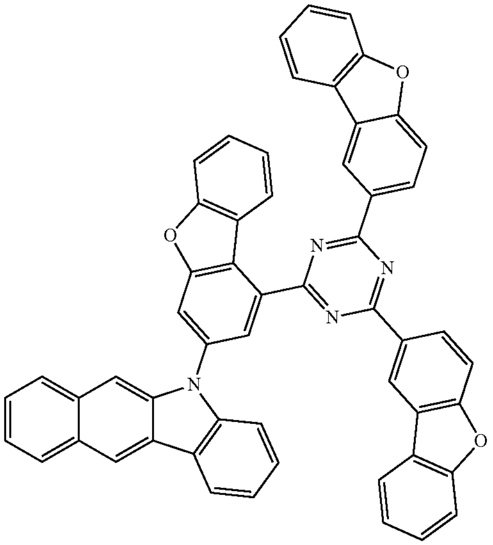
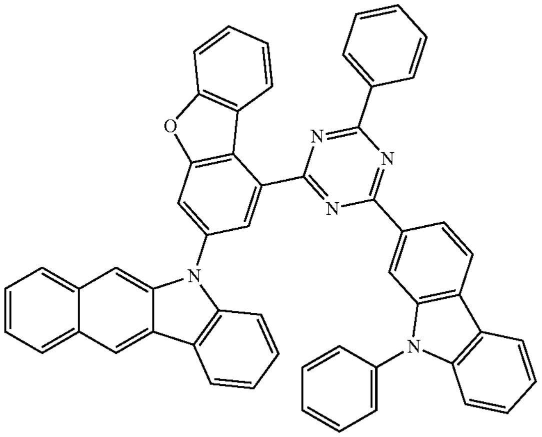
-continued
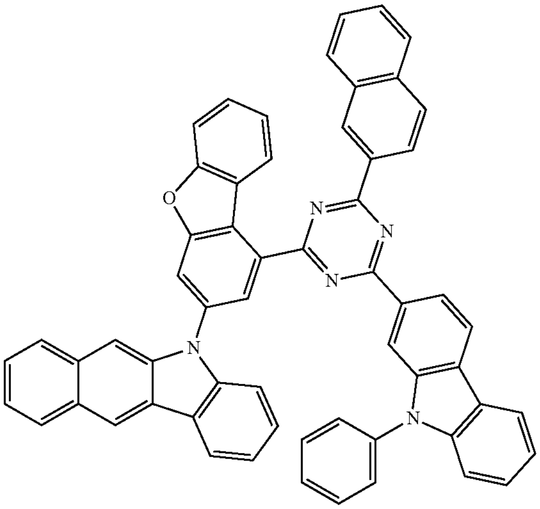
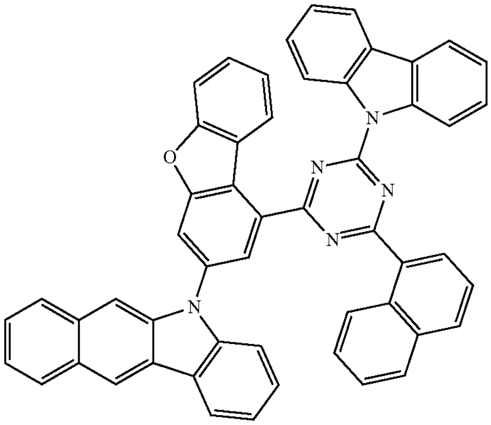
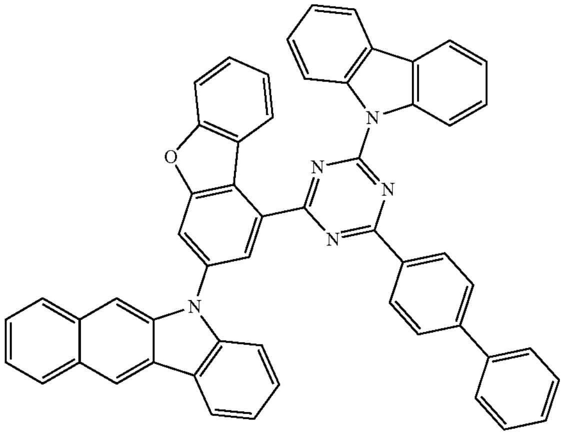

-continued
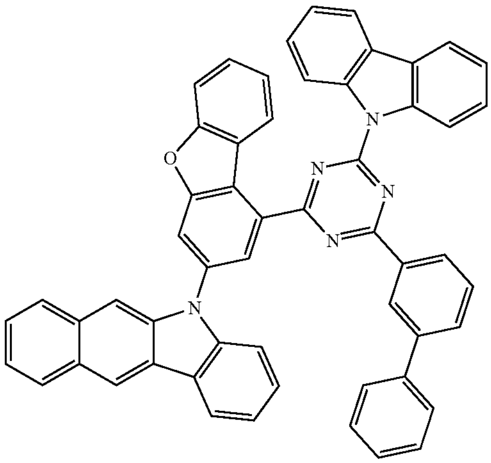
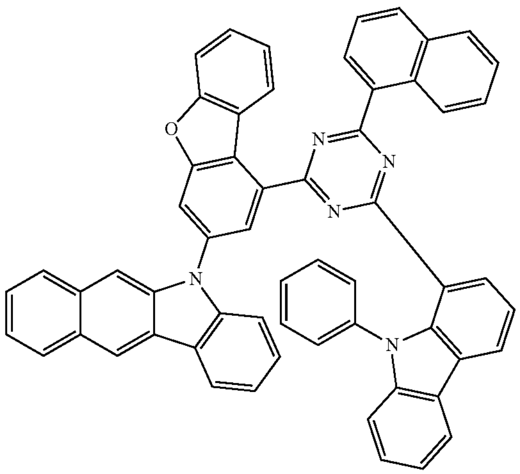
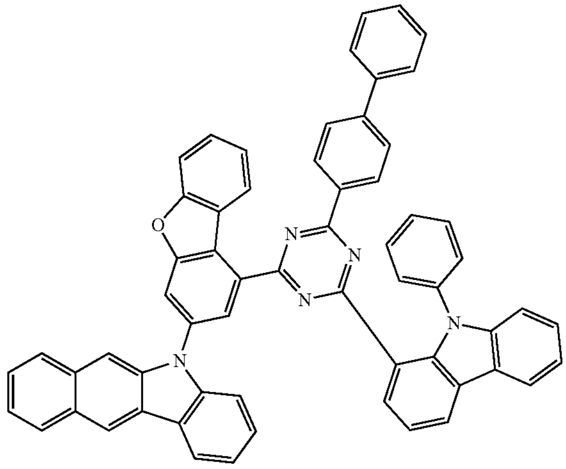
-continued
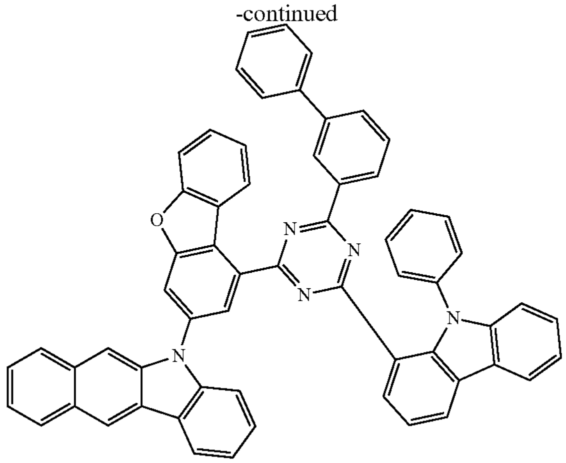
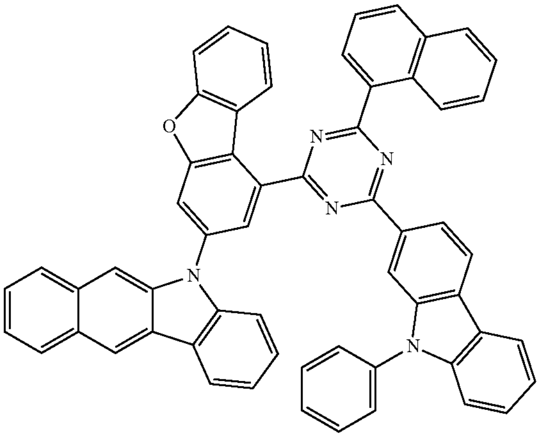
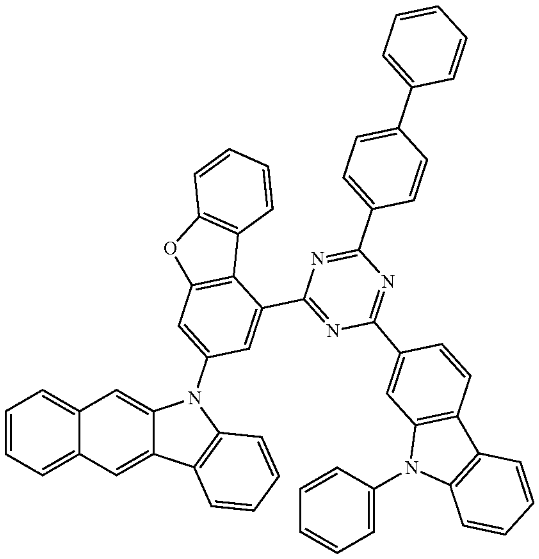

-continued
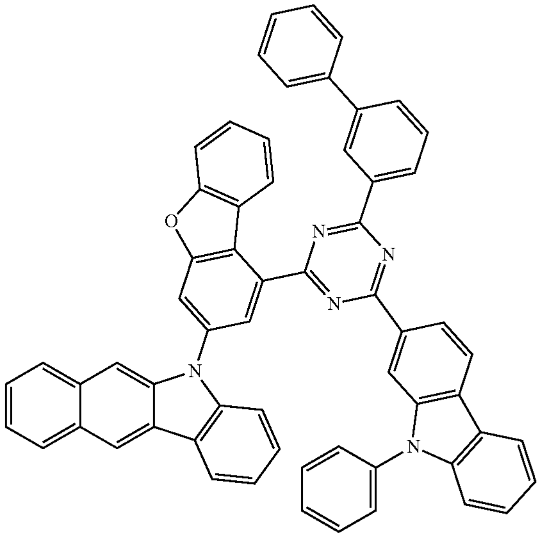
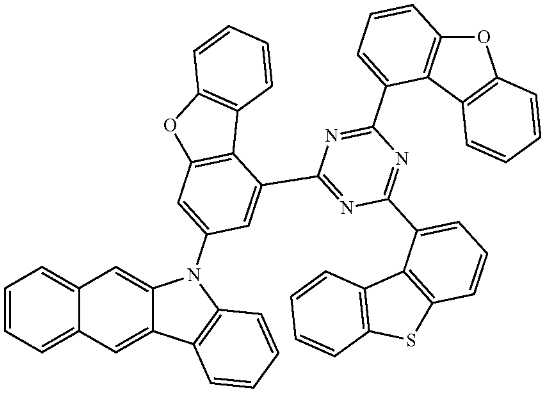
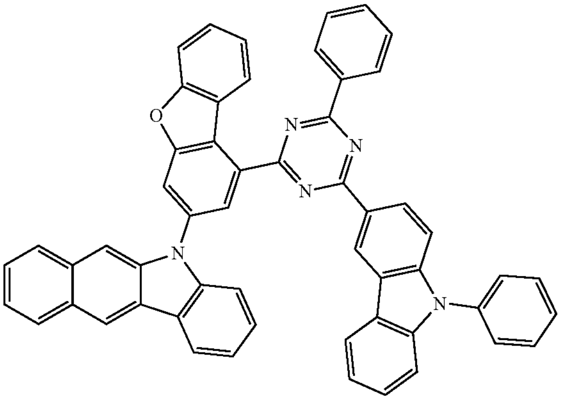
-continued
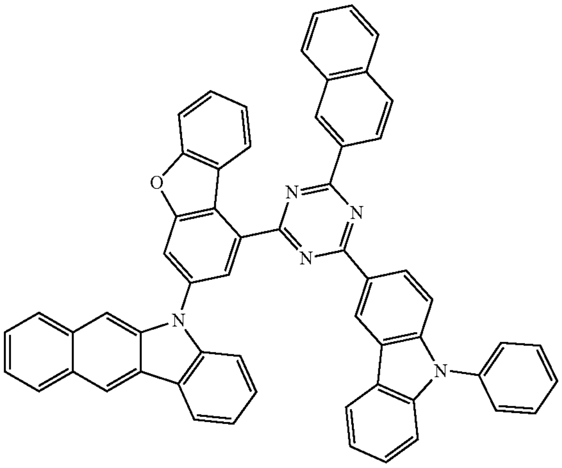
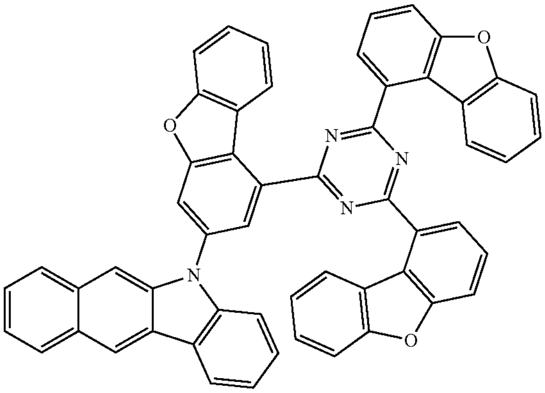
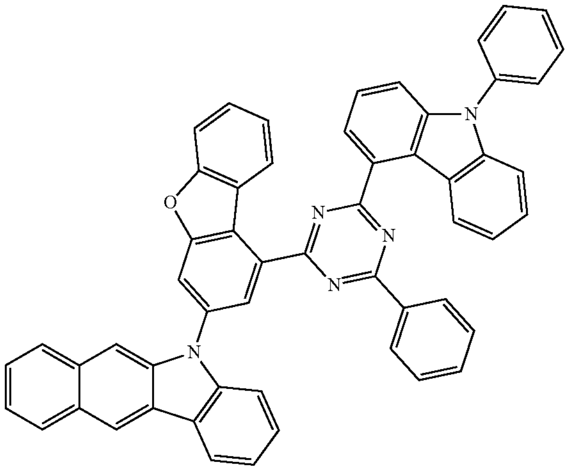

-continued
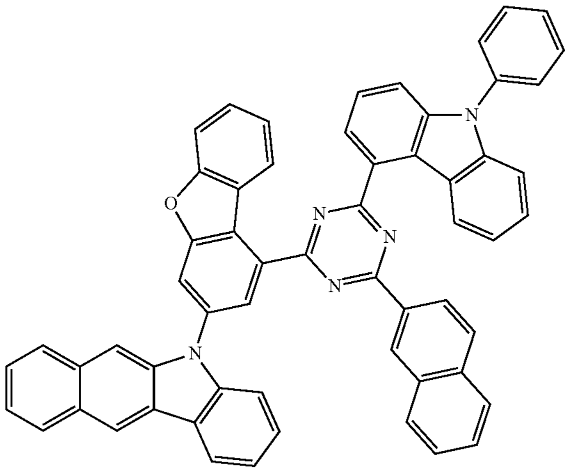
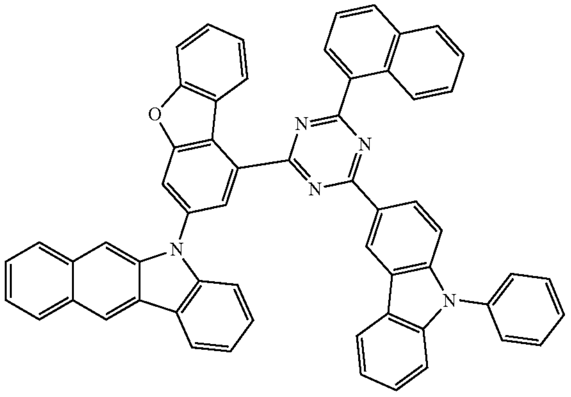
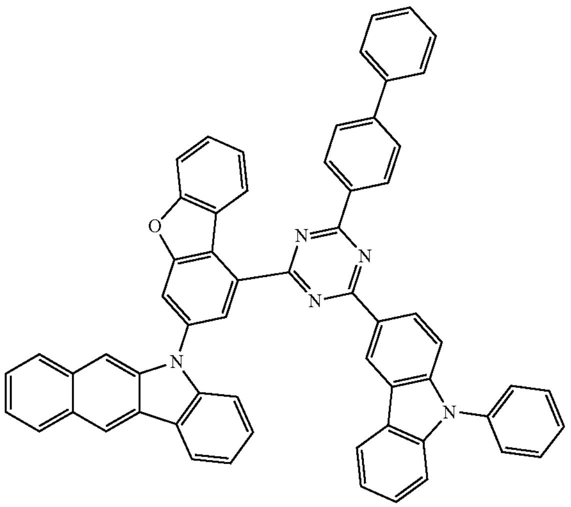
-continued
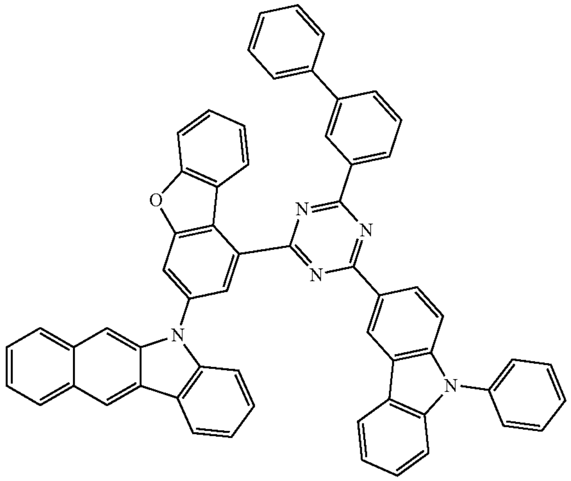
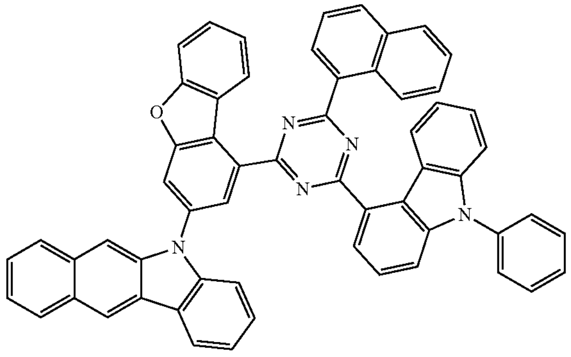
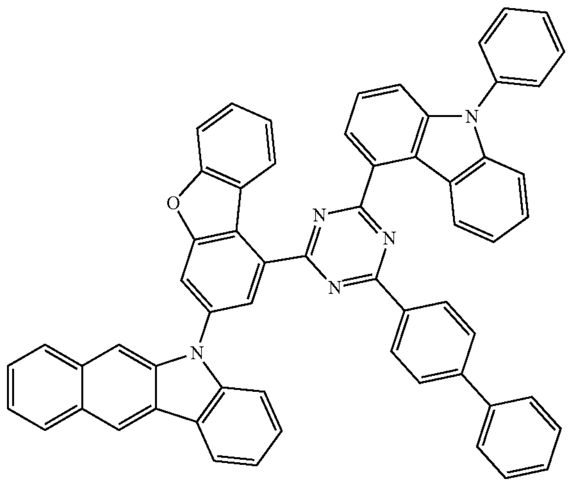

-continued
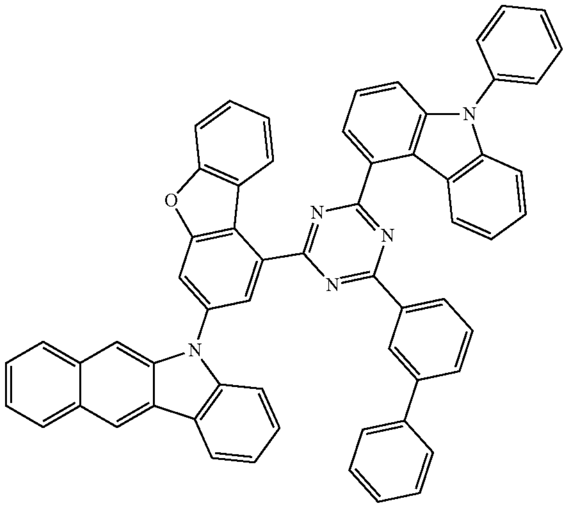
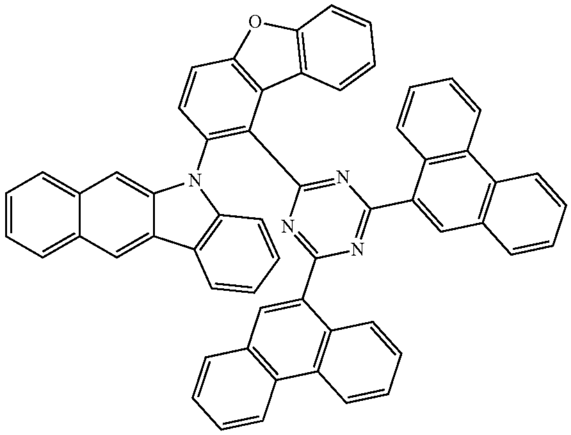
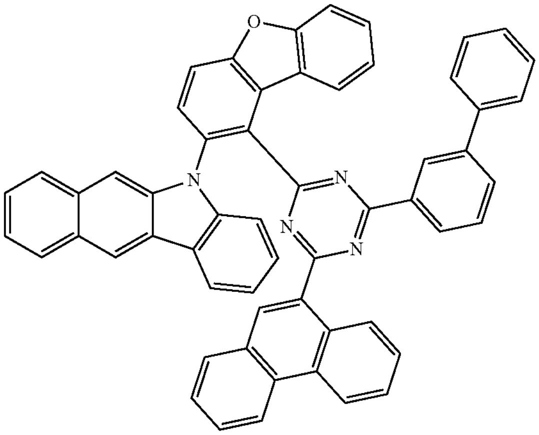
-continued
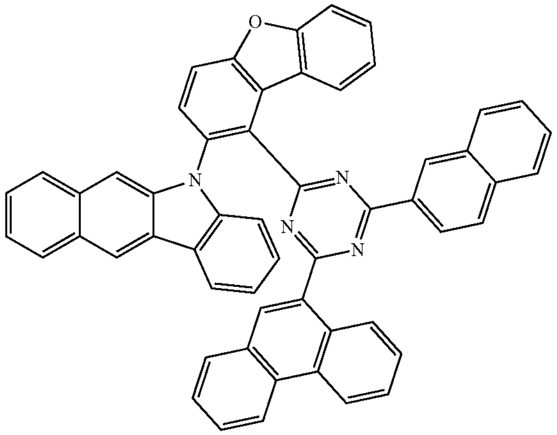
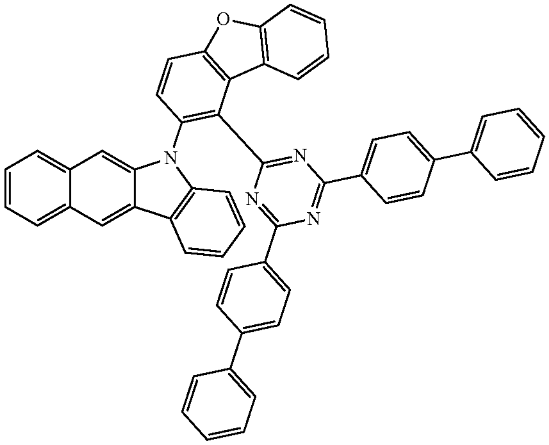
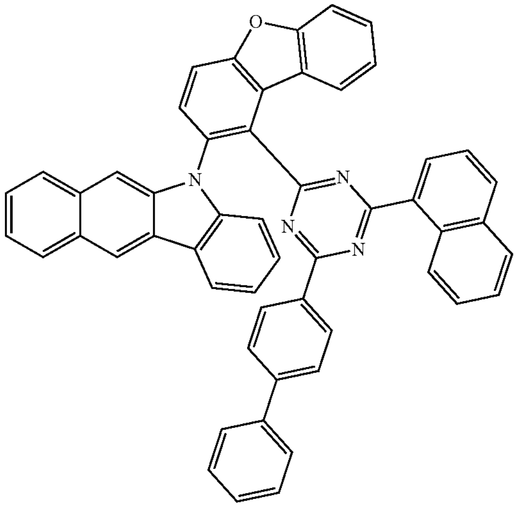

-continued
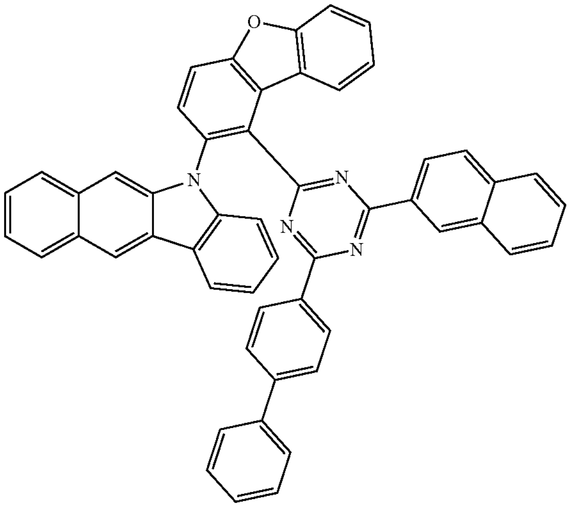
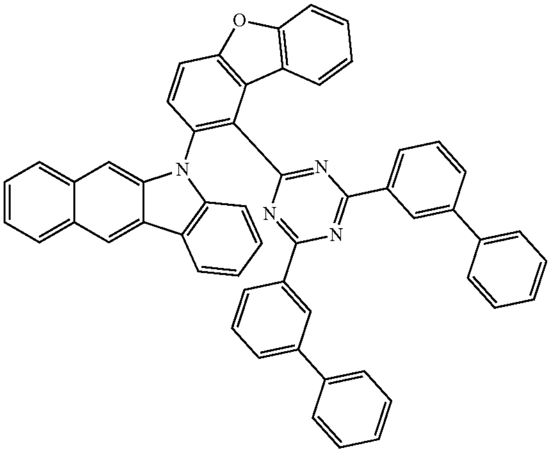
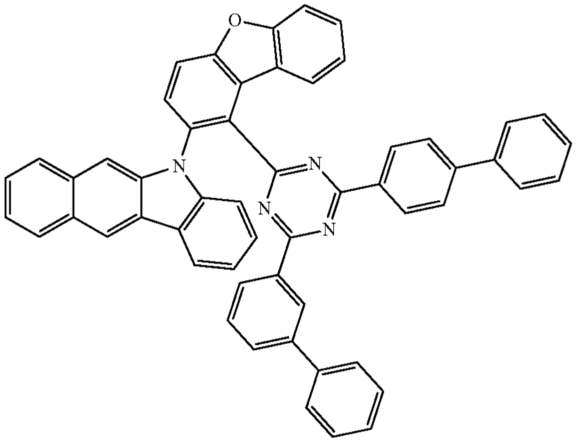
-continued
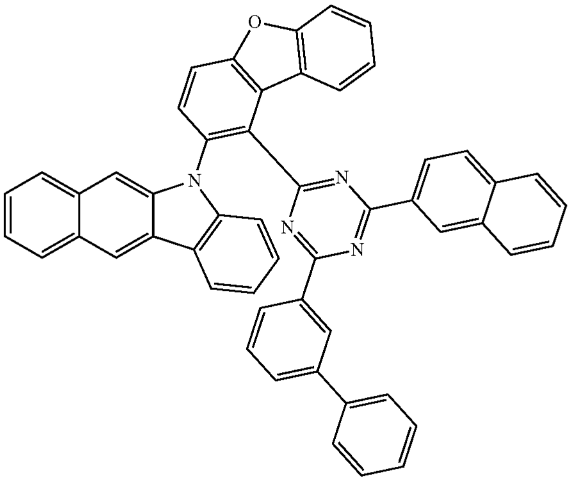
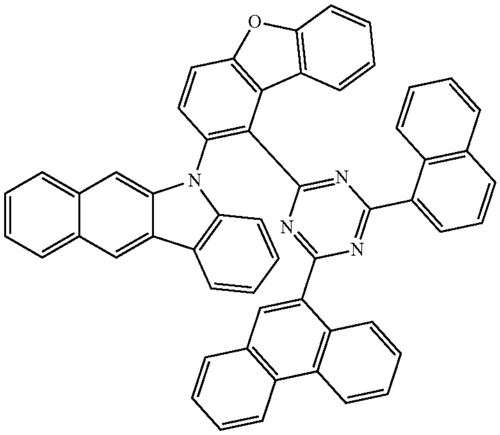
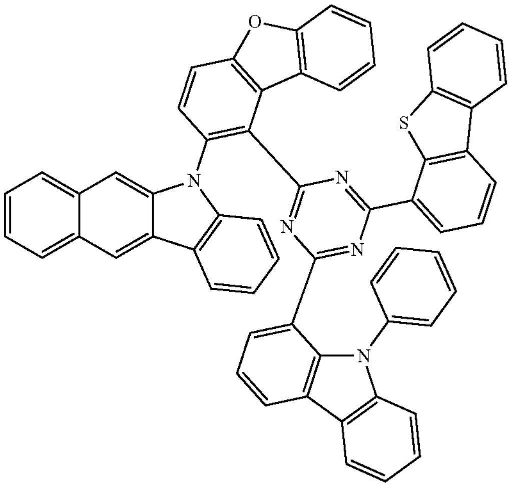

-continued
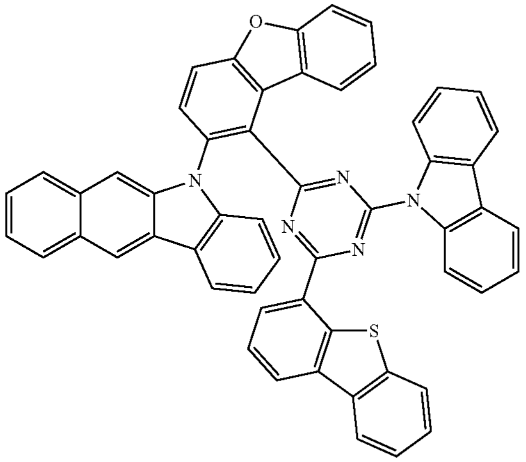
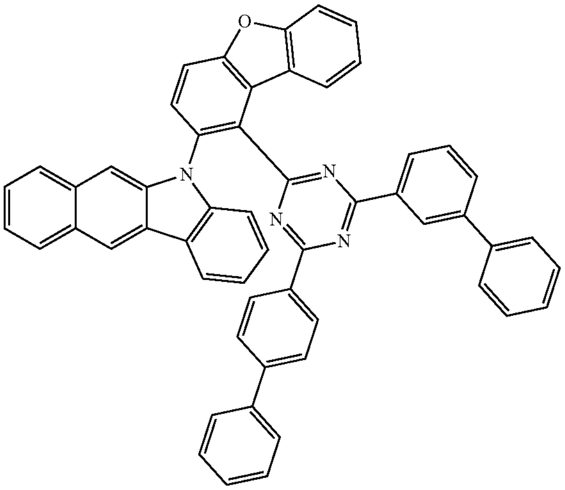
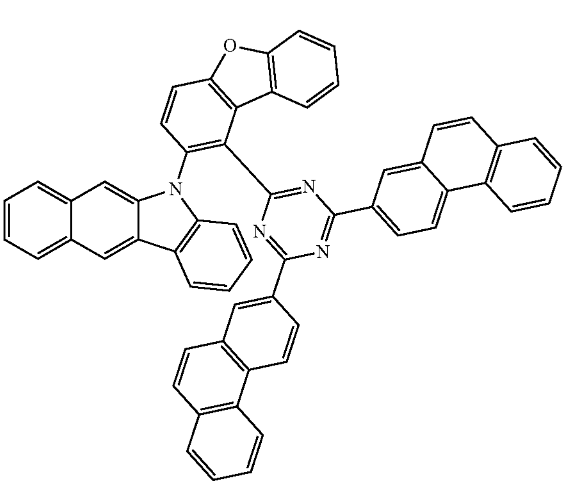
-continued
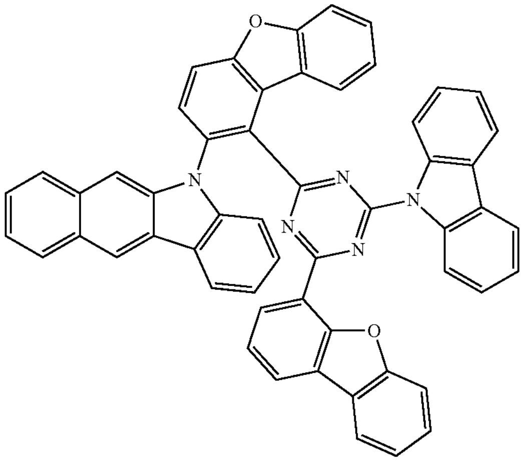
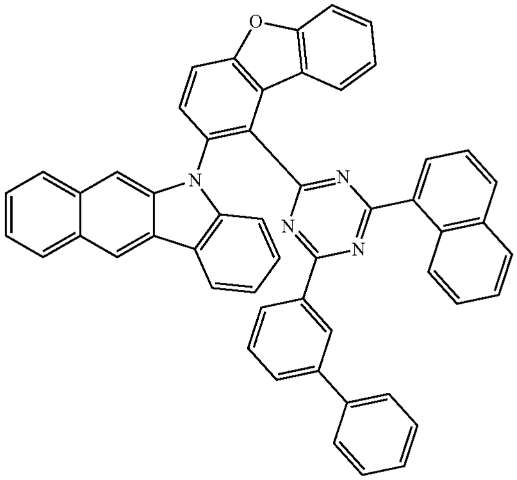
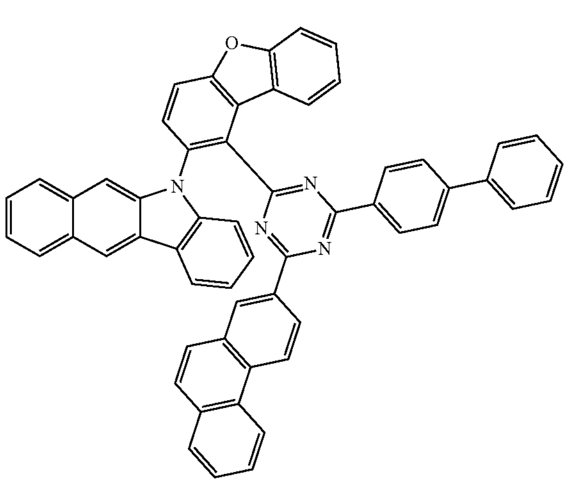

-continued
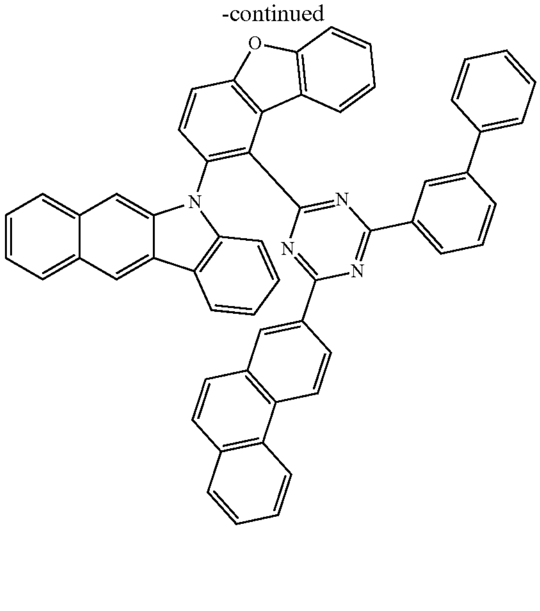
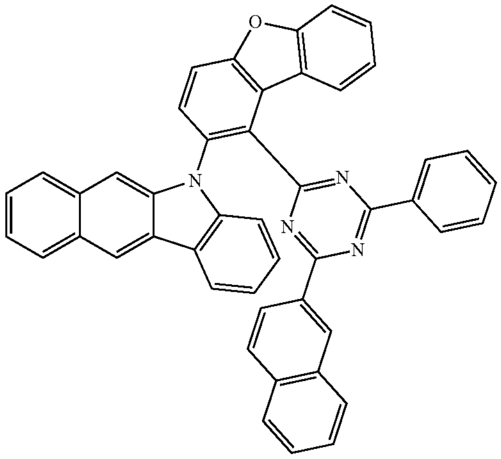
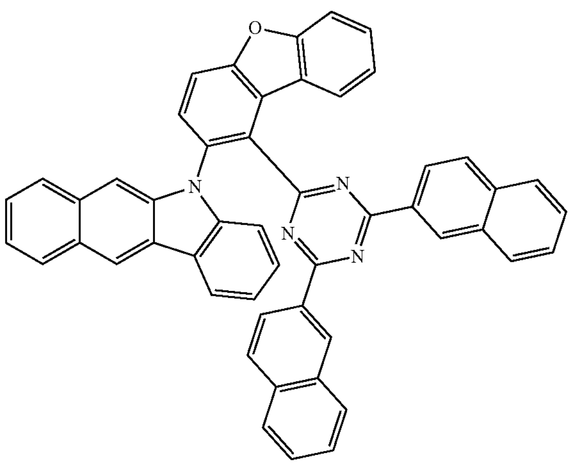
-continued
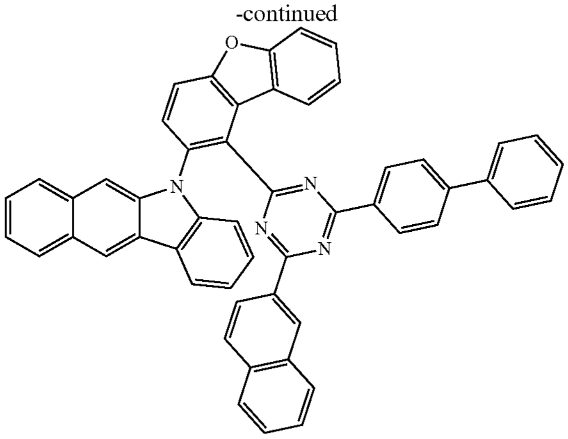
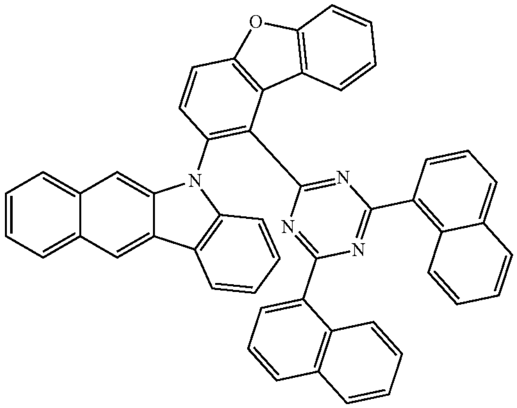
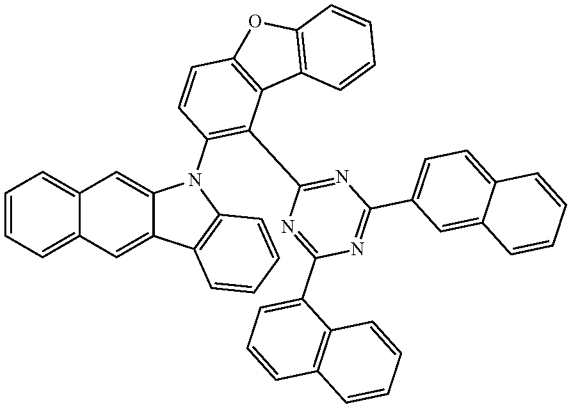
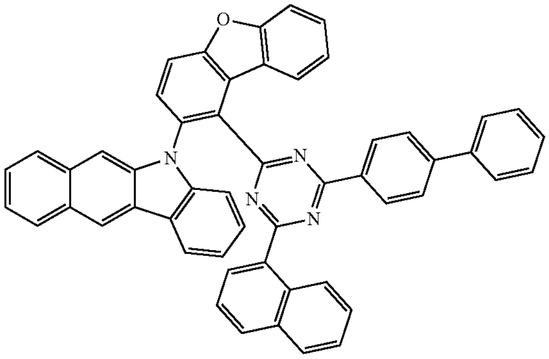

-continued
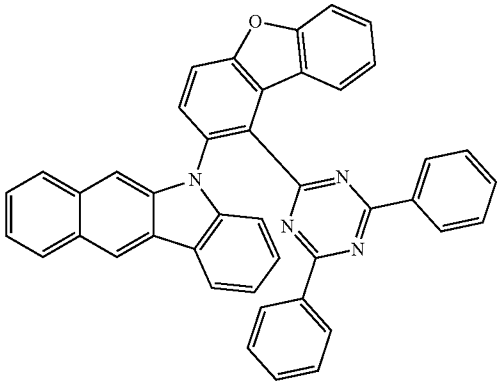
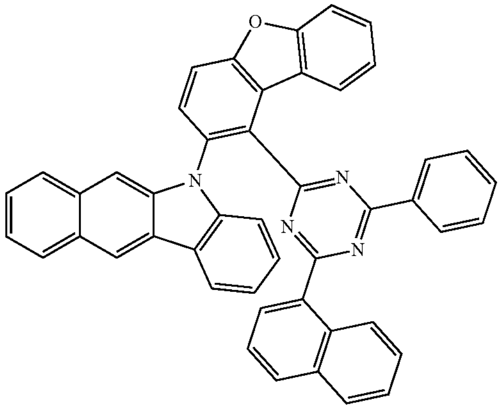
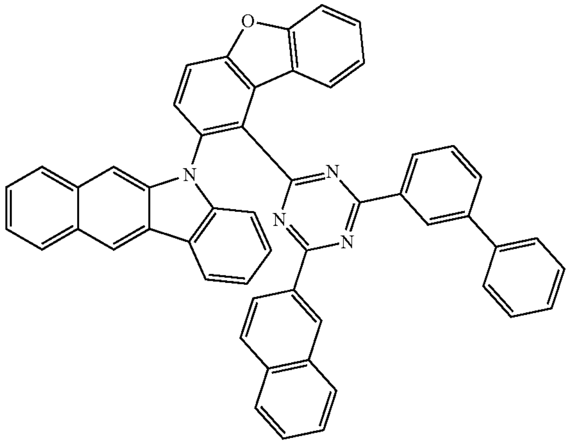
-continued
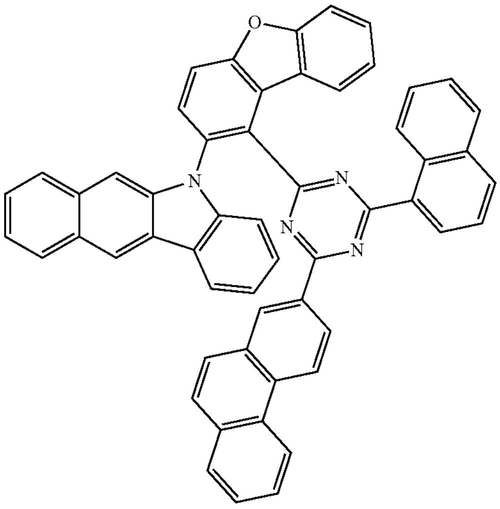
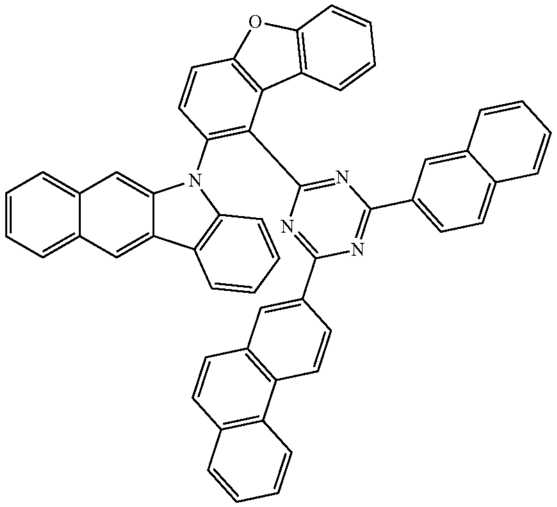
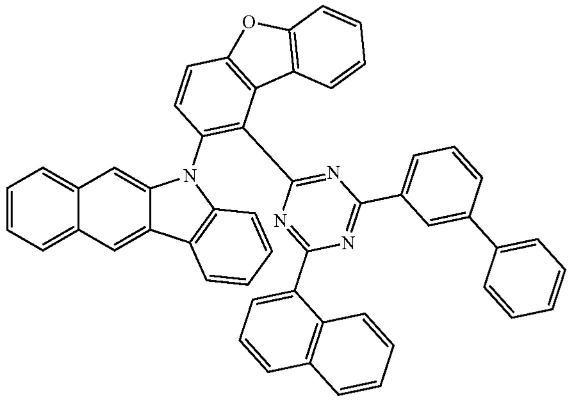

-continued
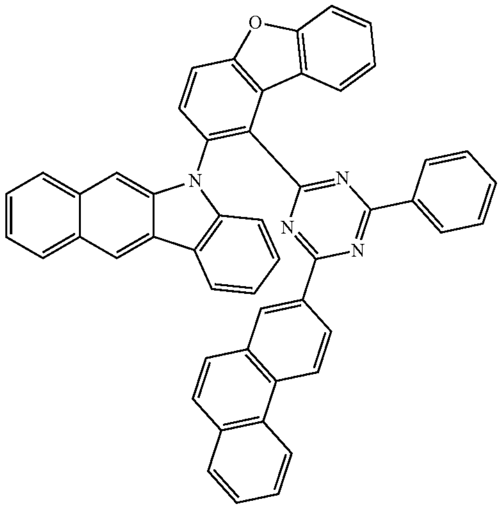
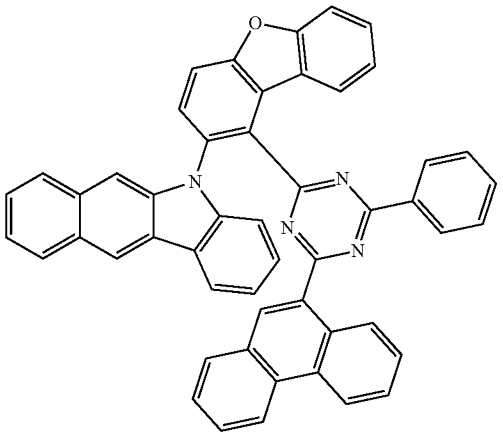
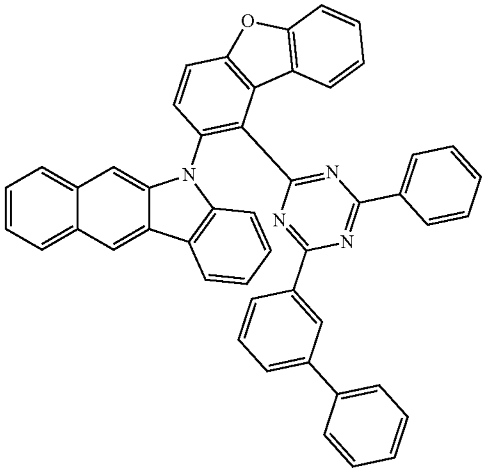
-continued
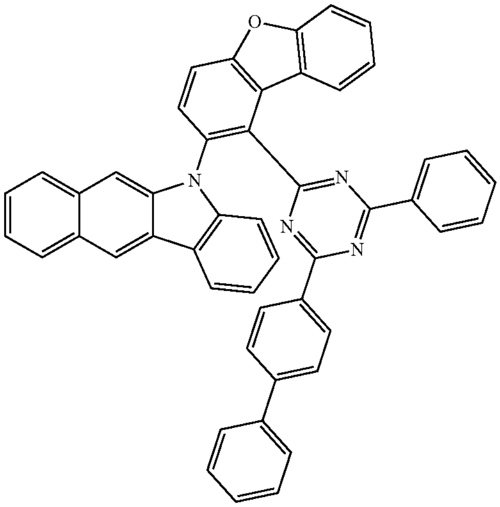
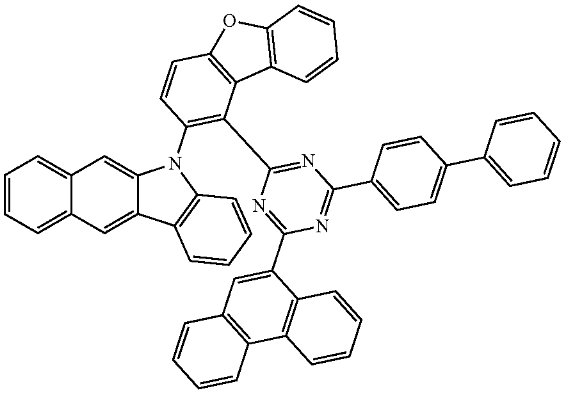
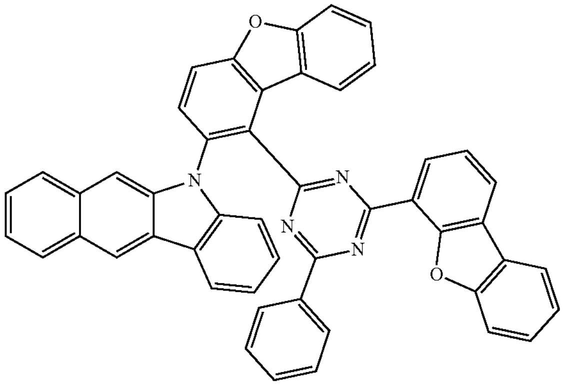

-continued
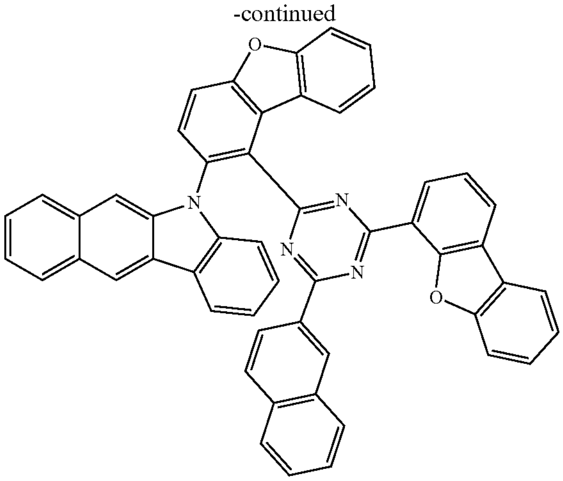
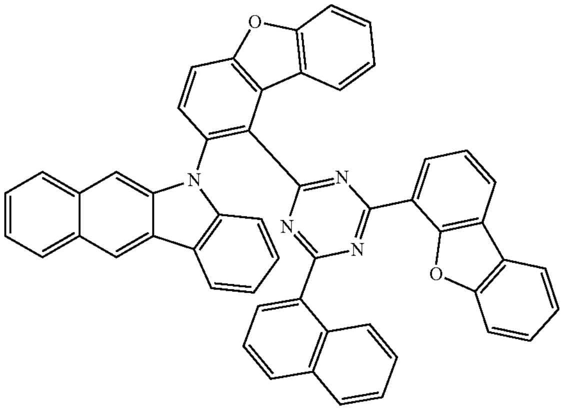
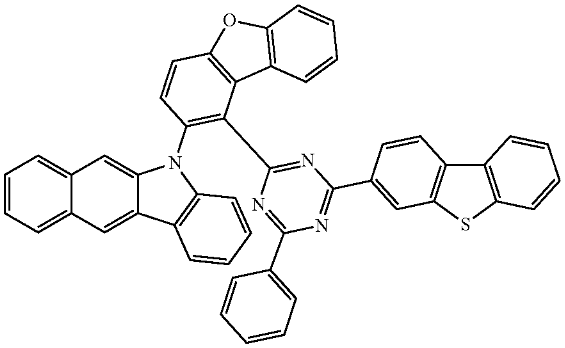
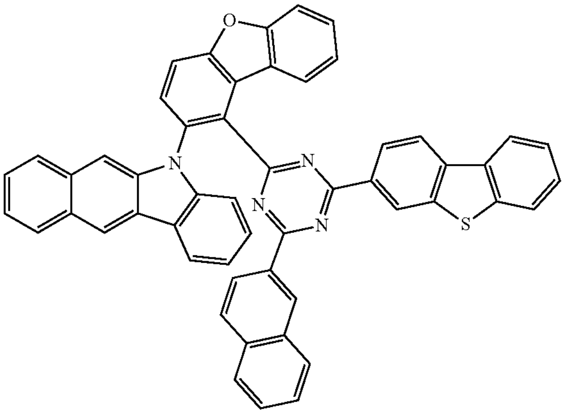
-continued
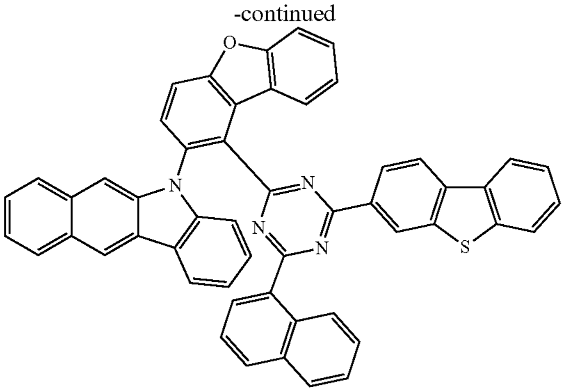
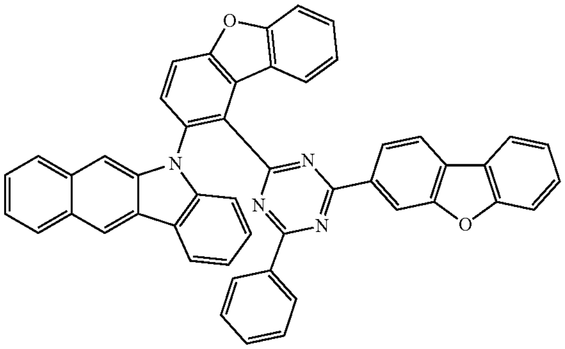
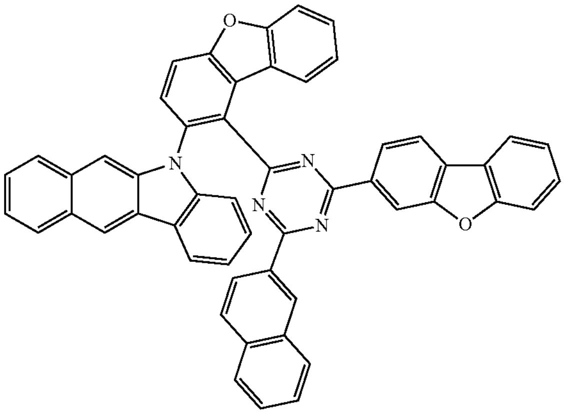
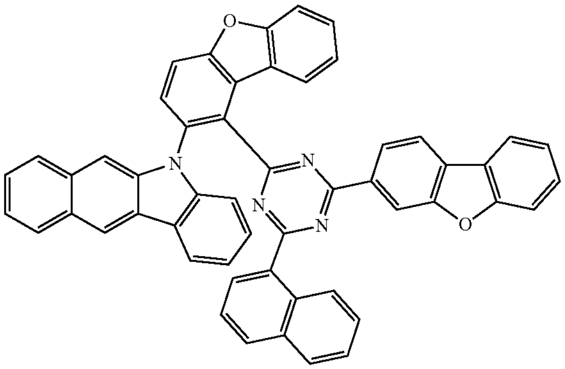

-continued
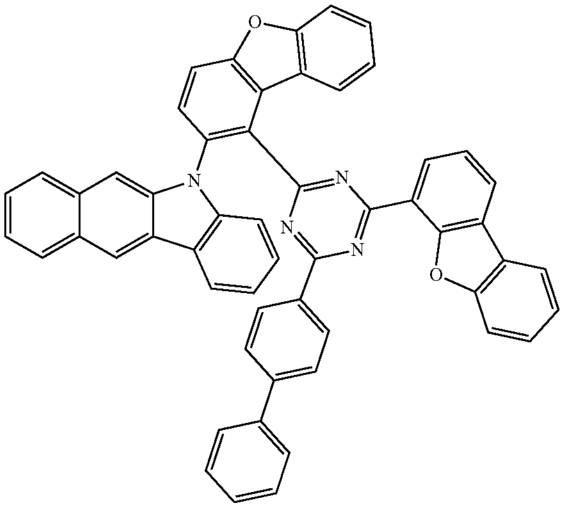
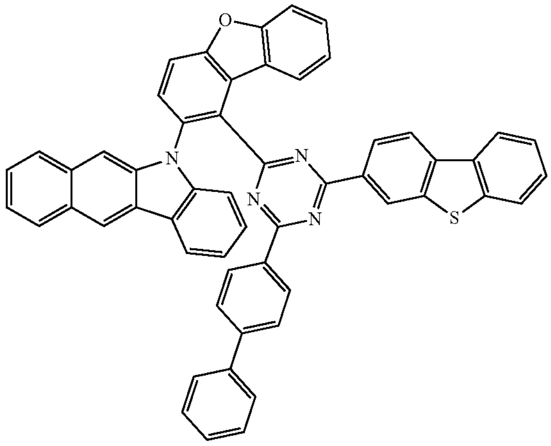
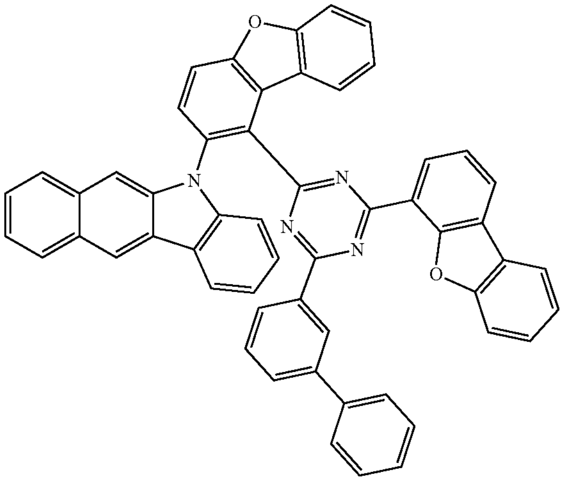
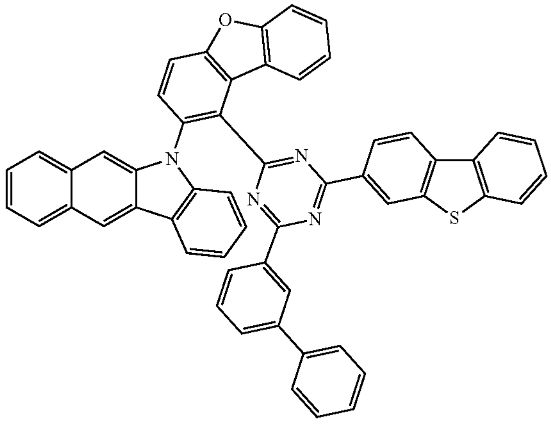
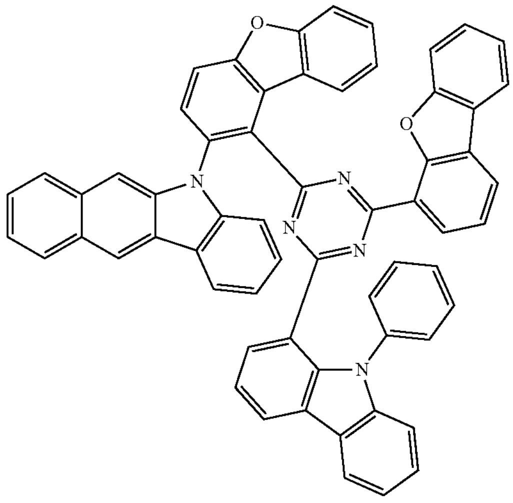
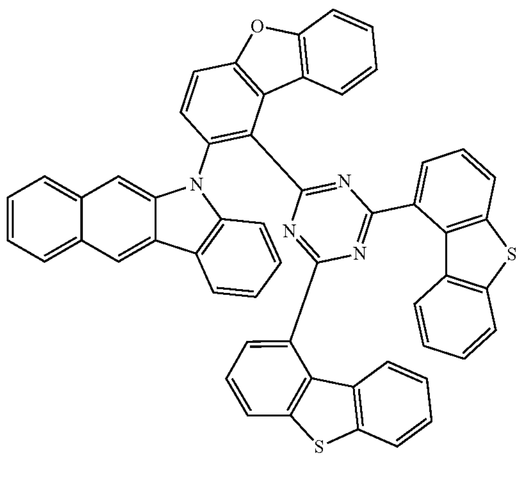
-continued -continued
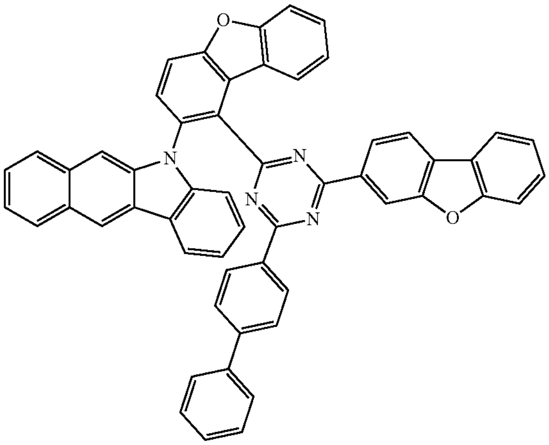
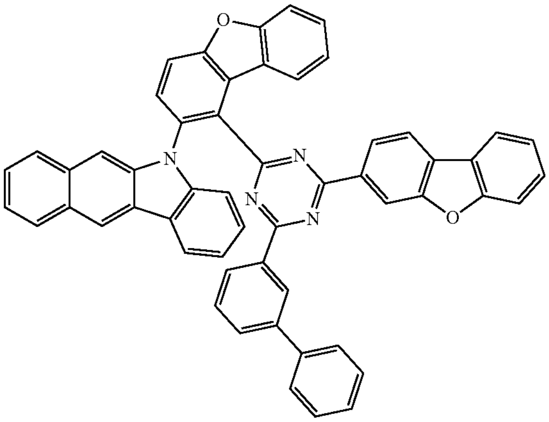
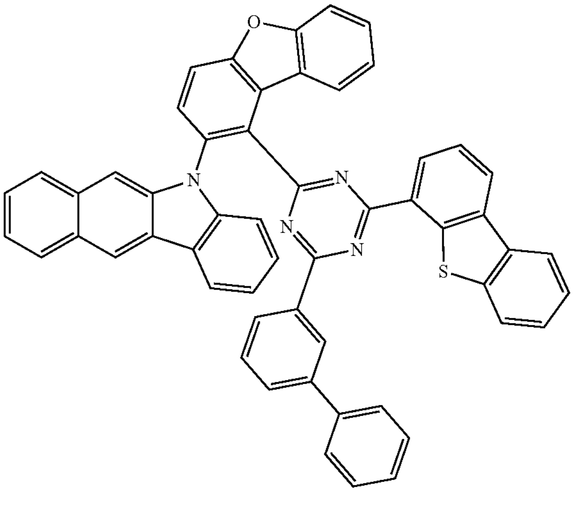
-continued
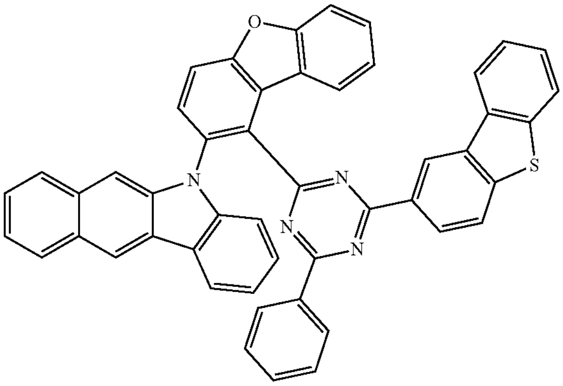
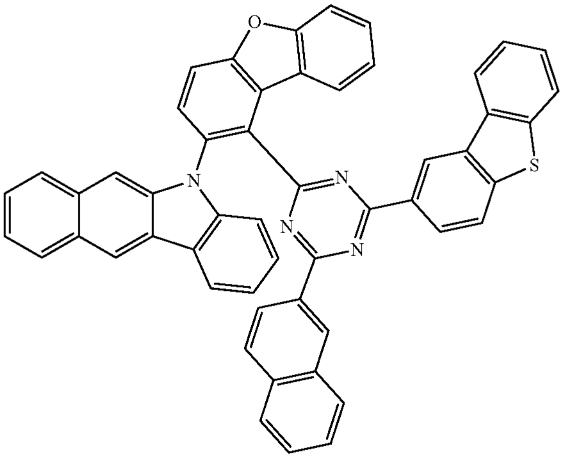
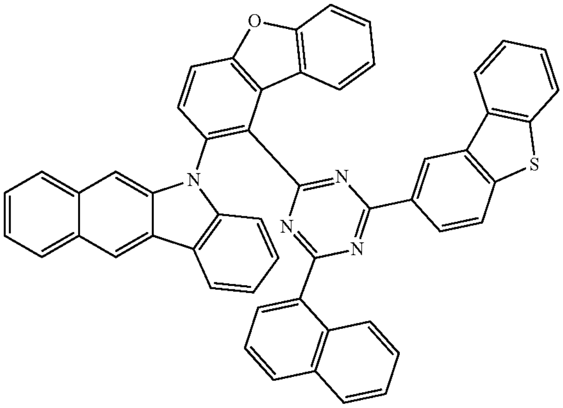
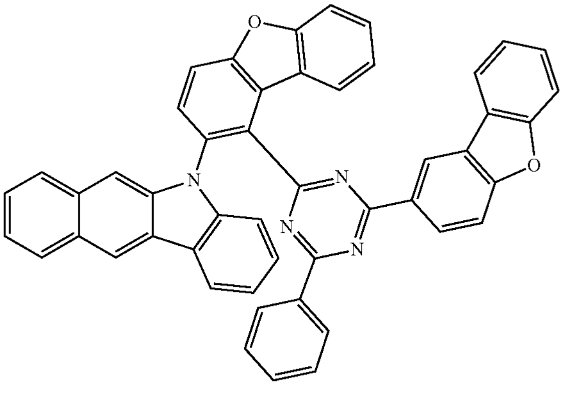

-continued
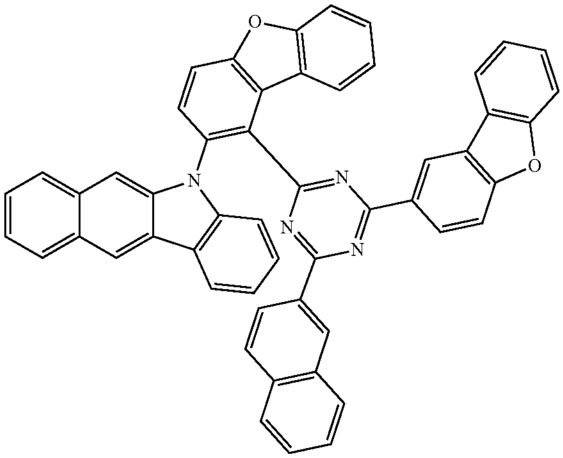
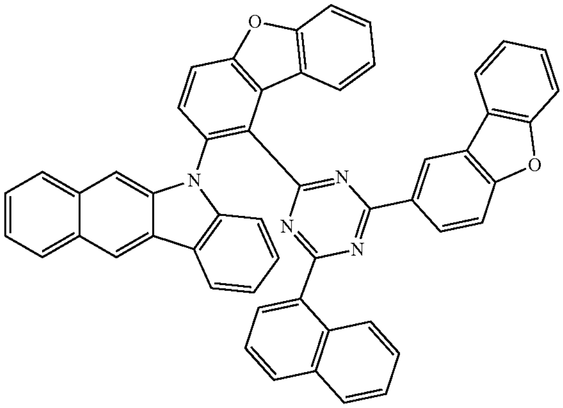
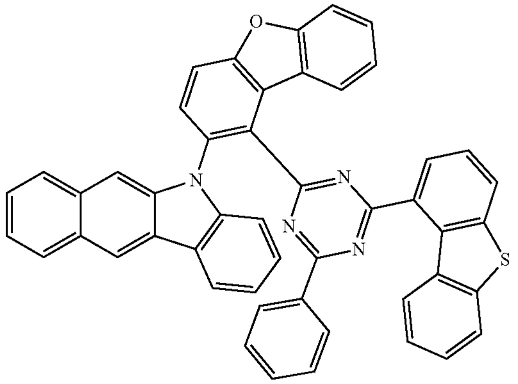
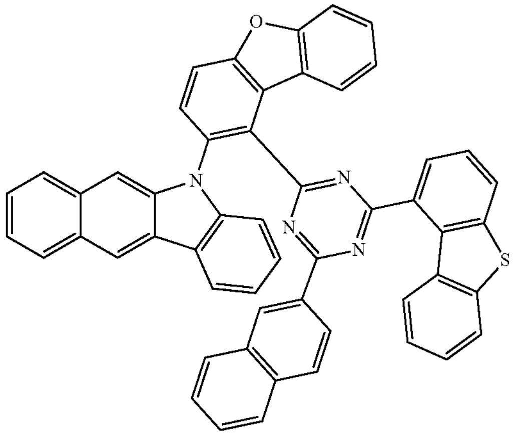
-continued
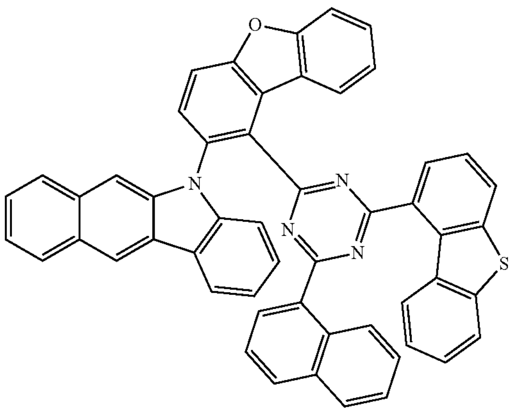
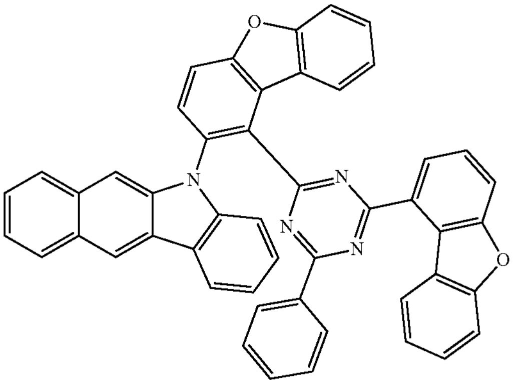
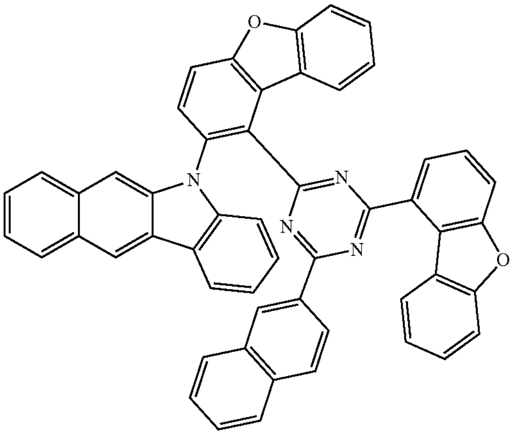
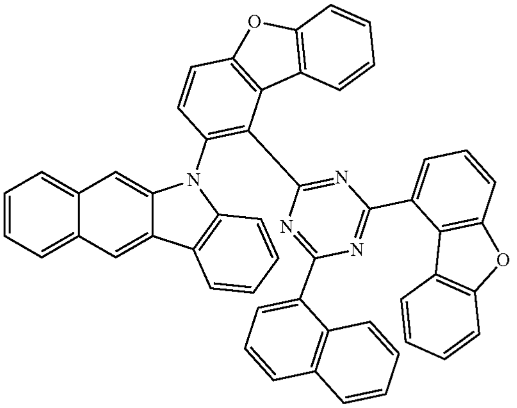

-continued
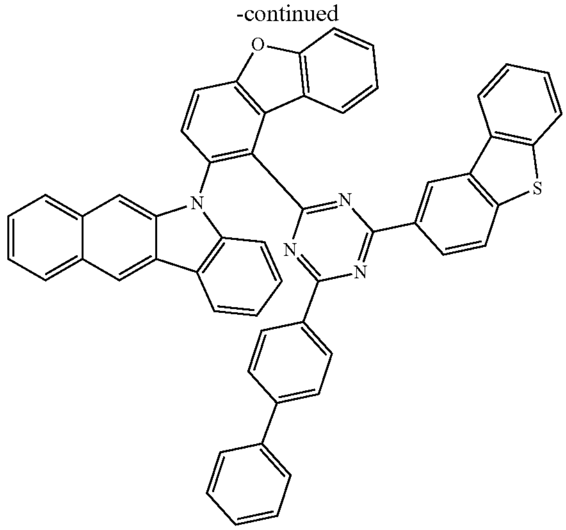
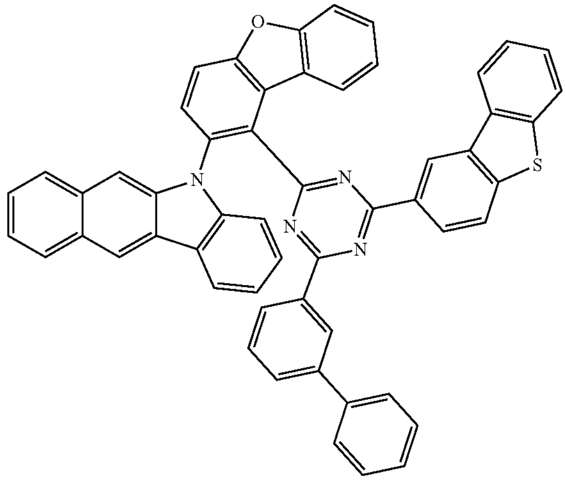
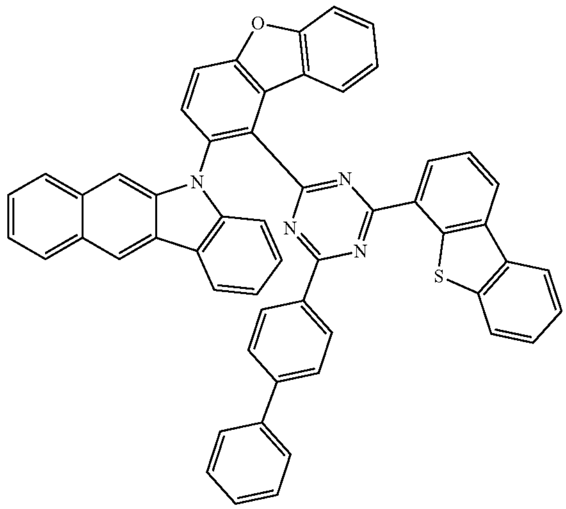
-continued
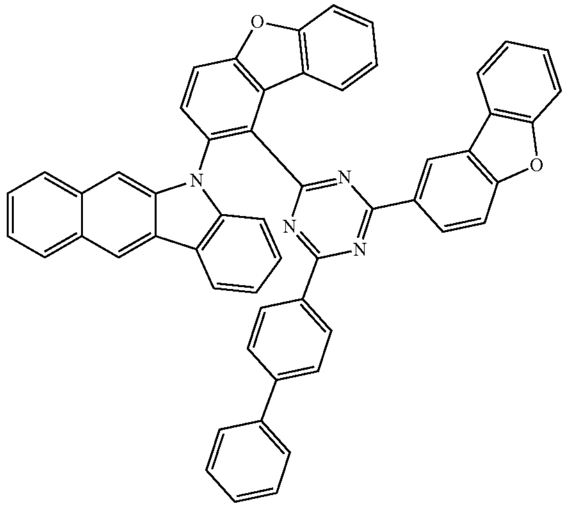
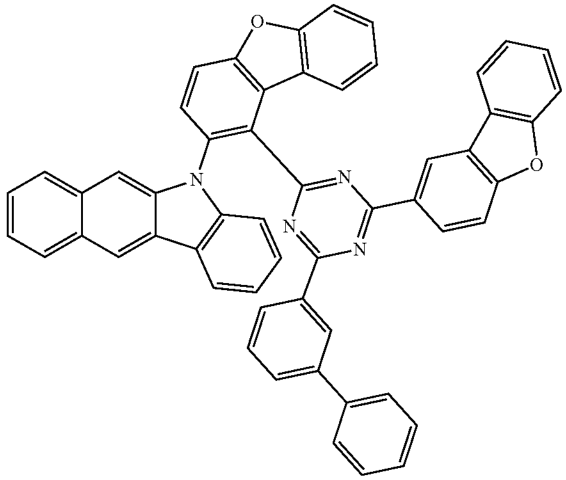
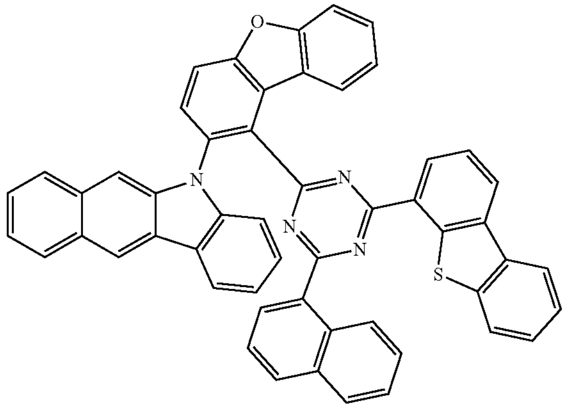

-continued
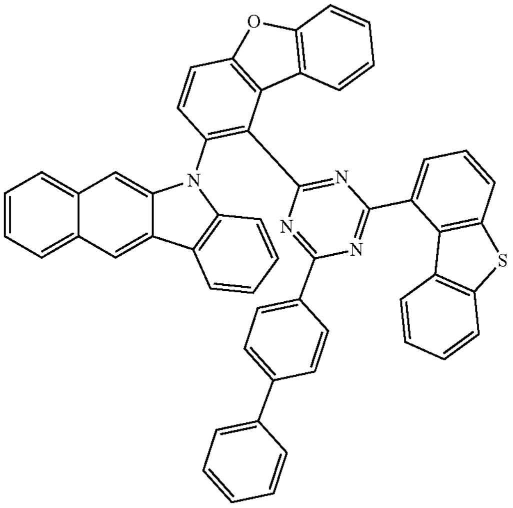
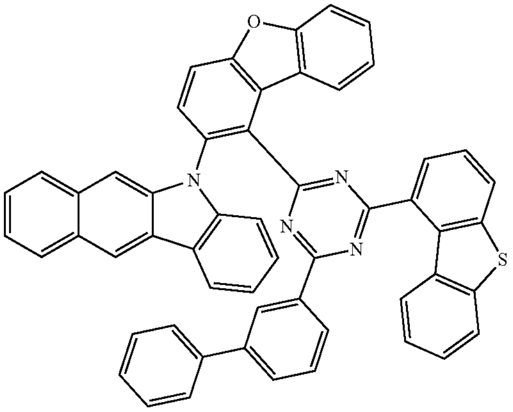
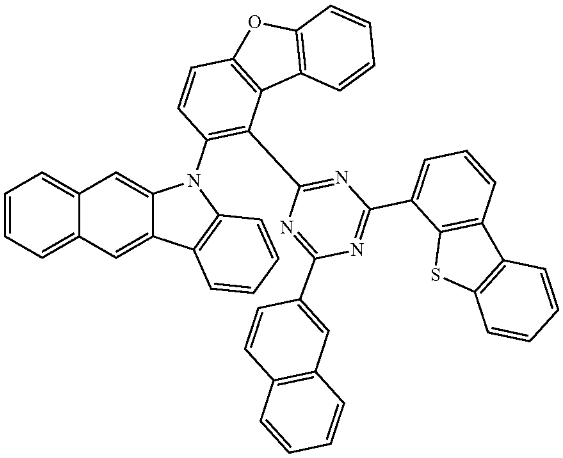
-continued
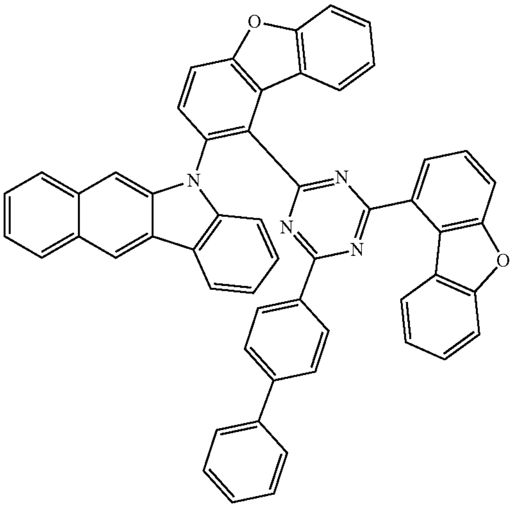
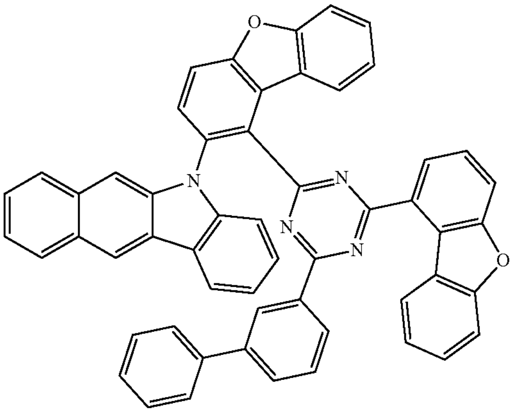
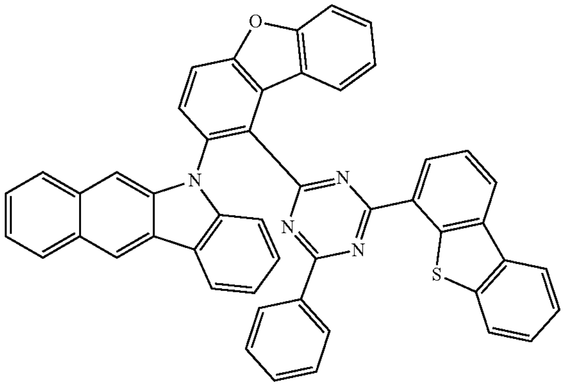

-continued
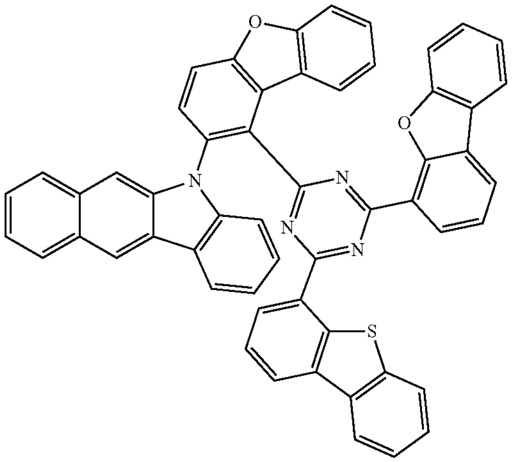
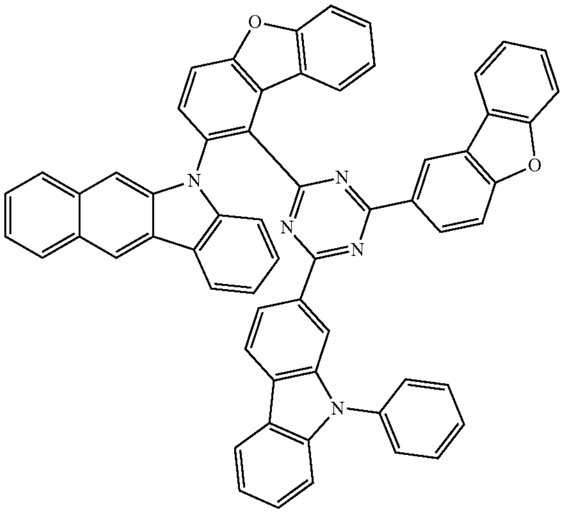
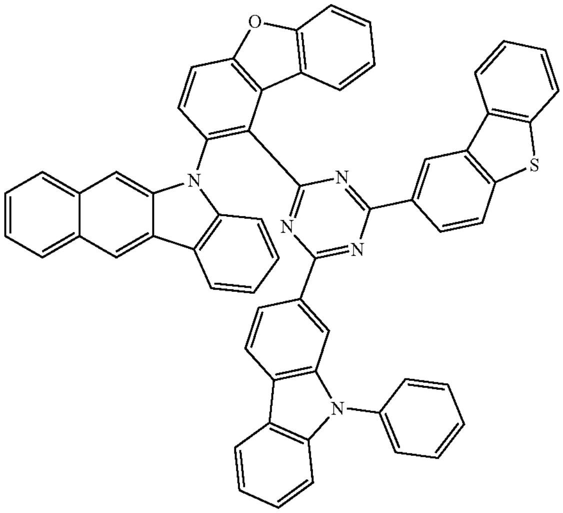
-continued
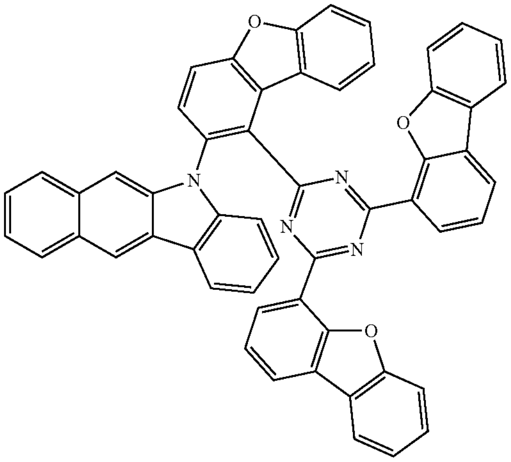
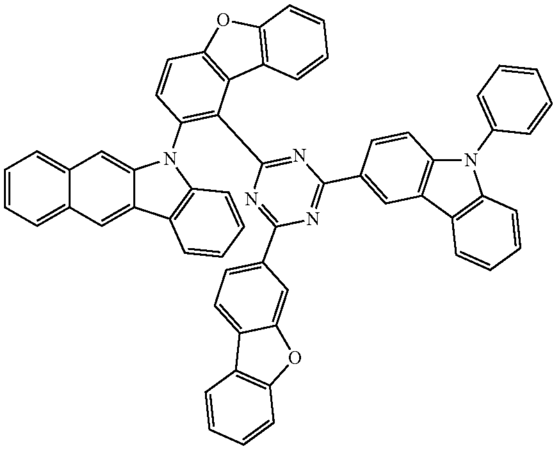
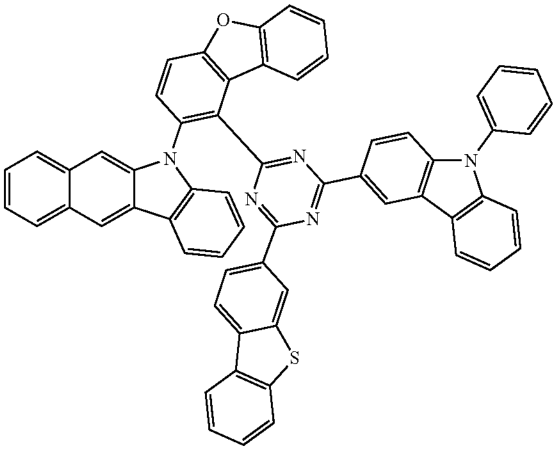

-continued
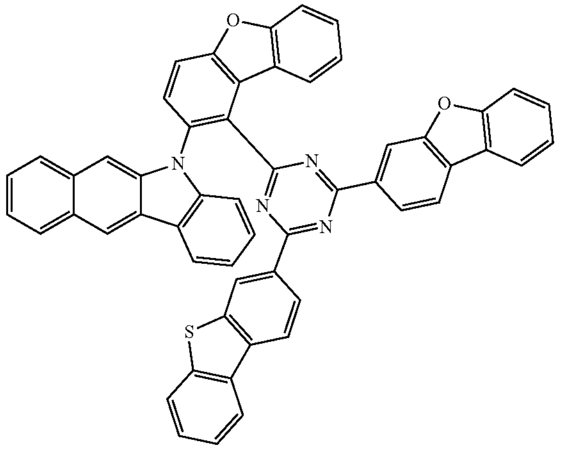
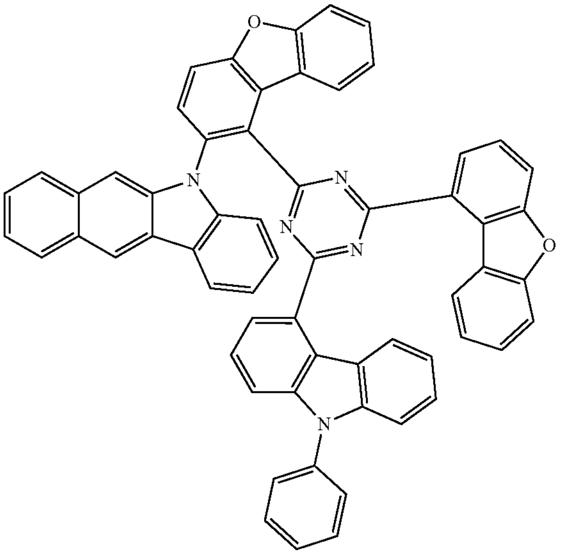
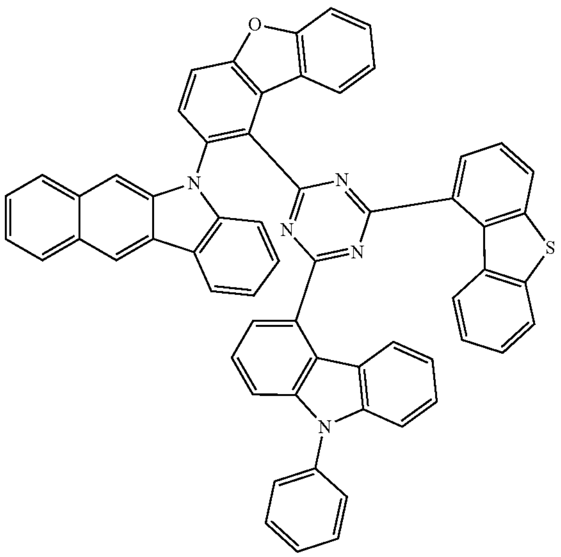
-continued
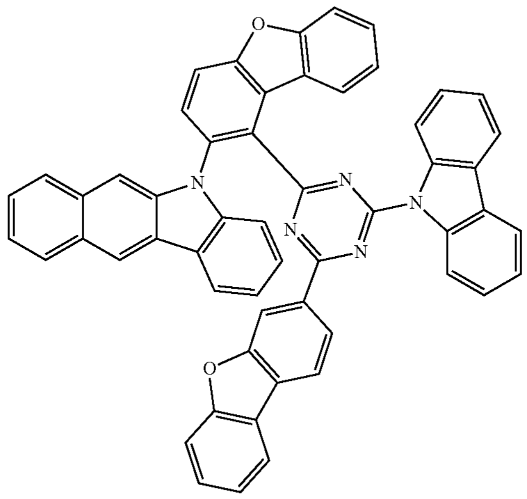
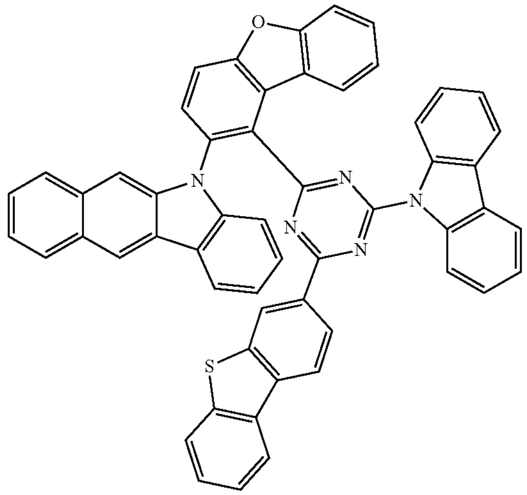
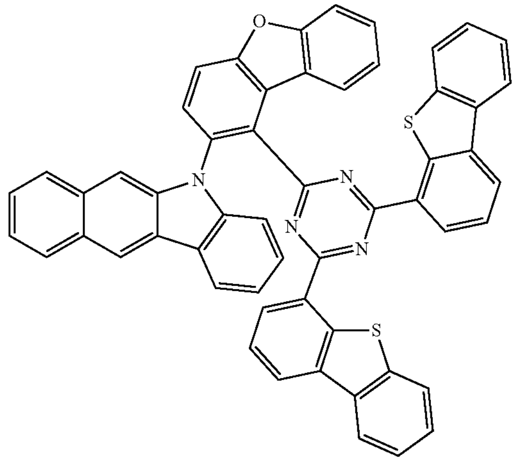

-continued
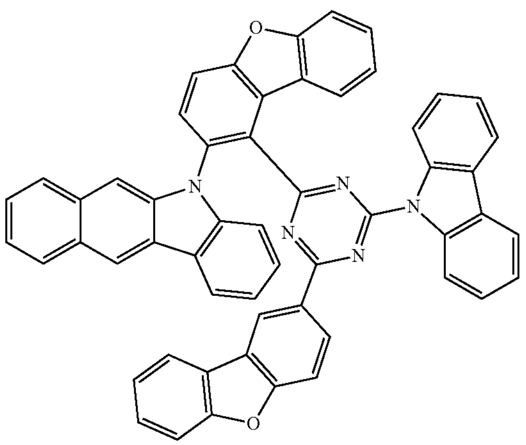
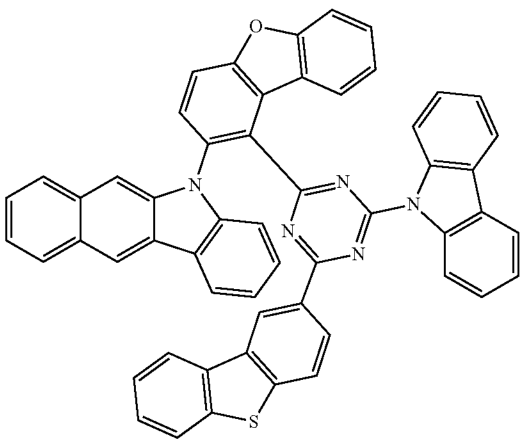
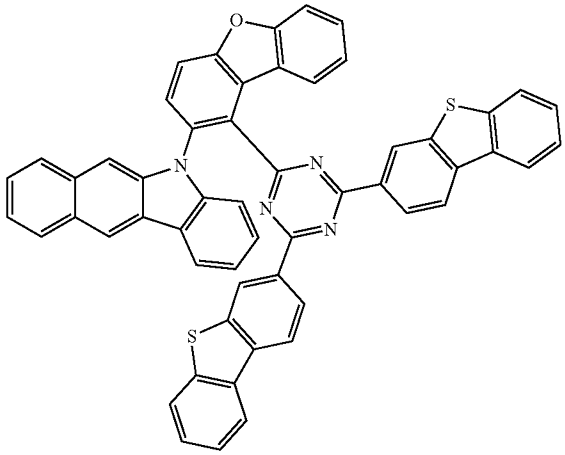
-continued
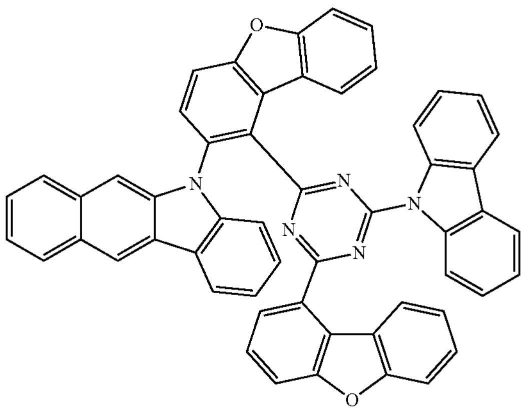
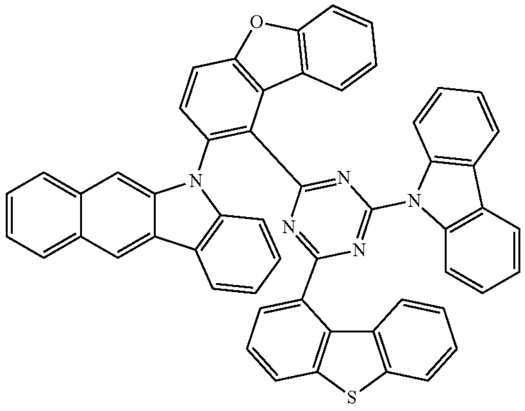
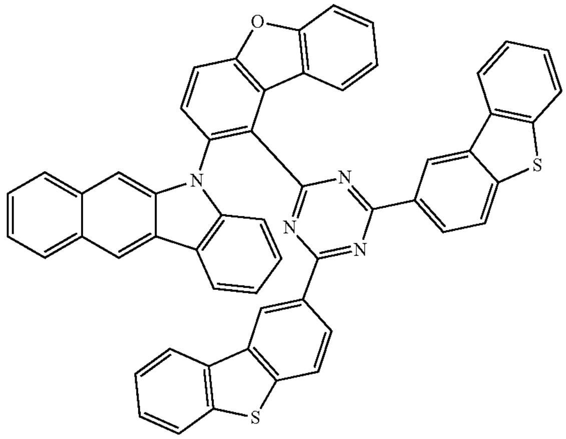
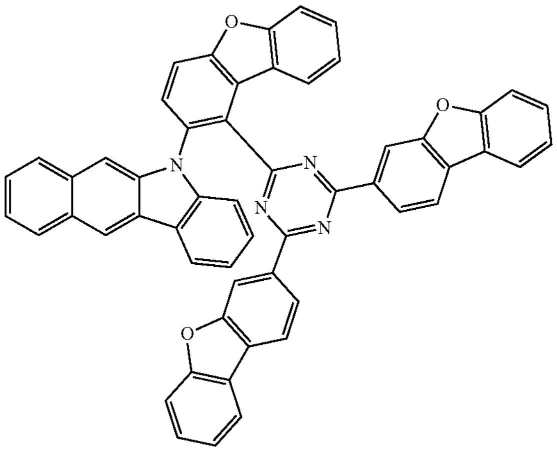

-continued
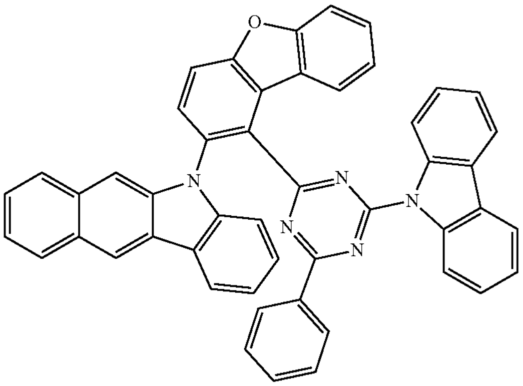
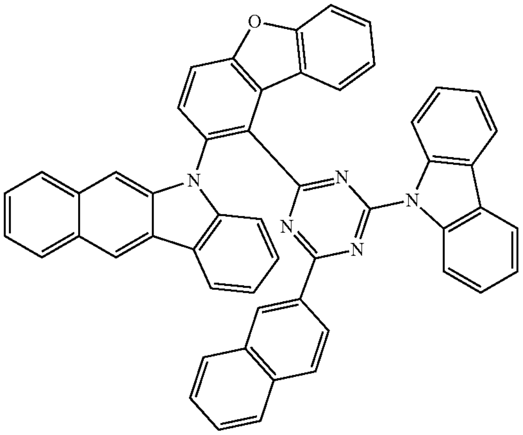
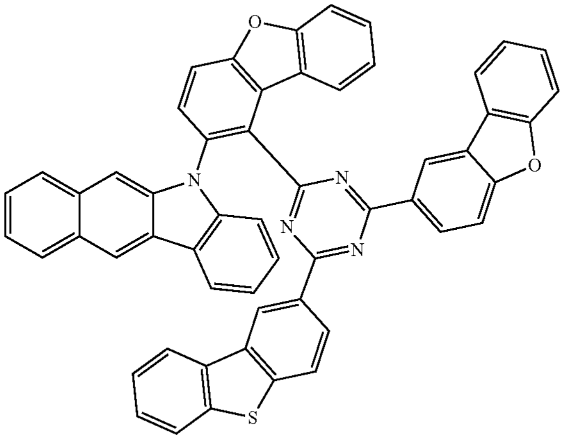
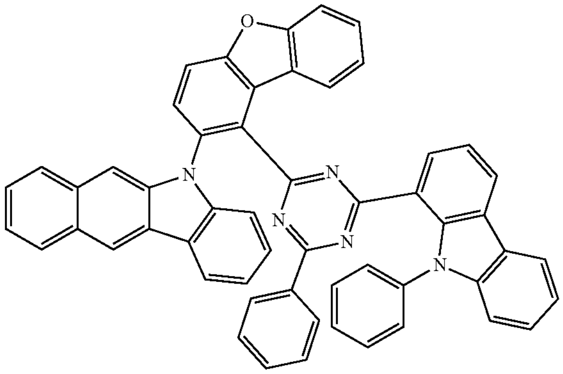
-continued
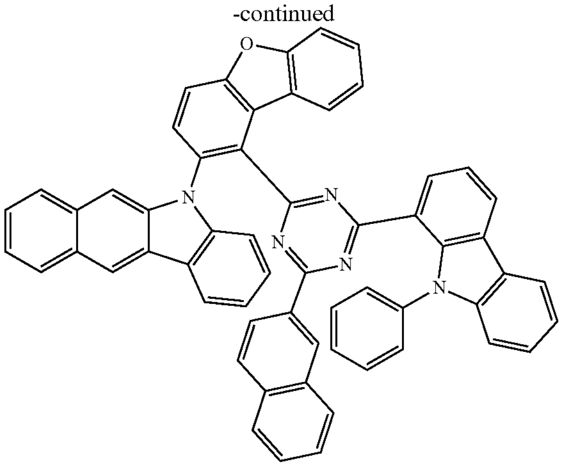
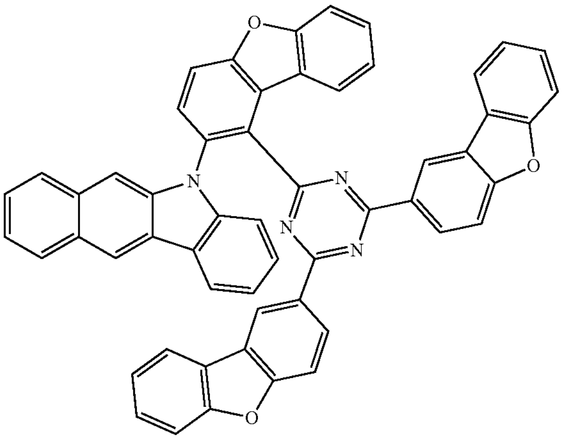
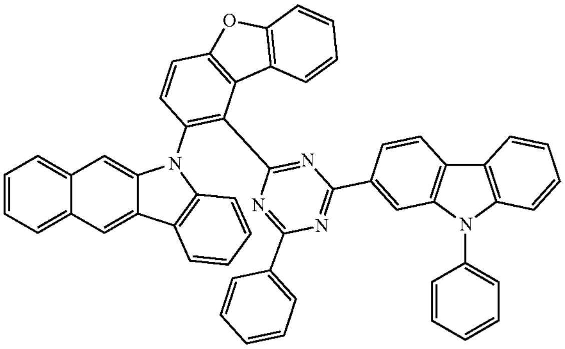
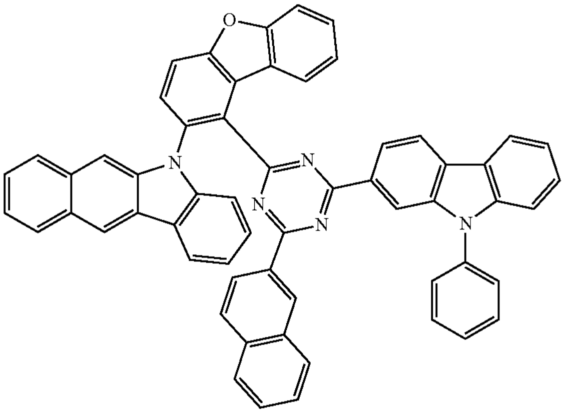

-continued
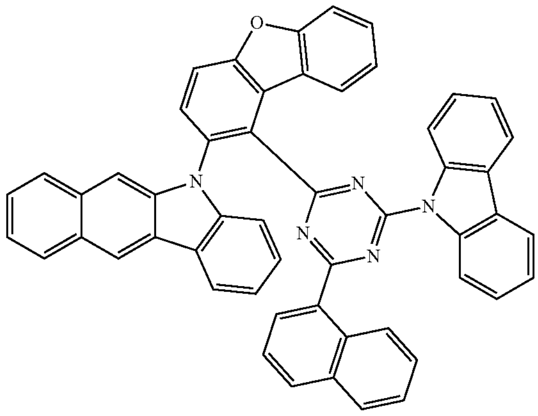
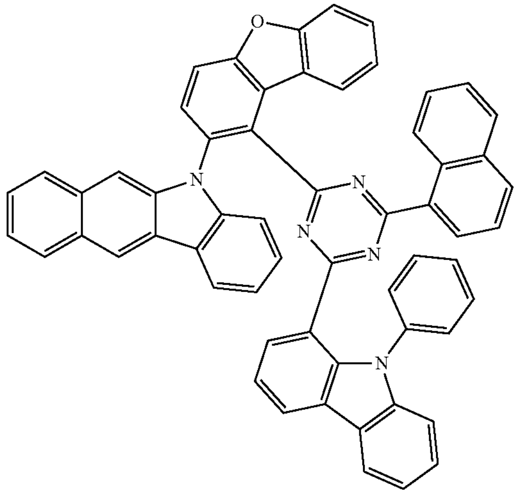
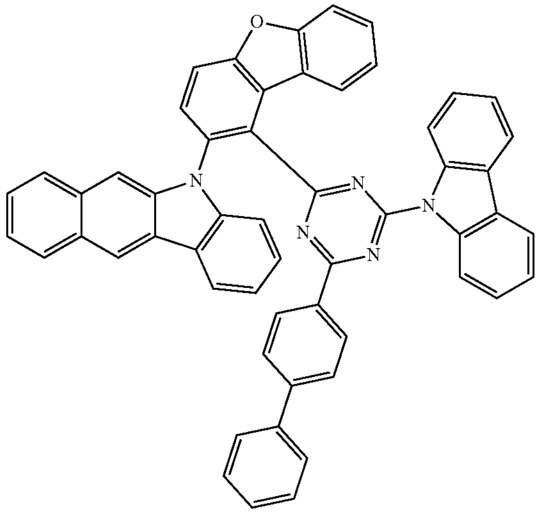
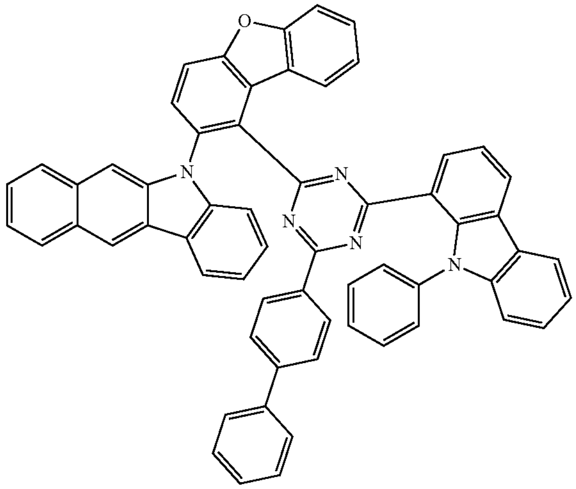
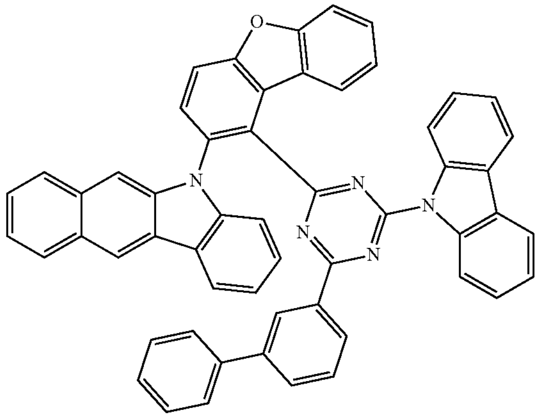
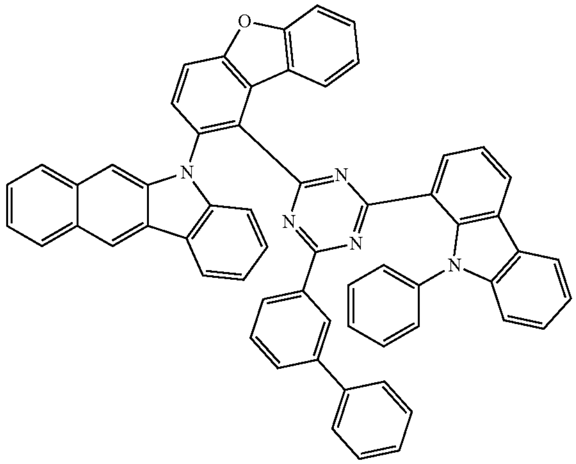

-continued
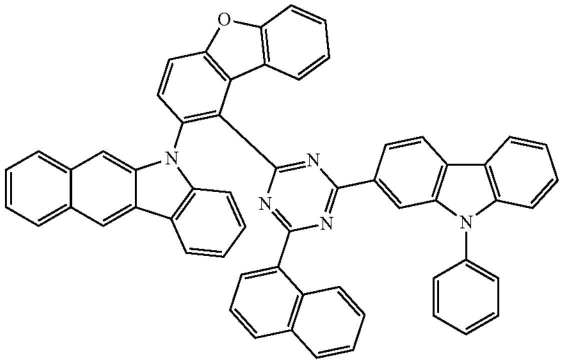
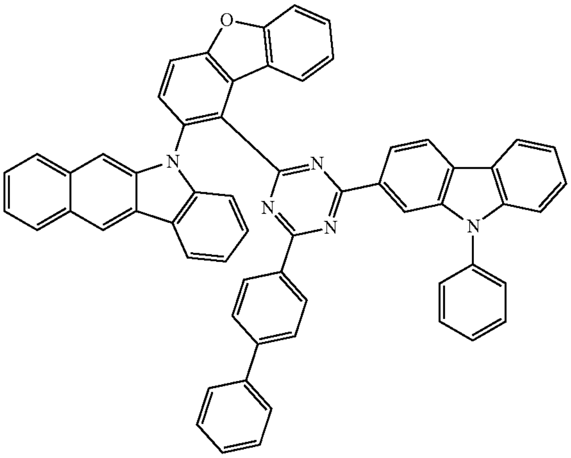
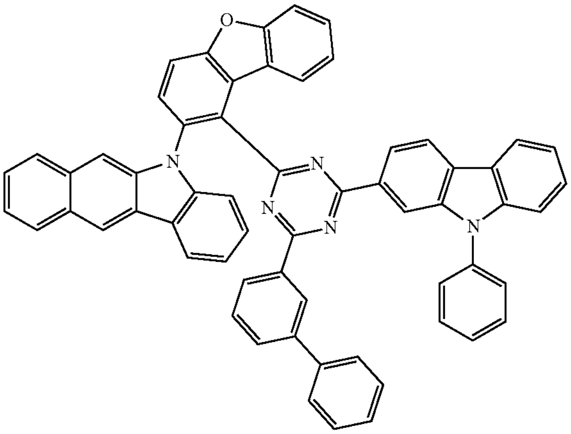
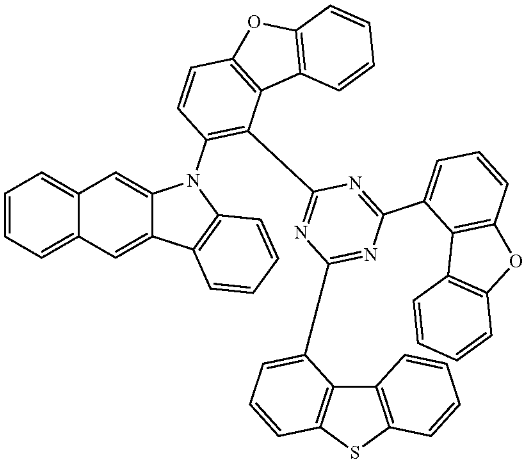
-continued
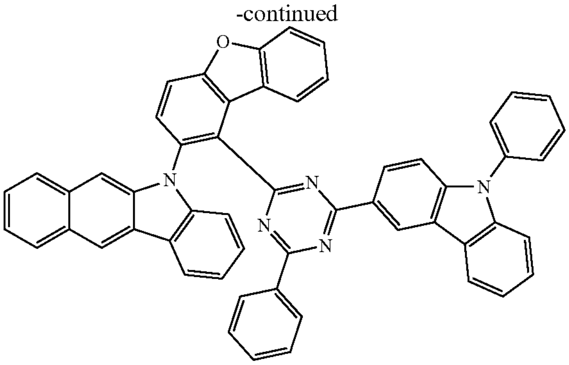
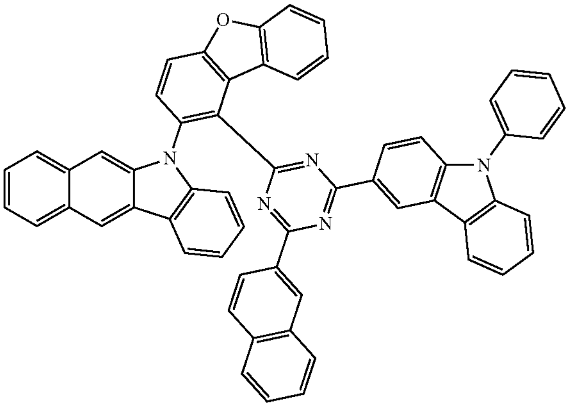
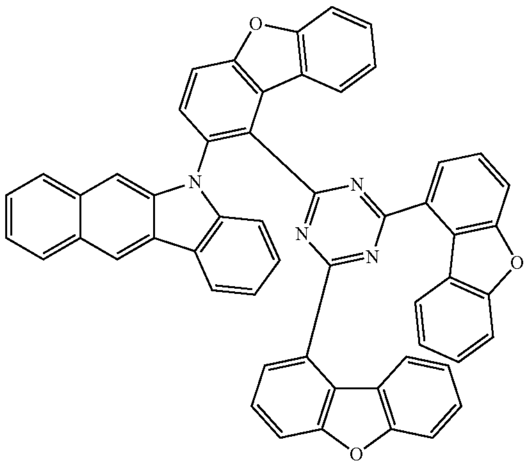
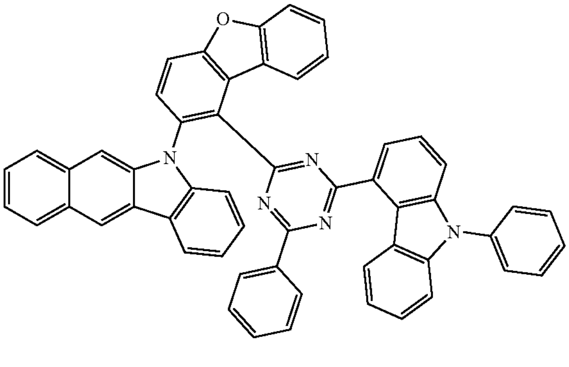

-continued
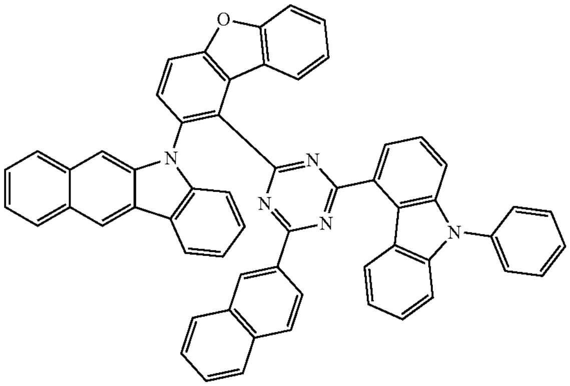
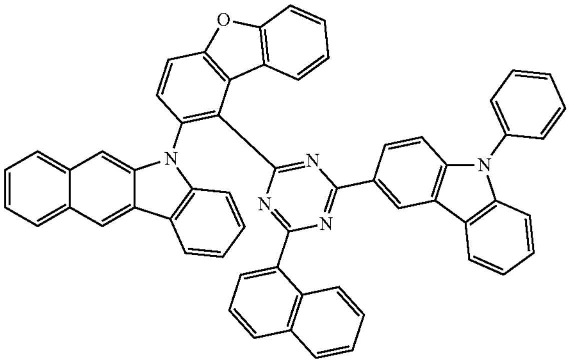
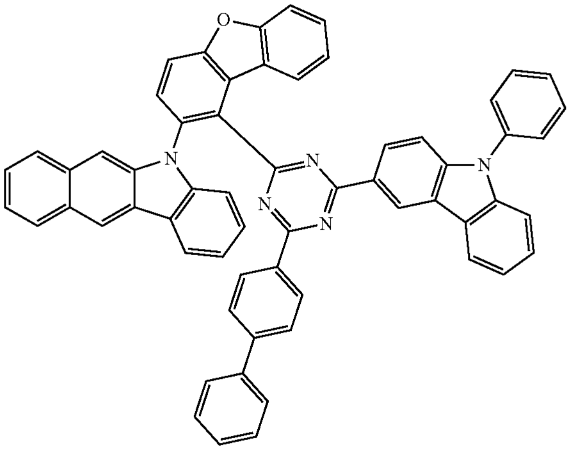
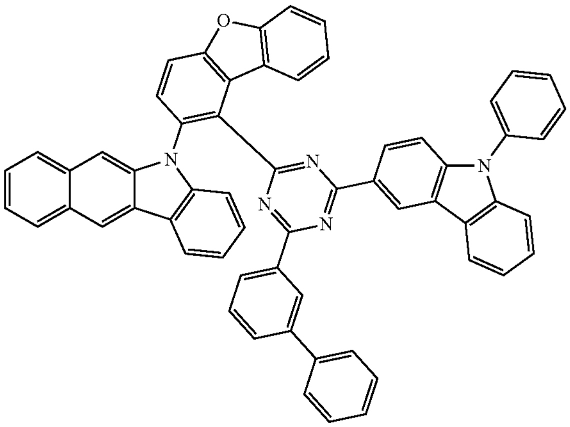
-continued
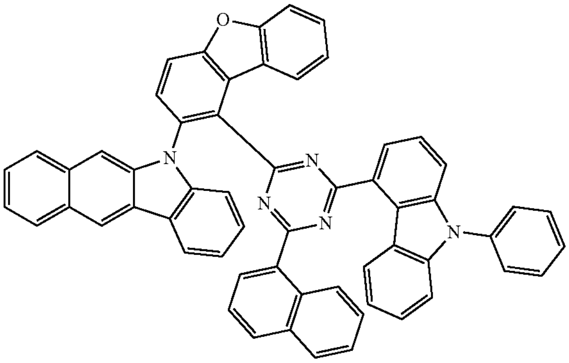
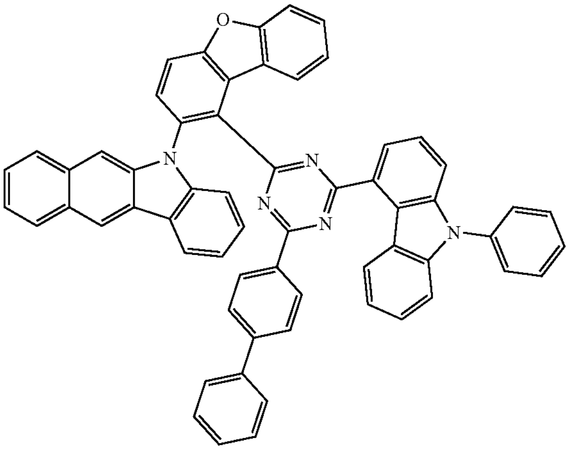
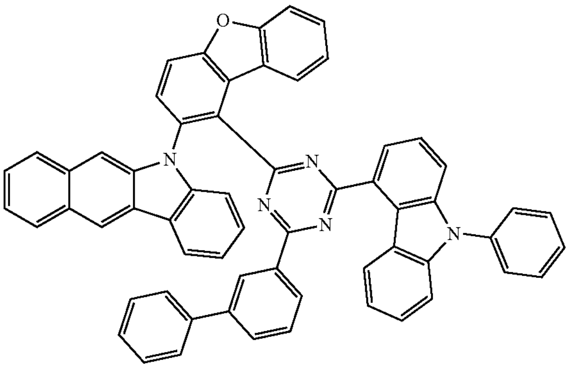

-continued
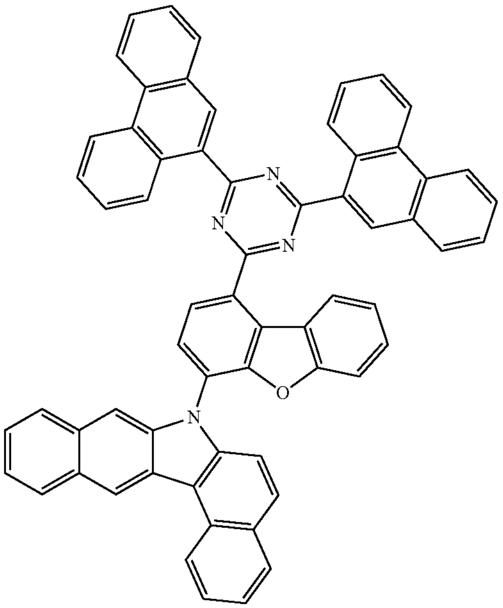
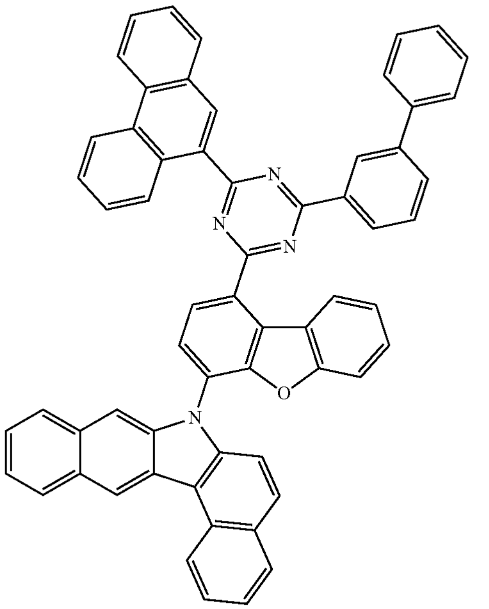
-continued
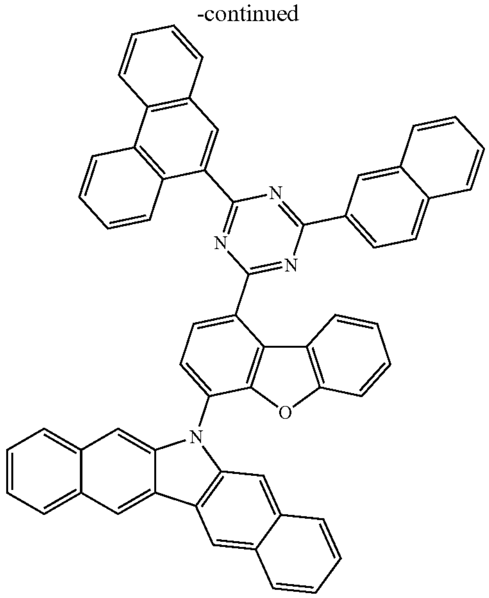
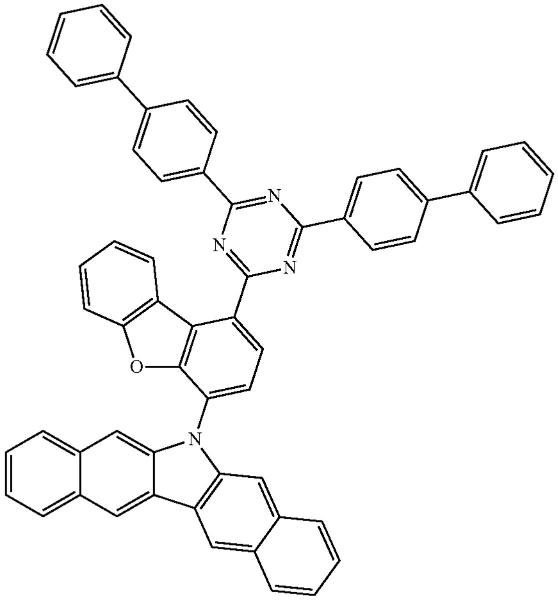
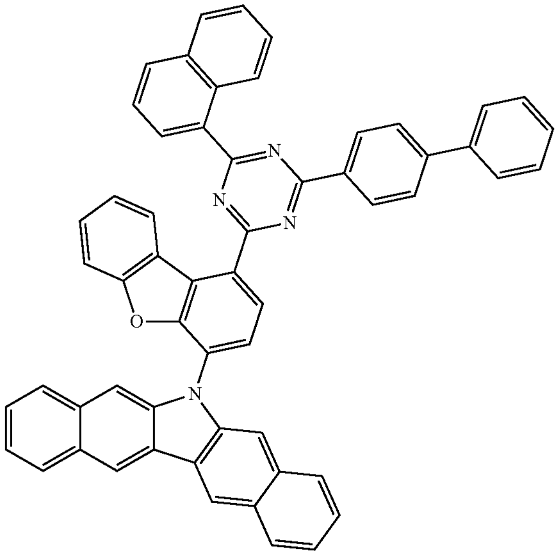

-continued
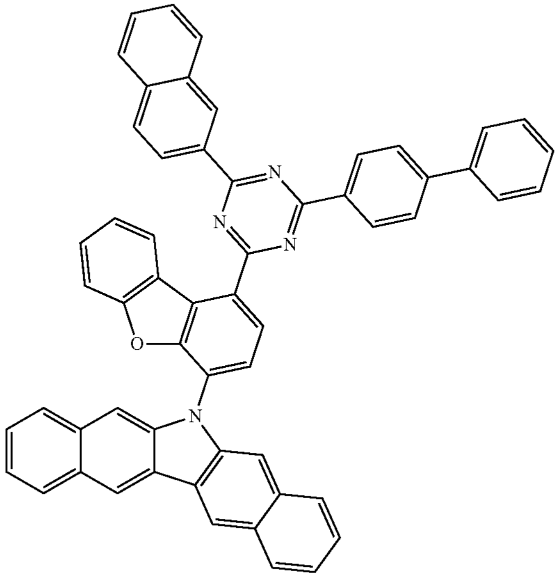
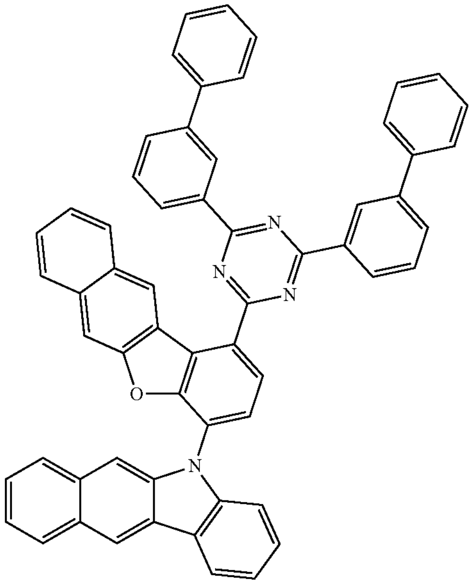
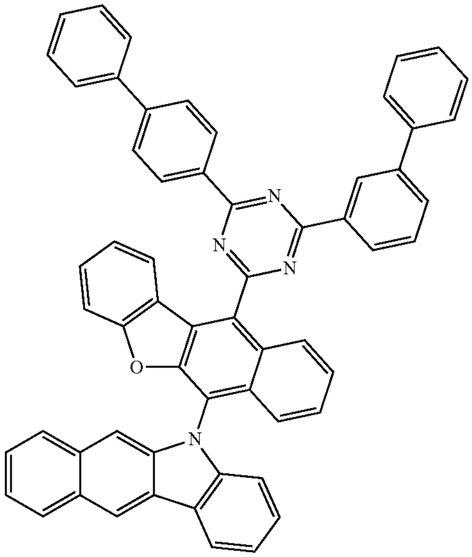
-continued
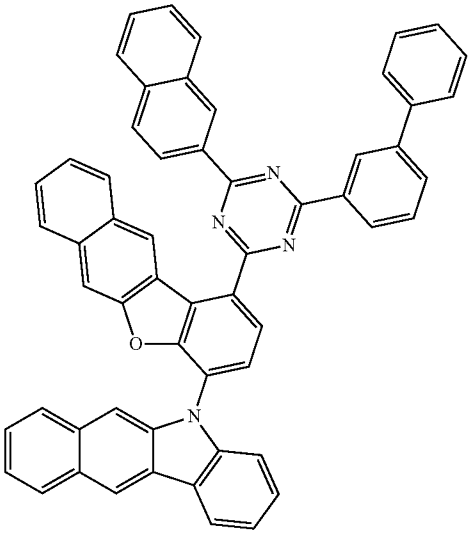
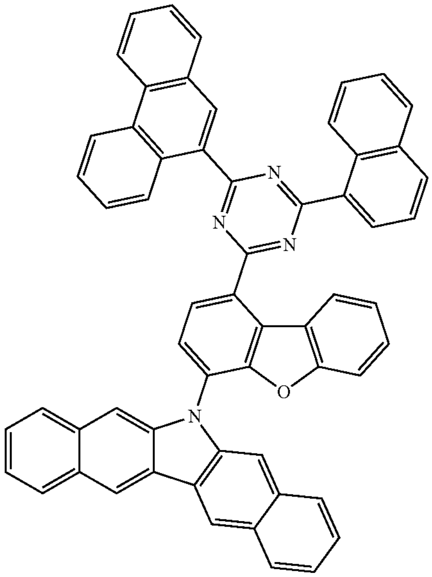

-continued
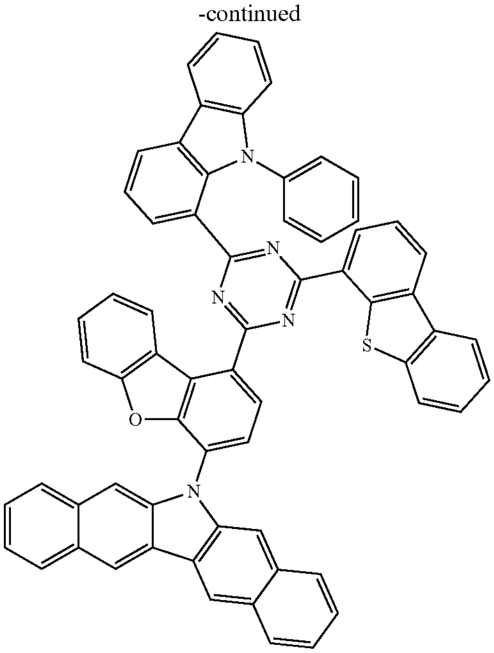
-continued
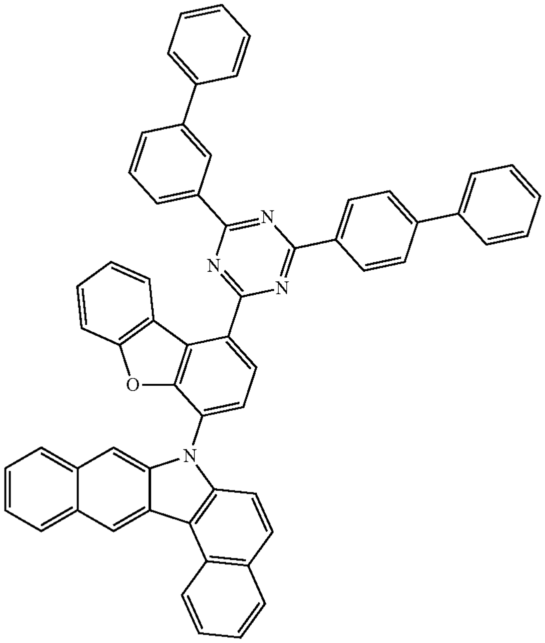
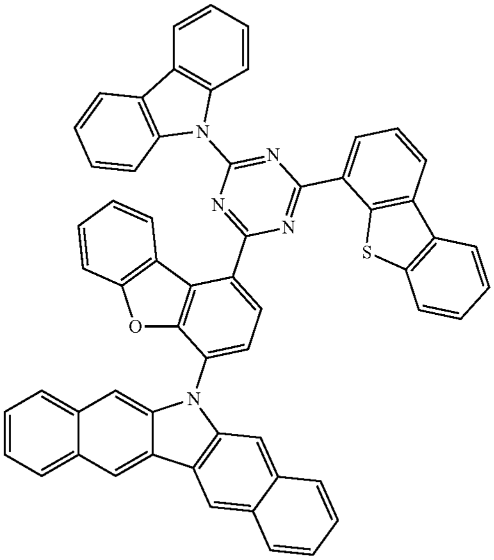
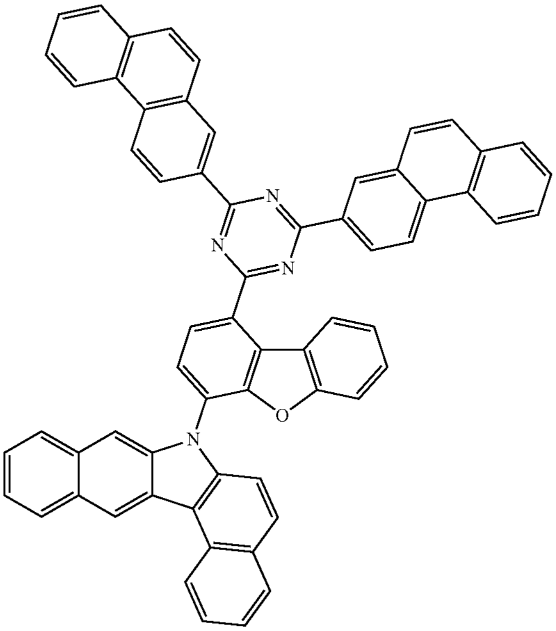

-continued
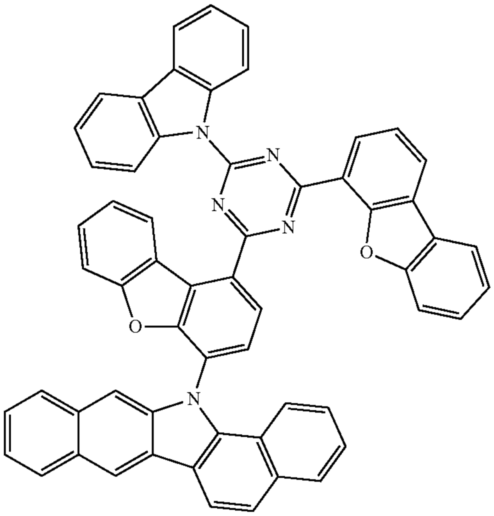
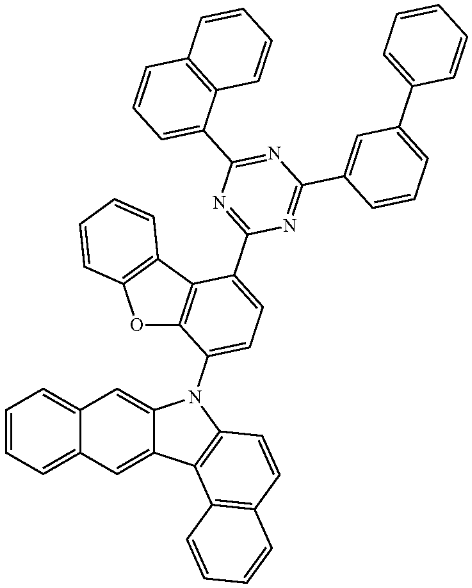
-continued
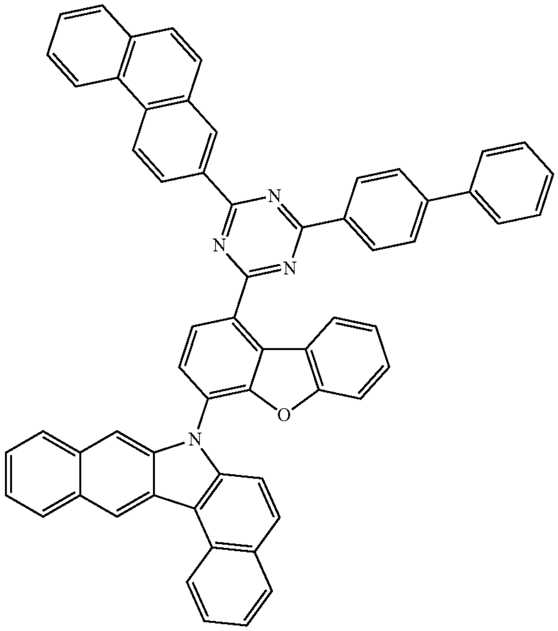
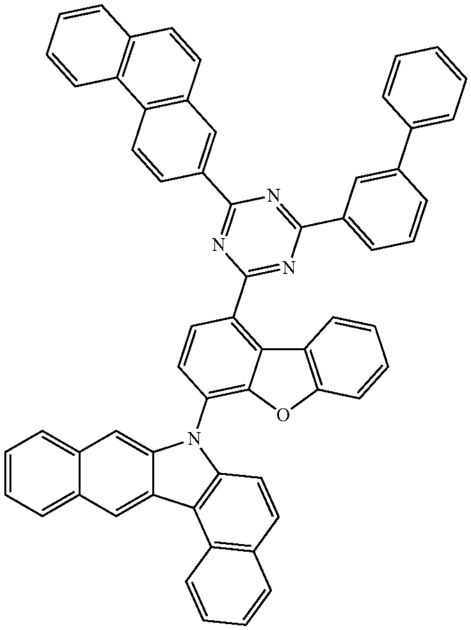
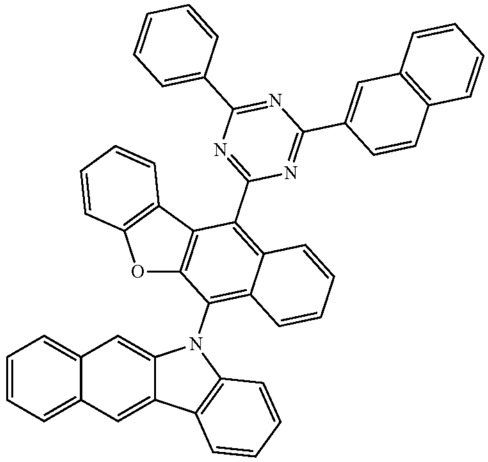

-continued
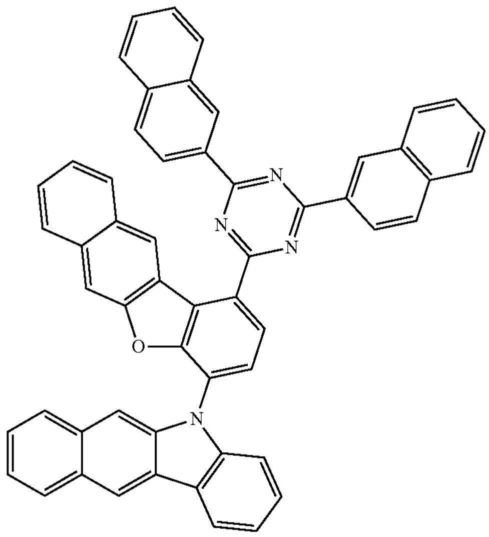
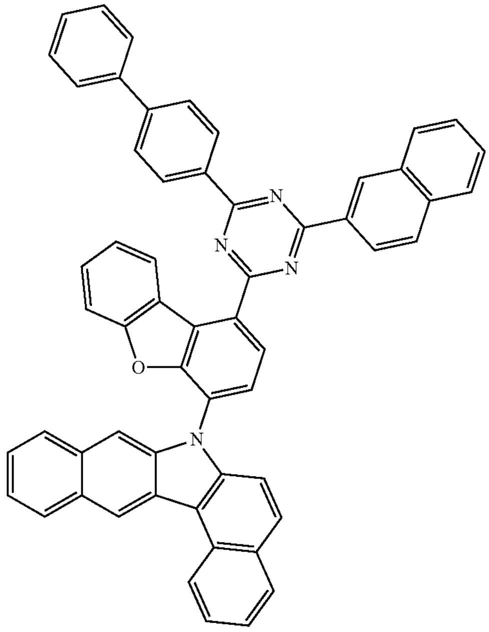
-continued
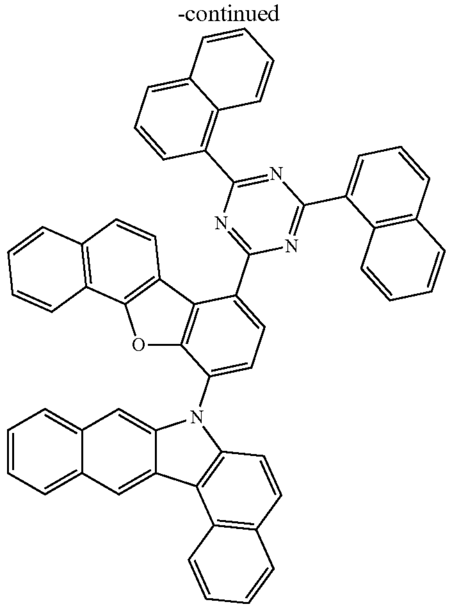
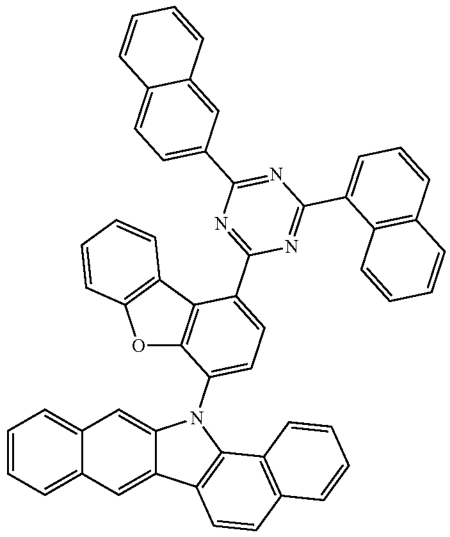
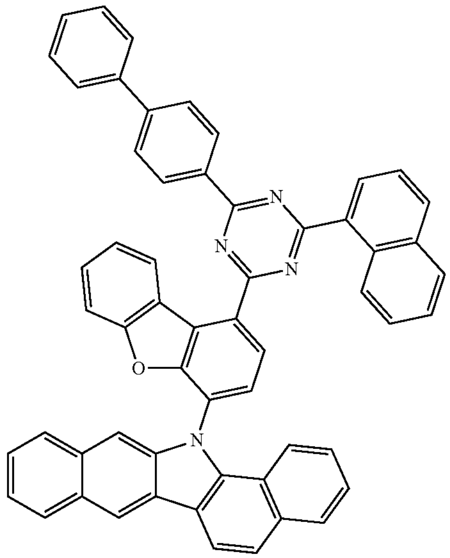

-continued
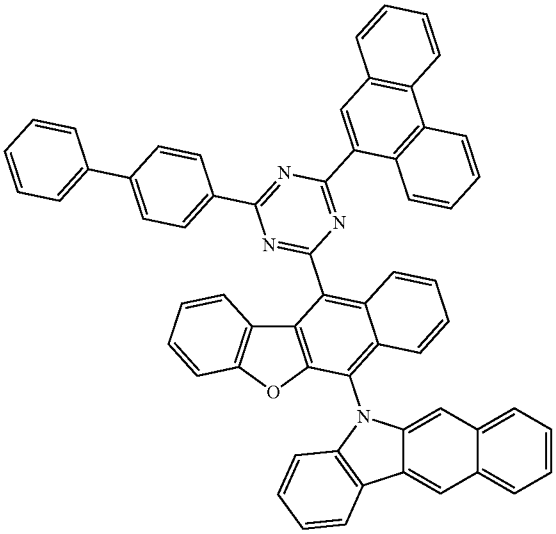
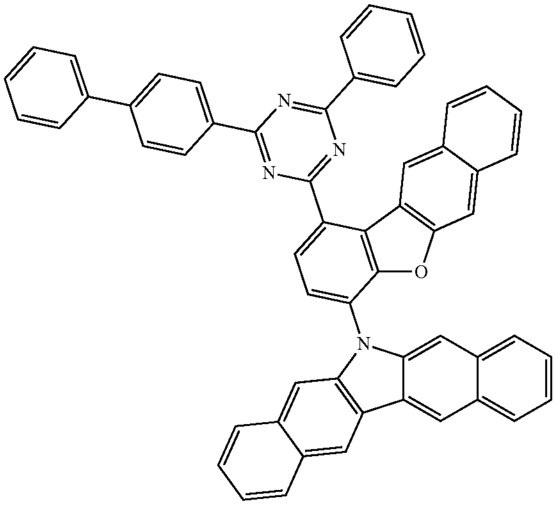
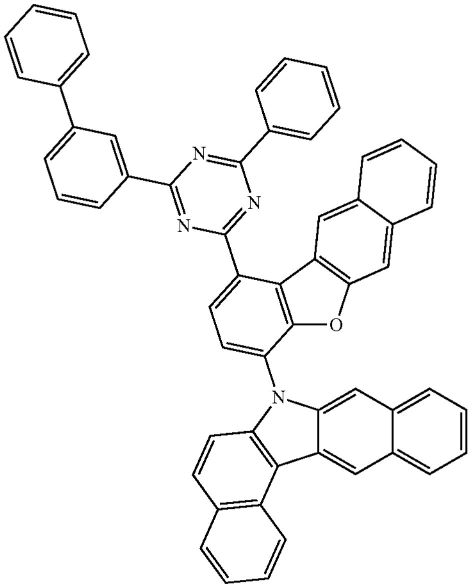
-continued
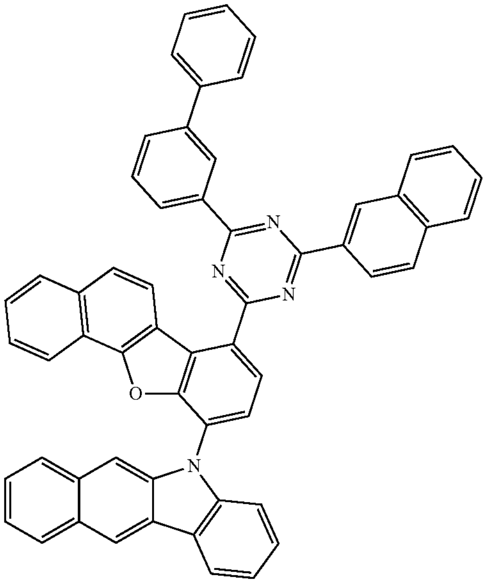
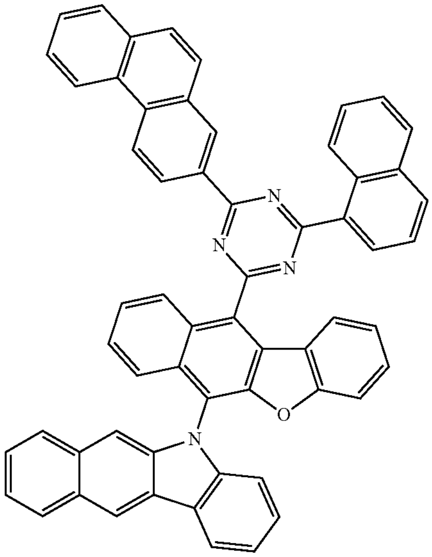
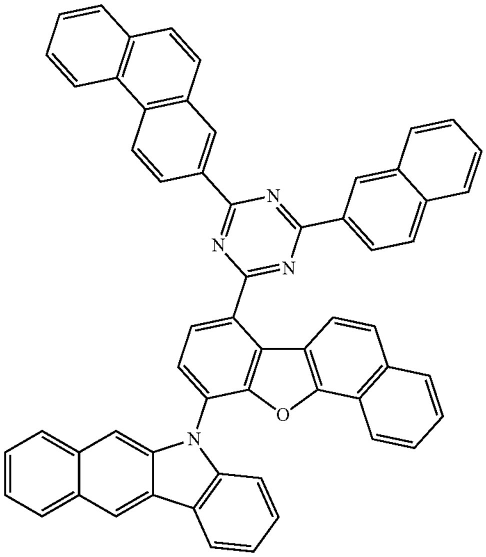

-continued
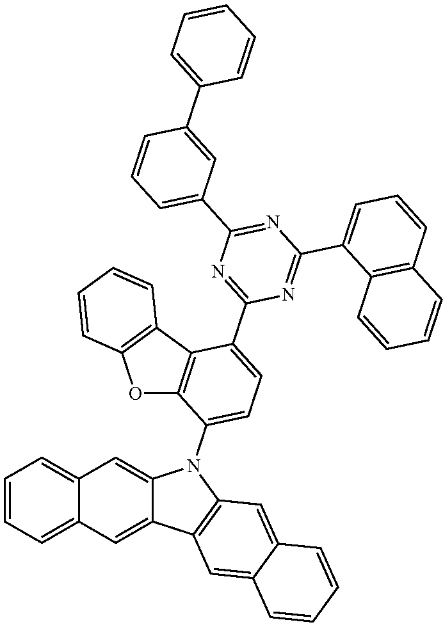
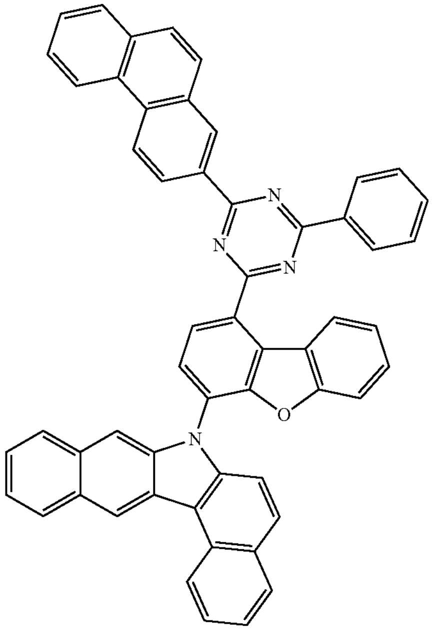
-continued
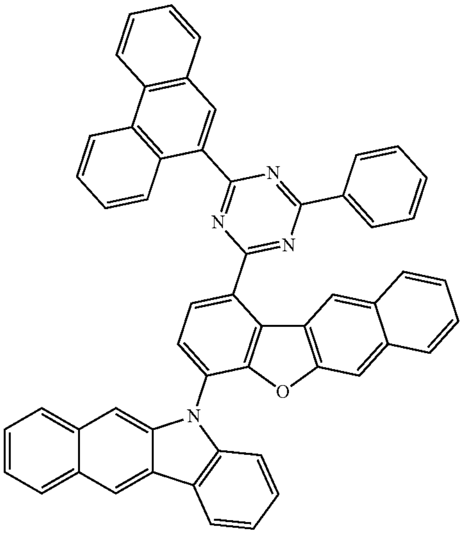
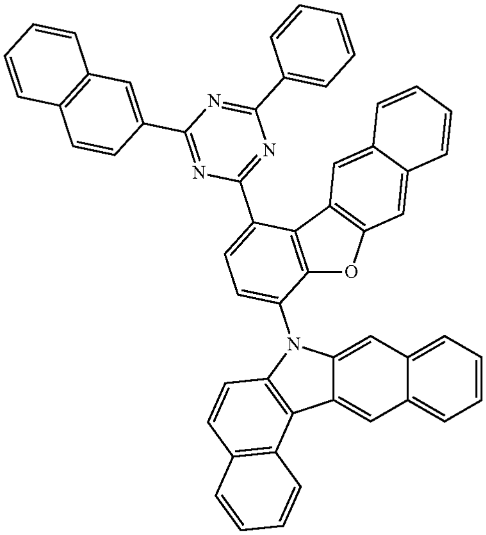
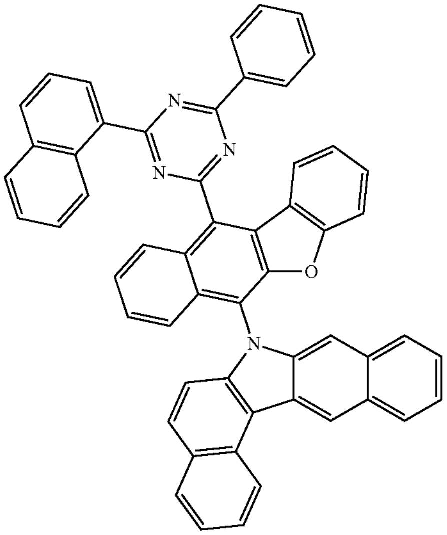

-continued
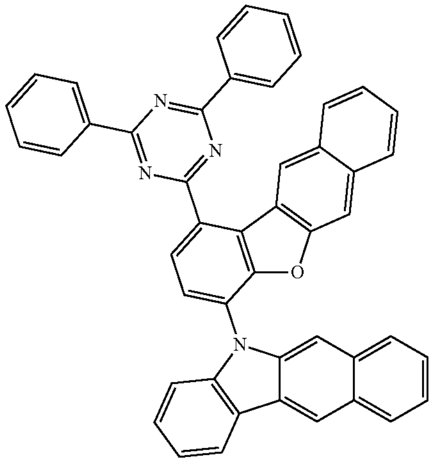
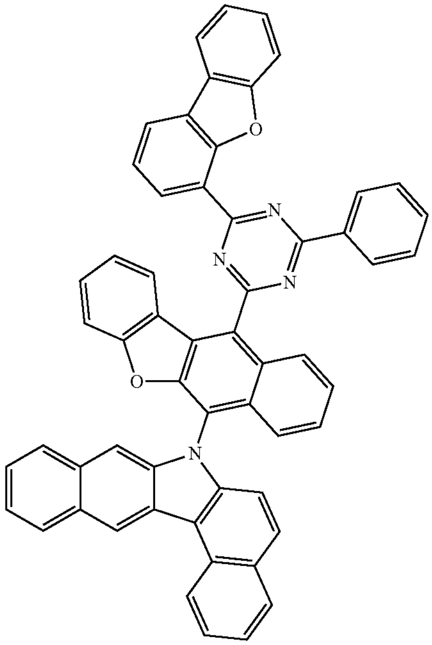
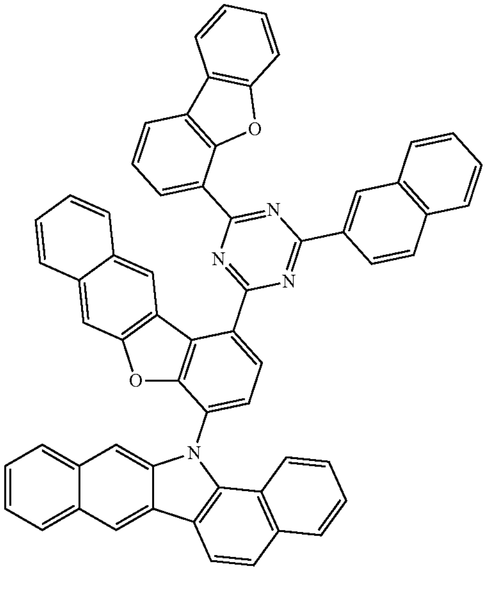
-continued
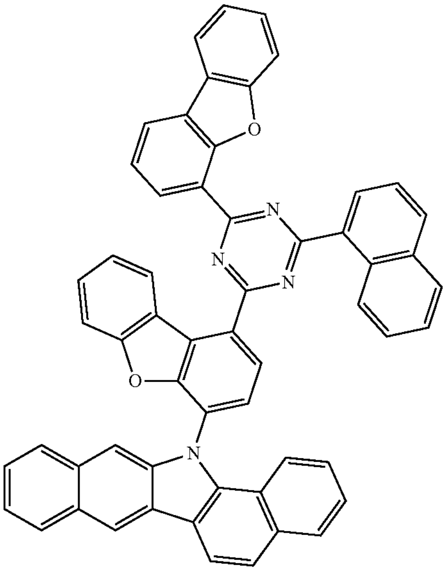
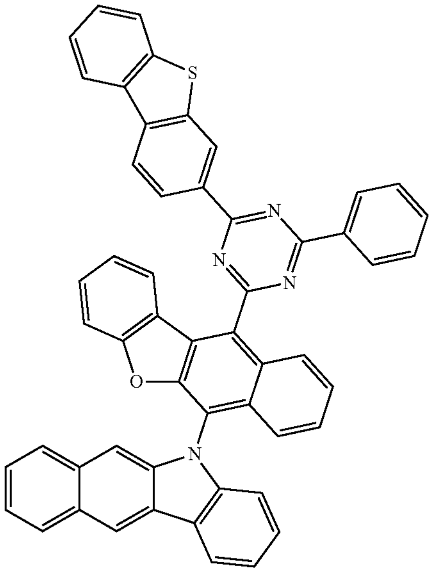

-continued
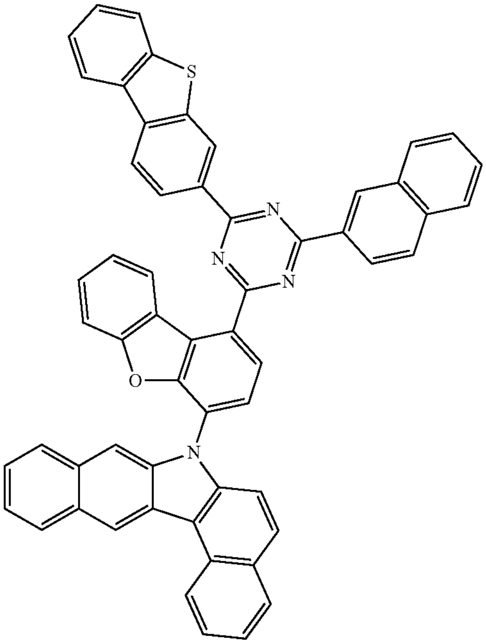
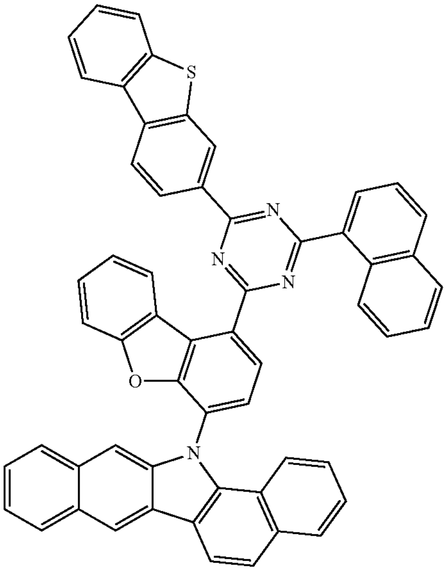
-continued
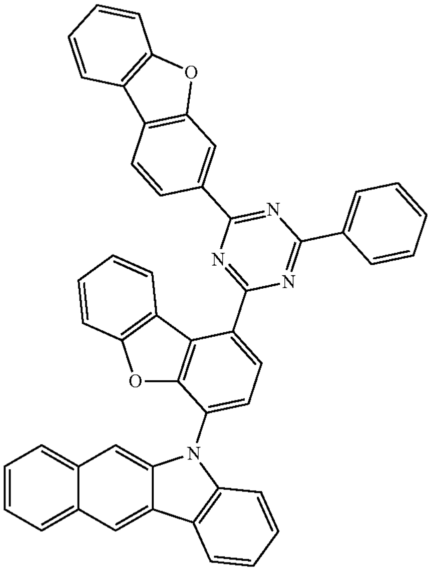
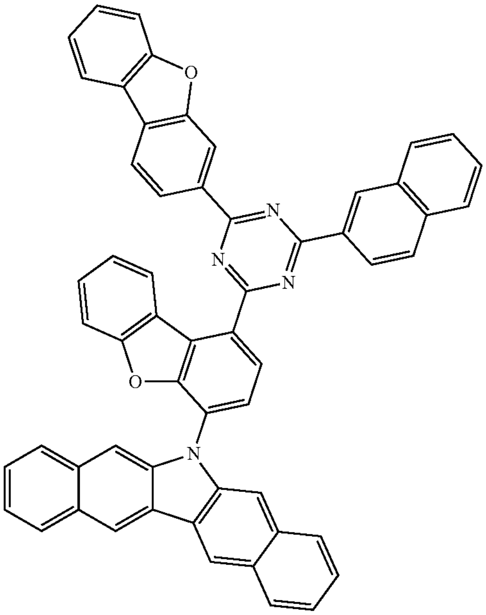

-continued
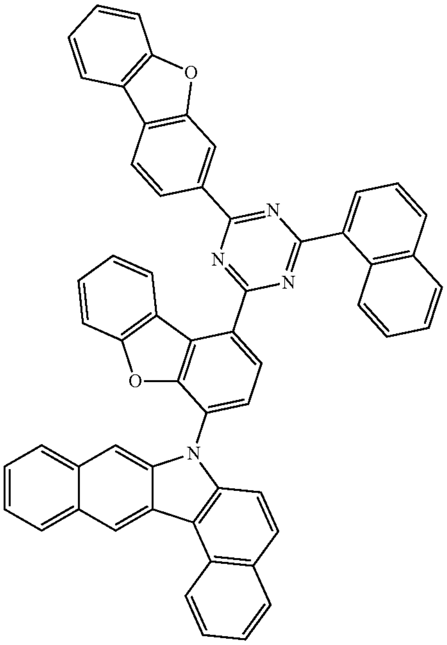
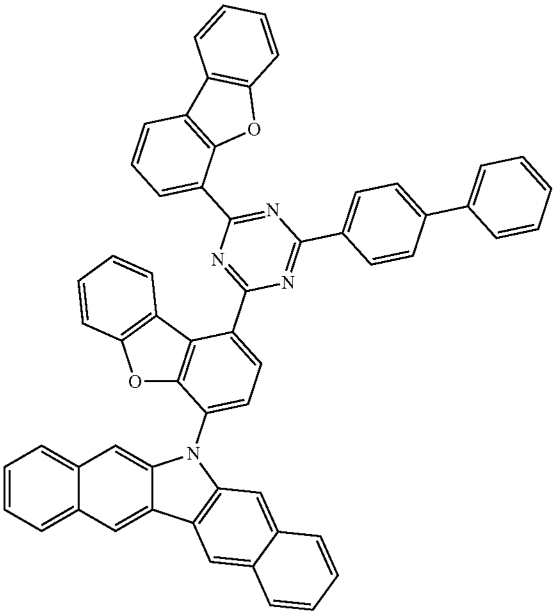
-continued
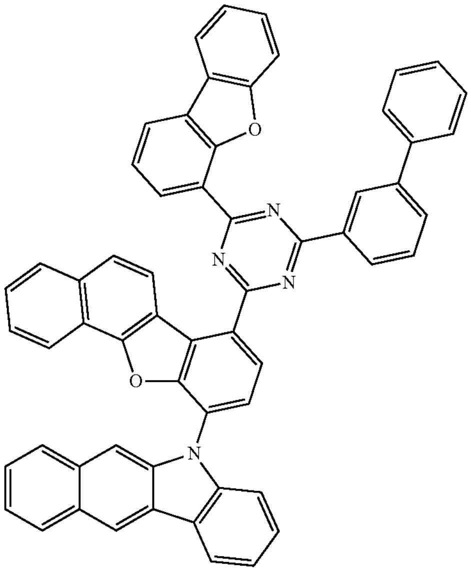
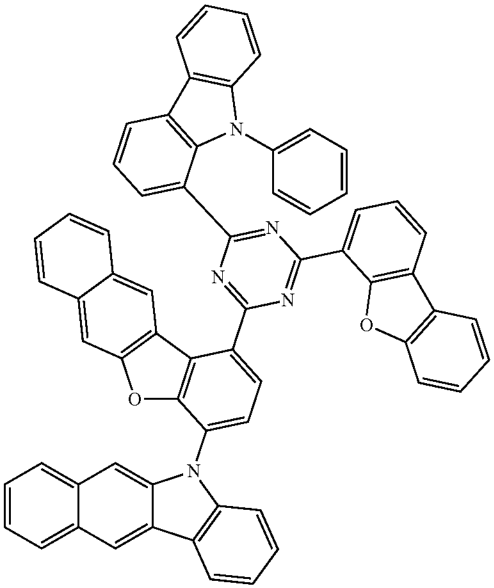

-continued
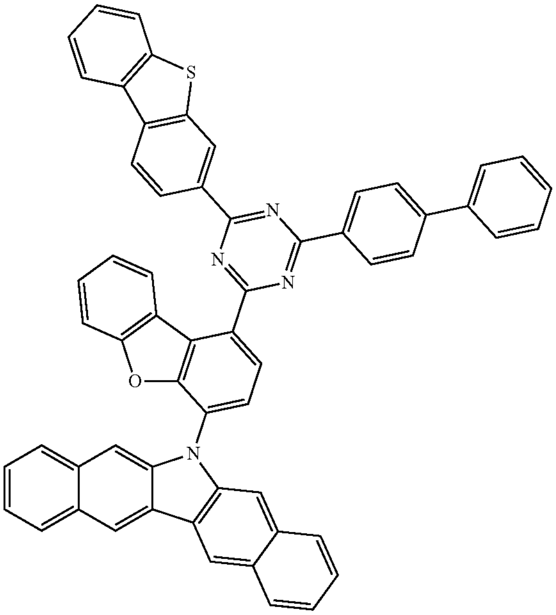
-continued
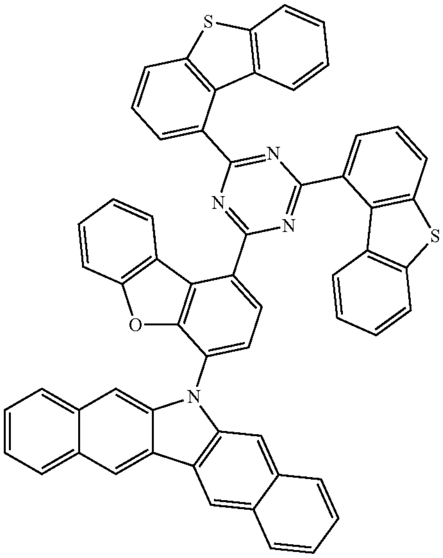
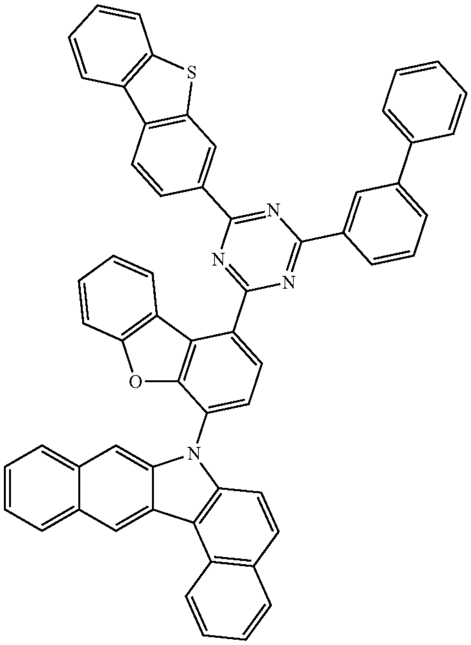
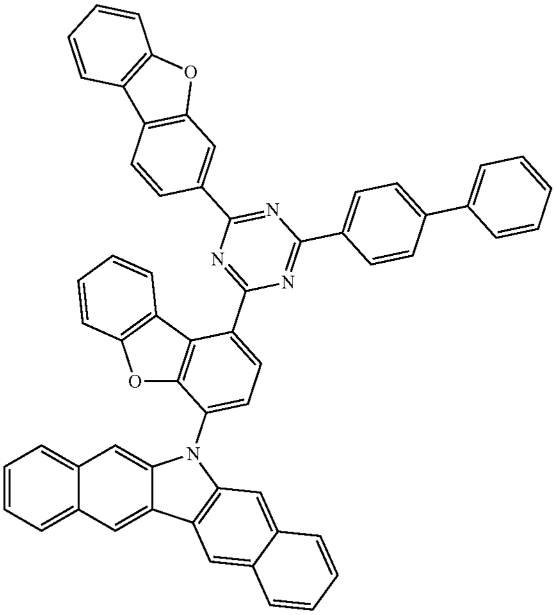

-continued
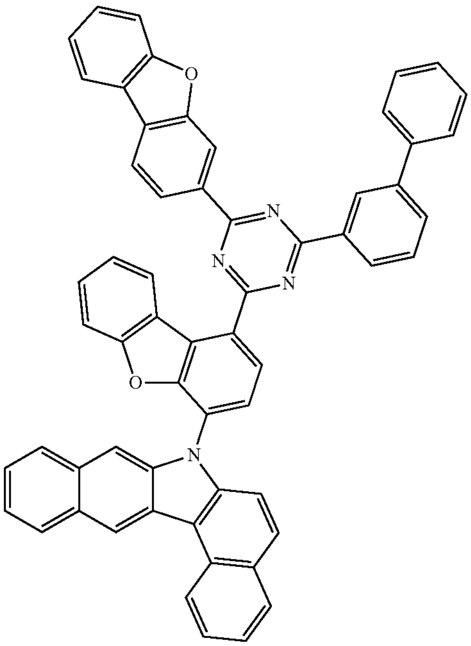
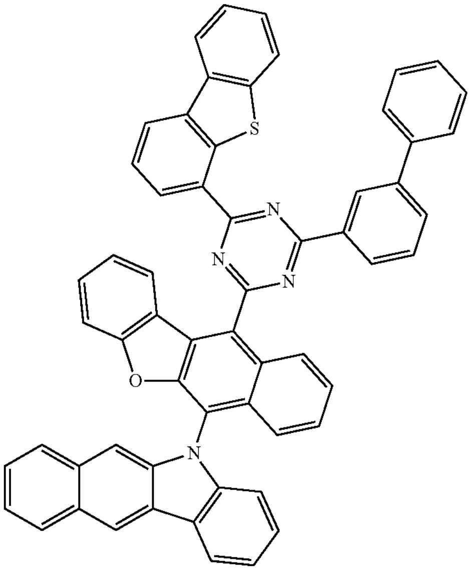
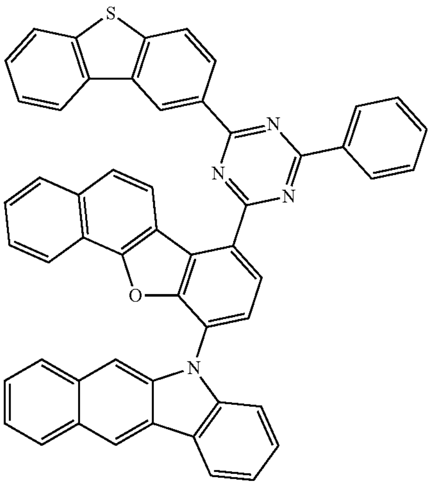
-continued
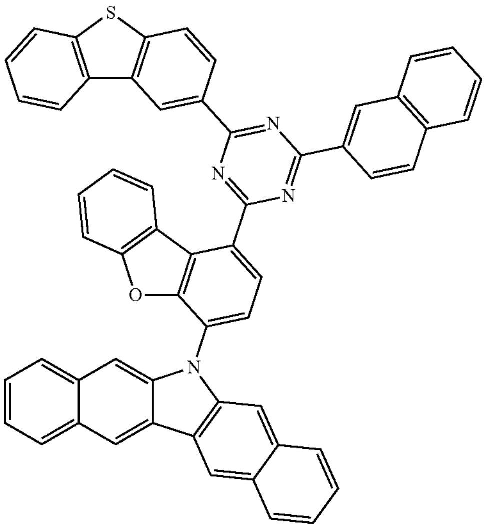
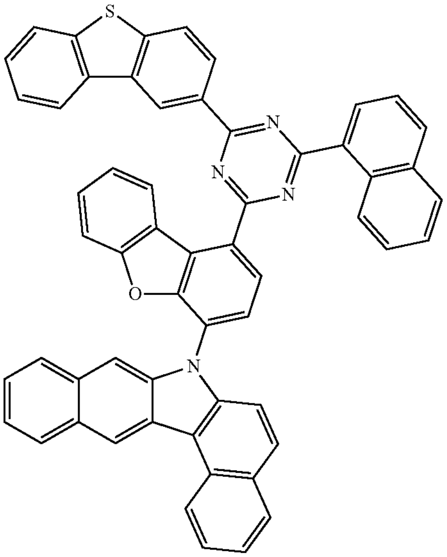
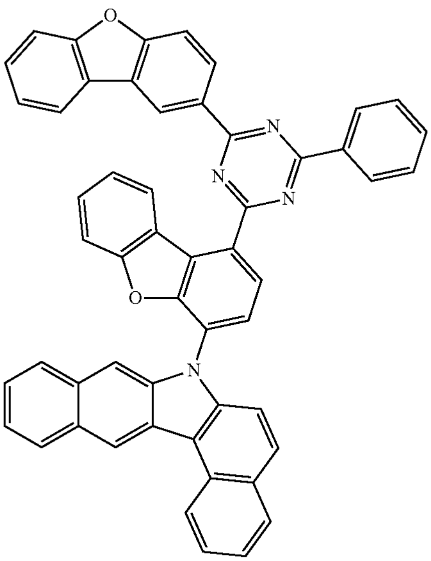

-continued
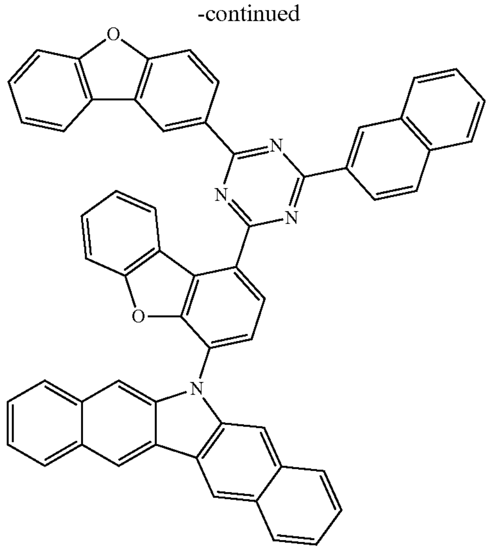
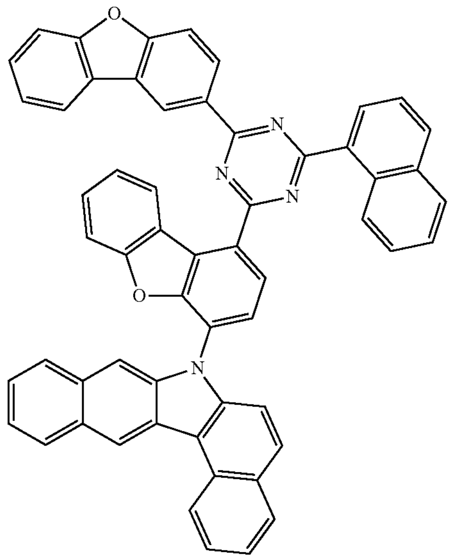
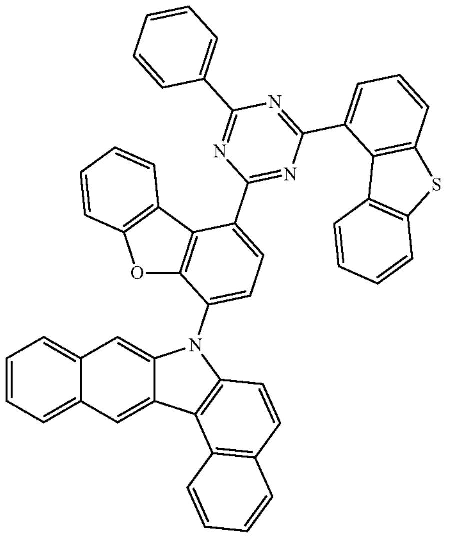
-continued
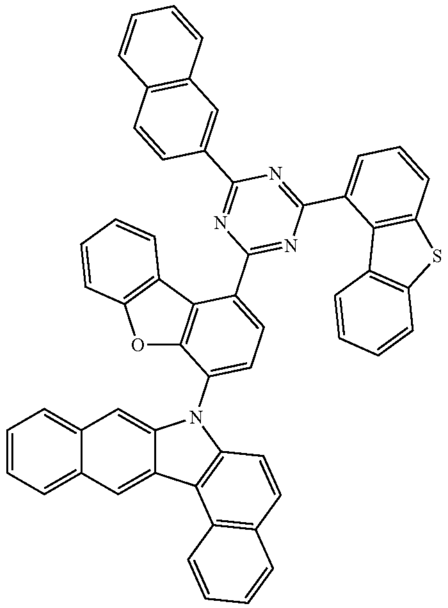
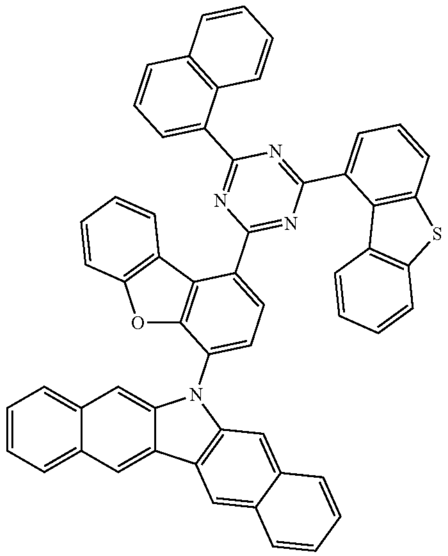
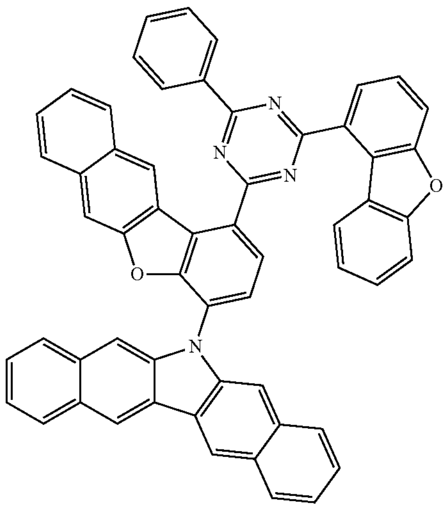

-continued
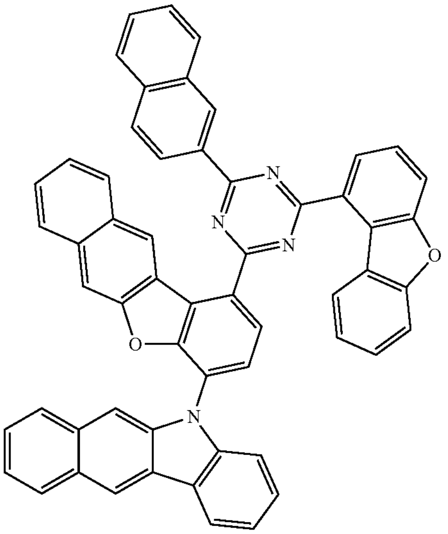
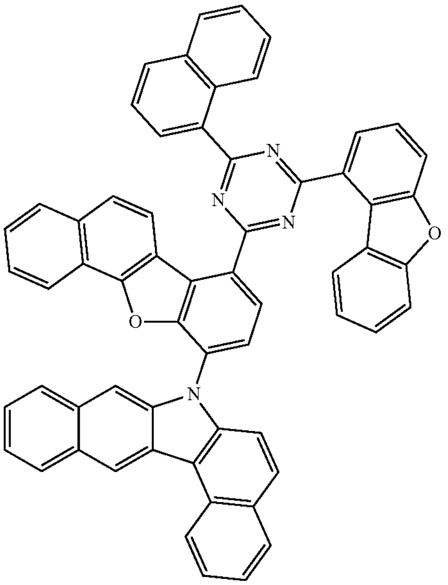
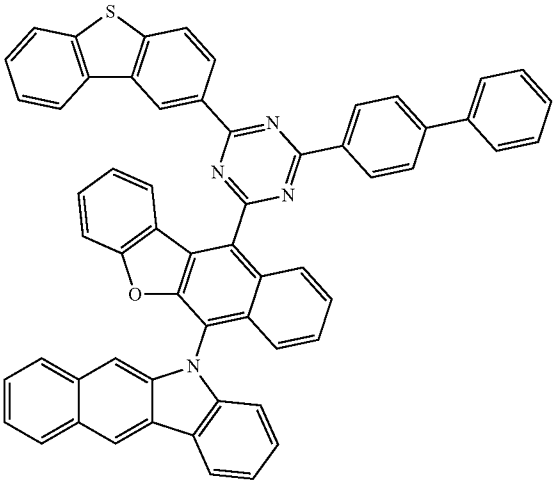
-continued
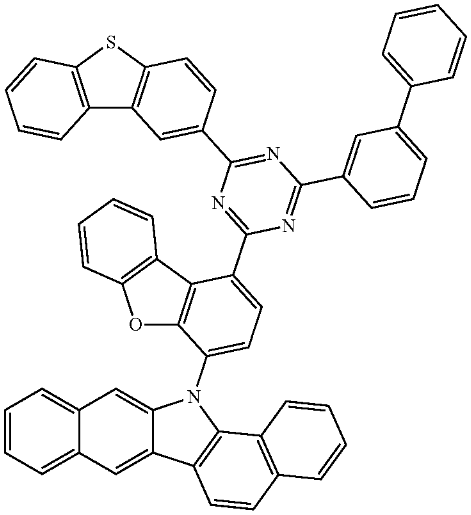
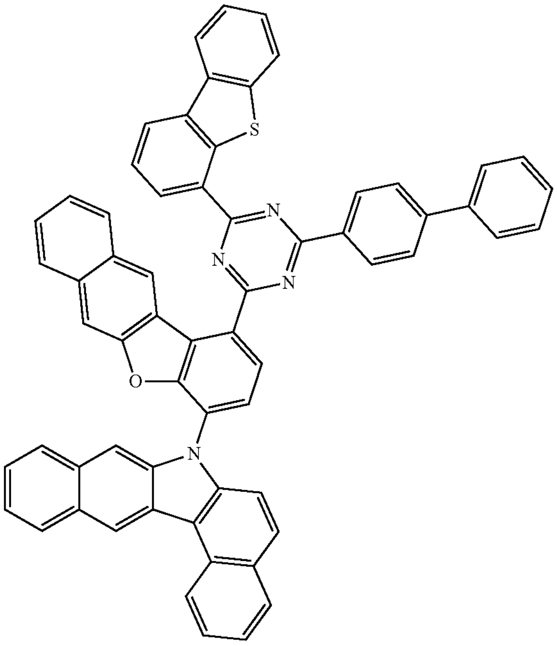
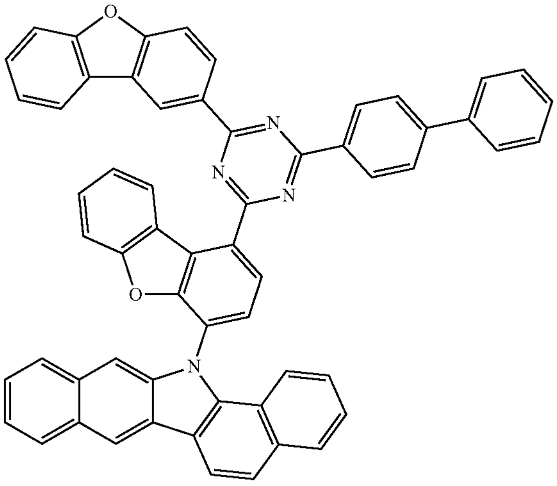

-continued
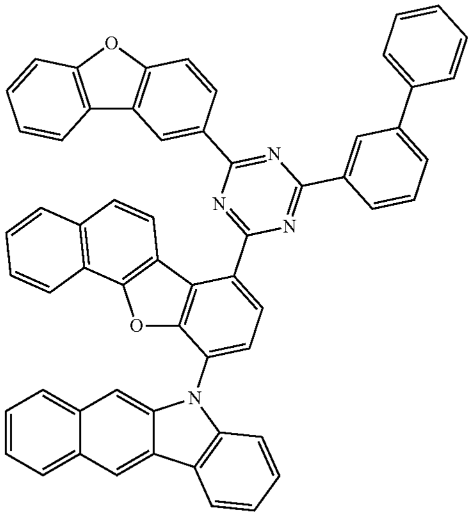
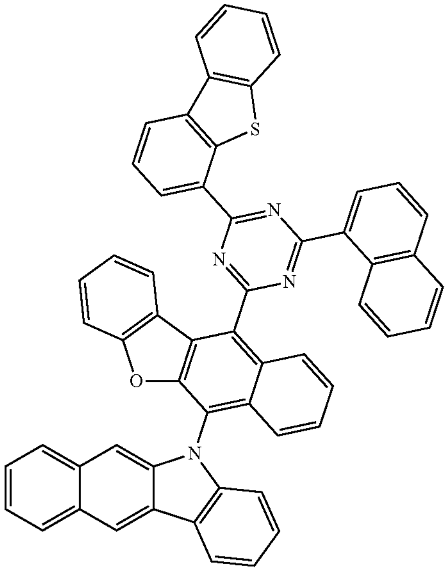
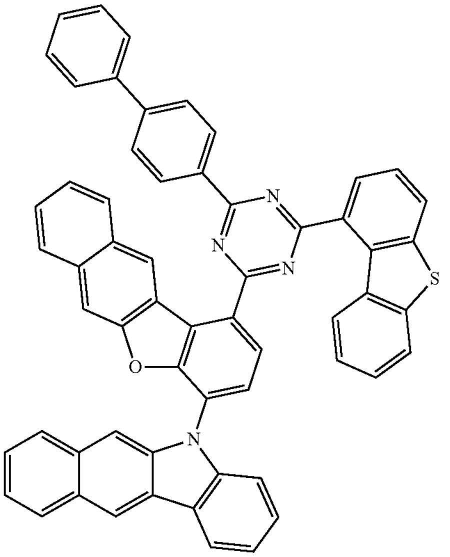
-continued
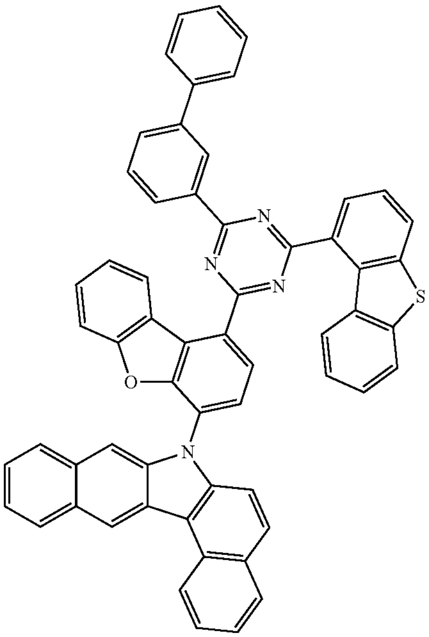
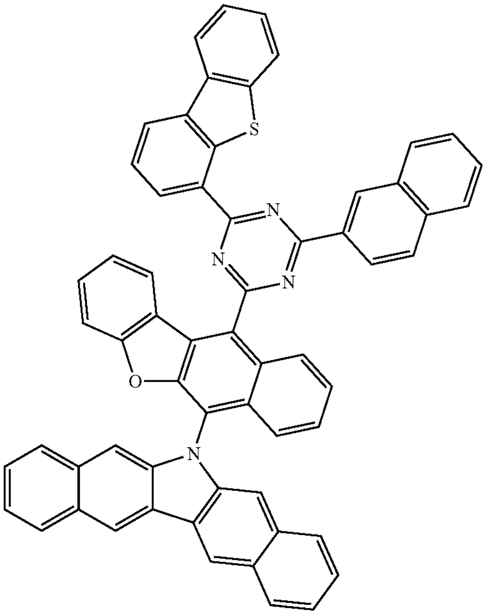

-continued
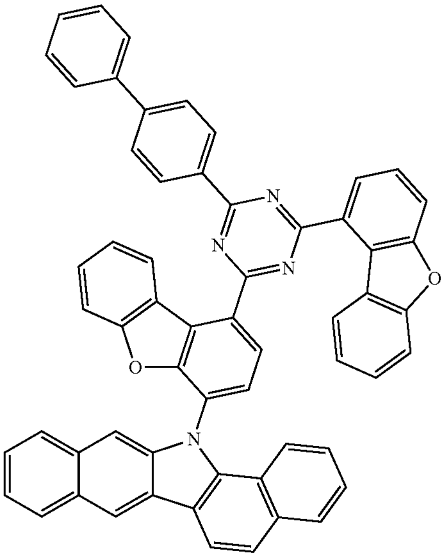
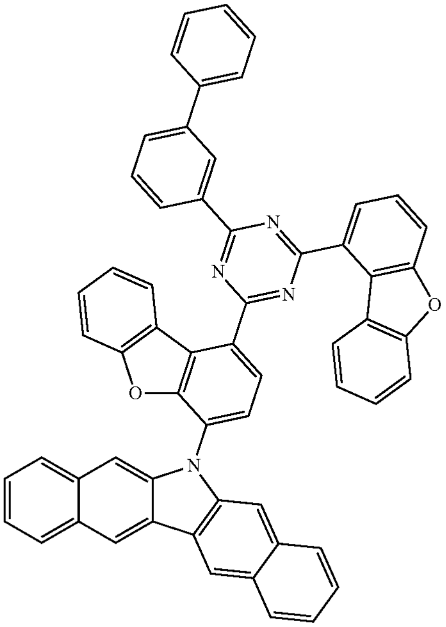
-continued
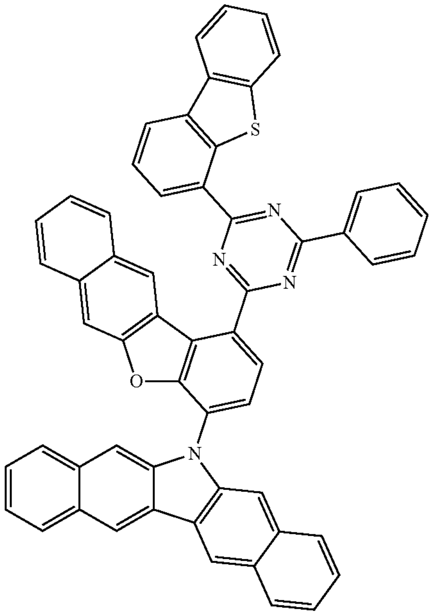
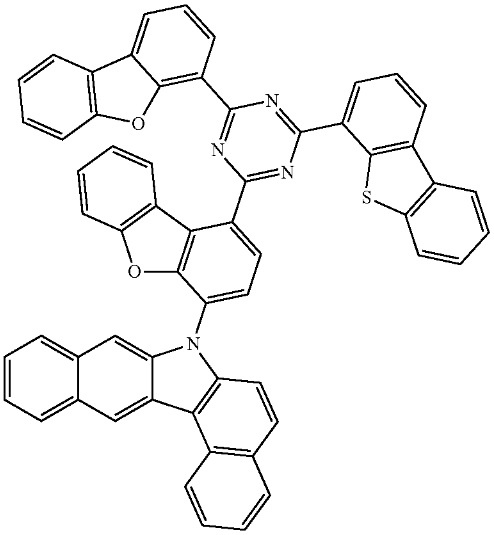
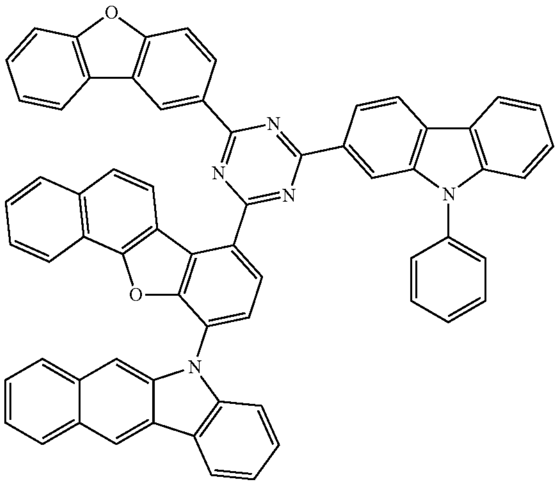

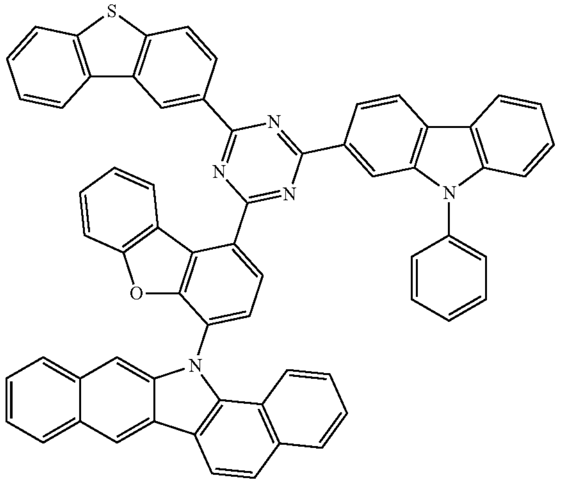
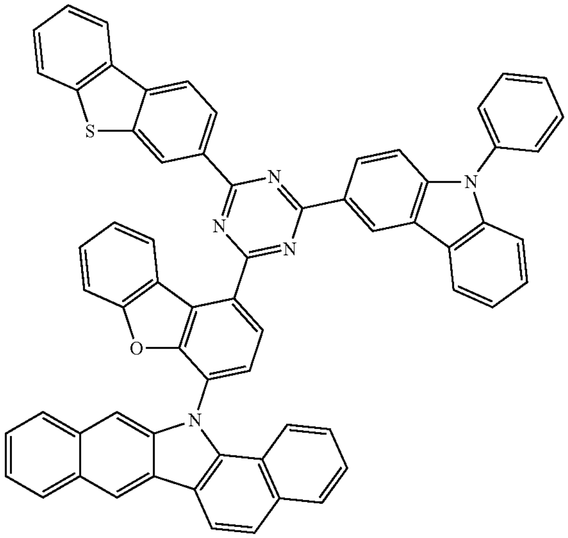
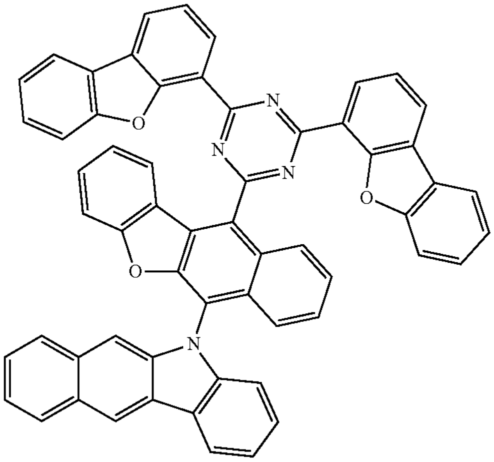
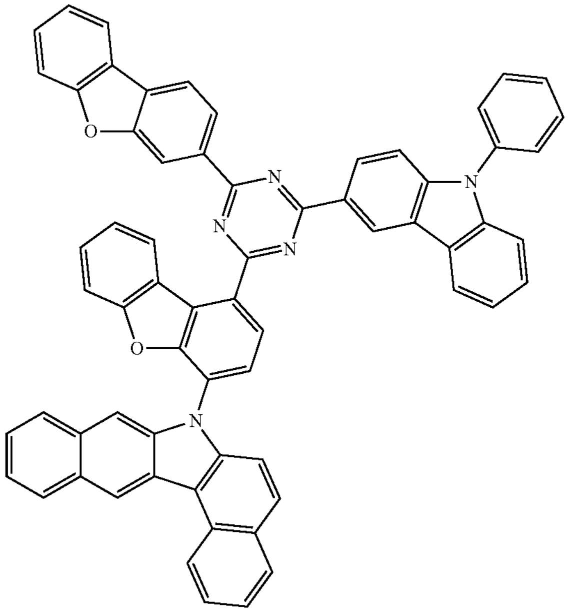
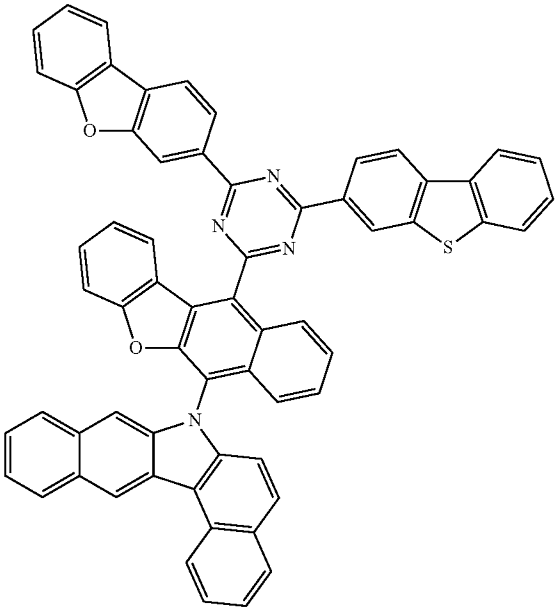

-continued
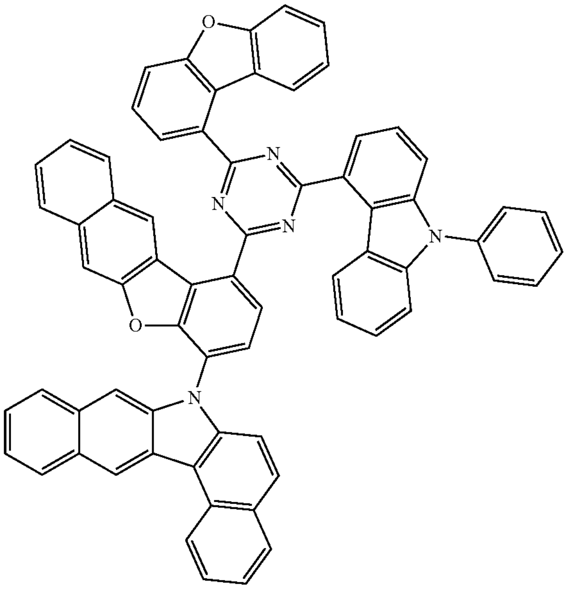
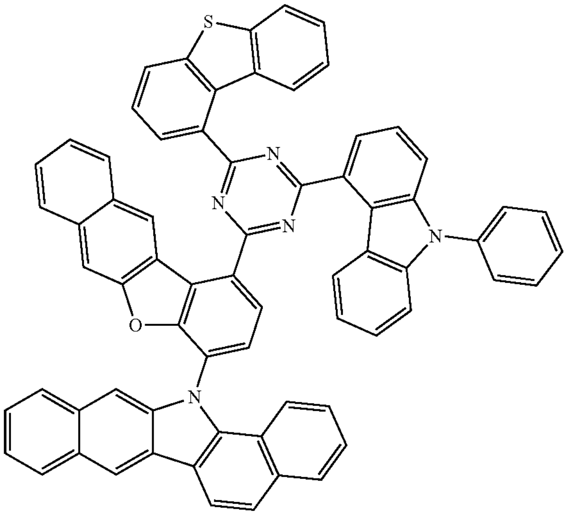
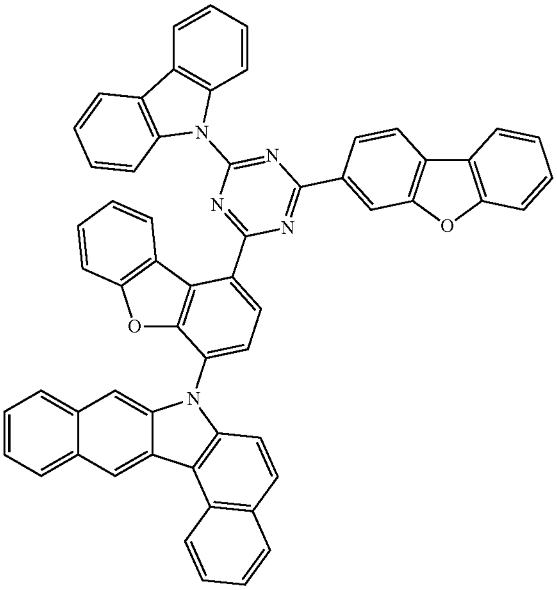
-continued
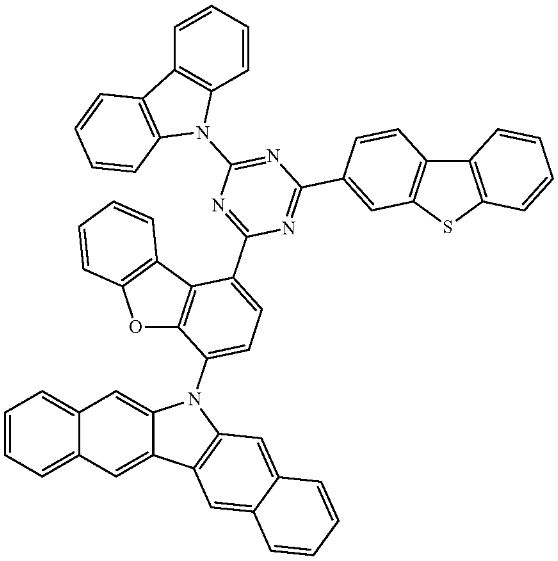
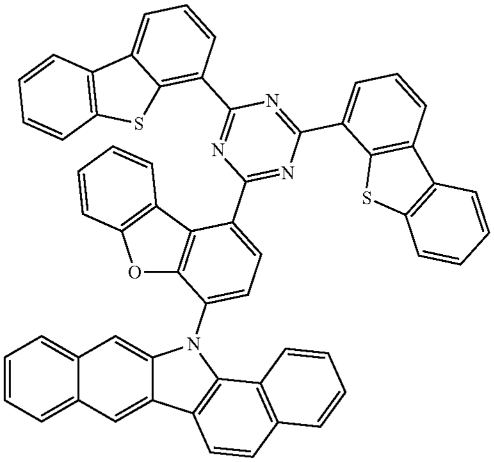
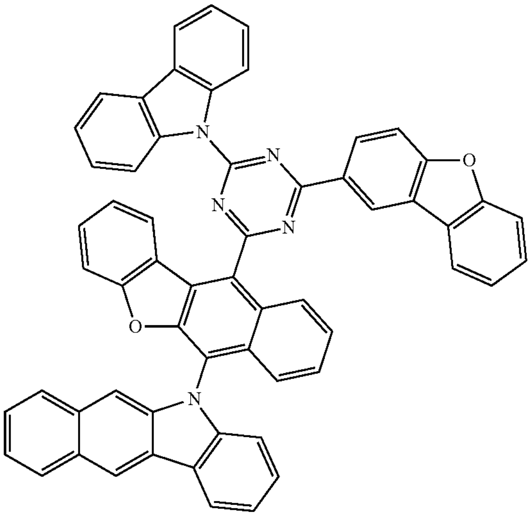

-continued
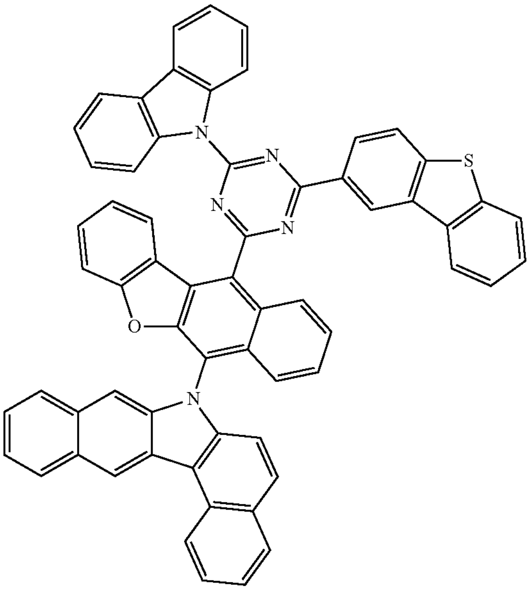
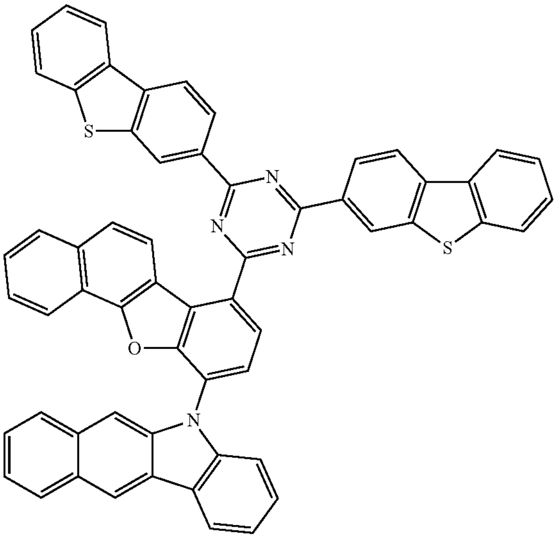
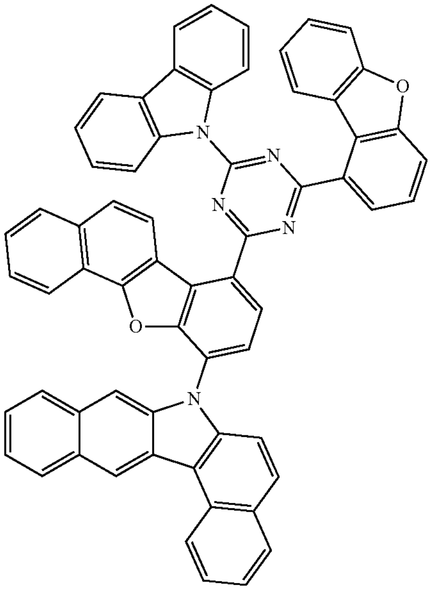
-continued
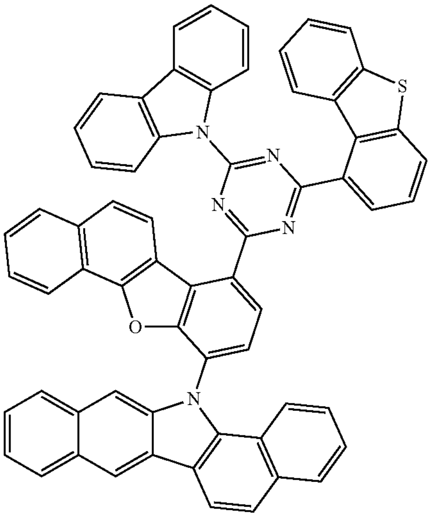
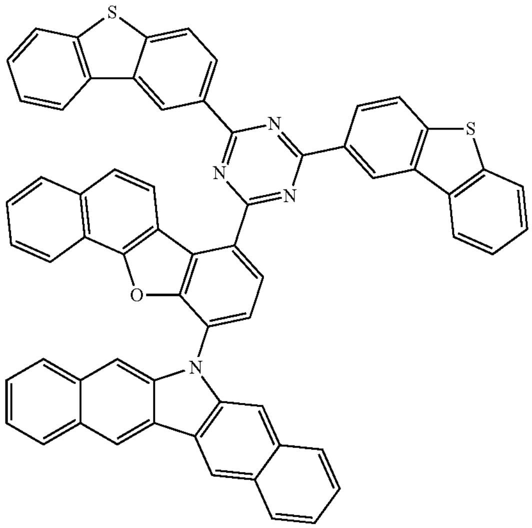
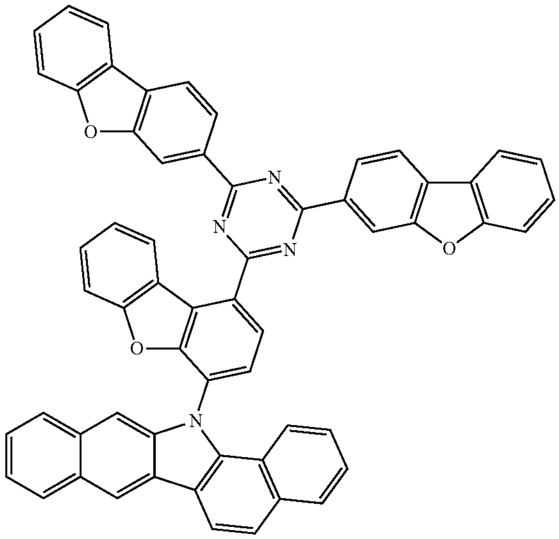

-continued
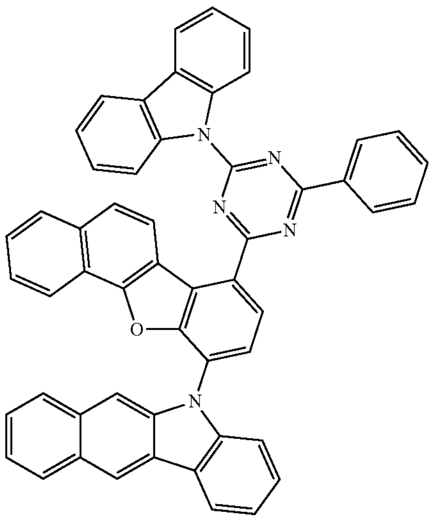
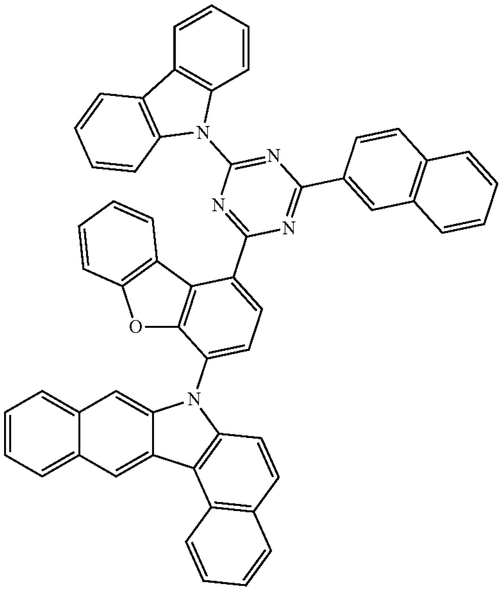
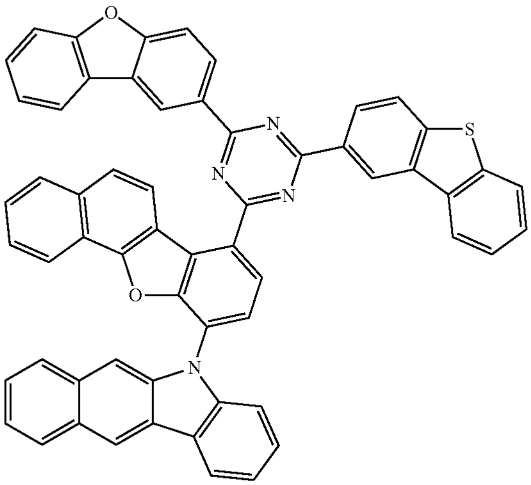
-continued
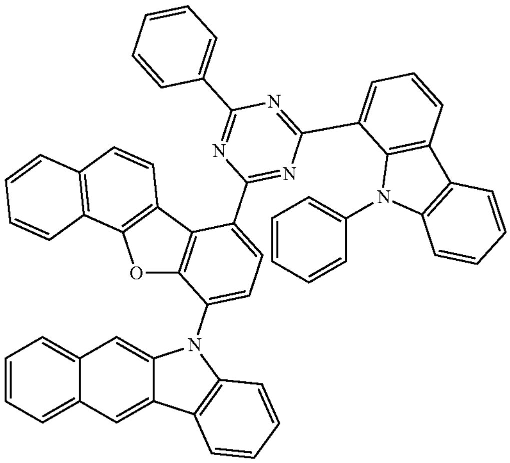
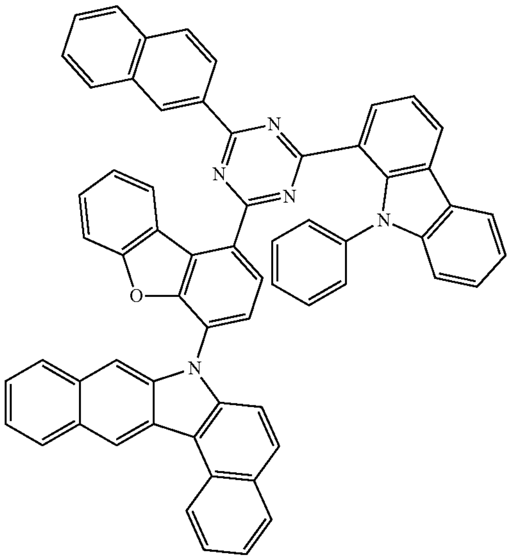
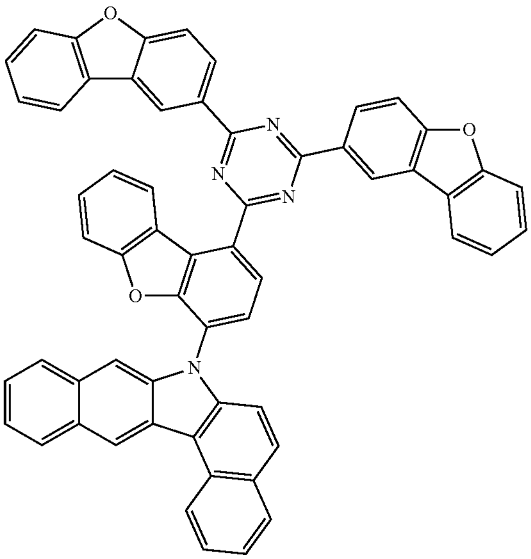

-continued
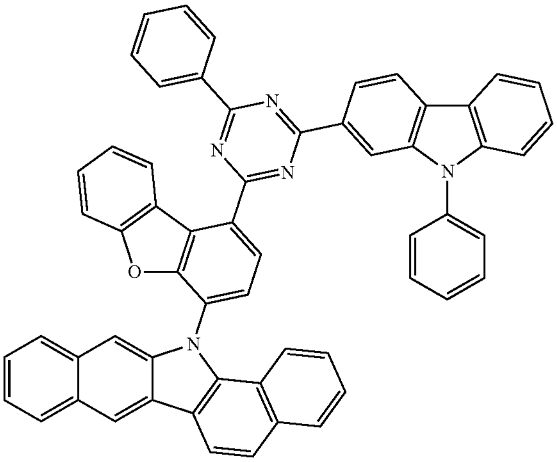
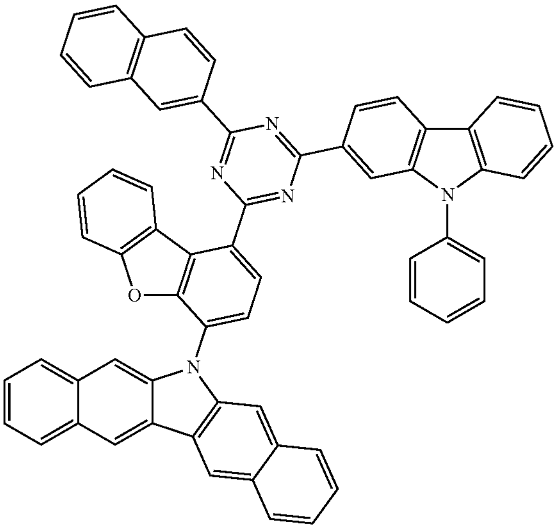
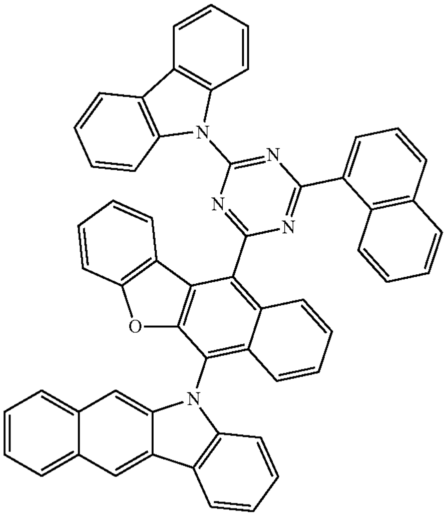
-continued
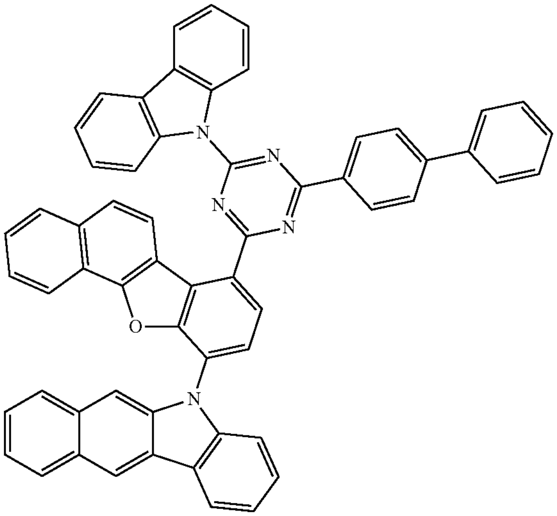
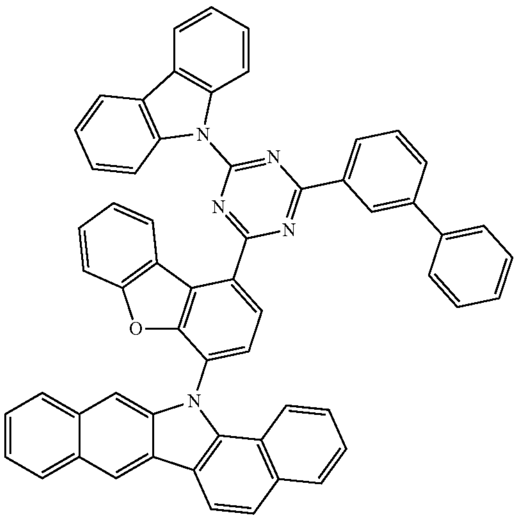
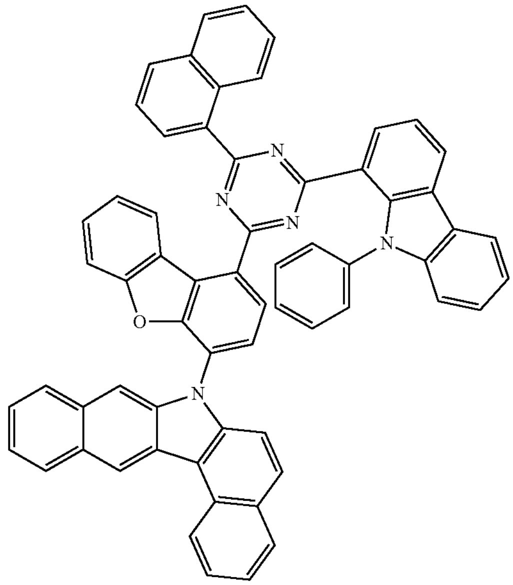

-continued
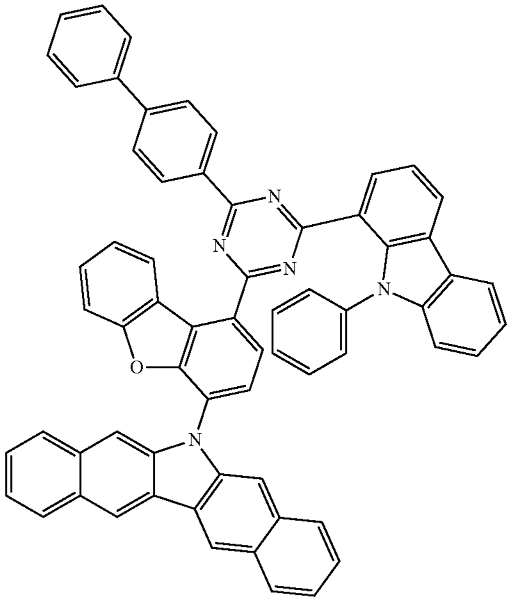
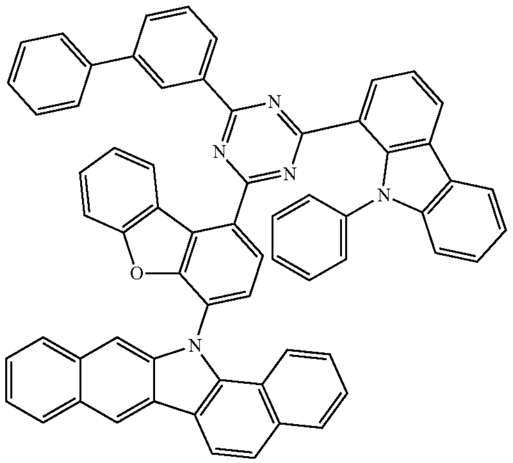
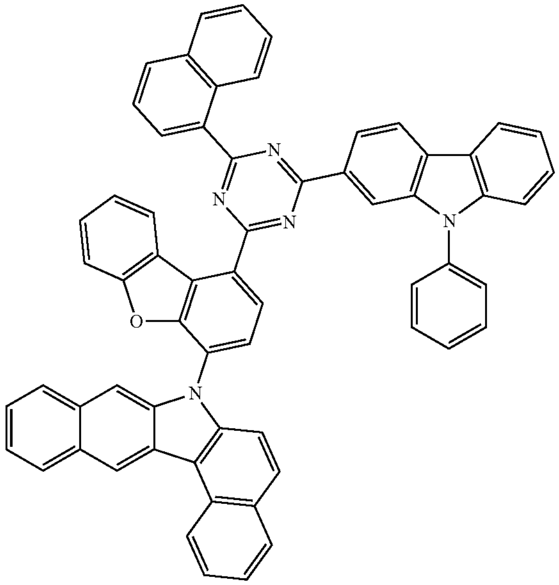
-continued
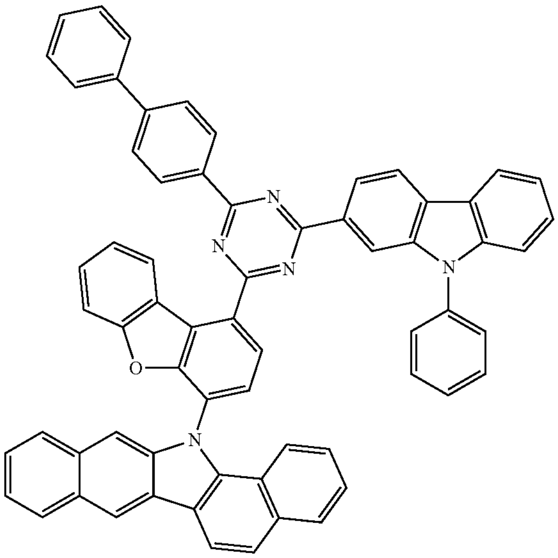
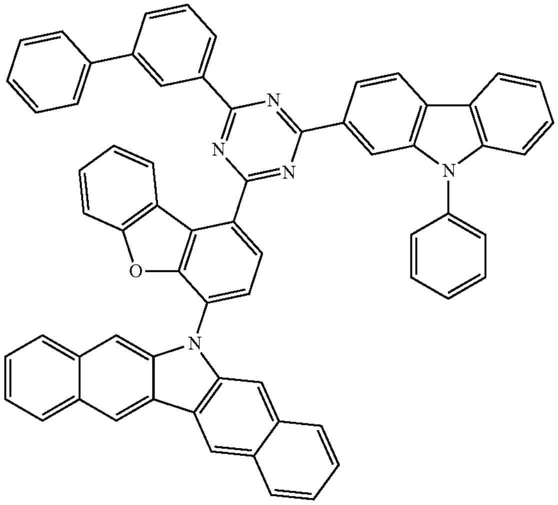
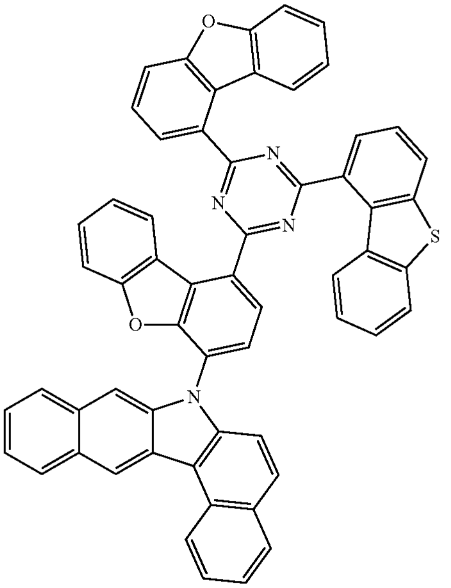

-continued
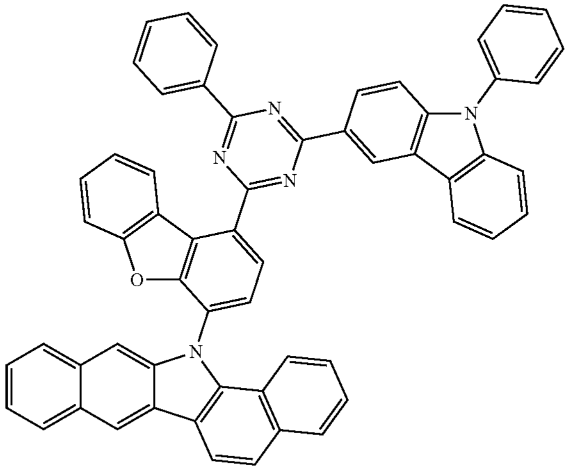
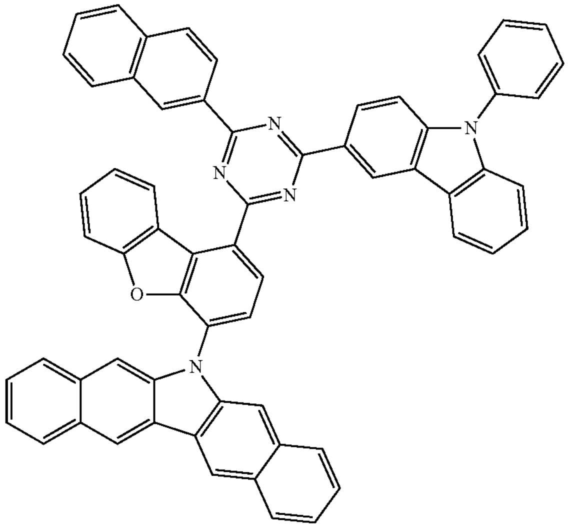
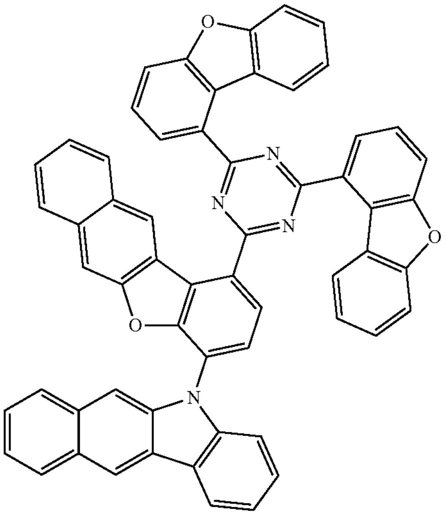
-continued
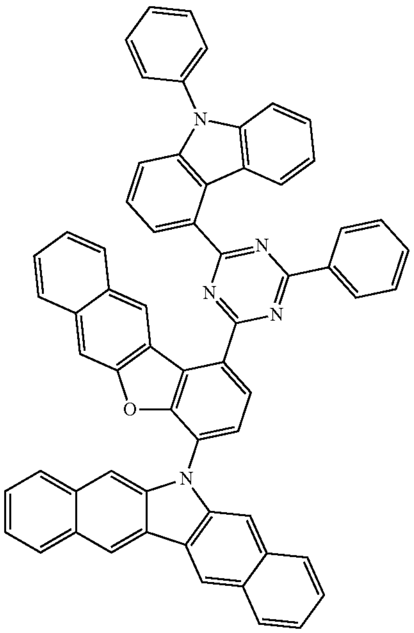
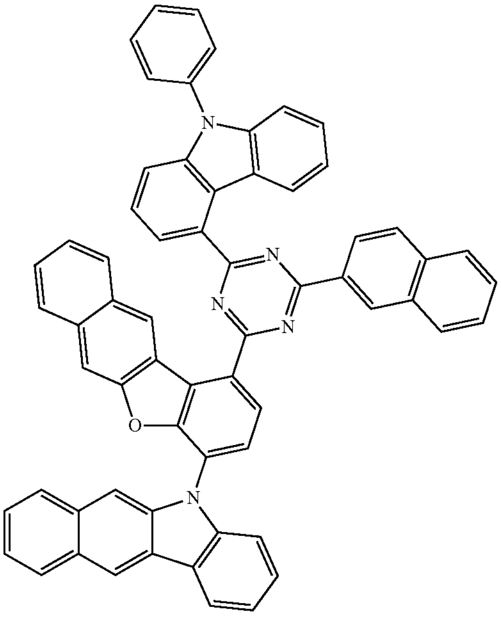

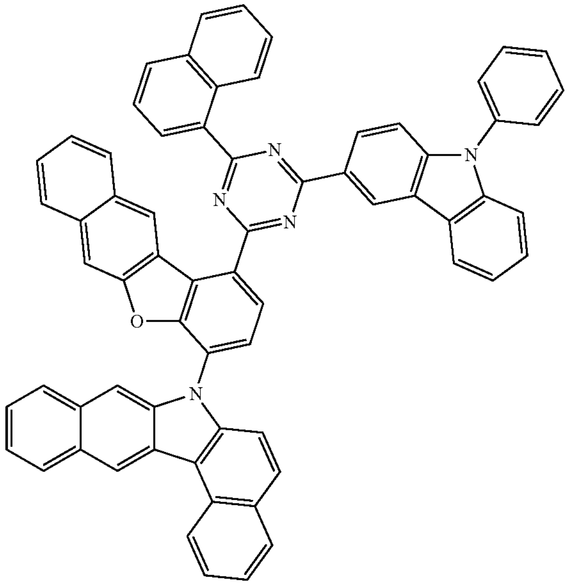
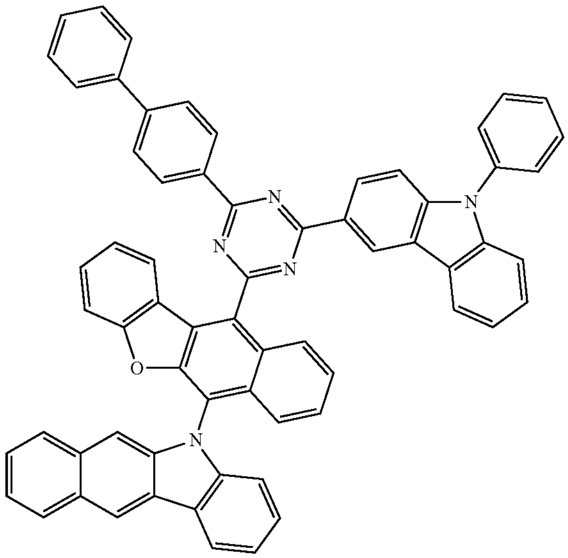
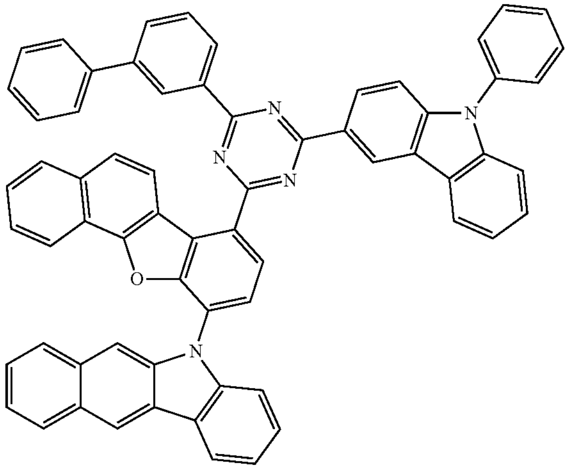
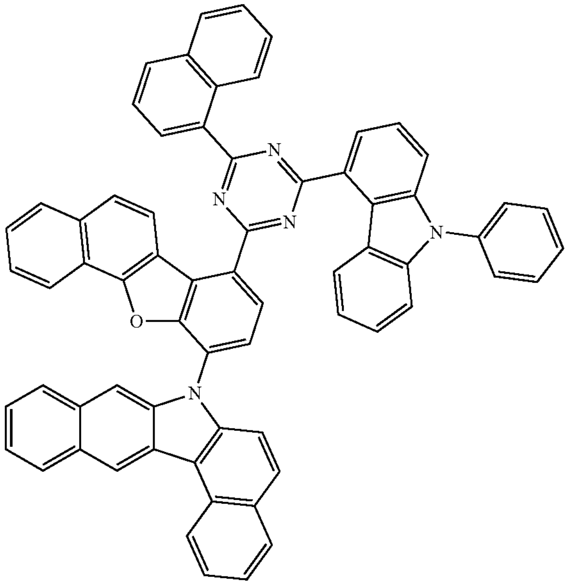
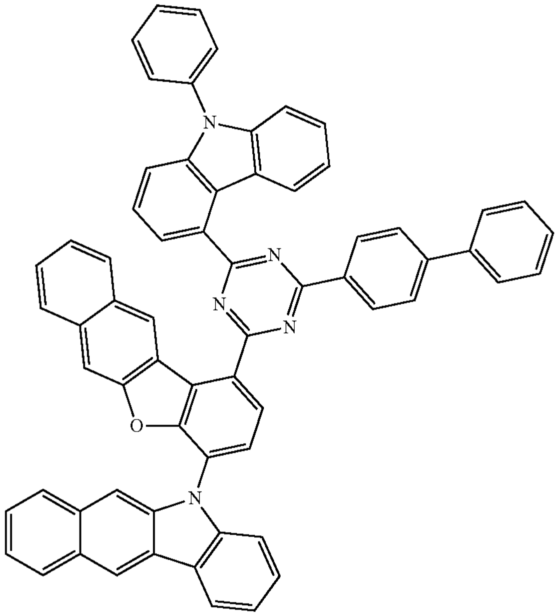

-continued
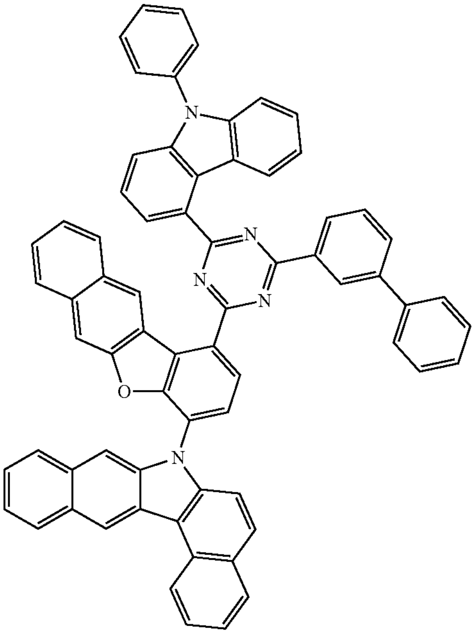
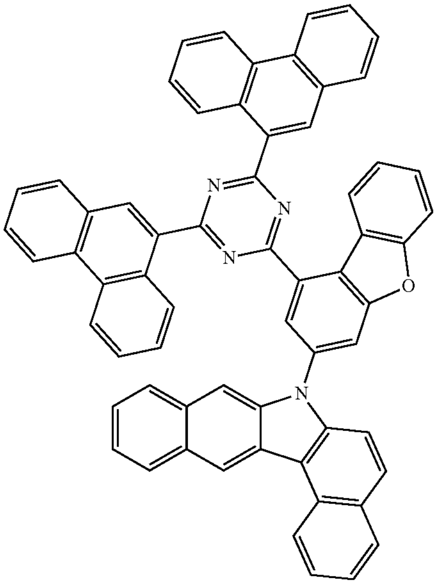
-continued
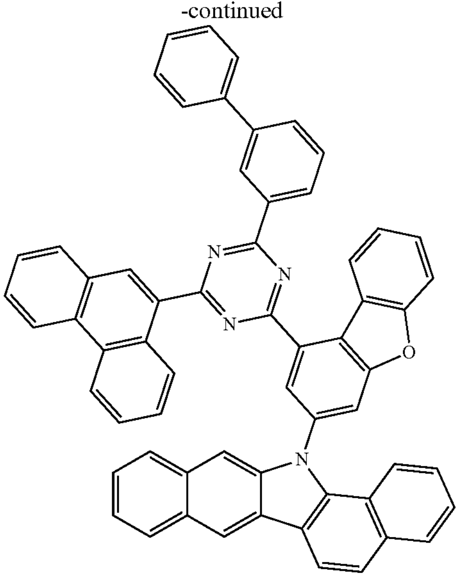
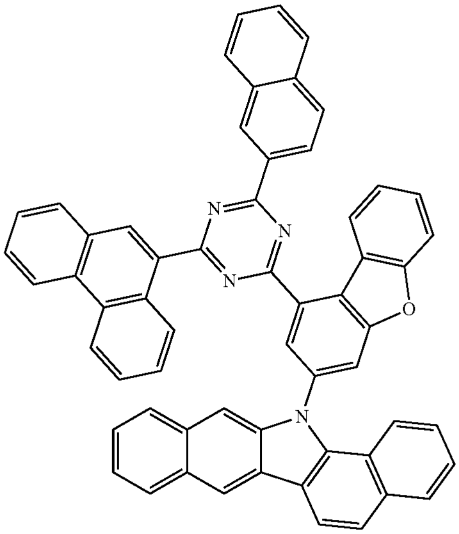
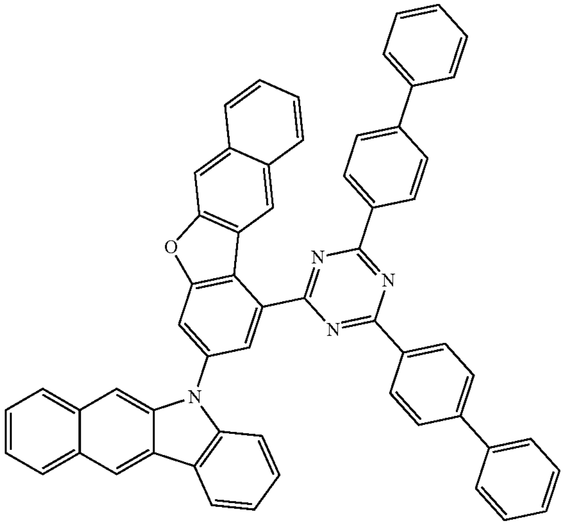

-continued
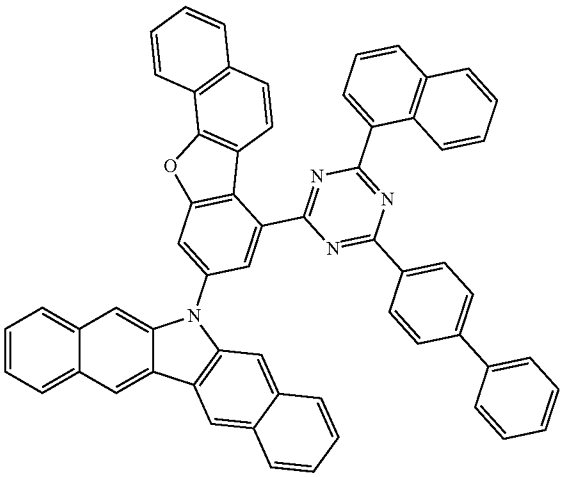
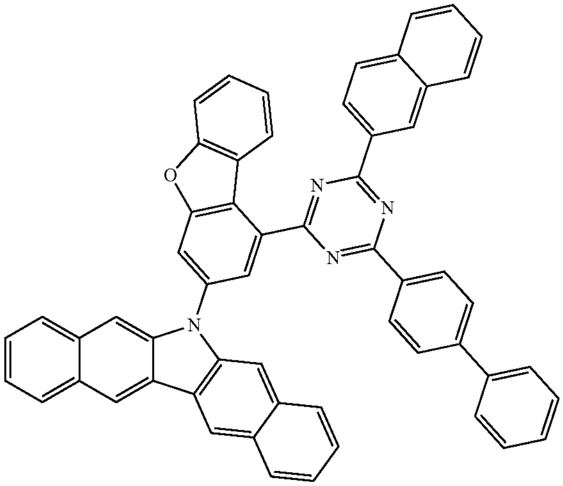
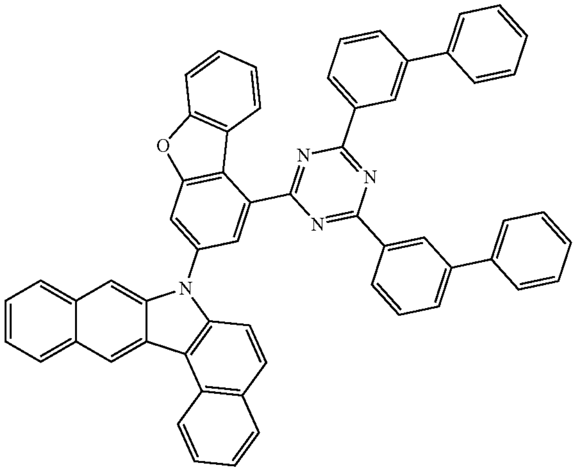
-continued
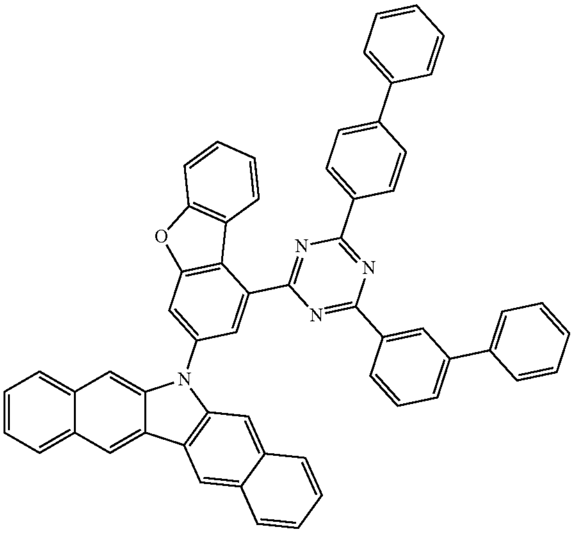
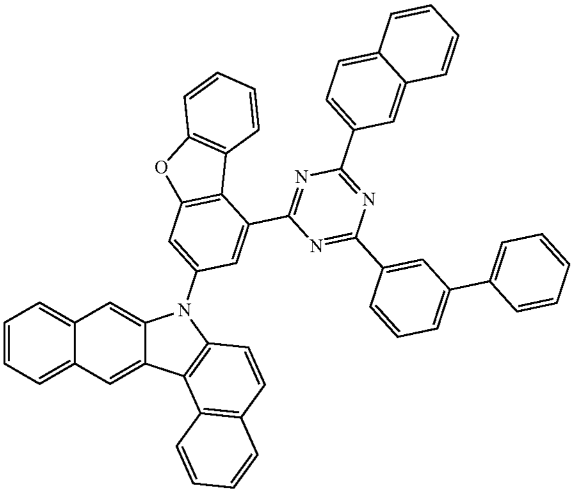
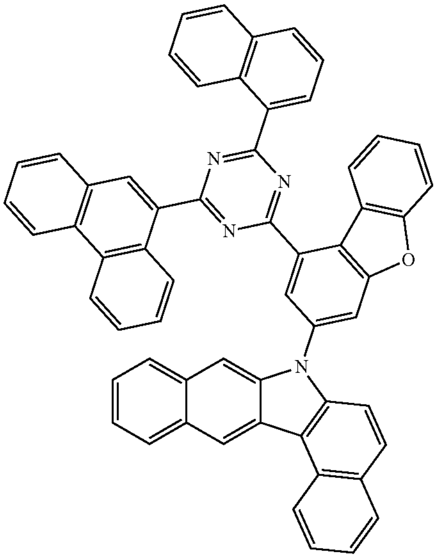

-continued
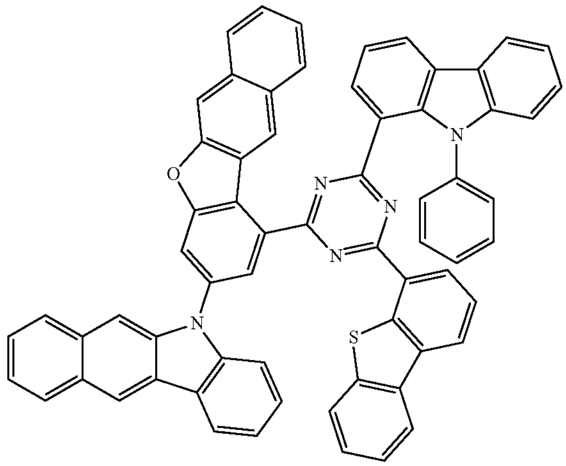
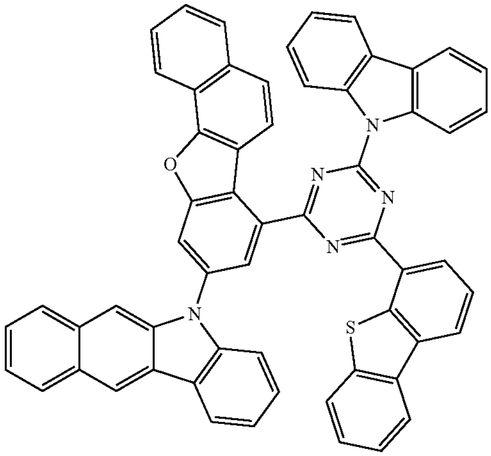
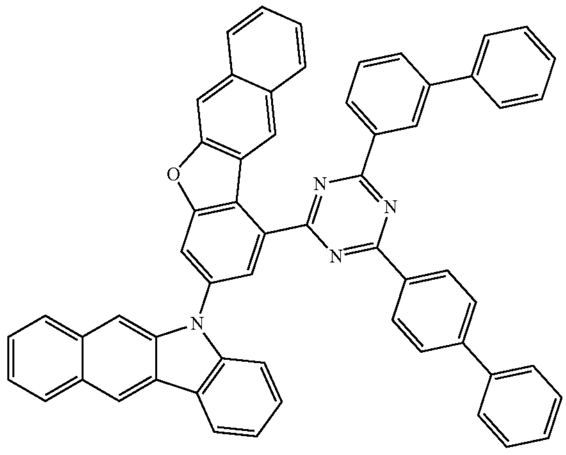
-continued
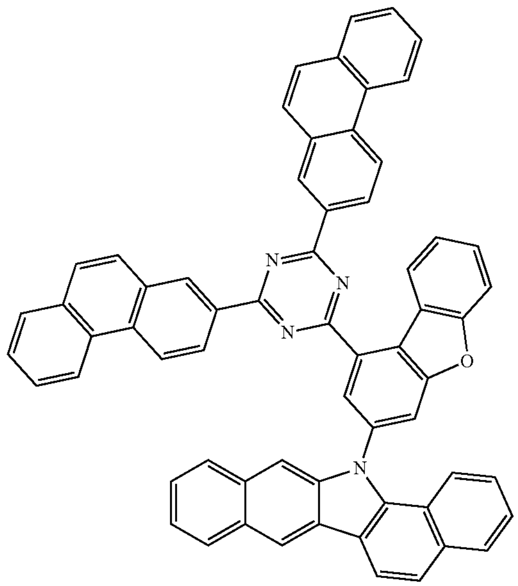
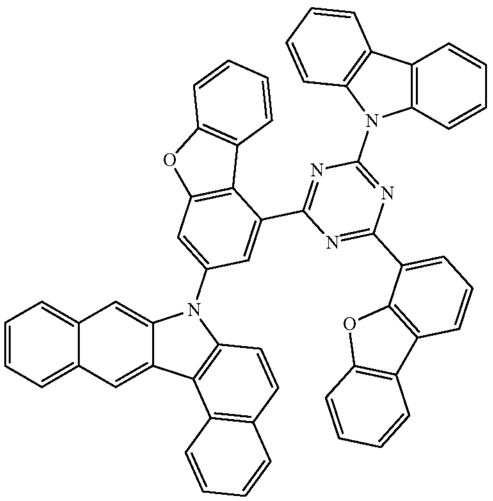
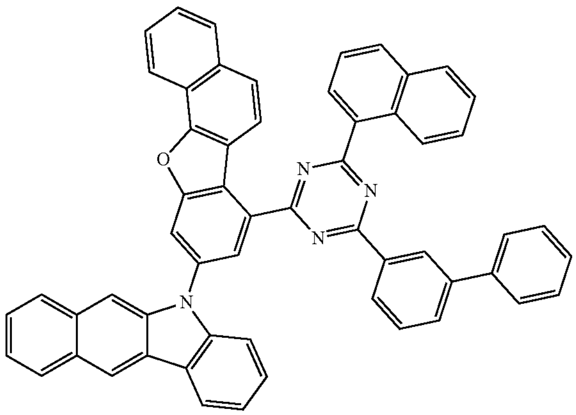

-continued
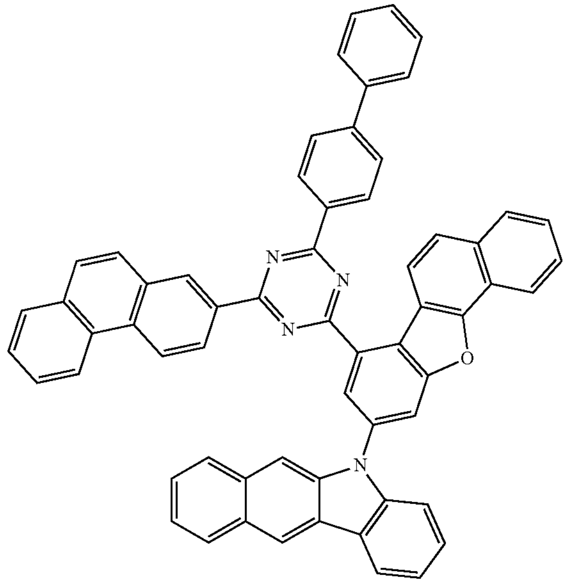
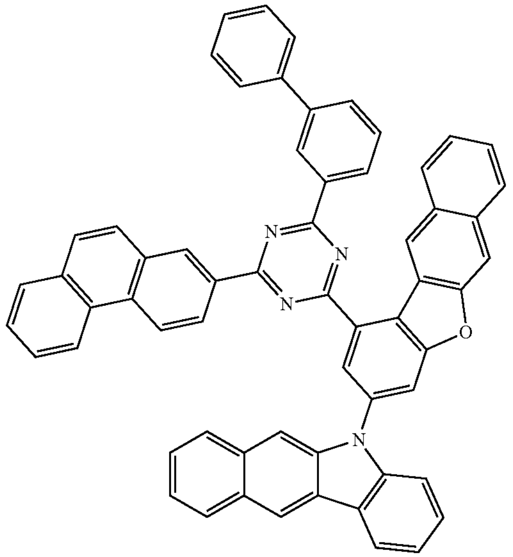
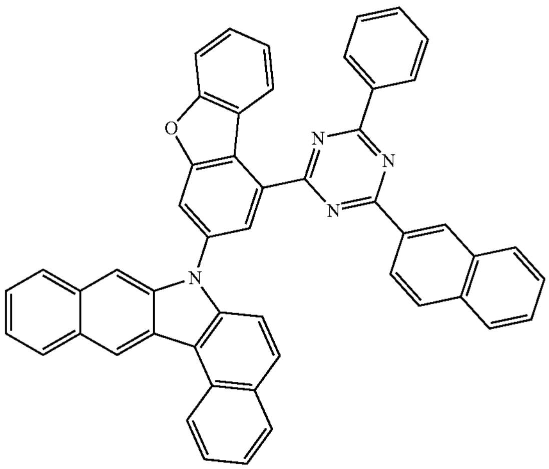
-continued
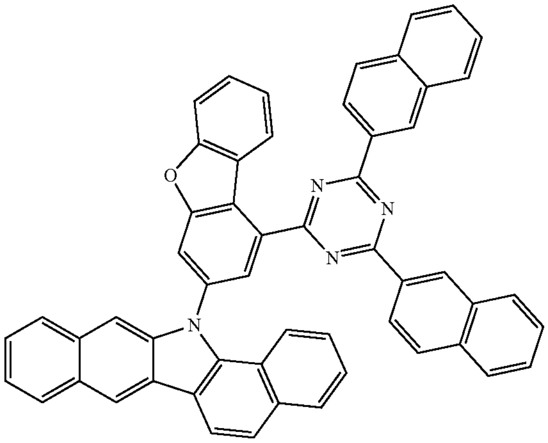
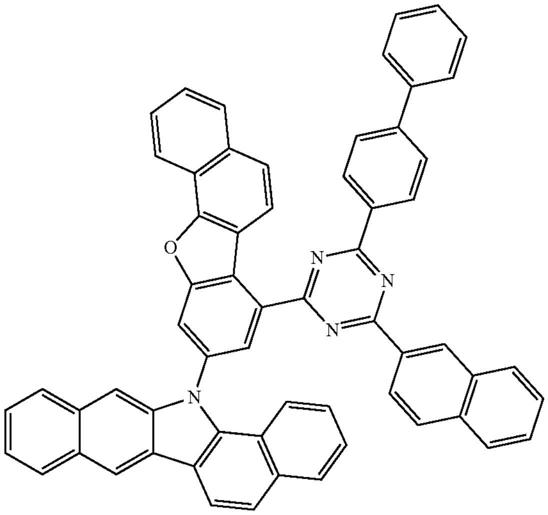
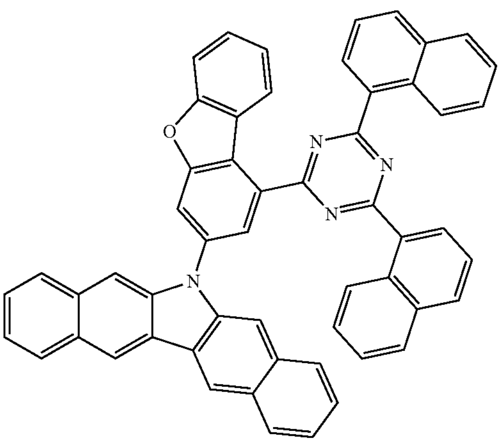

-continued
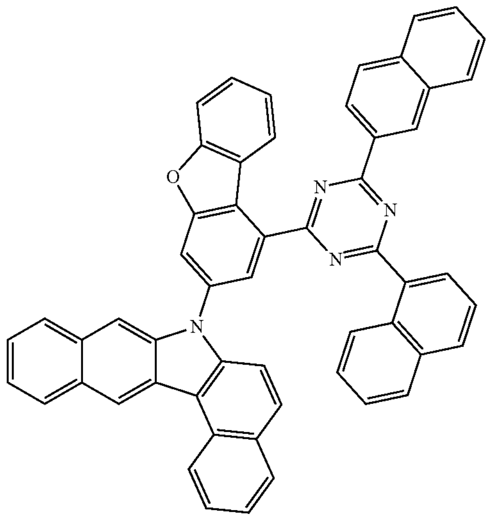
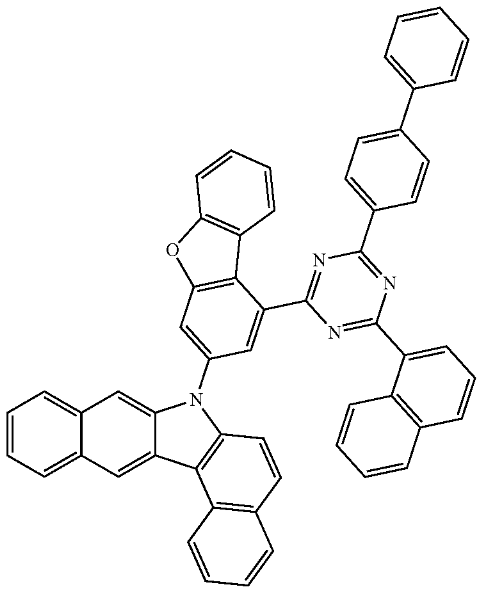
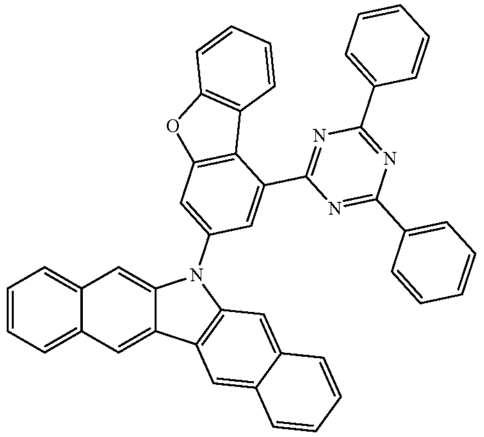
-continued
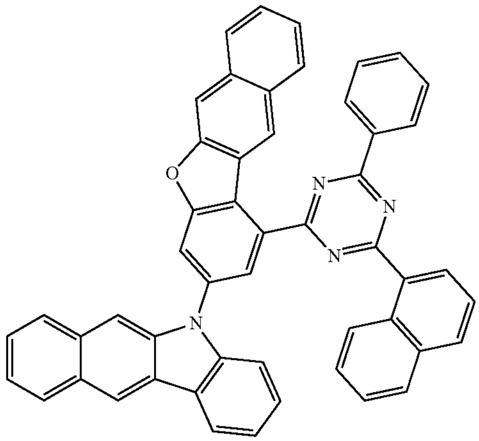
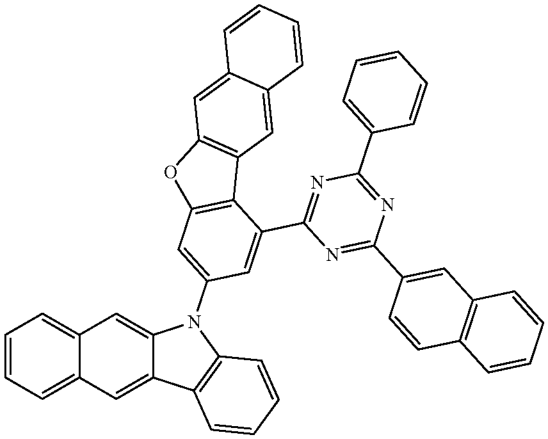
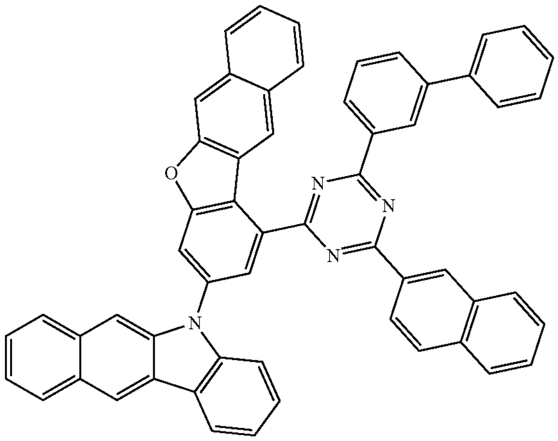

-continued
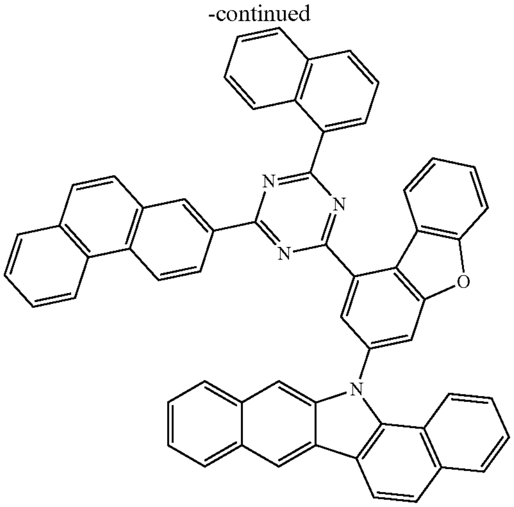
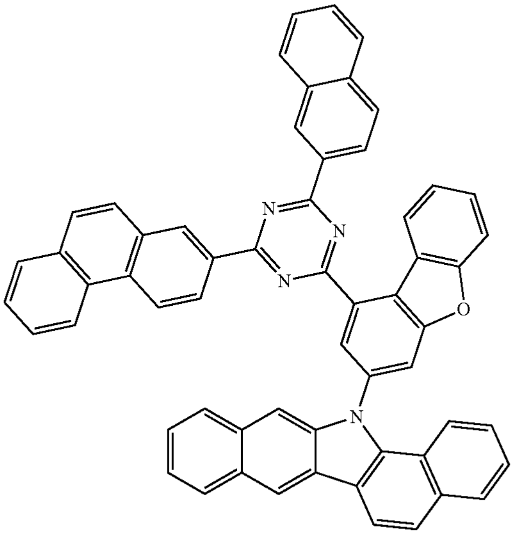
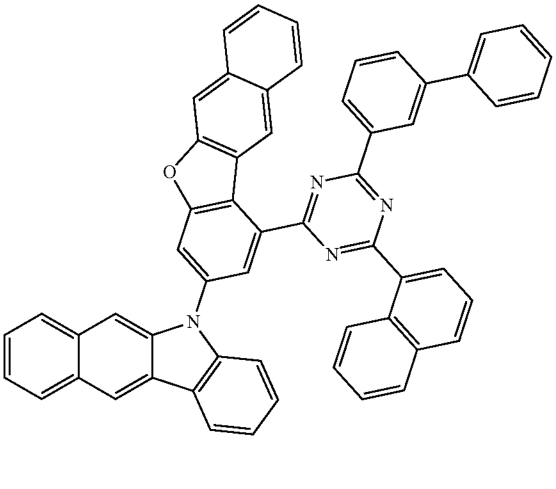
-continued
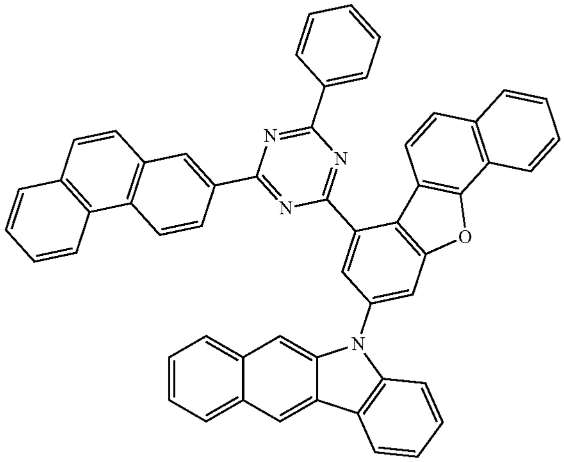
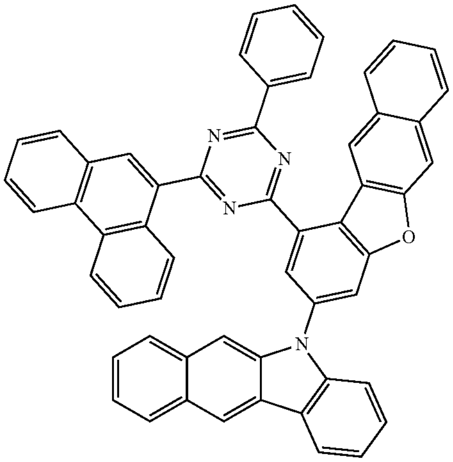
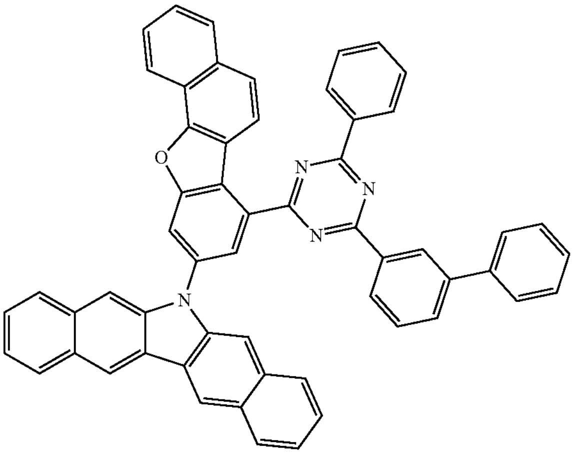

-continued
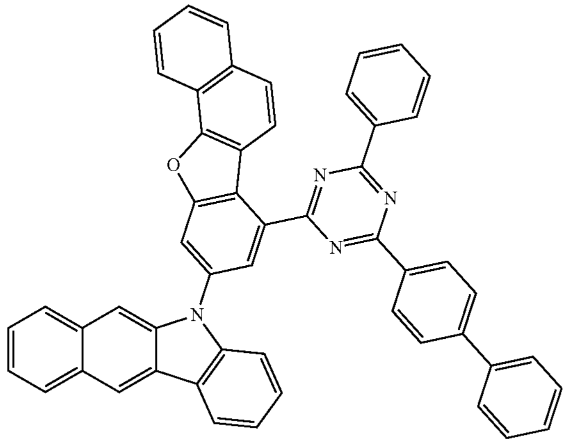
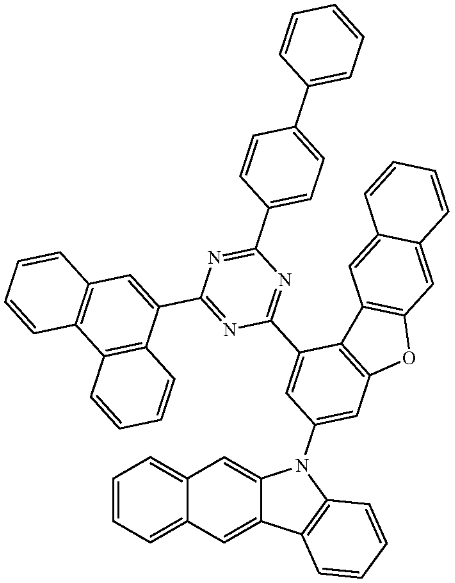
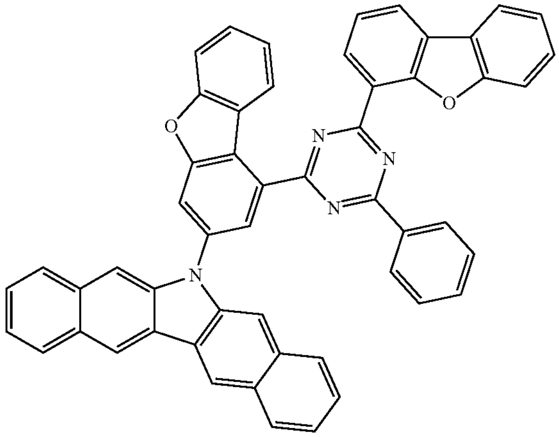
-continued
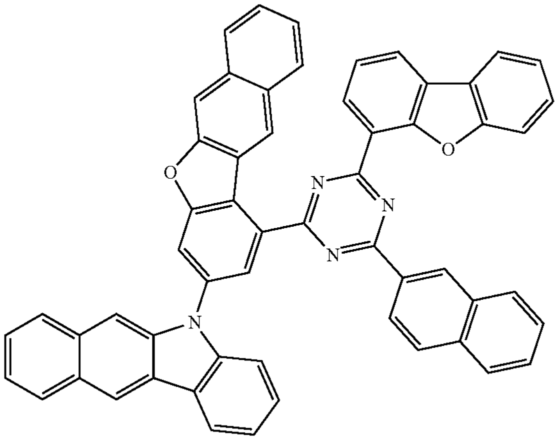
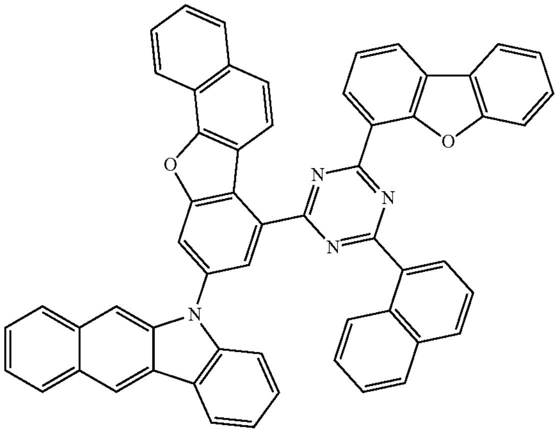
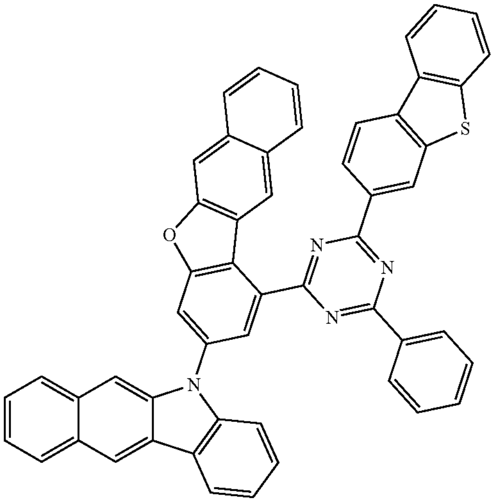

-continued
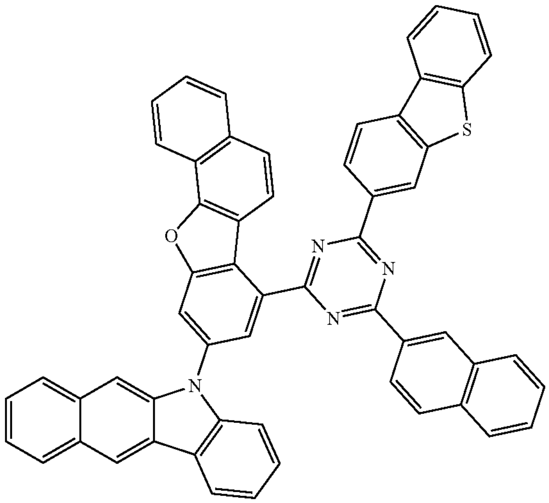
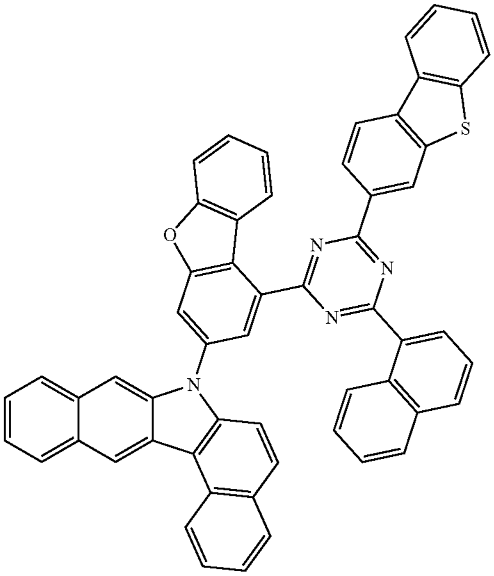
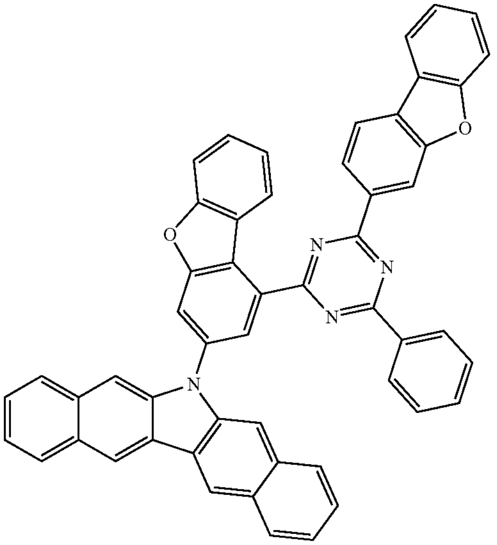
-continued
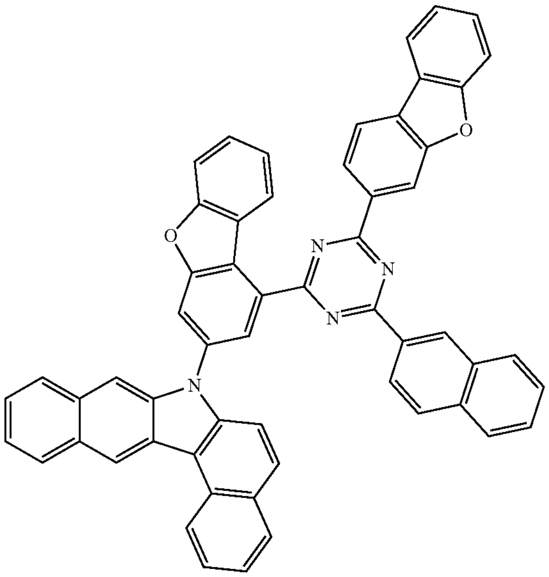
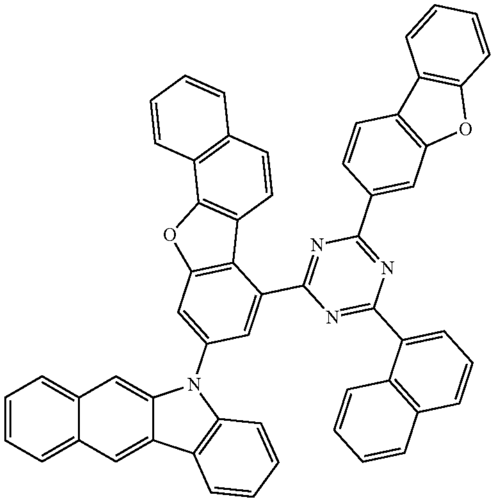
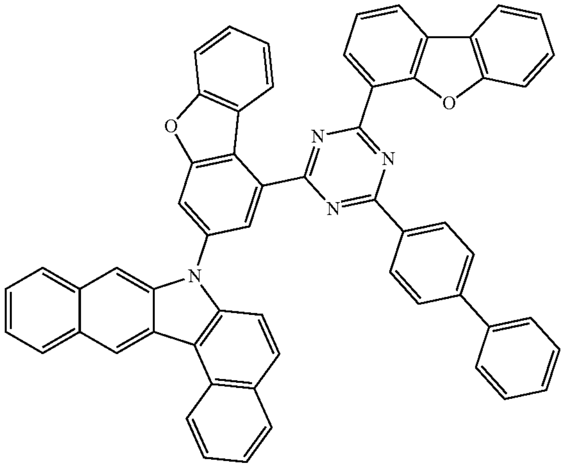

-continued
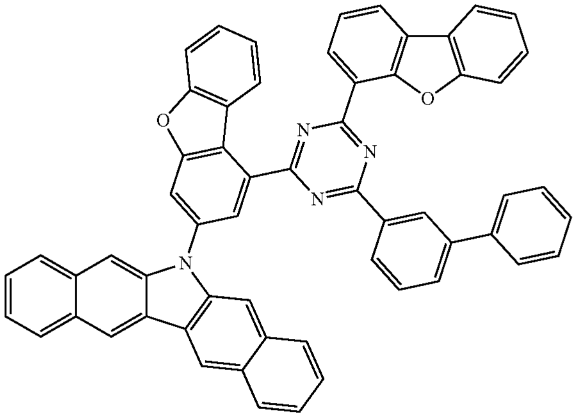
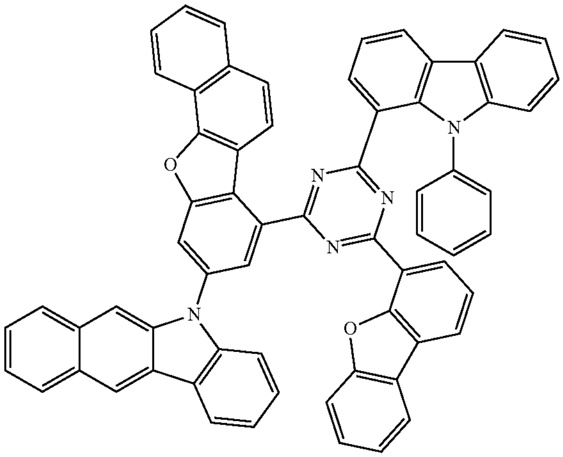
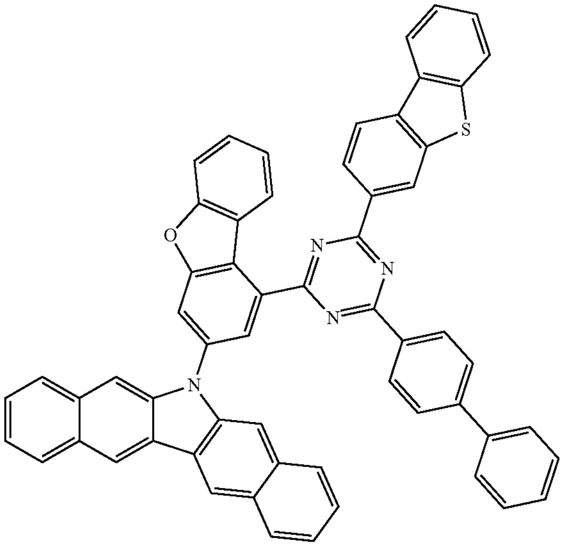
-continued
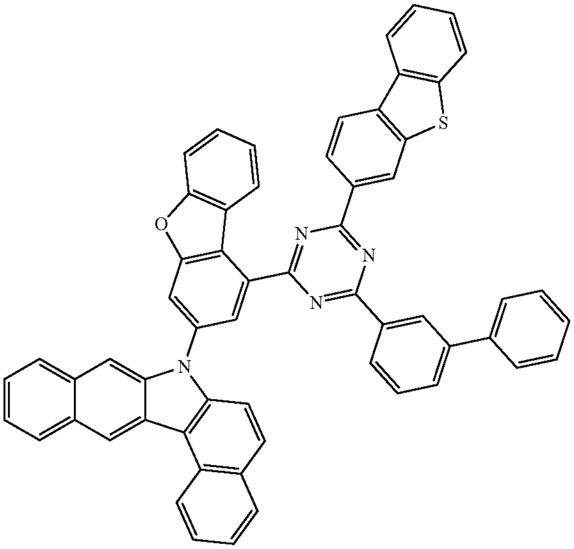
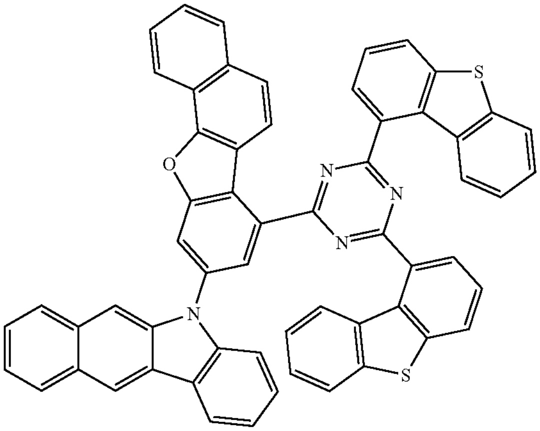
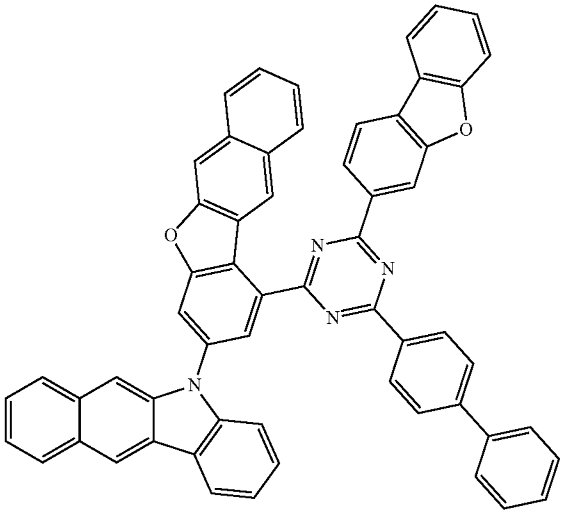

-continued
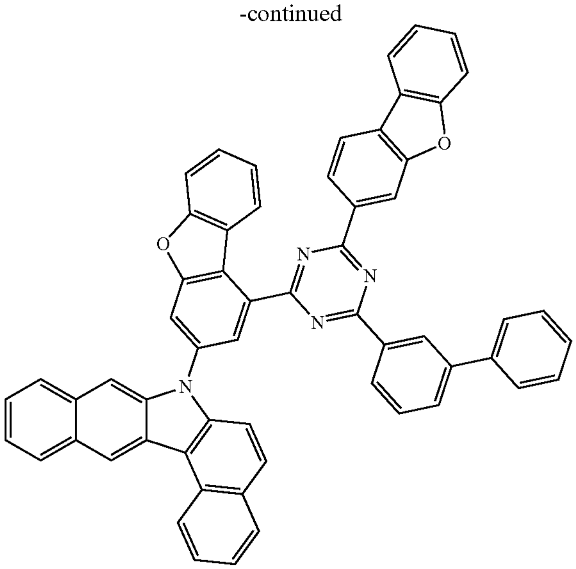
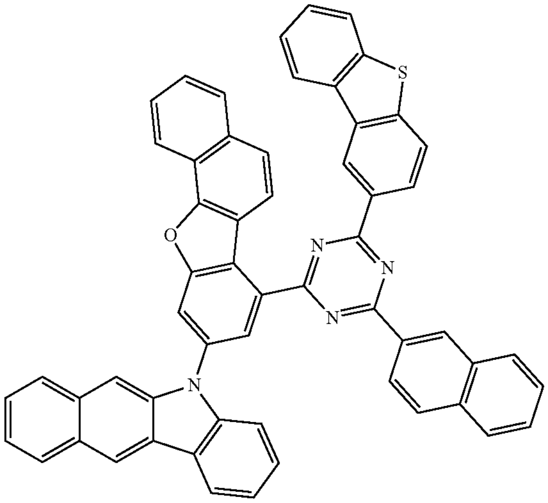
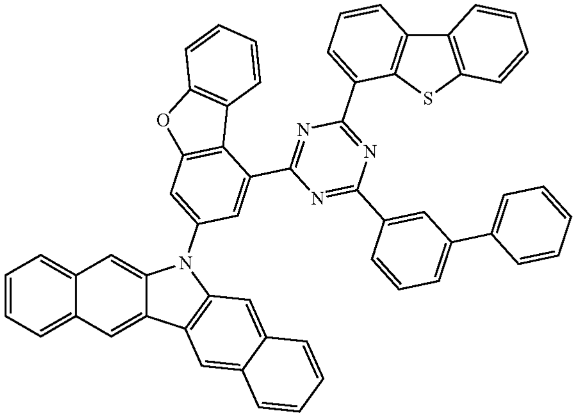
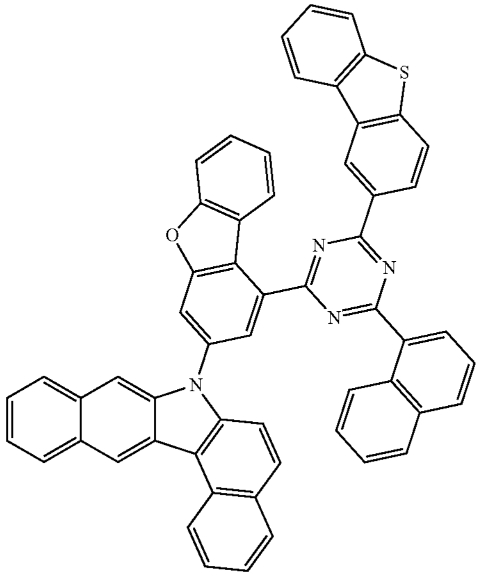
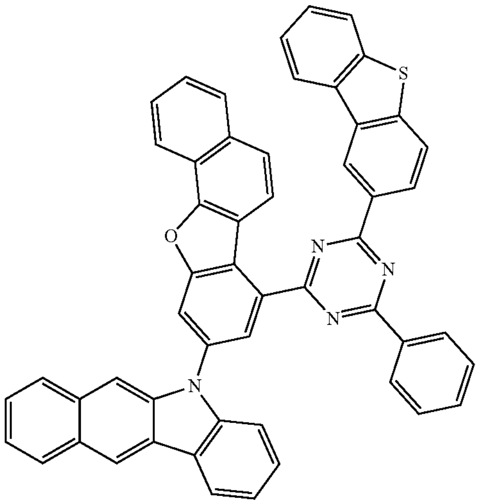
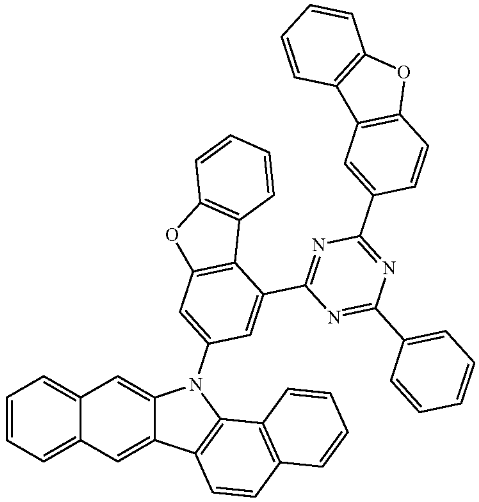
-continued -continued
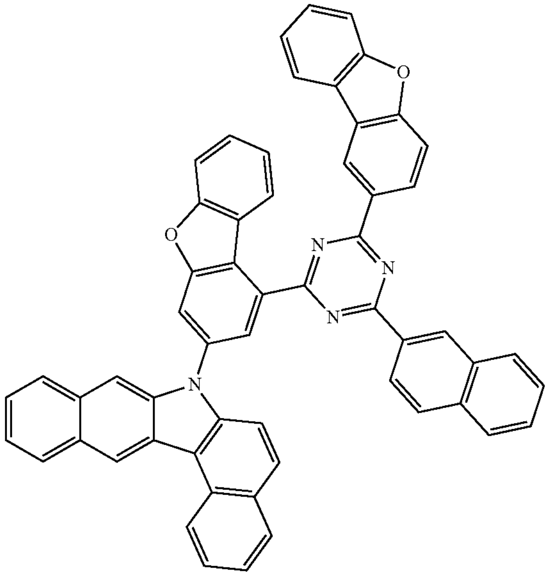
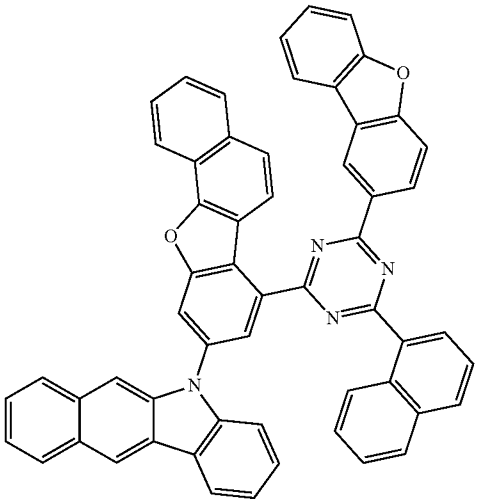
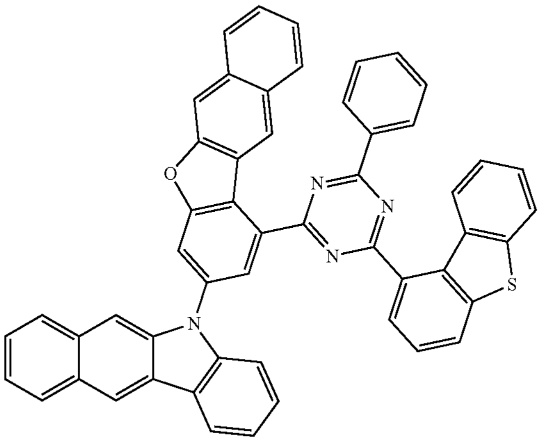
-continued
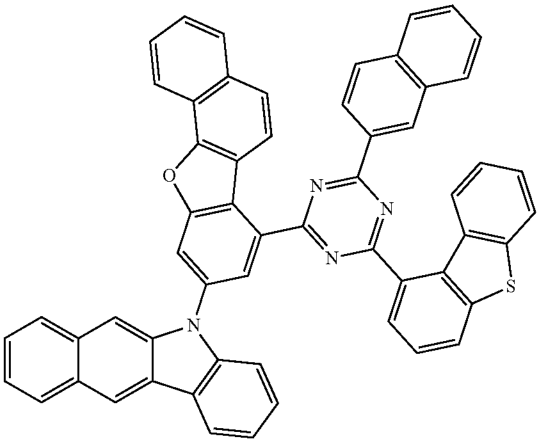
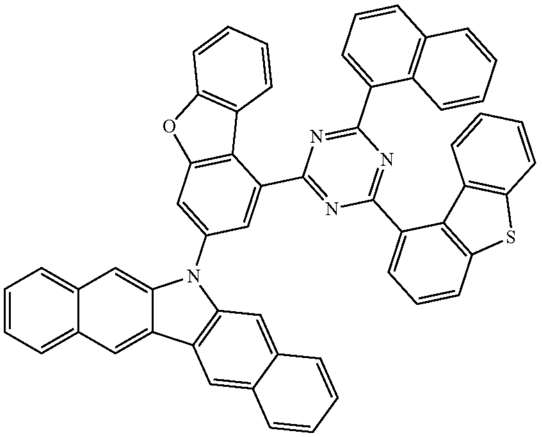
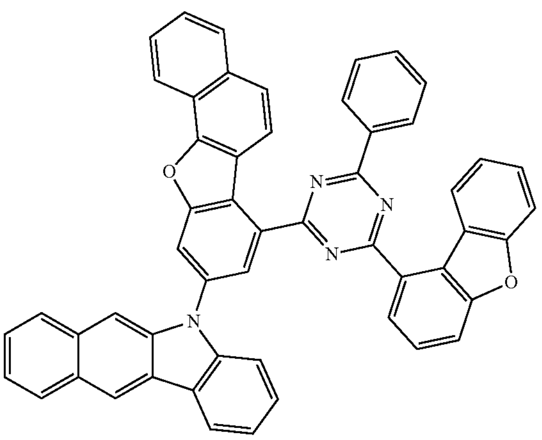

-continued
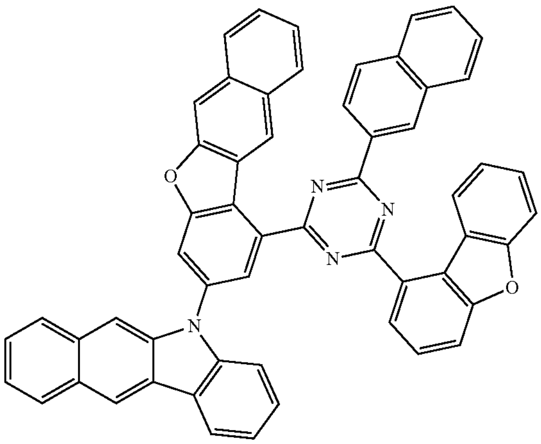
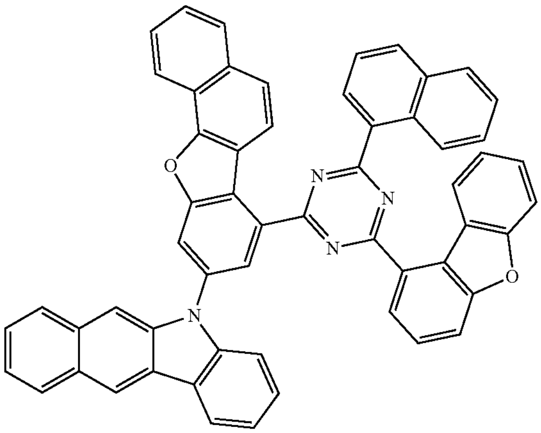
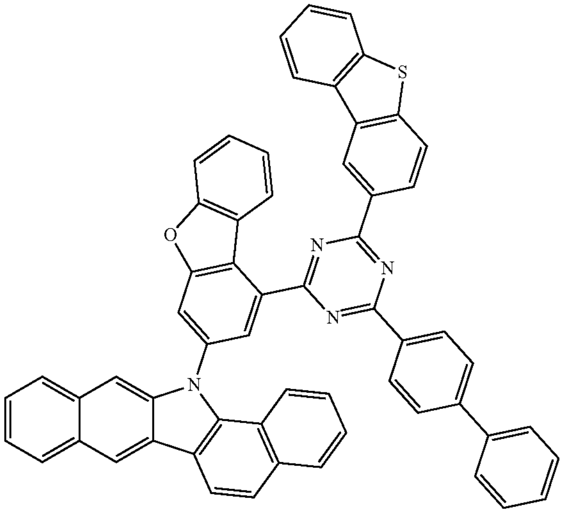
-continued
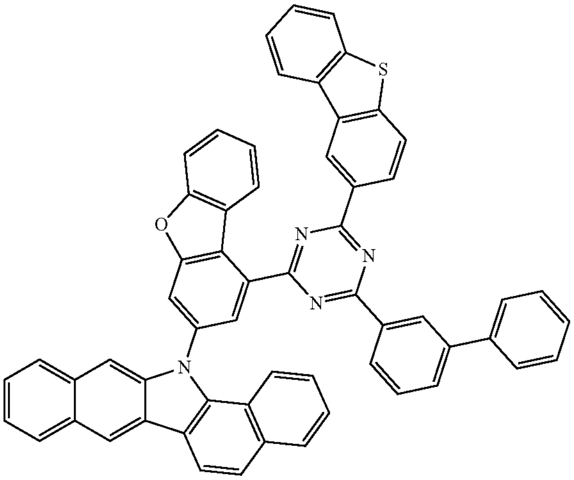
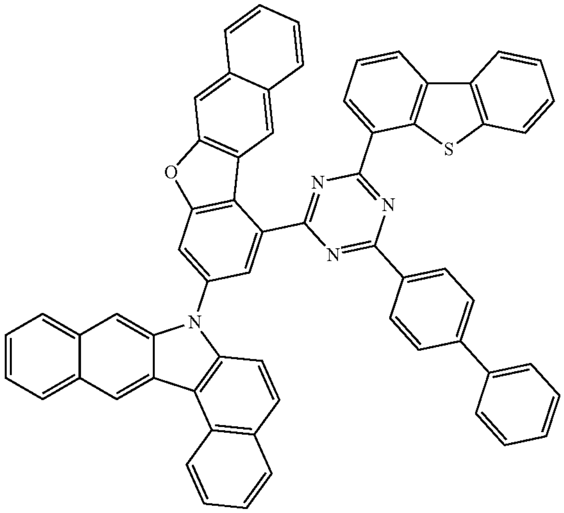
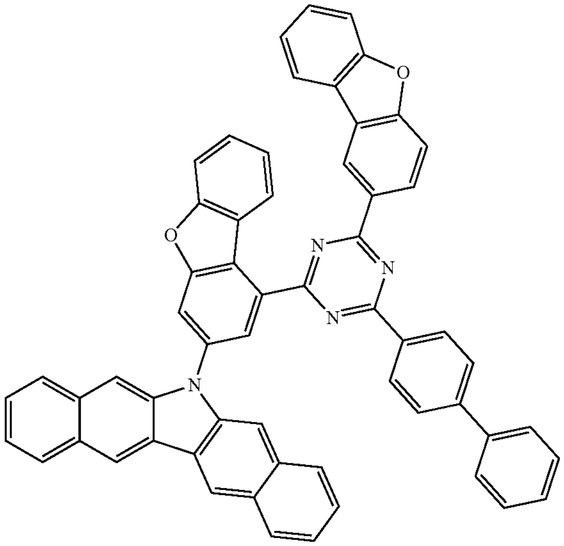

-continued
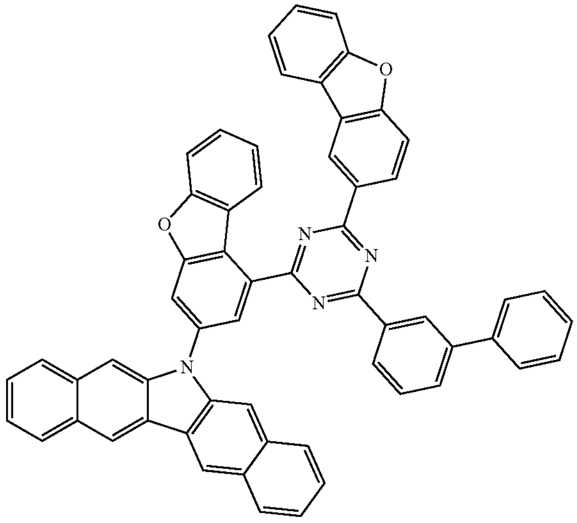
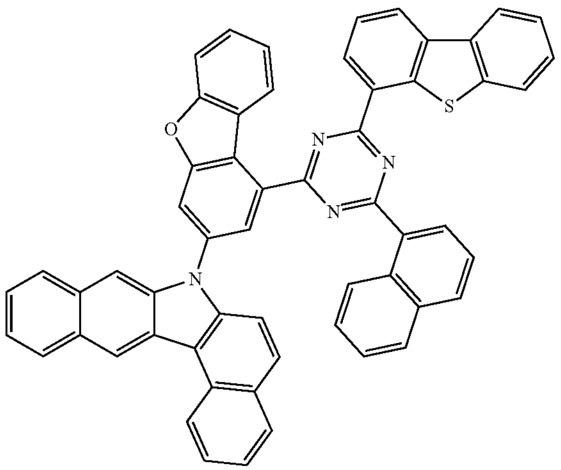
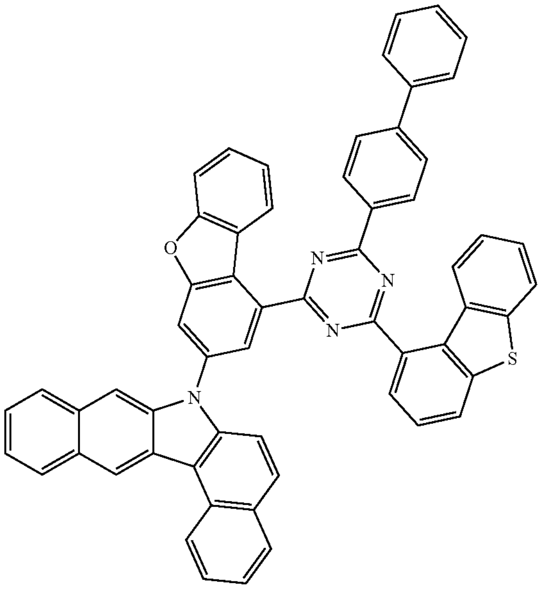
-continued
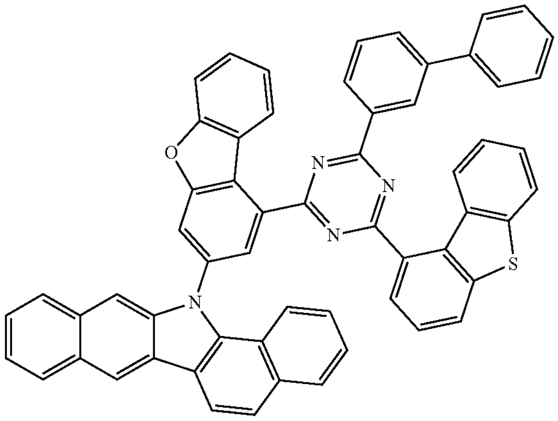
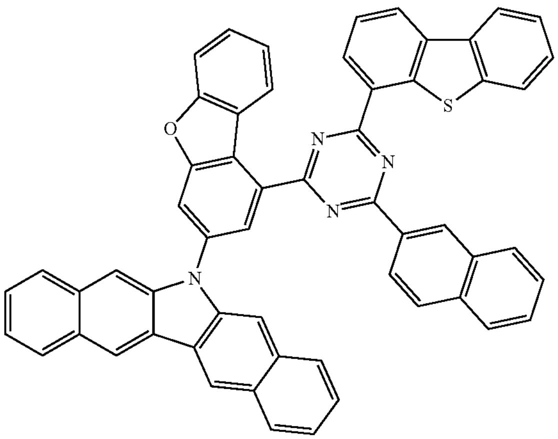
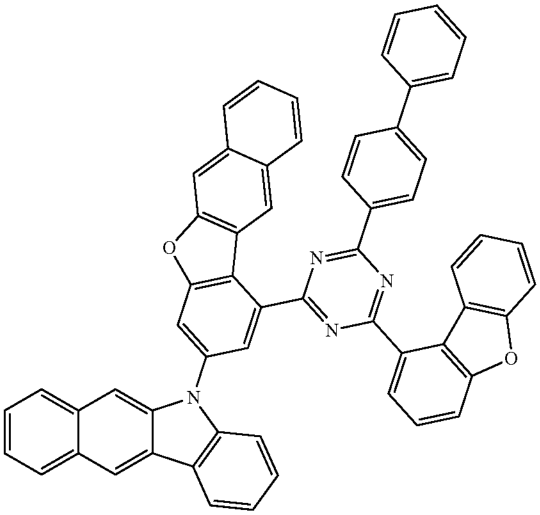

-continued
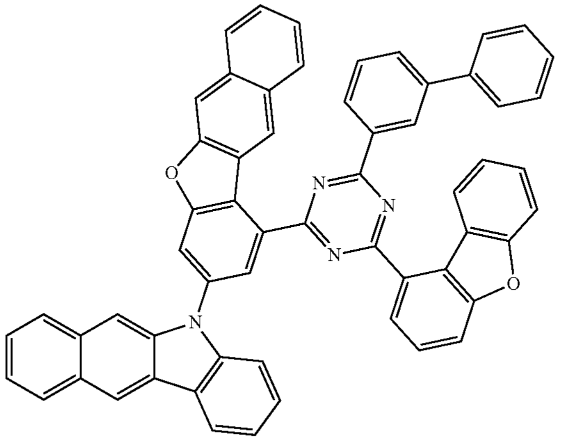
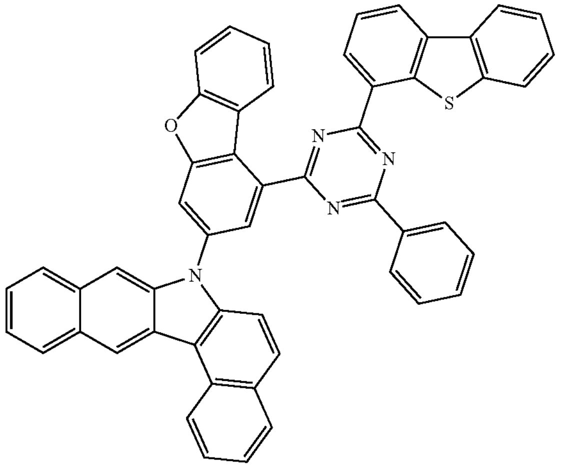
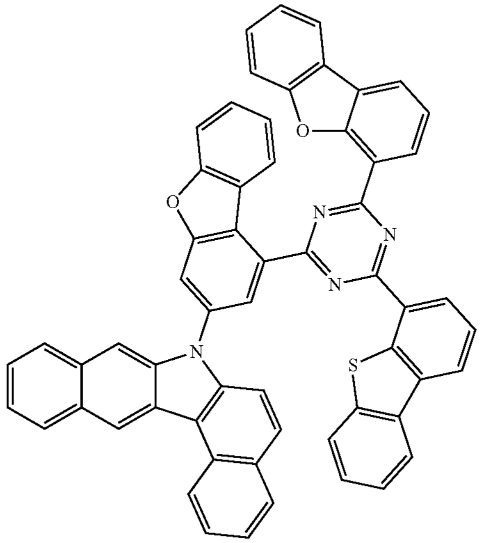
-continued
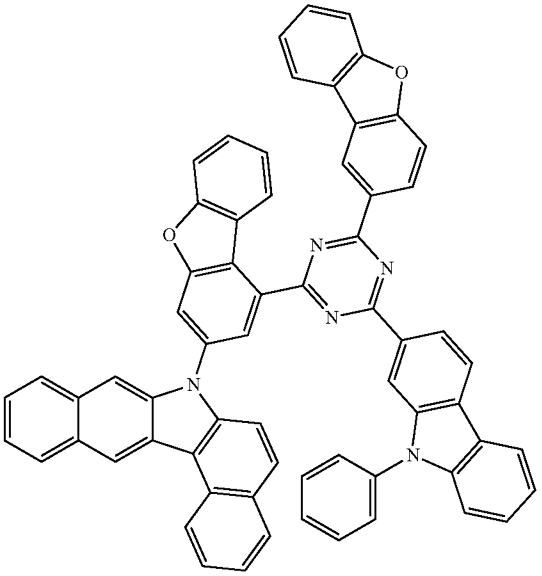
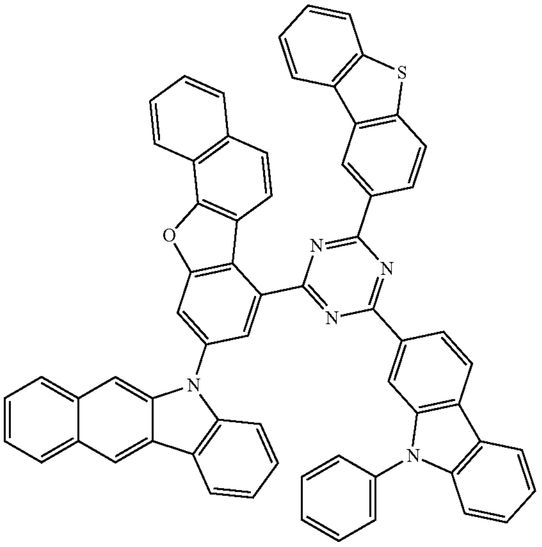
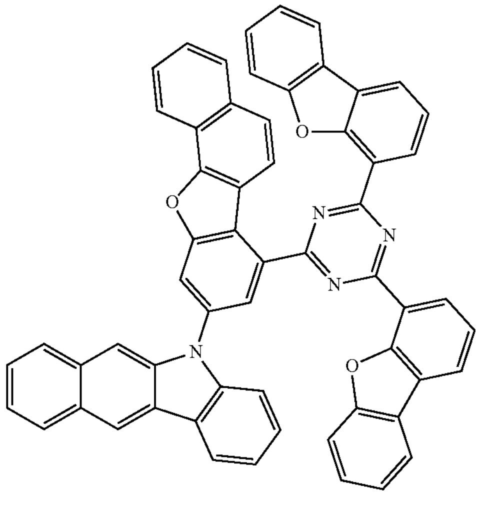

-continued
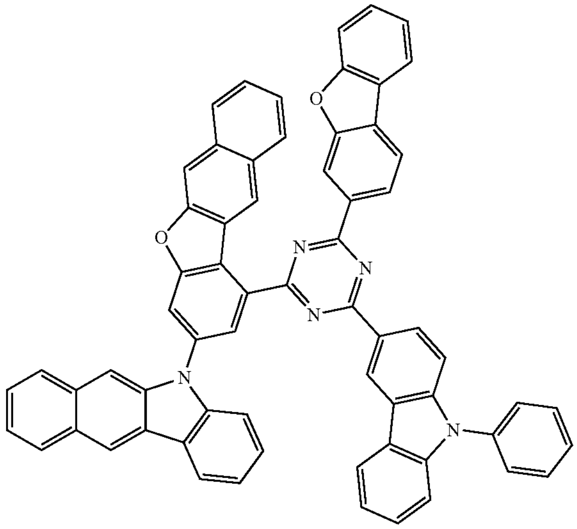
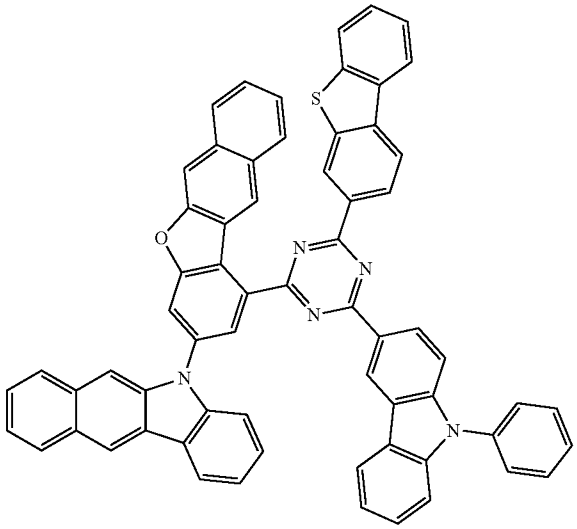
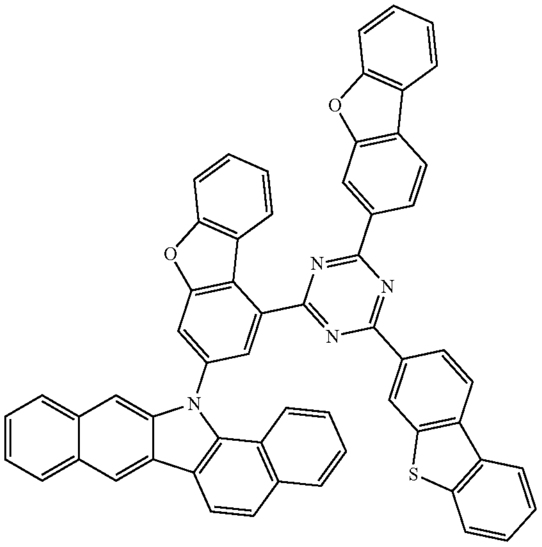
-continued
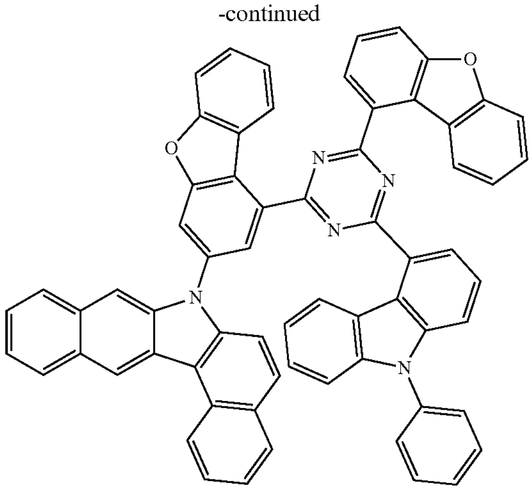
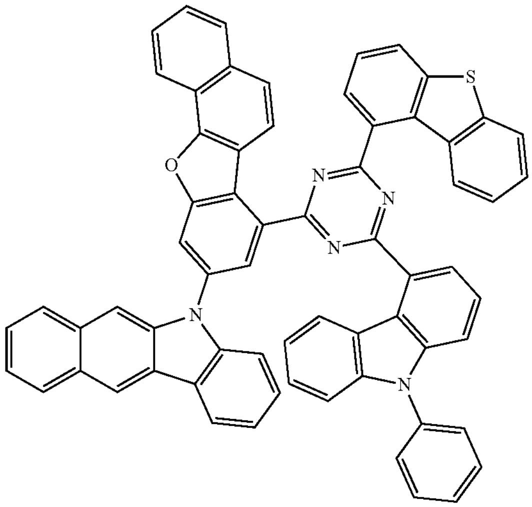
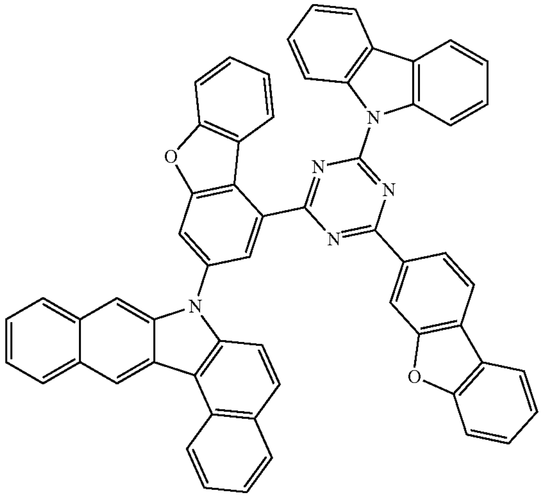

-continued
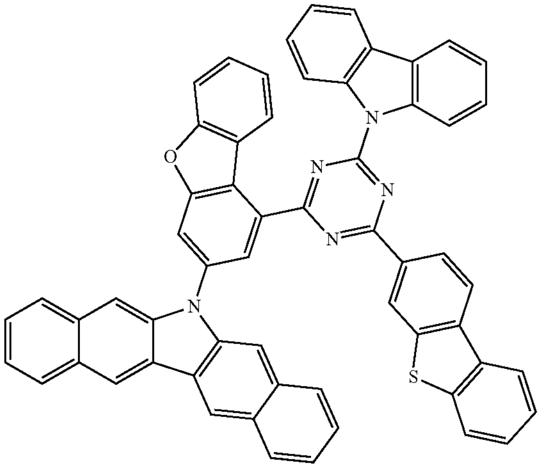
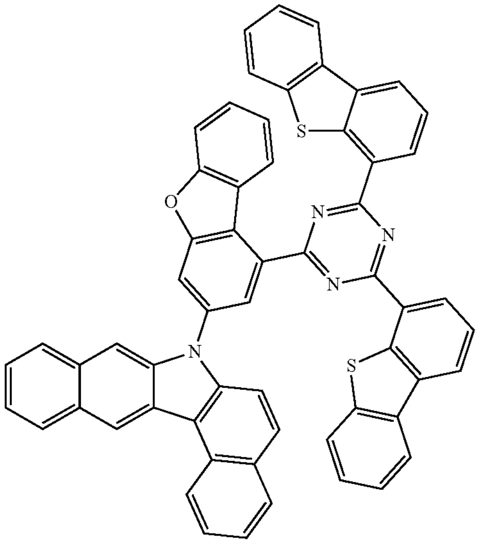
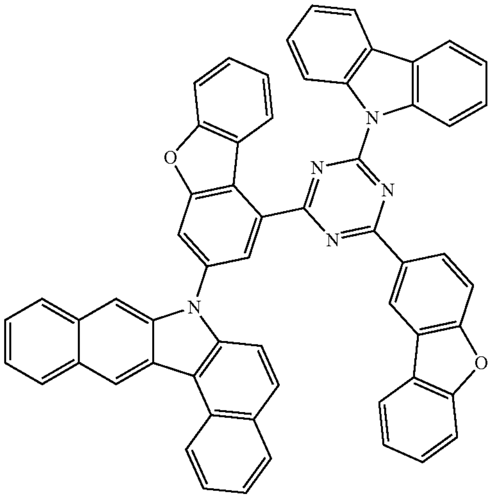
-continued
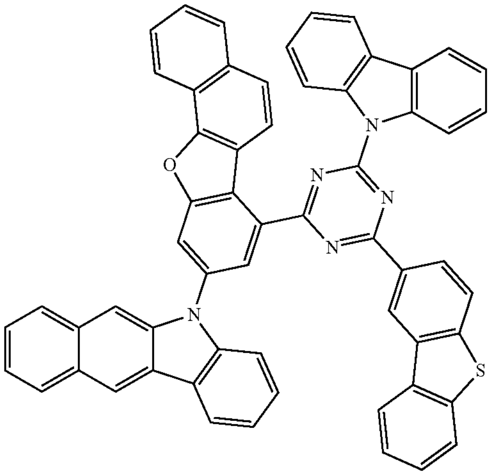
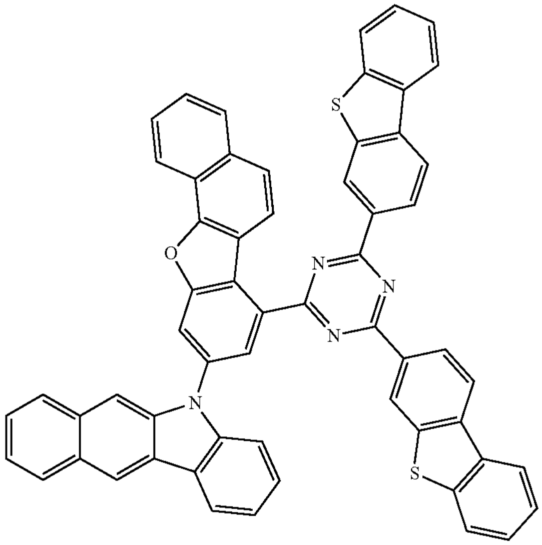
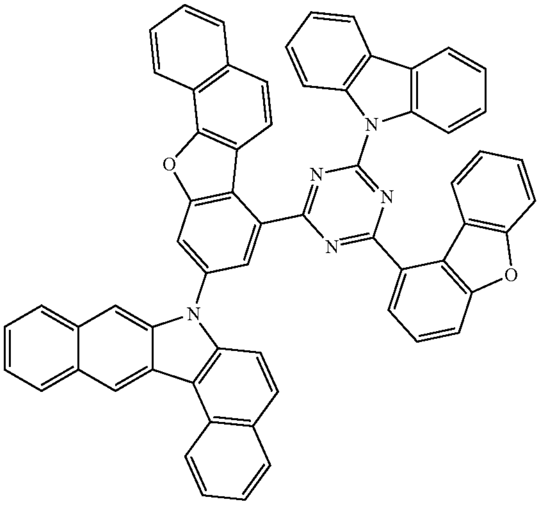

-continued
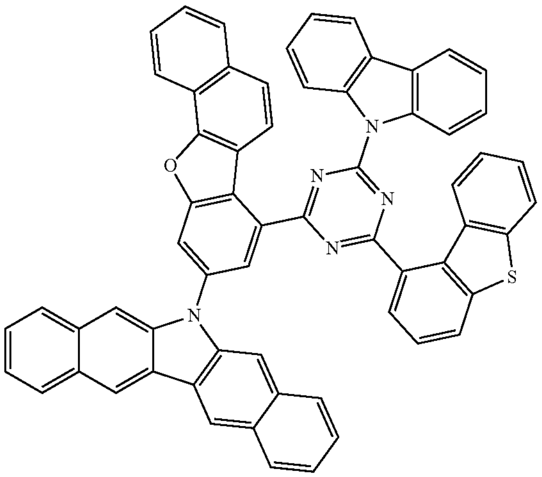
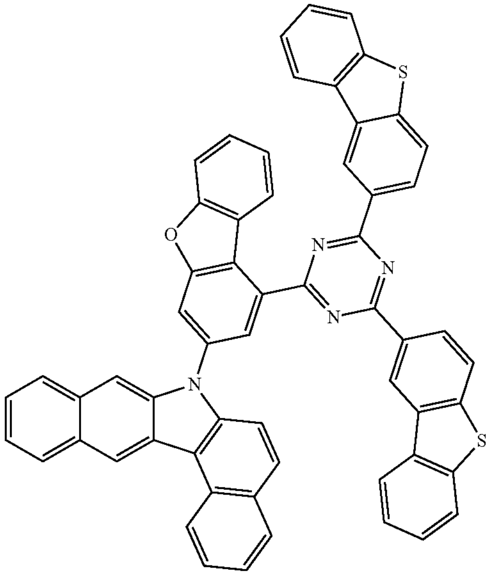
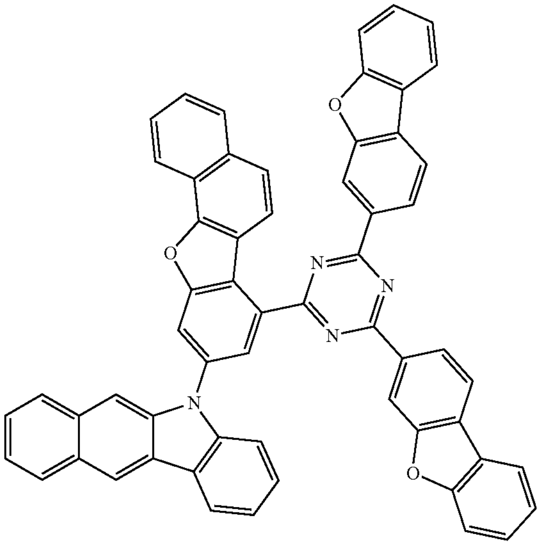
-continued
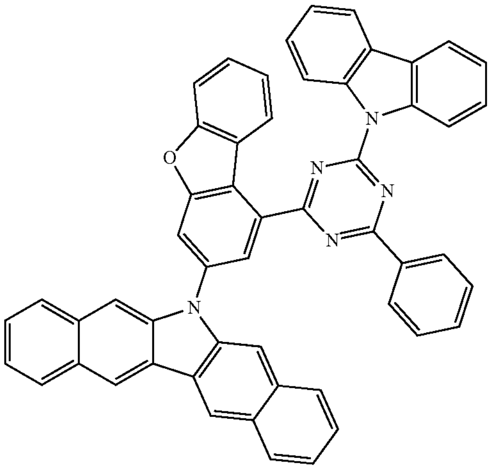
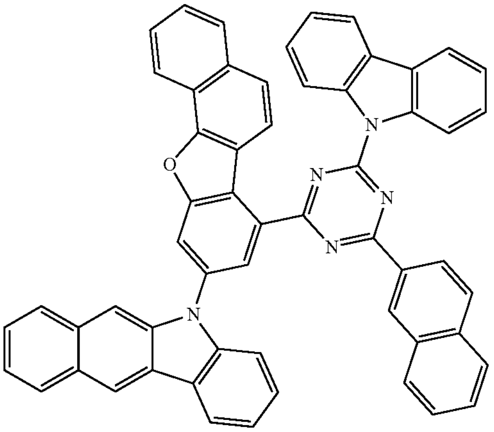
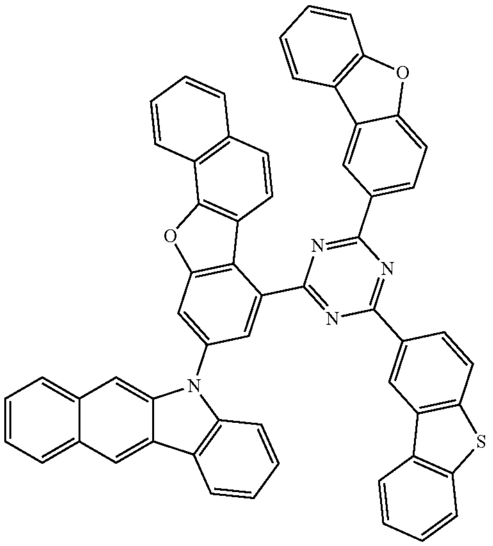

-continued
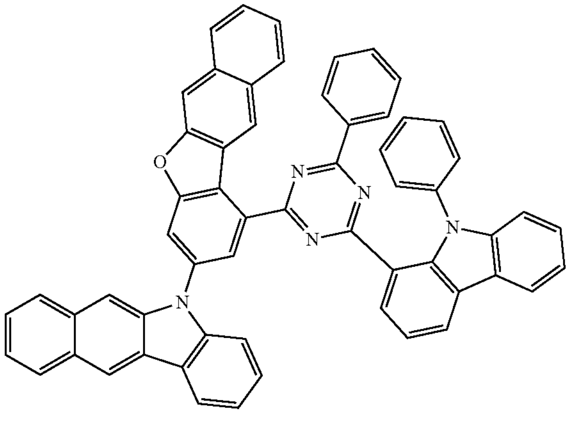
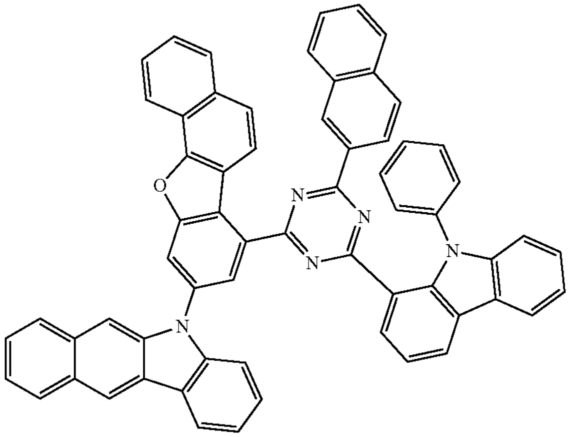
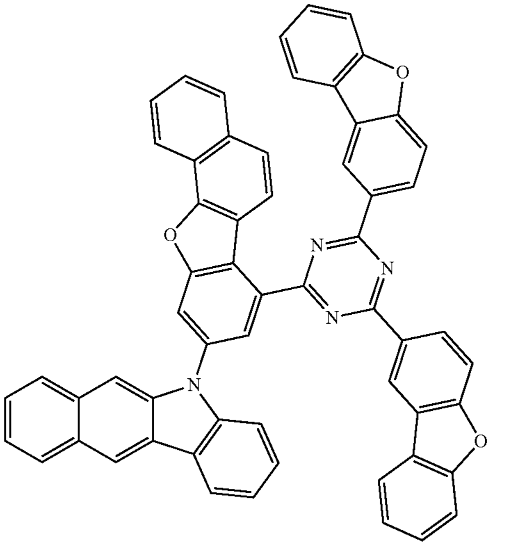
-continued
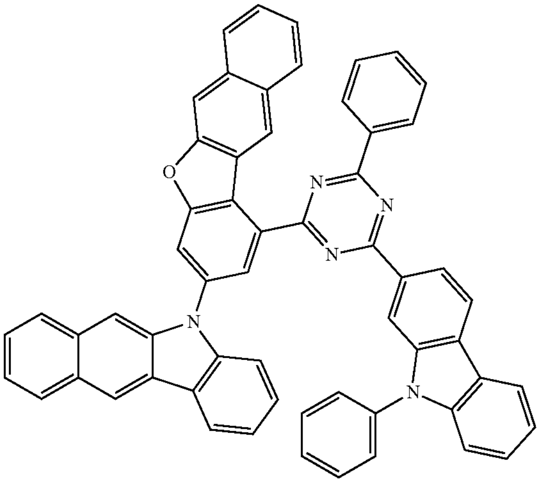
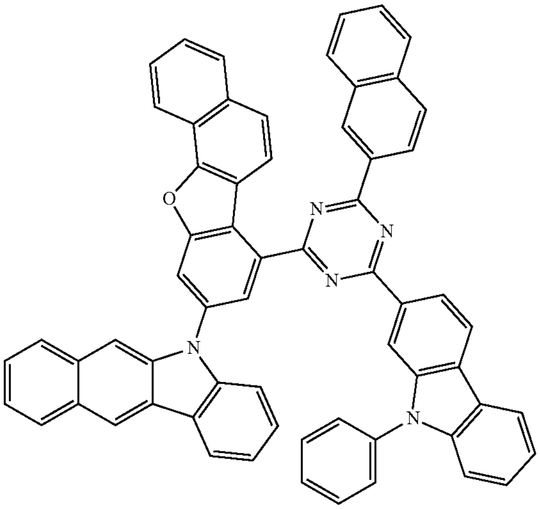
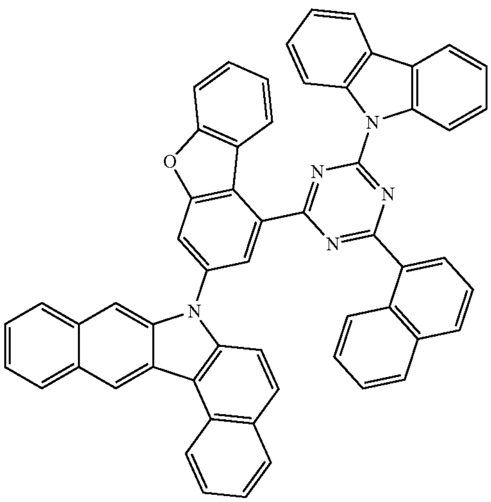

-continued
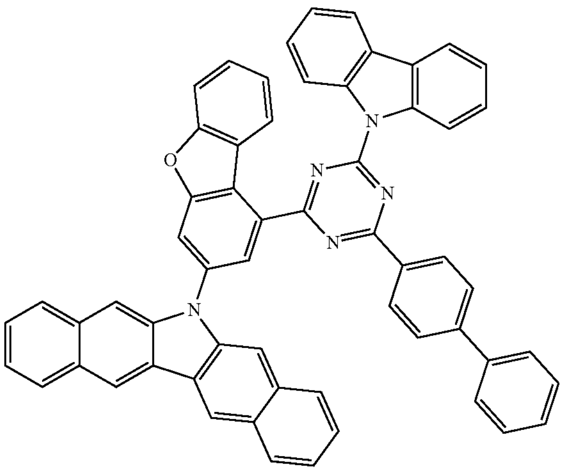
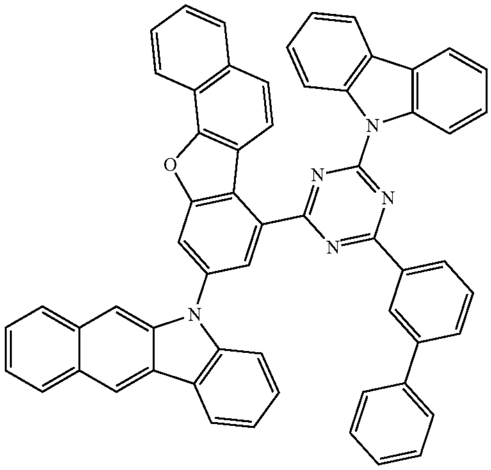
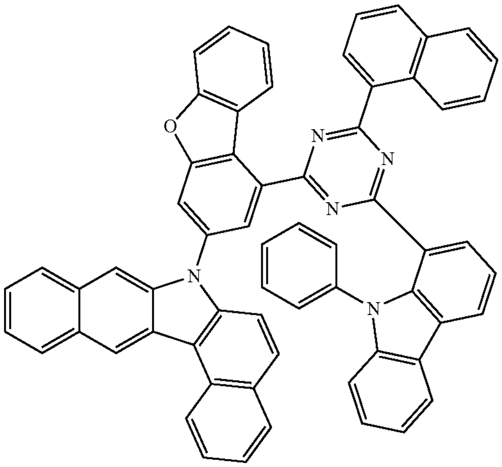
-continued
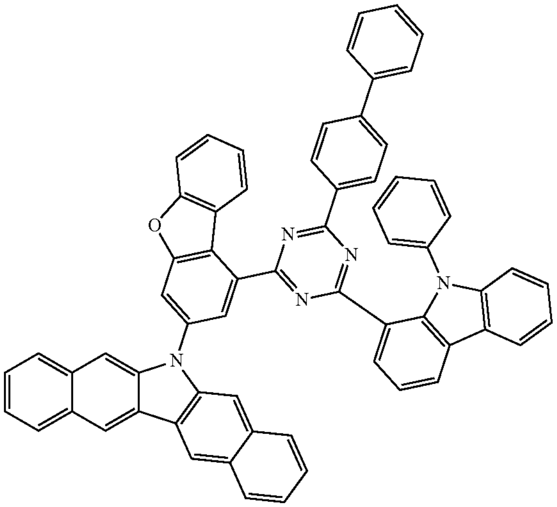
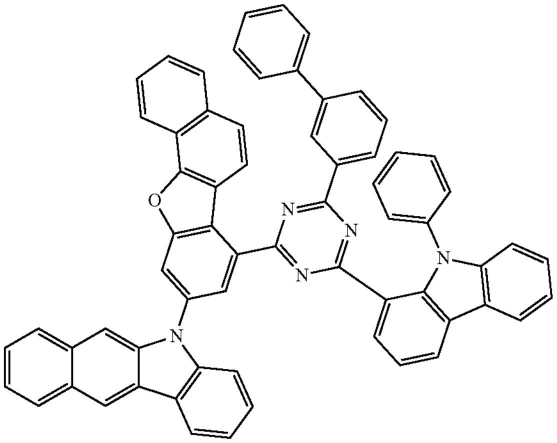
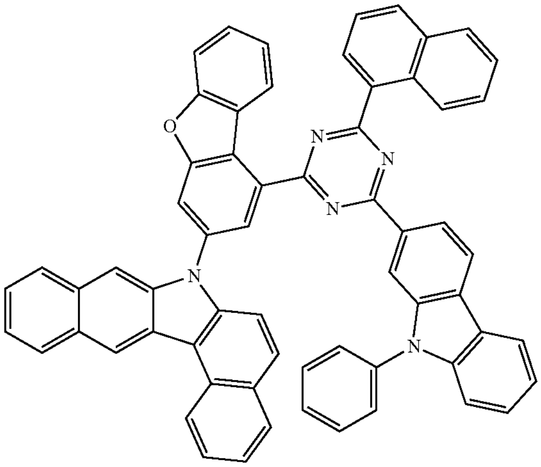

-continued
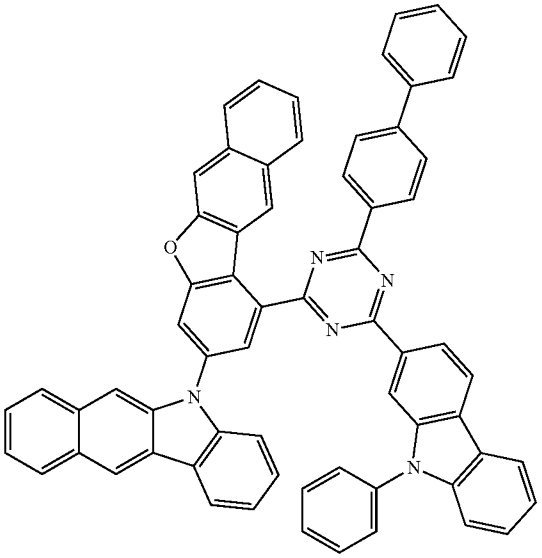
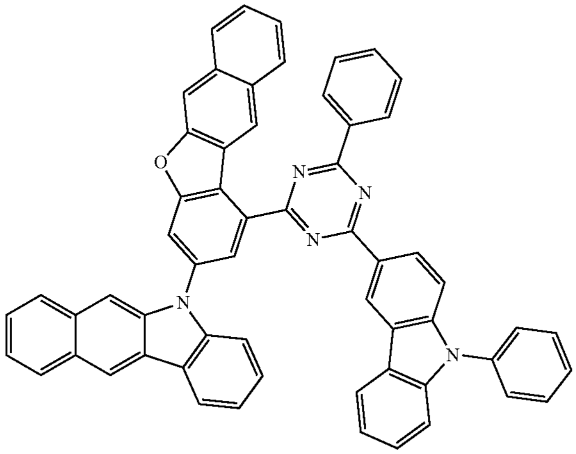
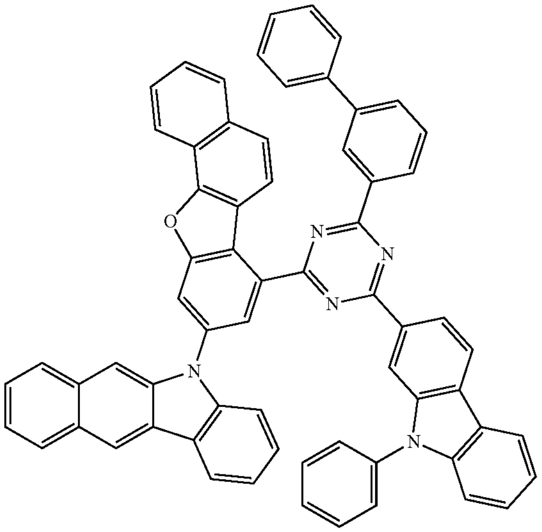
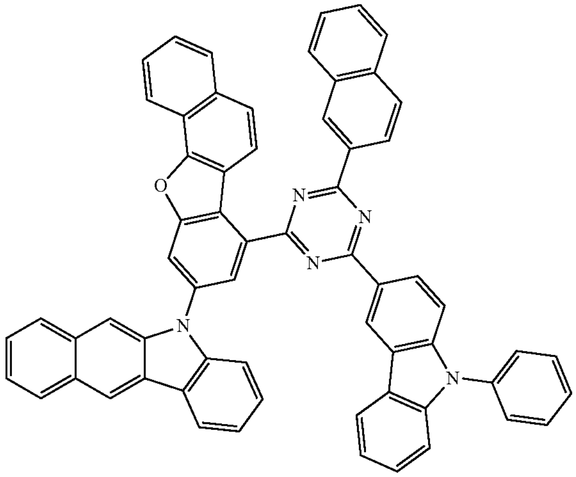
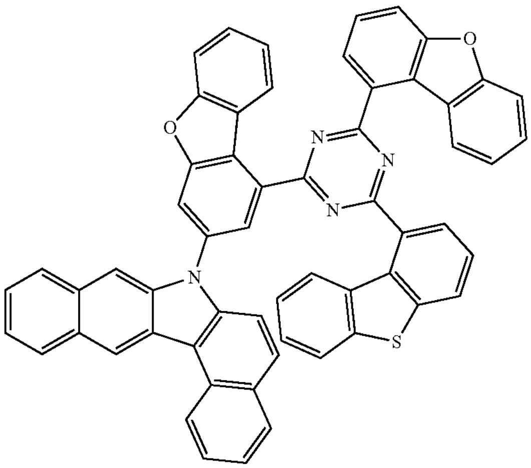
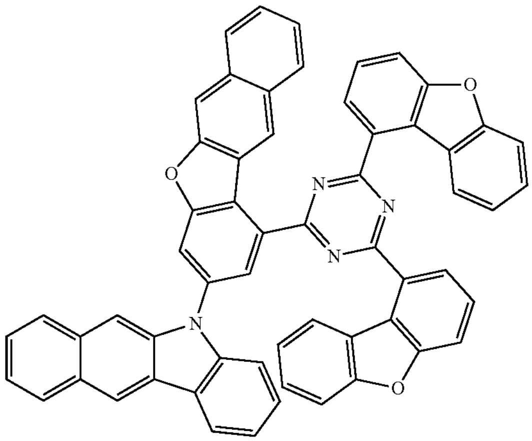
-continued -continued
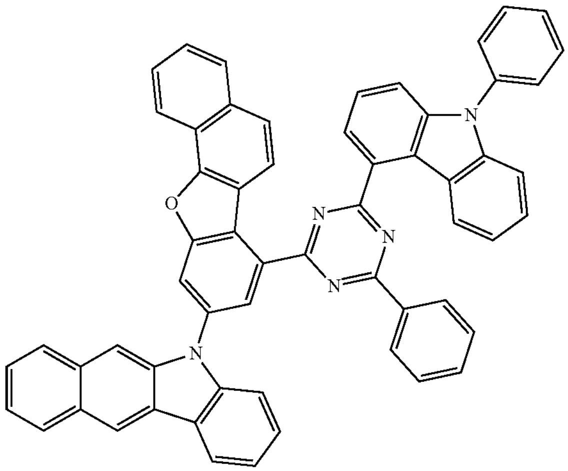
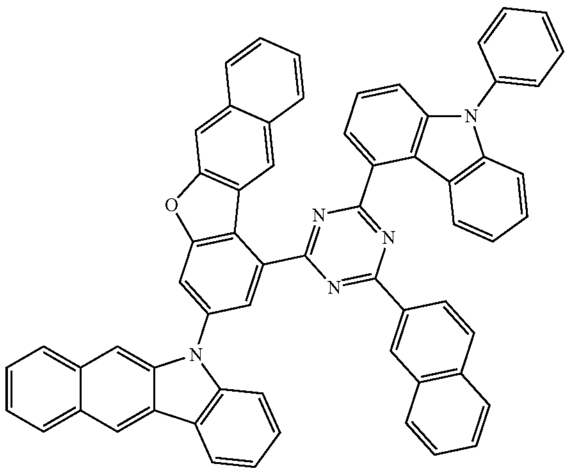
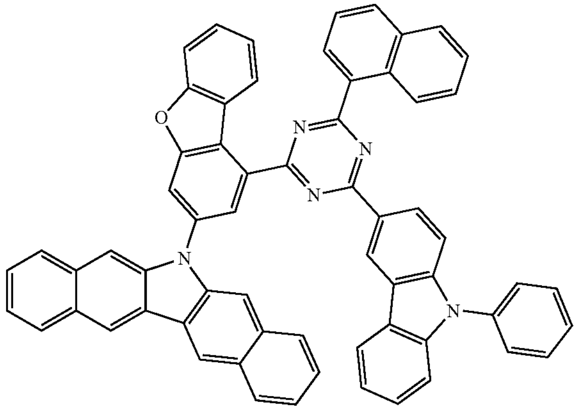
-continued
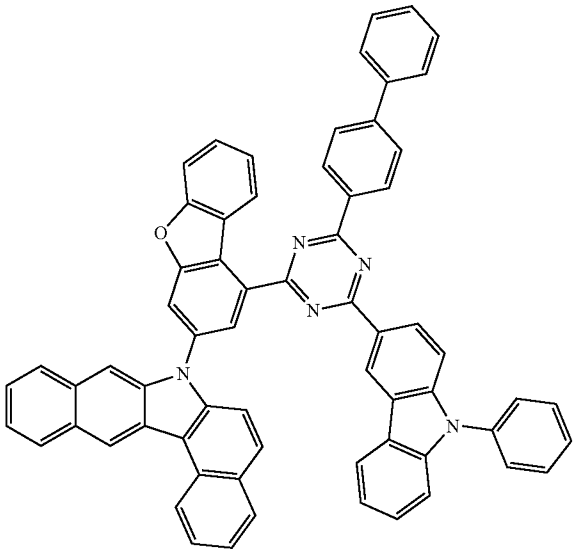
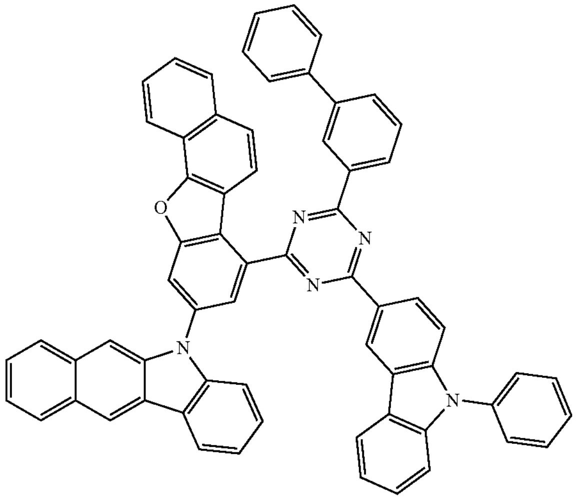
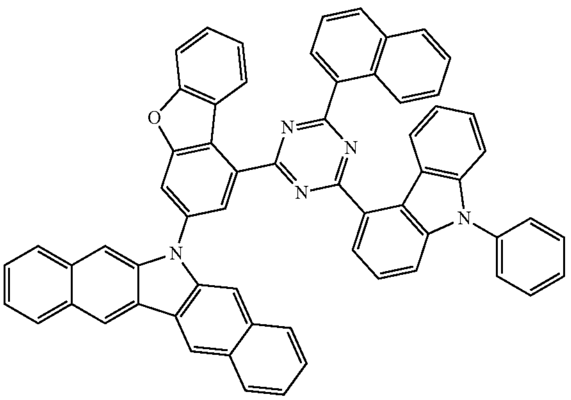

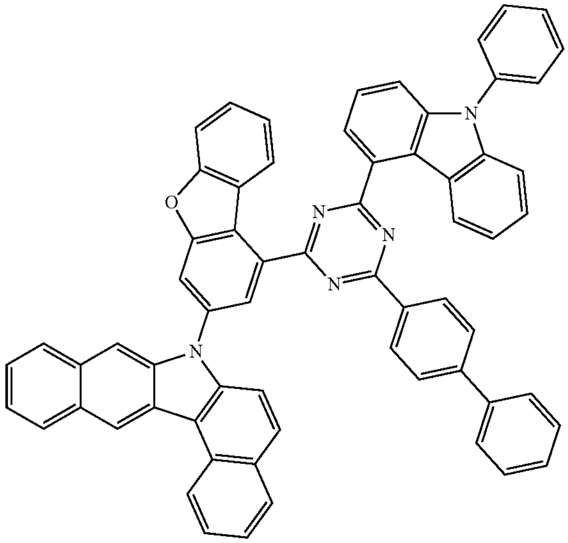
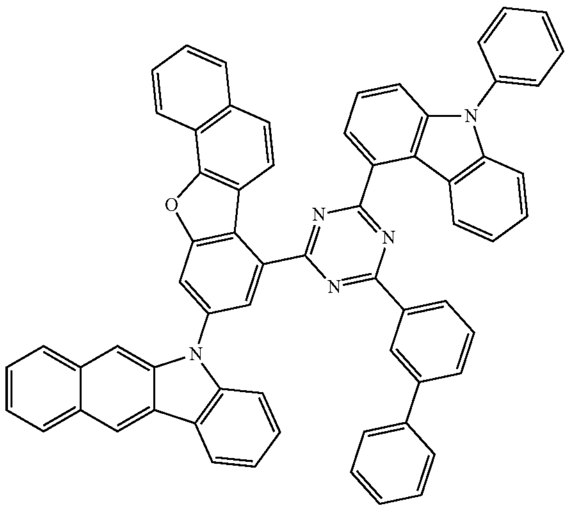
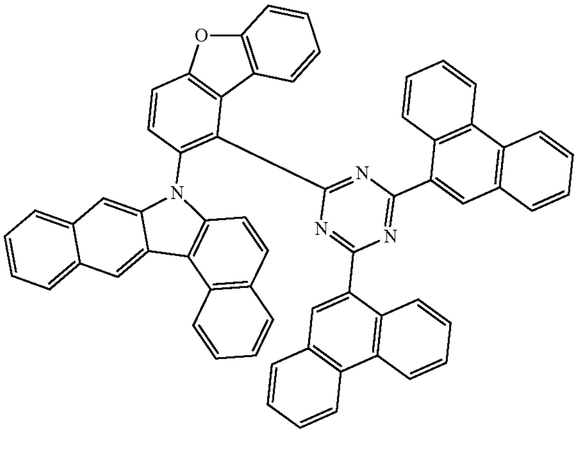
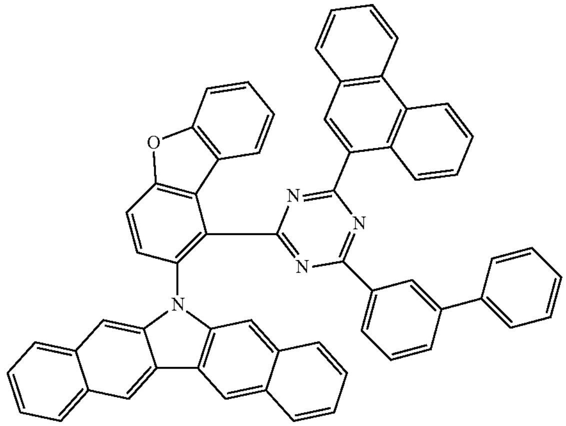
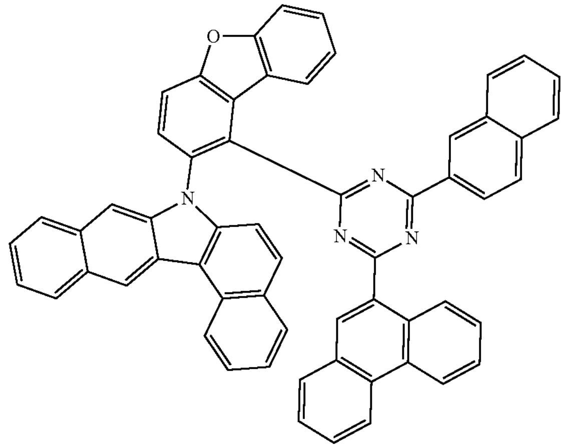
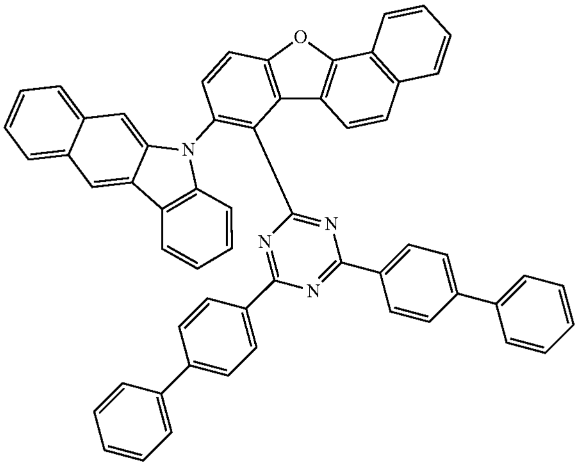

-continued
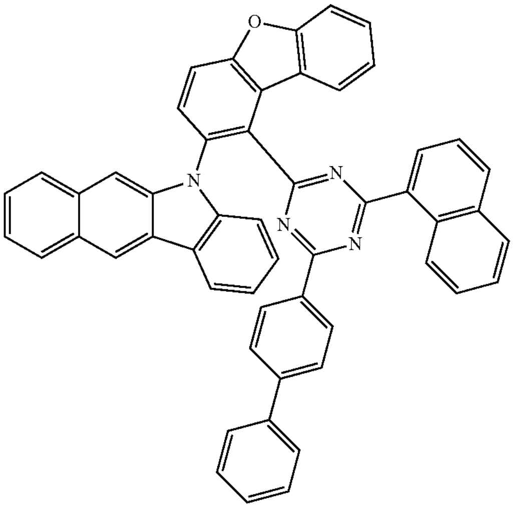
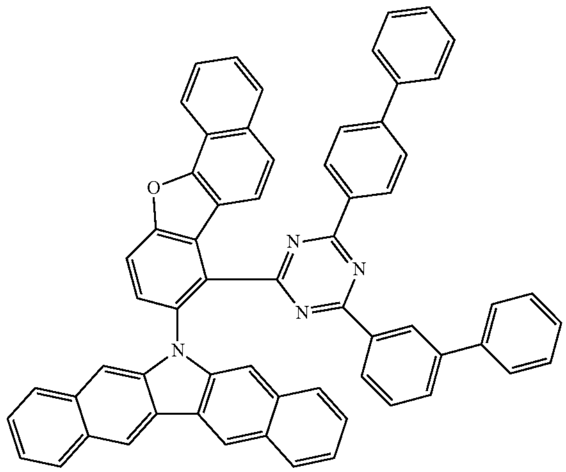
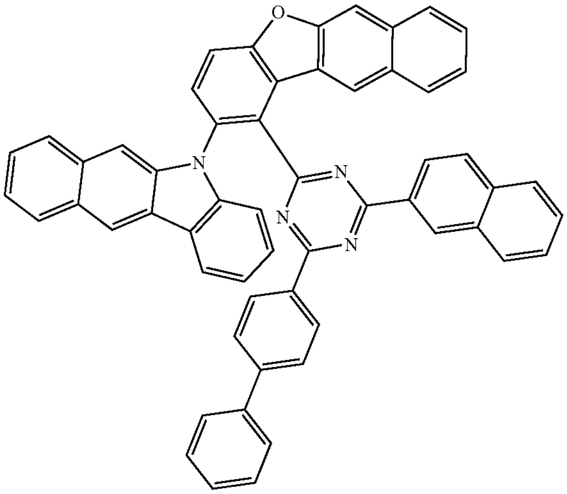
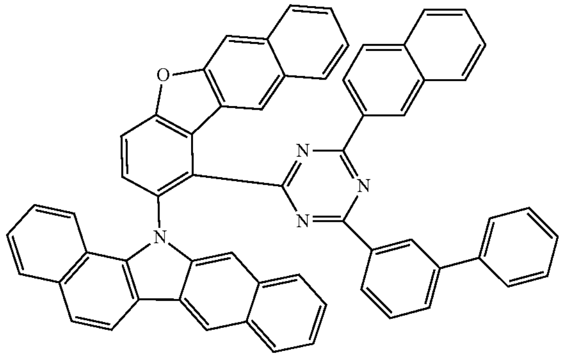
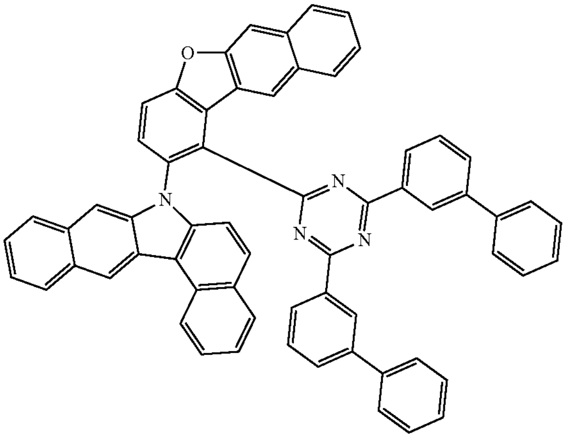
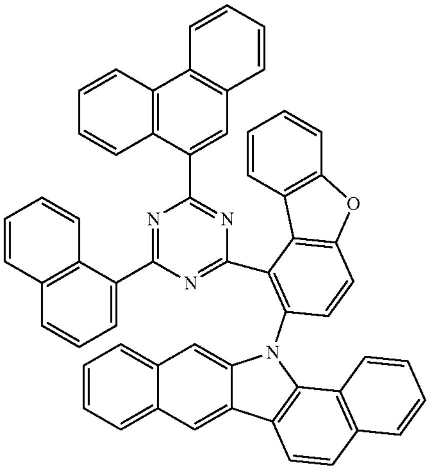

-continued
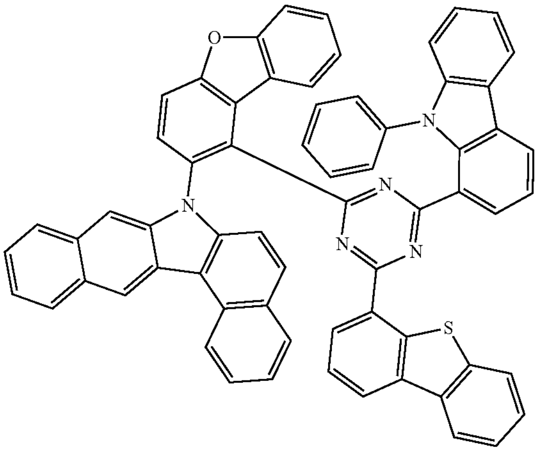
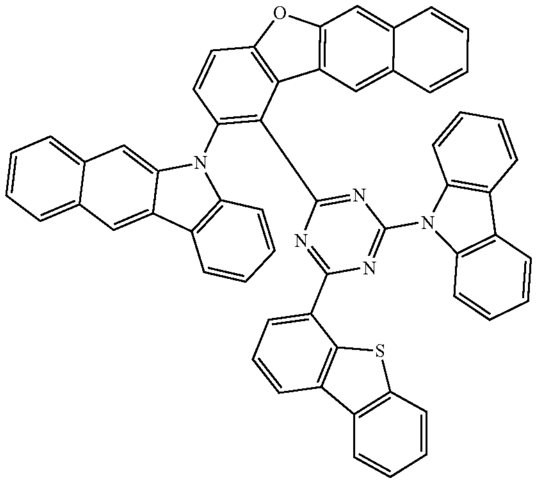
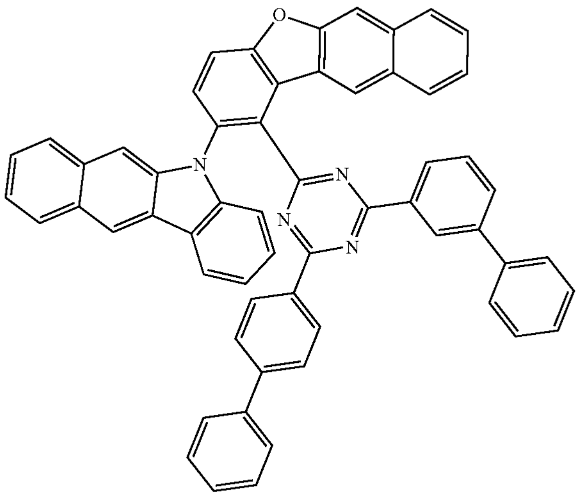
-continued
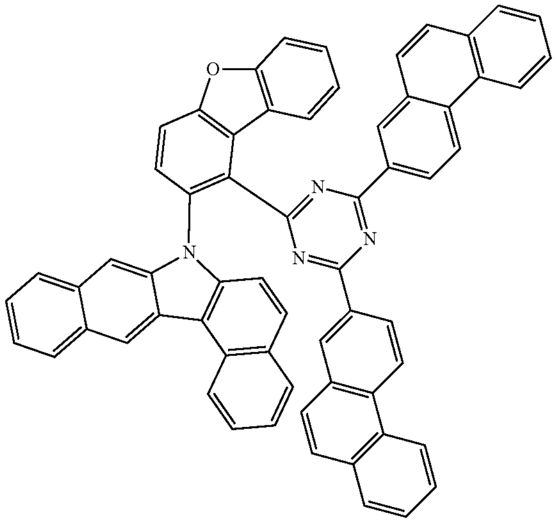
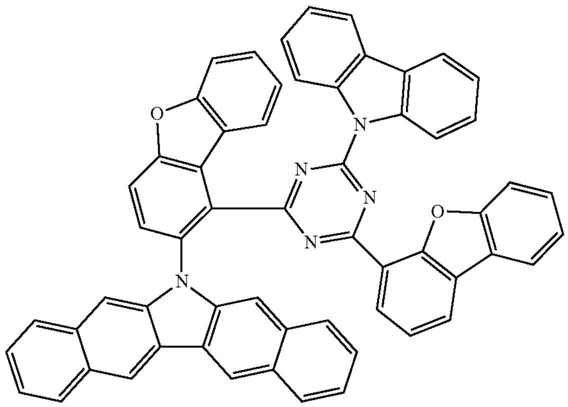
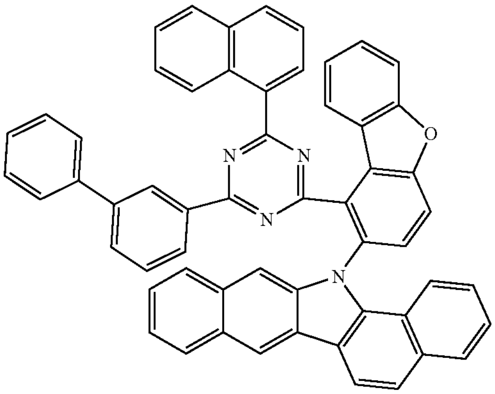

-continued
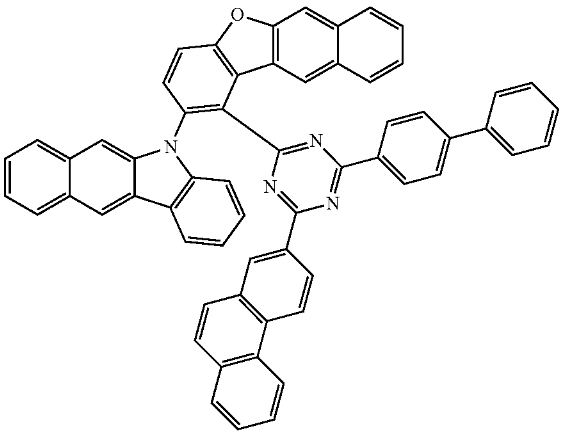
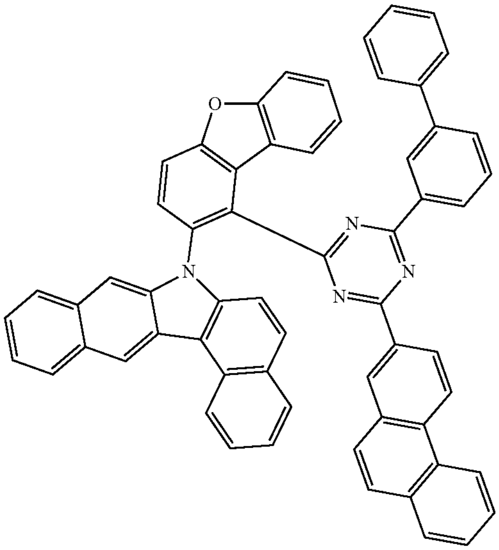
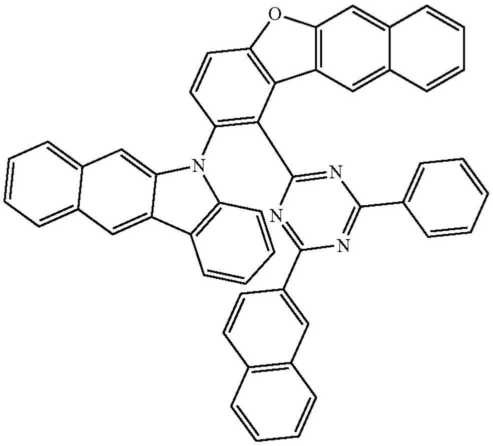
-continued
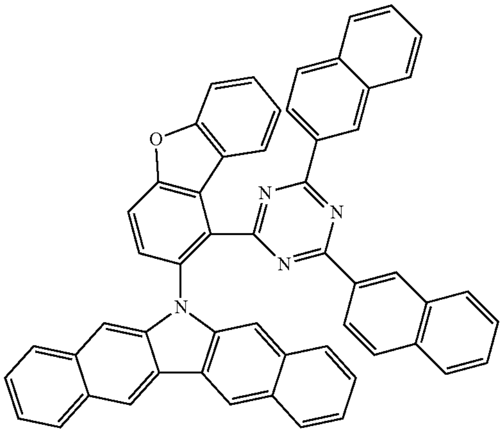
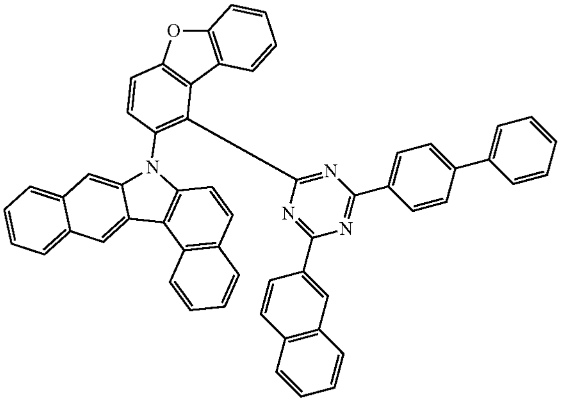
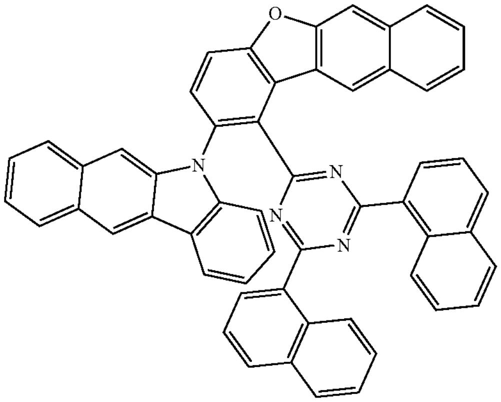
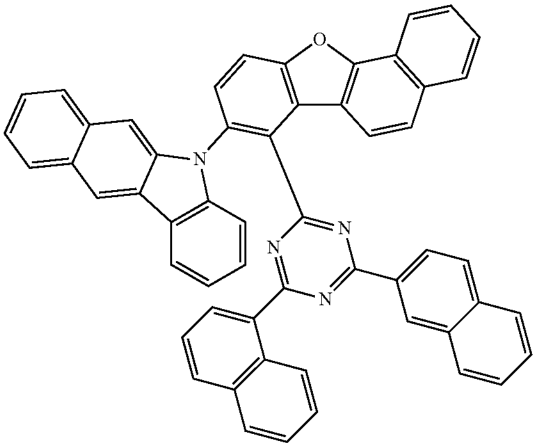

-continued
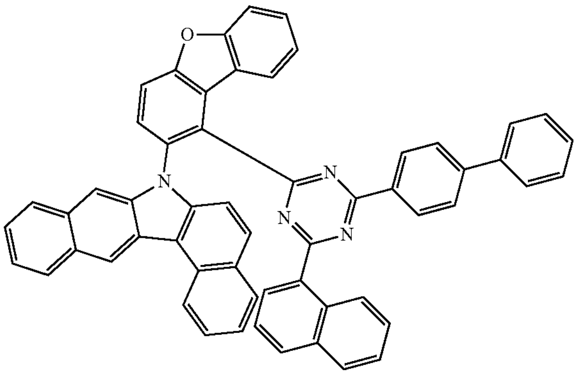
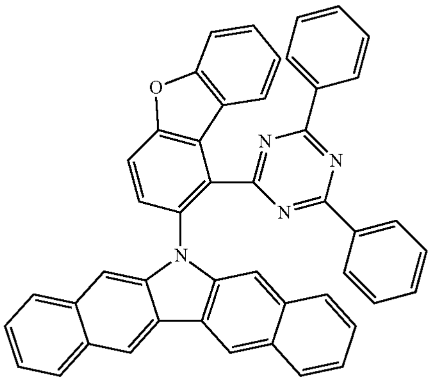
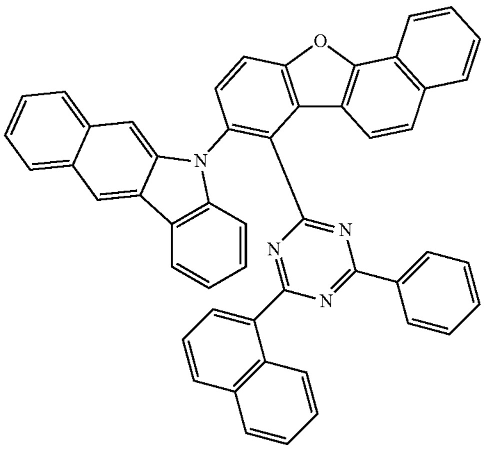
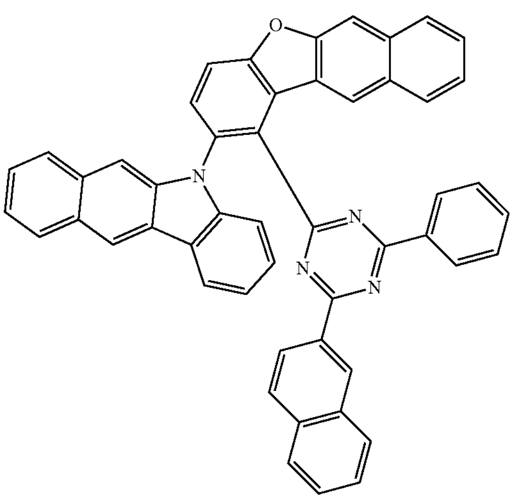
-continued
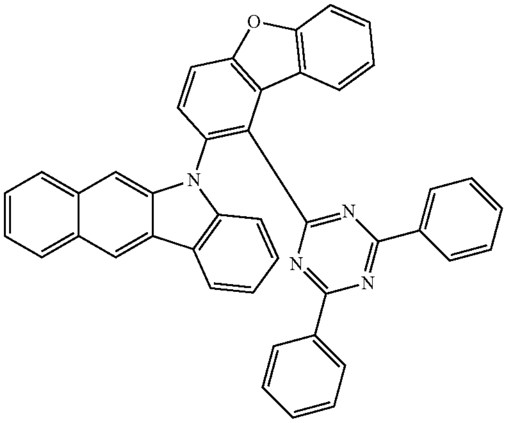
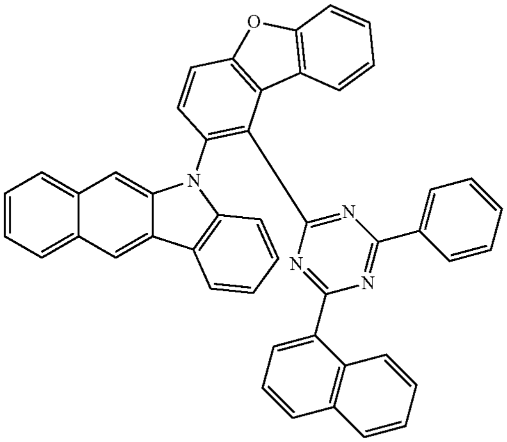
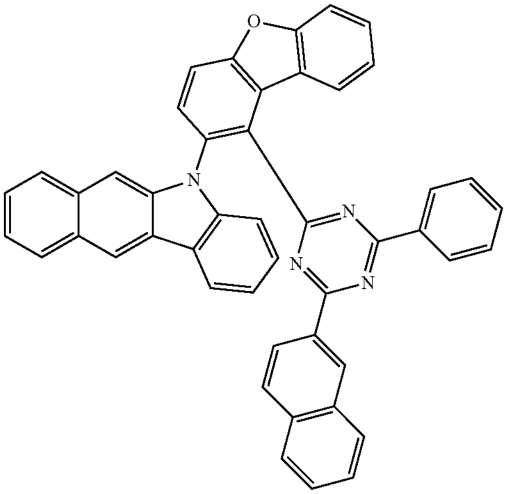

-continued
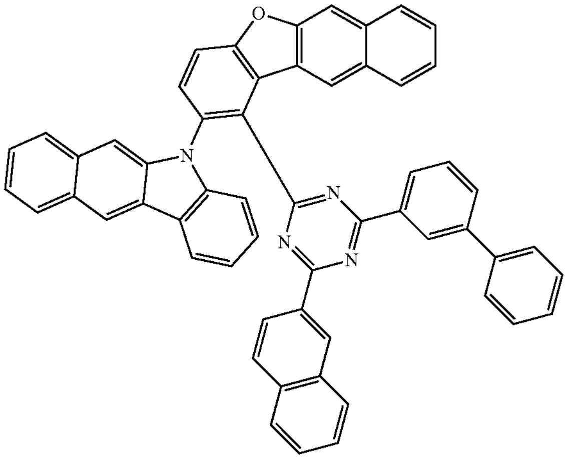
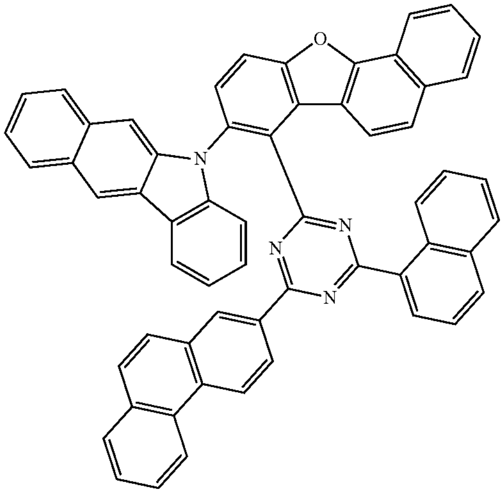
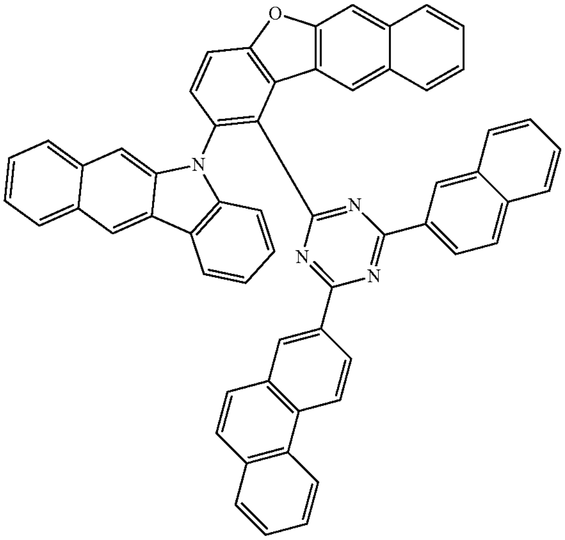
-continued
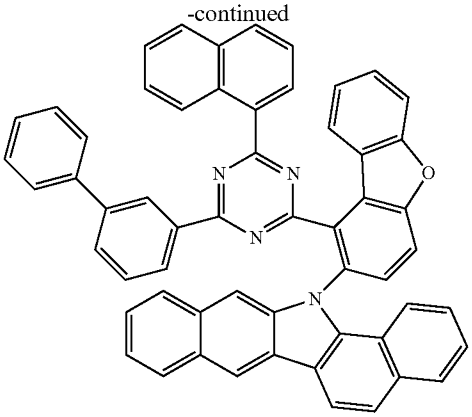
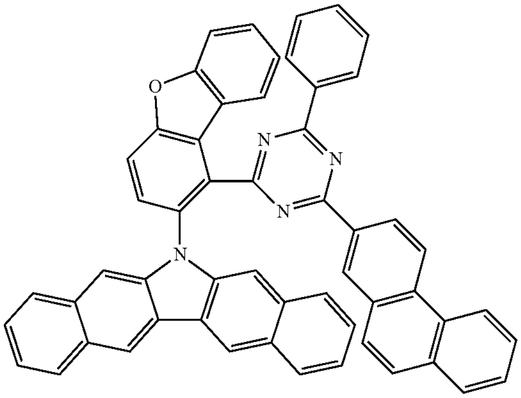
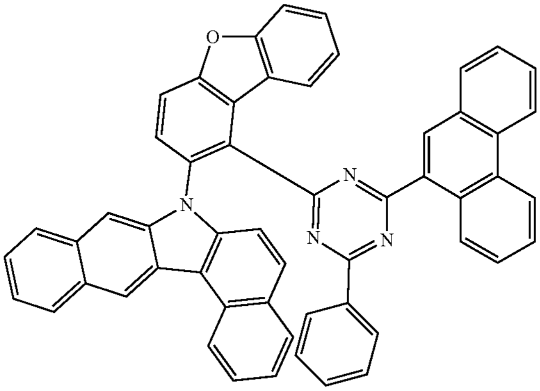
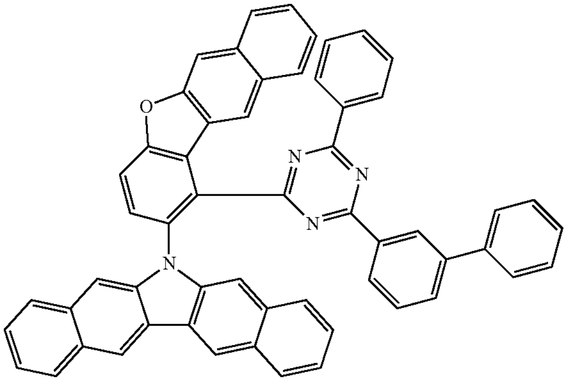

-continued
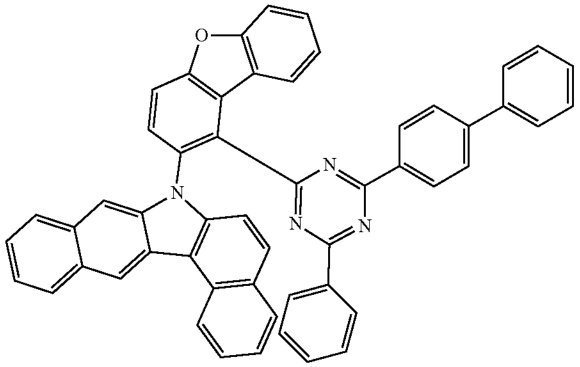
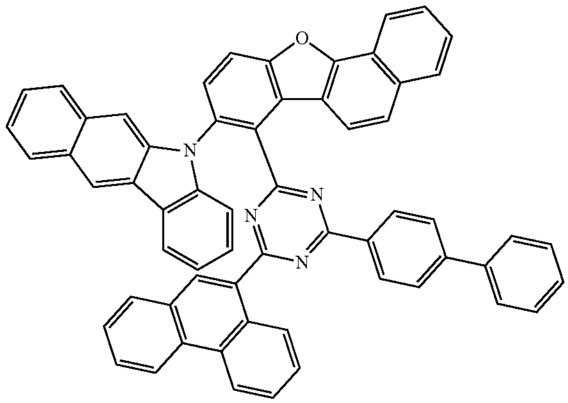
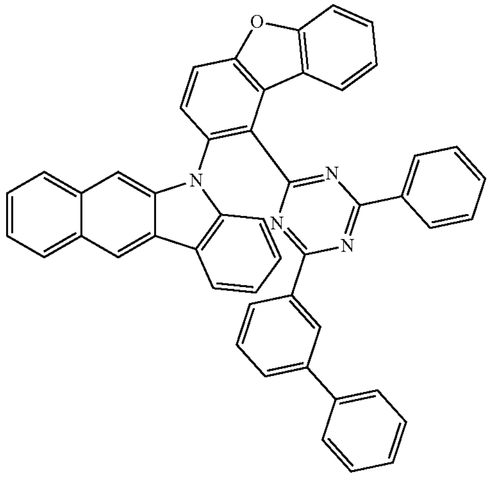
-continued
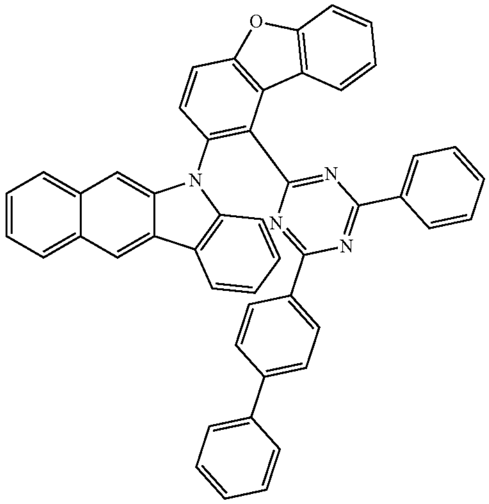
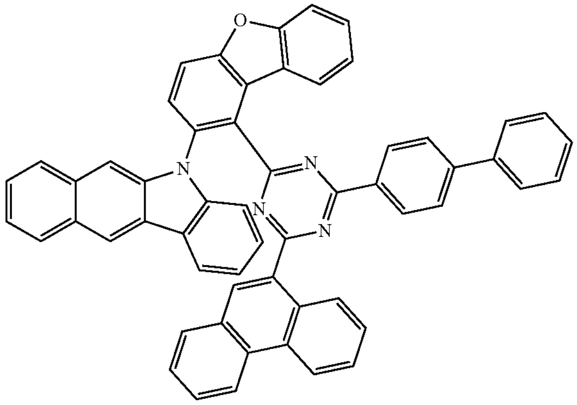
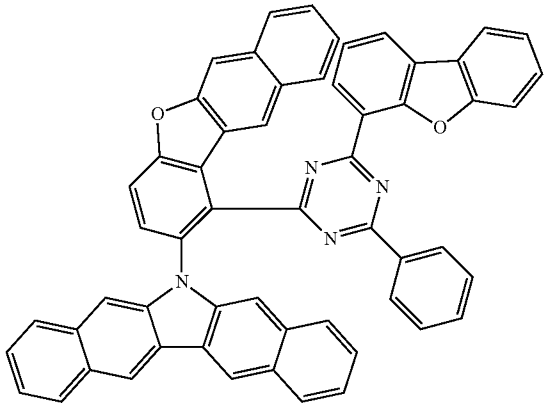

-continued
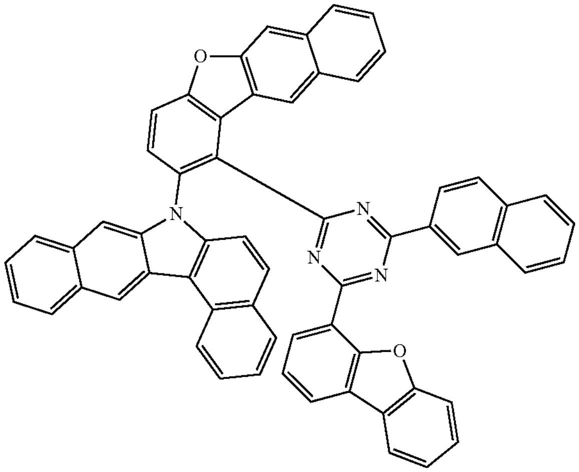
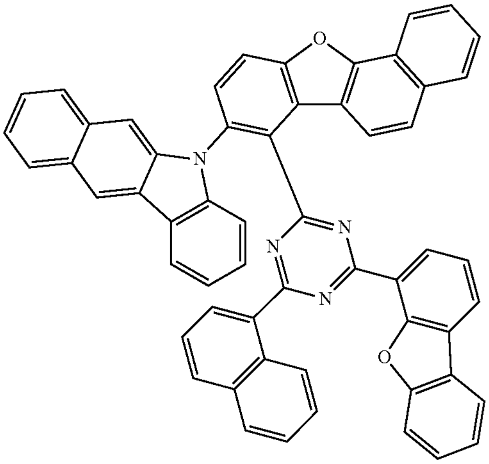
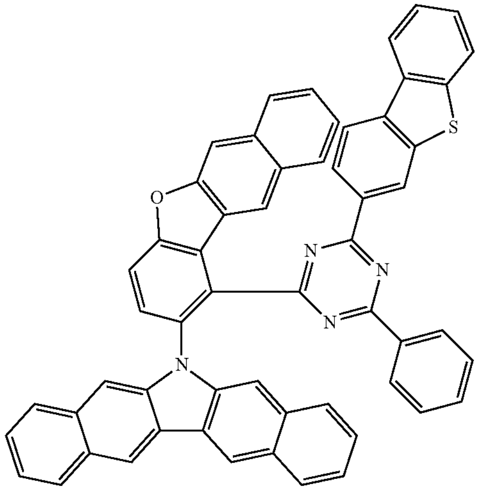
-continued
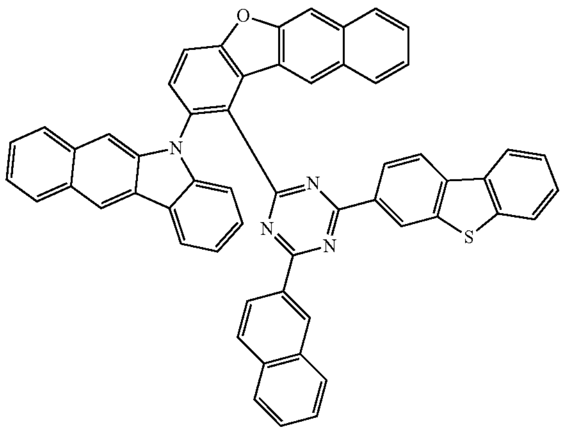
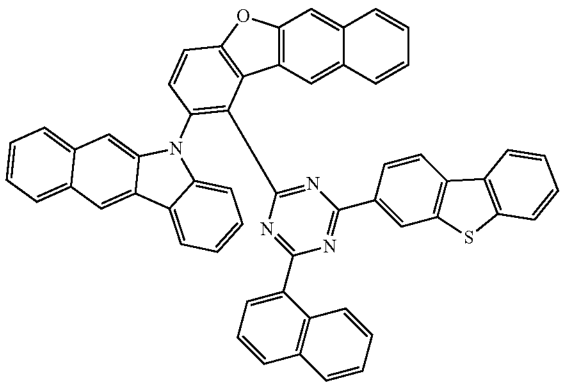
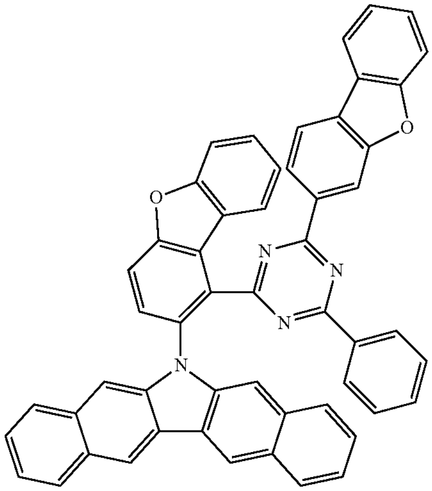

-continued
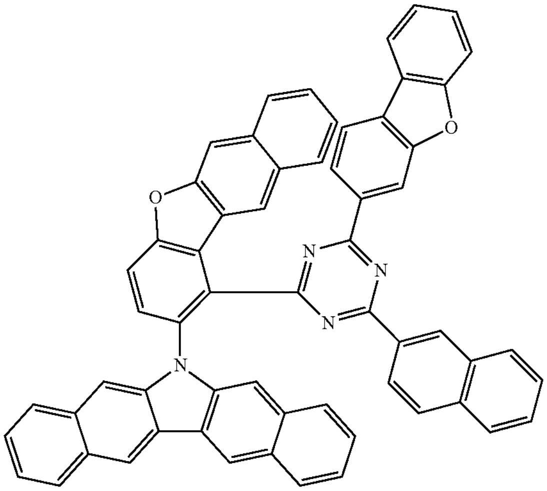
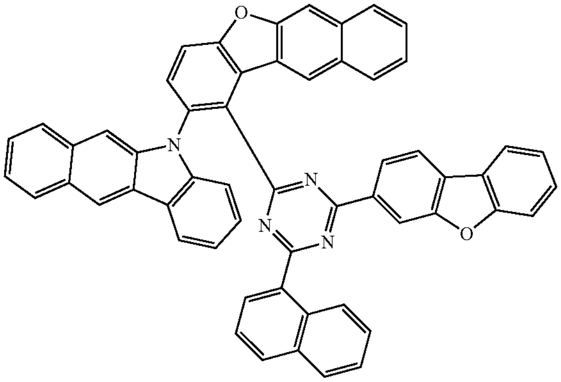
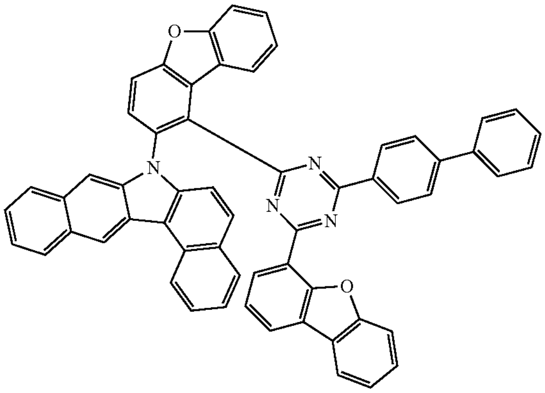
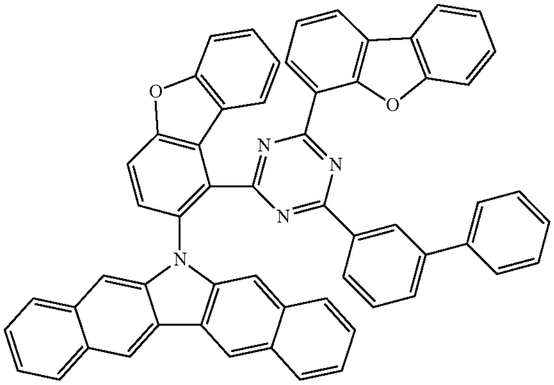
-continued
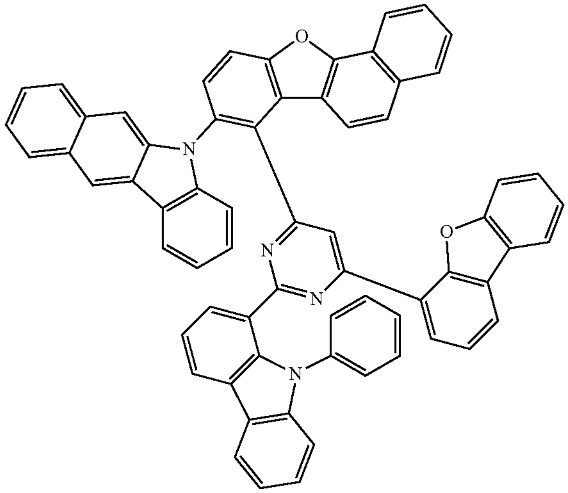
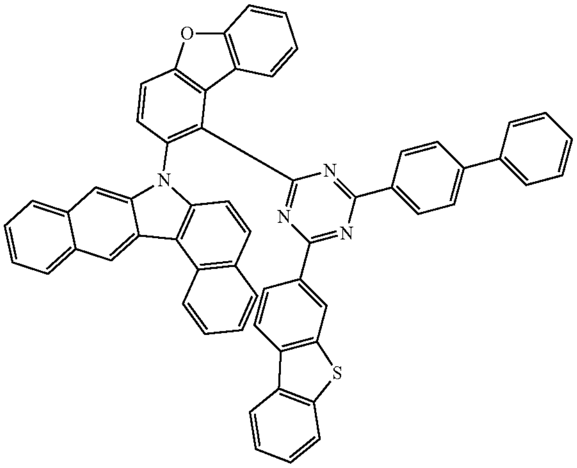
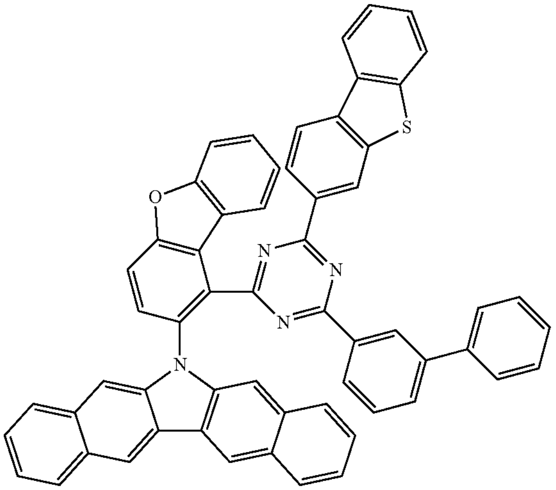

-continued
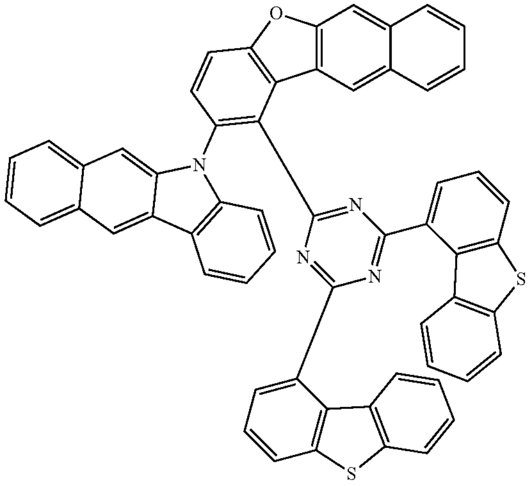
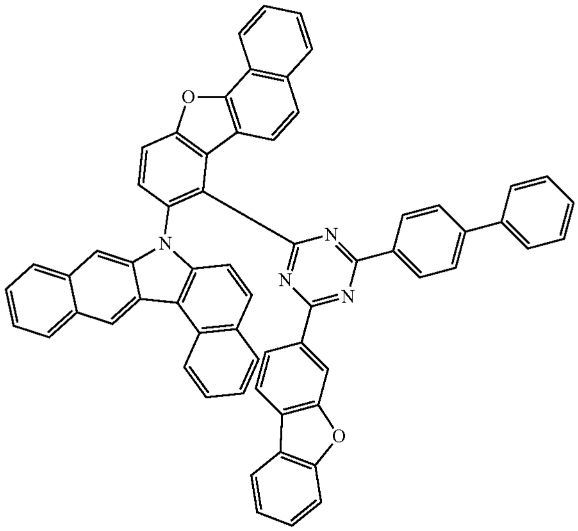
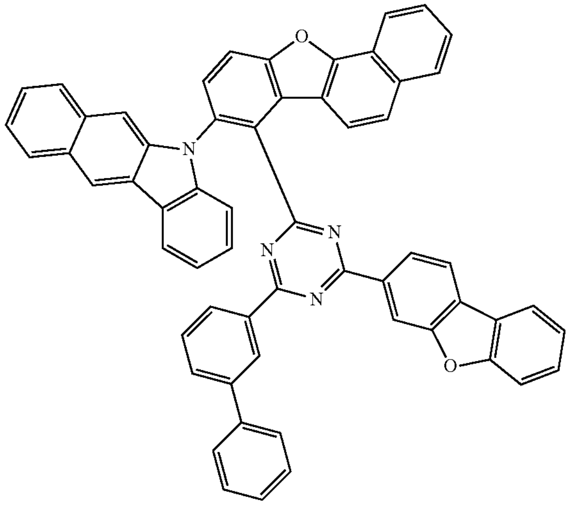
-continued
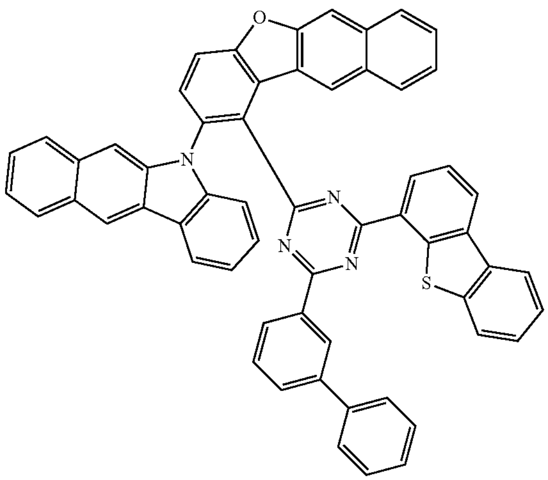
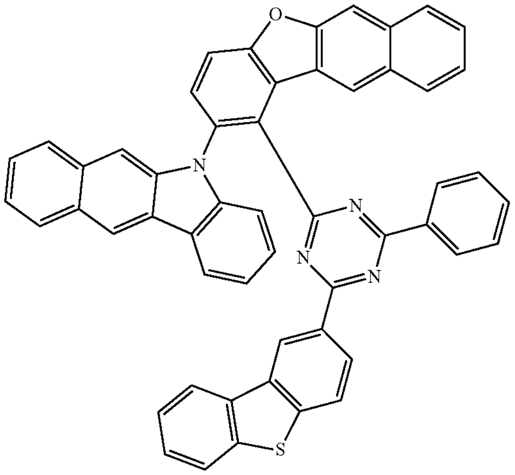
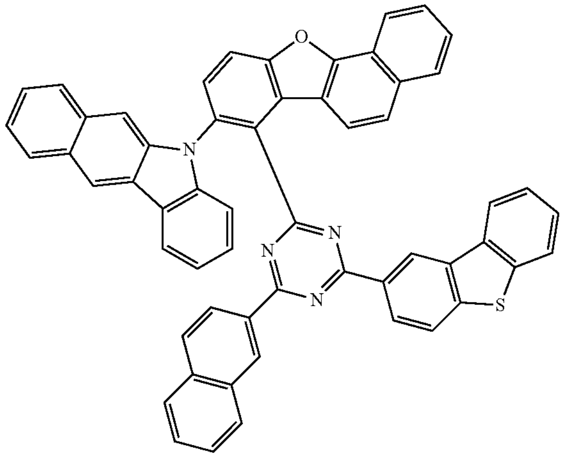

-continued
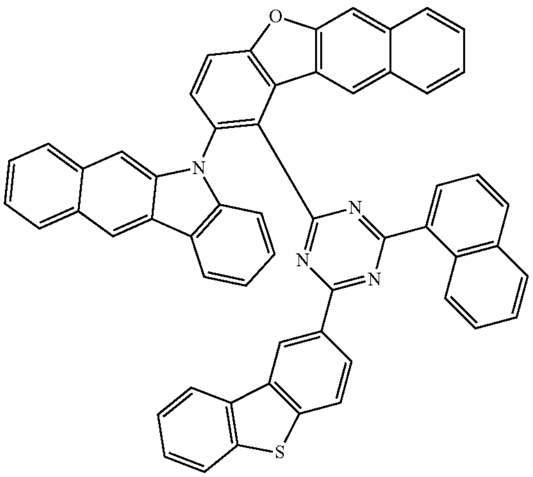
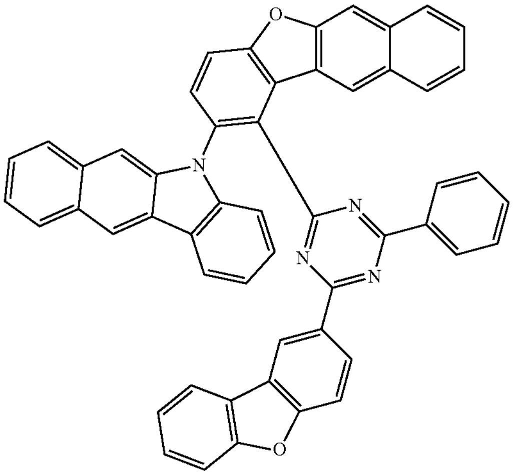
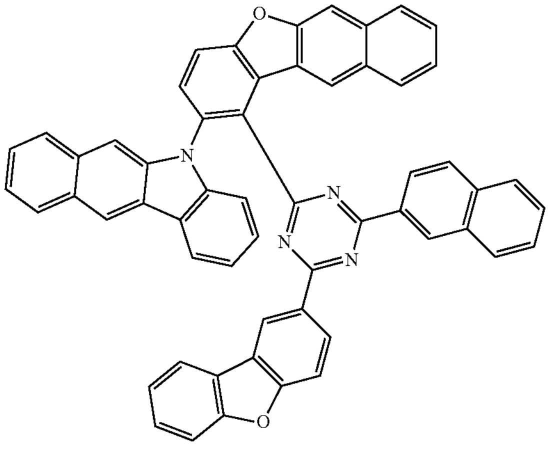
-continued
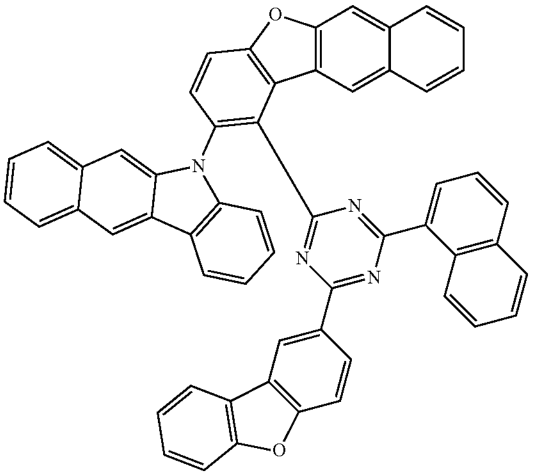
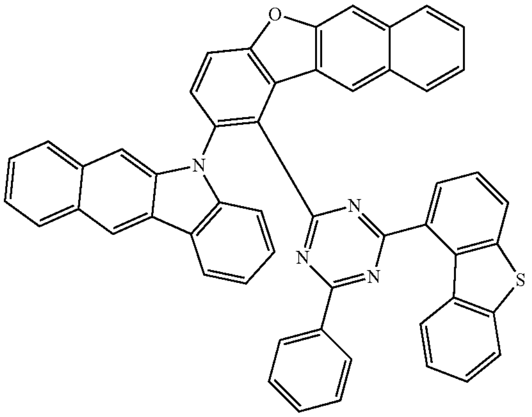
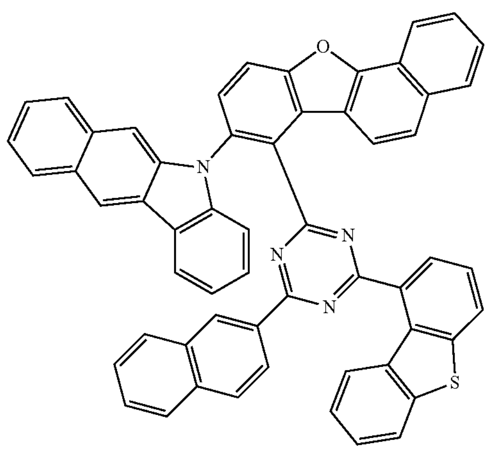

-continued
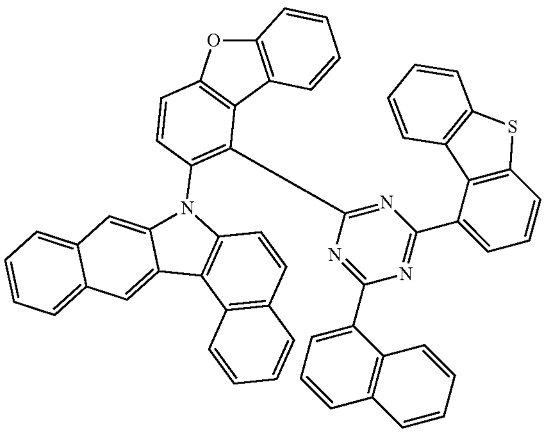
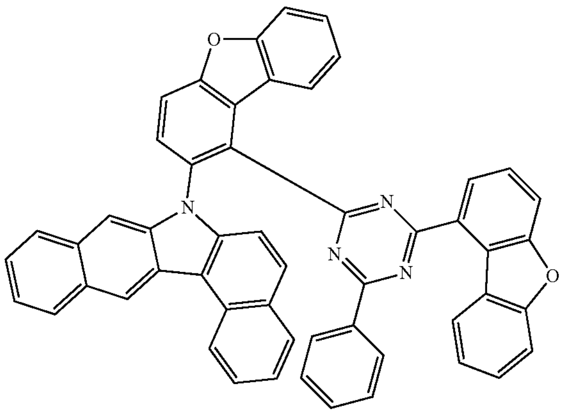
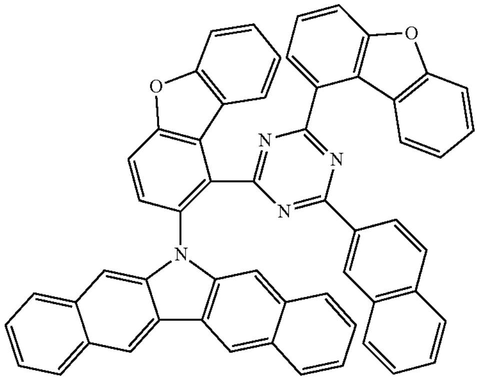
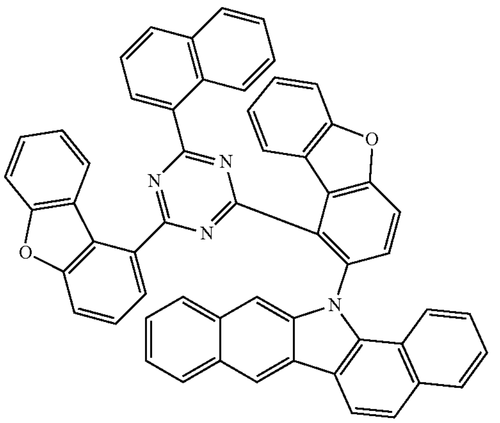
-continued
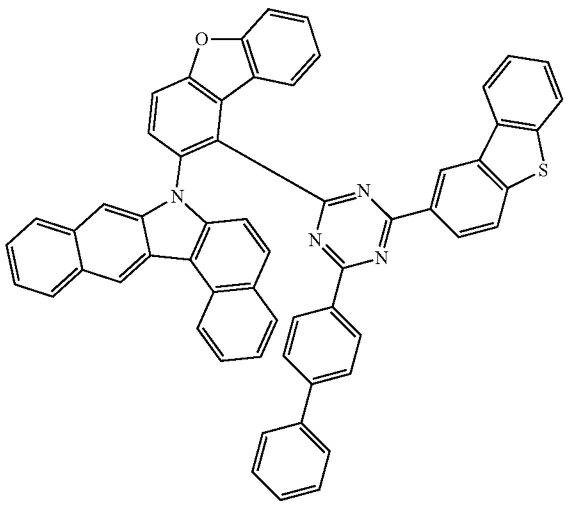
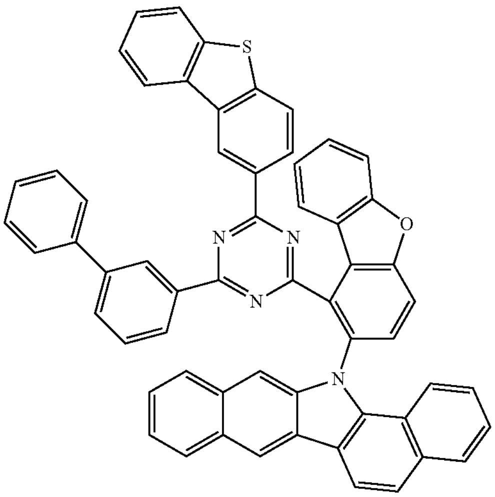
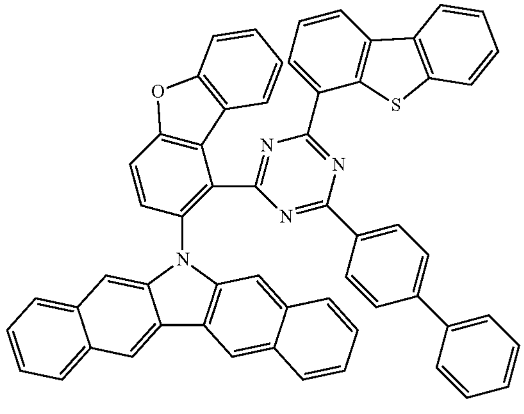

-continued
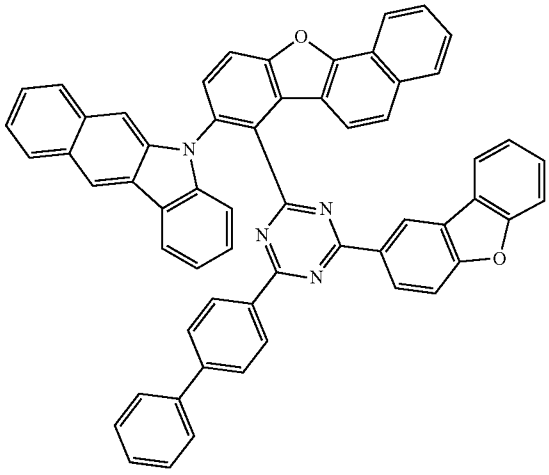
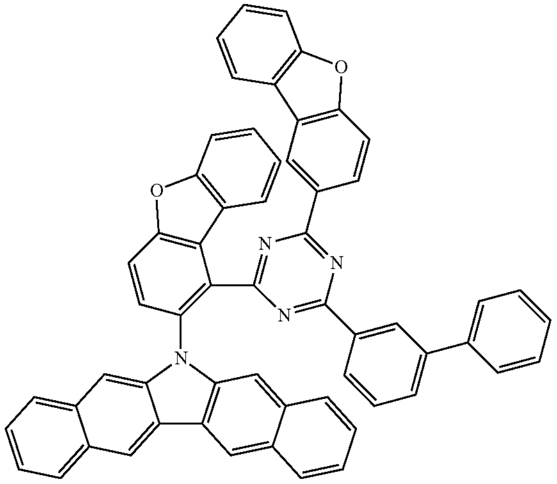
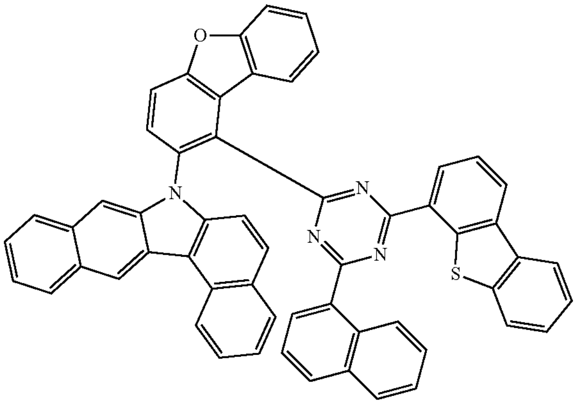
-continued
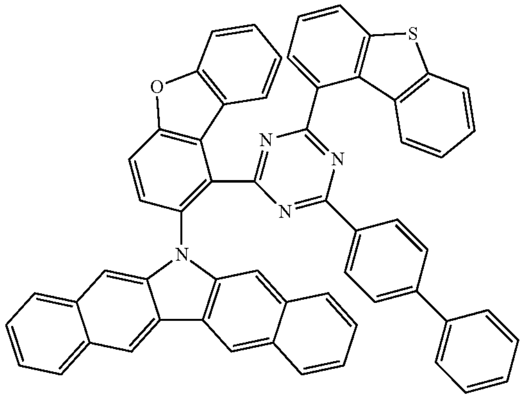
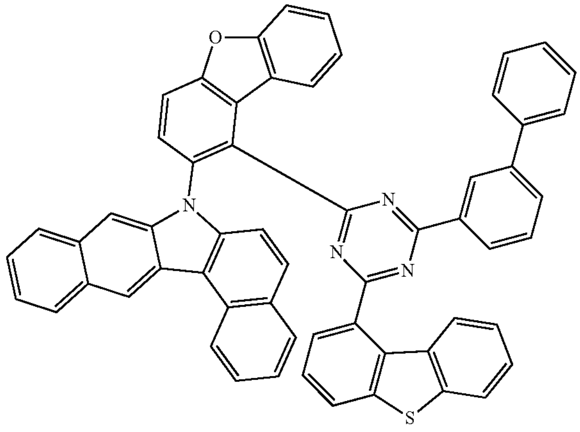
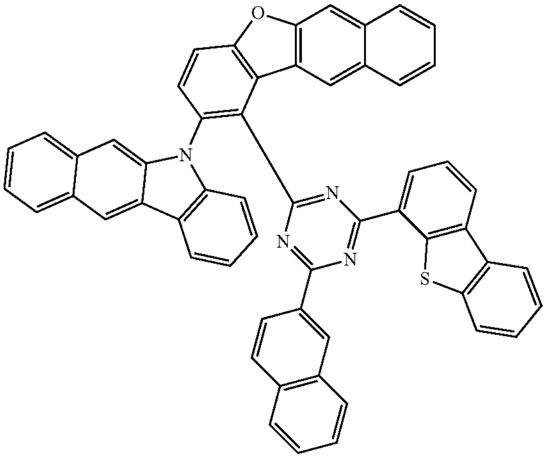
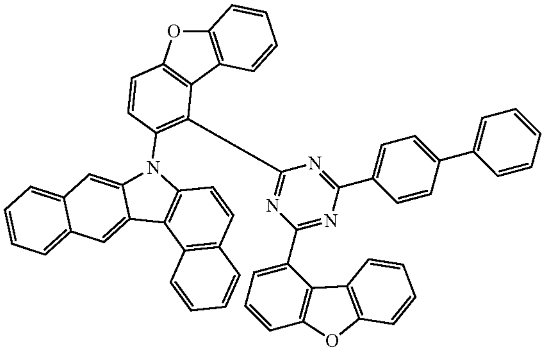

-continued
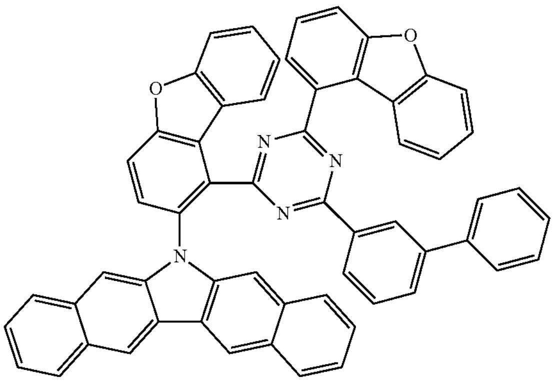
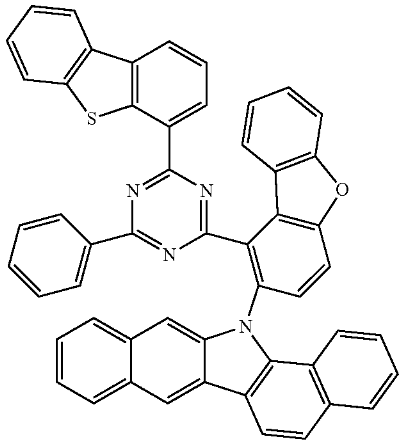
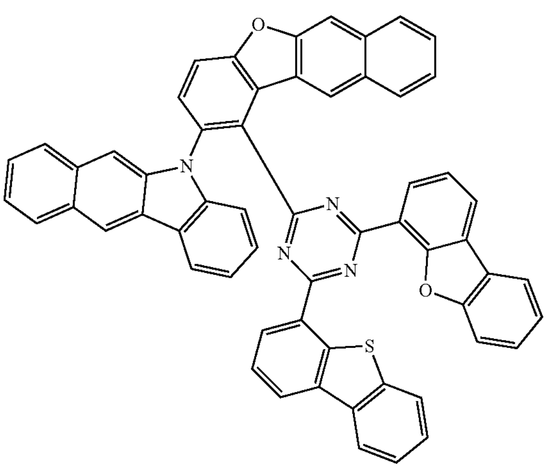
-continued
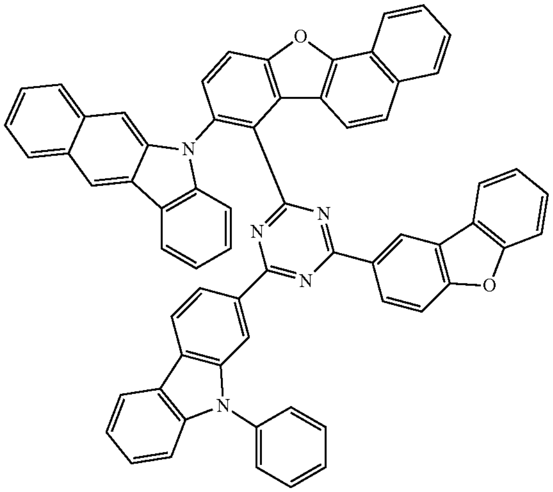
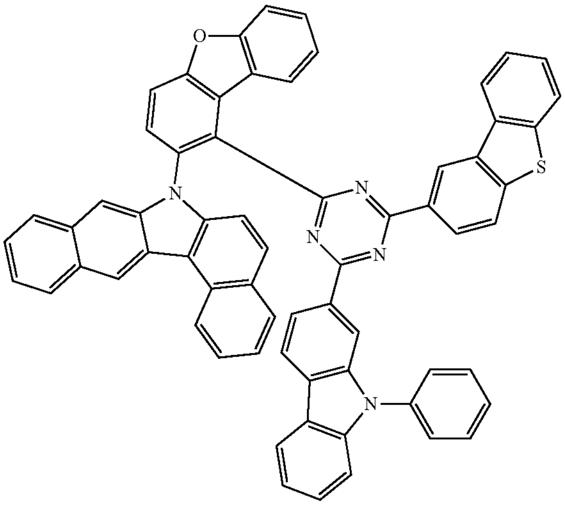
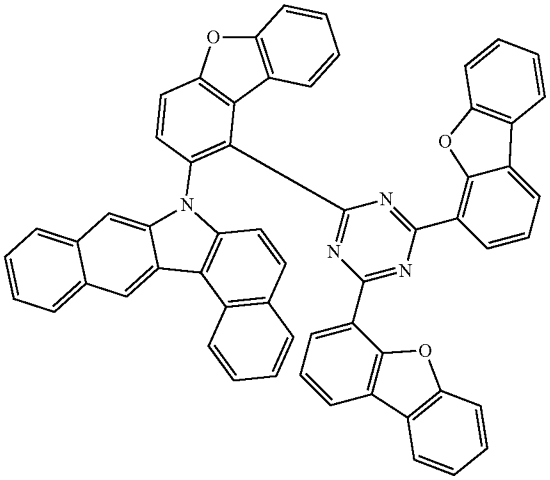

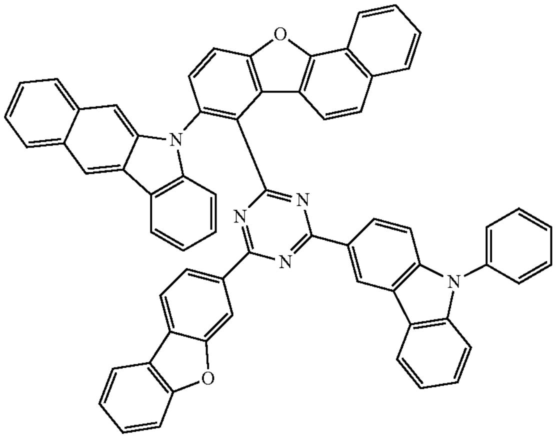
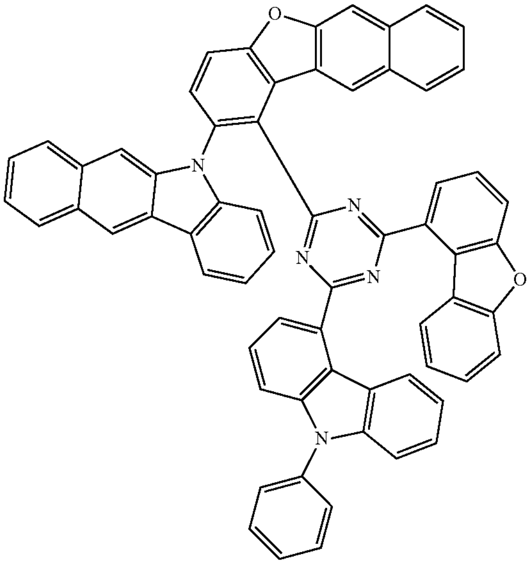
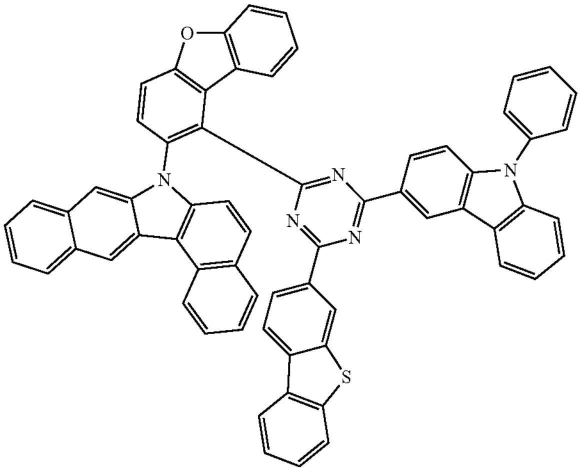
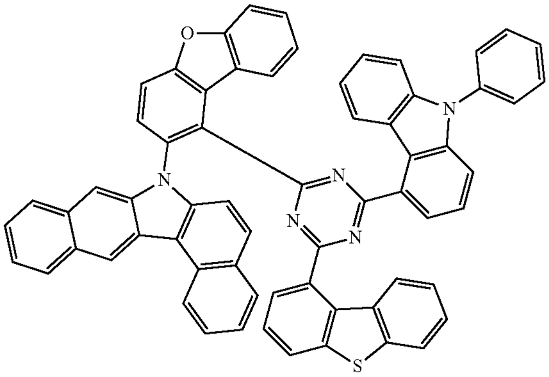
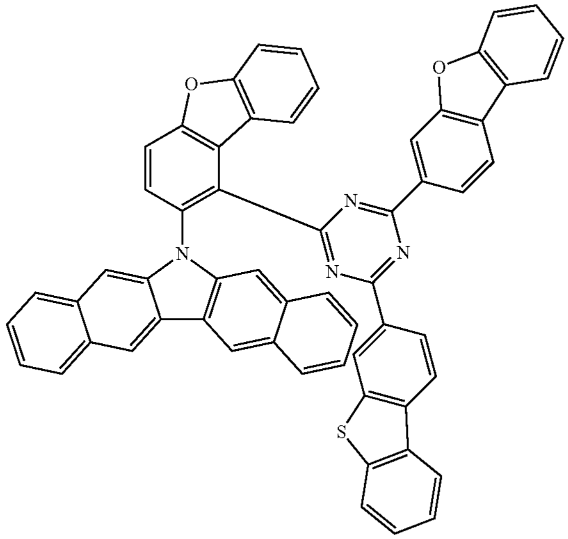
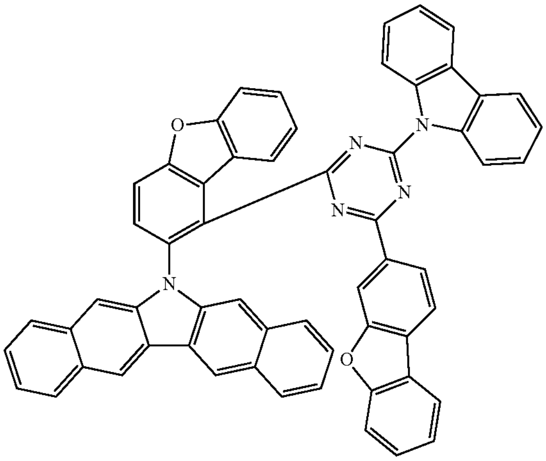

-continued
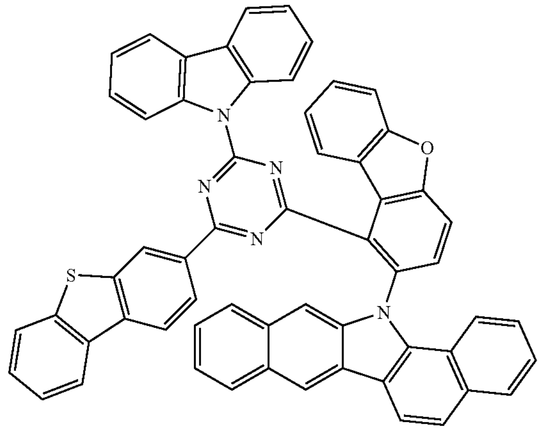
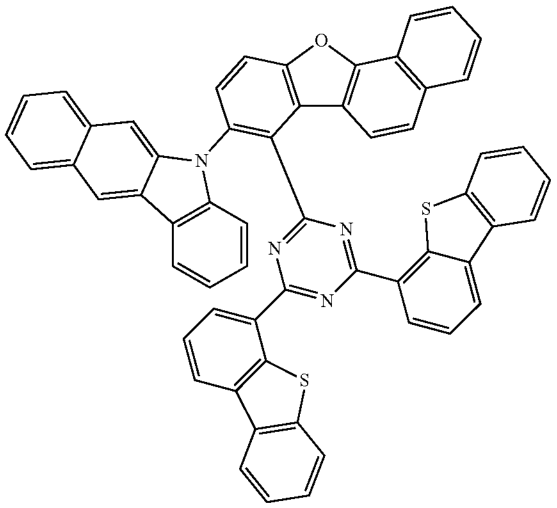
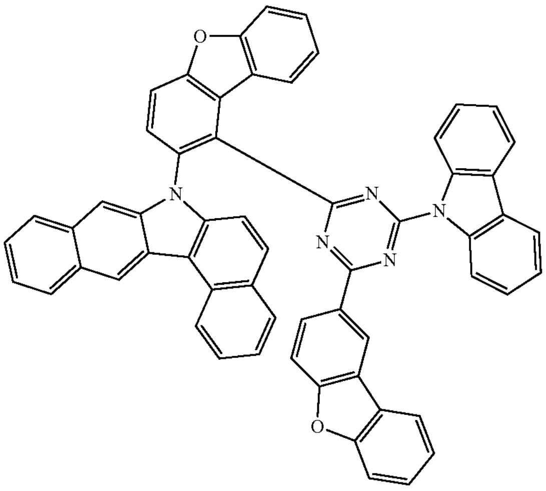
-continued
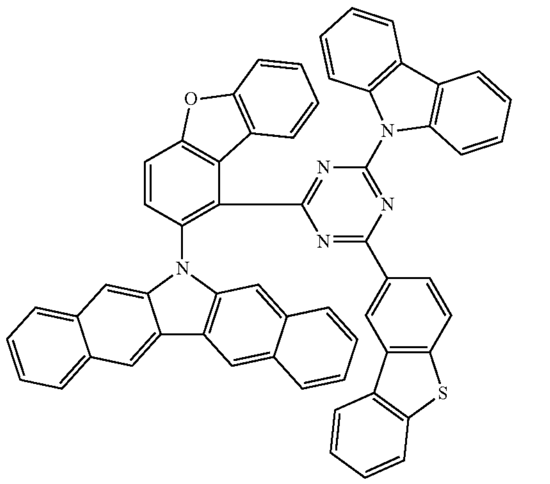
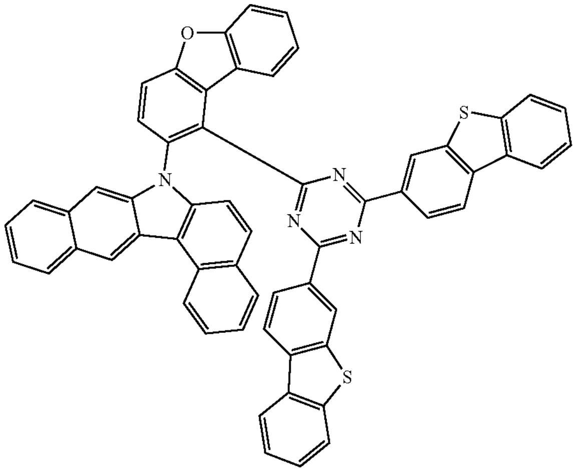
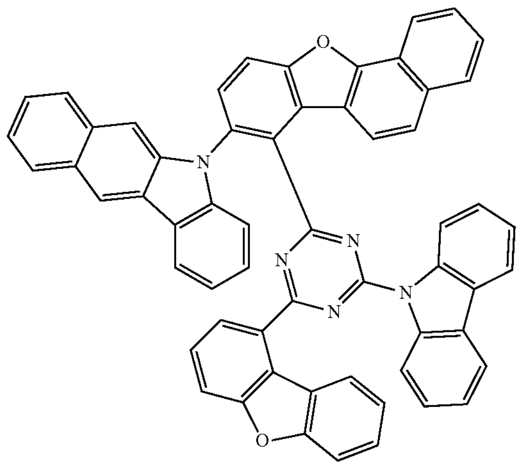

-continued
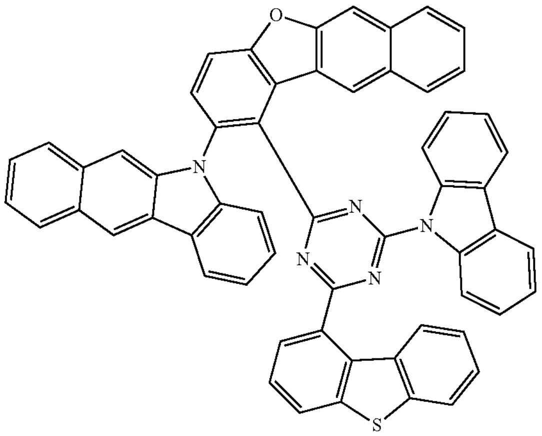
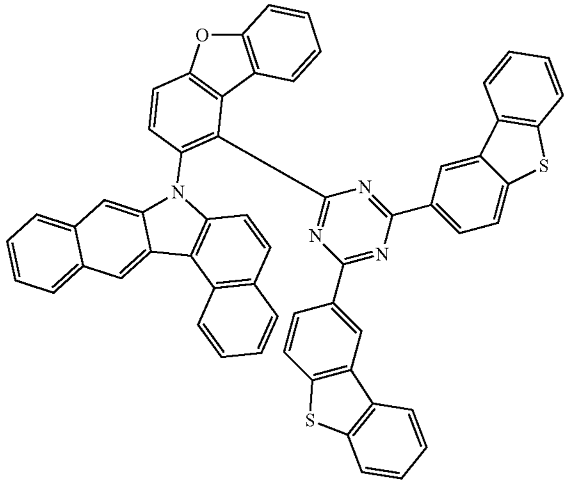
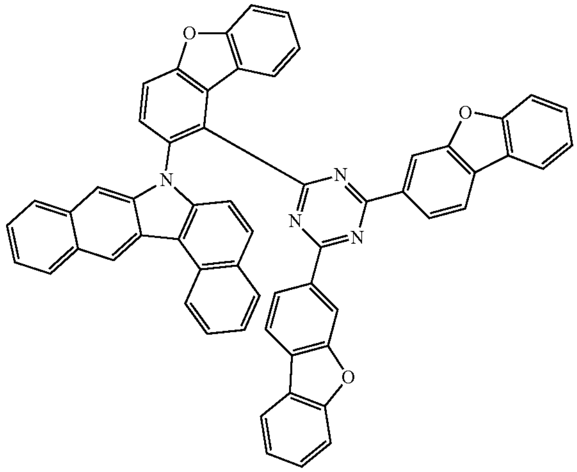
-continued
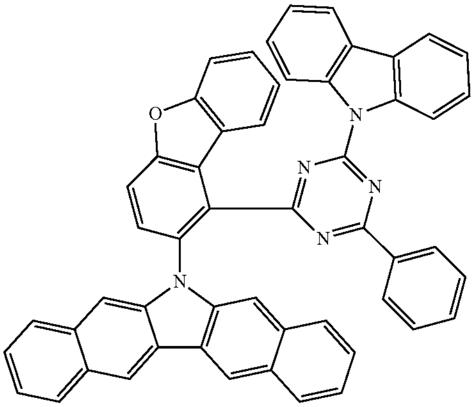
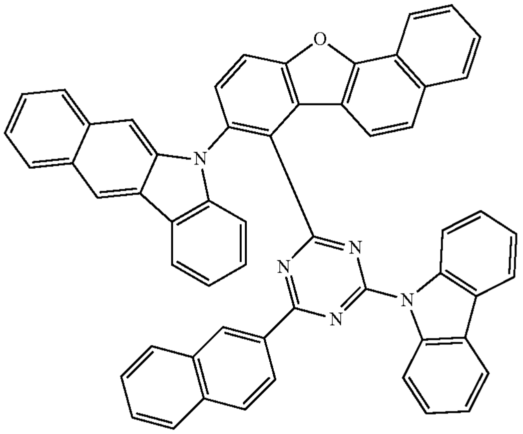
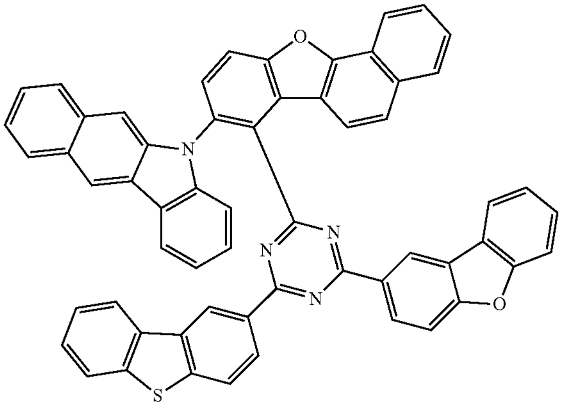
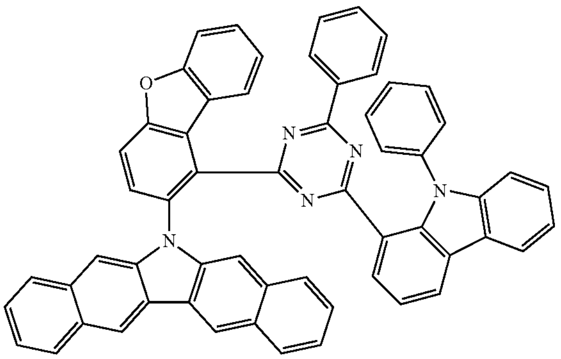

-continued
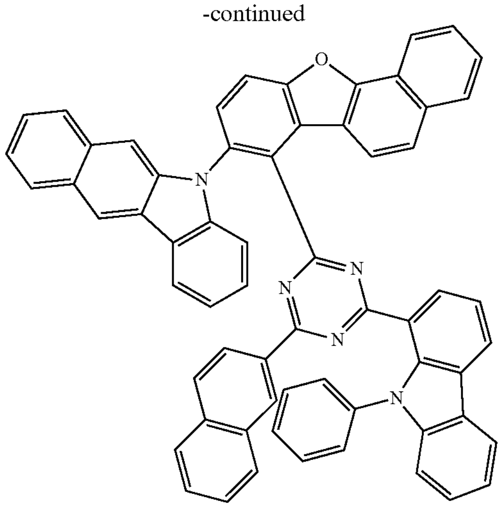
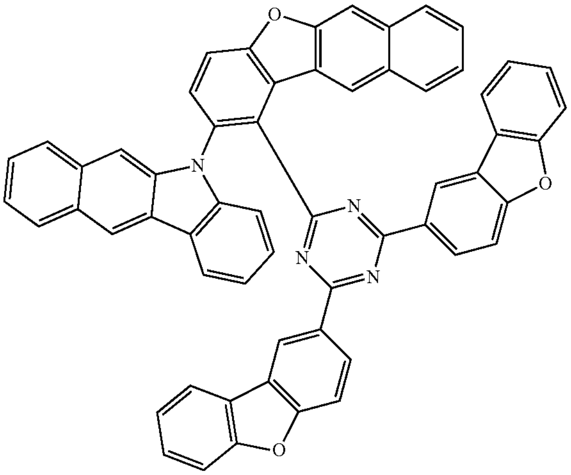
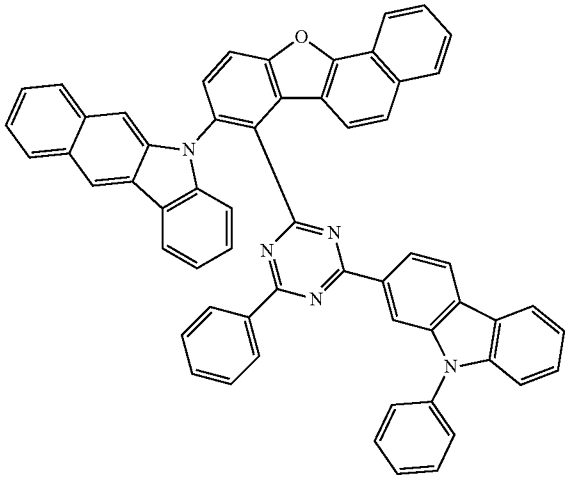
-continued
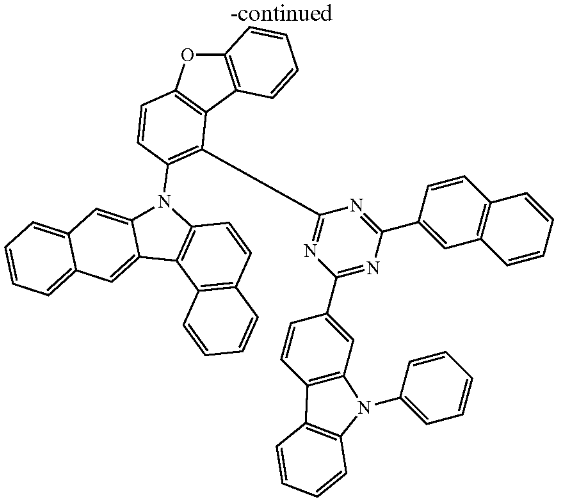
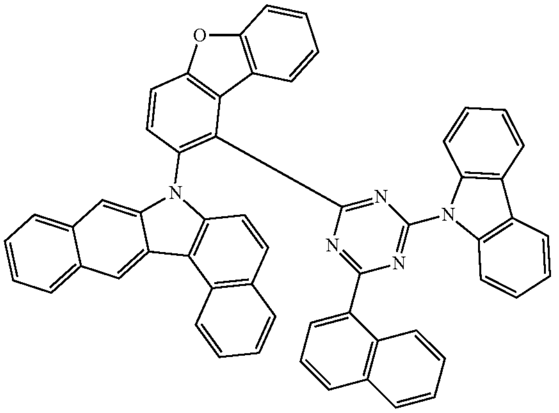
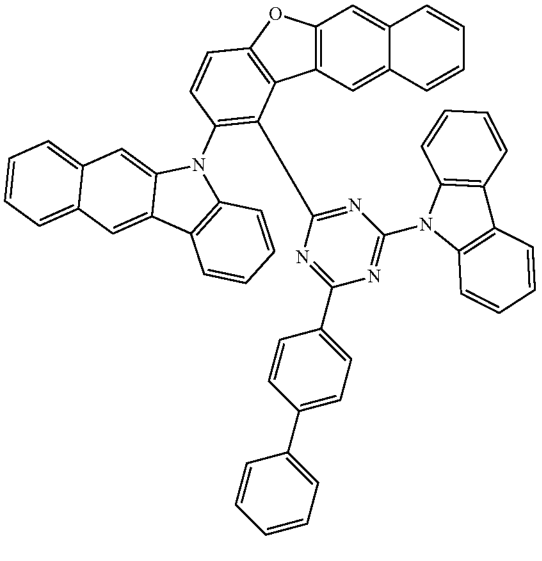

-continued
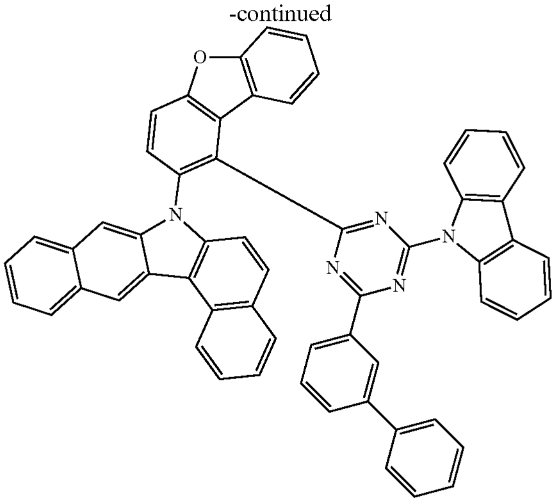
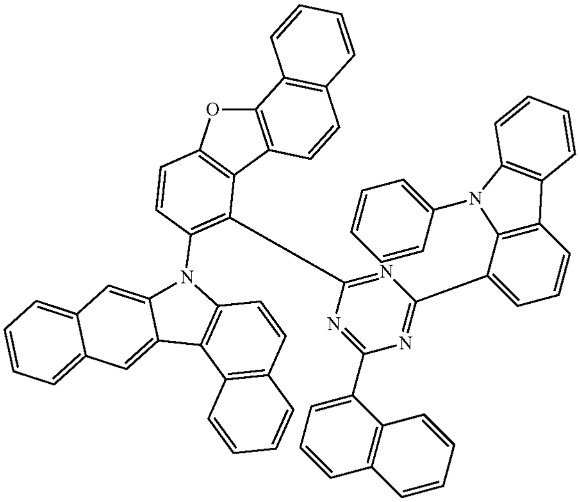
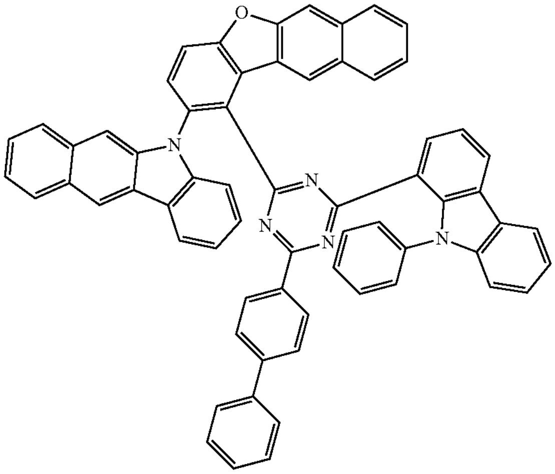
-continued
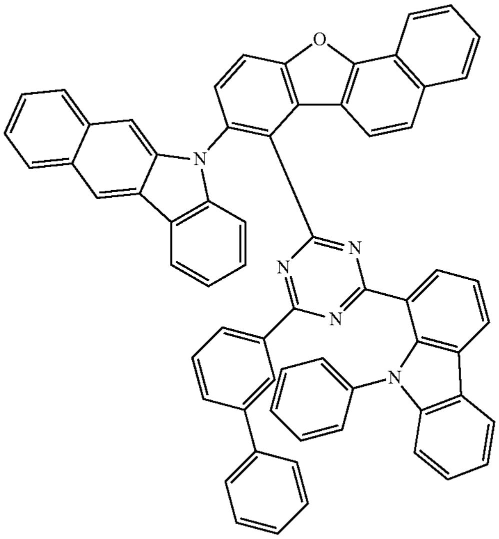
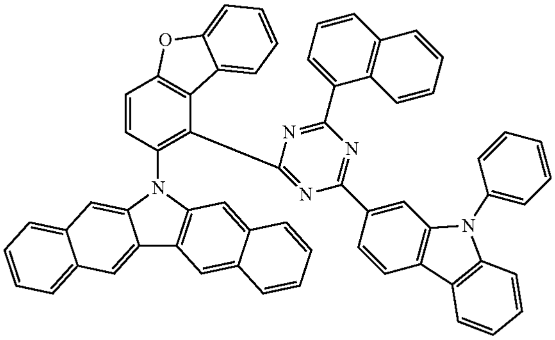
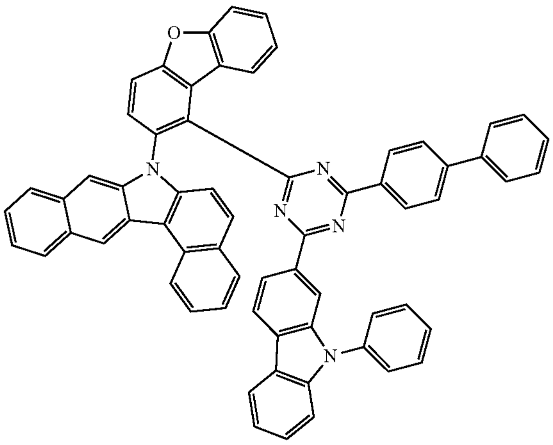

-continued
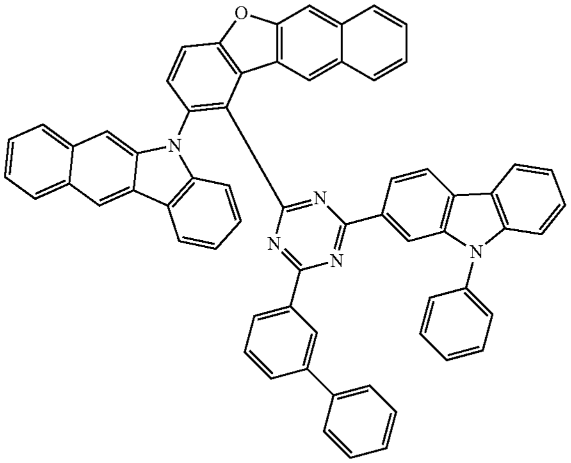
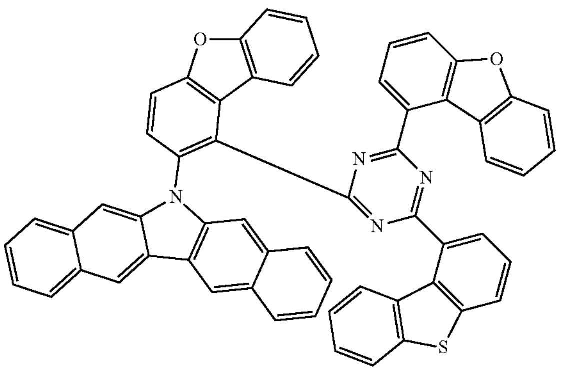
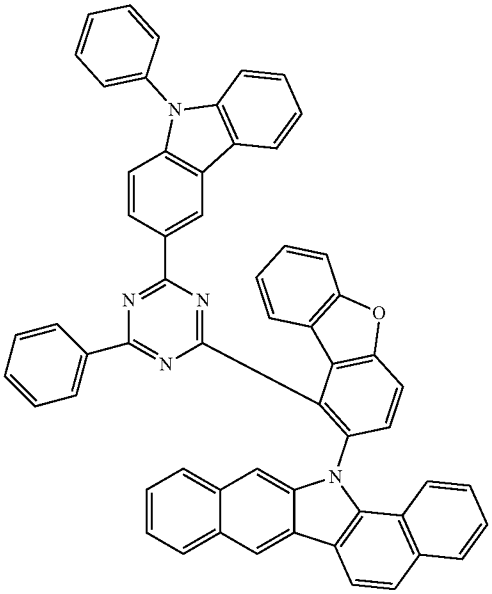
-continued
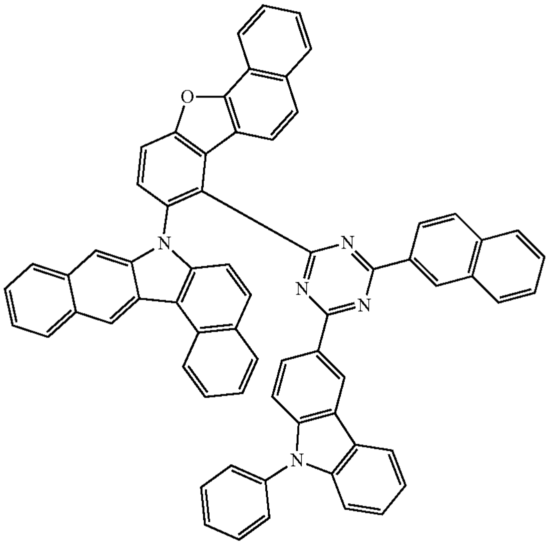
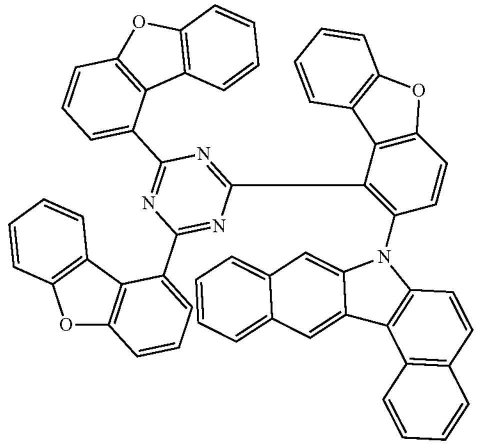
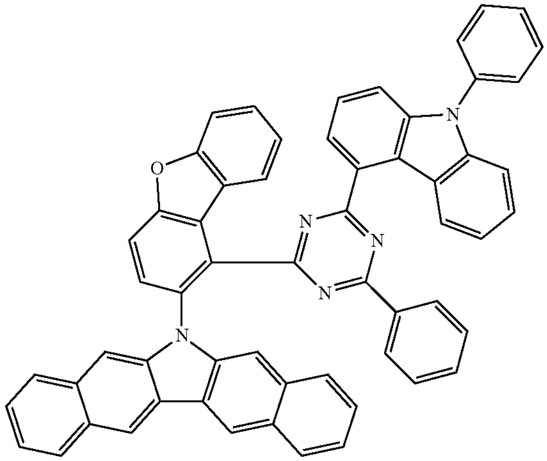

-continued
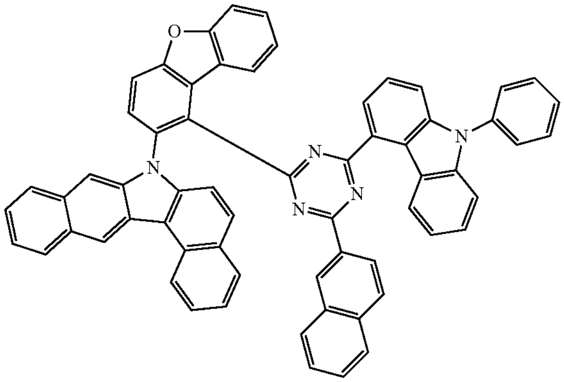
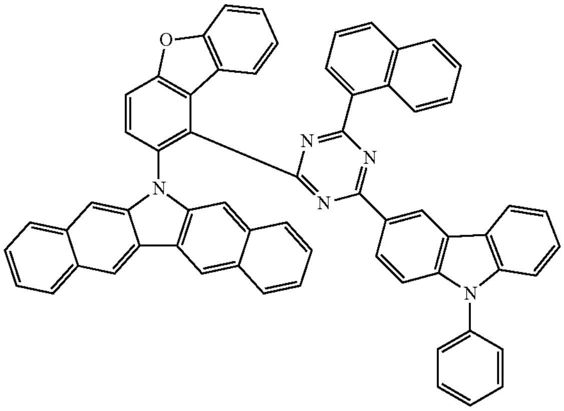
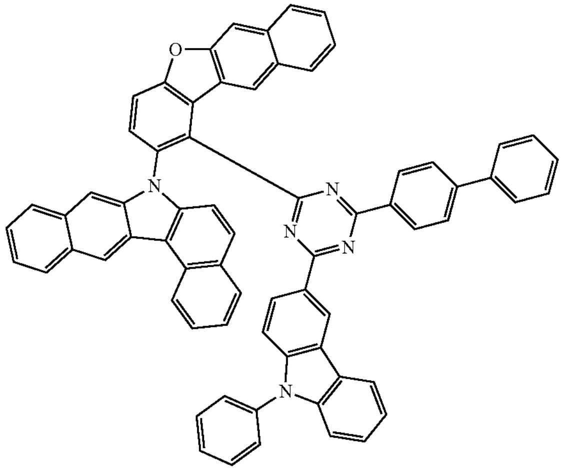
-continued
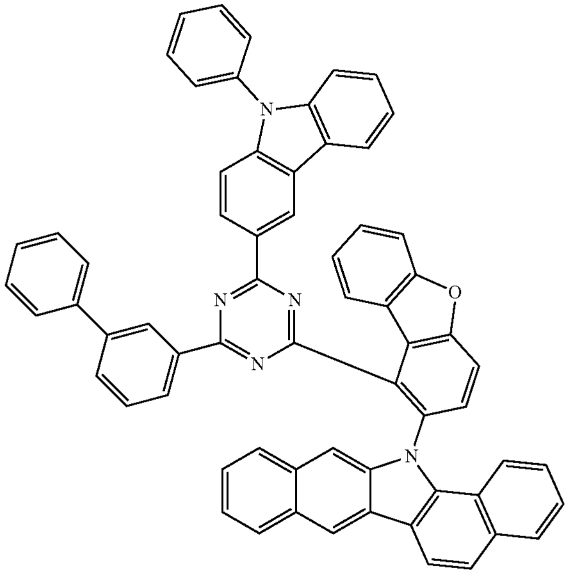
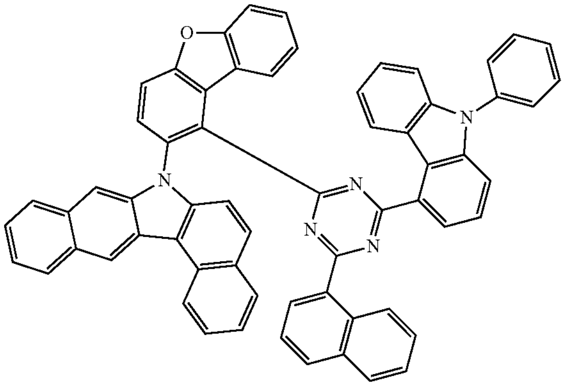
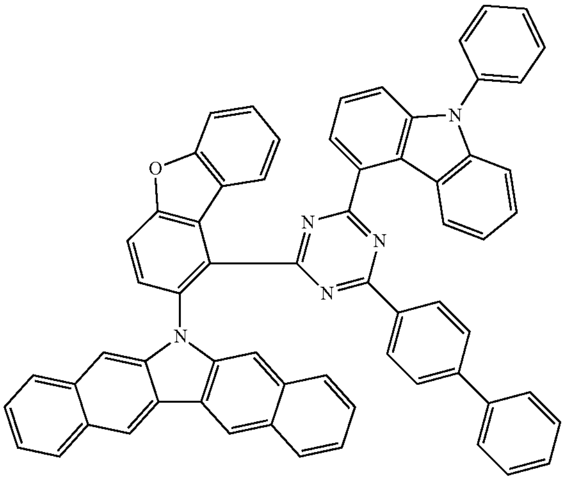

-continued

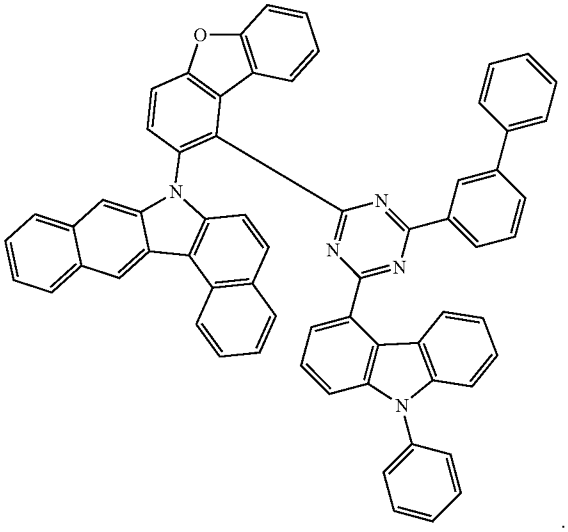

7. The organic light emitting device according to claim 1, wherein the second compound is represented by Chemical Formula 2-1:

[Chemical Formula 2-1]

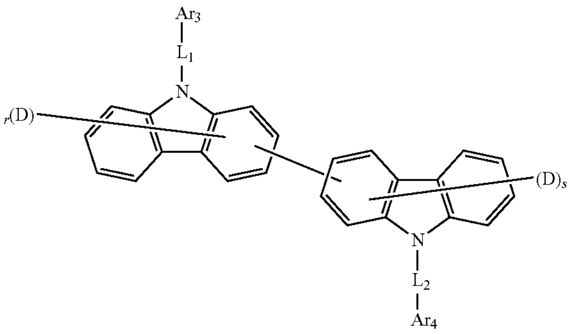

wherein, in Chemical Formula 2-1,

D is deuterium, r and s are each independently an integer from 0 to 7, and $L_1$, $L_2$, $Ar_3$ and $Ar_4$ are the same as defined in claim 1.

8. The organic light emitting device according to claim 1, wherein $L_1$ and $L_2$ are each independently a single bond, phenylene, or naphthylene.

9. The organic light emitting device according to claim 1, wherein $Ar_3$ and $Ar_4$ are each independently any one selected from the group consisting of the following:

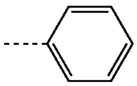
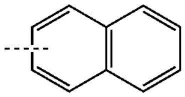
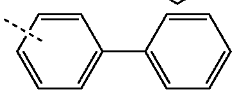
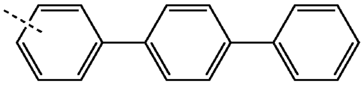

-continued

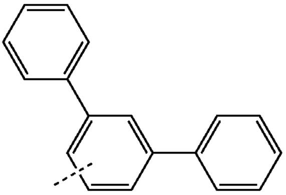
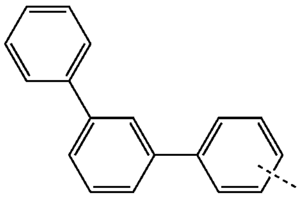
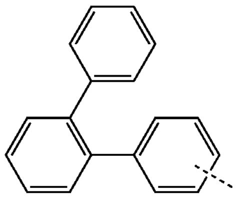
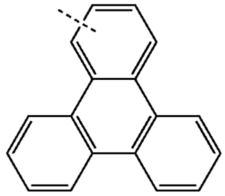
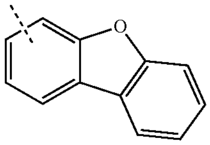
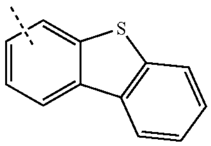
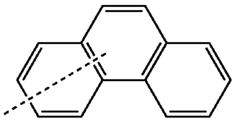
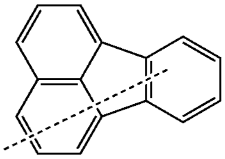
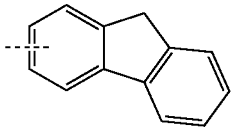
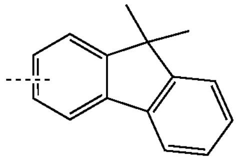
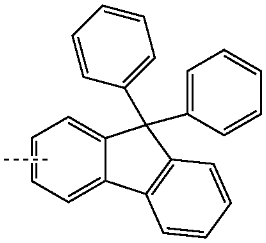
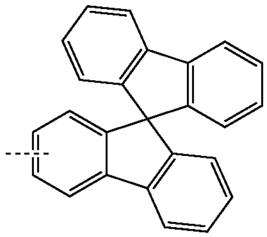.

10. The organic light emitting device according to claim 1, wherein the second compound is represented by Chemical Formula 2-2:

[Chemical Formula 2-2]

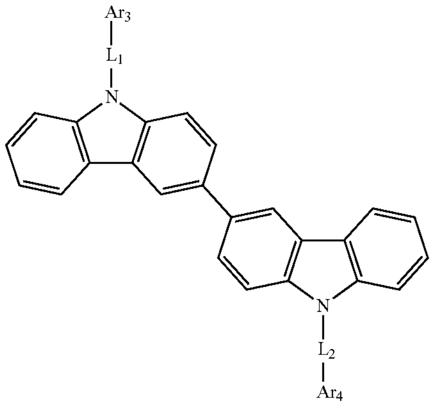

wherein, in the Chemical Formula 2-2, $L_1$ and $L_2$ are each independently a single bond, phenylene, or naphthylene, and $Ar_3$ and $Ar_4$ are the same as defined in claim 1.

11. The organic light emitting device according to claim 1, wherein the second compound is any one selected from the group consisting of the following:

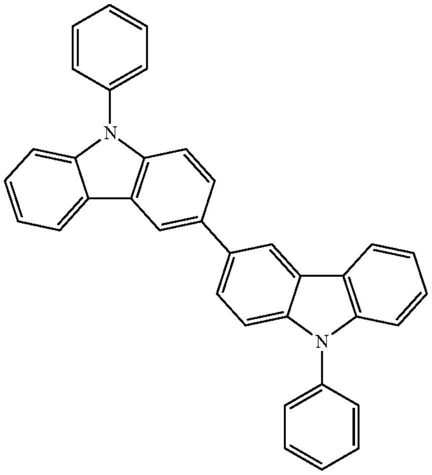

-continued

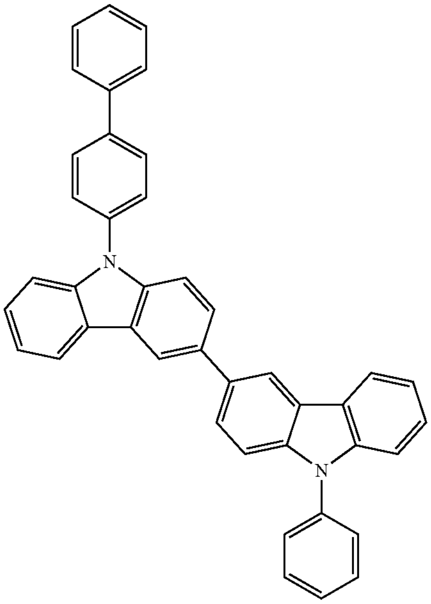

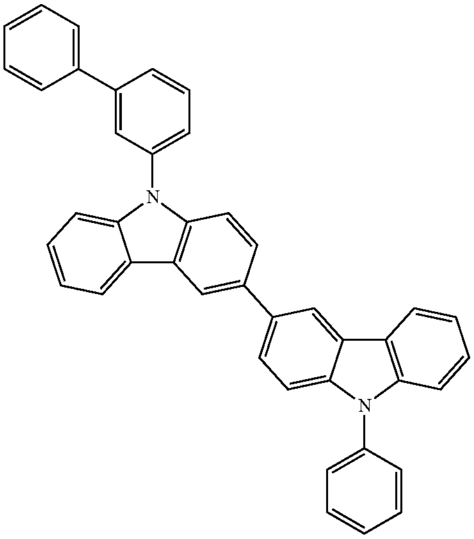

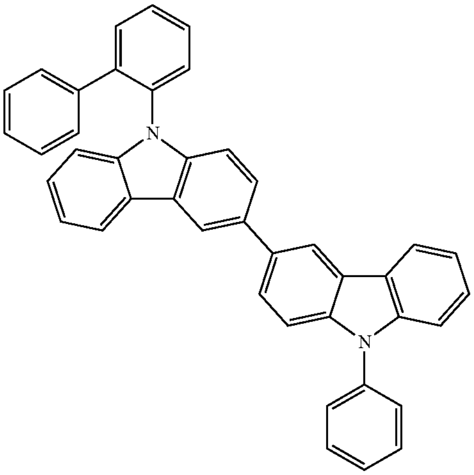

-continued
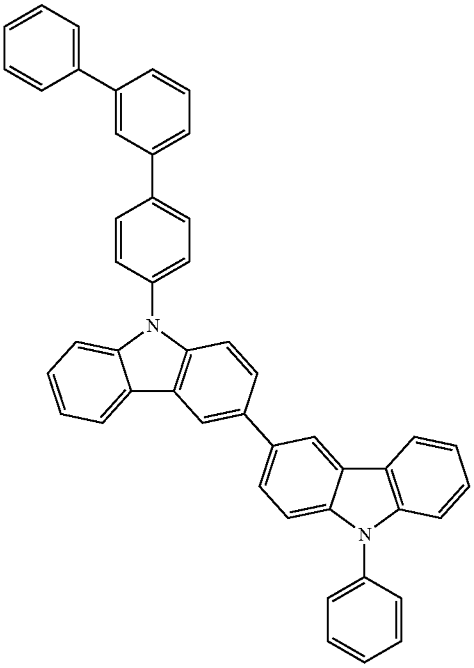
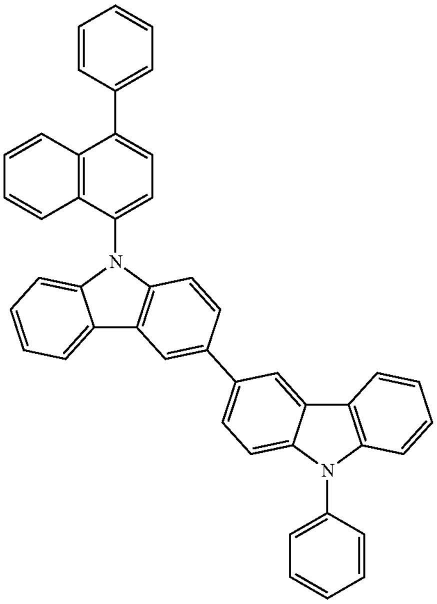
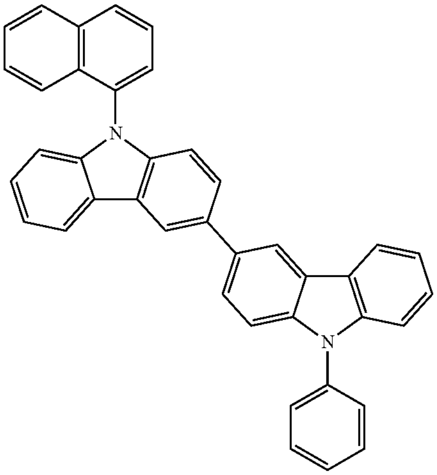
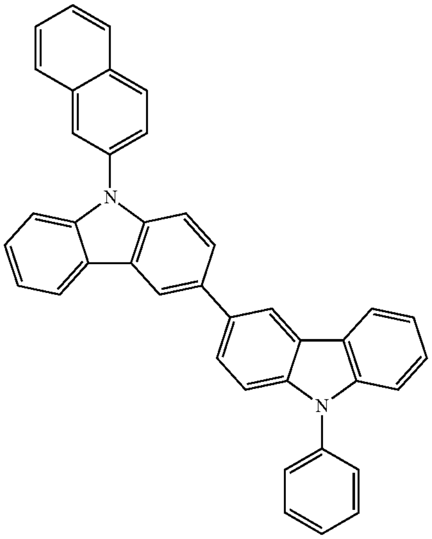
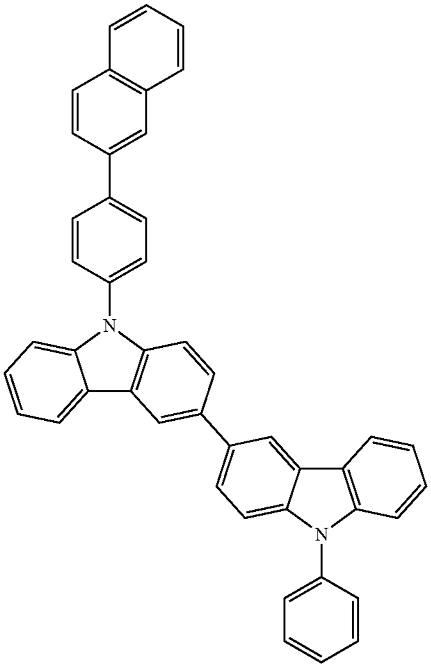

-continued
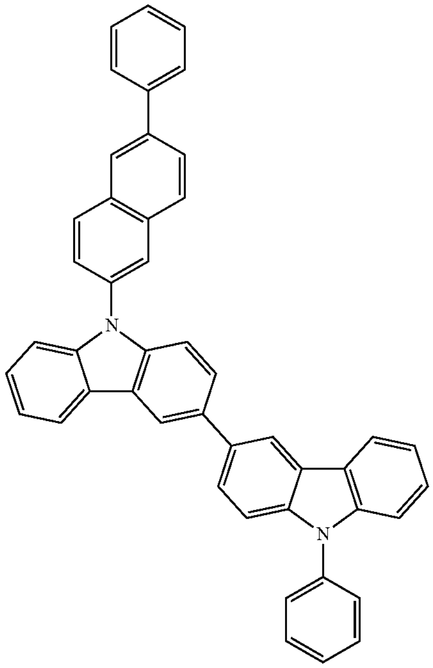
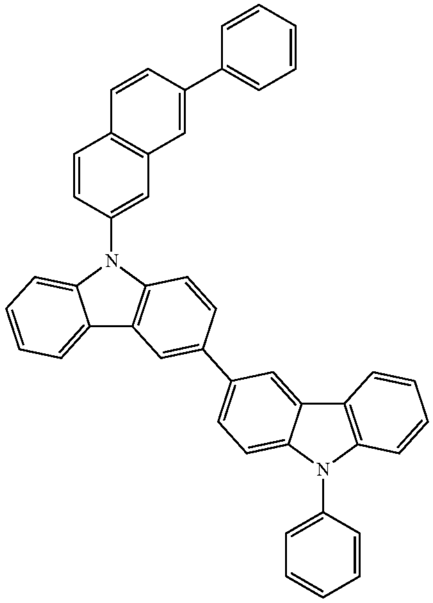
-continued
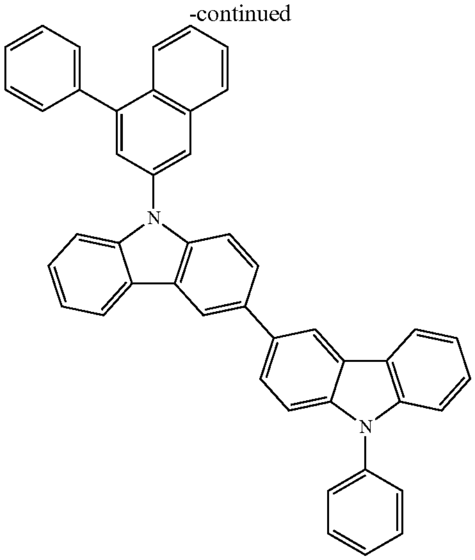
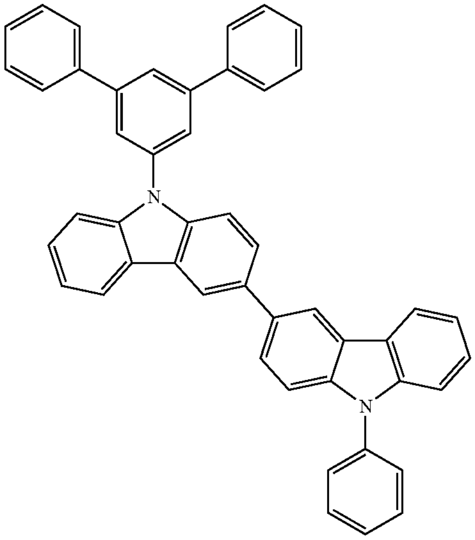
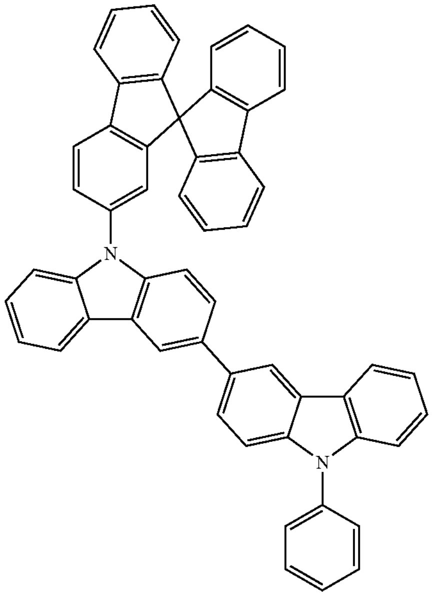

-continued
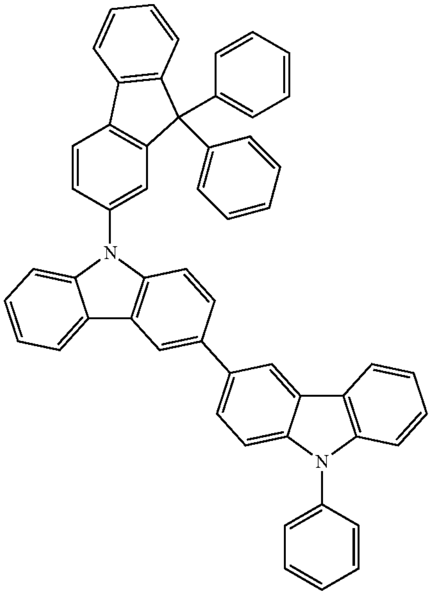
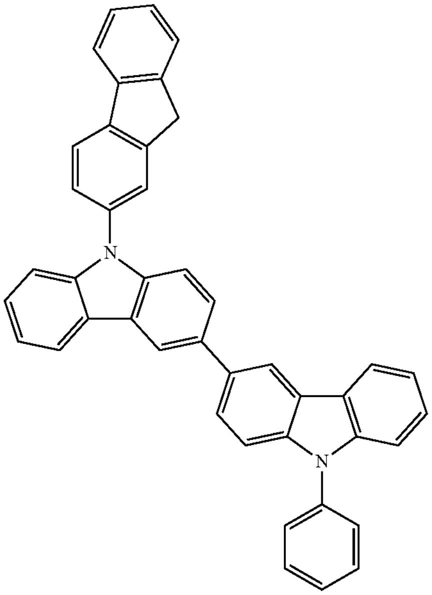
-continued
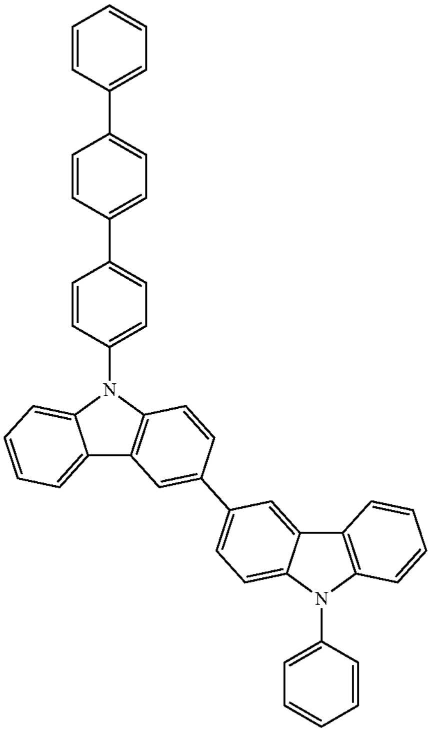
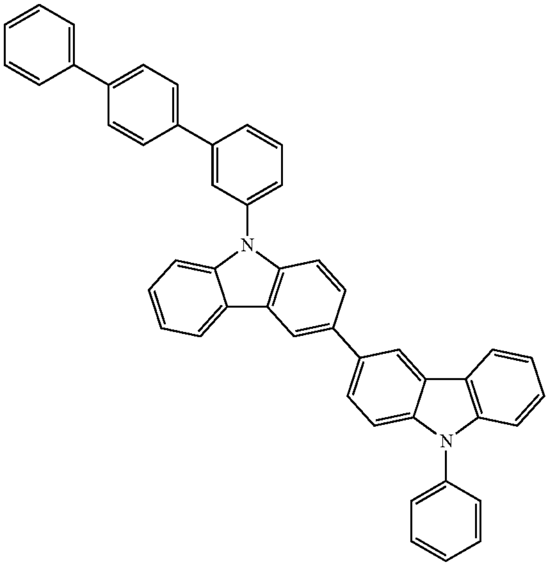

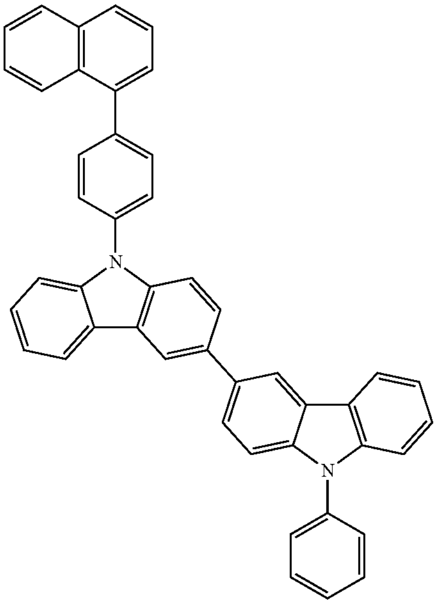
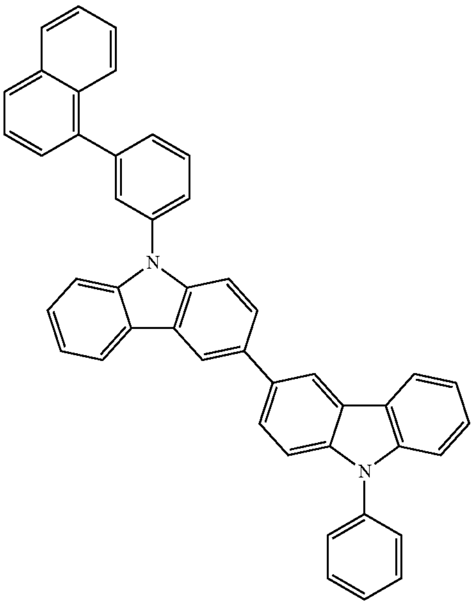
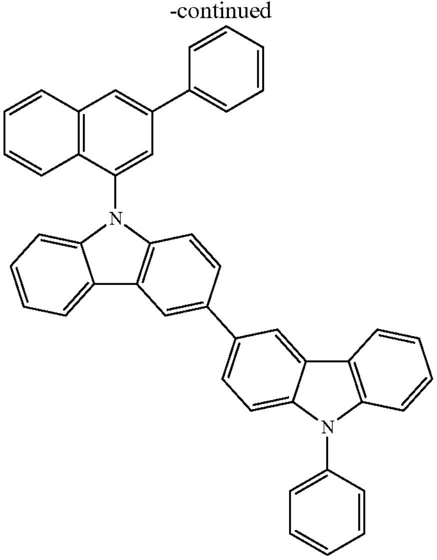
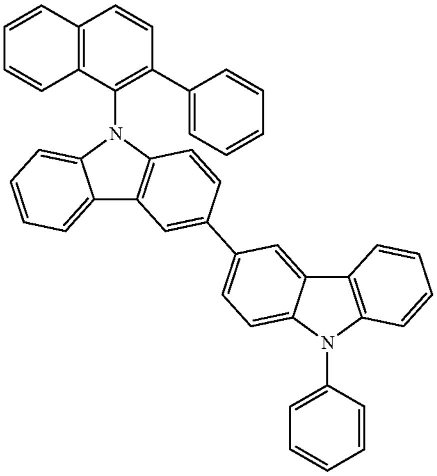
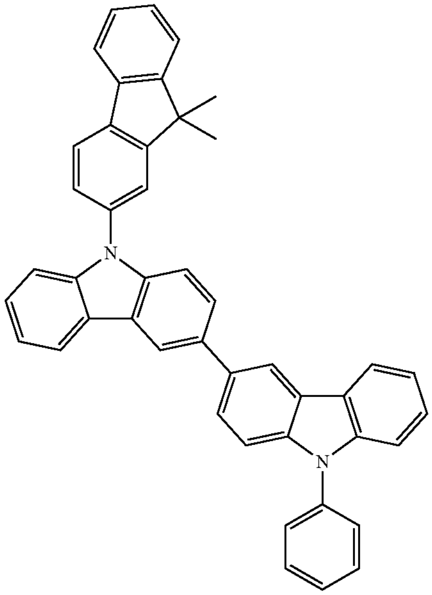

-continued
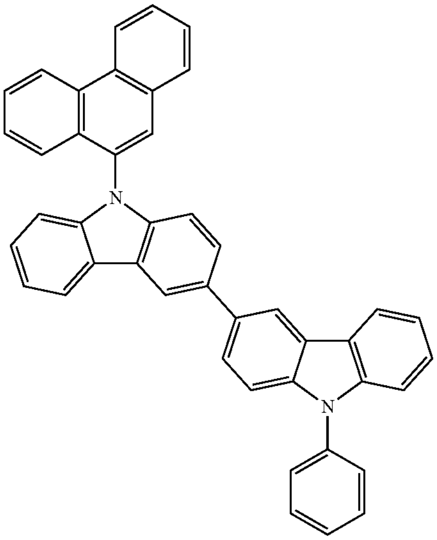
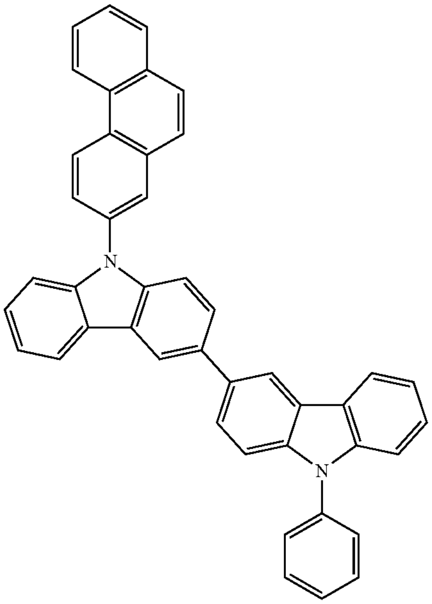
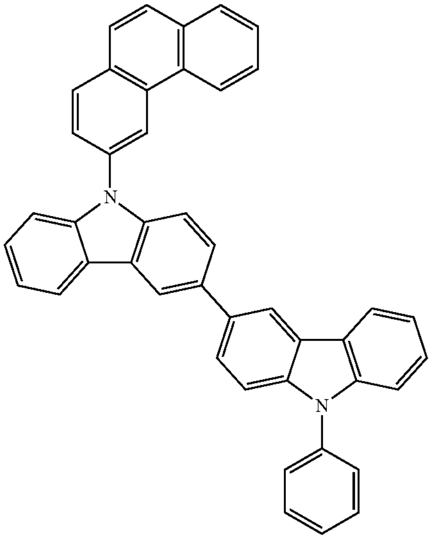
-continued
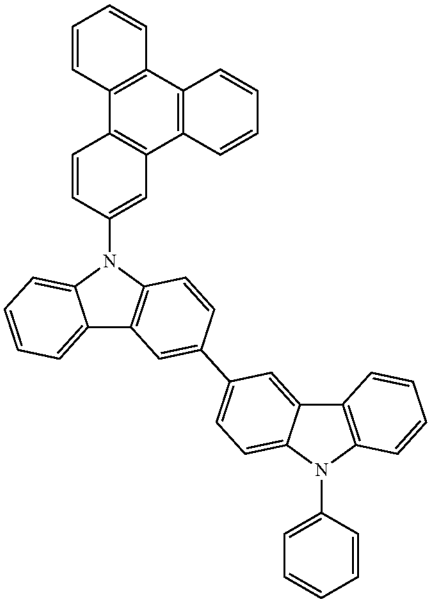
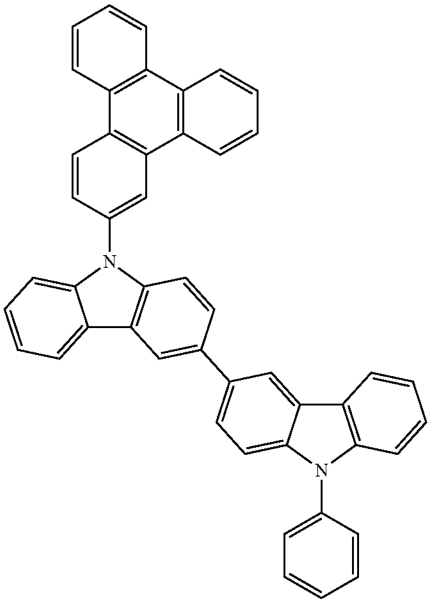

-continued
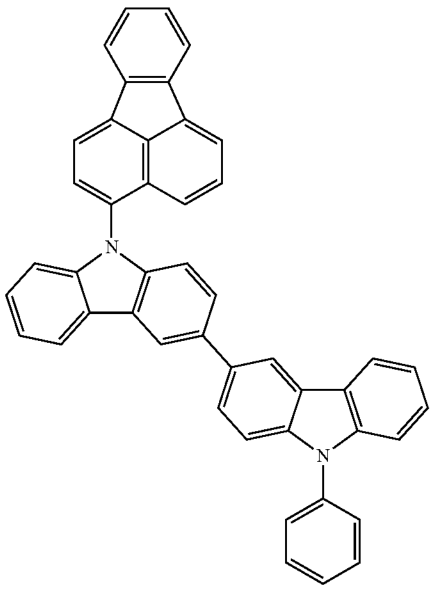
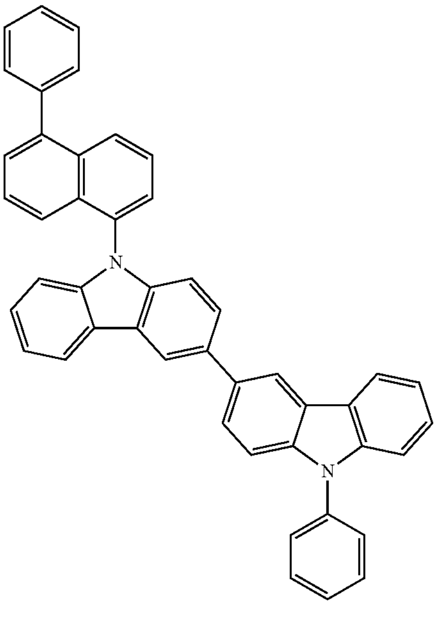
-continued
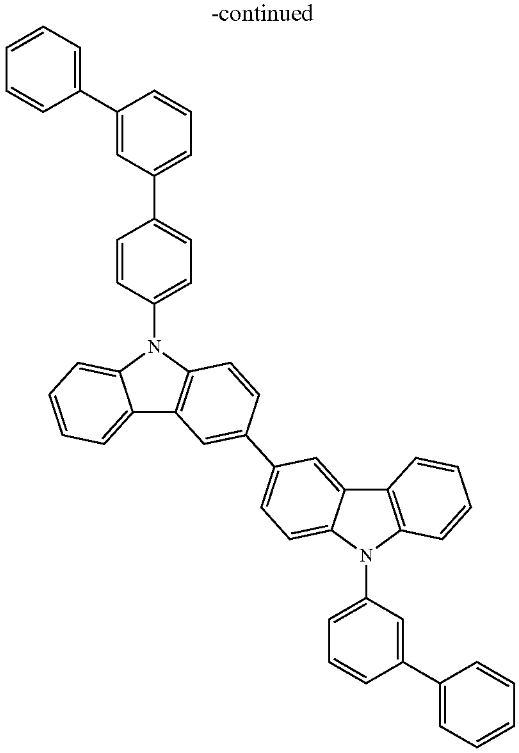
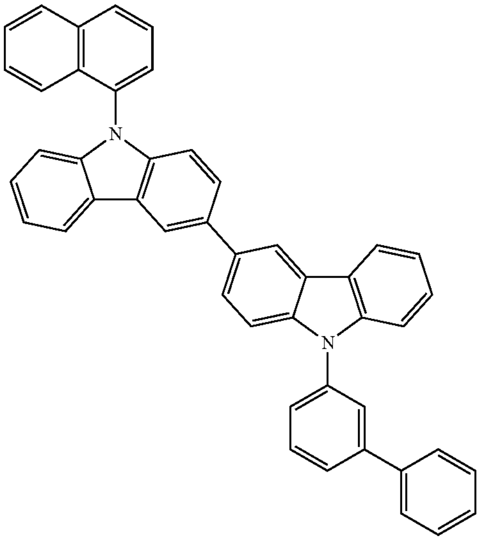

-continued
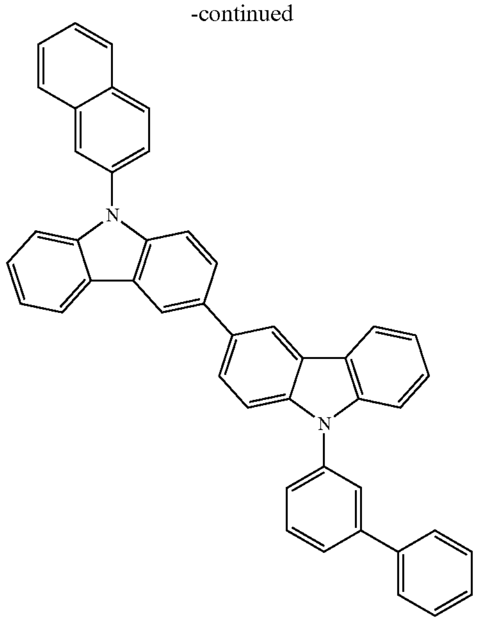
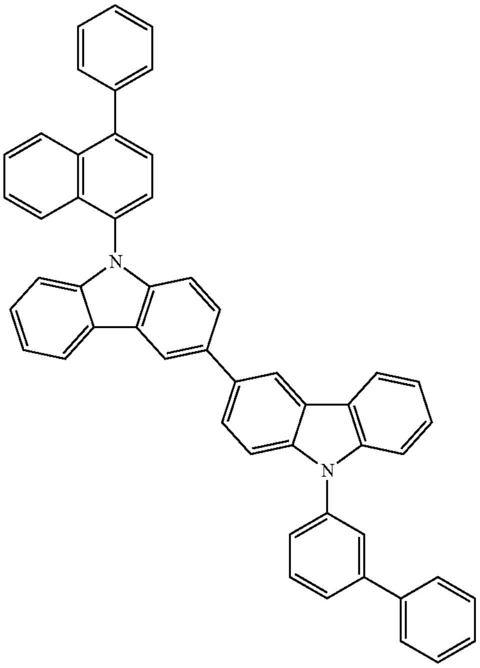
-continued
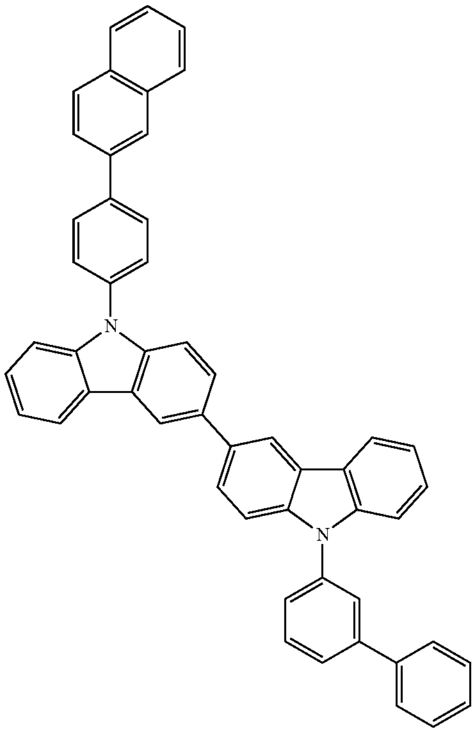
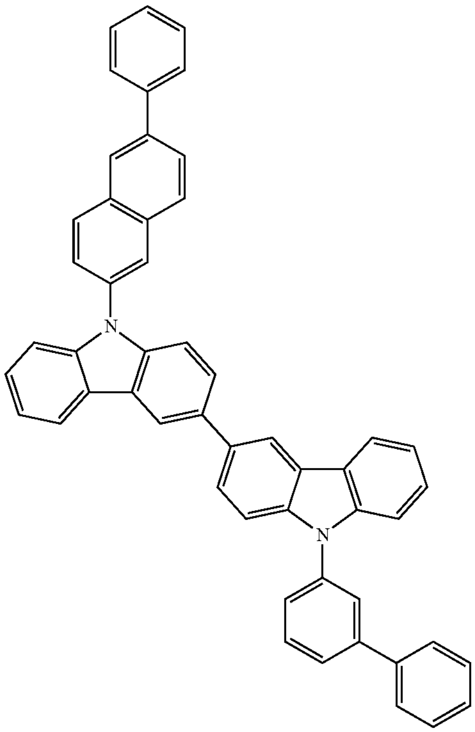

-continued
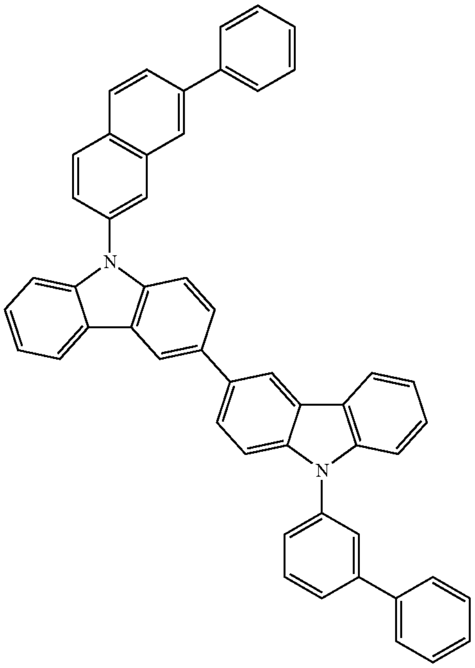
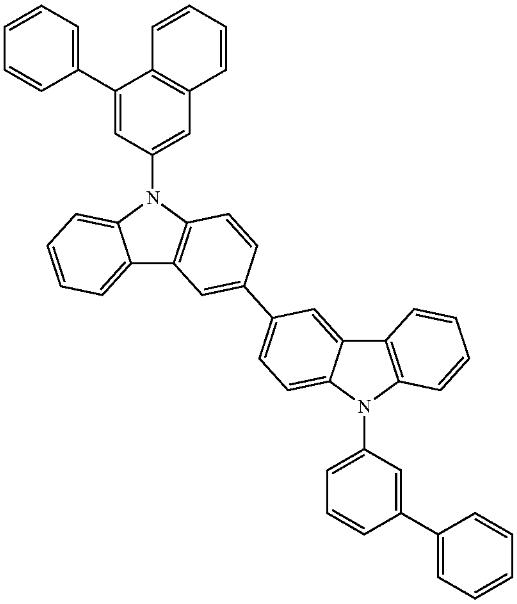
-continued
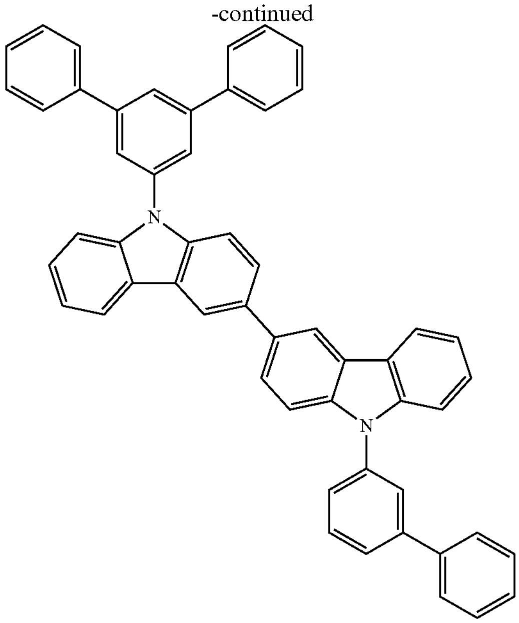
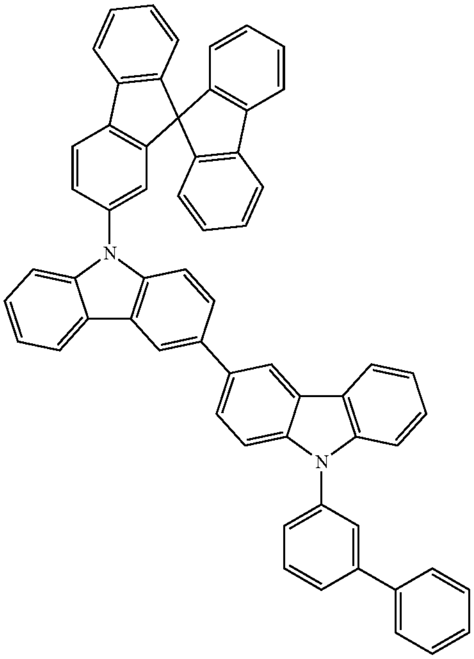

-continued
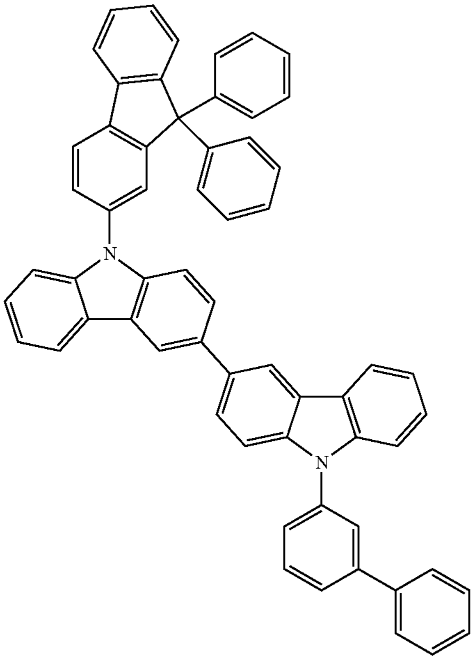
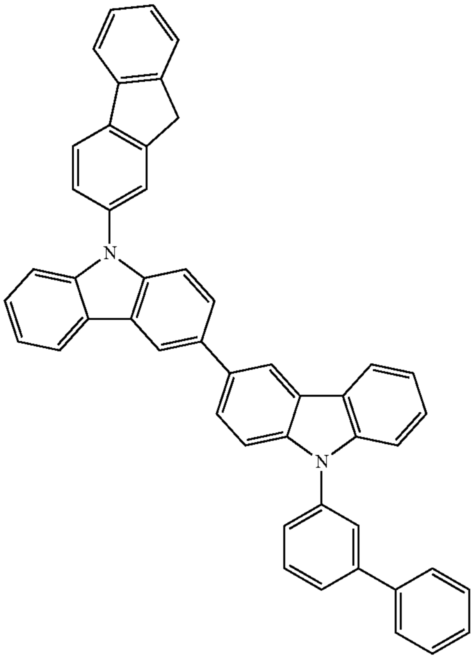
-continued
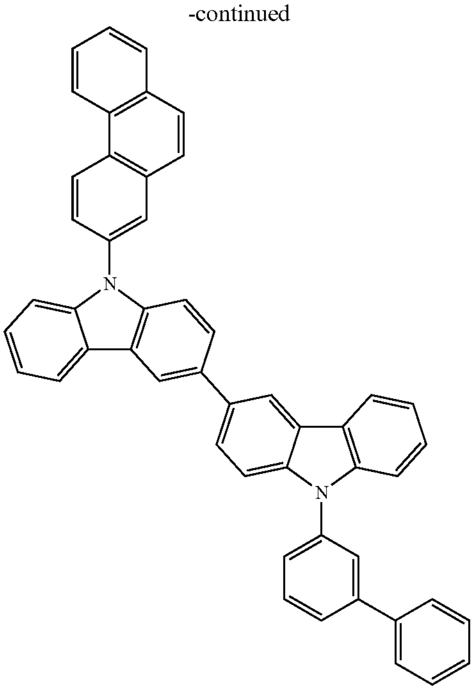
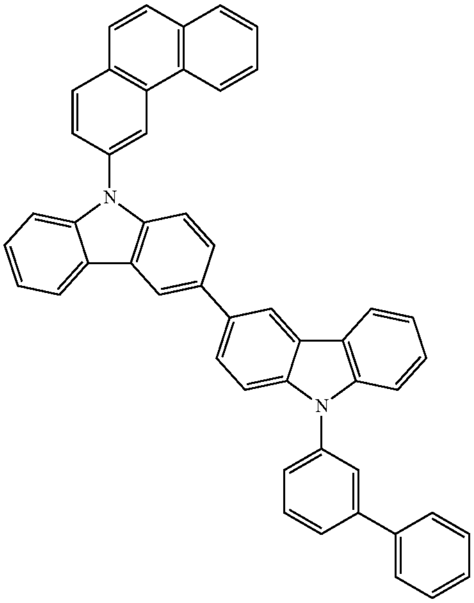

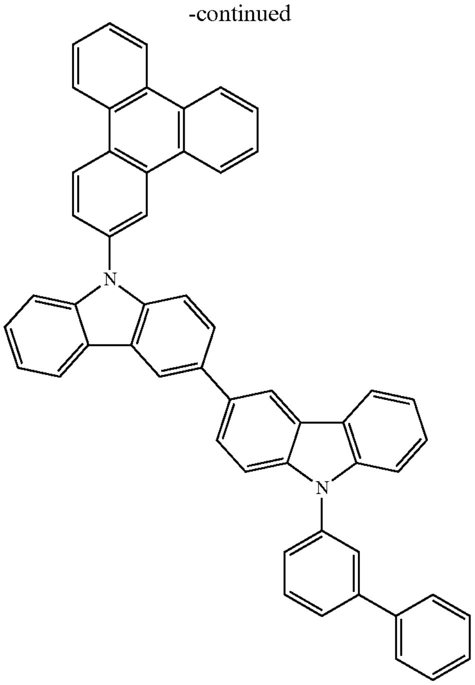
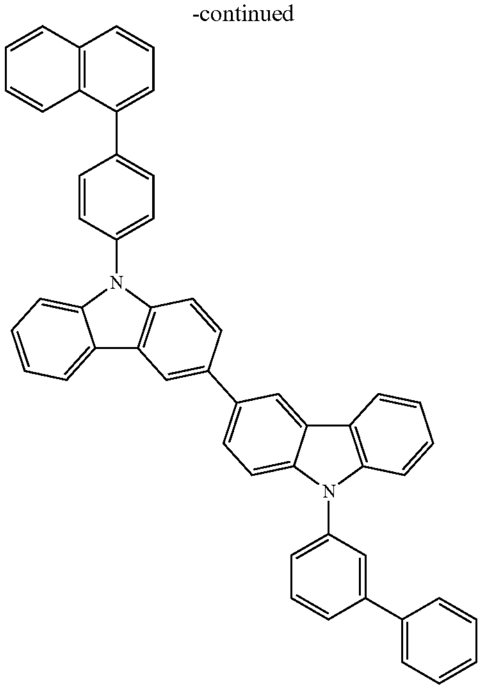
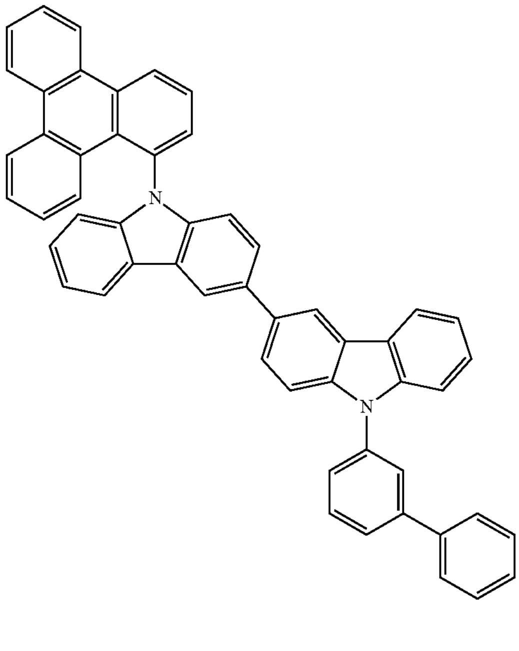
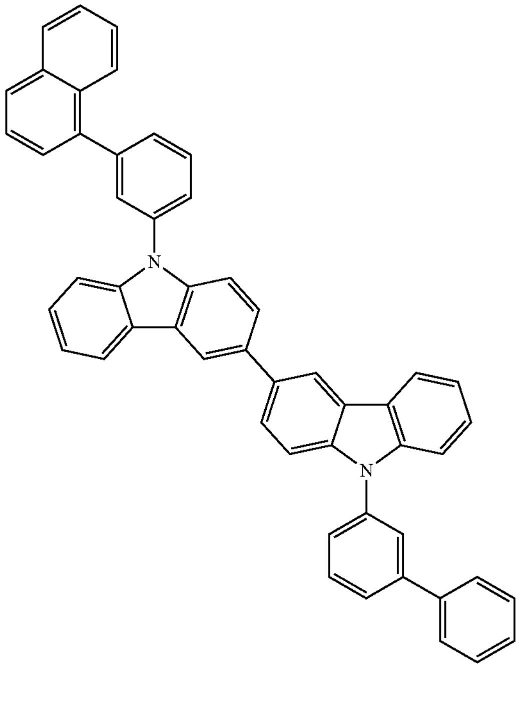

-continued
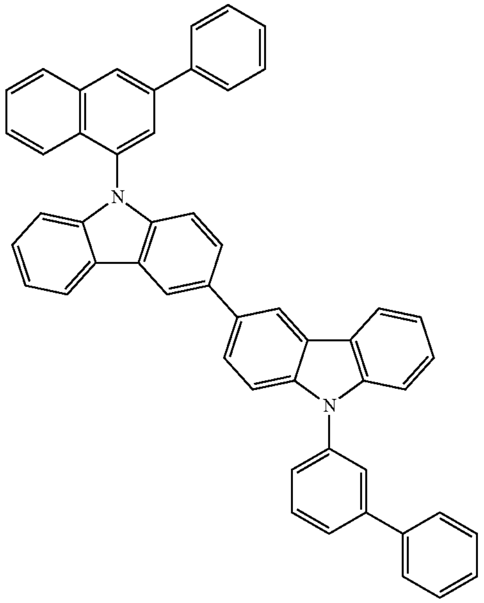
-continued
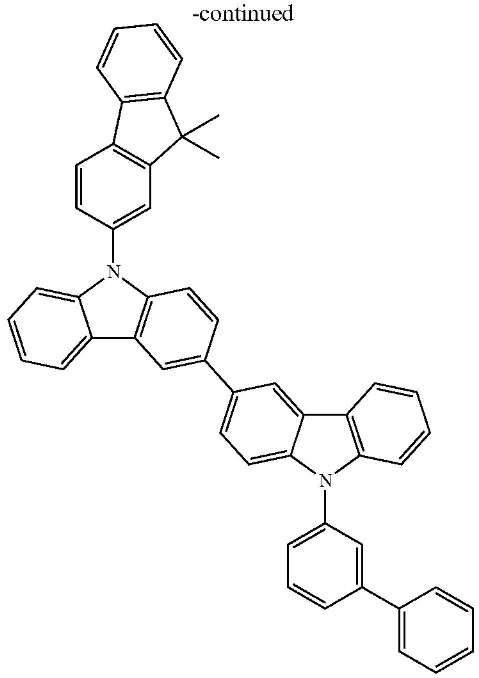
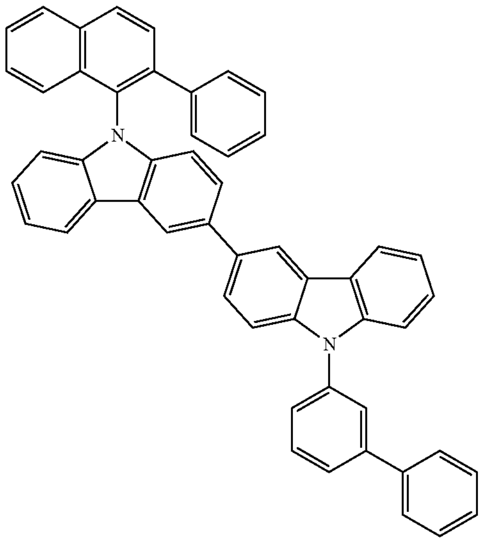
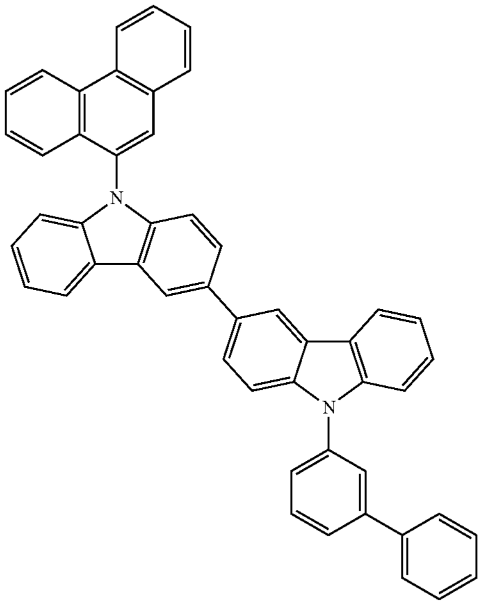

-continued
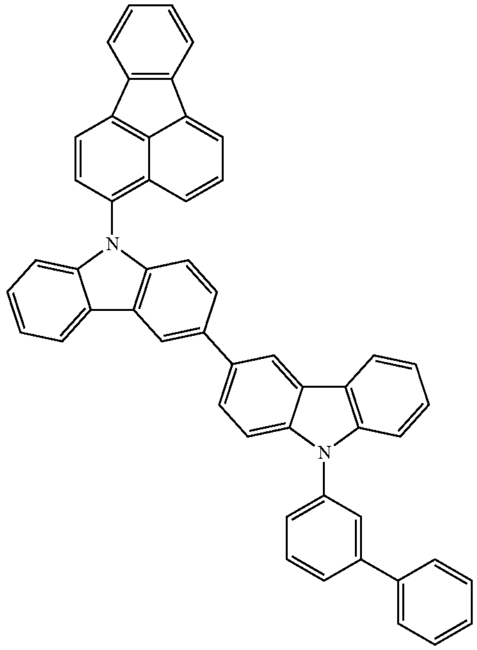
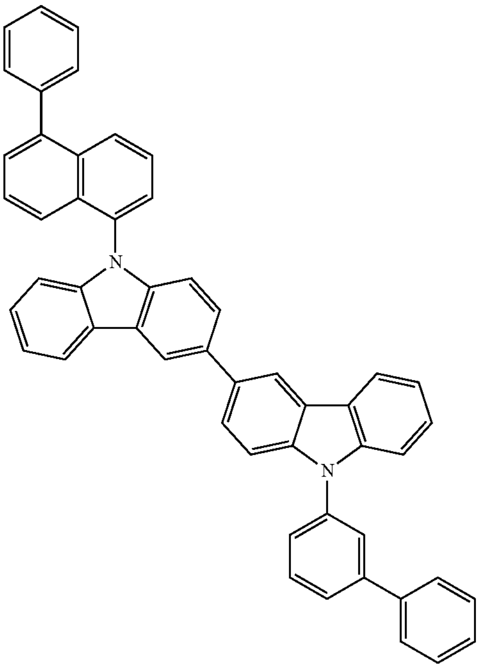
-continued
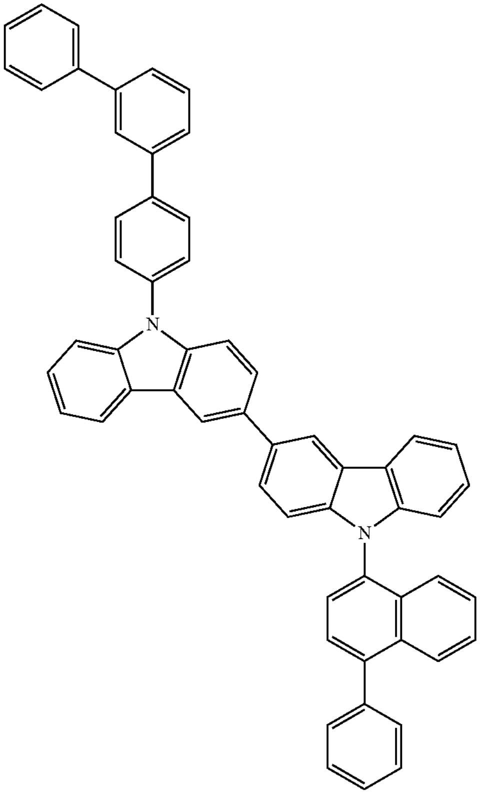
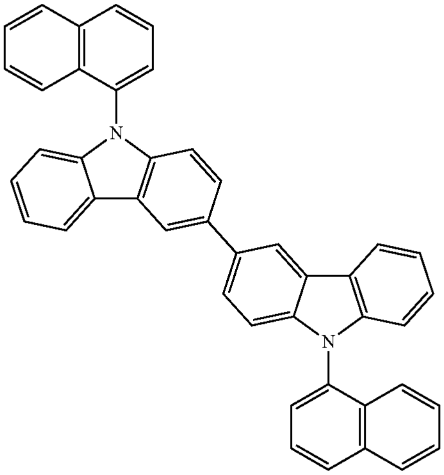

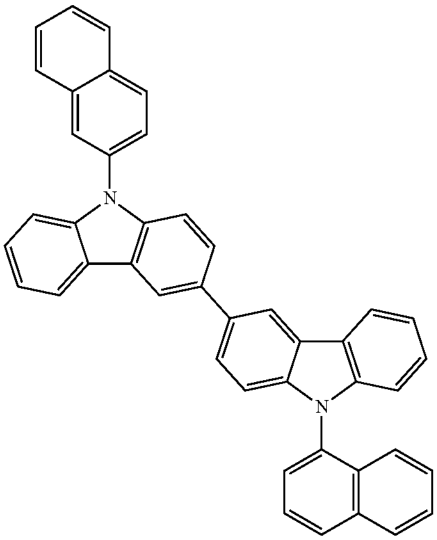
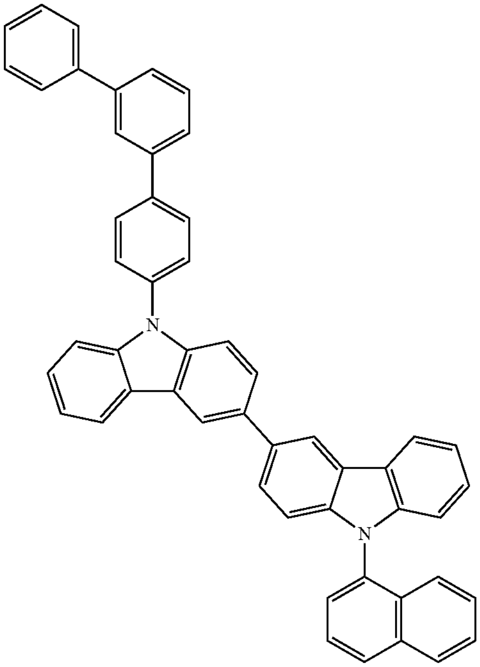
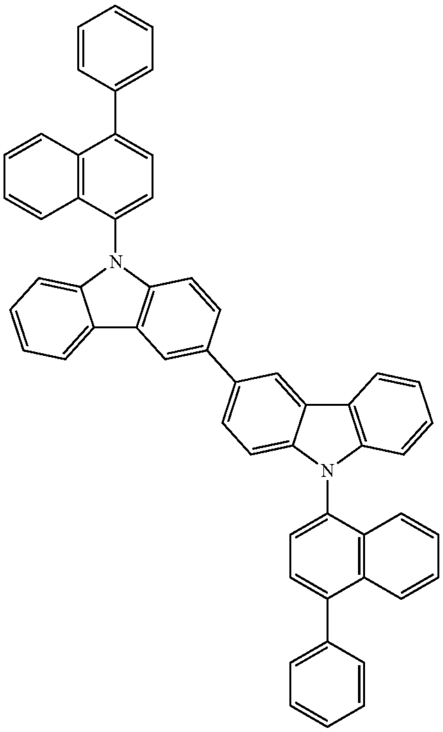
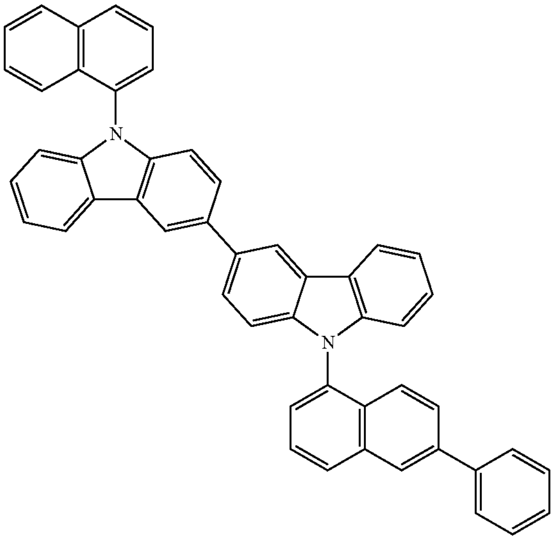

-continued
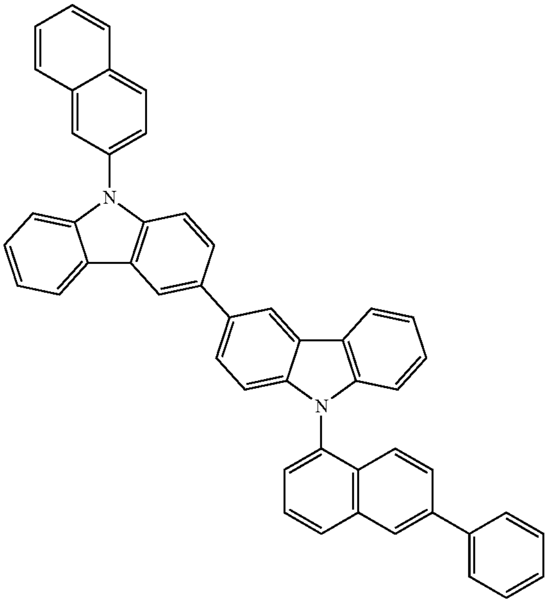
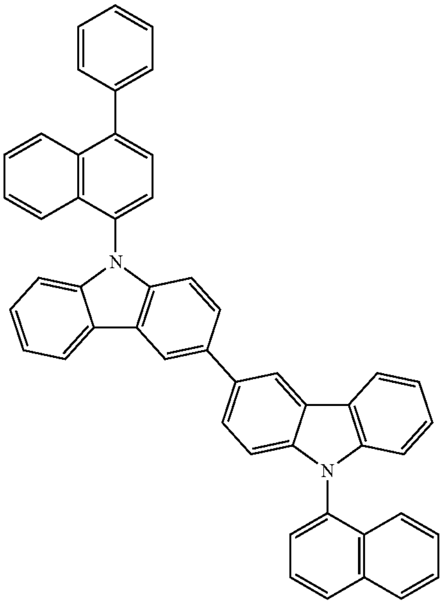
-continued
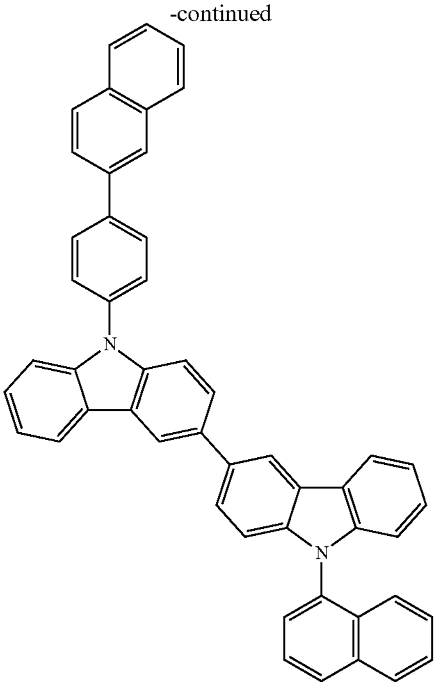
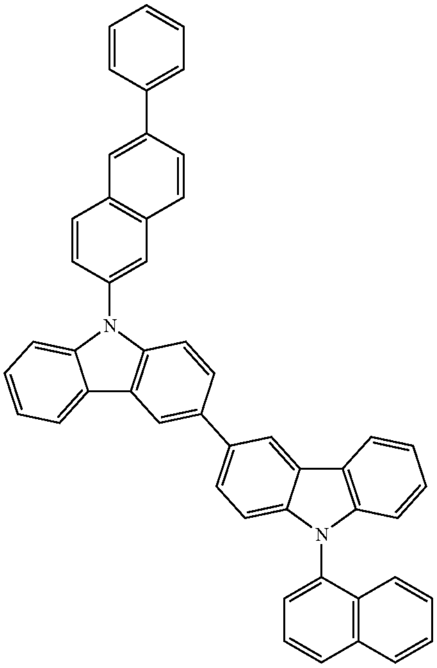

-continued
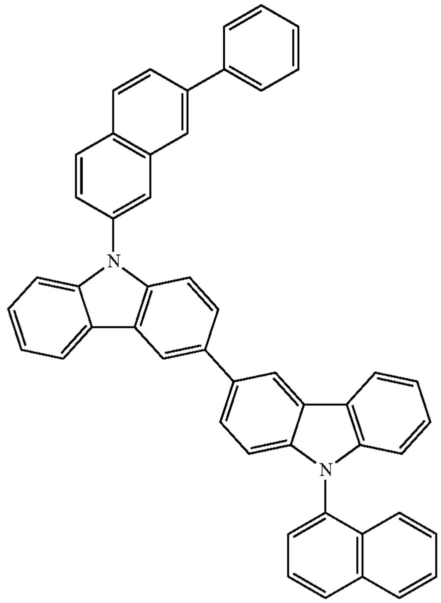
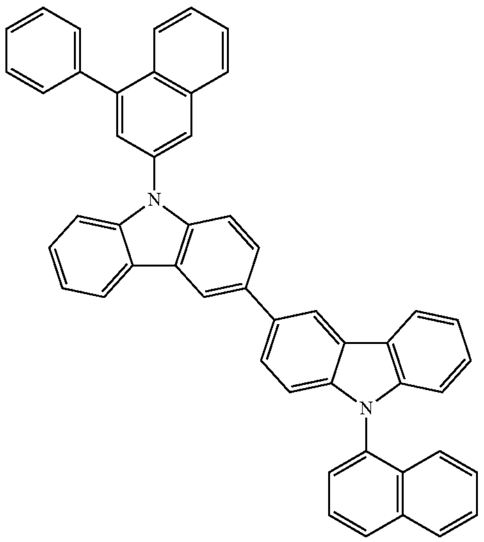
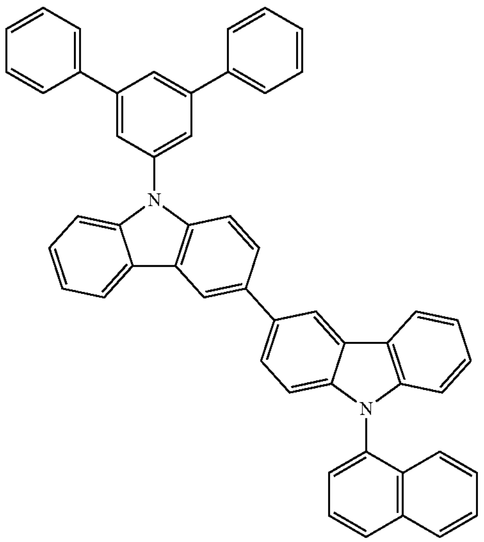
-continued
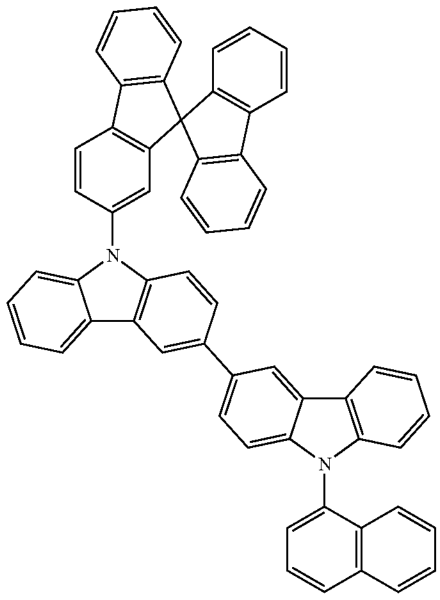
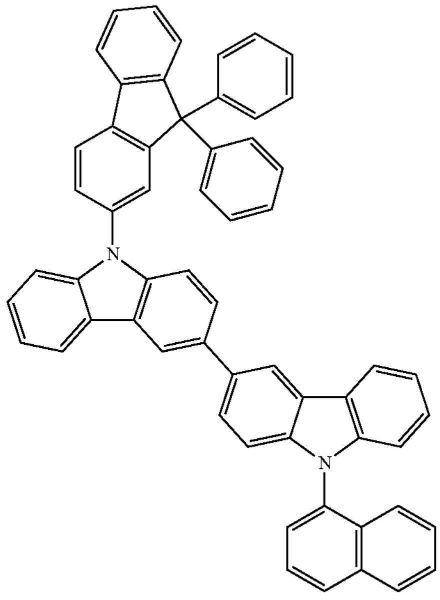

-continued
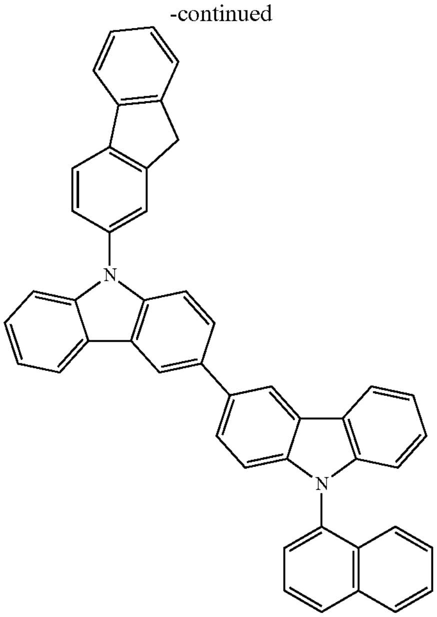
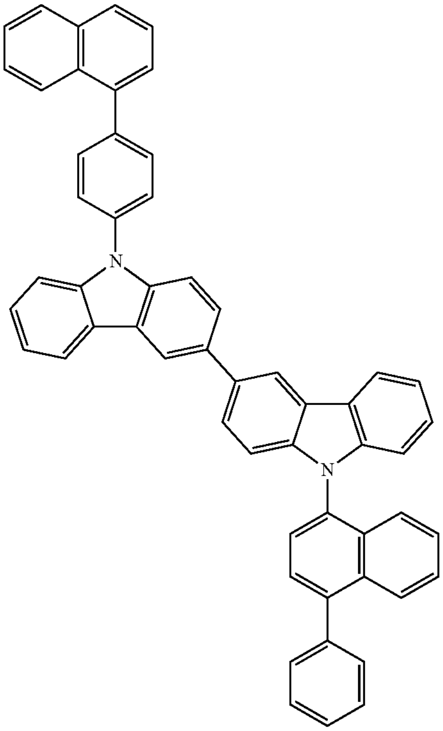
-continued
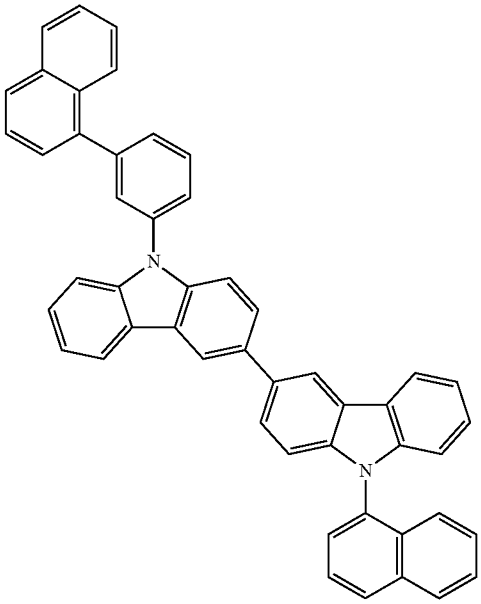
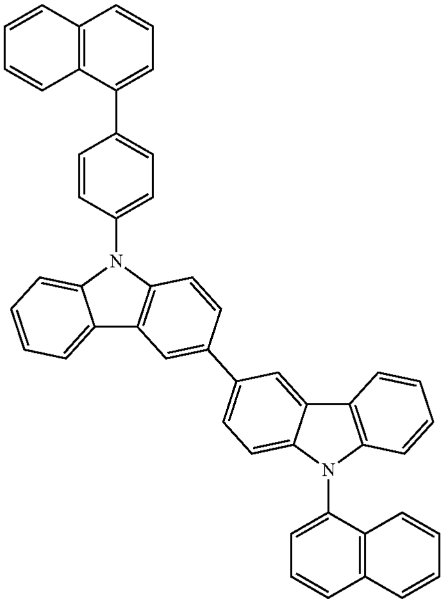

-continued
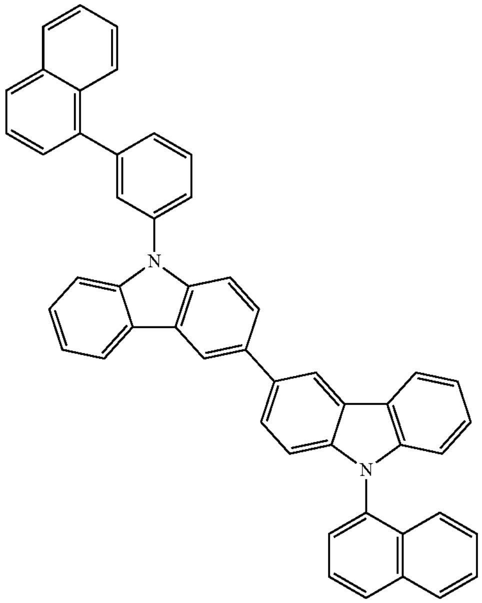
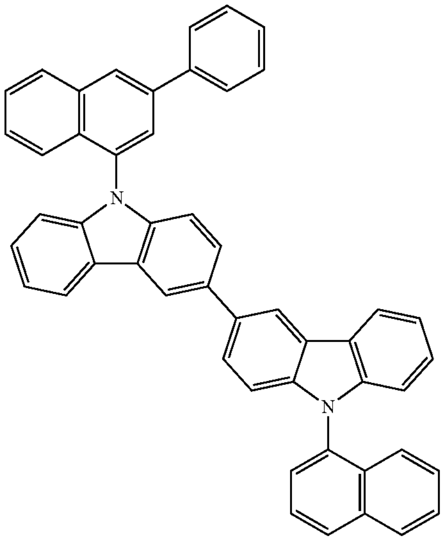
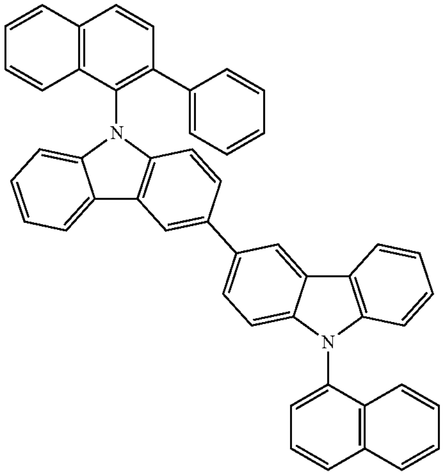
-continued
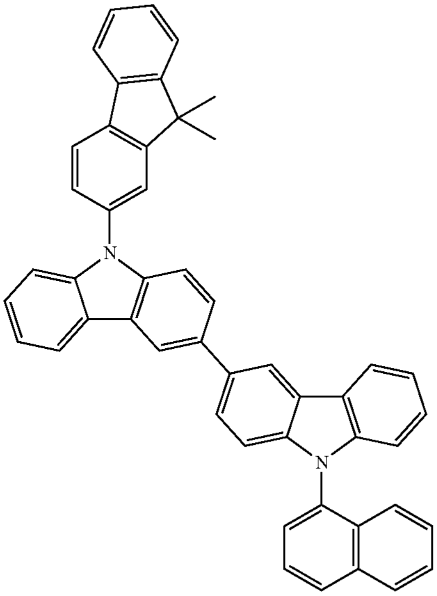
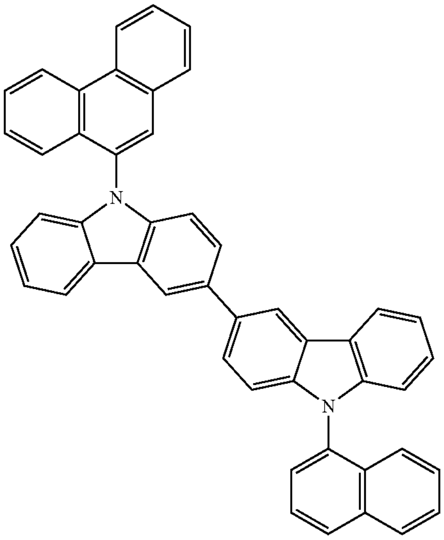

-continued
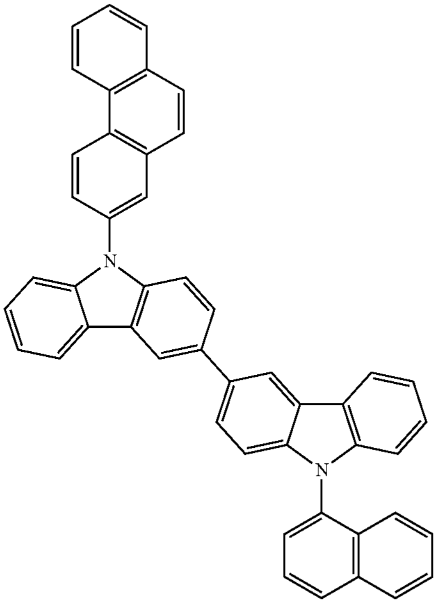
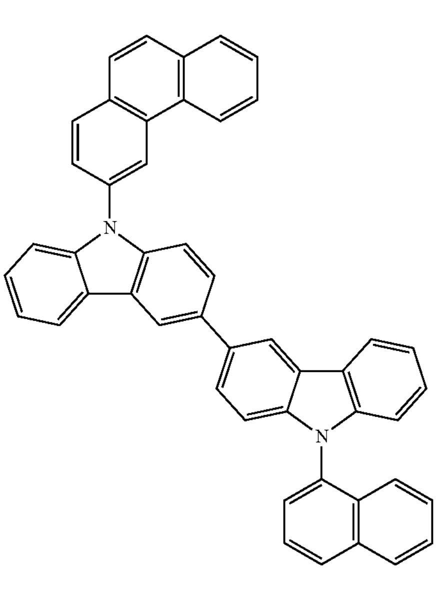
-continued
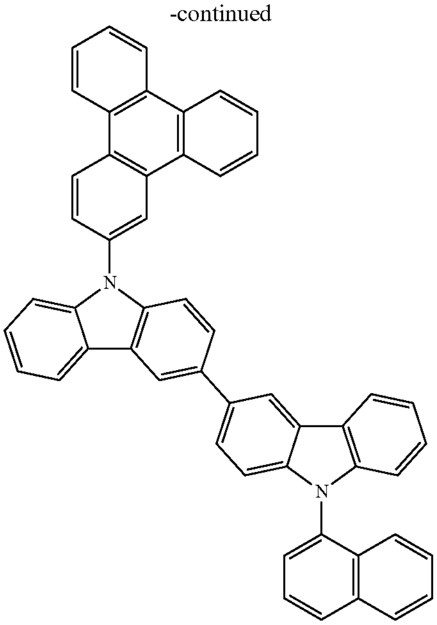
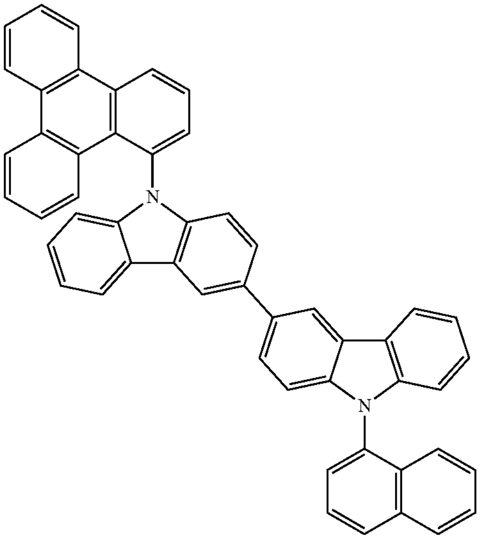
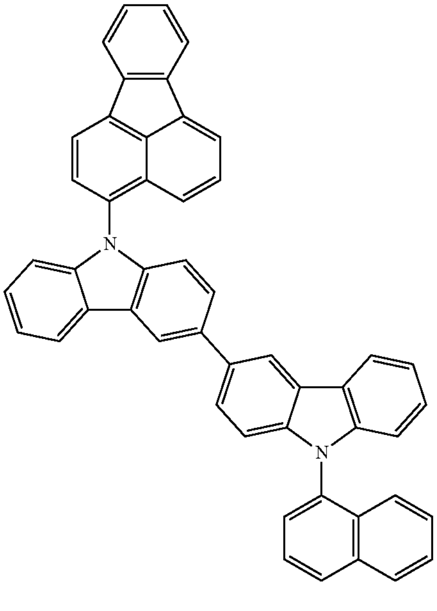

-continued
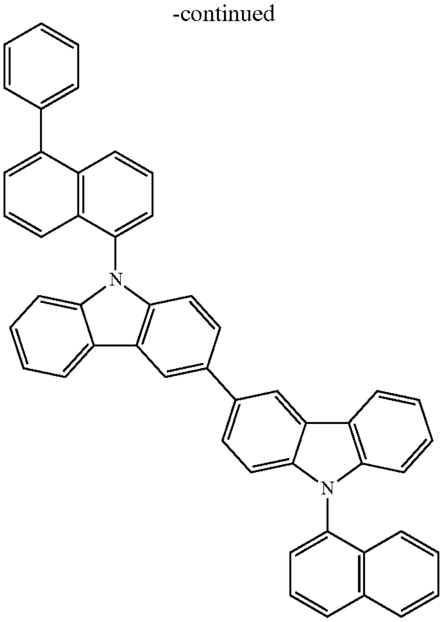
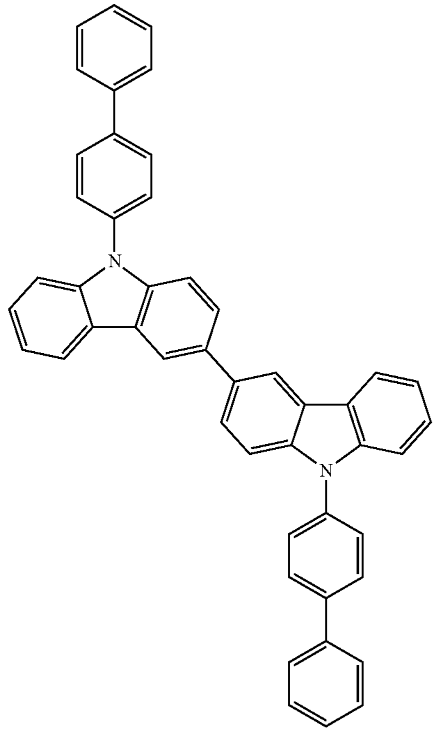
-continued
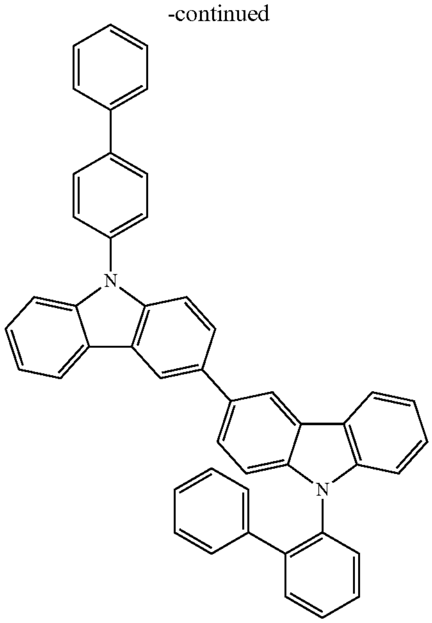
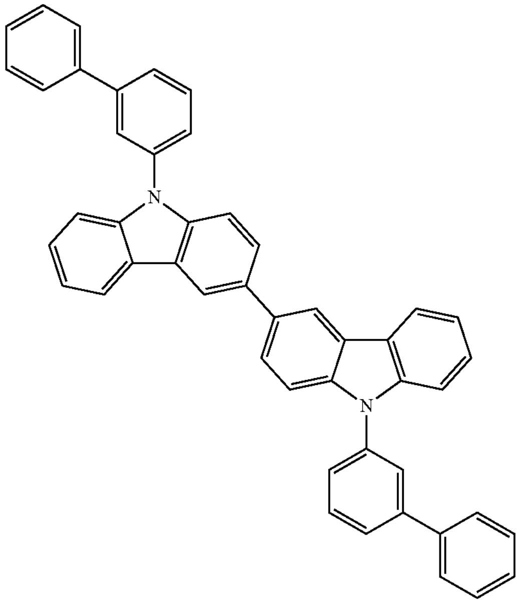
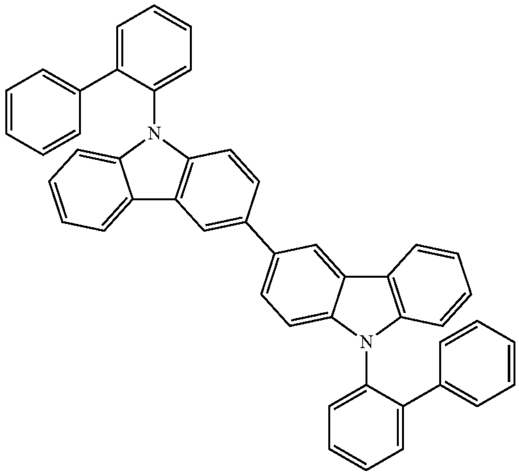

-continued
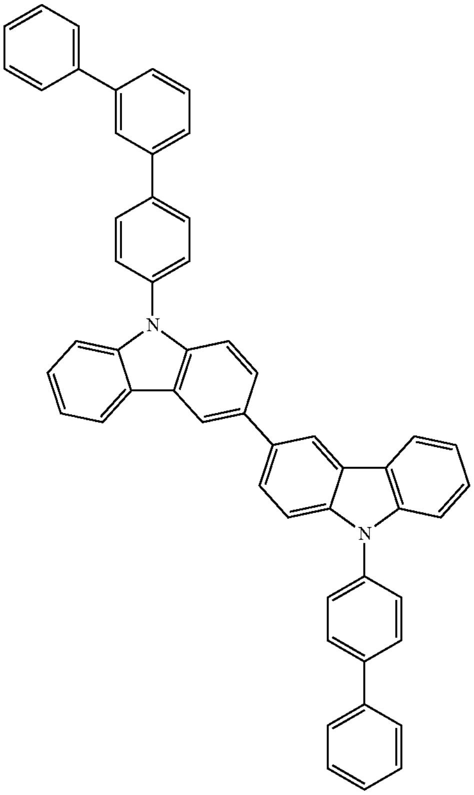
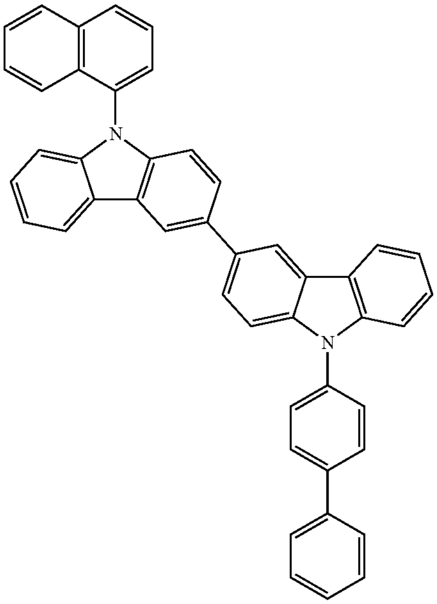
-continued
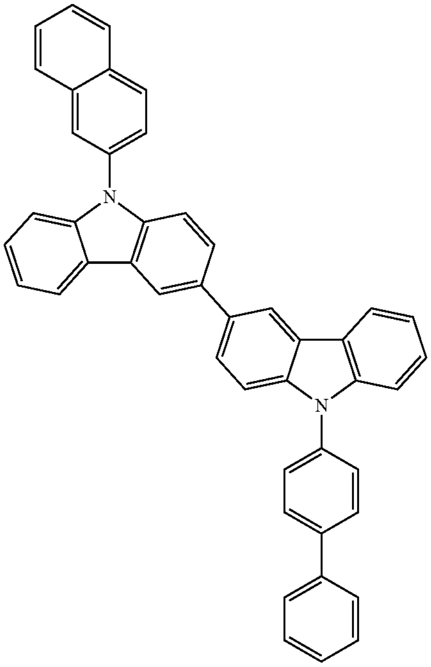
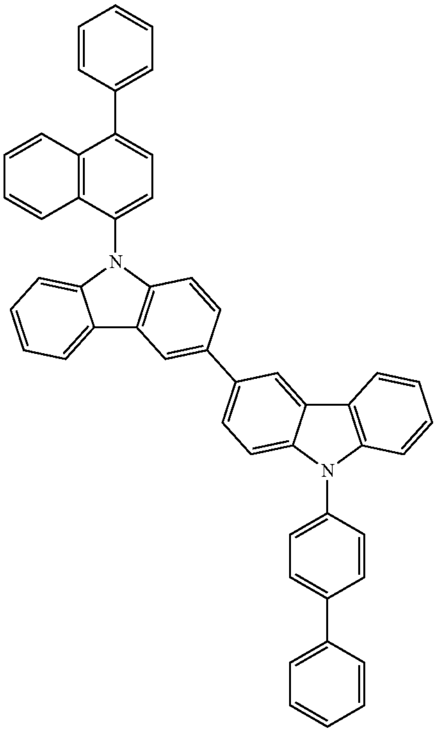

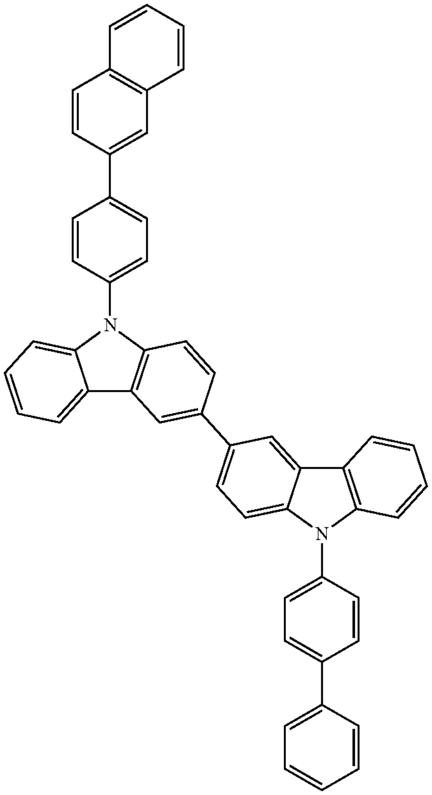
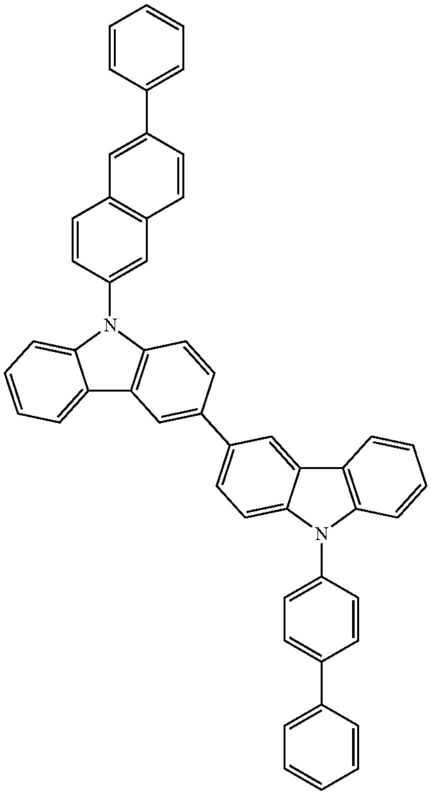
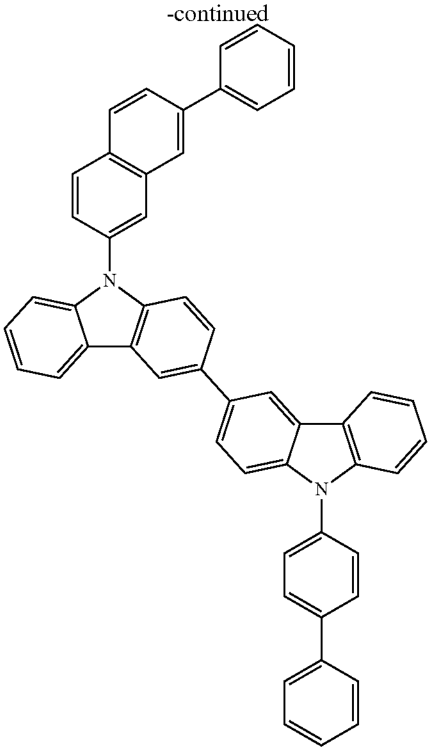
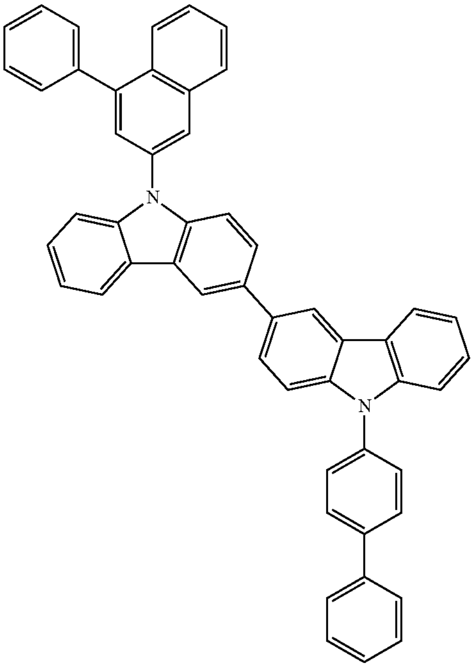

-continued
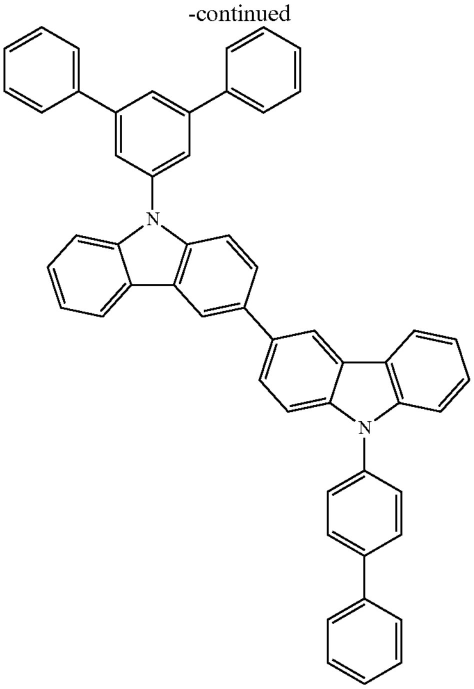
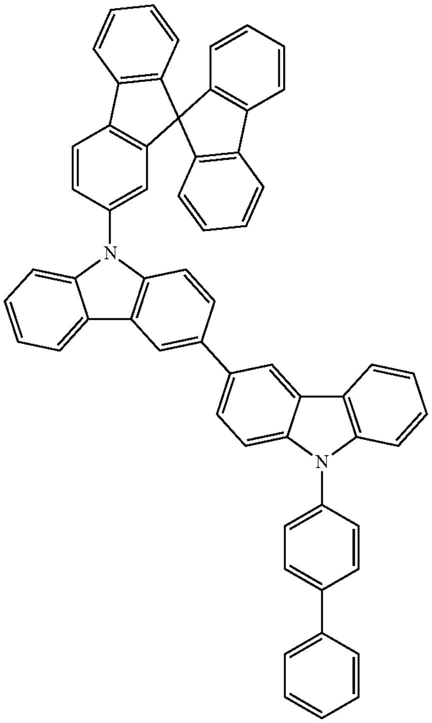
-continued
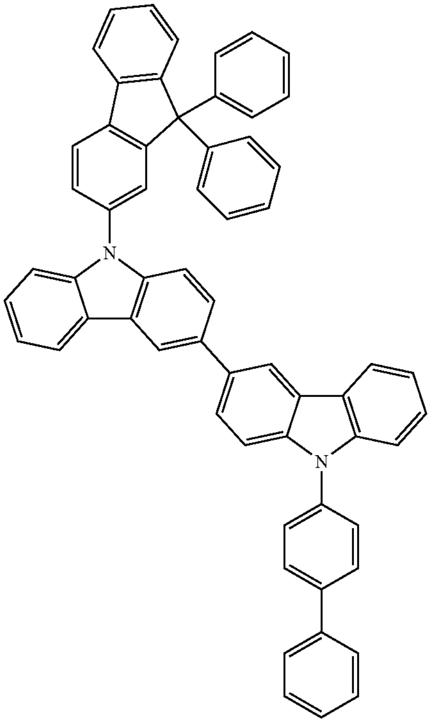
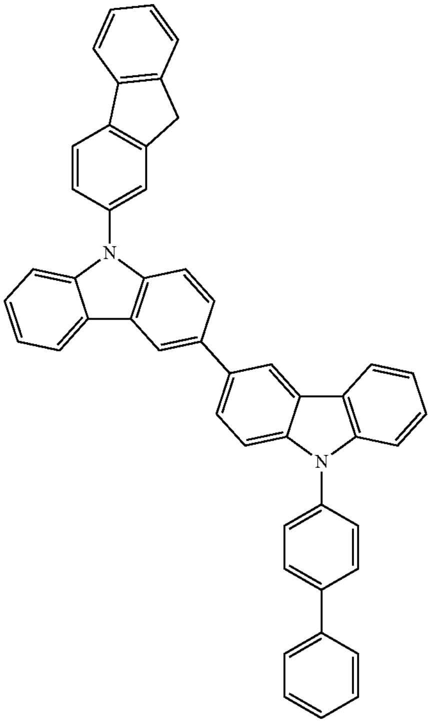

-continued
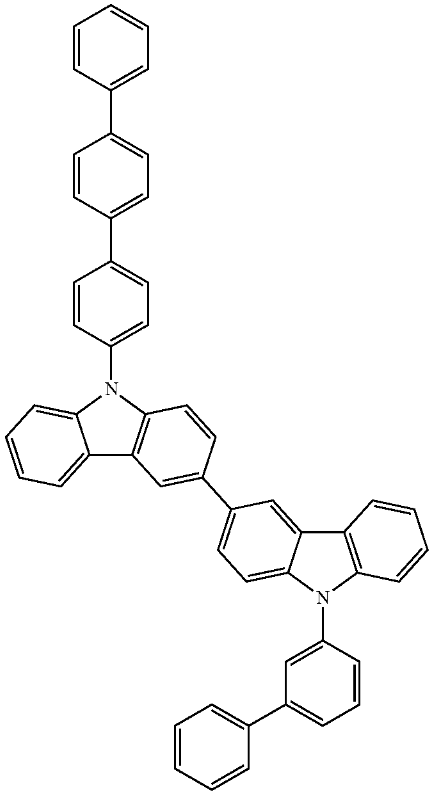
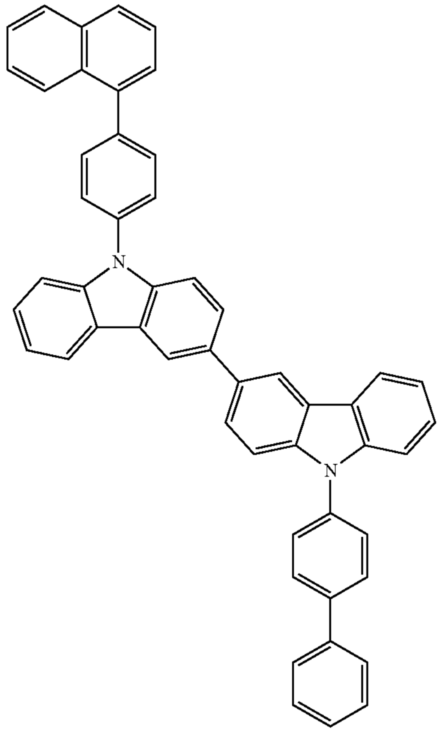
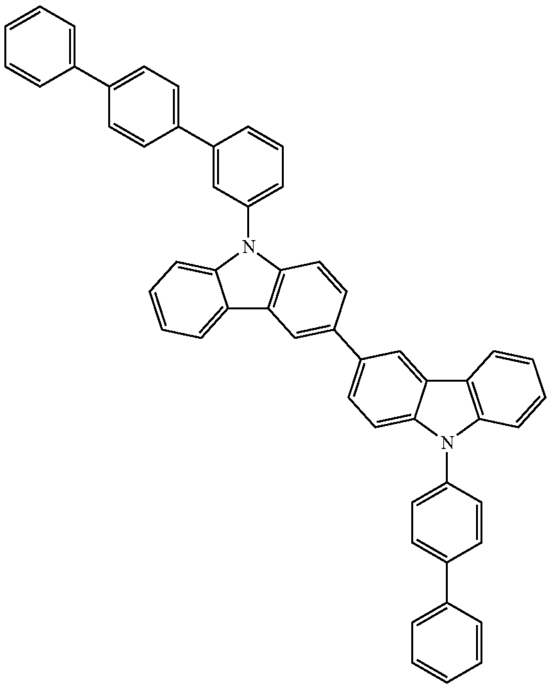
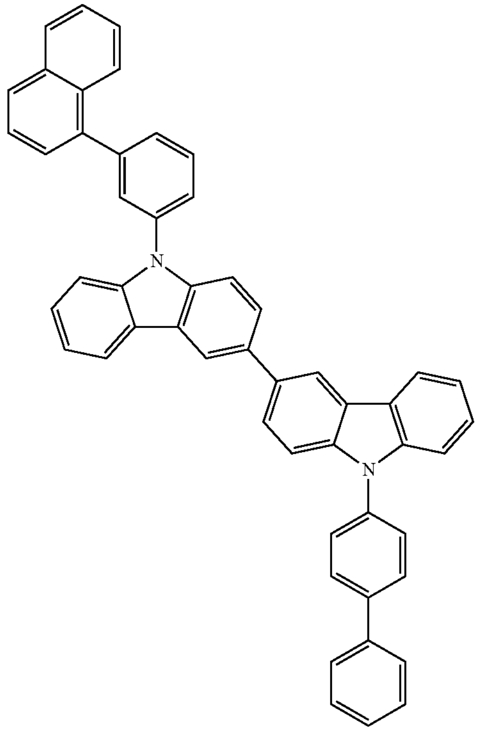
-continued

-continued
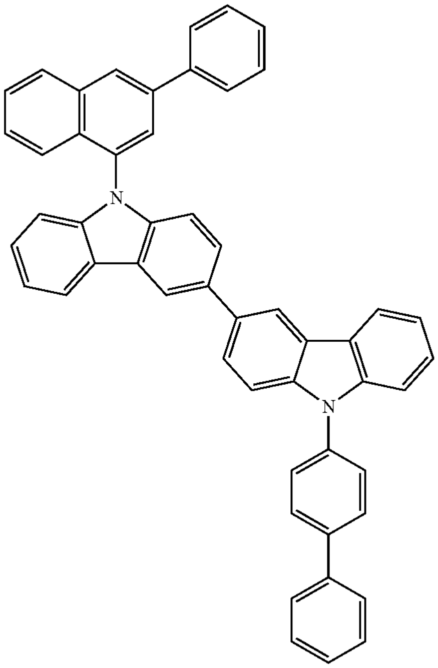
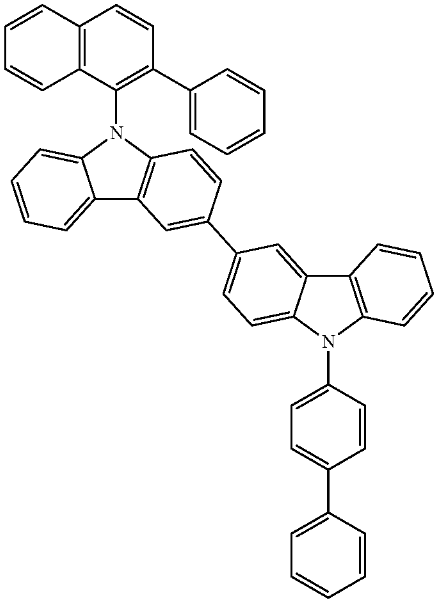
-continued
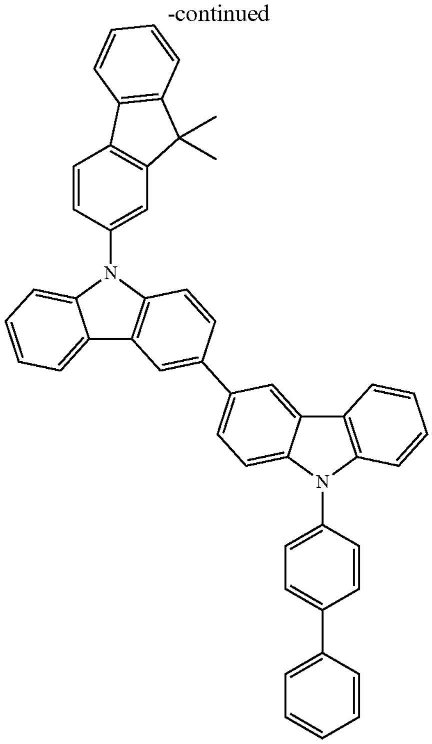
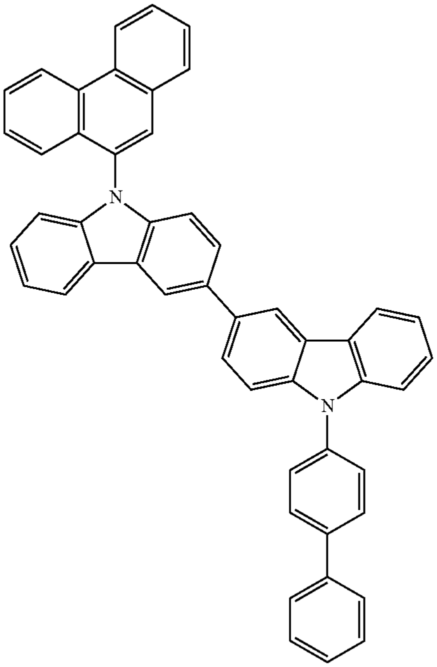

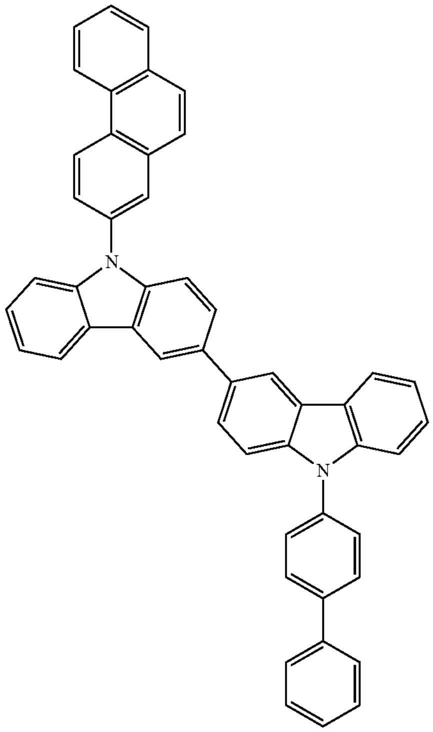
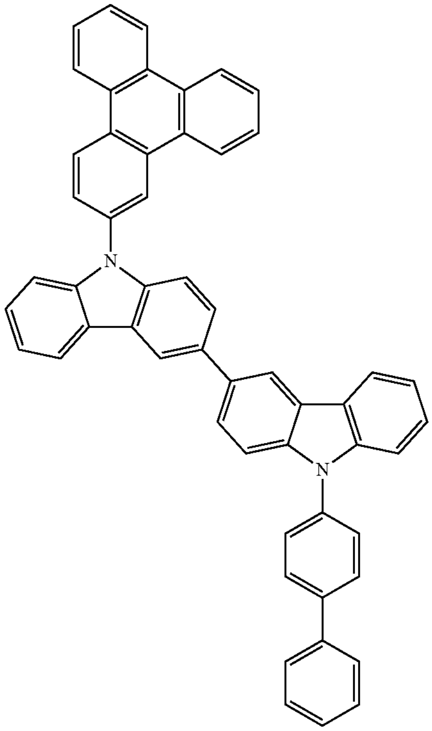
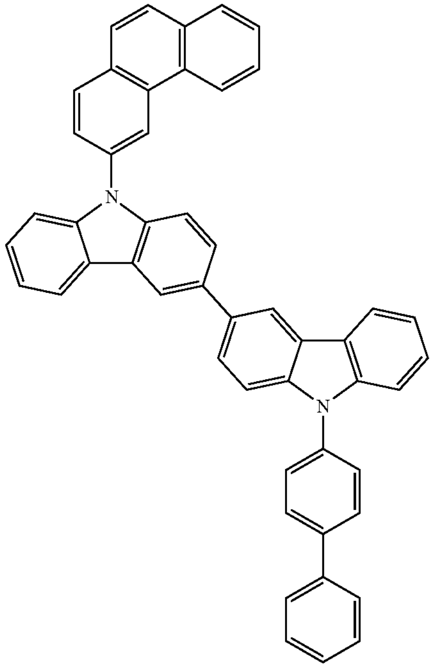
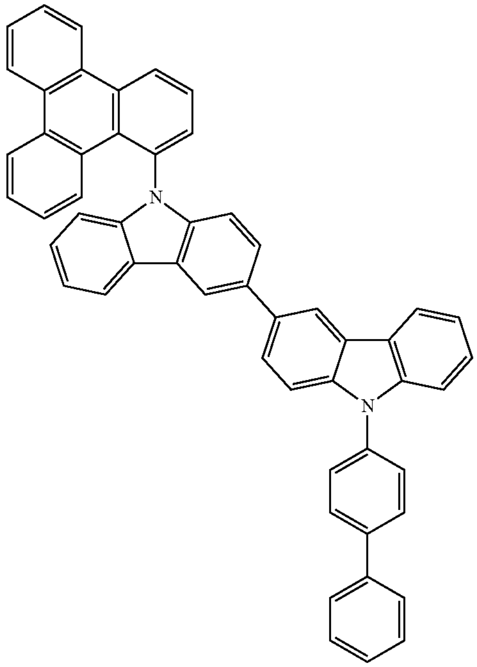

-continued
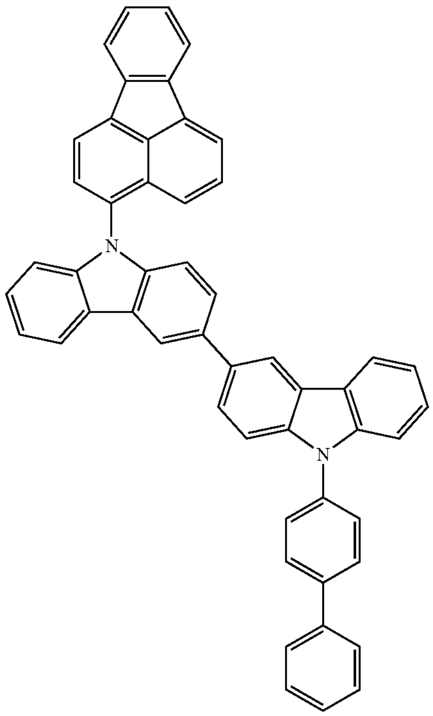
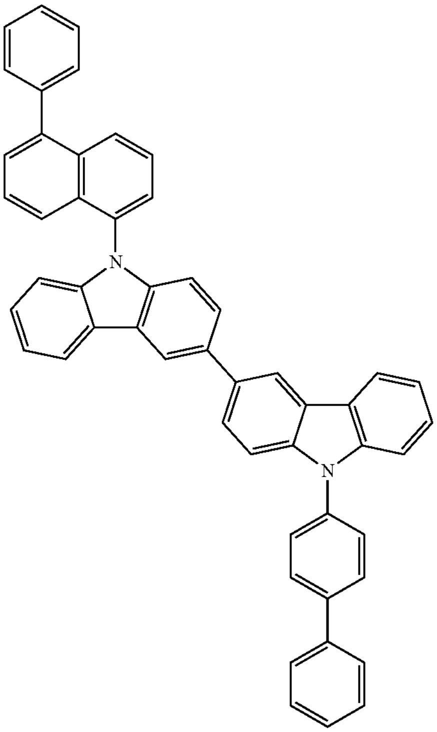
-continued
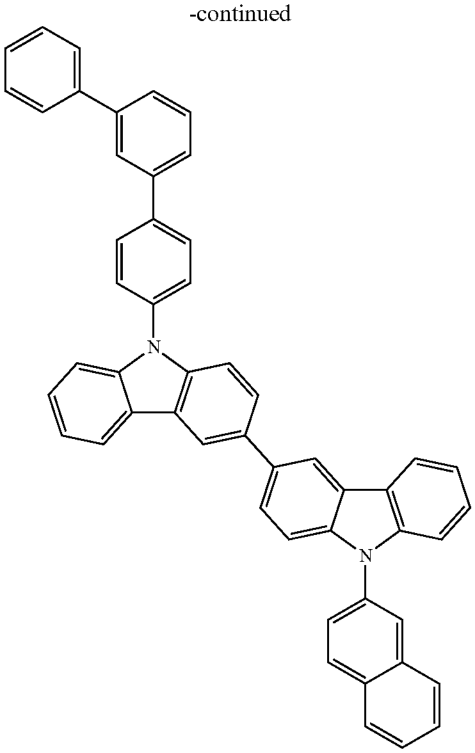
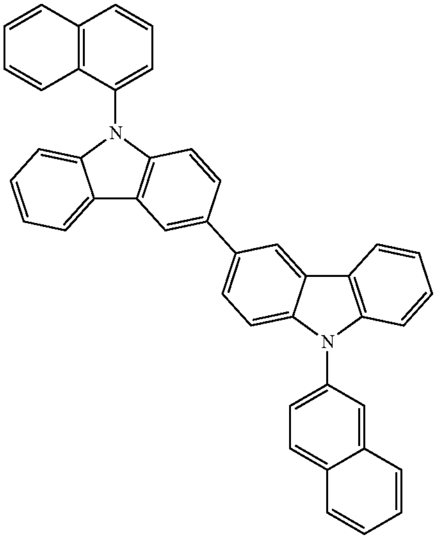

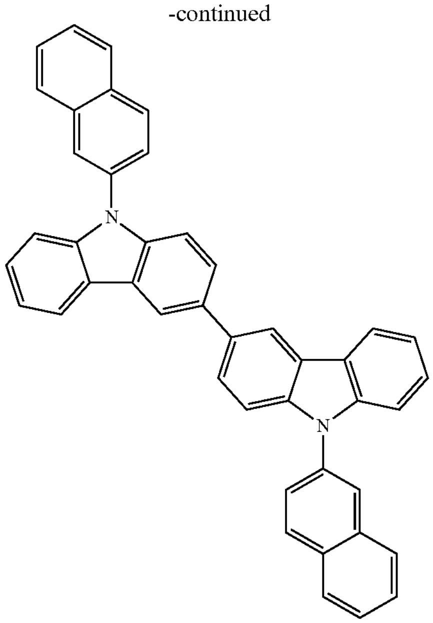
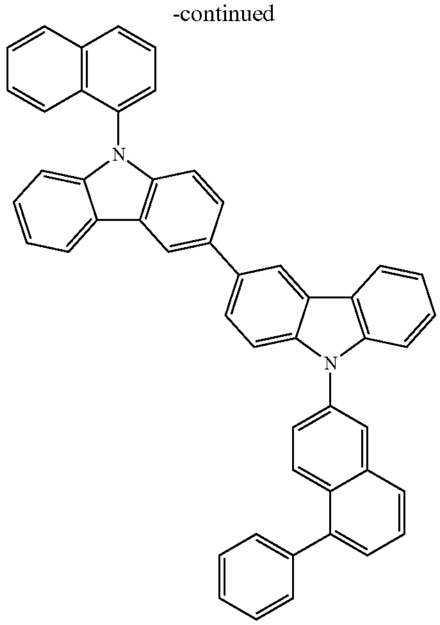
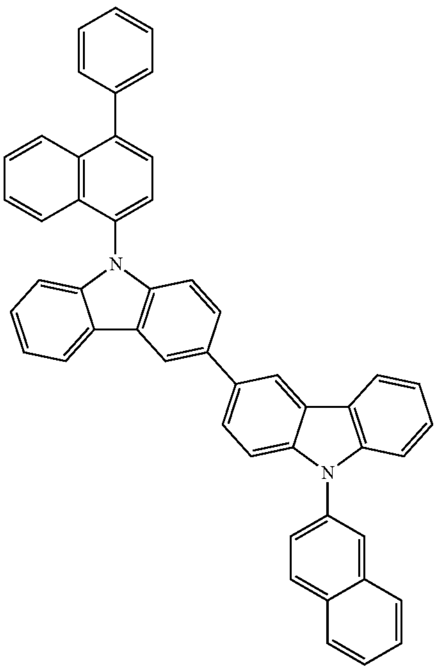
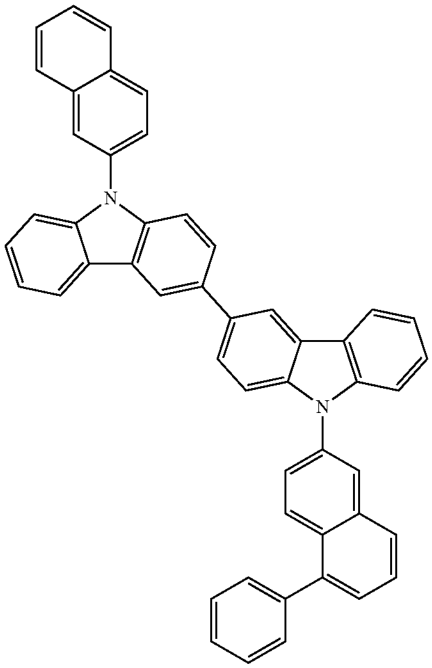

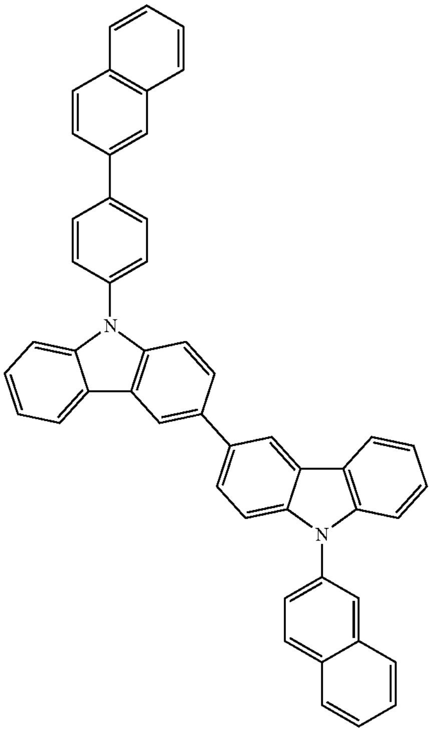
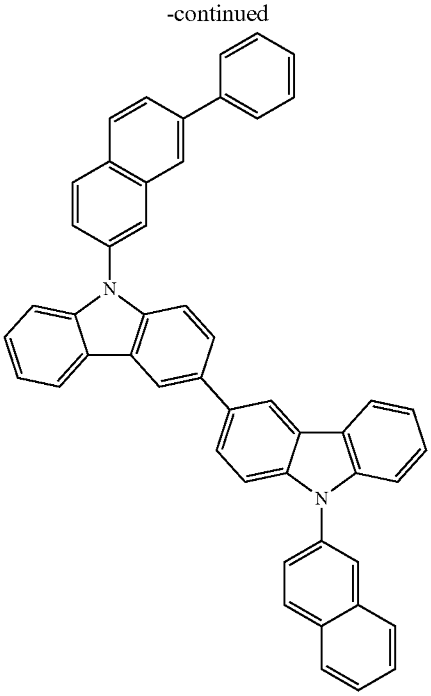
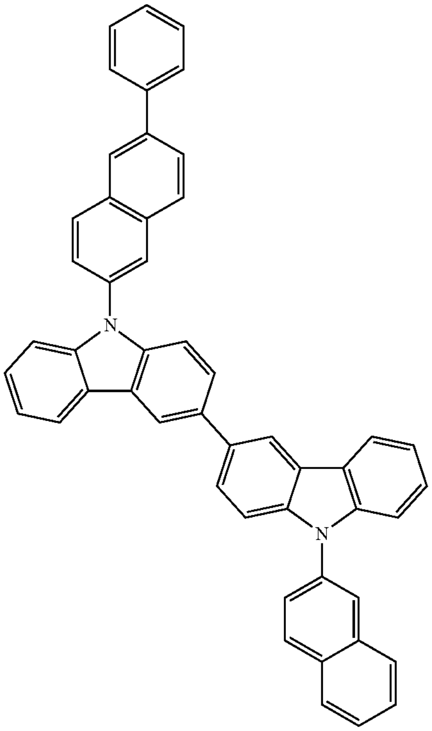
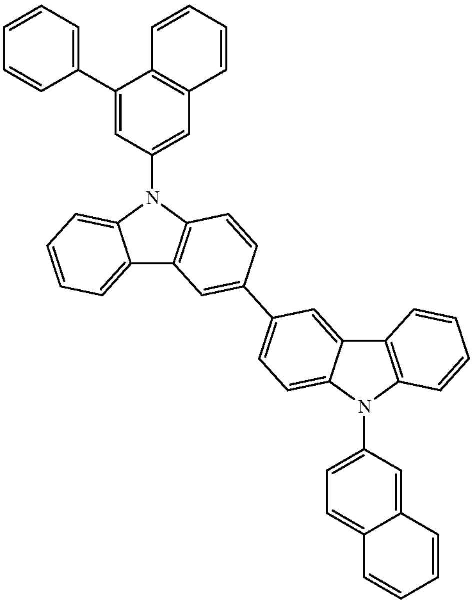

-continued
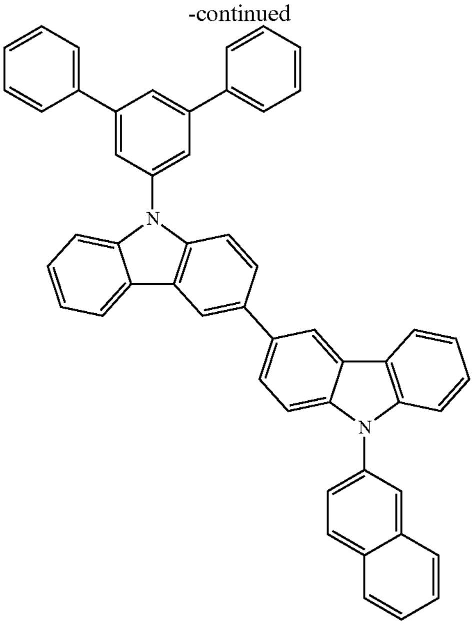
-continued
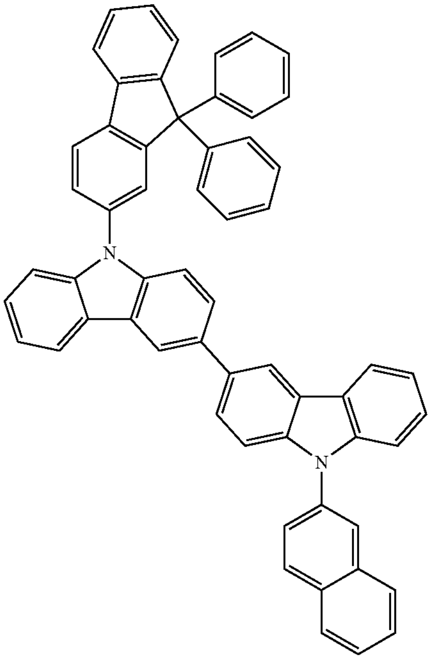
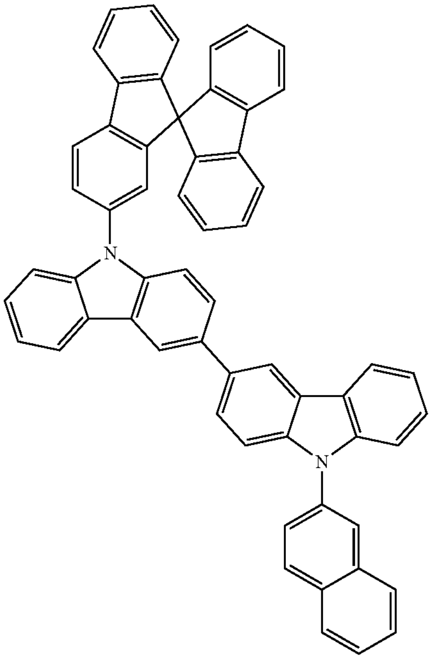
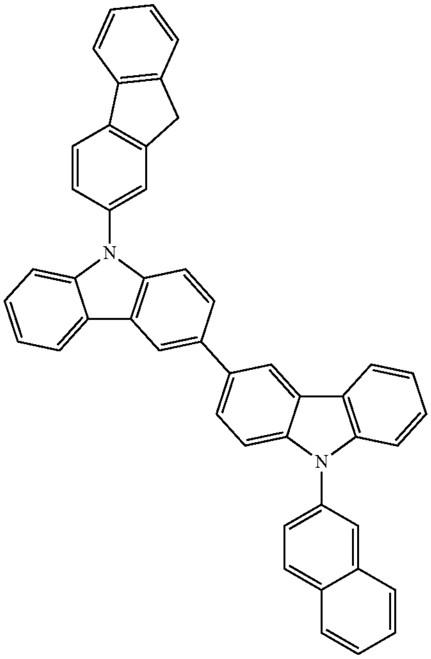

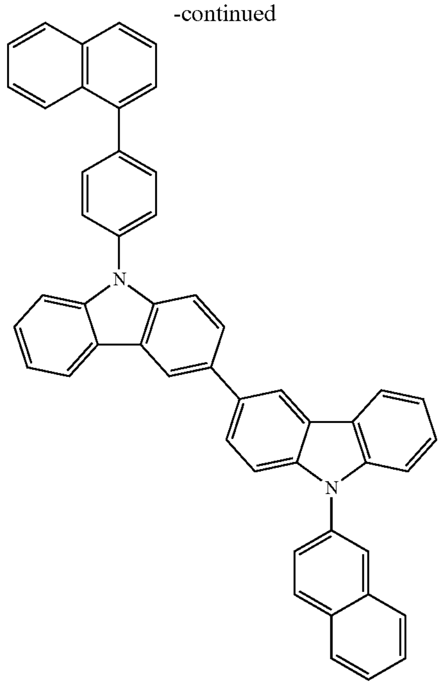
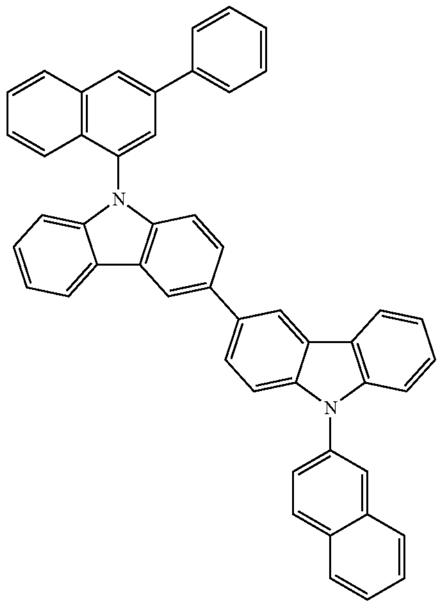
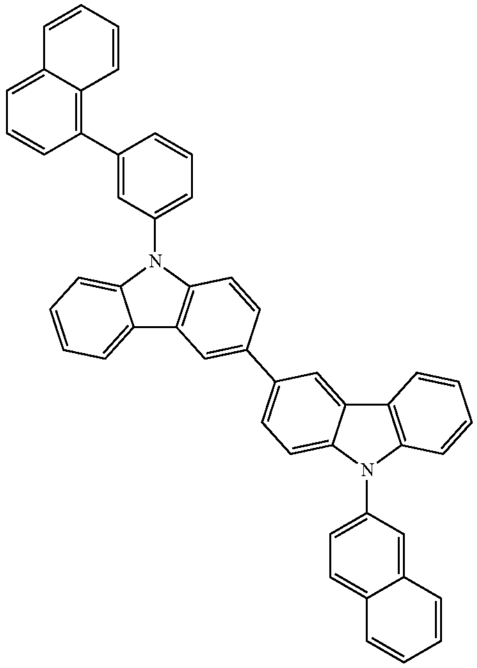
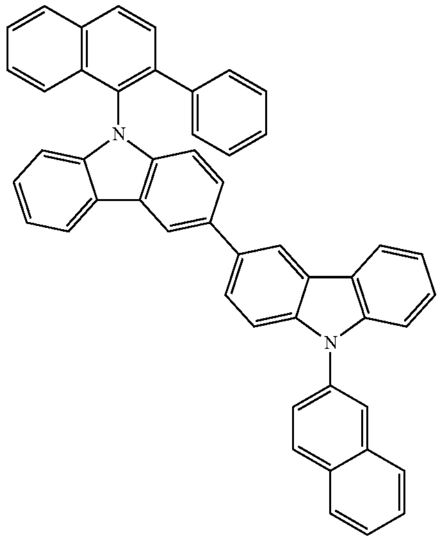

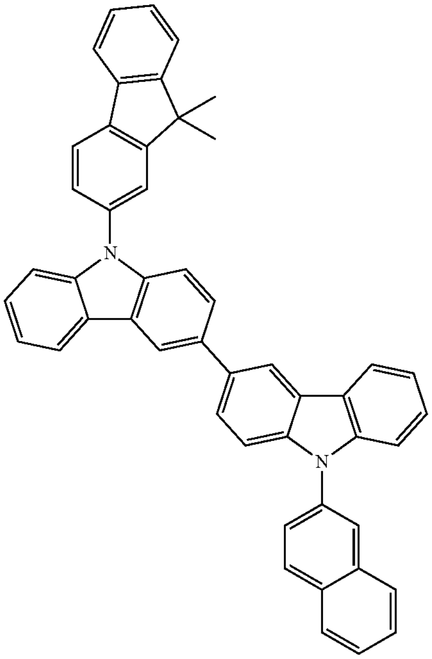
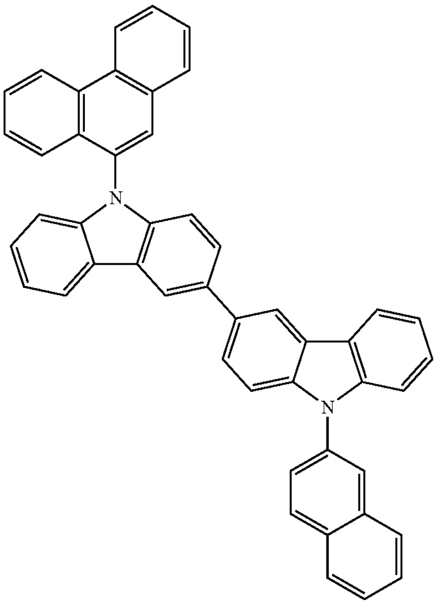
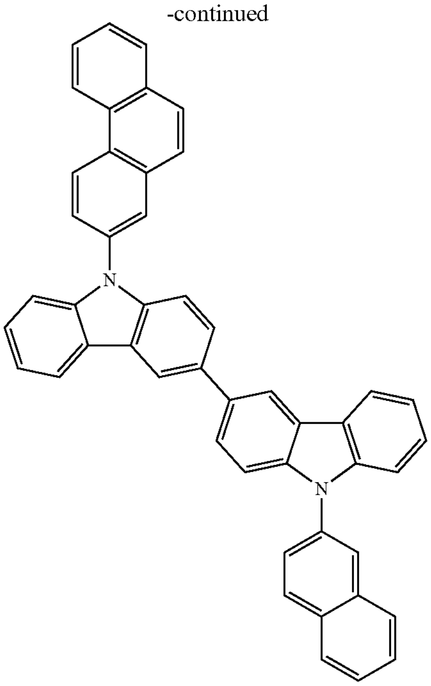
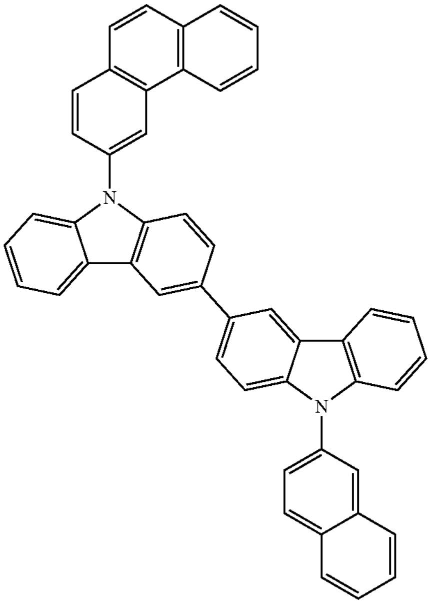

-continued
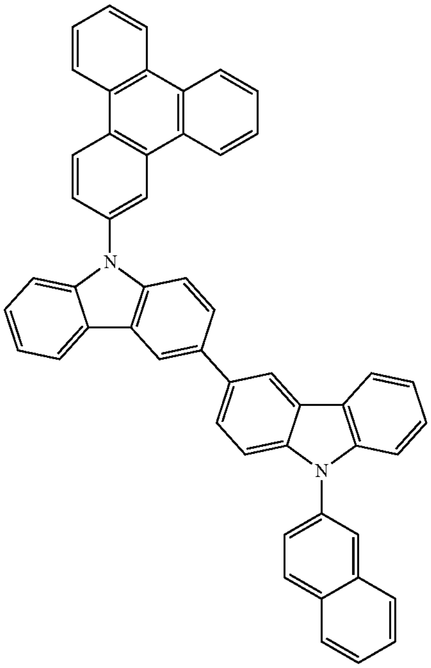
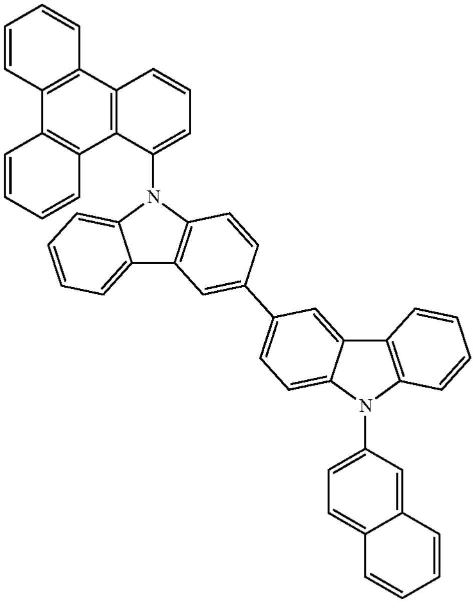
-continued
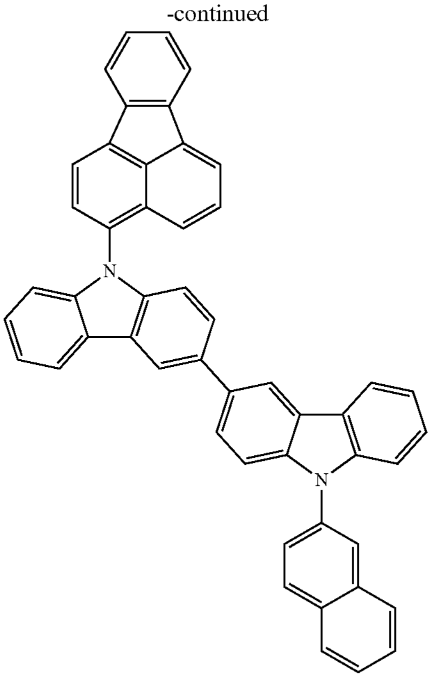
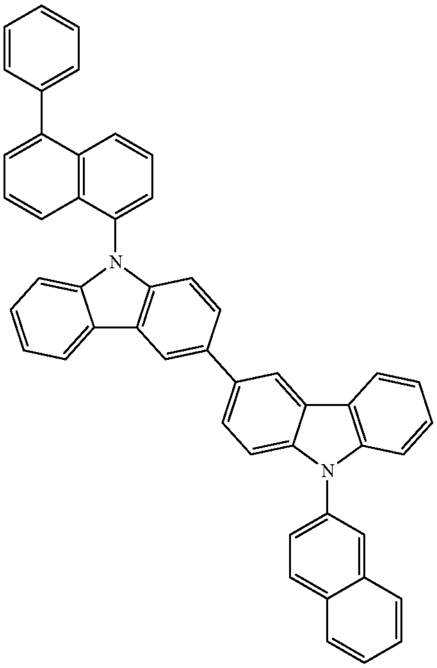

-continued
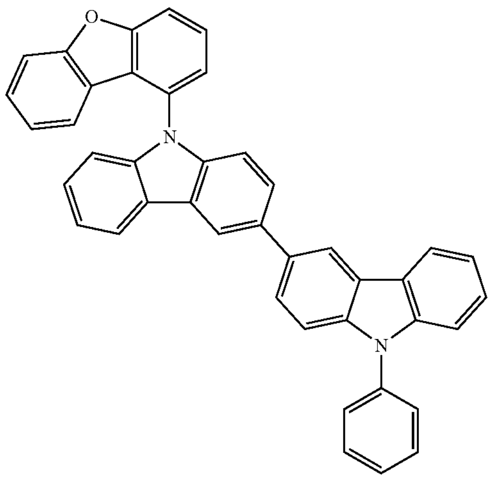
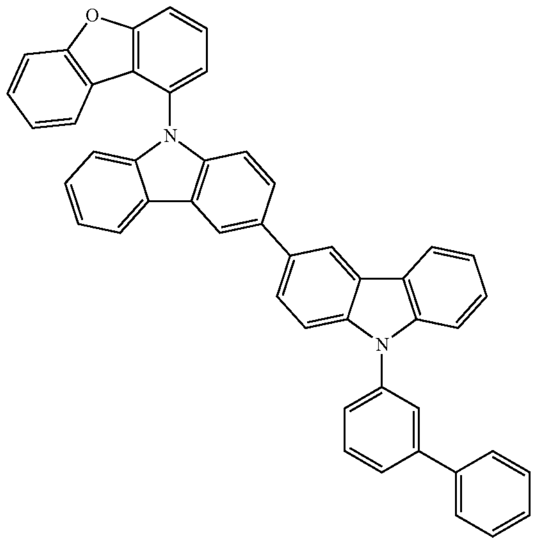
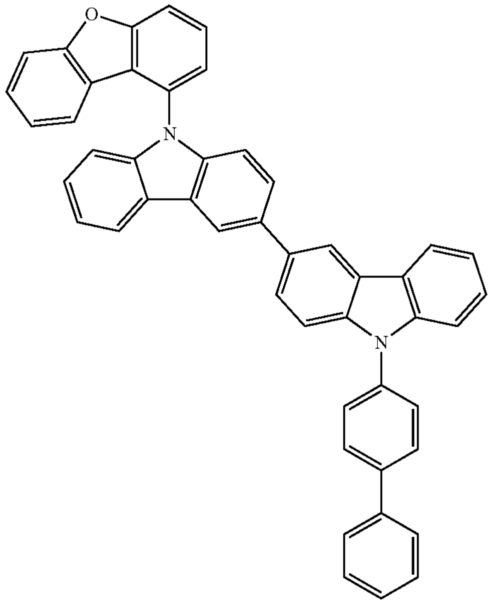
-continued
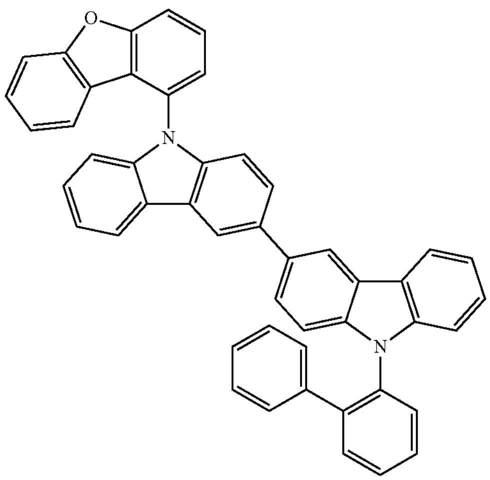
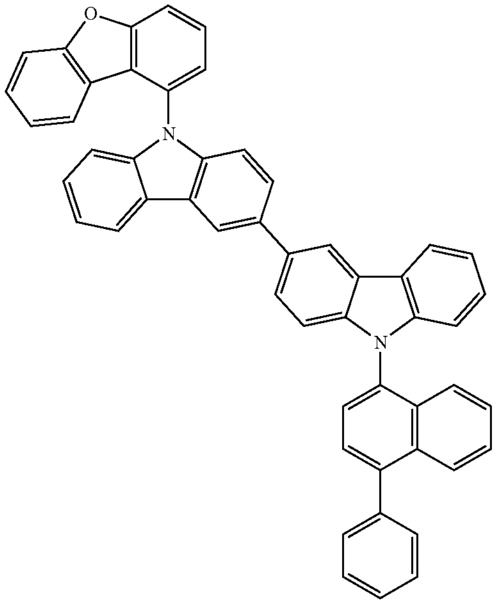
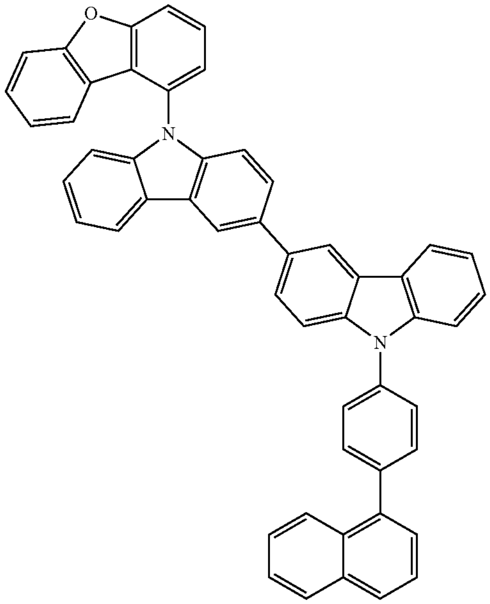

-continued
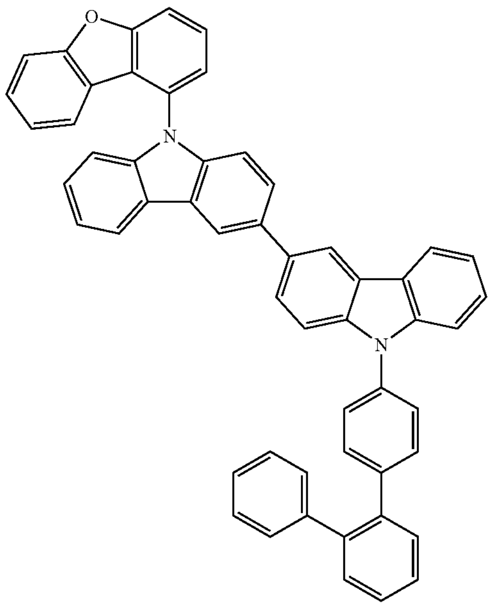
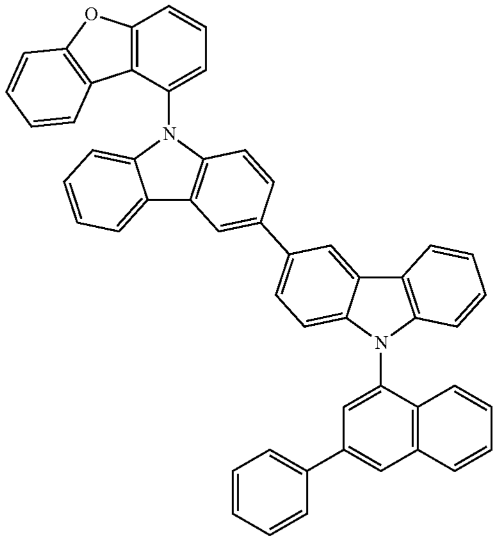
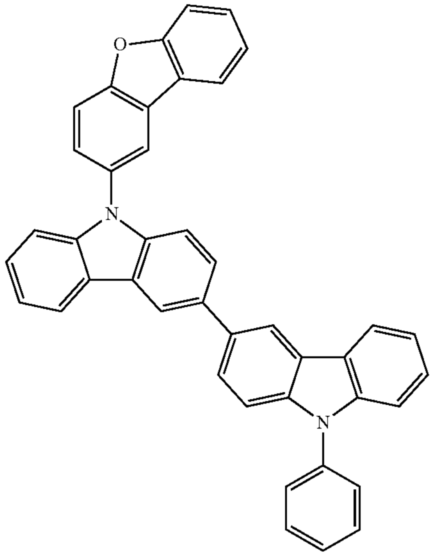
-continued
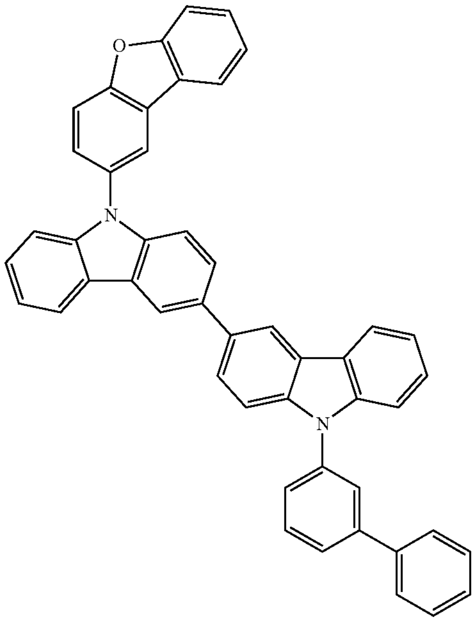
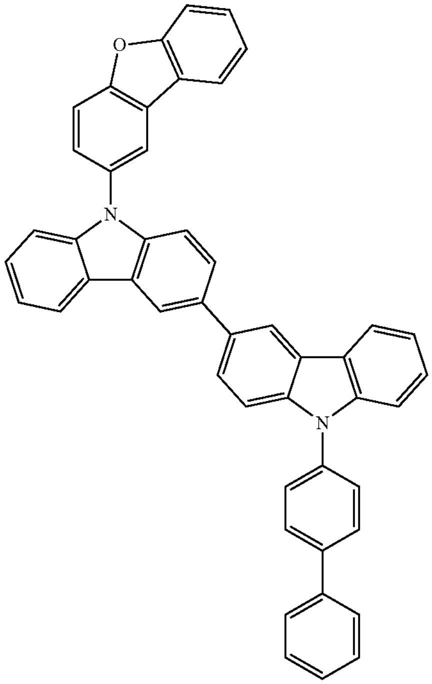

-continued
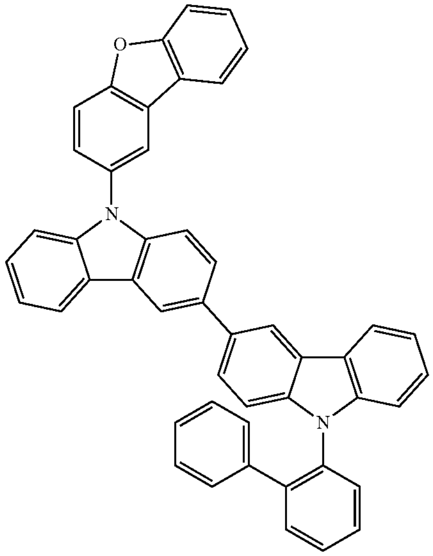
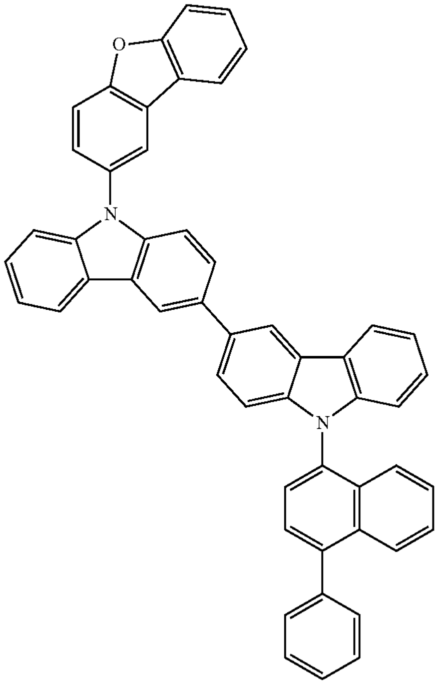
-continued
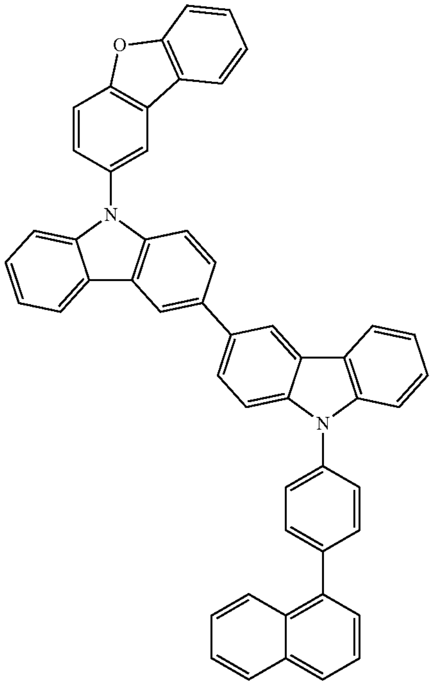
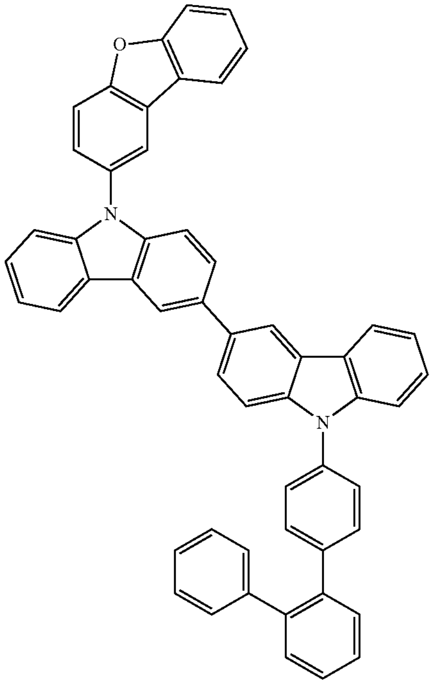

-continued
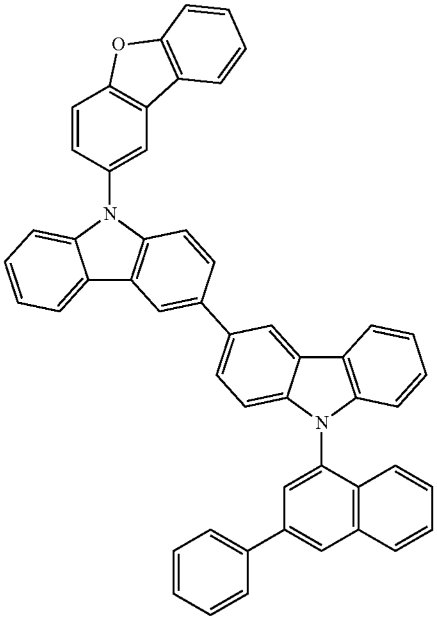
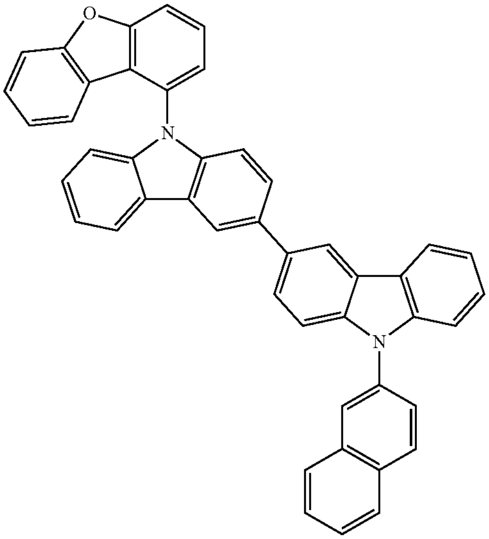
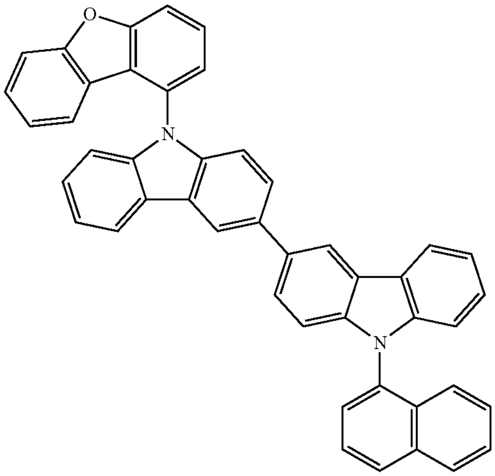
-continued
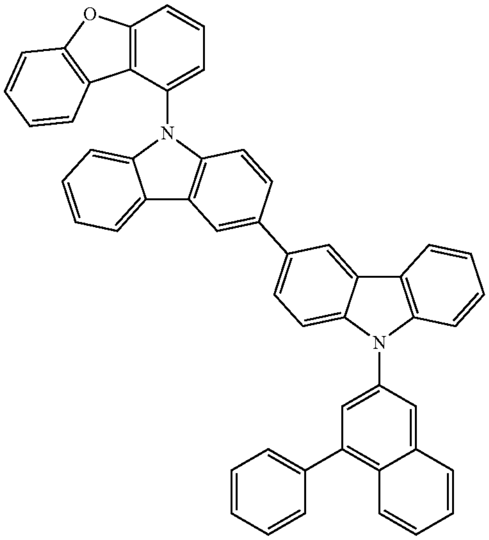
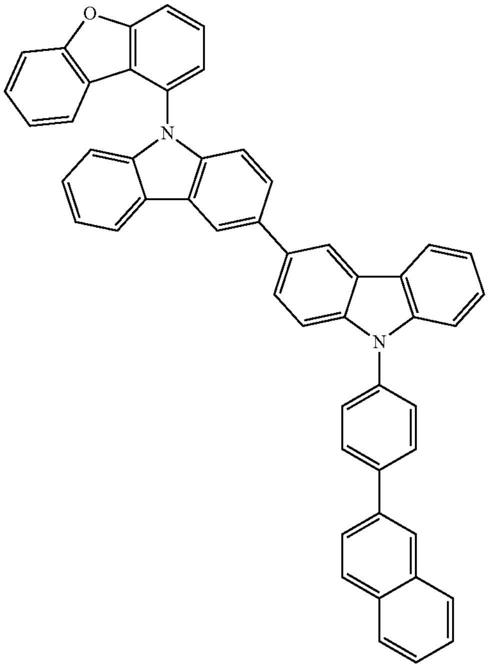

-continued
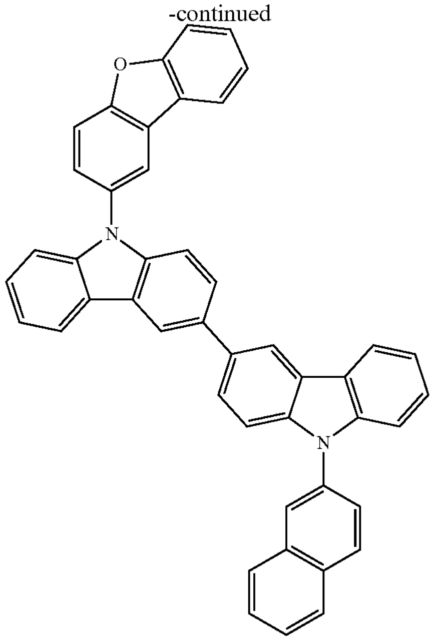
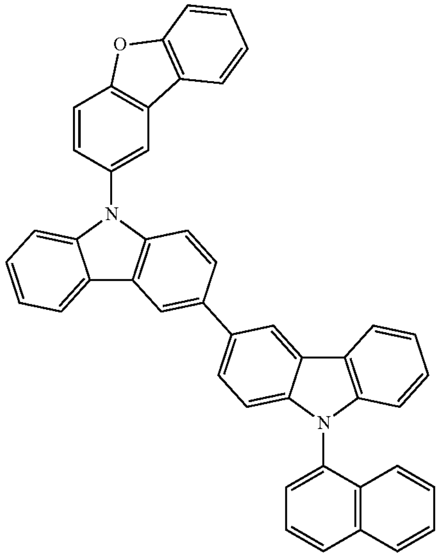
-continued
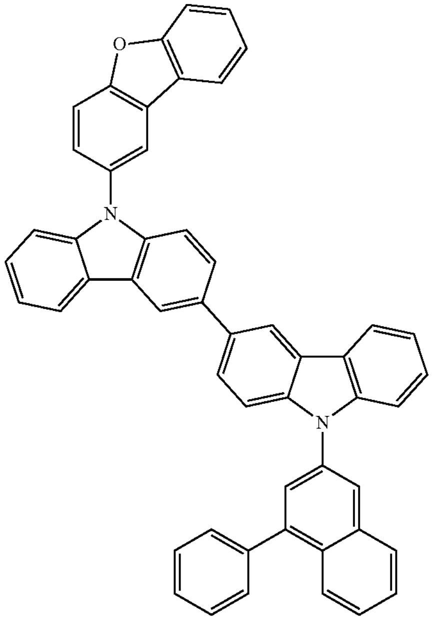
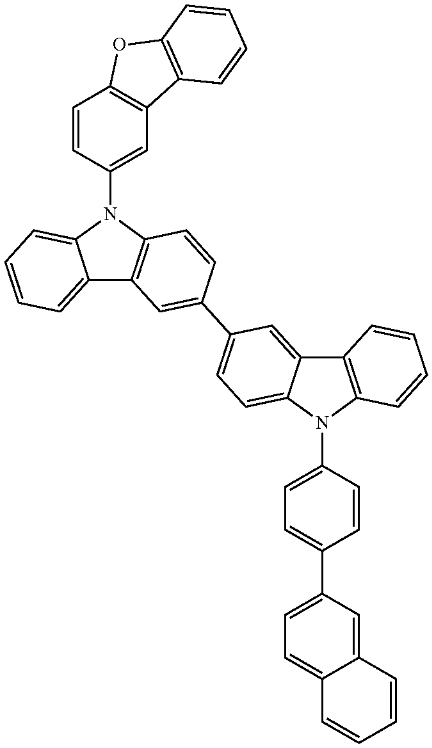

-continued
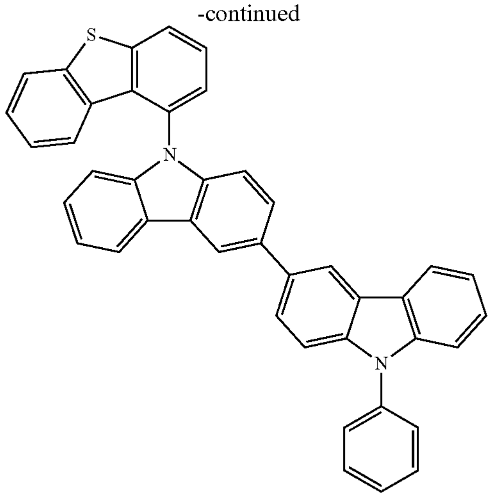
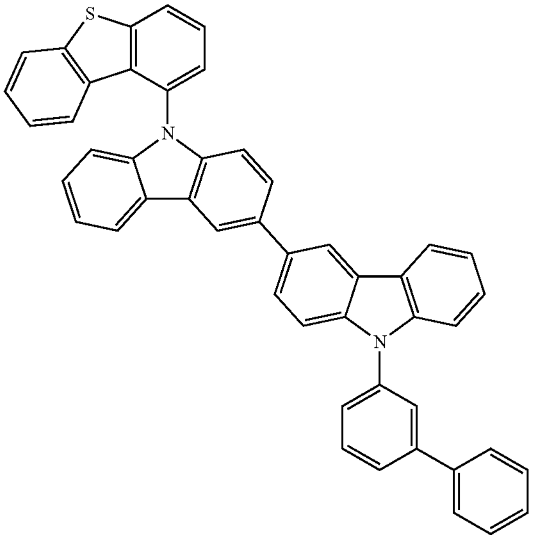
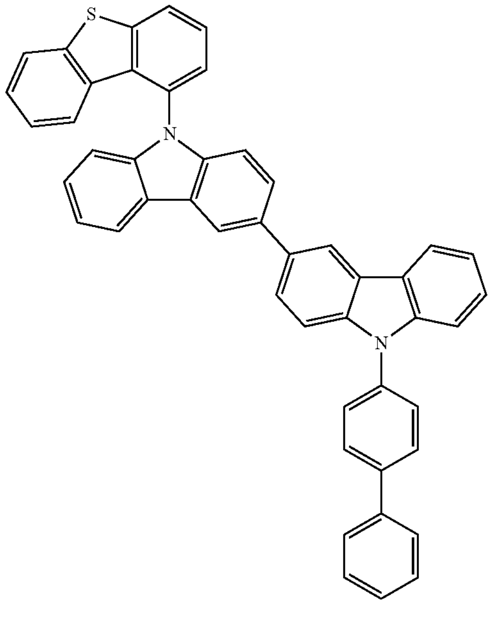
-continued
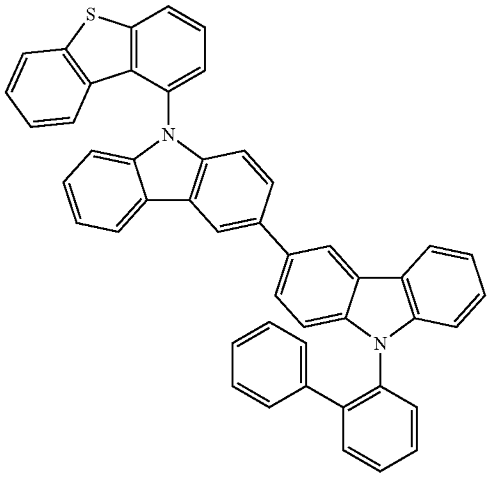
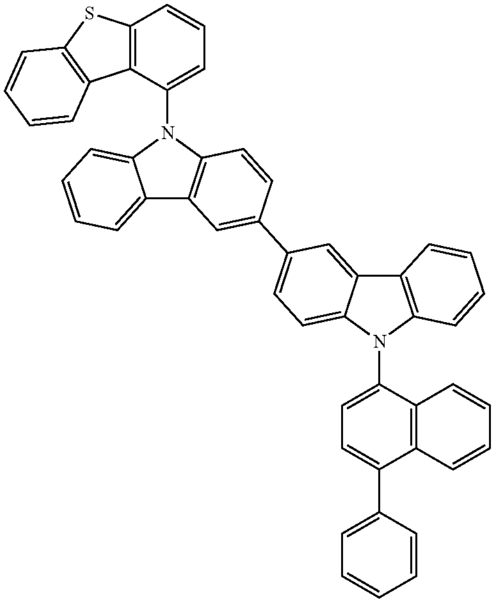
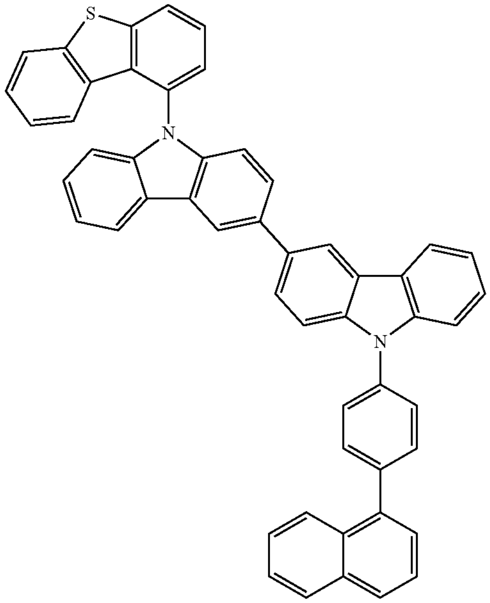

-continued
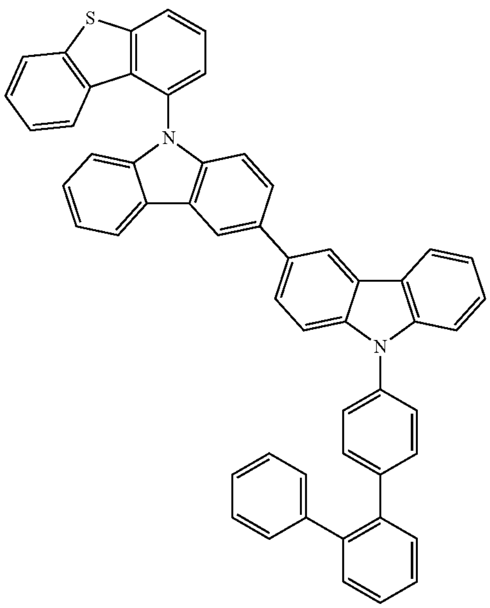
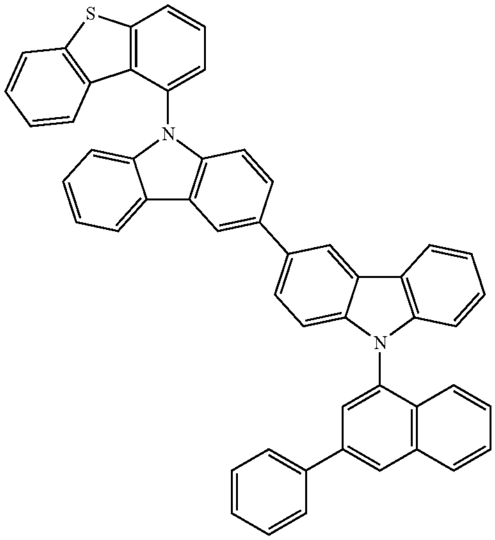
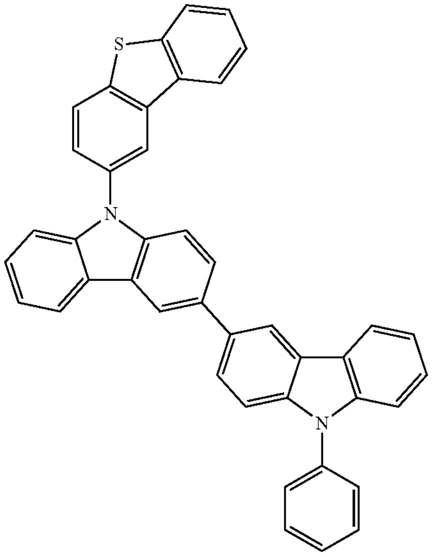
-continued
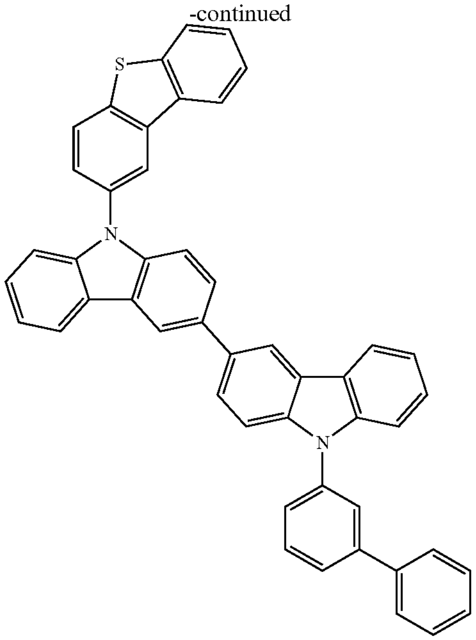
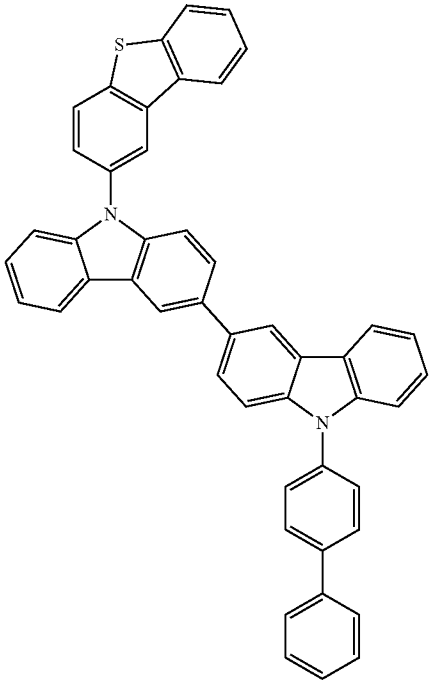

-continued
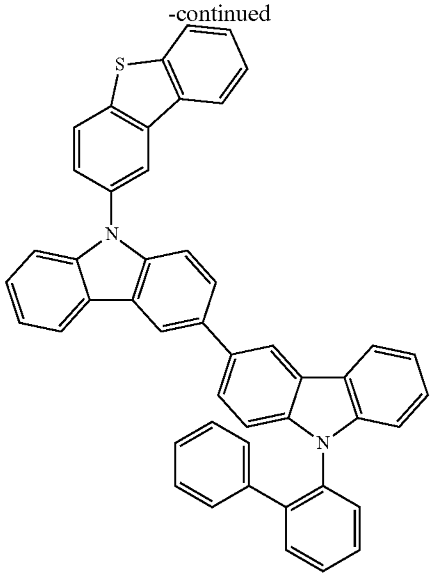
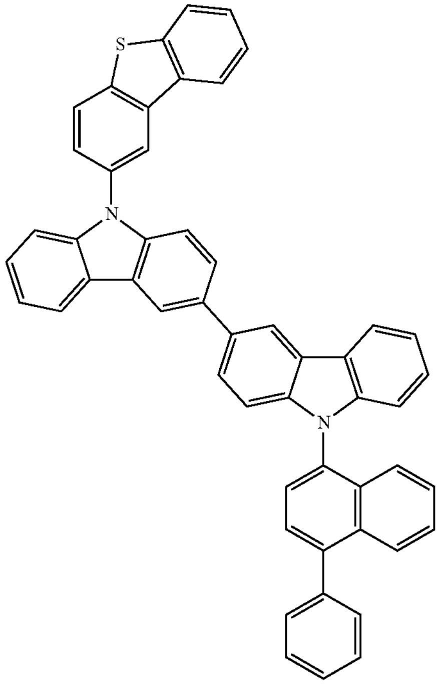
-continued
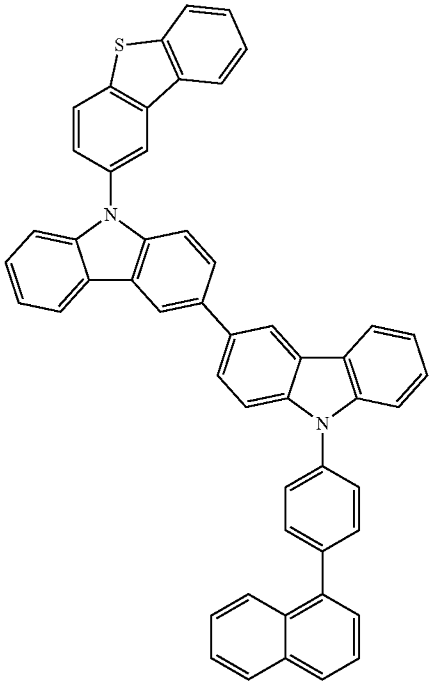
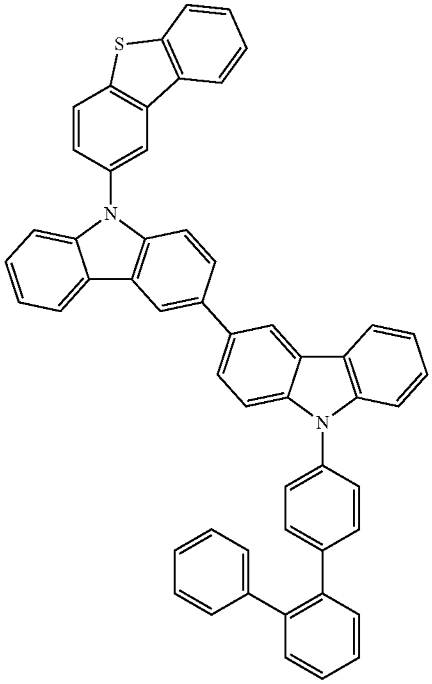

-continued
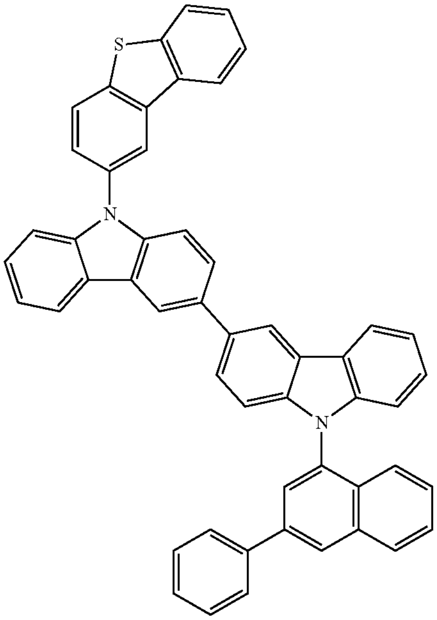
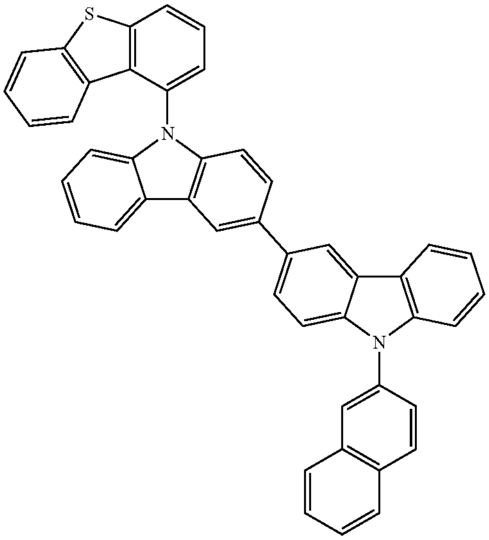
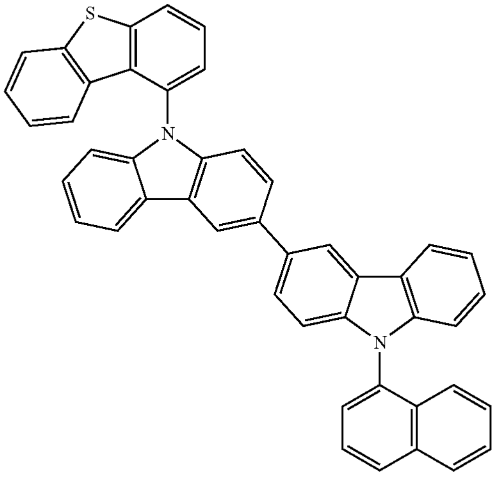
-continued
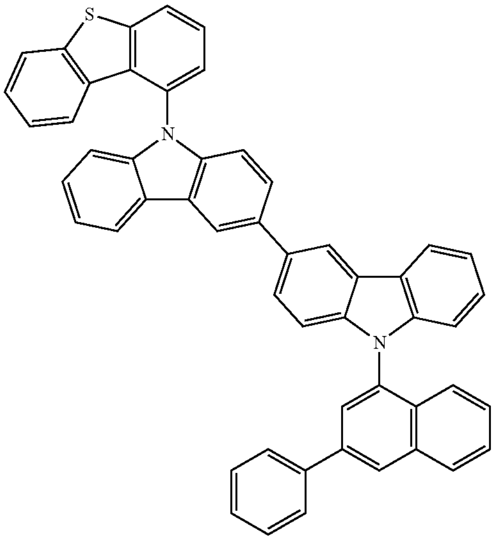
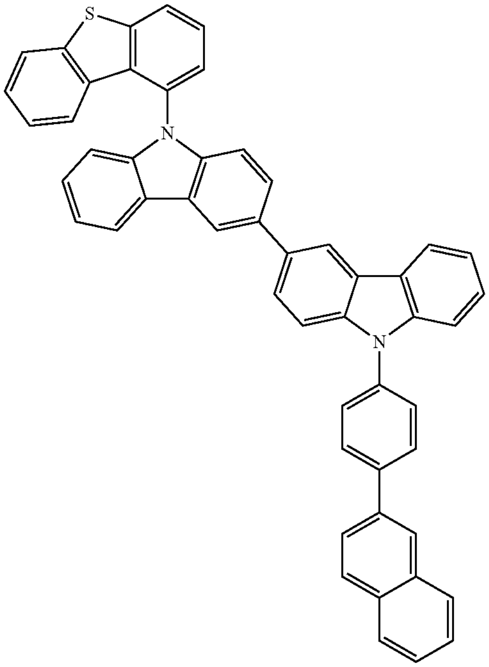

-continued
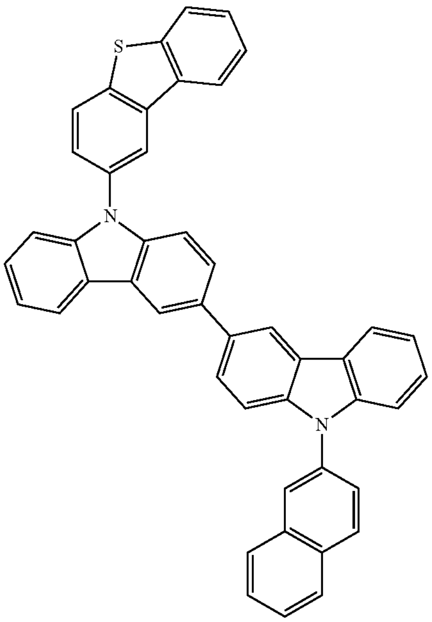
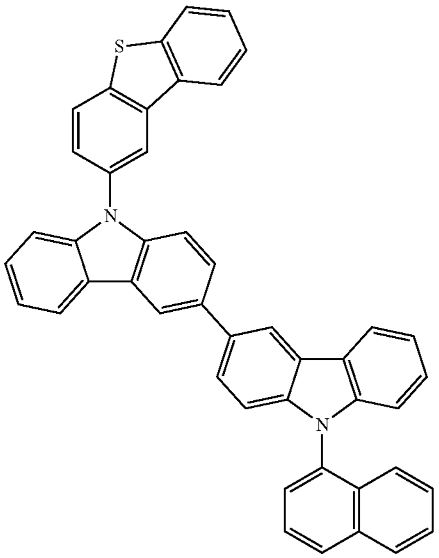
-continued
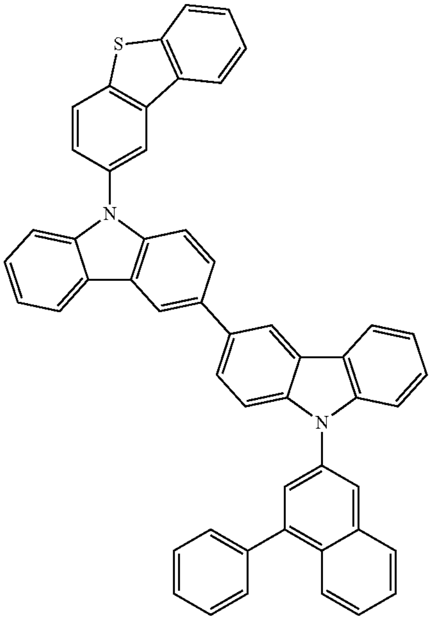
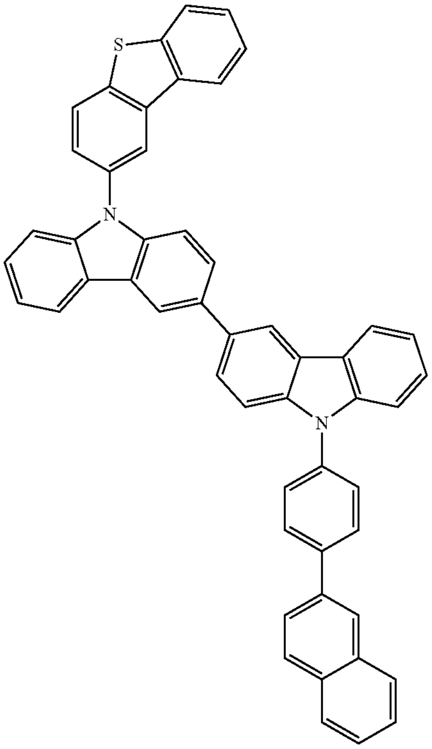

-continued
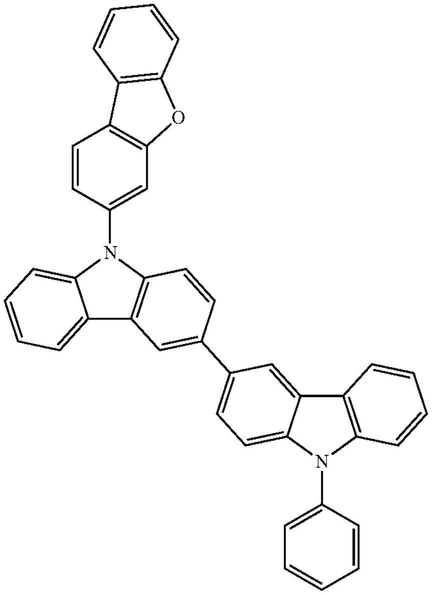
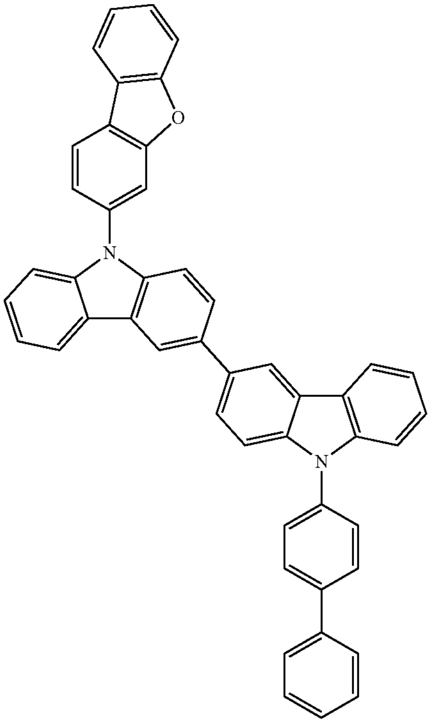
-continued
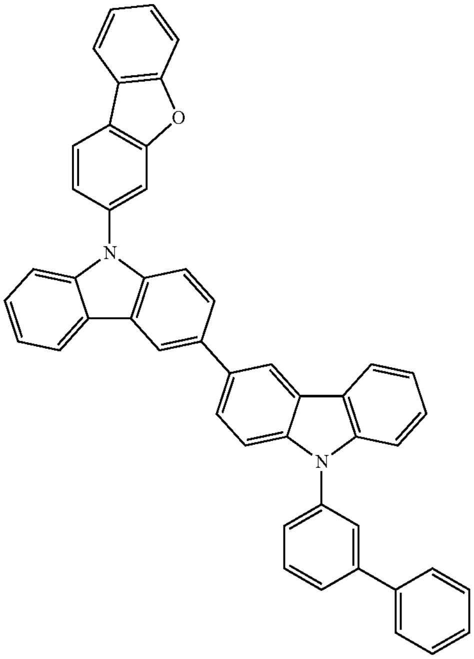
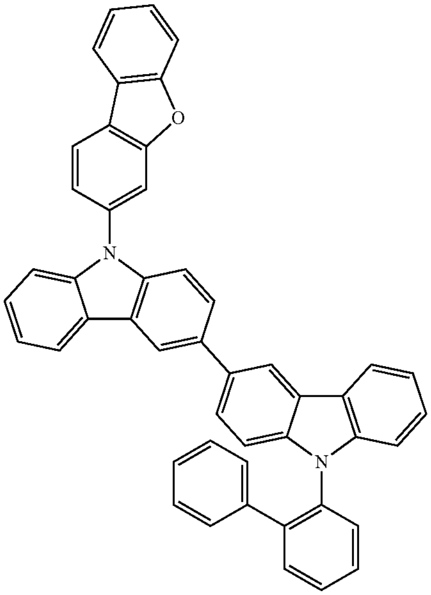

-continued
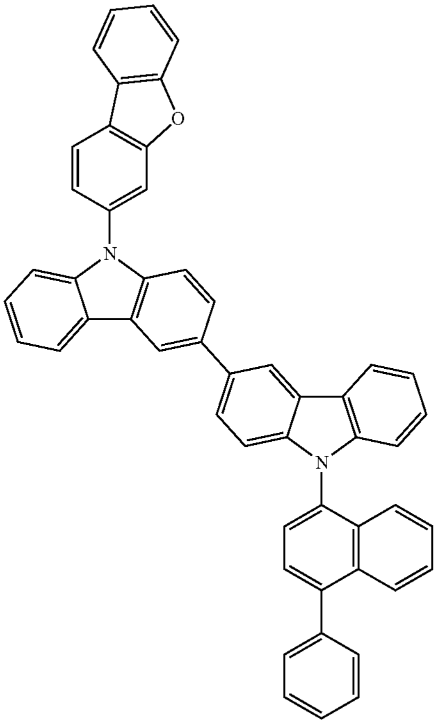
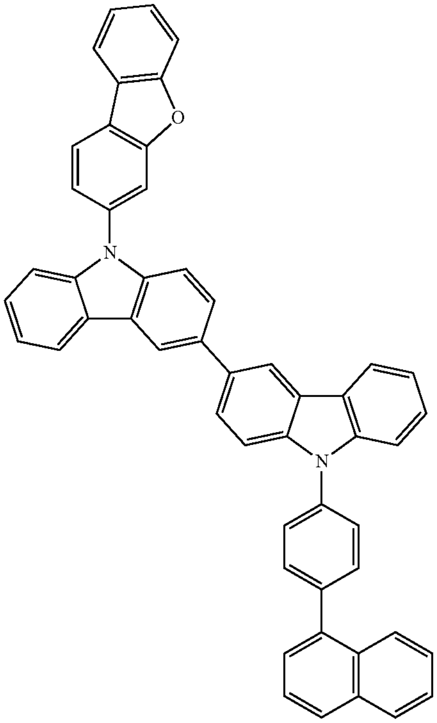
-continued
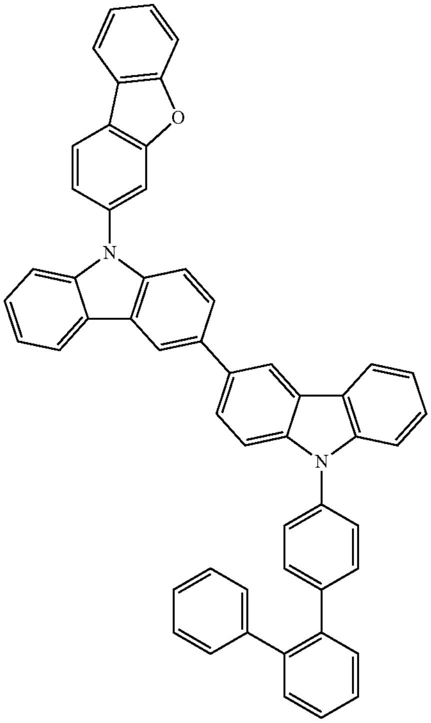
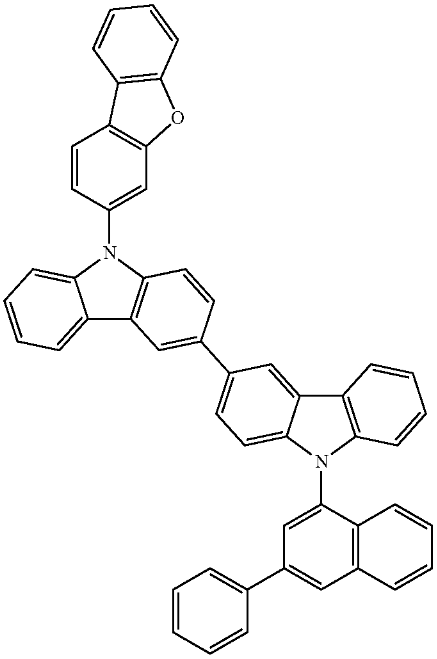

-continued
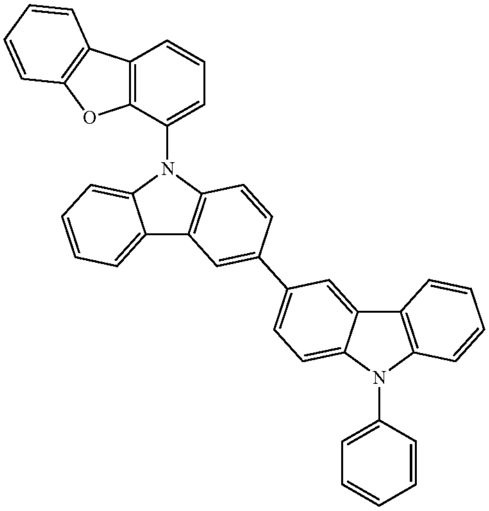
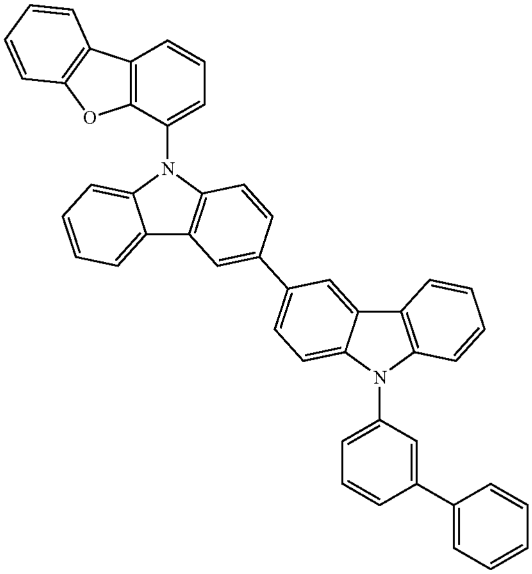
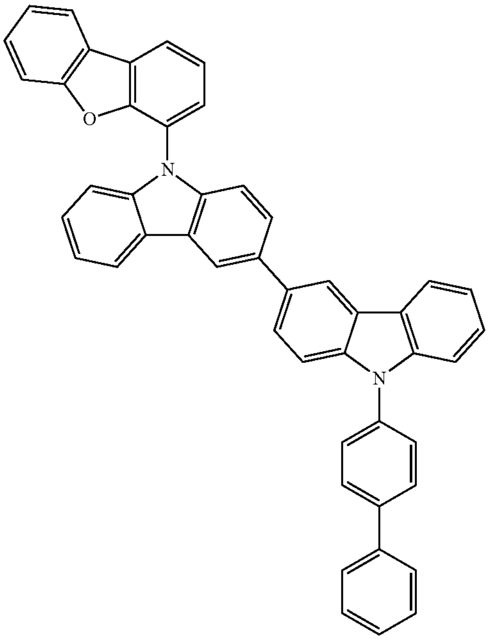
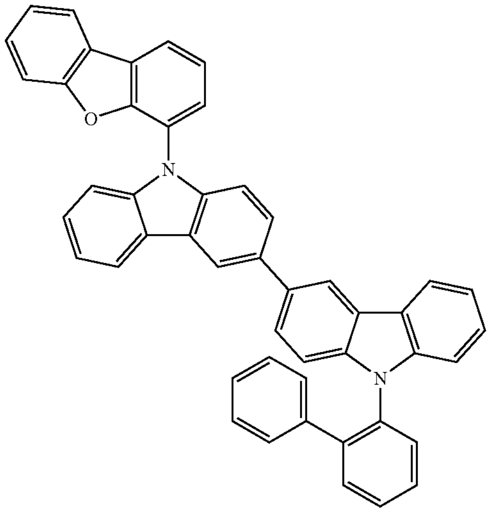
-continued
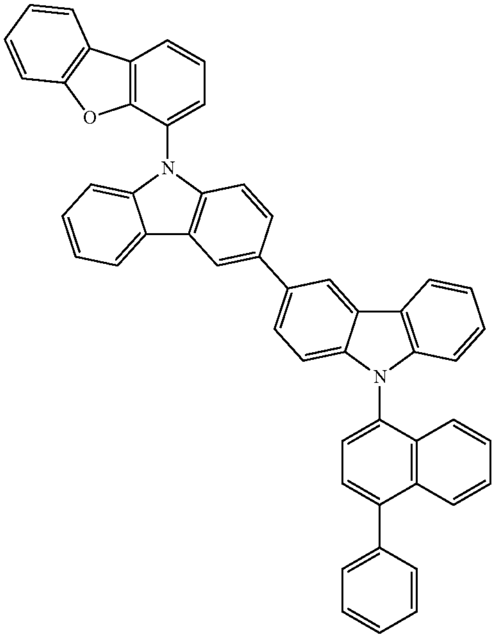

-continued
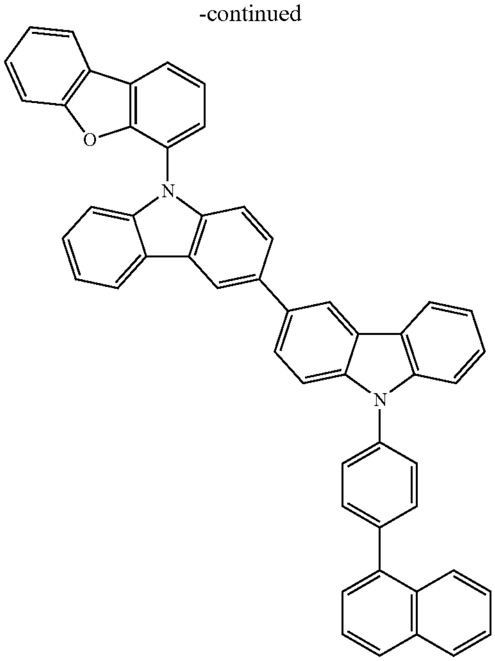
-continued
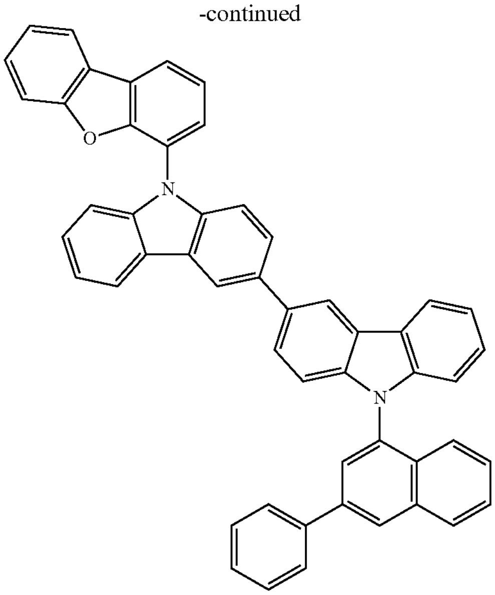
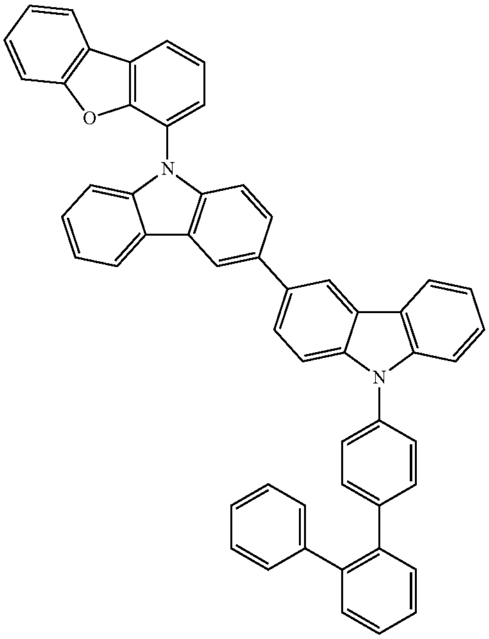
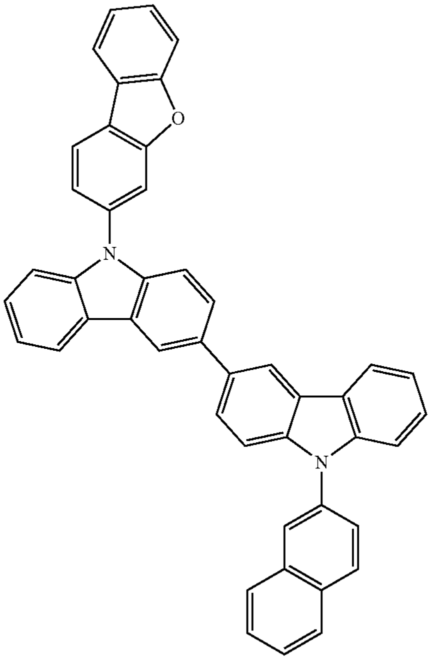

-continued
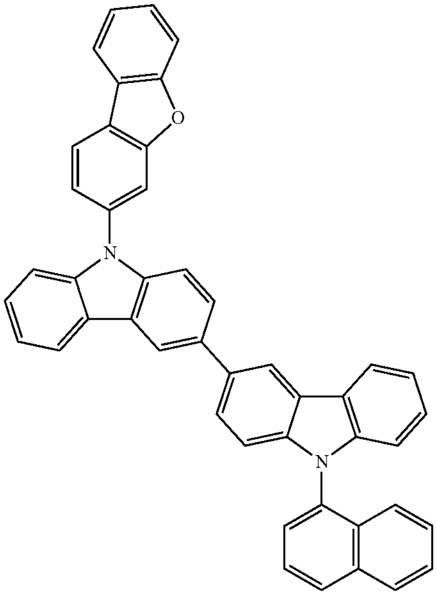
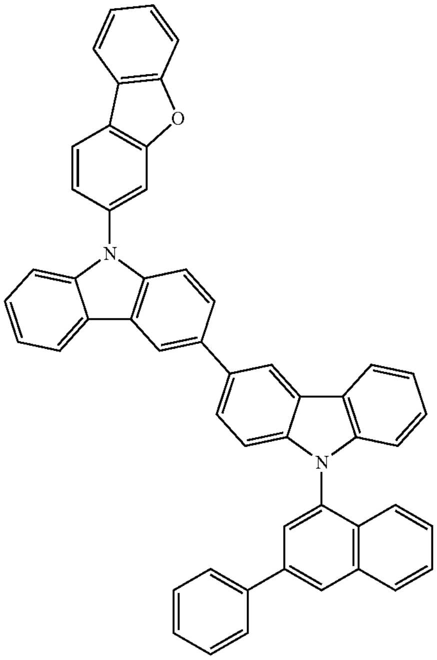
-continued
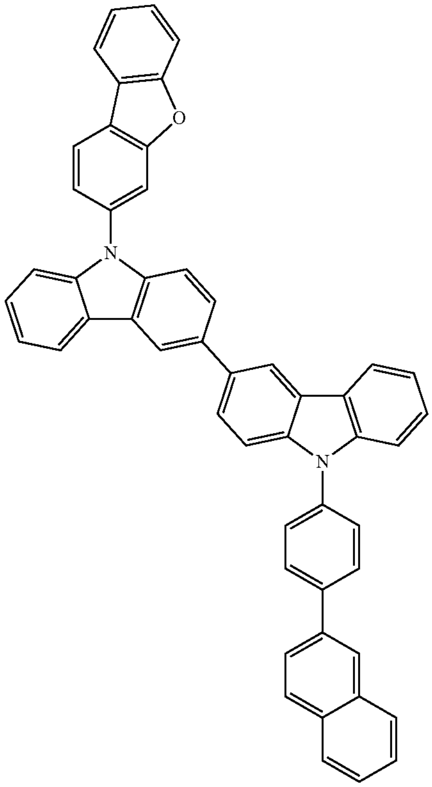
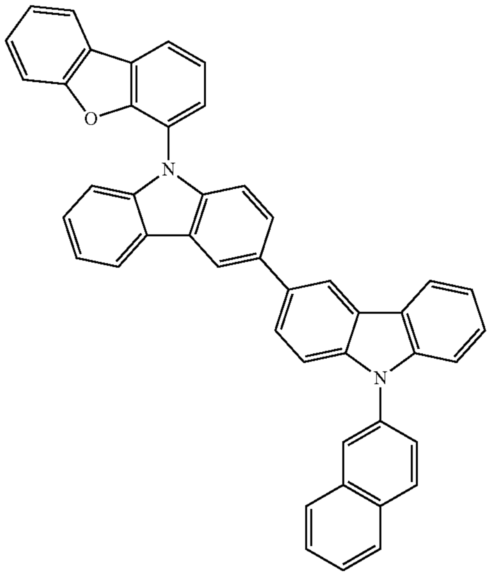

-continued
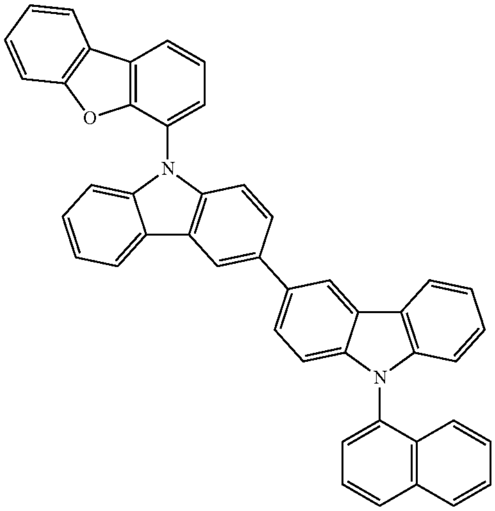
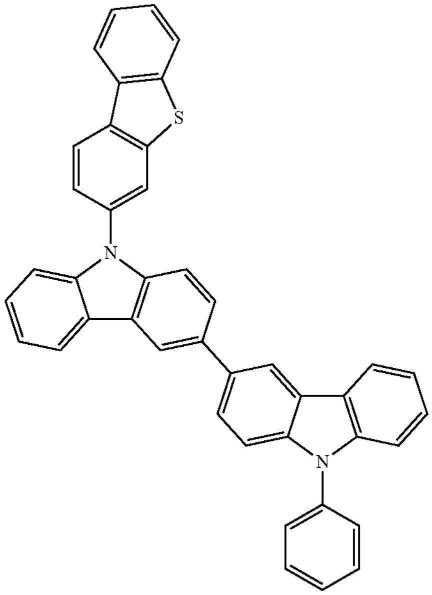
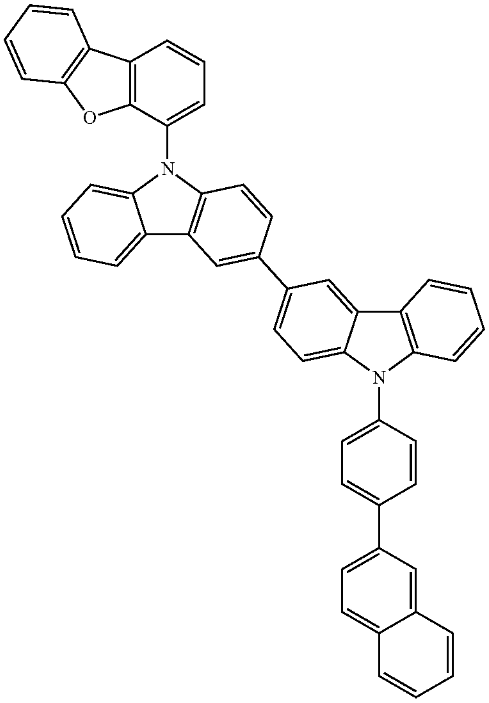
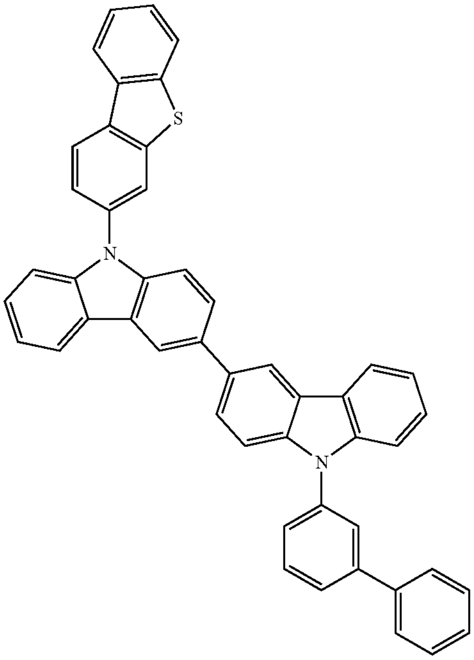
-continued

-continued
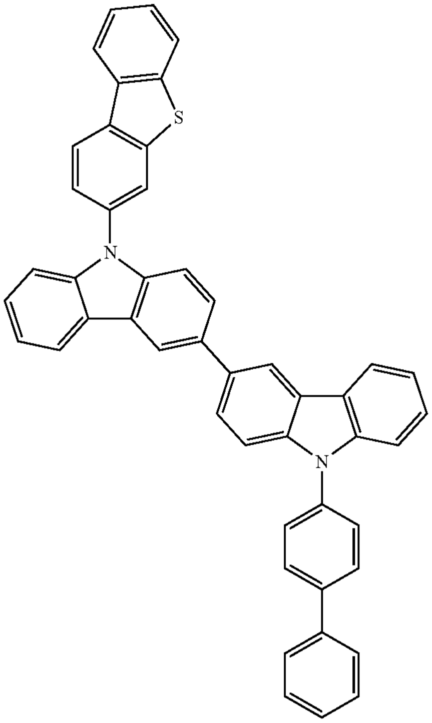
-continued
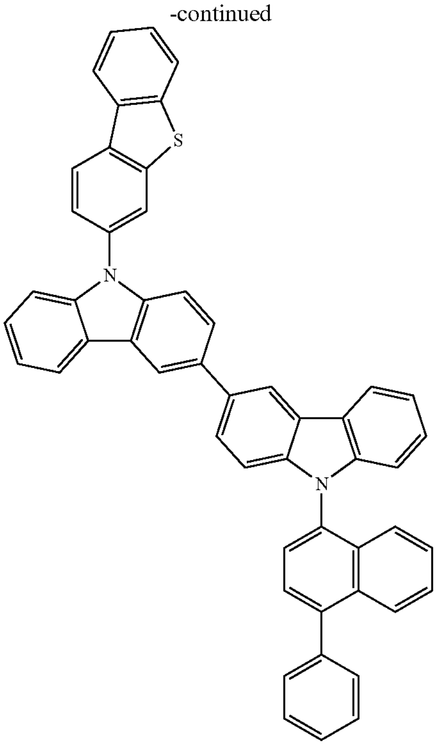
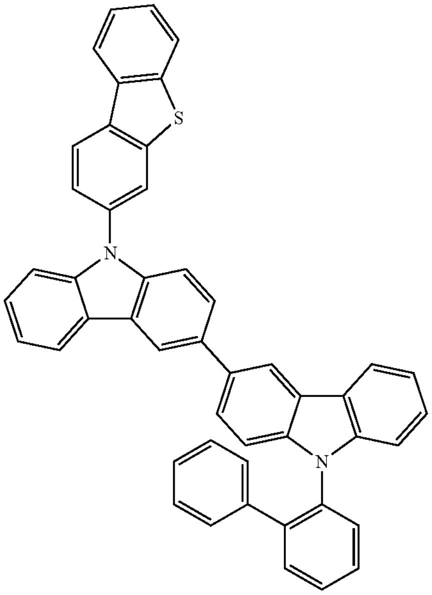
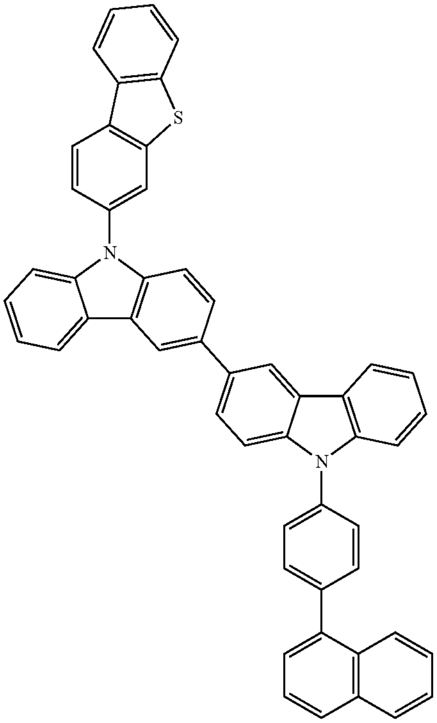

-continued
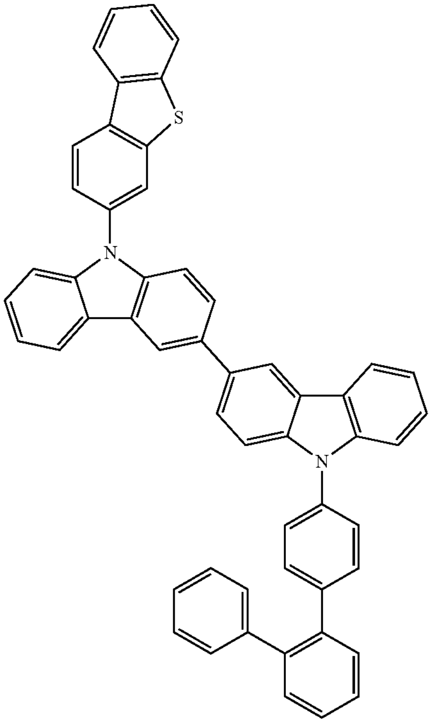
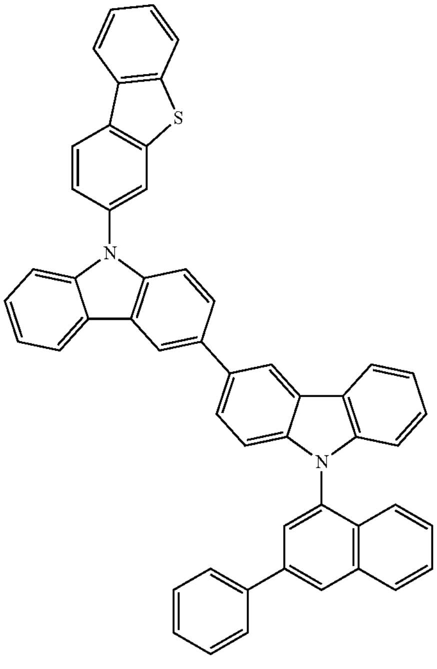
-continued
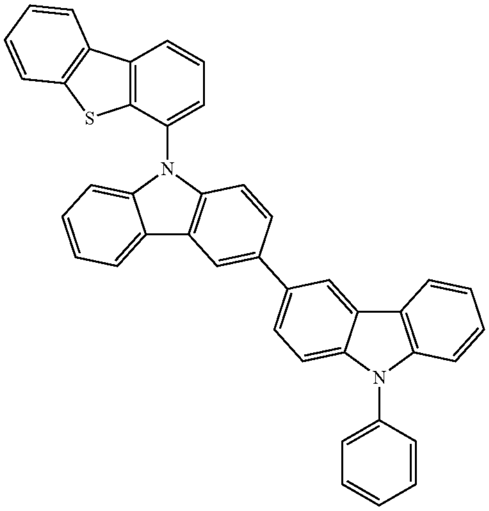
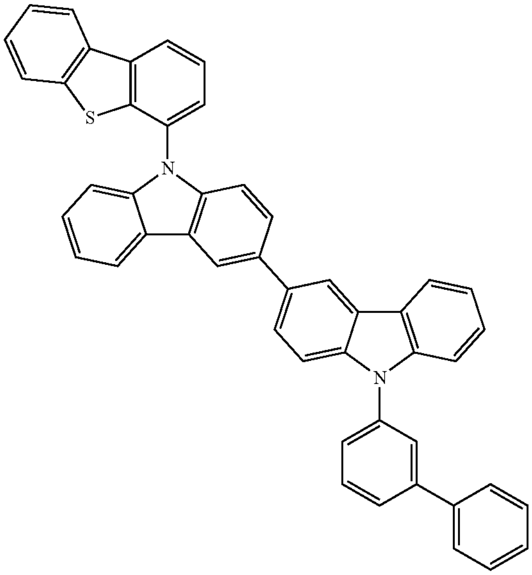
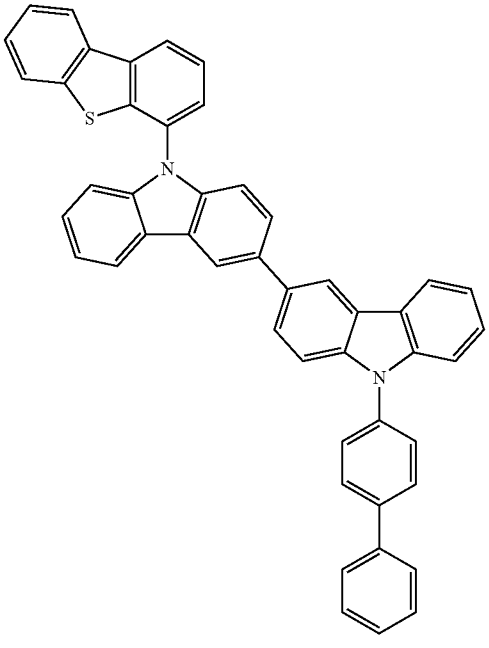

-continued
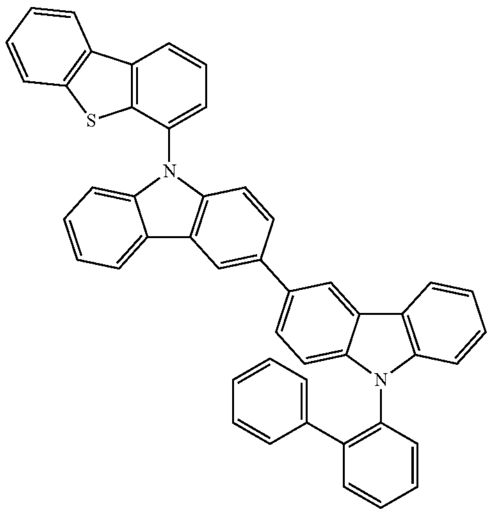
-continued
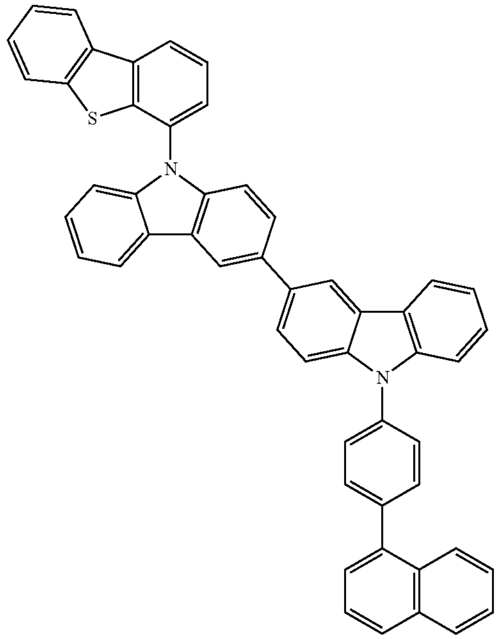
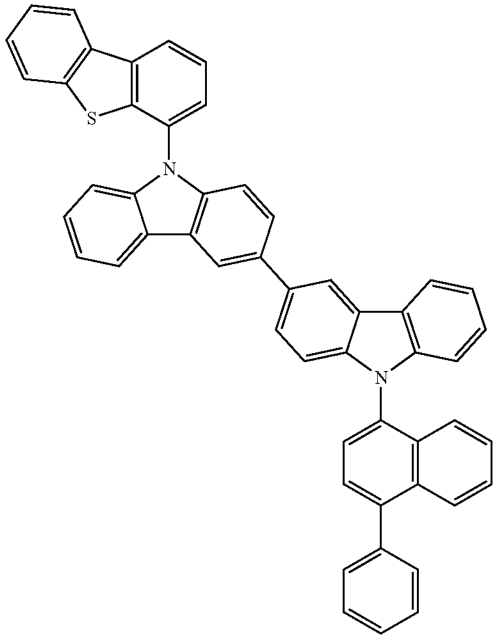
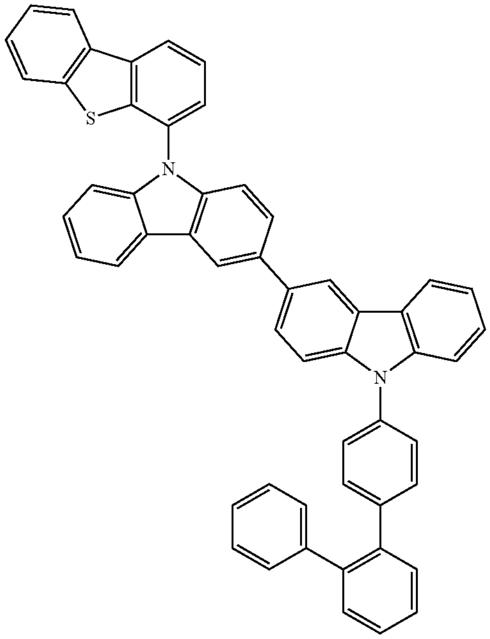

-continued
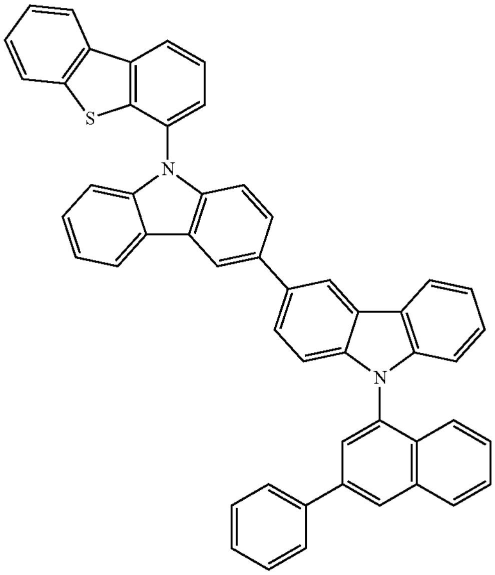
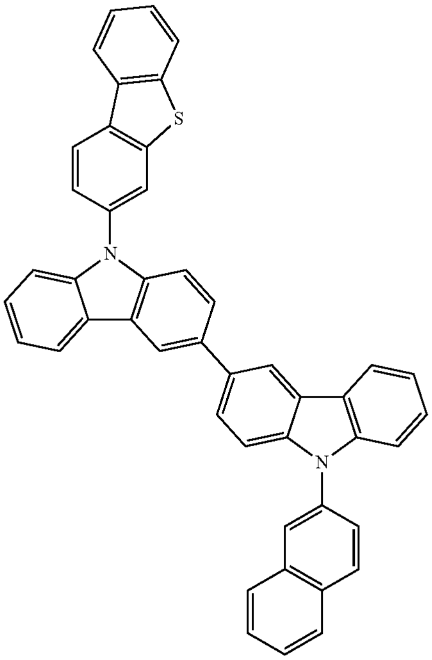
-continued
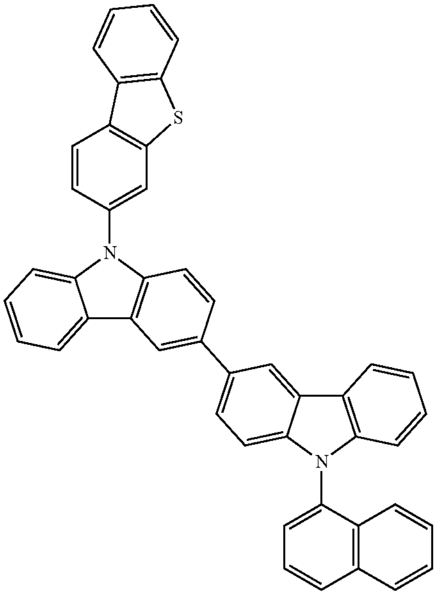
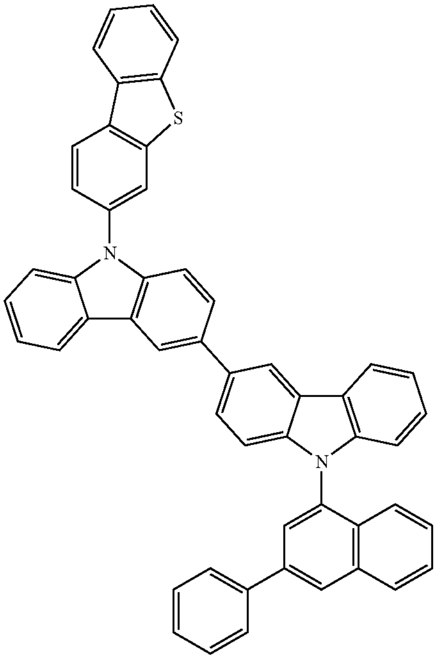

-continued
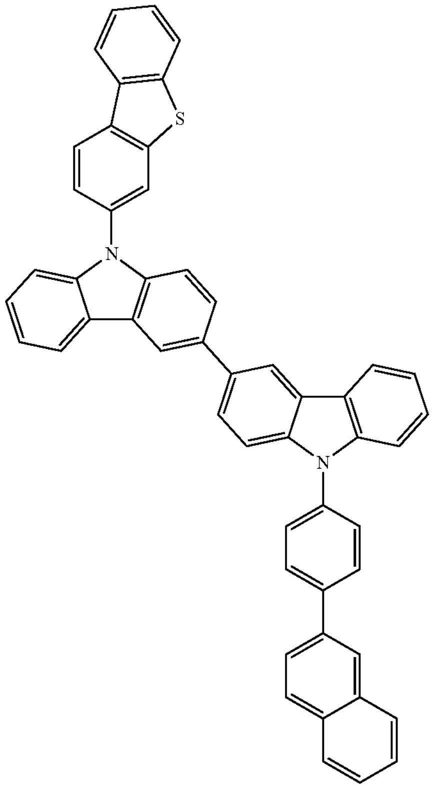
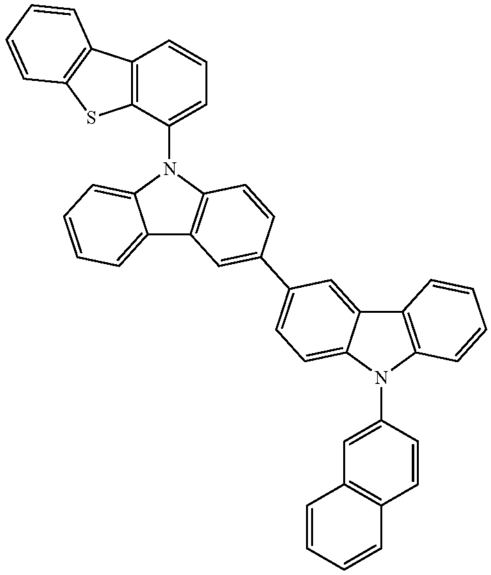
-continued
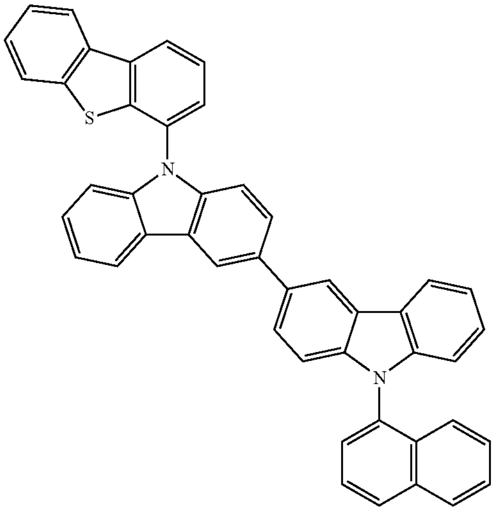
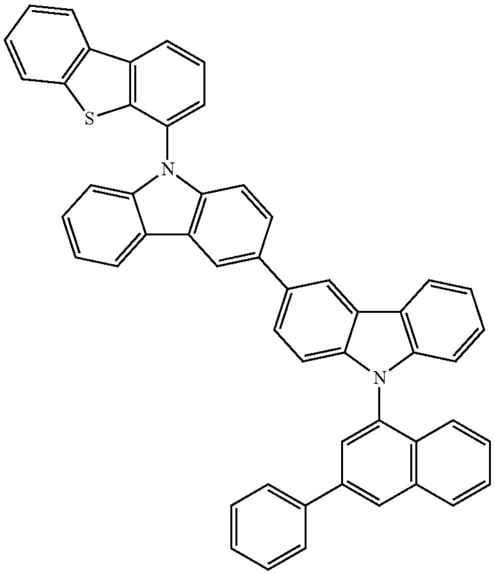

-continued
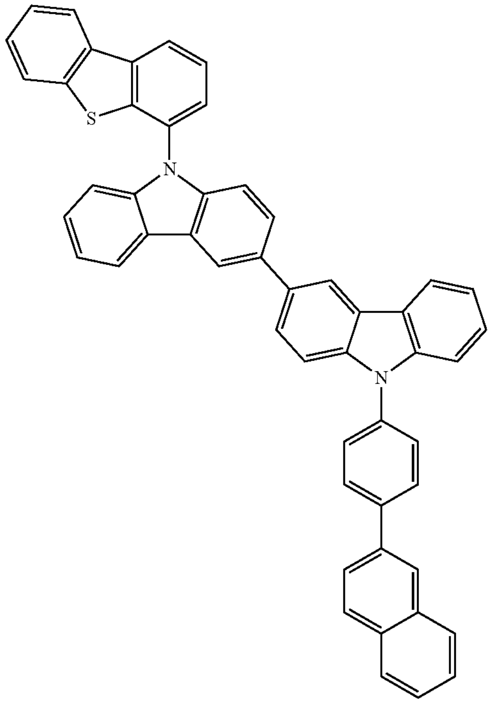
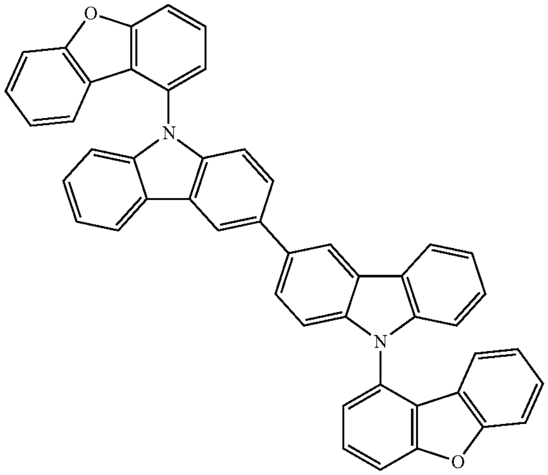
-continued
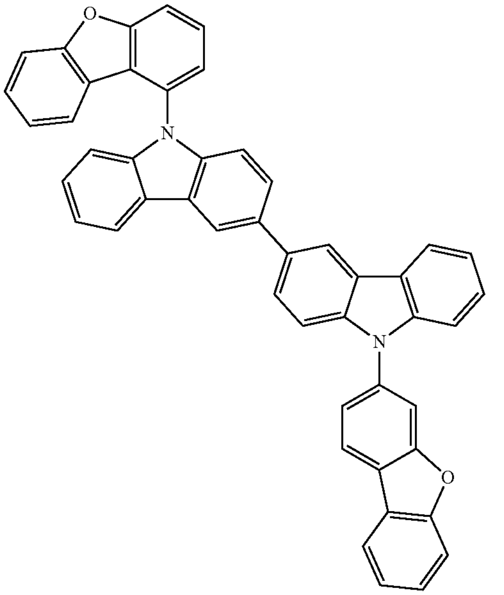
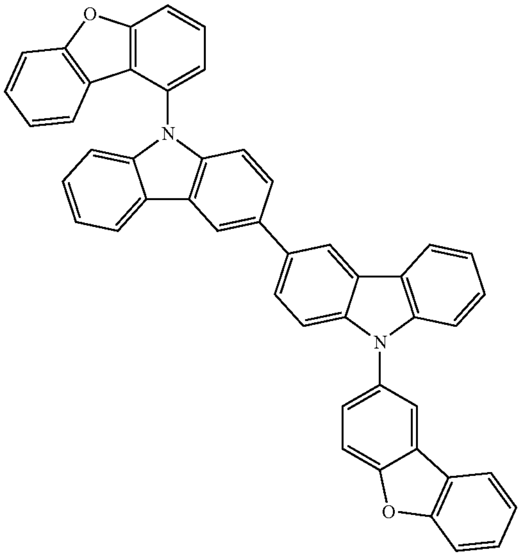
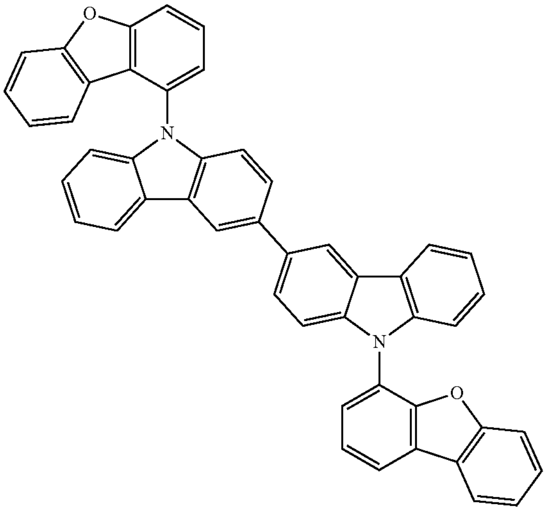

-continued
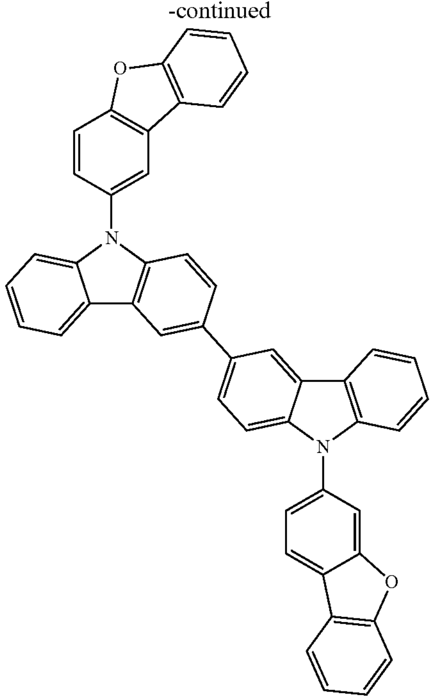
-continued
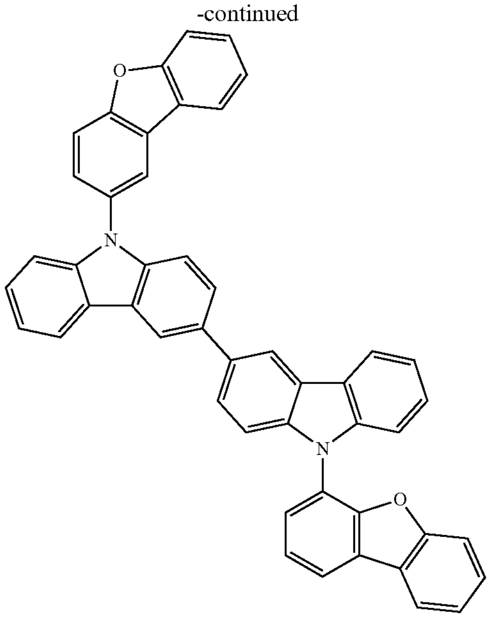
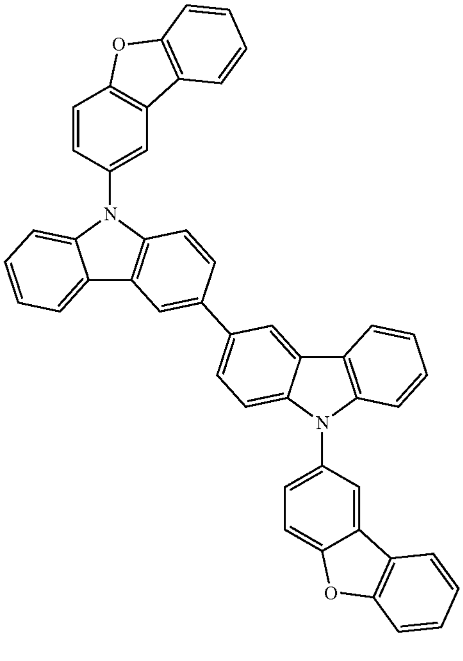
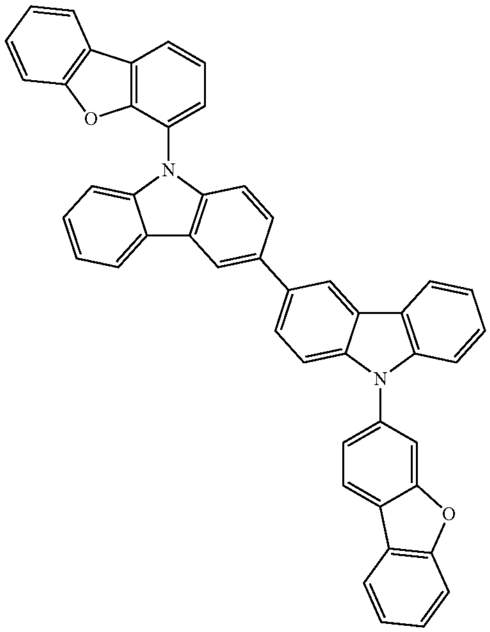

-continued
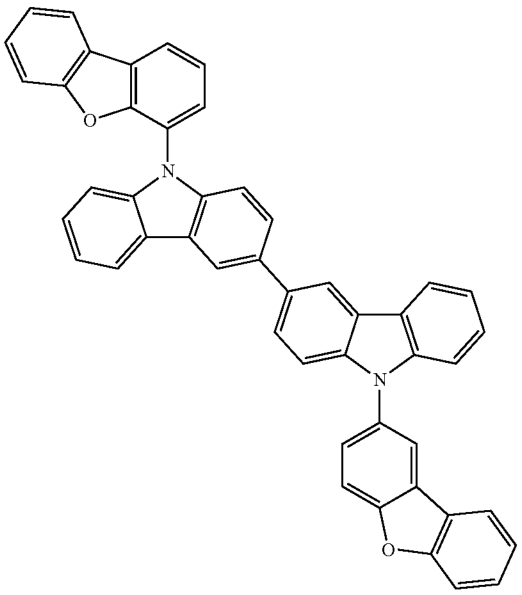
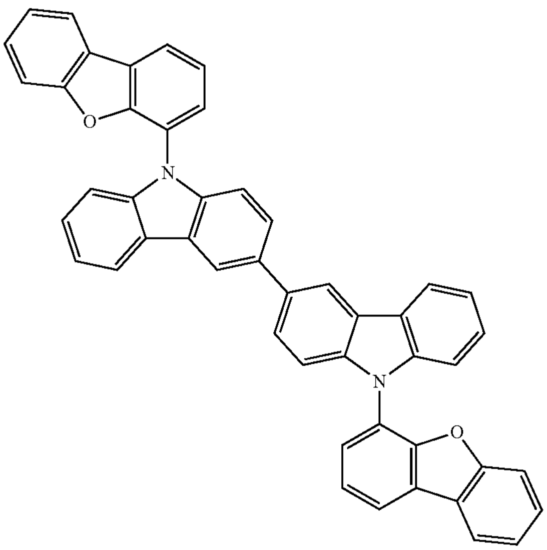
-continued
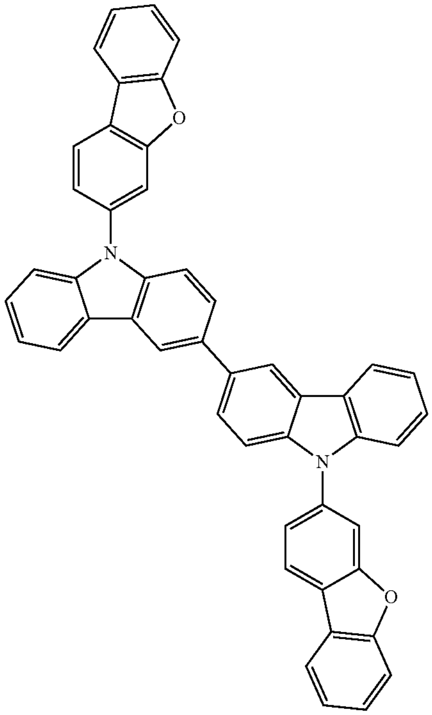
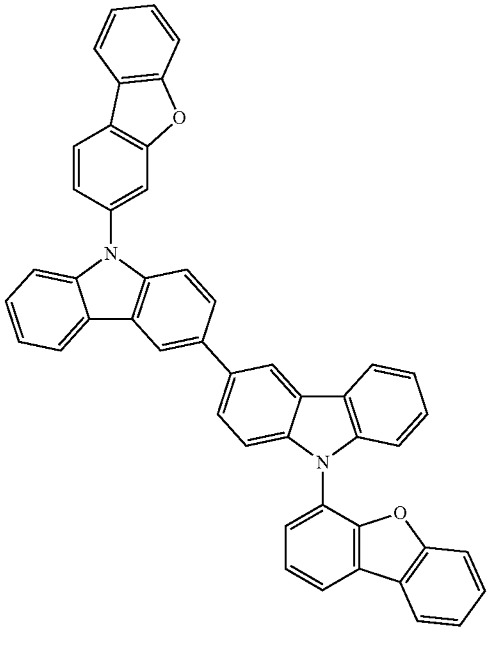

-continued
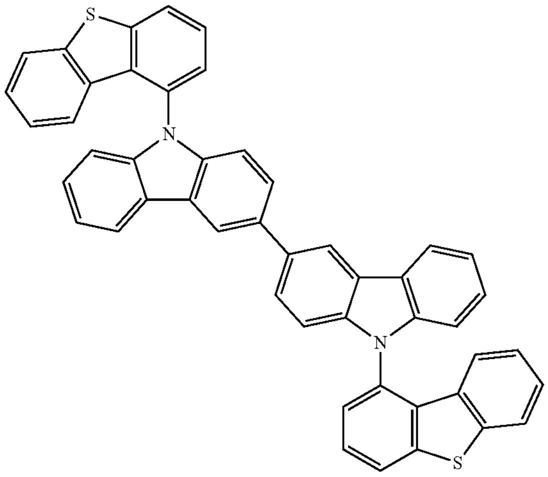
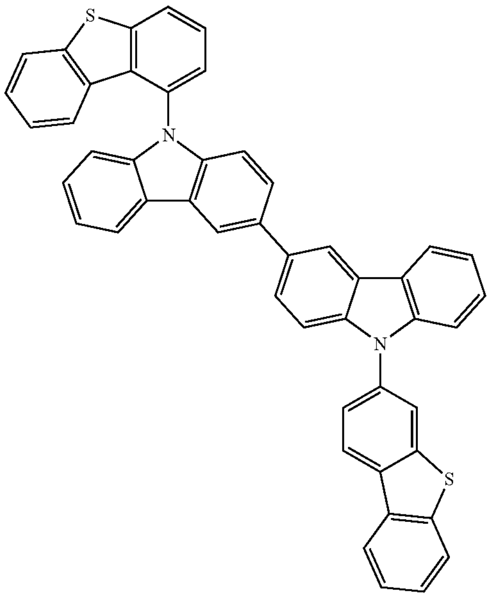
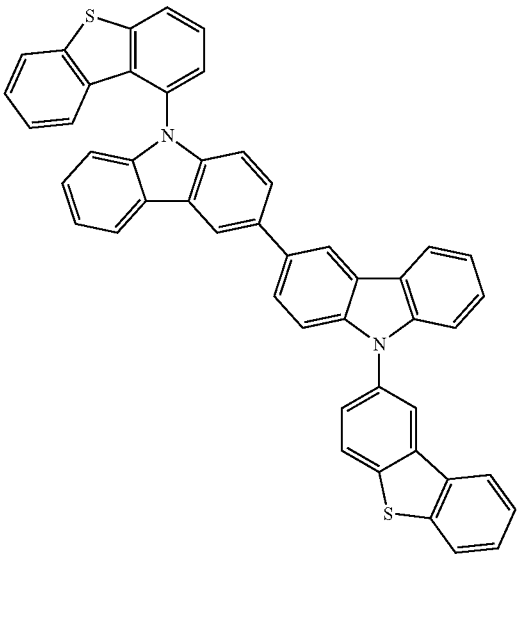
-continued
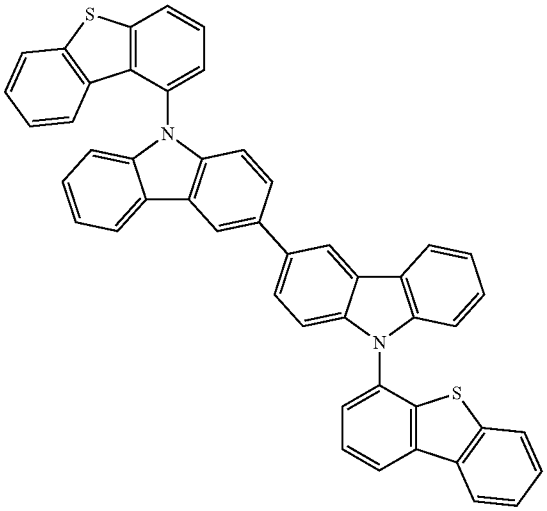
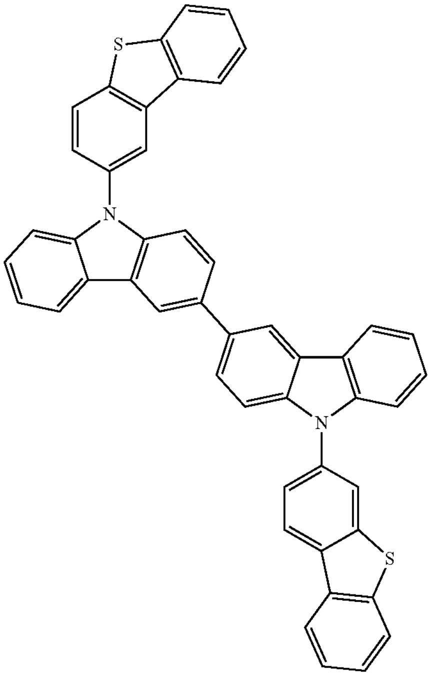

-continued
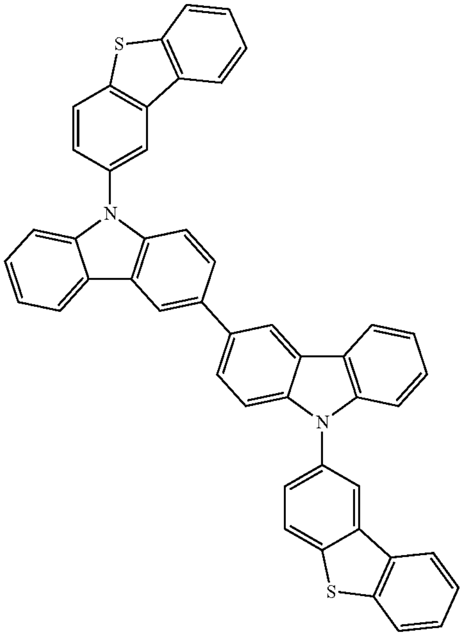
-continued
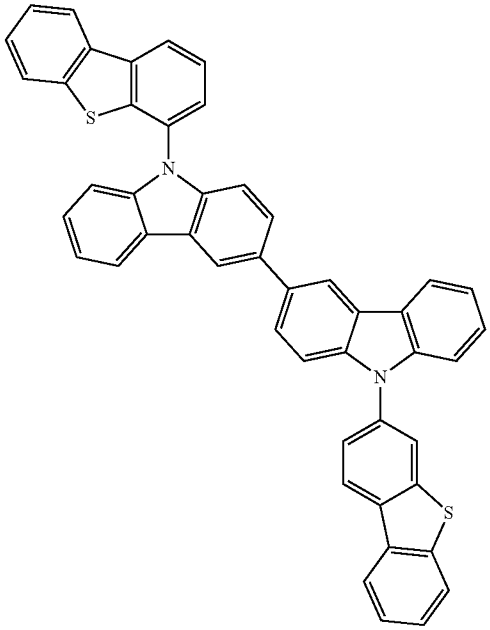
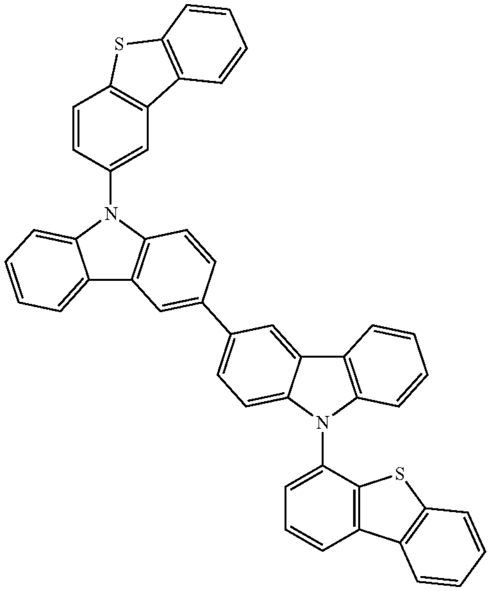
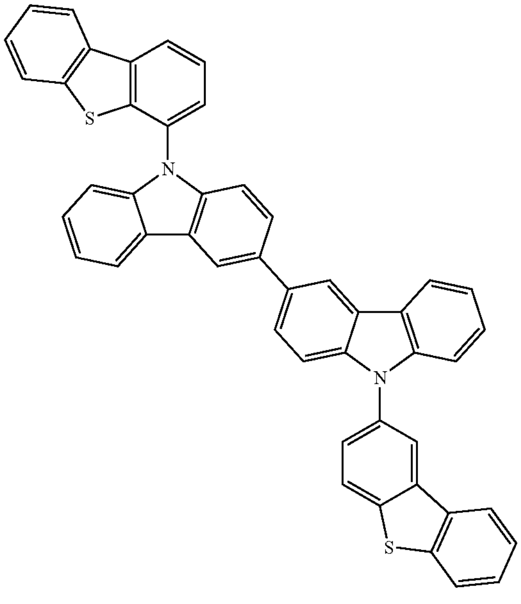

-continued
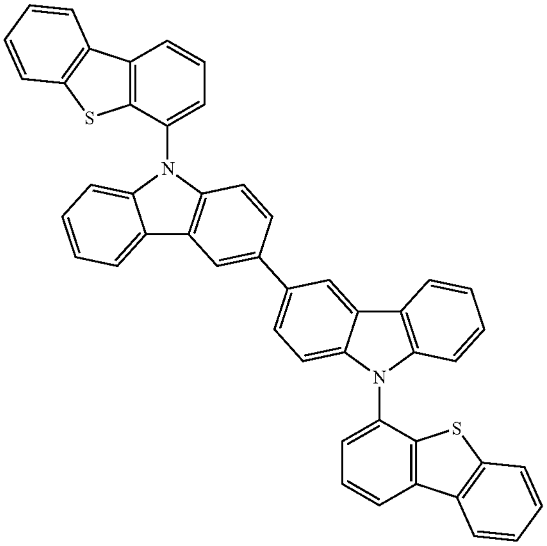
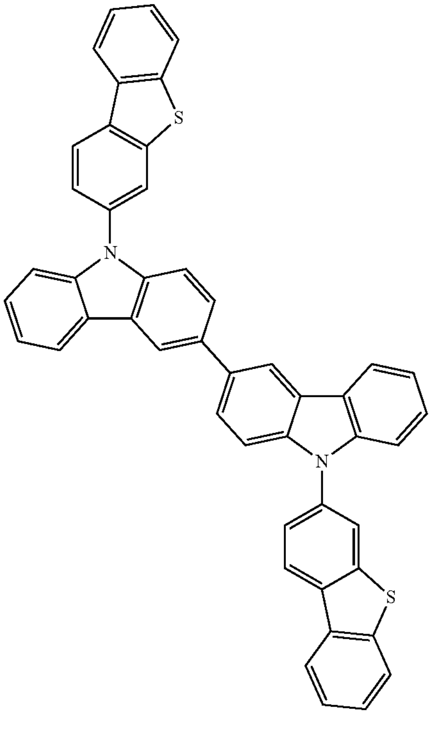
-continued
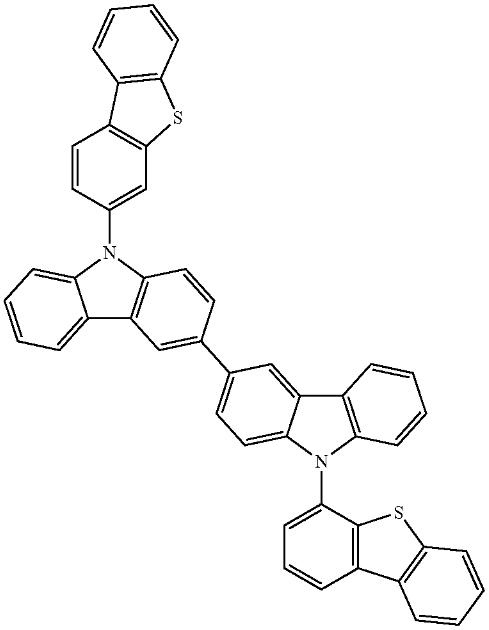
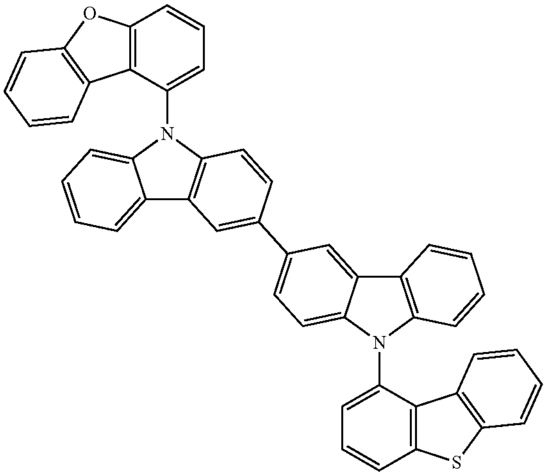
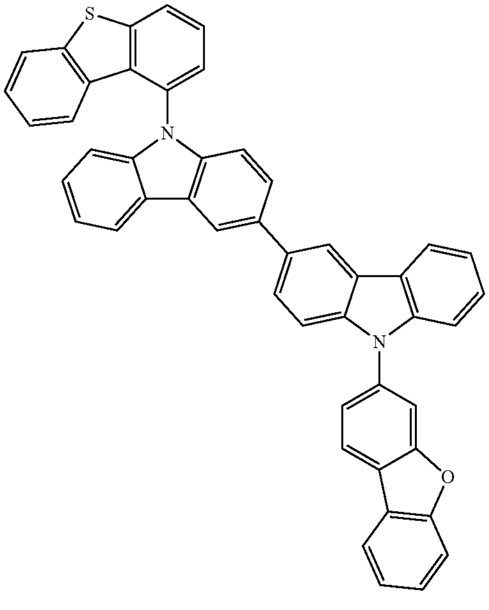

-continued
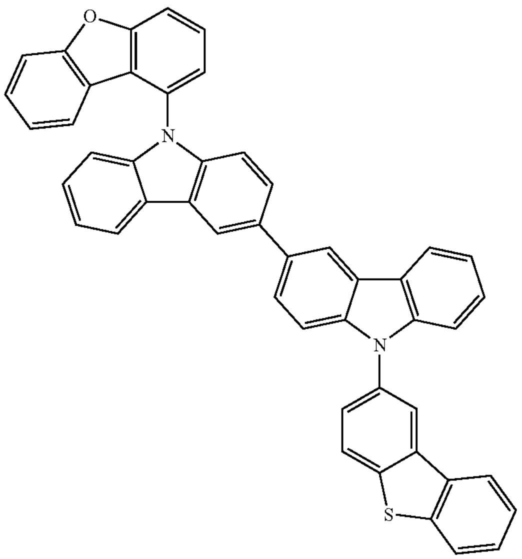
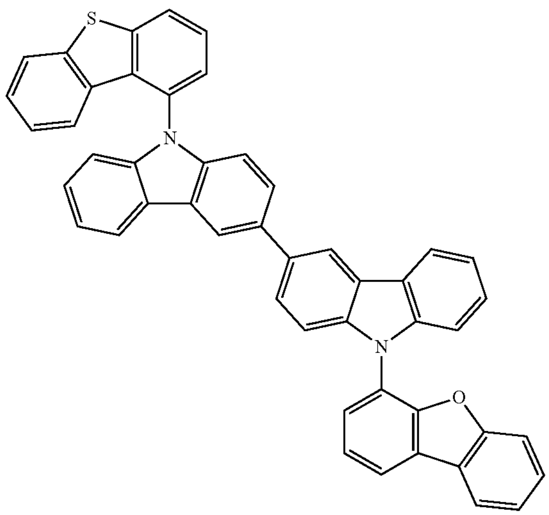
-continued
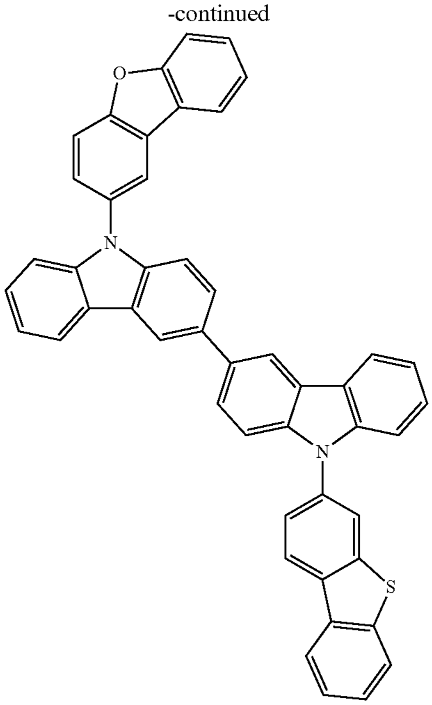
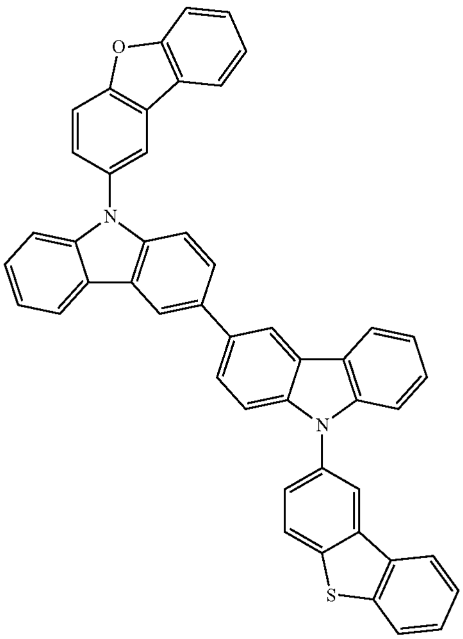

-continued
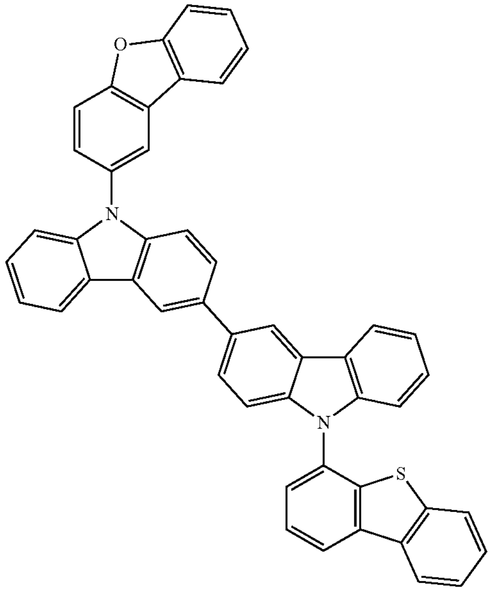
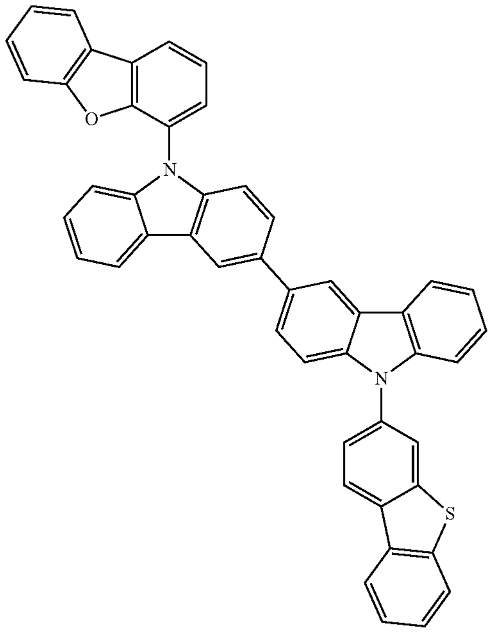
-continued
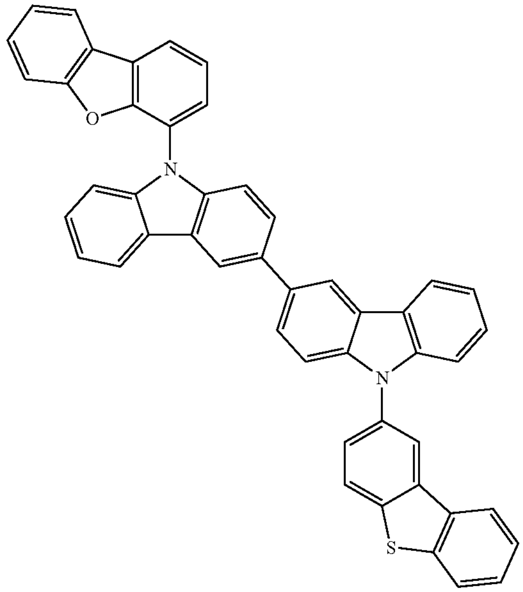
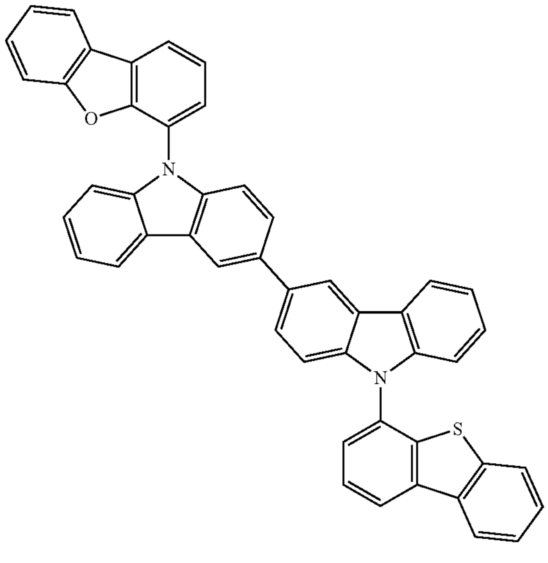

-continued
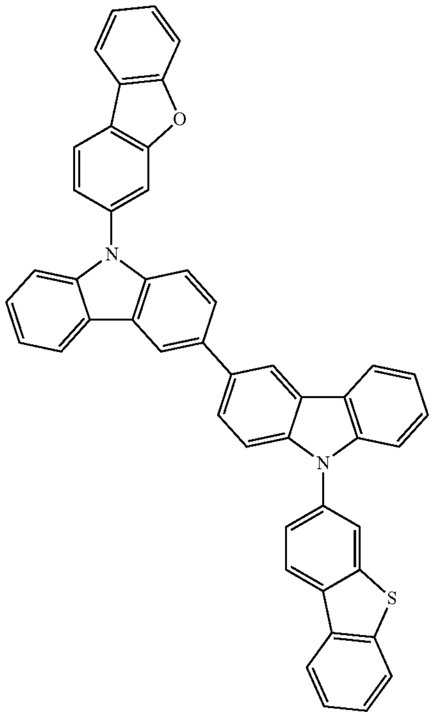
-continued
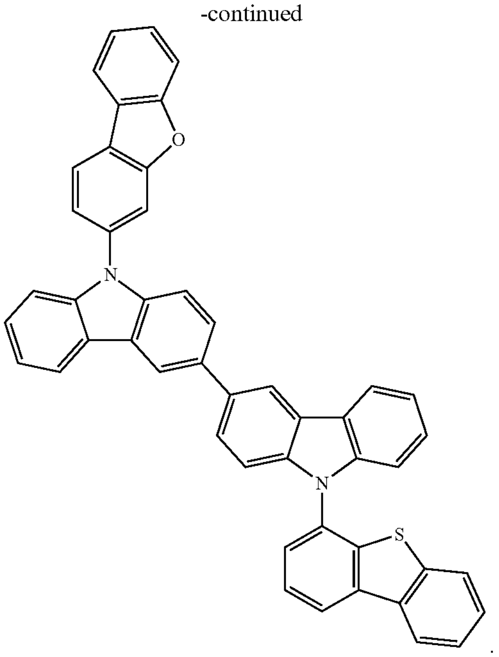
12. The organic light emitting device according to claim 1,
wherein the first compound and the second compound are contained in a weight ratio of 99:1 to 1:99.
* * * * *